US012497382B2

(12) United States Patent
Ammann et al.

(10) Patent No.: US 12,497,382 B2
(45) **Date of Patent: *Dec. 16, 2025**

(54) GLP-1R MODULATING COMPOUNDS

(71) Applicant: Gilead Sciences, Inc., Foster City, CA (US)

(72) Inventors: Stephen E. Ammann, Redwood City, CA (US); Gediminas J. Brizgys, San Carlos, CA (US); James S. Cassidy, Foster City, CA (US); Elbert Chin, San Mateo, CA (US); Chienhung Chou, Dublin, CA (US); Jeromy J. Cottell, Redwood City, CA (US); Michael Graupe, Pacifica, CA (US); Chao-I Hung, Foster City, CA (US); Kavoos Kolahdouzan, San Francisco, CA (US); Scott D. Schroeder, Union City, CA (US); Nathan D. Shapiro, Belmont, CA (US); Daniel G. Shore, Redwood City, CA (US); Suzanne M. Szewczyk, San Mateo, CA (US); James G. Taylor, Burlingame, CA (US); Rhiannon Thomas-Tran, San Jose, CA (US); Nathan E. Wright, Foster City, CA (US); Zheng-Yu Yang, Palo Alto, CA (US); Sheila M. Zipfel, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/195,767

(22) Filed: May 10, 2023

(65) Prior Publication Data

US 2023/0391747 A1 Dec. 7, 2023

Related U.S. Application Data

(63) Continuation of application No. 17/077,729, filed on Oct. 22, 2020, now Pat. No. 11,702,404.

(60) Provisional application No. 63/028,187, filed on May 21, 2020, provisional application No. 62/926,270, filed on Oct. 25, 2019.

(51) Int. Cl.

| | |
|---|---|
| ***A61K 31/4439*** | (2006.01) |
| ***A61K 31/506*** | (2006.01) |
| ***A61K 45/06*** | (2006.01) |
| ***C07D 235/16*** | (2006.01) |
| ***C07D 401/10*** | (2006.01) |
| ***C07D 401/14*** | (2006.01) |
| ***C07D 403/06*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |
| ***C07D 471/04*** | (2006.01) |
| ***C07D 493/08*** | (2006.01) |

(52) U.S. Cl.

CPC ........ *C07D 401/14* (2013.01); *A61K 31/4439* (2013.01); *A61K 31/506* (2013.01); *A61K 45/06* (2013.01); *C07D 235/16* (2013.01); *C07D 401/10* (2013.01); *C07D 403/06* (2013.01); *C07D 405/14* (2013.01); *C07D 409/14* (2013.01); *C07D 413/14* (2013.01); *C07D 417/14* (2013.01); *C07D 471/04* (2013.01); *C07D 493/08* (2013.01)

(58) Field of Classification Search

CPC .......................... A61K 31/4439; A61K 31/506

See application file for complete search history.

(56) References Cited

U.S. PATENT DOCUMENTS

| | | | |
|---|---|---|---|
| 8,957,073 | B2 | 2/2015 | Allen |
| 10,543,212 | B2 | 1/2020 | Matsunaga et al. |
| 10,954,221 | B2 | 3/2021 | Zhong et al. |
| 11,702,404 | B2 | 7/2023 | Ammann et al. |
| 11,851,419 | B2 | 12/2023 | Brizgys |
| 11,858,918 | B2 | 1/2024 | Armstrong |
| 11,981,666 | B2 | 5/2024 | Zhai |
| 12,091,404 | B2 | 9/2024 | Brizgys |
| 12,121,511 | B2 | 10/2024 | Ammann |
| 2017/0035881 | A1 | 2/2017 | Lannutti et al. |
| 2018/0170908 | A1 | 6/2018 | Aspnes et al. |
| 2020/0325121 | A1 | 10/2020 | Zhong et al. |
| 2021/0023072 | A1 | 1/2021 | Freeman et al. |
| 2021/0171499 | A1 | 6/2021 | Ammann |
| 2022/0177449 | A1 | 6/2022 | Brizgys et al. |
| 2022/0288030 | A1 | 9/2022 | Ammann et al. |
| 2022/0298148 | A1 | 9/2022 | Brizgys et al. |

(Continued)

FOREIGN PATENT DOCUMENTS

| | | | |
|---|---|---|---|
| CN | 112409331 | A | 2/2021 |
| CN | 113480534 | A | 10/2021 |

(Continued)

OTHER PUBLICATIONS

Ratziu et al., Journal of Hepatology, 2015, vol. 62, pp. S65-S75. (Year: 2015).*

(Continued)

*Primary Examiner* — Laura L Stockton

(74) *Attorney, Agent, or Firm* — Mintz, Levin, Cohn, Ferris, Glovsky and Popeo, P.C.

(57) ABSTRACT

The present disclosure provides GLP-1R agonists, and compositions, methods, and kits thereof. Such compounds are generally useful for treating a GLP-1R mediated disease or condition in a human.

10 Claims, No Drawings

(56) References Cited

U.S. PATENT DOCUMENTS

| | | | |
|---|---|---|---|
| 2022/0306614 A1 | 9/2022 | Brizgys et al. |
| 2023/0021705 A1 | 1/2023 | Armstrong et al. |
| 2024/0199580 A1 | 6/2024 | Brizgys |
| 2024/0199589 A1 | 6/2024 | Armstrong |
| 2025/0084072 A1 | 3/2025 | Brizgys |
| 2025/0099431 A1 | 3/2025 | Ammann |

FOREIGN PATENT DOCUMENTS

| | | | |
|---|---|---|---|
| CN | 113493447 A | 10/2021 |
| CN | 113816948 A | 12/2021 |
| EP | 3438095 A1 | 2/2019 |
| EP | 4057055 A1 | 9/2022 |
| TW | 201904959 A | 2/2019 |
| TW | 202015683 A | 5/2020 |
| WO | WO-2000/08015 A2 | 2/2000 |
| WO | 2001002369 A1 | 1/2001 |
| WO | WO-2003/026587 A2 | 4/2003 |
| WO | WO-2004/099192 A2 | 11/2004 |
| WO | 2004108672 A1 | 12/2004 |
| WO | WO-2005/014543 A1 | 2/2005 |
| WO | WO-2006/055708 A2 | 5/2006 |
| WO | WO-2006/066879 A2 | 6/2006 |
| WO | WO-2007/031791 A1 | 3/2007 |
| WO | WO-2007/115077 A2 | 10/2007 |
| WO | WO-2008/033455 A2 | 3/2008 |
| WO | 2009111700 | 11/2009 |
| WO | WO-2010/029299 A1 | 3/2010 |
| WO | WO-2010/029300 A1 | 3/2010 |
| WO | WO-2010/046780 A2 | 4/2010 |
| WO | 2011143365 | 11/2011 |
| WO | 2011156655 | 12/2011 |
| WO | WO-2011/163355 A1 | 12/2011 |
| WO | WO-2013/025733 A1 | 2/2013 |
| WO | WO-2013/056679 A1 | 4/2013 |
| WO | 2013/090454 | 6/2013 |
| WO | WO-2013/186229 A1 | 12/2013 |
| WO | WO-2016/018701 A1 | 2/2016 |
| WO | WO-2016/089060 A2 | 6/2016 |
| WO | WO-2016/118638 A1 | 7/2016 |
| WO | WO-2017/161028 A1 | 9/2017 |
| WO | WO-2018/109607 A1 | 6/2018 |
| WO | WO-2018/183112 A1 | 10/2018 |
| WO | WO-2019/055540 A1 | 3/2019 |
| WO | WO-2019/239319 A1 | 12/2019 |
| WO | WO-2019/239371 A1 | 12/2019 |
| WO | WO-2020/033413 A2 | 2/2020 |
| WO | WO-2020/103815 A1 | 5/2020 |
| WO | WO-2020/207474 A1 | 10/2020 |
| WO | WO-2020/263695 A1 | 12/2020 |
| WO | WO-2021/018023 A1 | 2/2021 |
| WO | WO-2021/018026 A1 | 2/2021 |
| WO | WO-2021/081207 A1 | 4/2021 |
| WO | WO-2021/096284 A1 | 5/2021 |
| WO | WO-2021/096304 A1 | 5/2021 |
| WO | WO-2021/112538 A1 | 6/2021 |
| WO | WO-2021/154796 A1 | 8/2021 |
| WO | WO-2021/155841 A1 | 8/2021 |
| WO | WO-2021/160127 A1 | 8/2021 |
| WO | WO-2021/187886 A1 | 9/2021 |
| WO | WO-2021/191812 A1 | 9/2021 |
| WO | WO-2021/197464 A1 | 10/2021 |
| WO | WO-2021/242817 A1 | 12/2021 |
| WO | WO-2021/244645 A1 | 12/2021 |
| WO | 2022031994 A1 | 2/2022 |
| WO | WO-2022/040600 A1 | 2/2022 |
| WO | WO-2022/068772 A1 | 4/2022 |
| WO | WO-2022/078152 A1 | 4/2022 |
| WO | WO-2022/109182 A1 | 5/2022 |
| WO | WO-2022/111624 A1 | 6/2022 |
| WO | 2022189191 | 9/2022 |
| WO | WO-2022/192428 A1 | 9/2022 |
| WO | WO-2022/192430 A1 | 9/2022 |
| WO | 2022216094 A1 | 10/2022 |
| WO | 2022224164 | 10/2022 |
| WO | WO-2022/225914 A1 | 10/2022 |
| WO | WO-2022/225941 A1 | 10/2022 |
| WO | 2023102378 | 6/2023 |

OTHER PUBLICATIONS

Andersen, A et al. (2018), "Glucagon-like peptide 1 in health and disease", Nat Rev Endocrinol., Jul;14(7):390-403.

Armstrong M J et al. (2016), "Liraglutide safety and efficacy in patients with non-alcoholic steatohepatitis (LEAN): a multicentre, double-blind, randomised, placebo-controlled phase 2 study", Lancet, 387(10019):679-690.

Armstrong, M et al. (2013), "Liraglutide efficacy and action in non-alcoholic steatohepatitis (LEAN): study protocol for a phase II multicentre, double-blinded, randomised, controlled trial", BMJ Open., 3(11):e003995, pp. 1-13.

Armstrong, M J et al. (2016), "Glucagon-like peptide 1 decreases lipotoxicity in non-alcoholic steatohepatitis", Randomized Controlled Trial J Hepatol., 64(2):399-408.

Armstrong, M. J. (2017), "Glucagon-like peptide-1 analogues in nonalcoholic steatohepatitis: From bench to bedside", Review Clin Liver Dis (Hoboken), 10(2):32-35.

Ben-Shlomo, S et al. (2011), "Glucagon-like peptide-1 reduces hepatic lipogenesis via activation of AMP-activated protein kinase", J Hepatol. 54(6):1214-23.

Bernsmeier, C et al. (2014), "Glucose-Induced Glucagon-Like Peptide 1 Secretion Is Deficient in Patients with Non-Alcoholic Fatty Liver Disease", PLoS One, 9(1):e87488, 1-7.

Bueno, A B et al. (2016), "Positive Allosteric Modulation of the Glucagon-like Peptide-1 Receptor by Diverse Electrophiles", J Biol Chem, May 13, 2016; 291(20):10700-15.

Carbone L J et al. (2016), "Incretin-based therapies for the treatment of non-alcoholic fatty liver disease: A systemic review and meta-analysis", J Gastroenterol Hepatol, 31(1):23-31.

Chen D et al. (2007), "A nonpeptidic agonist of glucagon-like peptide 1 receptors with efficacy in diabetic db/db mice", Proc Natl Acad Sci USA, 104(3):943-948.

Chen, J et al. (2017), "GLP-1/GLP-1R Signaling in Regulation of Adipocyte Differentiation and Lipogenesis", Cell Physiol Biochem, 42(3):1165-1176.

Dalsgaard N B et al. (2018), "Effects of glucagon-like peptide-1 receptor agonists on cardiovascular risk factors: A narrative review of head-to-head comparisons", Diabetes Obes Metab, 20(3):508-519.

Davies, M et al. (2017), "Effect of Oral Semaglutide Compared With Placebo and Subcutaneous Semaglutide on Glycemic Control in Patients With Type 2 Diabetes: A Randomized Clinical Trial", JAMA, 318(15):1460-1470.

De Graaf C et al. (2016), "Glucagon-Like Peptide-1 and Its Class B G Protein-Coupled Receptors: A Long March to Therapeutic Successes", Pharmacol Rev., 68(4):954-1013.

Donnelly K L et al. (2005), "Sources of fatty acids stored in liver and secreted via lipoproteins in patients with nonalcoholic fatty liver disease", J Clin Invest, 115(5):1343-1351.

Edmonds, D J et al. (2013), "Oral GLP-1 Modulators for the Treatment of Diabetes", Annual Reports in Medicinal Chemistry, Chapter Nine, 48:119-130.

Eguchi Y et al. (2015), "Pilot study of liraglutide effects in non-alcoholic steatohepatitis and non-alcoholic fatty liver disease with glucose intolerance in Japanese patients (LEAN-J)", Hepatol Res, 45(3):269-278.

Gastaldelli A et al. (2016), "Exenatide improves both hepatic and adipose tissue insulin resistance: A dynamic positron emission tomography study", Hepatology, 64(6):2028-2037.

Intl. Search Report—Written Opinion dated Jan. 21, 2021 for Intl. Appl. No. PCT/US2020/056867.

Jazayeri A et al. (2017), "Crystal structure of the GLP-1 receptor bound to a peptide agonist", Nature, 546(7657):254-258.

Jones, B et al. (2018), "Targeting GLP-1 receptor trafficking to improve agonist efficacy", Nature Communications, 9:1602, pp. 1-17.

(56) References Cited

OTHER PUBLICATIONS

Knudsen, L B et al. (2007), "Small-molecule agonists for the glucagon-like peptide 1 receptor", Proc Natl Acad Sci USA, 104(3):937-942.
Koole C et al. (2013), "Recent advances in understanding GLP-1R (glucagon-like peptide-1 receptor) function", Biochem Soc Trans, 41(1):172-179.
Ma H et al. (2020), "Structural insights into the activation of GLP-1R by a small molecule agonist", Cell Res 30, 1140-1142.
Mendez M et al. (2019), "Design, Synthesis and Pharmacological Evaluation of Potent Positive Allosteric Modulators of the Glucagon-like Peptide-1 Receptor (GLP-1R)", J. Med. Chem., Just Accepted Manuscript, Publication Date (Web): Oct. 9, 2019.
Nauck, M A et al. (2011), "Rapid tachyphylaxis of the glucagon-like peptide 1-induced deceleration of gastric emptying in humans", Diabetes, 60(5):1561-1565.
Nauck, M A et al. (2016), "A Phase 2, Randomized, Dose-Finding Study of the Novel Once-Weekly Human GLP-1 Analog, Semaglutide, Compared With Placebo and Open-Label Liraglutide in Patients With Type 2 Diabetes", Diabetes Care, 39(2):231-241.
Petit, J-M et al. (2017), "GLP-1 receptor agonists in NAFLD", Diabetes Metab., 43 Suppl 1:2S28-2S33.
Plisson F et al. (2017), "Helixconstraints and amino acid substitution in GLP-1 increase CAMP and insulin secretion but not beta-arrestin 2 signaling", Eur J Med Chem, 127:703-714.
Portillo-Sanchez P et al. (2016), "Treatment of Nonalcoholic Fatty Liver Disease (NAFLD) in patients with Type 2 Diabetes Mellitus", Clin Diabetes Endocrinol, 2:9.
Sloop K W et al. (2010), "Novel small molecule glucagon-like peptide-1 receptor agonist stimulates insulin secretion in rodents and from human islets", Diabetes, 59(12):3099-3107.
Song G et al. (2017), "Human GLP-1 receptor transmembrane domain structure in complex with allosteric modulators", Nature, 546(7657):312-315.
Svegliati-Baroni G et al. (2011), "Glucagon-like peptide-1 receptor activation stimulates hepatic lipid oxidation and restores hepatic signalling alteration induced by a high-fat diet in nonalcoholic steatohepatitis", Liver Int., 31(9):1285-1297.
Takayanagi R et al. (2018), "Evaluation of Drug Efficacy of GLP-1 Receptor Agonists and DPP-4 Inhibitors Based on Target Molecular Binding Occupancy", Biol Pharm Bull, 41(2):153-157.
Tong W et al. (2016), "Liraglutide ameliorates non-alcoholic fatty liver disease by enhancing mitochondrial architecture and promoting autophagy through the SIRT1/SIRT3-FOXO3a pathway", Hepatol Res., 46(9):933-943.
Umapathysivam M M et al. (2014), "Comparative effects of prolonged and intermittent stimulation of the glucagon-like peptide 1 receptor on gastric emptying and glycemia", Diabetes, 63(2):785-790.
Vendrell J et al. (2011), "Study of the potential association of adipose tissue GLP-1 receptor with obesity and insulin resistance", Endocrinology, 152(11):4072-4079.
Vilar-Gomez E et al. (2015), "Weight Loss Through Lifestyle Modification Significantly Reduces Features of Nonalcoholic Steatohepatitis", Gastroenterology, 149(2):367-378.e5.
Villanueva-Penacarrillo M L et al. (2001), "Effect of GLP-1 on lipid metabolism in human adipocytes", Horm Metab Res, 33(2):73-77.
VTv Therapeutics (2016), "Oral Small Molecule GLP-1 Receptor (GLP-1R) Agonists for Type 2 Diabetes (T2DM) with Negligible Nausea and Vomiting", Presentation from Keystone Symposia 2016.
Wang X-C et al. (2014), "Effects of glucagon-like peptide-1 receptor agonists on non-alcoholic fatty liver disease and inflammation", World J Gastroenterol, 20(40):14821-14830.
Wootten D et al. (2013), "Differential activation and modulation of the glucagon-like peptide-1 receptor by small molecule ligands", Mol Pharmacol, 83(4):822-834.
Wootten D et al. (2016), "A Hydrogen-Bonded Polar Network in the Core of the Glucagon-Like Peptide-1 Receptor Is a Fulcrum for Biased Agonism: Lessons from Class B Crystal Structures", Mol Pharmacol, 89(3):335-347.
Yang D et al. (2015), "Landmark studies on the glucagon subfamily of GPCRs: from small molecule modulators to a crystal structure", Acta Pharmacol Sin, 36(9):1033-42.
Intl. Preliminary Report on Patentability dated May 5, 2022 for Intl. Appl. No. PCT/US2020/056867.
Examination Report dated Aug. 25, 2022 for Indian Appl. No. 202217023266.
Notice of Opposition dated Sep. 8, 2022 for Colombian Appl. No. NC2022/0005077.
Notice of Allowance dated Sep. 26, 2022 for Taiwanese Appl. No. 109136833.
Examination Report dated Sep. 27, 2021 for Gulf Cooperation Council Appl. No. 40714.
Office Action dated Dec. 27, 2021 for Taiwanese Appl. No. 109136833.
Office Action dated Mar. 8, 2023 Australia Application No. 2020369568.
Office Action of May 8, 2023 for Japan Application No. 2022-523351.
Office Action of May 11, 2023 for Canada Application No. 3157525.
Office Action of Jun. 13, 2023 for Malaysia Application No. PI2022002017.
N. Foloppe, Potter, Bioorganic & Medicinal Chemistry, 2006, 14, 1792-1804.
Office Action and Search Report AP No. AP/P/2023/015172 Oct. 12, 2024.

* cited by examiner

GLP-1R MODULATING COMPOUNDS

CROSS REFERENCE TO RELATED APPLICATIONS

This application is a continuation of U.S. application Ser. No. 17/077,729, filed Oct. 22, 2020, which claims priority to U.S. Provisional Application No. 62/926,270, filed Oct. 25, 2019 and U.S. Provisional Application No. 63/028,187 filed May 21, 2020, all of which applications are incorporated herein in their entireties for all purposes.

FIELD

The present disclosure relates to compounds that bind to and act as agonists or modulators of the glucagon-like peptide-1 receptor (GLP-1R) and act as agonists or modulators of GLP-1R. The disclosure further relates to the use of the compounds for the treatment and/or prevention of diseases and/or conditions by said compounds.

BACKGROUND

Glucagon-like peptide-1 (GLP-1) is a peptide hormone that is secreted from the enteroendocrine cells in the gut in response to a meal. GLP-1 is believed to play a role in regulation of post-prandial glycemia, via directly augmenting meal-induced insulin secretion from the pancreatic beta-cells, as well as in promoting satiety by delaying the transit of food through the gut. GLP-1 mediates intracellular signaling via the GLP-1 receptor (GLP-1R) which belongs to a family of G-protein coupled receptors that are present on the cell membrane and can result in accumulation of the secondary messenger cyclic adenosine monophosphate (cAMP) upon activation. Non-alcoholic steatohepatitis (NASH) can be associated with features of metabolic syndrome, including obesity, type 2 diabetes, insulin resistance and cardiovascular disease.

GLP-1R agonists are currently being investigated in connection with diabetes, obesity, and NASH. GLP-1R agonists include peptides, such as exenatide, liraglutide, and dulaglutide, that have been approved for the management of type 2 diabetes. Such peptides are predominantly administered by subcutaneous injection. Oral GLP-1 agonists are also under investigation for treatment of type 2 diabetes. Some GLP-1R agonists, such as liraglutide, dulaglutide, and exenatide, are resistant to rapid degradation by dipeptidyl peptidase 4, resulting in longer half-lives than endogenous GLP-1.

There remains a need for compounds, such as agonists of GLP-1R, with desirable therapeutic properties, metabolic properties, and/or easy administration in the treatment of metabolic diseases and related diseases, including but not limited to NASH, obesity, and Type 2 diabetes.

SUMMARY

In one embodiment, the present disclosure provides a compound of Formula (I-A-1):

(I-A-1)

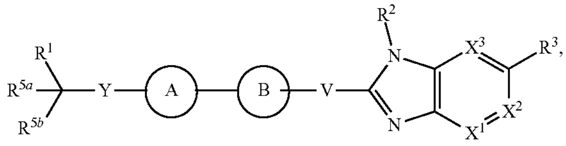

or a pharmaceutically acceptable salt thereof, wherein $R^1$ is $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, $—S—R^{1b}$, $—S(O)R^{1b}$, $—S(O)(NH)R^{1b}$, $—S(O)_2R^{1b}$, $—S(O)_2N(R^{1b})(R^{1c})$, $—S(O)(NR^{1b})R^{1c}$, $—C(O)N(R^{1b})(R^{1c})$, $—C(O)R^{1b}$, or $—C(O)OR^{1c}$, wherein the alkyl, haloalkyl, cycloalkyl, aryl, heteroaryl, or heterocyclyl is each optionally substituted with one to four $Z^1$;

ring A is $C_{6-10}$ aryl or heteroaryl, which is each optionally substituted with one to four $Z^{1a}$;

ring B is $C_{6-10}$ aryl or heteroaryl, which is each optionally substituted with one to four $R^4$;

$R^2$ is H, $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —CN, $—OR^{2a}$, $—S—R^{2a}$, $—S(O)R^{2a}$, $—S(O)(NH)R^{2a}$, $—S(O)_2R^{2a}$, $—S(O)_2N(R^{2a})(R^{2b})$, or $—S(O)(NR^{2a})R^{2b}$, wherein the alkyl, cycloalkyl, heterocyclyl, aryl, or heteroaryl is each optionally substituted with one to four $Z^1$;

$X^1$, $X^2$, and $X^3$ are each independently —N═, —C(H)═, or $—C(R^8)═$ $R^3$ is H, $C_{1-6}$ alkyl, $C_{1-6}$ haloalkyl, $C_{2-6}$alkenyl, $C_{2-6}$ alkynyl, halogen, $C_{3-10}$ cycloalkyl, heterocyclyl, $C_{6-10}$ aryl, heteroaryl, —CN, $—NO_2$, $—OR^{3a}$, $—C(O)R^{3a}$, $—CH_2C(O)OR^{3a}$, $—C(O)OR^{3a}$, $—C(O)N(R^{3a})(R^{3b})$, —N($R^{3a}$)C(O)$R^{3b}$, $—N(R^{3a})C(O)OR^{3b}$, $—N(R^{3a})C(O)N(R^{3b})_2$, $—C(O)NHS(O)_2R^{3a}$, $—C(O)NR^{3a}S(O)_2R^{3b}$, $—C(O)NR^{3a}S(O)_2NR^{3b}R^{3c}$, $—C(O)NR^{3a}—S(O)(═NR^{3b})R^{3c}$, $—S(O)_2R^{3a}$, $—S(O)_2OR^{3a}$, $—S(O)_2N(R^{3a})(R^{3b})$, $—N(R^{3a})S(O)_2R^{3b}$, $—S(O)_2NHC(O)R^{3a}$, $—S(O)(═NR^{3a})R^{3b}$, $—S(O)(═NR^{3a})NR^{3b}$, $—S(═NR^{3a})(═NR^{3b})R^{3c}$, $—P(O)(OR^{3a})(R^{3b})$, $—P(O)(OR^{3a})(OR^{3b})$, $—B(OR^{3a})(OR^{3b})$, or $—O—C_{1-6}$alkyl-C(O)$OR^{3a}$, wherein the alkyl, haloalkyl, alkenyl, alkynyl, cycloalkyl, heterocyclyl, aryl, or heteroaryl is each optionally substituted with one to four $R^{3d}$;

each $R^{3a}$, $R^{3b}$, and $R^{3c}$ is independently H, $C_{1-6}$ alkyl, $C_{1-6}$ haloalkyl, $C_{2-8}$ alkoxyalkyl, $—C_{1-4}$ alkyl-N($R^{9a}$)($R^{9b}$), $—C_{1-4}$ alkyl-N($R^{9a}$)C(O)—O—$C_{1-4}$ alkyl-OP(O)$(OR^{9c})_2$, $—C_{1-4}$ alkyl-C(O)N($R^{9a}$)($R^{9b}$), $—C_{1-4}$ alkyl-O—C(O)—$C_{1-4}$ alkyl, $—C_{1-4}$ alkyl-O—C(O)—O—$C_{1-4}$ alkyl, $—C_{1-4}$ alkyl-O—C(O)—$C_{1-4}$ alkyl-N($R^{9a}$)($R^{9b}$), $—C_{1-4}$ alkyl-O—C(O)—$C_{1-4}$ alkyl-OP(O)$(OR^{9c})_2$, $—C_{1-4}$ alkyl-$C_{3-8}$ cycloalkyl, $—C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, $—CH_2CH(N(R^{9a})_2)C(O)OR^{9b}$, $—P(O)(OR^{9c})_2$, $—OP(O)(OR^{9c})_2$, $—CH_2P(O)(OR^{9c})_2$, $—CH_2OP(O)(OR^{9c})_2$, $—OCH_2P(O)(OR^{9c})_2$, $—C(O)OCH_2P(O)(OR^{9c})_2$, $—P(O)(R^{9c})(OR^{9d})$, $—OP(O)(R^{9c})(OR^{9d})$, $—CH_2P(O)(R^{9c})(OR^{9d})$, $—OCH_2P(O)(R^{9c})(OR^{9d})$, $—C(O)OCH_2P(O)(R^{9c})(OR^{9d})$, $—P(O)(N(R^{9c})_2)_2$, $—OP(O)(N(R^{9c})_2)_2$, $—CH_2P(O)(N(R^{9c})_2)_2$, $—OCH_2P(O)(N(R^{9c})_2)_2$, $—C(O)OCH_2P(O)(N(R^{9c})_2)_2$, $—P(O)(N(R^{9c})_2)(OR^{9d})$, $—OP(O)(N(R^{9c})_2)(OR^{9d})$, $—CH_2P(O)(N(R^{9c})_2)(OR^{9d})$, $—OCH_2P(O)(N(R^{9c})_2)(OR^{9d})$, $—C(O)OCH_2P(O)(N(R^{9c})_2)(OR^{9d})$, $—P(O)(R^{9c})(N(R^{9d})_2)$, $—OP(O)(R^{9c})(N(R^{9d})_2)$, $—CH_2P(O)(R^{9c})(N(R^{9d})_2)$, $—OCH_2P(O)(R^{9c})(N(R^{9d})_2)$, $—C(O)OCH_2P(O)(R^{9c})(N(R^{9d})_2)$, or $C_{1-6}$ alkyl-heterocyclyl;

wherein the alkyl, alkenyl, cycloalkyl, heterocyclyl, aryl, or heteroaryl is each optionally substituted with one to four $Z^{1b}$, each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2R^{4a}$, —S(O)$_2$N($R^{4a}$)($R^{4b}$), —S(O)(N$R^{4a}$)$R^{4b}$, or —Si($R^{4a}$)$_3$;

wherein the alkyl, haloalkyl, alkenyl, alkynyl, cycloalkyl, heterocyclyl, aryl, or heteroaryl is each optionally substituted with one to four $Z^{1b}$;

or two $R^4$ groups attached to adjacent ring atoms are combined with the atoms to which they are attached to form a $C_{5-10}$ cycloalkyl or heterocyclyl, which is each optionally substituted with one to four $Z^{1b}$;

$R^{5a}$ and $R^{5b}$ are each independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{5a}$, or —N($R^{5a1}$)($R^{5a2}$);

or $R^{5a}$ and $R^{5b}$ are combined with the atoms to which they are attached to form a $C_{3-10}$ cycloalkyl or heterocyclyl, which is each optionally substituted with one to four $R^{5a3}$.

each $R^{5a1}$ and $R^{5a2}$ is independently H, $C_{1-6}$ alkyl, $C_{2-6}$ alkenyl, $C_{2-6}$ alkynyl, $C_{3-10}$ cycloalkyl, heterocyclyl, $C_{6-10}$ aryl, or heteroaryl, wherein the cycloalkyl, heterocyclyl, aryl, or heteroaryl is each optionally substituted with one to four $R^{5a4}$;

V is —C(O)—, —O—, —N($R^{6a}$)—, or —C($R^{6b}$)($R^{6c}$)—;

$R^{6a}$ is H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$) wherein the cycloalkyl or heterocyclyl is each optionally substituted with $C_{1-6}$ alkyl, F, or —CN;

each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{6c1}$, or —N($R^{6c2}$)($R^{6c3}$), wherein the alkyl, cycloalkyl, or heterocyclyl is each optionally substituted with one to four $R^{6b1}$;

or $R^{6b}$ and $R^{6c}$ are combined with the atom to which they are attached to form $C_{3-10}$ cycloalkyl or heterocyclyl, which is each optionally substituted with one to four $R^{6b1}$;

or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;

Y is —N($R^7$)—, —O—, —S—, —S(O)—, —S(O)$_2$—, —S(O)(=NH)—, or —S(O)(=N$R^7$)—;

each $R^{1a}$, $R^{3d}$, $R^{5a3}$, $R^{5a4}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, $CO_2R^{3e}$, —$NO_2$, or —C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, $R^{6c3}$ and $R^7$ is independently H, $C_{1-6}$ alkyl or $C_{3-10}$ cycloalkyl;

each $R^8$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, $CO_2R^{3e}$, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —$NH_2$, $CO_2H$—O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O ($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), $S(O)_2$($C_{1-9}$ alkyl), —$S(O)_2$($C_{1-8}$ haloalkyl), —$S(O)_2$($C_{3-15}$ cycloalkyl), —$S(O)_2$(heterocyclyl), —$S(O)_2$(aryl), —$S(O)_2$(heteroaryl), —S(O)(NH)($C_{1-9}$ alkyl), —$S(O)_2$NH($C_{1-9}$ alkyl), or —$S(O)_2$N($C_{1-9}$ alkyl)$_2$;

each $R^{9a}$ and $R^{9b}$ is independently H, $C_{1-6}$ alkyl, or $C_{1-6}$ haloalkyl, or $R^{9a}$ and $R^{9b}$ together form a 6-membered heterocyclyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —$N_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)$S(O)_2$($R^{12b}$), —N$R^{12a}$$S(O)_2$N($R^{12b}$)($R^{12c}$), —N$R^{12a}$$S(O)_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —$S(O)_2$$R^{12a}$, —$S(O)_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)$S(O)_2$($R^{12b}$), —N($R^{12a}$)$S(O)_2$—N($R^{12b}$)($R^{12c}$), —N($R^{12a}$)$S(O)_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —$S(O)_2$$R^{12a}$, —$S(O)_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1b}$;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, $CO_2R^{3e}$, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —$S(O)_2$($C_{1-9}$ alkyl), —$S(O)_2$($C_{1-8}$ haloalkyl), —$S(O)_2$($C_{2-6}$ alkenyl), —$S(O)_2$($C_{2-6}$ alkynyl), —$S(O)_2$($C_{3-15}$ cycloalkyl), —$S(O)_2$(heterocyclyl), —$S(O)_2$($C_{6-10}$ aryl), —$S(O)_2$(heteroaryl), —S(O)(NH)($C_{1-9}$ alkyl), —$S(O)_2$NH($C_{1-9}$ alkyl), or —$S(O)_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —$NH_2$, $CO_2H$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), $S(O)_2$($C_{1-9}$ alkyl), —$S(O)_2$($C_{1-8}$ haloalkyl), —$S(O)_2$($C_{3-15}$ cycloalkyl), —$S(O)_2$(heterocyclyl), —$S(O)_2$(aryl), —$S(O)_2$(heteroaryl), —S(O)(NH)($C_{1-9}$ alkyl), —$S(O)_2$NH($C_{1-9}$ alkyl), or —$S(O)_2$N($C_{1-9}$ alkyl)$_2$;

each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$; and each $R^{3e}$ is independently H, $C_{1-6}$ alkyl, $C_{1-6}$ haloalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{3-10}$ cycloalkyl, heterocyclyl, $C_{6-10}$ aryl, heteroaryl, $—P(O)(OR^{9c})_2$, $—CH_2P(O)(OR^{9c})_2$, $—OCH_2P(O)(OR^{9c})_2$, $—C(O)OCH_2P(O)(OR^{9c})_2$, $—P(O)(R^{9c})(OR^{9d})$, $—OP(O)(R^{9c})(OR^{9d})$, $—CH_2P(O)(R^{9c})(OR^{9d})$, $—C(O)OCH_2P(O)(R^{9c})(OR^{9d})$, $—P(O)(N(R^{9c})_2)_2$, $—CH_2P(O)(N(R^{9c})_2)_2$, $—C(O)OCH_2P(O)(N(R^{9c})_2)_2$, $—P(O)(N(R^{9c})_2)(OR^{9d})$, $—CH_2P(O)(N(R^{9c})_2)(OR^{9d})$, $—C(O)OCH_2P(O)(N(R^{9c})_2)(OR^{9d})$, $—P(O)(R^{9c})(N(R^{9d})_2)$, $—CH_2P(O)(R^{9c})(N(R^{9d})_2)$, or $—C(O)OCH_2P(O)(R^{9c})(N(R^{9d})_2)$; wherein the alkyl, alkenyl, cycloalkyl, heterocyclyl, aryl, or heteroaryl is each optionally substituted with one to four $Z^{1b}$; wherein each heteroaryl has 5 to 12 ring members and has one to four heteroatoms each independently N, O, or S; and wherein each heterocyclyl has 3 to 12 ring members and has one to four heteroatoms each independently N, O, or S.

The present disclosure further provides pharmaceutical compositions, methods, and uses comprising the compound of Formula (I), (I-A-1), (I-A-2), or pharmaceutically acceptable salts thereof. For example, the compounds of the present disclosure are generally useful in a method of treating a GLP-1R-mediated disease or condition.

DETAILED DESCRIPTION

I. Definitions

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or "$C_u$-$C_v$" indicates that the following group has from u to v carbon atoms, where u and v are integers. For example, "$C_{1-6}$ alkyl" or "$C_1$-$C_6$ alkyl" indicates that the alkyl group has from 1 to 6 carbon atoms.

"Alkyl" is a monovalent or divalent linear or branched saturated hydrocarbon radical. For example, an alkyl group can have 1 to 10 carbon atoms (i.e., $C_{1-10}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$, and octyl ($—(CH_2)_7CH_3$). Alkyl groups can be unsubstituted or substituted.

"Alkoxy" refers to the group —O-alkyl, where alkyl is as defined above. For example, $C_{1-4}$ alkoxy refers to an —O-alkyl group having 1 to 4 carbons. Alkoxy groups can be unsubstituted or substituted.

"Alkoxyalkyl" is an alkoxy group attached to an alkyl as defined above, such that the alkyl is divalent. For example, $C_{2-6}$ alkoxyalkyl includes $—CH_2—OMe$, $—CH_2—O\text{-iPr}$, $—CH_2—CH_2—OMe$, $—CH_2—CH_2—O—CH_2—CH_3$, and $—CH_2—CH_2—O\text{-tBu}$. Alkoxyalkyl groups can be unsubstituted or substituted.

"Alkenyl" is a monovalent or divalent linear or branched hydrocarbon radical with at least one carbon-carbon double bond. For example, an alkenyl group can have 2 to 8 carbon atoms (i.e., $C_{2-8}$ alkenyl) or 2 to 6 carbon atoms (i.e., $C_{2-6}$ alkenyl) or 2 to 4 carbon atoms (i.e., $C_{2-4}$ alkenyl). Examples of alkenyl groups include, but are not limited to, ethenyl ($—CH═CH_2$), allyl ($—CH_2CH═CH_2$), and $—CH_2—CH═CH—CH_3$. Alkenyl groups can be unsubstituted or substituted.

"Alkynyl" is a monovalent or divalent linear or branched hydrocarbon radical with at least one carbon-carbon triple bond. For example, an alkynyl group can have 2 to 8 carbon atoms (i.e., $C_{2-8}$ alkynyl) or 2 to 6 carbon atoms (i.e., $C_{2-6}$ alkynyl) or 2 to 4 carbon atoms (i.e., $C_{2-4}$ alkynyl). Examples of alkynyl groups include, but are not limited to, acetylenyl ($—C≡CH$), propargyl ($—CH_2C≡CH$), and $—CH_2—C≡C—CH_3$. Alkynyl groups can be unsubstituted or substituted.

"Halogen" refers to fluoro (—F), chloro (—Cl), bromo (—Br) and iodo (—I).

"Haloalkyl" is an alkyl as defined herein, wherein one or more hydrogen atoms of the alkyl are independently replaced by a halogen, which may be the same or different, such that the alkyl is divalent. The alkyl group and the halogen can be any of those described above. In some embodiments, the haloalkyl defines the number of carbon atoms in the alkyl portion, e.g., $C_{1-4}$ haloalkyl includes $CF_3$, $CH_2F$, $CHF_2$, $CH_2CF_3$, $CH_2CH_2CF_3$, $CCl_2CH_2CH_2CH_3$, and $C(CH_3)_2(CF_2H)$. Haloalkyl groups can be unsubstituted or substituted.

"Haloalkoxy" is an alkoxy as defined herein, wherein one or more hydrogen atoms of the alkyl in the alkyloxy are independently replaced by a halogen, which may be the same or different, such that the alkyl is divalent. The alkoxy group and the halogen can be any of those described above. In some embodiments, the haloalkoxy defines the number of carbon atoms in the alkyl portion, e.g., $C_{1-4}$ haloalkoxy includes $OCF_3$, $OCH_2F$, $OCH_2CF_3$, $OCH_2CH_2CF_3$, $OCCl_2CH_2CH_2CH_3$, and $OC(CH_3)_2(CF_2H)$. Haloalkoxy groups can be unsubstituted or substituted.

"Cycloalkyl" is a monovalent or divalent single all carbon ring or a multiple condensed all carbon ring system wherein the ring in each instance is a non-aromatic saturated or unsaturated ring. For example, in some embodiments, a cycloalkyl group has 3 to 12 carbon atoms, 3 to 10 carbon atoms, 3 to 8 carbon atoms, 3 to 6 carbon atoms, 3 to 5 carbon atoms, or 3 to 4 carbon atoms. Exemplary single ring cycloalkyl groups include cyclopropyl, cyclobutyl, cyclopentyl, cyclohexyl, cyclohexenyl, cycloheptyl, cycloheptenyl, and cyclooctyl. Cycloalkyl also includes multiple condensed ring systems (e.g., ring systems comprising 2 rings) having about 7 to 12 carbon atoms. The rings of the multiple condensed ring system can be connected to each other via fused, spiro, or bridged bonds when allowed by valency requirements. Exemplary multiple ring cycloalkyl groups include octahydropentalene, bicyclo[2.2.1]heptane, bicyclo

[2.2.2]octane, bicyclo[2.2.2]oct-2-ene, and spiro[2.5]octane. Cycloalkyl groups can be unsubstituted or substituted.

"Alkylcycloalkyl" refers to an alkyl as defined herein, wherein one or more hydrogen atoms of the alkyl are independently replaced by a cycloalkyl group, which may be the same or different. The alkyl group and the cycloalkyl group can be any of those described above. In some embodiments, the number of carbon atoms in the alkyl and cycloalkyl portion can be designated separately, e.g., $C_{1-6}$ alkyl-$C_{3-12}$ cycloalkyl. Alkylcycloalkyl groups can be unsubstituted or substituted.

"Aryl" as used herein refers to a monovalent or divalent single all carbon aromatic ring or a multiple condensed all carbon ring system wherein the ring is aromatic. For example, in some embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which multiple rings are aromatic. The rings of the multiple condensed ring system can be connected to each other via fused bonds when allowed by valency requirements. It is also understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl. Non-limiting examples of aryl groups include, but are not limited to, phenyl, naphthyl, anthracenyl, and the like. Aryl groups can be unsubstituted or substituted.

"Alkylaryl" refers to an alkyl as defined herein, wherein one or more hydrogen atoms of the alkyl are independently replaced by an aryl group, which may be the same or different. The alkyl group and the aryl group can be any of those described above, such that the alkyl is divalent. In some embodiments, an alkylaryl group has 7 to 24 carbon atoms, 7 to 16 carbon atoms, 7 to 13 carbon atoms, or 7 to 11 carbon atoms. An alkylaryl group defined by the number of carbon atoms refers to the total number of carbon atoms present in the constitutive alkyl and aryl groups combined. For example, $C_7$ alkylaryl refers to benzyl, while $C_{11}$ alkylaryl includes 1-methylnaphthyl and n-pentylphenyl. In some embodiments the number of carbon atoms in the alkyl and aryl portion can be designated separately, e.g., $C_{1-6}$ alkyl-$C_{6-10}$ aryl. Non-limiting examples of alkylaryl groups include, but are not limited to, benzyl, 2,2-dimethylphenyl, n-pentylphenyl, 1-methylnaphthyl, 2-ethylnaphthyl, and the like. Alkylaryl groups can be unsubstituted or substituted.

"Heterocyclyl" or "heterocycle" or "heterocycloalkyl" as used herein refers to a single saturated or partially unsaturated non-aromatic ring or a non-aromatic multiple ring system that has at least one heteroatom in the ring (i.e., at least one annular (i.e., ring-shaped) heteroatom selected from oxygen, nitrogen, and sulfur). Unless otherwise specified, a heterocyclyl group has from 3 to about 20 annular atoms, for example from 3 to 12 annular atoms, for example from 4 to 12 annular atoms, 4 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like. Heterocyclyl groups can be unsubstituted or substituted.

"Alkylheterocyclyl" refers to an alkyl as defined herein, wherein one or more hydrogen atoms of the alkyl are independently replaced by a heterocyclyl group, which may be the same or different. The alkyl group and the heterocyclyl group can be any of those described above, such that the alkyl is divalent. In some embodiments, the number of atoms in the alkyl and heterocyclyl portion can be designated separately, e.g., $C_{1-6}$ alkyl-3 to 12 membered heterocyclyl having one to three heteroatoms each independently N, O, or S. Alkylheterocyclyl groups can be unsubstituted or substituted.

"Heteroaryl" refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl) and aryls (to form, for example, benzimidazolyl or indazolyl) to form the multiple condensed ring system. Thus, a heteroaryl (a single aromatic ring or multiple condensed ring system) can have about 1-20 carbon atoms and about 1-6 heteroatoms within the heteroaryl ring. For example, tetrazolyl has 1 carbon atom and 4 nitrogen heteroatoms within the ring. The rings of the multiple condensed ring system can be connected to each other via fused bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. It is also to be understood that the rings of the multiple condensed ring system may include an aryl ring fused to a heterocyclic ring with saturated or partially unsaturated bonds (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. For example, a 5-membered heteroaryl includes thiazolyl and a 10-membered heteroaryl includes quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, benzofuranyl, benzimidazolyl, thianaphthenyl, pyrrolo[2,3-b]pyridinyl, quinazolinyl-4(3H)-one, triazolyl, and tetrazolyl. Heteroaryl groups can be unsubstituted or substituted.

"Alkylheteroaryl" refers to an alkyl as defined herein, wherein one or more hydrogen atoms of the alkyl are independently replaced by a heteroaryl group, which may be the same or different, such that the alkyl is divalent. The alkyl group and the heteroaryl group can be any of those described above. In some embodiments, the number of atoms in the alkyl and heteroaryl portion are designated separately, e.g., $C_{1-6}$ alkyl-5 to 10 membered heteroaryl having one to four heteroatoms each independently N, O, or S. Alkylheteroaryl groups can be unsubstituted or substituted.

"Oxo" as used herein refers to =O.

"Substituted" as used herein refers to wherein one or more hydrogen atoms of the group are independently replaced by one or more substituents (e.g., 1, 2, 3, or 4 or more) as indicated.

A "compound of the present disclosure" includes compounds disclosed herein, for example a compound of the present disclosure includes compounds of Formula (I), (Ia), (Ib), (Ic), and (Id), including the compounds of the Examples. In some embodiments, a "compound of the present disclosure" includes compounds of Formula (I-A-1), (I-A-2), (I), (Ia), (Ib), (Ib-1), (Ic), and (Id).

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Therapeutically effective amount" or "effective amount" as used herein refers to an amount that is effective to elicit the desired biological or medical response, including the amount of a compound that, when administered to a subject for treating a disease, is sufficient to affect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the subject.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $N(C_1 \equiv C_4\ alkyl)_4^+$. Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$ $^{31}P$, $^{32}P$, $^{35}S$, $^{18}F$, $^{36}Cl$, $^{123}I$ and $^{125}I$ respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I-A-1) and/or (I) can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Stereoisomer" as used herein refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Tautomer" as used herein refers to a proton shift from one atom of a molecule to another atom of the same molecule. In some embodiments, the present disclosure includes tautomers of said compounds.

"Solvate" as used herein refers to the result of the interaction of a solvent and a compound. Solvates of salts of the compounds described herein are also provided. Hydrates of the compounds described herein are also provided.

"Hydrate" as used herein refers to a compound of the disclosure that is chemically associated with one or more molecules of water.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Prodrug" as used herein refers to a derivative of a drug that upon administration to the human body is converted to the parent drug according to some chemical or enzymatic pathway. In some embodiments, a prodrug is a biologically inactive derivative of a drug that upon administration to the human body is converted to the biologically active parent drug according to some chemical or enzymatic pathway.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival. "At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

II. Compounds

In some embodiments, the compound of the present disclosure is a compound of Formula (I-A-1):

(I-A-1)

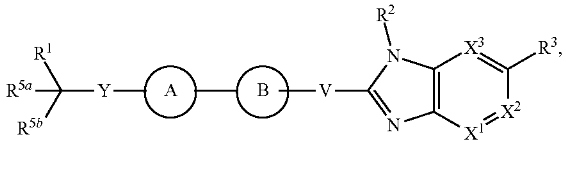

or a pharmaceutically acceptable salt thereof, wherein $R^1$ is $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{1b}$, —S(O)$R^{1b}$, —S(O)(NH)$R^{1b}$, —S(O)$_2R^{1b}$, —S(O)$_2$N($R^{1b}$)($R^{1c}$), —S(O)(N$R^{1b}$)$R^{1c}$, —C(O)N($R^{1b}$)($R^{1c}$), —C(O)$R^{1b}$, or —C(O)ORIC, wherein the alkyl, haloalkyl, cycloalkyl, aryl, heteroaryl, or heterocyclyl is each optionally substituted with one to four $Z^1$;

ring A is $C_{6-10}$ aryl or heteroaryl, which is each optionally substituted with one to four $Z^{1a}$;

ring B is $C_{6-10}$ aryl or heteroaryl, which is each optionally substituted with one to four $R^4$;

$R^2$ is H, $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —CN, —O$R^{2a}$, —S—$R^{2a}$, —S(O)$R^{2a}$, —S(O)(NH)$R^{2a}$, —S(O)$_2R^{2a}$, —S(O)$_2$N($R^{2a}$)($R^{2b}$), or —S(O)(N$R^{2a}$)$R^{2b}$, wherein the alkyl, cycloalkyl, heterocyclyl, aryl, or heteroaryl is each optionally substituted with one to four $Z^1$;

$X^1$, $X^2$, and $X^3$ are each independently —N═, —C(H)═, or —C($R^8$)═

$R^3$ is H, $C_{1-6}$ alkyl, $C_{1-6}$ haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —$NO_2$, —O$R^{3a}$, —C(O)$R^{3a}$, —$CH_2$C(O)O$R^{3a}$, —C(O)O$R^{3a}$, —C(O)N($R^{3a}$)($R^{3b}$), —N($R^{3a}$)C(O)$R^{3b}$, —N($R^{3a}$)C(O)O$R^{3b}$, —N($R^{3a}$)C(O)N($R^{3b}$)$_2$, —C(O)NHS(O)$_2R^{3a}$, —C(O)N$R^{3a}$S(O)$_2R^{3b}$, —C(O)N$R^{3a}$S(O)$_2$N$R^{3b}R^{3c}$, —C(O)N$R^{3a}$—S(O)(═N$R^{3b}$)$R^{3c}$, —S(O)$_2R^{3a}$, —S(O)$_2$O$R^{3a}$, —S(O)$_2$N($R^{3a}$)($R^{3b}$), —N($R^{3a}$)S(O)$_2R^{3b}$, —S(O)$_2$NHC(O)$R^{3a}$, —S(O)(═N$R^{3a}$)$R^{3b}$, —S(O)(═N$R^{3a}$)N$R^{3b}$, —S(═N$R^{3a}$)(═N$R^{3b}$)$R^{3c}$, —P(O)(O$R^{3a}$)($R^{3b}$), —P(O)(O$R^{3a}$)(O$R^{3b}$), —B(O$R^{3a}$)(O$R^{3b}$), or —O—$C_{1-6}$alkyl-C(O)O$R^{3a}$, wherein the alkyl, haloalkyl, alkenyl, alkynyl, cycloalkyl, heterocyclyl, aryl, or heteroaryl is each optionally substituted with one to four $R^{3d}$;

each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-N($R^{9a}$)C(O)—O—$C_{1-4}$ alkyl-OP(O)(O$R^{9c}$)$_2$, —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$ alkyl, —$C_{1-4}$ alkyl-O—C(O)—$C_{1-4}$ alkyl-N($R^{9a}$)($R^{9b}$), —$C_{1-4}$ alkyl-O—C(O)—$C_{1-4}$ alkyl-OP(O)(O$R^{9c}$)$_2$, —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, —$CH_2$CH(N($R^{9a}$)$_2$)C(O)O$R^{9b}$, —P(O)(O$R^{9c}$)$_2$, —OP(O)(O$R^{9c}$)$_2$, —$CH_2$P(O)(O$R^{9c}$)$_2$, —$CH_2$OP(O)(O$R^{9c}$)$_2$, —O$CH_2$P(O)(O$R^{9c}$)$_2$, —C(O)O$CH_2$P(O)(O$R^{9c}$)$_2$, —P(O)($R^{9c}$)(O$R^{9d}$), —OP(O)($R^{9c}$)(O$R^{9d}$), —$CH_2$P(O)($R^{9c}$)(O$R^{9d}$), —O$CH_2$P(O)($R^{9c}$)(O$R^{9d}$), —C(O)O$CH_2$P(O)($R^{9c}$)(O$R^{9d}$), —P(O)(N($R^{9c}$)$_2$)$_2$, —OP(O)(N($R^{9c}$)$_2$)$_2$, —$CH_2$P(O)(N($R^{9c}$)$_2$)$_2$, —O$CH_2$P(O)(N($R^{9c}$)$_2$)$_2$, —C(O)O$CH_2$P(O)(N($R^{9c}$)$_2$)$_2$, —P(O)(N($R^{9c}$)$_2$)(O$R^{9d}$), —OP(O)(N($R^{9c}$)$_2$)(O$R^{9d}$), —$CH_2$P(O)(N($R^{9c}$)$_2$)(O$R^{9d}$), —O$CH_2$P(O)(N($R^{9c}$)$_2$)(O$R^{9d}$), —C(O)O$CH_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —$CH_2$P(O)($R^{9c}$)(N($R^{9d}$)$_2$), —O$CH_2$P(O)($R^{9c}$)(N($R^{9d}$)$_2$), —C(O)O$CH_2$P(O)($R^{9c}$)(N($R^{9d}$)$_2$), or $C_{1-6}$ alkyl-heterocyclyl;

wherein the alkyl, alkenyl, cycloalkyl, heterocyclyl, aryl, or heteroaryl is each optionally substituted with one to four $Z^{1b}$, each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2R^{4a}$, —S(O)$_2$N($R^{4a}$)($R^{4b}$), —S(O)(N$R^{4a}$)$R^{4b}$, or —Si($R^{4a}$)$_3$;

wherein the alkyl, haloalkyl, alkenyl, alkynyl, cycloalkyl, heterocyclyl, aryl, or heteroaryl is each optionally substituted with one to four $Z^{1b}$;

or two $R^4$ groups attached to adjacent ring atoms are combined with the atoms to which they are attached to form a $C_{5-10}$ cycloalkyl or heterocyclyl, which is each optionally substituted with one to four $Z^{1b}$;

$R^{5a}$ and $R^{5b}$ are each independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{5a}$, or —N($R^{5a1}$)($R^{5a2}$).

or $R^{5a}$ and $R^{5b}$ are combined with the atoms to which they are attached to form a $C_{3-10}$ cycloalkyl or heterocyclyl, which is each optionally substituted with one to four $R^{5a3}$;

each $R^{5a1}$ and $R^{5a2}$ is independently H, $C_{1-6}$ alkyl, $C_{2-6}$ alkenyl, $C_{2-6}$ alkynyl, $C_{3-10}$ cycloalkyl, heterocyclyl, $C_{6-10}$ aryl, or heteroaryl, wherein the cycloalkyl, heterocyclyl, aryl, or heteroaryl is each optionally substituted with one to four $R^{5a4}$;

V is —C(O)—, —O—, —N($R^{6a}$)—, or —C($R^{6b}$)($R^{6c}$)—;

$R^{6a}$ is H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the cycloalkyl or heterocyclyl is each optionally substituted with $C_{1-6}$ alkyl, F, or —CN;

each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{6c1}$, or —N($R^{6c2}$)($R^{6c3}$), wherein the alkyl, cycloalkyl, or heterocyclyl is each optionally substituted with one to four $R^{6b1}$;

or $R^{6b}$ and $R^{6c}$ are combined with the atom to which they are attached to form $C_{3-10}$ cycloalkyl or heterocyclyl, which is each optionally substituted with one to four $R^{6b1}$;

or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;

Y is —N($R^7$)—, —O—, —S—, —S(O)—, —S(O)$_2$—, —S(O)(═NH)—, or —S(O)(═N$R^7$)—;

each $R^{1a}$, $R^{3d}$, $R^{5a3}$, $R^{5a4}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, $CO_2R^{3e}$, —$NO_2$, or —C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, $R^{6c3}$ and $R^7$ is independently H, $C_{1-6}$ alkyl or $C_{3-10}$ cycloalkyl;

each $R^8$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, $CO_2R^{3e}$, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —$NH_2$, $CO_2$H—O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

each $R^{9a}$ and $R^{9b}$ is independently H, $C_{1-6}$ alkyl, or $C_{1-6}$ haloalkyl, or $R^{9a}$ and $R^{9b}$ together form a 6-membered heterocyclyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —$N_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$ ($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$ wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$ wherein the alkyl, haloalkyl, alkenyl, alkynyl, cycloalkyl, heterocyclyl, aryl, or heteroaryl is each optionally substituted with one to four $Z^{1b}$;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, $CO_2R^{3e}$, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)

O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —$NH_2$, $CO_2H$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$; and each $R^{3e}$ is independently H, $C_{1-6}$ alkyl, $C_{1-6}$ haloalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$ alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{3-10}$ cycloalkyl, heterocyclyl, $C_{6-10}$ aryl, heteroaryl, —P(O)($OR^{9c}$)$_2$, —$CH_2$P(O)($OR^{9c}$)$_2$, —$OCH_2$P(O)($OR^{9c}$)$_2$, —C(O)$OCH_2$P(O)($OR^{9c}$)$_2$, —P(O)($R^{9c}$)($OR^{9d}$), —OP(O)($R^{9c}$)($OR^{9d}$), —$CH_2$P(O)($R^{9c}$)($OR^{9d}$), —C(O)$OCH_2$P(O)($R^{9c}$)($OR^{9d}$), —P(O)(N($R^{9c}$)$_2$)$_2$, —$CH_2$P(O)(N($R^{9c}$)$_2$)$_2$, —C(O)$OCH_2$P(O)(N($R^{9c}$)$_2$)$_2$, —P(O)(N($R^{9c}$)$_2$)($OR^{9d}$), —$CH_2$P(O)(N($R^{9c}$)$_2$)($OR^{9d}$), —C(O)$OCH_2$P(O)(N($R^{9c}$)$_2$)($OR^{9d}$), —P(O)($R^{9c}$)(N($R^{9d}$)$_2$), —$CH_2$P(O)($R^{9c}$)(N($R^{9d}$)$_2$), or —C(O)$OCH_2$P(O)($R^{9c}$)(N($R^{9d}$)$_2$); wherein the alkyl, alkenyl, cycloalkyl, heterocyclyl, aryl, or heteroaryl is each optionally substituted with one to four $Z^{1b}$; wherein each heteroaryl has 5 to 12 ring members and has one to four heteroatoms each independently N, O, or S; and wherein each heterocyclyl has 3 to 12 ring members and has one to four heteroatoms each independently N, O, or S.

In some embodiments, the compound of the present disclosure is a compound of Formula (I-A-1):

(I-A-1)

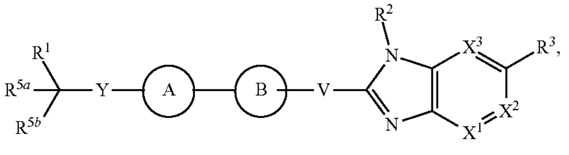

or a pharmaceutically acceptable salt thereof, wherein $R^1$ is $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{1b}$, —S(O)$R^{1b}$, —S(O)(NH)$R^{1b}$, —S(O)$_2R^{1b}$, —S(O)$_2$N($R^{1b}$)($R^{1c}$), —S(O)($NR^{1b}$)$R^{1c}$, —C(O)N($R^{1b}$)($R^{1c}$), —C(O)$R^{1b}$, or —C(O)$OR^{1c}$, wherein the alkyl, haloalkyl, cycloalkyl, aryl, heteroaryl, or heterocyclyl is each optionally substituted with one to four $Z^1$;

ring A is $C_{6-10}$ aryl or heteroaryl, which is each optionally substituted with one to four $Z^{1a}$;

ring B is $C_{6-10}$ aryl or heteroaryl, which is each optionally substituted with one to four $R^4$;

$R^2$ is H, $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —CN, —$OR^{2a}$, —S—$R^{2a}$, —S(O)$R^{2a}$, —S(O)(NH)$R^{2a}$, —S(O)$_2R^{2a}$, —S(O)$_2$N($R^{2a}$)($R^{2b}$), or —S(O)($NR^{2a}$)$R^{2b}$, wherein the alkyl, cycloalkyl, heterocyclyl, aryl, or heteroaryl is each optionally substituted with one to four $Z^1$;

$X^1$, $X^2$, and $X^3$ are each independently —N=, —C(H)=, or —C($R^8$)=

$R^3$ is H, $C_{1-6}$ alkyl, $C_{1-6}$ haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —$NO_2$, —$OR^{3a}$, —C(O)$R^{3a}$, —C(O)$OR^{3a}$, —C(O)N($R^{3a}$)($R^{3b}$), —N($R^{3a}$)C(O)$R^{3b}$, —N($R^{3a}$)C(O)$OR^{3b}$, —N($R^{3a}$)C(O)N($R^{3b}$)$_2$, —C(O)NHS(O)$_2R^{3a}$, —C(O)$NR^{3a}$S(O)$_2R^{3b}$, —C(O)$NR^{3a}$S(O)$_2NR^{3b}R^{3c}$, —C(O)$NR^{3a}$—S(O)(=$NR^{3b}$)$R^{3c}$, —S(O)$_2R^{3a}$, —S(O)$_2OR^{3a}$, —S(O)$_2$N($R^{3a}$)($R^{3b}$), —N($R^{3a}$)S(O)$_2R^{3b}$, —S(O)$_2$NHC(O)$R^{3a}$, —S(O)(=$NR^{3a}$)$R^{3b}$, —S(O)(=$NR^{3a}$)$NR^{3b}$, —S(=$NR^{3a}$)(=$NR^{3b}$)$R^{3c}$, —P(O)($OR^{3a}$)($R^{3b}$), —P(O)($OR^{3a}$)($OR^{3b}$), or —B($OR^{3a}$)($OR^{3b}$), wherein the alkyl, haloalkyl, alkenyl, alkynyl, cycloalkyl, heterocyclyl, aryl, or heteroaryl is each optionally substituted with one to four $R^{3d}$;

each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, —P(O)($OR^{9c}$)$_2$, —OP(O)($OR^{9c}$)$_2$, —$CH_2$P(O)($OR^{9c}$)$_2$, —$OCH_2$P(O)($OR^{9c}$)$_2$, —C(O)$OCH_2$P(O)($OR^{9c}$)$_2$, —P(O)($R^{9c}$)($OR^{9d}$), —OP(O)($R^{9c}$)($OR^{9d}$), —$CH_2$P(O)($R^{9c}$)($OR^{9d}$), —$OCH_2$P(O)($R^{9c}$)($OR^{9d}$), —C(O)$OCH_2$P(O)($R^{9c}$)($OR^{9d}$), —P(O)(N($R^{9c}$)$_2$)$_2$, —OP(O)(N($R^{9c}$)$_2$)$_2$, —$CH_2$P(O)(N($R^{9c}$)$_2$)$_2$, —$OCH_2$P(O)(N($R^{9c}$)$_2$)$_2$, —C(O)$OCH_2$P(O)(N($R^{9c}$)$_2$)$_2$, —P(O)(N($R^{9c}$)$_2$)($OR^{9d}$), —OP(O)(N($R^{9c}$)$_2$)($OR^{9d}$), —$CH_2$P(O)(N($R^{9c}$)$_2$)($OR^{9d}$), —$OCH_2$P(O)(N($R^{9c}$)$_2$)($OR^{9d}$), —C(O)$OCH_2$P(O)(N($R^{9c}$)$_2$)($OR^{9d}$), —P(O)($R^{9c}$)(N($R^{9d}$)$_2$), —OP(O)($R^{9c}$)(N($R^{9d}$)$_2$), —$CH_2$P(O)($R^{9c}$)(N($R^{9d}$)$_2$), —$OCH_2$P(O)($R^{9c}$)(N($R^{9d}$)$_2$), or —C(O)$OCH_2$P(O)($R^{9c}$)(N($R^{9d}$)$_2$);

wherein the alkyl, alkenyl, cycloalkyl, heterocyclyl, aryl, or heteroaryl is each optionally substituted with one to four $Z^{1b}$, each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2R^{4a}$, —S(O)$_2$N($R^{4a}$)($R^{4b}$), —S(O)(N$R^{4a}$)$R^{4b}$, or —Si($R^{4a}$)$_3$;

wherein the alkyl, haloalkyl, alkenyl, alkynyl, cycloalkyl, heterocyclyl, aryl, or heteroaryl is each optionally substituted with one to four $Z^{1b}$;

or two $R^4$ groups attached to adjacent ring atoms are combined with the atoms to which they are attached to form a $C_{5-10}$ cycloalkyl or heterocyclyl, which is each optionally substituted with one to four $Z^{1b}$;

$R^{5a}$ and $R^{5b}$ are each independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —$OR^{5a}$, or —N($R^{5a1}$)($R^{5a2}$);

or $R^{5a}$ and $R^{5b}$ are combined with the atoms to which they are attached to form a $C_{3-10}$ cycloalkyl or heterocyclyl, which is each optionally substituted with one to four $R^{5a3}$;

each $R^{5a1}$ and $R^{5a2}$ is independently H, $C_{1-6}$ alkyl, $C_{2-6}$ alkenyl, $C_{2-6}$ alkynyl, $C_{3-10}$ cycloalkyl, heterocyclyl, $C_{6-10}$ aryl, or heteroaryl, wherein the cycloalkyl, heterocyclyl, aryl, or heteroaryl is each optionally substituted with one to four $R^{5a4}$;

V is —C(O)—, —O—, —N($R^{6a}$)—, or —C($R^{6b}$)($R^{6c}$)—;

$R^{6a}$ is H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the cycloalkyl or heterocyclyl is each optionally substituted with $C_{1-6}$ alkyl, F, or —CN;

each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —$OR^{6c}$, or —N($R^{6c2}$)($R^{6c3}$), wherein the alkyl, cycloalkyl, or heterocyclyl is each optionally substituted with one to four $R^{6b1}$;

or $R^{6b}$ and $R^{6c}$ are combined with the atom to which they are attached to form $C_{3-10}$ cycloalkyl or heterocyclyl, which is each optionally substituted with one to four $R^{6b1}$;

or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;

Y is —N($R^7$)—, —O—, —S—, —S(O)—, —S(O)$_2$—, —S(O)(=NH)—, or —S(O)(=N$R^7$)—;

each $R^{1a}$, $R^{3d}$, $R^{5a3}$, $R^{5a4}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, $CO_2R^{3e}$, —$NO_2$, or —C(O)N($R^{2a}$)($R^{2b}$)

wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, $R^{6c3}$ and $R^7$ is independently H, $C_{1-6}$ alkyl or $C_{3-10}$ cycloalkyl;

each $R^8$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, $CO_2R^{3e}$, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S (O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —NH$_2$, CO$_2$H—O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

each $R^{9a}$ and $R^{9b}$ is independently H, $C_{1-6}$ alkyl, or $C_{1-6}$ haloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$ wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1b}$;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, CO$_2R^{3e}$, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —NH$_2$, CO$_2$H, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$; and each $R^{3e}$ is independently H, $C_{1-6}$ alkyl, $C_{1-6}$ haloalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$ alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{3-10}$ cycloalkyl, heterocyclyl, $C_{6-10}$ aryl, heteroaryl, —P(O)(OR$^{9c}$)$_2$, —CH$_2$P(O)(OR$^{9c}$)$_2$, —OCH$_2$P(O)(OR$^{9c}$)$_2$, —C(O)OCH$_2$P(O)(OR$^{9c}$)$_2$, —P(O)($R^{9c}$)(OR$^{9d}$), —OP(O)($R^{9c}$)(OR$^{9d}$), —CH$_2$P(O)($R^{9c}$)(OR$^{9d}$), —C(O)OCH$_2$P(O)($R^{9c}$)(OR$^{9d}$), —P(O)(N($R^{9c}$)$_2$)$_2$, —CH$_2$P(O)(N($R^{9c}$)$_2$)$_2$, —C(O)OCH$_2$P(O)(N($R^{9c}$)$_2$)$_2$, —P(O)(N($R^{9c}$)$_2$)(OR$^{9d}$), —CH$_2$P(O)(N($R^{9c}$)$_2$)(OR$^{9d}$), —C(O)OCH$_2$P(O)(N($R^{9c}$)$_2$)(OR$^{9d}$), —P(O)($R^{9c}$)(N($R^{9d}$)$_2$), CH$_2$P(O)($R^{9c}$)(N($R^{9d}$)$_2$), or —C(O)OCH$_2$P(O)($R^{9c}$)(N($R^{9d}$)$_2$); wherein the alkyl, alkenyl, cycloalkyl, heterocyclyl, aryl, or heteroaryl is each optionally substituted with one to four $Z^{1b}$; wherein each heteroaryl has 5 to 12 ring members and has one to four heteroatoms each independently N, O, or S; and wherein each heterocyclyl has 3 to 12 ring members and has one to four heteroatoms each independently N, O, or S.

In some embodiments, the compound of the present disclosure is a compound of Formula (I):

(I)

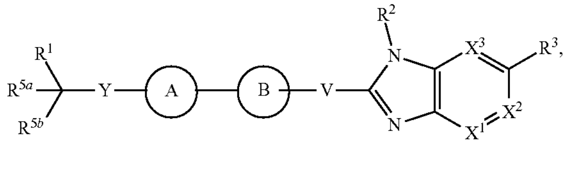

or a pharmaceutically acceptable salt thereof, wherein $R^1$ is $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{1b}$, —S(O)$R^{1b}$, —S(O)(NH)$R^{1b}$, —S(O)$_2$$R^{1b}$, —S(O)$_2$N($R^{1b}$)($R^{1c}$), —S(O)(N$R^{1b}$)$R^{1c}$, —C(O)N($R^{1b}$)($R^{1c}$), —C(O)$R^{1b}$, or —C(O)OR$^{1c}$, wherein the alkyl, haloalkyl, cycloalkyl, aryl, heteroaryl, or heterocyclyl is each optionally substituted with one to four $Z^1$;

ring A is $C_{6-10}$ aryl or heteroaryl, which is each optionally substituted with one to four $Z^{1a}$;

ring B is $C_{6-10}$ aryl or heteroaryl, which is each optionally substituted with one to four $R^4$;

$R^2$ is H, $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —CN, —OR$^{2a}$, —S—$R^{2a}$, —S(O)$R^{2a}$, —S(O)(NH)$R^{2a}$, —S(O)$_2$$R^{2a}$, —S(O)$_2$N($R^{2a}$)($R^{2b}$), or —S(O)(NR$^{2a}$)$R^{2b}$, wherein the alkyl, cycloalkyl, heterocyclyl, aryl, or heteroaryl is each optionally substituted with one to four $Z^1$;

$X^1$, $X^2$, and $X^3$ are each independently —N═, —C(H)═, or —C($R^8$)═;

$R^3$ is H, $C_{1-6}$ alkyl, $C_{1-6}$ haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —NO$_2$, —OR$^{3a}$, —C(O)$R^{3a}$, —C(O)OR$^{3a}$, —C(O)N($R^{3a}$)($R^{3b}$), —N($R^{3a}$)C(O)$R^{3b}$, —N($R^{3a}$)C(O)OR$^{3b}$, —N($R^{3a}$)C(O)N($R^{3b}$)$_2$, —C(O)NHS(O)$_2$$R^{3a}$, —C(O)NR$^{3a}$S(O)$_2$$R^{3b}$, —C(O)NR$^{3a}$S(O)$_2$NR$^{3b}$$R^{3c}$, —C(O)NR$^{3a}$—S(O)(═NR$^{3b}$)$R^{3c}$—S(O)$_2$$R^{3a}$, —S(O)$_2$OR$^{3a}$, —S(O)$_2$N($R^{3a}$)($R^{3b}$), —N($R^{3a}$)S(O)$_2$$R^{3b}$, —S(O)$_2$NHC(O)$R^{3a}$, —S(O)(═NR$^{3a}$)$R^{3b}$, —S(O)(═NR$^{3a}$)NR$^{3b}$, —S(═NR$^{3a}$)(═NR$^{3b}$)$R^{3c}$, —P(O)(OR$^{3a}$)($R^{3b}$), —P(O)(OR$^{3a}$)(OR$^{3b}$), or —B(OR$^{3a}$)(OR$^{3b}$), wherein the alkyl, haloalkyl, alkenyl, alkynyl, cycloalkyl, heterocyclyl, aryl, or heteroaryl is each optionally substituted with one to four $R^{3d}$;

each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, —P(O)(OR$^{9c}$)$_2$, —OP(O)(OR$^{9c}$)$_2$, —CH$_2$P(O)(OR$^{9c}$)$_2$, —OCH$_2$P(O)(OR$^{9c}$)$_2$, —C(O)OCH$_2$P(O)(OR$^{9c}$)$_2$, —P(O)($R^{9c}$)(OR$^{9d}$), —OP(O)($R^{9c}$)(OR$^{9d}$), —CH$_2$P(O)($R^{9c}$)(OR$^{9d}$), —OCH$_2$P(O)($R^{9c}$)(OR$^{9d}$), —C(O)OCH$_2$P(O)($R^{9c}$)(OR$^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$)(OR$^{9d}$), —OP(O)(N($R^{9c}$)$_2$)(OR$^{9d}$), —CH$_2$P(O)(N($R^{9c}$)$_2$)(OR$^{9d}$), —OCH$_2$P(O)(N($R^{9c}$)$_2$)(OR$^{9d}$), —C(O)OCH$_2$P(O)(N($R^{9c}$)$_2$)(OR$^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), or —C(O)OCH$_2$P(O)($R^{9c}$)(N($R^{9d}$)$_2$);

wherein the alkyl, alkenyl, cycloalkyl, heterocyclyl, aryl, or heteroaryl is each optionally substituted with one to four $Z^{1b}$;

each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)+, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)OR$^{4a}$, —OC(O)—N($R^{4a}$)($R^{4b}$), —S—$R^{4a}$, —S(O)$R^{4a}$, —S(O)(NH)$R^{4a}$, —S(O)$_2$$R^{4a}$, —S(O)$_2$N($R^{4a}$)($R^{4b}$), —S(O)(NR$^{4a}$)$R^{4b}$, or —Si($R^{4a}$)$_3$;

wherein the alkyl, haloalkyl, alkenyl, alkynyl, cycloalkyl, heterocyclyl, aryl, or heteroaryl is each optionally substituted with one to four $Z^{1b}$;

or two $R^4$ groups attached to adjacent ring atoms are combined with the atoms to which they are attached to form a $C_{5-10}$ cycloalkyl or heterocyclyl, which is each optionally substituted with one to four $Z^{1b}$;

$R^{5a}$ and $R^{5b}$ are each independently H, $C_{1-6}$ alkyl, $C_{1-6}$ haloalkyl, $C_{2-6}$ alkoxyalkyl, halogen, $C_{3-10}$ cycloalkyl, heterocyclyl, —CN, —$OR^{5a}$, or —$N(R^{5a1})(R^{5a2})$;

or $R^{5a}$ and $R^{5b}$ are combined with the atoms to which they are attached to form a $C_{3-10}$ cycloalkyl or heterocyclyl, which is each optionally substituted with one to four $R^{5a3}$;

each $R^{5a1}$ and $R^{5a2}$ is independently H, $C_{1-6}$ alkyl, $C_{2-6}$ alkenyl, $C_{2-6}$ alkynyl, $C_{3-10}$ cycloalkyl, heterocyclyl, $C_{6-10}$ aryl, or heteroaryl, wherein the cycloalkyl, heterocyclyl, aryl, or heteroaryl is each optionally substituted with one to four $R^{5a4}$;

V is —C(O)—, —O—, —$N(R^{6a})$—, or —$C(R^{6b})(R^{6c})$—

$R^{6a}$ is H, $C_{1-6}$ alkyl, $C_{3-10}$ cycloalkyl, heterocyclyl, —$S(O)_2R^{6a1}$, or —$S(O)_2N(R^{6a1})(NR^{6a2})$, wherein the cycloalkyl or heterocyclyl is each optionally substituted with $C_{1-6}$ alkyl, F, or —CN;

each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —CN, —$OR^{6c}$, or —$N(R^{6c2})(R^{6c3})$, wherein the alkyl, cycloalkyl, or heterocyclyl is each optionally substituted with one to four $R^{6b1}$;

or $R^{6b}$ and $R^{6c}$ are combined with the atom to which they are attached to form $C_{3-10}$ cycloalkyl or heterocyclyl, which is each optionally substituted with one to four $R^{6b1}$;

or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;

Y is —$N(R^7)$—, —O—, —S—, —S(O)—, —$S(O)_2$—, —S(O)(=NH)—, or —$S(O)(=NR^7)$—;

each $R^{1a}$, $R^{3d}$, $R^{5a3}$, $R^{5a4}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —$NO_2$, or —$C(O)N(R^{2a})(R^{2b})$, wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, $R^{6c3}$ and $R^7$ is independently H, $C_{1-6}$ alkyl or $C_{3-10}$ cycloalkyl;

each $R^{9a}$ and $R^{9b}$ is independently H, $C_{1-6}$ alkyl, or $C_{1-6}$ haloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —$N_3$, —CN, —O—$R^{12a}$, —C(O)—$R^{12a}$, —C(O)O—$R^{12a}$, —C(O)—$N(R^{12a})(R^{12b})$, —$N(R^{12a})(R^{12b})$, $N(R^{12a})_2(R^{12b})^+$, —$N(R^{12a})C(O)$—$R^{12b}$, —$N(R^{12a})C(O)O$—$R^{12b}$, —$N(R^{12a})C(O)N(R^{12b})(R^{12c})$, —$N(R^{12a})S(O)_2(R^{12b})$, —$NR^{12a}S(O)_2N(R^{12b})(R^{12c})$, —$NR^{12a}S(O)_2O(R^{12b})$, —$OC(O)R^{12a}$, —$OC(O)OR^{12a}$, —OC(O)—$N(R^{12a})(R^{12b})$, —S—$R^{12a}$, —$S(O)R^{12a}$, —$S(O)(NH)R^{12a}$, —$S(O)_2R^{12a}$, —$S(O)_2N(R^{12a})(R^{12b})$, —$S(O)(NR^{12a})R^{12b}$, or —$Si(R^{12a})_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{12a}$, —$C(O)R^{12a}$, —C(O)O—$R^{12a}$, —$C(O)N(R^{12a})(R^{12b})$, —$N(R^{12a})(R^{12b})$, —$N(R^{12a})_2(R^{12b})^+$, —$N(R^{12a})$—$C(O)R^{12b}$, —$N(R^{12a})C(O)O(R^{12b})$, —$N(R^{12a})C(O)N(R^{12b})(R^{12c})$, —$N(R^{12a})S(O)_2(R^{12b})$, —$N(R^{12a})S(O)_2$—$N(R^{12b})(R^{12c})$, —$N(R^{12a})S(O)_2O(R^{12b})$, —$OC(O)R^{12a}$, —$OC(O)OR^{12a}$, —OC(O)—$N(R^{12a})(R^{12b})$, —S—$R^{12a}$, —$S(O)R^{12a}$, —$S(O)(NH)R^{12a}$, —$S(O)_2R^{12a}$, —$S(O)_2N(R^{12a})(R^{12b})$, —$S(O)(NR^{12a})R^{12b}$, or —$Si(R^{12a})_3$;

wherein the alkyl, haloalkyl, alkenyl, alkynyl, cycloalkyl, heterocyclyl, aryl, or heteroaryl is each optionally substituted with one to four $Z^{1b}$;

each $R^8$ or $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —$N(C_{1-9}\ alkyl)_2$, —$N(C_{1-8}\ haloalkyl)_2$, —$N(C_{2-6}\ alkenyl)_2$, —$N(C_{2-6}\ alkynyl)_2$, —$N(C_{3-15}\ cycloalkyl)_2$, —N(heterocyclyl)$_2$, —$N(C_{6-10}\ aryl)_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —$C(O)NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —$C(O)N(C_{1-9}\ alkyl)_2$, —$C(O)N(C_{1-8}\ haloalkyl)_2$, —$C(O)N(C_{2-6}\ alkenyl)_2$, —$C(O)N(C_{2-6}\ alkynyl)_2$, —$C(O)N(C_{3-15}\ cycloalkyl)_2$, —C(O)N(heterocyclyl)$_2$, —$C(O)N(C_{6-10}\ aryl)_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —$S(O)N(C_{1-9}\ alkyl)_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —$S(O)_2$($C_{1-9}$ alkyl), —$S(O)_2$($C_{1-8}$ haloalkyl), —$S(O)_2$($C_{2-6}$ alkenyl), —$S(O)_2$($C_{2-6}$ alkynyl), —$S(O)_2$($C_{3-15}$ cycloalkyl), —$S(O)_2$(heterocyclyl), —$S(O)_2$($C_{6-10}$ aryl), —$S(O)_2$ (heteroaryl), —S(O)(NH)($C_{1-9}$ alkyl), —$S(O)_2$NH ($C_{1-9}$ alkyl), or —$S(O)_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —$NH_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O ($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), $S(O)_2$($C_{1-9}$ alkyl), —$S(O)_2$($C_{1-8}$ haloalkyl), —$S(O)_2$($C_{3-15}$ cycloalkyl), —$S(O)_2$(heterocyclyl), —$S(O)_2$(aryl), —$S(O)_2$(heteroaryl), —S(O)(NH) ($C_{1-9}$ alkyl), —$S(O)_2$NH($C_{1-9}$ alkyl), or —$S(O)_2$N ($C_{1-9}$ alkyl)$_2$; and each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$;

wherein each heteroaryl has 5 to 12 ring members and has one to four heteroatoms each independently N, O, or S; and wherein each heterocyclyl has 3 to 12 ring members and has one to four heteroatoms each independently N, O, or S.

In some embodiments of the compound of Formula (I), (I-A-1), and/or other formula described herein, or pharmaceutically acceptable salt thereof, $R^1$ is $C_{1-6}$ alkyl, $C_{2-6}$ alkenyl, $C_{2-6}$ alkynyl, $C_{3-10}$ cycloalkyl, $C_{6-10}$ aryl, 5 to 10 membered heteroaryl having one to three heteroatoms each independently N, O or S, or 3 to 12 membered heterocyclyl having one to three heteroatoms each independently N, O or S, wherein the cycloalkyl, aryl, heteroaryl and heterocyclyl are each optionally substituted with one to three $Z^1$;

ring A is $C_{6-10}$ aryl, 5 to 10 membered heteroaryl having one to three heteroatoms each independently N, O or S, or 3 to 12 membered heterocyclyl having one to three heteroatoms each independently N, O or S, wherein the aryl, heteroaryl and heterocyclyl are each optionally substituted with one to four $Z^1$;

ring B is $C_{6-10}$ aryl or 5 to 10 membered heteroaryl having one to three heteroatoms each independently N, O or S, wherein the aryl and heteroaryl are each optionally substituted with one to four $R^4$;

$R^2$ is H, $C_{1-6}$ alkyl, $C_{2-6}$ alkenyl, $C_{2-6}$ alkynyl, $C_{1-6}$ haloalkyl, $C_{2-6}$ alkoxyalkyl, $C_{3-10}$ cycloalkyl, heterocyclyl, $C_{6-10}$ aryl, heteroaryl, $C_{1-6}$ alkyl-$C_{3-10}$ cycloalkyl, $C_{1-6}$ alkyl-heterocyclyl, $C_{1-6}$ alkyl-$C_{6-10}$ aryl, $C_{1-6}$ alkyl-heteroaryl, $C_{1-6}$ alkyl-$C_{3-10}$ cycloalkyl-$C_{1-6}$ alkyl, $C_{1-6}$ alkyl-heterocyclyl-$C_{1-6}$ alkyl, —CN, —C(O)$R^{2a}$, —C(O)O$R^{2a}$, —C(O)N($R^{2a}$)($R^{2b}$), —C(O)N$R^{2c}$ $S(O)_2R^{2a}$, —$S(O)_2R^{2a}$, —$S(O)_2$N($R^{2a}$)($R^{2b}$), or —$S(O)_2$N$R^{2c}$C(O)$R^{2a}$, wherein each heterocyclyl comprises 3 to 12 ring members and 1 to 3 heteroatoms each independently N, O or S, wherein each heteroaryl comprises 5 to 10 ring members and 1 to 3 heteroatoms each independently N, O or S, and wherein the cycloalkyl, aryl, heteroaryl, and heterocyclyl are each optionally substituted with one to four $Z^{1b}$;

$X^1$, $X^2$, and $X^3$ are each independently —N═ or —C($R^8$)═;

$R^3$ is H, $C_{1-6}$ alkyl, $C_{2-6}$ alkenyl, $C_{2-6}$ alkynyl, $C_{1-6}$ haloalkyl, halogen, $C_{3-10}$ cycloalkyl, $C_{6-10}$ aryl, 3 to 12 membered heterocyclyl having one to three heteroatoms each independently N, O or S, 5 to 10 membered heteroaryl having one to four heteroatoms each independently N, O or S, —CN, —$NO_2$, —C(O)$R^{3a}$, —C(O)O$R^{3a}$, —C(O)N($R^{3a}$)($R^{3b}$), —N($R^{3a}$)C(O)$R^{3b}$, —N($R^{3a}$)C(O)O$R^{3b}$, —N($R^{3a}$)C(O)N($R^{3b}$)$_2$, —C(O)NH$S(O)_2R^{3a}$, —$S(O)_2R^{3a}$, —$S(O)_2$O$R^{3a}$, —$S(O)_2$N($R^{3a}$)($R^{3b}$), —N($R^{3a}$)$S(O)_2R^{3b}$, —$S(O)_2$NHC(O)$R^{3a}$, —S(O)(═N$R^{3a}$)$R^{3b}$, —S(O)(═N$R^{3a}$)N$R^{3b}$, —S(═N$R^{3a}$)(═N$R^{3b}$)$R^{3c}$, —P(O)(O$R^{3a}$)($R^{3b}$), —P(O)(O$R^{3a}$)(O$R^{3b}$), or —B(O$R^{3a}$)(O$R^{3b}$), wherein the alkyl, alkenyl, alkynyl, haloalkyl, cycloalkyl, aryl, heteroaryl, or heterocyclyl are each optionally substituted with one to four $R^{3d}$;

each $R^{2a}$, $R^{2b}$, $R^{2c}$, $R^{3a}$, $R^{3b}$, and $R^{3c}$ is independently H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 3 to 12 membered heterocyclyl having one to three heteroatoms each independently N, O or S, or 5 to 10 membered heteroaryl having one to four heteroatoms each independently N, O or S;

each $R^4$ is independently H, $C_{1-6}$ alkyl, $C_{1-6}$ alkoxy, $C_{1-6}$ haloalkyl, $C_{1-6}$ haloalkoxy, halogen, $C_{3-10}$ cycloalkyl, 3 to 12 membered heterocyclyl having one to three heteroatoms each independently N, O or S, oxo, OH, —CN, —$NO_2$, —$N_3$, C(O)O$R^{4a}$, or C(O)N($R^{4a}$)($R^{4b}$) wherein the cycloalkyl and heterocyclyl are each optionally substituted with one to four $R^{4c}$;

each $R^{4a}$ and $R^{4b}$ is independently H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 3 to 12 membered heterocyclyl having one to three heteroatoms each independently N, O or S, or 5 to 10 membered heteroaryl having one to four heteroatoms each independently N, O or S;

alternatively, two $R^4$ groups attached to adjacent ring atoms are combined with the atoms to which they are attached to form a $C_{3-10}$ cycloalkyl or 3 to 12 membered heterocyclyl having one to three heteroatoms each independently N, O or S, wherein the cycloalkyl and heterocyclyl are each optionally substituted with one to four $R^{4c}$;

$R^{5a}$ and $R^{5b}$ are each independently H, $C_{1-6}$ alkyl, halogen, $C_{3-10}$ cycloalkyl, 3 to 12 membered heterocyclyl having one to three heteroatoms each independently N, O or S, —CN, —O$R^{5a}$, or —N($R^{5a1}$)($R^{5a2}$), wherein the cycloalkyl and heterocyclyl are each optionally substituted with one to four $R^{5a3}$;

each $R^{5a1}$, $R^{5a1}$, and $R^{5a2}$ is independently H, $C_{1-6}$ alkyl, $C_{2-6}$ alkenyl, $C_{2-6}$ alkynyl, $C_{3-10}$ cycloalkyl, $C_{6-10}$ aryl, 3 to 12 membered heterocyclyl having one to three heteroatoms each independently N, O or S, or 5 to 10 membered heteroaryl having one to three heteroatoms each independently N, O or S, wherein the cycloalkyl, aryl, heteroaryl, and heterocyclyl are each optionally substituted with one to four $R^{5a4}$;

V is —C(O)—, —O—, —$N(R^{6a})$—, —$C(R^{6b})(R^{6c})$—;

$R^{6a}$ is H, $C_{1-6}$ alkyl, $C_{3-10}$ cycloalkyl, 3 to 12 membered heterocyclyl having one to three heteroatoms each independently N, O or S, —$S(O)_2R^{6a1}$, or —$S(O)_2N(R^{6a1})(NR^{6a2})$, wherein the cycloalkyl and heterocyclyl are each optionally substituted with F, CN, or $C_{1-6}$ alkyl;

each $R^{6b}$ and $R^{6c}$ is independently H, halogen, —CN, $C_{1-6}$ alkyl, $C_{3-10}$ cycloalkyl, 3 to 12 membered heterocyclyl having one to three heteroatoms each independently N, O or S, —$OR^{6c1}$, or —$N(R^{6c2})(R^{6c3})$, wherein the alkyl, cycloalkyl and heterocyclyl are each optionally substituted with one to four $R^{6b1}$;

alternatively, $R^{6b}$ and $R^{6c}$ are combined with the atom to which they are attached to form $C_{3-10}$ cycloalkyl, optionally substituted with one to four $R^{6b1}$;

alternatively, $R^{6c}$ is combined with one $R^4$ group and the atoms to which they are attached to form a $C_{3-10}$ cycloalkyl or 3 to 12 membered heterocyclyl having one to three heteroatoms each independently N, O or S, wherein the cycloalkyl and heterocyclyl are each optionally substituted with one to four $R^{4c}$;

Y is —$N(R^7)$—, —O—, —S—, —S(O)—, —S(=NH)— or —$S(=NR^7)$—;

each $R^8$ is H, $C_{1-6}$ alkyl, $C_{2-6}$ alkenyl, $C_{2-6}$ alkynyl, $C_{1-6}$ haloalkyl, halogen, $C_{3-10}$ cycloalkyl, $C_{6-10}$ aryl, 3 to 12 membered heterocyclyl having one to three heteroatoms each independently N, O or S, or 5 to 10 membered heteroaryl having one to four heteroatoms each independently N, O or S, —CN, —$NO_2$, —$C(O)R^{3a}$, —$C(O)OR^{3a}$, —$C(O)N(R^{3a})(R^{3b})$, —$N(R^{3a})C(O)R^{3b}$, —$N(R^{3a})C(O)OR^{3b}$, —$N(R^{3a})C(O)N(R^{3b})_2$, —$C(O)NHS(O)_2R^{3a}$, —$S(O)_2R^{3a}$, —$S(O)_2OR^{3a}$, —$S(O)_2N(R^{3a})(R^{3b})$, —$N(R^{3a})S(O)_2R^{3b}$, —$S(O)_2NHC(O)R^{3a}$, —$S(O)(=NR^{3a})R^{3b}$, —$S(O)(=NR^{3a})NR^{3b}$, —$S(=NR^{3a})(=NR^{3b})R^{3c}$, —$P(O)(OR^{3a})(R^{3b})$, —$P(O)(OR^{3a})(OR^{3b})$, or —$B(OR^{3a})(OR^{3b})$;

each $Z^{1b}$, $R^{3d}$, $R^{4c}$, $R^{5a3}$, $R^{5a4}$, and $R^{6b1}$ is independently $C_{1-6}$ alkyl, $C_{1-6}$ alkoxy, $C_{1-6}$ haloalkyl, $C_{1-6}$ haloalkoxy, halogen, $C_{3-10}$ cycloalkyl, 3 to 12 membered heterocyclyl having one to three heteroatoms each independently N, O or S, 5 to 10 membered heteroaryl having one to three heteroatoms each independently N, O or S, oxo, —OH, —CN, or —$NO_2$; and each $R^{6a1}$, $R^{6a2}$, $R^{6c1}$, $R^{6c2}$, $R^{6c3}$ and $R^7$ is independently $C_{1-6}$ alkyl or $C_{3-10}$ cycloalkyl.

In some embodiments of the compound of Formula (I), (I-A-1), and/or other formula described herein, or pharmaceutically acceptable salt thereof, $R^1$ is $C_{6-10}$ aryl, heteroaryl, or heterocyclyl, wherein the aryl, heteroaryl or heterocyclyl is optionally substituted with one to three $Z^1$. In some embodiments of the compound of Formula (I), (I-A-1), and/or other formula described herein, or pharmaceutically acceptable salt thereof, $R^1$ is $C_{6-10}$ aryl, heteroaryl, or heterocyclyl, wherein the aryl, heteroaryl or heterocyclyl is optionally substituted with one to three $R^{1a}$. In some embodiments of the compound of Formula (I), (I-A-1), and/or other formula described herein, or pharmaceutically acceptable salt thereof, $R^1$ is $C_{6-10}$ aryl, 5 to 10 membered heteroaryl having one to three heteroatoms each independently O, N, or S, or 4 to 12 membered heterocyclyl having one to three heteroatoms each independently O, N, or S, wherein the aryl, heteroaryl or heterocyclyl is optionally substituted with one to three $R^{1a}$. In some embodiments of the compound of Formula (I), (I-A-1), and/or other formula described herein, $R^1$ is heterocyclyl, $C_{6-10}$ aryl, or 6-membered heteroaryl, which is each optionally substituted with one to three $Z^1$, wherein $Z^1$ is independently $C_{1-6}$ alkyl, $C_{1-6}$ haloalkyl, $C_{1-6}$ alkoxy, $C_{1-6}$ haloalkoxy, halogen, oxo, —OH, —CN, or —$NO_2$, $C_{3-10}$ cycloalkyl, 3 to 12 membered heterocyclyl having one to three heteroatoms, or 5 to 10 membered heteroaryl having one to three heteroatoms In some embodiments of the compound of Formula (I), (I-A-1), and/or other formula described herein, or pharmaceutically acceptable salt thereof, each $R^{5a}$ and $R^{5b}$ is independently H, $C_{1-6}$ alkyl, F, Cl, —$OR^{5a}$, —CN, $C_{3-10}$ cycloalkyl, or heterocyclyl. In some embodiments of the compound of Formula (I), (I-A-1), and/or (I-A-2), or pharmaceutically acceptable salt thereof, $R^{5a}$ is H; and $R^{5b}$ is H, $C_{1-6}$ alkyl, F, Cl, —$OR^{5a}$, —CN, $C_{3-10}$ cycloalkyl, or heterocyclyl. In some embodiments, each $R^{5a}$ and $R^{5b}$ is H.

In some embodiments of the compound of Formula (I), (I-A-1), and/or other formula described herein, or pharmaceutically acceptable salt thereof, Y is —O—.

In some embodiments, the compound of Formula (I) or pharmaceutically acceptable salt thereof has a structure of Formula (Ia):

(Ia)

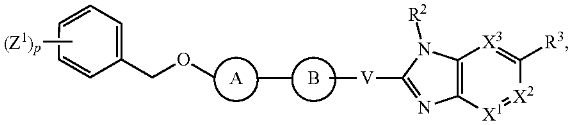

wherein subscript p is 1, 2, or 3.

In some embodiments of the compound of Formula (I), (I-A-1), (Ia), and/or other formula described herein, or pharmaceutically acceptable salt thereof, ring A is $C_{6-10}$ aryl or 5 to 10 membered heteroaryl, wherein the aryl or heteroaryl is optionally substituted with one to three $Z^{1a}$, wherein each $Z^{1a}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{3-10}$ cycloalkyl, $C_{6-10}$ aryl, $C_{1-6}$ haloalkyl, $C_{1-6}$ haloalkoxy, —$C(O)N(R^{2a})(R^{2b})$, oxo, —OH, halogen, —CN, —$NO_2$, —$OR^{12a}$, $C_{3-10}$ cycloalkyl, heterocyclyl, heterocyclyl-$C_{1-6}$ alkyl, heterocyclyl-$C_{1-6}$ haloalkyl, heteroaryl, heteroaryl-$C_{1-6}$ alkyl, or heteroaryl-$C_{1-6}$ haloalkyl, each of which is optionally substituted with $Z^{1b}$. In some embodiments of the compound of Formula (I), (I-A-1), (Ia), and/or other formula described herein, or pharmaceutically acceptable salts thereof, ring A is $C_{6-10}$ aryl or 5 to 10 membered heteroaryl having one to three heteroatoms each independently O, N, or S, wherein the aryl or heteroaryl is optionally substituted with one to three $Z^{1a}$. In some embodiments of the compound of Formula (I), (I-A-1), (Ia), and/or other formula described herein, or pharmaceutically acceptable salt thereof, ring A is phenyl or 5 to 6 membered heteroaryl, wherein the phenyl or heteroaryl is optionally substituted with one to three $Z^{1a}$. In some embodiments of the compound of Formula (I), (I-A-1), (I-A-2), and/or (Ia), or pharmaceutically acceptable salt thereof, ring A is phenyl or 5 to 6 membered heteroaryl having one to three heteroatoms each independently O, N, or S, wherein the phenyl or heteroaryl is optionally substituted with one to three $Z^{1a}$. In some embodiments of the compound of Formula (I), (I-A-1), (Ia), and/or other formula described herein, or pharmaceutically acceptable salt thereof, ring A is

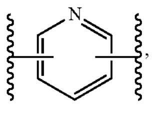, 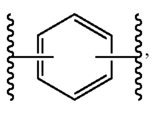, 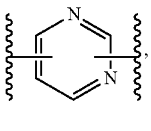, or

-continued

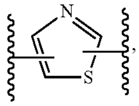

wherein each ring is optionally substituted with one or two $Z^{1a}$.

In some embodiments of the compound of Formula (I), (I-A-1), (Ia), and/or other formula described herein, or pharmaceutically acceptable salt thereof, ring A is

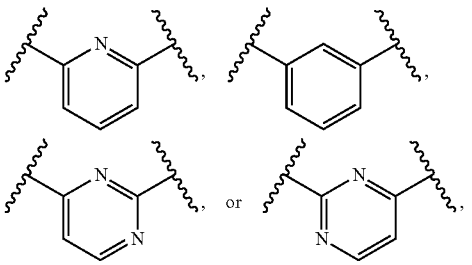

or wherein each ring is optionally substituted with one or two $Z^{1a}$.

In some embodiments of the compound of Formula (I), (I-A-1), (I-A-2), and/or (Ia), or pharmaceutically acceptable salt thereof, ring A is

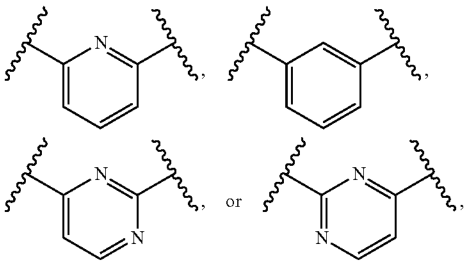

or wherein each ring is optionally substituted with one or two halogens.

In some embodiments, the compound of Formula (I), (I-A-1), and/or (Ia), or pharmaceutically acceptable salt thereof, has a structure of Formula (Ib):

(Ib)

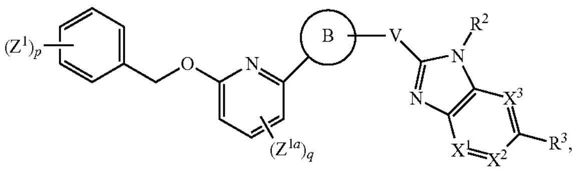

wherein $Z^{1a}$ is halogen, $C_{1-4}$ alkyl, —$OR^{12a}$, or —CN, wherein the $C_{1-4}$ alkyl is optionally substituted with $Z^{1b}$.

subscript p is 1, 2, or 3; and subscript q is 0, 1, or 2.

In some embodiments, the compound of Formula (I), (I-A-1), and/or (Ia), or a pharmaceutically acceptable salt thereof, has a structure of Formula (Ib-1):

(Ib-1)

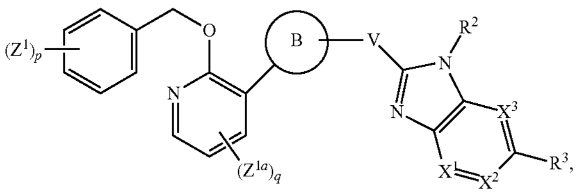

wherein subscript p is 1, 2, or 3; and subscript q is 0, 1 or 2.

In some embodiments of the compound of Formula (I-A-1), (I), (Ia), (Ib) and/or (Ib-1), or pharmaceutically acceptable salt thereof, ring B is phenyl or 5 to 6 membered heteroaryl, wherein the phenyl or heteroaryl is optionally substituted with one to four $R^4$. In some embodiments of the compound of Formula (I-A-1), (I), (Ia), (Ib) and/or (Ib-1), or pharmaceutically acceptable salt thereof, ring B is phenyl or 5 to 6 membered heteroaryl having one to three heteroatoms each independently O, N, or S, wherein the phenyl or heteroaryl is optionally substituted with one to four $R^4$. In some embodiments of the compound of Formula (I-A-1), (I), (Ia), (Ib) and/or (Ib-1), or pharmaceutically acceptable salt thereof, ring B is

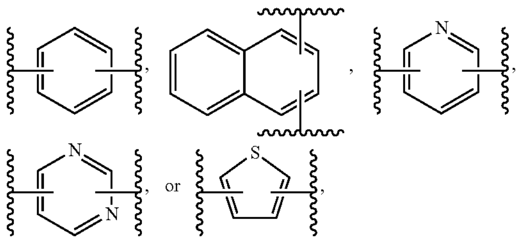

or which are each optionally substituted with one or two $R^4$.

In some embodiments of the compound of Formula (I-A-1), (I), (Ia), (Ib) and/or (Ib-1), or pharmaceutically acceptable salt thereof, ring B is

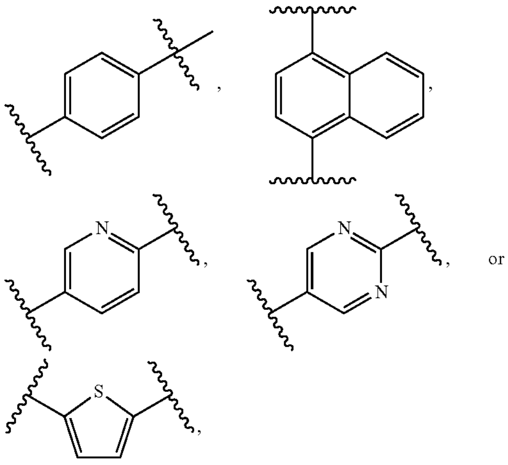

or which are each optionally substituted with one or two $R^4$.

In some embodiments of the compound of Formula (I-A-1), (I), (Ia), (Ib) and/or (Ib-1), or pharmaceutically acceptable salt thereof, ring B is

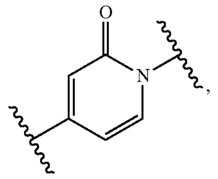 [SMILES: *c1ccn(*)c(=O)c1]

which is optionally substituted with one or two $R^4$.

In some embodiments of the compound of Formula (I), (I-A-1), and/or other formula described herein, or pharmaceutically acceptable salt thereof, ring B is substituted with one, two, or three halogens. In some embodiments of the compound of Formula (I), (I-A-1), and/or other formula described herein, or pharmaceutically acceptable salt thereof, ring B is substituted with one, two, or three fluoro.

In some embodiments, the compound of Formula (I), (I-A-1), and/or (Ia), and/or other formula described herein, or pharmaceutically acceptable salt thereof, has a formula:

(Ic)

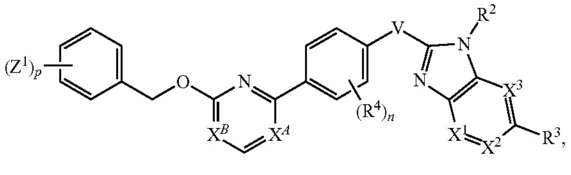

wherein $X^A$ and $X^B$ are each independently —CH= or —N=;

subscript n is 0, 1, 2, or 3; and subscript p is 1, 2, or 3.

In some embodiments of the compound of Formula (I), (I-A-1), (Ia), (Ib), (Ib-1) and/or (Ic), and/or other formula described herein, or pharmaceutically acceptable salt thereof, $X^1$, $X^2$, and $X^3$ are each independently —N=, —CH=, —C(F)=, —C(Cl)=, —C(Br)=, or —C(CN)=. In some embodiments of the compound of Formula (I), (I-A-1), and/or other formula described herein, or a pharmaceutically acceptable salt thereof, $X^1$, $X^2$, and $X^3$ are each independently —CH=, —C(F)=, —C(Cl)=, —C(Br)=, or —C(CN)=. In some embodiments of the compound of Formula (I), (I-A-1), and/or other formula described herein, or a pharmaceutically acceptable salt thereof, $X^1$, $X^2$, and $X^3$ are each independently —N=, —CH= or —C(F)=. In some embodiments, two of $X^1$, $X^2$, and $X^3$ is —CH= and one is —N=. For example, $X^1$ can be —N= while $X^2$ and $X^3$ is each —CH=. In some embodiments of the compound of Formula (I), (I-A-1), and/or other formula described herein, or a pharmaceutically acceptable salt thereof, two of $X^1$, $X^2$, and $X^3$ is —CH= and one is —C(F)=. In some embodiments, $X^1$, $X^2$, and $X^3$ is each —CH=.

In some embodiments of the compound of Formula (I), (I-A-1), (I-A-2), (Ia), (Ib), (Ib-1) and/or (Ic), or pharmaceutically acceptable salt thereof, V is —O—, —NH—, or —$CH_2$—. In some embodiments of the compound of Formula (I), (I-A-1), and/or other formula described herein, or pharmaceutically acceptable salt thereof, V is —O—. In some embodiments, V is —$CH_2$—. In some embodiments of Formula (I), (I-A-I), (I-A-2), and/or other formula described herein, V is —$CH_2$— —$CH(CH_3)$—, or —$C(CH_3)_2$—. In some embodiments, V is —$CH_2$—.

In some embodiments, the compound of Formula (I), (I-A-1) (Ia), and/or (Ic), and/or other formula described herein, or pharmaceutically acceptable salt thereof, has a formula:

(Id)

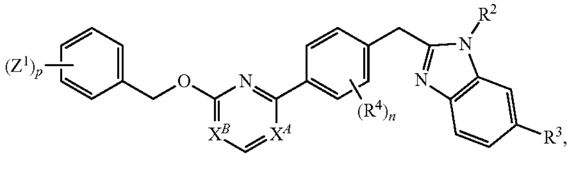

wherein $X^A$ and $X^B$ are each independendy —CH= or —N=;

subscript n is 0, 1, 2, or 3; and subscript p is 1, 2, or 3.

In some embodiments of the compound of Formula (Ic) and/or (Id), or pharmaceutically acceptable salt thereof, subscript n is 0, 1 or 2. In some embodiments, subscript n is 0. In some embodiments of a compound of Formula (I) or other compound described herein, subscript n is 1. In some embodiments, subscript n is 2.

In some embodiments of the compound of Formula (Ia), (Ib), (Ib-1), (Ic) and/or (Id), or pharmaceutically acceptable salt thereof, subscript p is 1 or 2. In some embodiments, subscript p is 1. In some embodiments of a compound of Formula (I) or other compound described herein, subscript p is 2.

In some embodiments of the compound of Formula (Ib) and/or (Ib-1) or pharmaceutically acceptable salt thereof, subscript q is 0 or 1. In some embodiments, subscript q is 0. In some embodiments, subscript q is 1.

In some embodiments of the compound of Formula (Ic) and/or (Id), or pharmaceutically acceptable salt thereof, one of $X^A$ and $X^B$ is —CH= and the other is —N=. In some embodiments, $X^A$ is —N= and $X^B$ is —CH=. In some embodiments, $X^A$ is —CH= and $X^B$ is —N=.

In some embodiments of the compound of Formula (I-A-1), (I), (Ia), (Ib), (Ib-1), (Ic) and/or (Id), and/or other formula described herein, or pharmaceutically acceptable salt thereof, each $Z^1$ is $C_{1-6}$ alkyl, $C_{1-6}$ haloalkyl, $C_{1-6}$ alkoxy, $C_{1-6}$ haloalkoxy, halogen, $C_{3-10}$ cycloalkyl, 3 to 12 membered heterocyclyl having one to three heteroatoms each independently N, O or S, 5 to 10 membered heteroaryl having one to three heteroatoms each independently N, O or S, oxo, —OH, —CN, or —$NO_2$. In some embodiments of the compound of Formula (I-A-1), (I-A-2), (I), (Ia), (Ib), (Ib-1), (Ic) and/or (Id), or pharmaceutically acceptable salt thereof, each $Z^1$ is independently halogen, $C_{1-6}$ haloalkyl, $C_{1-6}$ haloalkoxy, —CN, or 5 to 6 membered heteroaryl. In some embodiments of the compound of Formula (I-A-1), (I-A-2), (I), (Ia), (Ib), (Ib-1), (Ic) and/or (Id), or pharmaceutically acceptable salt thereof, each $Z^1$ is independently halogen, $C_{1-6}$ haloalkyl, $C_{1-6}$ haloalkoxy, —CN, or 5 to 6 membered heteroaryl having one to three heteroatoms each independently N, O or S. In some embodiments of the compound of Formula (I-A-1), (I-A-2), (I), (Ia), (Ib), (Ib-1), (Ic) and/or (Id), or pharmaceutically acceptable salt thereof, each $Z^1$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, heterocyclyl-$C_{1-6}$ alkyl, heterocyclyl-$C_{1-6}$ haloalkyl, heteroaryl-$C_{1-6}$ alkyl, heteroaryl-$C_{1-6}$ haloalkyl, oxo, —OH, —CN, —$NO_2$, or —$C(O)N(R^{12a})(R^{12b})$, wherein the heteroaryl or heterocyclyl is each optionally substituted with one to four halogen, —CN, $C_{1-6}$ haloalkyl, $C_{3-6}$ cycloalkyl or 4-6 membered heterocyclyl. In some embodiments, each $Z^1$ is independently halogen, $C_{1-6}$ haloalkyl, —CN, $C_{1-3}$ alkoxy, or $C_{3-10}$ cycloalkyl. In some embodiments of the compound of Formula (I-A-1), (I-A-2), (I), (Ia), (Ib), (Ib-1), (Ic) and/or (Id), or pharmaceutically acceptable salt thereof, each $Z^1$ is independently $C_{1-6}$ haloalkyl, $C_{1-6}$ haloalkoxy, halogen, 5 to 6 membered heteroaryl having one to three heteroatoms each independently N, O or S, or —CN. In some embodiments, each $Z^1$ is independently halogen, $C_{1-6}$ haloalkyl, or —CN. In some embodiments of the compound of Formula (I-A-1), (I-A-2), (I), (Ia), (Ib), (Ib-1), (Ic) and/or (Id), or pharmaceutically acceptable salt thereof, each $Z^1$ is independently halogen, $C_{1-6}$ haloalkyl, $C_{1-3}$ alkoxy, $C_{3-10}$ cycloalkyl, or —CN. In some embodiments of the compound of Formula (I-A-1), (I-A-2), (I), (Ia), (Ib), (Ib-1), (Ic) and/or (Id), or pharmaceutically acceptable salt thereof, each $Z^1$ is independently halogen, $C_{1-3}$ haloalkyl, $C_{1-3}$ haloalkoxy, or —CN. In some embodiments of the compound of Formula (I-A-1), (I-A-2), (I), (Ia), (Ib), (Ib-1), (Ic) and/or (Id), or pharmaceutically acceptable salt thereof, each $R^{2d}$ is independently F, $C_{1-6}$ haloalkyl, —CN, or $C_{3-10}$ cycloalkyl. In some embodiments of the compound of Formula (I-A-1), (I-A-2), (I), (Ia), (Ib), (Ib-1), (Ic) and/or (Id), or pharmaceutically acceptable salt thereof, each $Z^1$ is independently halogen or —CN. In some embodiments of the compound of Formula (I-A-1), (I-A-2), (I), (Ia), (Ib), (Ib-1), (Ic) and/or (Id), or pharmaceutically acceptable salt thereof, $Z^1$ is —CN. In some embodiments of the compound of Formula (I-A-1), (I-A-2), (I), (Ia), (Ib), (Ib-1), (Ic) and/or (Id), or pharmaceutically acceptable salt thereof, $Z^1$ is a halogen, such as F.

In some embodiments, the compound of Formula (I), (I-A-1) and/or other formula described herein, or pharmaceutically acceptable salt thereof, has a formula (I-A-2):

(I-A-2)

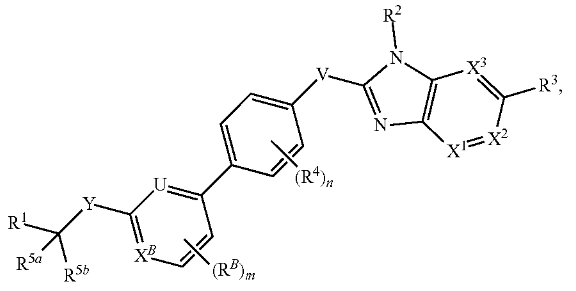

wherein

U is —CH═ or —N═;

$X^B$ is —CH═ or —N═;

$R^B$ IS $C_{1-6}$ alkyl, $C_{1-6}$ haloalkyl, $C_{1-6}$ alkoxy, $C_{1-6}$ haloalkoxy, halogen, or —CN;

$X^1$, and $X^2$, are each independently —N═, —C(H)═, or —C($R^8$)═.

$X^3$ is —C(H)═;

each $R^4$ is independently $C_{1-9}$ alkyl, $C_{1-8}$ haloalkyl, $C_{1-6}$ haloalkoxy, $C_{2-6}$ alkenyl, $C_{2-6}$ alkynyl, halogen, $C_{3-15}$ cycloalkyl, heterocyclyl, $C_{6-10}$ aryl, oxo, —$NO_2$, —$N_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)C(O)O($R^{4b}$), —N($R^{4a}$)C(O)N($R^{4b}$)($R^{4c}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2R^{4a}$, —S(O)$_2$N($R^{4a}$)($R^{4b}$), —S(O)(N$R^{4a}$)$R^{4b}$, or —Si($R^{4a}$)$_3$;

wherein the alkyl, haloalkyl, alkenyl, alkynyl, cycloalkyl, heterocyclyl, aryl, or heteroaryl is each optionally substituted with one to four $Z^{1b}$;

or two $R^4$ groups attached to adjacent ring atoms are combined with the atoms to which they are attached to form a $C_{5-10}$ cycloalkyl or heterocyclyl, which is each optionally substituted with one to four $Z^{1b}$;

V is —C(O)—, —O—, —N($R^{6a}$)—, or —C($R^{6b}$)($R^{6c}$)—;

$R^{6a}$ is H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the cycloalkyl or heterocyclyl is each optionally substituted with $C_{1-6}$ alkyl, F, or —CN;

each $R^{6b}$ and $R^{6c}$ is independently H or $C_{1-6}$ alkyl;

each $R^{1a}$, $R^{3d}$, $R^{5a3}$, $R^{5a4}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, $CO_2R^{3e}$, —$NO_2$, or —C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, $R^{6c3}$ and $R^7$ is independently H, $C_{1-6}$ alkyl or $C_{3-10}$ cycloalkyl;

each $R^8$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, $CO_2R^{3e}$, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC (O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —NH$_2$, CO$_2$H—O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

each $R^{9a}$ and $R^{9b}$ is independently H, $C_{1-6}$ alkyl, or $C_{1-6}$ haloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1b}$;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, CO$_2$$R^{3e}$, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —$NH_2$, $CO_2H$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), $S(O)_2$($C_{1-9}$ alkyl), —$S(O)_2$($C_{1-8}$ haloalkyl), —$S(O)_2$($C_{3-15}$ cycloalkyl), —$S(O)_2$(heterocyclyl), —$S(O)_2$(aryl), —$S(O)_2$(heteroaryl), —S(O)(NH)($C_{1-9}$ alkyl), —$S(O)_2$NH($C_{1-9}$ alkyl), or —$S(O)_2$N($C_{1-9}$ alkyl)$_2$;

each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$; and each $R^{3e}$ is independently H, $C_{1-6}$ alkyl, $C_{1-6}$ haloalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$ alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{3-10}$ cycloalkyl, heterocyclyl, $C_{6-10}$ aryl, heteroaryl, —P(O)($OR^{9c}$)$_2$, —$CH_2$P(O)($OR^{9c}$)$_2$, —$OCH_2$P(O)($OR^{9c}$)$_2$, —C(O)$OCH_2$P(O)($OR^{9c}$)$_2$, —P(O)($R^{9c}$)($OR^{9d}$), —OP(O)($R^{9c}$)($OR^{9d}$), —$CH_2$P(O)($R^{9c}$)($OR^{9d}$), —C(O)$OCH_2$P(O)($R^{9c}$)($OR^{9d}$), —P(O)(N($R^{9c}$)$_2$)$_2$, —$CH_2$P(O)(N($R^{9c}$)$_2$)$_2$, —C(O)$OCH_2$P(O)(N($R^{9c}$)$_2$)$_2$, —P(O)(N($R^{9c}$)$_2$)($OR^{9d}$), —$CH_2$P(O)(N($R^{9c}$)$_2$)($OR^{9d}$), —C(O)$OCH_2$P(O)(N($R^{9c}$)$_2$)($OR^{9d}$), —P(O)($R^{9c}$)(N($R^{9d}$)$_2$), —$CH_2$P(O)($R^{9c}$)(N($R^{9d}$)$_2$), or —C(O)$OCH_2$P(O)($R^9$)(N($R^{9d}$)$_2$); wherein the alkyl, alkenyl, cycloalkyl, heterocyclyl, aryl, or heteroaryl is each optionally substituted with one to four $Z^{1b}$; wherein each heteroaryl has 5 to 12 ring members and has one to four heteroatoms each independently N, O, or S; and wherein each heterocyclyl, unless otherwise stated, has 3 to 12 ring members and has one to four heteroatoms each independently N, O, or S; and m is 0, 1, or 2.

In some embodiments of the compound of Formula (I-A-1), (I-A-2), (I), (Ia), (Ib), (Ib-1), (Ic) and/or (Id), or pharmaceutically acceptable salt thereof, $R^2$ is H, $C_{1-6}$ alkyl, $C_{2-6}$ alkenyl, $C_{2-6}$ alkynyl, $C_{1-6}$ haloalkyl, $C_{2-6}$ alkoxyalkyl, —CN, —C(O)$R^{2a}$, —C(O)$OR^{2a}$, —C(O)N($R^{2a}$)($R^{2b}$), —C(O)$NR^{2c}S(O)_2R^{2a}$, —$S(O)_2R^{2a}$, —$S(O)_2$N($R^{2a}$)($R^{2b}$), —$S(O)_2NR^{2c}C(O)R^{2a}$, $C_{3-10}$ cycloalkyl, $C_{1-6}$ alkyl-$C_{3-10}$ cycloalkyl, $C_{1-6}$ alkyl-$C_{3-10}$ cycloalkyl-$C_{1-6}$ alkyl, $C_{1-6}$ alkyl-heterocyclyl-$C_{1-6}$ alkyl, $C_{6-10}$ aryl, $C_{1-6}$ alkyl-$C_{6-10}$ aryl, heterocyclyl, $C_{1-6}$ alkyl-heterocyclyl, heteroaryl or $C_{1-6}$ alkyl-heteroaryl wherein the alkyl, cycloalkyl, aryl, heteroaryl, and heterocyclyl are each optionally substituted with one or more $Z^{1b}$. In some embodiments of the compound of Formula (I-A-1), (I-A-2), (I), (Ia), (Ib), (Ib-1), (Ic) and/or (Id), or pharmaceutically acceptable salt thereof, $R^2$ is H, $C_{1-6}$ alkyl, $C_{1-6}$ haloalkyl, $C_{2-6}$ alkoxyalkyl, $C_{2-6}$ alkenyl, $C_{2-6}$ alkynyl, $C_{3-10}$ cycloalkyl, heterocyclyl, $C_{6-10}$ aryl, heteroaryl, $C_{1-6}$ alkyl-$C_{3-10}$ cycloalkyl, $C_{1-6}$ alkyl-heterocyclyl, $C_{1-6}$ alkyl-$C_{6-10}$ aryl, $C_{1-6}$ alkyl-heteroaryl, $C_{1-6}$ alkyl-$C_{3-10}$ cycloalkyl-$C_{1-6}$ alkyl, $C_{1-6}$ alkyl-heterocyclyl-$C_{1-6}$ alkyl, —CN, —C(O)$R^{2a}$, —C(O)$OR^{2a}$, —C(O)N($R^{2a}$)($R^{2b}$), —C(O)$NR^{2c}S(O)_2R^{2a}$, —$S(O)_2R^{2a}$, —$S(O)_2$N($R^{2a}$)($R^{2b}$), or —$S(O)_2NR^{2c}C(O)R^{2a}$, wherein the alkyl, cycloalkyl, aryl, heteroaryl, and heterocyclyl are each optionally substituted with one to four $Z^{1b}$. In some embodiments of the compound of Formula (I-A-1), (I-A-2), (I), (Ia), (Ib), (Ib-1), (Ic) and/or (Id), or pharmaceutically acceptable salt thereof, $R^2$ is H, $C_{1-6}$ alkyl, $C_{1-6}$ haloalkyl, $C_{2-6}$ alkoxyalkyl, $C_{2-6}$ alkenyl, $C_{2-6}$ alkynyl, $C_{3-10}$ cycloalkyl, heterocyclyl, $C_{6-10}$ aryl, heteroaryl, $C_{1-6}$ alkyl-$C_{3-10}$ cycloalkyl, $C_{1-6}$ alkyl-heterocyclyl, $C_{1-6}$ alkyl-$C_{6-10}$ aryl, $C_{1-6}$ alkyl-heteroaryl, $C_{1-6}$ alkyl-$C_{3-10}$ cycloalkyl-$C_{1-6}$ alkyl, $C_{1-6}$ alkyl-heterocyclyl-$C_{1-6}$ alkyl, —CN, —C(O)$R^{2a}$, —C(O)$OR^{2a}$, —C(O)N($R^{2a}$)($R^{2b}$), —C(O)$NR^{2c}S(O)_2R^{2a}$, —$S(O)_2R^{2a}$, —$S(O)_2$N($R^{2a}$)($R^{2b}$), or —$S(O)_2NR^{2c}C(O)R^{2a}$, wherein the alkyl, cycloalkyl, aryl, heteroaryl, and heterocyclyl are each optionally substituted with one to four $Z^{1b}$, wherein each $Z^{1b}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, heterocyclyl-$C_{1-6}$ alkyl, heterocyclyl-$C_{1-6}$ haloalkyl, heteroaryl-$C_{1-6}$ alkyl, heteroaryl-$C_{1-6}$ haloalkyl, oxo, —OH, —CN, —$NO_2$, or —C(O)N($R^{12a}$)($R^{12b}$). In some embodiments of the compound of Formula (I-A-1), (I-A-2), (I), (Ia), (Ib), (Ib-1), (Ic) and/or (Id), or pharmaceutically acceptable salt thereof, $R^2$ is H, $C_{1-6}$ alkyl, $C_{2-6}$ alkoxyalkyl, $C_{3-10}$ cycloalkyl, $C_{1-6}$ alkyl-$C_{3-10}$ cycloalkyl, heterocyclyl, $C_{1-6}$ alkyl-heterocyclyl, heteroaryl or $C_{1-6}$ alkyl-heteroaryl, wherein each heterocyclyl comprises 3 to 12 ring members and 1 to 3 heteroatoms each independently N, O or S, wherein each heteroaryl comprises 5 to 10 ring members and 1 to 3 heteroatoms each independently N, O or S, wherein the cycloalkyl, heterocyclyl and heteroaryl are each optionally substituted with one to four $Z^{1b}$. In some embodiments of the compound of Formula (I-A-1), (I-A-2), (I), (Ia), (Ib), (Ib-1), (Ic) and/or (Id), or pharmaceutically acceptable salt thereof, $R^2$ is $C_{1-6}$ alkyl, $C_{2-6}$ alkoxyalkyl, $C_{3-10}$ cycloalkyl, $C_{1-6}$ alkyl-$C_{3-10}$ cycloalkyl, $C_{1-6}$ alkyl-heteroaryl, or $C_{1-6}$ alkyl-heterocyclyl, wherein each heterocyclyl comprises 3 to 12 ring members and 1 to 3 heteroatoms each independently N, O or S, wherein each heteroaryl comprises 5 to 10 ring members and 1 to 3 heteroatoms each independently N, O or S, and wherein the cycloalkyl, heterocyclyl and heteroaryl are each optionally substituted with one or two $Z^{1b}$. In some embodiments of the compound of Formula (I-A-1), (I-A-2), (I), (Ia), (Ib), (Ib-1), (Ic) and/or (Id), or pharmaceutically acceptable salt thereof, $R^2$ is $C_{1-6}$ alkyl, $C_{3-10}$ cycloalkyl, $C_{1-6}$ alkyl-$C_{3-10}$ cycloalkyl, $C_{1-6}$ alkyl-$C_{3-10}$ cycloalkyl-$C_{1-6}$ alkyl, $C_{1-6}$ alkyl-heterocyclyl-$C_{1-6}$ alkyl, heterocyclyl, $C_{1-6}$ alkyl-heterocyclyl, heteroaryl or $C_{1-6}$ alkyl-heteroaryl, each of which is optionally substituted with one to four $Z^{1b}$. In some embodiments of the compound of Formula (I-A-1), (I-A-2), (I), (Ia), (Ib), (Ib-1), (Ic) and/or (Id), or pharmaceutically acceptable salt thereof, $R^2$ is $C_{1-6}$ alkyl-$C_{3-10}$ cycloalkyl or $C_{1-6}$ alkyl-$C_{3-10}$ cycloalkyl-$C_{1-6}$ alkyl optionally substituted with one to four $Z^{1b}$.

In some embodiments of the compound of Formula (I-A-1), (I-A-2), (I), (Ia), (Ib), (Ib-1), (Ic) and/or (Id), or pharmaceutically acceptable salt thereof. $R^2$ is $C_{1-6}$ alkyl, which is optionally substituted with one to four $Z^{1b}$. In some embodiments of the compound of Formula (I-A-1), (I-A-2), (I), and/or other formula described herein, $R^2$ is $C_{3-10}$ cycloalkyl or heterocyclyl, each of which is optionally substituted with one to four $Z^{1b}$. In some embodiments of the compound of Formula (I-A-1), (I-A-2), (I), and/or other formula described herein, $R^2$ is $C_{1-6}$ alkyl-heterocyclyl-$C_{1-6}$ alkyl or $C_{1-6}$ alkyl-heterocyclyl, each of which is optionally substituted with one to four $Z^{1b}$.

In some embodiments of the compound of Formula (I-A-1), (I-A-2), (I), and/or other formula described herein, $R^2$ is

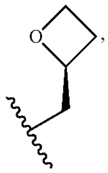, 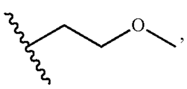, 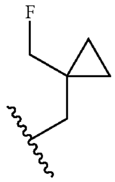, or 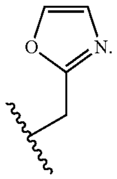.

In some embodiments of the compound of Formula (I-A-1), (I-A-2), and/or other formula described herein, or pharmaceutically acceptable salt thereof $R^1$ is heterocyclyl, $C_{6-10}$ aryl, or 6 membered heteroaryl, which is each optionally substituted with one to three $C_{1-6}$ haloalkyl, halogen, or —CN;

$R^B$ is methyl, halogen, —CN, or —$OCH_3$;

$R^2$ is

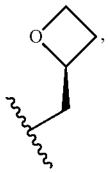, 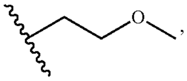, 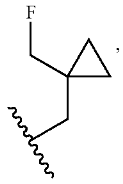, or 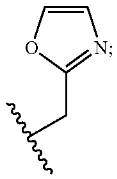;

$R^3$ is —$C(O)R^{3a}$;

$R^{3a}$ is H, $C_{1-4}$ alkyl-$N(R^{9a})(R^{9b})$, —$C_{1-4}$ alkyl-$N(R^{9a})C(O)$—O—$C_{1-4}$ alkyl-$OP(O)(OR^{9c})_2$, —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-$N(R^{9a})(R^{9b})$, —$C_{1-4}$ alkyl-O—C(O)—$C_{1-4}$ alkyl-$OP(O)(OR^{9c})_2$, —$CH_2CH(N(R^{9a})_2)C(O)OR^{9b}$, —$P(O)(OR^{9c})_2$, —$OP(O)(OR^{9c})_2$, —$CH_2P(O)(OR^{9c})_2$, —$CH_2OP(O)(OR^{9c})_2$, or $C_{1-6}$ alkyl-heterocyclyl, wherein the wherein the alkyl or heterocyclyl is each optionally substituted with one to four halogens;

each $R^4$ is independently F, oxo, or —CN;

$R^{5a}$ and $R^{5b}$ are each H; and

Y is —O—; and each $R^8$ is independently H or halogen;

each $R^{9a}$, $R^{9b}$, and $R^{9c}$ is independently H or $C_{1-6}$ alkyl;

m is 0 or 1; and n is 1 or 2.

In some embodiments of the compound of Formula (I-A-1), (I-A-2), (I), (Ia), (Ib), (Ib-1), (Ic) and/or (Id), or pharmaceutically acceptable salt thereof, $R^3$ is —$C(O)OR^{3a}$, —$C(O)N(R^{3a})(R^{3b})$, —$N(R^{3a})C(O)R^{3b}$, —$N(R^{3a})C(O)OR^{3b}$, —$N(R^{3a})C(O)N(R^{3b})(R^{3c})$, —$C(O)NHS(O)_2R^{3a}$, —$S(O)_2R^{3a}$, —$S(O)_2OR^{3a}$, —$S(O)_2N(R^{3a})(R^{3b})$, —$N(R^{3a})S(O)_2R^{3b}$, —$S(O)_2NHC(O)R^{3a}$, —$S(O)(=NR^{3a})R^{3b}$, —$S(O)(=NR^{3a})NR^{3b}$, —$S(=NR^{3a})(=NR^{3b})R^{3c}$, —$P(O)(OR^{3a})(R^{3b})$, —$P(O)(OR^{3a})(OR^{3b})$, —$B(OR^{3a})(OR^{3b})$, or 5 to 10 membered heteroaryl having one to four heteroatoms each independently N, O or S. In some embodiments of the compound of Formula (I-A-1), (I-A-2), (I), (Ia), (Ib), (Ib-1), (Ic) and/or (Id), or pharmaceutically acceptable salt thereof, $R^3$ is H, halogen, heteroaryl, —$C(O)NH_2$, —C(O)OH, —$CH_2C(O)OR^{3a}$, —$C(O)OR^{3a}$, —$C(O)N(R^{3a})S(O)_2(R^{3b})$, —$S(O)_2NHC(O)R^{3a}$, —$P(O)(OR^{3a})_2$, —$C(O)N(R^{3a})S(O)_2N(R^{3b})(R^{3c})$, or —O—$C_{1-6}$alkyl-$C(O)OR^{3a}$, wherein the heteroaryl is optionally substituted with one to four $R^{3d}$. In some embodiments of the compound of Formula (I-A-1), (I-A-2), (I), (Ia), (Ib), (Ib-1), (Ic) and/or (Id), or pharmaceutically acceptable salt thereof, $R^3$ is —C(O)OH, —$C(O)OR^{3a}$, —$C(O)N(R^{3a})S(O)_2(R^{3b})$, —$S(O)_2NHC(O)R^{3a}$, —$C(O)NR^{3a}S(O)_2NR^{3b}R^{3c}$, or heteroaryl, wherein the heteroaryl is optionally substituted with one to four $R^{3d}$. In some embodiments of the compound of Formula (I-A-1), (I-A-2), (I), (Ia), (Ib), (Ib-1), (Ic) and/or (Id), or pharmaceutically acceptable salt thereof, $R^3$ is 5 to 6 membered heteroaryl optionally substituted with one to four $R^{3d}$. In some embodiments, $R^3$ is —$C(O)OR^{3a}$. In some embodiments of the compound of Formula (I-A-1), (I-A-2), (I), (Ia), (Ib), (Ib-1), (Ic) and/or (Id), or pharmaceutically acceptable salt thereof, $R^3$ is —C(O)OH.

In some embodiments of the compound of Formula (I-A-1), (I-A-2), (I), (Ia), (Ib), (Ib-1), (Ic) and/or (Id), or pharmaceutically acceptable salt thereof, $R^3$ is

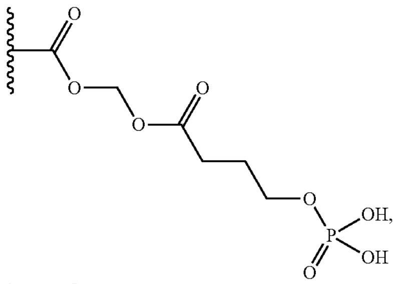

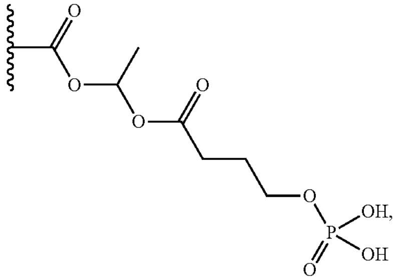

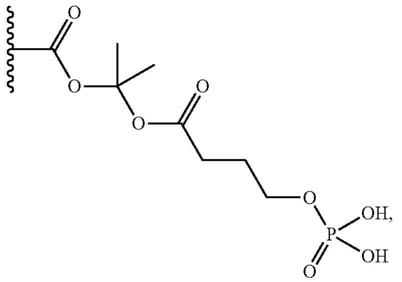

-continued
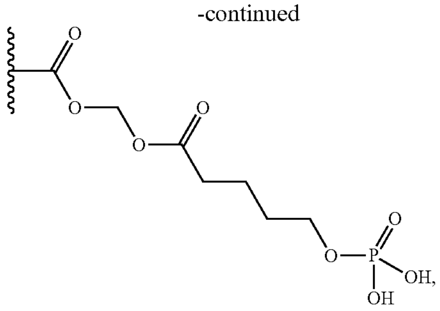
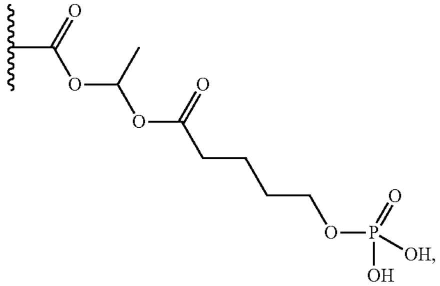
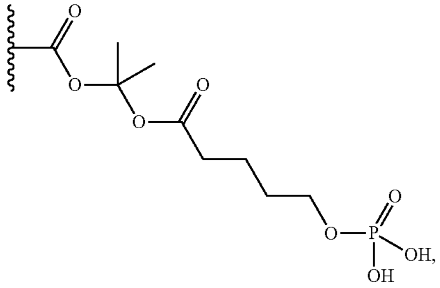
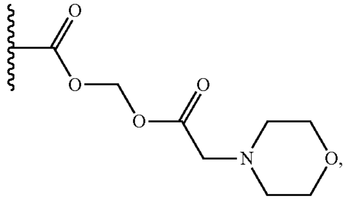
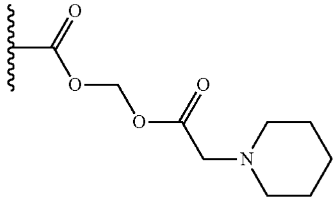
,
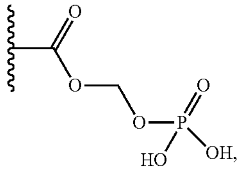
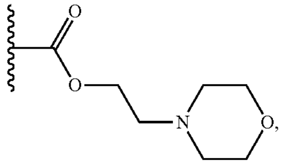
-continued
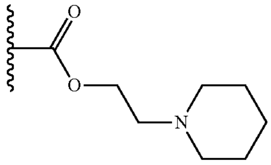
,
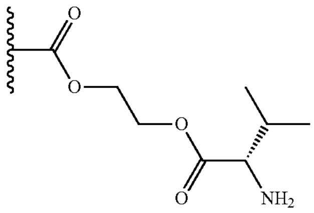
,
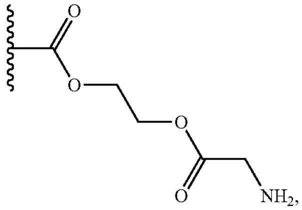
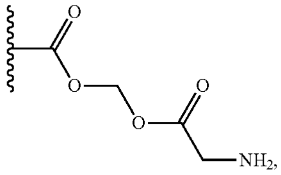
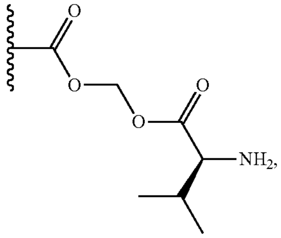
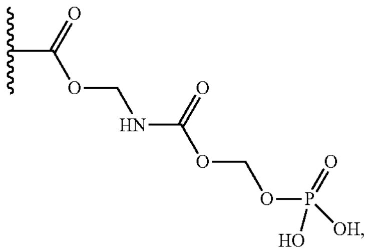
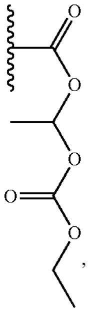
,
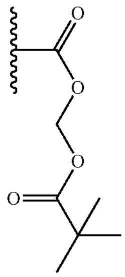
,
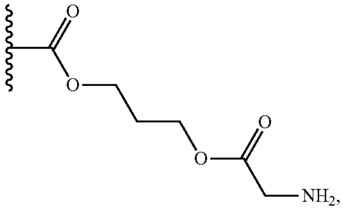

-continued

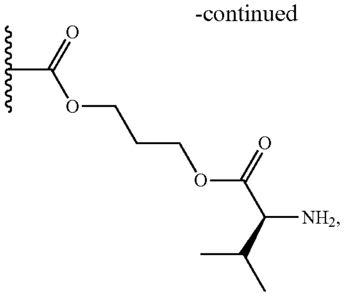

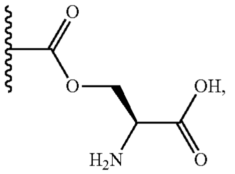

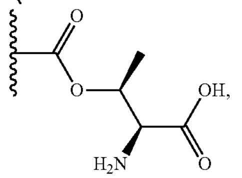

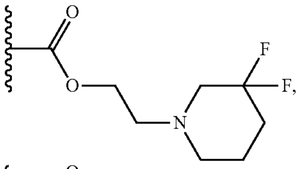

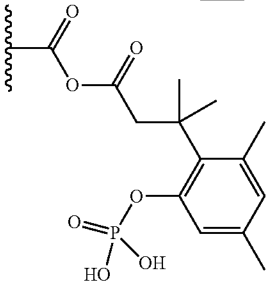

,

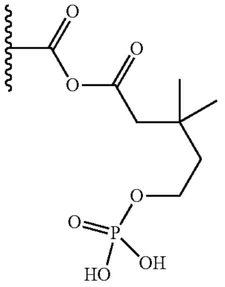, or 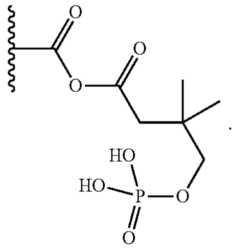.

In some embodiments of the compound of Formula (I-A-1), (I-A-2), (I), (Ia), (Ib), (Ib-1), (Ic) and/or (Id), or pharmaceutically acceptable salt thereof, $R^{3a}$ is H, $C_{1-4}$ alkyl-N($R^{9a}$)($R^{9b}$), —$C_{1-4}$ alkyl-N($R^{9a}$)C(O)—O—$C_{1-4}$ alkyl-OP(O)($OR^{9c}$)$_2$, $C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-O—C(O)—$C_{1-4}$ alkyl-OP(O)($OR^{9c}$)$_2$, —$CH_2CH$(N($R^{9a}$)$_2$)C(O)$OR^{9b}$, —P(O)($OR^{9c}$)$_2$, —OP(O)($OR^{9c}$)$_2$, —$CH_2$P(O)($OR^{9c}$)$_2$, —$CH_2$OP(O)($OR^{9c}$)$_2$, —$OCH_2$P(O)($OR^{9c}$)$_2$, —C(O)$OCH_2$P(O)($OR^{9c}$)$_2$, —P(O)($R^{9c}$)($OR^{9d}$), —OP(O)($R^{9c}$)($OR^{9d}$), —$CH_2$P(O)($R^{9c}$)($OR^{9d}$), —$OCH_2$P(O)($R^{9c}$)($OR^{9d}$), —C(O)$OCH_2$P(O)($R^{9c}$)($OR^{9d}$), —P(O)(N($R^{9c}$)$_2$)$_2$, —OP(O)(N($R^{9c}$)$_2$)$_2$, —$CH_2$P(O)(N($R^{9c}$)$_2$)$_2$, —$OCH_2$P(O)(N($R^{9c}$)$_2$)$_2$, —C(O)$OCH_2$P(O)(N($R^{9c}$)$_2$)$_2$, —P(O)(N($R^{9c}$)$_2$)($OR^{9d}$), —OP(O)(N($R^{9c}$)$_2$)($OR^{9d}$), —$CH_2$P(O)(N($R^{9c}$)$_2$)($OR^{9d}$), —$OCH_2$P(O)(N($R^{9c}$)$_2$)($OR^{9d}$), —C(O)$OCH_2$P(O)(N($R^{9c}$)$_2$)($OR^{9d}$), —P(O)($R^{9c}$)(N($R^{9d}$)$_2$), —OP(O)($R^{9c}$)(N($R^{9d}$)$_2$), —$CH_2$P(O)($R^{9c}$)(N($R^{9d}$)$_2$), —$OCH_2$P(O)($R^{9c}$)(N($R^{9d}$)$_2$), —C(O)$OCH_2$P(O)

($R^{9c}$)(N($R^{9d}$)$_2$), or $C_{1-6}$ alkyl-heterocyclyl, wherein the wherein the alkyl or heterocyclyl is each optionally substituted with one to four halogens.

In some embodiments of the compound of Formula (I-A-1), (I-A-2), (I), (Ia), (Ib), (Ib-1), (Ic) and/or (Id), or pharmaceutically acceptable salt thereof, $R^3$ is H, —Br,

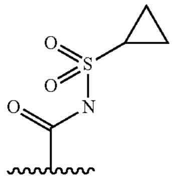, 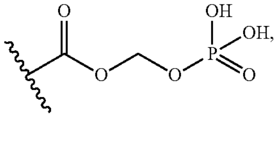

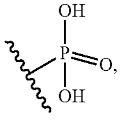 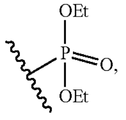 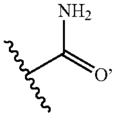

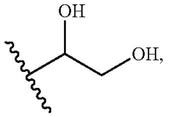 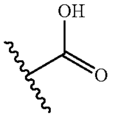 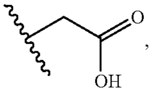,

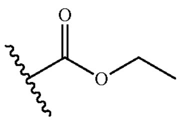, 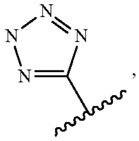,

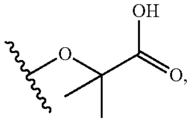 or 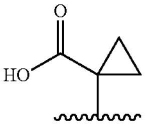.

In some embodiments of the compound of Formula (I), (I-A-1), (I-A-2), (Ia), (Ib), (Ic) and/or (Id), or pharmaceutically acceptable salt thereof, each $R^{3a}$, $R^{3b}$, and $R^{3c}$ is independently H, $C_{1-6}$ alkyl, $C_{1-6}$ haloalkyl, or $C_{3-10}$ cycloalkyl.

In some embodiments of the compound of Formula (I-A-1), (I-A-2), (I), (Ia), (Ib), (Ib-1), (Ic) and/or (Id), or pharmaceutically acceptable salt thereof, each $R^4$ is independently $C_{1-6}$ alkyl, $C_{1-6}$ haloalkyl, $C_{3-10}$ cycloalkyl, heterocyclyl, $C_{6-10}$ aryl, heteroaryl, halogen, oxo, —CN, or —O—$R^{4a}$. In some embodiments of the compound of Formula (I-A-1), (I-A-2), (I), (Ia), (Ib), (Ib-1), (Ic) and/or (Id), or pharmaceutically acceptable salt thereof, each $R^4$ is independently $C_{1-6}$ alkyl, $C_{2-6}$ alkoxyalkyl, $C_{1-6}$ alkoxy, $C_{1-6}$ haloalkoxy, halogen, oxo, OH, or —CN. In some embodiments of the compound of Formula (I-A-1), (I-A-2), (I), (Ia), (Ib), (Ib-1), (Ic) and/or (Id), or pharmaceutically acceptable salt thereof, two $R^4$ groups attached to adjacent ring atoms are combined with the atoms to which they are attached to form a $C_{3-10}$ cycloalkyl. In some embodiments of the compound of Formula (I-A-1), (I-A-2), (I), (Ia), (Ib), (Ib-1), (Ic) and/or (Id), or pharmaceutically acceptable salt thereof, each $R^4$ is independently $C_{1-6}$ alkyl, halogen, oxo, —CN, or —$OR^4$a. In some embodiments of the compound of Formula (I-A-1), (I-A-2), (I), (Ia), (Ib), (Ib-1), (Ic) and/or (Id), or pharmaceutically acceptable salt thereof, each $R^4$ is independently F, oxo, or —CN.

In some embodiments of the compound of Formula (I-A-1), (I-A-2), and/or (I) or pharmaceutically acceptable salt thereof, each $R^{5a}$ and $R^{5b}$ is independently H, $C_{1-6}$ alkyl, F, Cl, $C_{3-10}$ cycloalkyl, 3 to 12 membered heterocyclyl having one to three heteroatoms each independently O, N, or S, or —CN.

In some embodiments of the compound of Formula (I-A-1), (I-A-2), and/or (I) or pharmaceutically acceptable salt thereof, $R^{6a}$ is H, $C_{1-6}$ alkyl, $C_{3-10}$ cycloalkyl, or heterocyclyl. In some embodiments, $R^{6a}$ is H, $C_{1-6}$ alkyl, $C_{3-10}$ cycloalkyl, or 3 to 12 membered heterocyclyl having one to three heteroatoms each independently O, N, or S.

In some embodiments of the compound of Formula (I-A-1), (I-A-2), and/or (I) or pharmaceutically acceptable salt thereof, each $R^{6b}$ and $R^{6c}$ is independently H, F, Cl, $C_{1-3}$ alkyl, or —CN. In some embodiments, each $R^{6b}$ and $R^{6c}$ is independently H, F, Cl, or —CN.

In some embodiments of the compound of Formula (I-A-1), (I-A-2), and/or (I) or pharmaceutically acceptable salt thereof, $R^{6c}$ is combined with one $R^4$ group and the atoms to which they are attached to form a $C_{3-10}$ cycloalkyl or 3 to 12 membered heterocyclyl having one to three heteroatoms each independently N, O or S, wherein the cycloalkyl and heterocyclyl are each optionally substituted with one to four $R^{4c}$.

In some embodiments of the compound of Formula (I-A-1), (I-A-2), (I), (Ia), (Ib), (Ib-1), (Ic) and/or (Id), or pharmaceutically acceptable salt thereof, each $R^8$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$ NH($C_{1-9}$ alkyl), or —S(O)$_2$N($C_{1-9}$ alkyl)$_2$. In some embodiments, each $R^8$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), or —C(O)O(heteroaryl). In some embodiments, each $R^8$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, or —$NH_2$. In some embodiments, each $R^8$ is independently $C_{1-3}$ alkyl, $C_{1-3}$ haloalkyl, $C_{2-6}$ alkenyl, $C_{2-6}$ alkynyl, halogen, $C_{3-7}$ cycloalkyl, oxo, —OH, —CN, or —$NH_2$. In some embodiments of the compound of Formula (I), (I-A-1), and/or (I-A-2), or a pharmaceutically acceptable salt thereof, each $R^8$ is independently $C_{1-3}$ alkyl, $C_{1-3}$ haloalkyl, halogen, $C_{3-7}$ cycloalkyl, oxo, —OH, —CN, or —$NH_2$. In some embodiments, each $R^8$ is independently $C_{1-3}$ alkyl, $C_{1-3}$ haloalkyl, halogen, $C_{3-7}$ cycloalkyl, oxo, or —CN. the compound of Formula (I), (I-A-1), and/or (I-A-2), or a pharmaceutically acceptable salt thereof. $R^8$ is $C_{1-9}$ alkyl, halogen, or —O($C_{1-9}$ alkyl). In some embodiments of the compound of Formula (I-A-1), (I-A-2), (I), (Ia), (Ib), (Ib-1), (Ic) and/or (Id), or pharmaceutically acceptable salt thereof, each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$ NH($C_{1-9}$ alkyl), or —S(O)$_2$N($C_{1-9}$ alkyl)$_2$. In some embodiments Formula (I-A-1), (I-A-2), (I), (Ia), (Ib), (Ib-1), (Ic) and/or (Id), or pharmaceutically acceptable salt thereof, each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), or —C(O)O(heteroaryl). In some embodiments of the compound of Formula (I-A-1), (I-A-2), (I), (Ia), (Ib), (Ib-1), (Ic) and/or (Id), or pharmaceutically acceptable salt thereof, each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, or —$NH_2$. In some embodiments Formula (I-A-1), (I-A-2), (I), (Ia), (Ib), (Ib-1), (Ic) and/or (Id), or pharmaceutically acceptable salt thereof, each $Z^{1b}$ is independently $C_{1-3}$ alkyl, $C_{1-3}$ haloalkyl, $C_{2-6}$ alkenyl, $C_{2-6}$ alkynyl, halogen, $C_{3-7}$ cycloalkyl, oxo, —OH, —CN, or —$NH_2$. In some embodiments of the compound of Formula (I-A-1), (I-A-2), (I), (Ia), (Ib), (Ib-1), (Ic) and/or (Id), or pharmaceutically acceptable salt thereof, each $Z^{1b}$ is independently $C_{1-3}$ alkyl, $C_{1-3}$ haloalkyl, halogen, $C_{3-7}$ cycloalkyl, oxo, —OH, —CN, or —$NH_2$. In some embodiments of the compound of Formula (I-A-1), (I-A-2), (I), (Ia), (Ib), (Ib-1), (Ic) and/or (Id), or pharmaceutically acceptable salt thereof, each $Z^{1b}$ is independently $C_{1-3}$ alkyl, $C_{1-3}$ haloalkyl, halogen, $C_{3-7}$ cycloalkyl, oxo, or —CN.

In some embodiments, the compound of Formula (I), (I-A-1), (I-A-2), (Ia), (Ib), (Ic), and/or (Id), or pharmaceutically acceptable salt thereof has a formula:

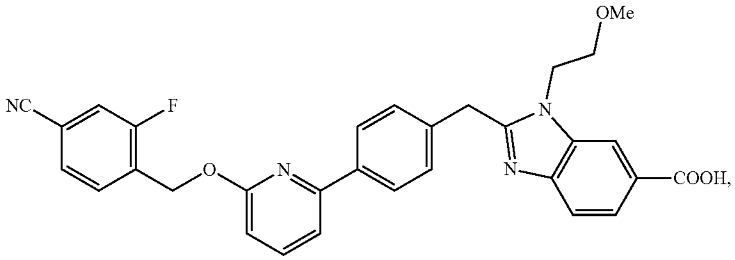

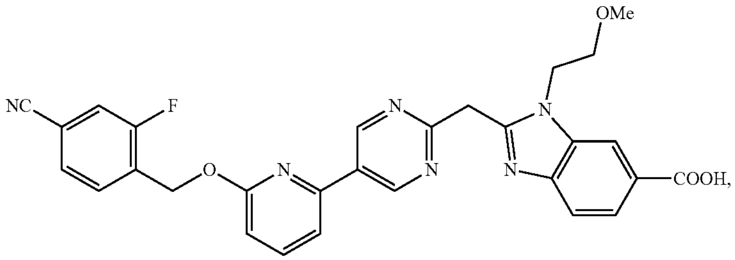

-continued
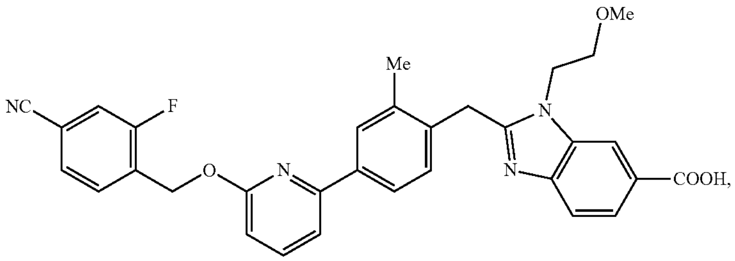
,
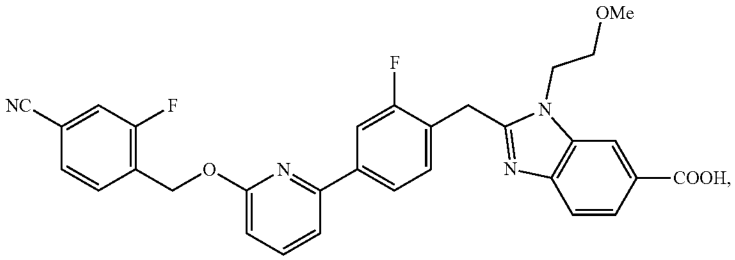
,
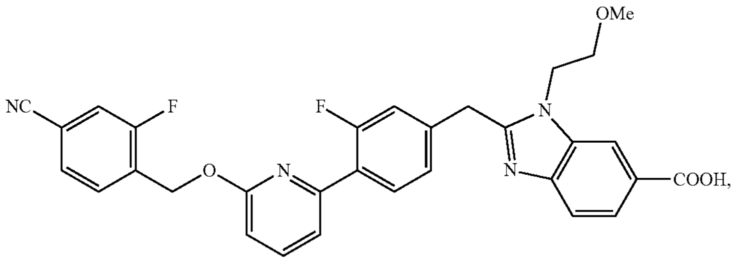
,
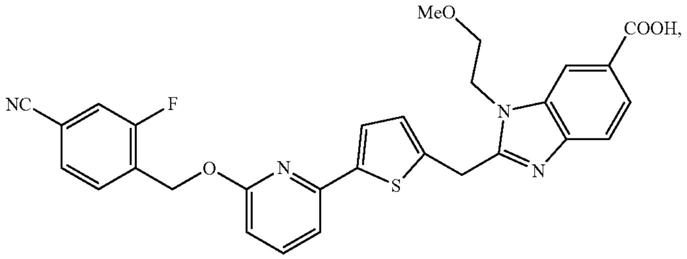
,
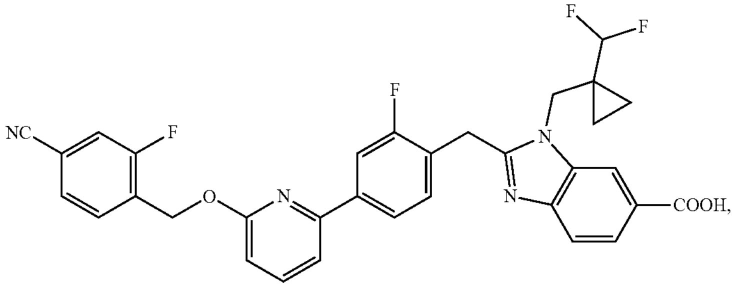
,
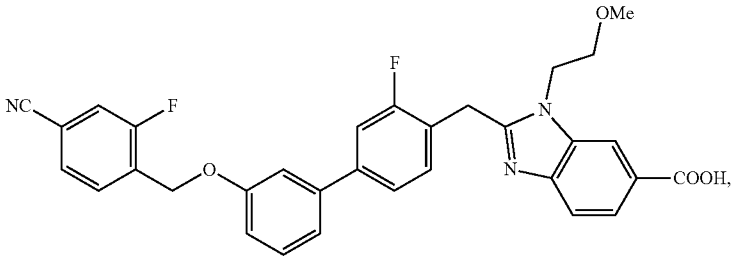
, -continued
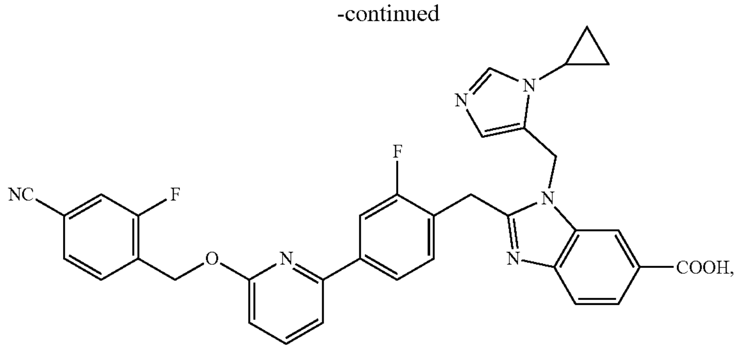
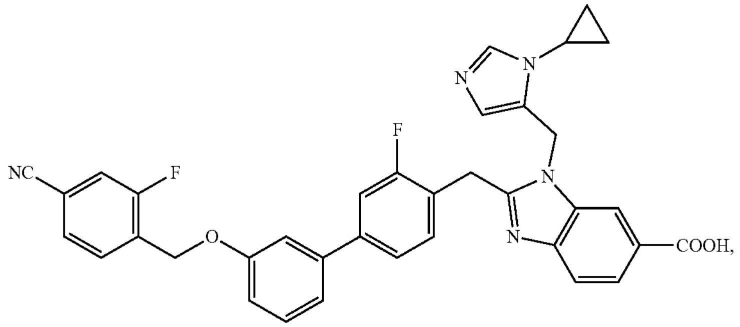
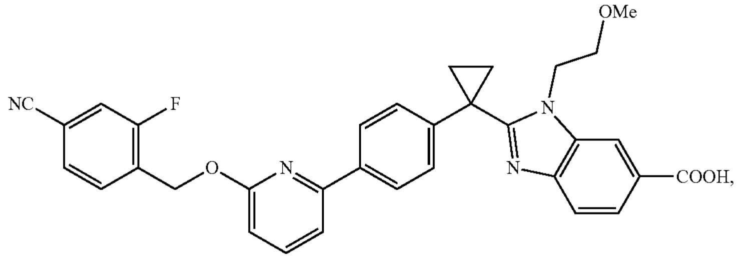
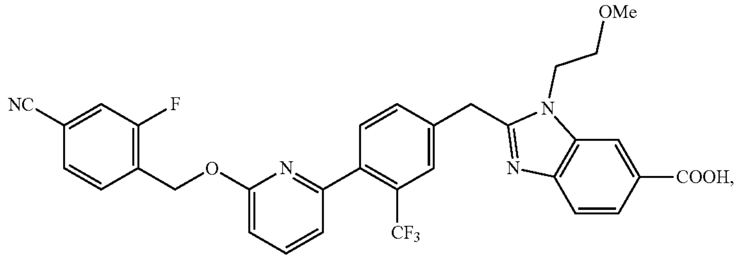
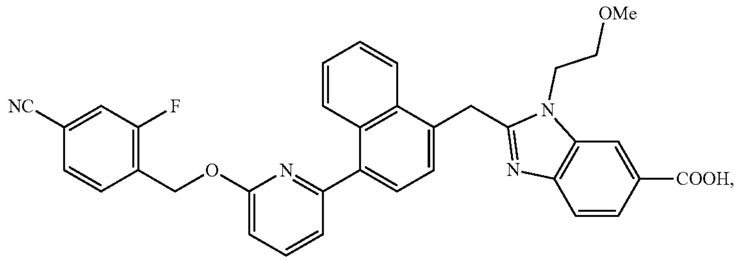
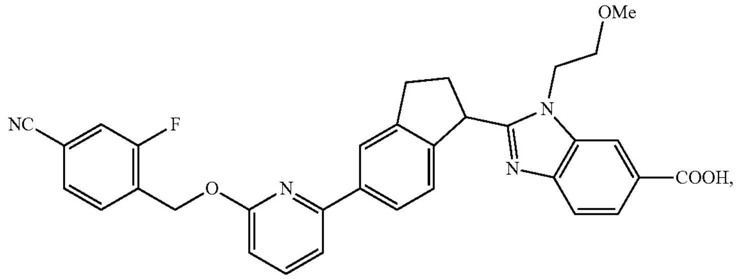

-continued
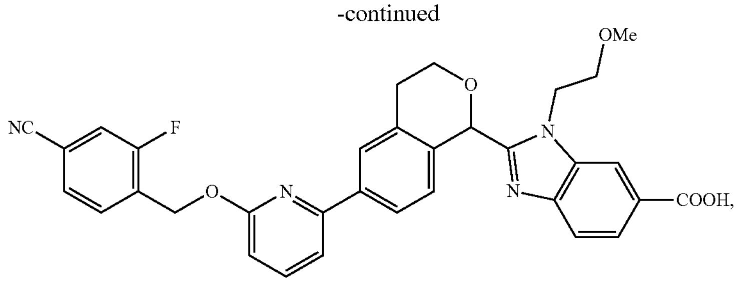
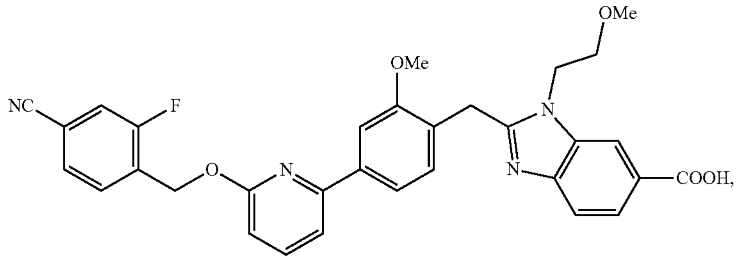
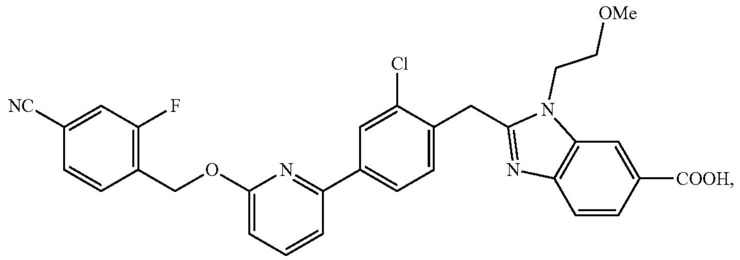
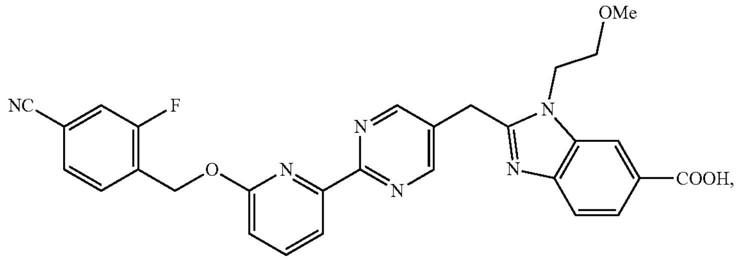
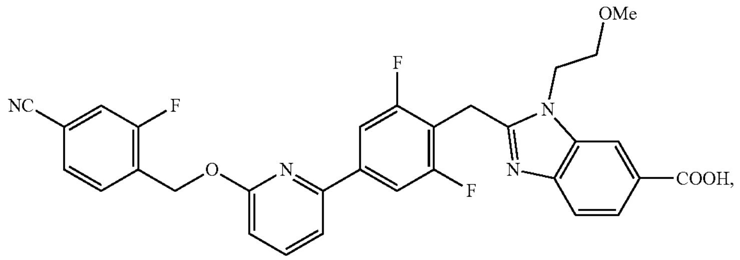
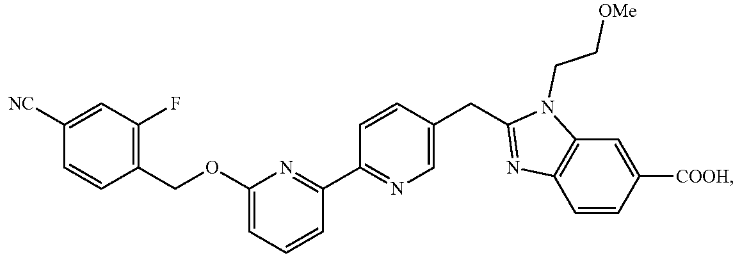

-continued
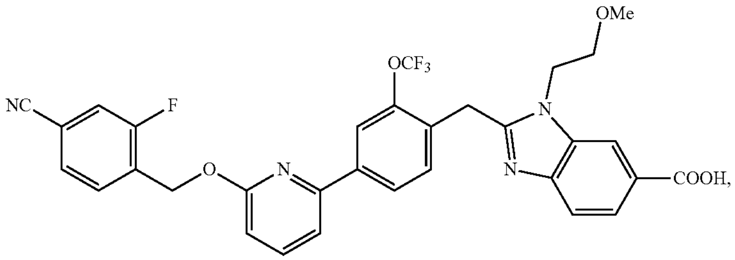
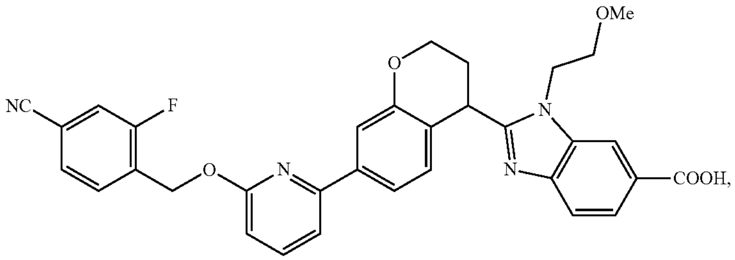
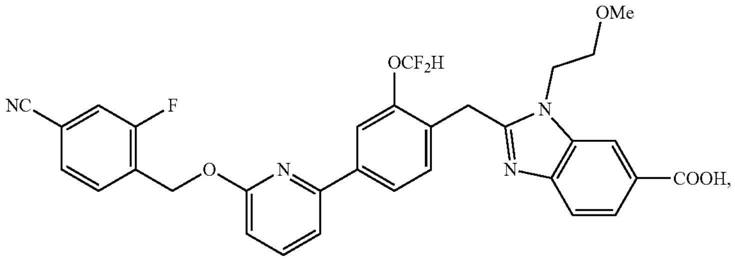
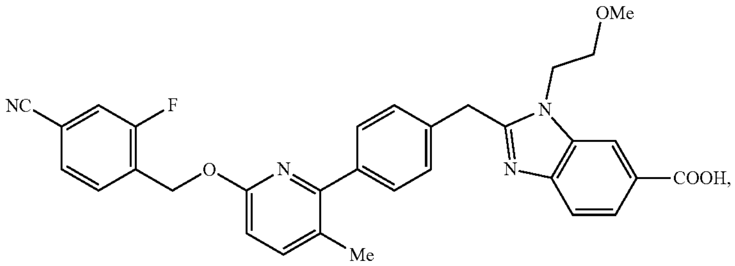
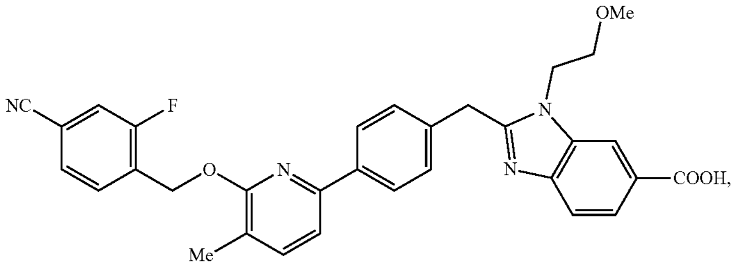
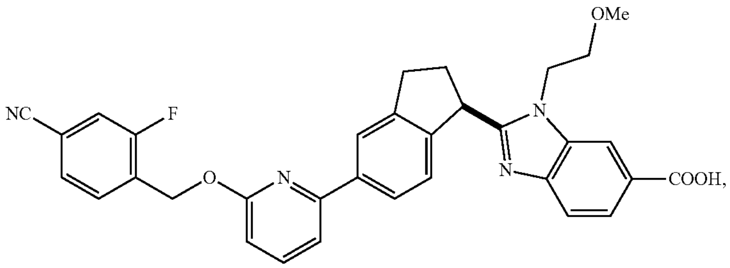

-continued
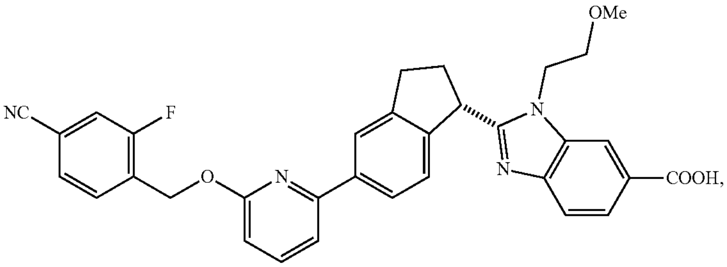
,
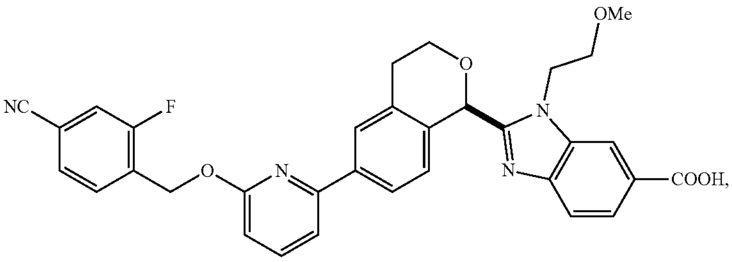
,
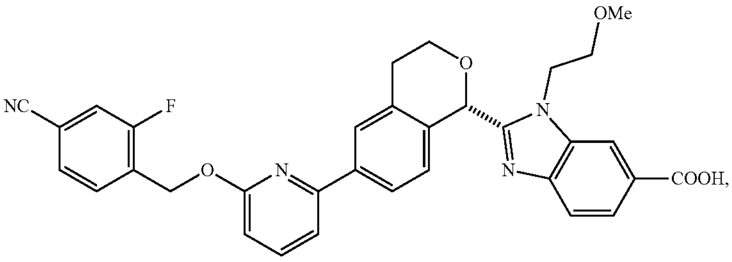
,
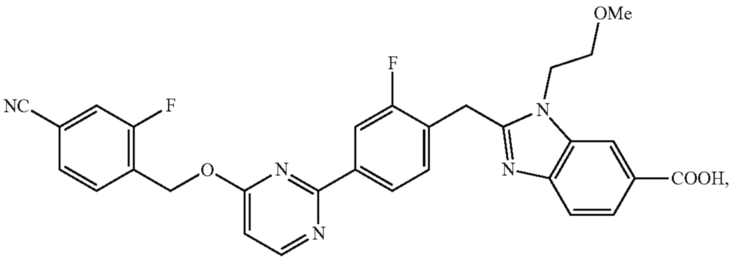
,
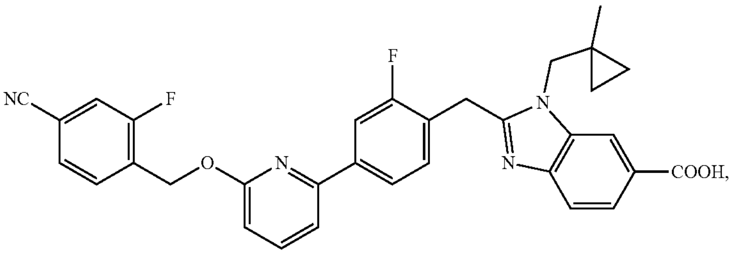
,
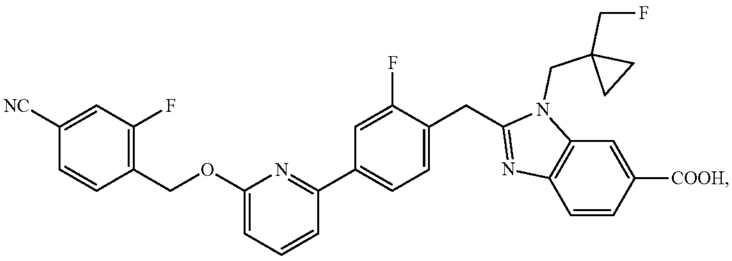
, -continued
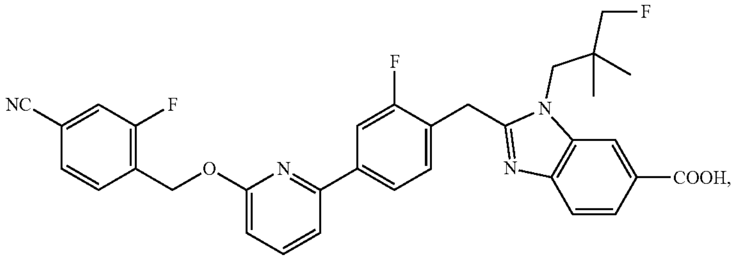
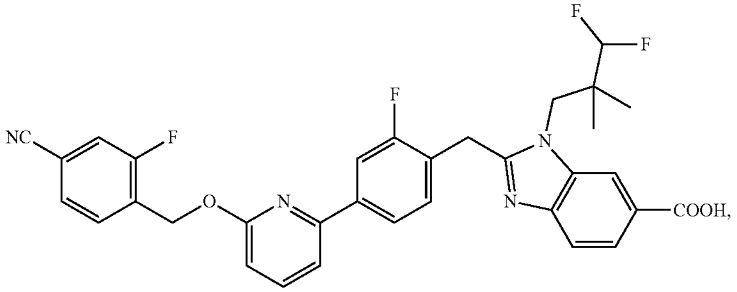
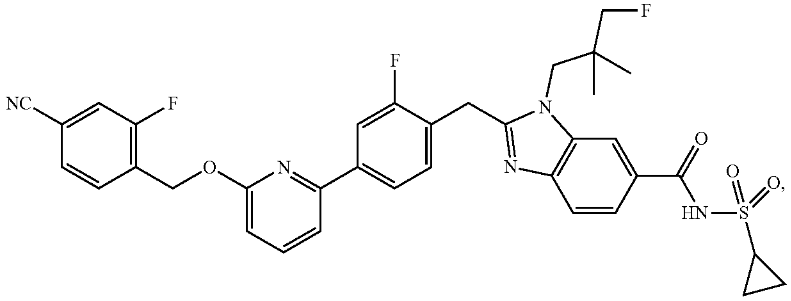
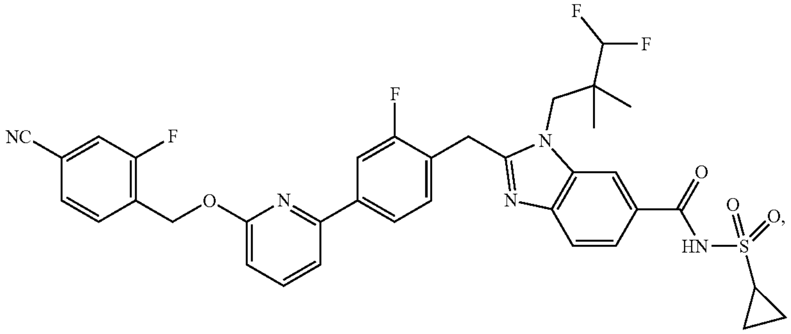
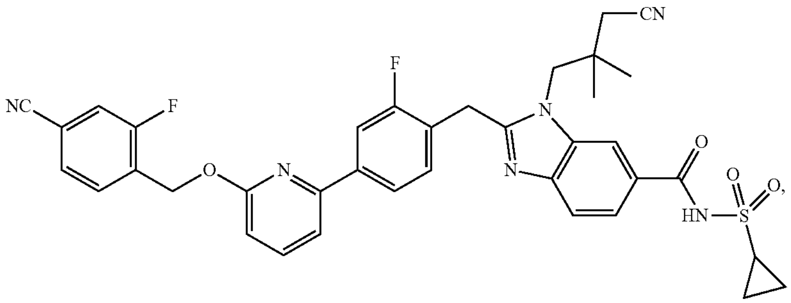

-continued
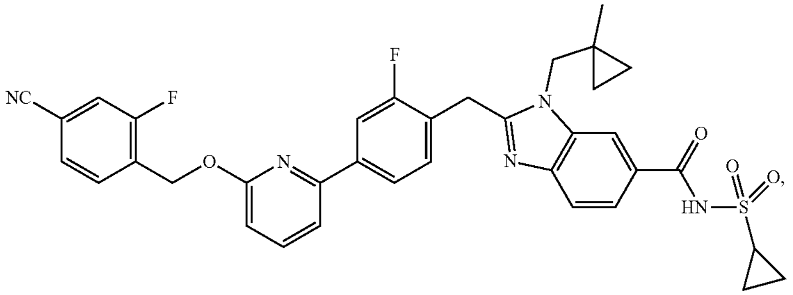
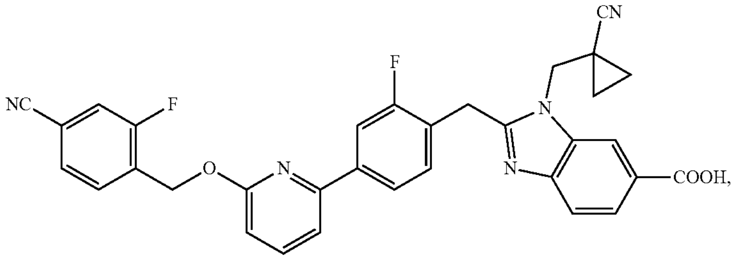
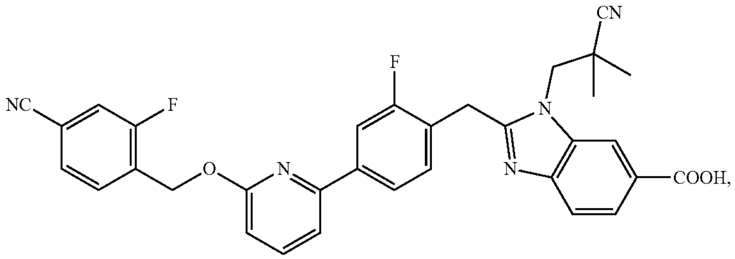
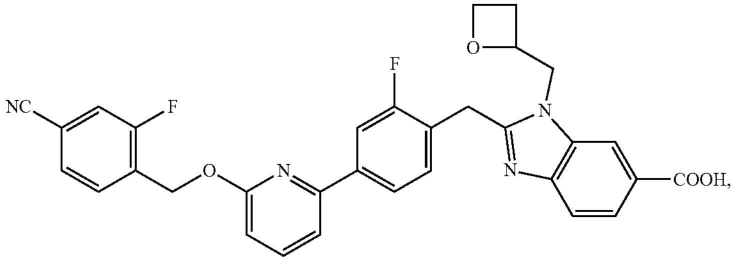
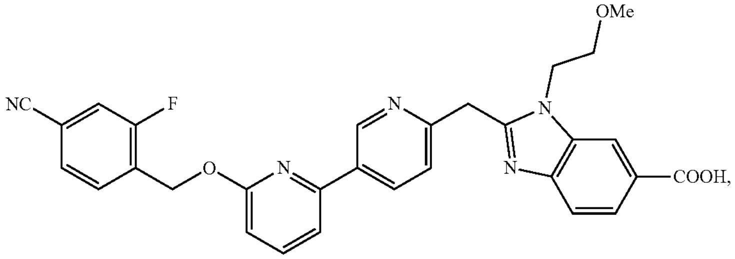
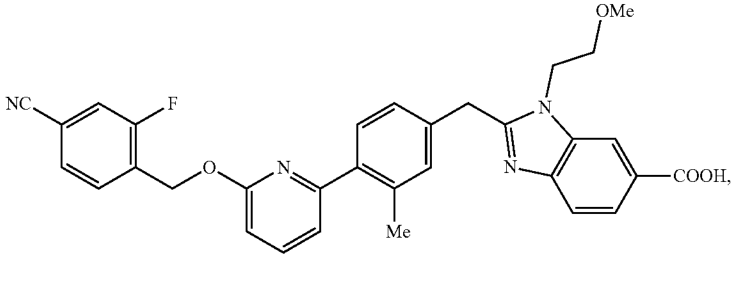

-continued
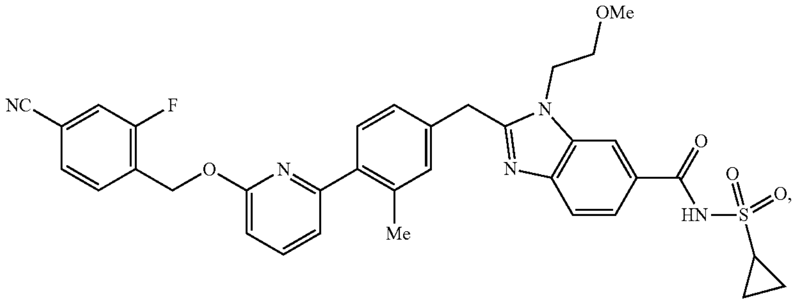
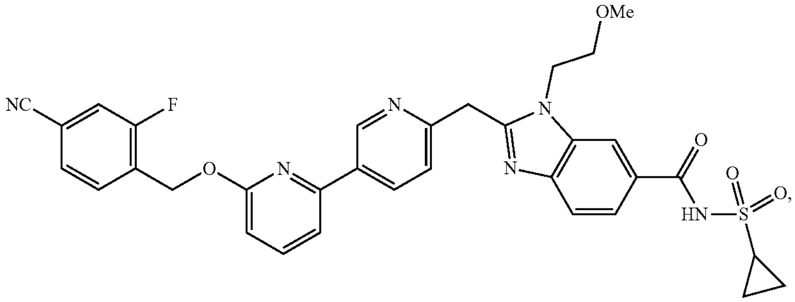
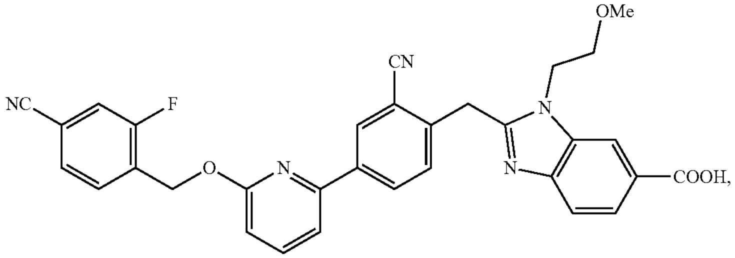
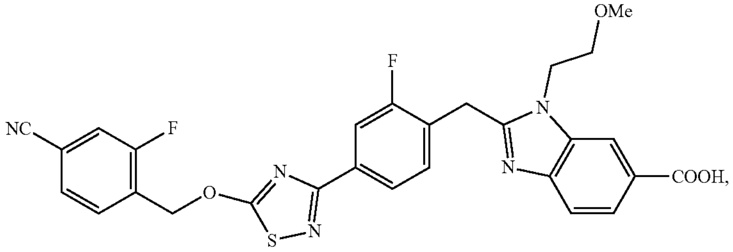
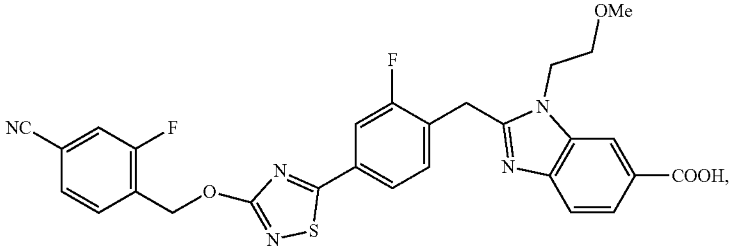
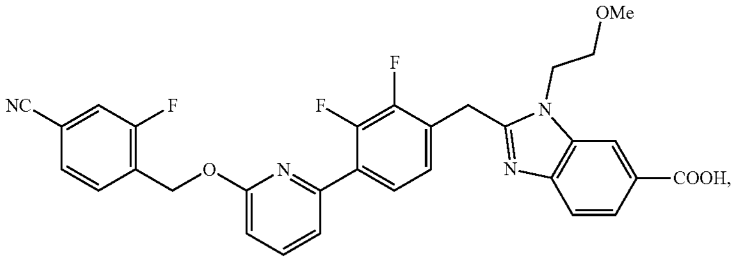

-continued
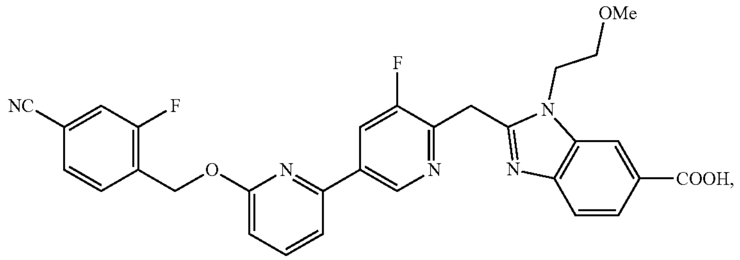
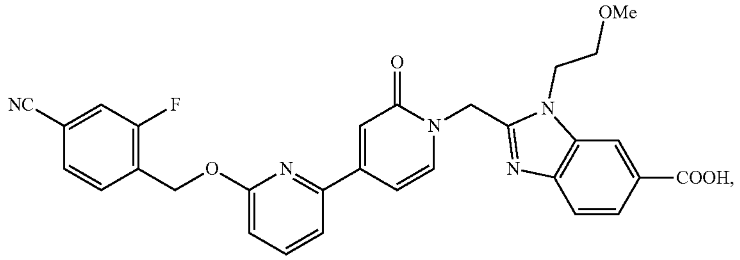
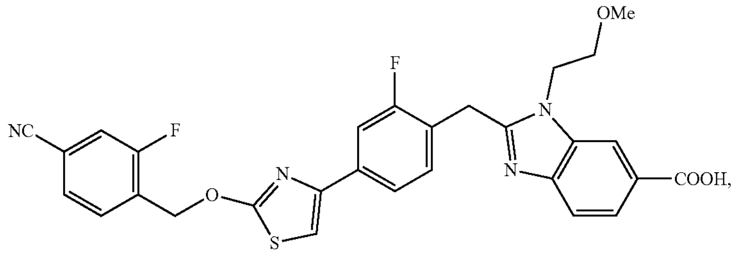
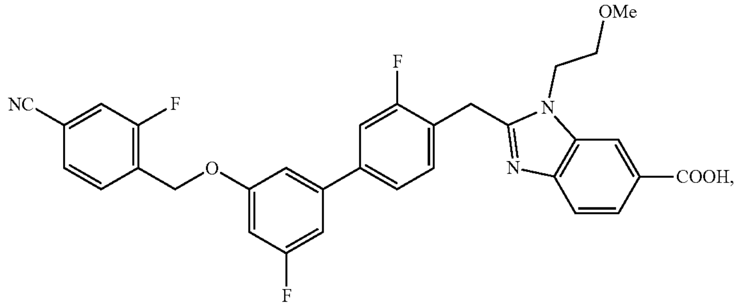
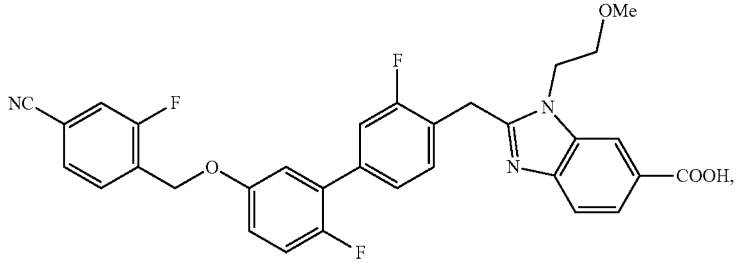
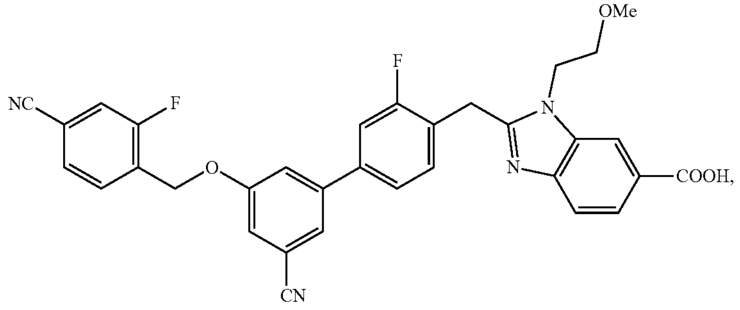

-continued
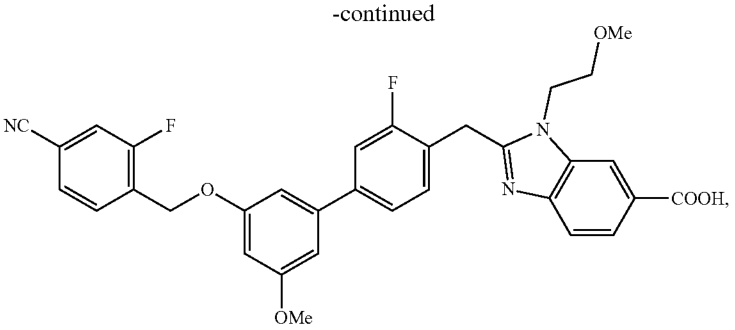
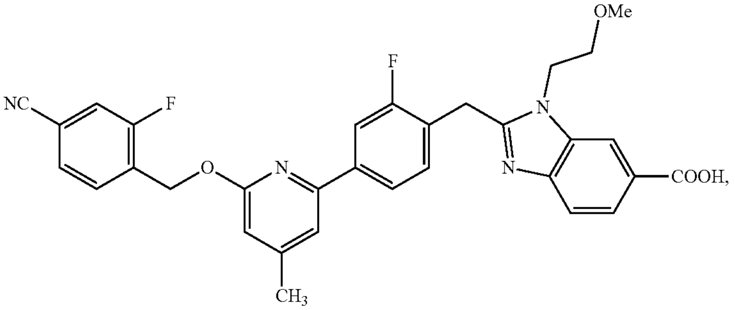
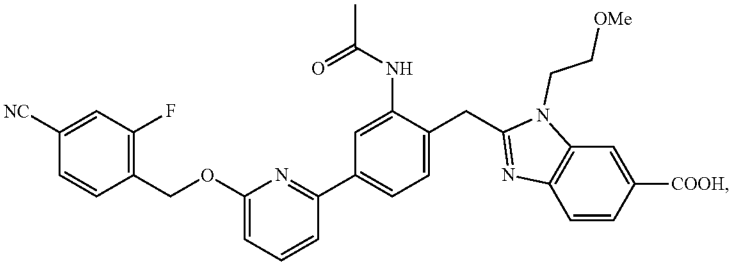
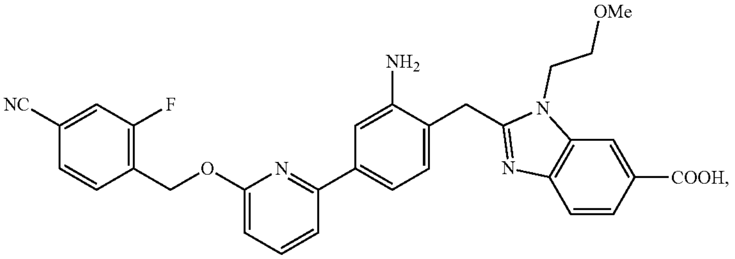
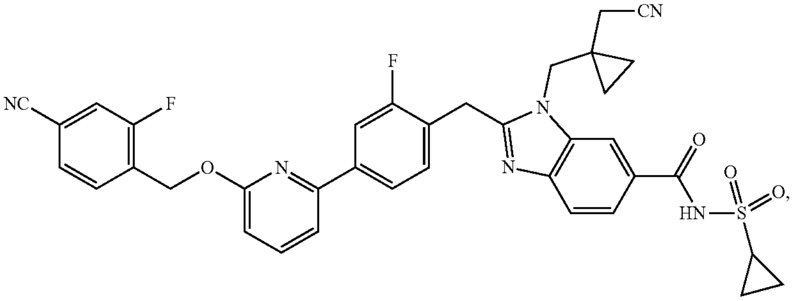
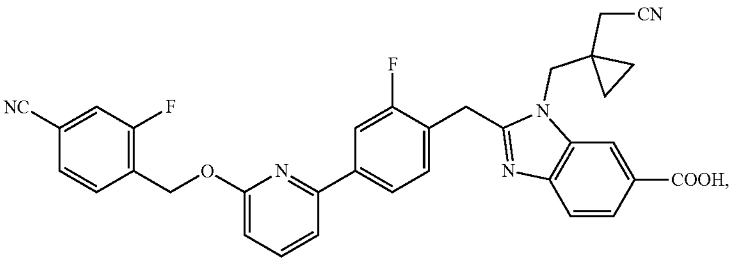

-continued
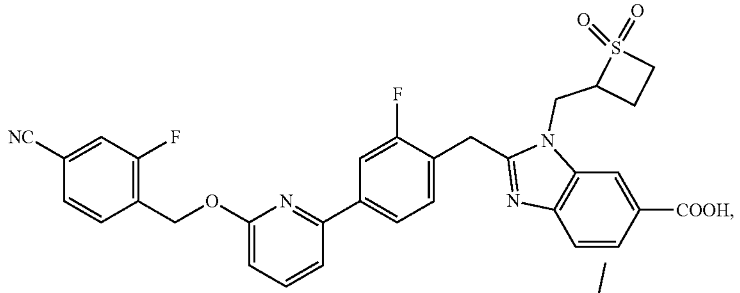
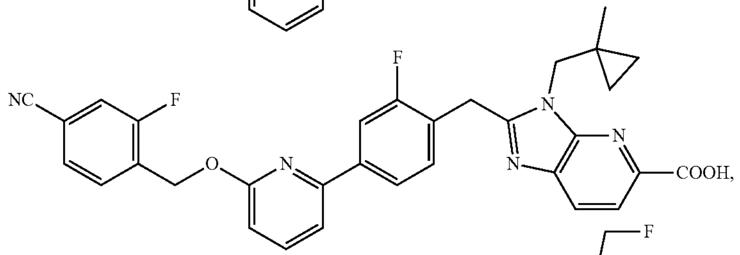
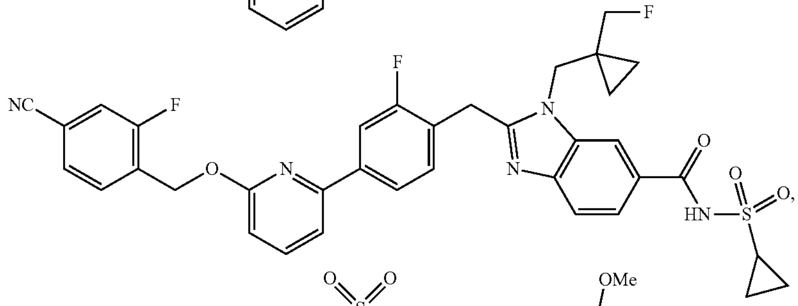
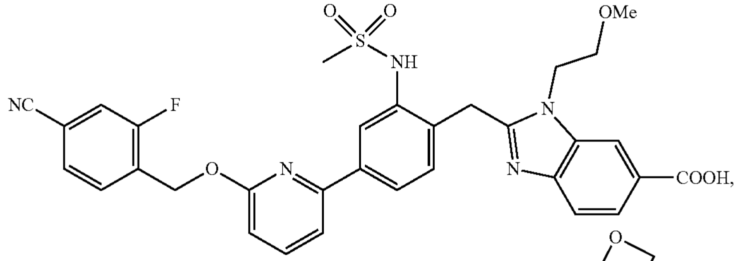
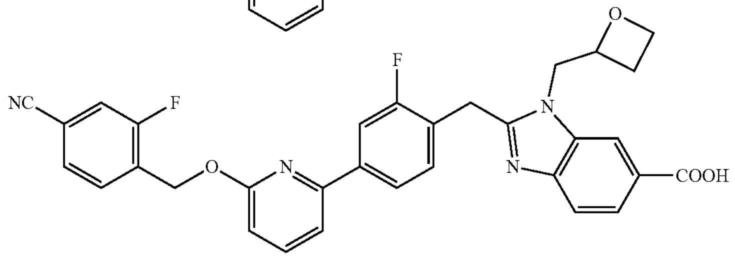
In some embodiments, a compound of the disclosure has the structure:
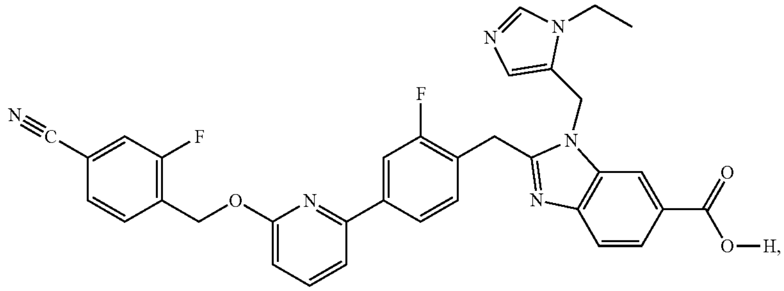

-continued
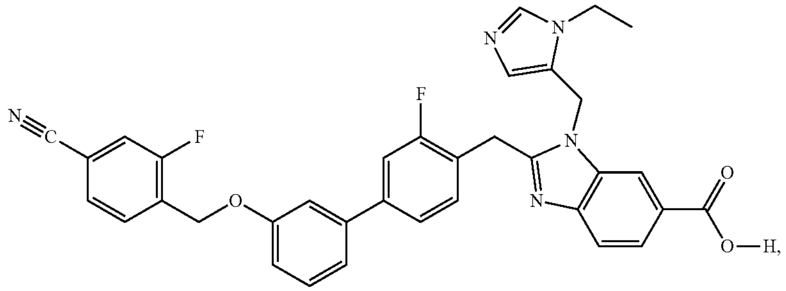
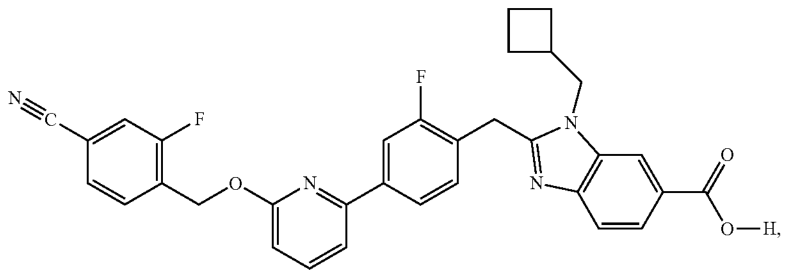
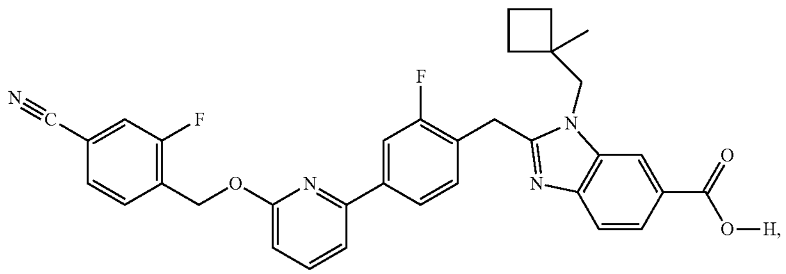
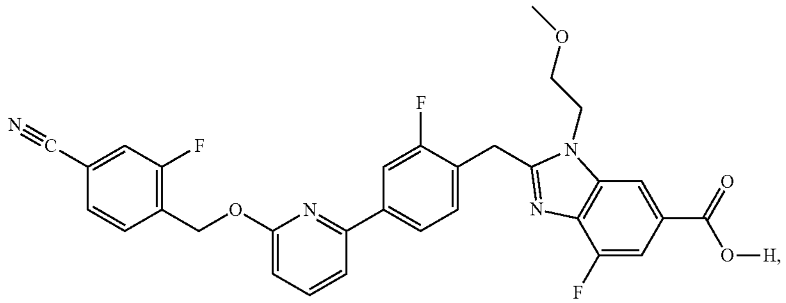
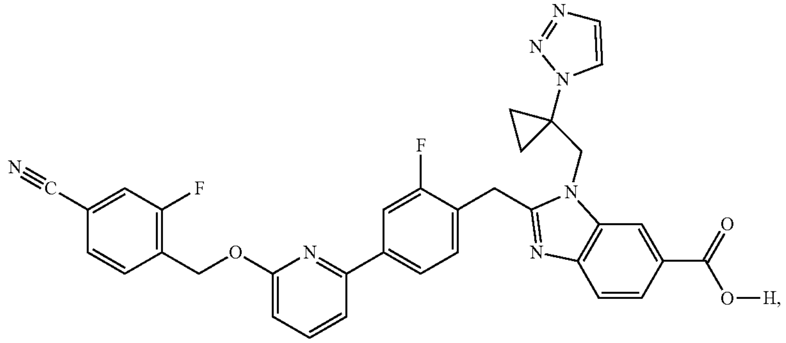

-continued
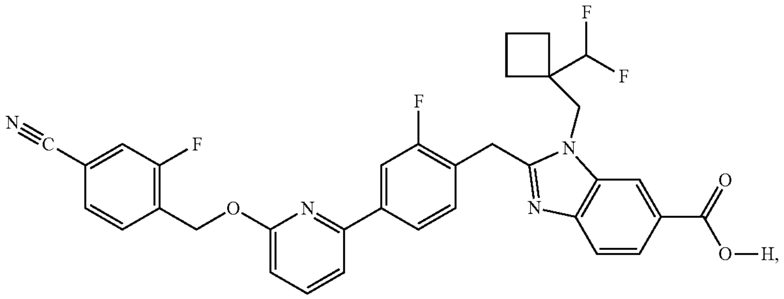
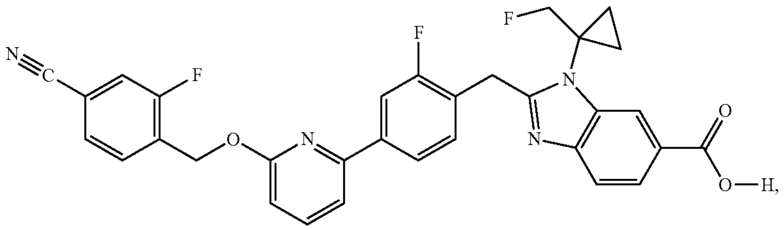
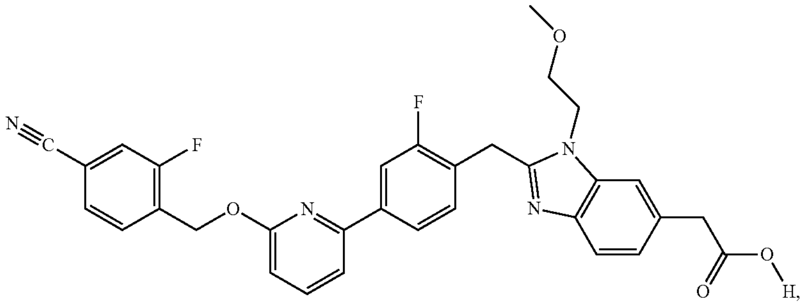
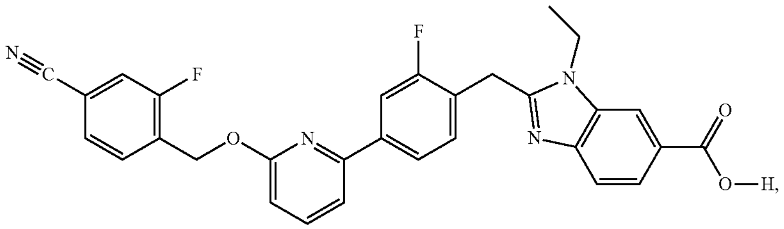
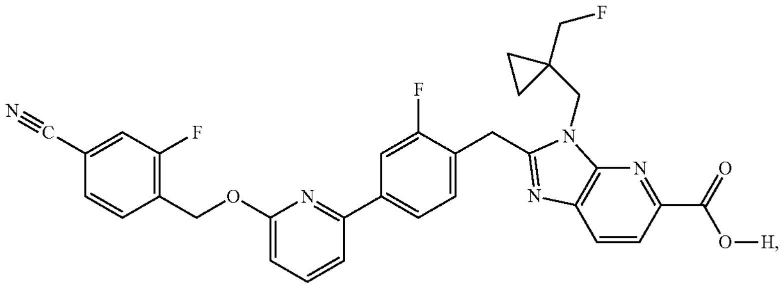
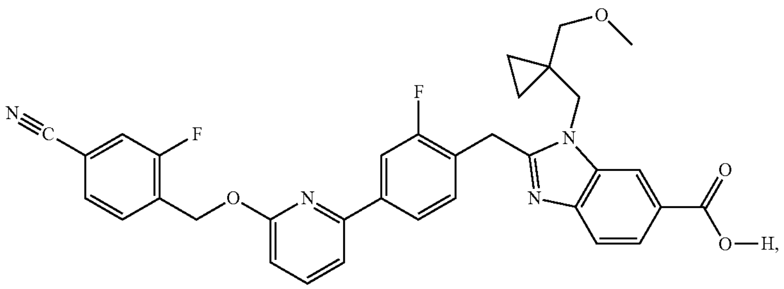

-continued
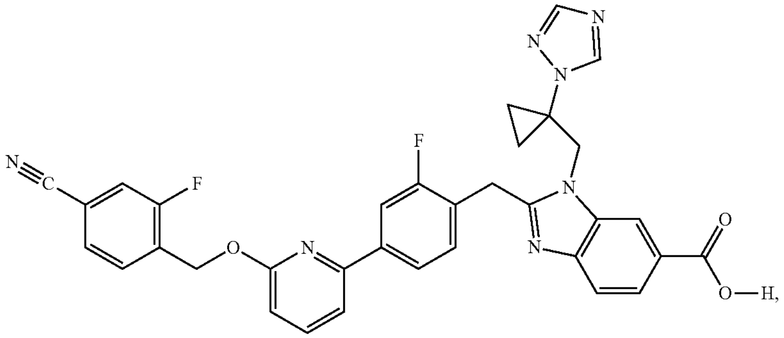
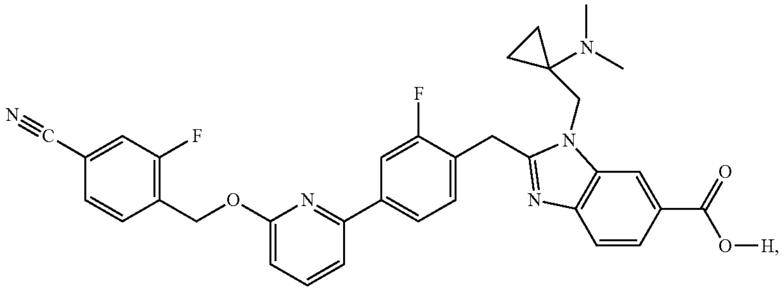
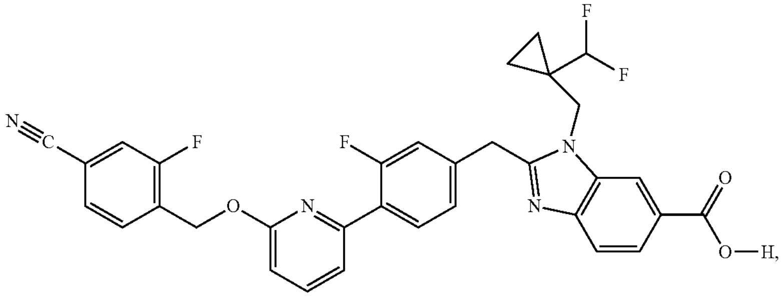
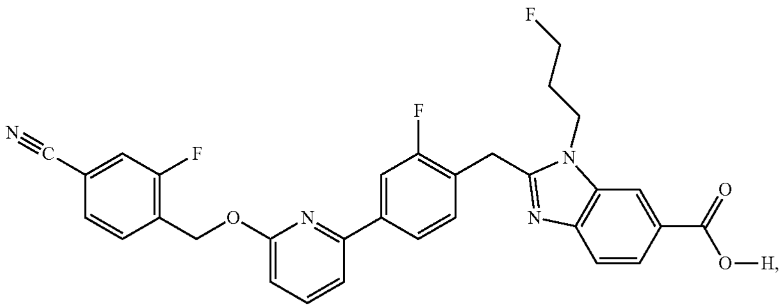
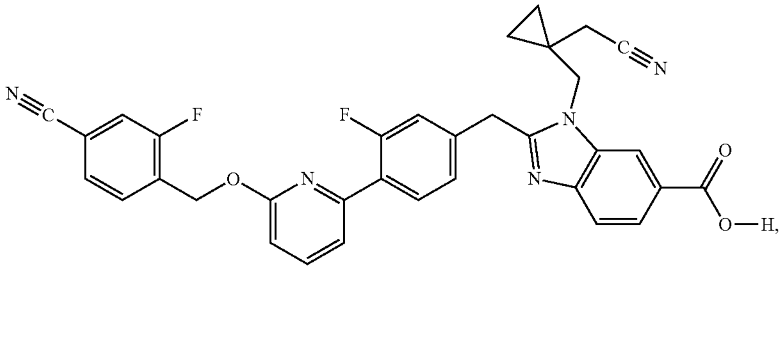

-continued
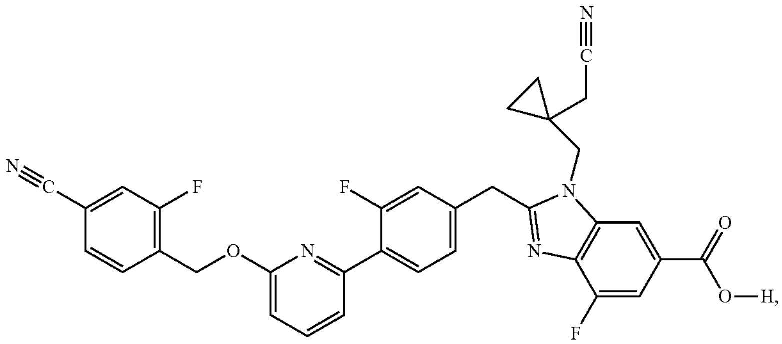
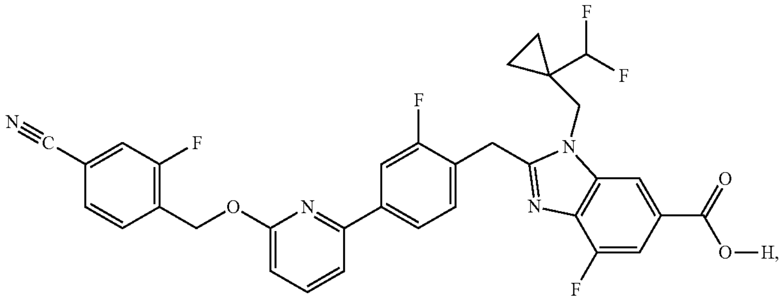
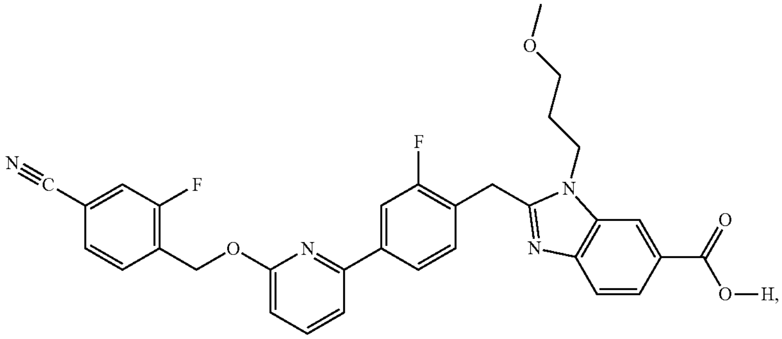
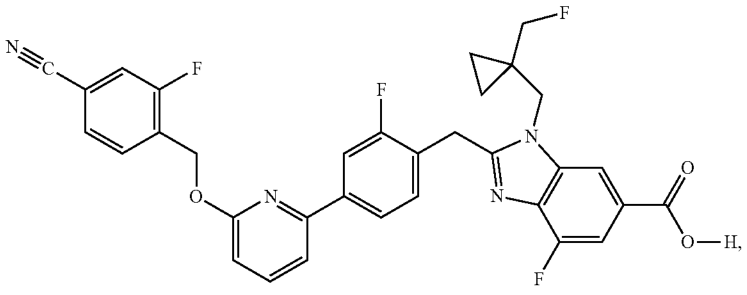
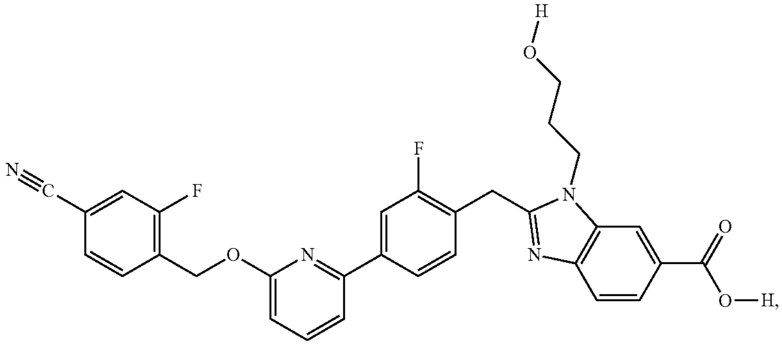

-continued
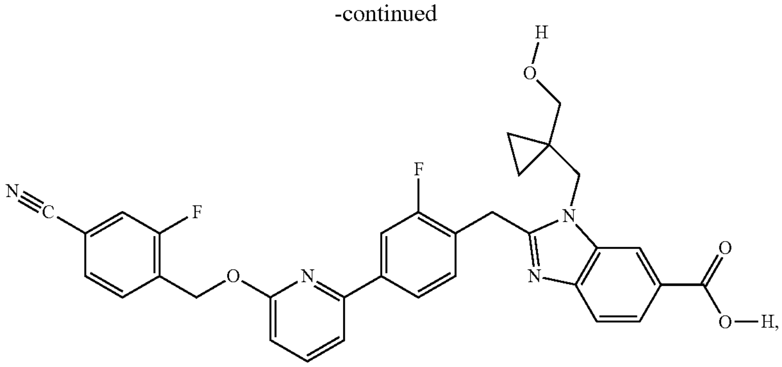
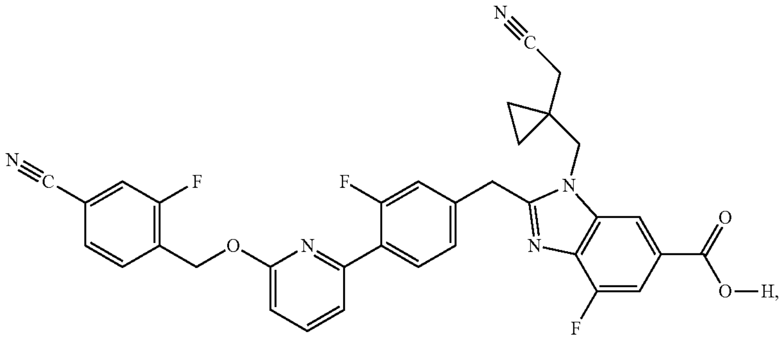
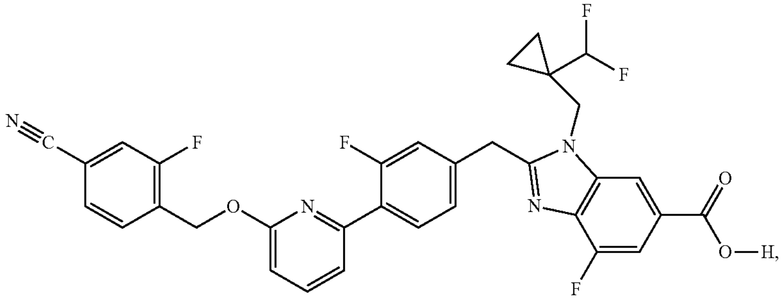
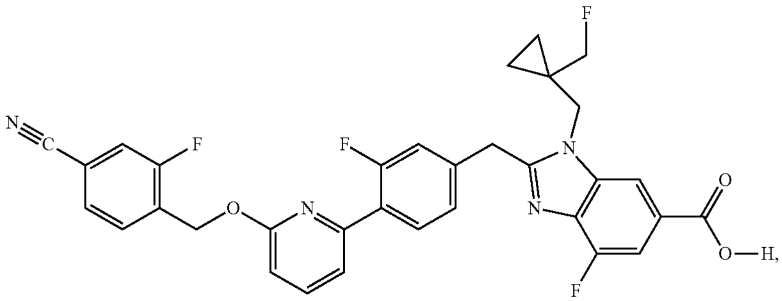
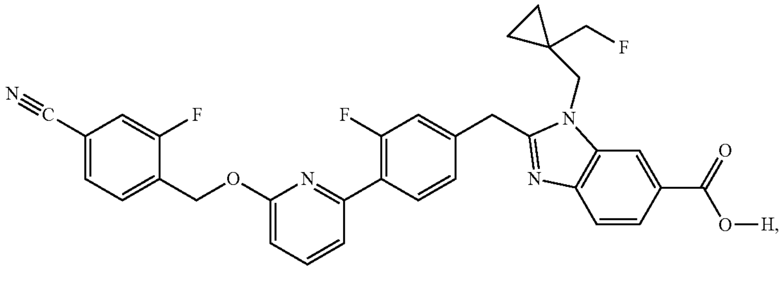

-continued
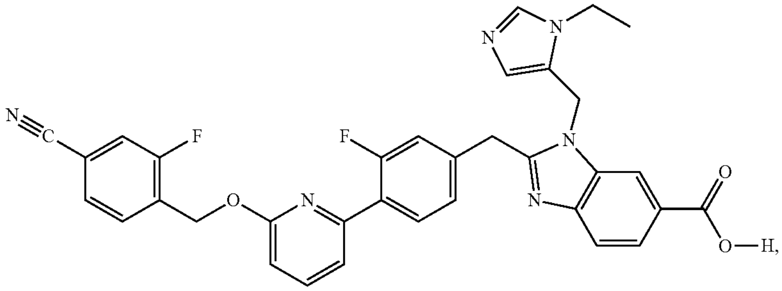
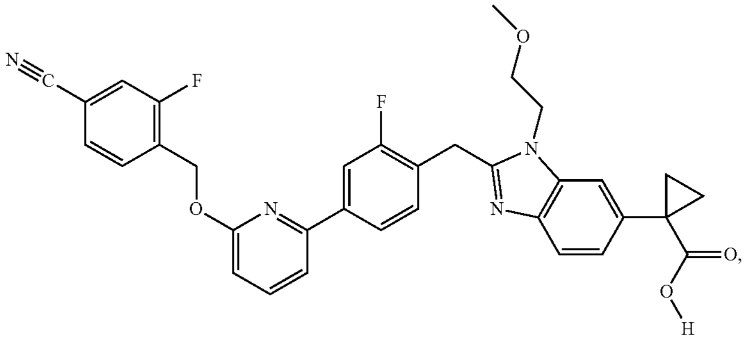
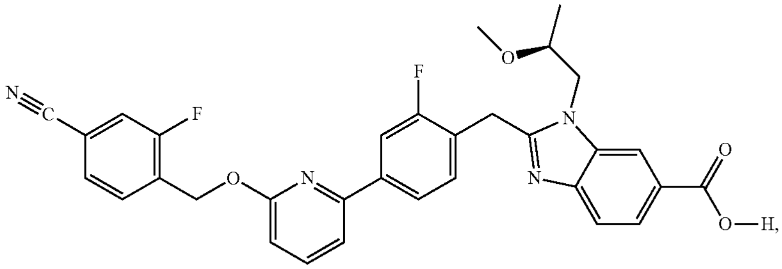
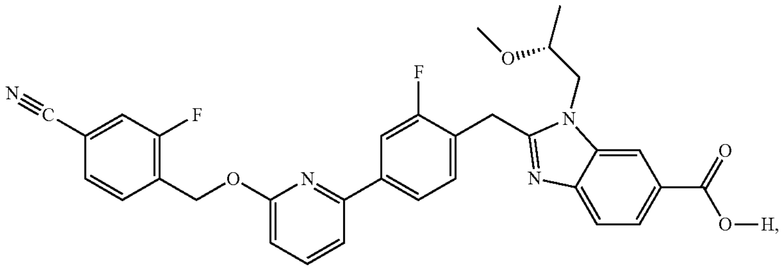
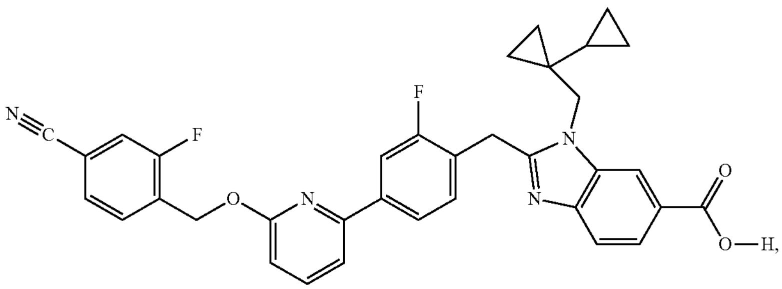

-continued
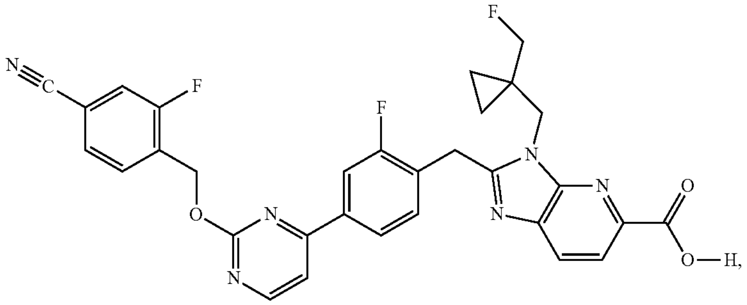
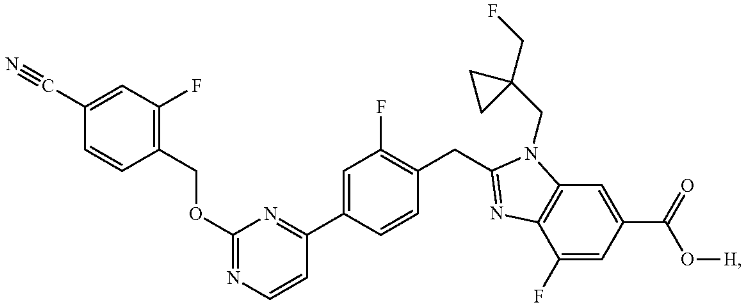
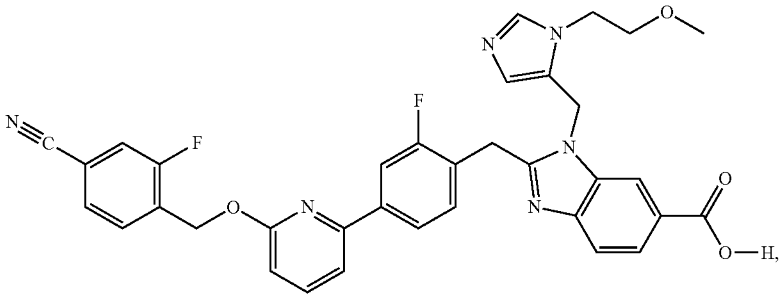
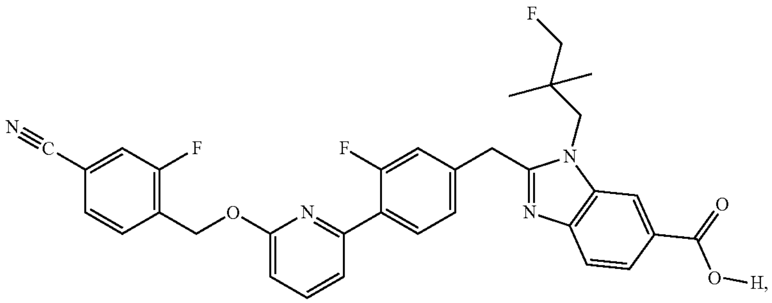
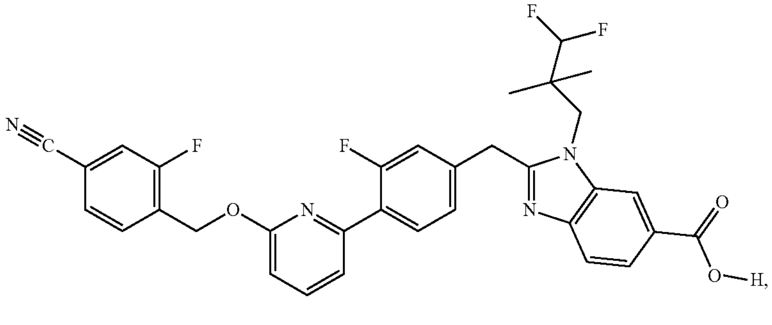

-continued
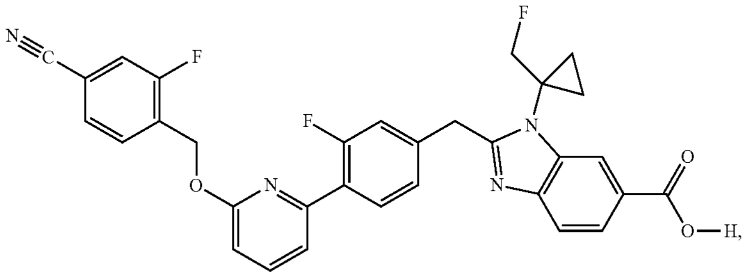
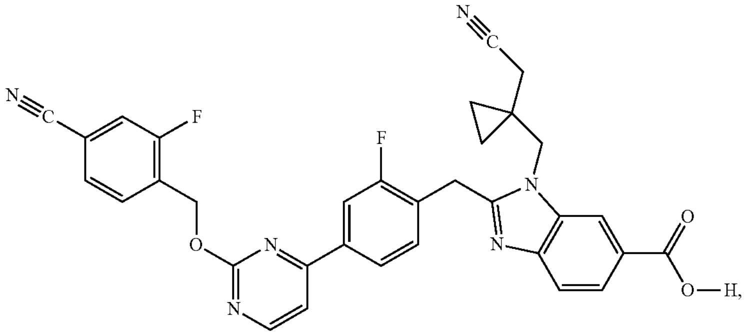
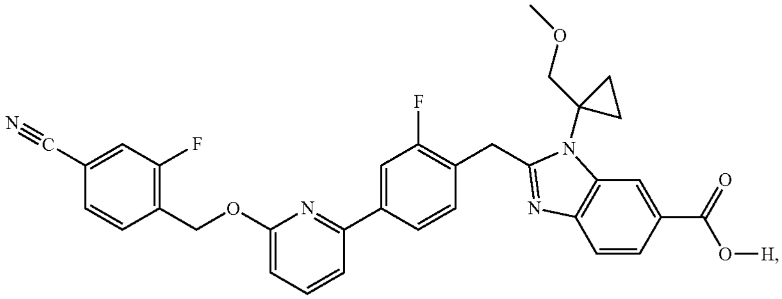
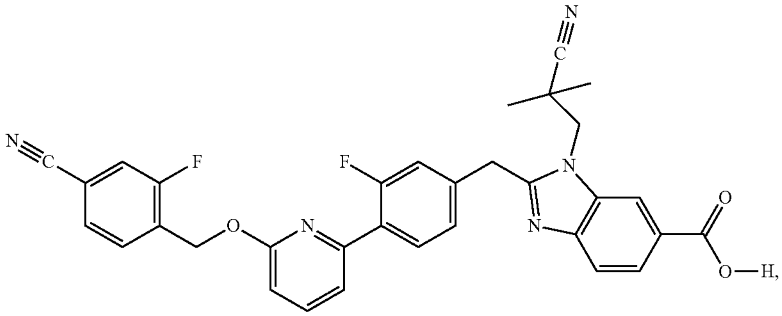
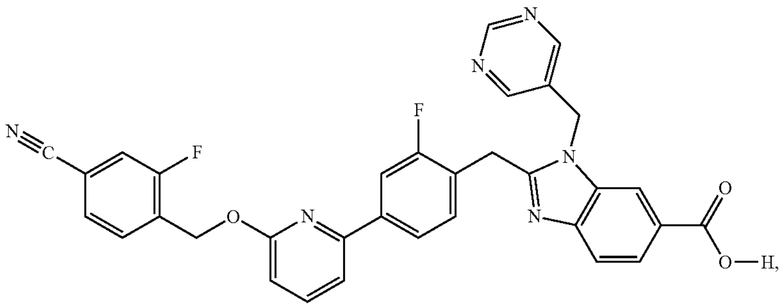

-continued
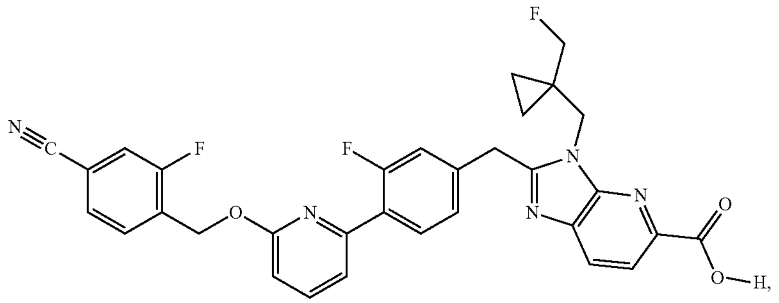
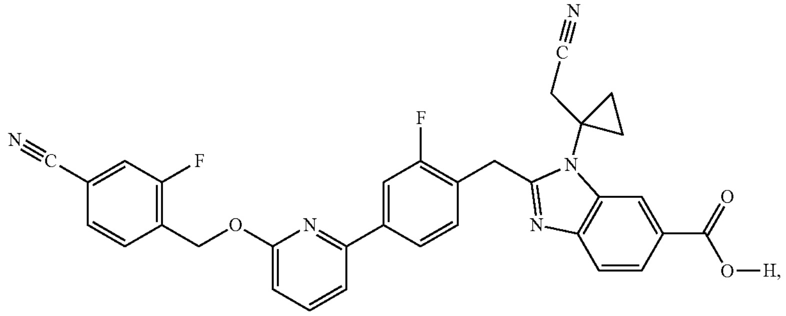
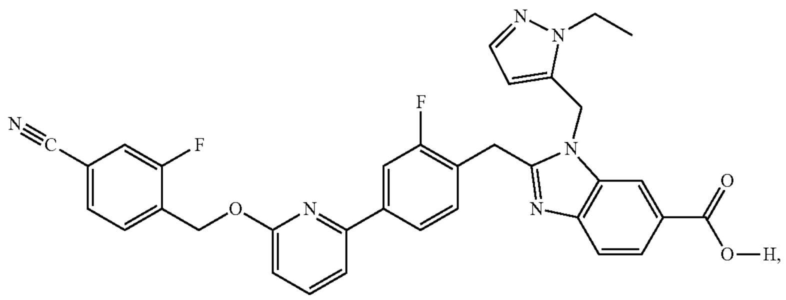
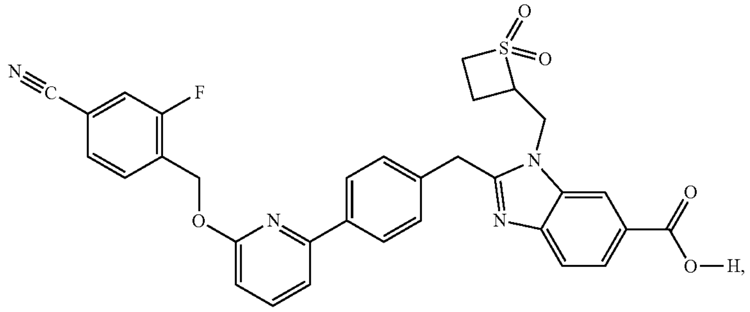
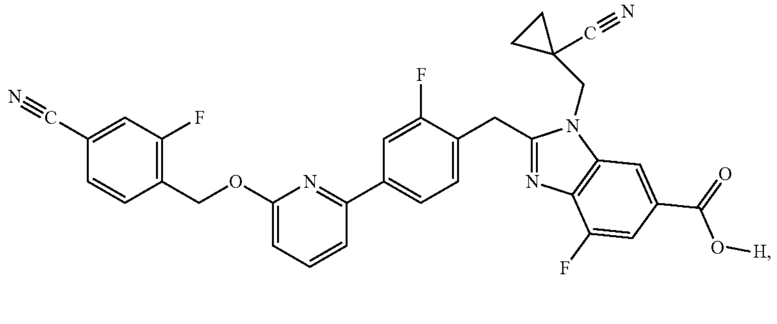

-continued
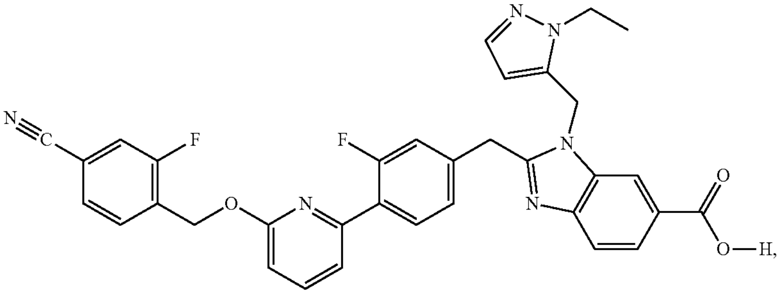
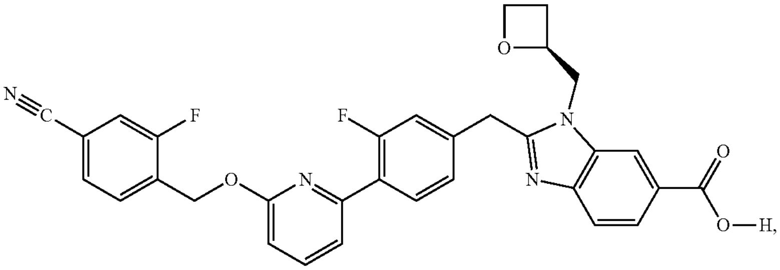
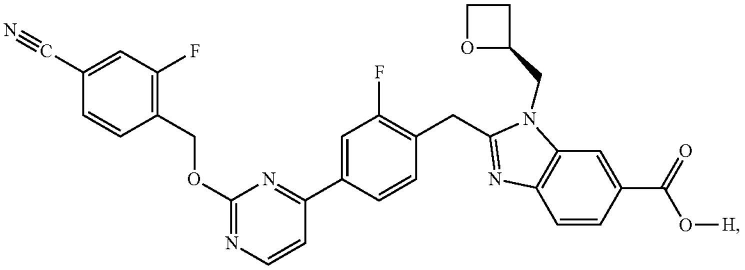
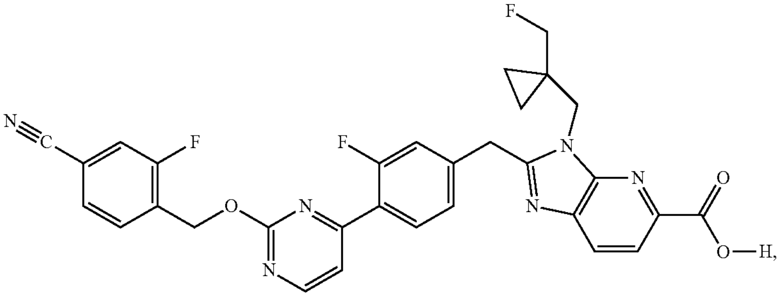
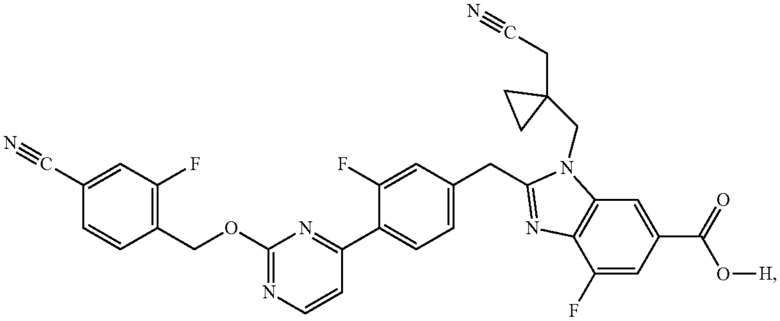

-continued
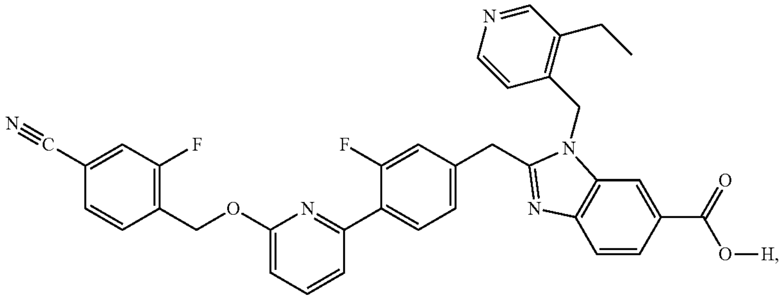
,
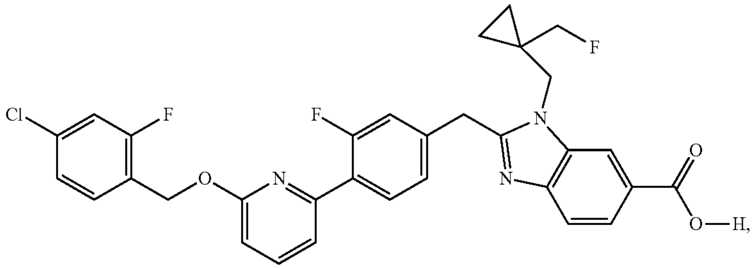
,
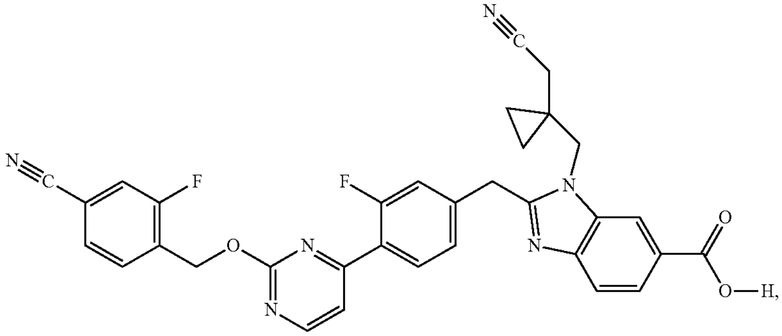
,
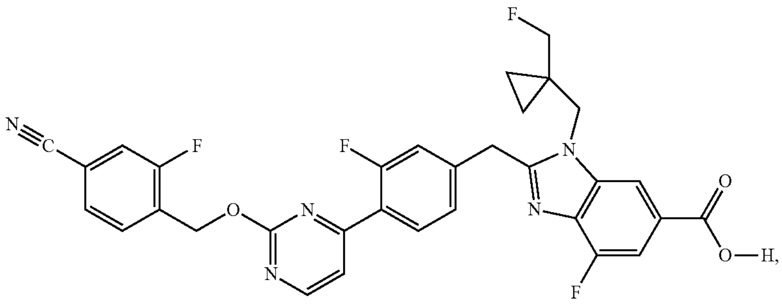
,
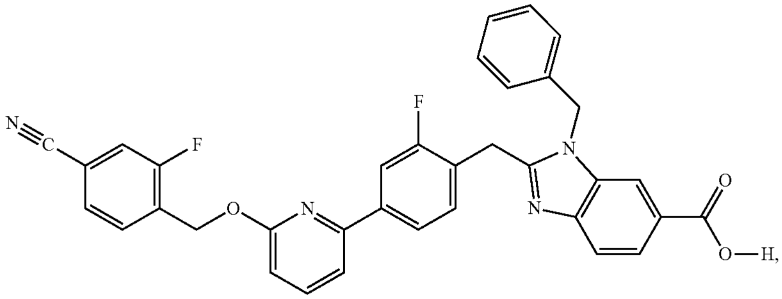
, -continued
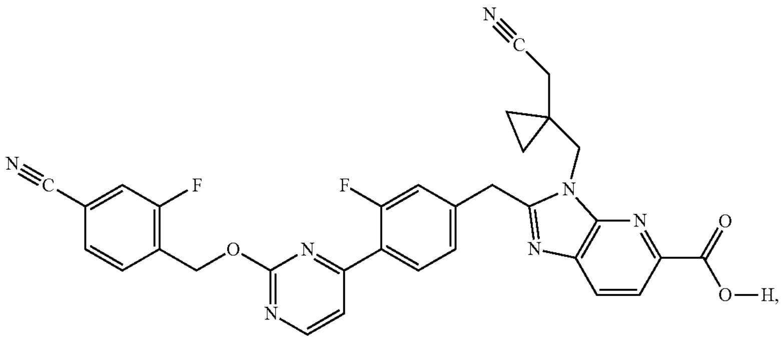
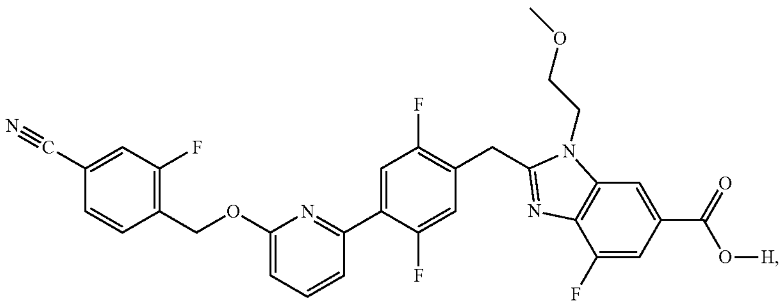
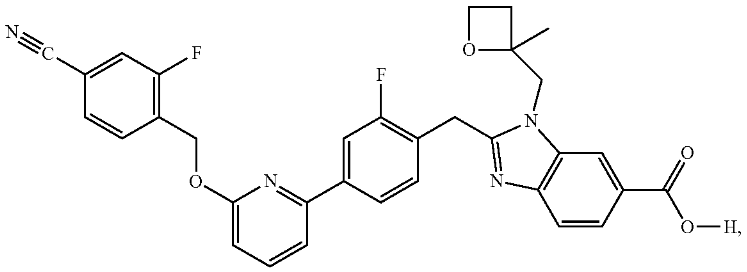
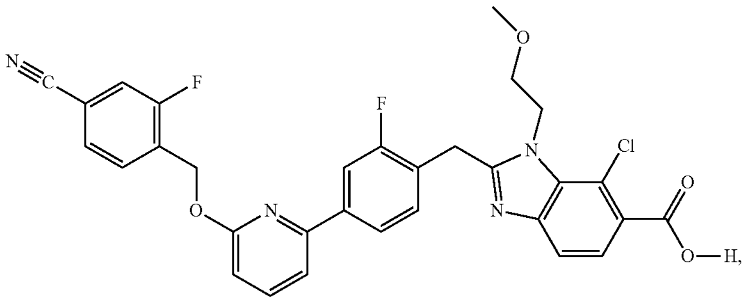
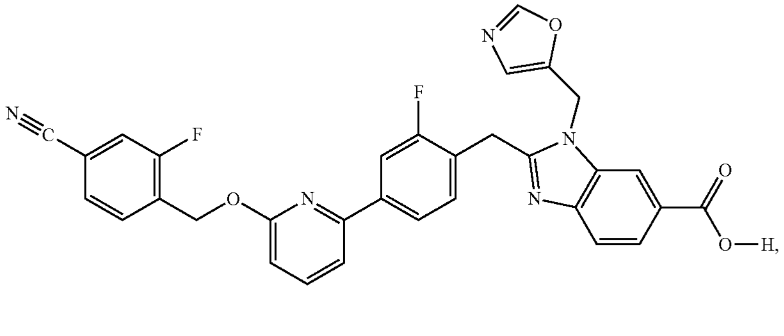

-continued
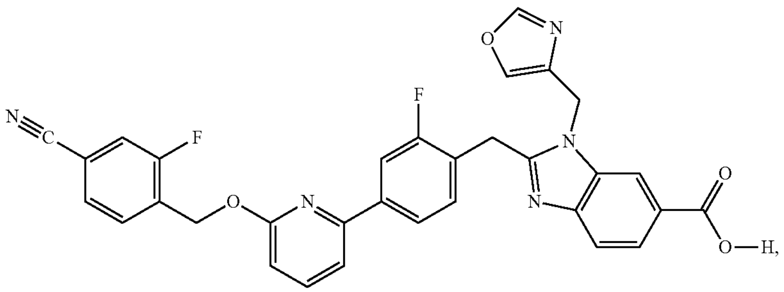
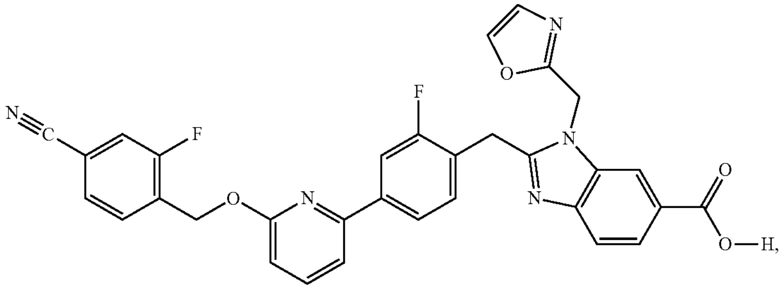
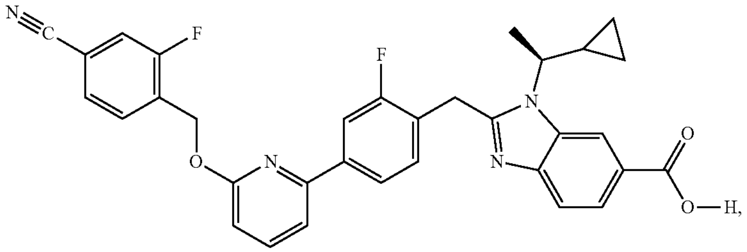
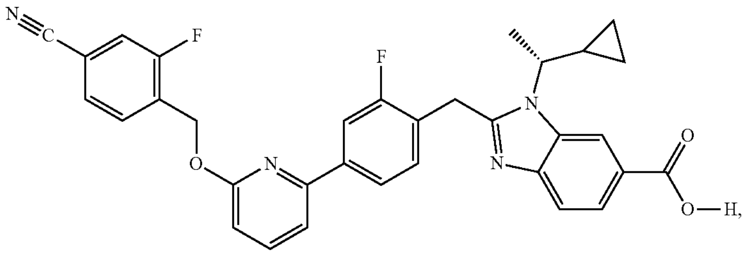
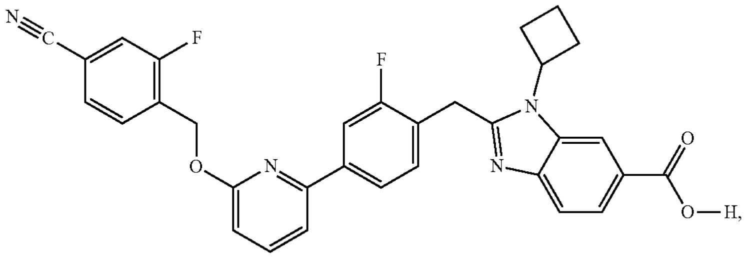
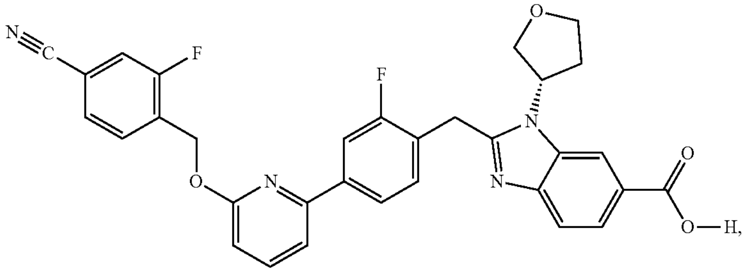

-continued
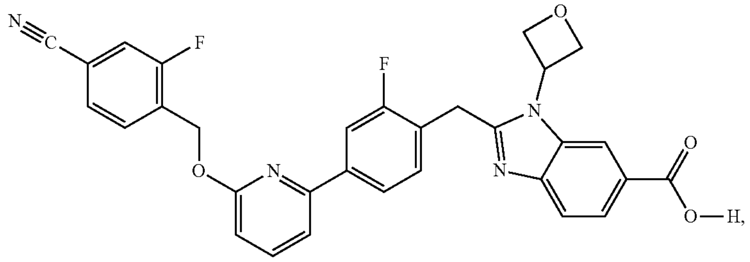
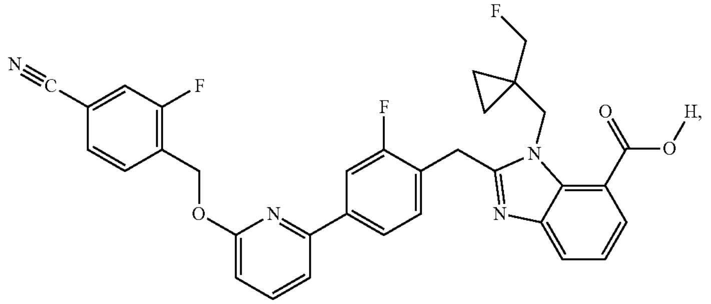
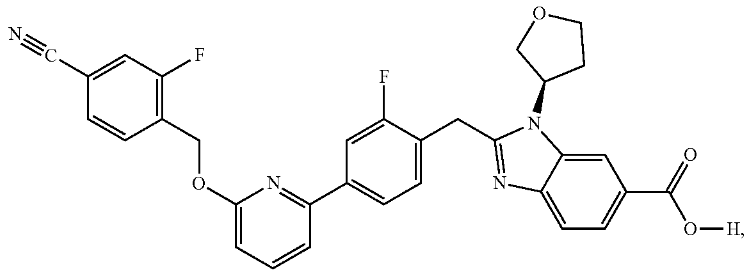
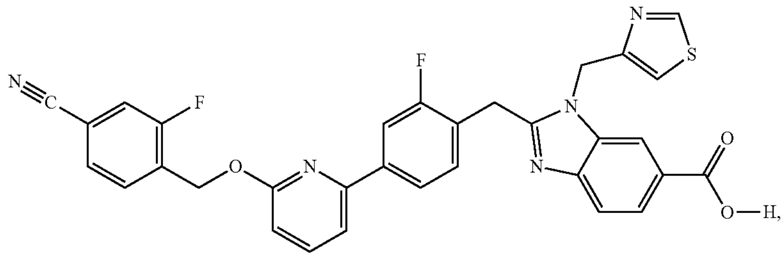
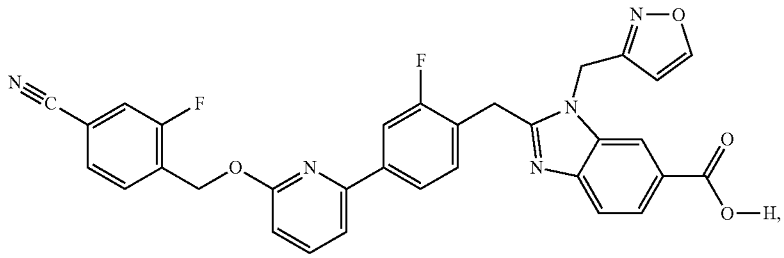
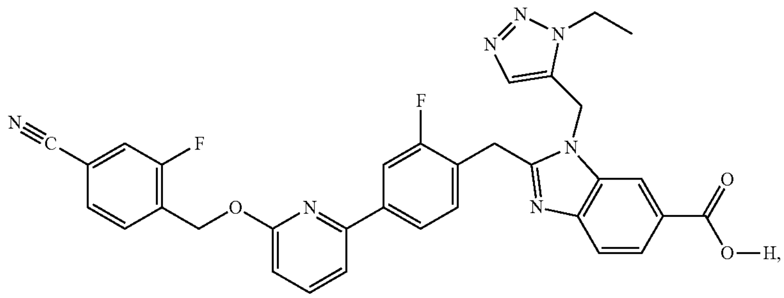

-continued
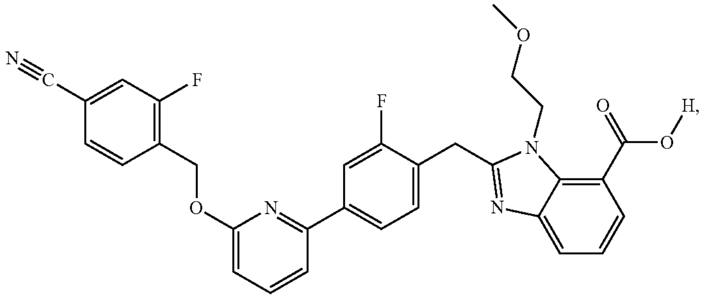
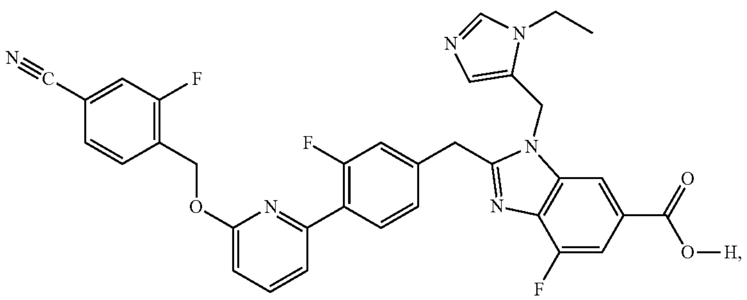
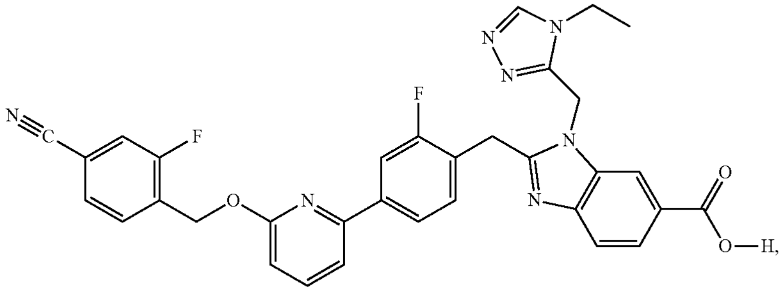
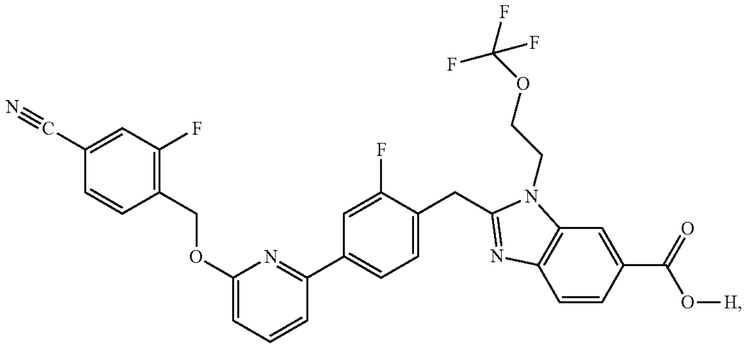
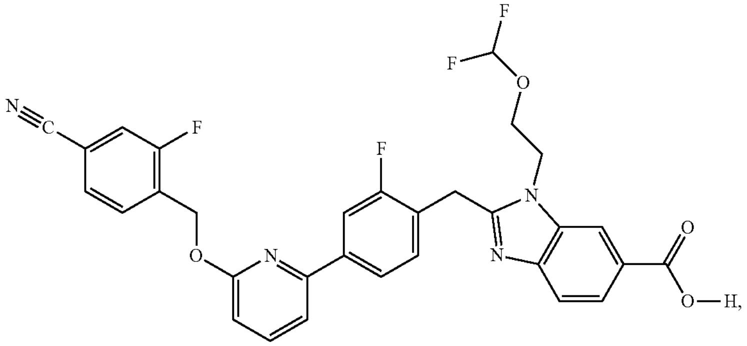

-continued
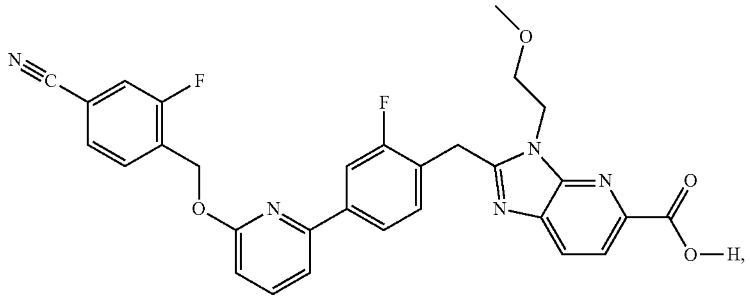
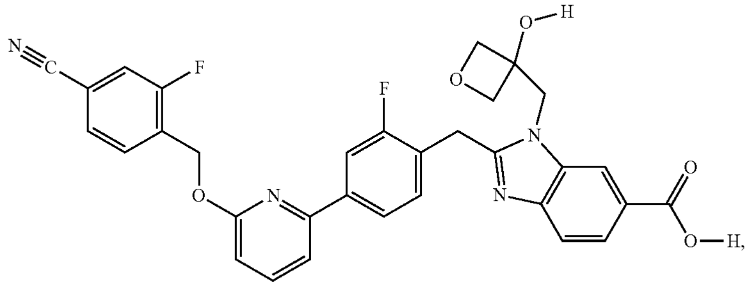
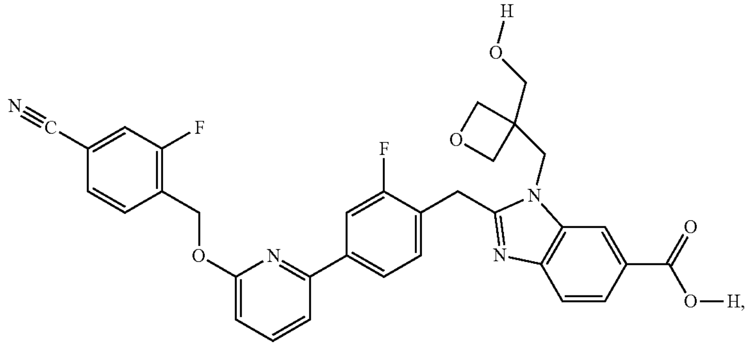
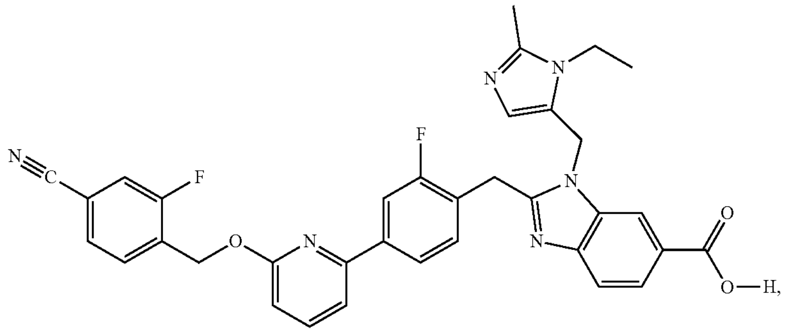
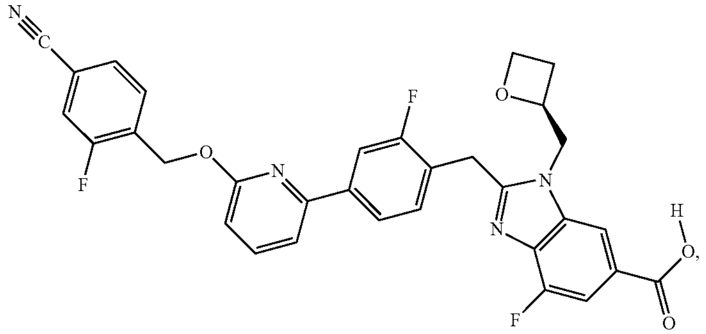

-continued
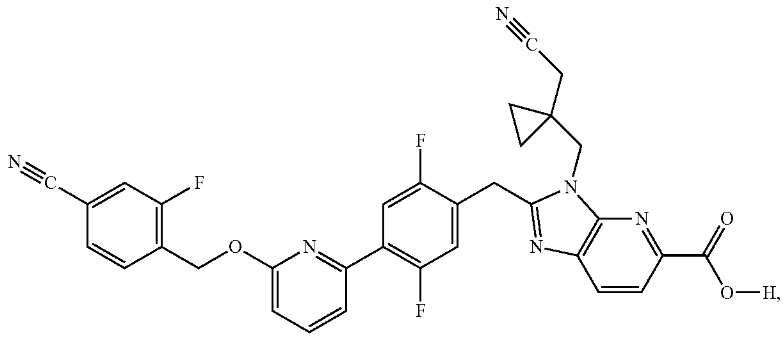
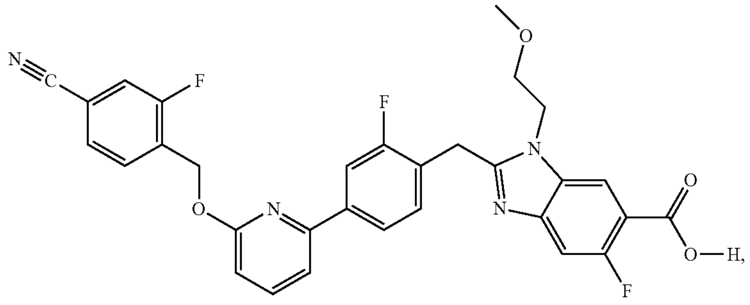
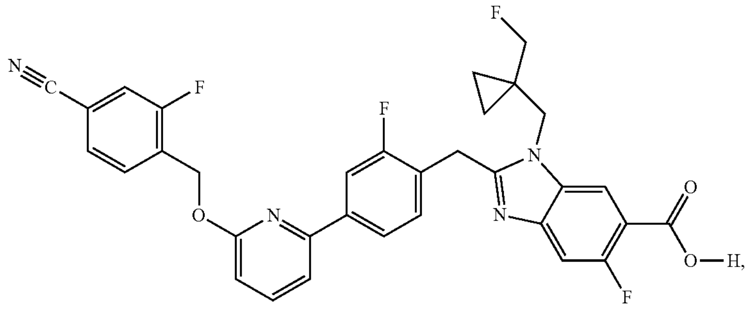
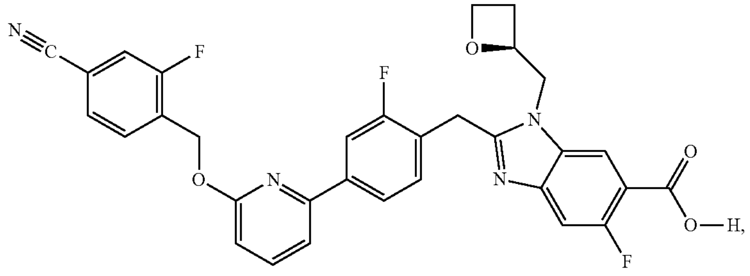
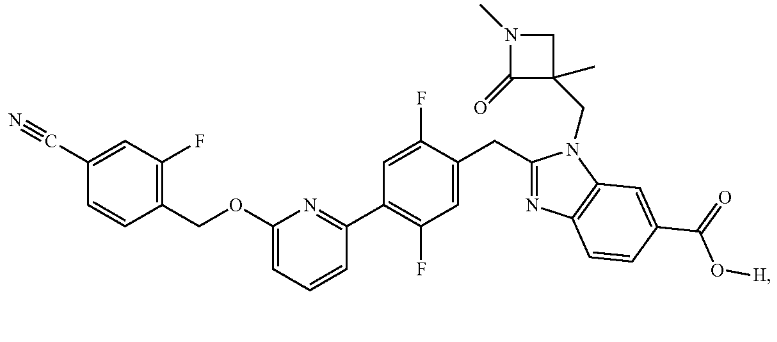

-continued
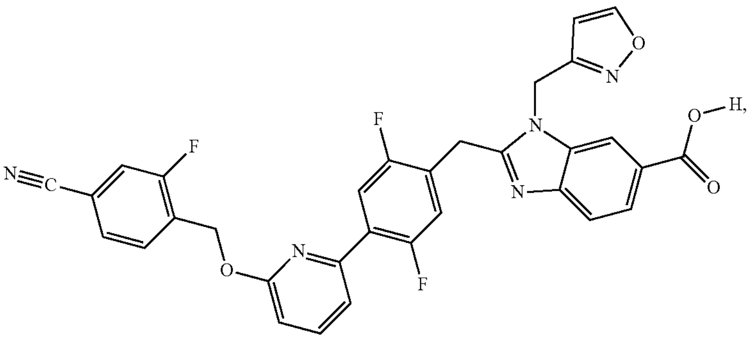
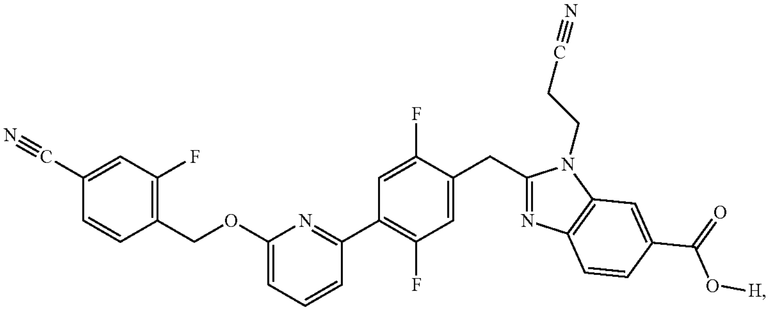
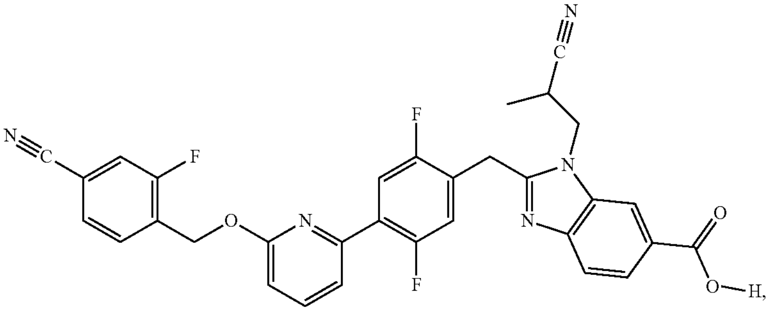
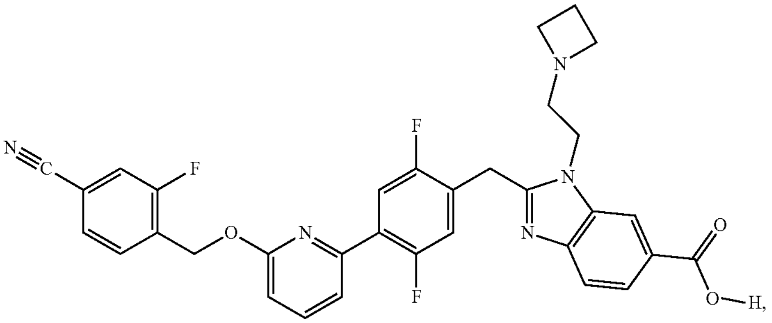
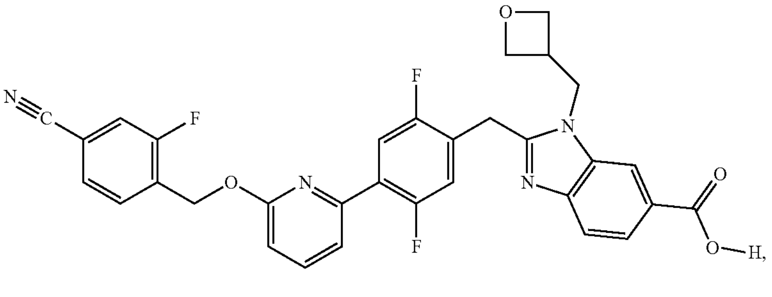

-continued
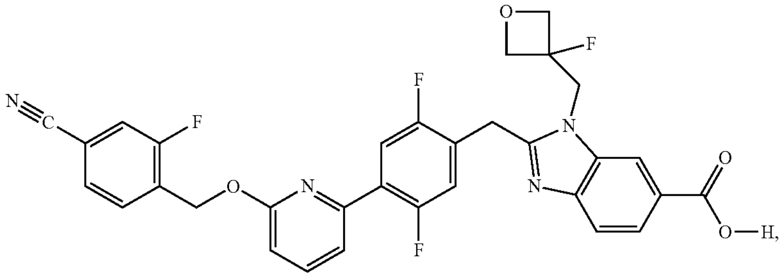
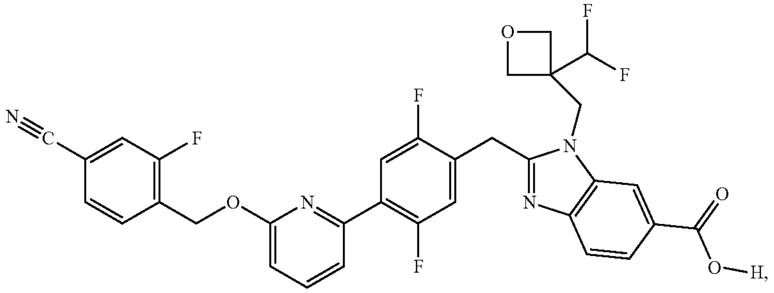
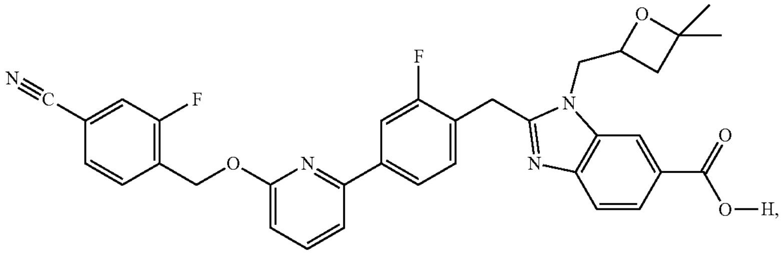
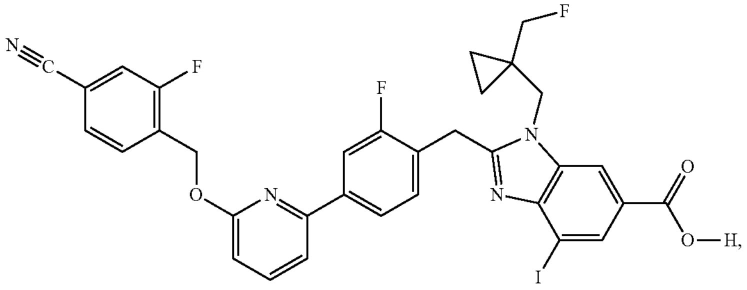
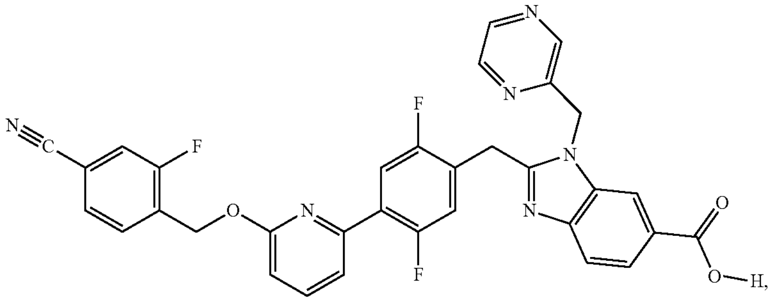
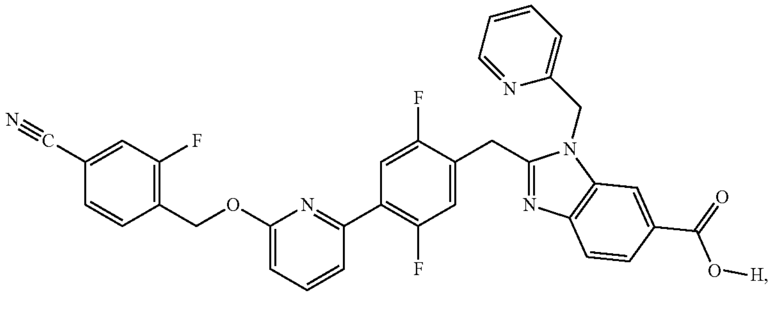

-continued
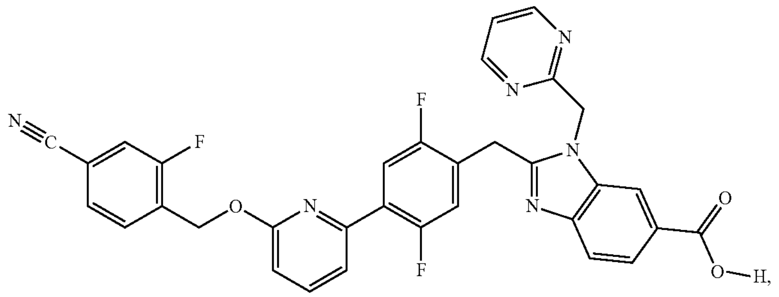
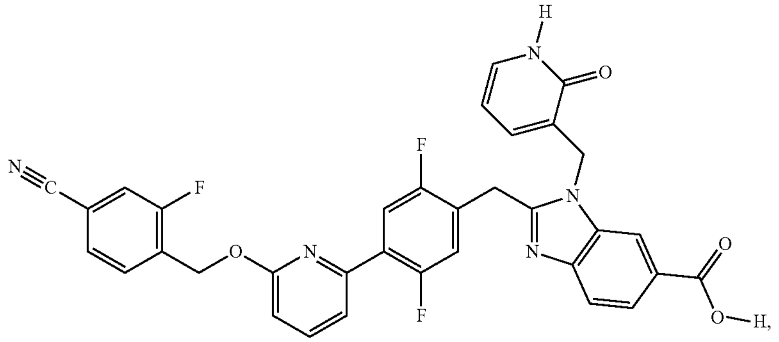
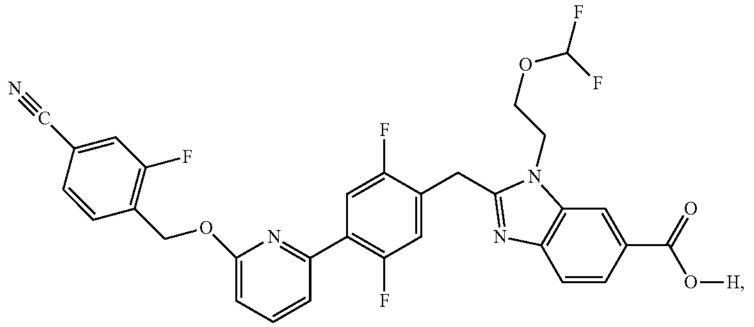
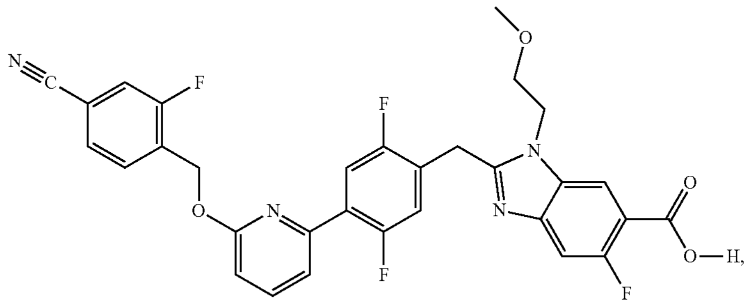
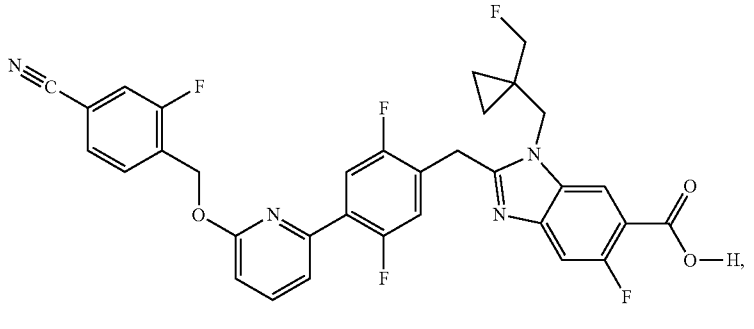

-continued
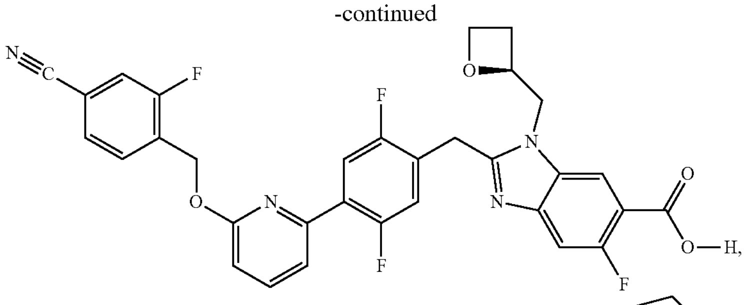
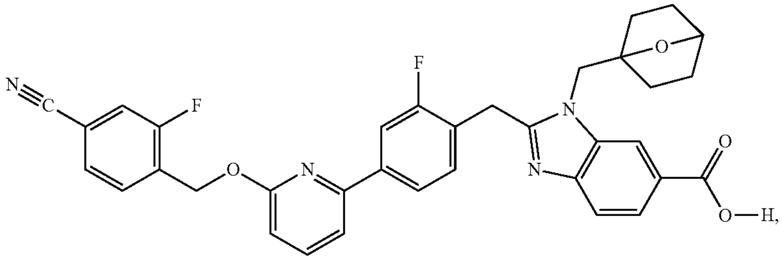
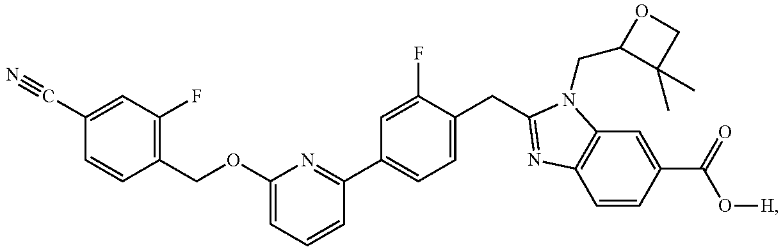
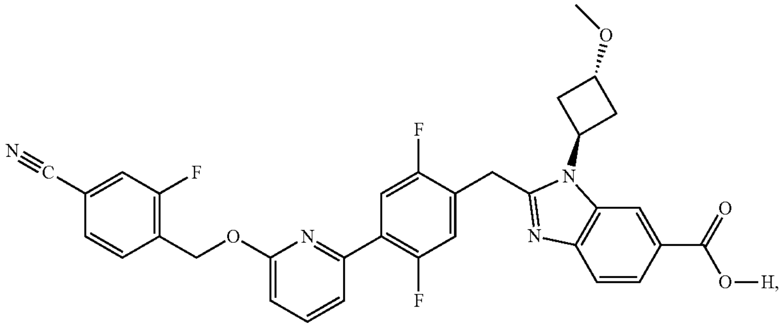
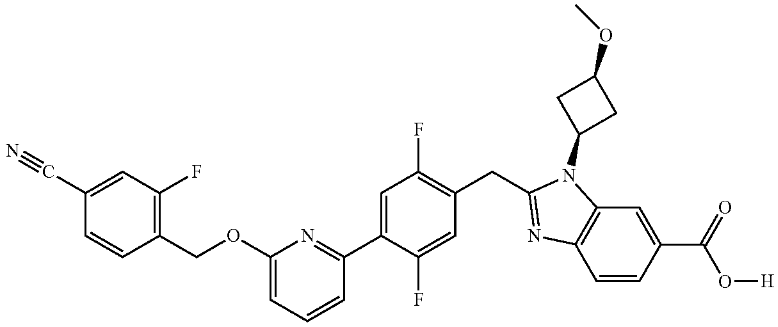
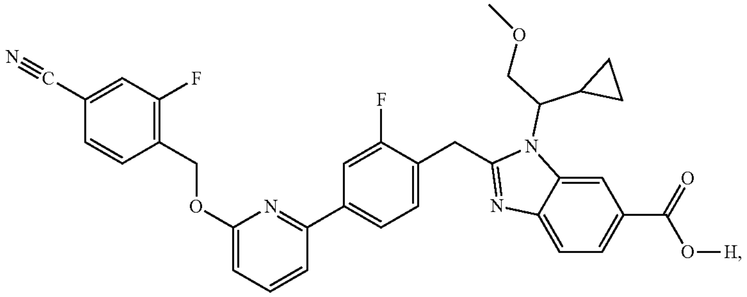

-continued
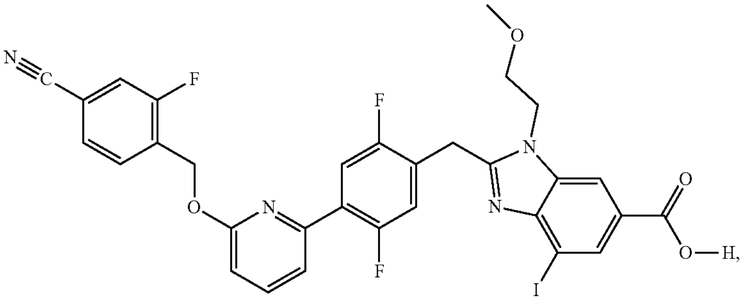
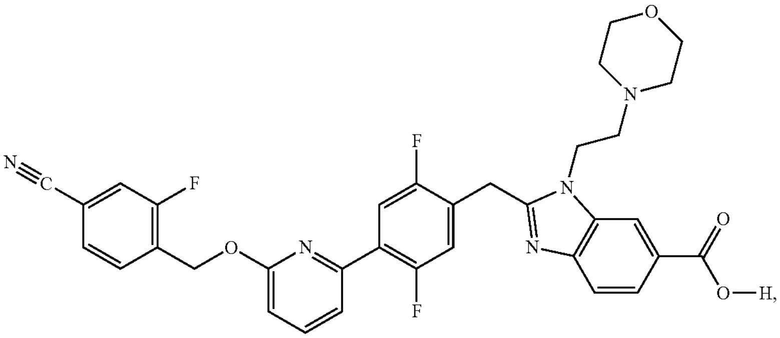
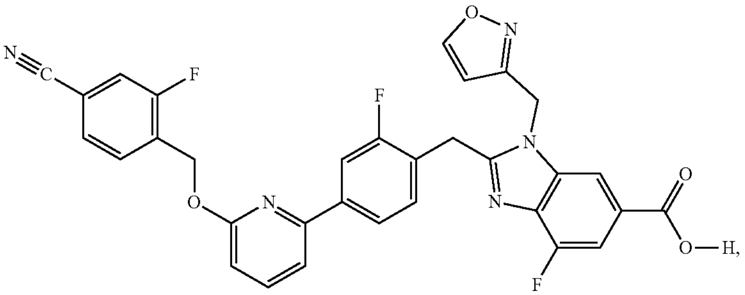
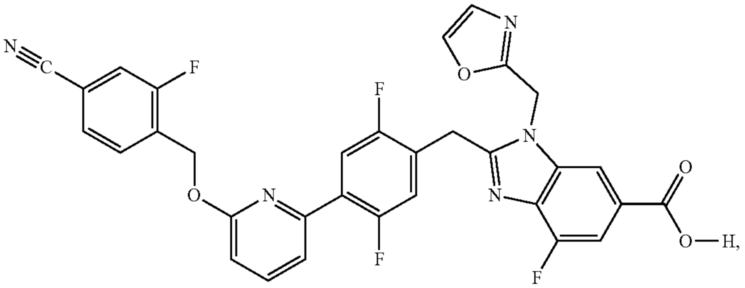
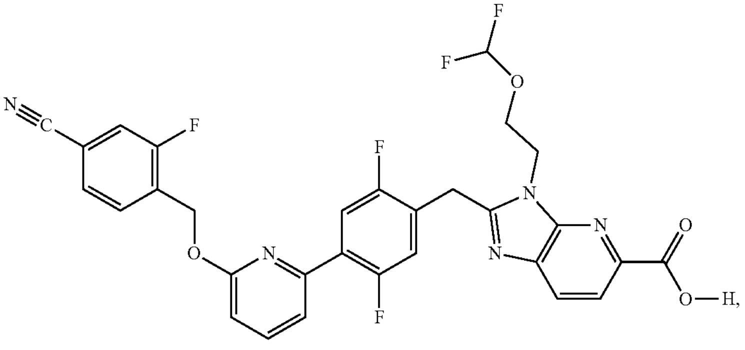

-continued
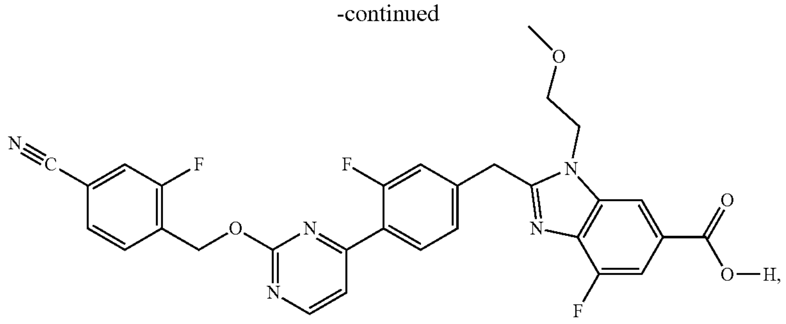
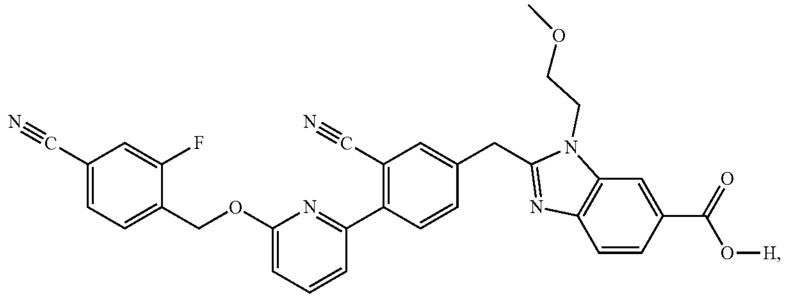
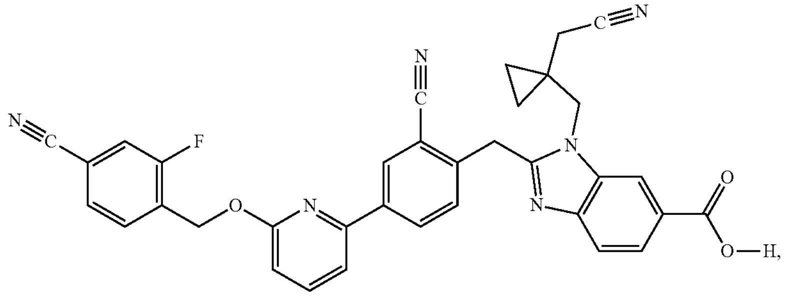
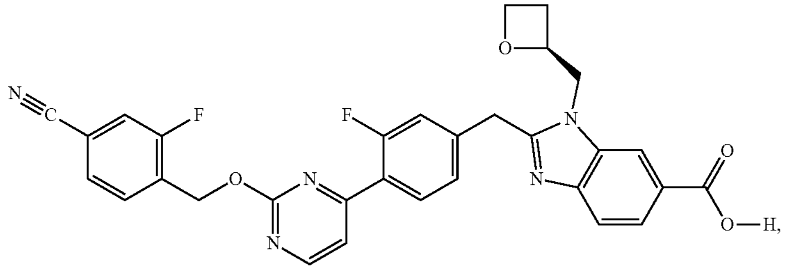
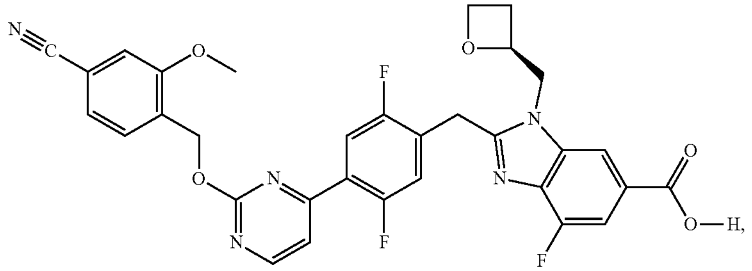
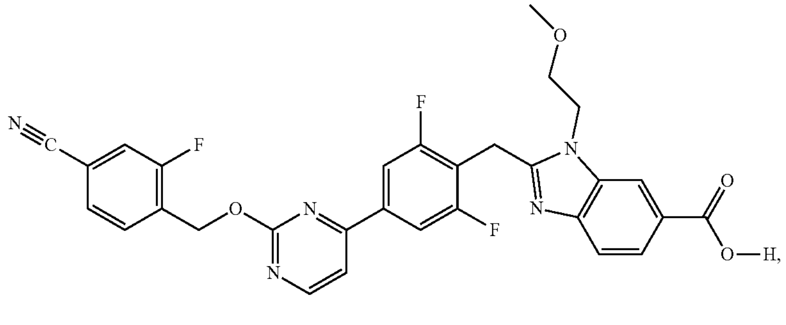

-continued
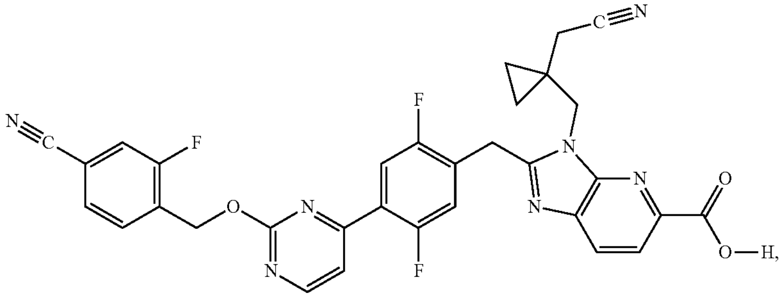
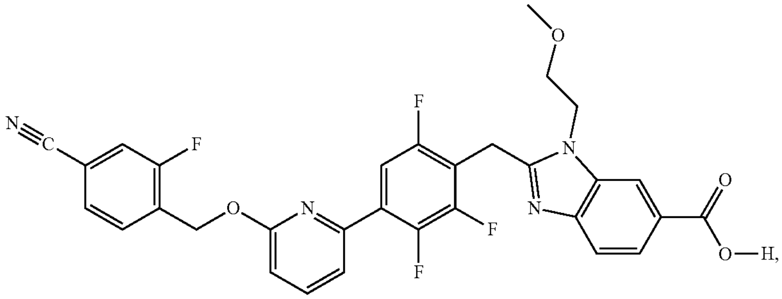
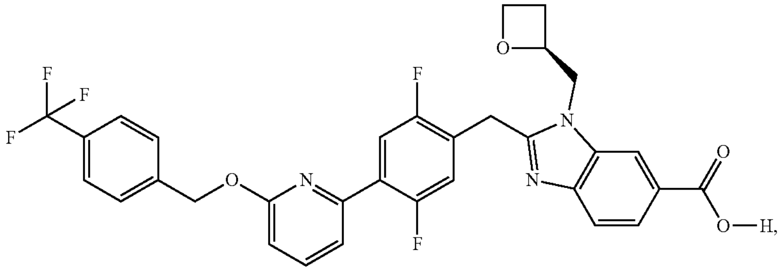
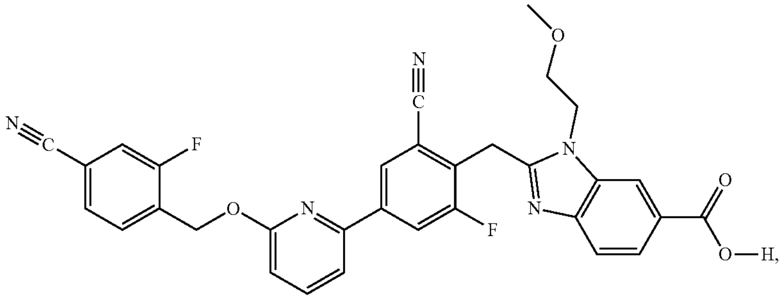
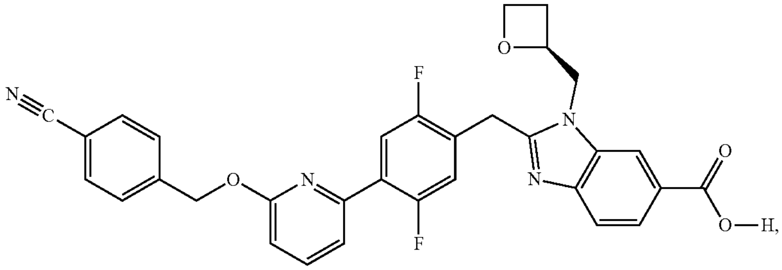
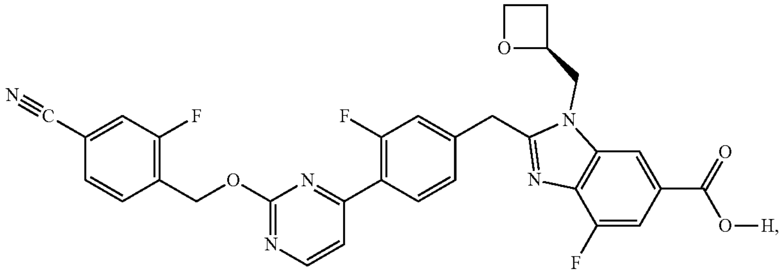

-continued
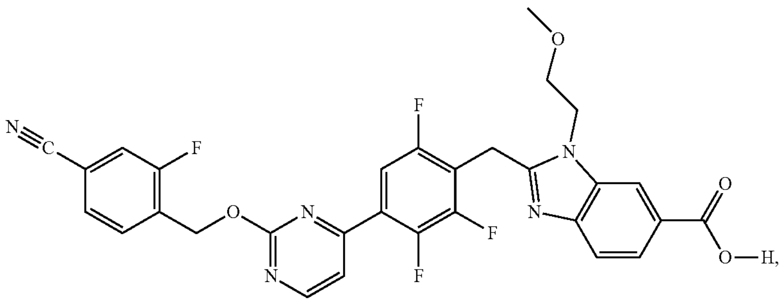
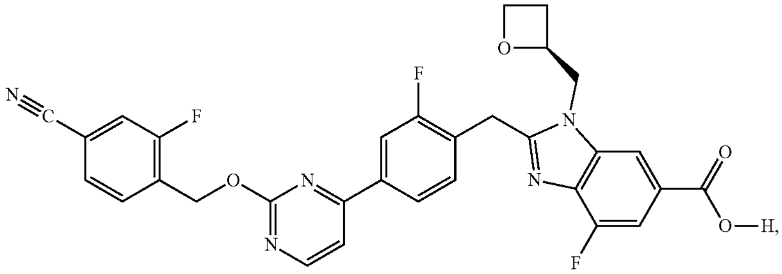
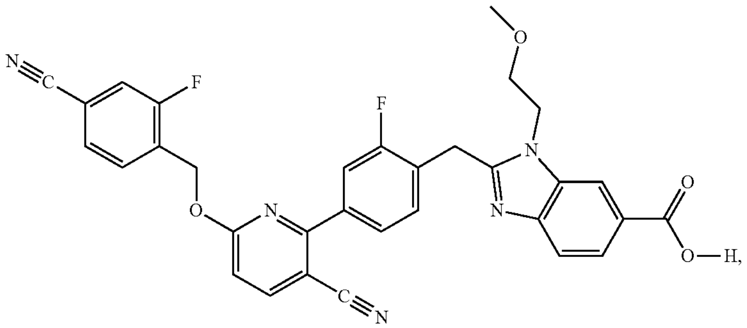
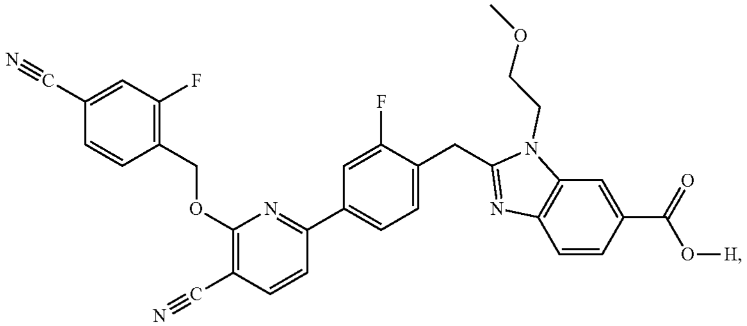
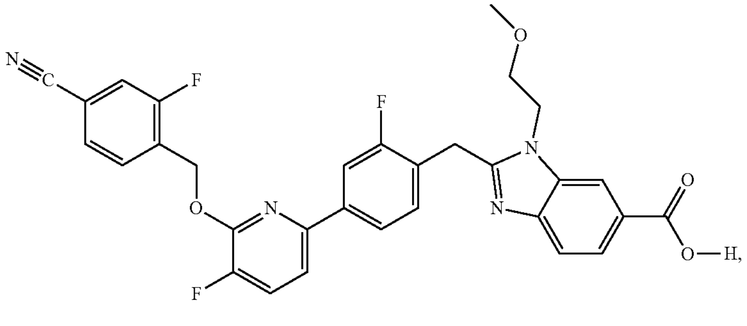

-continued
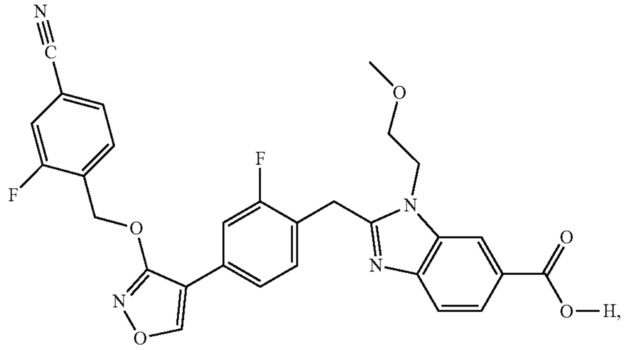
,
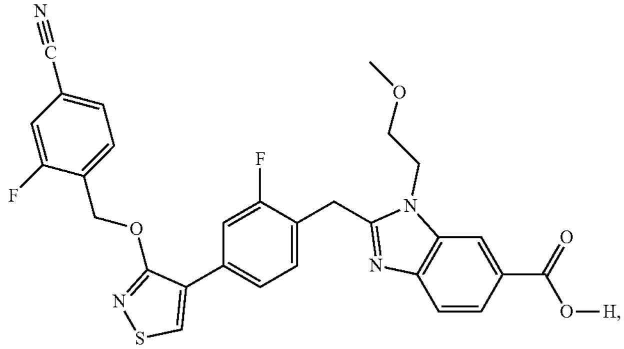
,
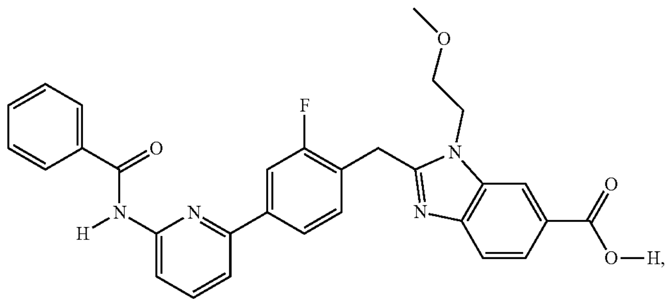
,
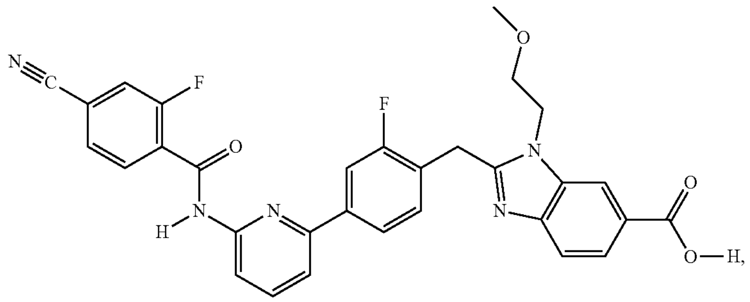
,
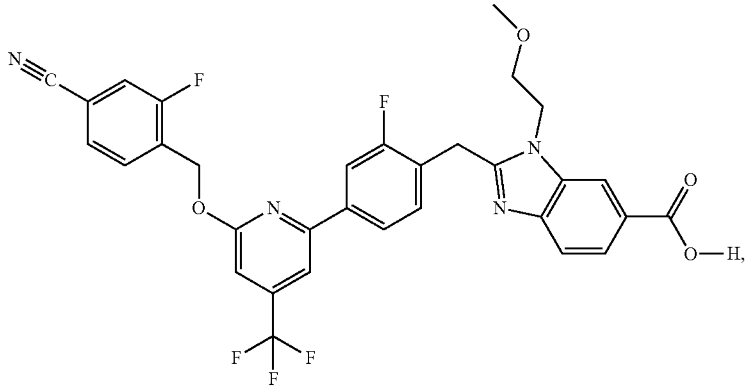
, -continued
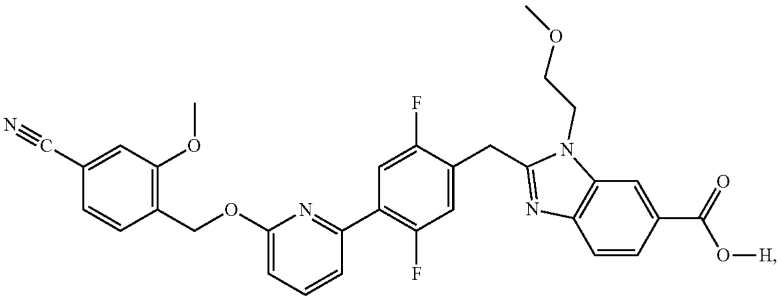
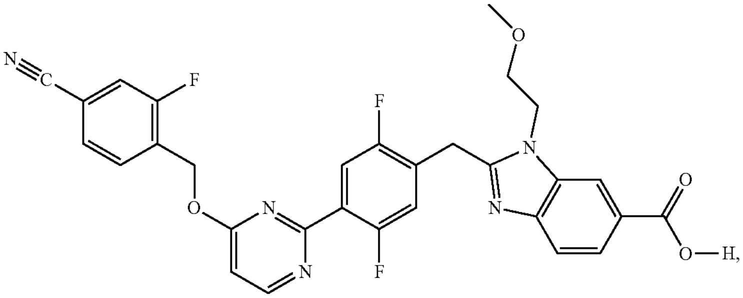
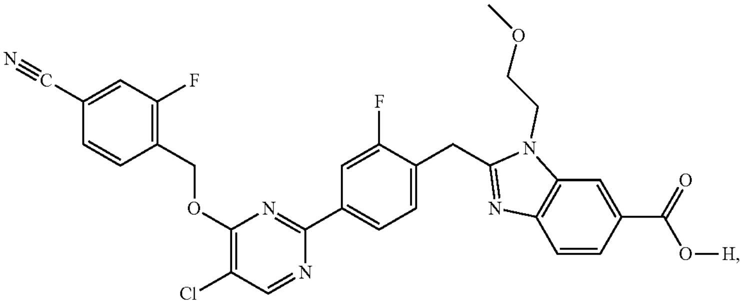
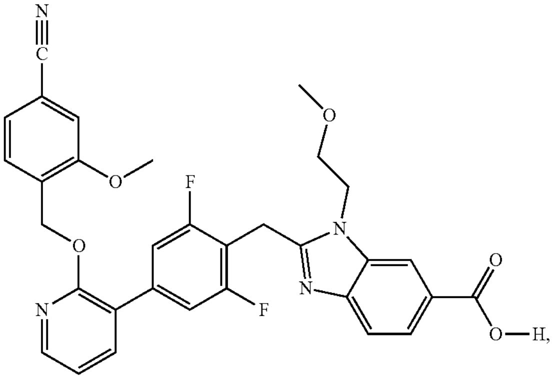
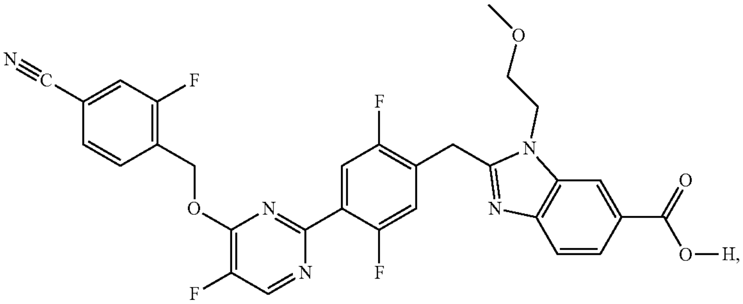

-continued
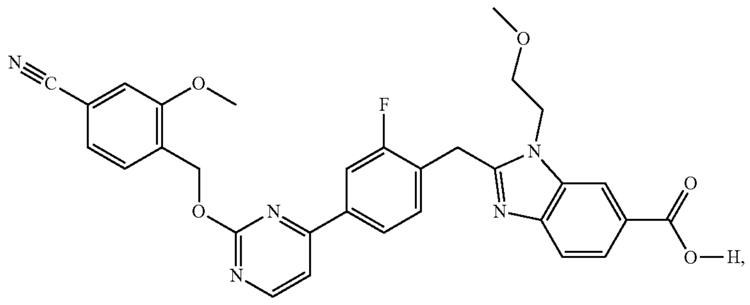
,
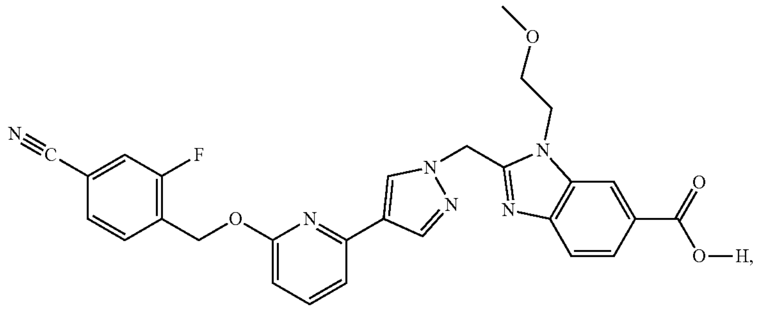
,
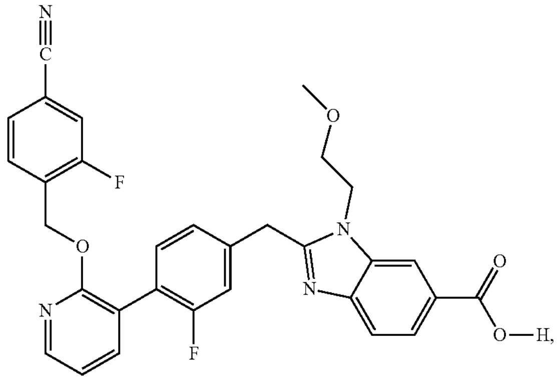
,
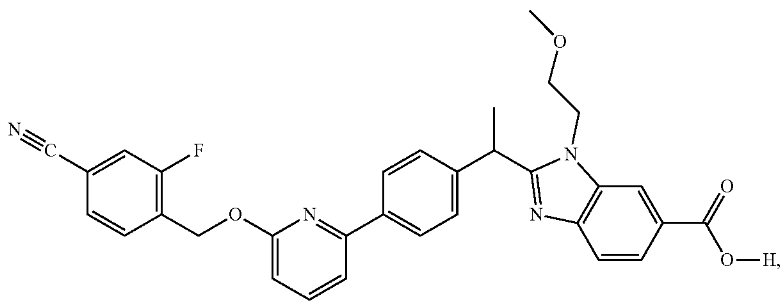
,
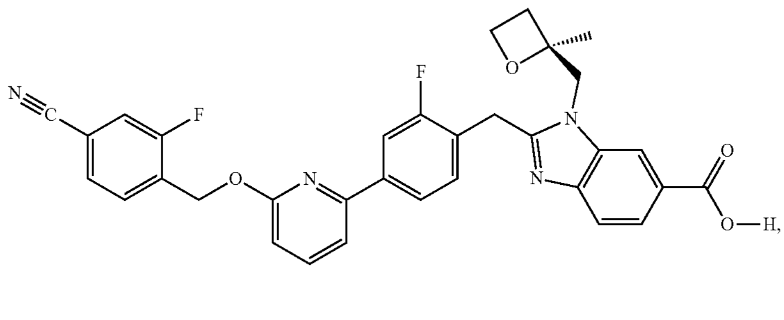
, -continued
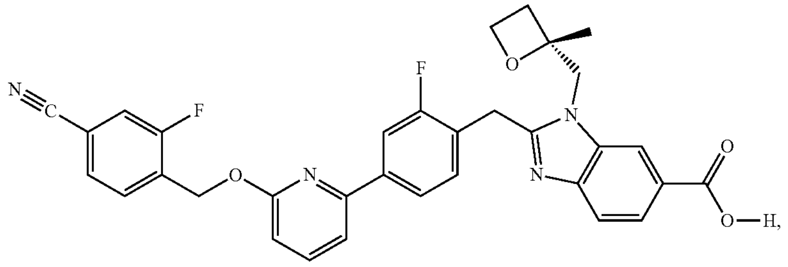
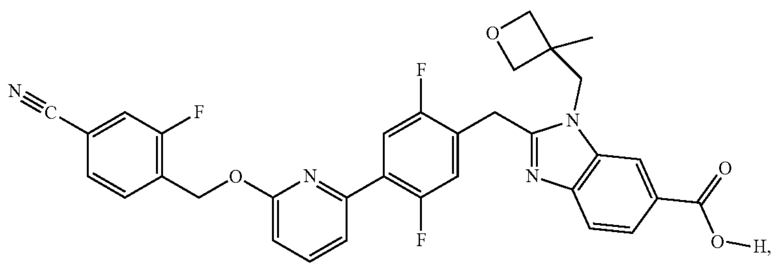
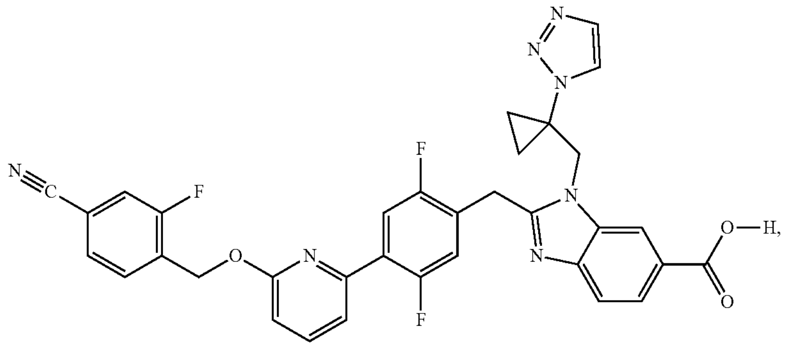
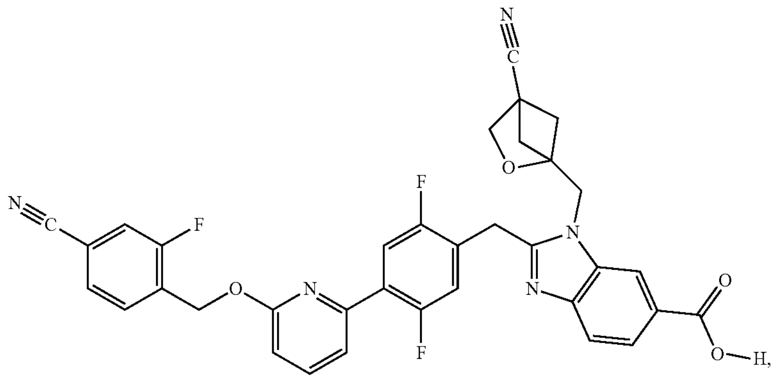
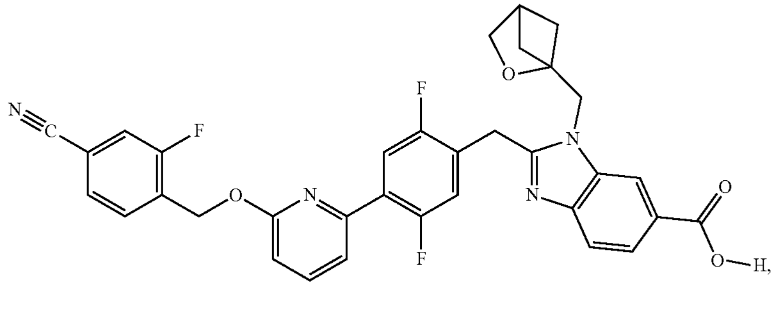

-continued
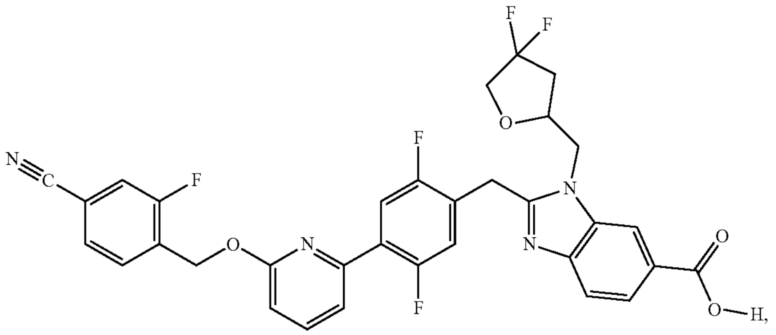
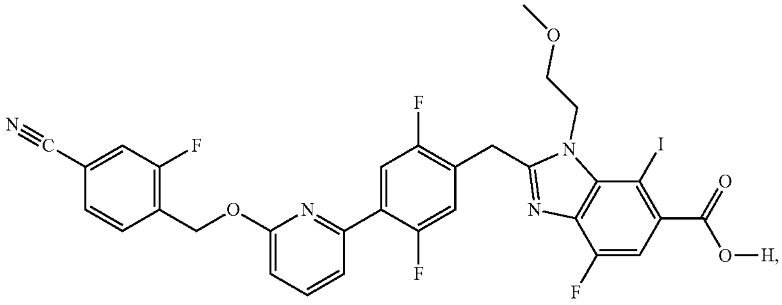
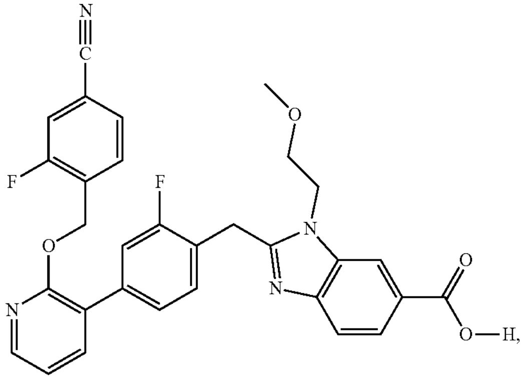
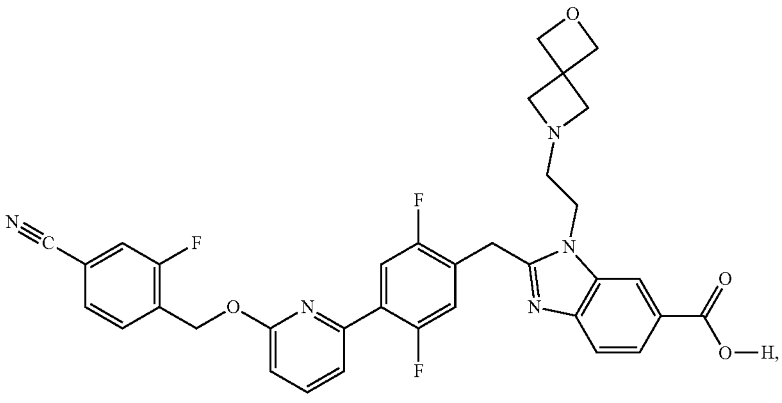
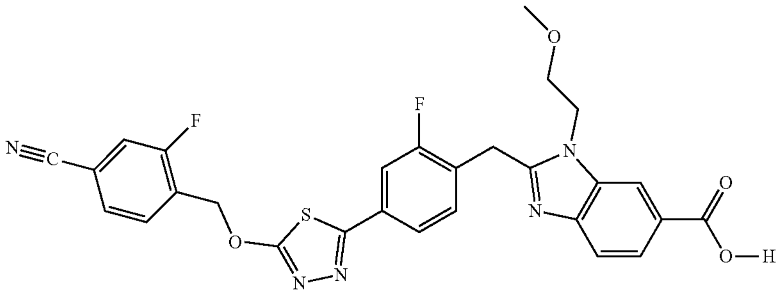

-continued
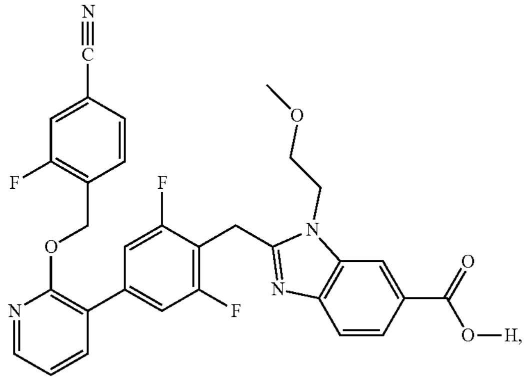
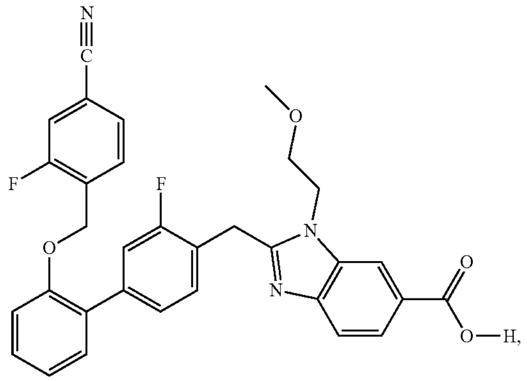
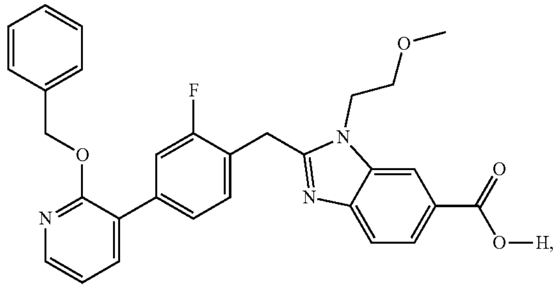
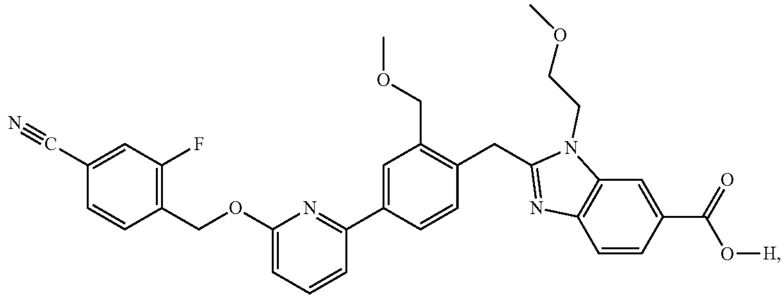
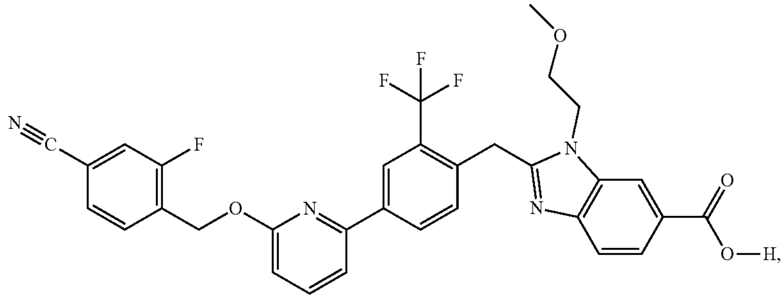

-continued
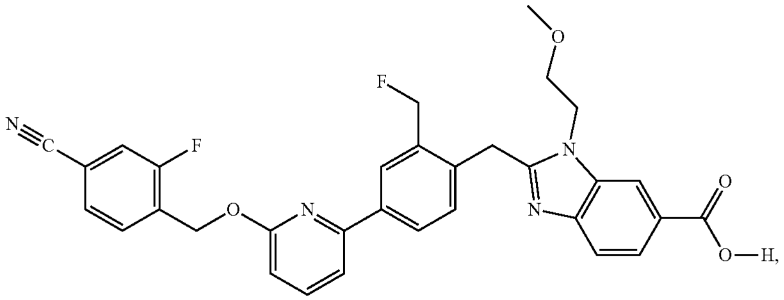
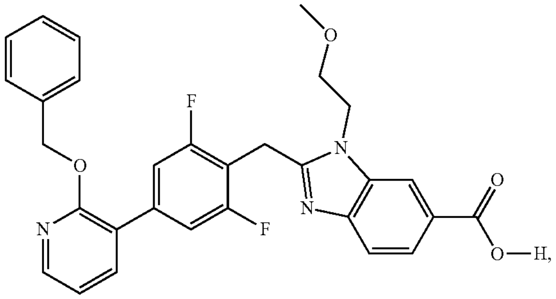
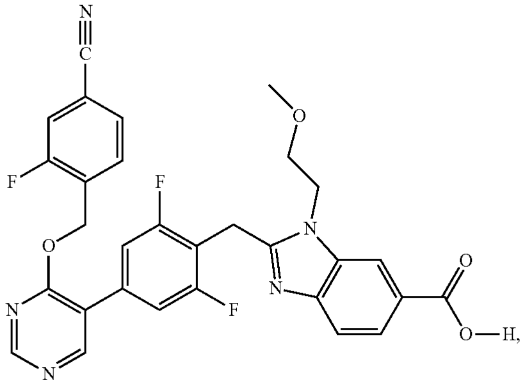
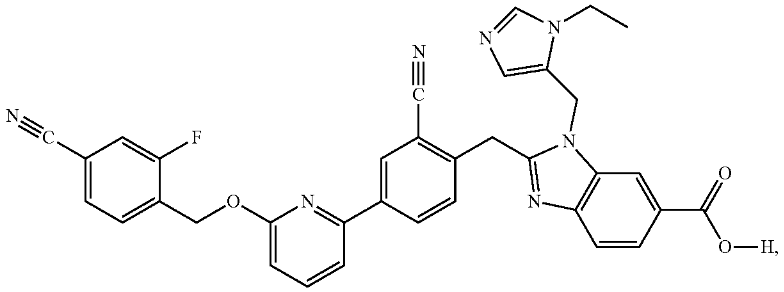
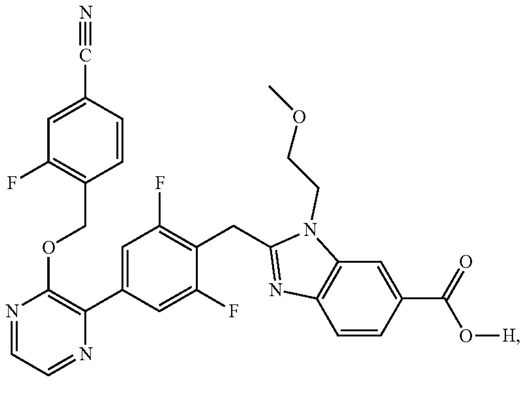

-continued
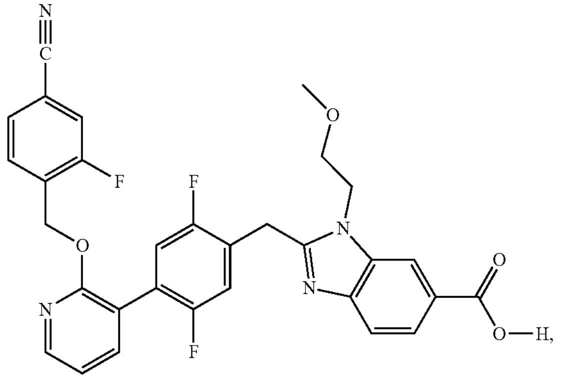
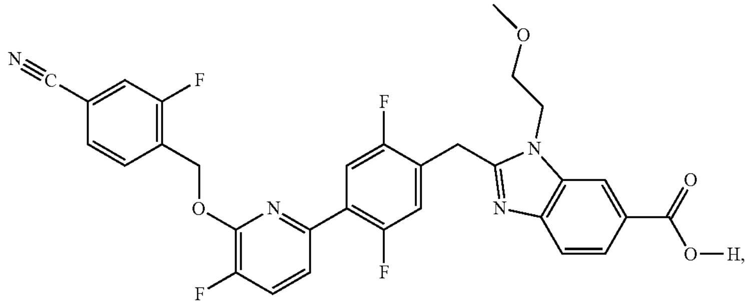
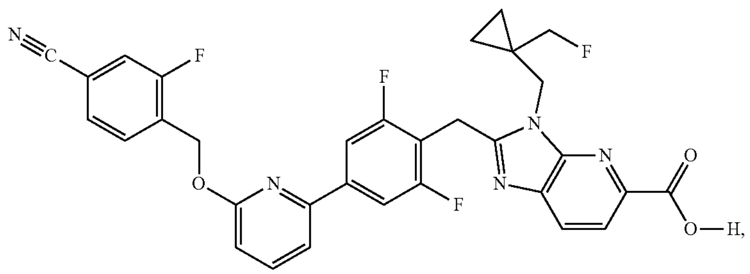
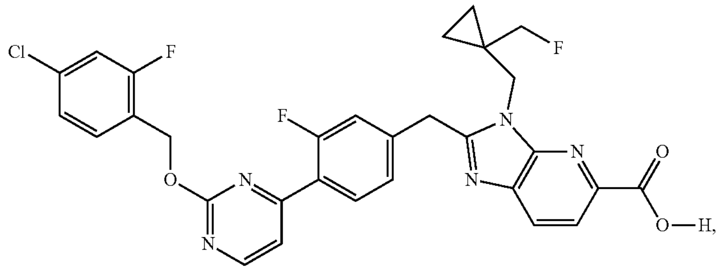
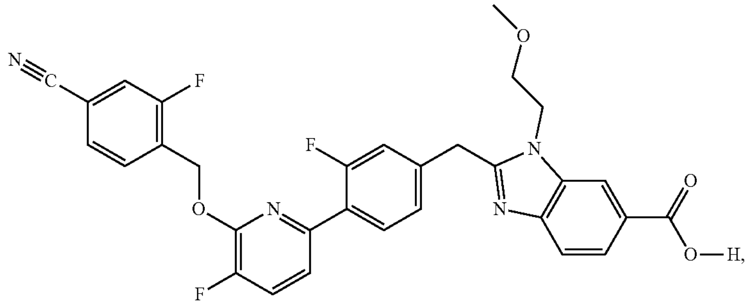

-continued
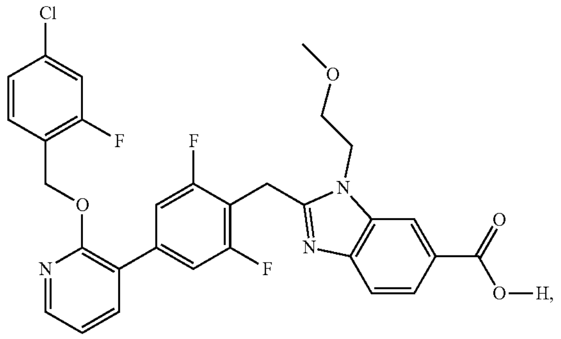
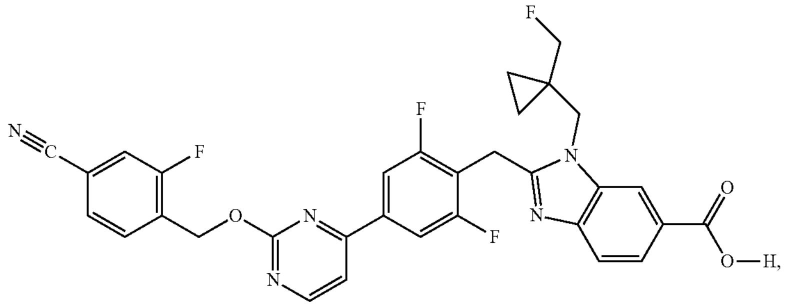
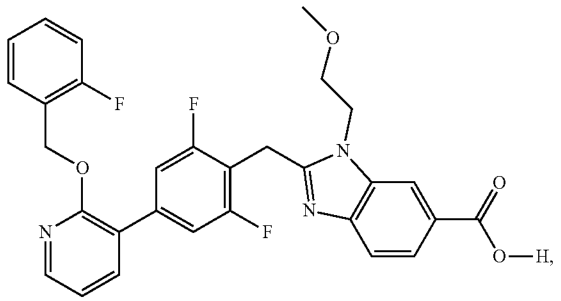
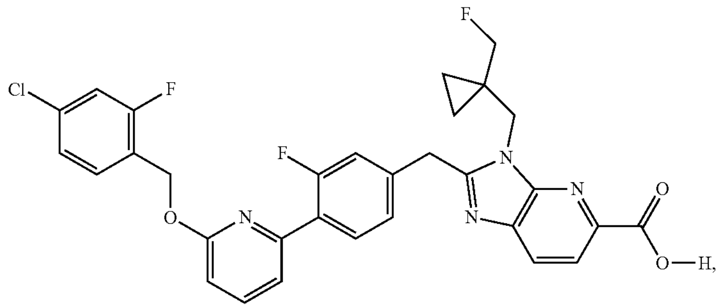
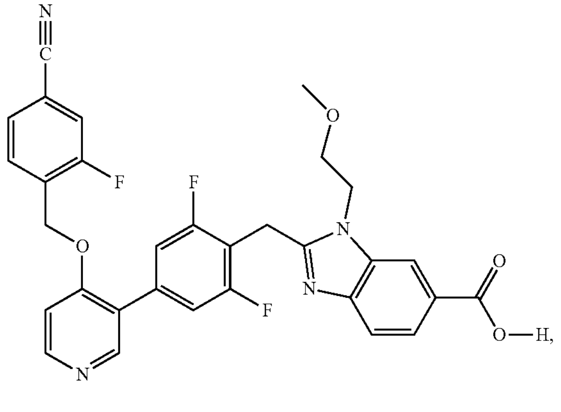

-continued
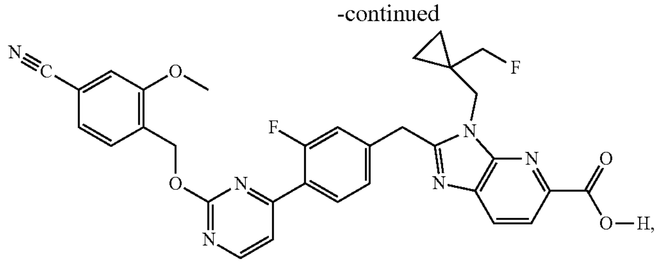
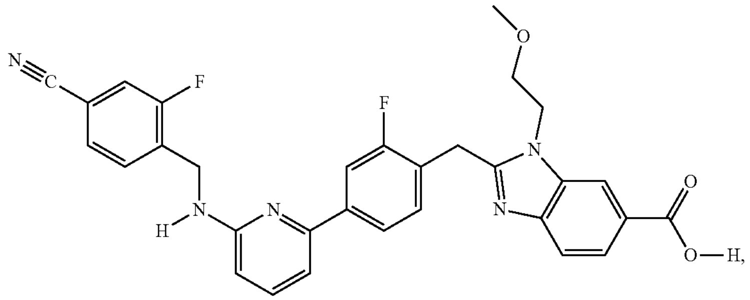
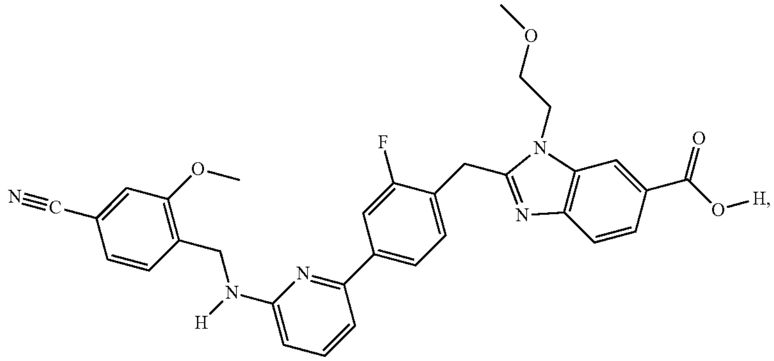
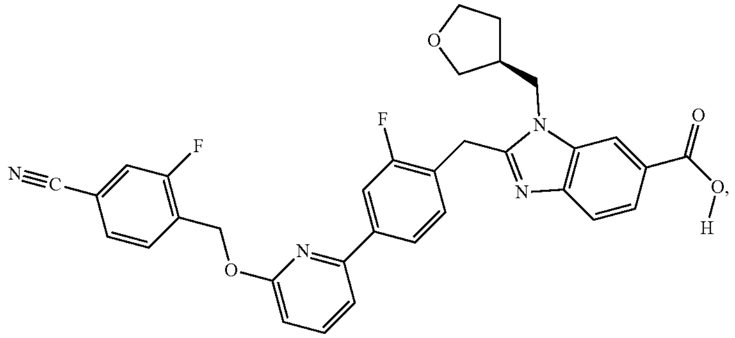
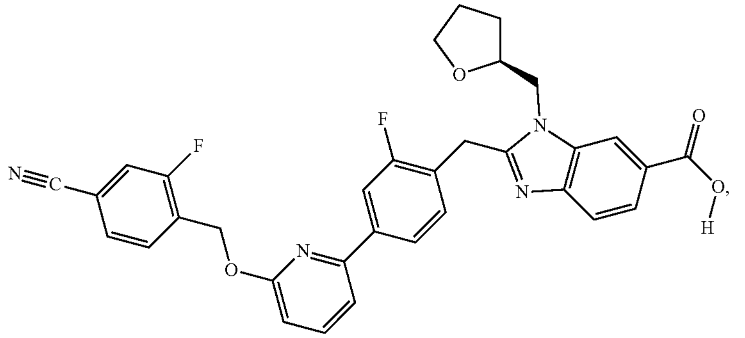

-continued
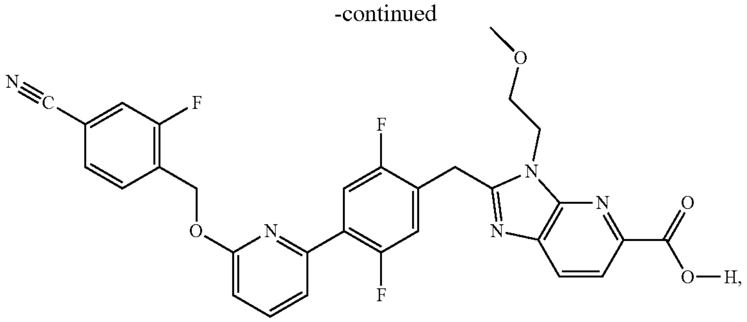
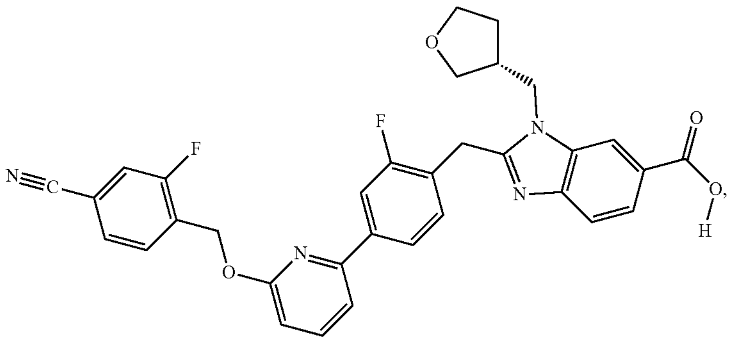
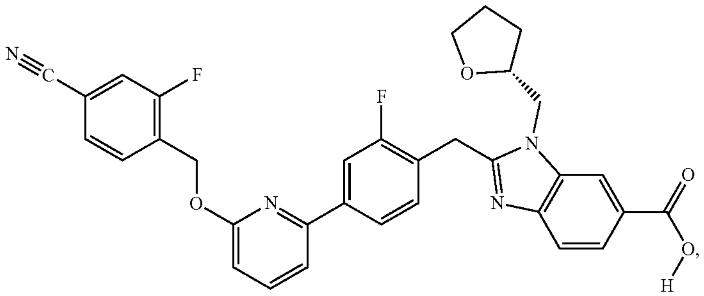
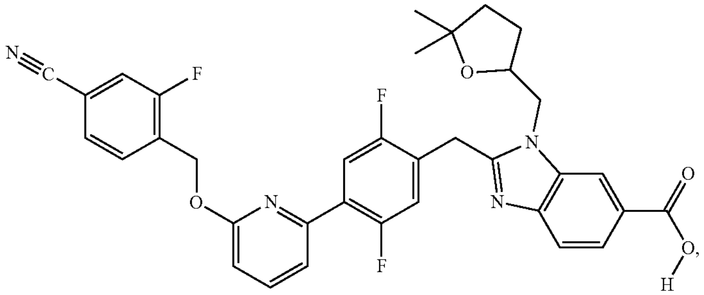
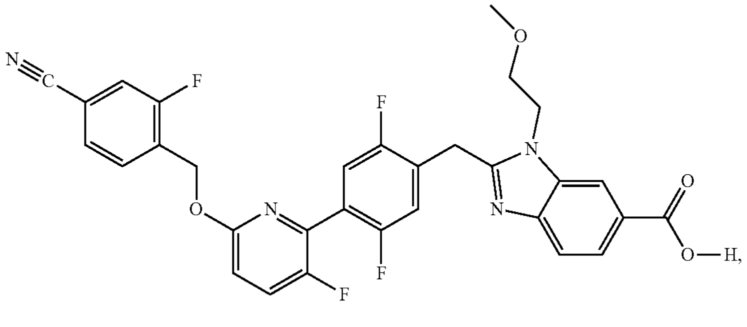

-continued
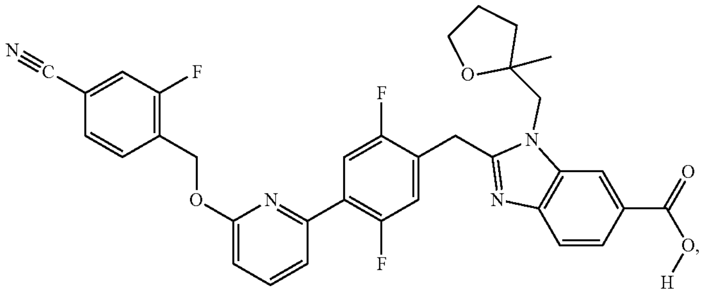
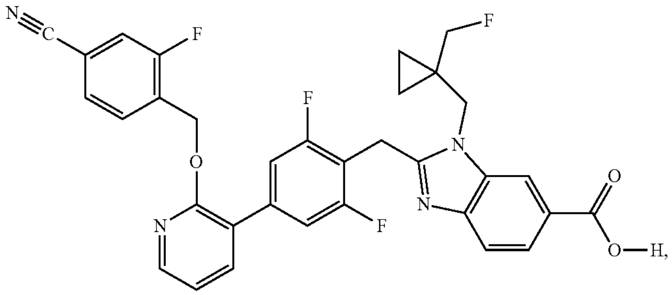
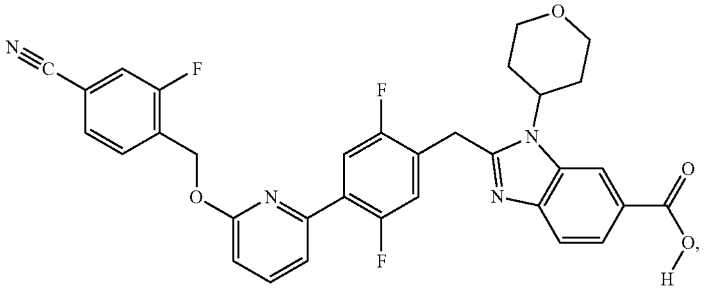
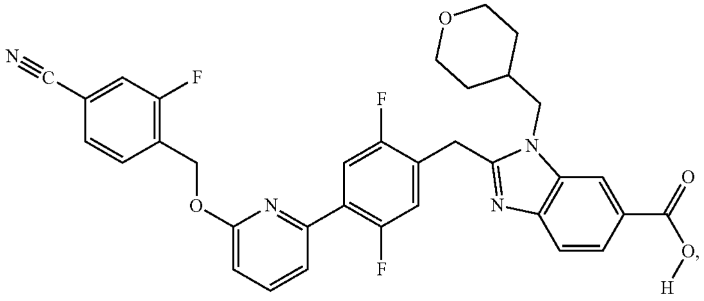
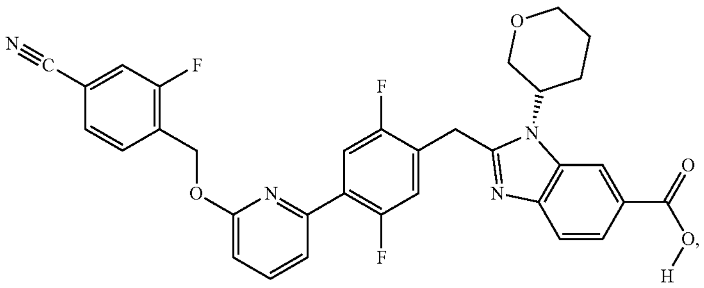

-continued
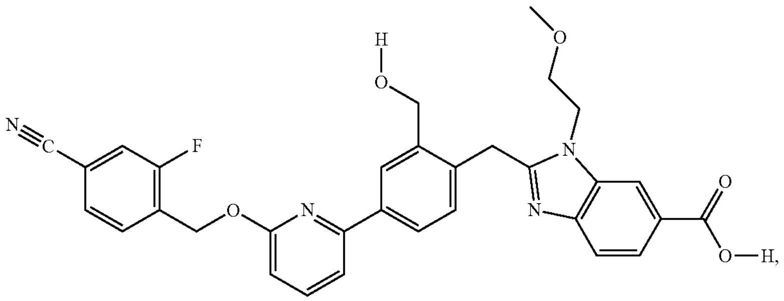
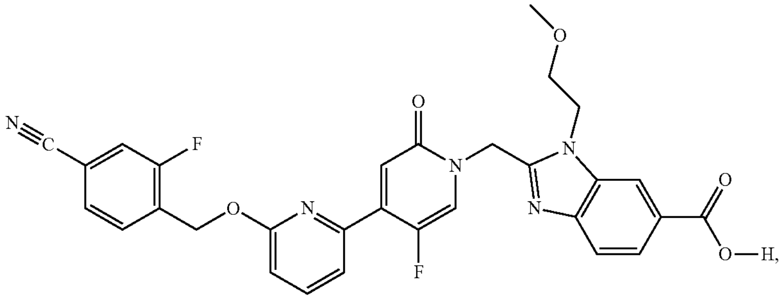
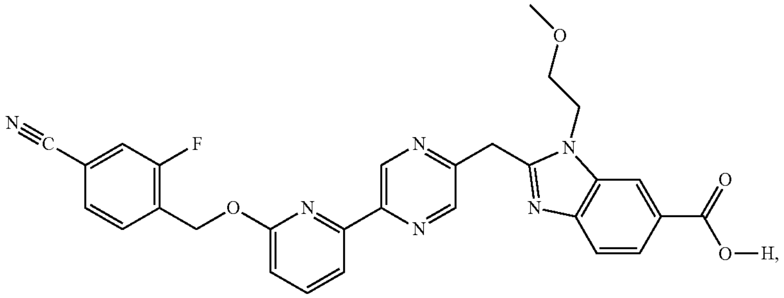
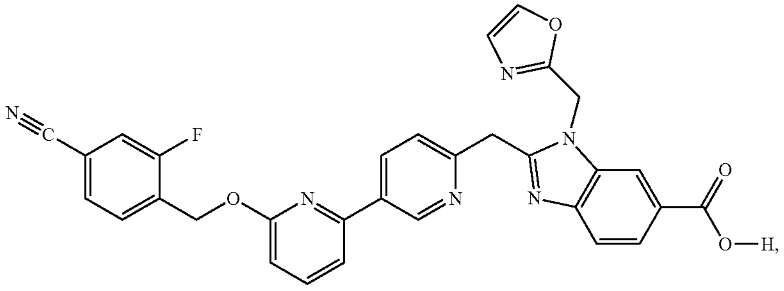
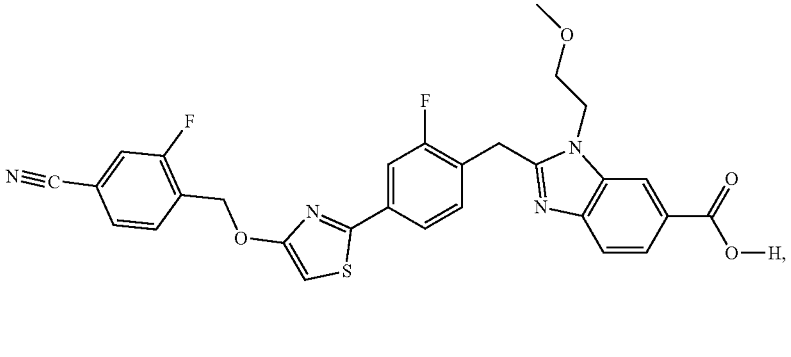

-continued
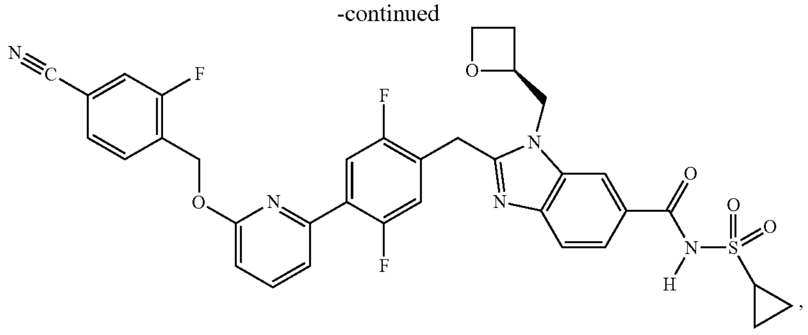
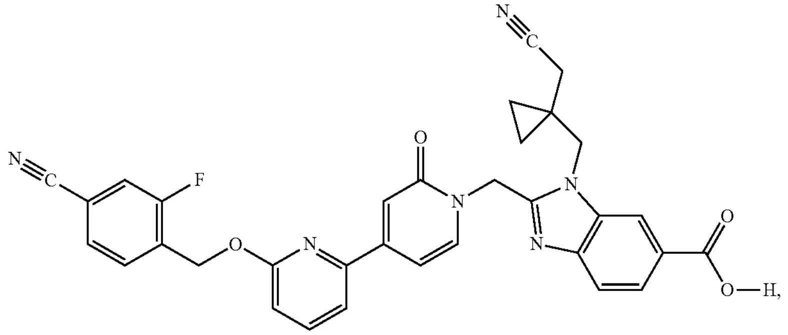
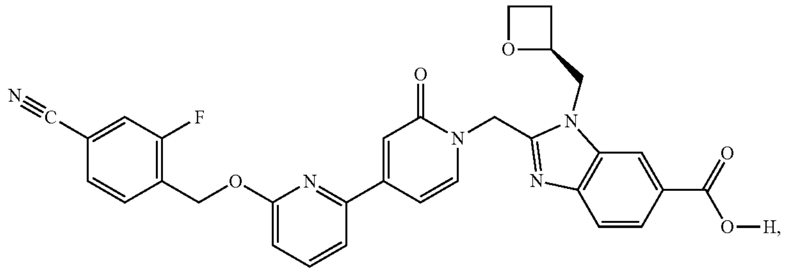
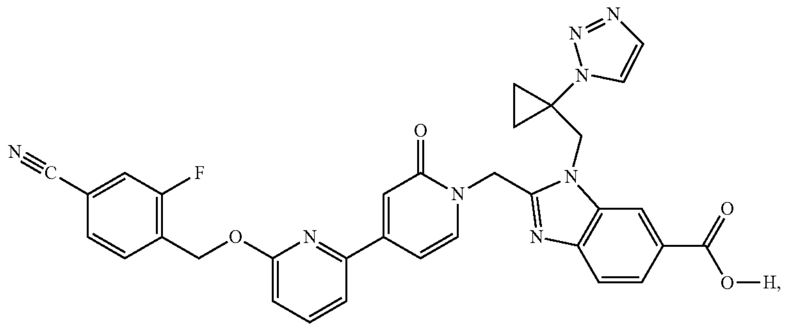
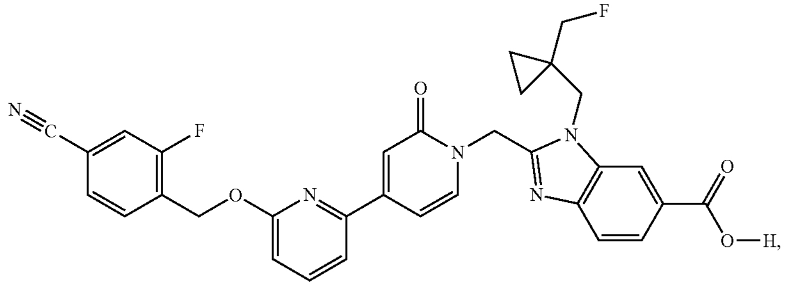

-continued
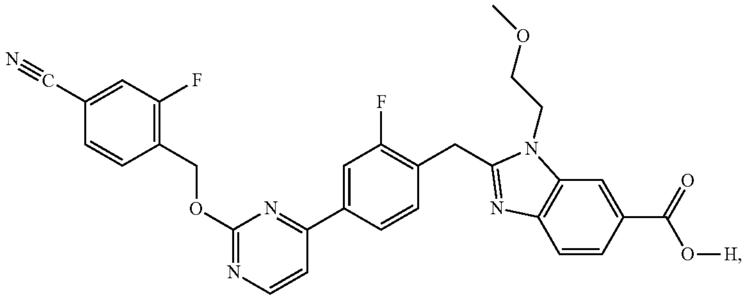
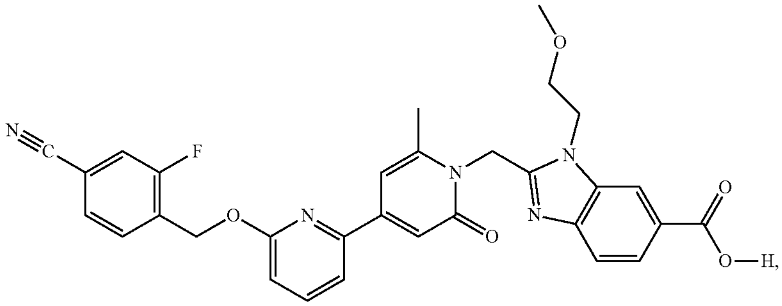
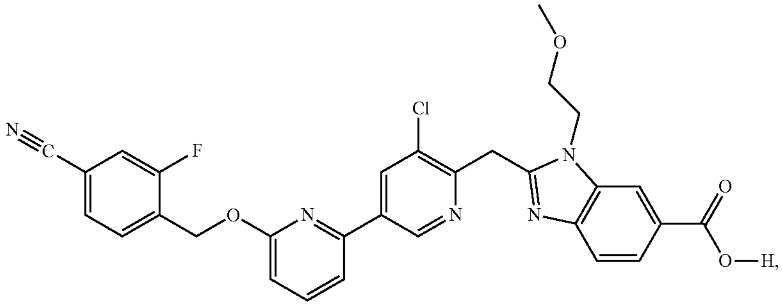
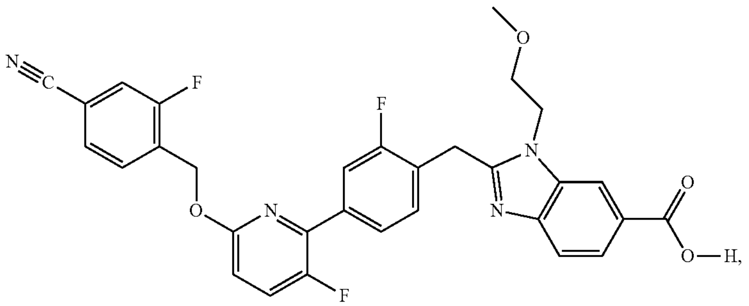
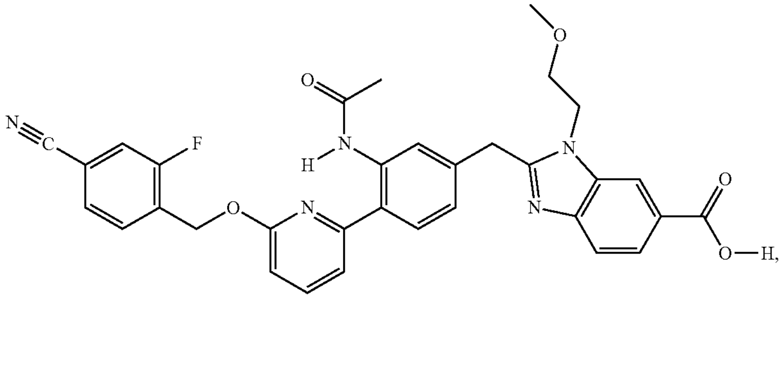

-continued
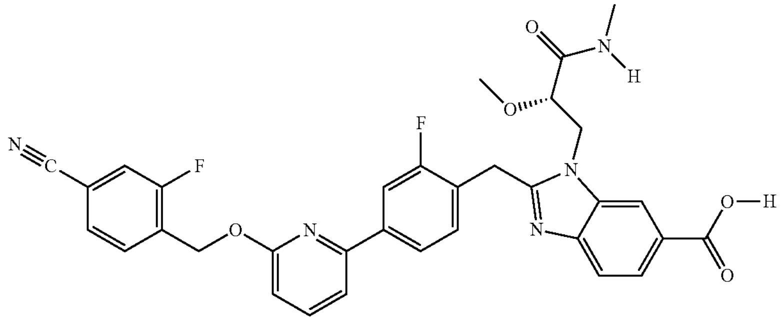
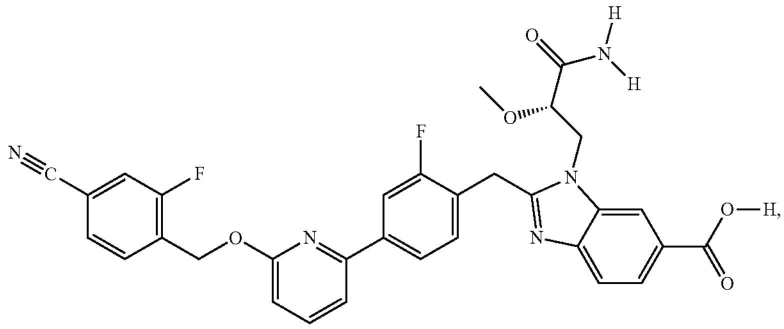
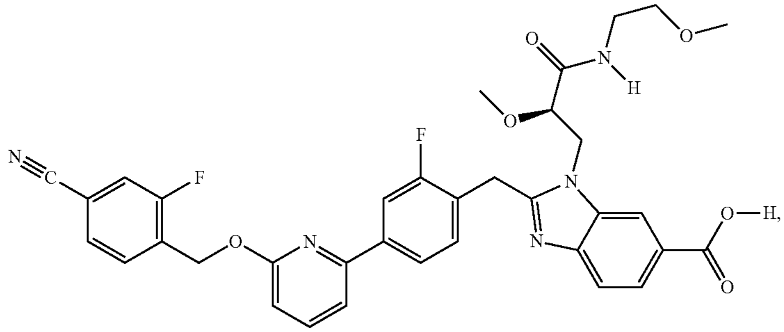
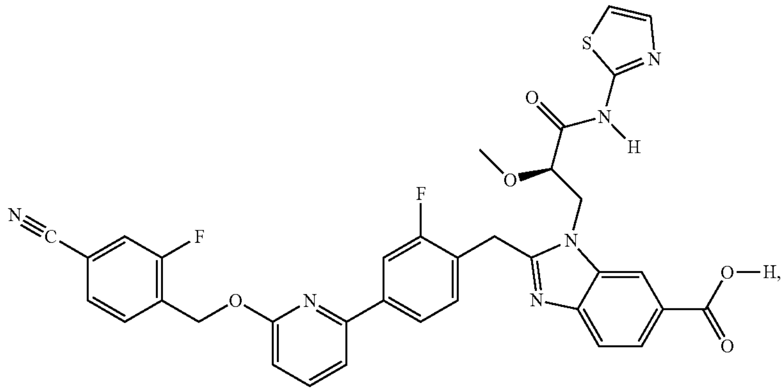
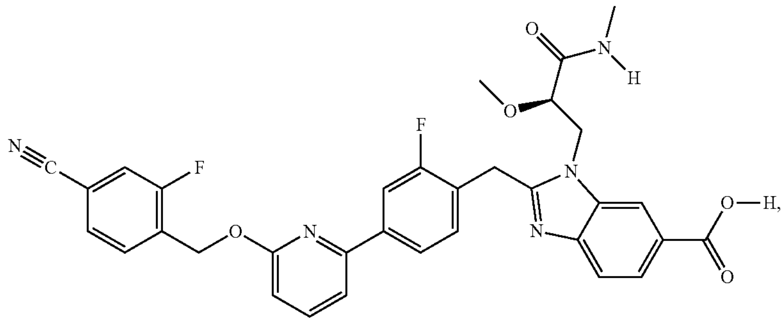

-continued
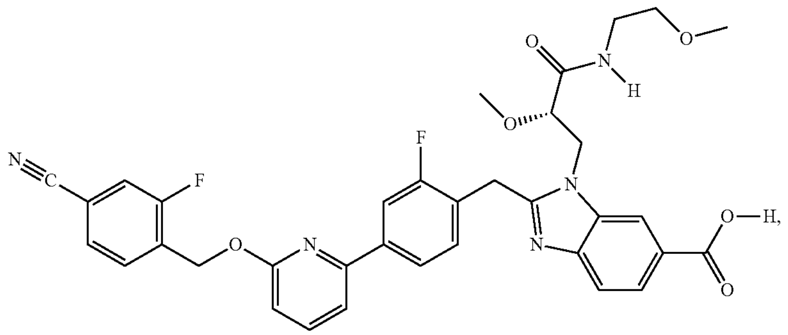
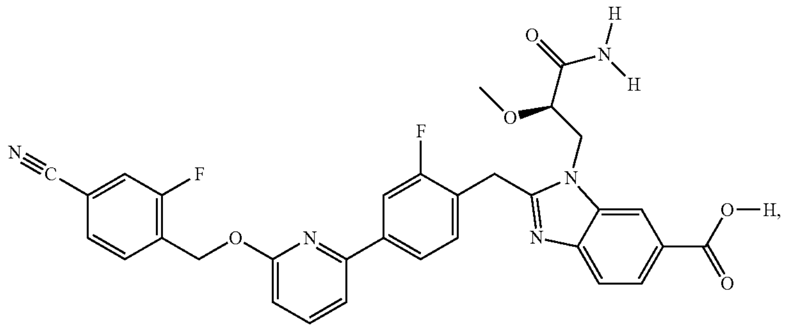
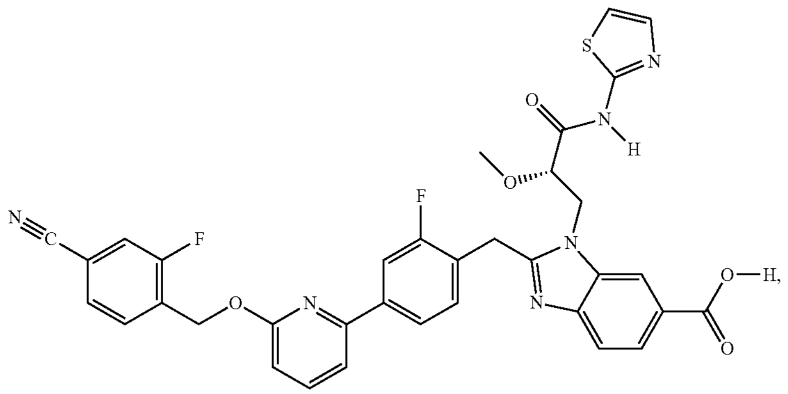
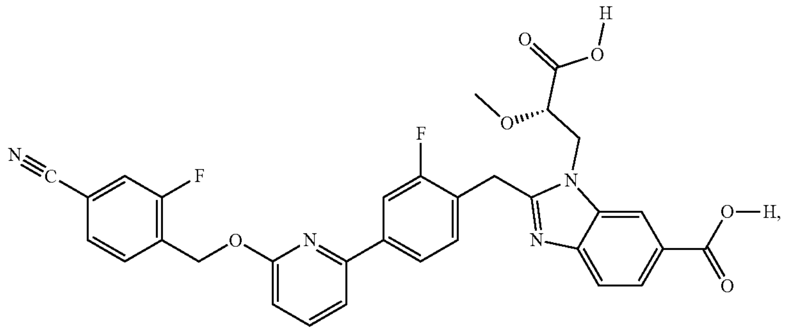

-continued
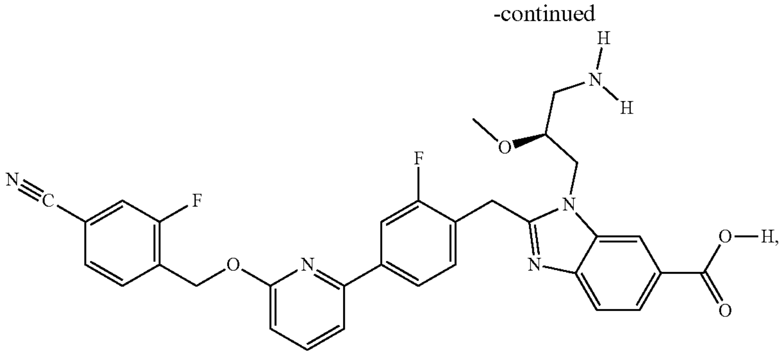
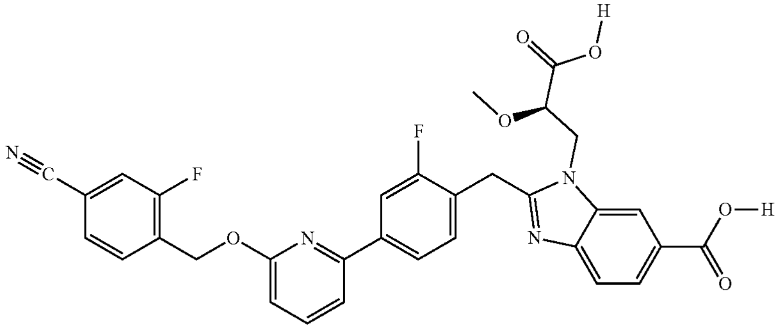
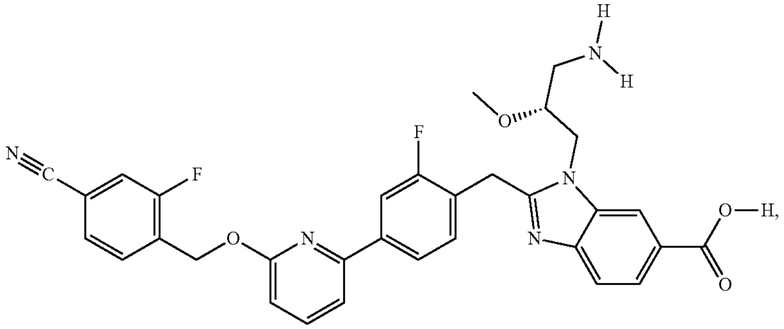
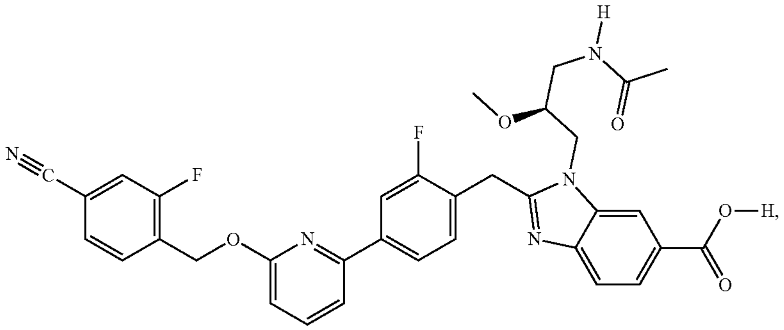
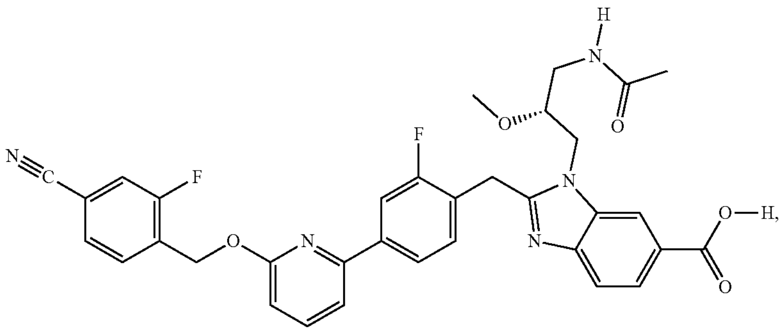

-continued
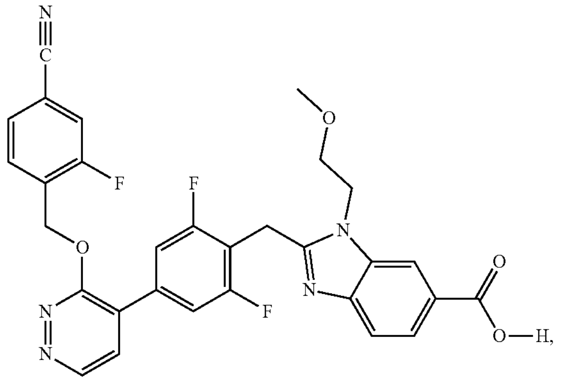
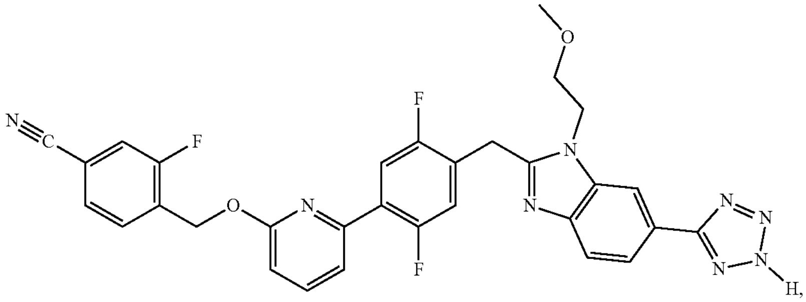
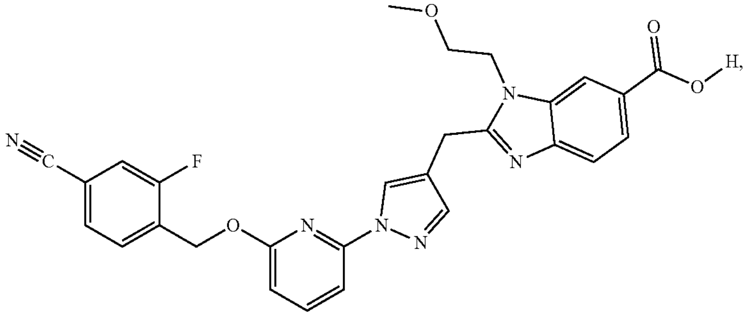
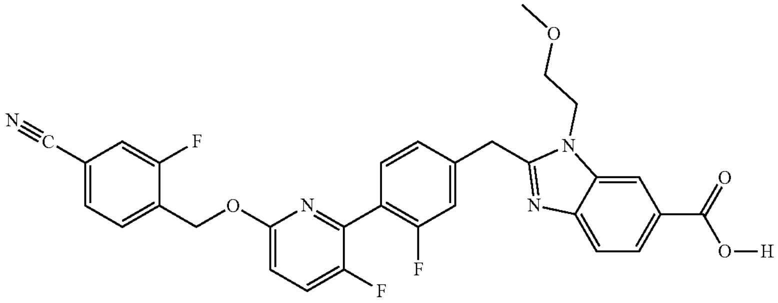
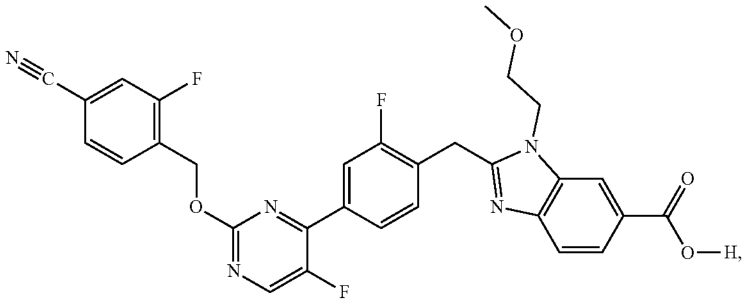

-continued
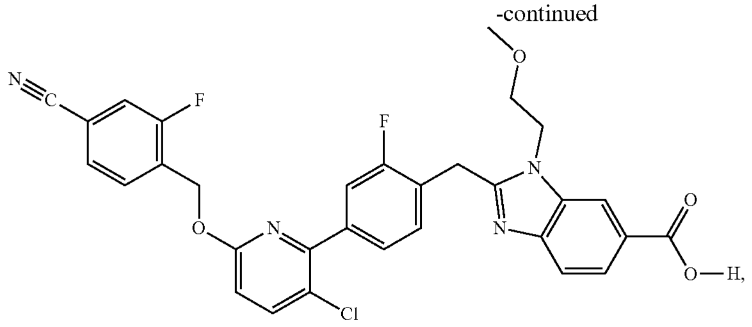
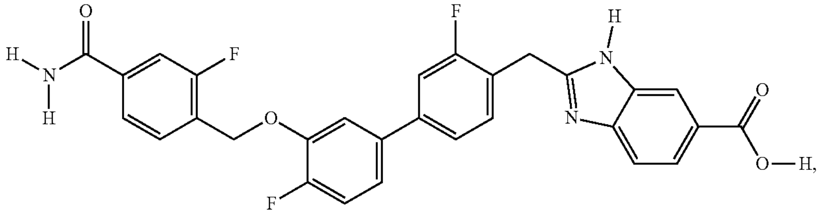
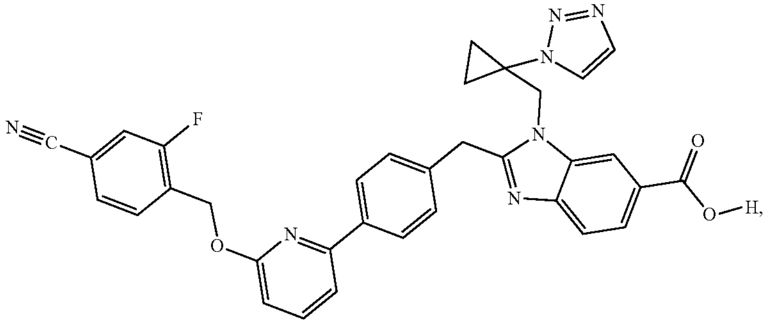
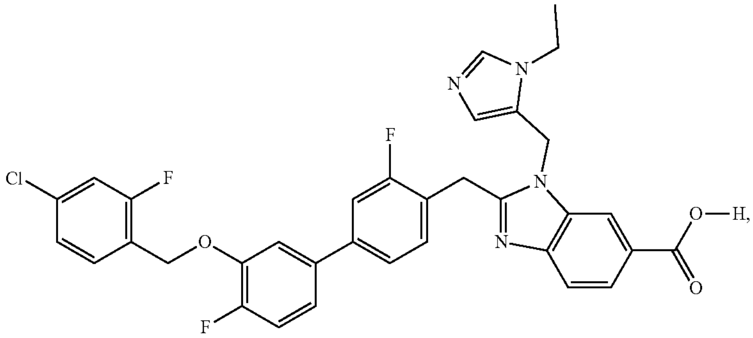
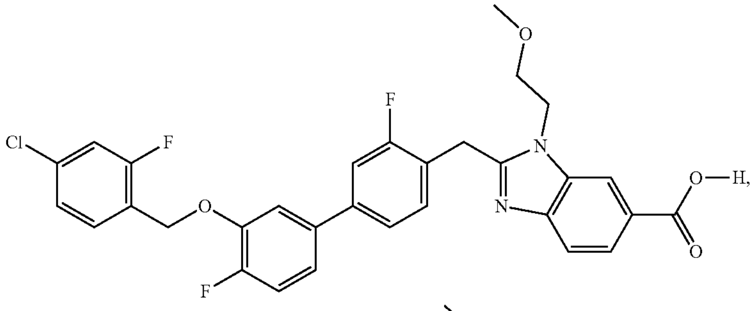
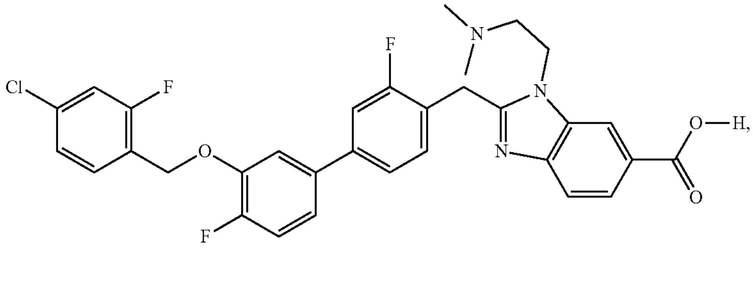

-continued
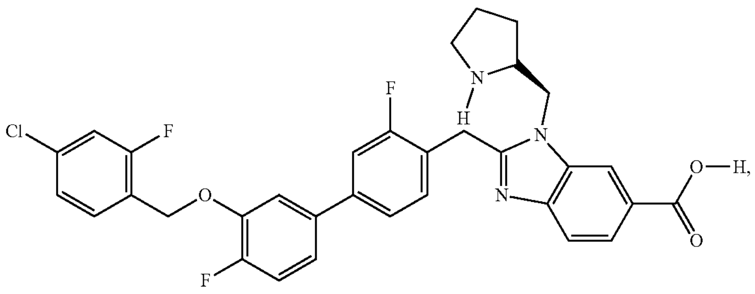
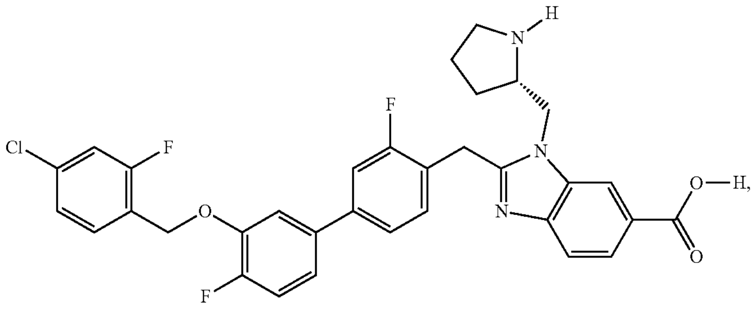
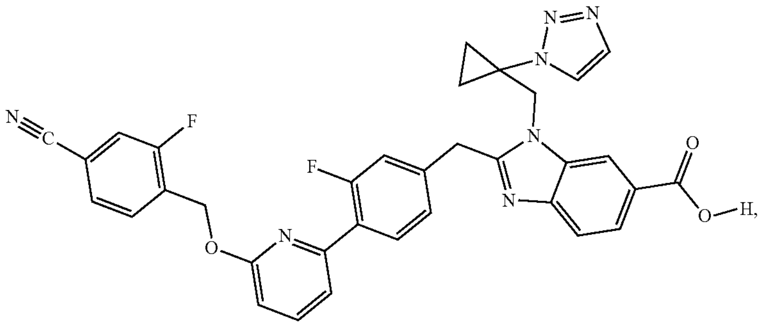
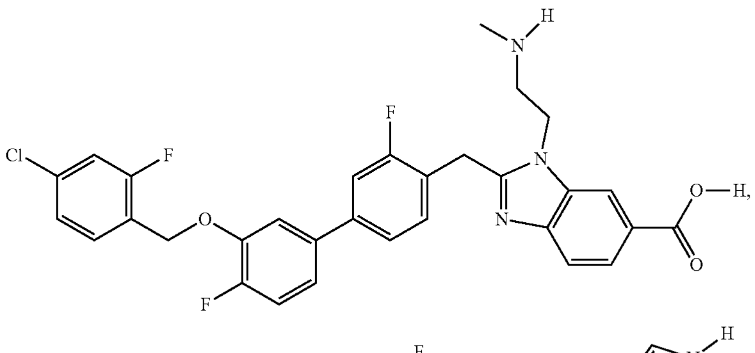
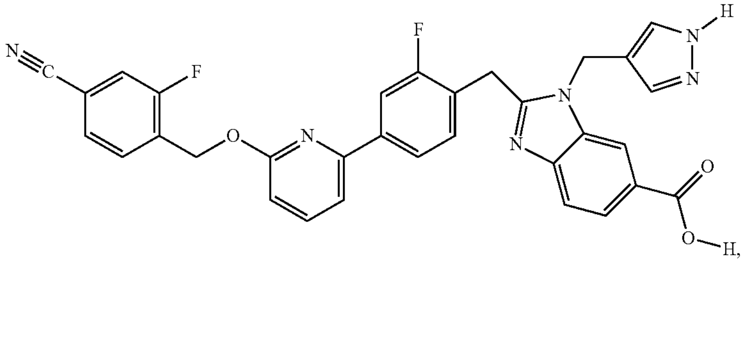

-continued
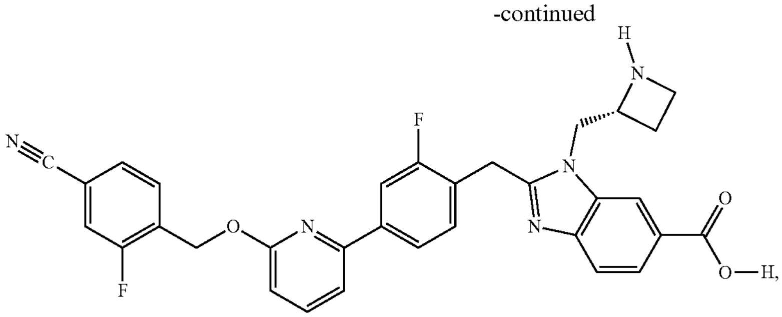
,
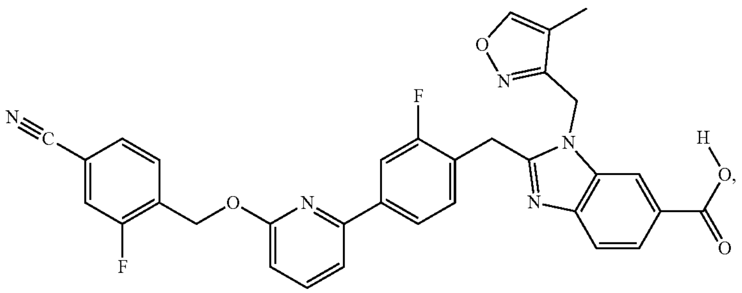
,
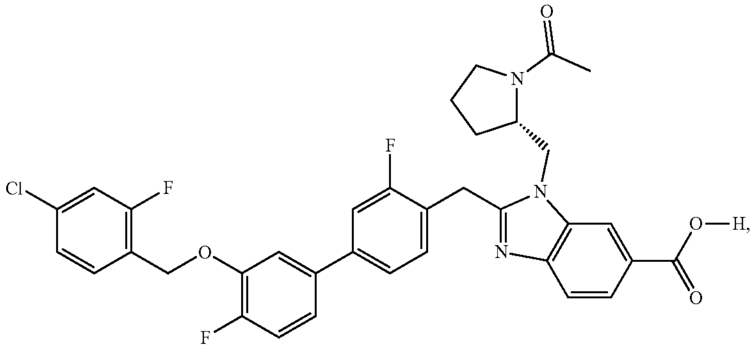
,
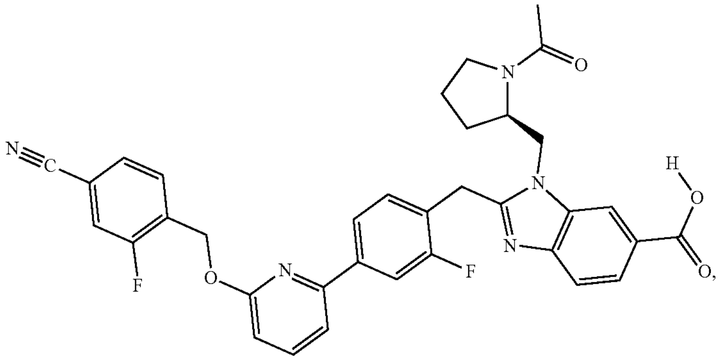
,
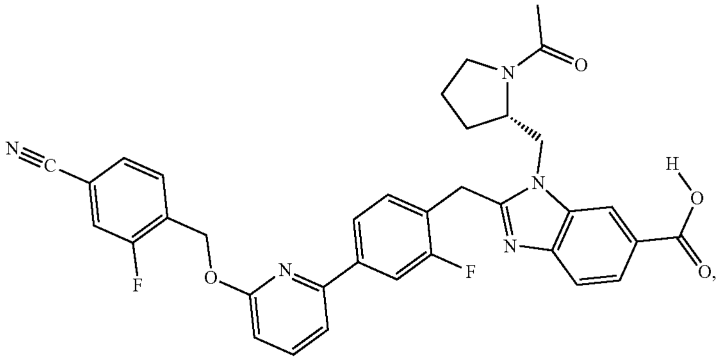
, -continued
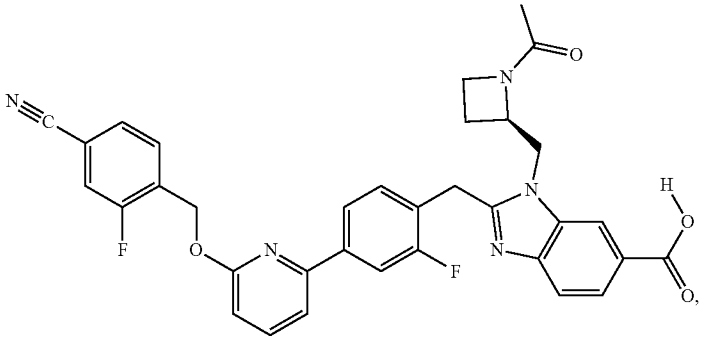
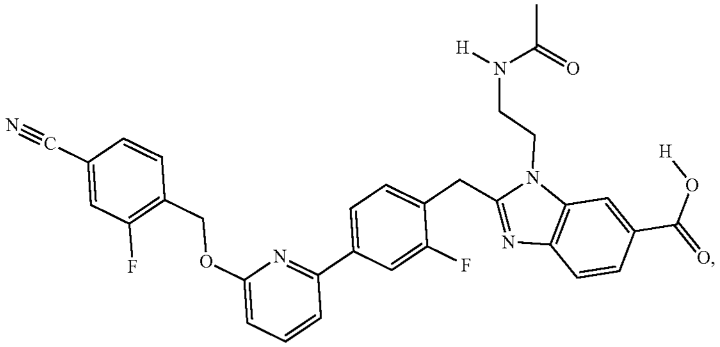
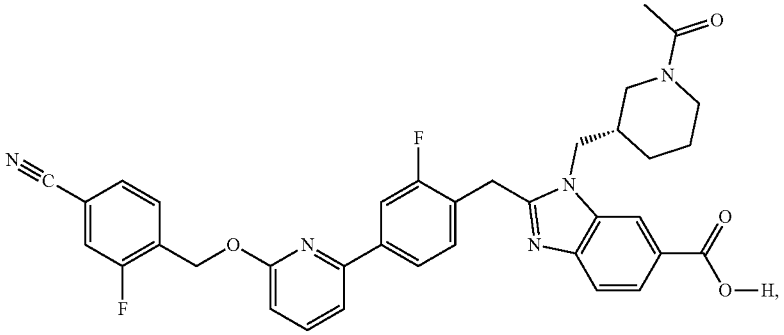
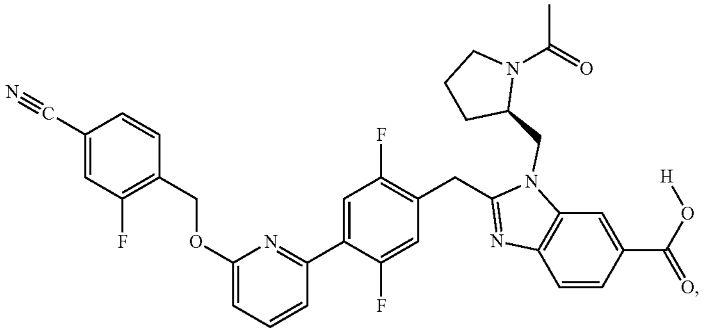
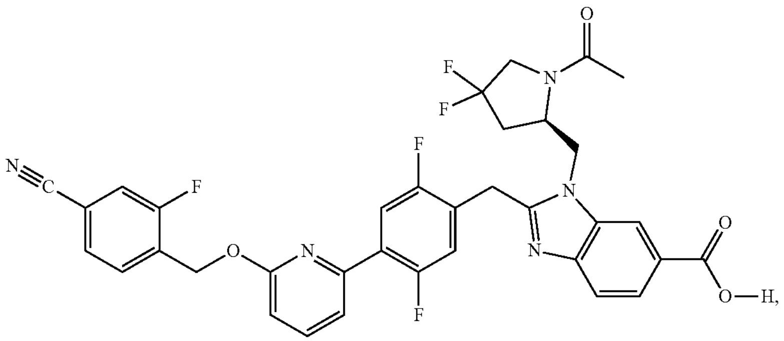

-continued
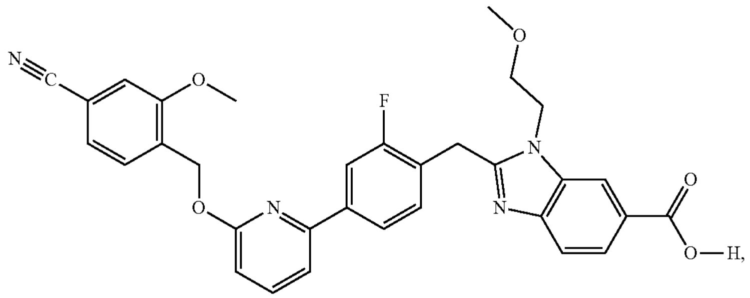
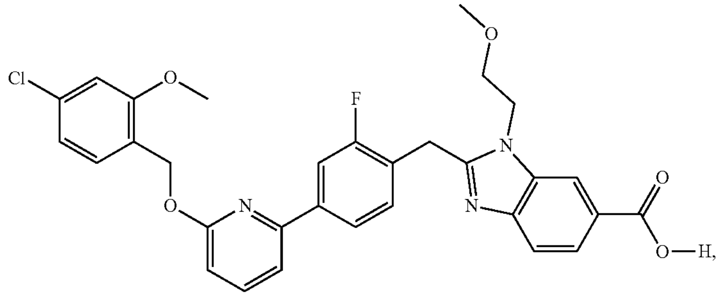
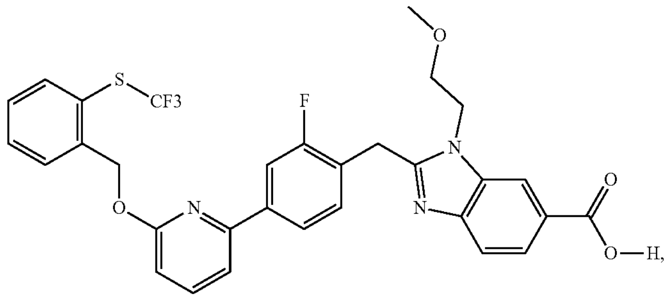
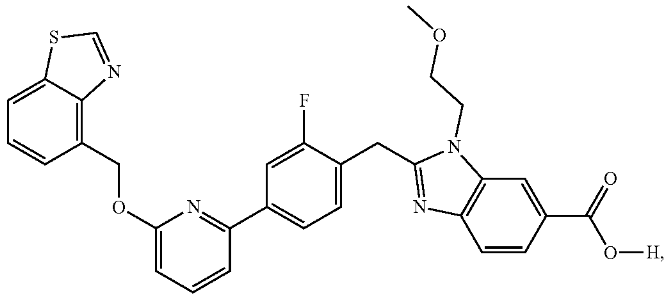
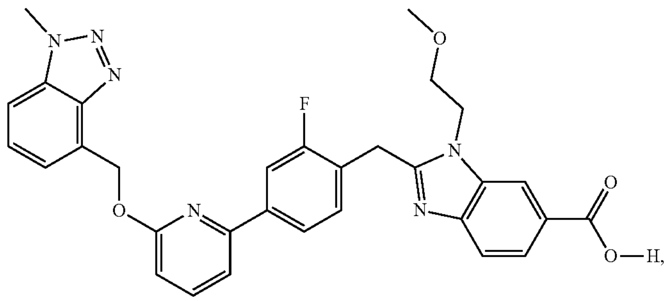

-continued
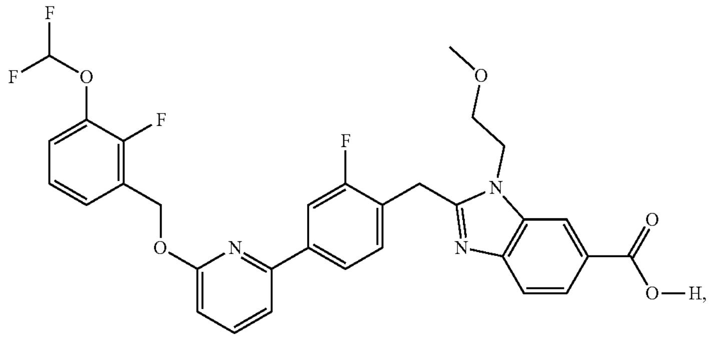
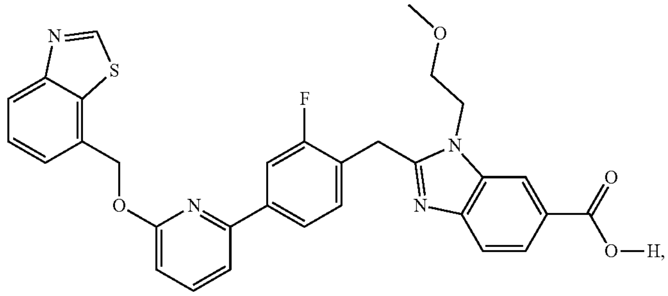
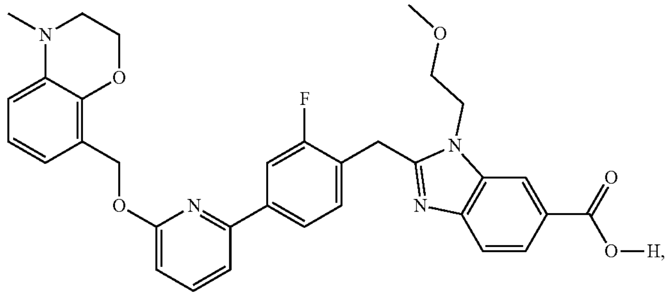
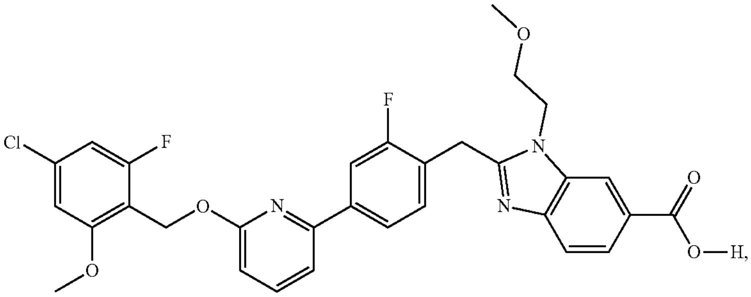
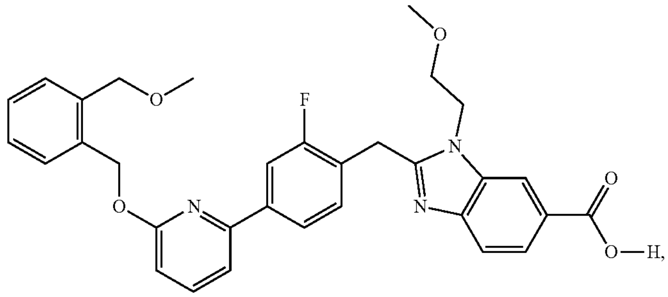

-continued
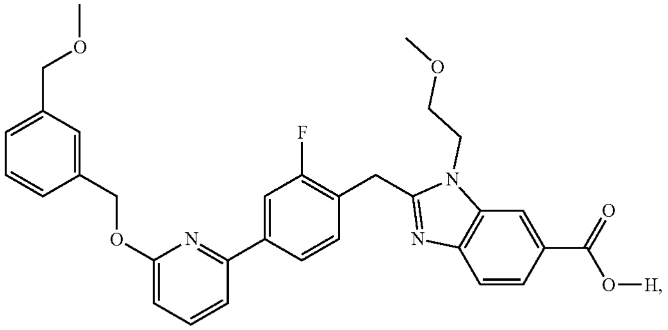
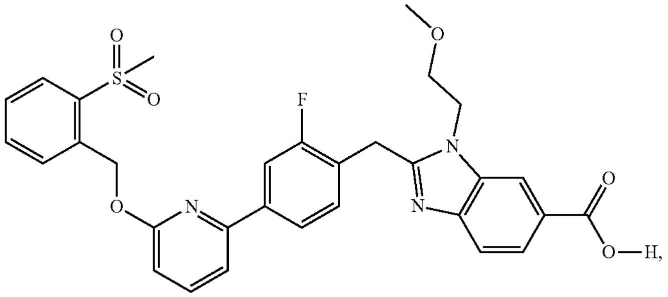
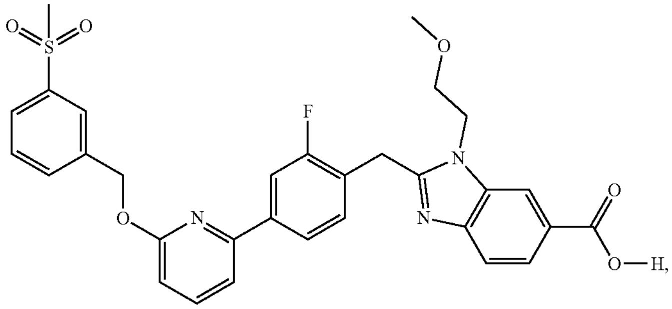
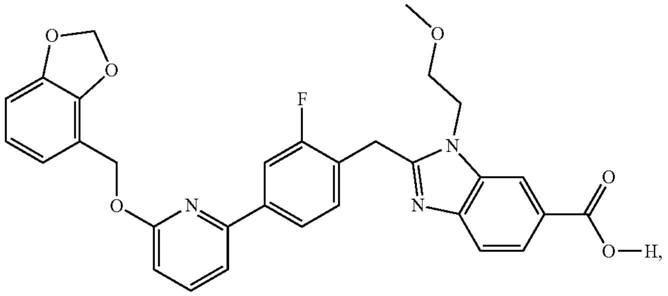
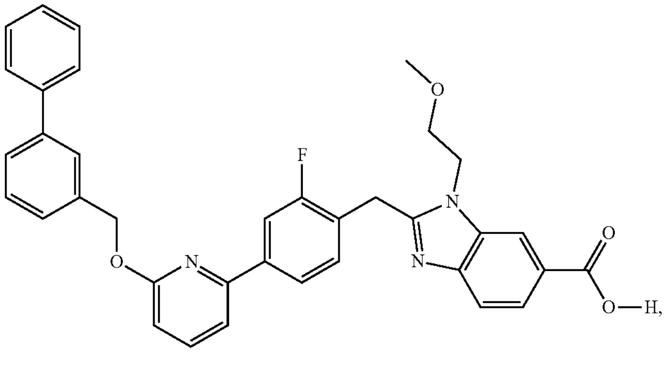

-continued
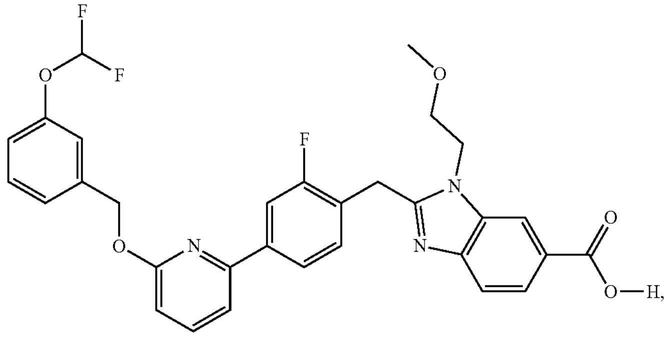
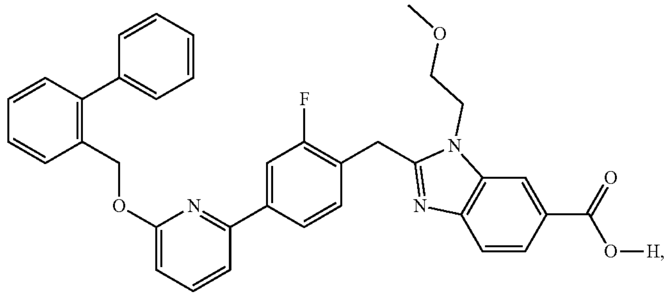
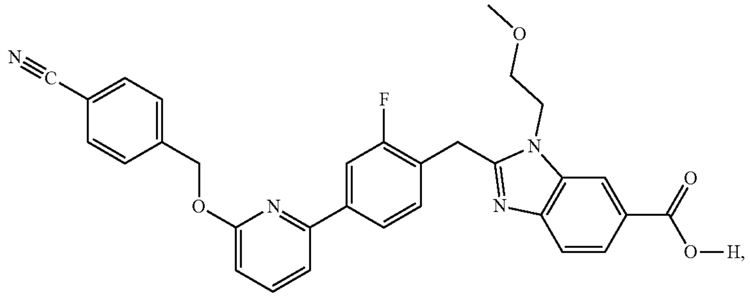
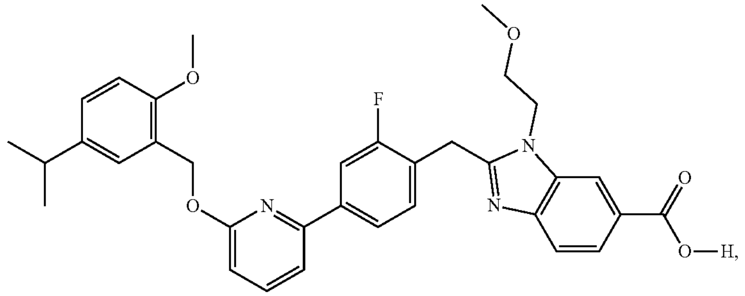
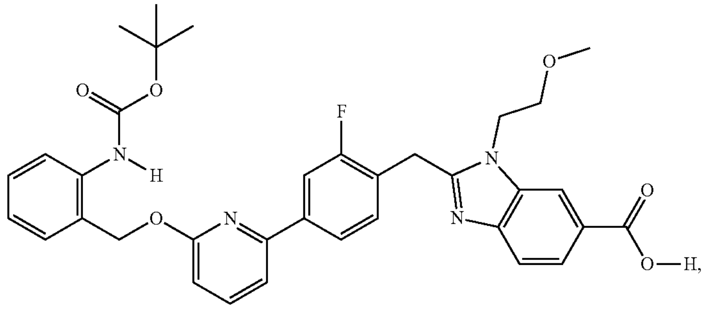

-continued
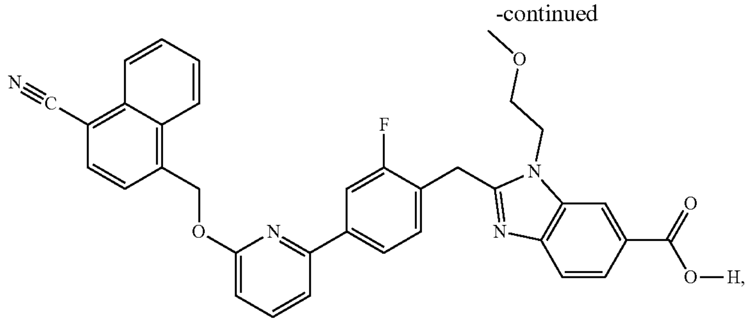
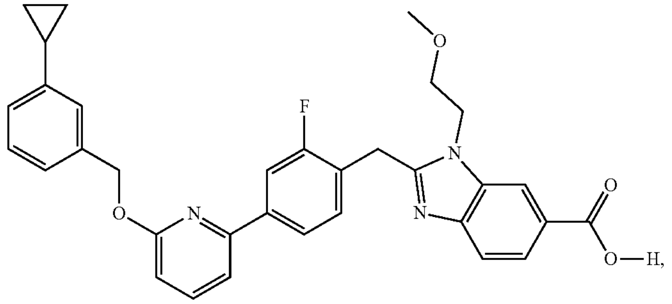
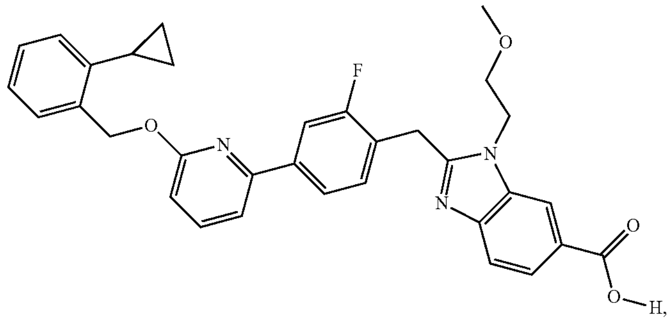
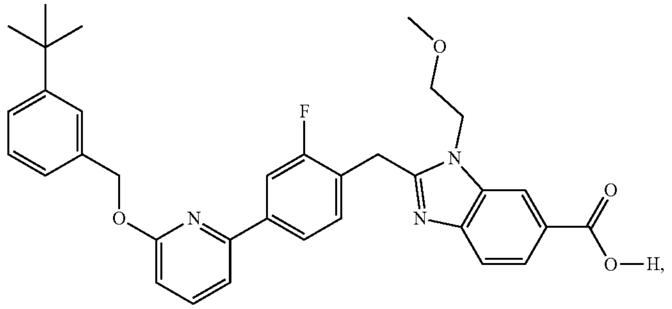
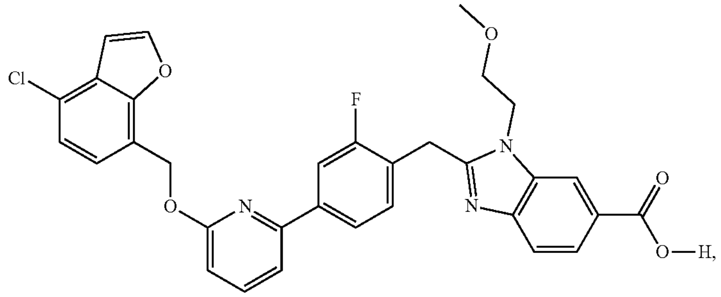

-continued
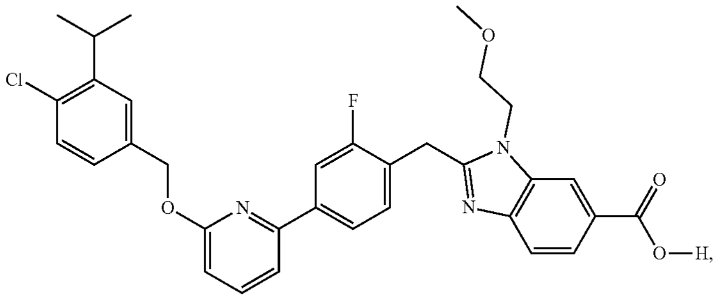
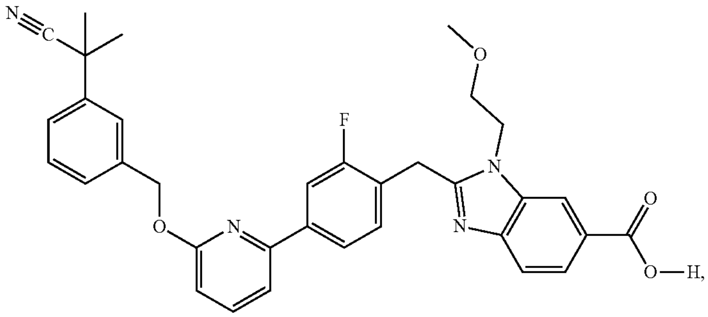
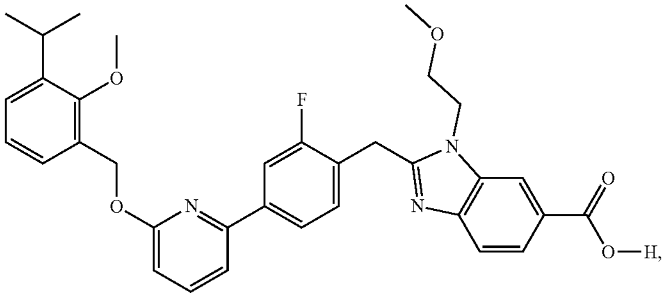
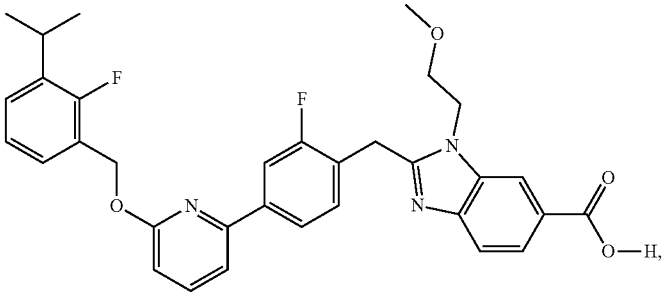
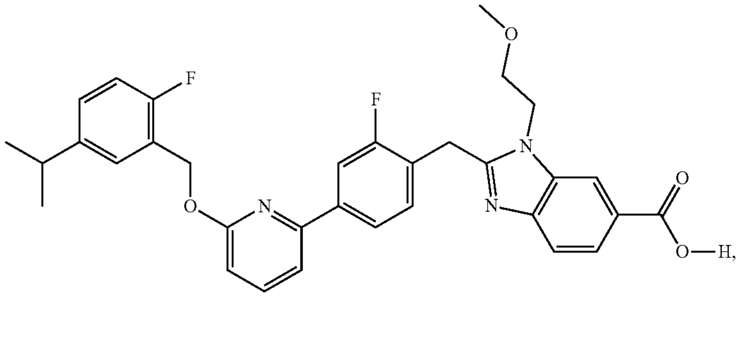

-continued
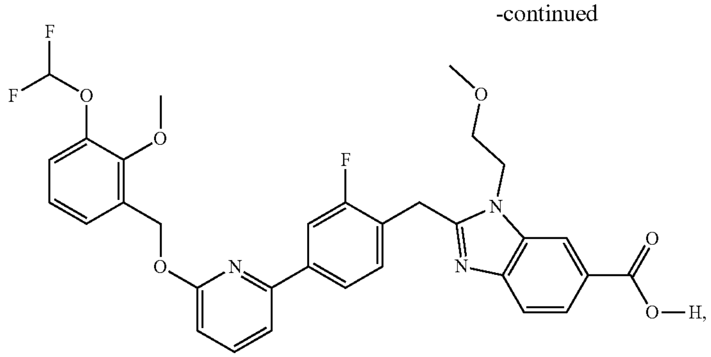
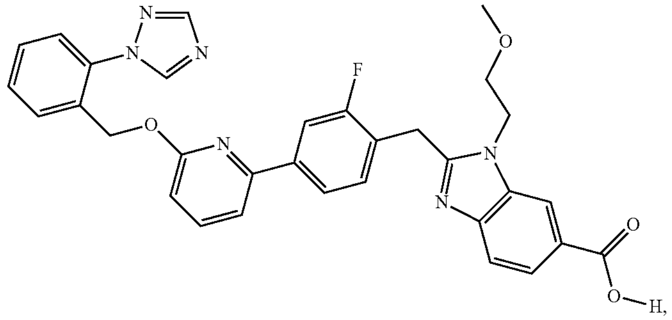
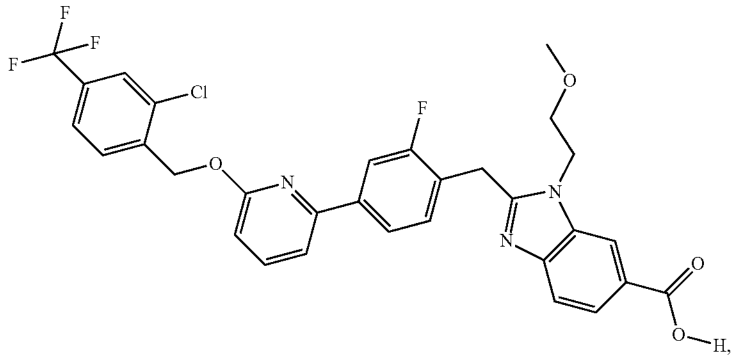
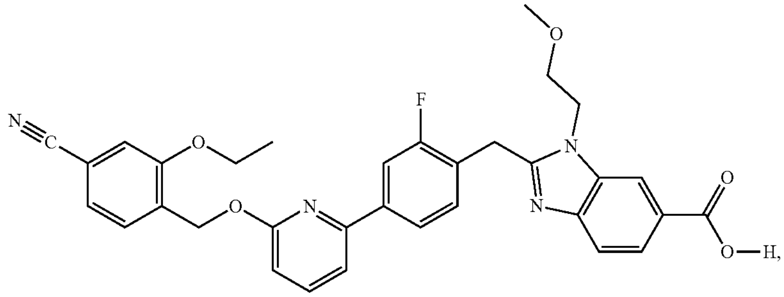
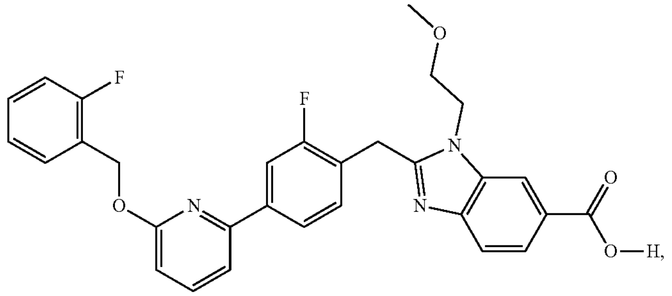

-continued
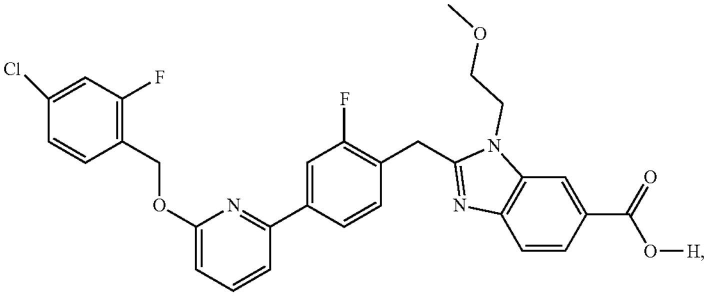
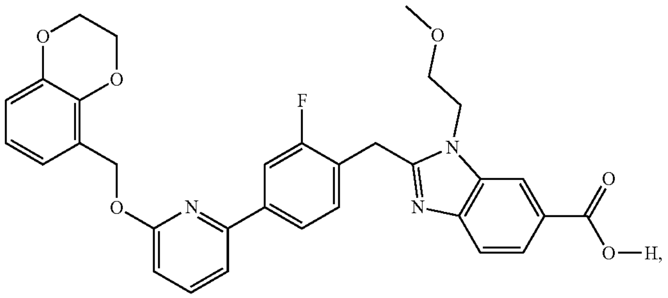
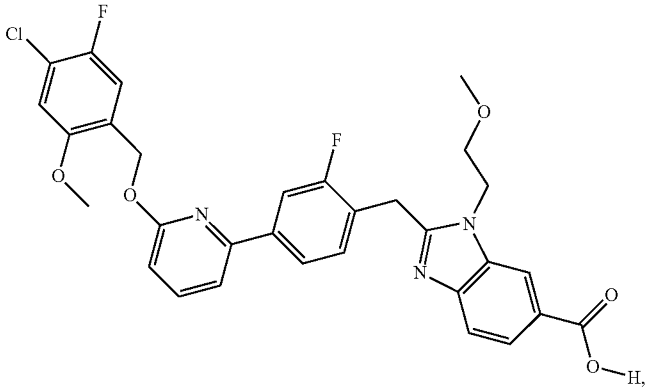
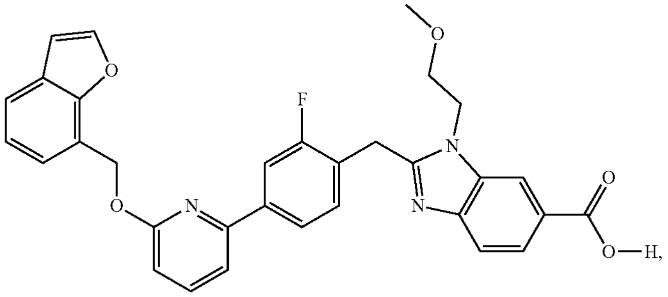
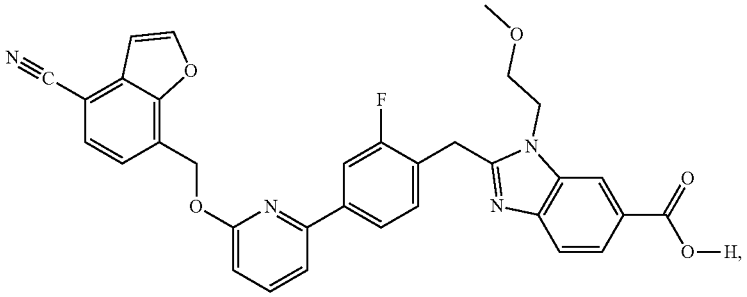

-continued
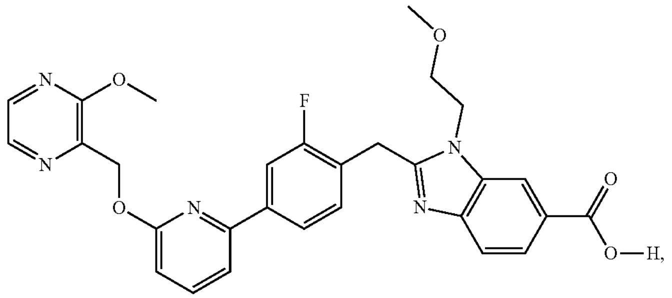
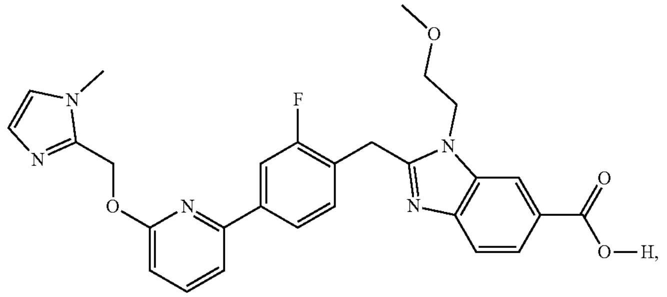
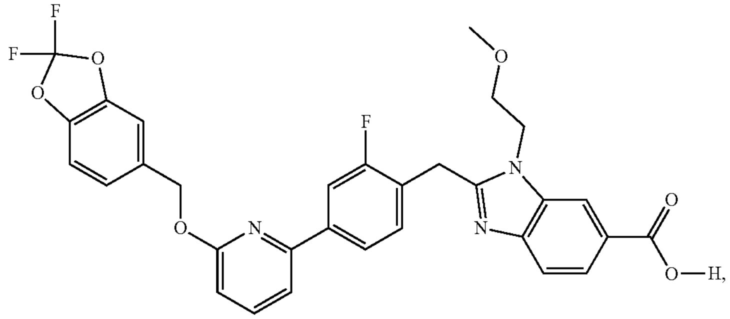
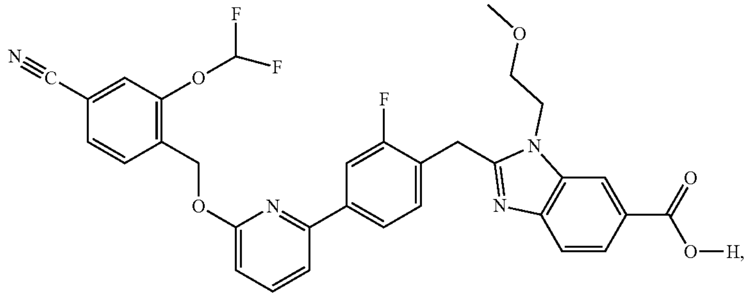
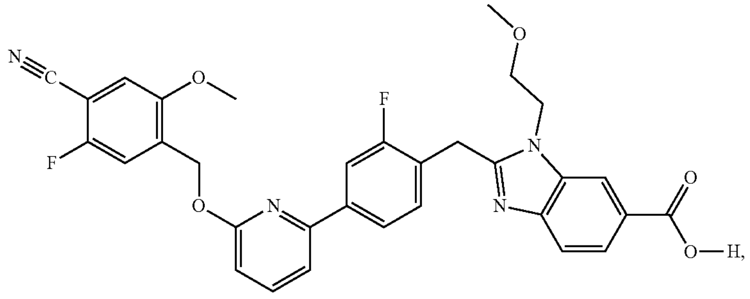

-continued
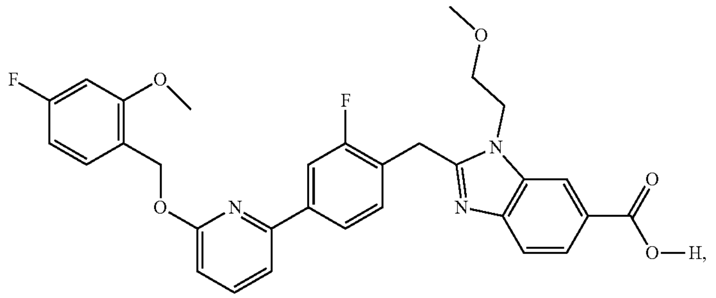
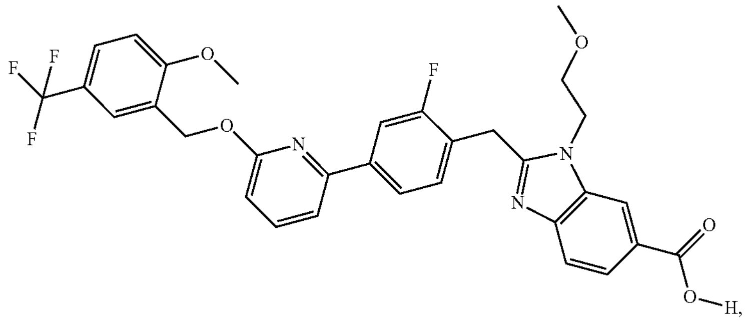
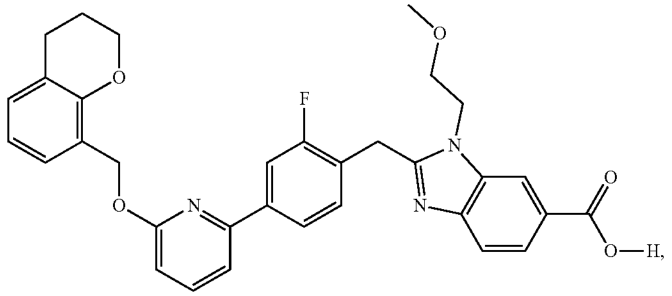
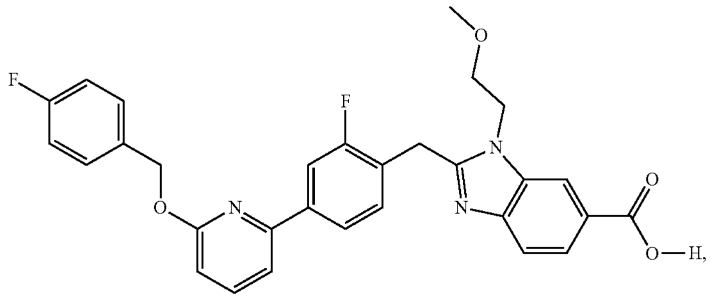
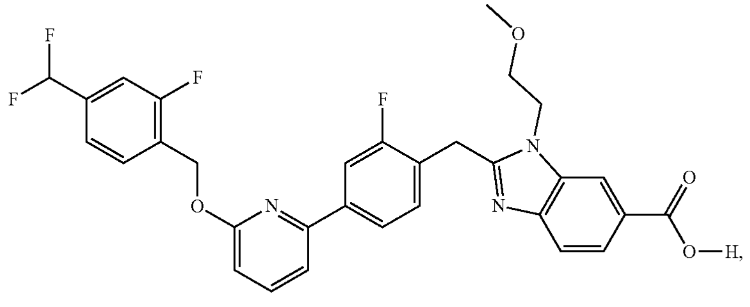

-continued
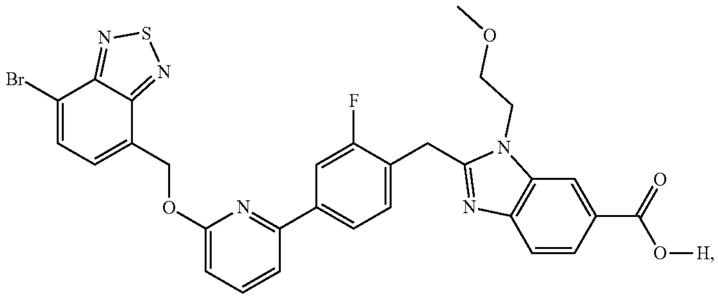
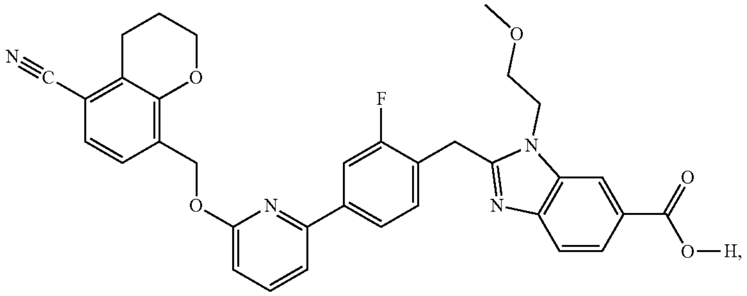
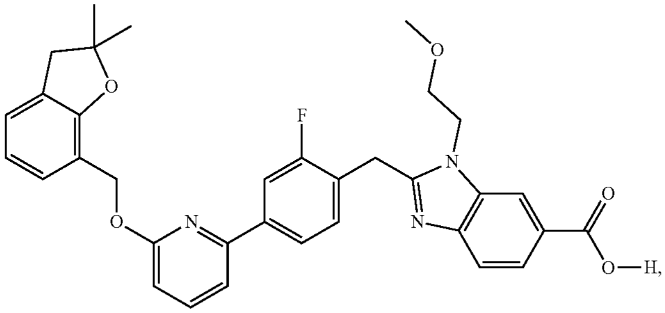
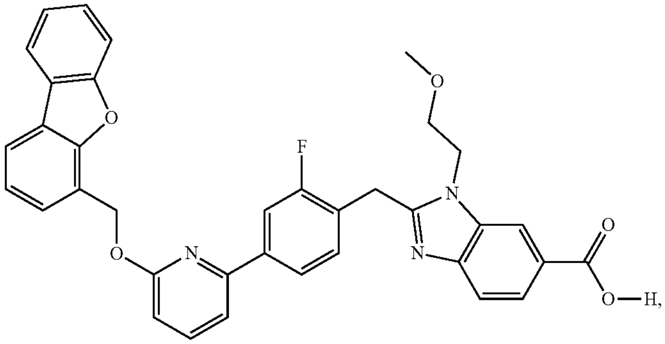
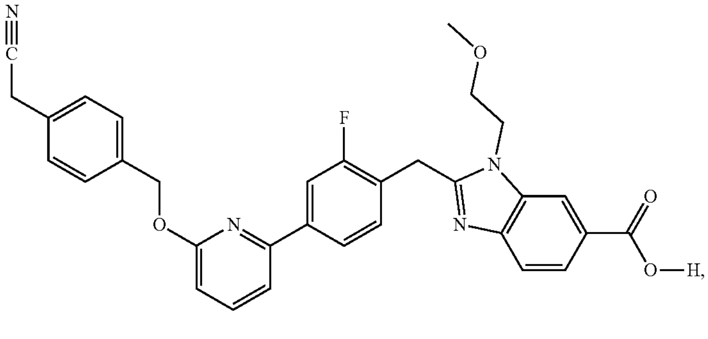

-continued
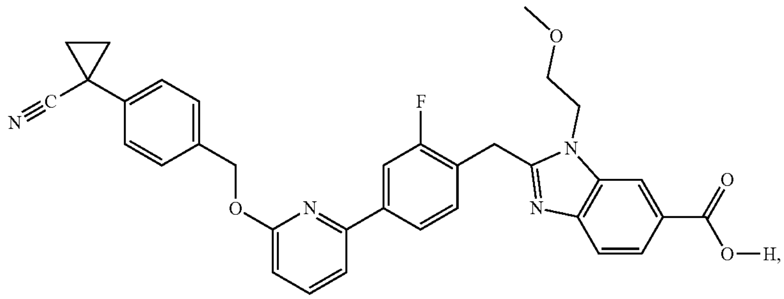
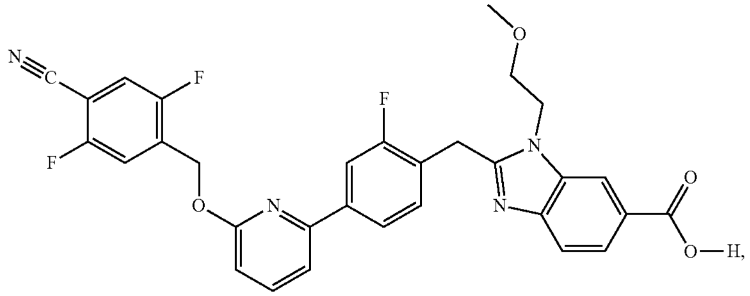
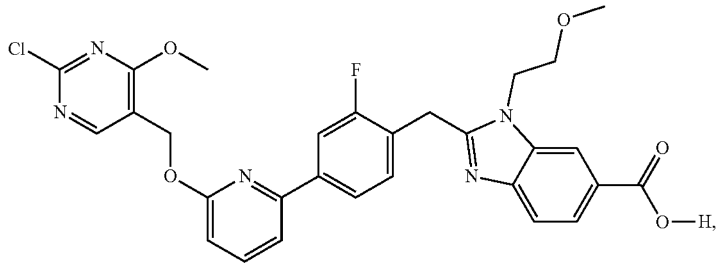
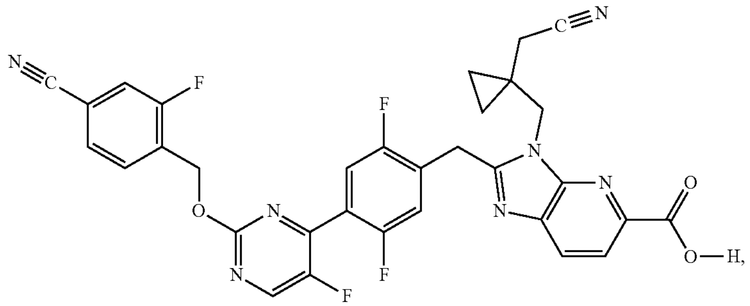
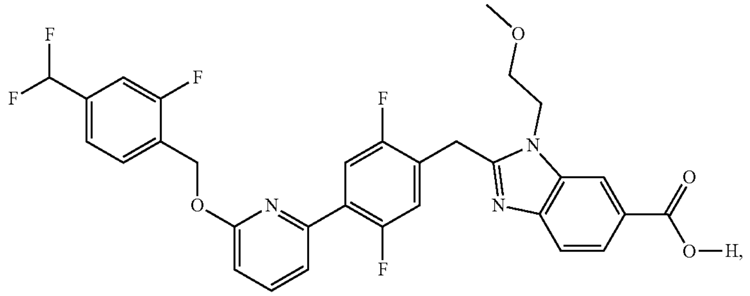

-continued
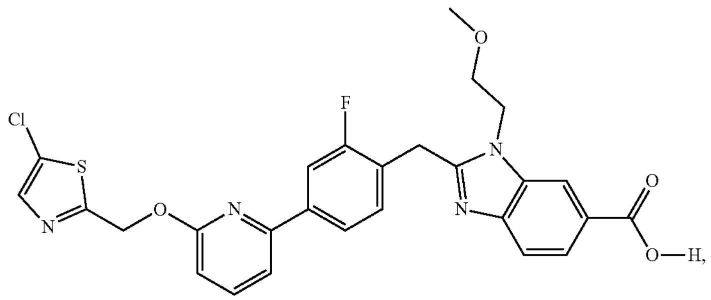
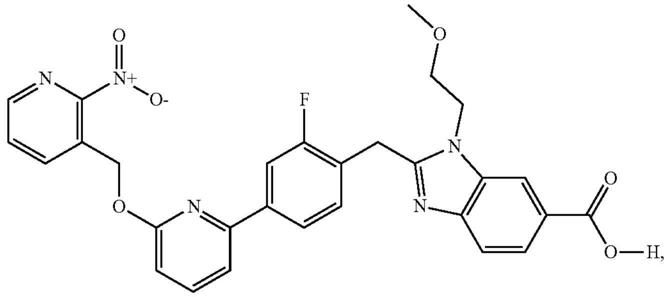
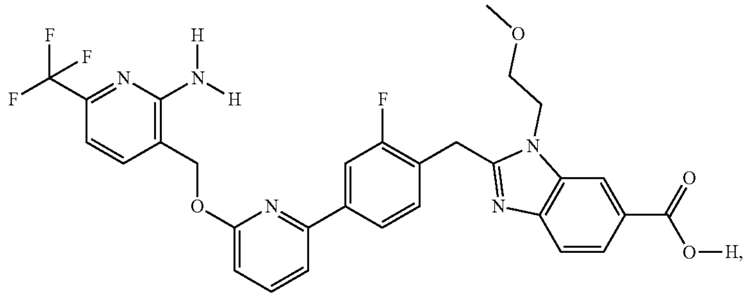
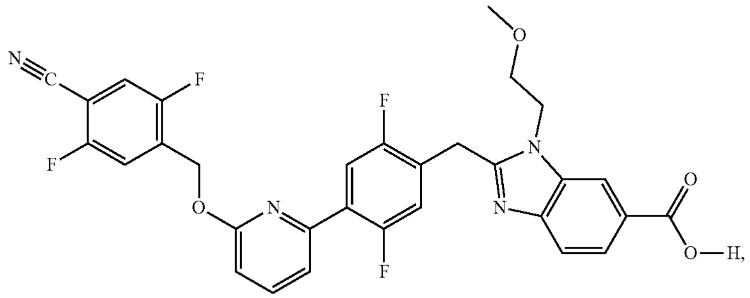
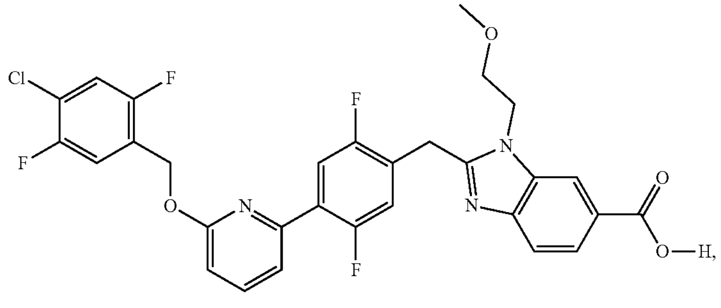

-continued
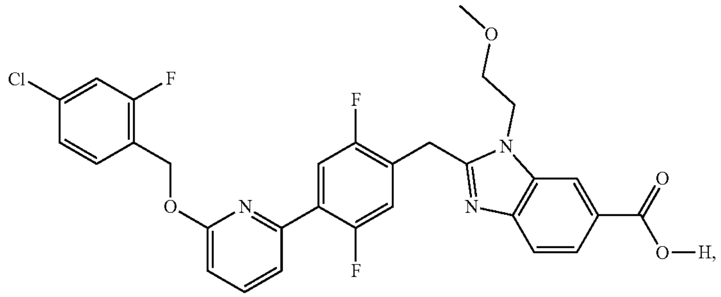
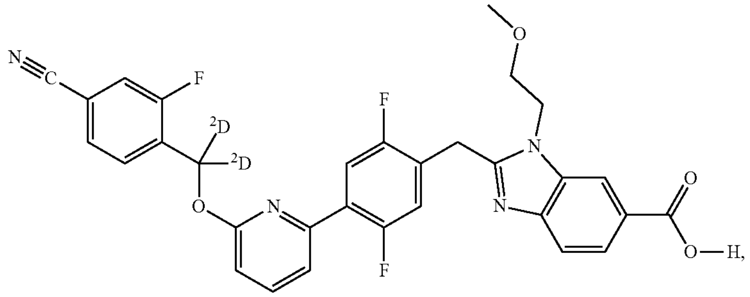
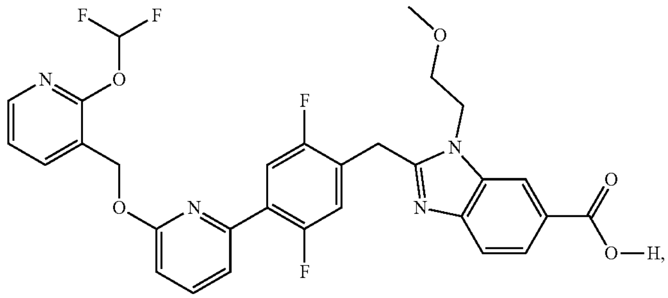
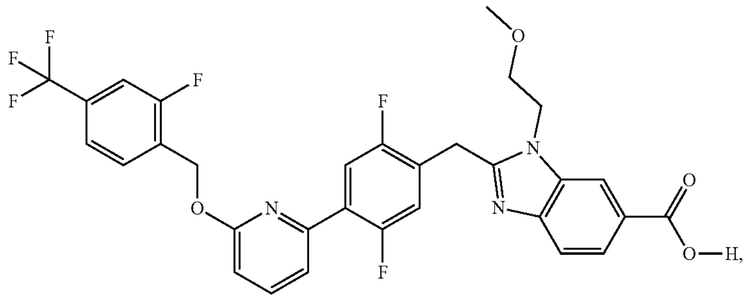
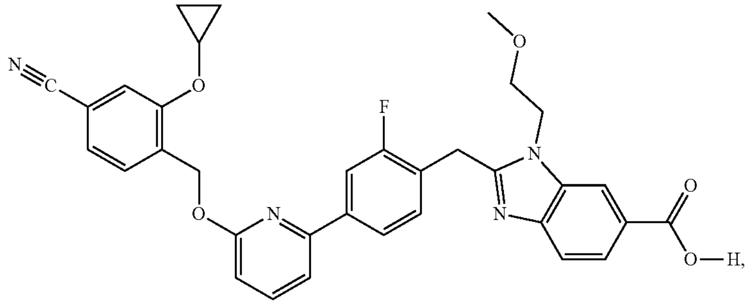

-continued
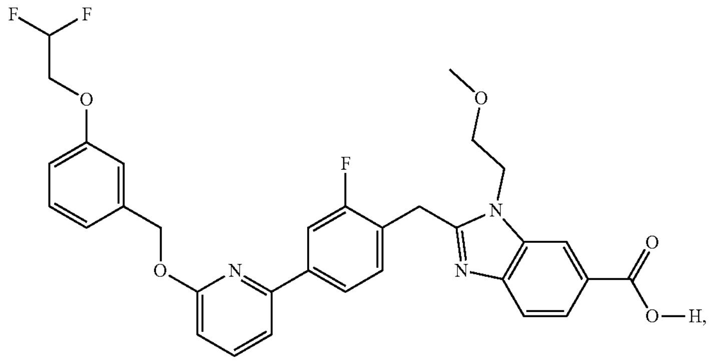
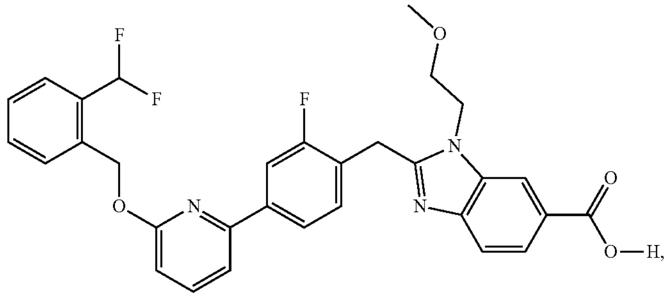
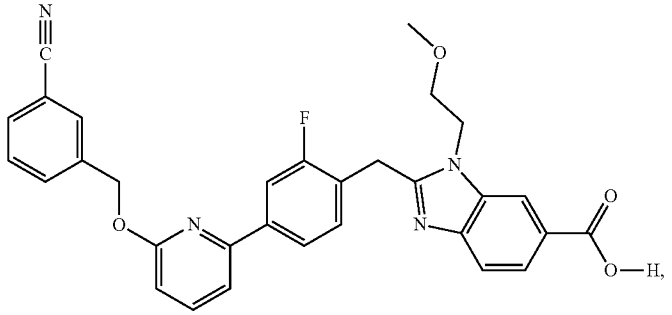
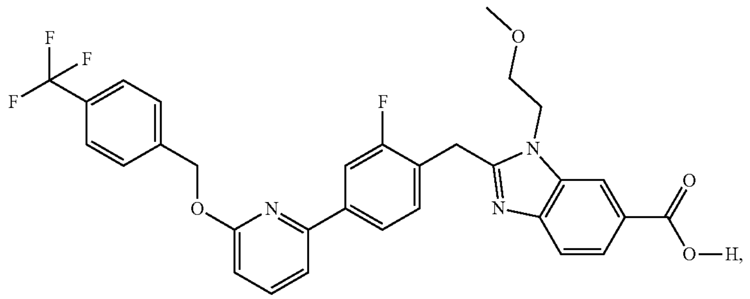
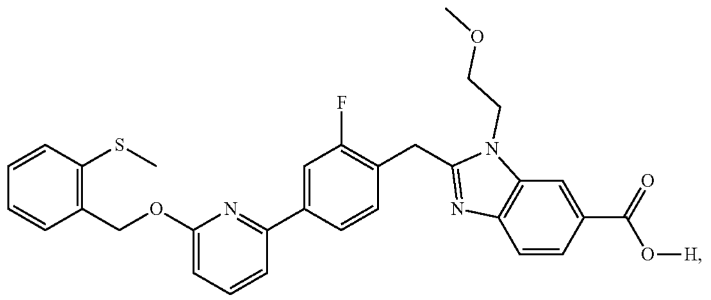

-continued
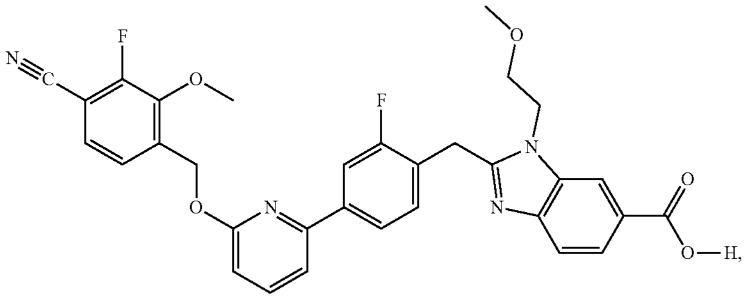
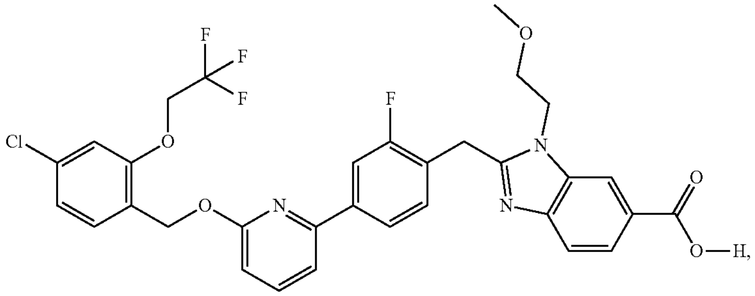
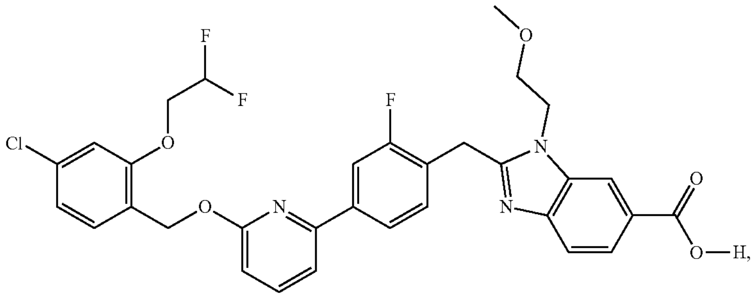
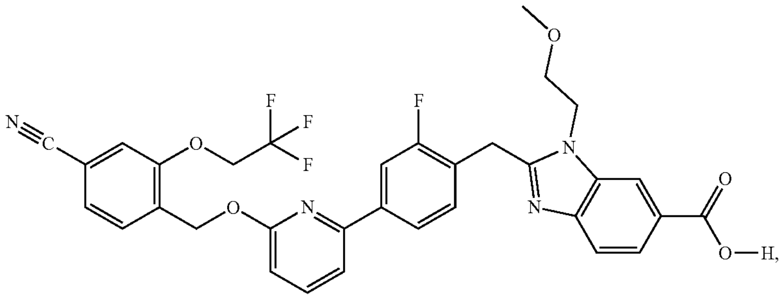
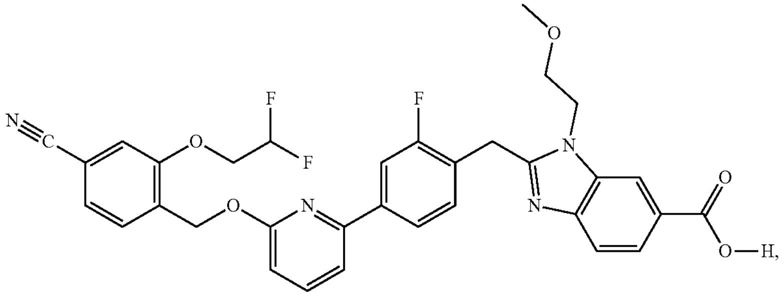

-continued
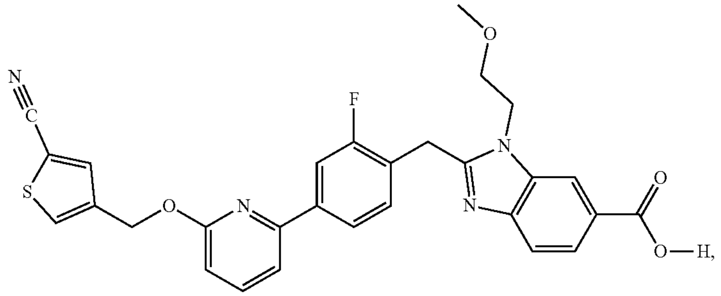
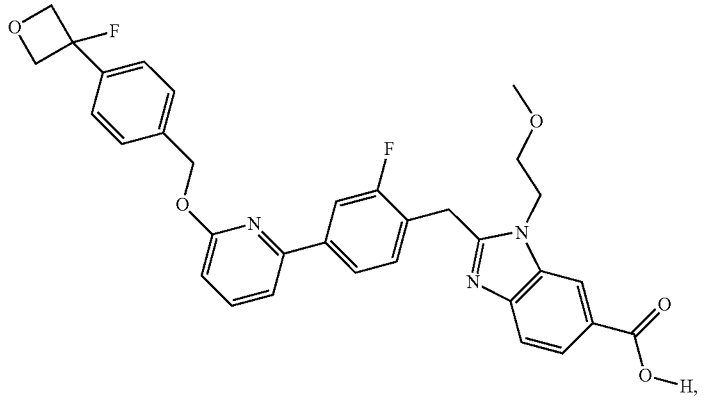
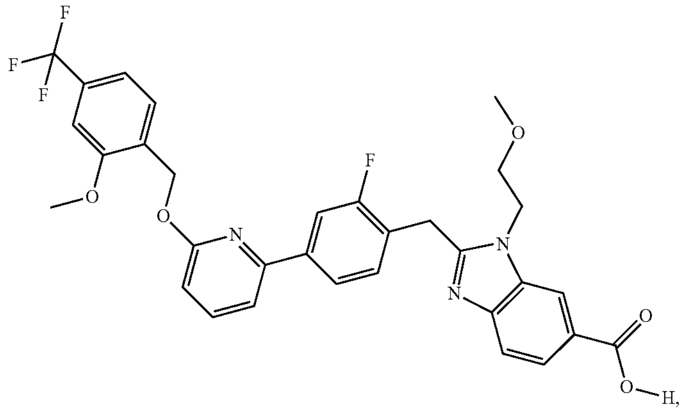
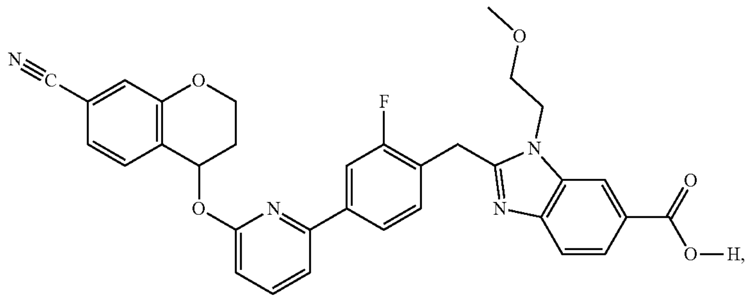
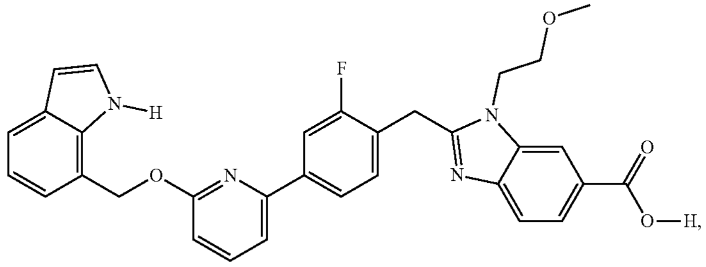

-continued
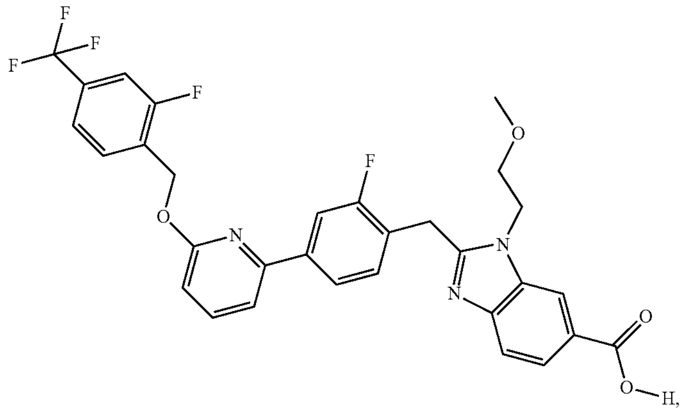
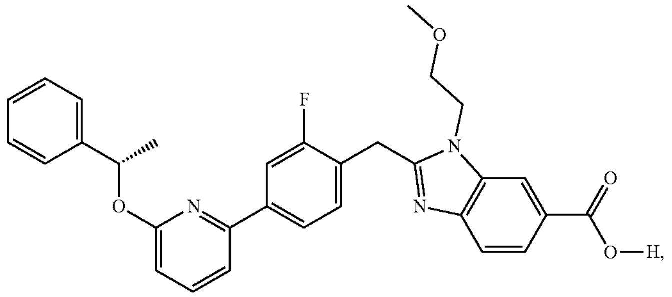
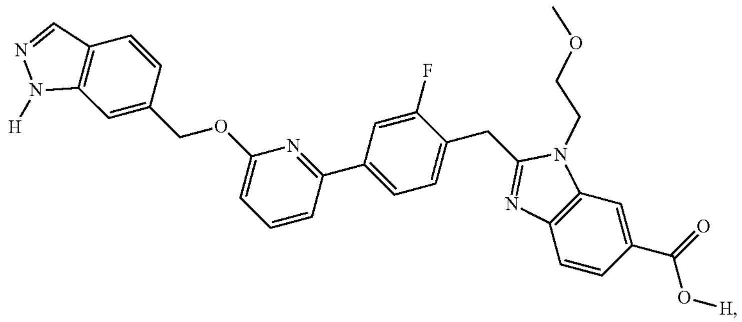
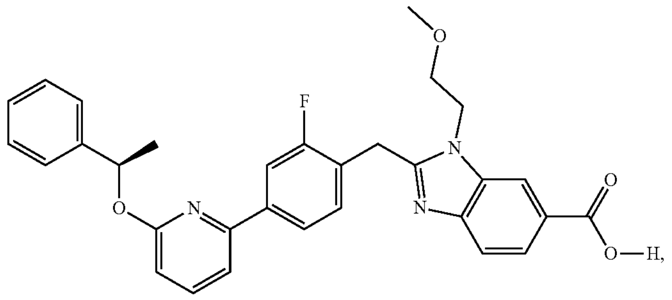
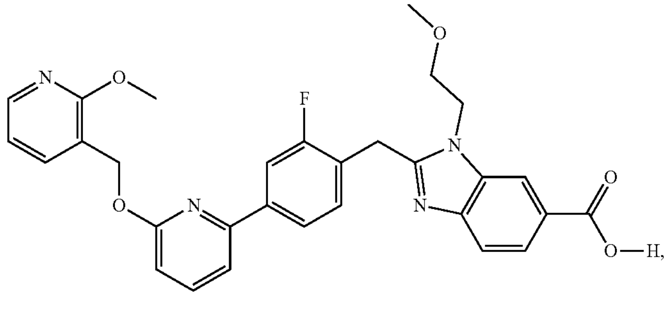

-continued
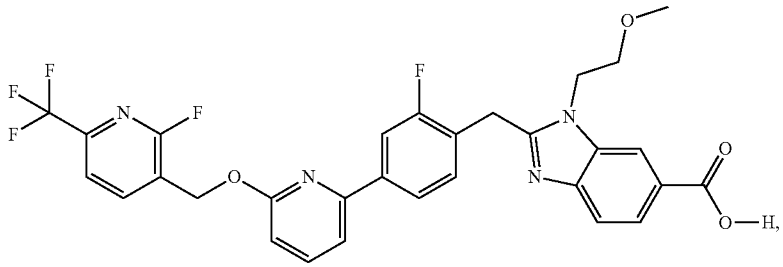
,
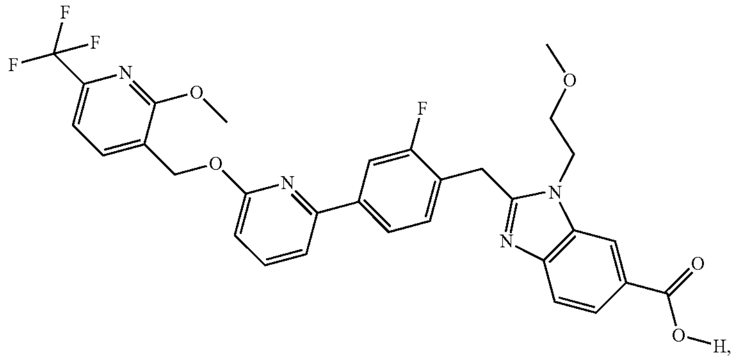
,
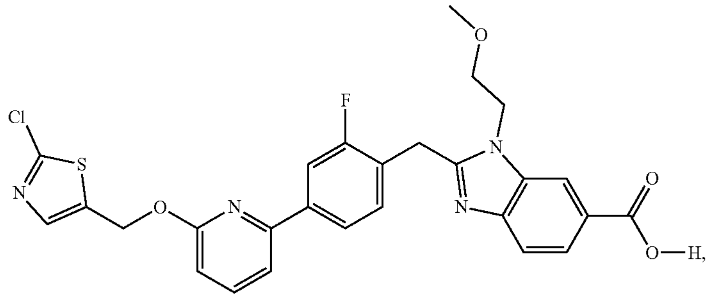
,
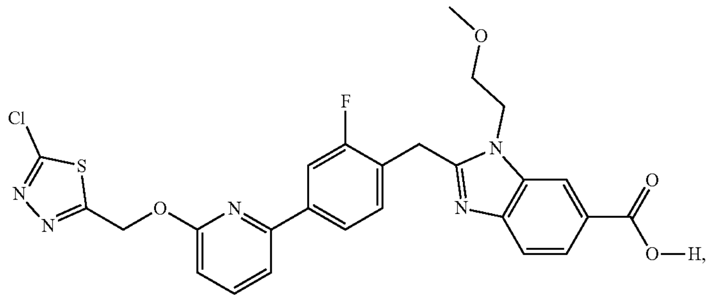
,
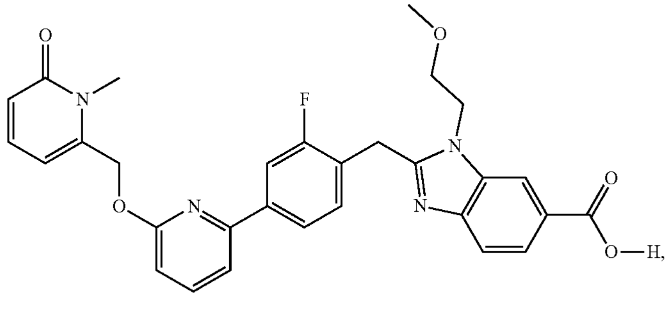
, -continued
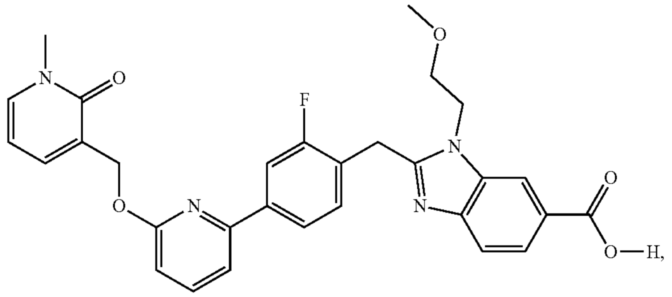
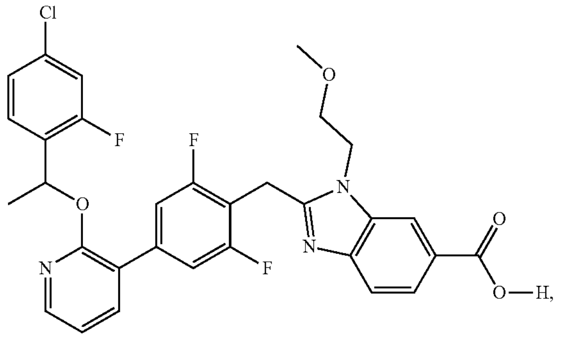
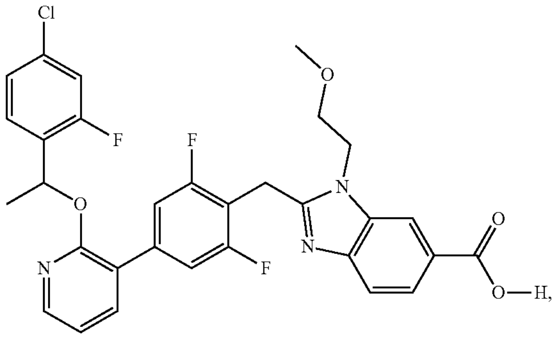
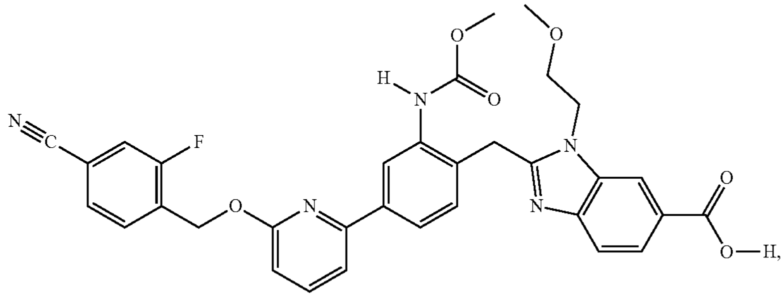
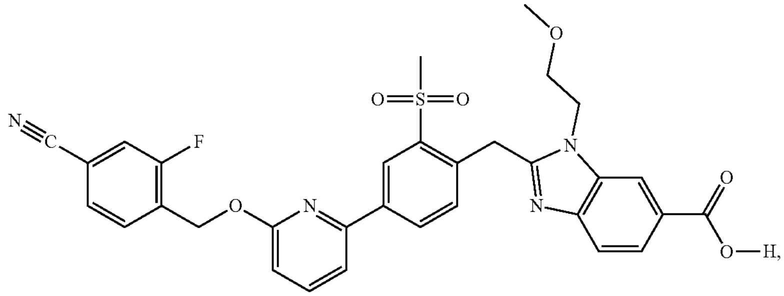
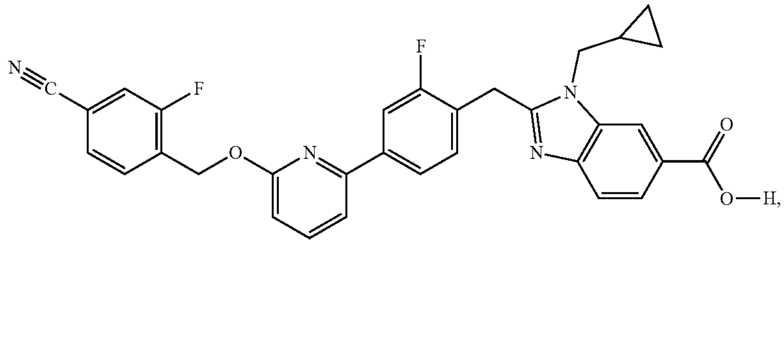

-continued
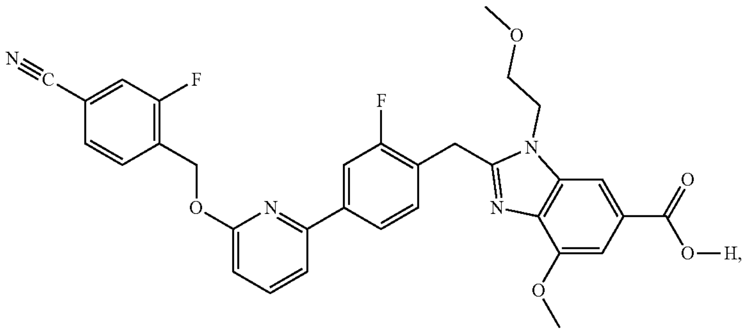
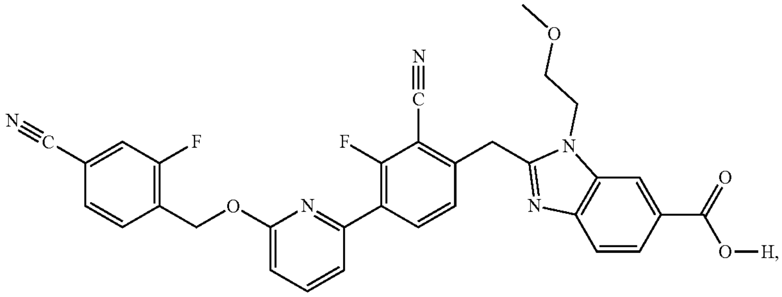
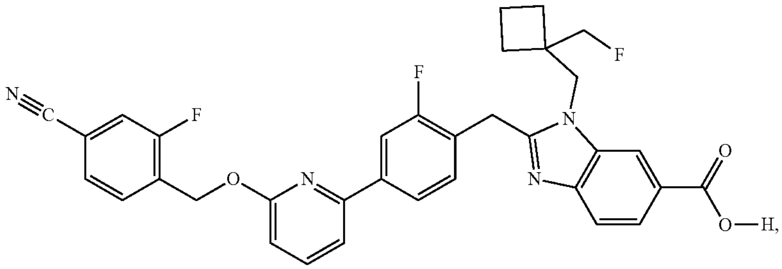
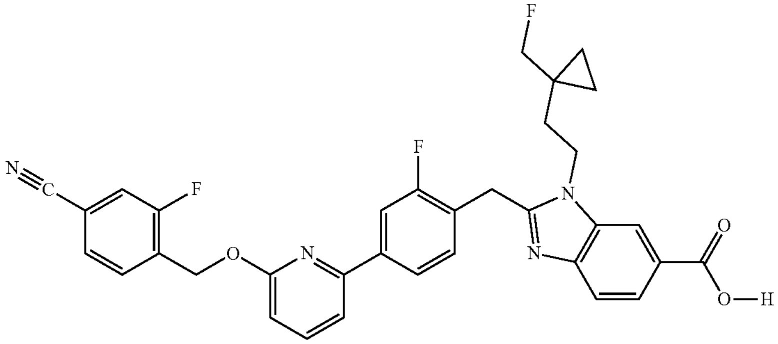
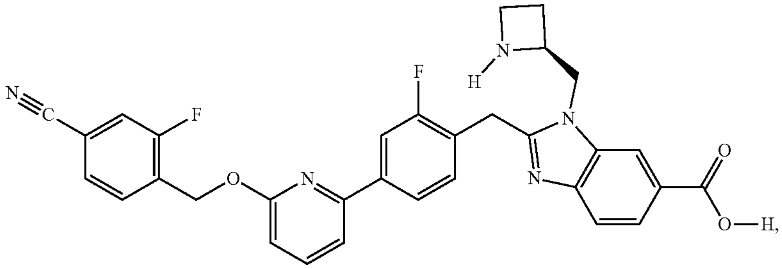

-continued
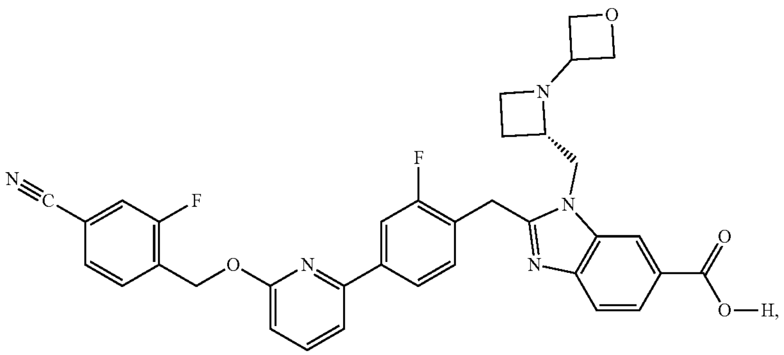
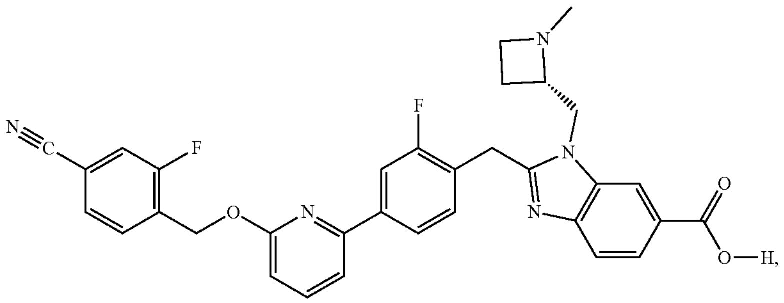
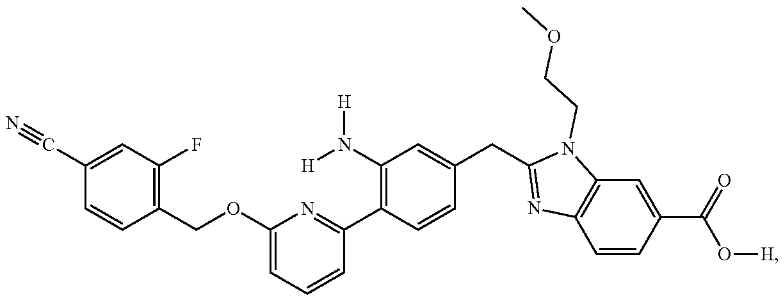
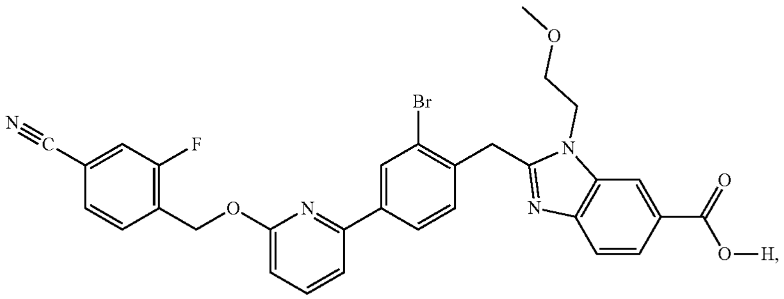
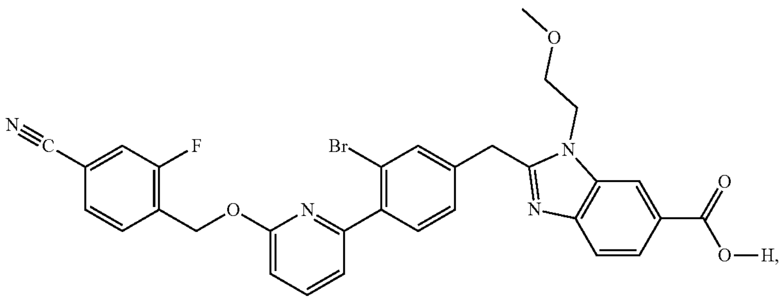

-continued
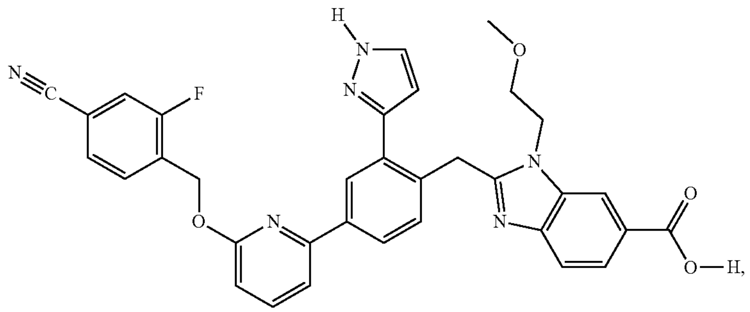
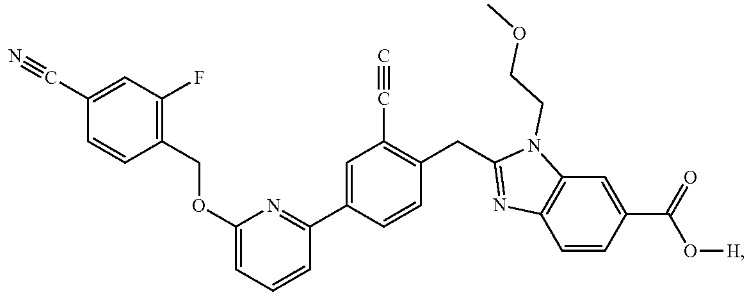
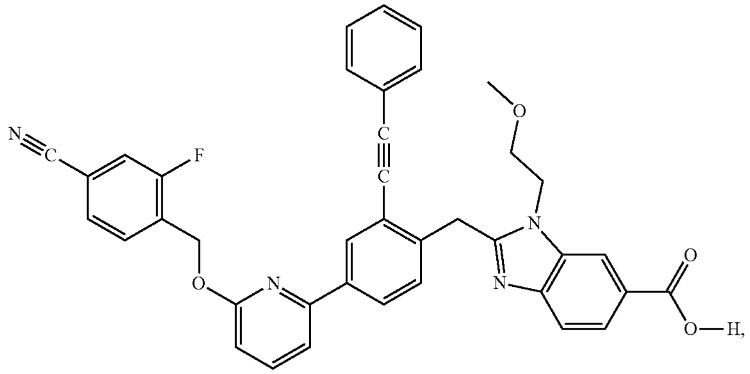
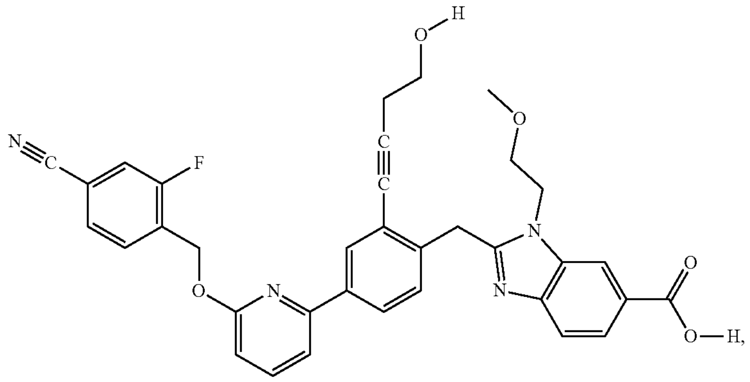
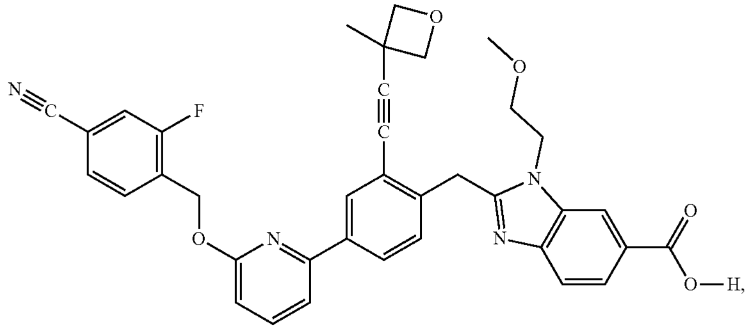

-continued
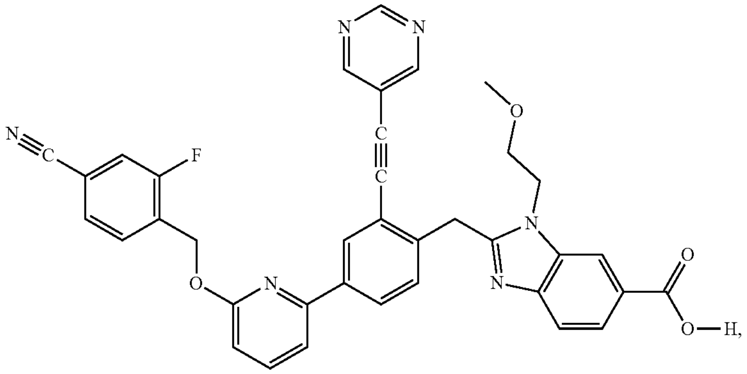
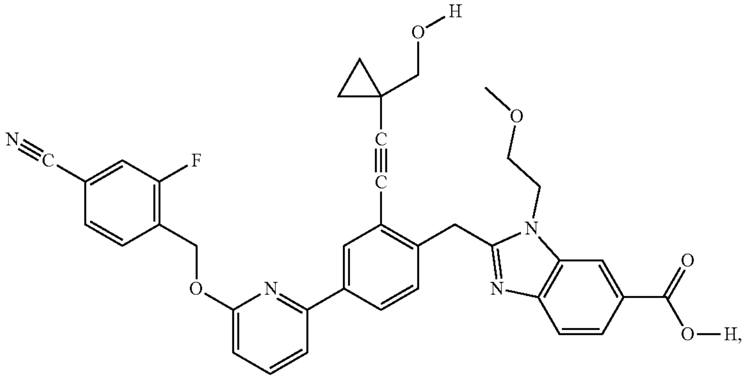
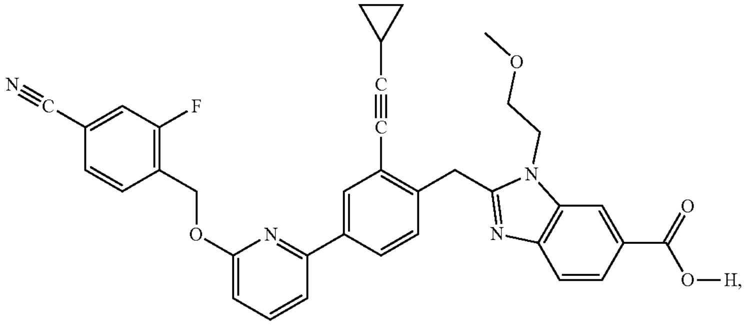
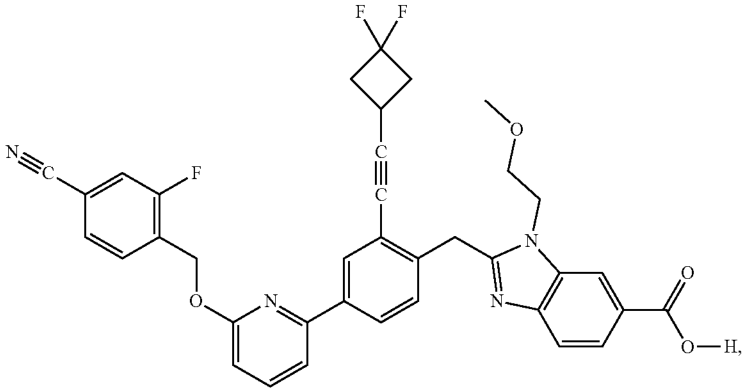
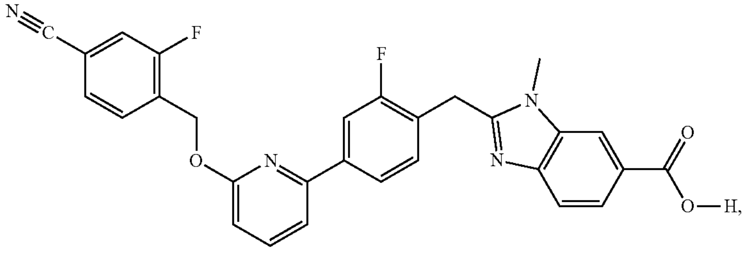

-continued
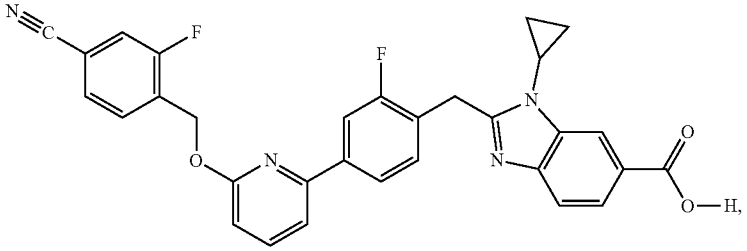
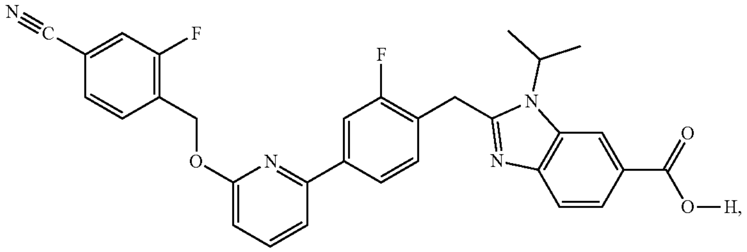
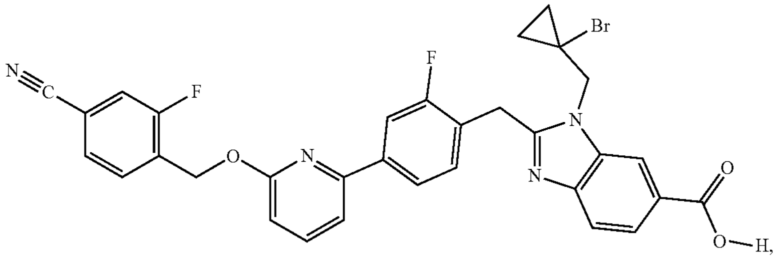
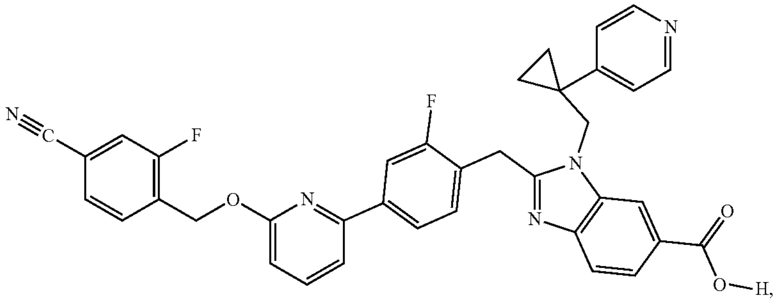
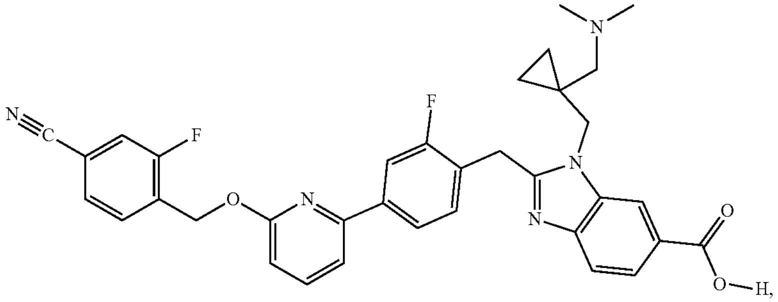
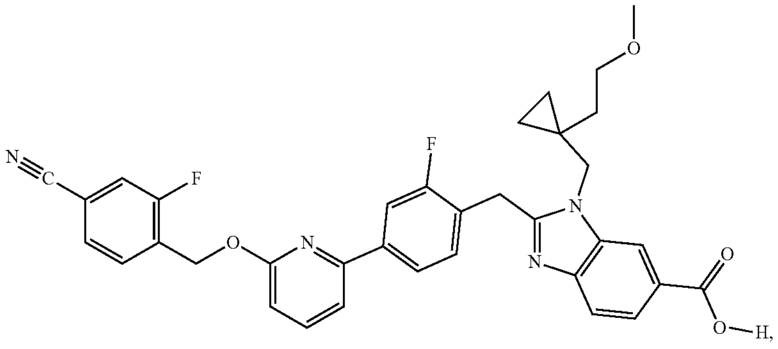

-continued
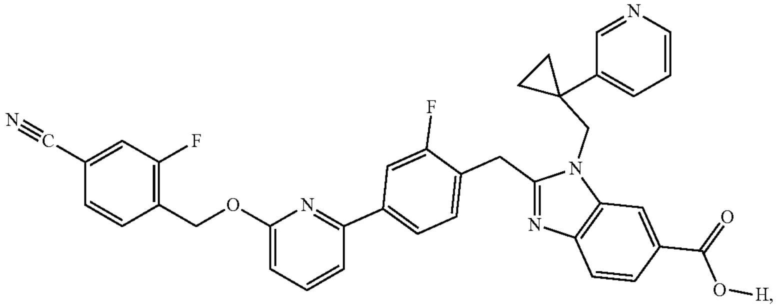
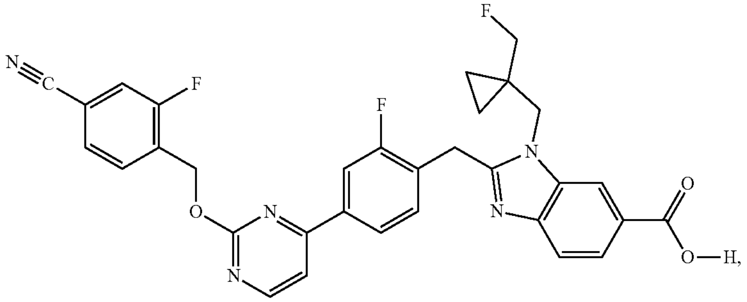
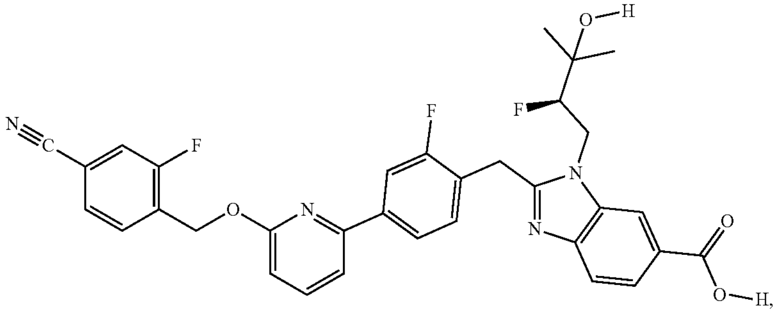
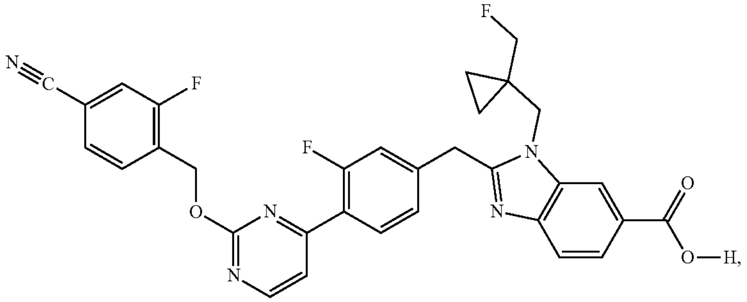
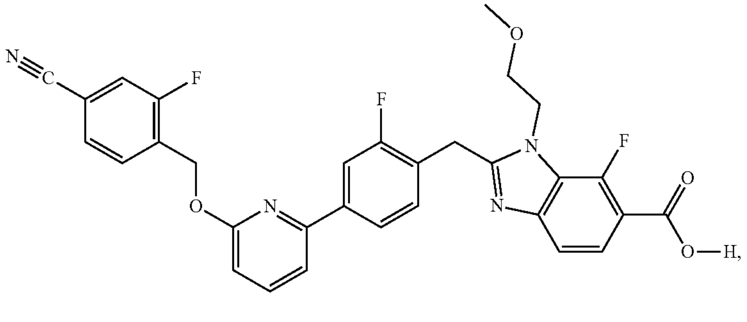

-continued
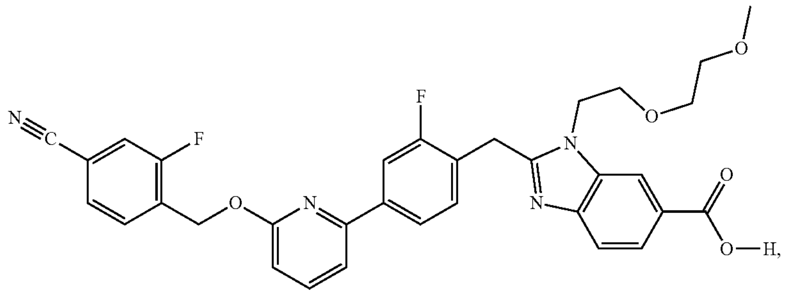
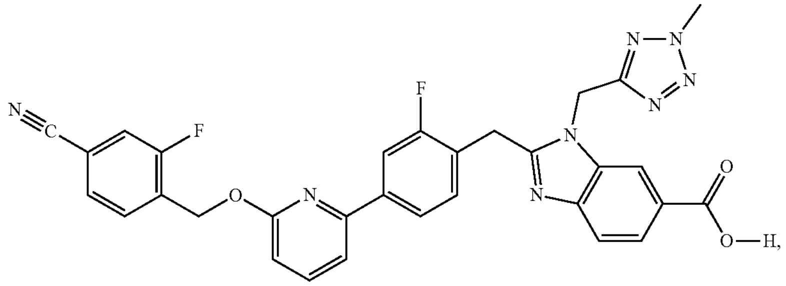
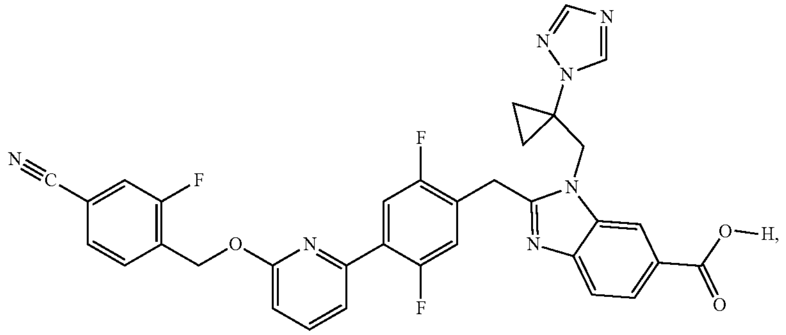
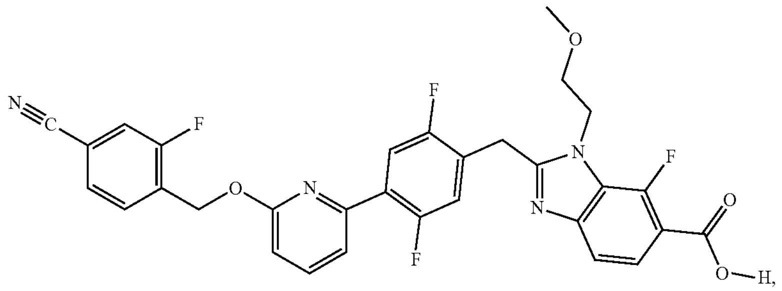
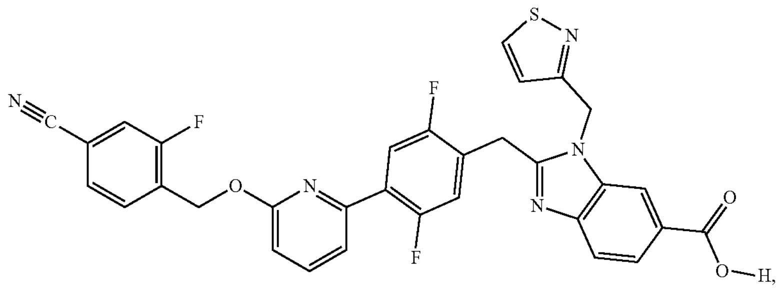

-continued
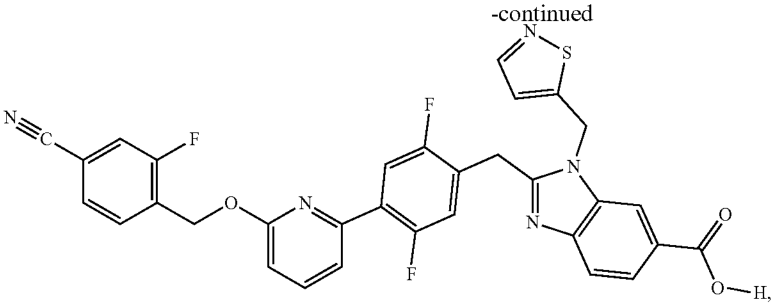
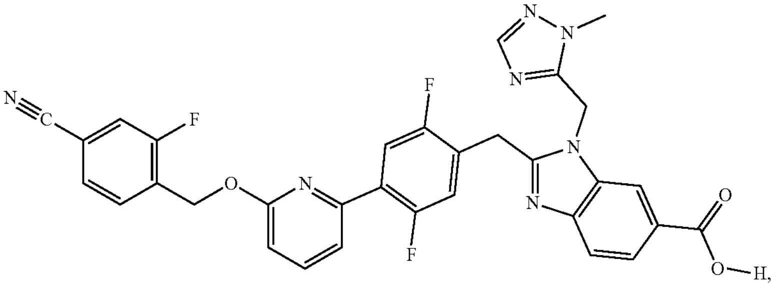
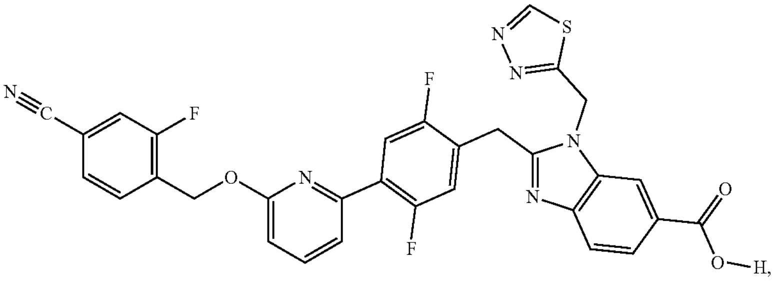
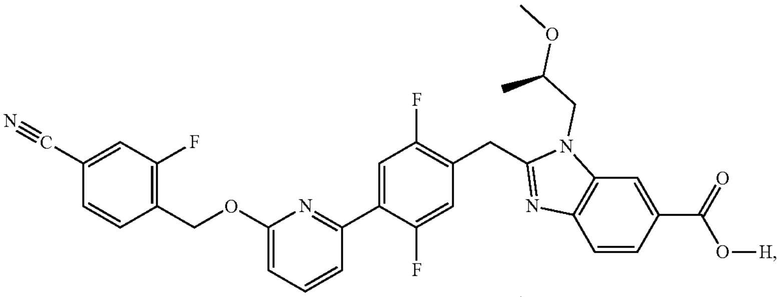
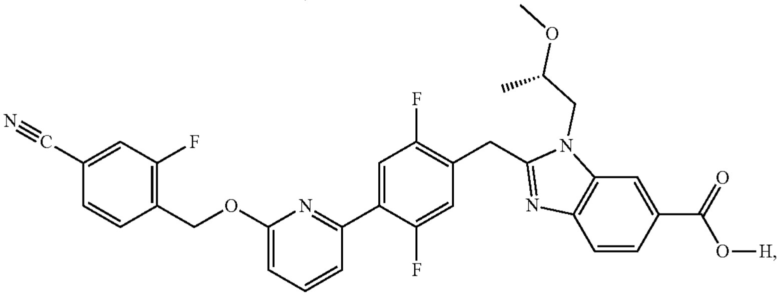
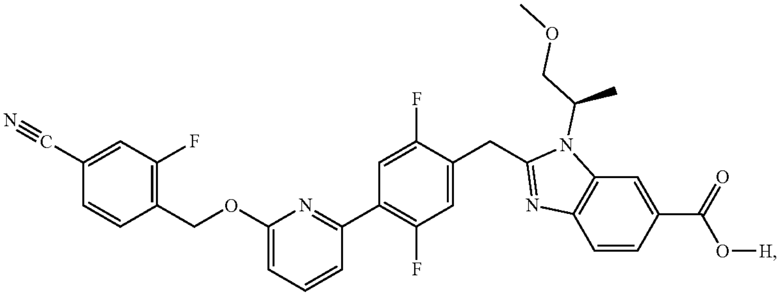

-continued
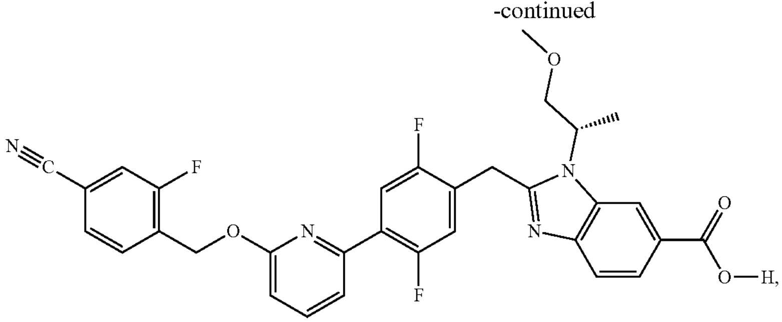
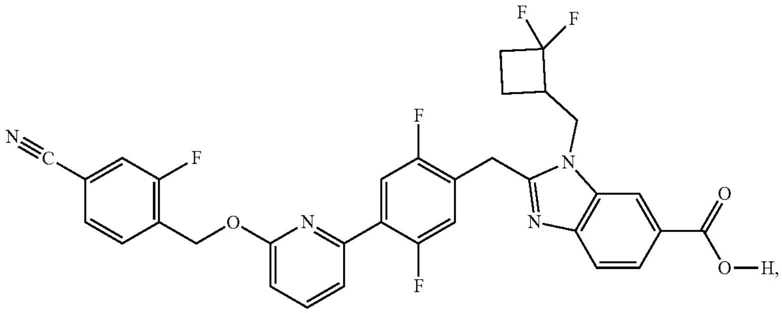
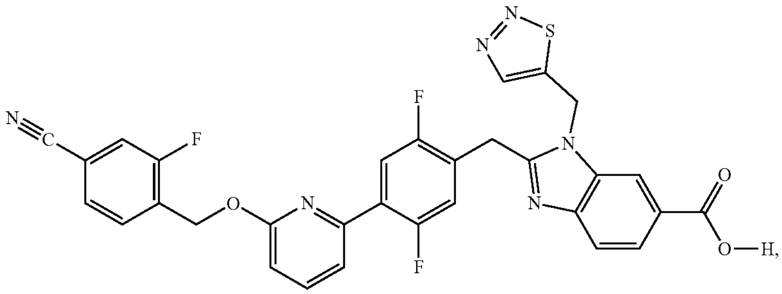
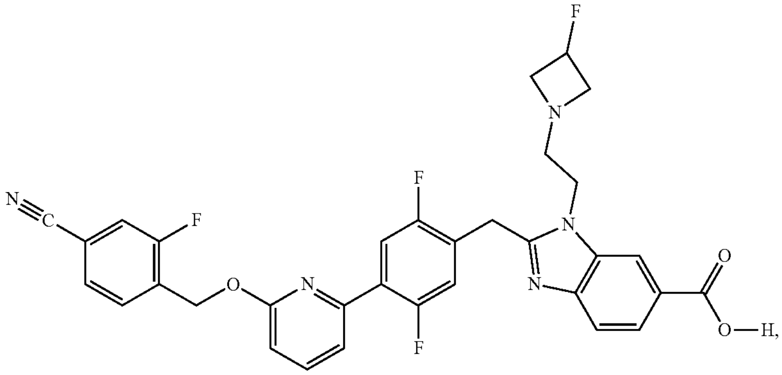
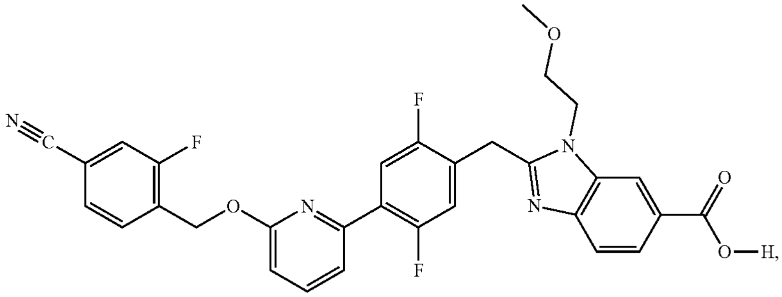

-continued
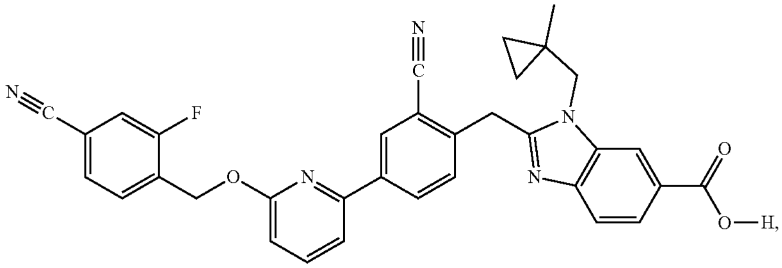
,
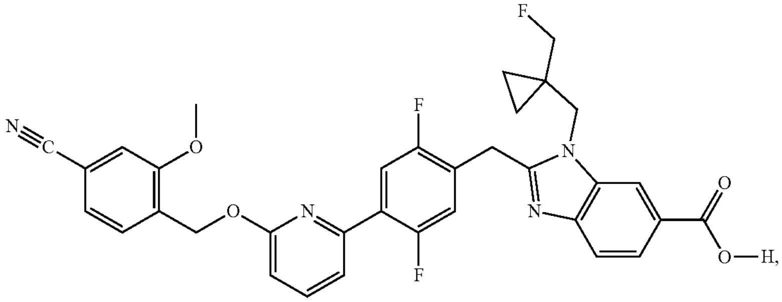
,
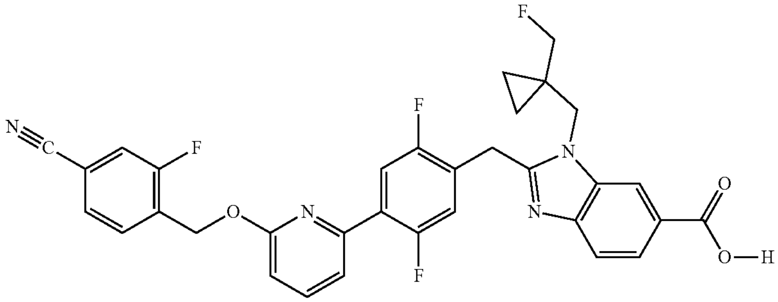
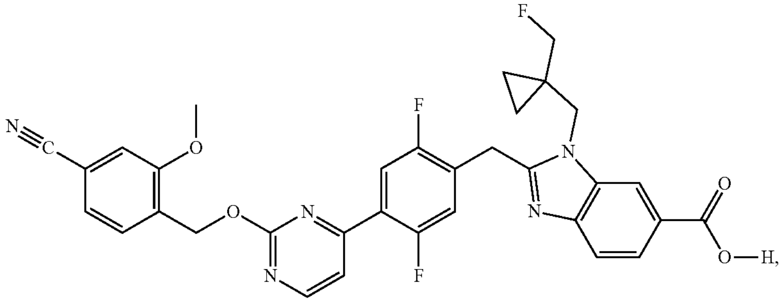
,
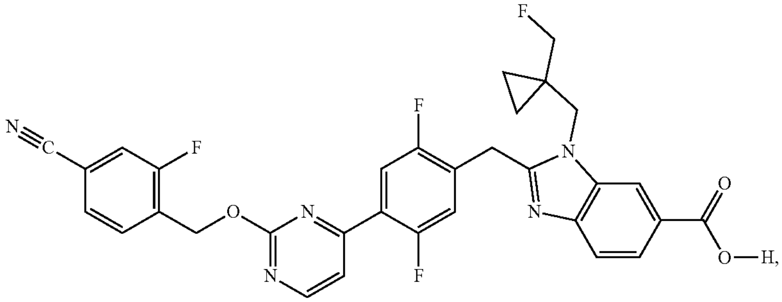
,

-continued
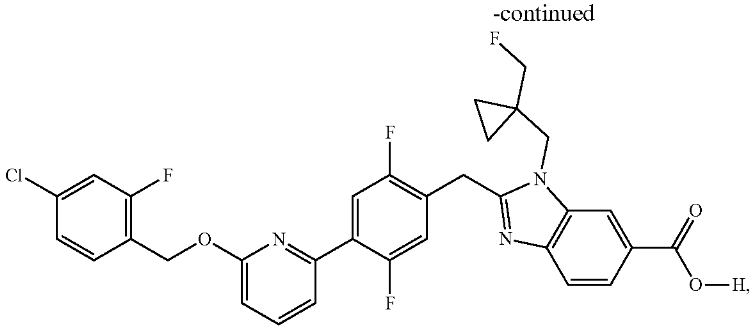
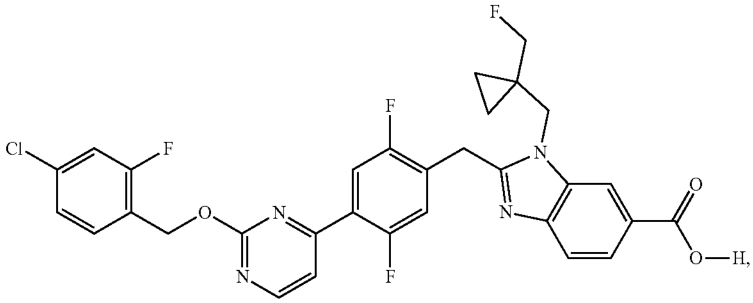
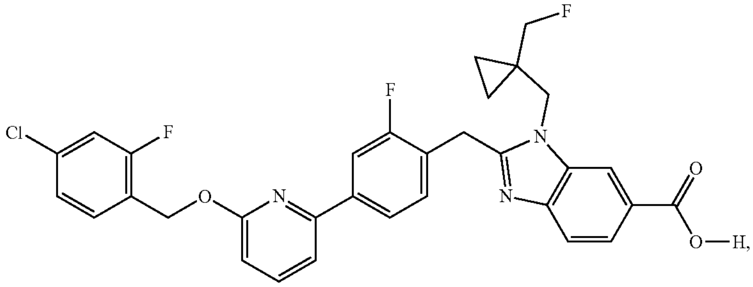
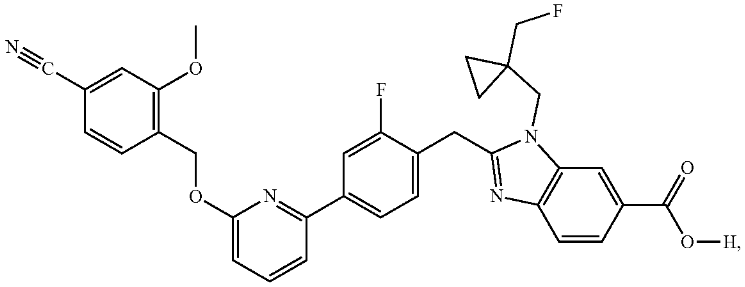
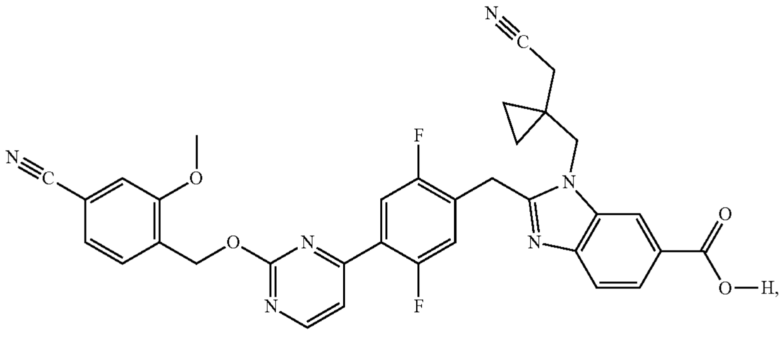

-continued
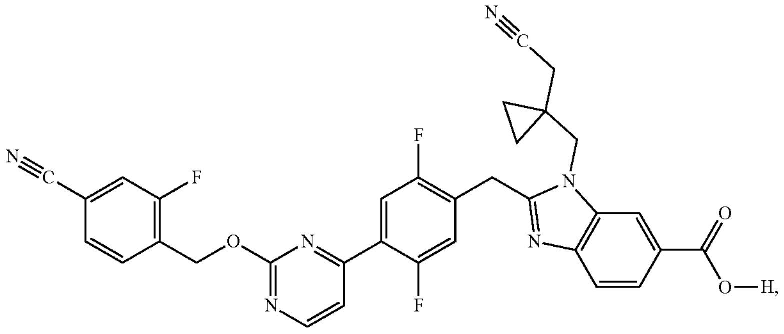
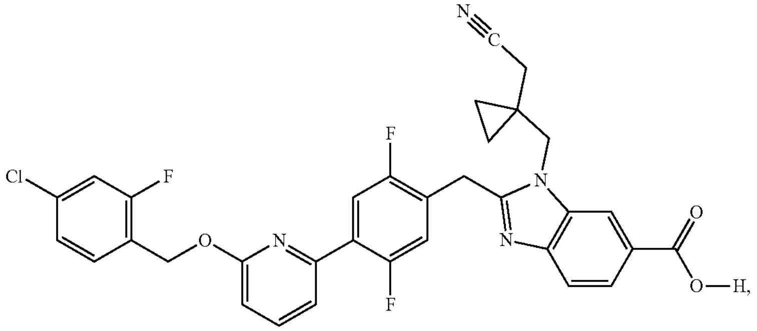
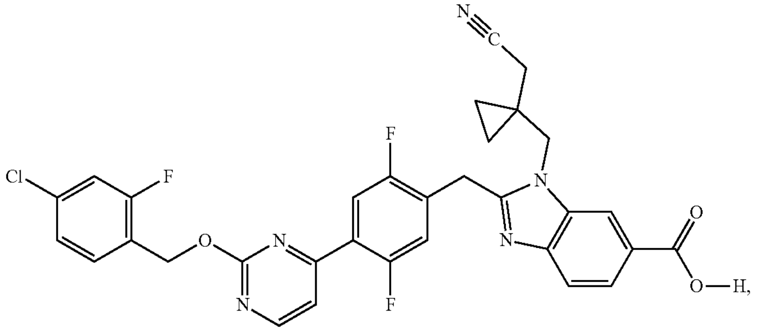
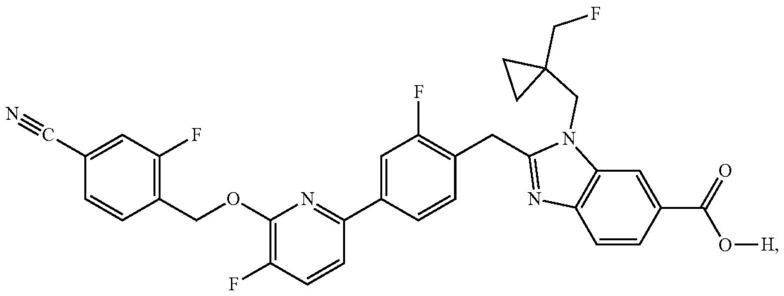
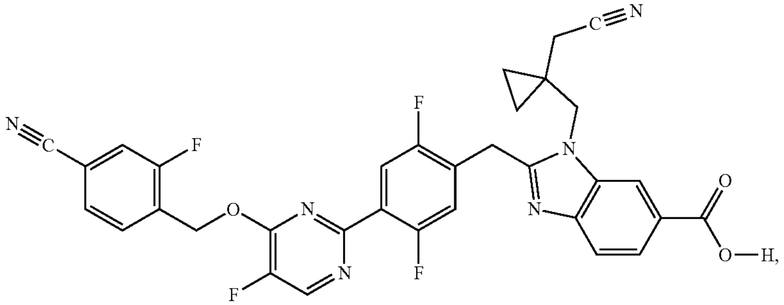

-continued
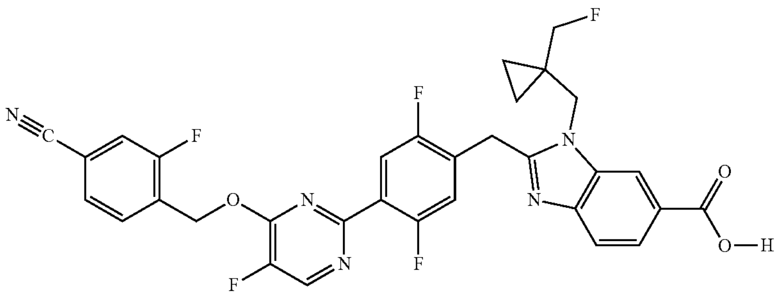
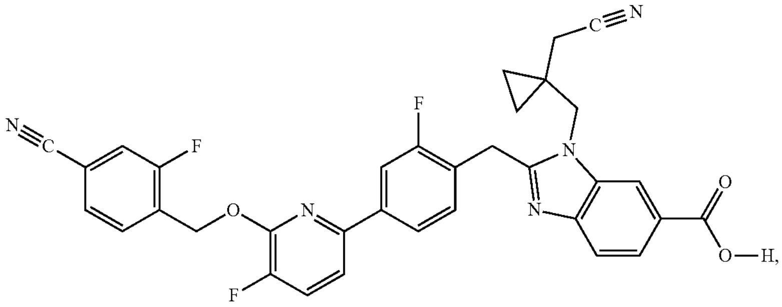
,
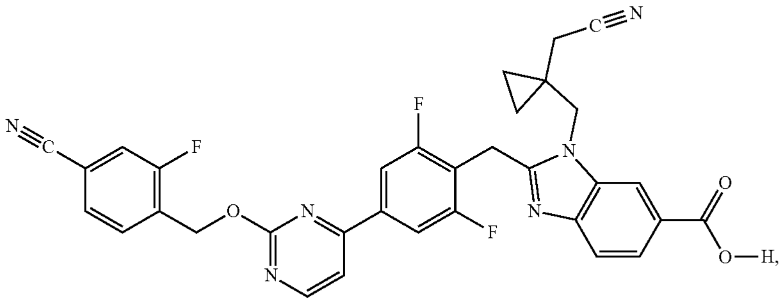
,
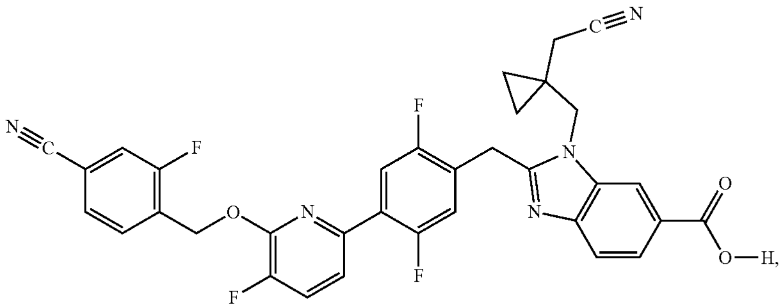
,
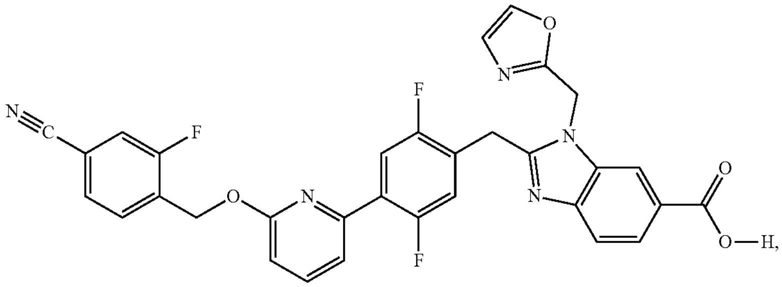
,

-continued
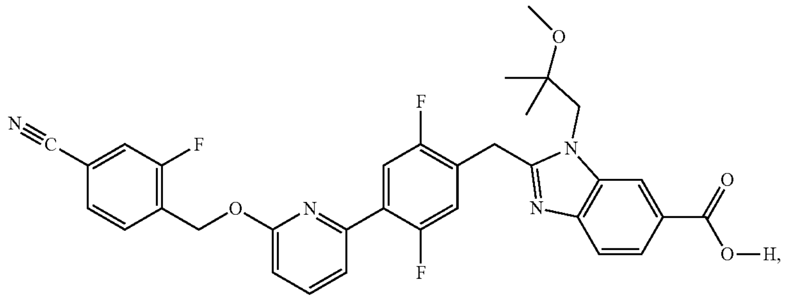
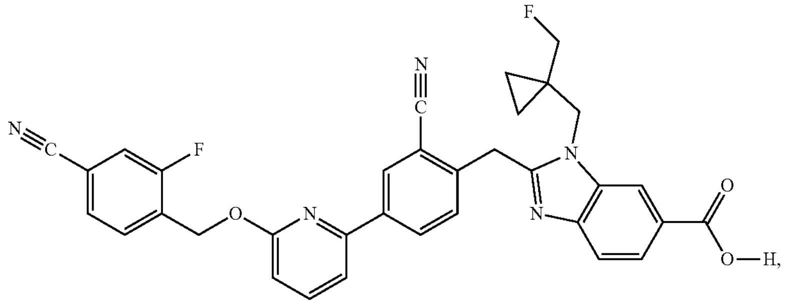
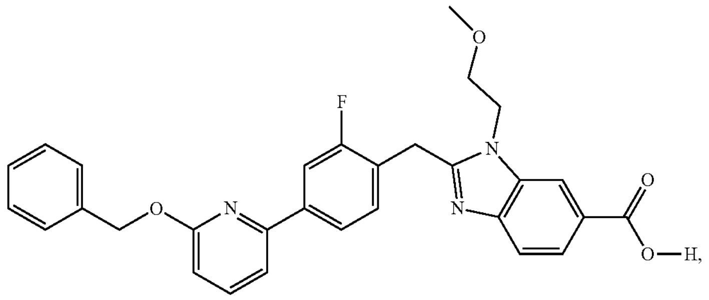
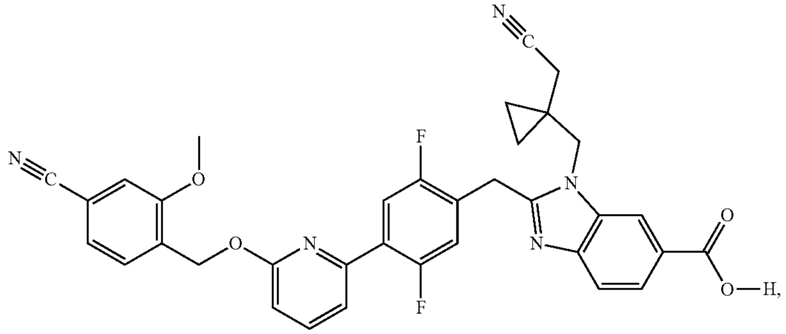
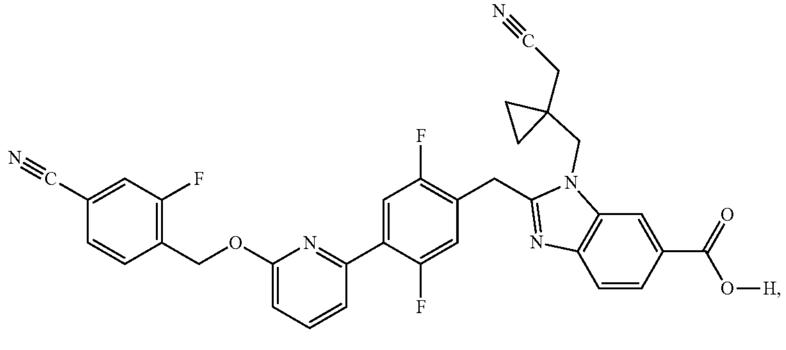

-continued
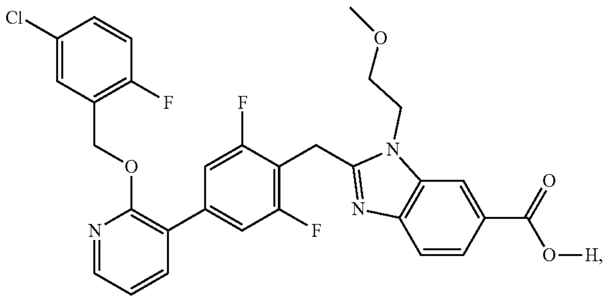
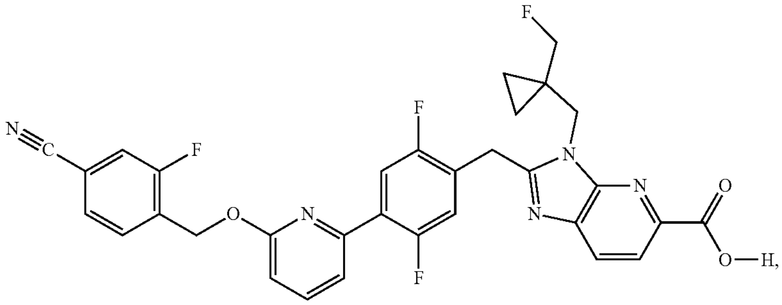
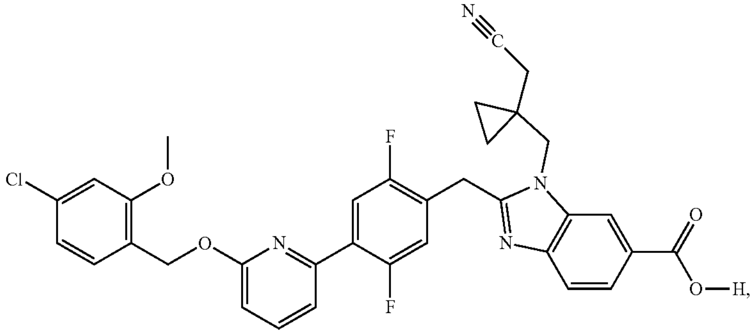
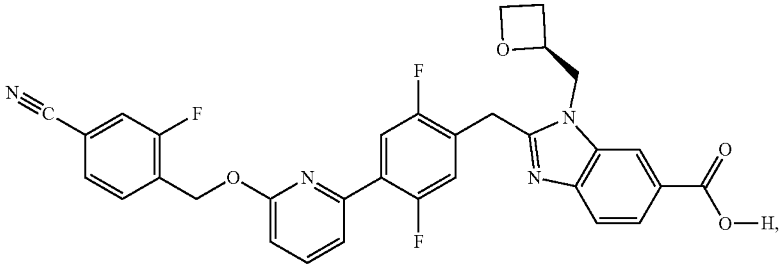
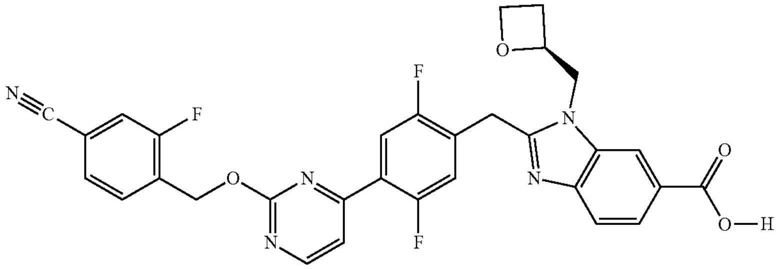

-continued
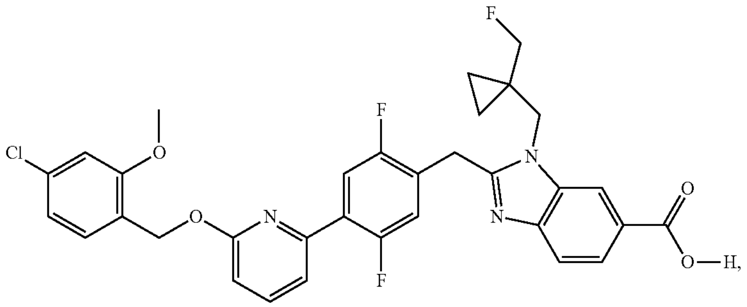
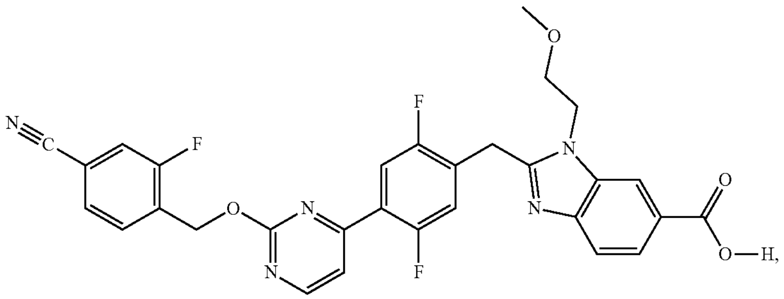
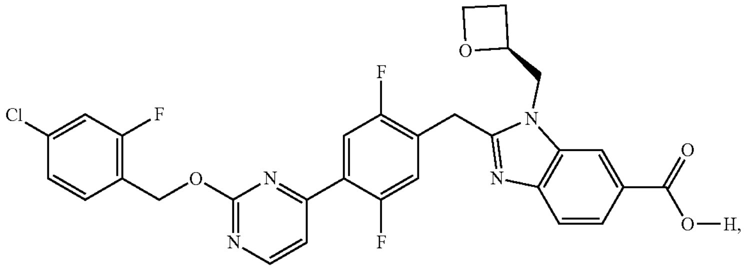
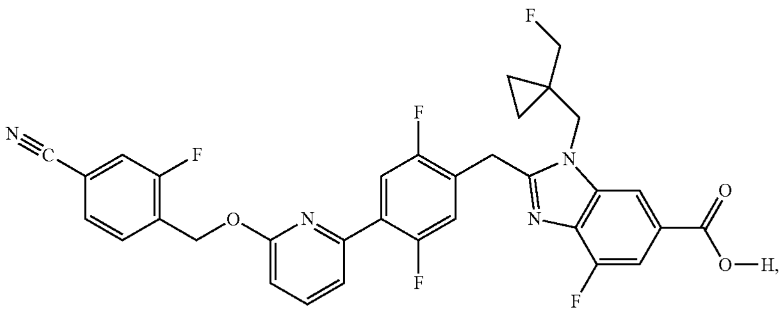
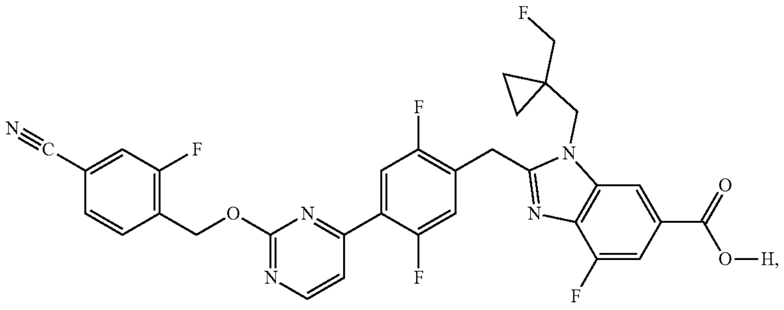

-continued
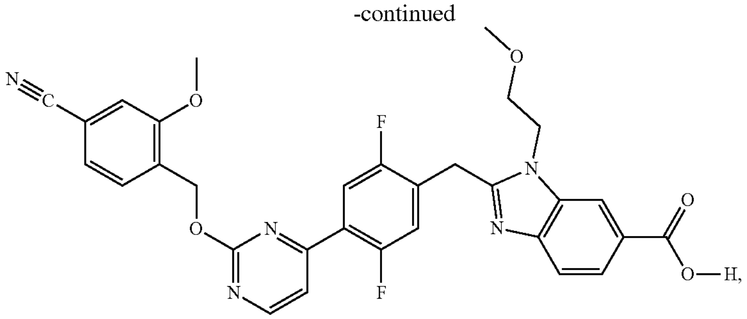
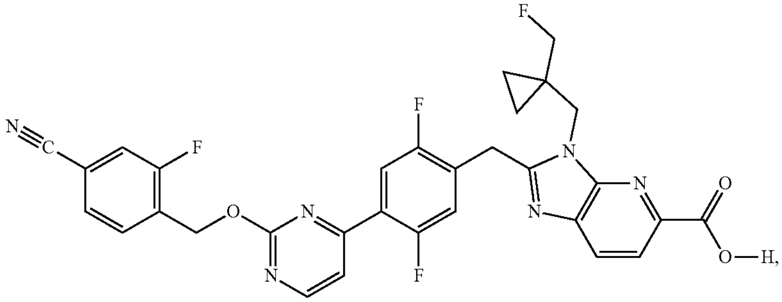
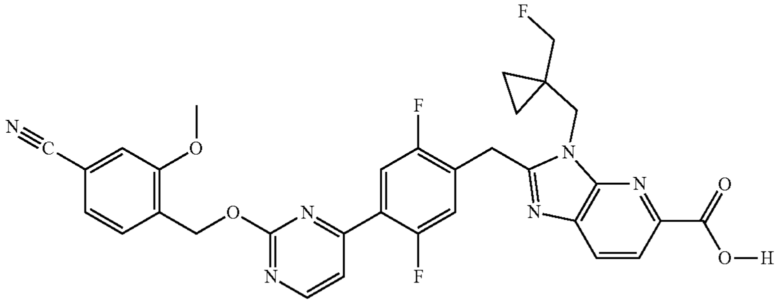
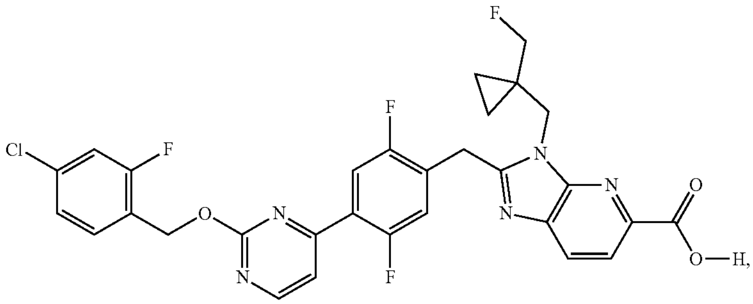
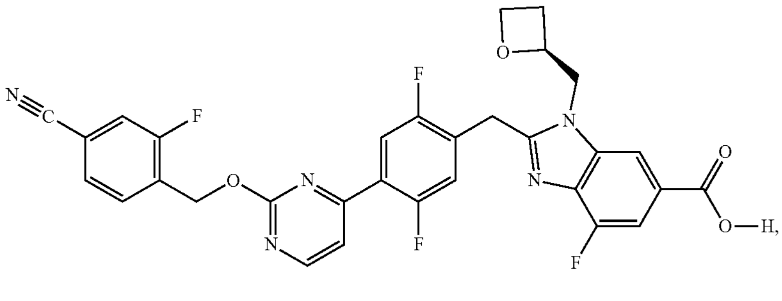

-continued
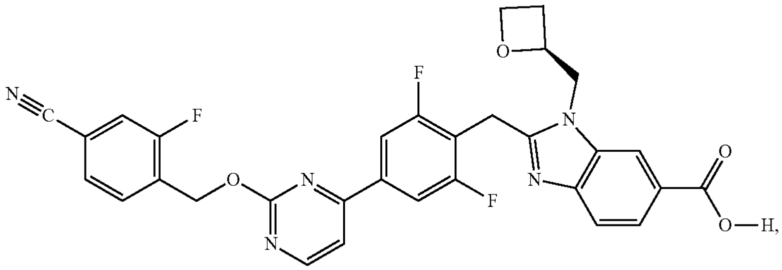
,
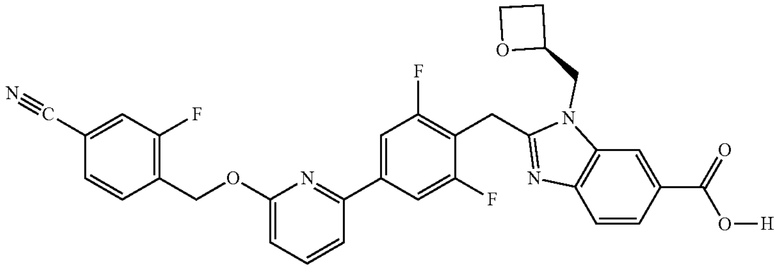
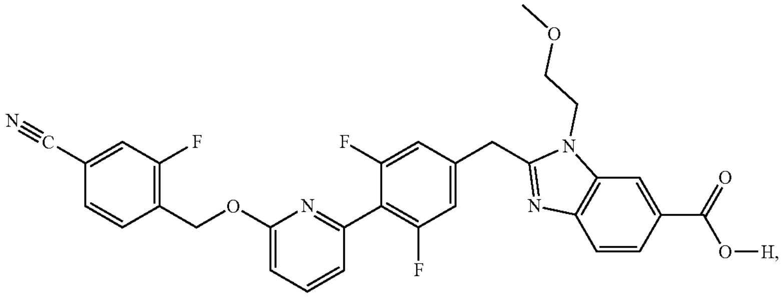
,
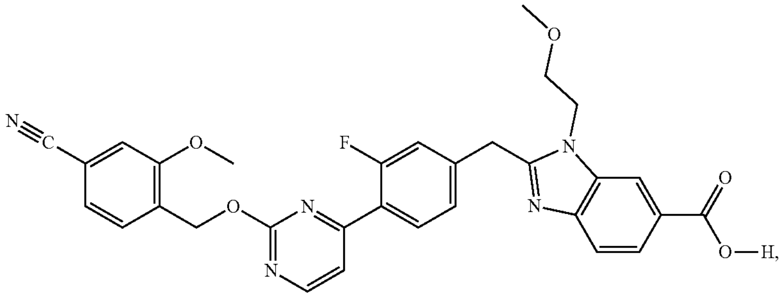
,
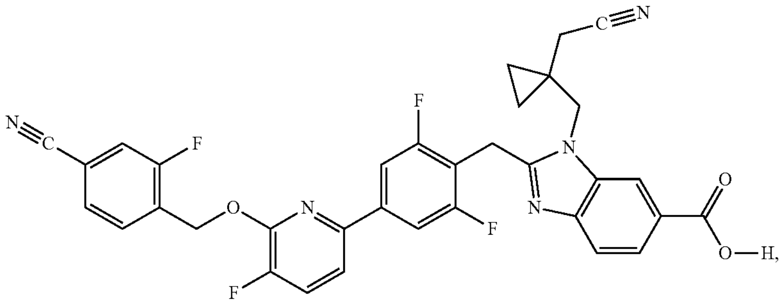
,
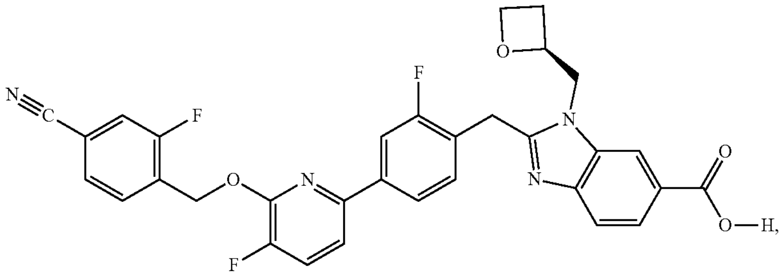
, -continued
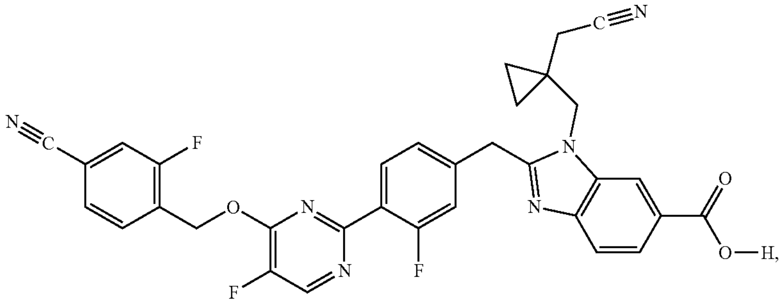
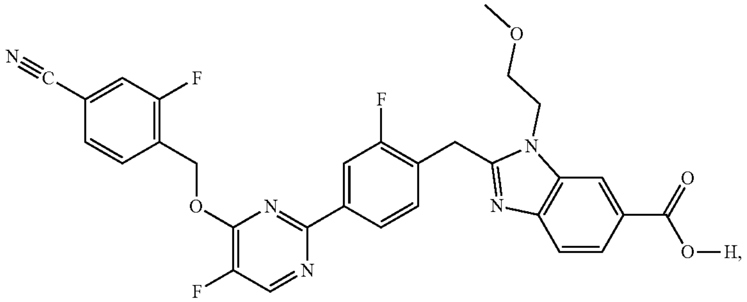
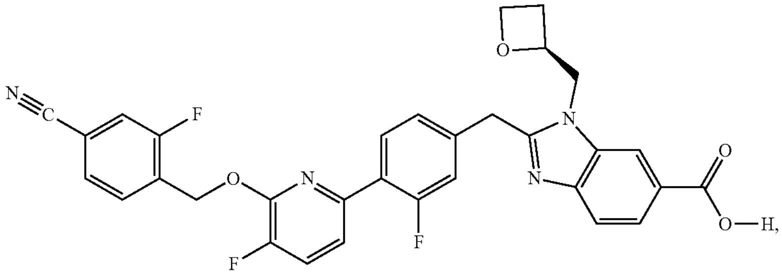
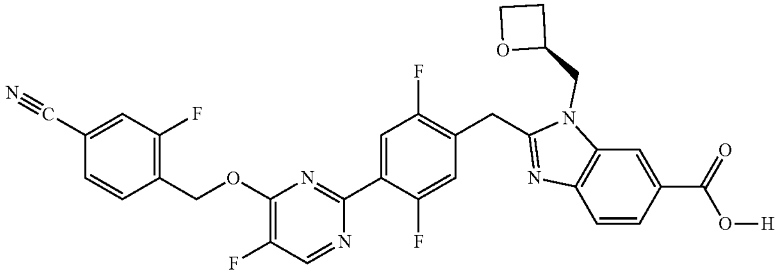
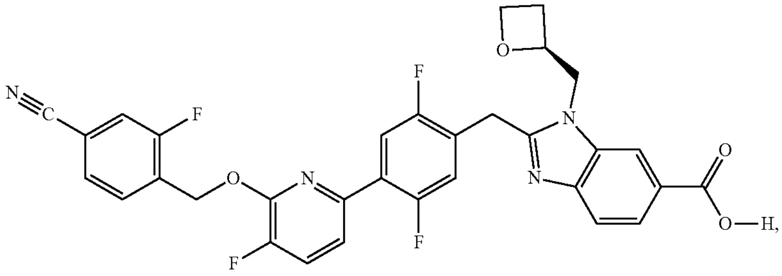
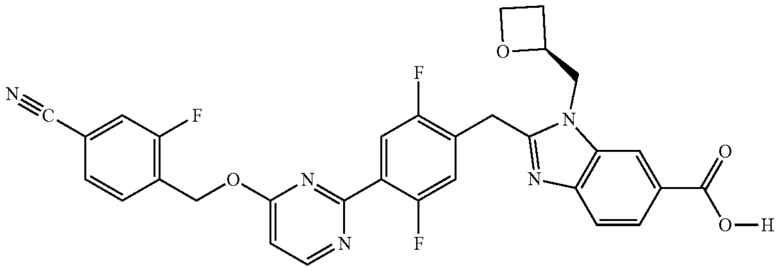

-continued
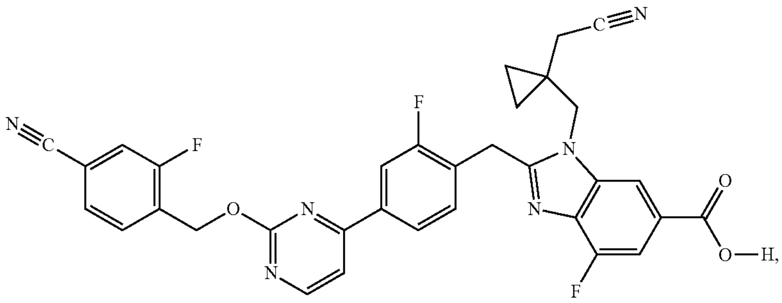
,
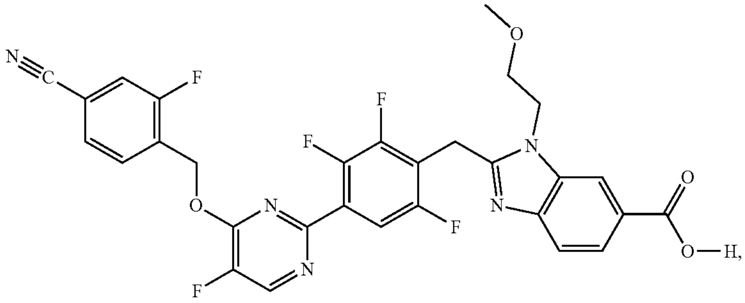
,
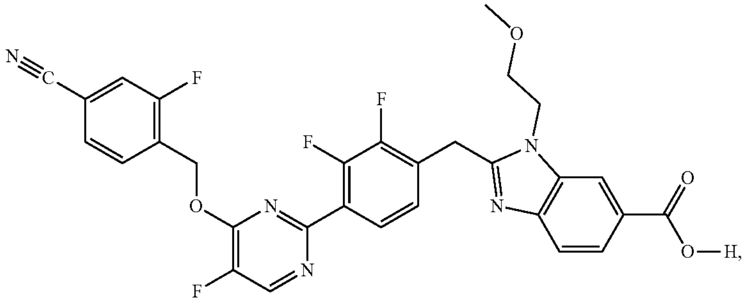
,
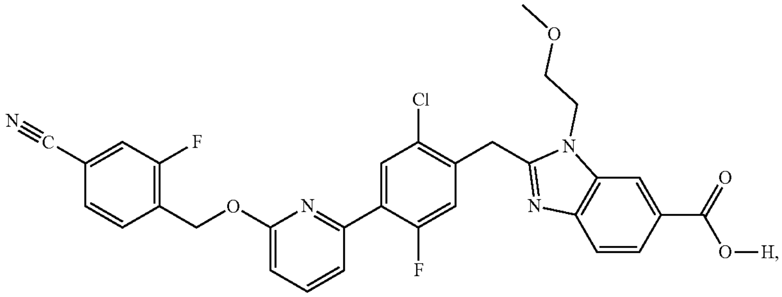
,
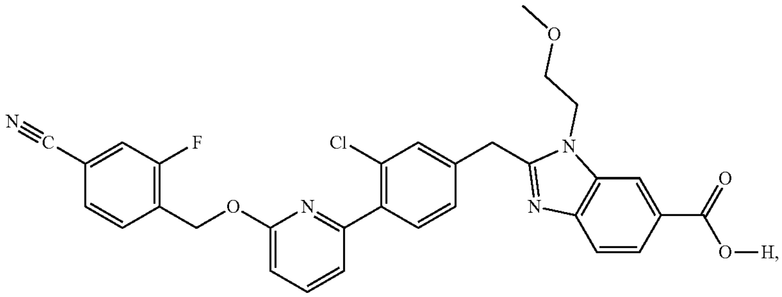
, -continued
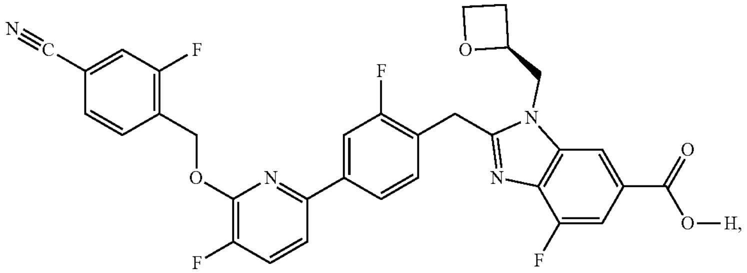
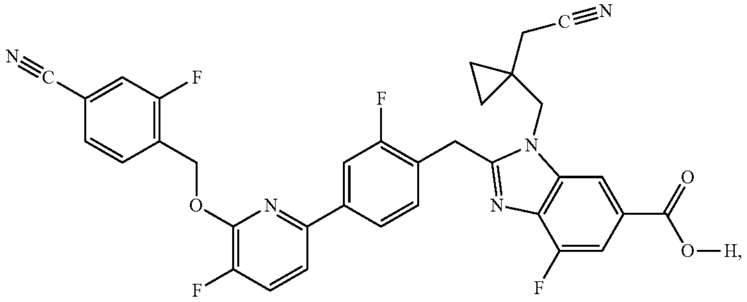
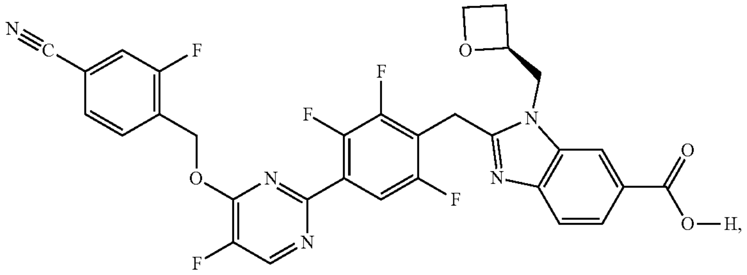
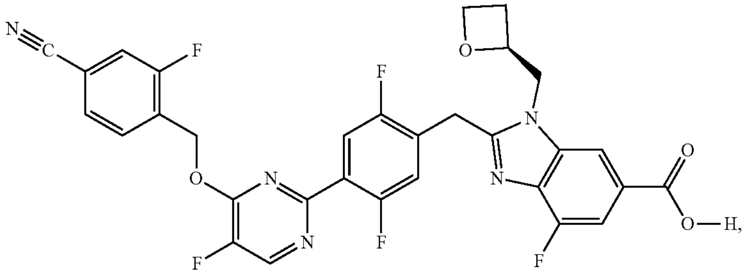
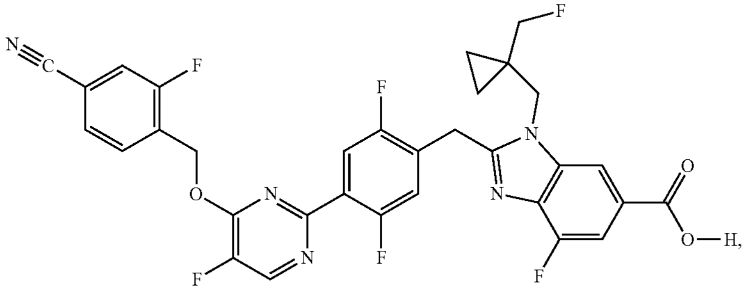
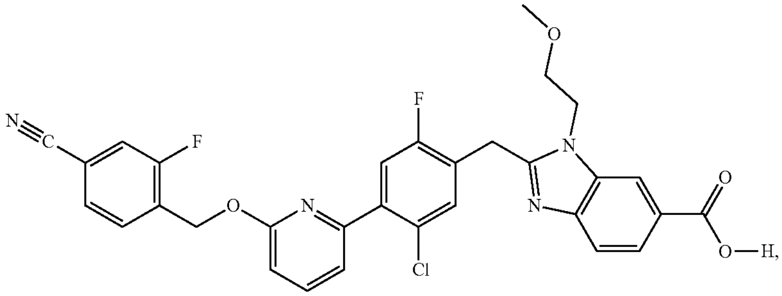

-continued
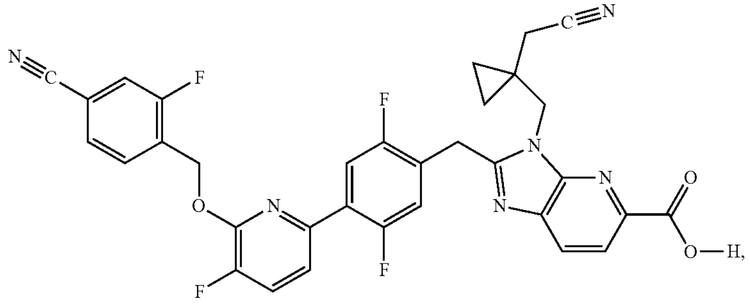
,
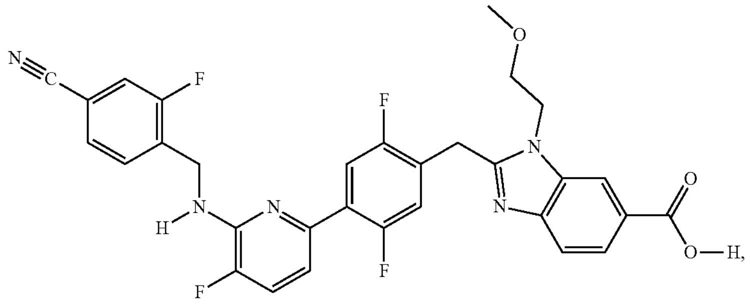
,
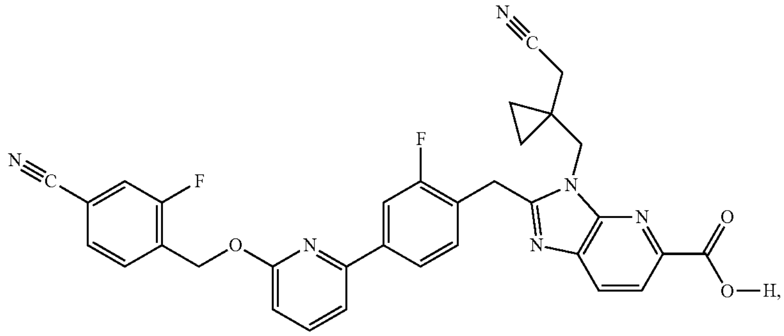
,
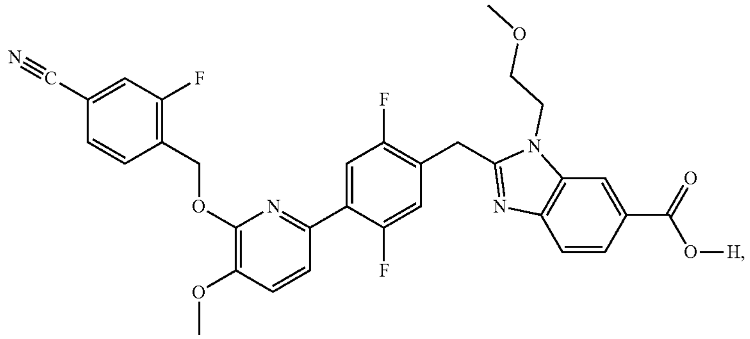
,
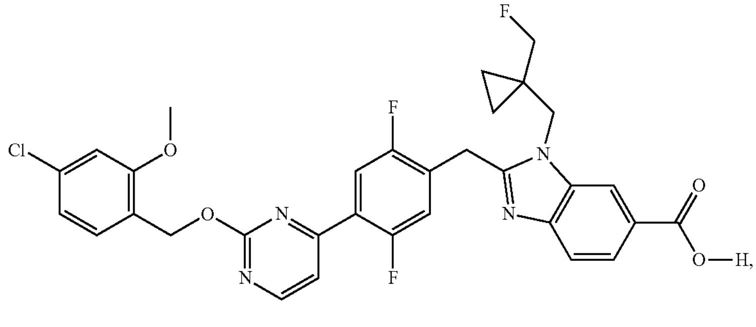
, -continued
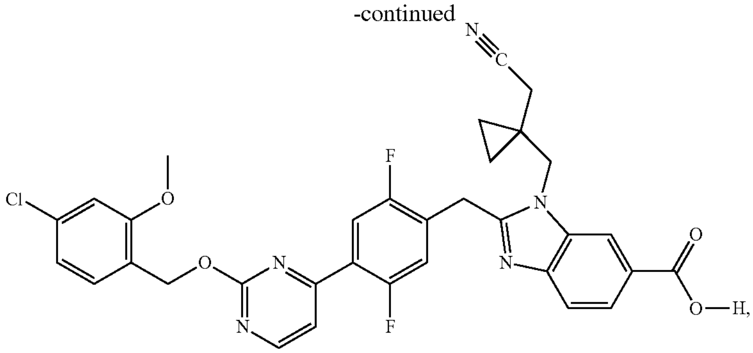
,
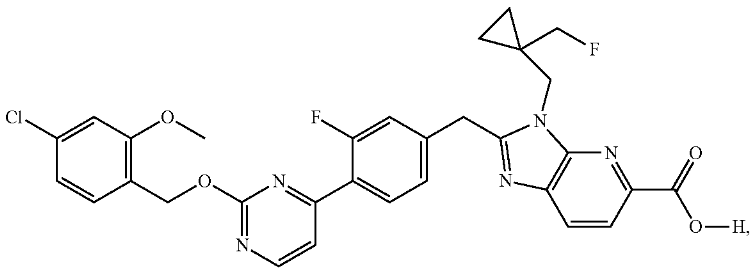
,
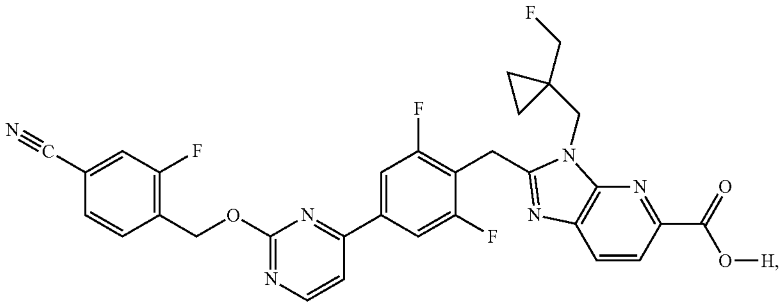
,
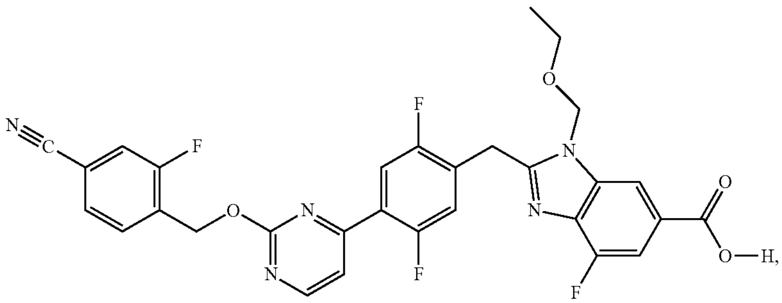
,
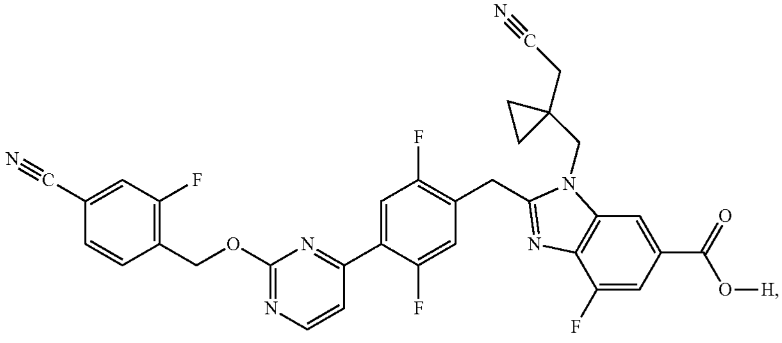
, -continued
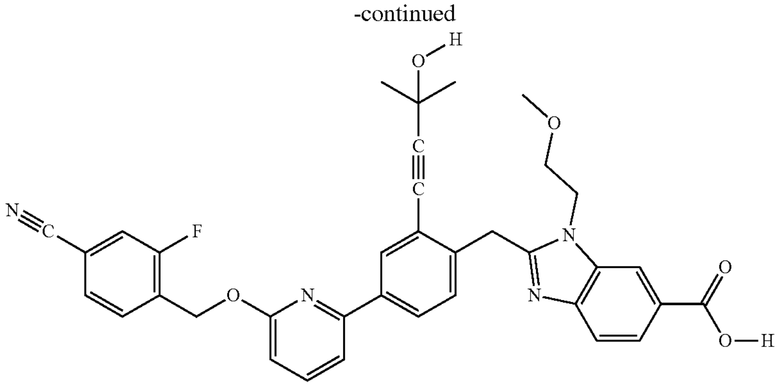
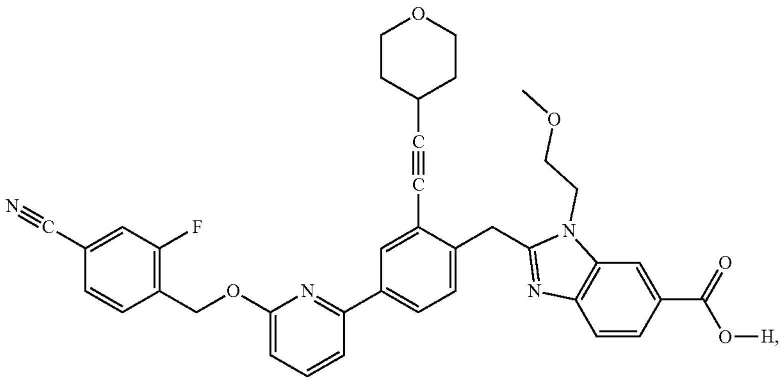
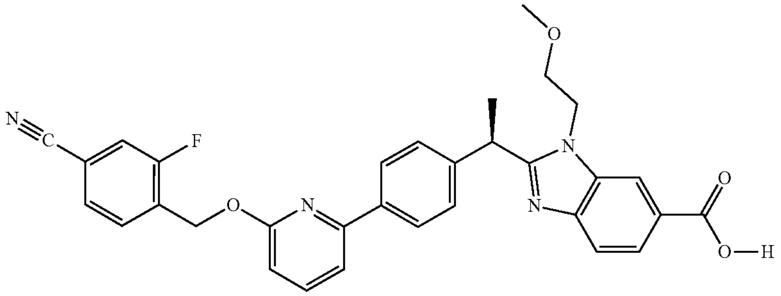
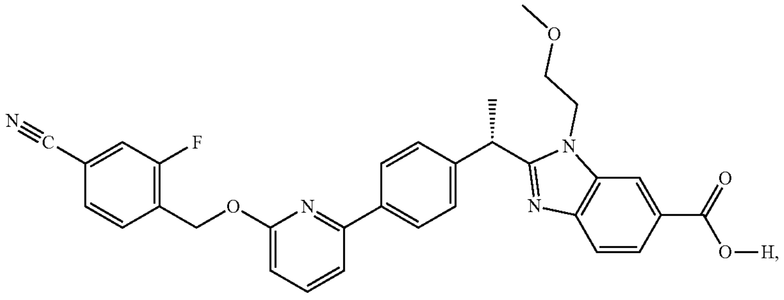
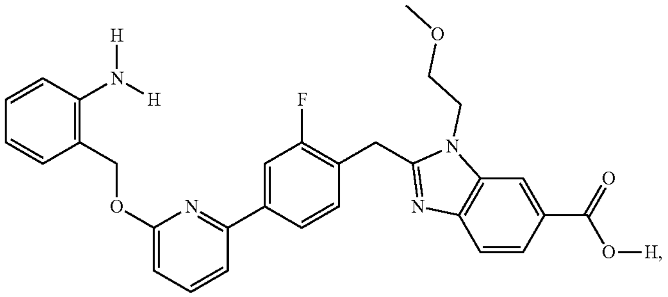

-continued
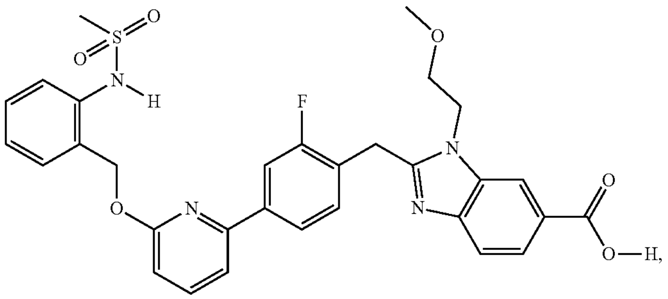
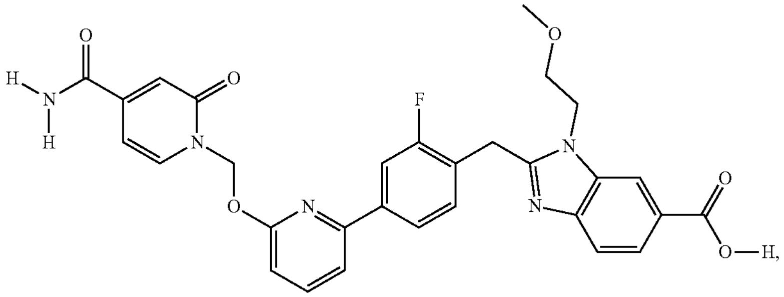
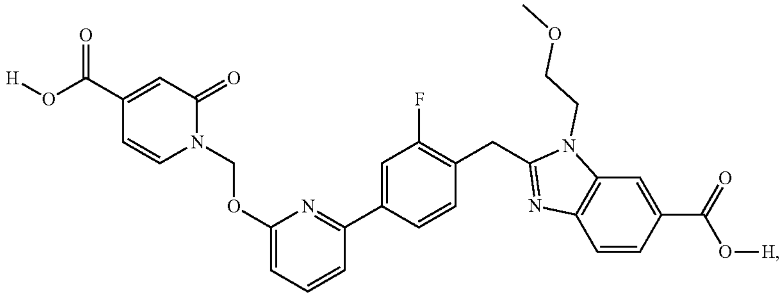
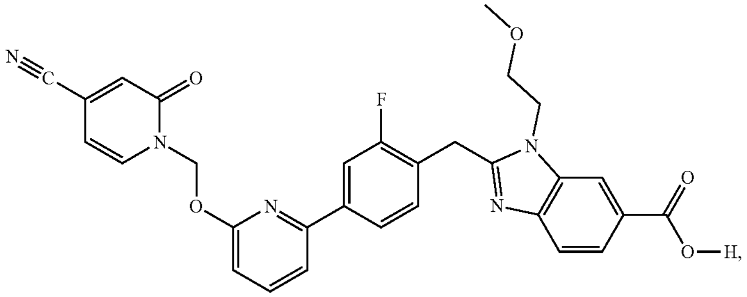
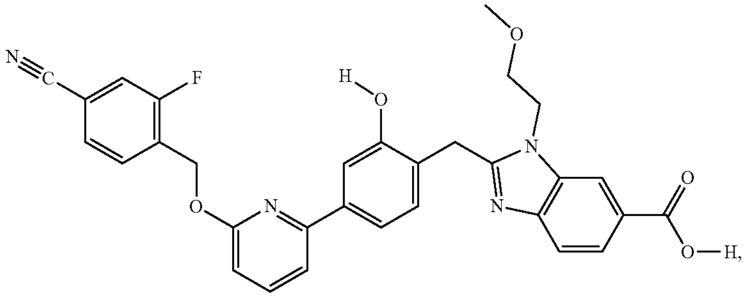

-continued
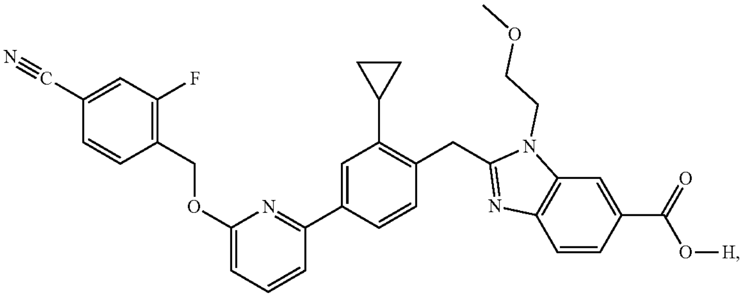
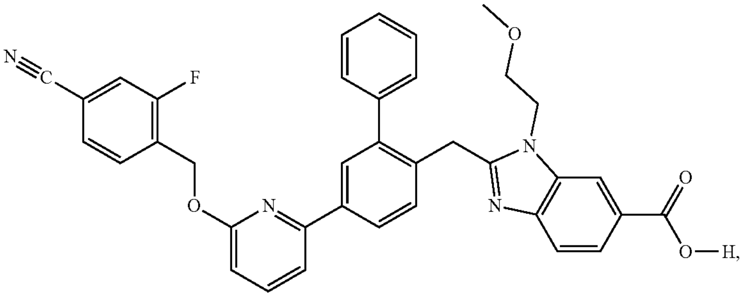
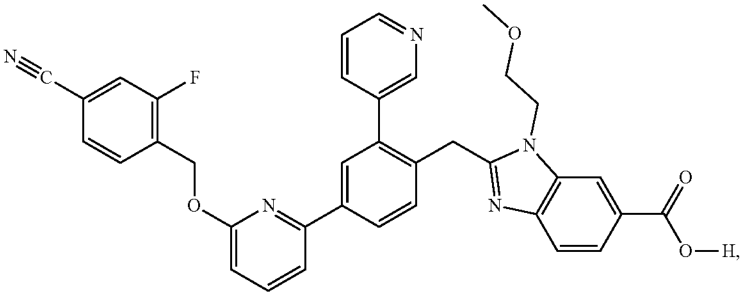
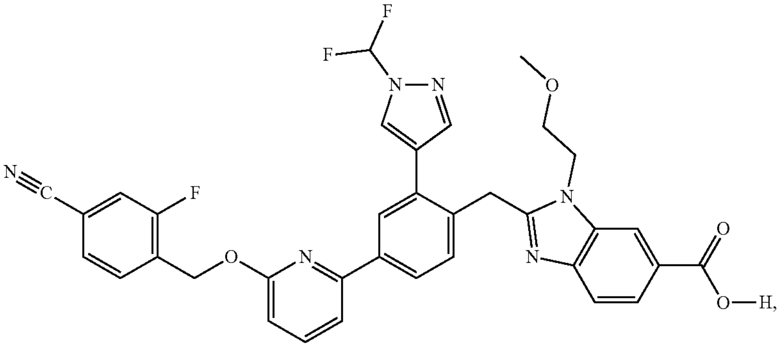
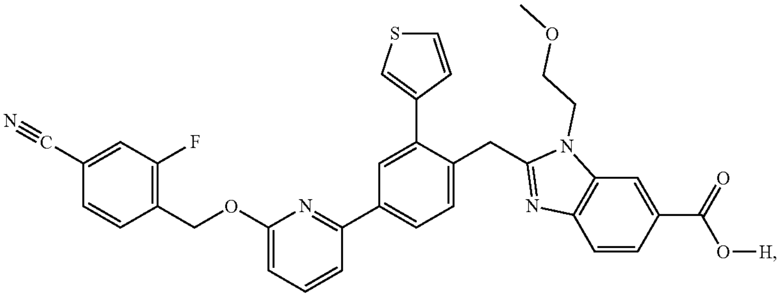

-continued
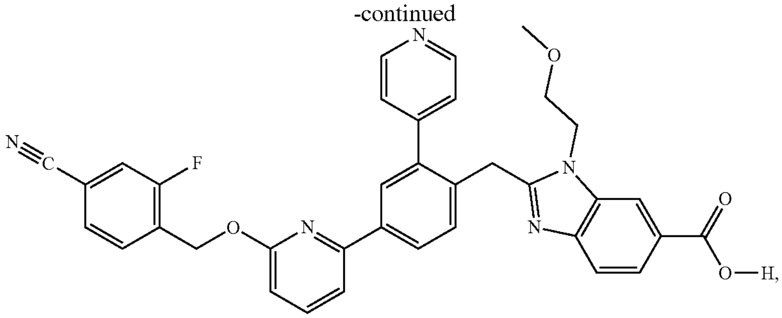
,
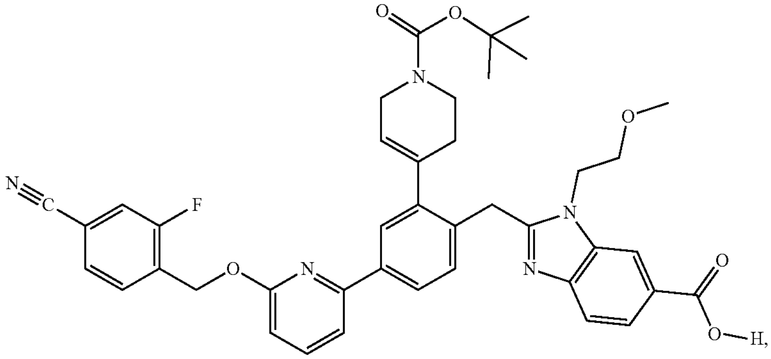
,
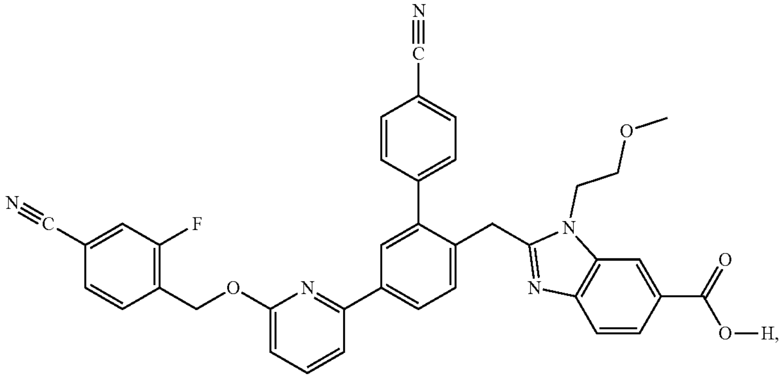
,
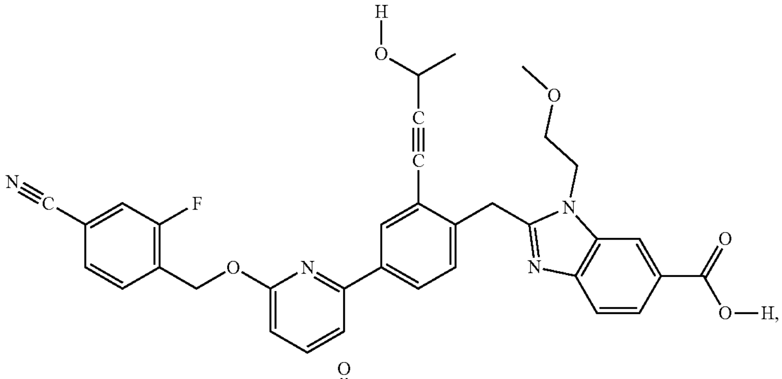
,
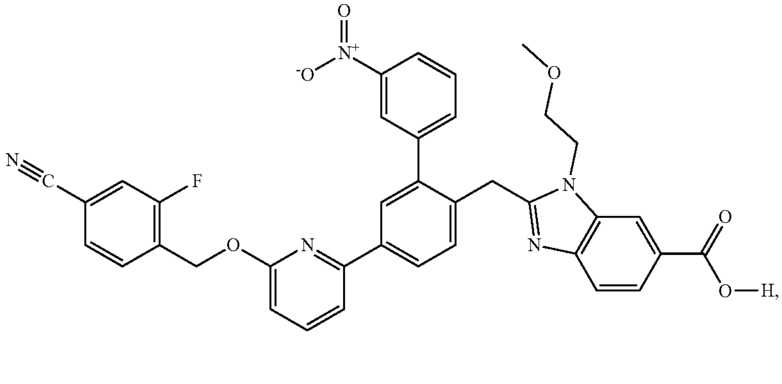
, -continued
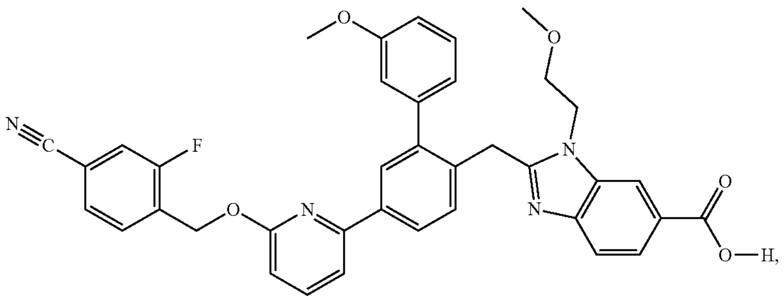
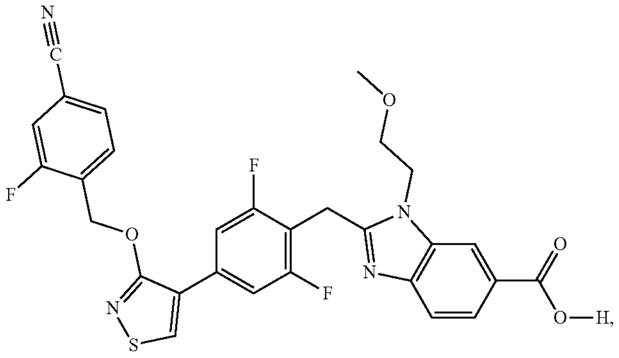
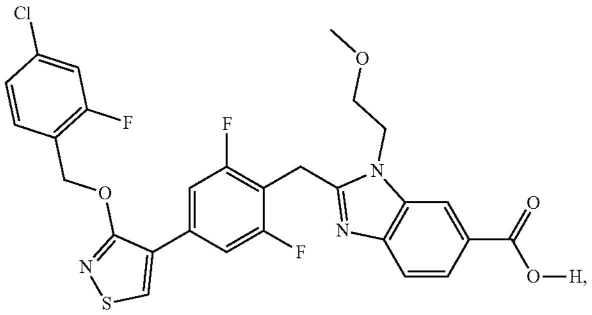
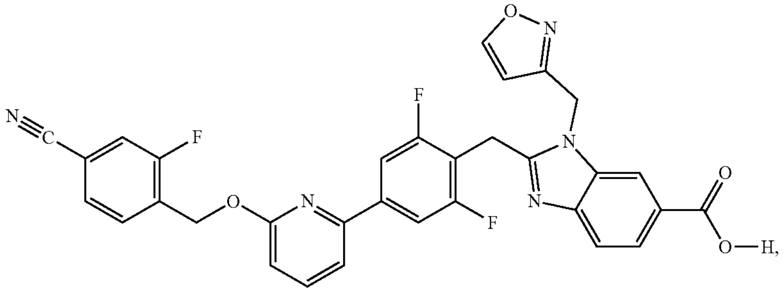
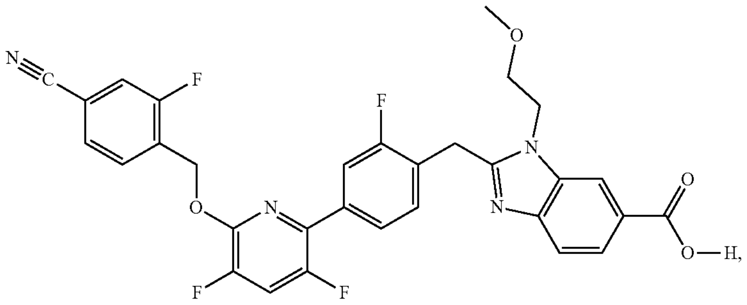

-continued
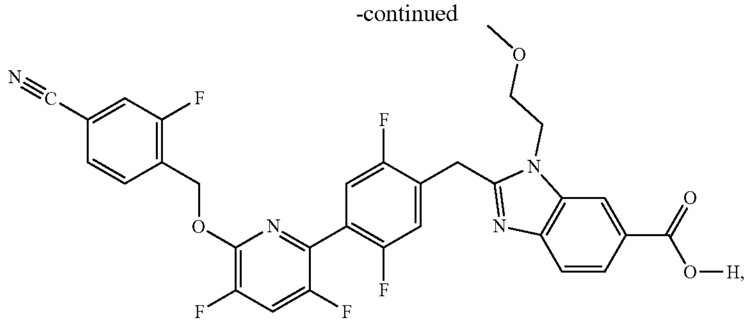
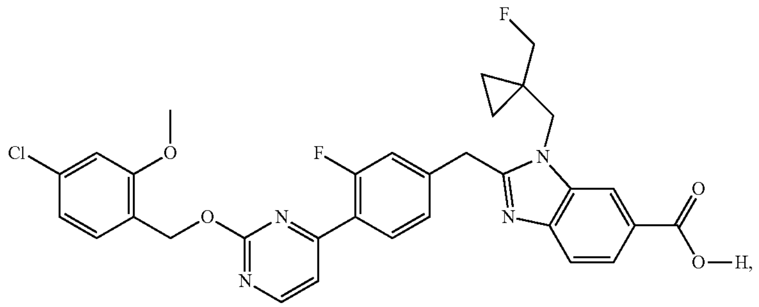
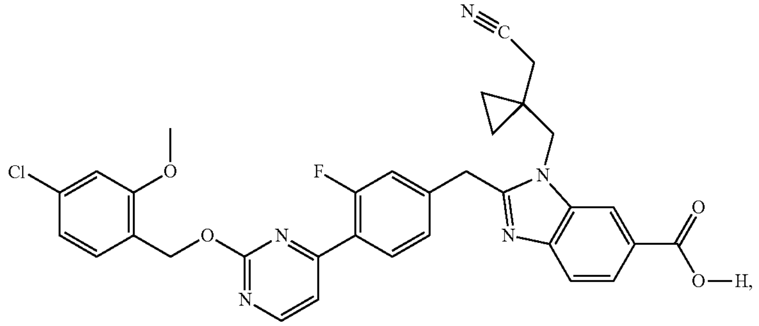
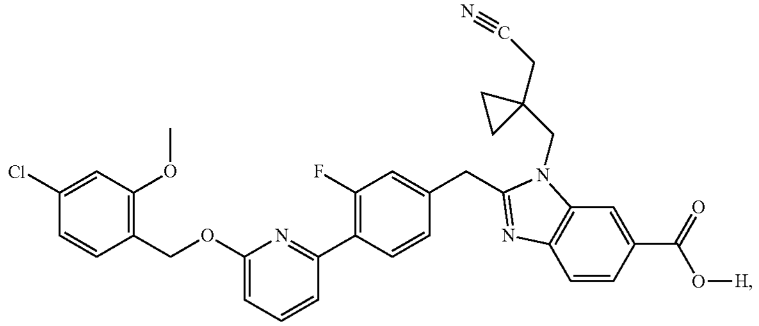
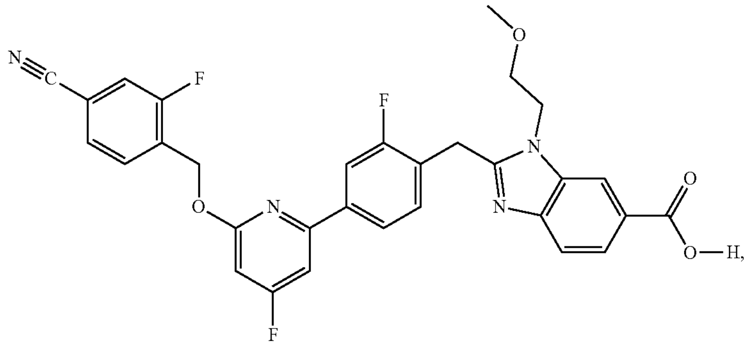

-continued
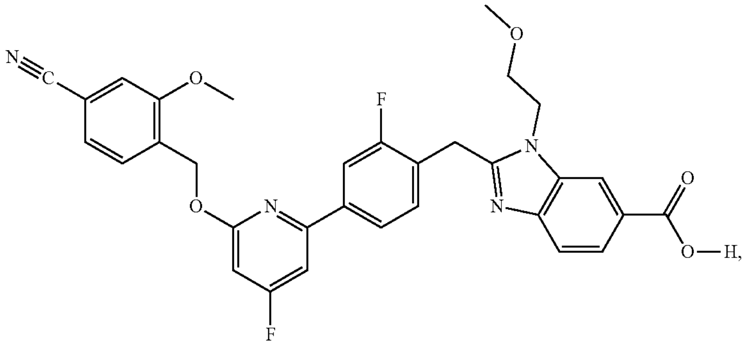
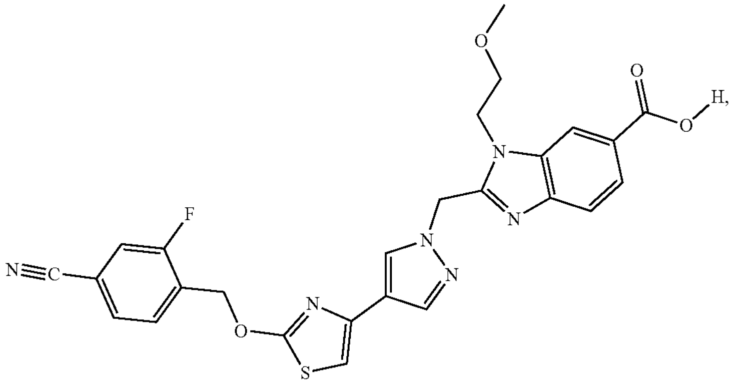
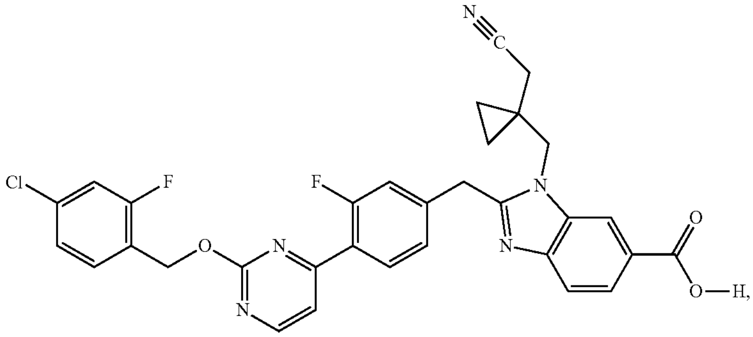
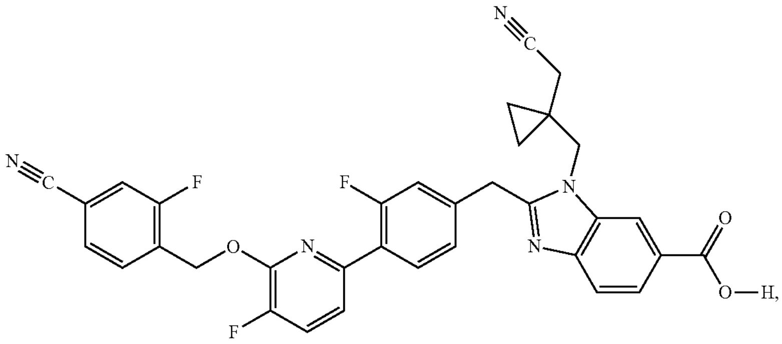

-continued
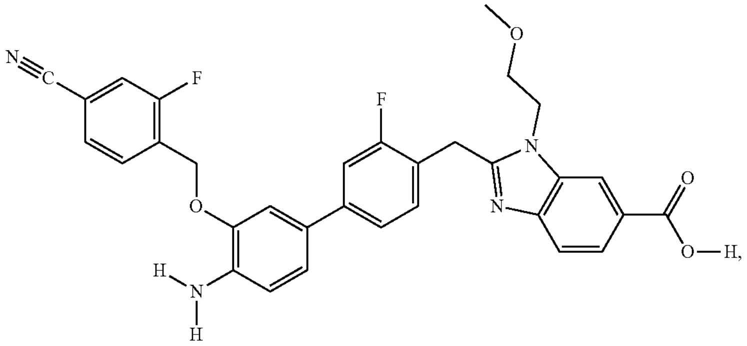
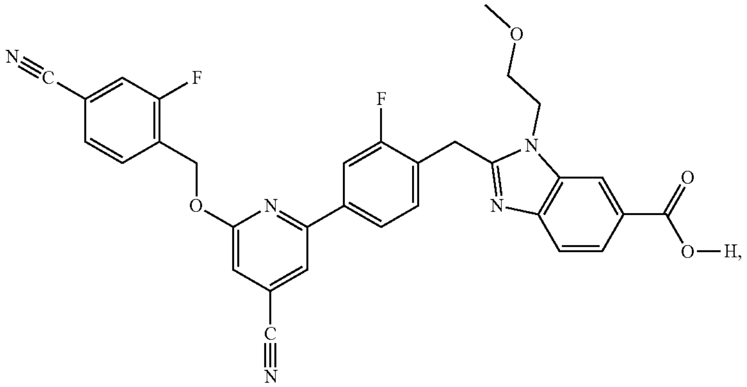
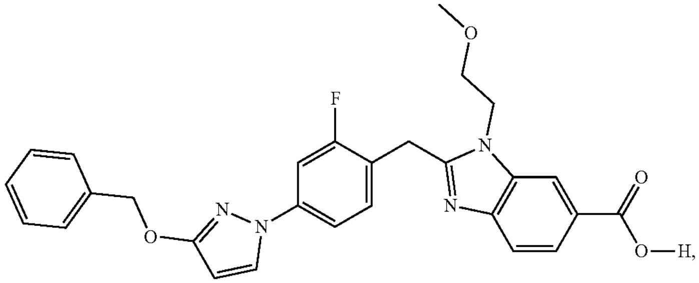
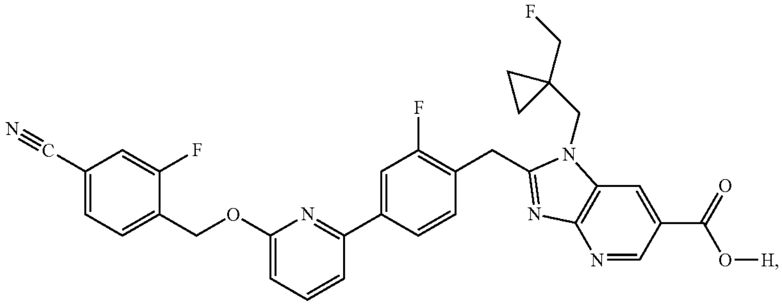
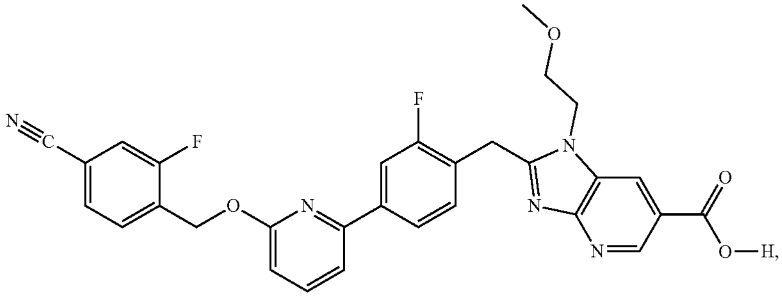

-continued
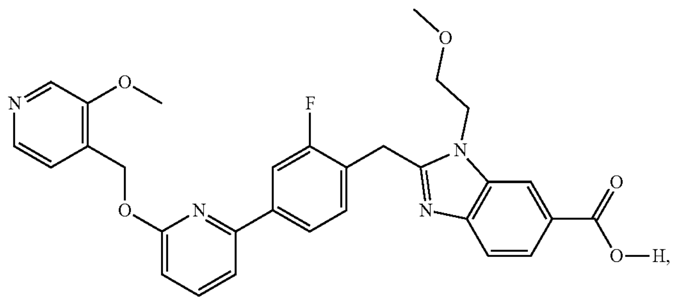
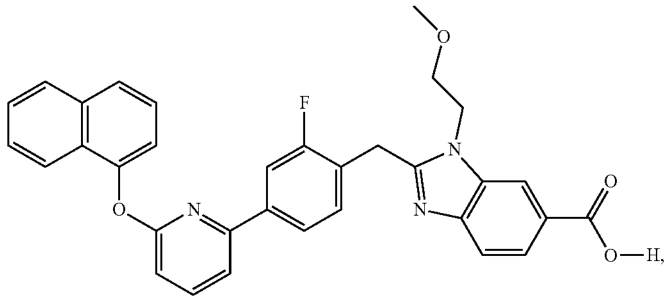
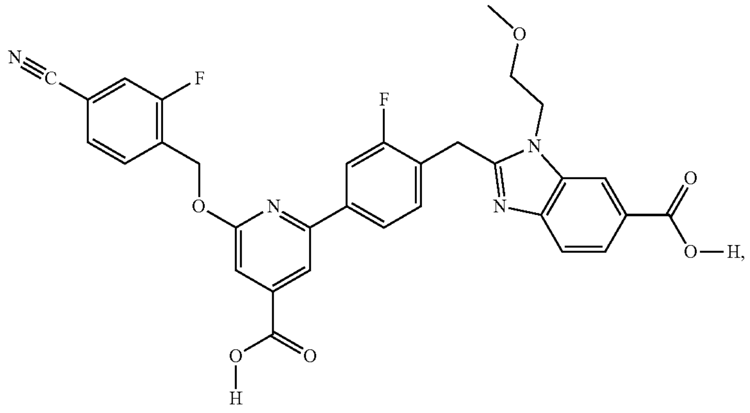
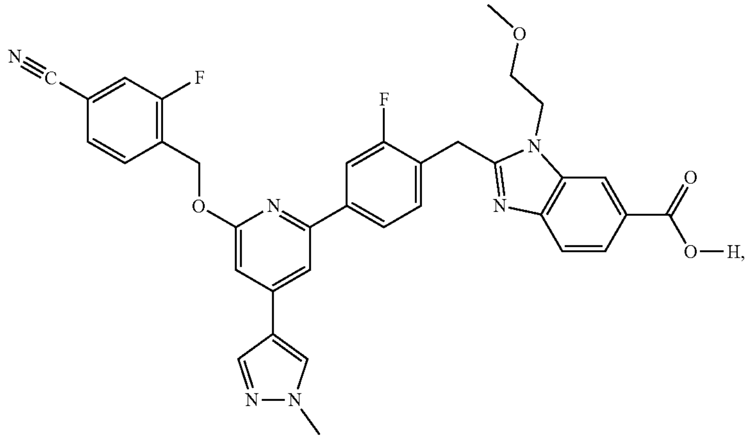

-continued
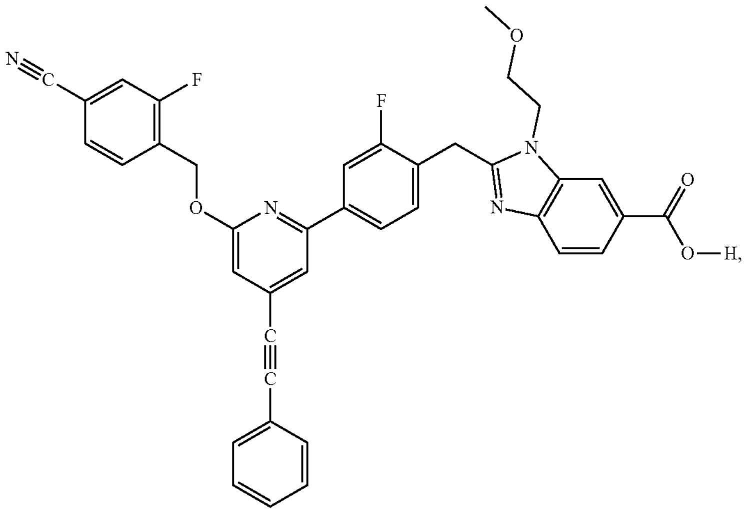
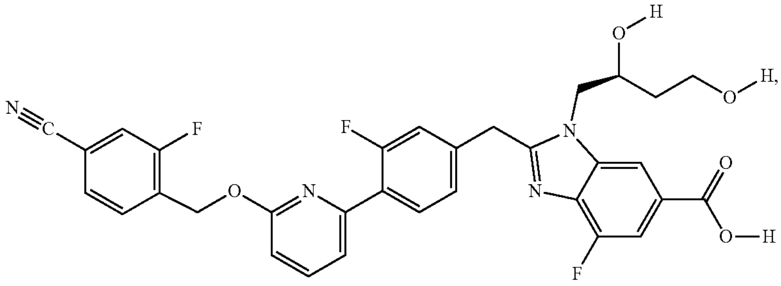
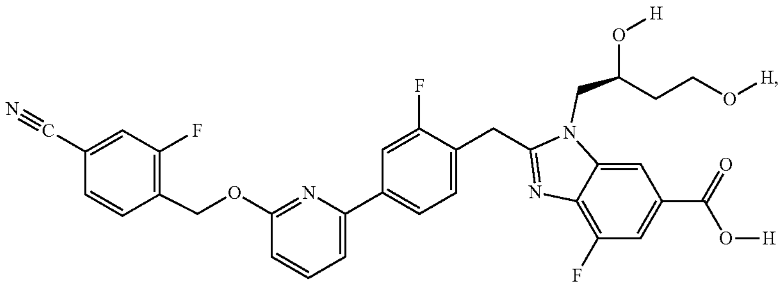
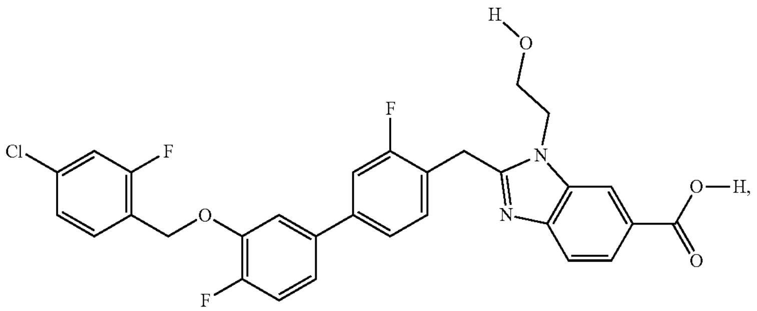
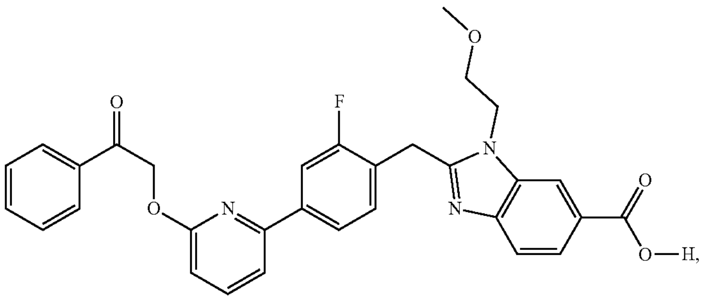

-continued
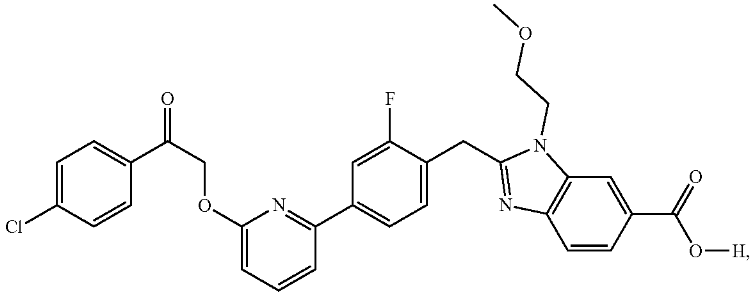
,
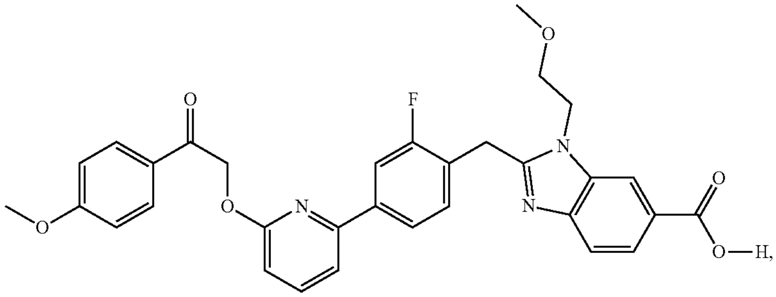
,
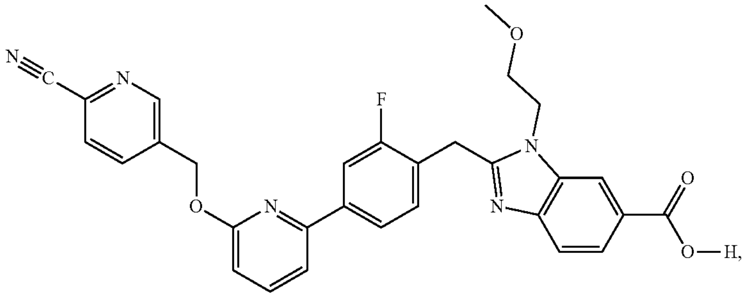
,
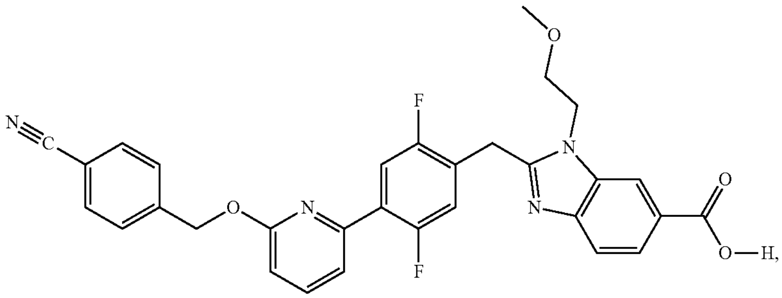
,
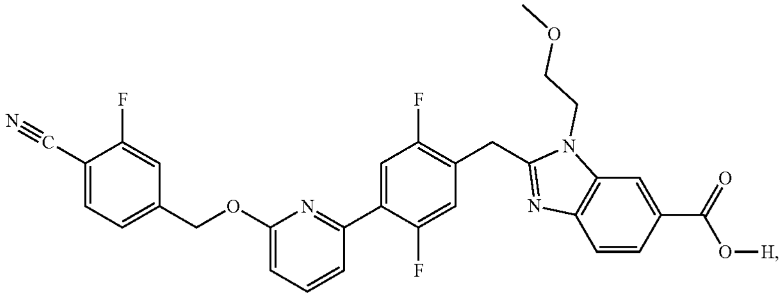
, -continued
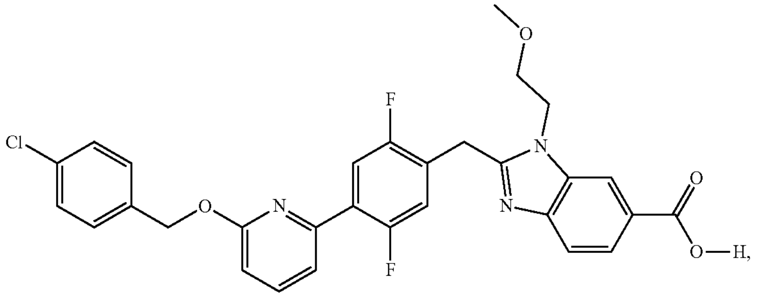
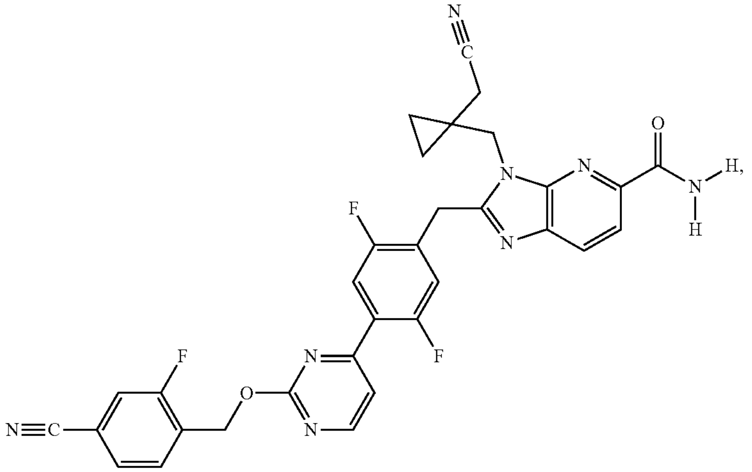
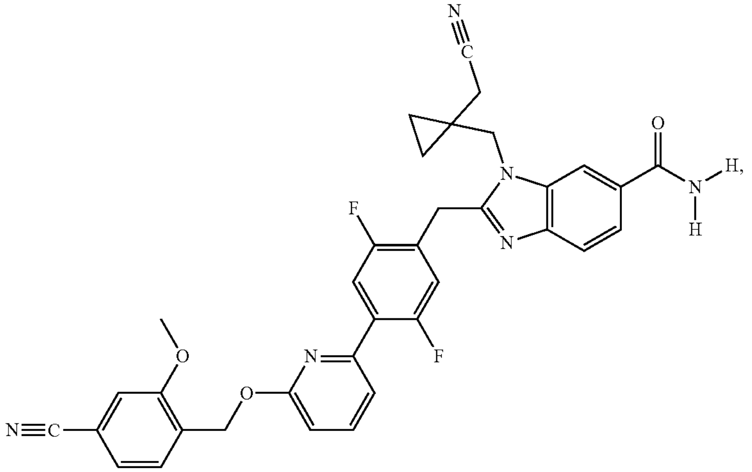
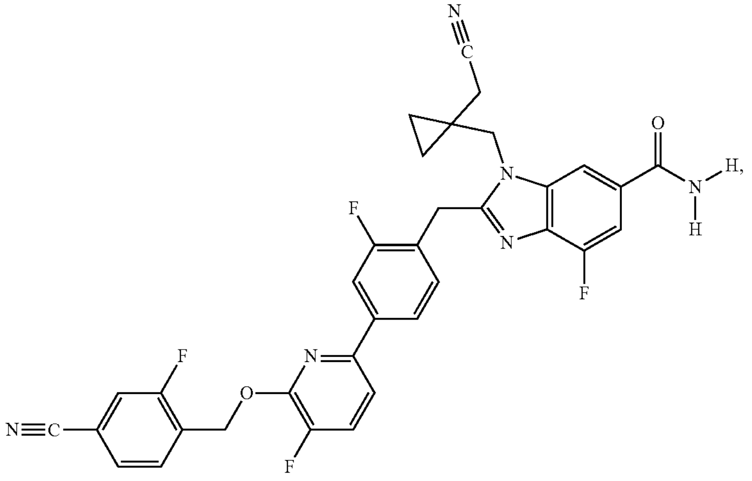

-continued
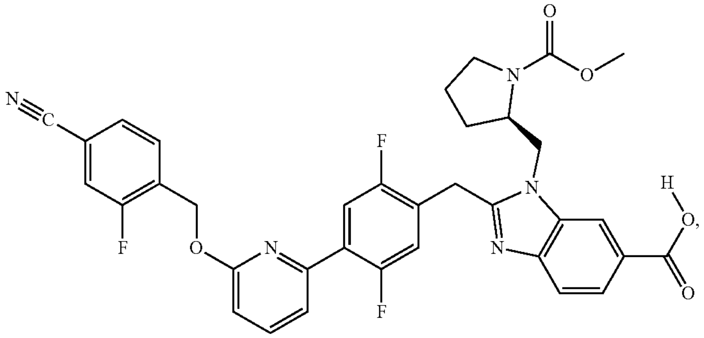
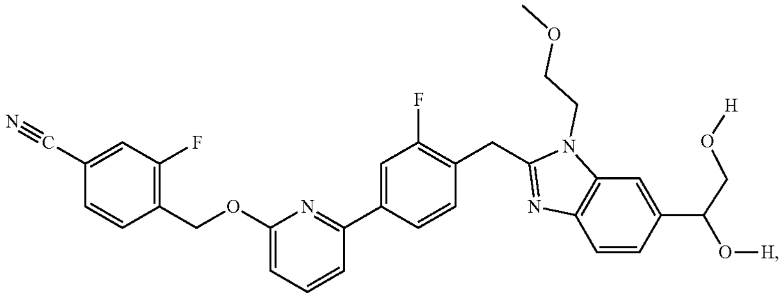
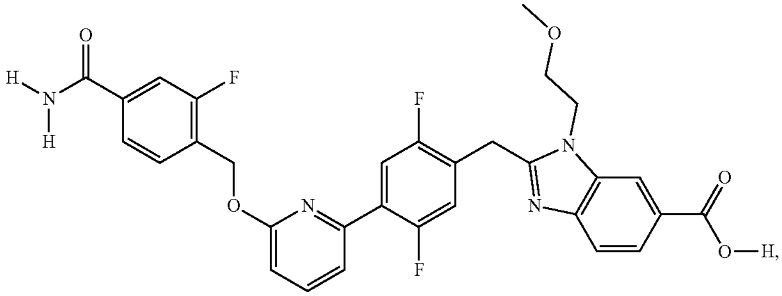
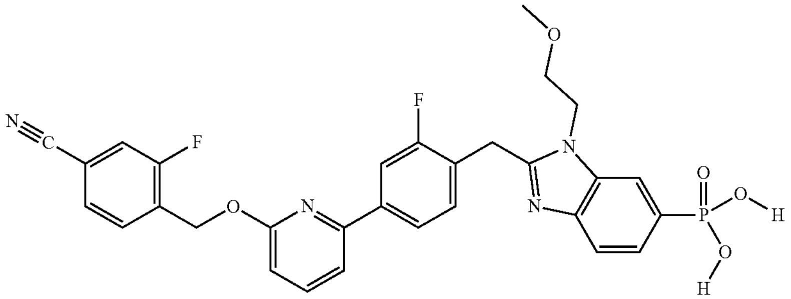
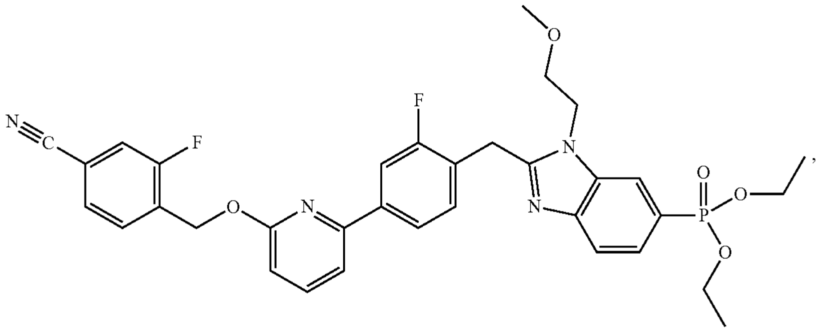

-continued
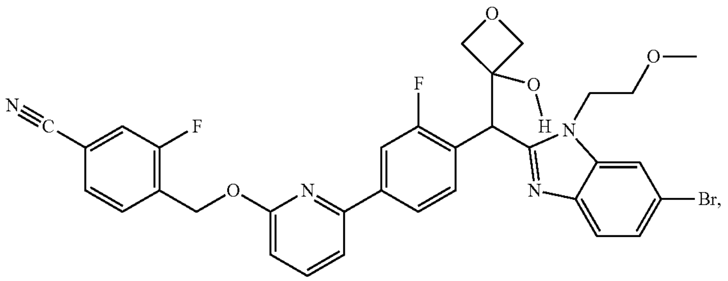
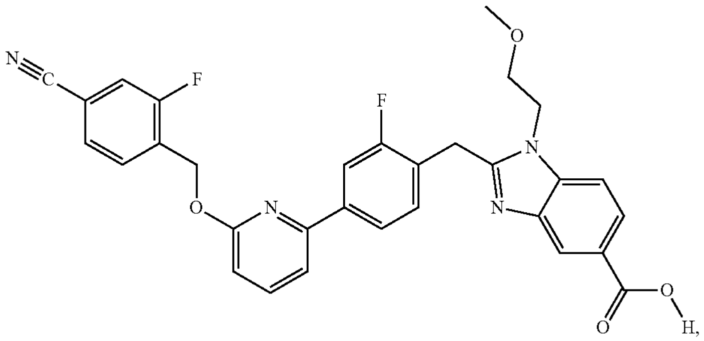
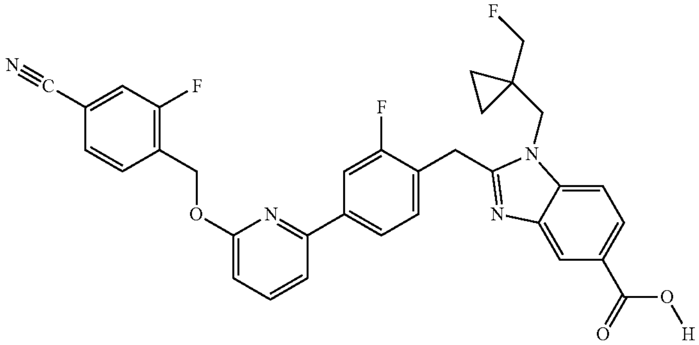
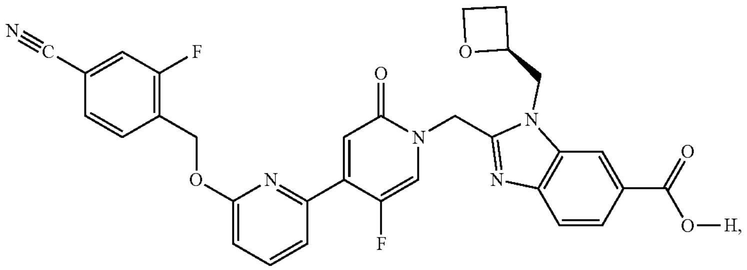
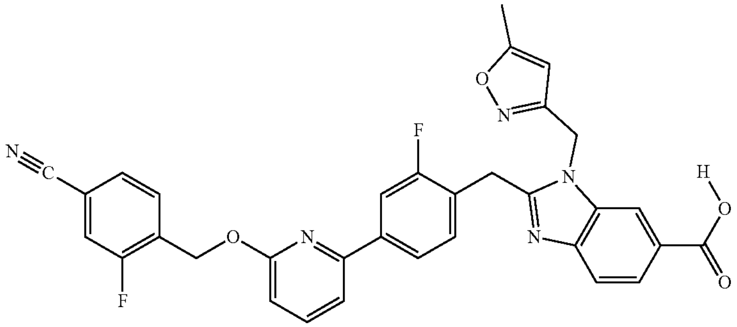

-continued
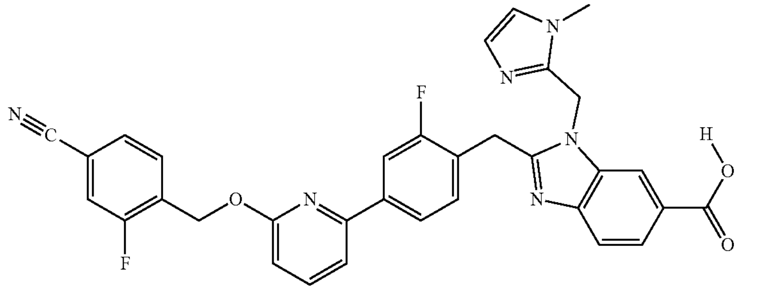
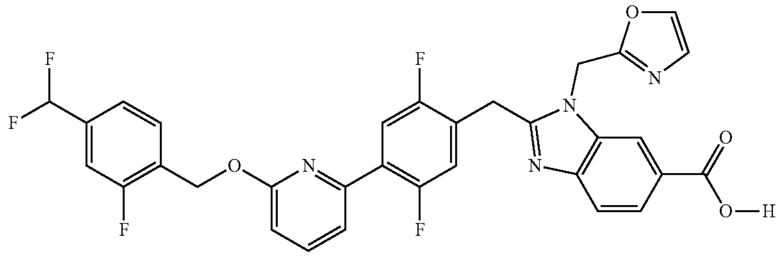
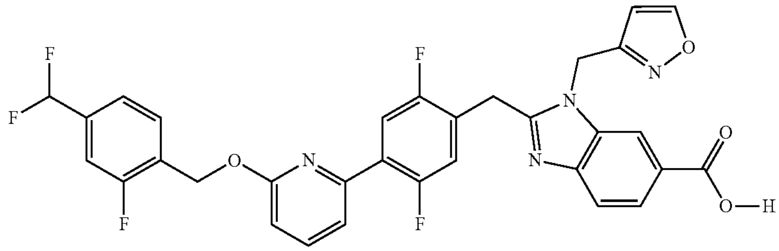
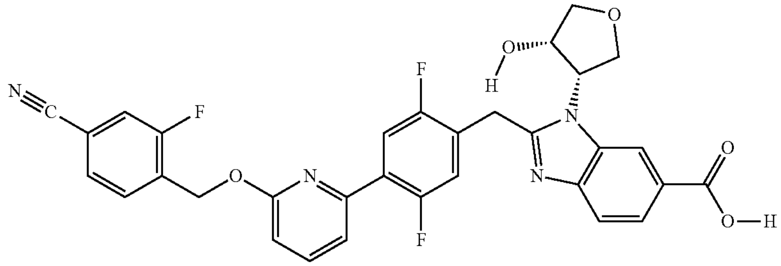
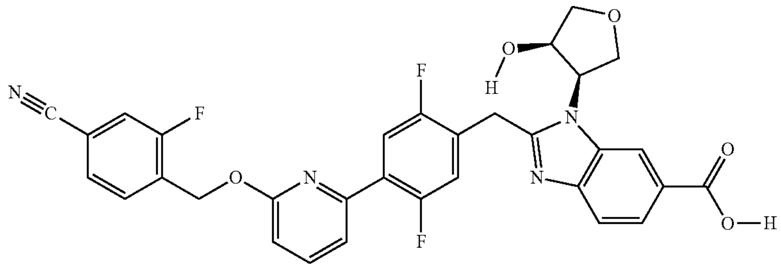
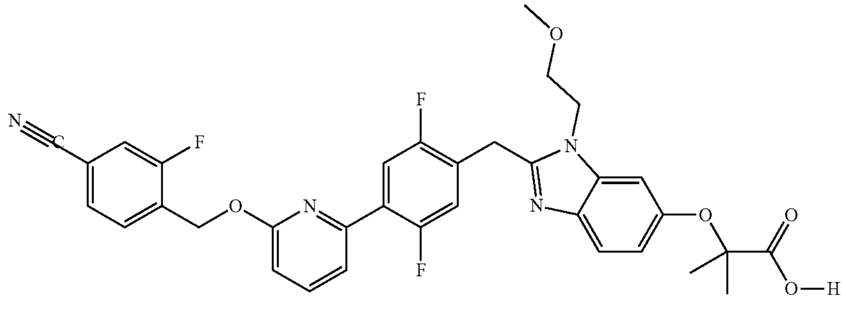

-continued
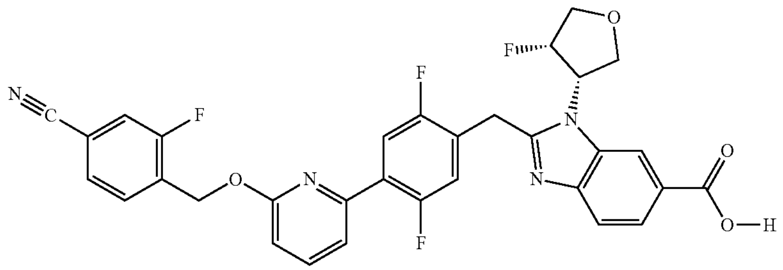
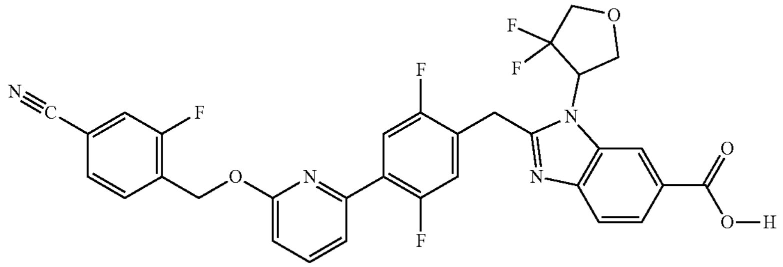
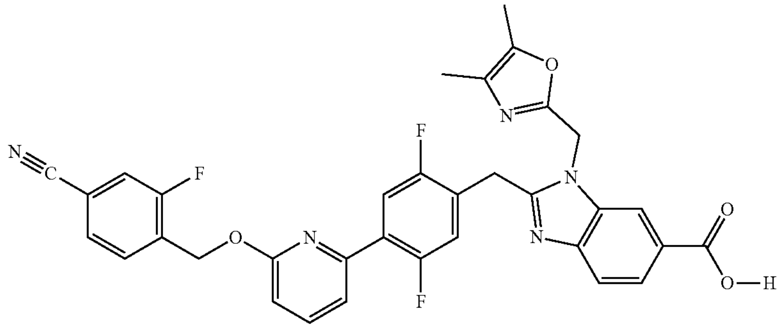
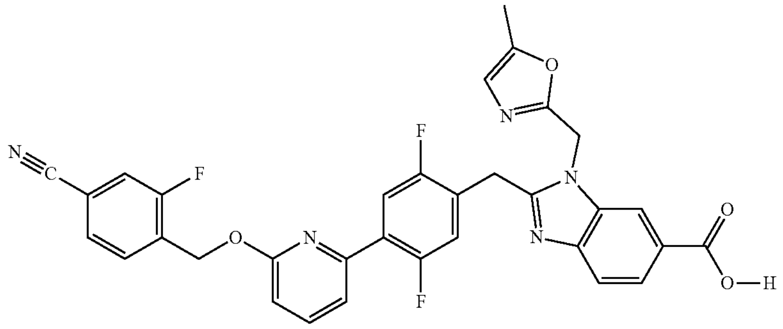
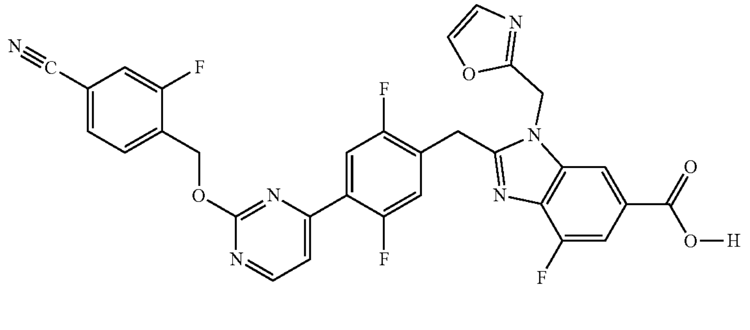

-continued
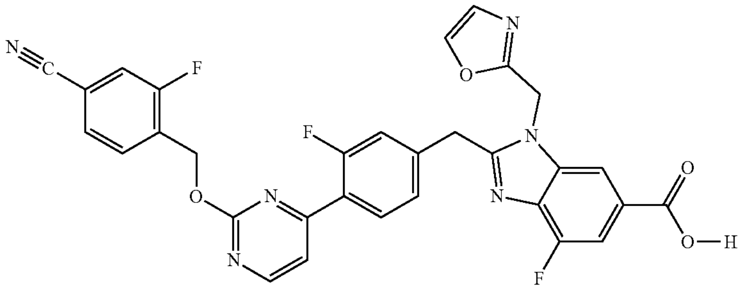
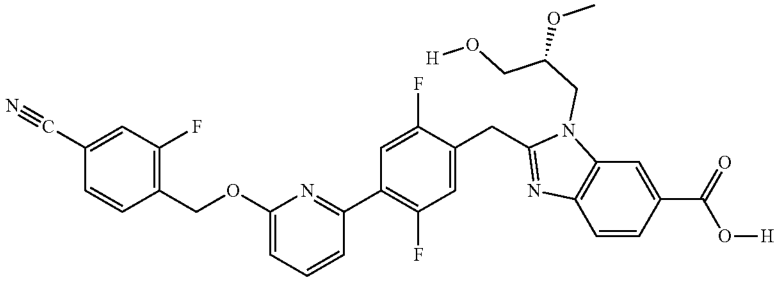
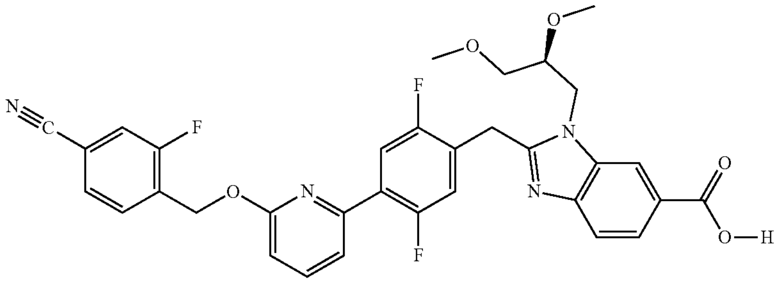
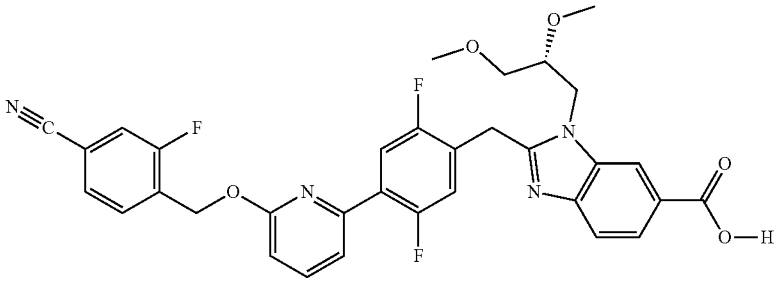
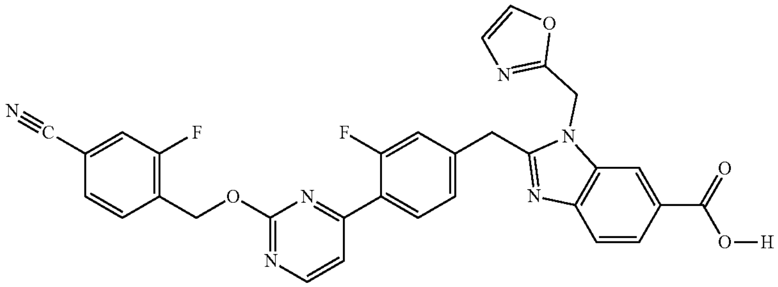
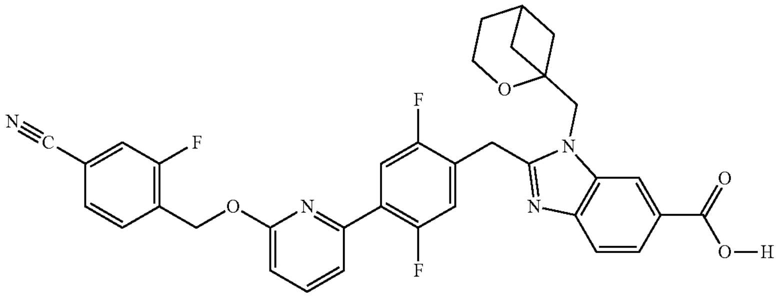

-continued
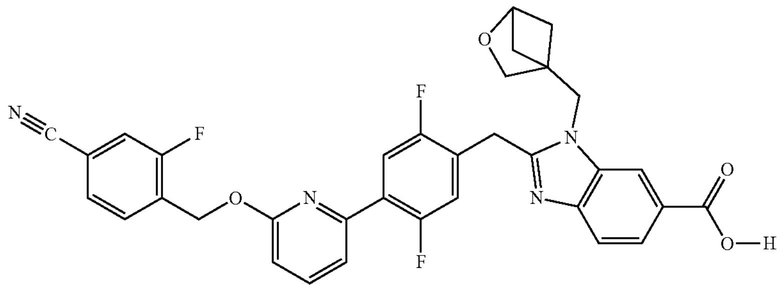
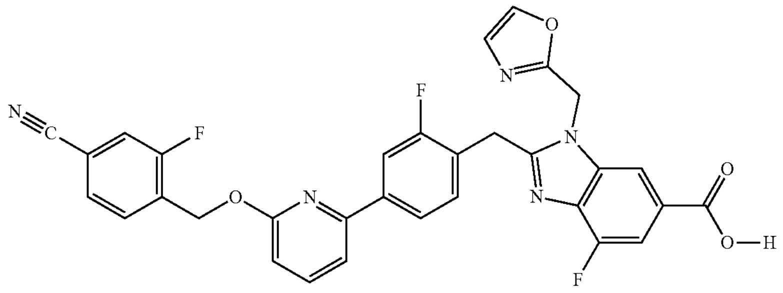
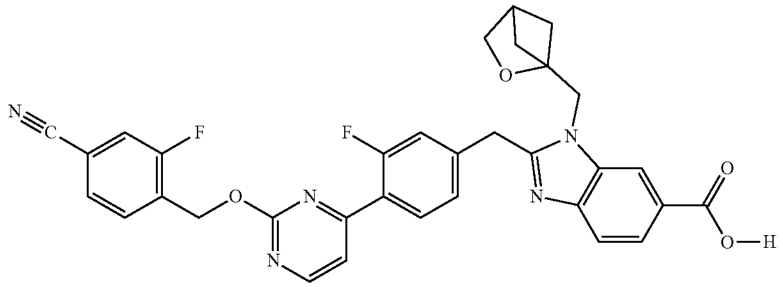
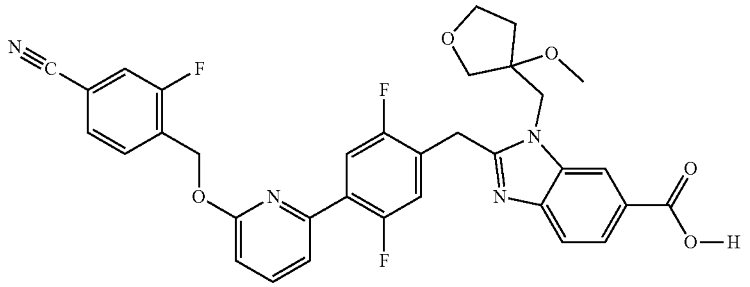
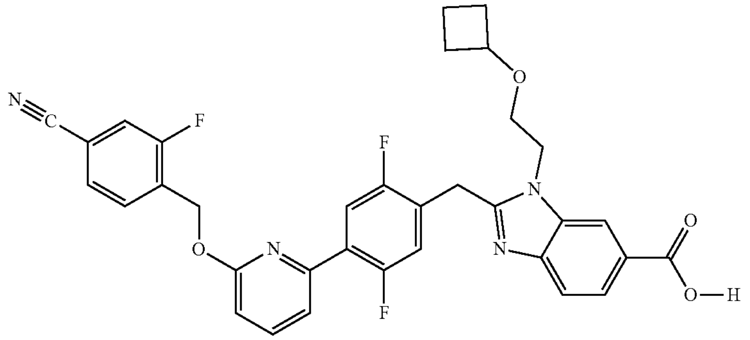

-continued
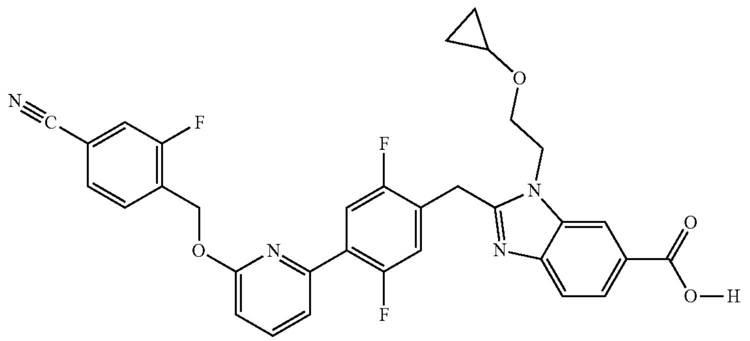
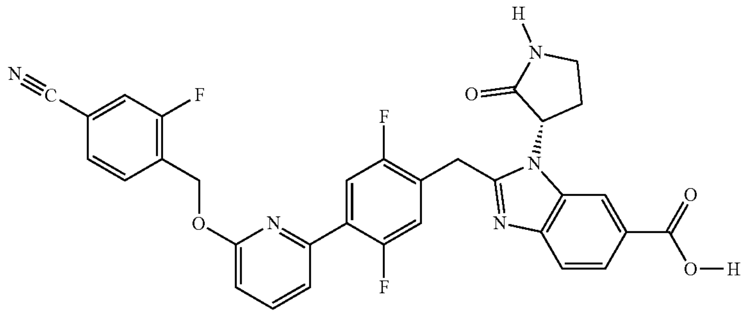
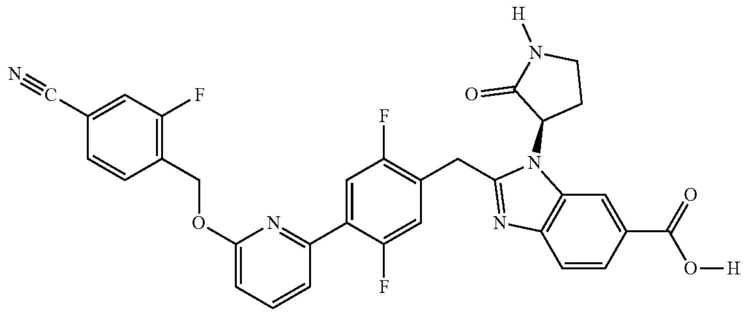
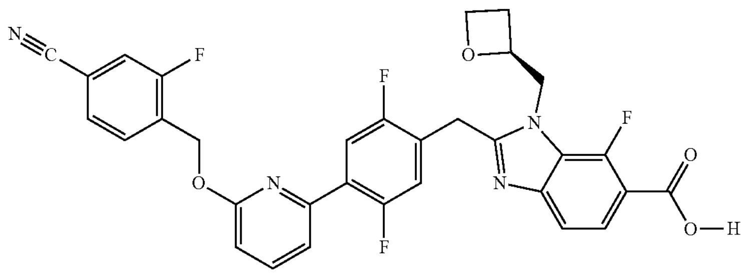
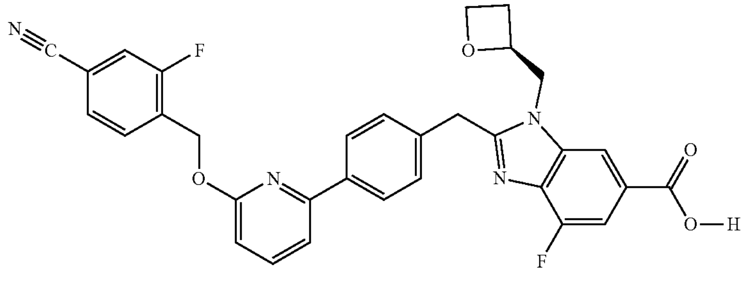

-continued
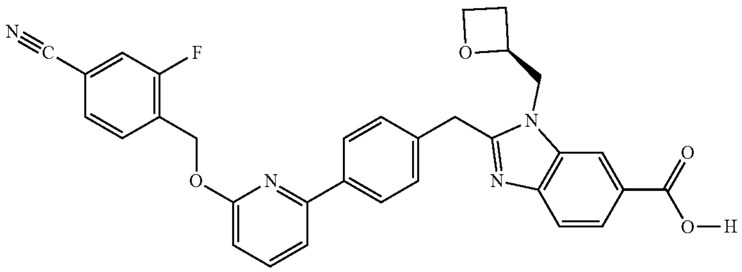
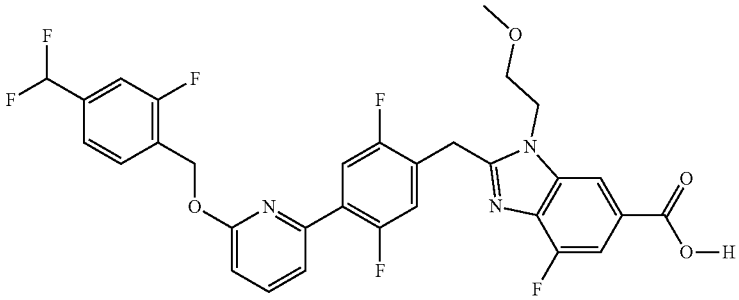
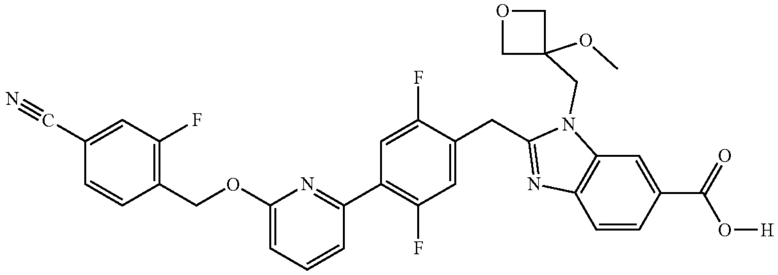
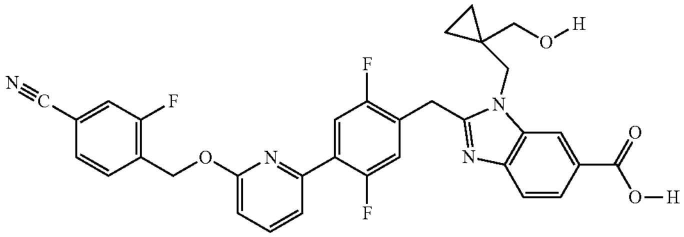
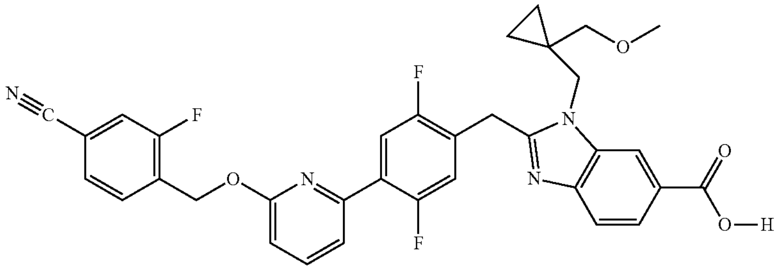
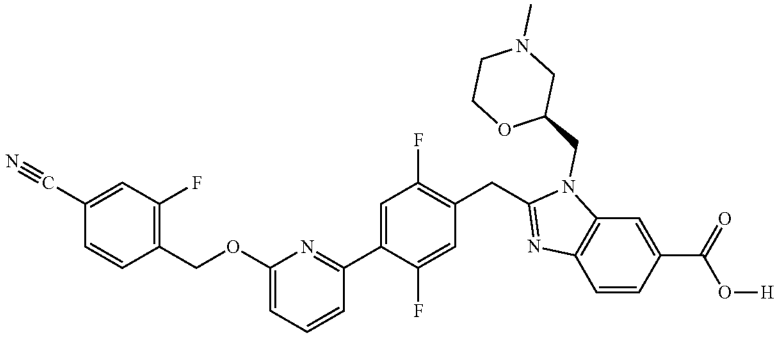

-continued
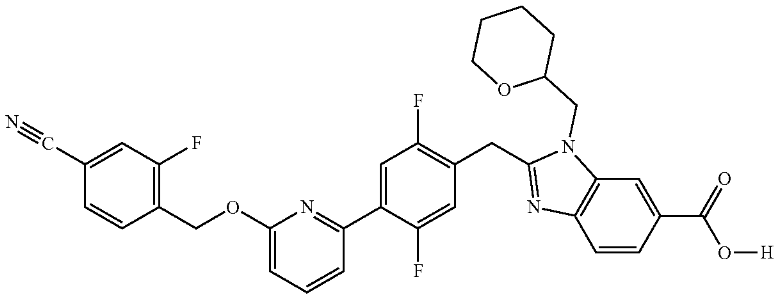
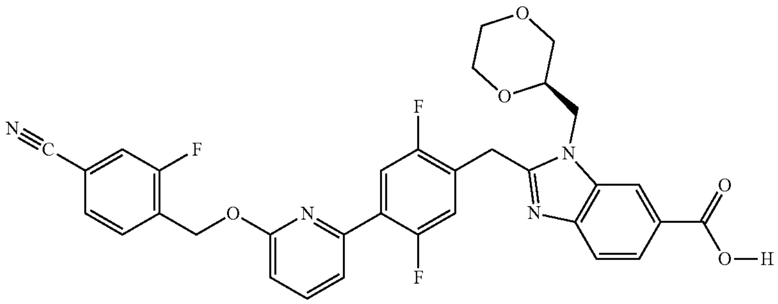
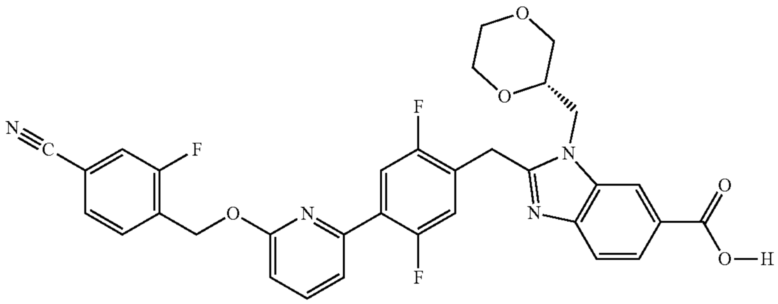
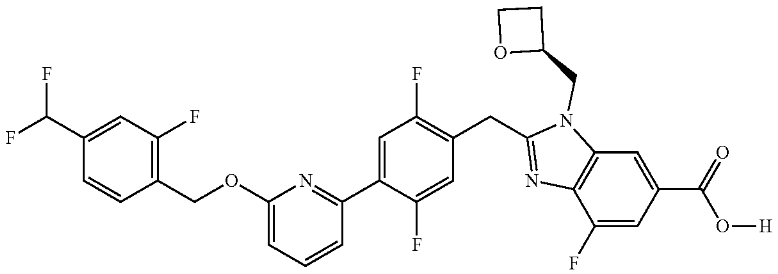
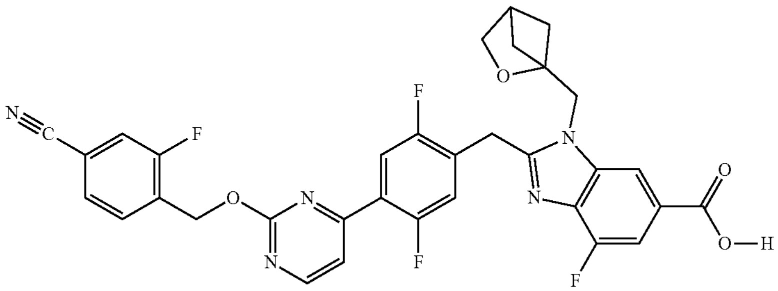

-continued
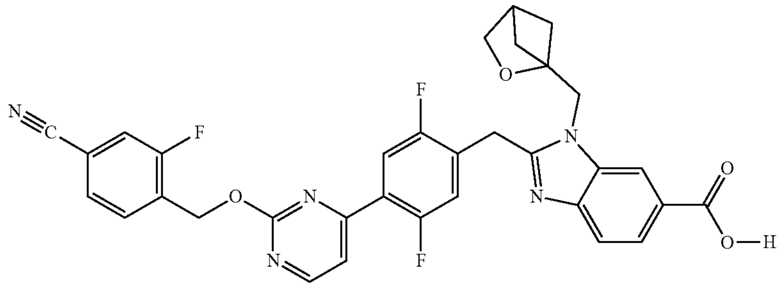
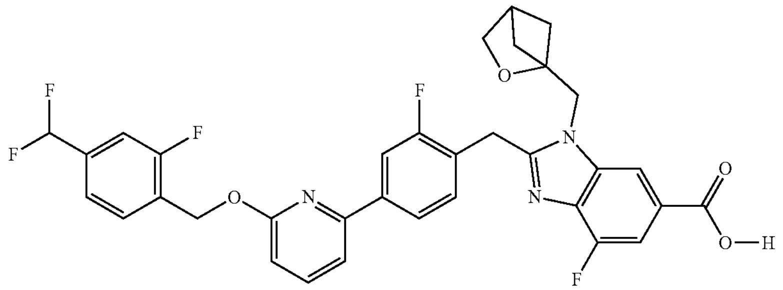
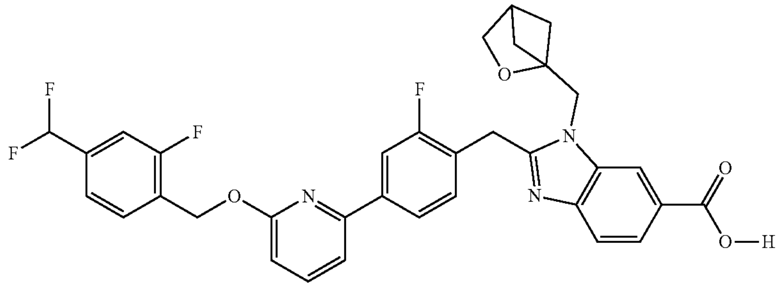
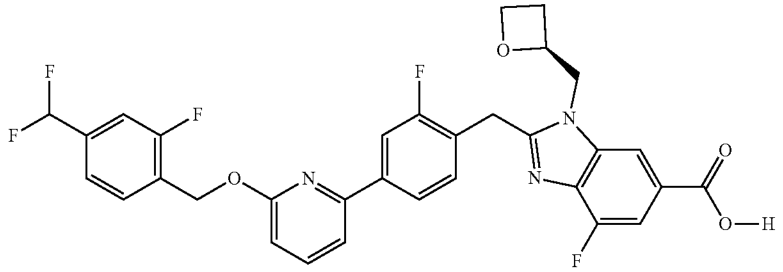
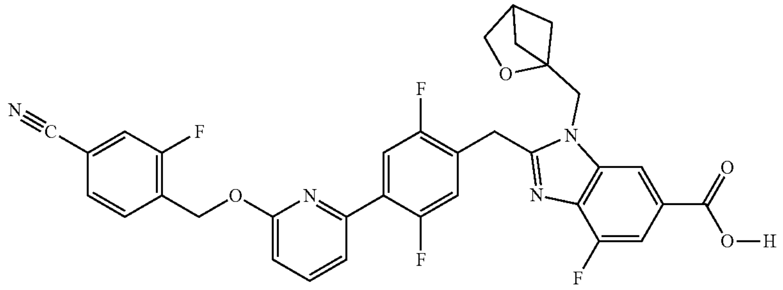
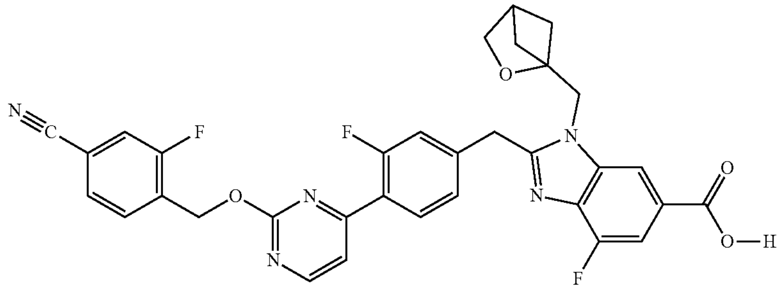

-continued
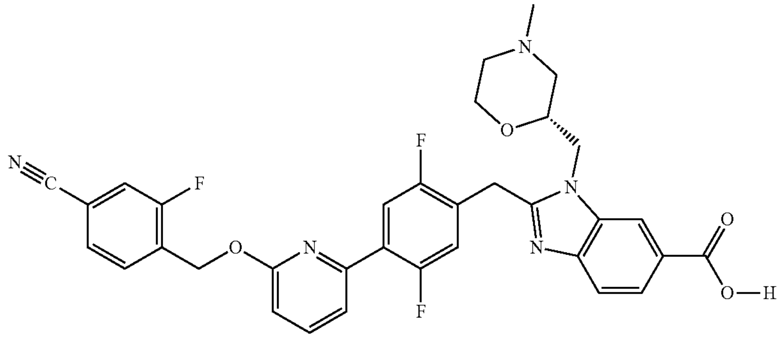
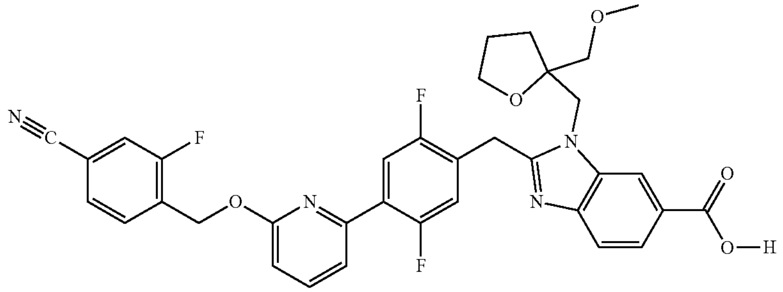
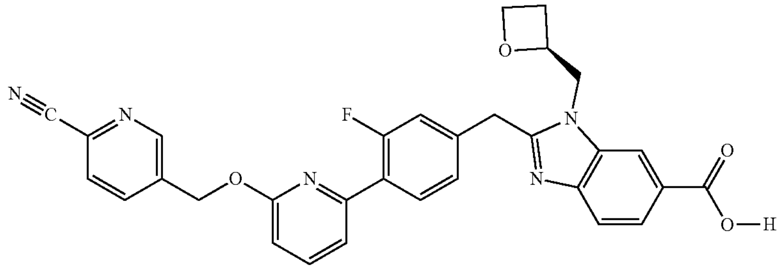
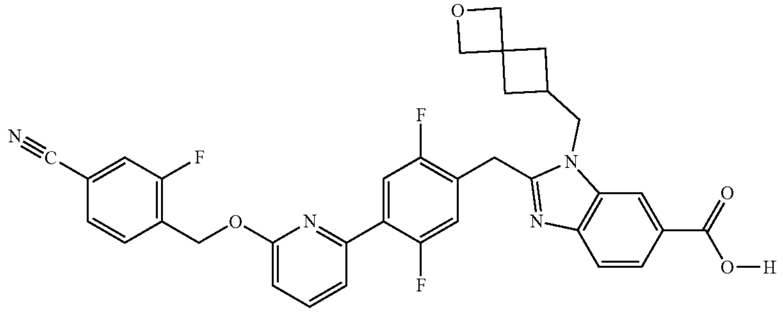
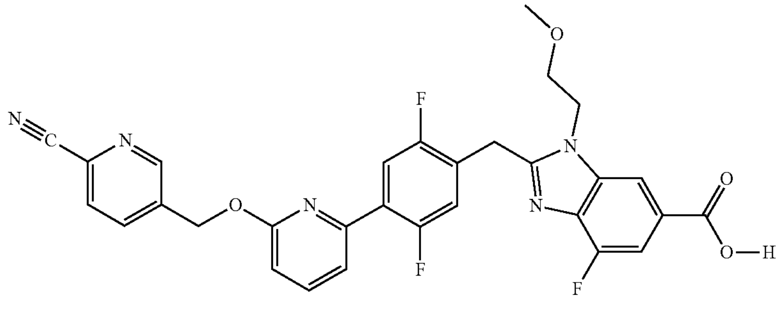

-continued
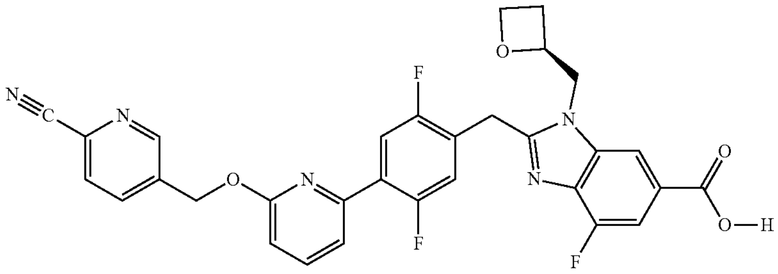
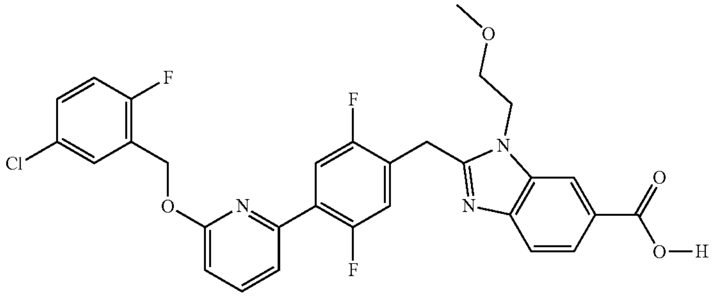
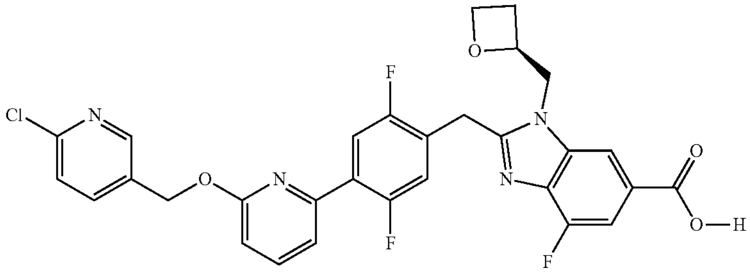
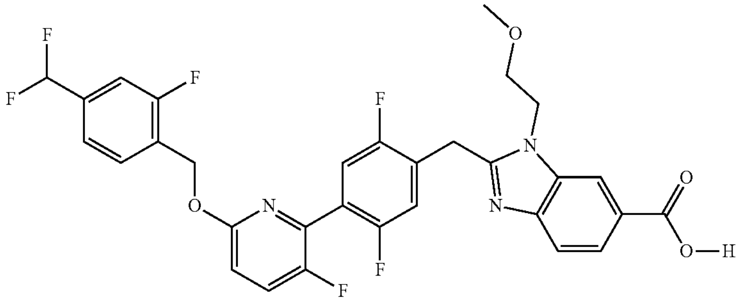
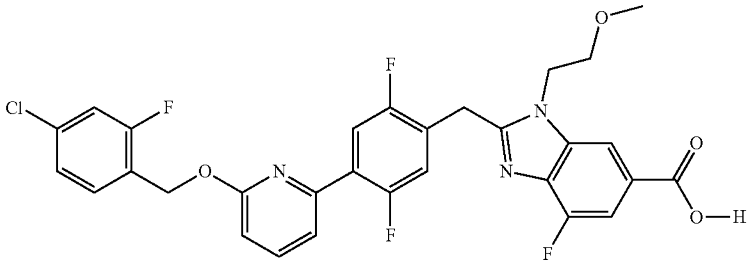
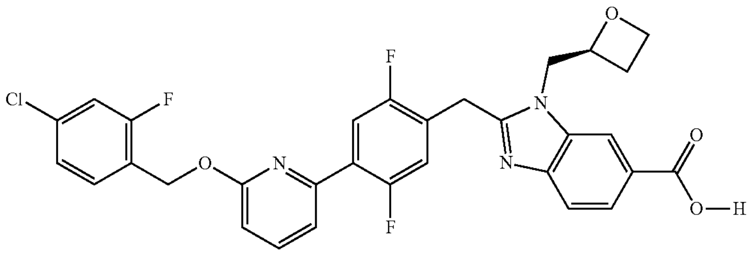

-continued
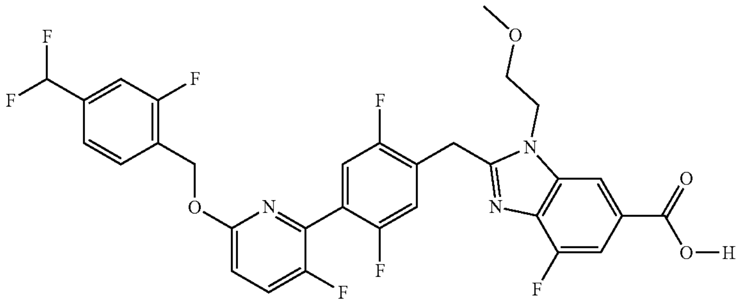
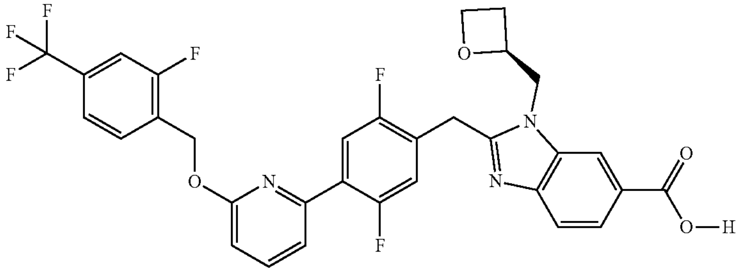
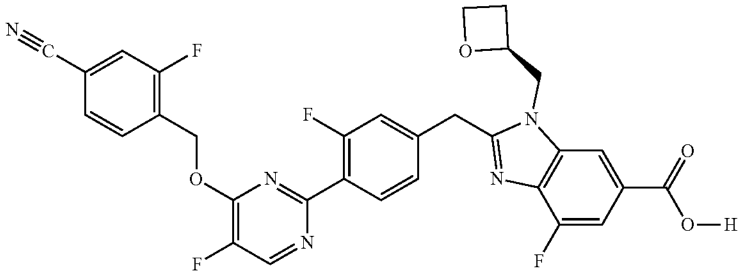
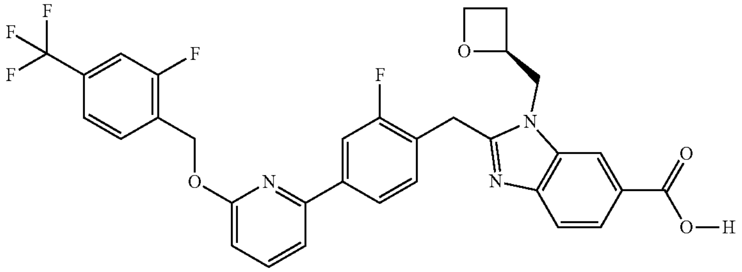
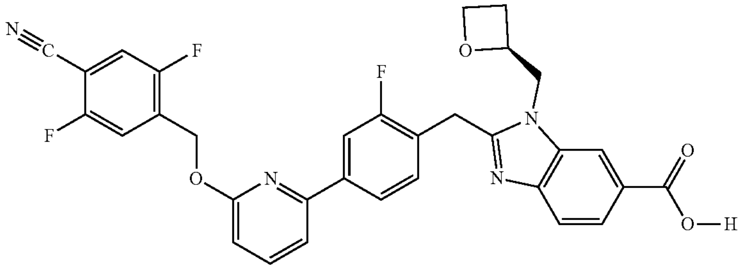
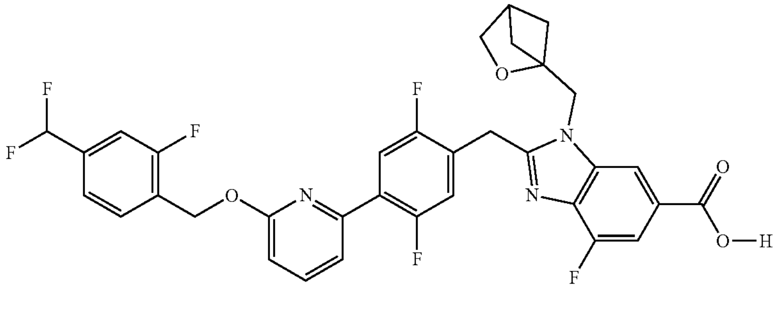

-continued
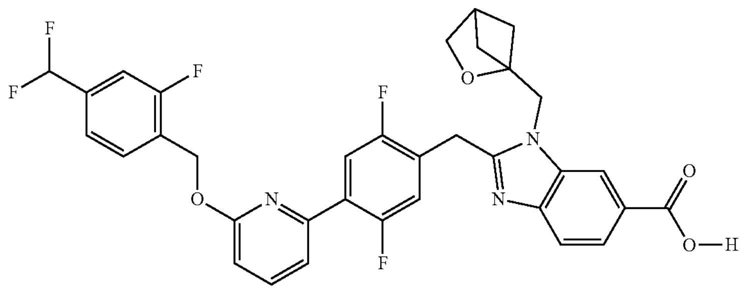
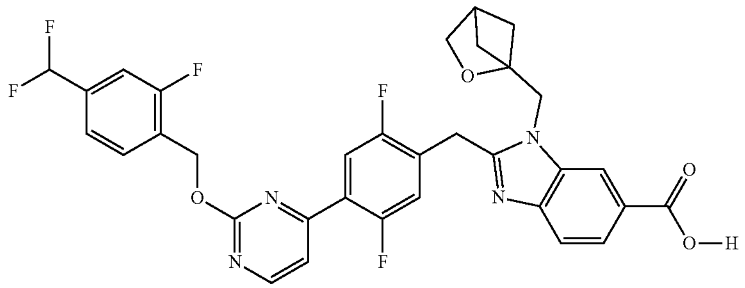
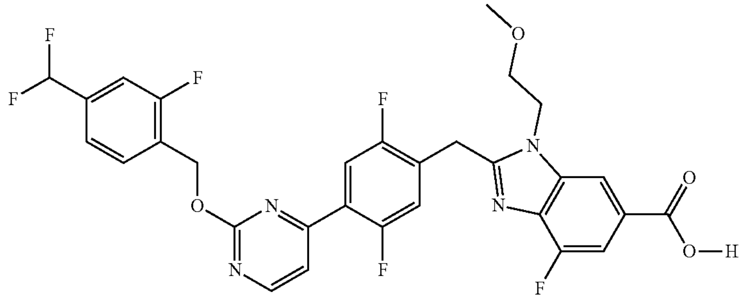
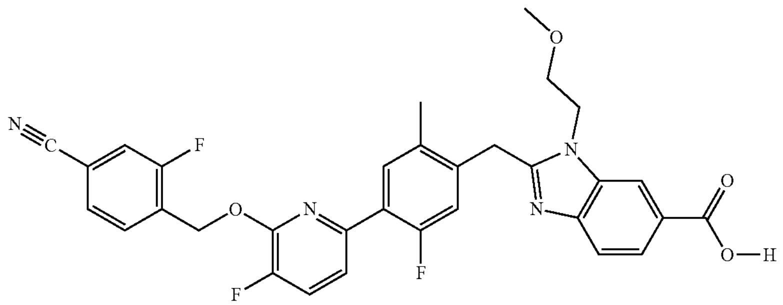
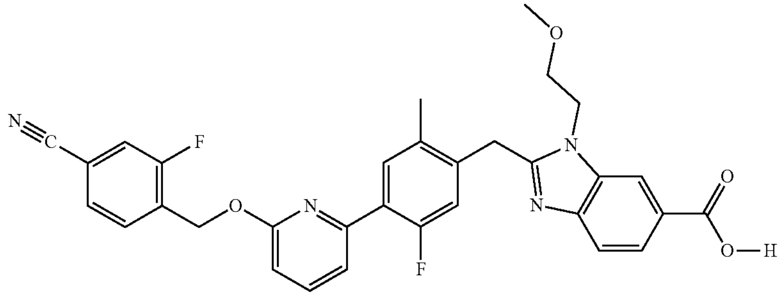

-continued
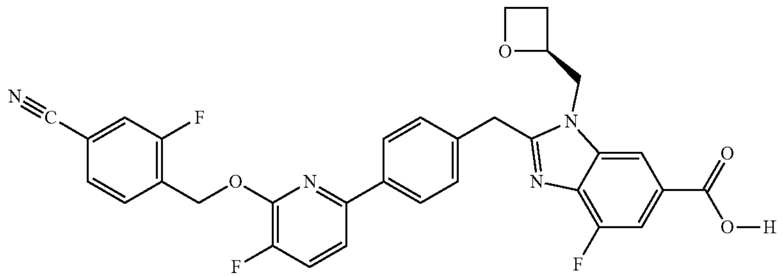
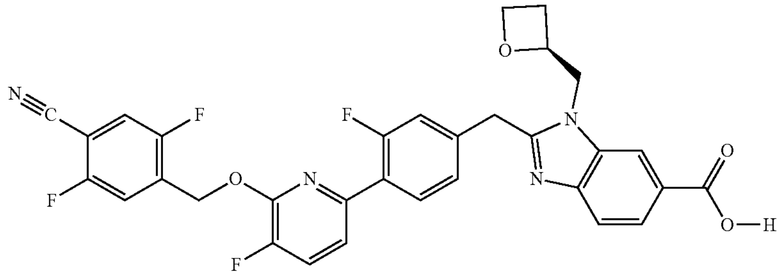
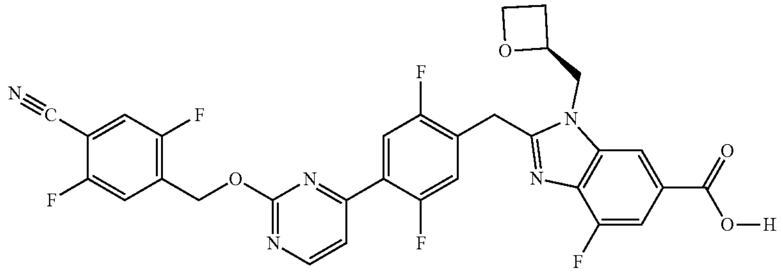
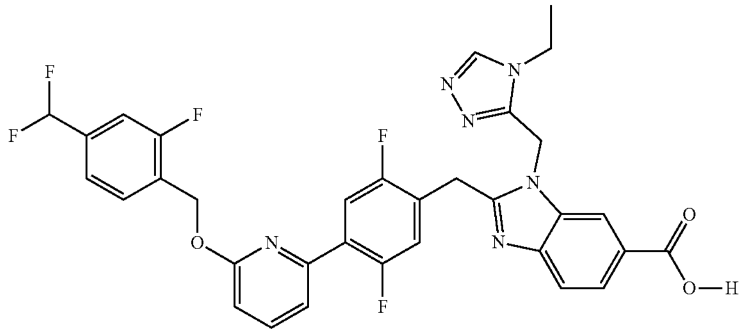
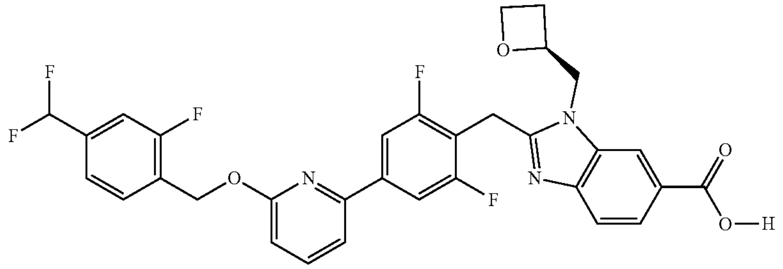
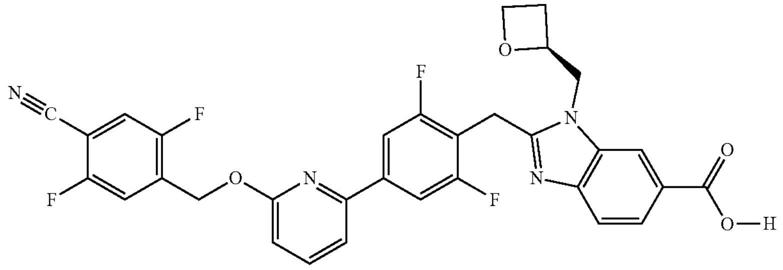

-continued
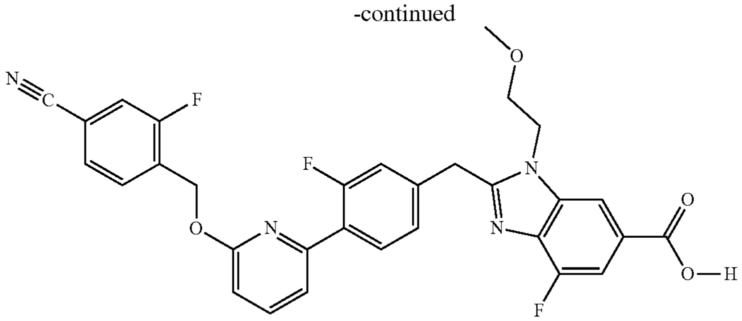
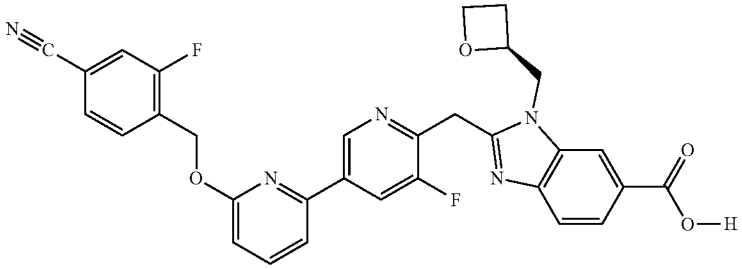
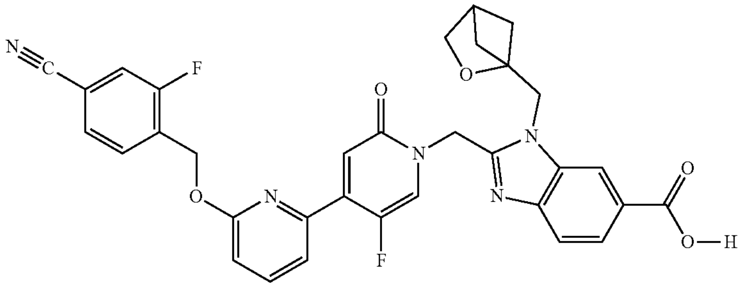
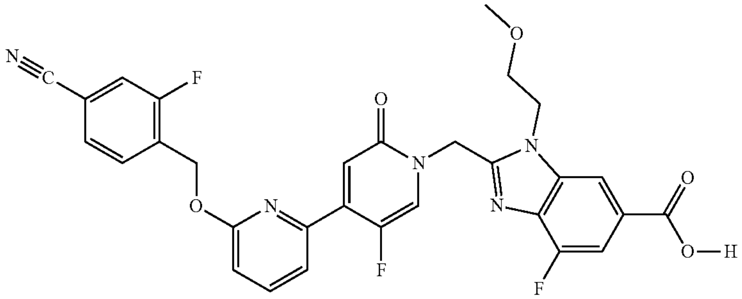
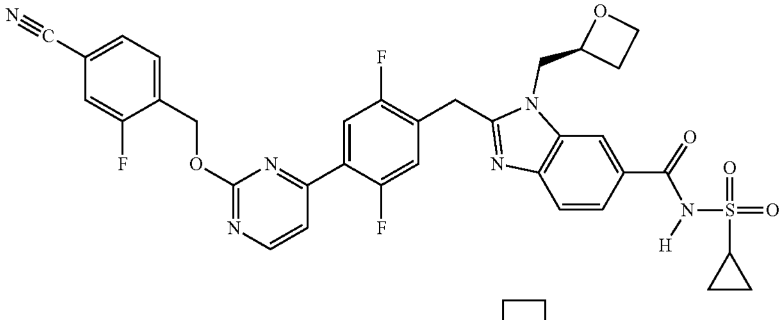
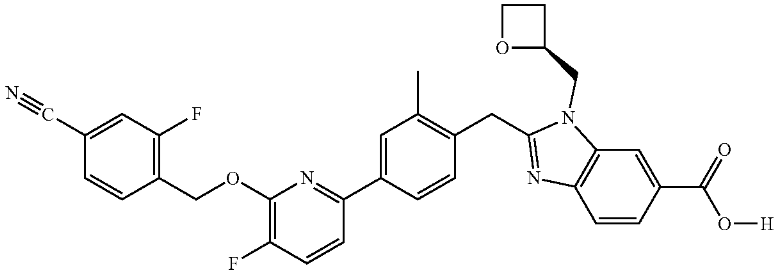

-continued
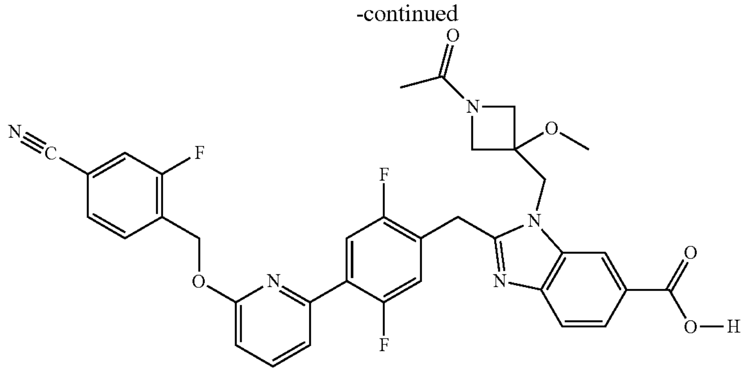
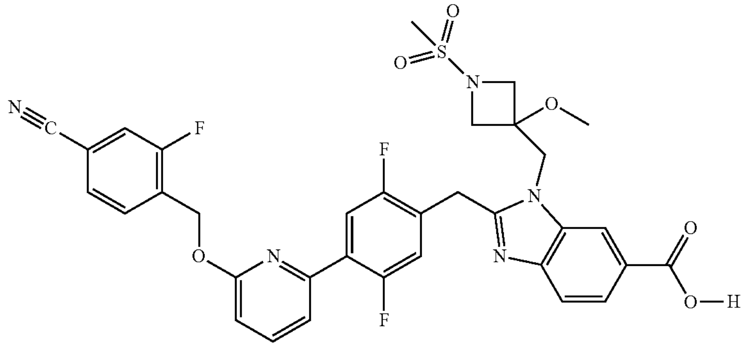
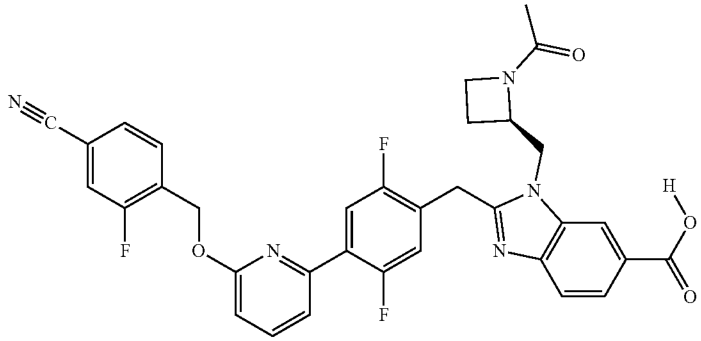
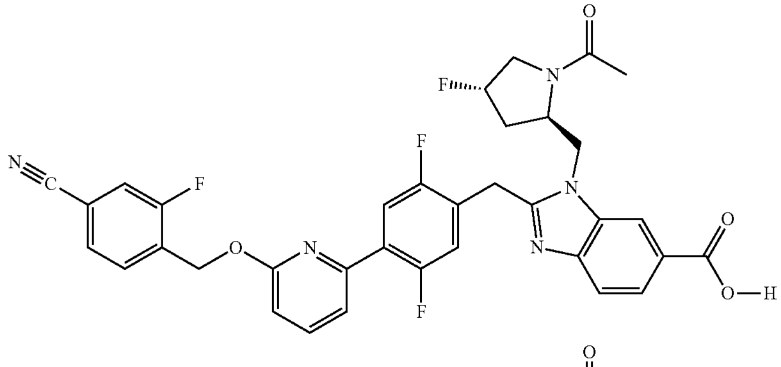
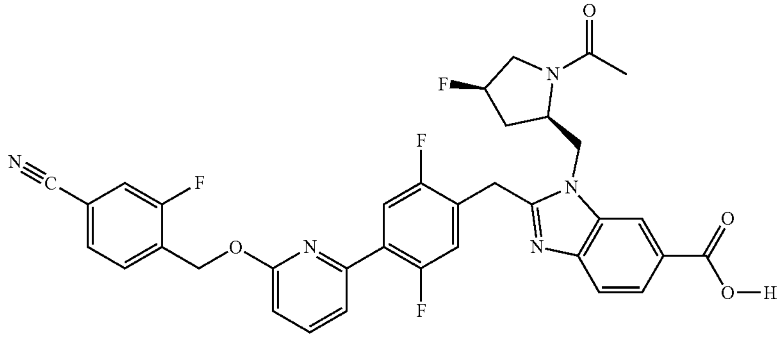

-continued
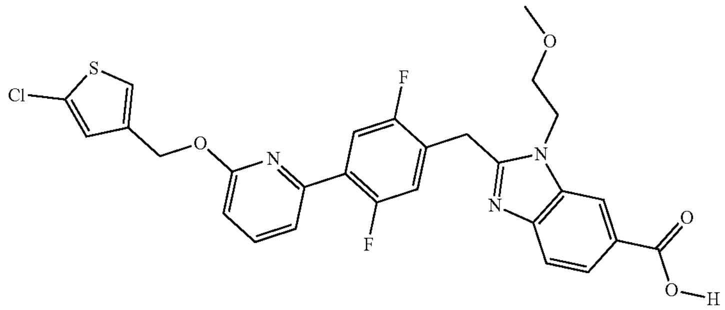
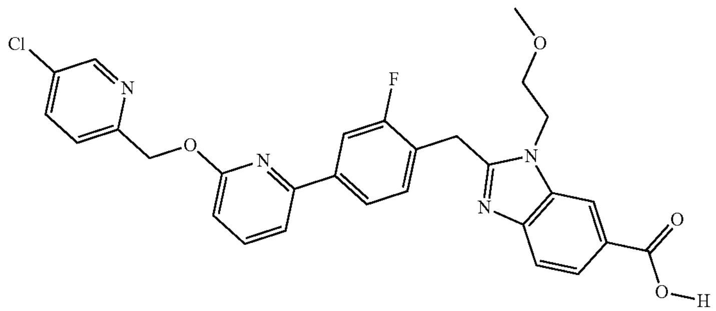
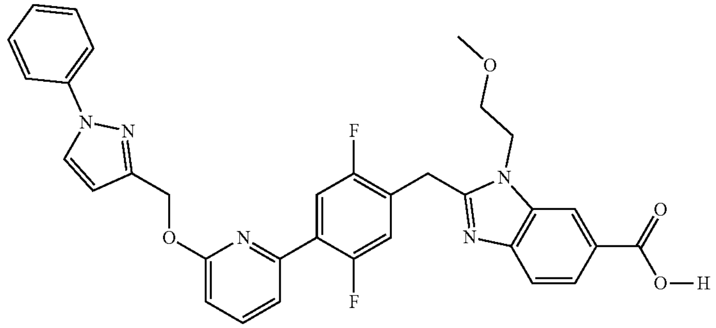
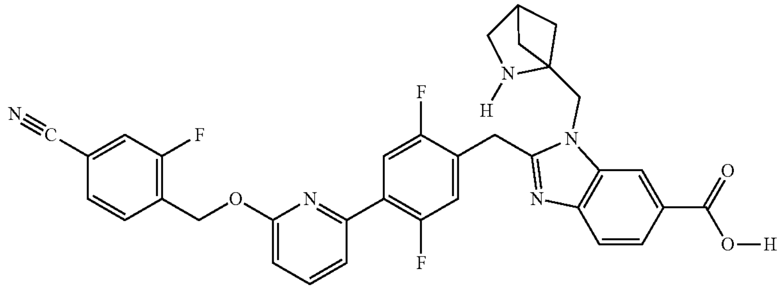
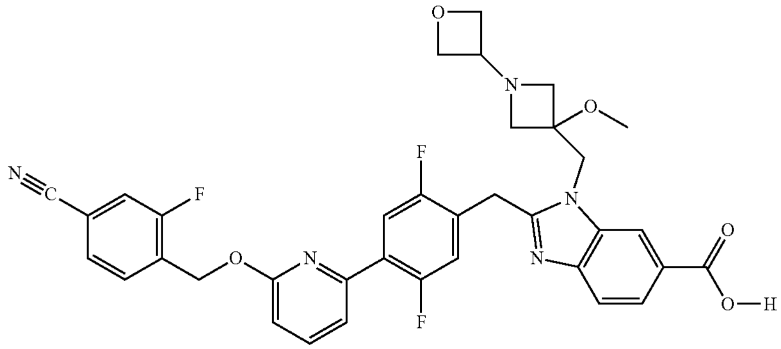

-continued
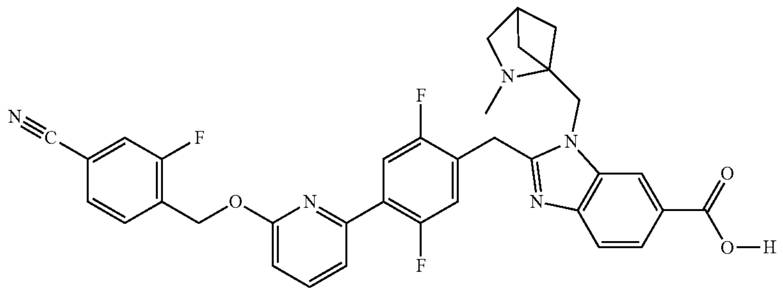
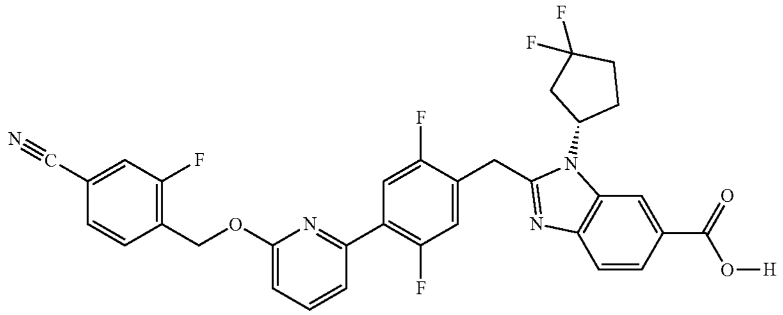
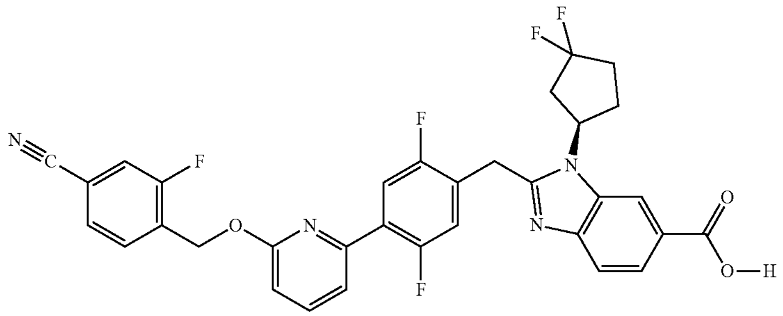
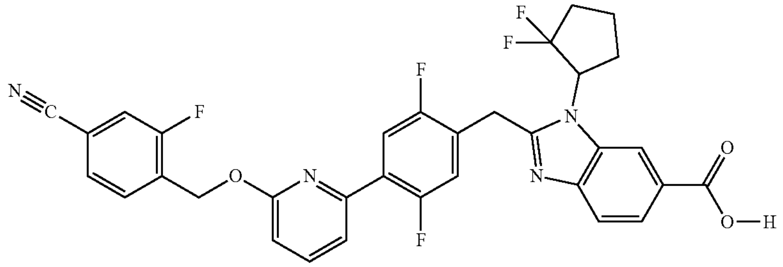
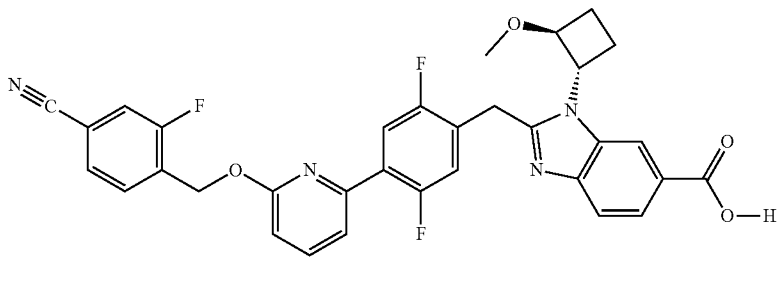

-continued
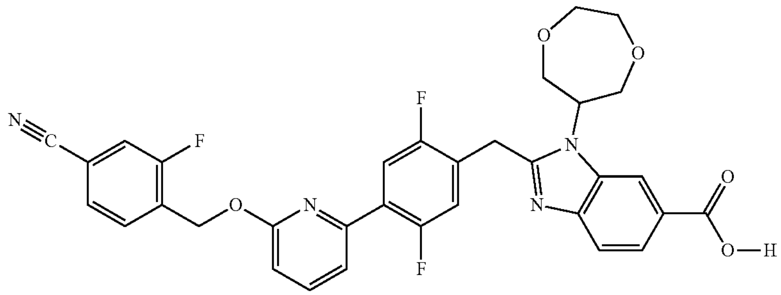
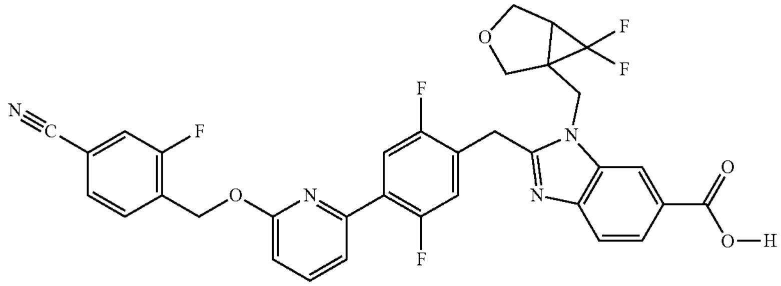
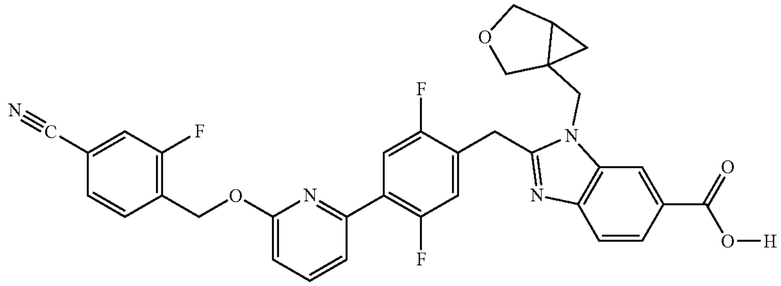
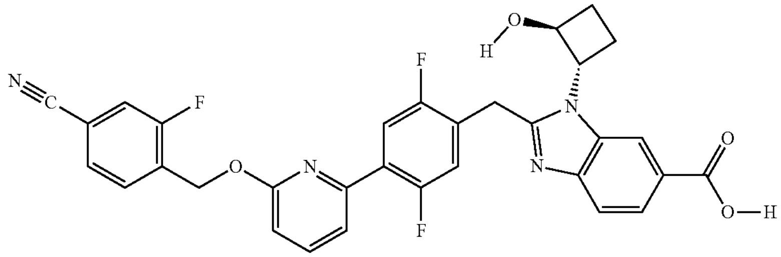
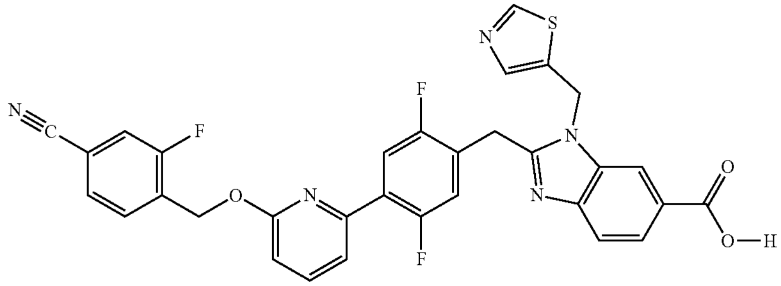
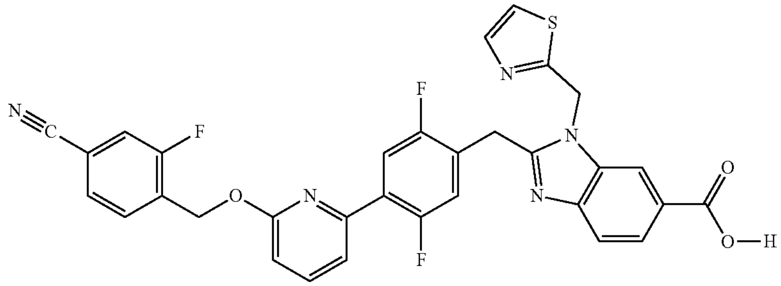

-continued
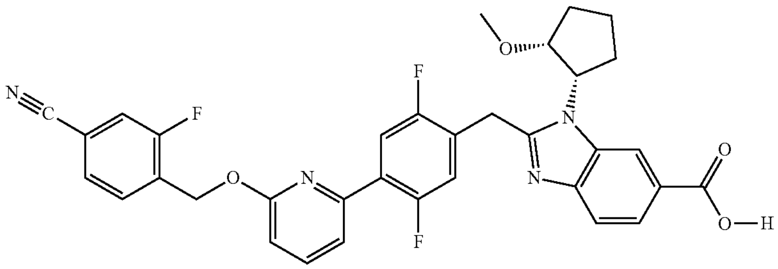
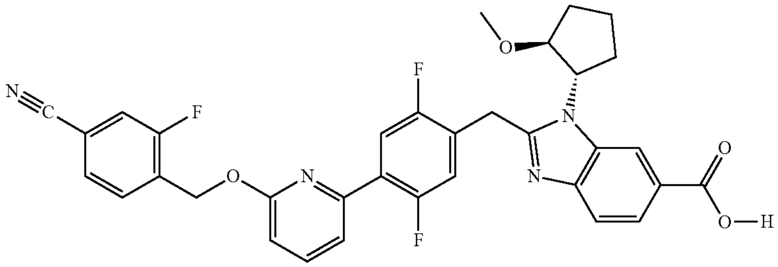
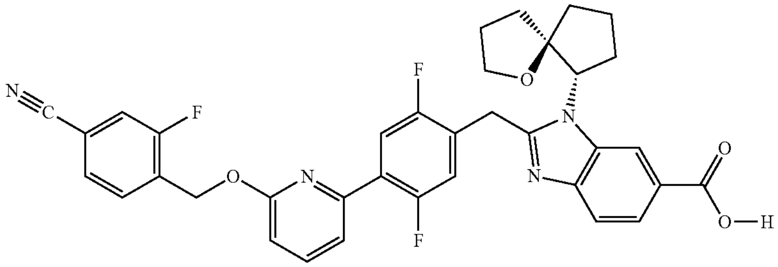
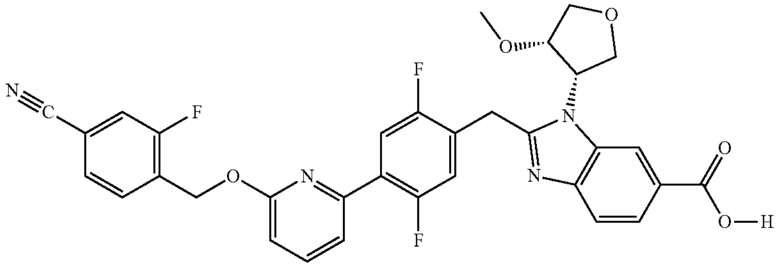
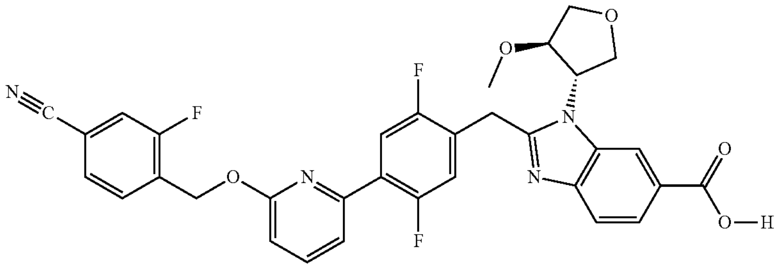
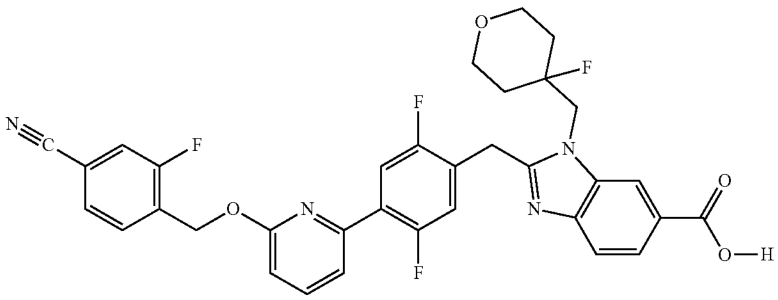

-continued
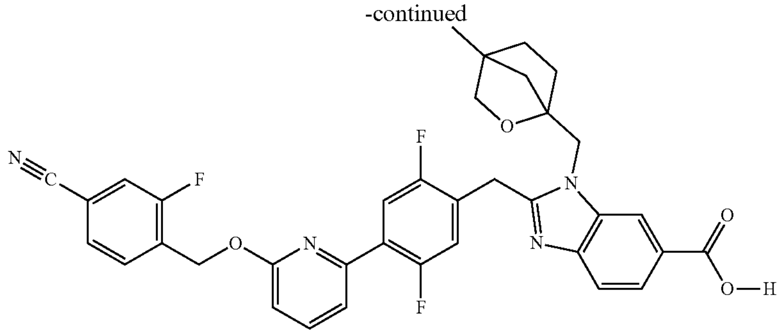
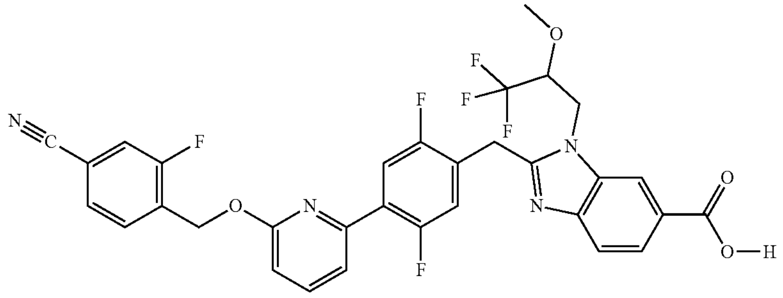
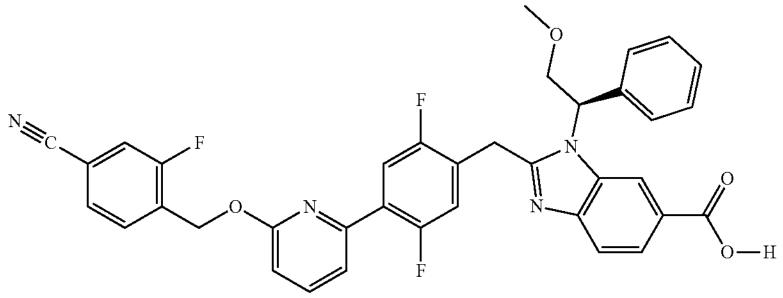
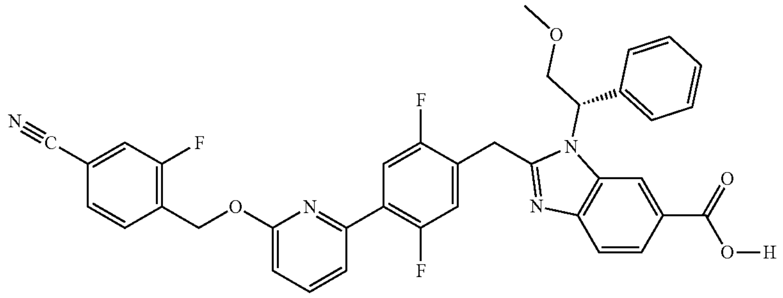
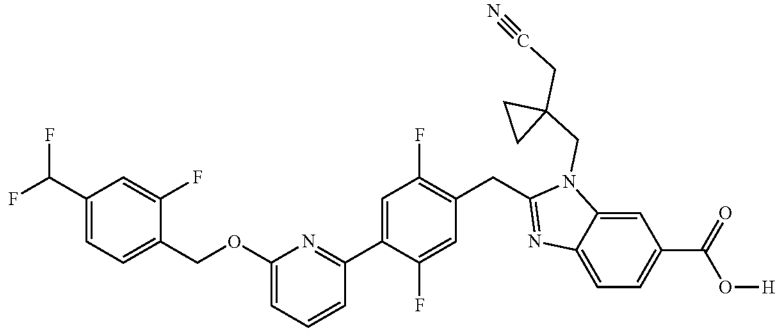

-continued
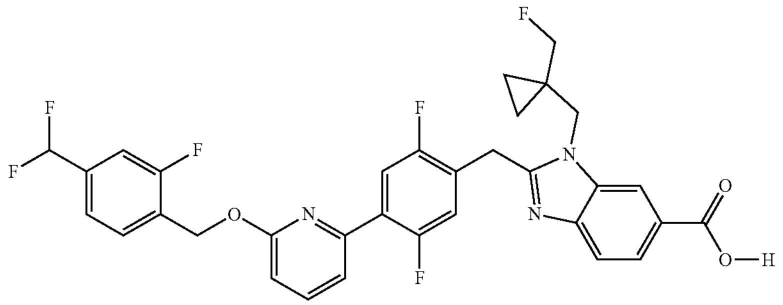
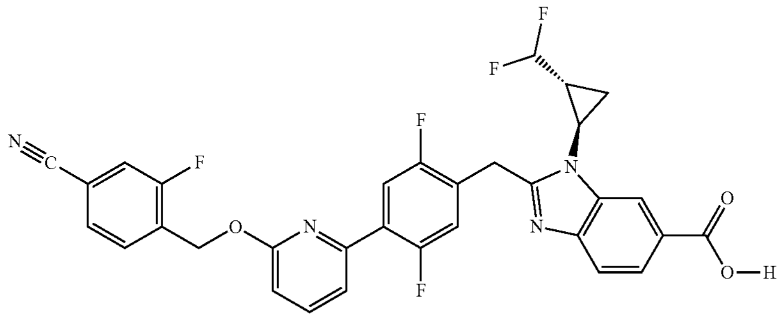
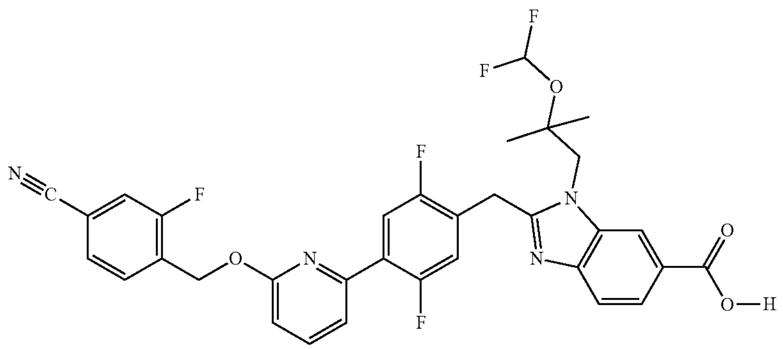
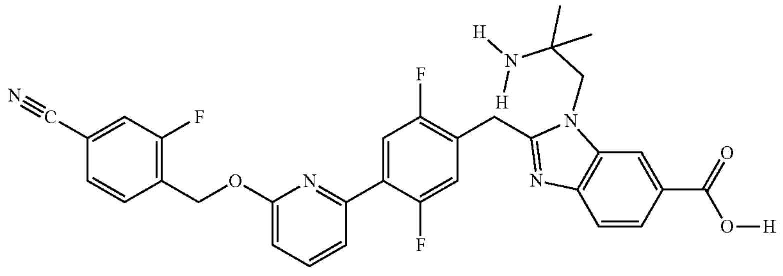
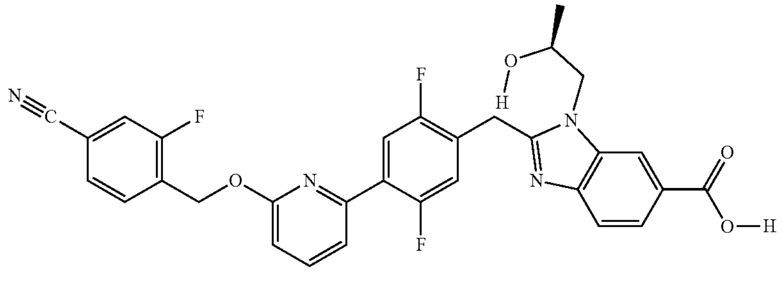

-continued
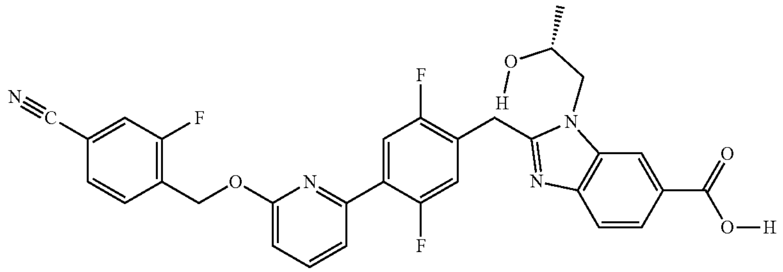
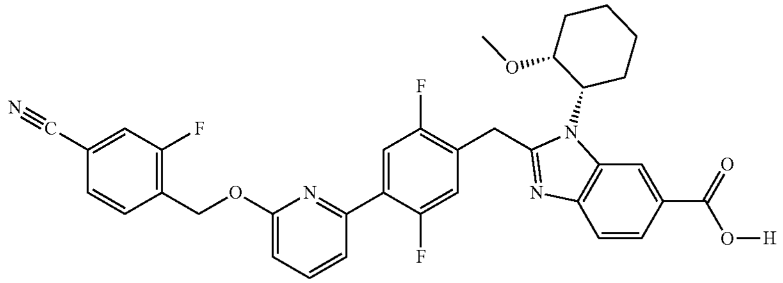
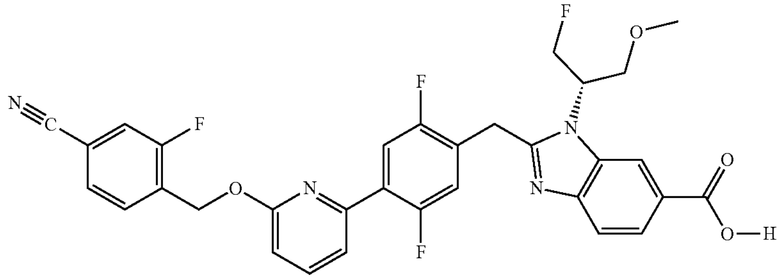
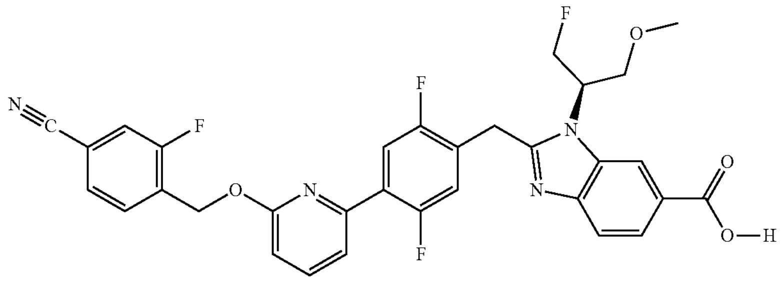
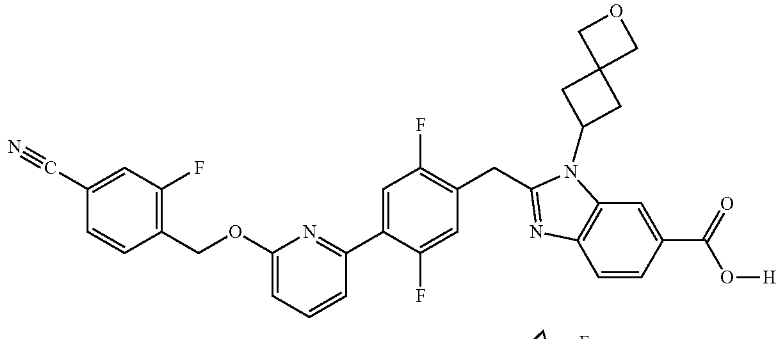
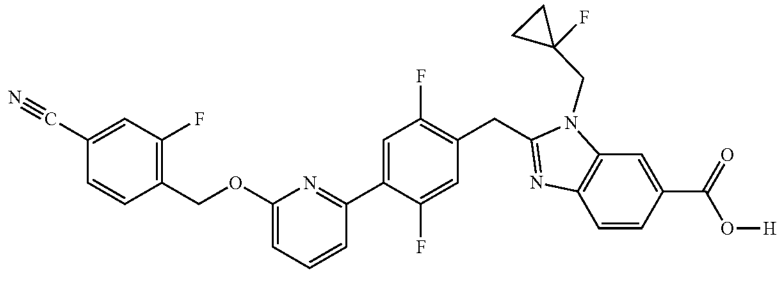

-continued
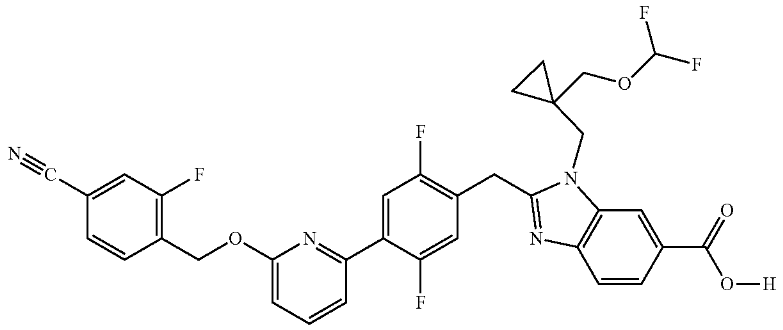
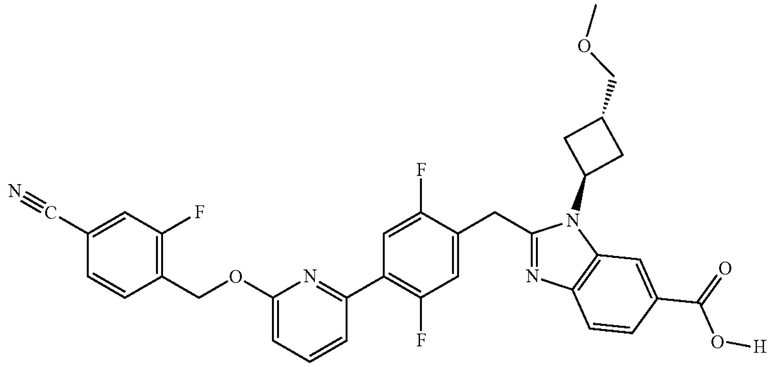
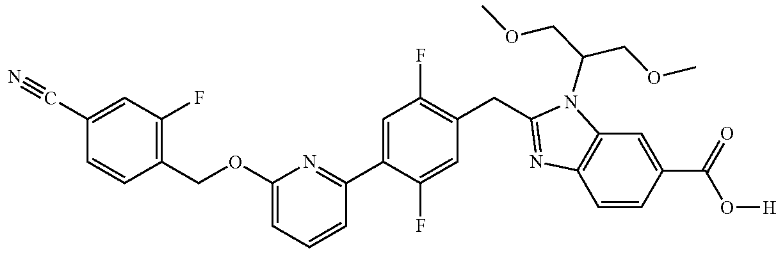
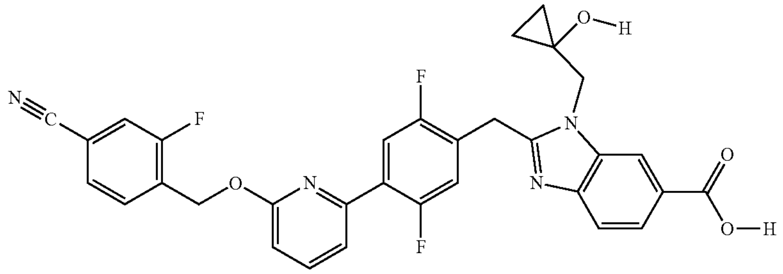
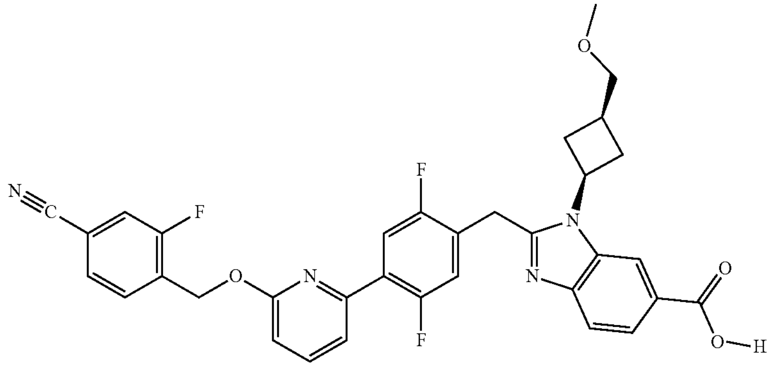

-continued
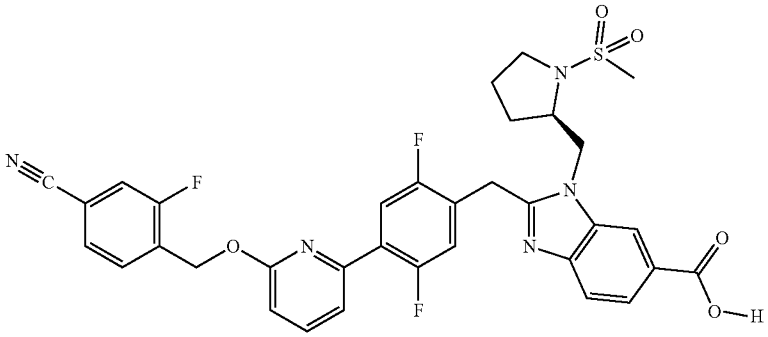
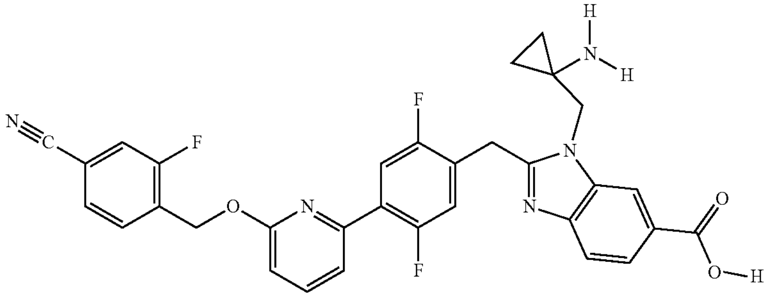
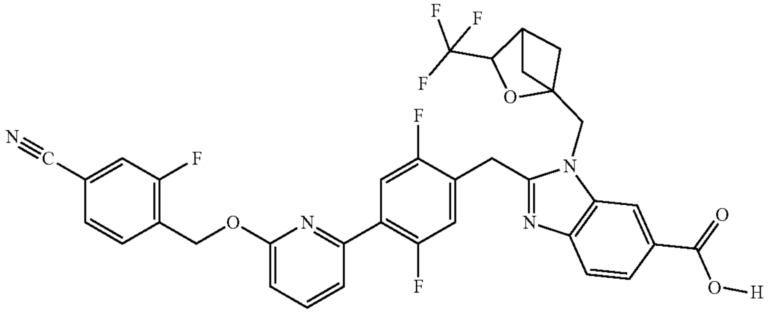
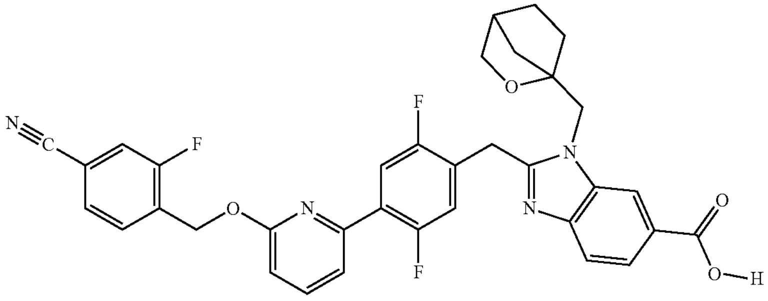
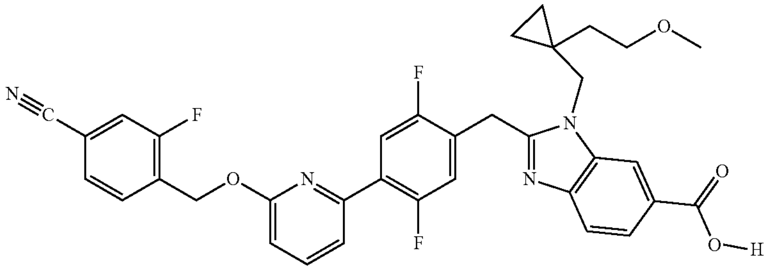

-continued
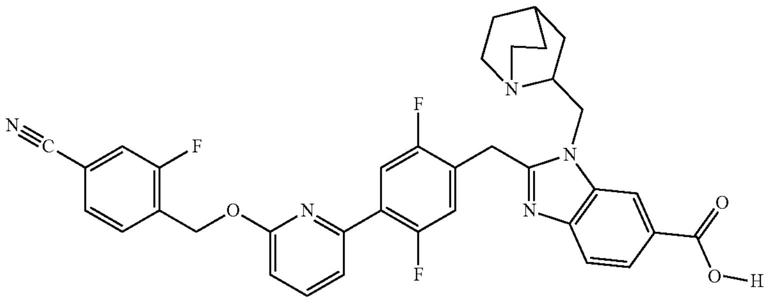
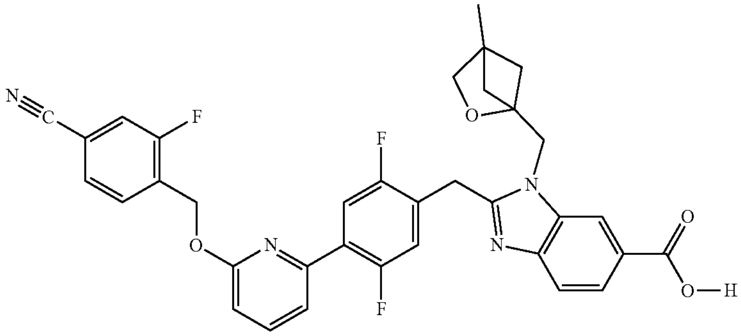
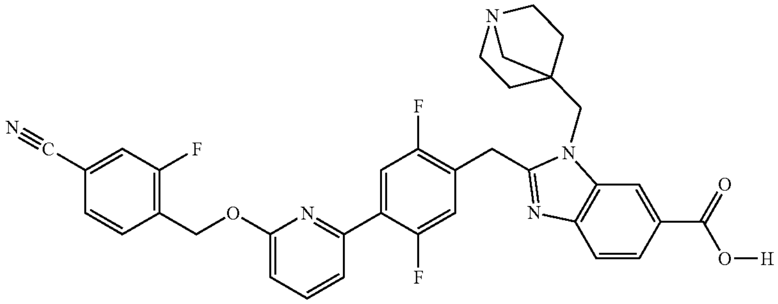
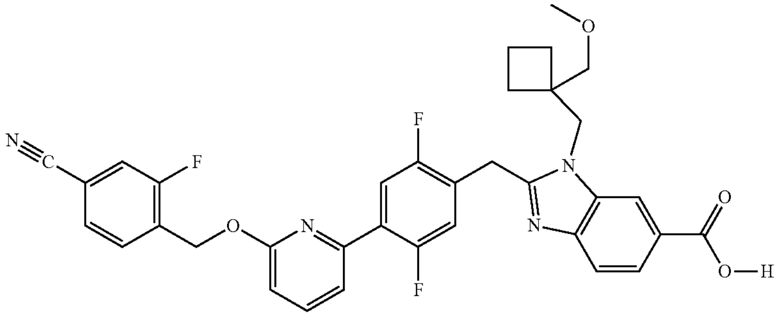
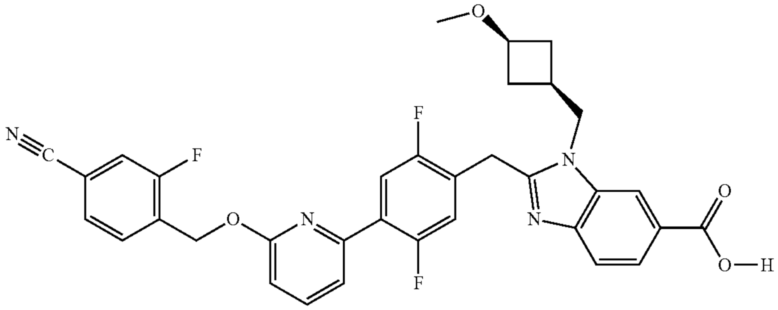

-continued
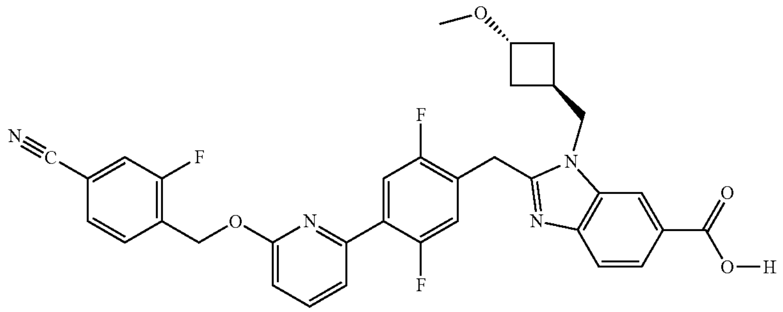
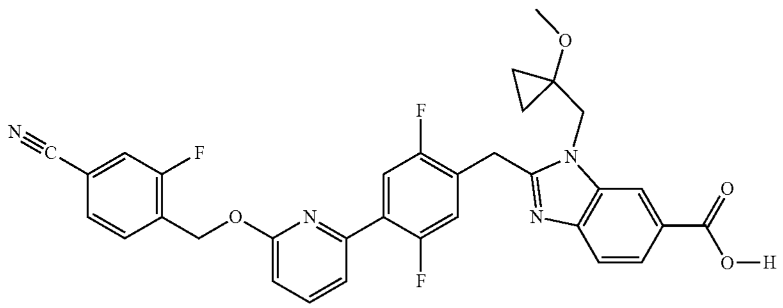
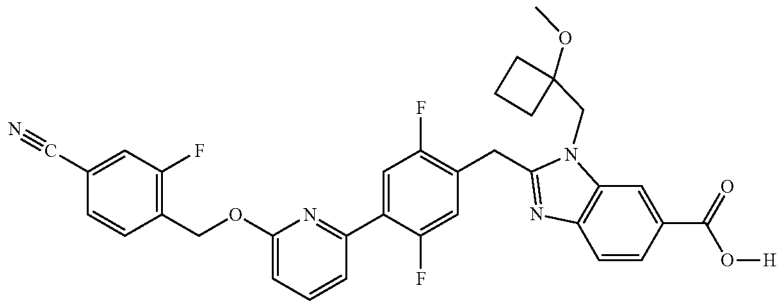
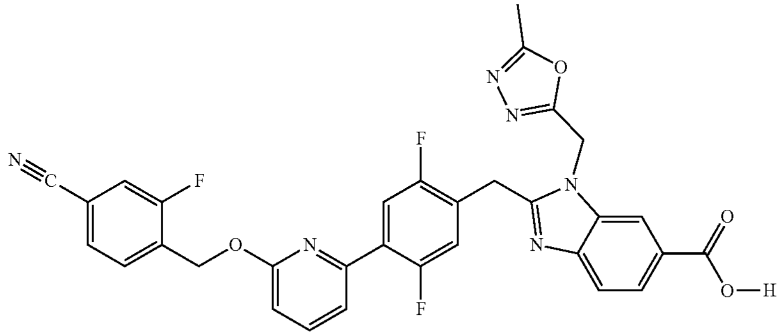
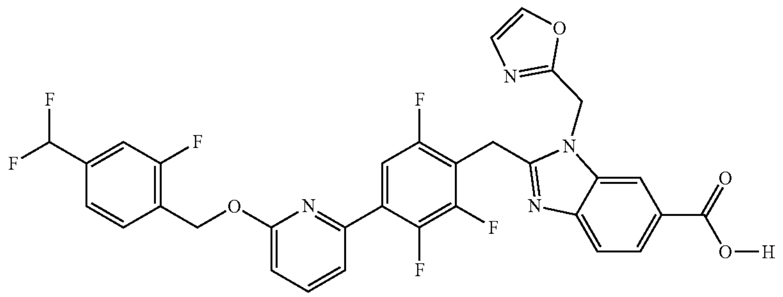

-continued
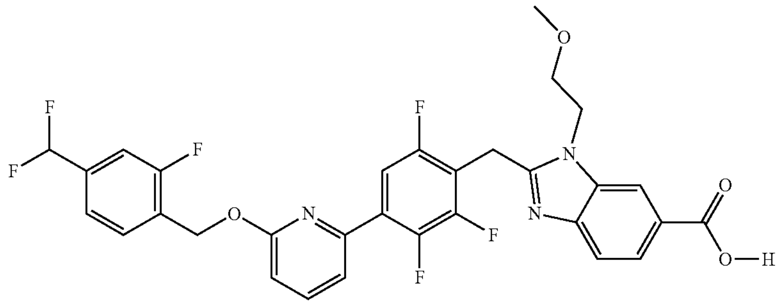
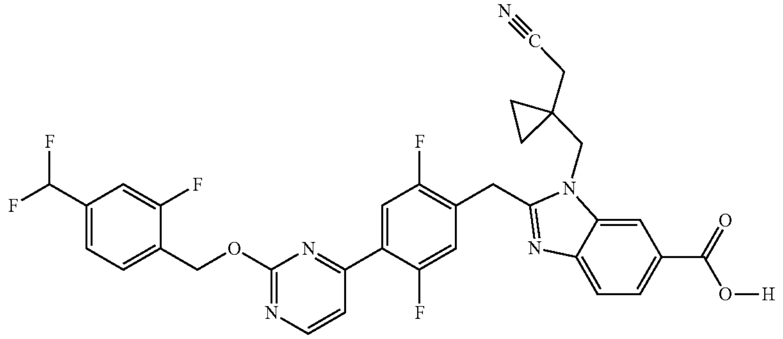
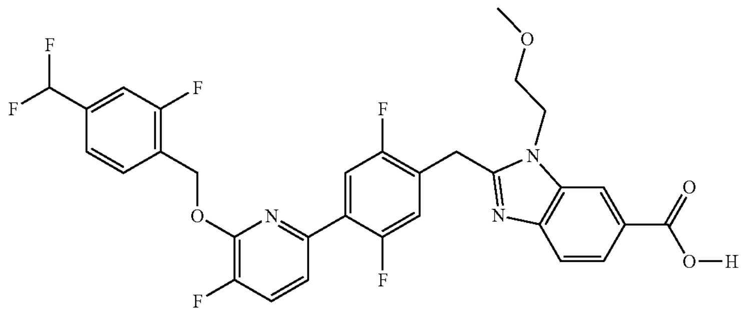
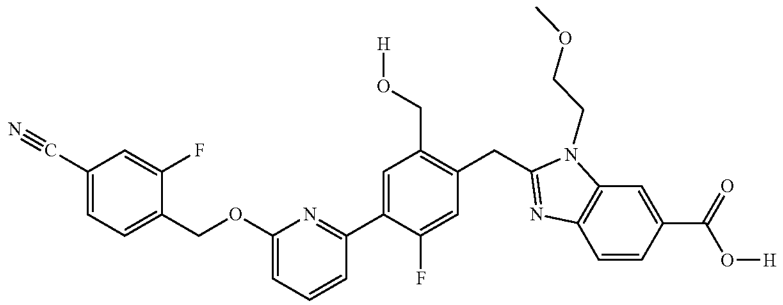
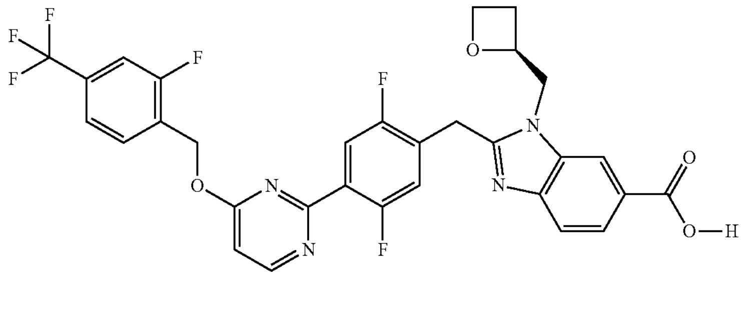

-continued
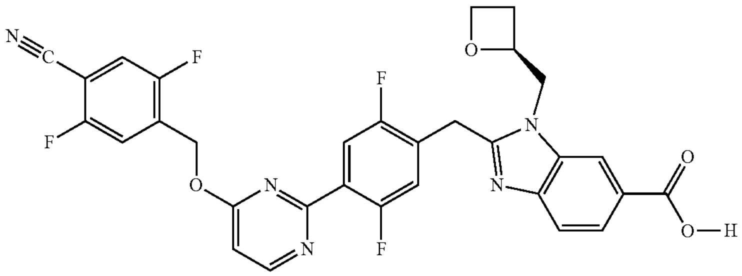
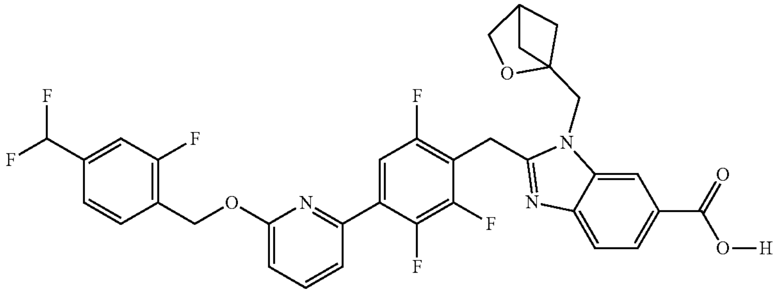
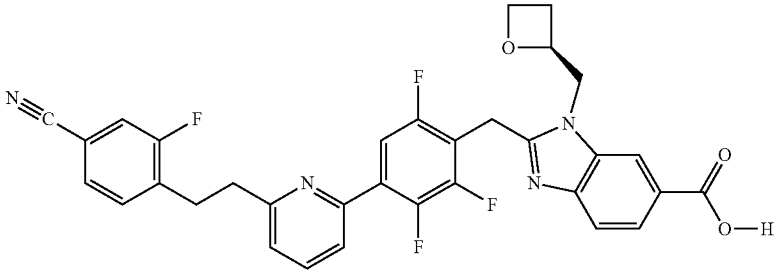
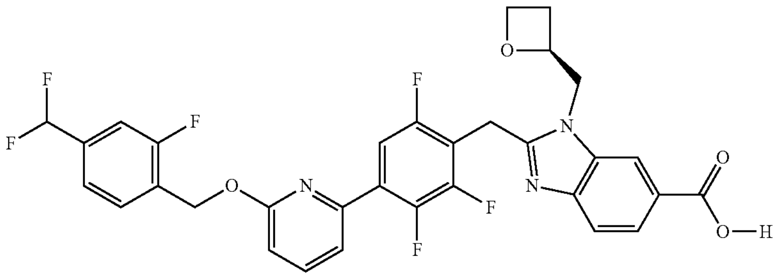
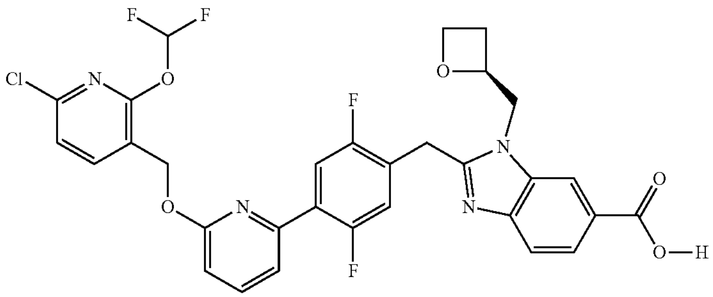
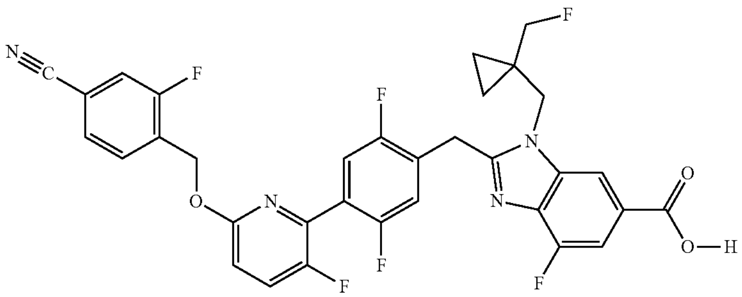

-continued
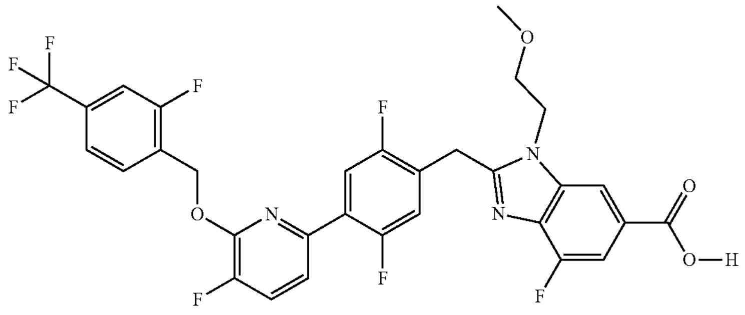
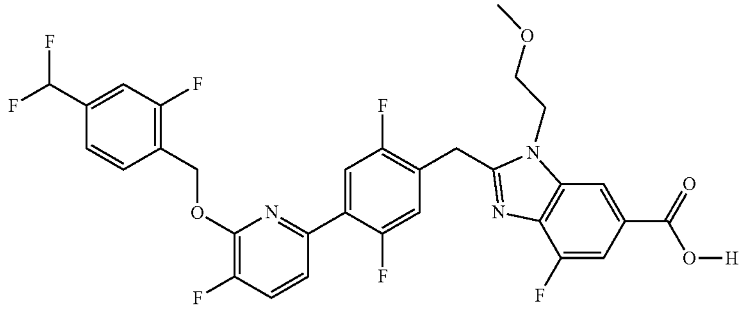
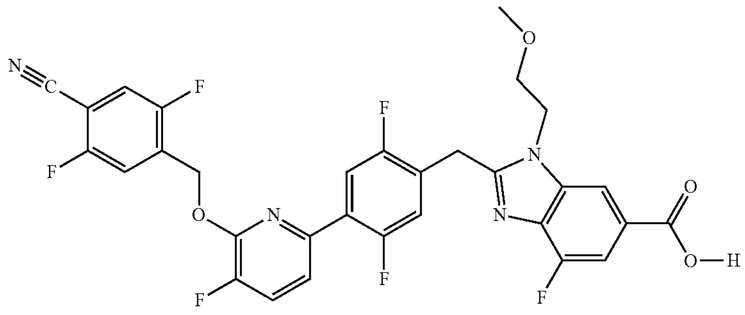
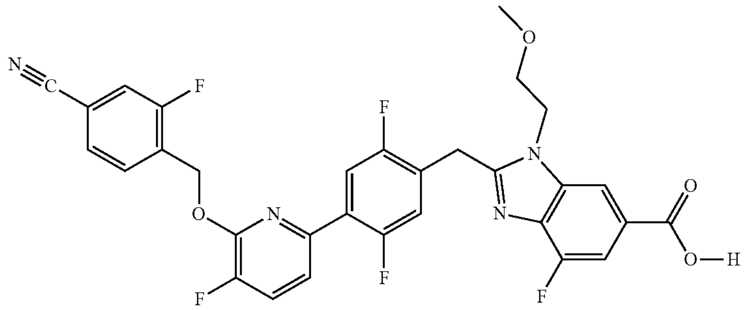
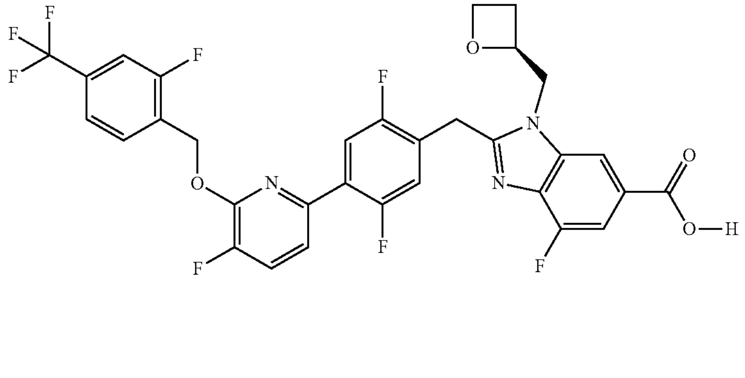

-continued
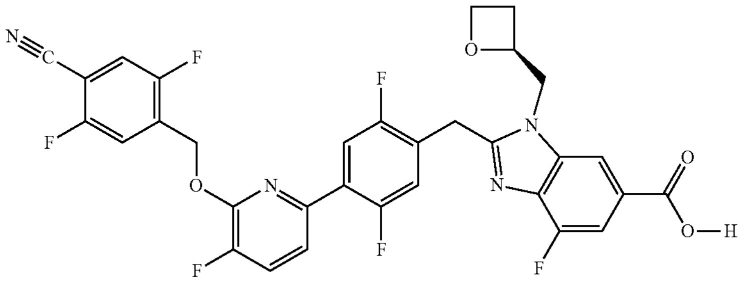
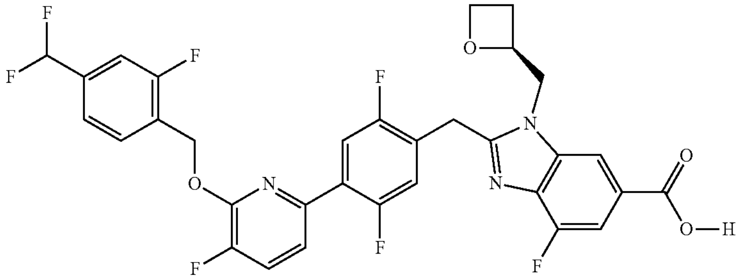
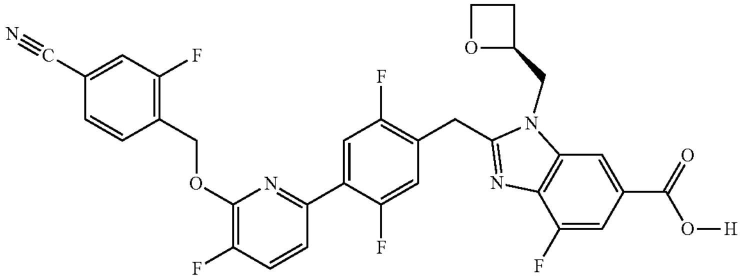
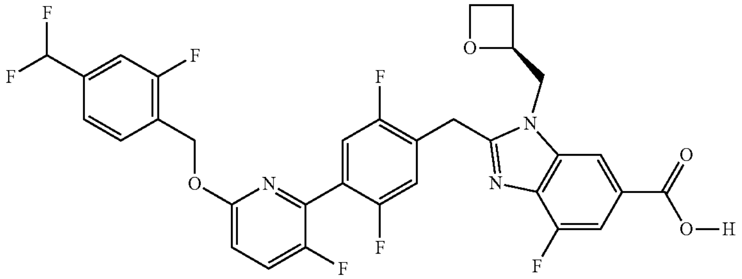
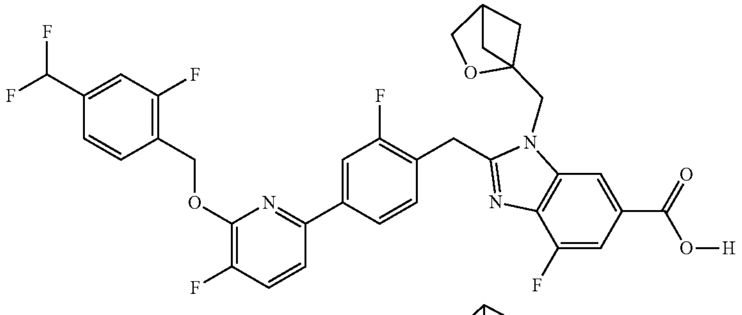
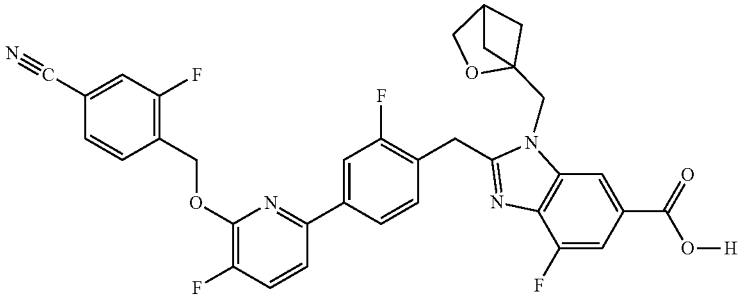

-continued
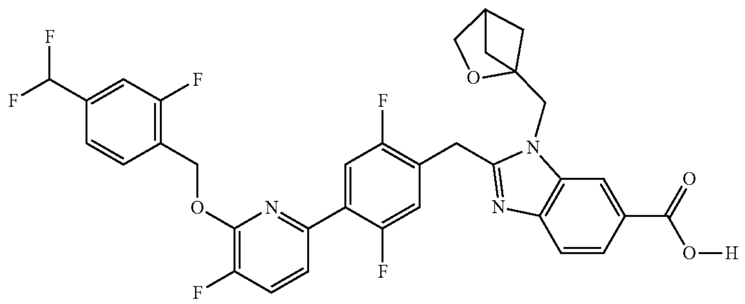
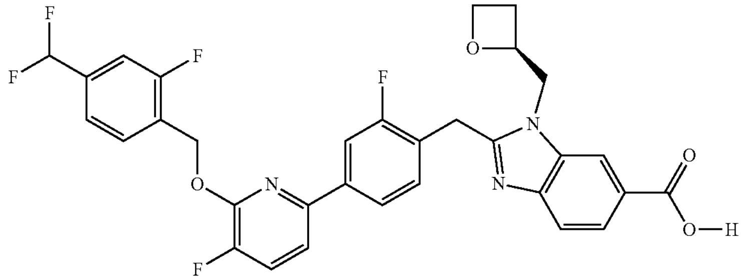
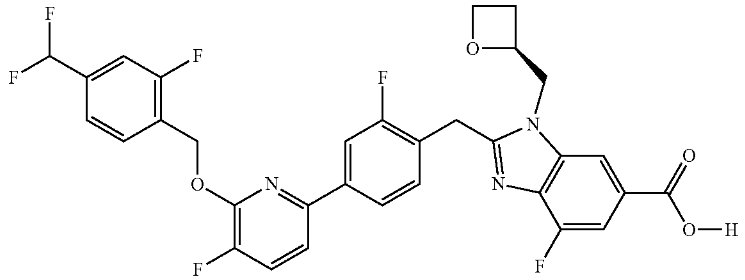 [SMILES: O=C(O)c1cc(F)c2nc(Cc3ccc(-c4ccc(F)c(OCc5ccc(C(F)F)cc5F)n4)cc3F)n(C[C@@H]3CCO3)c2c1]
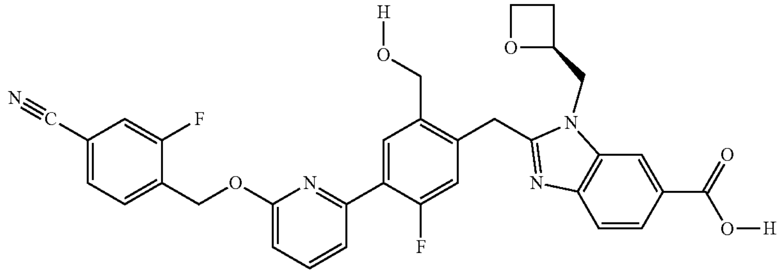
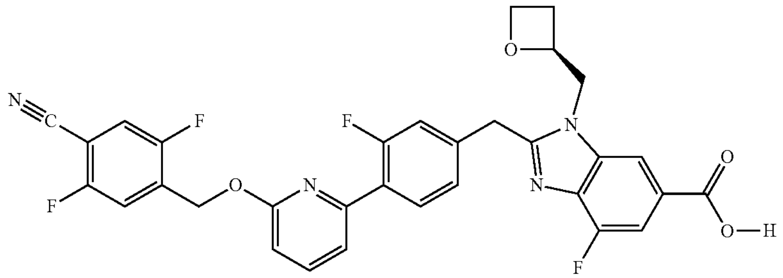
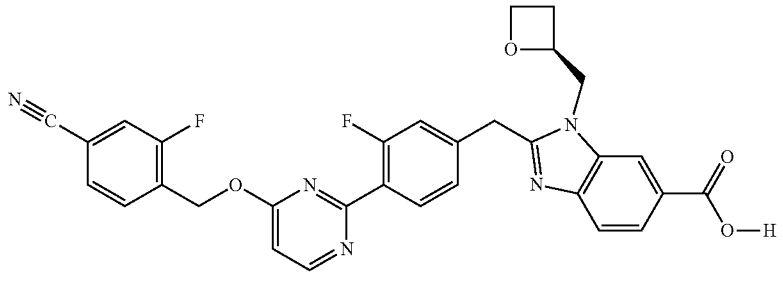

-continued
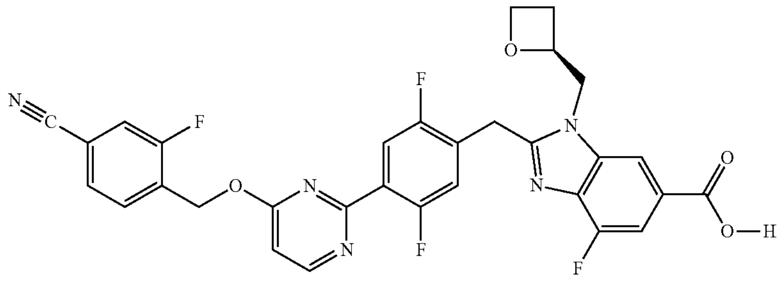
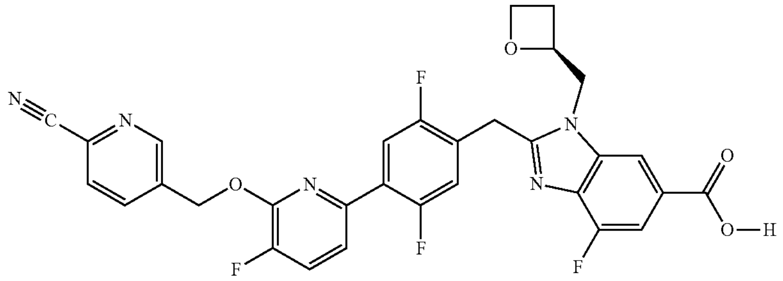
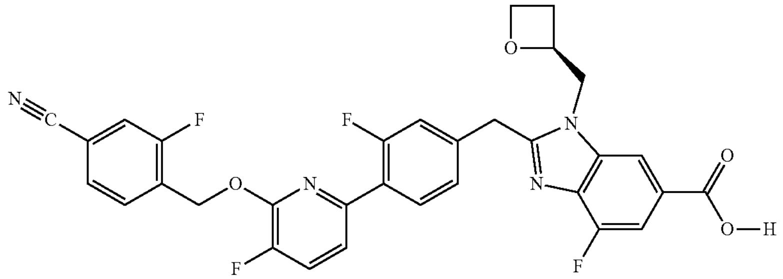
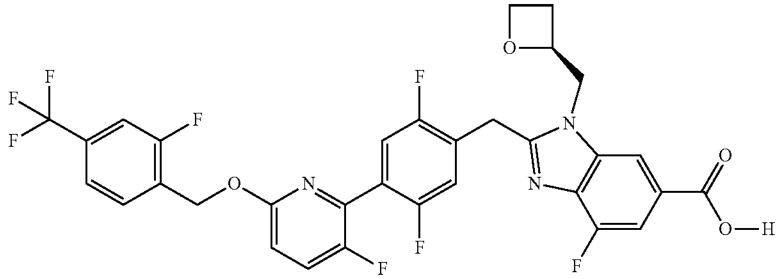
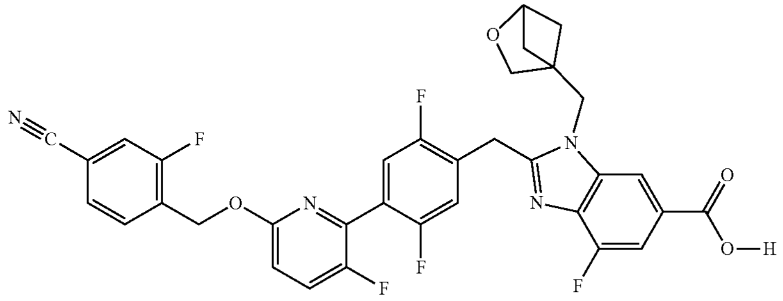
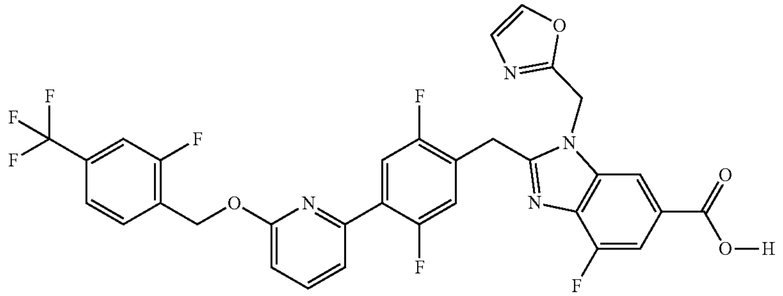

-continued
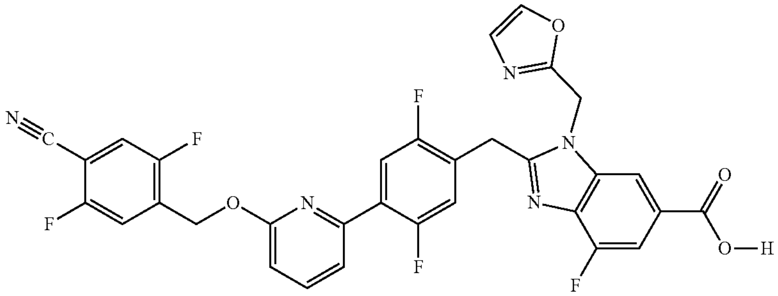
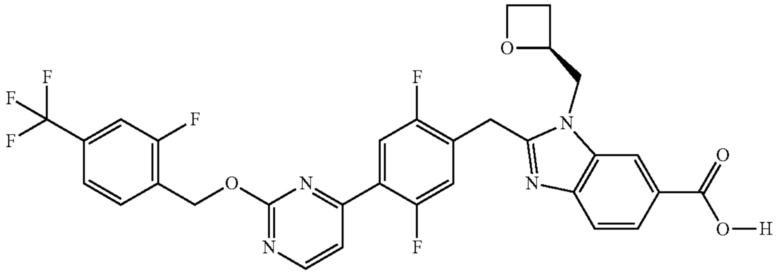
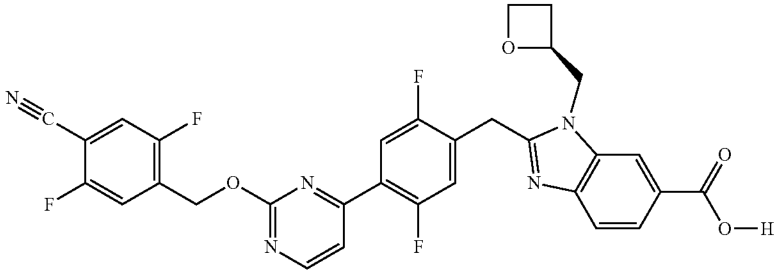
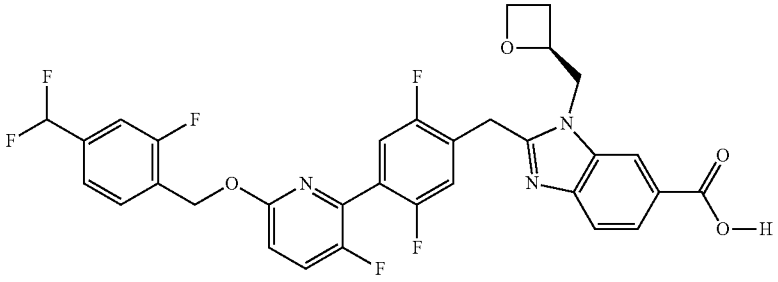
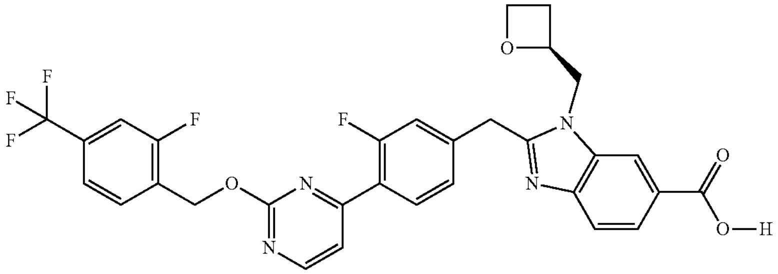
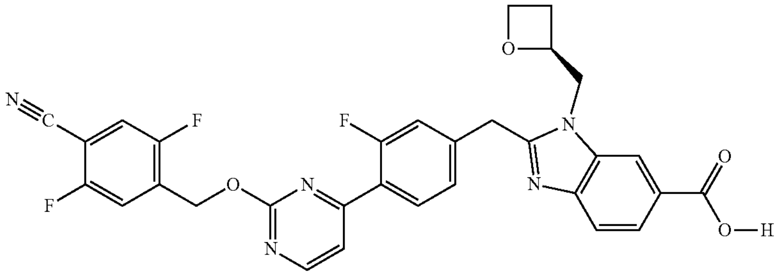

-continued
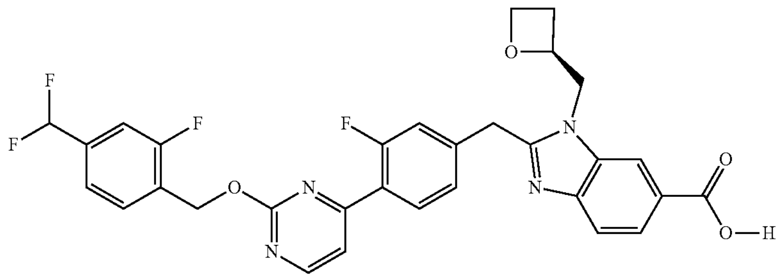 [SMILES: O=C(O)c1ccc2nc(Cc3ccc(-c4ccnc(OCc5ccc(C(F)F)cc5F)n4)c(F)c3)n(C[C@@H]3CCO3)c2c1]
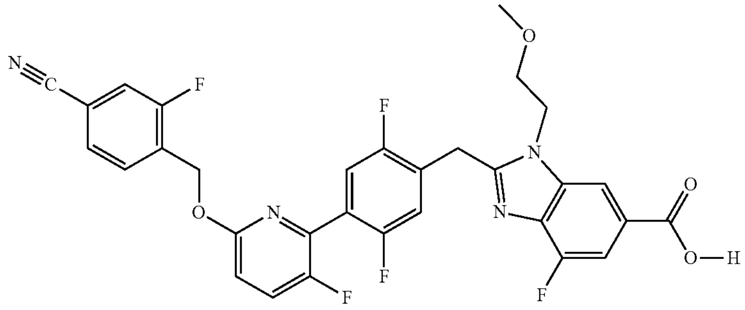
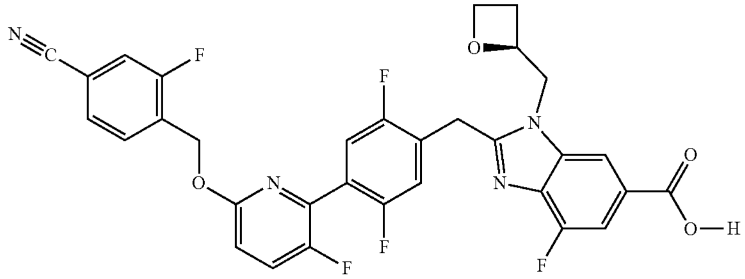
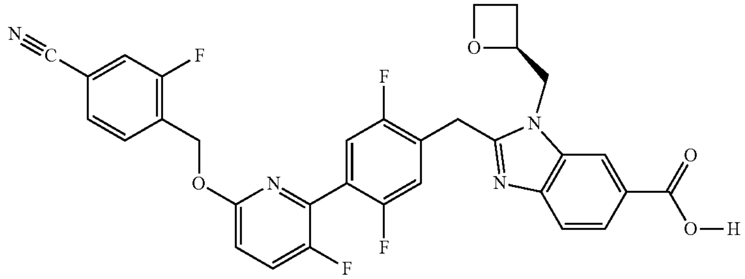
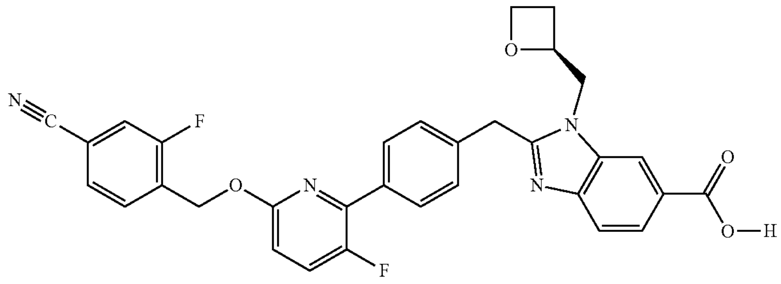
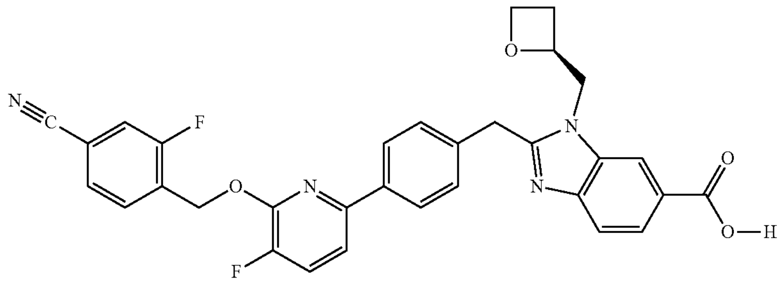

-continued
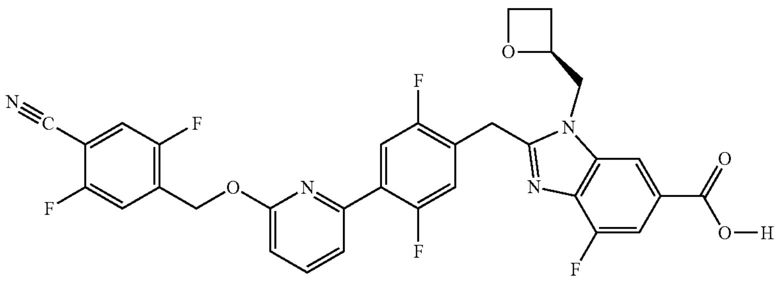
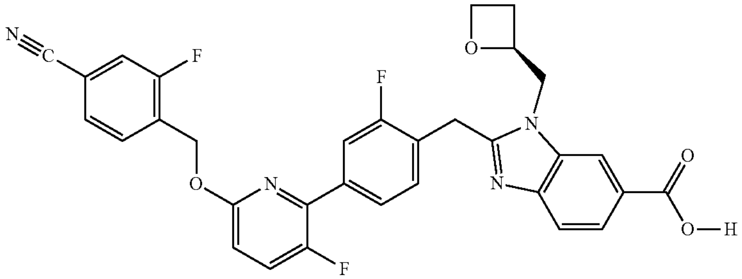
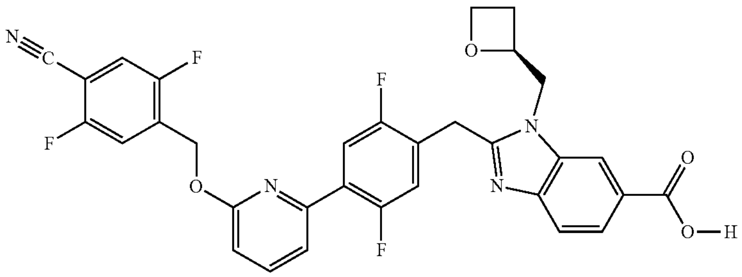
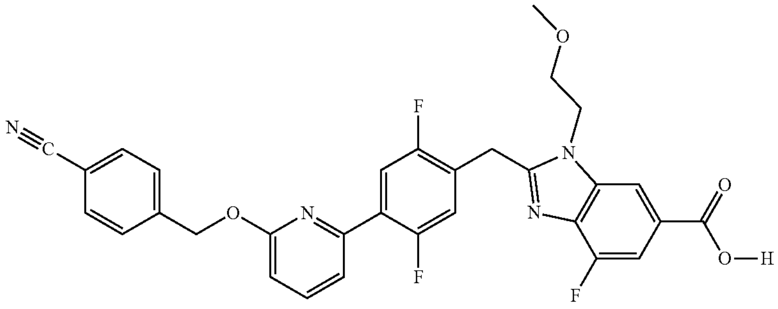
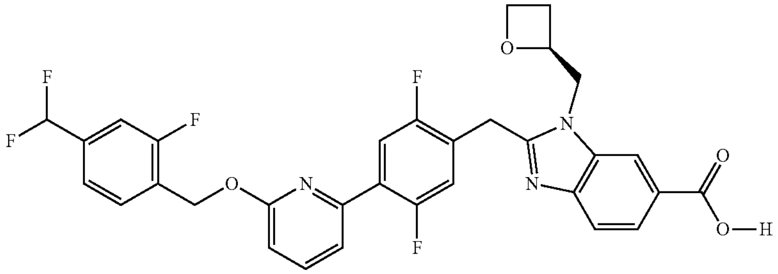
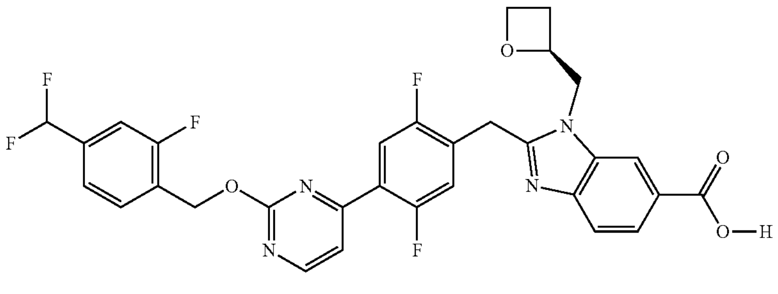

-continued
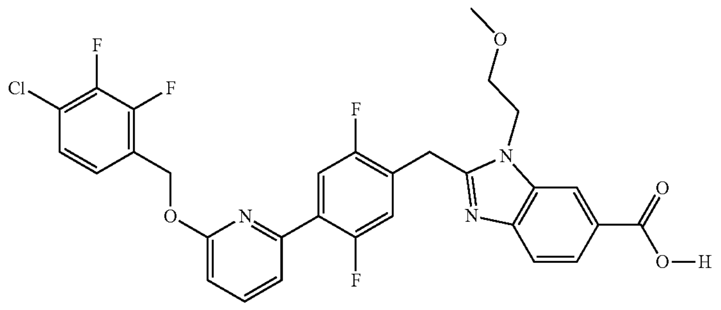
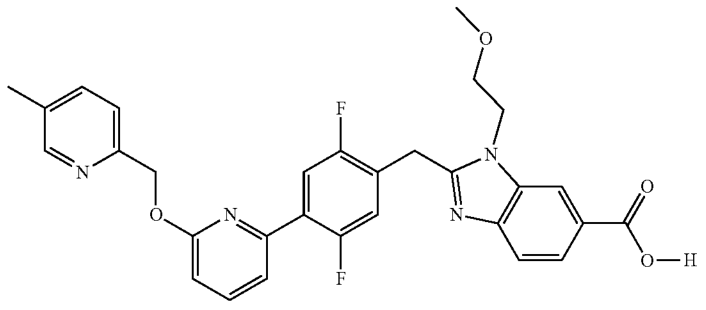
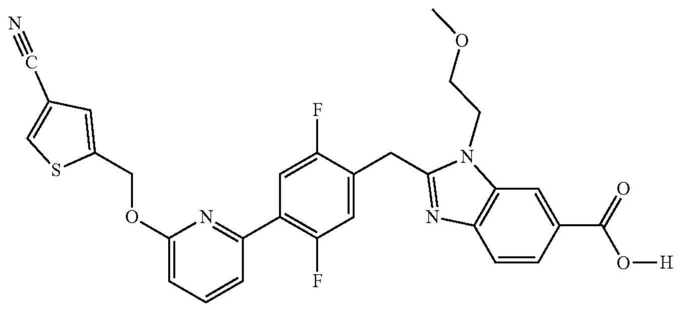
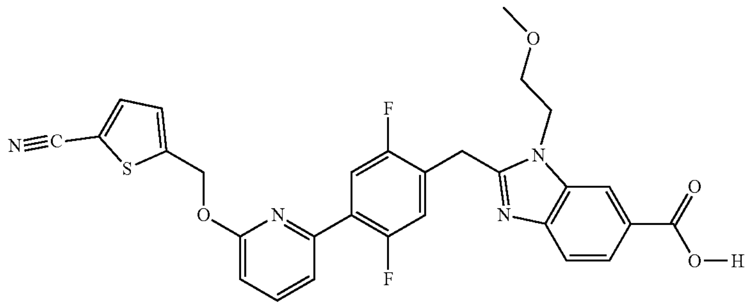
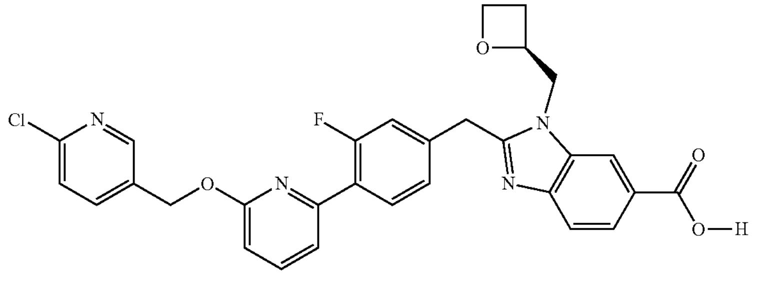 [SMILES: O=C(O)c1ccc2nc(Cc3ccc(-c4cccc(OCc5ccc(Cl)nc5)n4)c(F)c3)n(C[C@@H]3CCO3)c2c1]

-continued
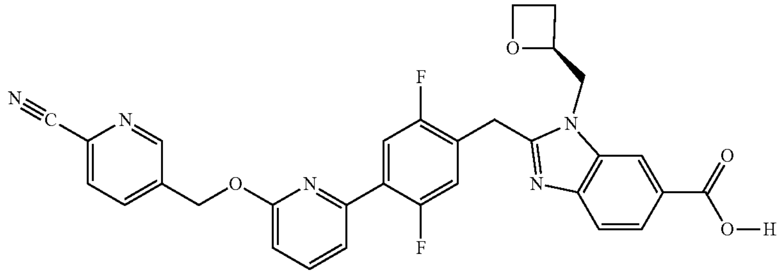
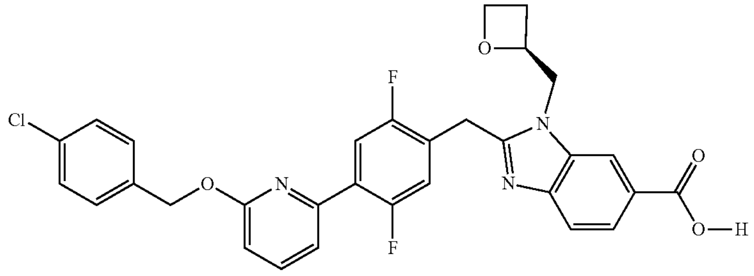
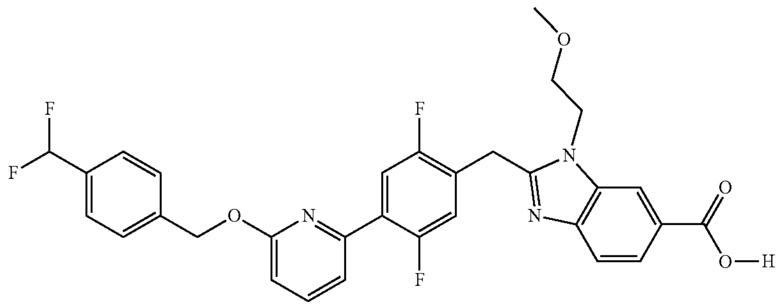
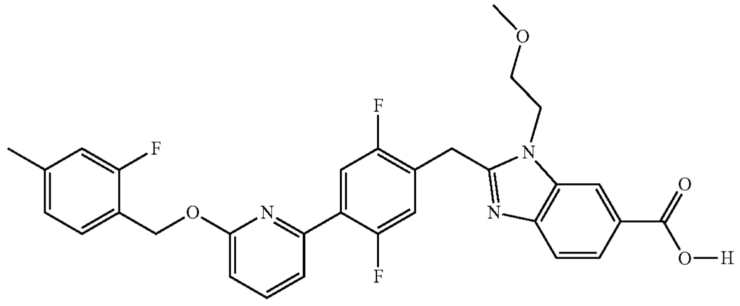
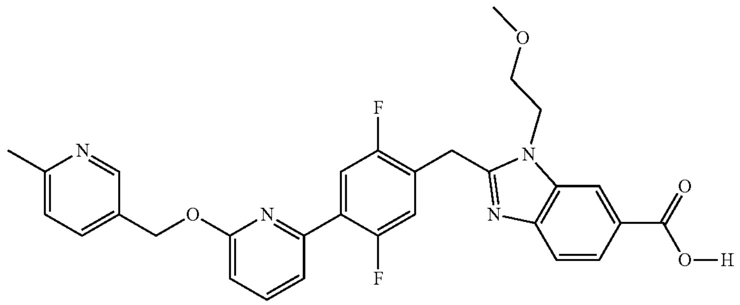

-continued
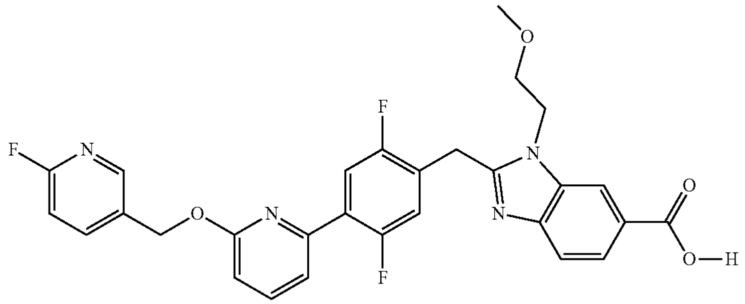
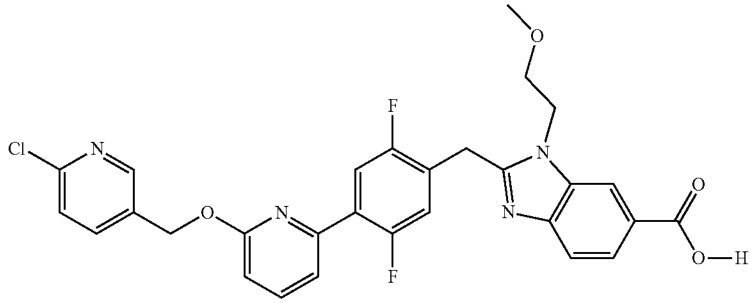
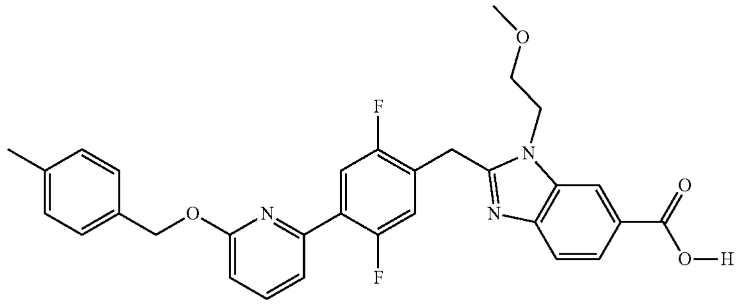
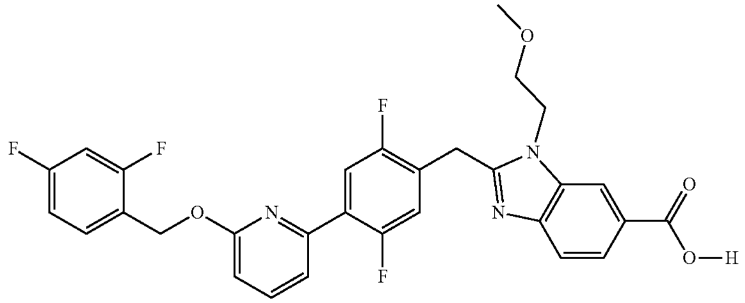
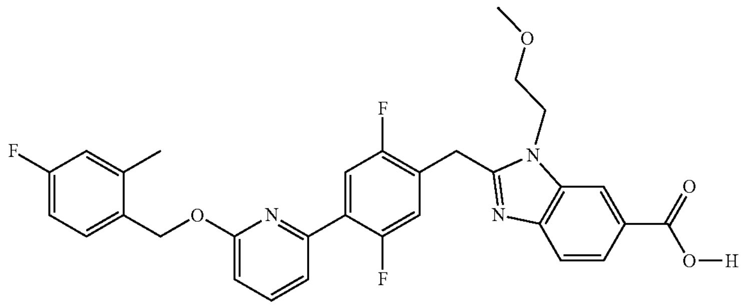

-continued
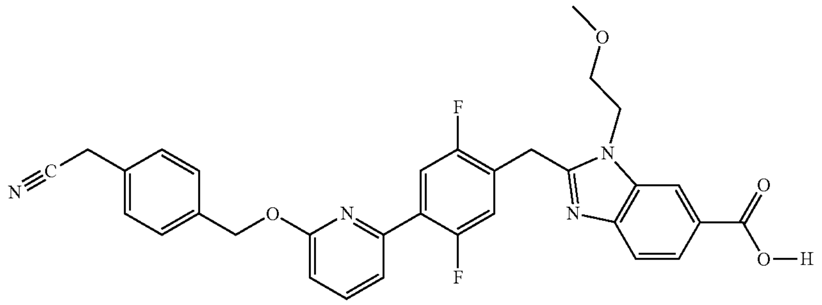
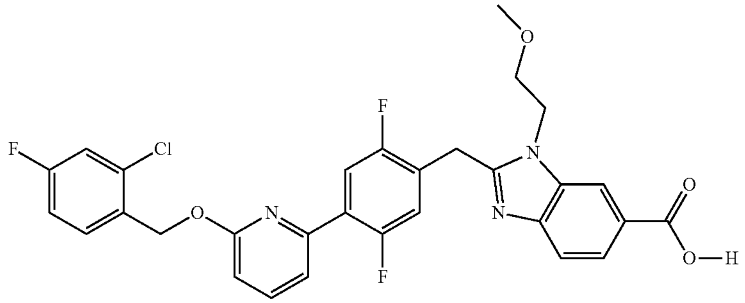
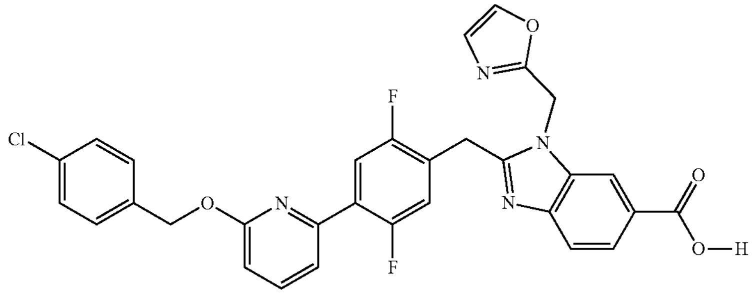
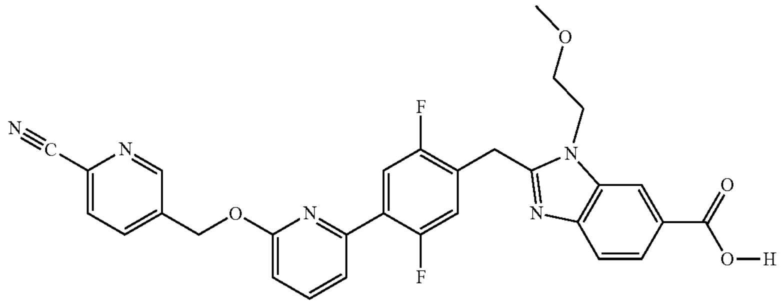
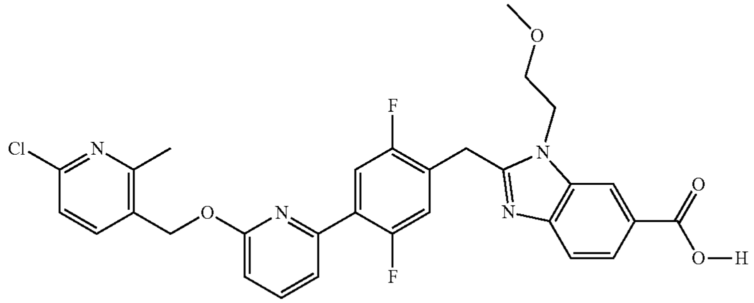

-continued
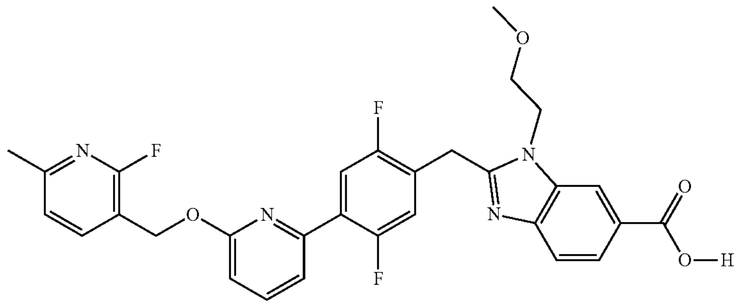 [SMILES: COCCn1c(Cc2cc(F)c(-c3cccc(OCc4ccc(C)nc4F)n3)cc2F)nc2ccc(C(=O)O)cc21]
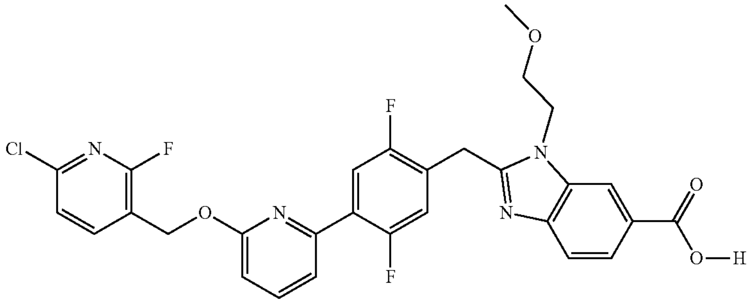
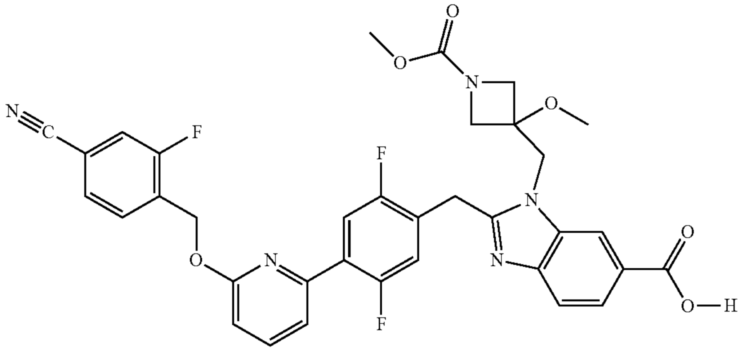
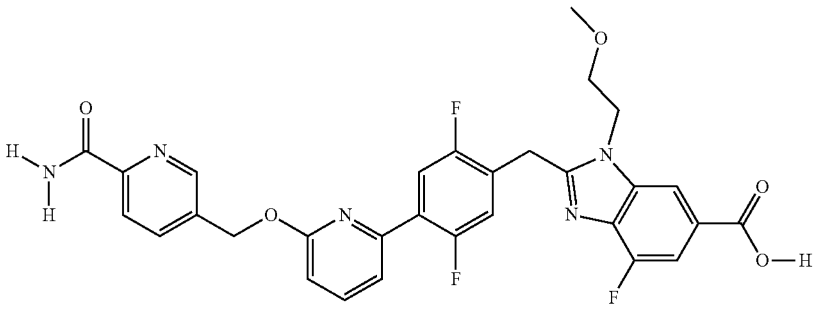
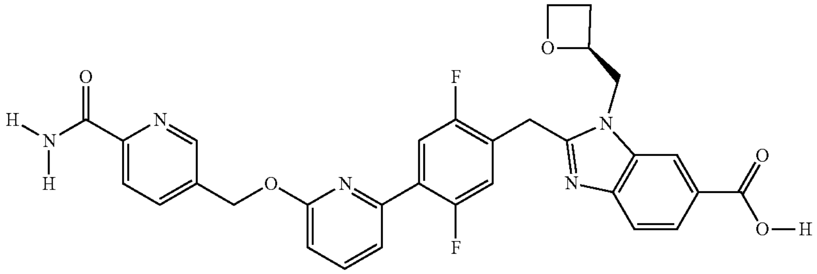

-continued
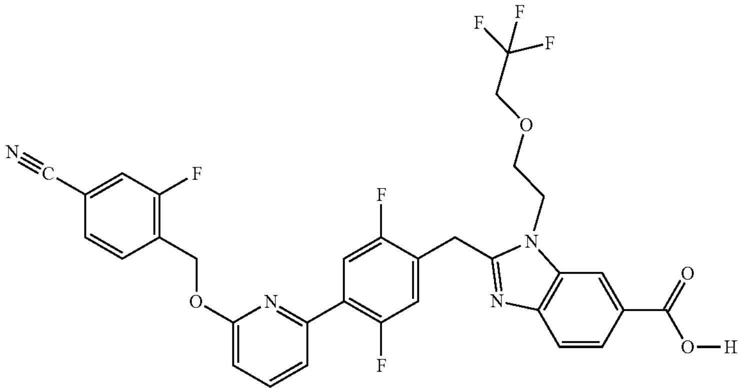
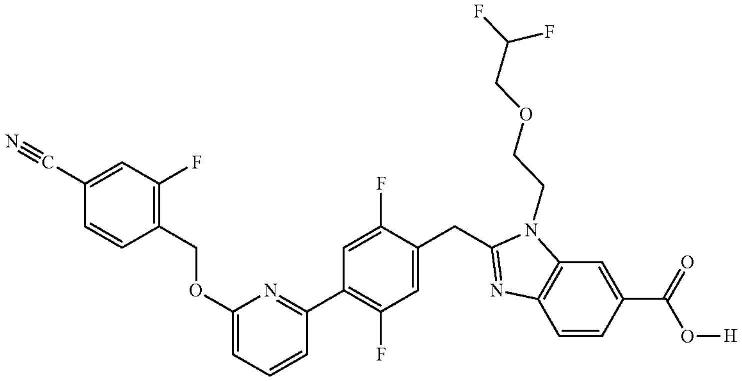
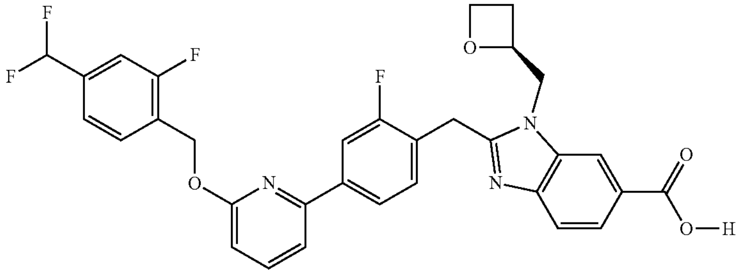
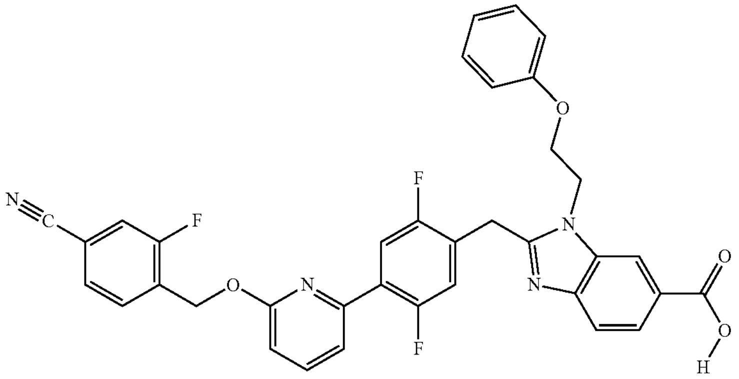
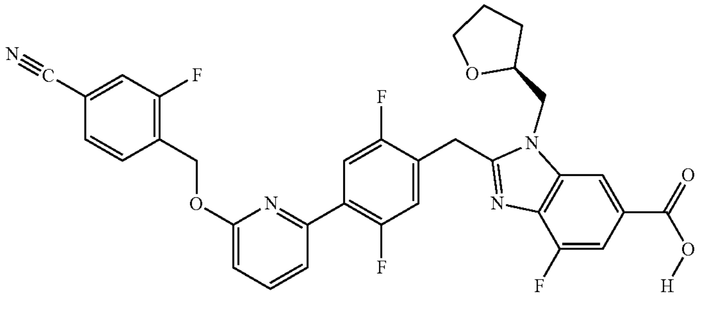

-continued
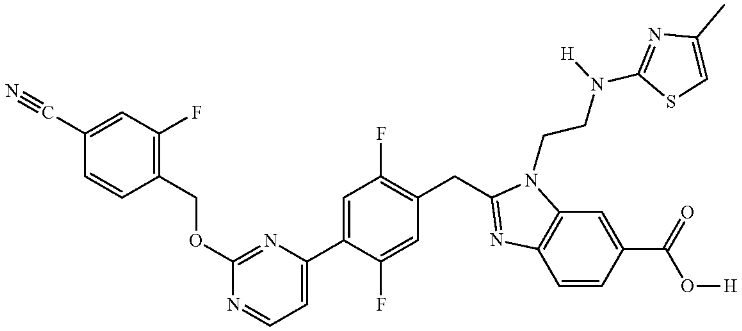
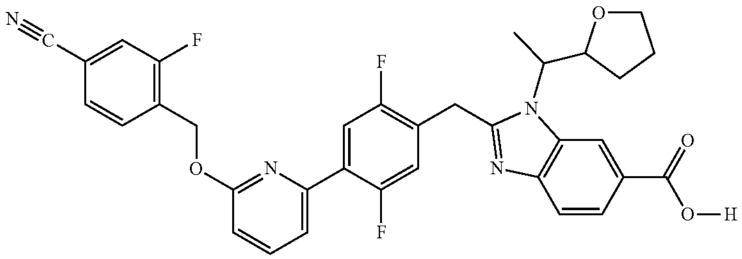
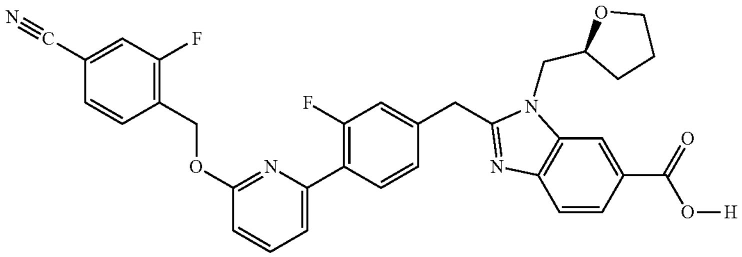
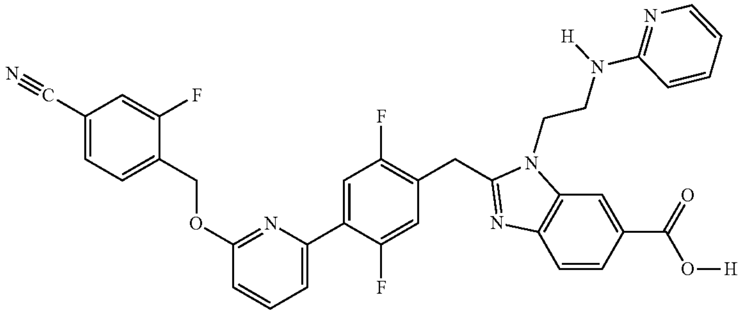
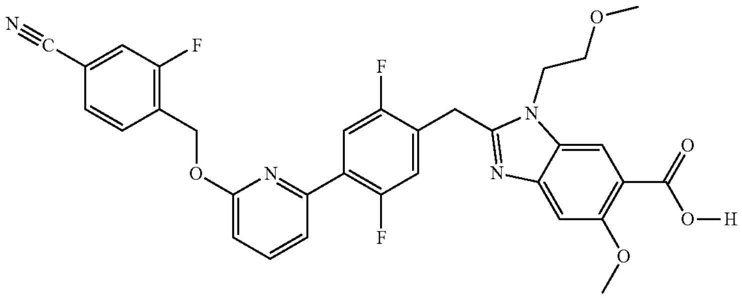
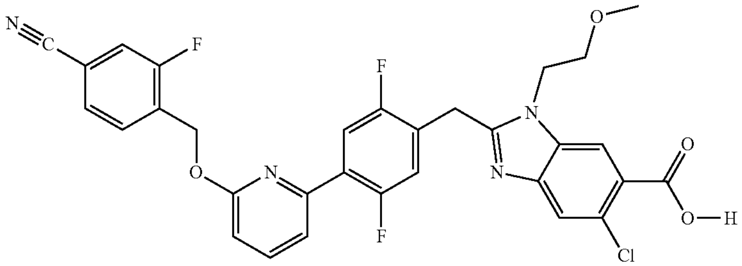

-continued
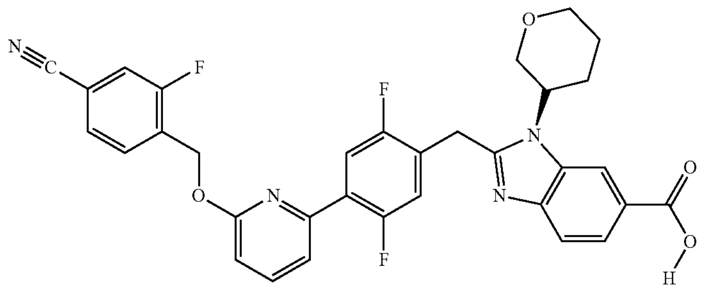
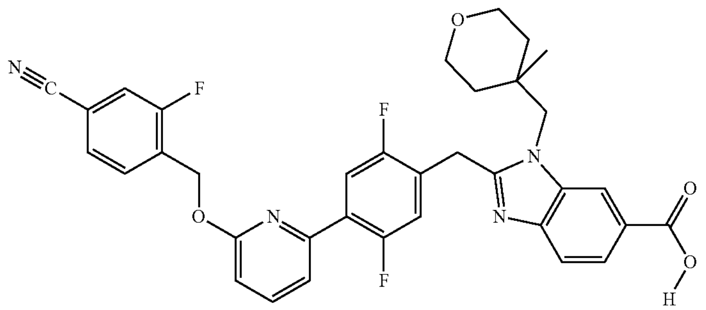
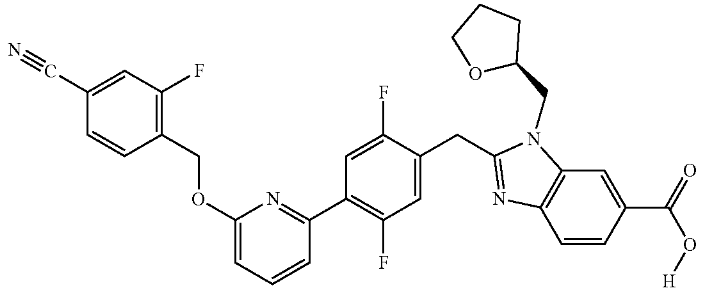
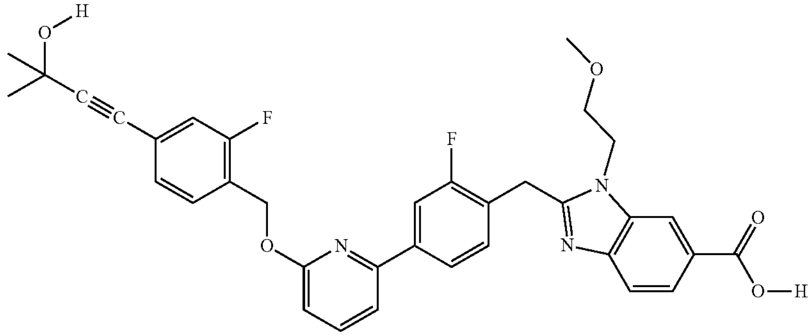
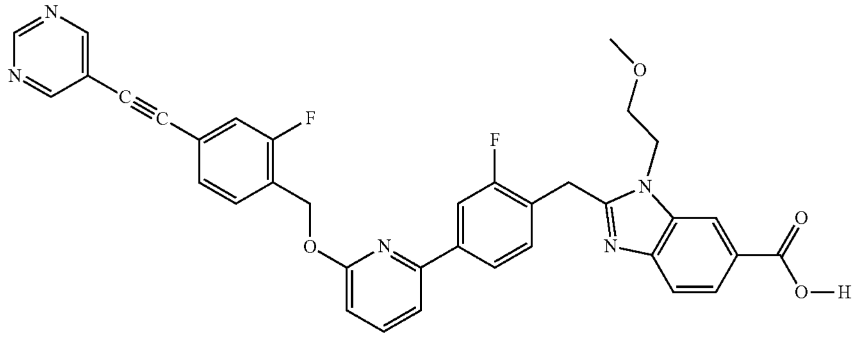

-continued
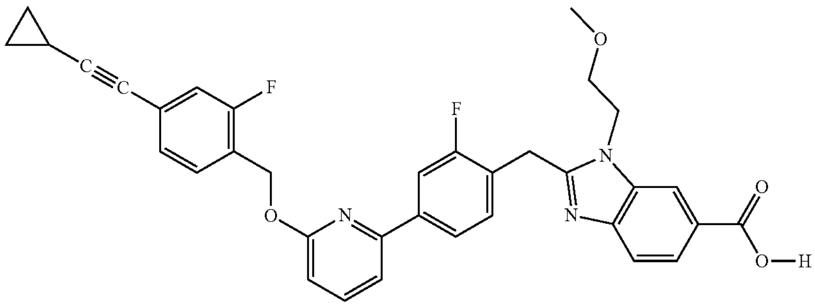
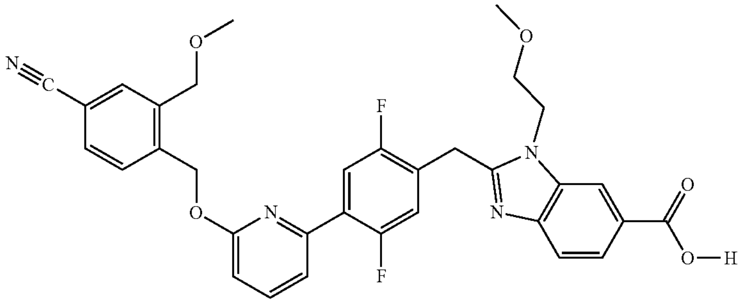
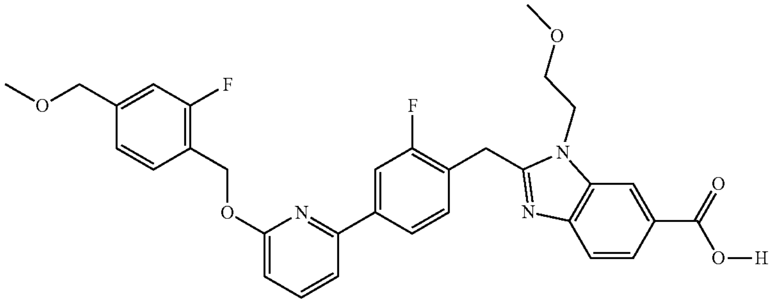
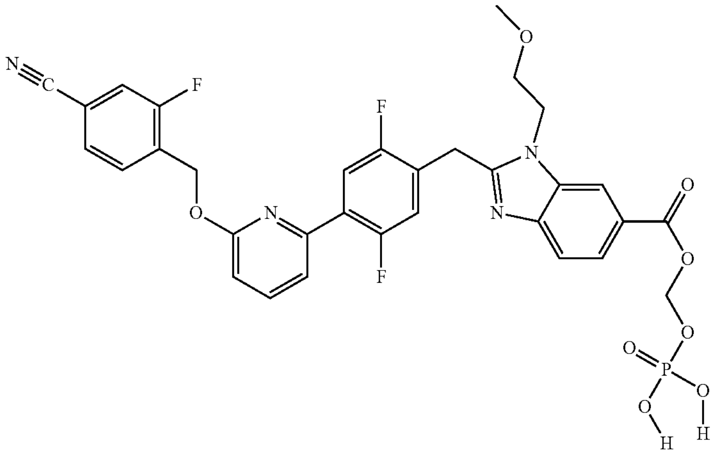
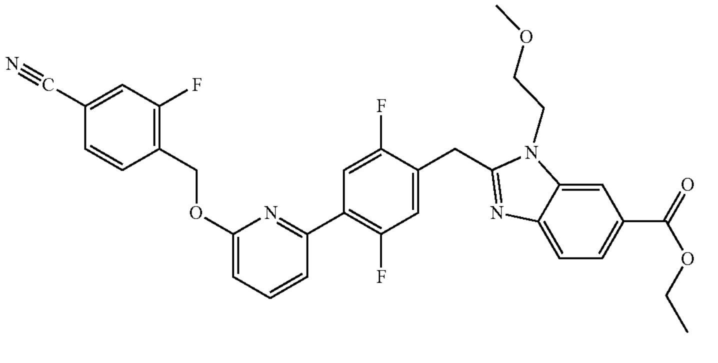

-continued
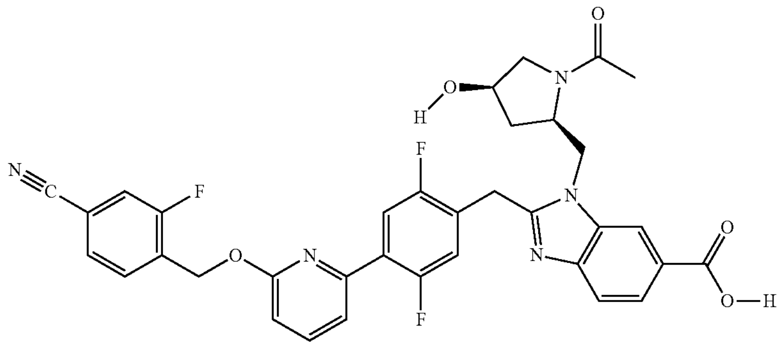
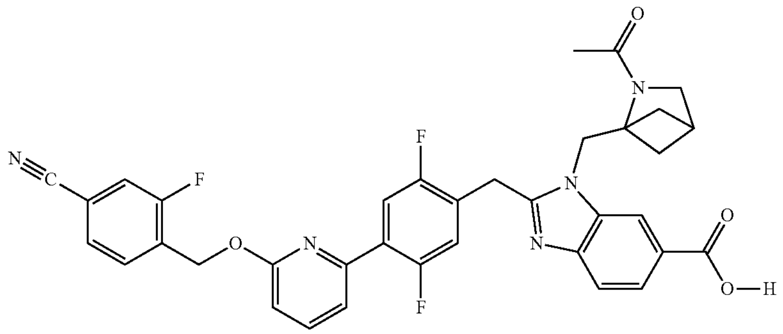
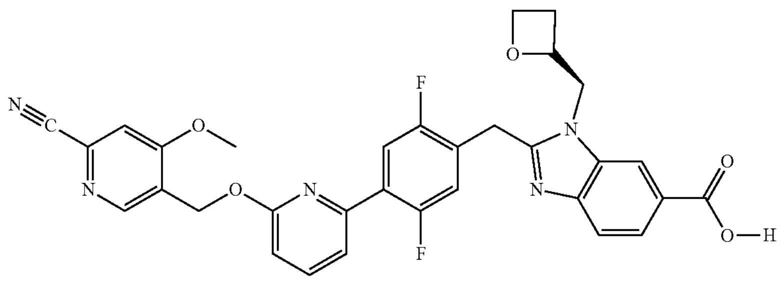
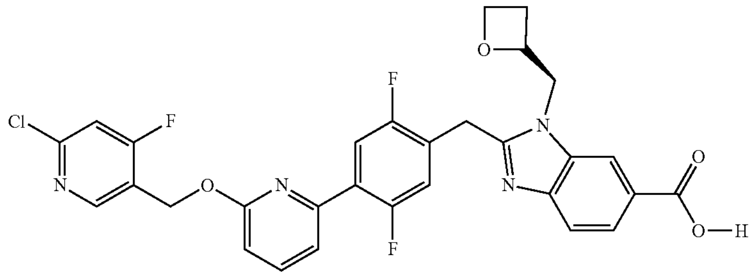
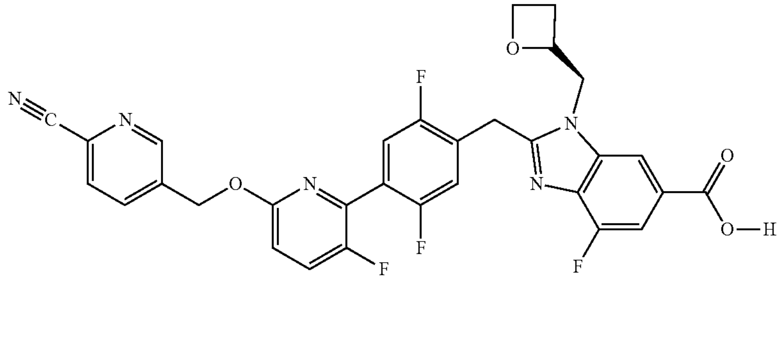

-continued
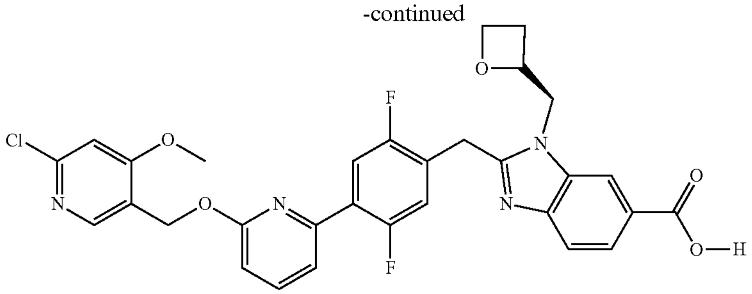
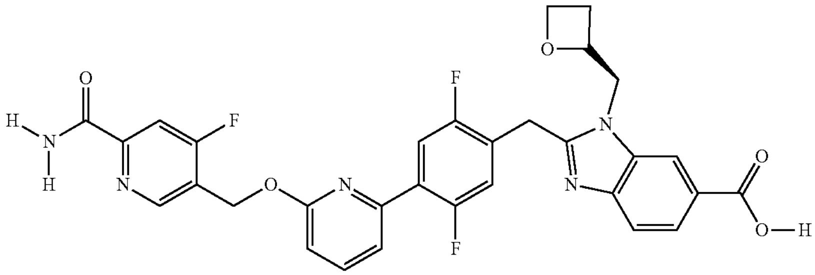
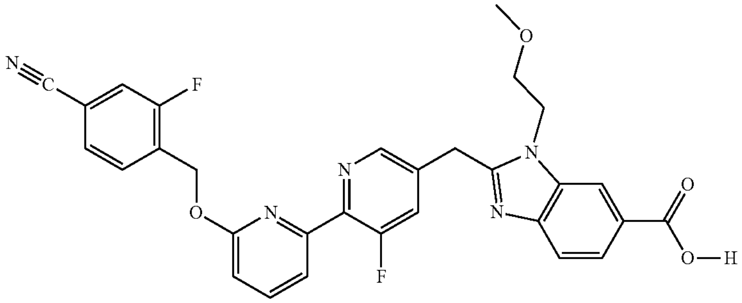
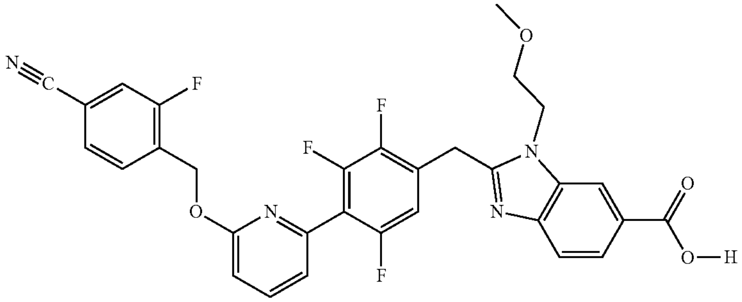
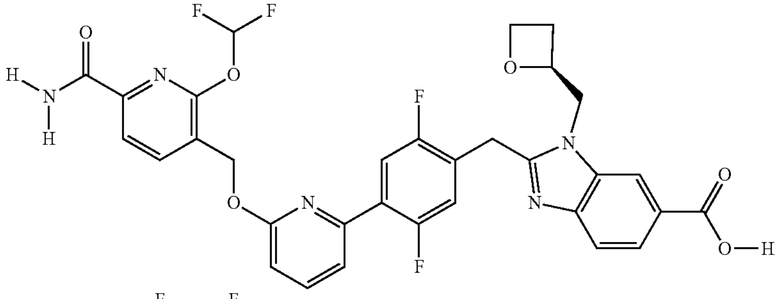
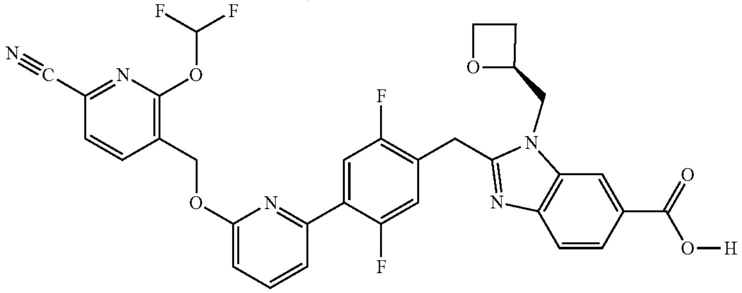

-continued
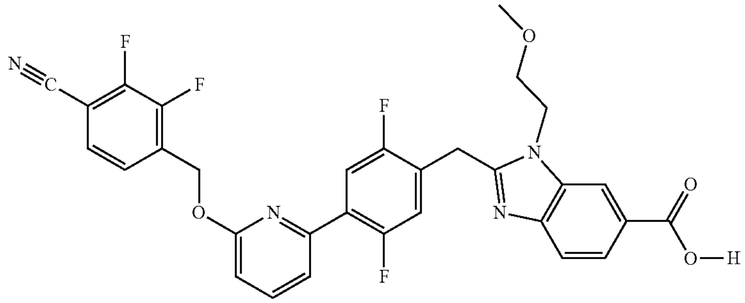
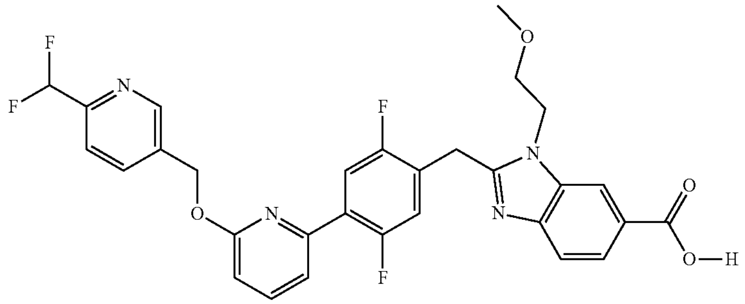
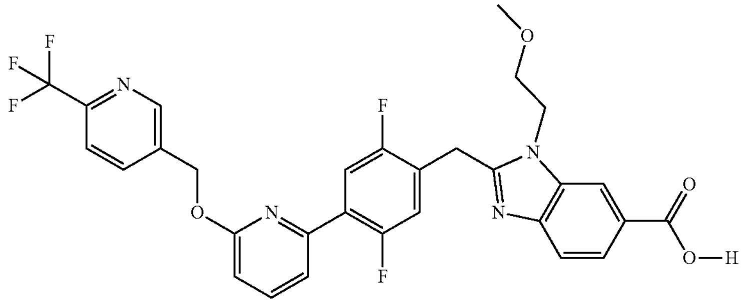
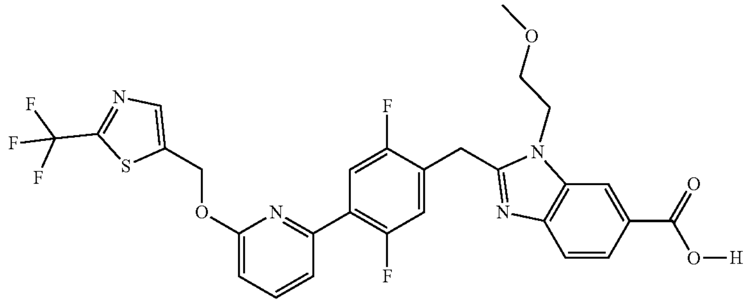
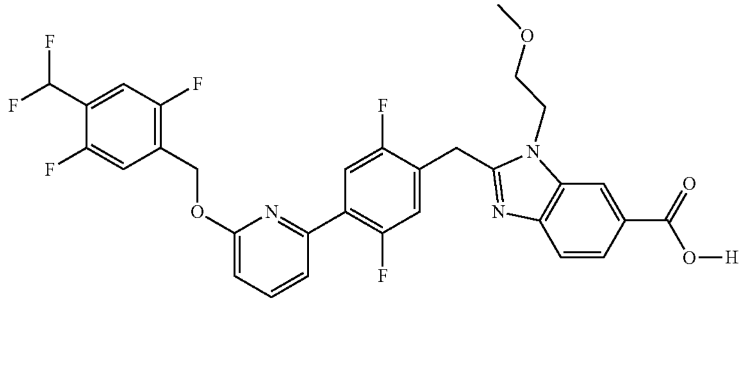

-continued
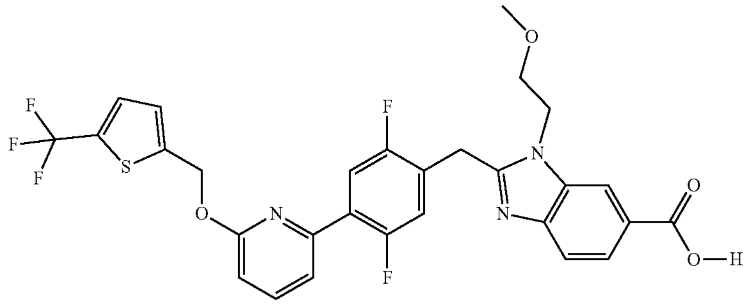
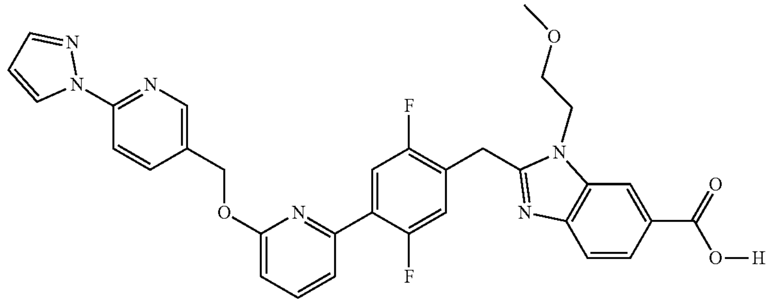
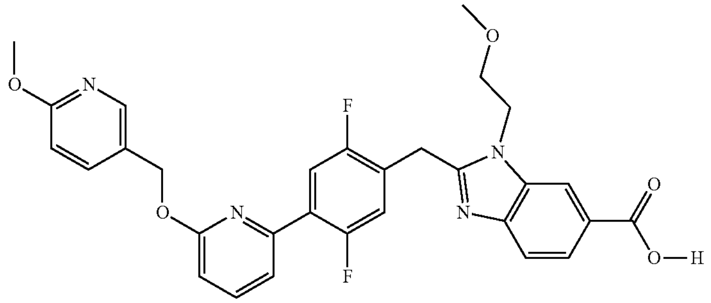
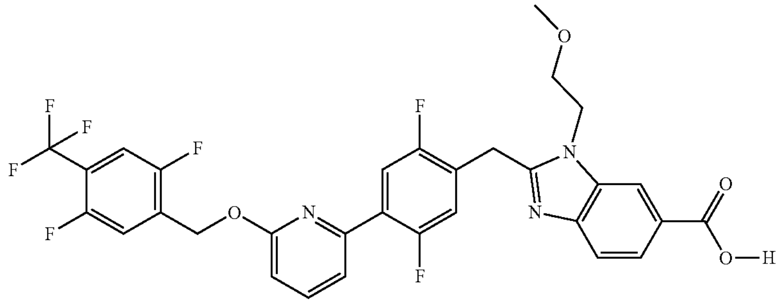
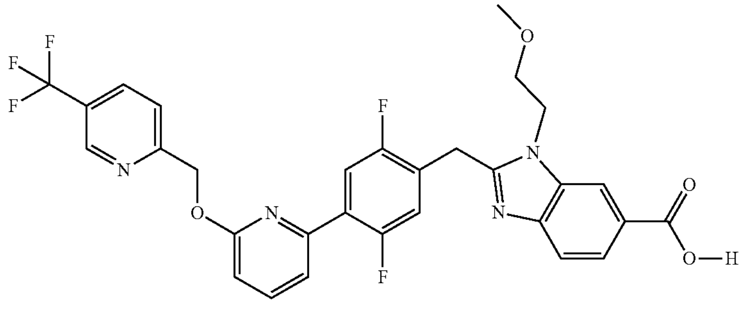

-continued

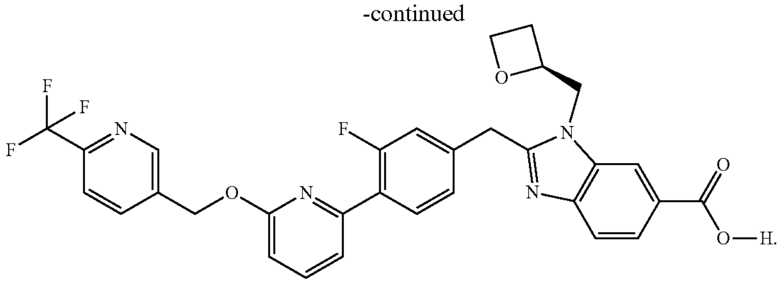

In some embodiments of a compound of Formula (I), (I-A-1), or other formula described herein, the compound has the structure:

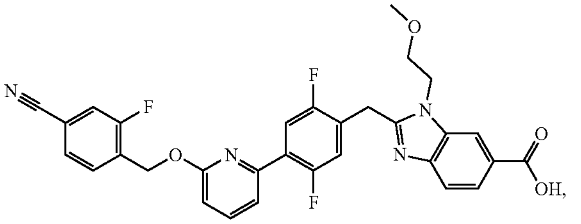

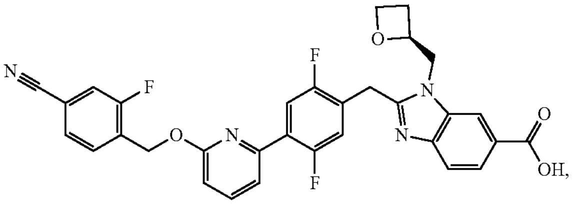

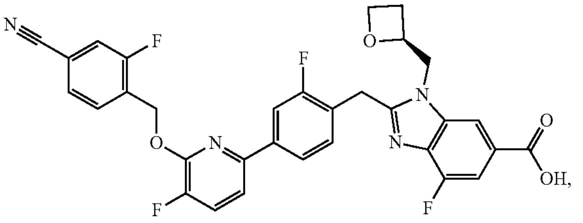

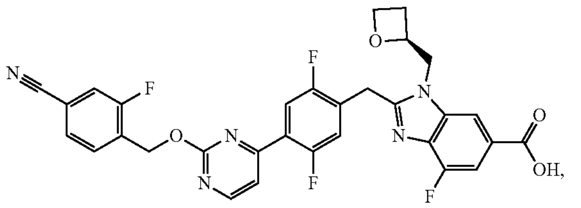

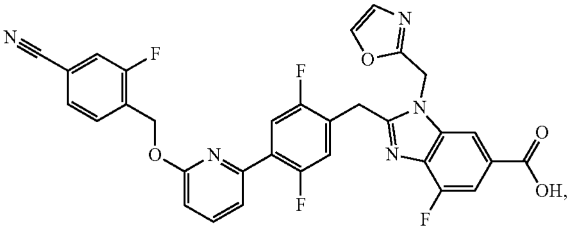

-continued

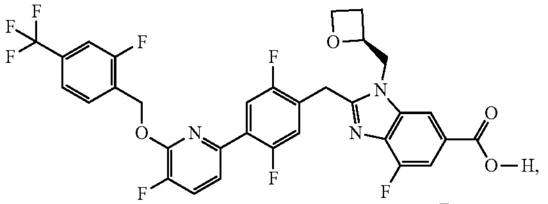

or

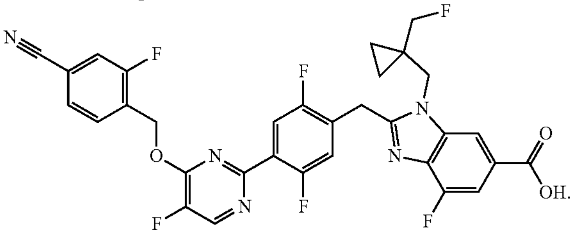

Also disclosed herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabeled (e.g. $^{14}C$ or $^{3}H$) compound, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products can be easily isolated since they are labeled (others are isolated by the use of antibodies capable of binding epitopes surviving in the metabolite). The metabolite structures are determined in conventional fashion, e.g. by MS or NMR analysis. In general, analysis of metabolites can be done in the same way as conventional drug metabolism studies well-known to those skilled in the art. The conversion products, so long as they are not otherwise found in vivo, can be useful in diagnostic assays for therapeutic dosing of the compounds even if they possess no GLP-1R activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo.

The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

III. Methods of Preparing Compounds

The compounds of the present disclosure can be prepared by any method known in the art. The following exemplary general methods illustrate routes that may be used to obtain a compound of the present disclosure.

Scheme 1

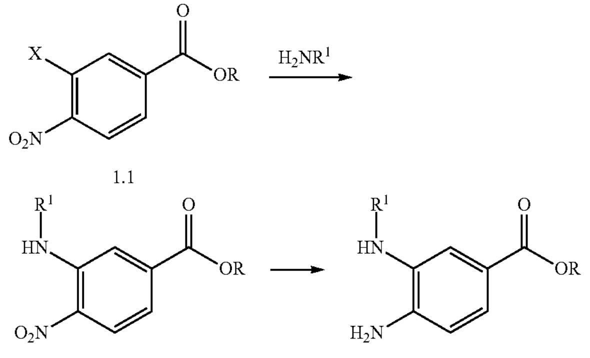

1.1

1.2

1.3

Intermediate 1.3 may be assembled by reacting an amine with Intermediate 1.1, wherein X is a halogen, and R is an alkyl, alkylaryl, or aryl, in the presence of a suitable base (e.g. DIPEA, KOtBu, etc.) to give Intermediate 1.2. Intermediate 1.2 can be converted to Intermediate 1.3 using suitable reducing conditions (e.g. $H_2$ and Pd/C, Fe and HCl, etc.).

Scheme 2

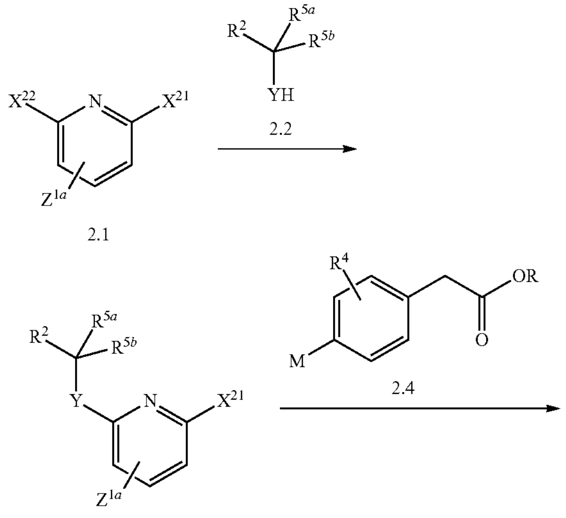

2.1

2.2

2.3

2.4

-continued

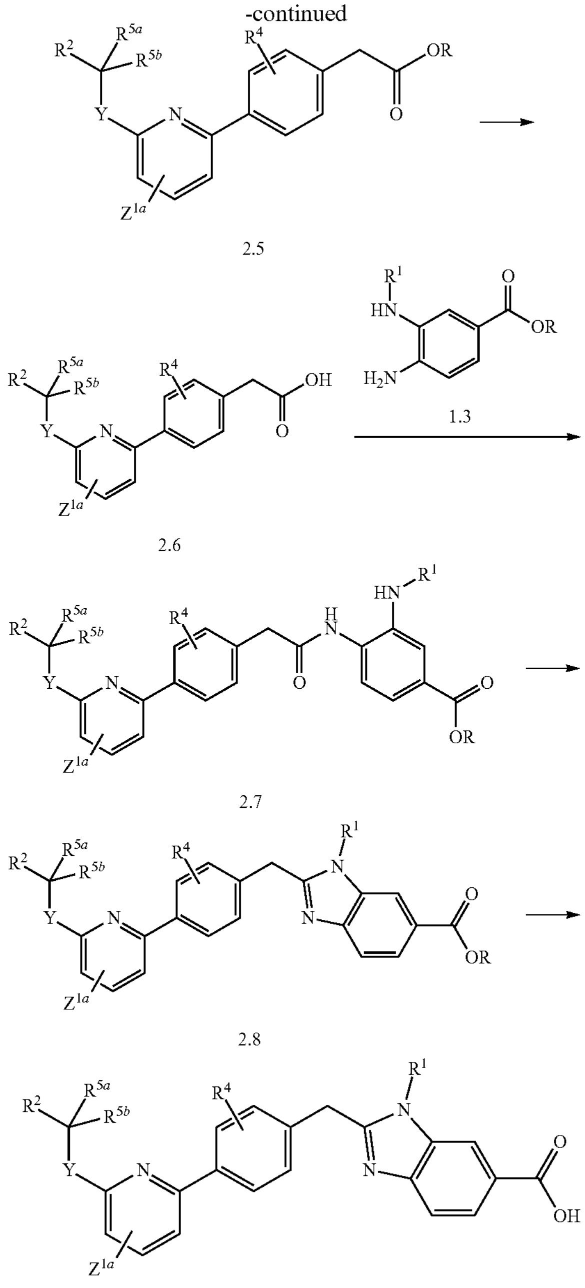

2.5

2.6

1.3

2.7

2.8

2.9

Compounds of Formula (I-A-1), (I-A-2), and/or Formula (I) having the structure of a compound of Formula 2.9 can be assembled by first coupling Intermediate 2.1, wherein $X^{21}$ and $X^{22}$ is each a leaving group, e.g., a halogen such as Cl or Br, With a heteroatom containing Intermediate 2.2 (where Y═O, NH, or S) using either a suitable base (e.g., DIPEA, KOtBu, etc.) or through metal mediated cross-coupling using a suitable palladium catalyst to give Intermediate 2.3 (Scheme 2). Intermediate 2.4 (where M=Li, MgBr, MgCl, or MgI, purchased commercially or obtained through metalation of a corresponding halide) can be combined with Intermediate 2.3 using a suitable palladium catalyst to deliver Intermediate 2.5. Following conversion to the acid Intermediate 2.6 using standard conditions (e.g. LiOH, LiI and pyridine, etc.), the Intermediate 1.3 can be added using standard amide bond forming conditions (e.g. DIPEA with HATU, etc.) to give Intermediate 2.7, which can, in turn, be converted to the corresponding benzimidazole Intermediate 2.8 under the influence of an acid catalyst (e.g. HCl, AcOH, etc.) This intermediate can be converted to the compound of Formula (I-A-1), (I-A-2), and/or Formula (I) using standard ester hydrolysis conditions (e.g., LiOH, LiI and pyridine, etc.).

While the above Scheme 2 is illustrated using Intermediate 2.1 as a dihalopyridine, any dihalogenated A-ring starting material can be used to obtain the analogous compound of Formula (I-A-1), (I-A-2), and/or Formula (I).

Scheme 3

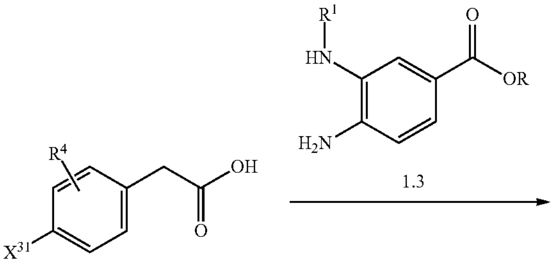

3.1

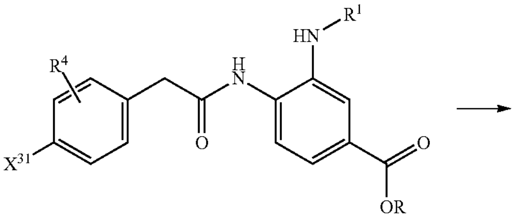

3.2

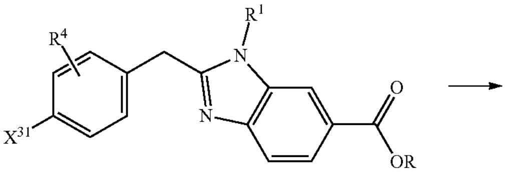

3.3

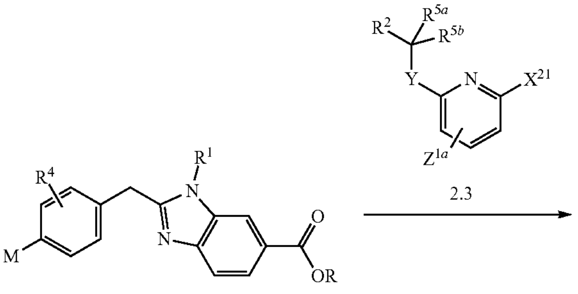

3.4

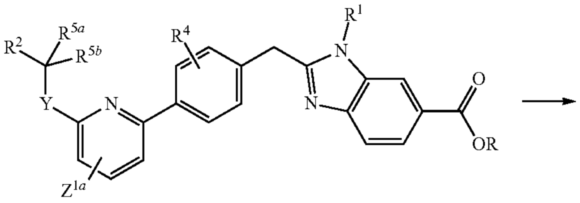

2.8

-continued

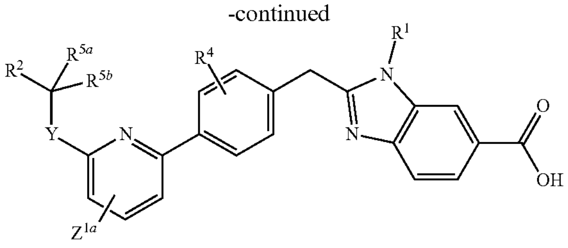

2.9

In some embodiments, a compound of Formula (I-A-1), (I-A-2), and/or Formula (I) having the structure of a compound of Formula 2.9 can be assembled first by the combination of Intermediate 3.1 (wherein $X^{31}$ is Cl, Br, or I) with Intermediate 1.3 (wherein R=alkyl, alkylaryl, or aryl) under standard amide bond forming conditions, e.g. DIPEA with HATU, etc. (Scheme 3). Treatment with a suitable acid catalyst (e.g. HCl, AcOH, etc.) can deliver Intermediate 3.3. Halogen metal exchange of —$X^{31}$ to -M can be achieved using a suitable reagent (e.g. iPrMgBr, etc.) or transition metal coupling using a suitable palladium catalyst and metal source (e.g. $B_2Pin_2$, $Bu_6Sn_2$, etc.) to give Intermediate 2.8 which can be converted to the compound of Formula (I-A-1), (I-A-2), and/or Formula (I) using standard ester hydrolysis conditions (e.g. LiOH, LiI and pyridine, etc.).

Scheme 4

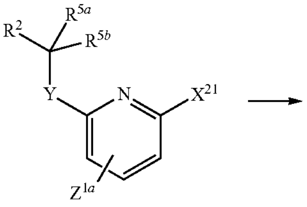

2.3

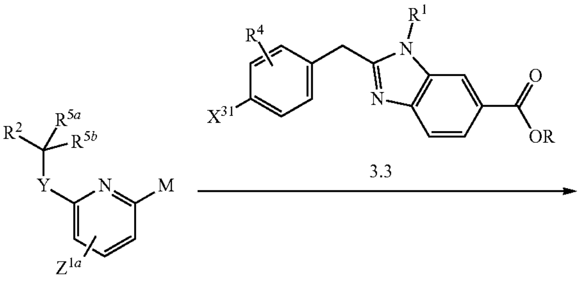

4.1

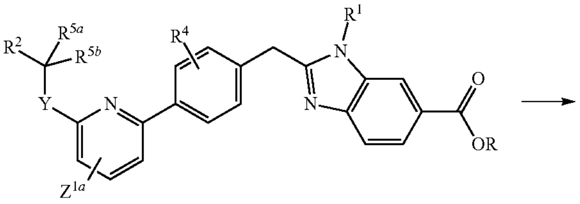

2.8

-continued

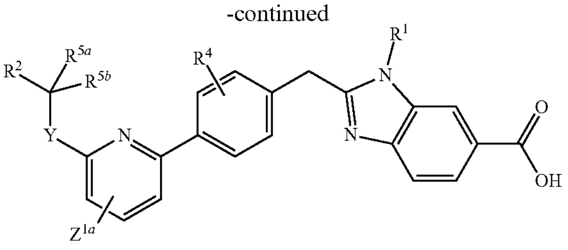

2.9

In some embodiments, a compound of Formula 2.9 can be formed by first conversion of Intermediate 2.3 to the metallated variant Intermediate 4.1 using a suitable palladium catalyst and metal source, e.g. $B_2Pin_2$, $Bu_6Sn_2$, etc. (Scheme 4). Intermediate 4.1 can be coupled to Intermediate 3.3 using a suitable palladium catalyst to deliver Intermediate 2.8 which can then be converted to the compound of Formula (I-A-1), (I-A-2), and/or Formula (I) using standard ester hydrolysis conditions, e.g. LiOH, LiI and pyridine, etc.

Scheme 5

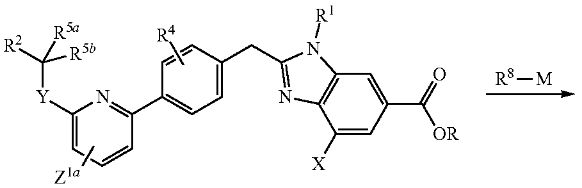

5.1

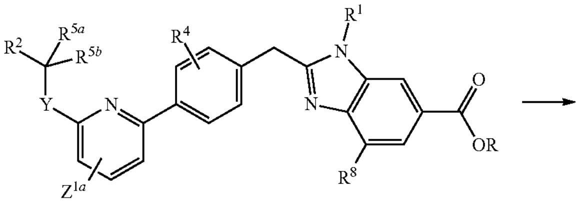

5.2

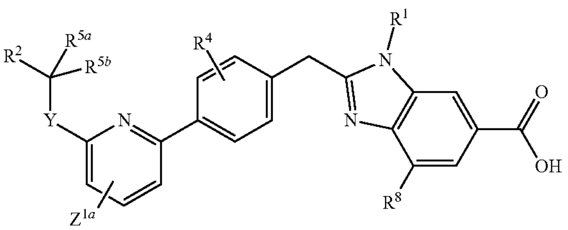

5.3

A compound of Formula (I-A-1), (I-A-2), and/or Formula (I) having the structure of a compound of Formula 5.3 can be assembled via first coupling to the halogen —X (wherein X is Cl, Br, or I) of Intermediate 5.1 using a suitable coupling partner and palladium catalyst to deliver Intermediate 5.2 which can be converted to a compound of Formula 5.3 using standard ester hydrolysis conditions, e.g. LiOH, LiI and pyridine, etc. (Scheme 5).

Scheme 6

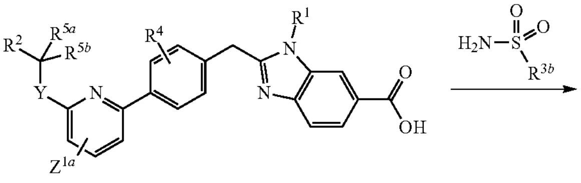

2.9

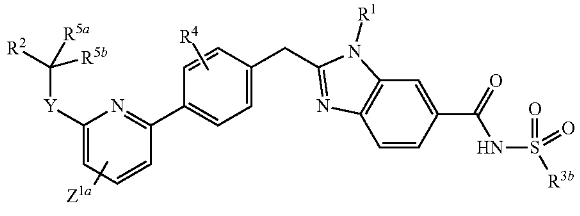

6.1

A compound of Formula (I-A-1), (I-A-2), and/or Formula (I) having the structure of a compound of Formula 6.1 can be obtained through the reaction of Intermediate 2.9 with a sulfonamide under suitable coupling conditions (e.g. EDC and DMAP, etc.) (Scheme 6).

Scheme 7

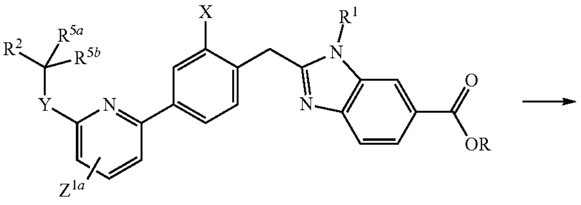

7.1

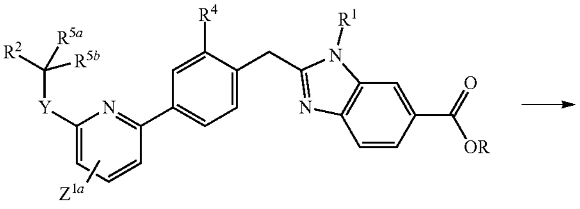

7.2

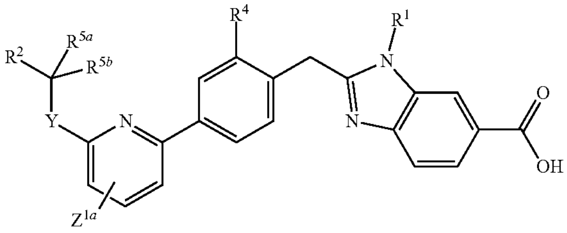

7.3

A compound of Formula (I-A-1), (I-A-2), and/or Formula (I) having the structure of a compound of Formula 7.3 can be assembled via first coupling to the halogen —X of Intermediate 7.1 using a suitable coupling partner and palladium catalyst to deliver Intermediate 7.2, which can be converted to a compound of Formula 7.3 using standard ester hydrolysis conditions (e.g. LiOH, LiI and pyridine, etc.) (Scheme 7).

Scheme 8

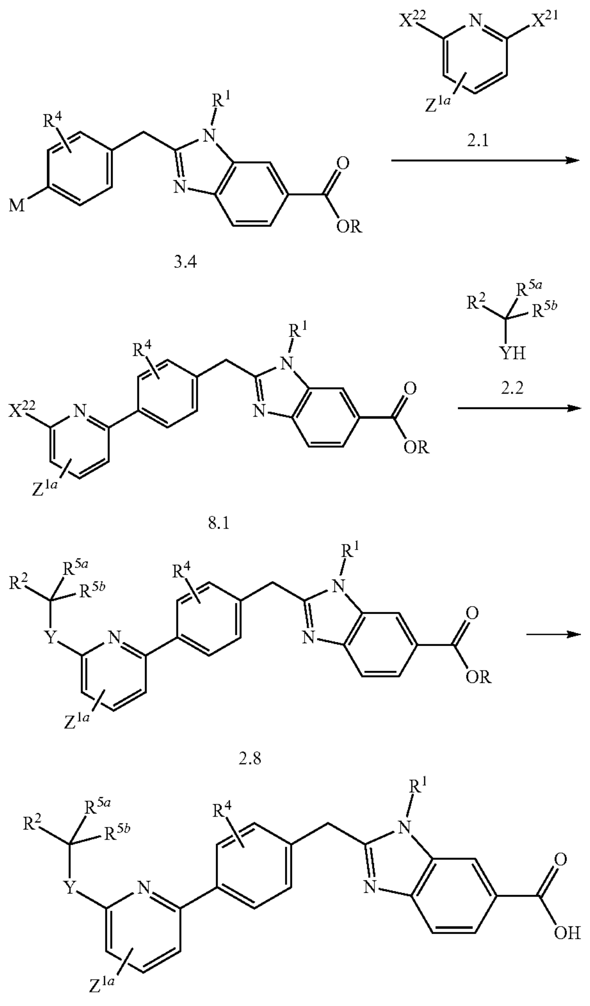

3.4

2.1

8.1

2.2

2.8

2.9

A compound of Formula (I-A-1), (I-A-2), and/or Formula (I) having the structure of a compound of Formula 2.9 can be assembled through first cross-coupling of an Intermediate 3.4 with Intermediate 2.1 using a suitable transition metal catalyst (e.g. palladium, etc.) (Scheme 8). This can then be coupled with a heteroatom containing Intermediate 2.2 (where Y=O, N or S) using either a suitable base (e.g. DIPEA, KOtBu, etc.) or through metal mediated cross-coupling using a suitable palladium catalyst to give Intermediate 2.8. Intermediate 2.8 can be converted to the compound of Formula (I-A-1), (I-A-2), and/or Formula (I) having the structure of a compound of Formula 2.9 using standard ester hydrolysis conditions (e.g. LiOH, LiI and pyridine, etc.).

IV. Pharmaceutical Formulations

In some embodiments, the present disclosure provides a pharmaceutical composition comprising a compound of the present disclosure (e.g. a compound of Formula (I-A-1), (I-A-2), (I), (Ia), (Ib), (Ib-1), (Ic), and/or (Id)), or a pharmaceutically acceptable salt thereof, and a pharmaceutically acceptable excipient.

In some embodiments of the disclosure, the pharmaceutical composition comprises a compound of Formula (I), (I-A-1), and/or (I-A-2), or a pharmaceutically acceptable salt thereof, and one or more additional therapeutic agents, as more fully set forth below.

Pharmaceutical compositions comprising the compounds disclosed herein, or pharmaceutically acceptable salts thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. In some embodiments, compositions may contain excipients such as those set forth in the Rowe et al, Handbook of Pharmaceutical Excipients, $6^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like. In some embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if desired, shaping the product. Techniques and formulations generally are found in Remington: The Science and Practice of Pharmacy, $21^{st}$ Edition, Lippincott Wiliams and Wilkins, Philadelphia, Pa., 2006.

Compositions described herein that are suitable for oral administration may be presented as discrete units (a unit dosage form) including but not limited to capsules, sachets or tablets each containing a predetermined amount of the active ingredient. In one embodiment, the pharmaceutical composition of the disclosure is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the mode of administration. For example, in some embodiments, a dosage form for oral administration to humans may contain approximately 1 to 1000 mg of active material formulated with an appropriate and convenient amount of a pharmaceutically acceptable excipient. In some embodiments, the pharmaceutically acceptable excipient varies from about 5 to about 95% of the total compositions (weight:weight).

In some embodiments, a composition comprising a compound of the present disclosure, or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

In some embodiments, the pharmaceutical compositions described above are for use in a human or an animal.

The disclosure further includes a compound of the present disclosure for administration as a single active ingredient of a pharmaceutically acceptable composition which can be prepared by conventional methods known in the art, for example by binding the active ingredient to a pharmaceutically acceptable, therapeutically inert organic and/or inorganic carrier or excipient, or by mixing therewith.

In one aspect, provided herein is the use of a compound of the present disclosure as a second or other active ingredient having a synergistic effect with other active ingredients in known drugs, or administration of the compound of the present disclosure together with such drugs.

The compound of the present disclosure may also be used in the form of a prodrug or other suitably modified form which releases the active ingredient in vivo.

V. Routes of Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intratumoral, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In some embodiments, a single dose can be administered once every week. A single dose can also be administered once every month.

Kits that comprise a compound of the present disclosure, or an enantiomer, or pharmaceutically acceptable salt thereof, or a pharmaceutical composition containing any of the above, are also included in the present disclosure. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, such as the diseases or conditions, described herein. In one embodiment, kits comprising a compound of the present disclosure, or a pharmaceutically acceptable salt thereof, in combination with one or more (e.g., one, two, three, four, one or two, or one to three, or one to four) additional therapeutic agents are provided.

Provided herein are also articles of manufacture that include a compound of the present disclosure or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

VI. Combination Therapy

In some embodiments, a compound of the present disclosure, or a pharmaceutically acceptable salt thereof, can be combined with a therapeutically effective amount of one or more (e.g., one, two, three, four, one or two, one to three, or one to four) additional therapeutic agents. In some embodiments, the additional therapeutic agent comprises an apoptotic signal-regulating kinase (ASK-1) inhibitor, a farnesoid X receptor (FXR) agonist, a peroxisome proliferator-activated receptor alpha (PPARα) agonist, fish oil, an acetyl-coA carboxylase (ACC) inhibitor, or a TGFβ antagonist, or a combination thereof.

In some embodiments, the therapeutic agent, or combination of therapeutic agents, are a(n) ACE inhibitor, 2-Acylglycerol O-acyltransferase 2 (DGAT2) inhibitor, Acetaldehyde dehydrogenase inhibitor, Acetyl CoA carboxylase inhibitor, Adrenergic receptor agonist, Alstrom syndrome protein 1 (ALMS1)/PKC alpha protein interaction inhibitor, Apelin receptor agonist, Diacylglycerol O acyltransferase 2 inhibitor, Adenosine A3 receptor agonist, Adenosine A3 receptor antagonist, Adiponectin receptor agonist, Aldehyde dehydrogenase 2 stimulator, AKT protein kinase inhibitor, AMP-activated protein kinases (AMPK), AMP kinase activator, ATP citrate lyase inhibitor, AMP activated protein kinase stimulator, Endothelial nitric oxide synthase stimulator, NAD-dependent deacetylase sirtuin-1 stimulator, Adrenergic receptor antagonist, Androgen receptor agonist, Amylin receptor agonist, Angiotensin II AT-1 receptor antagonist, Autophagy protein modulator, Autotaxin inhibitors, Axl tyrosine kinase receptor inhibitor, Bax protein stimulator, Beta-catenin inhibitor, Bioactive lipid, Calcitonin agonist, Cannabinoid receptor modulator, Caspase inhibitor, Caspase-3 stimulator, Cathepsin inhibitor, Caveolin 1 inhibitor, CCK receptor antagonist, CCL26 gene inhibitor, CCR2 chemokine antagonist, CCR2 chemokine antagonist, Angiotensin II AT-1 receptor antagonist, CCR3 chemokine antagonist, CCR5 chemokine antagonist, CD3 antagonist, CDGSH iron sulfur domain protein modulator, chitinase inhibitor, Chloride channel stimulator, Chitotriosidase 1 inhibitor, CNR1 inhibitor, Connective tissue growth factor ligand inhibitor, Cyclin D1 inhibitor, Cytochrome P450 7A1 inhibitor, DGAT1/2 inhibitor, Diacylglycerol O acyltransferase 1 inhibitor (DGAT1), Cytochrome P450 2E1 inhibitor (CYP2E1), CXCR4 chemokine antagonist, Dihydroceramide delta 4 desaturase inhibitor, Dihydroorotate dehydrogenase inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, fibroblast activation protein inhibitor, Free fatty acid receptor 1 agonist, Galectin-3 inhibitor, GDNF family receptor alpha like agonist, Glucagon receptor agonist, Glucagon-like peptide 1 agonist, Glucocorticoid receptor antagonist, Glucose 6-phosphate 1-dehydrogenase inhibitor, G-protein coupled bile acid receptor 1 agonist, G-protein coupled receptor-119 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, STAT-3 modulator, HMG CoA reductase inhibitor, HSD17B13 gene inhibitor, 5-HT 2a receptor antagonist, Hydrolase inhibitor, Hypoxia inducible factor-2 alpha inhibitor, IL-10 agonist, IL-17 antagonist, IL-22 agonist, Ileal sodium bile acid cotransporter inhibitor, Insulin sensitizer, Insulin ligand agonist, Insulin receptor agonist, integrin modulator, Integrin Antagonist, Integrin alpha-V/beta-1 antagonist, Integrin alpha-V/beta-6 antagonist, interleukin-1 receptor-associated kinase 4 (IRAK4) inhibitor, IL-6 receptor agonist, interleukin 17 ligand inhibitor, Jak2 tyrosine kinase inhibitor, Jun N terminal kinase-1 inhibitor, Kelch like ECH associated protein 1 modulator, Ketohexokinase (KHK) inhibitor, Klotho beta stimulator, Leukotriene A4 hydrolase inhibitor, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, LXR inverse agonists, Macrophage mannose receptor 1 modulator, Matrix metalloproteinases (MMPs) inhibitor, MEKK-5 protein kinase inhibitor, MCH receptor-1 antagonist, Membrane copper amine oxidase (VAP-1) inhibitor, Methionine aminopeptidase-2 inhibitor, Methyl CpG binding protein 2 modulator, MicroRNA-132 (miR-132) antagonist, MicroRNA-21 (miR-21) inhibitor, Mitochondrial uncoupler, Mixed lineage kinase-3 inhibitor, Motile sperm domain protein 2 inhibitor, Myelin basic protein stimulator, NACHT LRR PYD domain protein 3 (NLRP3) inhibitor, NAD-dependent deacetylase sirtuin stimulator, NADPH oxidase inhibitor (NOX), NFE2 L2 gene inhibitor, Nicotinic acid receptor 1 agonist, Opioid receptor mu antagonist, P2Y13 purinoceptor stimulator, Nuclear erythroid 2-related factor 2 stimulator, Nuclear receptor modulators, P2X7 purinoceptor modulator, PACAP type I receptor agonist, PDE 3 inhibitor, PDE 4 inhibitor, PDE 5 inhibitor, PDGF receptor beta modulator, Phenylalanine hydroxylase stimulator, Phospholipase C inhibitor, Phosphoric diester hydrolase inhibitor, PPAR alpha agonist, PPAR delta agonist, PPAR gamma agonist, Peptidyl-prolyl cis-trans isomerase A inhibitor, PNPLA3 gene inhibitor, PPAR gamma modulator, Protease-activated receptor-2 antagonist, Protein kinase modulator, Protein NOV homolog modulator, PTGS2 gene inhibitor, renin inhibitor, Resistin/CAP1 (adenylyl cyclase associated protein 1) interaction inhibitor, Rho associated protein kinase inhibitor, Snitrosoglutathione reductase (GSNOR) enzyme inhibitor, Sodium glucose transporter-2 inhibitor, Sphingolipid delta 4 desaturase DES1 inhibitor, SREBP transcription factor inhibitor, STAT-1 inhibitor, Stearoyl CoA desaturase-1 inhibitor, STK25 inhibitor, Suppressor of cytokine signalling-1 stimulator, Suppressor of cytokine signalling-3 stimulator, Telomerase stimulator, TERT gene modulator, TGF beta (TGFB1) ligand inhibitor, TNF antagonist, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, TLR-9 antagonist, VDR agonist, WNT modulators, or YAP/TAZ modulator and Zonulin inhibitor.

Non-limiting examples of the one or more additional therapeutic agents include:

ACE inhibitors, such as enalapril;
Acetaldehyde dehydrogenase inhibitors, such as ADX-629;
Acetyl CoA carboxylase (ACC) inhibitors, such as NDI-010976 (firsocostat), DRM-01, gemcabene, GS-834356, PF-05175157, QLT-091382, PF-05221304;
Acetyl CoA carboxylase/Diacylglycerol O acyltransferase 2 inhibitors, such as PF-07055341;
Adenosine receptor agonists, such as CF-102 (namodenoson), CF-101, CF-502, CGS21680;
Adenosine A3 receptor antagonist, such as FM-101;
Adiponectin receptor agonists, such as ADP-355, ADP-399;
Adrenergic receptor antagonist, such as bromocriptine, phentermine, VI-0521
Aldehyde dehydrogenase 2 stimulators, such as FP-045;
Alpha glucosidase inhibitors (e.g. voglibose, acarbose, or miglitol);
Amylin/calcitonin receptor agonists, such as KBP-042, KBP-089;
AMP activated protein kinase stimulators, such as, C-455, PXL-770, O-304;
AMP kinase activators/ATP citrate lyase inhibitors, such as bempedoic acid (ETC-1002, ESP-55016)
AMP activated protein kinase/Endothelial nitric oxide synthase/NAD-dependent deacetylase sirtuin-1 stimulators, such as NS-0200 (leucine+metformin+sildenafil);
Androgen receptor agonists, such as LPCN-1144, LPCN-1148, testosterone prodrug;
Angiotensin II AT-1 receptor antagonists, such as irbesartan; Angiopoietin-related protein-3 inhibitors, such as vupanorsen (IONIS-ANGPTL3-LRx);
Apelin receptor agonist, such as CB-5064, MBT-2;
Autophagy protein modulators, such as A-2906;
Autotaxin (ectonucleotide pyrophosphatase/phosphodiesterase 2 (NPP2 or ENPP2)) inhibitors, such as FP10.47, PAT-505, PAT-048, GLPG-1690, X-165, PF-8380, TJC-0265, TJC-0316, AM-063, BBT-877;
Axl tyrosine kinase receptor inhibitors, such as bemcentinib (BGB-324, R-428);
Bax protein stimulators, such as CBL-514;
Bioactive lipids, such as DS-102;
Cannabinoid receptor modulators, such as namacizumab (nimacimab), GWP-42004, REV-200, CRB-4001, INV-101, SCN-002;
Caspase inhibitors, such as emricasan;
Pan cathepsin B inhibitors, such as VBY-376;
Pan cathepsin inhibitors, such as VBY-825;
CCK receptor antagonist, such as proglumide;
CCL26 gene inhibitor, such as mosedipimod, KDDF-201410-10
CCR2/CCR5 chemokine antagonists, such as BMS-687681, cenicriviroc, maraviroc, CCX-872, leronlimab, WXSH-0213;
CCR2/CCR5 chemokine antagonists and FXR agonists, such as LJC-242 (tropifexor+cenivriviroc);
CCR2 chemokine antagonists, such as propagermanium;
CCR2 chemokine/Angiotensin II AT-1 receptor antagonists, such as DMX-200, DMX-250;
CCR3 chemokine antagonists, such as bertilimumab;
CD3 antagonists, such as NI-0401 (foralumab);
CDGSH iron sulfur domain protein modulators, such as EYP-002;
Chitinase inhibitor, such as OATD-01;
Chitotriosidase 1 inhibitors, such as OAT-2068;
Chloride channel stimulators, such as cobiprostone, and lubiprostone;
Casein kinase-1 (CK1) delta/epsilon inhibitors, such as PF-05006739;
Connective tissue growth factor ligand inhibitor, such as PBI-4050;
CXCR4 chemokine antagonists, such as AD-214;
Diglyceride acyltransferase 2 (DGAT2) inhibitors, such as IONIS-DGAT2Rx, PF-06865571;
Diglyceride acyltransferase 1 (DGAT1) inhibitors, such as GSK-3008356;
Diacylglycerol O acyltransferase 1 (DGAT1)/Cytochrome P450 2E1 inhibitors (CYP2E1), such as SNP-610;
Dihydroorotate dehydrogenase inhibitor, such as vidofludimus;
Dipeptidyl peptidase IV inhibitors, such as linagliptin, evogliptin;
Eotaxin ligand inhibitors, such as bertilimumab, CM-101;
Extracellular matrix protein modulators, such as CNX-024;
Farnesoid X receptor (FXR) agonists, such as AGN-242266, AGN-242256, ASC-42, EDP-297 (EP-024297), RDX-023, BWL-200, AKN-083, EDP-305, GNF-5120, cilofexor tromethamine (GS-9674), HPG-1860, IOT-022, LMB-763, obeticholic acid, Px-102, Px-103, M790, M780, M450, M-480, MET-409, MET-642, PX20606, SYHA-1805, vonafexor (EYP-001), TERN-101, TC-100, INT-2228, TQA-3526, ZG-5266;
Farnesoid X receptor (FXR)/G-protein coupled bile acid receptor 1 (TGR5) agonists, such as INT-767;
Fatty acid synthase inhibitors, such as TVB-2640, FT-8225;
Fibroblast growth factor 19 (rhFGF19)/cytochrome P450 (CYP) 7A1 inhibitors, such as aldafermin (NGM-282);
Fibroblast growth factor 21 (FGF-21) ligand modulators, such as AP-025, BMS-986171, B-1654, BIO89-100, BOS-580,
Pegbelfermin (BMS-986036), B-1344;
Fibroblast growth factor 21 (FGF-21)/glucagon like peptide 1 (GLP-1) agonists, such as YH-25723 (YH-25724; YH-22241), efruxifermin (AKR-001);
FGF receptor agonists/Klotho beta stimulators, such as BFKB-8488A (RG-7992);
Free fatty acid receptor 1 agonist, such as SCO-267;
Galectin-3 inhibitors, such as belapectin (GR-MD-02), GB-1107 (Gal-300), GB-1211 (Gal-400);
GDNF family receptor alpha like agonist, such as NGM-395
Glucagon-like peptide 1 (GLP1R) agonists, such as ALT-801, AC-3174, liraglutide, cotadutide (MEDI-0382), SAR-425899, LY-3305677, HM-15211, YH-25723, YH-GLP1, RPC-8844, PB-718, PF-06882961, semaglutide;
Glucagon-like peptide 1 receptor agonist; Oxyntomodulin ligand; Glucagon receptor agonist, such as efinopegdutide;
Gastric inhibitory polypeptide/Glucagon-like peptide-1 (GIP/GLP-1) receptor co-agonist, such as tirzepatide (LY-3298176);
PEGylated long-acting glucagon-like peptide-1/glucagon (GLP-1R/GCGR) receptor dual agonist, such as DD-01;
Glucagon/GLP1-receptor agonist, such as BI-456906;
Glucocorticoid receptor antagonists, such as CORT-118335 (miricorilant);

Glucose 6-phosphate 1-dehydrogenase inhibitors, such as ST001;

Glucokinase stimulator, such as dorzagliatin, sinogliatin (RO-5305552)

G-protein coupled bile acid receptor 1 (TGR5) agonists, such as RDX-009, INT-777, HY-209;

G-protein coupled receptor 84 antagonist, such as PBI-4547;

G-protein coupled receptor-119 agonist, such as DA-1241;

Heat shock protein 47 (HSP47) inhibitors, such as ND-L02-s0201;

Hedgehog protein and/or TGF beta ligand inhibitors, such as Oxy-210

Histone deacetylase inhibitors/STAT-3 modulators, such as SFX-01;

HMG CoA reductase inhibitors, such as atorvastatin, fluvastatin, pitavastatin, pravastatin, rosuvastatin, simvastatin;

HSD17B13 gene inhibitor, such as ALN-HSD, ARO-HSD

Hydrolase inhibitor, such as ABD-X;

Hypoxia inducible factor-2 alpha inhibitors, such as PT-2567;

IL-10 agonists, such as peg-ilodecakin;

Ileal sodium bile acid cotransporter inhibitors, such as odevixibat (A-4250), volixibat potassium ethanolate hydrate (SHP-262), GSK2330672, CJ-14199, elobixibat (A-3309);

Insulin sensitizers, such as, KBP-042, azemiglitazone potassium (MSDC-0602K), ION-224, MSDC-5514, Px-102, RG-125 (AZD4076), Tolimidone, VVP-100X, CB-4211, ETI-101, pioglitazone;

Insulin ligand/dsInsulin receptor agonists, such as ORMD-0801;

Integrin antagonists, such as IDL-2965;

IL-6 receptor agonists, such as KM-2702;

Integrin alpha-V/beta-6 and alpha-V/beta-1 dual inhibitor; such as PLN-74809;

Interleukin 17 ligand inhibitor, such as netakimab

Jak1/2 tyrosine kinase inhibitor, such as baricitinib

Jun N terminal kinase-1 inhibitor, such as CC-90001

Kelch like ECH associated protein 1 modulator, such as alpha-cyclodextrin-stabilized sulforaphane;

Ketohexokinase (KHK) inhibitors, such as PF-06835919, LY-3478045;

beta Klotho (KLB)-FGF1c agonists, such as MK-3655 (NGM-313);

Leukotriene A4 hydrolase inhibitor, such as LYS-006;

5-Lipoxygenase inhibitors, such as tipelukast (MN-001), epeleuton (DS-102, (AF-102);

Lipoprotein lipase inhibitors, such as CAT-2003;

LPL gene stimulators, such as alipogene tiparvovec;

Liver X receptor (LXR) inhibitors, such as PX-665, PX-L603, PX-L493, BMS-852927, T-0901317, GW-3965, SR-9238;

Lysophosphatidate-1 receptor antagonists, such as BMT-053011, UD-009 (CP-2090), AR-479, ITMN-10534, BMS-986020, KI-16198;

Lysyl oxidase homolog 2 inhibitors, such as simtuzumab, PXS-5382A (PXS-5338);

Macrophage mannose receptor 1 modulators, such as tilmanocept-Cy3 (technetium Tc 99m tilmanocept);

Matrix metalloprotease inhibitors, such as ALS-L1023;

Membrane copper amine oxidase (VAP-1) inhibitors, such as TERN-201, TT-01025;

MEKK-5 protein kinase (ASK-1) inhibitors, such as CJ-16871, CS-17919, selonsertib (GS-4997), SRT-015, GS-444217, GST-HG-151, TERN-301;

MCH receptor-1 antagonists, such as CSTI-100 (ALB-127158);

Semicarbazide-Sensitive Amine Oxidase/Vascular Adhesion Protein-1 (SSAO/VAP-1) Inhibitors, such as PXS-4728A (BI-1467335);

Methionine aminopeptidase-2 inhibitors, such as ZGN-1061, ZGN-839, ZN-1345;

Methyl CpG binding protein 2 modulators, such as mercaptamine;

Mineralocorticoid receptor antagonists (MCRA), such as MT-3995 (apararenone);

Mitochondrial uncouplers, such as 2,4-dinitrophenol, HU6, Mito-99-0053;

Mixed lineage kinase-3 inhibitors, such as URMC-099-C;

Motile sperm domain protein 2 inhibitors, such as VB-601;

Myelin basic protein stimulators, such as olesoxime;

Myeloperoxidase inhibitors, such as PF-06667272, AZM-198;

NADPH oxidase inhibitors, such as GKT-831, GenKyoTex, APX-311, setanaxib;

Nicotinic acid receptor 1 agonists, such as ARI-3037 MO;

NACHT LRR PYD domain protein 3 (NLRP3) inhibitors, such as KDDF-201406-03, NBC-6, IFM-514, JT-194 (JT-349);

NFE2 L2 gene inhibitor, such as GeRP-amiR-144

Nuclear receptor modulators, such as DUR-928 (DV-928);

Opioid receptor mu antagonists, such as methylnaltrexone;

P2X7 purinoceptor modulators, such as SGM-1019;

P2Y13 purinoceptor stimulators, such as CER-209;

PDE 3/4 inhibitors, such as tipelukast (MN-001);

PDE 5 inhibitors, such as sildenafil, MSTM-102;

PDGF receptor beta modulators, such as BOT-191, BOT-509;

Peptidyl-prolyl cis-trans isomerase inhibitors, such as CRV-431 (CPI-432-32), NVP-018, NV-556 (NVP-025);

Phenylalanine hydroxylase stimulators, such as HepaStem;

Phosphoric diester hydrolase inhibitor, such as ZSP-1601;

PNPLA3 gene inhibitor, such as AZD-2693;

PPAR agonists, such as Chiglitazar, elafibranor (GFT-505), seladelpar lysine (MBX-8025), deuterated pioglitazone R-enantiomer, pioglitazone, PXL-065 (DRX-065), saroglitazar, lanifibranor (IVA-337), CHS-131, pemafibrate (K-877), ZG-0588, ZSP-0678; ZSYM-008;

Protease-activated receptor-2 antagonists, such as PZ-235;

Protein kinase modulators, such as CNX-014;

Protein NOV homolog modulators, such as BLR-200;

PTGS2 gene inhibitors, such as STP-705, STP-707;

Renin inhibitors, such as PRO-20;

Resistin/CAP1 (adenylyl cyclase associated protein 1) interaction inhibitors, such as DWJ-211

Rev protein modulator, such as ABX-464;

Rho associated protein kinase (ROCK) inhibitors, such as REDX-10178 (REDX-10325), KD-025, RXC-007, TDI-01;

Snitrosoglutathione reductase (GSNOR) enzyme inhibitors, such as SL-891;

Sodium glucose transporter-2 (SGLT2) inhibitors, such as ipragliflozin, remogliflozin etabonate, ertugliflozin, dapagliflozin, tofogliflozin, sotagliflozin, Sodium glucose transporter-1/2 (SGLT 1/2) inhibitors, such as licogliflozin bis(prolinate) (LIK-066);

SREBP transcription factor inhibitors, such as CAT-2003, HPN-01, MDV-4463;

Stearoyl CoA desaturase-1 inhibitors, such as aramchol;

Thyroid hormone receptor beta agonists, such as ALG-009, ASC-41, CNPT-101101; CNPT-101207, CS-27186, KY-41111, resmetirom (MGL-3196), MGL-3745, TERN-501, VK-2809;

TLR-2/TLR-4 antagonists, such as VB-201 (CI-201);

TLR-4 antagonists, such as JKB-121, JKB-122, naltrexone;

Tyrosine kinase receptor modulators, such as CNX-025, GFE-2137 (repurposed nitazoxanide);

TLR-9 antagonist, such as GNKS-356

TNF antagonist, such as ALF-421

GPCR modulators, such as CNX-023;

Nuclear hormone receptor modulators, such as Px-102;

VDR agonist, such as CK-15;

Xanthine oxidase inhibitors, such as ACQT-1127;

Xanthine oxidase/Urate anion exchanger 1 (URAT1) inhibitors, such as RLBN-1001, RLBN-1127; and Zonulin Inhibitors, such as lorazotide acetate (INN-202).

In some embodiments, the one or more additional therapeutic agents are selected from A-4250, AC-3174, acetylsalicylic acid, AK-20, alipogene tiparvovec, AMX-342, AN-3015, anti-TAGE antibody, aramchol, ARI-3037 MO, ASP-8232, AZD-2693, bertilimumab, Betaine anhydrous, BI-1467335, BMS-986036, BMS-986171, BMT-053011, BOT-191, BTT-1023, budesonide, BX-003, CAT-2003, cenicriviroc, CBW-511, CER-209, CF-102, CGS21680, CNX-014, CNX-023, CNX-024, CNX-025, cobiprostone, colesevelam, dabigatran etexilate mesylate, dapagliflozin, DCR-LIV1, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, fluasterone (ST-002), FT-4101, GDD-3898, GH-509, GKT-831, GNF-5120, GRI-0621, GR-MD-02, GS-300, GS-4997, GS-9674, HEC-96719, HTD-1801, HS-10356, HSG-4112, HST-202, HST-201, HU-6, hydrochlorothiazide, icosabutate (PRC-4016), icosapent ethyl ester, IMM-124-E, INT-767, INV-240, IONIS-DGAT2Rx, ipragliflozin, Irbesarta, propagermanium, IVA-337, J2H-1702, JKB-121, KB-GE-001, KBLP-004, KBLP-009, KBP-042, KD-025, M790, M780, M450, metformin, sildenafil, LB-700, LC-280126, linagliptin, liraglutide, (LJN-452) (tropifexor), LM-011, LM-002 (CVI-LM-002), LMB-763, LYN-100, MB-N-008, MBX-8025, MDV-4463, mercaptamine, MGL-3196, MGL-3745, MP-301, MSDC-0602K, namacizumab, NC-101, NDI-010976, ND-L02-s0201 (BMS-986263), NGM-282, NGM-313, NGM-386, NGM-395, NP-011, NP-135, NP-160, norursodeoxycholic acid, NV-422, NVP-022, 0-304, obeticholic acid (OCA), 25HC3S, olesoxime, PAT-505, PAT-048, PBI-4547, pegilodecakin, pioglitazone, pirfenidone, PRI-724, PX20606, Px-102, PX-L603, PX-L493, PXS-4728A, PZ-235, PZH-2109, RCYM-001, RDX-009, remogliflozin etabonate, RG-125 (AZD4076), RPI-500, 5-723595, saroglitazar, SBP-301, semaglutide, SH-2442, SHC-028, SHC-023, simtuzumab, solithromycin, sotagliflozin, statins (atorvastatin, fluvastatin, pitavastatin, pravastatin, rosuvastatin, simvastatin), symbiotic, TCM-606F, TEV-45478, TQA-3526, TQA-3563, tipelukast (MN-001), TLY-012, TRX-318, TVB-2640, TXR-612, TS-20004, UD-009, UN-03, ursodeoxycholic acid, VBY-376, VBY-825, VK-2809, vismodegib, volixibat potassium ethanolate hydrate (SHP-626), VVP-100X, WAV-301, WNT-974, WXSH-0038, WXSH-0078, XEN-103, XRx-117, XTYW-003, XW-003, XW-004, ZGN-839, ZG-5216, ZSYM-008, ZYSM-007.

In some embodiments, the compound of present disclosure is combined with one or more therapeutic agents selected from an anti-obesity agent including but not limited to peptide YY or an analogue thereof, a neuropeptide Y receptor type 2 (NPYR2) agonist, a NPYR1 agonist, an NPYR5 antagonist, a cannabinoid receptor type 1 (CB1 R) antagonist, a lipase inhibitor (e.g., orlistat), a human proislet peptide (HIP), a melanocortin receptor 4 agonist (e.g., setmelanotide), a melanin concentrating hormone receptor 1 antagonist, a famesoid X receptor (FXR) agonist (e.g. obeticholic acid), apoptotic signal-regulating kinase (ASK-1) inhibitor, zonisamide, phentermine (alone or in combination with topiramate), a norepinephrine/dopamine reuptake inhibitor (e.g., bupropion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues thereof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1 R agonist, e.g., liraglutide, exenatide, dulaglutide, albiglutide, lixisenatide, or semaglutide), an insulin sensitizer such as thiazolidinediones (TZDs), a peroxisome proliferator-activated receptor alpha (PPARα) agonist, fish oil, an acetyl-coA carboxylase (ACC) inhibitor, a transforming growth factor beta (TGFβ) antagonist, a GDNF family receptor alpha like (GFRAL) agonist, a melanocortin-4 receptor (MC4R) agonist, including the pharmaceutically acceptable salts of the specifically named agents and the pharmaceutically acceptable solvates of said agents and salts.

In some embodiments, methods and compositions include a therapeutically effective amount of a compound of Formula (I-A-1), (I-A-2), and/or Formula (I) and a therapeutically effective amount of a Farnesoid X Receptor (FXR) agonist. In some embodiments, the FXR agonist is a compound of Formula (II) or (III):

(II)

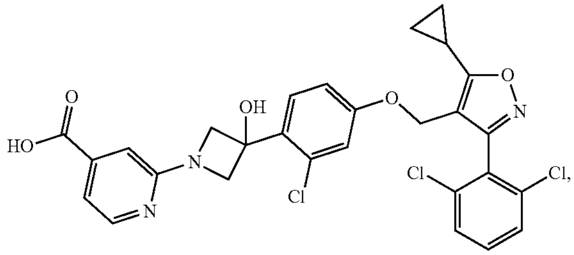

,

-continued (III)

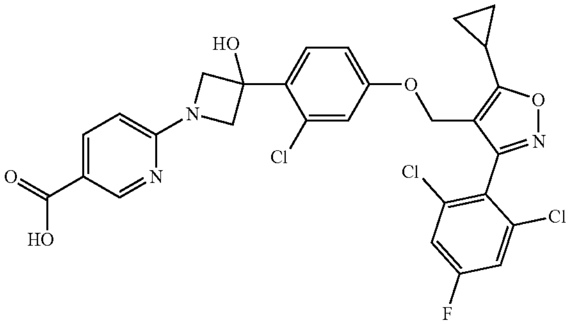

or a pharmaceutically acceptable salt, a stereoisomer, a mixture of stereoisomers, or a tautomer thereof.

In some embodiments, methods and compositions include a therapeutically effective amount of a compound of Formula (I-A-1), (I-A-2), and/or Formula (I) and a therapeutically effective amount of an ASK1 inhibitor. In some embodiments, the ASK1 inhibitor is a compound of Formula (IV):

(IV)

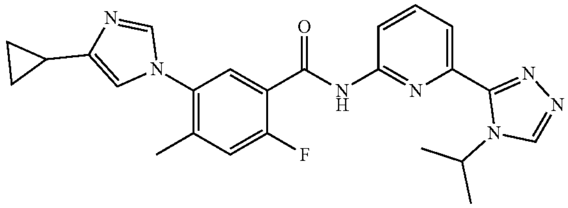

or a pharmaceutically acceptable salt, a stereoisomer, a mixture of stereoisomers, or a tautomer thereof.

In some embodiments, methods and compositions include a therapeutically effective amount of a compound of Formula (I-A-1), (I-A-2), and/or Formula (I) and a therapeutically effective amount of an Acetyl CoA Carboxylase (ACC) inhibitor. In certain embodiments, the ACC inhibitor is a compound of Formula (V):

(V)

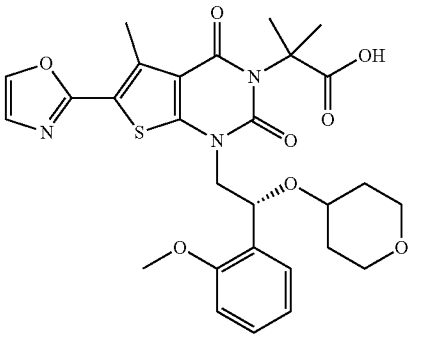

or a pharmaceutically acceptable salt thereof.

In some embodiments, methods and compositions include a therapeutically effective amount of a compound of Formula (I-A-1), (I-A-2), and/or Formula (I) and a therapeutically effective amount of a Thyroid Hormone Receptor (THR)β agonist. In certain embodiments, the THR β agonist is a compound of Formula (VI):

(VI)

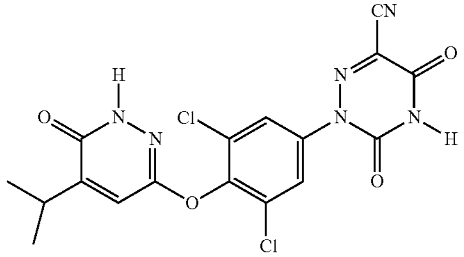

or a pharmaceutically acceptable salt, a stereoisomer, a mixture of stereoisomers, or a tautomer thereof.

VII. Methods of Treatment

In some embodiments, compounds of Formula (I-A-1), (I-A-2), (I), (Ia), (Ib), (Ib-1), (Ic) and/or (Id), or pharmaceutically acceptable salt thereof, are useful in a method of treating and/or preventing a GLP-1R mediated disease or condition. In some embodiments, a method for treating and/or preventing a GLP-1R mediated disease or condition includes administering to a subject in need thereof a pharmaceutically effective amount of a compound of the present disclosure or pharmaceutically acceptable salt thereof.

In some embodiments, the disease or condition comprises a liver disease or related diseases or conditions, e.g., liver fibrosis, non-alcoholic fatty liver disease (NAFLD), non-alcoholic steatohepatitis (NASH), liver cirrhosis, compensated liver fibrosis, decompensated liver fibrosis, hepatocellular carcinoma, Primary Biliary Cirrhosis (PBC), or Primary Sclerosing Cholangitis (PSC). In some embodiments, the disease or condition comprises a metabolic disease or related diseases or conditions, such as diabetes mellitus, obesity, or cardiometabolic diseases.

GLP-1R agonists are currently being investigated in connection with certain disorders and conditions, including for example diabetes. GLP-1 analogs that are DPP4 resistant and have longer half-lives than endogenous GLP-1 have been reported to be associated with weight loss and improved insulin action. Liraglutide, a peptide GLP-1R agonist approved in connection with treatment of diabetes, has been reported to show favorable improvements in outcomes in NASH subjects.

In some embodiments, the present disclosure relates to the use of compounds of Formula (I), (I-A-1), (I-A-2), or a pharmaceutically acceptable salt thereof in the preparation of a medicament for the prevention and/or treatment of a disease or condition mediated by GLP-1R, such as a liver disease or metabolic disease. In some embodiments, the present disclosure relates to the use of compounds of Formula (I-A-1), (I-A-2), or a pharmaceutically acceptable salt thereof in the preparation of a medicament for the prevention and/or treatment of a disease or condition mediated by GLP-1R, such as a liver disease or metabolic disease. For example, some embodiments provide a compound of Formula (I), (I-A-1), and/or (I-A-2), or a pharmaceutically acceptable salt thereof, or a use thereof, for treatment and/or prevention of chronic intrahepatic or some forms of extrahepatic cholestatic conditions, of liver fibrosis, of acute intrahepatic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of type II diabetes and clinical complications of type I and type II diabetes, of conditions and diseases which result from chronic fatty and fibrotic degeneration of organs due to enforced lipid and specifically triglyceride accumulation and subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistent infections by intracellular bacteria or parasitic protozoae, of non-malignant hyperproliferative disorders, of malignant hyperproliferative disorders, of colon adenocarcinoma and hepatocellular carcinoma for instance, of liver steatosis and associated syndromes, of liver failure or liver malfunction as an outcome of chronic liver diseases or of surgical liver resection, of Hepatitis B infection, of Hepatitis C infection and/or of cholestatic and fibrotic effects that are associated with alcohol-induced cirrhosis or with viral-borne forms of hepatitis, of type I diabetes, pre-diabetes, idiopathic type 1 diabetes, latent autoimmune diabetes, maturity onset diabetes of the young, early onset diabetes, malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, obesity, eating disorders, sleep apnea, weight gain, sugar craving, dyslipidemia, hyperinsulinemia, congestive heart failure, myocardial infarction, stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, left ventricular hypertrophy, Parkinson's Disease, peripheral arterial disease, macular degeneration, cataract, glomerulosclerosis, chronic renal failure, metabolic syndrome, angina pectoris, premenstrual syndrome, thrombosis, atherosclerosis, impaired glucose metabolism, or vascular restenosis.

In some embodiments, a method of treating and/or preventing a non-alcoholic fatty liver disease (NAFLD), comprises administering to a subject in need thereof a compound of the present disclosure or a pharmaceutically acceptable salt thereof.

The disclosure also relates to a compound according to Formula (I-A-1), (I-A-2), and/or Formula (I) or a pharmaceutical composition comprising said compound for preventive and posttraumatic treatment of a cardiovascular disorder, such as acute myocardial infarction, acute stroke, or thrombosis which occur as an endpoint of chronic obstructive atherosclerosis. In some embodiments, a method for treating and/or preventing cardiovascular disorder comprises administering a compounds of Formula (I-A-1), (I-A-2), and/or Formula (I) to a subject in need thereof.

The disclosure further relates to a compound or pharmaceutical composition for the treatment and/or prevention of obesity and associated disorders such as metabolic syndrome (combined conditions of dyslipidemias, diabetes and abnormally high body-mass index) which can be overcome by GLP1R-mediated lowering of serum triglycerides, blood glucose and increased insulin sensitivity and GLP1R-mediated weight loss. In some embodiments, a method for treating and/or preventing a metabolic disease comprises administering a compounds of Formula (I) to a subject in need thereof. In some embodiments, a method for treating and/or preventing a metabolic disease comprises administering a compounds of Formula (I-A-1) and/or (I-A-2), to a subject in need thereof.

In a further embodiment, the compounds or pharmaceutical composition of the present disclosure are useful in preventing and/or treating clinical complications of Type I and Type II Diabetes. Examples of such complications include diabetic nephropathy, diabetic retinopathy, diabetic neuropathies, or Peripheral Arterial Occlusive Disease (PAOD). Other clinical complications of diabetes are also encompassed by the present disclosure. In some embodiments, a method for treating and/or preventing complications of Type I and Type II Diabetes comprises administering a compounds of Formula (I) to a subject in need thereof. In some embodiments, a method for treating and/or preventing complications of Type I and Type II Diabetes comprises administering a compounds of Formula (I-A-1) and/or (I-A-2) to a subject in need thereof.

Furthermore, conditions and diseases which result from chronic fatty and fibrotic degeneration of organs due to enforced lipid and/or triglyceride accumulation and subsequent activation of profibrotic pathways may also be prevented and/or treated by administering the compounds or pharmaceutical composition of the present disclosure. Such conditions and diseases can include NASH and chronic cholestatic conditions in the liver, Glomerulosclerosis and Diabetic Nephropathy in the kidney, Macular Degeneration and Diabetic Retinopathy in the eye and neurodegenerative diseases, such as Alzheimer's Disease in the brain, or Diabetic Neuropathies in the peripheral nervous system. In some embodiments, a method for treating and/or preventing conditions and diseases which result from chronic fatty and fibrotic degeneration of organs due to enforced lipid and/or triglyceride accumulation and subsequent activation of profibrotic pathways comprises administering a compounds of Formula (I) to a subject in need thereof. In some embodiments, a method for treating and/or preventing conditions and diseases which result from chronic fatty and fibrotic degeneration of organs due to enforced lipid and/or triglyceride accumulation and subsequent activation of profibrotic pathways comprises administering a compounds of Formula (I-A-1) and/or (I-A-2) to a subject in need thereof. In some embodiments, a method for treating and/or preventing NASH comprises administering a compounds of Formula (I) to a subject in need thereof. In some embodiments, a method for treating and/or preventing NASH comprises administering a compounds of Formula (I-A-1) and/or (I-A-2) to a subject in need thereof.

Further provided herein is a pharmaceutical composition for use in treating a GLP-1R mediated disease or condition described herein, comprising a compound of the present disclosure or a pharmaceutically acceptable salt thereof.

The present disclosure also describes a use for the manufacture of a medicament in treating a GLP-1R mediated disease or condition comprising a compound of the present disclosure or a pharmaceutically acceptable salt thereof. Medicaments as referred to herein may be prepared by conventional processes, including the combination of a compound according to the present disclosure and a pharmaceutically acceptable carrier.

Also disclosed is a compound of the present disclosure or a pharmaceutically acceptable salt thereof for the treatment of a GLP-1R mediated disease or condition. Also disclosed is a compound of the present disclosure or a pharmaceutically acceptable salt thereof for the prevention of a GLP-1R mediated disease or condition.

VII. Examples

Many general references providing commonly known chemical synthetic schemes and conditions useful for synthesizing the disclosed compounds are available (see, e.g., Smith, March's Advanced Organic Chemistry: Reactions, Mechanisms, and Structure, 7*th* edition, Wiley-Interscience, 2013.)

Compounds as described herein can be purified by any of the means known in the art, including chromatographic means, such as high-performance liquid chromatography (HPLC), preparative thin layer chromatography, flash column chromatography and ion exchange chromatography. Any suitable stationary phase can be used, including normal and reversed phases as well as ionic resins. For example, the disclosed compounds can be purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the pendant groups. Each of the reactions depicted in the general schemes can be run at a temperature from about 0° C. to the reflux temperature of the organic solvent used.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The embodiments are also directed to processes and intermediates useful for preparing the subject compounds or pharmaceutically acceptable salts thereof. The following description is, therefore, not intended to limit the scope of the present disclosure.

In some embodiments, the present disclosure generally provides a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in schemes below, and the examples that follow.

The compounds detailed in the Examples were synthesized according to the general synthetic methods described below. Compounds were named using ChemDraw version 18.1.0.535 (PerkinElmer Informatics, Inc.) unless otherwise indicated.

Abbreviations

Certain abbreviations and acronyms are used in describing the experimental details. Although most of these would be understood by one skilled in the art, Table 1 contains a list of many of these abbreviations and acronyms.

TABLE 1

List of Abbreviations and Acronyms

| Abbreviation | Meaning |
|---|---|
| Ac | acetate |
| ACN | acetonitrile |
| AmPhos | di-tert-butyl(4-dimethylaminophenyl)phosphine |
| Bn | benzyl |
| Bpin | (pinacolato)boron |
| $B_2Pin_2$ | bis(pinacolato)diboron |
| Bu | butyl |
| Bz | benzoyl |
| BzCl | benzoyl chloride |
| cataCXium ® A Pd G3 | Mesylate[(di(1-adamantyl)-n-butylphosphine)-2-(2'-amino-1,1'-biphenyl)]palladium(II) |
| DBA | dibenzalacetone |
| DBU | 1,8-Diazabicyclo[5. 4. 0]undec-7-ene |
| DCM | dichloromethane |
| DCE | dichlorethane |
| DEA | diethylamine |
| Deoxofluor | Bis(2-methoxyethyl)aminosulfur trifluoride |
| DIPEA | diisopropylethylamine |
| DME | dimethoxyethane |
| DMEM | Dulbecco's Modified Eagle Medium |
| DMF | dimethylformamide |
| DMSO | dimethylsulfoxide |
| dppf | 1,1'-Ferrocenediyl-bis(diphenylphosphine) |
| EDCI | N-(3-dimethylaminopropyl)-N'-ethylcarbodiimide hydrochloride |
| ES/MS | electron spray mass spectrometry |
| Et | ethyl |
| FBS | fetal bovine serum |
| HATU | 1-[Bis(dimethylamino)methylene]-1H-1,2,3-triazolo[4,5-b]pyridinium 3-oxide hexafluorophosphate |
| IPA | isopropanol |
| JohnPhos | (2-Biphenyl)di-tert-butylphosphine |
| KOtBu | potassium tert-butoxide |
| LC | liquid chromatography |
| LCMS | liquid chromatography/mass spectrometry |
| MCPBA | meta-chloroperbenzoic acid |
| Me | methyl |
| m/z | mass to charge ratio |
| MS or ms | mass spectrum |
| NMP | N-methyl-2-pyrrolidone |
| Pd Rockphos | [(2-Di-tert-butylphosphino-3-methoxy-6-methyl-2',4',6'-triisopropyl-1,1'-biphenyl)-2-(2-amino- |

TABLE 1-continued

List of Abbreviations and Acronyms

| Abbreviation | Meaning |
|---|---|
| G3 | biphenyl)]palladium(II) methanesulfonate |
| Ph | phenyl |
| $Ph_3P$ | triphenylphosphine |
| pin | pinacol |
| Pyr | pyridine |
| RBF | round bottom flask |
| RP-HPLC | reverse phase high performance liquid chromatography |
| RT | room temperature |
| SFC | supercritical fluid chromatography |
| tBuXPhos Pd G3 | [(2-Di-tert-butylphosphino-2',4',6'-triisopropyl-1,1'-biphenyl)-2-(2'-amino-1,1'-biphenyl)] palladium(II) methanesulfonate |
| TEA | triethylamine |
| TFA | trifluoroacetic acid |
| THF | tetrahydrofuran |
| Ts | 4-toluenesulfonyl |
| XPhos Pd G2 | Chloro(2-dicyclohexylphosphino-2',4',6'-triisopropyl-1,1'-biphenyl)[2-(2'-amino-1,1'-biphenyl)]palladium(II) |
| δ | parts per million referenced to residual solvent peak |

A. Synthesis of Intermediates

Intermediate I-1

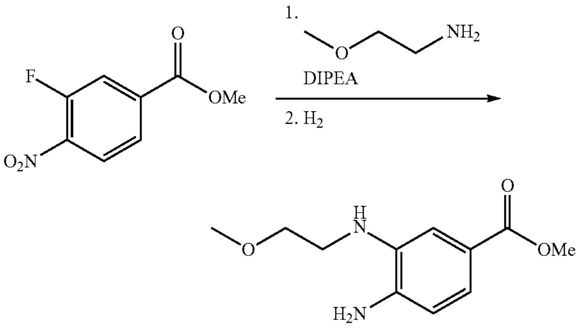

I-1

Methyl 4-amino-3-(2-methoxyethylamino)benzoate (I-1): To a solution of methyl 3-fluoro-4-nitro-benzoate (50.0 g, 251 mmol) in THF (400 mL) was added diisopropylethylamine (70.0 mL, 402 mmol) and 2-Methoxyethylamine (34.9 mL, 402 mmol). The resulting solution was heated to 55° C. for 6 hrs. Upon completion the solvent was removed, the resulting residue taken up in EtOAc (150 mL), washed with brine (30 mL), concentrated and carried forward without further purification. Methyl 3-(2-methoxyethylamino)-4-nitro-benzoate (20.0 g, 78.7 mmol) was then dissolved in EtOAc:EtOH (1:1, 140 mL) after which 10% palladium on carbon (5.02 g, 4.72 mmol) was then added. The resulting suspension was stirred under a hydrogen balloon at room temperature for 16 hrs. The reaction mixture was filtered through Celite washing with EtOAc (100 mL) and concentrated to give the desired compound without further purification: ES/MS: 225.2 ($M+H^+$).

Intermediates I-2 and I-3

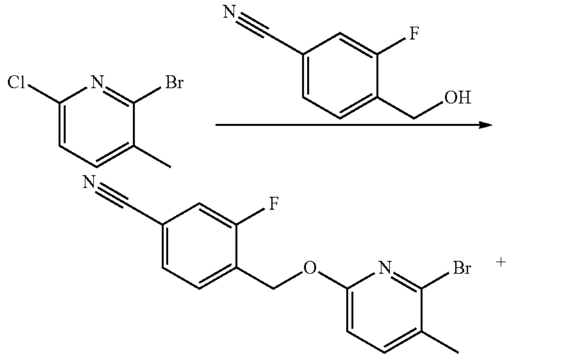

I-2

I-3

4-(((6-bromo-5-methylpyridin-2-yl)oxy)methyl)-3-fluorobenzonitrile (I-2) and 4-(((6-chloro-3-methylpyridin-2-yl)oxy)methyl)-3-fluorobenzonitrile (I-3): To a mixture of 3-fluoro-4-(hydroxymethyl)benzonitrile (0.659 g, 4.36 mmol) and 2-bromo-6-chloro-3-methyl-pyridine (750 mg, 3.63 mmol) in THF (36.0 mL) was added potassium tert-butoxide (0.736 g, 6.56 mmol) and the reaction mixture was stirred for 16 h at room temperature. The reaction was quenched by the addition of saturated aqueous ammonium chloride and the mixture was extracted with EtOAc (3×). The combined organic extracts were washed with brine, dried over sodium sulfate, filtered and the filtrate was concentrated in vacuo. The crude residue was purified by column chromatography (0-10% EtOAc in hexane then 1% MeOH in DCM) to give the title compounds (inseparable mixture, ~2:1 ratio): ES/MS m/z: 321.2, 208.0 ($M+H^+$).

Intermediate I-4

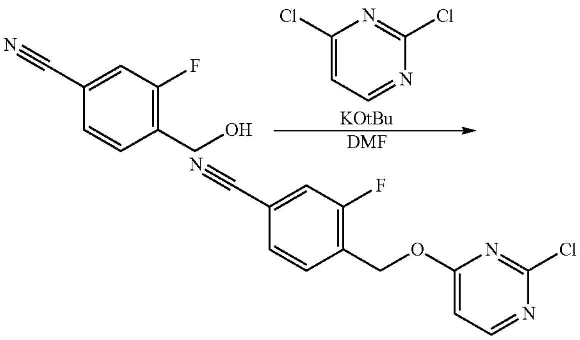

I-4

4-(((2-chloropyrimidin-4-yl)oxy)methyl)-3-fluorobenzonitrile (I-4): To a solution of 3-fluoro-4-(hydroxymethyl)benzonitrile (609 mg, 4.03 mmol) in tetrahydrofuran (1.00 mL) was added potassium tert-butoxide (237 mg, 2.11 mmol) and stirred for 5 min at room temperature. This solution was then added to a frozen solution of 2,4-dichloropyrimidine (300 mg, 2.01 mmol) in N,N-dimethylformamide (1.50 mL) cooled to −78° C. and the reaction mixture was warmed slowly to room temperature and stirred for 1 h. The mixture was poured into 50 mL of water, and stirred for 5 min. The precipitate was isolated to give the title compound which was used directly without further purification: ES/MS m/z: 264.1 ($M+H^+$); $^1H$ NMR (400 MHz, $CDCl_3$) δ 8.39 (d, J=5.7 Hz, 1H), 7.66 (t, J=7.4 Hz, 1H), 7.53 (dd, J=8.0, 1.5 Hz, 1H), 7.44 (dd, J=9.2, 1.5 Hz, 1H), 6.78 (d, J=5.7 Hz, 1H), 5.57 (s, 2H).

Intermediate I-5

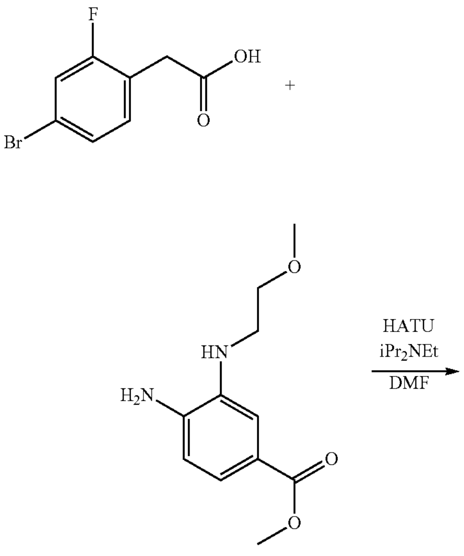

I-1

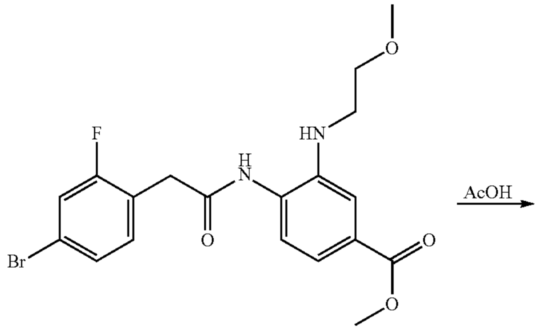

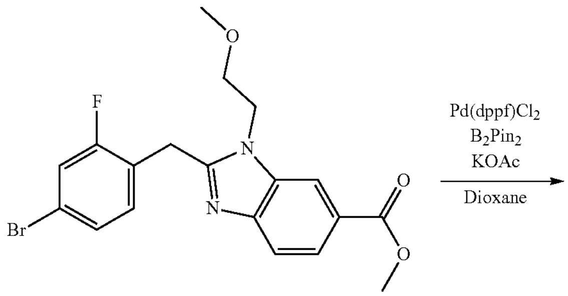

-continued

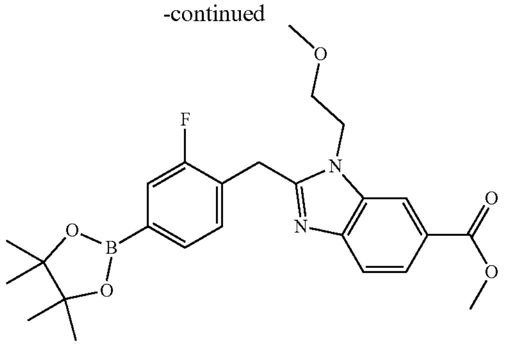

I-5

Methyl 4-{[2-(4-bromo-2-fluoro-phenyl)acetyl]amino}-3-(2-methoxyethylamino)benzoate: To a solution of 2-(4-bromo-2-fluoro-phenyl)acetic acid (1.00 g, 4.29 mmol) in DMF (20.0 mL) was added methyl 4-amino-3-(2-methoxyethylamino)benzoate (1.18 g, 5.28 mmol) and O-(7-Azabenzotriazol-1-yl)-N,N,N',N'-tetramethyluronium hexafluorophosphate (1.96 g, 5.15 mmol) followed by N,N-diisopropylethylamine (3.74 mL, 21.5 mmol) and the reaction mixture was stirred for 2 h at room temperature. The reaction was concentrated in vacuo, the residue was taken up in EtOAc and washed with water (1×) and brine (1×). The organic layer was dried over sodium sulfate, filtered and concentrated in vacuo. The crude residue was taken forward without further purification, assuming full conversion: ES/MS m/z: 583.5 ($M+H^+$).

Methyl 2-[(4-bromo-2-fluoro-phenyl)methyl]-3-(2-methoxyethyl)benzimidazole-5-carboxylate: The crude product from the previous step, methyl 4-{[2-(4-bromo-2-fluoro-phenyl)acetyl]amino}-3-(2-methoxyethylamino)benzoate (1.89 g, 4.29 mmol) was dissolved in AcOH (40.0 mL) and the reaction mixture was heated to 60° C. for 2 h. The reaction mixture was concentrated in vacuo and the crude residue was taken up in DCM and washed with saturated aqueous sodium bicarbonate. The layers were separated and the aqueous layer was extracted with DCM (2×). The combined organic extracts were dried over sodium sulfate, filtered and the filtrate was concentrated in vacuo. The crude residue was purified by column chromatography (0-100% EtOAc in hexane) to give the title compound: ES/MS m/z: 421.9 ($M+H^+$).

Methyl 2-{[2-fluoro-4-(4,4,5,5-tetramethyl-1,3,2-dioxaborolan-2-yl)phenyl]methyl}-3-(2-methoxyethyl)benzimidazole-5-carboxylate: To a vial was added methyl 2-[(4-bromo-2-fluoro-phenyl)methyl]-3-(2-methoxyethyl) benzimidazole-5-carboxylate (200 mg, 0.475 mmol), 4,4,5,5-tetramethyl-2-(4,4,5,5-tetramethyl-1,3,2-dioxaborolan-2-yl)-1,3,2-dioxaborolane (145 mg, 0.570 mmol), (1,1'-bis (diphenylphosphino)ferrocene)-dichloropalladium(II) (33.6 mg, 0.0475 mmol) and potassium acetate (0.140 g, 1.42 mmol). 1,4-dioxane (4.80 mL) was added and the reaction was heated to 100° C. for 24 h. The reaction mixture was filtered through Celite, eluting with DCM and the filtrate was concentrated in vacuo. The crude residue was purified by column chromatography (0-100% EtOAc in hexane) to give the title compound: ES/MS m/z: 469.4 ($M+H^+$).

Intermediate I-6

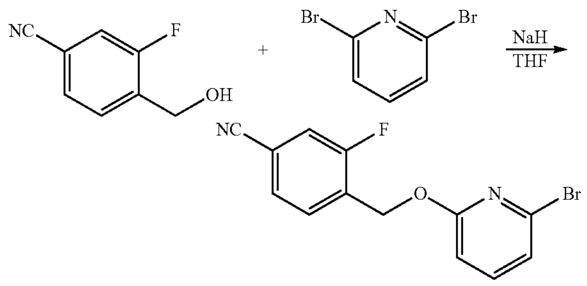

I-6

4-[(6-bromo-2-pyridyl)oxymethyl]-3-fluoro-benzonitrile (I-6): To a dried 100 mL RBF was added 3-fluoro-4-(hydroxymethyl)benzonitrile (2 g, 13.2 mmol). The material was dissolved in dry THF (20 mL) under a nitrogen atmosphere at 0° C. Sodium hydride (60% dispersion in mineral oil, 0.507 g, 13.2 mmol) was added in one portion, and the mixture was stirred for 30 minutes at 0° C. under $N_2$. Subsequently, 2,6-dibromopyridine (3.13 g, 13.2 mmol) was added, and the reaction mixture was stirred room temperature overnight. The mixture was diluted with EtOAc (100 mL) and water (20 mL). The layers were separated, and the aqueous layer was extracted with ethyl acetate (2×30 mL). The combined organic layers were dried over $MgSO_4$, filtered, and concentrated under reduced pressure. The crude material was purified by silica gel column chromatography (eluent: EtOAc/hexanes) to afford the Intermediate I-6: ES/MS: 307.058 (M+H$^+$); $^1$H NMR (400 MHz, Chloroform-d) δ 7.72-7.63 (m, 1H), 7.52-7.46 (m, 2H), 7.41 (dd, J=9.2, 1.5 Hz, 1H), 7.14 (dd, J=7.5, 0.7 Hz, 1H), 6.79 (dd, J=8.2, 0.7 Hz, 1H), 5.50 (t, J=0.9 Hz, 2H).

Intermediate I-7

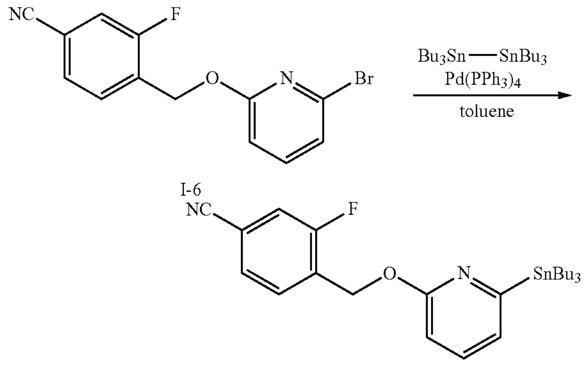

I-6

I-7

3-fluoro-4-[(6-tributylstannyl-2-pyridyl)oxymethyl]benzonitrile (I-7): To a 40 mL vial was added 4-[(6-bromo-2-pyridyl)oxymethyl]-3-fluoro-benzonitrile (I-6) (400 mg, 1.3 mmol), tetrakis(triphenylphosphine)palladium(0) (151 mg, 0.13 mmol), and tributyl(tributylstannyl)stannane (907 mg, 1.56 mmol). Toluene (8 mL) was added, and the mixture was degassed with argon for 2 minutes. The vial was sealed, and stirred overnight at 100° C. LCMS showed apparent formation of product, and the vial was cooled to room temperature. The mixture was dry-loaded onto silica gel, and purified by silica gel chromatography (eluent: Hexanes, then EtOAc/Hexanes) to afford Intermediate I-7: ES/MS: 517.402 (M+H$^+$).

Intermediate I-8

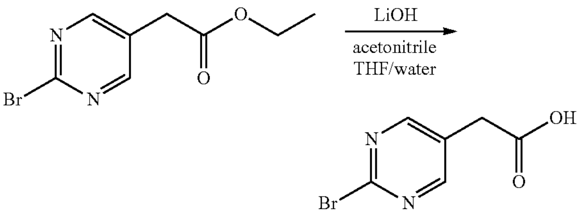

I-8

2-(2-bromopyrimidin-5-yl)acetic acid (I-8): To a 40 mL vial was added ethyl 2-(2-bromopyrimidin-5-yl)acetate (250 mg, 1.02 mmol), acetonitrile (3 mL), and THF (3 mL). Lithium hydroxide (49 mg, 2.04 mmol) dissolved in water (0.75 mL) was added, and the mixture was stirred 1 hour at 65° C. LCMS showed apparent formation of product, and mixture was diluted with EtOAc (60 mL) and acidified with 1 M HCl. The layers were separated, and the aqueous layer was extracted with EtOAc (2×30 mL). The combined organic layers were dried over $MgSO_4$, filtered, and concentrated under reduced pressure to afford the product, which was used without further purification: ES/MS: 217.006 (M+H$^+$).

Intermediate I-9

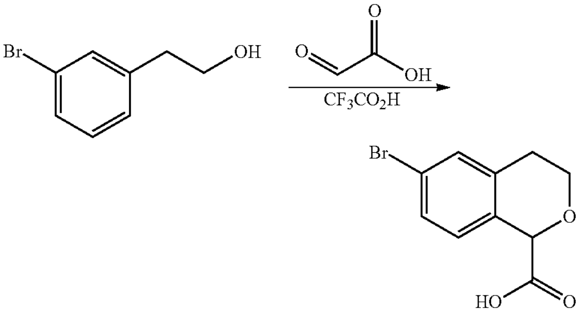

I-9

6-bromoisochromane-1-carboxylic acid (I-9): To a 40 mL vial was added 2-(3-bromophenyl)ethanol (500 mg, 2.49 mmol), and glyoxylic acid monohydrate (458 mg, 4.97 mmol). Trifluoroacetic acid (2 mL) was added, and the mixture was stirred overnight at 70° C. The mixture was concentrated under reduced pressure, and the crude residue was partitioned between EtOAc (75 mL) and water (50 mL), and basified with 1 M NaOH. The layers separated, and the aqueous layer was washed once more with EtOAc (50 mL). The aqueous layer was acidified with 1 M HCl (pH<4), and extracted with EtOAc (3×75 mL). These combined organic layers were dried over $MgSO_4$, filtered, and concentrated under reduced pressure. The Intermediate I-9 was used without further purification.

Intermediate I-10

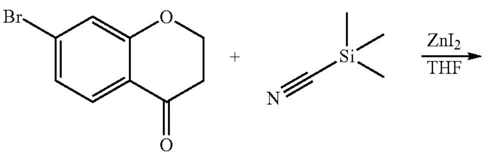

-continued

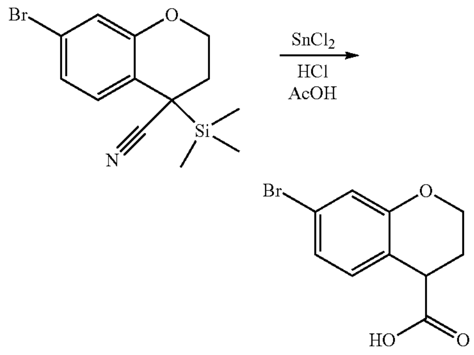

I-10

7-bromochromane-4-carboxylic acid (I-10): To a suspension of 7-bromochroman-4-one (1 g, 4.4 mmol) in THF (5 mL) was added zinc(II) iodide (85 mg, 0.264 mmol), followed by the dropwise addition of trimethylsilylformonitrile (1.65 mL, 13.2 mmol) via syringe. The reaction was stirred overnight at room temperature, then diluted with EtOAc (50 mL) and washed with water (50 mL) and brine (50 mL). The organic layer was dried over $MgSO_4$, filtered, and concentrated. The crude material was then dissolved in acetic acid (15 mL) and concentrated hydrochloric acid (15 mL), and stannous chloride (3.32 g, 17.5 mmol) was added. The reaction was heated at reflux for 24 hours. The mixture was cooled, diluted with dichloromethane (50 mL), and washed with water (50 mL) and brine (50 mL). The organic layer was dried over $MgSO_4$, filtered, and concentrated. The material was determined to be of sufficient purity to carry forward without further purification: $^1H$ NMR (400 MHz, $CDCl_3$) δ 7.21-7.15 (m, 1H), 7.09-7.00 (m, 2H), 4.33-4.23 (m, 2H), 3.79 (dd, J=6.1, 3.8 Hz, 1H), 2.46-2.30 (m, 1H), 2.21-2.13 (m, 1H).

Intermediate I-11

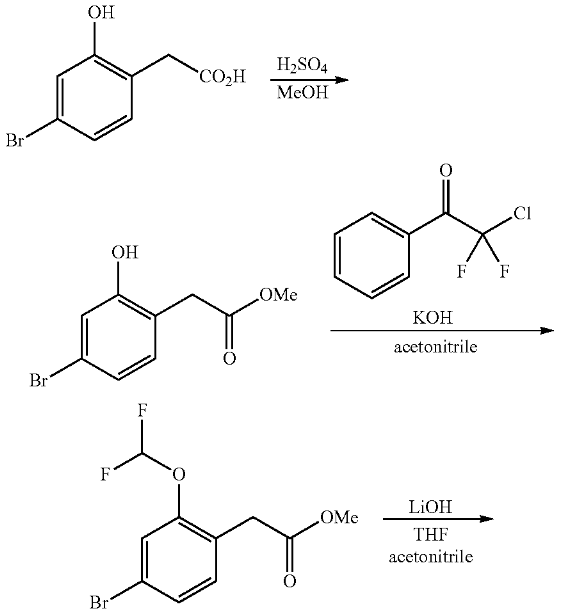

-continued

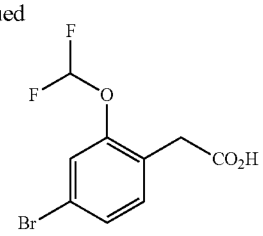

I-11

Methyl 2-(4-bromo-2-hydroxyphenyl)acetate: To a solution of 2-(4-bromo-2-hydroxy-phenyl)acetic acid (250 mg, 1.08 mmol) in methanol (10 mL) was added concentrated sulfuric acid (0.1 mL). The mixture was heated at 60° C. for 2 hours, then concentrated under reduced pressure. The residue was dissolved in water (10 mL) and the mixture was extracted with EtOAc (2×30 mL). The combined organic phases were dried over $MgSO_4$. Concentration under reduced pressure gave the product, which was carried forward without further purification: $^1H$ NMR (400 MHz, $CDCl_3$) δ 7.14 (d, J=2.0 Hz, 1H), 7.04 (dd, J=8.1, 2.0 Hz, 1H), 6.97 (d, J=8.1 Hz, 1H), 3.79 (s, 3H), 3.66 (s, 2H).

Methyl 2-(4-bromo-2-(difluoromethoxy)phenyl)acetate: Into a mixture of methyl 2-(4-bromo-2-hydroxy-phenyl) acetate (250 mg, 1.02 mmol), aqueous KOH (30 wt %, 4 mL), and acetonitrile (5 mL) at −78° C. was added chlorodifluoroacetophenone (972 mg, 5.1 mmol). The reaction mixture was warmed to room temperature, and was then heated to 80° C. overnight. The mixture was diluted with water (10 mL) and extracted with $Et_2O$ (3×50 mL). The combined organic layers were dried over $MgSO_4$, filtered, and concentrated under reduced pressure. The residue was purified by silica gel chromatography (eluent: EtOAc/hexane) to afford the product: $^1H$ NMR (400 MHz, $CDCl_3$) δ 7.40-7.33 (m, 2H), 7.19 (d, J=8.1 Hz, 1H), 6.50 (t, J=73.4 Hz, 1H), 3.73 (s, 3H), 3.67 (s, 2H).

2-[4-bromo-2-(difluoromethoxy)phenyl]acetic acid (I-11): To a 25 mL RBF was added methyl 2-(4-bromo-2-(difluoromethoxy)phenyl)acetate (154 mg, 0.522 mmol), THF (4 mL) and acetonitrile (4 mL). Lithium hydroxide (1 M in water, 2.61 mL, 2.61 mmol) was added, and the mixture was stirred overnight at 70° C. The mixture was acidified with 1 M HCl, and partitioned between water (20 mL) and EtOAc (50 mL). The layers were separated, and the aqueous layer was extracted with EtOAc (2×20 mL). The combined organic layers were dried over $MgSO_4$, filtered, and concentrated under reduced pressure. The crude material was carried forward without further purification.

Intermediate I-12

I-12

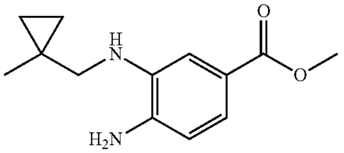

Methyl 4-amino-3-(((1-methylcyclopropyl)methyl)amino)benzoate (I-12): Methyl 4-amino-3-(((1-methylcyclopropyl)methyl)amino)benzoate was prepared identically as described for Intermediate I-1 substituting methoxyethylamine with (1-methylcyclopropyl)methanamine hydrochloride: ES/MS: 235.1 (M+H$^+$).

Intermediate I-13

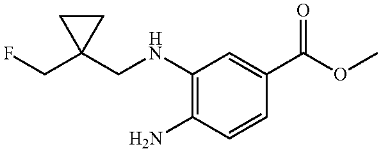

I-13

Methyl 4-amino-3-(((1-(fluoromethyl)cyclopropyl)methyl)amino)benzoate (I-13): Methyl 4-amino-3-(((1-(fluoromethyl)cyclopropyl)methyl)amino)benzoate was prepared identically as described for Intermediate I-1 substituting methoxyethylamine with (1-(fluoromethyl)cyclopropyl)methanamine; 2,2,2-trifluoroacetic acid: ES/MS: 253.3 (M+H$^+$).

Intermediate I-14

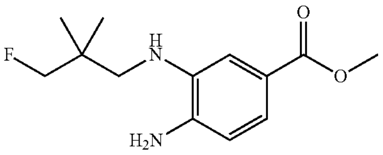

I-14

Methyl 4-amino-3-((3-fluoro-2,2-dimethylpropyl)amino)benzoate (I-14): Methyl 4-amino-3-((3-fluoro-2,2-dimethylpropyl)amino)benzoate was prepared identically as described for Intermediate I-1 substituting methoxyethylamine with 3-fluoro-2,2-dimethyl-propan-1-amine hydrochloride: ES/MS: 255.4 (M+H$^+$).

Intermediate I-15

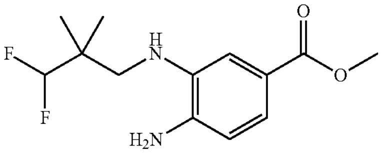

I-15

Methyl 4-amino-3-((3,3-difluoro-2,2-dimethylpropyl)amino)benzoate (I-15): Methyl 4-amino-3-((3,3-difluoro-2,2-dimethylpropyl)amino)benzoate was prepared identically as described for Intermediate I-1 substituting methoxyethylamine with 3,3-difluoro-2,2-dimethyl-propan-1-amine; hydrochloride: ES/MS: 273.2 (M+H$^+$).

Intermediate I-16

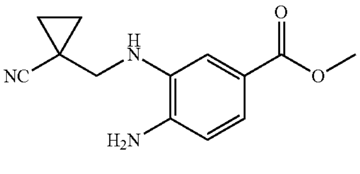

I-16

Methyl 4-amino-3-(((1-cyanocyclopropyl)methyl)amino)benzoate (I-16): Methyl 4-amino-3-(((1-cyanocyclopropyl)methyl)amino)benzoate was prepared identically as described for Intermediate I-1 substituting methoxyethylamine with 1-(aminomethyl)cyclopropanecarbonitrile hydrochloride: ES/MS: 246.3 (M+H$^+$).

Intermediate I-17

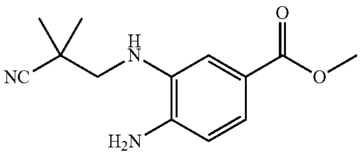

I-17

Methyl 4-amino-3-((2-cyano-2-methylpropyl)amino)benzoate (I-17): Methyl 4-amino-3-(((1-cyanocyclopropyl)methyl)amino)benzoate was prepared identically as described for Intermediate I-1 substituting methoxyethylamine with 3-amino-2,2-dimethyl-propanenitrile: ES/MS: 248.4 (M+H$^+$).

Intermediate I-18

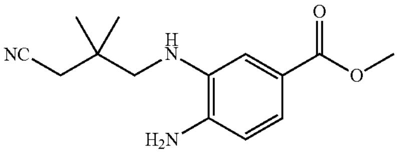

I-18

Methyl 4-amino-3-((3-cyano-2,2-dimethylpropyl)amino)benzoate (I-18): Methyl 4-amino-3-((3-cyano-2,2-dimethylpropyl)amino)benzoate was prepared identically as described for Intermediate I-1 substituting methoxyethylamine with 4-amino-3,3-dimethyl-butanenitrile: ES/MS: 262.5 (M+H$^+$).

Intermediate I-19

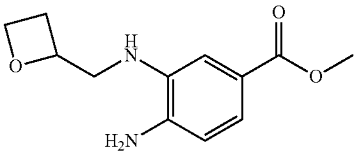

I-19

Methyl 4-amino-3-((oxetan-2-ylmethyl)amino)benzoate (I-19): Methyl 4-amino-3-((oxetan-2-ylmethyl)amino)benzoate was prepared identically as described for Intermediate I-1 substituting methoxyethylamine with oxetan-2-ylmethanamine: ES/MS: 237.0 (M+H$^+$).

Intermediate I-20

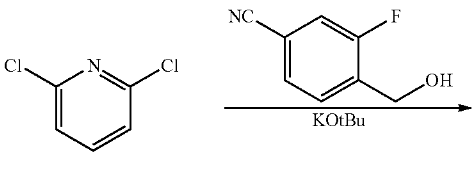

-continued

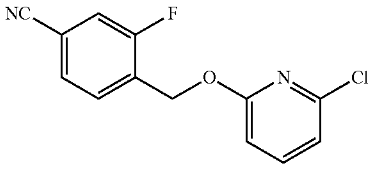

I-20

4-(((6-chloropyridin-2-yl)oxy)methyl)-3-fluorobenzonitrile: To a suspension of potassium tert-butoxide reagent grade, 95% (6.3 g, 56.14 mmol) in THF (80 mL) at 10-15° C. was added 3-fluoro-4-(hydroxymethyl)benzonitrile (5.64 g, 37.3 mmol). The black solution was stirred for 45 min after which 2,6-dichloropyridine (4.6 g, 31.08 mmol) was added and stirred for 18 hr. The mixture was poured into saturated $NH_4Cl$ (20 mL) solution. EtOAc (20 mL) was added and the mixture was stirred for 15 min. The resulting mixture was filtered through Celite, the organic layers separated, and the aqueous layer was extracted with EtOAc (2×120 mL). Combined organic extracts were washed with brine (100 mL) and dried over sodium sulfate to give crude product which was purified by silica gel chromatography (eluent: EtOAc/hexanes): ES/MS: 263.2 (M+H$^+$); $^1$H NMR (400 MHz, $CDCl_3$) δ 7.68 (t, J=7.5 Hz, 1H), 7.60 (dd, J=8.2, 7.5 Hz, 1H), 7.50 (dd, J=7.9, 1.6 Hz, 1H), 7.42 (dd, J=9.2, 1.6 Hz, 1H), 6.99 (dd, J=7.5, 0.7 Hz, 1H), 6.77 (dd, J=8.2, 0.7 Hz, 1H), 5.51 (t, J=0.9 Hz, 2H).

Intermediate I-21

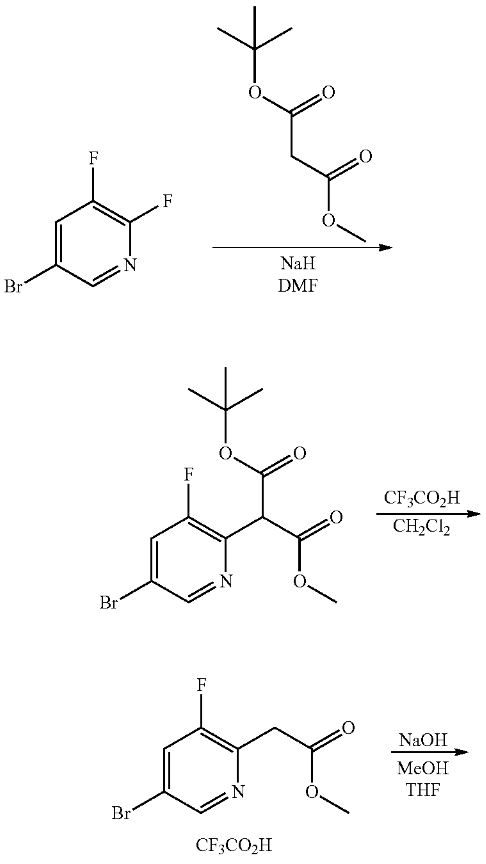

-continued

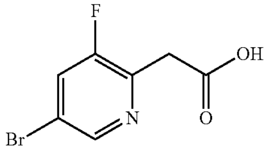

I-21

1-(tert-Butyl) 3-methyl 2-(5-bromo-3-fluoropyridin-2-yl) malonate: To a 40 mL vial was added tert-butyl methyl malonate (898 mg, 5.16 mmol) and DMF (10 mL). The solution was cooled to 0° C., and NaH (60% in mineral oil, 237 mg, 6.19 mmol) was added. The reaction mixture was stirred for 20 min at room temperature, and gas evolution was observed. The reaction was then cooled to 0° C. and 5-bromo-2,3-difluoropyridine (1.0 g, 5.16 mmol) was added, and the reaction was stirred overnight. LCMS showed formation of the product. The mixture was partitioned between EtOAc (50 mL) and water (20 mL) and the organic layer was separated, dried over $MgSO_4$, and concentrated under reduced pressure to afford 1-(tert-butyl) 3-methyl 2-(5-bromo-3-fluoropyridin-2-yl)malonate which was carried directly forward to the next step: ES/MS: 348.470 (M+H$^+$).

Methyl 2-(5-bromo-3-fluoropyridin-2-yl)acetate: To a 100 mL RBF was added 1-(tert-butyl) 3-methyl 2-(5-bromo-3-fluoropyridin-2-yl)malonate (1.4 g, 4.02 mmol), trifluoroacetic acid (10 mL), and $CH_2Cl_2$ (10 mL). The mixture was stirred at room temperature overnight. LC/MS showed formation of the product. The solvents were evaporated under reduced pressure to afford the product as a trifluoroacetate salt: ES/MS: 248.347 (M+H$^+$).

2-(5-bromo-3-fluoro-2-pyridyl)acetic acid (I-21): To a 40 mL RBF was added methyl 2-(5-bromo-3-fluoropyridin-2-yl)acetate (trifluoroacetate salt) (1.2 g, 3.31 mmol). Methanol (10 mL) and THF (5 mL) were added, and then 1 M NaOH (6.63 mL, 6.63 mmol) was added. The reaction mixture was stirred at 70° C. overnight. The mixture was concentrated under reduced pressure, and the residue was dissolved in water and acidified with 1N HCl. The resulting mixture was extracted 3× with a mixture of DCM and methanol. The combined organic layers were dried over $MgSO_4$, filtered, and concentrated under reduced pressure. The crude material was carried forward without further purification: ES/MS: 234.159 (M+H$^+$).

Intermediate I-22

I-22

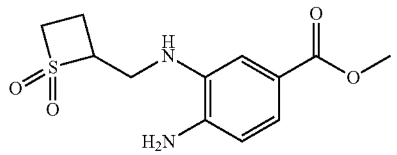

Methyl 4-amino-3-(((1,1-dioxidothietan-2-yl)methyl)amino)benzoate (I-22): Methyl 4-amino-3-(((1,1-dioxidothietan-2-yl)methyl)amino)benzoate was prepared identically as described for Intermediate I-1 substituting methoxyethylamine with (1,1-dioxothietan-2-yl)methanamine; hydrochloride: ES/MS: 285.2 (M+H$^+$).

Intermediate I-23

I-23

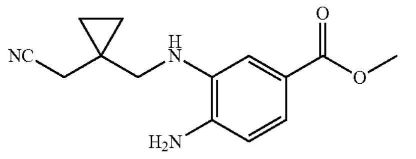

Methyl 4-amino-3-(((1-(cyanomethyl)cyclopropyl)methyl)amino)benzoate (I-23): Methyl 4-amino-3-(((1-(cyanomethyl)cyclopropyl)methyl)amino)benzoate was prepared identically as described for Intermediate I-1 substituting methoxyethylamine with 2-[1-(aminomethyl)cyclopropyl]acetonitrile; hydrochloride: ES/MS: 260.2 (M+H+).

Intermediate I-24

I-24

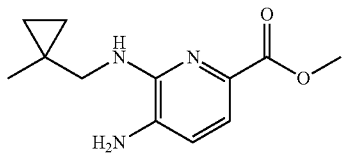

Methyl 5-amino-6-(((1-methylcyclopropyl)methyl)amino)picolinate (I-24): Methyl 4-amino-3-((oxetan-2-ylmethyl)amino)benzoate was prepared identically as described for Intermediate I-1 substituting methoxyethylamine with (1-methylcyclopropyl)methanamine hydrochloride and substituting methyl 3-fluoro-4-nitro-benzoate with methyl 6-chloro-5-nitro-pyridine-2-carboxylate: ES/MS: 236.3 (M+H+).

Intermediate I-25

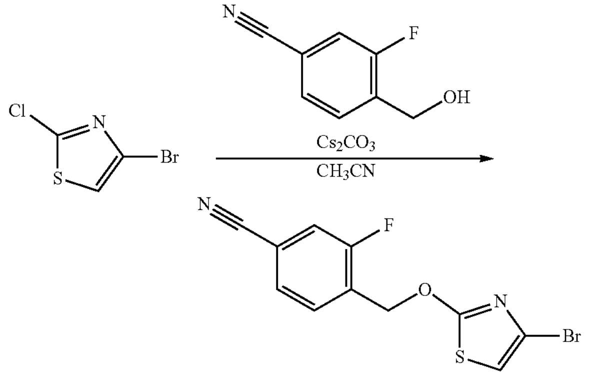

I-25

4-(((4-bromothiazol-2-yl)oxy)methyl)-3-fluorobenzonitrile (I-25):

To a vial was added 4-bromo-2-chloro-thiazole (250 mg, 1.26 mmol), 3-fluoro-4-(hydroxymethyl)benzonitrile (0.209 g, 1.39 mmol), cesium carbonate (0.821 g, 2.52 mmol) and acetonitrile (4 mL) and the reaction mixture was heated to 60° C. for 16 h. The reaction mixture was poured into water and the precipitate was filtered off, washed with water and dried under vacuum to yield the title compound: ES/MS m/z: 314.3 (M+H+); $^1$H NMR (400 MHz, $CDCl_3$) δ 7.66 (t, J=7.5 Hz, 1H), 7.56-7.50 (m, 1H), 7.44 (dd, J=9.1, 1.6 Hz, 1H), 6.68 (s, 1H), 5.60 (s, 2H).

Intermediate I-26

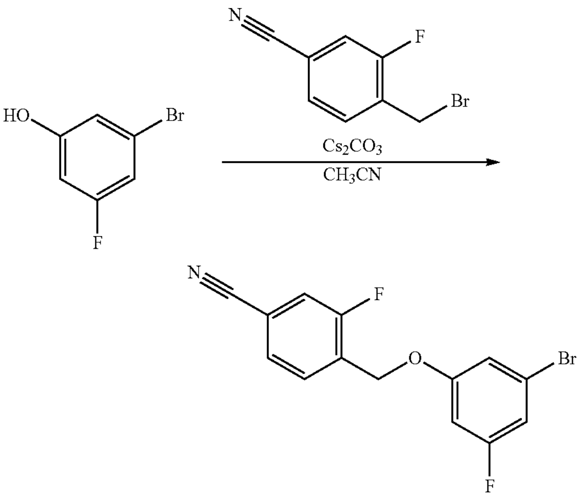

I-26

4-((3-bromo-5-fluorophenoxy)methyl)-3-fluorobenzonitrile (I-26)

To a vial was added 3-bromo-5-fluoro-phenol (300 mg, 1.57 mmol), 4-(bromomethyl)-3-fluoro-benzonitrile (370 mg, 1.73 mmol) and cesium carbonate (930 mg, 2.86 mmol) followed by acetonitrile (5.00 mL) and the reaction mixture was stirred for 16 h at 60° C. The reaction mixture was poured into water and the precipitate was filtered off, washed with water and dried under vacuum to yield the title compound: $^1$H NMR (400 MHz, $CDCl_3$) δ 7.67 (t, J=7.5 Hz, 1H), 7.56-7.52 (m, 1H), 7.44 (dd, J=9.3, 1.6 Hz, 1H), 6.99-6.92 (m, 2H), 6.70-6.64 (m, 1H), 5.17 (s, 2H).

Intermediate I-27

I-27

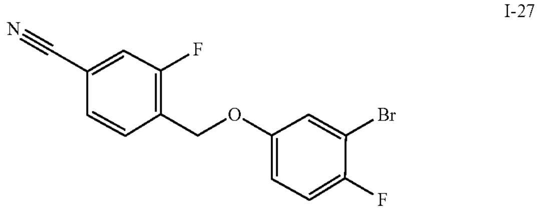

4-((3-bromo-4-fluorophenoxy)methyl)-3-fluorobenzonitrile (I-27): The title compound was prepared according to the procedure as described for Intermediate I-26 substituting 3-bromo-5-fluoro-phenol with 3-bromo-4-fluoro-phenol: $^1$H NMR (400 MHz, $CDCl_3$) δ 7.68 (t, J=7.5 Hz, 1H), 7.54 (dd, J=8.0, 1.6 Hz, 1H), 7.43 (dd, J=9.3, 1.5 Hz, 1H), 7.21-7.17 (m, 1H), 7.09 (dd, J=9.0, 8.0 Hz, 1H), 6.93-6.87 (m, 1H), 5.15 (s, 2H).

Intermediate I-28

I-28

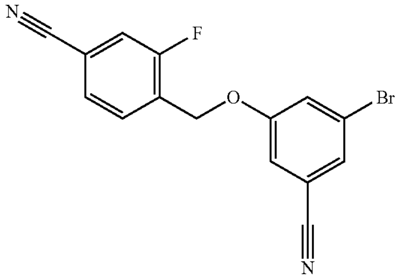

4-((3-bromo-5-cyanophenoxy)methyl)-3-fluorobenzonitrile (I-28): The title compound was prepared according to the procedure as described for Intermediate I-26 substituting 3-bromo-5-fluoro-phenol with 3-bromo-5-hydroxy-benzonitrile: $^{1}$H NMR (400 MHz, $CDCl_3$) δ 7.66 (t, J=7.5 Hz, 1H), 7.58-7.53 (m, 1H), 7.49-7.44 (m, 2H), 7.42-7.39 (m, 1H), 7.22-7.18 (m, 1H), 5.21 (s, 2H).

Intermediate I-29

I-29

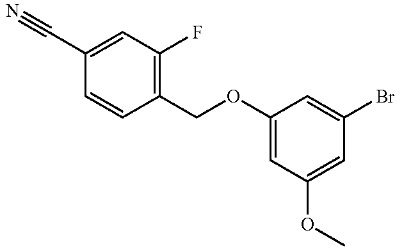

4-((3-bromo-5-methoxyphenoxy)methyl)-3-fluorobenzonitrile (I-29): The title compound was prepared according to the procedure as described for Intermediate I-26 substituting 3-bromo-5-fluoro-phenol with 3-bromo-5-methoxy-phenol: $^{1}$H NMR (400 MHz, $CDCl_3$) δ 7.71-7.64 (m, 1H), 7.56-7.51 (m, 1H), 7.45-7.40 (m, 1H), 6.79-6.72 (m, 2H), 6.47 (t, J=2.3 Hz, 1H), 5.16 (s, 2H), 3.80 (s, 3H).

Intermediate I-30

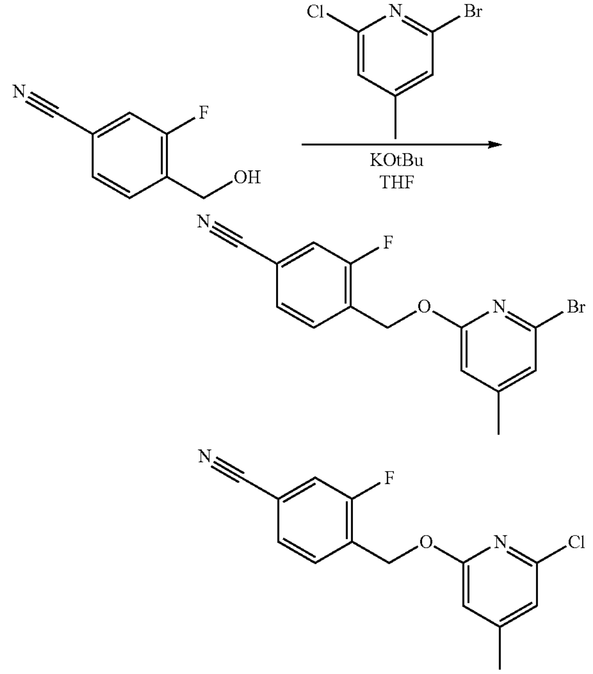

I-30

4-(((6-bromo-4-methylpyridin-2-yl)oxy)methyl)-3-fluorobenzonitrile (I-30): To a solution of 3-fluoro-4-(hydroxymethyl)benzonitrile (0.878 g, 5.81 mmol) in THF cooled to 0° C. was added potassium tert-butoxide (0.982 g, 8.75 mmol) and the reaction mixture was stirred for 10 min. 2-bromo-6-chloro-4-methyl-pyridine (1.00 g, 4.84 mmol) was then added and the reaction mixture was stirred at 0° for 1 h then heated to 50° C. for 3 h. The reaction mixture was cooled to room temperature, poured into water and the precipitate was filtered off and dried under vacuum to give title compound as a mixture of Br/Cl isomers: ES/MS m/z: 321.1 (M+H$^{+}$), 277.1 (M+H$^{+}$).

Intermediate I-31, I-32, I-33 and I-34

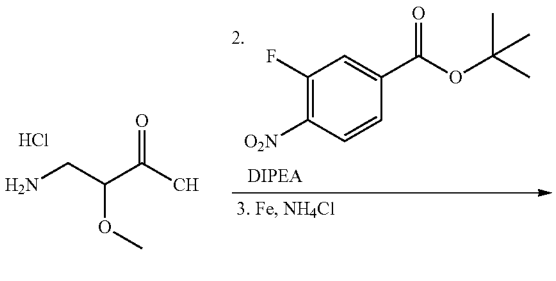

-continued
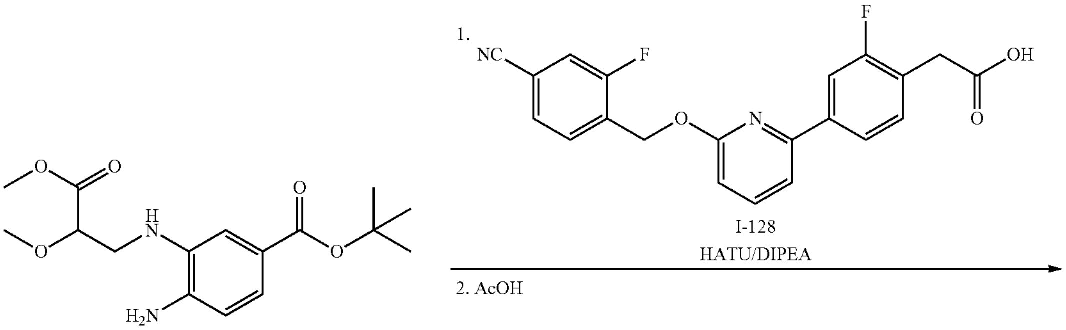
I-31
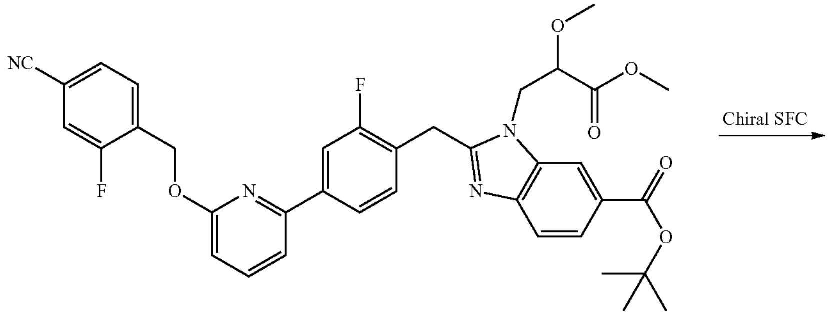
I-32
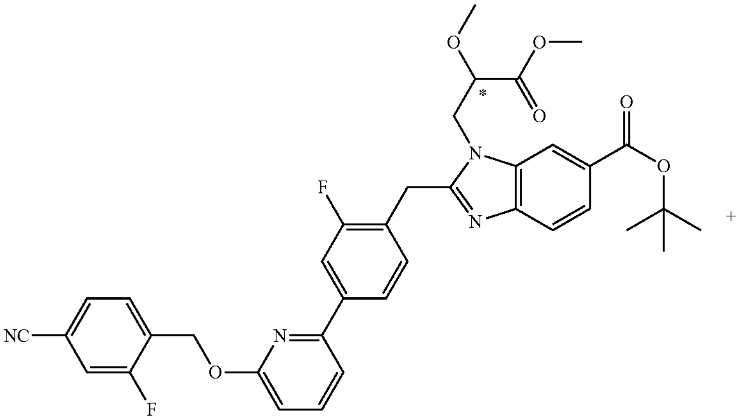
I-33
peak one
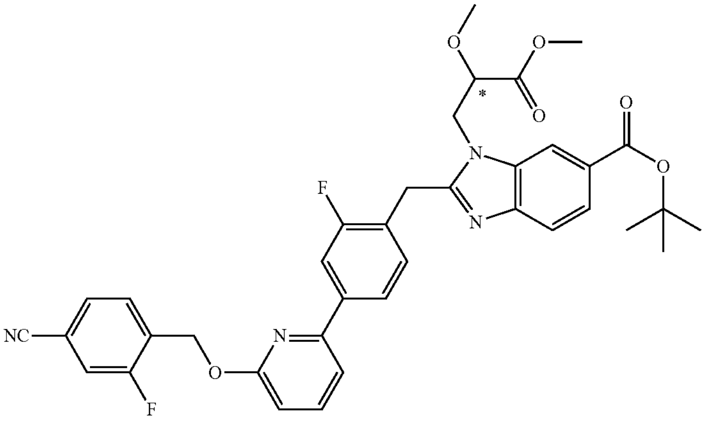
I-34
peak two Tert-butyl 4-nitro-3-((2,3-dimethoxy-3-oxopropyl)amino)benzoate: 3-amino-2-methoxy-propanoic acid hydrochloride (355 mg, 2.3 mmol) was suspended in DCM/methanol (5 mL, 3:1), and TMS diazomethane (2.0 M, 1.1 mL, 2.3 mmol) was added until a faint yellow color persisted. The reaction was quenched by addition of AcOH (~1 drop), concentrated to dryness, dissolved in MeTHF (3 mL), and again concentrated to dryness. To the resulting crude amino ester dissolved in MeTHF (3 mL); were added tert-butyl 3-fluoro-4-nitro-benzoate (500 mg, 2.1 mmol) and DIPEA (1.1 mL, 6.2 mmol). The mixture was stirred at 80° C. overnight. The reaction was then cooled, diluted with EtOAc, rinsed with aq $NH_4Cl$, dried over $Na_2SO_4$, filtered, and concentrated: ES/MS: 355.1 ($M+H^+$)

Tert-butyl 4-amino-3-[(2,3-dimethoxy-3-oxo-propyl)amino]benzoate (I-31): Crude tert-butyl 4-nitro-3-((2,3-dimethoxy-3-oxopropyl)amino)benzoate (~2.1 mmol) from the reaction above was combined in ethanol (5 mL) with sat. aq. $NH_4Cl$ (2.5 mL) and iron powder (579 mg, 10.4 mmol). The mixture was stirred at 60° C. for 45 minutes, then cooled, diluted with EtOAc (10 mL), filtered through $MgSO_4$ and Celite, concentrated to dryness, and purified by column chromatography (40-85% EtOAc in hexane) to give the title compound. ES/MS: 325.1 ($M+H^+$); $^1H$ NMR (400 MHz, Chloroform-d) δ 7.47 (dd, J=8.1, 1.8 Hz, 1H), 7.37 (d, J=1.9 Hz, 1H), 7.28 (s, 1H), 6.68 (d, J=8.1 Hz, 1H), 4.11 (dd, J=6.3, 3.6 Hz, 1H), 3.80 (s, 3H), 3.56 (dd, J=12.7, 3.8 Hz, 1H), 3.52 (s, 3H), 3.44 (dd, J=12.7, 6.4 Hz, 1H), 1.59 (s, 9H).

Tert-butyl 2-[[4-[6-[(4-cyano-2-fluoro-phenyl)methoxy]-2-pyridyl]-2-fluoro-phenyl]methyl]-3-(2,3-dimethoxy-3-oxo-propyl)benzimidazole-5-carboxylate (I-32): 2-[4-[6-[(4-cyano-2-fluoro-phenyl)methoxy]-2-pyridyl]-2-fluoro-phenyl]acetic acid (I-128, 240 mg, 0.63 mmol), tert-butyl 4-amino-3-[(2,3-dimethoxy-3-oxo-propyl)amino]benzoate (I-31, 235 mg, 0.73 mmol), HATU (360 mg, 0.95 mmol), and DIPEA (0.55 mL, 3.2 mmol) were combined in DCE/DMF (2:1, 3 mL) and stirred at 50° C. for 15 minutes. The reaction was cooled, diluted with EtOAc and rinsed with aq $NH_4Cl$, aq $NaHCO_3$, and brine. The organic fraction was dried over $Na_2SO_4$, filtered, and concentrated. The crude solids were dissolved in AcOH (2 mL) and stirred at 70° C. for 20 minutes, followed by stirring at 85° C. for 35 minutes, and at 90° C. for 40 minutes. The reaction was then cooled to room temperature, concentrated to dryness, and purified by column chromatography (40-85% EtOAc in hexane) to provide the title compound. ES/MS: 669.4 ($M+H^+$); $^1H$ NMR (400 MHz, Chloroform-d) δ 8.22-8.06 (m, 1H), 7.97 (d, J=8.5 Hz, 1H), 7.78 (d, J=8.4 Hz, 1H), 7.76-7.63 (m, 4H), 7.47 (dd, J=7.9, 1.5 Hz, 1H), 7.42 (dd, J=9.3, 1.6 Hz, 1H), 7.36 (d, J=7.4 Hz, 1H), 6.82 (d, J=8.2 Hz, 1H), 5.62 (s, 2H), 4.64-4.36 (m, 4H), 4.13-4.09 (m, 1H), 3.83 (s, 3H), 3.32 (s, 3H), 1.66 (s, 9H). $^{19}F$ NMR (376 MHz, Chloroform-d) δ −115.30–−115.58 (m), −117.61.

I-33 and I-34: Tert-butyl 2-[[4-[6-[(4-cyano-2-fluoro-phenyl)methoxy]-2-pyridyl]-2-fluoro-phenyl]methyl]-3-(2,3-dimethoxy-3-oxo-propyl)benzimidazole-5-carboxylate isomer 1 and isomer 2. Tert-butyl 2-[[4-[6-[(4-cyano-2-fluoro-phenyl)methoxy]-2-pyridyl]-2-fluoro-phenyl]methyl]-3-(2,3-dimethoxy-3-oxo-propyl)benzimidazole-5-carboxylate obtained as a mixture of 2 stereoisomers was separated by chiral SFC (IG column with 45% EtOH cosolvent) to give two distinct stereoisomers (I-33 and I-34).

Intermediates I-35 and I-36

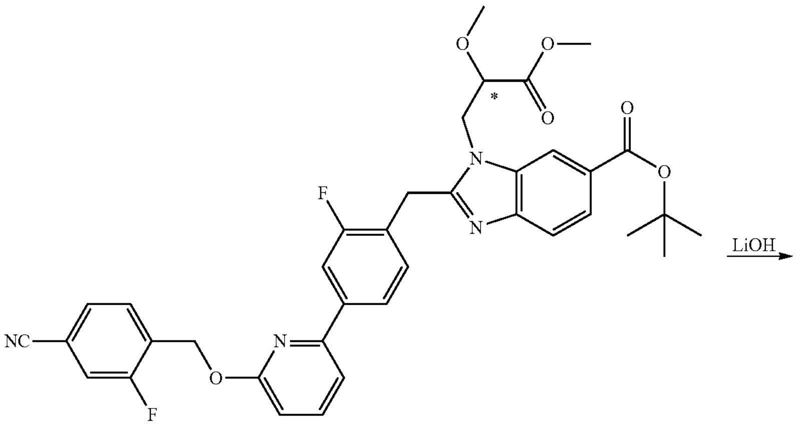

I-33
peak one

-continued

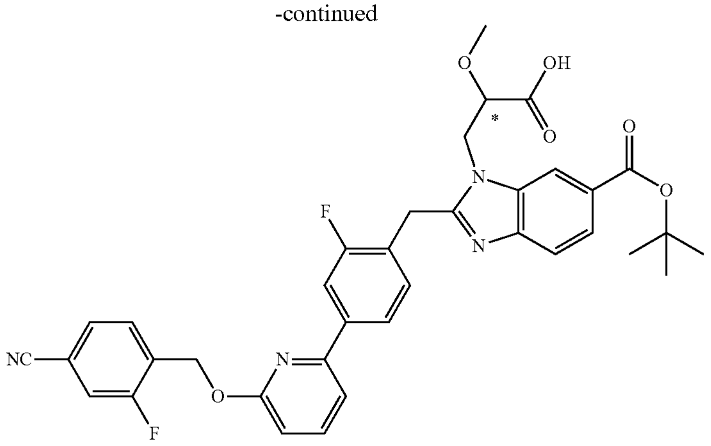

I-35

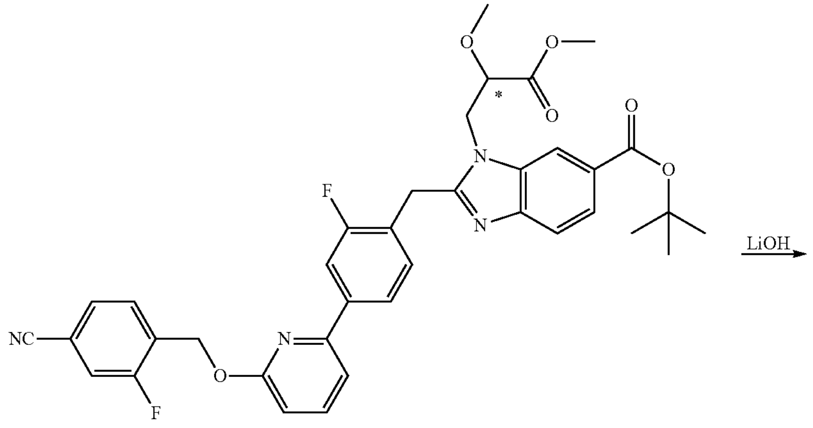

I-34
peak two

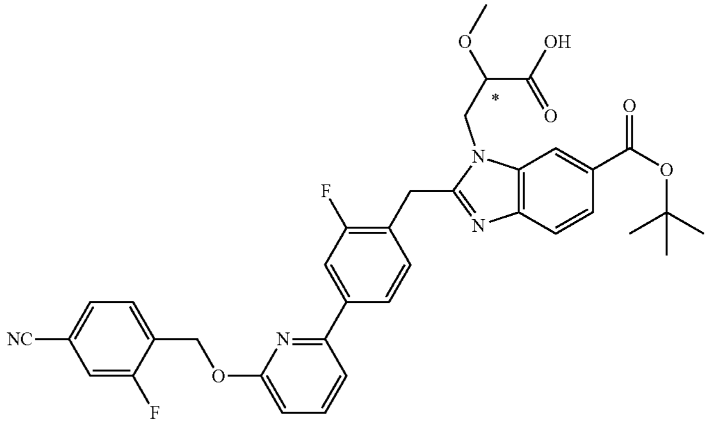

I-36

3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 1 (I-35): Tert-butyl 2-[[4-[6-[(4-cyano-2-fluoro-phenyl)methoxy]-2-pyridyl]-2-fluoro-phenyl]methyl]-3-(2,3-dimethoxy-3-oxo-propyl)benzimidazole-5-carboxylate (I-33 peak 1) (151 mg, 0.23 mmol) was combined with lithium hydroxide monohydrate (28 mg, 0.67 mmol) in THF (2 mL) and water (0.3 mL), and stirred at 30° C. After 45 minutes, the reaction was diluted with EtOAc (5 mL) and aq HCl (1 M, 2 mL). The organic layer was separated, rinsed with brine, dried over $MgSO_4$, filtered, and concentrated to provide the title compound: ES/MS: 655.2 ($M+H^+$).

3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 2 (I-36): An analogous procedure was used to hydrolyze tert-butyl 2-[[4-[6-[(4-cyano-2-fluoro-phenyl)methoxy]-2-pyridyl]-2-fluoro-phenyl]methyl]-3-(2,3-dimethoxy-3-oxo-propyl)benzimidazole-5-carboxylate peak 2: ES/MS: 655.2 ($M+H^+$).

Intermediates I-37, I-38, I-39, I-40, I-41
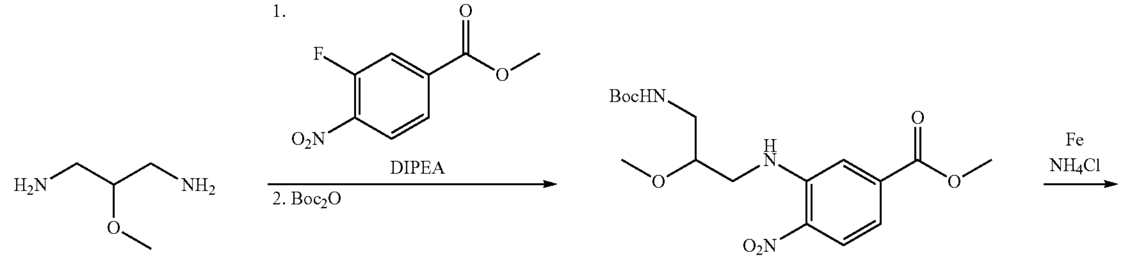
I-37
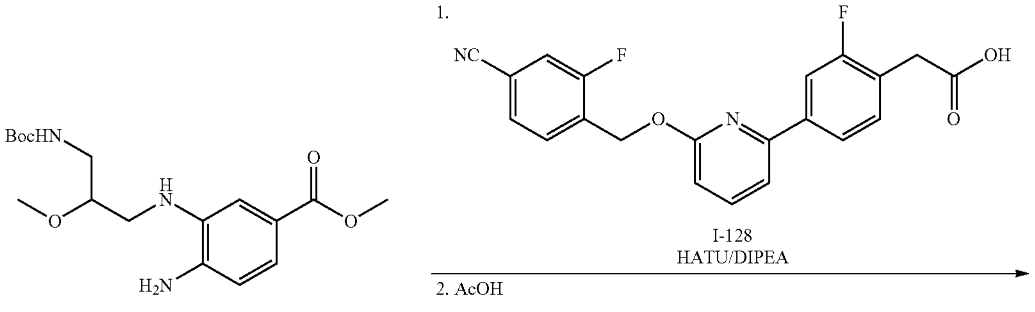
I-38
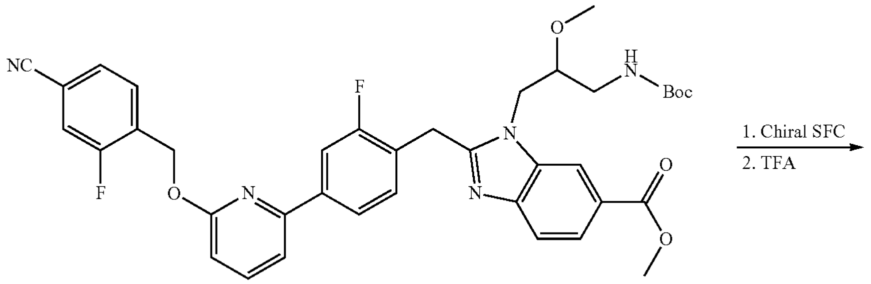
I-39
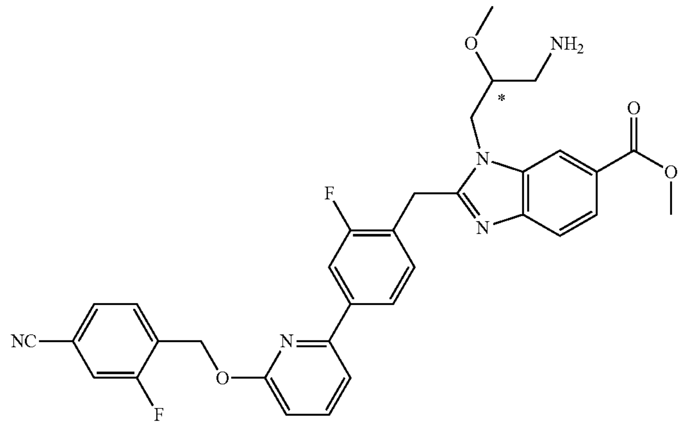
+
I-40
peak one -continued

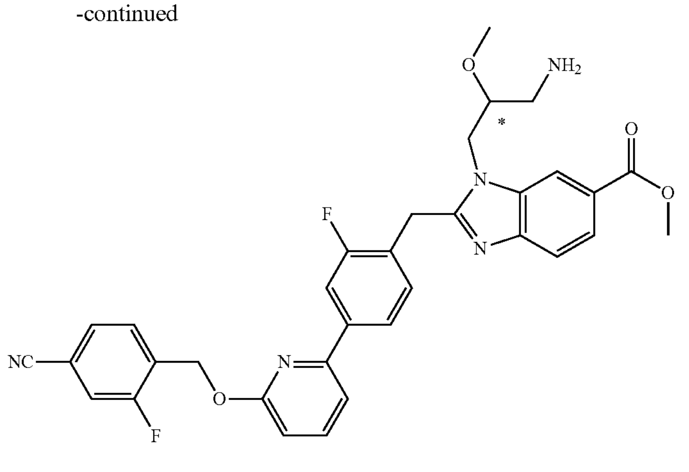

I-41
peak two

Methyl 3-[[3-(tert-butoxycarbonylamino)-2-methoxy-propyl]amino]-4-nitro-benzoate (I-37): methyl 3-fluoro-4-nitro-benzoate (1300 mg, 6.53 mmol), 2-methoxypropane-1,3-diamine (1020 mg, 9.79 mmol), and DIPEA (4.4 mL, 26 mmol) were combined in MeTHF (10 mL) and stirred for 3 hrs at 75° C. The reaction was cooled to RT, diluted with DCM (10 mL), and Di-tert-butyl dicarbonate (4.3 g, 20 mmol) was added. After 30 minutes, the reaction was diluted with EtOAc (50 mL) and rinsed twice with aq $NH_4Cl$, and once with brine. The organic fraction was dried over $Na_2SO_4$, filtered, concentrated, and purified by column chromatography to provide the title compound: ES/MS: 384.0 ($M+H^+$).

Methyl 4-amino-3-[[3-(tert-butoxycarbonylamino)-2-methoxy-propyl]amino]benzoate (I-38): Methyl 3-[[3-(tert-butoxycarbonylamino)-2-methoxy-propyl]amino]-4-nitro-benzoate (I-37, 1.8 g, 4.7 mmol) was combined with iron powder (1.05 g, 18.8 mmol) and sat. aq. $NH_4Cl$ (4.7 mL) in ethanol (20 mL). The mixture was stirred at 60° C. for 10 minutes, then cooled to RT, diluted with EtOAc (100 mL), filtered through Celite, and rinsed twice with brine. The organic fraction was dried over $Na_2SO_4$, filtered, and concentrated to provide the title compound: ES/MS: 354.1 ($M+H^+$).

Methyl 3-[3-(tert-butoxycarbonylamino)-2-methoxy-propyl]-2-[[4-[6-[(4-cyano-2-fluoro-phenyl)methoxy]-2-pyridyl]-2-fluoro-phenyl]methyl]benzimidazole-5-carboxylate (I-39): Methyl 4-amino-3-[[3-(tert-butoxycarbonylamino)-2-methoxy-propyl]amino]benzoate (I-38, 500 mg, 1.4 mmol), 2-[4-[6-[(4-cyano-2-fluoro-phenyl)methoxy]-2-pyridyl]-2-fluoro-phenyl]acetic acid (I-128, 460 mg, 1.2 mmol), HATU (689 mg, 1.81 mmol), and DIPEA (1.05 mL, 6.05 mmol) were combined with DCE/DMF (2:1, 6 mL) and stirred at 50° C. for 45 minutes. The reaction was cooled, diluted with EtOAc and rinsed with aq $NH_4Cl$, aq $NaHCO_3$, and brine. The organic fraction was dried over $Na_2SO_4$, filtered, and concentrated. The crude solids were dissolved in DCE/AcOH (1:2, 5 mL) and stirred at 80° C. for 30 minutes, then cooled to room temperature, concentrated to dryness, and purified by column chromatography (40-85% EtOAc in hexane) to provide the title compound: ES/MS: 698.3 ($M+H^+$); $^1H$ NMR (400 MHz, Chloroform-d) δ 8.13 (s, 1H), 8.05 (d, J=8.5 Hz, 1H), 7.85 (s, 1H), 7.78-7.63 (m, 4H), 7.48 (dd, J=7.9, 1.6 Hz, 1H), 7.42 (dd, J=9.2, 1.5 Hz, 1H), 7.37 (d, J=7.5 Hz, 1H), 6.83 (d, J=8.2 Hz, 1H), 5.62 (s, 2H), 4.89 (t, J=6.0 Hz, 1H), 4.56 (s, 1H), 4.30 (s, 2H), 3.98 (s, 3H), 3.67-3.56 (m, 1H), 3.42 (s, 2H), 3.12 (s, 3H), 2.12 (s, 1H), 1.49 (s, 9H).

Methyl 1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylate enantiomer 1 and 2 (I-40 and I-41): Methyl 3-[3-(tert-butoxycarbonylamino)-2-methoxy-propyl]-2-[[4-[6-[(4-cyano-2-fluoro-phenyl)methoxy]-2-pyridyl]-2-fluoro-phenyl]methyl]benzimidazole-5-carboxylate obtained as a mixture of 2 stereoisomers was separated by chiral SFC (IG column with 40% EtOH cosolvent) to give two distinct stereoisomers. The separated enantiomers were subjected separately to TFA (65 equiv) at RT for 5 minutes. The reactions were diluted with water, quenched to pH 7 with 1 M NaOH, and extracted three times with DCM. The combined organic fractions were rinsed with aq $NaHCO_3$ and brine, then dried over $Na_2SO_4$, filtered, and concentrated to provide the titled compounds. ES/MS: 598.5 ($M+H^+$).

Intermediates I-42 and I-43

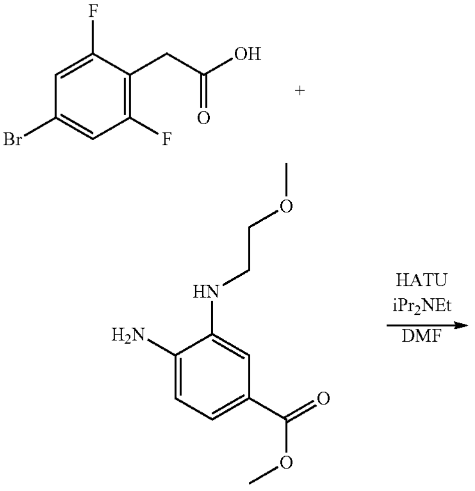

I-1

-continued

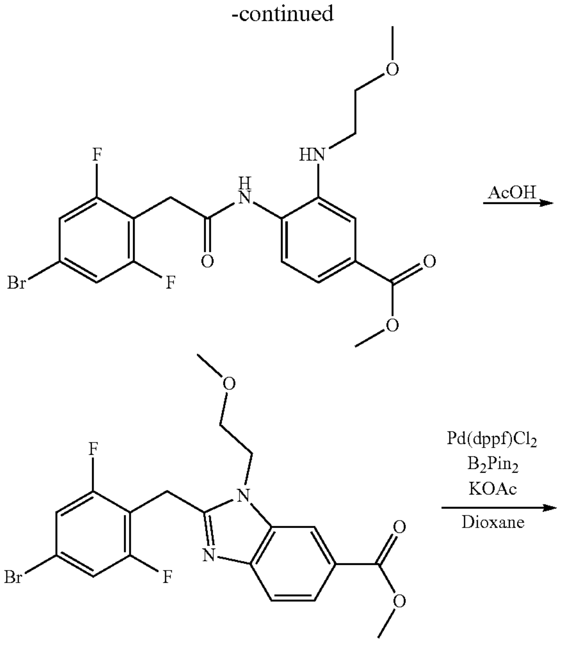

I-42

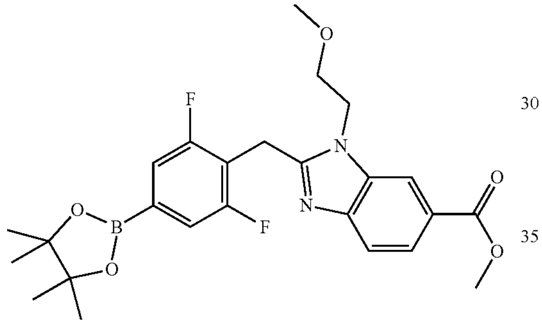

I-43

Methyl 4-[[2-(4-bromo-2,6-difluoro-phenyl)acetyl]amino]-3-(2-methoxyethylamino)benzoate: To a solution of 2-(4-bromo-2,6-difluoro-phenyl)acetic acid (3.67 g, 0.0146 mol), methyl 4-amino-3-(2-methoxyethylamino)benzoate (3.00 g, 0.0134 mol), and 2-(7-aza-1H-benzotriazole-1-yl)-1,1,3,3-tetramethyluronium hexafluorophosphate (HATU), 99% (3.78 g, 0.00993 mol) in DMF (35 mL), was added N,N-diisopropylethylamine (11.7 mL, 0.0669 mol). The mixture was stirred at RT overnight. The reaction was diluted with EtOAc washed with 5% LiCl, saturated $NaHCO_3$, and brine. The organic extract was dried over sodium sulfate and concentrated. The crude residue was taken forward without further purification. ES/MS m/z: 457.0, 459.0 $(M+H^+)$ Methyl 2-[(4-bromo-2,6-difluoro-phenyl)methyl]-3-(2-methoxyethyl)benzimidazole-5-carboxylate (I-42): A solution of methyl 4-[[2-(4-bromo-2,6-difluoro-phenyl)acetyl]amino]-3-(2-methoxyethylamino)benzoate (6.12 g, 0.0134 mol) in AcOH (24 mL) and DCE (24 mL) was heated at 60° C. for 7 hr. The mixture was concentrated and chromatographed (eluent: EtOAc/hexanes) to give the title compound. ES/MS m/z: 439.0, 441.0 $(M+H^+)$; $^1H$ NMR (400 MHz, CDCl3) δ 8.09 (dd, J=1.5, 0.7 Hz, 1H), 7.96 (dd, J=8.5, 1.6 Hz, 1H), 7.74 (d, J=8.5 Hz, 1H), 7.16 (d, J=6.8 Hz, 2H), 4.46 (t, J=5.2 Hz, 2H), 4.36 (s, 2H), 3.97 (s, 3H), 3.74 (t, J=5.1 Hz, 2H), 3.31 (s, 3H).

Methyl 2-[[2,6-difluoro-4-(4,4,5,5-tetramethyl-1,3,2-dioxaborolan-2-yl)phenyl]methyl]-3-(2-methoxyethyl)benzimidazole-5-carboxylate (I-43): In a 200 ml round bottomed flask, a mixture of methyl 2-[(4-bromo-2,6-difluoro-phenyl)methyl]-3-(2-methoxyethyl)benzimidazole-5-carboxylate (1000 mg, 2.28 mmol), 4,4,5,5-tetramethyl-2-(4,4,5,5-tetramethyl-1,3,2-dioxaborolan-2-yl)-1,3,2-dioxaborolane (695 mg, 2.74 mmol), (1,1'-bis(diphenylphosphino)ferrocene)-dichloropalladium(II) (81.5 mg, 0.115 mmol), and potassium acetate (671 mg, 6.84 mmol) was purged with Ar/vac 3×. To this was added dioxane (24 mL) and the mixture was degassed for 5 min with Ar. The mixture was heated at 100° C. for 3.5 hr. The mixture was filtered over a Celite plug, diluted with EtOAc and washed with brine. The organic extract was dried over sodium sulfate and chromatographed (eluent: EtOAc/hexanes). The resulting compound was diluted with EtOAc, washed with saturated $NaHCO_3$ twice, and dried over magnesium sulfate. The organic extract was filtered and concentrated, then diluted with $Et_2O$ (2 mL) and sonicated to give a precipitate. To this was added hexane, and the mixture was filtered and rinsed with hexane to give the title compound. ES/MS m/z: 487.2 $(M+H^+)$; $^1H$ NMR (400 MHz, CDCl3) δ 8.17-8.07 (m, 1H), 7.97 (d, J=8.5 Hz, 1H), 7.75 (d, J=8.4 Hz, 1H), 7.37 (d, J=7.3 Hz, 2H), 4.45 (t, J=5.2 Hz, 4H), 3.97 (s, 3H), 3.71 (t, J=5.2 Hz, 2H), 3.30 (s, 3H), 1.35 (s, 12H).

Intermediate I-44

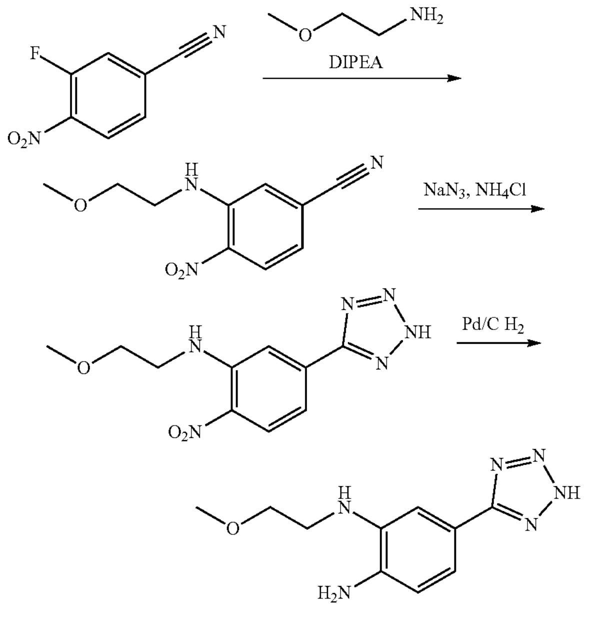

I-44

3-(2-methoxyethylamino)-4-nitro-benzonitrile: A solution of 3-fluoro-4-nitro-benzonitrile (2 g, 12.04 mmol), 2-methoxyethanamine (1.25 ml, 14.79 mmol), and N,N-diisopropylethylamine (3.2 ml, 18.37 mmol) in DMF was stirred at RT for two days. The mixture was diluted with EtOAc, washed with 5% LiCl twice and brine. The organic extract was dried over sodium sulfate to give the title compound. ES/MS m/z: 222 $(M+H^+)$; $^1H$ NMR (400 MHz, CDCl3) δ 8.26 (dd, J=8.7, 1.7 Hz, 1H), 8.23 (s, 1H), 7.21 (d, J=1.7 Hz, 1H), 6.89 (dt, J=8.8, 1.5 Hz, 1H), 3.71 (dd, J=5.6, 4.8 Hz, 2H), 3.51 (q, J=5.2 Hz, 2H), 3.45 (d, J=1.0 Hz, 3H).

N-(2-methoxyethyl)-2-nitro-5-(2H-tetrazol-5-yl)aniline: In a 200 ml round bottomed flask, a suspension of 3-(2-methoxyethylamino)-4-nitro-benzonitrile (2.563 g, 11.6 mmol), sodium azide (1.51 g, 23.2 mmol), and ammonium chloride (1.24 g, 23.2 mmol) in DMF (50 mL) was heated at 110° C. overnight. The mixture was diluted with EtOAc and washed with 5% LiCl (3×50 mL). The aqueous layer was extracted with EtOAc (2×100 mL). The combined organic extracts were dried over sodium sulfate to give the title compound. ES/MS m/z: 265.2 ($M+H^+$); $^1H$ NMR (400 MHz, MeOD) δ 8.32 (d, J=8.8 Hz, 1H), 7.77 (d, J=1.8 Hz, 1H), 7.35 (dd, J=8.9, 1.8 Hz, 1H), 3.82-3.69 (m, 2H), 3.66 (t, J=5.2 Hz, 2H), 3.46 (s, 3H), 3.01 (d, J=0.5 Hz, 4H).

N-2-(2-methoxyethyl)-4-(2H-tetrazol-5-yl)benzene-1,2-diamine (I-44): A solution of N-(2-methoxyethyl)-2-nitro-5-(2H-tetrazol-5-yl)aniline (93 mg, 352 μmol) in EtOH (25 mL) was degassed with Ar under vacuum three times. Pd/C (10%, 37.7 mg, 0.0354 mmol) was added and the mixture was stirred at RT with a balloon of hydrogen overnight. The mixture was filtered over a Celite plug, rinsed with EtOAc, and concentrated to give the title product, which was used in the subsequent steps without further purification. ES/MS m/z: 235.2 ($M+H^+$)

Intermediate I-45

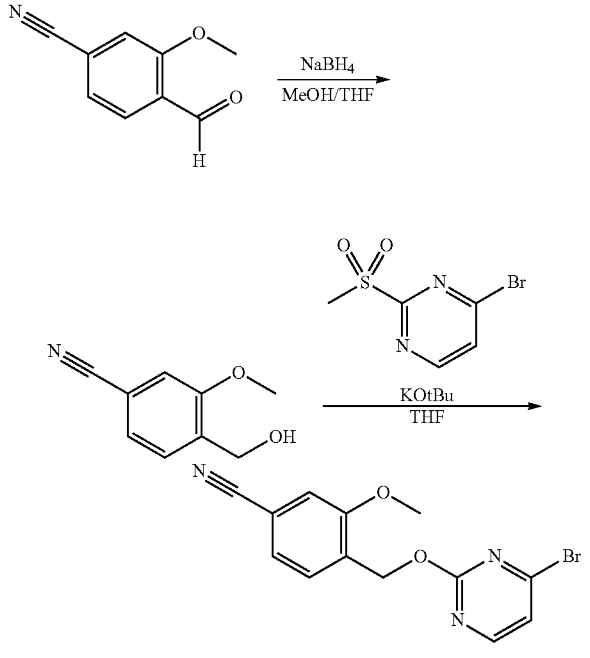

I-45

4-(hydroxymethyl)-3-methoxy-benzonitrile: In a 500 mL round bottomed flask, 4-formyl-3-methoxy-benzonitrile (3.46 g, 0.0215 mol) was dissolved in MeOH (115 mL) and THF (115 mL). The mixture was cooled to 0° C., then sodium borohydride (0.813 g, 0.0215 mol) was added in portions. The mixture was stirred at 0° C. under an $N_2$ atmosphere for 2 h. EtOAc (175 mL) was added, followed by water (50 mL), and $NH_4Cl$ slowly (50 mL, gas evolution). Brine was added and the mixture was partitioned. The organic extract was dried over $MgSO_4$ and concentrated, then rediluted with EtOAc and dried over sodium sulfate to give a crude residue, which was diluted with EtOAc (200 mL) and stirred with aqueous saturated Rochelle salt solution for 2 h. The layers were separated and the organic extract was dried over sodium sulfate and concentrated to give the title compound, which was carried forward without further purification. $^1H$ NMR (400 MHz, MeOD) δ 7.59 (dd, J=7.7, 1.0 Hz, 1H), 7.35 (dd, J=7.8, 1.5 Hz, 1H), 7.29 (d, J=1.4 Hz, 1H), 4.68 (s, 2H), 3.90 (s, 3H).

4-[(4-bromopyrimidin-2-yl)oxymethyl]-3-methoxy-benzonitrile (I-45): In a 100 mL RBF, a solution of 4-(hydroxymethyl)-3-methoxy-benzonitrile (0.918 g, 0.00563 mol) in THF (15 mL) was cooled to 0° C. Potassium tert-butoxide (1.00 M in THF, 5.10 mL, 0.00510 mol) was added and the mixture was stirred for 15 min at 0° C.

In a separate 100 mL RBF, a solution of 4-bromo-2-methylsulfonyl-pyrimidine (1.20 g, 0.00506 mol) in THF (15 mL) was cooled to −78° C. A solution of the benzyl alcohol and KOtBu mixture was added via syringe over 5 min and stirred at −78° C. for 1 h. The mixture was diluted with 60 mL EtOAc and 30 mL water. The organic extract was dried over sodium sulfate, concentrated, and purified by silica gel column chromatography (eluent: EtOAc/hexanes) to give the title compound. ES/MS m/z: 321.91 ($M+H^+$); $^1H$ NMR (400 MHz, CDCl3) δ 8.32 (d, J=5.1 Hz, 1H), 7.62 (d, J=7.8 Hz, 1H), 7.31 (dd, J=7.8, 1.4 Hz, 1H), 7.21 (d, J=5.2 Hz, 1H), 7.14 (d, J=1.4 Hz, 1H), 5.52 (s, 2H), 3.92 (s, 3H).

Intermediate I-46

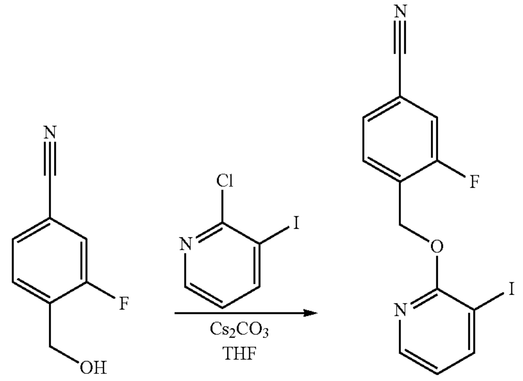

I-46

3-fluoro-4-[(3-iodo-2-pyridyl)oxymethyl]benzonitrile (I-46): A suspension of 3-fluoro-4-(hydroxymethyl)benzonitrile (0.757 g, 5.01 mmol), 2-chloro-3-iodo-pyridine (1.00 g, 4.18 mmol), and cesium carbonate (2.45 g, 7.52 mmol) in THF (15 mL) was heated at 80° C. until starting material was consumed. The mixture was diluted with EtOAc and washed with brine. The organic extract was dried over sodium sulfate, concentrated, and purified by silica gel column chromatography (eluent: EtOAc/hexanes) to give the title compound.

$^1H$ NMR (400 MHz, CDCl3) δ 8.16-8.07 (m, 2H), 7.79 (dd, J=8.0, 7.1 Hz, 1H), 7.52 (dd, J=7.9, 1.5 Hz, 1H), 7.41 (dd, J=9.3, 1.5 Hz, 1H), 6.74 (dd, J=7.6, 4.9 Hz, 1H), 5.57 (d, J=1.1 Hz, 2H).

Intermediates I-47

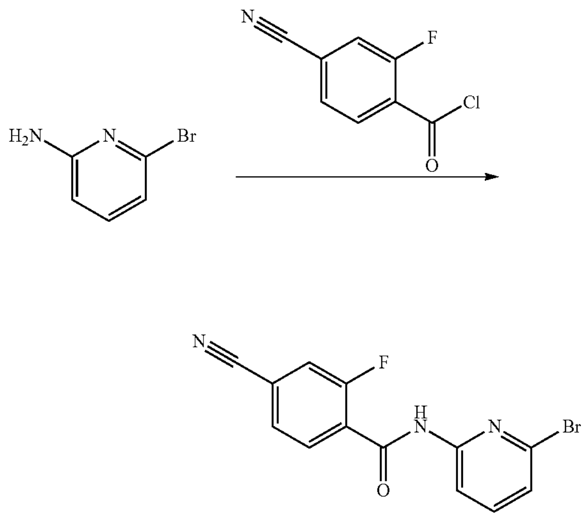

I-47

N-(6-bromo-2-pyridyl)-4-cyano-2-fluoro-benzamide (I-47): To a suspension of 6-bromopyridin-2-amine (1050 mg, 0.578 mmol) and 4-cyano-2-fluoro-benzoyl chloride (138 mg, 0.751 mmol) in DCM (5 mL), was added pyridine (0.1 mL, 1.24 mmol). The mixture was stirred at RT overnight. The mixture was diluted with EtOAc and washed with $NH_4Cl$, and brine. The organic extract was dried over sodium sulfate, concentrated, and purified by silica gel column chromatography (eluent: EtOAc/hexanes) to give titled compound. ES/MS m/z: 320.0, 322.0 ($M+H^+$); $^1H$ NMR (400 MHz, CDC13) δ 8.95 (d, J=11.9 Hz, 1H), 8.35 (dd, J=8.2, 0.7 Hz, 1H), 8.27 (t, J=7.8 Hz, 1H), 7.66 (ddd, J=8.0, 4.7, 3.2 Hz, 2H), 7.57 (dd, J=10.9, 1.5 Hz, 1H), 7.34 (dd, J=7.7, 0.7 Hz, 1H).

Intermediate I-48

I-48

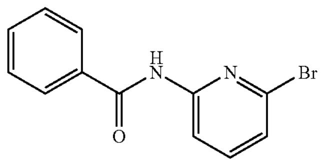

N-(6-bromo-2-pyridyl)benzamide (I-48): The title compound was prepared in the manner as described for 1-47, substituting 4-cyano-2-fluoro-benzoyl chloride with benzoyl chloride: ES/MS m/z: 277.0, 279.0 ($M+H^+$); $^1H$ NMR (400 MHz, CDC13) δ 8.59 (s, 1H), 8.39 (dd, J=8.2, 0.7 Hz, 1H), 8.07-7.87 (m, 2H), 7.70-7.57 (m, 2H), 7.57-7.47 (m, 2H), 7.41-7.19 (m, 1H).

Intermediate I-49

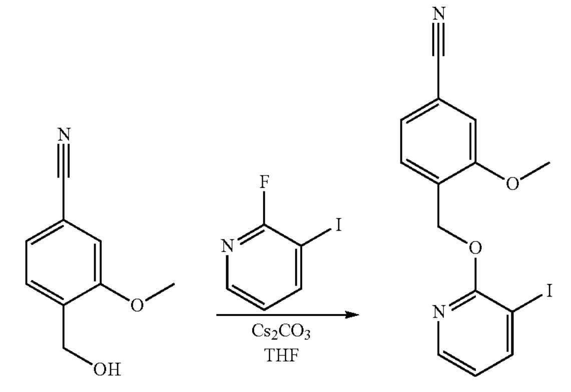

I-49

4-[(3-iodo-2-pyridyl)oxymethyl]-3-methoxy-benzonitrile (I-49): A suspension of 3-fluoro-4-(hydroxymethyl)benzonitrile (0.128 g, 0.784 mmol), 2-fluoro-3-iodo-pyridine (0.150 g, 0.673 mmol), and cesium carbonate (0.400 g, 1.23 mmol) in THF (3 mL) was heated at 80° C. overnight. The mixture was diluted with EtOAc and washed with brine. The organic extract was dried over sodium sulfate, concentrated, and purified by silica gel column chromatography (eluent: EtOAc/hexanes) to give the title compound. ES/MS: 366.9 ($M+H^+$); $^1H$ NMR (400 MHz, $CDCl_3$) δ 8.15 (dd, J=4.9, 1.7 Hz, 1H), 8.11 (dd, J=7.5, 1.7 Hz, 1H), 7.73 (d, J=7.8 Hz, 1H), 7.35 (dd, J=7.8, 1.4 Hz, 1H), 7.13 (d, J=1.4 Hz, 1H), 6.73 (dd, J=7.6, 4.9 Hz, 1H), 5.51 (d, J=1.1 Hz, 2H), 3.93 (s, 3H).

Intermediate I-50

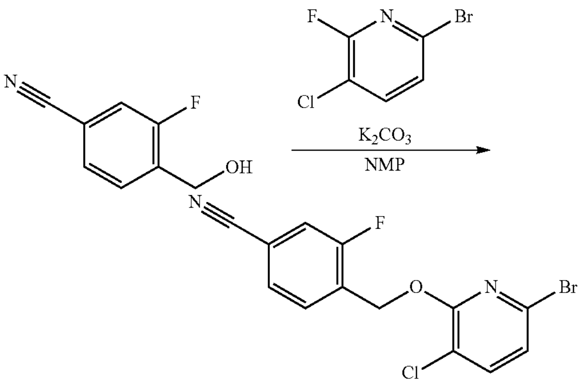

I-50

4-[(6-bromo-3-chloro-2-pyridyl)oxymethyl]-3-fluoro-benzonitrile (I-50): A suspension of 3-fluoro-4-(hydroxymethyl)benzonitrile (0.237 g, 1.57 mmol), 6-bromo-3-chloro-2-fluoro-pyridine (0.300 g, 1.43 mmol), and potassium carbonate (0.591 g, 4.28 mmol) in NMP (5 mL) was heated at 100° C. overnight. The mixture was diluted with EtOAc and washed with 5% LiCl solution (3×). The organic extract was dried over sodium sulfate, concentrated, and purified by silica gel column chromatography (eluent: EtOAc/hexanes) to give the title compound. $^1H$ NMR (400 MHz, $CDCl_3$) δ 7.74 (t, J=7.5 Hz, 1H), 7.59-7.47 (m, 2H), 7.43 (dd, J=9.3, 1.5 Hz, 1H), 7.11 (d, J=7.9 Hz, 1H), 5.57 (s, 2H); $^{19}F$ NMR (376 MHz, $CDCl_3$) δ −112.14−−116.85 (m).

Intermediate I-51

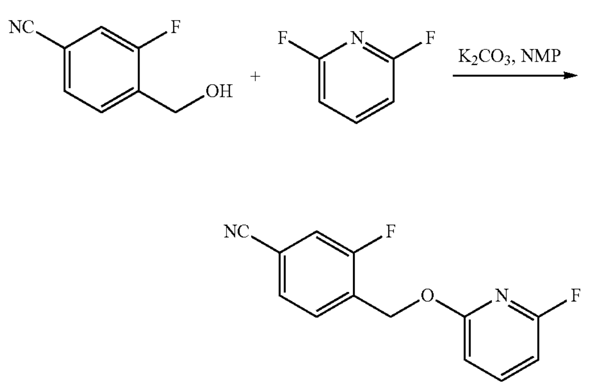

I-51

3-fluoro-4-[(6-fluoro-2-pyridyl)oxymethyl]benzonitrile (I-51): A suspension of 2,6-difluoropyridine (0.39 ml, 4.34 mmol), 3-fluoro-4-(hydroxymethyl)benzonitrile (0.72 g, 4.78 mmol), and potassium carbonate (1.8 g, 13.03 mmol) in NMP (10 mL) was heated at 100° C. overnight. The mixture was diluted with EtOAc and washed with aqueous 5% LiCl solution (3×). The organic extract was dried over sodium sulfate, concentrated and purified by silica gel column chromatography (eluent: EtOAc/hexanes) to afford the title product. ES/MS: 247.0 (M+H$^+$); $^1$H NMR (400 MHz, Chloroform-d) δ 7.73 (q, J=8.0 Hz, 1H), 7.67 (t, J=7.5 Hz, 1H), 7.50 (dd, J=7.9, 1.6 Hz, 1H), 7.41 (dd, J=9.3, 1.6 Hz, 1H), 6.73 (dd, J=8.0, 1.6 Hz, 1H), 6.56 (dd, J=7.8, 2.4 Hz, 1H), 5.48 (d, J=1.2 Hz, 2H); $^{19}$F NMR (376 MHz, Chloroform-d) δ −70.47 (d, J=8.7 Hz), −112.50-−117.78 (m).

Intermediate I-52

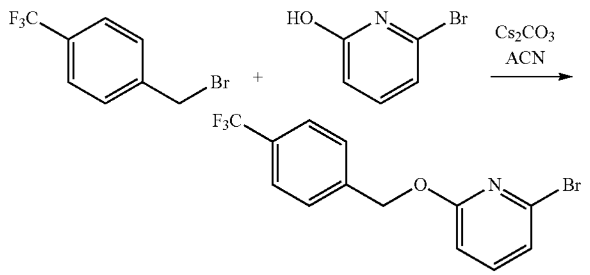

I-52

2-Bromo-6-((4-(trifluoromethyl)benzyl)oxy)pyridine (I-52): 1-(bromomethyl)-4-(trifluoromethyl)benzene (239 mg, 1 mmol) was added to 6-bromopyridin-2-ol (190 mg, 1.1 mmol) and cesium carbonate (360 mg, 1.1 mmol) in acetonitrile (4 mL). The mixture was stirred overnight at ambient temperature. The mixture was filtered through Celite and concentrated by rotary evaporation. The product was used without further purification to give the titled compound. $^1$H NMR (400 MHz, Chloroform-d) δ 7.66 (d, J=8.2 Hz, 2H), 7.60 (d, J=8.1 Hz, 2H), 7.48 (t, J=7.8 Hz, 1H), 7.13 (d, J=7.4 Hz, 1H), 6.79 (d, J=8.1 Hz, 1H), 5.45 (s, 2H).

Intermediate I-53

I-53

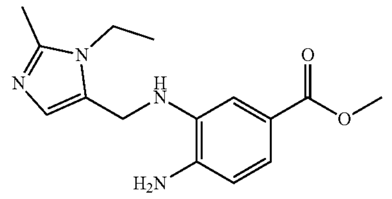

Methyl 4-amino-3-(((1-ethyl-2-methyl-1H-imidazol-5-yl)methyl)amino)benzoate (I-53): Methyl 4-amino-3-(((1-ethyl-2-methyl-1H-imidazol-5-yl)methyl)amino)benzoate was prepared in the manner as described for I-1 substituting methoxyethylamine with chloro-[(3-ethyl-2-methyl-imidazol-4-yl)methyl]-imino-lambda5-chlorane. ES/MS: 289.3 (M+H$^+$).

Intermediate I-54

I-54

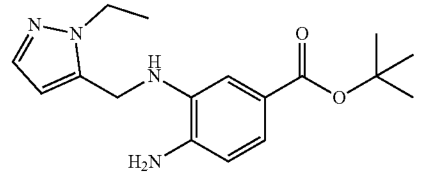

tert-Butyl 4-amino-3-(((1-ethyl-1H-pyrazol-5-yl)methyl)amino)benzoate (I-54): tert-butyl 4-amino-3-(((1-ethyl-1H-pyrazol-5-yl)methyl)amino)benzoate was prepared identically as described for I-1 but substituting methoxyethylamine with (1-ethyl-1H-pyrazol-5-yl)methanamine ES/MS: 317.4 (M+H$^+$).

Intermediate I-55

I-55

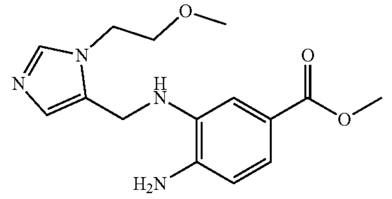

Methyl 4-amino-3-(((1-(2-methoxyethyl)-1H-imidazol-5-yl)methyl)amino)benzoate (I-55): Methyl 4-amino-3-(((1-(2-methoxyethyl)-1H-imidazol-5-yl)methyl)amino)benzoate was prepared identically as described for I-1 substituting methoxyethylamine with (1-(2-methoxyethyl)-1H-imidazol-5-yl)methanamine: ES/MS: 305.4 (M+H$^+$).

Intermediate I-56

I-56

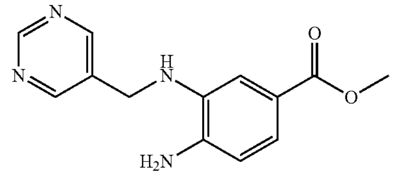

Methyl 4-amino-3-((pyrimidin-5-ylmethyl)amino)benzoate (I-56): Methyl 4-amino-3-((pyrimidin-5-ylmethyl)amino)benzoate was prepared identically as described for I-1 substituting methoxyethylamine with pyrimidin-5-ylmethanamine. ES/MS: 259.3 (M+H$^+$).

Intermediate I-57

I-57

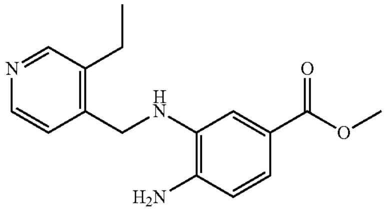

Methyl 4-amino-3-(((3-ethylpyridin-4-yl)methyl)amino)benzoate (I-57): Methyl 4-amino-3-(((3-ethylpyridin-4-yl)methyl)amino)benzoate was prepared identically as described for I-1 substituting methoxyethylamine with 3-ethyl-4-pyridyl)methanamine: ES/MS: 286.3 (M+H$^+$).

Intermediate I-58

I-58

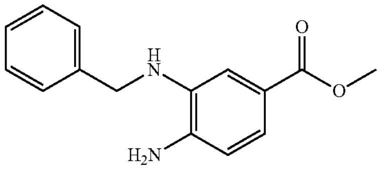

Methyl 4-amino-3-(benzylamino)benzoate (I-58): Methyl 4-amino-3-(benzylamino)benzoate was prepared identically as described for I-1 substituting methoxyethylamine with phenylmethanamine. ES/MS: 257.3 (M+H$^+$).

Intermediate I-59

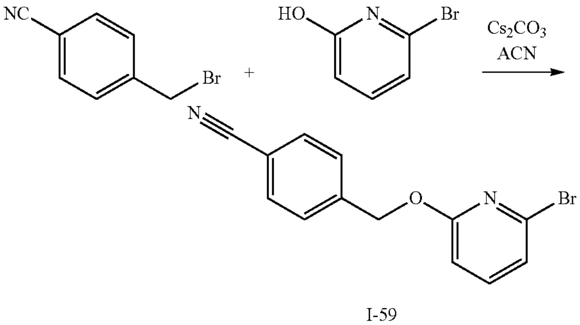

I-59

4-(((6-bromopyridin-2-yl)oxy)methyl)benzonitrile (I-59): 4-(((6-bromopyridin-2-yl)oxy)methyl)benzonitrile was prepared identically as described for I-51 substituting 1-(bromomethyl)-4-(trifluoromethyl)benzene with 4-(bromomethyl)benzonitrile. $^1$H NMR (400 MHz, Chloroform-d) δ 7.79-7.64 (m, 2H), 7.59 (d, J=8.1 Hz, 2H), 7.49 (dd, J=8.1, 7.5 Hz, 1H), 7.19-7.05 (m, 1H), 6.80 (dd, J=8.1, 0.6 Hz, 1H), 5.45 (s, 2H).

Intermediate I-60

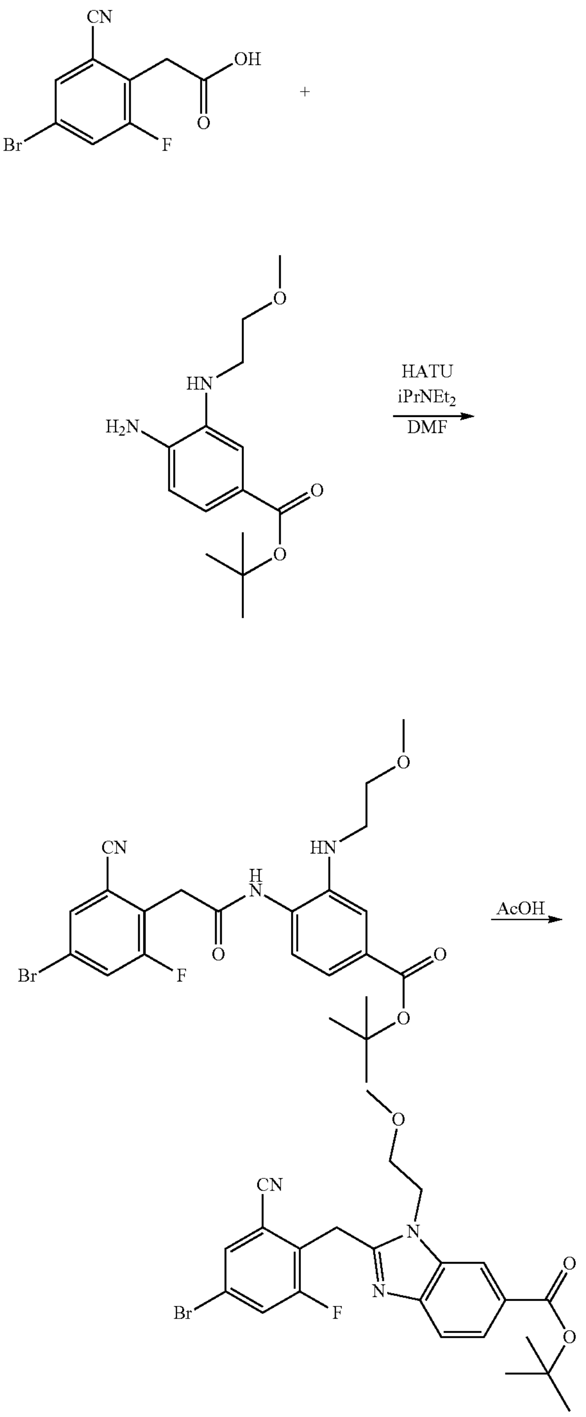

I-60

Tert-butyl 2-(4-Bromo-2-cyano-6-fluorobenzyl)-1-(2-methoxyethyl)-1H-benzo[d]imidazole-6-carboxylate (I-60): tert-butyl 2-(4-bromo-2-cyano-6-fluorobenzyl)-1-(2-methoxyethyl)-1H-benzo[d]imidazole-6-carboxylate was prepared identically as described for Intermediate I-5 substituting 2-(4-bromo-2-fluoro-phenyl)acetic acid with 2-(4-bromo-2-cyano-6-fluorophenyl)acetic acid. ES/MS: 488.7 (M+H$^+$).

Intermediate I-61

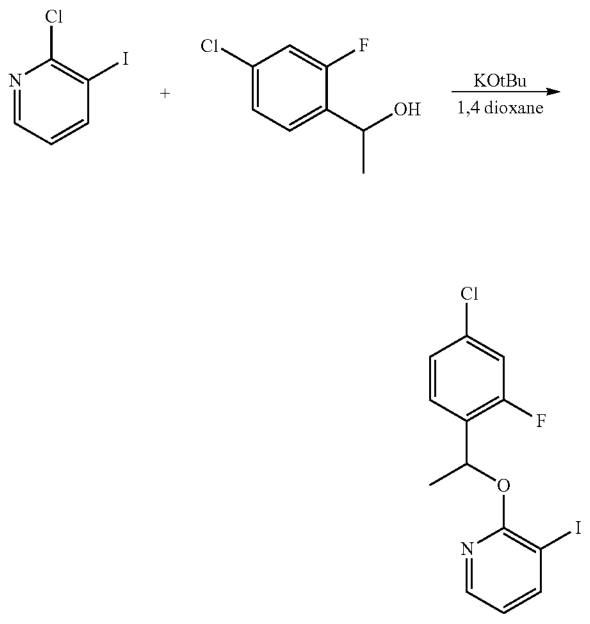

I-61

2-(1-(4-chloro-2-fluorophenyl)ethoxy)-3-iodopyridine (I-61): 3-fluoro-4-(hydroxymethyl)benzonitrile (0.875 g, 5.01 mmol) and 2-chloro-3-iodo-pyridine (1.00 g, 4.18 mmol) were taken up in 1,4-dioxane (8.0 mL), and potassium tert-butoxide (0.703 g, 6.26 mmol) was added portion-wise. Following addition, the mixture was sealed and heated to 110° C. for 8 hours. Upon completion, the mixture was cooled to RT and diluted with EtOAc (100 mL) and water (100 mL). The organic phase was collected and the aqueous phase was extracted with EtOAc (2×50 mL). The combined organics were dried over $MgSO_4$, filtered, and concentrated in vacuo. The residue was then purified by normal phase column chromatography (eluent: EtOAc/hexanes gradient) to afford the titled compound.

Intermediate I-62

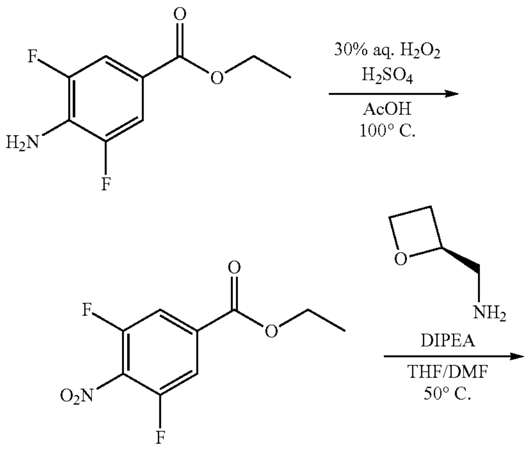

-continued

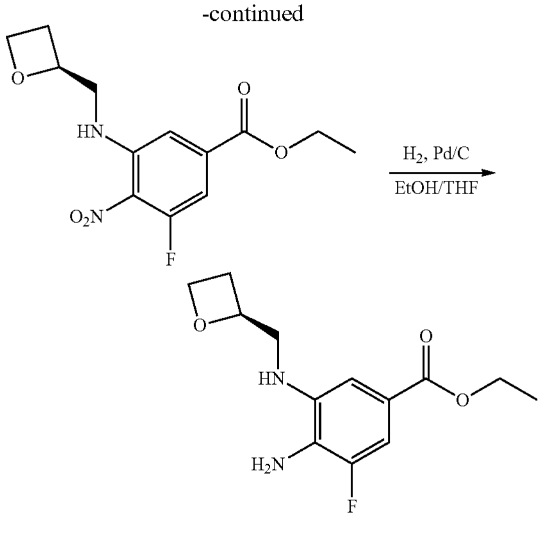

I-62

Ethyl 3,5-difluoro-4-nitrobenzoate: Ethyl 4-amino-3,5-difluorobenzoate (5.00 g, 24.9 mmol) was taken up in acetic acid (50.0 mL) and sulfuric acid (12.1 M, 2.05 mL, 24.9 mmol) and hydrogen peroxide (30% aqueous solution, 46.7 mL, 74.6 mmol) were added sequentially. The mixture was heated to 100° C. for 1 hour. The mixture was then cooled to room temperature and then slowly poured into 300 mL of ice water while swirling. The mixture was then diluted with EtOAc (200 mL), transferred to a separatory funnel, and the organic phase collected. The aqueous phase was extracted with EtOAc (2×100 mL) and the combined organics were dried over $MgSO_4$ and concentrated in vacuo. The residue was purified by column chromatography (eluent: EtOAc/Hexanes gradient) to afford the product.

Ethyl (S)-3-fluoro-4-nitro-5-((oxetan-2-ylmethyl)amino)benzoate: Ethyl 3,5-difluoro-4-nitro-benzoate (2.50 g, 10.8 mmol) and (S)-oxetan-2-ylmethanamine (989 mg, 11.4 mol) were taken up in tetrahydrofuran (12.0 mL) and N,N-dimethylformamide (6.0 mL), and N,N-diisopropylethylamine (9.42 mL, 54.1 mmol) was added. The mixture was heated to 50° C. for 16 hours. Following this time, the mixture was concentrated in vacuo and the residue purified by column chromatography (eluent: 0-25% EtOAc/Hexanes) to afford the product. ES/MS: 299.2 ($M+H^+$).

Ethyl (S)-4-amino-3-fluoro-5-((oxetan-2-ylmethyl)amino)benzoate (I-62): Ethyl (S)-3-fluoro-4-nitro-5-((oxetan-2-ylmethyl)amino)benzoate (2.20 g, 7.38 mmol) was taken up in ethanol (10 mL) and tetrahydrofuran (5 mL) and the mixture sparged with nitrogen for 5 minutes. Palladium on carbon (10 wt. % loading, 785 mg, 0.74 mmol) was then added and sparging continued for 5 minutes. Hydrogen was then bubbled through the solution for one minute and then the mixture was set up under balloon hydrogen atmosphere for 21 hours. Following this time, the reaction was stopped and the mixture was filtered through Celite. The filter was washed with EtOAc (2×20 mL) and methanol (2×10 mL) and the filtrate concentrated in vacuo to afford ethyl (S)-4-amino-3-fluoro-5-((oxetan-2-ylmethyl)amino)benzoate (I-62). ES/MS: 269.2 ($M+H^+$); $^1H$ NMR (400 MHz, chloroform) δ 7.44-7.30 (m, 2H), 5.13 (qd, J=7.1, 3.4 Hz, 1H), 4.72 (ddd, J=8.7, 7.4, 6.0 Hz, 1H), 4.62 (dt, J=9.1, 6.1 Hz, 1H), 4.33 (q, J=7.1 Hz, 2H), 3.58-3.30 (m, 2H), 2.76 (dtd, J=11.4, 8.0, 6.1 Hz, 1H), 2.56 (ddt, J=11.3, 9.0, 7.1 Hz, 1H), 1.37 (t, J=7.1 Hz, 3H).

Intermediate I-63

I-63

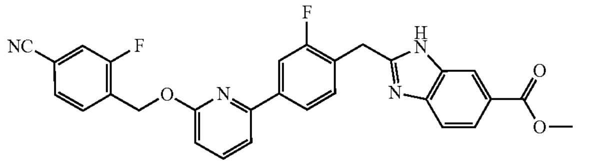

Methyl 2-(4-(6-((4-cyano-2-fluorobenzyl)oxy)pyridin-2-yl)-2-fluorobenzyl)-1H-benzo[d]imidazole-6-carboxylate (I-63): Methyl 2-(4-(6-((4-cyano-2-fluorobenzyl)oxy)pyridin-2-yl)-2-fluorobenzyl)-1H-benzo[d]imidazole-6-carboxylate was prepared identically as described for Procedure 29 substituting 2-(3'-((4-cyano-2-fluorobenzyl)oxy)-3,4'-difluoro-(1,1'-biphenyl)-4-yl)acetic acid with 2-(4-(6-((4-cyano-2-fluoro-phenyl)methoxy)-2-pyridyl)-2-fluoro-phenyl)acetic acid: ES/MS: 511.2 (M+H$^+$).

mmol), and O-(7-azabenzotriazol-1-yl)-N,N,N',N'-tetramethyluronium hexafluorophosphate (2485 mg, 5.77 mmol) were taken up in DMF (8 mL) and N,N-diisopropylethylamine (3.35 mL, 19.2 mmol) was added. The mixture was stirred at room temperature for 30 min. Following this time, the mixture was diluted with EtOAc (200 mL) and water (200 mL). The organic phase was collected, and the aqueous phase extracted with EtOAc (2×50 mL). The combined organic phases were dried over $Na_2SO_4$ and concentrated in vacuo. The resulting residue was taken up in acetic acid (20 mL) and heated to 75° C. After 7 hours, the mixture was concentrated in vacuo and the mixture was diluted with EtOAc (50 mL). The organic phase was washed with saturated aqueous $NaHCO_3$ (20 mL) and the aqueous phase extracted with EtOAc (2×50 mL). The combined organic phases were dried over $Na_2SO_4$ and concentrated in vacuo. The crude residue was purified by silica gel column chromatography (eluent: 20-100% hexanes/EtOAc): ES/MS: 448.1 (M+H$^+$).

Methyl 2-(4-(6-((4-cyano-2-fluorobenzyl)oxy)pyridin-2-yl)-3-nitrobenzyl)-1-(2-methoxyethyl)-1H-benzo[d]imida- Intermediate I-64

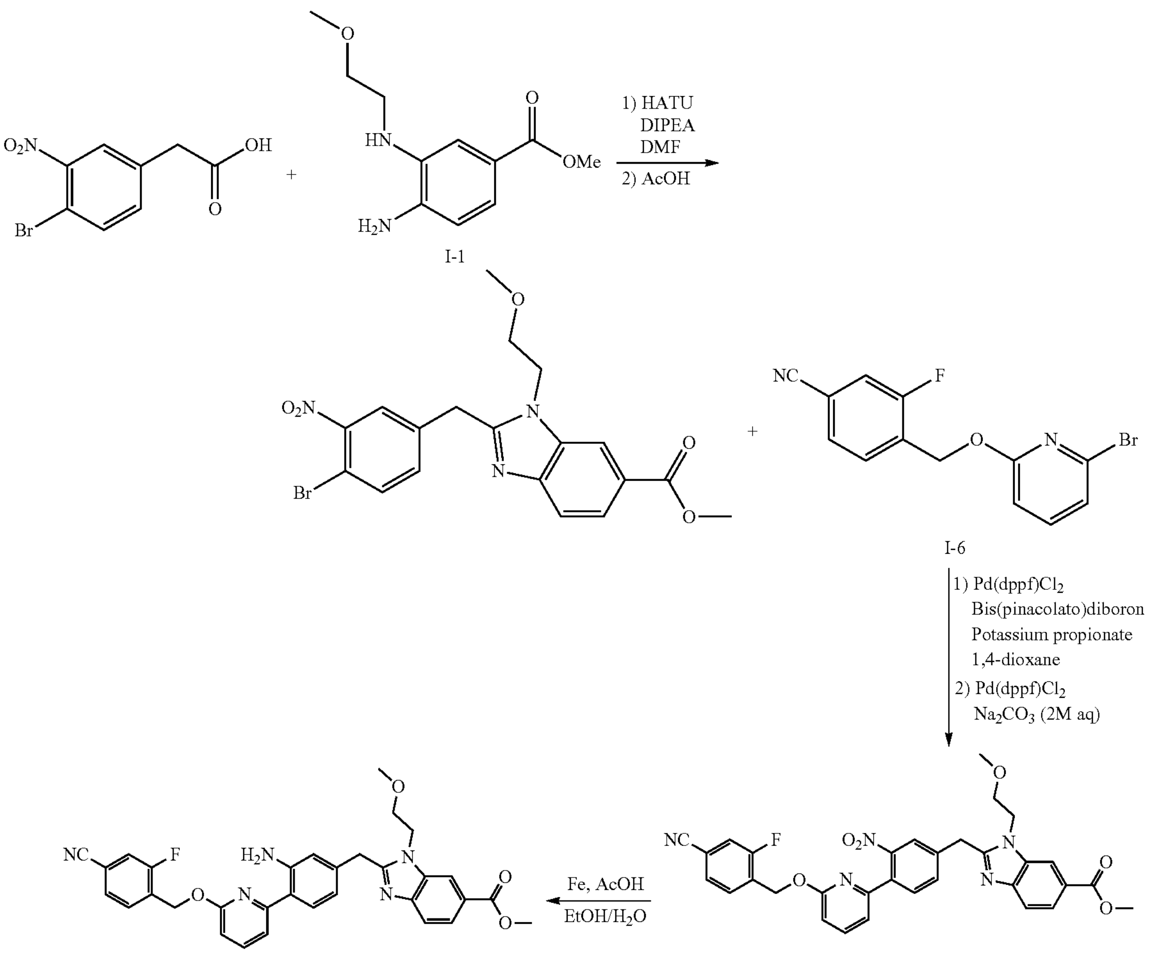

I-1

I-6

I-64

Methyl 2-(4-bromo-3-nitrobenzyl)-1-(2-methoxyethyl)-1H-benzo[d]imidazole-6-carboxylate: 2-(4-bromo-3-nitrophenyl)acetic acid (1000 mg, 3.85 mmol), methyl 4-amino-3-(2-methoxyethylamino)benzoate (I-1), 862 mg, 3.85 zole-6-carboxylate: To a vial was added methyl 2-(4-bromo-3-nitrobenzyl)-1-(2-methoxyethyl)-1H-benzo[d]imidazole-6-carboxylate (0.350 g, 0.781 mmol), bis(pinacolato) diboron (300 mg, 1.17 mmol), Pd(dppf)$Cl_2$ (54 mg, 0.078 mmol), and potassium propionate (263 mg, 2.34 mmol). DMF (10 mL) was added, and the mixture was degassed with argon for two minutes. The vial was sealed, and the mixture was heated for 1 hour at 100° C. Following this time, LC/MS showed conversion of the aryl bromide to the intermediate boronic acid and the mixture was cooled to room temperature. At this time, aqueous sodium carbonate (1.5 M, 1.56 mL, 2.34 mmol) was added followed by $Pd(dppf)Cl_2$ (54 mg, 0.078 mmol), and 4-[(6-bromo-2-pyridyl)oxymethyl]-3-fluoro-benzonitrile (I-6, 360 mg, 1.17 mmol). The vial was resealed and heated to 90° C. for 3 hours. Following this time, the mixture was cooled to room temperature, diluted with EtOAc (50 mL) and water (50 mL). The organic phase collected, and the aqueous phase extracted with EtOAc (2×50 mL). The combined organic phases were dried over $Na_2SO_4$ and concentrated in vacuo. The crude material was purified by silica gel chromatography (eluent: 20-80 EtOAc/hexanes) to afford the desired product: ES/MS: 596.2 (M+H$^+$).

Methyl 2-(3-amino-4-(6-((4-cyano-2-fluorobenzyl)oxy)pyridin-2-yl)benzyl)-1-(2-methoxyethyl)-1H-benzo[d]imidazole-6-carboxylate (I-64): Methyl 2-(4-(6-((4-cyano-2-

Intermediate I-65

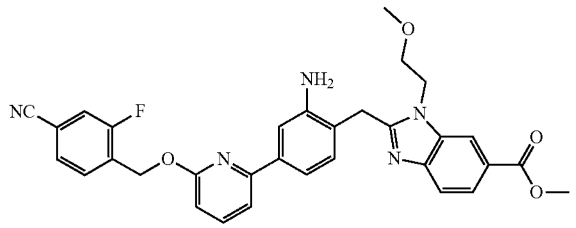

Methyl 2-(2-amino-4-(6-((4-cyano-2-fluorobenzyl)oxy)pyridin-2-yl)benzyl)-1-(2-methoxyethyl)-1H-benzo[d]imidazole-6-carboxylate (I-65): Methyl 2-(2-amino-4-(6-((4-cyano-2-fluorobenzyl)oxy)pyridin-2-yl)benzyl)-1-(2-methoxyethyl)-1H-benzo[d]imidazole-6-carboxylate was prepared identically as described for I-64 substituting 2-(4-bromo-3-nitrophenyl)acetic acid with 2-(4-bromo-2-nitrophenyl)acetic acid. ES/MS: 566.2 (M+H$^+$).

Intermediate I-66

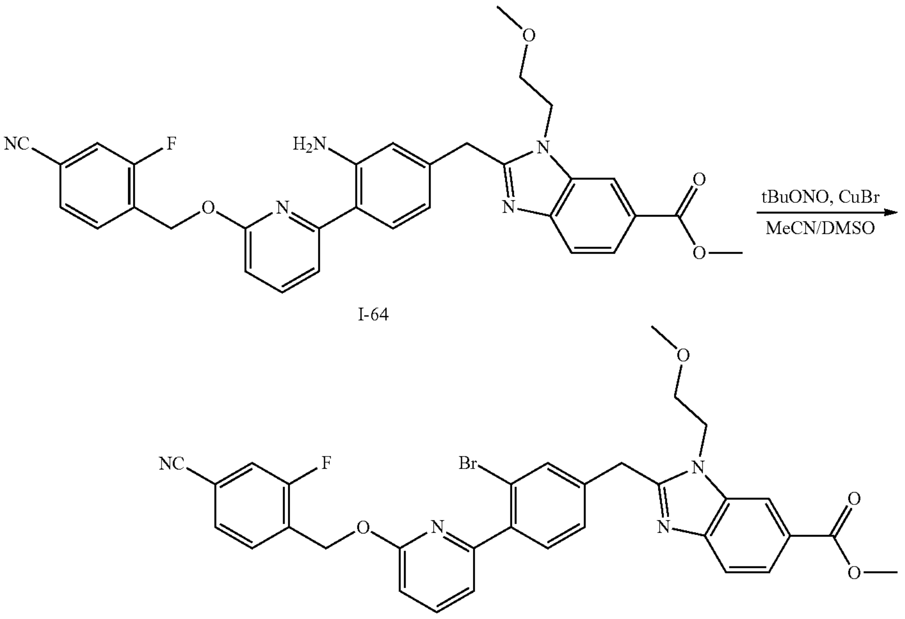

I-64

I-66 fluorobenzyl)oxy)pyridin-2-yl)-3-nitrobenzyl)-1-(2-methoxyethyl)-1H-benzo[d]imidazole-6-carboxylate (40 mg, 0.0675 mmol) was taken up in ethanol (0.50 mL) and water (0.15 mL) and acetic acid (0.15 mL) were added. Iron powder (38 mg, 0.675 mmol) was then added to the mixture and the mixture was heated to 70° C. After 2 hours, the mixture was cooled to room temperature and filtered through Celite. The residue was diluted with EtOAc (10 mL) and water (10 mL). The organic phase collected, and the aqueous phase extracted with EtOAc (2×10 mL). The combined organic phases were dried over $Na_2SO_4$ and concentrated in vacuo. The crude material was purified by silica gel chromatography (eluent: 20-80 EtOAc/hexanes) to afford the desired product. ES/MS: 566.3 (M+H$^+$).

Methyl 2-(3-bromo-4-(6-((4-cyano-2-fluorobenzyl)oxy)pyridin-2-yl)benzyl)-1-(2-methoxyethyl)-1H-benzo[d]imidazole-6-carboxylate (I-66): Methyl 2-(3-amino-4-(6-((4-cyano-2-fluorobenzyl)oxy)pyridin-2-yl)benzyl)-1-(2-methoxyethyl)-1H-benzo[d]imidazole-6-carboxylate (I-64, 26 mg, 0.0460 mmol) and copper (I) bromide (20 mg, 0.140 mmol) were suspended in EtOAc (1.0 mL) and MeCN (1.0 mL). After stirring for 5 minutes, tBuONO was added and the mixture was stirred at RT for 3 hours. The residue was then diluted with EtOAc (20 mL) and washed with aqueous saturated $NH_4Cl$ (5×5 mL). The combined organic layers were dried over $Na_2SO_4$ and concentrated in vacuo. The crude material was purified by silica gel chromatography (eluent: EtOAc in hexanes) to afford the desired product. ES/MS: 631.0 (M+H$^+$).

Intermediate I-67

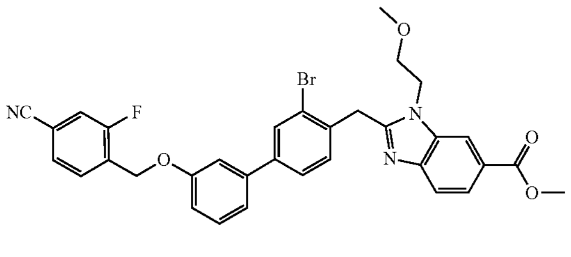

Methyl 2-(2-bromo-4-(6-((4-cyano-2-fluorobenzyl)oxy)pyridin-2-yl)benzyl)-1-(2-methoxyethyl)-1H-benzo[d]imidazole-6-carboxylate (I-67): Methyl 2-(2-bromo-4-(6-((4-cyano-2-fluorobenzyl)oxy)pyridin-2-yl)benzyl)-1-(2-methoxyethyl)-1H-benzo[d]imidazole-6-carboxylate was prepared identically as described for I-66 substituting Methyl 2-(3-amino-4-(6-((4-cyano-2-fluorobenzyl)oxy)pyridin-2-yl)benzyl)-1-(2-methoxyethyl)-1H-benzo[d]imidazole-6-carboxylate I-64 with methyl 2-(2-amino-4-(6-((4-cyano-2-fluorobenzyl)oxy)pyridin-2-yl)benzyl)-1-(2-methoxyethyl)-1H-benzo[d]imidazole-6-carboxylate I-65. ES/MS: 631.1 (M+H$^+$).

Intermediate I-68

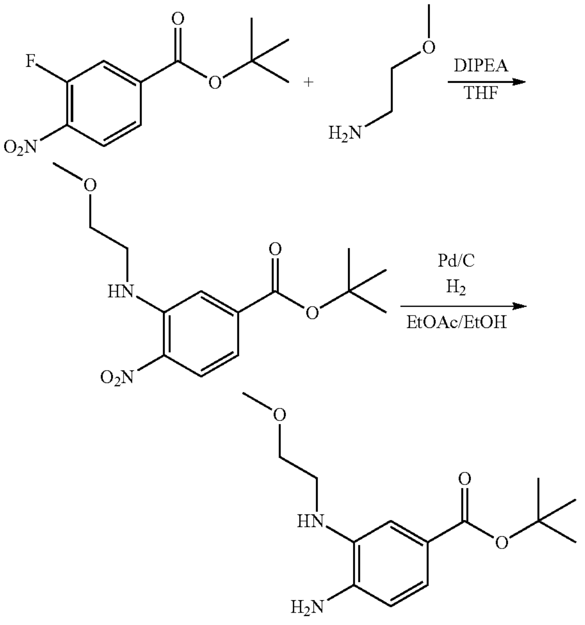

I-68

Tert-butyl 3-((2-methoxyethyl)amino)-4-nitrobenzoate: To a 500 mL RBF was added tert-butyl 3-fluoro-4-nitrobenzoate (10 g, 41.5 mmol). The material was dissolved in THF (150 mL), and 2-methoxyethanamine (7.2 mL, 82.9 mmol) and N,N-diisopropylethylamine (21.7 mL, 124 mmol) were added. The mixture was stirred at 50° C. overnight. Afterward, the mixture was concentrated to remove most of the THF, and the crude material was dissolved in EtOAc (400 mL). The organics were washed with 50% $NH_4Cl$ (2×100 mL) and with brine (1×50 mL). The organics were subsequently dried over $MgSO_4$, filtered, and concentrated under reduced pressure. The crude material was carried forward without further purification: ES/MS: 297.1 (M+H$^+$); $^1$H NMR (400 MHz, Chloroform-d) δ 8.21 (d, J=8.9 Hz, 1H), 7.55 (d, J=1.7 Hz, 1H), 7.20 (dd, J=8.9, 1.7 Hz, 1H), 3.72 (dd, J=5.8, 4.8 Hz, 2H), 3.57 (q, J=5.2 Hz, 2H), 3.46 (s, 3H), 1.62 (s, 9H).

Tert-butyl 4-amino-3-((2-methoxyethyl)amino)benzoate (I-68): To a 1 L RBF was added tert-butyl 3-((2-methoxyethyl)amino)-4-nitrobenzoate (13 g, 43.9 mmol), ethanol (100 mL), and EtOAc (50 mL). The mixture was stirred and sonicated until all material was dissolved. Nitrogen was bubbled through the mixture for 5 minutes, and then palladium on carbon (10% wt, 2.33 g, 2.19 mmol) was added. Hydrogen was bubbled through the mixture for 5 minutes, and the mixture was stirred overnight under a hydrogen balloon. Nitrogen was subsequently bubbled through the flask for 10 minutes, and then the mixture was filtered through Celite to remove the catalyst. The filtrate was concentrated under reduced pressure, and was used without further purification: ES/MS: 267.2 (M+H$^+$).

Intermediate I-69

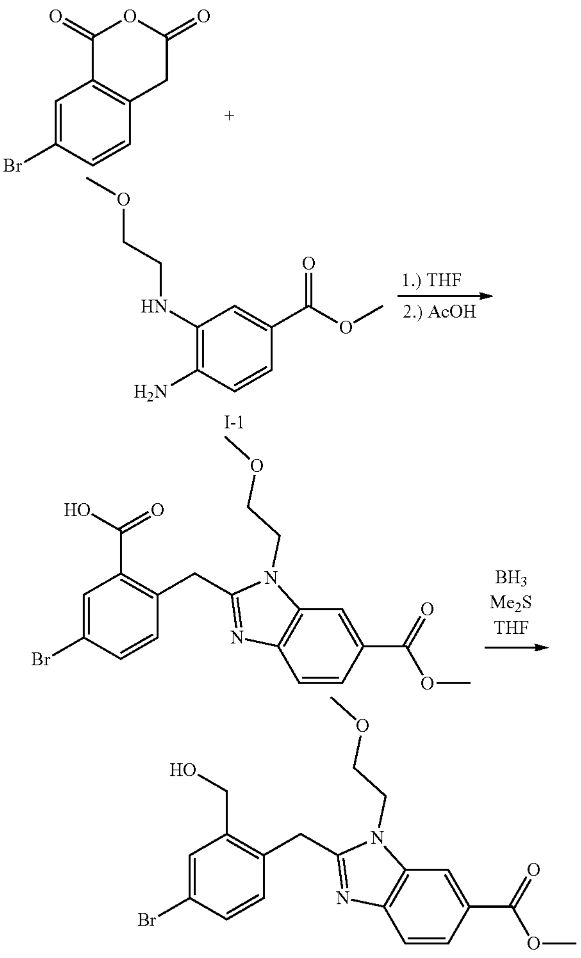

I-69

5-bromo-2-((6-(methoxycarbonyl)-1-(2-methoxyethyl)-1H-benzo[d]imidazol-2-yl)methyl)benzoic acid: To a 100 mL RBF was added 7-bromoisochromane-1,3-dione (1.18 g, 4.91 mmol), methyl 4-amino-3-(2-methoxyethylamino)benzoate (I-1, 1 g, 4.46 mmol), and THF (20 mL). The mixture was stirred 16 hours at 55° C. Afterwards, AcOH (6 mL) was added, and the mixture was stirred 24 hours at 60° C.

Analysis by LCMS showed conversion to the desired product. The volatiles were evaporated, and the crude mixture was triturated with $Et_2O$ (20 mL). The resulting solid was dried under vacuum, and carried forward: ES/MS. 447.6 (M+)

Methyl 2-(4-bromo-2-(hydroxymethyl)benzyl)-1-(2-methoxyethyl)-1H-benzo[d]imidazole-6-carboxylate (I-69): In a 100 mL RBF, 5-bromo-2-((6-(methoxycarbonyl)-1-(2-methoxyethyl)-1H-benzo[d]imidazol-2-yl)methyl)benzoic acid (300 mg, 0.67 mmol) was dissolved in dry THF (20 mL) under a nitrogen atmosphere, and the solution was cooled to 0° C. Borane dimethyl sulfide (0.083 mL, 0.87 mmol) was added via syringe dropwise, and the mixture was stirred at 0° C., then warmed slowly to room temperature. Methanol (2 mL) was added slowly to quench, then water (10 mL) and EtOAc (50 mL). The layers were separated, and the aqueous layer was extracted once with EtOAc (20 mL). The combined organic layers were dried over $MgSO_4$, filtered, and concentrated under reduced pressure. The crude residue was purified by silica column chromatography (eluent: EtOAc in hexanes) to give I-69. ES/MS: 433.1 (M+)

Intermediate I-70

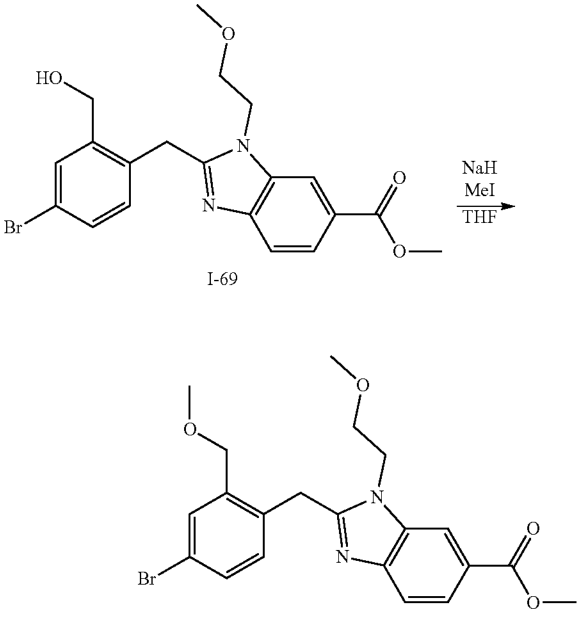

I-69

I-70

Methyl 2-(4-bromo-2-(methoxymethyl)benzyl)-1-(2-methoxyethyl)-1H-benzo[d]imidazole-6-carboxylate (I-70): To a 40 mL vial was added methyl 2-[[4-bromo-2-(hydroxymethyl)phenyl]methyl]-3-(2-methoxyethyl)benzimidazole-5-carboxylate (I-69) (100 mg, 0.23 mmol) and THF (2 mL). The solution was cooled to 0° C., and NaH (60% mineral dispersion, 18 mg, 0.46 mmol) was added under a nitrogen atmosphere. The mixture was stirred 15 min at 0° C., the iodomethane (0.073 mL, 1.15 mmol) was added, and the mixture was stirred overnight at room temperature. The mixture was quenched with 3 drops of water, and the crude mixture was added directly to a silica loading column. The crude material was purified by silica column chromatography (eluent: EtOAc in hexanes) to give I-70. ES/MS: 447.1 (M+).

Intermediate I-71

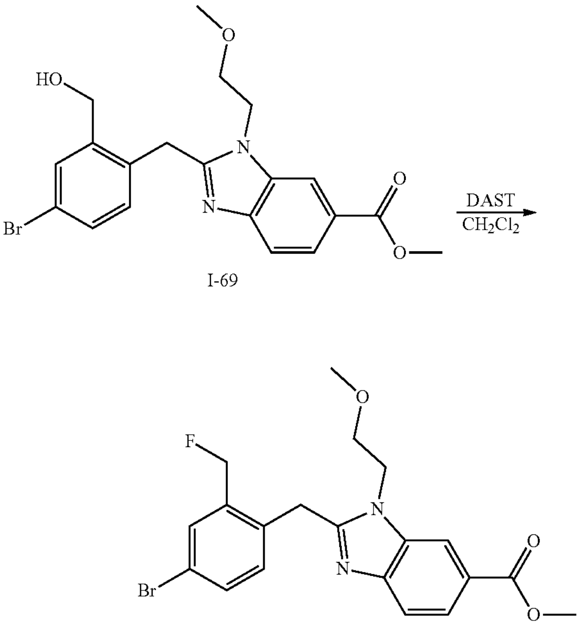

I-69

I-71

Methyl 2-(4-bromo-2-(fluoromethyl)benzyl)-1-(2-methoxyethyl)-1H-benzo[d]imidazole-6-carboxylate (I-71): To a 40 mL vial was added methyl 2-[[4-bromo-2-(hydroxymethyl)phenyl]methyl]-3-(2-methoxyethyl)benzimidazole-5-carboxylate (I-69) (100 mg, 0.23 mmol) and dichloromethane (5 mL). The solution was placed under a nitrogen atmosphere and cooled to 0° C. Diethylaminosulfur trifluoride (0.03 mL, 0.23 mmol) was added via syringe, and the mixture was stirred at 0° C. for 30 minutes. The mixture was diluted with $CH_2Cl_2$ (10 mL) and was washed once with water (5 mL). The organic layer was dried over $MgSO_4$, filtered, and concentrated under reduced pressure. The crude material was purified by silica column chromatography (eluent: EtOAc in hexanes) to give I-71. ES/MS: 435.1 (M+).

Intermediate I-72

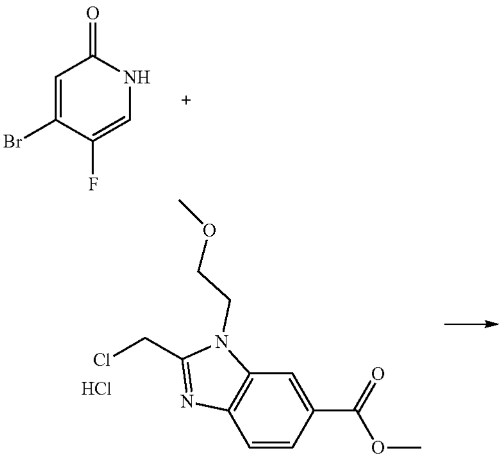

-continued

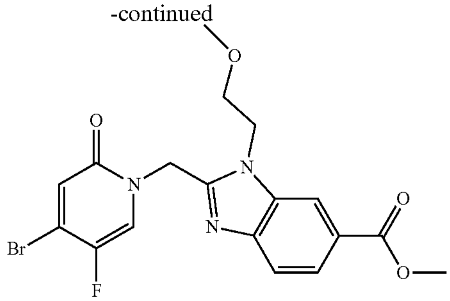

I-72

Methyl 2-((4-bromo-5-fluoro-2-oxopyridin-1(2H)-yl)methyl)-1-(2-methoxyethyl)-1H-benzo[d]imidazole-6-carboxylate (I-72): To a 20 mL vial were added methyl 2-(chloromethyl)-3-(2-methoxyethyl)benzimidazole-5-carboxylate hydrochloride (416 mg, 1.3 mmol), 4-bromo-5-fluoro-1H-pyridin-2-one (250 mg, 1.3 mmol), potassium carbonate (900 mg, 6.51 mmol), and DMF (4 mL). N,N-Diisopropylethylamine (0.45 mL, 2.6 mmol) was added, and the mixture was stirred at 60° C. for 1 hour. LCMS showed a mixture of two products (O-alkylation and N-alkylation), favoring the more polar product (N-alkylation). The mixture was diluted with EtOAc (50 mL) and was washed with water (15 mL). The organic layer was dried over $MgSO_4$, filtered, and concentrated under reduced pressure. The crude material was purified by silica chromatography (eluent: EtOAc in hexanes) to afford I-72. ES/MS: 438.1 (M+)

Intermediate I-73

I-73

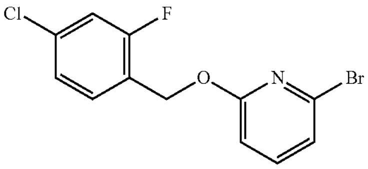

2-bromo-6-((4-chloro-2-fluorobenzyl)oxy)pyridine (I-73): 2-bromo-6-((4-chloro-2-fluorobenzyl)oxy)pyridine was prepared identically as described for I-6 substituting 3-fluoro-4-(hydroxymethyl)benzonitrile with (4-chloro-2-fluorophenyl)methanol. ES/MS: 317.8 ($M+H^+$); $^1H$ NMR (400 MHz, Chloroform-d) δ 7.52-7.45 (m, 2H), 7.19-7.02 (m, 3H), 6.75 (d, J=8.2 Hz, 1H), 5.43-5.38 (m, 2H).

Intermediate I-74

I-74

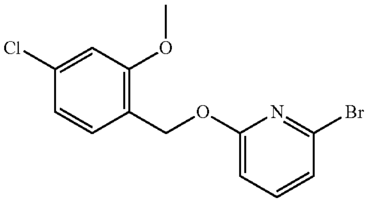

2-bromo-6-((4-chloro-2-methoxybenzyl)oxy)pyridine (I-74): 2-bromo-6-((4-chloro-2-methoxybenzyl)oxy)pyridine was prepared identically as described for I-6 substituting 3-fluoro-4-(hydroxymethyl)benzonitrile with (4-chloro-2-methoxyphenyl)methanol. ES/MS: 329.9 ($M+H^+$); $^1H$ NMR (400 MHz, Chloroform-d) δ 7.49-7.39 (m, 2H), 7.09 (d, J=7.4 Hz, 1H), 6.97 (dd, J=8.1, 2.0 Hz, 1H), 6.91 (d, J=1.9 Hz, 1H), 6.75 (d, J=8.2 Hz, 1H), 5.37 (s, 2H), 3.88 (s, 3H).

Intermediate I-75

I-75

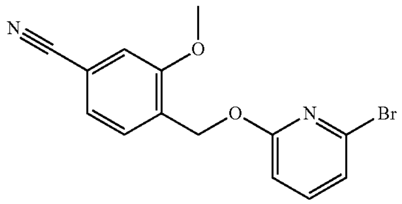

4-(((6-bromopyridin-2-yl)oxy)methyl)-3-methoxybenzonitrile (I-75): To a 20 mL vial were added 6-bromopyridin-2-ol (231 mg, 1.33 mmol), 4-(bromomethyl)-3-methoxybenzonitrile (300 mg, 1.33 mmol), silver(II) carbonate (1.1 g, 3.98 mmol), and toluene (10 mL). The mixture was heated at 100° C. for 1 hour. The mixture was subsequently cooled, and was filtered through Celite to remove the solid precipitate, rinsing with EtOAc. The filtrate was concentrated, and the crude residue was purified by silica chromatography (eluent: EtOAc in hexanes) to afford I-75. ES/MS: 319.1 (M+).

Intermediate I-76

I-76

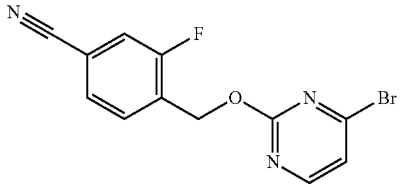

4-(((4-bromopyrimidin-2-yl)oxy)methyl)-3-fluorobenzonitrile (I-76): 4-(((4-bromopyrimidin-2-yl)oxy)methyl)-3-fluorobenzonitrile was prepared identically as described for I-45 substituting 4-(hydroxymethyl)-3-methoxy-benzonitrile with 3-fluoro-4-(hydroxymethyl)benzonitrile. ES/MS: 319.9 (M+); $^1H$ NMR (400 MHz, Chloroform-d) δ 8.32 (d, J=5.2 Hz, 1H), 7.62 (d, J=7.8 Hz, 1H), 7.31 (dd, J=7.8, 1.4 Hz, 1H), 7.21 (d, J=5.1 Hz, 1H), 7.14 (d, J=1.4 Hz, 1H), 5.55-5.48 (m, 2H), 3.93 (s, 3H).

Intermediate I-77

I-77

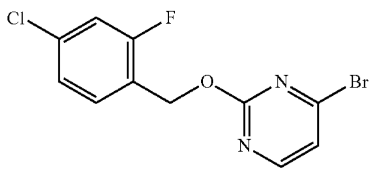

4-bromo-2-((4-chloro-2-fluorobenzyl)oxy)pyrimidine (I-77): 4-bromo-2-((4-chloro-2-fluorobenzyl)oxy)pyrimidine was prepared identically as described for I-45 substituting 4-(hydroxymethyl)-3-methoxy-benzonitrile with (4-chloro-2-fluorophenyl)methanol. ES/MS: 318.9 ($M+H^+$); $^1H$ NMR (400 MHz, Chloroform-d) δ 8.31 (d, J=5.1 Hz, 1H), 7.51 (t, J=8.1 Hz, 1H), 7.21 (d, J=5.2 Hz, 1H), 7.19-7.13 (m, 2H), 5.51-5.46 (m, 2H).

Intermediate I-78

I-78

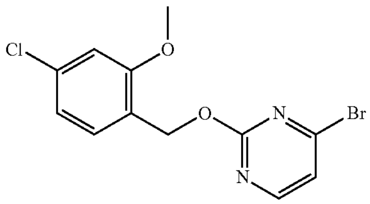

4-bromo-2-((4-chloro-2-methoxybenzyl)oxy)pyrimidine (I-78): 4-bromo-2-((4-chloro-2-methoxybenzyl)oxy)pyrimidine was prepared identically as described for I-45 substituting 4-(hydroxymethyl)-3-methoxy-benzonitrile with (4-chloro-2-methoxyphenyl)methanol. ES/MS: 318.9 ($M+H^+$); $^1H$ NMR (400 MHz, Chloroform-d) δ 8.31 (d, J=5.1 Hz, 1H), 7.51 (t, J=8.1 Hz, 1H), 7.21 (d, J=5.2 Hz, 1H), 7.19-7.13 (m, 2H), 5.51-5.46 (m, 2H).

Intermediate I-79

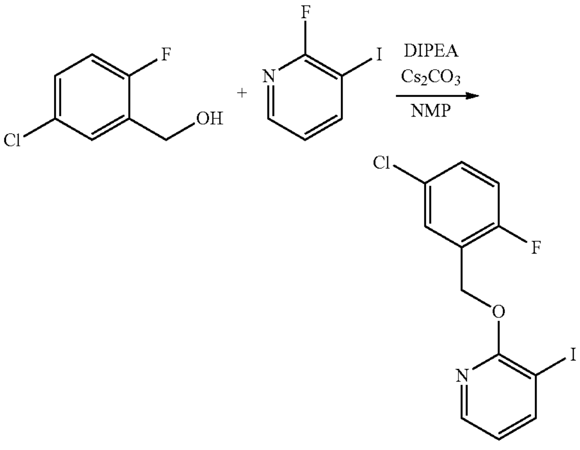

I-79

2-((5-chloro-2-fluorobenzyl)oxy)-3-iodopyridine (I-79): To a vial were added 2-chloro-3-iodo-pyridine (300 mg, 1.25 mmol), (5-chloro-2-fluoro-phenyl)methanol (302 mg, 1.88 mmol), $Cs_2CO_3$ (816 mg, 2.51 mmol), N,N-diisopropylethylamine (0.44 mL, 2.51 mmol) and NMP (1.5 mL). The mixture was heated at 120° C. overnight. The mixture was subsequently cooled and was dissolved in EtOAc (30 mL). The organics were washed with water (2×10 mL), and the organic layer was dried over $MgSO_4$, filtered, and concentrated under reduced pressure. The crude residue was purified by silica chromatography (eluent: EtOAc in hexanes) to afford I-79. ES/MS: 318.9 ($M+H^+$); $^1H$ NMR (400 MHz, Chloroform-d) δ 8.31 (d, J=5.1 Hz, 1H), 7.51 (t, J=8.1 Hz, 1H), 7.21 (d, J=5.2 Hz, 1H), 7.19-7.13 (m, 2H), 5.51-5.46 (m, 2H).

Intermediate I-80

I-80

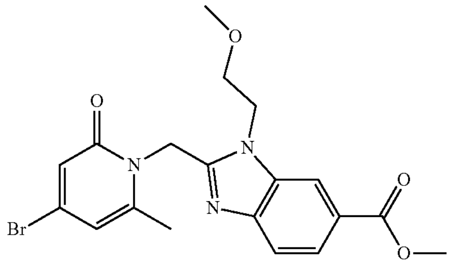

Methyl 2-((4-bromo-6-methyl-2-oxopyridin-1(2H)-yl)methyl)-1-(2-methoxyethyl)-1H-benzo[d]imidazole-6-carboxylate (I-80): Methyl 2-((4-bromo-6-methyl-2-oxopyridin-1(2H)-yl)methyl)-1-(2-methoxyethyl)-1H-benzo[d]imidazole-6-carboxylate was prepared identically as described for I-72 substituting 4-bromo-5-fluoro-1H-pyridin-2-one with 4-bromo-6-methylpyridin-2(1H)-one: ES/MS: 434.3 (M+); $^1H$ NMR (400 MHz, Chloroform-d) δ 8.08 (d, J=1.5 Hz, 1H), 7.94 (dd, J=8.5, 1.6 Hz, 1H), 7.69 (d, J=8.5 Hz, 1H), 6.70 (d, J=2.1 Hz, 1H), 6.33 (dd, J=2.2, 0.9 Hz, 1H), 5.46 (s, 2H), 4.66 (t, J=5.0 Hz, 2H), 3.95 (s, 3H), 3.72 (t, J=5.0 Hz, 2H), 3.28 (s, 3H), 2.62 (s, 3H).

Intermediate I-81

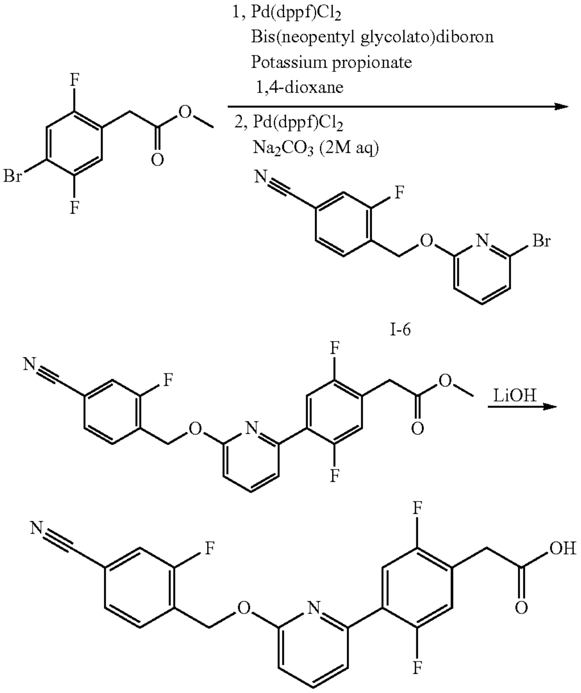

I-81

Methyl 2-(4-(6-((4-cyano-2-fluorobenzyl)oxy)pyridin-2-yl)-2,5-difluorophenyl)acetate: A suspension of methyl 2-(4-bromo-2,5-difluorophenyl)acetate (10.5 g, 39.6 mmol), Bis (neopentyl glycolato)diboron (17.9 g, 79.2 mmol), [1,1'-Bis (diphenylphosphino)ferrocene]dichloropalladium(II); $PdCl_2$ (dppf) (2.94 g, 3.96 mmol), and potassium propionate (15.6 g, 139 mmol) in dioxane (50 mL) was degassed with Ar for 20 min. The mixture was sealed and heated at 100° C. for 2 hours. Sodium carbonate (2.0 M, 39.6 mL, 79.2 mmol) was added and the mixture was stirred at RT for 10 min. [1,1'-Bis(diphenylphosphino)ferrocene]dichloropalladium (II); $PdCl_2$(dppf) (1.47 g, 1.98 mmol) and I-6 (14 g, 45.6 mmol) were added, the mixture was degassed for 10 min with Ar, then sealed and heated at 100° C. for 1 hour. The mixture was diluted with EtOAc and washed with brine. The organic extract was dried over sodium sulfate and chromatographed (eluent: EtOAc/hexanes) to give the title product: ES/MS: 413.2 ($M+H^+$).

2-(4-(6-((4-cyano-2-fluorobenzyl)oxy)pyridin-2-yl)-2,5-difluorophenyl)acetic acid (I-81). A solution of methyl 2-(4-(6-((4-cyano-2-fluorobenzyl)oxy)pyridin-2-yl)-2,5-difluorophenyl)acetate (12.5 g, 30.3 mmol) and lithium hydroxide (0.2 M, 19.7 mL, 39.4 mmol) in $CH_3CN$ (50 mL) was heated at 50° C. for 2 hours. The mixture was acidified with 1N of hydrochloride to pH=6-7. The material crashed out and was filtered by filter funnel. The solid was washed with water and dried overnight to yield the product: ES/MS: 399.2 ($M+H^+$); $^1H$ NMR (400 MHz, Methanol-d4) δ 7.83-7.77 (m, 1H), 7.78-7.65 (m, 2H), 7.64-7.59 (m, 2H), 7.58-7.51 (m, 1H), 7.26-7.14 (m, 1H), 6.91 (d, J=8.2 Hz, 1H), 5.63 (s, 2H), 3.73 (d, J=1.2 Hz, 2H).

Intermediate I-82

I-82

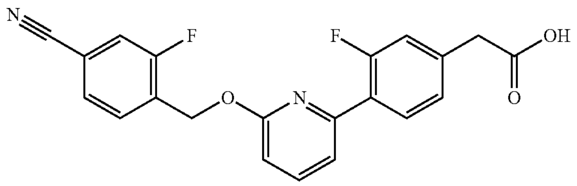

2-(4-(6-((4-cyano-2-fluorobenzyl)oxy)pyridin-2-yl)-3-fluorophenyl)acetic acid (I-82). 2-(4-(6-((4-cyano-2-fluorobenzyl)oxy)pyridin-2-yl)-3-fluorophenyl)acetic acid (I-82) was prepared in identical manner as I-81 substituting methyl 2-(4-bromo-2,5-difluorophenyl)acetate with methyl 2-(4-bromo-3-fluorophenyl)acetate. ES/MS: 381.2 ($M+H^+$); $^1H$ NMR (400 MHz, Methanol-d4) δ 7.92 (t, J=8.2 Hz, 1H), 7.76 (dt, J=14.4, 7.6 Hz, 2H), 7.66-7.55 (m, 2H), 7.49 (dd, J=7.3, 1.8 Hz, 1H), 7.27-7.12 (m, 2H), 6.88 (d, J=8.1 Hz, 1H), 5.63 (s, 2H), 3.70 (s, 2H).

Intermediate I-83

I-83

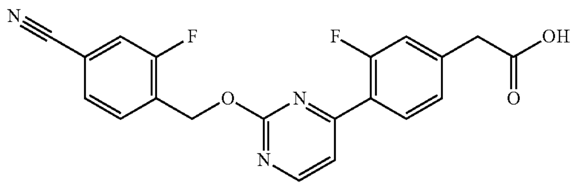

2-(4-(2-((4-cyano-2-fluorobenzyl)oxy)pyrimidin-4-yl)-3-fluorophenyl)acetic acid (I-83): 2-(4-(2-((4-cyano-2-fluorobenzyl)oxy)pyrimidin-4-yl)-3-fluorophenyl)acetic acid (I-83) was prepared in an identical manner as I-82 substituting 4-(((6-bromopyridin-2-yl)oxy)methyl)-3-fluorobenzonitrile (I-6) with 4-(((4-bromopyrimidin-2-yl)oxy)methyl)-3-fluorobenzonitrile (I-76). ES/MS: 382.2 ($M+H^+$); $^1H$ NMR (400 MHz, Methanol-d4) δ 8.65 (d, J=5.3 Hz, 1H), 8.11 (t, J=8.1 Hz, 1H), 7.81 (t, J=7.5 Hz, 1H), 7.69-7.59 (m, 3H), 7.36-7.22 (m, 2H), 5.70 (s, 2H), 3.74 (s, 2H).

Intermediate I-84

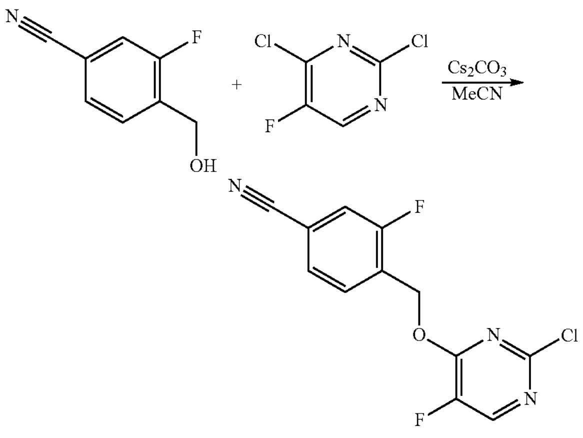

I-84

4-(((2-chloro-5-fluoropyrimidin-4-yl)oxy)methyl)-3-fluorobenzonitrile (I-84): 4-(((2-chloro-5-fluoropyrimidin-4-yl)oxy)methyl)-3-fluorobenzonitrile was prepared as described for I-25 substituting 2,4-dichloro-5-fluoropyrimidine for 4-bromo-2-chloro-thiazole. ES/MS: 282.2 $[M+H]^+$.

Intermediate I-85

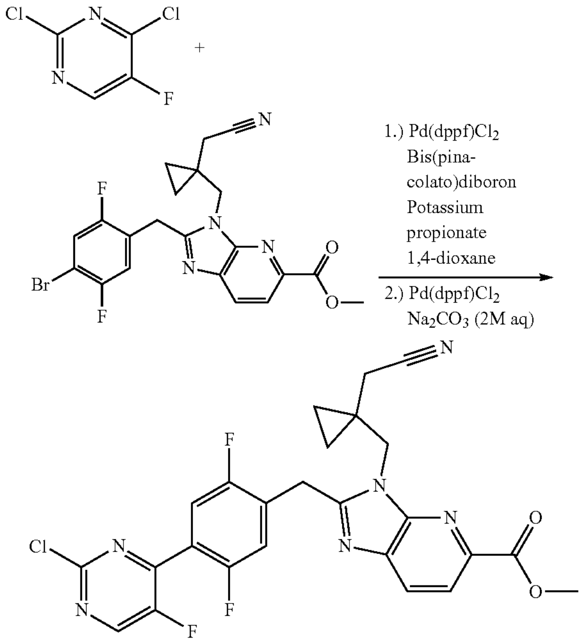

I-85

Methyl 2-(4-(2-chloro-5-fluoropyrimidin-4-yl)-2,5-difluorobenzyl)-3-((1-(cyanomethyl)cyclopropyl)methyl)-3H-imidazo[4,5-b]pyridine-5-carboxylate (I-85)

To a vial charged with methyl 2-(4-bromo-2,5-difluorobenzyl)-3-((1-(cyanomethyl)cyclopropyl)methyl)-3H-imidazo[4,5-b]pyridine-5-carboxylate (30.0 mg, 0.063 mmol) (synthesized in a manner analogous to I-96), bis(pinacolato)diboron (20.8 mg, 0.082 mmol), Pd(dppf)$Cl_2$ (7.0 mg, 0.0095 mmol), and potassium propionate (21.2 mg, 0.19 mmol) was added 1,4-dioxane (1.0 mL). The suspension was degassed by bubbling argon for 60 seconds, then the vial was sealed and heated thermally at 115° C. for 45 minutes. To the cooled mixture was added 2,4-dichloro-5-fluoropyrimidine (10.5 mg, 0.063 mmol), Pd(dppf)$Cl_2$ (3.5 mg, 0.0047 mmol), and aqueous sodium carbonate (2 M, 63 μL, 0.13 mmol). The mixture was degassed by bubbling argon for 60 seconds, then the vial was sealed and heated at 90° C. for 4 h. The cooled mixture was filtered through a pad of Celite (eluent: EtOAc), concentrated, and purified by silica gel chromatography (eluent: EtOAc/hexanes) to give the desired product. ES/MS: 527.0 $[M+H]^+$.

Intermediate I-86

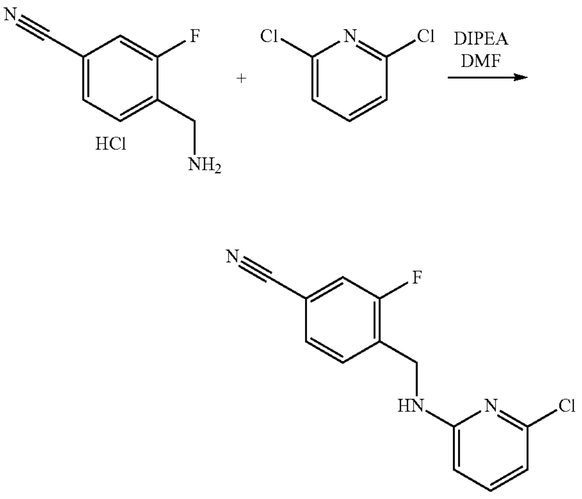

I-86

4-[[(6-chloro-2-pyridyl)amino]methyl]-3-fluoro-benzonitrile (I-86): To a microwave vial was added 4-(aminomethyl)-3-fluoro-benzonitrile; hydrochloride (277 mg, 1.49 mmol), 2,6-dichloropyridine (200 mg, 1.35 mmol), N,N-Diisopropylethylamine (0.942 mL, 5.41 mmol), and DMF. The solution was heated to 120° C. for 12 h. The crude solution was concentrated under reduced pressure and purified by silica column chromatography (50-100%) EtOAc in hexanes to give the title compound. ES/MS: 262.2 $(M+H^+)$.

Intermediate I-87

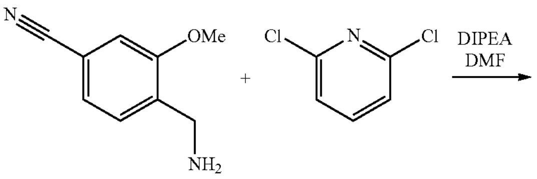

-continued

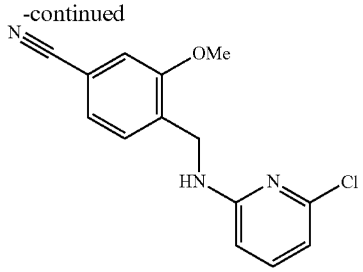

I-87

4-(((6-chloropyridin-2-yl)amino)methyl)-3-methoxybenzonitrile (I-87): 4-(((6-chloropyridin-2-yl)amino)methyl)-3-methoxybenzonitrile was made following procedure I-86, using 4-(aminomethyl)-3-fluoro-benzonitrile; hydrochloride, in place of 4-(aminomethyl)-3-methoxybenzonitrile. ES/MS: 274.1 $(M+H^+)$.

Intermediate I-88

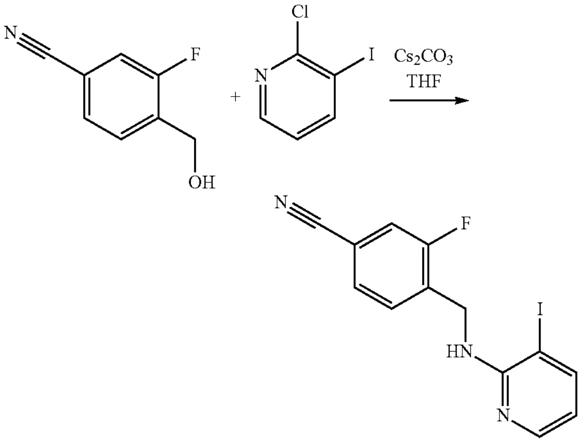

I-88

3-fluoro-4-[(3-iodo-2-pyridyl)oxymethyl]benzonitrile (I-88): To a microwave vial was added 3-fluoro-4-(hydroxymethyl)benzonitrile (114 mg, 0.75 mmol), 2-chloro-3-iodo-pyridine (150 mg, 0.63 mmol), cesium carbonate (367 mg, 1.13 mmol), and 5 mL of THF. The vial was sealed and the mixture heated to 80° C. for 16 h. The mixture was cooled to RT, concentrated, and purified on a silica column (35-100% EtOAc in hexanes) to give the title compound: ES/MS: 354.9 $(M+H^+)$.

Intermediate I-89

I-89

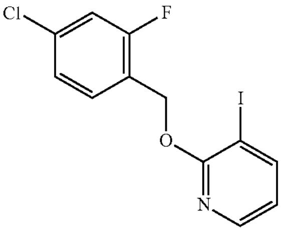

2-[(2-fluorophenyl)methoxy]-3-iodo-pyridine (I-89): To a microwave vial was added (4-chloro-2-fluoro-phenyl)

methanol (121 mg, 0.75 mmol), 2-chloro-3-iodo-pyridine (120 mg, 0.50 mmol), cesium carbonate (294 mg, 0.90 mmol), and 5 mL of THF. The vial was sealed and the mixture heated to 80° C. for 16 h. The mixture was cooled to RT, concentrated, and purified on a silica column (35-100% EtOAc in hexanes) to give the title compound. ES/MS: 363.8 (M+H$^+$).

Intermediate I-90

I-90

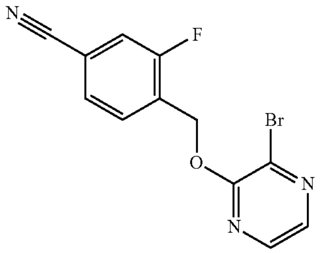

4-[(3-bromopyrazin-2-yl)oxymethyl]-3-fluoro-benzonitrile (I-90): To a microwave vial was added 3-fluoro-4-(hydroxymethyl)benzonitrile (335 mg, 2.22 mmol), 2,3-dibromopyrazine (440 mg, 1.85 mmol), cesium carbonate (1.08 g, 3.33 mmol), and THF (10 mL). The vial was sealed and the mixture heated to 80° C. for 16 h. The mixture was cooled to RT, concentrated, and purified on a silica column (35-100%) EtOAc in hexanes to give the title compound: ES/MS: 308.1 (M+).

Intermediate I-91

I-91

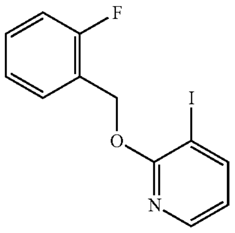

2-[(2-fluorophenyl)methoxy]-3-iodo-pyridine (I-91): To a microwave vial was added 3-fluoro-4-(hydroxymethyl)benzonitrile (94.8 mg, 0.75 mmol), 2-chloro-3-iodo-pyridine (120 mg, 0.50 mmol), cesium carbonate (294 mg, 0.90 mmol), and 5 mL of THF. The vial was sealed and the mixture heated to 80° C. for 16 h. The mixture was cooled to RT, concentrated, and purified on a silica column (35-100% EtOAc in hexanes) to give the title compound: ES/MS: 329.9 (M+H$^+$).

Intermediate I-92

I-92

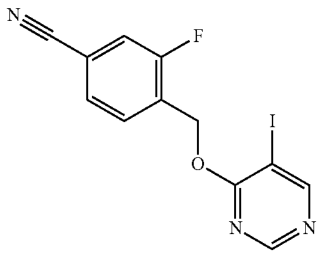

3-fluoro-4-[(5-iodopyrimidin-4-yl)oxymethyl]benzonitrile (I-92): 3-fluoro-4-[(5-iodopyrimidin-4-yl)oxymethyl]benzonitrile was made following procedure I-88, except substituting 2-chloro-3-iodo-pyridine for 4-chloro-5-iodo-pyrimidine. ES/MS: 356.0 (M+H$^+$).

Intermediate I-93

I-93

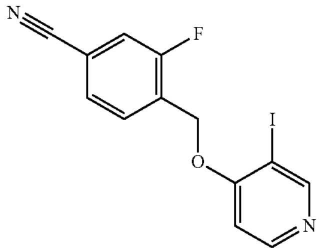

3-fluoro-4-[(3-iodo-4-pyridyl)oxymethyl]benzonitrile (I-93): 3-fluoro-4-[(3-iodo-4-pyridyl)oxymethyl]benzonitrile was made following procedure I-88, except substituting 2-chloro-3-iodo-pyridine for 4-chloro-3-iodo-pyridine. ES/MS: 354.9 (M+H$^+$).

Intermediate I-94

I-94

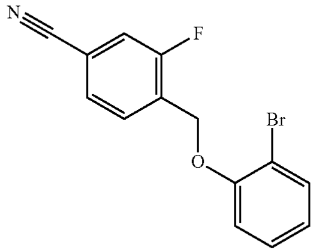

4-[(2-bromophenoxy)methyl]-3-fluoro-benzonitrile (I-94): 4-[(2-bromophenoxy)methyl]-3-fluoro-benzonitrile was made following procedure I-88, except substituting 2-chloro-3-iodo-pyridine for 2-bromophenol, and 4-cyano-2-fluorobenzyl bromide for 3-fluoro-4-(hydroxymethyl)benzonitrile. $^1$H NMR (400 MHz, Methanol-d4) δ 7.92-7.85 (m, 1H), 7.68-7.56 (m, 3H), 7.35 (ddd, J=8.2, 7.4, 1.6 Hz, 1H), 7.16 (dd, J=8.3, 1.4 Hz, 1H), 6.94 (td, J=7.7, 1.4 Hz, 1H), 5.33 (s, 2H).

Intermediate I-95

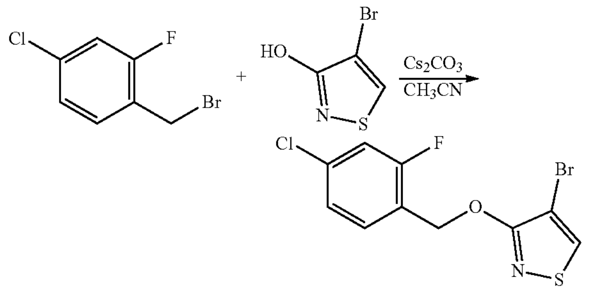

I-95

4-bromo-3-((4-chloro-2-fluorobenzyl)oxy)isothiazole (I-95): To a vial was added 4-bromoisothiazol-3-ol (50.0 mg, 0.278 mmol) and cesium carbonate (181 mg, 0.555 mmol) followed by acetonitrile (1.00 mL) and the mixture was stirred for 3 h at 80° C. The mixture was poured into water and the precipitate was filtered off, washed with water and dried under vacuum to yield the title compound: $^{1}$H NMR (400 MHz, Chloroform-d) δ 8.43 (s, 1H), 7.51 (t, J=8.0 Hz, 1H), 7.22-7.13 (m, 2H), 5.50 (d, J=1.1 Hz, 2H).

Intermediate I-96

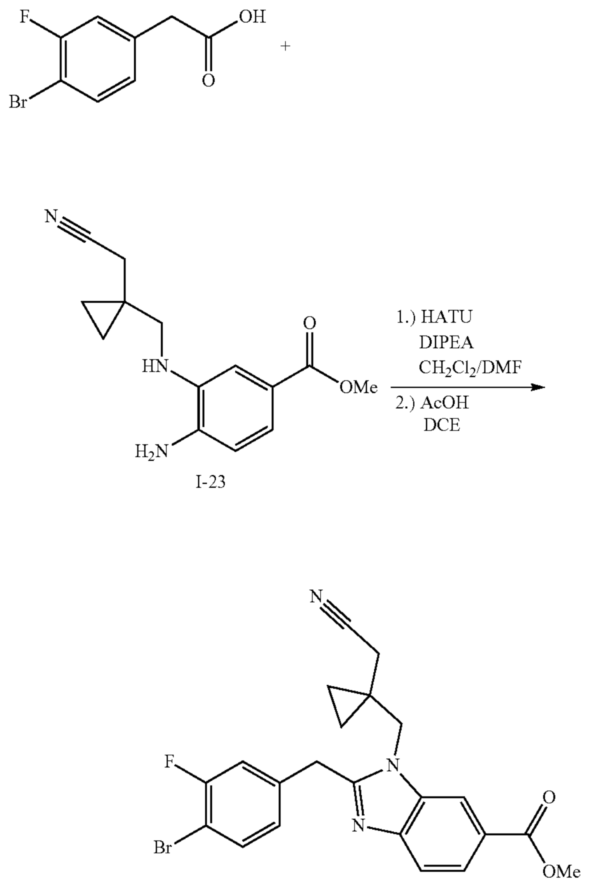

I-23

I-96

Methyl 2-(4-bromo-3-fluorobenzyl)-1-((1-(cyanomethyl) cyclopropyl)methyl)-1H-benzo[d]imidazole-6-carboxylate (I-96): To a solution of 2-(4-bromo-3-fluoro-phenyl)acetic acid (300 mg, 1.29 mmol) in DMF (6.00 mL) was added methyl 4-amino-3-(((1-(cyanomethyl)cyclopropyl)methyl) amino)benzoate (334 mg, 1.29 mmol) and o-(7-azabenzo-triazol-1-yl)-N,N,N',N'-tetramethyluronium hexafluoro-phosphate (588 mg, 1.55 mmol) followed by N,N-diisopropylethylamine purified by redistillation, 99.5% (1.12 mL, 6.44 mmol) and the mixture was stirred for 1 h at room temperature. The mixture was concentrated in vacuo, taken up in EtOAc and washed with water (1×) and brine (1×). The organic layer was dried over sodium sulfate, filtered and concentrated in vacuo. The crude residue was dissolved in AcOH (12 mL) and the mixture was heated to 60° C. for 3 h. The mixture was concentrated in vacuo, the crude residue was taken up in DCM and washed with saturated aqueous sodium bicarbonate. The layers were separated and the aqueous layer was extracted with DCM (2×). The combined organic extracts were dried over sodium sulfate, filtered and the filtrate was concentrated in vacuo. The crude residue was purified by column chromatography (0-100% EtOAc in hexane) to give the title compound. ES/MS m/z: 458.1 (M+H$^{+}$).

Intermediate I-97

I-97

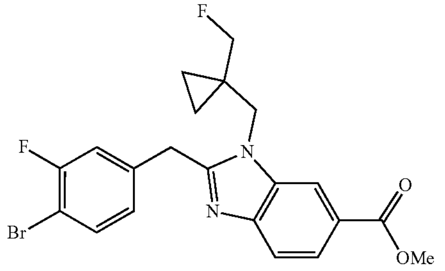

Methyl 2-(4-bromo-3-fluorobenzyl)-1-((1-(fluoromethyl) cyclopropyl)methyl)-1H-benzo[d]imidazole-6-carboxylate (I-97): Methyl 2-(4-bromo-3-fluorobenzyl)-1-((1-(fluoromethyl)cyclopropyl)methyl)-1H-benzo[d]imidazole-6-carboxylate was prepared identically as described for I-96 substituting methyl 4-amino-3-(((1-(cyanomethyl)cyclopropyl)methyl)amino)benzoate with methyl 4-amino-3-(((1-(fluoromethyl)cyclopropyl)methyl)amino)benzoate. ES/MS: 469.0 (M+H$^{+}$).

Intermediate I-98

I-98

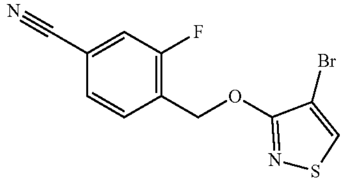

4-(((4-bromoisothiazol-3-yl)oxy)methyl)-3-fluorobenzonitrile (I-98): 4-(((4-bromoisothiazol-3-yl)oxy)methyl)-3-fluorobenzonitrile was prepared identically as described for I-95 substituting 1-(bromomethyl)-4-chloro-2-fluoro-benzene with 4-(bromomethyl)-3-fluoro-benzonitrile. $^{1}$H NMR (400 MHz, Chloroform-d) δ 8.46 (s, 1H), 7.72 (t, J=7.5 Hz, 1H), 7.53 (dd, J=8.0, 1.5 Hz, 1H), 7.42 (dd, J=9.2, 1.5 Hz, 1H), 5.60 (s, 2H).

Intermediate I-99

I-99

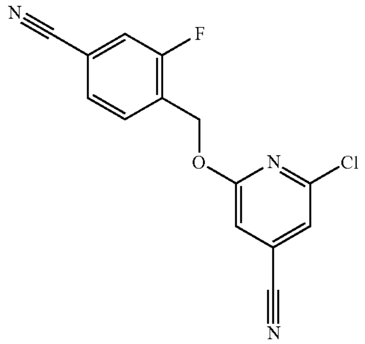

2-chloro-6-((4-cyano-2-fluorobenzyl)oxy)isonicotinonitrile (I-99): 2-chloro-6-((4-cyano-2-fluorobenzyl)oxy)isonicotinonitrile was prepared identically as described for I-25 substituting 4-bromo-2-chloro-thiazole with 2,6-dichloropyridine-4-carbonitrile. $^1$H NMR (400 MHz, Chloroform-d) δ 7.65 (t, J=7.5 Hz, 1H), 7.54-7.50 (m, 1H), 7.46-7.41 (m, 1H), 7.20 (d, J=1.0 Hz, 1H), 7.02 (d, J=1.0 Hz, 1H), 5.53 (s, 2H).

Intermediate I-100

I-100

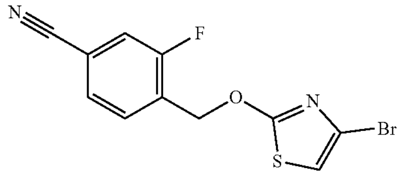

4-(((4-bromothiazol-2-yl)oxy)methyl)-3-fluorobenzonitrile (I-100): 4-(((4-bromothiazol-2-yl)oxy)methyl)-3-fluorobenzonitrile was prepared identically as described for I-25 substituting 4-bromo-2-chloro-thiazole with 2,6-dichloropyridine-4-carbonitrile. ES/MS: 469.0 (M+H$^+$); $^1$H NMR (400 MHz, Chloroform-d) δ 7.66 (t, J=7.5 Hz, 1H), 7.56-7.50 (m, 1H), 7.44 (dd, J=9.1, 1.6 Hz, 1H), 6.68 (s, 1H), 5.60 (s, 2H).

Intermediate I-101

I-101

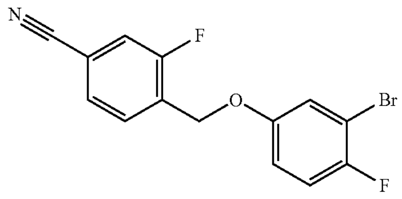

4-((3-bromo-4-fluorophenoxy)methyl)-3-fluorobenzonitrile (I-101): 4-((3-bromo-4-fluorophenoxy)methyl)-3-fluorobenzonitrile was prepared identically as described for I-26 substituting 3-bromo-5-fluoro-phenol with 3-bromo-4-fluoro-phenol: $^1$H NMR (400 MHz, Chloroform-d) δ 7.68 (t, J=7.5 Hz, 1H), 7.54 (dd, J=8.0, 1.6 Hz, 1H), 7.43 (dd, J=9.3, 1.5 Hz, 1H), 7.21-7.17 (m, 1H), 7.09 (dd, J=9.0, 8.0 Hz, 1H), 6.93-6.87 (m, 1H), 5.15 (s, 2H).

Intermediates I-102 and I-103

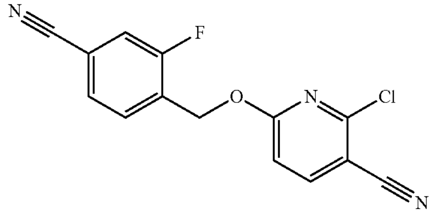

+

I-102

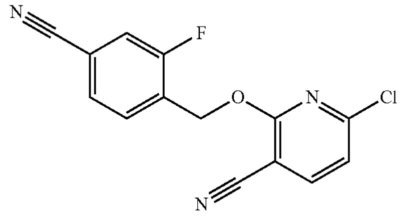

I-103

2-chloro-6-((4-cyano-2-fluorobenzyl)oxy)nicotinonitrile (I-102) & 6-chloro-2-((4-cyano-2-fluorobenzyl)oxy)nicotinonitrile (I-103): 2-chloro-6-((4-cyano-2-fluorobenzyl)oxy)nicotinonitrile (I-102) & 6-chloro-2-((4-cyano-2-fluorobenzyl)oxy)nicotinonitrile (I-103) were prepared identically as described for I-2 & I-3 substituting 2-bromo-6-chloro-3-methyl-pyridine with 2,6-dichloropyridine-3-carbonitrile: (mixture of regioisomers). $^1$H NMR (400 MHz, Chloroform-d) δ 7.93-7.85 (m, 2H), 7.74 (t, J=7.5 Hz, 1H), 7.65 (t, J=7.5 Hz, 1H), 7.57-7.49 (m, 2H), 7.47-7.41 (m, 2H), 7.12 (d, J=7.9 Hz, 1H), 6.87 (d, J=8.5 Hz, 1H), 5.62 (s, 2H), 5.56 (s, 1H).

Intermediates I-104 and I-105

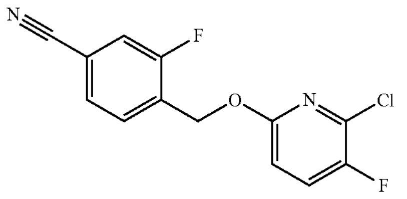

+

I-104

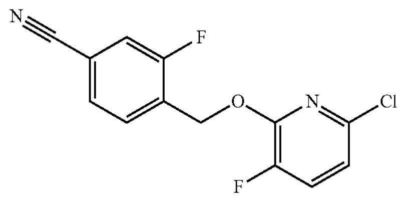

I-105

4-(((6-chloro-5-fluoropyridin-2-yl)oxy)methyl)-3-fluorobenzonitrile (I-104) & 4-(((6-chloro-3-fluoropyridin-2-yl)oxy)methyl)-3-fluorobenzonitrile (I-105): 4-(((6-chloro-5-fluoropyridin-2-yl)oxy)methyl)-3-fluorobenzonitrile (I-104) & 4-(((6-chloro-3-fluoropyridin-2-yl)oxy)methyl)-3-fluorobenzonitrile (I-105) were prepared identically as described for I-2 & I-3 substituting 2-bromo-6-chloro-3-methyl-pyridine with 2,6-dichloro-3-fluoro-pyridine: (mixture of regioisomers). $^1$H NMR (400 MHz, Chloroform-d) δ 7.79 (t, J=7.5

Hz, 1H), 7.71 (t, J=7.5 Hz, 1H), 7.58 (dd, J=7.9, 1.5 Hz, 1H), 7.52 (dd, J=7.9, 1.5 Hz, 1H), 7.47-7.41 (m, 2H), 7.41-7.35 (m, 1H), 7.28-7.28 (m, 2H), 6.97-6.93 (m, 1H), 5.57 (s, 2H), 5.27 (s, 2H).

Intermediate I-106

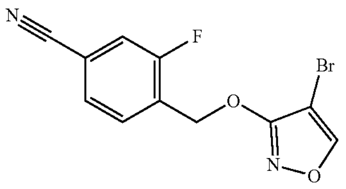

I-106

4-(((4-bromoisoxazol-3-yl)oxy)methyl)-3-fluorobenzonitrile (I-106): 4-(((4-bromoisoxazol-3-yl)oxy)methyl)-3-fluorobenzonitrile (I-106) were prepared identically as described for I-95 substituting 4-bromoisothiazol-3-ol with 4-bromoisoxazol-3-ol. $^{1}H$ NMR (400 MHz, Chloroform-d) δ 8.21 (s, 1H), 7.69 (t, J=7.5 Hz, 1H), 7.55-7.50 (m, 1H), 7.42 (dd, J=9.1, 1.5 Hz, 1H), 5.45 (s, 2H), 5.30 (s, 1H).

Intermediate I-107

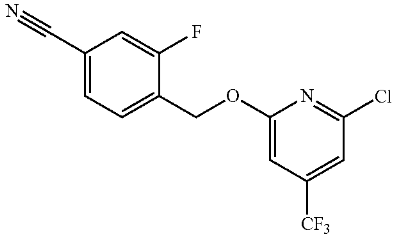

I-107

4-(((6-chloro-4-(trifluoromethyl)pyridin-2-yl)oxy)methyl)-3-fluorobenzonitrile (I-107): 4-(((6-chloro-4-(trifluoromethyl)pyridin-2-yl)oxy)methyl)-3-fluorobenzonitrile (I-107) was prepared identically as described for I-25 substituting 4-bromo-2-chloro-thiazole with 2,6-dichloro-4-(trifluoromethyl)pyridine. $^{1}H$ NMR (400 MHz, Chloroform-d) δ 7.67 (t, J=7.5 Hz, 1H), 7.52 (dd, J=7.9, 1.5 Hz, 1H), 7.43 (dd, J=9.1, 1.5 Hz, 1H), 7.20 (s, 1H), 7.00 (s, 1H), 5.55 (s, 2H).

Intermediate I-108

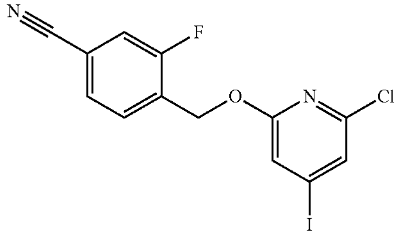

I-108

4-(((6-chloro-4-iodopyridin-2-yl)oxy)methyl)-3-fluorobenzonitrile (I-108): 4-(((6-chloro-4-iodopyridin-2-yl)oxy)methyl)-3-fluorobenzonitrile was prepared identically as described for I-25 substituting 4-bromo-2-chloro-thiazole with 2,6-dichloro-4-iodo-pyridine: ES/MS: 297.0 (M+H$^{+}$).

Intermediate I-109

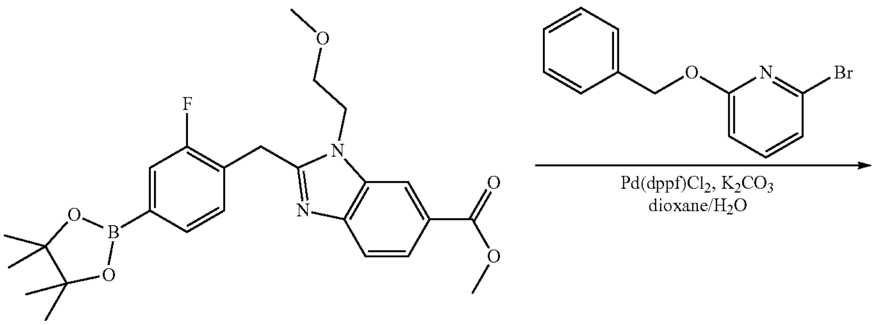

I-5

-continued

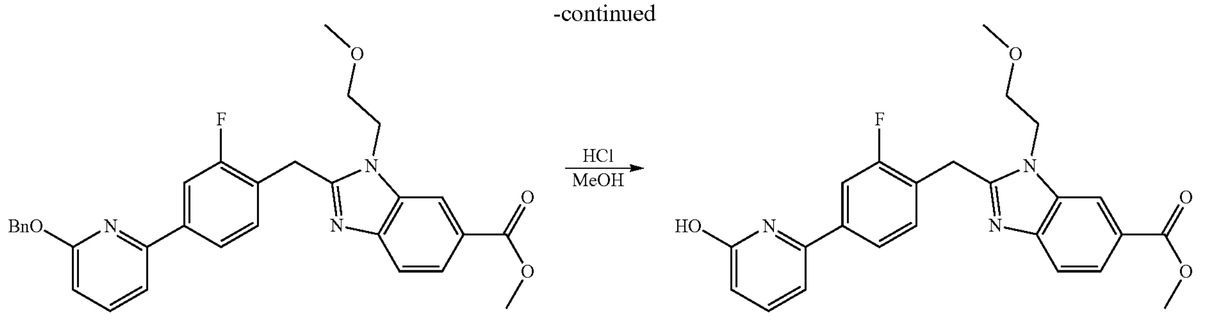

I-109

Step 1. Methyl 2-(4-(6-(benzyloxy)pyridin-2-yl)-2-fluorobenzyl)-1-(2-methoxyethyl)-1H-benzo[d]imidazole-6-carboxylate. To a solution of methyl 2-(2-fluoro-4-(4,4,5,5-tetramethyl-1,3,2-dioxaborolan-2-yl)benzyl)-1-(2-methoxyethyl)-1H-benzo[d]imidazole-6-carboxylate (I-5, 10 g, 21.4 mmol) and 2-benzyloxy-6-bromo-pyridine (6.50 g, 24.6 mmol) in dioxane (200 mL) was added Pd(dppf)$Cl_2$ (1.60 g, 2.19 mmol) and potassium carbonate (2.00 M aqueous, 22.0 mL, 44.0 mmol). The solution was degassed with nitrogen and heated to 90° C. (internal temperature) for 5.5 hours. Additional 2-benzyloxy-6-bromo-pyridine (0.850 g, 3.22 mmol) was added and heating was continued for 1 hour. The mixture was then cooled to room temperature and diluted with EtOAc. The solution was decanted from the residual solids and washed with brine (2×). The aqueous layer was back-extracted with EtOAc and the combined organic layers were dried over magnesium sulfate and concentrated to dryness. The crude material was purified by $SiO_2$ chromatography (eluent: 10-40% EtOAc/Hexanes) to provide methyl 2-(4-(6-(benzyloxy)pyridin-2-yl)-2-fluorobenzyl)-1-(2-methoxyethyl)-1H-benzo[d]imidazole-6-carboxylate. ES/MS: 526.402 ($M+H^+$).

Step 2. Methyl 2-(2-fluoro-4-(6-hydroxypyridin-2-yl)benzyl)-1-(2-methoxyethyl)-1H-benzo[d]imidazole-6-carboxylate (I-109). To a solution of methyl 2-(4-(6-(benzyloxy)pyridin-2-yl)-2-fluorobenzyl)-1-(2-methoxyethyl)-1H-benzo[d]imidazole-6-carboxylate (10.2 g, 19.4 mmol) in MeOH (200 mL) was added hydrogen chloride (4.00 M in 1,4-dioxane, 100 mL, 400 mmol). The solution was heated to 70° C. (external temperature) for 12 hours. The mixture was then concentrated, dissolved in 10% $MeOH/CH_2Cl_2$, and washed with aqueous bicarbonate. The aqueous layer was back-extracted with 10% $MeOH/CH_2Cl_2$. The resulting organic layers were combined, washed with brine and dried over magnesium sulfate. After concentration to dryness, the resulting material was triturated in $Et_2O$ with sonication, diluted with hexanes, and filtered to provide methyl 2-(2-fluoro-4-(6-hydroxypyridin-2-yl)benzyl)-1-(2-methoxyethyl)-1H-benzo[d]imidazole-6-carboxylate (I-109). ES/MS: 436.451 ($M+H^+$); $^1H$ NMR (400 MHz, DMSO-d6, TFA added) δ 8.52 (d, J=1.4 Hz, 1H), 8.06 (dd, J=8.6, 1.5 Hz, 1H), 7.83-7.77 (m, 2H), 7.75 (dd, J=8.0, 1.8 Hz, 1H), 7.63 (dd, J=8.8, 7.1 Hz, 1H), 7.53 (t, J=8.0 Hz, 1H), 6.97 (d, J=7.2 Hz, 1H), 6.51 (d, J=8.7 Hz, 1H), 4.80 (t, J=5.0 Hz, 2H), 4.70 (s, 2H), 3.71 (t, J=5.0 Hz, 2H), 3.20 (s, 3H).

Intermediate I-110

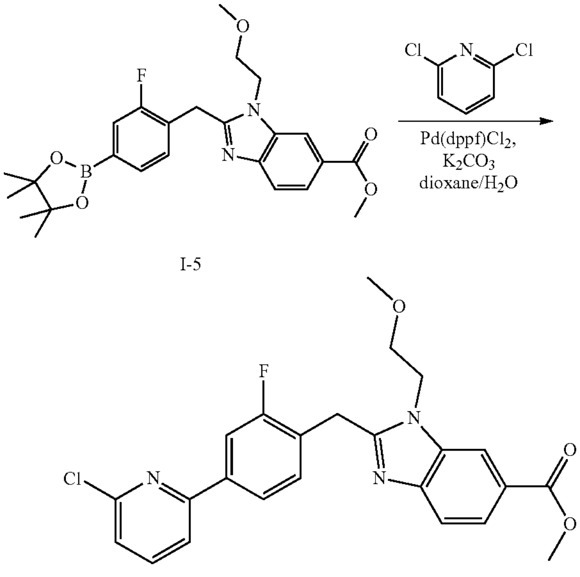

I-5

I-110

Methyl 2-(4-(6-chloropyridin-2-yl)-2-fluorobenzyl)-1-(2-methoxyethyl)-1H-benzo[d]imidazole-6-carboxylate (I-110). To a solution of methyl 2-(2-fluoro-4-(4,4,5,5-tetramethyl-1,3,2-dioxaborolan-2-yl)benzyl)-1-(2-methoxyethyl)-1H-benzo[d]imidazole-6-carboxylate (I-5, 10 g, 21.4 mmol) and 2,6-dichloropyridine (6.50 g, 43.9 mmol) in dioxane (200 mL) was added Pd(dppf)$Cl_2$ (1.60 g, 2.19 mmol) and potassium carbonate (2.00 M (aqueous), 22.0 mL, 44.0 mmol). The solution was degassed with nitrogen and heated to 90° C. (internal temperature) for 6 hours. The mixture was then cooled to room temperature and diluted with EtOAc. The solution was decanted from the residual solids and washed with brine (2×). The aqueous layer was back-extracted with EtOAc and the combined organic layers were dried over magnesium sulfate and concentrated to dryness. The crude material was purified by $SiO_2$ chromatography (eluent: 20-60% EtOAc/Hexanes) and the resulting material was triturated in 5% EtOAc/hexanes and filtered to provide methyl 2-(4-(6-chloropyridin-2-yl)-2-fluorobenzyl)-1-(2-methoxyethyl)-1H-benzo[d]imidazole-6-carboxylate (I-110). ES/MS: 454.319 ($M+H^+$); $^1H$ NMR (400 MHz, Chloroform-d) δ 8.12 (d, J=1.4 Hz, 1H), 8.01 (d, J=8.3 Hz, 1H), 7.82 (dd, J=15.5, 9.6 Hz, 2H), 7.72 (q, J=7.2, 6.6 Hz, 2H), 7.63 (d, J=7.7 Hz, 1H), 7.40 (s, 1H), 7.30 (d, J=7.8 Hz, 1H), 4.50 (s, 2H), 4.37 (s, 2H), 3.98 (s, 3H), 3.66 (s, 2H), 3.27 (s, 3H).

Intermediate I-111

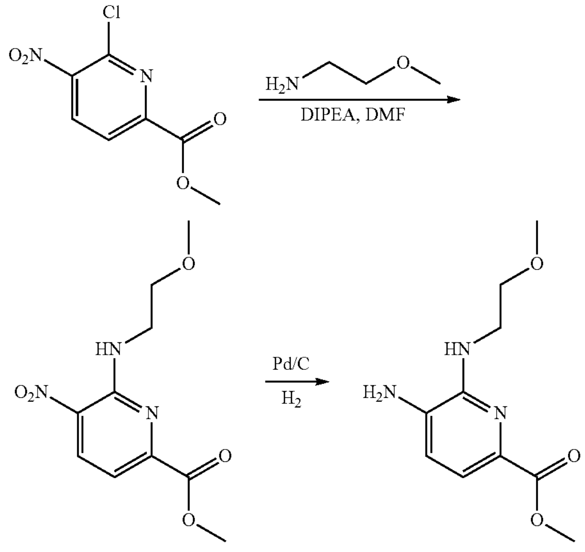

I-111

Step 1. Methyl 6-((2-methoxyethyl)amino)-5-nitropicolinate. To a solution of methyl 6-chloro-5-nitropicolinate (500 mg, 2.3 mmol) in DMF (4.5 mL) was added 2-methoxyethanamine (227 mg, 3.02 mmol) and N,N-diisopropylethylamine (0.800 mL, 4.59 mmol). The solution was heated to 70° C. (external temperature) for 18 hours and then concentrated to dryness. The crude material was purified by $SiO_2$ chromatography (eluent: 5-40% EtOAc/hexanes) to provide methyl 6-((2-methoxyethyl)amino)-5-nitropicolinate. ES/MS: 256.054 ($M+H^+$).

Step 2. Methyl 5-amino-6-((2-methoxyethyl)amino)picolinate (I-111): To a solution of methyl 6-((2-methoxyethyl)amino)-5-nitropicolinate (483 mg, 1.89 mmol) in a 1:1 mixture of EtOH/EtOAc (16 mL) was added palladium on carbon (10% wt, 257 mg, 0.24 mmol). The resulting slurry was stirred under a hydrogen atmosphere for 18 hours, filtered and concentrated to dryness to provide methyl 5-amino-6-((2-methoxyethyl)amino)picolinate (I-111). ES/MS: 226.129 ($M+H^+$).

Intermediate I-112

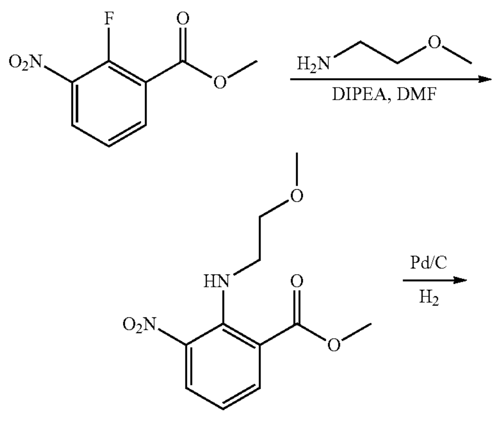

-continued

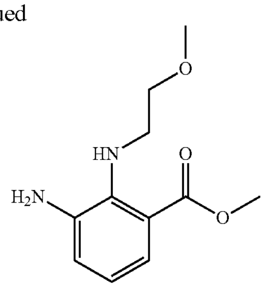

I-112

Step 1. Methyl 2-((2-methoxyethyl)amino)-3-nitrobenzoate: To a solution of methyl 2-fluoro-3-nitrobenzoate (100 mg, 0.5 mmol) in DMF (1 mL) was added 2-methoxyethanamine (56 mg, 0.75 mmol) and N,N-diisopropylethylamine (0.220 mL, 1.26 mmol). The solution was heated to 70° C. (external temperature) for 18 hours and cooled to room temperature. The resulting solution was diluted with EtOAc and washed twice with aqueous lithium chloride. The aqueous layer was back-extracted with EtOAc and the combined organic layers were concentrated to dryness to provide methyl 2-((2-methoxyethyl)amino)-3-nitrobenzoate: ES/MS: 255.128 ($M+H^+$).

Step 2. Methyl 3-amino-2-((2-methoxyethyl)amino)benzoate (I-112): To a solution of methyl 2-((2-methoxyethyl) amino)-3-nitrobenzoate (128 mg, 0.503 mmol) in a 1:1 mixture of EtOH/EtOAc (4 mL) was added palladium on carbon (10% wt, 75.0 mg, 0.0705 mmol). The resulting slurry was stirred under a hydrogen atmosphere for 18 hours, filtered and concentrated to dryness to provide methyl 3-amino-2-((2-methoxyethyl)amino)benzoate (I-112): ES/MS: 225.232 ($M+H^+$).

Intermediate I-113

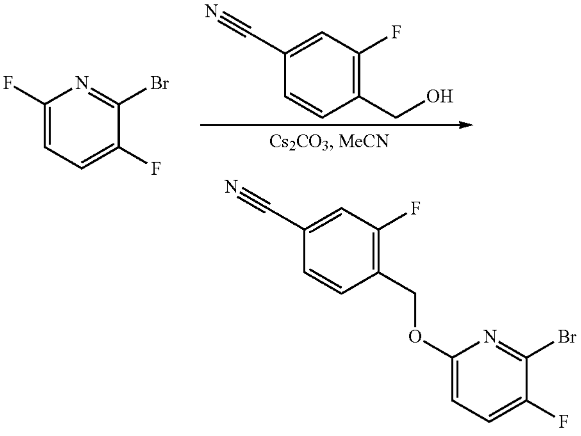

I-113

4-(((6-Bromo-5-fluoropyridin-2-yl)oxy)methyl)-3-fluorobenzonitrile (I-113): To a solution of 3-fluoro-4-(hydroxymethyl)benzonitrile (160 mg, 1.06 mmol) and 2-bromo-3,6-difluoro-pyridine (98.0 mg, 0.505 mmol) in acetonitrile (2 mL) was added cesium carbonate (332 mg, 1.02 mmol). The slurry was stirred at room temperature for 4 days, filtered and concentrated to dryness. The crude material was purified by $SiO_2$ chromatography (eluent: 5-40% EtOAc/hexanes) to provide 4-(((6-bromo-5-fluoro-pyridin-2-yl)oxy)methyl)-3-fluorobenzonitrile (I-113). ES/MS: 327.095 (M+H+); $^1$H NMR (400 MHz, CDCl3) δ 7.67 (t, J=7.5 Hz, 1H), 7.50 (dd, J=8.0, 1.5 Hz, 1H), 7.42 (ddd, J=8.7, 4.0, 2.4 Hz, 2H), 6.78 (dd, J=8.8, 2.8 Hz, 1H), 5.47 (s, 2H); $^{19}$F NMR (376 MHz, CDCl3) δ −114.88-−115.18 (m), −124.59 (dd, J=6.8, 2.7 Hz).

Intermediate I-114

I-114

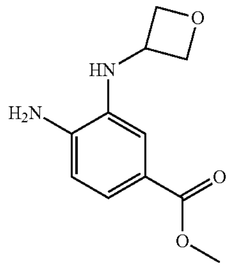

Methyl 4-amino-3-(oxetan-3-ylamino)benzoate (I-114): Methyl 4-amino-3-(oxetan-3-ylamino)benzoate was prepared following procedure Intermediate I-112 substituting methyl 3-fluoro-4-nitrobenzoate for methyl 2-fluoro-3-nitrobenzoate and oxetane-3-amine for 2-methoxyethanamine. ES/MS: 223.098 (M+H+).

Intermediate I-115

I-115

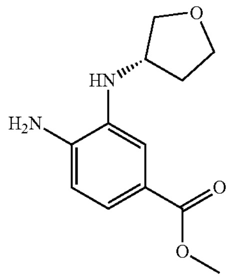

Methyl (S)-4-amino-3-((tetrahydrofuran-3-yl)amino)benzoate (I-115): Methyl (S)-4-amino-3-((tetrahydrofuran-3-yl)amino)benzoate was prepared following procedure Intermediate I-112 substituting methyl 3-fluoro-4-nitrobenzoate for methyl 2-fluoro-3-nitrobenzoate and (S)-tetrahydrofuran-3-amine for 2-methoxyethanamine. ES/MS: 237.118 (M+H+).

Intermediate I-116

I-116

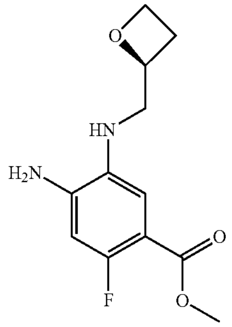

Methyl (S)-4-amino-2-fluoro-5-((oxetan-2-ylmethyl)amino)benzoate (I-116): Methyl (S)-4-amino-2-fluoro-5-((oxetan-2-ylmethyl)amino)benzoate was prepared following procedure Intermediate I-112 substituting methyl 2,5-difluoro-4-nitrobenzoate for methyl 2-fluoro-3-nitrobenzoate and (S)-oxetan-2-ylmethanamine for 2-methoxyethanamine. ES/MS: 255.083 (M+H+).

Intermediate I-117

I-117

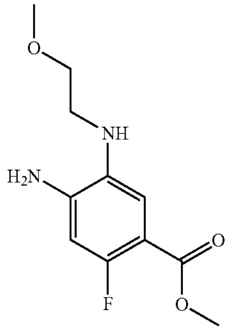

Methyl 4-amino-2-fluoro-5-((2-methoxyethyl)amino)benzoate (I-117): Methyl 4-amino-2-fluoro-5-((2-methoxyethyl)amino)benzoate was prepared following procedure Intermediate I-112 substituting methyl 2,5-difluoro-4-nitrobenzoate for methyl 2-fluoro-3-nitrobenzoate. ES/MS: 243.111 (M+H+).

Intermediate I-118

I-118

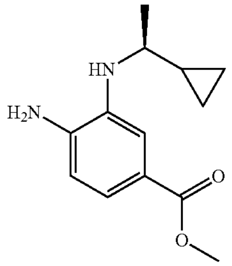

Methyl (S)-4-amino-3-((1-cyclopropylethyl)amino)benzoate (I-118): Methyl (S)-4-amino-3-((1-cyclopropylethyl)amino)benzoate was prepared following procedure Intermediate I-112 substituting methyl 3-fluoro-4-nitrobenzoate for methyl 2-fluoro-3-nitrobenzoate and (S)-1-cyclopropylethan-1-amine for 2-methoxyethanamine. ES/MS: 235.079 (M+H+).

Intermediate I-119

I-119

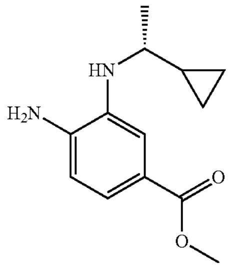

Methyl (R)-4-amino-3-((1-cyclopropylethyl)amino)benzoate (I-119): Methyl (R)-4-amino-3-((1-cyclopropylethyl)amino)benzoate was prepared following procedure Intermediate I-112 substituting methyl 3-fluoro-4-nitrobenzoate for methyl 2-fluoro-3-nitrobenzoate and (R)-1-cyclopropylethan-1-amine for 2-methoxyethanamine. ES/MS: 235.144 (M+H$^+$).

Intermediate I-120

I-120

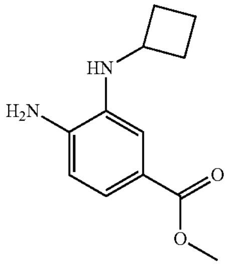

Methyl 4-amino-3-(cyclobutylamino)benzoate (I-120): Methyl 4-amino-3-(cyclobutylamino)benzoate was prepared following procedure Intermediate I-112 substituting methyl 3-fluoro-4-nitrobenzoate for methyl 2-fluoro-3-nitrobenzoate and cyclobutanamine for 2-methoxyethanamine. ES/MS: 221.156 (M+H$^+$).

Intermediate I-121

I-121

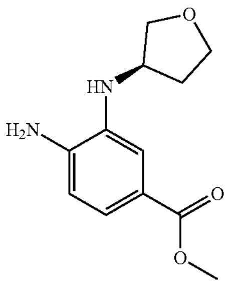

Methyl (R)-4-amino-3-((tetrahydrofuran-3-yl)amino)benzoate (I-121): Methyl (R)-4-amino-3-((tetrahydrofuran-3-yl)amino)benzoate was prepared following procedure Intermediate I-112 substituting methyl 3-fluoro-4-nitrobenzoate for methyl 2-fluoro-3-nitrobenzoate and (R)-tetrahydrofuran-3-amine for 2-methoxyethanamine. ES/MS: 237.173 (M+H$^+$).

Intermediate I-122

I-122

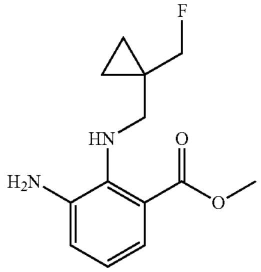

Methyl 3-amino-2-(((1-(fluoromethyl)cyclopropyl)methyl)amino)benzoate (I-122): Methyl 3-amino-2-(((1-(fluoromethyl)cyclopropyl)methyl)amino)benzoate was prepared following procedure Intermediate I-112 substituting (1-(fluoromethyl)cyclopropyl)methanamine 2,2,2-trifluoroacetate for 2-methoxyethanamine. ES/MS: 255.083 (M+H$^+$).

Intermediate I-123

I-123

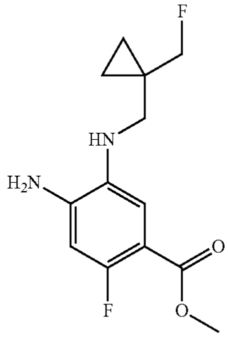

Methyl 4-amino-2-fluoro-5-(((1-(fluoromethyl)cyclopropyl)methyl)amino)benzoate (I-123): Methyl 4-amino-2-fluoro-5-(((1-(fluoromethyl)cyclopropyl)methyl)amino)benzoate was prepared following procedure Intermediate I-112 substituting methyl 4-nitro-2,5-difluorobenzoate for methyl 3-fluoro-4-nitrobenzoate and (1-(fluoromethyl)cyclopropyl)methanamine 2,2,2-trifluoroacetate for 2-methoxyethanamine. ES/MS: 271.158 (M+H$^+$).

Intermediate I-124

I-124

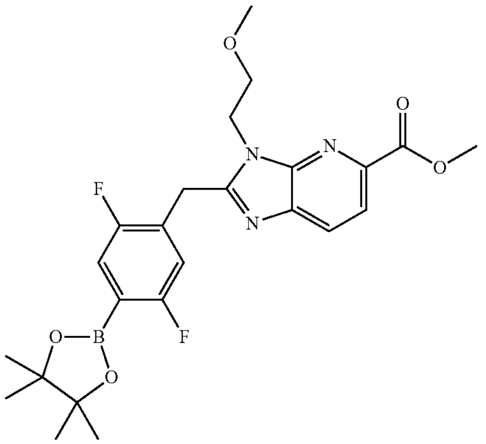

Methyl 2-(2,5-difluoro-4-(4,4,5,5-tetramethyl-1,3,2-dioxaborolan-2-yl)benzyl)-3-(2-methoxyethyl)-3H-imidazo[4,5-b]pyridine-5-carboxylate (I-124): Methyl 2-(2,5-difluoro-4-(4,4,5,5-tetramethyl-1,3,2-dioxaborolan-2-yl)benzyl)-3-(2-methoxyethyl)-3H-imidazo[4,5-b]pyridine-5-carboxylate was prepared following procedure Intermediate I-5 substituting 2-(4-bromo-2,5-difluorophenyl)acetic acid for 2-(4-bromo-2-fluorophenyl)acetic acid and methyl 5-amino-6-((2-methoxyethyl)amino)picolinate for methyl 4-amino-3-((2-methoxyethyl)amino)benzoate. ES/MS: 488.322 (M+H$^+$).

Intermediate I-125

I-125

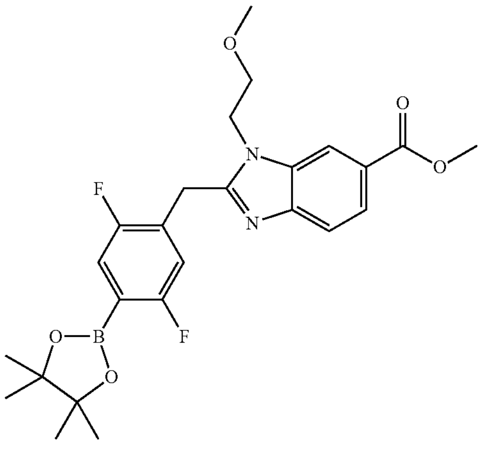

Methyl 2-(2,5-difluoro-4-(4,4,5,5-tetramethyl-1,3,2-dioxaborolan-2-yl)benzyl)-1-(2-methoxyethyl)-1H-benzo[d]imidazole-6-carboxylate (I-125): Methyl 2-(2,5-difluoro-4-(4,4,5,5-tetramethyl-1,3,2-dioxaborolan-2-yl)benzyl)-1-(2-methoxyethyl)-1H-benzo[d]imidazole-6-carboxylate was prepared following procedure Intermediate I-5 substituting 2-(4-bromo-2,5-difluorophenyl)acetic acid for 2-(4-bromo-2-fluorophenyl)acetic acid. ES/MS: 487.257 (M+H$^+$).

Intermediate I-126

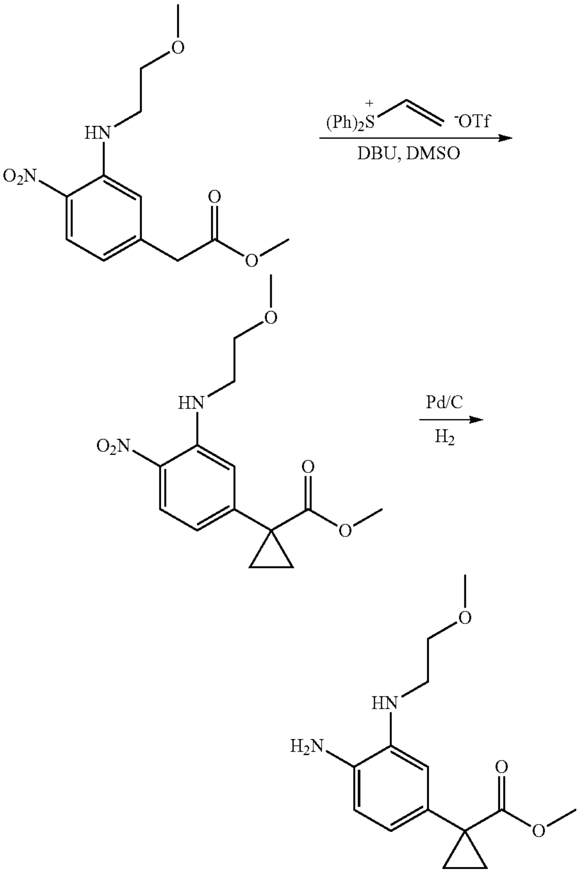

I-126

Step 1. Methyl 1-(3-((2-methoxyethyl)amino)-4-nitrophenyl)cyclopropane-1-carboxylate: To a solution of methyl 2-(3-((2-methoxyethyl)amino)-4-nitrophenyl)acetate (200 mg, 0.746 mmol) in DMSO (6 mL) was added diphenyl (vinyl)sulfonium trifluoromethanesulfonate (380 mg, 1.05 mmol) and 1,8-diazabicyclo(5.4.0)undec-7-ene (0.120 mL, 0.802 mmol). The solution was stirred at room temperature for 2 h. The mixture was diluted with EtOAc, washed with $H_2O$ (2×) and brine. The aqueous layers were back-extracted with EtOAc and the combined organic layers were dried over magnesium sulfate and concentrated to dryness. The crude material was purified by $SiO_2$ chromatography (eluent: 10-40% EtOAc/hexanes) to provide methyl 1-(3-((2-methoxyethyl)amino)-4-nitrophenyl)cyclopropane-1-carboxylate. ES/MS: 295.130 (M+H$^+$).

Step 2. Methyl 1-(4-amino-3-((2-methoxyethyl)amino)phenyl)cyclopropane-1-carboxylate (I-126): To a solution of methyl 1-(3-((2-methoxyethyl)amino)-4-nitrophenyl)cyclopropane-1-carboxylate (196 mg, 0.666 mmol) in a 2:1 mixture of EtOAc/EtOH (3 mL) was added palladium on carbon (10%, 32 mg, 0.03 mmol). The slurry was stirred at room temperature under an atmosphere of hydrogen for 20 hours and then filtered. The filtrate was concentrated to dryness and the crude material was purified by $SiO_2$ chromatography (eluent: 20-65% EtOAc/hexanes) to provide methyl 1-(4-amino-3-((2-methoxyethyl)amino)phenyl)cyclopropane-1-carboxylate (I-126). ES/MS: 265.423 (M+H$^+$).

Intermediate I-127

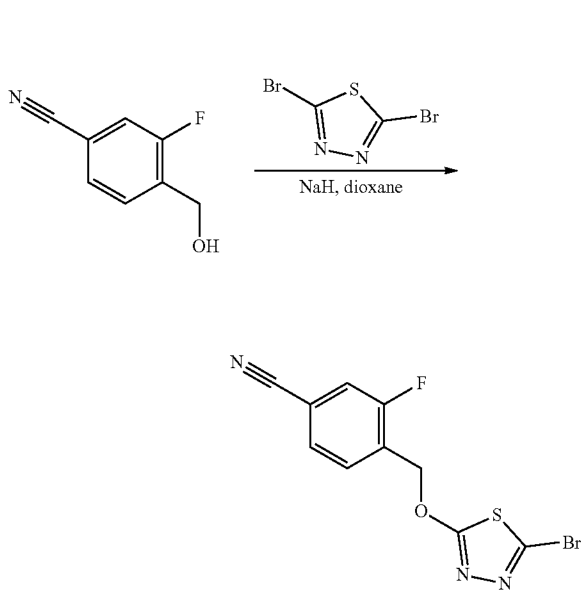

I-127

4-(((5-Bromo-1,3,4-thiadiazol-2-yl)oxy)methyl)-3-fluorobenzonitrile (I-127): To a solution of 3-fluoro-4-(hydroxymethyl)benzonitrile (140 mg, 0.926 mmol) in dioxane (2 mL) was added sodium hydride (22 mg, 0.957 mmol). The resulting slurry was stirred at room temperature for 15 min, followed by the addition of 2,5-dibromo-1,3,4-thiadiazole (100 mg, 0.410 mmol). The mixture was then heated to 50° C. (external temperature) for 2 hours and cooled to room temperature. The mixture was diluted with EtOAc and washed with $H_2O$ and brine. The aqueous layers were back-extracted and the combined organic layers were dried over magnesium sulfate and concentrated to dryness. The crude material was purified by $SiO_2$ chromatography (eluent: 2-30% EtOAc/hexanes) to provide 4-(((5-bromo-1,3,4-thiadiazol-2-yl)oxy)methyl)-3-fluorobenzonitrile (I-127). 1H NMR (400 MHz, Chloroform-d) δ 7.69 (t, J=7.4 Hz, 1H), 7.57-7.50 (m, 1H), 7.45 (dd, J=9.1, 1.5 Hz, 1H), 5.71-5.65 (m, 2H).

Intermediate I-128

I-128

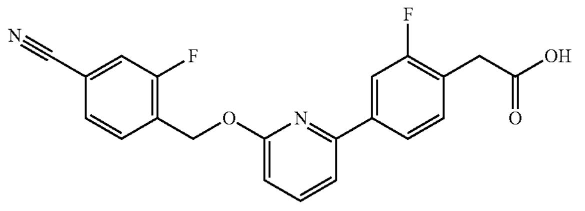

2-(4-(6-((4-cyano-2-fluorobenzyl)oxy)pyridin-2-yl)-2-fluorophenyl)acetic acid (I-128): 2-(4-(6-((4-cyano-2-fluorobenzyl)oxy)pyridin-2-yl)-3-fluorophenyl)acetic acid (I-128) was prepared in identical manner as I-81 substituting methyl 2-(4-bromo-2,5-difluorophenyl)acetate with methyl 2-(4-bromo-2-fluorophenyl)acetate. ES/MS: 381.1 (M+H$^+$).

Intermediate I-129

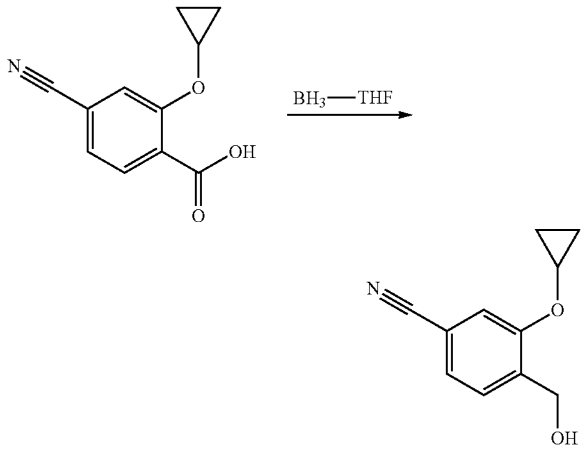

I-129

3-cyclopropoxy-4-(hydroxymethyl)benzonitrile (I-129): 4-cyano-2-cyclopropoxybenzoic acid (250 mg, 1.23 mmol) was dissolved in THF (5 mL) and brought to 0° C. at which point borane-THF complex (1.0 M in THF, 2.46 mL, 2.46 mmol) was added dropwise. The mixture was allowed to warm to ambient temperature over 2 h. Upon completion the reaction was quenched by the addition of saturated aq. $NaHCO_3$ (2 mL), poured into water (5 mL) and extracted with EtOAc (3×10 mL). The combined organic extracts were washed with brine (5 mL), dried over $MgSO_4$, and purified by silica gel chromatography (eluent: EtOAc/hexanes) to give the desired product.

Intermediate I-130

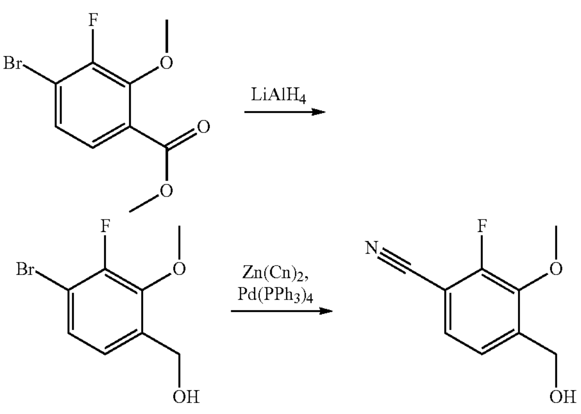

I-130

(4-bromo-3-fluoro-2-methoxyphenyl)methanol: Methyl 4-bromo-3-fluoro-2-methoxybenzoate (500 mg, 1.9 mmol) was dissolved in dry THF (10 mL) and brought to 0° C. Lithium aluminum hydride (1.0 M in THF, 1.9 mL, 1.9 mmol) was added dropwise after which it was allowed to stir for 10 minutes at 0° C. Upon completion the reaction contents were carefully quenched by the addition of saturated aqueous. Rochelle's salt (30 mL) and left to stir for 1 hr at room temperature. The reaction contents were then extracted with EtOAc (3×30 mL), washed with brine (5 mL), dried over $MgSO_4$, concentrated and carried forward without further purification.

2-fluoro-4-(hydroxymethyl)-3-methoxybenzonitrile (I-130): (4-bromo-3-fluoro-2-methoxyphenyl)methanol (424 mg, 1.8 mmol), tetrakis(triphenylphosphine)palladium (0) (521 mg, 0.45 mmol), zinc cyanide (1.06 g, 9.0 mmol) and NMP (10 mL) were combined in a 20 mL microwave vial under an atmosphere of argon. The mixture was heated to 150° C. for 90 minutes in a microwave reactor after which the reaction contents were poured into water (15 mL) and extracted with EtOAc (3x30 mL). The combined organic extracts were washed with brine (15 mL), dried over $MgSO_4$, and purified by silica gel chromatography (eluent: EtOAc/hexanes) to give the desired compound. ES/MS: 183.8 ($M+H^+$).

Intermediate I-131

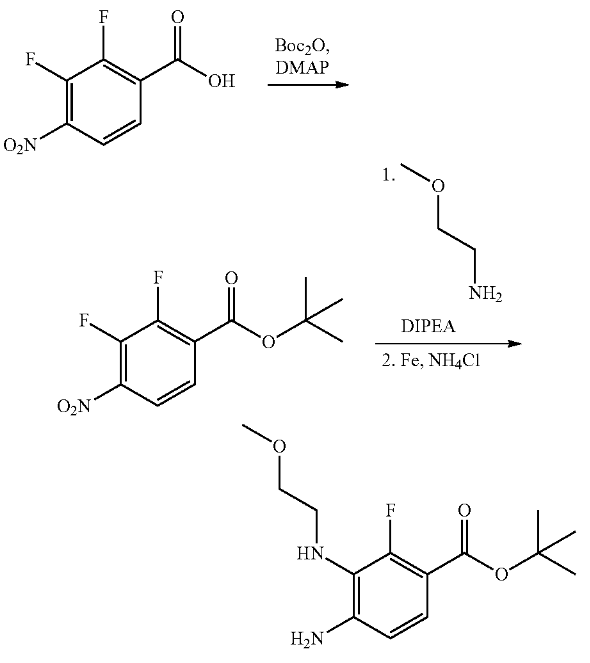

I-131

Tert-butyl 2,3-difluoro-4-nitrobenzoate: 2,3-difluoro-4-nitrobenzoic acid (1.00 g, 4.92 mmol) in THF (15 mL) at ambient temperature was treated with di-tert-butyl decarbonate (2.15 g, 9.9 mmol) followed by 4-dimethylaminopyridine (180 mg, 1.5 mmol) and the resulting mixture was heated to 40° C. for 3 hrs. Upon completion the reaction contents were poured into water (20 mL), and extracted with EtOAc (3x30 mL). The combined organic extracts were washed with brine (15 mL), dried over $MgSO_4$, and purified by silica gel chromatography (eluent: EtOAc/hexanes).

Tert-butyl 4-amino-2-fluoro-3-((2-methoxyethyl)amino) benzoate (I-131): tert-butyl 2,3-difluoro-4-nitrobenzoate (200 mg, 0.77 mmol) was dissolved in THF (2 mL) after which 2-methoxyethanamine (0.080 mL, 0.93 mmol) and diisopropylethylamine (0.40 mL, 2.3 mmol) were added and the resulting mixture heated to 60° C. for 16 hrs. Upon completion the mixture was concentrated directly, the crude residue then taken up in EtOAc (25 mL) and washed with saturated aq. $NH_4Cl$ (2x5 mL). The combined organic extracts were washed with brine (5 mL), dried over $MgSO_4$, concentrated and carried forward without purification. Crude tert-butyl 2-fluoro-3-((2-methoxyethyl)amino)-4-nitrobenzoate was dissolved in EtOH (5 mL) after which iron (216 mg, 3.9 mmol) and saturated aq. $NH_4Cl$ (2 mL) were added. The resulting mixture was heated to 60° C. for 3 hrs. Upon completion the solids were removed by filtration washing with EtOAc (20 mL) and MeOH (20 mL). The filtrate was then concentrated, taken up in EtOAc (25 mL), and washed with water (5 mL) and brine (5 mL). The organic layer was then dried over $MgSO_4$, and purified by silica gel chromatography (eluent: EtOAc/hexanes) to give the desired product. ES/MS: 284.9 ($M+H^+$).

Intermediate I-132

I-132

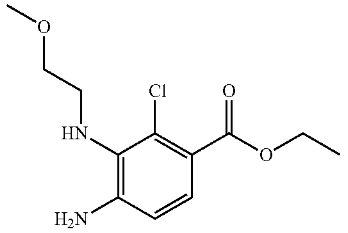

Ethyl 4-amino-2-chloro-3-((2-methoxyethyl)amino)benzoate (I-132): Ethyl 4-amino-2-chloro-3-((2-methoxyethyl) amino)benzoate (I-132) was made in an analogous manner as describe for 1-131 substituting tert-butyl 2,3-difluoro-4-nitrobenzoate with ethyl 2,3-difluoro-4-nitrobenzoate. ES/MS: 273.1 ($M+H^+$).

Intermediate I-133

I-133

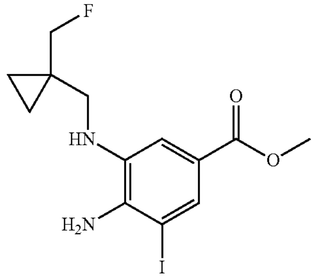

Methyl 4-amino-3-(((1-(fluoromethyl)cyclopropyl) methyl)amino)-5-iodobenzoate (I-133): Methyl 4-amino-3-(((1-(fluoromethyl)cyclopropyl)methyl)amino)-5-iodobenzoate (I-133) was prepared in analogous manner to I-62 substituting Ethyl 4-amino-3,5-difluorobenzoate with methyl 4-amino-3-fluoro-5-iodobenzoate and employing Fe, $NH_4Cl$ for the nitro reduction instead of $H_2$, Pd/C. ES/MS: 379.0 ($M+H^+$)

Intermediate I-134

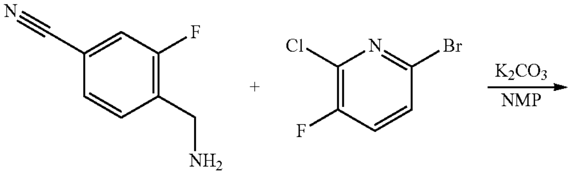

-continued

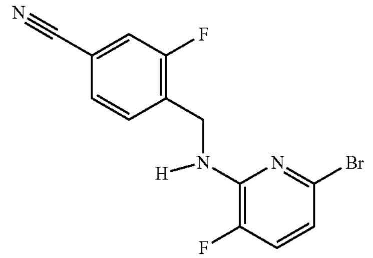

I-134

4-(((6-bromo-3-fluoropyridin-2-yl)oxy)methyl)-3-fluorobenzonitrile (I-134): To a solution of 6-bromo-2-chloro-3-fluoro-pyridine (200.0 mg, 0.95 mmol) and 4-(aminomethyl)-3-fluoro-benzonitrile (142.6 mg, 0.95 mmol) in NMP (3.0 mL) in a microwave vial was added potassium carbonate (393.9 mg, 2.85 mmol). The vial was sealed and the mixture was heated at 180° C. in a microwave reactor for 30 minutes. The cooled mixture was partitioned between water and ethyl acetate. The organic layer was collected, and the aqueous layer was extracted three additional times with ethyl acetate. The combined organic layers were washed with brine, dried over sodium sulfate, isolated by vacuum filtration, and concentrated in vacuo. The resulting residue was purified by silica gel column chromatography (eluent: EtOAc/Hex) to provide the desired product. ES/MS: 324.0, 326.0 $[M+H]^+$ Tert-butyl 2-[[2,5-difluoro-4-(6-hydroxy-2-pyridyl)phenyl]methyl]-3-(2-methoxyethyl)benzimidazole-5-carboxylate (I-135): A solution of tert-butyl 2-[[4-[6-[(4-cyano-2-fluoro-phenyl)methoxy]-2-pyridyl]-2,5-difluoro-phenyl]methyl]-3-(2-methoxyethyl)benzimidazole-5-carboxylate (130 mg) in EtOH (5 mL) was degassed with Ar under vacuum 3×. To this was added Pd/C (10%, 22 mg) and the mixture was stirred at RT with a balloon of hydrogen for 4 h. This was then filtered over a Celite plug and rinsed with EtOAc and then concentrated to give title product, and used in subsequent steps without further purification. ES/MS: 496.5 $(M+H^+)$ Intermediate I-136

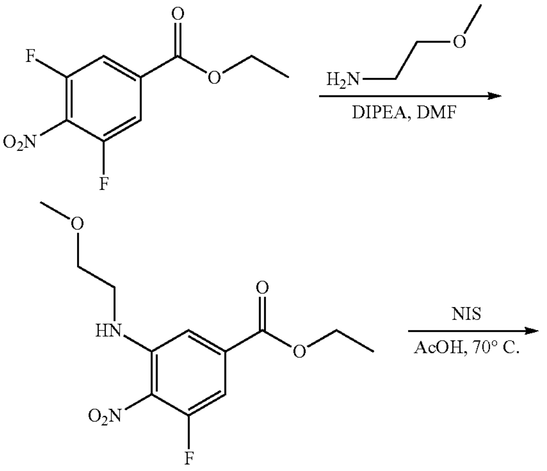

Intermediate I-135

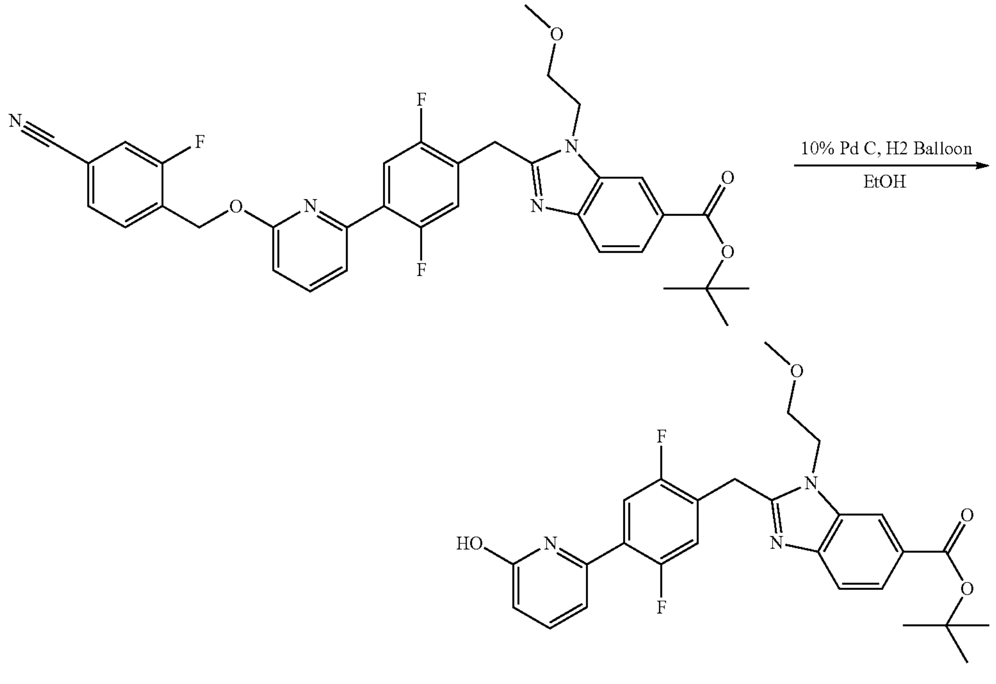

I-135

-continued

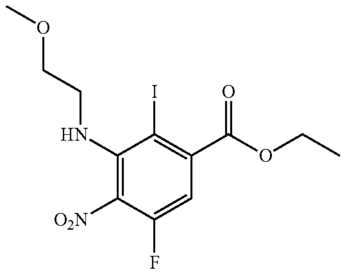

I-136

Ethyl 3-fluoro-5-((2-methoxyethyl)amino)-4-nitrobenzoate: Ethyl 3,5-difluoro-4-nitro-benzoate (0.5 g, 2.16 mmol) and 2-methoxyethanamine (162 mg, 2.16 mmol) in N,N-dimethylformamide (2.0 mL) and N,N-diisopropylethylamine (1.88 mL, 10.8 mmol) were combined. The mixture was stirred at RT for 16 hours. Following this time, the mixture was concentrated in vacuo and the residue was purified by column chromatography (eluent: 0-25% EtOAc/Hexanes) to afford the product. ES/MS: 287.2 (M+H+)

Ethyl 5-fluoro-2-iodo-3-((2-methoxyethyl)amino)-4-nitrobenzoate (I-136): To a solution of ethyl 3-fluoro-5-((2-methoxyethyl)amino)-4-nitrobenzoate (0.4 g, 1.4 mmol) in 2 mL of acetic acid, N-iodosuccinimide (0.314 g, 1.4 mmol) was added to the solution. It was heated to 70° C. for 2 hours and then diluted with EtOAc (50 mL) and washed with $NaHCO_3$(sat) and brine. The organic layer was dried and concentrated and the residue purified by column chromatography (eluent: 0-25% EtOAc/Hexanes) to afford the product. ES/MS: 413.1 ($M+H^+$)

Intermediate I-137

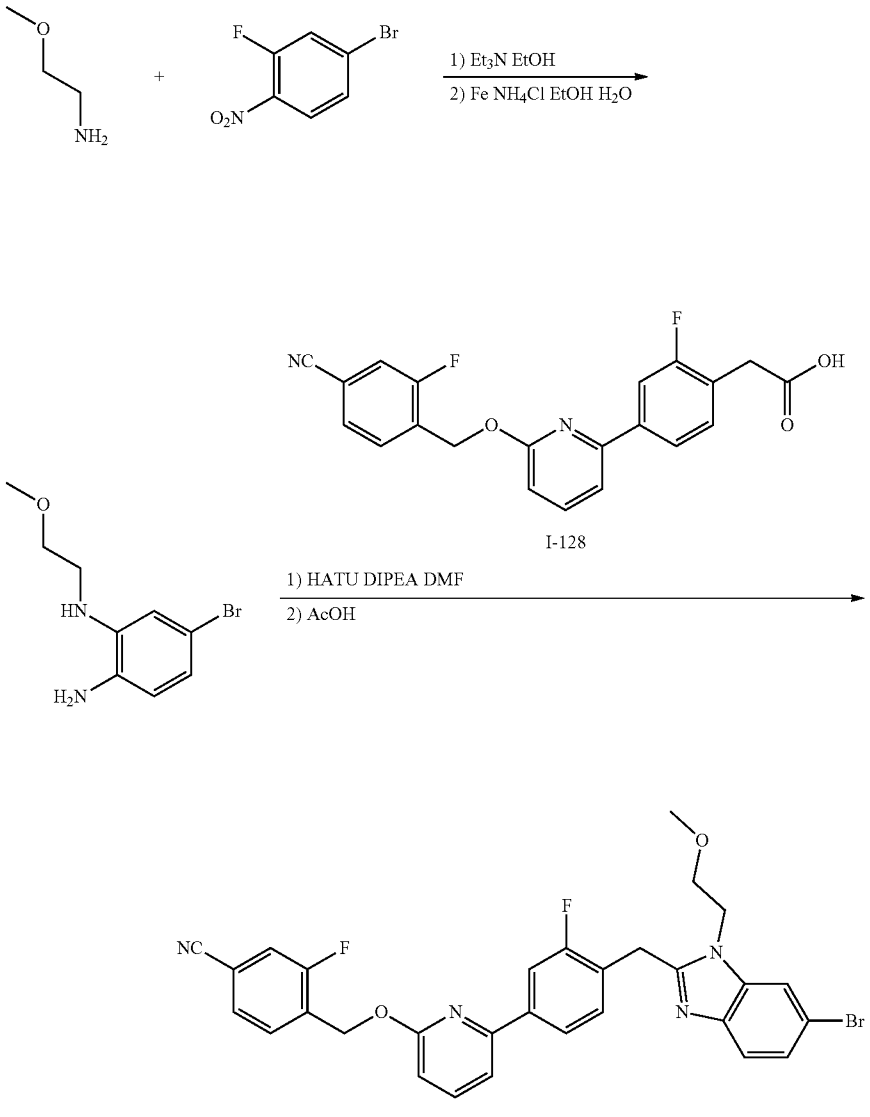

I-128

I-137

5-bromo-N'-(2-methoxyethyl)benzene-1,2-diamine: To a suspension of 4-bromo-2-fluoro-1-nitrobenzene (2.0 g, 9.09 mmol) in EtOH (10 mL) was added triethylamine (1.8 mL, 13.6 mmol) and 2-methoxyethylamine (0.95 mL, 10.9 mmol). The resulting solution was heated to 80° C. for 8 hrs. Upon completion the solvent was removed, and the resulting residue taken up in EtOAc (50 mL), washed with brine (30 mL), concentrated and carried forward without further purification. The crude mixture was taken up in a mixture of EtOH (25 mL) and water (10 mL), followed by addition of iron powder (5.07 g, 90.9 mmol) and $NH_4Cl$ (4.86 g, 90.9 mmol). The mixture was heated to 60° C. for 5 hrs. Upon completion, the mixture was filtered through a plug of Celite, and the resulting residue was diluted with EtOAc (100 mL) and water (100 mL). The organic phase was collected, and the aqueous phase extracted with EtOAc (2×50 mL). The combined organic phases were washed with saturated aqueous $NaHCO_3$ (100 mL), dried over $Na_2SO_4$, and concentrated in vacuo. The crude material was purified by silica gel chromatography (eluent: EtOAc in hexanes). ES/MS: 246.2 (M+H$^+$)

4-(((6-(4-((6-bromo-1-(2-methoxyethyl)-1H-benzo[d]imidazol-2-yl)methyl)-3-fluorophenyl)pyridin-2-yl)oxy)methyl)-3-fluorobenzonitrile (I-137): 5-bromo-N$^1$-(2-methoxyethyl)benzene-1,2-diamine (2.20 g, 9.0 mmol), 2-(4-(6-((4-cyano-2-fluorobenzyl)oxy)pyridin-2-yl)-2-fluorophenyl)acetic acid (I-128, 3.40 g, 9.0 mmol), and O-(7-azabenzotriazol-1-yl)-N,N,N',N'-tetramethyluronium hexafluorophosphate (4.26 g, 11.2 mmol) were taken up in DMF (15 mL) and N,N-diisopropylethylamine (7.8 mL, 45 mmol) was added. The mixture was stirred at room temperature for 3 hrs. The product was collected via vacuum filtration and carried forward without further purification. The solid was suspended in AcOH (20 mL) and heated to 80° C. When the reaction was complete, the mixture was concentrated and purified via column chromatography (eluent: EtOAc in hexanes). ES/MS m/z: 590.2 (M+H$^+$).

Intermediate I-138

I-138

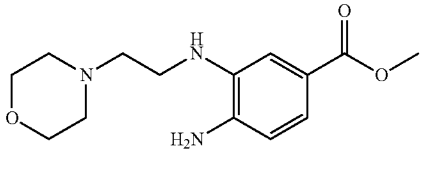

Methyl 4-amino-3-((2-morpholinoethyl)amino)benzoate (I-138): Methyl 4-amino-3-((2-morpholinoethyl)amino)benzoate (I-138) was prepared identically as described for I-1 substituting methoxyethylamine with 2-morpholinoethanamine. ES/MS: 280.2 (M+H$^+$)

Intermediate I-139

I-139

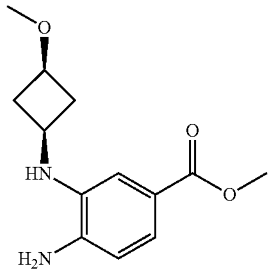

Methyl 4-amino-3-(((1s,3s)-3-methoxycyclobutyl)amino)benzoate (I-139): Methyl 4-amino-3-(((1s,3s)-3-methoxycyclobutyl)amino)benzoate (I-139) was prepared identically as described for I-1 substituting methoxyethylamine with cis-3-methoxycyclobutanamine hydrochloride. ES/MS: 251.2 (M+H$^+$)

Intermediate I-140

I-140

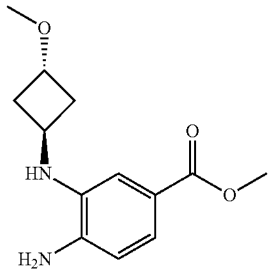

Methyl 4-amino-3-(((1r,3r)-3-methoxycyclobutyl)amino)benzoate (I-140): Methyl 4-amino-3-(((1r,3r)-3-methoxycyclobutyl)amino)benzoate (I-140) was prepared identically as described for I-1 substituting methoxyethylamine with trans-3-methoxycyclobutanamine hydrochloride. ES/MS: 251.2 (M+H$^+$)

Intermediate I-141

I-141

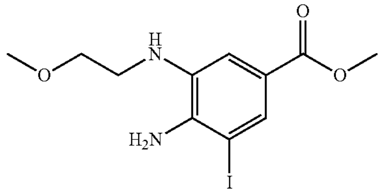

Methyl 4-amino-3-iodo-5-((2-methoxyethyl)amino)benzoate (I-141): Methyl 4-amino-3-iodo-5-((2-methoxyethyl)amino)benzoate was prepared following procedure Intermediate I-112 substituting methyl 3-fluoro-5-iodo-4-nitrobenzoate for methyl 2-fluoro-3-nitrobenzoate and employing Fe, $NH_4Cl$ for the nitro reduction instead of $H_2$, Pd/C. ES/MS: 351.048 (M+H$^+$).

Intermediate I-142

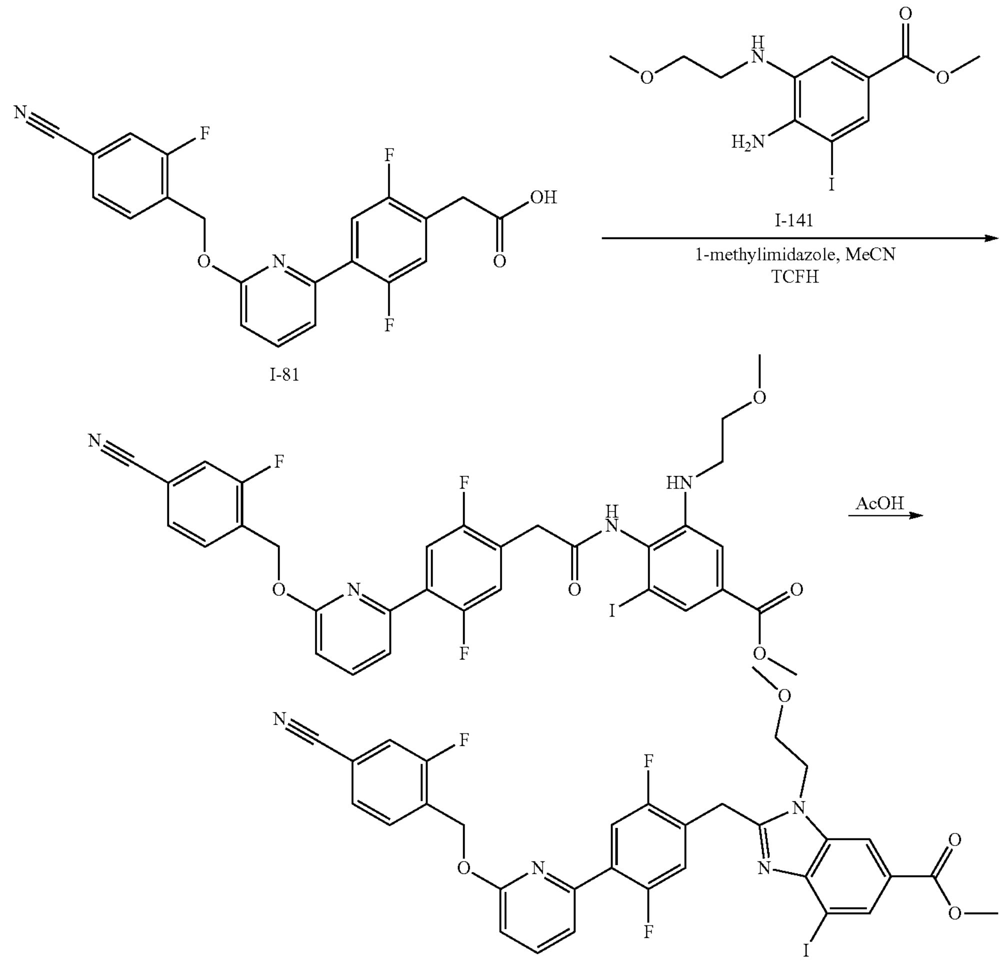

I-142

Step 1. Methyl 4-(2-(4-(6-((4-cyano-2-fluorobenzyl)oxy)pyridin-2-yl)-2,5-difluorophenyl)acetamido)-3-iodo-5-((2-methoxyethyl)amino)benzoate: To a solution of 2-(4-(6-((4-cyano-2-fluorobenzyl)oxy)pyridin-2-yl)-2,5-difluorophenyl)acetic acid (100 mg, 0.25 mmol) and methyl 4-amino-3-iodo-5-((2-methoxyethyl)amino)benzoate (I-141, 100 mg, 0.29 mmol) in MeCN (2.5 mL) was added 1-methylimidazole (0.1 mL, 1.25 mmol) and N,N,N',N'-tetramethylchloroformamidinium hexafluorophosphate (TCFH, 96 mg, 0.34 mmol). The solution was stirred at room temperature for 36 hours, diluted with EtOAc and washed with HCl (1 M, aqueous). The organic layer was concentrated to provide methyl 4-(2-(4-(6-((4-cyano-2-fluorobenzyl)oxy)pyridin-2-yl)-2,5-difluorophenyl)acetamido)-3-iodo-5-((2-methoxyethyl)amino)benzoate, which was used crude in the next step. ES/MS: 731.054 ($M+H^+$).

Step 2. Methyl 2-(4-(6-((4-cyano-2-fluorobenzyl)oxy)pyridin-2-yl)-2,5-difluorobenzyl)-4-iodo-1-(2-methoxyethyl)-1H-benzo[d]imidazole-6-carboxylate (I-142): A solution of methyl 4-(2-(4-(6-((4-cyano-2-fluorobenzyl)oxy)pyridin-2-yl)-2,5-difluorophenyl)acetamido)-3-iodo-5-((2-methoxyethyl)amino)benzoate (183 mg, 0.25 mmol) in acetic acid (4 mL) was heated to 100° C. for 1 h. The resulting solution was cooled to room temperature and concentrated to dryness. The residue was dissolved in $CH_2Cl_2$ and washed with aqueous bicarbonate. The aqueous layers were back-extracted with $CH_2Cl_2$ and the combined organic layers were dried over magnesium sulfate and concentrated to dryness. The crude material was purified by $SiO_2$ chromatography (eluent: 10-80% EtOAc/Hexanes) to provide methyl 2-(4-(6-((4-cyano-2-fluorobenzyl)oxy)pyridin-2-yl)-2,5-difluorobenzyl)-4-iodo-1-(2-methoxyethyl)-1H-benzo[d]imidazole-6-carboxylate. ES/MS: 713.299 ($M+H^+$).

Intermediate I-143

I-143

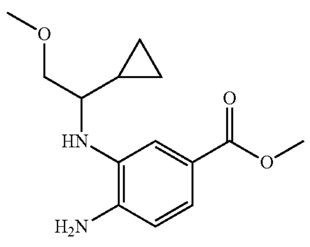

Methyl 4-amino-3-((1-cyclopropyl-2-methoxyethyl)amino)benzoate (I-143): Methyl 4-amino-3-((1-cyclopropyl-2-methoxyethyl)amino)benzoate was prepared following procedure Intermediate I-112 substituting 1-cyclopropyl-2-methoxyethan-1-amine for 2-methoxyethanamine. ES/MS: 265.092 (M+H$^+$).

Intermediate I-144

I-144

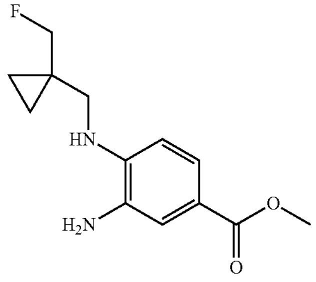

Methyl 3-amino-4-(((1-(fluoromethyl)cyclopropyl) methyl)amino)benzoate (I-144): Methyl 3-amino-4-(((1-(fluoromethyl)cyclopropyl)methyl)amino)benzoate was prepared following procedure Intermediate I-112 substituting methyl 4-fluoro-3-nitrobenzoate for methyl 2-fluoro-3-nitrobenzoate and (1-(fluoromethyl)cyclopropyl)methanamine; 2,2,2-trifluoroacetic acid for 2-methoxyethanamine. ES/MS: 283.067 (M+H$^+$).

Intermediate I-145

I-145

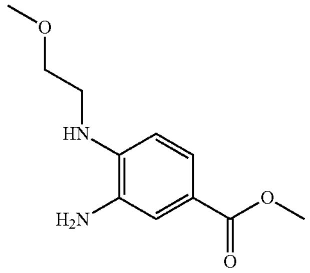

Methyl 3-amino-4-((2-methoxyethyl)amino)benzoate (I-145): Methyl 3-amino-4-((2-methoxyethyl)amino)benzoate was prepared following procedure Intermediate I-112 substituting methyl 4-fluoro-3-nitrobenzoate for methyl 2-fluoro-3-nitrobenzoate. ES/MS: 225.198 (M+H$^+$).

Intermediate I-146

I-146

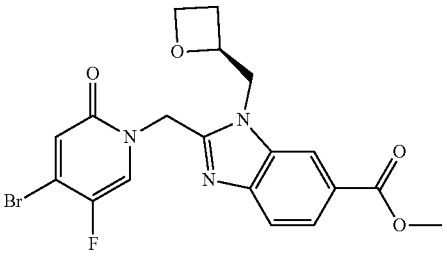

Methyl (S)-2-((4-bromo-5-fluoro-2-oxopyridin-1(2H)-yl) methyl)-1-(oxetan-2-ylmethyl)-1H-benzo[d]imidazole-6-carboxylate (I-146): Methyl (S)-2-((4-bromo-5-fluoro-2-oxopyridin-1(2H)-yl)methyl)-1-(oxetan-2-ylmethyl)-1H-benzo[d]imidazole-6-carboxylate (I-146) was synthesized as described for I-72, substituting methyl 2-(chloromethyl)-3-(2-methoxyethyl)benzimidazole-5-carboxylate hydrochloride with methyl (S)-2-(chloromethyl)-1-(oxetan-2-ylmethyl)-1H-benzo[d]imidazole-6-carboxylate. ES/MS: 450.0, 452.0 (M+H$^+$).

Intermediate I-147

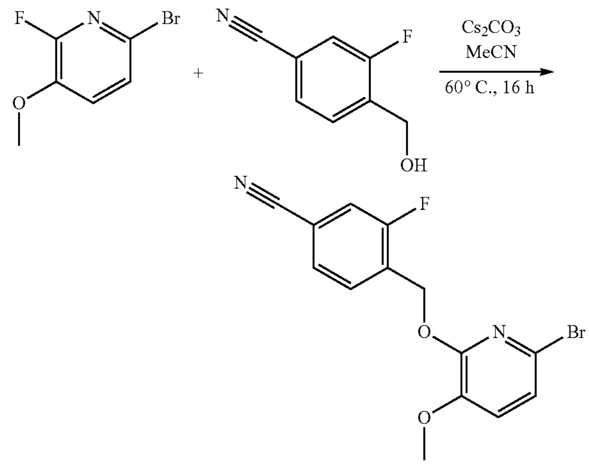

I-147

4-(((6-bromo-3-methoxypyridin-2-yl)oxy)methyl)-3-fluorobenzonitrile (I-147): To a solution of 6-bromo-2-fluoro-3-methoxypyridine (400 mg, 1.94 mmol) and 3-fluoro-4-(hydroxymethyl)benzonitrile (302 mg, 2.00 mmol) in acetonitrile (5 mL) was added cesium carbonate (1.27 g, 3.88 mmol). The mixture was heated at 60° C. overnight. The cooled mixture was partitioned between water and ethyl acetate. The aqueous layer was extracted with two additional portions of ethyl acetate. The combined organic layers were dried over sodium sulfate, isolated by vacuum filtration, concentrated in vacuo, and purified by silica gel column chromatography (eluent: Hexanes/EtOAc) to provide the desired product, I-147. ES/MS: 337.0, 339.0 (M+H$^+$)

Intermediate I-148

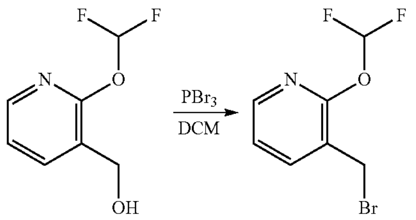

I-148

3-(bromomethyl)-2-(difluoromethoxy)pyridine (I-148): To a solution of (2-(difluoromethoxy)pyridin-3-yl)methanol (100 mg, 0.57 mmol) in DCM (1 mL) was added 1 M phosphorous tribromide in DCM (0.63 ml, 0.63 mmol). The mixture was stirred at RT for 3 h, then quenched by dropwise addition of saturated aqueous sodium bicarbonate until gas evolution ceased. The mixture was partitioned between water and ethyl acetate. The aqueous layer was extracted with two additional portions of EtOAc. The combined organic layers were dried over sodium sulfate, isolated by vacuum filtration, and concentrated in vacuo to provide the desired compound I-148 which was used without purification. 1H NMR (400 MHz, CDCl3) δ 8.14 (dd, J=4.9, 1.9 Hz, 1H), 7.78 (dd, J=7.4, 1.9 Hz, 1H), 7.52 (t, J=72.6 Hz, 1H), 7.11 (dd, J=7.5, 5.0 Hz, 1H), 4.49 (s, 2H).

Intermediate I-149

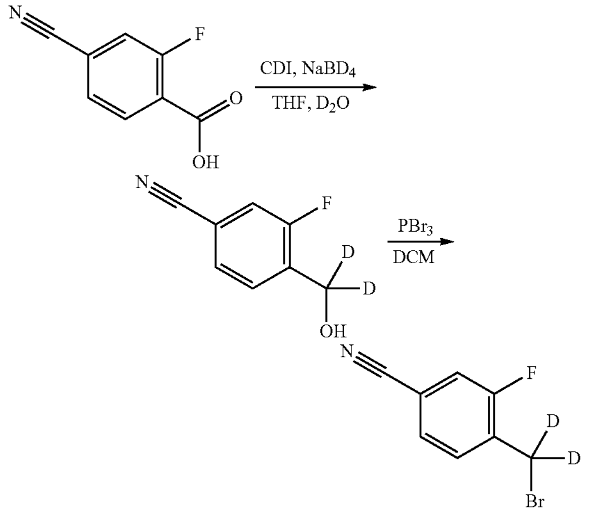

I-149

3-fluoro-4-(hydroxymethyl-d2)benzonitrile: To a solution of 4-cyano-2-fluorobenzoic acid (600 mg, 3.63 mmol) in THF (25 mL) was added 1,1'-carbonyldiimidazole (1.18 g, 7.27 mmol). The mixture was stirred at RT for 2 h, then sodium borodeuteride (304 mg, 7.27 mmol) in $D_2O$ (6.5 mL) was added rapidly dropwise. The mixture was stirred at RT for 15 minutes, then acidified to pH 2 by dropwise addition of concentrated HCl. The organic layer was removed in vacuo, and the aqueous layer was extracted with three portions of ethyl acetate. The combined organic layers were washed with brine, dried over sodium sulfate, isolated by vacuum filtration, and concentrated in vacuo to provide the title compound which was used without purification. ES/MS: 154.2 ($M+H^+$)

4-(bromomethyl-d2)-3-fluorobenzonitrile (I-149): 4-(bromomethyl-d2)-3-fluorobenzonitrile (I-149) was synthesized as described for I-148, substituting (2-(difluoromethoxy)pyridin-3-yl)methanol with 3-fluoro-4-(hydroxymethyl-d2)benzonitrile. 1H NMR (400 MHz, CDCl3) δ 7.53 (dd, J=7.9, 7.2 Hz, 1H), 7.46 (ddd, J=7.9, 1.6, 0.5 Hz, 1H), 7.38 (dd, J=9.1, 1.5 Hz, 1H).

Intermediate I-150

I-150

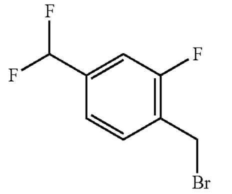

1-(bromomethyl)-4-(difluoromethyl)-2-fluorobenzene (I-150): 1-(bromomethyl)-4-(difluoromethyl)-2-fluorobenzene (I-150) was prepared as described for I-148, substituting (2-(difluoromethoxy)pyridin-3-yl)methanol with (4-(difluoromethyl)-2-fluorophenyl)methanol.

Intermediate I-151

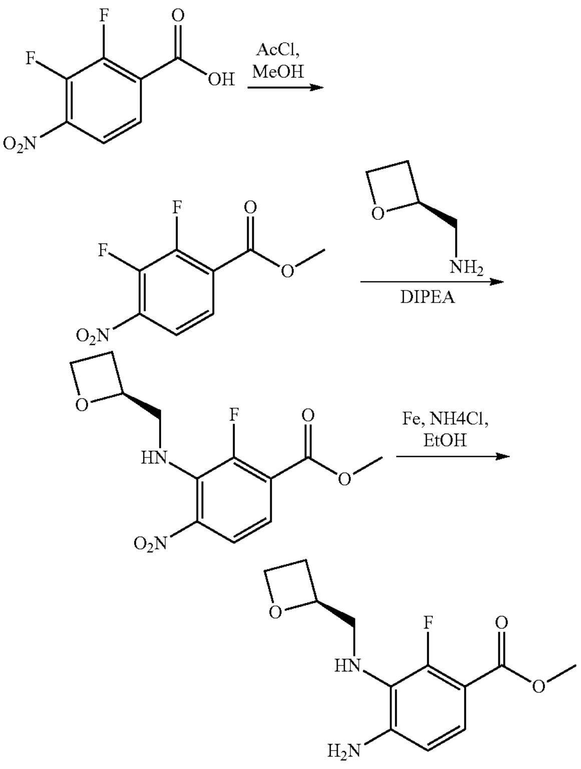

I-151

Methyl 2,3-difluoro-4-nitrobenzoate: To a solution containing actyl chloride (1.53 mL, 21.5 mmol) and MeOH (40 mL) was added 2,3-difluoro-4-nitrobenzoic acid (1.00 g, 4.92 mmol). The resulting mixture was stirred at 70° C. for 16 h. Upon completion the reaction mixture was concentrated in vacuo and separated between saturated aqueous $NaHCO_3$ (20 mL) and EtOAc (50 mL). The organic layer was washed with water (20 mL), brine (10 mL), dried over $MgSO_4$, filtered, concentrated, and used without further purification.

Methyl (S)-2-fluoro-4-nitro-3-((oxetan-2-ylmethyl)amino)benzoate: To a solution of methyl 2,3-difluoro-4-nitrobenzoate (600 mg, 2.76 mmol) in THF (10 mL) was added diisopropylethylamine (1.44 mL, 8.29 mmol) and (S)-oxetan-2-ylmethanamine (0.29 mL, 2.86 mmol). The resulting solution was heated to 60° C. for 4 hrs. Upon completion the solvent was removed, the resulting residue taken up in EtOAc (50 mL), washed with water (10 mL) then brine (10 mL), concentrated and carried forward without further purification. ES/MS: 285.0 ($M+H^+$)

Methyl (S)-4-amino-2-fluoro-3-((oxetan-2-ylmethyl)amino)benzoate (I-151): Methyl (S)-2-fluoro-4-nitro-3-((oxetan-2-ylmethyl)amino)benzoate (785 mg, 2.76 mmol) was taken up in ethanol (10 mL) and saturated aqueous ammonium chloride (3 mL) were added. Iron powder (1.54 g, 27.6 mmol) was then added to the mixture and the mixture heated to 60° C. After 3 hours, the mixture was cooled to room temperature, filtered through celite washing with water (10 mL), MeOH (10 mL, and EtOAc (25 mL), and concentrated in vacuo. To the resulting mixture was added EtOAc (50 mL). The organic solution was washed with water (25 mL), brine (25 mL), dried over $MgSO_4$, filtered and concentrated. The product I-151 was used without further purification. ES/MS: 255.1 ($M+H^+$)

Intermediate I-152

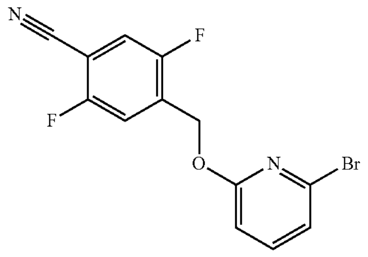

I-152 was prepared in an identical manner as described for I-6 substituting 3-fluoro-4-(hydroxymethyl)benzonitrile with 2,5-difluoro-4-(hydroxymethyl)benzonitrile.

Intermediate I-153

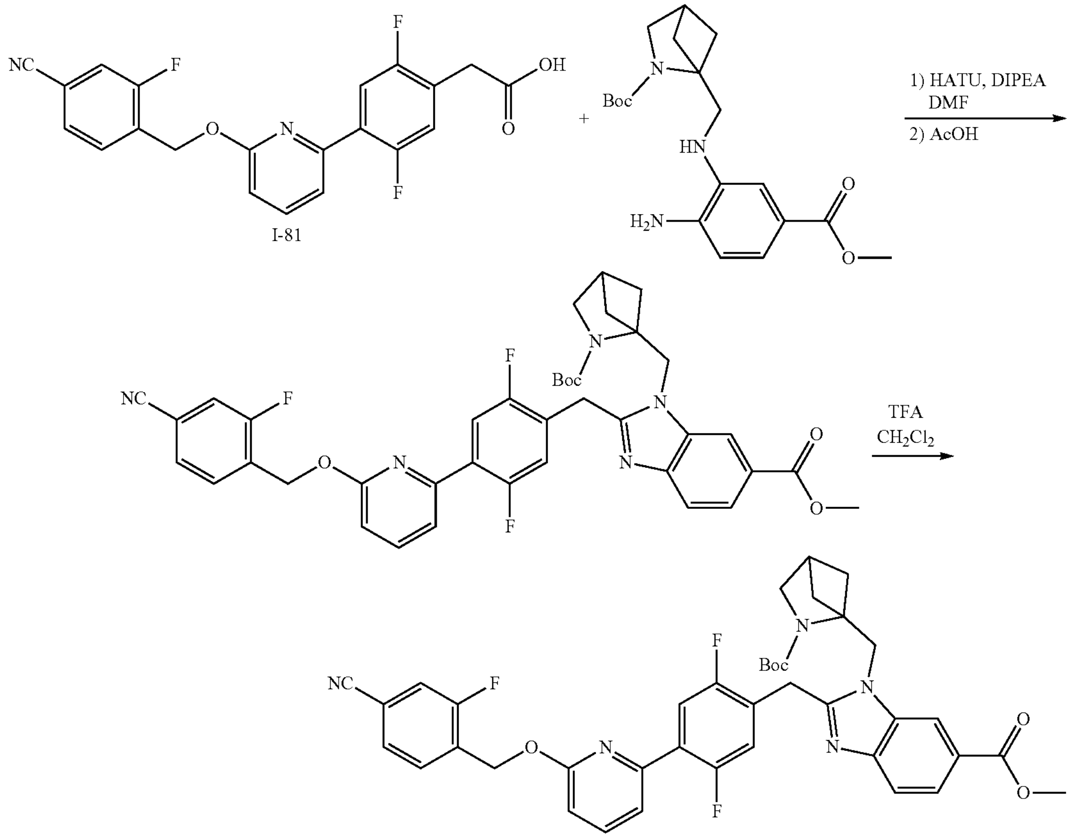

I-81

I-153 tert-Butyl 1-((2-(4-(6-((4-cyano-2-fluorobenzyl)oxy)pyridin-2-yl)-2,5-difluorobenzyl)-6-(methoxycarbonyl)-1H-benzo[d]imidazol-1-yl)methyl)-2-azabicyclo[2.1.1]hexane-2-carboxylate: tert-butyl 1-(((2-amino-5-(methoxycarbonyl)phenyl)amino)methyl)-2-azabicyclo[2.1.1]hexane-2-carboxylate was prepared in an identical manner to I-1 substituting 2-methoxymethanamine with tert-butyl 1-(aminomethyl)-2-azabicyclo[2.1.1]hexane-2-carboxylate. 2-(4-(6-((4-cyano-2-fluorobenzyl)oxy)pyridin-2-yl)-2,5-difluorophenyl)acetic acid (I-81, 250 mg, 0.628 mmol), tert-butyl 1-(((2-amino-5-(methoxycarbonyl)phenyl)amino)methyl)-2-azabicyclo[2.1.1]hexane-2-carboxylate (250 mg, 0.690 mmol), and HATU (286 mg, 0.754 mmol) were taken up in N,N-dimethylformamide (3.00 mL) and N,N-diisopropylethylamine (0.547 mL, 3.14 mmol) was added. The mixture was stirred at r.t. for one hour then diluted with saturated aqueous $NH_4Cl$ (10 mL) and extracted with EtOAc (3×7 mL). The combined organics were dried over $MgSO_4$ and concentrated in vacuo. The resulting residue was taken up in acetic acid (4 mL) and the mixture heated to 100° C. for 2 hours. Following this time, the mixture was cooled to r.t., concentrated in vacuo, and the material purified by normal phase column chromatography (eluent: EtOAc/$CH_2Cl_2$) to yield the product.

Methyl 1-((2-azabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylate (I-153): tert-Butyl 1-((2-(4-(6-((4-cyano-2-fluorobenzyl)oxy)pyridin-2-yl)-2,5-difluorobenzyl)-6-(methoxycarbonyl)-1H-benzo[d]imidazol-1-yl)methyl)-2-azabicyclo[2.1.1]hexane-2-carboxylate (155 mg, 0.214 mmol) was taken up in dichloromethane (2.00 mL) and trifluoroacetic acid (0.200 mL, 0.00175 mol) was added. The mixture was stirred at r.t. overnight and then diluted further with dichloromethane (10 mL) and quenched with saturated $NaHCO_3$ until pH~9. The organic phase was collected and the aqueous phase extracted with dichloromethane (3×5 mL). The combined organics were dried over $MgSO_4$ and concentrated in vacuo. The product (I-153) was used in subsequent reactions without further purification.

ES/MS: 624.2 (M+H$^+$)

Intermediate I-154

I-154

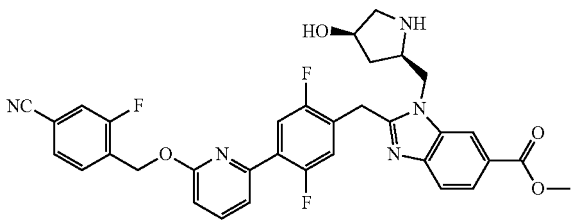

Methyl 2-(4-(6-((4-cyano-2-fluorobenzyl)oxy)pyridin-2-yl)-2,5-difluorobenzyl)-1-(((2R,4R)-4-hydroxypyrrolidin-2-yl)methyl)-1H-benzo[d]imidazole-6-carboxylate (I-154) was prepared identically as described for I-153 substituting tert-butyl 1-(((2-amino-5-(methoxycarbonyl)phenyl)amino)methyl)-2-azabicyclo[2.1.1]hexane-2-carboxylate with tert-butyl (2R,4R)-2-(((2-amino-5-(methoxycarbonyl)phenyl)amino)methyl)-4-hydroxypyrrolidine-1-carboxylate. ES/MS: 628.2 (M+H$^+$)

Intermediate I-155

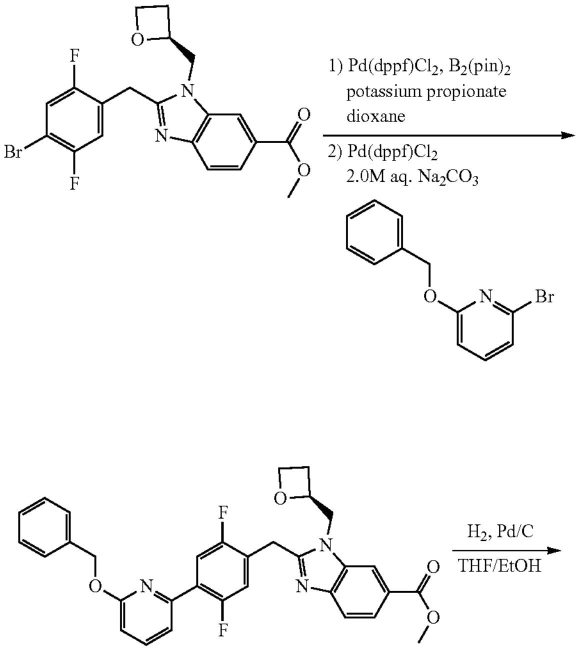

-continued

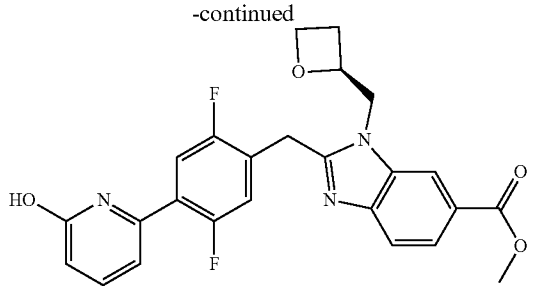

I-155

Methyl (S)-2-(4-(6-(benzyloxy)pyridin-2-yl)-2,5-difluorobenzyl)-1-(oxetan-2-ylmethyl)-1H-benzo[d]imidazole-6-carboxylate: Methyl (S)-2-(4-bromo-2,5-difluorobenzyl)-1-(oxetan-2-ylmethyl)-1H-benzo[d]imidazole-6-carboxylate (450 mg, 0.997 mmol), made as described for I-164 substituting ethyl (S)-4-amino-3-fluoro-5-((oxetan-2-ylmethyl)amino)benzoate (I-62) with methyl (S)-4-amino-3-((oxetan-2-ylmethyl)amino)benzoate and 2-(4-bromo-2-fluorophenyl)acetic acid with 2-(4-bromo-2,5-difluorophenyl)acetic acid, $Pd(dppf)Cl_2$ (74.0 mg, 0.100 mmol), potassium propionate (336 mg, 2.99 mmol), and bis(pinacolato)diboron (304 mg, 2.99 mmol) were taken up in 1,4-dioxane (4.00 mL) and the mixture sparged with argon for 5 minutes. The mixture was then heated to 110° C. for one hour. Following this time, complete conversion to the intermediate boronate ester was observed. The mixture was cooled to r.t. and aqueous sodium carbonate (2.0 M, 0.997 mL, 1.99 mmol) was added. The mixture was stirred for 5 minutes, then 2-(benzyloxy)-6-bromopyridine (290 mg, 1.10 mmol) and $Pd(dppf)Cl_2$ (37.0 mg, 0.050 mmol) were added and the mixture heated to 90° C. for 1 hour. The mixture was then loaded directly onto $SiO_2$ for purification with normal phase column chromatography (eluent: EtOAc/$CH_2Cl_2$ gradient) which afforded the desired product. ES/MS: 556.2 (M+H$^+$)

Methyl (S)-2-(2,5-difluoro-4-(6-hydroxypyridin-2-yl)benzyl)-1-(oxetan-2-ylmethyl)-1H-benzo[d]imidazole-6-carboxylate (1-155): Methyl (S)-2-(4-(6-(benzyloxy)pyridin-2-yl)-2,5-difluorobenzyl)-1-(oxetan-2-ylmethyl)-1H-benzo[d]imidazole-6-carboxylate (426.0 mg, 0.767 mmol) was taken up in ethanol (6.0 mL) and tetrahydrofuran (3.0 mL) and the solution sparged with nitrogen for 5 minutes. Pd/C (408 mg, 0.383 mmol) was then added and nitrogen bubbled through the suspension for an additional 5 minutes. Hydrogen was then bubbled through the solution for 5 minutes before the reaction was set up under balloon hydrogen atmosphere. The reaction was stirred at r.t. for 30 minutes. Following this time, the suspension was filtered through celite, washed with EtOAc (3×10 mL). The filtrate was concentrated in vacuo to afford the methyl (S)-2-(2,5-difluoro-4-(6-hydroxypyridin-2-yl)benzyl)-1-(oxetan-2-ylmethyl)-1H-benzo[d]imidazole-6-carboxylate (I-155). ES/MS: 466.2 (M+H$^+$)

Intermediate I-155

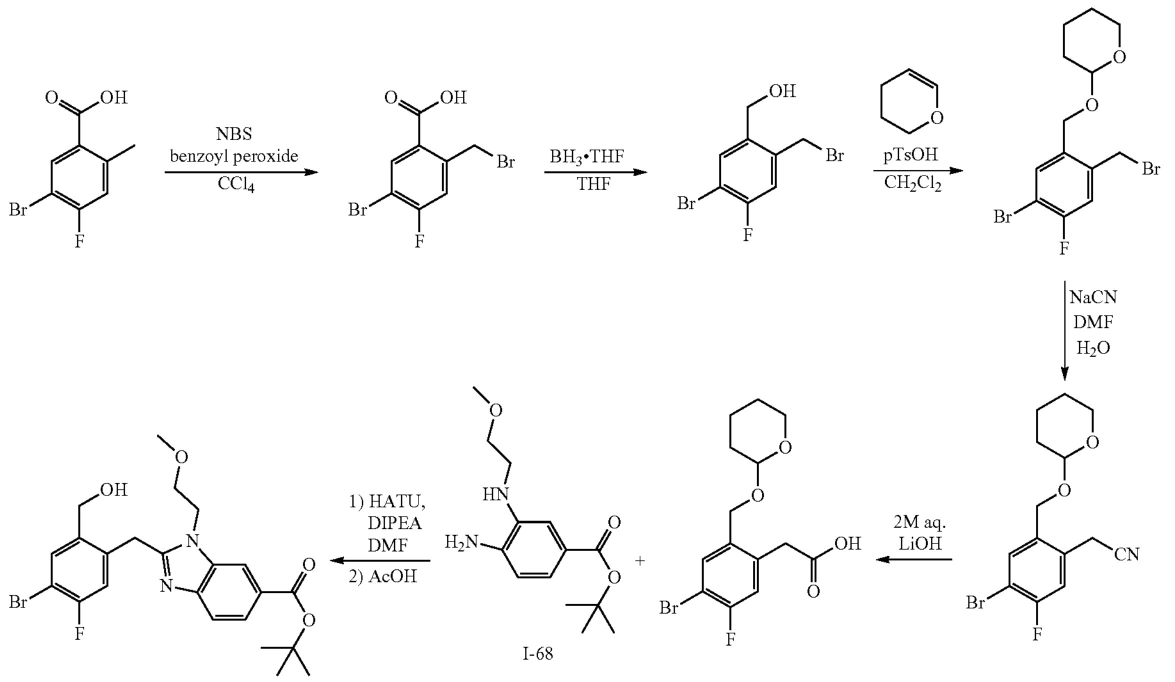

I-68

I-156

5-bromo-2-(bromomethyl)-4-fluorobenzoic acid: 5-bromo-4-fluoro-2-methylbenzoic acid (1.0 g, 4.29 mmol) was taken up in carbon tetrachloride (10.0 mL) and N-bromosuccinimide (917 mg, 5.15 mmol) was added. The mixture was heated to 80° C. and benzoyl peroxide (62.4 mg, 0.257 mmol) was added. The mixture was heated to 80° C. for 1 hour and then the mixture was cooled to r.t. and diluted with dichloromethane (30 mL) and saturated aqueous $NaHCO_3$ (40 mL). The organic phase was collected and the aqueous phase extracted with dichloromethane (30 mL). The combined organic extracts were then washed with brine (40 mL), dried over $MgSO_4$ and concentrated in vacuo. The residue was then purified by column chromatography (eluent: EtOAc/hexanes) to afford the product. $^1$H NMR (400 MHz, Chloroform-d) δ 8.38 (d, J=7.0 Hz, 1H), 7.32 (d, J=8.8 Hz, 1H), 4.95 (s, 2H).

(5-bromo-2-(bromomethyl)-4-fluorophenyl)methanol: Under a $N_2$ atmosphere, 5-bromo-2-(bromomethyl)-4-fluorobenzoic acid (1.53 g, 4.90 mmol) was taken up in tetrahydrofuran (7.5 mL) and the solution was cooled to 0° C. Borane-tetrahydrofuran complex (1.0 M in THF, 7.36 mL, 7.36 mmol) was added slowly to the mixture. Following addition, the mixture was allowed to warm to r.t. and stirred for 8 hours. The reaction was quenched by addition of methanol and then concentrated in vacuo. The residue was then partitioned between 1N HCl (30 mL) and EtOAc (30 mL). The organic phase was collected and washed with saturated aqueous $NaHCO_3$, water, and brine. The combined organic extracts were then dried over $MgSO_4$, concentrated in vacuo, and purified by column chromatography (eluent: EtOAc/Hexanes) to afford the product. ES/MS: 298.0 (M+H$^+$); $^1$H NMR (400 MHz, Chloroform-d) δ 7.67 (d, J=6.9 Hz, 1H), 7.16 (d, J=8.8 Hz, 1H), 4.81 (s, 2H), 4.54 (s, 2H).

2-((5-bromo-2-(bromomethyl)-4-fluorobenzyl)oxy)tetrahydro-2H-pyran: 5-bromo-2-(bromomethyl)-4-fluorophenyl)methanol (725 mg, 2.43 mmol) was taken up in dichloromethane (8.5 mL) and 3,4-dihydro-2H-pyran (0.266 mL, 2.92 mmol) was added followed by p-toluenesulfonic acid monohydrate (12.6 mg, 0.073 mmol). The mixture was stirred at r.t. overnight then concentrated in vacuo and loaded directly onto $SiO_2$ for purification (eluent: EtOAc/hexanes) to afford 2-((5-bromo-2-(bromomethyl)-4-fluorobenzyl)oxy)tetrahydro-2H-pyran. ES/MS: 382.0 (M+H$^+$)

2-(4-bromo-5-fluoro-2-(((tetrahydro-2H-pyran-2-yl)oxy)methyl)phenyl)acetonitrile: 2-((5-bromo-2-(bromomethyl)-4-fluorobenzyl)oxy)tetrahydro-2H-pyran (525 mg, 1.37 mmol) was taken up in N,N-dimethylformamide (4.0 mL) and a solution of sodium cyanide (103 mg, 2.06 mmol) in water (0.52 mL) was added. The mixture was stirred at 80° C. for 3 hours then diluted with EtOAc (15 mL) and washed with saturated aqueous $NaHCO_3$ (15 mL). The organic phase was collected, washed with water (10 mL) and brine (10 mL), dried over $MgSO_4$, and concentrated in vacuo. The resulting residue was purified by column chromatography (eluent: EtOAc/hexanes) to yield the desired product. ES/MS: 350.0 (M+Na$^+$)

2-(4-bromo-5-fluoro-2-(((tetrahydro-2H-pyran-2-yl)oxy)methyl)phenyl)acetic acid: A mixture of 2-(4-bromo-5-fluoro-2-(((tetrahydro-2H-pyran-2-yl)oxy)methyl)phenyl)acetonitrile (319 mg, 0.971 mmol) in aqueous sodium hydroxide (2.0 M, 4.86 mL) was heated to reflux overnight. Following completion of the reaction, the solution was cooled to r.t. and 1H aqueous HCl was added until pH~ 2. The aqueous mixture was extracted with EtOAc (3x10 mL) and the combined organic extracts dried over $MgSO_4$ and concentrated in vacuo. The material was used in the subsequent reaction without purification. ES/MS: 369.0 (M+Na$^+$)

tert-butyl 2-(4-bromo-5-fluoro-2-(hydroxymethyl)benzyl)-1-(2-methoxyethyl)-1H-benzo[d]imidazole-6-carboxylate (I-156): 2-(4-bromo-5-fluoro-2-(((tetrahydro-2H-pyran-2-yl)oxy)methyl)phenyl)acetic acid (164 mg, 0.472 mmol), tert-butyl 4-amino-3-((2-methoxyethyl)amino)benzoate (I-68, 138 mg, 0.519 mmol), and HATU (215 mg, 0.566 mmol) were taken up in N,N-dimethylformamide (2.00 mL) and N,N-diisopropylethylamine (0.411 mL, 2.36 mmol) was added. The mixture was stirred at r.t. for one hour then diluted with saturated aqueous $NH_4Cl$ (10 mL) and extracted with EtOAc (3×7 mL). The combined organics were dried over $MgSO_4$ and concentrated in vacuo. The resulting residue was taken up in acetic acid (4 mL) and the mixture heated to 100° C. for one hour. Following this time, the mixture was cooled to r.t., concentrated in vacuo, and the material purified by normal phase column chromatography (eluent: EtOAc/$CH_2Cl_2$) to yield the product I-156. ES/MS: 493.0 (M+H$^+$)

Intermediate I-157

I-157

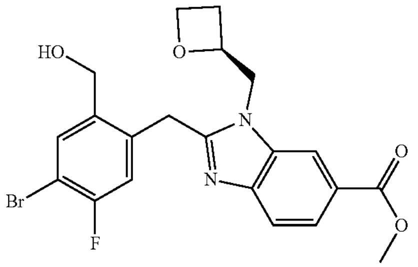

Methyl (S)-2-(4-bromo-5-fluoro-2-(hydroxymethyl)benzyl)-1-(oxetan-2-ylmethyl)-1H-benzo[d]imidazole-6-carboxylate: Methyl (S)-2-(4-bromo-5-fluoro-2-(hydroxymethyl)benzyl)-1-(oxetan-2-ylmethyl)-1H-benzo[d]imidazole-6-carboxylate (I-157) was prepared in an identical manner as described for I-156 substituting methyl (S)-4-amino-3-((oxetan-2-ylmethyl)amino)benzoate for tert-butyl 4-amino-3-((2-methoxyethyl)amino)benzoate. ES/MS: 363.0 (M+H$^+$)

Intermediate I-158

I-158

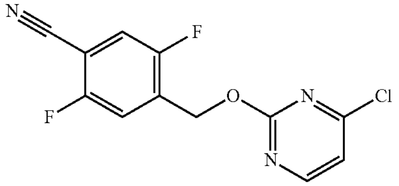

4-(((4-bromopyrimidin-2-yl)oxy)methyl)-2,5-difluorobenzonitrile: 4-(((4-bromopyrimidin-2-yl)oxy)methyl)-2,5-difluorobenzonitrile was prepared identically as described for I-45 substituting 4-(hydroxymethyl)-3-methoxy-benzonitrile with 2,5-difluoro-4-(hydroxymethyl)benzonitrile and 4-bromo-2-methylsulfonyl-pyrimidine with 4-chloro-2-methylsulfonyl-pyrimidine. ES/MS: 282.2 (M+H$^+$).

Intermediate I-159

I-159

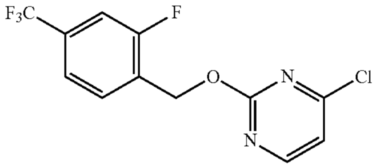

4-bromo-2-((2-fluoro-4-(trifluoromethyl)benzyl)oxy)pyrimidine: 4-bromo-2-((2-fluoro-4-(trifluoromethyl)benzyl)oxy)pyrimidine was prepared identically as described for I-45 substituting 4-(hydroxymethyl)-3-methoxy-benzonitrile with (2-fluoro-4-(trifluoromethyl)phenyl)methanol and 4-bromo-2-methylsulfonyl-pyrimidine with 4-chloro-2-methylsulfonyl-pyrimidine. ES/MS: 307.0 (M+H$^+$).

Intermediate I-160

I-160

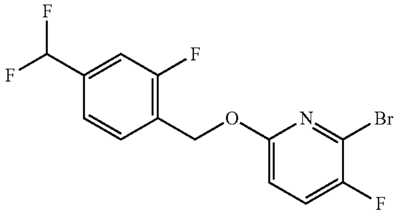

2-bromo-6-((4-(difluoromethyl)-2-fluorobenzyl)oxy)-3-fluoropyridine: 2-bromo-6-((4-(difluoromethyl)-2-fluorobenzyl)oxy)-3-fluoropyridine was prepared identically as described for I-113 substituting 3-fluoro-4-(hydroxymethyl)benzonitrile with (4-(difluoromethyl)-2-fluorophenyl)methanol. ES/MS: 351.0 (M+H$^+$).

Intermediate I-161

I-161

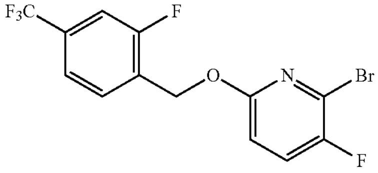

2-bromo-3-fluoro-6-((2-fluoro-4-(trifluoromethyl)benzyl)oxy)pyridine: 2-bromo-3-fluoro-6-((2-fluoro-4-(trifluoromethyl)benzyl)oxy)pyridine was prepared identically as described for I-113 substituting 3-fluoro-4-(hydroxymethyl)benzonitrile with (2-fluoro-4-(trifluoromethyl)phenyl)methanol. ES/MS: 369.0 (M+H$^+$).

Intermediate I-162

I-162

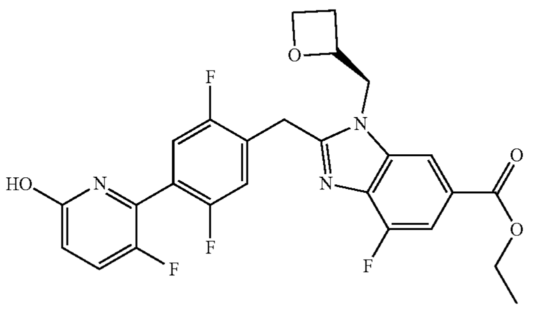

Ethyl (S)-2-(2,5-difluoro-4-(3-fluoro-6-hydroxypyridin-2-yl)benzyl)-4-fluoro-1-(oxetan-2-ylmethyl)-1H-benzo[d]imidazole-6-carboxylate: Ethyl (S)-2-(2,5-difluoro-4-(3-fluoro-6-hydroxypyridin-2-yl)benzyl)-4-fluoro-1-(oxetan-2-ylmethyl)-1H-benzo[d]imidazole-6-carboxylate (I-162) was prepared in an identical manner as described for I-155 substituting Methyl (S)-2-(4-bromo-2,5-difluorobenzyl)-1-(oxetan-2-ylmethyl)-1H-benzo[d]imidazole-6-carboxylate with ethyl (S)-2-(4-bromo-2,5-difluorobenzyl)-4-fluoro-1-(oxetan-2-ylmethyl)-1H-benzo[d]imidazole-6-carboxylate. ES/MS: 516.2 (M+H$^+$).

Intermediate I-163

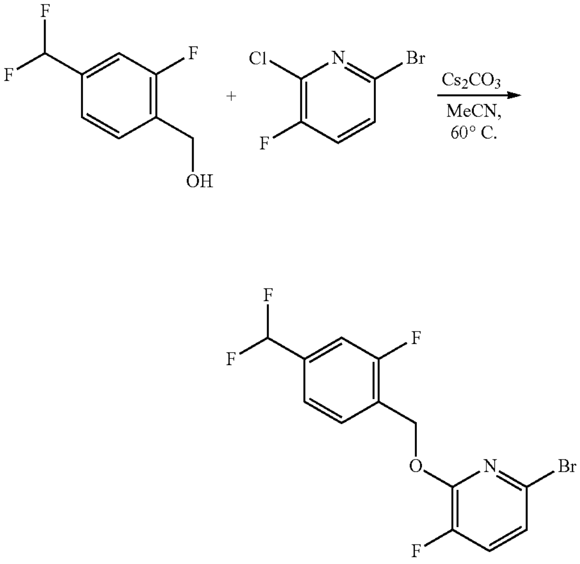

I-163

6-bromo-2-((4-(difluoromethyl)-2-fluorobenzyl)oxy)-3-fluoropyridine (I-163): To a solution of 6-bromo-2-chloro-3-fluoropyridine (500 mg, 2.38 mmol) and (4-(difluoromethyl)-2-fluorophenyl)methanol (431 mg, 2.45 mmol) in acetonitrile (8.0 mL) was added cesium carbonate (1.55 g, 4.75 mmol). The mixture was heated at 60° C. for 24 hours, then cooled, filtered through a pad of Celite (eluent: EtOAc), concentrated in vacuo, and purified by silica gel column chromatography (eluent: EtOAc/hexanes) to provide the desire product. ES/MS: 348.0, 350.0 [M−H]$^-$ Intermediate I-164

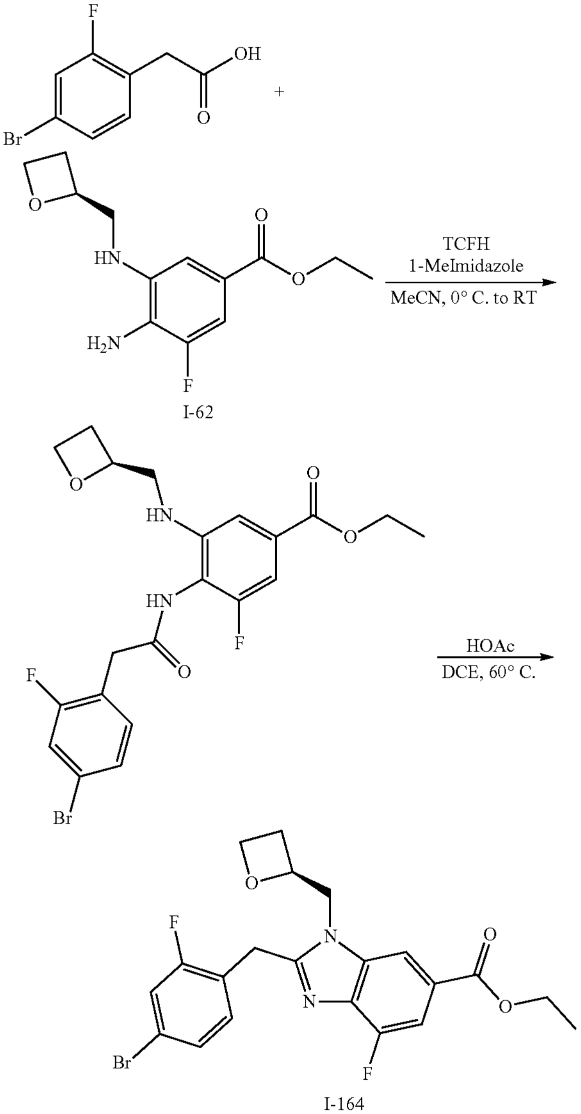

I-62

I-164

Ethyl (S)-4-(2-(4-bromo-2-fluorophenyl)acetamido)-3-fluoro-5-((oxetan-2-ylmethyl)amino)benzoate: To a solution of I-62 (500 mg, 1.86 mmol) and 2-(4-bromo-2-fluorophenyl)acetic acid (521 mg, 2.24 mmol) in MeCN (9.0 mL) and cooled to 0° C. was added 1-methylimidazole (765 mg, 0.74 mL, 9.32 mmol) followed by N,N,N',N'-Tetramethylchloroformamidinium Hexafluorophosphate (732 mg, 2.61 mmol). The mixture was warmed to RT and stirred for 30 minutes. The crude mixture was concentrated in vacuo, then partitioned between water and EtOAc. The organic layer was isolated and washed with an additional portion of water and then brine. The isolated organic layer was dried over sodium sulfate, isolated by vacuum filtration, concentrated in vacuo, and purified by silica gel column chromatography (eluent: EtOAc/hexanes) to provide the desired product. ES/MS: 483.0, 485.0 [M+H]$^+$ Ethyl (S)-2-(4-bromo-2-fluorobenzyl)-4-fluoro-1-(oxetan-2-ylmethyl)-1H-benzo[d]imidazole-6-carboxylate (I-164): To a solution of ethyl (S)-4-(2-(4-bromo-2-fluorophenyl)acetamido)-3-fluoro-5-((oxetan-2-ylmethyl)amino) benzoate (530 mg, 1.10 mmol) in DCE (12.0 mL) was added acetic acid (1.88 mL, 32.9 mmol). The mixture was heated to 60° C. for 12 hours. The mixture was concentrated and partitioned between EtOAc and saturated aqueous sodium bicarbonate. The organic layer was isolated and dried over sodium sulfate, isolated by vacuum filtration, concentrated in vacuo, and purified by silica gel column chromatography (eluent: EtOAc/hexanes) to provide I-164. ES/MS: 465.0, 467.0 $[M+H]^+$ Intermediate I-165

I-165

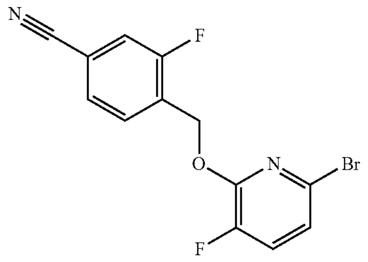

4-(((6-bromo-3-fluoropyridin-2-yl)oxy)methyl)-3-fluorobenzonitrile (I-165): I-165 was prepared in a manner analogous to I-163, replacing (4-(difluoromethyl)-2-fluorophenyl)methanol with 3-fluoro-4-(hydroxymethyl)benzonitrile. ES/MS: 323.0, 325.1 $[M-H]^-$ Intermediate I-166

I-166

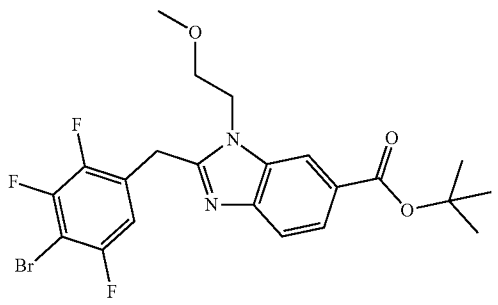

Tert-butyl 2-(4-bromo-2,3,5-trifluorobenzyl)-1-(2-methoxyethyl)-1H-benzo[d]imidazole-6-carboxylate (I-166): I-166 was prepared in a manner analogous to I-96, replacing 2-(4-bromo-3-fluoro-phenyl)acetic acid with 2-(4-bromo-2,3,5-trifluorophenyl)acetic acid and methyl 4-amino-3-(((1-(cyanomethyl)cyclopropyl)methyl)amino)benzoate with tert-butyl 4-amino-3-((2-methoxyethyl)amino)benzoate. ES/MS: 499.0, 501.0 $[M+H]^+$ Intermediate I-167

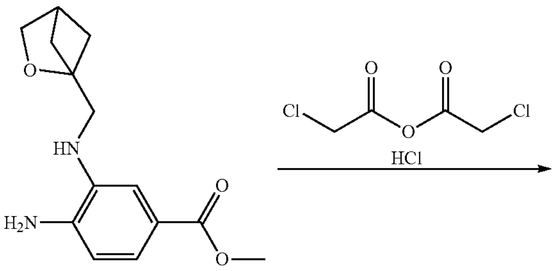

-continued

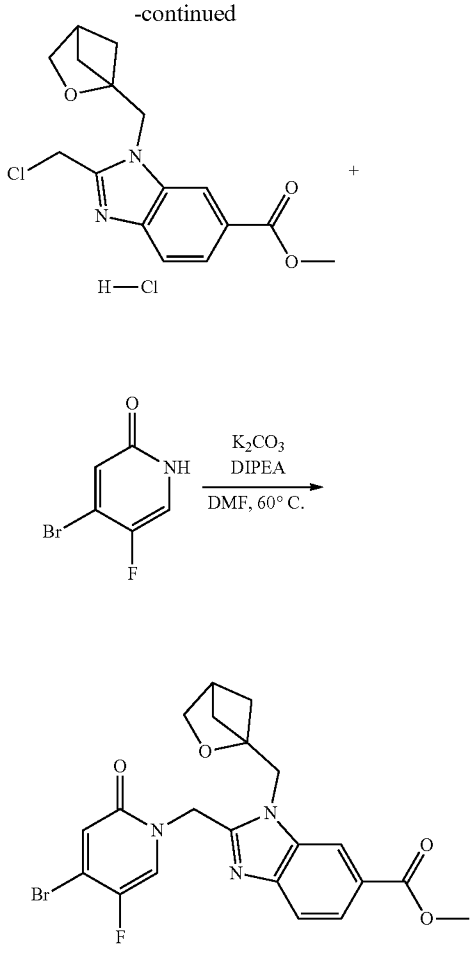

I-167

Methyl 1-((2-oxabicyclo[2.1.1]hexan-1-yl)methyl)-2-(chloromethyl)-1H-benzo[d]imidazole-6-carboxylate hydrochloride: To a solution of methyl 3-(((2-oxabicyclo[2.1.1]hexan-1-yl)methyl)amino)-4-aminobenzoate (300 mg, 1.14 mmol) in 1,4-dioxane (10 mL) heated to 100° C. was added chloroacetic anhydride (197 mg, 1.15 mmol). The mixture was heated at 100° C. for 16 hours, then cooled, concentrated in vacuo, and partitioned between EtOAc and saturated aqueous sodium bicarbonate. The organic layer was isolated, dried over sodium sulfate, and isolated by vacuum filtration. To the solution was added 4 M HCl in 1,4-dioxane (0.31 mL, 1.25 mmol). The solution was stirred for one hour, then the resulting solid was isolate by vacuum filtration to provide the desired product as the HCl salt. ES/MS: 321.2 $[M+H]^+$ Methyl 1-((2-oxabicyclo[2.1.1]hexan-1-yl)methyl)-2-((4-bromo-5-fluoro-2-oxopyridin-1(2H)-yl)methyl)-1H-benzo[d]imidazole-6-carboxylate (I-167): To a solution of 4-bromo-5-fluoropyridin-2(1H)-one (100 mg, 0.52 mmol) and methyl 1-((2-oxabicyclo[2.1.1]hexan-1-yl)methyl)-2-(chloromethyl)-1H-benzo[d]imidazole-6-carboxylate hydrochloride (205 mg, 0.57 mmol) in DMF was added potassium carbonate (360 mg, 2.6 mmol) and DIPEA (0.091 mL, 0.52 mmol). The mixture was heated at 60° C. for 16 hours, then filtered through a pad of Celite (eluent: EtOAc), concentrated in vacuo, and purified by silica gel column chromatography (eluent: EtOAc/DCM) to provide I-167. ES/MS: 476.0, 478.0 $[M+H]^+$ Intermediate I-168

I-168

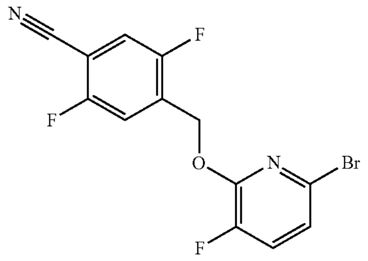

4-(((6-bromo-3-fluoropyridin-2-yl)oxy)methyl)-2,5-difluorobenzonitrile (I-168): I-168 was prepared in a manner analogous to I-163, replacing (4-(difluoromethyl)-2-fluorophenyl)methanol with 2,5-difluoro-4-(hydroxymethyl)benzonitrile. ES/MS: 341.0, 343.0 $[M-H]^-$ Intermediate I-169

I-169

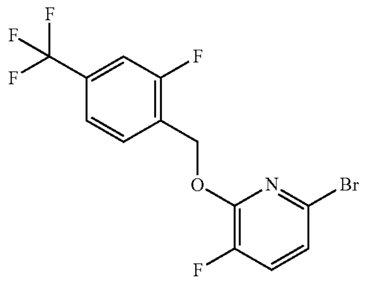

6-bromo-3-fluoro-2-((2-fluoro-4-(trifluoromethyl)benzyl)oxy)pyridine (I-169): I-169 was prepared in a manner analogous to I-163, replacing (4-(difluoromethyl)-2-fluorophenyl)methanol with (2-fluoro-4-(trifluoromethyl)phenyl) methanol. ES/MS: 366.0, 368.0 $[M-H]^-$ Intermediate I-170

I-170

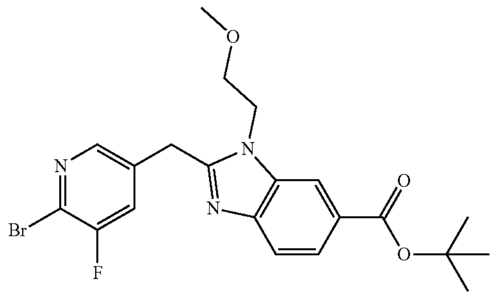

Tert-butyl 2-((6-bromo-5-fluoropyridin-3-yl)methyl)-1-(2-methoxyethyl)-1H-benzo[d]imidazole-6-carboxylate (I-170): I-170 was prepared in a manner analogous to I-164, replacing 2-(4-bromo-2-fluorophenyl)acetic acid with 2-(6-bromo-5-fluoropyridin-3-yl)acetic acid, and I-62 with tert-butyl 4-amino-3-((2-methoxyethyl)amino)benzoate. ES/MS: 464.0, 466.0 $[M+H]^+$ Intermediate I-171

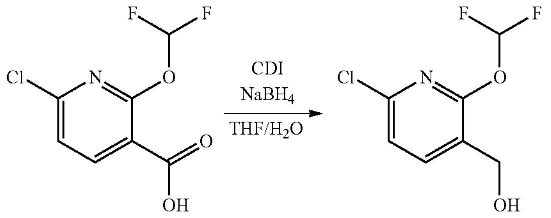

I-171

(6-chloro-2-(difluoromethoxy)pyridin-3-yl)methanol (I-171): To a solution of 6-chloro-2-(difluoromethoxy)nicotinic acid (1.00 g, 4.47 mmol) in THF (30.0 mL) was added 1,1'-carbonyldiimidazole (1.45 g, 8.95 mmol). The mixture was stirred at room temperature for 2 hours, cooled to 0° C., and then sodium borohydride (846 mg, 22.4 mmol) in water (6.0 mL) was added rapidly dropwise. The mixture was warmed to room temperature and stirred for 30 minutes. The mixture was cooled to 0° C., then neutralized by careful dropwise addition of concentrated HCl. The mixture was concentrated in vacuo to remove the THF, and the resulting aqueous suspension was extracted with three portions of EtOAc. The combined organic layers were washed with brine, dried over sodium sulfate, isolated by vacuum filtration, concentrated in vacuo, and the resulting crude product was used without additional purification.

ES/MS: 210.1 $[M+H]^+$

Intermediate I-172

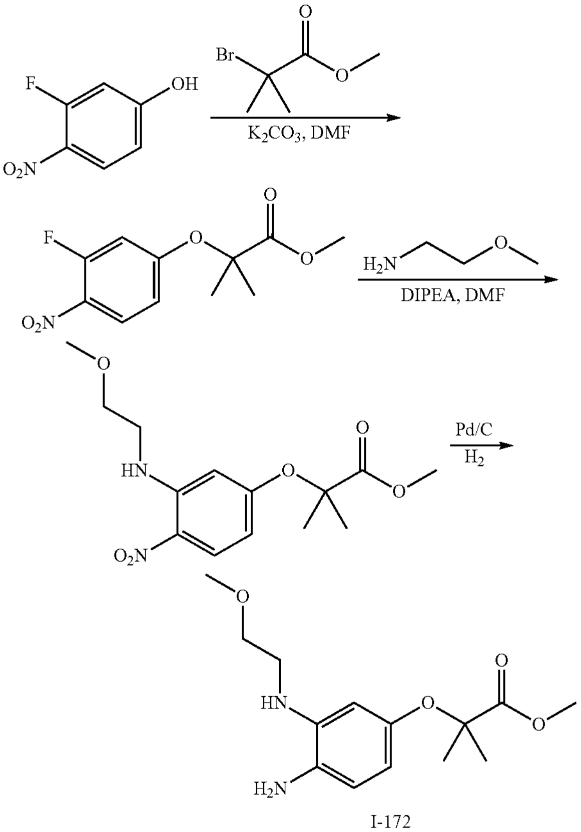

I-172

Methyl 2-(3-fluoro-4-nitro-phenoxy)-2-methyl-propanoate: A suspension of 3-fluoro-4-nitro-phenol (0.500 g, 3.18 mmol), methyl 2-bromo-2-methyl-propanoate (0.691 g, 3.82 mmol), and potassium carbonate (0.660 g, 4.77 mmol) in DMF (10 mL) was heated at 80° C. overnight. The mixture was diluted with EtOAc and washed with 5% LiCl and brine. The organic extract was dried over sodium sulfate, filtered and concentrated. The crude residue was purified by flash chromatography (10-20% EtOAc in hexane) to yield desired product. 1H NMR (400 MHz, Chloroform-d) δ 8.17-7.98 (m, 1H), 6.72-6.57 (m, 2H), 3.80 (s, 3H), 1.71 (s, 6H).

Methyl 2-[3-(2-methoxyethylamino)-4-nitro-phenoxy]-2-methyl-propanoate: A solution of methyl 2-(3-fluoro-4-nitro-phenoxy)-2-methyl-propanoate (166 mg, 0.645 mmol), 2-methoxyethanamine (0.0741 mL, 0.852 mmol), and N,N-diisopropylethylamine (0.562 mL, 3.23 mmol) in DMF (5 mL) was heated at 50° C. o/n. The mixture was diluted with EtOAc and washed with 5% LiCl twice and brine. The organic extract was dried over sodium sulfate, filtered and concentrated. The crude residue was purified by flash chromatography (15-30% EtOAc in hexane) to yield desired product. ES/MS: 313.2 $(M+H^+)$ Methyl 2-[4-amino-3-(2-methoxyethylamino)phenoxy]-2-methyl-propanoate (I-172): A solution of methyl 2-[3-(2-methoxyethylamino)-4-nitro-phenoxy]-2-methyl-propanoate (179 mg, 0.573 mmol) in EtOH (10 mL) was degassed with Ar/Vac three times. Added Pd/C (10.0%, 61.0 mg, 0.0573 mmol) and degassed 1× with Ar/vac and stirred at rt overnight with a balloon of hydrogen. The mixture was filtered over a plug of Celite and concentrated to give desired product. ES/MS: 283.2 $(M+H^+)$ Intermediate I-173

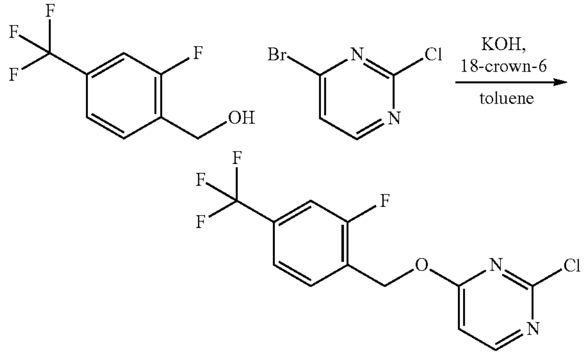

I-173

2-chloro-4-[[2-fluoro-4-(trifluoromethyl)phenyl]methoxy]pyrimidine (I-173): A suspension of 4-bromo-2-chloro-pyrimidine (400 mg, 2.07 mmol), [2-fluoro-4-(trifluoromethyl)phenyl]methanol (442 mg, 2.27 mmol), Potassium hydroxide (128 mg, 2.27 mmol), and 18-Crown-6 (40.0 mg, 0.151 mmol) in toluene (5 mL) was heated at 110° C. for 2 hr. The mixture was diluted with EtOAc and washed with brine. The organic extract was dried over sodium sulfate, filtered and concentrated. The crude residue was purified by flash chromatography (5-10% EtOAc in hexane) to yield desired product. ES/MS: 307.2 $(M+H^+)$ Intermediate I-174

I-174

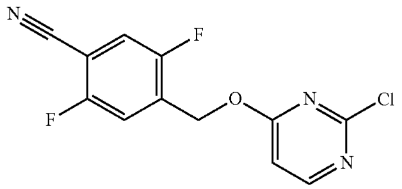

4-[(2-chloropyrimidin-4-yl)oxymethyl]-2,5-difluoro-benzonitrile (I-174): 4-[(2-chloropyrimidin-4-yl)oxymethyl]-2,5-difluoro-benzonitrile was made following the synthetic procedure for I-173, using 2,5-difluoro-4-(hydroxymethyl)benzonitrile, in place of [2-fluoro-4-(trifluoromethyl)phenyl]methanol. ES/MS: 282.2 $(M+H^+)$.

Intermediate I-175

I-175

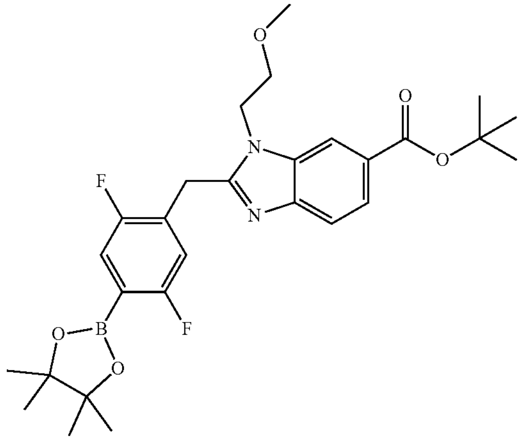

Tert-butyl 2-(2,5-difluoro-4-(4,4,5,5-tetramethyl-1,3,2-dioxaborolan-2-yl)benzyl)-1-(2-methoxyethyl)-1H-benzo[d]imidazole-6-carboxylate (I-175): tert-butyl 2-(2,5-difluoro-4-(4,4,5,5-tetramethyl-1,3,2-dioxaborolan-2-yl)benzyl)-1-(2-methoxyethyl)-1H-benzo[d]imidazole-6-carboxylate was prepared following procedure Intermediate I-5 substituting 2-(4-bromo-2,5-difluorophenyl)acetic acid for 2-(4-bromo-2-fluorophenyl)acetic acid and tert-butyl 4-amino-3-((2-methoxyethyl)amino)benzoate (intermediate I-68) for methyl 4-amino-3-(2-methoxyethylamino)benzoate. ES/MS: 529.3 $(M+H^+)$; $^1$H NMR (400 MHz, DMSO-$d^6$) δ 8.13 (s, 1H), 7.74 (dd, J=8.4, 1.6 Hz, 1H), 7.56 (d, J=8.4 Hz, 1H), 7.33 (dd, J=9.3, 4.6 Hz, 1H), 7.17 (dd, J=9.1, 5.5 Hz, 1H), 4.54 (t, J=5.1 Hz, 2H), 4.39 (s, 2H), 3.65 (t, J=5.1 Hz, 2H), 3.20 (s, 3H), 1.57 (s, 9H), 1.31 (s, 12H).

Intermediate I-176

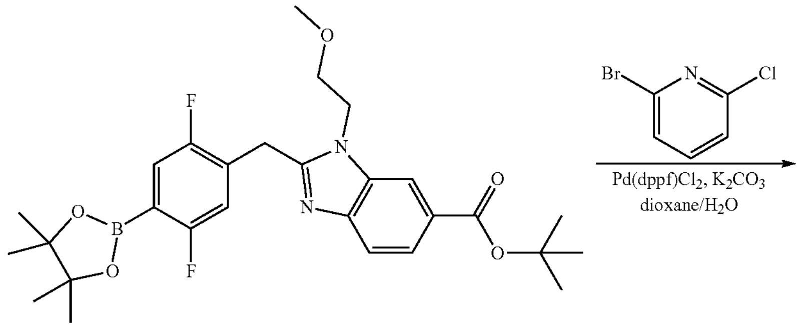

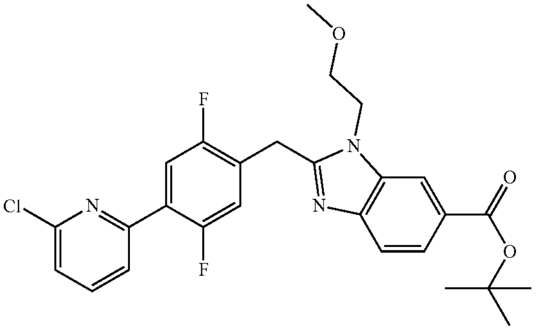

I-176

Tert-butyl 2-[[4-(6-chloropyridin-2-yl)-2,5-difluorophenyl]methyl]-3-(2-methoxyethyl)-1,3-benzodiazole-5-carboxylate (I-176): Tert-butyl 2-[[2,5-difluoro-4-(4,4,5,5-tetramethyl-1,3,2-dioxaborolan-2-yl)phenyl]methyl]-3-(2-methoxyethyl)-1,3-benzodiazole-5-carboxylate (30.0 g, 56.7 mmol, 1.00 equiv) and 2-bromo-6-chloropyridine (14.2 g, 73.8 mmol, 1.30 equiv) were dissolved in 1,4-dioxane (600 mL) and $H_2O$ (60 mL). To the above solution was added Pd(dppf)$Cl_2$ (4.15 g, 5.68 mmol, 0.1 equiv) and $K_2CO_3$ (15.7 g, 114 mmol, 2.0 equiv). The resulting solution was heated to 90° C. overnight under a nitrogen atmosphere. The resulting mixture was concentrated under reduced pressure. The residue was purified by silica gel column chromatography, eluted with Petroleum ether/EtOAc (2/1) to afford tert-butyl 2-[[4-(6-chloropyridin-2-yl)-2,5-difluorophenyl]methyl]-3-(2-methoxyethyl)-1,3-benzodiazole-5-carboxylate. ES/MS: 513.8 (M+$H^+$); $^1$H NMR (400 MHz, DMSO-$d^6$) δ 8.14 (s, 1H), 8.02 (t, J=7.9 Hz, 1H), 7.87 (d, J=7.7 Hz, 1H), 7.78-7.69 (m, 2H), 7.59 (d, J=8.2 Hz, 2H), 7.41 (dd, J=11.4, 6.0 Hz, 1H), 4.58 (t, J=5.1 Hz, 2H), 4.44 (s, 2H), 3.68 (t, J=5.1 Hz, 2H), 3.22 (s, 3H), 1.58 (s, 9H).

Intermediate I-177

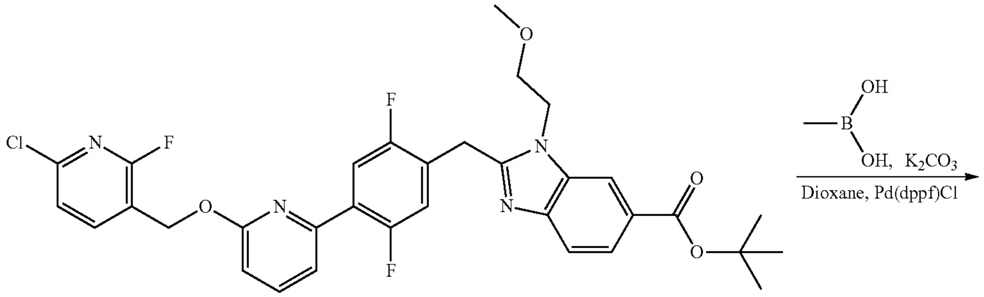

-continued

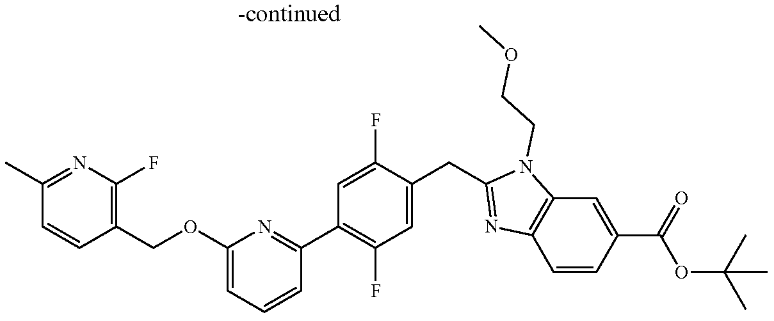

I-177

Tert-butyl 2-[[2,5-difluoro-4-[6-[(2-fluoro-6-methyl-3-pyridyl)methoxy]-2-pyridyl]phenyl]methyl]-3-(2-methoxy-ethyl)benzimidazole-5-carboxylate (I-177): A suspension of tert-butyl 2-[[4-[6-[(6-chloro-2-fluoro-3-pyridyl)methoxy]-2-pyridyl]-2,5-difluoro-phenyl]methyl]-3-(2-methoxyethyl) benzimidazole-5-carboxylate (160 mg, 0.25 mmol), methylboronic acid (0.15 g, 2.5 mmol), [1,1'-Bis (diphenylphosphino)ferrocene]dichloropalladium(II) (28 mmol, 0.038 mmol), and potassium carbonate (173 mg, 1.25 mmol) in 1 mL dioxane and 0.3 mL of water was heated to 120° C. for 3 hours. Upon cooling the crude reaction mixture was purified directly by flash column (Rf=0.3 EtOAc/Hexanes=50%) to afford 130 mg of desired product. ES/MS: 619.4 (M+H+)

Intermediate I-178

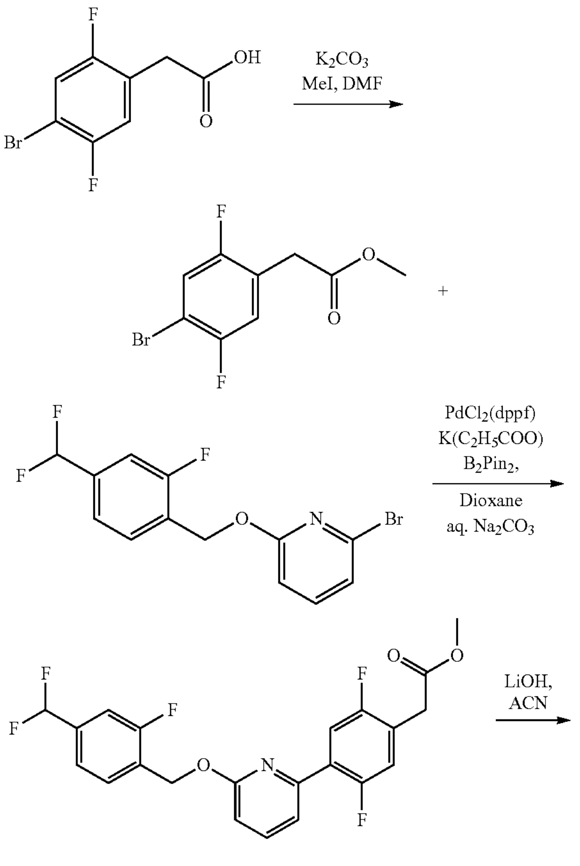

-continued

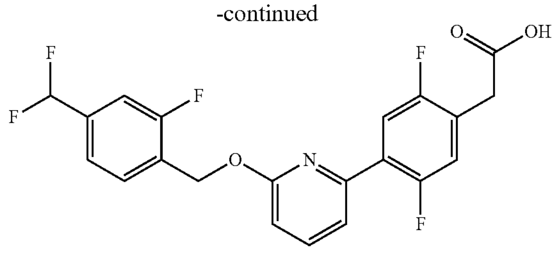

I-178

Methyl 2-(4-bromo-2,5-difluoro-phenyl)acetate: 2-(4-bromo-2,5-difluoro-phenyl)acetic acid (2.00 g, 7.97 mmol) was dissolved in DMF (16 mL). Potassium carbonate (1652 mg, 12.0 mmol) followed by iodomethane (1357 mg, 9.56 mmol) were added to the solution. The mixture was stirred at ambient temperature for 4 hours until the starting material was consumed by TLC. The mixture was diluted with water (20 mL) and extracted with EtOAc (3×20 mL). The combined organic layers were washed with brine (30 mL), dried with sodium sulfate, filtered and concentrated in vacuo. The mixture was purified by column chromatography (0-100% EtOAc in hexane) to give the title compound as a colorless liquid. 1H NMR (400 MHz, Chloroform-d) δ 7.32-7.23 (m, 2H), 7.06 (dd, J=8.4, 6.3 Hz, 1H), 3.71 (s, 3H), 3.61 (d, J=1.3 Hz, 2H).

Methyl 2-[4-[6-[[4-(difluoromethyl)-2-fluoro-phenyl] methoxy]-2-pyridyl]-2,5-difluoro-phenyl]acetate: Methyl 2-(4-bromo-2,5-difluoro-phenyl)acetate (0.500 g, 1.89 mmol) was dissolved in 1,4-dioxane (9.4 mL). [1,1'-Bis (diphenylphosphino)ferrocene]dichloropalladium(II) (0.140 g, 0.189 mol), potassium propanoate (0.635 g, 5.66 mmol) and bis(pinacolato)diboron (0.623 g, 0.00245 mol) were added to the solution. The mixture was degassed by bubbling $N_2$ through the mixture for 5 minutes. The mixture was heated to 100° C. for 2 hours after which the mixture was cooled to ambient temperature and (1,1'-bis(diphenylphosphino)ferrocene)-dichloropalladium(II) (0.0667 g, 9.43e-5 mol), 2-bromo-6-((4-(difluoromethyl)-2-fluorobenzyl)oxy) pyridine (658 mg, 1.98 mmol) and aqueous sodium carbonate (2.0 M, 1.89 mL, 3.77 mmol) were added. The mixture was heated to 100° C. and stirred for 2 hours. The mixture was cooled to ambient temperature and water (5 mL) was added. The aqueous layer was extracted with EtOAc (3×10 mL). The combined organic layers were washed with brine (20 mL), dried with sodium sulfate, filtered and concentrated in vacuo. The mixture was purified by column chromatography (0-100% EtOAc in hexane) to give the title compound. ES/MS: 437.95 (M+H+) 1H NMR (400 MHz, Chloroform-d) δ 7.77 (dd, J=10.5, 6.4 Hz, 1H), 7.65 (dt, J=22.8, 7.7 Hz, 2H), 7.51 (dd, J=7.7, 1.6 Hz, 1H), 7.30 (d, J=8.1 Hz, 2H), 7.09 (dd, J=11.2, 6.0 Hz, 1H), 6.81 (d, J=8.2 Hz, 1H), 6.63 (s, 1H), 5.56 (s, 2H), 3.75 (s, 3H), 3.70 (s, 2H).

2-(4-(6-((4-(difluoromethyl)-2-fluorobenzyl)oxy)pyridin-2-yl)-2,5-difluorophenyl)acetic acid (I-178): methyl 2-(4-(6-((4-(difluoromethyl)-2-fluorobenzyl)oxy)pyridin-2-yl)-2,5-difluorophenyl)acetate (0.535 g, 1.22 mmol) was dissolved in ACN (5 mL). Lithium hydroxide (2.0 M, 1.22 mL, 2.45 mmol) was added and the mixture was heated to 60° C. for 3 hours. The mixture was cooled to ambient temperature and neutralized with aq. HCl (2 M). The reaction was extracted with EtOAc (3×10 mL). The combined organic layers were washed with brine (5 mL), dried with sodium sulfate, filtered and concentrated in vacuo to yield the titled product as a white solid. ES/MS: 423.999 ($M+H^+$) 1H NMR (400 MHz, Methanol-d4) δ 7.82-7.68 (m, 2H), 7.66 (t, J=7.5 Hz, 1H), 7.57-7.41 (m, 1H), 7.41-7.26 (m, 2H), 7.20 (dd, J=11.5, 6.0 Hz, 1H), 6.96-6.56 (m, 2H), 5.58 (s, 2H), 3.84-3.61 (m, 2H). 19F NMR (377 MHz, Methanol-d4) δ −113.28 (d, J=56.2 Hz), −118.11--120.85 (m), −122.27--124.55 (m), −125.30 (ddd, J=18.1, 11.0, 6.0 Hz).

Intermediate I-179

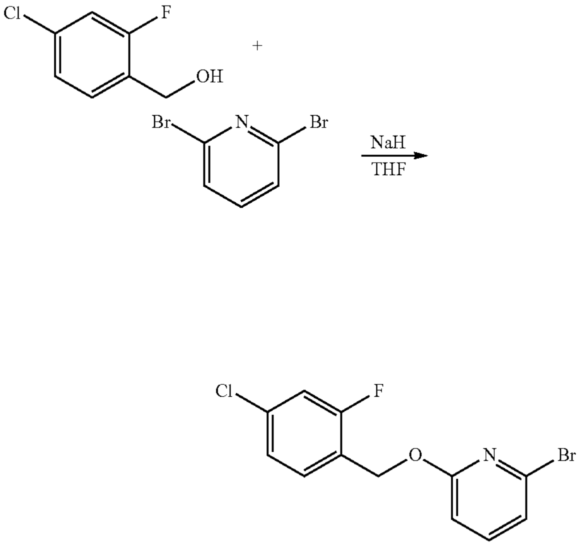

I-179

2-bromo-6-[(4-chloro-2-fluoro-phenyl)methoxy]pyridine (I-179): (4-chloro-2-fluoro-phenyl)methanol (1.00 g, 6.23 mol) and 2,6-dibromopyridine (1.48 g, 6.23 mmol) were dissolved in THF (15 mL). Sodium hydride (50.0%, 0.430 g, 9.34 mmol) was added and the mixture was stirred at ambient temperature overnight. The reaction was quenched with the addition of water (10 mL) and extracted with EtOAc (3×15 mL). The combined organic layers were washed with brine (30 mL), dried with sodium sulfate, filtered and concentrated in vacuo. The reaction was purified by column chromatography (0-100% EtOAc in hexane) to give the title compound. 1H NMR (400 MHz, Chloroform-d) δ 7.45 (dt, J=10.1, 7.8 Hz, 2H), 7.22-7.00 (m, 4H), 6.73 (d, J=8.1 Hz, 1H), 5.38 (d, J=1.2 Hz, 2H).

Intermediate I-180

I-180

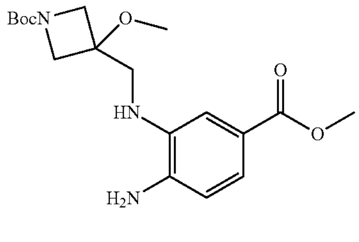

Tert-butyl 3-(((2-amino-5-(methoxycarbonyl)phenyl)amino)methyl)-3-methoxyazetidine-1-carboxylate (I-180): The title compound was prepared identically as described for I-1 substituting methoxyethylamine with tert-butyl 3-(aminomethyl)-3-methoxyazetidine-1-carboxylate; hydrochloride: ES/MS: 365.2 ($M+H^+$).

Intermediate I-181

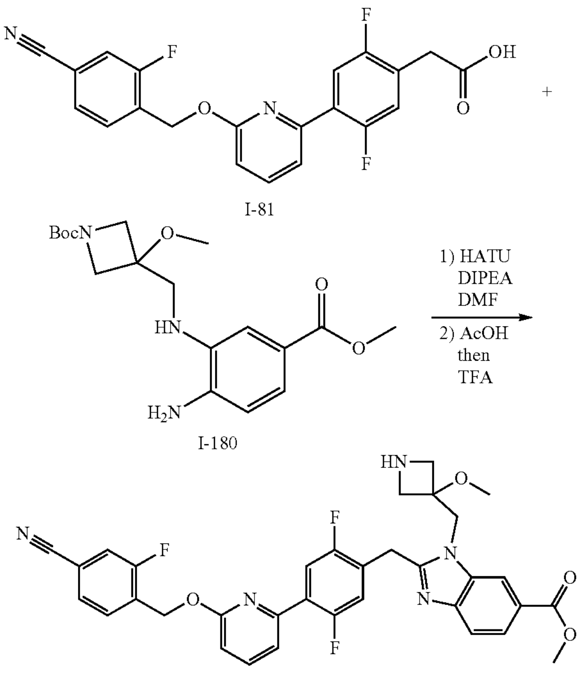

I-181

Methyl 2-(4-(6-((4-cyano-2-fluorobenzyl)oxy)pyridin-2-yl)-2,5-difluorobenzyl)-1-((3-methoxyazetidin-3-yl)methyl)-1H-benzo[d]imidazole-6-carboxylate (I-181): 2-(4-(6-((4-cyano-2-fluorobenzyl)oxy)pyridin-2-yl)-2,5-difluorophenyl)acetic acid (I-81) (830 mg, 2.08 mmol), tert-butyl 3-(((2-amino-5-(methoxycarbonyl)phenyl)amino)methyl)-3-methoxyazetidine-1-carboxylate (I-180) (634 mg, 1.73 mmol), and O-(7-azabenzotriazol-1-yl)-N,N,N',N'-tetramethyluronium hexafluorophosphate (923 mg, 2.43 mmol) were taken up in DMF (15 mL) and N,N-diisopropylethylamine (1.50 mL, 8.50 mmol) was added. The mixture was stirred at room temperature for 30 min. Following this time, the mixture was diluted with EtOAc (200 mL) and water (200 mL). The organic phase was collected, and the aqueous phase extracted with EtOAc (2×50 mL). The combined organic phases were dried over $Na_2SO_4$ and concentrated in vacuo.

The resulting residue was taken up in a mixture of dichloroethane (20 mL) and acetic acid (6.0 mL), and heated to 80° C. After 6 hours, the mixture was concentrated in vacuo and the residue was dissolved in DCM (25 mL). TFA (5.0 mL) was added, and the mixture was heated to 45° C. After 2.5 hours, the mixture was concentrated in vacuo and the residue was dissolved in EtOAc (80 mL). The organic phase was washed with saturated aqueous $NaHCO_3$ (30 mL) and the aqueous phase extracted with EtOAc (2×50 mL). The combined organic phases were dried over $Na_2SO_4$ and concentrated in vacuo. The crude residue was purified by silica gel column chromatography (eluent: EtOAc/hexanes): ES/MS: 628.2 ($M+H^+$).

Intermediate I-182

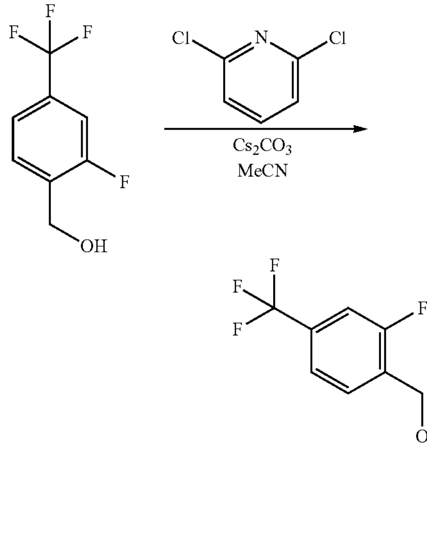

I-182

2-Chloro-6-((2-fluoro-4-(trifluoromethyl)benzyl)oxy) pyridine (I-182): A suspension of (2-fluoro-4-(trifluoromethyl)phenyl)methanol (2.70 g, 13.9 mmol), 2,6-dichloropyridine (2.00 g, 13.5 mmol), and cesium carbonate (8.81 g, 27.0 mmol) in MeCN (50 mL) was heated at 60° C. overnight. The mixture was filtered through a plug of Celite® and concentrated in vacuo. The residue was purified by silica gel column chromatography (eluent: EtOAc/hexanes) to give the title compound. ES/MS: 306.2 ($M+H^+$); $^1$H NMR (400 MHz, $CDCl_3$) δ 7.68 (t, J=7.5 Hz, 1H), 7.58 (t, J=7.9 Hz, 1H), 7.46 (dd, J=8.0, 1.7 Hz, 1H), 7.38 (dd, J=9.7, 1.8 Hz, 1H), 6.98 (d, J=7.5 Hz, 1H), 6.76 (d, J=8.2 Hz, 1H), 5.51 (s, 2H).

Intermediate I-183

I-183

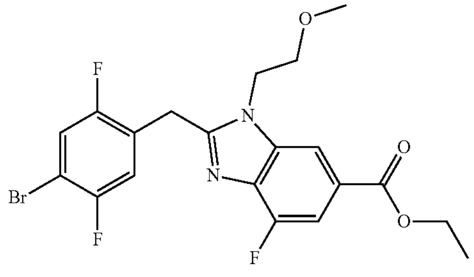

Ethyl 2-(4-bromo-2,5-difluorobenzyl)-4-fluoro-1-(2-methoxyethyl)-1H-benzo[d]imidazole-6-carboxylate (I-183): The title compound was prepared identically as described for I-164 substituting ethyl (S)-4-amino-3-fluoro-5-((oxetan-2-ylmethyl)amino)benzoate (I-62) with ethyl 4-amino-3-fluoro-5-((2-methoxyethyl)amino)benzoate: ES/MS: 471.2 (M+H+).

Intermediate I-184

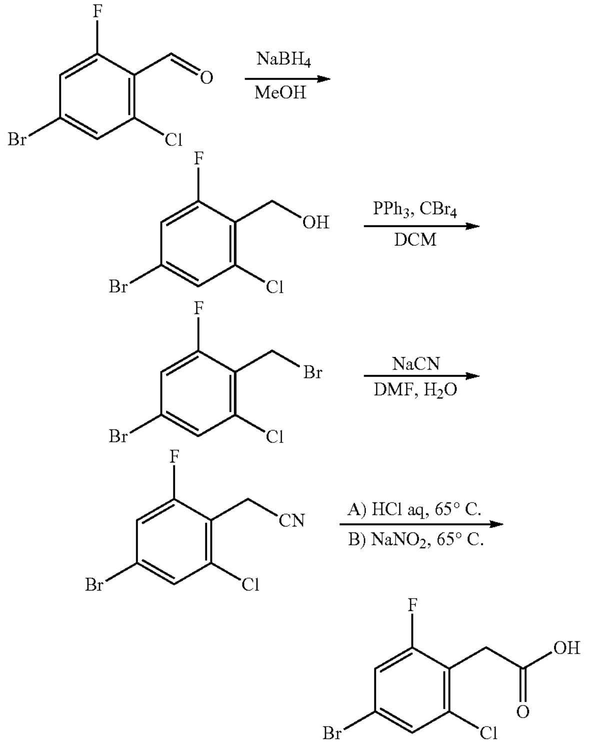

I-184

4-bromo-2-chloro-6-fluoro-phenyl)methanol: To a solution containing 4-bromo-2-chloro-6-fluoro-benzaldehyde (1 g, 4.2 mmol) and MeOH (20 mL) was added $NaBH_4$ (0.17 g, 4.4 mmol) in portions at 0° C. The resulting mixture was stirred and allowed to reach room temperature overnight. Upon completion, the reaction mixture was concentrated in vacuo and separated between saturated aqueous $NaHCO_3$ (20 mL) and EtOAc (50 mL). The organic layer was washed with water (20 mL), brine (10 mL), dried over $MgSO_4$, filtered, concentrated, and used without further purification.

5-bromo-2-(bromomethyl)-1-chloro-3-fluoro-benzene: To a solution of 4-bromo-2-chloro-6-fluoro-phenyl)methanol (1 g, 4.18 mmol) in DCM (10 mL) was added triphenylphosphine (1.26 g, 4.8 mmol) and carbon tetrabromide (1.6 g, 4.8 mmol). The resulting solution was stirred overnight. Upon completion the solvent was removed, concentrated and the resulting crude residue was purified by flash chromatography (0-20% EtOAc in hexane) to afford the product.

2-(4-bromo-2-chloro-6-fluoro-phenyl)acetonitrile: 5-bromo-2-(bromomethyl)-1-chloro-3-fluoro-benzene (450 mg, 1.5 mmol) was taken up in DMF (16 mL) and water (6 mL), followed by the addition of sodium cyanide (0.11 g, 2.2 mmol). The mixture was stirred overnight at room temperature. Upon completion, saturated aqueous $NaHCO_3$ (20 mL)

and EtOAc (50 mL) were added and the layers were separated. The organic solution was washed with water (25 mL), brine (25 mL), dried over $MgSO_4$, filtered and concentrated. The product was utilized for the next step without further purification.

2-(4-bromo-2-chloro-6-fluoro-phenyl)acetic acid (I-184): 2-(4-bromo-2-chloro-6-fluoro-phenyl)acetonitrile (350 mg, 1.5 mmol) was taken up in aqueous HCl (20 mL) and heated to 65° C. for 18 hours. After 18 hours, sodium nitrite (486 mg, 7.5 mmol) was added and the mixture was stirred at 65° C. overnight. Upon completion, water (30 mL) and EtOAc (50 mL) were added and the layers were separated. The organic solution was washed with water (25 mL), brine (25 mL), dried over $MgSO_4$, filtered and concentrated. The product was utilized for the next step without further purification. $^1$H NMR (400 MHz, DMSO-$d_6$): 12.8 (br s, 1H), 7.69-7.60 (m, 4H), 3.71 (s, 2H).

Intermediate I-185

I-185

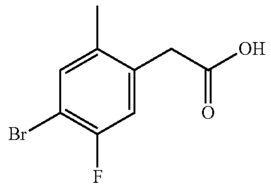

I-185 was prepared in an identical manner as described for I-184 substituting 4-bromo-2-chloro-6-fluoro-benzaldehyde with 4-bromo-3-fluoro-6-methyl-benzaldehyde.

Intermediate I-186

I-186

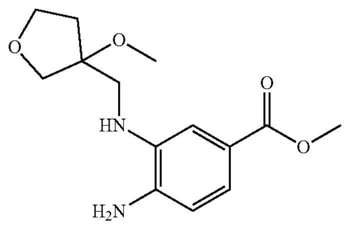

Methyl 4-amino-3-(((3-methoxytetrahydrofuran-3-yl)methyl)amino)benzoate (I-186): Methyl 4-amino-3-(((3-methoxytetrahydrofuran-3-yl)methyl)amino)benzoate was prepared following procedure Intermediate I-112 substituting methyl 3-fluoro-4-nitrobenzoate for methyl 2-fluoro-3-nitrobenzoate and (3-methoxytetrahydrofuran-3-yl)methanamine for 2-methoxyethan-1-amine. ES/MS: 281.2 (M+H$^+$).

Intermediate I-187

I-187

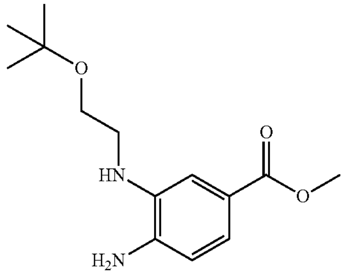

Methyl 4-amino-3-((2-(tert-butoxy)ethyl)amino)benzoate (I-187): Methyl 4-amino-3-((2-(tert-butoxy)ethyl)amino)benzoate was prepared following procedure Intermediate I-112 substituting methyl 3-fluoro-4-nitrobenzoate for methyl 2-fluoro-3-nitrobenzoate and 2-(tert-butoxy)ethan-1-amine for 2-methoxyethan-1-amine. ES/MS: 267.198 (M+H$^+$).

Intermediate I-188

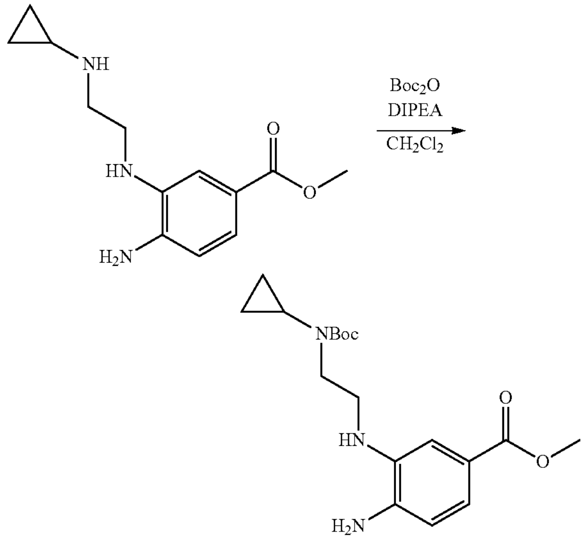

I-188

Methyl 4-amino-3-((2-(cyclopropylamino)ethyl)amino)benzoate: Methyl 4-amino-3-((2-(cyclopropylamino)ethyl)amino)benzoate was prepared following procedure Intermediate I-112 substituting methyl 3-fluoro-4-nitrobenzoate for methyl 2-fluoro-3-nitrobenzoate and N1-cyclopropylethane-1,2-diamine for 2-methoxyethan-1-amine. ES/MS: 250.140 (M+H$^+$).

Methyl 4-amino-3-((2-((tert-butoxycarbonyl)(cyclopropyl)amino)ethyl)amino)benzoate (I-188): To a solution of methyl 4-amino-3-((2-(cyclopropylamino)ethyl)amino)benzoate (285 mg, 1.14 mmol) in $CH_2Cl_2$ (10 mL) was added di-tert-butyl dicarbonate (277 mg, 1.27 mmol) and DIPEA (0.22 mL, 1.26 mmol). The resulting solution was stirred at room temperature for 16 hours and then concentrated to dryness. The crude material was then purified by $SiO_2$ column chromatography (eluent: EtOAc/hexanes) to provide methyl 4-amino-3-((2-((tert-butoxycarbonyl)(cyclopropyl)amino)ethyl)amino)benzoate (I-188). ES/MS: 350.046 (M+H$^+$).

Intermediate I-189

I-189

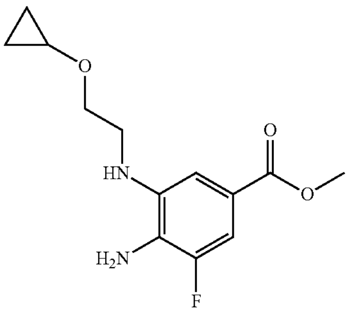

Methyl 4-amino-3-((2-cyclopropoxyethyl)amino)-5-fluorobenzoate (I-189): Methyl 4-amino-3-((2-cyclopropoxyethyl)amino)-5-fluorobenzoate was prepared following procedure Intermediate I-112 substituting methyl 3,5-difluoro-4-nitrobenzoate for methyl 2-fluoro-3-nitrobenzoate and 2-cyclopropoxyethan-1-amine for 2-methoxyethan-1-amine. ES/MS: 269.369 (M+H$^+$).

Intermediate I-190

I-190

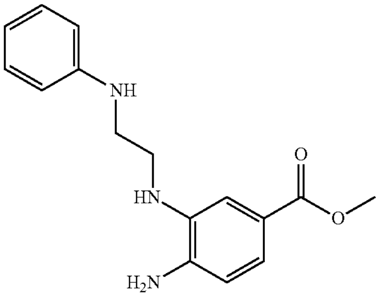

Methyl 4-amino-3-((2-(phenylamino)ethyl)amino)benzoate (I-190): Methyl 4-amino-3-((2-(phenylamino)ethyl)amino)benzoate was prepared following procedure Intermediate I-112 substituting methyl 3-fluoro-4-nitrobenzoate for methyl 2-fluoro-3-nitrobenzoate and N1-phenylethane-1,2-diamine for 2-methoxyethan-1-amine. ES/MS: 286.265 (M+H$^+$).

Intermediate I-191

I-191

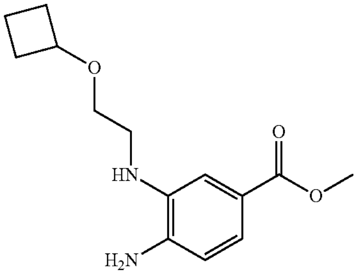

Methyl 4-amino-3-((2-cyclobutoxyethyl)amino)benzoate (I-191): Methyl 4-amino-3-((2-cyclobutoxyethyl)amino)benzoate was prepared following procedure Intermediate I-112 substituting methyl 3-fluoro-4-nitrobenzoate for methyl 2-fluoro-3-nitrobenzoate and 2-cyclobutoxyethan-1-amine for 2-methoxyethan-1-amine. ES/MS: 265.273 (M+H$^+$).

Intermediate I-192

I-192

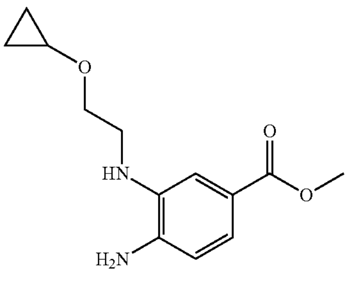

Methyl 4-amino-3-((2-cyclopropoxyethyl)amino)benzoate (I-192): Methyl 4-amino-3-((2-cyclopropoxyethyl)amino)benzoate was prepared following procedure Intermediate I-112 substituting methyl 3-fluoro-4-nitrobenzoate for methyl 2-fluoro-3-nitrobenzoate and 2-cyclopropoxyethan-1-amine for 2-methoxyethan-1-amine. ES/MS: 265.273 (M+H$^+$).

Intermediate I-193

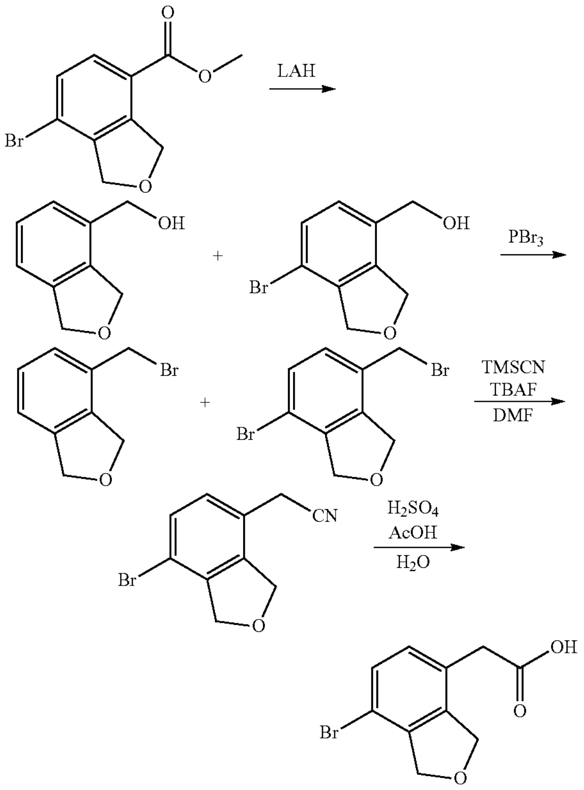

I-193

(7-Bromo-1,3-dihydroisobenzofuran-4-yl)methanol and (1,3-dihydroisobenzofuran-4-yl)methanol: To a solution of methyl 7-bromo-1,3-dihydroisobenzofuran-4-carboxylate (503 mg, 1.96 mmol) in MeTHF (20 mL) at 0° C. was added lithium aluminum hydride (1 M (THF), 2 mL, 2.0 mmol). The solution was stirred at 0° C. for 1.5 hours before $H_2O$ (0.1 mL) was slowly added. Aqueous sodium hydroxide (2 M, 0.2 mL) and $H_2O$ (0.3 mL) were added while stirring vigorously. To the resulting slurry was added $MgSO_4$ and the mixture was filtered through celite and concentrated to dryness. The resulting crude material was purified by $SiO_2$ column chromatography (eluent: EtOAc/hexanes) to provide a mixture of (7-bromo-1,3-dihydroisobenzofuran-4-yl) methanol (1H NMR (400 MHz, CDCl3) δ 7.40 (d, J=8.0 Hz, 1H), 7.15 (d, J=8.0 Hz, 1H), 5.28 (t, J=2.3 Hz, 2H), 5.10 (t, J=2.2 Hz, 2H), 4.64 (s, 2H)) and (1,3-dihydroisobenzofuran-4-yl)methanol.

4-Bromo-7-(bromomethyl)-1,3-dihydroisobenzofuran and 4-(bromomethyl)-1,3-dihydroisobenzofuran: To a mixture of (1,3-dihydroisobenzofuran-4-yl)methanol and (7-bromo-1,3-dihydroisobenzofuran-4-yl)methanol (352 mg, 1.54 mmol) in $CH_2Cl_2$ (10 mL) was added phosphorus tribromide (1 M ($CH_2Cl_2$), 1.5 mL, 1.5 mmol). The resulting solution was stirred at room temperature for 15 min, diluted with $CH_2Cl_2$, and washed with aqueous sodium bicarbonate. The aqueous layer was backextracted and the combine organic layers were dried over $MgSO_4$ and concentrated to dryness. The crude material was purified by $SiO_2$ column chromatography (eluent: EtOAc/hexanes) to provide 4-(bromomethyl)-1,3-dihydroisobenzofuran (1H NMR (400 MHz, CDCl3) δ 7.27 (d, J=4.8 Hz, 1H), 7.23 (t, J=7.5 Hz, 1H), 5.22 (d, J=2.3 Hz, 2H), 5.16 (d, J=2.3 Hz, 2H), 4.44 (s, 2H). (1H obscured by solvent)) and 4-bromo-7-(bromomethyl)-1,3-dihydroisobenzofuran (1H NMR (400 MHz, CDCl3) δ 7.40 (d, J=8.0 Hz, 1H), 7.14 (d, J=8.1 Hz, 1H), 5.29 (t, J=2.4 Hz, 2H), 5.14-5.10 (m, 2H), 4.37 (s, 2H)).

2-(7-Bromo-1,3-dihydroisobenzofuran-4-yl)acetonitrile: To a solution of 4-bromo-7-(bromomethyl)-1,3-dihydroisobenzofuran (100 mg, 0.34 mmol) in DMF (3 mL) was added trimethylsilyl cyanide (0.4 mL, 3.2 mmol) and tetrabutylammonium fluoride (1 M (THF), 3.4 mL, 3.4 mmol). The resulting solution was stirred at room temperature for 3 hours and diluted with EtOAc. The solution was then washed with aqueous lithium chloride (3×), dried over $MgSO_4$, and concentrated to dryness. The crude material was purified by $SiO_2$ column chromatography (eluent: EtOAc/hexanes) to provide 2-(7-bromo-1,3-dihydroisobenzofuran-4-yl)acetonitrile. 1H NMR (400 MHz, CDCl3) δ 7.45 (d, J=8.1 Hz, 1H), 7.17 (dd, J=8.0, 1.0 Hz, 1H), 5.26 (d, J=2.3 Hz, 2H), 5.15-5.10 (m, 2H), 3.60 (s, 2H).

2-(7-Bromo-1,3-dihydroisobenzofuran-4-yl)acetic acid (I-193): To a solution of 2-(7-bromo-1,3-dihydroisobenzofuran-4-yl)acetonitrile (68 mg, 0.29 mmol) in acetic acid (2.86 mL) and $H_2O$ (2.86 mL) was added sulfuric acid (2.3 mL, 42.8 mmol). The resulting solution was heated to 110° C. for 4.5 hours before cooling to room temperature. The mixture was diluted with $H_2O$ and extracted with $CH_2Cl_2$ (3 times). The combined organic layers were dried over $MgSO_4$ and concentrated to dryness to provide 2-(7-bromo-1,3-dihydroisobenzofuran-4-yl)acetic acid (I-193). ES/MS: 257.0 (M+H+).

Intermediate I-194

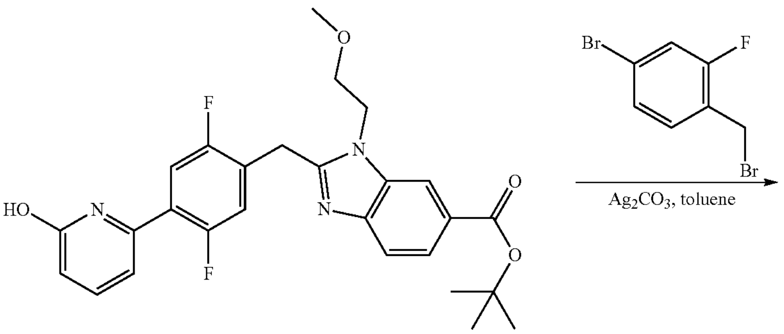

I-135

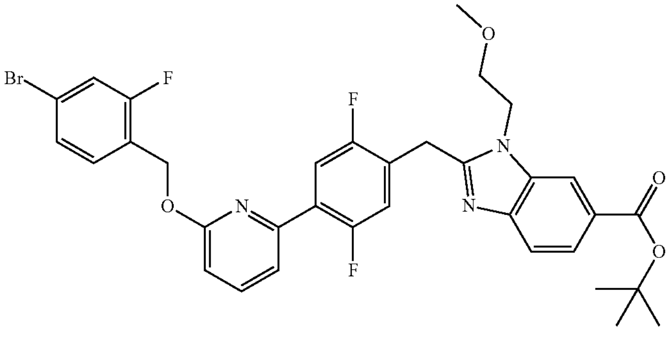

I-194

Tert-butyl 2-(4-(6-((4-bromo-2-fluorobenzyl)oxy)pyridin-2-yl)-2,5-difluorobenzyl)-1-(2-methoxyethyl)-1H-benzo[d]imidazole-6-carboxylate (I-194): To a solution of tert-butyl 2-[[2,5-difluoro-4-(6-hydroxy-2-pyridyl)phenyl]methyl]-3-(2-methoxyethyl)benzimidazole-5-carboxylate (500 mg, 1.0 mmol) in toluene (5 ml) was added 4-bromo-1-(bromomethyl)-2-fluoro-benzene (406 mg, 1.5 mmol) and Silver carbonate (835 mg, 3 mmol). The solution was stirred at 70° C. for 8 hours, cooled and filtered. The solution was concentrated and purified by purified by flash chromatography to obtain desired product. ES/MS: 683.2, 684.1 ($M+H^+$)

Intermediate I-195

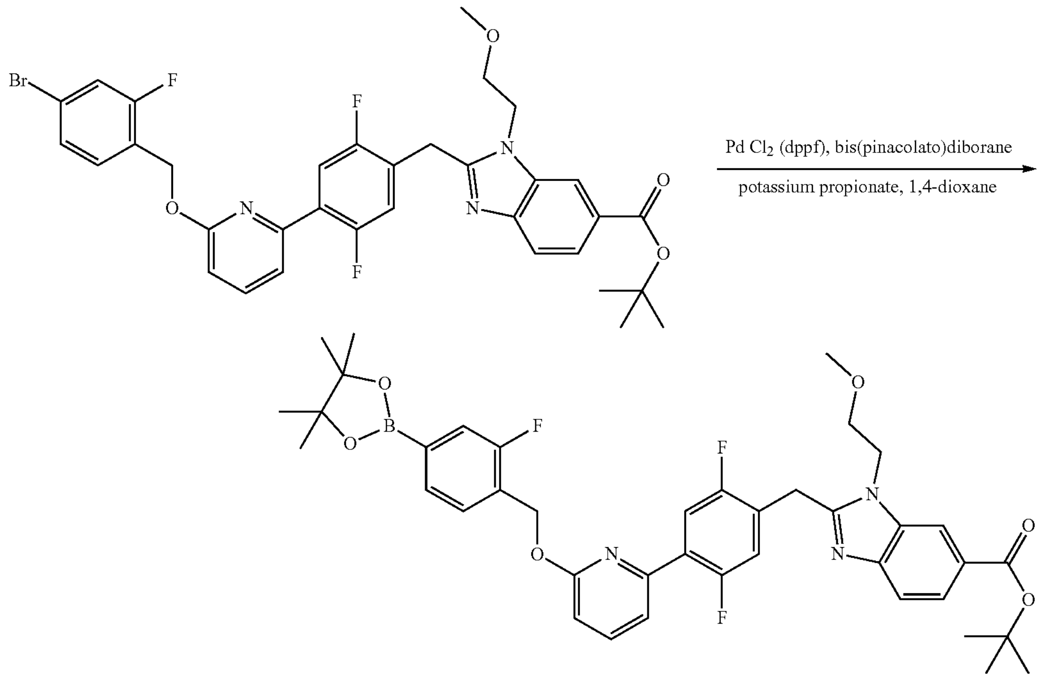

I-195

Tert-butyl 2-[[2,5-difluoro-4-[6-[[2-fluoro-4-(4,4,5,5-tetramethyl-1,3,2-dioxaborolan-2-yl)phenyl]methoxy]-2-pyridyl]phenyl]methyl]-3-(2-methoxyethyl)benzimidazole-5-carboxylate (I-195): A RB was charged with tert-butyl 2-[[4-[6-[(4-bromo-2-fluoro-phenyl)methoxy]-2-pyridyl]-2,5-difluoro-phenyl]methyl]-3-(2-methoxyethyl)benzimidazole-5-carboxylate (300 mg, 0.44 mmol), bis(pinacolato) diboron (134 mg, 0.53 mmol), potassium propionate (148 mg, 1.3 mmol), $PdCl_2(dppf)$ (33 mg, 0.44 mmol) and 1,4-dioxane (20 ml). The mixture was at 110° C. until complete (approx. 1 hour). The mixture was cooled, diluted with EtOAc, and filtered over celite. The solution was concentrated and purified by purified by flash chromatography to obtain desired product. ES/MS: 730.4 $(M+H^+)$ Intermediate I-196

I-196

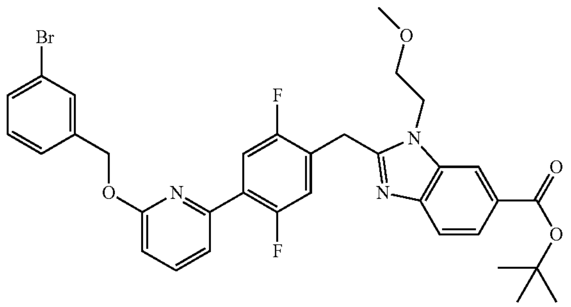

I-196 was prepared in an identical manner as described for I-194 substituting 4-bromo-1-(bromomethyl)-2-fluoro-benzene with 1-bromo-3-(bromomethyl)benzene. ES/MS: 665.1, 665.9 $(M+H^+)$ Intermediate I-197

I-197

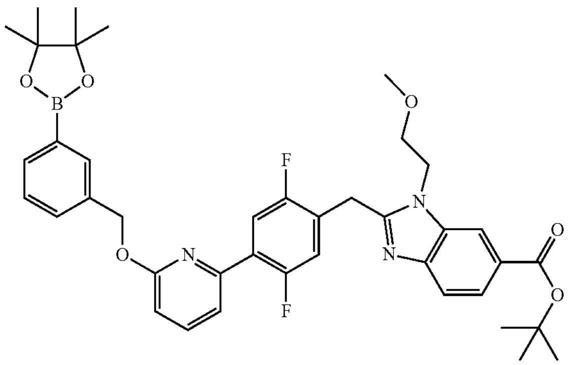

I-197 was prepared in an identical manner as described for I-195 substituting tert-butyl 2-[[4-[6-[(4-bromo-2-fluoro-phenyl)methoxy]-2-pyridyl]-2,5-difluoro-phenyl]methyl]-3-(2-methoxyethyl)benzimidazole-5-carboxylate with tert-butyl 2-[[4-[6-[(3-bromophenyl)methoxy]-2-pyridyl]-2,5-difluoro-phenyl]methyl]-3-(2-methoxyethyl)benzimidazole-5-carboxylate.

Intermediate I-198

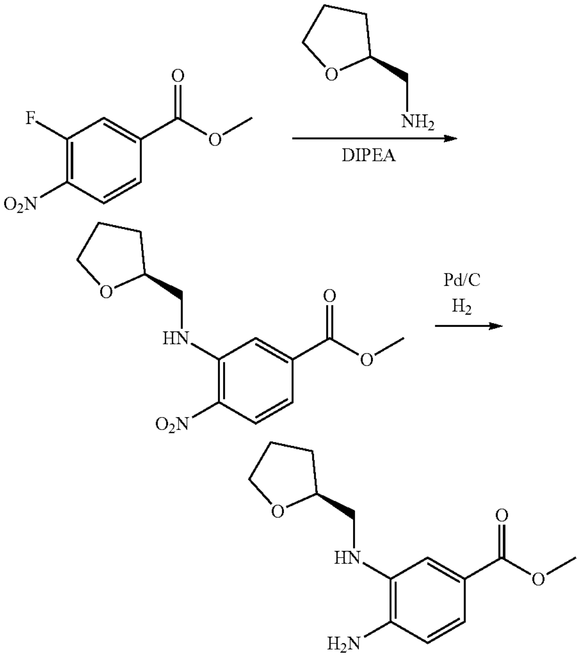

I-198

Methyl (S)-4-nitro-3-(((tetrahydrofuran-2-yl)methyl) amino)benzoate: To a solution of methyl 3-fluoro-4-nitrobenzoate (400 mg, 2.01 mmol) in DMF (4 mL) was added diisopropylethylamine (1.40 mL, 8.03 mmol) and [(2S)-tetrahydrofuran-2-yl]methanamine (214 mg, 2.11 mmol). The resulting solution was heated to 120° C. for 12 hrs. Upon completion the solvent was removed, the resulting residue was concentrated and carried forward without further purification. ES/MS: 281.2 ($M+H^+$)

Methyl (S)-4-amino-3-(((tetrahydrofuran-2-yl)methyl) amino)benzoate: (I-198): Methyl (S)-4-nitro-3-(((tetrahydrofuran-2-yl)methyl)amino)benzoate (563 mg, 2.01 mmol) was taken up in EtOAc (5 mL) and Palladium on Carbon (214 mg, 0.201 mmol, 10 wt %) was then added to the mixture at rt. After 3 hours, the mixture was filtered through celite washing with EtOAc and concentrated in vacuo. The product I-198 was used without further purification. ES/MS: 251.2 ($M+H^+$)

Intermediate I-199

I-199

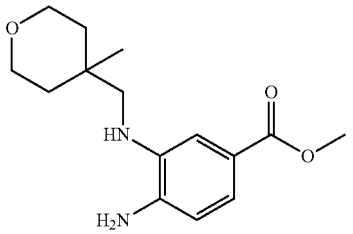

Methyl 4-amino-3-(((4-methyltetrahydro-2H-pyran-4-yl) methyl)amino)benzoate (I-199): Methyl 4-amino-3-(((4-methyltetrahydro-2H-pyran-4-yl)methyl)amino)benzoate was prepared following procedure Intermediate I-198 substituting (4-methyltetrahydro-2H-pyran-4-yl)methanamine for [(2S)-tetrahydrofuran-2-yl]methanamine. ES/MS: 279.2 ($M+H^+$).

Intermediate I-200

I-200

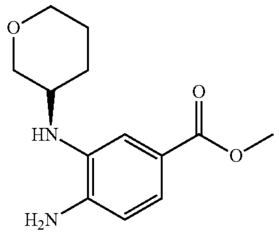

Methyl (S)-4-amino-3-((tetrahydro-2H-pyran-3-yl) amino)benzoate (I-200): Methyl (S)-4-amino-3-((tetrahydro-2H-pyran-3-yl)amino)benzoate was prepared following procedure Intermediate I-198 substituting (S)-tetrahydro-2H-pyran-3-amine for [(2S)-tetrahydrofuran-2-yl]methanamine. ES/MS: 251.2 (M+H+).

Intermediate I-201

I-201

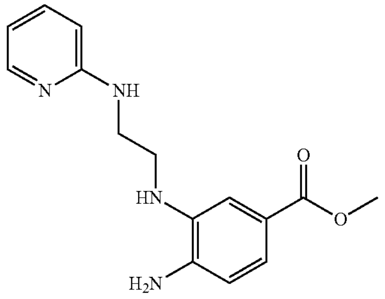

Methyl 4-amino-3-((2-(pyridin-2-ylamino)ethyl)amino) benzoate (I-201): Methyl 4-amino-3-((2-(pyridin-2-ylamino)ethyl)amino)benzoate was prepared following procedure Intermediate I-198 substituting N1-(pyridin-2-yl) ethane-1,2-diamine for [(2S)-tetrahydrofuran-2-yl] methanamine. ES/MS: 287.2 ($M+H^+$).

Intermediate I-202

I-202

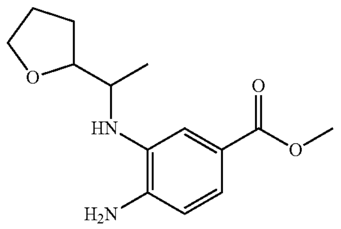

Methyl 4-amino-3-((1-(tetrahydrofuran-2-yl)ethyl) amino)benzoate (I-202): Methyl 4-amino-3-((1-(tetrahydrofuran-2-yl)ethyl)amino)benzoate was prepared following procedure Intermediate I-198 substituting 1-(tetrahydrofuran-2-yl)ethan-1-amine for [(2S)-tetrahydrofuran-2-yl] methanamine. ES/MS: 267.2 ($M+H^+$).

Intermediate I-203

I-203

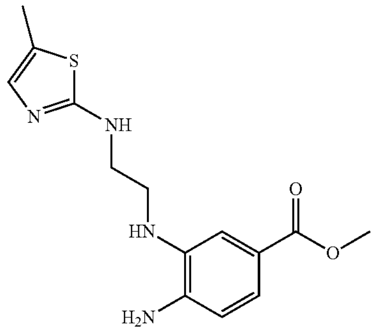

Methyl 4-amino-3-((2-((5-methylthiazol-2-yl)amino) ethyl)amino)benzoate (I-203): Methyl 4-amino-3-((2-((5-methylthiazol-2-yl)amino)ethyl)amino)benzoate was prepared following procedure Intermediate I-198 substituting 2-(5-methylthiazol-2-yl)ethan-1-amine for [(2S)-tetrahydrofuran-2-yl]methanamine. ES/MS: 307.2 (M+H$^+$).

I-204

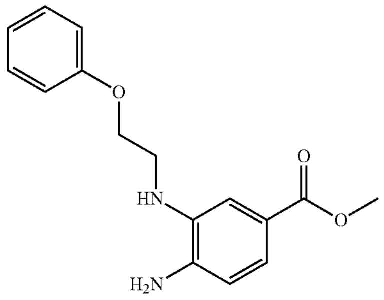

Methyl 4-amino-3-((2-phenoxyethyl)amino)benzoate (I-204): Methyl 4-amino-3-((2-phenoxyethyl)amino)benzoate was prepared following procedure Intermediate I-198 substituting 2-phenoxyethan-1-amine for [(2S)-tetrahydrofuran-2-yl]methanamine. ES/MS: 287.2 (M+H$^+$).

Intermediate I-205

I-205

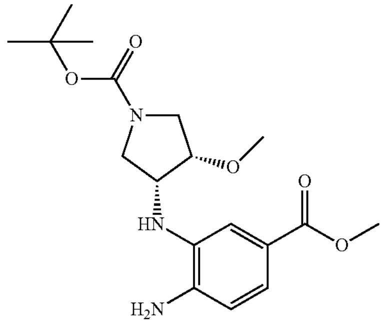

tert-butyl (3R,4S)-3-((2-amino-5-(methoxycarbonyl)phenyl)amino)-4-methoxypyrrolidine-1-carboxylate (I-205): tert-butyl (3R,4S)-3-((2-amino-5-(methoxycarbonyl)phenyl)amino)-4-methoxypyrrolidine-1-carboxylate was prepared following procedure Intermediate I-198 substituting tert-butyl (3R,4S)-3-amino-4-methoxypyrrolidine-1-carboxylate for [(2S)-tetrahydrofuran-2-yl]methanamine. ES/MS: 366.2 (M+H$^+$).

Intermediate I-206

I-206

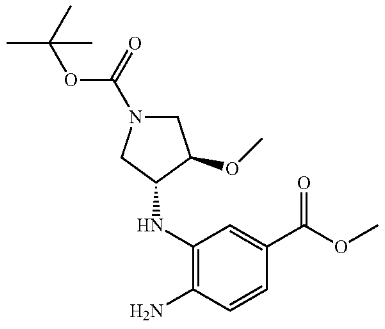

Tert-butyl (3R,4R)-3-((2-amino-5-(methoxycarbonyl) phenyl)amino)-4-methoxypyrrolidine-1-carboxylate (I-206): tert-butyl (3R,4R)-3-((2-amino-5-(methoxycarbonyl)phenyl)amino)-4-methoxypyrrolidine-1-carboxylate was prepared following procedure Intermediate I-198 substituting tert-butyl (3R,4R)-3-amino-4-methoxypyrrolidine-1-carboxylate for [(2S)-tetrahydrofuran-2-yl]methanamine. ES/MS: 366.2 (M+H$^+$).

Intermediate I-207

I-207

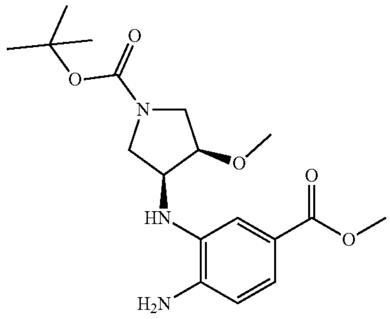

Tert-butyl (3S,4R)-3-((2-amino-5-(methoxycarbonyl) phenyl)amino)-4-methoxypyrrolidine-1-carboxylate (I-207): tert-butyl (3S,4R)-3-((2-amino-5-(methoxycarbonyl)phenyl)amino)-4-methoxypyrrolidine-1-carboxylate was prepared following procedure Intermediate I-198 substituting tert-butyl (3S,4R)-3-amino-4-methoxypyrrolidine-1-carboxylate for [(2S)-tetrahydrofuran-2-yl]methanamine. ES/MS: 366.2 (M+H$^+$).

Intermediate I-208

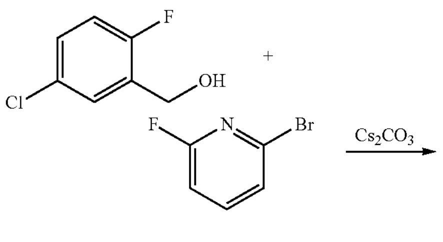

-continued

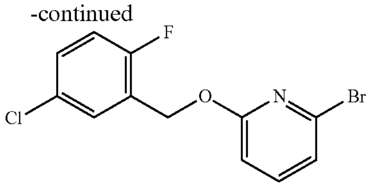

I-208

2-bromo-6-[(5-chloro-2-fluoro-phenyl)methoxy]pyridine (I-208): To a solution of 2-bromo-6-fluoro-pyridine (137 mg, 0.778 mmol) in ACN (4 mL) was added cesium carbonate (507 mg, 1.56 mmol) and (5-chloro-2-fluoro-phenyl) methanol (125 mg, 0.778 mmol). The resulting solution was heated to 100° C. for 12 hrs. Upon completion, the reaction mixture was filtered, concentrated, and purified by flash chromatography. (25-100% EtOAc/Hex) ES/MS: 317.2 $(M+H^+)$ Intermediate I-209

I-209

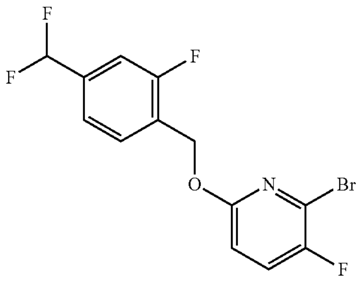

2-bromo-6-((4-(difluoromethyl)-2-fluorobenzyl)oxy)-3-fluoropyridine (I-209): 2-bromo-6-((4-(difluoromethyl)-2-fluorobenzyl)oxy)-3-fluoropyridine was prepared following procedure Intermediate I-208 substituting 2-bromo-3,6-difluoropyridine for 2-bromo-6-fluoropyridine and (4-(difluoromethyl)-2-fluorophenyl)methanol for (5-chloro-2-fluorophenyl)methanol. $^1H$ NMR (400 MHz, Acetonitrile-d3) δ 7.72-7.65 (m, 1H), 7.59 (dd, J=8.8, 7.4 Hz, 1H), 7.45-7.35 (m, 2H), 6.96 (s, 0H), 6.87 (dd, J=8.8, 2.9 Hz, 1H), 6.82 (s, 0H), 6.68 (s, 0H), 5.43 (t, J=1.0 Hz, 2H).

Intermediate I-210

I-210

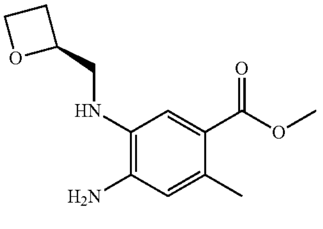

Methyl (S)-4-amino-2-methyl-5-((oxetan-2-ylmethyl) amino)benzoate (I-210): Methyl (S)-4-amino-2-methyl-5-((oxetan-2-ylmethyl)amino)benzoate was prepared following procedure Intermediate I-198 substituting (S)-oxetan-2-ylmethanamine for [(2S)-tetrahydrofuran-2-yl]methanamine and methyl 5-fluoro-2-methyl-4-nitrobenzoate for methyl 3-fluoro-4-nitrobenzoate. ES/MS: 281.2 $(M+H^+)$.

B. Compound Examples

Example 1. 2-(4-(6-((4-Cyano-2-fluorobenzyl)oxy) pyridin-2-yl)benzyl)-1-(2-methoxyethyl)-1H-benzo [d]imidazole-6-carboxylic acid Procedure 1

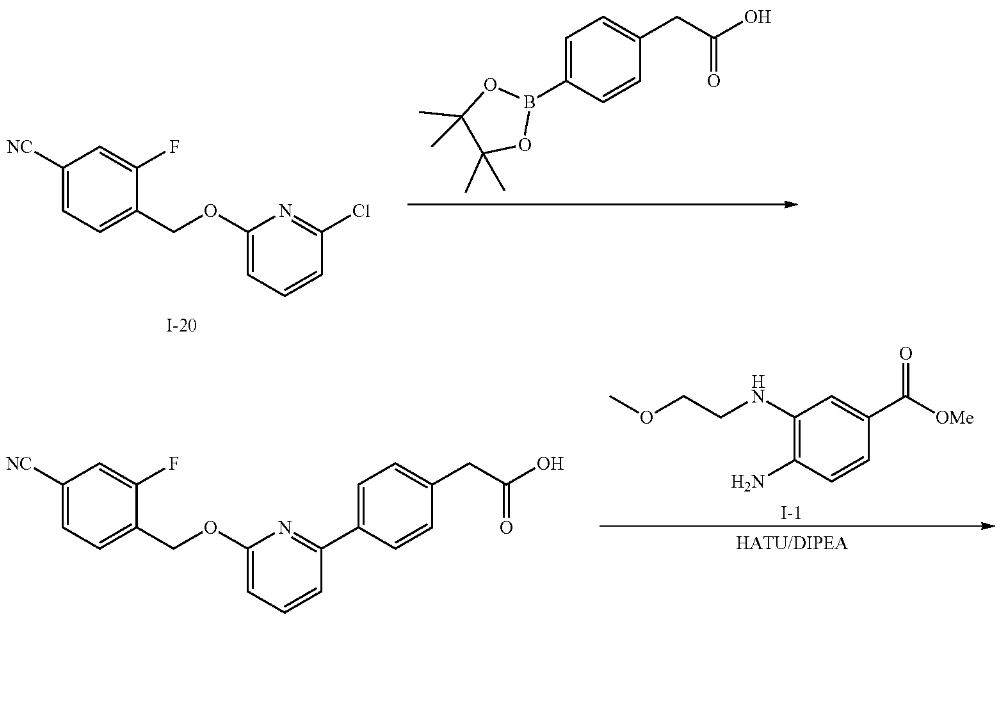

-continued

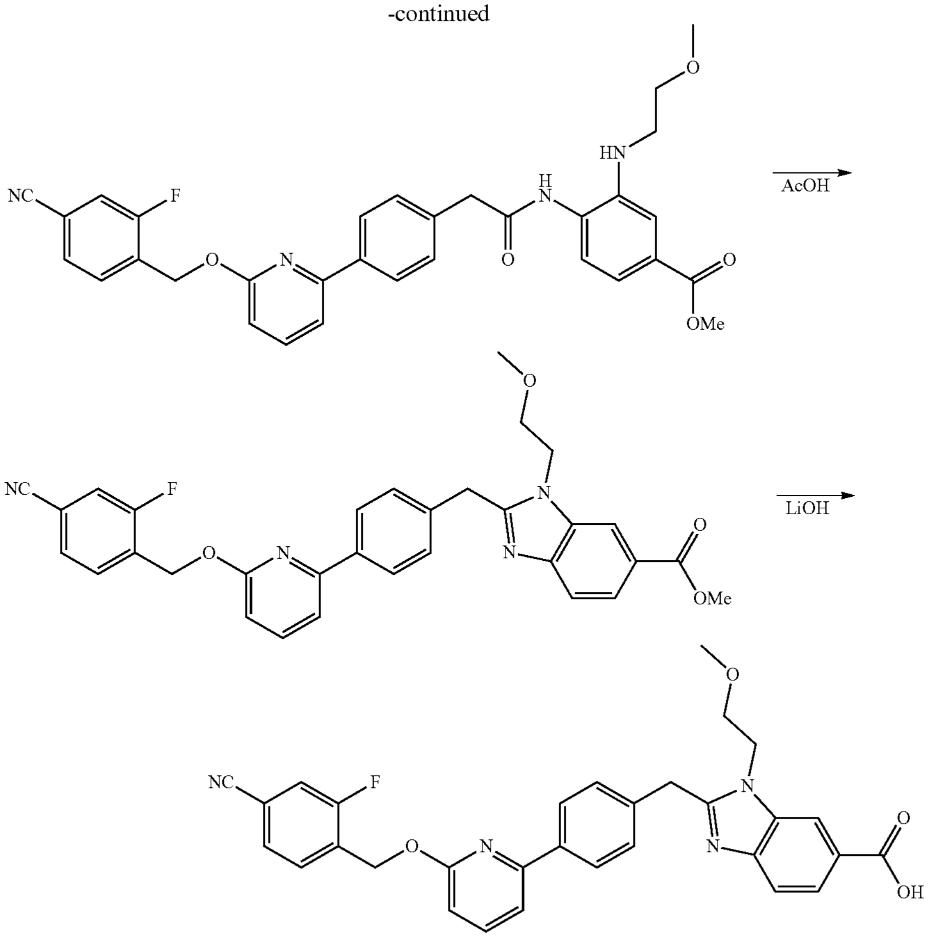

2-(4-(6-((4-Cyano-2-fluorobenzyl)oxy)pyridin-2-yl)phenyl)acetic acid: To a solution of 4-(((6-chloropyridin-2-yl)oxy)methyl)-3-fluorobenzonitrile (I-20) (100 mg, 0.38 mmol) in dioxane (1 mL) was added XPhos Pd G2 (30 mg, 0.04 mmol), sodium carbonate (24 mg, 0.38 mmol) and 2-(4-(4,4,5,5-tetramethyl-1,3,2-dioxaborolan-2-yl)phenyl) acetic acid (100 mg, 0.38 mmol). The resulting solution was degassed by bubbling argon for 5 minutes, sealed, and heated for 2 hrs at 100° C. Upon completion the reaction contents were poured into water (5 mL), and extracted with EtOAc (2×10 mL). The combined organic extracts were washed with brine (5 mL), dried over $MgSO_4$, and purified by silica gel chromatography (eluent: EtOAc/hexanes): ES/MS: 363.18 ($M+H^+$).

Methyl 4-(2-(4-(6-((4-cyano-2-fluorobenzyl)oxy)pyridin-2-yl)phenyl)acetamido)-3-((2-methoxyethyl)amino)benzoate: To a solution of 2-(4-(6-((4-Cyano-2-fluorobenzyl)oxy)pyridin-2-yl)phenyl)acetic acid (100 mg, 0.28 mmol) in DMF (1 mL) was added methyl 4-amino-3-(2-methoxyethylamino)benzoate (Intermediate I-1, 74 mg, 0.33 mmol), o-(7-Azabenzotriazol-1-yl)-N,N,N',N'-tetramethyluronium hexafluorophosphate (120 mg, 0.32 mmol), and DIPEA (0.19 mL, 1.1 mmol). The resulting solution was stirred at room temperature for 2 hrs after which the reaction contents were poured into water (5 mL) and extracted with EtOAc (2×15 mL). The combined organic extracts were washed with brine (5 mL), dried over $MgSO_4$, and purified by silica gel chromatography (eluent: EtOAc/hexanes) to give desired product: ES/MS: 569.56 ($M+H^+$).

Methyl 2-(4-(6-((4-cyano-2-fluorobenzyl)oxy)pyridin-2-yl)benzyl)-1-(2-methoxyethyl)-1H-benzo[d]imidazole-6-carboxylate: Methyl 4-(2-(4-(6-((4-cyano-2-fluorobenzyl)oxy)pyridin-2-yl)phenyl)acetamido)-3-((2-methoxyethyl)amino)benzoate (50 mg, 0.088 mmol) was dissolved in acetic acid (1 mL) and heated to 60° C. for 3 hrs. The reaction mixture was concentrated directly and purified by silica gel chromatography (eluent: EtOAc/hexanes): ES/MS: 551.37 ($M+H^+$).

2-(4-(6-((4-Cyano-2-fluorobenzyl)oxy)pyridin-2-yl)benzyl)-1-(2-methoxyethyl)-1H-benzo[d]imidazole-6-carboxylic acid (Example 1): Methyl 2-(4-(6-((4-cyano-2-fluorobenzyl)oxy)pyridin-2-yl)benzyl)-1-(2-methoxyethyl)-1H-benzo[d]imidazole-6-carboxylate (40 mg, 0.073 mmol) was dissolved in acetonitrile (1 mL) after which LiOH (3.5 mg, 0.145 mmol) as a solution in water (0.25 mL) was added and the resulting mixture stirred at 60° C. for 1 hr. The mixture was adjusted to pH 2 using 1.0 M citric acid solution and extracted with EtOAc (2×10 mL). The combined organics were then washed with brine (5 mL), dried over $MgSO_4$, filtered, concentrated and purified by RP-HPLC (eluent: water/MeCN 0.1% TFA) to yield the product (Example 1) as a trifluoroacetate salt: ES/MS: 537.58 ($M+H^+$); $^1H$ NMR (400 MHz, Methanol-d4) δ 8.55 (dd, J=1.5, 0.7 Hz, 1H), 8.22 (dd, J=8.6, 1.4 Hz, 1H), 8.15-7.96 (m, 2H), 7.87-7.66 (m, 3H), 7.63-7.39 (m, 6H), 6.85 (d, J=8.2 Hz, 1H), 5.62 (s, 2H), 4.82-4.64 (m, 4H), 3.77 (dd, J=5.4, 4.4 Hz, 2H), 3.33-3.28 (m, 3H).

Examples 2-19, 200-201, 203-207, 209-210, 218-225, 231, 242, 263-264, 269-273, 276-277, 279, 281, 283-285, 287-288, 293-297, 299-303, 305-308, 310-313, 315-316, 323-327, 331, 343, 351, 353, 355, 359-361, 365-366, 370-371, 375-377, 379-382, 384-386, 390, 392, 402, 404, 407, 452, 454-455, 475, 484, 486, 492, 519-521, 523-525, 527-535, 550-551, 558, 561, 566-567, and 583-585, and 606-653. Compounds Prepared Using Procedure 1

Other compounds of the present disclosure prepared using the general route described in Procedure 1 include the following Examples.

| Example | Structure/Name/Characterization |
|---|---|
| 2 | 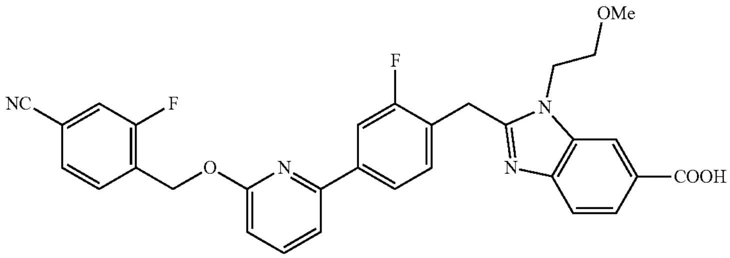 [SMILES: COCCn1c(Cc2ccc(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2-fluorobenzyl)-1-(2-methoxyethyl)-1H-benzo[d]imidazole-6-carboxylic acid: ES/MS 555.5; $^1$H NMR (400 MHz, DMSO-$d_6$) δ 8.20 (d, J = 1.5 Hz, 1H), 7.97-7.68 (m, 8H), 7.61 (dd, J = 24.8, 8.0 Hz, 2H), 7.41 (t, J = 7.9 Hz, 1H), 6.91 (d, J = 8.2 Hz, 1H), 5.60 (s, 2H), 4.82 (t, J = 2.6 Hz, 1H), 4.56 (t, J = 5.1 Hz, 2H), 4.43 (s, 2H), 3.70-3.27 (m, 4H). |
| 3 | 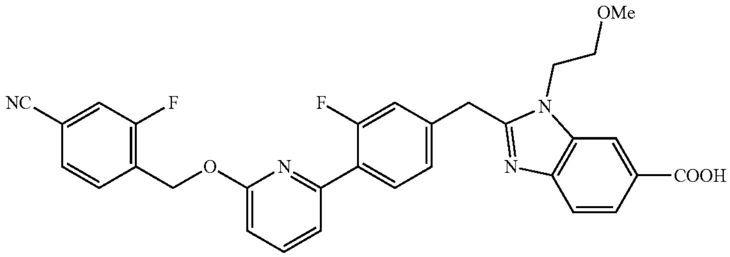 [SMILES: COCCn1c(Cc2ccc(-c3cccc(OCc4ccc(C#N)cc4F)n3)c(F)c2)nc2ccc(C(=O)O)cc21] 2-(4-(6-((4-cyano-2-fluorobenzyl)oxy)pyridin-2-yl)-3-fluorobenzyl)-1-(2-methoxyethyl)-1H-benzo[d]imidazole-6-carboxylic acid: ES/MS 555.4; $^1$H NMR (400 MHz, $CD_3OD$) δ 8.59-8.49 (m, 1H), 8.21 (dd, J = 8.6, 1.4 Hz, 1H), 8.01 (t, J = 8.2 Hz, 1H), 7.88-7.74 (m, 2H), 7.70 (t, J = 7.5 Hz, 1H), 7.66-7.43 (m, 3H), 7.34-7.20 (m, 2H), 6.97-6.85 (m, 1H), 5.60 (s, 2H), 4.81-4.67 (m, 4H), 3.79 (t, J = 4.9 Hz, 2H), 3.31 (dd, J = 3.3, 1.6 Hz, 4H). |
| 4 | 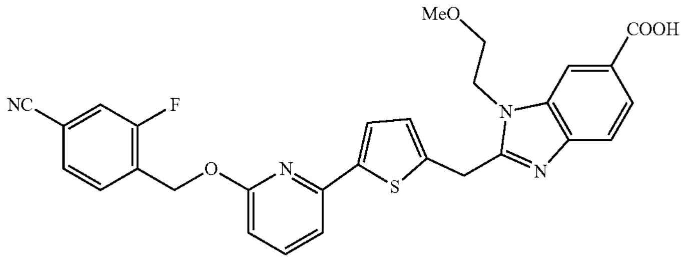 [SMILES: COCCn1c(Cc2ccc(-c3cccc(OCc4ccc(C#N)cc4F)n3)s2)nc2ccc(C(=O)O)cc21] 2-((5-(6-((4-cyano-2-fluorobenzyl)oxy)pyridin-2-yl)thiophen-2-yl)methyl)-1-(2-methoxyethyl)-1H-benzo[d]imidazole-6-carboxylic acid: ES/MS 543.4; $^1$H NMR (400 MHz, $CD_3OD$) δ 8.44 (s, 1H), 8.14 (dd, J = 8.5, 1.5 Hz, 1H), 7.77 (d, J = 8.5 Hz, 1H), 7.68 (q, J = 7.7 Hz, 2H), 7.55 (d, J = 3.8 Hz, 1H), 7.50-7.29 (m, 3H), 7.06 (d, J = 3.7 Hz, 1H), 6.74 (d, J = 8.2 Hz, 1H), 5.52 (s, 2H), 4.89 (t, J = 2.6 Hz, 1H), 4.80-4.61 (m, 1H), 4.15 (ddd, J = 12.3, 8.9, 3.7 Hz, 1H), 3.76-3.59 (m, 2H), 3.56-3.44 (m, 2H), 3.27 (s, 3H). |

-continued

| Example | Structure/Name/Characterization |
|---|---|
| 5 | 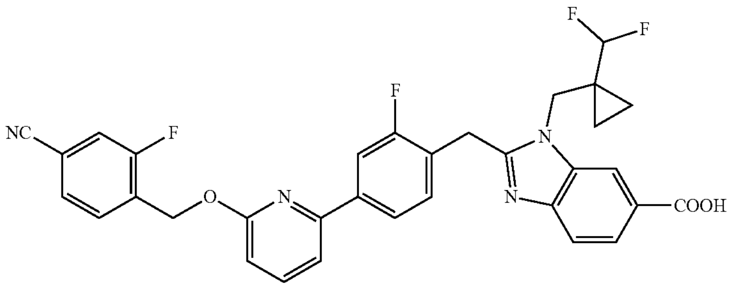 [SMILES: N#Cc1ccc(COc2cccc(-c3ccc(Cc4nc5ccc(C(=O)O)cc5n4CC4(C(F)F)CC4)c(F)c3)n2)c(F)c1]<br>2-(4-(6-((4-cyano-2-fluorobenzyl)oxy)pyridin-2-yl)-2-fluorobenzyl)-1-((1-(difluoromethyl)cyclopropyl)methyl)-1H-benzo[d]imidazole-6-carboxylic acid: ES/MS 601.3; $^1$H NMR (400 MHz, DMSO-$d_6$) δ 8.27 (d, J = 1.5 Hz, 1H), 7.97-7.78 (m, 5H), 7.78-7.56 (m, 4H), 7.44 (t, J = 7.9 Hz, 1H), 6.91 (d, J = 8.2 Hz, 1H), 5.84 (d, J = 55.4 Hz, 1H), 5.61 (d, J = 12.3 Hz, 2H), 4.71 (s, 2H), 4.46 (s, 2H), 0.86 (dt, J = 24.6, 5.9 Hz, 4H). |
| 6 | 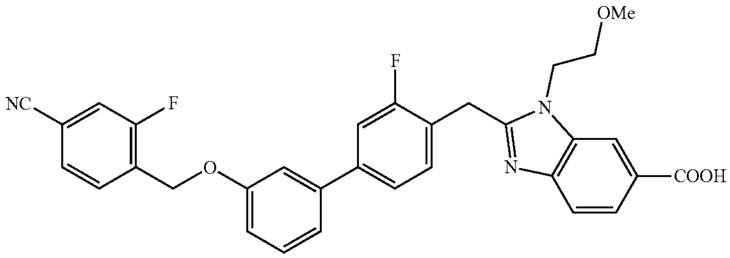 [SMILES: COCCn1c(Cc2ccc(-c3cccc(OCc4ccc(C#N)cc4F)c3)cc2F)nc2ccc(C(=O)O)cc21]<br>2-((3'-((4-cyano-2-fluorobenzyl)oxy)-3-fluoro-[1,1'-biphenyl]-4-yl)methyl)-1-(2-methoxyethyl)-1H-benzo[d]imidazole-6-carboxylic acid: ES/MS 554.6; $^1$H NMR (400 MHz, $CD_3OD$) δ 8.61-8.49 (m, 1H), 8.22 (dd, J = 8.6, 1.4 Hz, 1H), 7.77 (t, J = 7.6 Hz, 2H), 7.61 (dt, J = 9.0, 1.6 Hz, 2H), 7.56-7.46 (m, 3H), 7.41 (t, J = 8.2 Hz, 1H), 7.28 (dp, J = 3.9, 1.5 Hz, 2H), 7.07 (ddd, J = 8.2, 2.5, 1.0 Hz, 1H), 5.30 (s, 2H), 4.78 (d, J = 18.7 Hz, 4H), 3.86-3.73 (m, 3H), 3.35-3.30 (m, 3H). |
| 7 | 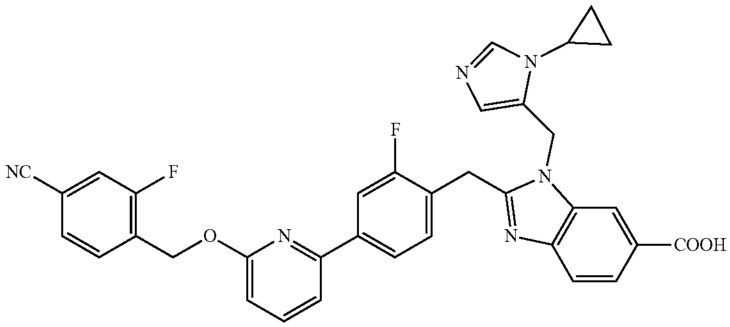<br>2-(4-(6-((4-cyano-2-fluorobenzyl)oxy)pyridin-2-yl)-2-fluorobenzyl)-1-((1-cyclopropyl-1H-imidazol-5-yl)methyl)-1H-benzo[d]imidazole-6-carboxylic acid: ES/MS 617.3; $^1$H NMR (400 MHz, $CD_3OD$) δ 8.95 (d, J = 1.5 Hz, 1H), 8.27 (d, J = 1.4 Hz, 1H), 8.07 (dd, J = 8.5, 1.5 Hz, 1H), 7.83-7.66 (m, 5H), 7.64-7.53 (m, 2H), 7.49 (d, J = 7.5 Hz, 1H), 7.39 (t, J = 8.0 Hz, 1H), 6.95-6.82 (m, 2H), 5.92 (d, J = 1.3 Hz, 2H), 5.61 (s, 2H), 4.56 (s, 2H), 3.70-3.59 (m, 1H), 1.23 (d, J = 5.7 Hz, 4H). |

-continued

| Example | Structure/Name/Characterization |
|---|---|
| 8 | 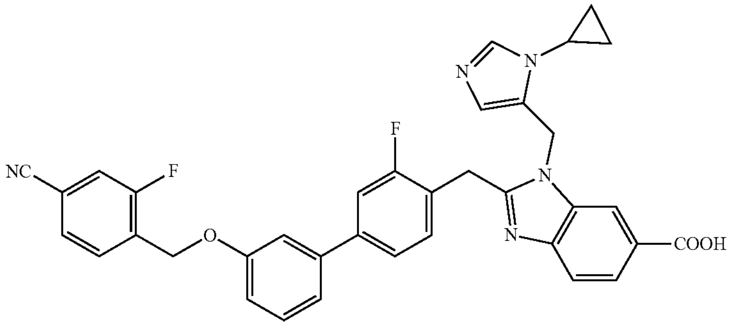 [SMILES: N#Cc1ccc(COc2cccc(-c3ccc(Cc4nc5ccc(C(=O)O)cc5n4Cc4cncn4C4CC4)c(F)c3)c2)c(F)c1] 2-((3'-((4-cyano-2-fluorobenzyl)oxy)-3-fluoro-[1,1'-biphenyl]-4-yl)methyl)-1-((1-cyclopropyl-1H-imidazol-5-yl)methyl)-1H-benzo[d]imidazole-6-carboxylic acid: ES/MS 616.5; $^{1}$H NMR (400 MHz, $CD_3OD$) δ 9.02-8.88 (m, 1H), 8.26 (d, J = 1.4 Hz, 1H), 8.07 (dd, J = 8.5, 1.5 Hz, 1H), 7.77 (t, J = 7.8 Hz, 2H), 7.66-7.54 (m, 2H), 7.47-7.28 (m, 5H), 7.27-7.13 (m, 2H), 7.13-6.97 (m, 1H), 6.86 (d, J = 1.5 Hz, 1H), 5.91 (d, J = 1.3 Hz, 2H), 5.28 (s, 2H), 4.55 (s, 2H), 3.63 (p, J = 5.8 Hz, 1H), 1.23 (d, J = 4.3 Hz, 4H). |
| 9 | 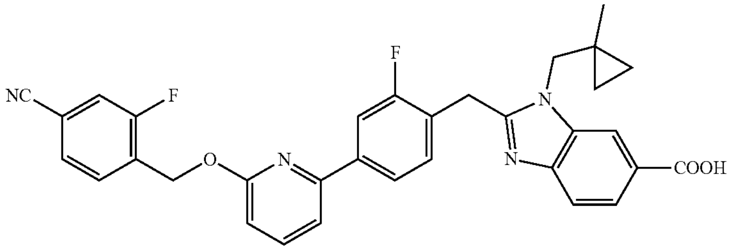 [SMILES: CC1(Cn2c(Cc3ccc(-c4cccc(OCc5ccc(C#N)cc5F)n4)cc3F)nc3ccc(C(=O)O)cc32)CC1] 2-(4-(6-((4-cyano-2-fluorobenzyl)oxy)pyridin-2-yl)-2-fluorobenzyl)-1-((1-methylcyclopropyl)methyl)-1H-benzo[d]imidazole-6-carboxylic acid: ES/MS 565.3; $^{1}$H NMR (400 MHz, $CD_3OD$) δ 8.63 (d, J = 1.3 Hz, 1H), 8.25 (dd, J = 8.6, 1.4 Hz, 1H), 7.98-7.87 (m, 2H), 7.86-7.77 (m, 2H), 7.74 (t, J = 7.6 Hz, 1H), 7.64-7.51 (m, 4H), 6.93 (d, J = 8.1 Hz, 1H), 5.66 (s, 2H), 4.79 (s, 2H), 4.62 (s, 2H), 1.06 (s, 3H), 0.87-0.84 (m, 2H), 0.70-0.55 (m, 2H). |
| 10 | 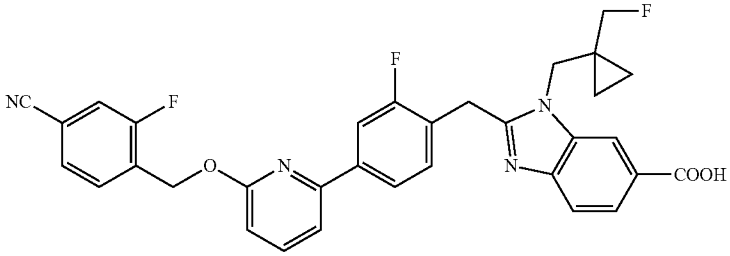 [SMILES: N#Cc1ccc(COc2cccc(-c3ccc(Cc4nc5ccc(C(=O)O)cc5n4CC4(CF)CC4)c(F)c3)n2)c(F)c1] 2-(4-(6-((4-cyano-2-fluorobenzyl)oxy)pyridin-2-yl)-2-fluorobenzyl)-1-((1-(fluoromethyl)cyclopropyl)methyl)-1H-benzo[d]imidazole-6-carboxylic acid: ES/MS 583.4; $^{1}$H NMR (400 MHz, $CD_3OD$) δ 8.58 (d, J = 1.1 Hz, 1H), 8.20 (dd, J = 8.6, 1.4 Hz, 1H), 7.96-7.87 (m, 2H), 7.83 (dd, J = 8.2, 7.5 Hz, 1H), 7.79-7.70 (m, 2H), 7.65-7.55 (m, 3H), 7.50 (t, J = 7.9 Hz, 1H), 6.96-6.89 (m, 1H), 5.66 (s, 2H), 4.75 (s, 2H), 4.74 (s, 2H), 4.24 (d, J = 48.7 Hz, 2H), 1.07-0.96 (m, 2H), 0.90-0.87 (m, 2H). |
| 11 | 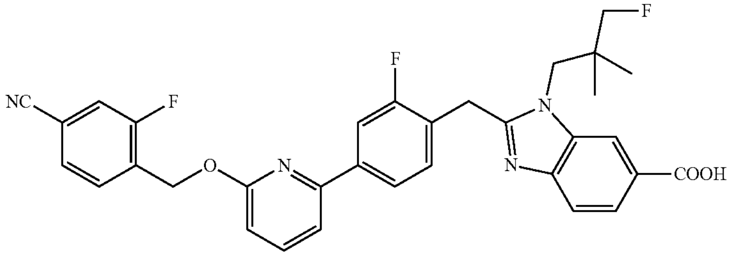 [SMILES: CC(C)(CF)Cn1c(Cc2ccc(-c3cccc(OCc4ccc(C#N)cc4F)n3)cc2F)nc2ccc(C(=O)O)cc21] |

-continued

| Example | Structure/Name/Characterization |
|---|---|
| | 2-(4-(6-((4-cyano-2-fluorobenzyl)oxy)pyridin-2-yl)-2-fluorobenzyl)-1-(3-fluoro-2,2-dimethylpropyl)-1H-benzo[d]imidazole-6-carboxylic acid: ES/MS 585.6; $^1$H NMR (400 MHz, $CD_3OD$) δ 8.61 (d, J = 1.1 Hz, 1H), 8.21 (dd, J = 8.6, 1.4 Hz, 1H), 7.97-7.86 (m, 2H), 7.83 (dd, J = 8.2, 7.5 Hz, 1H), 7.79-7.71 (m, 2H), 7.66-7.50 (m, 4H), 6.93 (d, J = 8.1 Hz, 1H), 5.66 (s, 2H), 4.75 (s, 2H), 4.63 (s, 2H), 4.35 (d, J = 47.6 Hz, 2H), 1.20 (d, J = 1.9 Hz, 6H). |
| 12 | 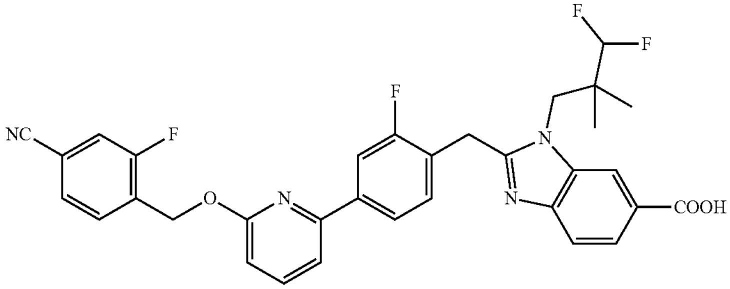 [SMILES: CC(C)(Cn1c(Cc2ccc(-c3cccc(OCc4ccc(C#N)cc4F)n3)cc2F)nc2ccc(C(=O)O)cc21)C(F)F] 2-(4-(6-((4-cyano-2-fluorobenzyl)oxy)pyridin-2-yl)-2-fluorobenzyl)-1-(3,3-difluoro-2,2-dimethylpropyl)-1H-benzo[d]imidazole-6-carboxylic acid: ES/MS 603.6; $^1$H NMR (400 MHz, $CD_3OD$) δ 8.55 (d, J = 1.2 Hz, 1H), 8.18 (dd, J = 8.6, 1.4 Hz, 1H), 7.95-7.85 (m, 2H), 7.82 (dd, J = 8.2, 7.5 Hz, 1H), 7.77-7.71 (m, 2H), 7.64-7.55 (m, 3H), 7.52 (t, J = 7.9 Hz, 1H), 6.92 (dd, J = 8.3, 0.6 Hz, 1H), 5.95 (t, J = 55.8 Hz, 1H), 5.66 (s, 2H), 4.71 (d, J = 6.5 Hz, 4H), 1.26 (d, J = 1.3 Hz, 6H). |
| 13 | 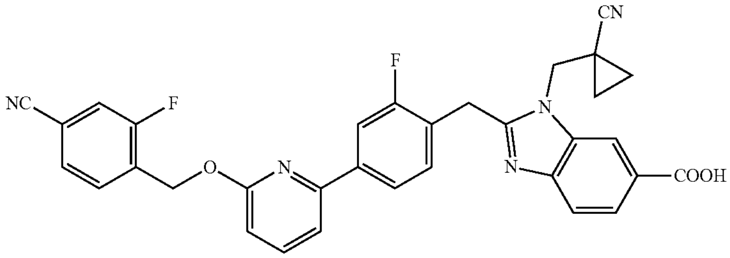 [SMILES: N#Cc1ccc(COc2cccc(-c3ccc(Cc4nc5ccc(C(=O)O)cc5n4CC4(C#N)CC4)c(F)c3)n2)c(F)c1] 2-(4-(6-((4-cyano-2-fluorobenzyl)oxy)pyridin-2-yl)-2-fluorobenzyl)-1-((1-cyanocyclopropyl)methyl)-1H-benzo[d]imidazole-6-carboxylic acid: ES/MS 576.5; $^1$H NMR (400 MHz, $CD_3OD$) δ 8.63 (dd, J = 1.3, 0.6 Hz, 1H), 8.23 (dd, J = 8.6, 1.4 Hz, 1H), 7.97-7.87 (m, 2H), 7.86-7.78 (m, 2H), 7.74 (t, J = 7.6 Hz, 1H), 7.66-7.50 (m, 4H), 6.92 (d, J = 8.2 Hz, 1H), 5.66 (s, 2H), 4.84 (s, 2H), 1.59-1.45 (m, 4H). |
| 14 | 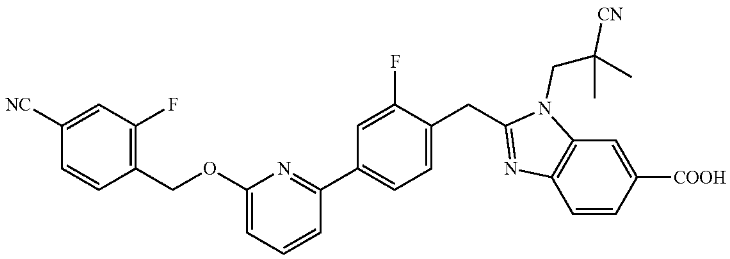 [SMILES: CC(C)(C#N)Cn1c(Cc2ccc(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2-fluorobenzyl)-1-(2-cyano-2-methylpropyl)-1H-benzo[d]imidazole-6-carboxylic acid: ES/MS 578.4; $^1$H NMR (400 MHz, $CD_3OD$) δ 8.65 (d, J = 1.4 Hz, 1H), 8.18 (dd, J = 8.6, 1.4 Hz, 1H), 7.94-7.85 (m, 2H), 7.82 (dd, J = 8.2, 7.5 Hz, 1H), 7.74 (t, J = 8.0 Hz, 2H), 7.64-7.49 (m, 4H), 5.65 (s, 2H), 4.85 (s, 2H), 1.64 (s, 6H). |

-continued

| Example | Structure/Name/Characterization |
|---|---|
| 15 | 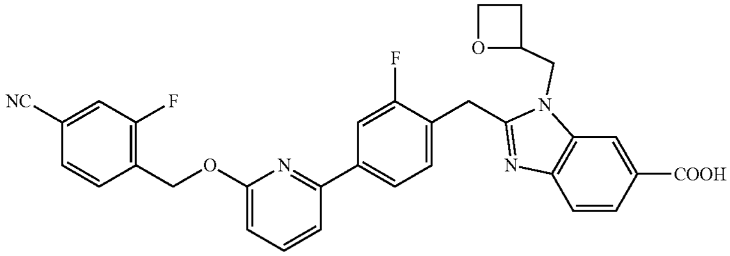 [SMILES: N#Cc1ccc(COc2cccc(-c3ccc(Cc4nc5ccc(C(=O)O)cc5n4CC4CCO4)c(F)c3)n2)c(F)c1] 2-(4-(6-((4-cyano-2-fluorobenzyl)oxy)pyridin-2-yl)-2-fluorobenzyl)-1-(oxetan-2-ylmethyl)-1H-benzo[d]imidazole-6-carboxylic acid: ES/MS 567.4; $^{1}$H NMR (400 MHz, $CD_3OD$) δ 8.60 (t, J = 1.0 Hz, 1H), 8.26-8.21 (m, 1H), 7.96-7.87 (m, 2H), 7.87-7.70 (m, 3H), 7.64-7.48 (m, 4H), 6.96-6.89 (m, 1H), 5.66 (s, 2H), 5.24 (qd, J = 7.5, 2.4 Hz, 1H), 5.00 (dd, J = 15.5, 7.6 Hz, 1H), 4.87-4.77 (m, 3H), 4.70 (ddd, J = 8.5, 7.4, 5.9 Hz, 1H), 4.55 (dt, J = 9.2, 6.0 Hz, 1H), 2.92-2.79 (m, 1H), 2.58 (ddt, J = 11.7, 9.1, 7.1 Hz, 1H). |
| 16 | 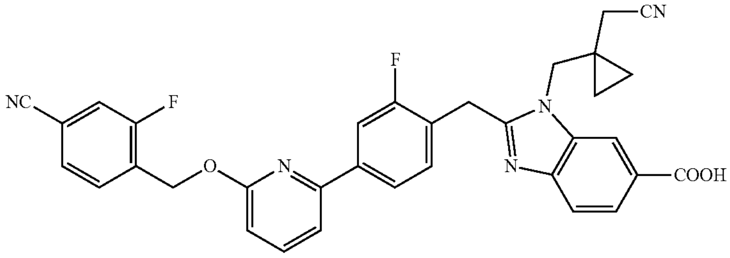 [SMILES: N#CCC1(Cn2c(Cc3ccc(-c4cccc(OCc5ccc(C#N)cc5F)n4)cc3F)nc3ccc(C(=O)O)cc32)CC1] 2-(4-(6-((4-cyano-2-fluorobenzyl)oxy)pyridin-2-yl)-2-fluorobenzyl)-1-((1-(cyanomethyl)cyclopropyl)methyl)-1H-benzo[d]imidazole-6-carboxylic acid: ES/MS 590.6; $^{1}$H NMR (400 MHz, $CD_3OD$) δ 8.65 (d, J = 1.3 Hz, 1H), 8.23 (dd, J = 8.6, 1.4 Hz, 1H), 7.96-7.87 (m, 2H), 7.87-7.77 (m, 2H), 7.74 (t, J = 7.6 Hz, 1H), 7.65-7.53 (m, 4H), 6.92 (d, J = 8.2 Hz, 1H), 5.65 (s, 2H), 4.81 (s, 2H), 4.78 (s, 2H), 2.64 (s, 2H), 1.07-0.99 (m, 2H), 0.97-0.89 (m, 2H). |
| 17 | 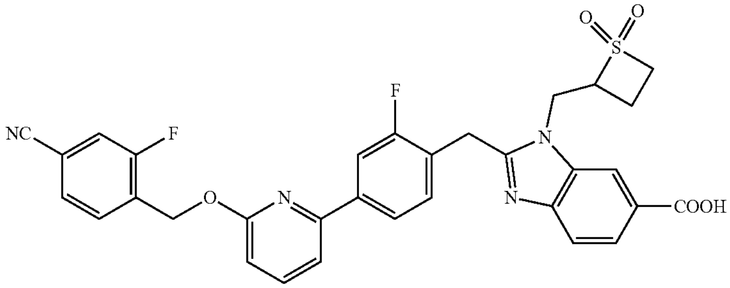 [SMILES: N#Cc1ccc(COc2cccc(-c3ccc(Cc4nc5ccc(C(=O)O)cc5n4CC4CCS4(=O)=O)c(F)c3)n2)c(F)c1] 2-(4-(6-((4-cyano-2-fluorobenzyl)oxy)pyridin-2-yl)-2-fluorobenzyl)-1-((1,1-dioxidothietan-2-yl)methyl)-1H-benzo[d]imidazole-6-carboxylic acid: ES/MS 615.4; $^{1}$H NMR (400 MHz, $CD_3OD$) δ 8.67 (s, 1H), 8.25 (d, J = 8.6 Hz, 1H), 8.04-7.67 (m, 5H), 7.67-7.48 (m, 4H), 6.93 (d, J = 8.2 Hz, 1H), 5.66 (s, 2H), 5.24 (dd, J = 15.3, 9.5 Hz, 1H), 5.13-4.96 (m, 2H), 4.94 (s, 2H), 4.17 (dq, J = 36.3, 11.9 Hz, 2H), 2.56 (q, J = 10.4 Hz, 1H), 2.08 (q, J = 10.2 Hz, 1H). |
| 18 | 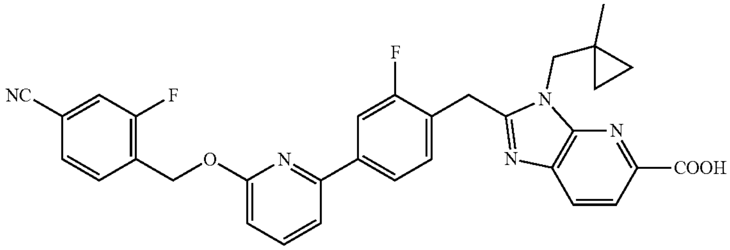 [SMILES: CC1(Cn2c(Cc3ccc(-c4cccc(OCc5ccc(C#N)cc5F)n4)cc3F)nc3ccc(C(=O)O)nc32)CC1] |

-continued

| Example | Structure/Name/Characterization |
|---|---|
| | 2-(4-(6-((4-cyano-2-fluorobenzyl)oxy)pyridin-2-yl)-2-fluorobenzyl)-3-((1-methylcyclo-propyl)methyl)-3H-imidazo[4,5-b]pyridine-5-carboxylic acid: ES/MS m/z 566.5; $^{1}$H NMR (400 MHz, $CD_3OD$) δ 8.22 (d, J = 8.3 Hz, 1H), 8.13 (d, J = 8.3 Hz, 1H), 7.90-7.78 (m, 3H), 7.74 (t, J = 7.5 Hz, 1H), 7.65-7.52 (m, 3H), 7.45 (t, J = 8.0 Hz, 1H), 6.90 (d, J = 8.1 Hz, 1H), 5.65 (s, 2H), 4.65 (s, 2H), 4.54 (s, 2H), 1.08 (s, 3H), 0.99-0.86 (m, 2H), 0.55-0.38 (m, 2H). |
| 19 | 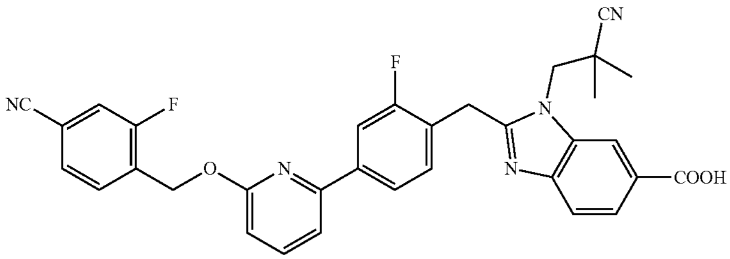<br>1-(3-cyano-2,2-dimethylpropyl)-2-(4-(6-((4-cyano-2-fluorobenzyl)oxy)pyridin-2-yl)-2-fluorobenzyl)-1H-benzo[d]imidazole-6-carboxylic acid: ES/MS 592.4; $^{1}$H NMR (400 MHz, $CD_3OD$) δ 8.59 (t, J = 1.0 Hz, 1H), 8.20 (dd, J = 8.6, 1.4 Hz, 1H), 7.98-7.79 (m, 3H), 7.79-7.70 (m, 2H), 7.67-7.50 (m, 4H), 6.92 (dd, J = 8.2, 0.6 Hz, 1H), 5.65 (s, 2H), 4.75 (s, 2H), 4.65 (s, 2H), 2.79 (s, 2H), 1.34 (s, 6H). |
| 200 | 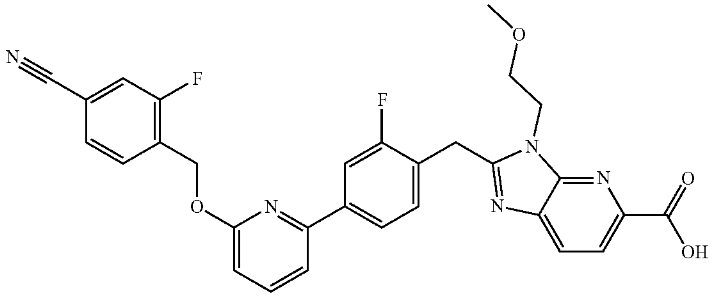 [SMILES: COCCn1c(Cc2ccc(-c3cccc(OCc4ccc(C#N)cc4F)n3)cc2F)nc2ccc(C(=O)O)nc21]<br>2-(4-(6-((4-cyano-2-fluorobenzyl)oxy)pyridin-2-yl)-2-fluorobenzyl)-3-(2-methoxyethyl)-3H-imidazo[4,5-b]pyridine-5-carboxylic acid: ES/MS 556.5; $^{1}$H NMR (400 MHz, MeOD) δ 8.22 (d, J = 8.3 Hz, 1H), 8.13 (d, J = 8.2 Hz, 1H), 7.88-7.83 (m, 2H), 7.80 (t, J = 7.8 Hz, 1H), 7.74 (t, J = 7.6 Hz, 1H), 7.61 (dd, J = 9.7, 1.5 Hz, 1H), 7.56 (t, J = 8.2 Hz, 2H), 7.41 (t, J = 7.9 Hz, 1H), 6.89 (d, J = 8.3 Hz, 1H), 5.66 (s, 2H), 4.73 (t, J = 5.1 Hz, 2H), 4.64 (s, 2H), 3.82 (t, J = 5.0 Hz, 2H), 3.32 (s, 3H). |
| 201 | 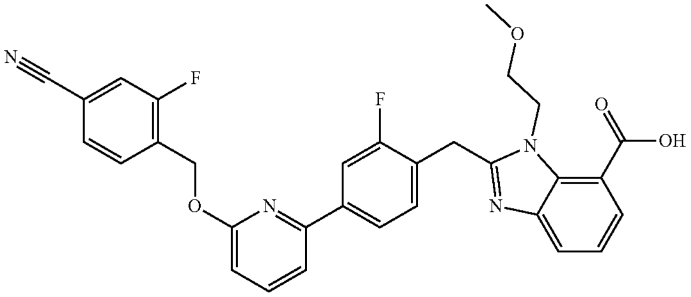 [SMILES: COCCn1c(Cc2ccc(-c3cccc(OCc4ccc(C#N)cc4F)n3)cc2F)nc2cccc(C(=O)O)c21]<br>2-(4-(6-((4-cyano-2-fluorobenzyl)oxy)pyridin-2-yl)-2-fluorobenzyl)-1-(2-methoxyethyl)-1H-benzo[d]imidazole-7-carboxylic acid: ES/MS 555.5; $^{1}$H NMR (400 MHz, MeOD) δ 8.09 (dd, J = 7.7, 1.2 Hz, 1H), 7.97-7.87 (m, 3H), 7.83 (t, J = 7.9 Hz, 1H), 7.74 (t, J = 7.6 Hz, 1H), 7.60 (ddt, J = 12.3, 7.9, 2.9 Hz, 4H), 7.50 (t, J = 7.9 Hz, 1H), 6.93 (d, J = 8.2 Hz, 1H), 5.66 (s, 2H), 5.10 (t, J = 4.9 Hz, 2H), 4.79 (s, 2H), 3.75 (t, J = 4.8 Hz, 2H), 3.26 (s, 3H). |

-continued

| Example | Structure/Name/Characterization |
|---|---|
| 203 | 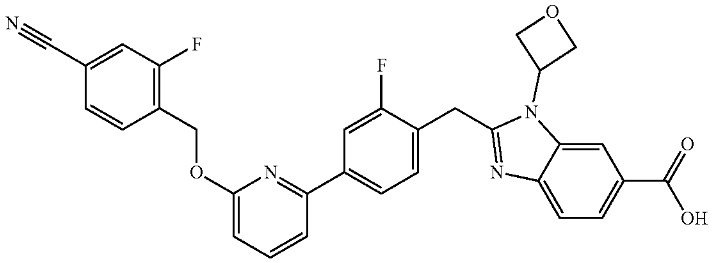 [SMILES: N#Cc1ccc(COc2cccc(-c3ccc(Cc4nc5ccc(C(=O)O)cc5n4C4COC4)c(F)c3)n2)c(F)c1] 2-(4-(6-((4-cyano-2-fluorobenzyl)oxy)pyridin-2-yl)-2-fluorobenzyl)-1-(oxetan-3-yl)-1H-benzo[d]imidazole-6-carboxylic acid: ES/MS 553.3; $^1$H NMR (400 MHz, MeOD) δ 9.09 (s, 1H), 8.20 (dd, J = 8.6, 1.4 Hz, 1H), 7.91-7.77 (m, 4H), 7.73 (t, J = 7.5 Hz, 1H), 7.65-7.52 (m, 3H), 7.38 (t, J = 8.0 Hz, 1H), 6.91 (d, J = 8.2 Hz, 1H), 6.05-5.94 (m, 1H), 5.65 (s, 2H), 5.29 (t, J = 7.8 Hz, 2H), 5.22 (dd, J = 8.1, 5.1 Hz, 2H), 4.61 (s, 2H). |
| 204 | 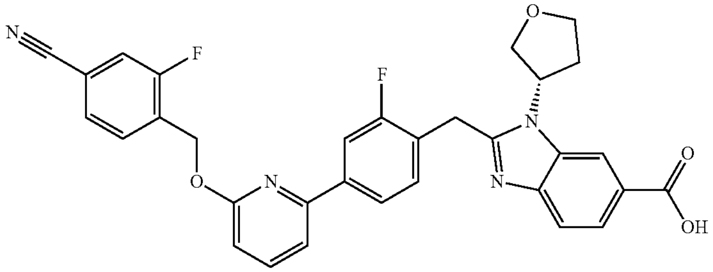 [SMILES: N#Cc1ccc(COc2cccc(-c3ccc(Cc4nc5ccc(C(=O)O)cc5n4[C@H]4CCOC4)c(F)c3)n2)c(F)c1] (S)-2-(4-(6-((4-cyano-2-fluorobenzyl)oxy)pyridin-2-yl)-2-fluorobenzyl)-1-(tetrahydrofuran-3-yl)-1H-benzo[d]imidazole-6-carboxylic acid: ES/MS 567.3; $^1$H NMR (400 MHz, MeOD) δ 8.84 (d, J = 4.2 Hz, 1H), 8.25 (dd, J = 8.5, 4.2 Hz, 1H), 8.01-7.87 (m, 2H), 7.82 (t, J = 7.7 Hz, 2H), 7.73 (t, J = 7.6 Hz, 1H), 7.64-7.49 (m, 4H), 6.93 (d, J = 8.2 Hz, 1H), 5.65 (s, 2H), 4.81 (s, 2H), 4.53-4.45 (m, 1H), 4.38 (d, J = 11.1 Hz, 1H), 4.06 (dd, J = 11.1, 7.5 Hz, 1H), 3.81 (td, J = 9.7, 6.7 Hz, 1H), 2.56 (q, J = 12.0, 10.2 Hz, 1H), 2.29 (d, J = 13.8 Hz, 1H). $^1$H obscured by solvent |
| 205 | 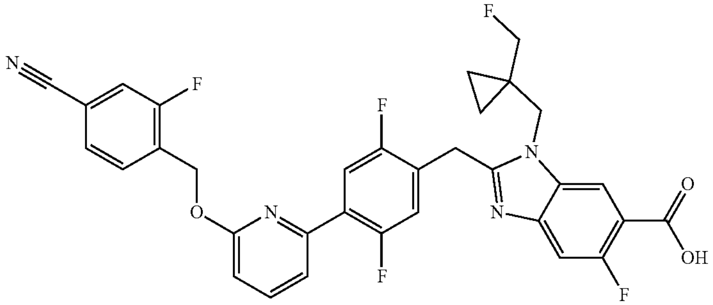 [SMILES: N#Cc1ccc(COc2cccc(-c3cc(F)c(Cc4nc5cc(F)c(C(=O)O)cc5n4CC4(CF)CC4)cc3F)n2)c(F)c1] 2-(4-(6-((4-cyano-2-fluorobenzyl)oxy)pyridin-2-yl)-2,5-difluorobenzyl)-5-fluoro-1-((1-(fluoromethyl)cyclopropyl)methyl)-1H-benzo[d]imidazole-6-carboxylic acid: ES/MS 619.2; $^1$H NMR (400 MHz, MeOD) δ 8.33 (d, J = 6.1 Hz, 1H), 7.87-7.70 (m, 3H), 7.65-7.53 (m, 3H), 7.42 (d, J = 10.9 Hz, 1H), 7.25 (dd, J = 11.4, 6.0 Hz, 1H), 6.94 (dd, J = 8.3, 0.7 Hz, 1H), 5.63 (s, 2H), 4.58 (d, J = 11.9 Hz, 4H), 4.24 (s, 1H), 4.12 (s, 1H), 0.94 (t, J = 5.0 Hz, 2H), 0.85 (d, J = 5.3 Hz, 2H). |

-continued

| Example | Structure/Name/Characterization |
|---|---|
| 206 | 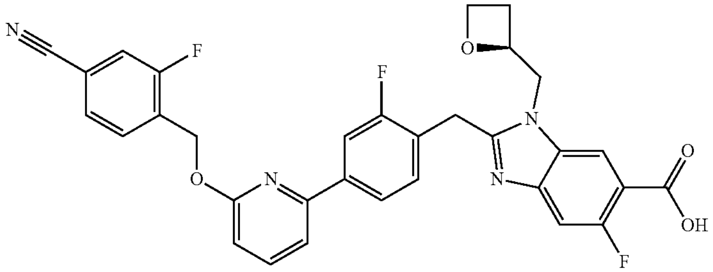 [SMILES: N#Cc1ccc(COc2cccc(-c3ccc(Cc4nc5cc(F)c(C(=O)O)cc5n4C[C@@H]4CCO4)c(F)c3)n2)c(F)c1] (S)-2-(4-(6-(((4-cyano-2-fluorobenzyl)oxy)pyridin-2-yl)-2-fluorobenzyl)-5-fluoro-1-(oxetan-2-ylmethyl)-1H-benzo[d]imidazole-6-carboxylic acid: ES/MS 585.3; $^1$H NMR (400 MHz, MeOD) δ 8.16 (d, J = 6.1 Hz, 1H), 7.85-7.77 (m, 3H), 7.74 (t, J = 7.5 Hz, 1H), 7.64-7.56 (m, 2H), 7.54 (d, J = 7.4 Hz, 1H), 7.38-7.33 (m, 2H), 6.88 (d, J = 8.2 Hz, 1H), 5.65 (s, 2H), 5.14 (tt, J = 7.3, 3.6 Hz, 1H), 4.73-4.58 (m, 2H), 4.56 (d, J = 3.2 Hz, 1H), 4.54-4.40 (m, 3H), 2.83-2.69 (m, 1H), 2.47 (ddd, J = 16.2, 10.4, 7.3 Hz, 1H). |
| 207 | 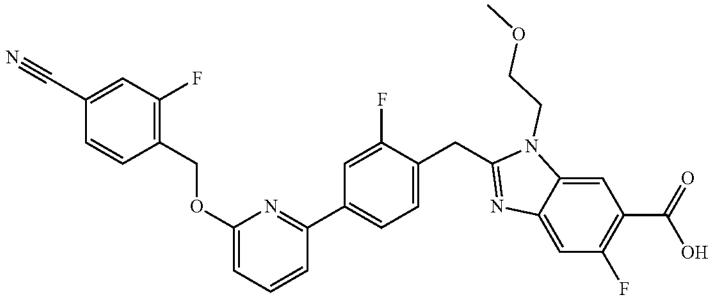 [SMILES: COCCn1c(Cc2ccc(-c3cccc(OCc4ccc(C#N)cc4F)n3)cc2F)nc2cc(F)c(C(=O)O)cc21] 2-(4-(6-((4-cyano-2-fluorobenzyl)oxy)pyridin-2-yl)-2-fluorobenzyl)-5-fluoro-1-(2-methoxyethyl)-1H-benzo[d]imidazole-6-carboxylic acid: ES/MS 573.3; $^1$H NMR (400 MHz, MeOD) δ 8.45 (s, 1H), 7.90 (t, J = 10.5 Hz, 2H), 7.82 (t, J = 7.8 Hz, 1H), 7.74 (t, J = 7.5 Hz, 1H), 7.66-7.55 (m, 3H), 7.51 (t, J = 7.7 Hz, 2H), 6.92 (d, J = 8.2 Hz, 1H), 5.66 (s, 2H), 4.74 (d, J = 19.4 Hz, 4H), 3.79 (t, J = 4.8 Hz, 2H). 3H obscured by solvent |
| 209 | 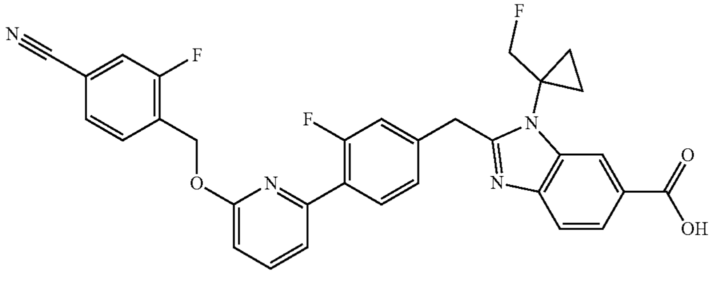 [SMILES: N#Cc1ccc(COc2cccc(-c3ccc(Cc4nc5ccc(C(=O)O)cc5n4C4(CF)CC4)cc3F)n2)c(F)c1] 2-(4-(6-((4-cyano-2-fluorobenzyl)oxy)pyridin-2-yl)-3-fluorobenzyl)-1-(1-(fluoromethyl)cyclopropyl)-1H-benzo[d]imidazole-6-carboxylic acid: ES/MS 569.3; $^1$H NMR (400 MHz, MeOD) δ 8.54-8.48 (m, 1H), 8.19 (dd, J = 8.6, 1.5 Hz, 1H), 8.04 (t, J = 8.2 Hz, 1H), 7.82 (dd, J = 8.3, 7.5 Hz, 1H), 7.79-7.70 (m, 2H), 7.59 (td, J = 9.8, 1.5 Hz, 2H), 7.53 (dd, J = 7.4, 1.8 Hz, 1H), 7.36-7.26 (m, 2H), 6.92 (d, J = 8.1 Hz, 1H), 5.63 (s, 2H), 4.77 (d, J = 14.3 Hz, 2H), 4.61 (d, J = 48.3 Hz, 1H), 1.72 (s, 2H), 1.64 (s, 2H). 1H obscured by solvent. |

-continued

| Example | Structure/Name/Characterization |
|---|---|
| 210 | 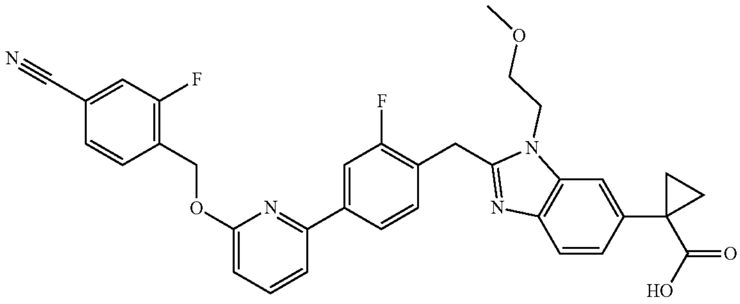 [SMILES: COCCn1c(Cc2ccc(-c3cccc(OCc4ccc(C#N)cc4F)n3)cc2F)nc2ccc(C3(C(=O)O)CC3)cc21] 1-(2-(4-(6-((4-cyano-2-fluorobenzyl)oxy)pyridin-2-yl)-2-fluorobenzyl)-1-(2-methoxyethyl)-1H-benzo[d]imidazol-6-yl)cyclopropane-1-carboxylic acid: ES/MS 595.6; $^1$H NMR (400 MHz, MeOD) δ 7.97 (t, J = 1.1 Hz, 1H), 7.94 (dd, J = 8.0, 1.8 Hz, 1H), 7.90 (dd, J = 11.7, 1.7 Hz, 1H), 7.83 (dd, J = 8.2, 7.5 Hz, 1H), 7.73 (t, J = 7.6 Hz, 1H), 7.67 (d, J = 1.1 Hz, 2H), 7.63-7.48 (m, 4H), 6.93 (d, J = 8.2 Hz, 1H), 5.66 (s, 2H), 4.79 (q, J = 3.8, 3.0 Hz, 4H), 3.85-3.78 (m, 2H), 3.32 (s, 3H), 1.73 (q, J = 4.0 Hz, 2H), 1.37 (q, J = 4.1 Hz, 2H). |
| 218 | 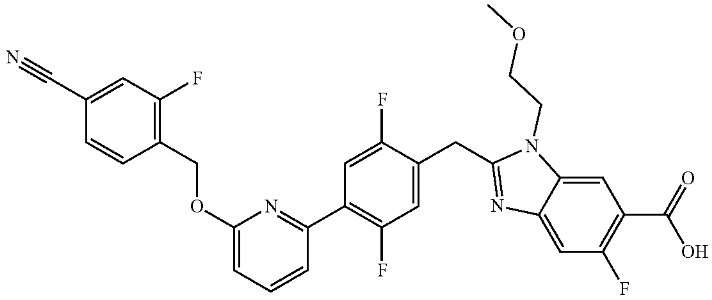 [SMILES: COCCn1c(Cc2cc(F)c(-c3cccc(OCc4ccc(C#N)cc4F)n3)cc2F)nc2cc(F)c(C(=O)O)cc21] 2-(4-(6-((4-cyano-2-fluorobenzyl)oxy)pyridin-2-yl)-2,5-difluorobenzyl)-5-fluoro-1-(2-methoxyethyl)-1H-benzo[d]imidazole-6-carboxylic acid: ES/MS 591.3; $^1$H NMR (400 MHz, MeOD) δ 8.33 (d, J = 6.0 Hz, 1H), 7.87-7.69 (m, 3H), 7.65-7.53 (m, 3H), 7.45 (d, J = 10.7 Hz, 1H), 7.26 (dd, J = 11.3, 6.0 Hz, 1H), 6.95 (dd, J = 8.3, 0.7 Hz, 1H), 5.63 (s, 2H), 4.68 (t, J = 5.0 Hz, 2H), 4.61 (s, 2H), 3.78 (t, J = 4.9 Hz, 2H), 3.30 (s, 3H). |
| 219 | 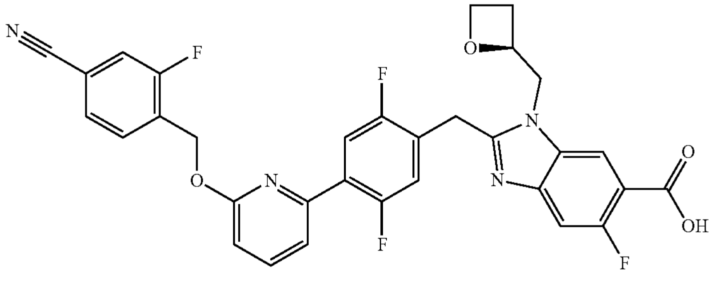 [SMILES: N#Cc1ccc(COc2cccc(-c3cc(F)c(Cc4nc5cc(F)c(C(=O)O)cc5n4C[C@@H]4CCO4)cc3F)n2)c(F)c1] (S)-2-(4-(6-((4-cyano-2-fluorobenzyl)oxy)pyridin-2-yl)-2,5-difluorobenzyl)-5-fluoro-1-(oxetan-2-ylmethyl)-1H-benzo[d]imidazole-6-carboxylic acid: ES/MS 603.3; $^1$H NMR (400 MHz, MeOD) δ 8.24 (d, J = 6.2 Hz, 1H), 7.86-7.70 (m, 3H), 7.65-7.52 (m, 4H), 7.38 (d, J = 11.2 Hz, 1H), 7.21 (dd, J = 11.5, 6.1 Hz, 1H), 6.96-6.90 (m, 1H), 5.64 (s, 2H), 5.25-5.13 (m, 1H), 4.74 (dd, J = 15.7, 7.0 Hz, 1H), 4.70-4.60 (m, 1H), 4.57 (s, 1H), 4.52 (s, 1H), 4.50-4.41 (m, 1H), 2.87-2.74 (m, 1H), 2.57-2.42 (m, 1H). |

-continued

| Example | Structure/Name/Characterization |
|---|---|
| 220 | 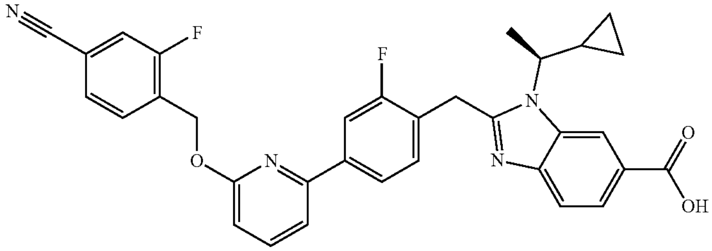 [SMILES: C[C@@H](C1CC1)n1c(Cc2ccc(-c3cccc(OCc4ccc(C#N)cc4F)n3)cc2F)nc2ccc(C(=O)O)cc21] (S)-2-(4-(6-((4-cyano-2-fluorobenzyl)oxy)pyridin-2-yl)-2-fluorobenzyl)-1-(1-cyclopropylethyl)-1H-benzo[d]imidazole-6-carboxylic acid: ES/MS 565.2; $^{1}H$ NMR (400 MHz, MeOD) δ 8.67 (s, 1H), 8.27-8.20 (m, 1H), 7.97-7.86 (m, 2H), 7.82 (t, J = 8.1 Hz, 2H), 7.73 (t, J = 7.5 Hz, 1H), 7.65-7.45 (m, 4H), 6.92 (d, J = 8.2 Hz, 1H), 5.65 (s, 2H), 4.69 (s, 2H), 4.35-4.16 (m, 1H), 1.78 (d, J = 6.7 Hz, 4H), 0.97-0.80 (m, 1H), 0.70-0.58 (m, 1H), 0.53 (t, J = 6.8 Hz, 1H), 0.11 (dd, J = 10.0, 5.2 Hz, 1H). |
| 221 | 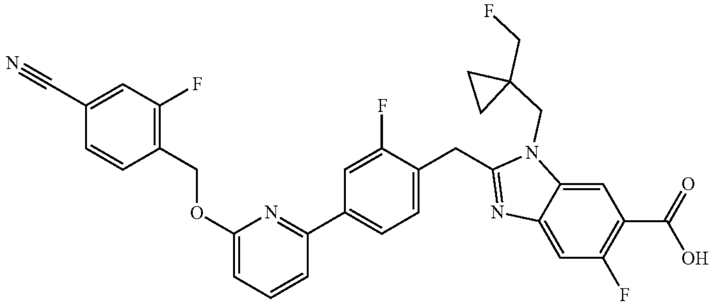 [SMILES: N#Cc1ccc(COc2cccc(-c3ccc(Cc4nc5cc(F)c(C(=O)O)cc5n4CC4(CF)CC4)c(F)c3)n2)c(F)c1] 2-(4-(6-((4-cyano-2-fluorobenzyl)oxy)pyridin-2-yl)-2-fluorobenzyl)-5-fluoro-1-((1-(fluoromethyl)cyclopropyl)methyl)-1H-benzo[d]imidazole-6-carboxylic acid: ES/MS 601.3; $^{1}H$ NMR (400 MHz, MeOD) δ 8.40 (d, J = 6.0 Hz, 1H), 7.91-7.84 (m, 2H), 7.81 (dd, J = 8.2, 7.5 Hz, 1H), 7.74 (t, J = 7.6 Hz, 1H), 7.65-7.54 (m, 3H), 7.49-7.44 (m, 2H), 6.94-6.87 (m, 1H), 5.65 (s, 2H), 4.64 (s, 4H), 4.26 (s, 1H), 4.14 (s, 1H), 0.97 (dt, J = 6.5, 4.9 Hz, 2H), 0.90-0.82 (m, 2H). |
| 222 | 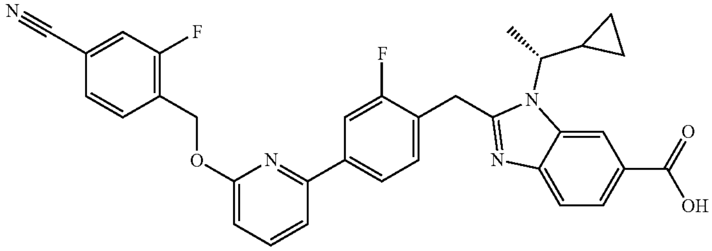 [SMILES: C[C@H](C1CC1)n1c(Cc2ccc(-c3cccc(OCc4ccc(C#N)cc4F)n3)cc2F)nc2ccc(C(=O)O)cc21] (R)-2-(4-(6-((4-cyano-2-fluorobenzyl)oxy)pyridin-2-yl)-2-fluorobenzyl)-1-(1-cyclopropylethyl)-1H-benzo[d]imidazole-6-carboxylic acid: ES/MS 565.2; $^{1}H$ NMR (400 MHz, MeOD) δ 8.66 (s, 1H), 8.23 (dd, J = 8.6, 1.4 Hz, 1H), 7.97-7.86 (m, 2H), 7.82 (dd, J = 8.4, 6.9 Hz, 2H), 7.73 (t, J = 7.5 Hz, 1H), 7.65-7.48 (m, 4H), 6.92 (d, J = 8.2 Hz, 1H), 5.65 (s, 2H), 4.69 (s, 2H), 4.30-4.21 (m, 1H), 1.77 (d, J = 6.9 Hz, 4H), 0.89 (s, 1H), 0.72-0.58 (m, 1H), 0.52 (s, 1H), 0.11 (dd, J = 9.8, 5.1 Hz, 1H). |
| 223 | 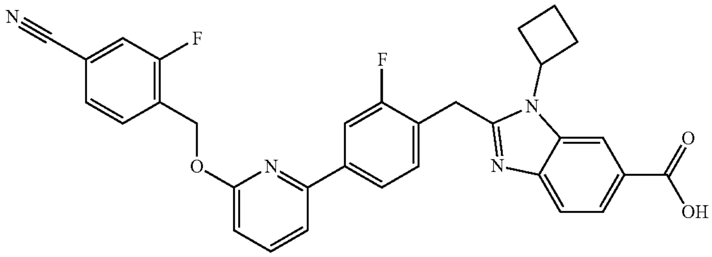 [SMILES: N#Cc1ccc(COc2cccc(-c3ccc(Cc4nc5ccc(C(=O)O)cc5n4C4CCC4)c(F)c3)n2)c(F)c1] |

-continued

| Example | Structure/Name/Characterization |
|---|---|
| | 2-(4-(6-((4-cyano-2-fluorobenzyl)oxy)pyridin-2-yl)-2-fluorobenzyl)-1-cyclobutyl-1H-benzo[d]imidazole-6-carboxylic acid: ES/MS 551.3; $^1$H NMR (400 MHz, MeOD) δ 8.70-8.65 (m, 1H), 8.22 (dd, J = 8.6, 1.6 Hz, 1H), 7.96-7.85 (m, 2H), 7.85-7.77 (m, 2H), 7.73 (t, J = 7.5 Hz, 1H), 7.59 (dd, J = 16.0, 8.6 Hz, 3H), 7.46 (t, J = 7.9 Hz, 1H), 6.92 (d, J = 8.2 Hz, 1H), 5.65 (s, 2H), 5.37 (p, J = 8.7 Hz, 1H), 4.70 (s, 2H), 3.04 (dq, J = 12.4, 9.7 Hz, 2H), 2.78-2.60 (m, 2H), 2.28-2.03 (m, 2H). |
| 224 | 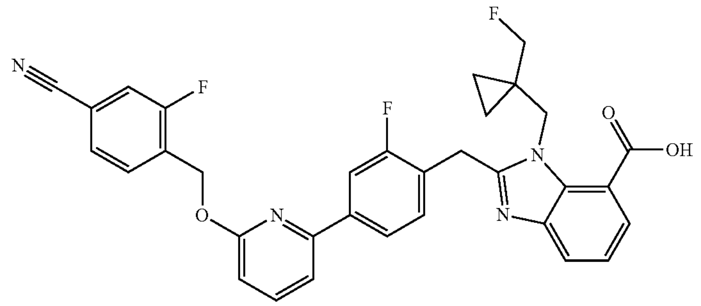 [SMILES: N#Cc1ccc(COc2cccc(-c3ccc(Cc4nc5cccc(C(=O)O)c5n4CC4(CF)CC4)c(F)c3)n2)c(F)c1] 2-(4-(6-((4-cyano-2-fluorobenzyl)oxy)pyridin-2-yl)-2-fluorobenzyl)-1-((1-(fluoromethyl)cyclopropyl)methyl)-1H-benzo[d]imidazole-7-carboxylic acid: ES/MS 583.3; $^1$H NMR (400 MHz, MeOD) δ 8.05 (dd, J = 7.6, 1.2 Hz, 1H), 7.91 (ddt, J = 9.1, 4.1, 1.8 Hz, 3H), 7.82 (dd, J = 8.2, 7.4 Hz, 1H), 7.74 (t, J = 7.5 Hz, 1H), 7.65-7.52 (m, 4H), 7.48 (t, J = 8.0 Hz, 1H), 6.92 (d, J = 8.2 Hz, 1H), 5.66 (s, 2H), 5.15 (s, 2H), 4.74 (s, 2H), 4.22 (s, 1H), 4.10 (s, 1H), 0.70 (s, 4H). |
| 225 | 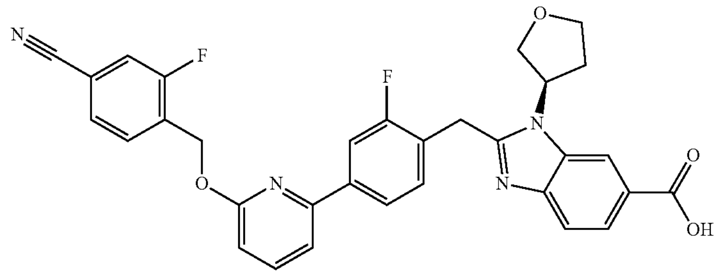 [SMILES: N#Cc1ccc(COc2cccc(-c3ccc(Cc4nc5ccc(C(=O)O)cc5n4[C@@H]4CCOC4)c(F)c3)n2)c(F)c1] (R)-2-(4-(6-((4-cyano-2-fluorobenzyl)oxy)pyridin-2-yl)-2-fluorobenzyl)-1-(tetrahydrofuran-3-yl)-1H-benzo[d]imidazole-6-carboxylic acid: ES/MS 567.4; $^1$H NMR (400 MHz, MeOD) δ 8.81 (d, J = 1.4 Hz, 1H), 8.22 (dd, J = 8.6, 1.4 Hz, 1H), 7.97-7.86 (m, 2H), 7.86-7.79 (m, 2H), 7.73 (t, J = 7.6 Hz, 1H), 7.61 (dd, J = 9.7, 1.5 Hz, 1H), 7.57 (dd, J = 7.7, 1.7 Hz, 2H), 7.50 (t, J = 7.9 Hz, 1H), 6.92 (d, J = 8.3 Hz, 1H), 5.65 (s, 3H), 4.78 (d, J = 2.6 Hz, 2H), 4.48 (t, J = 8.8 Hz, 1H), 4.40-4.32 (m, 1H), 4.04 (dd, J = 11.0, 7.5 Hz, 1H), 3.80 (td, J = 9.7, 6.9 Hz, 1H), 2.54 (dt, J = 14.3, 7.3 Hz, 1H), 2.35-2.20 (m, 1H). |
| 231 | 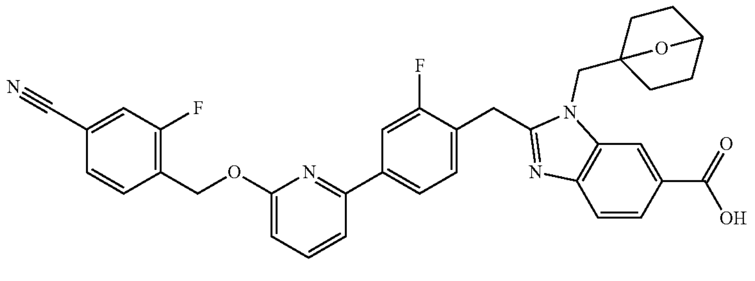 [SMILES: N#Cc1ccc(COc2cccc(-c3ccc(Cc4nc5ccc(C(=O)O)cc5n4CC45CCC(CC4)O5)c(F)c3)n2)c(F)c1] 1-(7-oxabicyclo[2.2.1]heptan-1-ylmethyl)-2-(4-(6-((4-cyano-2-fluorobenzyl)oxy)pyridin-2-yl)-2-fluorobenzyl)-1H-benzo[d]imidazole-6-carboxylic acid: ES/MS 607.2; $^1$H NMR (400 MHz, DMSO-d6) δ 12.75 (s, 1H), 8.24 (d, J = 1.5 Hz, 1H), 7.93 (dd, J = 10.0, 1.4 Hz, 1H), 7.88 (d, J = 2.4 Hz, 1H), 7.87-7.84 (m, 2H), 7.79-7.71 (m, 3H), 7.66 (d, J = 7.5 Hz, 1H), 7.57 (d, J = 8.4 Hz, 1H), 7.43 (t, J = 7.9 Hz, 1H), 6.93 (d, J = 8.2 Hz, 1H), 5.62 (s, 2H), 4.78 (s, 2H), 4.51 (t, J = 4.9 Hz, 1H), 4.45 (s, 2H), 1.73 (td, J = 9.9, 4.1 Hz, 2H), 1.69-1.57 (m, 2H), 1.53 (td, J = 11.6, 10.4, 4.1 Hz, 2H), 1.42-1.27 (m, 2H). |

-continued

| Example | Structure/Name/Characterization |
|---|---|
| 242 | 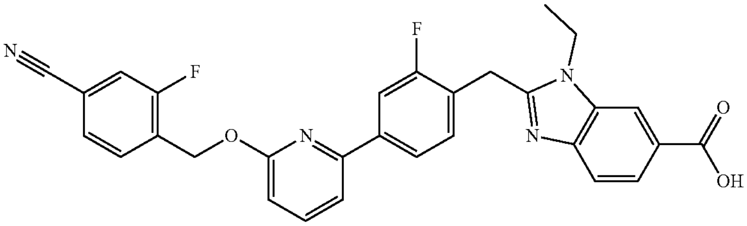 2-(4-(6-((4-cyano-2-fluorobenzyl)oxy)pyridin-2-yl)-2-fluorobenzyl)-1-ethyl-1H-benzo[d]imidazole-6-carboxylic acid: ES/MS 539.2; 1H NMR (400 MHz, Methanol-d4) δ 8.53 (d, J = 1.3 Hz, 1H), 8.24 (dd, J = 8.7, 1.4 Hz, 1H), 7.93 (dd, J = 8.0, 1.7 Hz, 1H), 7.88 (dd, J = 11.8, 1.7 Hz, 1H), 7.84-7.77 (m, 2H), 7.72 (t, J = 7.5 Hz, 1H), 7.62-7.51 (m, 4H), 6.91 (d, J = 8.2 Hz, 1H), 5.64 (s, 2H), 4.74 (s, 2H), 4.64 (q, J = 7.3 Hz, 2H), 1.46 (t, J = 7.2 Hz, 3H). |
| 263 | 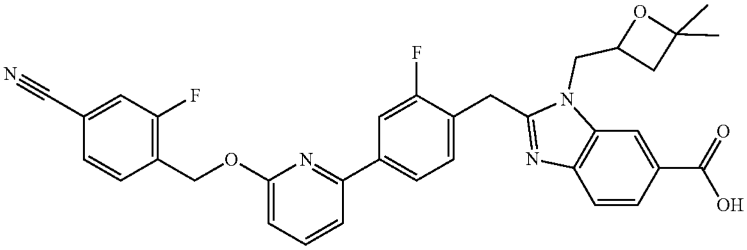 [SMILES: CC1(C)CC(Cn2c(Cc3ccc(-c4cccc(OCc5ccc(C#N)cc5F)n4)cc3F)nc3ccc(C(=O)O)cc32)O1] (mixture) 2-(4-(6-((4-cyano-2-fluorobenzyl)oxy)pyridin-2-yl)-2-fluorobenzyl)-1-((4,4-dimethyloxetan-2-yl)methyl)-1H-benzo[d]imidazole-6-carboxylic acid: ES/MS 595.2; $^1$H NMR (400 MHz, DMSO-d6) δ 8.15 (s, 1H), 7.93 (dd, J = 9.9, 1.5 Hz, 1H), 7.86 (td, J = 7.9, 3.5 Hz, 3H), 7.81-7.71 (m, 3H), 7.66 (d, J = 7.5 Hz, 1H), 7.52 (d, J = 8.4 Hz, 1H), 7.40 (t, J = 8.1 Hz, 1H), 6.93 (d, J = 8.2 Hz, 1H), 5.62 (s, 2H), 4.87 (dt, J = 7.7, 3.2 Hz, 1H), 4.58-4.48 (m, 3H), 4.42 (d, J = 16.7 Hz, 1H), 2.41 (dd, J = 11.1, 7.7 Hz, 1H), 2.13 (dd, J = 11.1, 7.2 Hz, 1H), 1.34 (s, 3H), 1.09 (s, 3H). |
| 264 | 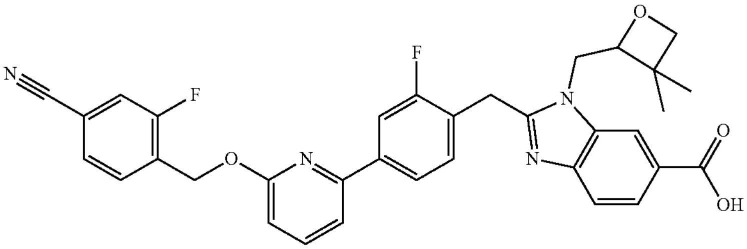 (mixture) 2-(4-(6-((4-cyano-2-fluorobenzyl)oxy)pyridin-2-yl)-2-fluorobenzyl)-1-((3,3-dimethyloxetan-2-yl)methyl)-1H-benzo[d]imidazole-6-carboxylic acid: ES/MS 609.2; $^1$H NMR (400 MHz, DMSO-d6) δ 8.31 (d, J = 1.5 Hz, 1H), 7.93 (dd, J = 10.0, 1.4 Hz, 1H), 7.91-7.84 (m, 3H), 7.82 (dd, J = 8.4, 1.5 Hz, 1H), 7.79-7.71 (m, 2H), 7.67 (d, J = 7.5 Hz, 1H), 7.60 (d, J = 8.4 Hz, 1H), 7.45 (t, J = 8.1 Hz, 1H), 5.62 (s, 2H), 4.77 (dd, J = 15.3, 10.3 Hz, 1H), 4.64 (d, J = 15.0 Hz, 1H), 4.58 (d, J = 16.7 Hz, 1H), 4.44 (d, J = 16.7 Hz, 1H), 4.39 (dd, J = 10.2, 2.0 Hz, 1H), 4.35 (d, J = 5.4 Hz, 1H), 4.19 (d, J = 5.4 Hz, 1H), 1.35 (s, 3H), 1.27 (s, 3H). |

-continued

| Example | Structure/Name/Characterization |
|---|---|
| 269 | 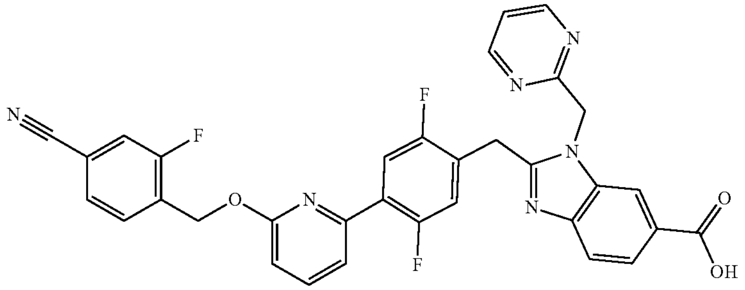 [SMILES: N#Cc1ccc(COc2cccc(-c3cc(F)c(Cc4nc5ccc(C(=O)O)cc5n4Cc4ncccn4)cc3F)n2)c(F)c1]<br>2-(4-(6-((4-cyano-2-fluorobenzyl)oxy)pyridin-2-yl)-2,5-difluorobenzyl)-1-(pyrimidin-2-ylmethyl)-1H-benzo[d]imidazole-6-carboxylic acid: ES/MS 607.3; $^{1}$H NMR (400 MHz, Methanol-d4) δ 8.62 (d, J = 4.9 Hz, 2H), 8.40 (dd, J = 1.4, 0.7 Hz, 1H), 8.23 (dd, J = 8.6, 1.5 Hz, 1H), 7.89-7.79 (m, 2H), 7.73 (t, J = 7.5 Hz, 1H), 7.68-7.54 (m, 3H), 7.50 (dd, J = 7.4, 1.7 Hz, 1H), 7.35-7.19 (m, 2H), 6.95 (dd, J = 8.3, 0.6 Hz, 1H), 6.05 (s, 2H), 5.62 (s, 2H), 4.77 (s, 2H). |
| 270 | 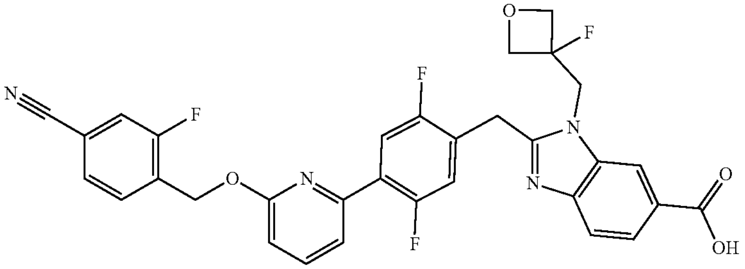 [SMILES: N#Cc1ccc(COc2cccc(-c3cc(F)c(Cc4nc5ccc(C(=O)O)cc5n4CC4(F)COC4)cc3F)n2)c(F)c1]<br>2-(4-(6-((4-cyano-2-fluorobenzyl)oxy)pyridin-2-yl)-2,5-difluorobenzyl)-1-((3-fluorooxetan-3-yl)methyl)-1H-benzo[d]imidazole-6-carboxylic acid: ES/MS 603.2; $^{1}$H NMR (400 MHz, Methanol-d4) δ 8.56 (s, 1H), 8.11 (dd, J = 8.6, 1.5 Hz, 1H), 7.92-7.67 (m, 4H), 7.67-7.51 (m, 3H), 7.29 (dd, J = 11.3, 6.1 Hz, 1H), 6.95 (dd, J = 8.2, 0.6 Hz, 1H), 5.63 (s, 2H), 5.23 (d, J = 21.9 Hz, 2H), 4.83-4.71 (m, 4H), 4.62 (s, 2H). |
| 271 | 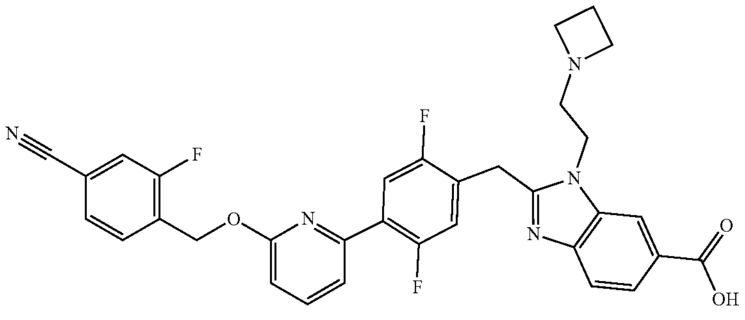 [SMILES: N#Cc1ccc(COc2cccc(-c3cc(F)c(Cc4nc5ccc(C(=O)O)cc5n4CCN4CCC4)cc3F)n2)c(F)c1]<br>1-(2-(azetidin-1-yl)ethyl)-2-(4-(6-((4-cyano-2-fluorobenzyl)oxy)pyridin-2-yl)-2,5-difluorobenzyl)-1H-benzo[d]imidazole-6-carboxylic acid: ES/MS 598.4; $^{1}$H NMR (400 MHz, Methanol-d4) δ 8.36 (dd, J = 1.5, 0.7 Hz, 1H), 8.07 (dd, J = 8.5, 1.5 Hz, 1H), 7.94-7.65 (m, 4H), 7.65-7.49 (m, 3H), 7.28 (dd, J = 11.3, 6.1 Hz, 1H), 6.95 (dd, J = 8.3, 0.7 Hz, 1H), 5.63 (s, 2H), 4.70 (t, J = 7.0 Hz, 2H), 4.52 (s, 2H), 4.29 (s, 4H), 3.80 (t, J = 7.0 Hz, 2H), 2.58 (s, 2H). |

-continued

| Example | Structure/Name/Characterization |
|---|---|
| 272 | 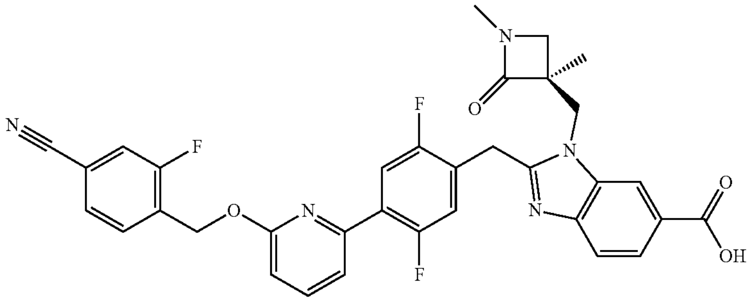 and 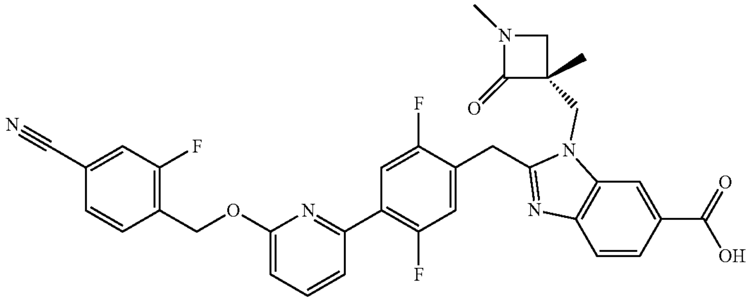 [SMILES: CN1C[C@](C)(Cn2c(Cc3cc(F)c(-c4cccc(OCc5ccc(C#N)cc5F)n4)cc3F)nc3ccc(C(=O)O)cc32)C1=O] 2-(4-(6-((4-cyano-2-fluorobenzyl)oxy)pyridin-2-yl)-2,5-difluorobenzyl)-1-((1,3-dimethyl-2-oxoazetidin-3-yl)methyl)-1H-benzo[d]imidazole-6-carboxylic acid: ES/MS 626.3; $^{1}$H NMR (400 MHz, Methanol-d4) δ 8.53 (d, J = 1.3 Hz, 1H), 8.14 (dd, J = 8.6, 1.4 Hz, 1H), 7.94-7.77 (m, 2H), 7.73 (dt, J = 7.4, 3.3 Hz, 2H), 7.60-7.53 (m, 3H), 7.33 (dd, J = 11.3, 6.0 Hz, 1H), 6.95 (d, J = 8.3 Hz, 1H), 5.63 (s, 2H), 4.85-4.75 (m, 2H), 4.71 (s, 2H), 3.42-3.34 (m, 2H), 2.75 (s, 3H), 1.50 (s, 3H). |
| 273 | 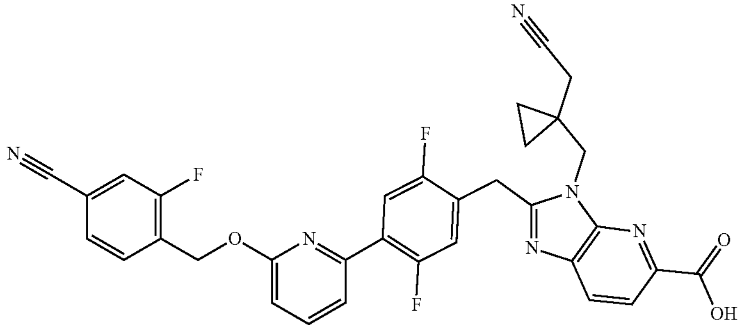 [SMILES: N#CCC1(Cn2c(Cc3cc(F)c(-c4cccc(OCc5ccc(C#N)cc5F)n4)cc3F)nc3ccc(C(=O)O)nc32)CC1] 2-(4-(6-((4-cyano-2-fluorobenzyl)oxy)pyridin-2-yl)-2,5-difluorobenzyl)-3-((1-(cyanomethyl)cyclopropyl)methyl)-3H-imidazo[4,5-b]pyridine-5-carboxylic acid: ES/MS 609.1; $^{1}$H NMR (400 MHz, Methanol-d4) δ 8.19 (d, J = 8.3 Hz, 1H), 8.10 (d, J = 8.3 Hz, 1H), 7.90-7.71 (m, 3H), 7.69-7.53 (m, 3H), 7.31 (dd, J = 11.4, 6.1 Hz, 1H), 6.93 (dd, J = 8.2, 3.5 Hz, 1H), 5.64 (s, 2H), 4.65 (s, 2H), 4.58 (s, 2H), 2.69 (d, J = 10.8 Hz, 2H), 1.13-1.04 (m, 2H), 0.91-0.73 (m, 2H). |
| 276 | 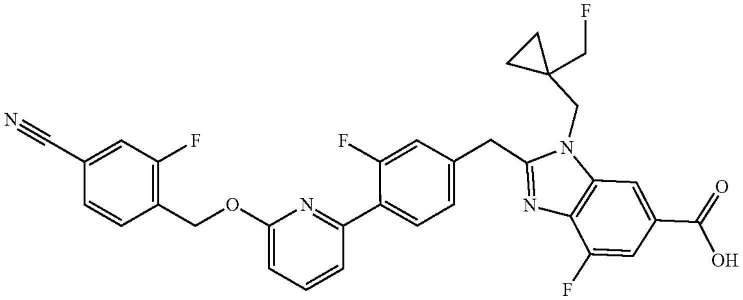 [SMILES: N#Cc1ccc(COc2cccc(-c3ccc(Cc4nc5c(F)cc(C(=O)O)cc5n4CC4(CF)CC4)cc3F)n2)c(F)c1] |

-continued

| Example | Structure/Name/Characterization |
|---|---|
| | 2-(4-(6-((4-cyano-2-fluorobenzyl)oxy)pyridin-2-yl)-3-fluorobenzyl)-4-fluoro-1-((1-(fluoromethyl)cyclopropyl)methyl)-1H-benzo[d]imidazole-6-carboxylic acid: ES/MS 601.1; $^{1}$H NMR (400 MHz, Methanol-d4) δ 8.24 (d, J = 1.2 Hz, 1H), 7.97 (t, J = 8.2 Hz, 1H), 7.87-7.68 (m, 3H), 7.58 (ddd, J = 11.3, 8.7, 1.5 Hz, 2H), 7.48 (dd, J = 7.4, 1.8 Hz, 1H), 7.28-7.10 (m, 2H), 6.88 (d, J = 8.2 Hz, 1H), 5.61 (s, 2H), 4.59 (s, 2H), 4.51 (s, 2H), 4.22 (s, 1H), 4.10 (s, 1H), 0.93-0.81 (m, 2H), 0.80 (d, J = 4.7 Hz, 2H). |
| 277 | 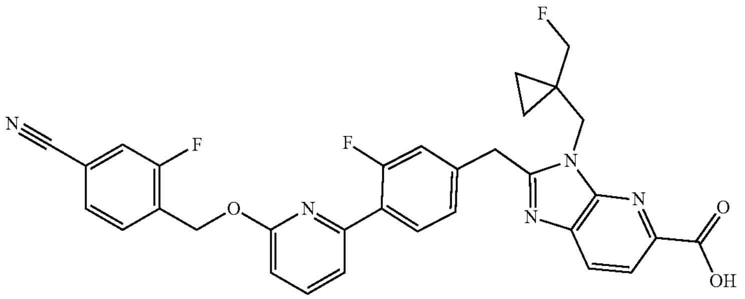 [SMILES: N#Cc1ccc(COc2cccc(-c3ccc(Cc4nc5ccc(C(=O)O)nc5n4CC4(CF)CC4)cc3F)n2)c(F)c1] 2-(4-(6-((4-cyano-2-fluorobenzyl)oxy)pyridin-2-yl)-3-fluorobenzyl)-3-((1-(fluoromethyl)cyclopropyl)methyl)-3H-imidazo[4,5-b]pyridine-5-carboxylic acid: ES/MS 584.3; $^{1}$H NMR (400 MHz, Methanol-d4) δ 8.26 (d, J = 8.3 Hz, 1H), 8.18 (d, J = 8.3 Hz, 1H), 8.00 (t, J = 8.1 Hz, 1H), 7.80 (t, J = 7.9 Hz, 1H), 7.73 (t, J = 7.4 Hz, 1H), 7.58 (td, J = 9.9, 1.6 Hz, 2H), 7.50 (dt, J = 8.4, 2.6 Hz, 1H), 7.33-7.16 (m, 2H), 6.90 (d, J = 8.3 Hz, 1H), 5.62 (s, 2H), 4.66 (d, J = 16.6 Hz, 4H), 4.39 (s, 1H), 4.27 (s, 1H), 1.20 (q, J = 5.5 Hz, 2H), 0.76 (d, J = 5.7 Hz, 2H). |
| 279 | 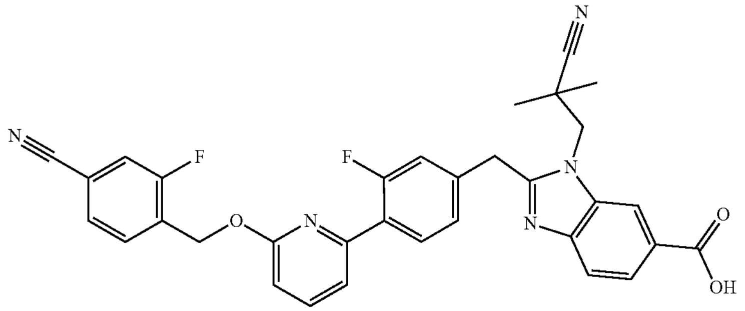 [SMILES: CC(C)(C#N)Cn1c(Cc2ccc(-c3cccc(OCc4ccc(C#N)cc4F)n3)c(F)c2)nc2ccc(C(=O)O)cc21] 2-(4-(6-((4-cyano-2-fluorobenzyl)oxy)pyridin-2-yl)-3-fluorobenzyl)-1-(2-cyano-2-methylpropyl)-1H-benzo[d]imidazole-6-carboxylic acid: ES/MS 578.4; $^{1}$H NMR (400 MHz, Methanol-d4) δ 8.56 (s, 1H), 8.14 (dd, J = 8.6, 1.4 Hz, 1H), 8.01 (s, 1H), 7.90-7.65 (m, 3H), 7.65-7.55 (m, 2H), 7.51 (dd, J = 7.4, 1.7 Hz, 1H), 7.37-7.12 (m, 2H), 6.91 (d, J = 8.2 Hz, 1H), 5.63 (s, 2H), 4.77 (s, 4H), 1.61 (s, 6H). |
| 281 | 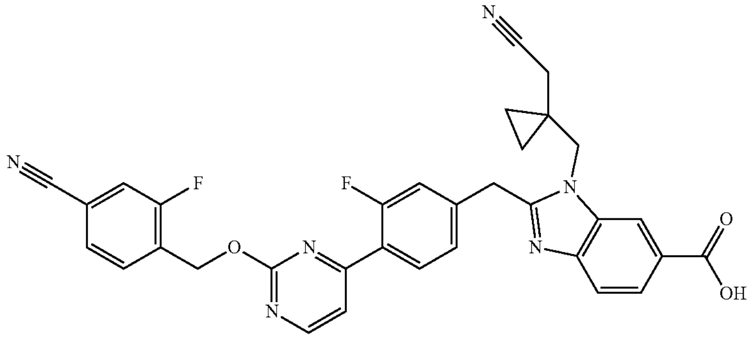 [SMILES: N#CCC1(Cn2c(Cc3ccc(-c4ccnc(OCc5ccc(C#N)cc5F)n4)c(F)c3)nc3ccc(C(=O)O)cc32)CC1] 2-(4-(2-((4-cyano-2-fluorobenzyl)oxy)pyrimidin-4-yl)-3-fluorobenzyl)-1-((1-(cyanomethyl)cyclopropyl)methyl)-1H-benzo[d]imidazole-6-carboxylic acid: ES/MS 591.2; $^{1}$H NMR (400 MHz, Methanol-d4) δ 8.70 (d, J = 5.2 Hz, 1H), 8.65 (d, J = 1.3 Hz, 1H), 8.29-8.16 (m, 2H), 7.80 (dd, J = 11.0, 8.0 Hz, 2H), 7.68-7.55 (m, 3H), 7.50-7.34 (m, 2H), 5.69 (s, 2H), 4.82 (s, 2H), 4.73 (s, 2H), 2.63 (s, 2H), 0.99 (d, J = 5.0 Hz, 2H), 0.92 (d, J = 5.0 Hz, 2H). |

-continued

| Example | Structure/Name/Characterization |
|---|---|
| 283 | 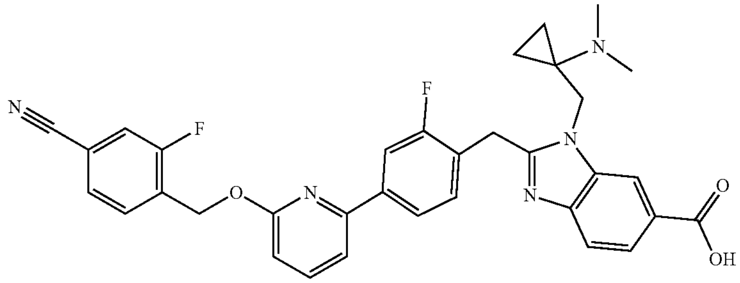 [SMILES: CN(C)C1(Cn2c(Cc3ccc(-c4cccc(OCc5ccc(C#N)cc5F)n4)cc3F)nc3ccc(C(=O)O)cc32)CC1]<br>2-(4-(6-((4-cyano-2-fluorobenzyl)oxy)pyridin-2-yl)-2-fluorobenzyl)-1-((1-(dimethylamino)cyclopropyl)methyl)-1H-benzo[d]imidazole-6-carboxylic acid: ES/MS 594.3; $^1$H NMR (400 MHz, Methanol-d4) δ 8.34 (d, J = 1.6 Hz, 1H), 8.06 (dd, J = 8.5, 1.5 Hz, 1H), 7.92-7.78 (m, 3H), 7.77-7.69 (m, 2H), 7.61 (dd, J = 9.7, 1.5 Hz, 1H), 7.59-7.55 (m, 2H), 7.48 (t, J = 7.9 Hz, 1H), 6.91 (d, J = 8.2 Hz, 1H), 5.66 (s, 2H), 5.12 (s, 2H), 4.53 (s, 2H), 3.19 (s, 6H), 1.23 (s, 2H), 0.75 (d, J = 7.4 Hz, 2H). |
| 284 | 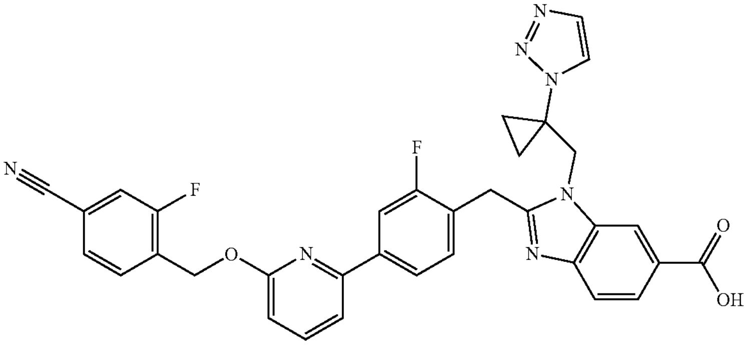 [SMILES: N#Cc1ccc(COc2cccc(-c3ccc(Cc4nc5ccc(C(=O)O)cc5n4CC4(n5ccnn5)CC4)c(F)c3)n2)c(F)c1]<br>1-((1-(1H-1,2,3-triazol-1-yl)cyclopropyl)methyl)-2-(4-(6-((4-cyano-2-fluorobenzyl)oxy)pyridin-2-yl)-2-fluorobenzyl)-1H-benzo[d]imidazole-6-carboxylic acid: ES/MS 618.3; $^1$H NMR (400 MHz, Methanol-d4) δ 8.10-8.01 (m, 2H), 7.79-7.65 (m, 6H), 7.59 (d, J = 1.1 Hz, 1H), 7.56-7.36 (m, 3H), 7.27 (t, J = 8.0 Hz, 1H), 6.85 (d, J = 8.2 Hz, 1H), 5.61 (s, 2H), 4.89 (s, 2H), 3.92 (s, 2H), 1.76-1.62 (m, 2H), 1.60-1.50 (m, 2H). |
| 285 | 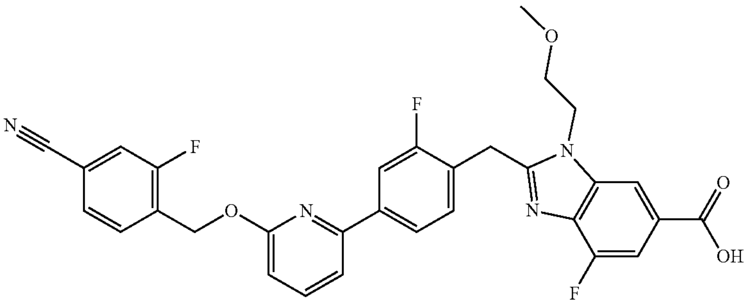 [SMILES: COCCn1c(Cc2ccc(-c3cccc(OCc4ccc(C#N)cc4F)n3)cc2F)nc2c(F)cc(C(=O)O)cc21]<br>2-(4-(6-((4-cyano-2-fluorobenzyl)oxy)pyridin-2-yl)-2-fluorobenzyl)-4-fluoro-1-(2-methoxyethyl)-1H-benzo[d]imidazole-6-carboxylic acid: ES/MS 573.3; $^1$H NMR (400 MHz, Methanol-d4) δ 8.13 (d, J = 1.3 Hz, 1H), 7.90-7.71 (m, 4H), 7.71-7.44 (m, 4H), 7.32 (t, J = 8.1 Hz, 1H), 6.88 (d, J = 8.2 Hz, 1H), 5.65 (s, 2H), 4.53 (d, J = 3.7 Hz, 4H), 3.67 (t, J = 5.0 Hz, 2H), 3.25 (s, 3H). |

-continued

| Example | Structure/Name/Characterization |
|---|---|
| 287 | 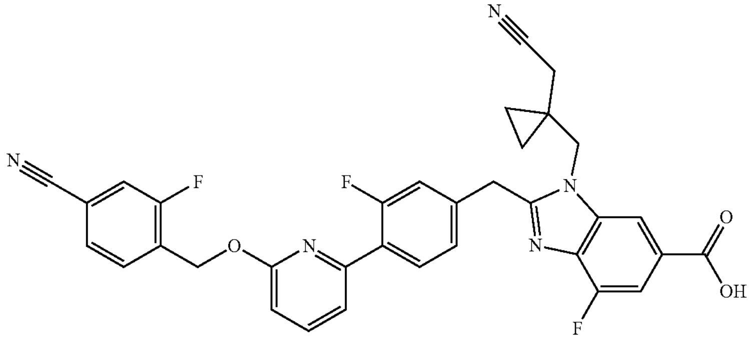 [SMILES: N#CCC1(Cn2c(Cc3ccc(-c4cccc(OCc5ccc(C#N)cc5F)n4)c(F)c3)nc3c(F)cc(C(=O)O)cc32)CC1]<br>2-(4-(6-((4-cyano-2-fluorobenzyl)oxy)pyridin-2-yl)-3-fluorobenzyl)-1-((1-(cyanomethyl)cyclopropyl)methyl)-4-fluoro-1H-benzo[d]imidazole-6-carboxylic acid: ES/MS 608.2; $^1$H NMR (400 MHz, Methanol-d4) δ 8.25 (d, J = 1.2 Hz, 1H), 7.97 (t, J = 8.2 Hz, 1H), 7.85-7.67 (m, 3H), 7.67-7.54 (m, 2H), 7.52-7.44 (m, 1H), 7.31-7.14 (m, 2H), 6.88 (dd, J = 8.3, 0.7 Hz, 1H), 5.61 (s, 2H), 4.59 (s, 2H), 4.51 (s, 2H), 2.52 (s, 2H), 0.80 (s, 4H). |
| 288 | 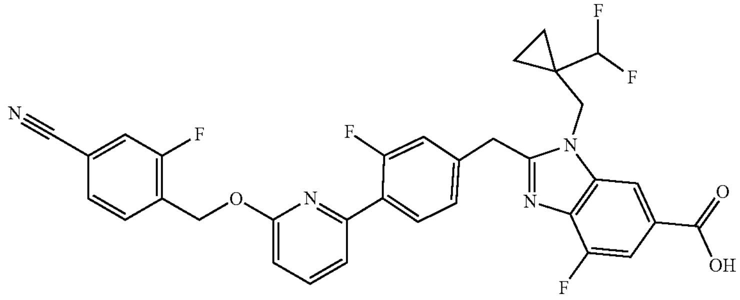 [SMILES: N#Cc1ccc(COc2cccc(-c3ccc(Cc4nc5c(F)cc(C(=O)O)cc5n4CC4(C(F)F)CC4)cc3F)n2)c(F)c1]<br>2-(4-(6-((4-cyano-2-fluorobenzyl)oxy)pyridin-2-yl)-3-fluorobenzyl)-1-((1-(difluoromethyl)cyclopropyl)methyl)-4-fluoro-1H-benzo[d]imidazole-6-carboxylic acid: ES/MS 619.2; $^1$H NMR (400 MHz, Methanol-d4) δ 8.24 (d, J = 1.2 Hz, 1H), 7.98 (t, J = 8.1 Hz, 1H), 7.82-7.74 (m, 2H), 7.74-7.66 (m, 1H), 7.63-7.46 (m, 3H), 7.28-7.12 (m, 2H), 6.89 (d, J = 8.2 Hz, 1H), 5.74-5.38 (m, 3H), 4.69 (s, 2H), 4.61 (s, 2H), 1.04-0.92 (m, 2H), 0.87-0.80 (m, 2H). |
| 293 | 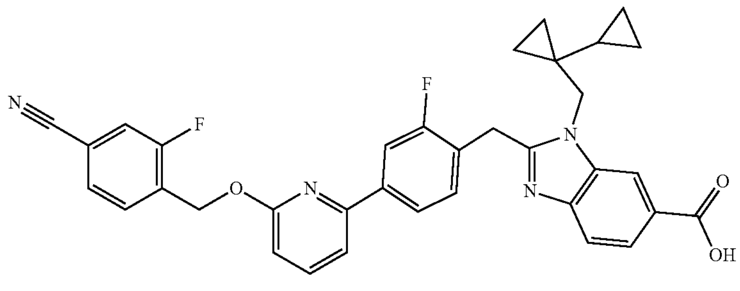 [SMILES: N#Cc1ccc(COc2cccc(-c3ccc(Cc4nc5ccc(C(=O)O)cc5n4CC4(C5CC5)CC4)c(F)c3)n2)c(F)c1]<br>1-([1,1'-bi(cyclopropan)]-1-ylmethyl)-2-(4-(6-((4-cyano-2-fluorobenzyl)oxy)pyridin-2-yl)-2-fluorobenzyl)-1H-benzo[d]imidazole-6-carboxylic acid: ES/MS 591.1; $^1$H NMR (400 MHz, Methanol-d4) δ 8.40 (d, J = 1.4 Hz, 1H), 8.10 (dd, J = 8.6, 1.4 Hz, 1H), 7.87-7.60 (m, 5H), 7.51-7.41 (m, 3H), 7.34 (t, J = 7.8 Hz, 1H), 6.85 (d, J = 8.2 Hz, 1H), 5.61 (s, 2H), 4.43 (s, 2H), 1.02-0.80 (m, 1H), 0.61 (d, J = 5.1 Hz, 2H), 0.52-0.37 (m, 2H), 0.38-0.22 (m, 2H), −0.04 (q, J = 5.2 Hz, 2H). |

-continued

| Example | Structure/Name/Characterization |
|---|---|
| 294 | 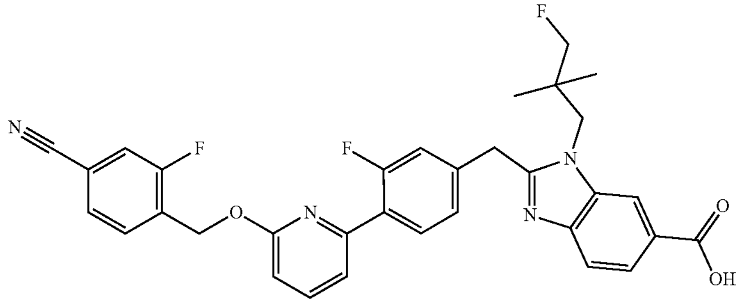 [SMILES: CC(C)(CF)Cn1c(Cc2ccc(-c3cccc(OCc4ccc(C#N)cc4F)n3)c(F)c2)nc2ccc(C(=O)O)cc21] 2-(4-(6-((4-cyano-2-fluorobenzyl)oxy)pyridin-2-yl)-3-fluorobenzyl)-1-(3-fluoro-2,2-dimethylpropyl)-1H-benzo[d]imidazole-6-carboxylic acid: ES/MS 585.2; $^{1}$H NMR (400 MHz, Methanol-d4) δ 8.58 (d, J = 7.7 Hz, 1H), 8.21 (dt, J = 8.6, 2.6 Hz, 1H), 8.03 (dd, J = 9.3, 7.3 Hz, 1H), 7.90-7.67 (m, 3H), 7.64-7.47 (m, 3H), 7.30 (dt, J = 10.2, 3.7 Hz, 2H), 6.93 (dd, J = 8.2, 1.9 Hz, 1H), 5.63 (s, 2H), 4.74 (d, J = 13.9 Hz, 2H), 4.57 (s, 2H), 4.40 (s, 1H), 4.28 (s, 1H), 1.24-1.14 (m, 6H). |
| 295 | 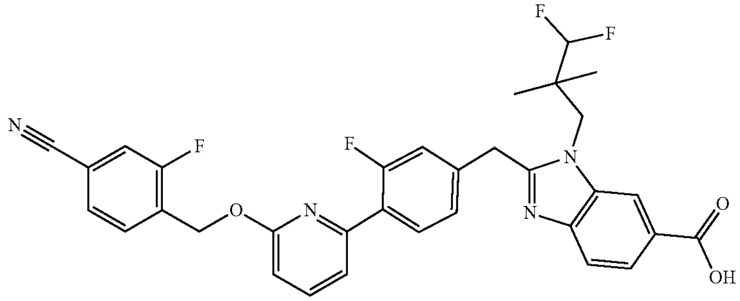 [SMILES: CC(C)(Cn1c(Cc2ccc(-c3cccc(OCc4ccc(C#N)cc4F)n3)c(F)c2)nc2ccc(C(=O)O)cc21)C(F)F] 2-(4-(6-((4-cyano-2-fluorobenzyl)oxy)pyridin-2-yl)-3-fluorobenzyl)-1-(3,3-difluoro-2,2-dimethylpropyl)-1H-benzo[d]imidazole-6-carboxylic acid: ES/MS 603.3; $^{1}$H NMR (400 MHz, Methanol-d4) δ 8.57 (d, J = 1.3 Hz, 1H), 8.21 (dd, J = 8.6, 1.4 Hz, 1H), 8.03 (t, J = 8.2 Hz, 1H), 7.89-7.66 (m, 3H), 7.66-7.56 (m, 2H), 7.52 (dd, J = 7.4, 1.7 Hz, 1H), 7.39-7.24 (m, 2H), 6.92 (d, J = 8.2 Hz, 1H), 5.96 (t, J = 55.8 Hz, 1H), 5.62 (s, 2H), 4.73 (s, 2H), 4.68 (s, 2H), 1.25 (s, 6H). |
| 296 | 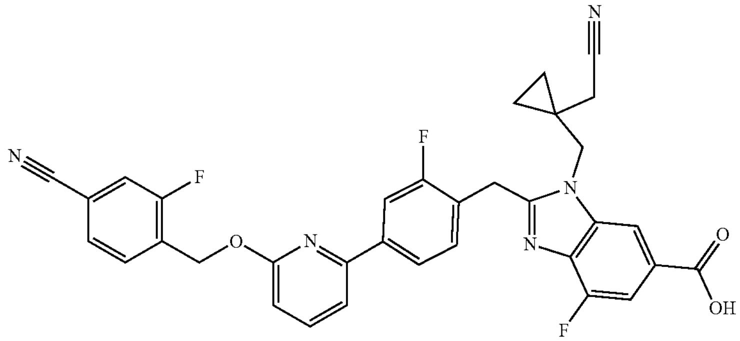 [SMILES: N#CCC1(Cn2c(Cc3ccc(-c4cccc(OCc5ccc(C#N)cc5F)n4)cc3F)nc3c(F)cc(C(=O)O)cc32)CC1] 2-(4-(6-((4-cyano-2-fluorobenzyl)oxy)pyridin-2-yl)-2-fluorobenzyl)-1-((1-(cyanomethyl)cyclopropyl)methyl)-4-fluoro-1H-benzo[d]imidazole-6-carboxylic acid: ES/MS 608.3; $^{1}$H NMR (400 MHz, Methanol-d4) δ 8.25 (d, J = 1.2 Hz, 1H), 7.92-7.66 (m, 5H), 7.64-7.44 (m, 3H), 7.37 (t, J = 7.8 Hz, 1H), 6.88 (d, J = 8.2 Hz, 1H), 5.65 (s, 2H), 4.56 (d, J = 4.6 Hz, 4H), 2.54 (s, 2H), 0.93-0.74 (m, 4H). |

-continued

| Example | Structure/Name/Characterization |
|---|---|
| 297 | 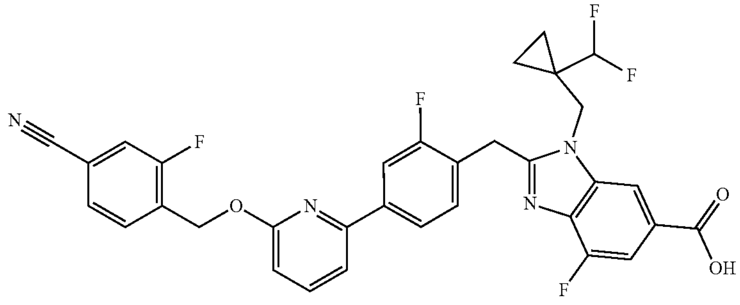 [SMILES: N#Cc1ccc(COc2cccc(-c3ccc(Cc4nc5c(F)cc(C(=O)O)cc5n4CC4(C(F)F)CC4)c(F)c3)n2)c(F)c1] 2-(4-(6-((4-cyano-2-fluorobenzyl)oxy)pyridin-2-yl)-2-fluorobenzyl)-1-((1-(difluoromethyl)cyclopropyl)methyl)-4-fluoro-1H-benzo[d]imidazole-6-carboxylic acid: ES/MS 619.2; $^1$H NMR (400 MHz, Methanol-d4) δ 8.03 (d, J = 1.2 Hz, 1H), 7.84-7.62 (m, 5H), 7.51-7.34 (m, 3H), 7.28 (t, J = 8.0 Hz, 1H), 6.83 (dd, J = 8.3, 0.6 Hz, 1H), 5.69-5.24 (m, 3H), 4.55 (s, 2H), 4.45 (s, 2H), 0.98-0.83 (m, 2H), 0.72 (s, 2H). |
| 299 | 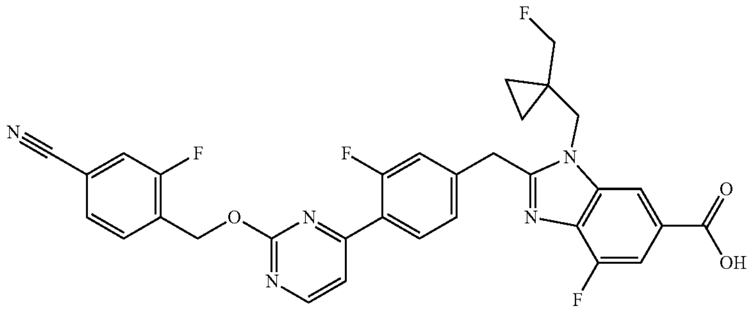 [SMILES: N#Cc1ccc(COc2nccc(-c3ccc(Cc4nc5c(F)cc(C(=O)O)cc5n4CC4(CF)CC4)cc3F)n2)c(F)c1] 2-(4-(2-((4-cyano-2-fluorobenzyl)oxy)pyrimidin-4-yl)-3-fluorobenzyl)-4-fluoro-1-((1-(fluoromethyl)cyclopropyl)methyl)-1H-benzo[d]imidazole-6-carboxylic acid: ES/MS 602.1; $^1$H NMR (400 MHz, Methanol-d4) δ 8.65 (d, J = 5.2 Hz, 1H), 8.21 (d, J = 1.2 Hz, 1H), 8.13 (d, J = 8.1 Hz, 1H), 7.79 (t, J = 7.5 Hz, 1H), 7.71 (dd, J = 11.1, 1.2 Hz, 1H), 7.66-7.54 (m, 3H), 7.37-7.18 (m, 2H), 5.68 (s, 2H), 4.59 (s, 2H), 4.50 (s, 2H), 4.21 (s, 1H), 4.09 (s, 1H), 0.84 (t, J = 4.9 Hz, 2H), 0.79 (d, J = 4.7 Hz, 2H). |
| 300 | 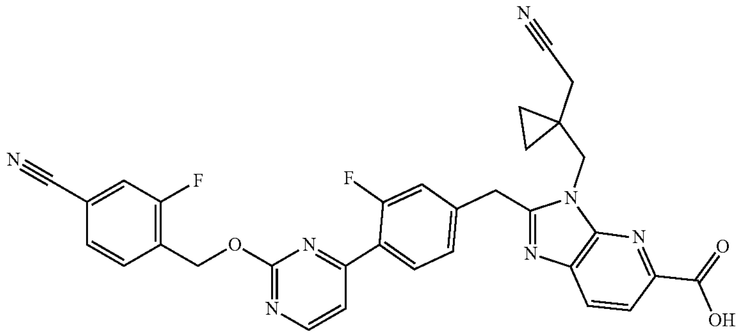 [SMILES: N#CCC1(Cn2c(Cc3ccc(-c4ccnc(OCc5ccc(C#N)cc5F)n4)c(F)c3)nc3ccc(C(=O)O)nc32)CC1] 2-(4-(2-((4-cyano-2-fluorobenzyl)oxy)pyrimidin-4-yl)-3-fluorobenzyl)-3-((1-(cyanomethyl)cyclopropyl)methyl)-3H-imidazo[4,5-b]pyridine-5-carboxylic acid: ES/MS 592.1; $^1$H NMR (400 MHz, Methanol-d4) δ 8.67 (d, J = 5.2 Hz, 1H), 8.30-8.12 (m, 3H), 7.80 (q, J = 8.0, 7.5 Hz, 1H), 7.69-7.55 (m, 3H), 7.44-7.27 (m, 2H), 5.70 (d, J = 7.6 Hz, 2H), 4.66 (s, 2H), 4.59 (s, 2H), 2.69 (s, 2H), 1.13-1.02 (m, 2H), 0.84-0.72 (m, 2H). |

-continued

| Example | Structure/Name/Characterization |
|---|---|
| 301 | 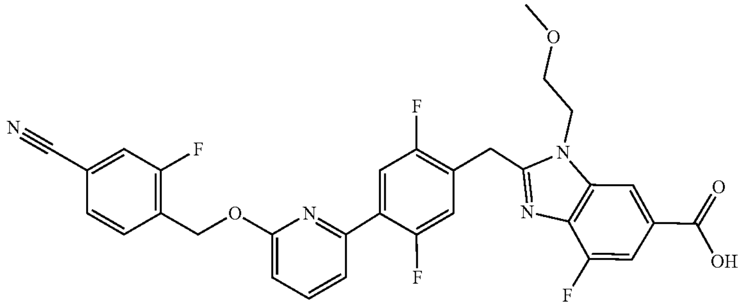 [SMILES: COCCn1c(Cc2cc(F)c(-c3cccc(OCc4ccc(C#N)cc4F)n3)cc2F)nc2c(F)cc(C(=O)O)cc21] 2-(4-(6-((4-cyano-2-fluorobenzyl)oxy)pyridin-2-yl)-2,5-difluorobenzyl)-4-fluoro-1-(2-methoxyethyl)-1H-benzo[d]imidazole-6-carboxylic acid: ES/MS 591.2; $^{1}$H NMR (400 MHz, Methanol-d4) δ 8.01 (d, J = 4.2 Hz, 1H), 7.69 (dt, J = 13.3, 6.2 Hz, 4H), 7.49 (q, J = 10.1, 7.6 Hz, 3H), 7.05 (dd, J = 10.9, 5.9 Hz, 1H), 6.85 (t, J = 6.2 Hz, 1H), 5.59 (d, J = 4.6 Hz, 2H), 4.46 (s, 4H), 3.69 (d, J = 5.4 Hz, 2H), 3.25 (d, J = 4.4 Hz, 3H). |
| 302 | 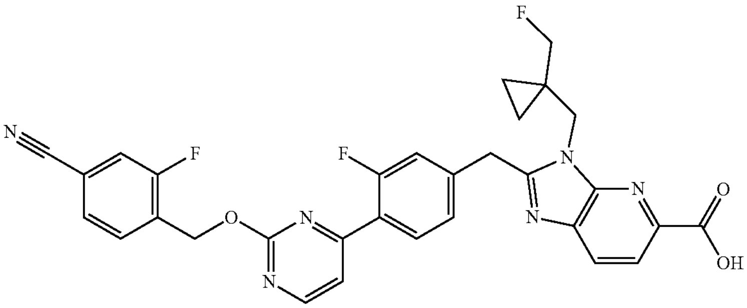 [SMILES: N#Cc1ccc(COc2nccc(-c3ccc(Cc4nc5ccc(C(=O)O)nc5n4CC4(CF)CC4)cc3F)n2)c(F)c1] 2-(4-(2-((4-cyano-2-fluorobenzyl)oxy)pyrimidin-4-yl)-3-fluorobenzyl)-3-((1-(fluoromethyl)cyclopropyl)methyl)-3H-imidazo[4,5-b]pyridine-5-carboxylic acid: ES/MS 585.1; $^{1}$H NMR (400 MHz, Methanol-d4) δ 8.63 (d, J = 5.2 Hz, 1H), 8.26-8.06 (m, 3H), 7.78 (d, J = 7.8 Hz, 1H), 7.65-7.51 (m, 3H), 7.31 (dd, J = 8.2, 1.6 Hz, 1H), 7.27-7.18 (m, 1H), 5.67 (s, 2H), 4.60 (s, 2H), 4.52 (s, 2H), 4.31 (s, 1H), 4.19 (s, 1H), 1.13 (t, J = 5.3 Hz, 2H), 0.69 (d, J = 5.8 Hz, 2H). |
| 303 | 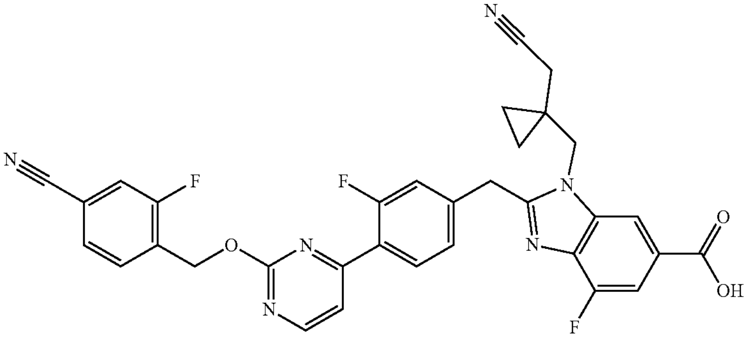 [SMILES: N#CCC1(Cn2c(Cc3ccc(-c4ccnc(OCc5ccc(C#N)cc5F)n4)c(F)c3)nc3c(F)cc(C(=O)O)cc32)CC1] 2-(4-(2-((4-cyano-2-fluorobenzyl)oxy)pyrimidin-4-yl)-3-fluorobenzyl)-1-((1-(cyanomethyl)cyclopropyl)methyl)-4-fluoro-1H-benzo[d]imidazole-6-carboxylic acid: ES/MS 609.2; $^{1}$H NMR (400 MHz, Methanol-d4) δ 8.65 (d, J = 5.3 Hz, 1H), 8.31-8.21 (m, 1H), 8.14 (t, J = 8.1 Hz, 1H), 7.79 (t, J = 7.4 Hz, 1H), 7.75-7.66 (m, 1H), 7.66-7.56 (m, 3H), 7.41-7.25 (m, 2H), 5.68 (s, 2H), 4.62 (s, 2H), 4.52 (s, 2H), 2.54 (s, 2H), 0.80 (s, 4H). |

-continued

| Example | Structure/Name/Characterization |
| --- | --- |
| 305 | 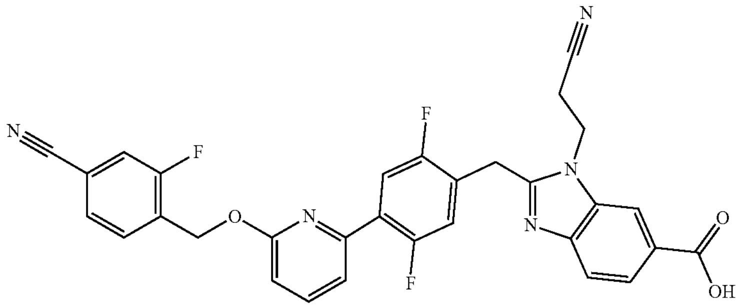 [SMILES: N#CCCn1c(Cc2cc(F)c(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2,5-difluorobenzyl)-1-(2-cyanoethyl)-1H-benzo[d]imidazole-6-carboxylic acid: ES/MS 568.2; $^{1}$H NMR (400 MHz, Methanol-d4) δ 8.51 (d, J = 1.4 Hz, 1H), 8.14 (dd, J = 8.6, 1.5 Hz, 1H), 7.87-7.78 (m, 2H), 7.74 (t, J = 8.1 Hz, 2H), 7.59 (ddt, J = 11.6, 7.6, 1.7 Hz, 3H), 7.34 (dd, J = 11.3, 6.1 Hz, 1H), 6.95 (d, J = 8.3 Hz, 1H), 5.64 (s, 2H), 4.90 (d, J = 6.7 Hz, 2H), 4.68 (s, 2H), 3.16 (t, J = 6.5 Hz, 2H). |
| 306 | (mixture) 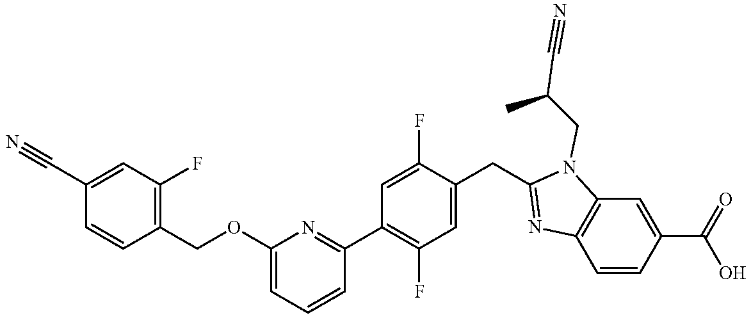 and 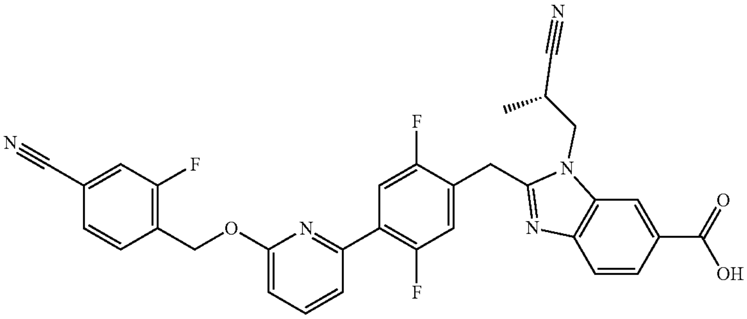 [SMILES: C[C@H](C#N)Cn1c(Cc2cc(F)c(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2,5-difluorobenzyl)-1-(2-cyanopropyl)-1H-benzo[d]imidazole-6-carboxylic acid: ES/MS 582.3; $^{1}$H NMR (400 MHz, Methanol-d4) δ 8.51 (dd, J = 1.5, 0.7 Hz, 1H), 8.13 (dd, J = 8.6, 1.5 Hz, 1H), 7.91-7.78 (m, 2H), 7.78-7.66 (m, 2H), 7.65-7.51 (m, 3H), 7.34 (dd, J = 11.3, 6.1 Hz, 1H), 6.95 (dd, J = 8.3, 0.7 Hz, 1H), 5.64 (s, 2H), 4.81-4.58 (m, 3H), 3.68-3.51 (m, 1H), 1.54 (d, J = 7.0 Hz, 3H). |
| 307 | 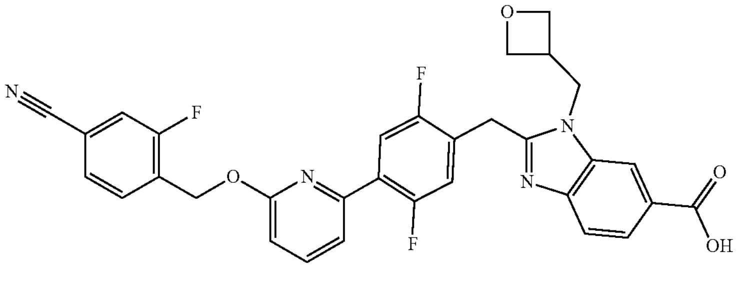 [SMILES: N#Cc1ccc(COc2cccc(-c3cc(F)c(Cc4nc5ccc(C(=O)O)cc5n4CC4COC4)cc3F)n2)c(F)c1] |

-continued

| Example | Structure/Name/Characterization |
|---|---|
| | 2-(4-(6-((4-cyano-2-fluorobenzyl)oxy)pyridin-2-yl)-2,5-difluorobenzyl)-1-(oxetan-3-ylmethyl)-1H-benzo[d]imidazole-6-carboxylic acid: ES/MS 585.2; $^{1}$H NMR (400 MHz, Methanol-d4) δ 8.53 (t, J = 1.0 Hz, 1H), 8.17 (dd, J = 8.6, 1.4 Hz, 1H), 7.91-7.77 (m, 2H), 7.77-7.64 (m, 2H), 7.69-7.55 (m, 3H), 7.36 (dd, J = 11.1, 6.1 Hz, 1H), 6.96 (d, J = 8.3 Hz, 1H), 5.63 (s, 2H), 4.94 (d, J = 7.5 Hz, 2H), 4.81 (dd, J = 7.7, 6.5 Hz, 2H), 4.69 (s, 2H), 4.62 (t, J = 6.2 Hz, 2H), 3.69 (m, 1H). |
| 308 | 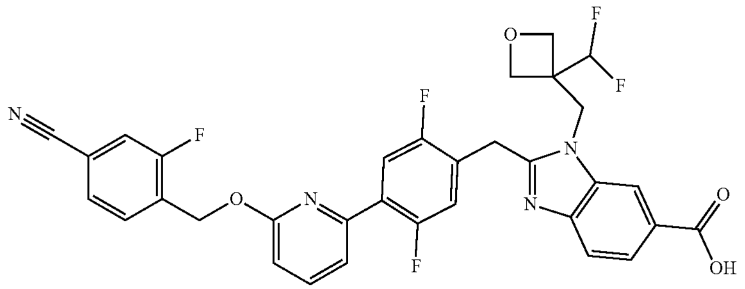 [SMILES: N#Cc1ccc(COc2cccc(-c3cc(F)c(Cc4nc5ccc(C(=O)O)cc5n4CC4(C(F)F)COC4)cc3F)n2)c(F)c1] 2-(4-(6-((4-cyano-2-fluorobenzyl)oxy)pyridin-2-yl)-2,5-difluorobenzyl)-1-((3-(difluoromethyl)oxetan-3-yl)methyl)-1H-benzo[d]imidazole-6-carboxylic acid: ES/MS 635.1; $^{1}$H NMR (400 MHz, Methanol-d4) δ 8.42 (d, J = 1.4 Hz, 1H), 8.13 (dd, J = 8.5, 1.5 Hz, 1H), 7.90-7.69 (m, 4H), 7.67-7.50 (m, 3H), 7.31 (dd, J = 11.3, 6.0 Hz, 1H), 6.95 (dd, J = 8.2, 0.7 Hz, 1H), 6.47 (t, J = 55.2 Hz, 1H), 5.63 (s, 2H), 4.97 (s, 2H), 4.72 (s, 4H), 4.57 (s, 2H). |
| 310 | 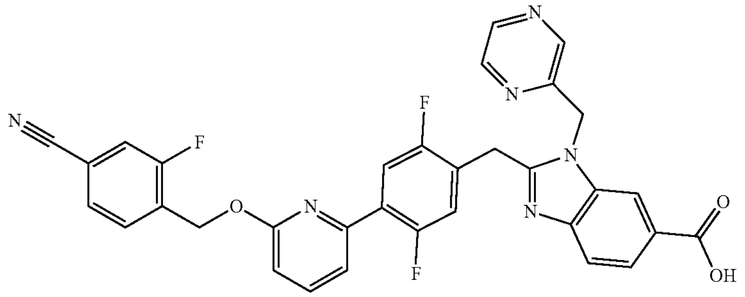 [SMILES: N#Cc1ccc(COc2cccc(-c3cc(F)c(Cc4nc5ccc(C(=O)O)cc5n4Cc4cnccn4)cc3F)n2)c(F)c1] 2-(4-(6-((4-cyano-2-fluorobenzyl)oxy)pyridin-2-yl)-2,5-difluorobenzyl)-1-(pyrazin-2-ylmethyl)-1H-benzo[d]imidazole-6-carboxylic acid: ES/MS 607.3; $^{1}$H NMR (400 MHz, Methanol-d4) δ 8.72 (d, J = 1.5 Hz, 1H), 8.45 (d, J = 2.5 Hz, 1H), 8.43-8.36 (m, 2H), 8.18 (dd, J = 8.6, 1.5 Hz, 1H), 7.88-7.78 (m, 2H), 7.73 (t, J = 7.5 Hz, 1H), 7.69-7.55 (m, 3H), 7.52 (dd, J = 7.6, 1.7 Hz, 1H), 7.25 (dd, J = 11.2, 6.0 Hz, 1H), 6.95 (d, J = 8.3 Hz, 1H), 6.03 (s, 2H), 5.63 (s, 2H), 4.74 (s, 2H). |
| 311 | 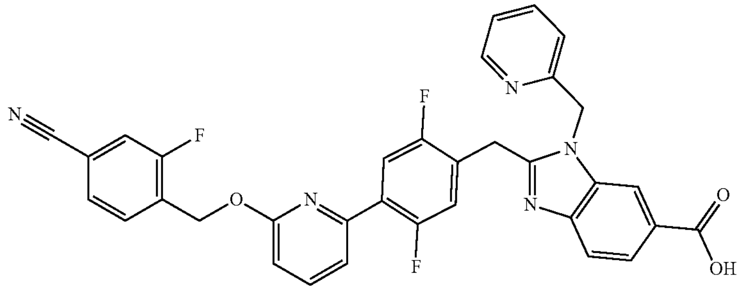 [SMILES: N#Cc1ccc(COc2cccc(-c3cc(F)c(Cc4nc5ccc(C(=O)O)cc5n4Cc4ccccn4)cc3F)n2)c(F)c1] 2-(4-(6-((4-cyano-2-fluorobenzyl)oxy)pyridin-2-yl)-2,5-difluorobenzyl)-1-(pyridin-2-ylmethyl)-1H-benzo[d]imidazole-6-carboxylic acid: ES/MS 606.2; $^{1}$H NMR (400 MHz, Methanol-d4) δ 8.44-8.32 (m, 2H), 8.22 (dd, J = 8.6, 1.5 Hz, 1H), 7.88-7.76 (m, 3H), 7.76-7.55 (m, 4H), 7.51 (dd, J = 7.5, 1.7 Hz, 1H), 7.44 (d, J = 7.9 Hz, 1H), 7.36-7.20 (m, 2H), 6.95 (d, J = 8.2 Hz, 1H), 5.98 (s, 2H), 5.62 (s, 2H), 4.79 (s, 2H). |

-continued

| Example | Structure/Name/Characterization |
|---|---|
| 312 | 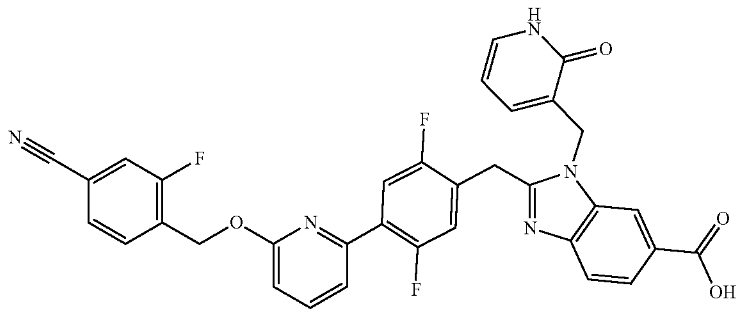 [SMILES: N#Cc1ccc(COc2cccc(-c3cc(F)c(Cc4nc5ccc(C(=O)O)cc5n4Cc4ccc[nH]c4=O)cc3F)n2)c(F)c1]<br>2-(4-(6-((4-cyano-2-fluorobenzyl)oxy)pyridin-2-yl)-2,5-difluorobenzyl)-1-((2-oxo-1,2-dihydropyridin-3-yl)methyl)-1H-benzo[d]imidazole-6-carboxylic acid: ES/MS 622.1; $^1$H NMR (400 MHz, Methanol-d4) δ 8.44-8.35 (m, 1H), 8.18 (ddd, J = 8.3, 6.8, 1.5 Hz, 1H), 7.91-7.78 (m, 2H), 7.78-7.69 (m, 2H), 7.67-7.53 (m, 4H), 7.43-7.30 (m, 2H), 6.96 (d, J = 8.2 Hz, 1H), 6.32 (dt, J = 10.5, 6.7 Hz, 1H), 5.68-5.54 (m, 4H), 4.89 (s, 2H). |
| 313 | 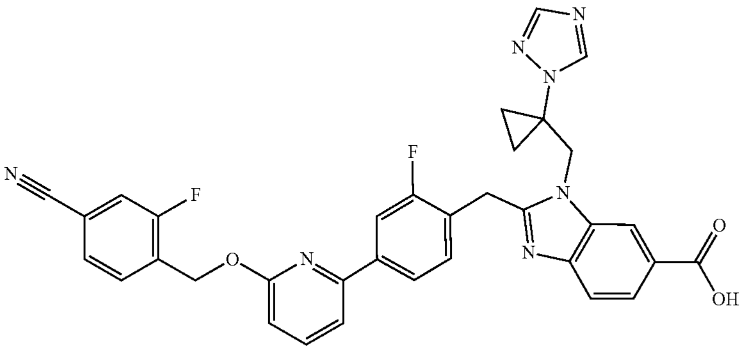 [SMILES: N#Cc1ccc(COc2cccc(-c3ccc(Cc4nc5ccc(C(=O)O)cc5n4CC4(n5cncn5)CC4)c(F)c3)n2)c(F)c1]<br>1-((1-(1H-1,2,4-triazol-1-yl)cyclopropyl)methyl)-2-(4-(6-((4-cyano-2-fluorobenzyl)oxy)pyridin-2-yl)-2-fluorobenzyl)-1H-benzo[d]imidazole-6-carboxylic acid: ES/MS 618.7; $^1$H NMR (400 MHz, Methanol-d4) δ 8.46 (s, 1H), 8.18 (dd, J = 8.6, 1.4 Hz, 1H), 8.13 (d, J = 1.3 Hz, 1H), 8.00-7.87 (m, 3H), 7.83 (t, J = 7.9 Hz, 1H), 7.73 (dt, J = 7.5, 3.3 Hz, 2H), 7.65-7.55 (m, 3H), 7.50 (t, J = 7.9 Hz, 1H), 6.93 (d, J = 8.2 Hz, 1H), 5.66 (s, 2H), 5.14 (s, 2H), 4.46 (s, 2H), 1.75-1.63 (m, 2H), 1.63-1.53 (m, 2H). |
| 315 | 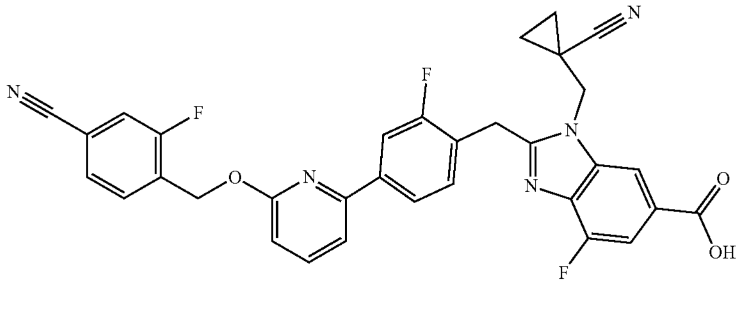 [SMILES: N#Cc1ccc(COc2cccc(-c3ccc(Cc4nc5c(F)cc(C(=O)O)cc5n4CC4(C#N)CC4)c(F)c3)n2)c(F)c1]<br>2-(4-(6-((4-cyano-2-fluorobenzyl)oxy)pyridin-2-yl)-2-fluorobenzyl)-1-((l-cyanocyclopropyl)methyl)-4-fluoro-1H-benzo[d]imidazole-6-carboxylic acid: ES/MS 594.2; $^1$H NMR (400 MHz, Methanol-d4) δ 8.06 (d, J = 1.2 Hz, 1H), 7.83-7.67 (m, 5H), 7.52-7.37 (m, 3H), 7.32 (t, J = 8.1 Hz, 1H), 6.83 (d, J = 8.1 Hz, 1H), 5.61 (s, 2H), 4.55 (s, 2H), 4.48 (s, 2H), 1.50-1.36 (m, 2H), 1.36-1.27 (m, 2H). |

-continued

| Example | Structure/Name/Characterization |
|---|---|
| 316 | 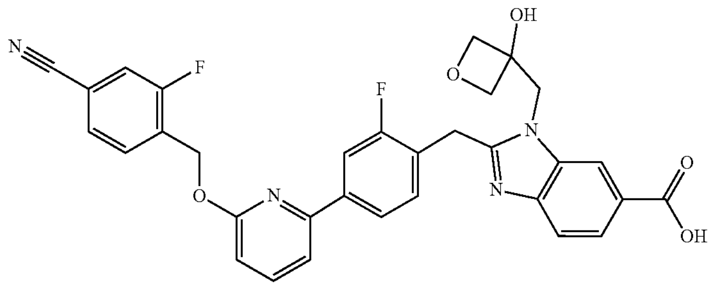 [SMILES: N#Cc1ccc(COc2cccc(-c3ccc(Cc4nc5ccc(C(=O)O)cc5n4CC4(O)COC4)c(F)c3)n2)c(F)c1] 2-(4-(6-((4-cyano-2-fluorobenzyl)oxy)pyridin-2-yl)-2-fluorobenzyl)-1-((3-hydroxyoxetan-3-yl)methyl)-1H-benzo[d]imidazole-6-carboxylic acid: ES/MS 583.2; $^{1}$H NMR (400 MHz, DMSO-d6) δ 8.32 (d, J = 1.3 Hz, 1H), 7.95-7.81 (m, 5H), 7.79-7.70 (m, 2H), 7.65 (dd, J = 15.1, 7.9 Hz, 2H), 7.45 (t, J = 8.0 Hz, 1H), 6.94 (d, J = 8.2 Hz, 1H), 5.62 (s, 2H), 4.66 (s, 2H), 4.51-4.39 (m, 3H), 4.29 (d, J = 6.2 Hz, 2H). |
| 323 | 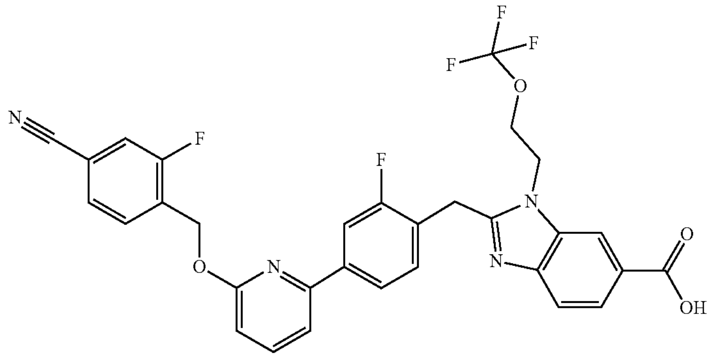 [SMILES: N#Cc1ccc(COc2cccc(-c3ccc(Cc4nc5ccc(C(=O)O)cc5n4CCOC(F)(F)F)c(F)c3)n2)c(F)c1] 2-(4-(6-((4-cyano-2-fluorobenzyl)oxy)pyridin-2-yl)-2-fluorobenzyl)-1-(2-(trifluoromethoxy)ethyl)-1H-benzo[d]imidazole-6-carboxylic acid: ES/MS 609.2; $^{1}$H NMR (400 MHz, DMSO-d6) δ 8.28 (d, J = 1.5 Hz, 1H), 7.95-7.80 (m, 5H), 7.80-7.69 (m, 2H), 7.64 (dd, J = 19.9, 7.9 Hz, 2H), 7.45 (t, J = 7.9 Hz, 1H), 6.94 (d, J = 8.2 Hz, 1H), 5.62 (s, 2H), 4.80 (d, J = 5.2 Hz, 2H), 4.45 (d, J = 4.2 Hz, 2H). |
| 324 | 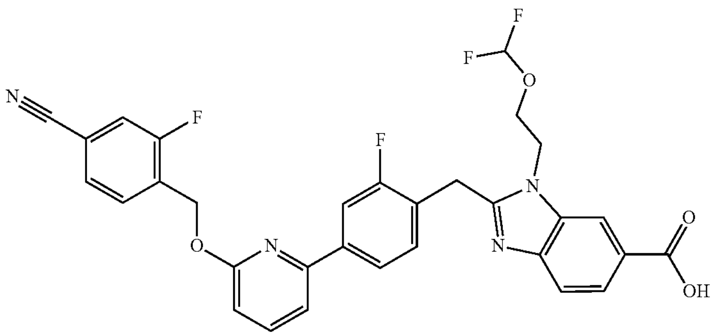 [SMILES: N#Cc1ccc(COc2cccc(-c3ccc(Cc4nc5ccc(C(=O)O)cc5n4CCOC(F)F)c(F)c3)n2)c(F)c1] 2-(4-(6-((4-cyano-2-fluorobenzyl)oxy)pyridin-2-yl)-2-fluorobenzyl)-1-(2-(difluoromethoxy)ethyl)-1H-benzo[d]imidazole-6-carboxylic acid; ES/MS 591.2; $^{1}$H NMR (400 MHz, DMSO-d6) δ 8.32 (d, J = 1.5 Hz, 1H), 7.96-7.83 (m, 5H), 7.80-7.70 (m, 2H), 7.66 (dd, J = 13.8, 8.0 Hz, 2H), 7.47 (t, J = 7.9 Hz, 1H), 6.94 (d, J = 8.2 Hz, 1H), 6.64 (t, J = 76 Hz, 1H), 5.62 (s, 2H), 4.76 (t, J = 5.1 Hz, 2H), 4.21 (t, J = 5.0 Hz, 2H). |

-continued

| Example | Structure/Name/Characterization |
|---|---|
| 325 | 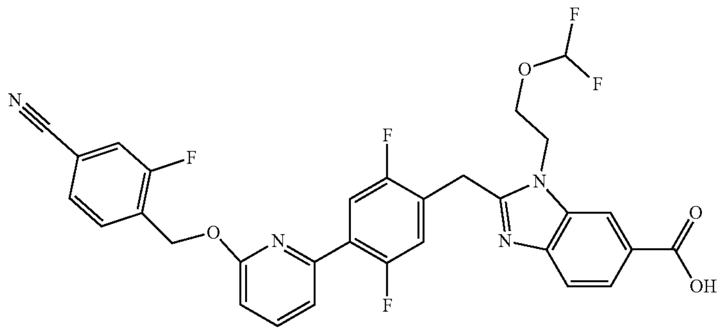 [SMILES: N#Cc1ccc(COc2cccc(-c3cc(F)c(Cc4nc5ccc(C(=O)O)cc5n4CCOC(F)F)cc3F)n2)c(F)c1]<br>2-(4-(6-((4-cyano-2-fluorobenzyl)oxy)pyridin-2-yl)-2,5-difluorobenzyl)-1-(2-(difluoromethoxy)ethyl)-1H-benzo[d]imidazole-6-carboxylic acid: ES/MS 602.2; $^1$H NMR (400 MHz, DMSO-d6) δ 8.25 (d, J = 1.5 Hz, 1H), 7.95-7.86 (m, 2H), 7.83-7.71 (m, 4H), 7.61 (d, J = 8.4 Hz, 1H), 7.53 (dd, J = 7.6, 1.7 Hz, 1H), 7.38 (dd, J = 11.6, 6.1 Hz, 1H), 6.99 (d, J = 8.2 Hz, 1H), 6.65 (t, J = 75.3 Hz, 1H), 5.61 (s, 2H), 4.72 (t, J = 5.1 Hz, 2H), 4.44 (s, 2H), 4.21 (t, J = 5.1 Hz, 2H). |
| 326 | 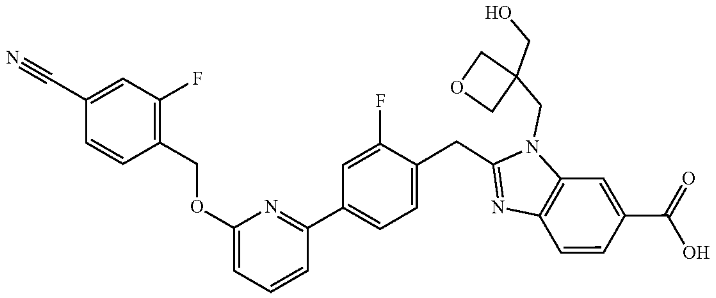 [SMILES: N#Cc1ccc(COc2cccc(-c3ccc(Cc4nc5ccc(C(=O)O)cc5n4CC4(CO)COC4)c(F)c3)n2)c(F)c1]<br>2-(4-(6-((4-cyano-2-fluorobenzyl)oxy)pyridin-2-yl)-2-fluorobenzyl)-1-((3-(hydroxymethyl)oxetan-3-yl)methyl)-1H-benzo[d]imidazole-6-carboxylic acid: ES/MS 597.2; $^1$H NMR (400 MHz, DMSO-d6) δ 8.38 (s, 1H), 7.96-7.55 (m, 9H), 7.42 (t, J = 7.5 Hz, 1H), 6.93 (d, J = 8.2 Hz, 1H), 5.62 (s, 2H), 4.80 (s, 1H), 4.65-4.36 (m, 6H). |
| 327 | 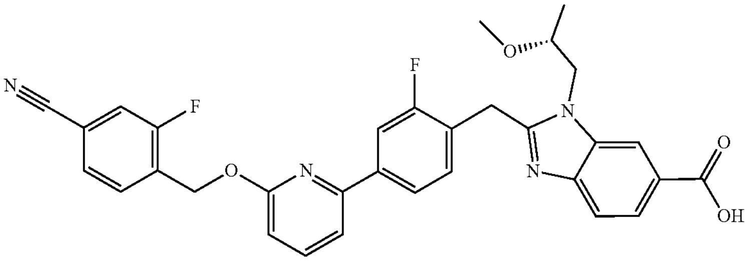 [SMILES: CO[C@H](C)Cn1c(Cc2ccc(-c3cccc(OCc4ccc(C#N)cc4F)n3)cc2F)nc2ccc(C(=O)O)cc21]<br>(R)-2-(4-(6-((4-cyano-2-fluorobenzyl)oxy)pyridin-2-yl)-2-fluorobenzyl)-1-(2-methoxypropyl)-1H-benzo[d]imidazole-6-carboxylic acid: ES/MS 569.3; $^1$H NMR (400 MHz, Acetonitrile-d3) δ 8.42 (dd, J = 1.5, 0.7 Hz, 1H), 8.10 (dd, J = 8.6, 1.5 Hz, 1H), 7.90-7.82 (m, 3H), 7.82-7.79 (m, 1H), 7.77 (dd, J = 8.6, 0.7 Hz, 1H), 7.73 (t, J = 7.6 Hz, 1H), 7.61-7.56 (m, 2H), 7.55-7.51 (m, 1H), 7.48 (t, J = 8.0 Hz, 1H), 6.90 (d, J = 8.2 Hz, 1H), 5.64 (s, 2H), 4.74-4.59 (m, 2H), 4.50 (dd, J = 15.2, 3.0 Hz, 1H), 4.39 (dd, J = 15.2, 9.3 Hz, 1H), 3.74 (ddd, J = 9.2, 6.1, 3.0 Hz, 1H), 3.14 (s, 3H), 1.31 (d, J = 6.2 Hz, 3H). |

-continued

| Example | Structure/Name/Characterization |
|---|---|
| 331 | 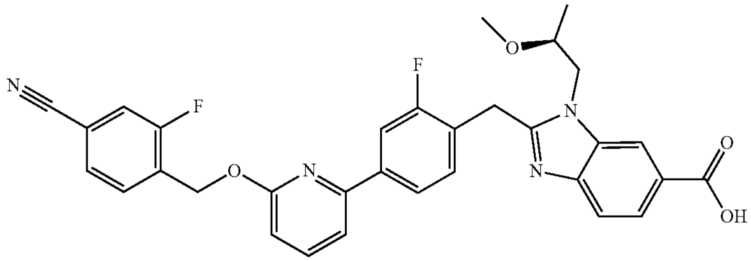 [SMILES: CO[C@@H](C)Cn1c(Cc2ccc(-c3cccc(OCc4ccc(C#N)cc4F)n3)cc2F)nc2ccc(C(=O)O)cc21] (S)-2-(4-(6-((4-cyano-2-fluorobenzyl)oxy)pyridin-2-yl)-2-fluorobenzyl)-1-(2-methoxypropyl)-1H-benzo[d]imidazole-6-carboxylic acid: ES/MS 569.5; $^{1}$H NMR (400 MHz, Acetonitrile-d3) δ 8.45 (t, J = 1.0 Hz, 1H), 8.13 (dd, J = 8.6, 1.4 Hz, 1H), 7.86 (d, J = 1.9 Hz, 1H), 7.86-7.77 (m, 3H), 7.76-7.68 (m, 1H), 7.58 (d, J = 8.7 Hz, 2H), 7.54-7.45 (m, 2H), 6.90 (d, J = 8.2 Hz, 1H), 5.64 (s, 2H), 4.81-4.60 (m, 2H), 4.53 (dd, J = 15.2, 2.9 Hz, 1H), 4.41 (dd, J = 15.2, 9.4 Hz, 1H), 3.75 (ddp, J = 9.4, 6.2, 3.0 Hz, 1H), 3.15 (s, 3H), 1.32 (d, J = 6.2 Hz, 3H). |
| 343 | 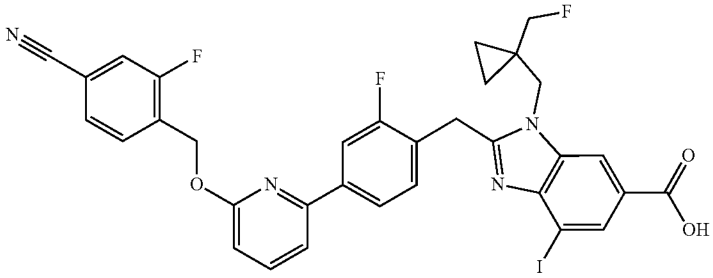 [SMILES: N#Cc1ccc(COc2cccc(-c3ccc(Cc4nc5c(I)cc(C(=O)O)cc5n4CC4(CF)CC4)c(F)c3)n2)c(F)c1] 2-(4-(6-((4-cyano-2-fluorobenzyl)oxy)pyridin-2-yl)-2-fluorobenzyl)-1-((1-(fluoromethyl)cyclopropyl)methyl)-4-iodo-1H-benzo[d]imidazole-6-carboxylic acid: ES/MS 708; $^{1}$H NMR (400 MHz, DMSO-d6) δ 8.26 (d, J = 1.4 Hz, 1H), 8.18 (d, J = 1.3 Hz, 1H), 7.97-7.82 (m, 4H), 7.81-7.70 (m, 2H), 7.67 (d, J = 7.4 Hz, 1H), 7.38 (t, J = 8.1 Hz, 1H), 6.93 (d, J = 8.1 Hz, 1H), 5.62 (s, 2H), 4.50 (s, 2H), 4.47 (s, 2H), 4.15 (d, J = 48.8 Hz, 2H), 0.86-0.75 (m, 2H), 0.72-0.64 (m, 2H). |
| 351 | 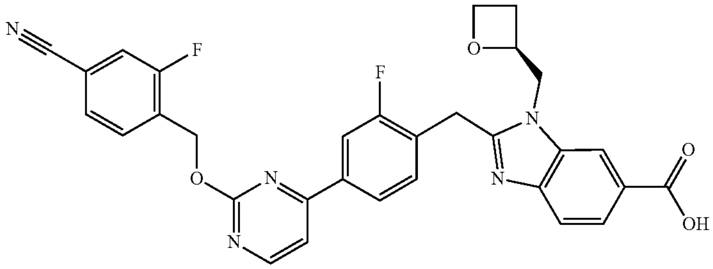 [SMILES: N#Cc1ccc(COc2nccc(-c3ccc(Cc4nc5ccc(C(=O)O)cc5n4C[C@@H]4CCO4)c(F)c3)n2)c(F)c1] (S)-2-(4-(2-((4-cyano-2-fluorobenzyl)oxy)pyrimidin-4-yl)-2-fluorobenzyl)-1-(oxetan-2-ylmethyl)-1H-benzo[d]imidazole-6-carboxylic acid: ES/MS 568.2; $^{1}$H NMR (400 MHz, DMSO-d6) δ 8.74 (d, J = 5.3 Hz, 1H), 8.29 (d, J = 1.4 Hz, 1H), 8.09-8.04 (m, 1H), 8.04-8.00 (m, 1H), 7.98-7.91 (m, 1H), 7.87-7.73 (m, 4H), 7.61 (d, J = 8.4 Hz, 1H), 7.54 (t, J = 8.0 Hz, 1H), 5.63 (s, 2H), 5.12-5.02 (m, 1H), 4.77 (dd, J = 15.6, 7.1 Hz, 1H), 4.68-4.55 (m, 2H), 4.54-4.46 (m, 2H), 4.41-4.32 (m, 1H), 2.78-2.66 (m, 1H), 2.43-2.35 (m, 1H). |

-continued

| Example | Structure/Name/Characterization |
|---|---|
| 353 | 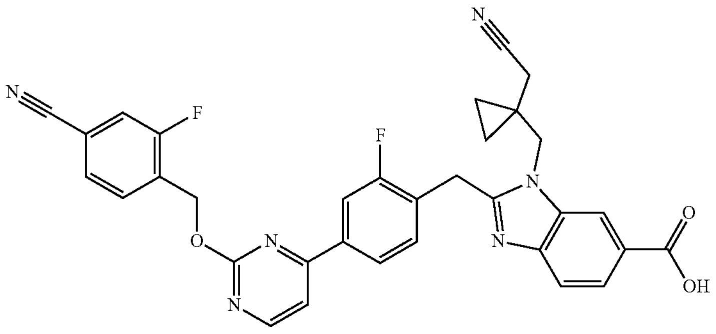 [SMILES: N#CCC1(Cn2c(Cc3ccc(-c4ccnc(OCc5ccc(C#N)cc5F)n4)cc3F)nc3ccc(C(=O)O)cc32)CC1]<br>2-(4-(2-((4-cyano-2-fluorobenzyl)oxy)pyrimidin-4-yl)-2-fluorobenzyl)-1-((1-(cyanomethyl)cyclopropyl)methyl)-1H-benzo[d]imidazole-6-carboxylic acid: ES/MS 591.2; $^1$H NMR (400 MHz, DMSO-d6) δ 8.75 (d, J = 5.2 Hz, 1H), 8.30 (d, J = 1.4 Hz, 1H), 8.04 (d, J = 9.5 Hz, 2H), 7.95 (dd, J = 9.9, 1.4 Hz, 1H), 7.87-7.71 (m, 4H), 7.58 (dd, J = 17.1, 8.2 Hz, 2H), 5.64 (s, 2H), 4.58 (s, 2H), 4.51 (s, 2H), 2.68 (s, 2H), 0.80-0.66 (m, 4H). |
| 355 | 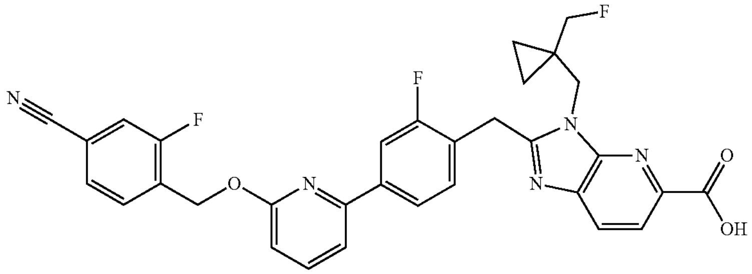 [SMILES: N#Cc1ccc(COc2cccc(-c3ccc(Cc4nc5ccc(C(=O)O)nc5n4CC4(CF)CC4)c(F)c3)n2)c(F)c1]<br>2-(4-(6-((4-cyano-2-fluorobenzyl)oxy)pyridin-2-yl)-2-fluorobenzyl)-3-((1-(fluoromethyl)cyclopropyl)methyl)-3H-imidazo[4,5-b]pyridine-5-carboxylic acid: ES/MS 584.4; 1H NMR (400 MHz, DMSO-d6) δ 8.06 (d, J = 8.2 Hz, 1H), 7.97 (d, J = 8.3 Hz, 1H), 7.92 (dd, J = 10.0, 1.4 Hz, 1H), 7.87 (dd, J = 11.0, 8.2 Hz, 3H), 7.82-7.70 (m, 2H), 7.67 (d, J = 7.5 Hz, 1H), 7.49 (t, J = 7.9 Hz, 1H), 6.94 (d, J = 8.2 Hz, 1H), 5.63 (s, 2H), 4.50 (s, 4H), 4.32 (d, J = 48.8 Hz, 2H), 1.12 (t, J = 5.4 Hz, 2H), 0.69 (d, J = 5.5 Hz, 2H). |
| 359 | 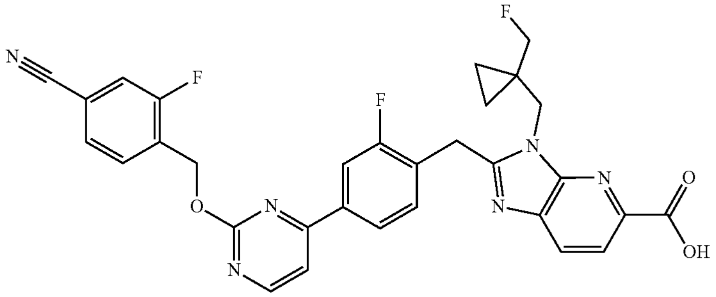 [SMILES: N#Cc1ccc(COc2nccc(-c3ccc(Cc4nc5ccc(C(=O)O)nc5n4CC4(CF)CC4)c(F)c3)n2)c(F)c1]<br>2-(4-(2-((4-cyano-2-fluorobenzyl)oxy)pyrimidin-4-yl)-2-fluorobenzyl)-3-((1-(fluoromethyl)cyclopropyl)methyl)-3H-imidazo[4,5-b]pyridine-5-carboxylic acid: ES/MS 585.1; $^1$H NMR (400 MHz, DMSO-d6) δ 8.75 (d, J = 5.2 Hz, 1H), 8.05 (dd, J = 8.9, 5.2 Hz, 3H), 8.00-7.91 (m, 2H), 7.84 (d, J = 5.3 Hz, 1H), 7.82-7.73 (m, 2H), 7.58 (t, J = 7.8 Hz, 1H), 5.64 (s, 2H), 4.54 (s, 2H), 4.50 (s, 2H), 4.32 (d, J = 48.9 Hz, 2H), 1.16-1.08 (m, 2H), 0.73-0.63 (m, 2H). |

-continued

| Example | Structure/Name/Characterization |
|---|---|
| 360 | 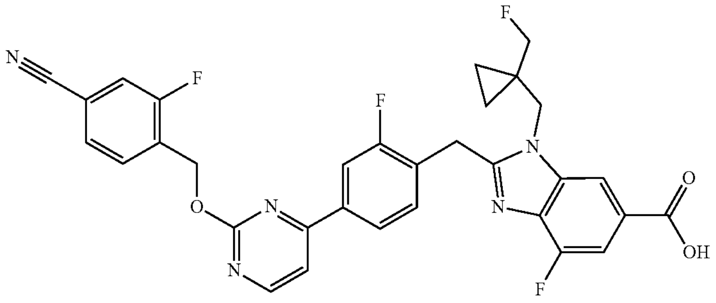 [SMILES: N#Cc1ccc(COc2nccc(-c3ccc(Cc4nc5c(F)cc(C(=O)O)cc5n4CC4(CF)CC4)c(F)c3)n2)c(F)c1] 2-(4-(2-((4-cyano-2-fluorobenzyl)oxy)pyrimidin-4-yl)-2-fluorobenzyl)-4-fluoro-1-((1-(fluoromethyl)cyclopropyl)methyl)-1H-benzo[d]imidazole-6-carboxylic acid: ES/MS 602.2; $^1$H NMR (400 MHz, DMSO-d6) δ 8.74 (d, J = 5.3 Hz, 1H), 8.13 (d, J = 1.2 Hz, 1H), 8.08-8.04 (m, 1H), 8.03 (s, 1H), 7.94 (dd, J = 9.9, 1.4 Hz, 1H), 7.84 (d, J = 5.2 Hz, 1H), 7.82-7.71 (m, 2H), 7.60-7.45 (m, 2H), 5.63 (s, 2H), 4.57 (s, 2H), 4.49 (s, 2H), 4.17 (d, J = 48.8 Hz, 2H), 0.88-0.79 (m, 2H), 0.76-0.67 (m, 2H). |
| 361 | 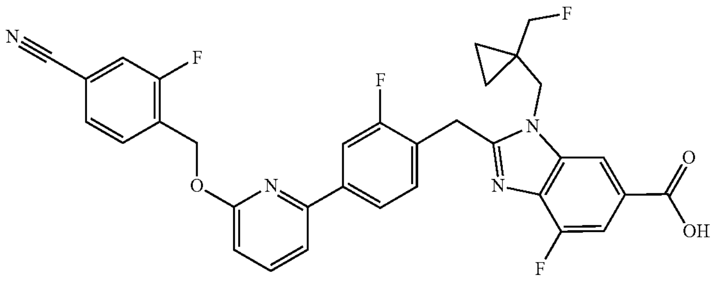 [SMILES: N#Cc1ccc(COc2cccc(-c3ccc(Cc4nc5c(F)cc(C(=O)O)cc5n4CC4(CF)CC4)c(F)c3)n2)c(F)c1] 2-(4-(6-((4-cyano-2-fluorobenzyl)oxy)pyridin-2-yl)-2-fluorobenzyl)-4-fluoro-1-((1-(fluoromethyl)cyclopropyl)methyl)-1H-benzo[d]imidazole-6-carboxylic acid: ES/MS 601.3; $^1$H NMR (400 MHz, DMSO-d6) δ 8.13 (d, J = 1.2 Hz, 1H), 7.96-7.82 (m, 4H), 7.80-7.70 (m, 2H), 7.67 (d, J = 7.4 Hz, 1H), 7.51 (dd, J = 11.3, 1.2 Hz, 1H), 7.45 (t, J = 7.9 Hz, 1H), 6.93 (d, J = 8.2 Hz, 1H), 5.62 (s, 2H), 4.56 (s, 2H), 4.45 (s, 2H), 4.18 (d, J = 48.8 Hz, 2H), 0.87-0.79 (m, 2H), 0.72 (q, J = 4.6 Hz, 2H). |
| 365 | 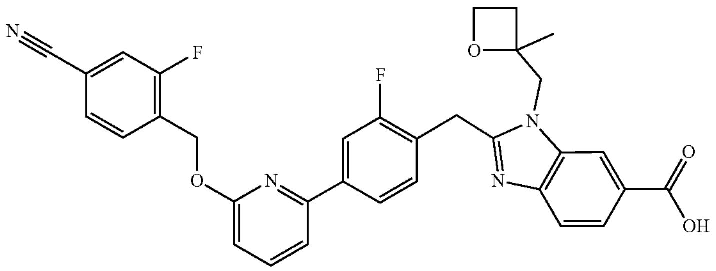 [SMILES: CC1(Cn2c(Cc3ccc(-c4cccc(OCc5ccc(C#N)cc5F)n4)cc3F)nc3ccc(C(=O)O)cc32)CCO1] (mixture) 2-(4-(6-((4-cyano-2-fluorobenzyl)oxy)pyridin-2-yl)-2-fluorobenzyl)-1-((2-methyloxetan-2-yl)methyl)-1H-benzo[d]imidazole-6-carboxylic acid: ES/MS 581.2; 1H NMR (400 MHz, DMSO-d6) δ 8.32 (d, J = 1.4 Hz, 1H), 7.93 (dd, J = 10.0, 1.4 Hz, 1H), 7.90-7.83 (m, 3H), 7.81-7.70 (m, 3H), 7.66 (d, J = 7.4 Hz, 1H), 7.60 (d, J = 8.4 Hz, 1H), 7.43 (t, J = 7.9 Hz, 1H), 6.93 (d, J = 8.2 Hz, 1H), 5.62 (s, 2H), 4.69 (d, J = 15.7 Hz, 1H), 4.48 (dt, J = 33.1, 16.3 Hz, 3H), 4.36-4.26 (m, 1H), 3.95 (td, J = 7.8, 5.8 Hz, 1H), 2.42 (t, J = 7.8 Hz, 2H), 1.46 (s, 3H). |

-continued

| Example | Structure/Name/Characterization |
|---|---|
| 366 | 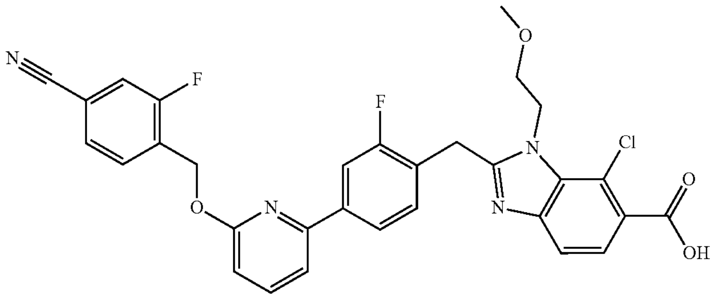 [SMILES: COCCn1c(Cc2ccc(-c3cccc(OCc4ccc(C#N)cc4F)n3)cc2F)nc2ccc(C(=O)O)c(Cl)c21]<br>7-chloro-2-(4-(6-((4-cyano-2-fluorobenzyl)oxy)pyridin-2-yl)-2-fluorobenzyl)-1-(2-methoxyethyl)-1H-benzo[d]imidazole-6-carboxylic acid: ES/MS 589.2; $^1$H NMR (400 MHz, DMSO-d6) δ 7.93 (dd, J = 10.0, 1.4 Hz, 1H), 7.90-7.83 (m, 3H), 7.80-7.71 (m, 2H), 7.67 (d, J = 7.4 Hz, 1H), 7.62-7.53 (m, 2H), 7.41 (t, J = 8.1 Hz, 1H), 6.94 (d, J = 8.2 Hz, 1H), 5.62 (s, 2H), 4.80 (t, J = 5.3 Hz, 2H), 4.45 (s, 2H), 3.75 (t, J = 5.2 Hz, 2H), 3.24 (s, 3H). |
| 370 | 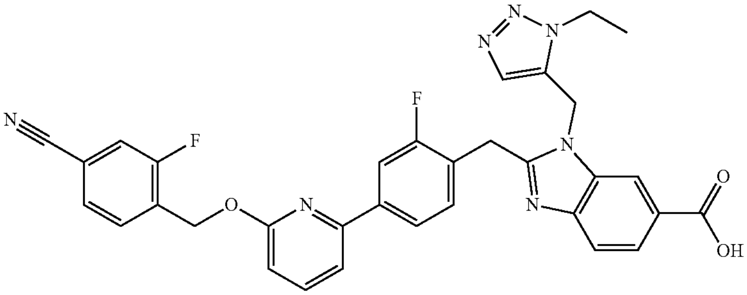 [SMILES: CCn1nncc1Cn1c(Cc2ccc(-c3cccc(OCc4ccc(C#N)cc4F)n3)cc2F)nc2ccc(C(=O)O)cc21]<br>2-(4-(6-((4-cyano-2-fluorobenzyl)oxy)pyridin-2-yl)-2-fluorobenzyl)-1-((l-ethyl-1H-1,2,3-triazol-5-yl)methyl)-1H-benzo[d]imidazole-6-carboxylic acid: ES/MS 606.2; $^1$H NMR (400 MHz, DMSO-d6) δ 8.19 (d, J = 1.5 Hz, 1H), 7.92 (dd, J = 10.0, 1.4 Hz, 1H), 7.90-7.82 (m, 2H), 7.86-7.71 (m, 4H), 7.75-7.61 (m, 2H), 7.44 (t, J = 8.0 Hz, 1H), 7.05 (s, 1H), 6.93 (d, J = 8.2 Hz, 1H), 5.95 (s, 2H), 5.62 (s, 2H), 4.50-4.37 (m, 4H), 1.39 (t, J = 7.3 Hz, 3H). |
| 371 | 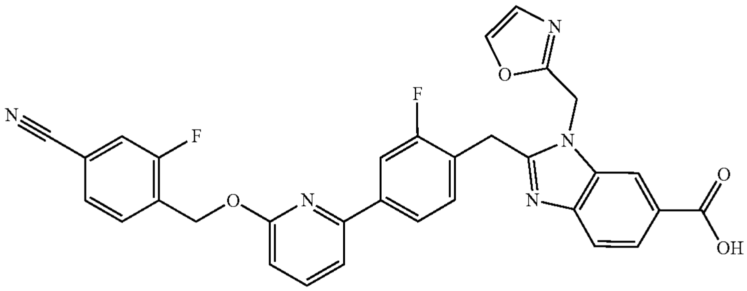 [SMILES: N#Cc1ccc(COc2cccc(-c3ccc(Cc4nc5ccc(C(=O)O)cc5n4Cc4ncco4)c(F)c3)n2)c(F)c1]<br>2-(4-(6-((4-cyano-2-fluorobenzyl)oxy)pyridin-2-yl)-2-fluorobenzyl)-1-(oxazol-2-ylmethyl)-1H-benzo[d]imidazole-6-carboxylic acid: ES/MS 578.2; $^1$H NMR (400 MHz, DMSO-d6) δ 8.27 (d, J = 1.4 Hz, 1H), 8.08 (d, J = 0.9 Hz, 1H), 7.93 (dd, J = 10.0, 1.4 Hz, 1H), 7.90-7.80 (m, 4H), 7.80-7.70 (m, 2H), 7.65 (dd, J = 7.9, 2.7 Hz, 2H), 7.40 (t, J = 8.1 Hz, 1H), 7.16 (d, J = 0.9 Hz, 1H), 6.93 (d, J = 8.2 Hz, 1H), 5.93 (s, 2H), 5.62 (s, 2H), 4.49 (s, 2H). |

-continued

| Example | Structure/Name/Characterization |
|---|---|
| 375 | 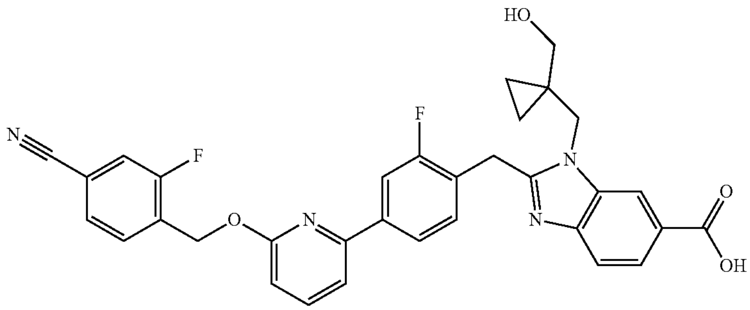 [SMILES: N#Cc1ccc(COc2cccc(-c3ccc(Cc4nc5ccc(C(=O)O)cc5n4CC4(CO)CC4)c(F)c3)n2)c(F)c1]<br>2-(4-(6-((4-cyano-2-fluorobenzyl)oxy)pyridin-2-yl)-2-fluorobenzyl)-1-((1-(hydroxymethyl)cyclopropyl)methyl)-1H-benzo[d]imidazole-6-carboxylic acid: ES/MS 581.2; $^{1}$H NMR (400 MHz, DMSO-d6) δ 8.27 (d, J = 1.5 Hz, 1H), 8.03-7.83 (m, 4H), 7.83-7.70 (m, 3H), 7.67 (d, J = 7.5 Hz, 1H), 7.58 (d, J = 8.4 Hz, 1H), 7.42 (t, J = 7.9 Hz, 1H), 6.93 (d, J = 8.3 Hz, 1H), 5.62 (s, 2H), 4.50 (s, 2H), 4.46 (s, 2H), 3.14 (s, 2H), 0.61 (d, J = 4.4 Hz, 2H), 0.54 (d, J = 4.5 Hz, 2H). |
| 376 | 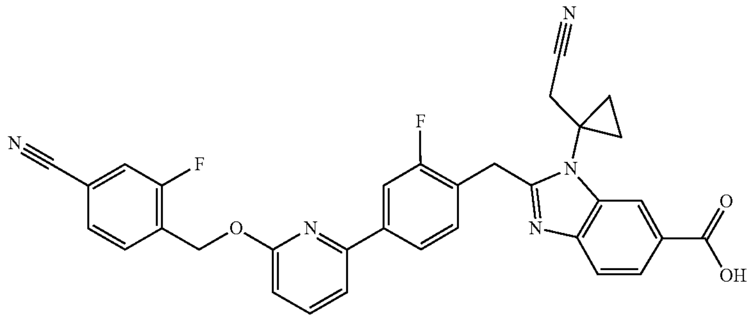 [SMILES: N#CCC1(n2c(Cc3ccc(-c4cccc(OCc5ccc(C#N)cc5F)n4)cc3F)nc3ccc(C(=O)O)cc32)CC1]<br>2-(4-(6-((4-cyano-2-fluorobenzyl)oxy)pyridin-2-yl)-2-fluorobenzyl)-1-(1-(cyanomethyl)cyclopropyl)-1H-benzo[d]imidazole-6-carboxylic acid: ES/MS 576.2; $^{1}$H NMR (400 MHz, DMSO-d6) δ 8.28 (d, J = 1.5 Hz, 1H), 7.96-7.71 (m, 7H), 7.69 (d, J = 7.4 Hz, 1H), 7.61 (d, J = 8.4 Hz, 1H), 7.54 (t, J = 7.9 Hz, 1H), 6.94 (d, J = 8.2 Hz, 1H), 5.63 (s, 2H), 4.55 (s, 2H), 3.43-3.12 (m, 2H), 1.64-1.34 (m, 4H). |
| 377 | 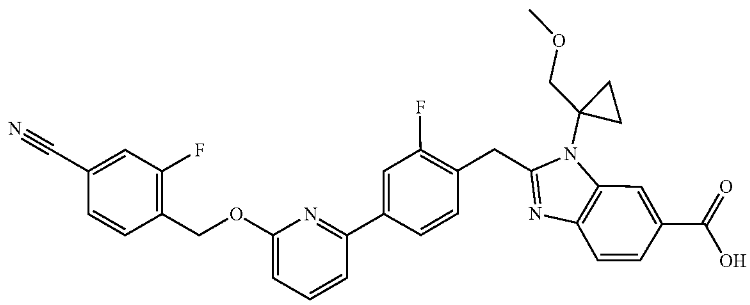 [SMILES: COCC1(n2c(Cc3ccc(-c4cccc(OCc5ccc(C#N)cc5F)n4)cc3F)nc3ccc(C(=O)O)cc32)CC1]<br>2-(4-(6-((4-cyano-2-fluorobenzyl)oxy)pyridin-2-yl)-2-fluorobenzyl)-1-(1-(methoxymethyl)cyclopropyl)-1H-benzo[d]imidazole-6-carboxylic acid: ES/MS 581.2; $^{1}$H NMR (400 MHz, Methanol-d4) δ 8.55 (d, J = 1.3 Hz, 1H), 8.20 (dd, J = 8.6, 1.5 Hz, 1H), 8.00-7.87 (m, 2H), 7.87-7.78 (m, 1H), 7.74 (dd, J = 8.2, 6.7 Hz, 2H), 7.68-7.55 (m, 3H), 7.51 (t, J = 7.9 Hz, 1H), 6.93 (d, J = 8.2 Hz, 1H), 5.66 (s, 2H), 4.88 (s, 3H), 3.89 (d, J = 10.8 Hz, 1H), 3.62-3.43 (m, 1H), 1.75-1.43 (m, 4H). |

-continued

| Example | Structure/Name/Characterization |
|---|---|
| 379 | 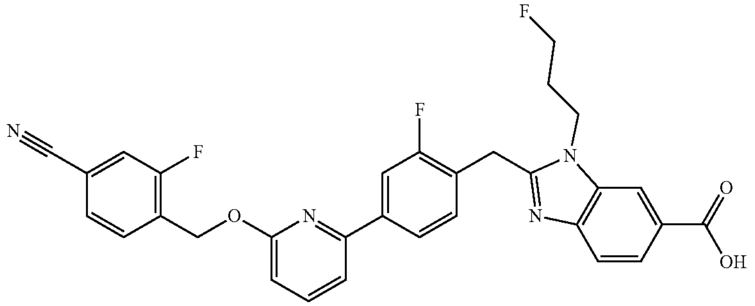 [SMILES: N#Cc1ccc(COc2cccc(-c3ccc(Cc4nc5ccc(C(=O)O)cc5n4CCCF)c(F)c3)n2)c(F)c1] 2-(4-(6-((4-cyano-2-fluorobenzyl)oxy)pyridin-2-yl)-2-fluorobenzyl)-1-(3-fluoropropyl)-1H-benzo[d]imidazole-6-carboxylic acid: ES/MS 557.2; $^1$H NMR (400 MHz, DMSO-d6) δ 8.30 (d, J = 1.5 Hz, 1H), 8.00-7.82 (m, 6H), 7.82-7.62 (m, 4H), 7.51 (t, J = 7.9 Hz, 1H), 6.94 (d, J = 8.2 Hz, 1H), 5.62 (s, 2H), 4.72-4.37 (m, 6H), 2.15 (dp, J = 26.3, 6.2 Hz, 2H). |
| 380 | 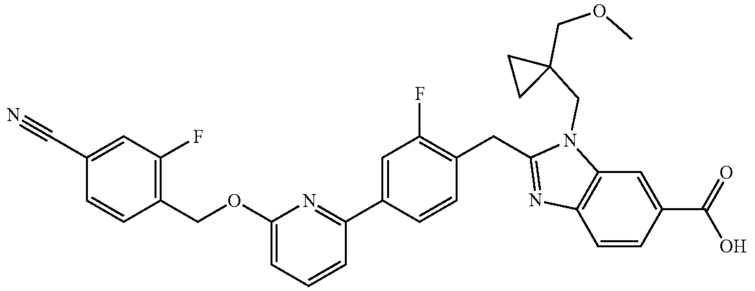 [SMILES: COCC1(Cn2c(Cc3ccc(-c4cccc(OCc5ccc(C#N)cc5F)n4)cc3F)nc3ccc(C(=O)O)cc32)CC1] 2-(4-(6-((4-cyano-2-fluorobenzyl)oxy)pyridin-2-yl)-2-fluorobenzyl)-1-((1-(methoxymethyl)cyclopropyl)methyl)-1H-benzo[d]imidazole-6-carboxylic acid: ES/MS 595.2; $^1$H NMR (400 MHz, DMSO-d6) δ 8.34 (s, 1H), 7.99-7.82 (m, 5H), 7.81-7.70 (m, 2H), 7.66 (dd, J = 13.4, 8.0 Hz, 2H), 7.45 (t, J = 7.9 Hz, 1H), 6.94 (d, J = 8.2 Hz, 1H), 5.62 (s, 2H), 4.53 (s, 2H), 4.48 (s, 3H), 3.17 (s, 3H), 3.00 (s, 2H), 0.77 (d, J = 4.9 Hz, 2H), 0.60 (d, J = 4.9 Hz, 2H). |
| 381 | 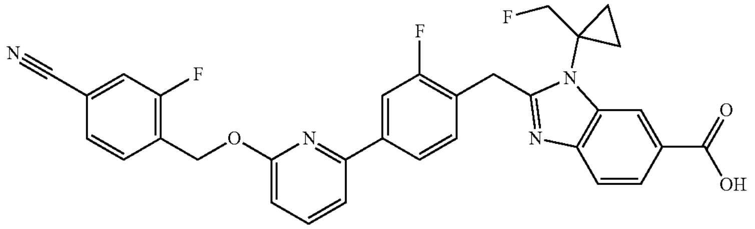 [SMILES: N#Cc1ccc(COc2cccc(-c3ccc(Cc4nc5ccc(C(=O)O)cc5n4C4(CF)CC4)c(F)c3)n2)c(F)c1] 2-(4-(6-((4-cyano-2-fluorobenzyl)oxy)pyridin-2-yl)-2-fluorobenzyl)-1-(1-(fluoromethyl)cyclopropyl)-1H-benzo[d]imidazole-6-carboxylic acid: ES/MS 569.4; $^1$H NMR (400 MHz, DMSO-d6) δ 8.18 (s, 1H), 7.99-7.73 (m, 7H), 7.68 (d, J = 7.5 Hz, 1H), 7.60 (d, J = 8.5 Hz, 1H), 7.51 (t, J = 8.0 Hz, 1H), 6.94 (d, J = 8.2 Hz, 1H), 5.63 (s, 2H), 4.66 (d, J = 48.4 Hz, 2H), 4.50 (s, 2H), 1.58-1.42 (m, 4H). |
| 382 | 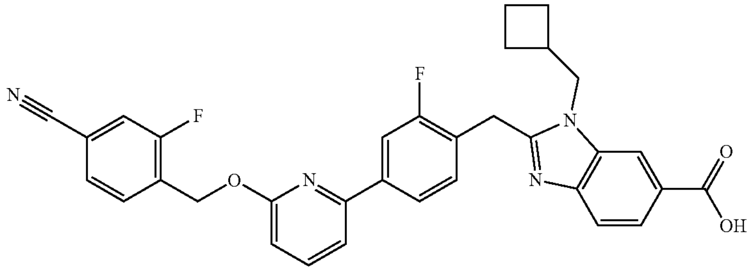 [SMILES: N#Cc1ccc(COc2cccc(-c3ccc(Cc4nc5ccc(C(=O)O)cc5n4CC4CCC4)c(F)c3)n2)c(F)c1] 2-(4-(6-((4-cyano-2-fluorobenzyl)oxy)pyridin-2-yl)-2-fluorobenzyl)-1-(cyclobutylmethyl)-1H-benzo[d]imidazole-6-carboxylic acid: ES/MS 565.7; $^1$H |

-continued

| Example | Structure/Name/Characterization |
|---|---|
| | NMR (400 MHz, DMSO-d6) δ 8.36 (d, J = 1.5 Hz, 1H), 7.99-7.83 (m, 5H), 7.82-7.71 (m, 2H), 7.68 (dd, J = 8.0, 3.0 Hz, 2H), 7.51 (t, J = 8.0 Hz, 1H), 6.95 (d, J = 8.2 Hz, 1H), 5.62 (s, 2H), 4.56 (s, 2H), 4.53 (d, J = 7.3 Hz, 2H), 2.79 (p, J = 7.6 Hz, 1H), 2.05-1.78 (m, 6H). |
| 384 | 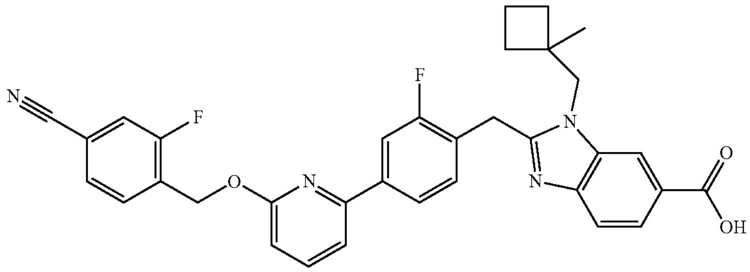 [SMILES: CC1(Cn2c(Cc3ccc(-c4cccc(OCc5ccc(C#N)cc5F)n4)cc3F)nc3ccc(C(=O)O)cc32)CCC1] 2-(4-(6-((4-cyano-2-fluorobenzyl)oxy)pyridin-2-yl)-2-fluorobenzyl)-1-((1-methylcyclobutyl)methyl)-1H-benzo[d]imidazole-6-carboxylic acid: ES/MS 579.6; $^1$H NMR (400 MHz, DMSO-d6) δ 8.33 (d, J = 1.5 Hz, 1H), 7.96-7.81 (m, 5H), 7.81-7.71 (m, 2H), 7.68 (dd, J = 8.0, 3.0 Hz, 2H), 7.51 (t, J = 8.1 Hz, 1H), 6.94 (d, J = 8.2 Hz, 1H), 5.62 (s, 2H), 4.52 (s, 2H), 4.45 (s, 2H), 2.08 (dt, J = 10.1, 7.8 Hz, 2H), 2.01-1.87 (m, 1H), 1.67 (tq, J = 11.8, 4.2, 3.1 Hz, 3H), 1.22 (s, 3H). |
| 385 | 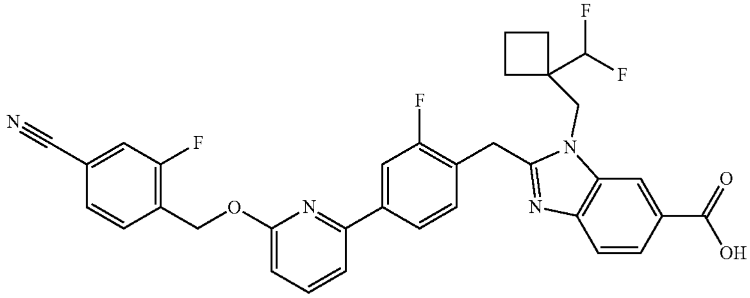 [SMILES: N#Cc1ccc(COc2cccc(-c3ccc(Cc4nc5ccc(C(=O)O)cc5n4CC4(C(F)F)CCC4)c(F)c3)n2)c(F)c1] 2-(4-(6-((4-cyano-2-fluorobenzyl)oxy)pyridin-2-yl)-2-fluorobenzyl)-1-((1-(difluoromethyl)cyclobutyl)methyl)-1H-benzo[d]imidazole-6-carboxylic acid: ES/MS 615.5; $^1$H NMR (400 MHz, DMSO-d6) δ 8.29 (d, J = 1.4 Hz, 1H), 8.01-7.82 (m, 5H), 7.81-7.70 (m, 2H), 7.66 (t, J = 8.5 Hz, 2H), 7.49 (t, J = 8.0 Hz, 1H), 6.94 (d, J = 8.2 Hz, 1H), 6.40 (t, J = 55.8 Hz, 1H), 5.62 (s, 2H), 4.63 (s, 2H), 4.45 (s, 2H), 2.18-2.00 (m, 4H), 1.93 (ddd, J = 17.8, 10.5, 7.9 Hz, 1H), 1.82-1.65 (m, 1H). |
| 386 | 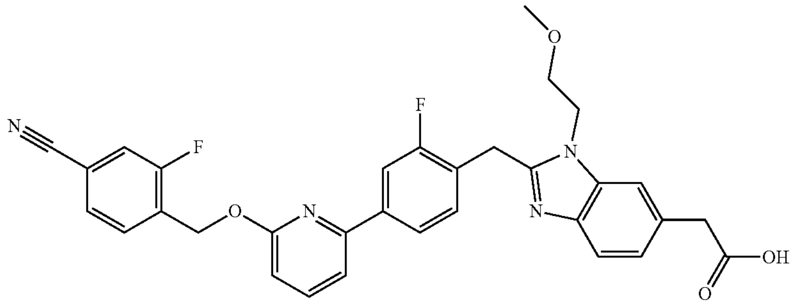 [SMILES: COCCn1c(Cc2ccc(-c3cccc(OCc4ccc(C#N)cc4F)n3)cc2F)nc2ccc(CC(=O)O)cc21] 2-(2-(4-(6-((4-cyano-2-fluorobenzyl)oxy)pyridin-2-yl)-2-fluorobenzyl)-1-(2-methoxyethyl)-1H-benzo[d]imidazol-6-yl)acetic acid: ES/MS 569.7; $^1$H NMR (400 MHz, DMSO-d6) δ 7.99-7.83 (m, 4H), 7.82-7.73 (m, 3H), 7.70 (t, J = 7.1 Hz, 1H), 7.62 (d, J = 8.4 Hz, 1H), 7.50 (t, J = 7.9 Hz, 1H), 7.36 (d, J = 8.4 Hz, 1H), 6.96 (d, J = 8.2 Hz, 1H), 5.62 (s, 2H), 4.66-4.63 (m, 4H), 3.76 (s, 2H), 3.69 (t, J = 5.1 Hz, 2H), 3.21 (s, 3H). |

-continued

| Example | Structure/Name/Characterization |
|---|---|
| 390 | 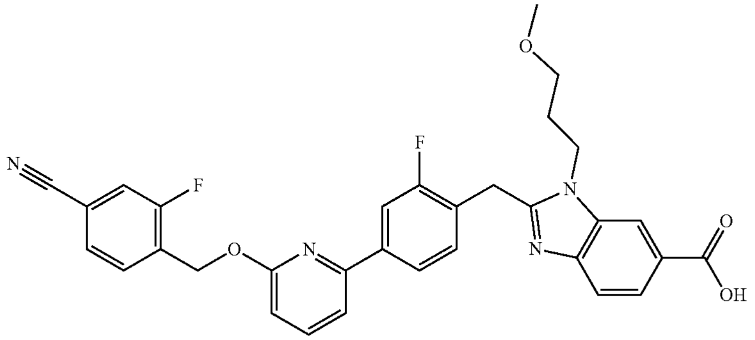 [SMILES: COCCCn1c(Cc2ccc(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2-fluorobenzyl)-1-(3-methoxypropyl)-1H-benzo[d]imidazole-6-carboxylic acid: ES/MS 569.2; $^1$H NMR (400 MHz, DMSO-d6) δ 8.28 (d, J = 1.5 Hz, 1H), 8.00-7.81 (m, 5H), 7.81-7.71 (m, 2H), 7.68 (dd, J = 8.0, 1.8 Hz, 2H), 7.50 (t, J = 7.9 Hz, 1H), 6.94 (d, J = 8.2 Hz, 1H), 5.62 (s, 2H), 4.53 (s, 2H), 4.48 (t, J = 7.0 Hz, 2H), 3.32 (t, J = 5.8 Hz, 2H), 1.99 (p, J = 6.5 Hz, 2H). |
| 392 | 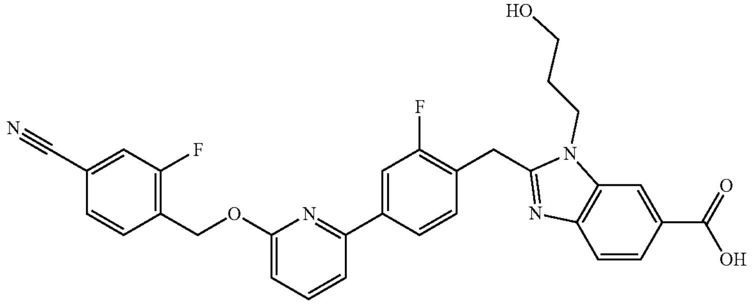 [SMILES: N#Cc1ccc(COc2cccc(-c3ccc(Cc4nc5ccc(C(=O)O)cc5n4CCCO)c(F)c3)n2)c(F)c1] 2-(4-(6-((4-cyano-2-fluorobenzyl)oxy)pyridin-2-yl)-2-fluorobenzyl)-1-(3-hydroxypropyl)-1H-benzo[d]imidazole-6-carboxylic acid: ES/MS 555.2; $^1$H NMR (400 MHz, DMSO-d6) δ 8.21 (d, J = 1.5 Hz, 1H), 8.01-7.81 (m, 5H), 7.81-7.70 (m, 2H), 7.67 (d, J = 7.5 Hz, 1H), 7.62 (d, J = 8.4 Hz, 1H), 7.46 (t, J = 7.9 Hz, 1H), 6.93 (d, J = 8.2 Hz, 1H), 5.62 (s, 2H), 4.47-4.42 (m, 4H), 3.45 (t, J = 5.8 Hz, 2H), 1.90 (q, J = 6.8, 5.7 Hz, 2H). |
| 402 | 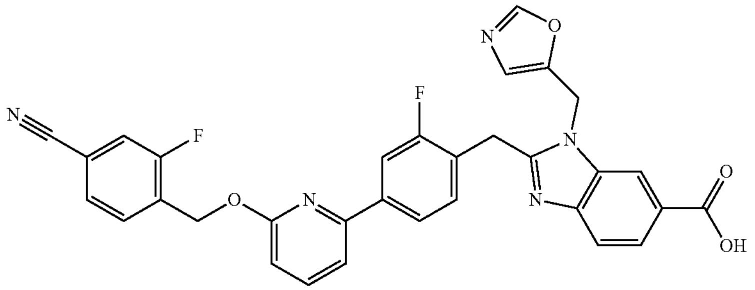 [SMILES: N#Cc1ccc(COc2cccc(-c3ccc(Cc4nc5ccc(C(=O)O)cc5n4Cc4cnco4)c(F)c3)n2)c(F)c1] 2-(4-(6-((4-cyano-2-fluorobenzyl)oxy)pyridin-2-yl)-2-fluorobenzyl)-1-(oxazol-5-ylmethyl)-1H-benzo[d]imidazole-6-carboxylic acid: ES/MS 578.2; $^1$H NMR (400 MHz, DMSO-d6) δ 8.38 (d, J = 1.5 Hz, 1H), 8.32 (s, 1H), 7.92 (dd, J = 10.0, 1.4 Hz, 1H), 7.90-7.83 (m, 4H), 7.81-7.70 (m, 2H), 7.65 (dd, J = 10.6, 8.0 Hz, 2H), 7.44 (t, J = 7.9 Hz, 1H), 7.29 (s, 1H), 6.94 (d, J = 8.2 Hz, 1H), 5.88 (s, 2H), 5.62 (s, 2H), 4.55 (s, 2H). |

-continued

| Example | Structure/Name/Characterization |
| --- | --- |
| 404 | 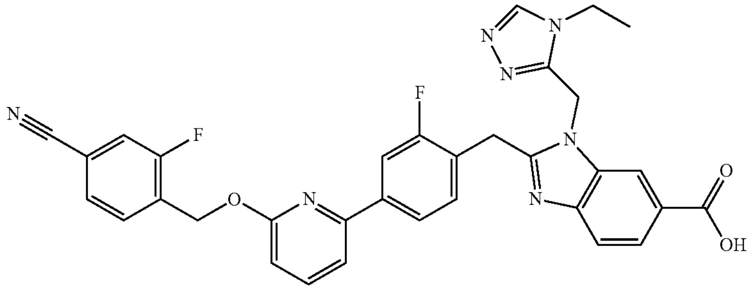 [SMILES: CCn1cnnc1Cn1c(Cc2ccc(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2-fluorobenzyl)-1-((4-ethyl-4H-1,2,4-triazol-3-yl)methyl)-1H-benzo[d]imidazole-6-carboxylic acid: ES/MS 606.2; $^{1}$H NMR (400 MHz, DMSO-d6) δ 8.79 (s, 1H), 8.29 (d, J = 1.5 Hz, 1H), 7.93 (dd, J = 10.0, 1.4 Hz, 1H), 7.91-7.80 (m, 4H), 7.80-7.71 (m, 2H), 7.67 (t, J = 8.4 Hz, 2H), 7.43 (t, J = 7.9 Hz, 1H), 6.94 (d, J = 8.2 Hz, 1H), 6.01 (s, 2H), 5.62 (s, 2H), 4.47 (s, 2H), 4.15 (q, J = 7.3 Hz, 2H), 1.35 (t, J = 7.3 Hz, 3H). |
| 407 | 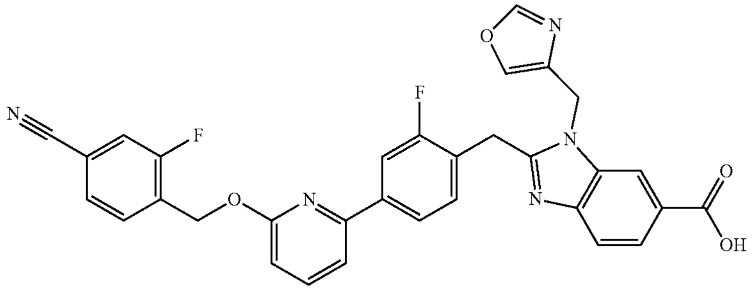 [SMILES: N#Cc1ccc(COc2cccc(-c3ccc(Cc4nc5ccc(C(=O)O)cc5n4Cc4cocn4)c(F)c3)n2)c(F)c1] 2-(4-(6-((4-cyano-2-fluorobenzyl)oxy)pyridin-2-yl)-2-fluorobenzyl)-1-(oxazol-4-ylmethyl)-1H-benzo[d]imidazole-6-carboxylic acid: ES/MS 578.2; $^{1}$H NMR (400 MHz, DMSO-d6) δ 8.37 (d, J = 1.5 Hz, 1H), 8.35 (d, J = 1.0 Hz, 1H), 8.22 (s, 1H), 7.93 (dd, J = 10.0, 1.4 Hz, 1H), 7.91-7.83 (m, 4H), 7.80-7.70 (m, 2H), 7.65 (dd, J = 14.5, 8.0 Hz, 2H), 7.46 (t, J = 8.1 Hz, 1H), 6.94 (d, J = 8.2 Hz, 1H), 5.64 (s, 2H), 5.62 (s, 2H), 4.62 (s, 2H). |
| 452 | 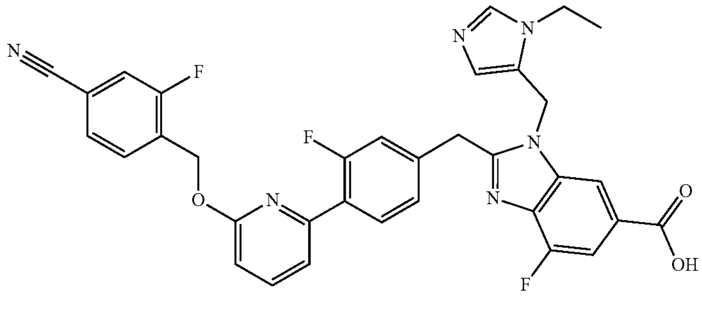 [SMILES: CCn1cncc1Cn1c(Cc2ccc(-c3cccc(OCc4ccc(C#N)cc4F)n3)c(F)c2)nc2c(F)cc(C(=O)O)cc21] 2-(4-(6-((4-cyano-2-fluorobenzyl)oxy)pyridin-2-yl)-3-fluorobenzyl)-1-((1-ethyl-1H-imidazol-5-yl)methyl)-4-fluoro-1H-benzo[d]imidazole-6-carboxylic acid: ES/MS 623.2; $^{1}$H NMR (400 MHz, Methanol-d4) δ 8.89 (d, J = 1.5 Hz, 1H), 8.03 (d, J = 1.3 Hz, 1H), 7.84 (t, J = 8.2 Hz, 1H), 7.80-7.70 (m, 3H), 7.60 (ddd, J = 12.2, 8.8, 1.5 Hz, 2H), 7.43 (dd, J = 7.4, 1.8 Hz, 1H), 7.19 (dd, J = 8.1, 1.7 Hz, 1H), 7.11 (dd, J = 12.3, 1.7 Hz, 1H), 6.89 (d, J = 8.3 Hz, 1H), 6.72 (d, J = 1.5 Hz, 1H), 5.84-5.70 (m, 2H), 5.60 (s, 3H), 4.54 (s, 2H), 4.25 (q, J = 7.3 Hz, 2H), 1.54 (t, J = 7.3 Hz, 3H). |

-continued

| Example | Structure/Name/Characterization |
|---|---|
| 454 | 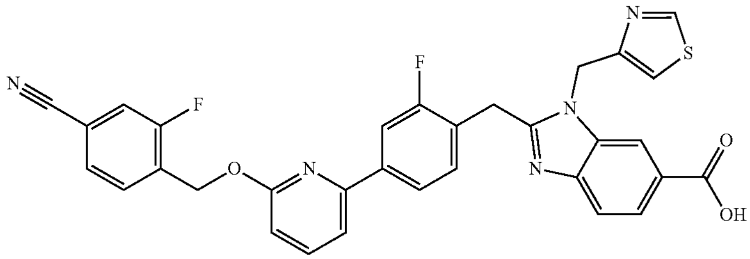 [SMILES: N#Cc1ccc(COc2cccc(-c3ccc(Cc4nc5ccc(C(=O)O)cc5n4Cc4cscn4)c(F)c3)n2)c(F)c1]<br>2-(4-(6-((4-cyano-2-fluorobenzyl)oxy)pyridin-2-yl)-2-fluorobenzyl)-1-(thiazol-4-ylmethyl)-1H-benzo[d]imidazole-6-carboxylic acid: ES/MS 594.2; $^{1}$H NMR (400 MHz, DMSO-d6) δ 9.06 (d, J = 2.0 Hz, 1H), 8.30 (d, J = 1.5 Hz, 1H), 7.93 (dd, J = 10.0, 1.4 Hz, 1H), 7.91-7.67 (m, 8H), 7.63 (dd, J = 17.5, 8.0 Hz, 2H), 7.40 (t, J = 8.1 Hz, 1H), 6.93 (d, J = 8.2 Hz, 1H), 5.79 (s, 2H), 5.62 (s, 2H), 4.58 (s, 2H). |
| 455 | 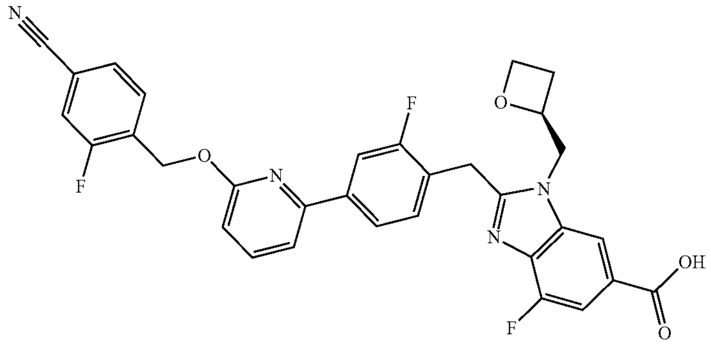 [SMILES: N#Cc1ccc(COc2cccc(-c3ccc(Cc4nc5c(F)cc(C(=O)O)cc5n4C[C@@H]4CCO4)c(F)c3)n2)c(F)c1]<br>(S)-2-(4-(6-((4-cyano-2-fluorobenzyl)oxy)pyridin-2-yl)-2-fluorobenzyl)-4-fluoro-1-(oxetan-2-ylmethyl)-1H-benzo[d]imidazole-6-carboxylic acid: ES/MS 585.2; $^{1}$H NMR (400 MHz, Methanol-d4) δ 8.16 (d, J = 1.3 Hz, 1H), 7.87-7.70 (m, 4H), 7.70-7.49 (m, 4H), 7.34 (t, J = 8.1 Hz, 1H), 6.88 (d, J = 8.2 Hz, 1H), 5.65 (s, 2H), 4.75-4.36 (m, 6H), 2.82-2.34 (m, 1H). |
| 475 | 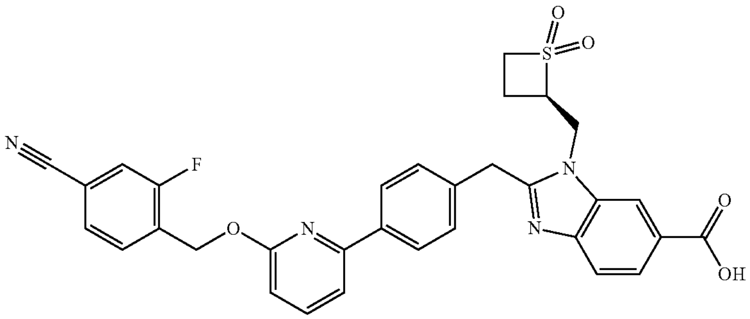 And<br>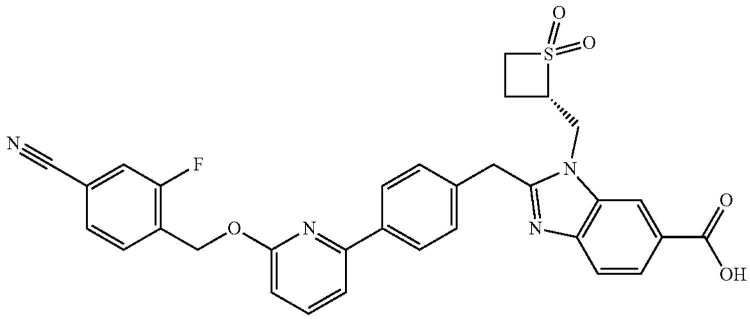 [SMILES: N#Cc1ccc(COc2cccc(-c3ccc(Cc4nc5ccc(C(=O)O)cc5n4C[C@@H]4CCS4(=O)=O)cc3)n2)c(F)c1]<br>2-(4-(6-((4-cyano-2-fluorobenzyl)oxy)pyridin-2-yl)benzyl)-1-((1,1-dioxidothietan-2-yl)methyl)-1H-benzo[d]imidazole-6-carboxylic acid: ES/MS 597.2; $^{1}$H NMR (400 MHz, Methanol-d4) δ 8.62 (s, 1H), 8.23 (dd, J = 8.6, 1.4 |

-continued

| Example | Structure/Name/Characterization |
|---|---|
| | Hz, 1H), 8.10 (d, J = 8.2 Hz, 3H), 7.86-7.69 (m, 4H), 7.66-7.42 (m, 7H), 6.88 (d, J = 8.2 Hz, 1H), 5.66 (s, 3H), 5.14 (dd, J = 15.3, 9.3 Hz, 1H), 5.06-4.91 (m, 2H), 4.80 (dd, J = 7.1, 1.8 Hz, 3H), 4.23-4.00 (m, 2H), 2.57-2.36 (m, 1H), 1.99 (dd, J = 19.7, 9.4 Hz, 1H). |
| 484 | 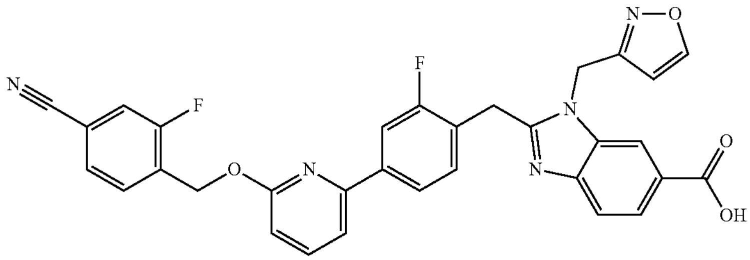 [SMILES: N#Cc1ccc(COc2cccc(-c3ccc(Cc4nc5ccc(C(=O)O)cc5n4Cc4ccon4)c(F)c3)n2)c(F)c1] 2-(4-(6-((4-cyano-2-fluorobenzyl)oxy)pyridin-2-yl)-2-fluorobenzyl)-1-(isoxazol-3-ylmethyl)-1H-benzo[d]imidazole-6-carboxylic acid: ES/MS 578; $^1$H NMR (400 MHz, DMSO-d6) δ 8.89 (s, 1H), 8.21 (s, 1H), 8.00-7.88 (m, 2H), 7.84 (q, J = 9.7, 8.7 Hz, 4H), 7.78 (s, 0H), 7.64 (dd, J = 10.7, 7.9 Hz, 2H), 7.44 (t, J = 7.9 Hz, 1H), 6.93 (d, J = 8.2 Hz, 1H), 6.49 (s, 1H), 5.84 (s, 2H), 5.61 (s, 2H), 4.47 (s, 2H). |
| 486 | 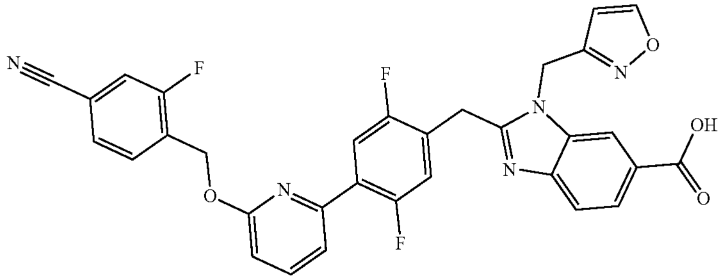 [SMILES: N#Cc1ccc(COc2cccc(-c3cc(F)c(Cc4nc5ccc(C(=O)O)cc5n4Cc4ccon4)cc3F)n2)c(F)c1] 2-(4-(6-((4-cyano-2-fluorobenzyl)oxy)pyridin-2-yl)-2,5-difluorobenzyl)-1-(isoxazol-3-ylmethyl)-1H-benzo[d]imidazole-6-carboxylic acid: ES/MS 596.2; $^1$H NMR (400 MHz, Methanol-d4) δ 8.65 (d, J = 1.7 Hz, 1H), 8.44 (s, 1H), 8.18 (dd, J = 8.6, 1.5 Hz, 1H), 7.87-7.78 (m, 2H), 7.78-7.68 (m, 2H), 7.66-7.49 (m, 3H), 7.29 (dd, J = 11.2, 6.1 Hz, 1H), 6.95 (d, J = 8.2 Hz, 1H), 6.48 (d, J = 1.7 Hz, 1H), 5.95 (s, 2H), 5.63 (s, 2H), 4.70 (s, 2H). |
| 492 | 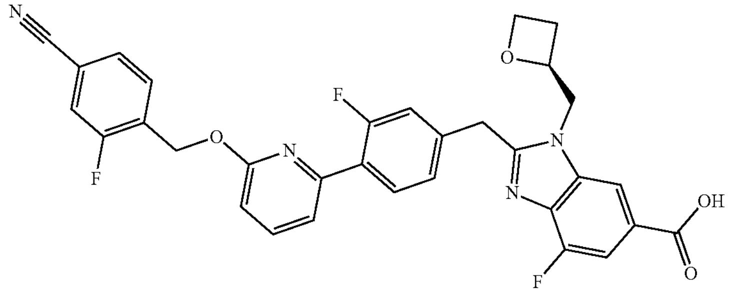 [SMILES: N#Cc1ccc(COc2cccc(-c3ccc(Cc4nc5c(F)cc(C(=O)O)cc5n4C[C@@H]4CCO4)cc3F)n2)c(F)c1] (S)-2-(4-(6-((4-cyano-2-fluorobenzyl)oxy)pyridin-2-yl)-3-fluorobenzyl)-4-fluoro-1-(oxetan-2-ylmethyl)-1H-benzo[d]imidazole-6-carboxylic acid: ES/MS 585.2; $^1$H NMR (400 MHz, Methanol-d4) δ 8.16 (d, J = 1.3 Hz, 1H), 7.95 (t, J = 8.1 Hz, 1H), 7.88-7.63 (m, 3H), 7.63-7.52 (m, 2H), 7.52-7.42 (m, 1H), 7.20 (dd, J = 20.9, 10.4 Hz, 2H), 6.88 (d, J = 8.2 Hz, 1H), 5.61 (s, 2H), 4.64 (td, J = 14.7, 13.9, 7.5 Hz, 2H), 4.56 (s, 2H), 4.54-4.40 (m, 2H), 2.83-2.23 (m, 1H). |

-continued

| Example | Structure/Name/Characterization |
|---|---|
| 519 | 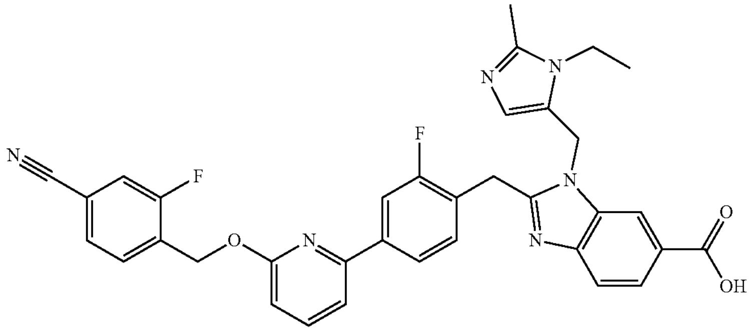 [SMILES: CCn1c(Cn2c(Cc3ccc(-c4cccc(OCc5ccc(C#N)cc5F)n4)cc3F)nc3ccc(C(=O)O)cc32)cnc1C] 2-(4-(6-((4-cyano-2-fluorobenzyl)oxy)pyridin-2-yl)-2-fluorobenzyl)-1-((l-ethyl-2-methyl-1H-imidazol-5-yl)methyl)-1H-benzo[d]imidazole-6-carboxylic acid: ES/MS 619.4; $^1$H NMR (400 MHz, Methanol-d4) δ 8.28 (dd, J = 1.6, 0.7 Hz, 1H), 8.10 (dd, J = 8.5, 1.5 Hz, 1H), 7.89-7.70 (m, 5H), 7.68-7.58 (m, 2H), 7.53 (dd, J = 7.5, 0.6 Hz, 1H), 7.38 (t, J = 8.0 Hz, 1H), 6.97-6.84 (m, 1H), 6.76 (d, J = 1.3 Hz, 1H), 5.85 (d, J = 1.3 Hz, 2H), 5.64 (s, 2H), 4.57 (s, 2H), 4.23 (q, J = 7.3 Hz, 2H), 2.54 (s, 3H), 1.39 (t, J = 7.3 Hz, 3H). |
| 520 | 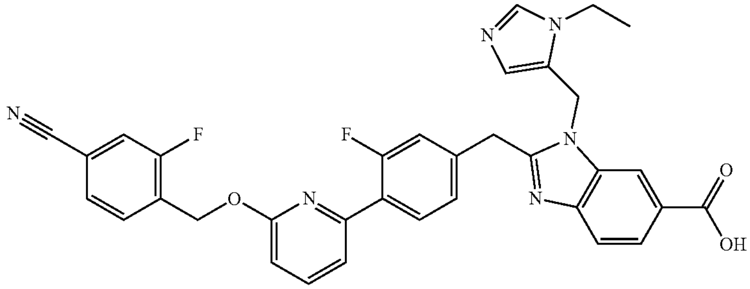 [SMILES: CCn1cncc1Cn1c(Cc2ccc(-c3cccc(OCc4ccc(C#N)cc4F)n3)c(F)c2)nc2ccc(C(=O)O)cc21] 2-(4-(6-((4-cyano-2-fluorobenzyl)oxy)pyridin-2-yl)-3-fluorobenzyl)-1-((1-ethyl-1H-imidazol-5-yl)methyl)-1H-benzo[d]imidazole-6-carboxylic acid: ES/MS 605.2; $^1$H NMR (400 MHz, Methanol-d4) δ 8.94 (d, J = 1.7 Hz, 1H), 8.24 (d, J = 1.6 Hz, 1H), 8.11 (dd, J = 8.5, 1.6 Hz, 1H), 7.96-7.68 (m, 4H), 7.66-7.54 (m, 2H), 7.45 (dd, J = 7.6, 1.9 Hz, 1H), 7.27-7.10 (m, 2H), 6.91 (d, J = 8.3 Hz, 1H), 6.79 (d, J = 1.8 Hz, 1H), 5.92-5.78 (m, 2H), 5.61 (s, 2H), 4.58 (s, 2H), 4.28 (q, J = 7.3 Hz, 2H), 2.05 (s, 1H), 1.56 (t, J = 7.3 Hz, 3H). |
| 521 | 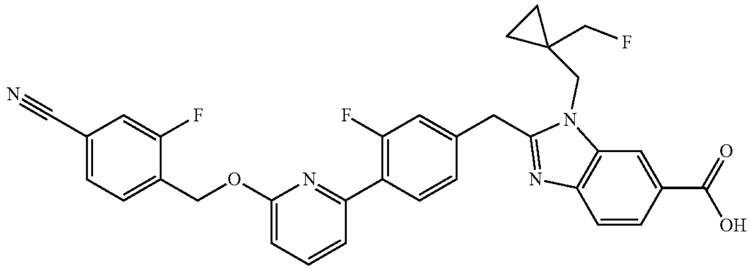 [SMILES: N#Cc1ccc(COc2cccc(-c3ccc(Cc4nc5ccc(C(=O)O)cc5n4CC4(CF)CC4)cc3F)n2)c(F)c1] 2-(4-(6-((4-cyano-2-fluorobenzyl)oxy)pyridin-2-yl)-3-fluorobenzyl)-1-((1-(fluoromethyl)cyclopropyl)methyl)-1H-benzo[d]imidazole-6-carboxylic acid: ES/MS 583.4; $^1$H NMR (400 MHz, Methanol-d4) δ 8.60 (d, J = 1.6 Hz, 1H), 8.23 (dd, J = 8.5, 1.5 Hz, 1H), 7.90-7.78 (m, 2H), 7.73 (t, J = 7.5 Hz, 1H), 7.67-7.47 (m, 3H), 7.36-7.25 (m, 2H), 6.92 (d, J = 8.2 Hz, 1H), 5.62 (s, 2H), 4.74 (d, J = 15.6 Hz, 5H), 4.31 (s, 1H), 4.19 (s, 1H), 2.05 (s, 1H), 1.02 (dt, J = 6.2, 3.1 Hz, 2H), 0.89 (t, J = 3.1 Hz, 2H). |

-continued

| Example | Structure/Name/Characterization |
| --- | --- |
| 523 | 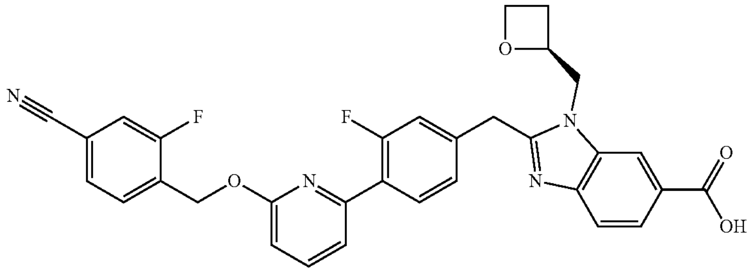 [SMILES: N#Cc1ccc(COc2cccc(-c3ccc(Cc4nc5ccc(C(=O)O)cc5n4C[C@@H]4CCO4)cc3F)n2)c(F)c1] (S)-2-(4-(6-((4-cyano-2-fluorobenzyl)oxy)pyridin-2-yl)-3-fluorobenzyl)-1-(oxetan-2-ylmethyl)-1H-benzo[d]imidazole-6-carboxylic acid: ES/MS 567.3; $^{1}H$ NMR (400 MHz, Methanol-d4) δ 8.57 (s, 1H), 8.21 (dd, J = 8.6, 1.5 Hz, 1H), 8.03 (t, J = 8.3 Hz, 1H), 7.89-7.68 (m, 3H), 7.67-7.46 (m, 3H), 7.31 (ddd, J = 10.2, 6.7, 1.9 Hz, 2H), 6.93 (d, J = 8.3 Hz, 1H), 5.63 (s, 2H), 5.23 (dd, J = 7.3, 2.5 Hz, 1H), 4.96 (dd, J = 15.5, 7.6 Hz, 1H), 4.79 (d, J = 11.8 Hz, 3H), 4.70 (td, J = 8.0, 5.8 Hz, 1H), 4.63-4.47 (m, 1H), 2.86 (ddd, J = 11.4, 5.5, 2.6 Hz, 1H), 2.68-2.50 (m, 1H). |
| 524 | 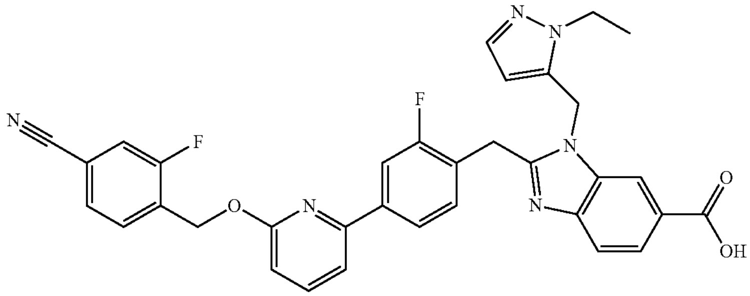 [SMILES: CCn1nccc1Cn1c(Cc2ccc(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2-fluorobenzyl)-1-((l-ethyl-1H-pyrazol-5-yl)methyl)-1H-benzo[d]imidazole-6-carboxylic acid: ES/MS 605.2; $^{1}H$ NMR (400 MHz, Methanol-d4) δ 8.28-8.20 (m, 1H), 8.12 (dd, J = 8.5, 1.6 Hz, 1H), 7.88-7.68 (m, 3H), 7.60 (ddd, J = 14.8, 8.8, 1.6 Hz, 2H), 7.50 (d, J = 7.5 Hz, 1H), 7.37 (t, J = 7.9 Hz, 1H), 7.26 (d, J = 2.0 Hz, 1H), 6.89 (d, J = 8.2 Hz, 1H), 5.82 (s, 2H), 5.64 (s, 2H), 5.56 (d, J = 2.1 Hz, 1H), 4.57 (s, 2H), 4.22 (q, J = 7.3 Hz, 2H), 3.74-3.62 (m, 2H), 1.40 (t, J = 7.2 Hz, 3H). |
| 525 | 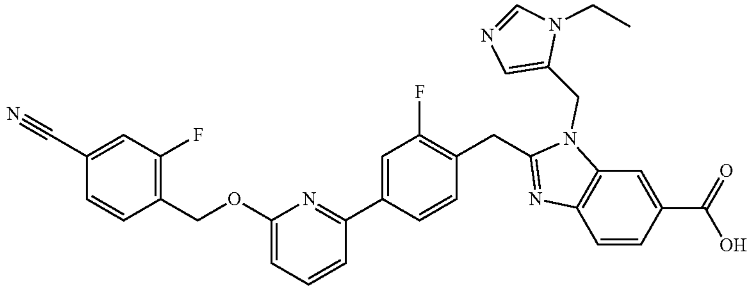 [SMILES: CCn1cncc1Cn1c(Cc2ccc(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2-fluorobenzyl)-1-((1-ethyl-1H-imidazol-5-yl)methyl)-1H-benzo[d]imidazole-6-carboxylic acid: ES/MS 605.4; $^{1}H$ NMR (400 MHz, Methanol-d4) δ 8.95 (d, J = 1.5 Hz, 1H), 8.25 (d, J = 1.4 Hz, 1H), 8.08 (dd, J = 8.6, 1.5 Hz, 1H), 7.88-7.66 (m, 5H), 7.61 (ddd, J = 14.8, 8.8, 1.5 Hz, 2H), 7.51 (d, J = 7.5 Hz, 1H), 7.40 (t, J = 7.9 Hz, 1H), 6.90 (d, J = 8.2 Hz, 1H), 6.79 (d, J = 1.5 Hz, 1H), 5.87 (d, J = 1.3 Hz, 2H), 5.64 (s, 2H), 4.55 (s, 2H), 4.31 (q, J = 7.3 Hz, 2H), 1.57 (t, J = 7.3 Hz, 3H). |

-continued

| Example | Structure/Name/Characterization |
|---|---|
| 527 | 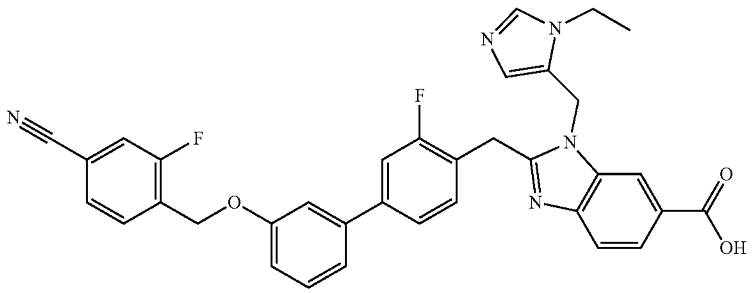 [SMILES: CCn1cncc1Cn1c(Cc2ccc(-c3cccc(OCc4ccc(C#N)cc4F)c3)cc2F)nc2ccc(C(=O)O)cc21] 2-((3'-((4-cyano-2-fluorobenzyl)oxy)-3-fluoro-[1,1'-biphenyl]-4-yl)methyl)-1-((1-ethyl-1H-imidazol-5-yl)methyl)-1H-benzo[d]imidazole-6-carboxylic acid: ES/MS 604.5; $^1$H NMR (400 MHz, Methanol-d4) δ 8.97 (d, J = 1.5 Hz, 1H), 8.28 (dd, J = 1.5, 0.6 Hz, 1H), 8.11 (dd, J = 8.6, 1.5 Hz, 1H), 7.88-7.73 (m, 2H), 7.70-7.56 (m, 2H), 7.48-7.31 (m, 4H), 7.30-7.17 (m, 2H), 7.16-7.01 (m, 1H), 6.80 (t, J = 1.4 Hz, 1H), 5.90 (d, J = 1.3 Hz, 2H), 5.31 (s, 2H), 4.58 (s, 2H), 4.32 (q, J = 7.3 Hz, 2H), 3.36 (d, J = 2.8 Hz, 1H), 1.58 (t, J = 7.3 Hz, 3H). |
| 528 | 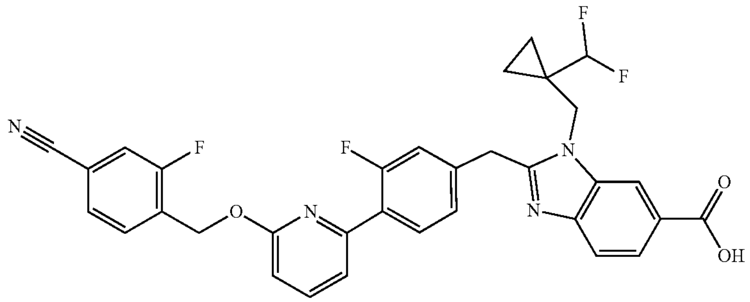 [SMILES: N#Cc1ccc(COc2cccc(-c3ccc(Cc4nc5ccc(C(=O)O)cc5n4CC4(C(F)F)CC4)cc3F)n2)c(F)c1] 2-(4-(6-((4-cyano-2-fluorobenzyl)oxy)pyridin-2-yl)-3-fluorobenzyl)-1-((1-(difluoromethyl)cyclopropyl)methyl)-1H-benzo[d]imidazole-6-carboxylic acid: ES/MS 601.3; $^1$H NMR (400 MHz, Methanol-d4) δ 8.54 (d, J = 1.2 Hz, 1H), 8.20 (dd, J = 8.6, 1.4 Hz, 1H), 8.03 (dd, J = 8.8, 7.6 Hz, 1H), 7.91-7.68 (m, 3H), 7.67-7.43 (m, 3H), 7.38-7.22 (m, 2H), 6.92 (dd, J = 8.2, 0.7 Hz, 1H), 5.78-5.42 (m, 3H), 4.82 (s, 2H), 4.73 (s, 2H), 1.11-0.96 (m, 5H). |
| 529 | 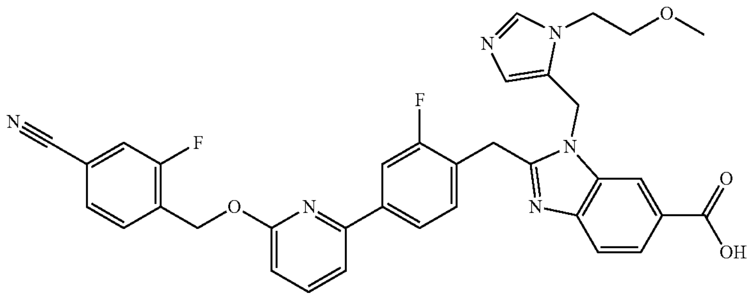 [SMILES: COCCn1cncc1Cn1c(Cc2ccc(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2-fluorobenzyl)-1-((1-(2-methoxyethyl)-1H-imidazol-5-yl)methyl)-1H-benzo[d]imidazole-6-carboxylic acid: ES/MS 635.2; $^1$H NMR (400 MHz, Methanol-d4) δ 8.95 (d, J = 1.6 Hz, 1H), 8.21 (d, J = 1.4 Hz, 1H), 8.09 (dd, J = 8.5, 1.5 Hz, 1H), 7.88-7.69 (m, 5H), 7.60 (ddd, J = 13.9, 8.8, 1.5 Hz, 2H), 7.51 (d, J = 7.5 Hz, 1H), 7.41 (t, J = 8.0 Hz, 1H), 6.90 (d, J = 8.2 Hz, 1H), 6.79 (d, J = 1.5 Hz, 1H), 5.97-5.84 (m, 2H), 5.64 (s, 2H), 4.61-4.43 (m, 4H), 3.87-3.73 (m, 2H), 3.46 (s, 3H). |

-continued

| Example | Structure/Name/Characterization |
| --- | --- |
| 530 | 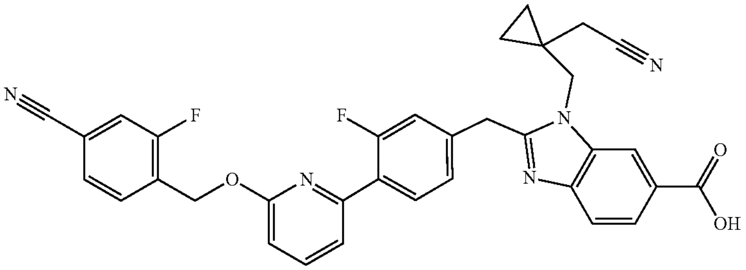 [SMILES: N#CCC1(Cn2c(Cc3ccc(-c4cccc(OCc5ccc(C#N)cc5F)n4)c(F)c3)nc3ccc(C(=O)O)cc32)CC1] 2-(4-(6-((4-cyano-2-fluorobenzyl)oxy)pyridin-2-yl)-3-fluorobenzyl)-1-((1-(cyanomethyl)cyclopropyl)methyl)-1H-benzo[d]imidazole-6-carboxylic acid: ES/MS 590.2; $^1$H NMR (400 MHz, Methanol-d4) δ 8.64 (d, J = 1.6 Hz, 1H), 8.23 (dd, J = 8.6, 1.5 Hz, 1H), 8.04 (t, J = 8.2 Hz, 1H), 7.91-7.67 (m, 3H), 7.67-7.44 (m, 3H), 7.42-7.24 (m, 2H), 6.92 (d, J = 8.2 Hz, 1H), 5.62 (s, 2H), 4.78 (s, 2H), 4.72 (s, 2H), 2.63 (s, 2H), 1.05-0.84 (m, 4H). |
| 531 | 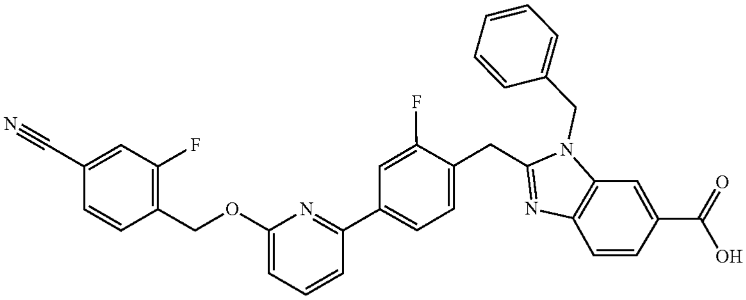 [SMILES: N#Cc1ccc(COc2cccc(-c3ccc(Cc4nc5ccc(C(=O)O)cc5n4Cc4ccccc4)c(F)c3)n2)c(F)c1] 1-benzyl-2-(4-(6-((4-cyano-2-fluorobenzyl)oxy)pyridin-2-yl)-2-fluorobenzyl)-1H-benzo[d]imidazole-6-carboxylic acid: ES/MS 587.5; $^1$H NMR (400 MHz, DMSO-d6) δ 8.10 (s, 1H), 7.98-7.70 (m, 8H), 7.64 (dd, J = 8.0, 3.1 Hz, 2H), 7.41 (t, J = 8.0 Hz, 1H), 7.37-7.19 (m, 3H), 7.11 (d, J = 7.3 Hz, 2H), 6.93 (d, J = 8.2 Hz, 1H), 5.70 (s, 2H), 5.62 (s, 2H), 4.41 (s, 2H). |
| 532 | 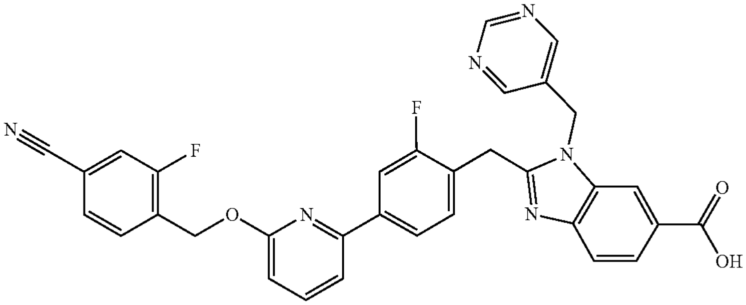 [SMILES: N#Cc1ccc(COc2cccc(-c3ccc(Cc4nc5ccc(C(=O)O)cc5n4Cc4cncnc4)c(F)c3)n2)c(F)c1] 2-(4-(6-((4-cyano-2-fluorobenzyl)oxy)pyridin-2-yl)-2-fluorobenzyl)-1-(pyrimidin-5-ylmethyl)-1H-benzo[d]imidazole-6-carboxylic acid: ES/MS 589.3; $^1$H NMR (400 MHz, DMSO-d6) δ 9.06 (s, 1H), 8.56 (s, 2H), 8.21 (d, J = 1.4 Hz, 1H), 8.01-7.57 (m, 10H), 7.45 (t, J = 8.0 Hz, 1H), 6.93 (d, J = 8.2 Hz, 1H), 5.83 (s, 2H), 5.61 (s, 2H), 4.52 (s, 2H) |
| 533 | 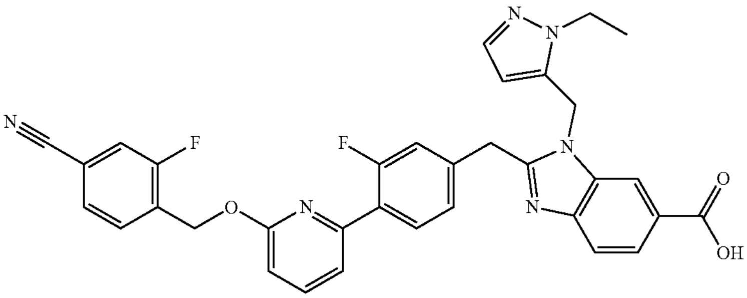 [SMILES: CCn1nccc1Cn1c(Cc2ccc(-c3cccc(OCc4ccc(C#N)cc4F)n3)c(F)c2)nc2ccc(C(=O)O)cc21] |

-continued

| Example | Structure/Name/Characterization |
|---|---|
| | 2-(4-(6-((4-cyano-2-fluorobenzyl)oxy)pyridin-2-yl)-3-fluorobenzyl)-1-((1-ethyl-1H-pyrazol-5-yl)methyl)-1H-benzo[d]imidazole-6-carboxylic acid: ES/MS 605.2; $^1$H NMR (400 MHz, Methanol-d4) δ 8.37-8.27 (m, 1H), 8.23 (dd, J = 8.6, 1.5 Hz, 1H), 7.98-7.86 (m, 2H), 7.75 (dt, J = 28.7, 7.6 Hz, 2H), 7.66-7.54 (m, 2H), 7.46 (dd, J = 7.4, 2.0 Hz, 1H), 7.29 (d, J = 2.1 Hz, 1H), 7.26-7.12 (m, 2H), 6.90 (d, J = 8.2 Hz, 1H), 5.92 (s, 2H), 5.62 (d, J = 14.4 Hz, 4H), 4.69 (s, 2H), 4.23 (q, J = 7.2 Hz, 2H), 1.43 (t, J = 7.2 Hz, 3H). |
| 534 | 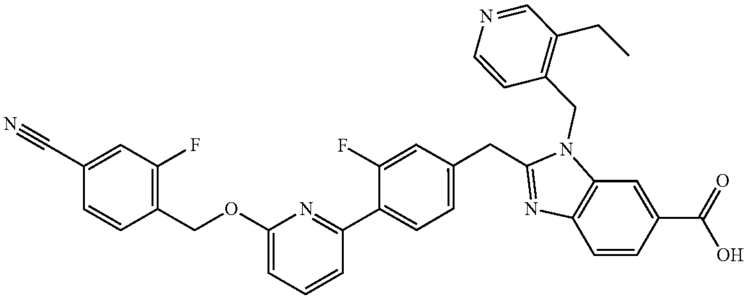 [SMILES: CCc1cnccc1Cn1c(Cc2ccc(-c3cccc(OCc4ccc(C#N)cc4F)n3)c(F)c2)nc2ccc(C(=O)O)cc21] 2-(4-(6-((4-cyano-2-fluorobenzyl)oxy)pyridin-2-yl)-3-fluorobenzyl)-1-((3-ethylpyridin-4-yl)methyl)-1H-benzo[d]imidazole-6-carboxylic acid: ES/MS 616.3; $^1$H NMR (400 MHz, Methanol-d4) δ 8.58 (s, 1H), 8.24-8.05 (m, 3H), 7.99-7.83 (m, 1H), 7.83-7.68 (m, 2H), 7.61 (ddd, J = 11.6, 8.7, 1.6 Hz, 2H), 7.36 (dd, J = 7.5, 2.0 Hz, 1H), 7.21-7.01 (m, 2H), 6.90 (d, J = 8.2 Hz, 1H), 6.48 (d, J = 6.0 Hz, 1H), 5.97 (s, 2H), 5.60 (s, 2H), 4.55 (s, 2H), 3.05 (q, J = 7.5 Hz, 2H), 1.50 (t, J = 7.4 Hz, 3H). |
| 535 | 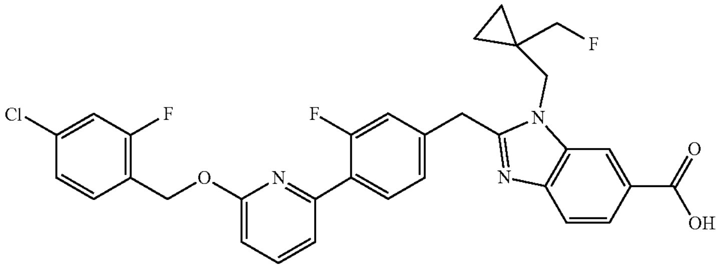 [SMILES: O=C(O)c1ccc2nc(Cc3ccc(-c4cccc(OCc5ccc(Cl)cc5F)n4)c(F)c3)n(CC3(CF)CC3)c2c1] 2-(4-(6-((4-chloro-2-fluorobenzyl)oxy)pyridin-2-yl)-3-fluorobenzyl)-1-((1-(fluoromethyl)cyclopropyl)methyl)-1H-benzo[d]imidazole-6-carboxylic acid: ES/MS 592.2; $^1$H NMR (400 MHz, Methanol-d4) δ 8.67-8.52 (m, 1H), 8.23 (dd, J = 8.5, 1.5 Hz, 1H), 8.11 (t, J = 8.2 Hz, 1H), 7.79 (t, J = 7.9 Hz, 2H), 7.60-7.45 (m, 2H), 7.39-7.15 (m, 4H), 6.87 (d, J = 8.2 Hz, 1H), 5.52 (s, 2H), 4.75 (d, J = 16.8 Hz, 4H), 4.32 (s, 1H), 4.19 (s, 1H), 1.10-0.96 (m, 2H), 0.90 (d, J = 5.2 Hz, 2H). |
| 550 | 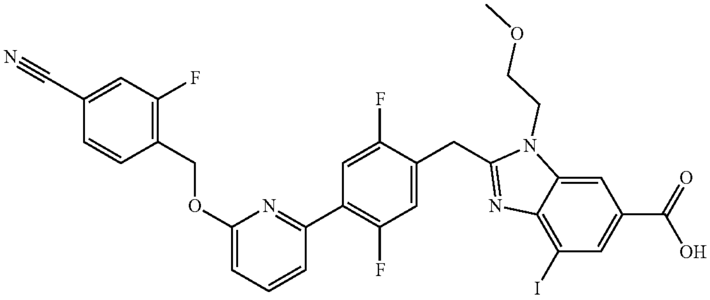 [SMILES: COCCn1c(Cc2cc(F)c(-c3cccc(OCc4ccc(C#N)cc4F)n3)cc2F)nc2c(I)cc(C(=O)O)cc21] 2-(4-(6-((4-cyano-2-fluorobenzyl)oxy)pyridin-2-yl)-2,5-difluorobenzyl)-4-iodo-1-(2-methoxyethyl)-1H-benzo[d]imidazole-6-carboxylic acid: ES/MS 699.2; $^1$H NMR (400 MHz, DMSO) δ 8.21 (s, 1H), 8.12 (s, 1H), 7.96-7.84 (m, 2H), 7.82-7.69 (m, 3H), 7.56-7.49 (m, 1H), 7.30 (dd, J = 11.7, 6.0 Hz, 1H), 6.98 (d, J = 8.2 Hz, 1H), 5.60 (s, 2H), 4.50 (s, 2H), 4.44 (s, 2H), 3.63 (t, J = 5.1 Hz, 2H), 3.16 (s, 3H). |

-continued

| Example | Structure/Name/Characterization |
|---|---|
| 551 | 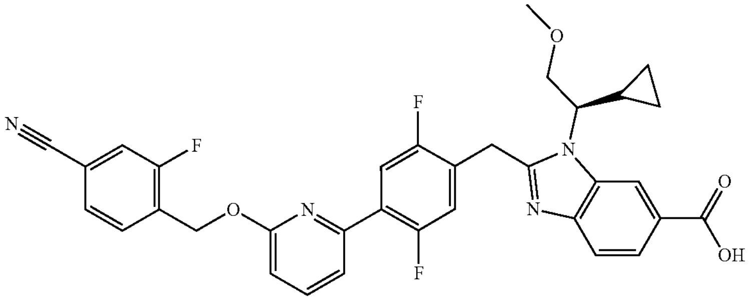 And 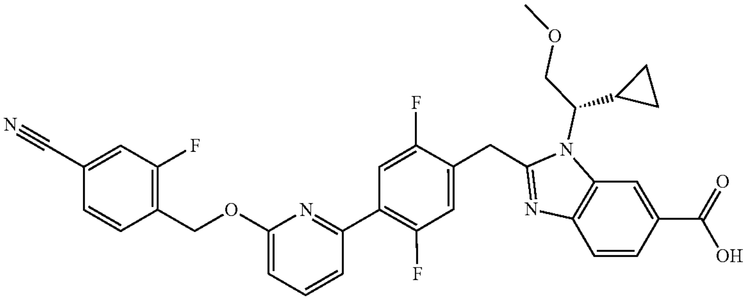 [SMILES: COC[C@H](C1CC1)n1c(Cc2cc(F)c(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2-fluorobenzyl)-1-(1-cyclopropyl-2-methoxyethyl)-1H-benzo[d]imidazole-6-carboxylic acid: ES/MS 595.4; $^{1}$H NMR (400 MHz, DMSO) δ 8.36 (d, J = 1.5 Hz, 1H), 7.96-7.81 (m, 5H), 7.81-7.70 (m, 2H), 7.66 (dd, J = 9.4, 7.9 Hz, 2H), 7.43 (t, J = 7.9 Hz, 1H), 6.94 (d, J = 8.1 Hz, 1H), 5.62 (s, 2H), 4.48 (d, J = 16.6 Hz, 1H), 4.37 (d, J = 16.7 Hz, 1H), 4.12 (s, 1H), 4.07-3.98 (m, 1H), 3.83 (dd, J = 10.2, 3.7 Hz, 1H), 3.19 (s, 3H), 1.68 (d, J = 7.2 Hz, 1H), 0.74 (tt, J = 8.6, 4.5 Hz, 1H), 0.67-0.57 (m, 1H), 0.46-0.33 (m, 1H), 0.08--0.06 (m, 1H). |
| 558 | 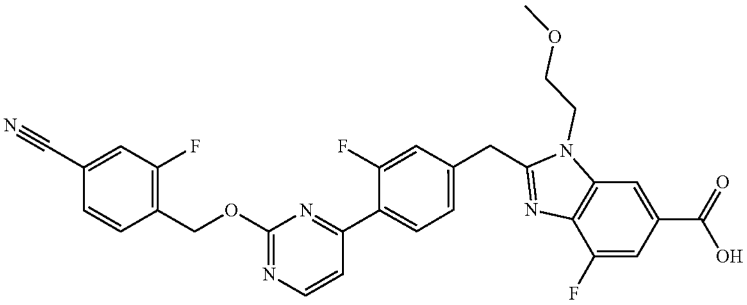 [SMILES: COCCn1c(Cc2ccc(-c3ccnc(OCc4ccc(C#N)cc4F)n3)c(F)c2)nc2c(F)cc(C(=O)O)cc21] 2-(4-(2-((4-cyano-2-fluorobenzyl)oxy)pyrimidin-4-yl)-3-fluorobenzyl)-4-fluoro-1-(2-methoxyethyl)-1H-benzo[d]imidazole-6-carboxylic acid: ES/MS 574.2; $^{1}$H NMR (400 MHz, DMSO-d6) δ 8.73 (d, J = 5.2 Hz, 1H), 8.11-8.02 (m, 2H), 7.94 (dd, J = 10.0, 1.4 Hz, 1H), 7.80-7.73 (m, 2H), 7.59 (dd, J = 5.2, 2.0 Hz, 1H), 7.52 (dd, J = 11.4, 1.3 Hz, 1H), 7.43-7.33 (m, 2H), 5.60 (s, 2H), 4.57 (t, J = 5.1 Hz, 2H), 4.49 (s, 2H), 3.61 (t, J = 5.1 Hz, 2H), 3.17 (s, 3H). |
| 561 | 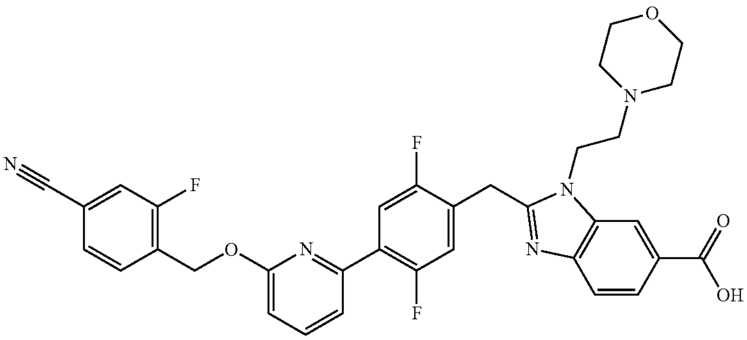 [SMILES: N#Cc1ccc(COc2cccc(-c3cc(F)c(Cc4nc5ccc(C(=O)O)cc5n4CCN4CCOCC4)cc3F)n2)c(F)c1] |

-continued

| Example | Structure/Name/Characterization |
| --- | --- |
| | 2-(4-(6-((4-cyano-2-fluorobenzyl)oxy)pyridin-2-yl)-2,5-difluorobenzyl)-1-(2-morpholinoethyl)-1H-benzo[d]imidazole-6-carboxylic acid: ES/MS 628.2; $^1$H NMR (400 MHz, Methanol-d4) δ 8.44 (d, J = 1.4 Hz, 1H), 8.12 (dd, J = 8.5, 1.5 Hz, 1H), 7.87-7.81 (m, 1H), 7.79 (dd, J = 10.8, 6.4 Hz, 1H), 7.76-7.71 (m, 2H), 7.64-7.54 (m, 3H), 7.32 (dd, J = 11.3, 6.1 Hz, 1H), 6.96 (d, J = 8.2 Hz, 1H), 5.63 (s, 2H), 4.84 (d, J = 8.2 Hz, 2H), 4.61 (s, 2H), 3.93 (s, 4H), 3.47 (t, J = 7.8 Hz, 2H), 3.32 (s, 4H). |
| 566 | 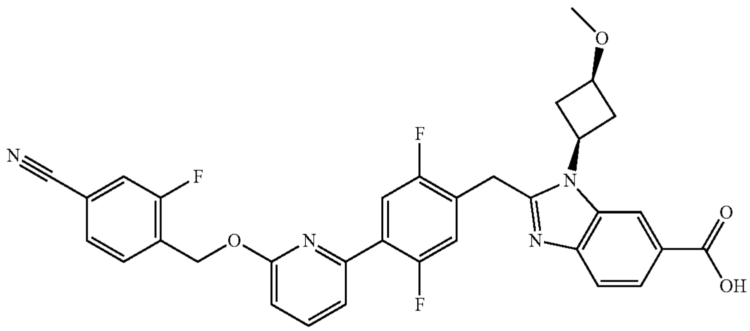 [SMILES: CO[C@H]1C[C@@H](n2c(Cc3cc(F)c(-c4cccc(OCc5ccc(C#N)cc5F)n4)cc3F)nc3ccc(C(=O)O)cc32)C1] 2-(4-(6-((4-cyano-2-fluorobenzyl)oxy)pyridin-2-yl)-2,5-difluorobenzyl)-1-((1s,3s)-3-methoxycyclobutyl)-1H-benzo[d]imidazole-6-carboxylic acid: ES/MS 599.2; $^1$H NMR (400 MHz, Methanol-d4) δ 8.87 (dd, J = 1.5, 0.7 Hz, 1H), 8.17 (dd, J = 8.6, 1.4 Hz, 1H), 7.88-7.76 (m, 3H), 7.73 (t, J = 7.5 Hz, 1H), 7.65-7.52 (m, 3H), 7.26 (dd, J = 11.3, 6.1 Hz, 1H), 6.95 (dd, J = 8.3, 0.6 Hz, 1H), 5.63 (s, 2H), 5.05 (p, J = 8.5 Hz, 1H), 4.65 (s, 2H), 4.00 (p, J = 6.6 Hz, 1H), 3.41 (s, 3H), 3.19-3.02 (m, 2H), 3.00-2.84 (m, 2H). |
| 567 | 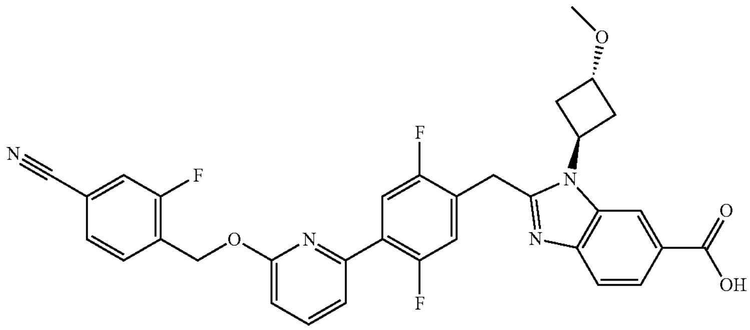 [SMILES: CO[C@H]1C[C@H](n2c(Cc3cc(F)c(-c4cccc(OCc5ccc(C#N)cc5F)n4)cc3F)nc3ccc(C(=O)O)cc32)C1] 2-(4-(6-((4-cyano-2-fluorobenzyl)oxy)pyridin-2-yl)-2,5-difluorobenzyl)-1-((1r,3r)-3-methoxycyclobutyl)-1H-benzo[d]imidazole-6-carboxylic acid: ES/MS 599.2; $^1$H NMR (400 MHz, Methanol-d4) δ 8.56 (dd, J = 1.5, 0.7 Hz, 1H), 8.17 (dd, J = 8.6, 1.4 Hz, 1H), 7.88-7.75 (m, 3H), 7.73 (t, J = 7.5 Hz, 1H), 7.63-7.54 (m, 3H), 7.26 (dd, J = 11.3, 6.1 Hz, 1H), 6.95 (dd, J = 8.3, 0.7 Hz, 1H), 5.63 (s, 2H), 5.53 (p, J = 8.6 Hz, 1H), 4.63 (s, 2H), 4.38 (t, J = 6.9 Hz, 1H), 3.39 (s, 3H), 3.25-3.14 (m, 2H), 2.75 (ddt, J = 11.0, 8.7, 2.1 Hz, 2H). |
| 583 | 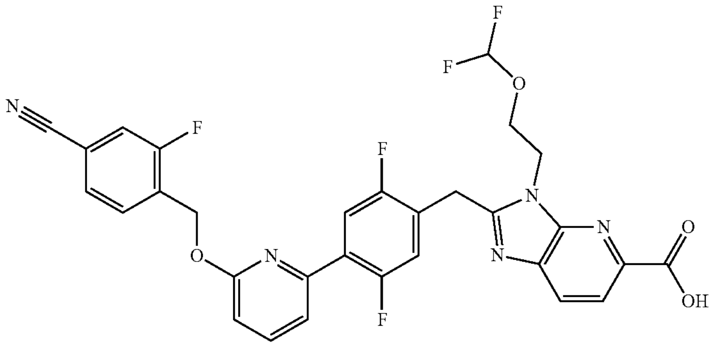 [SMILES: N#Cc1ccc(COc2cccc(-c3cc(F)c(Cc4nc5ccc(C(=O)O)nc5n4CCOC(F)F)cc3F)n2)c(F)c1] 2-(4-(6-((4-cyano-2-fluorobenzyl)oxy)pyridin-2-yl)-2,5-difluorobenzyl)-3-(2-(difluoromethoxy)ethyl)-3H-imidazo[4,5-b]pyridine-5-carboxylic acid: ES/MS 610.2; $^1$H NMR (400 MHz, DMSO-d6) δ 8.10 (d, J = 8.3 Hz, 1H), 7.99 (d, J = 8.2 Hz, 1H), 7.95-7.84 (m, 2H), 7.81-7.71 (m, 3H), 7.53 (dd, J = 7.4, 1.7 |

-continued

| Example | Structure/Name/Characterization |
|---|---|
| | Hz, 1H), 7.42 (dd, J = 11.4, 6.0 Hz, 1H), 6.99 (dd, J = 8.3, 5.5 Hz, 1H), 6.66 (t, J = 75.4 Hz, 1H), 5.61 (s, 2H), 4.71 (t, J = 5.3 Hz, 2H), 4.51 (s, 2H), 4.31 (t, J = 5.3 Hz, 2H). |
| 584 | 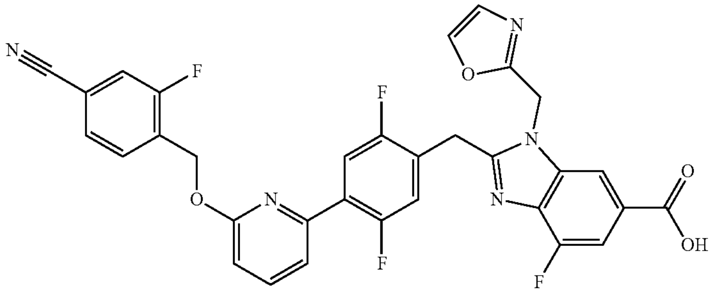 [SMILES: N#Cc1ccc(COc2cccc(-c3cc(F)c(Cc4nc5c(F)cc(C(=O)O)cc5n4Cc4ncco4)cc3F)n2)c(F)c1] 2-(4-(6-((4-cyano-2-fluorobenzyl)oxy)pyridin-2-yl)-2,5-difluorobenzyl)-4-fluoro-1-(oxazol-2-ylmethyl)-1H-benzo[d]imidazole-6-carboxylic acid: ES/MS 614; $^1$H NMR (400 MHz, DMSO-$d_6$) δ 8.14 (d, J = 1.2 Hz, 1H), 8.09 (s, 1H), 7.98-7.84 (m, 2H), 7.80-7.66 (m, 3H), 7.58-7.47 (m, 2H), 7.32 (dd, J = 11.5, 6.0 Hz, 1H), 7.15 (s, 1H), 6.99 (d, J = 8.3 Hz, 1H), 5.97 (s, 2H), 5.60 (s, 2H), 4.50 (s, 2H). |
| 585 | 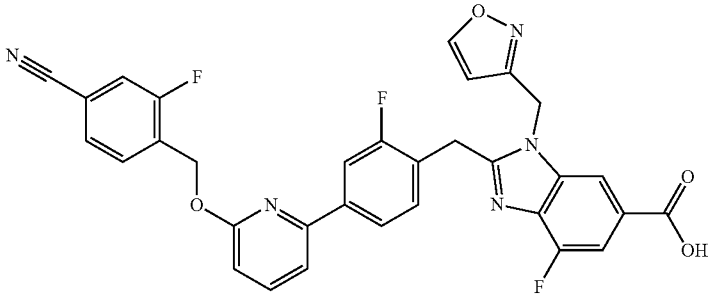 [SMILES: N#Cc1ccc(COc2cccc(-c3ccc(Cc4nc5c(F)cc(C(=O)O)cc5n4Cc4ccon4)c(F)c3)n2)c(F)c1] 2-(4-(6-((4-cyano-2-fluorobenzyl)oxy)pyridin-2-yl)-2-fluorobenzyl)-4-fluoro-1-(isoxazol-3-ylmethyl)-1H-benzo[d]imidazole-6-carboxylic acid: ES/MS 596.2; $^1$H NMR (400 MHz, DMSO-d6) δ 8.90 (d, J = 1.7 Hz, 1H), 8.09 (d, J = 1.2 Hz, 1H), 7.93 (dd, J = 10.0, 1.5 Hz, 1H), 7.89-7.83 (m, 3H), 7.81-7.70 (m, 3H), 7.66 (d, J = 7.4 Hz, 1H), 7.53 (dd, J = 11.3, 1.3 Hz, 1H), 7.45 (t, J = 7.9 Hz, 1H), 6.93 (d, J = 8.2 Hz, 1H), 6.51 (d, J = 1.7 Hz, 1H), 5.87 (s, 2H), 5.62 (s, 2H), 4.48 (s, 2H). |
| 606 | ES/MS (m/z) 592.1; 1H NMR (400 MHz, DMSO-d6) δ 8.21 (d, J = 1.5 Hz, 1H), 7.92 (dd, J = 10.0, 1.4 Hz, 1H), 7.88-7.79 (m, 5H), 7.79-7.69 (m, 2H), 7.64 (dd, J = 12.4, 8.0 Hz, 2H), 7.41 (t, J = 7.8 Hz, 1H), 6.93 (d, J = 8.2 Hz, 1H), 6.06 (s, 1H), 5.74 (s, 2H), 5.61 (s, 2H), 4.45 (s, 2H), 2.30 (s, 3H); (multiplet report) 19F NMR (376 MHz, DMSO-d6) δ −74.83, −115.95 (dd, J = 10.8, 7.2 Hz), −117.10 (dd, J = 13.1, 8.9 Hz). |
| 607 | 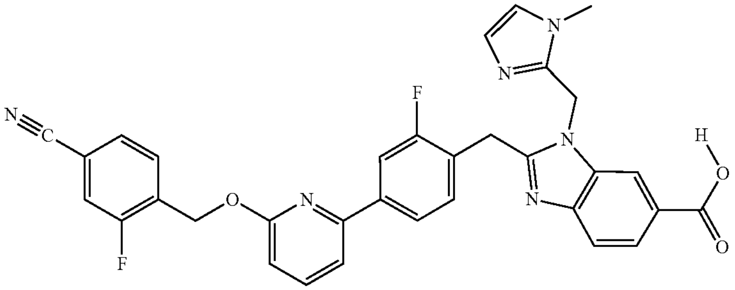 [SMILES: Cn1ccnc1Cn1c(Cc2ccc(-c3cccc(OCc4ccc(C#N)cc4F)n3)cc2F)nc2ccc(C(=O)O)cc21] ES/MS (m/z) 591.2; 1H NMR (400 MHz, Methanol-d4) δ 8.23 (d, J = 1.4 Hz, 1H), 8.10 (dd, J = 8.5, 1.5 Hz, 1H), 7.84-7.53 (m, 8H), 7.51-7.45 (m, 2H), 7.40 (t, J = 7.9 Hz, 1H), 7.12 (d, J = 2.0 Hz, 1H), 6.89 (d, J = 8.2 Hz, 1H), 6.11 (s, 2H), 5.62 (s, 2H), 4.52 (s, 2H), 3.94 (s, 3H).; Multiplet Report 1H NMR (400 MHz, Chloroform-d) δ 7.48-7.33 (m, 2H), 6.94 (dd, J = 49.1, 1.1 Hz, 2H), 6.67 (d, J = 8.1 Hz, 1H), 4.34 (s, 2H), 3.64 (s, 3H), 1.58 (s, 10H). |

-continued

| Example | Structure/Name/Characterization |
| --- | --- |
| 608 | 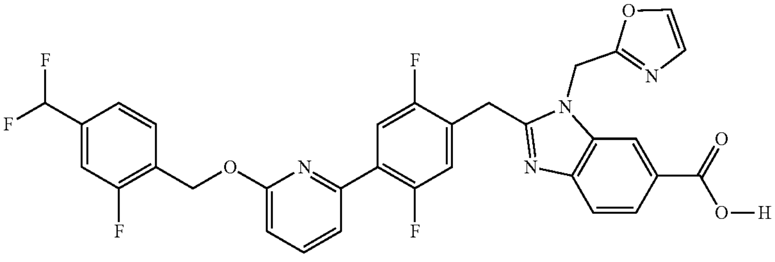 [SMILES: O=C(O)c1ccc2nc(Cc3cc(F)c(-c4cccc(OCc5ccc(C(F)F)cc5F)n4)cc3F)n(Cc3ncco3)c2c1] ES/MS (m/z) 621.1; 1H NMR (400 MHz, Methanol-d4) δ 8.57 (dd, J = 1.5, 0.7 Hz, 1H), 8.25-8.10 (m, 2H), 7.90-7.81 (m, 2H), 7.81-7.73 (m, 1H), 7.68 (t, J = 7.5 Hz, 1H), 7.56 (dd, J = 7.4, 1.6 Hz, 1H), 7.37 (dd, J = 12.0, 9.6 Hz, 2H), 7.32-7.21 (m, 2H), 6.97-6.60 (m, 2H), 6.00-5.88 (m, 2H), 5.60 (s, 2H), 4.76 (s, 2H). |
| 609 | 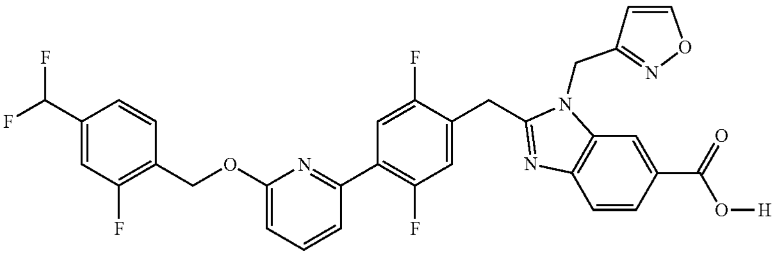 [SMILES: O=C(O)c1ccc2nc(Cc3cc(F)c(-c4cccc(OCc5ccc(C(F)F)cc5F)n4)cc3F)n(Cc3ccon3)c2c1] ES/MS (m/z) 621.1; 1H NMR (400 MHz, DMSO-d6) δ 8.84 (d, J = 1.7 Hz, 1H), 8.15 (d, J = 1.5 Hz, 1H), 7.86-7.79 (m, 1H), 7.76 (dd, J = 8.4, 1.6 Hz, 1H), 7.73-7.61 (m, 2H), 7.58 (d, J = 8.4 Hz, 1H), 7.48-7.35 (m, 4H), 7.32 (dd, J = 11.5, 6.1 Hz, 1H), 7.19-6.77 (m, 2H), 6.47 (d, J = 1.7 Hz, 1H), 5.80 (s, 2H), 5.51 (s, 2H), 4.42 (s, 2H). |
| 610 | 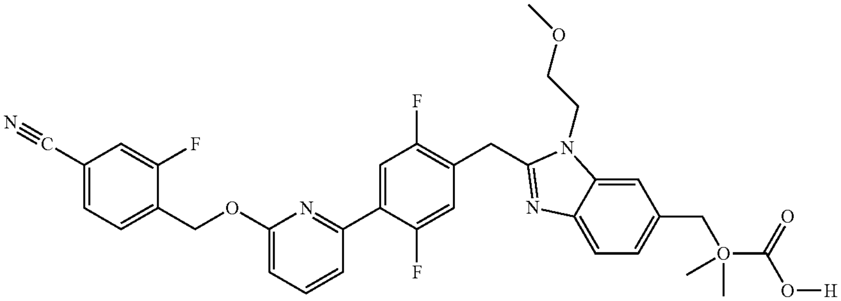 ES/MS (m/z) (M + H+) 631.2; 1H NMR (400 MHz, DMSO-d6) δ 7.97-7.87 (m, 2H), 7.84-7.71 (m, 3H), 7.61-7.50 (m, 2H), 7.47 (dd, J = 11.5, 6.1 Hz, 1H), 7.28 (d, J = 2.2 Hz, 1H), 7.00 (dd, J = 10.9, 7.6 Hz, 2H), 5.60 (s, 2H), 4.57 (s, 4H), 3.66 (t, J = 5.0 Hz, 2H), 3.21 (s, 3H), 1.55 (s, 6H); (Multiplet Report) 19F NMR (376 MHz, DMSO-d6) δ −74.82, −115.96 (dd, J = 10.0, 5.9 Hz), −121.36, −122.20 (d, J = 10.9 Hz). |
| 611 | 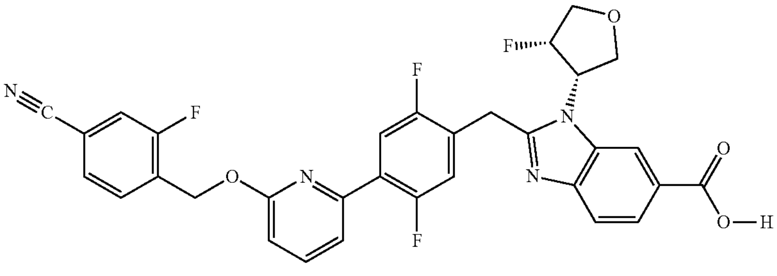 [SMILES: N#Cc1ccc(COc2cccc(-c3cc(F)c(Cc4nc5ccc(C(=O)O)cc5n4[C@H]4COC[C@H]4F)cc3F)n2)c(F)c1] ES/MS (m/z) 603.2; 1H NMR (400 MHz, DMSO-d6) δ 8.35 (dd, J = 3.1, 1.5 Hz, 1H), 7.96-7.88 (m, 2H), 7.85-7.70 (m, 4H), 7.63 (d, J = 8.4 Hz, 1H), 7.54 (dd, J = 7.5, 1.7 Hz, 1H), 7.34 (dd, J = 11.4, 6.1 Hz, 1H), 7.00 (d, J = 8.3 Hz, 1H), 5.71 (ddt, J = 19.6, 9.8, 5.0 Hz, 1H), 5.61 (s, 2H), 5.42 (ddd, J = 55.0, |

-continued

| Example | Structure/Name/Characterization |
|---|---|
| | 5.9, 2.8 Hz, 1H), 4.56 (s, 2H), 4.50 (dd, J = 10.4, 4.3 Hz, 1H), 4.37 (dd, J = 22.4, 11.8 Hz, 1H), 4.06 (dd, J = 10.4, 8.8 Hz, 1H), 3.97-3.75 (m, 1H). |
| 612 | 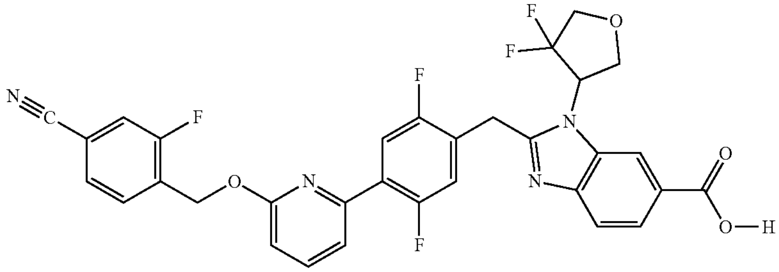 [SMILES: N#Cc1ccc(COc2cccc(-c3cc(F)c(Cc4nc5ccc(C(=O)O)cc5n4C4COCC4(F)F)cc3F)n2)c(F)c1] ES/MS (m/z) 621.0; 1H NMR (400 MHz, DMSO-d6) δ 8.36 (d, J = 1.9 Hz, 1H), 7.95-7.81 (m, 3H), 7.81-7.64 (m, 4H), 7.53 (dd, J = 7.5, 1.7 Hz, 1H), 7.34 (dd, J = 11.5, 6.1 Hz, 1H), 6.99 (d, J = 8.2 Hz, 1H), 5.87 (dtd, J = 12.4, 8.3, 3.6 Hz, 1H), 5.60 (s, 2H), 4.67-4.34 (m, 5H), 4.13 (ddd, J = 24.1, 11.4, 8.5 Hz, 1H). |
| 613 | 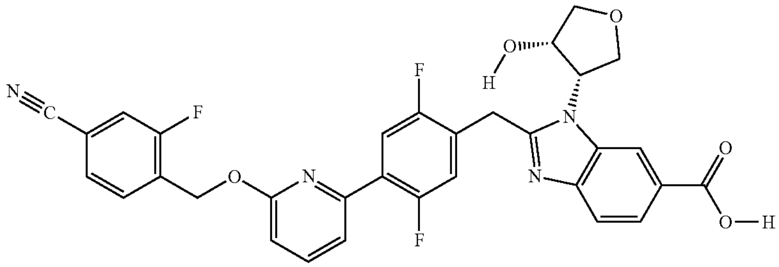 [SMILES: N#Cc1ccc(COc2cccc(-c3cc(F)c(Cc4nc5ccc(C(=O)O)cc5n4[C@H]4COC[C@H]4O)cc3F)n2)c(F)c1] ES/MS (m/z) 601.2; 1H NMR (400 MHz, DMSO-d6) δ 8.54 (d, J = 1.5 Hz, 1H), 7.99-7.82 (m, 3H), 7.82-7.70 (m, 3H), 7.65 (d, J = 8.5 Hz, 1H), 7.54 (dd, J = 7.5, 1.7 Hz, 1H), 7.39 (dd, J = 11.5, 6.1 Hz, 1H), 7.01 (d, J = 8.2 Hz, 1H), 5.61 (s, 2H), 5.47 (td, J = 7.4, 3.6 Hz, 1H), 4.69-4.53 (m, 3H), 4.53-4.43 (m, 1H), 4.07 (dd, J = 10.6, 7.9 Hz, 1H), 3.93-3.80 (m, 2H). |
| 614 | 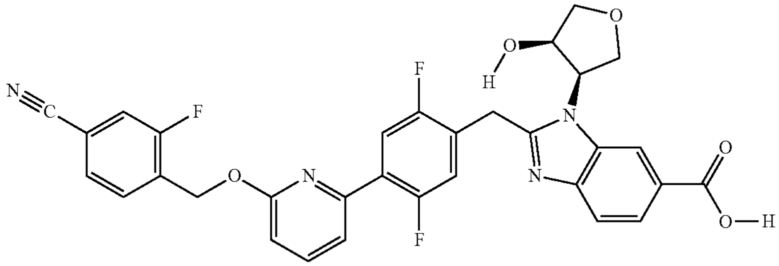 [SMILES: N#Cc1ccc(COc2cccc(-c3cc(F)c(Cc4nc5ccc(C(=O)O)cc5n4[C@@H]4COC[C@@H]4O)cc3F)n2)c(F)c1] ES/MS (m/z) 601.2; 1H NMR (400 MHz, DMSO-d6) δ 8.55 (d, J = 1.5 Hz, 1H), 7.99-7.83 (m, 3H), 7.83-7.70 (m, 3H), 7.66 (d, J = 8.5 Hz, 1H), 7.54 (dd, J = 7.6, 1.7 Hz, 1H), 7.39 (dd, J = 11.5, 6.1 Hz, 1H), 7.00 (d, J = 8.2 Hz, 1H), 5.61 (s, 2H), 5.47 (td, J = 7.4, 3.6 Hz, 1H), 4.73-4.42 (m, 4H), 4.07 (dd, J = 10.6, 7.9 Hz, 1H), 3.89 (d, J = 4.1 Hz, 2H). |
| 615 | 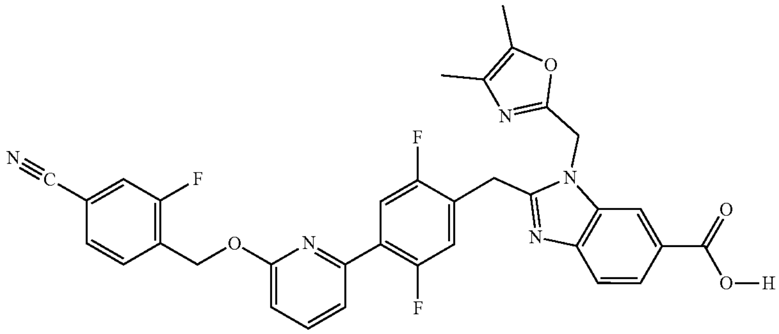 [SMILES: Cc1nc(Cn2c(Cc3cc(F)c(-c4cccc(OCc5ccc(C#N)cc5F)n4)cc3F)nc3ccc(C(=O)O)cc32)oc1C] |

-continued

| Example | Structure/Name/Characterization |
|---|---|
| | ES/MS (m/z) 624.2; 1H NMR (400 MHz, DMSO-d6) δ 8.30 (d, J = 1.4 Hz, 1H), 7.97-7.84 (m, 3H), 7.79-7.63 (m, 4H), 7.49 (dd, J = 7.5, 1.7 Hz, 1H), 7.24 (dd, J = 11.6, 6.1 Hz, 1H), 6.99 (d, J = 8.3 Hz, 1H), 5.83 (s, 2H), 5.60 (s, 2H), 4.52 (s, 2H), 2.07 (d, J = 1.1 Hz, 3H), 1.81 (d, J = 1.0 Hz, 3H). |
| 616 | 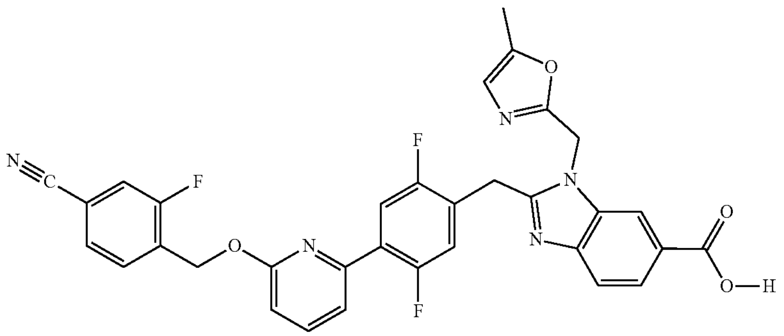 [SMILES: Cc1cnc(Cn2c(Cc3cc(F)c(-c4cccc(OCc5ccc(C#N)cc5F)n4)cc3F)nc3ccc(C(=O)O)cc32)o1] ES/MS (m/z) 610.2; 1H NMR (400 MHz, DMSO-d6) δ 8.28 (d, J = 1.5 Hz, 1H), 7.98-7.82 (m, 3H), 7.81-7.63 (m, 4H), 7.50 (dd, J = 7.5, 1.7 Hz, 1H), 7.30 (dd, J = 11.5, 6.1 Hz, 1H), 6.99 (d, J = 8.2 Hz, 1H), 6.73 (t, J = 1.3 Hz, 1H), 5.86 (s, 2H), 5.60 (s, 2H), 4.52 (s, 2H), 2.16 (d, J = 1.2 Hz, 3H). |
| 617 | 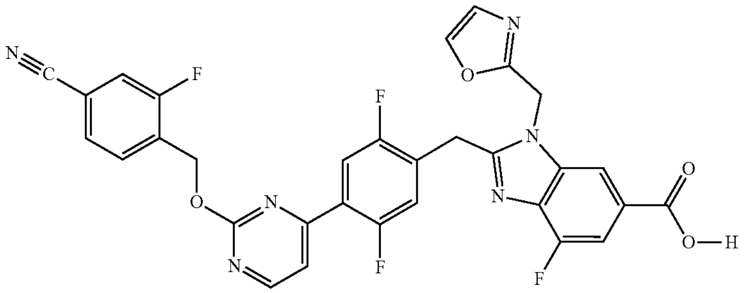 [SMILES: N#Cc1ccc(COc2nccc(-c3cc(F)c(Cc4nc5c(F)cc(C(=O)O)cc5n4Cc4ncco4)cc3F)n2)c(F)c1] ES/MS (m/z) 615.0; 1H NMR (400 MHz, DMSO-d6) δ 8.78 (d, J = 5.2 Hz, 1H), 8.15 (d, J = 1.3 Hz, 1H), 8.09 (d, J = 0.8 Hz, 1H), 7.95 (dd, J = 9.9, 1.4 Hz, 1H), 7.86 (dd, J = 10.2, 6.2 Hz, 1H), 7.83-7.71 (m, 2H), 7.62 (dd, J = 5.1, 1.8 Hz, 1H), 7.55 (dd, J = 11.3, 1.3 Hz, 1H), 7.41 (dd, J = 11.5, 6.0 Hz, 1H), 7.14 (d, J = 0.8 Hz, 1H), 5.97 (s, 2H), 5.63 (s, 2H), 4.53 (s, 2H). |
| 618 | 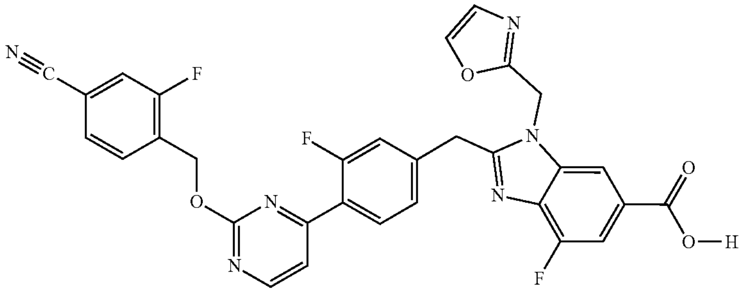 [SMILES: N#Cc1ccc(COc2nccc(-c3ccc(Cc4nc5c(F)cc(C(=O)O)cc5n4Cc4ncco4)cc3F)n2)c(F)c1] ES/MS (m/z) 597.0; 1H NMR (400 MHz, DMSO-d6) δ 8.73 (d, J = 5.1 Hz, 1H), 8.10 (d, J = 1.2 Hz, 1H), 8.06-7.89 (m, 3H), 7.80-7.70 (m, 2H), 7.60-7.51 (m, 2H), 7.35-7.25 (m, 2H), 7.10 (d, J = 0.9 Hz, 1H), 5.93 (s, 2H), 5.60 (s, 2H), 4.53 (s, 2H). |

-continued

| Example | Structure/Name/Characterization |
|---|---|
| 619 | 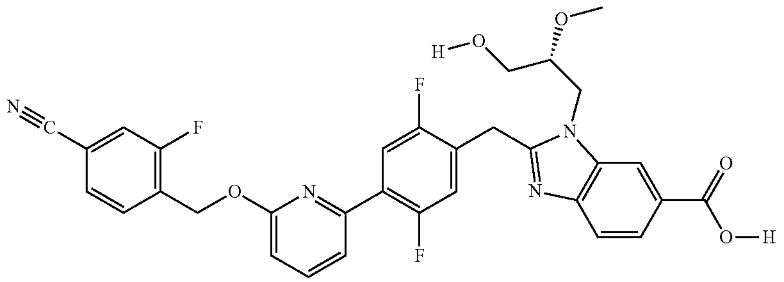 [SMILES: CO[C@@H](CO)Cn1c(Cc2cc(F)c(-c3cccc(OCc4ccc(C#N)cc4F)n3)cc2F)nc2ccc(C(=O)O)cc21] ES/MS (m/z) 603.2; 1H NMR (400 MHz, DMSO-d6) δ 8.31 (d, J = 1.4 Hz, 1H), 8.01-7.84 (m, 4H), 7.84-7.70 (m, 4H), 7.67 (dd, J = 8.4, 3.2 Hz, 1H), 7.54 (dd, J = 7.5, 1.8 Hz, 1H), 7.42 (dt, J = 11.4, 7.0 Hz, 1H), 7.00 (d, J = 8.2 Hz, 1H), 5.60 (s, 2H), 4.67-4.39 (m, 5H), 3.66-3.48 (m, 3H), 3.14 (s, 3H). |
| 620 | 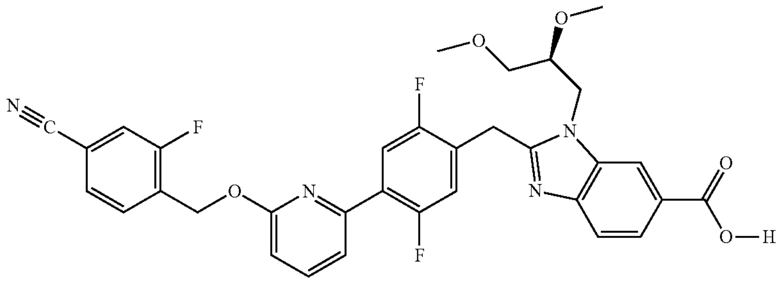 [SMILES: COC[C@H](Cn1c(Cc2cc(F)c(-c3cccc(OCc4ccc(C#N)cc4F)n3)cc2F)nc2ccc(C(=O)O)cc21)OC] ES/MS (m/z) 617.2; 1H NMR (400 MHz, DMSO-d6) δ 8.29 (d, J = 1.5 Hz, 1H), 7.96-7.85 (m, 3H), 7.81-7.71 (m, 3H), 7.67 (d, J = 8.4 Hz, 1H), 7.53 (dd, J = 7.4, 1.7 Hz, 1H), 7.42 (dd, J = 11.5, 6.1 Hz, 1H), 7.00 (d, J = 8.2 Hz, 1H), 5.60 (s, 2H), 4.62 (dd, J = 15.2, 3.5 Hz, 1H), 4.57-4.36 (m, 3H), 3.71 (dq, J = 8.4, 4.4 Hz, 1H), 3.52 (d, J = 4.6 Hz, 2H), 3.34 (s, 3H), 3.15 (s, 3H). |
| 621 | 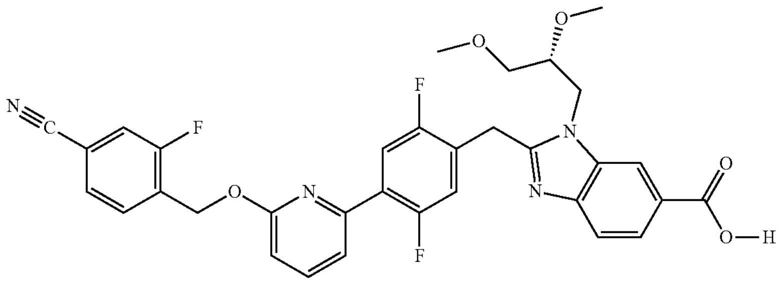 [SMILES: COC[C@@H](Cn1c(Cc2cc(F)c(-c3cccc(OCc4ccc(C#N)cc4F)n3)cc2F)nc2ccc(C(=O)O)cc21)OC] ES/MS (m/z) 617.2; 1H NMR (400 MHz, DMSO-d6) δ 8.29 (d, J = 1.5 Hz, 1H), 7.96-7.85 (m, 3H), 7.81-7.71 (m, 3H), 7.67 (d, J = 8.4 Hz, 1H), 7.53 (dd, J = 7.4, 1.7 Hz, 1H), 7.42 (dd, J = 11.5, 6.1 Hz, 1H), 7.00 (d, J = 8.2 Hz, 1H), 5.60 (s, 2H), 4.62 (dd, J = 15.2, 3.5 Hz, 1H), 4.57-4.36 (m, 3H), 3.71 (dq, J = 8.4, 4.4 Hz, 1H), 3.52 (d, J = 4.6 Hz, 2H), 3.34 (s, 3H), 3.15 (s, 3H). |
| 622 | 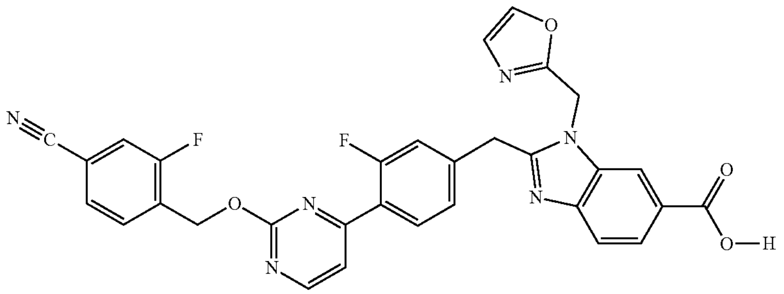 [SMILES: N#Cc1ccc(COc2nccc(-c3ccc(Cc4nc5ccc(C(=O)O)cc5n4Cc4ncco4)cc3F)n2)c(F)c1] ES/MS (m/z) 579.2; 1H NMR (400 MHz, DMSO-d6) δ 8.73 (d, J = 5.1 Hz, 1H), 8.24 (d, J = 1.5 Hz, 1H), 8.07-7.91 (m, 3H), 7.86 (dd, J = 8.4, 1.6 Hz, 1H), 7.76 (d, J = 6.1 Hz, 2H), 7.69 (d, J = 8.5 Hz, 1H), 7.56 (dd, J = 5.1, 2.0 |

-continued

| Example | Structure/Name/Characterization |
|---|---|
| | Hz, 1H), 7.36-7.24 (m, 2H), 7.11 (d, J = 0.9 Hz, 1H), 5.91 (s, 2H), 5.60 (s, 2H), 4.54 (s, 2H). |
| 623 | 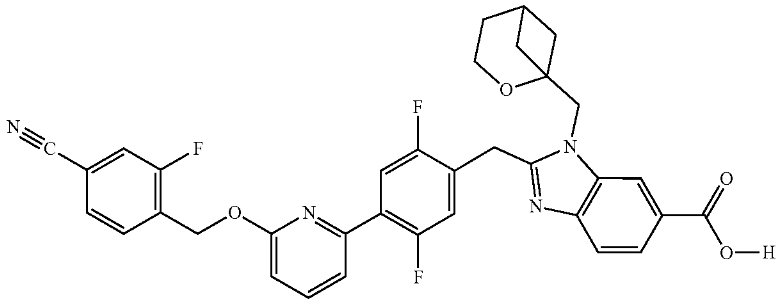 [SMILES: N#Cc1ccc(COc2cccc(-c3cc(F)c(Cc4nc5ccc(C(=O)O)cc5n4CC45CC(CCO4)C5)cc3F)n2)c(F)c1] ES/MS (m/z) 625.2; 1H NMR (400 MHz, DMSO-d6) δ 8.36 (d, J = 1.5 Hz, 1H), 8.01-7.82 (m, 3H), 7.81-7.70 (m, 3H), 7.63 (d, J = 8.4 Hz, 1H), 7.53 (dd, J = 7.5, 1.7 Hz, 1H), 7.40 (dd, J = 11.5, 6.0 Hz, 1H), 7.00 (d, J = 8.3 Hz, 1H), 5.60 (s, 2H), 4.54 (s, 2H), 4.51 (s, 2H), 3.93 (t, J = 6.8 Hz, 2H), 2.23 (td, J = 6.4, 2.5 Hz, 2H), 1.94 (td, J = 6.9, 3.2 Hz, 2H), 1.69 (dt, J = 8.9, 4.4 Hz, 2H). |
| 624 | 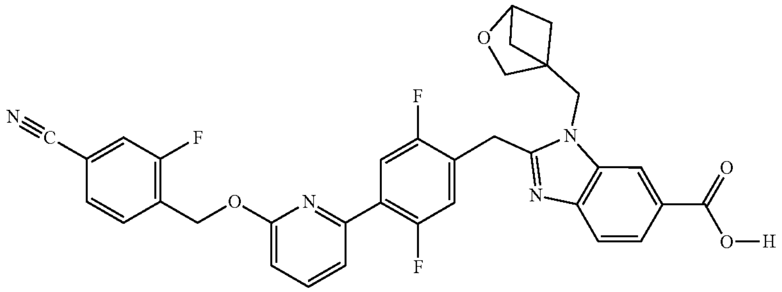 [SMILES: N#Cc1ccc(COc2cccc(-c3cc(F)c(Cc4nc5ccc(C(=O)O)cc5n4CC45COC(C4)C5)cc3F)n2)c(F)c1] ES/MS (m/z) 611.2; 1H NMR (400 MHz, DMSO-d6) δ 8.31 (d, J = 1.4 Hz, 1H), 7.97-7.82 (m, 3H), 7.80-7.70 (m, 3H), 7.67 (d, J = 8.5 Hz, 1H), 7.57-7.46 (m, 2H), 7.00 (d, J = 8.3 Hz, 1H), 5.60 (s, 2H), 4.91 (s, 2H), 4.47 (s, 2H), 4.42 (s, 1H), 3.61 (s, 2H), 1.65 (d, J = 4.6 Hz, 2H), 1.50 (dd, J = 4.5, 1.7 Hz, 2H). |
| 625 | 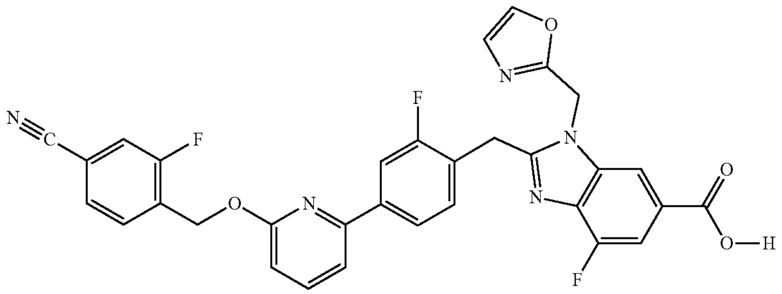 [SMILES: N#Cc1ccc(COc2cccc(-c3ccc(Cc4nc5c(F)cc(C(=O)O)cc5n4Cc4ncco4)c(F)c3)n2)c(F)c1] ES/MS (m/z) 596.2; 1H NMR (400 MHz, DMSO-d6) δ 8.13 (d, J = 1.3 Hz, 1H), 8.08 (d, J = 0.8 Hz, 1H), 7.93 (dd, J = 9.9, 1.4 Hz, 1H), 7.90-7.80 (m, 3H), 7.80-7.70 (m, 2H), 7.65 (d, J = 7.4 Hz, 1H), 7.54 (dd, J = 11.2, 1.3 Hz, 1H), 7.40 (t, J = 8.0 Hz, 1H), 7.16 (d, J = 0.8 Hz, 1H), 6.93 (d, J = 8.2 Hz, 1H), 5.95 (s, 2H), 5.62 (s, 2H), 4.48 (s, 2H). |

-continued

| Example | Structure/Name/Characterization |
|---|---|
| 626 | 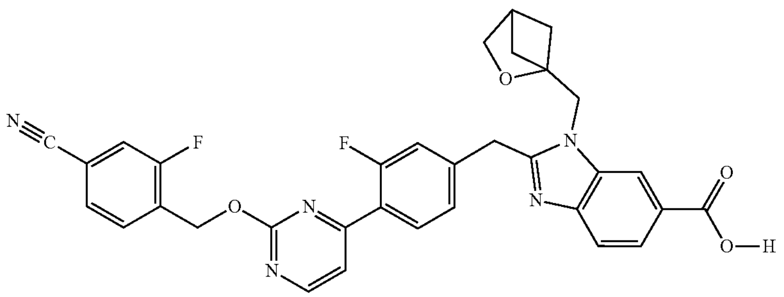 [SMILES: N#Cc1ccc(COc2nccc(-c3ccc(Cc4nc5ccc(C(=O)O)cc5n4CC45CC(CO4)C5)cc3F)n2)c(F)c1] ES/MS (m/z) 594.2; 1H NMR (400 MHz, DMSO-d6) δ 8.74 (d, J = 5.2 Hz, 1H), 8.35 (d, J = 1.4 Hz, 1H), 8.07 (t, J = 8.2 Hz, 1H), 7.98-7.92 (m, 1H), 7.88 (dd, J = 8.4, 1.5 Hz, 1H), 7.82-7.72 (m, 2H), 7.67 (d, J = 8.5 Hz, 1H), 7.59 (dd, J = 5.2, 2.0 Hz, 1H), 7.49-7.33 (m, 2H), 5.61 (s, 2H), 4.83 (s, 2H), 4.58 (s, 2H), 3.63 (s, 2H), 2.89 (t, J = 3.1 Hz, 1H), 1.91 (ddd, J = 4.6, 3.3, 1.7 Hz, 2H), 1.28 (dd, J = 4.4, 1.7 Hz, 2H). |
| 627 | 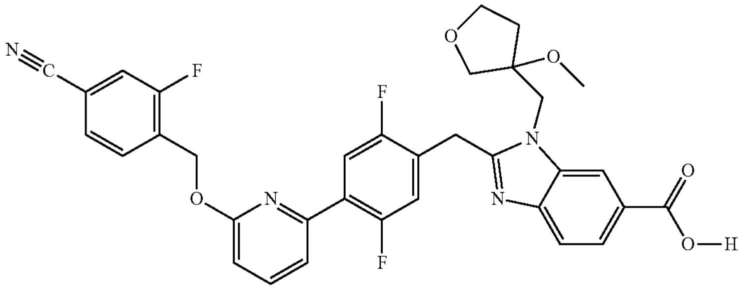 [SMILES: COC1(Cn2c(Cc3cc(F)c(-c4cccc(OCc5ccc(C#N)cc5F)n4)cc3F)nc3ccc(C(=O)O)cc32)CCOC1] ES/MS (m/z) 629.2; 1H NMR (400 MHz, DMSO) δ 8.36 (d, J = 1.6 Hz, 1H), 7.98-7.86 (m, 2H), 7.83 (dd, J = 8.5, 1.5 Hz, 1H), 7.75 (td, J = 6.6, 4.6 Hz, 3H), 7.62 (d, J = 8.4 Hz, 1H), 7.53 (dd, J = 7.4, 1.7 Hz, 1H), 7.41 (dd, J = 11.5, 6.1 Hz, 1H), 7.00 (d, J = 8.2 Hz, 1H), 5.60 (s, 2H), 4.80-4.66 (m, 2H), 4.50 (s, 2H), 3.92 (t, J = 7.3 Hz, 2H), 3.78-3.62 (m, 2H), 3.24 (s, 3H), 2.10 (dq, J = 8.7, 6.2, 5.7 Hz, 2H). 19F NMR (377 MHz, DMSO) δ −115.91 (dd, J = 9.8, 6.1 Hz), −121.92 (dt, J = 18.8, 9.5 Hz), −122.48 (ddd, J = 17.1, 10.3, 6.1 Hz). |
| 628 | 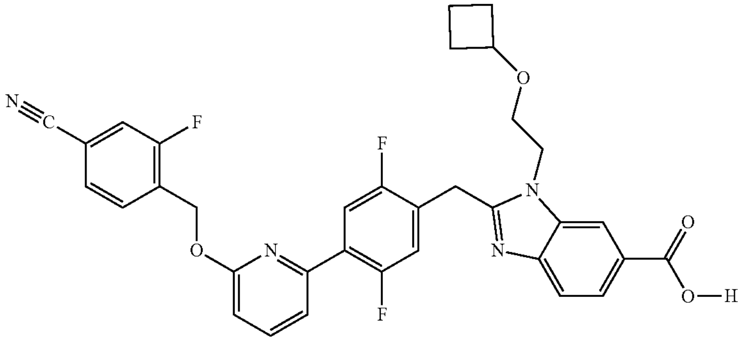 [SMILES: N#Cc1ccc(COc2cccc(-c3cc(F)c(Cc4nc5ccc(C(=O)O)cc5n4CCOC4CCC4)cc3F)n2)c(F)c1] ES/MS (m/z) 613.383; 1H NMR (400 MHz, DMSO) δ 8.22 (d, J = 1.6 Hz, 1H), 7.96-7.86 (m, 2H), 7.83-7.70 (m, 4H), 7.60 (d, J = 8.4 Hz, 1H), 7.53 (dd, J = 7.5, 1.8 Hz, 1H), 7.36 (dd, J = 11.5, 6.0 Hz, 1H), 6.99 (d, J = 8.2 Hz, 1H), 5.61 (s, 2H), 4.56 (t, J = 5.1 Hz, 2H), 4.46 (s, 2H), 3.84 (p, J = 6.9 Hz, 1H), 3.60 (t, J = 5.1 Hz, 2H), 2.08-1.96 (m, 2H), 1.68-1.46 (m, 3H), 1.44-1.30 (m, 1H). 19F NMR (376 MHz, DMSO) δ −115.91 (dd, J = 10.0, 6.3 Hz), −122.05 (ddd, J = 18.3, 11.7, 6.6 Hz), −122.55 (ddd, J = 17.1, 10.3, 6.1 Hz). |

-continued

| Example | Structure/Name/Characterization |
|---|---|
| 629 | 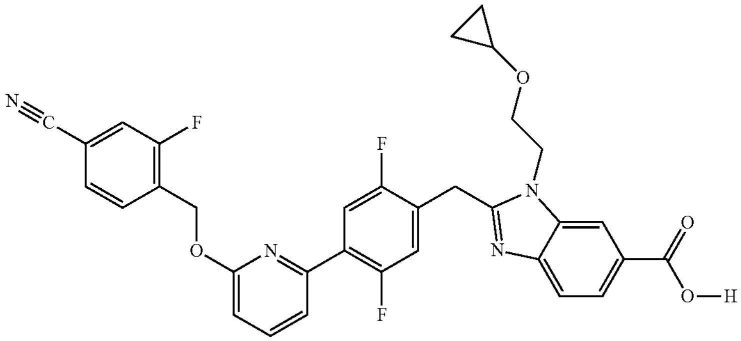 [SMILES: N#Cc1ccc(COc2cccc(-c3cc(F)c(Cc4nc5ccc(C(=O)O)cc5n4CCOC4CC4)cc3F)n2)c(F)c1] ES/MS (m/z) 599.375; 1H NMR (400 MHz, DMSO) δ 8.19 (d, J = 1.6 Hz, 1H), 7.96-7.86 (m, 2H), 7.76 (dtd, J = 12.9, 8.0, 1.9 Hz, 4H), 7.59 (d, J = 8.4 Hz, 1H), 7.53 (dd, J = 7.3, 1.8 Hz, 1H), 7.35 (dd, J = 11.5, 6.1 Hz, 1H), 6.99 (d, J = 8.2 Hz, 1H), 5.61 (s, 2H), 4.55 (t, J = 5.2 Hz, 2H), 4.40 (s, 2H), 3.77 (t, J = 5.1 Hz, 2H), 3.24 (tt, J = 6.0, 2.9 Hz, 1H), 0.32 (tt, J = 7.2, 4.6 Hz, 2H), 0.24 (h, J = 3.4 Hz, 2H). 19F NMR (376 MHz, DMSO) δ −115.90 (dd, J = 10.1, 6.3 Hz), −121.59-−122.26 (m), −122.26-−123.03 (m). |
| 630 | 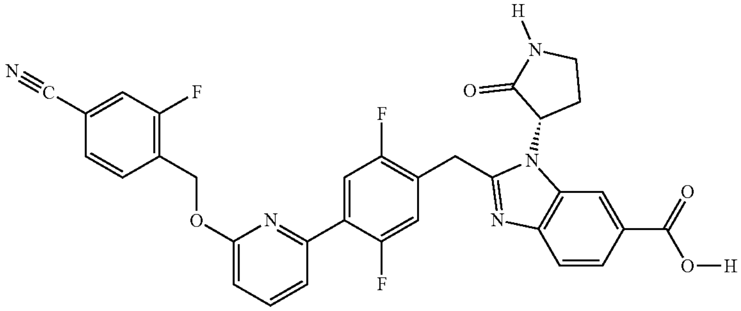 [SMILES: N#Cc1ccc(COc2cccc(-c3cc(F)c(Cc4nc5ccc(C(=O)O)cc5n4[C@H]4CCNC4=O)cc3F)n2)c(F)c1] ES/MS (m/z) 598.5; 1H NMR (400 MHz, DMSO-d6) δ 8.53 (s, 1H), 7.98 (s, 1H), 7.96-7.86 (m, 2H), 7.83 (dd, J = 8.4, 1.5 Hz, 1H), 7.81-7.70 (m, 3H), 7.67 (d, J = 8.4 Hz, 1H), 7.53 (dd, J = 7.6, 1.7 Hz, 1H), 7.39 (dd, J = 11.5, 6.1 Hz, 1H), 6.99 (d, J = 8.2 Hz, 1H), 5.65 (t, J = 10.0 Hz, 1H), 5.60 (s, 2H), 4.54-4.36 (m, 2H), 3.54 (t, J = 9.5 Hz, 1H), 3.48-3.38 (m, 1H), 2.72-2.59 (m, 1H), 2.47-2.32 (m, 1H). |
| 631 | 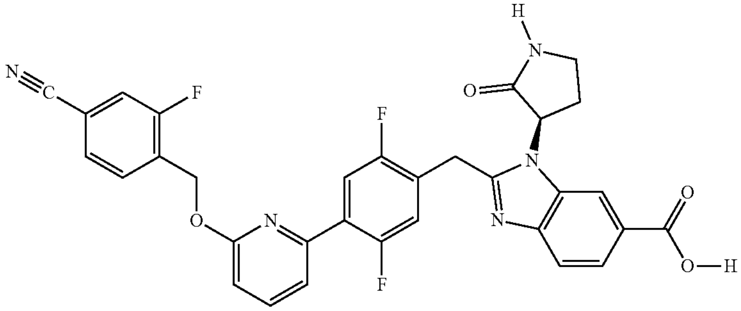 [SMILES: N#Cc1ccc(COc2cccc(-c3cc(F)c(Cc4nc5ccc(C(=O)O)cc5n4[C@@H]4CCNC4=O)cc3F)n2)c(F)c1] ES/MS (m/z) 598.5; 1H NMR (400 MHz, DMSO-d6) δ 8.52 (s, 1H), 7.98 (s, 1H), 7.96-7.86 (m, 2H), 7.83 (dd, J = 8.4, 1.5 Hz, 1H), 7.81-7.71 (m, 3H), 7.67 (d, J = 8.5 Hz, 1H), 7.53 (dd, J = 7.5, 1.7 Hz, 1H), 7.39 (dd, J = 11.5, 6.1 Hz, 1H), 6.99 (d, J = 8.3 Hz, 1H), 5.65 (t, J = 10.2 Hz, 1H), 5.60 (s, 2H), 4.57-4.35 (m, 2H), 3.54 (t, J = 9.5 Hz, 1H), 3.50-3.38 (m, 1H), 2.70-2.57 (m, 1H), 2.46-2.32 (m, 1H). |

-continued

| Example | Structure/Name/Characterization |
|---|---|
| 632 | 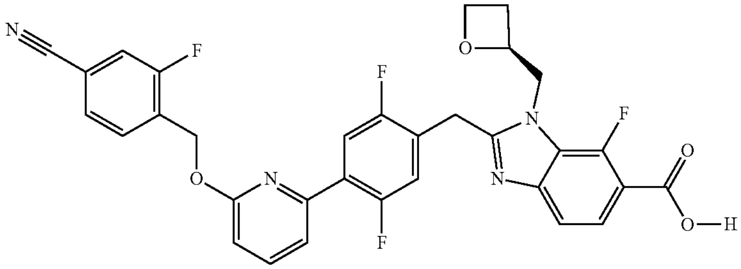 [SMILES: N#Cc1ccc(COc2cccc(-c3cc(F)c(Cc4nc5ccc(C(=O)O)c(F)c5n4C[C@@H]4CCO4)cc3F)n2)c(F)c1]<br>ES/MS (m/z) 603.2; 1H NMR (400 MHz, DMSO-d6) δ 7.99-7.84 (m, 2H), 7.82-7.69 (m, 3H), 7.65 (dd, J = 8.5, 6.7 Hz, 1H), 7.53 (dd, J = 7.5, 1.7 Hz, 1H), 7.47-7.34 (m, 2H), 7.00 (d, J = 8.3 Hz, 1H), 5.61 (s, 2H), 5.11 (qd, J = 7.2, 2.7 Hz, 1H), 4.81 (dd, J = 15.6, 7.3 Hz, 1H), 4.64 (dd, J = 15.7, 2.9 Hz, 1H), 4.58-4.35 (m, 4H), 2.83-2.71 (m, 1H), 2.48-2.38 (m, 1H). |
| 633 | 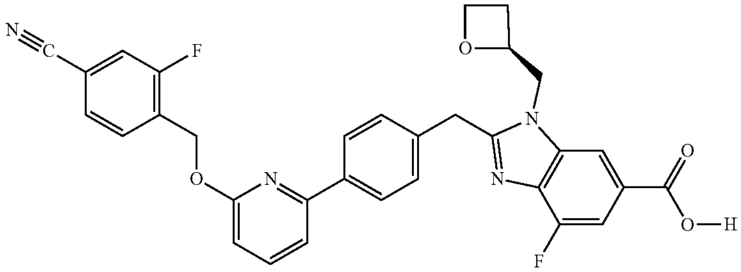 [SMILES: N#Cc1ccc(COc2cccc(-c3ccc(Cc4nc5c(F)cc(C(=O)O)cc5n4C[C@@H]4CCO4)cc3)n2)c(F)c1]<br>ES/MS (m/z) 567.3; 1H NMR (400 MHz, DMSO-d6) δ 8.14 (d, J = 1.3 Hz, 1H), 8.06-7.96 (m, 2H), 7.92 (dd, J = 9.9, 1.5 Hz, 1H), 7.83 (t, J = 7.8 Hz, 1H), 7.80-7.69 (m, 2H), 7.59 (d, J = 7.4 Hz, 1H), 7.52 (dd, J = 11.4, 1.3 Hz, 1H), 7.48-7.36 (m, 2H), 6.88 (d, J = 8.2 Hz, 1H), 5.61 (s, 2H), 4.94 (qd, J = 7.2, 2.6 Hz, 1H), 4.71 (dd, J = 15.5, 7.2 Hz, 1H), 4.57 (dd, J = 15.5, 2.7 Hz, 1H), 4.53-4.41 (m, 3H), 4.35 (dt, J = 9.1, 5.9 Hz, 1H), 2.71-2.57 (m, 1H), 2.34 (ddt, J = 11.3, 9.2, 7.0 Hz, 1H). |
| 634 | 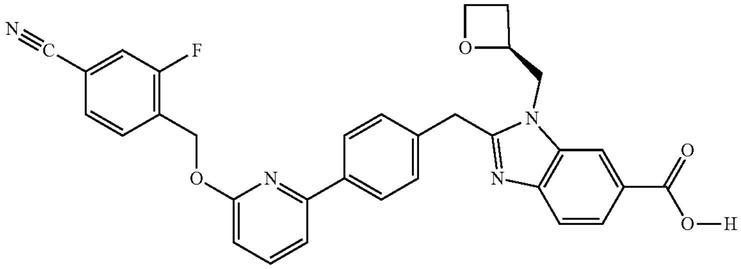 [SMILES: N#Cc1ccc(COc2cccc(-c3ccc(Cc4nc5ccc(C(=O)O)cc5n4C[C@@H]4CCO4)cc3)n2)c(F)c1]<br>ES/MS (m/z) 549.5; 1H NMR (400 MHz, DMSO-d6) δ 8.44 (d, J = 1.4 Hz, 1H), 8.13-8.02 (m, 2H), 7.94 (ddd, J = 16.7, 9.2, 1.4 Hz, 2H), 7.84 (t, J = 7.8 Hz, 1H), 7.80-7.68 (m, 3H), 7.61 (d, J = 7.5 Hz, 1H), 7.48 (d, J = 8.2 Hz, 2H), 6.90 (d, J = 8.2 Hz, 1H), 5.61 (s, 2H), 5.00 (qd, J = 7.4, 2.5 Hz, 1H), 4.87 (dd, J = 15.3, 7.5 Hz, 1H), 4.76-4.55 (m, 3H), 4.55-4.35 (m, 2H), 2.78-2.61 (m, 1H), 2.46-2.34 (m, 1H). |
| 635 | 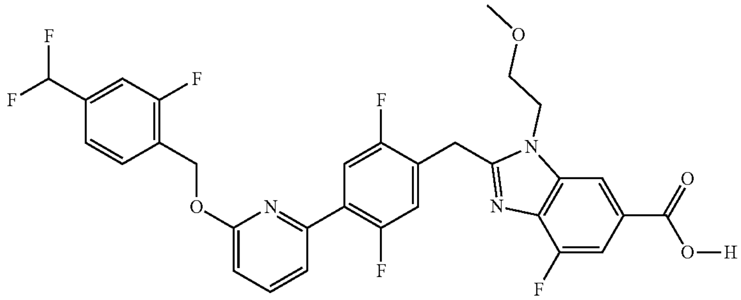 [SMILES: COCCn1c(Cc2cc(F)c(-c3cccc(OCc4ccc(C(F)F)cc4F)n3)cc2F)nc2c(F)cc(C(=O)O)cc21] |

-continued

| Example | Structure/Name/Characterization |
|---|---|
| | ES/MS (m/z) 616.6; 1H NMR (400 MHz, DMSO-d6) δ 8.10 (d, J = 1.3 Hz, 1H), 7.93-7.85 (m, 1H), 7.80 (dd, J = 10.5, 6.4 Hz, 1H), 7.72 (t, J = 7.6 Hz, 1H), 7.57-7.42 (m, 4H), 7.39 (dd, J = 11.5, 6.1 Hz, 1H), 7.06 (t, J = 55.6 Hz, 1H), 6.97 (d, J = 8.2 Hz, 1H), 5.58 (s, 2H), 4.62 (t, J = 5.1 Hz, 2H), 4.46 (s, 2H), 3.68 (t, J = 5.0 Hz, 2H), 3.21 (s, 3H). |
| 636 | 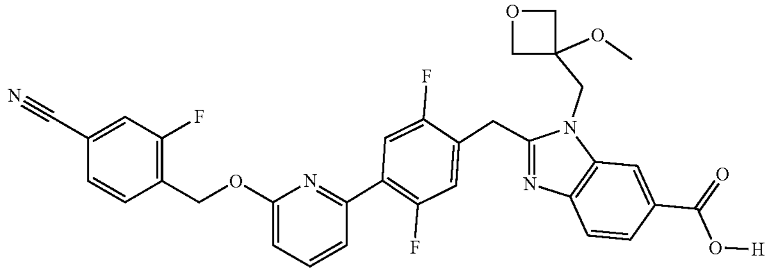 [SMILES: COC1(Cn2c(Cc3cc(F)c(-c4cccc(OCc5ccc(C#N)cc5F)n4)cc3F)nc3ccc(C(=O)O)cc32)COC1] ES/MS (m/z) 615.5; 1H NMR (400 MHz, Methanol-d4) δ 8.36 (s, 1H), 7.99 (dd, J = 8.5, 1.5 Hz, 1H), 7.76-7.61 (m, 4H), 7.49 (ddd, J = 13.8, 8.6, 1.5 Hz, 3H), 7.03 (dd, J = 11.4, 6.1 Hz, 1H), 6.85 (d, J = 8.2 Hz, 1H), 5.59 (s, 2H), 4.92 (d, J = 7.9 Hz, 2H), 4.75 (s, 2H), 4.57 (d, J = 8.0 Hz, 2H), 4.47 (s, 2H), 3.50 (s, 3H). |
| 637 | 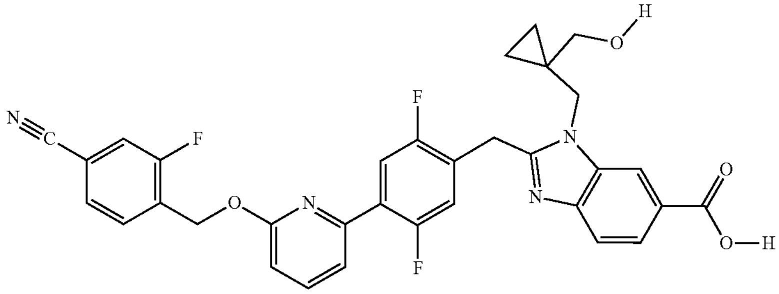 [SMILES: N#Cc1ccc(COc2cccc(-c3cc(F)c(Cc4nc5ccc(C(=O)O)cc5n4CC4(CO)CC4)cc3F)n2)c(F)c1] ES/MS (m/z) 599.4; 1H NMR (400 MHz, Methanol-d4) δ 8.57(d, J = 1.3 Hz, 1H), 8.15 (dd, J = 8.6, 1.4 Hz, 1H), 7.97-7.77 (m, 2H), 7.73 (t, J = 7.8 Hz, 2H), 7.70-7.52 (m, 3H), 7.33 (dd, J = 11.3, 6.1 Hz, 1H), 6.95 (d, J = 8.3 Hz, 1H), 5.63 (s, 2H), 4.80 (s, 2H), 4.65 (s, 2H), 0.93-0.81 (m, 2H), 0.80-0.65 (m, 2H). |
| 638 | 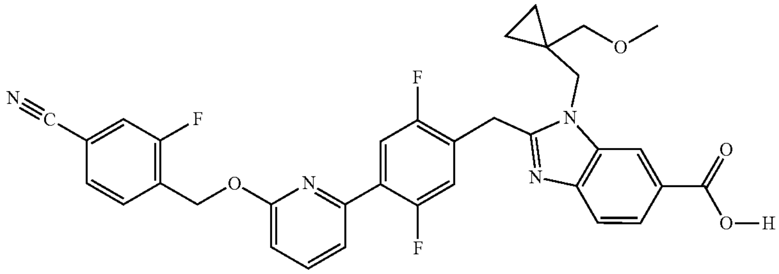 [SMILES: COCC1(Cn2c(Cc3cc(F)c(-c4cccc(OCc5ccc(C#N)cc5F)n4)cc3F)nc3ccc(C(=O)O)cc32)CC1] ES/MS (m/z) 613.5; 1H NMR (400 MHz, Methanol-d4) δ 8.41 (d, J = 1.4 Hz, 1H), 8.10 (d, J = 1.5 Hz, 1H), 7.81-7.62 (m, 4H), 7.54-7.41 (m, 3H), 7.10 (dd, J = 11.2, 6.0 Hz, 1H), 6.87 (d, J = 8.1 Hz, 1H), 5.58 (s, 2H), 4.56 (s, 2H), 4.42 (s, 2H), 3.26 (s, 3H), 3.05 (s, 2H), 0.82 (d, J = 5.2 Hz, 2H), 0.77-0.67 (m, 2H). |

-continued
| Example | Structure/Name/Characterization |
|---|---|
| 639 | 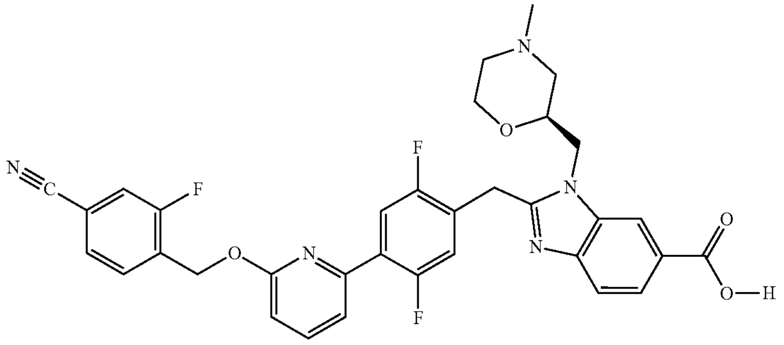 [SMILES: CN1CCO[C@H](Cn2c(Cc3cc(F)c(-c4cccc(OCc5ccc(C#N)cc5F)n4)cc3F)nc3ccc(C(=O)O)cc32)C1] ES/MS (m/z) 628.6; 1H NMR (400 MHz, Methanol-d4) δ 8.67-8.45 (m, 1H), 8.21 (dd, J = 8.6, 1.4 Hz, 1H), 7.92-7.69 (m, 4H), 7.68-7.49 (m, 3H), 7.34 (dd, J = 11.2, 6.0 Hz, 1H), 6.96 (d, J = 8.2 Hz, 1H), 5.63 (s, 2H), 4.75 (s, 2H), 4.70 (dd, J = 15.1, 2.8 Hz, 1H), 4.57 (dd, J = 15.1, 9.0 Hz, 1H), 3.93-3.80 (m, 1H), 3.74 (dd, J = 11.3, 8.7 Hz, 1H), 1.90 (d, J = 12.3 Hz, 2H), 1.71-1.31 (m, 4H). |
| 640 | 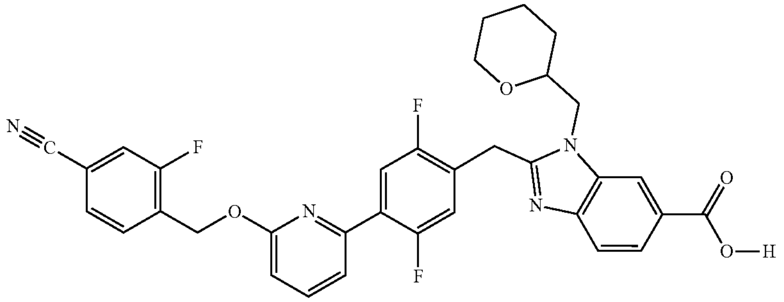 [SMILES: N#Cc1ccc(COc2cccc(-c3cc(F)c(Cc4nc5ccc(C(=O)O)cc5n4CC4CCCCO4)cc3F)n2)c(F)c1] ES/MS (m/z) 613.5; 1H NMR (400 MHz, Methanol-d4) δ 8.51 (d, J = 1.7 Hz, 1H), 8.17 (dt, J = 8.6, 1.3 Hz, 1H), 7.91-7.69 (m, 4H), 7.63-7.51 (m, 3H), 7.33 (dd, J = 11.3, 6.0 Hz, 1H), 6.95 (d, J = 8.2 Hz, 1H), 5.62 (s, 2H), 4.81-4.63 (m, 3H), 4.31 (t, J = 9.8 Hz, 1H), 4.19-4.05 (m, 1H), 3.85 (d, J = 12.2 Hz, 1H), 3.76 (t, J = 12.7 Hz, 1H), 3.57-3.43 (m, 1H), 3.23-3.09 (m, 2H), 3.00 (s, 3H), 2.05 (s, 1H). |
| 641 | 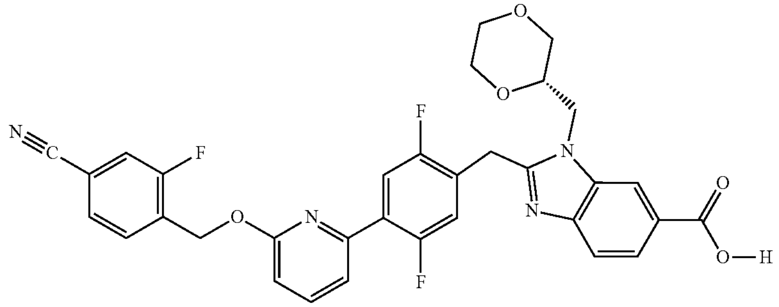 [SMILES: N#Cc1ccc(COc2cccc(-c3cc(F)c(Cc4nc5ccc(C(=O)O)cc5n4C[C@H]4COCCO4)cc3F)n2)c(F)c1] ES/MS (m/z) 615.6; 1H NMR (400 MHz, Methanol-d4) δ 8.53 (t, J = 1.0 Hz, 1H), 8.19 (dd, J = 8.6, 1.4 Hz, 1H), 7.94-7.68 (m, 4H), 7.67-7.54 (m, 3H), 7.33 (dd, J = 11.2, 6.0 Hz, 1H), 6.96 (dd, J = 8.3, 0.6 Hz, 1H), 5.63 (s, 2H), 4.78-4.65 (m, 3H), 4.57 (dd, J = 15.4, 9.0 Hz, 1H), 4.13-3.97 (m, 2H), 3.82-3.63 (m, 2H), 3.63-3.52 (m, 2H), 3.52-3.40 (m, 1H). |

-continued
| Example | Structure/Name/Characterization |
|---|---|
| 642 | 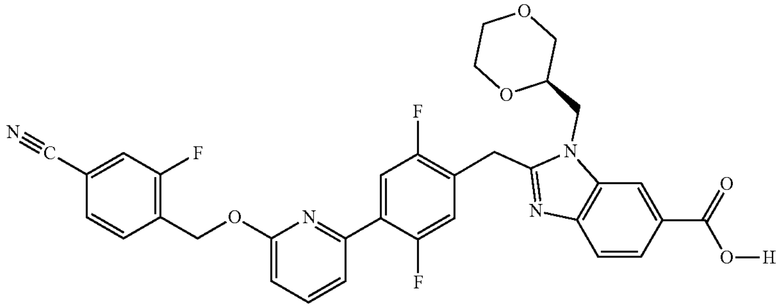 [SMILES: N#Cc1ccc(COc2cccc(-c3cc(F)c(Cc4nc5ccc(C(=O)O)cc5n4C[C@@H]4COCCO4)cc3F)n2)c(F)c1] ES/MS (m/z) 615.5; 1H NMR (400 MHz, Methanol-d4) δ 8.53 (t, J = 1.0 Hz, 1H), 8.19 (dd, J = 8.6, 1.4 Hz, 1H), 7.89-7.68 (m, 4H), 7.65-7.52 (m, 3H), 7.34 (dd, J = 11.3, 6.0 Hz, 1H), 6.95 (d, J = 8.2 Hz, 1H), 5.63 (s, 2H), 4.79-4.65 (m, 3H), 4.58 (dd, J = 15.3, 9.1 Hz, 1H), 4.17-3.96 (m, 2H), 3.80-3.64 (m, 2H), 3.62-3.53 (m, 2H), 3.49-3.41 (m, 1H). |
| 643 | 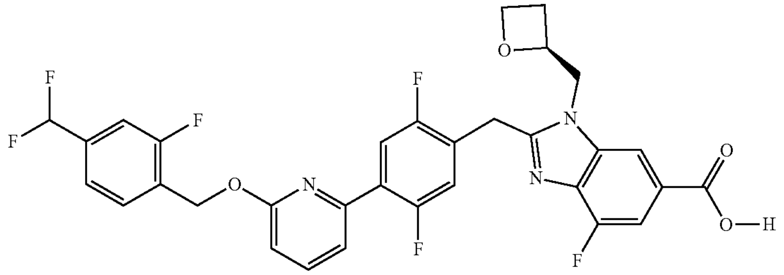 [SMILES: O=C(O)c1cc(F)c2nc(Cc3cc(F)c(-c4cccc(OCc5ccc(C(F)F)cc5F)n4)cc3F)n(C[C@@H]3CCO3)c2c1] ES/MS (m/z) 628.7; 1H NMR (400 MHz, Methanol-d4) δ 8.23 (dd, J = 2.8, 1.2 Hz, 1H), 7.94-7.76 (m, 2H), 7.76-7.64 (m, 2H), 7.54 (dd, J = 7.4, 1.6 Hz, 1H), 7.36 (t, J = 9.6 Hz, 2H), 7.22 (dd, J = 11.4, 6.0 Hz, 1H), 7.03-6.55 (m, 2H), 5.61 (d, J = 4.1 Hz, 2H), 5.18 (qd, J = 7.1, 2.5 Hz, 1H), 4.80 (dd, J = 15.6, 7.3 Hz, 1H), 4.73-4.51 (m, 4H), 4.51-4.37 (m, 1H), 2.91-2.74 (m, 1H), 2.60-2.42 (m, 1H). |
| 644 | 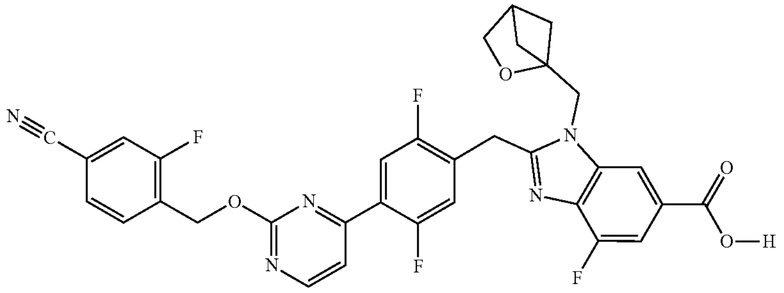 [SMILES: N#Cc1ccc(COc2nccc(-c3cc(F)c(Cc4nc5c(F)cc(C(=O)O)cc5n4CC45CC(CO4)C5)cc3F)n2)c(F)c1] ES/MS (m/z) 630.4; 1H NMR (400 MHz, Methanol-d4) δ 8.67 (d, J = 5.2 Hz, 1H), 8.14 (d, J = 1.2 Hz, 1H), 7.94 (dd, J = 10.3, 6.1 Hz, 1H), 7.79 (s, 1H), 7.70-7.53 (m, 4H), 7.25 (dd, J = 11.5, 5.9 Hz, 1H), 5.69 (s, 2H), 4.73 (s, 2H), 4.59 (s, 2H), 3.73 (s, 2H), 2.94 (t, J = 3.3 Hz, 1H), 2.04-1.89 (m, 2H), 1.41 (dd, J = 4.6, 1.8 Hz, 2H). |
| 645 | 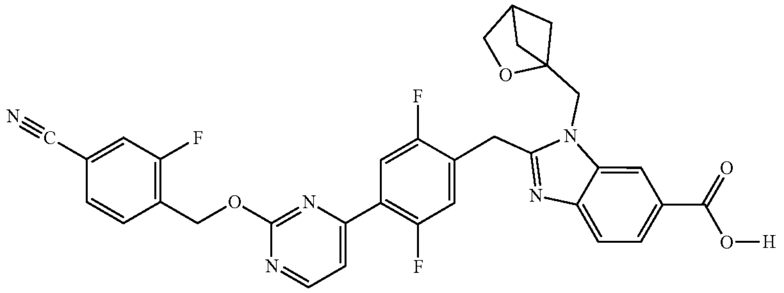 [SMILES: N#Cc1ccc(COc2nccc(-c3cc(F)c(Cc4nc5ccc(C(=O)O)cc5n4CC45CC(CO4)C5)cc3F)n2)c(F)c1] |

-continued

| Example | Structure/Name/Characterization |
|---|---|
| | ES/MS (m/z) 612.6; 1H NMR (400 MHz, Methanol-d4) δ 8.74 (dd, J = 7.8, 4.8 Hz, 1H), 8.59 (t, J = 1.0 Hz, 1H), 8.22 (dd, J = 8.6, 1.4 Hz, 1H), 8.02 (dd, J = 10.4, 6.1 Hz, 1H), 7.86-7.73 (m, 2H), 7.73-7.58 (m, 3H), 7.58-7.41 (m, 1H), 5.70 (s, 2H), 5.02 (s, 2H), 3.75 (s, 2H), 3.00 (q, J = 3.3, 2.9 Hz, 1H), 2.09 (ddd, J = 5.0, 3.3, 1.8 Hz, 2H), 1.44 (dd, J = 4.6, 1.8 Hz, 2H). |
| 646 | 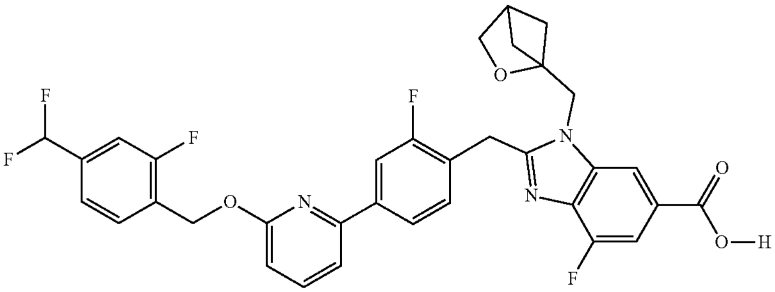 [SMILES: O=C(O)c1cc(F)c2nc(Cc3ccc(-c4cccc(OCc5ccc(C(F)F)cc5F)n4)cc3F)n(CC34CC(CO3)C4)c2c1] ES/MS (m/z) 636.7; 1H NMR (400 MHz, Methanol-d4) δ 8.23 (d, J = 1.2 Hz, 1H), 7.92-7.83 (m, 2H), 7.83-7.62 (m, 3H), 7.51 (dd, J = 7.5, 0.7 Hz, 1H), 7.45-7.29 (m, 3H), 6.95-6.46 (m, 2H), 5.61 (s, 2H), 4.77 (s, 2H), 4.64 (s, 2H), 3.74 (s, 2H), 2.94 (t, J = 3.2 Hz, 1H), 1.95 (ddd, J = 4.9, 3.2, 1.7 Hz, 2H), 1.40 (dd, J = 4.6, 1.8 Hz, 2H). |
| 647 | 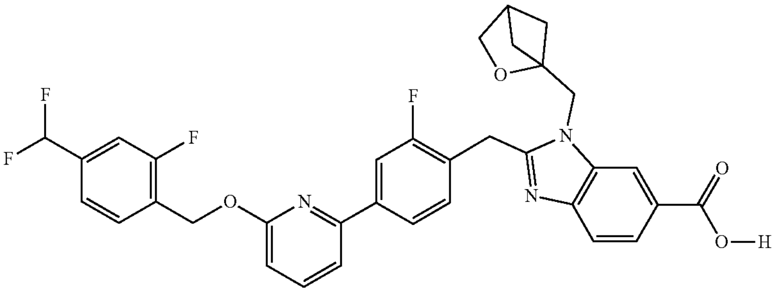 [SMILES: O=C(O)c1ccc2nc(Cc3ccc(-c4cccc(OCc5ccc(C(F)F)cc5F)n4)cc3F)n(CC34CC(CO3)C4)c2c1] ES/MS (m/z) 618.6; 1H NMR (400 MHz, Methanol-d4) δ 8.59 (t, J = 1.0 Hz, 1H), 8.22 (dd, J = 8.6, 1.4 Hz, 1H), 8.02-7.88 (m, 2H), 7.88-7.72 (m, 2H), 7.68 (t, J = 7.5 Hz, 1H), 7.62-7.44 (m, 2H), 7.44-7.24 (m, 2H), 6.95-6.61 (m, 2H), 5.63 (s, 2H), 5.01 (s, 2H), 4.84 (s, 2H), 3.77 (s, 2H), 2.99 (t, J = 3.2 Hz, 1H), 2.07 (ddd, J = 5.0, 3.2, 1.7 Hz, 2H), 1.44 (dd, J = 4.6, 1.8 Hz, 2H). |
| 648 | 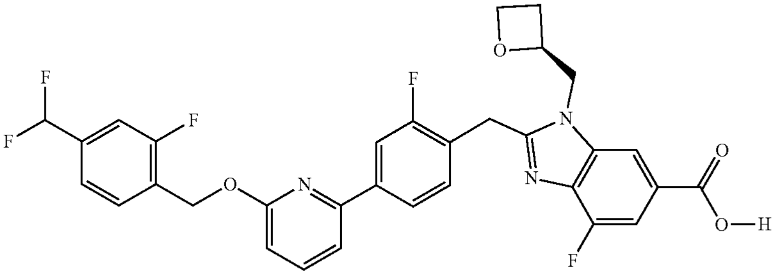 [SMILES: O=C(O)c1cc(F)c2nc(Cc3ccc(-c4cccc(OCc5ccc(C(F)F)cc5F)n4)cc3F)n(C[C@@H]3CCO3)c2c1] ES/MS (m/z) 610.8; 1H NMR (400 MHz, Methanol-d4) δ 8.23 (d, J = 1.2 Hz, 1H), 7.89-7.81 (m, 2H), 7.77 (dd, J = 8.2, 7.5 Hz, 1H), 7.73 (dd, J = 11.1, 1.2 Hz, 1H), 7.68 (t, J = 7.5 Hz, 1H), 7.50 (d, J = 7.5 Hz, 1H), 7.42-7.29 (m, 3H), 6.98-6.52 (m, 2H), 5.61 (s, 2H), 5.13 (qd, J = 7.4, 2.5 Hz, 1H), 4.83-4.56 (m, 5H), 4.49 (dt, J = 9.2, 6.0 Hz, 1H), 2.78 (dtd, J = 11.5, 8.2, 6.1 Hz, 1H), 2.49 (ddt, J = 11.5, 9.2, 7.2 Hz, 1H). |

-continued
| Example | Structure/Name/Characterization |
|---|---|
| 649 | 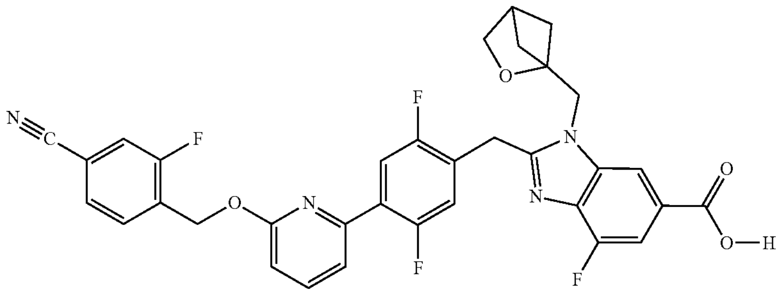<br>ES/MS (m/z) 629.6; 1H NMR (400 MHz, Methanol-d4) δ 8.22 (d, J = 1.2 Hz, 1H), 7.88-7.65 (m, 4H), 7.65-7.41 (m, 3H), 7.21 (dd, J = 11.4, 6.1 Hz, 1H), 7.01-6.83 (m, 1H), 5.63 (s, 2H), 4.79 (s, 2H), 4.61 (s, 2H), 3.73 (s, 2H), 2.95 (t, J = 3.3 Hz, 1H), 1.97 (ddd, J = 6.7, 3.3, 1.8 Hz, 2H), 1.40 (dd, J = 4.6, 1.8 Hz, 2H). |
| 650 | 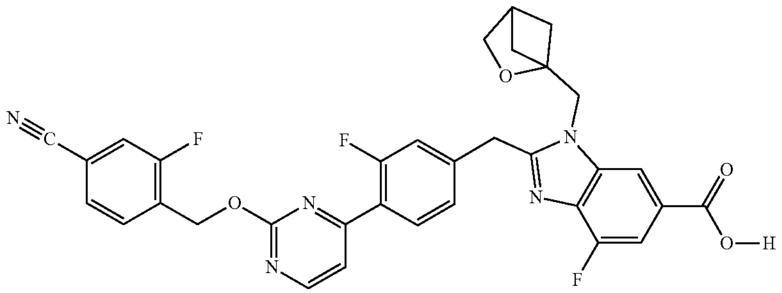 [SMILES: N#Cc1ccc(COc2nccc(-c3ccc(Cc4nc5c(F)cc(C(=O)O)cc5n4CC45CC(CO4)C5)cc3F)n2)c(F)c1]<br>ES/MS (m/z) 612.3; 1H NMR (400 MHz, Methanol-d4) δ 8.65 (d, J = 5.2 Hz, 1H), 8.24-8.05 (m, 2H), 7.79 (t, J = 7.6 Hz, 2H), 7.73-7.54 (m, 3H), 7.42-7.19 (m, 2H), 5.70 (d, J = 9.9 Hz, 2H), 4.69 (s, 2H), 4.62 (s, 2H), 3.74 (s, 2H), 1.92 (s, 2H), 1.46-1.30 (m, 3H). |
| 651 | 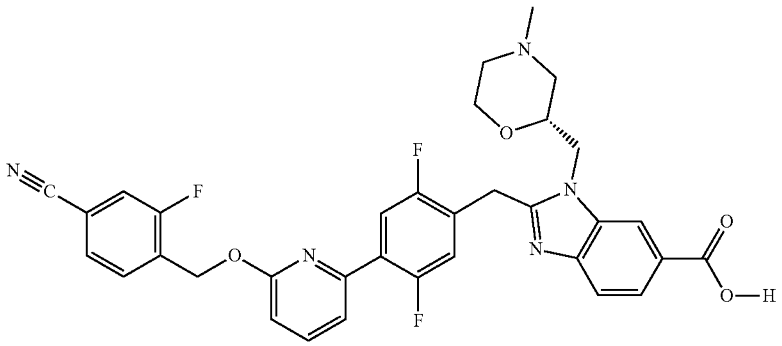 [SMILES: CN1CCO[C@@H](Cn2c(Cc3cc(F)c(-c4cccc(OCc5ccc(C#N)cc5F)n4)cc3F)nc3ccc(C(=O)O)cc32)C1]<br>ES/MS (m/z) 628.6; 1H NMR (400 MHz, Methanol-d4) δ 8.48-8.36 (m, 1H), 8.12 (dd, J = 8.5, 1.5 Hz, 1H), 7.90-7.80 (m, 1H), 7.80-7.69 (m, 3H), 7.64-7.52 (m, 3H), 7.26 (dd, J = 11.3, 6.1 Hz, 1H), 6.95 (dd, J = 8.3, 0.7 Hz, 1H), 5.63 (s, 2H), 4.79 (dd, J = 15.6, 2.8 Hz, 1H), 4.68 (dd, J = 15.6, 8.4 Hz, 1H), 4.63 (s, 2H), 4.24 (s, 1H), 4.12 (dd, J = 13.4, 3.5 Hz, 1H), 3.91-3.61 (m, 2H), 3.57-3.41 (m, 1H), 3.27-3.03 (m, 2H), 3.06-2.92 (m, 3H). |

-continued

| Example | Structure/Name/Characterization |
|---|---|
| 652 | 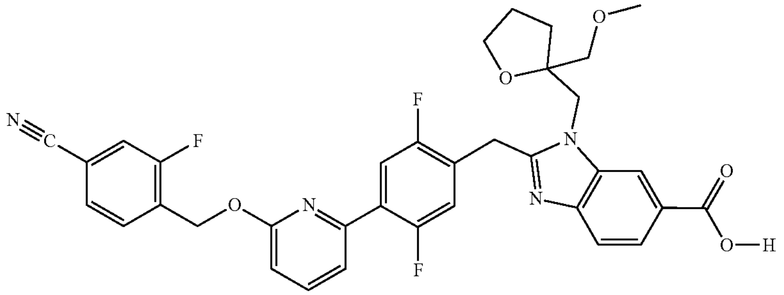 [SMILES: COCC1(Cn2c(Cc3cc(F)c(-c4cccc(OCc5ccc(C#N)cc5F)n4)cc3F)nc3ccc(C(=O)O)cc32)CCCO1] ES/MS (m/z) 643.6; 1H NMR (400 MHz, Methanol-d4) δ 8.65-8.56 (m, 1H), 8.16 (dd, J = 8.6, 1.5 Hz, 1H), 7.82 (ddd, J = 14.2, 9.5, 6.9 Hz, 2H), 7.73 (dq, J = 6.7, 3.4 Hz, 2H), 7.69-7.54 (m, 3H), 7.29 (dd, J = 11.3, 6.1 Hz, 1H), 6.95 (dd, J = 8.3, 0.7 Hz, 1H), 5.63 (s, 2H), 4.84-4.65 (m, 3H), 4.54 (d, J = 15.2 Hz, 1H), 4.03-3.84 (m, 2H), 3.36 (s, 3H), 3.24 (d, J = 9.4 Hz, 1H), 3.17-3.05 (m, 1H), 2.27-2.11 (m, 1H), 2.01 (s, 1H), 1.99-1.82 (m, 2H). |
| 653 | 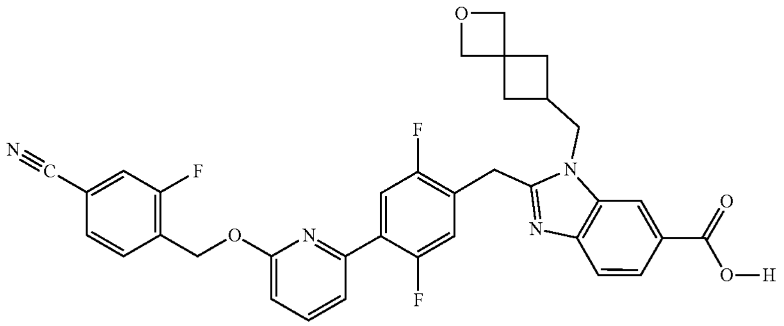 [SMILES: N#Cc1ccc(COc2cccc(-c3cc(F)c(Cc4nc5ccc(C(=O)O)cc5n4CC4CC5(COC5)C4)cc3F)n2)c(F)c1] ES/MS (m/z) 625.6; 1H NMR (400 MHz, Methanol-d4) δ 8.54-8.45 (m, 1H), 8.18 (dd, J = 8.6, 1.4 Hz, 1H), 7.88-7.68 (m, 4H), 7.67-7.52 (m, 3H), 7.37 (dd, J = 11.2, 6.1 Hz, 1H), 6.96 (dt, J = 8.2, 1.1 Hz, 1H), 5.63 (s, 2H), 4.68 (d, J = 6.3 Hz, 4H), 4.64-4.50 (m, 3H), 2.66 (h, J = 8.1 Hz, 1H), 2.46-2.30 (m, 2H), 2.16 (td, J = 9.3, 2.9 Hz, 2H), 2.07-1.89 (m, 1H). |

Example 20, 2-{[4-[6-[(4-cyano-2-fluoro-phenyl)methoxy]-2-pyridyl}-3-methyl-phenyl]methyl]-3-(2-methoxyethyl)benzimidazole-5-carboxylic acid Procedure 2

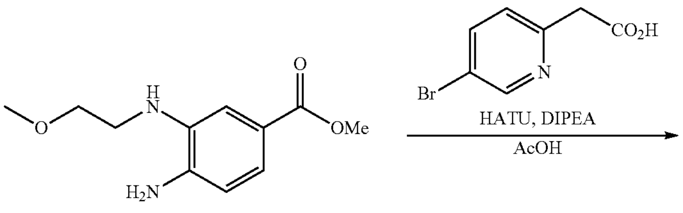

I-1

-continued

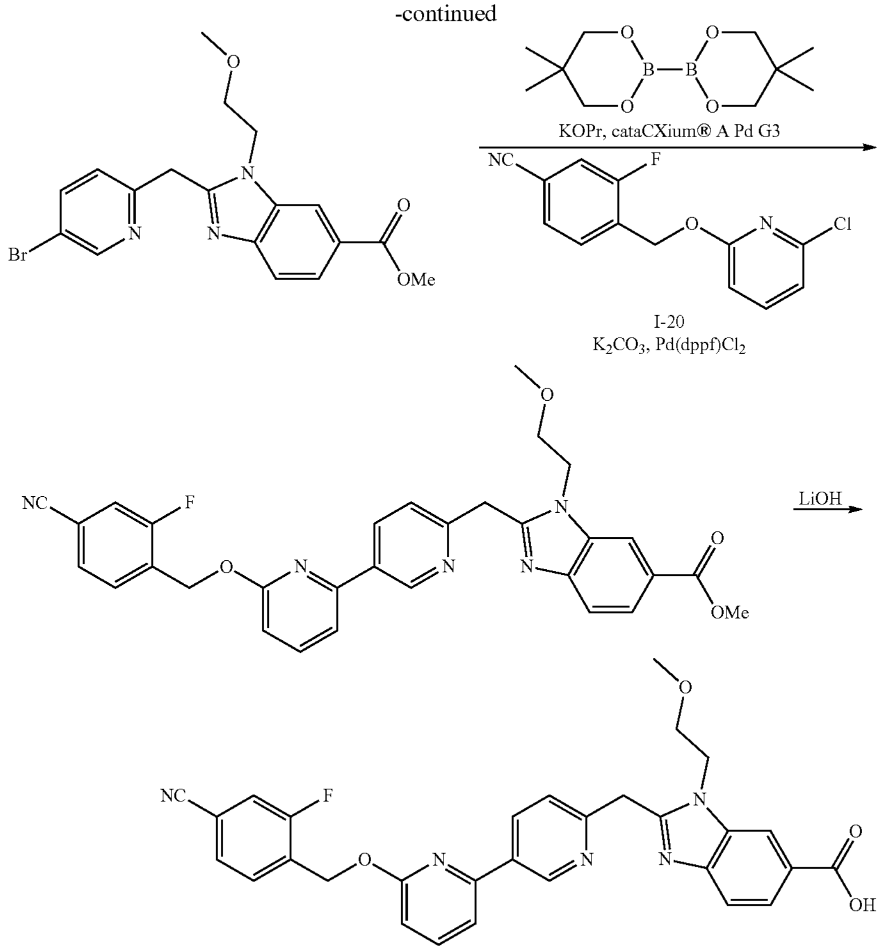

Methyl 2-[(5-bromo-2-pyridyl)methyl]-3-(2-methoxyethyl)benzimidazole-5-carboxylate: 2-(5-bromo-2-pyridyl) acetic acid (220 mg, 1.02 mmol), methyl 4-amino-3-(2-methoxyethylamino)benzoate (208 mg, 0.93 mmol), o-(7-Azabenzotriazol-1-yl)-N,N,N',N'-tetramethyluronium hexafluorophosphate (458 mg, 1.20 mmol), diisopropylethylamine (0.81 mL, 4.63 mmol) and DCM (3 mL) were combined and stirred at room temperature for 90 minutes. Upon completion the organic portion was washed with saturated aqueous $NH_4Cl$ (2×5 mL) and saturated aqueous $NaHCO_3$ (2×5 mL), dried over $MgSO_4$ and concentrated. The resultant crude residue was taken up in acetic acid (1 mL), heated at 60° C. for 2 hrs, concentrated and purified by silica gel chromatography (eluent: EtOAc/hexanes) to give the desired product: ES/MS: 404.9 ($M+H^+$).

Methyl 2-{[4-[6-[(4-cyano-2-fluoro-phenyl)methoxy]-2-pyridyl]-3-methyl-phenyl]methyl}-3-(2-methoxyethyl)benzimidazole-5-carboxylate: To a solution of methyl 2-[(4-bromo-3-methyl-phenyl)methyl]-3-(2-methoxyethyl) benzimidazole-5-carboxylate (200 mg, 0.50 mmol) in 2-Me-THF (10 mL) was added potassium propionate (166 mg, 1.48 mmol), Bis(neopentyl glycolato)diboron (145 mg, 0.64 mmol), and cataCXium® A Pd G3 (25.2 mg, 0.035 mmol). The resulting mixture was degassed with argon, sealed and heated at 100° C. for 2 hrs. Potassium propionate (166 mg, 1.48 mmol), Bis(neopentyl glycolato)diboron (145 mg, 0.64 mmol), and cataCXium® A Pd G3 (25.2 mg, 0.035 mmol) were added once more, the mixture degassed with argon, sealed and returned to 100° C. heating for 1 hr. The mixture was cooled to room temperature at which point potassium carbonate (1 M aqueous solution, 1.48 mL, 1.48 mmol), 4-[(6-chloro-2-pyridyl)oxymethyl]-3-fluoro-benzonitrile (I-20) (195 mg, 0.74 mmol) and [1,1'-Bis(diphenylphosphino)ferrocene]dichloropalladium(II) (25.3 mg, 0.035 mmol) were added. The result mixture was degassed with argon, sealed and heated at 100° C. for 2 hrs. Upon completion the reaction contents were poured into water (15 mL) and extracted with EtOAc (2×30 mL). The combined organic extracts were washed with brine (5 mL), dried over $MgSO_4$, and purified by silica gel chromatography (eluent: EtOAc/hexanes/MeOH) to give the desired product: ES/MS: 552.6 ($M+H^+$).

2-{[4-[6-[(4-cyano-2-fluoro-phenyl)methoxy]-2-pyridyl]-3-methyl-phenyl]methyl}-3-(2-methoxyethyl)benzimidazole-5-carboxylic acid (Example 20): Methyl 2-{[4-[6-[(4-cyano-2-fluoro-phenyl)methoxy]-2-pyridyl]-3-methyl-phenyl]methyl}-3-(2-methoxyethyl)benzimidazole-5-carboxylate was dissolved in acetonitrile (2 mL) after which LiOH (8.5 mg, 0.36 mmol) as a solution in water (0.5 mL) was added and the resulting mixture stirred at 60° C. for 1 hr. The mixture was adjusted to pH 5 using citric acid (5% aqueous solution) and extracted with EtOAc (2×15 mL). The combined organics were then washed with brine (5 mL), dried over $MgSO_4$, filtered, concentrated and purified by RP-HPLC (eluent: water/MeCN 0.1% TFA) to yield the product as a trifluoroacetate salt: ES/MS: 538.4 ($M+H^+$); $^1H$ NMR (400 MHz, Chloroform-d) δ 9.11 (dd, J=2.3, 0.7 Hz, 1H), 8.42 (dd, J=8.2, 2.3 Hz, 1H), 8.04-7.98 (m, 1H), 7.95 (dd, J=8.6, 1.4 Hz, 1H), 7.89 (d, J=8.6 Hz, 1H), 7.82-7.73 (m, 2H), 7.66 (t, J=7.5 Hz, 1H), 7.47 (dd, J=7.9, 1.5 Hz, 1H), 7.42 (dd, J=7.5, 0.7 Hz, 1H), 7.39 (dd, J=9.3, 1.5 Hz, 1H), 6.89 (dd, J=8.2, 0.6 Hz, 1H), 5.61 (s, 2H), 5.07 (s, 2H), 4.71 (t, J=4.8 Hz, 2H), 3.77 (t, J=4.9 Hz, 2H), 3.31 (s, 3H).

Examples 21-22, 369, 378, 388, 398, 400-401, 403, 405-406, 517, 536-537, and 654-659 Compounds Prepared Using Procedure 2

Other compounds of the present disclosure prepared using the general route described in Procedure 2 include the following Examples.

| Example | Structure/Name/Characterization |
|---|---|
| 21 | 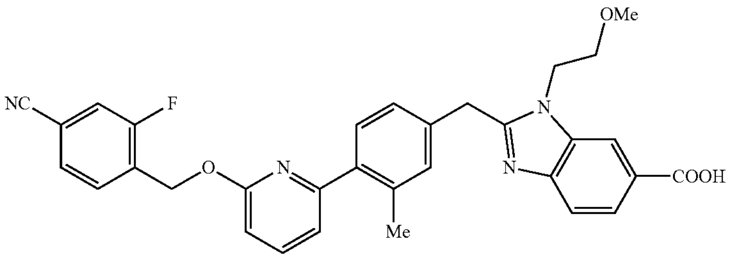 2-(4-(6-((4-cyano-2-fluorobenzyl)oxy)pyridin-2-yl)-3-methylbenzyl)-1-(2-methoxyethyl)-1H-benzo[d]imidazole-6-carboxylic acid: ES/MS m/z 551.5; $^1$H NMR (400 MHz, $CD_3CN$) δ 8.44 (dd, J = 1.5, 0.7 Hz, 1H), 8.14 (dd, J = 8.6, 1.5 Hz, 1H), 7.84 (dd, J = 8.7, 0.7 Hz, 1H), 7.81 (dd, J = 8.3, 7.4 Hz, 1H), 7.73-7.62 (m, 1H), 7.62-7.47 (m, 2H), 7.41 (d, J = 7.7 Hz, 1H), 7.27 (dd, J = 10.3, 2.6 Hz, 2H), 7.13 (dd, J = 7.4, 0.7 Hz, 1H), 6.89 (dd, J = 8.3, 0.7 Hz, 1H), 5.53 (t, J = 0.9 Hz, 2H), 4.69-4.44 (m, 4H), 3.71 (dd, J = 5.5, 4.5 Hz, 2H), 3.26 (s, 3H), 2.29 (s, 3H). |
| 22 | 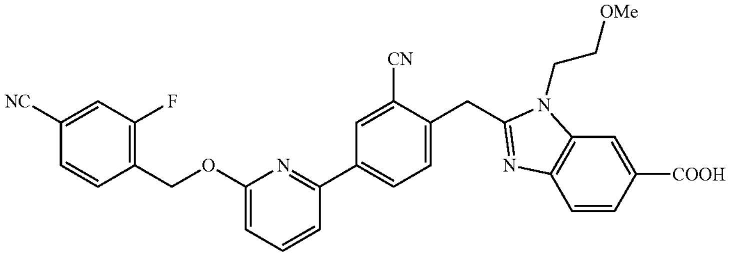 2-(2-cyano-4-(6-((4-cyano-2-fluorobenzyl)oxy)pyridin-2-yl)benzyl)-1-(2-methoxyethyl)-1H-benzo[d]imidazole-6-carboxylic acid: ES/MS m/z 562.5; $^1$H NMR (400 MHz, $CD_3OD$) δ 8.46 (d, J = 2.5 Hz, 2H), 8.34 (dd, J = 8.2, 2.0 Hz, 1H), 8.23-8.10 (m, 1H), 7.86 (q, J = 7.6 Hz, 1H), 7.80-7.68 (m, 3H), 7.68-7.52 (m, 3H), 6.95 (d, J = 8.1 Hz, 1H), 5.68 (d, J = 9.1 Hz, 2H), 4.86-4.72 (m, 3H), 4.02 (t, J = 5.2 Hz, 1H), 3.83 (t, J = 4.9 Hz, 1H), 3.50 (p, J = 1.6 Hz, 1H), 3.34 (s, 3H), 1.96 (s, 1H). |
| 369 | 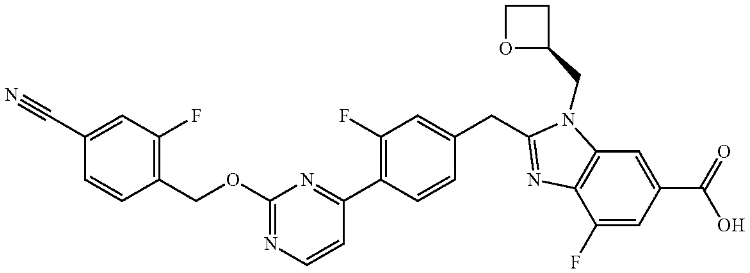 [SMILES: N#Cc1ccc(COc2nccc(-c3ccc(Cc4nc5c(F)cc(C(=O)O)cc5n4C[C@@H]4CCO4)cc3F)n2)c(F)c1] (S)-2-(4-(2-((4-cyano-2-fluorobenzyl)oxy)pyrimidin-4-yl)-3-fluorobenzyl)-4-fluoro-1-(oxetan-2-ylmethyl)-1H-benzo[d]imidazole-6-carboxylic acid: ES/MS m/z 586.2; $^1$H NMR (400 MHz, DMSO-d6) δ 8.73 (d, J = 5.1 Hz, 1H), 8.05 (t, J = 8.1 Hz, 1H), 7.99-7.89 (m, 2H), 7.84-7.71 (m, 2H), 7.59 (dd, J = 5.2, 2.0 Hz, 1H), 7.48 (d, J = 11.9 Hz, 1H), 7.45-7.27 (m, 2H), 5.61 (s, 2H), 4.99 (dt, J = 9.9, 5.0 Hz, 1H), 4.66 (dd, J = 15.5, 7.0 Hz, 1H), 4.59-4.42 (m, 4H), 4.35 (dt, J = 9.0, 5.9 Hz, 1H), 2.74-2.59 (m, 1H), 2.44-2.24 (m, 1H). |

-continued

| Example | Structure/Name/Characterization |
| --- | --- |
| 378 | 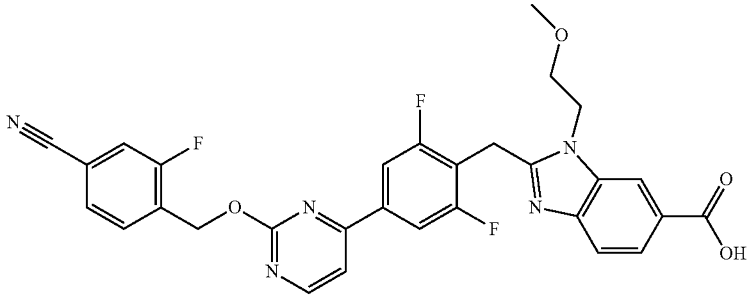 [SMILES: COCCn1c(Cc2c(F)cc(-c3ccnc(OCc4ccc(C#N)cc4F)n3)cc2F)nc2ccc(C(=O)O)cc21]<br>2-(4-(2-((4-cyano-2-fluorobenzyl)oxy)pyrimidin-4-yl)-2,6-difluorobenzyl)-1-(2-methoxyethyl)-1H-benzo[d]imidazole-6-carboxylic acid: ES/MS m/z 574.2; $^{1}$H NMR (400 MHz, Methanol-d4) δ 9.61 (d, J = 5.2 Hz, 1H), 9.03 (d, J = 1.5 Hz, 1H), 8.86-8.69 (m, 4H), 8.65-8.53 (m, 3H), 8.36 (d, J = 8.4 Hz, 1H), 6.46 (s, 2H), 5.46 (t, J = 5.1 Hz, 2H), 5.31 (s, 2H), 4.54 (t, J = 5.0 Hz, 2H), 4.05 (s, 3H). |
| 388 | 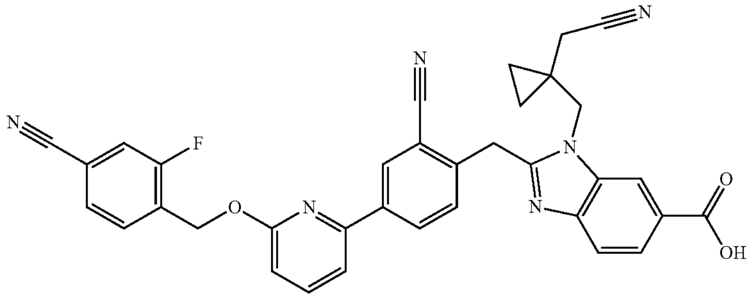 [SMILES: N#CCC1(Cn2c(Cc3ccc(-c4cccc(OCc5ccc(C#N)cc5F)n4)cc3C#N)nc3ccc(C(=O)O)cc32)CC1]<br>2-(2-cyano-4-(6-((4-cyano-2-fluorobenzyl)oxy)pyridin-2-yl)benzyl)-1-((1-(cyanomethyl)cyclopropyl)methyl)-1H-benzo[d]imidazole-6-carboxylic acid: ES/MS m/z 597.2; $^{1}$H NMR (400 MHz, DMSO-d6) δ 8.51 (d, J = 1.8 Hz, 1H), 8.43-8.35 (m, 1H), 8.30 (s, 1H), 7.91 (t, J = 8.6 Hz, 2H), 7.77 (dt, J = 16.9, 8.3 Hz, 4H), 7.67 (d, J = 8.3 Hz, 1H), 7.59 (d, J = 8.4 Hz, 1H), 6.98 (d, J = 8.1 Hz, 1H), 5.65 (s, 2H), 4.65 (s, 2H), 4.60 (s, 2H), 2.70 (s, 2H), 0.85-0.65 (m, 4H). |
| 398 | 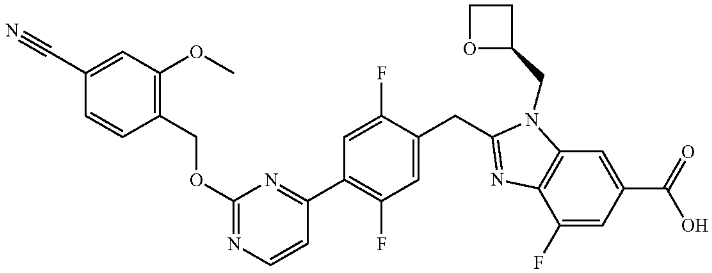 [SMILES: COc1cc(C#N)ccc1COc1nccc(-c2cc(F)c(Cc3nc4c(F)cc(C(=O)O)cc4n3C[C@@H]3CCO3)cc2F)n1]<br>(S)-2-(4-(2-((4-cyano-2-methoxybenzyl)oxy)pyrimidin-4-yl)-2,5-difluorobenzyl)-4-fluoro-1-(oxetan-2-ylmethyl)-1H-benzo[d]imidazole-6-carboxylic acid: ES/MS m/z 616.2; $^{1}$H NMR (400 MHz, DMSO-d6) δ 8.77 (d, J = 5.2 Hz, 1H), 8.16 (d, J = 1.2 Hz, 1H), 7.88 (dd, J = 10.2, 6.2 Hz, 1H), 7.71-7.56 (m, 3H), 7.56-7.40 (m, 3H), 5.54 (s, 2H), 5.08 (q, J = 7.8, 7.1 Hz, 1H), 4.80 (dd, J = 15.5, 7.1 Hz, 1H), 4.74-4.43 (m, 4H), 4.35 (dt, J = 9.3, 6.0 Hz, 1H), 3.92 (s, 3H), 2.78-2.63 (m, 1H), 2.39 (q, J = 9.5, 8.6 Hz, 1H). |

-continued

| Example | Structure/Name/Characterization |
|---|---|
| 400 | 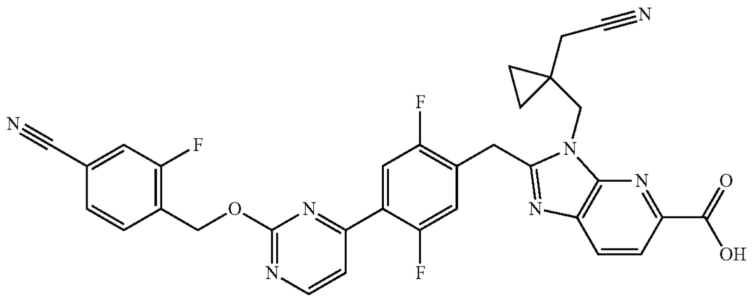 [SMILES: N#CCC1(Cn2c(Cc3cc(F)c(-c4ccnc(OCc5ccc(C#N)cc5F)n4)cc3F)nc3ccc(C(=O)O)nc32)CC1] 2-(4-(2-((4-cyano-2-fluorobenzyl)oxy)pyrimidin-4-yl)-2,5-difluorobenzyl)-3-((1-(cyanomethyl)cyclopropyl)methyl)-3H-imidazo[4,5-b]pyridine-5-carboxylic acid: ES/MS m/z 610.2; $^{1}$H NMR (400 MHz, DMSO-d6) δ 8.79 (d, J = 5.1 Hz, 1H), 8.09 (d, J = 8.2 Hz, 1H), 8.03-7.86 (m, 3H), 7.84-7.71 (m, 2H), 7.65 (dd, J = 5.2, 1.8 Hz, 1H), 7.57 (dd, J = 11.6, 5.9 Hz, 1H), 5.64 (s, 2H), 4.56 (s, 2H), 4.52 (s, 2H), 2.79 (s, 2H), 1.06 (t, J = 3.1 Hz, 2H), 0.75-0.62 (m, 2H). |
| 401 | 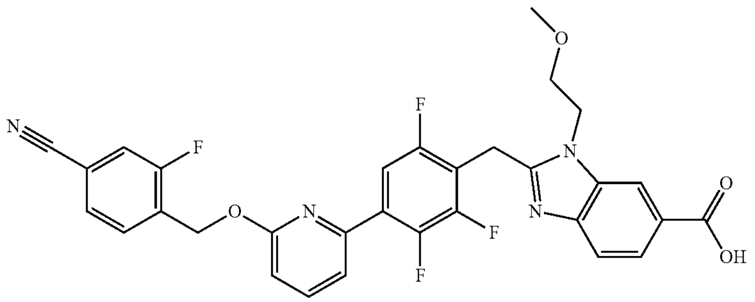 [SMILES: COCCn1c(Cc2c(F)cc(-c3cccc(OCc4ccc(C#N)cc4F)n3)c(F)c2F)nc2ccc(C(=O)O)cc21] 2-(4-(6-((4-cyano-2-fluorobenzyl)oxy)pyridin-2-yl)-2,3,6-trifluorobenzyl)-1-(2-methoxyethyl)-1H-benzo[d]imidazole-6-carboxylic acid: ES/MS m/z 591.2; $^{1}$H NMR (400 MHz, DMSO-d6) δ 8.23 (d, J = 1.5 Hz, 1H), 8.02-7.89 (m, 2H), 7.80-7.71 (m, 2H), 7.69-7.50 (m, 5H), 7.05 (d, J = 8.3 Hz, 1H), 5.61 (s, 2H), 4.66 (t, J = 5.1 Hz, 2H), 4.53 (s, 2H), 3.73 (t, J = 5.0 Hz, 2H). |
| 403 | 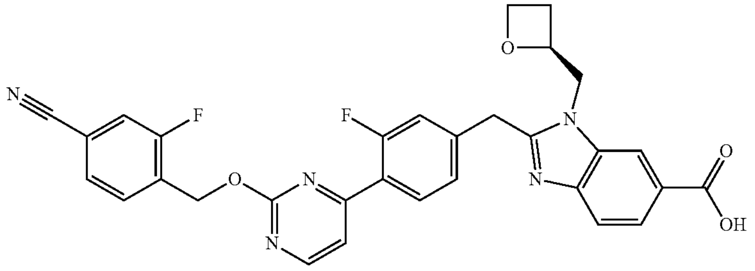 [SMILES: N#Cc1ccc(COc2nccc(-c3ccc(Cc4nc5ccc(C(=O)O)cc5n4C[C@@H]4CCO4)cc3F)n2)c(F)c1] (S)-2-(4-(2-((4-cyano-2-fluorobenzyl)oxy)pyrimidin-4-yl)-3-fluorobenzyl)-1-(oxetan-2-ylmethyl)-1H-benzo[d]imidazole-6-carboxylic acid: ES/MS 568.2; $^{1}$H NMR (400 MHz, DMSO-d6) δ 8.74 (d, J = 5.2 Hz, 1H), 8.34 (d, J = 1.5 Hz, 1H), 8.06 (t, J = 8.2 Hz, 1H), 7.98-7.92 (m, 1H), 7.88 (dd, J = 8.5, 1.5 Hz, 1H), 7.82-7.73 (m, 2H), 7.68 (d, J = 8.5 Hz, 1H), 7.59 (dd, J = 5.2, 2.0 Hz, 1H), 7.48-7.35 (m, 2H), 5.61 (s, 2H), 5.01 (tt, J = 7.2, 4.1 Hz, 1H), 4.80 (dd, J = 15.4, 7.4 Hz, 1H), 4.72-4.56 (m, 3H), 4.55-4.42 (m, 1H), 4.38 (dt, J = 9.0, 5.9 Hz, 1H), 2.75-2.61 (m, 1H), 2.47-2.31 (m, 1H). |

-continued

| Example | Structure/Name/Characterization |
|---|---|
| 405 | 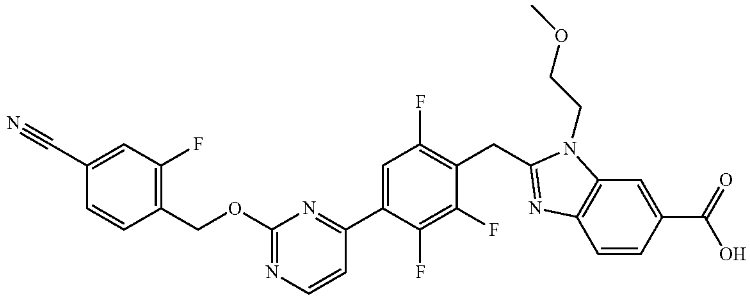 [SMILES: COCCn1c(Cc2c(F)cc(-c3ccnc(OCc4ccc(C#N)cc4F)n3)c(F)c2F)nc2ccc(C(=O)O)cc21]<br>2-(4-(2-((4-cyano-2-fluorobenzyl)oxy)pyrimidin-4-yl)-2,3,6-trifluorobenzyl)-1-(2-methoxyethyl)-1H-benzo[d]imidazole-6-carboxylic acid: ES/MS m/z 592.2; $^{1}$H NMR (400 MHz, DMSO-d6) δ 8.84 (d, J = 5.1 Hz, 1H), 8.25 (d, J = 1.4 Hz, 1H), 7.95 (dd, J = 10.0, 1.4 Hz, 1H), 7.84-7.73 (m, 4H), 7.70 (dd, J = 5.1, 1.8 Hz, 1H), 7.59 (d, J = 8.4 Hz, 1H), 5.64 (s, 2H), 4.67 (t, J = 5.0 Hz, 2H), 4.58 (s, 2H), 3.73 (t, J = 5.0 Hz, 2H), 3.24 (s, 3H). |
| 406 | 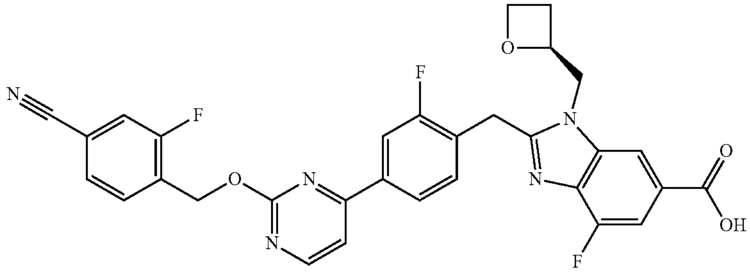 [SMILES: N#Cc1ccc(COc2nccc(-c3ccc(Cc4nc5c(F)cc(C(=O)O)cc5n4C[C@@H]4CCO4)c(F)c3)n2)c(F)c1]<br>(S)-2-(4-(2-((4-cyano-2-fluorobenzyl)oxy)pyrimidin-4-yl)-2-fluorobenzyl)-4-fluoro-1-(oxetan-2-ylmethyl)-1H-benzo[d]imidazole-6-carboxylic acid: ES/MS m/z 586.2; $^{1}$H NMR (400 MHz, DMSO-d6) δ 13.07 (s, 1H), 8.74 (d, J = 5.2 Hz, 1H), 8.15 (d, J = 1.3 Hz, 1H), 8.09-7.99 (m, 2H), 7.94 (dd, J = 10.0, 1.4 Hz, 1H), 7.83 (d, J = 5.2 Hz, 1H), 7.82-7.71 (m, 2H), 7.58-7.46 (m, 2H), 5.63 (s, 2H), 5.05 (qd, J = 7.1, 2.6 Hz, 1H), 4.78 (dd, J = 15.5, 7.1 Hz, 1H), 4.71-4.59 (m, 1H), 4.59-4.45 (m, 3H), 4.35 (dt, J = 9.0, 5.9 Hz, 1H), 2.79-2.63 (m, 1H), 2.37 (dddd, J = 14.3, 9.6, 8.3, 4.2 Hz, 1H). |
| 517 | 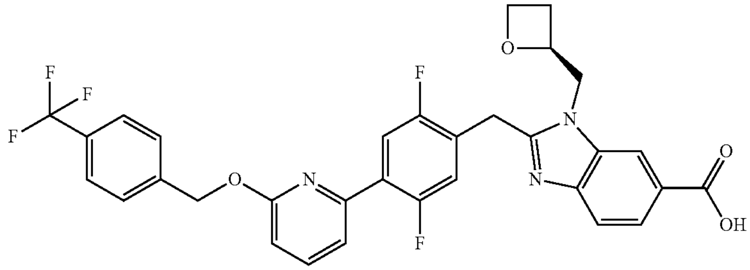 [SMILES: O=C(O)c1ccc2nc(Cc3cc(F)c(-c4cccc(OCc5ccc(C(F)(F)F)cc5)n4)cc3F)n(C[C@@H]3CCO3)c2c1]<br>(S)-2-(2,5-difluoro-4-(6-((4-(trifluoromethyl)benzyl)oxy)pyridin-2-yl)benzyl)-1-(oxetan-2-ylmethyl)-1H-benzo[d]imidazole-6-carboxylic acid: ES/MS m/z 610.2; $^{1}$H NMR (400 MHz, Methanol-d4) δ 8.55 (d, J = 1.6 Hz, 1H), 8.19 (dd, J = 8.6, 1.5 Hz, 1H), 7.89-7.75 (m, 3H), 7.68 (s, 4H), 7.56 (dd, J = 7.4, 1.8 Hz, 1H), 7.34 (dd, J = 11.2, 6.0 Hz, 1H), 6.96 (d, J = 8.3 Hz, 1H), 5.59 (s, 2H), 5.26 (qd, J = 7.3, 2.4 Hz, 1H), 4.96 (dd, J = 15.5, 7.5 Hz, 1H), 4.85-4.62 (m, 5H), 4.53 (dt, J = 9.0, 5.9 Hz, 1H), 2.96-2.78 (m, 1H), 2.58 (ddt, J = 9.0, 7.0, 4.7 Hz, 1H). |

-continued

| Example | Structure/Name/Characterization |
|---|---|
| 526 | 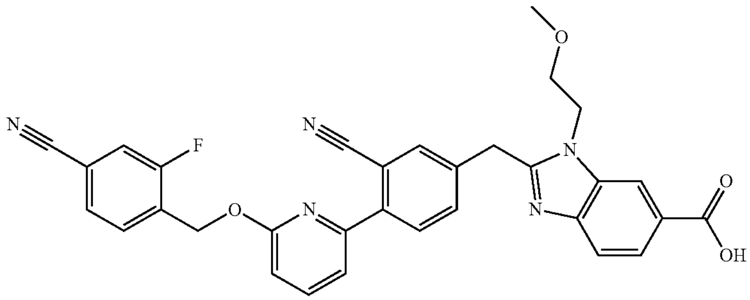 [SMILES: COCCn1c(Cc2ccc(-c3cccc(OCc4ccc(C#N)cc4F)n3)c(C#N)c2)nc2ccc(C(=O)O)cc21] 2-(3-cyano-4-(6-((4-cyano-2-fluorobenzyl)oxy)pyridin-2-yl)benzyl)-1-(2-methoxyethyl)-1H-benzo[d]imidazole-6-carboxylic acid: ES/MS m/z 562.5; $^1$H NMR (400 MHz, Methanol-d4) δ 8.57 (dd, J = 1.5, 0.7 Hz, 1H), 8.23 (dd, J = 8.6, 1.5 Hz, 1H), 8.01-7.95 (m, 2H), 7.91 (dd, J = 8.3, 7.4 Hz, 1H), 7.84-7.69 (m, 3H), 7.63-7.47 (m, 3H), 7.02 (dd, J = 8.3, 0.6 Hz, 1H), 5.73 (t, J = 0.9 Hz, 2H), 4.84-4.75 (m, 4H), 3.85 (dd, J = 5.4, 4.4 Hz, 2H), 3.34-3.32 (m, 3H). |
| 536 | 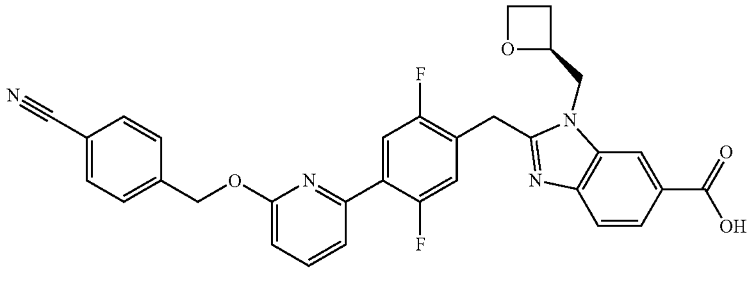 [SMILES: N#Cc1ccc(COc2cccc(-c3cc(F)c(Cc4nc5ccc(C(=O)O)cc5n4C[C@@H]4CCO4)cc3F)n2)cc1] (S)-2-(4-(6-((4-cyanobenzyl)oxy)pyridin-2-yl)-2,5-difluorobenzyl)-1-(oxetan-2-ylmethyl)-1H-benzo[d]imidazole-6-carboxylic acid: ES/MS 567.4; $^1$H NMR (400 MHz, Methanol-d4) δ 8.57 (s, 1H), 8.27-8.15 (m, 1H), 7.79 (ddd, J = 24.7, 14.2, 7.9 Hz, 4H), 7.66 (d, J = 7.9 Hz, 3H), 7.60-7.51 (m, 1H), 7.36 (dd, J = 11.2, 5.9 Hz, 1H), 6.96 (d, J = 8.2 Hz, 1H), 5.58 (s, 2H), 5.26 (qd, J = 7.4, 2.6 Hz, 1H), 4.99 (dd, J = 15.5, 7.5 Hz, 1H), 4.88-4.75 (m, 3H), 4.70 (ddd, J = 13.7, 9.0, 5.0 Hz, 1H), 4.54 (dt, J = 9.1, 5.7 Hz, 1H), 2.87 (dtd, J = 13.9, 8.0, 6.8, 4.0 Hz, 1H), 2.69-2.44 (m, 1H). |
| 537 | 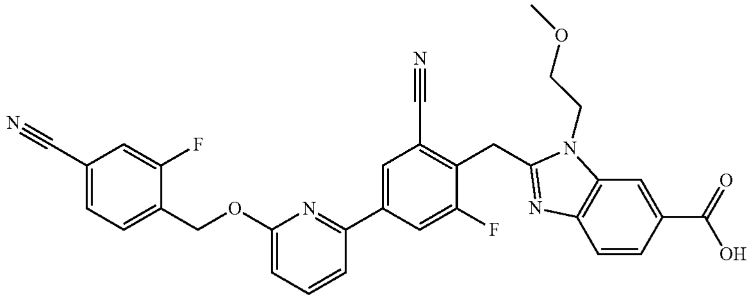 [SMILES: COCCn1c(Cc2c(F)cc(-c3cccc(OCc4ccc(C#N)cc4F)n3)cc2C#N)nc2ccc(C(=O)O)cc21] 2-(2-cyano-4-(6-((4-cyano-2-fluorobenzyl)oxy)pyridin-2-yl)-6-fluorobenzyl)-1-(2-methoxyethyl)-1H-benzo[d]imidazole-6-carboxylic acid: ES/MS m/z 580.2; $^1$H NMR (400 MHz, Chloroform-d) δ 8.23 (s, 1H), 8.10 (d, J = 8.5 Hz, 1H), 7.93 (d, J = 8.6 Hz, 1H), 7.86 (d, J = 7.1 Hz, 1H), 7.79 (dd, J = 8.3, 7.4 Hz, 1H), 7.68 (t, J = 7.5 Hz, 1H), 7.57 (d, J = 10.4 Hz, 1H), 7.52-7.38 (m, 3H), 6.95 (d, J = 8.3 Hz, 1H), 5.66 (s, 2H), 4.80 (s, 2H), 4.59 (t, J = 4.8 Hz, 2H), 3.82 (t, J = 4.7 Hz, 2H), 3.33 (s, 3H). |
| 654 | ES/MS (m/z) 565.42; 1H NMR (400 MHz, Methanol-d4) δ 8.53 (d, J = 2.4 Hz, 1H), 8.22 (d, J = 1.4 Hz, 1H), 7.96 (ddd, J = 19.4, 8.4, 2.0 Hz, 2H), 7.87-7.71 (m, 3H), 7.64-7.53 (m, 2H), 7.48 (d, J = 8.2 Hz, 1H), 6.90 (d, J = 8.2 Hz, 1H), 5.57 (s, 2H), 4.62 (t, J = 5.1 Hz, 2H), 4.50 (s, 2H), 4.18 (ddd, J = 12.2, 8.9, 3.7 Hz, 2H), 3.56 (dd, J = 11.8, 2.8 Hz, 1H), 3.37 (s, 3H). |

-continued

| Example | Structure/Name/Characterization |
|---|---|
| 655 | 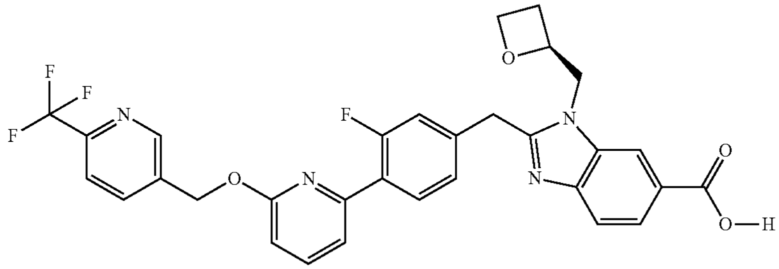 [SMILES: O=C(O)c1ccc2nc(Cc3ccc(-c4cccc(OCc5ccc(C(F)(F)F)nc5)n4)c(F)c3)n(C[C@@H]3CCO3)c2c1] ES/MS (m/z) 593.37; 1H NMR (400 MHz, Chloroform-d) δ 8.94-8.71 (m, 1H), 8.19 (d, J = 1.4 Hz, 1H), 8.11 (dd, J = 8.5, 1.5 Hz, 1H), 8.06-7.83 (m, 3H), 7.69 (t, J = 7.9 Hz, 2H), 7.47 (dd, J = 7.5, 1.7 Hz, 1H), 7.20 (dd, J = 8.1, 1.6 Hz, 1H), 7.12 (dd, J = 12.0, 1.7 Hz, 1H), 6.81 (d, J = 8.2 Hz, 1H), 5.57 (s, 2H), 5.17 (qd, J = 7.0, 2.7 Hz, 1H), 4.76-4.53 (m, 3H), 4.52-4.26 (m, 3H), 3.85-3.71 (m, 1H), 2.74 (dtd, J = 11.5, 8.0, 5.9 Hz, 1H), 2.41 (ddt, J = 11.4, 9.0, 7.2 Hz, 1H). |
| 656 | 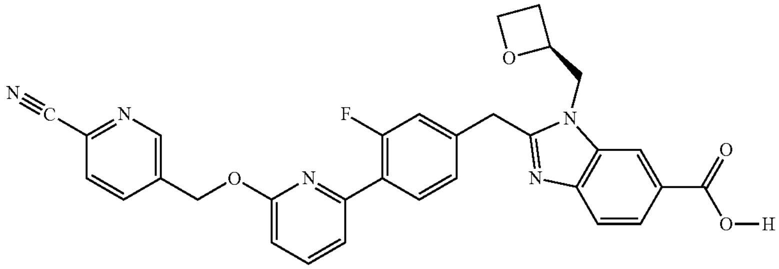 [SMILES: N#Cc1ccc(COc2cccc(-c3ccc(Cc4nc5ccc(C(=O)O)cc5n4C[C@@H]4CCO4)cc3F)n2)cn1] ES/MS (m/z) 550.29; 1H NMR (400 MHz, Chloroform-d) δ 8.84 (d, J = 2.1 Hz, 1H), 8.18 (d, J = 1.5 Hz, 1H), 8.10 (dd, J = 8.5, 1.5 Hz, 1H), 8.01-7.78 (m, 3H), 7.78-7.60 (m, 2H), 7.47 (dd, J = 7.5, 1.7 Hz, 1H), 7.22-7.06 (m, 2H), 6.82 (d, J = 8.2 Hz, 1H), 5.57 (s, 2H), 5.23-5.03 (m, 2H), 4.74-4.49 (m, 2H), 4.49-4.26 (m, 2H), 3.87-3.58 (m, 2H), 2.83-2.64 (m, 1H), 2.51-2.30 (m, 1H). |
| 657 | 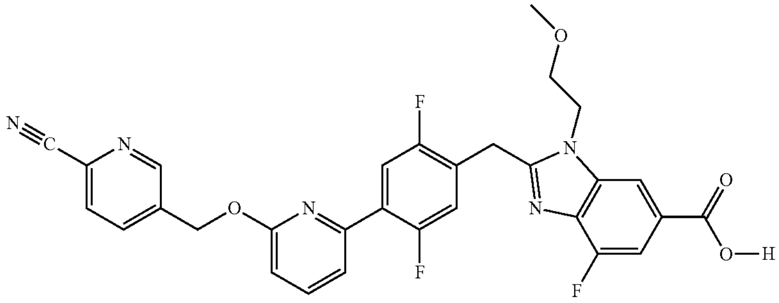 [SMILES: COCCn1c(Cc2cc(F)c(-c3cccc(OCc4ccc(C#N)nc4)n3)cc2F)nc2c(F)cc(C(=O)O)cc21] ES/MS (m/z) 574.31; 1H NMR (400 MHz, Methanol-d4) δ 8.85 (d, J = 2.0 Hz, 1H), 8.11 (dt, J = 4.3, 2.5 Hz, 2H), 7.89 (dd, J = 8.0, 0.8 Hz, 1H), 7.86-7.70 (m, 2H), 7.65 (dd, J = 11.3, 1.2 Hz, 1H), 7.54 (dd, J = 7.3, 1.6 Hz, 1H), 7.14 (dd, J = 11.5, 6.1 Hz, 1H), 6.93 (d, J = 8.2 Hz, 1H), 5.64 (s, 2H), 4.56 (t, J = 5.0 Hz, 2H), 4.50 (s, 2H), 3.80-3.62 (m, 3H), 3.26 (s, 3H). |

-continued

| Example | Structure/Name/Characterization |
|---|---|
| 658 | 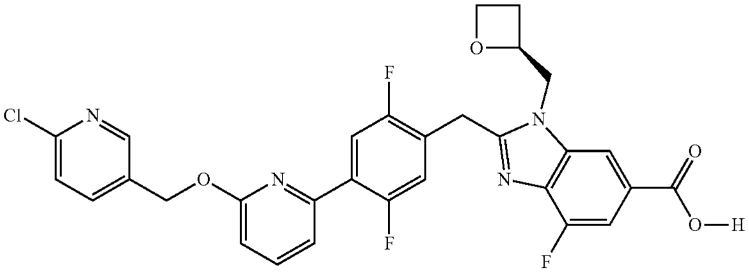 [SMILES: O=C(O)c1cc(F)c2nc(Cc3cc(F)c(-c4cccc(OCc5ccc(Cl)nc5)n4)cc3F)n(C[C@@H]3CCO3)c2c1]<br>ES/MS (m/z) 595.17; 1H NMR (400 MHz, Chloroform-d) δ 8.55 (d, J = 2.4 Hz, 1H), 8.02 (s, 1H), 7.89-7.61 (m, 4H), 7.49 (dd, J = 7.5, 1.4 Hz, 1H), 7.37 (d, J = 8.2 Hz, 1H), 7.15 (dd, J = 11.3, 6.0 Hz, 1H), 6.81 (d, J = 8.1 Hz, 1H), 5.23-5.11 (m, 1H), 4.77-4.31 (m, 6H), 4.19 (ddd, J = 11.8, 7.8, 4.2 Hz, 0H), 3.89-3.59 (m, 3H), 2.87-2.70 (m, 1H), 2.51-2.31 (m, 1H). |
| 659 | 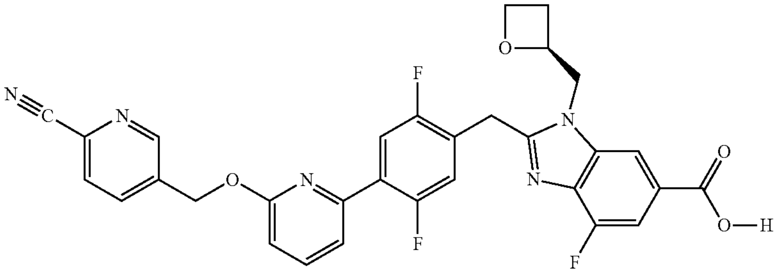 [SMILES: N#Cc1ccc(COc2cccc(-c3cc(F)c(Cc4nc5c(F)cc(C(=O)O)cc5n4C[C@@H]4CCO4)cc3F)n2)cn1]<br>ES/MS (m/z) 586.55; 1H NMR (400 MHz, Methanol-d4) δ 8.90-8.79 (m, 1H), 8.20 (d, J = 1.3 Hz, 1H), 8.12 (dd, J = 8.0, 2.1 Hz, 1H), 7.94-7.63 (m, 4H), 7.55 (dd, J = 7.1, 1.6 Hz, 1H), 7.21 (dd, J = 11.5, 6.0 Hz, 1H), 6.95 (d, J = 8.2 Hz, 1H), 5.64 (s, 2H), 5.17 (qd, J = 7.2, 2.5 Hz, 1H), 4.80-4.34 (m, 6H), 3.94 (hept, J = 6.1 Hz, 1H), 2.91-2.74 (m, 1H), 2.49 (ddt, J = 11.5, 9.1, 7.1 Hz, 1H). |

Example 23. 2-(4-(6-((4-cyano-2-fluorobenzyl)oxy)-3-methylpyridin-2-yl)benzyl)-1-(2-methoxyethyl)-1H-benzo[d]imidazole-6-carboxylic acid and

Example 24. 2-(4-(6-((4-cyano-2-fluorobenzyl)oxy)-5-methylpyridin-2-yl)benzyl)-1-(2-methoxyethyl)-1H-benzo[d]imidazole-6-carboxylic acid Procedure 3

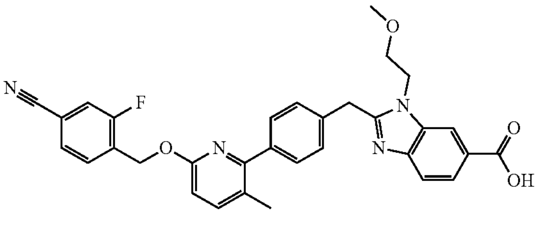

+

-continued

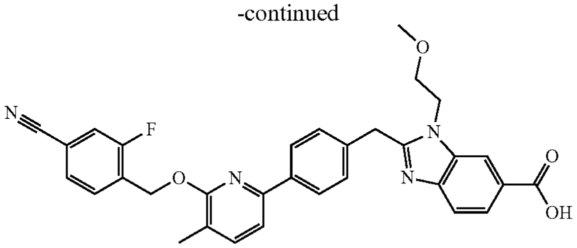

Procedure 1 was followed starting with a mixture of Intermediates I-2 and I-3 to give a crude mixture of final products which was purified by RP-HPLC (10-63.8% 0.1% TFA-ACN in 0.1% TFA Water, 15 min gradient, Column: Gemini 5 μM, NX-C18 110 Angstrom, 250x21.2 mm) to give the two title compounds Peak 1 (Example 23) and Peak 2 (Example 24). Structures were assigned arbitrarily. Peak 1 (Example 23): ES/MS m/z: 551.6 ($M+H^+$); $^1$H NMR (400 MHz, Methanol-d4) δ 8.62-8.59 (m, 1H), 8.27 (dd, J=8.6, 1.4 Hz, 1H), 7.82 (d, J=8.6 Hz, 1H), 7.74-7.64 (m, 2H), 7.63-7.55 (m, 4H), 7.51-7.46 (m, 2H), 6.85 (d, J=8.3 Hz, 1H), 5.52 (s, 2H), 4.84 (t, J=5.0 Hz, 2H), 4.79 (s, 2H), 3.83-3.78 (m, 2H), 2.33 (s, 3H); Peak 2 (Example 24): ES/MS m/z: 551.5 ($M+H^+$); $^1$H NMR (400 MHz, Methanol-d4) δ 8.50-8.47 (m, 1H), 8.18 (dd, J=8.6, 1.4 Hz, 1H), 8.08-8.02 (m, 2H), 7.77 (d, J=8.6 Hz, 1H), 7.73 (t, J=7.6 Hz, 1H), 7.65-7.55 (m, 3H), 7.44 (dd, J=10.0, 7.8 Hz, 3H), 5.69 (s, 2H), 4.70 (t, J=5.0 Hz, 2H), 4.67 (s, 2H), 3.74 (t, J=5.0 Hz, 2H), 3.30 (s, 3H), 2.31 (s, 3H).

Examples 81 and 86-87. Compounds Prepared Using Procedure 3

Other compounds of the present disclosure prepared using the general route described in Procedure 3 include the following Examples.

| Example | Structure/Name/Characterization |
|---|---|
| 81 | 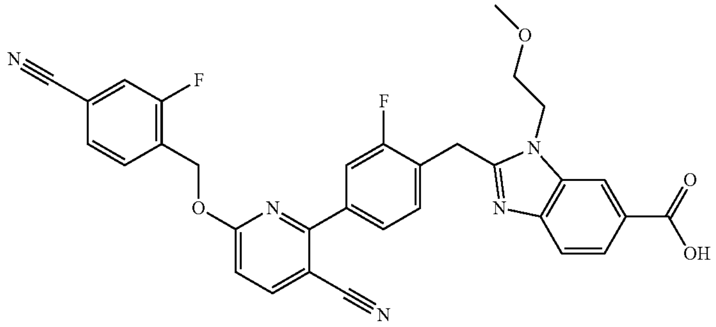 [SMILES: COCCn1c(Cc2ccc(-c3nc(OCc4ccc(C#N)cc4F)ccc3C#N)cc2F)nc2ccc(C(=O)O)cc21] 2-(4-(3-cyano-6-((4-cyano-2-fluorobenzyl)oxy)pyridin-2-yl)-2-fluorobenzyl)-1-(2-methoxyethyl)-1H-benzo[d]imidazole-6-carboxylic acid: ES/MS m/z 580.5; $^{1}$H NMR (400 MHz, Methanol-d4) δ 8.48 (s, 1H), 8.18-8.14 (m, 2H), 7.84 (dd, J = 8.0, 1.8 Hz, 1H), 7.78-7.71 (m, 3H), 7.65-7.53 (m, 3H), 7.08 (d, J = 8.6 Hz, 1H), 5.68 (s, 2H), 4.77-4.72 (m, 4H), 3.79 (t, J = 4.9 Hz, 2H), 3.30 (s, 3H). |
| 86 | 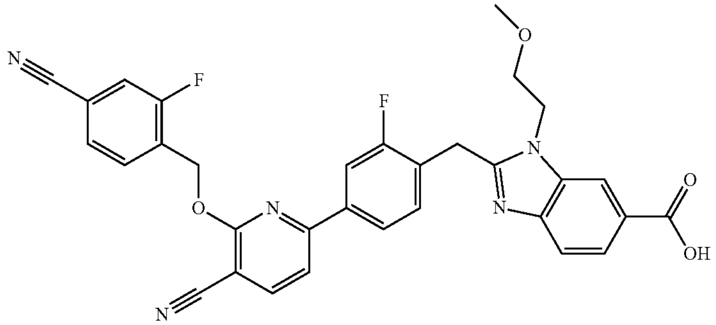 [SMILES: COCCn1c(Cc2ccc(-c3ccc(C#N)c(OCc4ccc(C#N)cc4F)n3)cc2F)nc2ccc(C(=O)O)cc21] 2-(4-(5-cyano-6-((4-cyano-2-fluorobenzyl)oxy)pyridin-2-yl)-2-fluorobenzyl)-1-(2-methoxyethyl)-1H-benzo[d]imidazole-6-carboxylic acid: ES/MS m/z 580.4; $^{1}$H NMR (400 MHz, Methanol-d4) δ 8.51 (s, 1H), 8.22 (d, J = 7.9 Hz, 1H), 8.21-8.16 (m, 1H), 8.03-7.95 (m, 2H), 7.83-7.73 (m, 3H), 7.68-7.61 (m, 2H), 7.55 (t, J = 8.0 Hz, 1H), 5.81 (s, 2H), 4.79-4.70 (m, 4H), 3.81 (t, J = 4.9 Hz, 2H), 3.31 (s, 3H). |
| 87 | 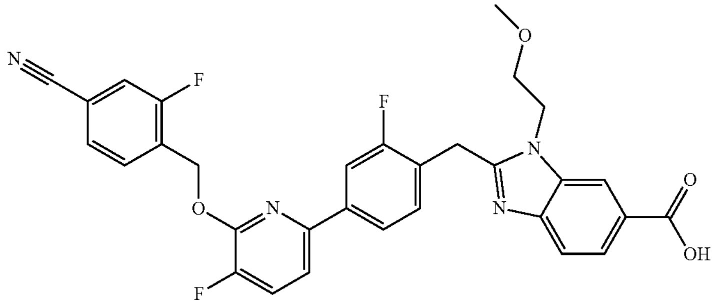 [SMILES: COCCn1c(Cc2ccc(-c3ccc(F)c(OCc4ccc(C#N)cc4F)n3)cc2F)nc2ccc(C(=O)O)cc21] 2-(4-(6-((4-cyano-2-fluorobenzyl)oxy)-5-fluoropyridin-2-yl)-2-fluorobenzyl)-1-(2-methoxyethyl)-1H-benzo[d]imidazole-6-carboxylic acid: ES/MS m/z 573.5; $^{1}$H NMR (400 MHz, Methanol-d4) δ 8.53 (s, 1H), 8.20 (dd, J = 8.5, 1.5 Hz, 1H), 7.91-7.83 (m, 2H), 7.81-7.73 (m, 2H), 7.69-7.56 (m, 4H), 7.49 (t, J = 8.0 Hz, 1H), 5.74 (s, 2H), 4.78 (t, J = 4.9 Hz, 2H), 4.73 (s, 2H), 3.81 (t, J = 4.8 Hz, 2H). |

Example 25. 2-{[4-[4-[(4-cyano-2-fluoro-phenyl)methoxy]pyrimidin-2-yl]-2-fluoro-phenyl]methyl}-3-(2-methoxyethyl)benzimidazole-5-carboxylic acid Procedure 4

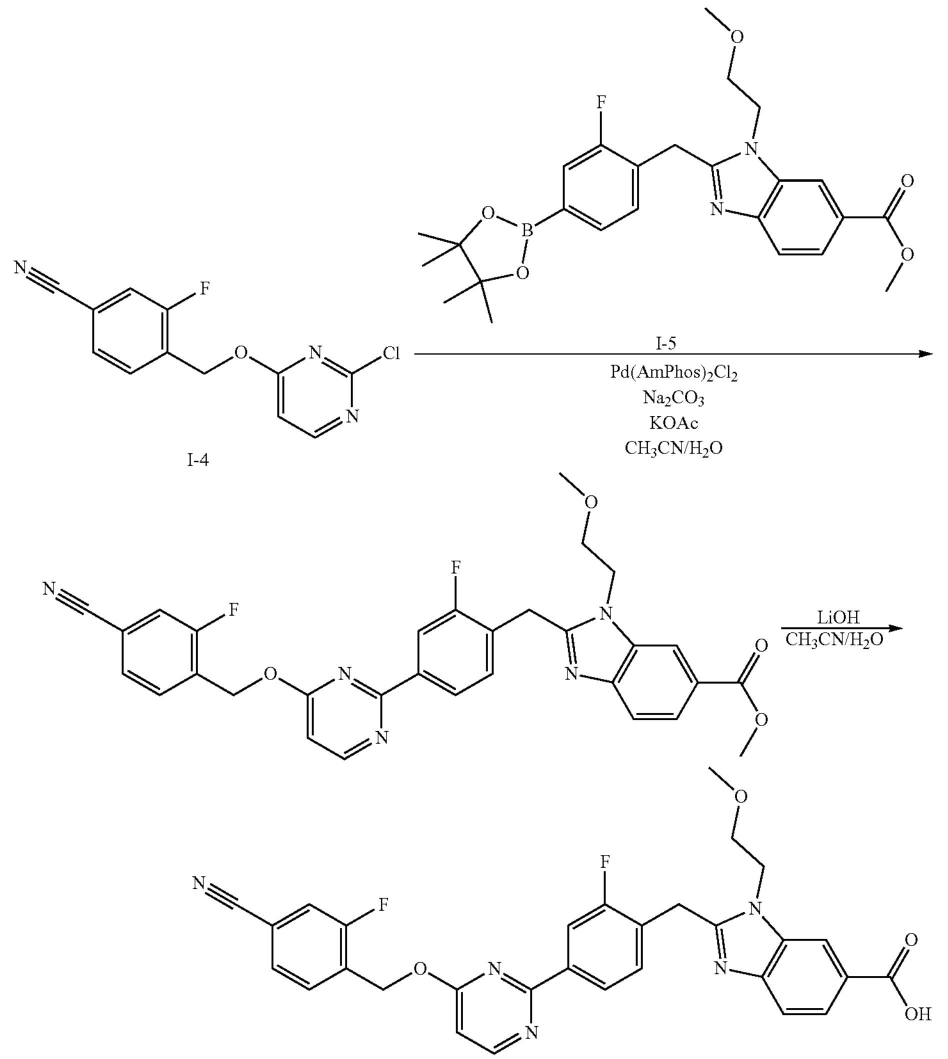

Methyl 2-{[4-[4-[(4-cyano-2-fluoro-phenyl)methoxy]pyrimidin-2-yl]-2-fluoro-phenyl]methyl}-3-(2-methoxyethyl)benzimidazole-5-carboxylate: To a microwave vial was added methyl 2-{[2-fluoro-4-(4,4,5,5-tetramethyl-1,3,2-dioxaborolan-2-yl)phenyl]methyl}-3-(2-methoxyethyl)benzimidazole-5-carboxylate (I-5) (79.1 mg, 0.169 mmol), 4-[(2-chloropyrimidin-4-yl)oxymethyl]-3-fluoro-benzonitrile (I-4) (40.5 mg, 0.154 mol), Bis(di-tert-butyl(4-dimethylaminophenyl)phosphine)dichloropalladium(II) (8.7 mg, 0.0123 mmol), sodium carbonate (48.8 mg, 0.461 mmol) and potassium acetate (30.2 mg, 0.307 mmol). Acetonitrile (1.0 mL) and water (0.50 mL) were added, argon was bubbled through the mixture for 3 min and the mixture was heated to 120° C. in a microwave for 30 min. The mixture was filtered through Celite, eluting with DCM and the filtrate was concentrated in vacuo. The crude residue was purified by column chromatography (0-100% EtOAc in hexane) to give the title compound: ES/MS m/z: 570.5 ($M+H^+$).

2-{[4-[4-[(4-cyano-2-fluoro-phenyl)methoxy]pyrimidin-2-yl]-2-fluoro-phenyl]methyl}-3-(2-methoxyethyl)benzimidazole-5-carboxylic acid: To a mixture of methyl 2-{[4-[6-[(4-cyano-2-fluoro-phenyl)methoxy]-2-pyridyl]-1-piperidyl]methyl}-3-methyl-benzimidazole-5-carboxylate (74.0 mg, 0.144 mmol) in acetonitrile (3.4 mL) and water (1.2 mL) was added lithium hydroxide monohydrate (16.1 mg, 0.383 mmol) and the mixture was heated to 60° C. for 90 min. The reaction was quenched by the addition of 5% aqueous citric acid and the mixture was extracted with EtOAc (3×). The combined organic extracts were washed with brine, dried over sodium sulfate, filtered and the filtrate was concentrated in vacuo. The crude residue was purified by RP-HPLC (15-54.18% 0.1% TFA-ACN in 0.1% TFA-Water, 15 min gradient, Column: Gemini 5 μM, NX-C18 110 Angstrom, 250×21.2 mm) to give the desired compound Example 25. ES/MS m/z: 556.6 ($M+H^+$); $^1H$ NMR (400 MHz, Methanol-d4) δ 8.64 (d, J=5.8 Hz, 1H), 8.59 (s, 1H), 8.31 (dd, J=8.1, 1.7 Hz, 1H), 8.25 (dd, J=8.6, 1.4 Hz, 1H), 8.22 (dd, J=11.4, 1.7 Hz, 1H), 7.82-7.74 (m, 2H), 7.68-7.55 (m, 3H), 6.95 (d, J=5.8 Hz, 1H), 5.75 (s, 2H), 4.87-4.80 (m, 4H), 3.84 (t, J=4.8 Hz, 2H), 3.33 (s, 3H).

Examples 26-31, 80, 88, 90, 112-113, 116, 118, 122, 159-160, 436, and 660-661. Compounds Prepared Using Procedure 4

Other compounds of the present disclosure prepared using the general route described in Procedure 4 include the following Examples.

| Example | Structure/Name/Characterization |
|---|---|
| 26 | 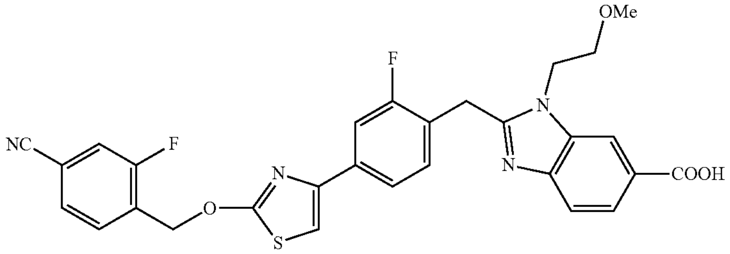 [SMILES: COCCn1c(Cc2ccc(-c3csc(OCc4ccc(C#N)cc4F)n3)cc2F)nc2ccc(C(=O)O)cc21] 2-(4-(2-((4-cyano-2-fluorobenzyl)oxy)thiazol-4-yl)-2-fluorobenzyl)-1-(2-methoxyethyl)-1H-benzo[d]imidazole-6-carboxylic acid: ES/MS m/z 561.5; $^1$H NMR (400 MHz, DMSO-$d_6$) δ 8.24 (d, J = 1.5 Hz, 1H), 7.96 (dd, J = 9.9, 1.5 Hz, 1H), 7.89-7.81 (m, 2H), 7.78 (dd, J = 7.9, 1.5 Hz, 1H), 7.74-7.67 (m, 2H), 7.65-7.59 (m, 2H), 7.39 (t, J = 8.0 Hz, 1H), 5.68 (s, 2H), 4.59 (t, J = 5.1 Hz, 2H), 4.44 (s, 2H), 3.66 (t, J = 5.1 Hz, 2H), 3.20 (s, 3H). |
| 27 | 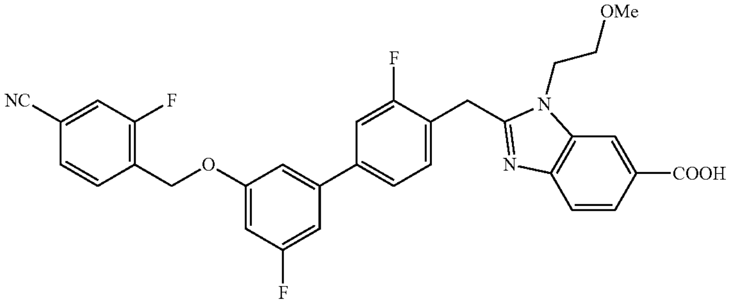 [SMILES: COCCn1c(Cc2ccc(-c3cc(F)cc(OCc4ccc(C#N)cc4F)c3)cc2F)nc2ccc(C(=O)O)cc21] 2-((3'-((4-cyano-2-fluorobenzyl)oxy)-3,5'-difluoro-[1,1'-biphenyl]-4-yl)methyl)-1-(2-methoxyethyl)-1H-benzop[d]imidazole-6-carboxylic acid: ES/MS m/z 572.6; $^1$H NMR (400 MHz, $CD_3OD$) δ 8.56 (s, 1H), 8.23 (dd, J = 8.6, 1.4 Hz, 1H), 7.83-7.76 (m, 2H), 7.68-7.62 (m, 2H), 7.61-7.49 (m, 3H), 7.19-7.14 (m, 1H), 7.13-7.06 (m, 1H), 6.94-6.87 (m, 1H), 5.33 (s, 2H), 4.81 (t, J = 5.0 Hz, 2H), 4.77 (s, 2H), 3. 83 (t, J = 4.9 Hz, 2H). |
| 28 | 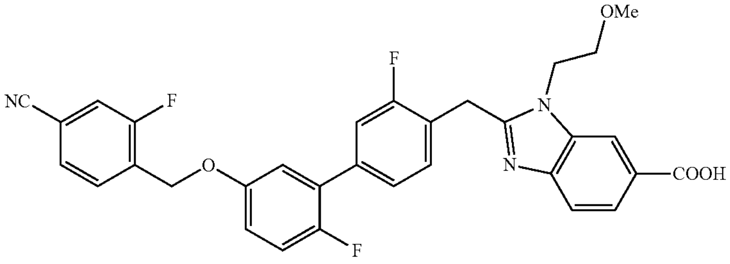 [SMILES: COCCn1c(Cc2ccc(-c3cc(OCc4ccc(C#N)cc4F)ccc3F)cc2F)nc2ccc(C(=O)O)cc21] 2-((5'-((4-cyano-2-fluorobenzyl)oxy)-2',3-difluoro-[1,1'-biphenyl]-4-yl)methyl)-1-(2-methoxyethyl)-1H-benzo[d]imidazole-6-carboxylic acid: ES/MS m/z 572.4; $^1$H NMR (400 MHz, $CD_3OD$) δ 8.56 (s, 1H), 8.26-8.20 (m, 1H), 7.82-7.75 (m, 2H), 7.67-7.61 (m, 2H), 7.56-7.45 (m, 3H), 7.24-7.15 (m, 2H), 7.14-7.06 (m, 1H), 5.29 (s, 2H), 4.83-4.80 (m, 2H), 4.78 (s, 2H), 3.83 (t, J = 4.9 Hz, 2H). |

-continued

| Example | Structure/Name/Characterization |
|---|---|
| 29 | 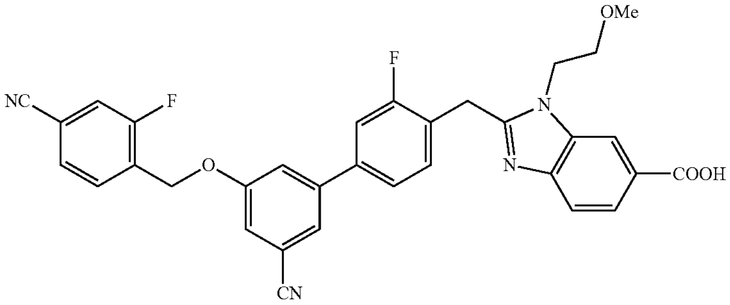 [SMILES: COCCn1c(Cc2ccc(-c3cc(C#N)cc(OCc4ccc(C#N)cc4F)c3)cc2F)nc2ccc(C(=O)O)cc21] 2-((3'-cyano-5'-((4-cyano-2-fluorobenzyl)oxy)-3-fluoro-[1,1'-biphenyl]-4-yl)methyl)-1-(2-methoxyethyl)-1H-benzo[d]imidazole-6-carboxylic acid: ES/MS m/z 579.7; $^{1}$H NMR (400 MHz, $CD_3OD$) δ 8.54-8.51 (m, 1H), 8.20 (dd, J = 8.6, 1.4 Hz, 1H), 7.81 (t, J = 7.6 Hz, 1H), 7.76 (d, J = 8.6 Hz, 1H), 7.70 (t, J = 1.5 Hz, 1H), 7.68-7.58 (m, 5H), 7.57-7.51 (m, 1H), 7.50-7.46 (m, 1H), 5.38 (s, 2H), 4.78 (t, J = 5.0 Hz, 2H), 4.75 (s, 2H), 3.85-3.79 (m, 2H). |
| 30 | 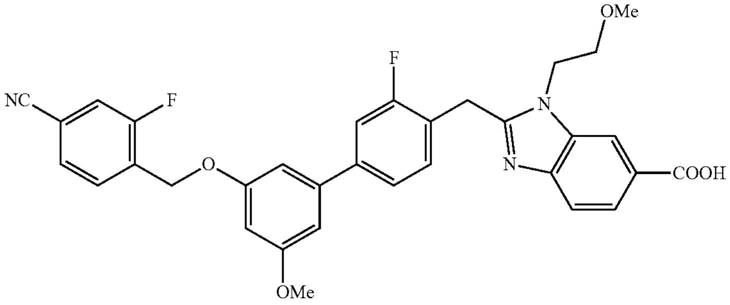 2-((3'-((4-cyano-2-fluorobenzyl)oxy)-3-fluoro-5'-methoxy-[1,1'-biphenyl]-4-yl)methyl)-1-(2-methoxyethyl)-1H-benzo[d]imidazole-6-carboxylic acid: ES/MS m/z 584.6; $^{1}$H NMR (400 MHz, $CD_3OD$) δ 8.58-8.54 (m, 1H), 8.23 (dd, J = 8.6, 1.4 Hz, 1H), 7.83-7.76 (m, 2H), 7.67-7.61 (m, 2H), 7.58-7.47 (m, 3H), 6.92-6.84 (m, 2H), 6.67 (t, J = 2.2 Hz, 1H), 5.31 (s, 2H), 4.81 (t, J = 5.0 Hz, 2H), 4.76 (s, 2H), 3.87 (s, 3H), 3.82 (t, J = 4.9 Hz, 2H). |
| 31 | 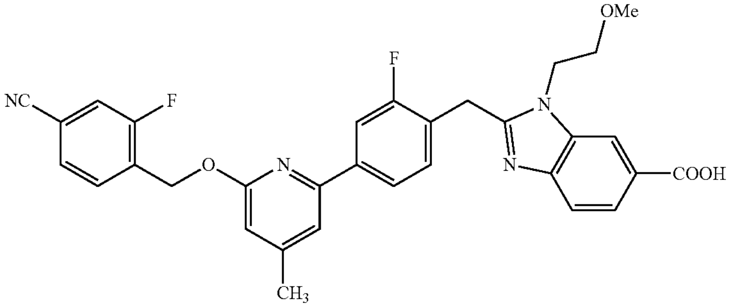 [SMILES: COCCn1c(Cc2ccc(-c3cc(C)cc(OCc4ccc(C#N)cc4F)n3)cc2F)nc2ccc(C(=O)O)cc21] 2-(4-(6-((4-cyano-2-fluorobenzyl)oxy)-4-methylpyridin-2-yl)-2-fluorobenzyl)-1-(2-methoxyethyl)-1H-benzo[d]imidazole-6-carboxylic acid: ES/MS m/z 569.7; $^{1}$H NMR (400 MHz, $CD_3OD$) δ 8.60-8.57 (m, 1H), 8.25 (dd, J = 8.6, 1.4 Hz, 1H), 7.95-7.86 (m, 2H), 7.79 (d, J = 8.6 Hz, 1H), 7.72 (t, J = 7.6 Hz, 1H), 7.63-7.55 (m, 2H), 7.52 (t, J = 7.9 Hz, 1H), 7.44 (s, 1H), 6.79-6.75 (m, 1H), 5.63 (s, 2H), 4.85-4.82 (m, 2H), 4.79 (s, 2H), 3.86-3.80 (m, 2H), 2.42 (s, 3H). |

-continued

| Example | Structure/Name/Characterization |
|---|---|
| 80 | 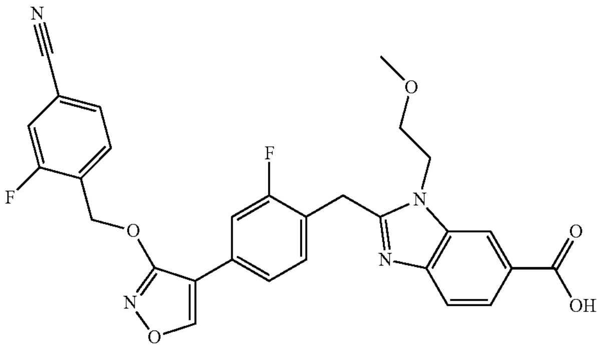 [SMILES: COCCn1c(Cc2ccc(-c3conc3OCc3ccc(C#N)cc3F)cc2F)nc2ccc(C(=O)O)cc21]<br>2-(4-(3-((4-cyano-2-fluorobenzyl)oxy)isoxazol-4-yl)-2-fluorobenzyl)-1-(2-methoxyethyl)-1H-benzo[d]imidazole-6-carboxylic acid: ES/MS 545.3; $^{1}$H NMR (400 MHz, Methanol-d4) δ 8.93 (s, 1H), 8.45 (s, 1H), 8.17-8.12 (m, 1H), 7.79 (t, J = 7.5 Hz, 1H), 7.73 (d, J = 8.5 Hz, 1H), 7.69-7.62 (m, 2H), 7.58-7.52 (m, 2H), 7.40 (t, J = 7.9 Hz, 1H), 5.58 (s, 2H), 4.70 (t, J = 4.9 Hz, 2H), 4.64 (s, 2H), 3.77 (t, J = 5.0 Hz, 2H), 3.29 (s, 3H). |
| 88 | 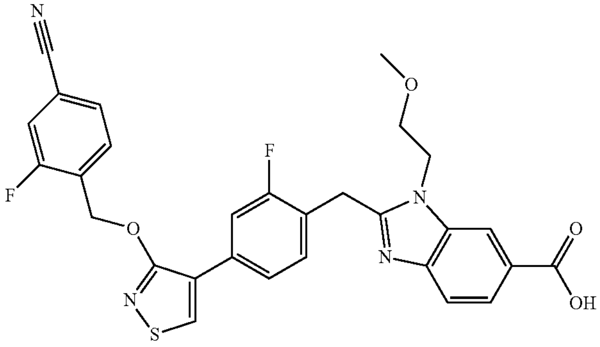 [SMILES: COCCn1c(Cc2ccc(-c3csnc3OCc3ccc(C#N)cc3F)cc2F)nc2ccc(C(=O)O)cc21]<br>2-(4-(3-((4-cyano-2-fluorobenzyl)oxy)isothiazol-4-yl)-2-fluorobenzyl)-1-(2-methoxyethyl)-1H-benzo[d]imidazole-6-carboxylic acid: ES/MS m/z 561.4; $^{1}$H NMR (400 MHz, Methanol-d4) δ 9.03 (s, 1H), 8.53-8.50 (m, 1H), 8.20 (dd, J = 8.6, 1.5 Hz, 1H), 7.78-7.72 (m, 2H), 7.67-7.58 (m, 4H), 7.45 (t, J = 8.1 Hz, 1H), 5.68 (s, 2H), 4.77 (t, J = 5.0 Hz, 2H), 4.70 (s, 2H), 3.79 (t, J = 4.9 Hz, 2H), 3.30 (s, 3H). |
| 90 | 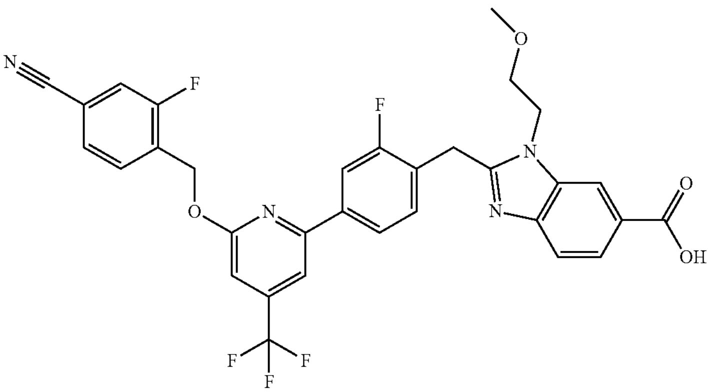 [SMILES: COCCn1c(Cc2ccc(-c3cc(C(F)(F)F)cc(OCc4ccc(C#N)cc4F)n3)cc2F)nc2ccc(C(=O)O)cc21]<br>2-(4-(6-((4-cyano-2-fluorobenzyl)oxy)-4-(trifluoromethyl)pyridin-2-yl)-2-fluorobenzyl)-1-(2-methoxyethyl)-1H-benzo[d]imidazole-6-carboxylic acid: ES/MS m/z 623.2; $^{1}$H NMR (400 MHz, Methanol-d4) δ 8.60 (s, 1H), 8.26 (dd, J = 8.5, 1.4 Hz, 1H), 8.05-7.96 (m, 2H), 7.87-7.74 (m, 3H), 7.67-7.55 (m, 3H), 7.24 (s, 1H), 5.73 (s, 2H), 4.82 (s, 3H), 3.84 (t, J = 4.8 Hz, 2H), 3.37 (s, 2H). |

-continued

| Example | Structure/Name/Characterization |
|---|---|
| 112 | 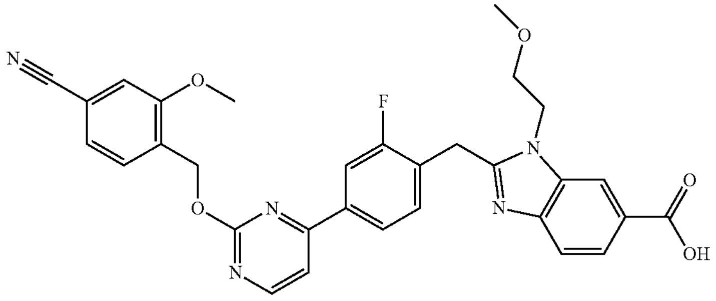 [SMILES: COCCn1c(Cc2ccc(-c3ccnc(OCc4ccc(C#N)cc4OC)n3)cc2F)nc2ccc(C(=O)O)cc21] 2-(4-(2-((4-cyano-2-methoxybenzyl)oxy)pyrimidin-4-yl)-2-fluorobenzyl)-1-(2-methoxyethyl)-1H-benzo[d]imidazole-6-carboxylic acid: ES/MS m/z 568.2; $^1$H NMR (400 MHz, MeOD) δ 8.67 (d, J = 5.2 Hz, 1H), 8.46 (s, 1H), 8.14 (dd, J = 8.6, 1.5 Hz, 1H), 8.03 (d, J = 9.5 Hz, 2H), 7.74 (d, J = 8.5 Hz, 1H), 7.68 (d, J = 5.3 Hz, 1H), 7.65 (d, J = 7.8 Hz, 1H), 7.54 (t, J = 7.7 Hz, 1H), 7.40 (d, J = 1.4 Hz, 1H), 7.35 (dd, J = 7.7, 1.5 Hz, 1H), 5.65 (s, 2H), 4.72 (d, J = 4.8 Hz, 3H), 3.98 (s, 3H), 3.79 (t, J = 5.0 Hz, 2H), 3.30 (s, 3H). |
| 113 | 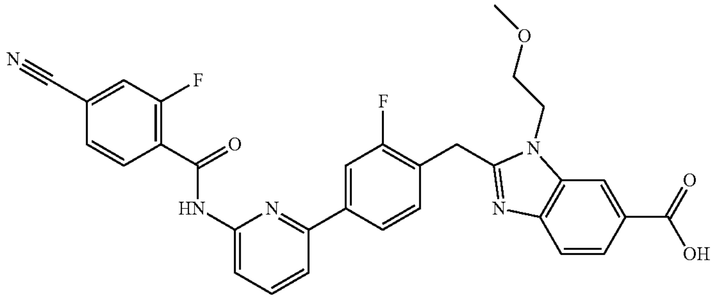 [SMILES: COCCn1c(Cc2ccc(-c3cccc(NC(=O)c4ccc(C#N)cc4F)n3)cc2F)nc2ccc(C(=O)O)cc21] 2-(4-(6-(4-cyano-2-fluorobenzamido)pyridin-2-yl)-2-fluorobenzyl)-1-(2-methoxyethyl)-1H-benzo[d]imidazole-6-carboxylic acid: ES/MS m/z 568.2; $^1$H NMR (400 MHz, DMSO) δ 11.24 (s, 1H), 8.20 (s, 1H), 8.05 (d, J = 9.8 Hz, 1H), 7.98 (d, J = 8.0 Hz, 1H), 7.89 (d, J = 7.0 Hz, 1H), 7.85 (dd, J = 7.9, 1.5 Hz, 1H), 7.80 (dd, J = 8.5, 1.5 Hz, 1H), 7.59 (d, J = 8.4 Hz, 1H), 7.44 (s, 1H), 4.57 (d, J = 5.0 Hz, 2H), 4.44 (s, 2H), 3.65 (t, J = 5.0 Hz, 2H), 3.20 (s, 3H). |
| 116 | 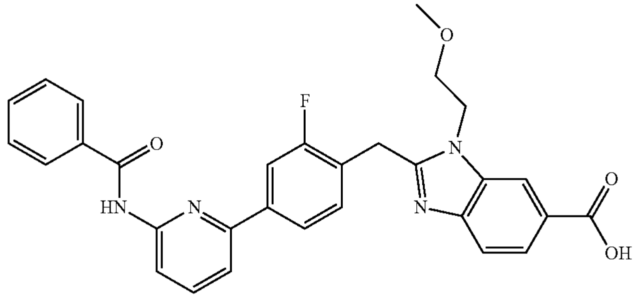 [SMILES: COCCn1c(Cc2ccc(-c3cccc(NC(=O)c4ccccc4)n3)cc2F)nc2ccc(C(=O)O)cc21] 2-(4-(6-benzamidopyridin-2-yl)-2-fluorobenzyl)-1-(2-methoxyethyl)-1H-benzo[d]imidazole-6-carboxylic acid: ES/MS m/z 525.2; $^1$H NMR (400 MHz, DMSO) δ 10.72 (s, 1H), 8.29 (d, J = 1.5 Hz, 1H), 8.17 (d, J = 8.2 Hz, 1H), 8.11-8.01 (m, 3H), 8.01-7.90 (m, 2H), 7.87 (dd, J = 8.5, 1.5 Hz, 1H), 7.82 (d, J = 7.6 Hz, 1H), 7.69-7.58 (m, 2H), 7.55 (dd, J = 8.2, 6.7 Hz, 2H), 7.49 (t, J = 8.0 Hz, 1H), 4.64 (t, J = 5.1 Hz, 2H), 4.53 (s, 2H), 3.68 (d, J = 5.0 Hz, 1H), 3.21 (s, 3H). |

-continued

| Example | Structure/Name/Characterization |
|---|---|
| 118 | 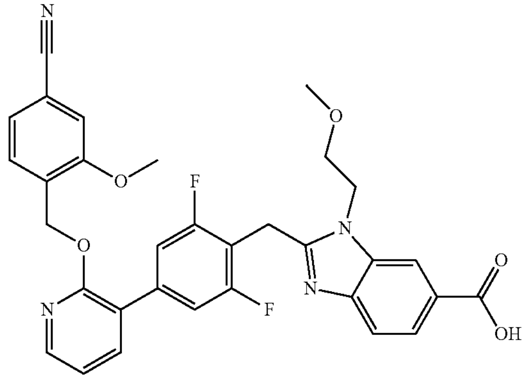 [SMILES: COCCn1c(Cc2c(F)cc(-c3cccnc3OCc3ccc(C#N)cc3OC)cc2F)nc2ccc(C(=O)O)cc21] 2-(4-(2-((4-cyano-2-methoxybenzyl)oxy)pyridin-3-yl)-2,6-difluorobenzyl)-1-(2-methoxyethyl)-1H-benzo[d]imidazole-6-carboxylic acid: ES/MS m/z 585.2; $^{1}$H NMR (400 MHz, MeOD) δ 8.53 (d, J = 1.5 Hz, 1H), 8.21 (ddd, J = 9.9, 6.8, 1.6 Hz, 2H), 7.88 (dd, J = 7.4, 1.8 Hz, 1H), 7.74 (d, J = 8.6 Hz, 1H), 7.48 (dd, J = 10.5, 8.3 Hz, 3H), 7.38 (d, J = 1.4 Hz, 1H), 7.29 (dd, J = 7.7, 1.4 Hz, 1H), 7.14 (dd, J = 7.4, 5.0 Hz, 1H), 5.53 (s, 2H), 4.82 (t, J = 5.0 Hz, 2H), 4.77 (s, 2H), 3.96 (s, 3H), 3.84 (t, J = 4.9 Hz, 2H), 3.30 (s, 3H). |
| 122 | 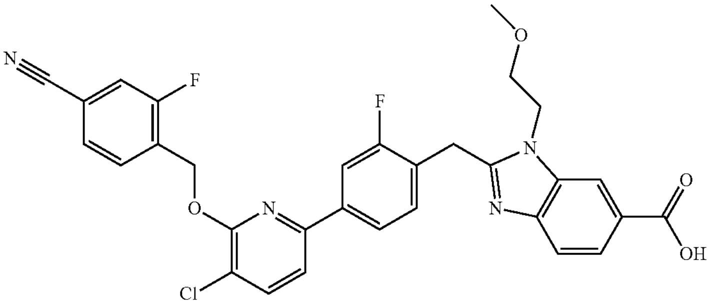 [SMILES: COCCn1c(Cc2ccc(-c3ccc(Cl)c(OCc4ccc(C#N)cc4F)n3)cc2F)nc2ccc(C(=O)O)cc21] 2-(4-(5-chloro-6-((4-cyano-2-fluorobenzyl)oxy)pyridin-2-yl)-2-fluorobenzyl)-1-(2-methoxyethyl)-1H-benzo[d]imidazole-6-carboxylic acid: ES/MS m/z 589.2; $^{1}$H NMR (400 MHz, DMSO) δ 8.28 (d, J = 1.5 Hz, 1H), 8.05 (d, J = 8.0 Hz, 1H), 7.97-7.93 (m, 1H), 7.93-7.81 (m, 3H), 7.77 (d, J = 4.7 Hz, 2H), 7.72 (d, J = 8.1 Hz, 1H), 7.64 (d, J = 8.4 Hz, 1H), 7.47 (t, J = 8.1 Hz, 1H), 5.72 (s, 2H), 4.63 (t, J = 5.1 Hz, 2H), 4.51 (s, 2H), 3.21 (s, 3H). |
| 159 | 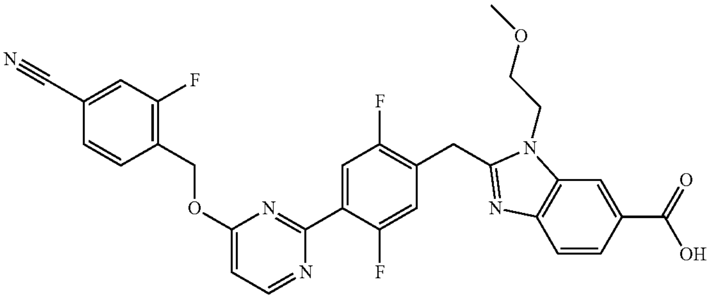 [SMILES: COCCn1c(Cc2cc(F)c(-c3nccc(OCc4ccc(C#N)cc4F)n3)cc2F)nc2ccc(C(=O)O)cc21] 2-(4-(4-((4-cyano-2-fluorobenzyl)oxy)pyrimidin-2-yl)-2,5-difluorobenzyl)-1-(2-methoxyethyl)-1H-benzo[d]imidazole-6-carboxylic acid: ES/MS 574.2; $^{1}$H NMR (400 MHz, MeOD) δ 8.65 (d, J = 5.8 Hz, 1H), 8.52 (d, J = 1.4 Hz, 1H), 8.19 (dd, J = 8.6, 1.5 Hz, 1H), 7.90 (dd, J = 10.3, 6.1 Hz, 1H), 7.82-7.69 (m, 2H), 7.69-7.55 (m, 2H), 7.44-7.32 (m, 1H), 6.98 (d, J = 5.8 Hz, 1H), 5.69 (s, 2H), 4.81-4.72 (m, 4H), 3.82 (t, J = 4.9 Hz, 2H). Additional peak (s, 3H) obscured by solvent. |

-continued

| Example | Structure/Name/Characterization |
|---|---|
| 160 | 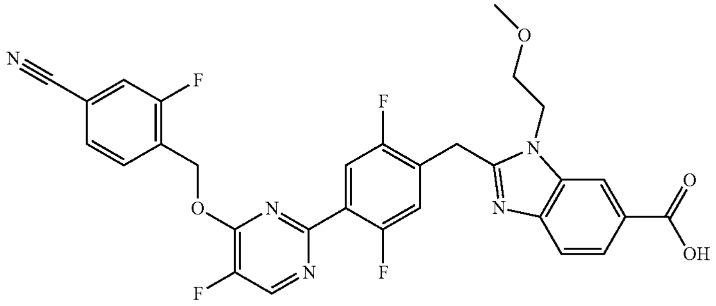 [SMILES: COCCn1c(Cc2cc(F)c(-c3ncc(F)c(OCc4ccc(C#N)cc4F)n3)cc2F)nc2ccc(C(=O)O)cc21] 2-(4-(4-((4-cyano-2-fluorobenzyl)oxy)-5-fluoropyrimidin-2-yl)-2,5-difluorobenzyl)-1-(2-methoxyethyl)-1H-benzo[d]imidazole-6-carboxylic acid: ES/MS m/z 592.2; $^1$H NMR (400 MHz, MeOD) δ 8.61 (d, J = 2.8 Hz, 1H), 8.49-8.45 (m, 1H), 8.15 (dd, J = 8.5, 1.5 Hz, 1H), 7.90 (dd, J = 10.4, 6.1 Hz, 1H), 7.81-7.70 (m, 2H), 7.67-7.57 (m, 2H), 7.32 (dd, J = 10.9, 6.0 Hz, 1H), 5.76 (s, 2H), 4.74 (t, J = 5.0 Hz, 2H), 4.70 (s, 2H), 3.80 (t, J = 5.0 Hz, 2H), 3.29 (s, 3H). |
| 436 | 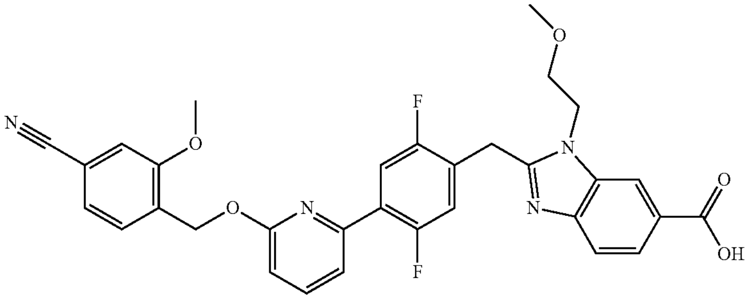 [SMILES: COCCn1c(Cc2cc(F)c(-c3cccc(OCc4ccc(C#N)cc4OC)n3)cc2F)nc2ccc(C(=O)O)cc21] 2-(4-(6-((4-cyano-2-methoxybenzyl)oxy)pyridin-2-yl)-2,5-difluorobenzyl)-1-(2-methoxyethyl)-1H-benzo[d]imidazole-6-carboxylic acid: ES/MS m/z 585.2; $^1$H NMR (400 MHz, Methanol-d4) δ 8.50 (s, 1H), 8.18 (dd, J = 8.5, 1.5 Hz, 1H), 7.86-7.71 (m, 3H), 7.57 (dd, J = 7.7, 3.5 Hz, 2H), 7.38 (d, J = 1.5 Hz, 1H), 7.35-7.22 (m, 2H), 6.95 (d, J = 8.3 Hz, 1H), 5.57 (s, 2H), 4.77 (t, J = 4.9 Hz, 2H), 4.70 (s, 2H), 3.97 (s, 3H), 3.82 (t, J = 4.9 Hz, 2H), 3.31 (s, 3H). |
| 660 | 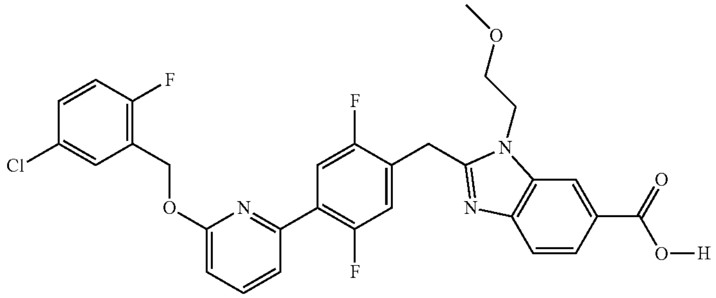 [SMILES: COCCn1c(Cc2cc(F)c(-c3cccc(OCc4cc(Cl)ccc4F)n3)cc2F)nc2ccc(C(=O)O)cc21] ES/MS m/z 582; 1H NMR (400 MHz, Acetonitrile-d3) δ 8.36 (d, J = 1.5 Hz, 1H), 8.05 (dd, J = 8.5, 1.5 Hz, 1H), 7.91-7.71 (m, 3H), 7.57 (ddd, J = 16.5, 6.9, 2.2 Hz, 2H), 7.38 (ddd, J = 8.8, 4.4, 2.8 Hz, 1H), 7.27 (dd, J = 11.5, 6.1 Hz, 1H), 7.18 (t, J = 9.2 Hz, 1H), 6.91 (d, J = 8.2 Hz, 1H), 5.54 (s, 2H), 4.58 (d, J = 5.0 Hz, 4H), 3.75 (t, J = 5.0 Hz, 2H), 3.26 (s, 3H). 19F NMR (377 MHz, Acetonitrile-d3) δ −122.30 (ddd, J = 18.1, 11.8, 6.7 Hz), −122.61 (dt, J = 10.3, 5.4 Hz), −123.82 (ddd, J = 17.7, 10.8, 6.1 Hz). |

-continued

| Example | Structure/Name/Characterization |
|---|---|
| 661 | 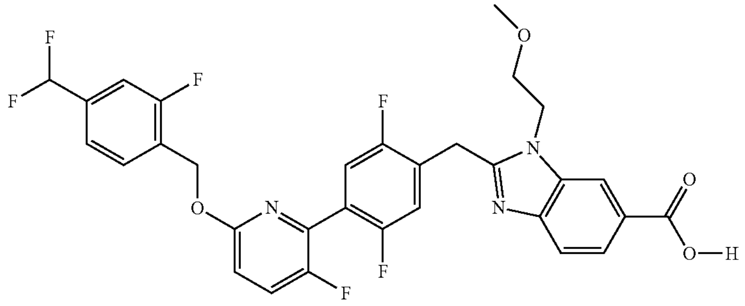 [SMILES: COCCn1c(Cc2cc(F)c(-c3nc(OCc4ccc(C(F)F)cc4F)ccc3F)cc2F)nc2ccc(C(=O)O)cc21] ES/MS m/z 616.3; 1H NMR (400 MHz, Methanol-d4) δ 8.57 (t, J = 1.0 Hz, 1H), 8.24 (dd, J = 8.6, 1.4 Hz, 1H), 7.80 (d, J = 8.6 Hz, 1H), 7.72-7.60 (m, 2H), 7.51-7.28 (m, 4H), 7.02 (dd, J = 9.0, 3.0 Hz, 1H), 6.80 (t, J = 56.0 Hz, 1H), 5.52 (s, 2H), 4.84 (t, J = 5.0 Hz, 2H), 4.81 (s, 2H), 3.85 (dd, J = 5.4, 4.4 Hz, 2H), 3.32 (s, 3H). (Multiplet Report) 19F NMR (376 MHz, Methanol-d4) δ −77.89, −113.29 (d, J = 56.4 Hz), −119.48 (dd, J = 10.3, 7.2 Hz), −119.90 (dddd, J = 35.4, 17.7, 9.7, 5.7 Hz), −124.38 (ddd, J = 16.8, 9.9, 6.0 Hz), −134.18 (ddd, J = 35.4, 8.9, 2.9 Hz). |

Example 32, 2-(1-(4-(6-((4-cyano-2-fluorobenzyl)oxy)pyridin-2-yl)phenyl)cyclopropyl)-1-(2-methoxyethyl)-1H-benzo[d]imidazole-6-carboxylic acid Procedure 5

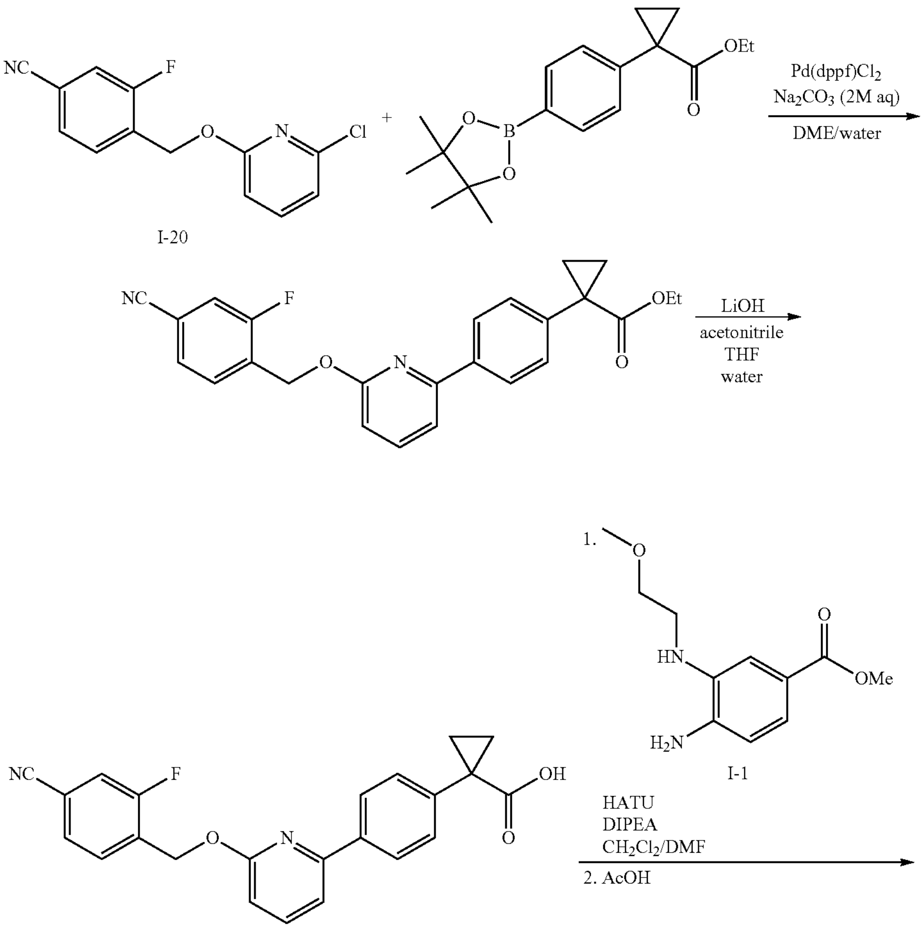

-continued

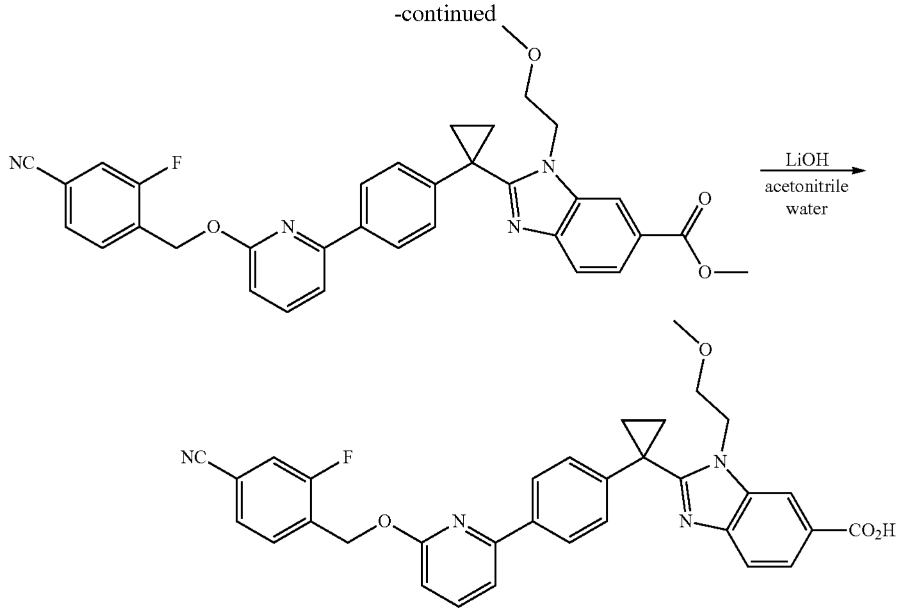

Ethyl 1-(4-(6-((4-cyano-2-fluorobenzyl)oxy)pyridin-2-yl)phenyl)cyclopropane-1-carboxylate: To a vial was added 4-(((6-chloropyridin-2-yl)oxy)methyl)-3-fluorobenzonitrile (I-20) (200 mg, 0.76 mmol), ethyl 1-[4-(4,4,5,5-tetramethyl-1,3,2-dioxaborolan-2-yl)phenyl]cyclopropanecarboxylate (289 mg, 0.914 mmol), and Pd(dppf)$Cl_2$ (57 mg, 0.076 mmol). To the vial was added dimethoxyethane (2 mL) and water (0.5 mL). Sodium carbonate (2 M aqueous, 0.61 mL, 1.22 mmol) was added, and the mixture was degassed with argon for 1 minute. The vial was sealed and stirred 3 hours at 100° C. LCMS showed conversion of the starting material to desired product, and the vial was cooled to room temperature. The organic layer was transferred directly to a loading column, and the crude material was purified by silica gel chromatography (eluent: EtOAc/hexanes) to afford the desired product: ES/MS: 417.379 ($M+H^+$).

1-(4-(6-((4-cyano-2-fluorobenzyl)oxy)pyridin-2-yl)phenyl)cyclopropane-1-carboxylic acid: To a 40 mL vial was added ethyl 1-(4-(6-((4-cyano-2-fluorobenzyl)oxy)pyridin-2-yl)phenyl)cyclopropane-1-carboxylate (300 mg, 0.72 mmol), and the material was dissolved in acetonitrile (4 mL) and THF (4 mL). Lithium hydroxide (26 mg, 1.08 mmol) dissolved in water (1 mL) was added, and the mixture was stirred overnight at 55° C. LCMS revealed a mixture of starting material and desired product. The mixture was partitioned between EtOAc (100 mL) and water (40 mL), and acidified with 50% aqueous citric acid. The layers were separated, and the aqueous layer was extracted with EtOAc (3×50 mL). The combined organic layers were dried over $MgSO_4$, filtered, and concentrated under reduced pressure. The crude material was triturated with a small amount of EtOAc, and the precipitate was dried and carried directly forward: ES/MS: 389.408 ($M+H^+$).

Methyl 2-(1-(4-(6-((4-cyano-2-fluorobenzyl)oxy)pyridin-2-yl)phenyl)cyclopropyl)-1-(2-methoxyethyl)-1H-benzo[d]imidazole-6-carboxylate: To a 25 mL RBF was added 1-(4-(6-((4-cyano-2-fluorobenzyl)oxy)pyridin-2-yl)phenyl)cyclopropane-1-carboxylic acid (105 mg, 0.27 mmol), methyl 4-amino-3-(2-methoxyethylamino)benzoate (I-1) (58 mg, 0.26 mmol), and 2-(7-Aza-1H-benzotriazole-1-yl)-1,1,3,3-tetramethyluronium hexafluorophosphate (HATU) (76 mg, 0.324 mmol). To the vial was added $CH_2Cl_2$ (4 mL) and DMF (1 mL), and the mixture was stirred for 15 minutes at room temperature. N,N-Diisopropylethylamine (0.235 mL, 1.35 mmol) was added, and the mixture was stirred at room temperature for 5 hours, at which time LCMS showed conversion of the starting materials to the intermediate amide. The mixture was diluted with EtOAc (50 mL) and washed with sat. aq. $NH_4Cl$ (2×10 mL) and sat. aq. $NaHCO_3$ (2×10 mL). The organic layer was dried over $MgSO_4$, filtered, and concentrated under reduced pressure. The crude material was dissolved in acetic acid (1 mL), and stirred 1 hour at 100° C. LCMS showed conversion of the intermediate amide to the desired product, and the mixture was concentrated under reduced pressure. The crude material was purified by silica gel chromatography (eluent: EtOAc/hexanes) to afford the desired product: ES/MS: 577.435 ($M+H^+$).

2-(1-(4-(6-((4-cyano-2-fluorobenzyl)oxy)pyridin-2-yl)phenyl)cyclopropyl)-1-(2-methoxyethyl)-1H-benzo[d]imidazole-6-carboxylic acid (Example 32): To a 40 mL vial was added methyl 2-(1-(4-(6-((4-cyano-2-fluorobenzyl)oxy)pyridin-2-yl)phenyl)cyclopropyl)-1-(2-methoxyethyl)-1H-benzo[d]imidazole-6-carboxylate (15 mg, 0.026 mmol), and acetonitrile (1 mL) was added. To the mixture was added LiOH (1 mg, 0.039 mmol) dissolved in water (0.2 mL), and the mixture was stirred overnight at room temperature. LCMS showed partial conversion to the desired product. LiOH (0.5 mg, 0.02 mmol) was added, and the mixture was stirred 2 hours at 55° C. LCMS showed conversion of the starting material to the product. The mixture was acidified with 50% citric acid (0.2 mL), and the material was purified by RP-HPLC (eluent: water/MeCN*0.1% TFA) to yield the product as a trifluoroacetate salt: ES/MS: 563.573 ($M+H^+$); $^1H$ NMR (400 MHz, Methanol-$d_4$) δ 8.54 (dd, J=1.4, 0.7 Hz, 1H), 8.26 (dd, J=8.6, 1.5 Hz, 1H), 8.08-7.98 (m, 2H), 7.88 (dd, J=8.6, 0.6 Hz, 1H), 7.83-7.67 (m, 2H), 7.64-7.54 (m, 2H), 7.54-7.45 (m, 1H), 7.38-7.29 (m, 2H), 6.86 (d, J=8.1 Hz, 1H), 5.63 (s, 2H), 4.67 (t, J=5.2 Hz, 2H), 3.52 (t, J=5.1 Hz, 2H), 3.14 (s, 3H), 1.99-1.79 (in, 4H).

Examples 105, 108, 123, 282, 447, 571-575, 577, and 581. Compounds Prepared Using Procedure 5

Other compounds of the present disclosure prepared using the general route described in Procedure 5 include the following Examples.

| Example | Structure/Name/Characterization |
|---|---|
| 105 | 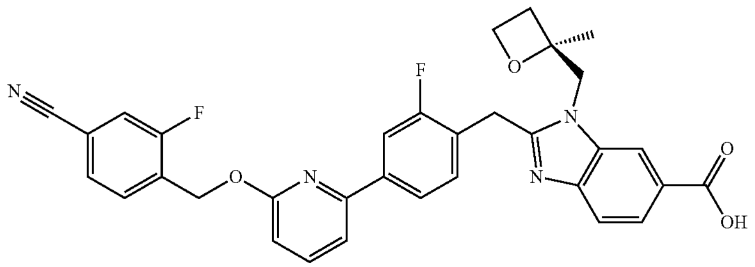 [SMILES: C[C@@]1(Cn2c(Cc3ccc(-c4cccc(OCc5ccc(C#N)cc5F)n4)cc3F)nc3ccc(C(=O)O)cc32)CCO1] (S)-2-(4-(6-((4-cyano-2-fluorobenzyl)oxy)pyridin-2-yl)-2-fluorobenzyl)-1-((2-methyloxetan-2-yl)methyl)-1H-benzo[d]imidazole-6-carboxylic acid: ES/MS m/z 581.2; $^1$H NMR (400 MHz, DMSO) δ 8.34 (d, J = 1.5 Hz, 1H), 7.93 (dd, J = 10.0, 1.4 Hz, 1H), 7.89-7.83 (m, 3H), 7.83-7.69 (m, 3H), 7.67 (d, J = 7.4 1H), 7.61 (d, J = 8.4 Hz, 1H), 7.44 (t, J = 7.9 Hz, 1H), 6.93 (d, J = 8.2 Hz, 5.62 (s, 2H), 4.71 (d, J = 15.6 Hz, 1H), 4.50 (dt, J = 33.6, 16.4 Hz, 3H), 4.37-4.19 (m, 1H), 4.01-3.85 (m, 1H), 2.42 (t, J = 7.8 Hz, 2H), 1.46 (s, 3H). |
| 108 | 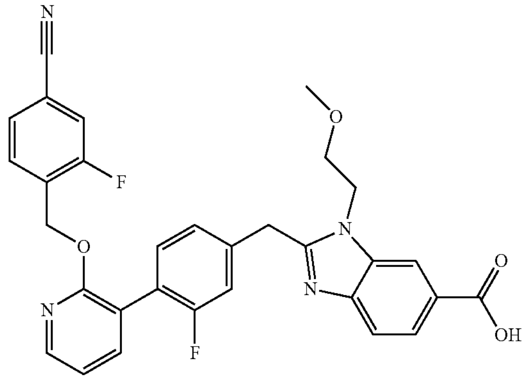 [SMILES: COCCn1c(Cc2ccc(-c3cccnc3OCc3ccc(C#N)cc3F)c(F)c2)nc2ccc(C(=O)O)cc21] 2-(4-(2-((4-cyano-2-fluorobenzyl)oxy)pyridin-3-yl)-3-fluorobenzyl)-1-(2-methoxyethyl)-1H-benzo[d]imidazole-6-carboxylic acid: ES/MS m/z 555.2; $^1$H NMR (400 MHz, MeOD) δ 8.54 (d, J = 1.3 Hz, 1H), 8.23 (dd, J = 3.4, 1.7 Hz, 1H), 8.21 (d, J = 1.7 Hz, 1H), 7.79 (dd, J = 8.6, 0.7 Hz, 1H), 7.76-7.68 (m, 1H), 7.61-7.46 (m, 4H), 7.27 (d, J = 9.2 Hz, 2H), 7.13 (dd, J = 7.3, 5.0 Hz, 1H), 5.55 (d, J = 1.2 Hz, 2H), 4.77 (t, J = 5.0 Hz, 2H), 4.72 (s, 2H), 3.78 (d, J = 5.0 Hz, 2H), 3.29 (s, 3H). |
| 123 | 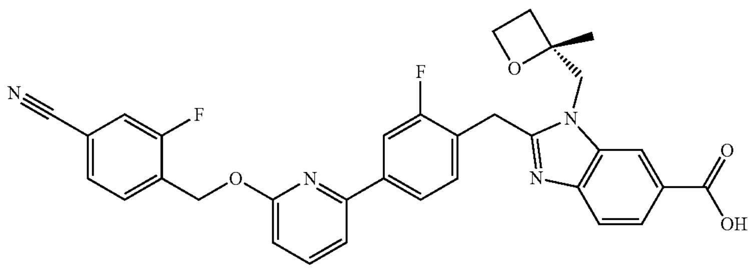 [SMILES: C[C@]1(Cn2c(Cc3ccc(-c4cccc(OCc5ccc(C#N)cc5F)n4)cc3F)nc3ccc(C(=O)O)cc32)CCO1] (R)-2-(4-(6-((4-cyano-2-fluorobenzyl)oxy)pyridin-2-yl)-2-fluorobenzyl)-1-((2-methyloxetan-2-yl)methyl)-1H-benzo[d]imidazole-6-carboxylic acid: ES/MS m/z 581.2; $^1$H NMR (400 MHz, DMSO) δ 8.34 (s, 1H), 7.93 (dd, J = 10.0, 1.4 Hz, 1H), 7.90-7.71 (m, 7H), 7.67 (d, J = 7.5 Hz, 1H), 7.62 (d, J = 8.4 Hz, 1H), 7.44 (t, J = 7.8 Hz, 1H), 6.93 (d, J = 8.2 Hz, 1H), 5.62 (s, 2H), 4.71 (d, J = 15.6 Hz, 1H), 4.51 (dt, J = 33.9, 16.4 Hz, 3H), 4.31 (q, J = 7.5 Hz, 1H), 4.03-3.89 (m, 1H), 2.42 (t, J = 7.8 Hz, 2H), 1.46 (s, 3H). |

-continued

| Example | Structure/Name/Characterization |
|---|---|
| 282 | 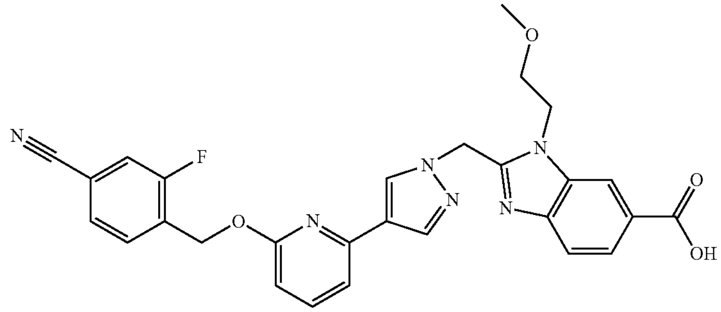 [SMILES: COCCn1c(Cn2cc(-c3cccc(OCc4ccc(C#N)cc4F)n3)cn2)nc2ccc(C(=O)O)cc21]<br>2-((4-(6-((4-cyano-2-fluorobenzyl)oxy)pyridin-2-yl)-1H-pyrazol-1-yl)methyl)-1-(2-methoxyethyl)-1H-benzo[d]imidazole-6-carboxylic acid: ES/MS m/z 527.5; $^{1}$H NMR (400 MHz, Methanol-d4) δ 8.46 (t, J = 1.0 Hz, 1H), 8.31 (s, 1H), 8.14 (dd, J = 8.6, 1.5 Hz, 1H), 8.07 (s, 1H), 7.90 (s, 0H), 7.79 (d, J = 8.6 Hz, 1H), 7.76-7.62 (m, 2H), 7.52 (ddd, J = 14.5, 8.8, 1.5 Hz, 2H), 7.26 (d, J = 7.4 Hz, 1H), 6.72 (d, J = 8.2 Hz, 1H), 5.96 (s, 2H), 5.58 (s, 2H), 4.84-4.79 (m, 0H), 4.76 (t, J = 5.0 Hz, 2H), 3.72 (t, J = 4.9 Hz, 2H), 3.29 (s, 3H). |
| 447 | 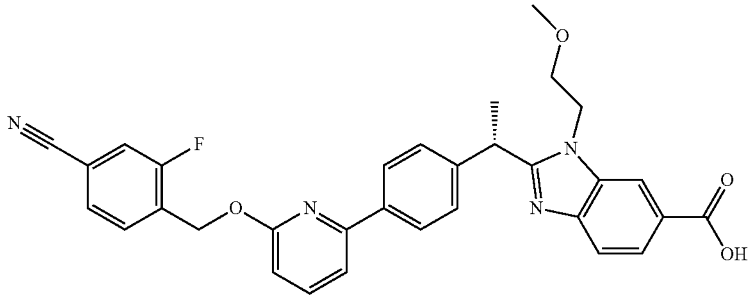 [SMILES: COCCn1c([C@@H](C)c2ccc(-c3cccc(OCc4ccc(C#N)cc4F)n3)cc2)nc2ccc(C(=O)O)cc21]<br>And<br>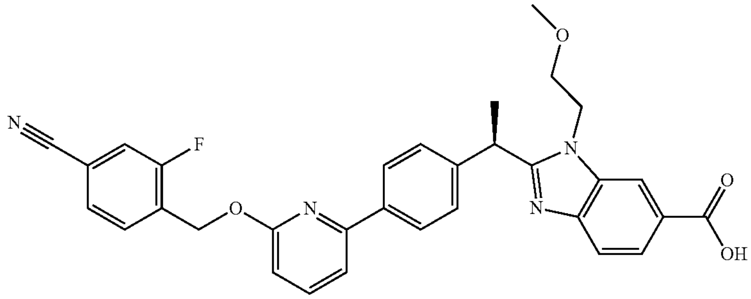 [SMILES: COCCn1c([C@H](C)c2ccc(-c3cccc(OCc4ccc(C#N)cc4F)n3)cc2)nc2ccc(C(=O)O)cc21]<br>2-(1-(4-(6-((4-cyano-2-fluorobenzyl)oxy)pyridin-2-yl)phenyl)ethyl)-1-(2-methoxyethyl)-1H-benzo[d]imidazole-6-carboxylic acid: ES/MS 551.4; $^{1}$H NMR (400 MHz, Methanol-d4) δ 8.52 (s, 1H), 8.25 (d, J = 8.6 Hz, 1H), 8.06 (d, J = 8.1 Hz, 2H), 7.88 (d, J = 8.7 Hz, 1H), 7.76 (dt, J = 23.3, 7.7 Hz, 2H), 7.66-7.50 (m, 3H), 7.43 (d, J = 8.1 Hz, 2H), 6.87 (d, J = 8.2 Hz, 1H), 5.64 (s, 2H), 5.08 (q, J = 7.2 Hz, 1H), 4.78-4.61 (m, 2H), 3.71 (dt, J = 8.6, 3.9 Hz, 1H), 3.55 (ddd, J = 10.8, 7.9, 3.4 Hz, 1H), 3.23 (s, 3H), 1.94 (d, J = 7.1 Hz, 3H). |

-continued

| Example | Structure/Name/Characterization |
|---|---|
| 571 | 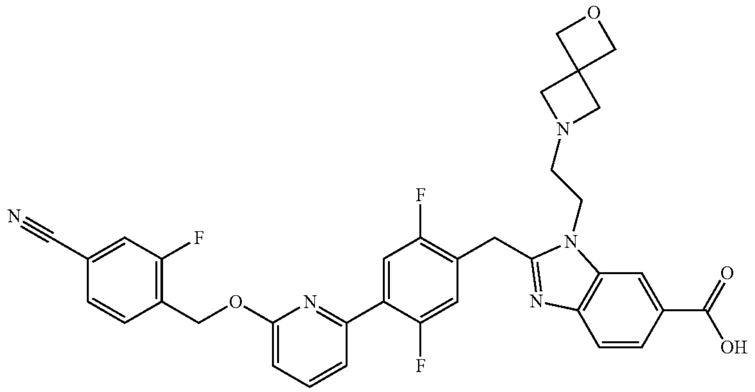 [SMILES: N#Cc1ccc(COc2cccc(-c3cc(F)c(Cc4nc5ccc(C(=O)O)cc5n4CCN4CC5(COC5)C4)cc3F)n2)c(F)c1] 1-(2-(2-oxa-6-azaspiro[3.3]heptan-6-yl)ethyl)-2-(4-(6-((4-cyano-2-fluorobenzyl)oxy)pyridin-2-yl)-2,5-difluorobenzyl)-1H-benzo[d]imidazole-6-carboxylic acid: ES/MS m/z 640.3; $^1$H NMR (400 MHz, Methanol-d4) δ 8.46 (d, J = 1.3 Hz, 1H), 8.14 (dd, J = 8.5, 1.4 Hz, 1H), 7.88-7.68 (m, 4H), 7.64-7.52 (m, 3H), 7.36 (dd, J = 11.2, 6.1 Hz, 1H), 6.95 (d, J = 8.3 Hz, 1H), 5.62 (s, 2H), 4.82 (d, J = 3.1 Hz, 6H), 4.63 (s, 2H), 4.50 (s, 4H), 3.83 (t, J = 6.9 Hz, 2H). |
| 572 | 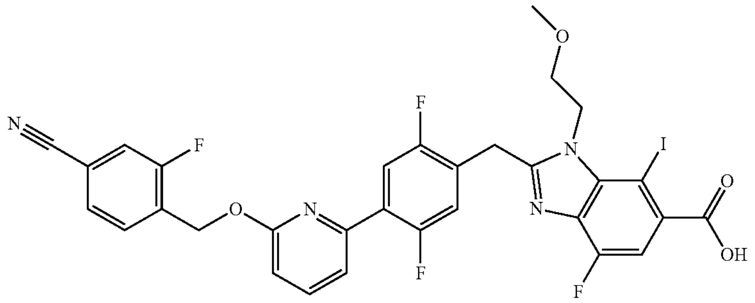 [SMILES: COCCn1c(Cc2cc(F)c(-c3cccc(OCc4ccc(C#N)cc4F)n3)cc2F)nc2c(F)cc(C(=O)O)c(I)c21] 2-(4-(6-((4-cyano-2-fluorobenzyl)oxy)pyridin-2-yl)-2,5-difluorobenzyl)-4-fluoro-7-iodo-1-(2-methoxyethyl)-1H-benzo[d]imidazole-6-carboxylic acid: ES/MS m/z 717.1; $^1$H NMR (400 MHz, Chloroform-d) δ 8.01 (s, 1H), 7.82-7.74 (m, 1H), 7.69 (dt, J = 14.8, 7.7 Hz, 2H), 7.56-7.46 (m, 2H), 7.42 (dd, J = 9.3, 1.5 Hz, 1H), 7.13 (dd, J = 11.1, 6.0 Hz, 1H), 6.86 (dd, J = 8.2, 0.7 Hz, 1H), 5.59 (s, 2H), 4.60 (s, 2H), 4.45 (t, J = 5.0 Hz, 2H), 3.70 (t, J = 4.9 Hz, 2H), 3.29 (s, 3H). |
| 573 | 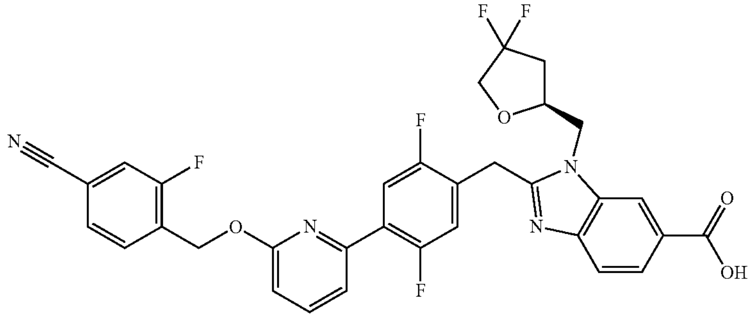 [SMILES: N#Cc1ccc(COc2cccc(-c3cc(F)c(Cc4nc5ccc(C(=O)O)cc5n4C[C@@H]4CC(F)(F)CO4)cc3F)n2)c(F)c1] |

-continued

| Example | Structure/Name/Characterization |
|---|---|
| | And<br>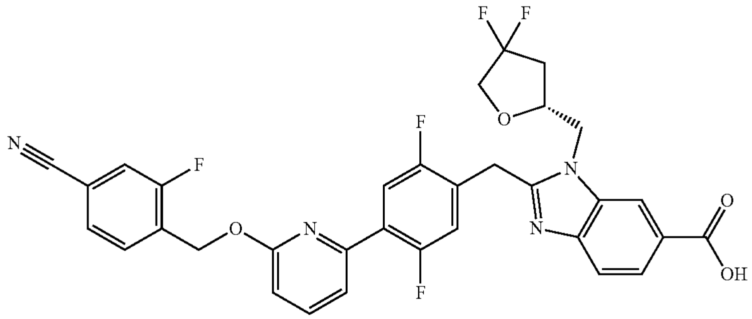 [SMILES: N#Cc1ccc(COc2cccc(-c3cc(F)c(Cc4nc5ccc(C(=O)O)cc5n4C[C@H]4CC(F)(F)CO4)cc3F)n2)c(F)c1]<br>2-(4-(6-((4-cyano-2-fluorobenzyl)oxy)pyridin-2-yl)-2,5-difluorobenzyl)-1-((4,4-difluorotetrahydrofuran-2-yl)methyl)-1H-benzo[d]imidazole-6-carboxylic acid: ES/MS m/z 635.5; $^{1}$H NMR (400 MHz, Methanol-d4) δ 8.56-8.45 (m, 1H), 8.16 (dd, J = 8.6, 1.5 Hz, 1H), 7.96-7.67 (m, 4H), 7.67-7.52 (m, 3H), 7.32 (dd, J = 11.3, 6.1 Hz, 1H), 6.96 (dd, J = 8.3, 0.7 Hz, 1H), 5.64 (s, 2H), 4.75 (t, J = 7.7 Hz, 1H), 4.70 (d, J = 8.5 Hz, 2H), 4.66-4.53 (m, 1H), 4.13 (q, J = 11.0 Hz, 1H), 3.97-3.72 (m, 1H), 2.77 (tt, J = 14.9, 7.8 Hz, 1H), 2.34 (qd, J = 14.8, 8.9 Hz, 1H). |
| 574 | 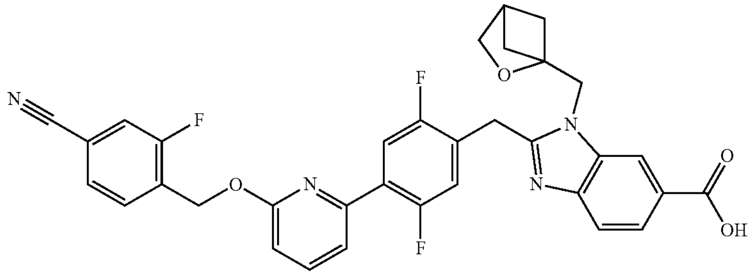 [SMILES: N#Cc1ccc(COc2cccc(-c3cc(F)c(Cc4nc5ccc(C(=O)O)cc5n4CC45CC(CO4)C5)cc3F)n2)c(F)c1]<br>1-(2-oxabicyclo[2.1.1]hexan-1-ylmethyl)-2-(4-(6-((4-cyano-2-fluorobenzyl)oxy)pyridin-2-yl)-2,5-difluorobenzyl)-1H-benzo[d]imidazole-6-carboxylic acid: ES/MS m/z 611.5; $^{1}$H NMR (400 MHz, Methanol-d4) δ 8.51 (t, J = 0.9 Hz, 1H), 8.15 (dd, J = 8.6, 1.5 Hz, 1H), 7.90-7.77 (m, 2H), 7.77-7.67 (m, 2H), 7.65-7.55 (m, 3H), 7.32 (dd, J = 11.3, 6.0 Hz, 1H), 6.96 (d, J = 8.2 Hz, 1H), 5.64 (s, 2H), 4.94 (s, 2H), 4.74 (s, 2H), 3.76 (s, 2H), 2.98 (t, J = 3.3 Hz, 1H), 2.11-1.99 (m, 2H), 1.44 (dd, J = 4.6, 1.8 Hz, 2H). |
| 575 | 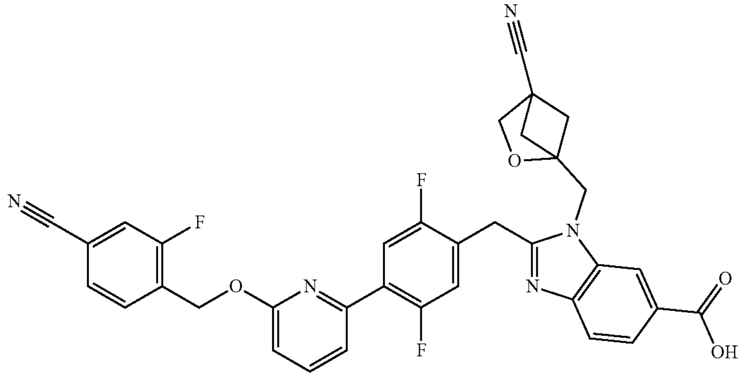 [SMILES: N#Cc1ccc(COc2cccc(-c3cc(F)c(Cc4nc5ccc(C(=O)O)cc5n4CC45CC(C#N)(CO4)C5)cc3F)n2)c(F)c1]<br>2-(4-(6-((4-cyano-2-fluorobenzyl)oxy)pyridin-2-yl)-2,5-difluorobenzyl)-1-((4-cyano-2-oxabicyclo[2.1.1]hexan-1-yl)methyl)-1H-benzo[d]imidazole-6-carboxylic acid: ES/MS m/z 636.5; $^{1}$H NMR (400 MHz, Methanol-d4) δ 8.54 (d, J = 1.3 Hz, 1H), 8.18 (dd, J = 8.6, 1.4 Hz, 1H), 7.90-7.78 (m, 2H), 7.74 (dd, J = 9.7, 8.0 Hz, 2H), 7.60 (ddd, J = 11.6, 8.9, 1.5 Hz, 3H), 7.34 (dd, J = 11.2, 6.0 Hz, 1H), 6.96 (d, J = 8.2 Hz, 1H), 5.64 (s, 2H), 5.03 (s, 2H), 4.74 (s, 2H), 3.97 (s, 2H), 2.59 (dd, J = 4.7, 1.7 Hz, 2H), 2.05-1.91 (m, 2H). |

-continued

| Example | Structure/Name/Characterization |
|---|---|
| 577 | 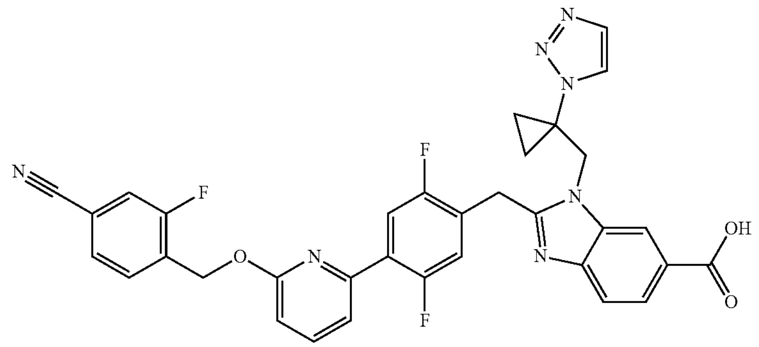 [SMILES: N#Cc1ccc(COc2cccc(-c3cc(F)c(Cc4nc5ccc(C(=O)O)cc5n4CC4(n5ccnn5)CC4)cc3F)n2)c(F)c1] 1-((1-(1H-1,2,3-triazol-1-yl)cyclopropyl)methyl)-2-(4-(6-((4-cyano-2-fluorobenzyl)oxy)pyridin-2-yl)-2,5-difluorobenzyl)-1H-benzo[d]imidazole-6-carboxylic acid: ES/MS m/z 636.4; $^1$H NMR (400 MHz, DMSO-d6) δ 8.05 (d, J = 1.5 Hz, 1H), 7.96 (d, J = 1.1 Hz, 1H), 7.94-7.85 (m, 2H), 7.82-7.64 (m, 4H), 7.64 (d, J = 1.1 Hz, 1H), 7.54 (dd, J = 11.3, 8.0 Hz, 2H), 7.21 (dd, J = 11.5, 6.1 Hz, 1H), 7.02-6.92 (m, 1H), 5.60 (s, 2H), 4.95 (s, 2H), 3.73 (s, 2H), 1.69-1.53 (m, 2H), 1.51-1.34 (m, 2H). |
| 581 | 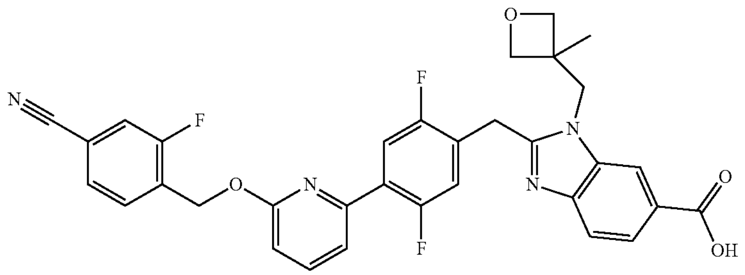 [SMILES: CC1(Cn2c(Cc3cc(F)c(-c4cccc(OCc5ccc(C#N)cc5F)n4)cc3F)nc3ccc(C(=O)O)cc32)COC1] 2-(4-(6-((4-cyano-2-fluorobenzyl)oxy)pyridin-2-yl)-2,5-difluorobenzyl)-1-((3-methyloxetan-3-yl)methyl)-1H-benzo[d]imidazole-6-carboxylic acid: ES/MS m/z 599.3; $^1$H NMR (400 MHz, Methanol-d4) δ 8.25 (d, J = 1.4 Hz, 1H), 7.99 (dd, J = 8.5, 1.5 Hz, 1H), 7.81 (t, J = 7.9 Hz, 1H), 7.78-7.70 (m, 2H), 7.67 (d, J = 8.5 Hz, 1H), 7.64-7.49 (m, 3H), 7.21 (dd, J = 11.5, 6.1 Hz, 1H), 6.92 (d, J = 8.2 Hz, 1H), 5.63 (s, 2H), 4.80 (d, J = 6.1 Hz, 2H), 4.63 (s, 2H), 4.43 (s, 2H), 4.35 (d, 2H), 1.43 (s, 3H). |

Example 33, 2-(4-(6-((4-cyano-2-fluorobenzyl)oxy)pyridin-2-yl)-2-methoxybenzyl)-1-(2-methoxyethyl)-1H-benzo[d]imidazole-6-carboxylic acid Procedure 6

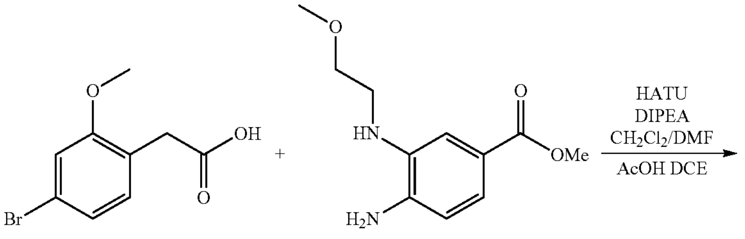

I-1

-continued

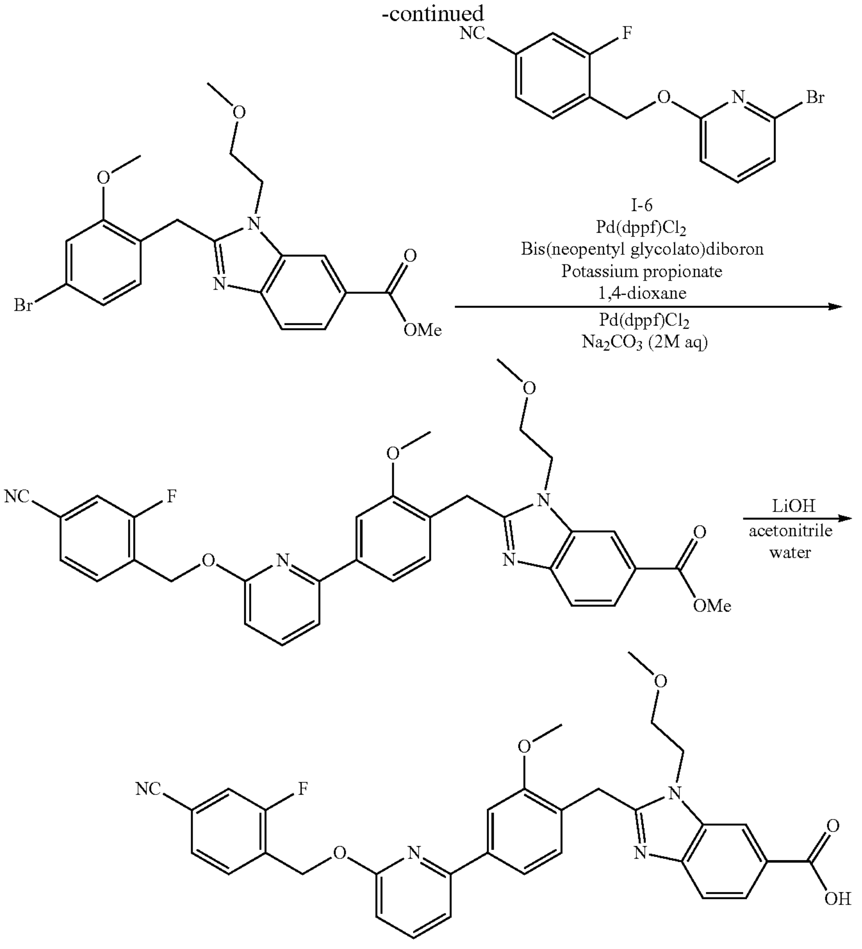

Methyl 2-(4-bromo-2-methoxybenzyl)-1-(2-methoxyethyl)-1H-benzo[d]imidazole-6-carboxylate: To a 25 mL vial was added 2-(4-bromo-2-methoxyphenyl)acetic acid (472 mg, 1.93 mmol), methyl 4-amino-3-(2-methoxyethylamino)benzoate (I-1) (360 mg, 1.61 mmol), and 2-(7-Aza-1H-benzotriazole-1-yl)-1,1,3,3-tetramethyluronium hexafluorophosphate (HATU) (453 mg, 1.93 mmol). To the vial was added $CH_2Cl_2$ (4 mL) and DMF (1 mL), and the mixture was stirred for 15 minutes at room temperature. N,N-Diisopropylethylamine (1.4 mL, 8.03 mmol) was added, and the mixture was stirred at room temperature for 4 hours, at which time LCMS showed conversion of the starting materials to the intermediate amide. The mixture was diluted with EtOAc (100 mL) and washed with sat. aq. $NH_4Cl$ (2×20 mL) and sat. aq. $NaHCO_3$ (2×20 mL). The organic layer was dried over $MgSO_4$, filtered, and concentrated under reduced pressure. The crude material was dissolved in acetic acid (2 mL) and dichloroethane (2 mL), and stirred 2 hours at 60° C. LCMS showed conversion of the intermediate amide to the desired product, and the mixture was concentrated under reduced pressure. The crude material was purified by silica gel chromatography (eluent: EtOAc/hexanes) to afford the desired product: ES/MS: 433.866 ($M+H^+$).

Methyl 2-(4-(6-((4-cyano-2-fluorobenzyl)oxy)pyridin-2-yl)-2-methoxybenzyl)-1-(2-methoxyethyl)-1H-benzo[d]imidazole-6-carboxylate: To a vial was added methyl 2-(4-bromo-2-methoxybenzyl)-1-(2-methoxyethyl)-1H-benzo[d]imidazole-6-carboxylate (353 mg, 0.815 mmol), bis(neopentyl glycolato)diboron (239 mg, 1.06 mmol), $Pd(dppf)Cl_2$ (91 mg, 0.122 mmol), and potassium propionate (274 mg, 2.44 mmol). 1,4-Dioxane (3 mL) was added, and the mixture was degassed with argon for 30 seconds. The vial was sealed, and the mixture was heated for 1 hour at 120° C. The vial was cooled, and LCMS showed conversion of the starting aryl bromide to the intermediate boronic acid. $Pd(dppf)Cl_2$ (45 mg, 0.06 mmol) and 4-[(6-bromo-2-pyridyl)oxymethyl]-3-fluoro-benzonitrile (I-6) (250 mg, 0.815 mmol) were added, and the flask was sealed and stirred 1 hour at 90° C. LCMS showed conversion to the desired product, and the flask was cooled to room temperature. The organic layer was transferred directly to a loading column, and the crude material was purified by silica gel chromatography (eluent: EtOAc/hexanes) to afford the desired product: ES/MS: 581.638 ($M+H^+$).

2-(4-(6-((4-cyano-2-fluorobenzyl)oxy)pyridin-2-yl)-2-methoxybenzyl)-1-(2-methoxyethyl)-1H-benzo[d]imidazole-6-carboxylic acid (Example 33): To a 40 mL vial was added methyl 2-(4-(6-((4-cyano-2-fluorobenzyl)oxy)pyridin-2-yl)-2-methoxybenzyl)-1-(2-methoxyethyl)-1H-benzo[d]imidazole-6-carboxylate (75 mg, 0.129 mmol), and acetonitrile (1 mL) was added. To the mixture was added LiOH (4.7 mg, 0.194 mmol) dissolved in water (0.2 mL), and the mixture was stirred overnight at room temperature. LCMS showed partial conversion to the desired product. LiOH (4.7 mg, 0.194 mmol) was added, and the mixture was stirred 5 hours at 55° C. LCMS showed conversion of the starting material to the product. The mixture was acidified with 50% citric acid (0.2 mL) and 2 drops of trifluoroacetic acid were added. The material was purified by RP-HPLC (eluent: water/MeCN*0.1% TFA) to yield the product as a trifluoroacetate salt: ES/MS: 567.566 (M+H$^+$); $^1$H NMR (400 MHz, Methanol-d4) δ 8.60 (d, J=1.3 Hz, 1H), 8.26 (dd, J=8.6, 1.4 Hz, 1H), 7.87-7.67 (m, 5H), 7.67-7.55 (m, 3H), 7.50 (d, J=7.8 Hz, 1H), 6.92 (d, J=8.2 Hz, 1H), 5.68 (s, 2H), 4.85 (t, J=5.0 Hz, 2H), 4.68 (s, 2H), 3.86 (s, 3H), 3.81 (t, J=4.9 Hz, 2H), 3.33 (s, 3H).

Examples 34-42, 170, 172, 174, 179-180, 182-183, 186, 189, 191-192, 194-199, 202, 208, 211, 213, 217, 317-322, 410-411, 522, 545-549, and 662-681. Compounds Prepared Using Procedure 6

Other compounds of the present disclosure prepared using the general route described in Procedure 6 include the following Examples.

| Example | Structure/Name/Characterization |
| --- | --- |
| 34 | 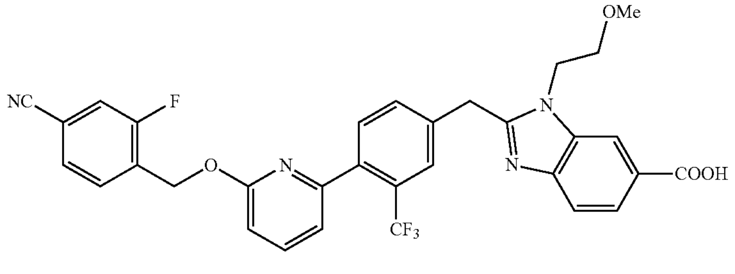 [SMILES: COCCn1c(Cc2ccc(-c3cccc(OCc4ccc(C#N)cc4F)n3)c(C(F)(F)F)c2)nc2ccc(C(=O)O)cc21]<br>2-(4-(6-((4-cyano-2-fluorobenzyl)oxy)pyridin-2-yl)-3-(trifluoromethyl)benzyl)-1-(2-methoxyethyl)-1H-benzo[d]imidazole-carboxylic acid: ES/MS m/z 605.4; $^1$H NMR (400 MHz, $CD_3OD$) δ 8. 54 (d, J = 1.1 Hz, 1H), 8.21 (dd, J = 8.6, 1.4 Hz, 1H), 7.89 (d, J = 1.8 Hz, 1H), 7.84 (dd, J = 8.4, 7.3 Hz, 1H), 7.78 (dd, J = 8.5, 0.7 Hz, 1H), 7.75-7.66 (m, 2H), 7.62-7.54 (m, 3H), 7.15 (d, J = 7.3 Hz, 1H), 6.98 (dd, J = 8.4, 0.8 Hz, 1H), 5.55 (s, 2H), 4.84-4.77 (m, 4H), 3.82 (t, J = 4.9 Hz, 2H), 3.32 (s, 3H). |
| 35 | 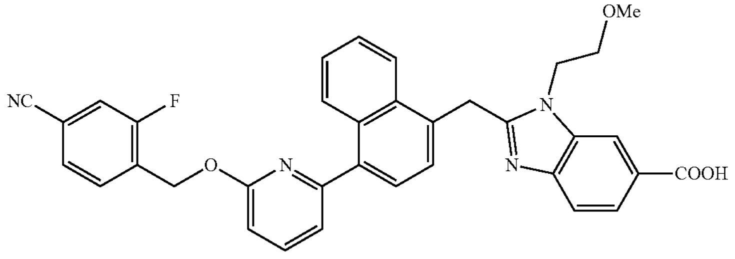 [SMILES: COCCn1c(Cc2ccc(-c3cccc(OCc4ccc(C#N)cc4F)n3)c3ccccc23)nc2ccc(C(=O)O)cc21]<br>2-((4-(6-((4-cyano-2-fluorobenzyl)oxy)pyridin-2-yl)naphthalen-1-yl)methyl)-1-(2-methoxyethyl)-1H-benzo[d]imidazole-carboxylic acid: ES/MS m/z 587.6; $^1$H NMR (400 MHz, $CD_3OD$) δ 8.62 (dd, J = 1.5, 0.7 Hz, 1H), 8.20 (dd, J = 8.6, 1.4 Hz, 1H), 8.08-8.03 (m, 1H), 8. 01 (dd, J = 8.4, 1.0 Hz, 1H), 7.94 (dd, J = 8.3, 7.3 Hz, 1H), 7.73 (t, J = 7.6 Hz, 1H), 7.67-7.54 (m, 6H), 7.43 (ddd, J = 8.2, 6.7, 1.2 Hz, 1H), 7.32 (dd, J = 7.2, 0.7 Hz, 1H), 7.05 (dd, J = 8.4, 0.7 Hz, 1H), 5.59 (s, 2H), 5.22 (s, 2H), 4.94 (t, J = 5.0 Hz, 2H), 4.00-3.91 (m, 2H), 3.45 (s, 3H). |
| 36 | 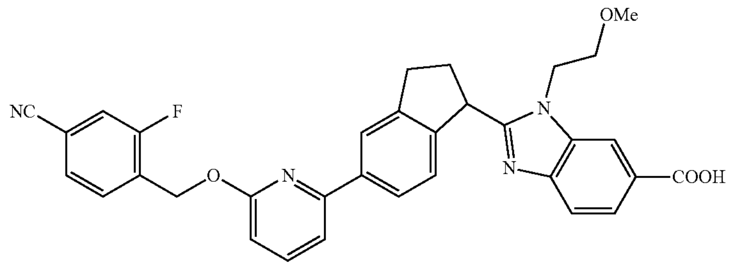 [SMILES: COCCn1c(C2CCc3cc(-c4cccc(OCc5ccc(C#N)cc5F)n4)ccc32)nc2ccc(C(=O)O)cc21]<br>2-(5-(6-((4-cyano-2-fluorobenzyl)oxy)pyridin-2-yl)-2,3-dihydro-1H-inden-1-yl)-1-(2-methoxyethyl)-1H-benzo[d]imidazole-carboxylic acid: ES/MS m/z 563.6; $^1$H NMR (400 MHz, $CD_3OD$) δ 8.66 (d, J = 1.3 Hz, 1H), 8.28 (dd, J = 8.6, 1.4 Hz, 1H), 8.07 (d, J = 1.5 Hz, 1H), 7.93 (dd, J = 8.0, 1.6 Hz, 1H), 7.85-7.70 (m, 3H), 7.66-7.51 (m, 3H), 7. 24 (d, J = 8.0 Hz, 1H), 6.89 (d, J = 8.2 Hz, 1H), 5.66 (s, 2H), 5.39 (t, J = 8.4 Hz, 1H), 5.00 (t, J = 4.9 Hz, 2H), 3.92 (t, J = 4.9 Hz, 2H), 3.39 (s, 3H), 3.32-3.19 (m, 2H), 2.96 (dtd, J = 12.4, 8.1, 3.9 Hz, 1H), 2.43 (dq, J = 13.0, 8.7 Hz, 1H). |

-continued

| Example | Structure/Name/Characterization |
|---|---|
| 37 | 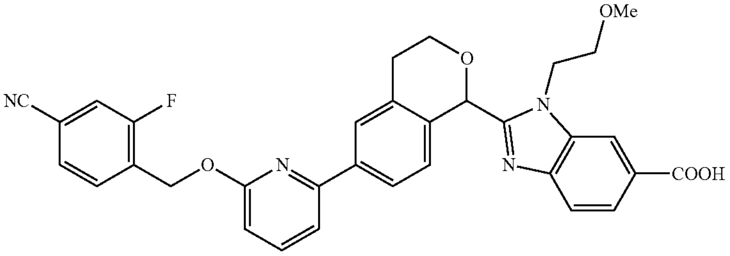 [SMILES: COCCn1c(C2OCCc3cc(-c4cccc(OCc5ccc(C#N)cc5F)n4)ccc32)nc2ccc(C(=O)O)cc21]<br>2-(6-(6-((4-cyano-2-fluorobenzyl)oxy)pyridin-2-yl)isochroman-1-yl)-1-(2-methoxyethyl)-1H-benzo[d]imidazole-carboxylic acid: ES/MS m/z 579.5; $^1$H NMR (400 MHz, $CD_3OD$) δ 8.54 (d, J = 1.4 Hz, 1H), 8.17 (dd, J = 8.6, 1.5 Hz, 1H), 7.98 (d, J = 1.8 Hz, 1H), 7.87 (dd, J = 8.2, 1.8 Hz, 1H), 7.84-7.68 (m, 3H), 7.68-7.50 (m, 3H), 7.06 (d, J = 8.2 Hz, 1H), 6.88 (d, J = 8.2 Hz, 1H), 6.61 (s, 1H), 5.65 (s, 2H), 4.86-4.76 (m, 2H), 4.27-4.16 (m, 1H), 4.12 (td, J = 7.3, 3.9 Hz, 1H), 3.80 (dt, J = 10.4, 4.3 Hz, 1H), 3.71 (td, J = 7.2, 6.6, 3.8 Hz, 1H), 3.30 (s, 3H), 3.26-3.04 (m, 2H). |
| 38 | 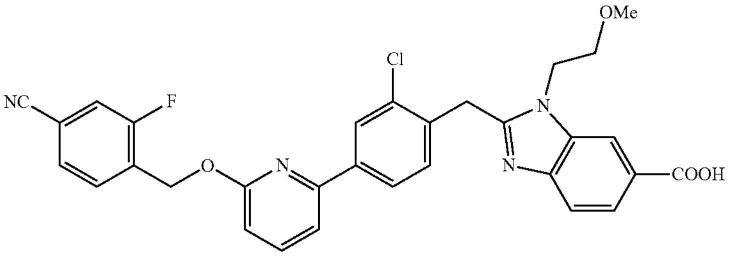 [SMILES: COCCn1c(Cc2ccc(-c3cccc(OCc4ccc(C#N)cc4F)n3)cc2Cl)nc2ccc(C(=O)O)cc21]<br>2-(2-chloro-4-(6-((4-cyano-2-fluorobenzyl)oxy)pyridin-2-yl)benzyl)-1-(2-methoxyethyl)-1H-benzo[d]imidazole-carboxylic acid: ES/MS m/z 571.7; $^1$H NMR (400 MHz, $CD_3OD$) δ 8.60 (s, 1H), 8.25 (d, J = 8.6 Hz, 1H), 8.18 (d, J = 1.7 Hz, 1H), 8.06 (d, J = 8.1 Hz, 1H), 7.84 (t, J = 7.9 Hz, 1H), 7.80-7.69 (m, 2H), 7.68-7.52 (m, 4H), 6.95 (d, J = 8.2 Hz, 1H), 5.66 (s, 2H), 4.92-4.81 (m, 4H), 3.87 (t, J = 4.9 Hz, 2H), 3.35 (s, 3H). |
| 39 | 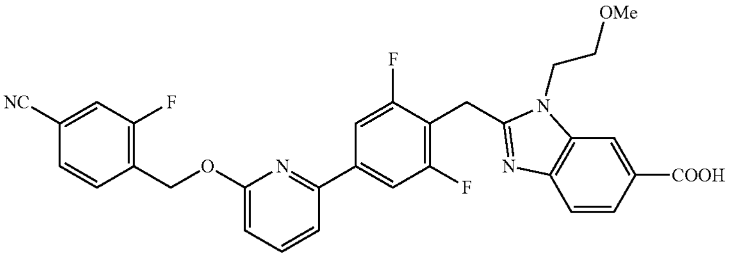 [SMILES: COCCn1c(Cc2c(F)cc(-c3cccc(OCc4ccc(C#N)cc4F)n3)cc2F)nc2ccc(C(=O)O)cc21]<br>2-(4-(6-((4-cyano-2-fluorobenzyl)oxy)pyridin-2-yl)-2,6-difluorobenzyl)-1-(2-methoxyethyl)-1H-benzo[d]imidazole-carboxylic acid: ES/MS m/z 573.6; $^1$H NMR (400 MHz, $CD_3OD$) δ 8.52 (dd, J = 1.5, 0.7 Hz, 1H), 8.19 (dd, J = 8.6, 1.5 Hz, 1H), 7.89-7.70 (m, 5H), 7.67-7.56 (m, 3H), 6.99-6.94 (m, 1H), 5.66 (s, 2H), 4.82 (t, J = 5.0 Hz, 2H), 4.77 (s, 2H), 3.87-3.78 (m, 2H), 3.34 (s, 3H). |
| 40 | 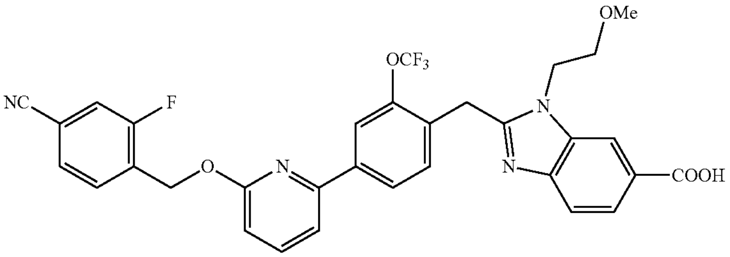<br>2-(4-(6-((4-cyano-2-fluorobenzyl)oxy)pyridin-2-yl)-2-(trifluoromethoxy)benzyl)-1-(2-methoxyethyl)-1H-benzo[d]imidazole-6-carboxylic acid: ES/MS m/z 621.5; $^1$H NMR (400 MHz, $CD_3OD$) δ 8.54 |

-continued

| Example | Structure/Name/Characterization |
| --- | --- |
| | 1H), 8.21 (dd, J = 8.6, 1.5 Hz, 1H), 8.13-8.01 (m, 2H), 7.85 (t, J = 7.9 Hz, 1H), 7.76 (d, J = 8.6 Hz, 1H), 7.71 (t, J = 7.6 Hz, 1H), 7.65-7.52 (m, 4H), 6.96 (d, J = 8.2 Hz, 1H), 5.67 (s, 2H), 4.80-4.75 (m, 4H), 3.80 (t, J = 4.9 Hz, 2H), 3.31 (s, 3H). |
| 41 | 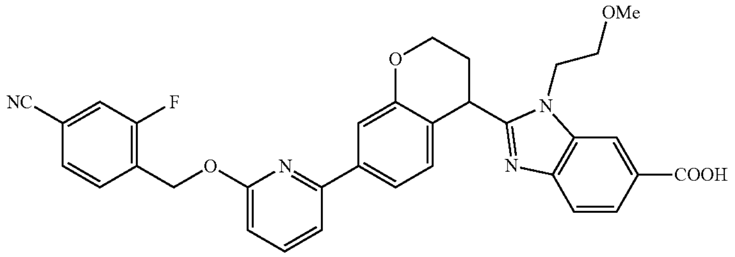 [SMILES: COCCn1c(C2CCOc3cc(-c4cccc(OCc5ccc(C#N)cc5F)n4)ccc32)nc2ccc(C(=O)O)cc21] 2-(7-(6-((4-cyano-2-fluorobenzyl)oxy)pyridin-2-yl)chroman-4-yl)-1-(2-methoxyethyl)-1H-benzo[d]imidazole-carboxylic acid:ES/MS m/z 579.5; $^{1}$H NMR (400 MHz, $CD_3OD$) δ 8.60 (t, J = 1.0 Hz, 1H), 8.23 (dd, J = 8.6, 1.4 Hz, 1H), 7.84-7.69 (m, 3H), 7.66-7.47 (m, 5H), 7.04-6.92 (m, 1H), 6.87 (d, J = 8.2 Hz, 1H), 5.64 (s, 2H), 5.26 (t, J = 7.0 Hz, 1H), 4.95 (dd, J = 5.9, 3.9 Hz, 2H), 4.51-4.30 (m, 2H), 3.99-3.82 (m, 2H), 3.39 (s, 3H), 2.60 (ddt, J = 12.9, 6.5, 3.2 Hz, 1H), 2.41 (dtd, J = 13.8, 8.0, 3.3 Hz, 1H). |
| 42 | 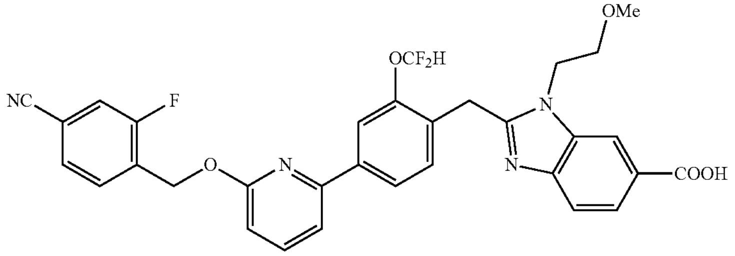 2-(4-(6-((4-cyano-2-fluorobenzyl)oxy)pyridin-2-yl)-2-(difluoromethoxy)benzyl)-1-(2-methoxyethyl)-1H-benzo[d]imidazole-6-carboxylic acid: ES/MS m/z 603.4; $^{1}$H NMR (400 MHz, $CD_3OD$) δ 8.55-8.51 (m, 1H), 8.20 (dd, J = 8.6, 1.4 Hz, 1H), 7.95 (d, J = 7.4 Hz, 2H), 7.87-7.81 (m, 1H), 7.79-7.67 (m, 2H), 7.65-7.50 (m, 4H), 7.18-6.78 (m, 2H), 5.67 (s, 2H), 4.77 (t, J = 5.0 Hz, 2H), 4.73 (s, 2H), 3.81 (t, J = 4.9 Hz, 2H), 3.32 (s, 3H). |
| 170 | 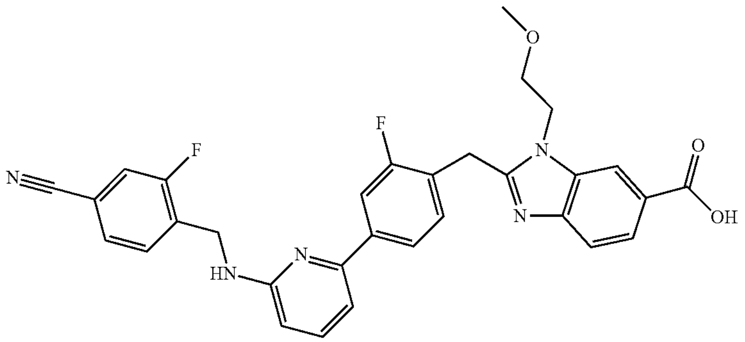 [SMILES: COCCn1c(Cc2ccc(-c3cccc(NCc4ccc(C#N)cc4F)n3)cc2F)nc2ccc(C(=O)O)cc21] 2-(4-(6-((4-cyano-2-fluorobenzyl)amino)pyridin-2-yl)-2-fluorobenzyl)-1-(2-methoxyethyl)-1H-benzo[d]imidazole-carboxylic acid: ES/MS m/z 554.4; $^{1}$H NMR (400 MHz, Acetonitrile-d3) δ 8.42 (d, J = 1.4 Hz, 1H), 8.11 (dd, J = 8.6, 1.5 Hz, 1H), 7.94-7.76 (m, 4H), 7.66 (t, J = 7.8 Hz, 1H), 7.61-7.54 (m, 3H), 7.19 (dd, J = 7.5, 0.8 Hz, 1H), 6.85 (d, J = 8.8 Hz, 1H), 4.73 (d, J = 29.8 Hz, 4H), 4.63 (t, J = 5.0 Hz, 2H), 3.75 (t, J = 4.9 Hz, 2H), 3.25 (s, 3H). |

-continued

| Example | Structure/Name/Characterization |
|---|---|
| 172 | 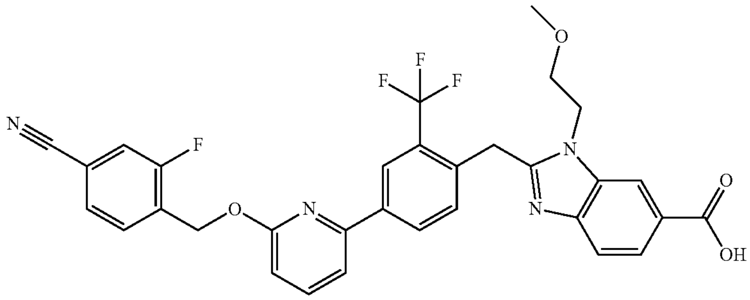 [SMILES: COCCn1c(Cc2ccc(-c3cccc(OCc4ccc(C#N)cc4F)n3)cc2C(F)(F)F)nc2ccc(C(=O)O)cc21] 2-(4-(6-((4-cyano-2-fluorobenzyl)oxy)pyridin-2-yl)-2-(trifluoromethyl)benzyl)-1-(2-methoxyethyl)-1H-benzo[d]imidazole-carboxylic acid: ES/MS m/z 605.2; $^{1}$H NMR (400 MHz, Acetonitrile-d3) δ 8.48-8.41 (m, 2H), 8.27 (d, J = 8.1 Hz, 1H), 8.11 (dd, J = 8.6, 1.5 Hz, 1H), 7.86 (t, J = 7.9 Hz, 1H), 7.73 (t, J = 8.3 Hz, 2H), 7.65-7.56 (m, 3H), 7.49 (d, J = 8.1 Hz, 1H), 6.95 (d, J = 8.2 Hz, 1H), 5.67 (s, 2H), 4.82 (s, 2H), 4.62 (t, J = 5.0 Hz, 2H), 3.78 (t, J = 4.9 Hz, 2H), 3.28 (s, 3H). |
| 174 | 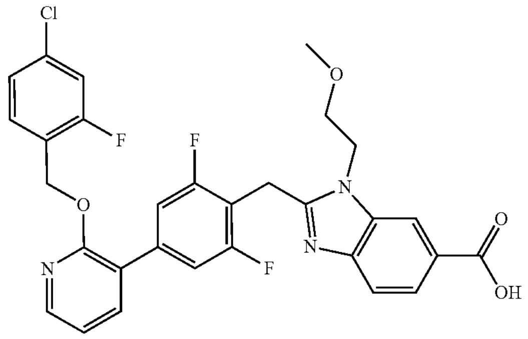 [SMILES: COCCn1c(Cc2c(F)cc(-c3cccnc3OCc3ccc(Cl)cc3F)cc2F)nc2ccc(C(=O)O)cc21] 2-(4-(2-((4-chloro-2-fluorobenzyl)oxy)pyridin-3-yl)-2,6-difluorobenzyl)-1-(2-methoxyethyl)-1H-benzo[d]imidazole-carboxylic acid: ES/MS m/z 582.2; 1H NMR (400 MHz, Acetonitrile-d3) δ 8.40 (s, 1H), 8.24 (dd, J = 5.0, 2.0 Hz, 1H), 8.16-8.06 (m, 1H), 7.79 (dd, J = 21.3, 7.7 Hz, 2H), 7.51 (t, J = 8.1 Hz, 1H), 7.36 (d, J = 9.2 Hz, 2H), 7.25 (ddd, J = 18.1, 9.1, 2.1 Hz, 1H), 7.18-7.01 (m, 1H), 5.50 (s, 2H), 4.72-4.55 (m, 5H), 3.77 (t, J = 4.9 Hz, 2H), 3.25 (s, 3H). |
| 177 | 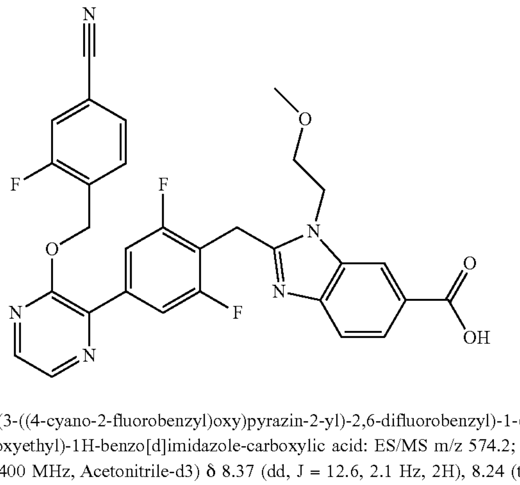 2-(4-(3-((4-cyano-2-fluorobenzyl)oxy)pyrazin-2-yl)-2,6-difluorobenzyl)-1-(2-methoxyethyl)-1H-benzo[d]imidazole-carboxylic acid: ES/MS m/z 574.2; $^{1}$H NMR (400 MHz, Acetonitrile-d3) δ 8.37 (dd, J = 12.6, 2.1 Hz, 2H), 8.24 (t, J = 2.8 Hz, 1H), 8.08 (dd, J = 8.6, 1.6 Hz, 1H), 7.79 (d, J = 8.6 Hz, 1H), 7.70-7.51 (m, 3H), 7.43 (dd, J = 9.8, 5.8 Hz, 1H), 7.28 (dd, J = 10.1, 6.0 Hz, 1H), 5.57 (d, J = 2.5 Hz, 2H), 4.61 (d, J = 6.8 Hz, 4H), 3.75 (t, J = 5.1 Hz, 2H), 3.23 (d, J = 4.1 Hz, 3H). |

-continued

| Example | Structure/Name/Characterization |
|---|---|
| 179 | 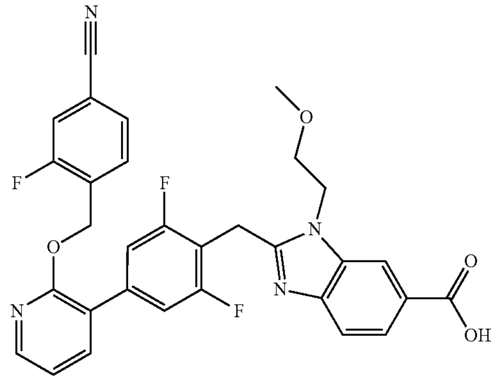 [SMILES: COCCn1c(Cc2c(F)cc(-c3cccnc3OCc3ccc(C#N)cc3F)cc2F)nc2ccc(C(=O)O)cc21]<br>2-(4-(2-((4-cyano-2-fluorobenzyl)oxy)pyridin-3-yl)-2,6-difluorobenzyl)-1-(2-methoxyethyl)-1H-benzo[d]imidazole-carboxylic acid: ES/MS m/z 573.3; $^1$H NMR (400 MHz, Acetonitrile-d3) δ 8.27 (d, J = 1.6 Hz, 1H), 8.21 (dd, J = 4.9, 1.9 Hz, 1H), 7.94 (dd, J = 8.5, 1.5 Hz, 1H), 7.86 (dd, J = 7.4, 1.9 Hz, 1H), 7.69-7.61 (m, 2H), 7.61-7.52 (m, 2H), 7.35 (d, J = 8.6 Hz, 2H), 7.15 (dd, J = 7.4, 4.9 Hz, 1H), 5.60 (s, 2H), 4.58 (t, J = 5.1 Hz, 2H), 4.50 (s, 3H), 3.77 (t, J = 5.0 Hz, 2H), 3.28 (s, 3H). |
| 180 | 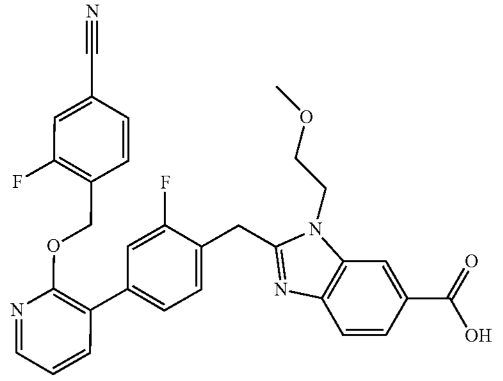 [SMILES: COCCn1c(Cc2ccc(-c3cccnc3OCc3ccc(C#N)cc3F)cc2F)nc2ccc(C(=O)O)cc21]<br>2-(4-(2-((4-cyano-2-fluorobenzyl)oxy)pyridin-3-yl)-2-fluorobenzyl)-1-(2-methoxyethyl)-1H-benzo[d]imidazole-carboxylic acid: ES/MS m/z 555.5; $^1$H NMR (400 MHz, Acetonitrile-d3) δ 8.35-8.33 (m, 1H), 8.19 (dd, J = 4.9, 1.9 Hz, 1H), 8.04 (dd, J = 8.5, 1.5 Hz, 1H), 7.78 (dd, J = 14.2, 7.9 Hz, 2H), 7.63 (t, J = 7.7 Hz, 1H), 7.58-7.52 (m, 2H), 7.50-7.38 (m, 3H), 7.13 (dd, J = 7.4, 5.0 Hz, 1H), 5.57 (s, 2H), 4.61-4.54 (m, 4H), 3.72 (t, J = 5.0 Hz, 2H), 3.23 (s, 3H). |
| 182 | 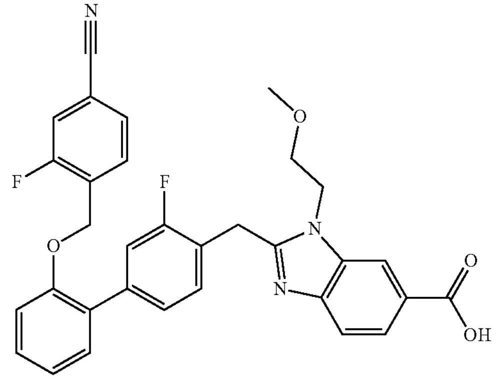 [SMILES: COCCn1c(Cc2ccc(-c3ccccc3OCc3ccc(C#N)cc3F)cc2F)nc2ccc(C(=O)O)cc21]<br>2-((2'-((4-cyano-2-fluorobenzyl)oxy)-3-fluoro-[1,1'-biphenyl]-4-yl)methyl)-1-(2-methoxyethyl)-1H-benzo[d]imidazole-carboxylic acid: ES/MS m/z 554.3; $^1$H NMR (400 MHz, Acetonitrile-d3) δ 8.30 (s, 1H), 8.00 (dd, J = 8.5, 1.5 Hz, 1H), 7.72 (d, J = 8.5 Hz, 1H), 7.60-7.49 (m, 3H), 7.45-7.34 (m, 5H), 7.24- |

-continued

| Example | Structure/Name/Characterization |
| --- | --- |
| | 7.18 (m, 1H), 7.13 (td, J = 7.5, 1.0 Hz, 1H), 5.25 (s, 2H), 4.55 (t, J = 5.1 Hz, 2H), 4.52 (s, 2H), 3.71 (t, J = 5.1 Hz, 2H), 3.24 (s, 3H). |
| 183 | 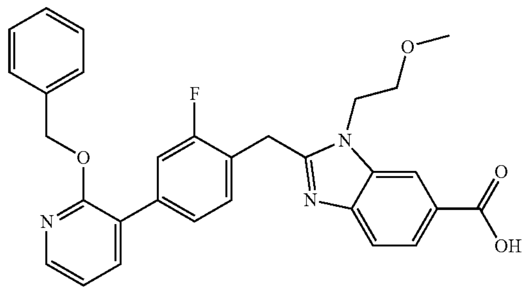 [SMILES: COCCn1c(Cc2ccc(-c3cccnc3OCc3ccccc3)cc2F)nc2ccc(C(=O)O)cc21] 2-(4-(2-(benzyloxy)pyridin-3-yl)-2-fluorobenzyl)-1-(2-methoxyethyl)-1H-benzo[d]imidazole-carboxylic acid: ES/MS m/z 512.5; $^1$H NMR (400 MHz, Acetonitrile-d3) δ 8.38 (d, J = 1.4 Hz, 1H), 8.19 (dd, J = 5.0, 1.8 Hz, 1H), 8.08 (dd, J = 8.5, 1.4 Hz, 1H), 7.77 (d, J = 8.6 Hz, 1H), 7.70 (dd, J = 7.4, 1.9 Hz, 1H), 7.50-7.40 (m, 5H), 7.39-7.29 (m, 3H), 7.07 (dd, J = 7.4, 4.9 Hz, 1H), 5.45 (s, 2H), 4.62 (s, 2H), 4.60 (t, J = 5.0 Hz, 2H), 3.70 (t, J = 5.0 Hz, 2H), 3.21 (s, 3H). |
| 186 | 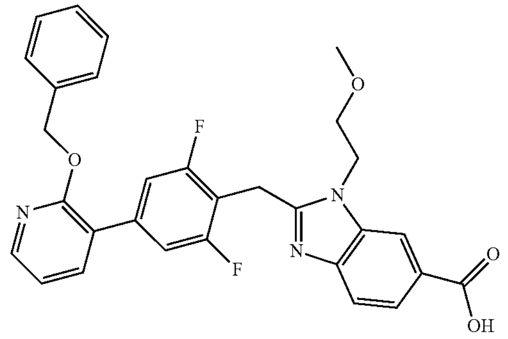 [SMILES: COCCn1c(Cc2c(F)cc(-c3cccnc3OCc3ccccc3)cc2F)nc2ccc(C(=O)O)cc21] 2-(4-(2-(benzyloxy)pyridin-3-yl)-2,6-difluorobenzyl)-1-(2-methoxyethyl)-1H-benzo[d]imidazole-carboxylic acid: ES/MS m/z 530.5; $^1$H NMR (400 MHz, Acetonitrile-d3) δ 8.36 (d, J = 1.6 Hz, 1H), 8.23 (dd, J = 4.9, 1.9 Hz, 1H), 8.05 (dd, J = 8.6, 1.5 Hz, 1H), 7.78 (dd, J = 7.4, 1.9 Hz, 1H), 7.71 (d, J = 8.6 Hz, 1H), 7.49-7.44 (m, 2H), 7.42-7.32 (m, 5H), 7.10 (dd, J = 7.4, 5.0 Hz, 1H), 5.48 (s, 2H), 4.65-4.58 (m, 4H), 3.76 (t, J = 5.0 Hz, 2H), 3.25 (s, 3H). |
| 189 | 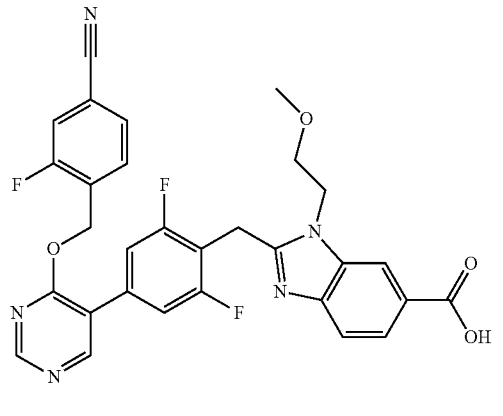 [SMILES: COCCn1c(Cc2c(F)cc(-c3cncnc3OCc3ccc(C#N)cc3F)cc2F)nc2ccc(C(=O)O)cc21] 2-(4-(4-((4-cyano-2-fluorobenzyl)oxy)pyrimidin-5-yl)-2,6-difluorobenzyl)-1-(2-methoxyethyl)-1H-benzo[d]imidazole-carboxylic acid: ES/MS m/z 574.2; $^1$H NMR (400 MHz, Acetonitrile-d3) δ 8.83 (d, J = 3.9 Hz, 1H), 8.58 (d, J = 4.1 Hz, 1H), 8.40 (s, 1H), 8.10 (d, J = 8.5 Hz, 1H), 7.82 (d, J = 8.5 Hz, 1H), 7.64-7.51 (m, 3H), 7.33 (ddd, J = 23.2, 10.0, 5.9 Hz, 2H), 5.62 (s, 1H), 4.62 (d, J = 5.5 Hz, 4H), 3.75 (d, J = 4.9 Hz, 2H), 3.22 (d, J = 3.7 Hz, 3H). |

-continued

| Example | Structure/Name/Characterization |
|---|---|
| 191 | 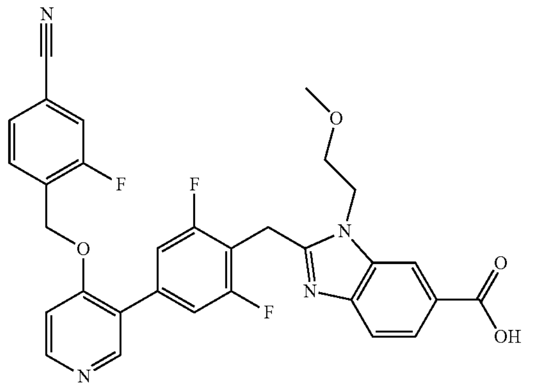 [SMILES: COCCn1c(Cc2c(F)cc(-c3cnccc3OCc3ccc(C#N)cc3F)cc2F)nc2ccc(C(=O)O)cc21] 2-(4-(4-((4-cyano-2-fluorobenzyl)oxy)pyridin-3-yl)-2,6-difluorobenzyl)-1-(2-methoxyethyl)-1H-benzo[d]imidazole-carboxylic acid: ES/MS m/z 573.2; $^1$H NMR (400 MHz, Acetonitrile-d3) δ 8.74 (d, J = 6.6 Hz, 1H), 8.67 (s, 1H), 8.33 (s, 1H), 8.01 (d, J = 8.6 Hz, 1H), 7.75-7.56 (m, 5H), 7.32 (d, J = 8.4 Hz, 2H), 5.54 (s, 2H), 4.61 (d, J = 4.3 Hz, 2H), 4.58 (s, 2H), 3.78 (t, J = 4.7 Hz, 3H), 3.26 (s, 3H). |
| 192 | 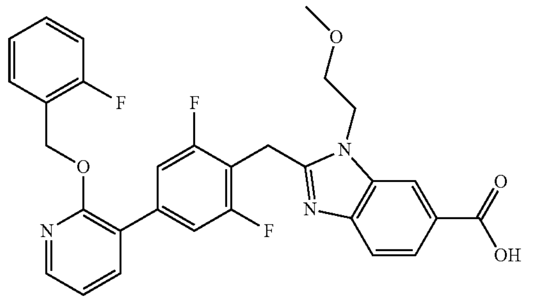 [SMILES: COCCn1c(Cc2c(F)cc(-c3cccnc3OCc3ccccc3F)cc2F)nc2ccc(C(=O)O)cc21] 2-(2,6-difluoro-4-(2-((2-fluorobenzyl)oxy)pyridin-3-yl)benzyl)-1-(2-methoxyethyl)-1H-benzo[d]imidazole-carboxylic acid: ES/MS m/z 548.2; $^1$H NMR (400 MHz, Acetonitrile-d3) δ 8.36-8.29 (m, 1H), 8.24 (dd, J = 4.9, 2.0 Hz, 1H), 8.03-7.96 (m, 1H), 7.88-7.80 (m, 1H), 7.67 (d, J = 8.5 Hz, 1H), 7.53 (dt, J = 7.6, 3.9 Hz, 1H), 7.44-7.31 (m, 3H), 7.25-7.11 (m, 3H), 5.54 (s, 2H), 4.59 (t, J = 5.0 Hz, 2H), 4.53 (d, J = 4.3 Hz, 2H), 3.76 (t, J = 5.0 Hz, 2H), 3.26 (s, 2H). |
| 194 | 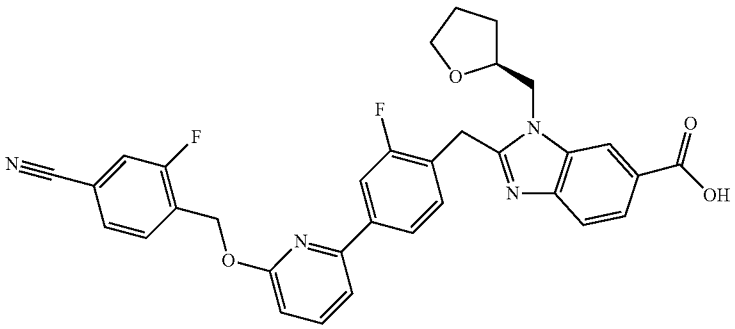 (S)-2-(4-(6-((4-cyano-2-fluorobenzyl)oxy)pyridin-2-yl)-2-fluorobenzyl)-1-((tetrahydrofuran-2-yl)methyl)-1H-benzo[d]imidazole-carboxylic acid: ES/MS m/z 581.5; $^1$H NMR (400 MHz, Acetonitrile-d3) δ 8.52 (d, J = 3.2 Hz, 1H), 8.17 (dd, J = 8.5, 3.0 Hz, 1H), 8.02-7.77 (m, 4H), 7.73 (t, J = 7.5 Hz, 1H), 7.64-7.45 (m, 4H), 6.91 (d, J = 8.2 Hz, 1H), 5.64 (s, 2H), 4.74 (s, 2H), 4.68 (dd, J = 15.1, 2.6 Hz, 1H), 4.47 (dd, J = 15.0, 8.7 Hz, 1H), 4.37-4.19 (m, 1H), 3.89 (q, J = 7.0 Hz, 1H), 3.81-3.64 (m, 1H), 2.32-2.13 (m, 1H), 1.74 (dt, J = 12.1, 7.6 Hz, 1H). |

-continued

| Example | Structure/Name/Characterization |
|---|---|
| 195 | 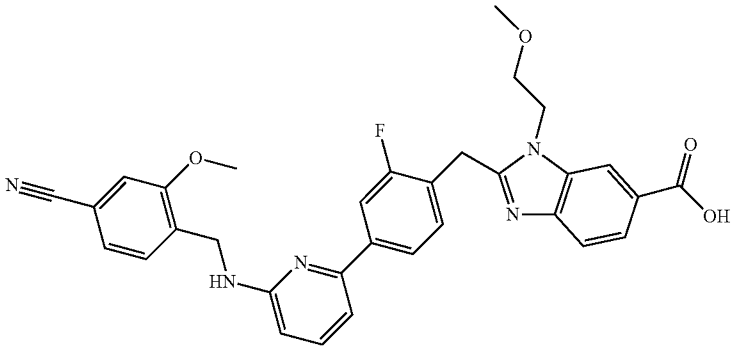 [SMILES: COCCn1c(Cc2ccc(-c3cccc(NCc4ccc(C#N)cc4OC)n3)cc2F)nc2ccc(C(=O)O)cc21]<br>2-(4-(6-((4-cyano-2-methoxybenzyl)amino)pyridin-2-yl-2-fluorobenzyl)-1-(2-methoxyethyl)-1H-benzo[d]imidazole-carboxylic acid: ES/MS m/z 566.4; $^1$H NMR (400 MHz, Acetonitrile-d3) δ 8.34 (d, J = 1.5 Hz, 1H), 8.03 (dd, J = 8.5, 1.5 Hz, 1H), 7.78-7.67 (m, 4H), 7.53-7.42 (m, 2H), 7.34 (d, J = 1.4 Hz, 1H), 7.30 (dd, J = 7.8, 1.5 Hz, 1H), 7.10 (d, J = 7.4 Hz, 1H), 6.73 (d, J = 8.7 Hz, 1H), 4.65 (s, 2H), 4.61-4.51 (m, 4H), 3.94 (s, 3H), 3.73 (t, J = 5.0 Hz, 2H), 3.25 (s, 3H). |
| 196 | 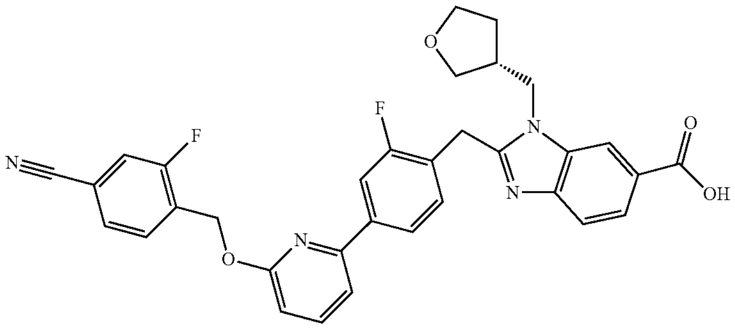 [SMILES: N#Cc1ccc(COc2cccc(-c3ccc(Cc4nc5ccc(C(=O)O)cc5n4C[C@H]4CCOC4)c(F)c3)n2)c(F)c1]<br>(R)-2-(4-(6-((4-cyano-2-fluorobenzyl)oxy)pyridin-2-yl)-2-fluorobenzyl)-1-((tetrahydrofuran-3-yl)methyl)-1H-benzo[d]imidazole-carboxylic acid: ES/MS m/z 581.2; $^1$H NMR (400 MHz, Acetonitrile-d3) δ 8.50-8.42 (m, 1H), 8.16 (dd, J = 8.6, 1.4 Hz, 1H), 7.92-7.86 (m, 3H), 7.86-7.79 (m, 2H), 7.76-7.69 (m, 1H), 7.63-7.49 (m, 5H), 6.91 (d, J = 8.3 Hz, 1H), 5.65 (s, 2H), 4.67 (s, 2H), 4.46 (d, J = 8.1 Hz, 2H), 3.98 (td, J = 8.4, 5.5 Hz, 1H), 3.74 (td, J = 8.3, 6.6 Hz, 1H), 3.67 (dd, J = 9.1, 6.2 Hz, 1H), 3.55 (dd, J = 9.1, 4.8 Hz, 1H), 2.89 (td, J = 11.3, 5.4 Hz, 1H). |
| 197 | 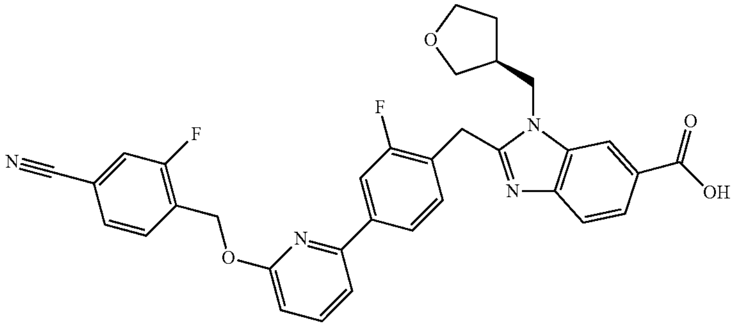 [SMILES: N#Cc1ccc(COc2cccc(-c3ccc(Cc4nc5ccc(C(=O)O)cc5n4C[C@@H]4CCOC4)c(F)c3)n2)c(F)c1]<br>(S)-2-(4-(6-((4-cyano-2-fluorobenzyl)oxy)pyridin-2-yl)-2-fluorobenzyl)-1-((tetrahydrofuran-3-yl)methyl)-1H-benzo[d]imidazole-carboxylic acid: ES/MS m/z 581.3; $^1$H NMR (400 MHz, Acetonitrile-d3) δ 8.44 (dd, J = 1.5, 0.7 Hz, 1H), 8.14 (dd, J = 8.6, 1.5 Hz, 1H), 7.91-7.78 (m, 4H), 7.73 (t, J = 7.7 Hz, 1H), 7.63-7.46 (m, 5H), 6.91 (dd, J = 8.3, 0.6 Hz, 1H), 5.65 (s, 2H), 4.65 (s, 2H), 4.45 (d, J = 8.1 Hz, 2H), 3.98 (td, J = 8.3, 5.5 Hz, 1H), 3.74 (td, J = 8.3, 6.6 Hz, 1H), 3.67 (dd, J = 9.1, 6.2 Hz, 1H), 3.55 (dd, J = 9.1, 4.8 Hz, 1H). |

-continued

| Example | Structure/Name/Characterization |
|---|---|
| 198 | 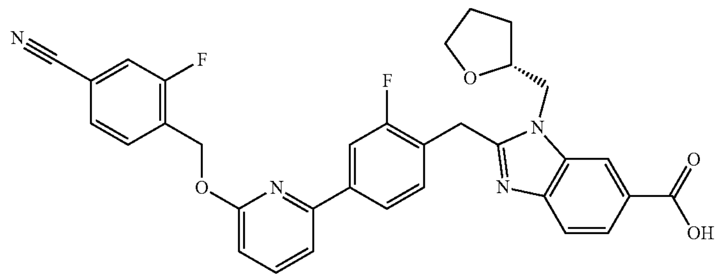 [SMILES: N#Cc1ccc(COc2cccc(-c3ccc(Cc4nc5ccc(C(=O)O)cc5n4C[C@H]4CCCO4)c(F)c3)n2)c(F)c1] (R)-2-(4-(6-((4-cyano-2-fluorobenzyl)oxy)pyridin-2-yl)-2-fluorobenzyl)-1-((tetrahydrofuran-2-yl)methyl)-1H-benzo[d]imidazole-carboxylic acid: ES/MS m/z 581.3; $^1$H NMR (400 MHz, Acetonitrile-d3) δ 8.46 (d, J = 1.3 Hz, 1H), 8.12 (dd, J = 8.3, 1.2 Hz, 1H), 7.89-7.76 (m, 4H), 7.73 (t, J = 7.6 Hz, 1H), 7.61-7.56 (m, 2H), 7.50 (dd, J = 15.8, 7.7 Hz, 2H), 6.90 (d, J = 8.2 Hz, 1H), 5.64 (s, 2H), 4.70 (s, 2H), 4.63 (dd, J = 15.1, 2.6 Hz, 1H), 4.43 (dd, J = 15.1, 8.8 Hz, 1H), 4.25 (q, J = 7.2 Hz, 1H), 3.88 (dt, J = 8.4, 6.8 Hz, 1H), 3.71 (q, J = 7.3 Hz, 1H), 2.18 (dt, J = 12.9, 6.6 Hz, 1H), 1.93-1.88 (m, 1H), 1.76-1.66 (m, 1H). |
| 199 | 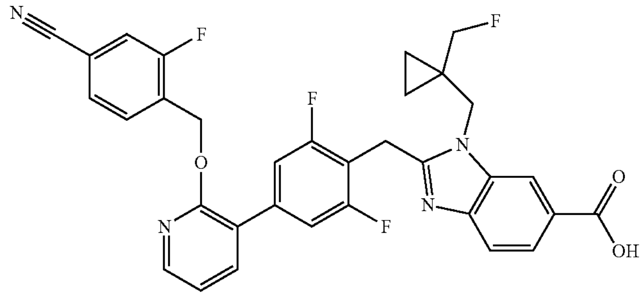 [SMILES: N#Cc1ccc(COc2ncccc2-c2cc(F)c(Cc3nc4ccc(C(=O)O)cc4n3CC3(CF)CC3)c(F)c2)c(F)c1] 2-(4-(2-((4-cyano-2-fluorobenzyl)oxy)pyridin-3-yl)-2,6-difluorobenzyl)-1-((1-(fluoromethyl)cyclopropyl)methyl)-1H-benzo[d]imidazole-carboxylic acid: ES/MS m/z 601.2; $^1$H NMR (400 MHz, Acetonitrile-d3) δ 8.46 (s, 1H), 8.23 (s, 1H), 8.17-8.04 (m, 1H), 7.95-7.72 (m, 2H), 7.65 (s, 1H), 7.56 (s, 3H), 7.44-7.35 (m, 3H), 7.16 (d, J = 7.2 Hz, 1H), 5.60 (s, 2H), 4.62 (s, 3H), 4.22 (d, J = 48.6 Hz, 2H), 0.92 (d, J = 42.3 Hz, 4H). |
| 202 | 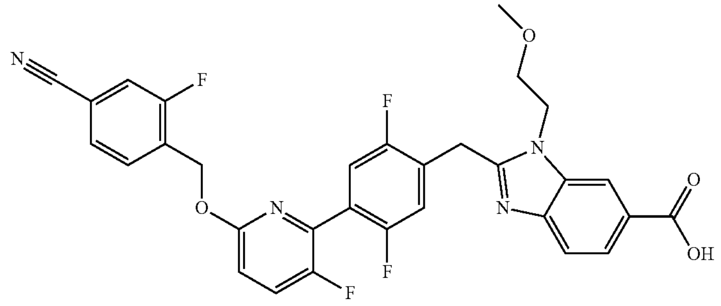 [SMILES: COCCn1c(Cc2cc(F)c(-c3nc(OCc4ccc(C#N)cc4F)ccc3F)cc2F)nc2ccc(C(=O)O)cc21] 2-(4-(6-((4-cyano-2-fluorobenzyl)oxy)-3-fluoropyridin-2-yl)-2,5-difluorobenzyl)-1-(2-methoxyethyl)-1H-benzo[d]imidazole-carboxylic acid: ES/MS m/z 591.3; $^1$H NMR (400 MHz, MeOD) δ 8.54 (d, J = 1.4 Hz, 1H), 8.21 (dd, J = 8.6, 1.4 Hz, 1H), 7.78 (d, J = 8.6 Hz, 1H), 7.76-7.66 (m, 2H), 7.64-7.55 (m, 2H), 7.39 (ddd, J = 14.0, 9.8, 5.8 Hz, 2H), 7.04 (dd, J = 8.9, 2.9 Hz, 1H), 5.55 (s, 2H), 4.81 (t, J = 4.9 Hz, 2H), 4.77 (s, 2H), 3.84 (t, J = 4.9 Hz, 2H), 3.32 (s, 3H). |

-continued

| Example | Structure/Name/Characterization |
|---|---|
| 208 | 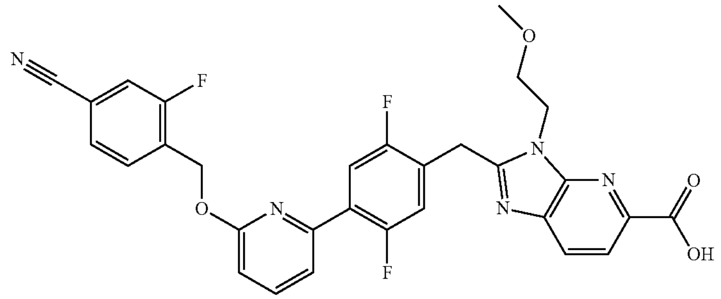 [SMILES: COCCn1c(Cc2cc(F)c(-c3cccc(OCc4ccc(C#N)cc4F)n3)cc2F)nc2ccc(C(=O)O)nc21]<br>2-(4-(6-((4-cyano-2-fluorobenzyl)oxy)pyridin-2-yl)-2,5-difluorobenzyl)-3-(2-methoxyethyl)-3H-imidazo[4,5-b]pyridine-5-carboxylic acid: ES/MS m/z 574.5; $^1$H NMR (400 MHz, MeOD) δ 8.22 (d, J = 8.3 Hz, 1H), 8.13 (d, J = 8.3 Hz, 1H), 7.86-7.78 (m, 1H), 7.77-7.70 (m, 2H), 7.65-7.52 (m, 3H), 7.25 (dd, J = 11.4, 6.0 Hz, 1H), 6.93 (dd, J = 8.3, 0.7 Hz, 1H), 5.63 (s, 2H), 4.75 (t, J = 5.0 Hz, 2H), 4.63 (s, 2H), 3.84 (dd, J = 5.4, 4.5 Hz, 2H), 3.31 (s, 3H). |
| 211 | 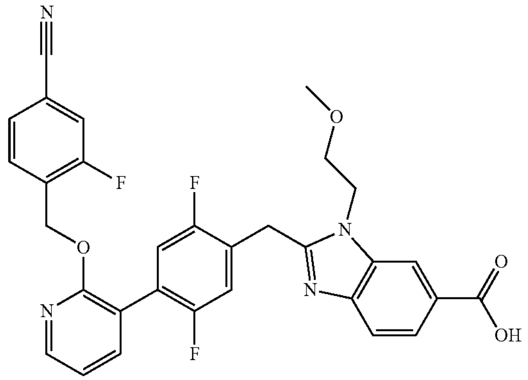 [SMILES: COCCn1c(Cc2cc(F)c(-c3cccnc3OCc3ccc(C#N)cc3F)cc2F)nc2ccc(C(=O)O)cc21]<br>2-(4-(2-((4-cyano-2-fluorobenzyl)oxy)pyridin-3-yl)-2,5-difluorobenzyl)-1-(2-methoxyethyl)-1H-benzo[d]imidazole-carboxylic acid: ES/MS m/z 573.3; $^1$H NMR (400 MHz, MeOD) δ 8.50 (d, J = 1.3 Hz, 1H), 8.24 (dd, J = 5.0, 1.8 Hz, 1H), 8.18 (dd, J = 8.6, 1.5 Hz, 1H), 7.80-7.73 (m, 2H), 7.64-7.54 (m, 2H), 7.51 (dd, J = 7.9, 1.5 Hz, 1H), 7.36 (dd, J = 9.9, 6.0 Hz, 1H), 7.29 (dd, J = 9.8, 6.1 Hz, 1H), 7.15 (dd, J = 7.4, 5.0 Hz, 1H), 5.57 (s, 2H), 4.77 (t, J = 4.9 Hz, 2H), 4.70 (s, 2H), 3.81 (t, J = 4.9 Hz, 2H), 3.28 (s, 3H). |
| 213 | 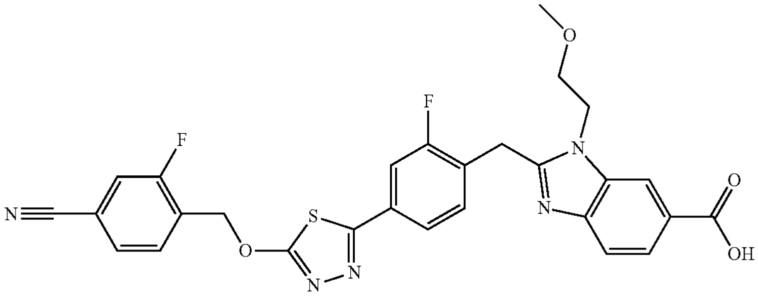 [SMILES: COCCn1c(Cc2ccc(-c3nnc(OCc4ccc(C#N)cc4F)s3)cc2F)nc2ccc(C(=O)O)cc21]<br>2-(4-(5-((4-cyano-2-fluorobenzyl)oxy)-1,3,4-thiadiazol-2-yl)-2-fluorobenzyl)-1-(2-methoxyethyl)-1H-benzo[d]imidazole-carboxylic acid: ES/MS m/z 562.2; $^1$H NMR (400 MHz, Methanol-d4) δ 8.43 (d, J = 1.4 Hz, 1H), 8.11 (dd, J = 8.6, 1.4 Hz, 1H), 7.83 (t, J = 7.5 Hz, 1H), 7.77 (dd, J = 10.5, 1.7 Hz, 1H), 7.74-7.64 (m, 4H), 7.50 (t, J = 7.8 Hz, 1H), 5.77 (s, 2H), 4.69 (t, J = 5.0 Hz, 2H), 4.67 (s, 2H), 3.78 (t, J = 4.9 Hz, 2H), 3.29 (s, 3H). |

-continued

| Example | Structure/Name/Characterization |
|---|---|
| 217 | 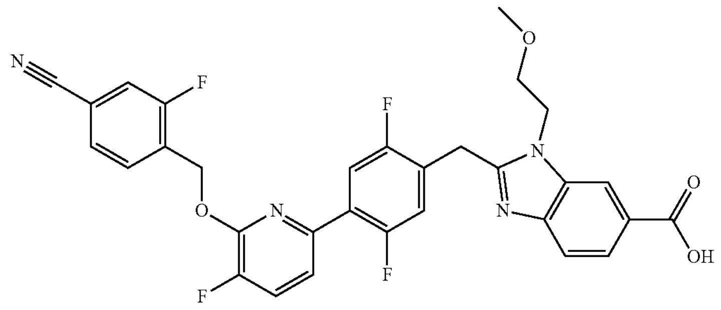 [SMILES: COCCn1c(Cc2cc(F)c(-c3ccc(F)c(OCc4ccc(C#N)cc4F)n3)cc2F)nc2ccc(C(=O)O)cc21]<br>2-(4-(6-((4-cyano-2-fluorobenzyl)oxy)-5-fluoropyridin-2-yl)-2,5-difluorobenzyl)-1-(2-methoxyethyl)-1H-benzo[d]imidazole-carboxylic acid: ES/MS m/z 591.26; $^{1}$H NMR (400 MHz, MeOD) δ 8.45 (t, J = 1.0 Hz, 1H), 8.13 (dd, J = 8.5, 1.5 Hz, 1H), 7.81-7.70 (m, 3H), 7.70-7.55 (m, 4H), 7.28 (dd, J = 11.4, 6.1 Hz, 1H), 5.71 (s, 2H), 4.72 (t, J = 5.0 Hz, 2H), 4.65 (s, 2H), 3.81 (t, J = 4.9 Hz, 2H), 3.30 (s, 3H). |
| 317 | 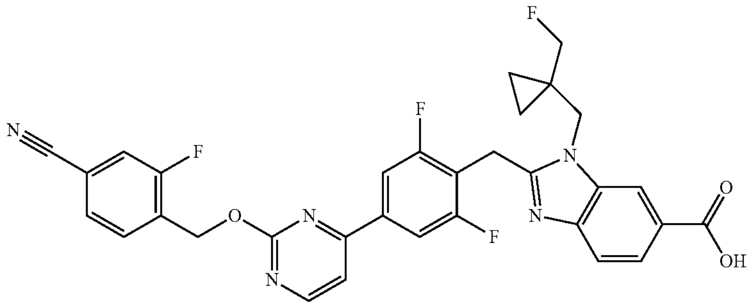 [SMILES: N#Cc1ccc(COc2nccc(-c3cc(F)c(Cc4nc5ccc(C(=O)O)cc5n4CC4(CF)CC4)c(F)c3)n2)c(F)c1]<br>2-(4-(2-((4-cyano-2-fluorobenzyl)oxy)pyrimidin-4-yl)-2,6-difluorobenzyl)-1-((1-(fluoromethyl)cyclopropyl)methyl)-1H-benzo[d]imidazole-6-carboxylic acid: ES/MS m/z 602.2; $^{1}$H NMR (400 MHz, DMSO-d6) δ 8.80 (d, J = 5.2 Hz, 1H), 8.25 (d, J = 1.5 Hz, 1H), 8.00 (d, J = 8.2 Hz, 2H), 7.95 (dd, J = 10.0, 1.5 Hz, 1H), 7.91 (d, J = 5.2 Hz, 1H), 7.82-7.73 (m, 3H), 7.56 (d, J = 8.5 Hz, 1H), 5.66 (s, 2H), 4.61 (s, 2H), 4.47 (s, 2H), 4.19 (d, J = 48.8 Hz, 2H), 2.48 (d, J = 1.9 Hz, 20H), 0.90-0.80 (m, 2H), 0.80-0.72 (m, 2H). |
| 318 | 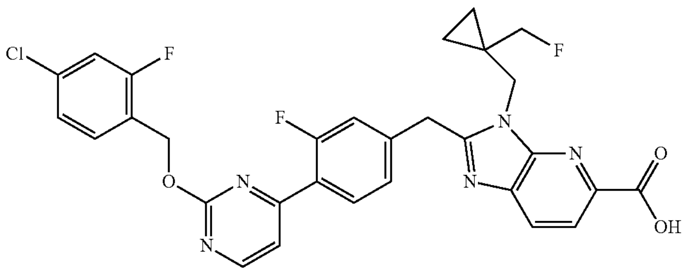 [SMILES: O=C(O)c1ccc2nc(Cc3ccc(-c4ccnc(OCc5ccc(Cl)cc5F)n4)c(F)c3)n(CC3(CF)CC3)c2n1]<br>2-(4-(2-((4-chloro-2-fluorobenzyl)oxy)pyrimidin-4-yl)-3-fluorobenzyl)-3-((1-(fluoromethyl)cyclopropyl)methyl)-3H-imidazo[4,5-b]pyridine-5-carboxylic acid: ES/MS m/z 594.2; $^{1}$H NMR (400 MHz, DMSO-d6) δ 8.73 (d, J = 5.2 Hz, 1H), 8.14-8.05 (m, 2H), 7.98 (d, J = 8.2 Hz, 1H), 7.63 (t, J = 8.2 Hz, 1H), 7.58 (dd, J = 5.2, 2.0 Hz, 1H), 7.52 (dd, J = 10.0, 2.1 Hz, 1H), 7.47-7.32 (m, 3H), 5.51 (s, 3H), 4.54 (s, 2H), 4.46 (s, 2H), 4.32 (d, J = 48.8 Hz, 3H), 1.09 (t, J = 5.3 Hz, 2H), 0.65 (d, J = 5.5 Hz, 2H). |

-continued

| Example | Structure/Name/Characterization |
|---|---|
| 319 | 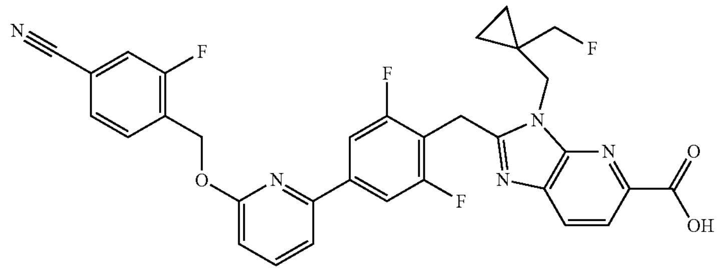 [SMILES: N#Cc1ccc(COc2cccc(-c3cc(F)c(Cc4nc5ccc(C(=O)O)nc5n4CC4(CF)CC4)c(F)c3)n2)c(F)c1]<br>2-(4-(6-((4-cyano-2-fluorobenzyl)oxy)pyridin-2-yl)-2,6-difluorobenzyl)-3-((1-(fluoromethyl)cyclopropyl)methyl)-3H-imidazo[4,5-b]pyridine-5-carboxylic acid: ES/MS m/z 602.2; $^{1}$H NMR (400 MHz, DMSO-d6) δ 8.03 (d, J = 8.2 Hz, 1H), 7.96-7.73 (m, 8H), 6.99 (d, J = 8.3 Hz, 1H), 5.64 (s, 2H), 4.56 (s, 2H), 4.52 (s, 2H), 4.33 (d, J = 48.9 Hz, 2H), 1.22-1.10 (m, 2H), 0.79-0.66 (m, 2H). |
| 320 | 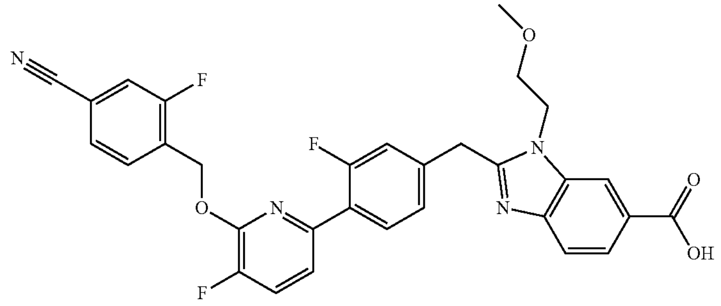 [SMILES: COCCn1c(Cc2ccc(-c3ccc(F)c(OCc4ccc(C#N)cc4F)n3)c(F)c2)nc2ccc(C(=O)O)cc21]<br>2-(4-(6-((4-cyano-2-fluorobenzyl)oxy)-5-fluoropyridin-2-yl)-3-fluorobenzyl)-1-(2-methoxyethyl)-1H-benzo[d]imidazole-carboxylic acid: ES/MS m/z 573.2; $^{1}$H NMR (400 MHz, DMSO-d6) δ 8.22 (s, 1H), 7.96-7.71 (m, 6H), 7.65 (d, J = 8.5 Hz, 1H), 7.48 (d, J = 8.6 Hz, 1H), 7.35-7.26 (m, 2H), 5.66 (s, 2H), 4.61-4.52 (m, 2H), 4.46 (s, 2H), 3.18 (s, 3H). |
| 321 | 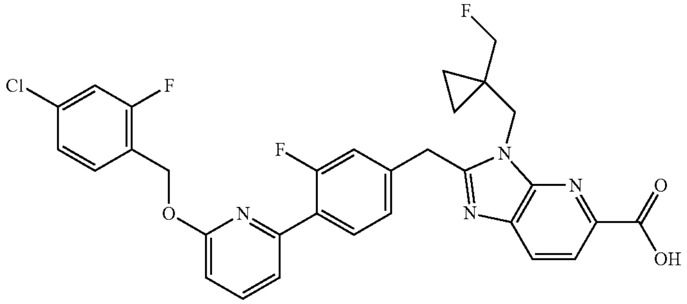 [SMILES: O=C(O)c1ccc2nc(Cc3ccc(-c4cccc(OCc5ccc(Cl)cc5F)n4)c(F)c3)n(CC3(CF)CC3)c2n1]<br>2-(4-(6-((4-chloro-2-fluorobenzyl)oxy)pyridin-2-yl)-3-fluorobenzyl)-3-((1-(fluoromethyl)cyclopropyl)methyl)-3H-imidazo[4,5-b]pyridine-5-carboxylic acid: ES/MS m/z 593.1; $^{1}$H NMR (400 MHz, DMSO-d6) δ 8.11 (d, J = 8.2 Hz, 1H), 7.97 (t, J = 8.6 Hz, 2H), 7.85 (t, J = 7.9 Hz, 1H), 7.61 (t, J = 8.2 Hz, 1H), 7.52-7.43 (m, 2H), 7.38-7.29 (m, 3H), 6.90 (d, J = 8.2 Hz, 1H), 5.48 (s, 2H), 4.51 (s, 2H), 4.46 (s, 2H), 4.33 (d, J = 48.8 Hz, 2H), 1.09 (t, J = 5.2 Hz, 2H), 0.65 (m, J = 5.6 Hz, 2H). |
| 322 | 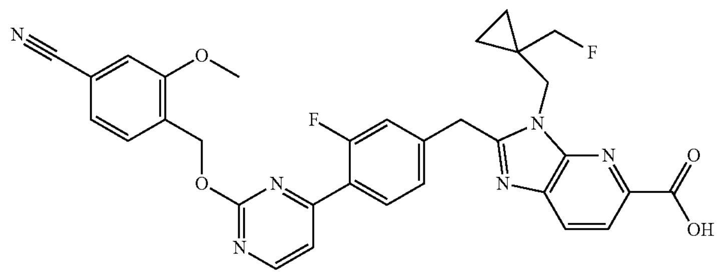 [SMILES: COc1cc(C#N)ccc1COc1nccc(-c2ccc(Cc3nc4ccc(C(=O)O)nc4n3CC3(CF)CC3)cc2F)n1] |

-continued

| Example | Structure/Name/Characterization |
|---|---|
| | 2-(4-(2-((4-cyano-2-methoxybenzyl)oxy)pyrimidin-4-yl)-3-fluorobenzyl)-3-((1-(fluoromethyl)cyclopropyl)methyl)-3H-imidazo[4,5-b]pyridine-5-carboxylic acid: ES/MS m/z 597.2; $^1$H NMR (400 MHz, DMSO-d6) δ 8.73 (d, J = 5.3 Hz, 1H), 8.10 (d, J = 8.2 Hz, 1H), 8.04 (t, J = 8.1 Hz, 1H), 7.98 (d, J = 8.3 Hz, 1H), 7.60-7.55 (m, 3H), 7.47-7.36 (m, 3H), 5.52 (s, 2H), 4.54 (s, 2H), 4.46 (s, 2H), 4.32 (d, J = 49.0 Hz, 2H), 3.91 (s, 3H), 1.12-1.03 (m, 2H), 0.70-0.61 (m, 2H). |
| 410 | 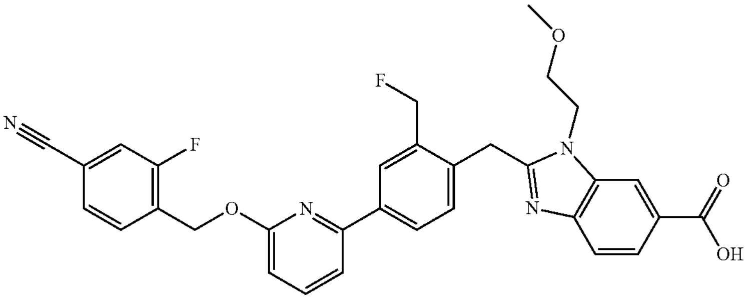 [SMILES: COCCn1c(Cc2ccc(-c3cccc(OCc4ccc(C#N)cc4F)n3)cc2CF)nc2ccc(C(=O)O)cc21] 2-(4-(6-((4-cyano-2-fluorobenzyl)oxy)pyridin-2-yl)-2-(fluoromethyl)benzyl)-1-(2-methoxyethyl)-1H-benzo[d]imidazole-carboxylic acid: ES/MS m/z 569.2; $^1$H NMR (400 MHz, Methanol-d4) δ 8.51 (s, 1H), 8.22-8.15 (m, 2H), 8.12 (d, J = 8.1 Hz, 1H), 7.83 (t, J = 7.9 Hz, 1H), 7.79-7.69 (m, 2H), 7.66-7.54 (m, 3H), 7.42 (d, J = 8.0 Hz, 1H), 6.91 (d, J = 8.2 Hz, 1H), 5.71-5.53 (m, 4H), 4.82 (s, 2H), 4.78-4.73 (m, 2H), 3.86-3.76 (m, 2H), 3.34 (s, 3H). |
| 411 | 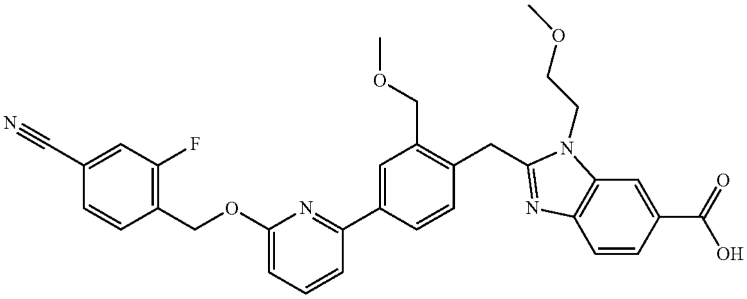 [SMILES: COCCn1c(Cc2ccc(-c3cccc(OCc4ccc(C#N)cc4F)n3)cc2COC)nc2ccc(C(=O)O)cc21] 2-(4-(6-((4-cyano-2-fluorobenzyl)oxy)pyridin-2-yl)-2-(methoxymethyl)benzyl)-1-(2-methoxyethyl)-1H-benzo[d]imidazole-6-carboxylic acid: ES/MS m/z 581.2; $^1$H NMR (400 MHz, Methanol-d4) δ 8.55 (s, 1H), 8.21 (dd, J = 8.5, 1.5 Hz, 1H), 8.13-8.03 (m, 2H), 7.82 (t, J = 7.9 Hz, 1H), 7.79-7.68 (m, 2H), 7.66-7.54 (m, 3H), 7.42 (d, J = 7.9 Hz, 1H), 6.91 (d, J = 8.2 Hz, 1H), 5.67 (s, 2H), 4.82-4.76 (m, 4H), 4.60 (s, 2H), 3.83 (t, J = 4.9 Hz, 2H), 3.35 (s, 3H), 3.24 (s, 3H). |
| 522 | 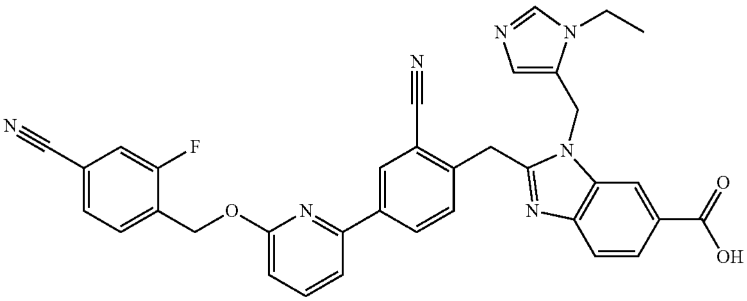 [SMILES: CCn1cncc1Cn1c(Cc2ccc(-c3cccc(OCc4ccc(C#N)cc4F)n3)cc2C#N)nc2ccc(C(=O)O)cc21] 2-(2-cyano-4-(6-((4-cyano-2-fluorobenzyl)oxy)pyridin-2-yl)benzyl)-1-((1-ethyl-1H-imidazol-5-yl)methyl)-1H-benzo[d]imidazole-carboxylic acid: ES/MS m/z 612.2; $^1$H NMR (400 MHz, Methanol-d4) δ 9.31 (s, 1H), 9.03 (s, 1H), 8.81 (d, J = 8.9 Hz, 1H), 8.64 (dd, J = 8.8, 1.7 Hz, 1H), 8.50-8.35 (m, 1H), 8.26 (dd, J = 8.8, 1.6 Hz, 1H), 8.04 (d, J = 8.8 Hz, 1H), 8.00-7.70 (m, 3H), 7.70-7.56 (m, 2H), 7.44 (d, J = 9.0 Hz, 2H), 6.97 (d, J = 8.1 Hz, 1H), 5.97 (s, 2H), 5.76 (s, 2H), 4.45 (q, J = 7.3 Hz, 2H), 1.68 (t, J = 7.3 Hz, 3H). |

-continued

| Example | Structure/Name/Characterization |
|---|---|
| 545 | 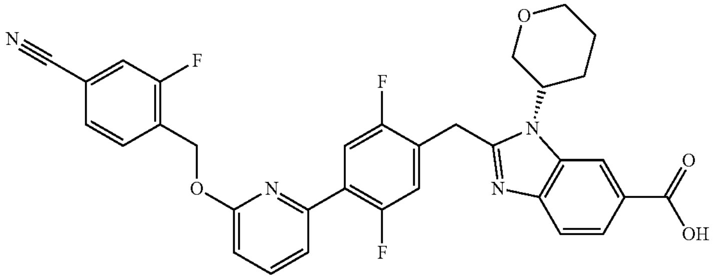 2-(4-(6-((4-cyano-2-fluorobenzyl)oxy)pyridin-2-yl)-2,5-difluorobenzyl)-1-(tetrahydro-2H-pyran-3-yl)-1H-benzo[d]imidazole-carboxylic acid: ES/MS m/z 599.2; $^1$H NMR (400 MHz, Acetonitrile-d3) δ 8.49-8.45 (m, 1H), 7.99 (dd, J = 8.5, 1.4 Hz, 1H), 7.87-7.78 (m, 2H), 7.73 (dd, J = 12.5, 8.0 Hz, 2H), 7.61-7.54 (m, 3H), 7.24 (dd, J = 11.5, 6.1 Hz, 1H), 6.93 (dd, J = 8.2, 0.7 Hz, 1H), 5.63 (s, 2H), 4.72-4.61 (m, 1H), 4.56 (s, 2H), 4.09 (t, J = 10.9 Hz, 1H), 4.02-3.89 (m, 2H), 3.62 (td, J = 11.2, 4.1 Hz, 1H). |
| 546 | 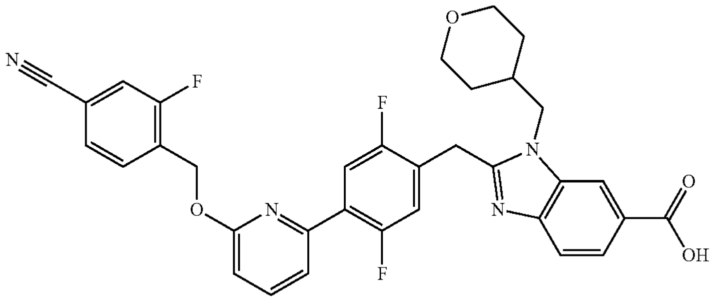 [SMILES: N#Cc1ccc(COc2cccc(-c3cc(F)c(Cc4nc5ccc(C(=O)O)cc5n4CC4CCOCC4)cc3F)n2)c(F)c1] 2-(4-(6-((4-cyano-2-fluorobenzyl)oxy)pyridin-2-yl)-2,5-difluorobenzyl)-1-((tetrahydro-2H-pyran-4-yl)methyl)-1H-benzo[d]imidazole-carboxylic acid: ES/MS m/z 613.2; $^1$H NMR (400 MHz, Acetonitrile-d3) δ 8.34-8.31 (m, 1H), 7.92 (dd, J = 8.4, 1.6 Hz, 1H), 7.87-7.69 (m, 3H), 7.65 (d, J = 8.4 Hz, 1H), 7.57 (dd, J = 10.5, 8.2 Hz, 3H), 7.23 (dd, J = 11.6, 6.1 Hz, 1H), 6.92 (d, J = 8.2 Hz, 1H), 5.63 (s, 2H), 4.51 (d, J = 3.8 Hz, 2H), 4.41 (d, J = 6.3 Hz, 2H), 3.85-3.77 (m, 1H), 3.67 (q, J = 7.4, 7.0 Hz, 1H), 1.90-1.82 (m, 2H). |
| 547 | 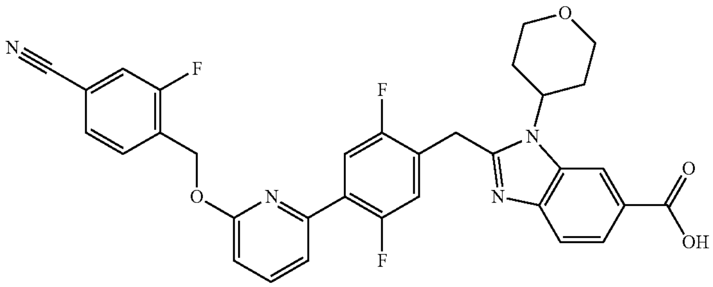 [SMILES: N#Cc1ccc(COc2cccc(-c3cc(F)c(Cc4nc5ccc(C(=O)O)cc5n4C4CCOCC4)cc3F)n2)c(F)c1] 2-(4-(6-((4-cyano-2-fluorobenzyl)oxy)pyridin-2-yl)-2,5-difluorobenzyl)-1-(tetrahydro-2H-pyran-4-yl)-1H-benzo[d]imidazole-carboxylic acid: ES/MS m/z 599.2; $^1$H NMR (400 MHz, Methanol-d4) δ 8.62 (d, J = 1.2 Hz, 1H), 8.16 (dd, J = 8.6, 1.4 Hz, 1H), 7.89-7.76 (m, 3H), 7.77-7.70 (m, 1H), 7.63-7.53 (m, 3H), 7.34 (dd, J = 11.3, 6.0 Hz, 1H), 6.95 (dd, J = 8.3, 0.7 Hz, 1H), 5.63 (s, 2H), 4.72 (s, 2H), 4.21 (t, J = 10.8 Hz, 1H), 4.09-3.93 (m, 2H), 3.76-3.65 (m, 1H), 2.67-2.50 (m, 1H), 2.12 (d, J = 12.7 Hz, 1H), 2.00-1.89 (m, 2H). |

-continued

| Example | Structure/Name/Characterization |
|---|---|
| 548 | 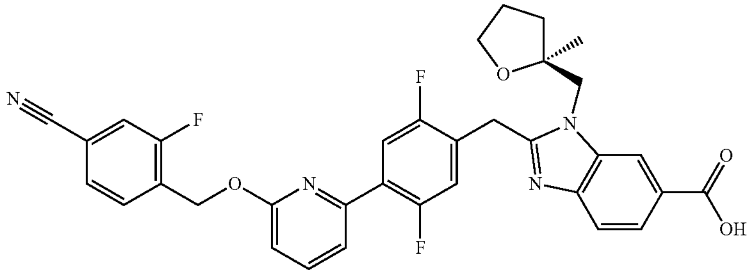 [SMILES: C[C@@]1(Cn2c(Cc3cc(F)c(-c4cccc(OCc5ccc(C#N)cc5F)n4)cc3F)nc3ccc(C(=O)O)cc32)CCCO1] And 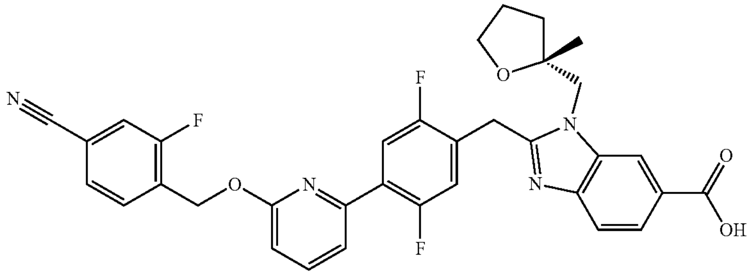 [SMILES: C[C@]1(Cn2c(Cc3cc(F)c(-c4cccc(OCc5ccc(C#N)cc5F)n4)cc3F)nc3ccc(C(=O)O)cc32)CCCO1] 2-(4-(6-((4-cyano-2-fluorobenzyl)oxy)pyridin-2-yl)-2,5-difluorobenzyl)-1-((2-methyltetrahydrofuran-2-yl)methyl)-1H-benzo[d]imidazole-carboxylic acid: ES/MS m/z 613.2; $^{1}$H NMR (400 MHz, Acetonitrile-d3) δ 8.38 (t, J = 1.0 Hz, 1H), 8.06 (dd, J = 8.6, 1.5 Hz, 1H), 7.88-7.69 (m, 4H), 7.62-7.53 (m, 3H), 7.32 (dd, J = 11.4, 6.1 Hz, 1H), 6.94 (dd, J = 8.3, 0.7 Hz, 1H), 5.63 (s, 3H), 4.55 (s, 2H), 4.31 (d, J = 7.6 Hz, 2H), 3.95-3.81 (m, 2H), 3.26 (td, J = 11.4, 3.1 Hz, 2H), 1.56-1.43 (m, 4H). |
| 549 | 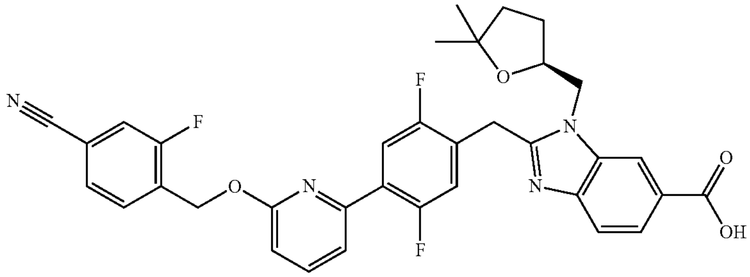 [SMILES: CC1(C)CC[C@@H](Cn2c(Cc3cc(F)c(-c4cccc(OCc5ccc(C#N)cc5F)n4)cc3F)nc3ccc(C(=O)O)cc32)O1] and 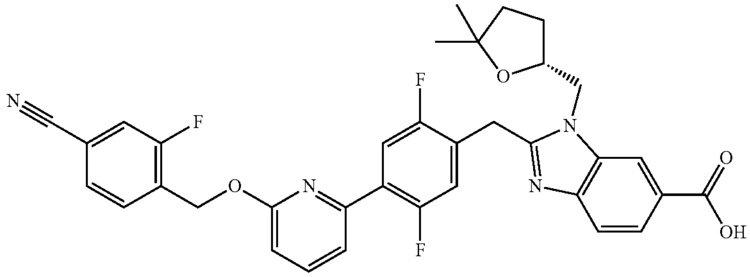 [SMILES: CC1(C)CC[C@H](Cn2c(Cc3cc(F)c(-c4cccc(OCc5ccc(C#N)cc5F)n4)cc3F)nc3ccc(C(=O)O)cc32)O1] 2-(4-(6-((4-cyano-2-fluorobenzyl)oxy)pyridin-2-yl)-2,5-difluorobenzyl)-1-((5,5-dimethyltetrahydrofuran-2-yl)methyl)-1H-benzo[d]imidazole-6-carboxylic acid: ES/MS m/z 627.2; $^{1}$H NMR (400 MHz, Acetonitrile-d3) δ 8.46 (dd, J = 1.6, 0.7 Hz, 1H), 8.08 (dd, J = 8.6, 1.5 Hz, 1H), 7.86-7.70 (m, 4H), 7.62-7.54 (m, 3H), 7.29 (dd, J = 11.4, 6.1 Hz, 1H), 6.94 (dd, J = 8.2, 0.6 Hz, 1H), 5.62 (s, 2H), 4.68 (d, J = 4.3 Hz, 2H), 4.62 (dd, J = 14.7, 2.2 Hz, 1H), 4.47-4.31 (m, 2H), 2.25 (q, J = 6.3 Hz, 1H), 1.85-1.75 (m, 3H), 1.23 (s, 3H), 1.15 (s, 3H). |

-continued

| Example | Structure/Name/Characterization |
|---|---|
| 662 | 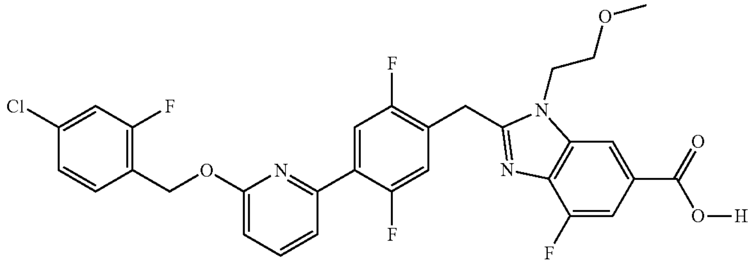 [SMILES: COCCn1c(Cc2cc(F)c(-c3cccc(OCc4ccc(Cl)cc4F)n3)cc2F)nc2c(F)cc(C(=O)O)cc21]<br>ES/MS m/z 600.1; 1H NMR (400 MHz, Methanol-d4) δ 8.17 (d, J = 1.3 Hz, 1H), 7.84 (dd, J = 10.8, 6.4 Hz, 1H), 7.78 (t, J = 7.9 Hz, 1H), 7.69 (dd, J = 11.2, 1.2 Hz, 1H), 7.54 (t, J = 8.0 Hz, 2H), 7.31-7.08 (m, 3H), 6.87 (d, J = 8.1 Hz, 1H), 5.52 (s, 2H), 4.60 (t, J = 5.0 Hz, 2H), 4.54 (s, 2H), 3.73 (t, J = 5.0 Hz, 2H), 3.27 (s, 3H). |
| 663 | 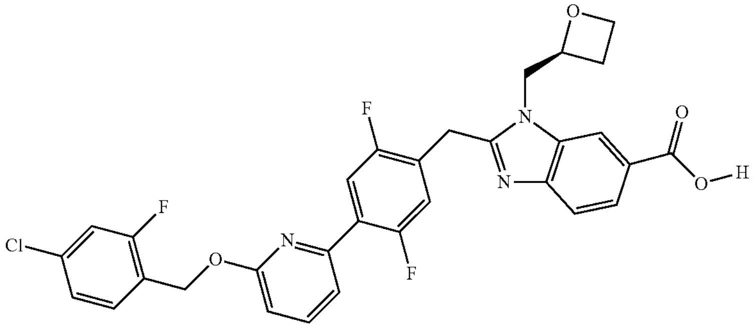 [SMILES: O=C(O)c1ccc2nc(Cc3cc(F)c(-c4cccc(OCc5ccc(Cl)cc5F)n4)cc3F)n(C[C@@H]3CCO3)c2c1]<br>ES/MS m/z 594.1; 1H NMR (400 MHz, Methanol-d4) δ 8.30 (d, J = 1.4 Hz, 1H), 7.98 (dd, J = 8.4, 1.5 Hz, 1H), 7.84 (dd, J = 10.8, 6.4 Hz, 1H), 7.78 (t, J = 7.9 Hz, 1H), 7.66 (d, J = 8.5 Hz, 1H), 7.54 (t, J = 8.0 Hz, 2H), 7.29-7.11 (m, 3H), 6.87 (d, J = 8.2 Hz, 1H), 5.53 (s, 2H), 5.20 (td, J = 8.2, 7.7, 5.2 Hz, 1H), 4.79-4.35 (m, 6H), 2.92-2.69 (m, 1H), 2.50 (ddd, J = 16.0, 10.2, 7.3 Hz, 1H). |
| 664 | 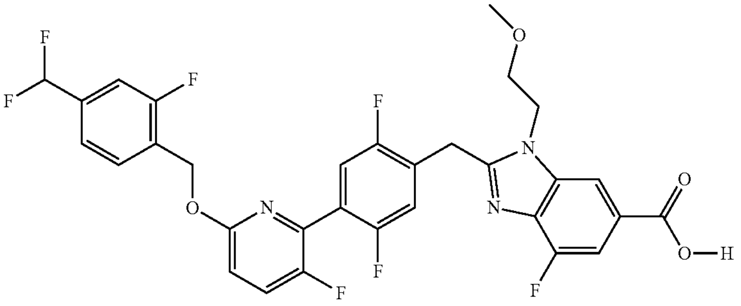 [SMILES: COCCn1c(Cc2cc(F)c(-c3nc(OCc4ccc(C(F)F)cc4F)ccc3F)cc2F)nc2c(F)cc(C(=O)O)cc21]<br>ES/MS m/z 634.2; 1H NMR (400 MHz, DMSO-d6) δ 8.10 (d, J = 1.3 Hz, 1H), 7.88 (t, J = 8.9 Hz, 1H), 7.71 (t, J = 7.5 Hz, 1H), 7.57-7.34 (m, 5H), 7.23-6.90 (m, 2H), 5.48 (s, 2H), 4.63 (t, J = 5.1 Hz, 2H), 4.48 (s, 2H), 3.68 (t, J = 5.0 Hz, 2H), 3.21 (s, 3H). 19F NMR (377 MHz, DMSO-d6) δ −75.42, −110.82 (d, J = 55.6 Hz), −117.07 (dd, J = 10.3, 7.5 Hz), −119.65-−120.85 (m), −122.52 (ddd, J = 16.5, 9.9, 6.3 Hz), −129.47 (d, J = 11.7 Hz), −132.64 (dd, J = 34.2, 9.2 Hz). |
| 665 | 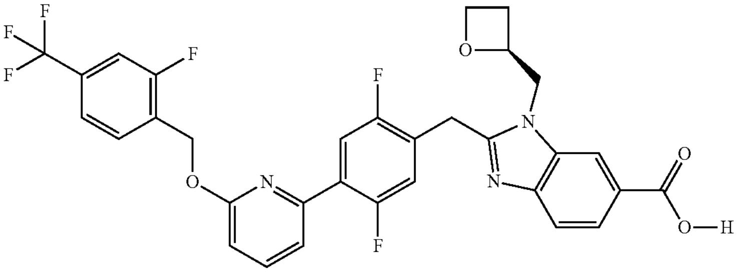 [SMILES: O=C(O)c1ccc2nc(Cc3cc(F)c(-c4cccc(OCc5ccc(C(F)(F)F)cc5F)n4)cc3F)n(C[C@@H]3CCO3)c2c1] |

-continued

| Example | Structure/Name/Characterization |
|---|---|
| | ES/MS m/z 628.1; 1H NMR (400 MHz, DMSO-d6) δ 8.26 (d, J = 1.5 Hz, 1H), 7.90 (dd, J = 8.3, 7.5 Hz, 1H), 7.86-7.69 (m, 4H), 7.62 (dd, J = 13.1, 7.9 Hz, 2H), 7.53 (dd, J = 7.5, 1.7 Hz, 1H), 7.38 (dd, J = 11.5, 6.1 Hz, 1H), 6.99 (d, J = 8.2 Hz, 1H), 5.61 (s, 2H), 5.07 (qd, J = 7.1, 2.7 Hz, 1H), 4.76 (dd, J = 15.6, 7.0 Hz, 1H), 4.62 (dd, J = 15.6, 2.8 Hz, 1H), 4.56-4.41 (m, 3H), 4.36 (dt, J = 9.0, 6.0 Hz, 1H), 2.84-2.64 (m, 1H), 2.46-2.30 (m, 1H). |
| 666 | 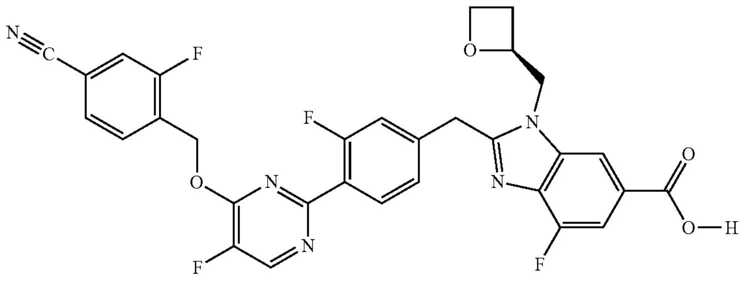 [SMILES: N#Cc1ccc(COc2nc(-c3ccc(Cc4nc5c(F)cc(C(=O)O)cc5n4C[C@@H]4CCO4)cc3F)ncc2F)c(F)c1] ES/MS m/z 604.2; 1H NMR (400 MHz, DMSO-d6) δ 8.81 (d, J = 2.9 Hz, 1H), 8.14 (d, J = 1.2 Hz, 1H), 8.00 (t, J = 8.1 Hz, 1H), 7.95 (dd, J = 10.0, 1.4 Hz, 1H), 7.84-7.73 (m, 2H), 7.52 (dd, J = 11.4, 1.2 Hz, 1H), 7.32 (dd, J = 16.3, 10.0 Hz, 2H), 5.73 (s, 2H), 5.06-4.90 (m, 1H), 4.74 (dd, J = 15.5, 7.3 Hz, 1H), 4.64-4.54 (m, 1H), 4.51 (d, J = 3.5 Hz, 2H), 4.47 (t, J = 7.7 Hz, 1H), 4.35 (dt, J = 9.0, 5.9 Hz, 1H), 2.78-2.59 (m, 1H), 2.43-2.29 (m, 1H). |
| 667 | 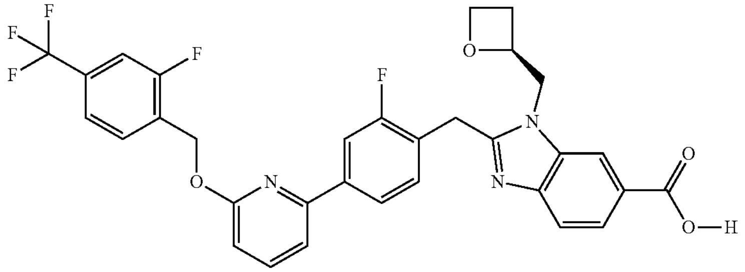 [SMILES: O=C(O)c1ccc2nc(Cc3ccc(-c4cccc(OCc5ccc(C(F)(F)F)cc5F)n4)cc3F)n(C[C@@H]3CCO3)c2c1] ES/MS m/z 610.2; 1H NMR (400 MHz, DMSO-d6) δ 8.25 (d, J = 1.6 Hz, 1H), 7.90-7.84 (m, 3H), 7.84-7.73 (m, 3H), 7.66 (d, J = 7.5 Hz, 1H), 7.63 (d, J = 7.8 Hz, 1H), 7.59 (d, J = 8.4 Hz, 1H), 7.43 (t, J = 7.8 Hz, 1H), 6.93 (d, J = 8.2 Hz, 1H), 5.63 (s, 2H), 5.04 (d, J = 6.8 Hz, 1H), 4.73 (dd, J = 15.5, 7.1 Hz, 1H), 4.65-4.56 (m, 1H), 4.56-4.40 (m, 3H), 4.36 (dt, J = 9.1, 5.9 Hz, 1H), 2.79-2.65 (m, 1H), 2.42-2.31 (m, 1H). (Multiplet Report) 19F NMR (376 MHz, DMSO-d6) δ −73.94, −116.09, −117.40. |
| 668 | 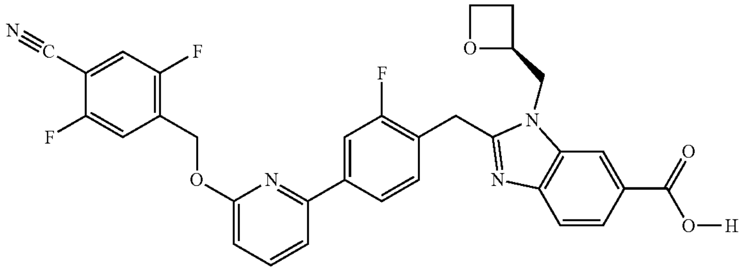 [SMILES: N#Cc1cc(F)c(COc2cccc(-c3ccc(Cc4nc5ccc(C(=O)O)cc5n4C[C@@H]4CCO4)c(F)c3)n2)cc1F] ES/MS m/z 585.2; 1H NMR (400 MHz, DMSO-d6) δ 8.25 (d, J = 1.5 Hz, 1H), 8.06 (dd, J = 9.2, 5.2 Hz, 1H), 7.96-7.84 (m, 3H), 7.83-7.70 (m, 2H), 7.68 (d, J = 7.5 Hz, 1H), 7.59 (d, J = 8.4 Hz, 1H), 7.43 (t, J = 8.0 Hz, 1H), 6.96 (d, J = 8.2 Hz, 1H), 5.60 (s, 2H), 5.05 (d, J = 7.9 Hz, 1H), 4.73 (dd, J = 15.6, 7.1 Hz, 1H), 4.60 (dd, J = 15.6, 2.7 Hz, 1H), 4.56-4.40 (m, 3H), 4.36 (dt, J = 9.1, 5.9 Hz, 1H), 2.75-2.61 (m, 1H), 2.43-2.28 (m, 1H). (Multiplet Report) 19F NMR (376 MHz, DMSO-d6) δ −113.85 (ddd, J = 17.1, 9.4, 5.3 Hz), −117.32 (dd, J = 11.6, 7.8 Hz), −121.05 (ddd, J = 15.8, 9.2, 5.8 Hz). |

-continued

| Example | Structure/Name/Characterization |
|---|---|
| 669 | 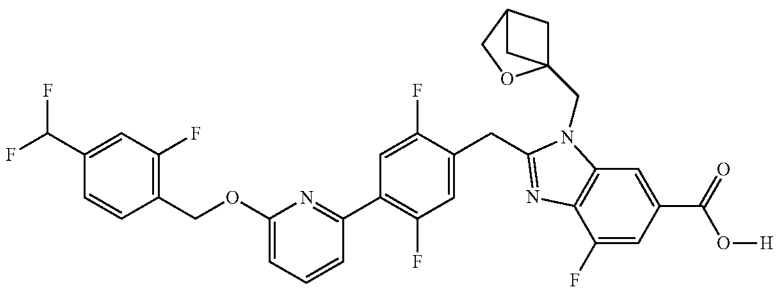 [SMILES: O=C(O)c1cc(F)c2nc(Cc3cc(F)c(-c4cccc(OCc5ccc(C(F)F)cc5F)n4)cc3F)n(CC34CC(CO3)C4)c2c1]<br>ES/MS m/z 654.2; 1H NMR (400 MHz, DMSO-d6) δ 8.14 (d, J = 1.3 Hz, 1H), 7.93-7.84 (m, 1H), 7.80 (dd, J = 10.5, 6.4 Hz, 1H), 7.73 (t, J = 7.6 Hz, 1H), 7.53 (dd, J = 7.5, 1.8 Hz, 1H), 7.49 (dd, J = 11.3, 1.3 Hz, 2H), 7.45 (dd, J = 7.9, 1.4 Hz, 1H), 7.41 (dd, J = 11.5, 6.1 Hz, 1H), 7.06 (t, J = 55.6 Hz, 1H), 6.97 (d, J = 8.3 Hz, 1H), 5.58 (s, 2H), 4.82 (s, 2H), 4.48 (s, 2H), 3.64 (s, 2H), 2.90 (t, J = 3.2 Hz, 1H), 1.93 (ddd, J = 4.7, 3.2, 1.6 Hz, 2H), 1.30 (dd, J = 4.4, 1.7 Hz, 2H). 19F NMR (376 MHz, DMSO-d6) δ −75.33, −110.79 (d, J = 55.6 Hz), −117.20 (d, J = 7.7 Hz), −121.46-−122.20 (m), −122.12-−122.93 (m), −129.78 (d, J = 12.1 Hz). |
| 670 | 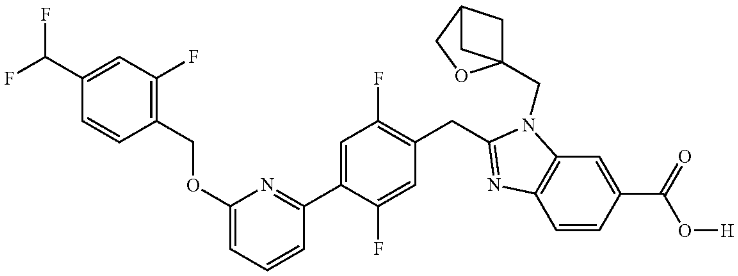<br>ES/MS m/z 636.3; 1H NMR (400 MHz, DMSO) δ 8.32 (d, J = 1.6 Hz, 1H), 7.94-7.85 (m, 1H), 7.88-7.76 (m, 2H), 7.72 (t, J = 7.6 Hz, 1H), 7.63 (d, J = 8.4 Hz, 1H), 7.56-7.38 (m, 4H), 7.06 (t, J = 55.6 Hz, 1H), 6.98 (d, J = 8.3 Hz, 1H), 5.58 (s, 2H), 4.85 (s, 2H), 4.53 (s, 2H), 3.64 (s, 2H), 2.90 (t, J = 3.1 Hz, 1H), 2.03-1.84 (m, 2H). 19F NMR (376 MHz, DMSO) δ −75.27, −110.78 (d, J = 55.7 Hz), −117.22 (dd, J = 10.3, 7.4 Hz), −121.80 (q, J = 13.9, 10.4 Hz), −122.35 (ddd, J = 17.2, 10.3, 6.1 Hz). |
| 671 | 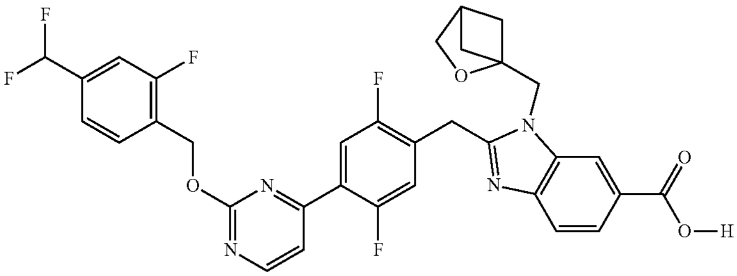 [SMILES: O=C(O)c1ccc2nc(Cc3cc(F)c(-c4ccnc(OCc5ccc(C(F)F)cc5F)n4)cc3F)n(CC34CC(CO3)C4)c2c1]<br>ES/MS m/z 651.2; 1H NMR (400 MHz, DMSO) δ 8.79 (d, J = 5.2 Hz, 1H), 8.32 (d, J = 1.5 Hz, 1H), 7.93 (dd, J = 10.2, 6.3 Hz, 1H), 7.84 (dd, J = 8.4, 1.5 Hz, 1H), 7.75 (t, J = 7.6 Hz, 1H), 7.67-7.59 (m, 2H), 7.56-7.44 (m, 3H), 7.07 (t, J = 55.6 Hz, 1H), 5.61 (s, 2H), 4.85 (s, 2H), 4.56 (s, 2H), 3.63 (s, 2H), 2.90 (t, J = 3.1 Hz, 1H), 1.94 (ddd, J = 4.7, 3.3, 1.6 Hz, 2H), 1.31 (dd, J = 4.4, 1.8 Hz, 2H). 19F NMR (376 MHz, DMSO) δ −75.36, −110.87 (d, J = 55.7 Hz), −117.08 (dd, J = 10.3, 7.4 Hz), −120.12 (ddd, J = 18.3, 11.7, 6.2 Hz), −121.63 (ddd, J = 16.3, 10.2, 6.1 Hz). |

-continued

| Example | Structure/Name/Characterization |
|---|---|
| 672 | 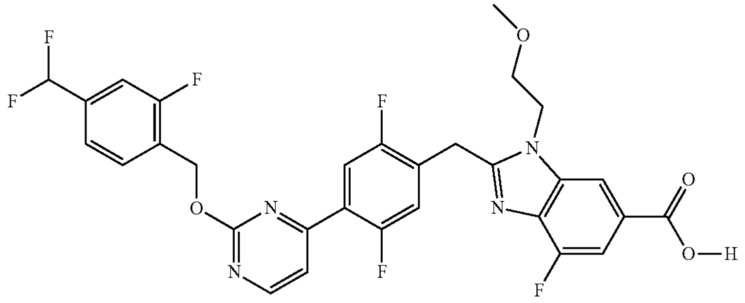 [SMILES: COCCn1c(Cc2cc(F)c(-c3ccnc(OCc4ccc(C(F)F)cc4F)n3)cc2F)nc2c(F)cc(C(=O)O)cc21] ES/MS m/z 617; 1H NMR (400 MHz, DMSO) δ 8.78 (d, J = 5.1 Hz, 1H), 8.10 (d, J = 1.3 Hz, 1H), 7.93 (dd, J = 10.2, 6.3 Hz, 1H), 7.75 (t, J = 7.6 Hz, 1H), 7.64 (dd, J = 5.2, 1.8 Hz, 1H), 7.57-7.38 (m, 4H), 7.07 (t, J = 55.6 Hz, 1H), 5.61 (s, 2H), 4.62 (t, J = 5.1 Hz, 2H), 4.49 (s, 2H), 3.68 (t, J = 5.0 Hz, 2H), 3.21 (s, 3H). 19F NMR (376 MHz, DMSO) δ −74.83, −110.87 (d, J = 55.7 Hz), −117.06 (dd, J = 10.2, 7.4 Hz), −119.43-−121.02 (m), −121.72 (ddd, J = 16.8, 10.1, 6.1 Hz), −129.53 (d, J = 11.3 Hz). |
| 673 | 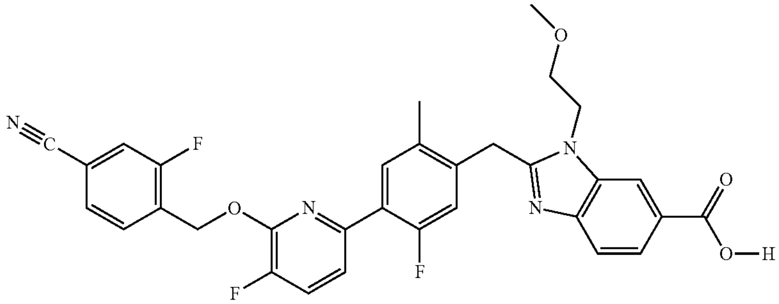 [SMILES: COCCn1c(Cc2cc(F)c(-c3ccc(F)c(OCc4ccc(C#N)cc4F)n3)cc2C)nc2ccc(C(=O)O)cc21] ES/MS m/z 587.2; Multiplet Report 1H NMR (400 MHz, DMSO-d6) δ 8.30 (s, 1H), 8.00-7.93 (m, 1H), 7.91-7.72 (m, 4H), 7.66 (dd, J = 11.0, 8.3 Hz, 2H), 7.51-7.44 (m, 1H), 7.12 (d, J = 12.3 Hz, 1H), 5.68 (s, 2H), 4.63 (t, J = 5.1 Hz, 2H), 4.47 (s, 2H), 3.69 (t, J = 5.0 Hz, 2H), 3.22 (s, 3H), 2.27 (s, 3H). |
| 674 | 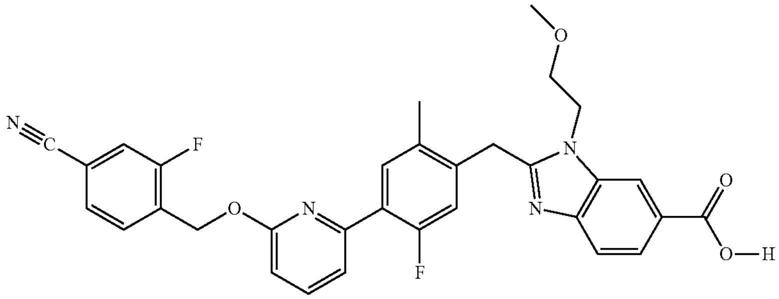 [SMILES: COCCn1c(Cc2cc(F)c(-c3cccc(OCc4ccc(C#N)cc4F)n3)cc2C)nc2ccc(C(=O)O)cc21] ES/MS m/z 569.2; Multiplet Report 1H NMR (400 MHz, DMSO-d6) δ 8.32 (s, 1H), 7.95 (d, J = 10.2 Hz, 1H), 7.92-7.82 (m, 2H), 7.80-7.67 (m, 3H), 7.65 (d, J = 8.4 Hz, 1H), 7.46 (d, J = 6.5 Hz, 1H), 7.13 (d, J = 12.2 Hz, 1H), 6.96 (d, J = 8.2 Hz, 1H), 5.59 (s, 2H), 4.64 (d, J = 5.5 Hz, 2H), 4.49 (br s, 2H), 3.69 (d, J = 10.0 Hz, 1H), 3.22 (s, 3H), 2.27 (s, 3H). |
| 675 | 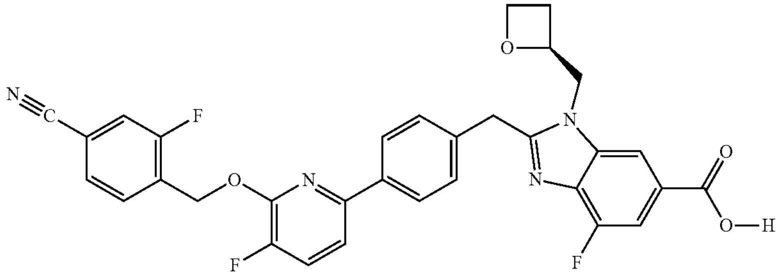 [SMILES: N#Cc1ccc(COc2nc(-c3ccc(Cc4nc5c(F)cc(C(=O)O)cc5n4C[C@@H]4CCO4)cc3)ccc2F)c(F)c1] |

-continued

| Example | Structure/Name/Characterization |
|---|---|
| | ES/MS m/z 585.2; Multiplet Report 1H NMR (400 MHz, DMSO-d6) δ 8.13 (d, J = 1.3 Hz, 1H), 8.01-7.90 (m, 3H), 7.85-7.71 (m, 3H), 7.62 (dd, J = 8.3, 2.8 Hz, 1H), 7.55-7.47 (m, 1H), 7.43 (d, J = 8.1 Hz, 2H), 5.69 (s, 2H), 4.94 (d, J = 8.6 Hz, 1H), 4.70 (dd, J = 15.5, 7.3 Hz, 1H), 4.61-4.52 (m, 1H), 4.54-4.40 (m, 3H), 4.40-4.30 (m, 1H), 2.63 (d, J = 8.8 Hz, 1H). |
| 676 | 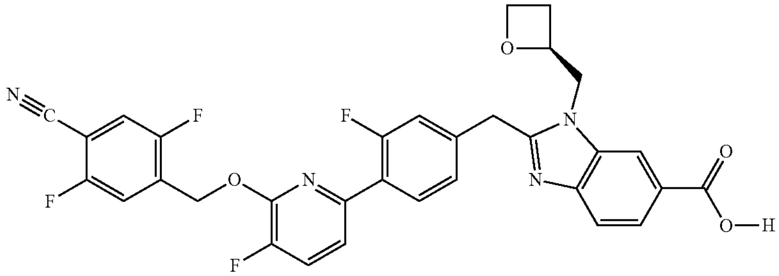 [SMILES: N#Cc1cc(F)c(COc2nc(-c3ccc(Cc4nc5ccc(C(=O)O)cc5n4C[C@@H]4CCO4)cc3F)ccc2F)cc1F] ES/MS m/z 603.2; Multiplet Report 1H NMR (400 MHz, DMSO-d6) δ 8.26 (s, 2H), 8.07 (dd, J = 9.2, 5.1 Hz, 1H), 7.90-7.78 (m, 3H), 7.75 (dd, J = 9.2, 5.5 Hz, 1H), 7.64 (d, J = 8.4 Hz, 1H), 7.49 (d, J = 8.6 Hz, 1H), 7.31 (t, J = 11.0 Hz, 2H), 5.64 (s, 2H), 4.99 (d, J = 7.7 Hz, 1H), 4.72 (dd, J = 15.5, 7.2 Hz, 1H), 4.58 (m, 1H), 4.47 (m, 3H), 4.39 (m, 1H). |
| 677 | 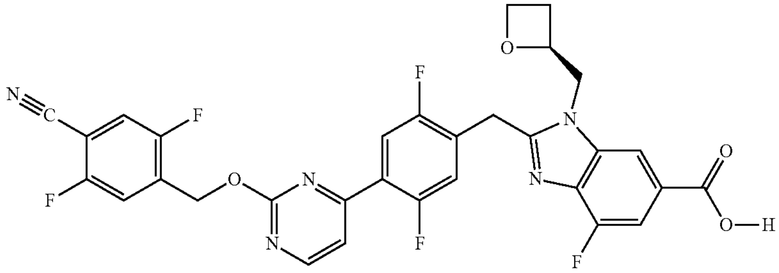 [SMILES: N#Cc1cc(F)c(COc2nccc(-c3cc(F)c(Cc4nc5c(F)cc(C(=O)O)cc5n4C[C@@H]4CCO4)cc3F)n2)cc1F] ES/MS m/z 622.2; Multiplet Report 1H NMR (400 MHz, DMSO-d6) δ 8.79 (d, J = 5.2 Hz, 1H), 8.16 (d, J = 1.2 Hz, 1H), 8.08 (dd, J = 9.2, 5.2 Hz, 1H), 7.92 (dd, J = 10.2, 6.2 Hz, 1H), 7.76 (dd, J = 9.3, 5.6 Hz, 1H), 7.66 (dd, J = 5.2, 1.8 Hz, 1H), 7.55-7.45 (m, 2H), 5.62 (s, 2H), 5.07 (dt, J = 9.3, 4.6 Hz, 1H), 4.80 (dd, J = 15.6, 7.1 Hz, 1H), 4.66 (dd, J = 15.6, 2.8 Hz, 1H), 4.59 (d, J = 16.9 Hz, 1H), 4.55-4.45 (m, 2H), 4.35 (dt, J = 9.0, 5.9 Hz, 1H), 2.73 (m, 1H), 2.45-2.33 (m, 1H). |
| 678 | 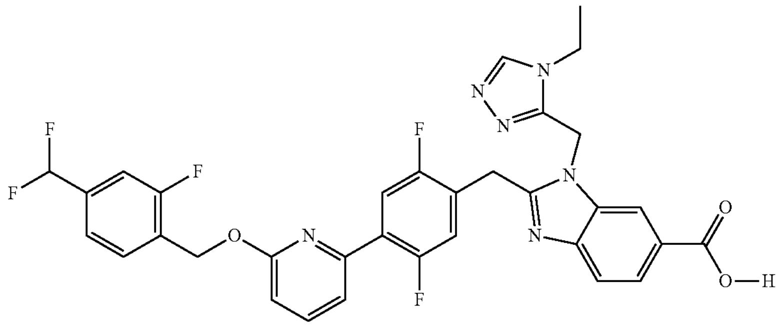 [SMILES: CCn1cnnc1Cn1c(Cc2cc(F)c(-c3cccc(OCc4ccc(C(F)F)cc4F)n3)cc2F)nc2ccc(C(=O)O)cc21] ES/MS m/z 649.2; Multiplet Report 1H NMR (400 MHz, DMSO-d6) δ 8.74 (s, 1H), 8.27 (d, J = 1.5 Hz, 1H), 7.93-7.81 (m, 2H), 7.79-7.64 (m, 3H), 7.54-7.42 (m, 3H), 7.36 (dd, J = 11.5, 6.1 Hz, 1H), 7.06 (t, J = 56 Hz, 1H), 7.00-6.90 (m, 1H), 6.00 (s, 2H), 5.57 (s, 2H), 4.46 (s, 2H), 4.15 (q, J = 7.3 Hz, 2H), 1.35 (t, J = 7.3 Hz, 3H). |

-continued

| Example | Structure/Name/Characterization |
| --- | --- |
| 679 | 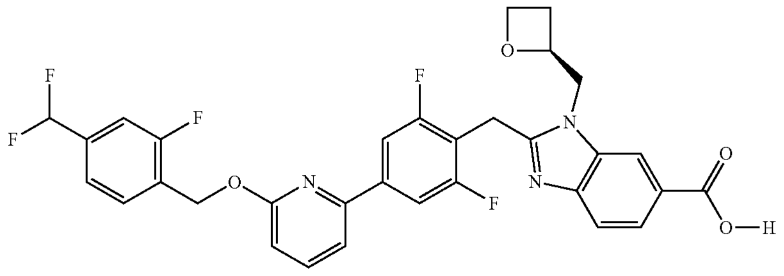 ES/MS m/z 610.2; Multiplet Report 1H NMR (400 MHz, DMSO-d6) δ 8.32 (d, J = 1.5 Hz, 1H), 7.94-7.79 (m, 4H), 7.74 (dd, J = 10.2, 7.5 Hz, 2H), 7.60 (d, J = 8.4 Hz, 1H), 7.54-7.42 (m, 2H), 7.06 (t, J = 56 Hz, 1H), 7.00-6.89 (m, 1H), 5.12 (qd, J = 7.0, 2.6 Hz, 1H), 4.86 (dd, J = 15.6, 7.0 Hz, 1H), 4.71 (dd, J = 15.5, 2.7 Hz, 1H), 4.63 (d, J = 17.3 Hz, 1H), 4.57-4.47 (m, 2H), 4.37 (dt, J = 9.0, 5.9 Hz, 1H), 2.82-2.69 (m, 1H), 2.41 (ddt, J = 11.2, 8.9, 6.9 Hz, 1H). |
| 680 | 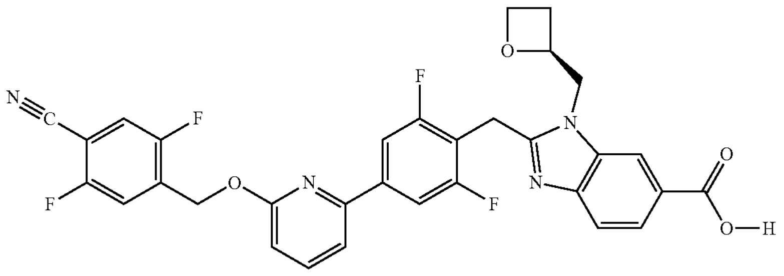 [SMILES: N#Cc1cc(F)c(COc2cccc(-c3cc(F)c(Cc4nc5ccc(C(=O)O)cc5n4C[C@@H]4CCO4)c(F)c3)n2)cc1F] ES/MS m/z 603.2; Multiplet Report 1H NMR (400 MHz, DMSO-d6) δ 8.33 (d, J = 1.5 Hz, 1H), 8.06 (dd, J = 9.2, 5.2 Hz, 1H), 7.90 (q, J = 9.0, 8.4 Hz, 1H), 7.89-7.79 (m, 3H), 7.82-7.72 (m, 2H), 7.60 (d, J = 8.5 Hz, 1H), 7.01 (d, J = 8.2 Hz, 1H), 5.13 (qd, J = 7.1, 2.6 Hz, 1H), 4.86 (dd, J = 15.6, 7.0 Hz, 1H), 4.72 (dd, J = 15.6, 2.7 Hz, 1H), 4.63 (d, J = 17.3 Hz, 1H), 4.58-4.47 (m, 2H), 4.38 (dt, J = 9.0, 5.9 Hz, 1H), 2.75 (dtd, J = 10.6, 8.1, 6.2 Hz, 1H), 2.41 (ddt, J = 11.2, 9.0, 7.0 Hz, 1H). |
| 681 | 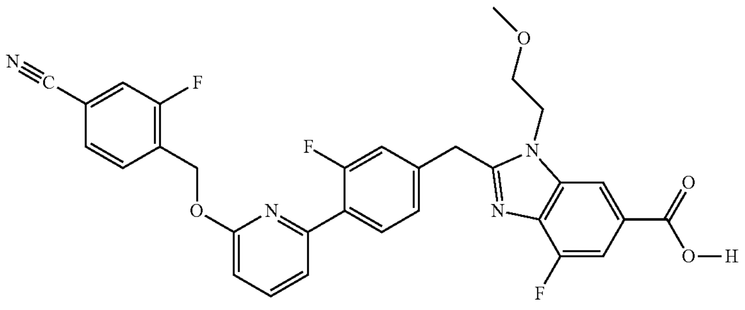 [SMILES: COCCn1c(Cc2ccc(-c3cccc(OCc4ccc(C#N)cc4F)n3)c(F)c2)nc2c(F)cc(C(=O)O)cc21] ES/MS m/z 573.2; Multiplet Report 1H NMR (400 MHz, DMSO-d6) δ 8.08 (d, J = 1.3 Hz, 1H), 7.95-7.82 (m, 3H), 7.80-7.69 (m, 2H), 7.56-7.43 (m, 2H), 7.35-7.25 (m, 2H), 6.94 (d, J = 8.3 Hz, 1H), 5.57 (s, 2H), 4.56 (s, 2H), 4.46 (s, 2H), 3.60 (t, J = 5.0 Hz, 2H), 3.17 (s, 3H). |

Example 43, 2-{[6-[6-[(4-cyano-2-fluoro-phenyl) methoxy]-2-pyridyl]-3-pyridyl]methyl}-3-(2-methoxyethyl)benzimidazole-5-carboxylic acid Procedure 7

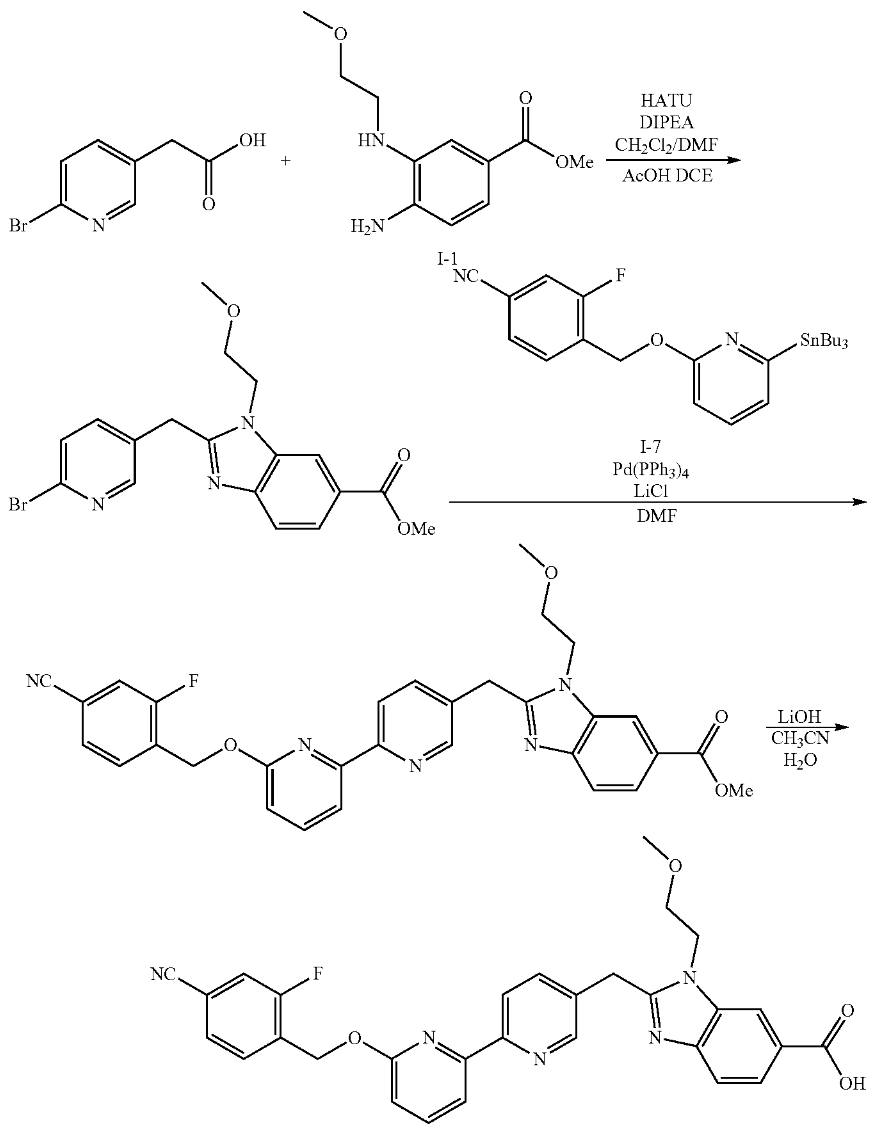

Methyl 2-[(6-bromo-3-pyridyl)methyl]-3-(2-methoxyethyl)benzimidazole-5-carboxylate: To a 25 mL vial was added 2-(6-bromopyridin-3-yl)acetic acid (347 mg, 1.61 mmol), methyl 4-amino-3-(2-methoxyethylamino)benzoate (I-1) (300 mg, 1.34 mmol), and 2-(7-Aza-1H-benzotriazole-1-yl)-1,1,3,3-tetramethyluronium hexafluorophosphate (HATU) (378 mg, 1.61 mmol). To the vial was added $CH_2Cl_2$ (4 mL) and DMF (1 mL), and the mixture was stirred for 15 minutes at room temperature. N,N-Diisopropylethylamine (1.17 mL, 6.69 mmol) was added, and the mixture was stirred at room temperature for 2 hours, at which time LCMS showed conversion of the starting materials to the intermediate amide. The mixture was diluted with EtOAc (100 mL) and washed with sat. aq. $NH_4Cl$ (2×20 mL) and sat. aq. $NaHCO_3$ (2×20 mL). The organic layer was dried over $MgSO_4$, filtered, and concentrated under reduced pressure. The crude material was dissolved in acetic acid (1.5 mL) and dichloroethane (1 mL), and stirred 2 hours at 60° C. LCMS showed conversion of the intermediate amide to the desired product, and the mixture was concentrated under reduced pressure. The crude material was purified by silica gel chromatography (eluent: EtOAc/hexanes, then MeOH/EtOAc) to afford the product: ES/MS: 404.066 ($M+H^+$).

Methyl 2-{[6-[6-[(4-cyano-2-fluoro-phenyl)methoxy]-2-pyridyl]-3-pyridyl]methyl}-3-(2-methoxyethyl)benzimidazole-5-carboxylate: To a 1 dram vial was added methyl 2-[(6-bromo-3-pyridyl)methyl]-3-(2-methoxyethyl)benzimidazole-5-carboxylate (40 mg, 0.0989 mmol), 3-fluoro-4-[(6-tributylstannyl-2-pyridyl)oxymethyl]benzonitrile (I-7) (51 mg, 0.0989 mmol), tetrakis(triphenylphosphine)palladium(0) (23 mg, 0.0198 mmol), and lithium chloride (12.6 mg, 0.297 mmol). DMF (0.5 mL) was added, and the mixture was degassed with argon for 30 seconds. The vial was sealed and stirred overnight at 100° C. LCMS showed conversion of the starting material to the desired product, and the vial was cooled to room temperature. The mixture was transferred directly to a loading column, and the crude material was purified by silica gel chromatography (eluent: EtOAc/hexanes, then MeOH/EtOAc) to afford the desired product: ES/MS: 552.274 ($M+H^+$).

2-{[6-[6-[(4-cyano-2-fluoro-phenyl)methoxy]-2-pyridyl]-3-pyridyl]methyl}-3-(2-methoxyethyl)benzimidazole-5-carboxylic acid: To a 40 mL vial was added methyl 2-{[6-[6-[(4-cyano-2-fluoro-phenyl)methoxy]-2-pyridyl]-3-pyridyl]methyl}-3-(2-methoxyethyl)benzimidazole-5-carboxylate (16.9 mg, 0.0306 mmol), and acetonitrile (1 mL) was added. To the mixture was added LiOH (2 mg, 0.09 mmol) dissolved in water (0.2 mL), and the mixture was stirred 1 hour at 60° C. LCMS showed conversion of the starting material to the product. The mixture was acidified with 50% citric acid (0.2 mL) and 2 drops of trifluoroacetic acid were added. The material was purified by RP-HPLC (eluent: water/MeCN*0.1% TFA) to yield the product Example 43 as a trifluoroacetate salt: ES/MS: 538.448 ($M+H^+$); $^1$H NMR (400 MHz, Methanol-d4) δ 8.78-8.70 (m, 1H), 8.54 (dd, J=1.5, 0.7 Hz, 1H), 8.45 (dd, J=8.2, 0.8 Hz, 1H), 8.20 (dd, J=8.6, 1.5 Hz, 1H), 8.12-8.02 (m, 2H), 7.92 (dd, J=8.3, 7.5 Hz, 1H), 7.81-7.73 (m, 2H), 7.68-7.56 (m, 2H), 7.05 (dd, J=8.2, 0.7 Hz, 1H), 5.71 (s, 2H), 4.83 (t, J=4.9 Hz, 2H), 4.80 (s, 2H), 3.85 (dd, J=5.4, 4.4 Hz, 2H), 3.32 (s, 3H).

Examples 44-45, 102, 425, 434, 601, and 682-684. Compounds Prepared Using Procedure 7

Other compounds of the present disclosure prepared using the general route described in Procedure 7 include the following Examples.

| Example | Structure/Name/Characterization |
|---|---|
| 44 | 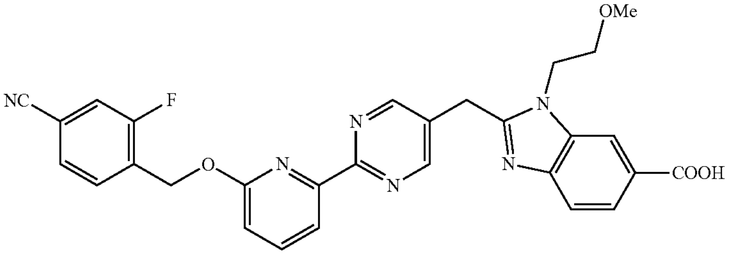 [SMILES: COCCn1c(Cc2cnc(-c3cccc(OCc4ccc(C#N)cc4F)n3)nc2)nc2ccc(C(=O)O)cc21]<br>2-((2-(6-((4-cyano-2-fluorobenzyl)oxy)pyridin-2-yl)pyrimidin-5-yl)methyl)-1-(2-methoxyethyl)-1H-benzo[d]imidazole-6-carboxylic acid: ES/MS m/z 539.3; $^1$H NMR (400 MHz, $CD_3OD$) δ 9.01 (s, 2H), 8.51 (t, J = 1.0 Hz, 1H), 8.22 (dd, J = 7.5, 0.8 Hz, 1H), 8.17 (dd, J = 8.6, 1.5 Hz, 1H), 7.93 (dd, J = 8.3, 7.4 Hz, 1H), 7.87 (t, J = 7.6 Hz, 1H), 7.75 (dd, J = 8.6, 0.6 Hz, 1H), 7.65-7.51 (m, 2H), 7.09 (dd, J = 8.3, 0.8 Hz, 1H), 5.76 (s, 2H), 4.82 (t, J = 5.0 Hz, 2H), 4.76 (s, 2H), 3.86 (t, J = 4.9 Hz, 2H), 3.31 (s, 3H). |
| 45 | 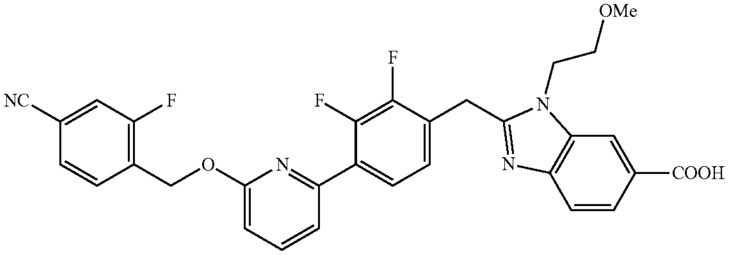 [SMILES: COCCn1c(Cc2ccc(-c3cccc(OCc4ccc(C#N)cc4F)n3)c(F)c2F)nc2ccc(C(=O)O)cc21]<br>2-(4-(6-((4-cyano-2-fluorobenzyl)oxy)pyridin-2-yl)-2,3-difluorobenzyl)-1-(2-methoxyethyl)-1H-benzo[d]imidazole-6-carboxylic acid: ES/MS m/z 573.3; $^1$H NMR (400 MHz, $CD_3OD$) δ 8.45 (d, J = 1.2 Hz, 1H), 8.13 (dd, J = 8.5, 1.5 Hz, 1H), 7.85 (dd, J = 8.3, 7.5 Hz, 1H), 7.82-7.56 (m, 5H), 7.53 (dd, J = 7.4, 1.5 Hz, 1H), 7.28-7.20 (m, 1H), 6.95 (dd, J = 8.3, 0.7 Hz, 1H), 5.62 (s, 2H), 4.82-4.64 (m, 4H), 3.81 (t, J = 4.9 Hz, 2H), 3.31 (s, 3H). |
| 102 | 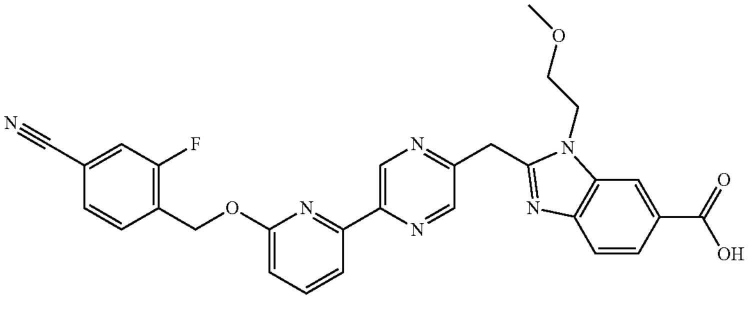 [SMILES: COCCn1c(Cc2cnc(-c3cccc(OCc4ccc(C#N)cc4F)n3)cn2)nc2ccc(C(=O)O)cc21] |

-continued

| Example | Structure/Name/Characterization |
|---|---|
| | 2-((5-(6-((4-cyano-2-fluorobenzyl)oxy)pyridin-2-yl)pyrazin-2-yl)methyl)-1-(2-methoxyethyl)-1H-benzo[d]imidazole-6-carboxylic acid: ES/MS m/z 539.2; $^1$H NMR (400 MHz, MeOD) δ 9.39 (d, J = 1.5 Hz, 1H), 8.80 (d, J = 1.5 Hz, 1H), 8.51 (s, 1H), 8.29-8.13 (m, 1H), 8.07 (d, J = 7.4 Hz, 1H), 7.90 (t, J = 7.9 Hz, 1H), 7.80 (d, J = 8.6 Hz, 1H), 7.74 (t, J = 7.5 Hz, 1H), 7.65-7.50 (m, 2H), 7.03 (d, J = 8.2 Hz, 1H), 5.67 (s, 2H), 4.82 (t, J = 5.0 Hz, 2H), 3.81 (t, J = 4.9 Hz, 2H), 3.24 (s, 3H). |
| 425 | 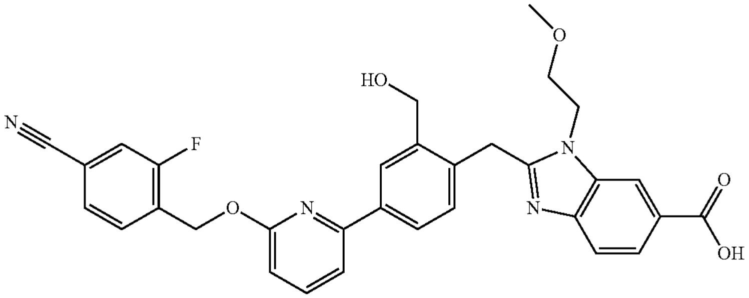 [SMILES: COCCn1c(Cc2ccc(-c3cccc(OCc4ccc(C#N)cc4F)n3)cc2CO)nc2ccc(C(=O)O)cc21] 2-(4-(6-((4-cyano-2-fluorobenzyl)oxy)pyiridn-2-yl)-2-(hydroxymethyl)benzyl)-1-(2-methoxyethyl)-1H-benzo[d]imidazole-6-carboxylic acid: ES/MS m/z 567.5; $^1$H NMR (400 MHz, Methanol-d4) δ 8.57 (s, 1H), 8.23 (dd, J = 8.6, 1.5 Hz, 1H), 8.15 (d, J = 1.9 Hz, 1H), 8.04 (dd, J = 8.0, 1.9 Hz, 1H), 7.82 (t, J = 7.9 Hz, 1H), 7.75 (dt, J = 7.6, 3.2 Hz, 2H), 7.65-7.54 (m, 3H), 7.41 (d, J = 8.0 Hz, 1H), 6.90 (d, J = 8.2 Hz, 1H), 5.67 (s, 2H), 4.85-4.80 (m, 4H), 4.76 (s, 2H), 3.85 (t, J = 4.9 Hz, 2H), 3.36 (s, 3H). |
| 434 | 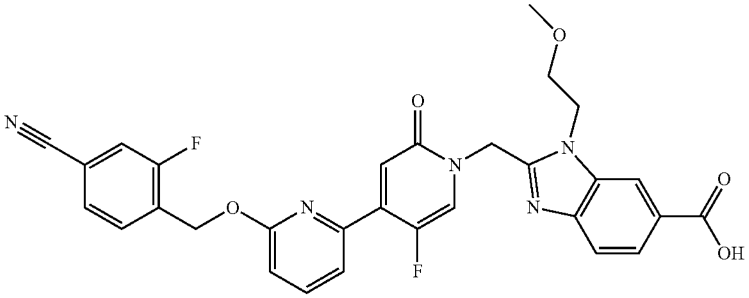 [SMILES: COCCn1c(Cn2cc(F)c(-c3cccc(OCc4ccc(C#N)cc4F)n3)cc2=O)nc2ccc(C(=O)O)cc21] 2-((6-((4-cyano-2-fluorobenzyl)oxy)-5'-fluoro-2'-oxo-[2,4'-bipyridin]-1'(2'H)-yl)methyl)-1-(2-methoxyethyl)-1H-benzo[d]imidazole-6-carboxylic acid: ES/MS m/z 572.1; $^1$H NMR (400 MHz, Methanol-d4) δ 8.35 (s, 1H), 8.08-7.98 (m, 2H), 7.91-7.84 (m, 1H), 7.74 (t, J = 7.5 Hz, 1H), 7.69 (d, J = 8.5 Hz, 1H), 7.64-7.55 (m, 3H), 7.15 (d, J = 7.3 Hz, 1H), 7.05 (d, J = 8.3 Hz, 1H), 5.62 (s, 2H), 5.59 (s, 2H), 4.76 (t, J = 5.0 Hz, 2H), 3.81 (t, J = 4.9 Hz, 2H), 3.32 (s, 3H). |
| 601 | 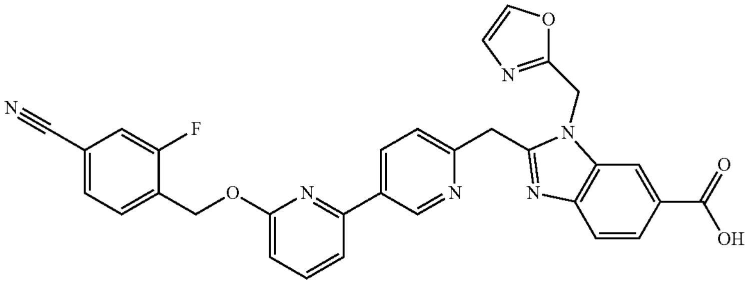 [SMILES: N#Cc1ccc(COc2cccc(-c3ccc(Cc4nc5ccc(C(=O)O)cc5n4Cc4ncco4)nc3)n2)c(F)c1] 2-((6-((4-cyano-2-fluorobenzyl)oxy)-[2,3'-bipyridin]-6'-yl)methyl)-1-(oxazol-2-ylmethyl)-1H-benzo[d]imidazole-6-carboxylic acid: ES/MS m/z 561.5; $^1$H NMR (400 MHz, Methanol-d4) δ 9.07 (dd, J = 2.3, 0.8 Hz, 1H), 8.55-8.40 (m, 2H), 8.16 (dd, J = 8.6, 1.5 Hz, 1H), 7.89-7.77 (m, 3H), 7.73 (d, J = 7.4 Hz, 1H), 7.68-7.50 (m, 4H), 7.07 (d, J = 0.8 Hz, 1H), 7.00-6.92 (m, 1H), 6.00 (s, 2H), 5.66 (s, 2H), 3.32 (d, J = 1.7 Hz, 2H). |

-continued

| Example | Structure/Name/Characterization |
| --- | --- |
| 682 | ES/MS m/z 568.2; 1H NMR (400 MHz, DMSO-d6) δ 9.04 (t, J = 1.5 Hz, 1H), 8.33 (dd, J = 10.9, 1.8 Hz, 1H), 8.26 (d, J = 1.5 Hz, 1H), 7.96-7.86 (m, 2H), 7.81-7.69 (m, 4H), 7.57 (d, J = 8.4 Hz, 1H), 6.99 (d, J = 8.2 Hz, 1H), 5.64 (s, 2H), 5.14-4.98 (m, 1H), 4.82-4.59 (m, 4H), 4.50 (q, J = 7.5 Hz, 1H), 4.36 (dt, J = 9.1, 6.0 Hz, 1H), 2.71 (dt, J = 15.4, 7.1 Hz, 1H), 2.43-2.30 (m, 1H). 19F NMR (376 MHz, DMSO-d6) δ −115.87 (dd, J = 10.0, 6.9 Hz), −125.19 (d, J = 10.9 Hz). |
| 683 | 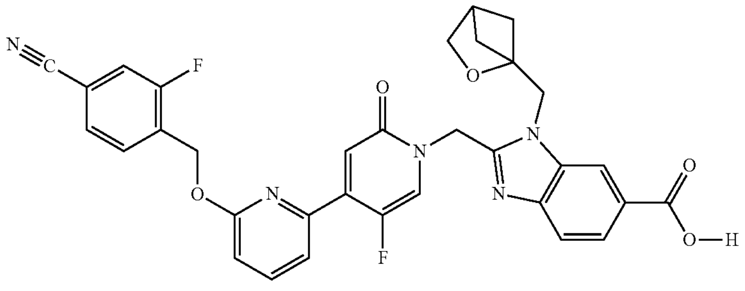 [SMILES: N#Cc1ccc(COc2cccc(-c3cc(=O)n(Cc4nc5ccc(C(=O)O)cc5n4CC45CC(CO4)C5)cc3F)n2)c(F)c1] ES/MS m/z 610.2; 1H NMR (400 MHz, DMSO) δ 8.28 (d, J = 1.5 Hz, 1H), 8.24 (d, J = 7.0 Hz, 1H), 7.97-7.87 (m, 2H), 7.80 (dd, J = 8.5, 1.6 Hz, 1H), 7.77-7.68 (m, 2H), 7.63 (d, J = 8.5 Hz, 1H), 7.51 (dd, J = 7.3, 1.9 Hz, 1H), 7.08 (d, J = 8.3 Hz, 1H), 6.87 (d, J = 7.5 Hz, 1H), 5.56 (s, 2H), 5.47 (s, 2H), 4.89 (s, 2H), 3.62 (s, 2H), 2.90 (t, J = 3.2 Hz, 1H), 1.98-1.92 (m, 2H), 1.42-1.23 (m, 2H). |
| 684 | 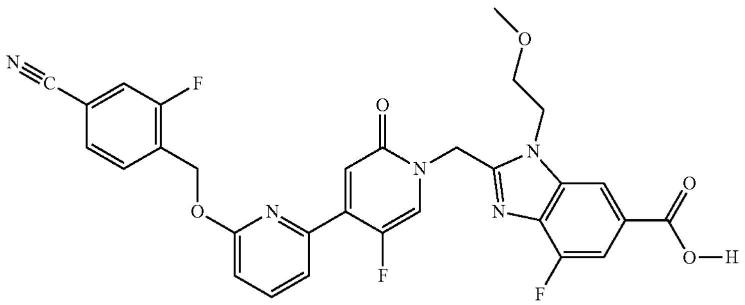 ES/MS m/z 584.2; 1H NMR (400 MHz, DMSO) δ 8.30 (d, J = 1.6 Hz, 1H), 8.25 (d, J = 7.0 Hz, 1H), 7.97-7.87 (m, 2H), 7.81 (dd, J = 8.4, 1.6 Hz, 1H), 7.77-7.69 (m, 2H), 7.65 (d, J = 8.5 Hz, 1H), 7.51 (dd, J = 7.4, 1.9 Hz, 1H), 7.08 (d, J = 8.3 Hz, 1H), 6.88 (d, J = 7.5 Hz, 1H), 5.58-5.50 (m, 3H), 5.42 (d, J = 15.9 Hz, 1H), 5.14-5.04 (m, 1H), 4.84 (dd, J = 15.5, 6.9 Hz, 1H), 4.71 (dd, J = 15.4, 2.7 Hz, 1H), 4.54-4.44 (m, 1H), 4.40-4.30 (m, 1H), 2.79-2.68 (m, 1H), 2.43-2.34 (m, 1H). |

Example 46, 2-(5-(6-((4-cyano-2-fluorobenzyl)oxy)pyridin-2-yl)-2,3-dihydro-1H-inden-1-yl)-1-(2-methoxyethyl)-1H-benzo[d]imidazole-6-carboxylic acid Isomer 1

Example 47, 2-(5-(6-((4-cyano-2-fluorobenzyl)oxy)pyridin-2-yl)-2,3-dihydro-1H-inden-1-yl)-1-(2-methoxyethyl)-1H-benzo[d]imidazole-6-carboxylic acid Isomer 2

Procedure 8

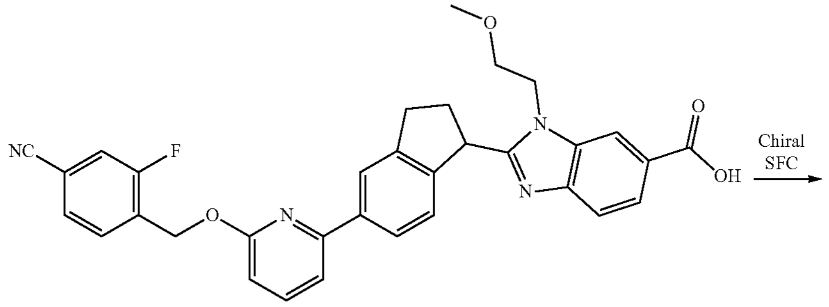

(±)

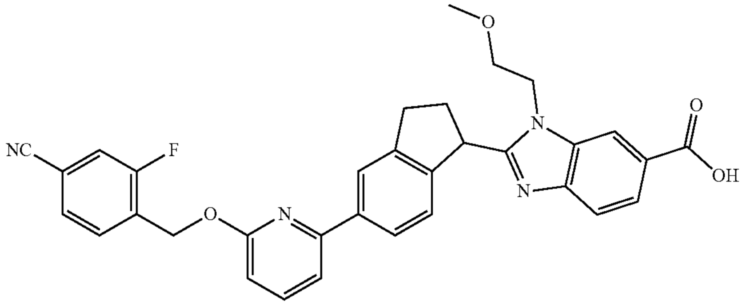

Isomer 1

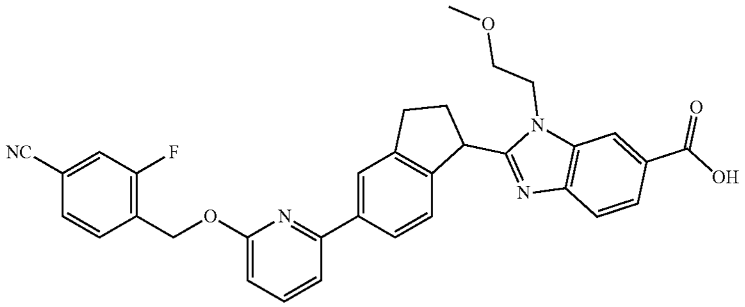

Isomer 2

2-(5-(6-((4-cyano-2-fluorobenzyl)oxy)pyridin-2-yl)-2,3-dihydro-1H-inden-1-yl)-1-(2-methoxyethyl)-1H-benzo[d]imidazole-6-carboxylic acid: Example 36 was prepared in an analogous fashion to Procedure 6, starting from 5-bromo-2,3-dihydro-1H-indene-1-carboxylic acid. The racemic mixture was subjected to SFC (IB column, 45% MeOH-DEA) to afford the corresponding enantiomers. Isomer 1 (Example 46): ES/MS: 563.532 (M+H$^+$); $^1$H NMR (400 MHz, Methanol-$d_4$) δ 8.62 (d, J=1.2 Hz, 1H), 8.25 (dd, J=8.6, 1.4 Hz, 1H), 8.06 (s, 1H), 7.97-7.89 (m, 1H), 7.85-7.70 (m, 3H), 7.67-7.51 (m, 3H), 7.22 (d, J=8.0 Hz, 1H), 6.88 (d, J=8.1 Hz, 1H), 5.66 (s, 2H), 5.36 (t, J=8.4 Hz, 1H), 4.97 (t, J=4.9 Hz, 2H), 3.95-3.86 (m, 2H), 3.38 (s, 3H), 3.30-3.20 (m, 2H), 2.94 (dtd, J=12.3, 8.1, 3.8 Hz, 1H), 2.43 (dq, J=12.9, 8.7 Hz, 1H); Isomer 2 (Example 47): ES/MS: 563.385 (M+H$^+$); $^1$H NMR (400 MHz, Methanol-$d_4$) δ 8.62 (d, J=1.3 Hz, 1H), 8.25 (dd, J=8.6, 1.4 Hz, 1H), 8.06 (d, J=1.6 Hz, 1H), 7.92 (d, J=8.1 Hz, 1H), 7.86-7.69 (m, 3H), 7.67-7.47 (m, 3H), 7.22 (d, J=8.0 Hz, 1H), 6.88 (d, J=8.1 Hz, 1H), 5.66 (s, 2H), 5.36 (t, J=8.5 Hz, 1H), 5.00-4.94 (m, 2H), 3.91 (t, J=4.9 Hz, 2H), 3.38 (s, 3H), 3.29-3.22 (m, 2H), 2.94 (dtd, J=12.2, 8.0, 3.7 Hz, 1H), 2.43 (dq, J=12.8, 8.7 Hz, 1H).

Example 48, 2-(6-(6-((4-cyano-2-fluorobenzyl)oxy)pyridin-2-yl)isochroman-1-yl)-1-(2-methoxyethyl)-1H-benzo[d]imidazole-6-carboxylic acid Isomer 1

Example 49, 2-(6-(6-((4-cyano-2-fluorobenzyl)oxy)pyridin-2-yl)isochroman-1-yl)-1-(2-methoxyethyl)-1H-benzo[d]imidazole-6-carboxylic acid Isomer 2

Procedure 9

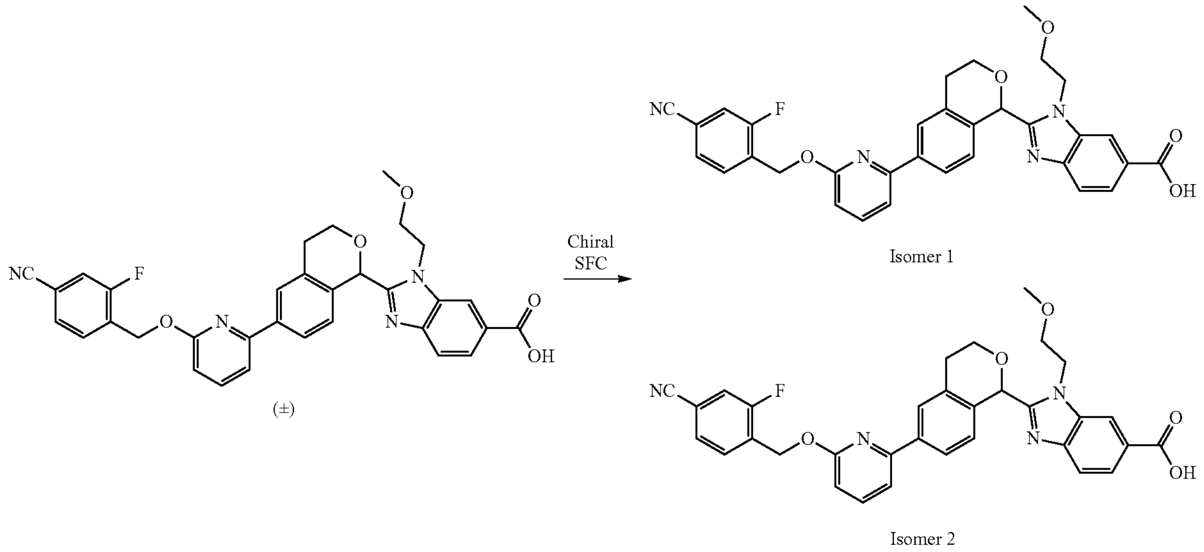 [SMILES: COCCn1c(C2OCCc3cc(-c4cccc(OCc5ccc(C#N)cc5F)n4)ccc32)nc2ccc(C(=O)O)cc21 ; COCCn1c(C2OCCc3cc(-c4cccc(OCc5ccc(C#N)cc5F)n4)ccc32)nc2ccc(C(=O)O)cc21 ; COCCn1c(C2OCCc3cc(-c4cccc(OCc5ccc(C#N)cc5F)n4)ccc32)nc2ccc(C(=O)O)cc21]

2-(6-(6-((4-cyano-2-fluorobenzyl)oxy)pyridin-2-yl)isochroman-1-yl)-1-(2-methoxyethyl)-1H-benzo[d]imidazole-6-carboxylic acid: Example 37 was prepared in an analogous fashion to Procedure 6, starting from I-9. The racemic mixture was subjected to SFC (IG column, 45% EtOH—IPA-NH3) to afford the corresponding enantiomers. Isomer 1 (Example 48): ES/MS: 579.357 ($M+H^+$); $^1H$ NMR (400 MHz, Methanol-d4) δ 8.44 (d, J=1.3 Hz, 1H), 8.08 (dd, J=8.6, 1.5 Hz, 1H), 7.96 (s, 1H), 7.88-7.70 (m, 4H), 7.68-7.49 (m, 3H), 7.01 (d, J=8.2 Hz, 1H), 6.87 (d, J=8.2 Hz, 1H), 6.51 (s, 1H), 5.65 (s, 2H), 4.78-4.59 (m, 2H), 4.25 (dt, J=10.8, 5.2 Hz, 1H), 4.08 (ddd, J=11.8, 7.9, 4.5 Hz, 1H), 3.72 (dt, J=9.4, 4.4 Hz, 1H), 3.66-3.56 (m, 1H), 3.26 (s, 3H), 3.26-3.00 (m, 2H); Isomer 2 (Example 49): ES/MS: 579.489 ($M+H^+$); $^1H$ NMR (400 MHz, Methanol-d4) δ 8.52-8.45 (m, 1H), 8.12 (dd, J=8.6, 1.5 Hz, 1H), 7.97 (s, 1H), 7.86 (dd, J=8.2, 1.9 Hz, 1H), 7.83-7.70 (m, 3H), 7.66-7.51 (m, 3H), 7.03 (d, J=8.2 Hz, 1H), 6.88 (d, J=8.1 Hz, 1H), 6.55 (s, 1H), 5.65 (s, 2H), 4.83-4.63 (m, 2H), 4.23 (dt, J=10.9, 5.2 Hz, 1H), 4.09 (ddd, J=11.7, 7.6, 4.4 Hz, 1H), 3.75 (dt, J=9.4, 4.4 Hz, 1H), 3.70-3.59 (m, 1H), 3.28 (s, 3H), 3.25-3.03 (m, 2H).

Example 50. 2-(4-(6-((4-Cyano-2-fluorobenzyl)oxy)pyridin-2-yl)-2-fluorobenzyl)-N-(cyclopropylsulfonyl)-1-((1-methylcyclopropyl)methyl)-1H-benzo[d]imidazole-6-carboxamide Procedure 10

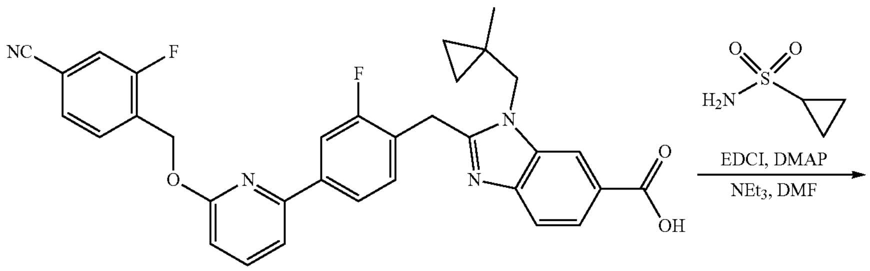

-continued

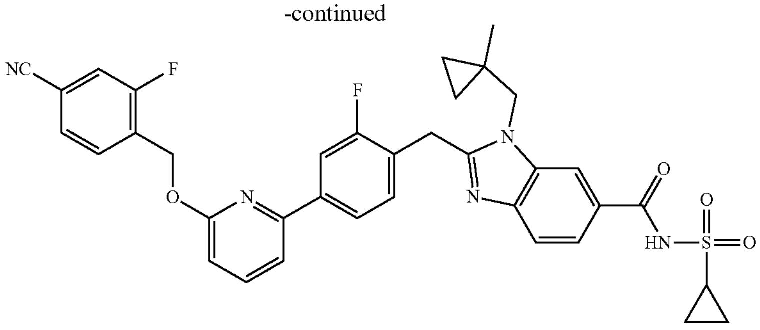

2-(4-(6-((4-Cyano-2-fluorobenzyl)oxy)pyridin-2-yl)-2-fluorobenzyl)-N-(cyclopropylsulfonyl)-1-((1-methylcyclopropyl)methyl)-1H-benzo[d]imidazole-6-carboxamide (Example 50): 2-(4-(6-((4-Cyano-2-fluorobenzyl)oxy)pyridin-2-yl)-2-fluorobenzyl)-1-((1-methylcyclopropyl)methyl)-1H-benzo[d]imidazole-6-carboxylic acid (Example 9, 18.5 mg, 0.033 mmol), cyclopropane sulfonamide (11.9 mg, 0.098 mmol), 4-(Dimethylamino)-pyridine (16.8 mg, 0.14 mmol) and N-(3-dimethylaminopropyl)-N'-ethylcarbodiimide hydrochloride (26.4 mg, 0.138 mmol) were taken up in N,N-dimethylformamide (1.0 mL) and N,N-diisopropylethylamine (0.051 mL, 0.29 mmol) was added. The mixture was stirred at room temperature for 16 hours. Following this time, the reaction was quenched by addition of 0.1 mL trifluoroacetic acid and purified by RP-HPLC (eluent: 15-70% MeCN/water with 0.1% TFA) to yield the product as the trifluoroacetate salt: ES/MS: 668.3 ($M+H^+$); $^1H$ NMR (400 MHz, Methanol-d4) δ 8.47 (dd, J=1.6, 0.6 Hz, 1H), 8.03 (dd, J=8.6, 1.6 Hz, 1H), 7.95-7.77 (m, 4H), 7.74 (t, J=7.6 Hz, 1H), 7.68-7.54 (m, 3H), 7.49 (t, J=7.9 Hz, 1H), 6.92 (d, J=8.1 Hz, 1H), 5.66 (s, 2H), 4.70 (s, 2H), 4.53 (s, 2H), 3.22 (ddd, J=12.9, 8.2, 4.9 Hz, 1H), 1.44-1.29 (m, 2H), 1.27-1.13 (m, 2H), 1.06 (s, 3H), 0.81-0.78 (m, 2H), 0.68-0.51 (m, 2H).

Examples 51-57 163, and 685. Compounds Prepared Using Procedure 10

Other compounds of the present disclosure prepared using the general route described in Procedure 10 include the following Examples.

| Example | Structure/Name/Characterization |
|---|---|
| 51 | 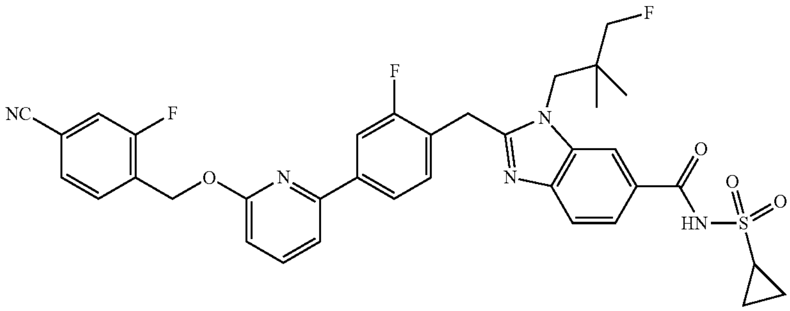<br>2-(4-(6-((4-cyano-2-fluorobenzyl)oxy)pyridin-2-yl)-2-fluorobenzyl)-N-(cyclopropylsulfonyl)-1-(3-fluoro-2,2-dimethylpropyl)-1H-benzo[d]imidazole-6-carboxamide: ES/MS m/z 668.5; $^1H$ NMR (400 MHz, $CD_3OD$) δ 8.58-8.48 (m, 1H), 8.07 (dd, J = 8.6, 1.6 Hz, 1H), 7.97-7.86 (m, 2H), 7.85-7.77 (m, 2H), 7.73 (t, J = 7.5 Hz, 1H), 7.64-7.50 (m, 4H), 6.92 (d, J = 8.2 Hz, 1H), 5.65 (s, 2H), 4.75 (s, 2H), 4.62 (s, 2H), 4.35 (d, J = 47.6 Hz, 2H), 3.21 (tt, J = 8.0, 4.8 Hz, 1H), 1.43-1.27 (m, 2H), 1.27-1.09 (m, 8H). |
| 52 | 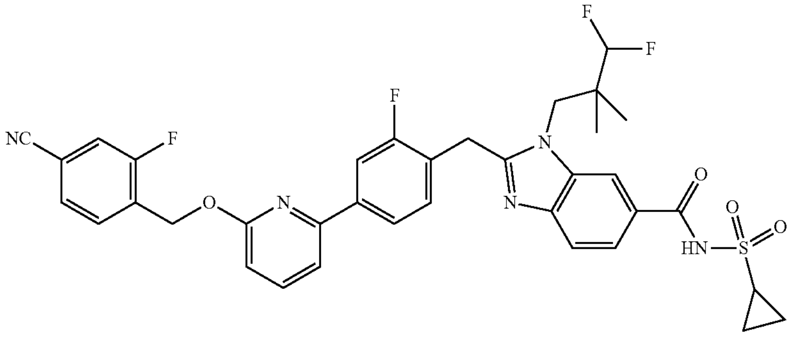 [SMILES: CC(C)(Cn1c(Cc2ccc(-c3cccc(OCc4ccc(C#N)cc4F)n3)cc2F)nc2ccc(C(=O)NS(=O)(=O)C3CC3)cc21)C(F)F] |

-continued

| Example | Structure/Name/Characterization |
|---|---|
| | 2-(4-(6-((4-cyano-2-fluorobenzyl)oxy)pyridin-2-yl)-2-fluorobenzyl)-N-(cyclopropylsulfonyl)-1-(3,3-difluoro-2,2-dimethylpropyl)-1H-benzo[d]imidazole-6-carboxamide: ES/MS m/z 706.3; $^{1}$H NMR (400 MHz, $CD_3OD$) δ 8.49 (d, J = 1.4 Hz, 1H), 8.06 (dd, J = 8.6, 1.6 Hz, 1H), 7.96-7.85 (m, 2H), 7.85-7.77 (m, 2H), 7.73 (t, J = 7.5 Hz, 1H), 7.65-7.49 (m, 4H), 5.97 (d, J = 55.7 Hz, 1H), 5.65 (s, 2H), 4.74 (s, 2H), 4.71 (s, 2H), 3.21 (tt, J = 8.0, 4.7 Hz, 1H), 1.36 (qd, J = 5.7, 1.3 Hz, 2H), 1.27 (s, 6H), 1.23-1.09 (m, 2H). |
| 53 | 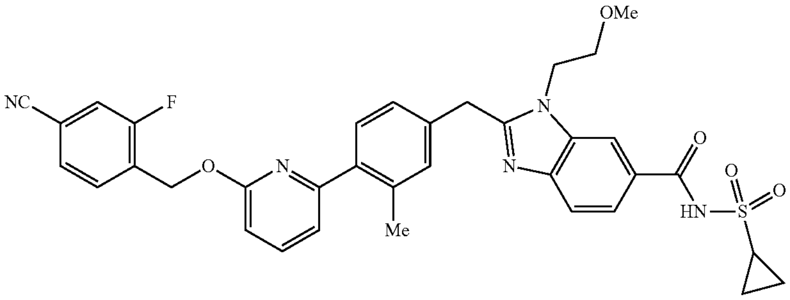 [SMILES: COCCn1c(Cc2ccc(-c3cccc(OCc4ccc(C#N)cc4F)n3)c(C)c2)nc2ccc(C(=O)NS(=O)(=O)C3CC3)cc21] 2-(4-(6-((4-cyano-2-fluorobenzyl)oxy)pyridin-2-yl)-3-methylbenzyl)-N-(cyclopropylsulfonyl)-1-(2-methoxyethyl)-1H-benzo[d]imidazole-6-carboxamide: ES/MS m/z 654.6; $^{1}$H NMR (400 MHz, $CD_3CN$) δ 8.40 (s, 1H), 8.09 (d, J = 8.4 Hz, 1H), 7.88 (d, J = 8.6 Hz, 1H), 7.86-7.77 (m, 1H), 7.67 (t, J = 7.7 Hz, 1H), 7.55 (t, J = 7.8 Hz, 2H), 7.41 (d, J = 7.7 Hz, 1H), 7.31-7.23 (m, 2H), 7.14 (d, J = 7.3 Hz, 1H), 6.90 (d, J = 8.3 Hz, 1H), 5.51 (s, 2H), 4.76-4.57 (m, 4H), 3.76 (t, J = 5.0 Hz, 2H), 3.26 (s, 3H), 3.20-3.07 (m, 1H), 2.28 (s, 3H), 1.34-1.27 (m, 2H), 1.20-1.09 (m, 2H). |
| 54 | 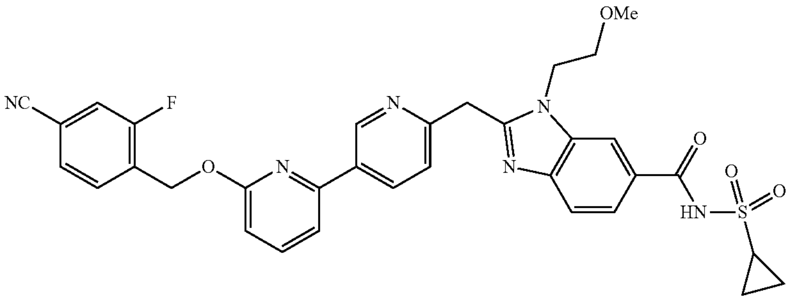 [SMILES: COCCn1c(Cc2ccc(-c3cccc(OCc4ccc(C#N)cc4F)n3)cn2)nc2ccc(C(=O)NS(=O)(=O)C3CC3)cc21] 2-((6-((4-cyano-2-fluorobenzyl)oxy)-[2,3'-bipyridin]-6'-yl)methyl)-N-(cyclopropylsulfonyl)-1-(2-methoxyethyl)-1H-benzo[d]imidazole-6-carboxamide: ES/MS m/z 641.3; $^{1}$H NMR (400 MHz, $CD_3OD$) δ 9.15 (dd, J = 2.3, 0.8 Hz, 1H), 8.52 (dd, J = 8.2, 2.3 Hz, 1H), 8.47 (d, J = 1.6 Hz, 1H), 8.08 (dd, J = 8.6, 1.6 Hz, 1H), 7.89-7.78 (m, 2H), 7.76-7.65 (m, 2H), 7.63-7.49 (m, 3H), 6.94 (d, J = 8.2 Hz, 1H), 5.63 (s, 2H), 4.85 (s, 2H), 4.80 (t, J = 5.0 Hz, 2H), 3.81 (t, J = 4.9 Hz, 2H), 3.25 (s, 3H), 3.21-3.14 (m, 1H), 1.42-1.28 (m, 2H), 1.22-1.08 (m, 2H). |
| 55 | 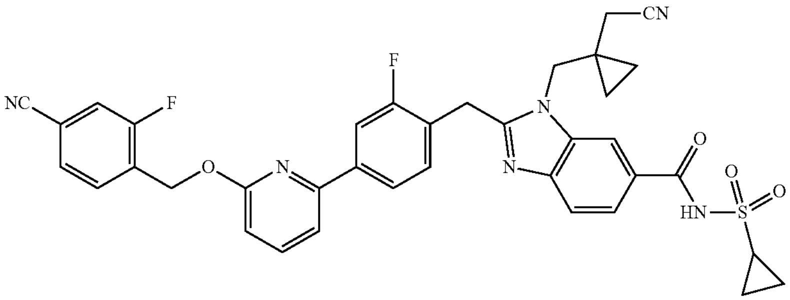 [SMILES: N#CCC1(Cn2c(Cc3ccc(-c4cccc(OCc5ccc(C#N)cc5F)n4)cc3F)nc3ccc(C(=O)NS(=O)(=O)C4CC4)cc32)CC1] 2-(4-(6-((4-cyano-2-fluorobenzyl)oxy)pyridin-2-yl)-2-fluorobenzyl)-1-((1-(cyanomethyl)cyclopropyl)methyl)-N-(cyclopropylsulfonyl)-1H-benzo[d]imidazole-6-carboxamide; ES/MS m/z 693.2; $^{1}$H NMR (400 MHz, DMSO-$d_6$) δ 12.03 (s, 1H), 8.36 (d, J = 1.6 Hz, 1H), 7.98-7.83 (m, 5H), 7.83-7.78 (m, 1H), 7.77-7.71 (m, 2H), 7.66 (dd, J = 12.8, 8.0 Hz, 2H), 7.49 (t, J = 7.9 Hz, 1H), 6.94 (d, J = 8.1 Hz, 1H), 5.63 (s, 2H), 4.55 (s, 2H), 4.49 |

-continued

| Example | Structure/Name/Characterization |
|---|---|
| | (s, 2H), 3.19 (tt, J = 7.9, 4.9 Hz, 1H), 2.73 (s, 2H), 1.27-1.08 (m, 4H), 0.78 (d, J = 4.3 Hz, 2H), 0.74 (d, J = 4.4 Hz, 2H). |
| 56 | 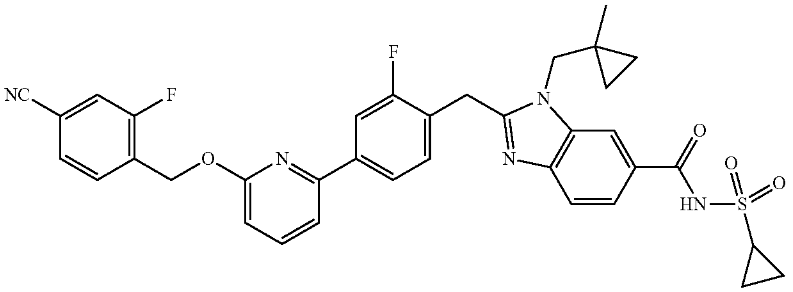 [SMILES: CC1(Cn2c(Cc3ccc(-c4cccc(OCc5ccc(C#N)cc5F)n4)cc3F)nc3ccc(C(=O)NS(=O)(=O)C4CC4)cc32)CC1]<br>2-(4-(6-((4-cyano-2-fluorobenzyl)oxy)pyridin-2-yl)-2-fluorobenzyl)-N-(cyclopropylsulfonyl)-3-((1-methylcyclopropyl)methyl)-3H-imidazo[4,5-b]pyridine-5-carboxamide: ES/MS m/z 669.3; $^1$H NMR (400 MHz, DMSO-$d_6$) δ 11.80 (s, 1H), 8.14 (d, J = 8.2 Hz, 1H), 7.99 (d, J = 8.3 Hz, 1H), 7.95-7.82 (m, 4H), 7.82-7.71 (m, 3H), 7.68 (d, J = 7.4 Hz, 1H), 7.50 (d, J = 8.0 Hz, 1H), 6.94 (d, J = 8.2 Hz, 1H), 5.63 (s, 3H), 4.54 (s, 2H), 4.53 (s, 3H), 3.22-3.10 (m, 1H), 1.23 (q, J = 3.4 Hz, 2H), 1.19-1.08 (m, 2H), 0.97 (s, 3H), 0.86 (d, J = 4.6 Hz, 3H), 0.44 (t, J = 3.0 Hz, 2H). |
| 57 | 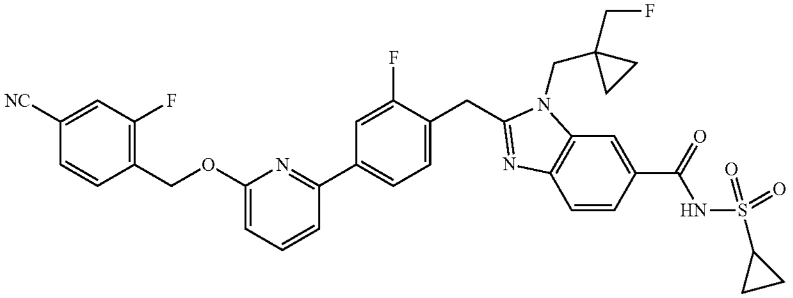 [SMILES: N#Cc1ccc(COc2cccc(-c3ccc(Cc4nc5ccc(C(=O)NS(=O)(=O)C6CC6)cc5n4CC4(CF)CC4)c(F)c3)n2)c(F)c1]<br>2-(4-(6-((4-cyano-2-fluorobenzyl)oxy)pyridin-2-yl)-2-fluorobenzyl)-N-(cyclopropylsulfonyl)-1-((1-(fluoromethyl)cyclopropyl)methyl)-1H-benzo[d]imidazole-6-carboxamide; ES/MS m/z 686.6; $^1$H NMR (400 MHz, $CD_3OD$) δ 8.48 (s, 1H), 8.04 (dd, J = 8.5, 1.5 Hz, 1H), 7.94-7.85 (m, 2H), 7.85-7.77 (m, 2H), 7.73 (t, J = 7.5 Hz, 1H), 7.61 (dd, J = 9.7, 1.5 Hz, 1H), 7.57 (d, J = 7.6 Hz, 2H), 7.50 (t, J = 7.9 Hz, 1H), 5.65 (s, 2H), 4.74 (s, 2H), 4.72 (s, 2H), 4.26 (d, J = 48.7 Hz, 2H), 3.21 (tt, J = 8.0, 4.8 Hz, 1H), 1.35 (tt, J = 5.5, 3.2 Hz, 2H), 1.22-1.13 (m, 2H), 1.01 (t, J = 5.2 Hz, 2H), 0.90 (t, J = 5.4 Hz, 2H). |
| 163 | 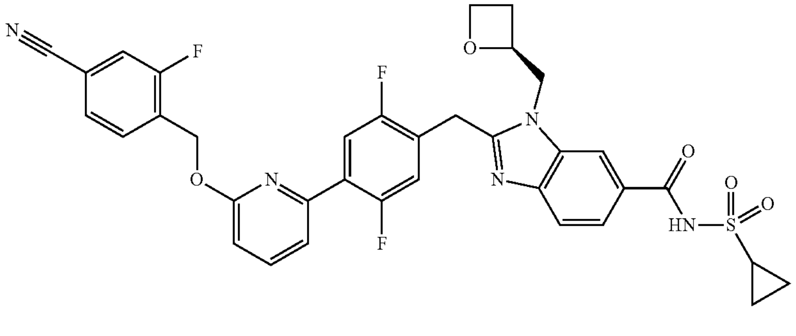 [SMILES: N#Cc1ccc(COc2cccc(-c3cc(F)c(Cc4nc5ccc(C(=O)NS(=O)(=O)C6CC6)cc5n4C[C@@H]4CCO4)cc3F)n2)c(F)c1]<br>(S)-2-(4-(6-((4-cyano-2-fluorobenzyl)oxy)pyridin-2-yl)-2,5-difluorobenzyl)-N-(cyclopropylsulfonyl)-1-(oxetan-2-ylmethyl)-1H-benzo[d]imidazole-6-carboxamide: ES/MS m/z 688.2; $^1$H NMR (400 MHz, DMSO) δ 11.98 (s, 1H), 8.32 (d, J = 1.8 Hz, 1H), 7.95-7.86 (m, 2H), 7.81-7.69 (m, 4H), 7.65 (d, J = 8.5 Hz, 1H), 7.56-7.50 (m, 1H), 7.39 (dd, J = 11.4, 6.1 Hz, 1H), 6.99 (d, J = 8.2 Hz, 1H), 5.60 (s, 2H), 5.18-5.08 (m, 1H), 4.76 (dd, J = 15.4, 7.3 Hz, 1H), 4.66-4.37 (m, 5H), 3.23-3.13 (m, 1H), 2.80-2.70 (m, 1H), 2.48-2.45 (m, 1H), 1.25-1.08 (m, 4H). |

-continued
| Example | Structure/Name/Characterization |
| --- | --- |
| 685 | 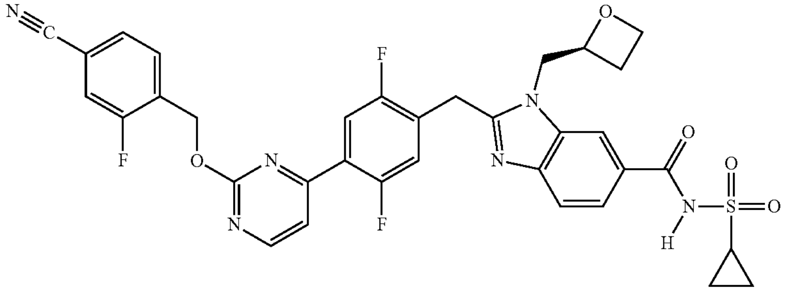 [SMILES: N#Cc1ccc(COc2nccc(-c3cc(F)c(Cc4nc5ccc(C(=O)NS(=O)(=O)C6CC6)cc5n4C[C@@H]4CCO4)cc3F)n2)c(F)c1] ES/MS m/z 689.2; 1H NMR (400 MHz, Methanol-d4) δ 8.71 (d, J = 5.2 Hz, 1H), 8.41-8.23 (m, 1H), 8.08-7.89 (m, 2H), 7.89-7.70 (m, 2H), 7.70-7.54 (m, 3H), 7.37 (dd, J = 11.3, 5.9 Hz, 1H), 5.70 (s, 2H), 5.27 (d, J = 6.2 Hz, 1H), 4.79-4.56 (m, 4H), 4.51 (dt, J = 9.1, 5.9 Hz, 1H), 3.26-3.12 (m, 1H), 3.01-2.70 (m, 1H), 2.64-2.40 (m, 1H), 1.48-1.23 (m, 3H), 1.23-1.00 (m, 2H). (Multiplet Report) 19F NMR (376 MHz, Methanol-d4) δ −77.91, −117.57 (t, J = 9.4 Hz), −118.99-−121.85 (m), −121.85-−124.78 (m). |
Example 58. 2-((5-(6-((4-cyano-2-fluorobenzyl)oxy)pyridin-2-yl)pyrimidin-2-yl)methyl)-1-(2-methoxyethyl)-1H-benzo[d]imidazole-6-carboxylic acid
Procedure 11
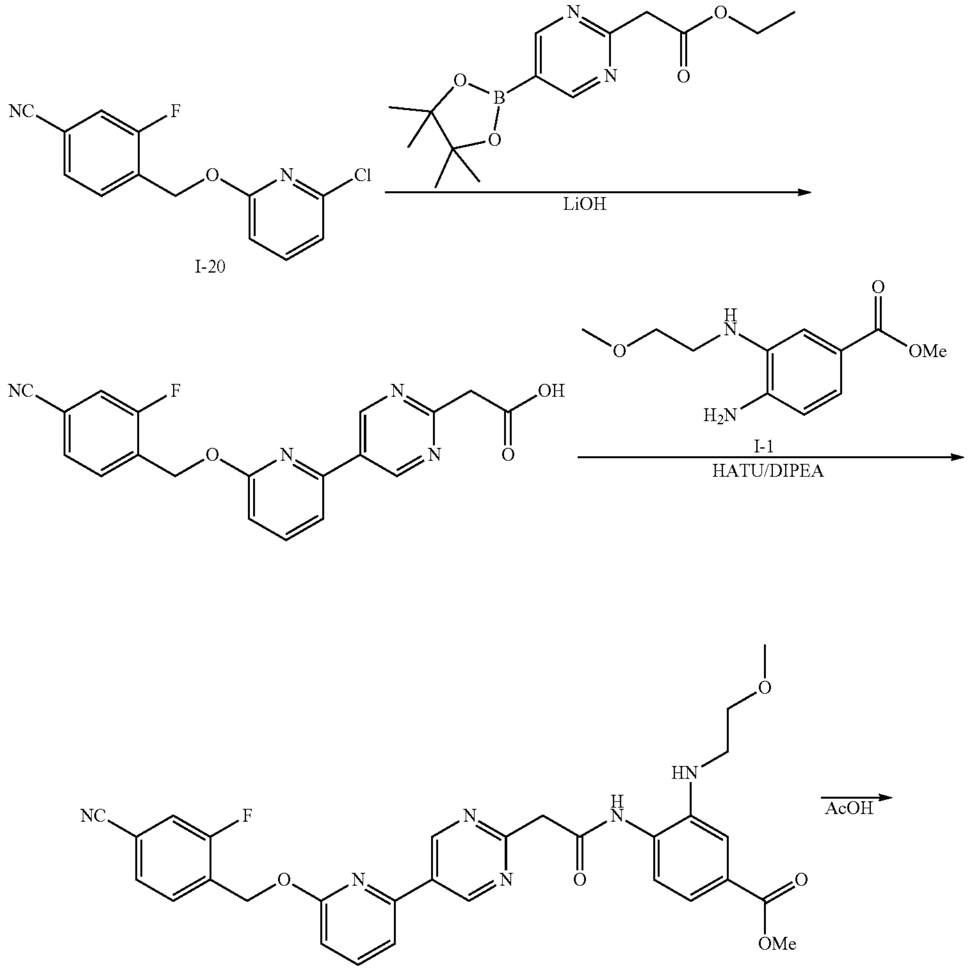

-continued

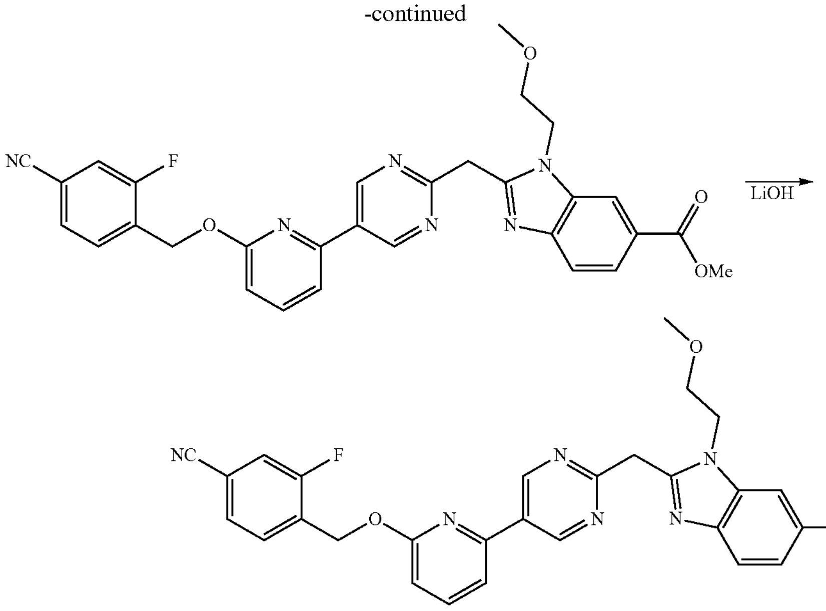

2-(5-(6-((4-cyano-2-fluorobenzyl)oxy)pyridin-2-yl)pyrimidin-2-yl)acetic acid: To a solution of 4-(((6-chloropyridin-2-yl)oxy)methyl)-3-fluorobenzonitrile (I-20) (200 mg, 0.76 mmol) in dioxane (3 mL) was added XPhos Pd G2 (52 mg, 0.069 mmol), sodium carbonate (43 mg, 0.69 mmol) and ethyl 2-(5-(4,4,5,5-tetramethyl-1,3,2-dioxaborolan-2-yl)pyrimidin-2-yl)acetate (200 mg, 0.69 mmol). The resulting solution was degassed by bubbling argon for 5 minutes, sealed, and heated for 2 hrs at 100° C. Upon completion the reaction contents were poured into water (5 mL), and extracted with EtOAc (2×10 mL). The combined organic extracts were washed with brine (5 mL), dried over $MgSO_4$, and purified by silica gel chromatography (eluent: EtOAc/hexanes). Then ethyl 2-(5-(6-((4-cyano-2-fluorobenzyl)oxy)pyridin-2-yl)pyrimidin-2-yl)acetate (20 mg, 0.05 mmol) was dissolved in acetonitrile (1 mL) after which LiOH (2.5 mg, 0.1 mmol) as a solution in water (0.25 mL) was added and the resulting mixture stirred at 60° C. for 1 hr. The mixture was adjusted to pH 2 using 1.0 M citric acid solution and extracted with EtOAc (2×10 mL). The combined organics were then washed with brine (5 mL), dried over $MgSO_4$, filtered, concentrated: ES/MS: 365.1 ($M+H^+$).

2-((5-(6-((4-cyano-2-fluorobenzyl)oxy)pyridin-2-yl)pyrimidin-2-yl)methyl)-1-(2-methoxyethyl)-1H-benzo[d]imidazole-6-carboxylic acid (Example 58): 2-(5-(6-((4-cyano-2-fluorobenzyl)oxy)pyridin-2-yl)pyrimidin-2-yl)acetic acid was elaborated to the final compound as described in Procedure 1 substituting 2-(4-(6-((4-Cyano-2-fluorobenzyl)oxy)pyridin-2-yl)phenyl)acetic acid with 2-(5-(6-((4-cyano-2-fluorobenzyl)oxy)pyridin-2-yl)pyrimidin-2-yl)acetic acid. ES/MS: 539.3 ($M+H^+$); $^1H$ NMR (400 MHz, $CD_3OD$) δ 9.33 (s, 2H), 8.53 (d, J=1.3 Hz, 1H), 8.21 (dd, J=8.6, 1.4 Hz, 1H), 7.92-7.77 (m, 2H), 7.77-7.49 (m, 4H), 6.97 (d, J=8.2 Hz, 1H), 5.63 (s, 2H), 4.79 (t, J=5.0 Hz, 4H), 3.78 (t, J=4.9 Hz, 2H), 3.21 (s, 3H).

Examples 59 and 686. Compounds Prepared Using Procedure 11

Other compounds of the present disclosure prepared using the general route described in Procedure 11 includes the following Example.

| Example | Structure/Name/Characterization |
|---|---|
| 59 | 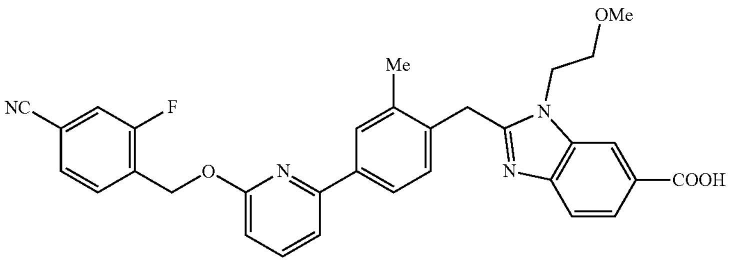 [SMILES: COCCn1c(Cc2ccc(-c3cccc(OCc4ccc(C#N)cc4F)n3)cc2C)nc2ccc(C(=O)O)cc21] 2-(4-(6-((4-cyano-2-fluorobenzyl)oxy)pyridin-2-yl)-2-methylbenzyl)-1-(2-methoxyethyl)-1H-benzo[d]imidazole-6-carboxylic acid: ES/MS m/z 551.7; $^1H$ NMR (400 MHz, $CD_3OD$) δ 8.56 (s, 1H), 8.22 (dd, J = 8.6, 1.4 Hz, 1H), 7.96 (d, J = 1.9 Hz, 1H), 7.88 (dd, J = 8.0, 1.9 Hz, 1H), 7.83-7.66 (m, 4H), 7.65-7.47 (m, 4H), 7.29 (d, J = 8.0 Hz, 1H), 6.86 (d, J = 8.2 Hz, 1H), 5.63 (s, 2H), 4.84-4.67 (m, 5H), 3.83 (t, J = 4.9 Hz, 2H), 3.33-3.24 (m, 2H), 2.38 (s, 3H). |

-continued
| Example | Structure/Name/Characterization |
|---|---|
| 686 | 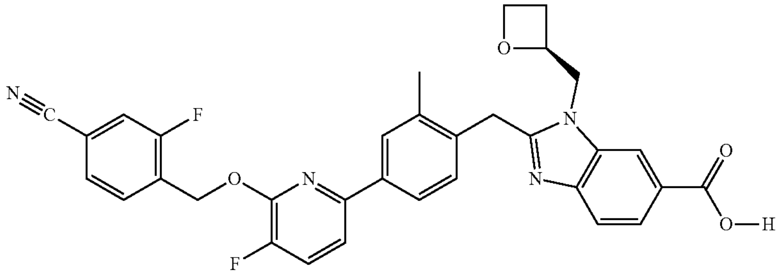 [SMILES: Cc1cc(-c2ccc(F)c(OCc3ccc(C#N)cc3F)n2)ccc1Cc1nc2ccc(C(=O)O)cc2n1C[C@@H]1CCO1]<br>ES/MS m/z 581.2; (Multiplet report) 1H NMR (400 MHz, DMSO-d6) δ 8.27 (s, 1H), 7.95 (d, J = 9.8 Hz, 1H), 7.79 (m, 7H), 7.60 (d, J = 8.4 Hz, 1H), 7.17 (d, J = 8.2 Hz, 1H), 5.70 (s, 2H), 4.52-4.42 (m, 3H), 2.7 (m, 2H), 2.33 (m, 2H). |
Example 60, 2-{[5-[6-[(4-cyano-2-fluoro-phenyl)methoxy]-2-pyridyl]-3-fluoro-2-pyridyl]methyl}-3-(2-methoxyethyl)benzimidazole-5-carboxylic acid
Procedure 12
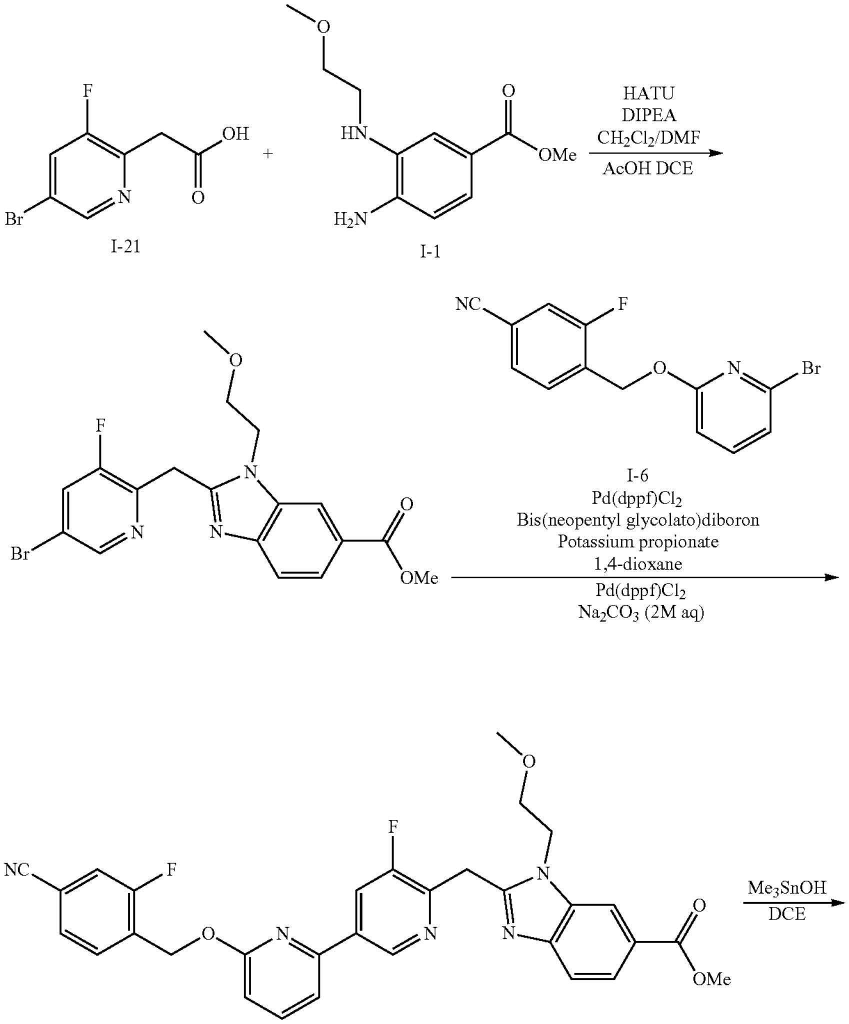

-continued

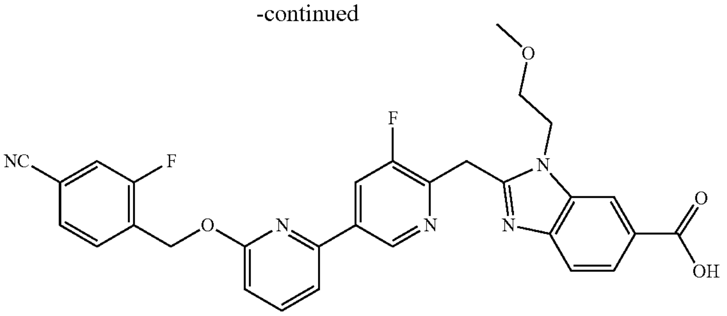

Methyl 2-[(5-bromo-3-fluoro-2-pyridyl)methyl]-3-(2-methoxyethyl)benzimidazole-5-carboxylate: To a 40 mL vial was added 2-(5-bromo-3-fluoro-2-pyridyl)acetic acid (344 mg, 1.47 mmol) (I-21), methyl 4-amino-3-(2-methoxyethylamino)benzoate (I-1) (300 mg, 1.34 mmol), and 2-(7-Aza-1H-benzotriazole-1-yl)-1,1,3,3-tetramethyluronium hexafluorophosphate (HATU) (378 mg, 1.61 mmol). To the vial was added $CH_2Cl_2$ (4 mL) and DMF (1 mL), and the mixture was stirred for 15 minutes at room temperature. N,N-Diisopropylethylamine (1.17 mL, 6.69 mmol) was added, and the mixture was stirred at room temperature for 4 hours, at which time LCMS showed conversion of the starting materials to the intermediate amide. The mixture was diluted with EtOAc (100 mL) and washed with sat. aq. $NH_4Cl$ (2×20 mL) and sat. aq. $NaHCO_3$ (2×20 mL). The organic layer was dried over $MgSO_4$, filtered, and concentrated under reduced pressure. The crude material was dissolved in acetic acid (2 mL) and dichloroethane (2 mL), and stirred 4 hours at 60° C. LCMS showed conversion of the intermediate amide to the desired product, and the mixture was concentrated under reduced pressure. The crude material was purified by silica gel chromatography (eluent: EtOAc/hexanes) to afford the desired product: ES/MS: 422.701 ($M+H^+$).

Methyl 2-{[5-[6-[(4-cyano-2-fluoro-phenyl)methoxy]-2-pyridyl]-3-fluoro-2-pyridyl]methyl}-3-(2-methoxyethyl)benzimidazole-5-carboxylate: To a vial was added methyl 2-[(5-bromo-3-fluoro-2-pyridyl)methyl]-3-(2-methoxyethyl)benzimidazole-5-carboxylate (150 mg, 0.355 mmol), bis(neopentyl glycolato)diboron (104 mg, 0.462 mmol), $Pd(dppf)Cl_2$ (40 mg, 0.053 mmol), and potassium propionate (120 mg, 1.07 mmol). 1,4-Dioxane (1.5 mL) was added, and the mixture was degassed with argon for 30 seconds. The vial was sealed, and the mixture was heated for 1 hour at 120° C. The vial was cooled, and LCMS showed conversion of the starting aryl bromide to the intermediate boronic acid. $Pd(dppf)Cl_2$ (20 mg, 0.025 mmol) and 4-[(6-bromo-2-pyridyl)oxymethyl]-3-fluoro-benzonitrile (I-6) (109 mg, 0.355 mmol) were added, and the flask was sealed and stirred 1 hour at 90° C. LCMS showed conversion to the desired product, and the flask was cooled to room temperature. The organic layer was transferred directly to a loading column, and the crude material was purified by silica gel chromatography (eluent: EtOAc/hexanes) to afford the desired product: ES/MS: 570.585 ($M+H^+$).

2-{[5-[6-[(4-cyano-2-fluoro-phenyl)methoxy]-2-pyridyl]-3-fluoro-2-pyridyl]methyl}-3-(2-methoxyethyl)benzimidazole-5-carboxylic acid): To a 40 mL vial was added methyl 2-{[5-[6-[(4-cyano-2-fluoro-phenyl)methoxy]-2-pyridyl]-3-fluoro-2-pyridyl]methyl}-3-(2-methoxyethyl)benzimidazole-5-carboxylate (105 mg, 0.184 mmol), and 1,2-dichloroethane (1 mL) was added. To the mixture was added trimethyltin hydroxide (333 mg, 1.84 mmol), and the mixture was stirred 48 hours at 80° C. LCMS showed conversion of the starting material to the product. The mixture was concentrated under reduced pressure, and acetonitrile (1.5 mL) and water (0.2 mL) were added. The mixture was acidified with 10 drops of trifluoroacetic acid, and the mixture was filtered through an acrodisc. The filtrate was purified by RP-HPLC (eluent: water/MeCN*0.1% TFA) to yield the product Example 60 as a trifluoroacetate salt: ES/MS: 556.450 ($M+H^+$); $^1H$ NMR (400 MHz, $CD_3OD$) δ 8.99 (q, J=1.4 Hz, 1H), 8.54 (s, 1H), 8.29 (dt, J=10.7, 1.3 Hz, 1H), 8.22 (dd, J=8.5, 1.5 Hz, 1H), 7.90-7.77 (m, 2H), 7.73 (t, J=7.5 Hz, 1H), 7.68-7.54 (m, 3H), 6.97 (d, J=8.3 Hz, 1H), 5.66 (s, 2H), 4.83-4.79 (m, 2H), 3.81 (t, J=5.0 Hz, 2H), 3.26 (s, 3H).

Examples 61, 421-424, 437, and 518. Compounds Prepared Using Procedure 12

Other compounds of the present disclosure prepared using the general route described in Procedure 12 include the following Example.

| Example | Structure/Name/Characterization |
|---|---|
| 61 | 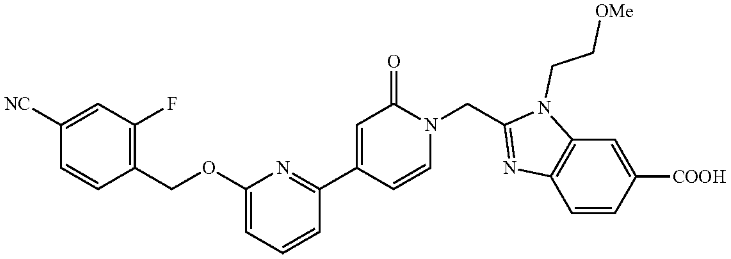 [SMILES: COCCn1c(Cn2ccc(-c3cccc(OCc4ccc(C#N)cc4F)n3)cc2=O)nc2ccc(C(=O)O)cc21] 2-((6-((4-cyano-2-fluorobenzyl)oxy)-2'-oxo-[2,4'-bipyridin]-1'(2'H)-yl)methyl)-1-(2-methoxyethyl)-1H-benzo[d]imidazole-6-carboxylic acid: ES/MS m/z 554.3; $^1H$ NMR (400 MHz, $CD_3OD$) δ 8.35 (s, 1H), 8.01 (dd, J = 8.6, 1.5 Hz, 1H), 7.93 (d, J = 7.1 Hz, 1H), 7.86 (t, J = 7.9 Hz, 1H), 7.75 (t, J = 7.5 Hz, |

-continued

| Example | Structure/Name/Characterization |
|---|---|
| | 1H), 7.68 (d, J = 8.6 Hz, 1H), 7.65-7.52 (m, 3H), 7.25 (d, J = 1.9 Hz, 1H), 7.17-7.05 (m, 1H), 7.01 (d, J = 8.3 Hz, 1H), 5.65 (s, 2H), 5.60 (s, 2H), 4.79-4.75 (m, 2H), 3.80 (t, J = 4.9 Hz, 2H), 3.31 (s, 3H). |
| 421 | 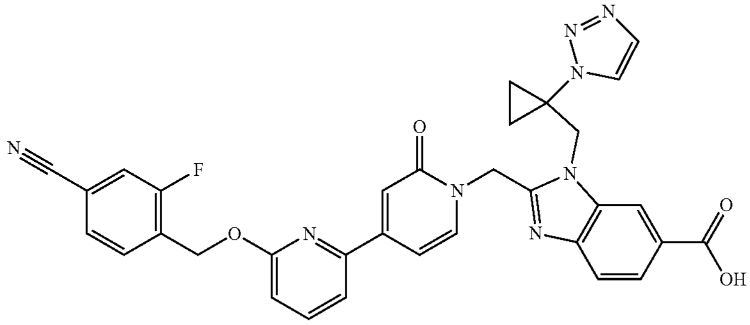 [SMILES: N#Cc1ccc(COc2cccc(-c3ccn(Cc4nc5ccc(C(=O)O)cc5n4CC4(n5ccnn5)CC4)c(=O)c3)n2)c(F)c1] 1-((1-(1H-1,2,3-triazol-1-yl)cyclopropyl)methyl)-2-((6-((4-cyano-2-fluorobenzyl)oxy)-2'-oxo-[2,4'-bipyridin]-1'(2'H)-yl)methyl)-1H-benzo[d]imidazole-6-carboxylic acid: ES/MS m/z 617.2; $^1$H NMR (400 MHz, Methanol-d4) δ 8.01-7.91 (m, 3H), 7.90-7.82 (m, 2H), 7.74 (t, J = 7.5 Hz, 1H), 7.66-7.53 (m, 5H), 7.22 (d, J = 1.9 Hz, 1H), 7.13 (dd, J = 7.2, 2.0 Hz, 1H), 7.01 (d, J = 8.3 Hz, 1H), 5.64 (s, 2H), 5.19 (s, 2H), 5.13 (s, 2H), 1.81-1.72 (m, 2H), 1.64-1.54 (m, 2H). |
| 422 | 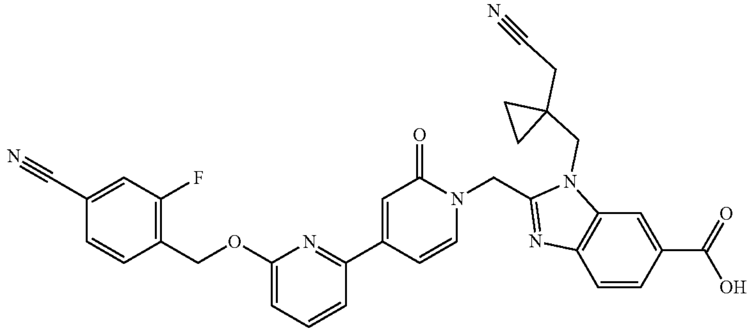 [SMILES: N#CCC1(Cn2c(Cn3ccc(-c4cccc(OCc5ccc(C#N)cc5F)n4)cc3=O)nc3ccc(C(=O)O)cc32)CC1] 2-((6-((4-cyano-2-fluorobenzyl)oxy)-2'-oxo-[2,4'-bipyridin]-1'(2'H)-yl)methyl)-1-((1-(cyanomethyl)cyclopropyl)methyl)-1H-benzo[d]imidazole-6-carboxylic acid: ES/MS m/z 589.4; 1H NMR (400 MHz, Methanol-d4) δ 8.52-8.44 (m, 1H), 8.06 (dd, J = 8.5, 1.5 Hz, 1H), 7.98 (d, J = 7.1 Hz, 1H), 7.87 (dd, J = 8.3, 7.4 Hz, 1H), 7.78-7.52 (m, 5H), 7.26 (d, J = 1.9 Hz, 1H), 7.17 (dd, J = 7.2, 2.0 Hz, 1H), 7.02 (d, J = 8.2 Hz, 1H), 5.69-5.58 (m, 4H), 4.76 (s, 2H), 2.68 (s, 2H), 1.02-0.94 (m, 2H), 0.94-0.83 (m, 2H). |
| 423 | 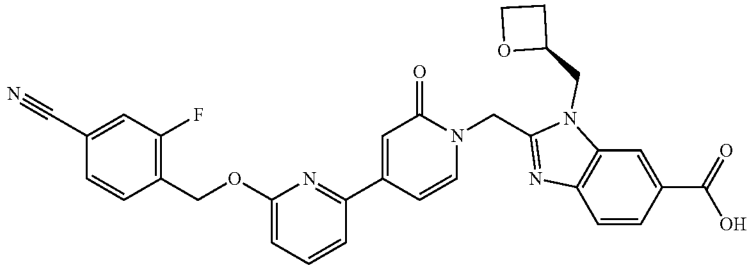 [SMILES: N#Cc1ccc(COc2cccc(-c3ccn(Cc4nc5ccc(C(=O)O)cc5n4C[C@@H]4CCO4)c(=O)c3)n2)c(F)c1] (S)-2-((6-((4-cyano-2-fluorobenzyl)oxy)-2'-oxo-[2,4'-bipyridin]-1'(2'H)-yl)methyl)-1-(oxetan-2-ylmethyl)-1H-benzo[d]imidazole-6-carboxylic acid: ES/MS m/z 566.3; $^1$H NMR (400 MHz, Methanol-d4) δ 8.42 (s, 1H), 8.06 (d, J = 8.5 Hz, 1H), 7.95 (d, J = 7.2 Hz, 1H), 7.87 (t, J = 7.9 Hz, 1H), 7.72 (t, J = 8.3 Hz, 2H), 7.60 (ddd, J = 15.3, 7.7, 1.8 Hz, 3H), 7.25 (s, 1H), 7.14 (d, J = 7.0 Hz, 1H), 7.02 (d, J = 8.3 Hz, 1H), 5.77 (d, J = 16.0 Hz, 1H), 5.65 (s, 2H), 5.60 (d, J = 16.1 Hz, 1H), 5.26 (d, J = 7.3 Hz, 1H), 5.03-4.90 (m, 2H), 4.67 (q, J = 7.4 Hz, 1H), 4.48 (dt, J = 9.2, 6.0 Hz, 1H), 2.85 (p, J = 7.6 Hz, 1H), 2.53 (p, J = 7.9 Hz, 1H). |

-continued

| Example | Structure/Name/Characterization |
|---|---|
| 424 | 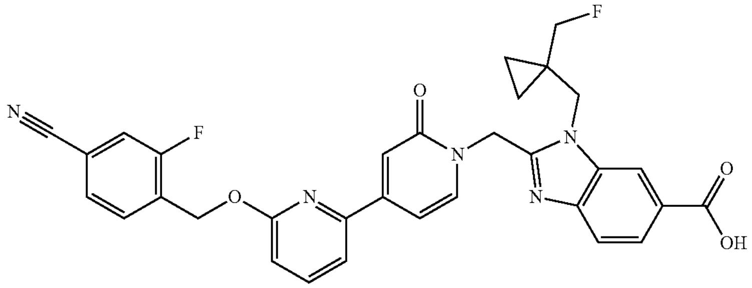 [SMILES: N#Cc1ccc(COc2cccc(-c3ccn(Cc4nc5ccc(C(=O)O)cc5n4CC4(CF)CC4)c(=O)c3)n2)c(F)c1] 2-((6-((4-cyano-2-fluorobenzyl)oxy)-2'-oxo-[2,4'-bipyridin]-1'(2'H)-yl)methyl)-1-((1-(fluoromethyl)cyclopropyl)methyl)-1H-benzo[d]imidazole-6-carboxylic acid: ES/MS m/z 582.5; $^1$H NMR (400 MHz, Methanol-d4) δ 8.41 (s, 1H), 8.03 (dd, J = 8.5, 1.5 Hz, 1H), 7.96 (d, J = 7.2 Hz, 1H), 7.87 (t, J = 7.9 Hz, 1H), 7.75 (t, J = 7.5 Hz, 1H), 7.71-7.53 (m, 4H), 7.25 (d, J = 1.9 Hz, 1H), 7.15 (dd, J = 7.1, 2.0 Hz, 1H), 7.02 (d, J = 8.3 Hz, 1H), 5.64 (d, J = 8.7 Hz, 4H), 4.73 (s, 2H), 4.30 (s, 1H), 4.18 (s, 1H), 1.05-0.96 (m, 2H), 0.92-0.79 (m, 2H). |
| 437 | 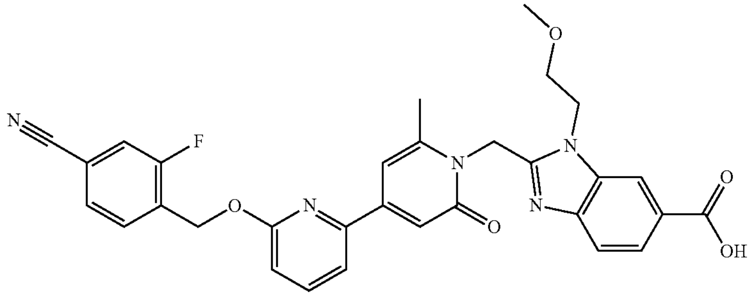 [SMILES: COCCn1c(Cn2c(C)cc(-c3cccc(OCc4ccc(C#N)cc4F)n3)cc2=O)nc2ccc(C(=O)O)cc21] 2-((6-((4-cyano-2-fluorobenzyl)oxy)-6'-methyl-2'-oxo-[2,4'-bipyridin]-1'(2'H)-yl)methyl)-1-(2-methoxyethyl)-1H-benzo[d]imidazole-6-carboxylic acid: ES/MS m/z 568.3; $^1$H NMR (400 MHz, Methanol-d4) δ 8.38 (d, J = 1.4 Hz, 1H), 8.04 (dd, J = 8.5, 1.5 Hz, 1H), 7.87 (t, J = 7.8 Hz, 1H), 7.75 (t, J = 7.5 Hz, 1H), 7.62 (dt, J = 19.8, 8.4 Hz, 4H), 7.15 (d, J = 1.9 Hz, 1H), 7.07 (d, J = 1.8 Hz, 1H), 7.02 (d, J = 8.3 Hz, 1H), 5.78 (s, 2H), 5.66 (s, 2H), 4.77 (t, J = 4.9 Hz, 2H), 3.86 (t, J = 4.9 Hz, 2H), 3.37 (s, 3H), 2.61 (s, 3H). |
| 518 | 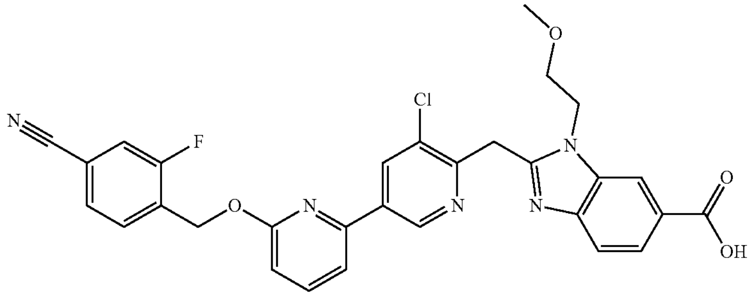 [SMILES: COCCn1c(Cc2ncc(-c3cccc(OCc4ccc(C#N)cc4F)n3)cc2Cl)nc2ccc(C(=O)O)cc21] 2-((5'-chloro-6-((4-cyano-2-fluorobenzyl)oxy)-[2,3'-bipyridin]-6'-yl)methyl)-1-(2-methoxyethyl)-1H-benzo[d]imidazole-6-carboxylic acid: ES/MS m/z 573.2; $^1$H NMR (400 MHz, Methanol-d4) δ 9.02 (d, J = 2.0 Hz, 1H), 8.59 (d, J = 1.3 Hz, 1H), 8.51 (d, J = 1.9 Hz, 1H), 8.25 (dd, J = 8.6, 1.4 Hz, 1H), 7.91-7.79 (m, 2H), 7.72 (t, J = 7.5 Hz, 1H), 7.69-7.50 (m, 3H), 6.97 (d, J = 8.2 Hz, 1H), 5.63 (s, 2H), 4.83-4.72 (m, 2H), 3.81 (dd, J = 5.4, 4.3 Hz, 2H), 3.32 (d, J = 1.7 Hz, 2H), 3.25 (s, 3H). |

Example 62, 2-(4-(3-((4-cyano-2-fluorobenzyl)oxy)-1,2,4-thiadiazol-5-yl)-2-fluorobenzyl)-1-(2-methoxyethyl)-1H-benzo[d]imidazole-6-carboxylic acid Procedure 13

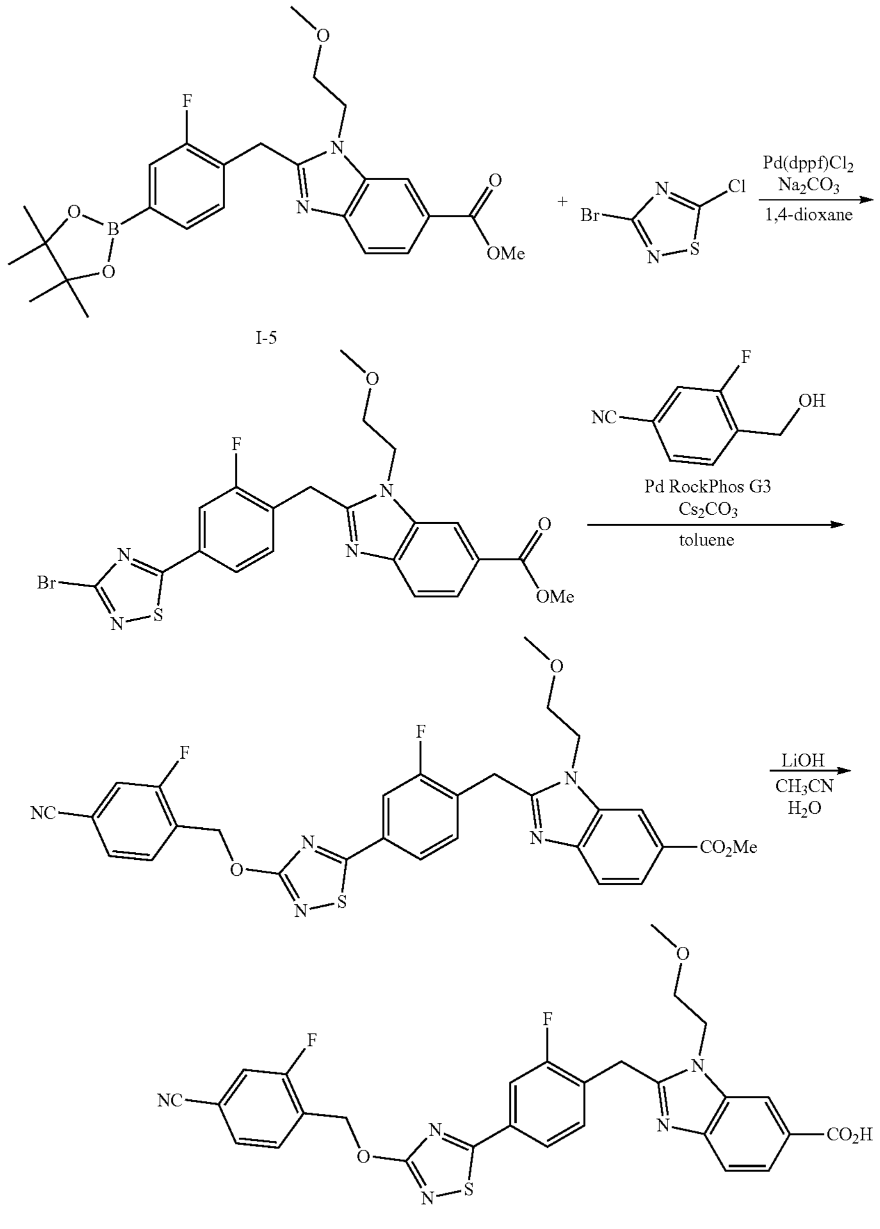

I-5

Methyl 2-{[4-(3-bromo-1,2,4-thiadiazol-5-yl)-2-fluorophenyl]methyl}-3-(2-methoxyethyl)benzimidazole-5-carboxylate: To a vial was added methyl 2-{[2-fluoro-4-(4,4,5,5-tetramethyl-1,3,2-dioxaborolan-2-yl)phenyl]methyl}-3-(2-methoxyethyl)benzimidazole-5-carboxylate (I-5) (75 mg, 0.16 mmol), 3-bromo-5-chloro-1,2,4-thiadiazole (39 mg, 0.192 mmol), and Pd(dppf)$Cl_2$ (18 mg, 0.024 mmol). To the vial was added 1,4-dioxane (1.5 mL). Sodium carbonate (2 M aqueous, 0.12 mL, 0.24 mmol) was added, and the mixture was degassed with argon for 30 seconds. The vial was sealed and stirred 3 hours at 90° C. LCMS showed conversion of the starting material to desired product, and the vial was cooled to room temperature. The organic layer was transferred directly to a loading column, and the crude material was purified by silica gel chromatography (eluent: EtOAc/hexanes) to afford the desired product: ES/MS: 505.232 (M+$H^+$).

Methyl 2-{[4-[3-[(4-cyano-2-fluoro-phenyl)methoxy]-1,2,4-thiadiazol-5-yl]-2-fluoro-phenyl]methyl}-3-(2-methoxyethyl)benzimidazole-5-carboxylate: To a vial was added methyl 2-{[4-(3-bromo-1,2,4-thiadiazol-5-yl)-2-fluoro-phenyl]methyl}-3-(2-methoxyethyl)benzimidazole-5-carboxylate (60 mg, 0.12 mmol), 3-fluoro-4-(hydroxymethyl)benzonitrile (36 mg, 0.24 mmol), cesium carbonate (116 mg, 0.356 mmol) and Pd Rockphos G3 (15 mg, 0.018 mmol). To the vial was added toluene (1 mL), and the mixture was degassed with argon for 30 seconds. The vial was sealed and stirred overnight at 110° C. LCMS showed conversion of the starting material to desired product, and the vial was cooled to room temperature. The organic layer was transferred directly to a loading column, and the crude material was purified by silica gel chromatography (eluent: EtOAc/hexanes) to afford the desired product: ES/MS: 576.308 (M+$H^+$).

2-{[4-[3-[(4-cyano-2-fluoro-phenyl)methoxy]-1,2,4-thiadiazol-5-yl]-2-fluoro-phenyl]methyl}-3-(2-methoxyethyl) benzimidazole-5-carboxylic acid: To a 40 mL vial was added methyl 2-{[4-[3-[(4-cyano-2-fluoro-phenyl) methoxy]-1,2,4-thiadiazol-5-yl]-2-fluoro-phenyl]methyl}-3-(2-methoxyethyl)benzimidazole-5-carboxylate (34 mg, 0.059 mmol), and acetonitrile (1 mL) was added. To the mixture was added LiOH (3 mg, 0.12 mmol) dissolved in water (0.2 mL), and the mixture was stirred overnight at 55° C. LCMS showed conversion of the starting material to the product. The mixture was acidified with 50% citric acid (0.2 mL) and 2 drops of trifluoroacetic acid were added. The material was purified by RP-HPLC (eluent: water/MeCN*0.1% TFA) to yield the product Example 62 as a trifluoroacetate salt: ES/MS: 562.396 (M+$H^+$); $^1$H NMR (400 MHz, $CD_3OD$) δ 8.43 (t, J=1.0 Hz, 1H), 8.12 (dd, J=8.6, 1.5 Hz, 1H), 7.89-7.77 (m, 3H), 7.72 (d, J=8.6 Hz, 1H), 7.69-7.62 (m, 2H), 7.55 (t, J=7.7 Hz, 1H), 5.68 (s, 2H), 4.74-4.67 (m, 4H), 3.79 (t, J=4.9 Hz, 2H), 3.29 (s, 3H).

Examples 83-84 and 91. Compounds Prepared Using Procedure 13

Other compounds of the present disclosure prepared using the general route described in Procedure 13 include the following Examples.

| Example | Structure/Name/Characterization |
|---|---|
| 83 | 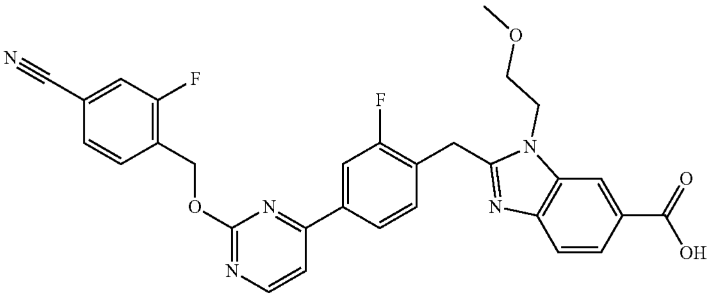 [SMILES: COCCn1c(Cc2ccc(-c3ccnc(OCc4ccc(C#N)cc4F)n3)cc2F)nc2ccc(C(=O)O)cc21]<br>2-(4-(2-((4-cyano-2-fluorobenzyl)oxy)pyrimidin-4-yl)-2-fluorobenzyl)-1-(2-methoxyethyl)-1H-benzo[d]imidazole-6-carboxylic acid: ES/MS m/z 556.4; $^1$H NMR (400 MHz, Methanol-d4) δ 8.68 (d, J = 5.4 Hz, 1H), 8.46 (s, 1H), 8.14 (d, J = 8.5 Hz, 1H), 8.08-8.02 (m, 2H), 7.80 (t, J = 7.5 Hz, 1H), 7.76-7.59 (m, 4H), 7.59-7.50 (m, 1H), 5.71 (s, 2H), 4.77-4.69 (m, 4H), 3.80 (t, J = 5.1 Hz, 2H), 3.30 (s, 3H). |
| 84 | 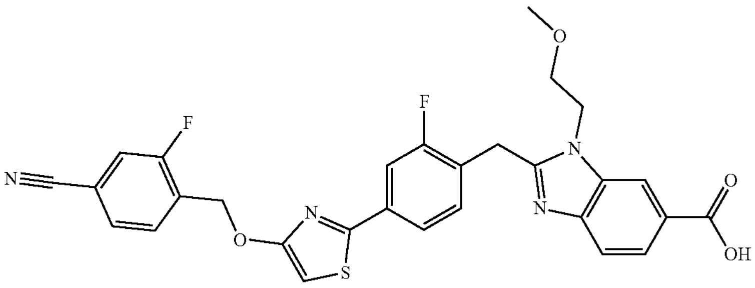 [SMILES: COCCn1c(Cc2ccc(-c3nc(OCc4ccc(C#N)cc4F)cs3)cc2F)nc2ccc(C(=O)O)cc21]<br>2-(4-(4-((4-cyano-2-fluorobenzyl)oxy)thiazol-2-yl)-2-fluorobenzyl)-1-(2-methoxyethyl)-1H-benzo[d]imidazole-6-carboxylic acid: ES/MS m/z 561.2; $^1$H NMR (400 MHz, DMSO-d6) δ 8.21 (s, 1H), 7.97-7.92 (m, 1H), 7.85-7.69 (m, 6H), 7.59 (d, J = 8.5 Hz, 1H), 7.46 (t, J = 7.9 Hz, 1H), 6.87 (s, 1H), 5.41 (s, 2H), 4.61-4.53 (m, 4H), 4.44 (s, 2H), 3.66 (t, J = 5.0 Hz, 2H), 3.20 (s, 3H). |

-continued

| Example | Structure/Name/Characterization |
|---|---|
| 91 | 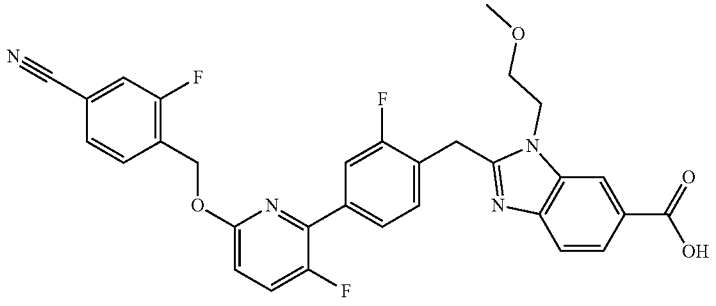 [SMILES: COCCn1c(Cc2ccc(-c3nc(OCc4ccc(C#N)cc4F)ccc3F)cc2F)nc2ccc(C(=O)O)cc21] 2-(4-(6-((4-cyano-2-fluorobenzyl)oxy)-3-fluoropyridin-2-yl)-2-fluorobenzyl)-1-(2-methoxyethyl)-1H-benzo[d]imidazole-6-carboxylic acid: ES/MS m/z 573.2; $^{1}$H NMR (400 MHz, Methanol-d4) δ 8.53 (d, J = 1.5 Hz, 1H), 8.21 (dd, J = 8.6, 1.5 Hz, 1H), 8.15 (d, J = 2.4 Hz, 1H), 7.80-7.72 (m, 2H), 7.65-7.54 (m, 5H), 7.10 (d, J = 5.2 Hz, 1H), 5.55 (s, 2H), 4.83-4.74 (m, 4H), 3.82 (t, J = 4.9 Hz, 2H), 3.37 (s, 2H). |

Example 63. 2-{[4-[5-[(4-cyano-2-fluoro-phenyl)methoxy]-1,2,4-thiadiazol-3-yl]-2-fluoro-phenyl]methyl}-3-(2-methoxyethyl)benzimidazole-5-carboxylic acid Procedure 14

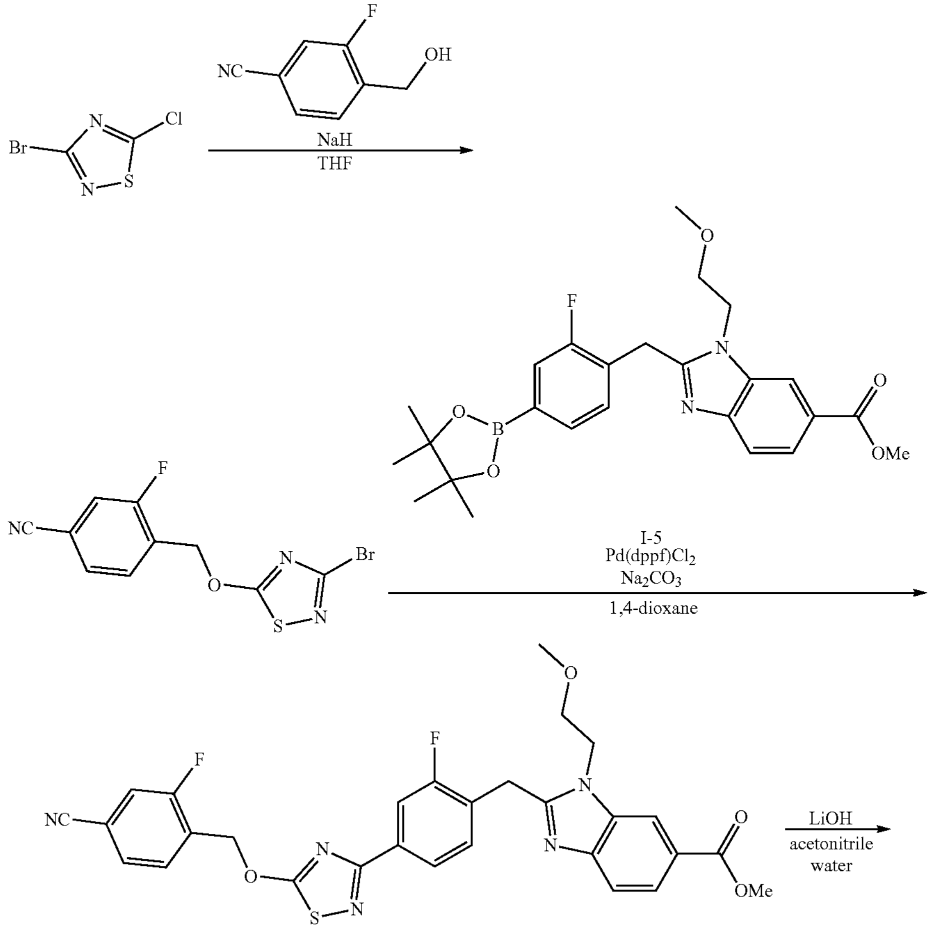

-continued

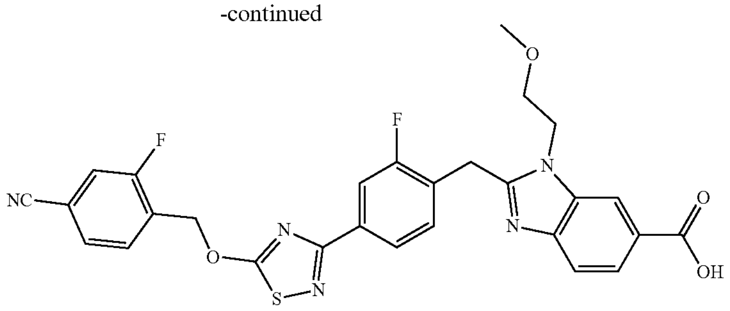

4-[(3-bromo-1,2,4-thiadiazol-5-yl)oxymethyl]-3-fluoro-benzonitrile: To a vial was added 3-bromo-5-chloro-1,2,4-thiadiazole (500 mg, 2.51 mmol) and 3-fluoro-4-(hydroxymethyl)benzonitrile (379 mg, 2.51 mmol). To the vial was added THF (5 mL) under $N_2$, and the mixture was cooled to 0° C. Sodium hydride (60% dispersion in mineral oil, 95 mg, 2.5 mmol) was added, and the mixture was stirred 3 h at room temperature. The mixture was partitioned between EtOAc (50 mL) and water (20 mL) and the organic layer was separated, dried over $MgSO_4$, and concentrated under reduced pressure. The crude residue was purified by silica chromatography (eluent EtOAc/hexanes) to afford the product.

Methyl 2-{[4-[5-[(4-cyano-2-fluoro-phenyl)methoxy]-1,2,4-thiadiazol-3-yl]-2-fluoro-phenyl]methyl}-3-(2-methoxyethyl)benzimidazole-5-carboxylate: To a vial was added methyl 2-{[2-fluoro-4-(4,4,5,5-tetramethyl-1,3,2-dioxaborolan-2-yl)phenyl]methyl}-3-(2-methoxyethyl)benzimidazole-5-carboxylate (I-5) (50 mg, 0.107 mmol), 4-[(3-bromo-1,2,4-thiadiazol-5-yl)oxymethyl]-3-fluoro-benzonitrile (34 mg, 0.107 mmol), and Pd(dppf)$Cl_2$ (12 mg, 0.016 mmol). To the vial was added 1,4-dioxane (1.5 mL). Sodium carbonate (2 M aqueous, 0.08 mL, 0.16 mmol) was added, and the mixture was degassed with argon for 30 seconds. The vial was sealed and stirred 3 hours at 90° C. LCMS showed conversion of the starting material to desired product, and the vial was cooled to room temperature. The organic layer was transferred directly to a loading column, and the crude material was purified by silica gel chromatography (eluent: EtOAc/hexanes) to afford the desired product: ES/MS: 576.240 (M+$H^+$).

2-{[4-[5-[(4-cyano-2-fluoro-phenyl)methoxy]-1,2,4-thiadiazol-3-yl]-2-fluoro-phenyl]methyl}-3-(2-methoxyethyl)benzimidazole-5-carboxylic acid: To a 40 mL vial was added methyl 2-{[4-[5-[(4-cyano-2-fluoro-phenyl)methoxy]-1,2,4-thiadiazol-3-yl]-2-fluoro-phenyl]methyl}-3-(2-methoxyethyl)benzimidazole-5-carboxylate (14 mg, 0.024 mmol), and acetonitrile (1 mL) was added. To the mixture was added LiOH (1.2 mg, 0.049 mmol) dissolved in water (0.2 mL), and the mixture was stirred overnight at 55° C. LCMS showed conversion of the starting material to the product. The mixture was acidified with 50% citric acid (0.2 mL) and 2 drops of trifluoroacetic acid were added. The material was purified by RP-HPLC (eluent: water/MeCN*0.1% TFA) to yield the product Example 63 as a trifluoroacetate salt: ES/MS: 562.258 (M+$H^+$); $^1$H NMR (400 MHz, $CD_3OD$) δ 8.44 (d, J=1.2 Hz, 1H), 8.12 (dd, J=8.5, 1.5 Hz, 1H), 8.06 (dd, J=7.9, 1.6 Hz, 1H), 7.99 (dd, J=11.0, 1.6 Hz, 1H), 7.85 (t, J=7.5 Hz, 1H), 7.77-7.63 (m, 3H), 7.48 (t, J=7.8 Hz, 1H), 5.82 (s, 2H), 4.74-4.65 (m, 4H), 3.78 (t, J=4.9 Hz, 2H), 3.30 (s, 3H).

Example 64, 2-(2-amino-4-(6-((4-cyano-2-fluorobenzyl)oxy)pyridin-2-yl)benzyl)-1-(2-methoxyethyl)-1H-benzo[d]imidazole-6-carboxylic acid Procedure 15

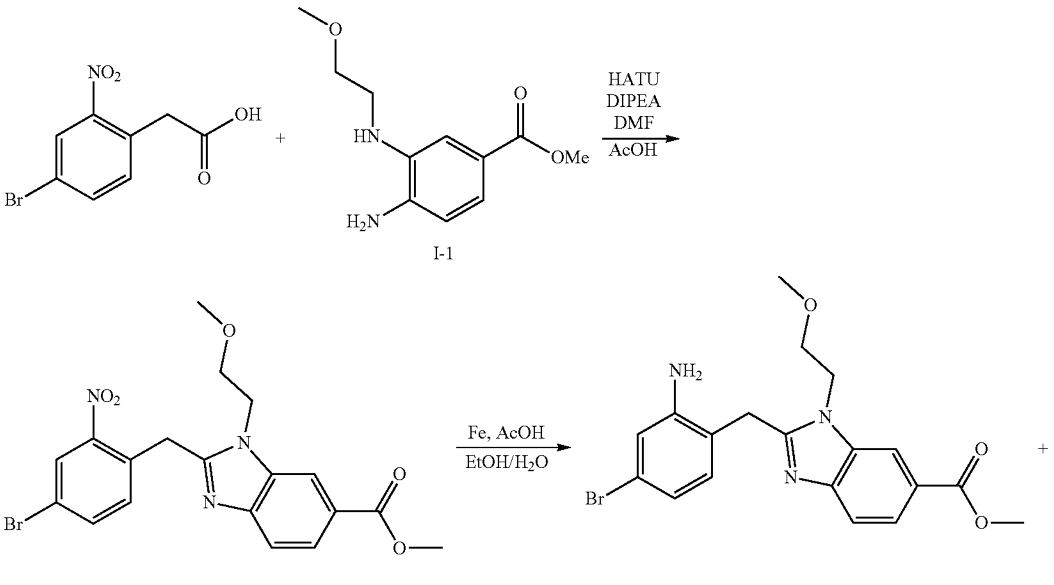

I-1

-continued

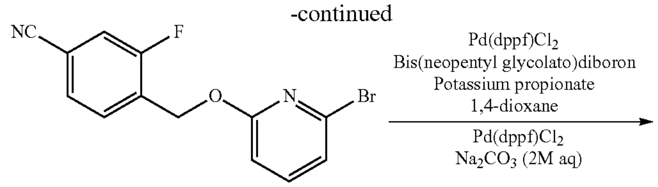

I-6

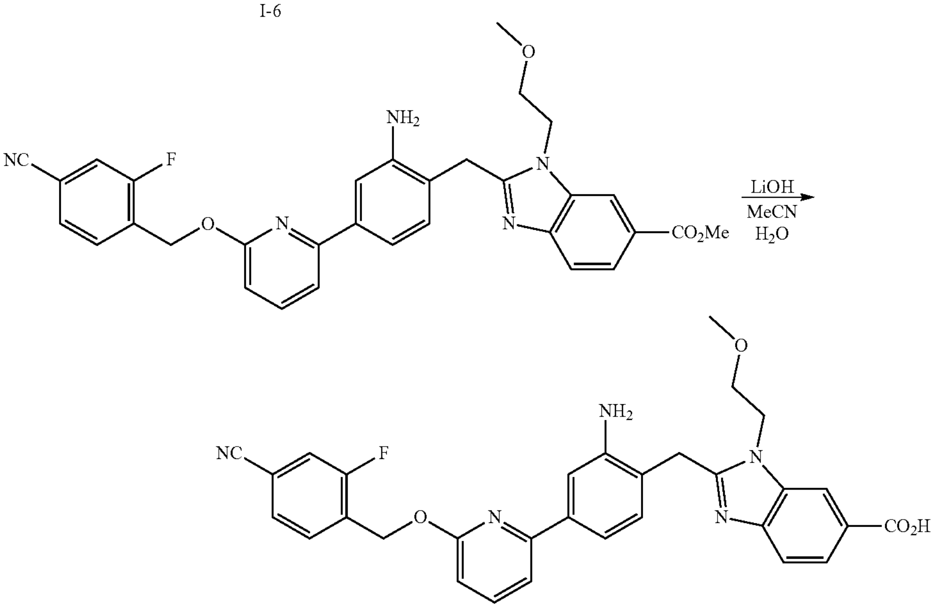

Methyl 2-(4-bromo-2-nitrobenzyl)-1-(2-methoxyethyl)-1H-benzo[d]imidazole-6-carboxylate: 2-(4-bromo-2-nitro-phenyl)acetic acid (800 mg, 3.08 mmol), methyl 4-amino-3-(2-methoxyethylamino)benzoate (I-1, 828 mg, 3.69 mmol), and O-(7-Azabenzotriazol-1-yl)-N,N,N',N'-tetramethyluronium hexafluorophosphate (1404 mg, 3.69 mmol) were taken up in DMF (12 mL) and N,N-diisopropylethylamine (2.68 mL, 15.4 mmol) was added. The mixture was stirred at room temperature for one hour. Following this time, the mixture was diluted with EtOAc (30 mL) and water (30 mL). The organic phase was collected and the aqueous phase extracted with EtOAc (2×20 mL). The combined organic phases were dried over $Na_2SO_4$ and concentrated in vacuo. The resulting residue was taken up in acetic acid (20 mL) and heated to 100° C. After an hour, the mixture was concentrated in vacuo and purified by silica gel column chromatography (eluent: 20-70% EtOAc/$CH_2Cl_2$): ES/MS: 450.1 ($M+H^+$).

Methyl 2-(2-amino-4-bromobenzyl)-1-(2-methoxyethyl)-1H-benzo[d]imidazole-6-carboxylate: Methyl 2-[(4-bromo-2-nitro-phenyl)methyl]-3-(2-methoxyethyl)benzimidazole-5-carboxylate (250 mg, 0.558 mmol) was taken up in ethanol (1.80 mL), and water (0.15 mL) and acetic acid (0.10 mL) were added. Iron powder (0.311 g, 0.558 mmol) was then added to the mixture and the mixture was heated to 70° C. After one hour, the mixture was cooled to room temperature, filtered through Celite, and concentrated in vacuo. The desired product was used in the subsequent reaction without further purification: ES/MS: 420.0 ($M+H^+$).

Methyl 2-(2-amino-4-(6-((4-cyano-2-fluorobenzyl)oxy)pyridin-2-yl)benzyl)-1-(2-methoxyethyl)-1H-benzo[d]imidazole-6-carboxylate: To a vial was added methyl 2-[(2-amino-4-bromo-phenyl)methyl]-3-(2-methoxyethyl)benzimidazole-5-carboxylate (0.100 g, 0.000239 mol), bis(neopentyl glycolato)diboron (70 mg, 0.311 mmol mmol), Pd(dppf)$Cl_2$ (27 mg, 0.036 mmol), and potassium propionate (80 mg, 0.717 mmol). 1,4-Dioxane (1 mL) was added, and the mixture was degassed with argon for two minutes. The vial was sealed, and the mixture was heated for 1 hour at 90° C. Following this time, LC/MS showed conversion of the aryl bromide to the intermediate boronic acid and the mixture was cooled to room temperature. At this time, aqueous sodium carbonate (2.0 M, 0.24 mL, 0.478 mmol) was added followed by Pd(dppf)$Cl_2$ (27 mg, 0.036 mmol), and 4-[(6-bromo-2-pyridyl)oxymethyl]-3-fluoro-benzonitrile (I-6) (73 mg, 0.24 mmol). The vial was resealed and heated to 90° C. for one hour. Following this time, the mixture was cooled to room temperature, filtered through Celite, and concentrated in vacuo. The crude material was purified by silica gel chromatography (eluent: 10-70% EtOAc/hexanes) to afford the desired product: ES/MS: 566.2 ($M+H^+$).

2-(2-Amino-4-(6-((4-cyano-2-fluorobenzyl)oxy)pyridin-2-yl)benzyl)-1-(2-methoxyethyl)-1H-benzo[d]imidazole-6-carboxylic acid: Methyl 2-(2-amino-4-(6-((4-cyano-2-fluorobenzyl)oxy)pyridin-2-yl)benzyl)-1-(2-methoxyethyl)-1H-benzo[d]imidazole-6-carboxylate (27 mg, 0.048 mmol) was taken up in acetonitrile (0.8 mL) and aqueous lithium hydroxide (0.3 M, 0.80 mL, 0.238 mmol) was added. The mixture was heated to 50° C. for one hour. Following this time, the mixture was diluted with water (5 mL), the pH adjusted to ~5 with 5% aqueous citric acid solution and the mixture extracted with EtOAc (3×5 mL). The combined organics were dried over $Na_2SO_4$, concentrated in vacuo, and purified by RP-HPLC (eluent: 15-60% MeCN/water with 0.1% TFA) to yield the product (Example 64) as the trifluoroacetate salt: ES/MS: 552.2 ($M+H^+$); $^1H$ NMR (400 MHz, DMSO-$d_6$) δ 8.36 (s, 1H), 7.98-7.91 (m, 2H), 7.86-

7.65 (m, 5H), 7.55 (d, J=1.9 Hz, 1H), 7.48 (d, J=7.4 Hz, 1H), 7.34 (dd, J=7.9, 1.9 Hz, 1H), 7.16 (d, J=8.0 Hz, 1H), 6.88 (d, J=8.1 Hz, 1H), 5.61 (s, 2H), 4.68 (s, 2H), 4.40 (s, 2H), 3.69 (t, J=5.1 Hz, 2H), 3.23 (s, 3H).

Example 65. 2-(2-Acetamido-4-(6-((4-cyano-2-fluorobenzyl)oxy)pyridin-2-yl)benzyl)-1-(2-methoxyethyl)-1H-benzo[d]imidazole-6-carboxylic acid Procedure 16

2-(2-Acetamido-4-(6-((4-cyano-2-fluorobenzyl)oxy)pyridin-2-yl)benzyl)-1-(2-methoxyethyl)-1H-benzo[d]imidazole-6-carboxylic acid: Methyl 2-(2-acetamido-4-(6-((4-cyano-2-fluorobenzyl)oxy)pyridin-2-yl)benzyl)-1-(2-methoxyethyl)-1H-benzo[d]imidazole-6-carboxylate (28 mg, 0.047 mmol) was taken up in acetonitrile (0.8 mL) and aqueous lithium hydroxide (0.3 M, 0.80 mL, 0.238 mmol) was added. The mixture was heated to 100° C. for 10 minutes. Following this time, the mixture was diluted with water (5 mL), the pH adjusted to ~5 with 5% aqueous citric

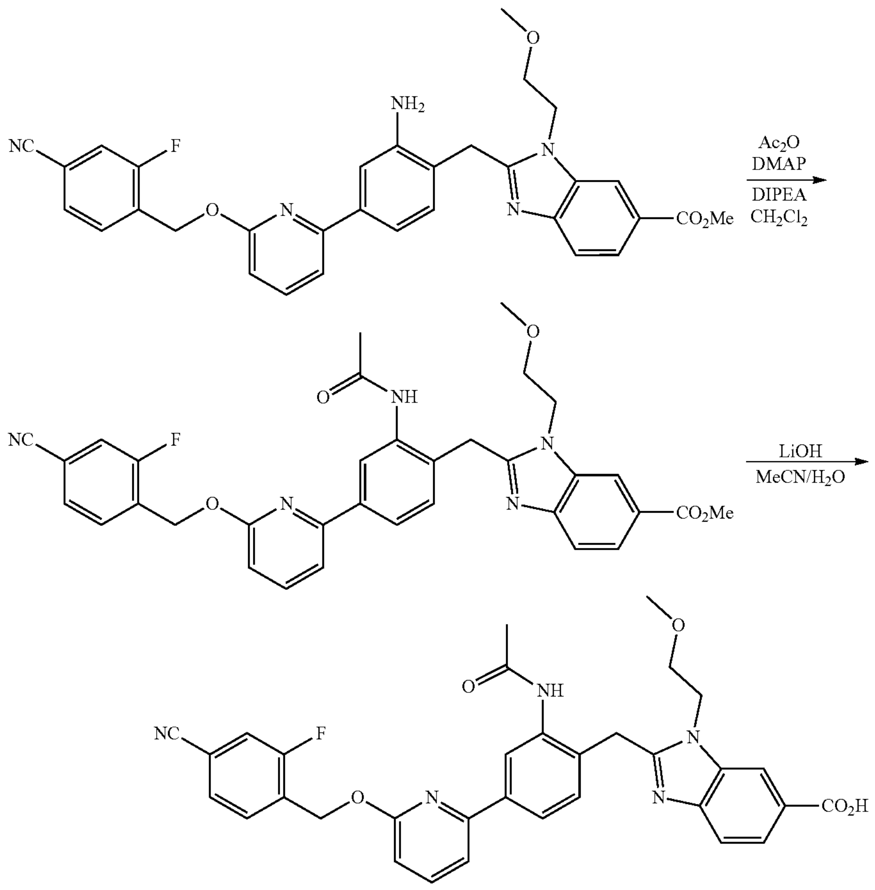

Methyl 2-(2-acetamido-4-(6-((4-cyano-2-fluorobenzyl)oxy)pyridin-2-yl)benzyl)-1-(2-methoxyethyl)-1H-benzo[d]imidazole-6-carboxylate: Methyl 2-{[2-amino-4-[6-[(4-cyano-2-fluoro-phenyl)methoxy]-2-pyridyl]phenyl]methyl}-3-(2-methoxyethyl)benzimidazole-5-carboxylate (89 mg, 0.158 mmol) was taken up in dichloromethane (1.6 mL) and the solution cooled to 0° C. N,N-diisopropylethylamine (0.165 mL, 0.945 mmol) was added followed by 4-dimethylaminopyridine (2 mg, 0.016 mmol). Acetic anhydride (0.08 mL, 0.788 mmol) was then added dropwise and, following addition, the mixture was warmed to room temperature. After 2.5 hours the mixture was diluted with EtOAc (5 mL) and $H_2O$ (5 mL). The organic phase was collected and the aqueous phase was extracted with EtOAc (2×5 mL). The combined organics were dried over $Na_2SO_4$, concentrated in vacuo, and purified by silica gel column chromatography (eluent: 20-80% EtOAc/hexanes) to afford the product: ES/MS: 608.3 ($M+H^+$).

acid solution and the mixture extracted with EtOAc (3×5 mL). The combined organics were dried over $Na_2SO_4$, concentrated in vacuo, and purified by RP-HPLC (eluent: 15-65% MeCN/water with 0.1% TFA) to yield the product (Example 65) as the trifluoroacetate salt: ES/MS: 594.2 ($M+H^+$); $^1H$ NMR (400 MHz, DMSO-d6) δ 9.99 (s, 1H), 8.25 (s, 1H), 8.11 (d, J=1.8 Hz, 1H), 7.98-7.75 (m, 5H), 7.75-7.63 (in, 2H), 7.55 (d, J=7.5 Hz, 1H), 7.33 (d, J=8.1 Hz, 1H), 6.90 (d, J=8.2 Hz, 1H), 5.59 (s, 2H), 4.54 (t, J=5.3 Hz, 2H), 4.41 (s, 2H), 3.60 (t, J=5.1 Hz, 2H), 3.19 (s, 3H), 2.10 (s, 3H).

Examples 253 and 687. Compounds Prepared Using Procedure 16

Other compounds of the present disclosure prepared using the general route described in Procedure 16 include the following Examples.

| Example | Structure/Name/Characterization |
|---|---|
| 253 | 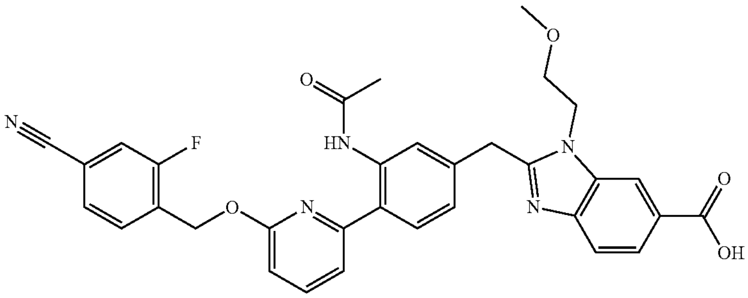 [SMILES: COCCn1c(Cc2ccc(-c3cccc(OCc4ccc(C#N)cc4F)n3)c(NC(C)=O)c2)nc2ccc(C(=O)O)cc21] 2-(3-acetamido-4-(6-((4-cyano-2-fluorobenzyl)oxy)pyridin-2-yl)benzyl)-1-(2-methoxyethyl)-1H-benzo[d]imidazole-6-carboxylic acid: ES/MS m/z 594.2; $^1H$ NMR (400 MHz, Methanol-d4) δ 8.53 (s, 1H), 8.21 (dd, J = 8.6, 1.4 Hz, 1H), 8.04 (s, 1H), 7.89 (dd, J = 8.3, 7.5 Hz, 1H), 7.78 (t, J = 8.9 Hz, 2H), 7.69 (d, J = 8.0 Hz, 1H), 7.65-7.59 (m, 2H), 7.36 (d, J = 7.5 Hz, 1H), 7.29 (d, J = 8.2 Hz, 1H), 6.97 (d, J = 8.2 Hz, 1H), 5.59 (s, 2H), 4.77 (t, J = 5.0 Hz, 2H), 4.72 (s, 2H), 3.80 (t, J = 4.9 Hz, 2H), 2.11 (s, 3H). |
| 687 | 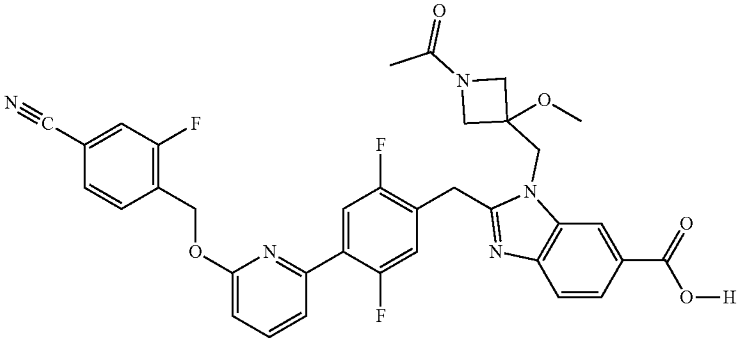 [SMILES: COC1(Cn2c(Cc3cc(F)c(-c4cccc(OCc5ccc(C#N)cc5F)n4)cc3F)nc3ccc(C(=O)O)cc32)CN(C(C)=O)C1] ES/MS m/z 656.2; 1H NMR (400 MHz, DMSO-d6) δ 8.45 (d, J = 1.5 Hz, 1H), 7.95-7.87 (m, 2H), 7.83 (dd, J = 8.5, 1.5 Hz, 1H), 7.79-7.71 (m, 3H), 7.62 (d, J = 8.4 Hz, 1H), 7.53 (dd, J = 7.6, 1.7 Hz, 1H), 7.41 (dd, J = 11.5, 6.1 Hz, 1H), 7.00 (d, J = 8.3 Hz, 1H), 5.60 (s, 2H), 4.92 (s, 2H), 4.49 (s, 2H), 4.32 (d, J = 9.8 Hz, 1H), 4.12 (d, J = 9.8 Hz, 1H), 3.99 (d, J = 10.8 Hz, 1H), 3.90 (d, J = 10.7 Hz, 1H), 3.36 (s, 3H), 1.83 (s, 3H). |

Example 66. 2-(4-(6-((4-Cyano-2-fluorobenzyl)oxy)pyridin-2-yl)-2-(methylsulfonamido)benzyl)-1-(2-methoxyethyl)-1H-benzo[d]imidazole-6-carboxylic acid Procedure 17

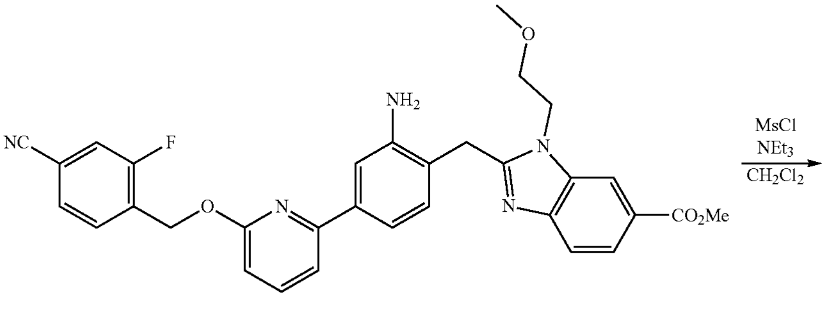

-continued

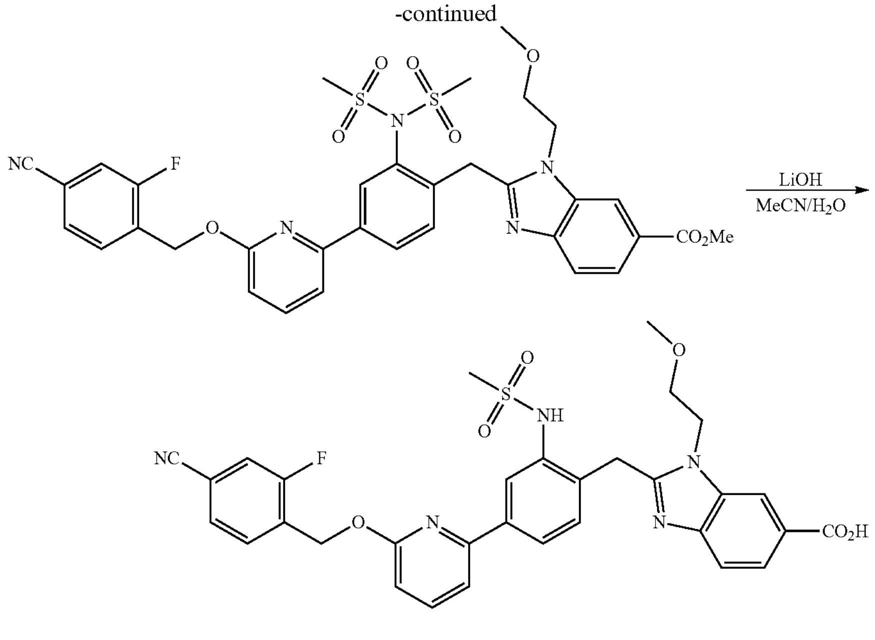

Methyl 2-(4-(6-((4-cyano-2-fluorobenzyl)oxy)pyridin-2-yl)-2-(N-(methylsulfonyl)methylsulfonamido)benzyl)-1-(2-methoxyethyl)-1H-benzo[d]imidazole-6-carboxylate: Methyl 2-{[2-amino-4-[6-[(4-cyano-2-fluoro-phenyl)methoxy]-2-pyridyl]phenyl]methyl}-3-(2-methoxyethyl)benzimidazole-5-carboxylate (50 mg, 0.088 mmol) was taken up in dichloromethane (1.0 mL) and the solution cooled to 0° C. Triethylamine (0.044 mL, 0.318 mmol) was added followed by methanesulfonyl chloride (0.012 mL, 0.159 mmol) and the mixture was stirred at 0° C. for 5 minutes then warmed to room temperature. After 30 minutes the mixture was diluted with EtOAc (5 mL) and $H_2O$ (5 mL). The organic phase was collected and the aqueous phase was extracted with EtOAc (2×5 mL). The combined organics were dried over $Na_2SO_4$, concentrated in vacuo, and purified by silica gel column chromatography (eluent: 20-70% EtOAc/hexanes) to afford the product: ES/MS: 722.2 ($M+H^+$).

2-(4-(6-((4-Cyano-2-fluorobenzyl)oxy)pyridin-2-yl)-2-(methylsulfonamido)benzyl)-1-(2-methoxyethyl)-1H-benzo[d]imidazole-6-carboxylic acid: Methyl 2-(4-(6-((4-cyano-2-fluorobenzyl)oxy)pyridin-2-yl)-2-(N-(methylsulfonyl)methylsulfonamido)benzyl)-1-(2-methoxyethyl)-1H-benzo[d]imidazole-6-carboxylate (64 mg, 0.088 mmol) was taken up in acetonitrile (1.8 mL) and aqueous lithium hydroxide (0.3 M, 1.5 mL, 0.442 mmol) was added. The mixture was heated to 50° C. for one hour. Following this time, the mixture was diluted with water (5 mL), the pH adjusted to ~5 with 5% aqueous citric acid solution and the mixture extracted with EtOAc (3×5 mL). The combined organics were dried over $Na_2SO_4$, concentrated in vacuo, and purified by RP-HPLC (eluent: 15-65% MeCN/water with 0.1% TFA) to yield the product (Example 66) as the trifluoroacetate salt: ES/MS: 630.2 ($M+H^+$); $^1H$ NMR (400 MHz, DMSO-$d_6$) δ 9.99 (s, 1H), 8.25 (s, 1H), 8.11 (d, J=1.8 Hz, 1H), 7.98-7.75 (m, 5H), 7.75-7.63 (m, 2H), 7.55 (d, J=7.5 Hz, 1H), 7.33 (d, J=8.1 Hz, 1H), 6.90 (d, J=8.2 Hz, 1H), 5.59 (s, 2H), 4.54 (d, J=5.3 Hz, 2H), 4.41 (s, 2H), 3.60 (t, J=5.1 Hz, 2H), 3.34 (s, 3H), 3.19 (s, 3H), 2.10 (s, 3H).

Example 688. Compounds Prepared Using Procedure 17

Other compounds of the present disclosure prepared using the general route described in Procedure 17 include the following Example.

| Example | Structure/Name/Characterization |
|---|---|
| 688 | 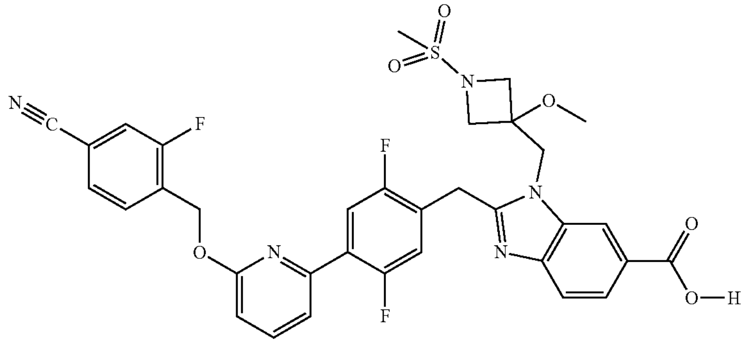 [SMILES: COC1(Cn2c(Cc3cc(F)c(-c4cccc(OCc5ccc(C#N)cc5F)n4)cc3F)nc3ccc(C(=O)O)cc32)CN(S(C)(=O)=O)C1] ES/MS m/z 692.2; 1H NMR (400 MHz, DMSO-d6) δ 8.35 (d, J = 1.5 Hz, 1H), 7.96-7.86 (m, 2H), 7.83 (dd, J = 8.4, 1.5 Hz, 1H), 7.75 (td, J = 6.5, 4.4 Hz, |

-continued

| Example | Structure/Name/Characterization |
|---|---|
| | 3H), 7.63 (d, J = 8.5 Hz, 1H), 7.54 (dd, J = 7.5, 1.7 Hz, 1H), 7.41 (dd, J = 11.5, 6.1 Hz, 1H), 7.00 (d, J = 8.3 Hz, 1H), 5.61 (s, 2H), 4.91 (s, 2H), 4.48 (s, 2H), 4.16 (d, J = 9.3 Hz, 2H), 3.77 (d, J = 9.3 Hz, 2H), 3.40 (s, 3H), 3.11 (s, 3H). |

Example 67, 2-(4-(6-((4-Cyano-2-fluorobenzyl)oxy)pyridin-2-yl)-2-fluorobenzyl)-1-(oxetan-2-ylmethyl)-1H-benzo[d]imidazole-6-carboxylic acid isomer 1

Example 68, 2-(4-(6-((4-Cyano-2-fluorobenzyl)oxy)pyridin-2-yl)-2-fluorobenzyl)-1-(oxetan-2-ylmethyl)-1H-benzo[d]imidazole-6-carboxylic acid isomer 2

Procedure 18

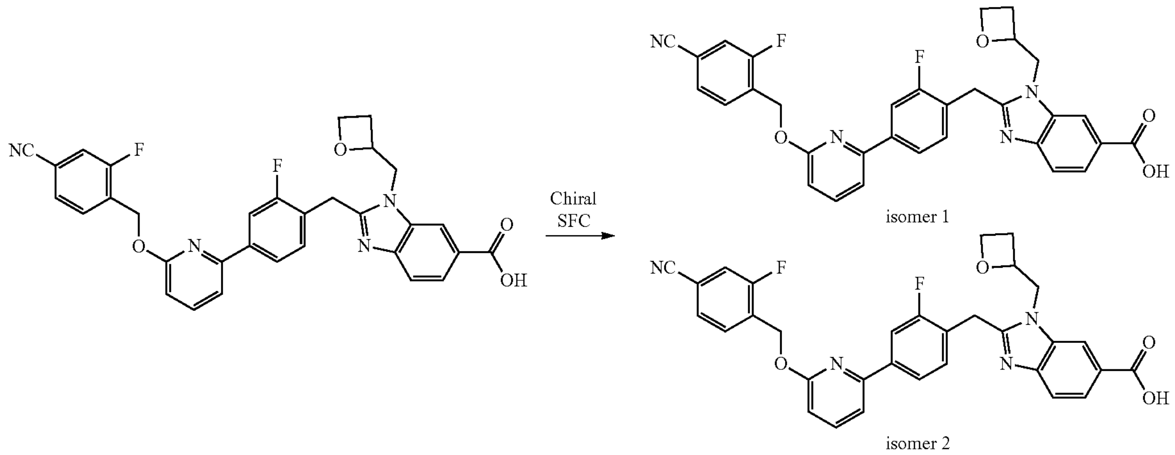 [SMILES: N#Cc1ccc(COc2cccc(-c3ccc(Cc4nc5ccc(C(=O)O)cc5n4CC4CCO4)c(F)c3)n2)c(F)c1 ; N#Cc1ccc(COc2cccc(-c3ccc(Cc4nc5ccc(C(=O)O)cc5n4CC4CCO4)c(F)c3)n2)c(F)c1 ; N#Cc1ccc(COc2cccc(-c3ccc(Cc4nc5ccc(C(=O)O)cc5n4CC4CCO4)c(F)c3)n2)c(F)c1]

2-(4-(6-((4-Cyano-2-fluorobenzyl)oxy)pyridin-2-yl)-2-fluorobenzyl)-1-(oxetan-2-ylmethyl)-1H-benzo[d]imidazole-6-carboxylic acid: 2-(4-(6-((4-Cyano-2-fluorobenzyl)oxy)pyridin-2-yl)-2-fluorobenzyl)-1-(oxetan-2-ylmethyl)-1H-benzo[d]imidazole-6-carboxylic acid (obtained as described in Procedure 1) as a mixture of 2 stereoisomers was separated by chiral SFC (AZ-H column with 45% EtOH cosolvent) to give two different stereoisomers.

2-(4-(6-((4-cyano-2-fluorobenzyl)oxy)pyridin-2-yl)-2-fluorobenzyl)-1-(oxetan-2-ylmethyl)-1H-benzo[d]imidazole-6-carboxylic acid isomer 1 (Example 67): ES/MS: 567.4 ($M+H^+$); $^1H$ NMR (400 MHz, $CD_3OD$) δ 8.60 (t, J=1.0 Hz, 1H), 8.26-8.21 (m, 1H), 7.96-7.87 (m, 2H), 7.87-7.70 (m, 3H), 7.64-7.48 (m, 4H), 6.96-6.89 (m, 1H), 5.66 (s, 2H), 5.24 (qd, J=7.5, 2.4 Hz, 1H), 5.00 (dd, J=15.5, 7.6 Hz, 1H), 4.87-4.77 (m, 3H), 4.70 (ddd, J=8.5, 7.4, 5.9 Hz, 1H), 4.55 (dt, J=9.2, 6.0 Hz, 1H), 2.92-2.79 (m, 1H), 2.58 (ddt, J=11.7, 9.1, 7.1 Hz, 1H).

2-(4-(6-((4-cyano-2-fluorobenzyl)oxy)pyridin-2-yl)-2-fluorobenzyl)-1-(oxetan-2-ylmethyl)-1H-benzo[d]imidazole-6-carboxylic acid isomer 2 (Example 68): ES/MS: 567.4 ($M+H^+$); $^1H$ NMR (400 MHz, $CD_3OD$) δ 8.60 (t, J=1.0 Hz, 1H), 8.26-8.21 (m, 1H), 7.96-7.87 (m, 2H), 7.87-7.70 (m, 3H), 7.64-7.48 (m, 4H), 6.96-6.89 (m, 1H), 5.66 (s, 2H), 5.24 (qd, J=7.5, 2.4 Hz, 1H), 5.00 (dd, J=15.5, 7.6 Hz, 1H), 4.87-4.77 (m, 3H), 4.70 (ddd, J=8.5, 7.4, 5.9 Hz, 1H), 4.55 (dt, J=9.2, 6.0 Hz, 1H), 2.92-2.79 (m, 1H), 2.58 (ddt, J=11.7, 9.1, 7.1 Hz, 1H).

Example 69, 2-(4-(6-((4-cyano-2-fluorobenzyl)oxy)pyridin-2-yl)-2-fluorobenzyl)-1-((1,1-dioxidothietan-2-yl)methyl)-1H-benzo[d]imidazole-6-carboxylic acid isomer 1

Example 70, 2-(4-(6-((4-cyano-2-fluorobenzyl)oxy)pyridin-2-yl)-2-fluorobenzyl)-1-((1,1-dioxidothietan-2-yl)methyl)-1H-benzo[d]imidazole-6-carboxylic acid isomer 2

Procedure 19

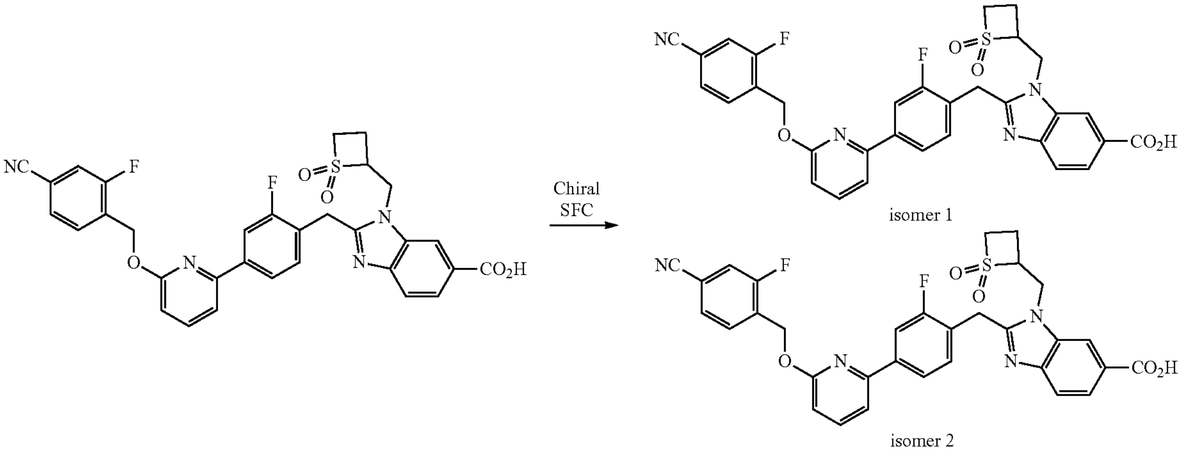 [SMILES: N#Cc1ccc(COc2cccc(-c3ccc(Cc4nc5ccc(C(=O)O)cc5n4CC4CCS4(=O)=O)c(F)c3)n2)c(F)c1 ; N#Cc1ccc(COc2cccc(-c3ccc(Cc4nc5ccc(C(=O)O)cc5n4CC4CCS4(=O)=O)c(F)c3)n2)c(F)c1 ; N#Cc1ccc(COc2cccc(-c3ccc(Cc4nc5ccc(C(=O)O)cc5n4CC4CCS4(=O)=O)c(F)c3)n2)c(F)c1]

2-(4-(6-((4-Cyano-2-fluorobenzyl)oxy)pyridin-2-yl)-2-fluorobenzyl)-1-((1,1-dioxidothietan-2-yl)methyl)-1H-benzo[d]imidazole-6-carboxylic acid: 2-(4-(6-((4-Cyano-2-fluorobenzyl)oxy)pyridin-2-yl)-2-fluorobenzyl)-1-(oxetan-2-ylmethyl)-1H-benzo[d]imidazole-6-carboxylic acid (obtained as described in procedure 1) as a mixture of 2 stereoisomers was separated by chiral SFC (AZ-H column with 50% EtOH/TFA cosolvent) to give two different stereoisomers.

2-(4-(6-((4-Cyano-2-fluorobenzyl)oxy)pyridin-2-yl)-2-fluorobenzyl)-1-((1,1-dioxidothietan-2-yl)methyl)-1H-benzo[d]imidazole-6-carboxylic acid isomer 1 (Example 69): ES/MS: 615.4 (M+H$^+$); $^1$H NMR (400 MHz, $CD_3OD$) δ 8.67 (s, 1H), 8.25 (d, J=8.6 Hz, 1H), 8.04-7.67 (m, 5H), 7.67-7.48 (m, 4H), 6.93 (d, J=8.2 Hz, 1H), 5.66 (s, 2H), 5.24 (dd, J=15.3, 9.5 Hz, 1H), 5.13-4.96 (m, 2H), 4.94 (s, 2H), 4.17 (dq, J=36.3, 11.9 Hz, 2H), 2.56 (q, J=10.4 Hz, 1H), 2.08 (q, J=10.2 Hz, 1H).

2-(4-(6-((4-Cyano-2-fluorobenzyl)oxy)pyridin-2-yl)-2-fluorobenzyl)-1-((1,1-dioxidothietan-2-yl)methyl)-1H-benzo[d]imidazole-6-carboxylic acid (Example 70): ES/MS: 615.4 (M+H$^+$); $^1$H NMR (400 MHz, $CD_3OD$) δ 8.67 (s, 1H), 8.25 (d, J=8.6 Hz, 1H), 8.04-7.67 (m, 5H), 7.67-7.48 (m, 4H), 6.93 (d, J=8.2 Hz, 1H), 5.66 (s, 2H), 5.24 (dd, J=15.3, 9.5 Hz, 1H), 5.13-4.96 (m, 2H), 4.94 (s, 2H), 4.17 (dq, J=36.3, 11.9 Hz, 2H), 2.56 (q, J=10.4 Hz, 1H), 2.08 (q, J=10.2 Hz, 1H).

Example 332 and 333. 1-(2-carboxy-2-methoxyethyl)-2-(4-(6-((4-cyano-2-fluorobenzyl)oxy)pyridin-2-yl)-2-fluorobenzyl)-1H-benzo[d]imidazole-6-carboxylic acid enantiomer 1 and Enantiomer 2

Procedure 20

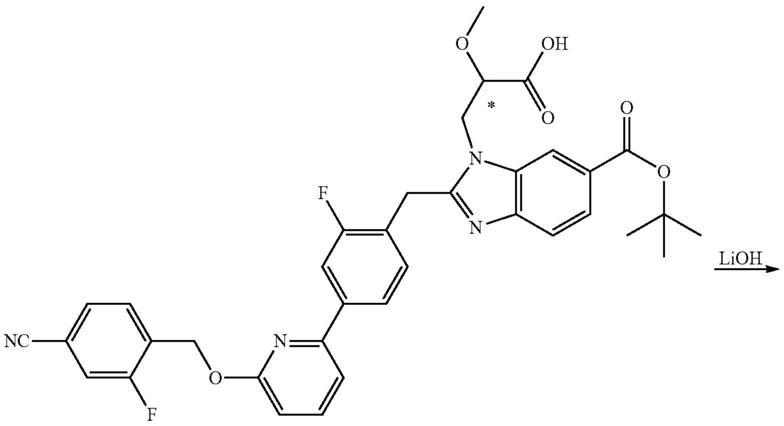

I-35

-continued

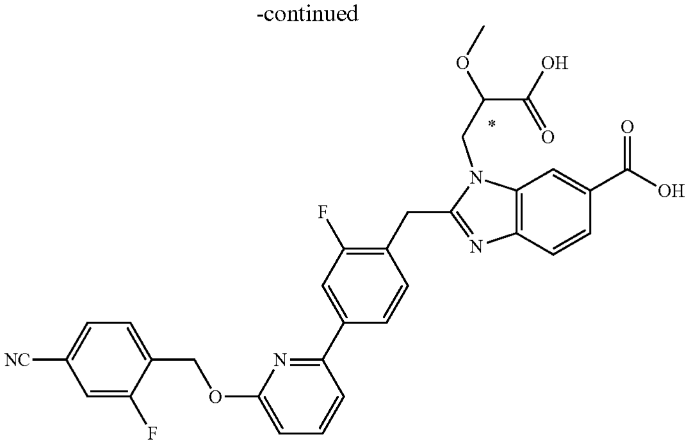

Example 332

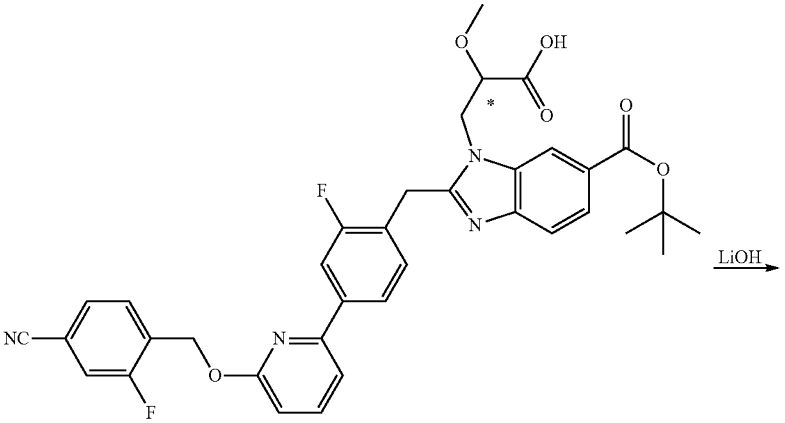

I-36

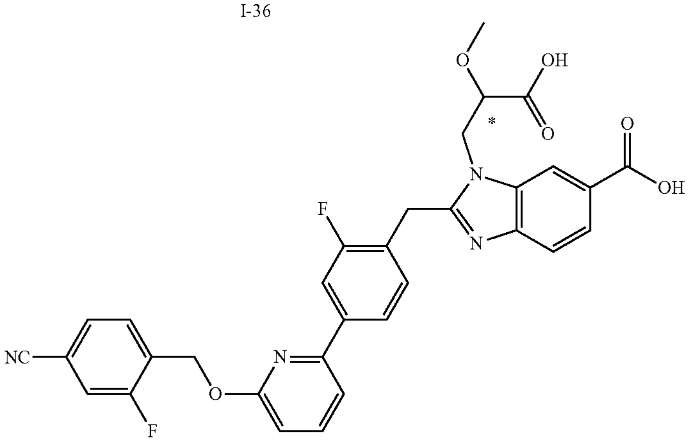

Example 333

1-(2-carboxy-2-methoxyethyl)-2-(4-(6-((4-cyano-2-fluorobenzyl)oxy)pyridin-2-yl)-2-fluorobenzyl)-1H-benzo[d]imidazole-6-carboxylic acid enantiomer 1 (Example 332): 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 1 (I-35) 11 mg, 0.017 mmol) was dissolved in DCM/TFA (3:1, 0.5 mL) and stirred at 30° C. After 20 minutes, the mixture was concentrated, and purified by RP-HPLC (eluent: MeCN/water with 0.1% TFA) to provide the title compound. ES/MS: 599.2 ($M+H^+$); 1H NMR (400 MHz, Acetonitrile-d3) δ 8.31 (d, J=1.4 Hz, 1H), 8.02 (dd, J=8.5, 1.5 Hz, 1H), 7.90-7.77 (m, 3H), 7.76-7.65 (m, 2H), 7.64-7.55 (m, 2H), 7.53 (d, J=7.4 Hz, 1H), 7.45 (t, J=7.8 Hz, 1H), 6.89 (d, J=8.2 Hz, 1H), 5.65 (s, 2H), 4.80-4.64 (m, 2H), 4.58 (d, J=1.8 Hz, 2H), 4.23 (dd, J=7.7, 3.6 Hz, 1H), 3.31 (s, 3H).

1-(2-carboxy-2-methoxyethyl)-2-(4-(6-((4-cyano-2-fluorobenzyl)oxy)pyridin-2-yl)-2-fluorobenzyl)-1H-benzo[d]imidazole-6-carboxylic acid enantiomer 2 (Example 333): A procedure analogous to that used for Example 332 was used to hydrolyze 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 2 (I-36). ES/MS: 599.3 ($M+H^+$). 1H NMR (400 MHz, Acetonitrile-d3) δ 8.33 (dd, J=1.6, 0.7 Hz, 1H), 8.04 (dd, J=8.5, 1.5 Hz, 1H), 7.92-7.78 (m, 3H), 7.73 (t, J=7.9 Hz, 2H), 7.62-7.56 (m, 2H), 7.53 (d, J=7.4 Hz, 1H), 7.46 (t, J=7.9 Hz, 1H), 6.89 (d, J=8.2 Hz, 1H), 5.65 (s, 2H), 4.84-4.64 (m, 2H), 4.60 (d, J=2.0 Hz, 2H), 4.23 (dd, J=7.7, 3.5 Hz, 1H), 3.32 (s, 3H).

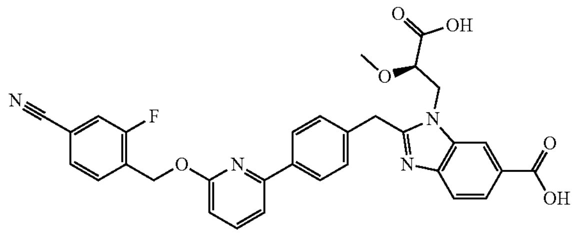

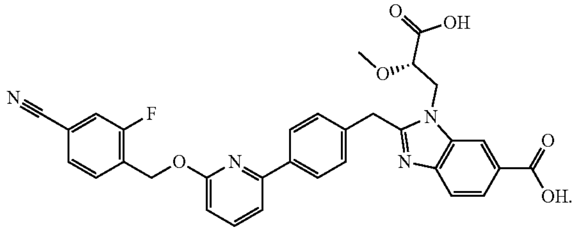

Examples 332 and 333 are depicted below, in no particular order:

Example 328. 2-(4-(6-((4-cyano-2-fluorobenzyl)oxy)pyridin-2-yl)-2-fluorobenzyl)-1-(2-methoxy-3-((2-methoxyethyl)amino)-3-oxopropyl)-1H-benzo[d]imidazole-6-carboxylic acid enantiomer 2

Example 329. 2-(4-(6-((4-cyano-2-fluorobenzyl)oxy)pyridin-2-yl)-2-fluorobenzyl)-1-(2-methoxy-3-oxo-3-(thiazol-2-ylamino)propyl)-1H-benzo[d]imidazole-6-carboxylic acid enantiomer 1

Example 330. 2-(4-(6-((4-cyano-2-fluorobenzyl)oxy)pyridin-2-yl)-2-fluorobenzyl)-1-(2-methoxy-3-(methylamino)-3-oxopropyl)-1H-benzo[d]imidazole-6-carboxylic acid enantiomer 1

Example 334. 1-(3-amino-2-methoxy-3-oxopropyl)-2-(4-(6-((4-cyano-2-fluorobenzyl)oxy)pyridin-2-yl)-2-fluorobenzyl)-1H-benzo[d]imidazole-6-carboxylic acid enantiomer 1

Example 335. 2-(4-(6-((4-cyano-2-fluorobenzyl)oxy)pyridin-2-yl)-2-fluorobenzyl)-1-(2-methoxy-3-((2-methoxyethyl)amino)-3-oxopropyl)-1H-benzo[d]imidazole-6-carboxylic acid enantiomer 1

Example 336. 2-(4-(6-((4-cyano-2-fluorobenzyl)oxy)pyridin-2-yl)-2-fluorobenzyl)-1-(2-methoxy-3-(methylamino)-3-oxopropyl)-1H-benzo[d]imidazole-6-carboxylic acid enantiomer 2

Example 337. 2-(4-(6-((4-cyano-2-fluorobenzyl)oxy)pyridin-2-yl)-2-fluorobenzyl)-1-(2-methoxy-3-(methylamino)-3-oxopropyl)-1H-benzo[d]imidazole-6-carboxylic acid enantiomer 2

Example 338. 2-(4-(6-((4-cyano-2-fluorobenzyl)oxy)pyridin-2-yl)-2-fluorobenzyl)-1-(2-methoxy-3-oxo-3-(thiazol-2-ylamino)propyl)-1H-benzo[d]imidazole-6-carboxylic acid enantiomer 2

Procedure 21

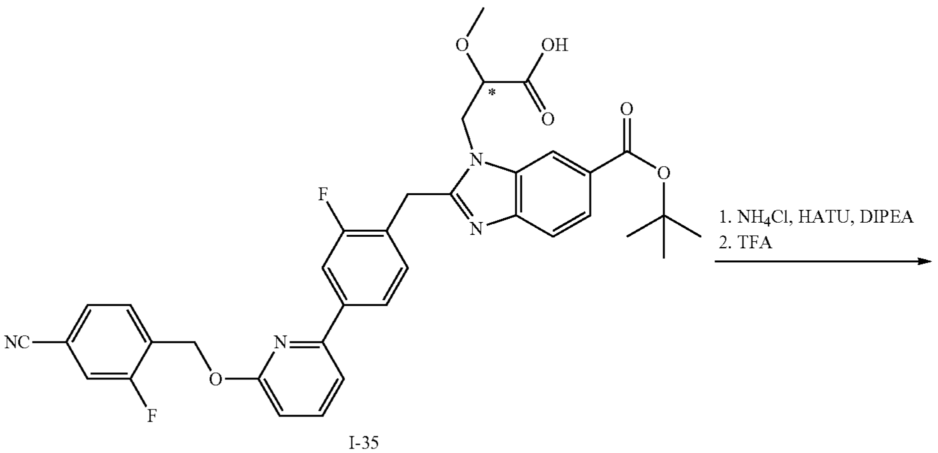

I-35

-continued

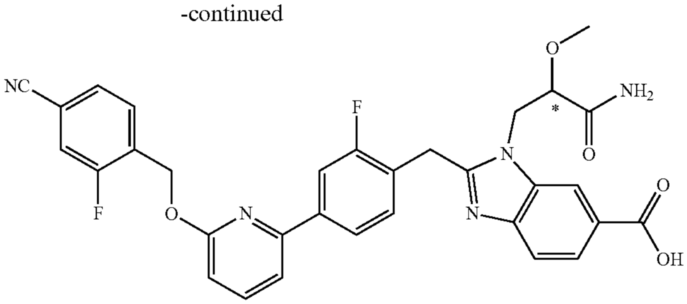

Example 334

1-(3-amino-2-methoxy-3-oxopropyl)-2-(4-(6-((4-cyano-2-fluorobenzyl)oxy)pyridin-2-yl)-2-fluorobenzyl)-1H-benzo[d]imidazole-6-carboxylic acid enantiomer 1 (Example 334): 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 1 (I-35, 16 mg, 0.024 mmol) was combined with DIPEA (0.021 mL, 0.12 mmol), and $NH_4Cl$ (5 mg, 0.09 mmol) in DCM/MeCN (1:1, 0.5 mL). HATU (12 mg, 0.037 mmol) was added and the mixture was stirred at room temperature. After 1 hr, the mixture was concentrated to dryness, dissolved in DCM/TFA (3:1, 0.5 mL), and stirred for 45 minutes to affect the tert-butyl ester deprotection. The crude mixture was concentrated to ~0.1 mL, then purified by RP-HPLC (eluent: MeCN/water with 0.1% TFA) to provide the title compound. ES/MS: 598.3 ($M+H^+$); $^1H$ NMR (400 MHz, Acetonitrile-d3) δ 8.52 (s, 1H), 8.28-8.16 (m, 1H), 7.99-7.90 (m, 2H), 7.85 (t, J=7.9 Hz, 1H), 7.79 (d, J=8.6 Hz, 1H), 7.74 (t, J=7.6 Hz, 1H), 7.64-7.52 (m, 4H), 6.93 (d, J=8.3 Hz, 1H), 6.78 (s, 1H), 6.15 (s, 1H), 5.66 (s, 2H), 4.86-4.81 (m, 2H), 4.80-4.71 (m, 2H), 4.15 (s, 1H), 3.42 (s, 3H).

Example 328

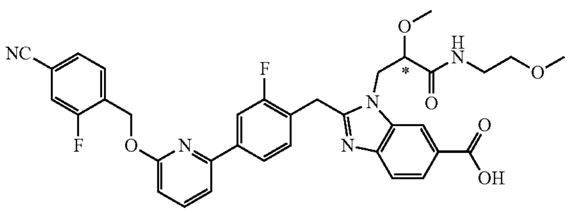

2-(4-(6-((4-cyano-2-fluorobenzyl)oxy)pyridin-2-yl)-2-fluorobenzyl)-1-(2-methoxy-3-((2-methoxyethyl)amino)-3-oxopropyl)-1H-benzo[d]imidazole-6-carboxylic acid enantiomer 2 (Example 328): 2-(4-(6-((4-cyano-2-fluorobenzyl)oxy)pyridin-2-yl)-2-fluorobenzyl)-1-(2-methoxy-3-((2-methoxyethyl)amino)-3-oxopropyl)-1H-benzo[d]imidazole-6-carboxylic acid enantiomer 2 was prepared as described for Example 334, replacing 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 1 (I-35) with 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 2 (I-36) and $NH_4Cl$ with methoxyethylamine: ES/MS: 656.2 ($M+H^+$); $^1H$ NMR (400 MHz, DMSO-d6) δ 8.22 (d, J=1.5 Hz, 1H), 7.96-7.82 (m, 5H), 7.80-7.71 (m, 2H), 7.68 (d, J=7.5 Hz, 1H), 7.61 (d, J=8.4 Hz, 1H), 7.44 (dd, J=9.2, 6.8 Hz, 1H), 6.94 (d, J=8.2 Hz, 1H), 5.63 (s, 2H), 4.77-4.56 (m, 2H), 4.50 (s, 2H), 4.11 (dd, J=6.8, 4.1 Hz, 1H), 3.23 (s, 3H), 3.23-3.19 (m, 4H), 3.17 (s, 3H).

Example 329

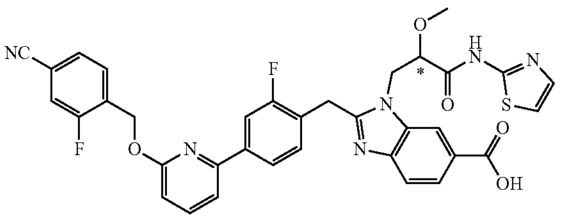

2-(4-(6-((4-cyano-2-fluorobenzyl)oxy)pyridin-2-yl)-2-fluorobenzyl)-1-(2-methoxy-3-oxo-3-(thiazol-2-ylamino)propyl)-1H-benzo[d]imidazole-6-carboxylic acid enantiomer 1 (Example 329): 2-(4-(6-((4-cyano-2-fluorobenzyl)oxy)pyridin-2-yl)-2-fluorobenzyl)-1-(2-methoxy-3-oxo-3-(thiazol-2-ylamino)propyl)-1H-benzo[d]imidazole-6-carboxylic acid enantiomer 1 was prepared as described for Example 334, replacing $NH_4Cl$ with 2-aminothiazole: ES/MS: 681.2 ($M+H^+$); $^1H$ NMR (400 MHz, Acetonitrile-d3) δ 8.39 (s, 1H), 8.06 (dt, J=8.7, 2.0 Hz, 1H), 7.88 (d, J=9.8 Hz, 2H), 7.82 (t, J=7.9 Hz, 1H), 7.77-7.67 (m, 2H), 7.62-7.45 (m, 5H), 7.16 (dd, J=3.7, 2.5 Hz, 1H), 6.91 (d, J=8.2 Hz, 1H), 5.65 (s, 2H), 4.94-4.81 (m, 2H), 4.76-4.65 (m, 2H), 4.51-4.42 (m, 1H), 3.45 (s, 3H).

Example 330

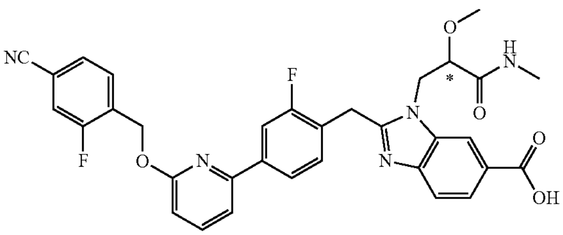

2-(4-(6-((4-cyano-2-fluorobenzyl)oxy)pyridin-2-yl)-2-fluorobenzyl)-1-(2-methoxy-3-(methylamino)-3-oxopropyl)-1H-benzo[d]imidazole-6-carboxylic acid enantiomer 1 (Example 330): 2-(4-(6-((4-cyano-2-fluorobenzyl)oxy)pyridin-2-yl)-2-fluorobenzyl)-1-(2-methoxy-3-(methylamino)-3-oxopropyl)-1H-benzo[d]imidazole-6-carboxylic acid enantiomer 1 was prepared according to Procedure 21 as described for Example 334, replacing $NH_4Cl$ with $MeNH_2 \cdot HCl$: ES/MS: 612.2 (M+H$^+$); $^1$H NMR (400 MHz, Acetonitrile-d3) δ 8.36 (t, J=1.0 Hz, 1H), 8.08 (dd, J=8.6, 1.5 Hz, 1H), 7.91-7.85 (m, 2H), 7.82 (dd, J=8.2, 7.5 Hz, 1H), 7.79-7.70 (m, 2H), 7.62-7.57 (m, 2H), 7.55 (d, J=7.5 Hz, 1H), 7.49 (t, J=7.8 Hz, 1H), 7.00-6.93 (m, 1H), 6.91 (d, J=8.2 Hz, 1H), 5.65 (s, 2H), 4.80-4.67 (m, 2H), 4.66 (s, 2H), 4.17-4.04 (m, 1H), 3.35 (s, 3H), 2.60 (d, J=4.8 Hz, 3H).

Example 335

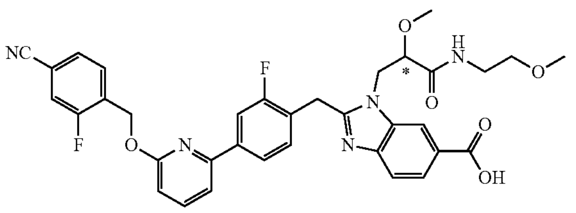

2-(4-(6-((4-cyano-2-fluorobenzyl)oxy)pyridin-2-yl)-2-fluorobenzyl)-1-(2-methoxy-3-((2-methoxyethyl)amino)-3-oxopropyl)-1H-benzo[d]imidazole-6-carboxylic acid enantiomer 1 (Example 335): 2-(4-(6-((4-cyano-2-fluorobenzyl)oxy)pyridin-2-yl)-2-fluorobenzyl)-1-(2-methoxy-3-((2-methoxyethyl)amino)-3-oxopropyl)-1H-benzo[d]imidazole-6-carboxylic acid enantiomer 1 was prepare as described for Example 334, replacing $NH_4Cl$ with methoxyethylamine: ES/MS: 656.2 (M+H$^+$); $^1$H NMR (400 MHz, Acetonitrile-d3) δ 8.40-8.36 (m, 1H), 8.08 (dd, J=8.6, 1.5 Hz, 1H), 7.91-7.79 (m, 3H), 7.79-7.69 (m, 2H), 7.62-7.52 (m, 3H), 7.48 (t, J=7.7 Hz, 1H), 7.00 (s, 1H), 6.90 (dd, J=8.1, 1.9 Hz, 1H), 5.65 (s, 2H), 4.74 (d, J=4.6 Hz, 2H), 4.66 (s, 2H), 4.12 (t, J=4.6 Hz, 1H), 3.39 (s, 3H), 3.28-3.20 (m, 2H), 3.18 (s, 3H).

Examples 328 and 335 are depicted below, in no particular order:

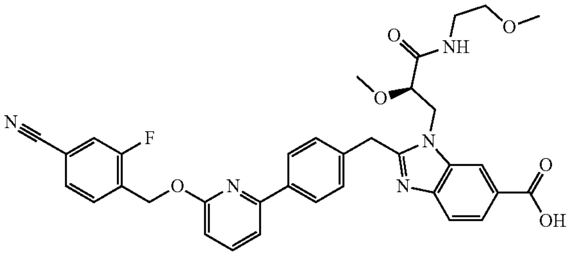

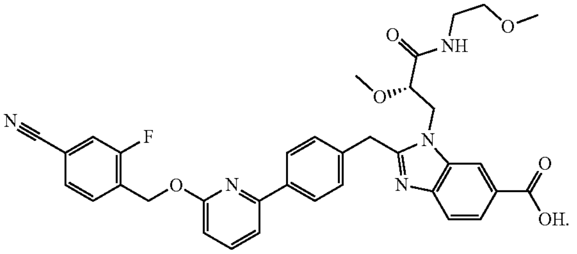

-continued

Example 336

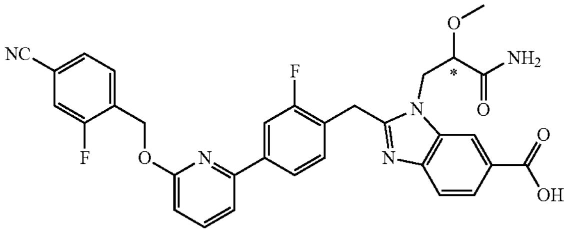

2-(4-(6-((4-cyano-2-fluorobenzyl)oxy)pyridin-2-yl)-2-fluorobenzyl)-1-(2-methoxy-3-(methylamino)-3-oxopropyl)-1H-benzo[d]imidazole-6-carboxylic acid enantiomer 2 (Example 336): 2-(4-(6-((4-cyano-2-fluorobenzyl)oxy)pyridin-2-yl)-2-fluorobenzyl)-1-(2-methoxy-3-(methylamino)-3-oxopropyl)-1H-benzo[d]imidazole-6-carboxylic acid enantiomer 2 was prepared as described for Example 334, but replacing 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 1 (I-35) with 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 2 (I-36): ES/MS: 598.2 (M+H$^+$); $^1$H NMR (400 MHz, DMSO-d6) δ 8.26 (d, J=1.5 Hz, 1H), 7.97-7.82 (m, 5H), 7.80-7.71 (m, 2H), 7.71-7.66 (m, 2H), 7.62 (d, J=8.5 Hz, 1H), 7.53 (s, 1H), 7.45 (t, J=8.0 Hz, 1H), 6.94 (d, J=8.2 Hz, 1H), 5.63 (s, 2H), 4.68 (dd, J=15.3, 3.7 Hz, 1H), 4.58 (dd, J=15.3, 7.8 Hz, 1H), 4.51 (s, 2H), 4.01 (dd, J=7.7, 3.7 Hz, 1H), 3.21 (s, 3H).

Examples 334 and 336 are depicted below, in no particular order:

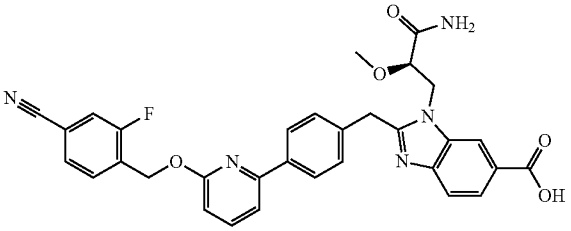

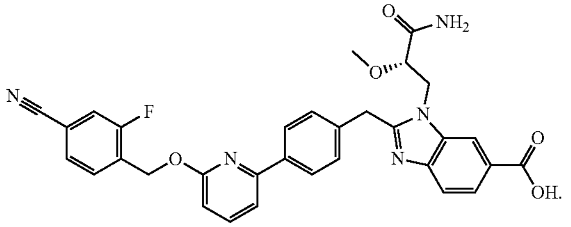

Example 337

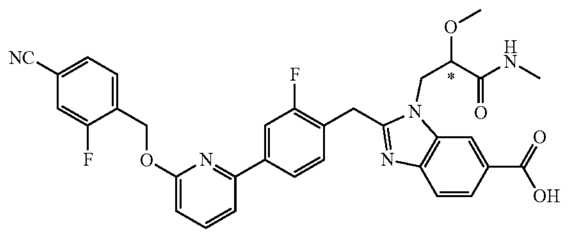

2-(4-(6-((4-cyano-2-fluorobenzyl)oxy)pyridin-2-yl)-2-fluorobenzyl)-1-(2-methoxy-3-(methylamino)-3-oxopropyl)-1H-benzo[d]imidazole-6-carboxylic acid enantiomer 2 (Example 337): 2-(4-(6-((4-cyano-2-fluorobenzyl)oxy)pyridin-2-yl)-2-fluorobenzyl)-1-(2-methoxy-3-(methylamino)-3-oxopropyl)-1H-benzo[d]imidazole-6-carboxylic acid enantiomer 2 was prepared as described for Example 334, but replacing 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 1 (I-35) with 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 2 (I-36) and $NH_4Cl$ with $MeNH_2{\cdot}HCl$: ES/MS: 612.3 (M+$H^+$); $^1H$ NMR (400 MHz, DMSO-d6) δ 8.21 (d, J=1.5 Hz, 1H), 8.13 (q, J=4.5 Hz, 1H), 7.97-7.81 (m, 5H), 7.80-7.71 (m, 2H), 7.68 (d, J=7.5 Hz, 1H), 7.61 (d, J=8.5 Hz, 1H), 7.44 (t, J=8.0 Hz, 1H), 6.94 (d, J=8.2 Hz, 1H), 5.63 (s, 2H), 4.69 (dd, J=15.2, 3.9 Hz, 1H), 4.58 (dd, J=15.3, 7.1 Hz, 1H), 4.48 (s, 2H), 4.05 (dd, J=7.0, 3.9 Hz, 1H), 3.21 (s, 3H), 2.58 (d, J=4.6 Hz, 3H).

Examples 330 and 337 are depicted below, in no particular order:

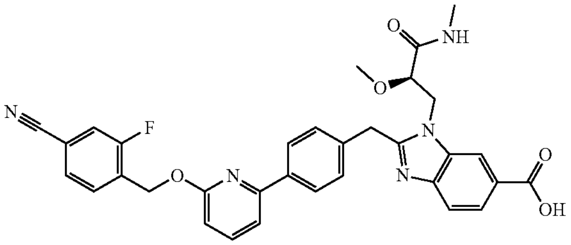

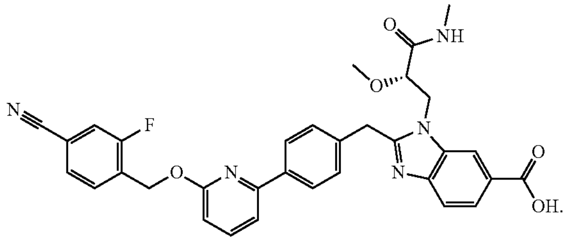

Example 338

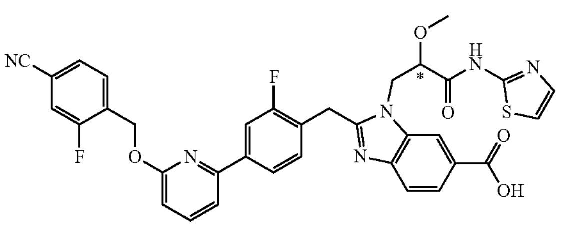

2-(4-(6-((4-cyano-2-fluorobenzyl)oxy)pyridin-2-yl)-2-fluorobenzyl)-1-(2-methoxy-3-oxo-3-(thiazol-2-ylamino)propyl)-1H-benzo[d]imidazole-6-carboxylic acid enantiomer 2 (Example 338): 2-(4-(6-((4-cyano-2-fluorobenzyl)oxy)pyridin-2-yl)-2-fluorobenzyl)-1-(2-methoxy-3-oxo-3-(thiazol-2-ylamino)propyl)-1H-benzo[d]imidazole-6-carboxylic acid enantiomer 2 was prepared as described for Example 334, replacing 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 1 (I-35) with 3-(6-(tert-butoxycarbonyl)-2-(4-(6-((4-cyano-2-fluorobenzyl)oxy)pyridin-2-yl)-2-fluorobenzyl)-1H-benzo[d]imidazol-1-yl)-2-methoxypropanoic acid enantiomer 2 (I-36) and $NH_4Cl$ with 2-aminothiazole:

ES/MS: 681.2 (M+$H^+$); $^1H$ NMR (400 MHz, DMSO-d6) δ 12.63 (s, 1H), 8.36 (d, J=1.4 Hz, 1H), 7.96-7.82 (m, 5H), 7.81-7.70 (m, 2H), 7.68 (d, J=7.5 Hz, 1H), 7.62 (d, J=8.4 Hz, 1H), 7.54 (d, J=3.6 Hz, 1H), 7.44 (t, J=8.1 Hz, 1H), 7.31 (d, J=3.5 Hz, 1H), 6.94 (d, J=8.2 Hz, 1H), 5.63 (s, 2H), 4.86 (dd, J=15.2, 3.8 Hz, 1H), 4.71 (dd, J=15.3, 8.6 Hz, 1H), 4.53 (s, 2H), 4.47 (dd, J=8.6, 3.8 Hz, 1H), 3.21 (s, 3H).

Examples 329 and 338 are depicted below, in no particular order:

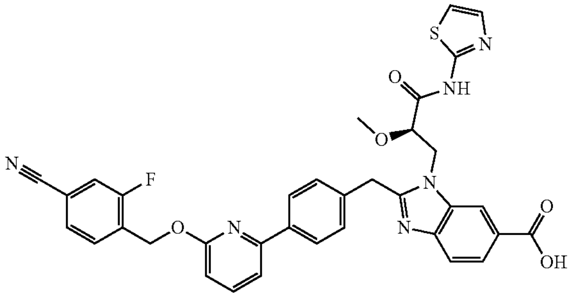

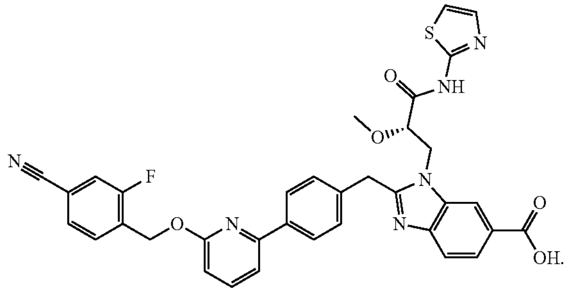

Example 339. 1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylic acid enantiomer 1

Example 340. 1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylic acid enantiomer 2

Procedure 22

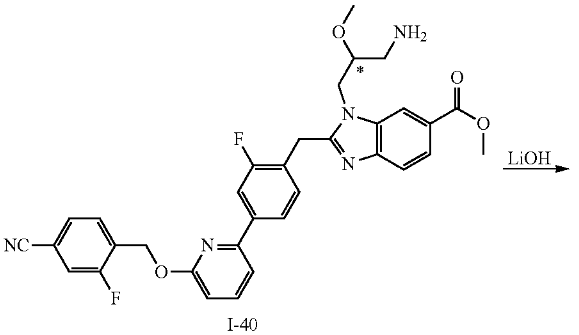

I-40
peak 1

-continued

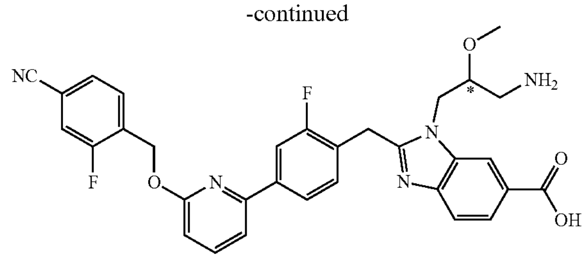

Example 339

1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylic acid enantiomer 1 (Example 339): Methyl 1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylate enantiomer 1 (1-40, 12 mg, 0.020 mmol) was dissolved in THF/water (2:1, 0.5 mL) with lithium hydroxide monohydrate (4.2 mg, 0.10 mmol) and stirred at 45° C. overnight. The mixture was then diluted with acetonitrile and aqueous TFA and purified by HPLC to provide the title compound: ES/MS: 584.2 ($M+H^+$); $^1H$ NMR (400 MHz, Acetonitrile-d3+D2O) δ 8.33 (d, J=1.4 Hz, 1H), 7.97 (dd, J=8.4, 1.5 Hz, 1H), 7.86-7.79 (m, 3H), 7.73 (t, J=7.7 Hz, 1H), 7.67 (d, J=8.5 Hz, 1H), 7.64-7.56 (m, 2H), 7.55 (d, J=7.4 Hz, 1H), 7.43 (t, J=7.9 Hz, 1H), 6.90 (d, J=8.2 Hz, 1H), 5.65 (s, 2H), 4.59-4.40 (m, 3H), 3.95 (dt, J=7.8, 3.8 Hz, 1H), 3.30 (dd, J=13.3, 3.5 Hz, 1H), 3.11 (s, 3H), 3.04 (dd, J=13.4, 7.9 Hz, 1H), 2.00-1.98 (m, 1H).

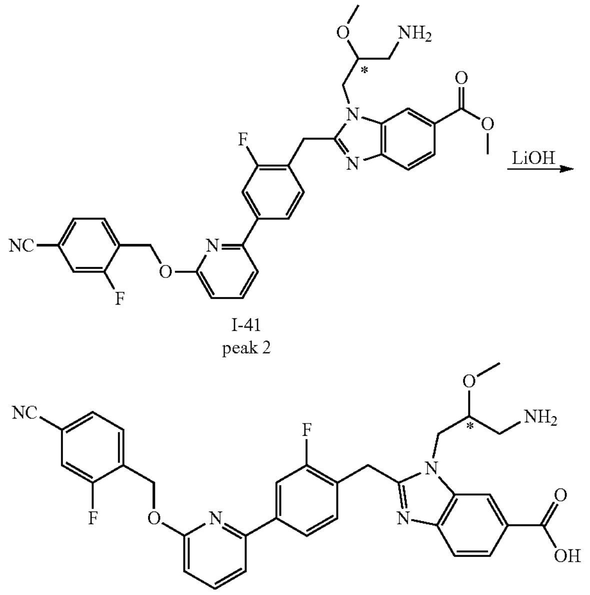

I-41
peak 2

Example 340

1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylic acid enantiomer 2 (Example 340): 1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylic acid enantiomer 2 was prepared according to the procedure for Example 339, replacing methyl 1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylate enantiomer 1 (I-40) with methyl 1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylate enantiomer 2 (I-41): ES/MS: 584.2 ($M+H^+$); 1H NMR (400 MHz, DMSO-d6) δ 8.33 (d, J=1.5 Hz, 1H), 8.03-7.85 (m, 6H), 7.82 (dd, J=8.4, 1.5 Hz, 1H), 7.79-7.72 (m, 2H), 7.67 (d, J=7.4 Hz, 1H), 7.62 (d, J=8.4 Hz, 1H), 7.45 (t, J=8.0 Hz, 1H), 6.95 (d, J=8.2 Hz, 1H), 5.63 (s, 2H), 4.67-4.59 (m, 1H), 4.53 (dd, J=15.2, 8.7 Hz, 1H), 4.44 (s, 2H), 3.05 (s, 3H), 3.02-2.93 (m, 1H).

Examples 339 and 340 are depicted below, in no particular order:

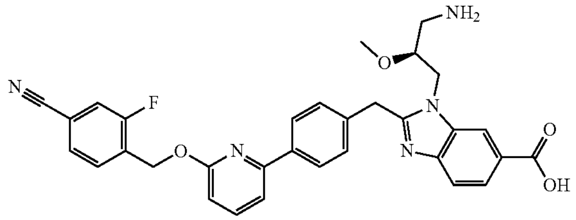

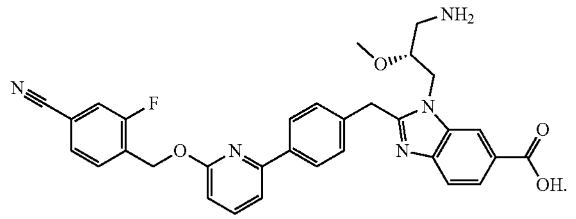

Example 341. 1-(3-acetamido-2-methoxypropyl)-2-(4-(6-((4-cyano-2-fluorobenzyl)oxy)pyridin-2-yl)-2-fluorobenzyl)-1H-benzo[d]imidazole-6-carboxylic acid isomer 1

Example 342. 1-(3-acetamido-2-methoxypropyl)-2-(4-(6-((4-cyano-2-fluorobenzyl)oxy)pyridin-2-yl)-2-fluorobenzyl)-1H-benzo[d]imidazole-6-carboxylic acid isomer 2

Procedure 23

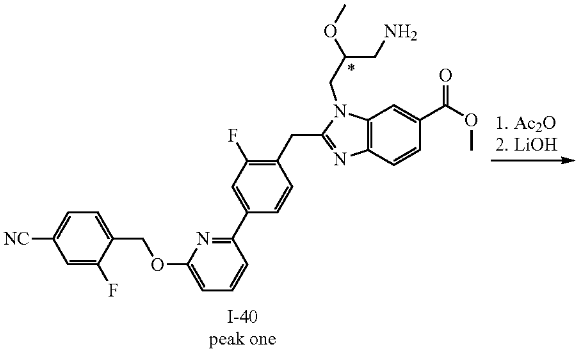

I-40
peak one

-continued

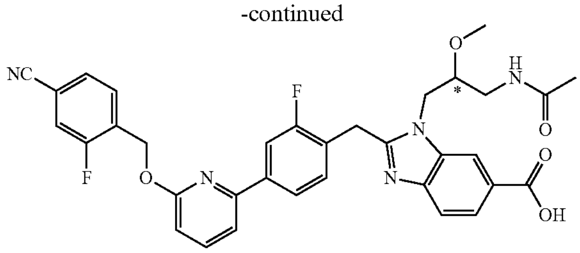

Example 342

1-(3-acetamido-2-methoxypropyl)-2-(4-(6-((4-cyano-2-fluorobenzyl)oxy)pyridin-2-yl)-2-fluorobenzyl)-1H-benzo[d]imidazole-6-carboxylic acid (Example 342): Methyl 1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylate enantiomer 1 (I-40, 20 mg, 0.033 mmol) was dissolved in DCM (0.5 mL) with $Et_3N$ (0.02 mL). Acetic Anhydride (6.8 mg, 0.067 mmol) was added and the mixture was stirred for 5 minutes, concentrated to dryness, and dissolved in THF (0.5 mL) and water (0.1 mL). Lithium hydroxide monohydrate (11 mg, 0.27 mmol) was added and the mixture was stirred at 55° C. overnight. The mixture was then diluted with acetonitrile and aqueous TFA and purified by HPLC to provide the title compound: ES/MS: 626.2 (M+H$^+$); $^1$H NMR (400 MHz, Acetonitrile-d3) δ 8.45 (s, 1H), 8.17 (d, J=8.4 Hz, 1H), 7.91 (d, J=9.5 Hz, 2H), 7.89-7.78 (m, 2H), 7.73 (t, J=7.5 Hz, 1H), 7.65-7.55 (m, 3H), 7.51 (t, J=8.0 Hz, 1H), 6.92 (d, J=8.1 Hz, 1H), 6.78-6.63 (m, 1H), 5.66 (s, 2H), 4.68 (d, J=7.2 Hz, 2H), 4.62-4.54 (m, 1H), 4.50-4.37 (m, 1H), 3.75-3.54 (m, 2H), 3.50-3.38 (m, 1H), 3.18 (s, 3H), 2.12 (s, 3H).

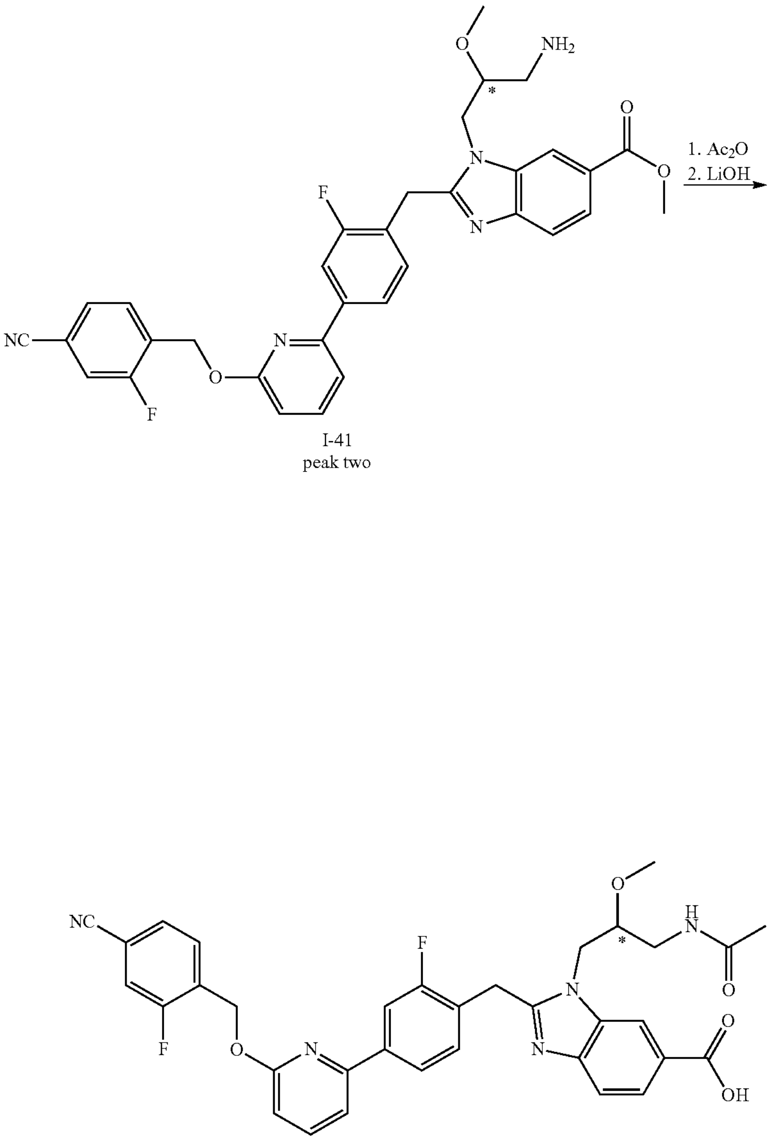

I-41
peak two

Example 341

1-(3-acetamido-2-methoxypropyl)-2-(4-(6-((4-cyano-2-fluorobenzyl)oxy)pyridin-2-yl)-2-fluorobenzyl)-1H-benzo[d]imidazole-6-carboxylic acid (Example 341): 1-(3-acetamido-2-methoxypropyl)-2-(4-(6-((4-cyano-2-fluorobenzyl)oxy)pyridin-2-yl)-2-fluorobenzyl)-1H-benzo[d]imidazole-6-carboxylic acid was prepared according to the procedure described for Example 342, replacing methyl 1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylate enantiomer 1 (I-40) with methyl 1-(3-amino-2-methoxypropyl)-2-(4-(6-((4-cyano-2-fluorobenzyl)oxy)pyridin-2-yl)-2-fluorobenzyl)-1H-benzo[d]imidazole-6-carboxylate enantiomer 2 (I-41): ES/MS: 626.2 ($M+H^+$); $^1H$ NMR (400 MHz, DMSO-d6) δ 8.22 (s, 1H), 8.12 (t, J=5.9 Hz, 1H), 7.93 (dd, J=10.1, 1.2 Hz, 1H), 7.91-7.81 (m, 4H), 7.80-7.71 (m, 2H), 7.67 (d, J=7.5 Hz, 1H), 7.62 (d, J=8.5 Hz, 1H), 7.43 (t, J=7.8 Hz, 1H), 6.94 (d, J=8.2 Hz, 1H), 5.62 (s, 2H), 4.59-4.42 (m, 2H), 4.36 (dd, J=15.2, 9.6 Hz, 1H), 3.46-3.21 (m, 4H), 3.07 (s, 3H), 1.91 (s, 3H).

Examples 341 and 342 are depicted below, in no particular order:

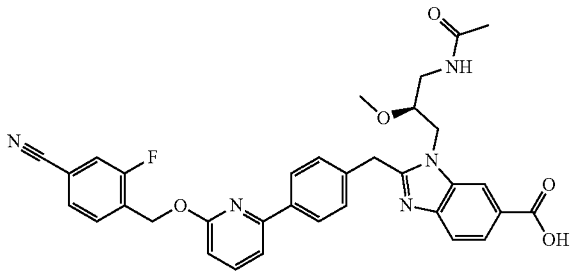

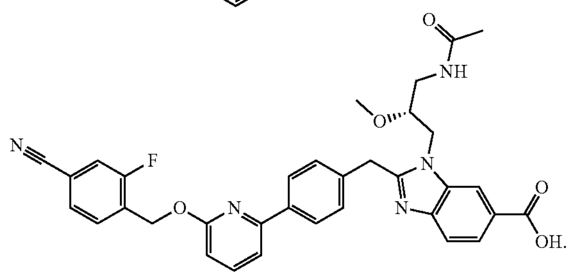

Example 103. 2-[[4-[3-[(4-cyano-2-fluoro-phenyl)methoxy]pyridazin-4-yl]-2,6-difluoro-phenyl]methyl]-3-(2-methoxyethyl)benzimidazole-5-carboxylic acid Procedure 24

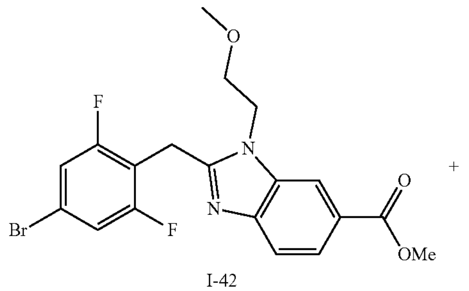

I-42

-continued

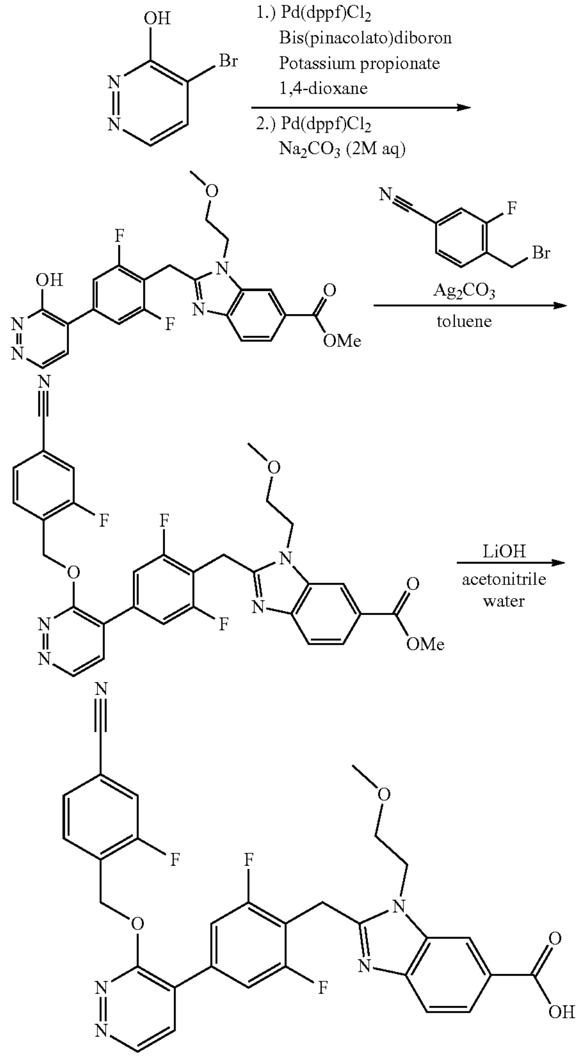

Example 103

Methyl 2-[[2,6-difluoro-4-(3-hydroxypyridazin-4-yl)phenyl]methyl]-3-(2-methoxyethyl)benzimidazole-5-carboxylate: In an 8 mL vial, a suspension of methyl 2-[(4-bromo-2,6-difluoro-phenyl)methyl]-3-(2-methoxyethyl)benzimidazol)-5-carboxylate (I-42, 100 mg, 0.228 mmol), bis(pinacolato)diboron (70.5 mg, 0.278 mmol), [1,1'-bis(diphenylphosphino)ferrocene]dichloropalladium(II), $PdCl_2$(dppf) (25.3 mg, 0.0341 mmol), and potassium propionate (76.6 mg, 0.683 mmol) in dioxane (2 mL) was degassed with Ar for 5 min. The mixture was sealed and heated at 110° C. for 30 min. Aqueous sodium carbonate (2.0 M, 0.260 mL, 0.520 mmol) was added. The mixture was stirred at RT for 2 min. To this was added [1,1'-bis(diphenylphosphino)ferrocene]dichloropalladium(II), $PdCl_2$ (dppf) (16.8 mg, 0.0226 mmol), and 4-bromopyridazin-3-ol (39.8 mg, 0.228 mmol). The mixture was degassed for 5 min with Ar, then sealed and heated at 90° C. overnight. The mixture was diluted with EtOAc and washed with brine. The organic extract was dried over sodium sulfate and purified by silica gel column chromatography (eluent: EtOAc/hexanes) to give the title product: ES/MS: 455.2 ($M+H^+$); 1H NMR (400 MHz, $CDCl_3$) δ 10.59 (s, 1H), 8.12 (s, 1H), 7.95 (d, J=24.2 Hz, 2H), 7.76 (s, 1H), 7.54 (s, 2H), 7.40 (s, 1H), 4.49 (s, 4H), 3.98 (s, 3H), 3.77 (s, 2H), 3.33 (s, 3H).

Methyl 2-[[4-[3-[(4-cyano-2-fluoro-phenyl)methoxy]pyridazin-4-yl]-2,6-difluoro-phenyl]methyl]-3-(2-methoxy-ethyl)benzimidazole-5-carboxylate: In a 40 mL reaction vial, a suspension of 4-(bromomethyl)-3-fluoro-benzonitrile (27.0 mg, 0.126 mmol), methyl 2-[[2,6-difluoro-4-(3-hydroxypyridazin-4-yl)phenyl]methyl]-3-(2-methoxyethyl)benzimidazole-5-carboxylate (37.0 mg, 0.0814 mmol), and silver carbonate (67.4 mg, 0.244 mmol) in toluene (7 mL) was heated at 100° C. overnight. The mixture was filtered through Celite, concentrated, and purified by silica gel column chromatography (eluent: EtOAc/hexanes) to give the title product: ES/MS: 588.2 ($M+H^+$).

1.5 Hz, 1H), 7.82 (d, J=4.8 Hz, 1H), 7.76 (t, J=7.6 Hz, 1H), 7.70 (d, J=8.6 Hz, 1H), 7.65 (dd, J=9.7, 1.5 Hz, 1H), 7.60 (dd, J=8.0, 1.6 Hz, 1H), 7.56 (d, J=8.4 Hz, 2H), 5.80 (s, 2H), 4.78 (t, J=5.0 Hz, 2H), 4.73 (s, 2H), 3.83 (t, J=4.9 Hz, 2H), 3.30 (s, 3H).

Example 104. 4-[[6-[2,5-difluoro-4-[[1-(2-methoxyethyl)-6-(2H-tetrazol-5-yl)benzimidazol-2-yl]methyl]phenyl]-2-pyridyl]oxymethyl]-3-fluoro-benzonitrile Procedure 25

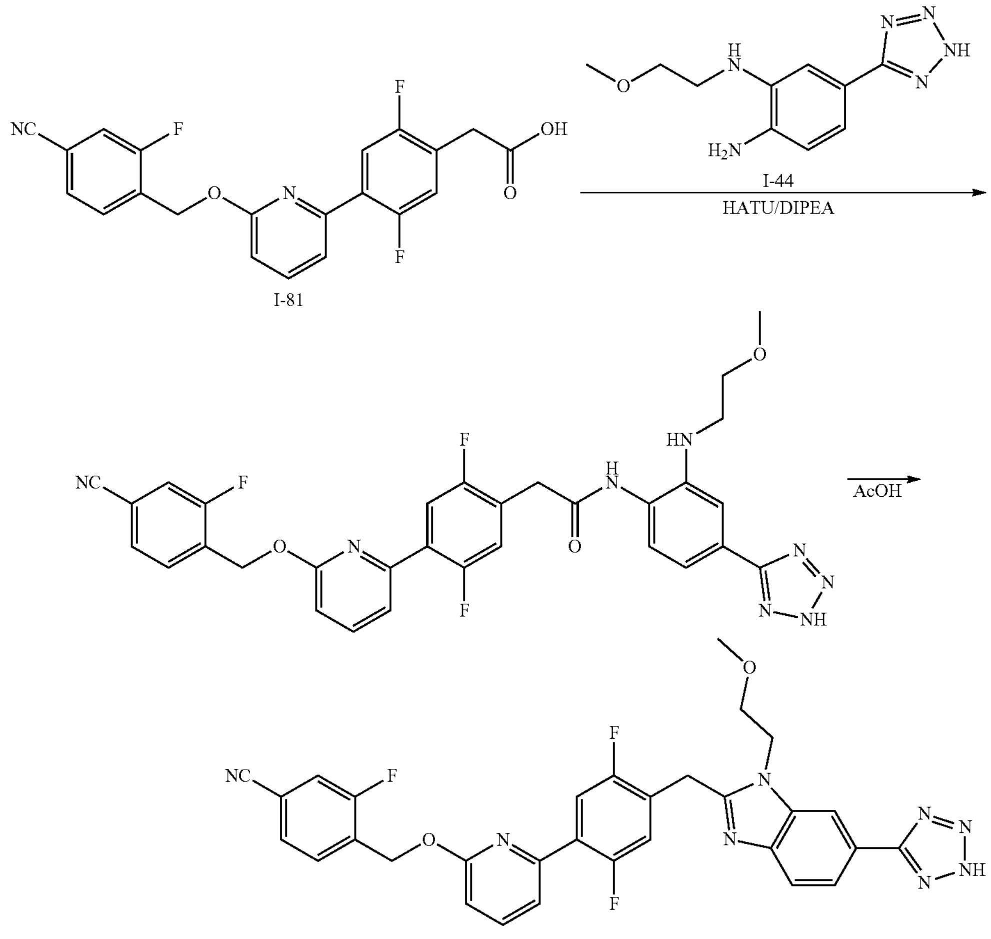

I-81

Example 104

2-[[4-[3-[(4-cyano-2-fluoro-phenyl)methoxy]pyridazin-4-yl]-2,6-difluoro-phenyl]methyl]-3-(2-methoxyethyl)benzimidazole-5-carboxylic acid (Example 103): A suspension of methyl 2-[[4-[3-[(4-cyano-2-fluoro-phenyl)methoxy]pyridazin-4-yl]-2,6-difluoro-phenyl]methyl]-3-(2-methoxyethyl)benzimidazole-5-carboxylate (8.40 mg, 0.0143 mmol) and lithium hydroxide (0.3 M, 0.15 mL, 0.045 mmol) in $CH_3CN$ (1 mL) in a 40 ml reaction vial was sealed and heated at 90° C. for 2.5 hr. The mixture was acidified by addition of 3 drops of trifluoroacetic acid. The material was purified by RP-HPLC (eluent: water/MeCN*0.1% TFA) to yield the product Example 103 as a trifluoroacetate salt. ES/MS: 574.2 ($M+H^+$); $^1H$ NMR (400 MHz, MeOD) δ 9.00 (d, J=4.9 Hz, 1H), 8.46 (d, J=1.2 Hz, 1H), 8.14 (dd, J=8.6, 2-[4-[6-[(4-cyano-2-fluoro-phenyl)methoxy]-2-pyridyl]-2,5-difluoro-phenyl]-N-[2-(2-methoxyethylamino)-4-(2H-tetrazol-5-yl)phenyl]acetamide: To a solution of 2-[4-[6-[(4-cyano-2-fluoro-phenyl)methoxy]-2-pyridyl]-2,5-difluoro-phenyl]acetic acid (I-81, 52.0 mg, 0.131 mmol), N2-(2-methoxyethyl)-4-(2H-tetrazol-5-yl)benzene-1,2-diamine (I-44, 30.6 mg, 0.131 mmol), and o-(7-azabenzotriazol-1-yl)-N,N,N',N'-tetramethyluronium hexafluorophosphate (73.6 mg, 0.194 mmol) in DMF (3 mL), was added N,N-diisopropylethylamine (0.124 mL, 0.713 mmol). The mixture was stirred at RT overnight. The mixture was diluted with EtOAc and washed with aqueous 5% LiCl and brine. The organic extract was dried over sodium sulfate, concentrated and carried onto the next step without further purification: ES/MS: 615.2.2 ($M+H^+$).

4-[[6-[2,5-difluoro-4-[[1-(2-methoxyethyl)-6-(2H-tetrazol-5-yl)benzimidazol-2-yl]methyl]phenyl]-2-pyridyl]oxymethyl]-3-fluoro-benzonitrile (Example 104): A solution of 2-[4-[6-[(4-cyano-2-fluoro-phenyl)methoxy]-2-pyridyl]-2,5-difluoro-phenyl]-N-[2-(2-methoxyethylamino)-4-(2H-tetrazol-5-yl)phenyl]acetamide (44.8 mg, 0.0729 mmol) and glacial acetic acid (0.271 mL, 4.74 mmol) in DCE (3 mL) was heated at 60° C. overnight. The mixture was concentrated to dryness, then diluted with DMF and purified by RP-HPLC (eluent: water/MeCN 0.1% TFA) to yield the product (Example 104) as a trifluoroacetate salt: ES/MS: 597.2 ($M+H^+$); $^1H$ NMR (400 MHz, MeOD) δ 8.36 (s, 1H), 8.00 (d, J=8.3 Hz, 1H), 7.85-7.71 (m, 4H), 7.64-7.54 (m, 3H), 7.22 (dd, J=11.4, 6.1 Hz, 1H), 6.94 (d, J=8.3 Hz, 1H), 5.64 (s, 2H), 4.67 (t, J=5.1 Hz, 2H), 4.58 (s, 2H), 3.81 (t, J=5.0 Hz, 2H), 3.30 (s, 3H).

Example 107. 2-[[1-[6-[(4-cyano-2-fluoro-phenyl)methoxy]-2-pyridyl]pyrazol-4-yl]methyl]-3-(2-methoxyethyl)benzimidazole-5-carboxylic acid Procedure 26

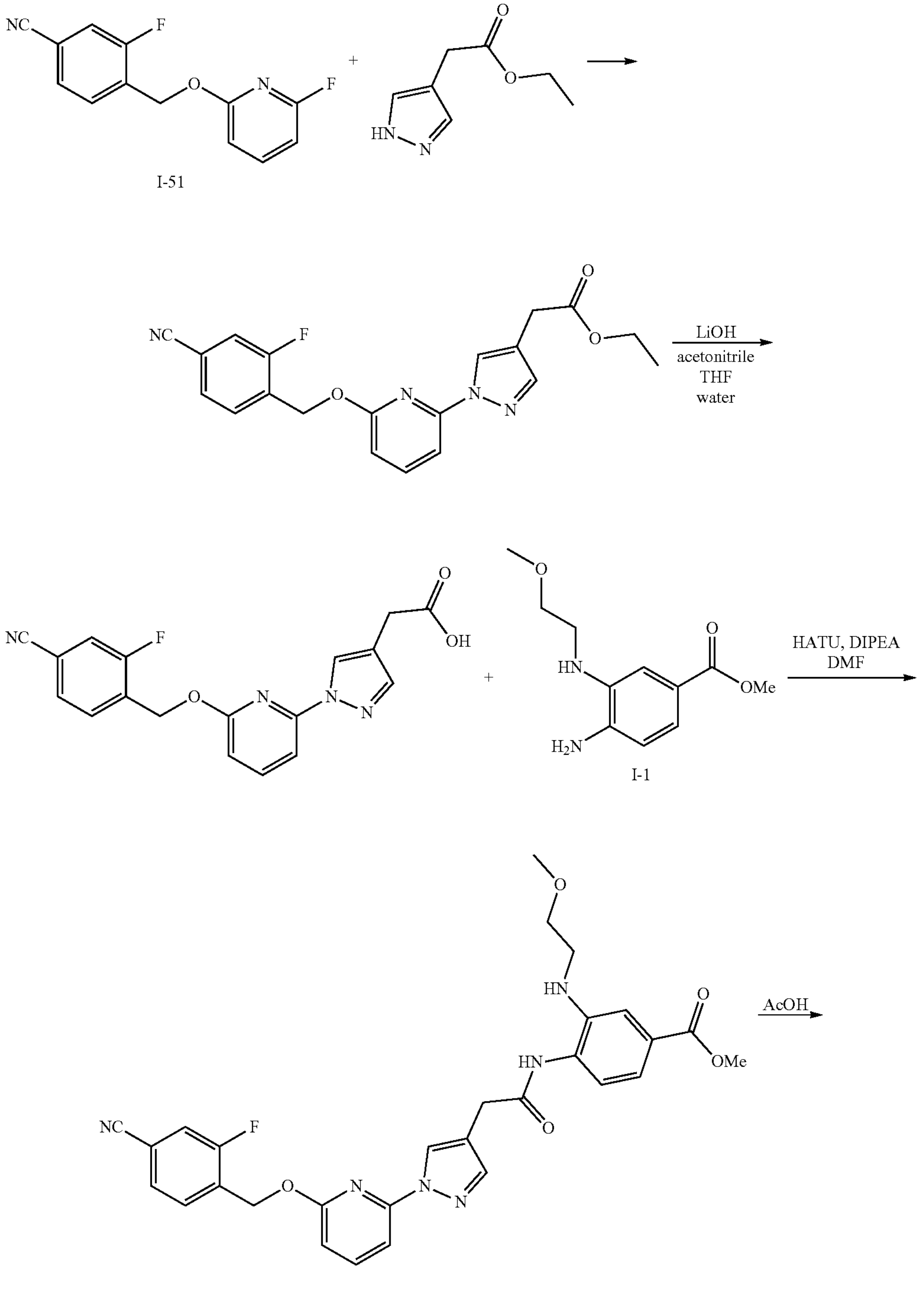

-continued

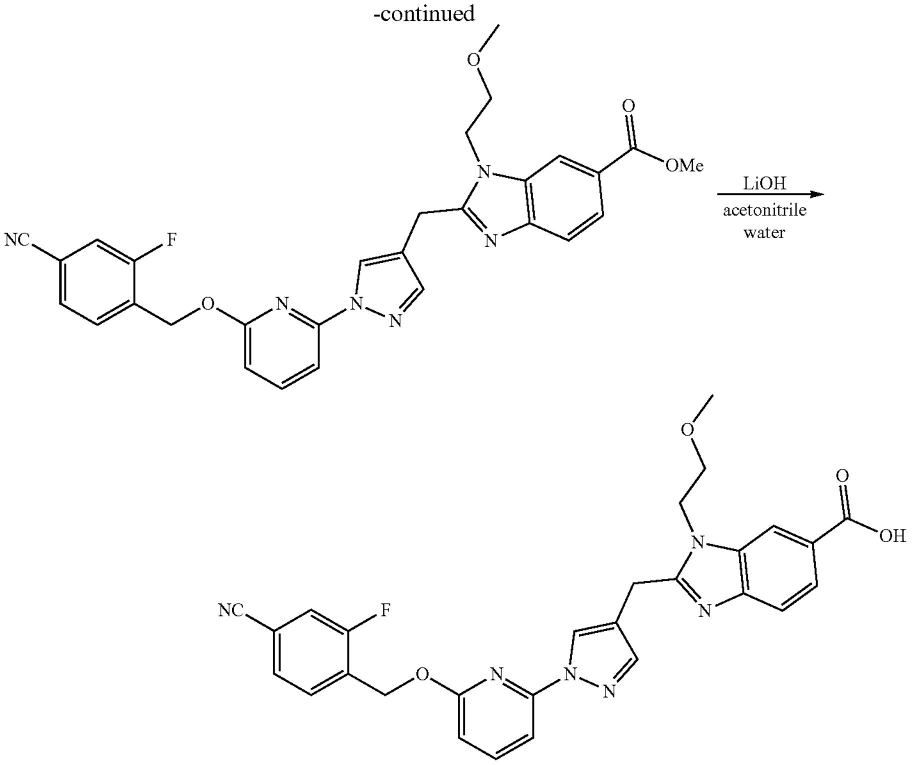

Example 107

Ethyl 2-[1-[6-[(4-cyano-2-fluoro-phenyl)methoxy]-2-pyridyl]pyrazol-4-yl]acetate: A suspension of 3-fluoro-4-[(6-fluoro-2-pyridyl)oxymethyl]benzonitrile (I-51, 0.10 g, 406 μmol), ethyl 2-(1H-pyrazol-4-yl)acetate (0.098 g, 636 μmol), and potassium carbonate (0.178 g, 1.29 mmol) in NMP (2 mL) was heated at 100° C. for 72 h. LCMS was conducted and indicated a mixture of regio-isomeric products. The mixture was diluted with EtOAc and washed with aqueous 5% LiCl solution 3×. The organic extract was dried over sodium sulfate, concentrated and purified by silica gel column chromatography (eluent: EtOAc/hexanes) to afford the desired product as the less polar peak: ES/MS: 381.2 ($M+H^+$); $^1H$ NMR (400 MHz, CDCl3) δ 8.39 (s, 1H), 7.75 (t, J=7.9 Hz, 1H), 7.72-7.64 (m, 2H), 7.56 (d, J=7.7 Hz, 1H), 7.50 (d, J=8.0 Hz, 1H), 7.44 (d, J=9.3 Hz, 1H), 6.73 (d, J=8.1 Hz, 1H), 5.57 (s, 2H), 4.23 (q, J=7.1 Hz, 2H), 3.60 (s, 2H), 1.32 (t, J=7.1 Hz, 3H).

2-[1-[6-[(4-cyano-2-fluoro-phenyl)methoxy]-2-pyridyl]pyrazol-4-yl]acetic acid: A solution of ethyl 2-[1-[6-[(4-cyano-2-fluoro-phenyl)methoxy]-2-pyridyl]pyrazol-4-yl]acetate (42.5 mg, 0.112 mmol) and lithium hydroxide, monohydrate (14.1 mg, 0.335 mmol) in $CH_3CN$ (3 mL) and water (1 mL) was stirred at RT overnight. The mixture was diluted with EtOAc and adjusted to pH~6 with 1N HCl (335 μL). The organic extract was dried over sodium sulfate and concentrated to yield the title compound: ES/MS: 353.2 ($M+H^+$).

Methyl 4-[[2-[1-[6-[(4-cyano-2-fluoro-phenyl)methoxy]-2-pyridyl]pyrazol-4-yl]acetyl]amino]-3-(2-methoxyethylamino)benzoate: To a solution of 2-[1-[6-[(4-cyano-2-fluoro-phenyl)methoxy]-2-pyridyl]pyrazol-4-yl]acetic acid (38.8 mg, 0.110 mmol), methyl 4-amino-3-(2-methoxyethylamino)benzoate (31.2 mg, 0.139 mmol), and o-(7-azabenzotriazol-1-yl)-N,N,N',N'-tetramethyluronium hexafluorophosphate (59.5 mg, 0.157 mmol) in DMF (3 mL), was added N,N-diisopropylethylamine (90.0 μL, 0.517 mmol). The mixture was stirred at RT overnight. The mixture was diluted with EtOAc and washed with aqueous 5% LiCl, saturated $NaHCO_3$, and brine. The organic extract was dried over sodium sulfate and concentrated. The crude residue was carried on to the next step without purification: ES/MS: 559.2 ($M+H^+$).

Methyl 2-[[1-[6-[(4-cyano-2-fluoro-phenyl)methoxy]-2-pyridyl]pyrazol-4-yl]methyl]-3-(2-methoxyethyl)benzimidazole-5-carboxylate: A solution of methyl 4-[[2-[1-[6-[(4-cyano-2-fluoro-phenyl)methoxy]-2-pyridyl]pyrazol-4-yl]acetyl]amino]-3-(2-methoxyethylamino)benzoate (61.5 mg, 0.110 mmol) in AcOH (3 mL) was heated at 60° C. overnight. The mixture was concentrated and purified by silica gel column chromatography (eluent: EtOAc/hexanes) to afford the desired product. ES/MS: 541.2 ($M+H^+$); $^1H$ NMR (400 MHz, $CDCl_3$) δ 8.32 (s, 1H), 8.12 (d, J=1.6 Hz, 1H), 8.02 (dd, J=8.5, 1.5 Hz, 1H), 7.78 (d, J=8.5 Hz, 1H), 7.73 (t, J=8.0 Hz, 1H), 7.68 (s, 1H), 7.61 (t, J=7.5 Hz, 1H), 7.52 (d, J=7.7 Hz, 1H), 7.41 (dd, J=8.0, 1.5 Hz, 1H), 7.20 (dd, J=9.3, 1.5 Hz, 1H), 6.71 (d, J=8.1 Hz, 1H), 5.49 (s, 2H), 4.38 (t, J=5.2 Hz, 2H), 4.35 (s, 2H), 3.98 (s, 3H), 3.71 (t, J=5.2 Hz, 2H), 3.29 (s, 3H).

2-[[1-[6-[(4-cyano-2-fluoro-phenyl)methoxy]-2-pyridyl]pyrazol-4-yl]methyl]-3-(2-methoxyethyl)benzimidazole-5-carboxylic acid (Example 107): A suspension of methyl 2-[[1-[6-[(4-cyano-2-fluoro-phenyl)methoxy]-2-pyridyl]pyrazol-4-yl]methyl]-3-(2-methoxyethyl)benzimidazole-5-carboxylate (33.5 mg, 0.0620 mmol) and lithium hydroxide, monohydrate (7.9 mg, 0.188 mmol) in $CH_3CN$ (3 mL) and water (1 mL) was stirred at RT overnight. The mixture was heated at 40° C. for 1.5 h. The mixture was diluted with EtOAc and water. To this was added aqueous 5% citric acid (~190 uL) to adjust the mixture to pH 5. The organic layer was dried over sodium sulfate, concentrated, and purified by RP-HPLC (eluent: water/MeCN 0.1% TFA) to yield the product (Example 107) as a trifluoroacetate salt: ES/MS: 527.2 (M+H$^+$); $^1$H NMR (400 MHz, MeOD) δ 8.64-8.55 (m, 2H), 8.25 (dd, J=8.6, 1.4 Hz, 1H), 7.89 (t, J=8.0 Hz, 1H), 7.85-7.77 (m, 2H), 7.73 (t, J=7.6 Hz, 1H), 7.61-7.53 (m, 2H), 7.46 (dd, J=9.8, 1.5 Hz, 1H), 6.86 (d, J=8.1 Hz, 1H), 5.59 (s, 2H), 4.82 (t, J=5.0 Hz, 2H), 4.65 (s, 2H), 3.85 (t, J=4.9 Hz, 2H).

Example 114. 2-[[4-[6-[(4-cyano-2-fluoro-phenyl) methoxy]-3-fluoro-2-pyridyl]-3-fluoro-phenyl] methyl]-3-(2-methoxyethyl)benzimidazole-5-carboxylic acid Procedure 27

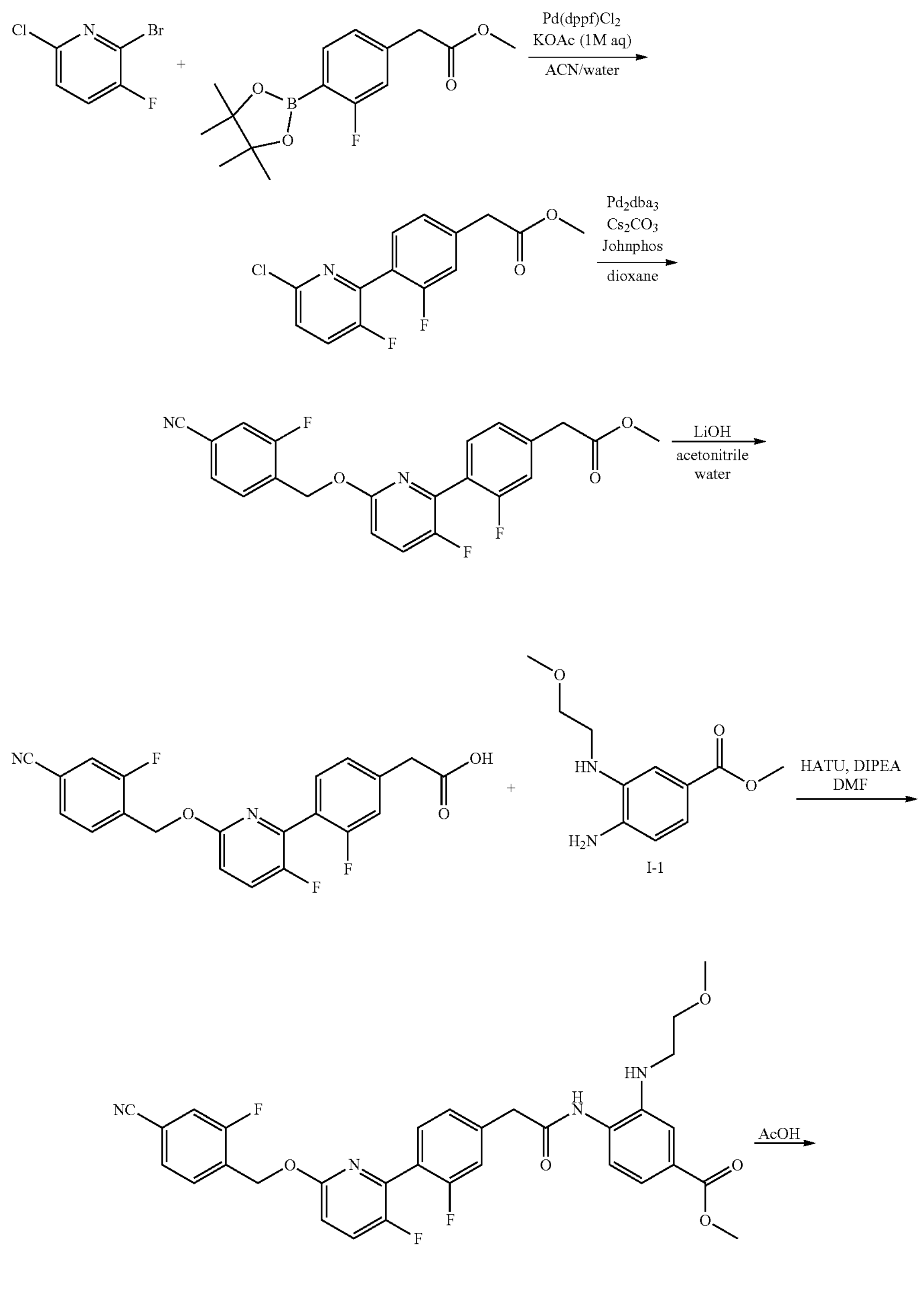

-continued

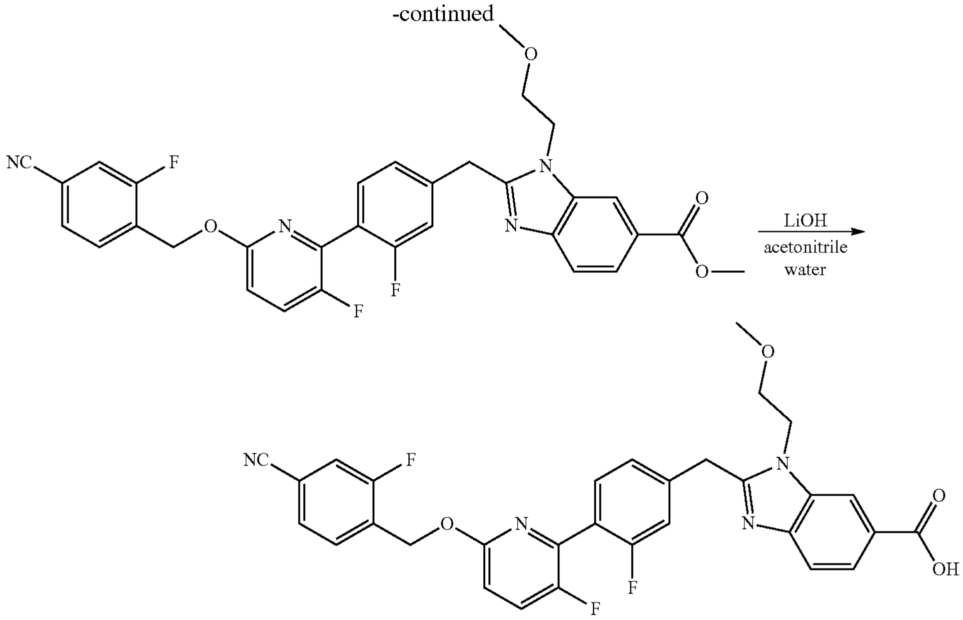

Example 114

Methyl 2-[4-(6-chloro-3-fluoro-2-pyridyl)-3-fluoro-phenyl]acetate: In a 20 mL vial, a suspension of methyl 2-[3-fluoro-4-(4,4,5,5-tetramethyl-1,3,2-dioxaborolan-2-yl)phenyl]acetate (150 mg, 0.510 mmol), 2-bromo-6-chloro-3-fluoro-pyridine (109 mg, 0.520 mmol), (1,1'-bis(diphenylphosphino)ferrocene)-dichloropalladium(II) (28.9 mg, 0.0408 mmol), and aqueous potassium acetate (1.0 M, 1.02 mL, 1.02 mmol) in acetonitrile (4 mL) was degassed with Ar for 5 min. The mixture was heated at 80° C. for 10 minutes. The mixture was diluted with EtOAc and washed with brine. The organic extract was dried over sodium sulfate, concentrated, and purified by silica gel column chromatography (eluent: EtOAc/hexanes) to afford the desired product: ES/MS: 298.2 ($M+H^+$); 1H NMR (400 MHz, CDC13) δ 8.36 (d, J=1.4 Hz, 1H), 7.47-7.35 (m, 2H), 7.26-7.17 (m, 2H), 3.77 (s, 3H), 3.72 (d, J=1.6 Hz, 2H). 19F NMR (376 MHz, CDC13) δ −114.15 (ddd, J=18.3, 10.7, 7.3 Hz), −132.86 (dd, J=18.2, 5.2 Hz).

Methyl 2-[4-[6-[(4-cyano-2-fluoro-phenyl)methoxy]-3-fluoro-2-pyridyl]-3-fluoro-phenyl]acetate: A suspension of methyl 2-[4-(6-chloro-3-fluoro-2-pyridyl)-3-fluoro-phenyl]acetate (101 mg, 0.338 mmol), 3-fluoro-4-(hydroxymethyl)benzonitrile (66.3 mg, 0.439 mmol), cesium carbonate (170 mg, 0.523 mmol), 2-(di-t-butylphosphino)biphenyl (15 mg, 0.0503 mmol), and $Pd_2(DBA)_3$ (15.0 mg, 0.0197 mmol) in dioxane (3 mL) was degassed with Ar for 5 min, then heated at 100° C. overnight. The mixture was diluted with EtOAc and washed with brine. The organic extract was dried over sodium sulfate, concentrated, and purified by silica gel column chromatography (eluent: EtOAc/hexanes) to afford the desired product: ES/MS: 413.2 ($M+H^+$); $^1H$ NMR (400 MHz, CDC13) δ 8.08 (d, J=1.6 Hz, 1H), 7.67 (t, J=7.5 Hz, 1H), 7.49 (dd, J=7.8, 1.5 Hz, 1H), 7.45-7.35 (m, 2H), 7.23-7.15 (m, 2H), 6.90 (dd, J=4.9, 1.0 Hz, 1H), 5.53 (s, 2H), 3.76 (s, 3H), 3.71 (s, 2H). 19F NMR (376 MHz, CDC13) δ −114.45 (ddd, J=17.8, 10.7, 7.4 Hz), −114.83-−116.84 (m), −141.34 (dd, J=17.4, 4.8 Hz).

2-[4-[6-[(4-cyano-2-fluoro-phenyl)methoxy]-3-fluoro-2-pyridyl]-3-fluoro-phenyl]acetic acid: A solution of methyl 2-[4-[6-[(4-cyano-2-fluoro-phenyl)methoxy]-3-fluoro-2-pyridyl]-3-fluoro-phenyl]acetate (37.6 mg, 0.0912 mmol) and lithium hydroxide, monohydrate (10.7 mg, 0.255 mmol) in $CH_3CN$ (3 mL) and water (1 mL) was stirred at room temperature overnight. The mixture was diluted with EtOAc and adjusted to pH~6 with 1N HCl (250 μL). The organic extract was dried over sodium sulfate and concentrated to provide the title compound. ES/MS: 399.2 ($M+H^+$).

Methyl 4-[[2-[4-[6-[(4-cyano-2-fluoro-phenyl)methoxy]-3-fluoro-2-pyridyl]-3-fluoro-phenyl]acetyl]amino]-3-(2-methoxyethylamino)benzoate: To a solution of 2-[4-[6-[(4-cyano-2-fluoro-phenyl)methoxy]-3-fluoro-2-pyridyl]-3-fluoro-phenyl]acetic acid (32.2 mg, 0.0808 mmol), methyl 4-amino-3-(2-methoxyethylamino)benzoate (22.9 mg, 0.102 mmol), and o-(7-azabenzotriazol-1-yl)-N,N,N',N'-tetramethyluronium hexafluorophosphate (43.7 mg, 0.115 mmol) in DMF (3 mL), was added N,N-diisopropylethylamine (70.0 μL, 0.402 mmol). The mixture was stirred at RT for 4 hr. The mixture was diluted with EtOAc and washed with aqueous 5% LiCl, saturated $NaHCO_3$, and brine. The organic extract was dried over sodium sulfate and concentrated. The crude residue was carried on to next step without purification. ES/MS: 605.2 ($M+H^+$).

Methyl 2-[[4-[6-[(4-cyano-2-fluoro-phenyl)methoxy]-3-fluoro-2-pyridyl]-3-fluoro-phenyl]methyl]-3-(2-methoxyethyl)benzimidazole-5-carboxylate: A solution of methyl 4-[[2-[4-[6-[(4-cyano-2-fluoro-phenyl)methoxy]-3-fluoro-2-pyridyl]-3-fluoro-phenyl]acetyl]amino]-3-(2-methoxyethylamino)benzoate (48.9 mg, 0.0809 mmol) in AcOH (3 mL) was heated at 60° C. for 3 h. The mixture was concentrated and purified by silica gel column chromatography (eluent: EtOAc/hexanes) to afford the desired product: ES/MS: 587.2 ($M+H^+$).

2-[[4-[6-[(4-cyano-2-fluoro-phenyl)methoxy]-3-fluoro-2-pyridyl]-3-fluoro-phenyl]methyl]-3-(2-methoxyethyl)benzimidazole-5-carboxylic acid (Example 114): A suspension of methyl 2-[[4-[6-[(4-cyano-2-fluoro-phenyl)methoxy]-3-fluoro-2-pyridyl]-3-fluoro-phenyl]methyl]-3-(2-methoxyethyl)benzimidazole-5-carboxylate (29.0 mg, 0.0494 mmol)

and lithium hydroxide, monohydrate (7.6 mg, 0.181 mmol) in $CH_3CN$ (3 mL) and water (1 mL) was stirred at RT overnight, and then heated at 60° C. for 2 h. The mixture was diluted with EtOAc and water. To this was added aqueous 5% citric acid (~180 μL) to pH 5. The organic extract was dried over sodium sulfate, concentrated and purified by RP-HPLC (eluent: water/MeCN 0.1% TFA) to yield the product (Example 114) as a trifluoroacetate salt. ES/MS: 573.2 (M+H$^+$); $^1$H NMR (400 MHz, MeOD) δ 8.50 (d, J=1.4 Hz, 1H), 8.18 (dd, J=8.6, 1.5 Hz, 1H), 8.13 (d, J=1.6 Hz, 1H), 7.78 (d, J=8.4 Hz, 1H), 7.74 (d, J=7.6 Hz, 1H), 7.66-7.51 (m, 3H), 7.35 (d, J=4.3 Hz, 1H), 7.33 (s, 1H), 6.99 (d, J=4.8 Hz, 1H), 5.55 (s, 2H), 4.73 (d, J=7.2 Hz, 4H), 3.79 (t, J=5.0 Hz, 2H), 3.31 (s, 3H). 19F NMR (376 MHz, MeOD) δ −77.74, −113.42--116.11 (m), −117.08--121.64 (m), −143.46 (dd, J=18.9, 5.1 Hz).

Example 115. 2-[[4-[3-chloro-6-[(4-cyano-2-fluoro-phenyl)methoxy]-2-pyridyl]-2-fluoro-phenyl]methyl]-3-(2-methoxyethyl)benzimidazole-5-carboxylic acid Procedure 28

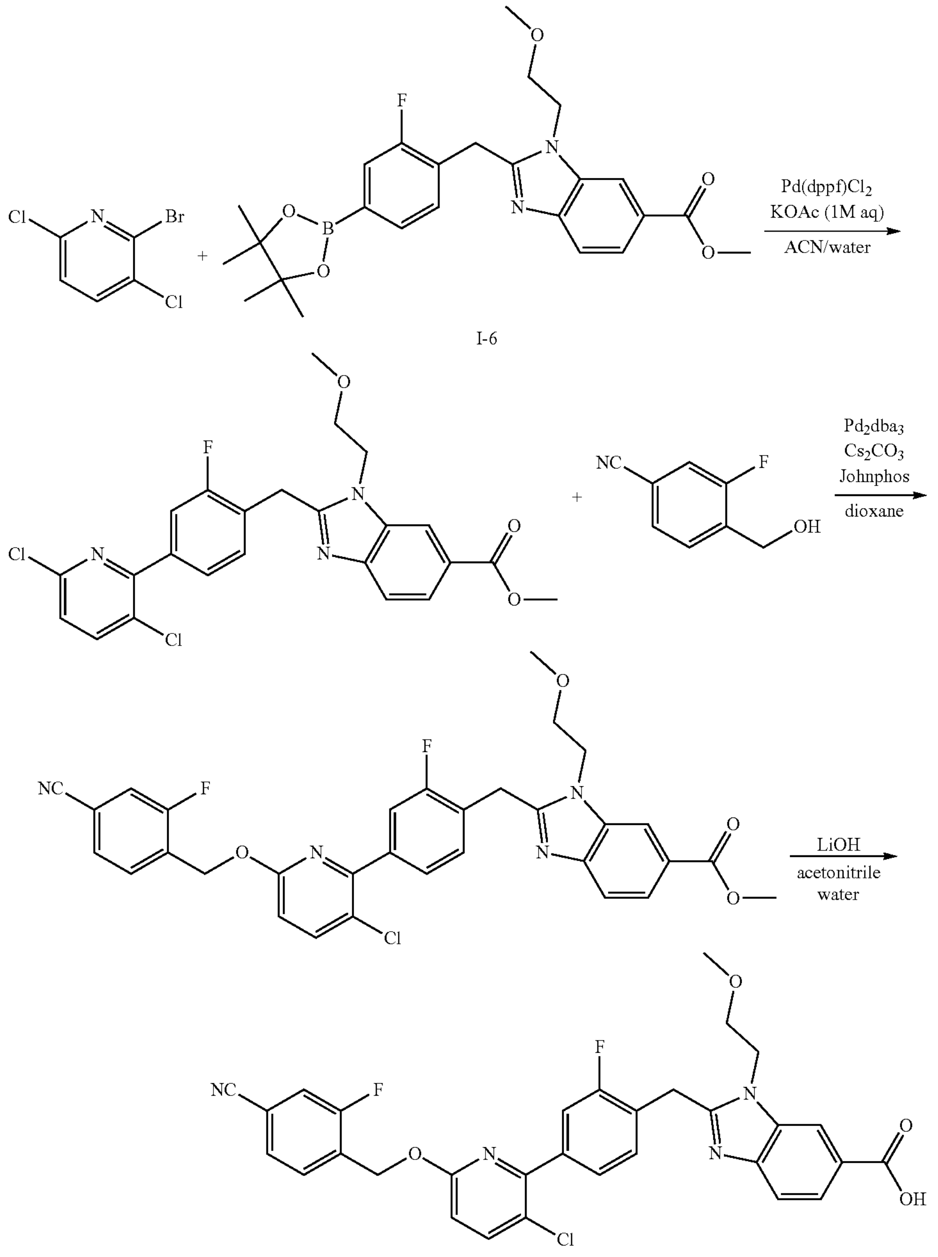

I-6

Example 115

Methyl 2-[[4-(3,6-dichloro-2-pyridyl)-2-fluoro-phenyl]methyl]-3-(2-methoxyethyl)benzimidazole-5-carboxylate: In a 5 mL microwave vial, a suspension of 2-bromo-3,6-dichloro-pyridine (50.9 mg, 0.224 mmol), methyl 2-[[2-fluoro-4-(4,4,5,5-tetramethyl-1,3,2-dioxaborolan-2-yl)phenyl]methyl]-3-(2-methoxyethyl)benzimidazole-5-carboxylate (I-5, 100 mg, 0.214 mmol), [1,1'-Bis(diphenylphosphino)ferrocene]dichloropalladium(II); $PdCl_2$ (dppf) (12.7 mg, 0.0171 mmol), and potassium acetate (1.00 M in water, 0.427 mL, 0.427 mmol) in acetonitrile (2 mL) was degassed with Ar for 5 min. The mixture was heated at 80° C. for 40 min, then at 90° C. for 20 min. The mixture was diluted with EtOAc and washed with brine. The organic extract was dried over sodium sulfate, concentrated, and purified by silica gel chromatography (eluent: EtOAc/hexanes) to afford the desired product: ES/MS: 603.2 ($M+H^+$); $^1H$ NMR (400 MHz, CDCl3) δ 8.16-8.09 (m, 1H), 7.99 (ddd, J=8.0, 6.4, 1.6 Hz, 1H), 7.82-7.67 (m, 2H), 7.59-7.46 (m, 2H), 7.35 (t, J=7.8 Hz, 1H), 7.26 (d, J=1.1 Hz, 0H), 4.49 (s, 2H), 4.35 (t, J=5.3 Hz, 2H), 4.08-3.90 (m, 3H), 3.65 (t, J=5.3 Hz, 2H), 3.30-3.24 (m, 3H).

Methyl 2-[[4-[3-chloro-6-[(4-cyano-2-fluoro-phenyl)methoxy]-2-pyridyl]-2-fluoro-phenyl]methyl]-3-(2-methoxyethyl)benzimidazole-5-carboxylate: A suspension of methyl 2-[[4-(3,6-dichloro-2-pyridyl)-2-fluoro-phenyl]methyl]-3-(2-methoxyethyl)benzimidazole-5-carboxylate (84.6 mg, 0.173 mmol), 3-fluoro-4-(hydroxymethyl)benzonitrile (34.0 mg, 0.225 mmol), cesium carbonate (87.3 mg, 0.268 mmol), 2-(di-t-butylphosphino)biphenyl (10.5 mg, 0.0352 mmol), and $Pd_2(DBA)_3$ (11.8 mg, 0.0129 mmol) in dioxane (3 mL) was degassed with Ar for 5 min, then heated at 100° C. overnight. To this mixture was added $Pd_2(DBA)_3$ (12 mg) and 2-(di-t-butylphosphino)biphenyl (10 mg). The mixture was degassed for 5 min with Ar, then heated at 100° C. for 7 hr. The mixture was diluted with EtOAc and washed with brine. The organic extract was dried over sodium sulfate, concentrated, and purified by silica gel chromatography (eluent: EtOAc/hexanes) to afford the desired product. ES/MS: 603.2 ($M+H^+$); $^1H$ NMR (400 MHz, CDCl3) δ 8.24-8.08 (m, 2H), 8.03 (ddd, J=18.0, 8.5, 1.5 Hz, 2H), 7.79 (d, J=8.4 Hz, 1H), 7.68 (dd, J=11.4, 8.6 Hz, 1H), 7.62 (q, J=7.1 Hz, 1H), 7.56-7.43 (m, 4H), 7.43-7.31 (m, 5H), 6.99-6.92 (m, 1H), 6.80 (d, J=8.7 Hz, 1H), 5.49 (d, J=13.5 Hz, 2H), 4.49 (s, 2H), 4.39 (t, J=5.3 Hz, 2H), 3.98 (d, J=3.1 Hz, 4H), 3.65 (t, J=5.3 Hz, 2H), 3.26 (d, J=3.5 Hz, 4H).

2-[[4-[3-chloro-6-[(4-cyano-2-fluoro-phenyl)methoxy]-2-pyridyl]-2-fluoro-phenyl]methyl]-3-(2-methoxyethyl)benzimidazole-5-carboxylic acid (Example 115): A suspension of methyl 2-[[4-[3-chloro-6-[(4-cyano-2-fluoro-phenyl)methoxy]-2-pyridyl]-2-fluoro-phenyl]methyl]-3-(2-methoxyethyl)benzimidazole-5-carboxylate (20.9 mg, 0.0347 mmol) and lithium hydroxide monohydrate (7.30 mg, 0.174 mmol) in $CH_3CN$ (3 mL) and water (1 mL) was stirred at RT overnight. The mixture was diluted with EtOAc and water, and 5% citric acid (~0.200 mL) was added to pH 5. The organic extract was dried over sodium sulfate, concentrated and purified by RP-HPLC (eluent: water/MeCN 0.1% TFA) to yield the product (Example 115) as a trifluoroacetate salt. ES/MS: 589.2 ($M+H^+$); $^1H$ NMR (400 MHz, MeOD) δ 8.51 (d, J=1.3 Hz, 1H), 8.19 (dd, J=8.6, 1.5 Hz, 1H), 7.87 (d, J=8.7 Hz, 1H), 7.77 (d, J=8.6 Hz, 1H), 7.71 (t, J=7.6 Hz, 1H), 7.67-7.52 (m, 5H), 7.50 (t, J=7.8 Hz, 1H), 6.96 (d, J=8.7 Hz, 1H), 5.56 (s, 2H), 4.81-4.65 (m, 4H), 3.80 (t, J=4.9 Hz, 2H), 3.31 (s, 4H).

Example 358. Compound Prepared Using Procedure 28

Other compound of the present disclosure prepared using the general route described in Procedure 28 include the following Example.

| Example | Structure/Name/Characterization |
|---|---|
| 358 | 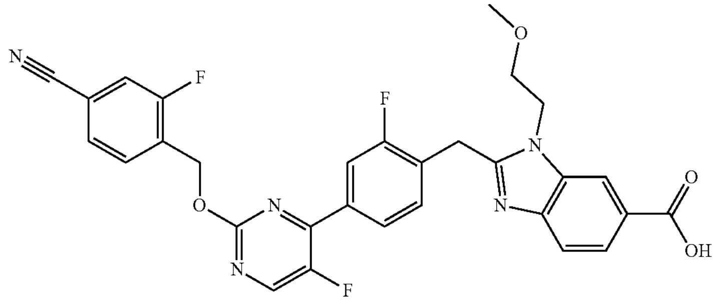 [SMILES: COCCn1c(Cc2ccc(-c3nc(OCc4ccc(C#N)cc4F)ncc3F)cc2F)nc2ccc(C(=O)O)cc21]<br>2-(4-(2-((4-cyano-2-fluorobenzyl)oxy)-5-fluoropyrimidin-4-yl)-2-fluorobenzyl)-1-(2-methoxyethyl)-1H-benzo[d]imidazole-6-carboxylic acid: ES/MS 574.3; $^1H$ NMR (400 MHz, DMSO-d6) δ 8.85 (d, J = 3.2 Hz, 1H), 8.27 (d, J = 1.5 Hz, 1H), 8.00-7.92 (m, 1H), 7.91-7.82 (m, 3H), 7.81-7.73 (m, 2H), 7.63 (d, J = 8.5 Hz, 1H), 7.58 (t, J = 8.0 Hz, 1H), 5.60 (s, 2H), 4.63 (t, J = 5.1 Hz, 2H), 4.54 (s, 2H), 3.68 (t, J = 5.0 Hz, 2H), 3.21 (s, 3H). |

Example 469, 2-((3'-((4-carbamoyl-2-fluorobenzyl)oxy)-3,4'-difluoro-[1,1'-biphenyl]-4-yl)methyl)-1H-benzo[d]imidazole-6-carboxylic acid Procedure 29

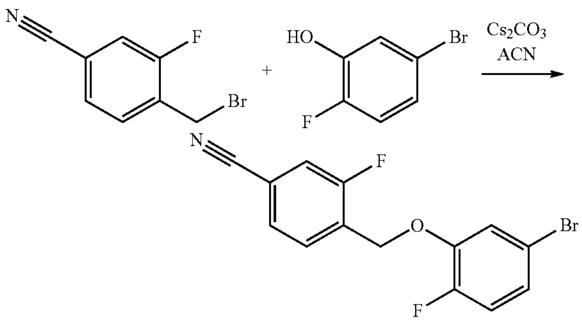

4-[(3-bromo-2,6-difluoro-phenoxy)methyl]-3-fluoro-benzonitrile: 4-(chloromethyl)-3-fluoro-benzonitrile (4.28 g, 20.0 mmol) was added to 3-bromo-2,6-difluoro-phenol (4.24 g, 22.2 mmol) and cesium carbonate (13.0 g, 40.0 mmol) in acetonitrile (100 mL). The mixture was stirred overnight at ambient temperature. The mixture was filtered through Celite and concentrated by rotary evaporation. The product was used without further purification to give the titled compound. $^1$H NMR (400 MHz, Chloroform-d) δ 7.72 (t, J=7.5 Hz, 1H), 7.53 (dd, J=8.0, 1.5 Hz, 1H), 7.41 (dd, J=9.3, 1.5 Hz, 1H), 7.16 (dd, J=7.4, 2.3 Hz, 1H), 7.10 (ddd, J=8.6, 4.1, 2.3 Hz, 1H), 7.00 (dd, J=10.8, 8.6 Hz, 1H), 5.21 (s, 2H).

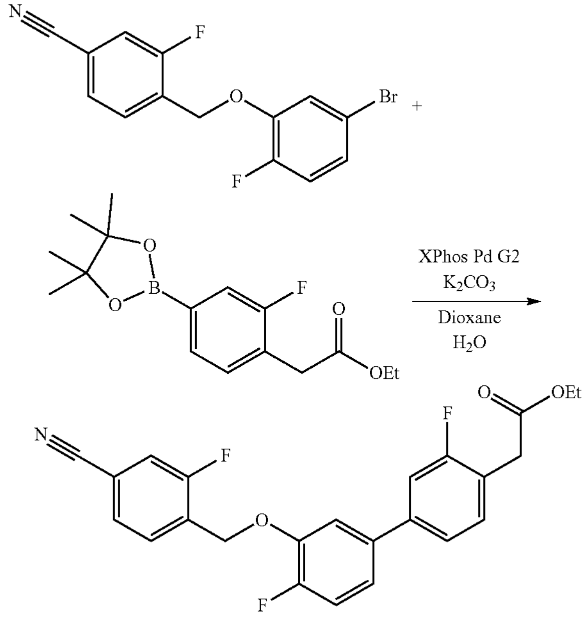

Ethyl 2-[4-[3-[(4-cyano-2-fluoro-phenyl)methoxy]-4-fluoro-phenyl]-2-fluoro-phenyl]acetate: 4-[(5-bromo-2-fluoro-phenoxy)methyl]-3-fluoro-benzonitrile (2.40 g, 7.40 mmol) was added to ethyl 2-[2-fluoro-4-(4,4,5,5-tetramethyl-1,3,2-dioxaborolan-2-yl)phenyl]acetate (2737 mg, 8.88 mmol), chloro(2-dicyclohexylphosphino-2',4',6'-triisopropyl-1,1'-biphenyl)[2-(2'-amino-1,1'-biphenyl)]palladium (II) (582 mg, 0.370 mmol) and potassium carbonate (2455 mg, 17.8 mmol) in 1,4-1,4-dioxane (37.0 mL) and water (13.0 mL). The mixture was stirred at 100° C. for 3 hours. The mixture was cooled to ambient temperature and extracted with EtOAc (3x40 mL). The combined organic layers were dried with $Mg_2SO_4$, filtered and concentrated by rotary evaporation. The product was purified by flash chromatography (0-100% EtOAc in hexane) to yield the titled product: $^1$H NMR (400 MHz, Chloroform-d) δ 7.79 (t, J=7.5 Hz, 1H), 7.55 (dd, J=7.9, 1.4 Hz, 1H), 7.48-7.39 (m, 2H), 7.35 (t, J=7.6 Hz, 1H), 7.28-7.22 (m, 1H), 7.22-7.11 (m, 3H), 5.32 (s, 2H), 4.14 (q, J=7.2 Hz, 2H), 3.72 (q, J=2.4 Hz, 3H), 1.29-1.26 (m, 3H). ES/MS m/z: 448.081 (M+Na$^+$).

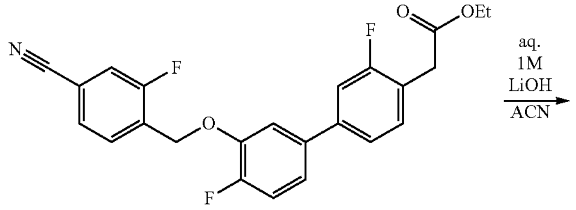

-continued

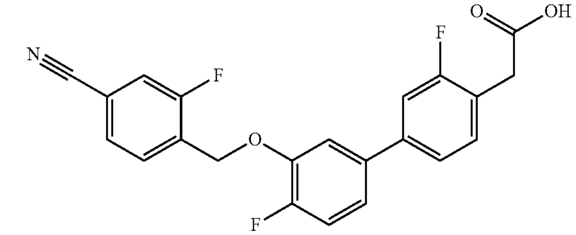

2-(3'-((4-cyano-2-fluorobenzyl)oxy)-3,4'-difluoro-[1,1'-biphenyl]-4-yl)acetic acid: Ethyl 2-[4-[3-[(4-cyano-2-fluoro-phenyl)methoxy]-4-fluoro-phenyl]-2-fluoro-phenyl] acetate (2.81 g, 6.61 mmol) was dissolved in acetonitrile (13.5 mL) and 1 M aq. LiOH (13.5 mL). The reaction vial was sealed and heated to 80° C. for 1 hour. The mixture was cooled to ambient temperature and acidified with 1 M aqueous HCl. The mixture was extracted with EtOAc (3x20 mL) and the combined organic layers were dried with $Mg_2SO_4$, filtered and concentrated by rotary evaporation. The product was used without further purification: ES/MS m/z: 396.147 (M–H$^-$); $^1$H NMR (400 MHz, Methanol-d4) δ 7.79-7.58 (m, 2H), 7.49-7.30 (m, 4H), 7.23 (ddd, J=10.5, 6.6, 3.8 Hz, 2H), 5.38 (d, J=8.8 Hz, 2H), 3.78-3.63 (m, 2H).

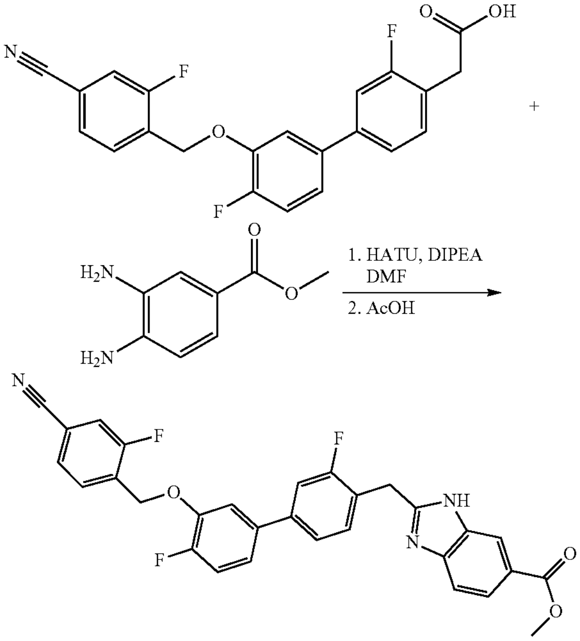

Methyl 2-((3'-((4-cyano-2-fluorobenzyl)oxy)-3,4'-difluoro-[1,1'-biphenyl]-4-yl)methyl)-1H-benzo[d]imidazole-6-carboxylate: 2-[4-[3-[(4-cyano-2-fluoro-phenyl) methoxy]-4-fluoro-phenyl]-2-fluoro-phenyl]acetic acid (0.358 g, 0.900 mmol) was added to methyl 3,4-diaminobenzoate (165 mg, 0.990 mmol), 2-(7-aza-1H-benzotriazole-1-yl)-1,1,3,3-tetramethyluronium hexafluorophosphate (HATU), (412 mg, 1.08 mmol), and N,N-diisopropylethylamine (116 mg, 0.900 mmol) in DMF (3.50 mL). The mixture was stirred at ambient temperature for 5 hours. The mixture was diluted with water (3 mL) and extracted with EtOAc (3x3 mL). The combined organic layers were washed with brine (10 mL), dried with $Mg_2SO_4$, filtered and concentrated by rotary evaporation. The product was used without further purification: ES/MS m/z: 546.150 (M+H$^+$).

Crude methyl 3-amino-4-[[2-[4-[3-[(4-cyano-2-fluoro-phenyl)methoxy]-4-fluoro-phenyl]-2-fluoro-phenyl]acetyl]amino]benzoate (491 mg, 0.900 mmol) was dissolved in acetic acid (10 mL). The mixture was heated to 100° C. for 3 hours. The mixture was cooled to ambient temperature and neutralized with 2 M aq. NaOH. The mixture was extracted with EtOAc (3×10 mL). The combined organic layers washed with brine (10 mL), dried with $Mg_2SO_4$, filtered and concentrated by rotary evaporation. The product was purified by flash chromatography (10-80% EtOAc in hexanes) to yield the titled product: ES/MS m/z: 528.155 ($M+H^+$); $^1H$ NMR (400 MHz, Chloroform-d) δ 8.24-8.16 (m, 1H), 7.90 (dd, J=8.5, 1.6 Hz, 1H), 7.82-7.71 (m, 2H), 7.56-7.30 (m, 4H), 7.22-6.95 (m, 2H), 5.26 (d, J=5.0 Hz, 3H), 4.30 (s, 2H), 3.87 (d, J=11.4 Hz, 4H).

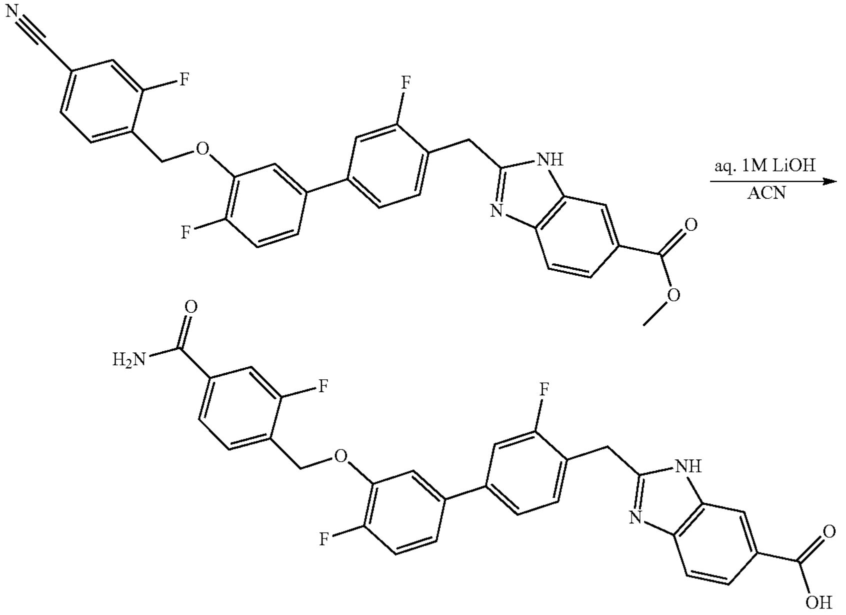

Example 469

2-((3'-((4-carbamoyl-2-fluorobenzyl)oxy)-3,4'-difluoro-[1,1'-biphenyl]-4-yl)methyl)-1H-benzo[d]imidazole-6-carboxylic acid (Example 469): Methyl 2-[[4-[3-[(4-cyano-2-fluoro-phenyl)methoxy]-4-fluoro-phenyl]-2-fluoro-phenyl]methyl]-3H-benzimidazole-5-carboxylate (1.18 g, 2.24 mmol) was dissolved in 1 M aq. LiOH (2.0 mL) and acetonitrile (5.0 mL). The reaction vial was sealed and heated to 80° C. and the mixture was heated overnight. The product was purified by RP-HPLC (eluent: water/MeCN 0.1% TFA) to yield the titled product. ES/MS m/z: 532.200 ($M+H^+$); $^1H$ NMR (400 MHz, Methanol-d4) δ 8.38 (s, 1H), 8.21 (s, 1H), 7.84-7.62 (m, 2H), 7.62-7.38 (m, 2H), 7.35-7.14 (m, 2H), 5.38 (s, 2H), 4.64 (s, 2H). 19F NMR (377 MHz, Methanol-d4) δ −77.70, −118.85, −119.65, −120.64 (m), −137.07.

Example 465, 2-[[4-[3-[(4-chloro-2-fluoro-phenyl)methoxy]-4-fluoro-phenyl]-2-fluoro-phenyl]methyl]-3-(pyrrolidin-2-ylmethyl)benzimidazole-5-carboxylic acid Procedure 30

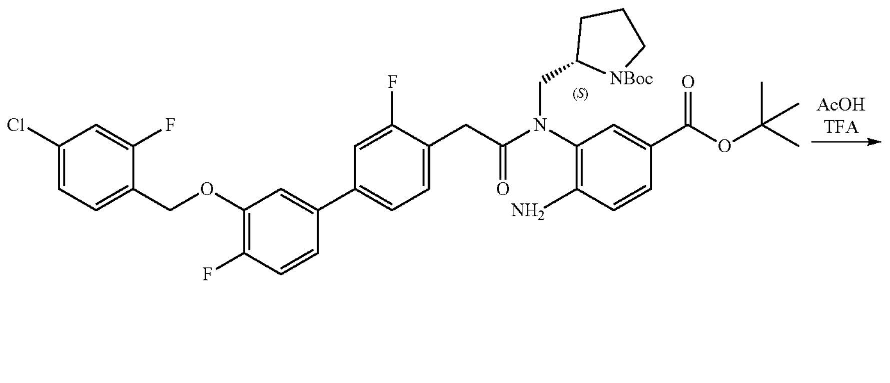

-continued

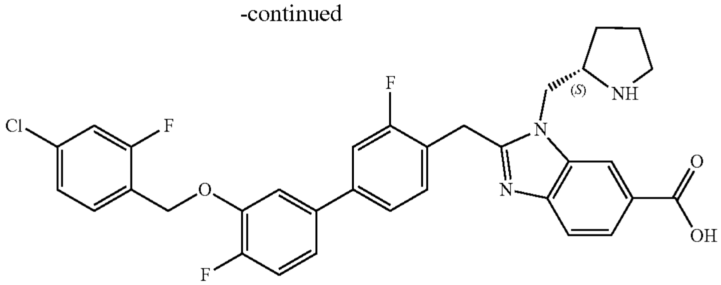

Example 465

2-[[4-[3-[(4-chloro-2-fluoro-phenyl)methoxy]-4-fluoro-phenyl]-2-fluoro-phenyl]methyl]-3-(pyrrolidin-2-ylmethyl) benzimidazole-5-carboxylic acid (Example 465): Crude tert-butyl 2-[[5-tert-butoxycarbonyl-2-[[2-[4-[3-[(4-chloro-2-fluoro-phenyl)methoxy]-4-fluoro-phenyl]-2-fluoro-phenyl] acetyl]amino]anilino]methyl]pyrrolidine-1-carboxylate (95.9 mg, 0.123 mmol) was obtained as described in Procedure 29 substituting methyl 3,4-diaminobenzoate with tert-butyl (S)-2-(((2-amino-5-(tert-butoxycarbonyl)phenyl) amino)methyl)pyrrolidine-1-carboxylate in the fourth step. This was dissolved in acetic acid (1 mL) and the mixture was heated for 12 hours at 80° C. Excess trifluoroacetic acid (0.1 mL) was added and the mixture was continued heating for 2 hours. The mixture was cooled to ambient temperature, concentrated and purified by RP-HPLC (eluent: water/MeCN 0.1% TFA) to yield the titled product: ES/MS m/z: 606.200 ($M+H^+$); $^1H$ NMR (400 MHz, Methanol-d4) δ 8.46-8.34 (m, 1H), 8.14-7.99 (m, 1H), 7.74 (d, J=8.5 Hz, 1H), 7.57 (t, J=7.9 Hz, 1H), 7.51-7.34 (m, 3H), 7.32-7.15 (m, 4H), 5.28 (s, 2H), 4.58 (s, 2H), 4.08 (dd, J=10.4, 6.7 Hz, 1H), 3.61-3.44 (m, 1H), 2.36-2.15 (m, 1H), 2.09 (dt, J=14.2, 7.9 Hz, 1H), 1.93 (dt, J=12.4, 9.6 Hz, 1H). 19F NMR (376 MHz, Methanol-d4) δ −77.92 (d, J=4.7 Hz), −118.15 (dd, J=83.8, 10.8 Hz), −136.23, −137.54 (m).

Example 456, 457, 461, 462, 466, 472, 477, 489, 490, 491. Compounds Prepared Using Procedure 30

Other compounds of the present disclosure prepared using the general route described in Procedure 30 include the following Examples.

| Example | Structure/Name/Characterization |
|---|---|
| 456 | 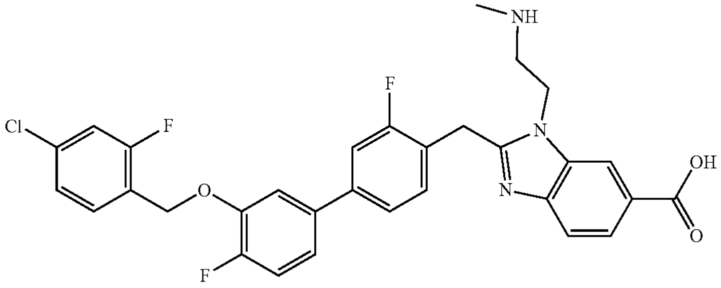 [SMILES: CNCCn1c(Cc2ccc(-c3ccc(F)c(OCc4ccc(Cl)cc4F)c3)cc2F)nc2ccc(C(=O)O)cc21] 2-((3'-((4-chloro-2-fluorobenzyl)oxy)-3,4'-difluoro-[1,1'-biphenyl]-4-yl)methyl)-1-(2-(methylamino)ethyl)-1H-benzo[d]imidazole-6-carboxylic acid: ES/MS 580.2; $^1H$ NMR (400 MHz, Acetonitrile-d3) δ 8.42 (d, J = 1.4 Hz, 1H), 8.03 (dd, J = 8.5, 1.4 Hz, 1H), 7.73 (d, J = 8.5 Hz, 1H), 7.53 (q, J = 7.9 Hz, 1H), 7.49-7.37 (m, 4H), 7.33-7.16 (m, 4H), 5.26 (s, 2H), 4.77 (t, J = 6.8 Hz, 2H), 4.55 (s, 2H), 3.45 (t, J = 6.8 Hz, 2H), 2.67 (s, 3H). |
| 457 | 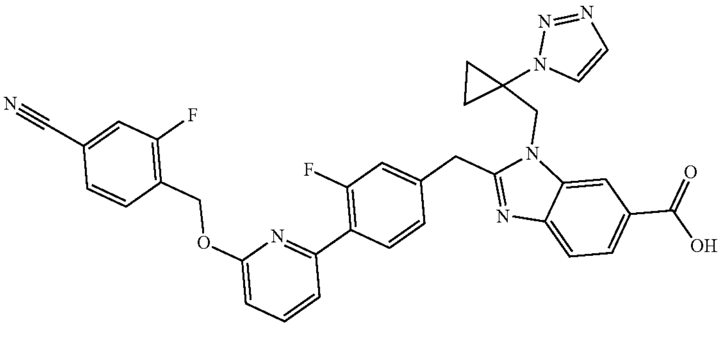 [SMILES: N#Cc1ccc(COc2cccc(-c3ccc(Cc4nc5ccc(C(=O)O)cc5n4CC4(n5ccnn5)CC4)cc3F)n2)c(F)c1] 1-((1-(1H-1,2,3-triazol-1-yl)cyclopropyl)methyl)-2-(4-(6-((4-cyano-2-fluorobenzyl)oxy)pyridin-2-yl)-3-fluorobenzyl)-1H-benzo[d]imidazole-6-carboxylic acid: ES/MS m/z 618.2; $^1H$ NMR (400 MHz, DMSO-d6) δ 8.07 (d, |

-continued

| Example | Structure/Name/Characterization |
|---|---|
| | J = 1.4 Hz, 1H), 7.99 (s, 1H), 7.96-7.82 (m, 3H), 7.82-7.69 (m, 3H), 7.65 (s, 1H), 7.59 (d, J = 8.4 Hz, 1H), 7.45 (dd, J = 7.5, 1.8 Hz, 1H), 7.24-7.05 (m, 2H), 6.94 (d, J = 8.3 Hz, 1H), 5.57 (s, 2H), 4.90 (s, 2H), 3.71 (s, 2H), 2.09 (s, 1H), 1.57 (t, J = 3.6 Hz, 2H), 1.47-1.30 (m, 2H). |
| 461 | 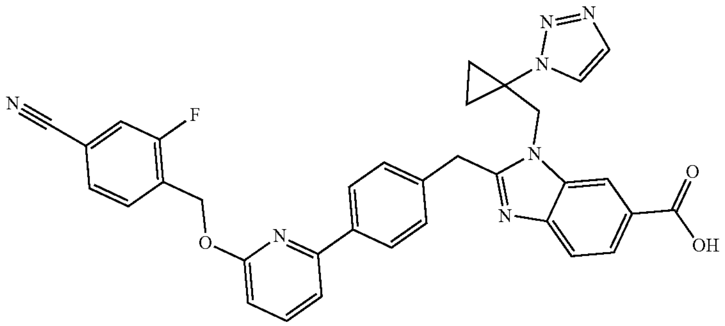 [SMILES: N#Cc1ccc(COc2cccc(-c3ccc(Cc4nc5ccc(C(=O)O)cc5n4CC4(n5ccnn5)CC4)cc3)n2)c(F)c1] 1-((1-(1H-1,2,3-triazol-1-yl)cyclopropyl)methyl)-2-(4-(6-((4-cyano-2-fluorobenzyl)oxy)pyridin-2-yl)benzyl)-1H-benzo[d]imidazole-6-carboxylic acid: ES/MS m/z 600.2; $^1$H NMR (400 MHz, Methanol-d4) δ 8.47-8.39 (m, 1H), 8.17 (dt, J = 8.7, 1.5 Hz, 1H), 8.13-8.05 (m, 3H), 7.90 (s, 1H), 7.81 (t, J = 7.9 Hz, 1H), 7.74 (dd, J = 8.1, 5.3 Hz, 2H), 7.65-7.51 (m, 3H), 7.43 (d, J = 7.8 Hz, 2H), 6.89 (d, J = 8.2 Hz, 1H), 5.66 (s, 2H), 5.11-5.00 (m, 2H), 4.39 (d, J = 3.0 Hz, 2H), 1.67-1.50 (m, 4H). |
| 462 | 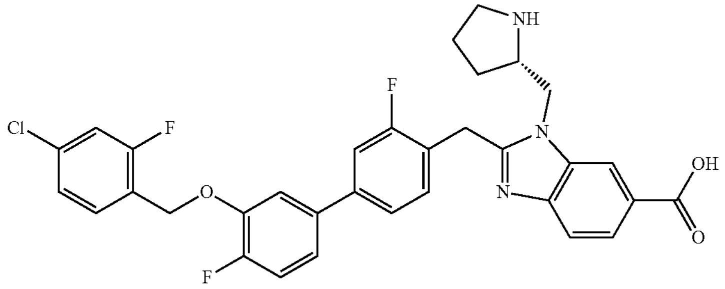 [SMILES: O=C(O)c1ccc2nc(Cc3ccc(-c4ccc(F)c(OCc5ccc(Cl)cc5F)c4)cc3F)n(C[C@@H]3CCCN3)c2c1] (S)-2-((3'-((4-chloro-2-fluorobenzyl)oxy)-3,4'-difluoro-[1,1'-biphenyl]-4-yl)methyl)-1-(pyrrolidin-2-ylmethyl)-1H-benzo[d]imidazole-6-carboxylic acid: ES/MS m/z 606.2; $^1$H NMR (400 MHz, Methanol-d4) δ 8.40 (d, J = 1.4 Hz, 1H), 8.08 (dd, J = 8.6, 1.4 Hz, 1H), 7.73 (d, J = 8.6 Hz, 1H), 7.58 (t, J = 8.0 Hz, 1H), 7.54-7.37 (m, 4H), 7.37-7.17 (m, 4H), 5.29 (s, 2H), 4.55 (s, 2H), 4.14-3.98 (m, 1H), 3.56-3.43 (m, 1H), 2.32-2.14 (m, 1H), 2.14-1.98 (m, 1H), 1.94 (d, J = 16.1 Hz, 2H), 1.68-1.54 (m, 2H), 1.16 (d, J = 11.7 Hz, 1H). |
| 466 | 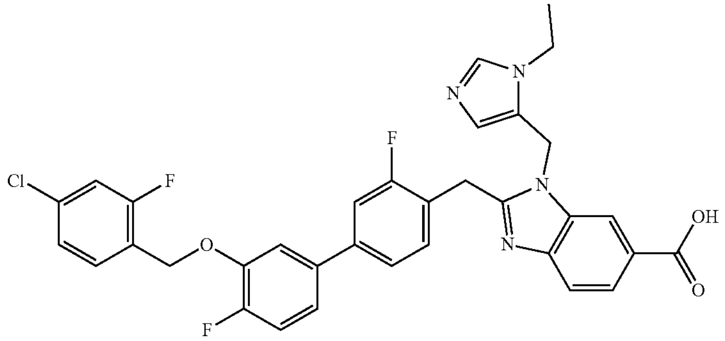 [SMILES: CCn1cncc1Cn1c(Cc2ccc(-c3ccc(F)c(OCc4ccc(Cl)cc4F)c3)cc2F)nc2ccc(C(=O)O)cc21] 2-((3'-((4-chloro-2-fluorobenzyl)oxy)-3,4'-difluoro-[1,1'-biphenyl]-4-yl)methyl)-1-((1-ethyl-1H-imidazol-5-yl)methyl)-1H-benzo[d]imidazole-6-carboxylic acid: ES/MS m/z 631.2; $^1$H NMR (400 MHz, Methanol-d4) δ 9.03-8.88 (m, 1H), 8.31-8.15 (m, 1H), 8.07 (dd, J = 8.5, 1.5 Hz, 1H), 7.79 (d, J = 8.6 Hz, 1H), 7.58 (t, J = 8.0 Hz, 1H), 7.43-7.33 (m, 3H), 7.33-7.25 (m, 2H), 7.21 (dd, J = 7.0, 1.8 Hz, 2H), 6.84-6.71 (m, 1H), 5.86 (s, 2H), 5.28 (s, 2H), 4.52 (s, 2H), 4.31 (q, J = 7.3 Hz, 2H), 1.57 (t, J = 7.3 Hz, 2H). |

-continued

| Example | Structure/Name/Characterization |
|---|---|
| 472 | 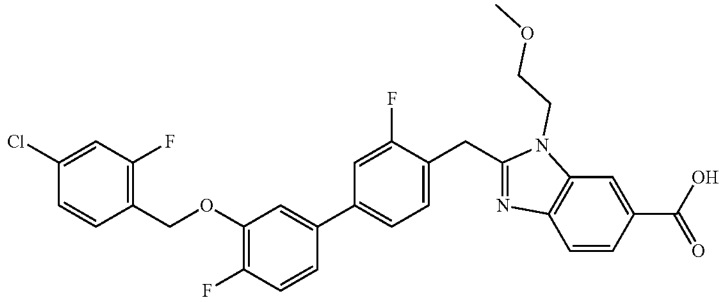 [SMILES: COCCn1c(Cc2ccc(-c3ccc(F)c(OCc4ccc(Cl)cc4F)c3)cc2F)nc2ccc(C(=O)O)cc21]<br>2-((3'-((4-chloro-2-fluorobenzyl)oxy)-3,4'-difluoro-[1,1'-biphenyl]-4-yl)methyl)-1-(2-methoxyethyl)-1H-benzo[d]imidazole-6-carboxylic acid: ES/MS 581.2; $^1$H NMR (400 MHz, Methanol-d4) δ 8.60 (d, J = 1.3 Hz, 1H), 8.26 (dd, J = 8.6, 1.4 Hz, 1H), 7.80 (d, J = 8.6 Hz, 1H), 7.61-7.48 (m, 4H), 7.44 (dd, J = 7.9, 2.2 Hz, 1H), 7.35-7.17 (m, 4H), 5.29 (s, 2H), 4.80 (s, 2H), 3.89-3.75 (m, 2H). |
| 477 | 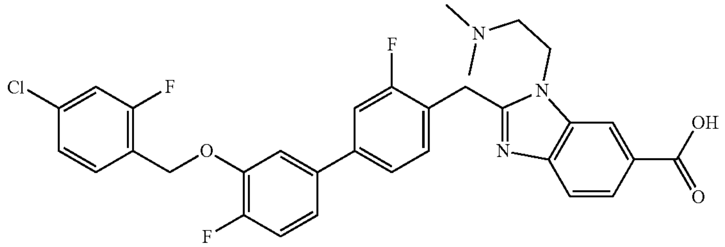 [SMILES: CN(C)CCn1c(Cc2ccc(-c3ccc(F)c(OCc4ccc(Cl)cc4F)c3)cc2F)nc2ccc(C(=O)O)cc21]<br>2-((3'-((4-chloro-2-fluorobenzyl)oxy)-3,4'-difluoro-[1,1'-biphenyl]-4-yl)methyl)-1-(2-(dimethylamino)ethyl)-1H-benzo[d]imidazole-6-carboxylic acid: ES/MS 594.55; $^1$H NMR (400 MHz, Methanol-d4) δ 8.42 (d, J = 1.4 Hz, 1H), 8.10 (dd, J = 8.5, 1.4 Hz, 1H), 7.73 (d, J = 8.5 Hz, 1H), 7.57 (t, J = 8.0 Hz, 1H), 7.53-7.38 (m, 5H), 7.32-7.16 (m, 4H), 5.28 (s, 2H), 4.59 (s, 2H), 3.67-3.52 (m, 2H), 3.07 (s, 6H). |
| 489 | 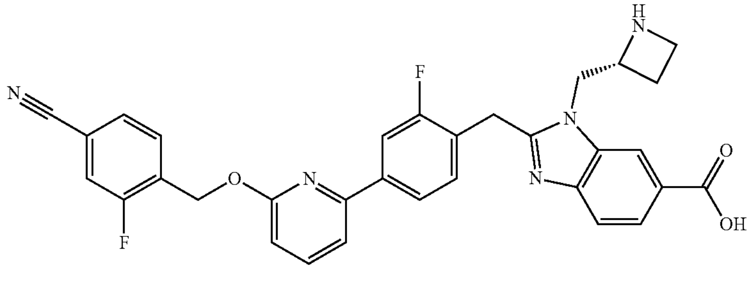 [SMILES: N#Cc1ccc(COc2cccc(-c3ccc(Cc4nc5ccc(C(=O)O)cc5n4C[C@H]4CCN4)c(F)c3)n2)c(F)c1]<br>(R)-1-(azetidin-2-ylmethyl)-2-(4-(6-((4-cyano-2-fluorobenzyl)oxy)pyridin-2-yl)-2-fluorobenzyl)-1H-benzo[d]imidazole-6-carboxylic acid: ES/MS 566.2; $^1$H NMR (400 MHz, Methanol-d4) δ 8.14-8.02 (m, 1H), 7.93-7.77 (m, 3H), 7.77-7.65 (m, 2H), 7.65-7.49 (m, 3H), 7.41 (t, J = 8.0 Hz, 1H), 6.90 (d, J = 1.0 Hz, 1H), 5.65 (s, 2H), 4.55 (s, 2H), 4.13 (q, J = 9.4 Hz, 1H), 3.97 (td, J = 10.0, 4.5 Hz, 1H), 2.68 (p, J = 9.6 Hz, 1H), 2.60-2.45 (m, 1H). |
| 490 | 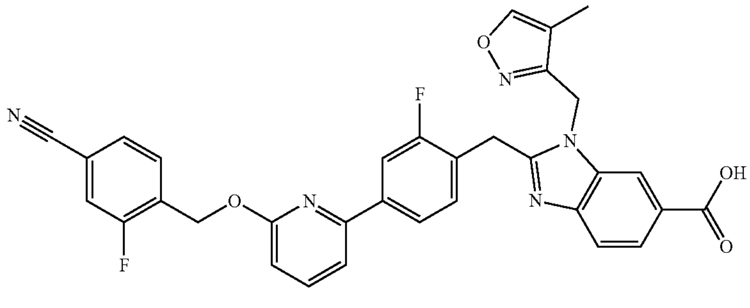 [SMILES: Cc1conc1Cn1c(Cc2ccc(-c3cccc(OCc4ccc(C#N)cc4F)n3)cc2F)nc2ccc(C(=O)O)cc21] |

-continued

| Example | Structure/Name/Characterization |
|---|---|
| | 2-(4-(6-((4-cyano-2-fluorobenzyl)oxy)pyridin-2-yl)-2-fluorobenzyl)-1-((4-methylisoxazol-3-yl)methyl)-1H-benzo[d]imidazole-6-carboxylic acid: ES/MS 592.2; $^1$H NMR (400 MHz, DMSO-d6) δ 8.63 (d, J = 1.2 Hz, 1H), 8.25 (d, J = 1.5 Hz, 1H), 7.93 (dt, J = 9.9, 2.2 Hz, 1H), 7.89-7.80 (m, 4H), 7.79-7.70 (m, 2H), 7.66 (dd, J = 8.0, 5.3 Hz, 2H), 7.43 (t, J = 7.9 Hz, 1H), 6.93 (d, J = 8.2 Hz, 1H), 5.86 (s, 2H), 5.62 (s, 2H), 4.47 (s, 2H), 1.94 (d, J = 1.1 Hz, 3H). |
| 491 | 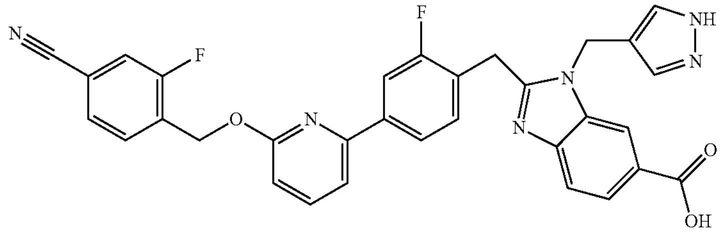 [SMILES: N#Cc1ccc(COc2cccc(-c3ccc(Cc4nc5ccc(C(=O)O)cc5n4Cc4cn[nH]c4)c(F)c3)n2)c(F)c1] 1-((1H-pyrazol-4-yl)methyl)-2-(4-(6-((4-cyano-2-fluorobenzyl)oxy)pyridin-2-yl)-2-fluorobenzyl)-1H-benzo[d]imidazole-6-carboxylic acid: ES/MS m/z 577.2; $^1$H NMR (400 MHz, DMSO-d6) δ 8.29 (d, J = 1.5 Hz, 1H), 7.96-7.79 (m, 6H), 7.79-7.68 (m, 2H), 7.68-7.56 (m, 3H), 7.45 (t, J = 8.1 Hz, 1H), 6.93 (d, J = 8.2 Hz, 1H), 6.17 (d, J = 2.2 Hz, 1H), 5.63 (d, J = 9.3 Hz, 4H), 4.58 (s, 2H). |

Example 482, 3-[[(2S)-1-acetylpyrrolidin-2-yl]methyl]-2-[[4-[3-[(4-chloro-2-fluoro-phenyl)methoxy]-4-fluoro-phenyl]-2-fluoro-phenyl]methyl]benzimidazole-5-carboxylic Acid Procedure 31

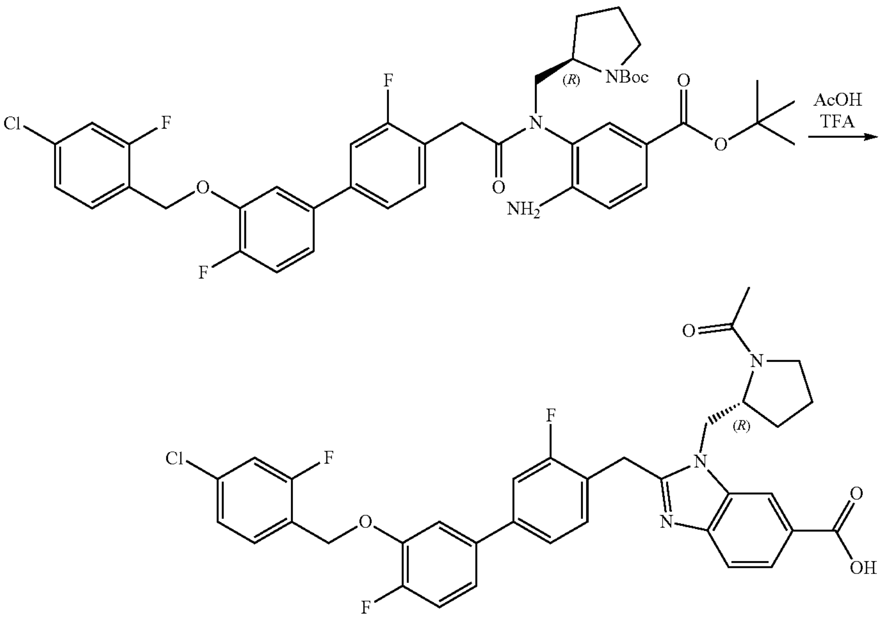

Example 482

3-[[(2S)-1-acetylpyrrolidin-2-yl]methyl]-2-[[4-[3-[(4-chloro-2-fluoro-phenyl)methoxy]-4-fluoro-phenyl]-2-fluoro-phenyl]methyl]benzimidazole-5-carboxylic acid (Example 482): Crude tert-butyl (2S)-2-[[5-tert-butoxycarbonyl-2-[[2-[4-[3-[(4-chloro-2-fluoro-phenyl)methoxy]-4-fluoro-phenyl]-2-fluoro-phenyl]acetyl]amino]anilino]methyl]pyrrolidine-1-carboxylate (95.9 mg, 0.123 mmol) was dissolved in acetic acid (1 mL) and the mixture was heated to 80° C. for 12 hours. Excess trifluoroacetic acid was added (0.1 mL). Heating was continued for 6 hours. The mixture was cooled to ambient temperature, concentrated and purified by RP-HPLC (eluent: water/MeCN 0.1% TFA) to yield the titled product: ES/MS m/z: 648.200 (M+H$^+$); $^1$H NMR (400 MHz, Methanol-d4) δ 8.53 (s, 1H), 8.27-8.16 (m, 1H), 7.76 (d, J=8.5 Hz, 1H), 7.66-7.39 (m, 5H), 7.27 (dd, J=11.6, 9.7 Hz, 4H), 5.30 (s, 2H), 4.80 (d, J=4.5 Hz, 2H), 4.70 (s, 1H), 3.74-3.61 (m, 1H), 3.58 (d, J=12.2 Hz, 1H), 1.96 (s, 2H), 1.31 (d, J=3.8 Hz, 1H), 1.14 (s, 1H). 19F NMR (376 MHz, Methanol-d4) δ −77.78, −118.03 (d, J=10.8 Hz), −118.35 (d, J=8.7 Hz), −136.92.

Examples 453, 464, 482, 483, 485, 488, 539, 591 and 689-691. Compounds Prepared Using Procedure 31

Other compounds of the present disclosure prepared using the general route described in Procedure 31 include the following Examples.

| Example | Structure/Name/Characterization |
|---|---|
| 453 | 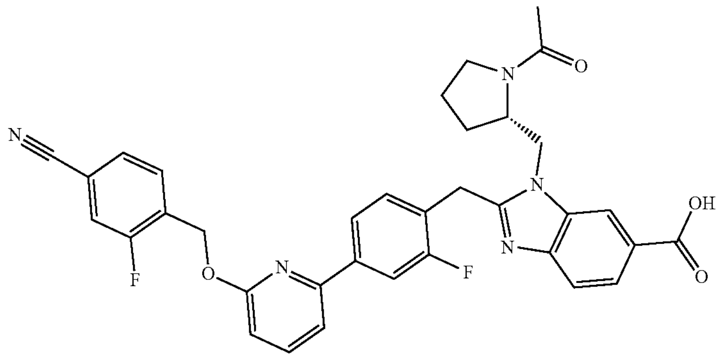 [SMILES: CC(=O)N1CCC[C@H]1Cn1c(Cc2ccc(-c3cccc(OCc4ccc(C#N)cc4F)n3)cc2F)nc2ccc(C(=O)O)cc21]<br>(S)-1-((1-acetylpyrrolidin-2-yl)methyl)-2-(4-(6-((4-cyano-2-fluorobenzyl)oxy)pyridin-2-yl)-2-fluorobenzyl)-1H-benzo[d]imidazole-6-carboxylic acid: ES/MS 622.2; $^{1}$H NMR (400 MHz, Methanol-d4) δ 8.52 (t, J = 0.9 Hz, 1H), 8.20 (dd, J = 8.6, 1.4 Hz, 1H), 8.00-7.85 (m, 2H), 7.85-7.67 (m, 3H), 7.67-7.49 (m, 4H), 6.91 (d, J = 8.2 Hz, 1H), 5.64 (s, 2H), 4.80 (d, J = 4.3 Hz, 1H), 4.68 (s, 3H), 3.73-3.60 (m, 1H), 3.55 (td, J = 9.7, 7.0 Hz, 1H), 2.33 (hept, J = 9.3, 8.5 Hz, 1H), 2.20-2.00 (m, 0H), 1.95 (dd, J = 12.2, 6.5 Hz, 1H), 1.73 (s, 3H). |
| 464 | 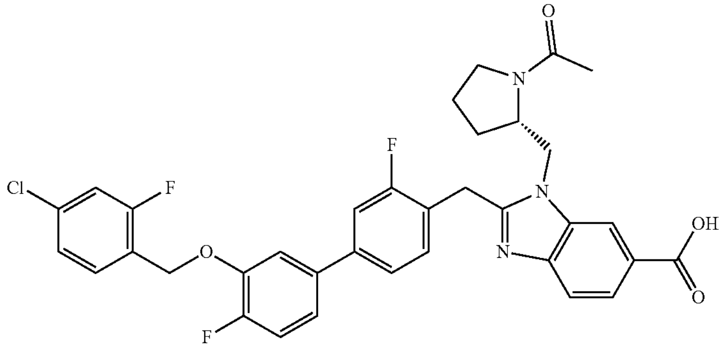 [SMILES: CC(=O)N1CCC[C@H]1Cn1c(Cc2ccc(-c3ccc(F)c(OCc4ccc(Cl)cc4F)c3)cc2F)nc2ccc(C(=O)O)cc21]<br>(S)-1-((1-acetylpyrrolidin-2-yl)methyl)-2-((3'-((4-chloro-2-fluorobenzyl)oxy)-3,4'-difluoro-[1,1'-biphenyl]-4-yl)methyl)-1H-benzo[d]imidazole-6-carboxylic acid: ES/MS m/z 648.2; $^{1}$H NMR (400 MHz, Methanol-d4) δ 8.53 (s, 1H), 8.27-8.16 (m, 1H), 7.76 (d, J = 8.5 Hz, 1H), 7.66-7.39 (m, 5H), 7.27 (dd, J = 11.6, 9.7 Hz, 4H), 5.30 (s, 2H), 4.80 (d, J = 4.5 Hz, 2H), 4.70 (s, 1H), 3.74-3.61 (m, 1H), 3.58 (d, J = 12.2 Hz, 1H), 1.96 (s, 2H), 1.31 (d, J = 3.8 Hz, 1H), 1.14 (s, 1H). |

-continued

| Example | Structure/Name/Characterization |
|---|---|
| 483 | 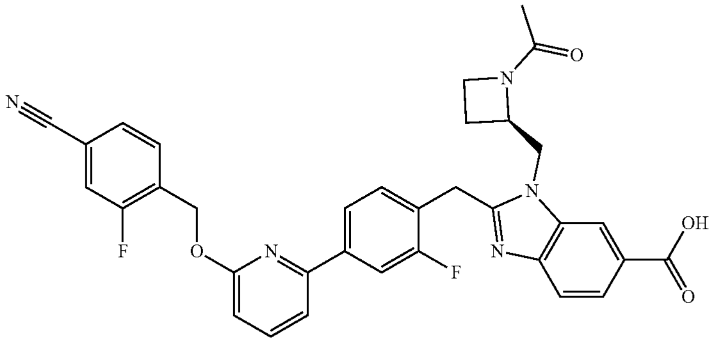 [SMILES: CC(=O)N1CC[C@@H]1Cn1c(Cc2ccc(-c3cccc(OCc4ccc(C#N)cc4F)n3)cc2F)nc2ccc(C(=O)O)cc21] (R)-1-((1-acetylazetidin-2-yl)methyl)-2-(4-(6-((4-cyano-2-fluorobenzyl)oxy)pyridin-2-yl)-2-fluorobenzyl)-1H-benzo[d]imidazole-6-carboxylic acid: ES/MS m/z 608.2; $^1$H NMR (400 MHz, Methanol-d4) δ 8.60 (s, 1H), 8.22 (dd, J = 8.6, 1.4 Hz, 1H), 7.98-7.84 (m, 2H), 7.84-7.67 (m, 4H), 7.67-7.46 (m, 5H), 6.92 (d, J = 8.2 Hz, 1H), 5.64 (s, 2H), 5.03 (dd, J = 15.5, 9.5 Hz, 1H), 4.93 (d, J = 3.4 Hz, 1H), 4.82-4.63 (m, 3H), 4.15 (dtd, J = 31.8, 8.7, 6.0 Hz, 2H), 2.58 (dtd, J = 11.6, 9.1, 5.8 Hz, 1H), 2.32-2.14 (m, 1H), 1.67 (s, 3H). |
| 485 | 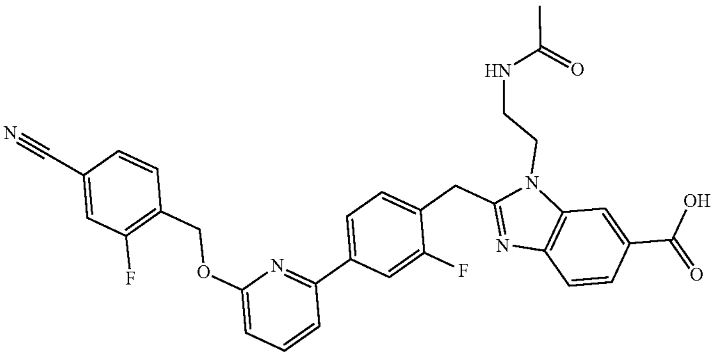 [SMILES: CC(=O)NCCn1c(Cc2ccc(-c3cccc(OCc4ccc(C#N)cc4F)n3)cc2F)nc2ccc(C(=O)O)cc21] 1-(2-acetamidoethyl)-2-(4-(6-((4-cyano-2-fluorobenzyl)oxy)pyridin-2-yl)-2-fluorobenzyl)-1H-benzo[d]imidazole-6-carboxylic acid: ES/MS m/z 582.2; $^1$H NMR (400 MHz, DMSO-d6) δ 8.23 (d, J = 1.5 Hz, 1H), 8.10 (t, J = 5.9 Hz, 1H), 8.03-7.80 (m, 5H), 7.80-7.69 (m, 2H), 7.65 (dd, J = 13.8, 8.0 Hz, 2H), 7.48 (t, J = 7.9 Hz, 1H), 6.93 (d, J = 8.2 Hz, 1H), 5.62 (s, 2H), 4.46 (d, J = 4.2 Hz, 4H), 3.44 (q, J = 5.8 Hz, 2H), 1.72 (s, 3H). |
| 488 | 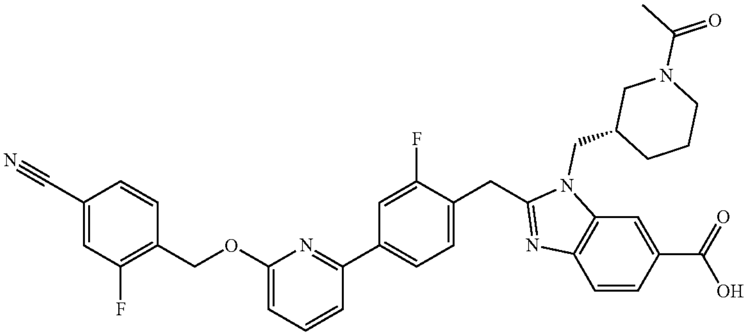 [SMILES: CC(=O)N1CCC[C@H](Cn2c(Cc3ccc(-c4cccc(OCc5ccc(C#N)cc5F)n4)cc3F)nc3ccc(C(=O)O)cc32)C1] (R)-1-((1-acetylpiperidin-3-yl)methyl)-2-(4-(6-((4-cyano-2-fluorobenzyl)oxy)pyridin-2-yl)-2-fluorobenzyl)-1H-benzo[d]imidazole-6-carboxylic acid: ES/MS m/z 636.2; $^1$H NMR (400 MHz, Methanol-d4) δ 8.50 (s, 1H), 8.28-8.14 (m, 1H), 7.96-7.76 (m, 5H), 7.73 (t, J = 7.5 Hz, 1H), 7.66-7.46 (m, 4H), 6.98-6.83 (m, 1H), 5.65 (s, 2H), 4.71 (d, J = 8.6 Hz, 2H), 4.50 (qd, J = 15.1, 7.9 Hz, 2H), 4.24 (d, J = 12.4 Hz, 1H), 3.80 (d, J = 13.5 Hz, 1H), 2.82-2.59 (m, 1H), 2.03 (s, 2H), 1.90-1.64 (m, 2H), 1.64-1.37 (m, 2H). |

-continued

| Example | Structure/Name/Characterization |
| --- | --- |
| 539 | 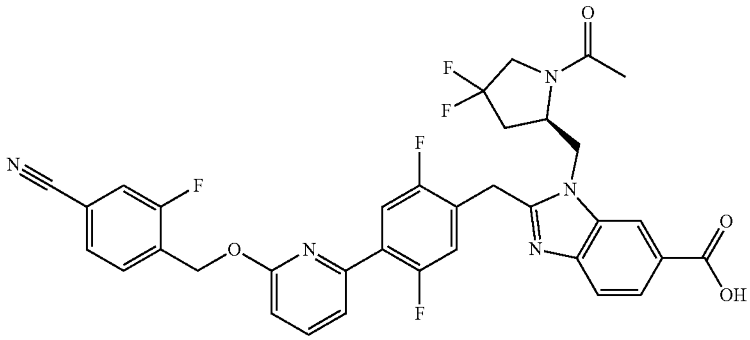 [SMILES: CC(=O)N1CC(F)(F)C[C@@H]1Cn1c(Cc2cc(F)c(-c3cccc(OCc4ccc(C#N)cc4F)n3)cc2F)nc2ccc(C(=O)O)cc21]<br>(R)-1-((1-acetyl-4,4-difluoropyrrolidin-2-yl)methyl)-2-(4-(6-((4-cyano-2-fluorobenzyl)oxy)pyridin-2-yl)-2,5-difluorobenzyl)-1H-benzo[d]imidazole-6-carboxylic acid: ES/MS m/z 676.2; $^{1}$H NMR (400 MHz, DMSO) δ 8.33 (d, J = 1.6 Hz, 1H), 7.98-7.86 (m, 2H), 7.81 (dd, J = 8.4, 1.6 Hz, 1H), 7.79-7.70 (m, 3H), 7.61 (d, J = 8.5 Hz, 1H), 7.53 (dd, J = 7.5, 1.7 Hz, 1H), 7.45 (dd, J = 11.5, 6.1 Hz, 1H), 7.00 (d, J = 8.3 Hz, 1H), 5.60 (s, 2H), 4.72 (s, 1H), 4.68-4.57 (m, 1H), 4.46 (d, J = 10.2 Hz, 2H), 4.09 (dd, J = 15.8, 10.3 Hz, 2H), 2.48 (d, J = 1.8 Hz, 1H), 1.94 (s, 2H). |
| 591 | 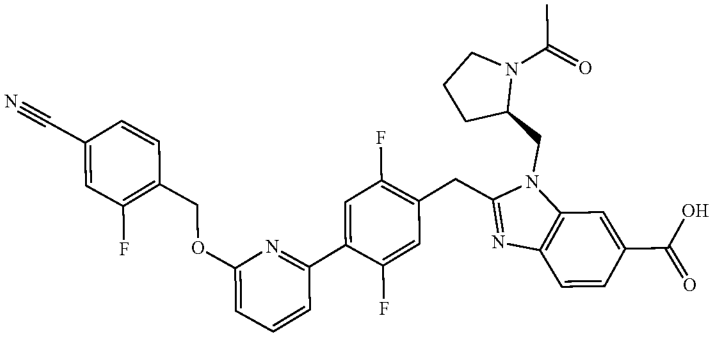 [SMILES: CC(=O)N1CCC[C@@H]1Cn1c(Cc2cc(F)c(-c3cccc(OCc4ccc(C#N)cc4F)n3)cc2F)nc2ccc(C(=O)O)cc21]<br>(R)-1-((1-acetylpyrrolidin-2-yl)methyl)-2-(4-(6-((4-cyano-2-fluorobenzyl)oxy)pyridin-2-yl)-2,5-difluorobenzyl)-1H-benzo[d]imidazole-6-carboxylic acid: ES/MS m/z 640.1; $^{1}$H NMR (400 MHz, DMSO-d6) δ 8.41 (d, J = 1.5 Hz, 1H), 7.98-7.83 (m, 3H), 7.83-7.70 (m, 3H), 7.65 (d, J = 8.4 Hz, 1H), 7.57-7.46 (m, 2H), 6.99 (dd, J = 8.3, 2.1 Hz, 1H), 5.59 (s, 2H), 4.57 (d, J = 8.3 Hz, 2H), 3.45 (ddt, J = 26.2, 10.1, 5.4 Hz, 2H), 2.21-2.04 (m, 1H), 1.85 (s, 2H), 1.79-1.65 (m, 1H). |
| 689 | 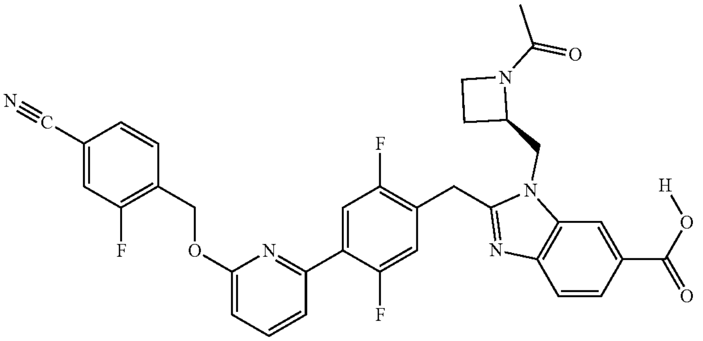 [SMILES: CC(=O)N1CC[C@@H]1Cn1c(Cc2cc(F)c(-c3cccc(OCc4ccc(C#N)cc4F)n3)cc2F)nc2ccc(C(=O)O)cc21]<br>ES/MS m/z 626.3; 1H NMR (400 MHz, Methanol-d4) δ 8.59 (d, J = 1.3 Hz, 1H), 8.22 (dd, J = 8.6, 1.4 Hz, 1H), 7.90-7.74 (m, 3H), 7.72 (t, J = 7.5 Hz, 1H), 7.65-7.51 (m, 4H), 7.43 (dd, J = 11.2, 6.1 Hz, 1H), 6.96 (d, J = 8.3 Hz, 1H), 5.62 (s, 2H), 5.10-4.89 (m, 3H), 4.26-4.04 (m, 2H), 2.69-2.49 (m, 1H), 2.24 (ddd, J = 11.8, 9.0, 5.9 Hz, 1H), 1.70 (s, 3H). |

-continued

| Example | Structure/Name/Characterization |
| --- | --- |
| 690 | 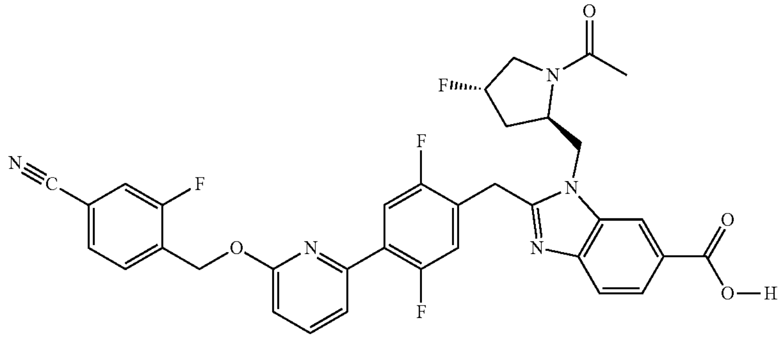 [SMILES: CC(=O)N1C[C@@H](F)C[C@@H]1Cn1c(Cc2cc(F)c(-c3cccc(OCc4ccc(C#N)cc4F)n3)cc2F)nc2ccc(C(=O)O)cc21] ES/MS (M + H+) 658.0; 1H NMR (400 MHz, DMSO) δ 8.44 (d, J = 9.9 Hz, 1H), 7.98-7.83 (m, 3H), 7.83-7.70 (m, 3H), 7.65 (d, J = 8.5 Hz, 1H), 7.58-7.45 (m, 2H), 7.00 (dd, J = 8.3, 1.9 Hz, 1H), 5.60 (s, 2H), 5.40 (s, 0H), 5.27 (s, 0H), 4.69-4.43 (m, 3H), 2.37-1.99 (m, 1H), 1.91 (s, 2H). Multiplet Report 19F NMR (376 MHz, DMSO) δ −75.23, −115.92 (dd, J = 10.0, 6.2 Hz), −121.62, −122.22. |
| 691 | 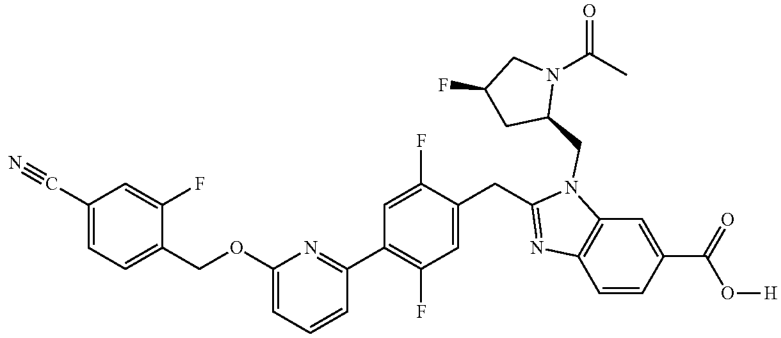 [SMILES: CC(=O)N1C[C@H](F)C[C@@H]1Cn1c(Cc2cc(F)c(-c3cccc(OCc4ccc(C#N)cc4F)n3)cc2F)nc2ccc(C(=O)O)cc21] ES/MS (M + H+) 658.2; 1H NMR (400 MHz, DMSO) δ 8.33 (d, J = 1.5 Hz, 1H), 8.00-7.82 (m, 3H), 7.82-7.70 (m, 3H), 7.65 (dd, J = 8.4, 2.8 Hz, 1H), 7.53 (dd, J = 7.5, 1.7 Hz, 1H), 7.47 (dd, J = 11.5, 6.1 Hz, 1H), 7.00 (d, J = 8.2 Hz, 1H), 5.60 (s, 2H), 4.62 (dt, J = 10.8, 5.8 Hz, 2H), 4.54 (s, 1H), 4.42 (dd, J = 11.0, 5.5 Hz, 1H), 4.01-3.81 (m, 1H), 2.17-2.01 (m, 1H), 1.91 (s, 2H). Multiplet Report 19F NMR (376 MHz, DMSO) δ −75.09, −115.91 (dd, J = 9.8, 6.5 Hz), −121.69, −122.25. |

Example 467, 2-(4-(6-((2-cyclopropylbenzyl)oxy)pyridin-2-yl)-2-fluorobenzyl)-1-(2-methoxyethyl)-1H-benzo[d]imidazole-6-carboxylic acid Procedure 32

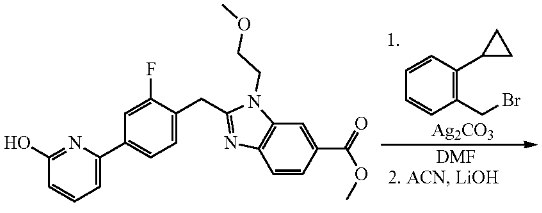

I-109

-continued

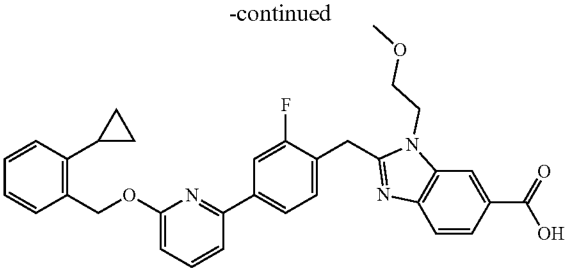

Example 467

2-(4-(6-((2-cyclopropylbenzyl)oxy)pyridin-2-yl)-2-fluorobenzyl)-1-(2-methoxyethyl)-1H-benzo[d]imidazole-6-carboxylic acid (Example 467): Methyl 2-[[2-fluoro-4-(6-hydroxy-2-pyridyl)phenyl]methyl]-3-(2-methoxyethyl)benzimidazole-5-carboxylate (I-109, 50.0 mg, 0.115 mmol) was added to 1-(bromomethyl)-2-cyclopropyl-benzene (37.7 mg, 0.179 mmol) and silver carbonate (95.0 mg, 0.344 mmol) in DMF (1 mL). The mixture was heated to 80° C. for 12 hours. The mixture was cooled to ambient temperature and filtered. The mixture was diluted with acetonitrile (2 mL) and excess 1 M aq. LiOH was added (0.5 mL). The mixture was heated to 60° C. for 2 hours. The reaction was cooled to ambient temperature and quenched with excess trifluoroacetic acid (0.1 mL). The mixture was purified by RP-HPLC (eluent: water/MeCN 0.1% TFA) to yield the titled product: ES/MS m/z: 659.200 (M+H$^+$); $^1$H NMR (400 MHz, Methanol-d4) δ 8.58-8.51 (m, 1H), 8.27 (dd, J=8.7, 1.4 Hz, 1H), 8.01 (dd, J=8.1, 1.7 Hz, 1H), 7.95-7.85 (m, 2H), 7.78 (t, J=7.8 Hz, 1H), 7.69 (t, J=7.9 Hz, 1H), 7.54 (d, J=7.4 Hz, 1H), 7.42 (dd, J=7.5, 1.5 Hz, 1H), 7.22 (td, J=7.5, 1.5 Hz, 1H), 7.15 (td, J=7.5, 1.4 Hz, 1H), 7.11-6.99 (m, 1H), 6.87 (d, J=8.2 Hz, 1H), 6.72 (s, 1H), 5.69 (s, 2H), 4.76-4.64 (m, 1H), 4.54 (ddd, J=15.2, 8.1, 3.4 Hz, 1H), 3.71 (ddd, J=10.6, 5.2, 3.4 Hz, 1H), 3.57 (ddd, J=10.7, 7.8, 3.1 Hz, 1H), 3.22 (s, 3H), 2.10 (ddd, J=13.9, 8.5, 5.3 Hz, 1H), 1.02-0.80 (m, 3H), 0.80-0.56 (m, 2H). 19F NMR (376 MHz, Methanol-d4) δ −77.82, −119.74 (dd, J=12.4, 7.7 Hz).

Example 129, 135-138, 140-152, 155-158, 227, 229, 234, 238, 241, 243, 247-248, 250-252, 256, 262, 265, 266, 348, 357, 362, 435, 470, 473-474, 478, 481, 493, 495, 496, 499, 500, 504-506, 509-510, 512, 514, 542-544, 557, 563-565, 592, 595-596, and 692-693. Compounds Prepared Using Procedure 32

Other compounds of the present disclosure prepared using the general route described in Procedure 32 include the following Examples.

| Example | Structure/Name/Characterization |
|---|---|
| 129 | 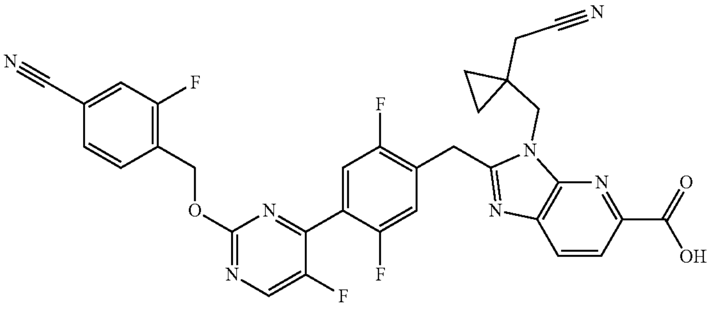 [SMILES: N#CCC1(Cn2c(Cc3cc(F)c(-c4nc(OCc5ccc(C#N)cc5F)ncc4F)cc3F)nc3ccc(C(=O)O)nc32)CC1] 2-(4-(2-((4-cyano-2-fluorobenzyl)oxy)-5-fluoropyrimidin-4-yl)-2,5-difluorobenzyl)-3-((1-(cyanomethyl)cyclopropyl)methyl)-3H-imidazo[4,5-b]pyridine-5-carboxylic acid: ES/MS m/z 628.2; $^1$H NMR (400 MHz, DMSO) δ 8.90 (d, J = 1.8 Hz, 1H), 8.09 (d, J = 8.2 Hz, 1H), 7.97 (d, J = 8.3 Hz, 1H), 7.95-7.90 (m, 1H), 7.81-7.72 (m, 2H), 7.65-7.54 (m, 2H), 5.57 (s, 2H), 4.56 (s, 2H), 4.51 (s, 2H), 2.79 (s, 2H), 1.10-1.02 (m, 2H), 0.72-0.65 (m, 2H). |
| 135 | 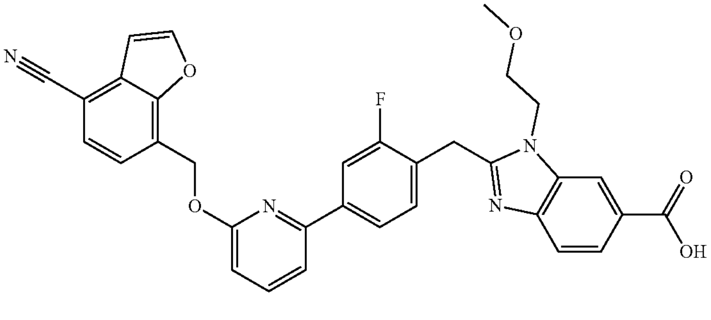 [SMILES: COCCn1c(Cc2ccc(-c3cccc(OCc4ccc(C#N)c5ccoc45)n3)cc2F)nc2ccc(C(=O)O)cc21] 2-(4-(6-((4-cyanobenzofuran-7-yl)methoxy)pyridin-2-yl)-2-fluorobenzyl)-1-(2-methoxyethyl)-1H-benzo[d]imidazole-6-carboxylic acid: ES/MS m/z 577.2; $^1$H NMR (400 MHz, DMSO) δ 8.36 (d, J = 2.3 Hz, 1H), 8.25 (d, J = 1.6 Hz, 1H), 7.90-7.75 (m, 5H), 7.68-7.56 (m, 3H), 7.41 (t, J = 8.0 Hz, 1H), 7.24 (d, J = 2.3 Hz, 1H), 6.94 (d, J = 8.2 Hz, 1H), 5.87 (s, 2H), 4.60 (t, J = 5.1 Hz, 2H), 4.47 (s, 2H), 3.66 (t, J = 5.1 Hz, 2H), 3.20 (s, 3H). |
| 136 | 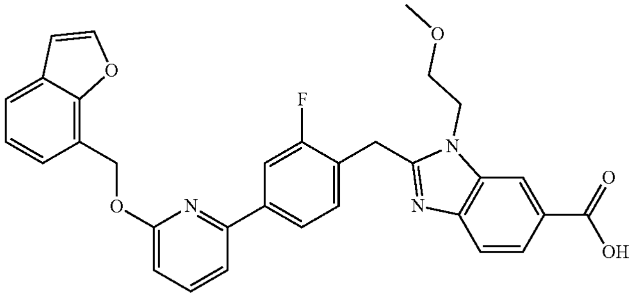 |

-continued

| Example | Structure/Name/Characterization |
| --- | --- |
| | 2-(4-(6-(benzofuran-7-ylmethoxy)pyridin-2-yl)-2-fluorobenzyl)-1-(2-methoxyethyl)-1H-benzo[d]imidazole-6-carboxylic acid: ES/MS m/z 552.2; $^{1}H$ NMR (400 MHz, MeOD) δ 8.52 (s, 1H), 8.23-8.16 (m, 1H), 7.91 (d, J = 9.8 Hz, 2H), 7.82-7.72 (m, 3H), 7.59-7.38 (m, 4H), 7.26-7.17 (m, 1H), 6.89-6.82 (m, 2H), 5.81 (s, 2H), 4.78 (t, J = 4.8 Hz, 2H), 4.73 (s, 2H), 3.79 (t, J = 4.9 Hz, 2H). Additional peak (s, 3H) obscured by solvent. |
| 137 | 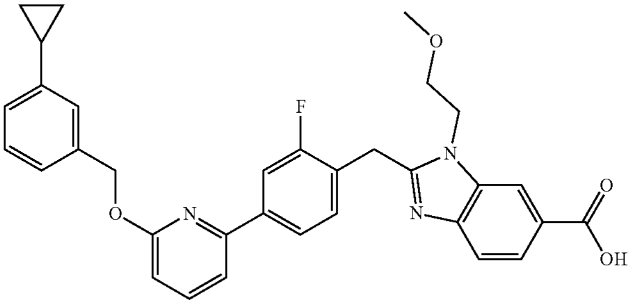 [SMILES: COCCn1c(Cc2ccc(-c3cccc(OCc4cccc(C5CC5)c4)n3)cc2F)nc2ccc(C(=O)O)cc21] 2-(4-(6-((3-cyclopropylbenzyl)oxy)pyridin-2-yl)-2-fluorobenzyl)-1-(2-methoxyethyl)-1H-benzo[d]imidazole-6-carboxylic acid: ES/MS m/z 552.2; 1H NMR (400 MHz, MeOD) δ 8.50 (d, J = 1.4 Hz, 1H), 8.18 (dd, J = 8.6, 1.4 Hz, 1H), 7.93 (s, 1H), 7.90 (dd, J = 4.5, 1.6 Hz, 1H), 7.80-7.71 (m, 2H), 7.53-7.43 (m, 2H), 7.26-7.17 (m, 3H), 7.03-6.95 (m, 1H), 6.83 (d, J = 8.2 Hz, 1H), 5.44 (s, 2H), 4.75 (t, J = 5.0 Hz, 2H), 4.72 (s, 2H), 3.82-3.75 (m, 2H), 3.29 (s, 3H), 1.89 (tt, J = 8.4, 5.1 Hz, 1H), 0.96-0.85 (m, 2H), 0.68-0.60 (m, 2H). |
| 138 | 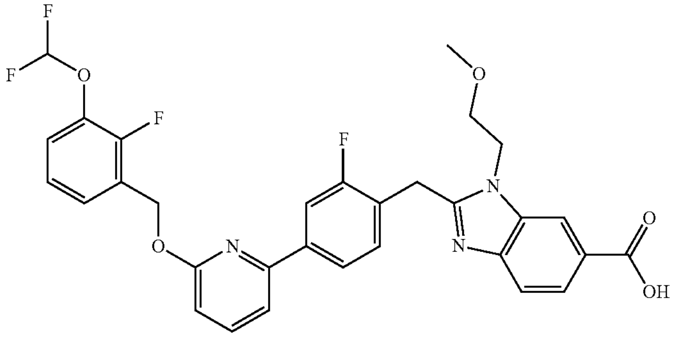 [SMILES: COCCn1c(Cc2ccc(-c3cccc(OCc4cccc(OC(F)F)c4F)n3)cc2F)nc2ccc(C(=O)O)cc21] 2-(4-(6-((3-(difluoromethoxy)-2-fluorobenzyl)oxy)pyridin-2-yl)-2-fluorobenzyl)-1-(2-methoxyethyl)-1H-benzo[d]imidazole-6-carboxylic acid: ES/MS m/z 596.2; $^{1}H$ NMR (400 MHz, Methanol-d4) δ 8.54 (t, J = 0.9 Hz, 1H), 8.21 (dd, J = 8.6, 1.4 Hz, 1H), 7.96-7.90 (m, 2H), 7.82-7.74 (m, 2H), 7.55 (d, J = 7.5 Hz, 1H), 7.50 (t, J = 8.0 Hz, 1H), 7.41 (ddd, J = 7.8, 6.3, 1.7 Hz, 1H), 7.25 (t, J = 7.9 Hz, 1H), 7.17 (td, J = 8.0, 1.3 Hz, 1H), 7.04-6.58 (m, 2H), 5.59 (s, 2H), 4.79 (t, J = 5.0 Hz, 2H), 4.75 (s, 2H), 3.80 (t, J = 4.9 Hz, 2H). Additional peak (s, 3H) obscured by solvent. |
| 140 | 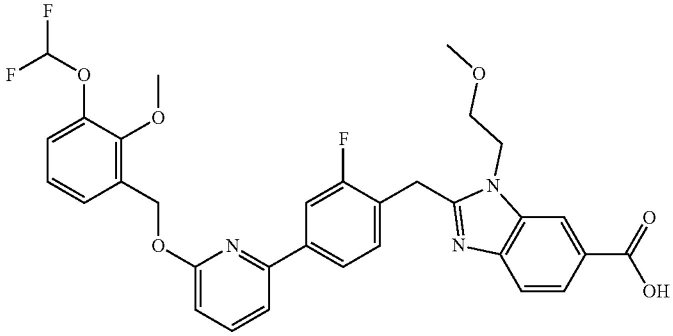 [SMILES: COCCn1c(Cc2ccc(-c3cccc(OCc4cccc(OC(F)F)c4OC)n3)cc2F)nc2ccc(C(=O)O)cc21] 2-(4-(6-((3-(difluoromethoxy)-2-methoxybenzyl)oxy)pyridin-2-yl)-2-fluorobenzyl)-1-(2-methoxyethyl)-1H-benzo[d]imidazole-6-carboxylic acid: ES/MS m/z 608.2; $^{1}H$ NMR (400 MHz, MeOD) δ 8.45 (d, J = 1.6 Hz, 1H), 8.14 (dd, J = 8.6, 1.5 Hz, 1H), 7.93 (dd, J = 4.2, 1.6 Hz, 1H), 7.90 (s, 1H), 7.77 (dd, |

-continued

| Example | Structure/Name/Characterization |
|---|---|
| | J = 8.2, 7.5 Hz, 1H), 7.72 (d, J = 8.6 Hz, 1H), 7.52 (d, J = 7.5 Hz, 1H), 7.44 (t, J = 7.9 Hz, 1H), 7.35 (dd, J = 7.5, 1.8 Hz, 1H), 7.19-7.06 (m, 2H), 7.02-6.54 (m, 2H), 5.56 (s, 2H), 4.71 (t, J = 5.0 Hz, 2H), 4.67 (s, 2H), 3.91 (s, 3H), 3.77 (t, J = 5.0 Hz, 2H), 3.29 (s, 3H). *NOTE* NMR reported for major conformer observed in NMR. LC/MS is clean, and NMR appears to show a second confirmation at approximately4:1/5:1 ratio |
| 141 | 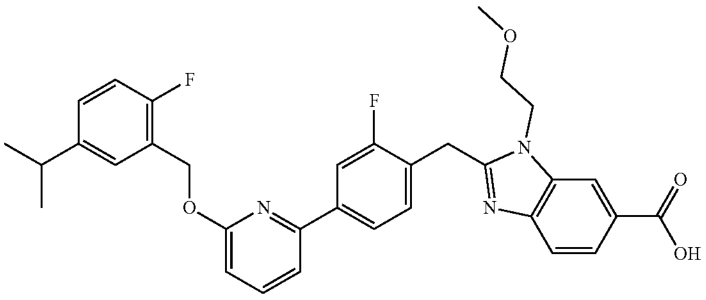 [SMILES: COCCn1c(Cc2ccc(-c3cccc(OCc4cc(C(C)C)ccc4F)n3)cc2F)nc2ccc(C(=O)O)cc21] 2-(2-fluoro-4-(6-((2-fluoro-5-isopropylbenzyl)oxy)pyridin-2-yl)benzyl)-1-(2-methoxyethyl)-1H-benzo[d]imidazole-6-carboxylic acid: ES/MS m/z 572.2; $^1$H NMR (400 MHz, MeOD) δ 8.54 (d, J = 1.4 Hz, 1H), 8.21 (dd, J = 8.6, 1.4 Hz, 1H), 7.97 (s, 1H), 7.96-7.93 (m, 1H), 7.82-7.73 (m, 2H), 7.56-7.45 (m, 2H), 7.40 (dd, J = 7.1, 2.4 Hz, 1H), 7.19 (ddd, J = 7.9, 5.0, 2.4 Hz, 1H), 7.02 (dd, J = 10.0, 8.5 Hz, 1H), 6.85 (d, J = 8.2 Hz, 1H), 5.53 (s, 2H), 4.80 (t, J = 5.0 Hz, 2H), 4.76 (s, 2H), 3.83-3.77 (m, 2H), 2.87 (hept, J = 7.0 Hz, 1H), 1.18 (d, J = 6.9 Hz, 6H). Additional peak (s, 3H) obscured by solvent) |
| 142 | 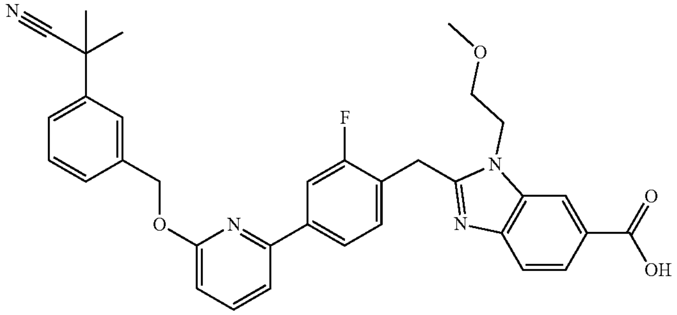 [SMILES: COCCn1c(Cc2ccc(-c3cccc(OCc4cccc(C(C)(C)C#N)c4)n3)cc2F)nc2ccc(C(=O)O)cc21] 2-(4-(6-((3-(2-cyanopropan-2-yl)benzyl)oxy)pyridin-2-yl)-2-fluorobenzyl)-1-(2-methoxyethyl)-1H-benzo[d]imidazole-6-carboxylic acid: ES/MS m/z 579.2; $^1$H NMR (400 MHz, MeOD) δ 8.55 (d, J = 1.6 Hz, 1H), 8.22 (dd, J = 8.6, 1.5 Hz, 1H), 7.98-7.88 (m, 2H), 7.82-7.74 (m, 2H), 7.67 (d, J = 2.2 Hz, 1H), 7.56-7.36 (m, 5H), 6.87 (d, J = 8.2 Hz, 1H), 5.54 (s, 2H), 4.85-4.74 (m, 4H), 3.81 (t, J = 4.9 Hz, 2H), 1.68 (s, 6H). Additional peak (s, 3H) obscured by solvent. |
| 143 | 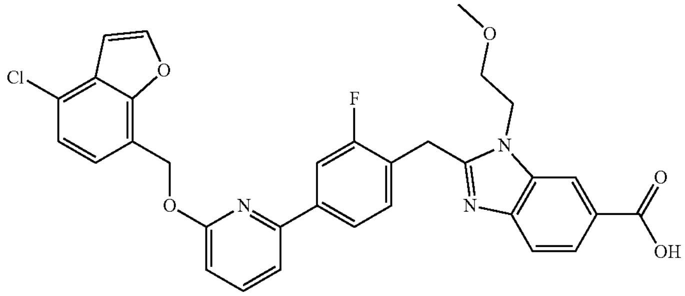 [SMILES: COCCn1c(Cc2ccc(-c3cccc(OCc4ccc(Cl)c5ccoc45)n3)cc2F)nc2ccc(C(=O)O)cc21] 2-(4-(6-((4-chlorobenzofuran-7-yl)methoxy)pyridin-2-yl)-2-fluorobenzyl)-1-(2-methoxyethyl)-1H-benzo[d]imidazole-6-carboxylic acid: ES/MS m/z 586; $^1$H NMR (400 MHz, MeOD) δ 8.57-8.52 (m, 1H), 8.22 (dd, J = 8.6, 1.5 Hz, 1H), 7.94-7.85 (m, 3H), 7.82-7.73 (m, 2H), 7.53 (d, J = 7.4 Hz, 1H), 7.48 (t, J = 8.0 Hz, 1H), 7.40 (d, J = 8.0 Hz, 1H), 7.24 (d, J = 8.0 Hz, 1H), 6.94 (d, J = 2.2 Hz, 1H), 6.86 (d, J = 8.2 Hz, 1H), 5.79 (s, 2H), 4.80 (t, J = 4.9 Hz, 2H), 4.75 (s, 2H), 3.80 (dd, J = 5.4, 4.4 Hz, 2H). Additional peak (s, 3H) obscured by solvent. |

-continued

| Example | Structure/Name/Characterization |
|---|---|
| 144 | 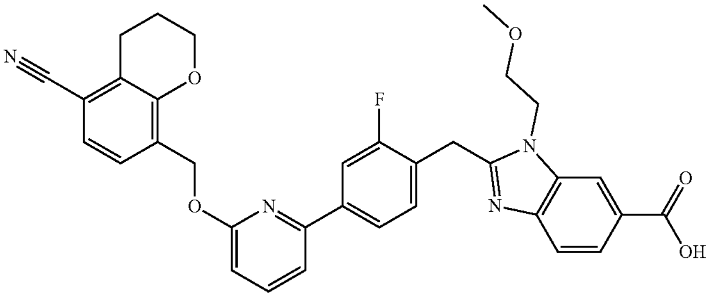 [SMILES: COCCn1c(Cc2ccc(-c3cccc(OCc4ccc(C#N)c5c4OCCC5)n3)cc2F)nc2ccc(C(=O)O)cc21] 2-(4-(6-((5-cyanochroman-8-yl)methoxy)pyridin-2-yl)-2-fluorobenzyl)-1-(2-methoxyethyl)-1H-benzo[d]imidazole-6-carboxylic acid: ES/MS m/z 593.2; $^{1}$H NMR (400 MHz, DMSO) δ 8.26 (s, 1H), 7.90-7.80 (m, 4H), 7.63 (dd, J = 8.0, 5.5 Hz, 2H), 7.44 (t, J = 8.1 Hz, 1H), 7.40-7.24 (m, 2H), 6.92 (d, J = 8.2 Hz, 1H), 5.48 (s, 2H), 4.61 (t, J = 5.1 Hz, 2H), 4.49 (s, 2H), 4.32-4.25 (m, 2H), 3.67 (t, J = 5.1 Hz, 2H), 3.20 (s, 3H), 2.91 (t, J = 6.5 Hz, 2H), 2.02 (p, J = 6.1 Hz, 2H). |
| 145 | 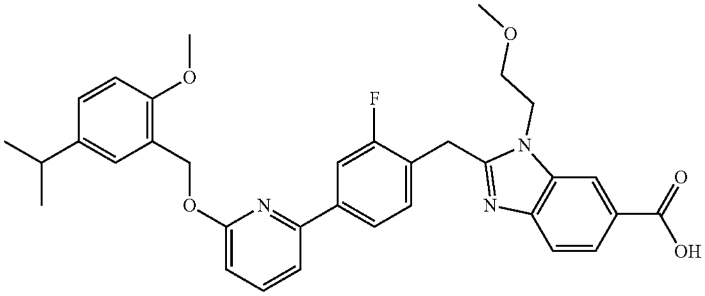 [SMILES: COCCn1c(Cc2ccc(-c3cccc(OCc4cc(C(C)C)ccc4OC)n3)cc2F)nc2ccc(C(=O)O)cc21] 2-(2-fluoro-4-(6-((5-isopropyl-2-methoxybenzyl)oxy)pyridin-2-yl)benzyl)-1-(2-methoxyethyl)-1H-benzo[d]imidazole-6-carboxylic acid: ES/MS m/z 584.2; $^{1}$H NMR (400 MHz, MeOD) δ 8.51 (d, J = 1.5 Hz, 1H), 8.18 (dd, J = 8.6, 1.4 Hz, 1H), 7.99-7.94 (m, 1H), 7.93 (s, 1H), 7.80-7.71 (m, 2H), 7.55-7.44 (m, 2H), 7.30 (d, J = 2.3 Hz, 1H), 7.14 (dd, J = 8.4, 2.3 Hz, 1H), 6.91 (d, J = 8.4 Hz, 1H), 6.83 (d, J = 8.2 Hz, 1H), 5.48 (s, 2H), 4.76 (t, J = 5.0 Hz, 2H), 4.73 (s, 2H), 3.85 (s, 3H), 3.79 (t, J = 5.0 Hz, 2H), 3.30 (s, 3H), 2.94-2.69 (m, J = 7.1 Hz, 1H), 1.17 (d, J = 7.0 Hz, 6H). |
| 146 | 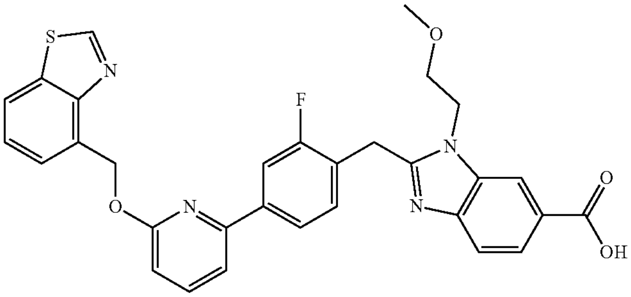 [SMILES: COCCn1c(Cc2ccc(-c3cccc(OCc4cccc5scnc45)n3)cc2F)nc2ccc(C(=O)O)cc21] 2-(4-(6-(benzo[d]thiazol-4-ylmethoxy)pyridin-2-yl)-2-fluorobenzyl)-1-(2-methoxyethyl)-1H-benzo[d]imidazole-6-carboxylic acid: ES/MS 569.2; $^{1}$H NMR (400 MHz, Methanol-d4) δ 9.29 (s, 1H), 8.55 (t, J = 0.9 Hz, 1H), 8.22 (dd, J = 8.6, 1.4 Hz, 1H), 8.02 (dd, J = 8.1, 1.1 Hz, 1H), 7.93-7.86 (m, 2H), 7.82-7.74 (m, 2H), 7.68 (dd, J = 7.4, 1.1 Hz, 1H), 7.53 (d, J = 7.4 Hz, 1H), 7.49 (d, J = 7.6 Hz, 1H), 7.45 (d, J = 7.6 Hz, 1H), 6.91 (d, J = 8.2 Hz, 1H), 6.07 (s, 2H), 4.80 (t, J = 5.0 Hz, 2H), 4.75 (s, 2H), 3.84-3.77 (m, 2H). Additional peak (s, 3H) obscured by solvent. |

-continued

| Example | Structure/Name/Characterization |
|---|---|
| 147 | 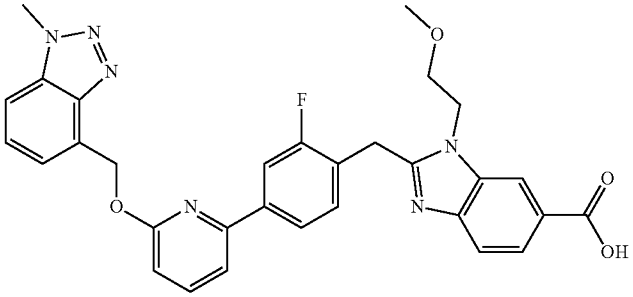 [SMILES: COCCn1c(Cc2ccc(-c3cccc(OCc4cccc5c4nnn5C)n3)cc2F)nc2ccc(C(=O)O)cc21] 2-(2-fluoro-4-(6-((1-methyl-1H-benzo[d][1,2,3]triazol-4-yl)methoxy)pyridin-2-yl)benzyl)-1-(2-methoxyethyl)-1H-benzo[d]imidazole-6-carboxylic acid: ES/MS m/z 567.2; $^1$H NMR (400 MHz, Methanol-d4) δ 8.55 (t, J = 1.0 Hz, 1H), 8.22 (dd, J = 8.6, 1.4 Hz, 1H), 7.91 (dd, J = 8.1, 1.7 Hz, 1H), 7.83 (dd, J = 11.7, 1.7 Hz, 1H), 7.81-7.74 (m, 2H), 7.73-7.67 (m, 1H), 7.58-7.52 (m, 3H), 7.47 (t, J = 7.9 Hz, 1H), 6.92 (d, J = 8.2 Hz, 1H), 6.04 (s, 2H), 4.80 (t, J = 5.0 Hz, 2H), 4.75 (s, 2H), 4.34 (s, 3H), 3.80 (t, J = 4.9 Hz, 2H). Additional peak (s, 3H) obscured by solvent. |
| 148 | 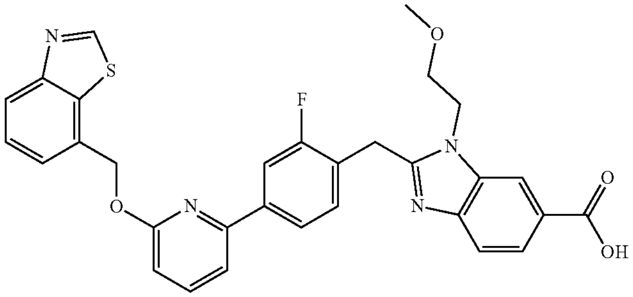 [SMILES: COCCn1c(Cc2ccc(-c3cccc(OCc4cccc5ncsc45)n3)cc2F)nc2ccc(C(=O)O)cc21] 2-(4-(6-(benzo[d]thiazol-7-ylmethoxy)pyridin-2-yl)-2-fluorobenzyl)-1-(2-methoxyethyl)-1H-benzo[d]imidazole-6-carboxylic acid: ES/MS m/z 569.2; $^1$H NMR (400 MHz, Methanol-d4) δ 9.27 (s, 1H), 8.57 (t, J = 1.0 Hz, 1H), 8.24 (dd, J = 8.6, 1.4 Hz, 1H), 8.04 (dd, J = 8.1, 1.1 Hz, 1H), 7.91 (dd, J = 8.0, 1.7 Hz, 1H), 7.86 (dd, J = 11.6, 1.7 Hz, 1H), 7.84-7.74 (m, 2H), 7.69-7.64 (m, 1H), 7.62-7.54 (m, 2H), 7.50 (t, J = 7.9 Hz, 1H), 6.96 (d, J = 8.2 Hz, 1H), 5.82 (s, 2H), 4.82 (t, J = 4.9 Hz, 2H), 4.77 (s, 2H), 3.85-3.79 (m, 2H). Additional peak (s, 3H) obscured by solvent. |
| 149 | 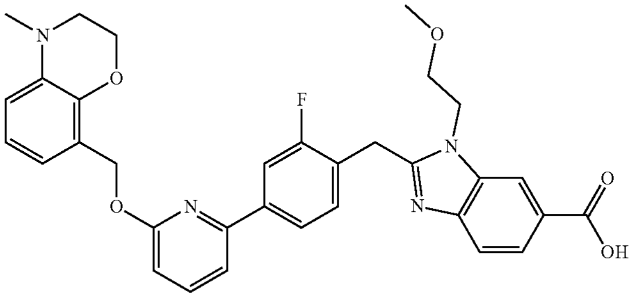 [SMILES: COCCn1c(Cc2ccc(-c3cccc(OCc4cccc5c4OCCN5C)n3)cc2F)nc2ccc(C(=O)O)cc21] 2-(2-fluoro-4-(6-((4-methyl-3,4-dihydro-2H-benzo[b][1,4]oxazin-8-yl)methoxy)pyridin-2-yl)benzyl)-1-(2-methoxyethyl)-1H-benzo[d]imidazole-6-carboxylic acid: ES/MS m/z 583.2; $^1$H NMR (400 MHz, MeOD) δ 8.39 (s, 1H), 8.12-8.05 (m, 1H), 7.97-7.85 (m, 2H), 7.77-7.67 (m, 2H), 7.48 (d, J = 7.5 Hz, 1H), 7.39 (t, J = 7.9 Hz, 1H), 6.82-6.71 (m, 3H), 6.70-6.64 (m, 1H), 5.43 (s, 2H), 4.68-4.55 (m, 4H), 4.34 (t, J = 4.4 Hz, 2H), 3.73 (t, J = 5.0 Hz, 2H), 3.26 (d, J = 7.1 Hz, 4H), 2.86 (s, 3H). |

-continued

| Example | Structure/Name/Characterization |
|---|---|
| 150 | 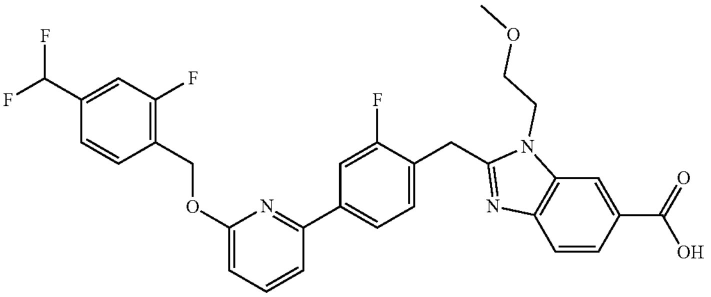 [SMILES: COCCn1c(Cc2ccc(-c3cccc(OCc4ccc(C(F)F)cc4F)n3)cc2F)nc2ccc(C(=O)O)cc21] 2-(4-(6-((4-(difluoromethyl)-2-fluorobenzyl)oxy)pyridin-2-yl)-2-fluorobenzyl)-1-(2-methoxyethyl)-1H-benzo[d]imidazole-6-carboxylic acid: ES/MS m/z 580.2; $^1$H NMR (400 MHz, MeOD) δ 8.57 (d, J = 1.4 Hz, 1H), 8.23 (dd, J = 8.6, 1.4 Hz, 1H), 7.98-7.88 (m, 2H), 7.83-7.74 (m, 2H), 7.66 (t, J = 7.5 Hz, 1H), 7.58-7.48 (m, 2H), 7.39-7.29 (m, 2H), 6.92-6.59 (m, 2H), 5.61 (s, 2H), 4.82 (t, J = 5.0 Hz, 2H), 4.78 (s, 2H), 3.81 (t, J = 4.9 Hz, 2H). Additional peak (s, 3H) obscured by solvent. |
| 151 | 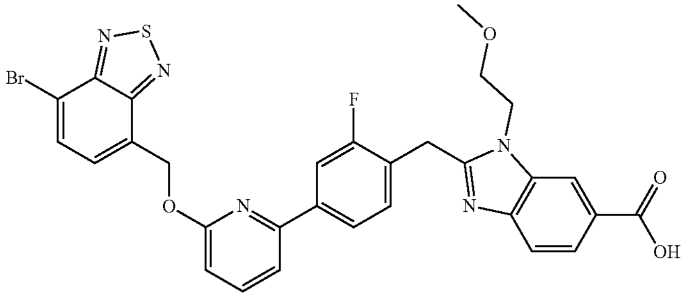 [SMILES: COCCn1c(Cc2ccc(-c3cccc(OCc4ccc(Br)c5nsnc45)n3)cc2F)nc2ccc(C(=O)O)cc21] 2-(4-(6-((7-bromobenzo[c][1,2,5]thiadiazol-4-yl)methoxy)pyridin-2-yl)-2-fluorobenzyl)-1-(2-methoxyethyl)-1H-benzo[d]imidazole-6-carboxylic acid: ES/MS m/z 648.0, 650.0; $^1$H NMR (400 MHz, DMSO) δ 8.22 (d, J = 1.5 Hz, 1H), 8.06 (d, J = 7.5 Hz, 1H), 7.90-7.77 (m, 4H), 7.72 (d, J = 7.5 Hz, 1H), 7.66 (d, J = 7.4 Hz, 1H), 7.60 (d, J = 8.5 Hz, 1H), 7.39 (t, J = 7.9 Hz, 1H), 6.94 (d, J = 8.2 Hz, 1H), 5.94 (s, 2H), 4.57 (t, J = 5.3 Hz, 2H), 4.44 (s, 2H), 3.65 (t, J = 5.1 Hz, 2H), 3.19 (s, 3H). |
| 152 | 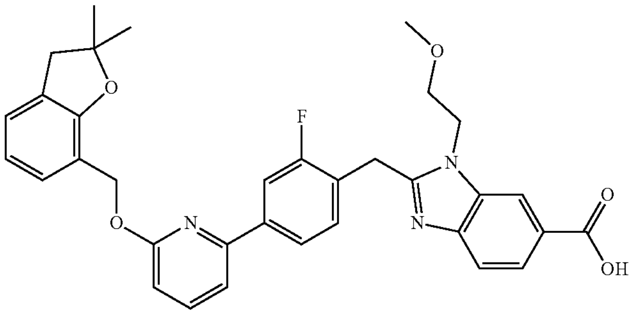 [SMILES: COCCn1c(Cc2ccc(-c3cccc(OCc4cccc5c4OC(C)(C)C5)n3)cc2F)nc2ccc(C(=O)O)cc21] 2-(4-(6-((2,2-dimethyl-2,3-dihydrobenzofuran-7-yl)methoxy)pyridin-2-yl)-2-fluorobenzyl)-1-(2-methoxyethyl)-1H-benzo[d]imidazole-6-carboxylic acid: ES/MS m/z 582.2; $^1$H NMR (400 MHz, MeOD) δ 8.52 (s, 1H), 8.20 (dd, J = 8.6, 1.4 Hz, 1H), 8.00-7.91 (m, 2H), 7.80-7.72 (m, 2H), 7.50 (dd, J = 14.6, 7.5 Hz, 2H), 7.19 (d, J = 7.7 Hz, 1H), 7.09 (d, J = 7.3 Hz, 1H), 6.82 (d, J = 8.3 Hz, 1H), 6.78 (t, J = 7.5 Hz, 1H), 5.42 (s, 2H), 4.78 (t, J = 4.9 Hz, 2H), 4.74 (s, 2H), 3.80 (t, J = 4.9 Hz, 2H), 3.04 (s, 2H), 1.46 (s, 6H). Additional peak (s, 3H) obscured by solvent. |

-continued

| Example | Structure/Name/Characterization |
|---|---|
| 155 | 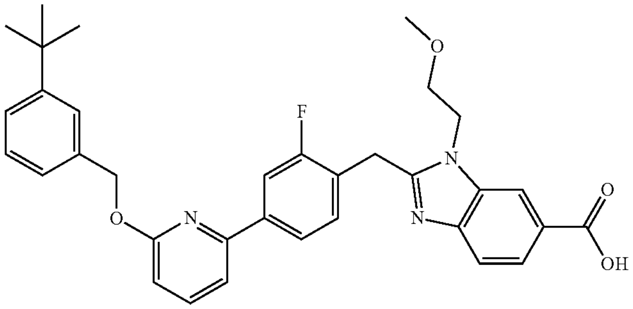 [SMILES: COCCn1c(Cc2ccc(-c3cccc(OCc4cccc(C(C)(C)C)c4)n3)cc2F)nc2ccc(C(=O)O)cc21] 2-(4-(6-((3-(tert-butyl)benzyl)oxy)pyridin-2-yl)-2-fluorobenzyl)-1-(2-methoxyethyl)-1H-benzo[d]imidazole-6-carboxylic acid: ES/MS m/z 568.2; $^1$H NMR (400 MHz, MeOD) δ 8.55 (d, J = 1.6 Hz, 1H), 8.22 (dd, J = 8.6, 1.5 Hz, 1H), 7.99-7.91 (m, 2H), 7.81-7.73 (m, 2H), 7.55-7.46 (m, 3H), 7.37-7.30 (m, 1H), 7.30-7.24 (m, 2H), 6.85 (d, J = 8.2 Hz, 1H), 5.48 (s, 2H), 4.84-4.74 (m, 4H), 3.81 (t, J = 4.9 Hz, 2H), 1.29 (s, 9H). Additional peak (s, 3H) obscured by solvent. |
| 156 | 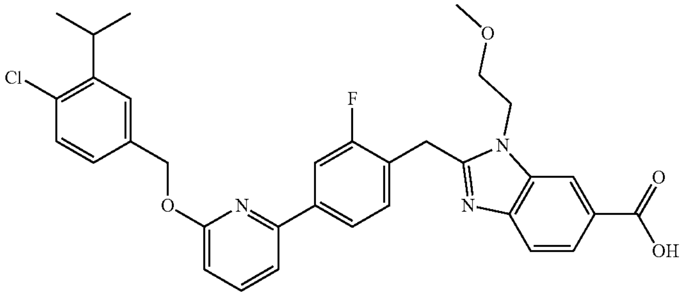 [SMILES: COCCn1c(Cc2ccc(-c3cccc(OCc4ccc(Cl)c(C(C)C)c4)n3)cc2F)nc2ccc(C(=O)O)cc21] 2-(4-(6-((4-chloro-3-isopropylbenzyl)oxy)pyridin-2-yl)-2-fluorobenzyl)-1-(2-methoxyethyl)-1H-benzo[d]imidazole-6-carboxylic acid: ES/MS m/z 588.2; $^1$H NMR (400 MHz, MeOD) δ 8.53 (d, J = 1.5 Hz, 1H), 8.21 (dd, J = 8.6, 1.4 Hz, 1H), 7.94 (s, 1H), 7.92 (d, J = 4.7 Hz, 1H), 7.82-7.73 (m, 2H), 7.56-7.45 (m, 3H), 7.32 (d, J = 8.2 Hz, 1H), 7.26 (dd, J = 8.2, 2.1 Hz, 1H), 6.85 (d, J = 8.2 Hz, 1H), 5.48 (s, 2H), 4.79 (t, J = 5.0 Hz, 2H), 4.75 (s, 2H), 3.80 (t, J = 4.9 Hz, 2H), 3.38 (p, J = 6.9 Hz, 1H), 3.30 (s, 3H), 1.20 (d, J = 6.8 Hz, 6H). |
| 157 | 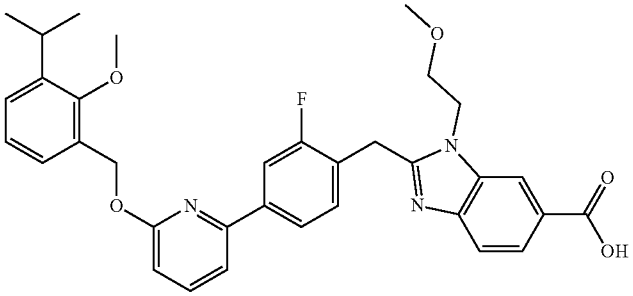 2-(2-fluoro-4-(6-((3-isopropyl-2-methoxybenzyl)oxy)pyridin-2-yl)benzyl)-1-(2-methoxyethyl)-1H-benzo[d]imidazole-6-carboxylic acid: ES/MS m/z 584.2; $^1$H NMR (400 MHz, MeOD) δ 8.56 (d, J = 1.5 Hz, 1H), 8.23 (dd, J = 8.6, 1.5 Hz, 1H), 7.98 (s, 1H), 7.96-7.93 (m, 1H), 7.82-7.73 (m, 2H), 7.56-7.47 (m, 2H), 7.32-7.24 (m, 2H), 7.08 (t, J = 7.6 Hz, 1H), 6.84 (d, J = 8.2 Hz, 1H), 5.55 (s, 2H), 4.85-4.75 (m, 4H), 3.85-3.75 (m, 5H), 3.42-3.33 (m, 1H), 1.23 (d, J = 6.9 Hz, 6H). Additional peak (s, 3H) obscured by solvent. |

-continued

| Example | Structure/Name/Characterization |
|---|---|
| 158 | 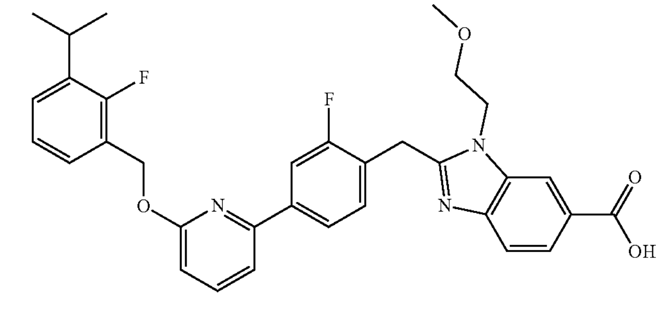 2-(2-fluoro-4-(6-((2-fluoro-3-isopropylbenzyl)oxy)pyridin-2-yl)benzyl)-1-(2-methoxyethyl)-1H-benzo[d]imidazole-6-carboxylic acid: ES/MS m/z 572.2; $^1$H NMR (400 MHz, MeOD) δ 8.55 (d, J = 1.4 Hz, 1H), 8.22 (dd, J = 8.6, 1.4 Hz, 1H), 7.96 (q, J = 1.8 Hz, 1H), 7.93 (dd, J = 6.1, 1.6 Hz, 1H), 7.81-7.73 (m, 2H), 7.56-7.46 (m, 2H), 7.33 (td, J = 7.3, 1.8 Hz, 1H), 7.25 (td, J = 7.5, 1.8 Hz, 1H), 7.09 (t, J = 7.6 Hz, 1H), 6.85 (d, J = 8.2 Hz, 1H), 5.54 (d, J = 1.3 Hz, 2H), 4.80 (t, J = 4.9 Hz, 2H), 4.76 (s, 2H), 3.84-3.77 (m, 2H), 3.29-3.19 (m, 1H), 1.25 (d, J = 6.9 Hz, 6H). Additional peak (s, 3H) obscured by solvent. |
| 227 | 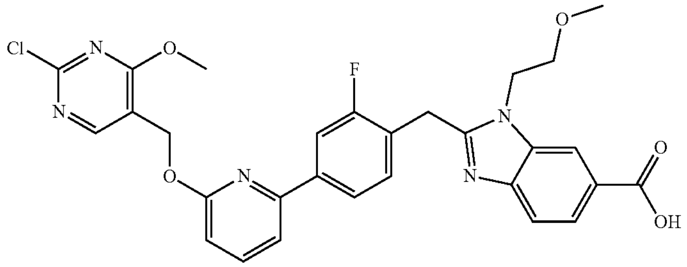 [SMILES: COCCn1c(Cc2ccc(-c3cccc(OCc4cnc(Cl)nc4OC)n3)cc2F)nc2ccc(C(=O)O)cc21] 2-(4-(6-((2-chloro-4-methoxypyrimidin-5-yl)methoxy)pyridin-2-yl)-2-fluorobenzyl)-1-(2-methoxyethyl)-1H-benzo[d]imidazole-6-carboxylic acid: ES/MS m/z 578.3; $^1$H NMR (400 MHz, Methanol-d4) δ 8.46 (s, 1H), 8.40 (s, 1H), 8.09 (d, J = 8.8 Hz, 1H), 7.94-7.84 (m, 3H), 7.82-7.74 (m, 1H), 7.71 (d, J = 8.6 Hz, 1H), 7.55 (d, J = 7.5 Hz, 1H), 7.42 (t, J = 8.1 Hz, 1H), 6.86 (d, J = 8.2 Hz, 1H), 5.48 (d, J = 0.9 Hz, 2H), 4.66 (t, J = 5.0 Hz, 2H), 4.63 (s, 2H), 4.10 (s, 3H), 3.75 (t, J = 5.0 Hz, 2H), 3.28 (s, 3H). |
| 229 | 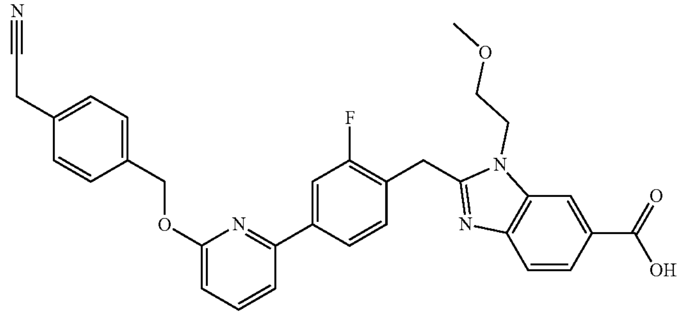 [SMILES: COCCn1c(Cc2ccc(-c3cccc(OCc4ccc(CC#N)cc4)n3)cc2F)nc2ccc(C(=O)O)cc21] 2-(4-(6-((4-(cyanomethyl)benzyl)oxy)pyridin-2-yl)-2-fluorobenzyl)-1-(2-methoxyethyl)-1H-benzo[d]imidazole-6-carboxylic acid: ES/MS 551.2; $^1$H NMR (400 MHz, Methanol-d4) δ 8.57 (s, 1H), 8.30-8.17 (m, 1H), 8.01-7.89 (m, 2H), 7.84-7.71 (m, 2H), 7.60-7.46 (m, 4H), 7.44-7.30 (m, 2H), 6.88 (d, J = 8.2 Hz, 1H), 5.53 (s, 2H), 4.82 (t, J = 5.0 Hz, 1H), 4.78 (s, 2H), 3.91 (s, 2H), 3.83 (t, J = 4.9 Hz, 2H), 3.34 (s, 3H). |

-continued

| Example | Structure/Name/Characterization |
|---|---|
| 234 | 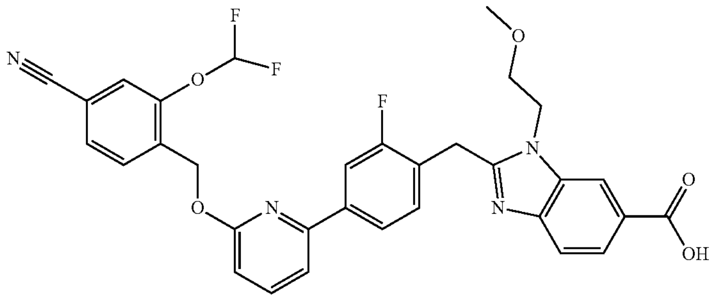 [SMILES: COCCn1c(Cc2ccc(-c3cccc(OCc4ccc(C#N)cc4OC(F)F)n3)cc2F)nc2ccc(C(=O)O)cc21]<br>2-(4-(6-((4-cyano-2-(difluoromethoxy)benzyl)oxy)pyridin-2-yl)-2-fluorobenzyl)-1-(2-methoxyethyl)-1H-benzo[d]imidazole-6-carboxylic acid: ES/MS m/z 603.3; $^1$H NMR (400 MHz, Methanol-d4) δ 8.60-8.53 (m, 1H), 8.23 (dd, J = 8.6, 1.5 Hz, 1H), 7.96-7.71 (m, 5H), 7.66-7.55 (m, 3H), 7.51 (t, J = 7.9 Hz, 1H), 7.14 (t, J = 72.9 Hz, 1H), 6.94 (d, J = 8.1 Hz, 1H), 5.66 (s, 2H), 4.81 (t, J = 4.8 Hz, 2H), 4.77 (s, 2H), 3.82 (t, J = 4.9 Hz, 2H), 3.32 (s, 3H). |
| 238 | 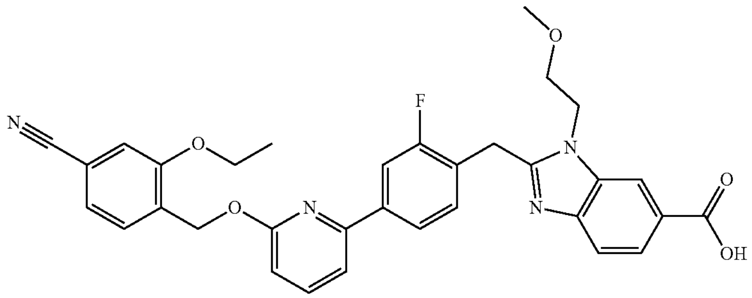 [SMILES: CCOc1cc(C#N)ccc1COc1cccc(-c2ccc(Cc3nc4ccc(C(=O)O)cc4n3CCOC)c(F)c2)n1]<br>2-(4-(6-((4-cyano-2-ethoxybenzyl)oxy)pyridin-2-yl)-2-fluorobenzyl)-1-(2-methoxyethyl)-1H-benzo[d]imidazole-6-carboxylic acid: ES/MS m/z 581.2; $^1$H NMR (400 MHz, Methanol-d4) δ 8.49 (d, J = 1.3 Hz, 1H), 8.17 (dd, J = 8.6, 1.4 Hz, 1H), 7.91-7.82 (m, 2H), 7.79 (dd, J = 8.2, 7.5 Hz, 1H), 7.74 (d, J = 8.6 Hz, 1H), 7.54 (dd, J = 7.6, 2.8 Hz, 2H), 7.45 (t, J = 8.0 Hz, 1H), 7.33 (d, J = 1.4 Hz, 1H), 7.28 (dd, J = 7.8, 1.4 Hz, 1H), 6.89 (d, J = 8.2 Hz, 1H), 5.59 (s, 2H), 4.75 (t, J = 5.0 Hz, 2H), 4.70 (s, 2H), 4.18 (q, J = 7.0 Hz, 2H), 3.78 (t, J = 4.9 Hz, 2H), 3.29 (s, 3H), 1.44 (t, J = 7.0 Hz, 3H). |
| 241 | 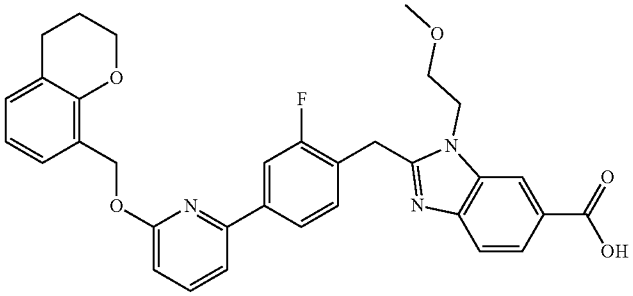 [SMILES: COCCn1c(Cc2ccc(-c3cccc(OCc4cccc5c4OCCC5)n3)cc2F)nc2ccc(C(=O)O)cc21]<br>2-(4-(6-(chroman-8-ylmethoxy)pyridin-2-yl)-2-fluorobenzyl)-1-(2-methoxyethyl)-1H-benzo[d]imidazole-6-carboxylic acid: ES/MS m/z 568.2; $^1$H NMR (400 MHz, Methanol-d4) δ 8.55 (d, J = 1.1 Hz, 1H), 8.23 (dd, J = 8.6, 1.4 Hz, 1H), 7.98 (s, 1H), 7.96-7.91 (m, 1H), 7.81-7.72 (m, 2H), 7.56-7.44 (m, 2H), 7.24-7.17 (m, 1H), 7.00 (d, J = 7.7 Hz, 1H), 6.85 (d, J = 8.2 Hz, 1H), 6.79 (t, J = 7.5 Hz, 1H), 5.47 (s, 2H), 4.81 (t, J = 5.0 Hz, 2H), 4.77 (s, 2H), 4.30-4.23 (m, 2H), 3.82 (t, J = 4.9 Hz, 2H), 3.34 (s, 13H), 2.83 (t, J = 6.5 Hz, 2H), 2.06-1.98 (m, 2H). |

-continued

| Example | Structure/Name/Characterization |
| --- | --- |
| 243 | 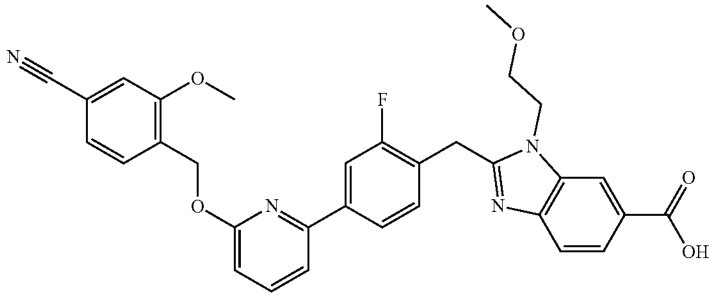 [SMILES: COCCn1c(Cc2ccc(-c3cccc(OCc4ccc(C#N)cc4OC)n3)cc2F)nc2ccc(C(=O)O)cc21] 2-(4-(6-((4-cyano-2-methoxybenzyl)oxy)pyridin-2-yl)-2-fluorobenzyl)-1-(2-methoxyethyl)-1H-benzo[d]imidazole-6-carboxylic acid: ES/MS m/z 567.3; $^1$H NMR (400 MHz, DMSO-d6) δ 8.27 (d, J = 1.5 Hz, 1H), 7.88-7.80 (m, 4H), 7.64 (dd, J = 8.0, 5.6 Hz, 2H), 7.60-7.52 (m, 2H), 7.50-7.40 (m, 2H), 6.93 (d, J = 8.2 Hz, 1H), 5.52 (s, 2H), 4.67-4.58 (m, 2H), 4.50 (s, 2H), 3.92 (s, 3H), 3.67 (t, J = 5.1 Hz, 2H), 3.20 (s, 3H). |
| 247 | 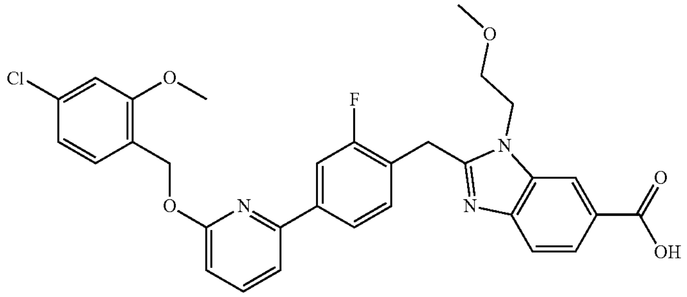 [SMILES: COCCn1c(Cc2ccc(-c3cccc(OCc4ccc(Cl)cc4OC)n3)cc2F)nc2ccc(C(=O)O)cc21] 2-(4-(6-((4-chloro-2-methoxybenzyl)oxy)pyridin-2-yl)-2-fluorobenzyl)-1-(2-methoxyethyl)-1H-benzo[d]imidazole-6-carboxylic acid: ES/MS m/z 576.1; $^1$H NMR (400 MHz, Methanol-d4) δ 8.54 (t, J = 1.0 Hz, 1H), 8.21 (dd, J = 8.6, 1.4 Hz, 1H), 7.99-7.88 (m, 2H), 7.83-7.71 (m, 2H), 7.52 (dd, J = 18.1, 7.6 Hz, 2H), 7.39 (d, J = 8.1 Hz, 1H), 7.05 (d, J = 1.9 Hz, 1H), 6.95 (dd, J = 8.1, 2.0 Hz, 1H), 6.86 (d, J = 8.2 Hz, 1H), 5.49 (s, 2H), 4.79 (t, J = 5.0 Hz, 2H), 4.75 (s, 2H), 3.91 (s, 3H), 3.85-3.76 (m, 2H), 3.32 (s, 3H). |
| 248 | 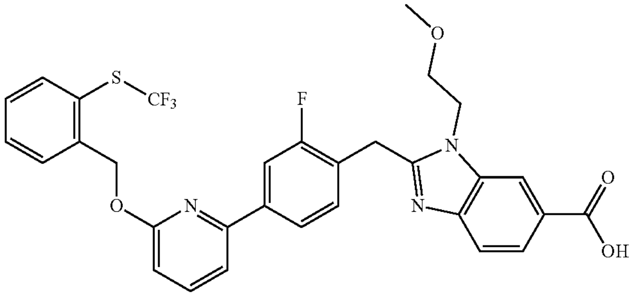 [SMILES: COCCn1c(Cc2ccc(-c3cccc(OCc4ccccc4SC(F)(F)F)n3)cc2F)nc2ccc(C(=O)O)cc21] 2-(2-fluoro-4-(6-((2-((trifluoromethyl)thio)benzyl)oxy)pyridin-2-yl)benzyl)-1-(2-methoxyethyl)-1H-benzo[d]imidazole-6-carboxylic acid: ES/MS m/z 612.1; $^1$H NMR (400 MHz, Methanol-d4) δ 8.53 (d, J = 1.2 Hz, 1H), 8.21 (dd, J = 8.6, 1.5 Hz, 1H), 7.95-7.86 (m, 2H), 7.85-7.75 (m, 3H), 7.72 (dd, J = 7.8, 1.5 Hz, 1H), 7.60 (dd, J = 7.6, 1.4 Hz, 1H), 7.56 (d, J = 7.3 Hz, 1H), 7.53-7.43 (m, 2H), 6.89 (d, J = 8.2 Hz, 1H), 5.78 (s, 2H), 4.79 (t, J = 5.0 Hz, 2H), 4.75 (s, 2H), 3.85-3.74 (m, 2H), 3.31 (s, 3H). |

-continued

| Example | Structure/Name/Characterization |
|---|---|
| 250 | 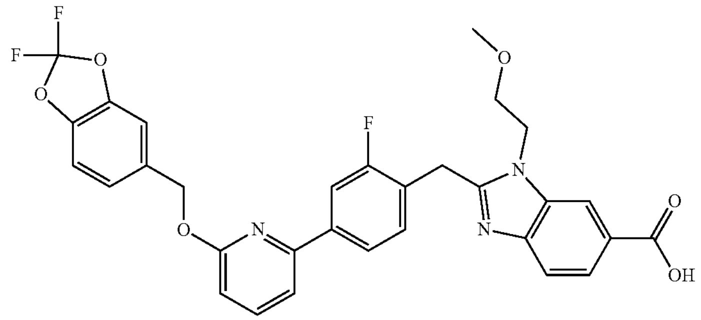 [SMILES: COCCn1c(Cc2ccc(-c3cccc(OCc4ccc5c(c4)OC(F)(F)O5)n3)cc2F)nc2ccc(C(=O)O)cc21] 2-(4-(6-((2,2-difluorobenzo[d][1,3]dioxol-5-yl)methoxy)pyridin-2-yl)-2-fluorobenzyl)-1-(2-methoxyethyl)-1H-benzo[d]imidazole-6-carboxylic acid: ES/MS m/z 592.1; $^1$H NMR (400 MHz, DMSO-d6) δ 8.32 (d, J = 1.5 Hz, 1H), 7.97-7.94 (m, 1H), 7.93 (s, 1H), 7.89 (dd, J = 8.5, 1.5 Hz, 1H), 7.85 (t, J = 7.8 Hz, 1H), 7.67 (s, 1H), 7.65 (s, 1H), 7.57 (d, J = 1.5 Hz, 1H), 7.47 (t, J = 7.9 Hz, 1H), 7.42 (d, J = 8.2 Hz, 1H), 7.37 (dd, J = 8.3, 1.6 Hz, 1H), 6.90 (d, J = 8.1 Hz, 1H), 5.49 (s, 2H), 4.66 (t, J = 5.1 Hz, 2H), 4.55 (s, 2H), 3.68 (t, J = 5.0 Hz, 2H), 3.21 (s, 3H). |
| 251 | 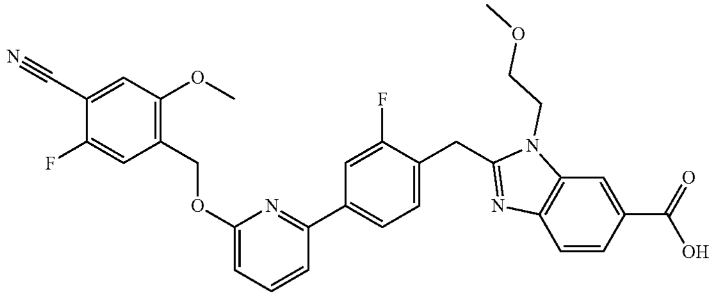 [SMILES: COCCn1c(Cc2ccc(-c3cccc(OCc4cc(F)c(C#N)cc4OC)n3)cc2F)nc2ccc(C(=O)O)cc21] 2-(4-(6-((4-cyano-5-fluoro-2-methoxybenzyl)oxy)pyridin-2-yl)-2-fluorobenzyl)-1-(2-methoxyethyl)-1H-benzo[d]imidazole-6-carboxylic acid: ES/MS m/z 585.2; $^1$H NMR (400 MHz, Methanol-d4) δ 8.51 (s, 1H), 8.24-8.15 (m, 1H), 7.93-7.80 (m, 3H), 7.76 (d, J = 8.5 Hz, 1H), 7.58 (d, J = 7.3 Hz, 1H), 7.47 (t, J = 7.8 Hz, 1H), 7.44-7.33 (m, 2H), 6.96 (d, J = 8.1 Hz, 1H), 5.58 (s, 2H), 4.76 (s, 2H), 4.72 (s, 2H), 3.98 (s, 3H), 3.80 (t, J = 4.8 Hz, 2H), 3.31 (s, 3H). |
| 252 | 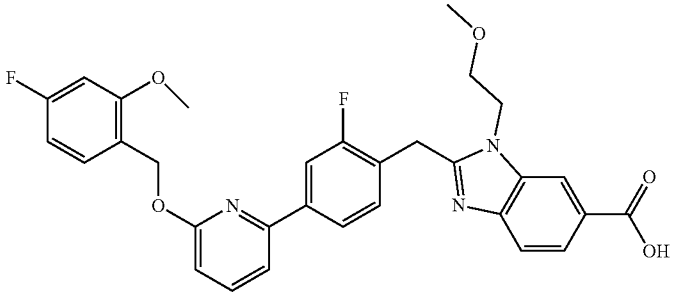 [SMILES: COCCn1c(Cc2ccc(-c3cccc(OCc4ccc(F)cc4OC)n3)cc2F)nc2ccc(C(=O)O)cc21] 2-(2-fluoro-4-(6-((4-fluoro-2-methoxybenzyl)oxy)pyridin-2-yl)benzyl)-1-(2-methoxyethyl)-1H-benzo[d]imidazole-6-carboxylic acid: ES/MS m/z 560.2; $^1$H NMR (400 MHz, DMSO-d6) δ 8.33 (d, J = 1.5 Hz, 1H), 7.96-7.87 (m, 3H), 7.82 (dd, J = 8.2, 7.5 Hz, 1H), 7.70-7.59 (m, 2H), 7.52-7.42 (m, 2H), 6.97 (dd, J = 11.4, 2.4 Hz, 1H), 6.87 (d, J = 8.2 Hz, 1H), 6.77 (td, J = 8.5, 2.5 Hz, 1H), 5.42 (s, 2H), 4.67 (t, J = 5.0 Hz, 2H), 4.55 (s, 2H), 3.85 (s, 3H), 3.69 (t, J = 5.0 Hz, 2H), 3.21 (d, J = 2.0 Hz, 3H). |

-continued

| Example | Structure/Name/Characterization |
| --- | --- |
| 256 | 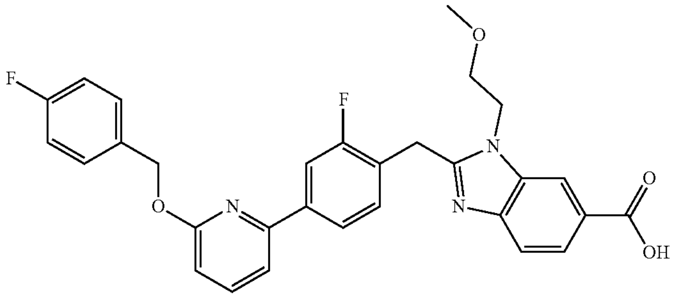 [SMILES: COCCn1c(Cc2ccc(-c3cccc(OCc4ccc(F)cc4)n3)cc2F)nc2ccc(C(=O)O)cc21] 2-(2-fluoro-4-(6-((4-fluorobenzyl)oxy)pyridin-2-yl)benzyl)-1-(2-methoxyethyl)-1H-benzo[d]imidazole-6-carboxylic acid: ES/MS m/z 530.2; $^1$H NMR (400 MHz, Methanol-d4) δ 8.57 (d, J = 1.3 Hz, 1H), 8.24 (dd, J = 8.6, 1.4 Hz, 1H), 8.01-7.91 (m, 2H), 7.78 (dt, J = 8.2, 3.5 Hz, 2H), 7.59-7.46 (m, 4H), 7.10 (t, J = 8.8 Hz, 2H), 6.86 (d, J = 8.2 Hz, 1H), 5.49 (s, 2H), 4.83 (t, J = 5.0 Hz, 2H), 4.79 (s, 2H), 3.89-3.78 (m, 2H), 3.32 (s, 3H). |
| 262 | 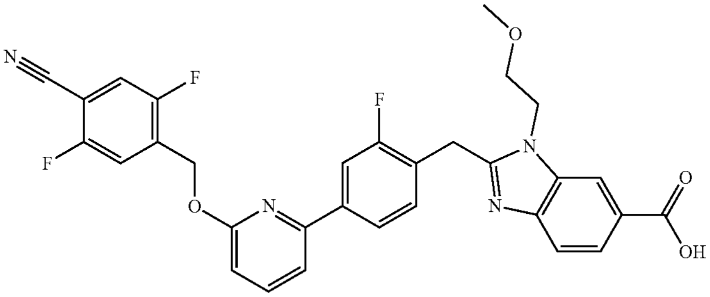 [SMILES: COCCn1c(Cc2ccc(-c3cccc(OCc4cc(F)c(C#N)cc4F)n3)cc2F)nc2ccc(C(=O)O)cc21] 2-(4-(6-((4-cyano-2,5-difluorobenzyl)oxy)pyridin-2-yl)-2-fluorobenzyl)-1-(2-methoxyethyl)-1H-benzo[d]imidazole-6-carboxylic acid: ES/MS m/z 573.2; $^1$H NMR (400 MHz, DMSO-d6) δ 8.27 (d, J = 1.6 Hz, 1H), 8.06 (dd, J = 9.2, 5.2 Hz, 1H), 7.95-7.81 (m, 4H), 7.75 (dd, J = 9.4, 5.6 Hz, 1H), 7.69 (d, J = 7.5 Hz, 1H), 7.63 (d, J = 8.4 Hz, 1H), 7.45 (t, J = 8.0 Hz, 1H), 6.96 (d, J = 8.2 Hz, 1H), 5.60 (s, 2H), 4.62 (t, J = 5.1 Hz, 2H), 4.50 (s, 2H), 3.67 (t, J = 5.1 Hz, 2H), 3.21 (s, 3H). |
| 265 | 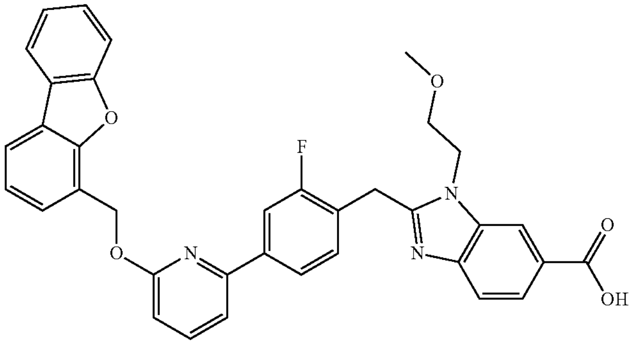 [SMILES: COCCn1c(Cc2ccc(-c3cccc(OCc4cccc5c4oc4ccccc45)n3)cc2F)nc2ccc(C(=O)O)cc21] 2-(4-(6-(dibenzo[b,d]furan-4-ylmethoxy)pyridin-2-yl)-2-fluorobenzyl)-1-(2-methoxyethyl)-1H-benzo[d]imidazole-6-carboxylic acid: ES/MS m/z 602.2; $^1$H NMR (400 MHz, Methanol-d4) δ 8.57 (s, 1H), 8.29-8.20 (m, 1H), 8.07-7.94 (m, 2H), 7.92-7.83 (m, 1H), 7.83-7.76 (m, 2H), 7.67-7.58 (m, 2H), 7.53 (d, J = 7.5 Hz, 1H), 7.40-7.24 (m, 4H), 6.91 (d, J = 8.4 Hz, 1H), 5.90 (s, 2H), 4.77 (t, J = 4.9 Hz, 2H), 4.72 (d, J = 4.2 Hz, 2H), 3.77 (t, J = 4.8 Hz, 2H), 3.29 (s, 3H). |

-continued

| Example | Structure/Name/Characterization |
| --- | --- |
| 266 | 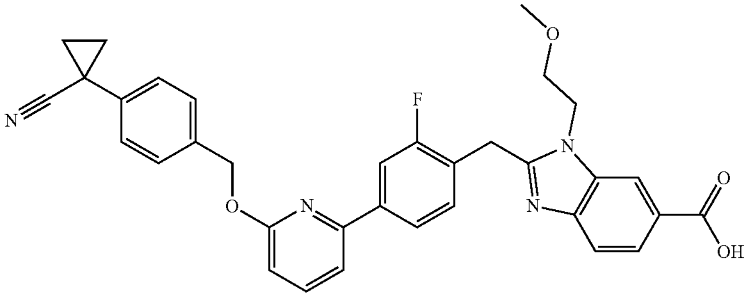 [SMILES: COCCn1c(Cc2ccc(-c3cccc(OCc4ccc(C5(C#N)CC5)cc4)n3)cc2F)nc2ccc(C(=O)O)cc21] 2-(4-(6-((4-(1-cyanocyclopropyl)benzyl)oxy)pyridin-2-yl)-2-fluorobenzyl)-1-(2-methoxyethyl)-1H-benzo[d]imidazole-6-carboxylic acid: ES/MS m/z 577.2; $^1$H NMR (400 MHz, Methanol-d4) δ 8.62-8.47 (m, 1H), 8.30-8.12 (m, 1H), 7.99-7.87 (m, 2H), 7.78 (d, J = 8.3 Hz, 2H), 7.59-7.47 (m, 4H), 7.35 (dt, J = 8.5, 2.4 Hz, 2H), 6.86 (d, J = 8.2 Hz, 1H), 5.51 (s, 2H), 4.80 (t, J = 4.9 Hz, 2H), 4.76 (s, 2H), 3.82 (t, J = 4.8 Hz, 2H), 3.32 (s, 3H), 1.72 (q, J = 4.8 Hz, 2H), 1.48 (q, J = 4.9 Hz, 2H). |
| 348 | 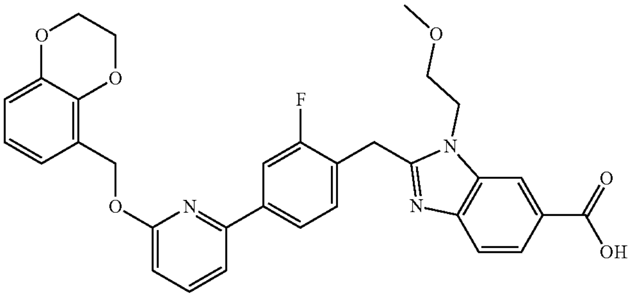 [SMILES: COCCn1c(Cc2ccc(-c3cccc(OCc4cccc5c4OCCO5)n3)cc2F)nc2ccc(C(=O)O)cc21] 2-(4-(6-((2,3-dihydrobenzo[b][1,4]dioxin-5-yl)methoxy)pyridin-2-yl)-2-fluorobenzyl)-1-(2-methoxyethyl)-1H-benzo[d]imidazole-6-carboxylic acid: ES/MS 570.3; $^1$H NMR (400 MHz, Methanol-d4) δ 8.60 (d, J = 1.4 Hz, 1H), 8.26 (dd, J = 8.6, 1.4 Hz, 1H), 8.03-7.99 (m, 1H), 7.98 (s, 1H), 7.79 (t, J = 8.5 Hz, 2H), 7.60-7.48 (m, 2H), 6.98 (dd, J = 5.4, 3.8 Hz, 1H), 6.85 (d, J = 8.2 Hz, 1H), 6.83-6.75 (m, 2H), 5.49 (s, 2H), 4.85 (t, J = 5.0 Hz, 2H), 4.81 (s, 2H), 4.39-4.29 (m, 2H), 4.30-4.23 (m, 2H), 3.84 (t, J = 4.9 Hz, 2H), 3.33 (s, 3H). |
| 357 | 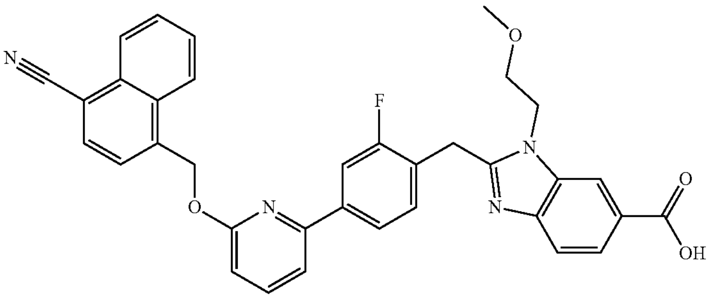 [SMILES: COCCn1c(Cc2ccc(-c3cccc(OCc4ccc(C#N)c5ccccc45)n3)cc2F)nc2ccc(C(=O)O)cc21] 2-(4-(6-((4-cyanonaphthalen-1-yl)methoxy)pyridin-2-yl)-2-fluorobenzyl)-1-(2-methoxyethyl)-1H-benzo[d]imidazole-6-carboxylic acid: ES/MS m/z 587.3; $^1$H NMR (400 MHz, DMSO-d6) δ 8.44-8.34 (m, 1H), 8.29 (d, J = 1.5 Hz, 1H), 8.24-8.15 (m, 2H), 7.95-7.76 (m, 7H), 7.68 (d, J = 7.5 Hz, 1H), 7.64 (d, J = 8.5 Hz, 1H), 7.43 (t, J = 7.9 Hz, 1H), 6.96 (d, J = 8.2 Hz, 1H), 6.07 (s, 2H), 4.63 (t, J = 5.1 Hz, 2H), 4.51 (s, 2H), 3.67 (t, J = 5.0 Hz, 2H), 3.20 (s, 3H). |

-continued

| Example | Structure/Name/Characterization |
|---|---|
| 362 | 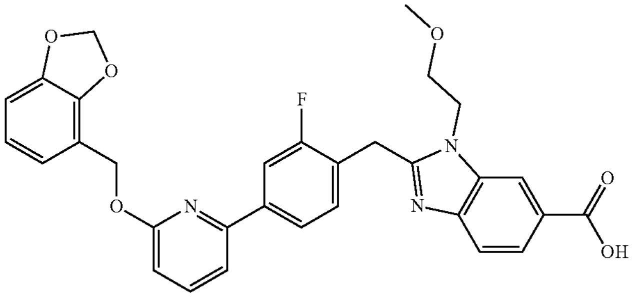 [SMILES: COCCn1c(Cc2ccc(-c3cccc(OCc4cccc5c4OCO5)n3)cc2F)nc2ccc(C(=O)O)cc21] 2-(4-(6-(benzo[d][1,3]dioxol-4-ylmethoxy)pyridin-2-yl)-2-fluorobenzyl)-1-(2-methoxyethyl)-1H-benzo[d]imidazole-6-carboxylic acid: ES/MS m/z 556.4; $^{1}$H NMR (400 MHz, Methanol-d4) δ 8.57 (t, J = 1.0 Hz, 1H), 8.24 (dd, J = 8.6, 1.4 Hz, 1H), 8.08-7.93 (m, 2H), 7.84-7.74 (m, 2H), 7.59-7.46 (m, 2H), 6.97 (dd, J = 7.6, 1.5 Hz, 1H), 6.91-6.73 (m, 3H), 6.01 (s, 2H), 5.49 (s, 2H), 4.83 (t, J = 5.0 Hz, 2H), 4.79 (s, 2H), 3.83 (t, J = 5.4, 4.4 Hz, 2H), 3.32 (s, 3H). |
| 435 | 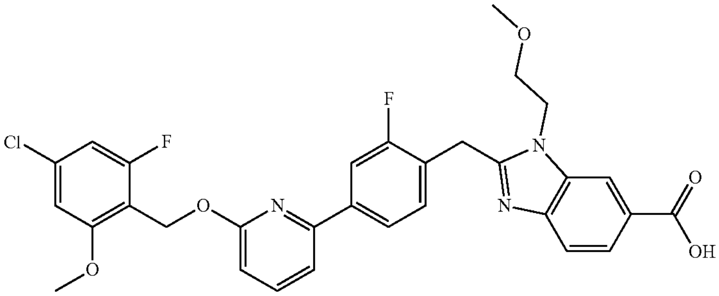 [SMILES: COCCn1c(Cc2ccc(-c3cccc(OCc4c(F)cc(Cl)cc4OC)n3)cc2F)nc2ccc(C(=O)O)cc21] 2-(4-(6-((4-chloro-2-fluoro-6-methoxybenzyl)oxy)pyridin-2-yl)-2-fluorobenzyl)-1-(2-methoxyethyl)-1H-benzo[d]imidazole-6-carboxylic acid: ES/MS 594.3; $^{1}$H NMR (400 MHz, Methanol-d4) δ 8.57 (d, J = 1.5 Hz, 1H), 8.24 (dd, J = 8.6, 1.4 Hz, 1H), 8.09-7.97 (m, 2H), 7.83-7.69 (m, 2H), 7.61-7.49 (m, 2H), 6.99-6.93 (m, 1H), 6.88 (dd, J = 9.2, 1.9 Hz, 1H), 6.77 (d, J = 8.2 Hz, 1H), 5.50 (s, 2H), 4.83 (t, J = 5.0 Hz, 2H), 4.80 (s, 2H), 3.90 (s, 3H), 3.83 (t, J = 4.9 Hz, 2H), 3.32 (s, 3H). |
| 470 | 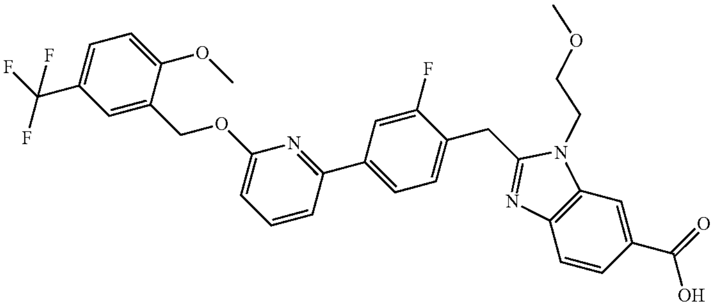 [SMILES: COCCn1c(Cc2ccc(-c3cccc(OCc4cc(C(F)(F)F)ccc4OC)n3)cc2F)nc2ccc(C(=O)O)cc21] 2-(2-fluoro-4-(6-((2-methoxy-5-(trifluoromethyl)benzyl)oxy)pyridin-2-yl)benzyl)-1-(2-methoxyethyl)-1H-benzo[d]imidazole-6-carboxylic acid: ES/MS m/z 610.2; $^{1}$H NMR (400 MHz, Acetonitrile-d3) δ 8.33 (s, 1H), 8.02 (s, 1H), 7.85 (d, J = 10.1 Hz, 2H), 7.76 (s, 2H), 7.73-7.53 (m, 2H), 7.52-7.35 (m, 2H), 7.23-7.06 (m, 1H), 6.86 (d, J = 8.4 Hz, 1H), 5.54 (d, J = 3.4 Hz, 2H), 4.56 (d, J = 4.7 Hz, 4H), 3.94 (d, J = 2.9 Hz, 3H), 3.72 (d, J = 5.2 Hz, 2H), 3.24 (t, J = 2.7 Hz, 3H), 2.87 (s, 1H). |

-continued

| Example | Structure/Name/Characterization |
|---|---|
| 473 | 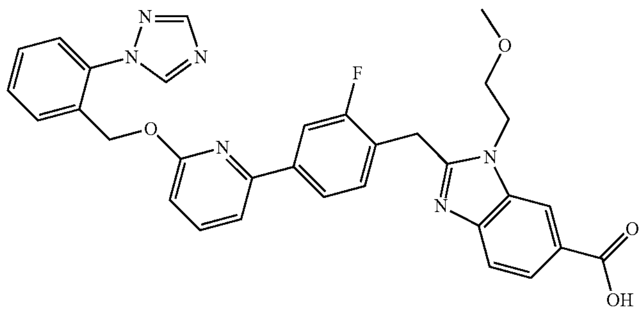 [SMILES: COCCn1c(Cc2ccc(-c3cccc(OCc4ccccc4-n4cncn4)n3)cc2F)nc2ccc(C(=O)O)cc21] 2-(4-(6-((2-(1H-1,2,4-triazol-1-yl)benzyl)oxy)pyridin-2-yl)-2-fluorobenzyl)-1-(2-methoxyethyl)-1H-benzo[d]imidazole-6-carboxylic acid: ES/MS m/z 578.3; $^1$H NMR (400 MHz, Methanol-d4) δ 8.68 (s, 1H), 8.30 (s, 1H), 8.07 (s, 1H), 7.98 (d, J = 8.7 Hz, 1H), 7.77-7.52 (m, 6H), 7.52-7.31 (m, 4H), 6.69 (d, J = 8.2 Hz, 1H), 6.22 (s, 1H), 5.41 (d, J = 5.5 Hz, 2H), 4.61 (d, J = 11.9 Hz, 1H), 3.67 (s, 2H), 3.59 (s, 1H), 3.06 (s, 3H). |
| 474 | 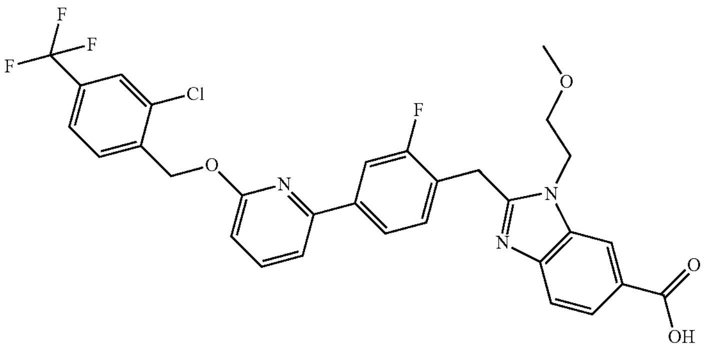 [SMILES: COCCn1c(Cc2ccc(-c3cccc(OCc4ccc(C(F)(F)F)cc4Cl)n3)cc2F)nc2ccc(C(=O)O)cc21] 2-(4-(6-((2-chloro-4-(trifluoromethyl)benzyl)oxy)pyridin-2-yl)-2-fluorobenzyl)-1-(2-methoxyethyl)-1H-benzo[d]imidazole-6-carboxylic acid: ES/MS m/z 613.8; $^1$H NMR (400 MHz, Methanol-d4) δ 8.28 (s, 1H), 8.09 (s, 1H), 7.86 (d, J = 8.5 Hz, 1H), 7.82-7.66 (m, 4H), 7.61 (d, J = 8.1 Hz, 1H), 7.50 (d, J = 7.6 Hz, 1H), 7.42 (t, J = 7.8 Hz, 2H), 7.32 (d, J = 8.1 Hz, 1H), 6.91 (d, J = 8.2 Hz, 1H), 5.65 (s, 2H), 5.46 (s, 1H), 4.39 (d, J = 19.6 Hz, 2H), 3.96 (dd, J = 13.7, 6.6 Hz, 1H), 3.76 (s, 1H), 3.59 (s, 1H), 3.12 (s, 3H). |
| 478 | 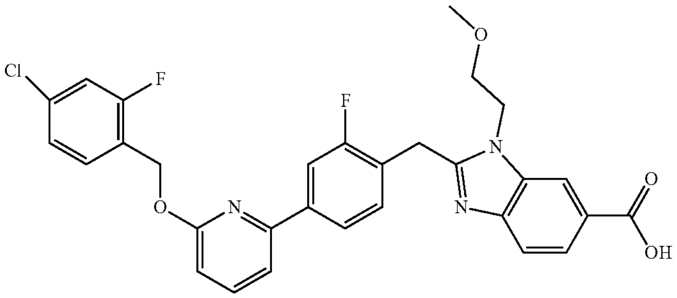 [SMILES: COCCn1c(Cc2ccc(-c3cccc(OCc4ccc(Cl)cc4F)n3)cc2F)nc2ccc(C(=O)O)cc21] 2-(4-(6-((4-chloro-2-fluorobenzyl)oxy)pyridin-2-yl)-2-fluorobenzyl)-1-(2-methoxyethyl)-1H-benzo[d]imidazole-6-carboxylic acid: ES/MS m/z 564.2; $^1$H NMR (400 MHz, Methanol-d4) δ 8.56 (t, J = 1.0 Hz, 1H), 8.23 (dd, J = 8.5, 1.5 Hz, 1H), 8.01-7.89 (m, 2H), 7.85-7.72 (m, 2H), 7.61-7.46 (m, 3H), 7.23 (ddd, J = 12.5, 8.9, 2.1 Hz, 2H), 6.87 (d, J = 8.0 Hz, 1H), 5.55 (s, 2H), 4.84-4.79 (m, 3H), 4.78 (s, 2H), 3.86-3.74 (m, 2H), 3.33 (s, 4H). |

-continued

| Example | Structure/Name/Characterization |
|---|---|
| 481 | 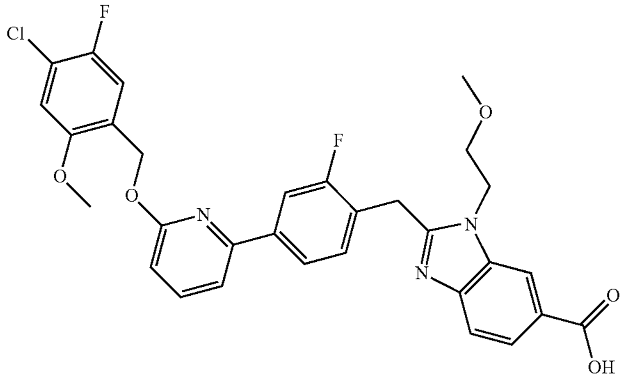 [SMILES: COCCn1c(Cc2ccc(-c3cccc(OCc4cc(F)c(Cl)cc4OC)n3)cc2F)nc2ccc(C(=O)O)cc21] 2-(4-(6-((4-chloro-5-fluoro-2-methoxybenzyl)oxy)pyridin-2-yl)-2-fluorobenzyl)-1-(2-methoxyethyl)-1H-benzo[d]imidazole-6-carboxylic acid: ES/MS m/z 594.1; $^1$H NMR (400 MHz, Acetonitrile-d3) δ 8.42 (s, 1H), 8.11 (dd, J = 8.6, 1.4 Hz, 1H), 7.87 (d, J = 11.8 Hz, 2H), 7.83-7.70 (m, 2H), 7.49 (dd, J = 19.8, 7.7 Hz, 2H), 7.33 (d, J = 9.7 Hz, 1H), 7.11 (d, J = 6.2 Hz, 1H), 6.87 (d, J = 8.2 Hz, 1H), 5.47 (s, 2H), 4.69-4.58 (m, 4H), 3.87 (s, 3H), 3.75 (t, J = 4.9 Hz, 2H), 3.25 (s, 3H). |
| 493 | 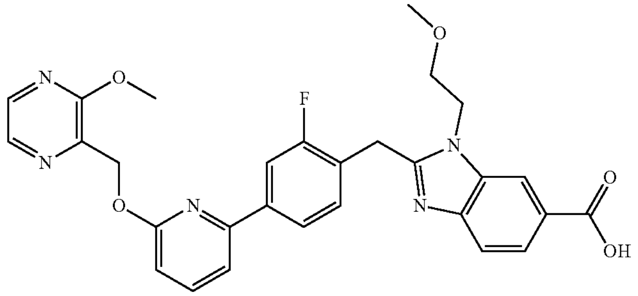 [SMILES: COCCn1c(Cc2ccc(-c3cccc(OCc4nccnc4OC)n3)cc2F)nc2ccc(C(=O)O)cc21] 2-(2-fluoro-4-(6-((3-methoxypyrazin-2-yl)methoxy)pyridin-2-yl)benzyl)-1-(2-methoxyethyl)-1H-benzo[d]imidazole-6-carboxylic acid: ES/MS m/z 544.2; $^1$H NMR (400 MHz, Methanol-d4) δ 8.50 (d, J = 1.2 Hz, 1H), 8.22-8.09 (m, 2H), 8.06 (d, J = 2.8 Hz, 1H), 7.89-7.72 (m, 4H), 7.53 (d, J = 7.4 Hz, 1H), 7.45 (t, J = 8.0 Hz, 1H), 6.90 (d, J = 8.2 Hz, 1H), 5.61 (s, 2H), 4.76 (t, J = 5.0 Hz, 2H), 4.71 (s, 2H), 4.09 (s, 3H), 3.79 (t, J = 4.9 Hz, 2H), 3.31 (s, 3H). |
| 495 | 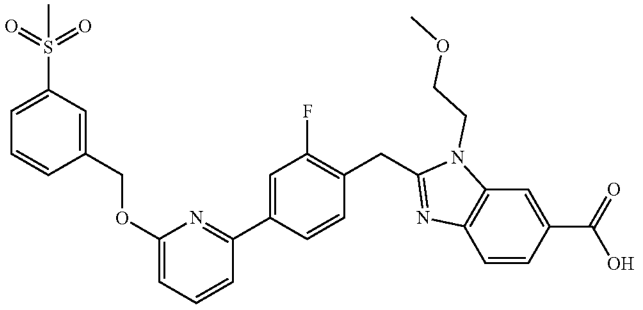 [SMILES: COCCn1c(Cc2ccc(-c3cccc(OCc4cccc(S(C)(=O)=O)c4)n3)cc2F)nc2ccc(C(=O)O)cc21] 2-(2-fluoro-4-(6-((3-(methylsulfonyl)benzyl)oxy)pyridin-2-yl)benzyl)-1-(2-methoxyethyl)-1H-benzo[d]imidazole-6-carboxylic acid: ES/MS m/z 590.2; $^1$H NMR (400 MHz, Methanol-d4) δ 8.56 (d, J = 1.2 Hz, 1H), 8.23 (dd, J = 8.6, 1.4 Hz, 1H), 8.13 (s, 1H), 7.97-7.75 (m, 6H), 7.65 (t, J = 7.8 Hz, 1H), 7.59-7.47 (m, 2H), 6.92 (d, J = 8.2 Hz, 1H), 5.63 (s, 2H), 4.81 (t, J = 5.0 Hz, 2H), 4.77 (s, 2H), 3.82 (t, J = 4.9 Hz, 2H), 3.08 (s, 3H). one methyl group is under solvent |

-continued

| Example | Structure/Name/Characterization |
|---|---|
| 496 | 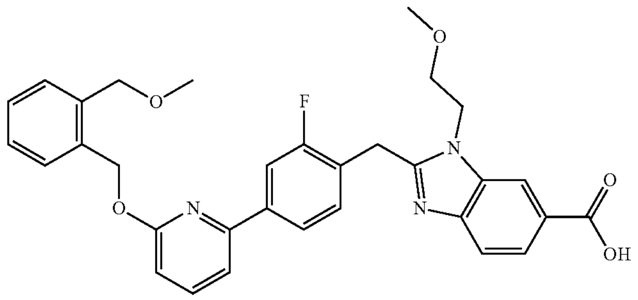 [SMILES: COCCn1c(Cc2ccc(-c3cccc(OCc4ccccc4COC)n3)cc2F)nc2ccc(C(=O)O)cc21]<br>2-(2-fluoro-4-(6-((2-(methoxymethyl)benzyl)oxy)pyridin-2-yl)benzyl)-1-(2-methoxyethyl)-1H-benzo[d]imidazole-6-carboxylic acid: ES/MS m/z 556.2; $^1H$ NMR (400 MHz, Methanol-d4) δ 8.53 (d, J = 1.3 Hz, 1H), 8.21 (dd, J = 8.7, 1.5 Hz, 1H), 7.98-7.90 (m, 2H), 7.84-7.74 (m, 2H), 7.57-7.46 (m, 3H), 7.42 (dd, J = 5.3, 3.7 Hz, 1H), 7.37-7.27 (m, 2H), 6.87 (d, J = 8.0 Hz, 1H), 5.61 (s, 2H), 4.79 (t, J = 5.0 Hz, 2H), 4.75 (s, 2H), 4.64 (s, 2H), 3.81 (t, J = 4.9 Hz, 2H), 3.39 (s, 3H), 3.32 (s, 3H). |
| 499 | 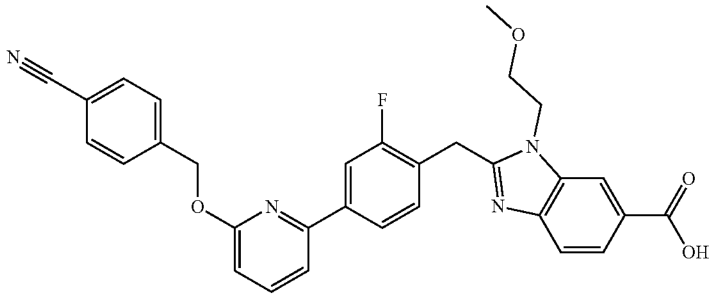 [SMILES: COCCn1c(Cc2ccc(-c3cccc(OCc4ccc(C#N)cc4)n3)cc2F)nc2ccc(C(=O)O)cc21]<br>2-(4-(6-((4-cyanobenzyl)oxy)pyridin-2-yl)-2-fluorobenzyl)-1-(2-methoxyethyl)-1H-benzo[d]imidazole-6-carboxylic acid: ES/MS m/z 537.2; $^1H$ NMR (400 MHz, Methanol-d4) δ 8.51 (d, J = 1.3 Hz, 1H), 8.19 (dd, J = 8.6, 1.5 Hz, 1H), 7.94-7.71 (m, 6H), 7.67 (d, J = 8.1 Hz, 2H), 7.56 (d, J = 7.5 Hz, 1H), 7.47 (t, J = 7.9 Hz, 1H), 6.92 (d, J = 8.1 Hz, 1H), 5.61 (s, 2H), 4.77 (t, J = 5.0 Hz, 2H), 4.72 (s, 2H), 3.80 (t, J = 4.9 Hz, 2H), 3.31 (s, 3H). |
| 500 | 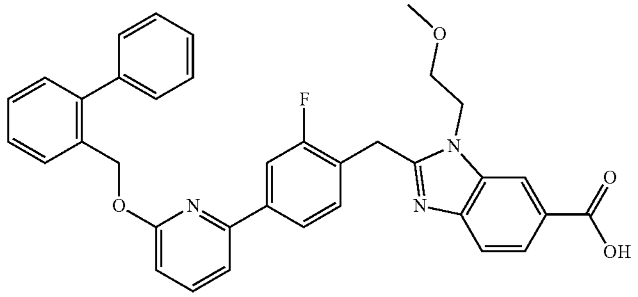 [SMILES: COCCn1c(Cc2ccc(-c3cccc(OCc4ccccc4-c4ccccc4)n3)cc2F)nc2ccc(C(=O)O)cc21]<br>2-(4-(6-([1,1'-biphenyl]-2-ylmethoxy)pyridin-2-yl)-2-fluorobenzyl)-1-(2-methoxyethyl)-1H-benzo[d]imidazole-6-carboxylic acid: ES/MS m/z 588.2; $^1H$ NMR (400 MHz, Methanol-d4) δ 8.54 (d, J = 1.7 Hz, 1H), 8.22 (dd, J = 8.6, 1.4 Hz, 1H), 7.86-7.70 (m, 4H), 7.65-7.57 (m, 1H), 7.51-7.27 (m, 10H), 6.80 (d, J = 8.2 Hz, 1H), 5.42 (s, 2H), 4.79 (t, J = 5.0 Hz, 2H), 4.75 (s, 2H), 3.81 (t, J = 4.9 Hz, 2H), 3.31 (s, 3H). |

-continued

| Example | Structure/Name/Characterization |
| --- | --- |
| 504 | 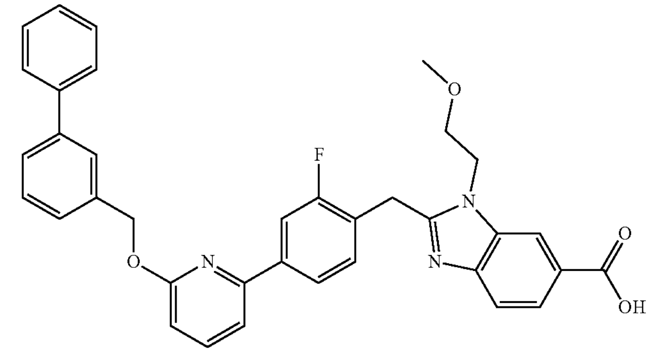 [SMILES: COCCn1c(Cc2ccc(-c3cccc(OCc4cccc(-c5ccccc5)c4)n3)cc2F)nc2ccc(C(=O)O)cc21] 2-(4-(6-([1,1'-biphenyl]-3-ylmethoxy)pyridin-2-yl)-2-fluorobenzyl)-1-(2-methoxyethyl)-1H-benzo[d]imidazole-6-carboxylic acid: ES/MS m/z 588.2; $^{1}$H NMR (400 MHz, Methanol-d4) δ 8.57 (d, J = 1.2 Hz, 1H), 8.25 (dd, J = 8.7, 1.4 Hz, 1H), 8.01-7.93 (m, 2H), 7.84-7.75 (m, 3H), 7.63-7.32 (m, 9H), 7.31-7.22 (m, 1H), 6.90 (d, J = 8.2 Hz, 1H), 5.59 (s, 2H), 4.81 (t, J = 5.0 Hz, 2H), 4.77 (s, 2H), 3.81 (t, J = 4.9 Hz, 2H), 3.30 (s, 3H). |
| 505 | 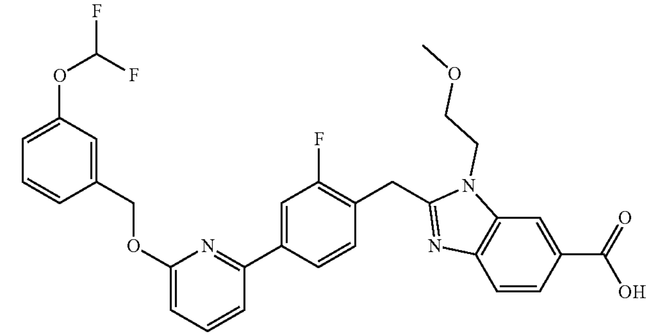 [SMILES: COCCn1c(Cc2ccc(-c3cccc(OCc4cccc(OC(F)F)c4)n3)cc2F)nc2ccc(C(=O)O)cc21] 2-(4-(6-((3-(difluoromethoxy)benzyl)oxy)pyridin-2-yl)-2-fluorobenzyl)-1-(2-methoxyethyl)-1H-benzo[d]imidazole-6-carboxylic acid: ES/MS m/z 578.2; $^{1}$H NMR (400 MHz, Methanol-d4) δ 8.50 (d, J = 1.4 Hz, 1H), 8.18 (dd, J = 8.6, 1.5 Hz, 1H), 7.96-7.87 (m, 2H), 7.84-7.72 (m, 2H), 7.57-7.32 (m, 4H), 7.29 (d, J = 2.2 Hz, 1H), 7.11-7.04 (m, 1H), 6.89 (d, J = 8.2 Hz, 1H), 6.81 (t, J = 74.2 Hz, 1H), 5.53 (s, 2H), 4.75 (t, J = 5.0 Hz, 2H), 4.72 (s, 2H), 3.80 (t, J = 4.9 Hz, 2H), 3.31 (s, 3H). |
| 506 | 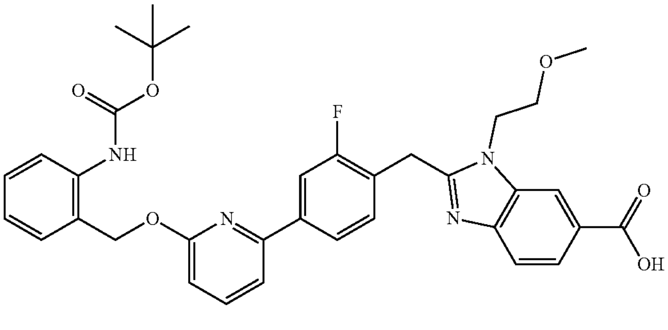 [SMILES: COCCn1c(Cc2ccc(-c3cccc(OCc4ccccc4NC(=O)OC(C)(C)C)n3)cc2F)nc2ccc(C(=O)O)cc21] 2-(4-(6-((2-((tert-butoxycarbonyl)amino)benzyl)oxy)pyridin-2-yl)-2-fluorobenzyl)-1-(2-methoxyethyl)-1H-benzo[d]imidazole-6-carboxylic acid: ES/MS 627.2; $^{1}$H NMR (400 MHz, Methanol-d4) δ 8.48 (s, 1H), 8.17 (dd, J = 8.7, 1.5 Hz, 1H), 7.99-7.91 (m, 2H), 7.84-7.72 (m, 2H), 7.58-7.41 (m, 4H), 7.31 (t, J = 7.7 Hz, 1H), 7.18 (t, J = 7.3 Hz, 1H), 6.87 (d, J = 8.2 Hz, 1H), 5.54 (s, 2H), 4.73 (t, J = 5.1 Hz, 2H), 4.70 (s, 2H), 3.78 (t, J = 4.9 Hz, 2H), 3.31 (s, 3H), 1.44 (s, 9H). |

-continued

| Example | Structure/Name/Characterization |
|---|---|
| 509 | 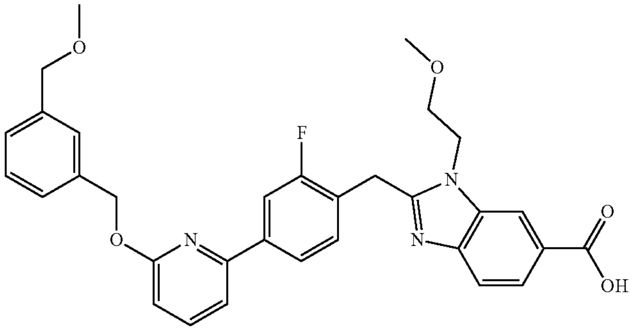 [SMILES: COCCn1c(Cc2ccc(-c3cccc(OCc4cccc(COC)c4)n3)cc2F)nc2ccc(C(=O)O)cc21]<br>2-(2-fluoro-4-(6-((3-(methoxymethyl)benzyl)oxy)pyridin-2-yl)benzyl)-1-(2-methoxyethyl)-1H-benzo[d]imidazole-6-carboxylic acid: ES/MS m/z 556.2; $^{1}H$ NMR (400 MHz, Methanol-d4) δ 8.53 (d, J = 1.4 Hz, 1H), 8.20 (dd, J = 8.7, 1.4 Hz, 1H), 7.98-7.89 (m, 2H), 7.83-7.73 (m, 2H), 7.56-7.40 (m, 4H), 7.36 (t, J = 7.5 Hz, 1H), 7.28 (d, J = 7.5 Hz, 1H), 6.87 (d, J = 8.2 Hz, 1H), 5.52 (s, 2H), 4.78 (t, J = 5.0 Hz, 2H), 4.74 (s, 2H), 4.47 (s, 2H), 3.81 (t, J = 4.9 Hz, 2H), 3.33 (d, J = 14.3 Hz, 6H). |
| 510 | 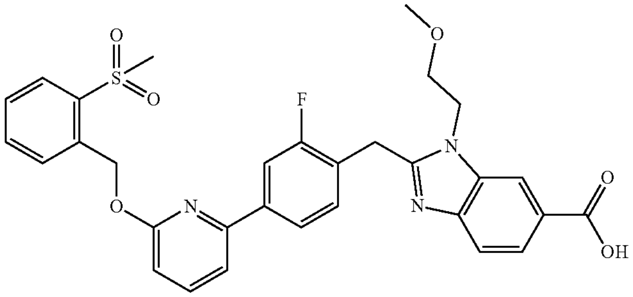 [SMILES: COCCn1c(Cc2ccc(-c3cccc(OCc4ccccc4S(C)(=O)=O)n3)cc2F)nc2ccc(C(=O)O)cc21]<br>2-(2-fluoro-4-(6-((2-(methylsulfonyl)benzyl)oxy)pyridin-2-yl)benzyl)-1-(2-methoxyethyl)-1H-benzo[d]imidazole-6-carboxylic acid: ES/MS m/z 590.2; $^{1}H$ NMR (400 MHz, Methanol-d4) δ 8.56 (t, J = 1.0 Hz, 1H), 8.23 (dd, J = 8.6, 1.4 Hz, 1H), 8.14-8.06 (m, 1H), 7.96-7.67 (m, 6H), 7.66-7.54 (m, 2H), 7.51 (t, J = 7.9 Hz, 1H), 6.94 (d, J = 8.2 Hz, 1H), 5.97 (s, 2H), 4.81 (t, J = 5.0 Hz, 2H), 4.77 (s, 2H), 3.82 (t, J = 4.9 Hz, 2H), 3.32 (s, 3H), 3.25 (s, 3H). |
| 512 | 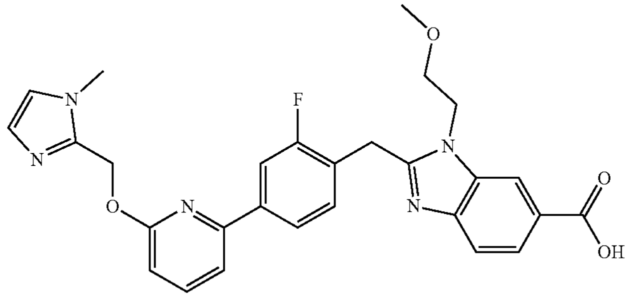 [SMILES: COCCn1c(Cc2ccc(-c3cccc(OCc4nccn4C)n3)cc2F)nc2ccc(C(=O)O)cc21]<br>2-(2-fluoro-4-(6-((1-methyl-1H-imidazol-2-yl)methoxy)pyridin-2-yl)benzyl)-1-(2-methoxyethyl)-1H-benzo[d]imidazole-6-carboxylic acid: ES/MS m/z 516.2; $^{1}H$ NMR (400 MHz, Methanol-d4) δ 8.42 (d, J = 1.3 Hz, 1H), 8.11 (dd, J = 8.6, 1.5 Hz, 1H), 7.94-7.80 (m, 3H), 7.72 (d, J = 8.5 Hz, 1H), 7.68-7.58 (m, 2H), 7.57 (d, J = 2.0 Hz, 1H), 7.46 (t, J = 7.8 Hz, 1H), 7.01 (d, J = 8.2 Hz, 1H), 5.82 (s, 2H), 4.69 (t, J = 5.0 Hz, 2H), 4.65 (s, 2H), 4.01 (s, 3H), 3.78 (t, J = 4.9 Hz, 2H), 3.30 (s, 3H). |

-continued

| Example | Structure/Name/Characterization |
|---|---|
| 514 | 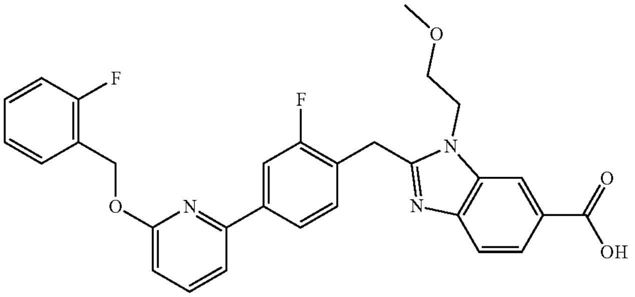 [SMILES: COCCn1c(Cc2ccc(-c3cccc(OCc4ccccc4F)n3)cc2F)nc2ccc(C(=O)O)cc21] 2-(2-fluoro-4-(6-((2-fluorobenzyl)oxy)pyridin-2-yl)benzyl)-1-(2-methoxyethyl)-1H-benzo[d]imidazole-6-carboxylic acid: ES/MS m/z 530.2; $^{1}$H NMR (400 MHz, Methanol-d4) δ 8.51 (t, J = 0.9 Hz, 1H), 8.18 (dd, J = 8.6, 1.5 Hz, 1H), 7.99-7.90 (m, 2H), 7.83-7.72 (m, 2H), 7.60-7.50 (m, 2H), 7.49 (t, J = 7.9 Hz, 1H), 7.40-7.30 (m, 1H), 7.22-7.09 (m, 2H), 6.86 (d, J = 8.2 Hz, 1H), 5.58 (s, 2H), 4.77 (t, J = 5.0 Hz, 2H), 4.73 (s, 2H), 3.80 (t, J = 5.0 Hz, 2H), 3.31 (s, 3H). |
| 542 | 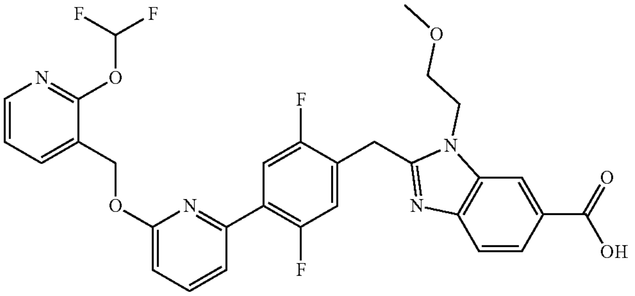 [SMILES: COCCn1c(Cc2cc(F)c(-c3cccc(OCc4cccnc4OC(F)F)n3)cc2F)nc2ccc(C(=O)O)cc21] 2-(4-(6-((2-(difluoromethoxy)pyridin-3-yl)methoxy)pyridin-2-yl)-2,5-difluorobenzyl)-1-(2-methoxyethyl)-1H-benzo[d]imidazole-6-carboxylic acid: ES/MS m/z 597.2; $^{1}$H NMR (400 MHz, DMSO) δ 8.27-8.21 (m, 2H), 8.02 (dd, J = 7.5, 1.9 Hz, 1H), 7.98-7.57 (m, 5H), 7.52 (dd, J = 7.4, 1.8 Hz, 1H), 7.39 (dd, J = 11.5, 6.1 Hz, 1H), 7.31 (dd, J = 7.5, 4.9 Hz, 1H), 6.98 (d, J = 8.3 Hz, 1H), 5.49 (s, 2H), 4.62 (t, J = 5.1 Hz, 2H), 4.48 (s, 2H), 3.68 (t, J = 5.0 Hz, 2H), 3.21 (s, 3H). |
| 543 | 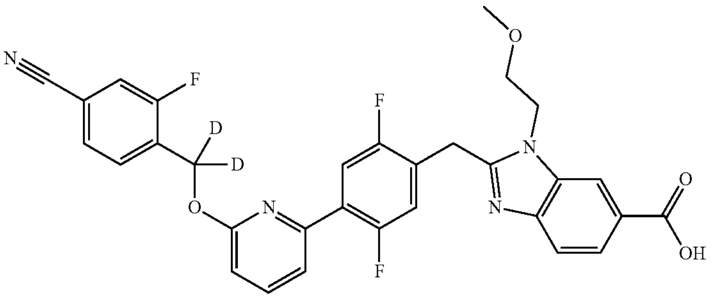 [SMILES: [2H]C([2H])(Oc1cccc(-c2cc(F)c(Cc3nc4ccc(C(=O)O)cc4n3CCOC)cc2F)n1)c1ccc(C#N)cc1F] 2-(4-(6-((4-cyano-2-fluorophenyl)methoxy-d2)pyridin-2-yl)-2,5-difluorobenzyl)-1-(2-methoxyethyl)-1H-benzo[d]imidazole-6-carboxylic acid: ES/MS m/z 575.2; $^{1}$H NMR (400 MHz, DMSO) δ 8.28 (d, J = 1.6 Hz, 1H), 7.95-7.82 (m, 3H), 7.80-7.69 (m, 3H), 7.64 (d, J = 8.5 Hz, 1H), 7.52 (dd, J = 7.6, 1.8 Hz, 1H), 7.41 (dd, J = 11.5, 6.1 Hz, 1H), 6.99 (d, J = 8.2 Hz, 1H), 4.64 (t, J = 5.0 Hz, 2H), 4.51 (s, 2H), 3.69 (t, J = 5.0 Hz, 2H), 3.21 (s, 3H). |

-continued

| Example | Structure/Name/Characterization |
|---|---|
| 544 | 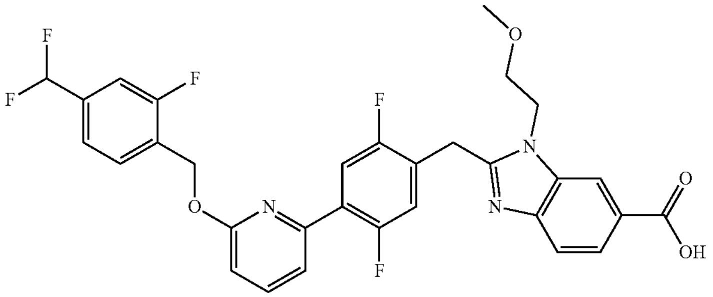 [SMILES: COCCn1c(Cc2cc(F)c(-c3cccc(OCc4ccc(C(F)F)cc4F)n3)cc2F)nc2ccc(C(=O)O)cc21] 2-(4-(6-((4-(difluoromethyl)-2-fluorobenzyl)oxy)pyridin-2-yl)-2,5-difluorobenzyl)-1-(2-methoxyethyl)-1H-benzo[d]imidazole-6-carboxylic acid: ES/MS 598.2; $^{1}$H NMR (400 MHz, DMSO) δ 8.22 (d, J = 1.6 Hz, 1H), 7.92-7.84 (m, 1H), 7.83-7.76 (m, 2H), 7.72 (t, J = 7.6 Hz, 1H), 7.61 (d, J = 8.5 Hz, 1H), 7.54-7.43 (m, 3H), 7.38 (dd, J = 11.5, 6.1 Hz, 1H), 7.26-6.82 (m, 2H), 5.57 (s, 2H), 4.59 (d, J = 5.4 Hz, 2H), 4.45 (s, 2H), 3.68 (t, J = 5.1 Hz, 2H), 3.21 (s, 3H). |
| 557 | 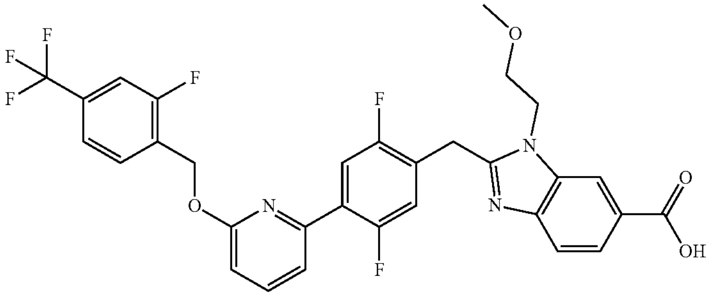 [SMILES: COCCn1c(Cc2cc(F)c(-c3cccc(OCc4ccc(C(F)(F)F)cc4F)n3)cc2F)nc2ccc(C(=O)O)cc21] 2-(2,5-difluoro-4-(6-((2-fluoro-4-(trifluoromethyl)benzyl)oxy)pyridin-2-yl)benzyl)-1-(2-methoxyethyl)-1H-benzo[d]imidazole-6-carboxylic acid: ES/MS m/z 616.2; $^{1}$H NMR (400 MHz, DMSO-d6) δ 8.23 (d, J = 1.5 Hz, 1H), 7.93-7.87 (m, 1H), 7.85-7.71 (m, 4H), 7.66-7.59 (m, 2H), 7.53 (dd, J = 7.4, 1.7 Hz, 1H), 7.39 (dd, J = 11.5, 6.1 Hz, 1H), 6.99 (d, J = 8.3 Hz, 1H), 5.61 (s, 2H), 4.61 (t, J = 5.1 Hz, 2H), 4.46 (s, 2H), 3.69 (t, J = 5.1 Hz, 2H), 3.21 (s, 3H). |
| 563 | 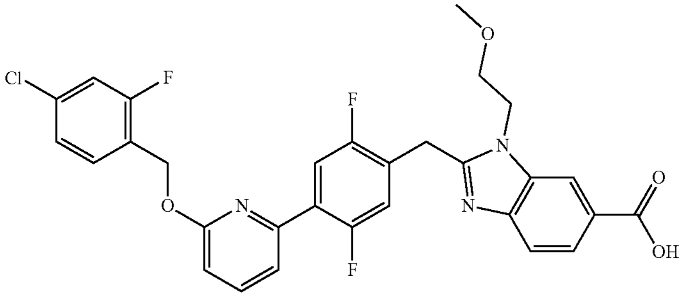 [SMILES: COCCn1c(Cc2cc(F)c(-c3cccc(OCc4ccc(Cl)cc4F)n3)cc2F)nc2ccc(C(=O)O)cc21] 2-(4-(6-((4-chloro-2-fluorobenzyl)oxy)pyridin-2-yl)-2,5-difluorobenzyl)-1-(2-methoxyethyl)-1H-benzo[d]imidazole-6-carboxylic acid: ES/MS m/z 582.2; $^{1}$H NMR (400 MHz, Methanol-d4) δ 8.56 (dd, J = 1.5, 0.7 Hz, 1H), 8.23 (dd, J = 8.6, 1.4 Hz, 1H), 7.91 (dd, J = 10.8, 6.3 Hz, 1H), 7.85-7.76 (m, 2H), 7.63-7.50 (m, 2H), 7.37 (dd, J = 11.2, 6.0 Hz, 1H), 7.29-7.20 (m, 2H), 6.91 (dd, J = 8.3, 0.7 Hz, 1H), 5.53 (s, 2H), 4.83 (t, J = 5.0 Hz, 2H), 4.77 (s, 2H), 3.85 (dd, J = 5.4, 4.4 Hz, 2H), 3.33 (s, 3H). |

-continued

| Example | Structure/Name/Characterization |
|---|---|
| 564 | 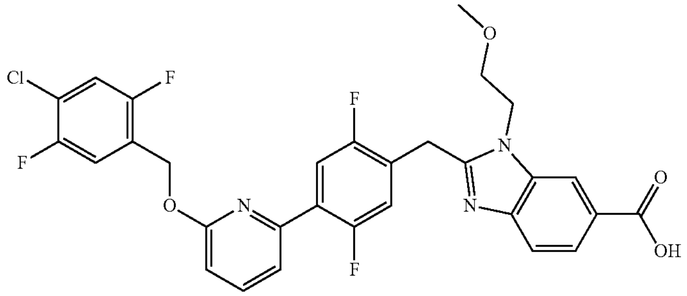 [SMILES: COCCn1c(Cc2cc(F)c(-c3cccc(OCc4cc(F)c(Cl)cc4F)n3)cc2F)nc2ccc(C(=O)O)cc21] 2-(4-(6-((4-chloro-2,5-difluorobenzyl)oxy)pyridin-2-yl)-2,5-difluorobenzyl)-1-(2-methoxyethyl)-1H-benzo[d]imidazole-6-carboxylic acid: ES/MS 600.1; $^{1}$H NMR (400 MHz, Methanol-d4) δ 8.52 (dd, J = 1.4, 0.7 Hz, 1H), 8.20 (dd, J = 8.6, 1.5 Hz, 1H), 7.88 (dd, J = 10.8, 6.3 Hz, 1H), 7.83 (dd, J = 8.3, 7.5 Hz, 1H), 7.77 (dd, J = 8.6, 0.7 Hz, 1H), 7.62-7.55 (m, 1H), 7.45 (dd, J = 9.0, 6.6 Hz, 1H), 7.38 (dd, J = 8.8, 6.4 Hz, 1H), 7.34 (dd, J = 11.3, 6.1 Hz, 1H), 6.94 (dd, J = 8.3, 0.6 Hz, 1H), 5.53 (s, 2H), 4.79 (t, J = 5.0 Hz, 2H), 4.73 (s, 2H), 3.83 (t, J = 4.9 Hz, 2H), 3.32 (s, 3H). |
| 565 | 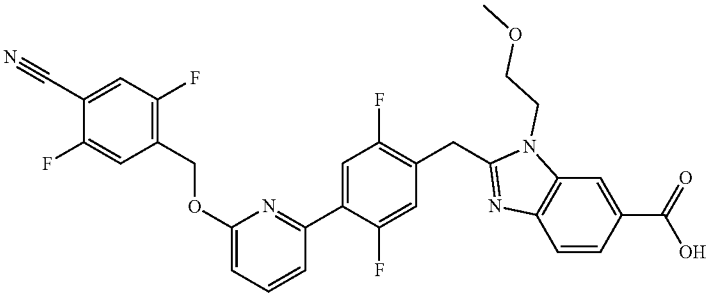 [SMILES: COCCn1c(Cc2cc(F)c(-c3cccc(OCc4cc(F)c(C#N)cc4F)n3)cc2F)nc2ccc(C(=O)O)cc21] 2-(4-(6-((4-cyano-2,5-difluorobenzyl)oxy)pyridin-2-yl)-2,5-difluorobenzyl)-1-(2-methoxyethyl)-1H-benzo[d]imidazole-6-carboxylic acid: ES/MS m/z 591.2; $^{1}$H NMR (400 MHz, Methanol-d4) δ 8.49 (d, J = 1.0 Hz, 1H), 8.17 (dd, J = 8.6, 1.5 Hz, 1H), 7.88-7.83 (m, 1H), 7.80 (dd, J = 10.7, 6.3 Hz, 1H), 7.75 (d, J = 8.6 Hz, 1H), 7.67 (dd, J = 8.9, 5.1 Hz, 1H), 7.63-7.51 (m, 2H), 7.31 (dd, J = 11.3, 6.1 Hz, 1H), 6.99 (d, J = 8.2 Hz, 1H), 5.62 (s, 2H), 4.76 (t, J = 5.0 Hz, 2H), 4.69 (s, 2H), 3.82 (t, J = 4.9 Hz, 2H), 3.31 (s, 3H). |
| 592 | 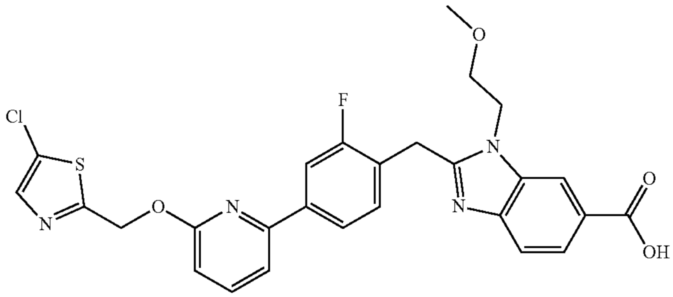 2-(4-(6-((5-chlorothiazol-2-yl)methoxy)pyridin-2-yl)-2-fluorobenzyl)-1-(2-methoxyethyl)-1H-benzo[d]imidazole-6-carboxylic acid: ES/MS m/z 553.3; $^{1}$H NMR (400 MHz, DMSO-d6) δ 7.75 (s, 1H), 7.42 (d, J = 8.7 Hz, 1H), 7.17 (d, J = 10.2 Hz, 2H), 7.04 (t, J = 7.9 Hz, 1H), 6.97 (d, J = 8.4 Hz, 1H), 6.83 (dt, J = 7.8, 3.9 Hz, 2H), 6.71 (d, J = 8.3 Hz, 1H), 6.11 (d, J = 8.0 Hz, 1H), 4.91 (s, 2H), 3.00 (t, J = 4.9 Hz, 2H). |

-continued

| Example | Structure/Name/Characterization |
|---|---|
| 595 | 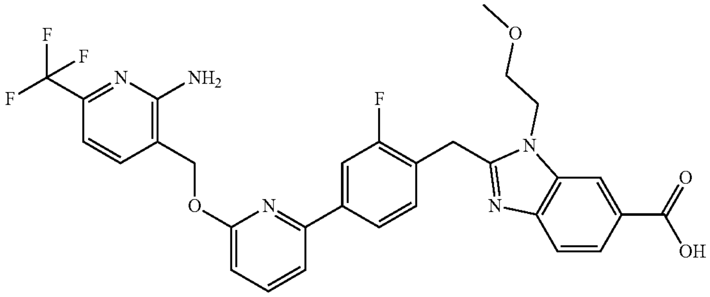 [SMILES: COCCn1c(Cc2ccc(-c3cccc(OCc4ccc(C(F)(F)F)nc4N)n3)cc2F)nc2ccc(C(=O)O)cc21]<br>2-(4-(6-((2-amino-6-(trifluoromethyl)pyridin-3-yl)methoxy)pyridin-2-yl)-2-fluorobenzyl)-1-(2-methoxyethyl)-1H-benzo[d]imidazole-6-carboxylic acid: ES/MS m/z 596.2; Multiplet Report $^1$H NMR (400 MHz, Methanol-d4) δ 8.43 (s, 1H), 8.13 (d, J = 7.4 Hz, 1H), 7.76-7.63 (m, 2H), 7.39 (t, J = 7.9 Hz, 1H), 7.15 (dd, J = 20.7, 9.0 Hz, 2H), 6.86 (s, 2H), 6.74 (dd, J = 9.2, 1.2 Hz, 2H), 6.42 (dd, J = 6.9, 1.3 Hz, 2H), 5.07 (s, 2H), 4.71-4.62 (m, 4H), 3.78 (t, J = 4.9 Hz, 2H), 3.27 (s, 3H). |
| 596 | 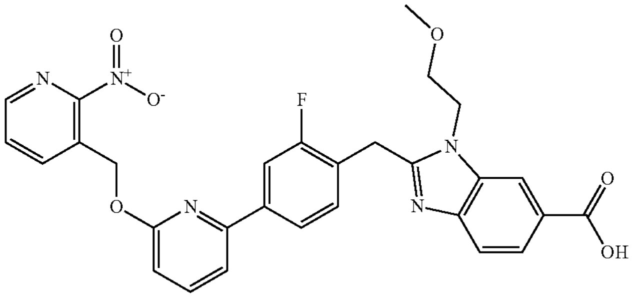 [SMILES: COCCn1c(Cc2ccc(-c3cccc(OCc4cccnc4[N+](=O)[O-])n3)cc2F)nc2ccc(C(=O)O)cc21]<br>2-(2-fluoro-4-(6-((2-nitropyridin-3-yl)methoxy)pyridin-2-yl)benzyl)-1-(2-methoxyethyl)-1H-benzo[d]imidazole-6-carboxylic acid: ES/MS m/z 558.2; Multiplet Report $^1$H NMR (400 MHz, Methanol-d4) δ 8.56-8.48 (m, 2H), 8.35 (d, J = 7.2 Hz, 1H), 8.21 (d, J = 8.3 Hz, 1H), 7.88-7.72 (m, 5H), 7.57 (d, J = 7.4 Hz, 1H), 7.48 (t, J = 7.9 Hz, 1H), 6.96 (d, J = 8.2 Hz, 1H), 5.81 (s, 2H), 4.78 (t, J = 5.0 Hz, 2H), 4.74 (s, 2H), 3.81 (t, J = 4.9 Hz, 2H), 3.31 (s, 3H). |
| 692 | 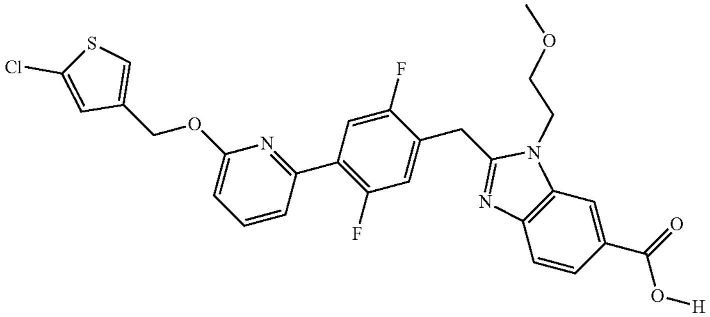 [SMILES: COCCn1c(Cc2cc(F)c(-c3cccc(OCc4csc(Cl)c4)n3)cc2F)nc2ccc(C(=O)O)cc21]<br>ES/MS 570.1; 1H NMR (400 MHz, Methanol-d4) δ 8.24 (s, 1H), 8.03-7.90 (m, 2H), 7.78 (t, J = 7.9 Hz, 1H), 7.64 (d, J = 8.4 Hz, 1H), 7.60-7.44 (m, 1H), 7.15 (dd, J = 11.6, 6.1 Hz, 1H), 7.03 (d, J = 3.7 Hz, 1H), 6.86 (d, J = 3.8 Hz, 1H), 6.82 (d, J = 8.3 Hz, 1H), 5.59 (s, 2H), 4.64-4.52 (m, 3H), 4.50 (s, 2H), 3.74 (t, J = 5.0 Hz, 2H), 3.27 (s, 3H). (Multiplet Report) 19F NMR (377 MHz, Methanol-d4) δ −77.49, −121.24-−124.22 (m), −124.22-−127.56 (m). |

-continued

| Example | Structure/Name/Characterization |
|---|---|
| 693 | 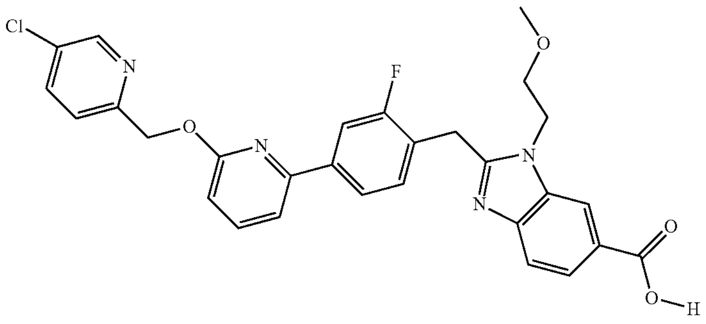 [SMILES: COCCn1c(Cc2ccc(-c3cccc(OCc4ccc(Cl)cn4)n3)cc2F)nc2ccc(C(=O)O)cc21]<br>ES/MS 547.3; 1H NMR (400 MHz, DMSO-d6) δ 8.62 (d, J = 2.5 Hz, 1H), 8.24 (s, 1H), 7.94 (dd, J = 8.4, 2.5 Hz, 1H), 7.89-7.74 (m, 5H), 7.63 (dd, J = 14.6, 8.0 Hz, 2H), 7.54 (d, J = 8.4 Hz, 1H), 7.41 (t, J = 8.0 Hz, 1H), 6.95 (d, J = 8.2 Hz, 1H), 5.55 (s, 2H), 4.60 (t, J = 5.1 Hz, 2H), 4.47 (s, 2H), 3.66 (t, J = 5.1 Hz, 2H), 3.20 (s, 3H). Multiplet Report 19F NMR (376 MHz, DMSO-d6) δ −74.84, −115.72−−119.83 (m). |

Example 480, 2-[[2-fluoro-4-[6-[[2-fluoro-4-(trifluoromethyl)phenyl]methoxy]-2-pyridyl]phenyl]methyl]-3-(2-methoxyethyl)benzimidazole-5-carboxylic acid Procedure 33

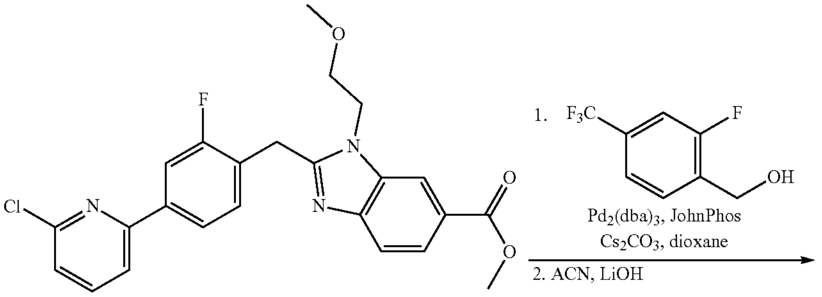

I-110

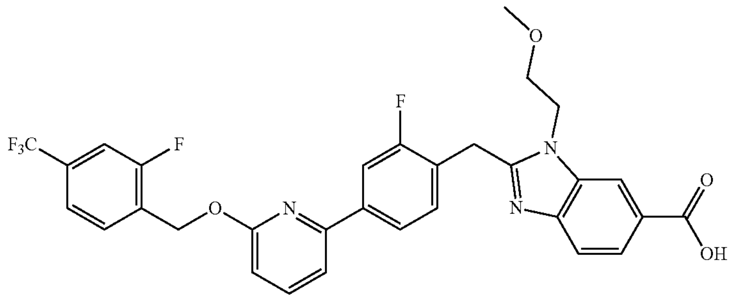

Example 480

2-[[2-fluoro-4-[6-[[2-fluoro-4-(trifluoromethyl)phenyl]methoxy]-2-pyridyl]phenyl]methyl]-3-(2-methoxyethyl)benzimidazole-5-carboxylic acid (Example 480): Methyl 2-[[4-(6-chloro-2-pyridyl)-2-fluoro-phenyl]methyl]-3-(2-methoxyethyl)benzimidazole-5-carboxylate (I-110, 50.0 mg, 0.110 mmol) was added to [2-fluoro-4-(trifluoromethyl)phenyl]methanol (23.5 mg, 0.121 mmol), $Pd_2$(DBA)3 (15.1 mg, 0.0165 mmol), 2-(di-tert-butylphosphino)biphenyl (JohnPhos), (9.86 mg, 0.0330 mmol), and cesium carbonate (71.8 mg, 0.220 mmol) in 1,4-dioxane. The mixture was heated to 80° C. for 4 hours. The mixture was cooled to ambient temperature then filtered. The mixture was diluted with acetonitrile (2 mL) and excess 1 M aq. LiOH (0.5 mL) was added. The mixture was heated to 40° C. for 5 hours. The reaction was cooled to ambient temperature and quenched with excess trifluoroacetic acid (0.1 mL). The mixture was purified by RP-HPLC (eluent: water/MeCN 0.1% TFA) to yield the titled product: ES/MS m/z: 598.138 ($M+H^+$); $^1$H NMR (400 MHz, Methanol-d4) δ 8.59 (s, 1H), 8.25 (dd, J=8.6, 1.4 Hz, 1H), 7.99-7.85 (m, 3H), 7.85-7.66 (m, 4H), 7.60-7.42 (m, 5H), 6.91 (d, J=8.2 Hz, 1H), 5.65 (s, 2H), 4.83 (d, J=4.7 Hz, 1H), 4.80 (s, 3H), 3.82 (t, J=4.9 Hz, 2H). 19F NMR (376 MHz, Methanol-d4) δ −64.72, −77.93, −117.39-121.09 (m).

Example 139, 235, 236, 244-246, 267, 346, 363, 459, 460, 463, 479, 487, 494, 497, 507, 508, 511, 515. Compounds Prepared Using Procedure 33

Other compounds of the present disclosure prepared using the general route described in Procedure 33 include the following Examples.

| Example | Structure/Name/Characterization |
|---|---|
| 139 | 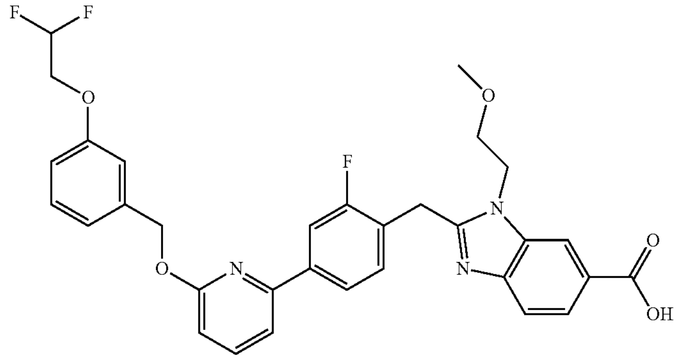 [SMILES: COCCn1c(Cc2ccc(-c3cccc(OCc4cccc(OCC(F)F)c4)n3)cc2F)nc2ccc(C(=O)O)cc21] 2-(4-(6-((3-(2,2-difluoroethoxy)benzyl)oxy)pyridin-2-yl)-2-fluorobenzyl)-1-(2-methoxyethyl)-1H-benzo[d]imidazole-6-carboxylic acid: ES/MS m/z 592.2; $^{1}$H NMR (400 MHz, Methanol-d4) δ 8.43 (s, 1H), 8.12 (dd, J = 8.6, 1.5 Hz, 1H), 7.91 (s, 1H), 7.89 (s, 1H), 7.76 (dd, J = 8.2, 7.5 Hz, 1H), 7.72 (d, J = 8.6 Hz, 1H), 7.51 (d, J = 7.4 Hz, 1H), 7.42 (t, J = 7.8 Hz, 1H), 7.29 (t, J = 8.2 Hz, 1H), 7.17-7.06 (m, 2H), 6.94-6.87 (m, 1H), 6.85 (d, J = 8.2 Hz, 1H), 6.12 (tt, J = 55.1, 3.8 Hz, 1H), 5.48 (s, 2H), 4.69 (t, J = 5.0 Hz, 2H), 4.65 (s, 2H), 4.20 (td, J = 13.7, 3.9 Hz, 2H), 3.75 (t, J = 5.0 Hz, 2H), 3.28 (s, 3H). |
| 235 | 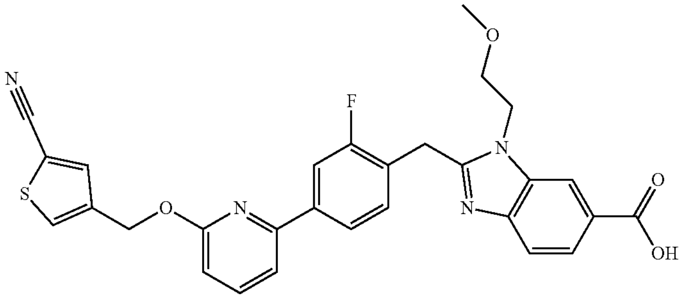 [SMILES: COCCn1c(Cc2ccc(-c3cccc(OCc4csc(C#N)c4)n3)cc2F)nc2ccc(C(=O)O)cc21] 2-(4-(6-((5-cyanothiophen-3-yl)methoxy)pyridin-2-yl)-2-fluorobenzyl)-1-(2-methoxyethyl)-1H-benzo[d]imidazole-6-carboxylic acid: ES/MS m/z 543.2; $^{1}$H NMR (400 MHz, Methanol-d4) δ 8.54 (d, J = 1.3 Hz, 1H), 8.21 (dd, J = 8.6, 1.4 Hz, 1H), 8.17 (d, J = 1.4 Hz, 1H), 8.02 (s, 1H), 7.99 (q, J = 1.6 Hz, 1H), 7.84-7.72 (m, 2H), 7.58 (d, J = 7.5 Hz, 1H), 7.53 (t, J = 7.9 Hz, 1H), 7.45 (d, J = 1.3 Hz, 1H), 6.83 (d, J = 8.2 Hz, 1H), 5.70 (d, J = 0.8 Hz, 2H), 4.80 (t, J = 5.0 Hz, 2H), 4.76 (s, 2H), 3.84-3.76 (m, 2H), 3.30 (s, 3H). |
| 236 | 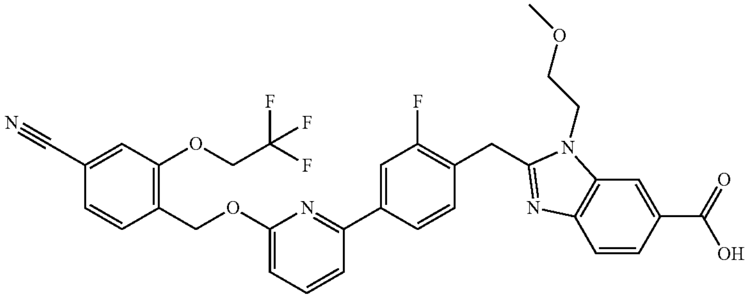 2-(4-(6-((4-cyano-2-(2,2,2-trifluoroethoxy)benzyl)oxy)pyridin-2-yl)-2-fluorobenzyl)-1-(2-methoxyethyl)-1H-benzo[d]imidazole-6-carboxylic acid: ES/MS m/z 649.2; $^{1}$H NMR (400 MHz, Methanol-d4) δ 8.48 (s, 1H), 8.16 (dd, J = 8.6, 1.5 Hz, 1H), 7.90-7.83 (m, 2H), 7.80 (t, J = 7.9 Hz, 1H), 7.73 (d, J = 8.6 Hz, 1H), 7.63 (d, J = 7.8 Hz, 1H), 7.55 (d, J = 7.5 Hz, 1H), 7.49 (d, J = 1.3 |

-continued

| Example | Structure/Name/Characterization |
|---|---|
| | Hz, 1H), 7.47-7.39 (m, 2H), 6.90 (d, J = 8.2 Hz, 1H), 5.62 (s, 2H), 4.79-4.65 (m, 6H), 3.77 (t, J = 4.9 Hz, 2H), 3.28 (s, 3H). |
| 244 | 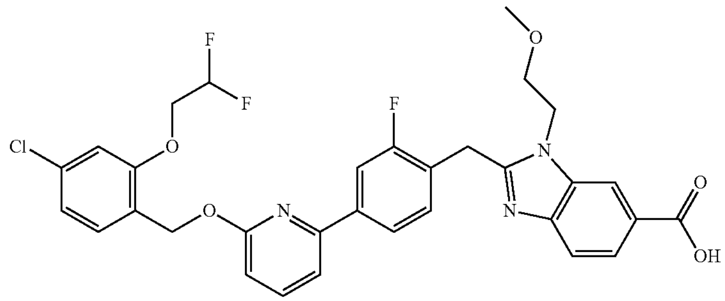 [SMILES: COCCn1c(Cc2ccc(-c3cccc(OCc4ccc(Cl)cc4OCC(F)F)n3)cc2F)nc2ccc(C(=O)O)cc21] 2-(4-(6-((4-chloro-2-(2,2-difluoroethoxy)benzyl)oxy)pyridin-2-yl)-2-fluorobenzyl)-1-(2-methoxyethyl)-1H-benzo[d]imidazole-6-carboxylic acid: ES/MS 626.1; $^1$H NMR (400 MHz, Methanol-d4) δ 8.49 (d, J = 1.3 Hz, 1H), 8.17 (dd, J = 8.6, 1.5 Hz, 1H), 7.98-7.86 (m, 2H), 7.81-7.70 (m, 2H), 7.52 (d, J = 7.4 Hz, 1H), 7.46 (t, J = 8.1 Hz, 1H), 7.42 (d, J = 8.2 Hz, 1H), 7.11 (d, J = 1.9 Hz, 1H), 7.01 (dd, J = 8.1, 1.9 Hz, 1H), 6.84 (d, J = 8.1 Hz, 1H), 6.16 (tt, J = 54.9, 3.8 Hz, 1H), 5.52 (s, 2H), 4.75 (t, J = 5.0 Hz, 2H), 4.71 (s, 2H), 4.33 (td, J = 13.7, 3.8 Hz, 2H), 3.78 (t, J = 4.9 Hz, 2H), 3.29 (s, 3H). |
| 245 | 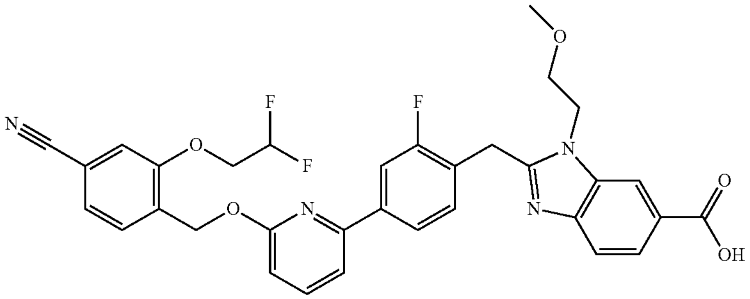 [SMILES: COCCn1c(Cc2ccc(-c3cccc(OCc4ccc(C#N)cc4OCC(F)F)n3)cc2F)nc2ccc(C(=O)O)cc21] 2-(4-(6-((4-cyano-2-(2,2-difluoroethoxy)benzyl)oxy)pyridin-2-yl)-2-fluorobenzyl)-1-(2-methoxyethyl)-1H-benzo[d]imidazole-6-carboxylic acid: ES/MS m/z 617.2; $^1$H NMR (400 MHz, Methanol-d4) δ 8.50 (s, 1H), 8.18 (dd, J = 8.6, 1.5 Hz, 1H), 7.92-7.83 (m, 2H), 7.80 (t, J = 7.9 Hz, 1H), 7.74 (d, J = 8.6 Hz, 1H), 7.60 (d, J = 7.8 Hz, 1H), 7.54 (d, J = 7.4 Hz, 1H), 7.48-7.43 (m, 2H), 7.37 (dd, J = 7.8, 1.4 Hz, 1H), 6.90 (d, J = 8.2 Hz, 1H), 6.22 (tt, J = 54.8, 3.7 Hz, 1H), 5.62 (s, 2H), 4.76 (t, J = 5.0 Hz, 2H), 4.71 (s, 2H), 4.41 (td, J = 13.7, 3.7 Hz, 2H), 3.78 (t, J = 4.9 Hz, 2H), 3.29 (s, 3H). |
| 246 | 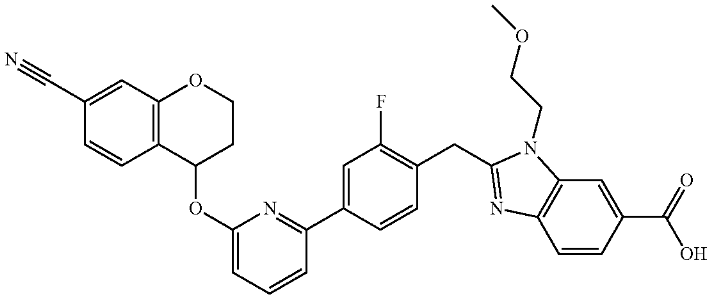 2-(4-(6-((7-cyanochroman-4-yl)oxy)pyridin-2-yl)-2-fluorobenzyl)-1-(2-methoxyethyl)-1H-benzo[d]imidazole-6-carboxylic acid: ES/MS m/z 593.1; $^1$H NMR (400 MHz, Methanol-d4) δ 8.51 (s, 1H), 8.19 (dd, J = 8.6, 1.4 Hz, 1H), 8.07-7.95 (m, 2H), 7.81 (t, J = 7.9 Hz, 1H), 7.76 (d, J = 8.6 Hz, 1H), 7.59 (d, J = 7.5 Hz, 1H), 7.57-7.48 (m, 2H), 7.22 (d, J = 1.5 Hz, 1H), 7.18 (dd, J = 7.8, 1.6 Hz, 1H), 6.81 (d, J = 8.2 Hz, 1H), 6.53 (t, J = 4.4 Hz, 1H), 4.77 (t, J = 5.0 Hz, 2H), 4.74 (s, 2H), 4.46-4.35 (m, 2H), 3.80 (t, J = 4.9 Hz, 2H), 3.31 (s, 3H), 2.46-2.29 (m, 2H). |

-continued

| Example | Structure/Name/Characterization |
|---|---|
| 249 | 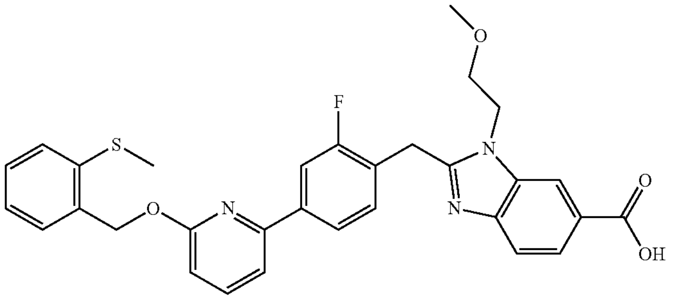 [SMILES: COCCn1c(Cc2ccc(-c3cccc(OCc4ccccc4SC)n3)cc2F)nc2ccc(C(=O)O)cc21]<br>2-(2-fluoro-4-(6-((2-(methylthio)benzyl)oxy)pyridin-2-yl)benzyl)-1-(2-methoxyethyl)-1H-benzo[d]imidazole-6-carboxylic acid: ES/MS m/z 558.2; $^1$H NMR (400 MHz, Methanol-d4) δ 8.52 (d, J = 1.3 Hz, 1H), 8.20 (dd, J = 8.6, 1.4 Hz, 1H), 7.95 (s, 1H), 7.93 (q, J = 1.6 Hz, 1H), 7.81-7.72 (m, 2H), 7.55-7.43 (m, 3H), 7.37 (dd, J = 7.9, 1.2 Hz, 1H), 7.30 (td, J = 7.6, 1.5 Hz, 1H), 7.16 (td, J = 7.5, 1.3 Hz, 1H), 6.85 (d, J = 8.2 Hz, 1H), 5.56 (s, 2H), 4.78 (t, J = 5.0 Hz, 2H), 4.74 (s, 2H), 3.80 (t, J = 4.9 Hz, 2H), 3.30 (s, 3H), 2.50 (s, 3H). |
| 267 | 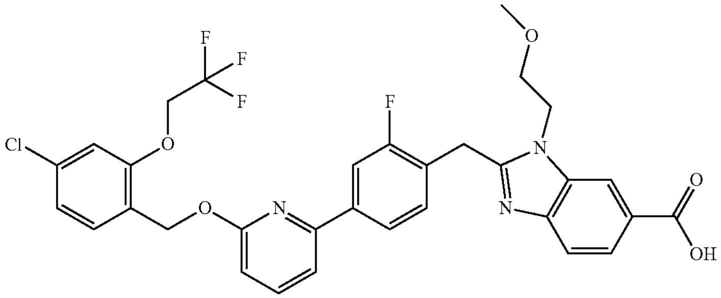 [SMILES: COCCn1c(Cc2ccc(-c3cccc(OCc4ccc(Cl)cc4OCC(F)(F)F)n3)cc2F)nc2ccc(C(=O)O)cc21]<br>2-(4-(6-((4-chloro-2-(2,2,2-trifluoroethoxy)benzyl)oxy)pyridin-2-yl)-2-fluorobenzyl)-1-(2-methoxyethyl)-1H-benzo[d]imidazole-6-carboxylic acid: ES/MS m/z 644.1; $^1$H NMR (400 MHz, Methanol-d4) δ 8.51 (d, J = 1.3 Hz, 1H), 8.18 (dd, J = 8.6, 1.4 Hz, 1H), 7.97-7.87 (m, 2H), 7.79-7.71 (m, 2H), 7.53 (d, J = 7.4 Hz, 1H), 7.50-7.42 (m, 2H), 7.16 (d, J = 1.9 Hz, 1H), 7.06 (dd, J = 8.2, 1.9 Hz, 1H), 6.85 (d, J = 8.2 Hz, 1H), 5.53 (s, 2H), 4.76 (t, J = 5.0 Hz, 2H), 4.72 (s, 2H), 4.64 (q, J = 8.4 Hz, 2H), 3.79 (t, J = 5.0 Hz, 2H), 3.29 (s, 3H). |
| 346 | 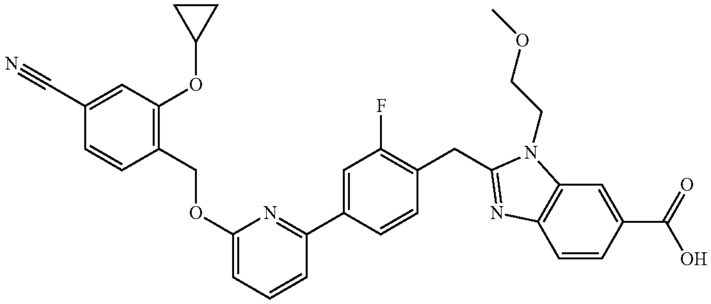 [SMILES: COCCn1c(Cc2ccc(-c3cccc(OCc4ccc(C#N)cc4OC4CC4)n3)cc2F)nc2ccc(C(=O)O)cc21]<br>2-(4-(6-((4-cyano-2-cyclopropoxybenzyl)oxy)pyridin-2-yl)-2-fluorobenzyl)-1-(2-methoxyethyl)-1H-benzo[d]imidazole-6-carboxylic acid: ES/MS m/z 593.3; $^1$H NMR (400 MHz, DMSO-d6) δ 8.23 (d, J = 1.5 Hz, 1H), 7.92-7.78 (m, 4H), 7.76 (d, J = 1.5 Hz, 1H), 7.64 (d, J = 7.5 Hz, 1H), 7.61 (d, J = 8.4 Hz, 1H), 7.55 (d, J = 7.8 Hz, 1H), 7.50-7.38 (m, 2H), 6.92 (d, J = 8.2 Hz, 1H), 5.48 (s, 2H), 4.59 (t, J = 5.2 Hz, 2H), 4.46 (s, 2H), 4.12-4.01 (m, 1H), 3.66 (t, J = 5.1 Hz, 2H), 3.21 (s, 3H), 0.85 (dt, J = 7.6, 5.7 Hz, 2H), 0.73-0.64 (m, 2H). |

-continued

| Example | Structure/Name/Characterization |
|---|---|
| 363 | 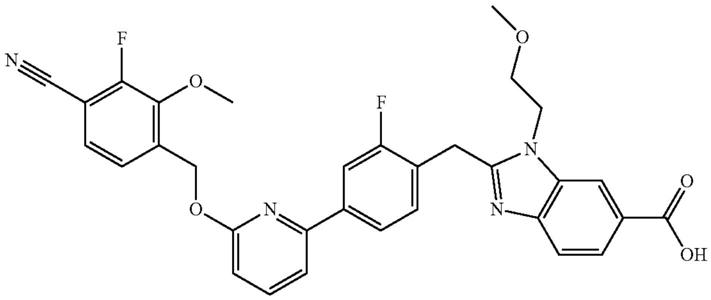 [SMILES: COCCn1c(Cc2ccc(-c3cccc(OCc4ccc(C#N)c(F)c4OC)n3)cc2F)nc2ccc(C(=O)O)cc21]<br>2-(4-(6-((4-cyano-3-fluoro-2-methoxybenzyl)oxy)pyridin-2-yl)-2-fluorobenzyl)-1-(2-methoxyethyl)-1H-benzo[d]imidazole-6-carboxylic acid: ES/MS m/z 585.3; $^1$H NMR (400 MHz, Methanol-d4) δ 8.57-8.40 (m, 1H), 8.20 (dd, J = 8.6, 1.5 Hz, 1H), 7.95-7.86 (m, 2H), 7.82 (t, J = 7.9 Hz, 1H), 7.77 (d, J = 8.6 Hz, 1H), 7.57 (d, J = 7.4 Hz, 1H), 7.49 (t, J = 8.0 Hz, 1H), 7.46-7.37 (m, 2H), 6.92 (d, J = 8.2 Hz, 1H), 5.63 (s, 2H), 4.78 (t, J = 5.0 Hz, 2H), 4.74 (s, 2H), 4.08 (d, J = 2.3 Hz, 3H), 3.81 (t, J = 4.9 Hz, 2H), 3.31 (s, 3H). |
| 459 | 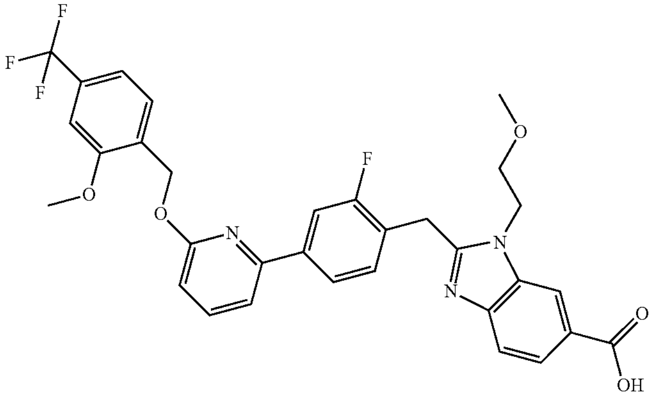 [SMILES: COCCn1c(Cc2ccc(-c3cccc(OCc4ccc(C(F)(F)F)cc4OC)n3)cc2F)nc2ccc(C(=O)O)cc21]<br>2-(2-fluoro-4-(6-((2-methoxy-4-(trifluoromethyl)benzyl)oxy)pyridin-2-yl)benzyl)-1-(2-methoxyethyl)-1H-benzo[d]imidazole-6-carboxylic acid: ES/MS m/z 610.2; $^1$H NMR (400 MHz, Methanol-d4) δ 8.58 (s, 1H), 8.25 (s, 1H), 7.93 (t, J = 10.6 Hz, 2H), 7.80 (q, J = 8.1 Hz, 2H), 7.57 (dt, J = 19.0, 9.5 Hz, 3H), 7.25 (d, J = 7.9 Hz, 2H), 6.91 (d, J = 8.3 Hz, 1H), 5.59 (s, 2H), 4.79 (s, 2H), 3.98 (s, 3H), 3.83 (s, 3H). |
| 460 | 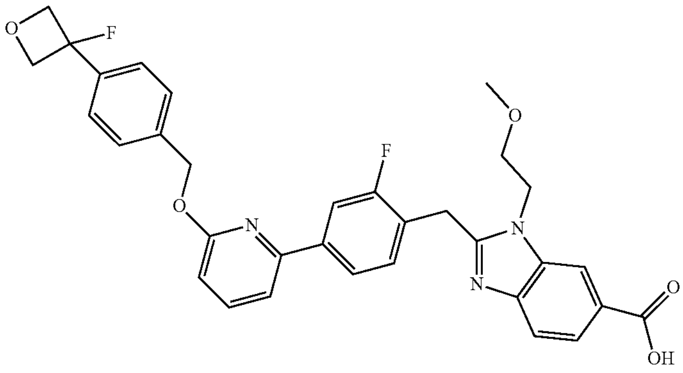 [SMILES: COCCn1c(Cc2ccc(-c3cccc(OCc4ccc(C5(F)COC5)cc4)n3)cc2F)nc2ccc(C(=O)O)cc21]<br>2-(2-fluoro-4-(6-((4-(3-fluorooxetan-3-yl)benzyl)oxy)pyridin-2-yl)benzyl)-1-(2-methoxyethyl)-1H-benzo[d]imidazole-6-carboxylic acid: ES/MS m/z 586.2; $^1$H NMR (400 MHz, Methanol-d4) δ 8.58 (s, 1H), 8.25 (d, J = 8.7 Hz, 1H), 7.95 (t, J = 11.5 Hz, 2H), 7.80 (t, J = 7.2 Hz, 2H), 7.59 (s, 4H), 7.57-7.47 (m, 2H), 6.88 (d, J = 8.2 Hz, 1H), 5.55 (d, J = 2.0 Hz, 2H), 5.04 (dd, J = 21.3, 7.9 Hz, 2H), 4.94 (d, J = 8.1 Hz, 2H), 4.79 (s, 2H), 3.82 (t, J = 4.6 Hz, 2H). |

-continued

| Example | Structure/Name/Characterization |
|---|---|
| 463 | 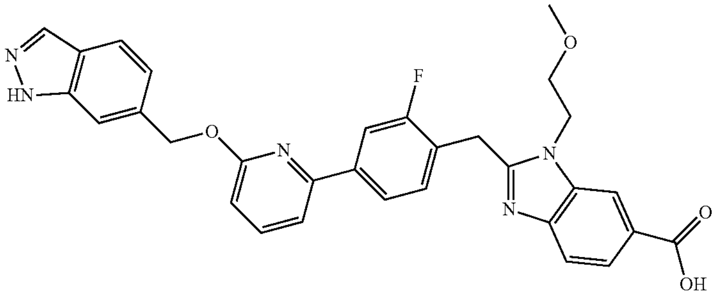 [SMILES: COCCn1c(Cc2ccc(-c3cccc(OCc4ccc5cn[nH]c5c4)n3)cc2F)nc2ccc(C(=O)O)cc21] 2-(4-(6-((1H-indazol-6-yl)methoxy)pyridin-2-yl)-2-fluorobenzyl)-1-(2-methoxyethyl)-1H-benzo[d]imidazole-6-carboxylic acid: ES/MS m/z 552.2; $^{1}$H NMR (400 MHz, Methanol-d4) δ 8.59 (s, 1H), 8.25 (dd, J = 8.6, 1.4 Hz, 1H), 7.99-7.85 (m, 3H), 7.85-7.66 (m, 4H), 7.60-7.42 (m, 5H), 6.91 (d, J = 8.2 Hz, 1H), 5.65 (s, 2H), 4.83 (d, J = 4.7 Hz, 1H), 4.80 (s, 3H), 3.82 (t, J = 4.9 Hz, 2H). |
| 479 | 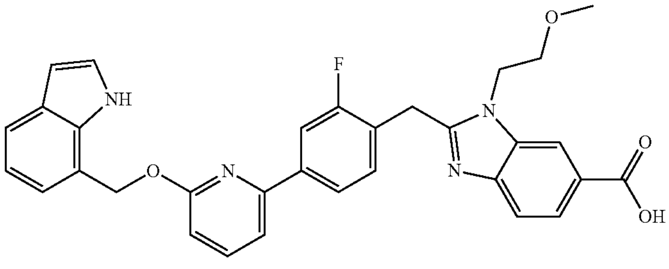 [SMILES: COCCn1c(Cc2ccc(-c3cccc(OCc4cccc5cc[nH]c45)n3)cc2F)nc2ccc(C(=O)O)cc21] 2-(4-(6-((1H-indol-7-yl)methoxy)pyridin-2-yl)-2-fluorobenzyl)-1-(2-methoxyethyl)-1H-benzo[d]imidazole-6-carboxylic acid: ES/MS m/z 551.2; $^{1}$H NMR (400 MHz, Methanol-d4) δ 8.56 (s, 1H), 8.23 (dd, J = 8.6, 1.5 Hz, 1H), 8.10 (t, J = 7.9 Hz, 1H), 8.06-7.90 (m, 3H), 7.78 (d, J = 8.5 Hz, 1H), 7.70-7.44 (m, 4H), 7.32 (d, J = 7.3 Hz, 1H), 7.19 (t, J = 7.6 Hz, 1H), 6.76 (d, J = 3.4 Hz, 1H), 4.94-4.91 (m, 2H), 4.79 (s, 2H), 4.58 (s, 2H), 3.81 (t, J = 4.9 Hz, 2H). |
| 487 | 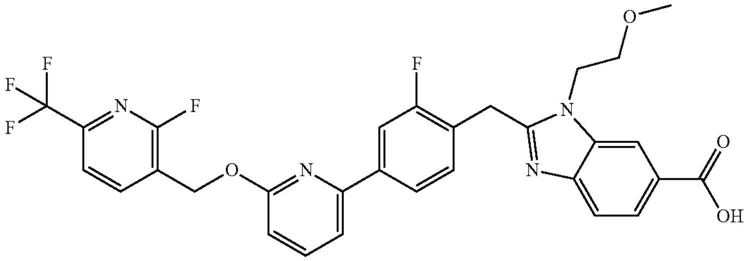 [SMILES: COCCn1c(Cc2ccc(-c3cccc(OCc4ccc(C(F)(F)F)nc4F)n3)cc2F)nc2ccc(C(=O)O)cc21] 2-(2-fluoro-4-(6-((2-fluoro-6-(trifluoromethyl)pyridin-3-yl)methoxy)pyridin-2-yl)benzyl)-1-(2-methoxyethyl)-1H-benzo[d]imidazole-6-carboxylic acid: ES/MS m/z 599.2; $^{1}$H NMR (400 MHz, Methanol-d4) δ 8.54 (s, 1H), 8.29 (t, J = 8.3 Hz, 1H), 8.22 (d, J = 8.6 Hz, 1H), 7.91 (t, J = 8.7 Hz, 2H), 7.80 (dt, J = 30.8, 7.8 Hz, 3H), 7.59 (d, J = 7.5 Hz, 1H), 7.51 (t, J = 8.0 Hz, 1H), 6.95 (d, J = 8.3 Hz, 1H), 5.66 (s, 2H), 4.83-4.78 (m, 1H), 4.76 (s, 2H), 3.81 (t, J = 4.9 Hz, 2H). |
| 494 | 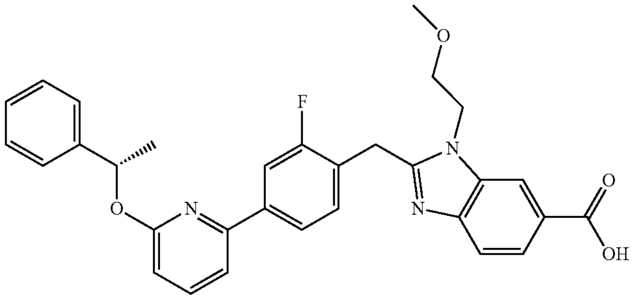 [SMILES: COCCn1c(Cc2ccc(-c3cccc(O[C@@H](C)c4ccccc4)n3)cc2F)nc2ccc(C(=O)O)cc21] |

-continued

| Example | Structure/Name/Characterization |
|---|---|
| | (S)-2-(2-fluoro-4-(6-(1-phenylethoxy)pyridin-2-yl)benzyl)-1-(2-methoxyethyl)-1H-benzo[d]imidazole-6-carboxylic acid: ES/MS m/z 526.2; $^1$H NMR (400 MHz, Methanol, d4) δ 8.52 (d, J = 1.3 Hz, 1H), 8.20 (dd, J = 8.6, 1.5 Hz, 1H), 7.85-7.70 (m, 4H), 7.50-7.41 (m, 4H), 7.37-7.28 (m, 2H), 7.27-7.17 (m, 1H), 6.83 (d, J = 8.2 Hz, 1H), 6.23 (q, J = 6.6 Hz, 1H), 4.77 (t, J = 5.0 Hz, 2H), 4.72 (s, 2H), 3.80 (t, J = 4.9 Hz, 2H), 3.31 (s, 3H), 1.67 (d, J = 6.6 Hz, 3H). |
| 497 | 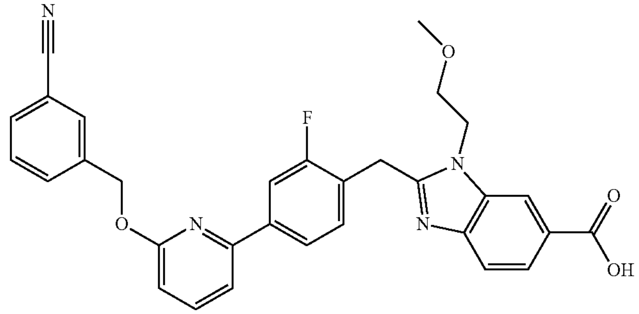 [SMILES: COCCn1c(Cc2ccc(-c3cccc(OCc4cccc(C#N)c4)n3)cc2F)nc2ccc(C(=O)O)cc21] 2-(4-(6-((3-cyanobenzyl)oxy)pyridin-2-yl)-2-fluorobenzyl)-1-(2-methoxyethyl)-1H-benzo[d]imidazole-6-carboxylic acid: ES/MS m/z 537.2; $^1$H NMR (400 MHz, Methanol-d4) δ 8.53 (d, J = 1.3 Hz, 1H), 8.21 (dd, J = 8.6, 1.5 Hz, 1H), 7.97-7.74 (m, 6H), 7.67 (d, J = 7.7 Hz, 1H), 7.61-7.46 (m, 3H), 6.92 (d, J = 8.2 Hz, 1H), 5.58 (s, 2H), 4.79 (t, J = 4.9 Hz, 2H), 4.75 (s, 2H), 3.81 (t, J = 4.9 Hz, 2H), 3.31 (s, 3H). |
| 507 | 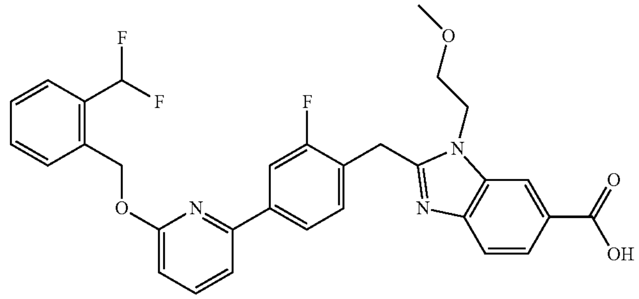 [SMILES: COCCn1c(Cc2ccc(-c3cccc(OCc4ccccc4C(F)F)n3)cc2F)nc2ccc(C(=O)O)cc21] 2-(4-(6-((2-(difluoromethyl)benzyl)oxy)pyridin-2-yl)-2-fluorobenzyl)-1-(2-methoxyethyl)-1H-benzo[d]imidazole-6-carboxylic acid: ES/MS m/z 562.2; $^1$H NMR (400 MHz, Methanol-d4) δ 8.55 (t, J = 1.0 Hz, 1H), 8.22 (dd, J = 8.6, 1.4 Hz, 1H), 7.98-7.88 (m, 2H), 7.85-7.74 (m, 2H), 7.64 (d, J = 8.0 Hz, 2H), 7.59-7.41 (m, 4H), 7.11 (t, J = 55.2 Hz, 1H), 6.90 (d, J = 8.1 Hz, 1H), 5.70 (s, 2H), 4.80 (t, J = 5.0 Hz, 2H), 4.76 (s, 2H), 3.82 (t, J = 5.0 Hz, 2H), 3.32 (s, 3H). |
| 508 | 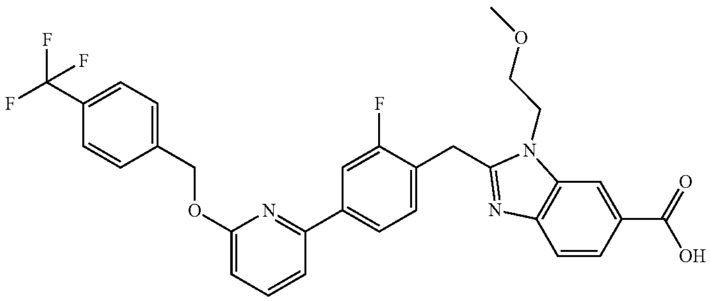 [SMILES: COCCn1c(Cc2ccc(-c3cccc(OCc4ccc(C(F)(F)F)cc4)n3)cc2F)nc2ccc(C(=O)O)cc21] 2-(2-fluoro-4-(6-((4-(trifluoromethyl)benzyl)oxy)pyridin-2-yl)benzyl)-1-(2-methoxyethyl)-1H-benzo[d]imidazole-6-carboxylic acid: ES/MS m/z 580.2; $^1$H NMR (400 MHz, Methanol-d4) δ 8.56 (t, J = 0.9 Hz, 1H), 8.23 (dd, J = 8.6, 1.4 Hz, 1H), 7.97-7.86 (m, 2H), 7.86-7.74 (m, 2H), 7.68 (s, 4H), 7.60-7.46 (m, 2H), 6.92 (d, J = 8.2 Hz, 1H), 5.61 (s, 2H), 4.81 (t, J = 5.0 Hz, 2H), 4.77 (s, 2H), 3.82 (t, J = 4.9 Hz, 2H), 3.32 (s, 3H). |

-continued

| Example | Structure/Name/Characterization |
| --- | --- |
| 511 | 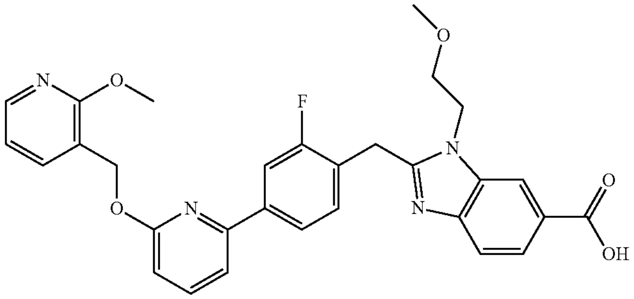 [SMILES: COCCn1c(Cc2ccc(-c3cccc(OCc4cccnc4OC)n3)cc2F)nc2ccc(C(=O)O)cc21] 2-(2-fluoro-4-(6-((2-methoxypyridin-3-yl)methoxy)pyridin-2-yl)benzyl)-1-(2-methoxyethyl)-1H-benzo[d]imidazole-6-carboxylic acid: ES/MS m/z 543.2; $^{1}$H NMR (400 MHz, Methanol-d4) δ 8.54 (s, 1H), 8.21 (dd, J = 8.6, 1.4 Hz, 1H), 8.08 (dd, J = 5.1, 1.8 Hz, 1H), 7.97-7.88 (m, 2H), 7.79 (q, J = 8.1 Hz, 3H), 7.59-7.46 (m, 2H), 7.00-6.86 (m, 2H), 5.51 (s, 2H), 4.80 (t, J = 5.0 Hz, 2H), 4.75 (s, 2H), 4.02 (s, 3H), 3.81 (t, J = 4.9 Hz, 2H), 3.32 (s, 3H). |
| 515 | 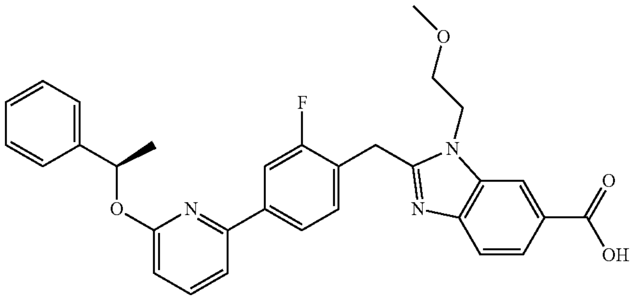 [SMILES: COCCn1c(Cc2ccc(-c3cccc(O[C@H](C)c4ccccc4)n3)cc2F)nc2ccc(C(=O)O)cc21] (R)-2-(2-fluoro-4-(6-(1-phenylethoxy)pyridin-2-yl)benzyl)-1-(2-methoxyethyl)-1H-benzo[d]imidazole-6-carboxylic acid: ES/MS m/z 526.2; $^{1}$H NMR (400 MHz, Methanol-d4) δ 8.52 (d, J = 1.4 Hz, 1H), 8.20 (dd, J = 8.6, 1.4 Hz, 1H), 7.78-7.69 (m, 4H), 7.50-7.41 (m, 4H), 7.32 (t, J = 7.7 Hz, 2H), 7.27-7.18 (m, 1H), 6.83 (d, J = 8.2 Hz, 1H), 6.23 (q, J = 6.6 Hz, 1H), 4.76 (t, J = 5.0 Hz, 2H), 4.72 (s, 2H), 3.80 (t, J = 5.0 Hz, 2H), 3.31 (s, 3H), 1.67 (d, J = 6.6 Hz, 3H). |

Example 458, 2-[[2-fluoro-4-[6-[[2-methoxy-6-(trifluoromethyl)-3-pyridyl]methoxy]-2-pyridyl]phenyl]methyl]-3-(2-methoxyethyl)benzimidazole-5-carboxylic acid Procedure 34

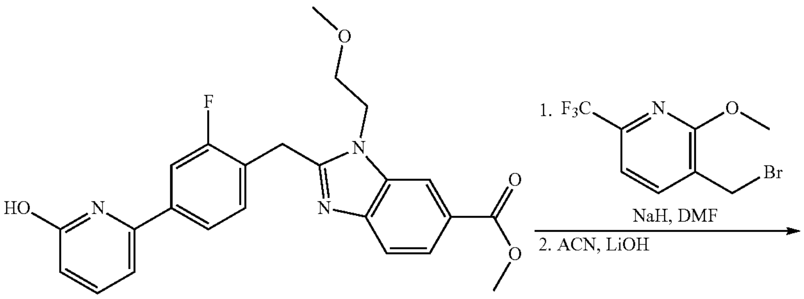

I-109

-continued

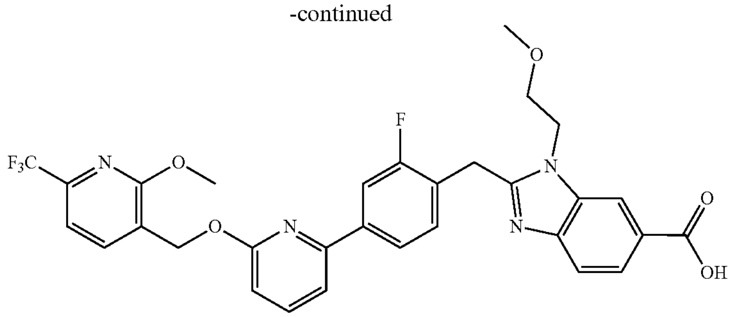

Example 458

2-[[2-fluoro-4-[6-[[2-methoxy-6-(trifluoromethyl)-3-pyridyl]methoxy]-2-pyridyl]phenyl]methyl]-3-(2-methoxy-ethyl)benzimidazole-5-carboxylic acid (Example 458): Methyl 2-[[2-fluoro-4-(6-hydroxy-2-pyridyl)phenyl]methyl]-3-(2-methoxyethyl)benzimidazole-5-carboxylate (50.0 mg, 0.115 mmol) was added to 3-(chloromethyl)-2-methoxy-6-(trifluoromethyl)pyridine (28.5 mg, 0.126 mmol) and sodium hydride (50.0%, 22.0 mg, 0.459 mmol) in DMF (1 mL). The mixture was heated to 80° C. for 4 hours. The mixture was cooled to ambient temperature and 1 M aq. LiOH was added (0.5 mL). The mixture was stirred at 60° C. for 4 hours. The reaction was cooled to ambient temperature and quenched with excess trifluoroacetic acid (0.1 mL). The mixture was purified by RP-HPLC (eluent: water/MeCN 0.1% TFA) to yield the titled product. ES/MS m/z: 611.162 (M+H$^+$); $^1$H NMR (400 MHz, Acetonitrile-d3) δ 8.34 (d, J=11.7 Hz, 1H), 8.04 (s, 1H), 7.94 (d, J=7.5 Hz, 1H), 7.88-7.62 (m, 3H), 7.51 (d, J=7.4 Hz, 1H), 7.43 (s, 1H), 7.36 (d, J=7.5 Hz, 1H), 6.90 (d, J=8.3 Hz, 1H), 5.54 (s, 2H), 4.57 (s, 5H), 4.03 (s, 3H), 3.72 (t, J=5.1 Hz, 2H), 3.23 (s, 2H). 19F NMR (377 MHz, Acetonitrile-d3) δ −69.24, −77.15, −117.89 (dd, J=11.7, 7.8 Hz).

Example 590 and 593. Compounds Prepared Using Procedure 34

Other compounds of the present disclosure prepared using the general route described in Procedure 34 include the following Example.

| Example | Structure/Name/Characterization |
|---|---|
| 590 | 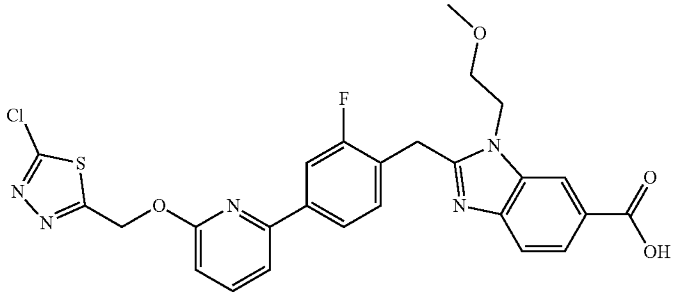<br>2-(4-(6-((5-chloro-1,3,4-thiadiazol-2-yl)methoxy)pyridin-2-yl)-2-fluorobenzyl)-1-(2-methoxyethyl)-1H-benzo[d]imidazole-6-carboxylic acid: ES/MS m/z 577.2; $^1$H NMR (400 MHz, Methanol-d4) δ 8.61-8.49 (m, 1H), 8.20 (dd, J = 8.6, 1.5 Hz, 1H), 8.02 (d, J = 9.8 Hz, 3H), 7.84 (dd, J = 8.2, 7.5 Hz, 1H), 7.78 (dd, J = 8.7, 0.7 Hz, 1H), 7.63 (d, J = 7.4 Hz, 1H), 7.52 (t, J = 7.8 Hz, 1H), 6.89 (d, J = 8.1 Hz, 1H), 5.71 (s, 2H), 4.89 (s, 2H), 4.75 (s, 2H), 3.99 (s, 3H), 3.81 (t, J = 4.9 Hz, 2H). |
| 593 | 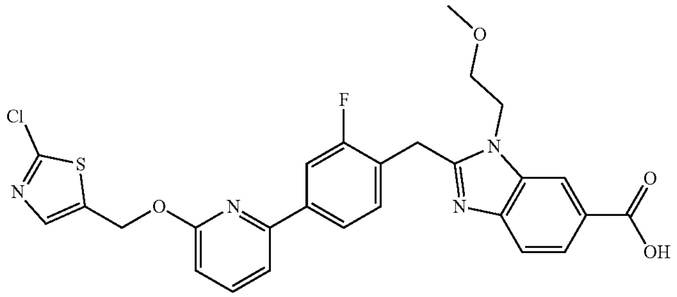 [SMILES: COCCn1c(Cc2ccc(-c3cccc(OCc4cnc(Cl)s4)n3)cc2F)nc2ccc(C(=O)O)cc21]<br>2-(4-(6-((2-chlorothiazol-5-yl)methoxy)pyridin-2-yl)-2-fluorobenzyl)-1-(2-methoxyethyl)-1H-benzo[d]imidazole-6-carboxylic acid: ES/MS m/z 553.2; $^1$H |

-continued

| Example | Structure/Name/Characterization |
|---|---|
| | NMR (400 MHz, DMSO-d6) δ 7.67 (s, 1H), 7.35 (dd, J = 8.5, 1.5 Hz, 1H), 7.20 (d, J = 9.7 Hz, 2H), 7.08-6.83 (m, 2H), 6.79 (d, J = 7.3 Hz, 1H), 6.69 (t, J = 7.8 Hz, 1H), 6.01 (d, J = 8.2 Hz, 1H), 4.87 (s, 1H), 3.91 (s, 2H), 2.97 (t, J = 5.1 Hz, 2H). |

Example 373, 2-(2-fluoro-4-(6-((1-methyl-6-oxo-1,6-dihydropyridin-2-yl)methoxy)pyridin-2-yl)benzyl)-1-(2-methoxyethyl)-1H-benzo[d]imidazole-6-carboxylic acid Procedure 35

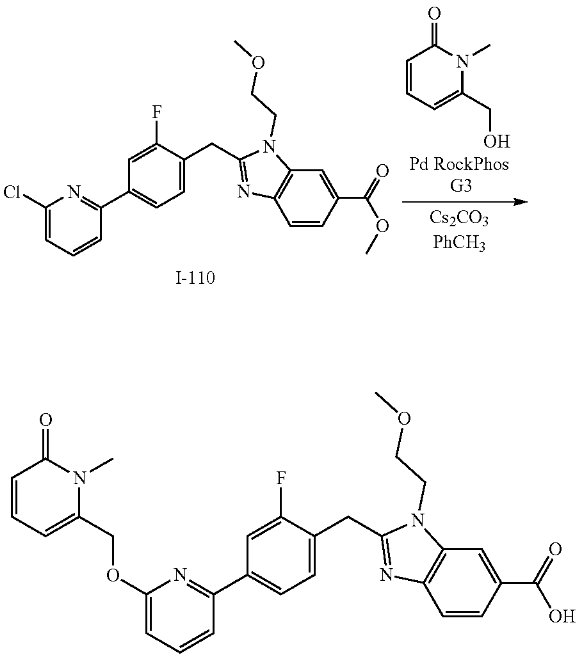

I-110

Example 373

2-(2-fluoro-4-(6-((1-methyl-6-oxo-1,6-dihydropyridin-2-yl)methoxy)pyridin-2-yl)benzyl)-1-(2-methoxyethyl)-1H-benzo[d]imidazole-6-carboxylic acid (Example 373): Methyl 2-((4-(6-chloro-2-pyridyl)-2-fluoro-phenyl)methyl)-3-(2-methoxyethyl)benzimidazole-5-carboxylate (I-110, 50.0 mg, 0.110 mmol), 6-(hydroxymethyl)-1-methyl-pyridin-2-one (23.0 mg, 0.165 mmol), Pd RockPhos G3 (13.9 mg, 0.017 mmol), and cesium carbonate (108 mg, 0.330 mmol) were taken up in toluene (1.5 mL) and the mixture was sparged with argon for 10 minutes. The mixture was then heated to 110° C. overnight. Following this time, the mixture was filtered through Celite, concentrated in vacuo, and purified by RP-HPLC (eluent: MeCN/water with 0.1% TFA) to yield the product (Example 373) as the trifluoroacetate salt. ES/MS: 543.2 ($M+H^+$); $^1H$ NMR (400 MHz, DMSO-d6) δ 8.25 (s, 1H), 8.02-7.77 (m, 4H), 7.65 (dd, J=16.9, 8.0 Hz, 2H), 7.52-7.35 (m, 2H), 6.93 (d, J=8.2 Hz, 1H), 6.41-6.21 (m, 2H), 5.29 (s, 2H), 4.60 (t, J=5.1 Hz, 2H), 4.46 (s, 2H), 3.89 (s, 3H), 3.67 (t, J=5.0 Hz, 2H), 3.21 (s, 3H).

Example 374, 2-(2-fluoro-4-(6-((1-methyl-2-oxo-1,2-dihydropyridin-3-yl)methoxy)pyridin-2-yl)benzyl)-1-(2-methoxyethyl)-1H-benzo[d]imidazole-6-carboxylic acid Procedure 36

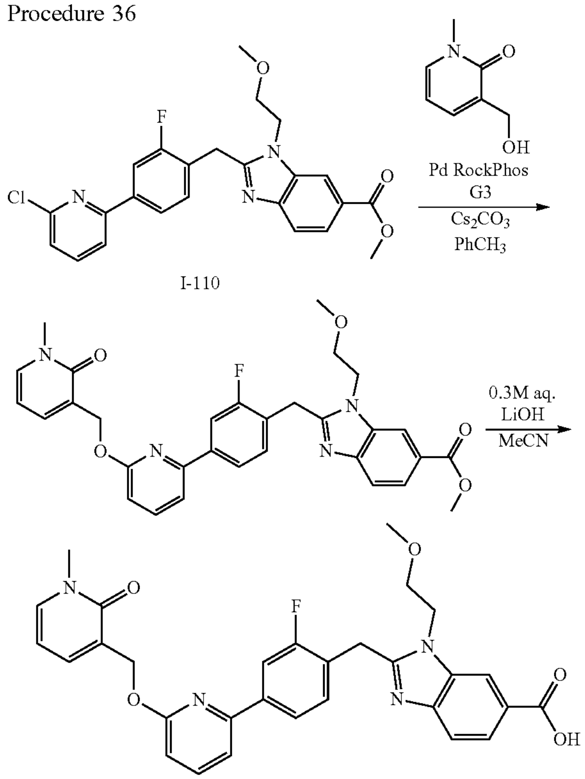

I-110

Example 374

Methyl 2-(2-fluoro-4-(6-((1-methyl-2-oxo-1,2-dihydropyridin-3-yl)methoxy)pyridin-2-yl)benzyl)-1-(2-methoxyethyl)-1H-benzo[d]imidazole-6-carboxylate: Methyl 2-((4-(6-chloro-2-pyridyl)-2-fluoro-phenyl)methyl)-3-(2-methoxyethyl)benzimidazole-5-carboxylate (I-110, 100 mg, 0.220 mmol), 3-(hydroxymethyl)-1-methyl-pyridin-2-one (66.6 mg, 0.479 mmol), Pd RockPhos G3 (27.7 mg, 0.033 mmol) and cesium carbonate (215 mg, 0.661 mmol) were taken up in toluene (1.5 mL). Argon was bubbled through the mixture for 3 minutes and the mixture was heated to 110° C. for 16 h. Following this time, the mixture was filtered through Celite (washed with $CH_2Cl_2$), concentrated in vacuo, and purified by normal phase column chromatography (eluent: $EtOAc/CH_2Cl_2$) to afford the product. ES/MS: 557.2 ($M+H^+$).

2-(2-fluoro-4-(6-((1-methyl-2-oxo-1,2-dihydropyridin-3-yl)methoxy)pyridin-2-yl)benzyl)-1-(2-methoxyethyl)-1H-benzo[d]imidazole-6-carboxylic acid (Example 374): Methyl 2-(2-fluoro-4-(6-((1-methyl-6-oxo-1,6-dihydropyridin-2-yl)methoxy)pyridin-2-yl)benzyl)-1-(2-methoxyethyl)-1H-benzo[d]imidazole-6-carboxylate (123 mg, 0.221 mmol) was taken up in acetonitrile (2.0 mL) and lithium hydroxide (0.3 M, 2.21 mL, 0.663 mmol) was added. The mixture was heated to 50° C. for 1 hour then cooled to RT and diluted with 5% aqueous citric acid to a pH~5. The mixture was extracted with EtOAc (3x5 mL) and the combined organic extracts dried over $MgSO_4$ and concentrated in vacuo. The material was purified by RP-HPLC (eluent: MeCN/water gradient with 0.1% TFA) to afford the title compound Example 374 as the trifluoroacetate salt. ES/MS: 543.2 ($M+H^+$); $^1H$ NMR (400 MHz, DMSO-d6) δ 8.19 (d, J=1.5 Hz, 1H), 7.95-7.75 (m, 4H), 7.70 (dd, J=6.8, 2.1 Hz, 1H), 7.67-7.49 (m, 3H), 7.42 (t, J=8.0 Hz, 1H), 6.88 (d, J=8.2 Hz, 1H), 6.24 (t, J=6.8 Hz, 1H), 5.30 (s, 2H), 4.56 (t, J=5.1 Hz, 2H), 4.43 (s, 2H), 3.66 (t, J=5.1 Hz, 2H), 3.48 (s, 3H), 3.21 (s, 3H).

Example 694. Compounds Prepared Using Procedure 36

Other compounds of the present disclosure prepared using the general route described in Procedure 36 include the following Example.

| Example | Structure/Name/Characterization |
|---|---|
| 694 | 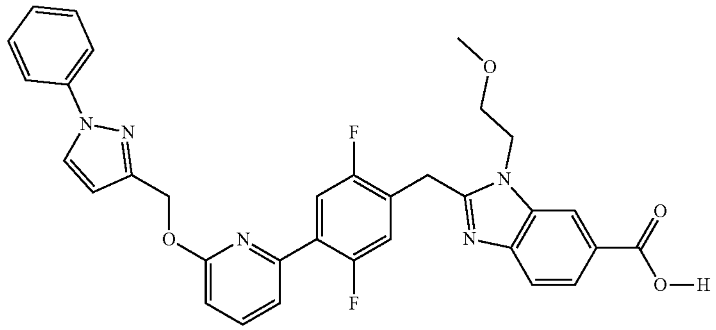 [SMILES: COCCn1c(Cc2cc(F)c(-c3cccc(OCc4ccn(-c5ccccc5)n4)n3)cc2F)nc2ccc(C(=O)O)cc21] ES/MS (M + H+) 596.2; 1H NMR (400 MHz, DMSO-d6) δ 8.49 (d, J = 2.5 Hz, 1H), 8.28 (d, J = 1.5 Hz, 1H), 8.02 (dd, J = 10.5, 6.5 Hz, 1H), 7.91-7.78 (m, 4H), 7.65 (d, J = 8.4 Hz, 1H), 7.53 (dd, J = 7.5, 1.7 Hz, 1H), 7.50-7.45 (m, 2H), 7.42 (dd, J = 11.6, 6.1 Hz, 1H), 7.33-7.25 (m, 1H), 6.94 (d, J = 8.3 Hz, 1H), 6.62 (d, J = 2.5 Hz, 1H), 5.52 (s, 2H), 4.65 (t, J = 5.1 Hz, 2H), 4.52 (s, 2H), 3.70 (t, J = 5.0 Hz, 2H), 3.22 (s, 3H). Multiplet Report 19F NMR (376 MHz, DMSO-d6) δ −75.03, −120.82−−121.85 (m), −121.97−−123.11 (m). |

Example 372. 2-(4-(2-(1-(4-chloro-2-fluorophenyl)ethoxy)pyridin-3-yl)-2,6-difluorobenzyl)-1-(2-methoxyethyl)-1H-benzo[d]imidazole-6-carboxylic acid Procedure 37

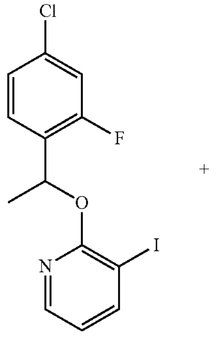

I-61

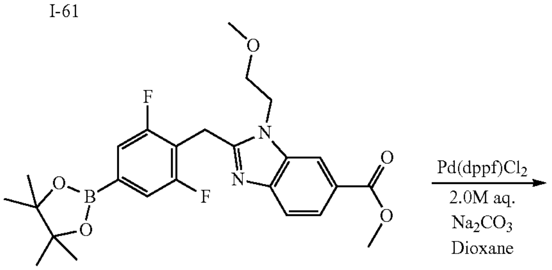

I-43

-continued

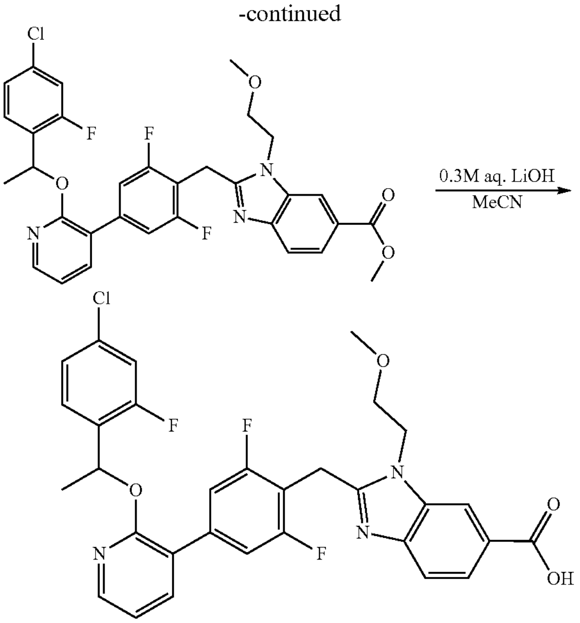

Example 372

Methyl 2-(4-(2-(1-(4-chloro-2-fluorophenyl)ethoxy)pyridin-3-yl)-2,6-difluorobenzyl)-1-(2-methoxyethyl)-1H-benzo[d]imidazole-6-carboxylate: 2-(1-(4-chloro-2-fluorophenyl)ethoxy)-3-iodopyridine (I-61, 65.0 mg, 0.134 mmol), methyl 2-(2,6-difluoro-4-(4,4,5,5-tetramethyl-1,3,2-dioxaborolan-2-yl)benzyl)-1-(2-methoxyethyl)-1H-benzo[d]imidazole-6-carboxylate (I-43, 50.5 mg, 0.134 mmol), and Pd(dppf)$Cl_2$ (0.0149 g, 0.020 mmol) were taken up in 1,4-dioxane (1.0 mL) and aqueous sodium carbonate (2.0 M, 0.20 mL, 0.401 mmol) was added. The mixture was sparged with argon for 5 minutes, then the mixture was sealed and heated to 90° C. After 1 hour, the reaction was complete as determined by LC/MS analysis and the mixture was cooled to RT, filtered through Celite, and concentrated in vacuo. The residue was purified by normal phase column chromatography (eluent: EtOAc/hexanes gradient) to afford the product. ES/MS: 610.2 (M+H$^+$).

2-(4-(2-(1-(4-Chloro-2-fluorophenyl)ethoxy)pyridin-3-yl)-2,6-difluorobenzyl)-1-(2-methoxyethyl)-1H-benzo[d]imidazole-6-carboxylic acid (Example 372): Methyl 2-(4-(2-(1-(4-chloro-2-fluorophenyl)ethoxy)pyridin-3-yl)-2,6-difluorobenzyl)-1-(2-methoxyethyl)-1H-benzo[d]imidazole-6-carboxylate (74.6 mg, 0.122 mmol) was taken up in acetonitrile (1.2 mL) and aqueous lithium hydroxide (0.3 M, 1.22 mL, 0.367 mmol) was added. The reaction vessel was sealed and heated to 100° C. for 2 minutes then cooled to RT and diluted with 5% aqueous citric acid to a pH~5. The mixture was extracted with EtOAc (3×5 mL) and the combined organic extracts dried over $MgSO_4$ and concentrated in vacuo. The material was purified by RP-HPLC (eluent: MeCN/water gradient with 0.1% TFA) to afford (Example 372) as the trifluoroacetate salt. ES/MS: 596.2 (M+H$^+$); $^1$H NMR (400 MHz, DMSO-d6) δ 8.27 (d, J=1.5 Hz, 1H), 8.16 (dd, J=5.0, 1.9 Hz, 1H), 7.95 (dd, J=7.4, 1.9 Hz, 1H), 7.84 (dd, J=8.5, 1.6 Hz, 1H), 7.62 (d, J=8.5 Hz, 1H), 7.53-7.37 (m, 4H), 7.25 (dd, J=8.4, 2.1 Hz, 1H), 7.13 (dd, J=7.4, 4.9 Hz, 1H), 6.42 (q, J=6.5 Hz, 1H), 4.69 (t, J=5.0 Hz, 2H), 4.52 (s, 2H), 3.73 (t, J=5.0 Hz, 2H), 3.24 (s, 3H), 1.62 (d, J=6.6 Hz, 3H).

Example 383. 2-(4-(6-((4-cyano-2-fluorobenzyl)oxy)pyridin-2-yl)-2-((methoxycarbonyl)amino)benzyl)-1-(2-methoxyethyl)-1H-benzo[d]imidazole-6-carboxylic Acid Procedure 38

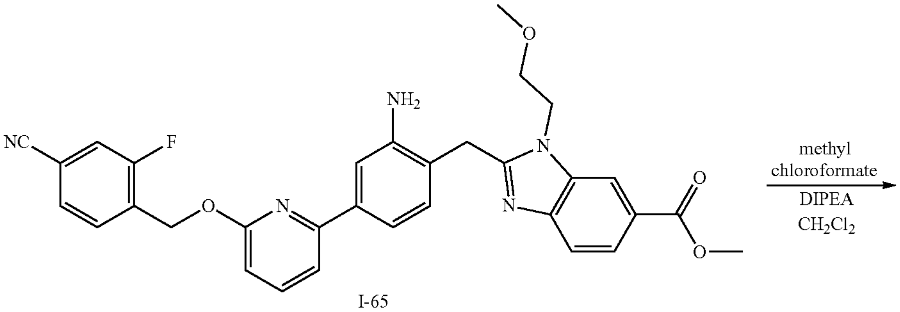

I-65

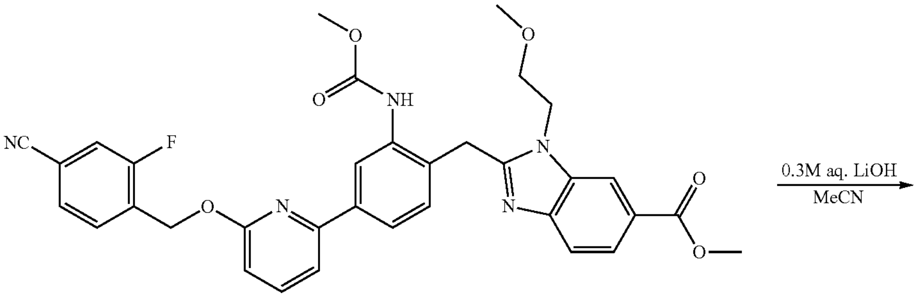

-continued

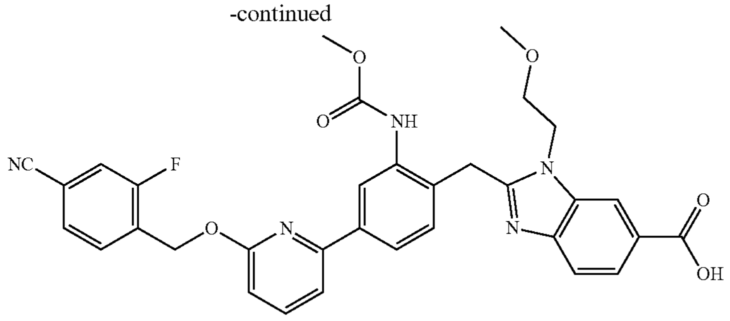

Example 383

Methyl 2-(4-(6-((4-cyano-2-fluorobenzyl)oxy)pyridin-2-yl)-2-((methoxycarbonyl)amino)benzyl)-1-(2-methoxyethyl)-1H-benzo[d]imidazole-6-carboxylate: A solution of methyl 2-(2-amino-4-(6-((4-cyano-2-fluorobenzyl)oxy)pyridin-2-yl)benzyl)-1-(2-methoxyethyl)-1H-benzo[d]imidazole-6-carboxylate (I-65, 36.1 mg, 0.064 mmol) in dichloromethane (1.0 mL) was cooled to 0° C. and N,N-diisopropylethylamine (0.056 mL, 0.319 mmol) was added, followed by methyl chloroformate (0.010 mL, 0.128 mmol). Following this addition, the mixture was warmed to RT and stirred for 5 minutes, at which time the reaction was determined complete by LC/MS analysis. The mixture was diluted with water (5 mL) and extracted with $CH_2Cl_2$ (3×5 mL). The combined organics extracts were dried over $MgSO_4$ and concentrated in vacuo. The residue was used in the subsequent reaction without further purification. ES/MS: 624.3 ($M+H^+$);

2-(4-(6-((4-Cyano-2-fluorobenzyl)oxy)pyridin-2-yl)-2-((methoxycarbonyl)amino)benzyl)-1-(2-methoxyethyl)-1H-benzo[d]imidazole-6-carboxylic acid (Example 383): Methyl 2-(4-(6-((4-cyano-2-fluorobenzyl)oxy)pyridin-2-yl)-2-((methoxycarbonyl)amino)benzyl)-1-(2-methoxyethyl)-1H-benzo[d]imidazole-6-carboxylate (39.8 mg, 0.064 mmol) was taken up in acetonitrile (1.0 mL) and lithium hydroxide (0.3 M, 0.64 mL, 0.191 mmol) was added. The mixture was heated to 50° C. for 20 minutes then cooled to RT and diluted with 5% aqueous citric acid to a pH~5. The mixture was extracted with EtOAc (3×5 mL) and the combined organic extracts dried over $MgSO_4$ and concentrated in vacuo. The material was purified by RP-HPLC (eluent: MeCN/water gradient with 0.1% TFA) to afford (Example 383) as the trifluoroacetate salt. ES/MS: 610.2 ($M+H^+$); $^1H$ NMR (400 MHz, DMSO-d6) δ 9.52 (s, 1H), 8.26 (s, 1H), 8.15 (s, 1H), 7.94-7.82 (m, 3H), 7.78 (t, J=7.7 Hz, 2H), 7.71 (dd, J=8.0, 1.6 Hz, 1H), 7.65 (d, J=8.4 Hz, 1H), 7.55 (d, J=7.5 Hz, 1H), 7.33 (d, J=8.2 Hz, 1H), 6.91 (d, J=8.1 Hz, 1H), 5.60 (s, 2H), 4.57 (s, 2H), 4.43 (s, 2H), 3.66 (s, 3H), 3.63 (t, J=5.1 Hz, 1H), 3.20 (s, 3H).

Example 387. 2-(4-(6-((4-cyano-2-fluorobenzyl)oxy)pyridin-2-yl)-2-(methylsulfonyl)benzyl)-1-(2-methoxyethyl)-1H-benzo[d]imidazole-6-carboxylic acid Procedure 39

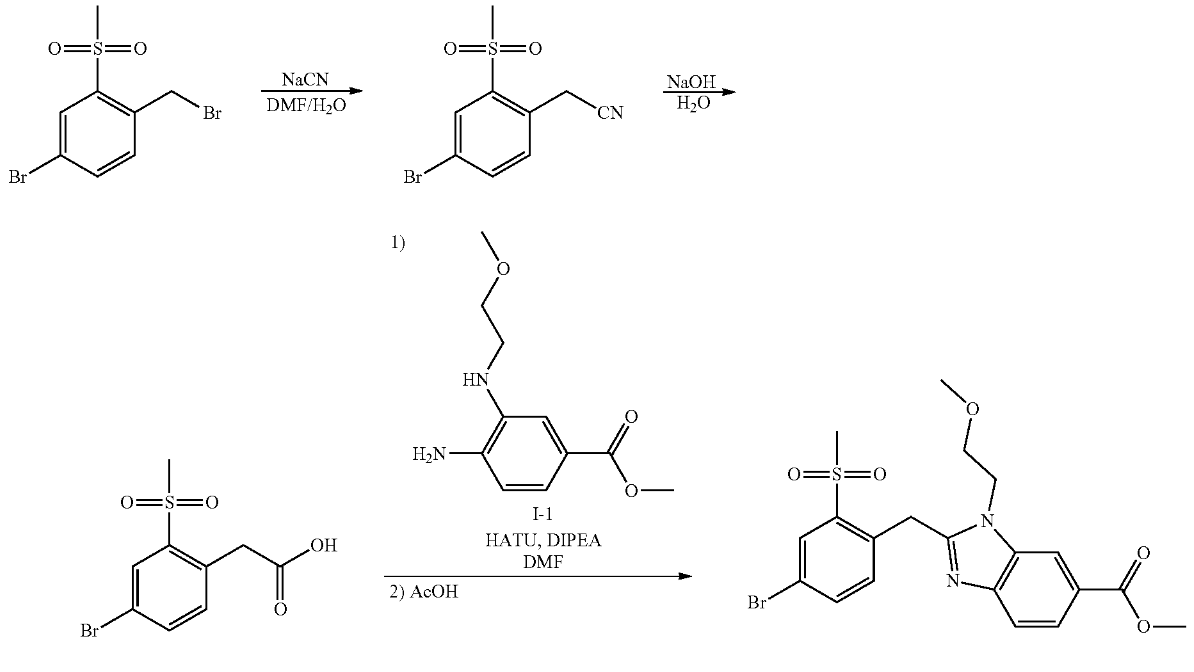

-continued

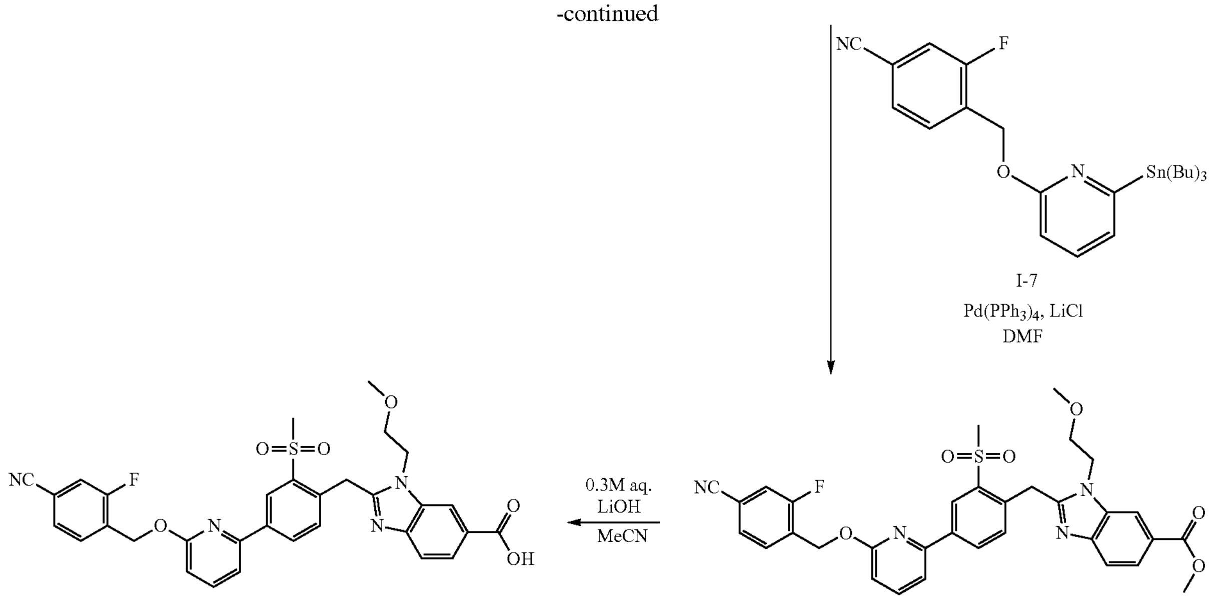

Example 387

2-(4-Bromo-2-(methylsulfonyl)phenyl)acetonitrile: 4-Bromo-1-(bromomethyl)-2-methylsulfonylbenzene (500 mg, 1.52 mmol) was taken up in DMF (4.5 mL) and water (0.575 mL) and sodium cyanide (114 mg, 2.29 mmol) was added. The mixture was stirred at RT overnight. Following this time, the reaction was quenched with 1:1 water:saturated aqueous sodium bicarbonate (50 mL) and extracted with EtOAc (3×50 mL). The combined organic extracts were dried over $MgSO_4$, concentrated in vacuo, and purified by normal phase column chromatography (eluent: 10-60% EtOAc/hexanes) to afford the product. $^1$H NMR (400 MHz, Chloroform-d) δ 8.26 (d, J=2.1 Hz, 1H), 7.85 (dd, J=8.2, 2.2 Hz, 1H), 7.56 (d, J=8.2 Hz, 1H), 4.29 (s, 2H), 3.20 (s, 3H).

2-(4-Bromo-2-(methylsulfonyl)phenyl)acetic acid: 2-(4-Bromo-2-methylsulfonylphenyl)acetonitrile (168 mg, 0.611 mmol) was taken up in aqueous sodium hydroxide (2.0 M, 3.1 mL, 6.11 mmol) and the mixture was heated to reflux overnight. The mixture was then cooled to RT and acidified to pH~2 with 1N aqueous hydrochloric acid. The resultant precipitate was collected via vacuum filtration, washed with water (3×10 mL), and dried under reduced pressure to yield to the product. $^1$H NMR (400 MHz, DMSO-$d_6$) δ 12.55 (s, 1H), 8.05 (d, J=2.2 Hz, 1H), 7.91 (dd, J=8.2, 2.2 Hz, 1H), 7.48 (d, J=8.2 Hz, 1H), 4.05 (s, 2H), 3.32 (s, 3H).

Methyl 2-(4-bromo-2-(methylsulfonyl)benzyl)-1-(2-methoxyethyl)-1H-benzo[d]imidazole-6-carboxylate: 2-(4-Bromo-2-(methylsulfonyl)phenyl)acetic acid (139 mg, 0.474 mmol), methyl 4-amino-3-(2-methoxyethylamino) benzoate (I-1, 128 mg, 0.569 mmol), and HATU (216 mg, 0.569 mmol) were taken up in N,N-dimethylformamide (1.5 mL) and N,N-diisopropylethylamine (0.413 mL, 2.37 mmol) was added. The mixture was stirred at RT for 2 hours then diluted with saturated aqueous $NH_4Cl$ (10 mL) and extracted with EtOAc (3×7 mL). The combined organics were dried over $MgSO_4$ and concentrated in vacuo. The resulting residue was taken up in acetic acid (1.5 mL) and the mixture heated to 100° C. for 1 hour. Following this time, the mixture was cooled to RT, concentrated in vacuo, and the material purified by normal phase column chromatography (eluent: EtOAc/$CH_2Cl_2$) to yield the product. ES/MS: 481.0 (M+H$^+$).

Methyl 2-(4-(6-((4-cyano-2-fluorobenzyl)oxy)pyridin-2-yl)-2-(methylsulfonyl)benzyl)-1-(2-methoxyethyl)-1H-benzo[d]imidazole-6-carboxylate: Methyl 2-(4-bromo-2-(methylsulfonyl)benzyl)-1-(2-methoxyethyl)-1H-benzo[d] imidazole-6-carboxylate (50.0 mg, 0.104 mmol), 3-fluoro-4-(((6-(tributylstannyl)pyridin-2-yl)oxy)methyl) benzonitrile (I-7, 53.7 mg, 0.104 mmol), lithium chloride (13.2 mg, 0.312 mmol), and $Pd(PPh_3)_4$ (24.0 mg, 0.021 mmol) were taken up in N,N-dimethylformamide (0.5 mL) and the mixture was sparged with argon for 5 minutes. The mixture was then heated to 100° C. for 20 hours. Following this time, the mixture was loaded directly onto $SiO_2$ for purification by normal phase column chromatography (eluent: EtOAc/hexanes) which afforded the desired product. ES/MS: 629.2 (M+H$^+$).

2-(4-(6-((4-Cyano-2-fluorobenzyl)oxy)pyridin-2-yl)-2-(methylsulfonyl)benzyl)-1-(2-methoxyethyl)-1H-benzo[d] imidazole-6-carboxylic acid (Example 387): Methyl 2-(4-(6-((4-cyano-2-fluorobenzyl)oxy)pyridin-2-yl)-2-(methylsulfonyl)benzyl)-1-(2-methoxyethyl)-1H-benzo[d] imidazole-6-carboxylate (18.5 mg, 0.029 mmol) was taken up in acetonitrile (0.6 mL) and aqueous lithium hydroxide (0.3 M, 0.490 mL, 0.147 mmol) was added. The reaction vessel was sealed and heated to 100° C. for 5 minutes then cooled to RT and diluted with 5% aqueous citric acid to a pH~5. The mixture was extracted with EtOAc (3×5 mL) and the combined organic extracts dried over $MgSO_4$ and concentrated in vacuo. The material was purified by RP-HPLC (eluent: MeCN/water gradient with 0.1% TFA) to afford (Example 387) as the trifluoroacetate salt. ES/MS: 615.3 (M+H$^+$); $^1$H NMR (400 MHz, DMSO-d6) δ 8.61 (d, J=2.0 Hz, 1H), 8.32 (d, J=8.2 Hz, 1H), 8.22 (s, 1H), 7.92 (dd, J=9.2, 5.8 Hz, 2H), 7.86-7.76 (m, 2H), 7.72 (t, J=7.0 Hz, 2H), 7.56 (dd, J=8.3, 5.2 Hz, 2H), 6.99 (d, J=8.2 Hz, 1H), 5.63 (s, 2H), 4.88 (s, 2H), 4.59 (s, 2H), 3.70 (t, J=5.1 Hz, 2H), 3.25 (s, 3H), 3.23 (s, 3H).

Example 389. 2-(4-(6-((4-cyano-2-fluorobenzyl) oxy)pyridin-2-yl)-2-fluorobenzyl)-1-(cyclopropylmethyl)-1H-benzo[d]imidazole-6-carboxylic acid Procedure 40

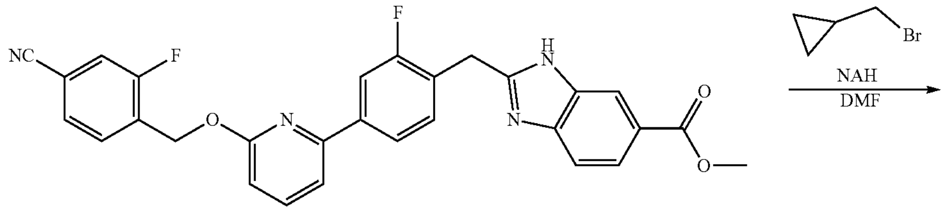

I-63

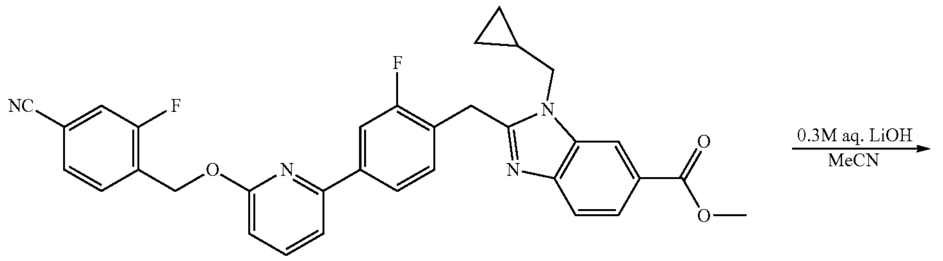

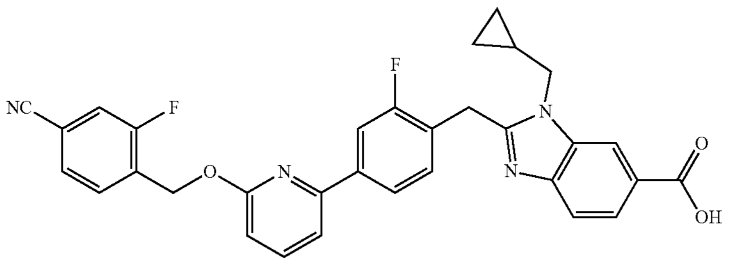

Example 389

Methyl 2-(4-(6-((4-cyano-2-fluorobenzyl)oxy)pyridin-2-yl)-2-fluorobenzyl)-1-(cyclopropylmethyl)-1H-benzo[d]imidazole-6-carboxylate: Methyl 2-(4-(6-((4-cyano-2-fluorobenzyl)oxy)pyridin-2-yl)-2-fluorobenzyl)-1H-benzo[d]imidazole-6-carboxylate (I-63, 40.0 mg, 0.078 mmol) was taken up in N,N-dimethylformamide (0.8 mL) and sodium hydride (60.0% by weight, 3.6 mg, 0.094 mmol) was added. (Bromomethyl)cyclopropane (12.7 mg, 0.94 mmol) was then added and the mixture was stirred at RT overnight. Following this time, the mixture was diluted with water (5 mL) and EtOAc (5 mL). The organic phase was collected and the aqueous phase was extracted with EtOAc (2x5 mL). The combined organics extracts were dried over $MgSO_4$, concentrated in vacuo, and purified by normal phase column chromatography (eluent: EtOAc/$CH_2Cl_2$ gradient) to afford the product as a 2:1 mixture with the N3-alkylated isomer. ES/MS: 565.2 ($M+H^+$)

2-(4-(6-((4-cyano-2-fluorobenzyl)oxy)pyridin-2-yl)-2-fluorobenzyl)-1-(cyclopropylmethyl)-1H-benzo[d]imidazole-6-carboxylic acid (Example 389): Methyl 2-(4-(6-((4-cyano-2-fluorobenzyl)oxy)pyridin-2-yl)-2-fluorobenzyl)-1-(cyclopropylmethyl)-1H-benzo[d]imidazole-6-carboxylate (12.2 mg, 0.022 mmol) was taken up in acetonitrile (0.75 mL) and aqueous lithium hydroxide (0.3 M, 0.36 mL, 0.108 mmol) was added. The mixture was heated to 50° C. for 1 hour then cooled to RT and diluted with 5% aqueous citric acid to a pH~5. The mixture was extracted with EtOAc (3x5 mL) and the combined organic extracts dried over $MgSO_4$ and concentrated in vacuo. The material was purified by RP-HPLC (eluent: MeCN/water gradient with 0.1% TFA) to yield (Example 389) as the trifluoroacetate salt. ES/MS: 551.2 ($M+H^+$); $^1H$ NMR (400 MHz, DMSO-d6) δ 8.13 (d, J=1.5 Hz, 1H), 8.01-7.81 (m, 6H), 7.81-7.72 (m, 3H), 7.72-7.63 (m, 1H), 7.46 (t, J=8.0 Hz, 1H), 6.94 (d, J=8.2 Hz, 1H), 5.62 (s, 3H), 4.46 (s, 3H), 4.27 (d, J=7.0 Hz, 2H), 1.25 (d, J=4.9 Hz, 1H), 0.65-0.33 (m, 5H).

Example 345. Compound Prepared Using Procedure 40

Other compounds of the present disclosure prepared using the general route described in Procedure 40 include the following Example.

| Example | Structure/Name/Characterization |
|---|---|
| 345 | 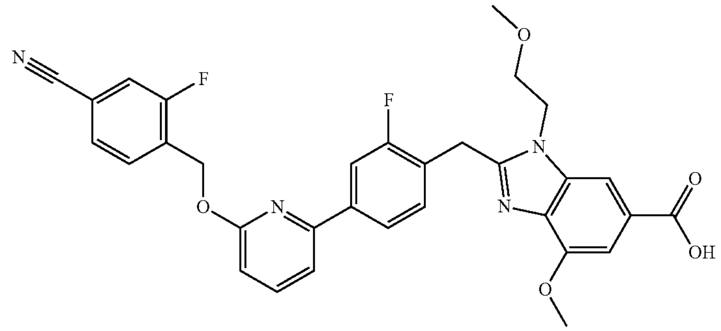 [SMILES: COCCn1c(Cc2ccc(-c3cccc(OCc4ccc(C#N)cc4F)n3)cc2F)nc2c(OC)cc(C(=O)O)cc21] 2-(4-(6-((4-cyano-2-fluorobenzyl)oxy)pyridin-2-yl)-2-fluorobenzyl)-4-methoxy-1-(2-methoxyethyl)-1H-benzo[d]imidazole-6-carboxylic acid: ES/MS m/z 585.2; $^1$H NMR (400 MHz, DMSO-d6) δ 7.97-7.82 (m, 4H), 7.80-7.70 (m, 3H), 7.67 (d, J = 7.4 Hz, 1H), 7.46-7.34 (m, 2H), 6.94 (d, J = 8.2 Hz, 1H), 5.62 (s, 2H), 4.61 (t, J = 5.3 Hz, 2H), 4.43 (s, 2H), 3.99 (s, 3H), 3.68 (t, J = 5.2 Hz, 2H), 3.22 (s, 3H). |
Example 391. 2-(2-cyano-4-(6-((4-cyano-2-fluorobenzyl)oxy)pyridin-2-yl)-3-fluorobenzyl)-1-(2-methoxyethyl)-1H-benzo[d]imidazole-6-carboxylic acid
Procedure 41
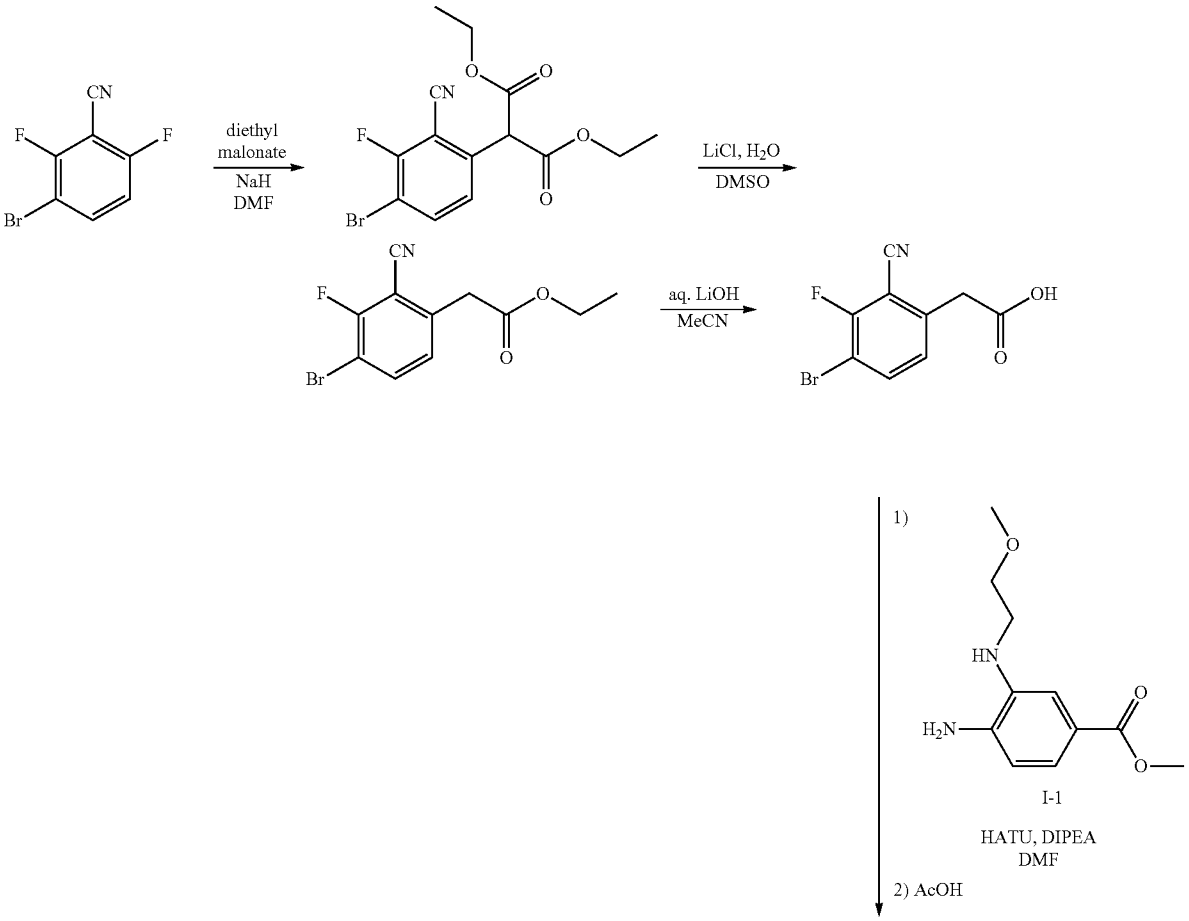

-continued

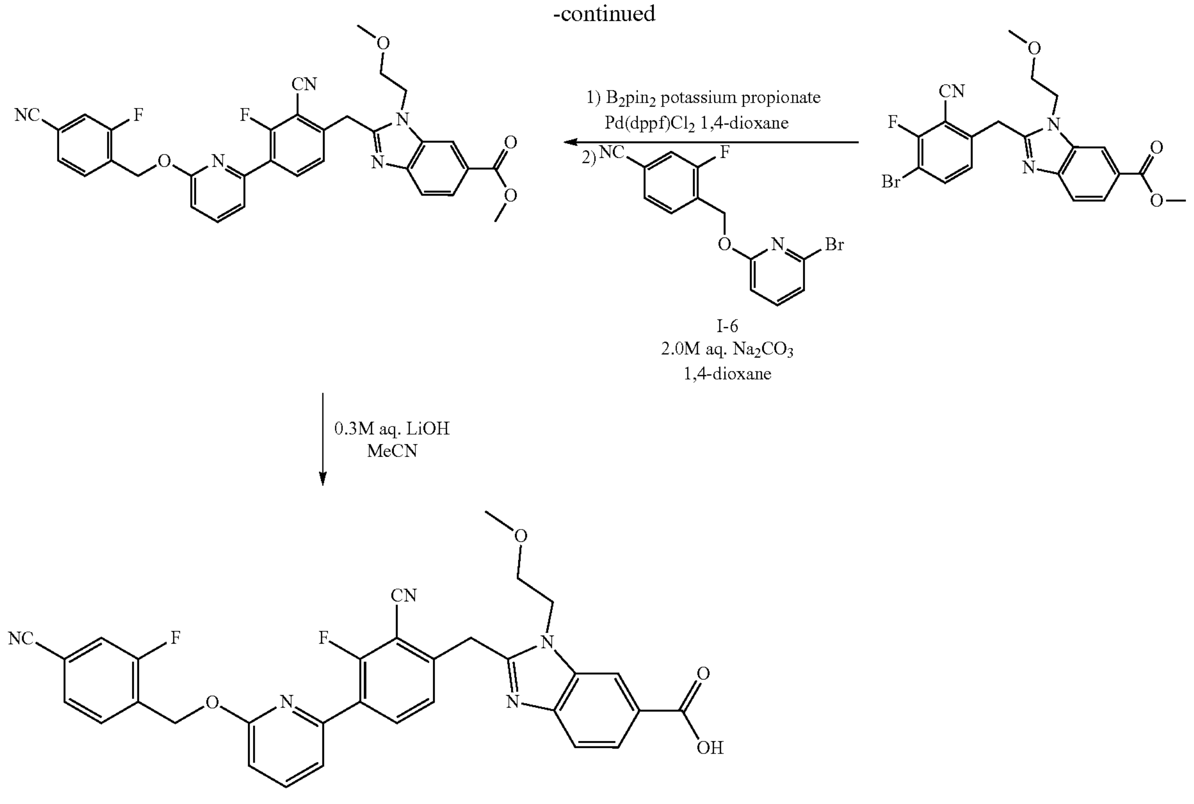

Example 391

Diethyl 2-(4-bromo-2-cyano-3-fluorophenyl)malonate: A suspension of sodium hydride (250 mg, 10.9 mmol) in dioxane (5 mL) was cooled to 0° C. To this was added a solution of 3-bromo-2,6-difluoro-benzonitrile (989 mg, 4.54 mmol) and diethyl propanedioate (836 mg, 5.22 mmol) in dioxane (5 mL) slowly dropwise. Following addition, the mixture was warmed to RT and stirred overnight. Following completion, the mixture was diluted with EtOAc (25 mL) and water (25 mL) and the organic phase collected. The aqueous phase was extracted with EtOAc (2×20 mL) and the combined organic extracts were dried over $MgSO_4$, concentrated in vacuo, and purified by normal phase column chromatography (eluent: EtOAc/hexanes gradient) to afford the desired product. ES/MS: 358.0 ($M+H^+$); $^1H$ NMR (400 MHz, Chloroform-d) δ 7.84 (dd, J=9.0, 5.3 Hz, 1H), 7.14 (dd, J=9.0, 7.7 Hz, 1H), 5.44 (d, J=0.9 Hz, 1H), 4.34 (qd, J=7.1, 1.2 Hz, 4H), 1.35 (t, J=7.1 Hz, 6H).

Ethyl 2-(4-bromo-2-cyano-3-fluorophenyl)acetate: Diethyl 2-(4-bromo-2-cyano-3-fluorophenyl)malonate (211 mg, 0.589 mmol) was taken up in DMSO (2.8 mL) and lithium chloride (25.0 mg, 0.589 mmol) and water (0.014 mL, 0.766 mmol) were added. The mixture was heated to 100° C. for 5 hours. Following this time, the mixture was diluted with EtOAc (10 mL) and water (10 mL) and the organic phase collected. The aqueous phase was extracted with EtOAc (2×5 mL) and the combined organic extracts were dried over $MgSO_4$, concentrated in vacuo, and purified by normal phase column chromatography (eluent: EtOAc/hexanes gradient) to afford the desired product. $^1H$ NMR (400 MHz, Chloroform-d) δ 7.81 (dd, J=9.0, 5.3 Hz, 1H), 7.10 (dd, J=9.0, 8.0 Hz, 1H), 4.25 (q, J=7.1 Hz, 2H), 4.08 (s, 2H), 1.31 (t, J=7.1 Hz, 3H).

2-(4-Bromo-2-cyano-3-fluorophenyl)acetic acid: Ethyl 2-(4-bromo-2-cyano-3-fluorophenyl)acetate (371 mg, 1.30 mmol) was taken up in acetonitrile (5.2 mL) and aqueous lithium hydroxide (1.0 M, 2.59 mmol, 2.6 mL) was added. The mixture was stirred at RT for 1 hour. Following this time, the mixture was concentrated in vacuo to remove the organics, and the resulting aqueous solution was acidified to pH~3. The precipitate was collected via vacuum filtration, washed with water (3×2 mL), and dried under high pressure to afford the product. ES/MS: 258.0 ($M+H^+$)

Methyl 2-(4-bromo-2-cyano-3-fluorobenzyl)-1-(2-methoxyethyl)-1H-benzo[d]imidazole-6-carboxylate: 2-(4-Bromo-2-cyano-3-fluorophenyl)acetic acid (323 mg, 1.25 mmol), methyl 4-amino-3-(2-methoxyethylamino)benzoate (I-1, 336 mg, 1.50 mmol), and HATU (570 mg, 1.50 mmol) were taken up in N,N-dimethylformamide (5.0 mL) and N,N-diisopropylethylamine (1.1 mL, 6.25 mmol) was added. The mixture was stirred at RT for 1 hour then diluted with saturated aqueous $NH_4Cl$ (15 mL) and extracted with EtOAc (3×15 mL). The combined organics were dried over $MgSO_4$ and concentrated in vacuo. The resulting residue was taken up in acetic acid (5 mL) and the mixture heated to 60° C. for 3 hours then to 100° C. for 1 hour. Following this time, the mixture was cooled to RT, concentrated in vacuo, and the material purified by normal phase column chromatography (eluent: $EtOAc/CH_2Cl_2$) to yield the product. ES/MS: 446.0 ($M+H^+$)

Methyl 2-(2-cyano-4-(6-((4-cyano-2-fluorobenzyl)oxy)pyridin-2-yl)-3-fluorobenzyl)-1-(2-methoxyethyl)-1H-benzo[d]imidazole-6-carboxylate: Methyl 2-(4-bromo-2-cyano-3-fluorobenzyl)-1-(2-methoxyethyl)-1H-benzo[d]imidazole-6-carboxylate (50.0 mg, 0.112 mmol), Pd(dppf)$Cl_2$ (8.3 mg, 0.011 mmol), potassium propionate (37.7 g, 0.336 mmol), and bis(pinacolato)diboron (56.9 mg, 0.224 mol) were taken up in 1,4-dioxane (0.75 mL) and the mixture sparged with argon for 5 minutes. The mixture was then heated to 90° C. for 2 hours. Following this time, complete conversion to the intermediate boronate ester was observed. The mixture was cooled to RT and aqueous sodium carbonate (2.0 M, 0.112 mL, 0.224 mmol) was added. The mixture was stirred for 5 minutes, then 4-((6-bromo-2-pyridyl)oxymethyl)-3-fluoro-benzonitrile (I-6, 0.0344 g, 0.000112 mol) and Pd(dppf)$Cl_2$ (12.5 mg, 0.016 mmol) were added and the mixture was heated to 90° C. for 1 hour. The mixture was then loaded directly onto $SiO_2$ for purification with normal phase column chromatography (eluent: EtOAc/$CH_2Cl_2$ gradient) which afforded the desired product. ES/MS: 594.2 (M+H$^+$).

2-(2-Cyano-4-(6-((4-cyano-2-fluorobenzyl)oxy)pyridin-2-yl)-3-fluorobenzyl)-1-(2-methoxyethyl)-1H-benzo[d]imidazole-6-carboxylic acid (Example 391): Methyl 2-(2-cyano-4-(6-((4-cyano-2-fluorobenzyl)oxy)pyridin-2-yl)-3-fluorobenzyl)-1-(2-methoxyethyl)-1H-benzo[d]imidazole-6-carboxylate (21.5 mg, 0.036 mmol) was taken up in N.N-dimethylformamide (0.5 mL) and aqueous lithium hydroxide (0.3 M, 0.36 mL, 0.109 mmol) was added. The mixture was heated to 130° C. in the microwave for 1 hour then cooled to RT and diluted with 5% aqueous citric acid to a pH~5. The mixture was extracted with EtOAc (3×5 mL) and the combined organic extracts dried over $MgSO_4$ and concentrated in vacuo. The material was purified by RP-HPLC (eluent: MeCN/water gradient with 0.1% TFA) to yield (Example 391) as the trifluoroacetate salt. ES/MS: 580.2 (M+H$^+$); $^1$H NMR (400 MHz, DMSO-d6) δ 8.10 (s, 1H), 7.90 (dd, J=8.8, 5.9 Hz, 1H), 7.84-7.73 (m, 2H), 7.73-7.60 (m, 3H), 7.54 (d, J=8.4 Hz, 1H), 7.48 (t, J=7.6 Hz, 1H), 7.13 (d, J=7.3 Hz, 1H), 6.90 (d, J=8.3 Hz, 1H), 4.91 (s, 2H), 4.61 (s, 2H), 4.48 (s, 2H), 3.59 (t, J=4.9 Hz, 2H), 3.08 (s, 3H).

Example 394. 2-(4-(6-((4-cyano-2-fluorobenzyl)oxy)pyridin-2-yl)-2-fluorobenzyl)-1-(2-(1-(fluoromethyl)cyclopropyl)ethyl)-1H-benzo[d]imidazole-6-carboxylic acid Procedure 42

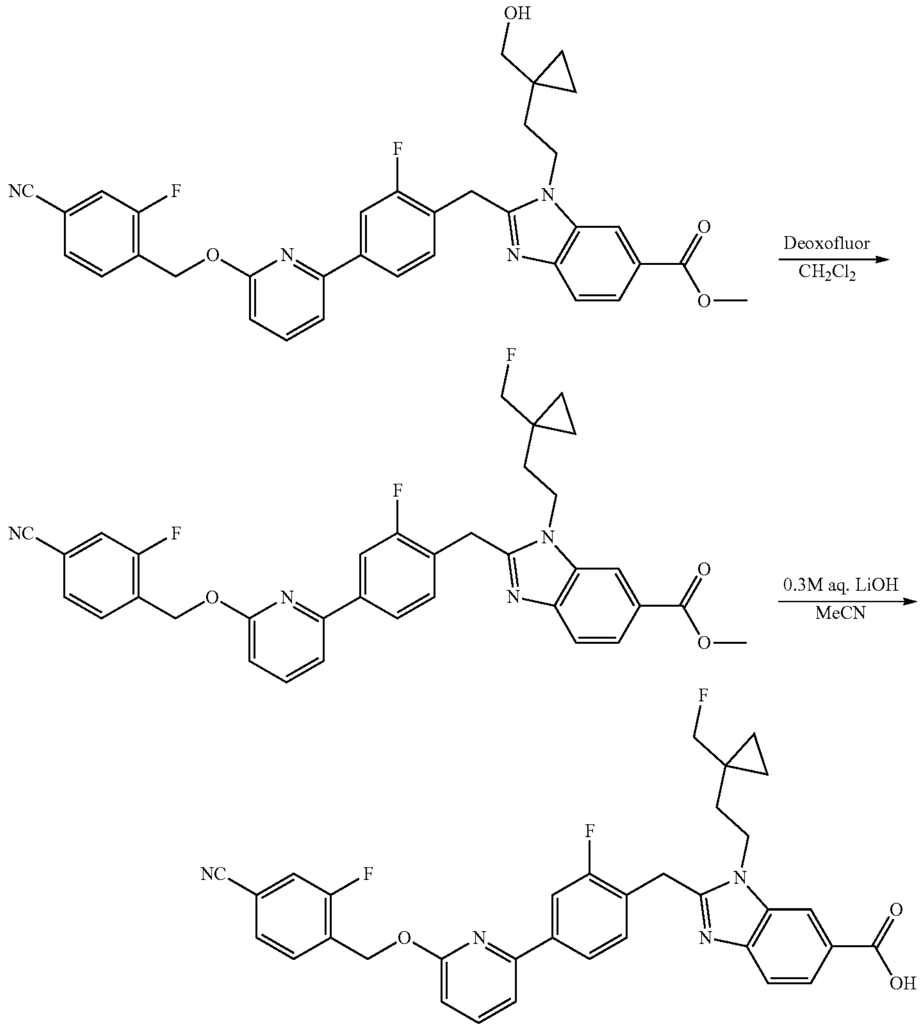

Example 394

Methyl 2-(4-(6-((4-cyano-2-fluorobenzyl)oxy)pyridin-2-yl)-2-fluorobenzyl)-1-(2-(1-(fluoromethyl)cyclopropyl)ethyl)-1H-benzo[d]imidazole-6-carboxylate: Methyl 2-(4-

(6-((4-cyano-2-fluorobenzyl)oxy)pyridin-2-yl)-2-fluorobenzyl)-1-(2-(1-(hydroxymethyl)cyclopropyl)ethyl)-1H-benzo[d]imidazole-6-carboxylate (25.0 mg, 4.11e-5 mol) which was synthesized according to the route generally described in Procedure 1 was taken up in dichloromethane (1.0 mL) and the mixture was cooled to 0° C. Deoxofluor (27.3 mg, 0.123 mmol) was added and the mixture was stirred at 0° C. for 10 minutes. Following this time, the reaction was complete as determined by LC/MS analysis and the reaction was quenched by addition of 10% aqueous $NH_4OH$ (5 mL). The mixture was extracted with EtOAc (3×5 mL), and the combined organics were washed with brine (5 mL), dried over $MgSO_4$, and concentrated in vacuo. The residue was purified by normal phase column chromatography (eluent: EtOAc, $CH_2Cl_2$) to afford the product. ES/MS: 611.2 (M+H$^+$).

2-(4-(6-((4-Cyano-2-fluorobenzyl)oxy)pyridin-2-yl)-2-fluorobenzyl)-1-(2-(1-(fluoromethyl)cyclopropyl)ethyl)-1H-benzo[d]imidazole-6-carboxylic acid (Example 394): Methyl 2-(4-(6-((4-cyano-2-fluorobenzyl)oxy)pyridin-2-yl)-2-fluorobenzyl)-1-(2-(1-(fluoromethyl)cyclopropyl)ethyl)-1H-benzo[d]imidazole-6-carboxylate (18.3 mg, 0.030 mmol) was taken up in acetonitrile (0.6 mL) and aqueous lithium hydroxide (0.3 M, 0.3 mL, 0.090 mmol) was added. The reaction vial was sealed and heated to 100° C. for 1 hour then cooled to RT and diluted with 5% aqueous citric acid to a pH~5. The mixture was extracted with EtOAc (3×5 mL) and the combined organic extracts dried over $MgSO_4$ and concentrated in vacuo. The material was purified by RP-HPLC (eluent: MeCN/water gradient with 0.1% TFA) to yield (Example 394) as the trifluoroacetate salt. ES/MS: 597.2 (M+H$^+$); $^1$H NMR (400 MHz, DMSO-d6) δ 8.18 (d, J=1.5 Hz, 1H), 7.99-7.82 (m, 5H), 7.81-7.71 (m, 2H), 7.67 (dd, J=8.0, 5.1 Hz, 2H), 7.48 (t, J=7.9 Hz, 1H), 6.94 (d, J=8.2 Hz, 1H), 5.62 (s, 2H), 4.50-4.46 (m, 4H), 2.31-1.99 (m, 4H), 1.81-1.63 (m, 1H), 1.52-1.37 (m, 1H).

Example 393. Compounds Prepared Using Procedure 42

Other compounds of the present disclosure prepared using the general route described in Procedure 42 include the following Example.

| Example | Structure/Name/Characterization |
|---|---|
| 393 | 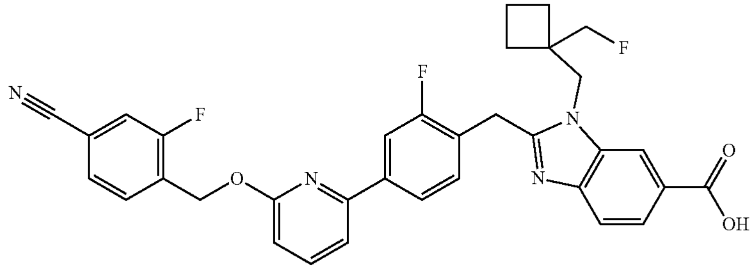 [SMILES: N#Cc1ccc(COc2cccc(-c3ccc(Cc4nc5ccc(C(=O)O)cc5n4CC4(CF)CCC4)c(F)c3)n2)c(F)c1]<br>2-(4-(6-((4-cyano-2-fluorobenzyl)oxy)pyridin-2-yl)-2-fluorobenzyl)-1-((1-(fluoromethyl)cyclobutyl)methyl)-1H-benzo[d]imidazole-6-carboxylic acid: ES/MS m/z 597.2; $^1$H NMR (400 MHz, DMSO-d6) δ 8.30 (s, 1H), 7.96-7.90 (m, 1H), 7.90-7.82 (m, 3H), 7.81-7.70 (m, 3H), 7.66 (d, J = 7.5 Hz, 1H), 7.58 (d, J = 8.5 Hz, 1H), 7.45 (t, J = 8.0 Hz, 1H), 6.93 (d, J = 8.2 Hz, 1H), 5.62 (s, 2H), 4.83 (d, J = 22.0 Hz, 2H), 4.42 (s, 2H), 1.76-1.72 (m, 6H). |

Example 395: (S)-2-(4-(6-((4-cyano-2-fluorobenzyl)oxy)pyridin-2-yl)-2-fluorobenzyl)-1-((1-(oxetan-3-yl)azetidin-2-yl)methyl)-1H-benzo[d]imidazole-6-carboxylic acid Procedure 43

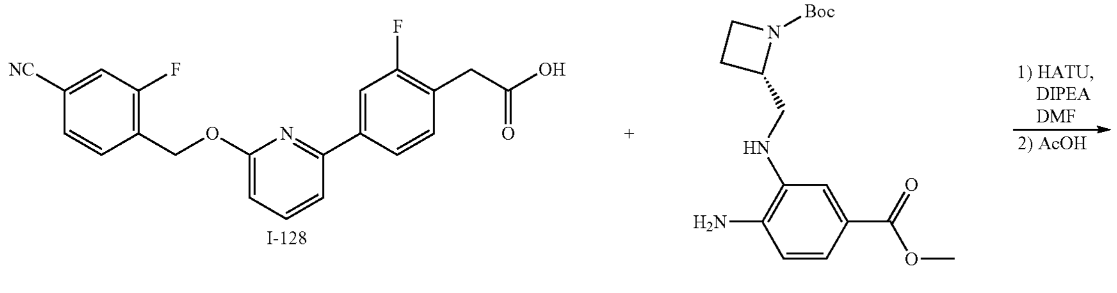

I-128

-continued

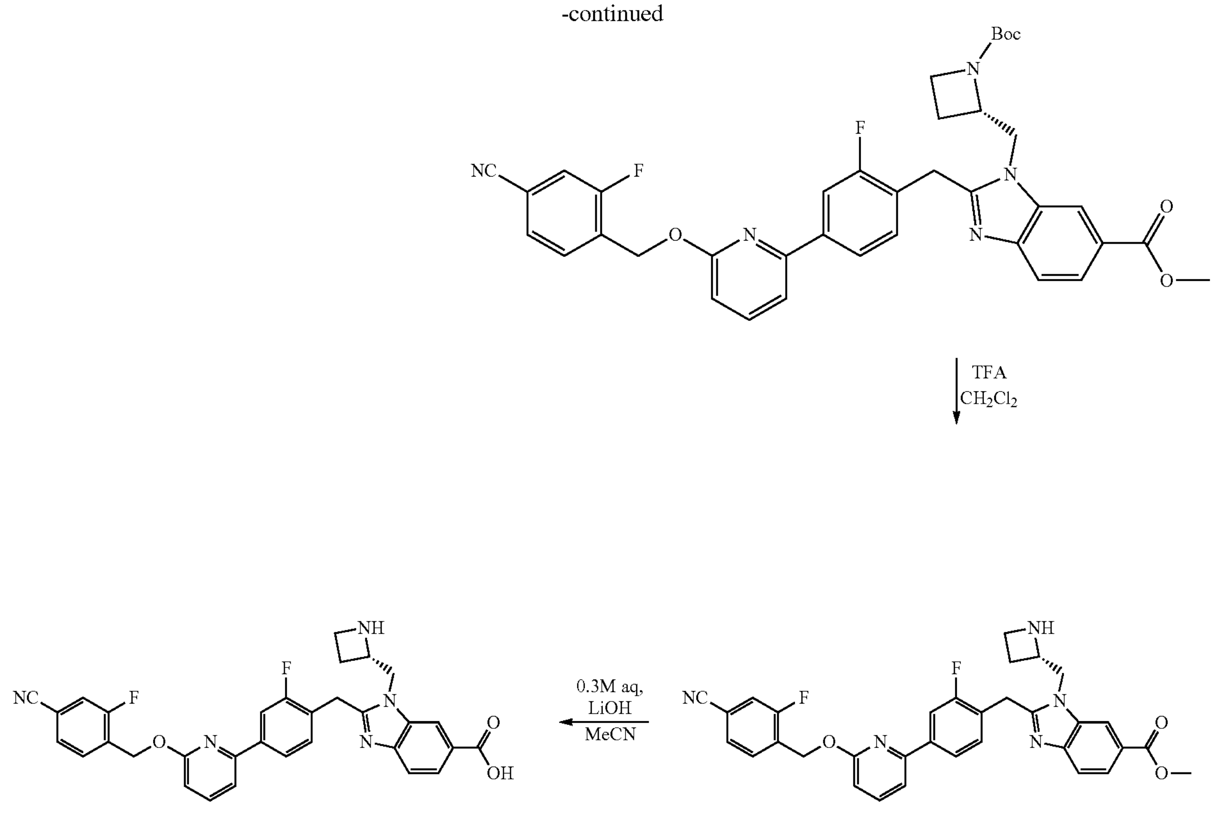

Example 395

Methyl (S)-1-((1-(tert-butoxycarbonyl)azetidin-2-yl)methyl)-2-(4-(6-((4-cyano-2-fluorobenzyl)oxy)pyridin-2-yl)-2-fluorobenzyl)-1H-benzo[d]imidazole-6-carboxylate: 2-(4-(6-((4-Cyano-2-fluorobenzyl)oxy)pyridin-2-yl)-2-fluorophenyl)acetic acid (I-128, 150 mg, 0.394 mmol), tert-Butyl (S)-2-(((2-amino-5-(methoxycarbonyl)phenyl)amino)methyl)azetidine-1-carboxylate (125 mg, 0.373 mmol), and HATU (180 mg, 0.473 mmol) were taken up in N,N-dimethylformamide (3.0 mL) and N,N-diisopropylethylamine (0.34 mL, 1.97 mmol) was added. The mixture was stirred at RT for 2 hours then diluted with saturated aqueous $NH_4Cl$ (15 mL) and extracted with EtOAc (3×15 mL). The combined organics were dried over $MgSO_4$ and concentrated in vacuo. The resulting residue was taken up in acetic acid (4 mL) and the mixture heated to 100° C. for 1 hour. Following this time, the mixture was cooled to RT, concentrated in vacuo, and the material was purified by normal phase column chromatography (eluent: EtOAc/$CH_2Cl_2$) to yield the product. ES/MS: 680.2 (M+$H^+$).

Methyl (S)-1-(azetidin-2-ylmethyl)-2-(4-(6-((4-cyano-2-fluorobenzyl)oxy)pyridin-2-yl)-2-fluorobenzyl)-1H-benzo[d]imidazole-6-carboxylate: Methyl (S)-1-((1-(tert-butoxycarbonyl)azetidin-2-yl)methyl)-2-(4-(6-((4-cyano-2-fluorobenzyl)oxy)pyridin-2-yl)-2-fluorobenzyl)-1H-benzo[d]imidazole-6-carboxylate (243 mg, 0.358 mmol) was taken up in dichloromethane (3.5 mL) and trifluoroacetic acid (0.35 mL, 3.07 mmol) was added. The mixture was stirred at RT overnight and then heated to 45° C. for 1.5 hours. Following this time, the mixture was concentrated in vacuo and the product was used in the subsequent reaction without purification. ES/MS: 580.2 (M+$H^+$).

(S)-2-(4-(6-((4-cyano-2-fluorobenzyl)oxy)pyridin-2-yl)-2-fluorobenzyl)-1-((1-(oxetan-3-yl)azetidin-2-yl)methyl)-1H-benzo[d]imidazole-6-carboxylic acid (Example 395): Methyl (S)-1-(azetidin-2-ylmethyl)-2-(4-(6-((4-cyano-2-fluorobenzyl)oxy)pyridin-2-yl)-2-fluorobenzyl)-1H-benzo[d]imidazole-6-carboxylate (25.0 mg, 0.043 mmol) was taken up in acetonitrile (0.6 mL) and aqueous lithium hydroxide (0.3 M, 0.43 mL, 0.129 mmol) was added. The reaction vial was sealed and heated to 100° C. for 15 minutes then cooled to RT and diluted with 5% aqueous citric acid to a pH~5. The mixture was extracted with EtOAc (3×5 mL) and the combined organic extracts were dried over $MgSO_4$ and concentrated in vacuo. The material was purified by RP-HPLC (eluent: MeCN/water gradient with 0.1% TFA) to yield (Example 395) as the trifluoroacetate salt. ES/MS: 566.2 (M+$H^+$); $^1H$ NMR (400 MHz, DMSO-d6) δ 8.41 (d, J=1.5 Hz, 1H), 7.96-7.81 (m, 5H), 7.81-7.71 (m, 2H), 7.68 (d, J=7.4 Hz, 1H), 7.62 (d, J=8.4 Hz, 1H), 7.44 (t, J=7.8 Hz, 1H), 6.95 (d, J=8.2 Hz, 1H), 5.63 (s, 2H), 4.92-4.75 (m, 2H), 4.46 (s, 2H), 4.05-3.89 (m, 1H), 3.85-3.80 (m, 1H).

Example 695. Compounds Prepared Using Procedure 43

Other compounds of the present disclosure prepared using the general route described in Procedure 43 include the following Example.

| Example | Structure/Name/Characterization |
|---|---|
| 695 | 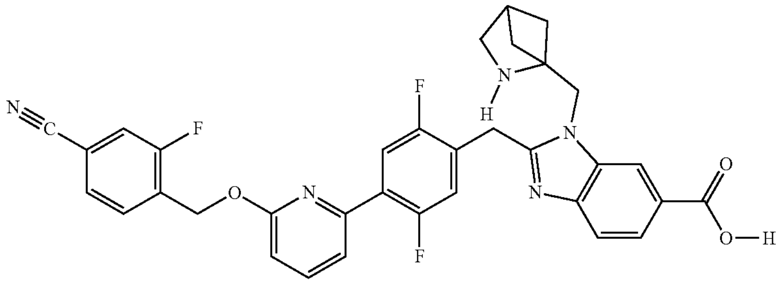 [SMILES: N#Cc1ccc(COc2cccc(-c3cc(F)c(Cc4nc5ccc(C(=O)O)cc5n4CC45CC(CN4)C5)cc3F)n2)c(F)c1]<br>ES/MS 610.2; 1H NMR (400 MHz, DMSO-d6) δ 8.30 (d, J = 1.4 Hz, 1H), 7.95-7.88 (m, 2H), 7.84 (dd, J = 8.4, 1.5 Hz, 1H), 7.80-7.71 (m, 3H), 7.66 (d, J = 8.4 Hz, 1H), 7.54 (dd, J = 7.5, 1.7 Hz, 1H), 7.45 (dd, J = 11.5, 6.1 Hz, 1H), 7.01 (d, J = 8.2 Hz, 1H), 5.61 (s, 2H), 4.92 (s, 2H), 4.38 (s, 2H), 3.31 (d, J = 4.9 Hz, 2H), 2.81 (d, J = 3.3 Hz, 1H), 2.06 (s, 2H), 1.59 (dd, J = 5.4, 2.0 Hz, 2H). |
Example 396. (S)-2-(4-(6-((4-cyano-2-fluorobenzyl)oxy)pyridin-2-yl)-2-fluorobenzyl)-1-((1-(oxetan-3-yl)azetidin-2-yl)methyl)-1H-benzo[d]imidazole-6-carboxylic acid
Procedure 44
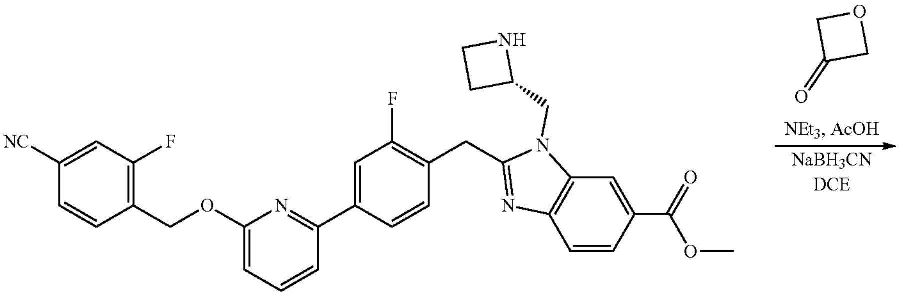
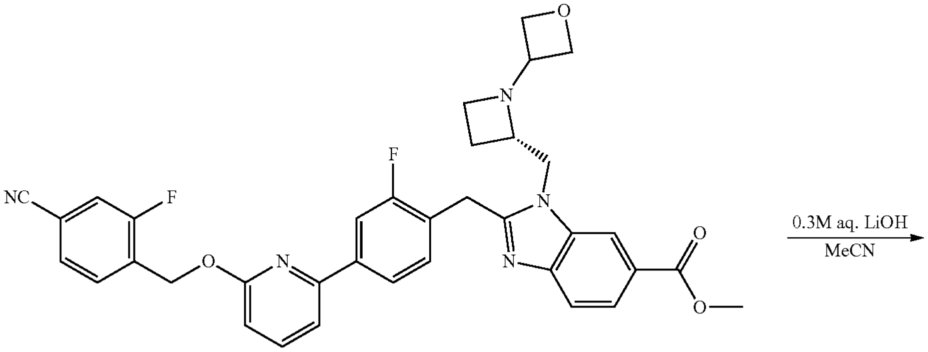

-continued

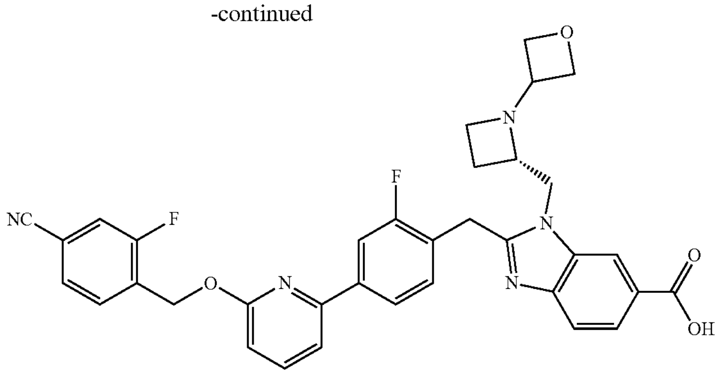

Example 396

Methyl (S)-2-(4-(6-((4-cyano-2-fluorobenzyl)oxy)pyridin-2-yl)-2-fluorobenzyl)-1-((1-(oxetan-3-yl)azetidin-2-yl)methyl)-1H-benzo[d]imidazole-6-carboxylate: Oxetan-3-one (0.040 mL, 0.690 mmol) was taken up in dichloroethane (2.5 mL) and triethylamine (0.048 mL, 0.345 mol) and acetic acid (0.040 mL, 0.690 mol) were added, followed by methyl (S)-1-(azetidin-2-ylmethyl)-2-(4-(6-((4-cyano-2-fluorobenzyl)oxy)pyridin-2-yl)-2-fluorobenzyl)-1H-benzo[d]imidazole-6-carboxylate (100 mg, 0.173 mol). $MgSO_4$ (small spatula tip) was added and the mixture stirred at RT for 30 minutes. Sodium cyanoborohydride (32.5 mg, 0.518 mol) was added to the mixture and the mixture was stirred at RT for an additional 30 minutes. Following this time, the mixture was diluted with $CH_2Cl_2$ (10 mL) and the mixture was washed with saturated aqueous $NaHCO_3$ (10 mL). The organic phase was collected and the aqueous phase was extracted with $CH_2Cl_2$ (2x5 mL). The combined organics were dried over $MgSO_4$, concentrated in vacuo, and purified by normal phase column chromatography (eluent: EtOAc/$CH_2Cl_2$ gradient) to afford the product. ES/MS: 636.2 ($M+H^+$).

(S)-2-(4-(6-((4-cyano-2-fluorobenzyl)oxy)pyridin-2-yl)-2-fluorobenzyl)-1-((1-(oxetan-3-yl)azetidin-2-yl)methyl)-1H-benzo[d]imidazole-6-carboxylic acid (Example 396): Methyl (S)-2-(4-(6-((4-cyano-2-fluorobenzyl)oxy)pyridin-2-yl)-2-fluorobenzyl)-1-((1-(oxetan-3-yl)azetidin-2-yl)methyl)-1H-benzo[d]imidazole-6-carboxylate (21.7 mg, 0.034 mmol) was taken up in acetonitrile (0.5 mL) and aqueous lithium hydroxide (0.3 M, 0.34 mL, 0.102 mmol) was added. The reaction vial was sealed and heated to 100° C. for 5 minutes then cooled to RT and diluted with 5% aqueous citric acid to a pH~5. The mixture was extracted with EtOAc (3x5 mL) and the combined organic extracts were dried over $MgSO_4$ and concentrated in vacuo. The material was purified by RP-HPLC (eluent: MeCN/water gradient with 0.1% TFA) to yield (Example 396) as the trifluoroacetate salt. ES/MS: 622.2 ($M+H^+$); $^1H$ NMR (400 MHz, DMSO-d6) δ 8.41 (d, J=1.5 Hz, 1H), 7.96-7.81 (m, 5H), 7.81-7.71 (m, 2H), 7.68 (d, J=7.4 Hz, 1H), 7.62 (d, J=8.4 Hz, 1H), 7.44 (t, J=7.8 Hz, 1H), 6.95 (d, J=8.2 Hz, 1H), 5.63 (s, 2H), 4.92-4.75 (m, 2H), 4.46 (s, 2H), 4.05-3.89 (m, 1H), 3.85-3.80 (m, 1H).

Example 696. Compounds Prepared Using Procedure 44

Other compounds of the present disclosure prepared using the general route described in Procedure 44 include the following Example.

| Example | Structure/Name/Characterization |
|---|---|
| 696 | 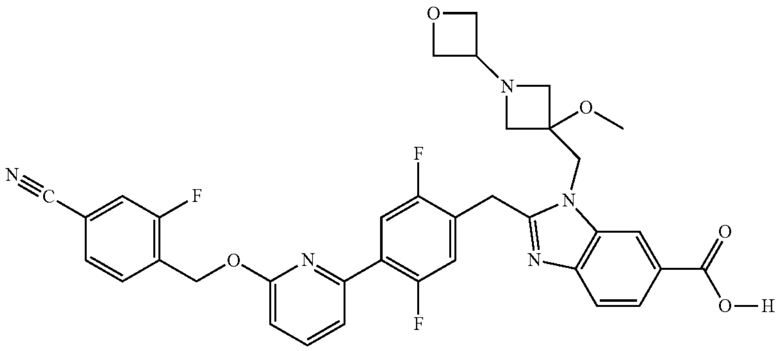 [SMILES: COC1(Cn2c(Cc3cc(F)c(-c4cccc(OCc5ccc(C#N)cc5F)n4)cc3F)nc3ccc(C(=O)O)cc32)CN(C2COC2)C1]<br>ES/MS 670.2; 1H NMR (400 MHz, DMSO-d6) δ 8.33 (s, 1H), 7.97-7.86 (m, 2H), 7.82-7.70 (m, 4H), 7.60 (d, J = 8.4 Hz, 1H), 7.53 (d, J = 7.2 Hz, 1H), 7.40 (dd, J = 11.6, 6.0 Hz, 1H), 7.00 (d, J = 8.2 Hz, 1H), 5.60 (s, 2H), 4.80 (s, 2H), 4.59 (s, 2H), 4.44 (d, J = 24.8 Hz, 4H), 3.80 (s, 1H), 3.31 (s, 3H), 3.21 (s, 4H). |

Example 397. (S)-2-(4-(6-((4-cyano-2-fluorobenzyl)oxy)pyridin-2-yl)-2-fluorobenzyl)-1-((1-methylazetidin-2-yl)methyl)-1H-benzo[d]imidazole-6-carboxylic acid Procedure 45

Methyl (S)-2-(4-(6-((4-cyano-2-fluorobenzyl)oxy)pyridin-2-yl)-2-fluorobenzyl)-1-((1-methylazetidin-2-yl)methyl)-1H-benzo[d]imidazole-6-carboxylate (22.1 mg, 0.037 mmol) was taken up in acetonitrile (0.5 mL) and aqueous lithium hydroxide (0.3 M, 0.37 mL, 0.112 mmol) was added. The reaction vial was sealed and heated to 100° C. for 5

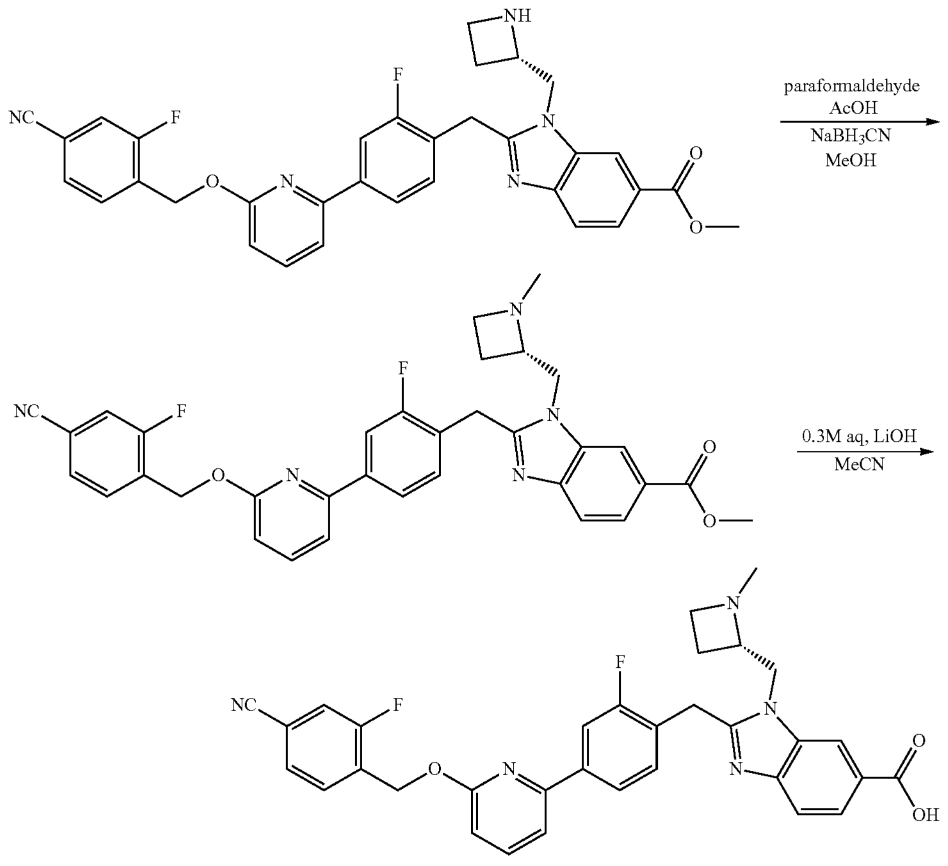

Example 397

Methyl (S)-2-(4-(6-((4-cyano-2-fluorobenzyl)oxy)pyridin-2-yl)-2-fluorobenzyl)-1-((1-methylazetidin-2-yl)methyl)-1H-benzo[d]imidazole-6-carboxylate: Paraformaldehyde (31.1 mg, 1.04 mmol) was taken up in methanol (2.5 mL) and acetic acid (0.25 mL, 4.37 mmol) was added followed by methyl (S)-1-(azetidin-2-ylmethyl)-2-(4-(6-((4-cyano-2-fluorobenzyl)oxy)pyridin-2-yl)-2-fluorobenzyl)-1H-benzo[d]imidazole-6-carboxylate (100 mg, 0.173 mmol). $MgSO_4$ (small spatula tip) was added and the mixture was stirred at RT for 30 minutes. Sodium cyanoborohydride (32.5 mg, 0.518 mmol) was added to the mixture and the mixture stirred at RT overnight. Following this time, the mixture was diluted with $CH_2Cl_2$ (10 mL) and the mixture was washed with saturated aqueous $NaHCO_3$ (10 mL). The organic phase was collected and the aqueous phase was extracted with $CH_2Cl_2$ (2x5 mL). The combined organics were dried over $MgSO_4$, concentrated in vacuo, and purified by normal phase column chromatography (eluent: $EtOAc/CH_2Cl_2$ gradient) to afford the product. ES/MS: 594.2 ($M+H^+$).

(S)-2-(4-(6-((4-cyano-2-fluorobenzyl)oxy)pyridin-2-yl)-2-fluorobenzyl)-1-((1-methylazetidin-2-yl)methyl)-1H-benzo[d]imidazole-6-carboxylic acid (Example 397): minutes then cooled to RT and diluted with 5% aqueous citric acid to a pH~5. The mixture was extracted with EtOAc (3×5 mL) and the combined organic extracts were dried over $MgSO_4$ and concentrated in vacuo. The material was purified by RP-HPLC (eluent: MeCN/water gradient with 0.1% TFA) to yield (Example 397) as the trifluoroacetate salt. ES/MS: 580.2 ($M+H^+$); $^1H$ NMR (400 MHz, DMSO-d6) δ 10.15 (s, 1H), 8.42 (d, J=1.4 Hz, 1H), 8.01-7.81 (m, 5H), 7.81-7.72 (m, 2H), 7.68 (d, J=7.5 Hz, 1H), 7.63 (d, J=8.5 Hz, 1H), 7.46 (t, J=8.1 Hz, 1H), 6.95 (d, J=8.2 Hz, 1H), 5.63 (s, 2H), 4.97 (q, J=8.4 Hz, 1H), 4.92-4.71 (m, 2H), 4.49 (s, 2H), 4.12-4.04 (m, 1H), 3.92-3/84 (m, 1H), 2.71 (s, 3H), 2.48-2.41 (m, 1H), 2.40-2.27 (m, 2H).

Example 697. Compounds Prepared Using Procedure 45

Other compounds of the present disclosure prepared using the general route described in Procedure 45 include the following Example.

| Example | Structure/Name/Characterization |
|---|---|
| 697 | 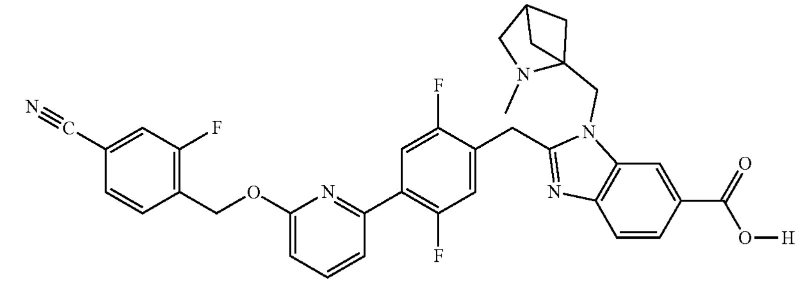 [SMILES: CN1CC2CC1(Cn1c(Cc3cc(F)c(-c4cccc(OCc5ccc(C#N)cc5F)n4)cc3F)nc3ccc(C(=O)O)cc31)C2]<br>ES/MS 624.2; 1H NMR (400 MHz, DMSO-d6) δ 10.37 (s, 1H), 8.25 (s, 1H), 7.96-7.87 (m, 2H), 7.84 (dd, J = 8.5, 1.5 Hz, 1H), 7.80-7.72 (m, 3H), 7.66 (d, J = 8.4 Hz, 1H), 7.54 (dd, J = 7.5, 1.7 Hz, 1H), 7.49 (dd, J = 11.5, 6.1 Hz, 1H), 7.01 (d, J = 8.3 Hz, 1H), 5.60 (s, 2H), 5.03 (d, J = 15.7 Hz, 1H), 4.84 (d, J = 15.6 Hz, 1H), 4.47-4.24 (m, 2H), 3.20 (d, J = 9.9 Hz, 1H), 3.09 (d, J = 5.0 Hz, 3H), 2.69 (q, J = 2.7, 1.9 Hz, 1H), 2.08-1.95 (m, 1H), 1.65 (t, J = 9.6 Hz, 1H), 1.49 (s, 1H). |

Example 259. 2-(3-amino-4-(6-((4-cyano-2-fluorobenzyl)oxy)pyridin-2-yl)benzyl)-1-(2-methoxyethyl)-1H-benzo[d]imidazole-6-carboxylic acid Procedure 46

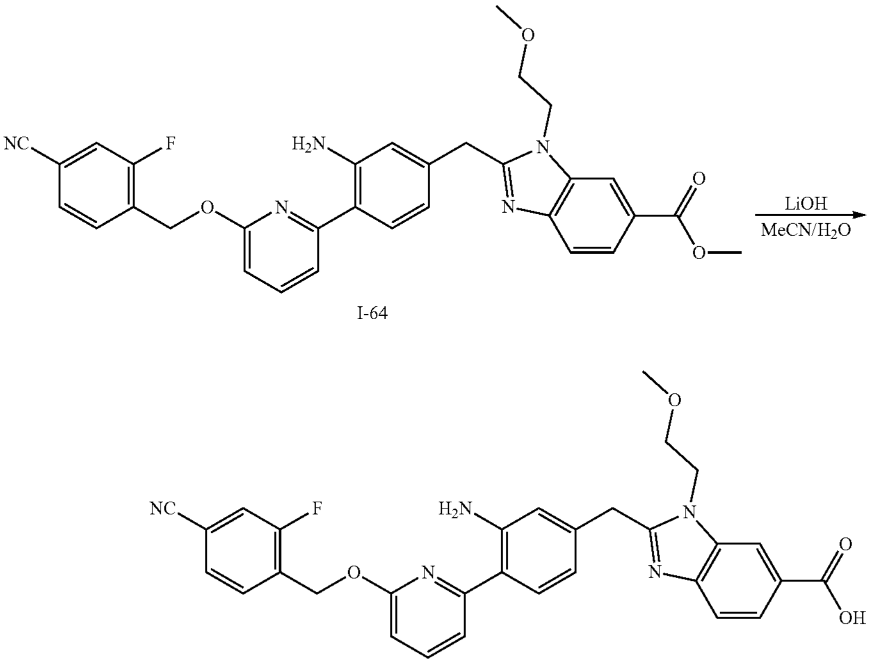

I-64

Example 259

2-(3-amino-4-(6-((4-cyano-2-fluorobenzyl)oxy)pyridin-2-yl)benzyl)-1-(2-methoxyethyl)-1H-benzo[d]imidazole-6-carboxylic acid: Methyl 2-(3-amino-4-(6-((4-cyano-2-fluorobenzyl)oxy)pyridin-2-yl)benzyl)-1-(2-methoxyethyl)-1H-benzo[d]imidazole-6-carboxylate (I-64, 37 mg, 0.065 mmol) was taken up in acetonitrile (1.0 mL) and aqueous lithium hydroxide (1.0 M, 0.33 mL, 0.33 mmol) was added. The mixture was heated to 50° C. for 90 minutes. Following this time, the mixture was diluted with EtOAc (5 mL), the pH adjusted to ~5 with 1 M aqueous citric acid solution and the mixture extracted with EtOAc (3x5 mL). The combined organics were dried over $Na_2SO_4$, concentrated in vacuo, and purified by RP-HPLC (eluent: 20-70% MeCN/water with 0.1% TFA) to yield the product (Example 259) as the trifluoroacetate salt. ES/MS: 552.3 ($M+H^+$); 1H NMR (400 MHz, Methanol-d4) δ 8.57-8.49 (m, 1H), 8.22 (dd, J=8.6, 1.4 Hz, 1H), 7.88-7.76 (m, 2H), 7.69 (t, J=7.6 Hz, 1H), 7.62-7.52 (m, 3H), 7.35 (d, J=7.5 Hz, 1H), 6.88 (d, J=8.2 Hz, 1H), 6.83-6.73 (m, 2H), 5.55 (s, 2H), 4.73 (t, J=5.0 Hz, 2H), 4.59 (s, 2H), 3.75 (t, J=4.9 Hz, 2H), 3.30 (s, 3H).

Example 261. 2-(3-bromo-4-(6-((4-cyano-2-fluorobenzyl)oxy)pyridin-2-yl)benzyl)-1-(2-methoxyethyl)-1H-benzo[d]imidazole-6-carboxylic acid Procedure 47

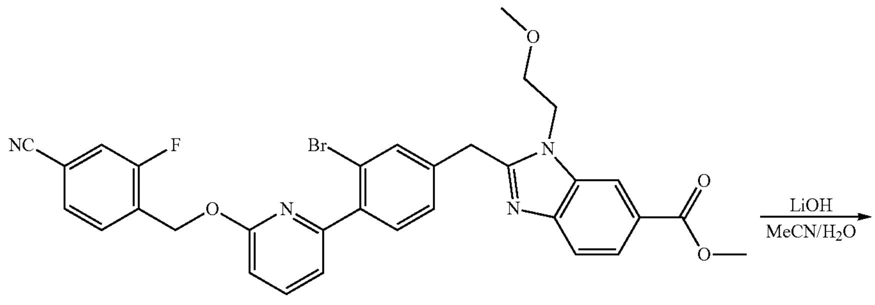

I-66

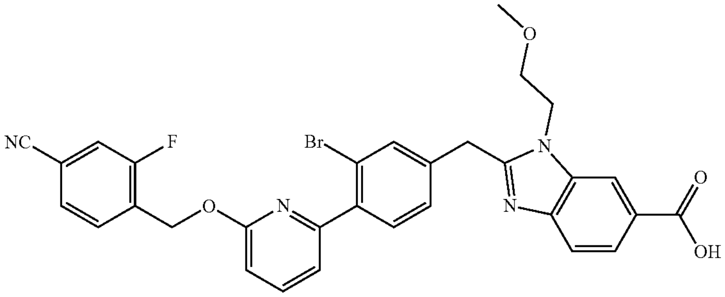

Example 261

2-(3-bromo-4-(6-((4-cyano-2-fluorobenzyl)oxy)pyridin-2-yl)benzyl)-1-(2-methoxyethyl)-1H-benzo[d]imidazole-6-carboxylic acid: Methyl 2-(3-bromo-4-(6-((4-cyano-2-fluorobenzyl)oxy)pyridin-2-yl)benzyl)-1-(2-methoxyethyl)-1H-benzo[d]imidazole-6-carboxylate (I-66, 16 mg, 0.025 mmol) was taken up in acetonitrile (0.3 mL) and aqueous lithium hydroxide (1.0 M, 0.13 mL, 0.13 mmol) was added. The mixture was heated to 50° C. for 90 minutes. Following this time, the mixture was diluted with EtOAc (5 mL), the pH adjusted to ~5 with 1 M aqueous citric acid solution, and the mixture extracted with EtOAc (3×5 mL). The combined organics were dried over $Na_2SO_4$, concentrated in vacuo, and purified by RP-HPLC (eluent: 20-70% MeCN/water with 0.1% TFA) to yield the product (Example 261) as the trifluoroacetate salt. ES/MS: 615.4 ($M+H^+$); 1H NMR (400 MHz, Methanol-d4) δ 8.57 (d, J=1.3 Hz, 1H), 8.24 (dd, J=8.6, 1.4 Hz, 1H), 7.86-7.76 (m, 3H), 7.69 (t, J=7.6 Hz, 1H), 7.59-7.51 (m, 3H), 7.45 (dd, J=7.9, 1.7 Hz, 1H), 7.24 (d, J=7.3 Hz, 1H), 6.94 (d, J=8.3 Hz, 1H), 5.56 (s, 2H), 4.81 (t, J=5.0 Hz, 2H), 4.74 (s, 2H), 3.82 (t, J=4.9 Hz, 2H), 3.32 (s, 3H).

Example 239. Compounds Prepared Using Procedure 47

Other compounds of the present disclosure prepared using the general route described in Procedure 47 include the following Example.

| Example | Structure/Name/Characterization |
|---|---|
| 239 | 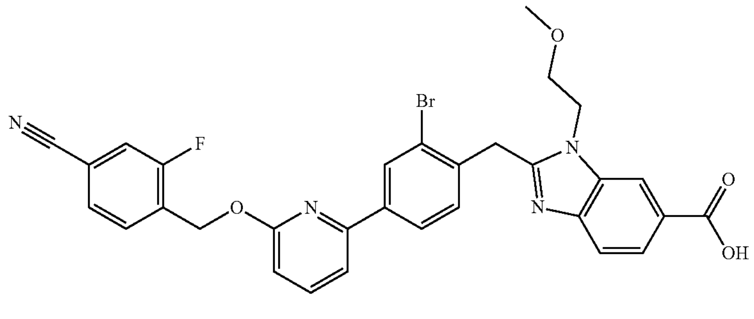 [SMILES: COCCn1c(Cc2ccc(-c3cccc(OCc4ccc(C#N)cc4F)n3)cc2Br)nc2ccc(C(=O)O)cc21]<br>2-(2-bromo-4-(6-((4-cyano-2-fluorobenzyl)oxy)pyridin-2-yl)benzyl)-1-(2-methoxyethyl)-1H-benzo[d]imidazole-6-carboxylic acid: ES/MS m/z 615.3; $^1H$ NMR (400 MHz, Methanol-d4) δ 8.5-8.48 (m, 1H), 8.31 (d, J = 1.8 Hz, 1H), 8.17 (dd, J = 8.5, 1.4 Hz, 1H), 8.04 (dd, J = 8.1, 1.8 Hz, 1H), 7.81 (t, J = 7.9 Hz, 1H), 7.75-7.67 (m, 2H), 7.61 (dd, J = 9.7, 1.5 Hz, 1H), 7.56 (dd, J = 7.8, 2.0 |

-continued

| Example | Structure/Name/Characterization |
|---|---|
| | Hz, 2H), 7.48 (d, J = 8.0 Hz, 1H), 6.92 (d, J = 8.2 Hz, 1H), 5.64 (s, 2H), 4.80 (s, 2H), 4.77 (t, J = 5.0 Hz, 2H), 3.83 (t, J = 4.9 Hz, 2H), 3.32 (s, 3H). |

Example 260. 2-(4-(6-((4-cyano-2-fluorobenzyl)oxy)pyridin-2-yl)-2-(1H-pyrazol-3-yl)benzyl)-1-(2-methoxyethyl)-1H-benzo[d]imidazole-6-carboxylic acid Procedure 48

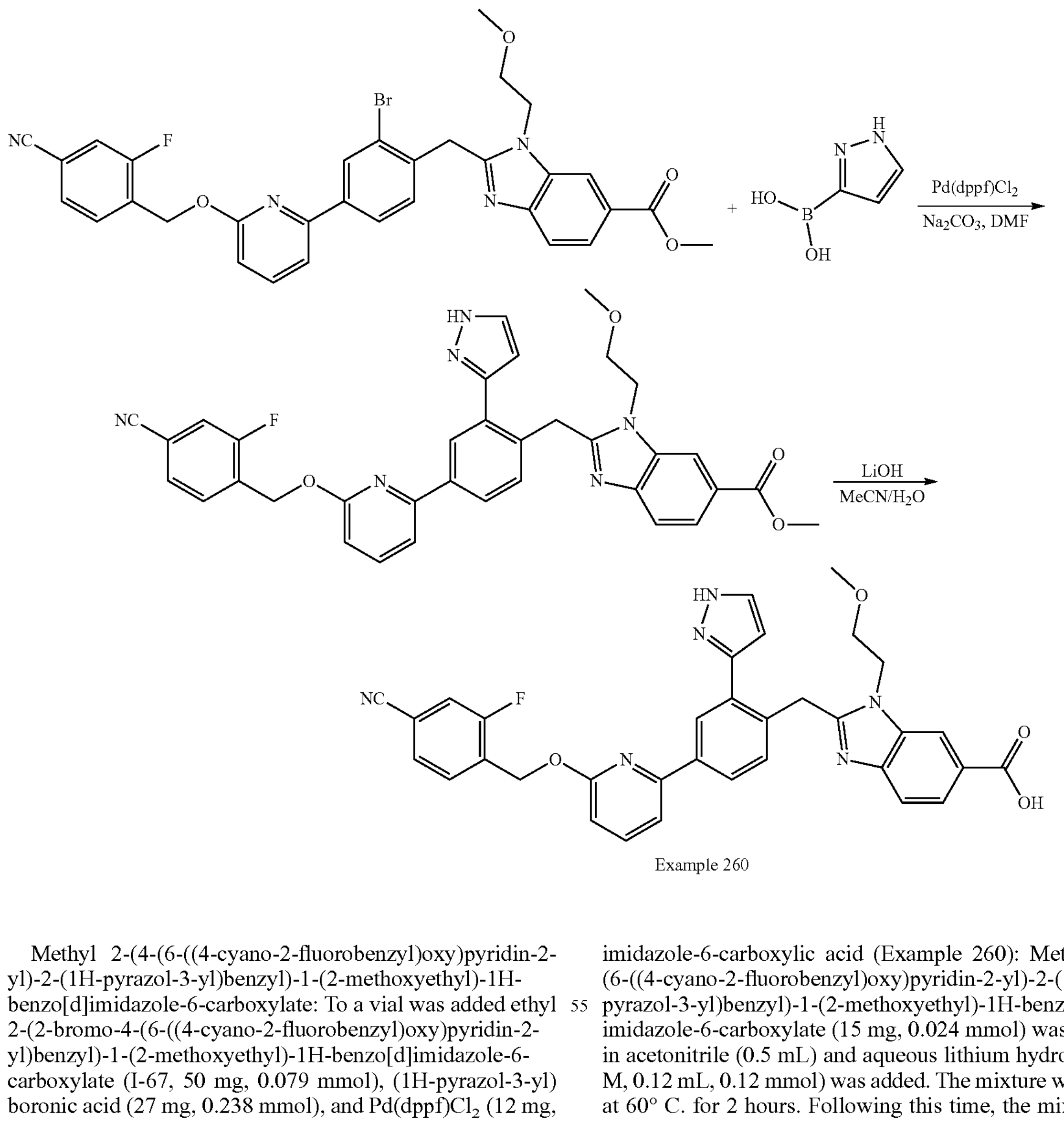

Example 260

Methyl 2-(4-(6-((4-cyano-2-fluorobenzyl)oxy)pyridin-2-yl)-2-(1H-pyrazol-3-yl)benzyl)-1-(2-methoxyethyl)-1H-benzo[d]imidazole-6-carboxylate: To a vial was added ethyl 2-(2-bromo-4-(6-((4-cyano-2-fluorobenzyl)oxy)pyridin-2-yl)benzyl)-1-(2-methoxyethyl)-1H-benzo[d]imidazole-6-carboxylate (I-67, 50 mg, 0.079 mmol), (1H-pyrazol-3-yl)boronic acid (27 mg, 0.238 mmol), and Pd(dppf)$Cl_2$ (12 mg, 0.016 mmol). DMF (2.0 mL) was added followed by aqueous sodium carbonate (3.0 M, 1.60 mL, 0.238 mmol), and the mixture was degassed with argon for two minutes. The vial was sealed, and the mixture was heated for 8 hours at 100° C. Following this time, the mixture was cooled to room temperature and diluted with EtOAc (50 mL) and water (50 mL). The organic phase was collected, and the aqueous phase extracted with EtOAc (2×50 mL). The combined organic phases were dried over $Na_2SO_4$ and concentrated in vacuo. The crude material was purified by silica gel chromatography (eluent: 30-80 EtOAc/hexanes) to afford the desired product. ES/MS: 617.3 (M+H$^+$).

2-(4-(6-((4-cyano-2-fluorobenzyl)oxy)pyridin-2-yl)-2-(1H-pyrazol-3-yl)benzyl)-1-(2-methoxyethyl)-1H-benzo[d]imidazole-6-carboxylic acid (Example 260): Methyl 2-(4-(6-((4-cyano-2-fluorobenzyl)oxy)pyridin-2-yl)-2-(1H-pyrazol-3-yl)benzyl)-1-(2-methoxyethyl)-1H-benzo[d]imidazole-6-carboxylate (15 mg, 0.024 mmol) was taken up in acetonitrile (0.5 mL) and aqueous lithium hydroxide (1.0 M, 0.12 mL, 0.12 mmol) was added. The mixture was heated at 60° C. for 2 hours. Following this time, the mixture was diluted with EtOAc (5 mL), the pH adjusted to ~5 with 1 M aqueous citric acid solution, and the mixture extracted with EtOAc (3×5 mL). The combined organics were dried over $Na_2SO_4$, concentrated in vacuo, and purified by RP-HPLC (eluent: 20-70% MeCN/water with 0.1% TFA) to yield the product (Example 260) as the trifluoroacetate salt. ES/MS: 603.2 (M+H$^+$); $^1$H NMR (400 MHz, Methanol-d4) δ 8.54 (d, J=1.3 Hz, 1H), 8.27 (d, J=1.9 Hz, 1H), 8.18 (dd, J=8.6, 1.4

Hz, 1H), 8.08 (dd, J=8.1, 2.0 Hz, 1H), 7.83 (t, J=7.9 Hz, 1H), 7.71 (t, J=7.6 Hz, 1H), 7.68-7.64 (m, 2H), 7.61 (d, J=7.7 Hz, 2H), 7.58-7.54 (m, 1H), 7.54-7.50 (m, 1H), 6.92 (d, J=8.2 Hz, 1H), 6.56 (d, J=2.4 Hz, 1H), 5.66 (s, 2H), 4.90 (s, 2H), 4.76 (t, J=5.0 Hz, 2H), 3.82 (t, J=4.9 Hz, 2H), 3.33 (s, 3H).

Example 240. 2-(4-(6-((4-cyano-2-fluorobenzyl)oxy)pyridin-2-yl)-2-((1-(hydroxymethyl)cyclopropyl)ethynyl)benzyl)-1-(2-methoxyethyl)-1H-benzo[d]imidazole-6-carboxylic acid Procedure 49 and the mixture was heated for 2 hours at 90° C. Following this time, the mixture was cooled to room temperature and concentrated in vacuo. The crude material was purified by silica gel chromatography (eluent: 20-80 EtOAc/hexanes) to afford the desired product. ES/MS: 645.2 (M+H$^+$).

2-(4-(6-((4-cyano-2-fluorobenzyl)oxy)pyridin-2-yl)-2-((1-(hydroxymethyl)cyclopropyl)ethynyl)benzyl)-1-(2-methoxyethyl)-1H-benzo[d]imidazole-6-carboxylic acid (Example 240): Methyl 2-(4-(6-((4-cyano-2-fluorobenzyl)oxy)pyridin-2-yl)-2-((1-(hydroxymethyl)cyclopropyl)ethynyl)benzyl)-1-(2-methoxyethyl)-1H-benzo[d]imidazole-6-carboxylate (22 mg, 0.034 mmol) was taken up in

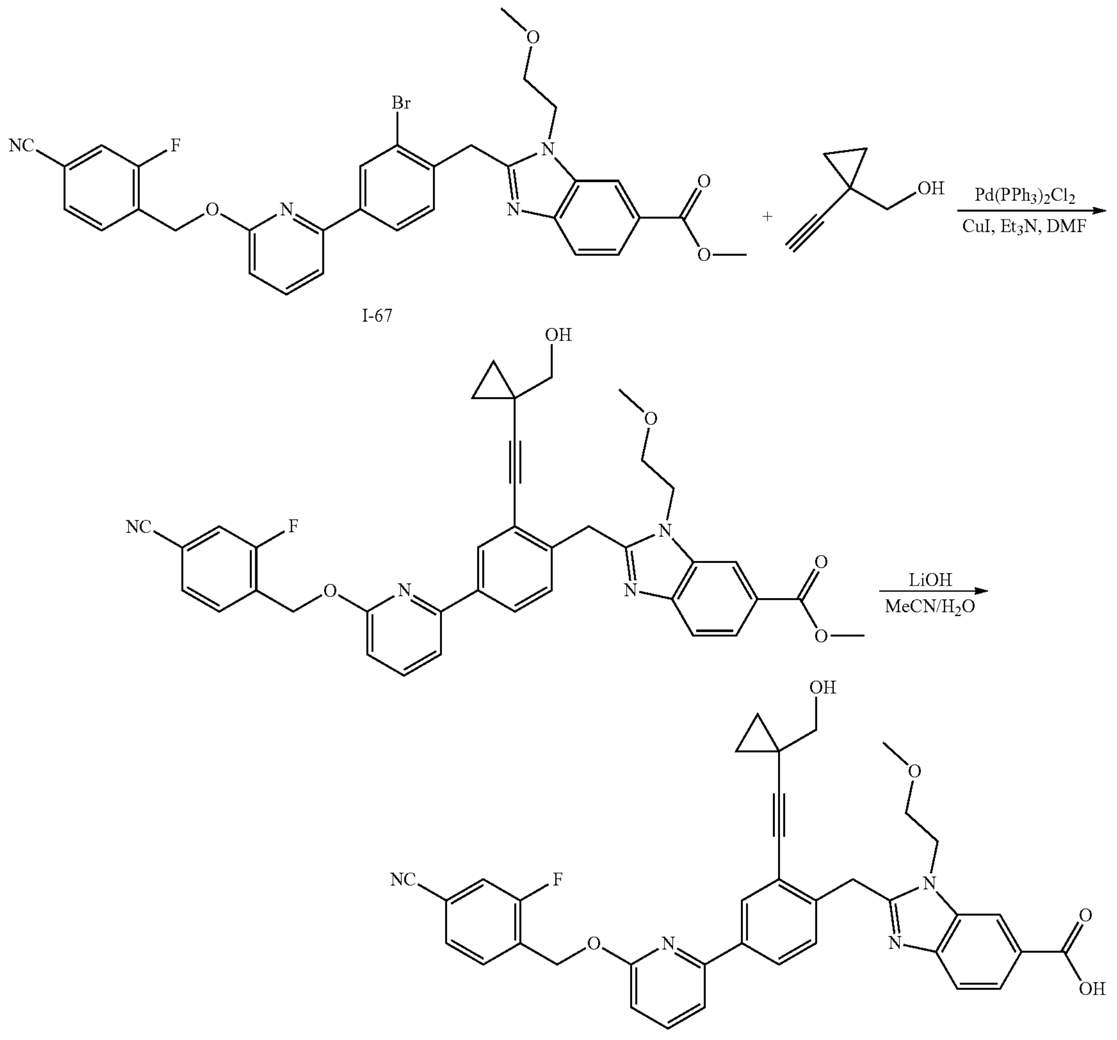

Example 240

Methyl 2-(4-(6-((4-cyano-2-fluorobenzyl)oxy)pyridin-2-yl)-2-((1-(hydroxymethyl)cyclopropyl)ethynyl)benzyl)-1-(2-methoxyethyl)-1H-benzo[d]imidazole-6-carboxylate: To a vial was added ethyl 2-(2-bromo-4-(6-((4-cyano-2-fluorobenzyl)oxy)pyridin-2-yl)benzyl)-1-(2-methoxyethyl)-1H-benzo[d]imidazole-6-carboxylate (I-67, 35 mg, 0.056 mmol), (1-ethynylcyclopropyl)methanol (16 mg, 0.17 mmol), CuI (5.0 mg, 0.026 mmol), and $Pd(PPh_3)_2Cl_2$ (10 mg, 0.014 mmol). DMF (1.0 mL) was added followed by triethylamine (0.15 mL, 1.11 mmol), and the mixture was degassed with argon for two minutes. The vial was sealed, acetonitrile (1.5 mL) and aqueous lithium hydroxide (1.0 M, 0.34 mL, 0.34 mmol) was added. The mixture was heated to 45° C. for 2 hours. Following this time, the mixture was diluted with EtOAc (5 mL), the pH adjusted to ~5 with 1 M aqueous citric acid solution and the mixture extracted with EtOAc (3x5 mL). The combined organics were dried over $Na_2SO_4$, concentrated in vacuo, and purified by RP-HPLC (eluent: 0-100% MeCN/water with 0.1% TFA) to yield the product (Example 240) as the trifluoroacetate salt. ES/MS: 631.2 (M+H$^+$); $^1$H NMR (400 MHz, Methanol-d4) δ 8.60 (s, 1H), 8.27 (dd, J=8.6, 1.4 Hz, 1H), 8.14 (d, J=1.9 Hz, 1H), 8.04 (dd, J=8.1, 1.9 Hz, 1H), 7.85-7.78 (m, 2H), 7.73 (t, J=7.6 Hz, 1H), 7.70-7.65 (m, 1H), 7.63 (dd, J=9.8, 1.5 Hz, 1H), 7.59 (d, J=1.7 Hz, 1H), 7.53 (d, J=8.7 Hz, 1H), 6.91 (d, J=8.2 Hz, 1H), 5.65 (s, 2H), 4.85 (d, J=4.5 Hz, 2H), 3.82 (t, J=4.9 Hz, 2H), 3.39 (s, 2H), 3.35 (s, 3H), 0.88-0.82 (m, 2H), 0.79 (td, J=6.2, 5.3, 2.9 Hz, 2H).

Example 228, 232, 237, 254, 255, 257, and 258. Compounds Prepared Using Procedure 49

Other compounds of the present disclosure prepared using the general route described in Procedure 49 include the following Example.

| Example | Structure/Name/Characterization |
|---|---|
| 228 | 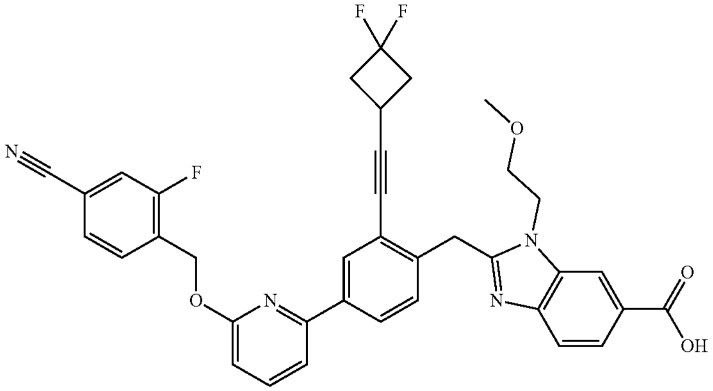 [SMILES: COCCn1c(Cc2ccc(-c3cccc(OCc4ccc(C#N)cc4F)n3)cc2C#CC2CC(F)(F)C2)nc2ccc(C(=O)O)cc21] 2-(4-(6-((4-cyano-2-fluorobenzyl)oxy)pyridin-2-yl)-2-((3,3-difluorocyclobutyl)ethynyl)benzyl)-1-(2-methoxyethyl)-1H-benzo[d]imidazole-6-carboxylic acid: ES/MS m/z 651.2; $^1$H NMR (400 MHz, Methanol-d4) δ 8.62 (s, 1H), 8.28 (dd, J = 8.6, 1.3 Hz, 1H), 8.17 (d, J = 1.9 Hz, 1H), 8.07 (dd, J = 8.2, 1.9 Hz, 1H), 7.87-7.78 (m, 2H), 7.73 (t, J = 7.5 Hz, 1H), 7.65-7.54 (m, 3H), 7.51 (d, J = 8.1 Hz, 1H), 6.93 (d, J = 8.2 Hz, 1H), 5.66 (s, 2H), 4.85 (t, J = 4.9 Hz, 2H), 3.85 (t, J = 4.9 Hz, 2H), 3.36 (s, 3H), 3.13 (tt, J = 9.6, 7.2 Hz, 1H), 3.00-2.81 (m, 2H), 2.46 (ddtd, J = 16.2, 10.2, 6.9, 3.2 Hz, 2H). |
| 232 | 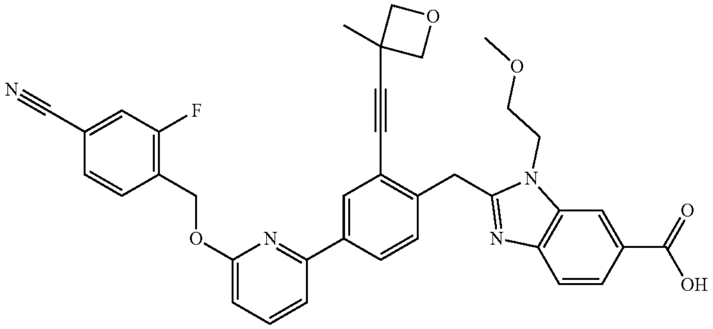 [SMILES: COCCn1c(Cc2ccc(-c3cccc(OCc4ccc(C#N)cc4F)n3)cc2C#CC2(C)COC2)nc2ccc(C(=O)O)cc21] 2-(4-(6-((4-cyano-2-fluorobenzyl)oxy)pyridin-2-yl)-2-((3-methyloxetan-3-yl)ethynyl)benzyl)-1-(2-methoxyethyl)-1H-benzo[d]imidazole-6-carboxylic acid: ES/MS m/z 631.3; $^1$H NMR (400 MHz, Methanol-d4) δ 8.50 (s, 1H), 8.25-8.12 (m, 2H), 8.04 (dd, J = 8.0, 2.1 Hz, 1H), 7.84-7.55 (m, 6H), 7.45 (d, J = 8.2 Hz, 1H), 6.92 (d, J = 8.2 Hz, 1H), 5.66 (s, 2H), 4.83 (s, 2H), 4.75 (s, 2H), 4.66 (d, J = 5.5 Hz, 2H), 4.44 (d, J = 5.5 Hz, 2H), 3.80 (t, J = 4.9 Hz, 2H), 1.56 (s, 3H). (OMe peak overlapping with solvent) |
| 237 | 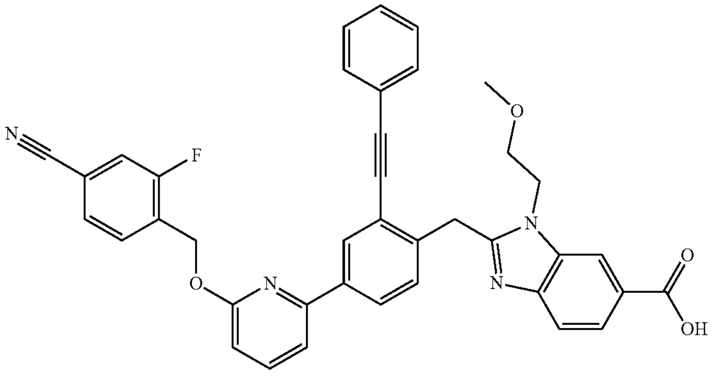 [SMILES: COCCn1c(Cc2ccc(-c3cccc(OCc4ccc(C#N)cc4F)n3)cc2C#Cc2ccccc2)nc2ccc(C(=O)O)cc21] |

-continued

| Example | Structure/Name/Characterization |
|---|---|
| | 2-(4-(6-((4-cyano-2-fluorobenzyl)oxy)pyridin-2-yl)-2-(phenylethynyl)benzyl)-1-(2-methoxyethyl)-1H-benzo[d]imidazole-6-carboxylic acid: ES/MS m/z 637.2; $^1$H NMR (400 MHz, Methanol-d4) δ 8.48 (s, 1H), 8.27 (d, J = 1.9 Hz, 1H), 8.20 (dd, J = 8.6, 1.4 Hz, 1H), 8.10 (dd, J = 8.2, 2.0 Hz, 1H), 7.83 (dd, J = 8.2, 7.5 Hz, 1H), 7.78-7.71 (m, 2H), 7.62-7.52 (m, 4H), 7.41-7.35 (m, 1H), 7.35-7.30 (m, 2H), 7.30-7.25 (m, 2H), 6.93 (d, J = 8.2 Hz, 1H), 5.67 (s, 2H), 4.94 (s, 2H), 4.76 (t, J = 5.0 Hz, 2H), 3.77 (t, J = 4.9 Hz, 2H), 3.21 (s, 3H). |
| 254 | 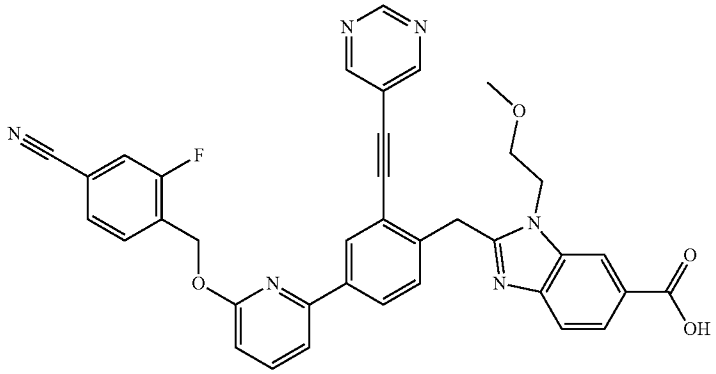 [SMILES: COCCn1c(Cc2ccc(-c3cccc(OCc4ccc(C#N)cc4F)n3)cc2C#Cc2cncnc2)nc2ccc(C(=O)O)cc21] 2-(4-(6-((4-cyano-2-fluorobenzyl)oxy)pyridin-2-yl)-2-(pyrimidin-5-ylethynyl)benzyl)-1-(2-methoxyethyl)-1H-benzo[d]imidazole-6-carboxylic acid: ES/MS m/z 639.2; $^1$H NMR (400 MHz, Methanol-d4) δ 9.12 (s, 1H), 8.84 (s, 2H), 8.30 (s, 1H), 8.25 (s, 1H), 8.07 (d, J = 8.3 Hz, 1H), 7.99 (d, J = 8.3 Hz, 1H), 7.81 (t, J = 7.8 Hz, 1H), 7.75 (t, J = 7.5 Hz, 1H), 7.67 (d, J = 8.6 Hz, 1H), 7.63-7.54 (m, 3H), 7.43 (d, J = 8.0 Hz, 1H), 5.66 (s, 2H), 4.75 (s, 2H), 4.52 (s, 2H), 3.68 (d, J = 5.1 Hz, 2H), 3.20 (s, 3H). |
| 255 | 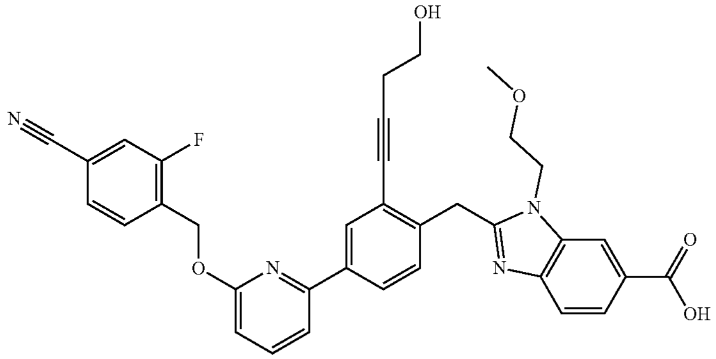 [SMILES: COCCn1c(Cc2ccc(-c3cccc(OCc4ccc(C#N)cc4F)n3)cc2C#CCCO)nc2ccc(C(=O)O)cc21] 2-(4-(6-((4-cyano-2-fluorobenzyl)oxy)pyridin-2-yl)-2-(4-hydroxybut-1-yn-1-yl)benzyl)-1-(2-methoxyethyl)-1H-benzo[d]imidazole-6-carboxylic acid: ES/MS m/z 605.2; $^1$H NMR (400 MHz, Methanol-d4) δ 8.57 (d, J = 1.2 Hz, 1H), 8.25 (dd, J = 8.6, 1.4 Hz, 1H), 8.13 (d, J = 1.9 Hz, 1H), 8.04 (dd, J = 8.1, 2.0 Hz, 1H), 7.86-7.76 (m, 2H), 7.73 (t, J = 7.5 Hz, 1H), 7.63 (dd, J = 9.7, 1.5 Hz, 1H), 7.60-7.48 (m, 3H), 6.91 (d, J = 8.2 Hz, 1H), 5.65 (s, 2H), 4.83 (t, J = 5.1 Hz, 2H), 3.82 (t, J = 4.9 Hz, 2H), 3.59 (t, J = 6.4 Hz, 2H), 3.34 (s, 3H), 2.58 (t, J = 6.4 Hz, 2H). One methylene overlapping with solvent. |
| 257 | 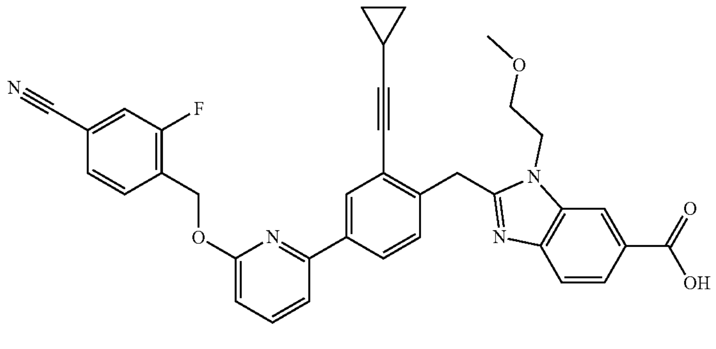 [SMILES: COCCn1c(Cc2ccc(-c3cccc(OCc4ccc(C#N)cc4F)n3)cc2C#CC2CC2)nc2ccc(C(=O)O)cc21] |

-continued

| Example | Structure/Name/Characterization |
|---|---|
| | 2-(4-(6-((4-cyano-2-fluorobenzyl)oxy)pyridin-2-yl)-2-(cyclopropylethynyl)benzyl)-1-(2-methoxyethyl)-1H-benzo[d]imidazole-6-carboxylic acid: ES/MS m/z 601; $^1$H NMR (400 MHz, Methanol-d4) δ 8.59 (t, J = 1.0 Hz, 1H), 8.25 (dd, J = 8.6, 1.4 Hz, 1H), 8.07 (d, J = 1.9 Hz, 1H), 8.01 (dd, J = 8.1, 2.0 Hz, 1H), 7.85-7.76 (m, 2H), 7.73 (t, J = 7.5 Hz, 1H), 7.61 (dd, J = 9.7, 1.4 Hz, 1H), 7.57 (dd, J = 7.9, 1.6 Hz, 1H), 7.54 (d, J = 7.4 Hz, 1H), 7.48 (d, J = 8.1 Hz, 1H), 6.91 (d, J = 8.2 Hz, 1H), 5.65 (s, 2H), 4.85-4.77 (m, 4H), 3.83 (t, J = 4.9 Hz, 2H), 3.36 (s, 3H), 1.39 (tt, J = 8.3, 5.0 Hz, 1H), 0.87-0.79 (m, 2H), 0.54-0.48 (m, 2H). |
| 258 | 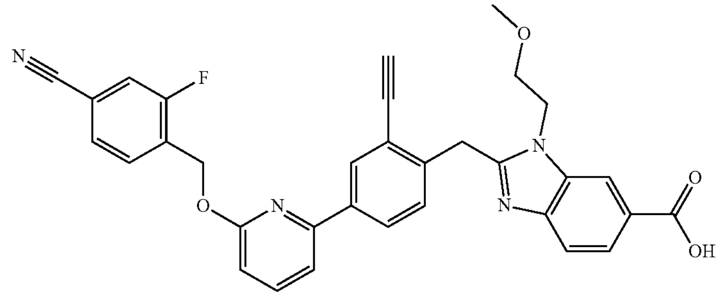 [SMILES: C#Cc1cc(-c2cccc(OCc3ccc(C#N)cc3F)n2)ccc1Cc1nc2ccc(C(=O)O)cc2n1CCOC] 2-(4-(6-((4-cyano-2-fluorobenzyl)oxy)pyridin-2-yl)-2-ethynylbenzyl)-1-(2-methoxyethyl)-1H-benzo[d]imidazole-6-carboxylic acid: ES/MS m/z 561.2; $^1$H NMR (400 MHz, Methanol-d4) δ 8.61-8.45 (m, 1H), 8.26-8.13 (m, 2H), 8.08 (dd, J = 8.1, 2.0 Hz, 1H), 7.81 (t, J = 7.9 Hz, 1H), 7.76-7.67 (m, 2H), 7.64-7.53 (m, 3H), 7.49 (d, J = 8.1 Hz, 1H), 6.91 (d, J = 8.3 Hz, 1H), 5.64 (s, 2H), 4.79 (t, J = 4.9 Hz, 2H), 3.91 (s, 1H), 3.81 (t, J = 5.0 Hz, 2H), 4H overlapping with solvent |

Example 226. 2-(4-(6-((4-cyano-2-fluorobenzyl)oxy)pyridin-2-yl)-2-fluorobenzyl)-1-((2-methyl-2H-tetrazol-5-yl)methyl)-1H-benzo[d]imidazole-6-carboxylic acid Procedure 50

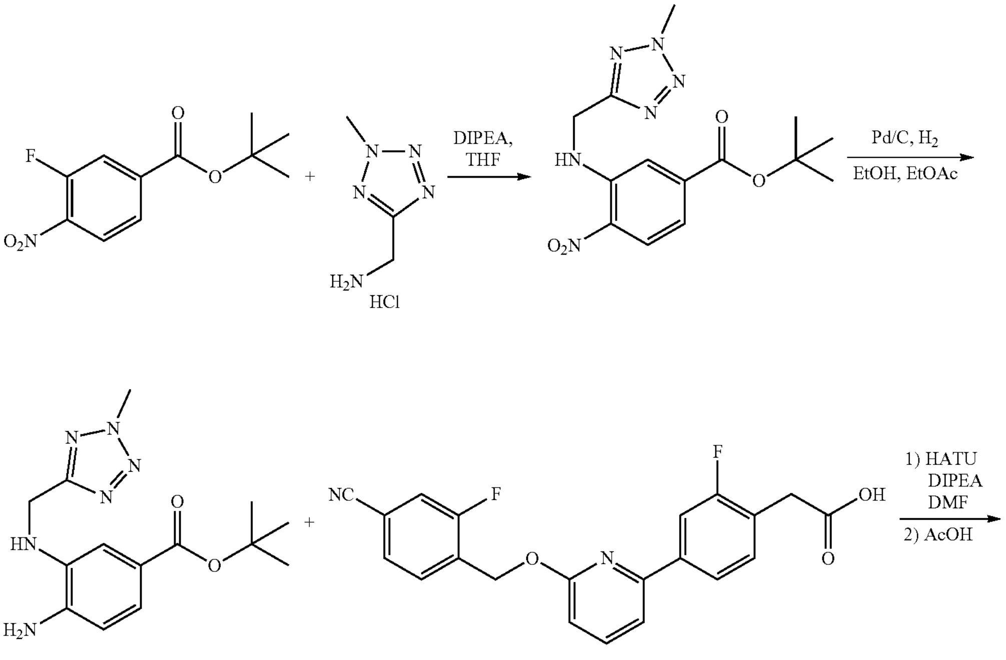

I-128

-continued

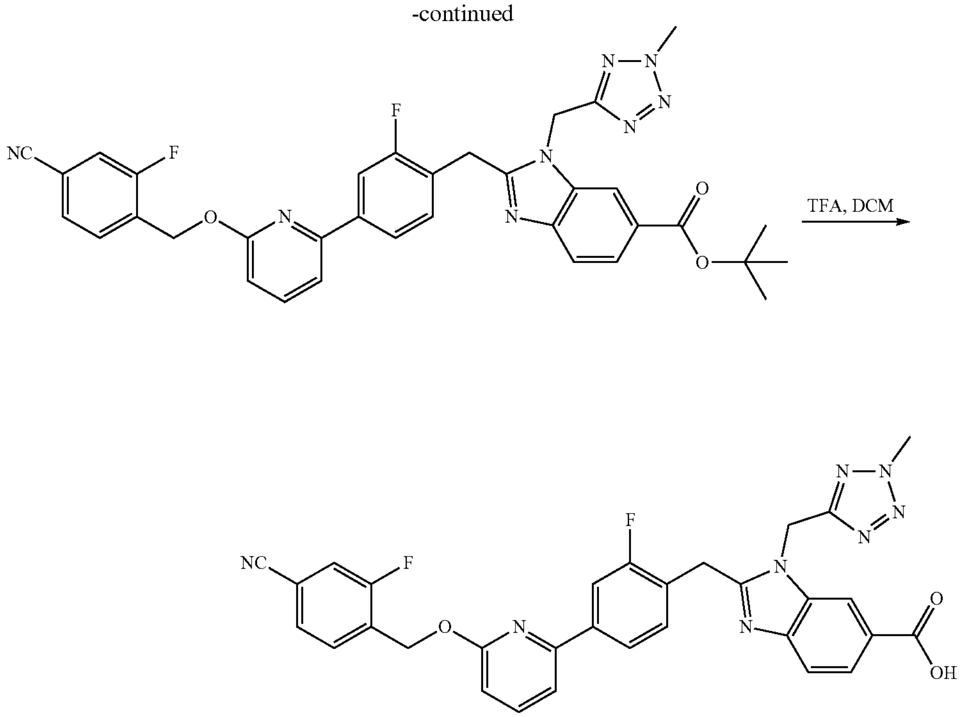

Example 226

Tert-butyl 3-(((2-methyl-2H-tetrazol-5-yl)methyl)amino)-4-nitrobenzoate: To a solution of tert-butyl 3-fluoro-4-nitrobenzoate (160 mg, 0.663 mmol) in THF (10 mL) was added diisopropylethylamine (0.35 mL, 2.00 mmol) and (2-methyl-2H-tetrazol-5-yl)methanamine hydrochloride (98 mg, 0.663 mmol). The resulting solution was heated to 55° C. for 10 hours. Upon completion the solvent was removed, the resulting residue taken up in EtOAc (150 mL), washed with brine (30 mL), concentrated and carried forward without further purification. ES/MS: 358.2 (M+Na+).

Tert-butyl 4-amino-3-(((2-methyl-2H-tetrazol-5-yl)methyl)amino)benzoate: Tert-butyl 3-(((2-methyl-2H-tetrazol-5-yl)methyl)amino)-4-nitrobenzoate (160 mg, 0.480 mmol) was dissolved in EtOH:EtOAc (5:1, 30 mL) after which 10% palladium on carbon (10 mg, 0.095 mmol) was then added. The resulting suspension was stirred under a hydrogen balloon at room temperature for 16 hours. The mixture was filtered through Celite washing with EtOAc (100 mL) and concentrated in vacuo to give the desired product without further purification. ES/MS: 327.2 (M+Na+).

Tert-butyl 2-(4-(6-((4-cyano-2-fluorobenzyl)oxy)pyridin-2-yl)-2-fluorobenzyl)-1-((2-methyl-2H-tetrazol-5-yl)methyl)-1H-benzo[d]imidazole-6-carboxylate: Tert-butyl 4-amino-3-(((2-methyl-2H-tetrazol-5-yl)methyl)amino)benzoate (117 mg, 0.38 mmol), 2-[4-[6-[(4-cyano-2-fluoro-phenyl)methoxy]-2-pyridyl]-3-fluoro-phenyl]acetic acid (I-128, 146 mg, 0.38 mmol), and O-(7-azabenzotriazol-1-yl)-N,N,N',N'-tetramethyluronium hexafluorophosphate (175 mg, 0.46 mmol) were taken up in DMF (3 mL) and N,N-diisopropylethylamine (0.37 mL, 2.11 mmol) was added. The mixture was stirred at room temperature for 16 hours. Following this time, the mixture was diluted with EtOAc (20 mL) and water (20 mL). The organic phase was collected, and the aqueous phase extracted with EtOAc (2×50 mL). The combined organic phases were dried over $Na_2SO_4$ and concentrated in vacuo. The resulting residue was taken up in acetic acid (10 mL) and heated to 80° C. After 1.5 hours, the mixture was concentrated in vacuo and used without further purification. ES/MS: 649.20 ($M+H^+$).

Tert-butyl 2-(4-(6-((4-cyano-2-fluorobenzyl)oxy)pyridin-2-yl)-2-fluorobenzyl)-1-((2-methyl-2H-tetrazol-5-yl)methyl)-1H-benzo[d]imidazole-6-carboxylate (Example 226): Methyl 2-(4-(6-((4-cyano-2-fluorobenzyl)oxy)pyridin-2-yl)benzyl)-1-(2-methoxyethyl)-1H-benzo[d]imidazole-6-carboxylate (170 mg, 0.27 mmol) was dissolved in DCM:TFA (4:1, 5 mL), and the resulting mixture was stirred at 40° C. for 2 hours. Following this time, the mixture was concentrated in vacuo and purified by RP-HPLC (eluent: 20-70% MeCN/water with 0.10% TFA) to yield the product (Example 226) as a trifluoroacetate salt. ES/MS: 593.2 ($M+H^+$); 1H NMR (400 MHz, DMSO-d6) δ 8.29 (d, J=1.5 Hz, 1H), 7.93 (dd, J=9.9, 1.4 Hz, 1H), 7.90-7.71 (m, 6H), 7.66 (d, J=2.3 Hz, 1H), 7.64 (d, J=3.3 Hz, 1H), 7.35 (t, J=8.0 Hz, 1H), 6.94 (d, J=8.2 Hz, 1H), 6.02 (s, 2H), 5.62 (s, 2H), 4.52 (s, 2H), 4.23 (s, 3H).

Example 230, 274, 275, 278, 289-292, 309, 344, 347, 350, 354, 356, 364, 559-560, 568-570, 576, 578-580, 587, 588, and 698-747. Compounds Prepared Using Procedure 50

Other compounds of the present disclosure prepared using the general route described in Procedure 50 include the following Example.

| Example | Structure/Name/Characterization |
|---|---|
| 230 | 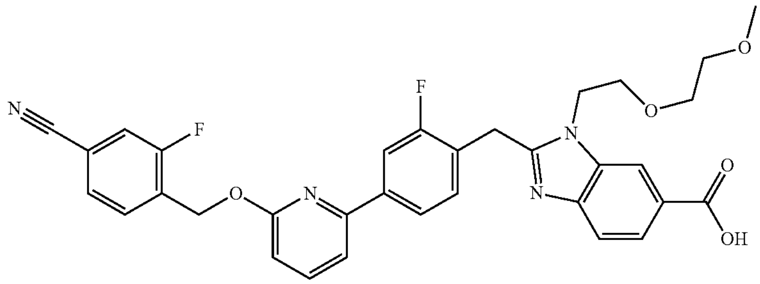 [SMILES: COCCOCCn1c(Cc2ccc(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2-fluorobenzyl)-1-(2-(2-methoxyethoxy)ethyl)-1H-benzo[d]imidazole-6-carboxylic acid: ES/MS m/z 599.2; $^1$H NMR (400 MHz, DMSO-d6) δ 8.35 (d, J = 1.4 Hz, 1H), 7.95-7.92 (m, 1H), 7.92-7.89 (m, 3H), 7.86 (d, J = 7.8 Hz, 1H), 7.79-7.74 (m, 1H), 7.73 (dd, J = 7.9, 1.4 Hz, 1H), 7.67 (t, J = 8.0 Hz, 2H), 7.48 (t, J = 7.9 Hz, 1H), 6.95 (d, J = 8.2 Hz, 1H), 5.62 (s, 2H), 4.66 (t, J = 5.0 Hz, 2H), 4.58 (s, 2H), 3.77 (t, J = 5.0 Hz, 2H), 3.48 (dd, J = 5.6, 3.6 Hz, 2H), 3.40-3.26 (m, 2H), 3.12 (s, 3H). |
| 274 | 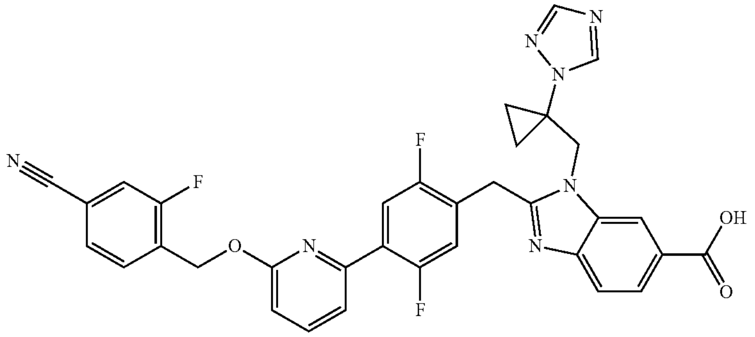 [SMILES: N#Cc1ccc(COc2cccc(-c3cc(F)c(Cc4nc5ccc(C(=O)O)cc5n4CC4(n5cncn5)CC4)cc3F)n2)c(F)c1] 1-((1-(1H-1,2,4-triazol-1-yl)cyclopropyl)methyl)-2-(4-(6-((4-cyano-2-fluorobenzyl)oxy)pyridin-2-yl)-2,5-difluorobenzyl)-1H-benzo[d]imidazole-6-carboxylic acid: ES/MS 636.2; $^1$H NMR (400 MHz, Methanol-d4) δ 8.04 (s, 1H), 8.04-7.96 (m, 2H), 7.91 (s, 1H), 7.80-7.64 (m, 3H), 7.63 (s, 1H), 7.57-7.45 (m, 3H), 7.08 (dd, J = 11.2, 6.1 Hz, 1H), 6.88 (dd, J = 8.3, 0.7 Hz, 1H), 5.59 (s, 2H), 4.83 (s, 2H), 4.08 (s, 2H), 1.66-1.55 (m, 2H), 1.55-1.47 (m, 2H). |
| 275 | 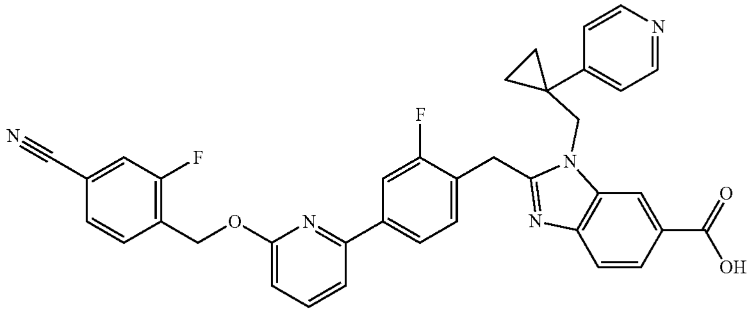 [SMILES: N#Cc1ccc(COc2cccc(-c3ccc(Cc4nc5ccc(C(=O)O)cc5n4CC4(c5ccncc5)CC4)c(F)c3)n2)c(F)c1] 2-(4-(6-((4-cyano-2-fluorobenzyl)oxy)pyridin-2-yl)-2-fluorobenzyl)-1-((1-(pyridin-4-yl)cyclopropyl)methyl)-1H-benzo[d]imidazole-6-carboxylic acid: ES/MS m/z 628.2; $^1$H NMR (400 MHz, Methanol-d4) δ 8.74-8.57 (m, 2H), 8.17-8.07 (m, 2H), 8.04-7.92 (m, 2H), 7.94-7.79 (m, 3H), 7.77-7.65 (m, 2H), 7.64-7.53 (m, 3H), 7.47 (t, J = 7.9 Hz, 1H), 6.93 (d, J = 8.2 Hz, 1H), 5.66 (s, 2H), 5.09 (s, 2H), 4.59 (s, 2H), 1.57-1.44 (m, 2H), 1.38 (t, J = 3.4 Hz, 2H). |

-continued

| Example | Structure/Name/Characterization |
|---|---|
| 278 | 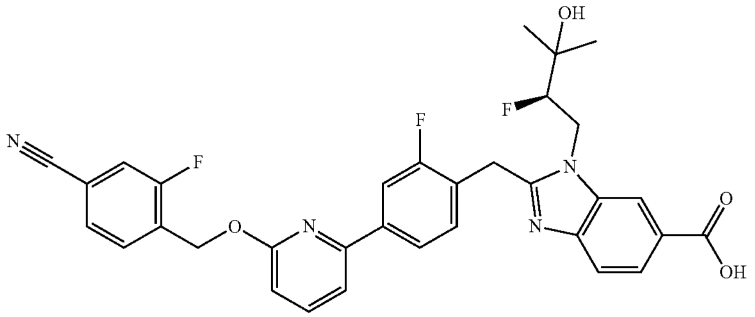 [SMILES: CC(C)(O)[C@H](F)Cn1c(Cc2ccc(-c3cccc(OCc4ccc(C#N)cc4F)n3)cc2F)nc2ccc(C(=O)O)cc21]<br>(R)-2-(4-(6-((4-cyano-2-fluorobenzyl)oxy)pyridin-2-yl)-2-fluorobenzyl)-1-(2-fluoro-3-hydroxy-3-methylbutyl)-1H-benzo[d]imidazole-6-carboxylic acid: ES/MS m/z 601.4; $^1$H NMR (400 MHz, Methanol-d4) δ 8.51 (s, 1H), 8.26 (dd, J = 8.5, 1.5 Hz, 1H), 8.02-7.86 (m, 2H), 7.86-7.79 (m, 2H), 7.73 (t, J = 7.5 Hz, 1H), 7.65-7.48 (m, 4H), 6.92 (d, J = 8.2 Hz, 1H), 5.65 (s, 2H), 5.12-4.94 (m, 2H), 4.83-4.51 (m, 3H), 1.40 (dd, J = 3.9, 1.8 Hz, 6H). |
| 289 | 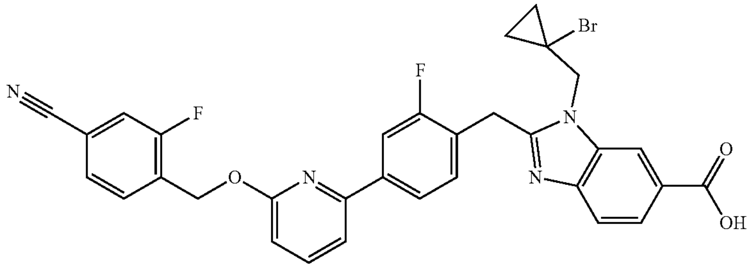 [SMILES: N#Cc1ccc(COc2cccc(-c3ccc(Cc4nc5ccc(C(=O)O)cc5n4CC4(Br)CC4)c(F)c3)n2)c(F)c1]<br>1-((1-bromocyclopropyl)methyl)-2-(4-(6-((4-cyano-2-fluorobenzyl)oxy)pyridin-2-yl)-2-fluorobenzyl)-1H-benzo[d]imidazole-6-carboxylic acid: ES/MS m/z 629; $^1$H NMR (400 MHz, Methanol-d4) δ 8.64 (d, J = 1.2 Hz, 1H), 8.26 (dd, J = 8.6, 1.4 Hz, 1H), 8.01-7.87 (m, 2H), 7.87-7.78 (m, 2H), 7.73 (t, J = 7.5 Hz, 1H), 7.66-7.46 (m, 4H), 6.92 (d, J = 8.2 Hz, 1H), 5.65 (s, 2H), 5.01 (s, 2H), 4.88 (s, 2H), 1.57-1.47 (m, 2H), 1.47-1.37 (m, 2H). |
| 290 | 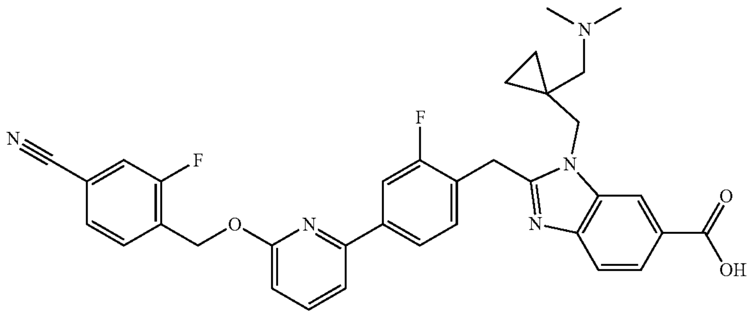 [SMILES: CN(C)CC1(Cn2c(Cc3ccc(-c4cccc(OCc5ccc(C#N)cc5F)n4)cc3F)nc3ccc(C(=O)O)cc32)CC1]<br>2-(4-(6-((4-cyano-2-fluorobenzyl)oxy)pyridin-2-yl)-2-fluorobenzyl)-1-((1-((dimethylamino)methyl)cyclopropyl)methyl)-1H-benzo[d]imidazole-6-carboxylic acid: ES/MS 608.2; $^1$H NMR (400 MHz, Methanol-d4) δ 8.56-8.42 (m, 1H), 8.22 (dd, J = 8.5, 1.4 Hz, 1H), 8.02-7.66 (m, 5H), 7.66-7.48 (m, 4H), 6.92 (d, J = 8.2 Hz, 1H), 5.65 (s, 2H), 5.02 (s, 2H), 4.71 (s, 2H), 3.49 (s, 2H), 3.09 (s, 6H), 0.90 (d, J = 5.9 Hz, 2H), 0.62 (d, J = 6.1 Hz, 2H). |

-continued

| Example | Structure/Name/Characterization |
|---|---|
| 291 | 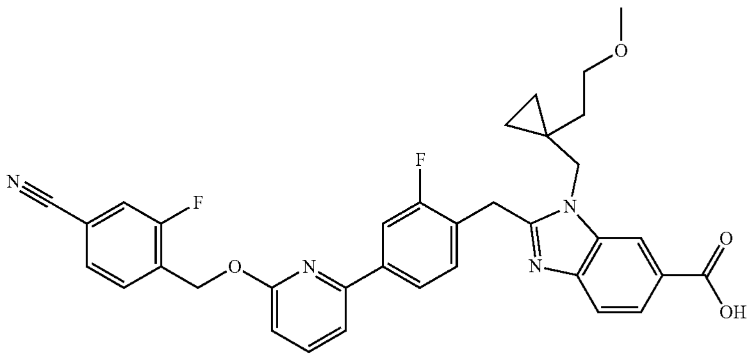 [SMILES: COCCC1(Cn2c(Cc3ccc(-c4cccc(OCc5ccc(C#N)cc5F)n4)cc3F)nc3ccc(C(=O)O)cc32)CC1] 2-(4-(6-((4-cyano-2-fluorobenzyl)oxy)pyridin-2-yl)-2-fluorobenzyl)-1-((1-(2-methoxyethyl)cyclopropyl)methyl)-1H-benzo[d]imidazole-6-carboxylic acid: ES/MS m/z 609.2; $^1$H NMR (400 MHz, Methanol-d4) δ 8.64 (s, 1H), 8.25 (d, J = 8.7 Hz, 1H), 7.93-7.59 (m, 5H), 7.52-7.38 (m, 4H), 6.87 (d, J = 8.2 Hz, 1H), 5.60 (s, 2H), 4.77 (s, 2H), 4.62 (s, 2H), 3.49 (t, J = 5.5 Hz, 2H), 1.57 (t, J = 5.5 Hz, 2H), 0.84-0.61 (m, 4H). |
| 292 | 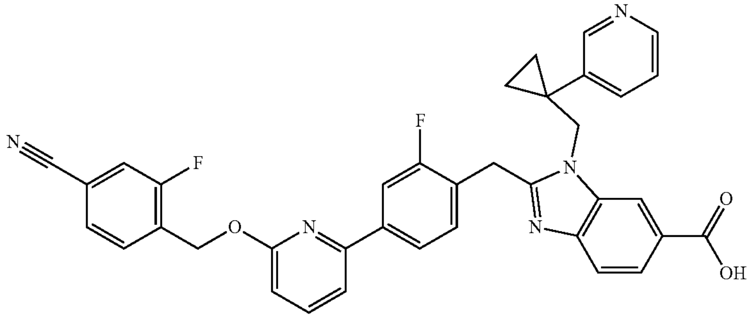 [SMILES: N#Cc1ccc(COc2cccc(-c3ccc(Cc4nc5ccc(C(=O)O)cc5n4CC4(c5cccnc5)CC4)c(F)c3)n2)c(F)c1] 2-(4-(6-((4-cyano-2-fluorobenzyl)oxy)pyridin-2-yl)-2-fluorobenzyl)-1-((1-(pyridin-3-yl)cyclopropyl)methyl)-1H-benzo[d]imidazole-6-carboxylic acid: ES/MS 628.2; $^1$H NMR (400 MHz, Methanol-d4) δ 8.87 (s, 1H), 8.72 (d, J = 5.7 Hz, 1H), 8.55 (dt, J = 8.2, 1.6 Hz, 1H), 8.14 (dd, J = 8.6, 1.4 Hz, 1H), 8.04-7.66 (m, 7H), 7.66-7.44 (m, 4H), 6.92 (d, J = 8.2 Hz, 1H), 5.64 (s, 2H), 5.06 (s, 3H), 4.68 (s, 2H), 1.89 (s, 2H), 1.52 (d, J = 5.5 Hz, 2H). |
| 309 | 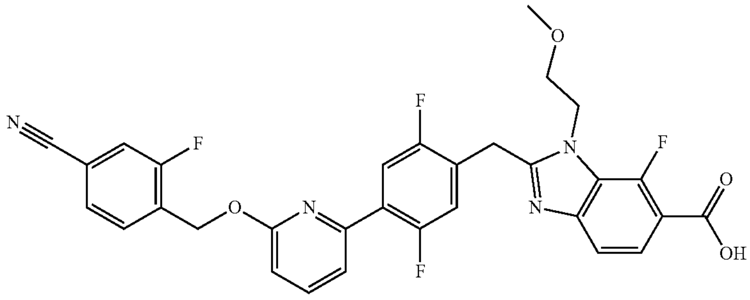 [SMILES: COCCn1c(Cc2cc(F)c(-c3cccc(OCc4ccc(C#N)cc4F)n3)cc2F)nc2ccc(C(=O)O)c(F)c21] 2-(4-(6-((4-cyano-2-fluorobenzyl)oxy)pyridin-2-yl)-2,5-difluorobenzyl)-7-fluoro-1-(2-methoxyethyl)-1H-benzo[d]imidazole-6-carboxylic acid: ES/MS m/z 591.5; $^1$H NMR (400 MHz, Methanol-d4) δ 7.85 (dd, J = 8.6, 6.7 Hz, 1H), 7.79-7.63 (m, 3H), 7.55-7.41 (m, 4H), 7.06 (dd, J = 11.3, 6.0 Hz, 1H), 6.86 (d, J = 8.2 Hz, 1H), 5.59 (s, 2H), 4.58 (t, J = 5.0 Hz, 2H), 4.44 (s, 2H), 3.77 (t, J = 4.9 Hz, 2H), 3.29 (s, 3H). |

-continued

| Example | Structure/Name/Characterization |
|---|---|
| 344 | 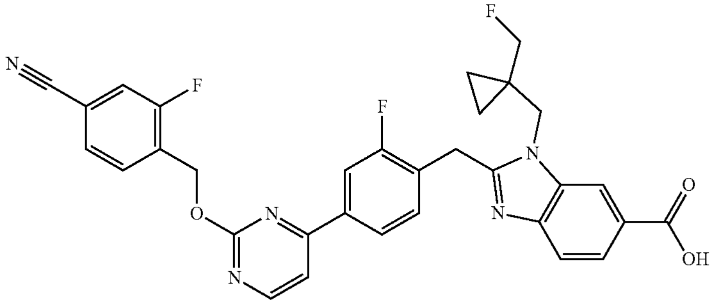 [SMILES: N#Cc1ccc(COc2nccc(-c3ccc(Cc4nc5ccc(C(=O)O)cc5n4CC4(CF)CC4)c(F)c3)n2)c(F)c1] 2-(4-(2-((4-cyano-2-fluorobenzyl)oxy)pyrimidin-4-yl)-2-fluorobenzyl)-1-((1-(fluoromethyl)cyclopropyl)methyl)-1H-benzo[d]imidazole-6-carboxylic acid: ES/MS m/z 584.3; $^1$H NMR (400 MHz, DMSO-d6) δ 8.75 (d, J = 5.3 Hz, 1H), 8.28 (d, J = 1.4 Hz, 1H), 8.10-7.99 (m, 2H), 7.95 (dd, J = 10.0, 1.4 Hz, 1H), 7.89-7.71 (m, 4H), 7.61 (d, J = 8.5 Hz, 1H), 7.55 (t, J = 7.8 Hz, 1H), 5.63 (s, 2H), 4.56 (s, 2H), 4.50 (s, 2H), 4.18 (d, J = 48.8 Hz, 2H), 0.90-0.79 (m, 2H), 0.77-0.66 (m, 2H). |
| 347 | 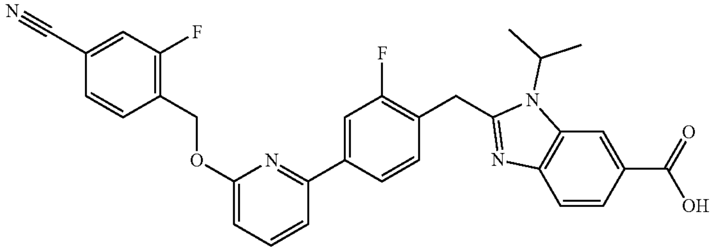 [SMILES: CC(C)n1c(Cc2ccc(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2-fluorobenzyl)-1-isopropyl-1H-benzo[d]imidazole-6-carboxylic acid: ES/MS m/z 539.3; $^1$H NMR (400 MHz, DMSO-d6) δ 8.30 (d, J = 1.4 Hz, 1H), 7.97-7.81 (m, 5H), 7.80-7.64 (m, 4H), 7.44 (t, J = 7.9 Hz, 1H), 6.94 (d, J = 8.2 Hz, 1H), 5.62 (s, 2H), 5.08-4.91 (m, 1H), 4.56 (s, 2H), 1.58 (d, J = 6.9 Hz, 6H). |
| 350 | 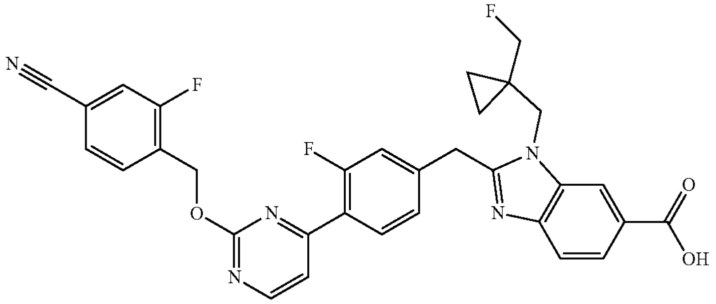 [SMILES: N#Cc1ccc(COc2nccc(-c3ccc(Cc4nc5ccc(C(=O)O)cc5n4CC4(CF)CC4)cc3F)n2)c(F)c1] 2-(4-(2-((4-cyano-2-fluorobenzyl)oxy)pyrimidin-4-yl)-3-fluorobenzyl)-1-((1-(fluoromethyl)cyclopropyl)methyl)-1H-benzo[d]imidazole-6-carboxylic acid: ES/MS m/z 584.3; $^1$H NMR (400 MHz, DMSO-d6) δ 8.74 (d, J = 5.1 Hz, 1H), 8.29 (d, J = 1.5 Hz, 1H), 8.06 (t, J = 8.2 Hz, 1H), 7.98-7.91 (m, 1H), 7.86 (dd, J = 8.4, 1.5 Hz, 1H), 7.82-7.72 (m, 2H), 7.67 (d, J = 8.5 Hz, 1H), 7.59 (dd, J = 5.2, 2.0 Hz, 1H), 7.41 (dd, J = 12.6, 1.6 Hz, 1H), 7.37 (dd, J = 8.1, 1.6 Hz, 1H), 5.61 (s, 2H), 4.54 (s, 2H), 4.53 (s, 2H), 4.18 (d, J = 48.8 Hz, 2H), 0.86-0.77 (m, 2H), 0.71 (d, J = 5.0 Hz, 2H). |
| 354 | 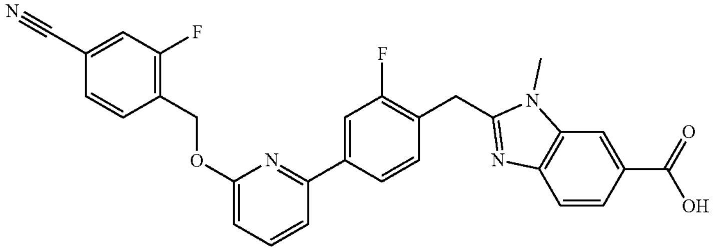 [SMILES: Cn1c(Cc2ccc(-c3cccc(OCc4ccc(C#N)cc4F)n3)cc2F)nc2ccc(C(=O)O)cc21] |

-continued

| Example | Structure/Name/Characterization |
|---|---|
| | 2-(4-(6-((4-cyano-2-fluorobenzyl)oxy)pyridin-2-yl)-2-fluorobenzyl)-1-methyl-1H-benzo[d]imidazole-6-carboxylic acid: ES/MS m/z 511.3; $^1$H NMR (400 MHz, DMSO-d6) δ 8.29 (d, J = 1.6 Hz, 1H), 8.03-7.81 (m, 5H), 7.80-7.71 (m, 2H), 7.70-7.63 (m, 2H), 7.49 (t, J = 7.9 Hz, 1H), 6.94 (d, J = 8.2 Hz, 1H), 5.62 (s, 2H), 4.53 (s, 2H), 3.96 (s, 3H). |
| 356 | 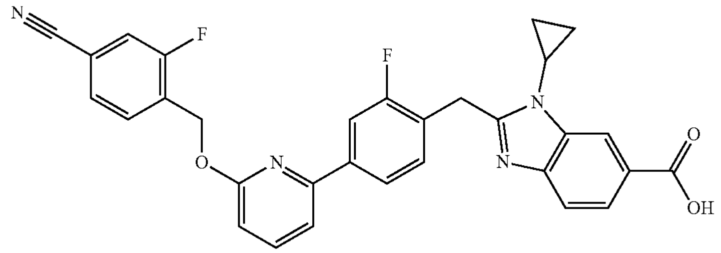 [SMILES: N#Cc1ccc(COc2cccc(-c3ccc(Cc4nc5ccc(C(=O)O)cc5n4C4CC4)c(F)c3)n2)c(F)c1] 2-(4-(6-((4-cyano-2-fluorobenzyl)oxy)pyridin-2-yl)-2-fluorobenzyl)-1-cyclopropyl-1H-benzo[d]imidazole-6-carboxylic acid: ES/MS m/z 537.3; $^1$H NMR (400 MHz, DMSO-d6) δ 8.21 (d, J = 1.5 Hz, 1H), 7.99-7.82 (m, 5H), 7.81-7.70 (m, 2H), 7.66 (dd, J = 11.5, 7.9 Hz, 2H), 7.50 (t, J = 7.9 Hz, 1H), 6.94 (d, J = 8.2 Hz, 1H), 5.62 (s, 2H), 4.54 (s, 2H), 3.47-3.33 (m, 1H), 1.36-1.26 (m, 2H), 1.19-1.10 (m, 2H). |
| 364 | 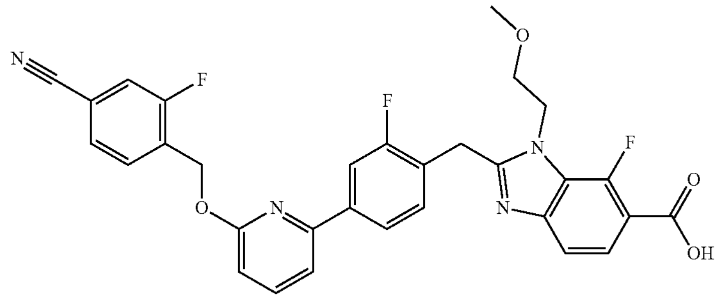 [SMILES: COCCn1c(Cc2ccc(-c3cccc(OCc4ccc(C#N)cc4F)n3)cc2F)nc2ccc(C(=O)O)c(F)c21] 2-(4-(6-((4-cyano-2-fluorobenzyl)oxy)pyridin-2-yl)-2-fluorobenzyl)-7-fluoro-1-(2-methoxyethyl)-1H-benzo[d]imidazole-6-carboxylic acid: ES/MS 573.2; $^1$H NMR (400 MHz, DMSO-d6) δ 7.96-7.81 (m, 4H), 7.80-7.69 (m, 2H), 7.69-7.61 (m, 2H), 7.48-7.37 (m, 2H), 6.93 (d, J = 8.2 Hz, 1H), 5.62 (s, 2H), 4.58 (t, J = 5.2 Hz, 2H), 4.42 (s, 2H), 3.71 (t, J = 5.2 Hz, 2H), 3.23 (s, 3H). |
| 559 | 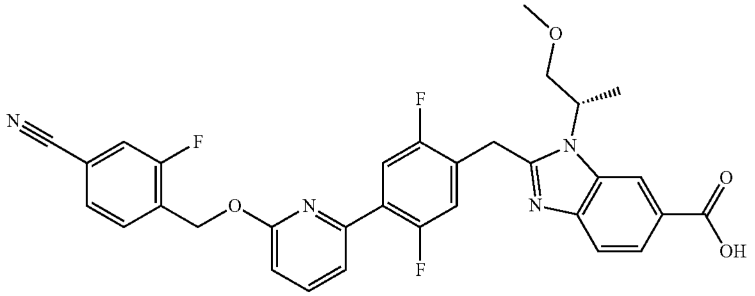 [SMILES: COC[C@H](C)n1c(Cc2cc(F)c(-c3cccc(OCc4ccc(C#N)cc4F)n3)cc2F)nc2ccc(C(=O)O)cc21] (S)-2-(4-(6-((4-cyano-2-fluorobenzyl)oxy)pyridin-2-yl)-2,5-difluorobenzyl)-1-(1-methoxypropan-2-yl)-1H-benzo[d]imidazole-6-carboxylic acid: ES/MS m/z 587.2; $^1$H NMR (400 MHz, Methanol-d4) δ 8.57 (t, J = 1.0 Hz, 1H), 8.17 (dd, J = 8.6, 1.4 Hz, 1H), 7.86-7.77 (m, 3H), 7.73 (t, J = 7.5 Hz, 1H), 7.69-7.51 (m, 3H), 7.31 (dd, J = 11.3, 6.1 Hz, 1H), 6.95 (d, J = 8.2 Hz, 1H), 5.63 (s, 2H), 5.20-5.09 (m, 1H), 4.74-4.60 (m, 2H), 4.03 (dd, J = 10.4, 9.0 Hz, 1H), 3.81 (dd, J = 10.4, 4.1 Hz, 1H), 3.26 (s, 3H), 1.76 (d, J = 7.1 Hz, 3H). |

-continued

| Example | Structure/Name/Characterization |
|---|---|
| 560 | 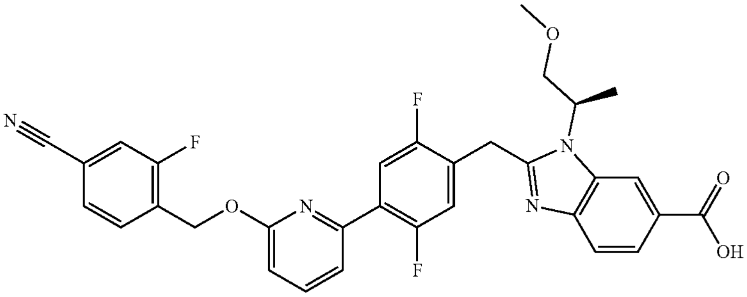 [SMILES: COC[C@@H](C)n1c(Cc2cc(F)c(-c3cccc(OCc4ccc(C#N)cc4F)n3)cc2F)nc2ccc(C(=O)O)cc21] (R)-2-(4-(6-((4-cyano-2-fluorobenzyl)oxy)pyridin-2-yl)-2,5-difluorobenzyl)-1-(1-methoxypropan-2-yl)-1H-benzo[d]imidazole-6-carboxylic acid: ES/MS m/z 587.2; $^1$H NMR (400 MHz, Methanol-d4) δ 8.62 (t, J = 1.0 Hz, 1H), 8.22 (dd, J = 8.6, 1.4 Hz, 1H), 7.88-7.78 (m, 3H), 7.73 (t, J = 7.5 Hz, 1H), 7.66-7.52 (m, 3H), 7.36 (dd, J = 11.2, 6.1 Hz, 1H), 6.96 (dd, J = 8.3, 0.6 Hz, 1H), 5.63 (s, 2H), 5.26-5.16 (m, 1H), 4.82-4.66 (m, 2H), 4.05 (dd, J = 10.4, 9.1 Hz, 1H), 3.83 (dd, J = 10.5, 4.0 Hz, 1H), 3.26 (s, 3H), 1.79 (d, J = 7.1 Hz, 3H). |
| 568 | 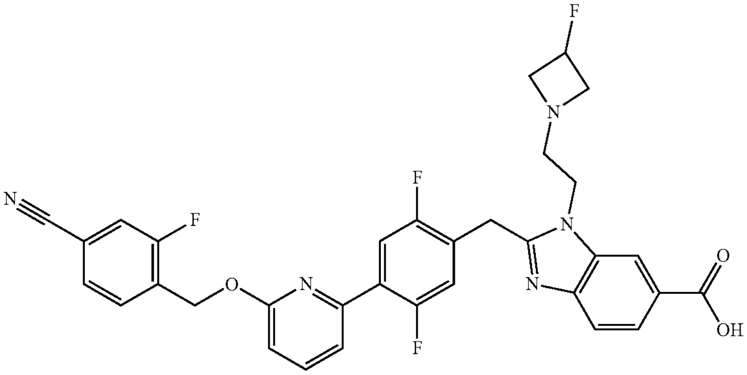 [SMILES: N#Cc1ccc(COc2cccc(-c3cc(F)c(Cc4nc5ccc(C(=O)O)cc5n4CCN4CC(F)C4)cc3F)n2)c(F)c1] 2-(4-(6-((4-cyano-2-fluorobenzyl)oxy)pyridin-2-yl)-2,5-difluorobenzyl)-1-(2-(3-fluoroazetidin-1-yl)ethyl)-1H-benzo[d]imidazole-6-carboxylic acid: ES/MS m/z 616.5; $^1$H NMR (400 MHz, Methanol-d4) δ 8.44 (s, 1H), 8.09 (s, 1H), 7.90-7.67 (m, 4H), 7.66-7.48 (m, 3H), 7.33 (s, 1H), 6.95 (d, J = 8.2 Hz, 1H), 5.63 (s, 2H), 5.44 (d, J = 56.6 Hz, 1H), 4.79-4.63 (m, 4H), 4.61 (d, J = 30.3 Hz, 2H), 4.45 (d, J = 19.2 Hz, 2H), 3.87 (s, 2H). |
| 569 | 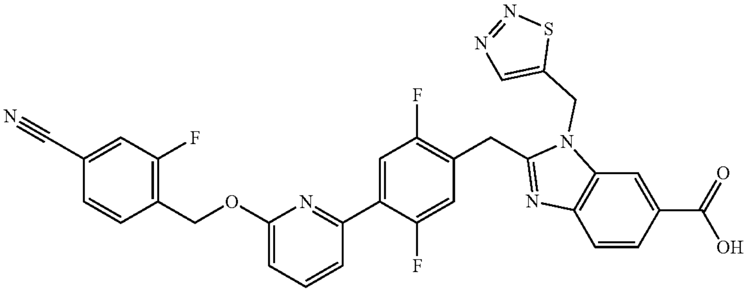 [SMILES: N#Cc1ccc(COc2cccc(-c3cc(F)c(Cc4nc5ccc(C(=O)O)cc5n4Cc4cnns4)cc3F)n2)c(F)c1] 1-((1,2,3-thiadiazol-5-yl)methyl)-2-(4-(6-((4-cyano-2-fluorobenzyl)oxy)pyridin-2-yl)-2,5-difluorobenzyl)-1H-benzo[d]imidazole-6-carboxylic acid: ES/MS m/z 613.1; $^1$H NMR (400 MHz, DMSO-d6) δ 8.79 (s, 1H), 8.26 (d, J = 1.5 Hz, 1H), 7.94-7.80 (m, 3H), 7.80-7.62 (m, 4H), 7.50 (dd, J = 7.3, 1.7 Hz, 1H), 7.39 (dd, J = 11.4, 6.1 Hz, 1H), 6.99 (d, J = 8.3 Hz, 1H), 6.27 (s, 2H), 5.59 (s, 2H), 4.48 (s, 2H). |

-continued

| Example | Structure/Name/Characterization |
|---|---|
| 570 | 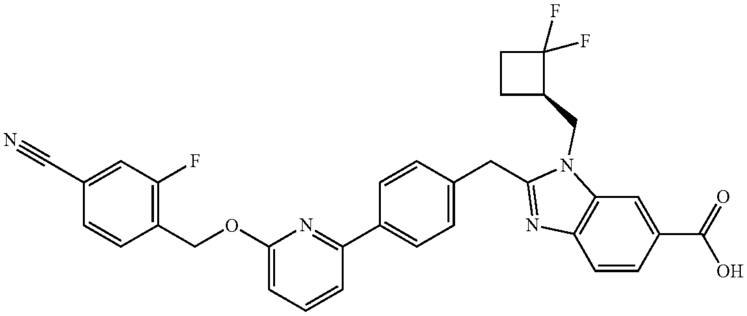 [SMILES: N#Cc1ccc(COc2cccc(-c3ccc(Cc4nc5ccc(C(=O)O)cc5n4C[C@H]4CCC4(F)F)cc3)n2)c(F)c1] And 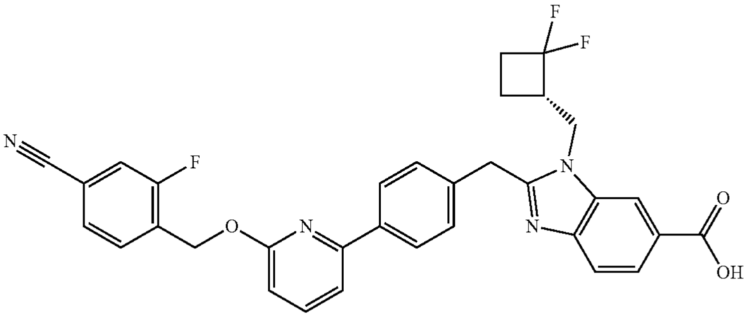 [SMILES: N#Cc1ccc(COc2cccc(-c3ccc(Cc4nc5ccc(C(=O)O)cc5n4C[C@@H]4CCC4(F)F)cc3)n2)c(F)c1] 2-(4-(6-((4-cyano-2-fluorobenzyl)oxy)pyridin-2-yl)-2,5-difluorobenzyl)-1-((2,2-difluorocyclobutyl)methyl)-1H-benzo[d]imidazole-6-carboxylic acid: ES/MS m/z 619.3; $^1$H NMR (400 MHz, Methanol-d4) δ 8.54-8.43 (m, 1H), 8.18 (dd, J = 8.6, 1.5 Hz, 1H), 7.89-7.68 (m, 4H), 7.68-7.51 (m, 3H), 7.34 (dd, J = 11.2, 6.1 Hz, 1H), 6.96 (dd, J = 8.3, 0.7 Hz, 1H), 5.63 (s, 2H), 4.77-4.59 (m, 3H), 3.57-3.36 (m, 1H), 2.73-2.44 (m, 2H), 2.19-1.91 (m, 1H), 1.78 (q, J = 9.5 Hz, 1H). |
| 576 | 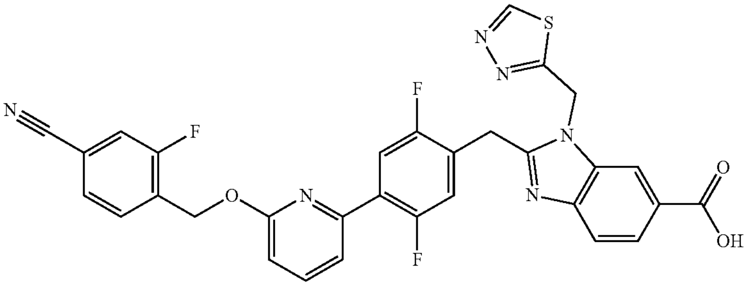 [SMILES: N#Cc1ccc(COc2cccc(-c3cc(F)c(Cc4nc5ccc(C(=O)O)cc5n4Cc4nncs4)cc3F)n2)c(F)c1] 1-((1,3,4-thiadiazol-2-yl)methyl)-2-(4-(6-((4-cyano-2-fluorobenzyl)oxy)pyridin-2-yl)-2,5-difluorobenzyl)-1H-benzo[d]imidazole-6-carboxylic acid: ES/MS m/z 613.5; $^1$H NMR (400 MHz, Methanol-d4) δ 9.39 (s, 1H), 8.46-8.35 (m, 1H), 8.09 (dd, J = 8.5, 1.5 Hz, 1H), 7.87-7.78 (m, 1H), 7.75 (dd, J = 14.9, 7.9 Hz, 2H), 7.68 (dd, J = 10.8, 6.3 Hz, 1H), 7.65-7.56 (m, 2H), 7.53 (d, J = 6.2 Hz, 1H), 7.19 (dd, J = 11.3, 6.1 Hz, 1H), 6.93 (d, J = 8.2 Hz, 1H), 6.25 (s, 2H), 5.63 (s, 2H), 4.63 (s, 2H). |
| 578 | 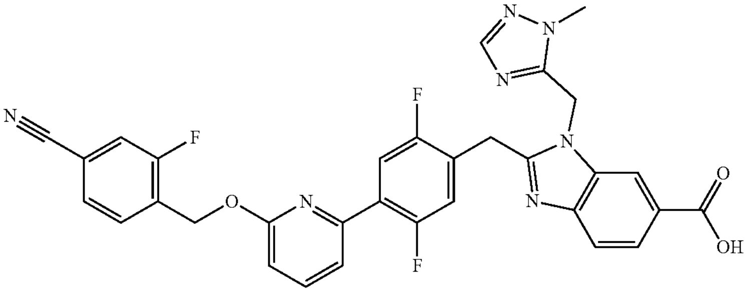 [SMILES: Cn1ncnc1Cn1c(Cc2cc(F)c(-c3cccc(OCc4ccc(C#N)cc4F)n3)cc2F)nc2ccc(C(=O)O)cc21] |

-continued

| Example | Structure/Name/Characterization |
|---|---|
| | 2-(4-(6-((4-cyano-2-fluorobenzyl)oxy)pyridin-2-yl)-2,5-difluorobenzyl)-1-((1-methyl-1H-1,2,4-triazol-5-yl)methyl)-1H-benzo[d]imidazole-6-carboxylic acid: ES/MS 610.3; $^1$H NMR (400 MHz, DMSO-d6) δ 8.22 (d, J = 1.5 Hz, 1H), 8.01-7.84 (m, 2H), 7.84-7.57 (m, 6H), 7.50 (dd, J = 7.5, 1.7 Hz, 1H), 7.32 (dd, J = 11.5, 6.0 Hz, 1H), 6.99 (d, J = 8.3 Hz, 1H), 5.97 (s, 2H), 5.60 (s, 2H), 4.42 (s, 2H), 3.95 (s, 3H). |
| 579 | 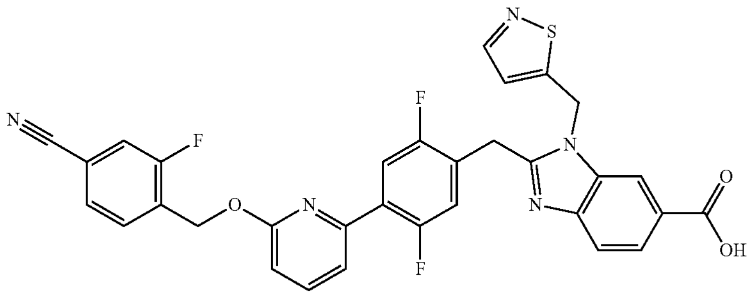 [SMILES: N#Cc1ccc(COc2cccc(-c3cc(F)c(Cc4nc5ccc(C(=O)O)cc5n4Cc4ccns4)cc3F)n2)c(F)c1] 2-(4-(6-((4-cyano-2-fluorobenzyl)oxy)pyridin-2-yl)-2,5-difluorobenzyl)-1-(isothiazol-5-ylmethyl)-1H-benzo[d]imidazole-6-carboxylic acid: ES/MS m/z 612.4; $^1$H NMR (400 MHz, Chloroform-d) δ 8.35 (d, J = 1.7 Hz, 1H), 8.20 (d, J = 7.6 Hz, 2H), 8.03 (d, J = 9.0 Hz, 1H), 7.77-7.62 (m, 3H), 7.49 (td, J = 5.9, 3.0 Hz, 2H), 7.42 (dd, J = 9.3, 1.5 Hz, 1H), 7.18 (dd, J = 10.8, 6.0 Hz, 1H), 6.97 (d, J = 1.7 Hz, 1H), 6.92-6.85 (m, 1H), 5.81 (s, 2H), 5.58 (s, 2H), 4.64 (s, 2H). |
| 580 | 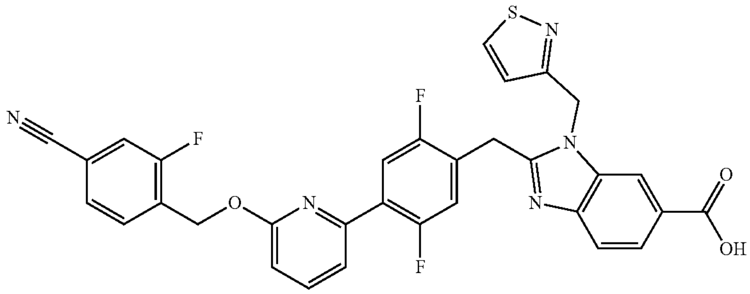 [SMILES: N#Cc1ccc(COc2cccc(-c3cc(F)c(Cc4nc5ccc(C(=O)O)cc5n4Cc4ccsn4)cc3F)n2)c(F)c1] 2-(4-(6-((4-cyano-2-fluorobenzyl)oxy)pyridin-2-yl)-2,5-difluorobenzyl)-1-(isothiazol-3-ylmethyl)-1H-benzo[d]imidazole-6-carboxylic acid: ES/MS m/z 612.3; $^1$H NMR (400 MHz, Methanol-d4) δ 8.71 (d, J = 4.6 Hz, 1H), 8.26-8.17 (m, 1H), 8.09 (dd, J = 8.5, 1.5 Hz, 1H), 7.81-7.59 (m, 4H), 7.53-7.38 (m, 3H), 7.04 (dd, J = 10.8, 5.4 Hz, 2H), 6.87 (dd, J = 8.3, 0.7 Hz, 1H), 5.72 (s, 2H), 5.58 (s, 2H), 4.52 (s, 2H). |
| 587 | 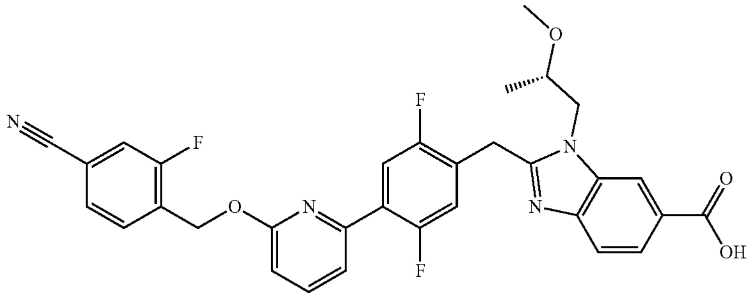 [SMILES: CO[C@@H](C)Cn1c(Cc2cc(F)c(-c3cccc(OCc4ccc(C#N)cc4F)n3)cc2F)nc2ccc(C(=O)O)cc21] (S)-2-(4-(6-((4-cyano-2-fluorobenzyl)oxy)pyridin-2-yl)-2,5-difluorobenzyl)-1-(2-methoxypropyl)-1H-benzo[d]imidazole-6-carboxylic acid: ES/MS m/z 587.5; $^1$H NMR (400 MHz, Methanol-d4) δ 8.53 (dd, J = 1.5, 0.7 Hz, 1H), 8.21 (dd, J = 8.6, 1.4 Hz, 1H), 7.89-7.69 (m, 4H), 7.66-7.53 (m, 3H), 7.35 (dd, J = 11.2, 6.0 Hz, 1H), 6.96 (dd, J = 8.3, 0.6 Hz, 1H), 5.63 (s, 2H), 4.81-4.64 (m, 3H), 4.54 (dd, J = 15.1, 9.3 Hz, 1H), 3.83 (ddd, J = 9.2, 6.1, 2.9 Hz, 1H), 3.20 (s, 3H), 1.38 (d, J = 6.2 Hz, 3H). |

-continued

| Example | Structure/Name/Characterization |
|---|---|
| 588 | 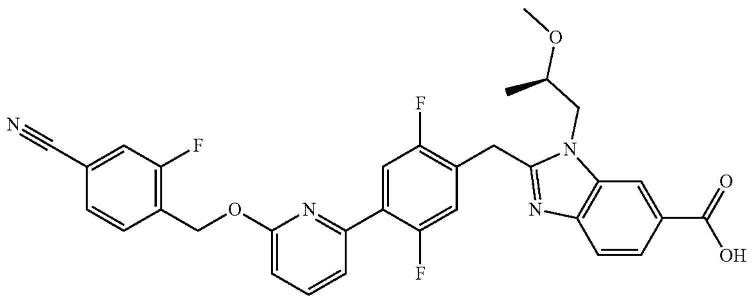 [SMILES: CO[C@H](C)Cn1c(Cc2cc(F)c(-c3cccc(OCc4ccc(C#N)cc4F)n3)cc2F)nc2ccc(C(=O)O)cc21]<br>(R)-2-(4-(6-((4-cyano-2-fluorobenzyl)oxy)pyridin-2-yl)-2,5-difluorobenzyl)-1-(2-methoxypropyl)-1H-benzo[d]imidazole-6-carboxylic acid: ES/MS m/z 587.5; $^1$H NMR (400 MHz, Methanol-d4) δ 8.53 (s, 1H), 8.21 (d, J = 8.6 Hz, 1H), 7.89-7.68 (m, 4H), 7.59 (t, J = 9.9 Hz, 3H), 7.35 (dd, J = 11.2, 6.0 Hz, 1H), 6.96 (d, J = 8.2 Hz, 1H), 5.63 (s, 2H), 4.82-4.63 (m, 3H), 4.54 (dd, J = 15.1, 9.3 Hz, 1H), 3.84 (pd, J = 6.5, 4.3, 3.3 Hz, 1H), 3.20 (s, 3H), 1.38 (d, J = 6.1 Hz, 3H). |
| 698 | 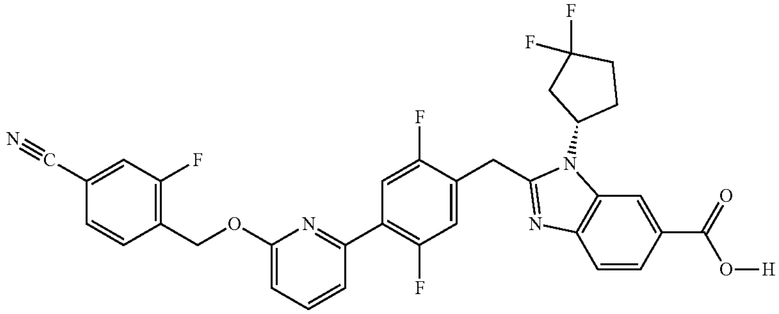 [SMILES: N#Cc1ccc(COc2cccc(-c3cc(F)c(Cc4nc5ccc(C(=O)O)cc5n4[C@H]4CCC(F)(F)C4)cc3F)n2)c(F)c1]<br>ES/MS m/z 619.2; 1H NMR (400 MHz, DMSO-d6) δ 8.24 (s, 1H), 7.95-7.87 (m, 2H), 7.85 (dd, J = 8.5, 1.4 Hz, 1H), 7.80-7.72 (m, 3H), 7.68 (d, J = 8.5 Hz, 1H), 7.54 (dd, J = 7.6, 1.7 Hz, 1H), 7.38 (dd, J = 11.5, 6.1 Hz, 1H), 7.00 (d, J = 8.3 Hz, 1H), 5.60 (s, 2H), 5.47 (p, J = 9.3 Hz, 1H), 4.54 (s, 2H), 2.95-2.67 (m, 2H), 2.52-2.20 (m, 4H). |
| 699 | 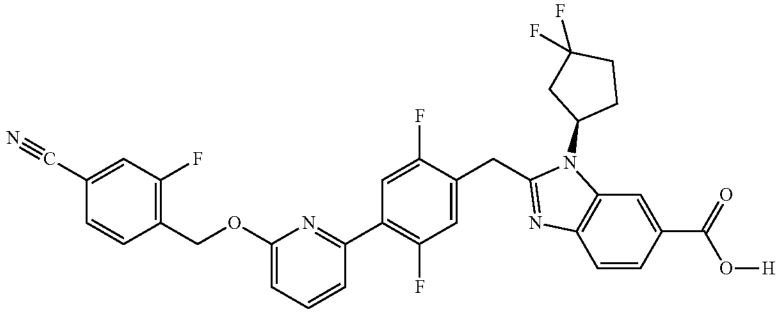 [SMILES: N#Cc1ccc(COc2cccc(-c3cc(F)c(Cc4nc5ccc(C(=O)O)cc5n4[C@@H]4CCC(F)(F)C4)cc3F)n2)c(F)c1]<br>ES/MS m/z 619.2; 1H NMR (400 MHz, DMSO-d6) δ 8.24 (s, 1H), 7.95-7.87 (m, 2H), 7.85 (dd, J = 8.5, 1.4 Hz, 1H), 7.80-7.72 (m, 3H), 7.68 (d, J = 8.5 Hz, 1H), 7.54 (dd, J = 7.6, 1.7 Hz, 1H), 7.38 (dd, J = 11.5, 6.1 Hz, 1H), 7.00 (d, J = 8.3 Hz, 1H), 5.60 (s, 2H), 5.47 (p, J = 9.3 Hz, 1H), 4.54 (s, 2H), 2.95-2.67 (m, 2H), 2.52-2.20 (m, 4H). |

-continued

| Example | Structure/Name/Characterization |
| --- | --- |
| 700 | 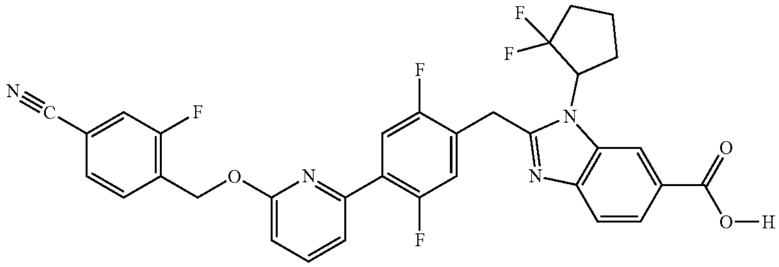 [SMILES: N#Cc1ccc(COc2cccc(-c3cc(F)c(Cc4nc5ccc(C(=O)O)cc5n4C4CCCC4(F)F)cc3F)n2)c(F)c1]<br>ES/MS m/z 619.2; 1H NMR (400 MHz, DMSO-d6) δ 8.23-8.10 (m, 1H), 7.95-7.88 (m, 2H), 7.82 (dd, J = 8.4, 1.5 Hz, 1H), 7.79-7.71 (m, 3H), 7.65 (d, J = 8.4 Hz, 1H), 7.54 (dd, J = 7.5, 1.7 Hz, 1H), 7.39 (dd, J = 11.5, 6.1 Hz, 1H), 7.00 (d, J = 8.2 Hz, 1H), 5.61 (s, 2H), 5.52 (dt, J = 20.2, 10.0 Hz, 1H), 4.54 (d, J = 17.0 Hz, 1H), 4.38 (d, J = 16.9 Hz, 1H), 2.76-2.60 (m, 1H), 2.40 (dtd, J = 17.7, 13.1, 10.5, 5.6 Hz, 2H), 2.09 (d, J = 16.8 Hz, 1H), 2.06-1.93 (m, 1H). One signal overlapping with solvent. |
| 701 | 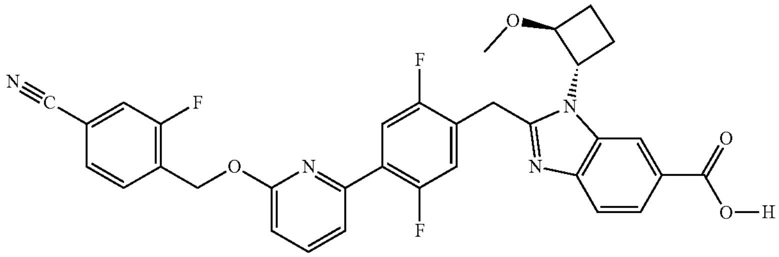 [SMILES: CO[C@H]1CC[C@@H]1n1c(Cc2cc(F)c(-c3cccc(OCc4ccc(C#N)cc4F)n3)cc2F)nc2ccc(C(=O)O)cc21]<br>ES/MS m/z 599.2; 1H NMR (400 MHz, DMSO-d6) δ 8.34 (d, J = 1.4 Hz, 1H), 7.96-7.87 (m, 2H), 7.84 (dd, J = 8.4, 1.4 Hz, 1H), 7.79-7.70 (m, 3H), 7.66 (d, J = 8.5 Hz, 1H), 7.53 (dd, J = 7.5, 1.7 Hz, 1H), 7.39 (dd, J = 11.5, 6.1 Hz, 1H), 7.00 (d, J = 8.3 Hz, 1H), 5.60 (s, 2H), 4.99 (q, J = 8.7 Hz, 1H), 4.62 (q, J = 7.8 Hz, 1H), 4.54-4.38 (m, 2H), 3.19 (s, 3H), 2.35 (dp, J = 38.3, 9.8 Hz, 3H), 1.74 (p, J = 9.5 Hz, 1H). |
| 702 | 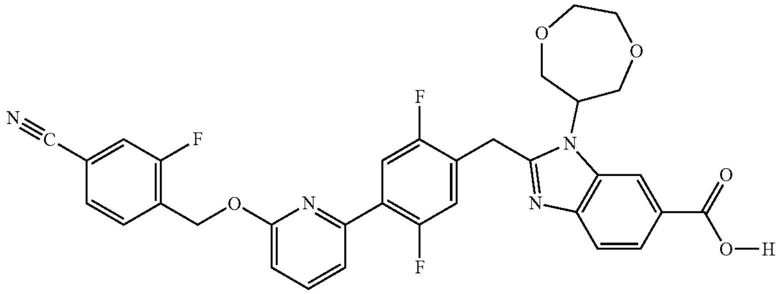 [SMILES: N#Cc1ccc(COc2cccc(-c3cc(F)c(Cc4nc5ccc(C(=O)O)cc5n4C4COCCOC4)cc3F)n2)c(F)c1]<br>ES/MS m/z 615.2; 1H NMR (400 MHz, DMSO-d6) δ 8.34 (d, J = 1.5 Hz, 1H), 7.95-7.83 (m, 3H), 7.75 (qd, J = 7.9, 3.9 Hz, 3H), 7.65 (d, J = 8.5 Hz, 1H), 7.53 (dd, J = 7.5, 1.7 Hz, 1H), 7.41 (dd, J = 11.5, 6.1 Hz, 1H), 7.00 (d, J = 8.3 Hz, 1H), 5.60 (s, 2H), 4.58 (dd, J = 15.3, 2.9 Hz, 1H), 4.52 (d, J = 3.0 Hz, 2H), 4.44 (dd, J = 15.2, 8.8 Hz, 1H), 4.01 (dd, J = 11.3, 2.5 Hz, 1H), 3.93- 3.84 (m, 1H), 3.64 (dd, J = 10.7, 8.2 Hz, 2H), 3.47 (d, J = 8.3 Hz, 2H), 3.34 (dd, J = 11.3, 10.0 Hz, 1H). |
| 703 | 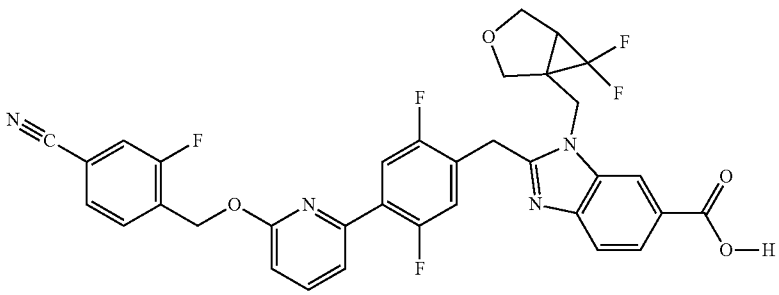 [SMILES: N#Cc1ccc(COc2cccc(-c3cc(F)c(Cc4nc5ccc(C(=O)O)cc5n4CC45COCC4C5(F)F)cc3F)n2)c(F)c1] |

-continued

| Example | Structure/Name/Characterization |
|---|---|
| | ES/MS m/z 647.1; 1H NMR (400 MHz, DMSO-d6) δ 8.34 (d, J = 1.4 Hz, 1H), 7.95-7.87 (m, 2H), 7.84 (dd, J = 8.4, 1.5 Hz, 1H), 7.79-7.71 (m, 3H), 7.64 (d, J = 8.4 Hz, 1H), 7.54 (dd, J = 7.5, 1.7 Hz, 1H), 7.44 (dd, J = 11.5, 6.1 Hz, 1H), 7.00 (d, J = 8.2 Hz, 1H), 5.60 (s, 2H), 5.06 (dd, J = 15.9, 4.1 Hz, 1H), 4.82 (d, J = 15.9 Hz, 1H), 4.46 (s, 2H), 4.12 (d, J = 9.1 Hz, 1H), 3.98 (ddd, J = 9.3, 5.8, 3.9 Hz, 1H), 3.90 (d, J = 4.1 Hz, 2H), 2.72 (dd, J = 14.0, 3.8 Hz, 1H). 19F NMR (376 MHz, DMSO-d6) δ −75.26, −115.91 (dd, J = 9.9, 6.4 Hz), −121.20- −122.97 (m), −131.69 (d, J = 159.1 Hz), −148.21 (dd, J = 159.7, 3.8 Hz). |
| 704 | 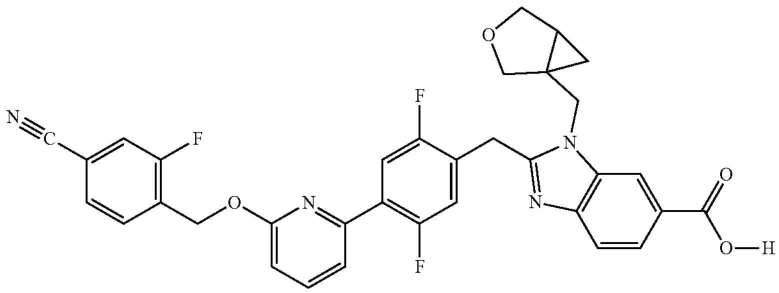 [SMILES: N#Cc1ccc(COc2cccc(-c3cc(F)c(Cc4nc5ccc(C(=O)O)cc5n4CC45COCC4C5)cc3F)n2)c(F)c1] ES/MS m/z 611.2; 1H NMR (400 MHz, DMSO-d6) δ 8.33 (d, J = 1.4 Hz, 1H), 7.94-7.82 (m, 3H), 7.81-7.71 (m, 3H), 7.65 (d, J = 8.5 Hz, 1H), 7.54 (dd, J = 7.6, 1.7 Hz, 1H), 7.48 (dd, J = 11.5, 6.1 Hz, 1H), 7.00 (d, J = 8.3 Hz, 1H), 5.60 (s, 2H), 4.90 (d, J = 15.6 Hz, 1H), 4.75 (d, J = 15.6 Hz, 1H), 4.50 (s, 2H), 3.68-3.57 (m, 4H), 1.73 (ddd, J = 7.7, 4.2, 2.6 Hz, 1H), 0.85 (dd, J = 8.2, 4.6 Hz, 1H), 0.54 (t, J = 4.5 Hz, 1H). |
| 705 | 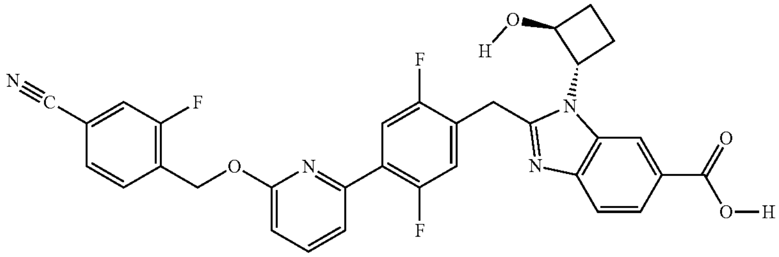 [SMILES: N#Cc1ccc(COc2cccc(-c3cc(F)c(Cc4nc5ccc(C(=O)O)cc5n4[C@H]4CC[C@@H]4O)cc3F)n2)c(F)c1] ES/MS m/z 585.2; 1H NMR (400 MHz, DMSO-d6) δ 8.38 (d, J = 1.4 Hz, 1H), 7.97-7.87 (m, 2H), 7.83-7.70 (m, 4H), 7.61 (d, J = 8.5 Hz, 1H), 7.53 (dd, J = 7.4, 1.7 Hz, 1H), 7.35 (dd, J = 11.5, 6.1 Hz, 1H), 6.99 (d, J = 8.3 Hz, 1H), 5.90 (d, J = 6.6 Hz, 1H), 5.61 (s, 2H), 4.75 (h, J = 7.9 Hz, 2H), 4.52-4.36 (m, 2H), 2.31 (q, J = 8.7, 8.1 Hz, 2H), 2.15 (q, J = 9.8 Hz, 1H), 1.73 (p, J = 10.0 Hz, 1H). |
| 706 | 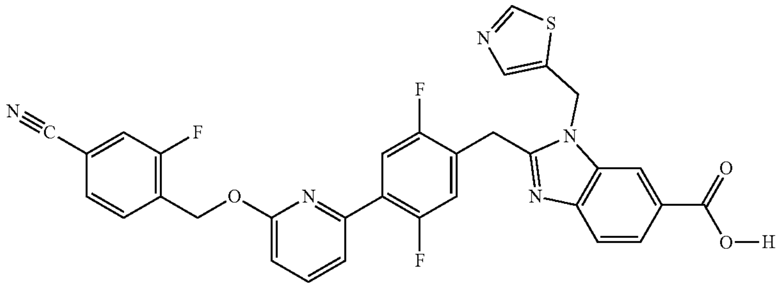 [SMILES: N#Cc1ccc(COc2cccc(-c3cc(F)c(Cc4nc5ccc(C(=O)O)cc5n4Cc4cncs4)cc3F)n2)c(F)c1] ES/MS m/z 612; 1H NMR (400 MHz, DMSO-d6) δ 9.02 (s, 1H), 8.31 (d, J = 1.5 Hz, 1H), 7.96 (s, 1H), 7.95-7.87 (m, 2H), 7.83 (dd, J = 8.4, 1.6 Hz, 1H), 7.73 (dt, J = 10.5, 6.7 Hz, 3H), 7.65 (d, J = 8.5 Hz, 1H), 7.52 (dd, J = 7.5, 1.7 Hz, 1H), 7.36 (dd, J = 11.4, 6.1 Hz, 1H), 6.99 (d, J = 8.2 Hz, 1H), 6.02 (s, 2H), 5.60 (s, 2H), 4.51 (s, 2H). |

-continued

| Example | Structure/Name/Characterization |
|---|---|
| 707 | 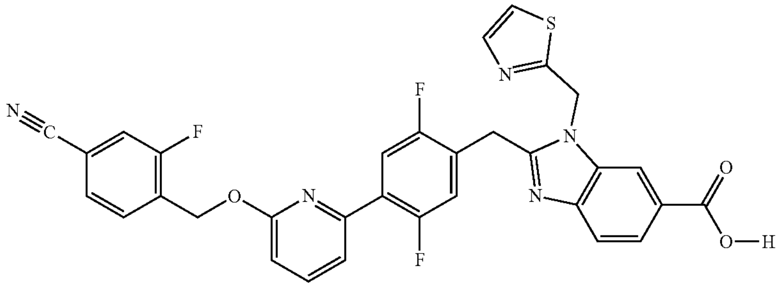 [SMILES: N#Cc1ccc(COc2cccc(-c3cc(F)c(Cc4nc5ccc(C(=O)O)cc5n4Cc4nccs4)cc3F)n2)c(F)c1]<br>ES/MS m/z 612; 1H NMR (400 MHz, DMSO-d6) δ 8.30 (d, J = 1.4 Hz, 1H), 7.95-7.87 (m, 2H), 7.84 (dd, J = 8.4, 1.6 Hz, 1H), 7.79-7.65 (m, 6H), 7.51 (dd, J = 7.5, 1.7 Hz, 1H), 7.34 (dd, J = 11.4, 6.1 Hz, 1H), 6.99 (d, J = 8.2 Hz, 1H), 6.12 (s, 2H), 5.60 (s, 2H), 4.54 (s, 2H). |
| 708 | 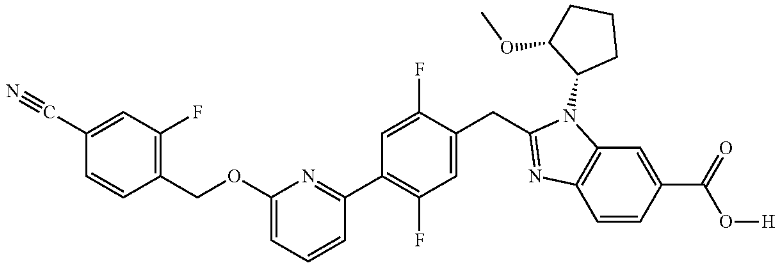 [SMILES: CO[C@@H]1CCC[C@@H]1n1c(Cc2cc(F)c(-c3cccc(OCc4ccc(C#N)cc4F)n3)cc2F)nc2ccc(C(=O)O)cc21]<br>ES/MS m/z 613.2; 1H NMR (400 MHz, DMSO-d6) δ 8.35 (d, J = 1.5 Hz, 1H), 7.95-7.86 (m, 2H), 7.83 (dd, J = 8.5, 1.5 Hz, 1H), 7.80-7.69 (m, 3H), 7.63 (d, J = 8.5 Hz, 1H), 7.54 (dd, J = 7.5, 1.7 Hz, 1H), 7.37 (dd, J = 11.5, 6.1 Hz, 1H), 7.00 (d, J = 8.2 Hz, 1H), 5.60 (s, 2H), 5.10 (td, J = 9.4, 5.5 Hz, 1H), 4.68-4.51 (m, 2H), 3.84 (dt, J = 7.4, 3.8 Hz, 1H), 2.92 (s, 3H), 2.23-1.88 (m, 4H), 1.83-1.64 (m, 1H). One signal overlapping with solvent. |
| 709 | 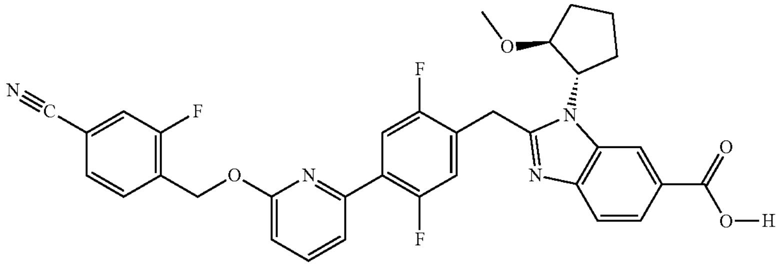 [SMILES: CO[C@H]1CCC[C@@H]1n1c(Cc2cc(F)c(-c3cccc(OCc4ccc(C#N)cc4F)n3)cc2F)nc2ccc(C(=O)O)cc21]<br>ES/MS m/z 613.2; 1H NMR (400 MHz, DMSO-d6) δ 8.13 (d, J = 1.4 Hz, 1H), 7.95-7.87 (m, 2H), 7.85 (dd, J = 8.5, 1.5 Hz, 1H), 7.80-7.72 (m, 3H), 7.68 (d, J = 8.4 Hz, 1H), 7.53 (dd, J = 7.5, 1.7 Hz, 1H), 7.38 (dd, J = 11.5, 6.1 Hz, 1H), 7.00 (d, J = 8.3 Hz, 1H), 5.60 (s, 2H), 4.93 (td, J = 9.4, 7.2 Hz, 1H), 4.59-4.39 (m, 2H), 4.33 (q, J = 7.0 Hz, 1H), 3.11 (s, 3H), 2.31-2.12 (m, 3H), 2.06-1.84 (m, 2H), 1.75 (dt, J = 12.8, 7.4 Hz, 1H). |
| 710 | 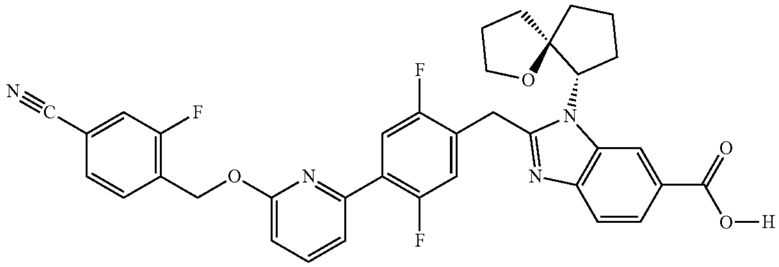 [SMILES: N#Cc1ccc(COc2cccc(-c3cc(F)c(Cc4nc5ccc(C(=O)O)cc5n4[C@H]4CCC[C@@]45CCCO5)cc3F)n2)c(F)c1]<br>ES/MS m/z 639.2; 1H NMR (400 MHz, DMSO-d6) δ 8.51 (s, 1H), 7.98-7.85 (m, 2H), 7.84-7.70 (m, 4H), 7.60 (d, J = 8.4 Hz, 1H), 7.54 (dd, J = 7.5, 1.7 Hz, 1H), 7.43 (s, 1H), 7.00 (d, J = 8.3 Hz, 1H), 5.61 (s, 2H), 4.95 (s, 1H), 4.50 |

-continued

| Example | Structure/Name/Characterization |
| --- | --- |
| | (d, J = 35.3 Hz, 1H), 3.62 (s, 1H), 3.03 (s, 1H), 2.29-1.62 (m, 10H), 1.23 (d, J = 61.5 Hz, 1H). |
| 711 | 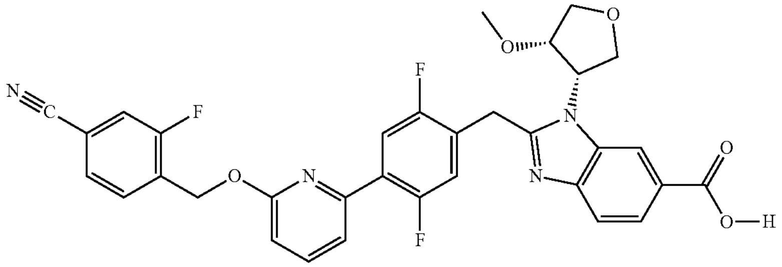 [SMILES: CO[C@@H]1COC[C@@H]1n1c(Cc2cc(F)c(-c3cccc(OCc4ccc(C#N)cc4F)n3)cc2F)nc2ccc(C(=O)O)cc21] ES/MS m/z 616.2; 1H NMR (400 MHz, DMSO-d6) δ 8.44 (d, J = 1.5 Hz, 1H), 7.96-7.86 (m, 2H), 7.82 (dd, J = 8.5, 1.5 Hz, 1H), 7.79-7.70 (m, 3H), 7.63 (d, J = 8.5 Hz, 1H), 7.53 (dd, J = 7.5, 1.7 Hz, 1H), 7.33 (dd, J = 11.4, 6.1 Hz, 1H), 7.00 (d, J = 8.2 Hz, 1H), 5.67-5.50 (m, 3H), 4.55 (s, 2H), 4.42 (dd, J = 10.5, 3.6 Hz, 1H), 4.12 (dt, J = 8.6, 2.0 Hz, 2H), 4.01 (dd, J = 10.6, 8.2 Hz, 1H), 3.79 (dd, J = 10.8, 4.9 Hz, 1H), 2.87 (s, 3H). |
| 712 | 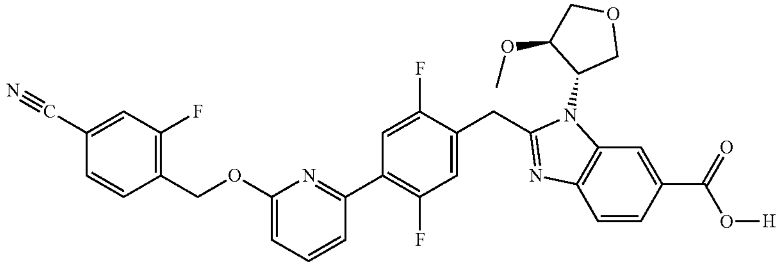 [SMILES: CO[C@H]1COC[C@@H]1n1c(Cc2cc(F)c(-c3cccc(OCc4ccc(C#N)cc4F)n3)cc2F)nc2ccc(C(=O)O)cc21] ES/MS m/z 615.2; 1H NMR (400 MHz, DMSO-d6) δ 8.34 (d, J = 1.4 Hz, 1H), 7.95-7.87 (m, 2H), 7.85 (dd, J = 8.5, 1.5 Hz, 1H), 7.79-7.71 (m, 3H), 7.68 (d, J = 8.4 Hz, 1H), 7.53 (dd, J = 7.4, 1.7 Hz, 1H), 7.40 (dd, J = 11.5, 6.1 Hz, 1H), 7.00 (d, J = 8.3 Hz, 1H), 5.60 (s, 2H), 5.29 (dt, J = 7.4, 3.6 Hz, 1H), 4.58 (d, J = 16.9 Hz, 1H), 4.47 (d, J = 16.8 Hz, 1H), 4.42-4.31 (m, 2H), 4.30-4.20 (m, 2H), 3.75 (dd, J = 9.4, 5.1 Hz, 1H), 3.22 (s, 3H). |
| 713 | 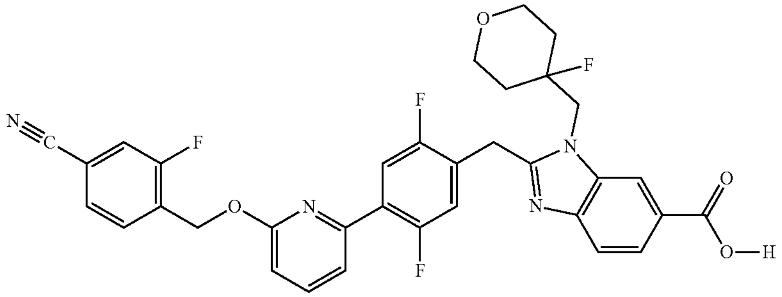 [SMILES: N#Cc1ccc(COc2cccc(-c3cc(F)c(Cc4nc5ccc(C(=O)O)cc5n4CC4(F)CCOCC4)cc3F)n2)c(F)c1] ES/MS m/z 631.2; 1H NMR (400 MHz, DMSO-d6) δ 8.36 (s, 1H), 7.95-7.87 (m, 2H), 7.81 (dd, J = 8.4, 1.5 Hz, 1H), 7.79-7.70 (m, 3H), 7.61 (d, J = 8.4 Hz, 1H), 7.54 (dd, J = 7.4, 1.7 Hz, 1H), 7.44 (dd, J = 11.5, 6.1 Hz, 1H), 7.00 (d, J = 8.2 Hz, 1H), 5.60 (s, 2H), 4.77 (d, J = 22.3 Hz, 2H), 4.46 (s, 2H), 3.81 (dd, J = 11.5, 5.0 Hz, 2H), 3.49 (t, J = 11.7 Hz, 2H), 2.16-1.87 (m, 2H), 1.59 (t, J = 11.1 Hz, 2H). |

-continued

| Example | Structure/Name/Characterization |
|---|---|
| 714 | 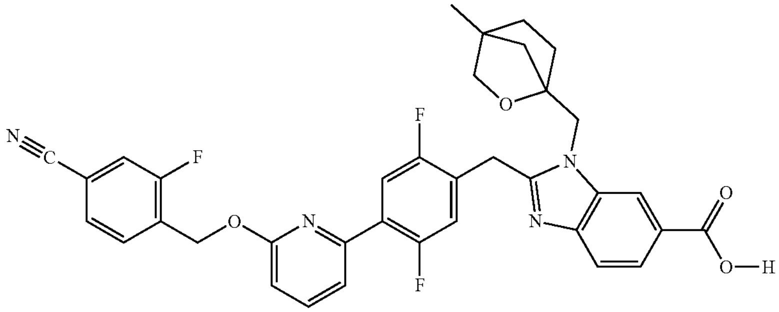 [SMILES: CC12CCC(Cn3c(Cc4cc(F)c(-c5cccc(OCc6ccc(C#N)cc6F)n5)cc4F)nc4ccc(C(=O)O)cc43)(C1)OC2] ES/MS m/z 639.2; 1H NMR (400 MHz, DMSO-d6) δ 8.31 (d, J = 1.5 Hz, 1H), 7.96-7.87 (m, 2H), 7.84 (dd, J = 8.5, 1.5 Hz, 1H), 7.75 (td, J = 6.3, 4.9 Hz, 3H), 7.63 (d, J = 8.4 Hz, 1H), 7.53 (dd, J = 7.5, 1.7 Hz, 1H), 7.38 (dd, J = 11.5, 6.1 Hz, 1H), 7.00 (d, J = 8.2 Hz, 1H), 5.60 (s, 2H), 4.81 (d, J = 15.6 Hz, 1H), 4.72 (d, J = 15.6 Hz, 1H), 4.59-4.45 (m, 2H), 3.46 (d, J = 6.5 Hz, 1H), 3.32 (dd, J = 6.5, 2.8 Hz, 1H), 2.06-1.90 (m, 1H), 1.65-1.49 (m, 4H), 1.13 (d, J = 9.5 Hz, 1H), 1.06 (s, 3H). |
| 715 | 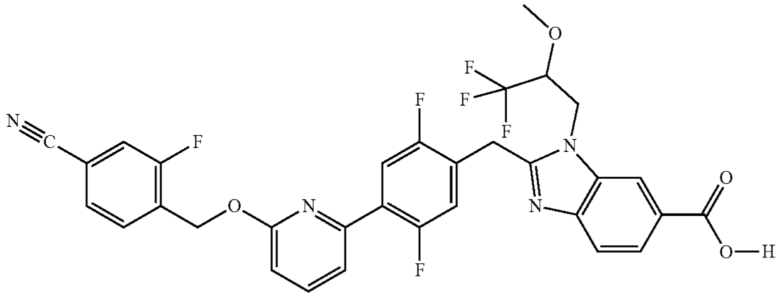 [SMILES: COC(Cn1c(Cc2cc(F)c(-c3cccc(OCc4ccc(C#N)cc4F)n3)cc2F)nc2ccc(C(=O)O)cc21)C(F)(F)F] ES/MS m/z 641.2; 1H NMR (400 MHz, DMSO-d6) δ 8.21 (d, J = 1.4 Hz, 1H), 7.95-7.87 (m, 2H), 7.83 (dd, J = 8.4, 1.6 Hz, 1H), 7.80-7.70 (m, 3H), 7.64 (d, J = 8.4 Hz, 1H), 7.54 (dd, J = 7.5, 1.7 Hz, 1H), 7.42 (dd, J = 11.5, 6.1 Hz, 1H), 7.00 (d, J = 8.2 Hz, 1H), 5.61 (s, 2H), 4.79 (dd, J = 15.3, 2.9 Hz, 1H), 4.62 (dd, J = 15.4, 9.1 Hz, 1H), 4.56-4.45 (m, 3H). 19F NMR (376 MHz, DMSO-d6) δ −75.19, −75.36 (d, J = 6.7 Hz), −115.91 (dd, J = 10.3, 6.5 Hz), −121.70-−122.19 (m), −122.33-−122.71 (m). |
| 716 | 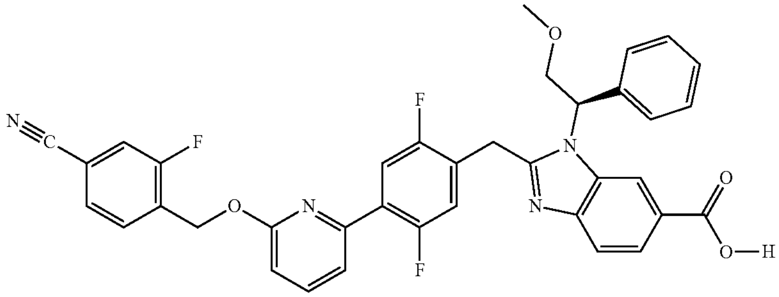 [SMILES: COC[C@@H](c1ccccc1)n1c(Cc2cc(F)c(-c3cccc(OCc4ccc(C#N)cc4F)n3)cc2F)nc2ccc(C(=O)O)cc21] ES/MS m/z 649.2; 1H NMR (400 MHz, DMSO-d6) δ 7.98-7.85 (m, 2H), 7.78-7.67 (m, 6H), 7.62 (d, J = 8.8 Hz, 1H), 7.52 (dd, J = 7.6, 1.7 Hz, 1H), 7.43-7.26 (m, 6H), 6.99 (d, J = 8.2 Hz, 1H), 6.24 (dd, J = 8.6, 5.0 Hz, 1H), 5.60 (s, 2H), 4.54 (d, J = 16.9 Hz, 1H), 4.43-4.31 (m, 2H), 4.31-4.24 (m, 1H), 3.28 (s, 3H). |

-continued

| Example | Structure/Name/Characterization |
|---|---|
| 717 | 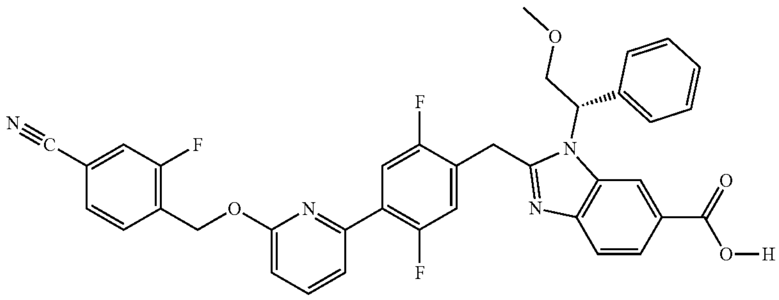 [SMILES: COC[C@H](c1ccccc1)n1c(Cc2cc(F)c(-c3cccc(OCc4ccc(C#N)cc4F)n3)cc2F)nc2ccc(C(=O)O)cc21] ES/MS m/z 649.2; 1H NMR (400 MHz, DMSO-d6) δ 7.98-7.85 (m, 2H), 7.78-7.67 (m, 6H), 7.62 (d, J = 8.8 Hz, 1H), 7.52 (dd, J = 7.6, 1.7 Hz, 1H), 7.43-7.26 (m, 6H), 6.99 (d, J = 8.2 Hz, 1H), 6.24 (dd, J = 8.6, 5.0 Hz, 1H), 5.60 (s, 2H), 4.54 (d, J = 16.9 Hz, 1H), 4.43-4.31 (m, 2H), 4.31-4.24 (m, 1H), 3.28 (s, 3H). |
| 718 | 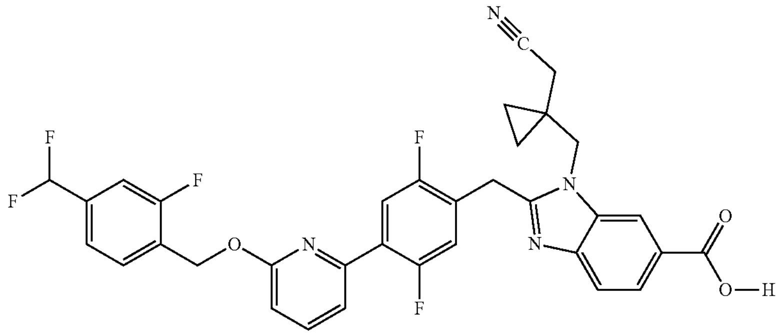 [SMILES: N#CCC1(Cn2c(Cc3cc(F)c(-c4cccc(OCc5ccc(C(F)F)cc5F)n4)cc3F)nc3ccc(C(=O)O)cc32)CC1] ES/MS MH+ 633.2; 1H NMR (400 MHz, DMSO) δ 8.36 (d, J = 1.5 Hz, 1H), 7.93-7.85 (m, 2H), 7.82 (dd, J = 10.5, 6.4 Hz, 1H), 7.72 (t, J = 7.6 Hz, 1H), 7.66 (d, J = 8.5 Hz, 1H), 7.57-7.41 (m, 4H), 7.06 (t, J = 55.6 Hz, 1H), 6.98 (d, J = 8.3 Hz, 1H), 5.58 (s, 2H), 4.62 (s, 2H), 4.53 (s, 2H), 2.70 (s, 2H), 0.87-0.64 (m, 4H). Multiplet Report 19F NMR (376 MHz, DMSO) δ −75.39, −110.77 (d, J = 55.7 Hz), −117.20 (dd, J = 10.3, 7.4 Hz), −120.22--126.64 (m). |
| 719 | 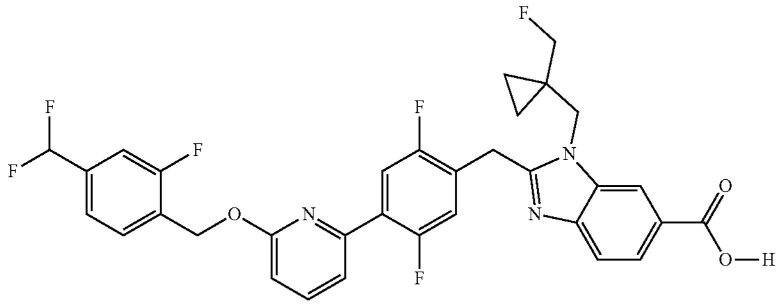 [SMILES: O=C(O)c1ccc2nc(Cc3cc(F)c(-c4cccc(OCc5ccc(C(F)F)cc5F)n4)cc3F)n(CC3(CF)CC3)c2c1] ES/MS MH+ 626.2; 1H NMR (400 MHz, DMSO) δ 8.31 (d, J = 1.5 Hz, 1H), 7.98-7.76 (m, 3H), 7.72 (t, J = 7.6 Hz, 1H), 7.65 (d, J = 8.5 Hz, 1H), 7.56-7.49 (m, 2H), 7.49-7.36 (m, 2H), 7.06 (t, J = 55.6 Hz, 1H), 6.98 (d, J = 8.2 Hz, 1H), 5.58 (s, 2H), 4.60 (s, 2H), 4.50 (s, 2H), 4.20 (d, J = 48.8 Hz, 2H), 1.00-0.77 (m, 2H), 0.75 (d, J = 5.1 Hz, 2H). Multiplet Report 19F NMR (376 MHz, DMSO) δ −75.26, −110.77 (d, J = 55.3 Hz), −117.20 (dd, J = 10.3, 7.4 Hz), −120.66--125.07 (m). |

-continued
| Example | Structure/Name/Characterization |
| --- | --- |
| 720 | 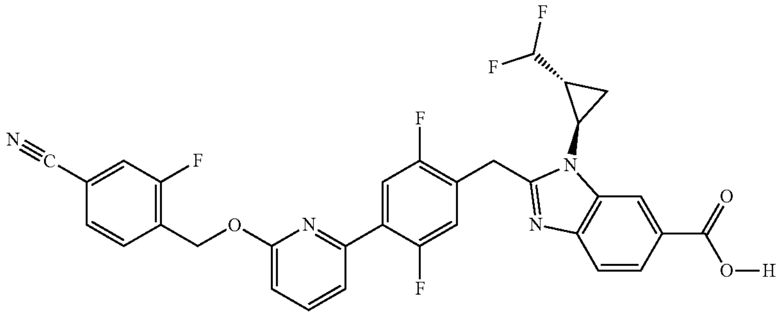 [SMILES: N#Cc1ccc(COc2cccc(-c3cc(F)c(Cc4nc5ccc(C(=O)O)cc5n4[C@@H]4C[C@H]4C(F)F)cc3F)n2)c(F)c1] ES/MS m/z 605.5; 1H NMR (400 MHz, Methanol-d4) δ 8.58 (dd, J = 1.3, 0.7 Hz, 1H), 8.17 (dd, J = 8.6, 1.5 Hz, 1H), 7.90-7.78 (m, 2H), 7.78-7.68 (m, 2H), 7.68-7.54 (m, 3H), 7.36 (dd, J = 11.2, 6.0 Hz, 1H), 6.96 (dd, J = 8.2, 0.6 Hz, 1H), 6.16 (td, J = 56.2, 4.4 Hz, 1H), 5.63 (s, 2H), 4.73 (d, J = 2.9 Hz, 2H), 4.01-3.84 (m, 1H), 2.56-2.29 (m, 1H), 1.90-1.74 (m, 2H). |
| 721 | 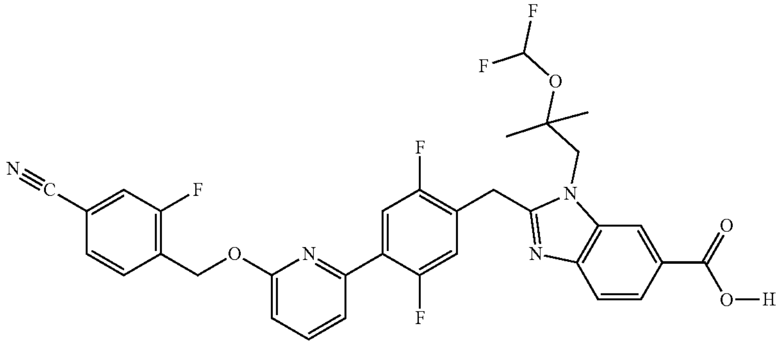 [SMILES: CC(C)(Cn1c(Cc2cc(F)c(-c3cccc(OCc4ccc(C#N)cc4F)n3)cc2F)nc2ccc(C(=O)O)cc21)OC(F)F] ES/MS m/z 637.5; 1H NMR (400 MHz, Methanol-d4) δ 8.52 (d, J = 1.4 Hz, 1H), 8.12 (dd, J = 8.5, 1.5 Hz, 1H), 7.88-7.75 (m, 2H), 7.72 (d, J = 8.2 Hz, 2H), 7.64-7.55 (m, 3H), 7.28 (dd, J = 11.3, 6.0 Hz, 1H), 6.94 (d, J = 8.3 Hz, 1H), 6.60 (t, J = 75.4 Hz, 1H), 5.63 (s, 2H), 4.71 (d, J = 6.6 Hz, 4H), 1.56 (s, 6H). |
| 722 | 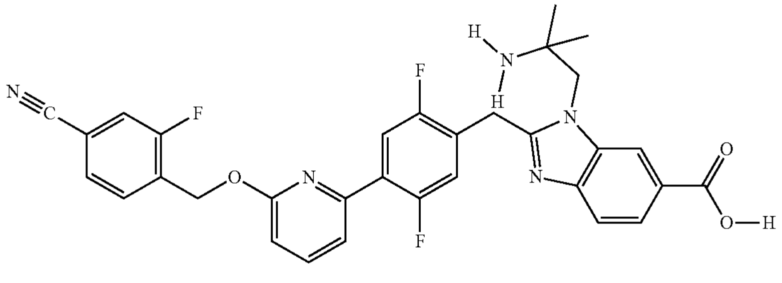 [SMILES: CC(C)(N)Cn1c(Cc2cc(F)c(-c3cccc(OCc4ccc(C#N)cc4F)n3)cc2F)nc2ccc(C(=O)O)cc21] ES/MS m/z 586.1; 1H NMR (400 MHz, Methanol-d4) δ 8.42-8.31 (m, 1H), 8.04 (dd, J = 8.5, 1.5 Hz, 1H), 7.81 (t, J = 7.9 Hz, 1H), 7.78-7.68 (m, 3H), 7.63-7.51 (m, 3H), 7.28 (dd, J = 11.4, 6.1 Hz, 1H), 6.99-6.87 (m, 1H), 5.61 (s, 2H), 4.68 (s, 2H), 4.47 (d, J = 7.1 Hz, 2H), 1.56 (s, 6H). |
| 723 | 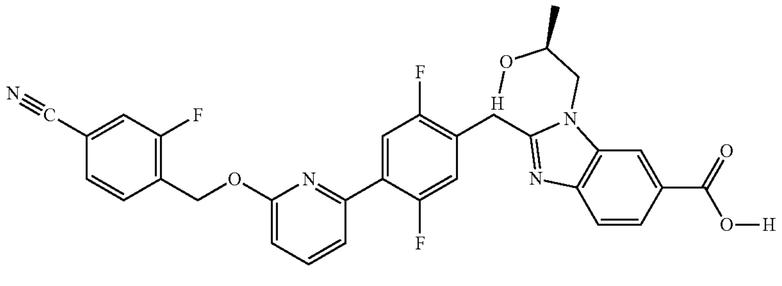 [SMILES: C[C@H](O)Cn1c(Cc2cc(F)c(-c3cccc(OCc4ccc(C#N)cc4F)n3)cc2F)nc2ccc(C(=O)O)cc21] |

-continued

| Example | Structure/Name/Characterization |
|---|---|
| | ES/MS m/z 573.3; 1H NMR (400 MHz, Methanol-d4) δ 8.55 (t, J = 1.0 Hz, 1H), 8.22 (dd, J = 8.6, 1.4 Hz, 1H), 7.89-7.82 (m, 2H), 7.82-7.77 (m, 1H), 7.74 (t, J = 7.5 Hz, 1H), 7.65-7.57 (m, 3H), 7.38 (dd, J = 11.2, 6.0 Hz, 1H), 6.97 (dd, J = 8.2, 0.6 Hz, 1H), 5.64 (s, 2H), 4.80 (d, J = 2.6 Hz, 2H), 4.68 (dd, J = 14.8, 2.9 Hz, 1H), 4.47 (dd, J = 14.9, 9.3 Hz, 1H), 4.23 (ddd, J = 9.2, 6.2, 2.9 Hz, 1H), 1.41 (d, J = 6.3 Hz, 3H). |
| 724 | 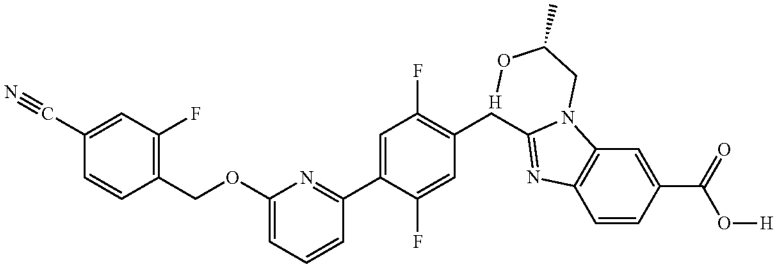 [SMILES: C[C@@H](O)Cn1c(Cc2cc(F)c(-c3cccc(OCc4ccc(C#N)cc4F)n3)cc2F)nc2ccc(C(=O)O)cc21] ES/MS m/z 573.5; 1H NMR (400 MHz, Methanol-d4) δ 8.63-8.49 (m, 1H), 8.22 (dd, J = 8.6, 1.4 Hz, 1H), 7.88-7.69 (m, 4H), 7.69-7.53 (m, 3H), 7.38 (dd, J = 11.2, 6.1 Hz, 1H), 6.97 (d, J = 8.3 Hz, 1H), 5.64 (s, 2H), 4.80 (d, J = 2.5 Hz, 2H), 4.68 (dd, J = 14.8, 2.9 Hz, 1H), 4.47 (dd, J = 14.8, 9.3 Hz, 1H), 4.23 (ddd, J = 9.2, 6.2, 2.9 Hz, 1H), 1.41 (d, J = 6.3 Hz, 3H). |
| 725 | 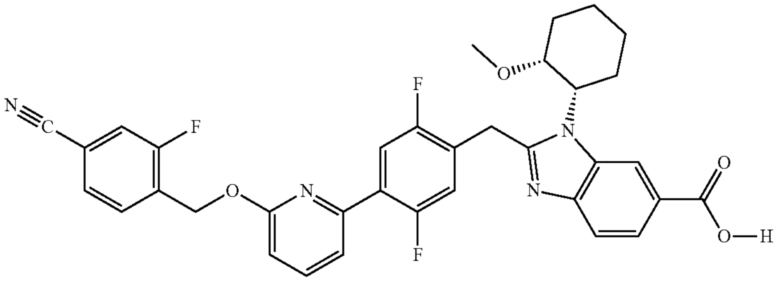 [SMILES: CO[C@@H]1CCCC[C@@H]1n1c(Cc2cc(F)c(-c3cccc(OCc4ccc(C#N)cc4F)n3)cc2F)nc2ccc(C(=O)O)cc21] ES/MS m/z 627.3; 1H NMR (400 MHz, Methanol-d4) δ 8.82 (s, 1H), 8.15 (dd, J = 8.6, 1.4 Hz, 1H), 7.88-7.76 (m, 2H), 7.73 (dd, J = 11.4, 8.0 Hz, 2H), 7.64-7.48 (m, 3H), 7.36 (dd, J = 11.2, 6.1 Hz, 1H), 6.96 (d, J = 8.2 Hz, 1H), 5.63 (s, 2H), 4.76 (t, J = 19.2 Hz, 3H), 3.63-3.49 (m, 1H), 3.18 (s, 3H), 2.98-2.77 (m, 1H), 2.22 (d, J = 14.1 Hz, 1H), 2.02 (d, J = 12.8 Hz, 1H), 1.84 (d, J = 12.5 Hz, 1H), 1.75 (t, J = 13.7 Hz, 1H), 1.61 (d, J = 13.0 Hz, 3H). |
| 726 | 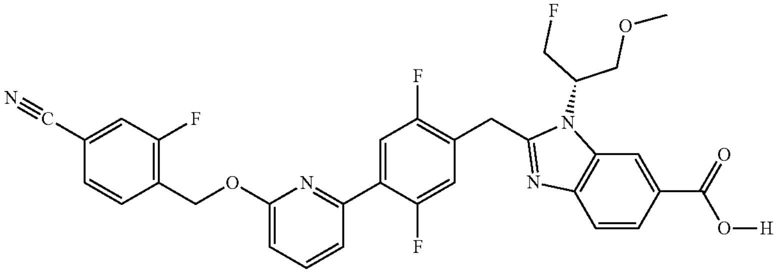 [SMILES: COC[C@@H](CF)n1c(Cc2cc(F)c(-c3cccc(OCc4ccc(C#N)cc4F)n3)cc2F)nc2ccc(C(=O)O)cc21] ES/MS m/z 605.5; "1H NMR (400 MHz, Methanol-d4) δ 8.59 (t, J = 0.9 Hz, 1H), 8.13 (dd, J = 8.6, 1.4 Hz, 1H), 7.90-7.65 (m, 4H), 7.66-7.50 (m, 3H), 7.26 (dd, J = 11.4, 6.1 Hz, 1H), 6.94 (dd, J = 8.3, 0.7 Hz, 1H), 5.62 (s, 2H), 5.41-5.16 (m, 1H), 5.13-4.99 (m, 1H), 4.93 (dd, J = 10.6, 3.6 Hz, 1H), 4.62 (s, 2H), 4.12 (dd, J = 10.5, 7.9 Hz, 1H), 3.98 (dd, J = 10.5, 4.4 Hz, 1H), 3.30 (s, 3H). |

-continued
| Example | Structure/Name/Characterization |
|---|---|
| 727 | 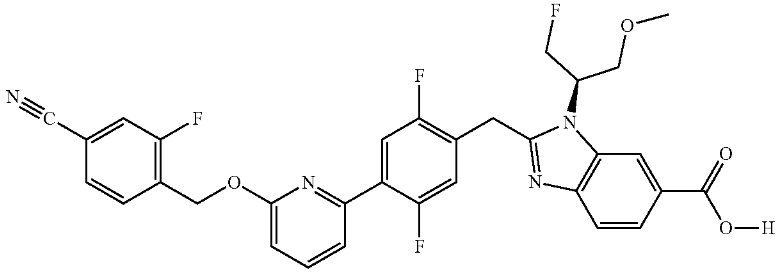 [SMILES: COC[C@H](CF)n1c(Cc2cc(F)c(-c3cccc(OCc4ccc(C#N)cc4F)n3)cc2F)nc2ccc(C(=O)O)cc21] ES/MS m/z 605.5; 1H NMR (400 MHz, Methanol-d4) δ 8.66-8.52 (m, 1H), 8.14 (dd, J = 8.6, 1.4 Hz, 1H), 7.86-7.75 (m, 3H), 7.73 (t, J = 7.5 Hz, 1H), 7.67-7.53 (m, 3H), 7.27 (dd, J = 11.4, 6.0 Hz, 1H), 7.01-6.88 (m, 1H), 5.63 (s, 2H), 5.42-5.18 (m, 1H), 5.16-5.01 (m, 1H), 4.94 (dd, J = 10.6, 3.6 Hz, 1H), 4.64 (s, 2H), 4.13 (dd, J = 10.5, 7.9 Hz, 1H), 3.99 (dd, J = 10.5, 4.5 Hz, 1H), 3.31 (s, 3H). |
| 728 | 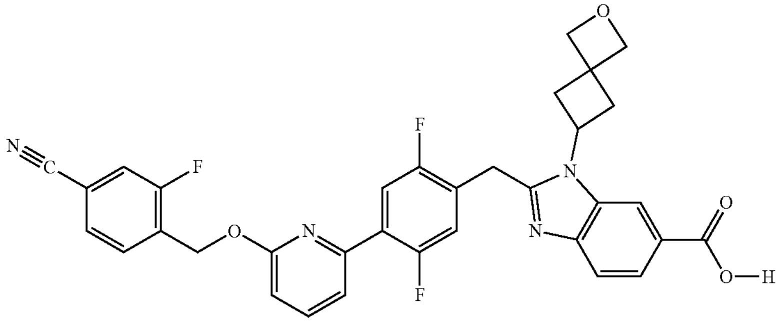 [SMILES: N#Cc1ccc(COc2cccc(-c3cc(F)c(Cc4nc5ccc(C(=O)O)cc5n4C4CC5(COC5)C4)cc3F)n2)c(F)c1] ES/MS m/z 611.5; 1H NMR (400 MHz, Methanol-d4) δ 8.40 (t, J = 1.0 Hz, 1H), 8.20-8.09 (m, 1H), 7.88-7.68 (m, 4H), 7.68-7.51 (m, 3H), 7.25 (dd, J = 11.2, 6.1 Hz, 1H), 6.95 (d, J = 8.2 Hz, 1H), 5.63 (s, 2H), 5.20 (p, J = 8.7 Hz, 1H), 4.92 (s, 2H), 4.76-4.53 (m, 3H), 3.19 (qd, J = 9.9, 2.2 Hz, 2H), 3.12-2.98 (m, 2H). |
| 729 | 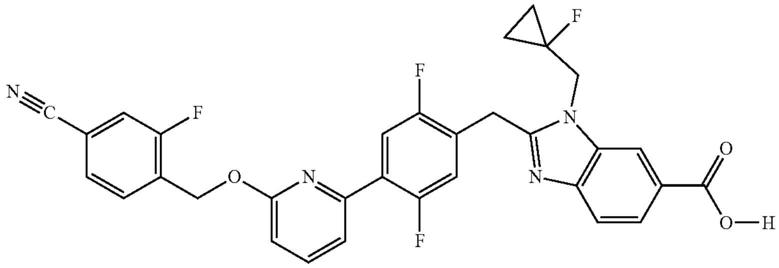 [SMILES: N#Cc1ccc(COc2cccc(-c3cc(F)c(Cc4nc5ccc(C(=O)O)cc5n4CC4(F)CC4)cc3F)n2)c(F)c1] ES/MS m/z 587.5; 1H NMR (400 MHz, Methanol-d4) δ 8.27-8.17 (m, 1H), 8.04 (dd, J = 8.5, 1.5 Hz, 1H), 7.84-7.62 (m, 4H), 7.55-7.42 (m, 3H), 7.10 (dd, J = 11.3, 6.0 Hz, 1H), 6.86 (d, J = 8.2 Hz, 1H), 5.59 (s, 2H), 4.73 (d, J = 20.0 Hz, 2H), 4.48 (s, 2H), 1.30-1.12 (m, 2H), 0.99 (td, J = 8.5, 6.5 Hz, 2H). |
| 730 | 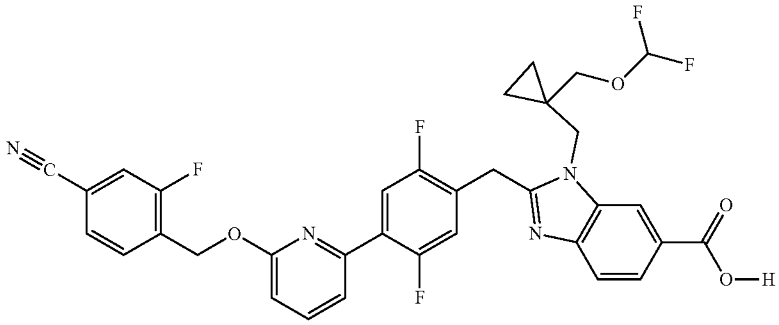 [SMILES: N#Cc1ccc(COc2cccc(-c3cc(F)c(Cc4nc5ccc(C(=O)O)cc5n4CC4(COC(F)F)CC4)cc3F)n2)c(F)c1] |

-continued

| Example | Structure/Name/Characterization |
| --- | --- |
| | ES/MS m/z 649.5; 1H NMR (400 MHz, Methanol-d4) δ 8.35 (d, J = 1.5 Hz, 1H), 8.06 (dd, J = 8.6, 1.5 Hz, 1H), 7.81-7.66 (m, 4H), 7.56-7.32 (m, 3H), 7.11 (dd, J = 11.2, 6.0 Hz, 1H), 6.88 (d, J = 8.2 Hz, 1H), 6.27 (t, J = 74.5 Hz, 1H), 5.59 (s, 2H), 4.50 (d, J = 7.2 Hz, 4H), 3.61 (s, 2H), 0.91-0.73 (m, 4H). |
| 731 | 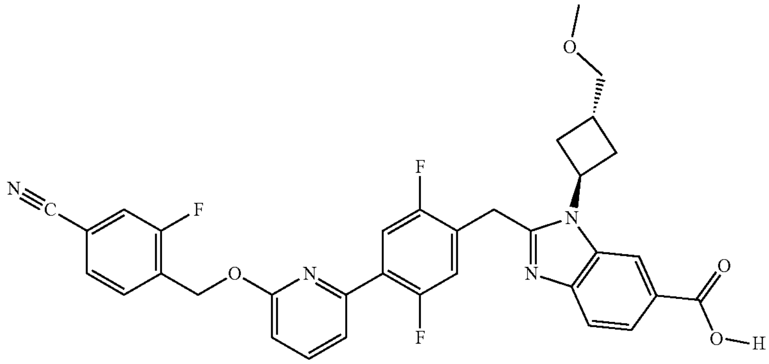 [SMILES: COC[C@H]1C[C@H](n2c(Cc3cc(F)c(-c4cccc(OCc5ccc(C#N)cc5F)n4)cc3F)nc3ccc(C(=O)O)cc32)C1] ES/MS m/z 613.5; 1H NMR (400 MHz, Methanol-d4) δ 8.69 (t, J = 1.0 Hz, 1H), 8.23 (dd, J = 8.6, 1.4 Hz, 1H), 7.92-7.77 (m, 3H), 7.72 (t, J = 7.5 Hz, 1H), 7.67-7.51 (m, 3H), 7.33 (dd, J = 11.2, 6.1 Hz, 1H), 6.96 (d, J = 8.2 Hz, 1H), 5.62 (s, 2H), 5.48 (p, J = 8.5 Hz, 1H), 4.68 (s, 2H), 3.63 (d, J = 5.6 Hz, 2H), 3.48 (s, 3H), 3.25-3.02 (m, 2H), 2.90 (t, J = 5.2 Hz, 1H), 2.55 (ddt, J = 11.6, 8.8, 3.1 Hz, 2H). |
| 732 | 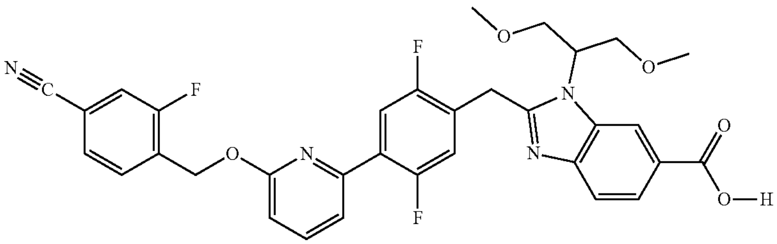 [SMILES: COCC(COC)n1c(Cc2cc(F)c(-c3cccc(OCc4ccc(C#N)cc4F)n3)cc2F)nc2ccc(C(=O)O)cc21] ES/MS m/z 617.5; 1H NMR (400 MHz, Methanol-d4) δ 8.70 (t, J = 0.9 Hz, 1H), 8.19 (dd, J = 8.6, 1.4 Hz, 1H), 7.88-7.75 (m, 3H), 7.72 (t, J = 7.5 Hz, 1H), 7.64-7.51 (m, 3H), 7.31 (dd, J = 11.4, 6.1 Hz, 1H), 6.95 (d, J = 8.2 Hz, 1H), 5.63 (s, 2H), 5.22 (dt, J = 8.5, 4.2 Hz, 1H), 4.69 (s, 2H), 4.14 (dd, J = 10.6, 8.3 Hz, 2H), 3.93 (dd, J = 10.6, 4.1 Hz, 2H), 3.30 (s, 6H). |
| 733 | 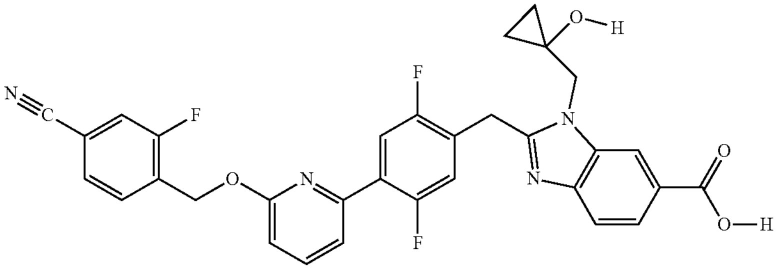 [SMILES: N#Cc1ccc(COc2cccc(-c3cc(F)c(Cc4nc5ccc(C(=O)O)cc5n4CC4(O)CC4)cc3F)n2)c(F)c1] ES/MS m/z 585.4; 1H NMR (400 MHz, Methanol-d4) δ 8.62-8.51 (m, 1H), 8.21 (dd, J = 8.6, 1.4 Hz, 1H), 7.92-7.81 (m, 2H), 7.81-7.68 (m, 2H), 7.69-7.55 (m, 3H), 7.37 (dd, J = 11.2, 6.0 Hz, 1H), 6.97 (d, J = 8.3 Hz, 1H), 5.65 (s, 2H), 4.83 (s, 2H), 4.76 (s, 2H), 1.11-0.98 (m, 2H), 0.94 (d, J = 5.3 Hz, 2H). |

-continued

| Example | Structure/Name/Characterization |
|---|---|
| 734 | 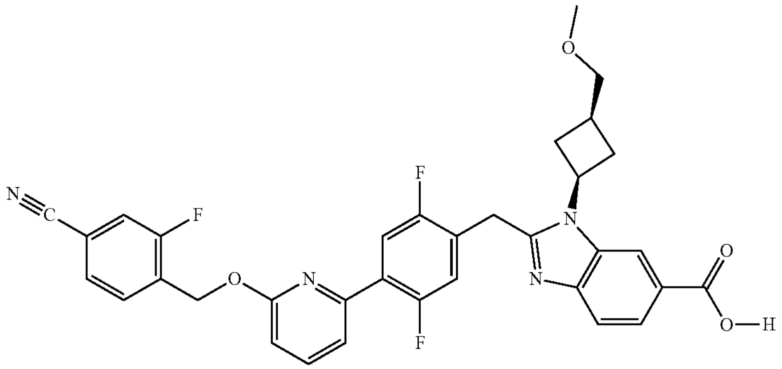 [SMILES: COC[C@H]1C[C@@H](n2c(Cc3cc(F)c(-c4cccc(OCc5ccc(C#N)cc5F)n4)cc3F)nc3ccc(C(=O)O)cc32)C1]<br>ES/MS m/z 613.5; 1H NMR (400 MHz, Chloroform-d) δ 9.05 (s, 1H), 8.13 (dd, J = 8.6, 1.3 Hz, 1H), 7.93 (d, J = 8.6 Hz, 1H), 7.79 (dd, J = 10.9, 6.2 Hz, 1H), 7.70 (dt, J = 21.5, 7.6 Hz, 2H), 7.59-7.52 (m, 1H), 7.49 (dd, J = 7.9, 1.5 Hz, 1H), 7.42 (dd, J = 9.3, 1.5 Hz, 1H), 7.24-7.12 (m, 1H), 6.87 (d, J = 8.1 Hz, 1H), 5.59 (s, 2H), 4.82-4.65 (m, 2H), 3.59 (s, 3H), 3.52 (d, J = 2.5 Hz, 2H), 3.26-3.06 (m, 2H), 2.55 (q, J = 13.0, 10.0 Hz, 4H). |
| 735 | 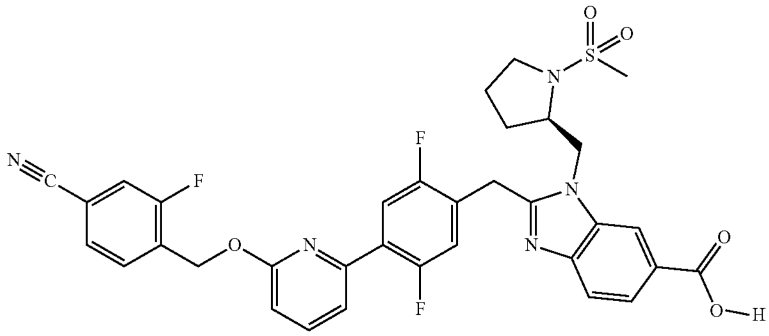 [SMILES: CS(=O)(=O)N1CCC[C@@H]1Cn1c(Cc2cc(F)c(-c3cccc(OCc4ccc(C#N)cc4F)n3)cc2F)nc2ccc(C(=O)O)cc21]<br>ES/MS m/z 676.6; 1H NMR (400 MHz, Methanol-d4) δ 8.57 (d, J = 1.3 Hz, 1H), 8.24 (dd, J = 8.6, 1.4 Hz, 1H), 7.96-7.81 (m, 2H), 7.74 (dd, J = 15.2, 8.0 Hz, 2H), 7.67-7.52 (m, 3H), 7.47 (dd, J = 11.1, 6.1 Hz, 1H), 6.97 (d, J = 8.2 Hz, 1H), 5.64 (s, 2H), 4.85 (s, 1H), 4.83-4.58 (m, 3H), 4.39-4.22 (m, 1H), 3.59 (ddd, J = 11.2, 6.8, 4.7 Hz, 1H), 3.49 (dt, J = 10.5, 7.3 Hz, 1H), 2.76 (s, 3H), 2.29 (ddd, J = 16.6, 13.0, 7.1 Hz, 2H), 2.18-2.00 (m, 2H). |
| 736 | 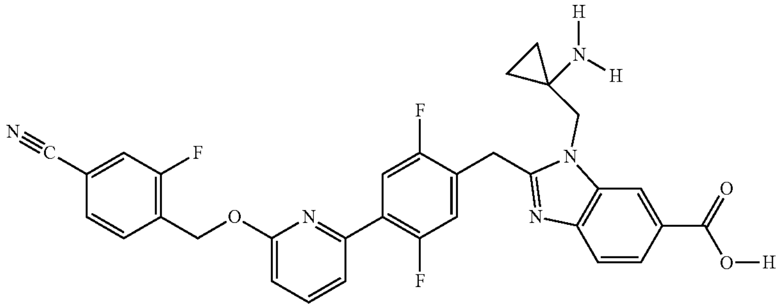 [SMILES: N#Cc1ccc(COc2cccc(-c3cc(F)c(Cc4nc5ccc(C(=O)O)cc5n4CC4(N)CC4)cc3F)n2)c(F)c1]<br>ES/MS m/z 584.4; 1H NMR (400 MHz, Methanol-d4) δ 8.44-8.33 (m, 1H), 8.05 (dd, J = 8.5, 1.5 Hz, 1H), 7.83 (t, J = 7.9 Hz, 1H), 7.79-7.67 (m, 3H), 7.63-7.52 (m, 3H), 7.27 (dd, J = 11.4, 6.1 Hz, 1H), 6.94 (dd, J = 8.3, 0.7 Hz, 1H), 5.63 (s, 2H), 4.83 (s, 2H), 4.50 (s, 2H), 1.17 (s, 4H). |

-continued

| Example | Structure/Name/Characterization |
|---|---|
| 737 | 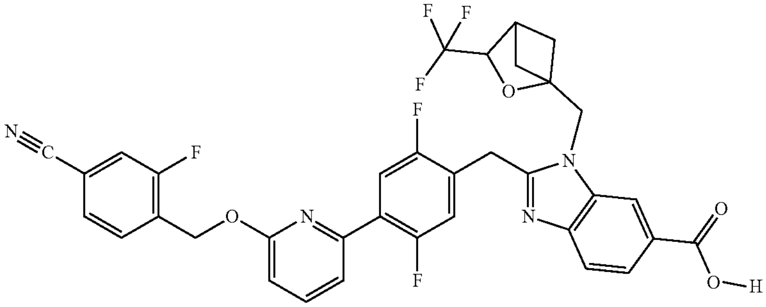 [SMILES: N#Cc1ccc(COc2cccc(-c3cc(F)c(Cc4nc5ccc(C(=O)O)cc5n4CC45CC(C4)C(C(F)(F)F)O5)cc3F)n2)c(F)c1] ES/MS m/z 679.6; 1H NMR (400 MHz, Methanol-d4) δ 8.56 (d, J = 1.2 Hz, 1H), 8.19 (dd, J = 8.6, 1.4 Hz, 1H), 7.93-7.79 (m, 2H), 7.79-7.70 (m, 2H), 7.60 (ddd, J = 11.5, 8.9, 1.5 Hz, 3H), 7.32 (dd, J = 11.2, 6.0 Hz, 1H), 6.96 (dd, J = 8.3, 0.7 Hz, 1H), 5.64 (s, 2H), 5.06 (s, 2H), 4.76 (s, 2H), 4.34 (q, J = 7.4 Hz, 1H), 3.14 (q, J = 3.8, 3.1 Hz, 1H), 2.31 (dd, J = 7.6, 3.3 Hz, 1H), 2.11 (d, J = 8.2 Hz, 1H), 1.82 (t, J = 9.7 Hz, 1H), 1.67 (dd, J = 10.9, 7.7 Hz, 1H). |
| 738 | 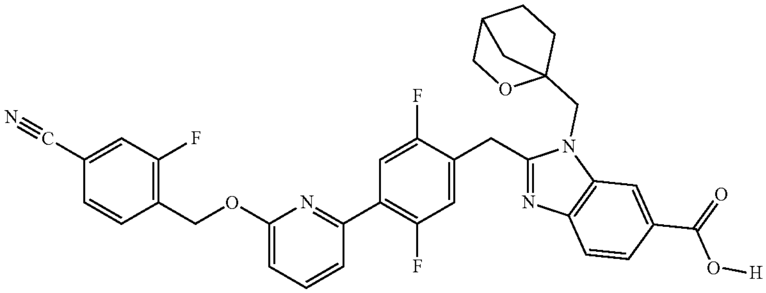 [SMILES: N#Cc1ccc(COc2cccc(-c3cc(F)c(Cc4nc5ccc(C(=O)O)cc5n4CC45CCC(CO4)C5)cc3F)n2)c(F)c1] ES/MS m/z 625.6; 1H NMR (400 MHz, Methanol-d4) δ 8.55 (t, J = 1.0 Hz, 1H), 8.19 (dd, J = 8.6, 1.4 Hz, 1H), 7.90-7.67 (m, 4H), 7.67-7.51 (m, 3H), 7.31 (dd, J = 11.2, 6.0 Hz, 1H), 6.96 (d, J = 8.2 Hz, 1H), 5.63 (s, 2H), 5.04-4.91 (m, 2H), 4.79 (d, J = 6.7 Hz, 2H), 3.70 (dt, J = 6.1, 2.8 Hz, 1H), 3.62 (d, J = 6.8 Hz, 1H), 2.51 (s, 1H), 2.09-1.80 (m, 2H), 1.80-1.73 (m, 1H), 1.73-1.54 (m, 2H), 1.37 (d, J = 9.5 Hz, 1H). |
| 739 | 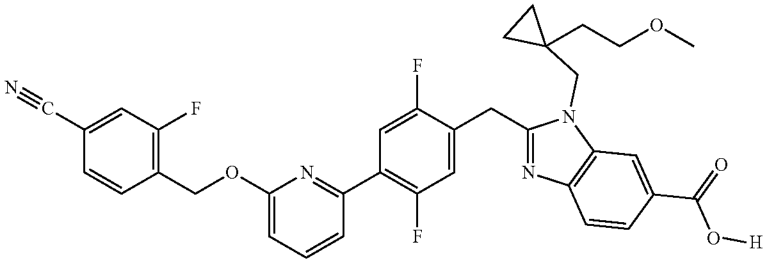 [SMILES: COCCC1(Cn2c(Cc3cc(F)c(-c4cccc(OCc5ccc(C#N)cc5F)n4)cc3F)nc3ccc(C(=O)O)cc32)CC1] ES/MS m/z 627.5; 1H NMR (400 MHz, Methanol-d4) δ 8.24 (d, J = 1.4 Hz, 1H), 7.98 (dd, J = 8.5, 1.5 Hz, 1H), 7.77-7.56 (m, 4H), 7.56-7.36 (m, 3H), 6.98 (dd, J = 11.3, 6.0 Hz, 1H), 6.80 (d, J = 8.2 Hz, 1H), 5.55 (s, 2H), 4.37 (d, J = 21.6 Hz, 4H), 3.44 (t, J = 6.1 Hz, 2H), 3.31 (s, 3H), 1.58 (t, J = 6.1 Hz, 2H), 0.51 (d, J = 5.1 Hz, 2H), 0.41 (d, J = 5.1 Hz, 2H). |
| 740 | 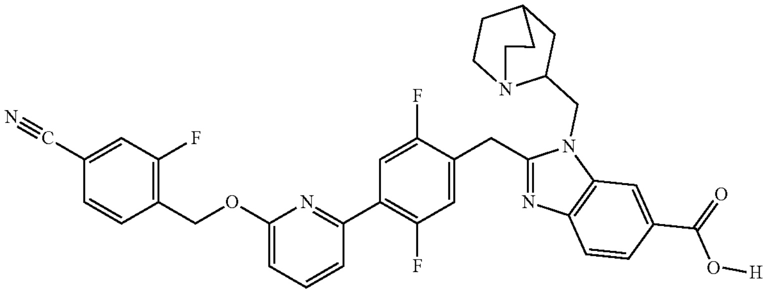 [SMILES: N#Cc1ccc(COc2cccc(-c3cc(F)c(Cc4nc5ccc(C(=O)O)cc5n4CC4CC5CCN4CC5)cc3F)n2)c(F)c1] |

-continued

| Example | Structure/Name/Characterization |
|---|---|
| | ES/MS m/z 638.6; 1H NMR (400 MHz, Methanol-d4) δ 8.44 (d, J = 1.4 Hz, 1H), 8.07 (dd, J = 8.5, 1.5 Hz, 1H), 7.83 (t, J = 7.9 Hz, 1H), 7.80-7.67 (m, 3H), 7.67-7.54 (m, 3H), 7.32 (dd, J = 11.3, 6.1 Hz, 1H), 6.95 (d, J = 8.2 Hz, 1H), 5.63 (s, 2H), 5.02-4.90 (m, 1H), 4.64-4.41 (m, 2H), 4.23 (p, J = 8.1 Hz, 1H), 3.87 (q, J = 10.3 Hz, 1H), 3.50-3.36 (m, 3H), 2.34-2.08 (m, 3H), 2.08-1.86 (m, 3H), 1.79 (dd, J = 13.4, 7.9 Hz, 1H). |
| 741 | 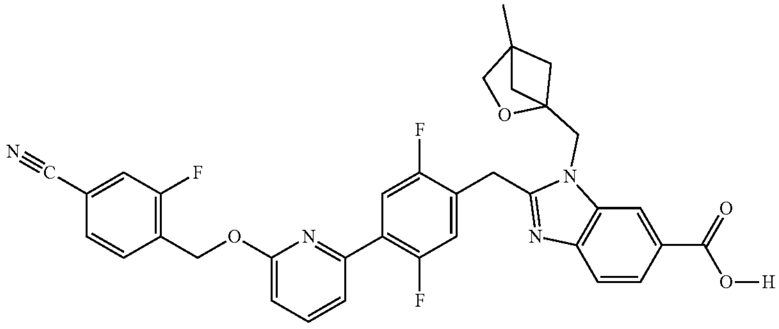 [SMILES: CC12COC(Cn3c(Cc4cc(F)c(-c5cccc(OCc6ccc(C#N)cc6F)n5)cc4F)nc4ccc(C(=O)O)cc43)(C1)C2] ES/MS m/z 625.6; 1H NMR (400 MHz, DMSO-d6) δ 8.27 (d, J = 1.5 Hz, 1H), 7.97-7.84 (m, 2H), 7.84-7.68 (m, 4H), 7.61 (d, J = 8.4 Hz, 1H), 7.53 (dd, J = 7.5, 1.7 Hz, 1H), 7.41 (dd, J = 11.5, 6.1 Hz, 1H), 7.00 (d, J = 8.2 Hz, 1H), 5.60 (s, 2H), 4.79 (s, 2H), 4.49 (s, 2H), 3.45 (s, 2H), 1.74 (dd, J = 4.3, 1.7 Hz, 2H), 1.39 (dd, J = 4.4, 1.7 Hz, 2H), 1.26 (s, 3H). |
| 742 | 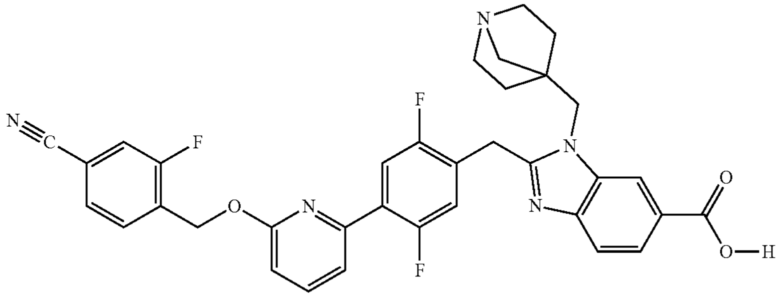 [SMILES: N#Cc1ccc(COc2cccc(-c3cc(F)c(Cc4nc5ccc(C(=O)O)cc5n4CC45CCN(CC4)C5)cc3F)n2)c(F)c1] ES/MS m/z 624.4; 1H NMR (400 MHz, Methanol-d4) δ 8.38 (dd, J = 1.4, 0.7 Hz, 1H), 8.10 (dd, J = 8.5, 1.4 Hz, 1H), 7.83 (dd, J = 8.3, 7.5 Hz, 1H), 7.80-7.67 (m, 3H), 7.67-7.54 (m, 3H), 7.34 (dd, J = 11.3, 6.1 Hz, 1H), 6.95 (dd, J = 8.3, 0.6 Hz, 1H), 5.63 (s, 2H), 4.98 (s, 2H), 4.54 (s, 2H), 3.58-3.39 (m, 3H), 3.37 (s, 2H), 3.33 (s, 3H), 2.27-2.00 (m, 5H). |
| 743 | 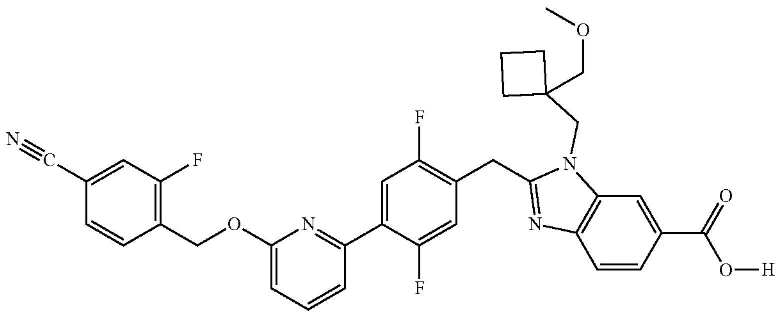 [SMILES: COCC1(Cn2c(Cc3cc(F)c(-c4cccc(OCc5ccc(C#N)cc5F)n4)cc3F)nc3ccc(C(=O)O)cc32)CCC1] ES/MS m/z 627.5; 1H NMR (400 MHz, Methanol-d4) δ 8.58 (dd, J = 1.5, 0.7 Hz, 1H), 8.17 (dd, J = 8.6, 1.4 Hz, 1H), 7.94-7.78 (m, 2H), 7.78-7.67 (m, 2H), 7.69-7.49 (m, 3H), 7.32 (dd, J = 11.2, 6.1 Hz, 1H), 6.95 (dd, J = 8.2, 0.7 Hz, 1H), 5.63 (s, 2H), 4.70 (s, 2H), 4.64 (s, 2H), 3.44 (s, 2H), 3.36 (s, 3H), 2.26-2.02 (m, 3H), 1.97 (ttd, J = 8.6, 5.0, 3.9, 2.1 Hz, 3H). |

-continued
| Example | Structure/Name/Characterization |
|---|---|
| 744 | 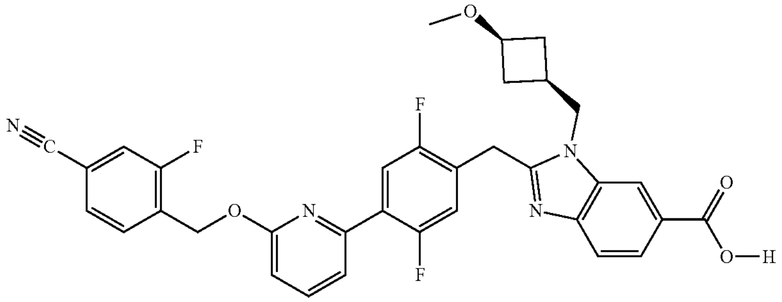 [SMILES: CO[C@H]1C[C@@H](Cn2c(Cc3cc(F)c(-c4cccc(OCc5ccc(C#N)cc5F)n4)cc3F)nc3ccc(C(=O)O)cc32)C1] ES/MS m/z 613.2; 1H NMR (400 MHz, Methanol-d4) δ 8.50 (t, J = 1.0 Hz, 1H), 8.19 (dd, J = 8.6, 1.4 Hz, 1H), 7.91-7.68 (m, 4H), 7.68-7.52 (m, 3H), 7.38 (dd, J = 11.2, 6.1 Hz, 1H), 6.96 (dd, J = 8.3, 0.6 Hz, 1H), 5.63 (s, 2H), 4.76-4.58 (m, 4H), 3.88-3.68 (m, 1H), 3.22 (s, 3H), 2.51-2.32 (m, 3H), 1.79 (tt, J = 8.0, 3.8 Hz, 2H). |
| 745 | 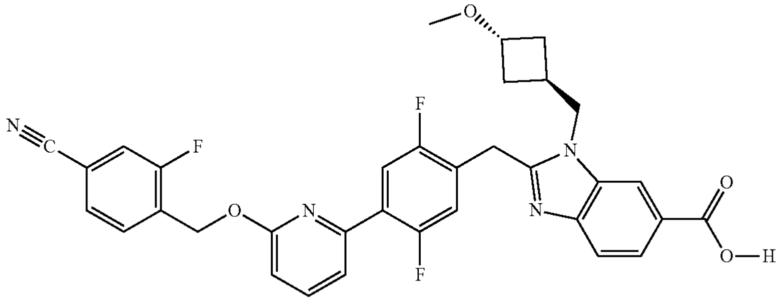 [SMILES: CO[C@H]1C[C@H](Cn2c(Cc3cc(F)c(-c4cccc(OCc5ccc(C#N)cc5F)n4)cc3F)nc3ccc(C(=O)O)cc32)C1] ES/MS m/z 613.5; 1H NMR (400 MHz, Methanol-d4) δ 8.54 (t, J = 1.0 Hz, 1H), 8.20 (dd, J = 8.6, 1.4 Hz, 1H), 7.96-7.68 (m, 4H), 7.68-7.47 (m, 3H), 7.39 (dd, J = 11.2, 6.0 Hz, 1H), 6.96 (d, J = 8.2 Hz, 1H), 5.63 (s, 2H), 4.77-4.60 (m, 4H), 4.19 (p, J = 6.1 Hz, 1H), 3.24 (s, 3H), 2.97 (tt, J = 9.1, 5.2 Hz, 1H), 2.33-1.99 (m, 4H). |
| 746 | 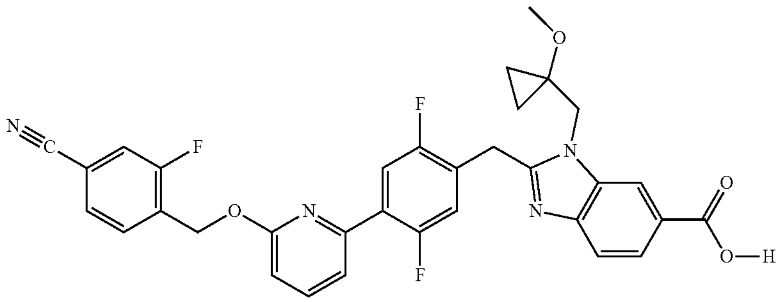 [SMILES: COC1(Cn2c(Cc3cc(F)c(-c4cccc(OCc5ccc(C#N)cc5F)n4)cc3F)nc3ccc(C(=O)O)cc32)CC1] ES/MS m/z 599.4; 1H NMR (400 MHz, DMSO-d6) δ 8.32 (d, J = 1.4 Hz, 1H), 7.96-7.87 (m, 2H), 7.83 (dd, J = 8.4, 1.5 Hz, 1H), 7.80-7.69 (m, 3H), 7.62 (d, J = 8.4 Hz, 1H), 7.54 (dd, J = 7.5, 1.7 Hz, 1H), 7.44 (dd, J = 11.5, 6.1 Hz, 1H), 7.00 (d, J = 8.2 Hz, 1H), 5.61 (s, 2H), 4.73 (s, 2H), 4.52 (s, 2H), 3.22 (s, 3H), 0.95-0.76 (m, 4H). 19F NMR (377 MHz, DMSO-d6) δ −75.16, −115.91 (dd, J = 9.9, 6.3 Hz), −121.04--123.78 (m). |

-continued
| Example | Structure/Name/Characterization |
| --- | --- |
| 747 | 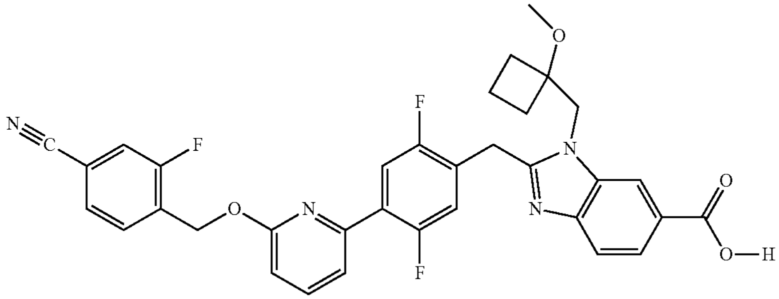 [SMILES: COC1(Cn2c(Cc3cc(F)c(-c4cccc(OCc5ccc(C#N)cc5F)n4)cc3F)nc3ccc(C(=O)O)cc32)CCC1] ES/MS m/z 613.5; 1H NMR (400 MHz, DMSO-d6) δ 8.37 (d, J = 1.5 Hz, 1H), 7.96-7.87 (m, 2H), 7.83 (dd, J = 8.4, 1.5 Hz, 1H), 7.80-7.69 (m, 3H), 7.62 (d, J = 8.4 Hz, 1H), 7.53 (dd, J = 7.5, 1.7 Hz, 1H), 7.41 (dd, J = 11.5, 6.1 Hz, 1H), 7.00 (d, J = 8.2 Hz, 1H), 5.60 (s, 2H), 4.70 (s, 2H), 4.52 (s, 2H), 3.24 (s, 3H), 2.40-2.24 (m, 2H), 2.04-1.68 (m, 4H). 19F NMR (377 MHz, DMSO-d6) δ −75.22, −115.92 (dd, J = 10.0, 6.1 Hz), −119.52-−124.31 (m). |
Example 426. 2-(4-(6-((4-cyano-2-fluorobenzyl)oxy)pyridin-2-yl)-2,5-difluorobenzyl)-1-(2-methoxyethyl)-1H-benzo[d]imidazole-6-carboxylic acid
Procedure 51
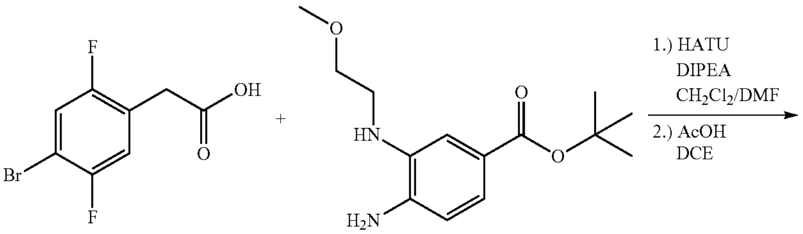
I-68
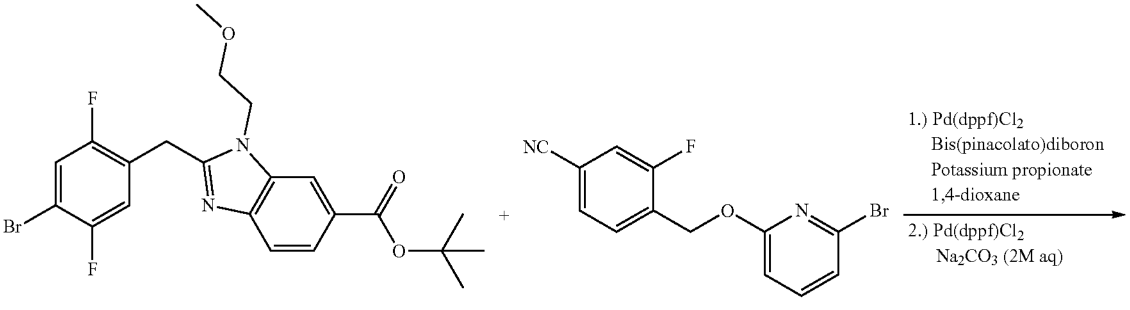
I-6
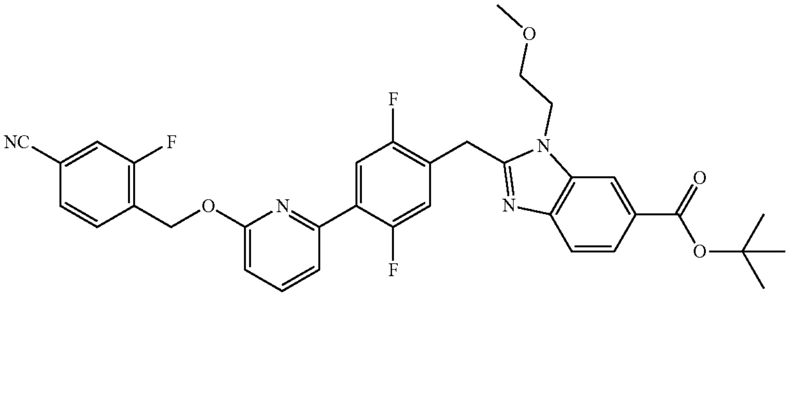

-continued

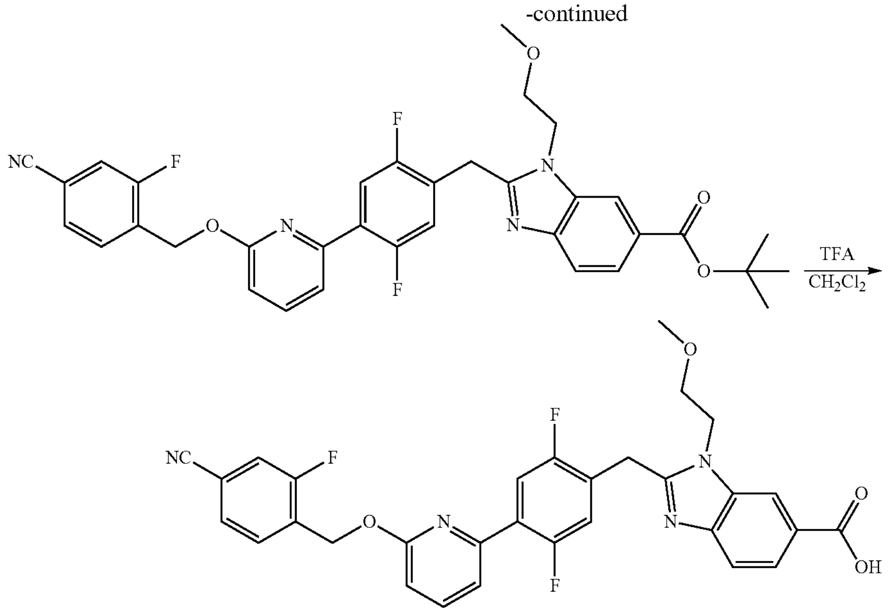

Example 426

Tert-butyl 2-(4-bromo-2,5-difluorobenzyl)-1-(2-methoxyethyl)-1H-benzo[d]imidazole-6-carboxylate: To a solution of tert-butyl 4-amino-3-(2-methoxyethylamino) benzoate (I-68) (10.7 g, 40.2 mmol) in $CH_2Cl_2$ (200 mL) and DMF (100 mL) at 0° C. was added O-(7-azabenzotriazol-1-yl)-N,N,N',N'-tetramethyluronium hexafluorophosphate (HATU) (19.8 g, 52.2 mmol) and 2-(4-bromo-2,5-difluorophenyl)acetic acid (13.1 g, 52.2 mmol), followed by N,N-diisopropylethylamine (21 mL, 121 mmol) and the mixture was warmed to room temperature and stirred for 72 hours. The mixture was diluted with $CH_2Cl_2$ (200 mL) and washed with 50% aq. $NH_4Cl$ (2×100 mL), sat. aq. $NaHCO_3$ (1×100 mL), and brine (1×100 mL). The organic layer was dried over $MgSO_4$, filtered and concentrated under reduced pressure. The crude residue was dissolved in 1,2-dichloroethane (100 mL) and AcOH (30 mL). The mixture was stirred at 70° C. for 4 hours. The mixture was dry-loaded onto silica and was purified by column chromatography (15-50% EtOAc in hexane) to give the title compound. ES/MS: 481.9 (M+); $^1H$ NMR (400 MHz, Methanol-d4) δ 8.18 (d, J=1.4 Hz, 1H), 7.90 (dd, J=8.5, 1.5 Hz, 1H), 7.61 (d, J=8.5 Hz, 1H), 7.52 (dd, J=8.8, 5.7 Hz, 1H), 7.20 (dd, J=8.8, 6.3 Hz, 1H), 4.55 (t, J=5.0 Hz, 2H), 4.42 (s, 2H), 3.73 (t, J=5.0 Hz, 2H), 3.27 (s, 3H), 1.65 (s, 9H).

Tert-butyl 2-(4-(6-((4-cyano-2-fluorobenzyl)oxy)pyridin-2-yl)-2,5-difluorobenzyl)-1-(2-methoxyethyl)-1H-benzo[d] imidazole-6-carboxylate: To a 250 mL RBF was added tert-butyl 2-(4-bromo-2,5-difluorobenzyl)-1-(2-methoxyethyl)-1H-benzo[d]imidazole-6-carboxylate (4 g, 8.31 mmol), potassium propionate (2.8 g, 2.49 mmol), bis(pinacolato)diboron (2.43 g, 9.56 mmol), 1,1'-Bis(diphenylphosphino)ferrocene]dichloropalladium(II) (616 mg, 0.831 mmol) and dioxane (50 mL). The resulting mixture was degassed by bubbling argon below the liquid surface for 5 minutes after which the flask was fitted with a reflux condenser and stirred at 110° C. for 90 minutes. Upon cooling the vial was opened and to the mixture was added 4-(((6-bromopyridin-2-yl)oxy)methyl)-3-fluorobenzonitrile (I-6) (2.18 g, 9.14 mmol), 1,1'-bis(diphenylphosphino)ferrocene]dichloropalladium(II) (185 mg, 0.25 mmol) and sodium carbonate (2 M aq. solution, 8.3 mL, 16.6 mmol), and water (8 mL). The resulting mixture was degassed by bubbling argon below the liquid surface for 1 minute after which the RBF was sealed and placed in a 90° C. heating block for 1 hour. Upon completion the mixture was cooled to room temperature and diluted with EtOAc (100 mL). The mixture was washed with water (50 mL). The layers were separated, and the aqueous layer was extracted with EtOAc (1×50 mL). The combined organic layers were dried over $MgSO_4$, filtered and concentrated. The crude residue was dry-loaded onto silica and purified by column chromatography (15-50% EtOAc in hexane) to give the title compound as a 1:1 mixture with pinacol. ES/MS: 629.5 (M+H$^+$); $^1H$ NMR (400 MHz, DMSO-d6) δ 8.14 (dd, J=1.6, 0.7 Hz, 1H), 7.96-7.86 (m, 2H), 7.82-7.70 (m, 4H), 7.59 (dd, J=8.4, 0.6 Hz, 1H), 7.53 (dd, J=7.3, 1.7 Hz, 1H), 7.37 (dd, J=11.5, 6.1 Hz, 1H), 6.99 (dd, J=8.3, 0.7 Hz, 1H), 5.60 (s, 2H), 4.58 (t, J=5.1 Hz, 2H), 4.43 (s, 2H), 3.69 (t, J=5.0 Hz, 2H), 3.22 (s, 3H), 1.58 (s, 9H).

2-(4-(6-((4-cyano-2-fluorobenzyl)oxy)pyridin-2-yl)-2,5-difluorobenzyl)-1-(2-methoxyethyl)-1H-benzo[d]imidazole-6-carboxylic acid (Example 426): To a solution of tert-butyl 2-(4-(6-((4-cyano-2-fluorobenzyl)oxy)pyridin-2-yl)-2,5-difluorobenzyl)-1-(2-methoxyethyl)-1H-benzo[d] imidazole-6-carboxylate (1:1 ratio with pinacol) (5.32 g, 7.12 mmol) in $CH_2Cl_2$ (20 mL) was added TFA (5 mL) and the resulting solution was stirred at 45° C. for 4 hours. The mixture was concentrated under reduced pressure, and acetonitrile (12 mL) was added. The mixture was purified by RP-HPLC (eluent: water/MeCN 0.1% TFA). The combined fractions were frozen and placed on a lyophilizer to ultimately deliver the final compound Example 426 (trifluoroacetate salt). ES/MS: 573.2 (M+H$^+$); $^1H$ NMR (400 MHz, Methanol-d4) δ 8.58-8.54 (m, 1H), 8.23 (dd, J=8.6, 1.5 Hz, 1H), 7.89-7.68 (m, 4H), 7.65-7.54 (m, 3H), 7.36 (dd, J=11.2, 6.1 Hz, 1H), 6.97 (dd, J=8.3, 0.6 Hz, 1H), 5.63 (s, 2H), 4.82 (t, J=4.9 Hz, 2H), 4.76 (s, 2H), 3.85 (dd, J=5.4, 4.4 Hz, 2H), 3.32 (s, 3H).

Example 117, 133, 134, 153, 161, 162, 352, 367, 399, 409, 416, 417, 429-433, 441, 442, 586, 605, and 748-753. Compounds Prepared Using Procedure 51

Other compounds of the present disclosure prepared using the general route described in Procedure 51 include the following Examples.

| Example | Structure/Name/Characterization |
|---|---|
| 117 | 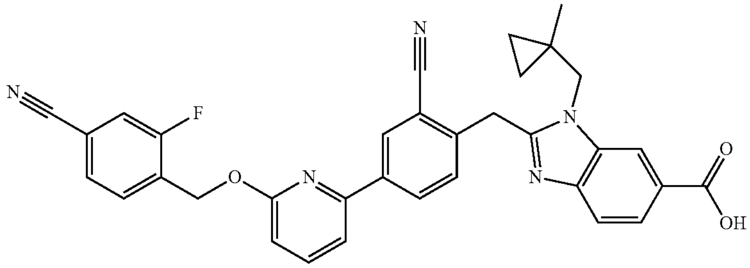 [SMILES: CC1(Cn2c(Cc3ccc(-c4cccc(OCc5ccc(C#N)cc5F)n4)cc3C#N)nc3ccc(C(=O)O)cc32)CC1] 2-(2-cyano-4-(6-((4-cyano-2-fluorobenzyl)oxy)pyridin-2-yl)benzyl)-1-((1-methylcyclopropyl)methyl)-1H-benzo[d]imidazole-6-carboxylic acid: ES/MS m/z 572.2; $^1$H NMR (400 MHz, MeOD) δ 9.26 (d, J = 1.4 Hz, 1H), 8.76 (d, J = 8.8 Hz, 1H), 8.61 (dd, J = 8.8, 1.7 Hz, 1H), 8.39 (d, J = 1.5 Hz, 1H), 8.21 (dd, J = 8.8, 1.6 Hz, 1H), 8.10 (d, J = 8.8 Hz, 1H), 7.98-7.86 (m, 1H), 7.81 (dd, J = 13.5, 7.3 Hz, 2H), 7.72-7.55 (m, 2H), 7.51 (s, 1H), 6.96 (d, J = 8.0 Hz, 1H), 5.76 (s, 2H), 4.51 (s, 2H), 1.18 (s, 3H), 0.90-0.86 (m, 2H), 0.66-0.48 (m, 2H). |
| 133 | 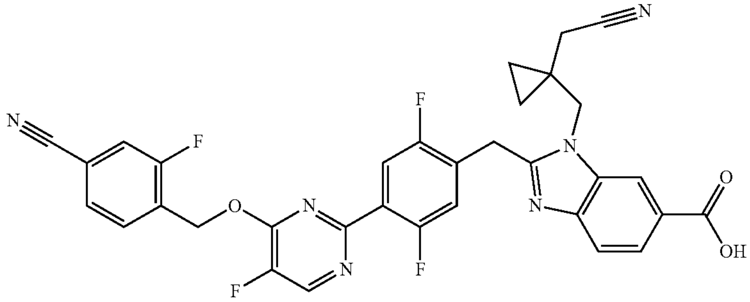 [SMILES: N#CCC1(Cn2c(Cc3cc(F)c(-c4ncc(F)c(OCc5ccc(C#N)cc5F)n4)cc3F)nc3ccc(C(=O)O)cc32)CC1] 2-(4-(4-((4-cyano-2-fluorobenzyl)oxy)-5-fluoropyrimidin-2-yl)-2,5-difluorobenzyl)-1-((1-(cyanomethyl)cyclopropyl)methyl)-1H-benzo[d]imidazole-6-carboxylic acid: ES/MS m/z 627.2; $^1$H NMR (400 MHz, MeOD) δ 8.64-8.58 (m, 2H), 8.25-8.15 (m, 1H), 7.92 (dd, J = 10.3, 6.1 Hz, 1H), 7.81-7.73 (m, 2H), 7.67-7.57 (m, 2H), 7.41 (dd, J = 10.7, 6.0 Hz, 1H), 5.76 (s, 2H), 4.76 (d, J = 10.9 Hz, 4H), 2.63 (s, 2H), 1.04-0.96 (m, 2H), 0.95-0.83 (m, 2H). |
| 134 | 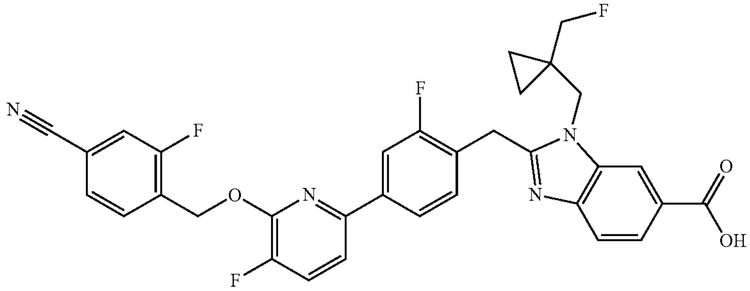 [SMILES: N#Cc1ccc(COc2nc(-c3ccc(Cc4nc5ccc(C(=O)O)cc5n4CC4(CF)CC4)c(F)c3)ccc2F)c(F)c1] 2-(4-(6-((4-cyano-2-fluorobenzyl)oxy)-5-fluoropyridin-2-yl)-2-fluorobenzyl)-1-((1-(fluoromethyl)cyclopropyl)methyl)-1H-benzo[d]imidazole-6-carboxylic acid: ES/MS m/z 601.2; $^1$H NMR (400 MHz, DMSO) δ 12.79 (br s, 1H), 8.24 (d, J = 1.5 Hz, 1H), 7.94 (dd, J = 10.0, 1.5 Hz, 1H), 7.88-7.72 (m, 6H), 7.69 (dd, J = 8.3, 2.8 Hz, 1H), 7.59 (d, J = 8.4 Hz, 1H), 7.43 (t, J = 8.0 Hz, 1H), 5.70 (s, 2H), 4.53 (s, 2H), 4.42 (s, 2H), 4.23 (s, 1H), 4.10 (s, 1H), 0.87-0.78 (m, 2H), 0.78-0.67 (m, 2H). |

-continued

| Example | Structure/Name/Characterization |
|---|---|
| 153 | 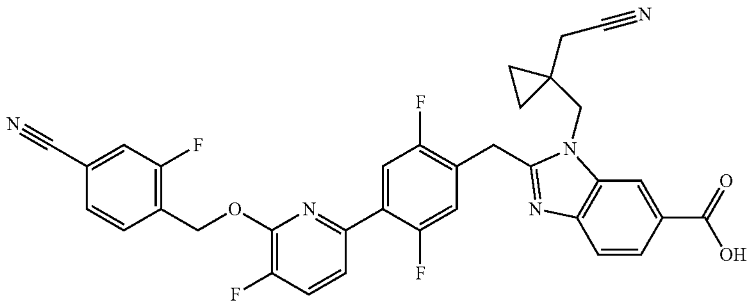 [SMILES: N#CCC1(Cn2c(Cc3cc(F)c(-c4ccc(F)c(OCc5ccc(C#N)cc5F)n4)cc3F)nc3ccc(C(=O)O)cc32)CC1] 2-(4-(6-((4-cyano-2-fluorobenzyl)oxy)-5-fluoropyridin-2-yl)-2,5-difluorobenzyl)-1-((1-(cyanomethyl)cyclopropyl)methyl)-1H-benzo[d]imidazole-6-carboxylic acid: ES/MS m/z 626.2; $^1$H NMR (400 MHz, DMSO) δ 8.30 (d, J = 1.5 Hz, 1H), 7.93 (dd, J = 10.0, 1.4 Hz, 1H), 7.87 (dd, J = 10.3, 8.2 Hz, 1H), 7.84-7.70 (m, 4H), 7.62 (d, J = 8.4 Hz, 1H), 7.55 (dd, J = 8.0, 2.8 Hz, 1H), 7.45 (dd, J = 9.9, 7.7 Hz, 1H), 5.69 (s, 2H), 4.58 (s, 2H), 4.47 (s, 2H), 2.68 (s, 2H), 0.78-0.67 (m, 4H). |
| 161 | 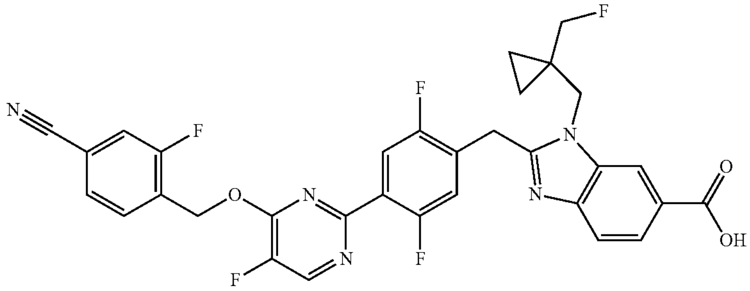 [SMILES: N#Cc1ccc(COc2nc(-c3cc(F)c(Cc4nc5ccc(C(=O)O)cc5n4CC4(CF)CC4)cc3F)ncc2F)c(F)c1] 2-(4-(4-((4-cyano-2-fluorobenzyl)oxy)-5-fluoropyrimidin-2-yl)-2,5-difluorobenzyl)-1-((1-(fluoromethyl)cyclopropyl)methyl)-1H-benzo[d]imidazole-6-carboxylic acid: ES/MS m/z 620.2; $^1$H NMR (400 MHz, MeOD) δ 8.61 (d, J = 2.8 Hz, 1H), 8.57 (d, J = 1.4 Hz, 1H), 8.19 (dd, J = 8.6, 1.4 Hz, 1H), 7.91 (dd, J = 10.3, 6.2 Hz, 1H), 7.81-7.72 (m, 2H), 7.67-7.57 (m, 2H), 7.37 (dd, J = 10.7, 6.0 Hz, 1H), 5.76 (s, 2H), 4.75 (d, J = 8.4 Hz, 4H), 4.29 (s, 1H), 4.17 (s, 1H), 1.12-0.98 (m, 2H), 0.90-0.86 (m, 2H). |
| 162 | 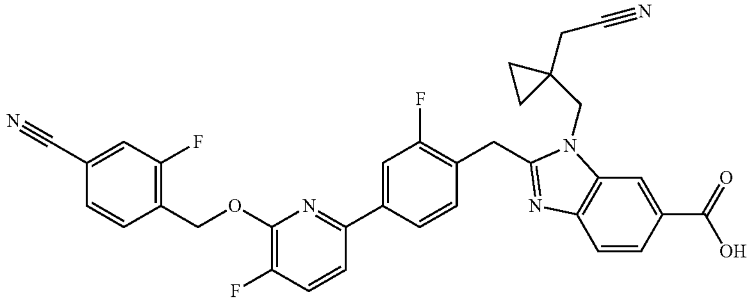 [SMILES: N#CCC1(Cn2c(Cc3ccc(-c4ccc(F)c(OCc5ccc(C#N)cc5F)n4)cc3F)nc3ccc(C(=O)O)cc32)CC1] 2-(4-(6-((4-cyano-2-fluorobenzyl)oxy)-5-fluoropyridin-2-yl)-2-fluorobenzyl)-1-((1-(cyanomethyl)cyclopropyl)methyl)-1H-benzo[d]imidazole-6-carboxylic acid: ES/MS m/z 608.2; $^1$H NMR (400 MHz, MeOD) δ 8.63 (s, 1H), 8.21 (dd, J = 8.6, 1.5 Hz, 1H), 7.92-7.81 (m, 2H), 7.80-7.71 (m, 2H), 7.67-7.51 (m, 5H), 5.71 (s, 2H), 4.77 (d, J = 9.2 Hz, 4H), 2.62 (s, 2H), 1.07-0.96 (m, 2H), 0.95-0.82 (m, 2H). |

-continued

| Example | Structure/Name/Characterization |
|---|---|
| 352 | 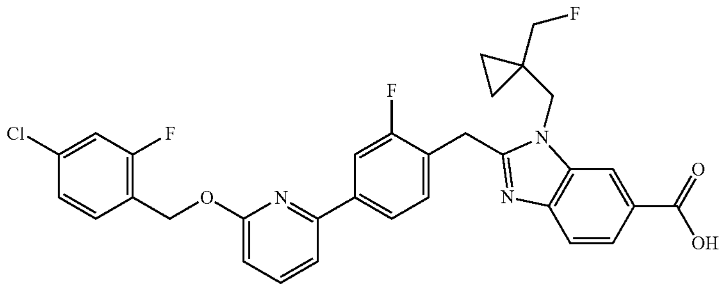 [SMILES: O=C(O)c1ccc2nc(Cc3ccc(-c4cccc(OCc5ccc(Cl)cc5F)n4)cc3F)n(CC3(CF)CC3)c2c1]<br>2-(4-(6-((4-chloro-2-fluorobenzyl)oxy)pyridin-2-yl)-2-fluorobenzyl)-1-((1-(fluoromethyl)cyclopropyl)methyl)-1H-benzo[d]imidazole-6-carboxylic acid: ES/MS m/z 592.2; $^{1}$H NMR (400 MHz, DMSO-d6) δ 8.33 (d, J = 1.4 Hz, 1H), 7.95 (dd, J = 4.9, 1.6 Hz, 1H), 7.92 (s, 1H), 7.90-7.81 (m, 2H), 7.71-7.58 (m, 3H), 7.53-7.44 (m, 2H), 7.33 (dd, J = 8.2, 2.0 Hz, 1H), 6.90 (d, J = 8.2 Hz, 1H), 5.53 (s, 2H), 4.61 (s, 2H), 4.52 (s, 2H), 4.20 (d, J = 48.8 Hz, 2H), 0.95-0.81 (m, 2H), 0.79-0.69 (m, 2H). |
| 367 | 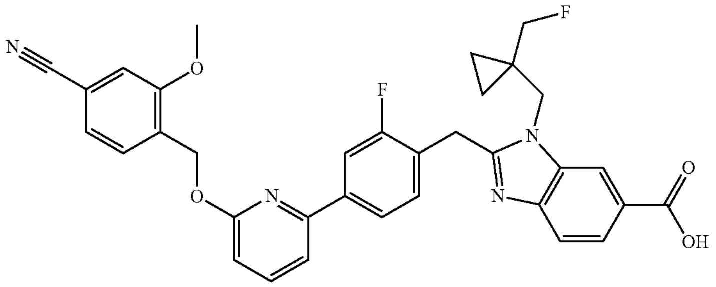 [SMILES: COc1cc(C#N)ccc1COc1cccc(-c2ccc(Cc3nc4ccc(C(=O)O)cc4n3CC3(CF)CC3)c(F)c2)n1]<br>2-(4-(6-((4-cyano-2-methoxybenzyl)oxy)pyridin-2-yl)-2-fluorobenzyl)-1-((1-(fluoromethyl)cyclopropyl)methyl)-1H-benzo[d]imidazole-6-carboxylic acid: ES/MS m/z 595.4; $^{1}$H NMR (400 MHz, DMSO-d6) δ 8.32 (d, J = 1.5 Hz, 1H), 7.94-7.81 (m, 4H), 7.65 (dd, J = 7.9, 5.8 Hz, 2H), 7.60-7.53 (m, 2H), 7.51-7.40 (m, 2H), 6.94 (d, J = 8.2 Hz, 1H), 5.53 (s, 2H), 4.59 (s, 2H), 4.50 (s, 2H), 4.19 (d, J = 48.8 Hz, 2H), 3.93 (s, 3H), 0.90-0.81 (m, 2H), 0.77-0.70 (m, 2H). |
| 399 | 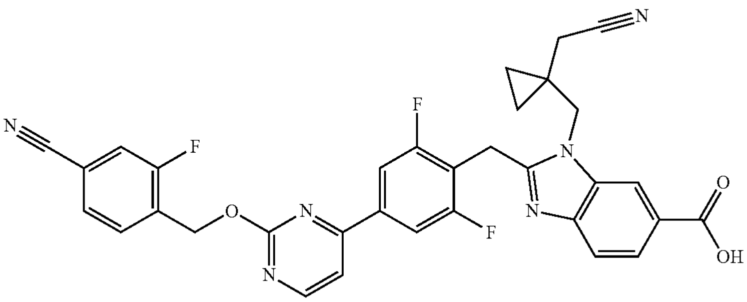 [SMILES: N#CCC1(Cn2c(Cc3c(F)cc(-c4ccnc(OCc5ccc(C#N)cc5F)n4)cc3F)nc3ccc(C(=O)O)cc32)CC1]<br>2-(4-(2-((4-cyano-2-fluorobenzyl)oxy)pyrimidin-4-yl)-2,6-difluorobenzyl)-1-((1-(cyanomethyl)cyclopropyl)methyl)-1H-benzo[d]imidazole-6-carboxylic acid: ES/MS m/z 609.2; $^{1}$H NMR (400 MHz, DMSO-d6) δ 8.80 (d, J = 5.2 Hz, 1H), 8.28 (d, J = 1.4 Hz, 1H), 8.09-7.86 (m, 4H), 7.87-7.71 (m, 3H), 7.56 (d, J = 8.4 Hz, 1H), 5.66 (s, 2H), 4.62 (s, 2H), 4.48 (s, 2H), 2.70 (s, 2H), 0.75 (s, 4H). |

-continued

| Example | Structure/Name/Characterization |
|---|---|
| 409 | 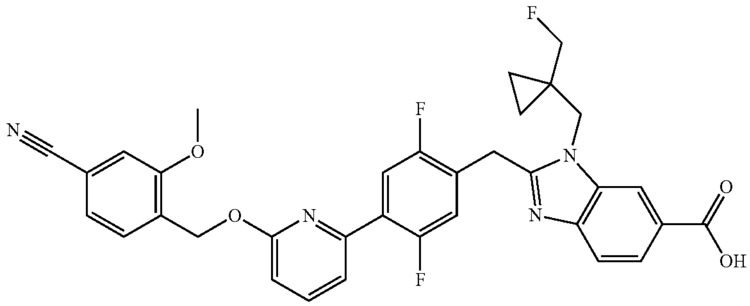 [SMILES: COc1cc(C#N)ccc1COc1cccc(-c2cc(F)c(Cc3nc4ccc(C(=O)O)cc4n3CC3(CF)CC3)cc2F)n1] 2-(4-(6-((4-cyano-2-methoxybenzyl)oxy)pyridin-2-yl)-2,5-difluorobenzyl)-1-((1-(fluoromethyl)cyclopropyl)methyl)-1H-benzo[d]imidazole-6-carboxylic acid: ES/MS m/z 613.2; $^1$H NMR (400 MHz, Methanol-d4) δ 8.62-8.56 (m, 1H), 8.21 (dd, J = 8.6, 1.5 Hz, 1H), 7.89-7.73 (m, 3H), 7.62-7.53 (m, 2H), 7.40-7.30 (m, 3H), 6.96 (d, J = 8.2 Hz, 1H), 5.57 (s, 2H), 4.78-4.71 (m, 4H), 4.24 (d, J = 48.7 Hz, 2H), 3.97 (s, 3H), 1.09-1.00 (m, 2H), 0.94-0.86 (m, 2H). |
| 416 | 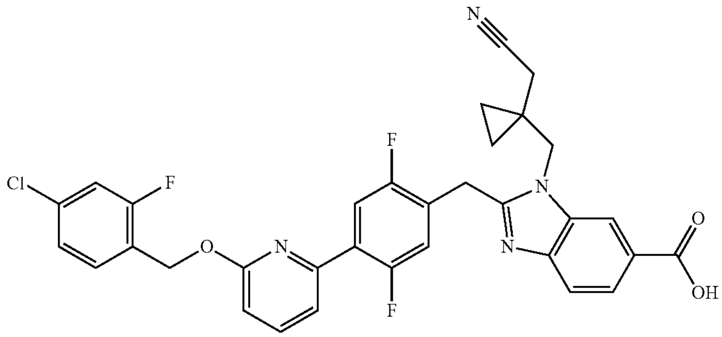 2-(4-(6-((4-chloro-2-fluorobenzyl)oxy)pyridin-2-yl)-2,5-difluorobenzyl)-1-((1-(cyanomethyl)cyclopropyl)methyl)-1H-benzo[d]imidazole-6-carboxylic acid: ES/MS m/z 617.2; $^1$H NMR (400 MHz, DMSO-d6) δ 8.32 (s, 1H), 7.92-7.80 (m, 3H), 7.68-7.58 (m, 2H), 7.57-7.42 (m, 3H), 7.33 (dd, J = 8.2, 2.0 Hz, 1H), 6.95 (d, J = 8.3 Hz, 1H), 5.51 (s, 2H), 4.60 (s, 2H), 4.50 (s, 2H), 2.69 (s, 2H), 0.79-0.65 (m, 4H). |
| 417 | 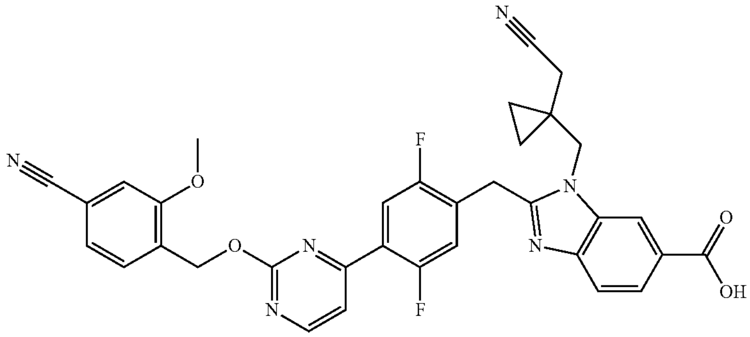 [SMILES: COc1cc(C#N)ccc1COc1nccc(-c2cc(F)c(Cc3nc4ccc(C(=O)O)cc4n3CC3(CC#N)CC3)cc2F)n1] 2-(4-(2-((4-cyano-2-methoxybenzyl)oxy)pyrimidin-4-yl)-2,5-difluorobenzyl)-1-((1-(cyanomethyl)cyclopropyl)methyl)-1H-benzo[d]imidazole-6-carboxylic acid: ES/MS m/z 621.2; $^1$H NMR (400 MHz, DMSO-d6) δ 8.77 (d, J = 5.2 Hz, 1H), 8.29 (d, J = 1.5 Hz, 1H), 7.88 (dd, J = 10.1, 6.3 Hz, 1H), 7.81 (dd, J = 8.4, 1.5 Hz, 1H), 7.65-7.50 (m, 5H), 7.46 (dd, J = 7.7, 1.5 Hz, 1H), 5.54 (s, 2H), 4.57 (s, 2H), 4.49 (s, 2H), 3.92 (s, 3H), 2.68 (s, 2H), 0.76-0.69 (m, 4H). |

-continued

| Example | Structure/Name/Characterization |
|---|---|
| 429 | 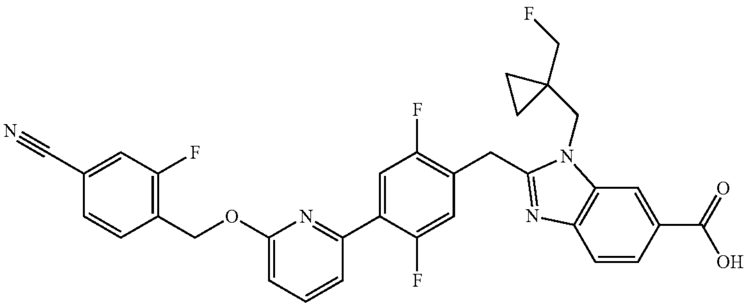 [SMILES: N#Cc1ccc(COc2cccc(-c3cc(F)c(Cc4nc5ccc(C(=O)O)cc5n4CC4(CF)CC4)cc3F)n2)c(F)c1] 2-(4-(6-((4-cyano-2-fluorobenzyl)oxy)pyridin-2-yl)-2,5-difluorobenzyl)-1-((1-(fluoromethyl)cyclopropyl)methyl)-1H-benzo[d]imidazole-6-carboxylic acid: ES/MS m/z 601.2; $^1$H NMR (400 MHz, Methanol-d4) δ 8.56 (s, 1H), 8.19 (dd, J = 8.5, 1.5 Hz, 1H), 7.87-7.71 (m, 4H), 7.67-7.55 (m, 3H), 7.34 (dd, J = 11.2, 6.0 Hz, 1H), 6.96 (d, J = 8.3 Hz, 1H), 5.64 (s, 2H), 4.76-4.68 (m, 4H), 4.24 (d, J = 48.6 Hz, 2H), 1.04-0.95 (m, 2H), 0.95-0.84 (m, 2H). |
| 430 | 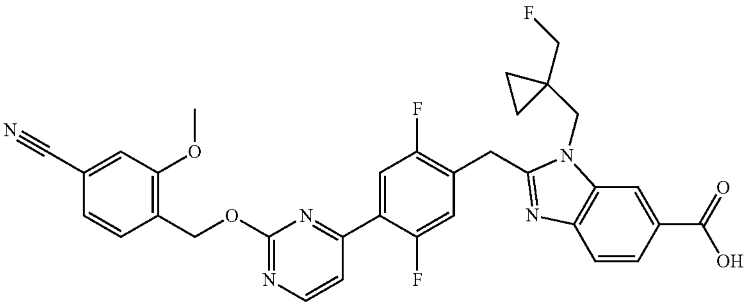 2-(4-(2-((4-cyano-2-methoxybenzyl)oxy)pyrimidin-4-yl)-2,5-difluorobenzyl)-1-((1-(fluoromethyl)cyclopropyl)methyl)-1H-benzo[d]imidazole-6-carboxylic acid: ES/MS m/z 614.2; $^1$H NMR (400 MHz, DMSO-d6) δ 8.77 (d, J = 5.1 Hz, 1H), 8.28 (d, J = 1.4 Hz, 1H), 7.88 (dd, J = 10.2, 6.2 Hz, 1H), 7.82 (dd, J = 8.4, 1.5 Hz, 1H), 7.66-7.55 (m, 4H), 7.51 (dd, J = 11.5, 6.0 Hz, 1H), 7.46 (dd, J = 7.8, 1.4 Hz, 1H), 5.54 (s, 2H), 4.58 (s, 2H), 4.50 (s, 2H), 4.19 (d, J = 48.8 Hz, 2H), 3.92 (s, 3H), 0.89-0.78 (m, 2H), 0.78-0.70 (m, 2H). |
| 431 | 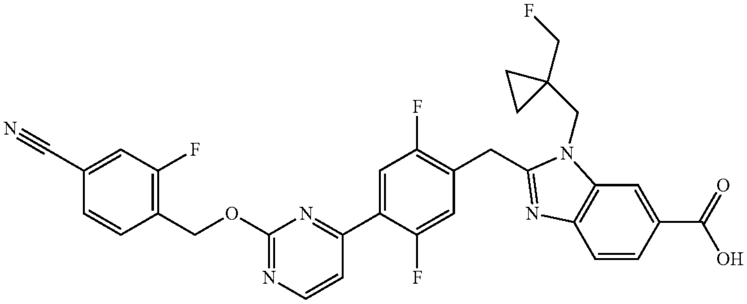 [SMILES: N#Cc1ccc(COc2nccc(-c3cc(F)c(Cc4nc5ccc(C(=O)O)cc5n4CC4(CF)CC4)cc3F)n2)c(F)c1] 2-(4-(2-((4-cyano-2-fluorobenzyl)oxy)pyrimidin-4-yl)-2,5-difluorobenzyl)-1-((1-(fluoromethyl)cyclopropyl)methyl)-1H-benzo[d]imidazole-6-carboxylic acid: ES/MS m/z 602.2; $^1$H NMR (400 MHz, DMSO-d6) δ 8.79 (d, J = 5.2 Hz, 1H), 8.27 (d, J = 1.4 Hz, 1H), 7.99-7.85 (m, 2H), 7.85-7.74 (m, 3H), 7.67-7.58 (m, 2H), 7.51 (dd, J = 11.5, 5.9 Hz, 1H), 5.64 (s, 2H), 4.57 (s, 2H), 4.49 (s, 2H), 4.18 (d, J = 48.8 Hz, 2H), 0.88-0.78 (m, 2H), 0.78-0.67 (m, 2H). |

-continued

| Example | Structure/Name/Characterization |
|---|---|
| 432 | 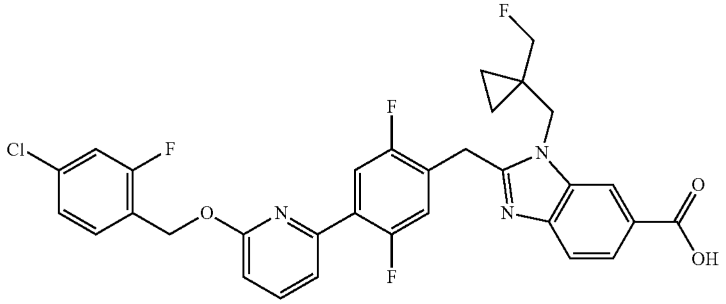 2-(4-(6-((4-chloro-2-fluorobenzyl)oxy)pyridin-2-yl)-2,5-difluorobenzyl)-1-((1-(fluoromethyl)cyclopropyl)methyl)-1H-benzo[d]imidazole-6-carboxylic acid: ES/MS m/z 610.2; $^1$H NMR (400 MHz, Methanol-d4) δ 8.49-8.44 (m, 1H), 8.11 (dd, J = 8.5, 1.6 Hz, 1H), 7.88 (dd, J = 10.7, 6.4 Hz, 1H), 7.81 (t, J = 7.9 Hz, 1H), 7.73 (d, J = 8.6 Hz, 1H), 7.60-7.49 (m, 2H), 7.34-7.18 (m, 3H), 6.90 (d, J = 8.2 Hz, 1H), 5.53 (s, 2H), 4.68-4.62 (m, 4H), 4.21 (d, J = 48.7 Hz, 2H), 1.02-0.93 (m, 2H), 0.89-0.79 (m, 2H). |
| 433 | 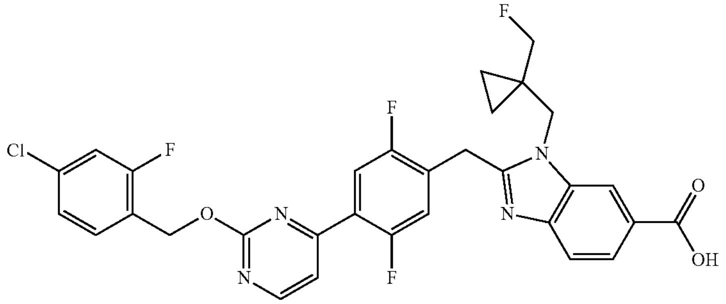 [SMILES: O=C(O)c1ccc2nc(Cc3cc(F)c(-c4cccc(OCc5ccc(Cl)cc5F)n4)cc3F)n(CC3(CF)CC3)c2c1] 2-(4-(2-((4-chloro-2-fluorobenzyl)oxy)pyrimidin-4-yl)-2,5-difluorobenzyl)-1-((1-(fluoromethyl)cyclopropyl)methyl)-1H-benzo[d]imidazole-6-carboxylic acid: ES/MS m/z 611.2; $^1$H NMR (400 MHz, Methanol-d4) δ 8.71 (d, J = 5.2 Hz, 1H), 8.53 (s, 1H), 8.16 (d, J = 8.5 Hz, 1H), 8.04 (dd, J = 10.4, 6.1 Hz, 1H), 7.75 (d, J = 8.6 Hz, 1H), 7.67 (d, J = 5.0 Hz, 1H), 7.60 (t, J = 8.1 Hz, 1H), 7.41 (dd, J = 11.5, 5.8 Hz, 1H), 7.27 (t, J = 9.3 Hz, 2H), 5.61 (s, 2H), 4.76-4.59 (m, 4H), 4.23 (d, J = 48.7 Hz, 2H), 1.09-0.97 (m, 2H), 0.91-0.76 (m, 2H). |
| 441 | 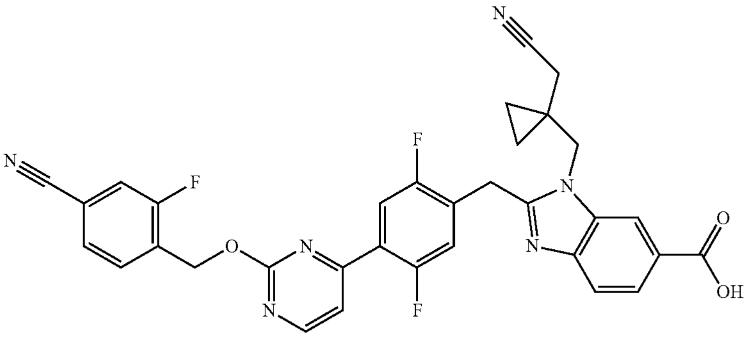 [SMILES: N#CCC1(Cn2c(Cc3cc(F)c(-c4ccnc(OCc5ccc(C#N)cc5F)n4)cc3F)nc3ccc(C(=O)O)cc32)CC1] 2-(4-(2-((4-cyano-2-fluorobenzyl)oxy)pyrimidin-4-yl)-2,5-difluorobenzyl)-1-((1-(cyanomethyl)cyclopropyl)methyl)-1H-benzo[d]imidazole-6-carboxylic acid: ES/MS m/z 609.2; $^1$H NMR (400 MHz, DMSO-d6) δ 8.79 (d, J = 5.2 Hz, 1H), 8.30 (d, J = 1.5 Hz, 1H), 7.98-7.87 (m, 2H), 7.85-7.72 (m, 3H), 7.69-7.58 (m, 2H), 7.54 (dd, J = 11.5, 5.9 Hz, 1H), 5.64 (s, 2H), 4.58 (s, 2H), 4.51 (s, 2H), 2.68 (s, 2H), 0.77-0.69 (m, 4H). |

-continued

| Example | Structure/Name/Characterization |
|---|---|
| 442 | 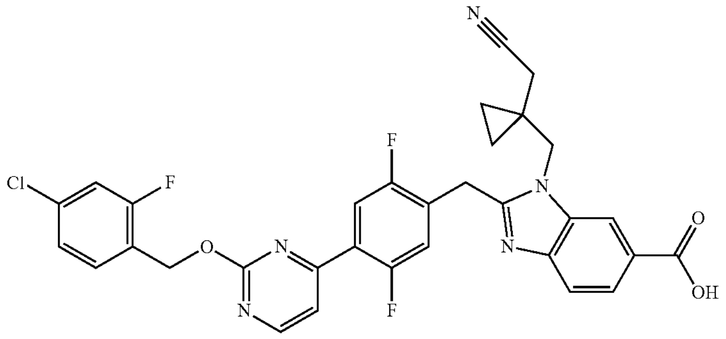 [SMILES: N#CCC1(Cn2c(Cc3cc(F)c(-c4ccnc(OCc5ccc(Cl)cc5F)n4)cc3F)nc3ccc(C(=O)O)cc32)CC1] 2-(4-(2-((4-chloro-2-fluorobenzyl)oxy)pyrimidin-4-yl)-2,5-difluorobenzyl)-1-((1-(cyanomethyl)cyclopropyl)methyl)-1H-benzo[d]imidazole-6-carboxylic acid: ES/MS m/z 618.2; $^1$H NMR (400 MHz, DMSO-d6) δ 8.78 (d, J = 5.2 Hz, 1H), 8.30 (d, J = 1.5 Hz, 1H), 7.94 (dd, J = 10.2, 6.2 Hz, 1H), 7.82 (dd, J = 8.4, 1.5 Hz, 1H), 7.69-7.58 (m, 3H), 7.58-7.48 (m, 2H), 7.36 (dd, J = 8.3, 2.1 Hz, 1H), 5.54 (s, 2H), 4.58 (s, 2H), 4.51 (s, 2H), 2.68 (s, 2H), 0.78 -0.68 (m, 4H). |
| 586 | 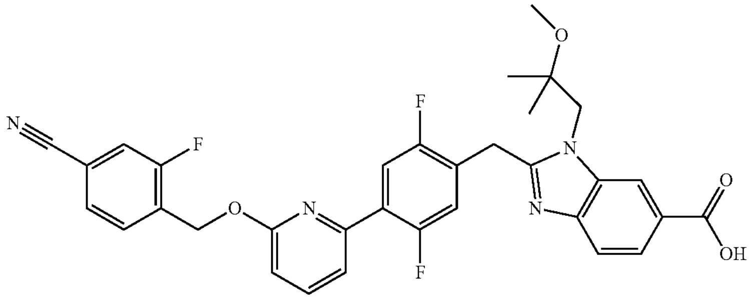 [SMILES: COC(C)(C)Cn1c(Cc2cc(F)c(-c3cccc(OCc4ccc(C#N)cc4F)n3)cc2F)nc2ccc(C(=O)O)cc21] 2-(4-(6-((4-cyano-2-fluorobenzyl)oxy)pyridin-2-yl)-2,5-difluorobenzyl)-1-(2-methoxy-2-methylpropyl)-1H-benzo[d]imidazole-6-carboxylic acid: ES/MS m/z 601.5; $^1$H NMR (400 MHz, Methanol-d4) δ 8.59 (dd, J = 1.5, 0.7 Hz, 1H), 8.19 (dd, J = 8.6, 1.4 Hz, 1H), 7.89-7.69 (m, 4H), 7.64-7.54 (m, 3H), 7.32 (dd, J = 11.2, 6.1 Hz, 1H), 6.96 (dd, J = 8.3, 0.7 Hz, 1H), 5.63 (s, 2H), 4.80 (s, 2H), 4.64 (s, 2H), 3.23 (s, 3H), 1.35 (s, 6H). |
| 605 | 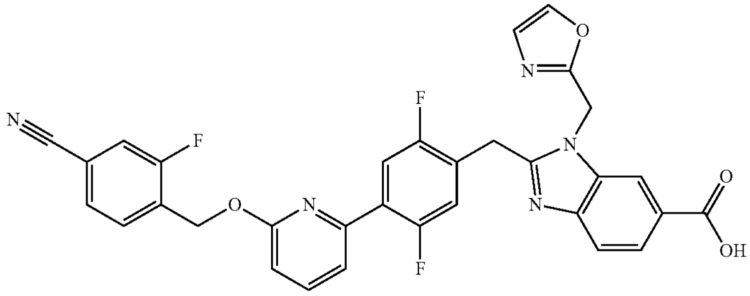 [SMILES: N#Cc1ccc(COc2cccc(-c3cc(F)c(Cc4nc5ccc(C(=O)O)cc5n4Cc4ncco4)cc3F)n2)c(F)c1] 2-(4-(6-((4-cyano-2-fluorobenzyl)oxy)pyridin-2-yl)-2,5-difluorobenzyl)-1-(oxazol-2-ylmethyl)-1H-benzo[d]imidazole-6-carboxylic acid: ES/MS m/z 596.2; $^1$H NMR (400 MHz, DMSO-d6) δ 8.25 (d, J = 1.5 Hz, 1H), 8.08 (s, 1H), 7.98-7.81 (m, 3H), 7.80-7.60 (m, 4H), 7.51 (dd, J = 7.6, 1.7 Hz, 1H), 7.32 (dd, J = 11.5, 6.1 Hz, 1H), 7.15 (s, 1H), 6.99 (d, J = 8.2 Hz, 1H), 5.93 (s, 2H), 5.60 (s, 2H), 4.48 (s, 2H). |

-continued

| Example | Structure/Name/Characterization |
|---|---|
| 748 | 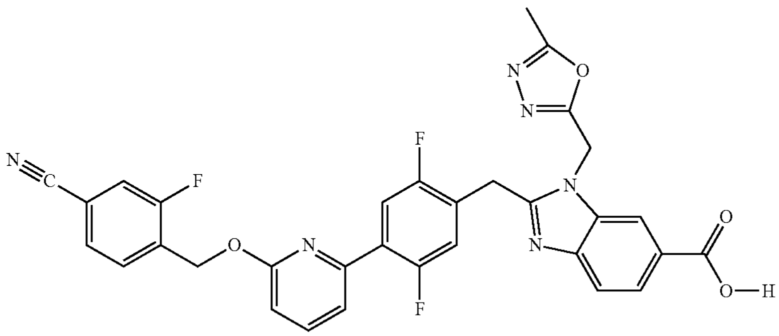 [SMILES: Cc1nnc(Cn2c(Cc3cc(F)c(-c4cccc(OCc5ccc(C#N)cc5F)n4)cc3F)nc3ccc(C(=O)O)cc32)o1]<br>ES/MS MH+ 611.1; 1H NMR (400 MHz, DMSO-d6) δ 8.36 (d, J = 1.8 Hz, 1H), 8.08-7.81 (m, 5H), 7.75 (d, J = 6.3 Hz, 2H), 7.65 (s, 1H), 7.49 (d, J = 7.5 Hz, 1H), 6.98 (d, J = 8.2 Hz, 1H), 5.59 (s, 2H), 2.90 (s, 2H), 2.74 (s, 2H), 2.72 (s, 3H). Multiplet Report 19F NMR (376 MHz, DMSO-d6) δ −74.51, −75.70, −115.88 (dd, J = 9.9, 6.0 Hz), −122.34 (d, J = 62.7 Hz). |
| 749 | 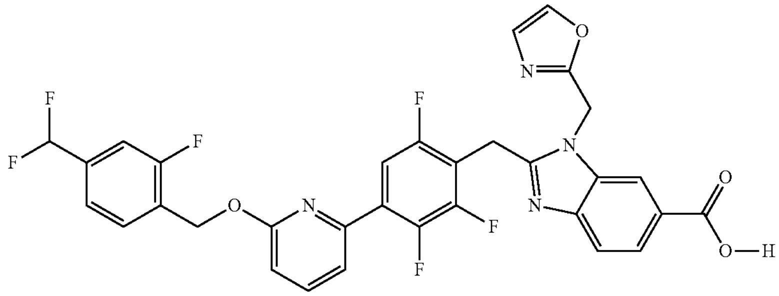 [SMILES: O=C(O)c1ccc2nc(Cc3c(F)cc(-c4cccc(OCc5ccc(C(F)F)cc5F)n4)c(F)c3F)n(Cc3ncco3)c2c1]<br>ES/MS MH+ 639.0; 1H NMR (400 MHz, DMSO) δ 8.27 (d, J = 1.5 Hz, 1H), 8.14 (s, 1H), 7.93 (t, J = 7.9 Hz, 1H), 7.81 (dd, J = 8.4, 1.6 Hz, 1H), 7.73 (t, J = 7.6 Hz, 1H), 7.67 (ddd, J = 10.3, 5.7, 2.0 Hz, 1H), 7.62 (d, J = 8.4 Hz, 1H), 7.56 (dd, J = 7.4, 1.7 Hz, 1H), 7.48 (dd, J = 15.7, 9.1 Hz, 2H), 7.22 (s, 1H), 7.06 (t, J = 55.6 Hz, 1H), 7.02 (d, J = 8.3 Hz, 1H), 5.98 (s, 2H), 5.58 (s, 2H), 4.55 (s, 2H). Multiplet Report 19F NMR (376 MHz, DMSO) δ −75.33, −110.78 (d, J = 55.7 Hz), −117.16 (dd, J = 10.2, 7.5 Hz), −118.20-−125.45 (m), −137.51 (d, J = 21.4 Hz), −146.76. |
| 750 | 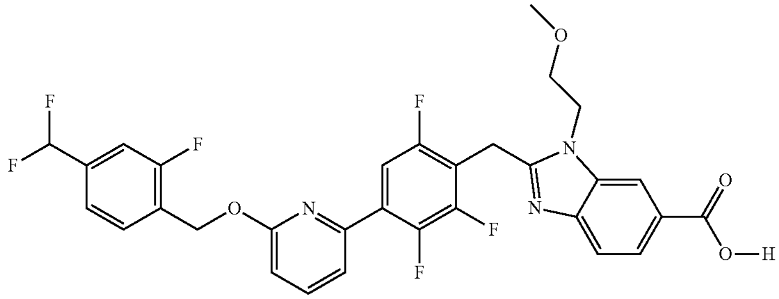 [SMILES: COCCn1c(Cc2c(F)cc(-c3cccc(OCc4ccc(C(F)F)cc4F)n3)c(F)c2F)nc2ccc(C(=O)O)cc21]<br>ES/MS MH+ 616.2; 1H NMR (400 MHz, DMSO) δ 8.25 (d, J = 1.5 Hz, 1H), 8.00-7.89 (m, 1H), 7.81 (dd, J = 8.4, 1.5 Hz, 1H), 7.77-7.64 (m, 2H), 7.62-7.52 (m, 2H), 7.53-7.40 (m, 2H), 7.06 (t, J = 55.6 Hz, 1H), 7.03 (d, J = 8.3 Hz, 1H), 5.58 (s, 2H), 4.67 (t, J = 5 .0 Hz, 2H), 4.55 (s, 2H), 3.73 (t, J = 5.0 Hz, 2H), 3.24 (s, 3H). Multiplet Report 19F NMR (376 MHz, DMSO) δ −75.27, −110.79 (d, J = 55.7 Hz), −117.17 (dd, J = 10.3, 7.4 Hz), −119.48 (t, J = 12.8 Hz), −137.49 (d, J = 21.5 Hz), −146.79. |

-continued

| Example | Structure/Name/Characterization |
|---|---|
| 751 | 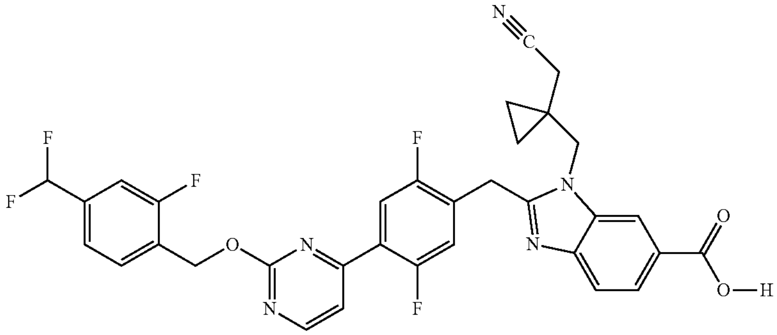 [SMILES: N#CCC1(Cn2c(Cc3cc(F)c(-c4ccnc(OCc5ccc(C(F)F)cc5F)n4)cc3F)nc3ccc(C(=O)O)cc32)CC1] ES/MS MH+ 634.2; 1H NMR (400 MHz, DMSO) δ 8.79 (d, J = 5.1 Hz, 1H), 8.32 (d, J = 1.5 Hz, 1H), 7.93 (dd, J = 10.2, 6.2 Hz, 1H), 7.83 (dd, J = 8.5, 1.5 Hz, 1H), 7.75 (t, J = 7.6 Hz, 1H), 7.70-7.58 (m, 2H), 7.58-7.37 (m, 3H), 7.07 (t, J = 55.6 Hz, 1H), 5.61 (s, 2H), 4.59 (s, 2H), 4.52 (s, 2H), 2.69 (s, 2H), 0.83-0.65 (m, 4H). Multiplet Report 19F NMR (376 MHz, DMSO) δ −75.24, −110.86 (d, J = 55.7 Hz), −117.06 (dd, J = 10.3, 7.4 Hz), −117.45-−121.41 (m), −121.54 (ddd, J = 17.2, 10.2, 6.1 Hz). |
| 752 | 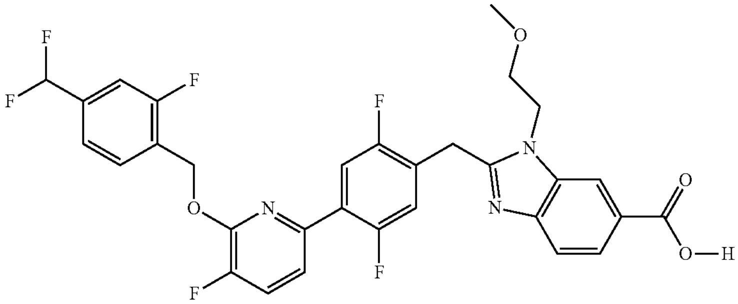 [SMILES: COCCn1c(Cc2cc(F)c(-c3ccc(F)c(OCc4ccc(C(F)F)cc4F)n3)cc2F)nc2ccc(C(=O)O)cc21] ES/MS m/z 616.2; 1H NMR (400 MHz, DMSO) δ 8.26 (d, J = 1.5 Hz, 1H), 7.92-7.81 (m, 2H), 7.81-7.70 (m, 2H), 7.63 (d, J = 8.4 Hz, 1H), 7.58-7.45 (m, 3H), 7.40 (dd, J = 11.5, 6.1 Hz, 1H), 7.06 (t, J = 55.6 Hz, 1H), 5.66 (s, 2H), 4.63 (t, J = 5.1 Hz, 2H), 4.49 (s, 2H), 3.69 (t, J = 5.0 Hz, 2H), 3.20 (s, 3H). |
| 753 | 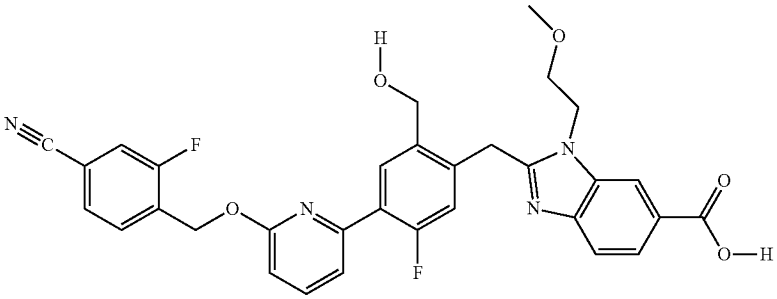 [SMILES: COCCn1c(Cc2cc(F)c(-c3cccc(OCc4ccc(C#N)cc4F)n3)cc2CO)nc2ccc(C(=O)O)cc21] ES/MS m/z 585.2; 1H NMR (400 MHz, DMSO-d6) δ 8.20 (d, J = 1.5 Hz, 1H), 7.97 (d, J = 8.3 Hz, 1H), 7.95-7.84 (m, 2H), 7.79 (ddd, J = 7.4, 4.1, 2.6 Hz, 2H), 7.73 (dd, J = 7.9, 1.5 Hz, 1H), 7.59 (d, J = 8.4 Hz, 1H), 7.45 (dd, J = 7.5, 1.8 Hz, 1H), 7.09 (d, J = 12.3 Hz, 1H), 6.95 (d, J = 8.2 Hz, 1H), 5.59 (s, 2H), 5.35 (s, 1H), 4.57 (d, J = 3.8 Hz, 4H), 4.45 (s, 2H), 3.66 (t, J = 5.1 Hz, 2H), 3.22 (s, 3H). |

Example 415. (S)-2-(4-(2-((4-cyano-2-fluorobenzyl)oxy)pyrimidin-4-yl)-2,5-difluorobenzyl)-1-(oxetan-2-ylmethyl)-1H-benzo[d]imidazole-6-carboxylic acid Procedure 52

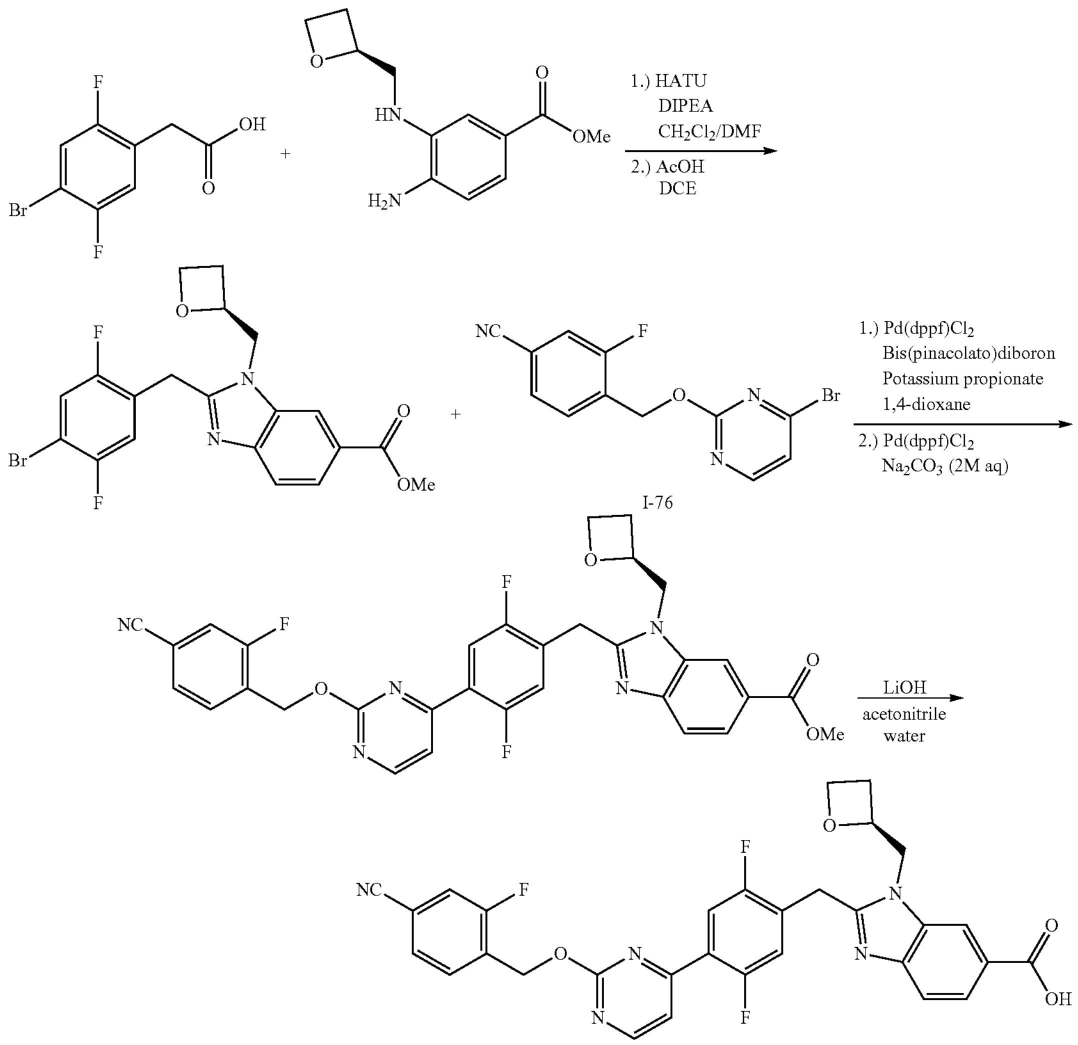

Example 415

Methyl (S)-2-(4-bromo-2,5-difluorobenzyl)-1-(oxetan-2-ylmethyl)-1H-benzo[d]imidazole-6-carboxylate: To a solution of 2-(4-bromo-2,5-difluorophenyl)acetic acid (237 mg, 0.94 mmol), methyl (S)-4-amino-3-((oxetan-2-ylmethyl)amino)benzoate (200 mg, 0.79 mmol), and O-(7-azabenzotriazol-1-yl)-N,N,N',N'-tetramethyluronium hexafluorophosphate (HATU) (241 mg, 0.63 mmol) in DCM (8 mL) and DMF (2 mL) was added DIPEA (0.69 mL, 3.9 mmol). The mixture was stirred at RT for 16 hours, then diluted with EtOAc (50 mL). The mixture was washed with sat. aq. $NH_4Cl$ (2×10 mL) and sat. aq. $NaHCO_3$ (1×10 mL). The organic layer was dried over $MgSO_4$, filtered and concentrated under reduced pressure. The crude residue was dissolved in 1,2-dichloroethane (4 mL) and AcOH (2 mL). The mixture was stirred at 70° C. for 16 hours. The mixture was concentrated in vacuo and purified by silica gel column chromatography (eluent: EtOAc/Hex) to provide the desired product. ES/MS: 469.6 (M+).

Methyl (S)-2-(4-(2-((4-cyano-2-fluorobenzyl)oxy)pyrimidin-4-yl)-2,5-difluorobenzyl)-1-(oxetan-2-ylmethyl)-1H-benzo[d]imidazole-6-carboxylate: A solution of methyl (S)-2-(4-bromo-2,5-difluorobenzyl)-1-(oxetan-2-ylmethyl)-1H-benzo[d]imidazole-6-carboxylate (150 mg, 0.33 mmol), bis(pinacolato)diboron (110 mg, 0.43 mmol), potassium propionate (112 mg, 1.0 mmol), and [1,1'-Bis(diphenylphosphino)ferrocene]dichloropalladium(II) (37 mg, 0.05 mmol) in 1,4-dioxane (1.0 mL) was degassed by bubbling argon for 30 seconds, then heated in a sealed tube at 110° C. for 45 minutes. The mixture was cooled, then 2 M aqueous sodium carbonate (330 μL, 0.67 mmol), [1,1'-bis(diphenylphosphino)ferrocene]dichloropalladium(II) (18 mg, 0.025 mmol), and 4-(((4-bromopyrimidin-2-yl)oxy)methyl)-3-fluorobenzonitrile (I-76) (109 mg, 0.35 mmol) were added.

The vial was sealed, then heated in a sealed tube at 90° C. for 1 hour. The mixture was cooled, and directly added to a silica loading column. The crude material was purified by silica gel column chromatography (eluent: EtOAc/Hex) to provide the desired product. ES/MS: 600.2 ($M+H^+$).

(S)-2-(4-(2-((4-cyano-2-fluorobenzyl)oxy)pyrimidin-4-yl)-2,5-difluorobenzyl)-1-(oxetan-2-ylmethyl)-1H-benzo[d]imidazole-6-carboxylic acid (Example 415): To a solution of methyl (S)-2-(4-(2-((4-cyano-2-fluorobenzyl)oxy)pyrimidin-4-yl)-2,5-difluorobenzyl)-1-(oxetan-2-ylmethyl)-1H-benzo[d]imidazole-6-carboxylate (137 mg, 0.230 mmol) in acetonitrile (1.50 mL) was added lithium hydroxide monohydrate (14.4 mg, 0.34 mmol) dissolved in water (1 mL). The mixture was heated in a sealed tube at 100° C. for 3 minutes. The cooled mixture was purified by RP-HPLC (eluent: water/MeCN*0.1% TFA) to provide the product Example 415 as a trifluoroacetate salt. ES/MS: 586.3 ($M+H^+$); $^1$H NMR (400 MHz, DMSO-d6) δ 8.79 (d, J=5.1 Hz, 1H), 8.32 (d, J=1.4 Hz, 1H), 7.98-7.89 (m, 2H), 7.87-7.73 (m, 3H), 7.68-7.60 (m, 2H), 7.51 (dd, J=11.5, 5.9 Hz, 1H), 5.63 (s, 2H), 5.09 (qd, J=7.1, 2.7 Hz, 1H), 4.81 (dd, J=15.5, 7.2 Hz, 1H), 4.73-4.44 (m, 4H), 4.37 (dt, J=9.0, 5.9 Hz, 1H), 2.81-2.64 (m, 1H), 2.40 (ddt, J=11.3, 9.0, 6.9 Hz, 1H).

Example 101, 106, 109-111, 119-121, 124-128, 130-132, 154, 164-169, 286, 304, 314, 349, 368, 408, 412, 413, 420, 427, 428, 440, 443-445, 448-451, 501, 541, 600, 754-801. Compounds Prepared Using Procedure 52

Other compounds of the present disclosure prepared using the general route described in Procedure 52 include the following Examples.

| Example | Structure/Name/Characterization |
| --- | --- |
| 101 | 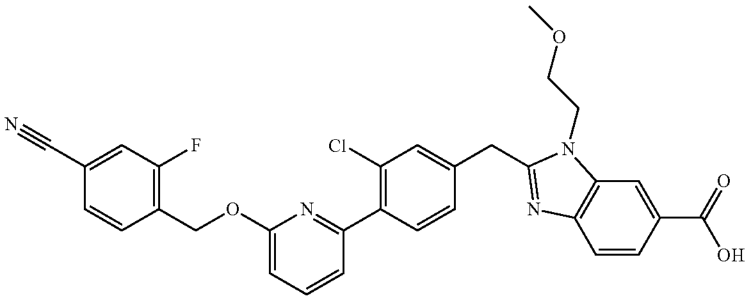 [SMILES: COCCn1c(Cc2ccc(-c3cccc(OCc4ccc(C#N)cc4F)n3)c(Cl)c2)nc2ccc(C(=O)O)cc21] 2-(3-chloro-4-(6-((4-cyano-2-fluorobenzyl)oxy)pyridin-2-yl)benzyl)-1-(2-methoxyethyl)-1H-benzo[d]imidazole-6-carboxylic acid: ES/MS 571.2; $^1$H NMR (400 MHz, DMSO) δ 12.96 (s, 1H), 8.30 (d, J = 1.5 Hz, 1H), 7.97-7.82 (m, 3H), 7.77-7.67 (m, 3H), 7.62-7.50 (m, 2H), 7.43 (dd, J = 8.0, 1.7 Hz, 1H), 7.32 (d, J = 7.3 Hz, 1H), 6.98 (d, J = 8.3 Hz, 1H), 5.51 (s, 2H), 4.64 (t, J = 5.1 Hz, 2H), 4.52 (s, 2H), 3.65 (t, J = 5.1 Hz, 2H), 3.20 (s, 3H). |
| 106 | 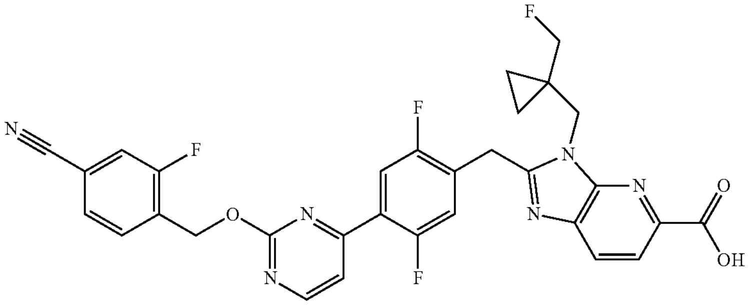 [SMILES: N#Cc1ccc(COc2nccc(-c3cc(F)c(Cc4nc5ccc(C(=O)O)nc5n4CC4(CF)CC4)cc3F)n2)c(F)c1] 2-(4-(2-((4-cyano-2-fluorobenzyl)oxy)pyrimidin-4-yl)-2,5-difluorobenzyl)-3-((1-(fluoromethyl)cyclopropyl)methyl)-3H-imidazo[4,5-b]pyridine-5-carboxylic acid: ES/MS m/z 603.2; $^1$H NMR (400 MHz, MeOD) δ 8.70 (d, J = 5.2 Hz, 1H), 8.16 (d, J = 8.3 Hz, 1H), 8.07 (d, J = 8.2 Hz, 1H), 7.98 (dd, J = 10.4, 6.2 Hz, 1H), 7.80 (t, J = 7.5 Hz, 1H), 7.73-7.57 (m, 3H), 7.36 (dd, J = 11.4, 5.9 Hz, 1H), 5.70 (s, 2H), 4.65 (s, 2H), 4.62 (s, 2H), 4.36 (s, 1H), 4.24 (s, 1H), 1.18 (d, J = 5.1 Hz, 2H), 0.77-0.68 (m, 2H). |

-continued

| Example | Structure/Name/Characterization |
|---|---|
| 109 | 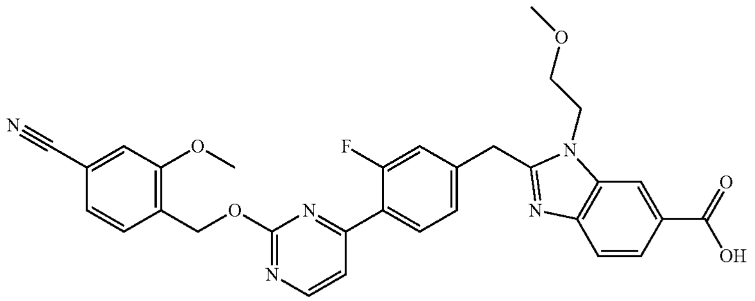 [SMILES: COCCn1c(Cc2ccc(-c3ccnc(OCc4ccc(C#N)cc4OC)n3)c(F)c2)nc2ccc(C(=O)O)cc21] 2-(4-(2-((4-cyano-2-methoxybenzyl)oxy)pyrimidin-4-yl)-3-fluorobenzyl)-1-(2-methoxyethyl)-1H-benzo[d]imidazole-6-carboxylic acid: ES/MS m/z 568.2; $^{1}$H NMR (400 MHz, MeOD) δ 8.67 (d, J = 5.3 Hz, 1H), 8.43 (s, 1H), 8.15 (q, J = 8.3 Hz, 1H), 7.75 (d, J = 8.6 Hz, OH), 7.63 (dd, J = 10.8, 6.5 Hz, 1H), 7.35 (dd, J = 21.7, 12.6 Hz, 2H), 5.62 (s, 1H), 4.90 (s, 2H), 4.67 (s, 2H), 3.96 (s, 1H), 3.76 (t, J = 5.0 Hz, 1H), 3.31-3.27 (m, 3H). |
| 110 | 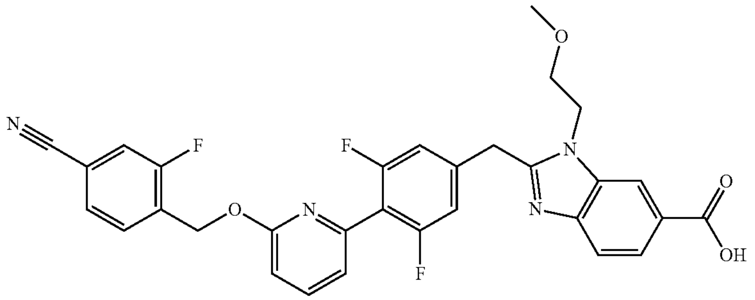 [SMILES: COCCn1c(Cc2cc(F)c(-c3cccc(OCc4ccc(C#N)cc4F)n3)c(F)c2)nc2ccc(C(=O)O)cc21] 2-(4-(6-((4-cyano-2-fluorobenzyl)oxy)pyridin-2-yl)-3,5-difluorobenzyl)-1-(2-methoxyethyl)-1H-benzo[d]imidazole-6-carboxylic acid: ES/MS m/z 573.2; $^{1}$H NMR (400 MHz, MeOD) δ 8.46 (s, 1H), 8.15 (d, J = 7.6 Hz, 1H), 7.84 (dd, J = 8.4, 7.3 Hz, 1H), 7.77 (d, J = 8.6 Hz, 1H), 7.71 (t, J = 7.6 Hz, 1H), 7.57 (dd, J = 8.8, 3.8 Hz, 2H), 7.18 (d, J = 7.3 Hz, 1H), 7.13 (d, J = 8.1 Hz, 2H), 6.96 (d, J = 8.3 Hz, 1H), 5.53 (s, 2H), 4.71 (t, J = 5.0 Hz, 2H), 4.66 (s, 2H), 3.79 (t, J = 5.0 Hz, 2H), 3.31 (s, 3H). |
| 111 | 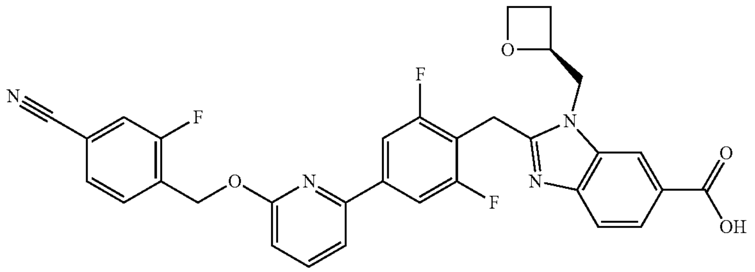 [SMILES: N#Cc1ccc(COc2cccc(-c3cc(F)c(Cc4nc5ccc(C(=O)O)cc5n4C[C@@H]4CCO4)c(F)c3)n2)c(F)c1] (S)-2-(4-(6-((4-cyano-2-fluorobenzyl)oxy)pyridin-2-yl)-2,6-difluorobenzyl)-1-(oxetan-2-ylmethyl)-1H-benzo[d]imidazole-6-carboxylic acid: ES/MS m/z 585.5; $^{1}$H NMR (400 MHz, MeOD) δ 8.26 (d, J = 1.5 Hz, 1H), 7.95 (dd, J = 8.4, 1.5 Hz, 1H), 7.83 (t, J = 7.9 Hz, 1H), 7.77-7.69 (m, 3H), 7.62 (dd, J = 9.7, 1.5 Hz, 1H), 7.58 (d, J = 8.1 Hz, 3H), 6.92 (d, J = 8.2 Hz, 1H), 5.66 (s, 2H), 5.26 (td, J = 7.4, 4.8 Hz, 1H), 4.79 (d, J = 6.6 Hz, 0H), 4.75 (d, J = 6.6 Hz, 1H), 4.70-4.56 (m, 3H), 4.53 (s, 1H), 4.46 (dt, J = 9.2, 6.3 Hz, 1H), 2.82 (dq, J = 11.4, 7.6 Hz, 1H), 2.52 (dq, J = 11.5, 7.4 Hz, 1H). |

-continued

| Example | Structure/Name/Characterization |
|---|---|
| 119 | 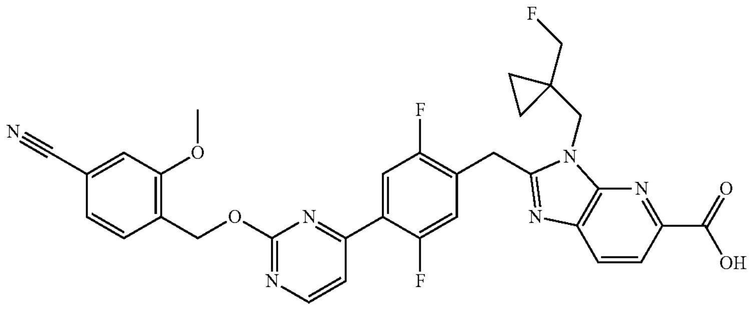 [SMILES: COc1cc(C#N)ccc1COc1nccc(-c2cc(F)c(Cc3nc4ccc(C(=O)O)nc4n3CC3(CF)CC3)cc2F)n1]<br>2-(4-(2-((4-cyano-2-methoxybenzyl)oxy)pyrimidin-4-yl)-2,5-difluorobenzyl)-3-((1-(fluoromethyl)cyclopropyl)methyl)-3H-imidazo[4,5-b]pyridine-5-carboxylic acid: ES/MS m/z 615.2; $^1$H NMR (400 MHz, MeOD) δ 8.70 (d, J = 5.3 Hz, 1H), 8.16 (d, J = 8.3 Hz, 1H), 8.07 (d, J = 8.3 Hz, 1H), 7.95 (dd, J = 10.4, 6.1 Hz, 1H), 7.68-7.59 (m, 2H), 7.40 (d, J = 1.4 Hz, 1H), 7.36 (q, J = 5.5, 5.1 Hz, 2H), 5.64 (s, 2H), 4.65 (s, 2H), 4.62 (s, 2H), 4.36 (s, 1H), 4.24 (s, 1H), 1.18 (d, J = 5.2 Hz, 2H), 0.74 (s, 2H). |
| 120 | 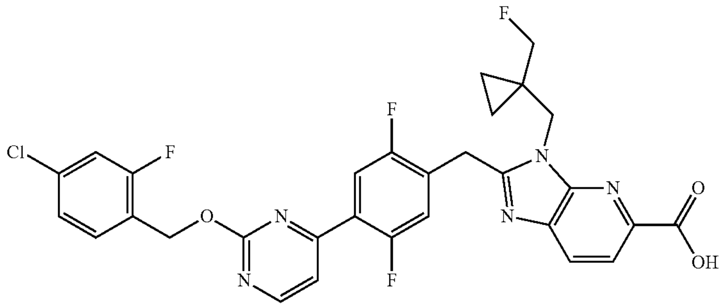 [SMILES: O=C(O)c1ccc2nc(Cc3cc(F)c(-c4ccnc(OCc5ccc(Cl)cc5F)n4)cc3F)n(CC3(CF)CC3)c2n1]<br>2-(4-(2-((4-chloro-2-fluorobenzyl)oxy)pyrimidin-4-yl)-2,5-difluorobenzyl)-3-((1-(fluoromethyl)cyclopropyl)methyl)-3H-imidazo[4,5-b]pyridine-5-carboxylic acid: ES/MS m/z 612.2; $^1$H NMR (400 MHz, MeOD) δ 8.69 (d, J = 5.3 Hz, 1H), 8.17 (d, J = 8.3 Hz, 1H), 8.08 (d, J = 8.3 Hz, 1H), 8.01 (dd, J = 10.3, 6.2 Hz, 1H), 7.66 (dd, J = 5.3, 1.7 Hz, 1H), 7.61 (t, J = 8.1 Hz, 1H), 7.37 (dd, J = 11.4, 5.9 Hz, 1H), 7.33-7.22 (m, 2H), 5.61 (s, 2H), 4.66 (s, 2H), 4.64 (s, 2H), 4.37 (s, 1H), 4.24 (s, 1H), 1.19 (t, J = 5.3 Hz, 2H), 0.75 (d, J = 5.7 Hz, 2H). |
| 121 | 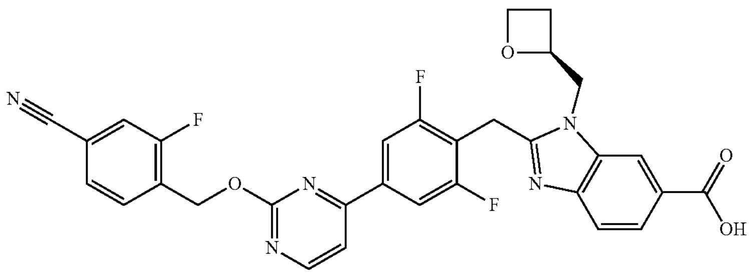<br>(S)-2-(4-(2-((4-cyano-2-fluorobenzyl)oxy)pyrimidin-4-yl)-2,6-difluorobenzyl)-1-(oxetan-2-ylmethyl)-1H-benzo[d]imidazole-6-carboxylic acid: ES/MS m/z 586.2; $^1$H NMR (400 MHz, MeOD) δ 8.71 (d, J = 5.1 Hz, 1H), 8.48 (d, J = 1.5 Hz, 1H), 8.10 (d, J = 1.4 Hz, 1H), 7.92 (s, 1H), 7.80 (t, J = 7.5 Hz, 1H), 7.75-7.58 (m, 4H), 5.71 (s, 2H), 5.29 (qd, J = 7.2, 2.4 Hz, 1H), 4.93 (d, J = 7.2 Hz, 1H), 4.86-4.75 (m, 2H), 4.76-4.63 (m, 1H), 4.52 (dt, J = 9.2, 6.0 Hz, 1H), 2.87 (dtd, J = 11.5, 8.2, 6.1 Hz, 1H), 2.65-2.45 (m, 1H). |

-continued

| Example | Structure/Name/Characterization |
|---|---|
| 124 | 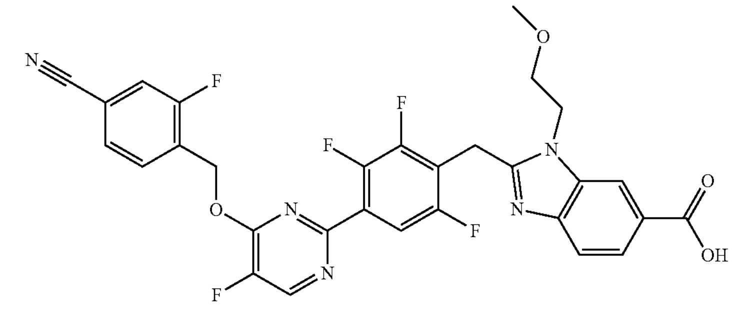 [SMILES: COCCn1c(Cc2c(F)cc(-c3ncc(F)c(OCc4ccc(C#N)cc4F)n3)c(F)c2F)nc2ccc(C(=O)O)cc21] 2-(4-(4-((4-cyano-2-fluorobenzyl)oxy)-5-fluoropyrimidin-2-yl)-2,3,6-trifluorobenzyl)-1-(2-methoxyethyl)-1H-benzo[d]imidazole-6-carboxylic acid: ES/MS m/z 610.2; $^{1}$H NMR (400 MHz, DMSO) δ 8.89 (d, J = 2.8 Hz, 1H), 8.21 (d, J = 1.6 Hz, 1H), 8.00-7.93 (m, 1H), 7.86-7.74 (m, 4H), 7.57 (d, J = 8.5 Hz, 1H), 5.77 (s, 2H), 4.68-4.62 (m, 2H), 4.54 (s, 2H), 3.72 (t, J = 5.0 Hz, 2H), 3.24 (s, 3H). |
| 125 | 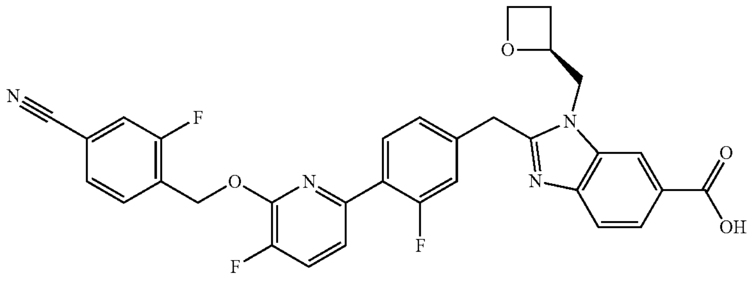 [SMILES: N#Cc1ccc(COc2nc(-c3ccc(Cc4nc5ccc(C(=O)O)cc5n4C[C@@H]4CCO4)cc3F)ccc2F)c(F)c1] (S)-2-(4-(6-((4-cyano-2-fluorobenzyl)oxy)-5-fluoropyridin-2-yl)-3-fluorobenzyl)-1-(oxetan-2-ylmethyl)-1H-benzo[d]imidazole-6-carboxylic acid: ES/MS m/z 585.2; $^{1}$H NMR (400 MHz, DMSO) δ 8.32 (s, 1H), 7.96-7.91 (m, 1H), 7.90-7.81 (m, 3H), 7.80-7.72 (m, 2H), 7.67 (d, J = 8.5 Hz, 1H), 7.51-7.44 (m, 1H), 7.38-7.27 (m, 2H), 5.65 (s, 2H), 5.05-4.96 (m, 1H), 4.78 (dd, J = 15.4, 7.3 Hz, 1H), 4.67-4.59 (m, 1H), 4.58-4.45 (m, 3H), 4.42-4.33 (m, 1H), 2.75-2.62 (m, 1H), 2.45-2.29 (m, 1H). |
| 126 | 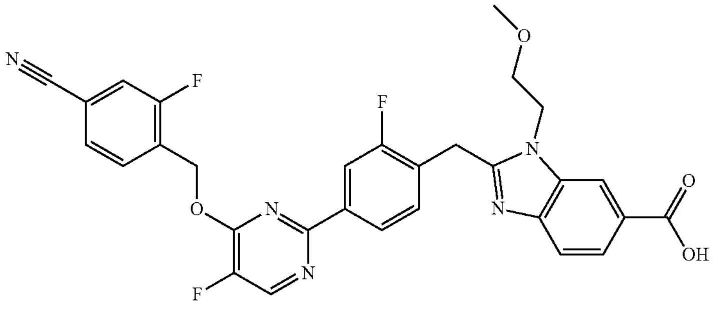 [SMILES: COCCn1c(Cc2ccc(-c3ncc(F)c(OCc4ccc(C#N)cc4F)n3)cc2F)nc2ccc(C(=O)O)cc21] 2-(4-(4-((4-cyano-2-fluorobenzyl)oxy)-5-fluoropyrimidin-2-yl)-2-fluorobenzyl)-1-(2-methoxyethyl)-1H-benzo[d]imidazole-6-carboxylic acid: ES/MS m/z 574.2; $^{1}$H NMR (400 MHz, DMSO) δ 8.78 (d, J = 2.8 Hz, 1H), 8.25 (s, 1H), 8.12 (dd, J = 8.0, 1.6 Hz, 1H), 8.06 (dd, J = 11.1, 1.7 Hz, 1H), 7.96 (dd, J = 9.9, 1.5 Hz, 1H), 7.88-7.80 (m, 2H), 7.77 (dd, J = 7.9, 1.5 Hz, 1H), 7.62 (d, J = 8.5 Hz, 1H), 7.49 (t, J = 7.9 Hz, 1H), 5.81 (s, 2H), 4.61 (t, J = 5.2 Hz, 2H), 4.51 (s, 2H), 3.66 (t, J = 5.1 Hz, 2H), 3.20 (s, 3H). |

-continued

| Example | Structure/Name/Characterization |
|---|---|
| 127 | 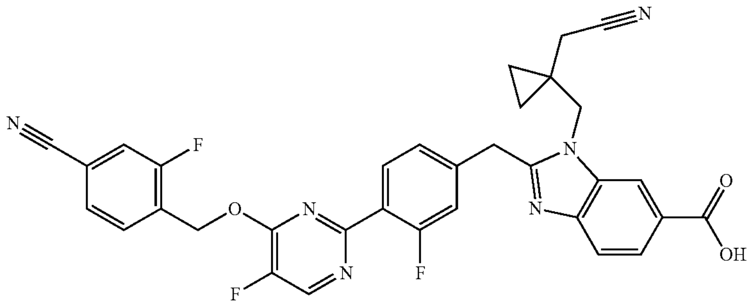 [SMILES: N#CCC1(Cn2c(Cc3ccc(-c4ncc(F)c(OCc5ccc(C#N)cc5F)n4)c(F)c3)nc3ccc(C(=O)O)cc32)CC1]<br>2-(4-(4-((4-cyano-2-fluorobenzyl)oxy)-5-fluoropyrimidin-2-yl)-3-fluorobenzyl)-1-((1-(cyanomethyl)cyclopropyl)methyl)-1H-benzo[d]imidazole-6-carboxylic acid: ES/MS m/z 609.2; $^1$H NMR (400 MHz, DMSO) δ 8.81 (d, J = 2.9 Hz, 1H), 8.35 (d, J = 1.6 Hz, 1H), 8.01 (t, J = 8.1 Hz, 1H), 7.94 (dd, J = 9.9, 1.4 Hz, 1H), 7.89 (dd, J = 8.4, 1.5 Hz, 1H), 7.84-7.74 (m, 2H), 7.69 (d, J = 8.4 Hz, 1H), 7.47-7.36 (m, 1H), 7.33 (dd, J = 8.1, 1.6 Hz, 1H), 5.72 (s, 2H), 4.56 (s, 4H), 2.69 (s, 2H), 0.79-0.60 (m, 4H). |
| 128 | 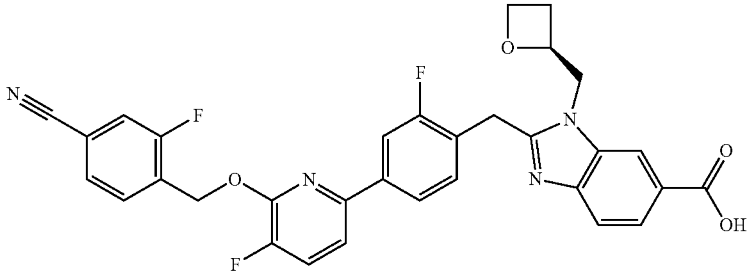 [SMILES: N#Cc1ccc(COc2nc(-c3ccc(Cc4nc5ccc(C(=O)O)cc5n4C[C@@H]4CCO4)c(F)c3)ccc2F)c(F)c1]<br>(S)-2-(4-(6-((4-cyano-2-fluorobenzyl)oxy)-5-fluoropyridin-2-yl)-2-fluorobenzyl)-1-(oxetan-2-ylmethyl)-1H-benzo[d]imidazole-6-carboxylic acid: ES/MS m/z 585.2; $^1$H NMR (400 MHz, DMSO) δ 8.31 (d, J = 1.5 Hz, 1H), 7.94 (dd, J = 10.1, 1.5 Hz, 1H), 7.89-7.66 (m, 7H), 7.62 (d, J = 8.5 Hz, 1H), 7.45 (t, J = 8.0 Hz, 1H), 5.70 (s, 2H), 5.10-5.00 (m, 1H), 4.78 (dd, J = 15.6, 7.2 Hz, 1H), 4.71-4.44 (m, 4H), 4.42-4.32 (m, 1H), 2.77-2.66 (m, 1H), 2.45-2.29 (m, 1H). |
| 130 | 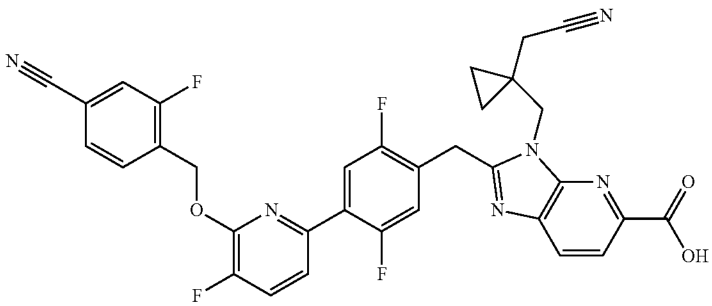 [SMILES: N#CCC1(Cn2c(Cc3cc(F)c(-c4ccc(F)c(OCc5ccc(C#N)cc5F)n4)cc3F)nc3ccc(C(=O)O)nc32)CC1]<br>2-(4-(6-((4-cyano-2-fluorobenzyl)oxy)-5-fluoropyridin-2-yl)-2,5-difluorobenzyl)-3-((1-(cyanomethyl)cyclopropyl)methyl)-3H-imidazo[4,5-b]pyridine-5-carboxylic acid: ES/MS m/z 627.2; $^1$H NMR (400 MHz, DMSO) δ 8.08 (d, J = 8.2 Hz, 1H), 7.97 (d, J = 8.2 Hz, 1H), 7.94 (dd, J = 10.1, 1.4 Hz, 1H), 7.87 (dd, J = 10.3, 8.2 Hz, 1H), 7.82-7.69 (m, 3H), 7.59-7.53 (m, 1H), 7.48 (dd, J = 11.3, 6.3 Hz, 1H), 5.69 (s, 2H), 4.51 (d, J = 4.1 Hz, 4H), 2.78 (s, 2H), 1.09-1.02 (m, 2H), 0.72-0.64 (m, 2H). |

-continued

| Example | Structure/Name/Characterization |
|---|---|
| 131 | 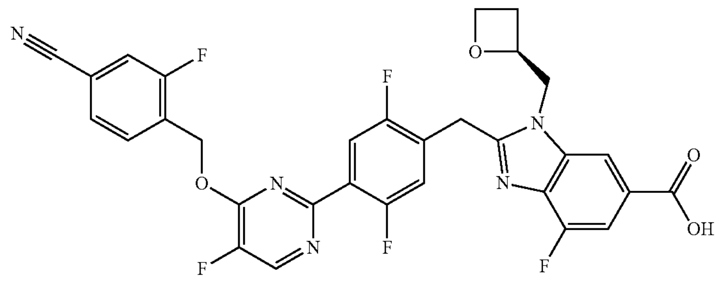 [SMILES: N#Cc1ccc(COc2nc(-c3cc(F)c(Cc4nc5c(F)cc(C(=O)O)cc5n4C[C@@H]4CCO4)cc3F)ncc2F)c(F)c1] (S)-2-(4-(4-((4-cyano-2-fluorobenzyl)oxy)-5-fluoropyrimidin-2-yl)-2,5-difluorobenzyl)-4-fluoro-1-(oxetan-2-ylmethyl)-1H-benzo[d]imidazole-6-carboxylic acid: ES/MS m/z 622.2; $^1$H NMR (400 MHz, DMSO) δ 8.83 (d, J = 2.8 Hz, 1H), 8.05 (s, 1H), 7.95 (dd, J = 9.9, 1.5 Hz, 1H), 7.89-7.73 (m, 3H), 7.48 (dd, J = 11.6, 1.2 Hz, 1H), 7.40 (dd, J = 11.1, 6.0 Hz, 1H), 5.75 (s, 2H), 5.06 (qd, J = 6.9, 2.8 Hz, 1H), 4.74 (dd, J = 15.6, 7.0 Hz, 1H), 4.61 (dd, J = 15.5, 2.8 Hz, 1H), 4.57-4.42 (m, 3H), 4.34 (dt, J = 9.1, 5.9 Hz, 1H), 2.74-2.64 (m, 1H), 2.43-2.35 (m, 1H). |
| 132 | 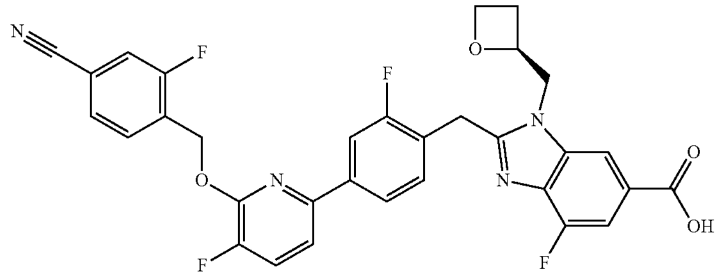 [SMILES: N#Cc1ccc(COc2nc(-c3ccc(Cc4nc5c(F)cc(C(=O)O)cc5n4C[C@@H]4CCO4)c(F)c3)ccc2F)c(F)c1] (S)-2-(4-(6-((4-cyano-2-fluorobenzyl)oxy)-5-fluoropyridin-2-yl)-2-fluorobenzyl)-4-fluoro-1-(oxetan-2-ylmethyl)-1H-benzo[d]imidazole-6-carboxylic acid: ES/MS m/z 603.2; $^1$H NMR (400 MHz, DMSO) δ 8.10 (d, J = 1.3 Hz, 1H), 7.94 (dd, J = 10.0, 1.5 Hz, 1H), 7.89-7.66 (m, 6H), 7.49 (dd, J = 11.5, 1.2 Hz, 1H), 7.43 (t, J = 8.1 Hz, 1H), 5.70 (s, 2H), 5.04 (qd, J = 6.9, 2.7 Hz, 1H), 4.74 (dd, J = 15.6, 7.1 Hz, 1H), 4.60 (dd, J = 15.6, 2.8 Hz, 1H), 4.56-4.39 (m, 3H), 4.35 (dt, J = 9.0, 5.9 Hz, 1H), 2.75-2.64 (m, 1H), 2.43-2.32 (m, 1H). |
| 154 | 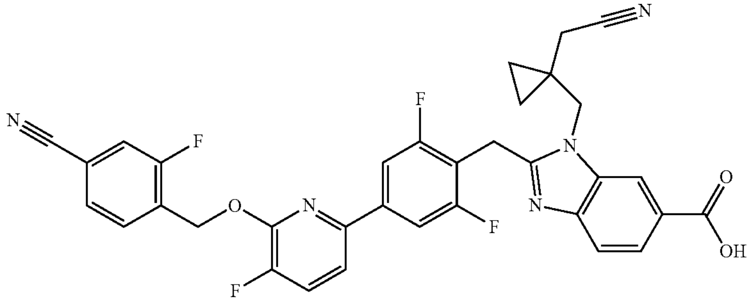 [SMILES: N#CCC1(Cn2c(Cc3c(F)cc(-c4ccc(F)c(OCc5ccc(C#N)cc5F)n4)cc3F)nc3ccc(C(=O)O)cc32)CC1] 2-(4-(6-((4-cyano-2-fluorobenzyl)oxy)-5-fluoropyridin-2-yl)-2,6-difluorobenzyl)-1-((1-(cyanomethyl)cyclopropyl)methyl)-1H-benzo[d]imidazole-6-carboxylic acid: ES/MS m/z 626.2; $^1$H NMR (400 MHz, DMSO) δ 8.30 (d, J = 1.6 Hz, 1H), 7.94 (dd, J = 10.0, 1.5 Hz, 1H), 7.88 (dd, J = 10.1, 8.2 Hz, 1H), 7.84-7.73 (m, 6H), 7.57 (d, J = 8.4 Hz, 1H), 5.73 (s, 2H), 4.63 (s, 2H), 4.46 (s, 2H), 2.70 (s, 2H), 0.80-0.67 (m, 4H). |

-continued

| Example | Structure/Name/Characterization |
|---|---|
| 164 | 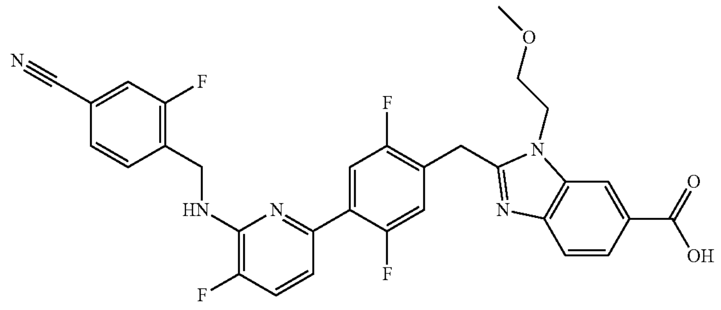 [SMILES: COCCn1c(Cc2cc(F)c(-c3ccc(F)c(NCc4ccc(C#N)cc4F)n3)cc2F)nc2ccc(C(=O)O)cc21] 2-(4-(6-((4-cyano-2-fluorobenzyl)amino)-5-fluoropyridin-2-yl)-2,5-difluorobenzyl)-1-(2-methoxyethyl)-1H-benzo[d]imidazole-6-carboxylic acid: ES/MS m/z 590.2; 1H NMR (400 MHz, DMSO) δ 8.28 (d, J = 1.6 Hz, 1H), 7.90-7.79 (m, 2H), 7.71-7.61 (m, 3H), 7.59-7.46 (m, 2H), 7.39 (dd, J = 10.8, 6.5 Hz, 1H), 7.32 (dd, J = 11.6, 6.1 Hz, 1H), 7.11-7.04 (m, 1H), 4.70 (d, J = 5.3 Hz, 2H), 4.63 (t, J = 5.1 Hz, 2H), 4.47 (s, 2H), 3.67 (t, J = 5.0 Hz, 2H), 3.19 (s, 3H). |
| 165 | 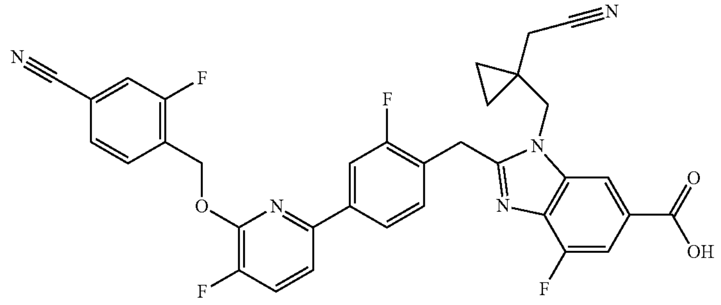 [SMILES: N#CCC1(Cn2c(Cc3ccc(-c4ccc(F)c(OCc5ccc(C#N)cc5F)n4)cc3F)nc3c(F)cc(C(=O)O)cc32)CC1] 2-(4-(6-((4-cyano-2-fluorobenzyl)oxy)-5-fluoropyridin-2-yl)-2-fluorobenzyl)-1-((1-(cyanomethyl)cyclopropyl)methyl)-4-fluoro-1H-benzo[d]imidazole-6-carboxylic acid: ES/MS m/z 626.2; $^{1}$H NMR (400 MHz, DMSO) δ 8.16 (d, J = 1.3 Hz, 1H), 7.93 (dd, J = 10.0, 1.5 Hz, 1H), 7.87-7.74 (m, 5H), 7.70 (dd, J = 8.2, 2.8 Hz, 1H), 7.55-7.43 (m, 2H), 5.71 (s, 2H), 4.57 (s, 2H), 4.46 (s, 2H), 2.66 (s, 2H), 0.77-0.66 (m, 4H). |
| 166 | 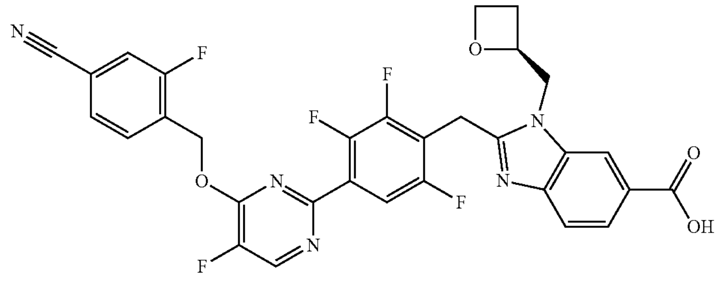 [SMILES: N#Cc1ccc(COc2nc(-c3cc(F)c(Cc4nc5ccc(C(=O)O)cc5n4C[C@@H]4CCO4)c(F)c3F)ncc2F)c(F)c1] (S)-2-(4-(4-((4-cyano-2-fluorobenzyl)oxy)-5-fluoropyrimidin-2-yl)-2,3,6-trifluorobenzyl)-1-(oxetan-2-ylmethyl)-1H-benzo[d]imidazole-6-carboxylic acid: ES/MS m/z 622; $^{1}$H NMR (400 MHz, DMSO) δ 8.88 (d, J = 2.8 Hz, 1H), 8.21 (s, 1H), 7.96 (dd, J = 9.9, 1.5 Hz, 1H), 7.86-7.73 (m, 4H), 7.53 (d, J = 8.4 Hz, 1H), 5.77 (s, 2H), 5.19-5.05 (m, 1H), 4.78 (dd, J = 15.8, 6.7 Hz, 1H), 4.70-4.61 (m, 2H), 4.57-4.46 (m, 2H), 4.34 (dt, J = 9.0, 5.9 Hz, 1H), 2.79-2.69 (m, 1H), 2.43-2.36 (m, 1H). |

-continued

| Example | Structure/Name/Characterization |
|---|---|
| 167 | 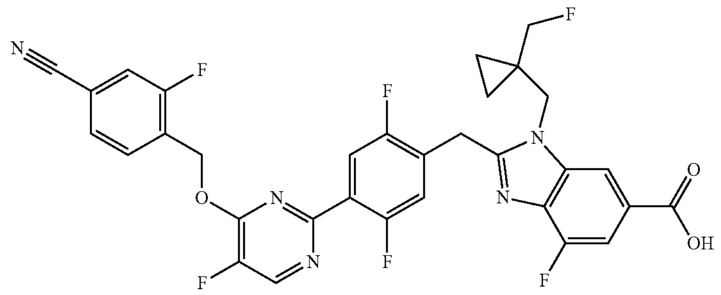 [SMILES: N#Cc1ccc(COc2nc(-c3cc(F)c(Cc4nc5c(F)cc(C(=O)O)cc5n4CC4(CF)CC4)cc3F)ncc2F)c(F)c1] 2-(4-(4-((4-cyano-2-fluorobenzyl)oxy)-5-fluoropyrimidin-2-yl)-2,5-difluorobenzyl)-4-fluoro-1-((1-(fluoromethyl)cyclopropyl)methyl)-1H-benzo[d]imidazole-6-carboxylic acid: ES/MS m/z 638.2; $^{1}$H NMR (400 MHz, DMSO) δ 8.84 (d, J = 2.9 Hz, 1H), 8.13 (d, J = 1.3 Hz, 1H), 7.95 (dd, J = 10.0, 1.5 Hz, 1H), 7.88-7.78 (m, 2H), 7.76 (dd, J = 7.9, 1.5 Hz, 1H), 7.51 (dd, J = 11.3, 1.2 Hz, 1H), 7.43 (dd, J = 11.1, 6.1 Hz, 1H), 5.75 (s, 2H), 4.57 (s, 2H), 4.47 (s, 2H), 4.23 (s, 1H), 4.11 (s, 1H), 0.89-0.80 (m, 2H), 0.74-0.69 (m, 2H). |
| 168 | 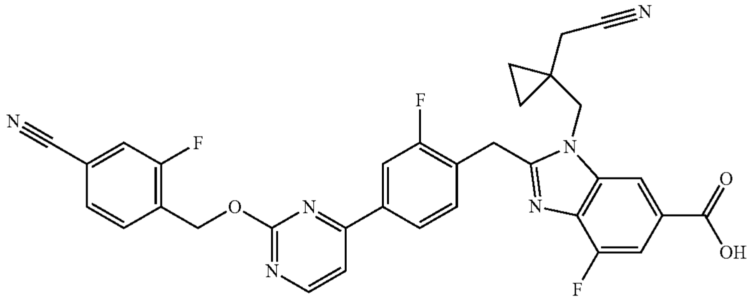 [SMILES: N#CCC1(Cn2c(Cc3ccc(-c4ccnc(OCc5ccc(C#N)cc5F)n4)cc3F)nc3c(F)cc(C(=O)O)cc32)CC1] 2-(4-(2-((4-cyano-2-fluorobenzyl)oxy)pyrimidin-4-yl)-2-fluorobenzyl)-1-((1-(cyanomethyl)cyclopropyl)methyl)-4-fluoro-1H-benzo[d]imidazole-6-carboxylic acid: ES/MS 609.2; $^{1}$H NMR (400 MHz, DMSO) δ 8.74 (d, J = 5.2 Hz, 1H), 8.16 (d, J = 1.3 Hz, 1H), 8.08-8.01 (m, 2H), 7.94 (dd, J = 10.0, 1.5 Hz, 1H), 7.83 (d, J = 5.3 Hz, 1H), 7.81-7.71 (m, 2H), 7.57 (t, J = 7.8 Hz, 1H), 7.51 (dd, J = 11.3, 1.2 Hz, 1H), 5.63 (s, 2H), 4.57 (s, 2H), 4.50 (s, 2H), 2.66 (s, 2H), 0.77-0.66 (m, 4H). |
| 169 | 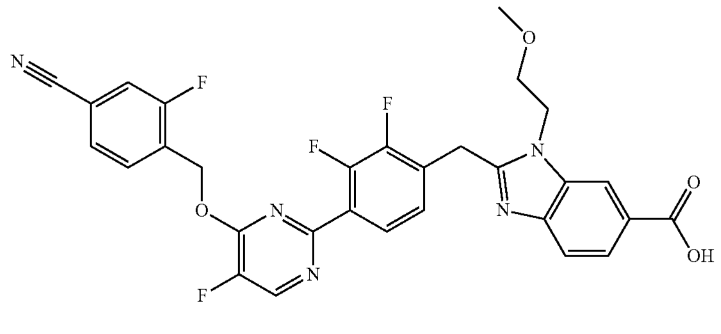 [SMILES: COCCn1c(Cc2ccc(-c3ncc(F)c(OCc4ccc(C#N)cc4F)n3)c(F)c2F)nc2ccc(C(=O)O)cc21] 2-(4-(4-((4-cyano-2-fluorobenzyl)oxy)-5-fluoropyrimidin-2-yl)-2,3-difluorobenzyl)-1-(2-methoxyethyl)-1H-benzo[d]imidazole-6-carboxylic acid: ES/MS m/z 592.2; $^{1}$H NMR (400 MHz, DMSO) δ 8.85 (d, J = 2.8 Hz, 1H), 8.22 (s, 1H), 7.99-7.92 (m, 1H), 7.88-7.73 (m, 4H), 7.60 (d, J = 8.4 Hz, 1H), 7.29 (t, J = 7.6 Hz, 1H), 5.74 (s, 2H), 4.64-4.57 (m, 2H), 4.52 (s, 2H), 3.68 (t, J = 5.1 Hz, 2H), 3.20 (s, 3H). |

-continued

| Example | Structure/Name/Characterization |
|---|---|
| 286 | 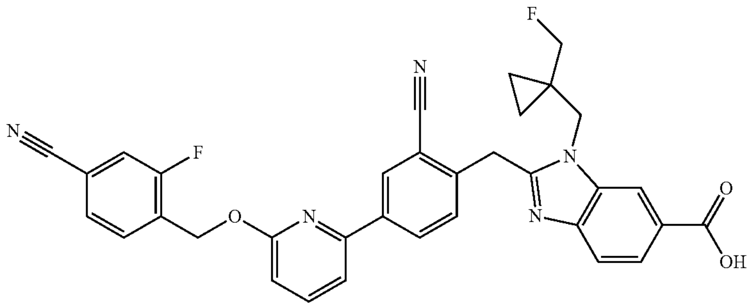 [SMILES: N#Cc1ccc(COc2cccc(-c3ccc(Cc4nc5ccc(C(=O)O)cc5n4CC4(CF)CC4)c(C#N)c3)n2)c(F)c1]<br>2-(2-cyano-4-(6-((4-cyano-2-fluorobenzyl)oxy)pyridin-2-yl)benzyl)-1-((1-(fluoromethyl)cyclopropyl)methyl)-1H-benzo[d]imidazole-6-carboxylic acid: ES/MS m/z 590.3; $^{1}$H NMR (400 MHz, DMSO-d6) δ 9.57 (s, 2H), 8.88 (s, 1H), 8.38-7.61 (m, 8H), 6.96 (s, 1H), 5.72 (s, 2H), 4.59 (s, 2H), 4.27 (d, J = 48.7 Hz, 2H), 1.76 (s, 1H), 1.24 (s, 1H), 0.99 (d, J = 5.3 Hz, 2H), 0.75 (s, 2H). |
| 304 | 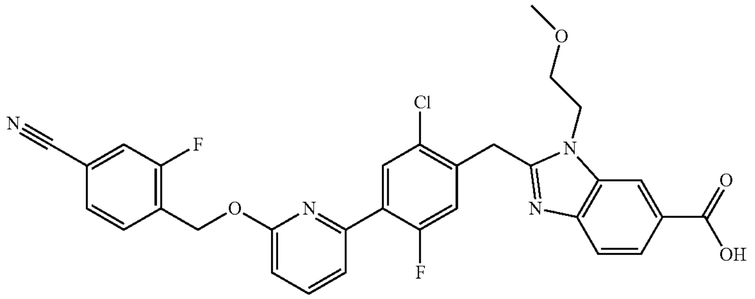 [SMILES: COCCn1c(Cc2cc(Cl)c(-c3cccc(OCc4ccc(C#N)cc4F)n3)cc2F)nc2ccc(C(=O)O)cc21]<br>2-(2-chloro-4-(6-((4-cyano-2-fluorobenzyl)oxy)pyridin-2-yl)-5-fluorobenzyl)-1-(2-methoxyethyl)-1H-benzo[d]imidazole-6-carboxylic acid: ES/MS m/z 589.4; $^{1}$H NMR (400 MHz, Methanol-d4) δ 8.37 (s, 1H), 8.15 (d, J = 8.6 Hz, 1H), 8.05-7.96 (m, 1H), 7.72 (dt, J = 17.1, 8.7 Hz, 3H), 7.52 (d, J = 7.4 Hz, 3H), 7.17 (d, J = 11.4 Hz, 1H), 6.96-6.83 (m, 1H), 5.60 (s, 2H), 4.64-4.54 (m, 4H), 3.79 (s, 2H). |
| 314 | 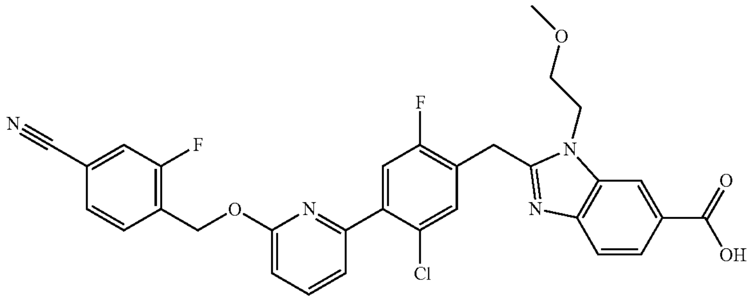<br>2-(5-chloro-4-(6-((4-cyano-2-fluorobenzyl)oxy)pyridin-2-yl)-2-fluorobenzyl)-1-(2-methoxyethyl)-1H-benzo[d]imidazole-6-carboxylic acid: ES/MS m/z 589.2; $^{1}$H NMR (400 MHz, Methanol-d4) δ 8.57-8.53 (m, 1H), 8.22 (dd, J = 8.6, 1.5 Hz, 1H), 7.85 (dd, J = 8.3, 7.4 Hz, 1H), 7.78 (dd, J = 8.6, 0.7 Hz, 1H), 7.72 (dd, J = 8.1, 7.2 Hz, 1H), 7.67-7.55 (m, 3H), 7.46-7.33 (m, 2H), 6.98 (dd, J = 8.4, 0.7 Hz, 1H), 5.58 (s, 2H), 4.82 (q, J = 5.0 Hz, 2H), 4.75 (s, 2H), 3.84 (dd, J = 5.4, 4.4 Hz, 2H). |

-continued

| Example | Structure/Name/Characterization |
|---|---|
| 349 | 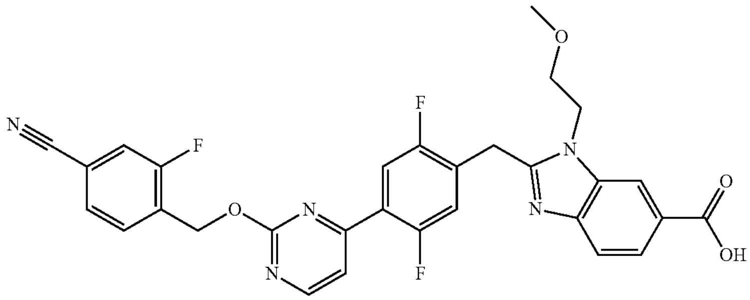 [SMILES: COCCn1c(Cc2cc(F)c(-c3ccnc(OCc4ccc(C#N)cc4F)n3)cc2F)nc2ccc(C(=O)O)cc21]<br>2-(4-(2-((4-cyano-2-fluorobenzyl)oxy)pyrimidin-4-yl)-2,5-difluorobenzyl)-1-(2-methoxyethyl)-1H-benzo[d]imidazole-6-carboxylic acid: ES/MS m/z 574.2; $^{1}$H NMR (400 MHz, DMSO-d6) δ 8.79 (d, J = 5.1 Hz, 1H), 8.26 (d, J = 1.4 Hz, 1H), 8.00-7.87 (m, 2H), 7.83 (dd, J = 8.4, 1.5 Hz, 1H), 7.81-7.73 (m, 2H), 7.68-7.59 (m, 2H), 7.49 (dd, J = 11.5, 5.9 Hz, 1H), 5.64 (s, 2H), 4.63 (t, J = 5.1 Hz, 2H), 4.51 (s, 2H), 3.69 (t, J = 5.0 Hz, 2H), 3.21 (s, 3H). |
| 368 | 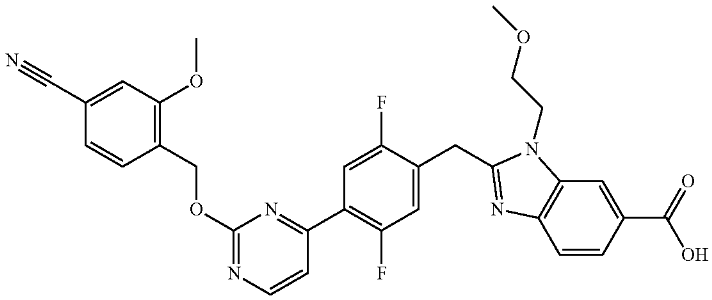 [SMILES: COCCn1c(Cc2cc(F)c(-c3ccnc(OCc4ccc(C#N)cc4OC)n3)cc2F)nc2ccc(C(=O)O)cc21]<br>2-(4-(2-((4-cyano-2-methoxybenzyl)oxy)pyrimidin-4-yl)-2,5-difluorobenzyl)-1-(2-methoxyethyl)-1H-benzo[d]imidazole-6-carboxylic acid: ES/MS m/z 586.2; $^{1}$H NMR (400 MHz, DMSO-d6) δ 8.77 (d, J = 5.1 Hz, 1H), 8.22 (d, J = 1.5 Hz, 1H), 7.87 (dd, J = 10.2, 6.2 Hz, 1H), 7.81 (dd, J = 8.4, 1.6 Hz, 1H), 7.64-7.55 (m, 4H), 7.51-7.42 (m, 2H), 5.54 (s, 2H), 4.61 (t, J = 5.1 Hz, 2H), 4.48 (s, 2H), 3.92 (s, 3H), 3.69 (t, J = 5.0 Hz, 2H), 3.21 (s, 3H). |
| 408 | 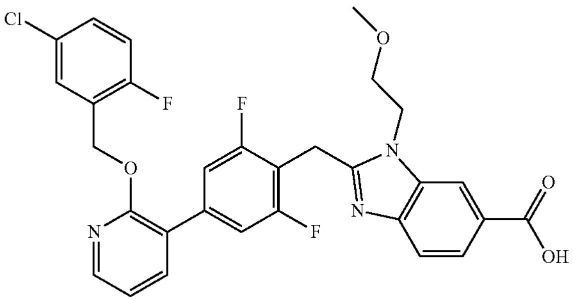 [SMILES: COCCn1c(Cc2c(F)cc(-c3cccnc3OCc3cc(Cl)ccc3F)cc2F)nc2ccc(C(=O)O)cc21]<br>2-(4-(2-((5-chloro-2-fluorobenzyl)oxy)pyridin-3-yl)-2,6-difluorobenzyl)-1-(2-methoxyethyl)-1H-benzo[d]imidazole-6-carboxylic acid: ES/MS m/z 582.4; $^{1}$H NMR (400 MHz, Methanol-d4) δ 8.53 (d, J = 1.6 Hz, 1H), 8.27 (dd, J = 5.1, 2.0 Hz, 1H), 8.21 (dd, J = 8.6, 1.5 Hz, 1H), 7.83-7.73 (m, 2H), 7.44-7.23 (m, 4H), 7.20-7.06 (m, 2H), 5.46 (s, 2H), 4.79 (t, J = 4.9 Hz, 2H), 4.73 (s, 2H), 3.80 (t, J = 4.9 Hz, 2H), 3.27 (s, 3H). |

-continued

| Example | Structure/Name/Characterization |
|---|---|
| 412 | 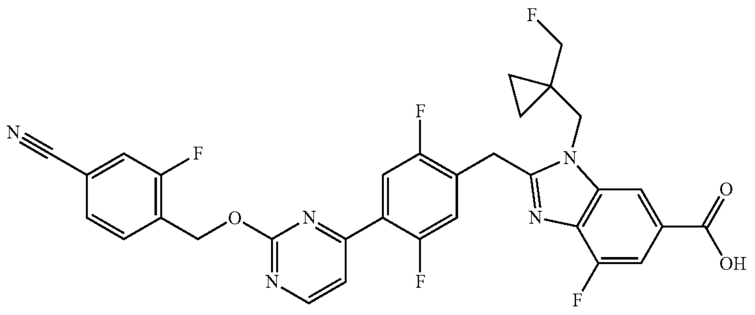 [SMILES: N#Cc1ccc(COc2nccc(-c3cc(F)c(Cc4nc5c(F)cc(C(=O)O)cc5n4CC4(CF)CC4)cc3F)n2)c(F)c1] 2-(4-(2-((4-cyano-2-fluorobenzyl)oxy)pyrimidin-4-yl)-2,5-difluorobenzyl)-4-fluoro-1-((1-(fluoromethyl)cyclopropyl)methyl)-1H-benzo[d]imidazole-6-carboxylic acid: ES/MS m/z 620.2; $^1$H NMR (400 MHz, DMSO-d6) δ 8.79 (d, J = 5.1 Hz, 1H), 8.14 (s, 1H), 7.97-7.88 (m, 2H), 7.82-7.73 (m, 2H), 7.65 (dd, J = 5.3, 1.8 Hz, 1H), 7.52 (dd, J = 11.4, 5.2 Hz, 2H), 5.64 (s, 2H), 4.58 (s, 2H), 4.49 (s, 2H), 4.18 (d, J = 48.8 Hz, 2H), 0.87-0.80 (m, 2H), 0.75-0.68 (m, 2H). |
| 413 | 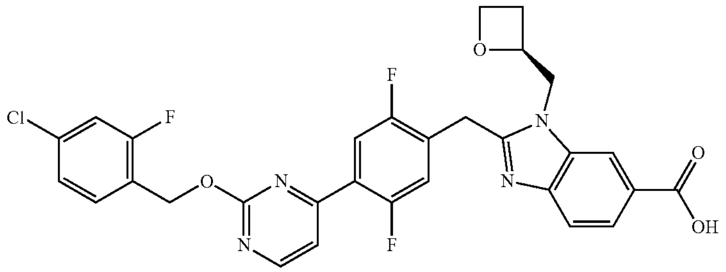 [SMILES: O=C(O)c1ccc2nc(Cc3cc(F)c(-c4ccnc(OCc5ccc(Cl)cc5F)n4)cc3F)n(C[C@@H]3CCO3)c2c1] (S)-2-(4-(2-((4-chloro-2-fluorobenzyl)oxy)pyrimidin-4-yl)-2,5-difluorobenzyl)-1-(oxetan-2-ylmethyl)-1H-benzo[d]imidazole-6-carboxylic acid: ES/MS m/z 595.2; $^1$H NMR (400 MHz, DMSO-d6) δ 8.78 (d, J = 5.2 Hz, 1H), 8.29 (d, J = 1.5 Hz, 1H), 7.93 (dd, J = 10.2, 6.2 Hz, 1H), 7.81 (dd, J = 8.5, 1.6 Hz, 1H), 7.68-7.59 (m, 3H), 7.55-7.44 (m, 2H), 7.36 (dd, J = 8.2, 2.1 Hz, 1H), 5.54 (s, 2H), 5.14-5.00 (m, 1H), 4.79 (dd, J = 15.6, 7.0 Hz, 1H), 4.69-4.45 (m, 4H), 4.36 (dt, J = 9.1, 6.0 Hz, 1H), 2.79-2.68 (m, 1H), 2.47-2.34 (m, 1H). |
| 420 | 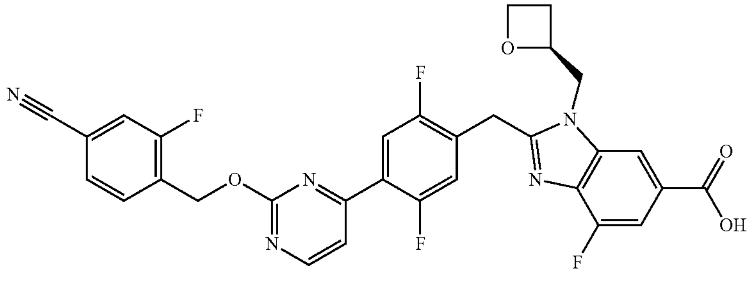 [SMILES: N#Cc1ccc(COc2nccc(-c3cc(F)c(Cc4nc5c(F)cc(C(=O)O)cc5n4C[C@@H]4CCO4)cc3F)n2)c(F)c1] (S)-2-(4-(2-((4-cyano-2-fluorobenzyl)oxy)pyrimidin-4-yl)-2,5-difluorobenzyl)-4-fluoro-1-(oxetan-2-ylmethyl)-1H-benzo[d]imidazole-6-carboxylic acid: ES/MS m/z 604.2; $^1$H NMR (400 MHz, DMSO-d6) δ 8.78 (d, J = 5.1 Hz, 1H), 8.16 (d, J = 1.3 Hz, 1H), 7.98-7.87 (m, 2H), 7.84-7.71 (m, 2H), 7.65 (dd, J = 5.1, 1.8 Hz, 1H), 7.54-7.46 (m, 2H), 5.64 (s, 2H), 5.08 (qd, J = 7.0, 2.7 Hz, 1H), 4.80 (dd, J = 15.6, 7.1 Hz, 1H), 4.71-4.46 (m, 4H), 4.35 (dt, J = 9.0, 5.9 Hz, 1H), 2.78-2.66 (m, 1H), 2.44-2.32 (m, 1H). |

-continued

| Example | Structure/Name/Characterization |
|---|---|
| 427 | 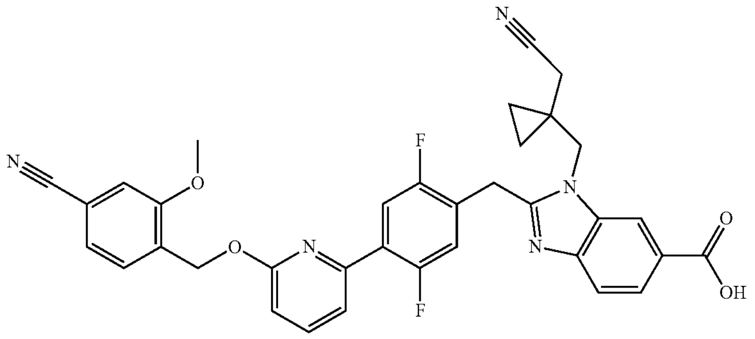<br>2-(4-(6-((4-cyano-2-methoxybenzyl)oxy)pyridin-2-yl)-2,5-difluorobenzyl)-1-((1-(cyanomethyl)cyclopropyl)methyl)-1H-benzo[d]imidazole-6-carboxylic acid: ES/MS m/z 620.2; $^1$H NMR (400 MHz, Methanol-d4) δ 8.66 (s, 1H), 8.24 (d, J = 8.5 Hz, 1H), 7.90-7.72 (m, 3H), 7.64-7.51 (m, 2H), 7.46-7.28 (m, 3H), 6.97 (d, J = 8.2 Hz, 1H), 5.57 (s, 2H), 4.81-4.77 (m, 4H), 3.96 (s, 3H), 2.65 (s, 2H), 1.06-0.99 (m, 2H), 0.98-0.89 (m, 2H). |
| 428 | 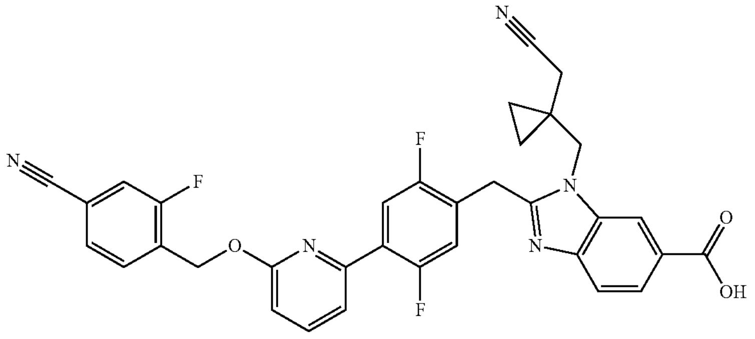 [SMILES: N#CCC1(Cn2c(Cc3cc(F)c(-c4cccc(OCc5ccc(C#N)cc5F)n4)cc3F)nc3ccc(C(=O)O)cc32)CC1]<br>2-(4-(6-((4-cyano-2-fluorobenzyl)oxy)pyridin-2-yl)-2,5-difluorobenzyl)-1-((1-(cyanomethyl)cyclopropyl)methyl)-1H-benzo[d]imidazole-6-carboxylic acid: ES/MS m/z 608.2; $^1$H NMR (400 MHz, Methanol-d4) δ 8.55 (s, 1H), 8.18-8.09 (m, 1H), 7.89-7.78 (m, 2H), 7.78-7.68 (m, 2H), 7.66-7.52 (m, 3H), 7.34 (dd, J = 11.2, 6.1 Hz, 1H), 6.95 (d, J = 8.2 Hz, 1H), 5.64 (s, 2H), 4.72-4.66 (m, 4H), 2.62 (s, 2H), 0.99-0.93 (m, 2H), 0.93-0.84 (m, 2H). |
| 440 | 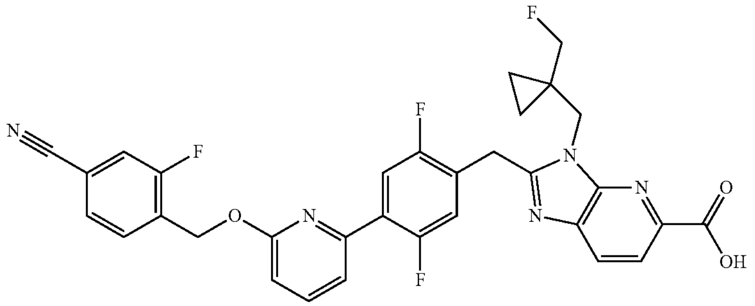 [SMILES: N#Cc1ccc(COc2cccc(-c3cc(F)c(Cc4nc5ccc(C(=O)O)nc5n4CC4(CF)CC4)cc3F)n2)c(F)c1]<br>2-(4-(6-((4-cyano-2-fluorobenzyl)oxy)pyridin-2-yl)-2,5-difluorobenzyl)-3-((1-(fluoromethyl)cyclopropyl)methyl)-3H-imidazo[4,5-b]pyridine-5-carboxylic acid: ES/MS m/z 602.2; $^1$H NMR (400 MHz, Methanol-d4) δ 8.20 (d, J = 8.3 Hz, 1H), 8.11 (d, J = 8.3 Hz, 1H), 7.89-7.69 (m, 3H), 7.66-7.51 (m, 3H), 7.28 (dd, J = 11.3, 5.9 Hz, 1H), 6.94 (d, J = 8.3 Hz, 1H), 5.64 (s, 2H), 4.67 (s, 2H), 4.63 (s, 2H), 4.32 (d, J = 48.9 Hz, 2H), 1.26-1.14 (m, 2H), 0.81-0.68 (m, 2H). |

-continued

| Example | Structure/Name/Characterization |
|---|---|
| 443 | 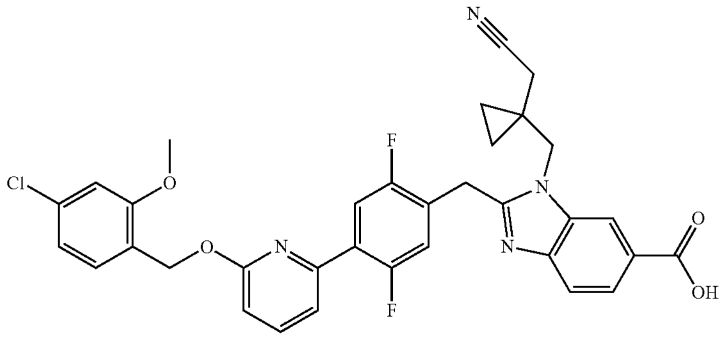 2-(4-(6-((4-chloro-2-methoxybenzyl)oxy)pyridin-2-yl)-2,5-difluorobenzyl)-1-((1-(cyanomethyl)cyclopropyl)methyl)-1H-benzo[d]imidazole-6-carboxylic acid: ES/MS m/z 629.2; $^{1}$H NMR (400 MHz, DMSO-d6) δ 8.32 (d, J = 1.4 Hz, 1H), 7.91-7.75 (m, 3H), 7.64 (d, J = 8.4 Hz, 1H), 7.55-7.39 (m, 3H), 7.14 (d, J = 2.0 Hz, 1H), 7.02 (dd, J = 8.0, 2.0 Hz, 1H), 6.94 (d, J = 8.2 Hz, 1H), 5.42 (s, 2H), 4.60 (s, 2H), 4.50 (s, 2H), 3.86 (s, 3H), 2.69 (s, 2H), 0.78-0.66 (m, 4H). |
| 444 | 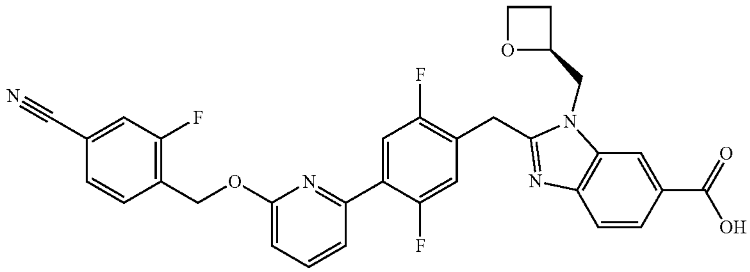 [SMILES: N#Cc1ccc(COc2cccc(-c3cc(F)c(Cc4nc5ccc(C(=O)O)cc5n4C[C@@H]4CCO4)cc3F)n2)c(F)c1] (S)-2-(4-(6-((4-cyano-2-fluorobenzyl)oxy)pyridin-2-yl)-2,5-difluorobenzyl)-1-(oxetan-2-ylmethyl)-1H-benzo[d]imidazole-6-carboxylic acid: ES/MS m/z 585.2; $^{1}$H NMR (400 MHz, DMSO-d6) δ 8.30 (d, J = 1.5 Hz, 1H), 7.97-7.86 (m, 2H), 7.83 (dd, J = 8.5, 1.6 Hz, 1H), 7.80-7.72 (m, 3H), 7.63 (d, J = 8.5 Hz, 1H), 7.53 (dd, J = 7.4, 1.7 Hz, 1H), 7.41 (dd, J = 11.5, 6.1 Hz, 1H), 7.00 (d, J = 8.3 Hz, 1H), 5.60 (s, 2H), 5.07 (td, J = 7.2, 2.7 Hz, 1H), 4.79 (dd, J = 15.5, 7.1 Hz, 1H), 4.66 (dd, J = 15.5, 2.8 Hz, 1H), 4.61-4.44 (m, 3H), 4.37 (dt, J = 9.0, 5.9 Hz, 1H), 2.79-2.64 (m, 1H), 2.46-2.33 (m, 1H). |
| 445 | 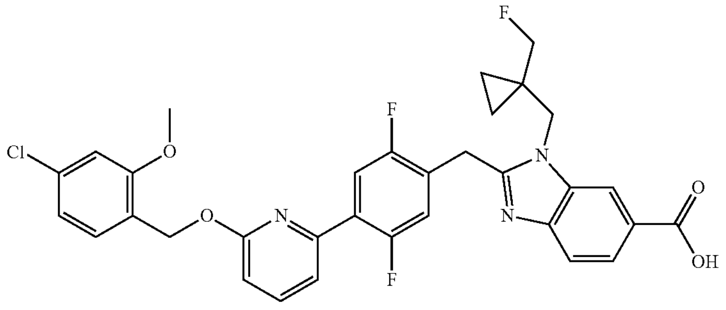 [SMILES: COc1cc(Cl)ccc1COc1cccc(-c2cc(F)c(Cc3nc4ccc(C(=O)O)cc4n3CC3(CF)CC3)cc2F)n1] 2-(4-(6-((4-chloro-2-methoxybenzyl)oxy)pyridin-2-yl)-2,5-difluorobenzyl)-1-((1-(fluoromethyl)cyclopropyl)methyl)-1H-benzo[d]imidazole-6-carboxylic acid: ES/MS m/z 622.2; $^{1}$H NMR (400 MHz, DMSO-d6) δ 8.28 (d, J = 1.4 Hz, 1H), 7.90-7.76 (m, 3H), 7.64 (d, J = 8.4 Hz, 1H), 7.50 (dd, J = 7.5, 1.7 Hz, 1H), 7.47-7.37 (m, 2H), 7.14 (d, J = 2.0 Hz, 1H), 7.02 (dd, J = 8.0, 2.0 Hz, 1H), 6.94 (d, J = 8.2 Hz, 1H), 5.42 (s, 2H), 4.58 (s, 2H), 4.47 (s, 2H), 4.19 (d, J = 48.8 Hz, 2H), 3.86 (s, 3H), 0.89-0.80 (m, 2H), 0.77-0.69 (m, 2H). |

-continued

| Example | Structure/Name/Characterization |
|---|---|
| 448 | 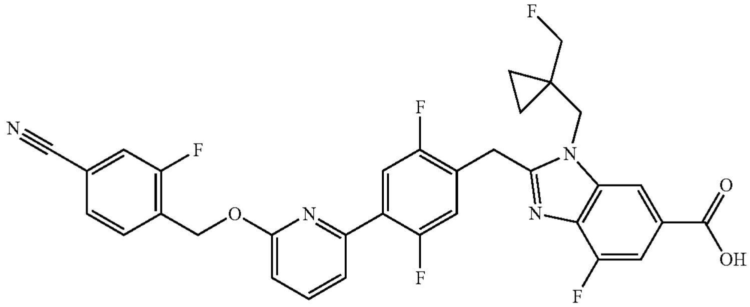 [SMILES: N#Cc1ccc(COc2cccc(-c3cc(F)c(Cc4nc5c(F)cc(C(=O)O)cc5n4CC4(CF)CC4)cc3F)n2)c(F)c1] 2-(4-(6-((4-cyano-2-fluorobenzyl)oxy)pyridin-2-yl)-2,5-difluorobenzyl)-4-fluoro-1-((1-(fluoromethyl)cyclopropyl)methyl)-1H-benzo[d]imidazole-6-carboxylic acid: ES/MS m/z 619.2; $^1$H NMR (400 MHz, DMSO-d6) δ 8.14 (s, 1H), 7.96-7.86 (m, 2H), 7.75 (dt, J = 10.3, 7.7 Hz, 3H), 7.53 (t, J = 9.6 Hz, 2H), 7.42 (dd, J = 11.5, 6.0 Hz, 1H), 6.99 (d, J = 8.2 Hz, 1H), 5.61 (s, 2H), 4.58 (s, 2H), 4.46 (s, 2H), 4.18 (d, J = 48.8 Hz, 2H), 0.88-0.77 (m, 2H), 0.74 (d, J = 5.0 Hz, 2H). |
| 449 | 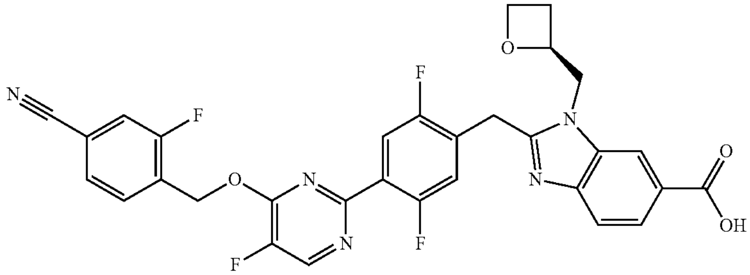 [SMILES: N#Cc1ccc(COc2nc(-c3cc(F)c(Cc4nc5ccc(C(=O)O)cc5n4C[C@@H]4CCO4)cc3F)ncc2F)c(F)c1] (S)-2-(4-(4-((4-cyano-2-fluorobenzyl)oxy)-5-fluoropyrimidin-2-yl)-2,5-difluorobenzyl)-1-(oxetan-2-ylmethyl)-1H-benzo[d]imidazole-6-carboxylic acid: ES/MS m/z 604.2; $^1$H NMR (400 MHz, DMSO-d6) δ 8.85 (d, J = 2.8 Hz, 1H), 8.31 (d, J = 1.4 Hz, 1H), 7.96 (dd, J = 9.9, 1.4 Hz, 1H), 7.89-7.75 (m, 4H), 7.63 (d, J = 8.4 Hz, 1H), 7.43 (dd, J = 11.1, 6.0 Hz, 1H), 5.76 (s, 2H), 5.08 (qd, J = 7.1, 2.6 Hz, 1H), 4.80 (dd, J = 15.6, 7.1 Hz, 1H), 4.71-4.44 (m, 4H), 4.37 (dt, J = 9.1, 5.9 Hz, 1H), 2.78-2.65 (m, 1H), 2.45-2.36 (m, 1H). |
| 450 | 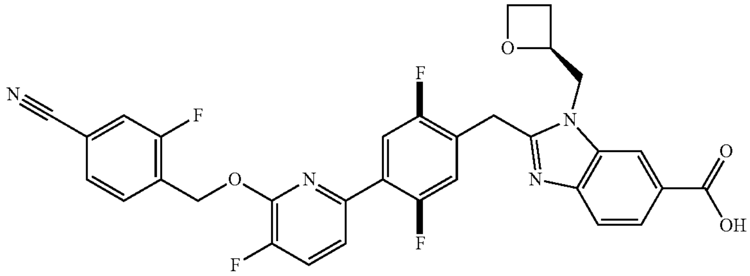 (S)-2-(4-(6-((4-cyano-2-fluorobenzyl)oxy)-5-fluoropyridin-2-yl)-2,5-difluorobenzyl)-1-(oxetan-2-ylmethyl)-1H-benzo[d]imidazole-6-carboxylic acid: ES/MS m/z 603.2; $^1$H NMR (400 MHz, DMSO-d6) δ 8.31 (d, J = 1.5 Hz, 1H), 7.95 (dd, J = 10.1, 1.3 Hz, 1H), 7.91-7.69 (m, 5H), 7.63 (d, J = 8.4 Hz, 1H), 7.55 (ddd, J = 8.2, 2.9, 1.4 Hz, 1H), 7.42 (dd, J = 11.3, 6.2 Hz, 1H), 5.70 (s, 2H), 5.08 (qd, J = 7.1, 2.6 Hz, 1H), 4.80 (dd, J = 15.6, 7.2 Hz, 1H), 4.71-4.44 (m, 4H), 4.37 (dt, J = 9.0, 5.9 Hz, 1H), 2.82-2.62 (m, 1H), 2.48-2.33 (m, 1H). |

-continued

| Example | Structure/Name/Characterization |
|---|---|
| 451 | 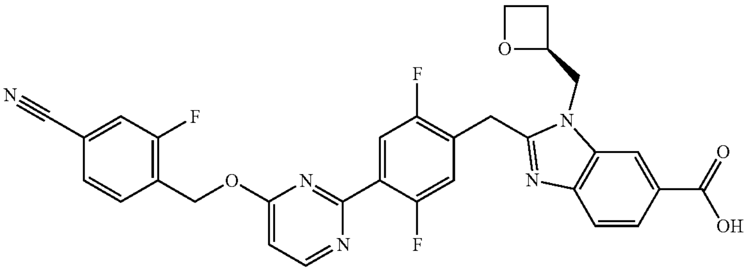 (S)-2-(4-(4-((4-cyano-2-fluorobenzyl)oxy)pyrimidin-2-yl)-2,5-difluorobenzyl)-1-(oxetan-2-ylmethyl)-1H-benzo[d]imidazole-6-carboxylic acid: ES/MS m/z 586.2; $^1$H NMR (400 MHz, DMSO-d6) δ 8.74 (d, J = 5.8 Hz, 1H), 8.27 (d, J = 1.5 Hz, 1H), 7.94 (dd, J = 10.0, 1.3 Hz, 1H), 7.87 (dd, J = 10.1, 6.2 Hz, 1H), 7.83-7.72 (m, 3H), 7.61 (d, J = 8.5 Hz, 1H), 7.40 (dd, J = 11.1, 6.0 Hz, 1H), 7.08 (d, J = 5.8 Hz, 1H), 5.67 (s, 2H), 5.08 (qd, J = 7.1, 2.7 Hz, 1H), 4.77 (dd, J = 15.6, 7.1 Hz, 1H), 4.68-4.56 (m, 1H), 4.56-4.43 (m, 3H), 4.36 (dt, J = 9.1, 5.9 Hz, 1H), 2.80-2.65 (m, 1H), 2.46-2.28 (m, 1H). |
| 501 | 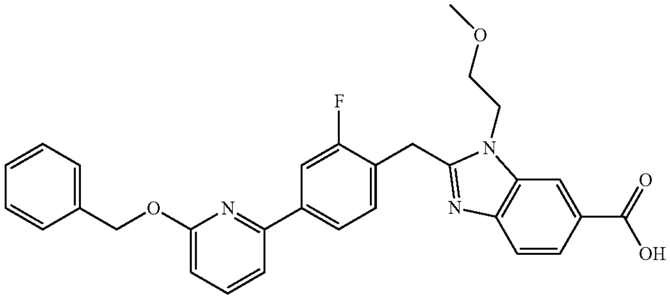 [SMILES: COCCn1c(Cc2ccc(-c3cccc(OCc4ccccc4)n3)cc2F)nc2ccc(C(=O)O)cc21] 2-(4-(6-(benzyloxy)pyridin-2-yl)-2-fluorobenzyl)-1-(2-methoxyethyl)-1H-benzo[d]imidazole-6-carboxylic acid: ES/MS m/z 512.2; $^1$H NMR (400 MHz, Chloroform-d) δ 8.35 (s, 1H), 8.29 (d, J = 6.6 Hz, 1H), 8.14 (d, J = 9.3 Hz, 1H), 7.84 (s, 2H), 7.71-7.55 (m, 2H), 7.50 (d, J = 7.5 Hz, 2H), 7.39 (d, J = 7.3 Hz, 2H), 7.34 (t, J = 6.3 Hz, 2H), 6.85-6.75 (m, 1H), 5.49 (s, 2H), 4.92 (s, 2H), 4.62 (s, 2H), 3.76 (s, 2H), 3.32 (s, 3H), 3.06 (s, 23H). |
| 541 | 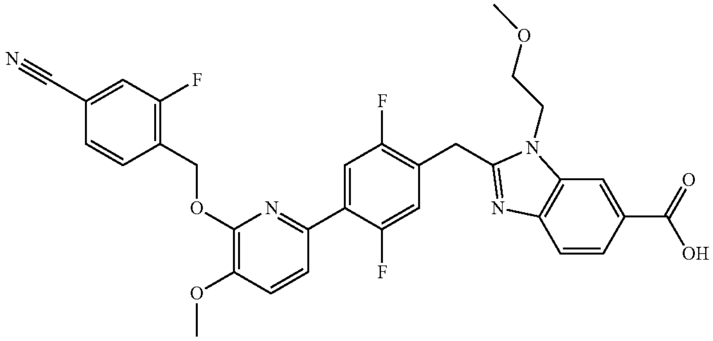 [SMILES: COCCn1c(Cc2cc(F)c(-c3ccc(OC)c(OCc4ccc(C#N)cc4F)n3)cc2F)nc2ccc(C(=O)O)cc21] 2-(4-(6-((4-cyano-2-fluorobenzyl)oxy)-5-methoxypyridin-2-yl)-2,5-difluorobenzyl)-1-(2-methoxyethyl)-1H-benzo[d]imidazole-6-carboxylic acid: ES/MS m/z 603.2; $^1$H NMR (400 MHz, DMSO) δ 8.31-8.27 (m, 1H), 7.97-7.90 (m, 1H), 7.87 (dd, J = 8.4, 1.5 Hz, 1H), 7.77-7.67 (m, 3H), 7.65 (d, J = 8.4 Hz, 1H), 7.51 (dd, J = 8.2, 1.5 Hz, 1H), 7.46 (d, J = 8.2 Hz, 1H), 7.36 (dd, J = 11.6, 6.1 Hz, 1H), 5.60 (s, 2H), 4.65 (t, J = 5.1 Hz, 2H), 4.49 (s, 2H), 3.87 (s, 3H), 3.69 (t, J = 5.0 Hz, 2H), 3.20 (s, 3H). |

-continued

| Example | Structure/Name/Characterization |
|---|---|
| 600 | 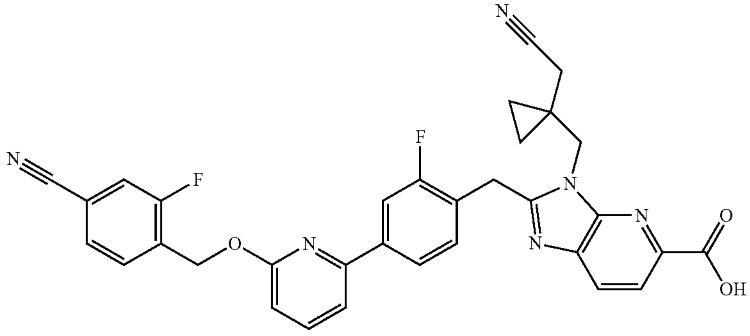 [SMILES: N#CCC1(Cn2c(Cc3ccc(-c4cccc(OCc5ccc(C#N)cc5F)n4)cc3F)nc3ccc(C(=O)O)nc32)CC1]<br>2-(4-(6-((4-cyano-2-fluorobenzyl)oxy)pyridin-2-yl)-2-fluorobenzyl)-3-((1-(cyanomethyl)cyclopropyl)methyl)-3H-imidazo[4,5-b]pyridine-5-carboxylic acid: ES/MS m/z 591.2; $^{1}$H NMR (400 MHz, Methanol-d4) δ 8.23 (d, J = 8.3 Hz, 1H), 8.13 (d, J = 8.3 Hz, 1H), 7.91-7.76 (m, 3H), 7.74 (t, J = 7.5 Hz, 1H), 7.65-7.53 (m, 3H), 7.48 (t, J = 8.0 Hz, 1H), 6.90 (d, J = 8.1 Hz, 1H), 5.66 (s, 2H), 4.65 (d, J = 10.5 Hz, 4H), 2.74-2.69 (m, 4H), 1.11 (d, J = 6.0 Hz, 2H), 0.92-0.68 (m, 2H). |
| 754 | ES/MS (M + H+) 629.2; 1H NMR (400 MHz, DMSO-d6) δ 8.73 (d, J = 5.8 Hz, 1H), 8.25 (d, J = 1.5 Hz, 1H), 7.94-7.72 (m, 4H), 7.65 (dd, J = 8.0, 1.7 Hz, 1H), 7.60 (d, J = 8.4 Hz, 1H), 7.40 (dd, J = 11.1, 6.0 Hz, 1H), 7.07 (d, J = 5.8 Hz, 1H), 5.68 (s, 2H), 5.08 (qd, J = 7.0, 2.7 Hz, 1H), 4.76 (dd, J = 15.6, 7.1 Hz, 1H), 4.65-4.42 (m, 4H), 4.35 (dt, J = 9.0, 5.9 Hz, 1H), 2.83-2.61 (m, 1H), 2.44-2.27 (m, 1H). Multiplet Report 19F NMR (377 MHz, DMSO-d6) δ −61.70, −73.95, −114.19--117.77 (m), −119.35 (ddd, J = 17.5, 11.0, 6.3 Hz), −122.74 (ddd, J = 17.0, 10.1, 5.9 Hz). |
| 755 | 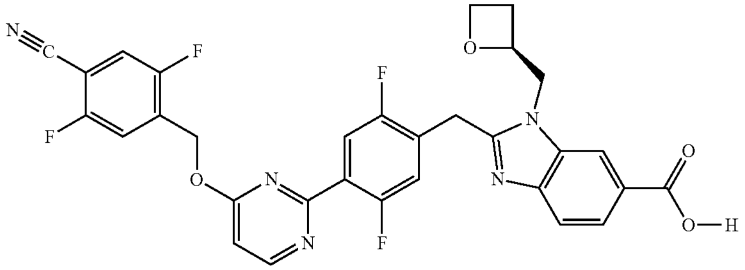 [SMILES: N#Cc1cc(F)c(COc2ccnc(-c3cc(F)c(Cc4nc5ccc(C(=O)O)cc5n4C[C@@H]4CCO4)cc3F)n2)cc1F]<br>ES/MS (M + H+) 604.2; 1H NMR (400 MHz, DMSO-d6) δ 8.75 (d, J = 5.8 Hz, 1H), 8.24 (d, J = 1.4 Hz, 1H), 8.07 (dd, J = 9.2, 5.2 Hz, 1H), 7.86 (dd, J = 10.1, 6.2 Hz, 1H), 7.81-7.70 (m, 2H), 7.58 (d, J = 8.5 Hz, 1H), 7.40 (dd, J = 11.1, 6.0 Hz, 1H), 7.10 (d, J = 5.7 Hz, 1H), 5.65 (s, 2H), 5.07 (d, J = 8.0 Hz, 1H), 4.75 (dd, J = 15.6, 7.0 Hz, 1H), 4.66-4.39 (m, 4H), 4.35 (dt, J = 8.9, 5.9 Hz, 1H), 2.73 (d, J = 10.7 Hz, 1H), 2.44-2.35 (m, 1H). Multiplet Report 19F NMR (376 MHz, DMSO-d6) δ −73.94, −113.72 (ddd, J = 17.2, 9.3, 5.2 Hz), −118.25--120.18 (m), −120.85 (dd, J = 16.2, 7.2 Hz), −122.77. |
| 756 | 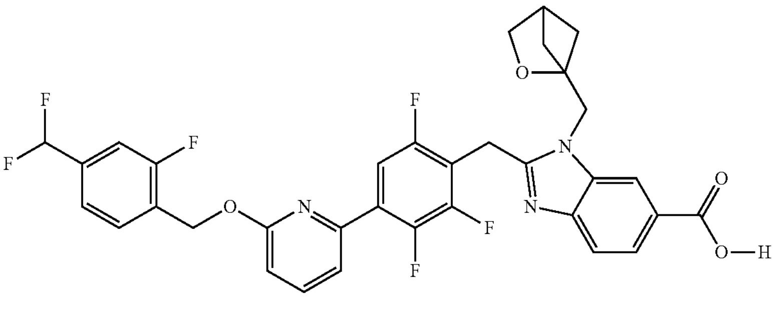 [SMILES: O=C(O)c1ccc2nc(Cc3c(F)cc(-c4cccc(OCc5ccc(C(F)F)cc5F)n4)c(F)c3F)n(CC34CC(CO3)C4)c2c1]<br>ES/MS (M + H+) 654.2; 1H NMR (400 MHz, DMSO) δ 8.28 (d, J = 1.5 Hz, 1H), 7.94 (t, J = 7.9 Hz, 1H), 7.79 (dd, J = 8.5, 1.5 Hz, 1H), 7.76-7.63 (m, 2H), 7.57 (d, J = 8.2 Hz, 2H), 7.48 (dd, J = 15.6, 9.1 Hz, 2H), 7.06 (t, J = 55.6 Hz, 1H), 7.03 (d, J = 8.3 Hz, 1H), 5.58 (s, 2H), 4.86 (s, 2H), 4.58 (s, 2H), 3.65 (s, 2H), 2.91 (t, J = 3.2 Hz, 1H), 2.06-1.89 (m, 2H), 1.32 (dd, J = 4.4, 1.7 Hz, |

-continued

| Example | Structure/Name/Characterization |
|---|---|
| | 2H). Multiplet Report 19F NMR (376 MHz, DMSO) δ −75.36, −110.78 (d, J = 55.7 Hz), −117.18 (dd, J = 10.3, 7.5 Hz), −119.36 (t, J = 12.7 Hz), −137.35 (d, J = 21.5 Hz), −146.80 (d, J = 5.8 Hz). |
| 757 | 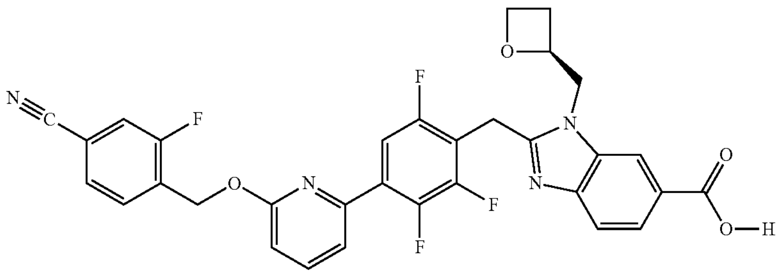 [SMILES: N#Cc1ccc(COc2cccc(-c3cc(F)c(Cc4nc5ccc(C(=O)O)cc5n4C[C@@H]4CCO4)c(F)c3F)n2)c(F)c1] ES/MS (M + H+) 603.2; 1H NMR (400 MHz, DMSO) δ 8.26 (s, 1H), 8.05-7.86 (m, 2H), 7.83-7.72 (m, 3H), 7.70-7.60 (m, 1H), 7.58 (d, J = 8.4 Hz, 2H), 7.05 (d, J = 8.3 Hz, 1H), 5.61 (s, 2H), 5.13 (s, 1H), 4.81 (dd, J = 15.6, 6.9 Hz, 1H), 4.74-4.58 (m, 2H), 4.57-4.44 (m, 2H), 4.35 (d, J = 8.8 Hz, 1H), 2.74 (s, 1H), 2.40 (d, J = 9.4 Hz, 2H). Multiplet Report 19F NMR (376 MHz, DMSO) δ −73.94, −111.40-−117.45 (m), −119.51, −137.58 (d, J = 21.8 Hz), −146.87. |
| 758 | 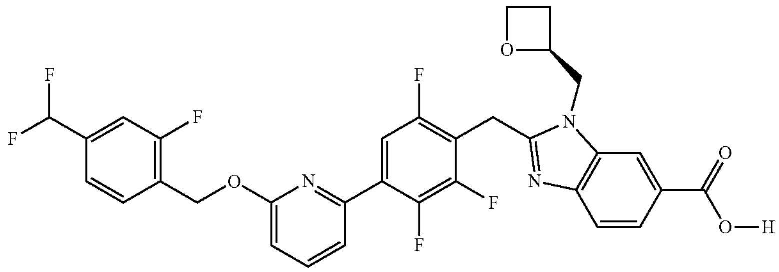 [SMILES: O=C(O)c1ccc2nc(Cc3c(F)cc(-c4cccc(OCc5ccc(C(F)F)cc5F)n4)c(F)c3F)n(C[C@@H]3CCO3)c2c1] ES/MS (M + H+) 628.2; 1H NMR (400 MHz, DMSO) δ 8.37-8.15 (m, 1H), 8.09-7.88 (m, 1H), 7.84-7.62 (m, 3H), 7.57 (dd, J = 7.6, 3.6 Hz, 2H), 7.48 (dd, J = 15.8, 9.1 Hz, 2H), 7.06 (d, J = 111.2 Hz, 1H), 7.14-6.99 (m, 2H), 5.58 (s, 2H), 5.13 (d, J = 6.8 Hz, 1H), 4.81 (dd, J = 15.6, 6.8 Hz, 1H), 4.71-4.57 (m, 2H), 4.57-4.39 (m, 2H), 4.35 (dt, J = 9.0, 5.9 Hz, 1H), 2.76 (dd, J = 17.4, 8.3 Hz, 1H), 2.40 (d, J = 8.6 Hz, 1H). Multiplet Report 19F NMR (376 MHz, DMSO) δ −110.79 (d, J = 55.2 Hz), −114.16-−117.82 (m), −117.82-−123.43 (m), −137.61 (d, J = 21.3 Hz), −146.86. |
| 759 | 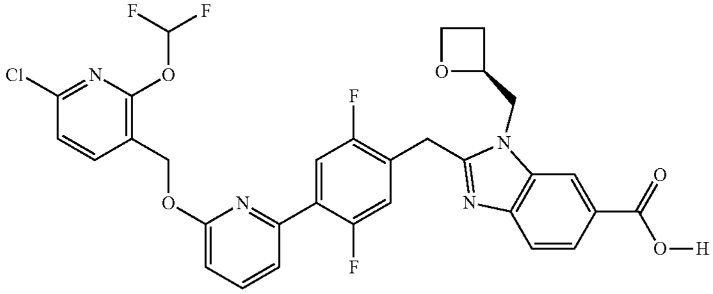 [SMILES: O=C(O)c1ccc2nc(Cc3cc(F)c(-c4cccc(OCc5ccc(Cl)nc5OC(F)F)n4)cc3F)n(C[C@@H]3CCO3)c2c1] ES/MS m/z 643.0; 1H NMR (400 MHz, DMSO) δ 11.95 (s, 1H), 7.43 (d, J = 1.6 Hz, 1H), 7.33 (d, J = 8.3 Hz, 1H), 7.07 (t, J = 7.9 Hz, 1H), 7.03-6.64 (m, 5H), 6.56 (dd, J = 11.5, 6.0 Hz, 1H), 6.35 (d, J = 8.3 Hz, 1H), 6.16 (d, J = 8.2 Hz, 1H), 4.71 (s, 2H), 4.29-4.20 (m, 1H), 3.93 (dd, J = 15.6, 7.1 Hz, 1H), 3.79 (dd, J = 15.5, 2.8 Hz, 1H), 3.74-3.58 (m, 3H), 3.53 (dt, J = 8.9, 5.9 Hz, 1H), 1.97-1.81 (m, 1H), 1.62-1.49 (m, 1H). |

-continued
| Example | Structure/Name/Characterization |
|---|---|
| 760 | 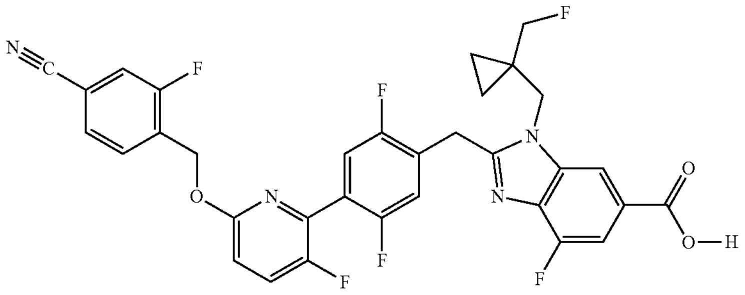 [SMILES: N#Cc1ccc(COc2ccc(F)c(-c3cc(F)c(Cc4nc5c(F)cc(C(=O)O)cc5n4CC4(CF)CC4)cc3F)n2)c(F)c1]<br>ES/MS m/z 637.2; 1H NMR (400 MHz, DMSO) δ 8.13 (s, 1H), 7.94-7.85 (m, 2H), 7.80-7.70 (m, 2H), 7.51 (d, J = 11.3 Hz, 1H), 7.48-7.40 (m, 2H), 7.10 (dd, J = 9.0, 3.0 Hz, 1H), 5.51 (s, 2H), 4.58 (s, 2H), 4.47 (s, 2H), 4.24 (s, 1H), 4.12 (s, 1H), 0.92-0.81 (m, 2H), 0.79-0.67 (m, 2H). |
| 761 | 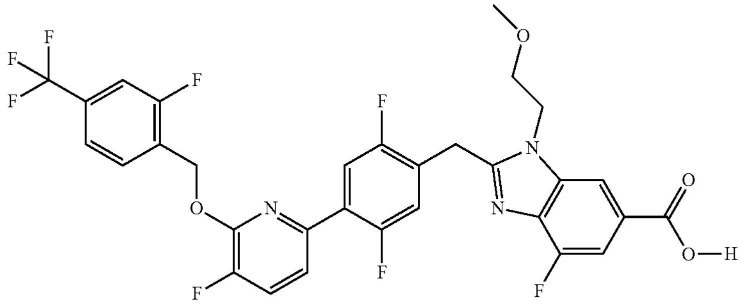 [SMILES: COCCn1c(Cc2cc(F)c(-c3ccc(F)c(OCc4ccc(C(F)(F)F)cc4F)n3)cc2F)nc2c(F)cc(C(=O)O)cc21]<br>ES/MS m/z 652.0; 1H NMR (400 MHz, DMSO) δ 13.08 (s, 1H), 8.09 (d, J = 1.3 Hz, 1H), 7.91-7.79 (m, 2H), 7.79-7.69 (m, 2H), 7.64 (dd, J = 8.1, 1.8 Hz, 1H), 7.57-7.52 (m, 1H), 7.50 (dd, J = 11.4, 1.2 Hz, 1H), 7.39 (dd, J = 11.4, 6.2 Hz, 1H), 5.70 (s, 2H), 4.61 (t, J = 5.1 Hz, 2H), 4.45 (s, 2H), 3.67 (t, J = 5.0 Hz, 2H), 3.20 (s, 3H). |
| 762 | 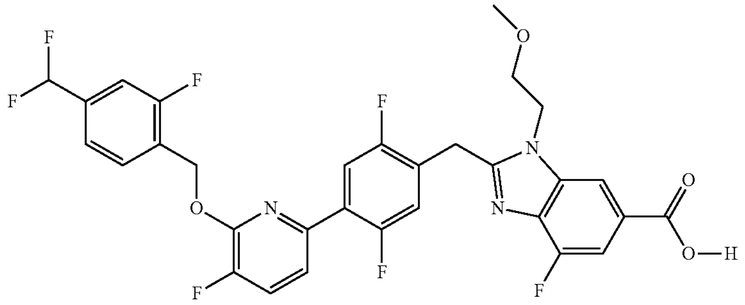 [SMILES: COCCn1c(Cc2cc(F)c(-c3ccc(F)c(OCc4ccc(C(F)F)cc4F)n3)cc2F)nc2c(F)cc(C(=O)O)cc21]<br>ES/MS m/z 634.2; 1H NMR (400 MHz, DMSO) δ 13.08 (s, 1H), 8.09 (d, J = 1.3 Hz, 1H), 7.85 (dd, J = 10.3, 8.2 Hz, 1H), 7.81-7.70 (m, 2H), 7.58-7.43 (m, 4H), 7.39 (dd, J = 11.5, 6.1 Hz, 1H), 7.06 (t, J = 55.6 Hz, 1H), 5.66 (s, 2H), 4.61 (t, J = 5.1 Hz, 2H), 4.45 (s, 2H), 3.67 (t, J = 5.0 Hz, 2H), 3.20 (s, 3H). |
| 763 | 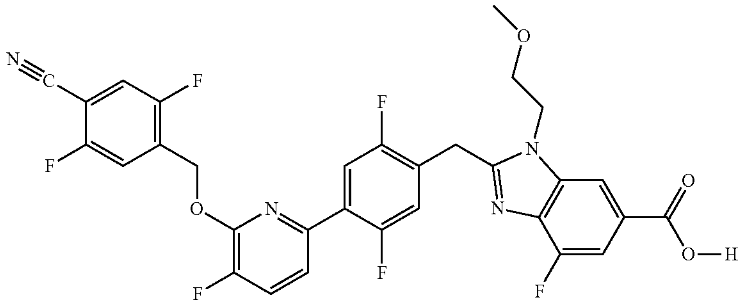 [SMILES: COCCn1c(Cc2cc(F)c(-c3ccc(F)c(OCc4cc(F)c(C#N)cc4F)n3)cc2F)nc2c(F)cc(C(=O)O)cc21] |

-continued

| Example | Structure/Name/Characterization |
|---|---|
| | ES/MS m/z 627.0; 1H NMR (400 MHz, DMSO) δ 13.08 (s, 1H), 8.11-8.02 (m, 2H), 7.87 (dd, J = 10.2, 8.2 Hz, 1H), 7.80-7.68 (m, 2H), 7.59-7.53 (m, 1H), 7.50 (dd, J = 11.4, 1.3 Hz, 1H), 7.39 (dd, J = 11.3, 6.3 Hz, 1H), 5.67 (s, 2H), 4.61 (t, J = 5.1 Hz, 2H), 4.45 (s, 2H), 3.67 (t, J = 5.0 Hz, 2H), 3.20 (s, 3H). |
| 764 | 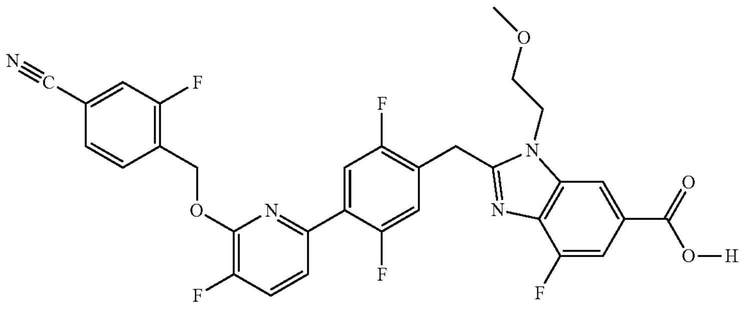 [SMILES: COCCn1c(Cc2cc(F)c(-c3ccc(F)c(OCc4ccc(C#N)cc4F)n3)cc2F)nc2c(F)cc(C(=O)O)cc21] ES/MS m/z 609.2; 1H NMR (400 MHz, DMSO) δ 13.08 (s, 1H), 8.09 (d, J = 1.3 Hz, 1H), 7.93 (dd, J = 10.0, 1.4 Hz, 1H), 7.86 (dd, J = 10.2, 8.2 Hz, 1H), 7.82-7.69 (m, 3H), 7.59-7.53 (m, 1H), 7.50 (dd, J = 11.4, 1.2 Hz, 1H), 7.39 (dd, J = 11.3, 6.2 Hz, 1H), 5.69 (s, 2H), 4.61 (t, J = 5.1 Hz, 2H), 4.45 (s, 2H), 3.69-3.66 (m, 2H), 3.20 (s, 3H). |
| 765 | 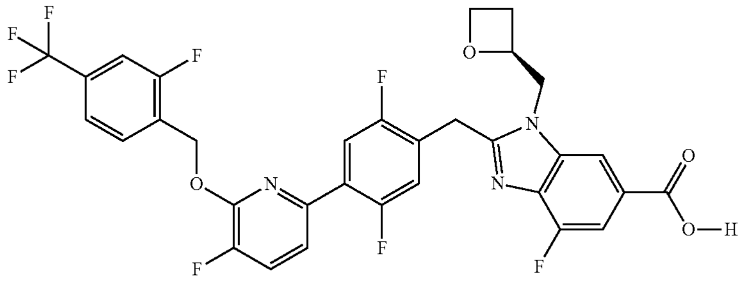 [SMILES: O=C(O)c1cc(F)c2nc(Cc3cc(F)c(-c4ccc(F)c(OCc5ccc(C(F)(F)F)cc5F)n4)cc3F)n(C[C@@H]3CCO3)c2c1] ES/MS m/z 664.0; 1H NMR (400 MHz, DMSO) δ 13.08 (s, 1H), 8.15 (d, J = 1.3 Hz, 1H), 7.94-7.80 (m, 2H), 7.78-7.71 (m, 2H), 7.68-7.62 (m, 1H), 7.57-7.53 (m, 1H), 7.50 (dd, J = 11.4, 1.3 Hz, 1H), 7.40 (dd, J = 11.4, 6.2 Hz, 1H), 5.70 (s, 2H), 5.11-5.01 (m, 1H), 4.78 (dd, J = 15.6, 7.1 Hz, 1H), 4.65 (dd, J = 15.6, 2.7 Hz, 1H), 4.58-4.41 (m, 3H), 4.35 (dt, J = 9.0, 5.9 Hz, 1H), 2.78-2.65 (m, 1H), 2.44-2.30 (m, 1H). |
| 766 | 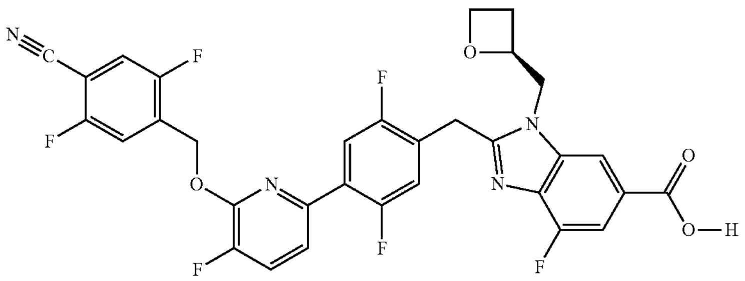 [SMILES: N#Cc1cc(F)c(COc2nc(-c3cc(F)c(Cc4nc5c(F)cc(C(=O)O)cc5n4C[C@@H]4CCO4)cc3F)ccc2F)cc1F] ES/MS m/z 639.0; 1H NMR (400 MHz, DMSO) δ 13.09 (s, 1H), 8.15 (d, J = 1.3 Hz, 1H), 8.07 (dd, J = 9.1, 5.2 Hz, 1H), 7.87 (dd, J = 10.2, 8.2 Hz, 1H), 7.80-7.68 (m, 2H), 7.60-7.53 (m, 1H), 7.50 (dd, J = 11.4, 1.3 Hz, 1H), 7.40 (dd, J = 11.3, 6.2 Hz, 1H), 5.67 (s, 2H), 5.12-5.02 (m, 1H), 4.78 (dd, J = 15.6, 7.0 Hz, 1H), 4.65 (dd, J = 15.6, 2.8 Hz, 1H), 4.58-4.41 (m, 3H), 4.35 (dt, J = 9.0, 6.0 Hz, 1H), 2.81-2.62 (m, 1H), 2.43-2.30 (m, 1H). |

-continued

| Example | Structure/Name/Characterization |
|---|---|
| 767 | 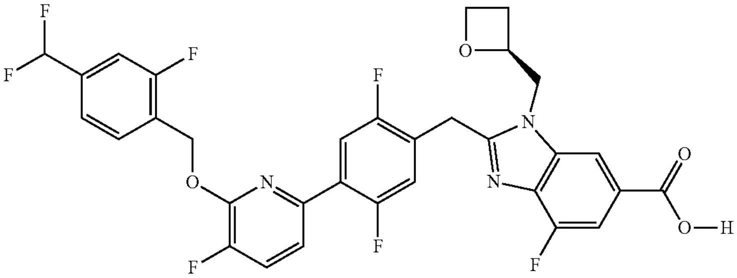 ES/MS m/z 646.2; 1H NMR (400 MHz, DMSO) δ 13.08 (s, 1H), 8.15 (d, J = 1.3 Hz, 1H), 7.85 (dd, J = 10.3, 8.2 Hz, 1H), 7.81-7.70 (m, 2H), 7.58-7.44 (m, 4H), 7.40 (dd, J = 11.5, 6.1 Hz, 1H), 7.06 (t, J = 55.6 Hz, 1H), 5.66 (s, 2H), 5.12-5.01 (m, 1H), 4.79 (dd, J = 15.6, 7.1 Hz, 1H), 4.65 (dd, J = 15.6, 2.7 Hz, 1H), 4.59-4.41 (m, 3H), 4.35 (dt, J = 9.0, 5.9 Hz, 1H), 2.71 (dq, J = 11.6, 7.9 Hz, 1H), 2.43-2.29 (m, 1H). |
| 768 | 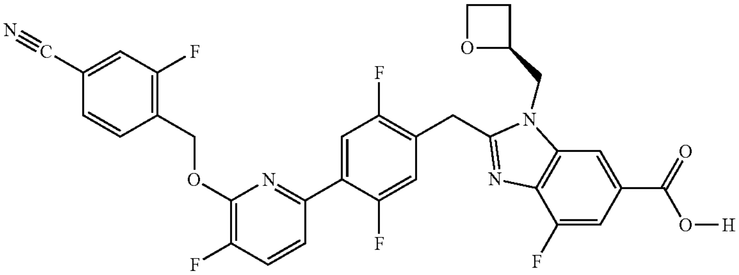 [SMILES: N#Cc1ccc(COc2nc(-c3cc(F)c(Cc4nc5c(F)cc(C(=O)O)cc5n4C[C@@H]4CCO4)cc3F)ccc2F)c(F)c1] ES/MS m/z 621.0; 1H NMR (400 MHz, DMSO) δ 8.09 (d, J = 1.2 Hz, 1H), 7.94 (dd, J = 10.0, 1.4 Hz, 1H), 7.86 (dd, J = 10.2, 8.2 Hz, 1H), 7.82-7.68 (m, 3H), 7.59-7.52 (m, 1H), 7.49 (dd, J = 11.5, 1.2 Hz, 1H), 7.39 (dd, J = 11.4, 6.2 Hz, 1H), 5.69 (s, 2H), 5.06 (qd, J = 7.0, 2.7 Hz, 1H), 4.76 (dd, J = 15.6, 7.0 Hz, 1H), 4.62 (dd, J = 15.6, 2.8 Hz, 1H), 4.57-4.40 (m, 3H), 4.35 (dt, J = 9.0, 5.9 Hz, 1H), 2.78-2.65 (m, 1H), 2.43-2.30 (m, 1H). |
| 769 | 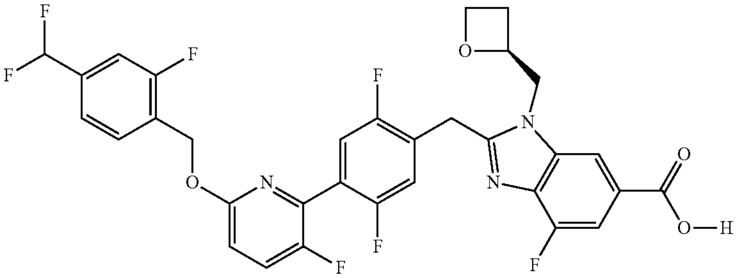 [SMILES: O=C(O)c1cc(F)c2nc(Cc3cc(F)c(-c4nc(OCc5ccc(C(F)F)cc5F)ccc4F)cc3F)n(C[C@@H]3CCO3)c2c1] ES/MS m/z 646.0; 1H NMR (400 MHz, DMSO) δ 8.15 (d, J = 1.3 Hz, 1H), 7.88 (t, J = 9.0 Hz, 1H), 7.71 (t, J = 7.6 Hz, 1H), 7.54-7.38 (m, 5H), 7.08 (dd, J = 9.1, 3.1 Hz, 1H), 7.06 (t, J = 55.6 Hz, 1H), 5.48 (s, 2H), 5.07 (qd, J = 6.9, 2.6 Hz, 1H), 4.80 (dd, J = 15.5, 7.1 Hz, 1H), 4.66 (dd, J = 15.6, 2.7 Hz, 1H), 4.60-4.44 (m, 3H), 4.35 (dt, J = 9.0, 5.9 Hz, 1H), 2.81-2.64 (m, 1H), 2.44-2.31 (m, 1H). |
| 770 | 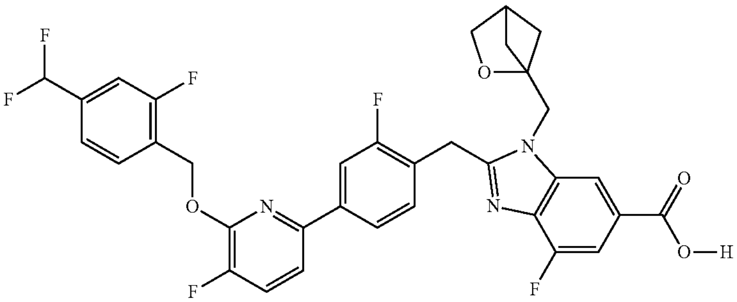 [SMILES: O=C(O)c1cc(F)c2nc(Cc3ccc(-c4ccc(F)c(OCc5ccc(C(F)F)cc5F)n4)cc3F)n(CC34CC(CO3)C4)c2c1] |

-continued

| Example | Structure/Name/Characterization |
|---|---|
| | ES/MS m/z 654.0; 1H NMR (400 MHz, DMSO) δ 8.12 (d, J = 1.3 Hz, 1H), 7.91-7.79 (m, 3H), 7.75 (t, J = 7.6 Hz, 1H), 7.69 (dd, J = 8.2, 2.8 Hz, 1H), 7.57-7.40 (m, 4H), 7.05 (t, J = 55.6 Hz, 1H), 5.68 (s, 2H), 4.78 (s, 2H), 4.46 (s, 2H), 3.63 (s, 2H), 2.88 (t, J = 3.2 Hz, 1H), 2.02-1.87 (m, 2H), 1.36-1.24 (m, 2H). |
| 771 | 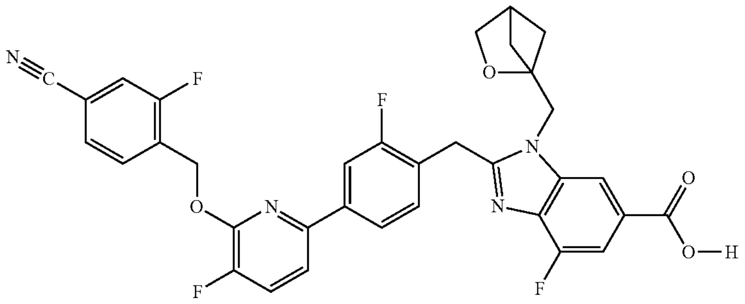 [SMILES: N#Cc1ccc(COc2nc(-c3ccc(Cc4nc5c(F)cc(C(=O)O)cc5n4CC45CC(CO4)C5)c(F)c3)ccc2F)c(F)c1] ES/MS m/z 629.2; 1H NMR (400 MHz, DMSO) δ 8.12 (d, J = 1.3 Hz, 1H), 7.94 (dd, J = 9.9, 1.5 Hz, 1H), 7.89-7.72 (m, 5H), 7.70 (dd, J = 8.2, 2.8 Hz, 1H), 7.52-7.40 (m, 2H), 5.70 (s, 2H), 4.78 (s, 2H), 4.46 (s, 2H), 3.63 (s, 2H), 2.88 (t, J = 3.1 Hz, 1H), 1.98-1.86 (m, 2H), 1.34-1.23 (m, 2H). |
| 772 | 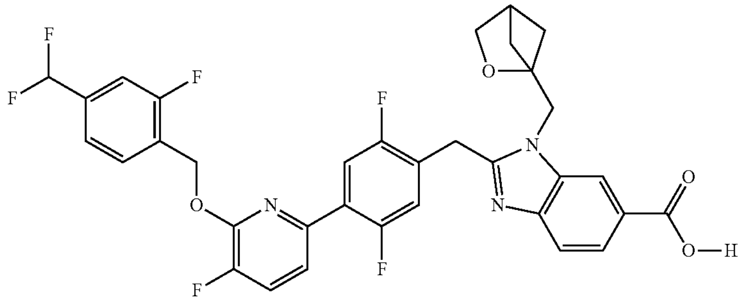 [SMILES: O=C(O)c1ccc2nc(Cc3cc(F)c(-c4ccc(F)c(OCc5ccc(C(F)F)cc5F)n4)cc3F)n(CC34CC(CO3)C4)c2c1] ES/MS m/z 654.2; 1H NMR (400 MHz, DMSO) δ 8.32 (d, J = 1.5 Hz, 1H), 7.90-7.81 (m, 2H), 7.81-7.70 (m, 2H), 7.62 (d, J = 8.4 Hz, 1H), 7.57-7.38 (m, 4H), 7.06 (t, J = 55.6 Hz, 1H), 5.66 (s, 2H), 4.84 (s, 2H), 4.52 (s, 2H), 3.63 (s, 2H), 2.89 (t, J = 3.1 Hz, 1H), 1.97-1.90 (m, 2H), 1.40-1.25 (m, 2H). |
| 773 | 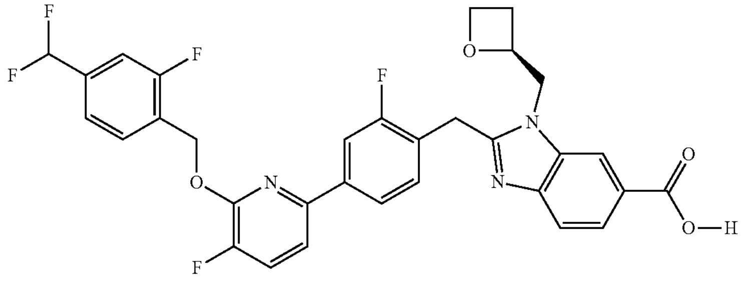 [SMILES: O=C(O)c1ccc2nc(Cc3ccc(-c4ccc(F)c(OCc5ccc(C(F)F)cc5F)n4)cc3F)n(C[C@@H]3CCO3)c2c1] ES/MS m/z 610.2; 1H NMR (400 MHz, DMSO) δ 8.23 (d, J = 1.6 Hz, 1H), 7.91-7.72 (m, 5H), 7.68 (dd, J = 8.2, 2.8 Hz, 1H), 7.57 (d, J = 8.4 Hz, 1H), 7.53-7.45 (m, 2H), 7.42 (t, J = 8.2 Hz, 1H), 7.05 (t, J = 55.6 Hz, 1H), 5.68 (s, 2H), 5.04 (qd, J = 7.1, 2.8 Hz, 1H), 4.72 (dd, J = 15.5, 7.1 Hz, 1H), 4.62-4.39 (m, 4H), 4.35 (dt, J = 9.0, 5.9 Hz, 1H), 2.81-2.63 (m, 1H), 2.44-2.31 (m, 1H). |

-continued

| Example | Structure/Name/Characterization |
|---|---|
| 774 | 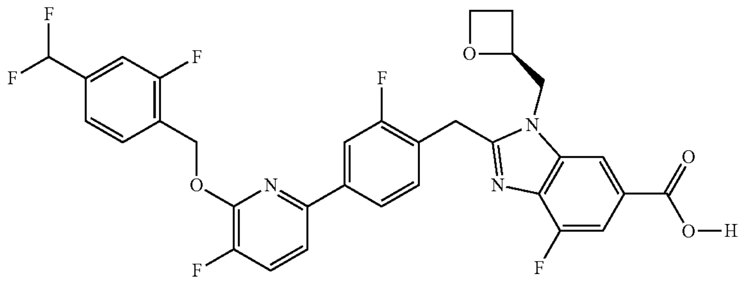 [SMILES: O=C(O)c1cc(F)c2nc(Cc3ccc(-c4ccc(F)c(OCc5ccc(C(F)F)cc5F)n4)cc3F)n(C[C@@H]3CCO3)c2c1] ES/MS m/z 628.0; 1H NMR (400 MHz, DMSO) δ 8.05 (s, 1H), 7.95-7.79 (m, 3H), 7.75 (t, J = 7.6 Hz, 1H), 7.69 (dd, J = 8.2, 2.8 Hz, 1H), 7.54-7.38 (m, 4H), 7.05 (t, J = 55.6 Hz, 1H), 5.68 (s, 2H), 5.04 (qd, J = 7.0, 2.9 Hz, 1H), 4.72 (dd, J = 15.6, 7.1 Hz, 1H), 4.64-4.39 (m, 4H), 4.39-4.30 (m, 1H), 2.74-2.61 (m, 1H), 2.41-2.25 (m, 1H). |
| 775 | 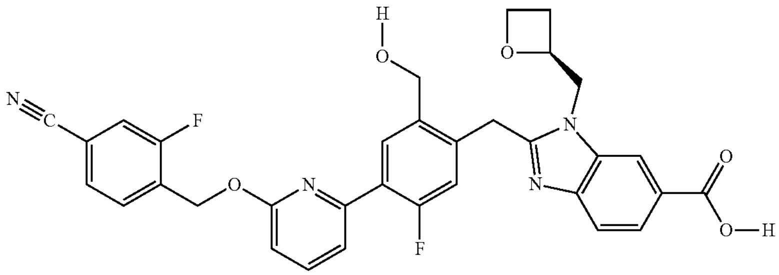 [SMILES: N#Cc1ccc(COc2cccc(-c3cc(CO)c(Cc4nc5ccc(C(=O)O)cc5n4C[C@@H]4CCO4)cc3F)n2)c(F)c1] ES/MS m/z 597.2; 1H NMR (400 MHz, DMSO-d6) δ 8.24 (s, 1H), 7.97 (d, J = 8.4 Hz, 1H), 7.95-7.83 (m, 2H), 7.83-7.77 (m, 2H), 7.73 (dd, J = 7.9, 1.5 Hz, 1H), 7.59 (d, J = 8.4 Hz, 1H), 7.45 (dd, J = 7.4, 1.8 Hz, 1H), 7.09 (d, J = 12.3 Hz, 1H), 6.95 (d, J = 8.2 Hz, 1H), 5.59 (s, 2H), 5.36 (s, 1H), 5.13-4.98 (m, 1H), 4.73 (dd, J = 15.6, 7.2 Hz, 1H), 4.66-4.46 (m, 6H), 4.46-4.32 (m, 1H), 2.79-2.62 (m, 1H), 2.46-2.34 (m, 1H). |
| 776 | 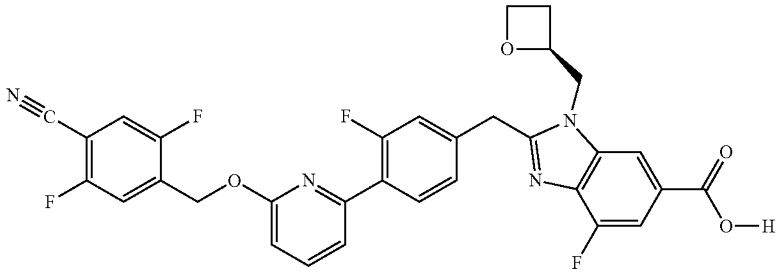 [SMILES: N#Cc1cc(F)c(COc2cccc(-c3ccc(Cc4nc5c(F)cc(C(=O)O)cc5n4C[C@@H]4CCO4)cc3F)n2)cc1F] ES/MS m/z 603.0; 1H NMR (400 MHz, DMSO-d6) δ 8.11 (s, 1H), 8.05 (dd, J = 9.2, 5.2 Hz, 1H), 7.89 (dt, J = 11.1,8.1 Hz, 2H), 7.74 (dd, J = 9.4, 5.6 Hz, 1H), 7.57-7.43 (m, 2H), 7.39-7.26 (m, 2H), 6.97 (d, J = 8.2 Hz, 1H), 5.55 (s, 2H), 4.99 (dt, J = 7.4, 3.7 Hz, 1H), 4.73 (dd, J = 15.5, 7.2 Hz, 1H), 4.65-4.52 (m, 1H), 4.48 (dd, J = 8.3, 2.7 Hz, 3H), 4.36 (dt, J = 9.1, 5.9 Hz, 1H), 2.73-2.61 (m, 1H), 2.43-2.29 (m, 1H). |
| 777 | 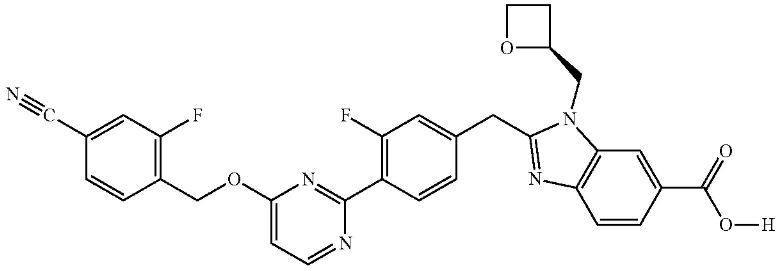 [SMILES: N#Cc1ccc(COc2ccnc(-c3ccc(Cc4nc5ccc(C(=O)O)cc5n4C[C@@H]4CCO4)cc3F)n2)c(F)c1] ES/MS m/z 568.2; 1H NMR (400 MHz, DMSO-d6) δ 8.70 (d, J = 5.7 Hz, 1H), 8.24 (d, J = 1.5 Hz, 1H), 8.02 (t, J = 8.1 Hz, 1H), 7.99-7.89 (m, 1H), 7.86- |

-continued

| Example | Structure/Name/Characterization |
|---|---|
| | 7.69 (m, 3H), 7.64 (d, J = 8.4 Hz, 1H), 7.42-7.24 (m, 2H), 7.03 (d, J = 5.8 Hz, 1H), 5.64 (s, 2H), 5.07-4.87 (m, 1H), 4.70 (dd, J = 15.5, 7.2 Hz, 1H), 4.63-4.53 (m, 1H), 4.53-4.41 (m, 3H), 4.36 (dt, J = 8.9, 5.9 Hz, 1H), 2.67 (h, J = 8.0 Hz, 1H), 2.38 (dd, J = 18.4, 9.3 Hz, 1H). |
| 778 | 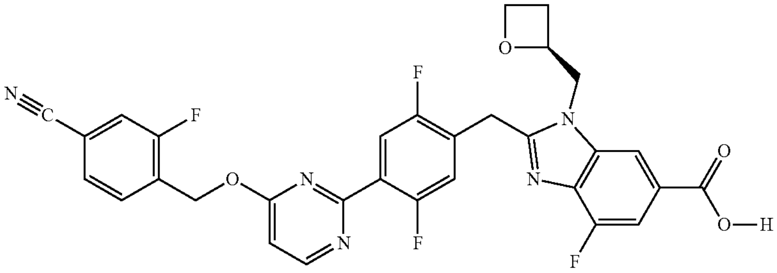 [SMILES: N#Cc1ccc(COc2ccnc(-c3cc(F)c(Cc4nc5c(F)cc(C(=O)O)cc5n4C[C@@H]4CCO4)cc3F)n2)c(F)c1] ES/MS m/z 604.2; 1H NMR (400 MHz, DMSO-d6) δ 8.74 (d, J = 5.7 Hz, 1H), 8.13 (s, 1H), 7.99-7.91 (m, 1H), 7.88 (dd, J = 10.2, 6.2 Hz, 1H), 7.83-7.72 (m, 2H), 7.50 (d, J = 11.4 Hz, 1H), 7.41 (dd, J = 11.1,6.1 Hz, 1H), 7.08 (d, J = 5.7 Hz, 1H), 5.67 (s, 2H), 5.12-5.04 (m, 1H), 4.78 (dd, J = 15.5, 6.9 Hz, 1H), 4.65 (d, J = 14.5 Hz, 1H), 4.52 (q, J = 17.1 Hz, 3H), 4.41-4.29 (m, 1H), 2.75-2.69 (m, 1H), 2.44-2.35 (m, 1H). |
| 779 | 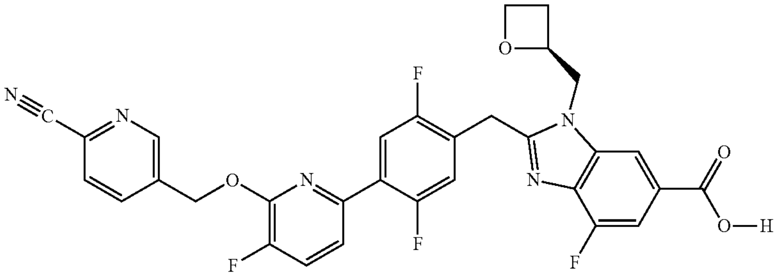 [SMILES: N#Cc1ccc(COc2nc(-c3cc(F)c(Cc4nc5c(F)cc(C(=O)O)cc5n4C[C@@H]4CCO4)cc3F)ccc2F)cn1] ES/MS m/z 604.2; 1H NMR (400 MHz, DMSO-d6) δ 8.92 (d, J = 2.0 Hz, 1H), 8.25-8.15 (m, 1H), 8.09 (d, J = 7.8 Hz, 2H), 7.88 (dd, J = 10.3, 8.2 Hz, 1H), 7.75 (dd, J = 10.0, 6.9 Hz, 1H), 7.56 (d, J = 6.6 Hz, 1H), 7.49 (d, J = 11.5 Hz, 1H), 7.40 (dd, J = 11.0, 6.5 Hz, 1H), 5.72 (s, 2H), 5.07 (d, J = 7.4 Hz, 1H), 4.76 (dd, J = 15.6, 7.0 Hz, 1H), 4.63 (d, J = 15.3 Hz, 1H), 4.59-4.40 (m, 3H), 4.36 (dd, J = 8.9, 5.8 Hz, 1H), 2.81-2.68 (m, 1H), 2.44-2.36 (m, 1H). |
| 780 | 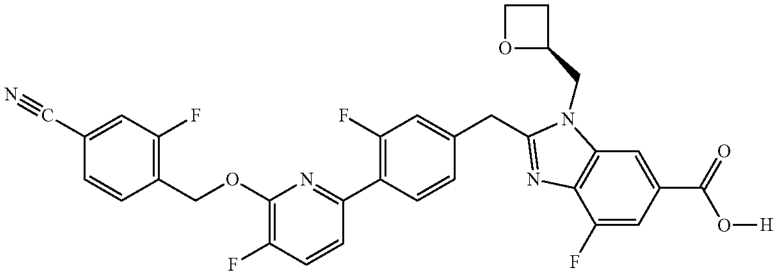 [SMILES: N#Cc1ccc(COc2nc(-c3ccc(Cc4nc5c(F)cc(C(=O)O)cc5n4C[C@@H]4CCO4)cc3F)ccc2F)c(F)c1] ES/MS m/z 603.2; 1H NMR (400 MHz, DMSO-d6) δ 8.10 (s, 1H), 7.93 (dd, J = 9.9, 1.4 Hz, 1H), 7.90-7.71 (m, 5H), 7.56-7.45 (m, 2H), 7.38-7.25 (m, 2H), 5.66 (s, 2H), 5.05-4.91 (m, 1H), 4.72 (dd, J = 15.5, 7.2 Hz, 1H), 4.67-4.42 (m, 4H), 4.36 (dt, J = 9.0, 5.9 Hz, 1H), 2.77-2.60 (m, 1H), 2.44-2.25 (m, 1H). |

-continued

| Example | Structure/Name/Characterization |
|---|---|
| 781 | 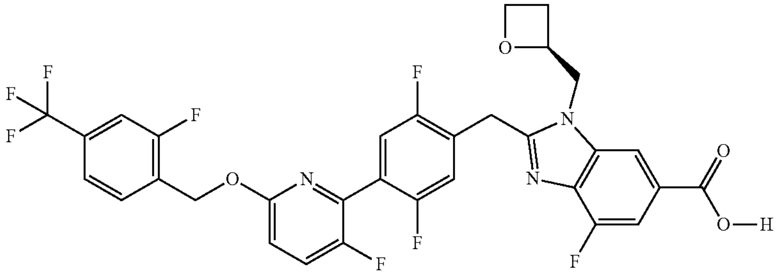 [SMILES: O=C(O)c1cc(F)c2nc(Cc3cc(F)c(-c4nc(OCc5ccc(C(F)(F)F)cc5F)ccc4F)cc3F)n(C[C@@H]3CCO3)c2c1]<br>ES/MS m/z 664.0; 1H NMR (400 MHz, DMSO-d6) δ 8.14 (d, J = 1.2 Hz, 1H), 7.90 (t, J = 8.9 Hz, 1H), 7.80 (t, J = 7.6 Hz, 1H), 7.74 (dd, J = 10.1, 1.7 Hz, 1H), 7.63 (dd, J = 8.1, 1.7 Hz, 1H), 7.54-7.36 (m, 3H), 7.11 (dd, J = 9.0, 2.9 Hz, 1H), 5.52 (s, 2H), 5.08 (qd, J = 7.0, 2.6 Hz, 1H), 4.79 (dd, J = 15.5, 7.1 Hz, 1H), 4.71-4.42 (m, 4H), 4.36 (dt, J = 9.0, 5.9 Hz, 1H), 2.72 (dtd, J = 11.2, 8.3, 6.3 Hz, 1H), 2.39 (ddt, J = 11.3, 8.9, 7.0 Hz, 1H). |
| 782 | 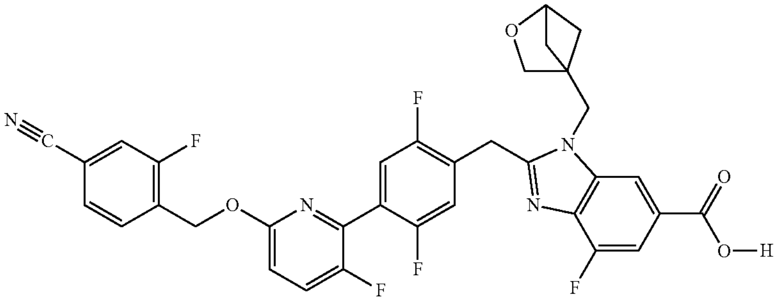 [SMILES: N#Cc1ccc(COc2ccc(F)c(-c3cc(F)c(Cc4nc5c(F)cc(C(=O)O)cc5n4CC45COC(C4)C5)cc3F)n2)c(F)c1]<br>ES/MS m/z 647.2; 1H NMR (400 MHz, DMSO-d6) δ 8.11 (d, J = 1.2 Hz, 1H), 7.96-7.85 (m, 2H), 7.75 (d, J = 6.1 Hz, 2H), 7.56-7.49 (m, 2H), 7.49-7.39 (m, 1H), 7.11 (dd, J = 9.0, 3.0 Hz, 1H), 5.51 (s, 2H), 4.87 (s, 2H), 4.41 (s, 3H), 3.60 (s, 2H), 1.62 (d, J = 4.6 Hz, 2H), 1.50 (dd, J = 4.5, 1.6 Hz, 2H). |
| 783 | 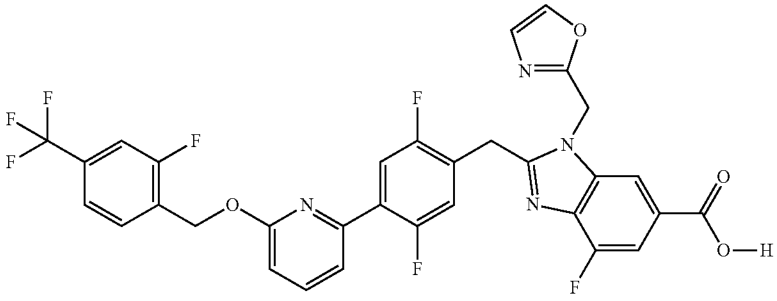 [SMILES: O=C(O)c1cc(F)c2nc(Cc3cc(F)c(-c4cccc(OCc5ccc(C(F)(F)F)cc5F)n4)cc3F)n(Cc3ncco3)c2c1]<br>ES/MS m/z 657.2; 1H NMR (400 MHz, DMSO-d6) δ 8.14 (d, J = 1.3 Hz, 1H), 8.08 (d, J = 0.9 Hz, 1H), 7.93-7.85 (m, 1H), 7.83-7.66 (m, 3H), 7.63 (d, J = 8.0 Hz, 1H), 7.60-7.45 (m, 2H), 7.32 (dd, J = 11.5, 6.1 Hz, 1H), 7.14 (d, J = 0.9 Hz, 1H), 6.99 (d, J = 8.3 Hz, 1H), 5.97 (s, 2H), 5.61 (s, 2H), 4.50 (s, 2H). |
| 784 | 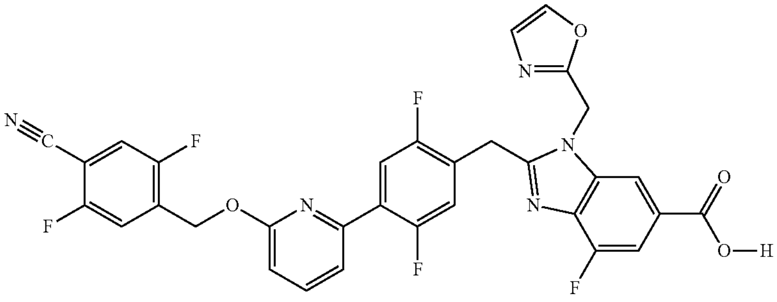 [SMILES: N#Cc1cc(F)c(COc2cccc(-c3cc(F)c(Cc4nc5c(F)cc(C(=O)O)cc5n4Cc4ncco4)cc3F)n2)cc1F]<br>ES/MS m/z 632.2; 1H NMR (400 MHz, DMSO-d6) δ 8.14 (d, J = 1.2 Hz, 1H), 8.11-8.01 (m, 2H), 7.95-7.86 (m, 1H), 7.79-7.67 (m, 2H), 7.59-7.49 (m, |

-continued

| Example | Structure/Name/Characterization |
|---|---|
| | 2H), 7.33 (dd, J = 11.5, 6.1 Hz, 1H), 7.15 (s, 1H), 7.01 (d, J = 8.3 Hz, 1H), 5.97 (s, 2H), 5.58 (s, 2H), 4.50 (s, 2H). |
| 785 | 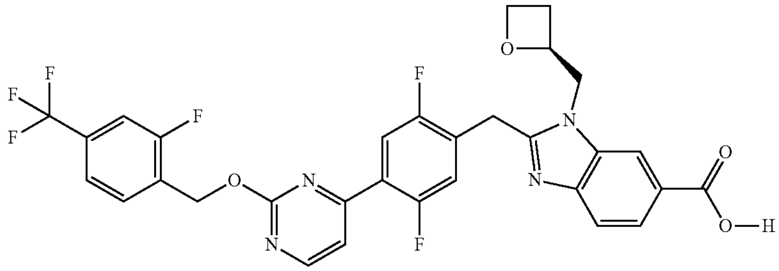 [SMILES: O=C(O)c1ccc2nc(Cc3cc(F)c(-c4ccnc(OCc5ccc(C(F)(F)F)cc5F)n4)cc3F)n(C[C@@H]3CCO3)c2c1]<br>ES/MS m/z 629.2; 1H NMR (400 MHz, DMSO-d6) δ 8.79 (d, J = 5.2 Hz, 1H), 8.26 (d, J = 1.5 Hz, 1H), 7.90 (dd, J = 10.2, 6.2 Hz, 1H), 7.87-7.73 (m, 3H), 7.70-7.62 (m, 2H), 7.59 (d, J = 8.4 Hz, 1H), 7.48 (dd, J = 11.5, 5.9 Hz, 1H), 5.65 (s, 2H), 5.07 (dd, J = 8.0, 5.4 Hz, 1H), 4.76 (dd, J = 15.6, 7.0 Hz, 1H), 4.68-4.56 (m, 1H), 4.56-4.42 (m, 3H), 4.35 (dt, J = 9.0, 5.9 Hz, 1H), 2.80-2.63 (m, 1H), 2.45-2.30 (m, 1H). |
| 786 | 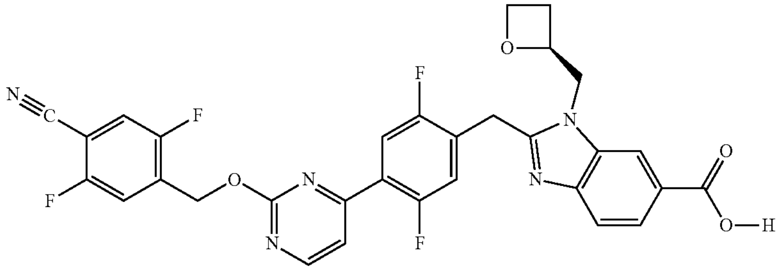 [SMILES: N#Cc1cc(F)c(COc2nccc(-c3cc(F)c(Cc4nc5ccc(C(=O)O)cc5n4C[C@@H]4CCO4)cc3F)n2)cc1F]<br>ES/MS m/z 604.2; 1H NMR (400 MHz, DMSO-d6) δ 8.79 (d, J = 5.2 Hz, 1H), 8.25 (d, J = 1.5 Hz, 1H), 8.08 (dd, J = 9.2, 5.2 Hz, 1H), 7.90 (dd, J = 10.2, 6.2 Hz, 1H), 7.82-7.71 (m, 2H), 7.65 (dd, J = 5.1, 1.8 Hz, 1H), 7.59 (d, J = 8.4 Hz, 1H), 7.48 (dd, J = 11.5, 5.9 Hz, 1H), 5.62 (s, 2H), 5.07 (dd, J = 7.9, 5.4 Hz, 1H), 4.76 (dd, J = 15.6, 7.0 Hz, 1H), 4.69-4.57 (m, 1H), 4.57-4.43 (m, 3H), 4.35 (dt, J = 9.1, 6.0 Hz, 1H), 2.80-2.58 (m, 1H), 2.44-2.30 (m, 1H). |
| 787 | 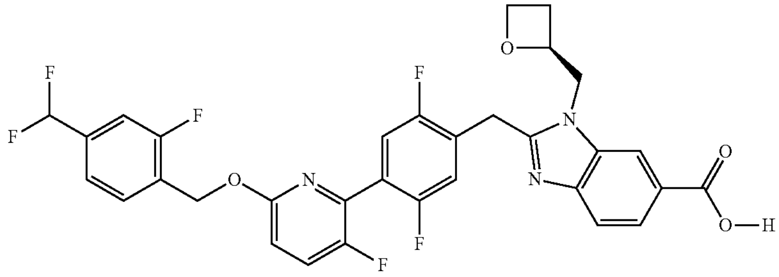 [SMILES: O=C(O)c1ccc2nc(Cc3cc(F)c(-c4nc(OCc5ccc(C(F)F)cc5F)ccc4F)cc3F)n(C[C@@H]3CCO3)c2c1]<br>ES/MS m/z 628.2; 1H NMR (400 MHz, DMSO-d6) δ 8.26 (d, J = 1.5 Hz, 1H), 7.89 (t, J = 9.0 Hz, 1H), 7.79 (dd, J = 8.4, 1.6 Hz, 1H), 7.72 (t, J = 7.6 Hz, 1H), 7.61 (d, J = 8.4 Hz, 1H), 7.53-7.37 (m, 4H), 7.23-6.90 (m, 2H), 5.48 (s, 2H), 5.09 (qd, J = 7.0, 2.7 Hz, 1H), 4.77 (dd, J = 15.6, 7.0 Hz, 1H), 4.70-4.42 (m, 4H), 4.36 (dt, J = 9.0, 5.9 Hz, 1H), 2.73 (dtd, J = 11.3, 8.1, 6.2 Hz, 1H), 2.40 (ddt, J = 11.2, 9.0, 6.9 Hz, 1H). |
| 788 | 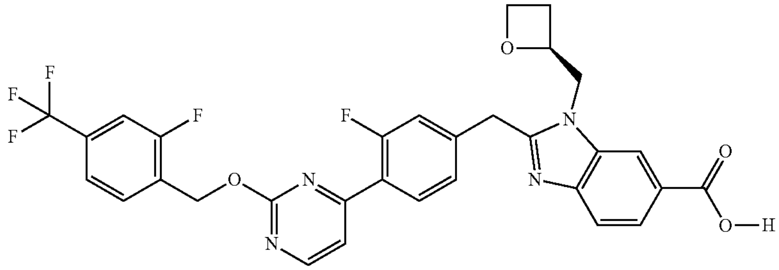 [SMILES: O=C(O)c1ccc2nc(Cc3ccc(-c4ccnc(OCc5ccc(C(F)(F)F)cc5F)n4)c(F)c3)n(C[C@@H]3CCO3)c2c1] |

-continued

| Example | Structure/Name/Characterization |
|---|---|
| | ES/MS m/z 611.2; 1H NMR (400 MHz, DMSO-d6) δ 8.74 (d, J = 5.2 Hz, 1H), 8.25 (d, J = 1.5 Hz, 1H), 8.06 (t, J = 8.2 Hz, 1H), 7.88-7.71 (m, 3H), 7.64 (t, J = 7.6 Hz, 2H), 7.58 (dd, J = 5.2, 1.9 Hz, 1H), 7.46-7.28 (m, 2H), 5.62 (s, 2H), 5.05-4.93 (m, 1H), 4.71 (dd, J = 15.5, 7.2 Hz, 1H), 4.63-4.42 (m, 4H), 4.35 (dt, J = 9.1, 5.9 Hz, 1H), 2.77-2.60 (m, 1H), 2.37 (dt, J = 18.2, 7.2 Hz, 1H). |
| 789 | 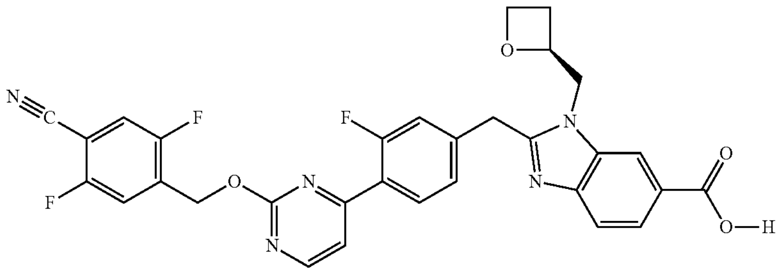 [SMILES: N#Cc1cc(F)c(COc2nccc(-c3ccc(Cc4nc5ccc(C(=O)O)cc5n4C[C@@H]4CCO4)cc3F)n2)cc1F] ES/MS m/z 586.2; H NMR (400 MHz, DMSO-d6) δ 12.77 (s, 1H), 8.74 (d, J = 5.2 Hz, 1H), 8.25 (d, J = 1.5 Hz, 1H), 8.13-7.99 (m, 2H), 7.80 (dd, J = 8.4, 1.6 Hz, 1H), 7.74 (dd, J = 9.3, 5.6 Hz, 1H), 7.69-7.55 (m, 2H), 7.45-7.31 (m, 2H), 5.58 (s, 2H), 5.00 (qd, J = 7.1, 2.7 Hz, 1H), 4.71 (dd, J = 15.5, 7.2 Hz, 1H), 4.58 (dd, J = 15.6, 3.0 Hz, 1H), 4.55-4.42 (m, 3H), 4.35 (dt, J = 9.0, 5.9 Hz, 1H), 2.68 (dtd, J = 11.1, 8.1, 6.2 Hz, 1H), 2.37 (ddt, J = 11.1, 8.8, 6.8 Hz, 1H). |
| 790 | 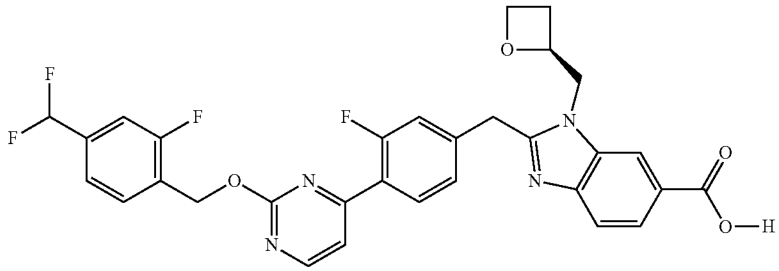 [SMILES: O=C(O)c1ccc2nc(Cc3ccc(-c4ccnc(OCc5ccc(C(F)F)cc5F)n4)c(F)c3)n(C[C@@H]3CCO3)c2c1] ES/MS m/z 593.2; 1H NMR (400 MHz, DMSO-d6) δ 8.73 (d, J = 5.2 Hz, 1H), 8.22 (d, J = 1.5 Hz, 1H), 8.06 (t, J = 8.1 Hz, 1H), 7.80 (dd, J = 8.4, 1.5 Hz, 1H), 7.74 (t, J = 7.6 Hz, 1H), 7.64-7.54 (m, 2H), 7.54-7.44 (m, 2H), 7.43-7.30 (m, 2H), 7.07 (t, J = 55.6 Hz, 1H), 5.58 (s, 2H), 5.00 (qd, J = 7.1, 2.8 Hz, 1H), 4.70 (dd, J = 15.5, 7.2 Hz, 1H), 4.62-4.42 (m, 4H), 4.35 (dt, J = 9.0, 5.9 Hz, 1H), 2.67 (dtd, J = 11.2, 8.1, 6.2 Hz, 1H), 2.37 (ddt, J = 11.1, 8.7, 6.8 Hz, 1H). |
| 791 | 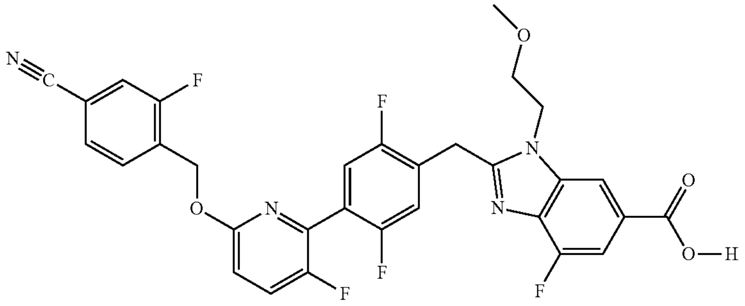 [SMILES: COCCn1c(Cc2cc(F)c(-c3nc(OCc4ccc(C#N)cc4F)ccc3F)cc2F)nc2c(F)cc(C(=O)O)cc21] ES/MS m/z 609.2; 1H NMR (400 MHz, DMSO) δ 8.10 (d, J = 1.3 Hz, 1H), 7.95-7.85 (m, 2H), 7.75 (d, J = 5.7 Hz, 2H), 7.51 (dd, J = 11.4, 1.3 Hz, 1H), 7.44 (ddd, J = 18.7, 9.9, 5.9 Hz, 2H), 7.11 (dd, J = 9.0, 3.0 Hz, 1H), 5.51 (s, 2H), 4.63 (t, J = 5.1 Hz, 2H), 4.48 (s, 2H), 3.68 (t, J = 5.0 Hz, 2H), 3.21 (s, 3H). |

-continued

| Example | Structure/Name/Characterization |
|---|---|
| 792 | 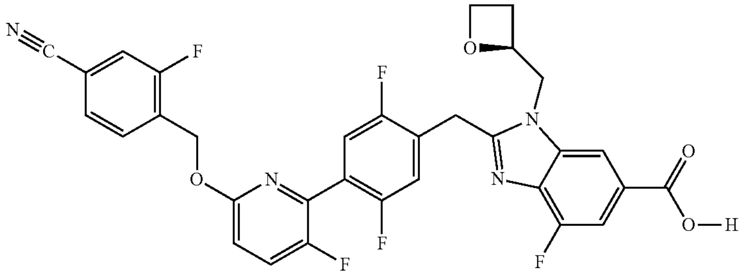 [SMILES: N#Cc1ccc(COc2ccc(F)c(-c3cc(F)c(Cc4nc5c(F)cc(C(=O)O)cc5n4C[C@@H]4CCO4)cc3F)n2)c(F)c1] ES/MS m/z 621.241; 1H NMR (400 MHz, DMSO) δ 8.16 (d, J = 1.3 Hz, 1H), 7.95-7.85 (m, 2H), 7.75 (d, J = 6.0 Hz, 2H), 7.55-7.40 (m, 3H), 7.11 (dd, J = 9.0, 3.0 Hz, 1H), 5.51 (s, 2H), 5.08 (d, J = 7.2 Hz, 1H), 4.80 (dd, J = 15.6, 7.1 Hz, 1H), 4.66 (d, J = 14.5 Hz, 1H), 4.62-4.43 (m, 3H), 4.36 (dt, J = 9.0, 5.9 Hz, 1H), 2.79-2.68 (m, 1H), 2.44-2.34 (m, 1H). |
| 793 | 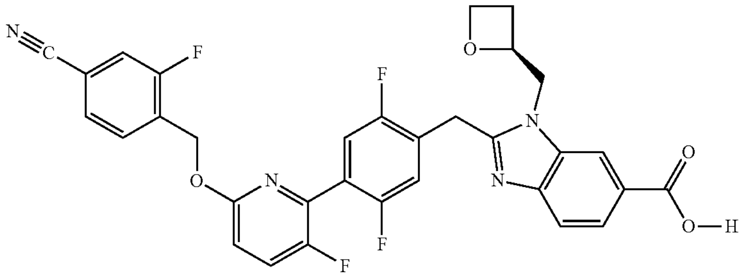 [SMILES: N#Cc1ccc(COc2ccc(F)c(-c3cc(F)c(Cc4nc5ccc(C(=O)O)cc5n4C[C@@H]4CCO4)cc3F)n2)c(F)c1] ES/MS m/z 603.238; 1H NMR (400 MHz, DMSO) δ 8.22 (s, 1H), 7.95-7.85 (m, 2H), 7.83-7.71 (m, 3H), 7.56 (d, J = 8.4 Hz, 1H), 7.43 (ddd, J = 13.6, 9.9, 5.9 Hz, 2H), 7.11 (dd, J = 9.0, 3.0 Hz, 1H), 5.51 (s, 2H), 5.09 (td, J = 7.1, 2.7 Hz, 1H), 4.74 (dd, J = 15.6, 6.9 Hz, 1H), 4.66-4.58 (m, 1H), 4.57-4.41 (m, 3H), 4.36 (dt, J = 9.0, 6.0 Hz, 1H), 2.79-2.65 (m, 1H), 2.45-2.36 (m, 1H). |
| 794 | 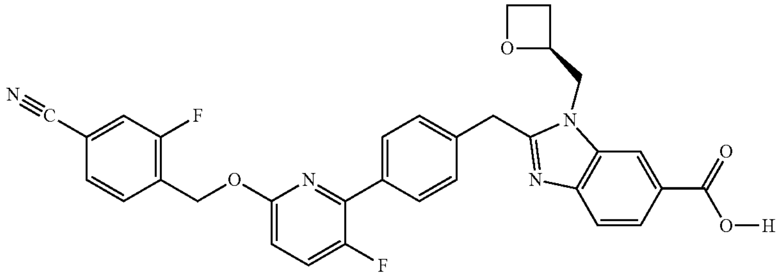 [SMILES: N#Cc1ccc(COc2ccc(F)c(-c3ccc(Cc4nc5ccc(C(=O)O)cc5n4C[C@@H]4CCO4)cc3)n2)c(F)c1] ES/MS m/z 567.3; 1H NMR (400 MHz, DMSO-d6) δ 8.24 (d, J = 1.5 Hz, 1H), 7.97-7.90 (m, 1H), 7.90-7.83 (m, 2H), 7.83-7.78 (m, 2H), 7.78-7.69 (m, 2H), 7.63 (d, J = 8.4 Hz, 1H), 7.52-7.35 (m, 2H), 6.97 (dd, J = 8.8, 2.6 Hz, 1H), 5.55 (s, 2H), 4.96 (qd, J = 7.0, 2.7 Hz, 1H), 4.68 (dd, J = 15.5, 7.2 Hz, 1H), 4.61-4.40 (m, 4H), 4.36 (dt, J = 9.0, 5.9 Hz, 1H), 2.65 (dtd, J = 11.2, 8.1, 6.2 Hz, 1H), 2.35 (ddt, J = 11.2, 8.9, 7.0 Hz, 1H). |
| 795 | 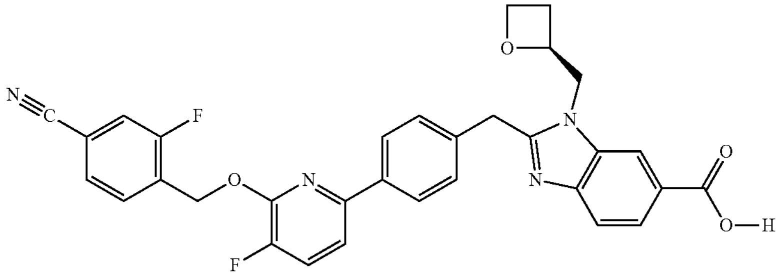 [SMILES: N#Cc1ccc(COc2nc(-c3ccc(Cc4nc5ccc(C(=O)O)cc5n4C[C@@H]4CCO4)cc3)ccc2F)c(F)c1] ES/MS m/z 567.3; 1H NMR (400 MHz, DMSO-d6) δ 8.23 (d, J = 1.5 Hz, 1H), 8.00-7.90 (m, 3H), 7.85-7.71 (m, 4H), 7.67-7.57 (m, 2H), 7.42 (d, J = 8.1 Hz, 2H), 5.69 (s, 2H), 4.94 (qd, J = 7.1, 2.7 Hz, 1H), 4.66 (dd, J = 15.5, 7.2 Hz, |

-continued

| Example | Structure/Name/Characterization |
|---|---|
| | 1H), 4.53 (dd, J = 15.5, 2.8 Hz, 1H), 4.50-4.41 (m, 3H), 4.41-4.30 (m, 1H), 2.70-2.59 (m, 1H), 2.34 (ddt, J = 11.4, 9.2, 7.0 Hz, 1H). |
| 796 | 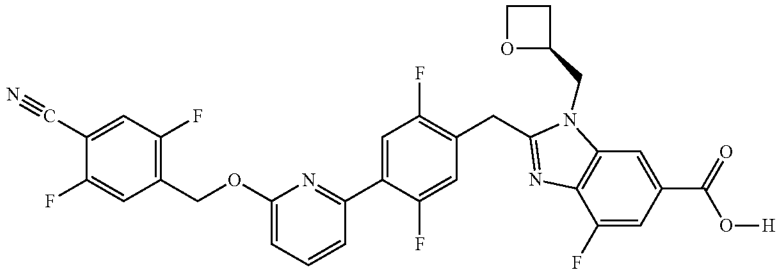 [SMILES: N#Cc1cc(F)c(COc2cccc(-c3cc(F)c(Cc4nc5c(F)cc(C(=O)O)cc5n4C[C@@H]4CCO4)cc3F)n2)cc1F] ES/MS m/z 621.3; 1H NMR (400 MHz, DMSO-d6) δ 8.16 (d, J = 1.3 Hz, 1H), 8.06 (dd, J = 9.2, 5.2 Hz, 1H), 7.91 (t, J = 7.9 Hz, 1H), 7.84-7.68 (m, 2H), 7.62-7.46 (m, 2H), 7.41 (dd, J = 11.5, 6.1 Hz, 1H), 7.02 (d, J = 8.3 Hz, 1H), 5.59 (s, 2H), 5.07 (td, J = 7.2, 2.6 Hz, 1H), 4.79 (dd, J = 15.6, 7.1 Hz, 1H), 4.66 (dd, J = 15.6, 2.8 Hz, 1H), 4.62-4.41 (m, 3H), 4.36 (dt, J = 9.0, 5.9 Hz, 1H), 2.79-2.62 (m, 1H), 2.45-2.28 (m, 1H). |
| 797 | 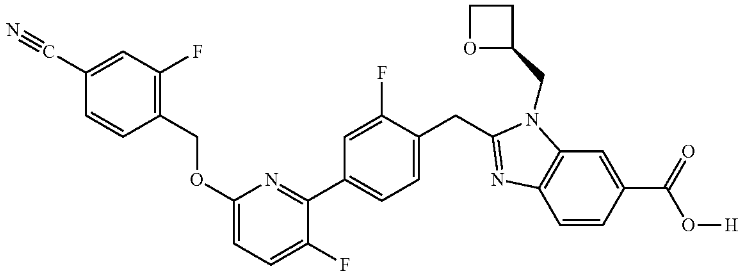 [SMILES: N#Cc1ccc(COc2ccc(F)c(-c3ccc(Cc4nc5ccc(C(=O)O)cc5n4C[C@@H]4CCO4)c(F)c3)n2)c(F)c1] ES/MS m/z 585.3; 1H NMR (400 MHz, DMSO-d6) δ 8.35 (d, J = 1.5 Hz, 1H), 7.97-7.91 (m, 1H), 7.91-7.83 (m, 2H), 7.81-7.69 (m, 4H), 7.65 (d, J = 8.5 Hz, 1H), 7.52 (t, J = 8.0 Hz, 1H), 7.04 (dd, J = 8.9, 2.7 Hz, 1H), 5.57 (s, 2H), 5.07 (qd, J = 7.2, 2.7 Hz, 1H), 4.83 (dd, J = 15.5, 7.2 Hz, 1H), 4.68 (dd, J = 15.6, 2.9 Hz, 1H), 4.66-4.46 (m, 3H), 4.39 (dt, J = 9.0, 5.9 Hz, 1H), 2.80-2.62 (m, 1H), 2.46-2.35 (m, 1H). |
| 798 | 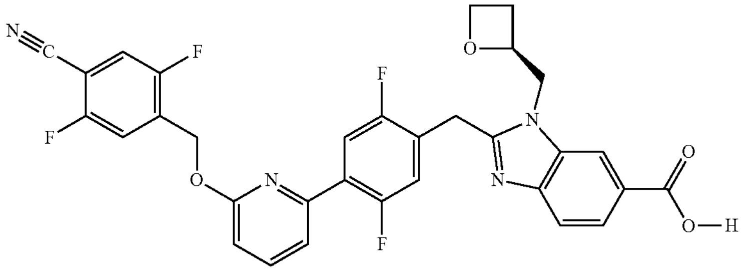 [SMILES: N#Cc1cc(F)c(COc2cccc(-c3cc(F)c(Cc4nc5ccc(C(=O)O)cc5n4C[C@@H]4CCO4)cc3F)n2)cc1F] ES/MS m/z 603.3; 1H NMR (400 MHz, DMSO-d6) δ 8.34 (d, J = 1.5 Hz, 1H), 8.06 (dd, J = 9.2, 5.2 Hz, 1H), 7.91 (t, J = 7.9 Hz, 1H), 7.85 (dd, J = 8.4, 1.5 Hz, 1H), 7.76 (dt, J = 9.4, 6.1 Hz, 2H), 7.65 (d, J = 8.4 Hz, 1H), 7.54 (dd, J = 7.5, 1.7 Hz, 1H), 7.43 (dd, J = 11.5, 6.1 Hz, 1H), 7.02 (d, J = 8.2 Hz, 1H), 5.59 (s, 2H), 5.09 (qd, J = 7.1, 2.6 Hz, 1H), 4.82 (dd, J = 15.5, 7.2 Hz, 1H), 4.68 (dd, J = 15.5, 2.7 Hz, 1H), 4.63-4.46 (m, 3H), 4.38 (dt, J = 9.1, 5.9 Hz, 1H), 2.79-2.65 (m, 1H), 2.45-2.35 (m, 1H). |

-continued

| Example | Structure/Name/Characterization |
| --- | --- |
| 799 | 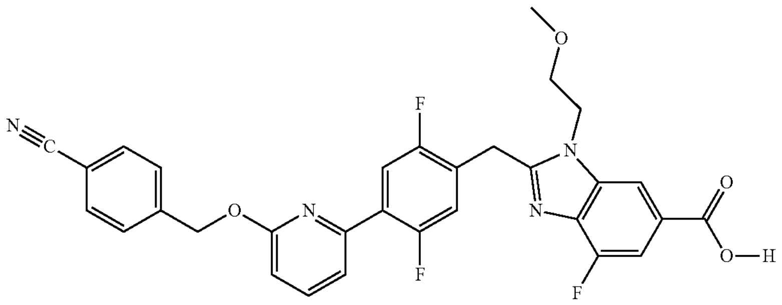 [SMILES: COCCn1c(Cc2cc(F)c(-c3cccc(OCc4ccc(C#N)cc4)n3)cc2F)nc2c(F)cc(C(=O)O)cc21] ES/MS m/z 573.4; 1H NMR (400 MHz, Methanol-d4) δ 8.73 (d, J = 6.8 Hz, 1H), 8.15 (d, J = 1.2 Hz, 1H), 7.87-7.78 (m, 3H), 7.77-7.63 (m, 4H), 7.58 (dd, J = 6.8, 2.6 Hz, 1H), 7.42 (dd, J = 10.6, 5.8 Hz, 1H), 5.58 (s, 2H), 4.62 (t, J = 5.0 Hz, 2H), 4.58 (s, 2H), 3.81-3.72 (m, 2H), 3.29 (s, 3H). |
| 800 | 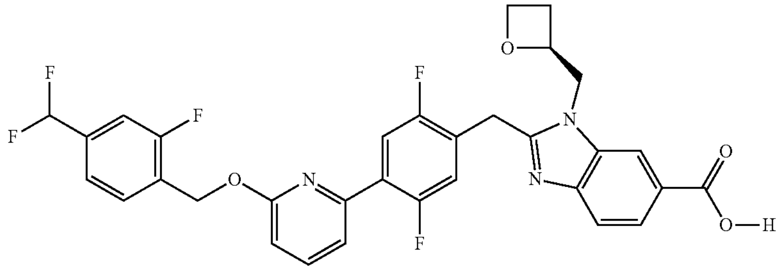 [SMILES: O=C(O)c1ccc2nc(Cc3cc(F)c(-c4cccc(OCc5ccc(C(F)F)cc5F)n4)cc3F)n(C[C@@H]3CCO3)c2c1] ES/MS m/z 610.5; 1H NMR (400 MHz, DMSO-d6) δ 8.31 (d, J = 1.5 Hz, 1H), 7.97-7.77 (m, 3H), 7.72 (t, J = 7.6 Hz, 1H), 7.64 (d, J = 8.4 Hz, 1H), 7.59-7.34 (m, 4H), 7.24-6.88 (m, 2H), 5.58 (s, 2H), 5.08 (qd, J = 7.1, 2.6 Hz, 1H), 4.80 (dd, J = 15.6, 7.1 Hz, 1H), 4.66 (dd, J = 15.5, 2.8 Hz, 1H), 4.62-4.44 (m, 3H), 4.37 (dt, J = 9.0, 5.9 Hz, 1H), 2.89-2.65 (m, 1H), 2.46-2.31 (m, 1H). 19F NMR (377 MHz, DMSO-d6) δ −75.07, −110.78 (d, J = 55.6 Hz), −117.21 (dd, J = 10.2, 7.5 Hz), −120.73--123.55 (m). |
| 801 | 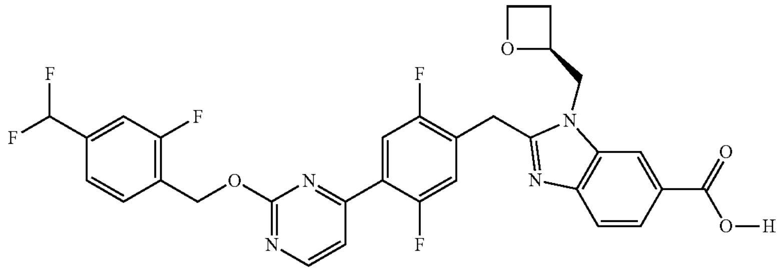 [SMILES: O=C(O)c1ccc2nc(Cc3cc(F)c(-c4ccnc(OCc5ccc(C(F)F)cc5F)n4)cc3F)n(C[C@@H]3CCO3)c2c1] ES/MS m/z 611.7; 1H NMR (400 MHz, DMSO-d6) δ 8.78 (d, J = 5.2 Hz, 1H), 8.31 (d, J = 1.5 Hz, 1H), 7.93 (dd, J = 10.2, 6.3 Hz, 1H), 7.83 (dd, J = 8.5, 1.6 Hz, 1H), 7.75 (t, J = 7.6 Hz, 1H), 7.66-7.58 (m, 2H), 7.55-7.45 (m, 3H), 7.07 (t, J = 55.6 Hz, 1H), 5.61 (s, 2H), 5.08 (qd, J = 7.0, 2.6 Hz, 1H), 4.80 (dd, J = 15.5, 7.1 Hz, 1H), 4.72-4.47 (m, 4H), 4.37 (dt, J = 9.0, 5.9 Hz, 1H), 2.79-2.64 (m, 1H), 2.46-2.25 (m, 1H). 19F NMR (377 MHz, DMSO-d6) δ −75.14, −110.87 (d, J = 55.8 Hz), −117.08 (dd, J = 10.3, 7.5 Hz), −120.16 (ddd, J = 18.0, 11.6, 6.5 Hz), −121.69 (ddd, J = 17.0, 10.1, 6.0 Hz). |

Example 446. 2-(4-(2-((4-chloro-2-methoxybenzyl)oxy)pyrimidin-4-yl)-2,5-difluorobenzyl)-1-((1-(cyanomethyl)cyclopropyl)methyl)-1H-benzo[d]imidazole-6-carboxylic acid Procedure 53

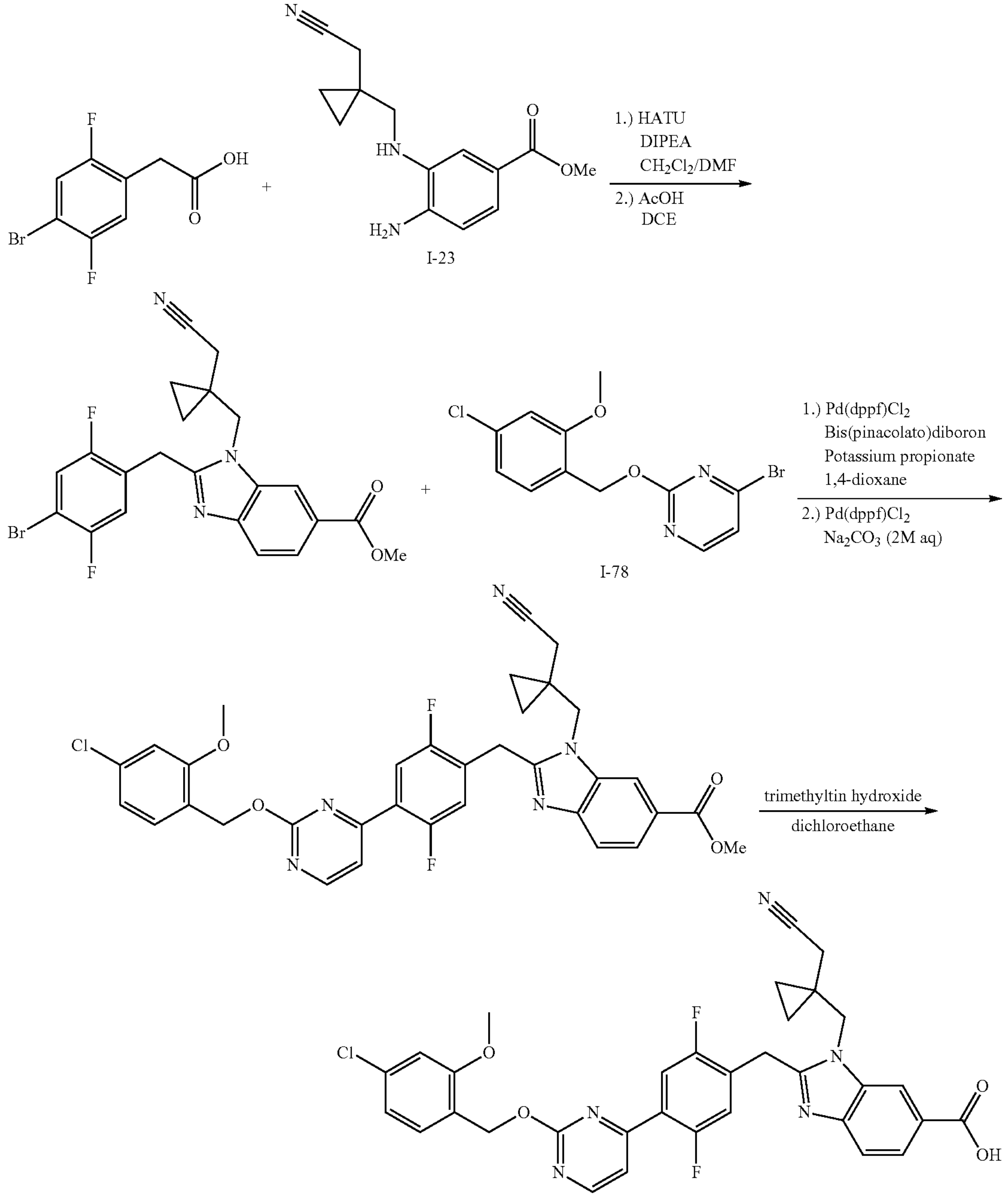

I-23

I-78

Example 446

Methyl 2-(4-bromo-2,5-difluorobenzyl)-1-((1-(cyanomethyl)cyclopropyl)methyl)-1H-benzo[d]imidazole-6-carboxylate: To a solution of 2-(4-bromo-2,5-difluorophenyl)acetic acid (174 mg, 0.69 mmol), methyl 4-amino-3-(((1-(cyanomethyl)cyclopropyl)methyl)amino)benzoate (I-23) (150 mg, 0.58 mmol), and O-(7-azabenzotriazol-1-yl)-N,N,N',N'-tetramethyluronium hexafluorophosphate (HATU) (177 mg, 0.47 mmol) in DCM (8 mL) and DMF (2 mL) was added DIPEA (0.5 mL, 2.9 mmol). The mixture was stirred at RT for 16 hours, then diluted with EtOAc (50 mL). The mixture was washed with sat. aq. $NH_4Cl$ (2×10 mL) and sat. aq. $NaHCO_3$ (1×10 mL). The organic layer was dried over $MgSO_4$, filtered, and concentrated under reduced pressure. The crude residue was dissolved in 1,2-dichloroethane (4 mL) and AcOH (2 mL). The mixture was stirred at 70° C. for 16 hours. The mixture was concentrated under reduced pressure and purified by silica gel column chromatography (eluent: EtOAc/Hex) to provide the desired product. ES/MS: 474.3 (M+).

Methyl 2-(4-(2-((4-chloro-2-methoxybenzyl)oxy)pyrimidin-4-yl)-2,5-difluorobenzyl)-1-((1-(cyanomethyl)cyclopropyl)methyl)-1H-benzo[d]imidazole-6-carboxylate: To a vial was added methyl 2-(4-bromo-2,5-difluorobenzyl)-1-((1-(cyanomethyl)cyclopropyl)methyl)-1H-benzo[d]imidazole-6-carboxylate (50 mg, 0.11 mmol), potassium propionate (36 mg, 0.32 mmol), bis(pinacolato)diboron (35 mg, 0.14 mmol), 1,1'-bis(diphenylphosphino)ferrocene]dichloropalladium(II) (12 mg, 0.016 mmol) and dioxane (1.0 mL). The resulting mixture was degassed by bubbling argon below the liquid surface for 1 minute after which the vial was sealed and placed in a 110° C. heating block for 30 minutes. Upon cooling the vial was opened and to the mixture was added 4-bromo-2-((4-chloro-2-methoxybenzyl)oxy)pyrimidine (35 mg, 0.11 mmol) (I-78), 1,1'-bis(diphenylphosphino)ferrocene]dichloropalladium(II) (6 mg, 0.008 mmol) and potassium carbonate (2 M aq. solution, 0.11 mL, 0.21 mmol). The vial was sealed, then heated in a sealed tube at 80° C. for 1 hour. The mixture was cooled, and directly added to a silica loading column. The crude material was purified by silica gel column chromatography (eluent: EtOAc/Hex) to provide the desired product. ES/MS: 644.2 (M+).

2-(4-(2-((4-chloro-2-methoxybenzyl)oxy)pyrimidin-4-yl)-2,5-difluorobenzyl)-1-((1-(cyanomethyl)cyclopropyl)methyl)-1H-benzo[d]imidazole-6-carboxylic acid (Example 446): To a 40 mL vial was added methyl 2-(4-(2-((4-chloro-2-methoxybenzyl)oxy)pyrimidin-4-yl)-2,5-difluorobenzyl)-1-((1-(cyanomethyl)cyclopropyl)methyl)-1H-benzo[d]imidazole-6-carboxylate (43 mg, 0.067 mmol), and 1,2-dichloroethane (1 mL) was added. To the mixture was added trimethyltin hydroxide (121 mg, 0.67 mmol), and the mixture was stirred 7 days at 80° C. LCMS showed significant conversion of the starting material to the product. The mixture was concentrated under reduced pressure, and acetonitrile (1.5 mL) and DMSO (0.3 mL) were added. The mixture was filtered through an acrodisc, and the filtrate was purified by RP-HPLC (eluent: water/MeCN*0.1% TFA) to yield the product Example 446 as a trifluoroacetate salt. ES/MS: 630.1 (M+); $^1$H NMR (400 MHz, DMSO-d6) δ 8.77 (d, J=5.2 Hz, 1H), 8.29 (d, J=1.5 Hz, 1H), 7.91 (dd, J=10.2, 6.3 Hz, 1H), 7.81 (dd, J=8.4, 1.5 Hz, 1H), 7.65-7.58 (m, 2H), 7.53 (dd, J=11.5, 5.9 Hz, 1H), 7.45 (d, J=8.1 Hz, 1H), 7.16 (d, J=2.0 Hz, 1H), 7.04 (dd, J=8.1, 2.0 Hz, 1H), 5.45 (s, 2H), 4.57 (s, 2H), 4.49 (s, 2H), 3.87 (s, 3H), 2.68 (s, 3H), 0.77-0.67 (m, 4H).

Example 233, 268, 280, 298, 414. Compounds Prepared Using Procedure 53

Other compounds of the present disclosure prepared using the general route described in Procedure 53 include the following Examples.

| Example | Structure/Name/Characterization |
|---|---|
| 233 | 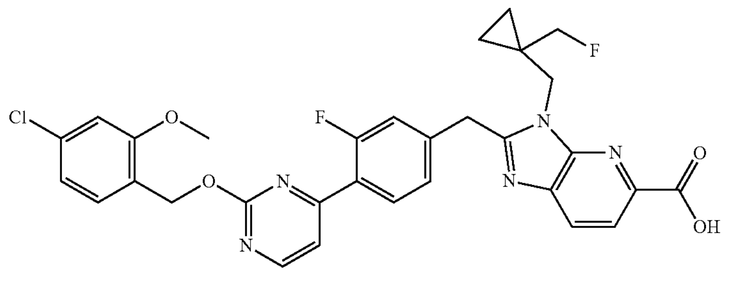 [SMILES: COc1cc(Cl)ccc1COc1nccc(-c2ccc(Cc3nc4ccc(C(=O)O)nc4n3CC3(CF)CC3)cc2F)n1]<br>2-(4-(2-((4-chloro-2-methoxybenzyl)oxy)pyrimidin-4-yl)-3-fluorobenzyl)-3-((1-(fluoromethyl)cyclopropyl)methyl)-3H-imidazo[4,5-b]pyridine-5-carboxylic acid: ES/MS m/z 606; $^1$H NMR (400 MHz, Methanol-d4) δ 8.62 (d, J = 5.2 Hz, 1H), 8.21-8.09 (m, 3H), 7.58 (dd, J = 5.2, 1.9 Hz, 1H), 7.43 (d, J = 8.1 Hz, 1H), 7.38-7.25 (m, 2H), 7.04 (d, J = 1.9 Hz, 1H), 6.95 (dd, J = 8.1, 1.9 Hz, 1H), 5.51 (s, 2H), 4.63 (s, 2H), 4.57 (s, 2H), 4.28 (d, J = 48.9 Hz, 2H), 3.87 (s, 3H), 1.14 (q, J = 5.5 Hz, 2H), 0.76-0.65 (m, 2H). |
| 268 | 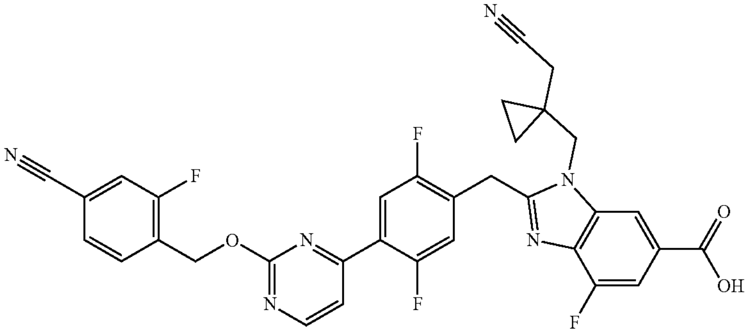 [SMILES: N#CCC1(Cn2c(Cc3cc(F)c(-c4ccnc(OCc5ccc(C#N)cc5F)n4)cc3F)nc3c(F)cc(C(=O)O)cc32)CC1]<br>2-(4-(2-((4-cyano-2-fluorobenzyl)oxy)pyrimidin-4-yl)-2,5-difluorobenzyl)-1-((1-(cyanomethyl)cyclopropyl)methyl)-4-fluoro-1H-benzo[d]imidazole-6-carboxylic acid: ES/MS m/z 627.2; $^1$H NMR (400 MHz, Methanol-d4) δ 8.70 (d, J = 5.2 Hz, 1H), 8.26 (s, 1H), 7.97 (dd, J = 10.6, 6.0 Hz, 1H), 7.80 (t, J = 7.5 Hz, 1H), 7.75-7.57 (m, 4H), 7.35 (dd, J = 11.6, 5.9 Hz, 1H), 5.70 (s, 2H), 4.59 (d, J = 5.2 Hz, 4H), 2.57 (s, 2H), 0.96-0.78 (m, 4H). |

-continued

| Example | Structure/Name/Characterization |
|---|---|
| 280 | 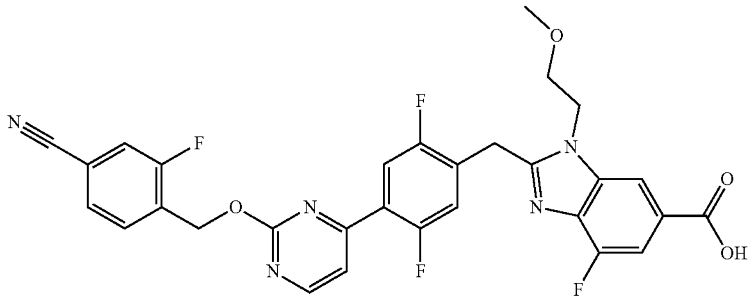 [SMILES: COCCn1c(Cc2cc(F)c(-c3ccnc(OCc4ccc(C#N)cc4F)n3)cc2F)nc2c(F)cc(C(=O)O)cc21] 2-(4-(2-((4-cyano-2-fluorobenzyl)oxy)pyrimidin-4-yl)-2,5-difluorobenzyl)-4-fluoro-1-(2-methoxyethyl)-1H-benzo[d]imidazole-6-carboxylic acid: ES/MS m/z 592.2; $^1H$ NMR (400 MHz, Methanol-d4) δ 8.70 (d, J = 5.2 Hz, 1H), 8.18 (d, J = 1.3 Hz, 1H), 7.96 (dd, J = 10.4, 6.2 Hz, 1H), 7.80 (t, J = 7.5 Hz, 1H), 7.75-7.56 (m, 4H), 7.28 (dd, J = 11.5, 5.8 Hz, 1H), 5.51 (s, 2H), 4.62 (t, J = 5.1 Hz, 2H), 4.58 (s, 2H), 3.76 (t, J = 4.9 Hz, 2H), 3.27 (s, 3H). |
| 298 | 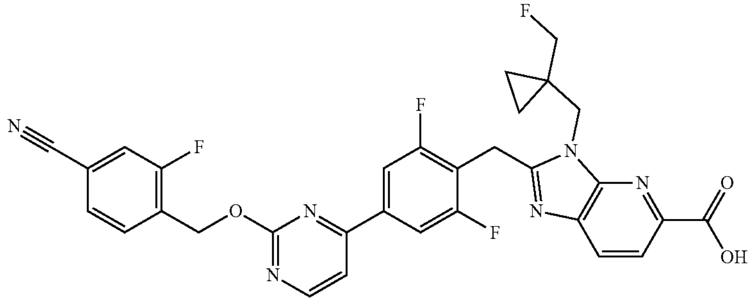 [SMILES: N#Cc1ccc(COc2nccc(-c3cc(F)c(Cc4nc5ccc(C(=O)O)nc5n4CC4(CF)CC4)c(F)c3)n2)c(F)c1] 2-(4-(2-((4-cyano-2-fluorobenzyl)oxy)pyrimidin-4-yl)-2,6-difluorobenzyl)-3-((1-(fluoromethyl)cyclopropyl)methyl)-3H-imidazo[4,5-b]pyridine-5-carboxylic acid: ES/MS m/z 603.2; $^1H$ NMR (400 MHz, Methanol-d4) δ 8.68 (d, J = 5.2 Hz, 1H), 8.13 (d, J = 8.3 Hz, 1H), 8.00 (d, J = 8.3 Hz, 1H), 7.85 (d, J = 8.2 Hz, 2H), 7.79 (t, J = 7.6 Hz, 1H), 7.65 (d, J = 5.2 Hz, 1H), 7.61-7.50 (m, 2H), 5.70 (s, 2H), 4.68 (s, 2H), 4.60 (s, 2H), 4.35 (s, 1H), 4.23 (s, 1H), 1.21 (d, J = 5.1 Hz, 2H), 0.74 (d, J = 5.8 Hz, 2H). |
| 414 | 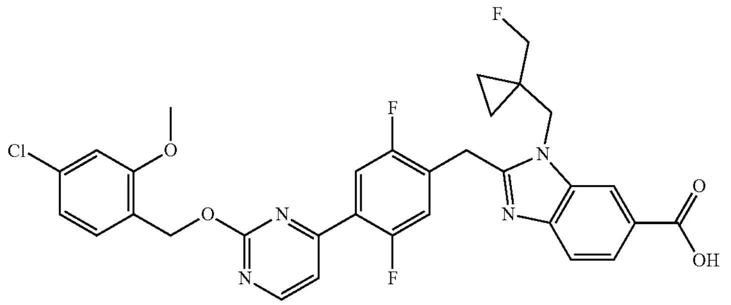 [SMILES: COc1cc(Cl)ccc1COc1nccc(-c2cc(F)c(Cc3nc4ccc(C(=O)O)cc4n3CC3(CF)CC3)cc2F)n1] 2-(4-(2-((4-chloro-2-methoxybenzyl)oxy)pyrimidin-4-yl)-2,5-difluorobenzyl)-1-((1-(fluoromethyl)cyclopropyl)methyl)-1H-benzo[d]imidazole-6-carboxylic acid: ES/MS m/z 623.1; $^1H$ NMR (400 MHz, DMSO-d6) δ 8.76 (d, J = 5.1 Hz, 1H), 8.26 (s, 1H), 7.90 (dd, J = 10.2, 6.2 Hz, 1H), 7.80 (d, J = 8.5 Hz, 1H), 7.64-7.57 (m, 2H), 7.50 (dd, J = 11.5, 6.0 Hz, 1H), 7.44 (d, J = 8.1 Hz, 1H), 7.16 (d, J = 1.9 Hz, 1H), 7.04 (dd, J = 8.1, 1.9 Hz, 1H), 5.45 (s, 2H), 4.56 (s, 2H), 4.48 (s, 2H), 4.18 (d, J = 48.8 Hz, 2H), 3.87 (s, 3H), 0.89-0.79 (m, 2H), 0.77-0.67 (m, 2H). |

Example 419. 2-(4-(6-((4-cyano-2-fluorobenzyl)oxy)pyridin-2-yl)-2-(3-hydroxy-3-methylbut-1-yn-1-yl)benzyl)-1-(2-methoxyethyl)-1H-benzo[d]imidazole-6-carboxylic acid Procedure 54

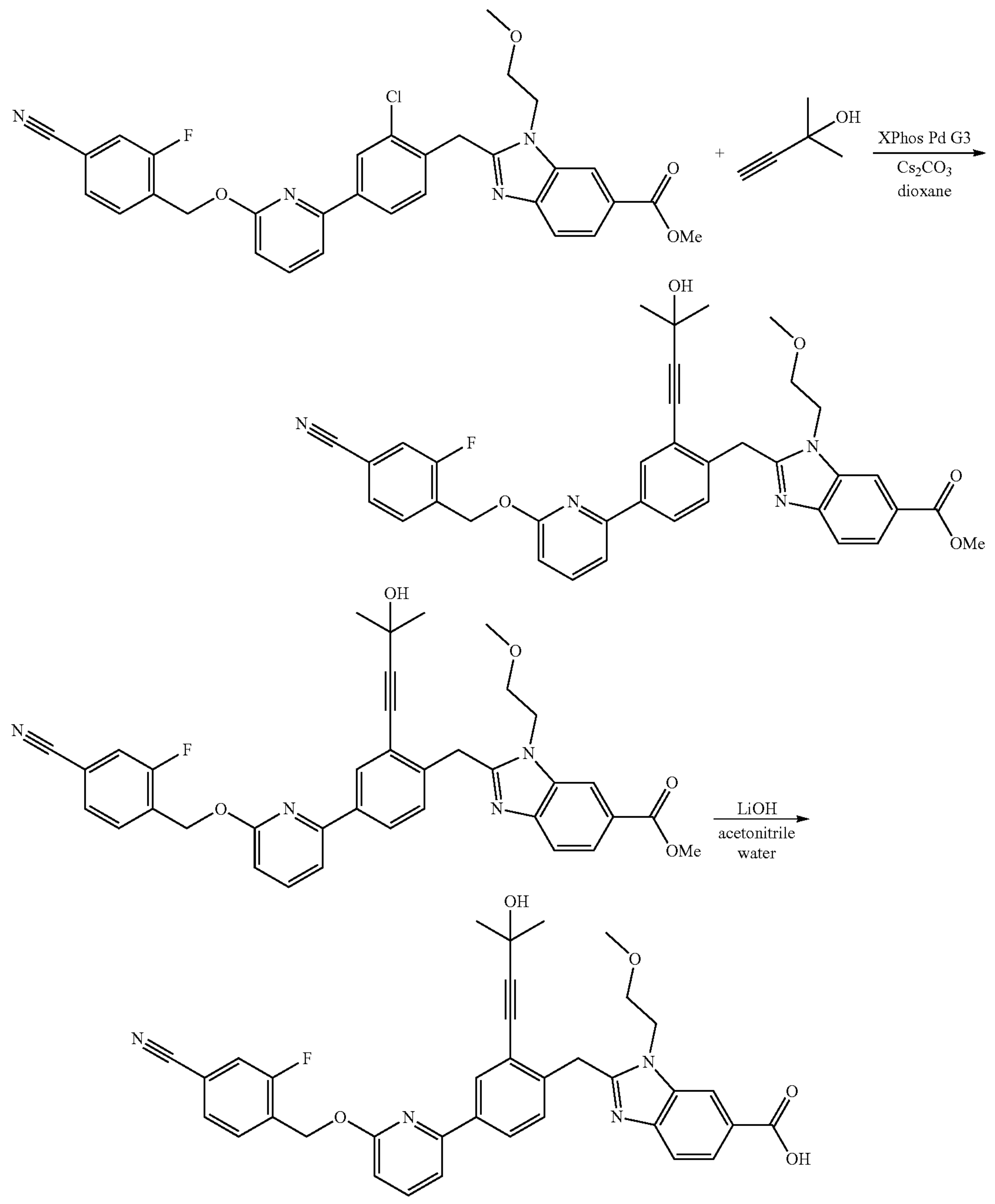

Example 419

Methyl 2-(4-(2-((4-chloro-2-methoxybenzyl)oxy)pyrimidin-4-yl)-2,5-difluorobenzyl)-1-((1-(cyanomethyl)cyclopropyl)methyl)-1H-benzo[d]imidazole-6-carboxylate: To a vial was added methyl 2-(2-chloro-4-(6-((4-cyano-2-fluorobenzyl)oxy)pyridin-2-yl)benzyl)-1-(2-methoxyethyl)-1H-benzo[d]imidazole-6-carboxylate (prepared in a similar fashion to Example 17) (40 mg, 0.068 mmol), 2-methylbut-3-yn-2-ol (17.2 mg, 0.205 mmol), XPhos Pd G3 (7.7 mg, 0.01 mmol), cesium carbonate (67 mg, 0.21 mmol) and dioxane (1.0 mL). The resulting mixture was degassed with argon for 30 seconds and the vial was sealed. The mixture was stirred overnight at 100° C. Upon cooling, the crude mixture was directly added to a silica loading column. The crude material was purified by silica gel column chromatography (eluent: EtOAc/Hex) to provide the desired product. ES/MS: 633.2 ($M+H^+$).

2-(4-(6-((4-cyano-2-fluorobenzyl)oxy)pyridin-2-yl)-2-(3-hydroxy-3-methylbut-1-yn-1-yl)benzyl)-1-(2-methoxyethyl)-1H-benzo[d]imidazole-6-carboxylic acid (Example 419): To a solution of methyl 2-(4-(2-((4-chloro-2-methoxy-benzyl)oxy)pyrimidin-4-yl)-2,5-difluorobenzyl)-1-((1-(cyanomethyl)cyclopropyl)methyl)-1H-benzo[d]imidazole-6-carboxylate (10.4 mg, 0.016 mmol) in acetonitrile (0.6 mL) was added lithium hydroxide monohydrate (1.1 mg, 0.025 mmol) dissolved in water (0.2 mL). The mixture was heated in a sealed tube at 100° C. for 3 minutes. The cooled mixture was purified by RP-HPLC (eluent: water/MeCN*0.100 TFA) to provide the product Example 419 as a trifluoroacetate salt. ES/MS: 619.2 (M+H$^+$); $^1$H NMR (400 MHz, Methanol-d4) δ 8.55 (s, 1H), 8.25-8.13 (m, 2H), 8.10-8.01 (m, 1H), 7.88-7.68 (m, 3H), 7.64 (d, J=9.8 Hz, 1H), 7.57 (t, J=7.3 Hz, 2H), 7.49 (d, J=8.4 Hz, 1H), 6.92 (d, J=8.3 Hz, 1H), 5.66 (s, 2H), 4.86-4.75 (m, 5H), 3.86-3.79 (m, 2H), 1.42 (s, 6H).

Example 438. Compounds Prepared Using Procedure 54

Other compounds of the present disclosure prepared using the general route described in Procedure 54 include the following Example.

| Example | Structure/Name/Characterization |
|---|---|
| 438 | 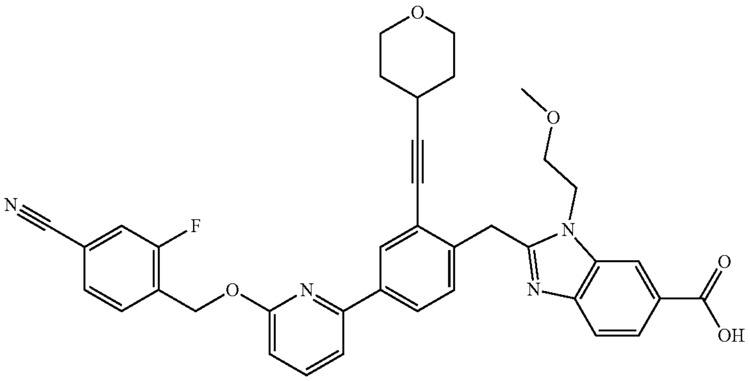 [SMILES: COCCn1c(Cc2ccc(-c3cccc(OCc4ccc(C#N)cc4F)n3)cc2C#CC2CCOCC2)nc2ccc(C(=O)O)cc21] 2-(4-(6-((4-cyano-2-fluorobenzyl)oxy)pyridin-2-yl)-2-((tetrahydro-2H-pyran-4-yl)ethynyl)benzyl)-1-(2-methoxyethyl)-1H-benzo[d]imidazole-6-carboxylic acid: ES/MS m/z 645.3; $^1$H NMR (400 MHz, Methanol-d4) δ 8.55 (s, 1H), 8.26-8.18 (m, 1H), 8.13 (d, J = 2.0 Hz, 1H), 8.02 (dd, J = 8.0, 2.0 Hz, 1H), 7.89-7.68 (m, 3H), 7.65-7.52 (m, 3H), 7.45 (d, J = 8.1 Hz, 1H), 6.92 (d, J = 8.2 Hz, 1H), 5.66 (s, 2H), 4.85-4.73 (m, 4H), 3.85-3.74 (m, 4H), 3.53-3.41 (m, 2H), 3.32 (s, 3H), 2.84 (d, J = 9.1 Hz, 1H), 1.75 (d, J = 13.3 Hz, 2H), 1.51 (d, J = 9.4 Hz, 2H). |

Examples 418 and 439. 2-(1-(4-(6-((4-cyano-2-fluorobenzyl)oxy)pyridin-2-yl)phenyl)ethyl)-1-(2-methoxyethyl)-1H-benzo[d]imidazole-6-carboxylic acid Procedure 55

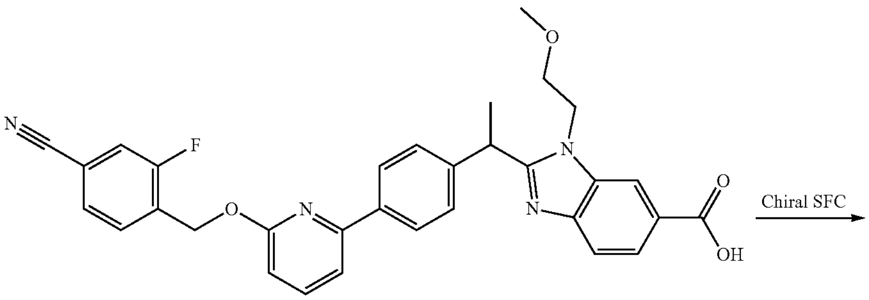

Example 447

-continued

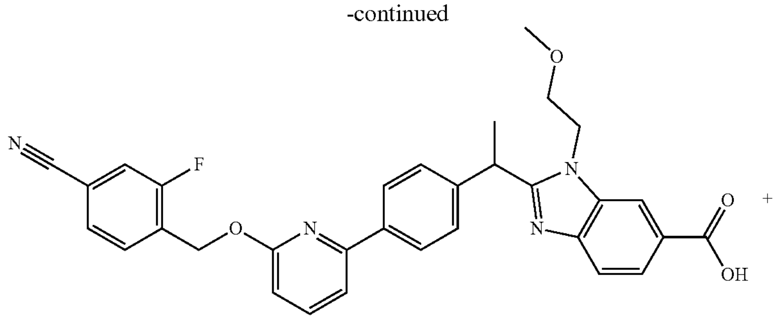

Isomer 1
Example 418

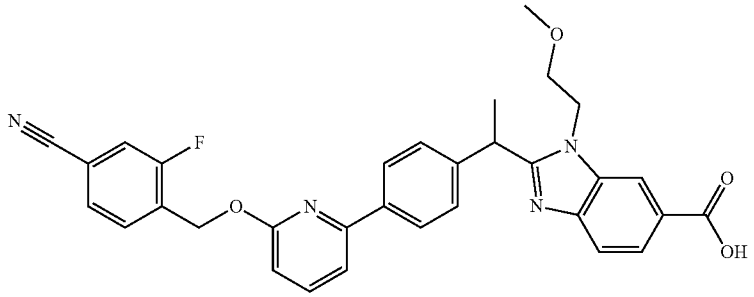

Isomer 2
Example 439

2-(1-(4-(6-((4-cyano-2-fluorobenzyl)oxy)pyridin-2-yl)phenyl)ethyl)-1-(2-methoxyethyl)-1H-benzo[d]imidazole-6-carboxylic acid (Example 418 and Example 439): 2-(1-(4-(6-((4-cyano-2-fluorobenzyl)oxy)pyridin-2-yl)phenyl)ethyl)-1-(2-methoxyethyl)-1H-benzo[d]imidazole-6-carboxylic acid (Example 447, obtained as described in Procedure 5) as a mixture of 2 stereoisomers was separated by chiral supercritical fluid chromatography (SFC) (IG column with 30% EtOH cosolvent) to give two distinct stereoisomers.

2-(1-(4-(6-((4-cyano-2-fluorobenzyl)oxy)pyridin-2-yl)phenyl)ethyl)-1-(2-methoxyethyl)-1H-benzo[d]imidazole-6-carboxylic acid (Example 418): ES/MS: 551.3 (M+H$^+$); $^1$H NMR (400 MHz, Methanol-d4) δ 8.45 (s, 1H), 8.24-8.17 (m, 1H), 8.09-7.99 (m, 2H), 7.85 (d, J=8.5 Hz, 1H), 7.82-7.68 (m, 2H), 7.65-7.54 (m, 2H), 7.51 (d, J=7.4 Hz, 1H), 7.42 (d, J=8.0 Hz, 2H), 6.86 (d, J=8.1 Hz, 1H), 5.64 (s, 2H), 4.98 (dd, J=28.8, 8.0 Hz, 1H), 4.74-4.47 (m, 2H), 3.76-3.61 (m, 1H), 3.61-3.44 (m, 1H), 3.22 (s, 3H), 1.92 (d, J=7.0 Hz, 3H).

2-(1-(4-(6-((4-cyano-2-fluorobenzyl)oxy)pyridin-2-yl)phenyl)ethyl)-1-(2-methoxyethyl)-1H-benzo[d]imidazole-6-carboxylic acid (Example 439): ES/MS: 551.3 (M+H$^+$); $^1$H NMR (400 MHz, Methanol-d4) δ 8.44 (d, J=1.3 Hz, 1H), 8.19 (dd, J=8.5, 1.5 Hz, 1H), 8.08-8.02 (m, 2H), 7.85 (d, J=8.6 Hz, 1H), 7.81-7.70 (m, 2H), 7.63-7.53 (m, 2H), 7.51 (d, J=7.5 Hz, 1H), 7.41 (d, J=8.4 Hz, 2H), 6.86 (d, J=8.2 Hz, 1H), 5.64 (s, 2H), 5.00 (q, J=7.1 Hz, 1H), 4.95-4.89 (m, 1H), 4.60 (dt, J=12.8, 4.0 Hz, 1H), 3.66 (dt, J=9.3, 4.1 Hz, 1H), 3.60-3.49 (m, 1H), 3.22 (s, 3H), 1.91 (d, J=7.1 Hz, 3H).

Example 498. 2-(4-(6-((2-aminobenzyl)oxy)pyridin-2-yl)-2-fluorobenzyl)-1-(2-methoxyethyl)-1H-benzo[d]imidazole-6-carboxylic acid Example 516. 2-(2-fluoro-4-(6-((2-(methylsulfonamido)benzyl)oxy)pyridin-2-yl)benzyl)-1-(2-methoxyethyl)-1H-benzo[d]imidazole-6-carboxylic acid Procedure 56:

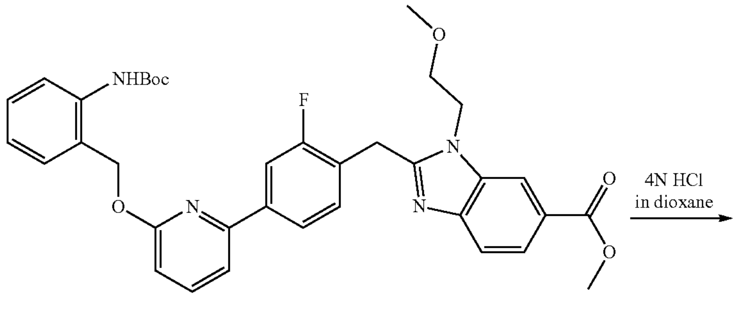

-continued

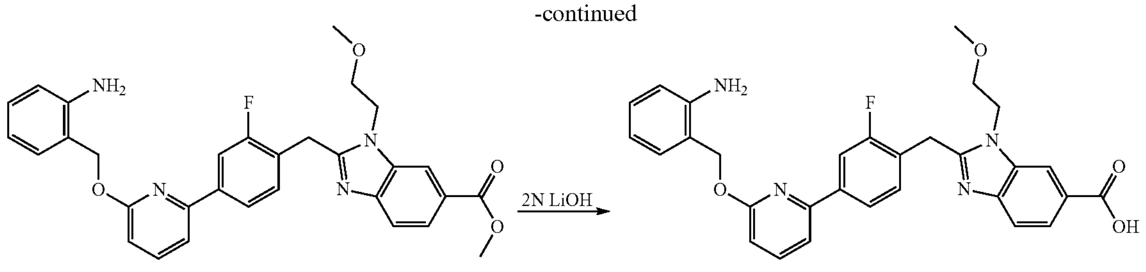

Example 498

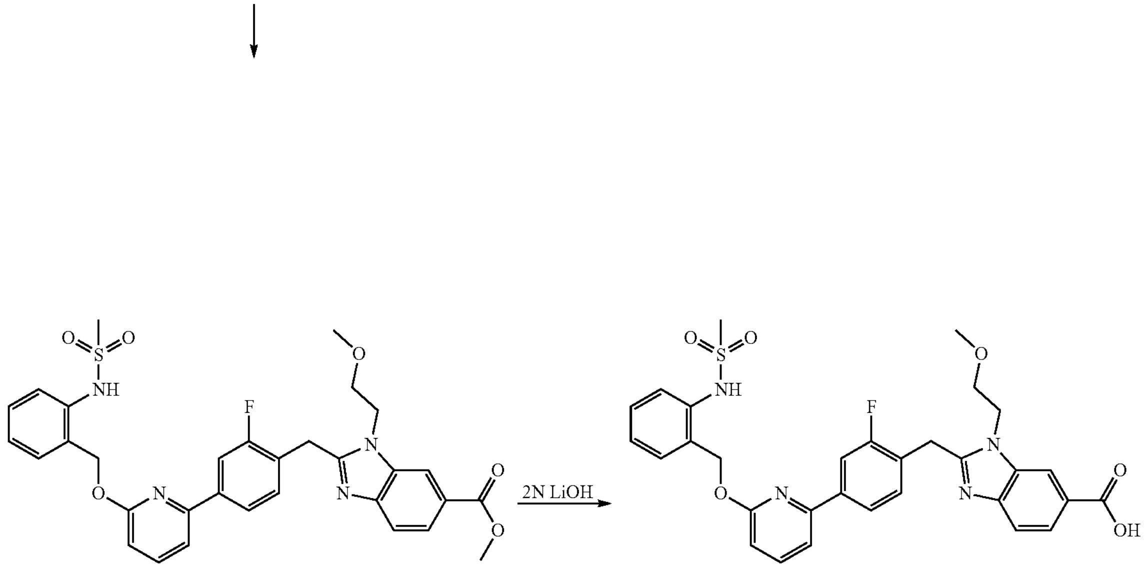

Example 516

2-(4-(6-((2-aminobenzyl)oxy)pyridin-2-yl)-2-fluorobenzyl)-1-(2-methoxyethyl)-1H-benzo[d]imidazole-6-carboxylate (Example 498): Methyl 2-(4-(6-((2-((tert-butoxycarbonyl)amino)benzyl)oxy)pyridin-2-yl)-2-fluorobenzyl)-1-(2-methoxyethyl)-1H-benzo[d]imidazole-6-carboxylate (15 mg, 0.015 mmol), prepared in the manner described in Procedure 32, was treated with 0.5 mL of 4N HCl in dioxane at room temperature. When the reaction was complete, the mixture was concentrated to provide methyl 2-(4-(6-((2-aminobenzyl)oxy)pyridin-2-yl)-2-fluorobenzyl)-1-(2-methoxyethyl)-1H-benzo[d]imidazole-6-carboxylate hydrochloride salt, which was used without further purification. This material was dissolved in 500 μL methanol and treated with 250 μL 2N LiOH at 30° C. overnight. The mixture was acidified with formic acid and purified by RP-HPLC (eluent: water/MeCN 0.10% TFA) to yield 2-(4-(6-((2-aminobenzyl)oxy)pyridin-2-yl)-2-fluorobenzyl)-1-(2-methoxyethyl)-1H-benzo[d]imidazole-6-carboxylic acid. ES/MS m/z: 527.20 ($M+H^+$); $^1H$ NMR (400 MHz, Methanol-d4) δ 8.39 (s, 1H), 8.08 (dd, J=8.5, 1.5 Hz, 1H), 7.72-7.61 (m, 2H), 7.43 (t, J=7.6 Hz, 1H), 7.20 (dd, J=15.0, 8.2 Hz, 3H), 7.03-6.89 (m, 2H), 6.74-6.62 (m, 2H), 6.44 (dd, J=6.9, 1.4 Hz, 1H), 5.19 (s, 2H), 4.67 (t, J=5.0 Hz, 2H), 4.61 (s, 2H), 3.79 (t, J=4.9 Hz, 2H), 3.29 (s, 3H).

2-(2-fluoro-4-(6-((2-(methylsulfonamido)benzyl)oxy)pyridin-2-yl)benzyl)-1-(2-methoxyethyl)-1H-benzo[d]imidazole-6-carboxylic acid (Example 516): Methyl 2-(4-(6-((2-((tert-butoxycarbonyl)amino)benzyl)oxy)pyridin-2-yl)-2-fluorobenzyl)-1-(2-methoxyethyl)-1H-benzo[d]imidazole-6-carboxylate (13 mg, 0.020 mmol), prepared in the manner described in Procedure 32, was treated with 0.5 mL of 4N HCl in dioxane at room temperature. When the reaction was complete, the mixture was concentrated to provide methyl 2-(4-(6-((2-aminobenzyl)oxy)pyridin-2-yl)-2-fluorobenzyl)-1-(2-methoxyethyl)-1H-benzo[d]imidazole-6-carboxylate hydrochloride salt, which was used without further purification. This material was dissolved in dichloromethane (1 mL) and treated with excess diisopropylamine (>5 eq) and methanesulfonyl chloride (>2 eq) at room temperature overnight to form methyl 2-(2-fluoro-4-(6-((2-(methylsulfonamido)benzyl)oxy)pyridin-2-yl)benzyl)-1-(2-methoxyethyl)-1H-benzo[d]imidazole-6-carboxylate. The mixture was concentrated and then re-dissolved in 500 μL methanol and treated with 250 μL 2N LiOH at 30° C. overnight. The mixture was acidified with formic acid and purified by RP-HPLC (eluent: water/MeCN 0.1% TFA) to yield 2-(2-fluoro-4-(6-((2-(methylsulfonamido)benzyl)oxy)pyridin-2-yl)benzyl)-1-(2-methoxyethyl)-1H-benzo[d]imidazole-6-carboxylic acid. ES/MS m/z: 605.20 ($M+H^+$); 1H NMR (400 MHz, Methanol-d4) δ 8.45 (s, 1H), 8.18-8.08 (m, 1H), 7.80 (d, J=8.7 Hz, 1H), 7.65 (dd, J=9.1, 6.9 Hz, 1H), 7.38 (t, J=7.7 Hz, 1H), 7.31-7.19 (m, 3H), 7.07 (d, J=7.8 Hz, 1H), 6.99 (d, J=10.2 Hz, 1H), 6.87 (d, J=7.3 Hz, 1H), 6.72 (d, J=8.3 Hz, 1H), 6.42-6.35 (m, 1H), 5.51 (s, 1H), 5.36 (s, 2H), 4.69 (t, J=5.1 Hz, 2H), 4.63 (s, 2H), 3.80 (t, J=4.9 Hz, 2H), 3.30 (s, 3H), 2.84 (s, 3H).

Example 502. 2-(4-(6-((4-carbamoyl-2-oxopyridin-1(2H)-yl)methoxy)pyridin-2-yl)-2-fluorobenzyl)-1-(2-methoxyethyl)-1H-benzo[d]imidazole-6-carboxylic acid Example 503. 2-(4-(6-((4-carboxy-2-oxopyridin-1(2H)-yl)methoxy)pyridin-2-yl)-2-fluorobenzyl)-1-(2-methoxyethyl)-1H-benzo[d]imidazole-6-carboxylic acid Example 513. 2-(4-(6-((4-cyano-2-oxopyridin-1(2H)-yl)methoxy)pyridin-2-yl)-2-fluorobenzyl)-1-(2-methoxyethyl)-1H-benzo[d]imidazole-6-carboxylic acid Procedure 57

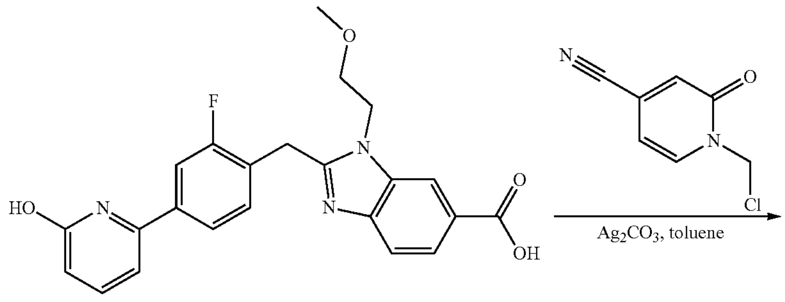

I-109

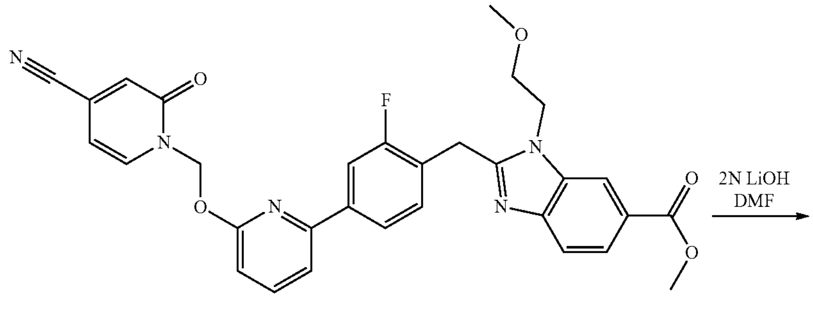

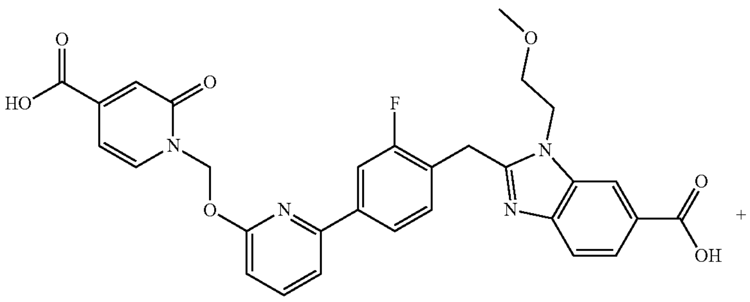

Example 503

-continued

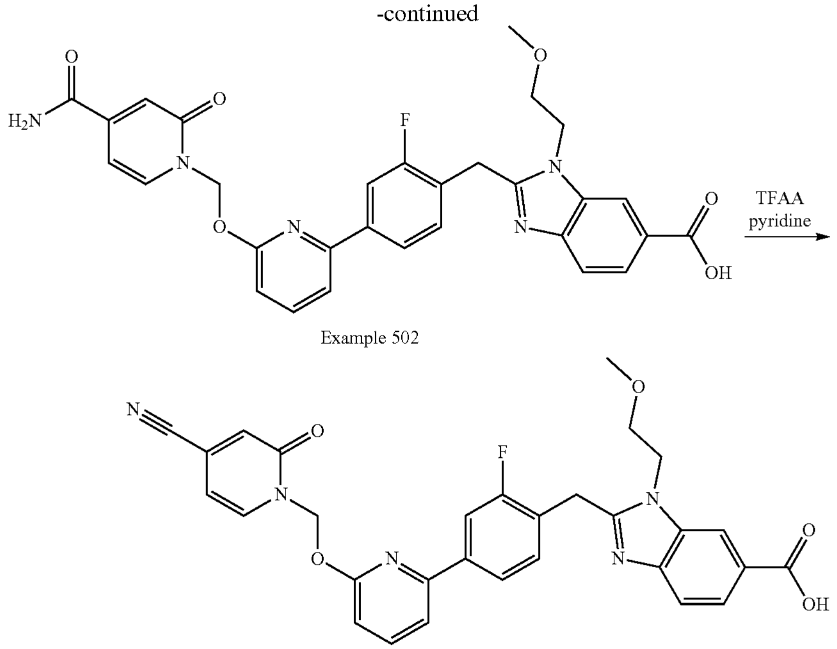

Example 502

Example 513

2-(4-(6-((4-cyano-2-oxopyridin-1(2H)-yl)methoxy)pyridin-2-yl)-2-fluorobenzyl)-1-(2-methoxyethyl)-1H-benzo[d]imidazole-6-carboxylic acid: A mixture of methyl 2-(2-fluoro-4-(6-hydroxypyridin-2-yl)benzyl)-1-(2-methoxyethyl)-1H-benzo[d]imidazole-6-carboxylate (I-109, 20 mg, 0.046 mmol), 1-(chloromethyl)-2-oxo-1,2-dihydropyridine-4-carbonitrile (23.2 mg, 0.138 mmol), and silver carbonate (51 mg, 0.184 mmol), in toluene (0.5 mL) was stirred at 100° C. for 30 minutes, when LCMS indicated full conversion to desired product. After cooling to room temperature, the mixture was diluted with dichloromethane, filtered, and concentrated to give methyl 2-(4-(6-((4-cyano-2-oxopyridin-1(2H)-yl)methoxy)pyridin-2-yl)-2-fluorobenzyl)-1-(2-methoxyethyl)-1H-benzo[d]imidazole-6-carboxylate, which was used without further purification. The residue was dissolved in DMF (200 μL), treated with aqueous LiOH (2 M, 20 eq), and stirred at 30° C. overnight. The resulting mixture was purified by RP-HPLC (eluent: water/MeCN 0.1% TFA) to give 2-(4-(6-((4-carboxy-2-oxopyridin-1(2H)-yl)methoxy)pyridin-2-yl)-2-fluorobenzyl)-1-(2-methoxyethyl)-1H-benzo[d]imidazole-6-carboxylic acid (Example 503) and 2-(4-(6-((4-carbamoyl-2-oxopyridin-1(2H)-yl)methoxy)pyridin-2-yl)-2-fluorobenzyl)-1-(2-methoxyethyl)-1H-benzo[d]imidazole-6-carboxylic acid (Example 502). When the reaction was performed at room temperature, 2-(4-(6-((4-carbamoyl-2-oxopyridin-1(2H)-yl)methoxy)pyridin-2-yl)-2-fluorobenzyl)-1-(2-methoxyethyl)-1H-benzo[d]imidazole-6-carboxylic acid (Example 502) was obtained, and was isolated by RP-HPLC (eluent: water/MeCN 0.1% TFA). 2-(4-(6-((4-carbamoyl-2-oxopyridin-1(2H)-yl)methoxy)pyridin-2-yl)-2-fluorobenzyl)-1-(2-methoxyethyl)-1H-benzo[d]imidazole-6-carboxylic acid (Example 502) (13.9 mg, 0.024 mmol) in pyridine (1 mL) was treated with trifluoroacetic anhydride (10 mg, 0.046 mmol) at room temperature to provide 2-(4-(6-((4-cyano-2-oxopyridin-1(2H)-yl)methoxy)pyridin-2-yl)-2-fluorobenzyl)-1-(2-methoxyethyl)-1H-benzo[d]imidazole-6-carboxylic acid (Example 513), which was concentrated, acidified with formic acid and purified by RP-HPLC (eluent: water/MeCN 0.1% TFA).

2-(4-(6-((4-carboxy-2-oxopyridin-1(2H)-yl)methoxy)pyridin-2-yl)-2-fluorobenzyl)-1-(2-methoxyethyl)-1H-benzo[d]imidazole-6-carboxylic acid (Example 503): ES/MS m/z: 573.2 ($M+H^+$); $^1H$ NMR (400 MHz, Methanol-d4) δ 8.50 (s, 1H), 8.24-8.13 (m, 1H), 8.04-7.94 (m, 3H), 7.84 (t, J=7.9 Hz, 1H), 7.77 (d, J=7.8 Hz, 1H), 7.63 (d, J=7.6 Hz, 1H), 7.50 (s, 1H), 7.14 (s, 1H), 6.90 (d, J=8.0 Hz, 1H), 6.76 (d, J=7.0 Hz, 1H), 6.38 (s, 2H), 4.76 (s, 2H), 4.73 (s, 2H), 3.80 (s, 2H), 3.31 (s, 3H).

2-(4-(6-((4-carbamoyl-2-oxopyridin-1(2H)-yl)methoxy)pyridin-2-yl)-2-fluorobenzyl)-1-(2-methoxyethyl)-1H-benzo[d]imidazole-6-carboxylic acid (Example 502): ES/MS m/z: 572.18 ($M+H^+$); $^1H$ NMR (400 MHz, Methanol-d4) δ 8.48 (s, 1H), 8.20-8.13 (m, 1H), 8.00 (t, J=8.1 Hz, 3H), 7.84 (t, J=7.9 Hz, 1H), 7.76 (d, J=8.5 Hz, 1H), 7.63 (d, J=7.5 Hz, 1H), 7.50 (t, J=8.0 Hz, 1H), 6.97 (d, J=1.9 Hz, 1H), 6.89 (d, J=8.3 Hz, 1H), 6.65 (dd, J=7.2, 1.9 Hz, 1H), 6.38 (s, 2H), 4.74 (t, J=5.0 Hz, 2H), 4.71 (s, 2H), 3.80 (t, J=5.0 Hz, 2H), 3.31 (s, 3H).

2-(4-(6-((4-cyano-2-oxopyridin-1(2H)-yl)methoxy)pyridin-2-yl)-2-fluorobenzyl)-1-(2-methoxyethyl)-1H-benzo[d]imidazole-6-carboxylic acid (Example 513): ES/MS m/z: 554.20 ($M+H^+$); $^1H$ NMR (400 MHz, Methanol-d4) δ 8.52 (s, 1H), 8.24-8.16 (m, 1H), 8.05 (d, J=7.1 Hz, 1H), 7.99 (dd, J=9.0, 5.7 Hz, 2H), 7.86 (t, J=7.9 Hz, 1H), 7.77 (d, J=8.5 Hz, 1H), 7.65 (d, J=7.5 Hz, 1H), 7.52 (t, J=7.9 Hz, 1H), 7.00 (d, J=1.8 Hz, 1H), 6.91 (d, J=8.2 Hz, 1H), 6.49 (dd, J=7.1, 1.8 Hz, 1H), 6.37 (s, 2H), 4.78 (t, J=4.9 Hz, 2H), 4.75 (s, 2H), 3.81 (t, J=4.9 Hz, 2H).

Example 181. 2-(4-(6-((4-cyano-2-fluorobenzyl)oxy)pyridin-2-yl)-2-hydroxybenzyl)-1-(2-methoxyethyl)-1H-benzo[d]imidazole-6-carboxylic acid Procedure 58

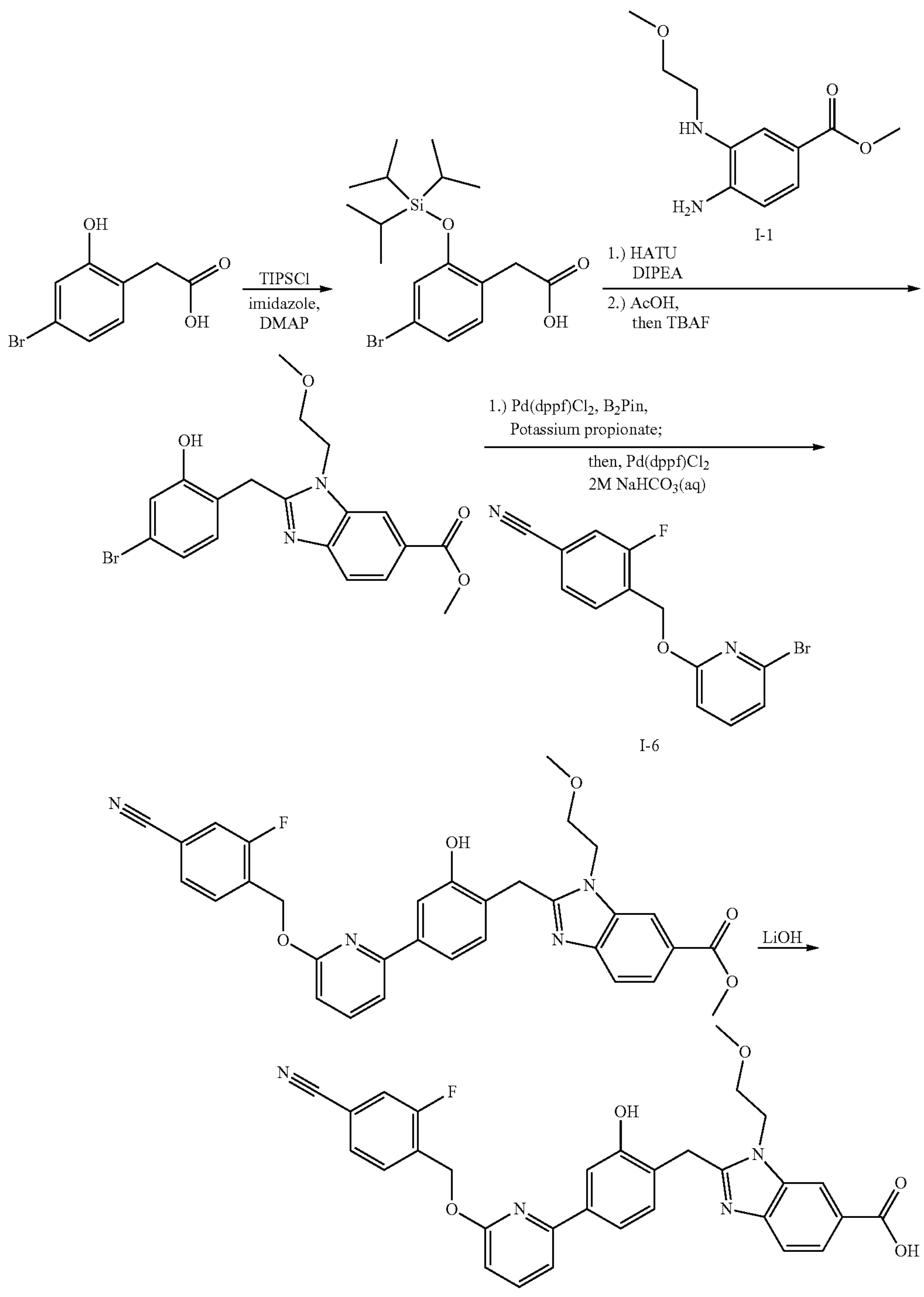

Example 181

2-(4-bromo-2-((triisopropylsilyl)oxy)phenyl)acetic acid: To a 50 mL RBF containing 2-(4-bromo-2-hydroxy-phenyl) acetic acid (2.02 g, 8.74 mmol) in DMF (20 mL) was added imidazole (2.38 g, 35.0 mmol), triisopropylsilyl chloride (2.06 mL, 9.62 mmol), and 4-dimethylaminopyridine (107 mg, 0.874 mmol). The solution was stirred at RT overnight. The solution was treated with 1 M HCl (40 mL), stirred for about 5 minutes, then extracted with of EtOAc (40 mL), washed with brine, dried over $MgSO_4$, filtered and concentrated to give the title compound. $^1$H NMR (400 MHz, Acetonitrile-d3) δ 7.14 (s, 1H), 6.98 (d, J=7.4 Hz, 2H), 6.91 (d, J=8.4 Hz, 1H), 3.54 (d, J=28.1 Hz, 2H), 1.10 (d, J=7.5 Hz, 3H), 1.02 (s, 22H).

Methyl 2-(4-bromo-2-hydroxybenzyl)-1-(2-methoxyethyl)-1H-benzo[d]imidazole-6-carboxylate: To a 50 mL RBF containing 2-(4-bromo-2-((triisopropylsilyl)oxy)phenyl)acetic acid (3.00 g, 7.74 mmol), methyl 4-amino-3-(2-methoxyethylamino)benzoate (I-1, 1.65 g, 7.36 mmol), and 2-(7-aza-1H-benzotriazole-1-yl)-1,1,3,3-tetramethyluronium hexafluorophosphate (2.00 g, 8.52 mmol) in DMF (15 mL) was added DIPEA (6.13 mL, 35.2 mmol). The solution was stirred at RT for four hours. The solution was diluted with EtOAc, washed with $NH_4Cl$ (aq), washed with brine, dried over $Na_2SO_4$, filtered, and concentrated. The crude residue was then dissolved in AcOH (9 mL) and transferred to a 50 mL RBF. The solution was stirred at 60° C. for 4 h. After LCMS confirmed completion of condensation, TBAF (1 M in THF, 8.75 mmol, 8.75 mL) was added, and the solution was stirred for 20 minutes. The solution was concentrated and split between 40 mL aqueous bicarbonate and EtOAc. The organic layer was washed with brine, dried over sodium sulfate, filtered, concentrated, and chromatographed (eluent: EtOAc/hexanes) to give the title product. ES/MS: 419.2 (M+H$^+$).

Methyl 2-(4-(6-((4-cyano-2-fluorobenzyl)oxy)pyridin-2-yl)-2-hydroxybenzyl)-1-(2-methoxyethyl)-1H-benzo[d]imidazole-6-carboxylate: To a 20 mL microwave vial was added methyl 2-(4-bromo-2-hydroxybenzyl)-1-(2-methoxyethyl)-1H-benzo[d]imidazole-6-carboxylate (600 mg, 1.43 mmol), potassium propionate (482 mg, 4.30 mmol), bis(pinacolato)diboron (485 mg, 2.15 mmol), 1,1'-bis(diphenylphosphino)ferrocene]dichloropalladium(II) (159 mg, 0.22 mmol) and dioxane (10.0 mL). The resulting mixture was degassed by bubbling argon below the liquid surface for 1 minute after which the vial was sealed and heated in a microwave reactor to 120° C. for 20 minutes. Upon cooling the vial was opened and to the mixture was added 4-[(6-bromo-2-pyridyl)oxymethyl]-3-fluoro-benzonitrile (I-6, 483 mg, 1.57 mmol), 1,1'-bis(diphenylphosphino)ferrocene]dichloropalladium(II) (80 mg, 0.11 mmol) and sodium carbonate (2 M aq. solution, 1.43 mL, 2.86 mmol). The vial was sealed, then heated in a microwave at 90° C. for 1 hour. The mixture was cooled and directly added to a silica loading column. The crude material was purified by silica gel column chromatography (eluent: EtOAc/Hex) to provide the desired product. ES/MS: 567.2 (M+H$^+$).

2-(4-(6-((4-cyano-2-fluorobenzyl)oxy)pyridin-2-yl)-2-hydroxybenzyl)-1-(2-methoxyethyl)-1H-benzo[d]imidazole-6-carboxylic acid (Example 181): To a mixture of methyl 2-(4-(6-((4-cyano-2-fluorobenzyl)oxy)pyridin-2-yl)-2-hydroxybenzyl)-1-(2-methoxyethyl)-1H-benzo[d]imidazole-6-carboxylate (38.8 mg, 68.5 μmol) in acetonitrile (3.00 mL) and water (1.00 mL) was added lithium hydroxide monohydrate (8.6 mg, 0.205 mmol) and the mixture was stirred at RT for 12 hours. An aliquot of trifluoroacetic acid (5.24 μL, 68.5 μmol) was added, the mixture was concentrated under reduced pressure, and the crude material was taken up in DMF (1.5 mL). The mixture was filtered through a syringe filter and purified by RP-HPLC (eluent: water/MeCN*0.1% TFA) to yield the product Example 181 as a trifluoroacetate salt. ES/MS: 553.4 (M+H$^+$); $^1$H NMR (400 MHz, Acetonitrile-d3) δ 8.43-8.39 (m, 1H), 8.13 (dd, J=8.6, 1.5 Hz, 1H), 7.83-7.78 (m, 2H), 7.78-7.72 (m, 1H), 7.67 (d, J=1.7 Hz, 1H), 7.61-7.56 (m, 2H), 7.56-7.53 (m, 1H), 7.50-7.47 (m, 1H), 7.40 (d, J=8.0 Hz, 1H), 6.86 (d, J=8.2 Hz, 1H), 5.65 (s, 2H), 4.69 (t, J=5.0 Hz, 2H), 4.55 (s, 2H), 3.76 (t, J=5.0 Hz, 2H), 3.27 (s, 3H).

Example 184. 2-((5-(6-((4-cyano-2-fluorobenzyl)oxy)pyridin-2-yl)-[1,1'-biphenyl]-2-yl)methyl)-1-(2-methoxyethyl)-1H-benzo[d]imidazole-6-carboxylic acid Procedure 59

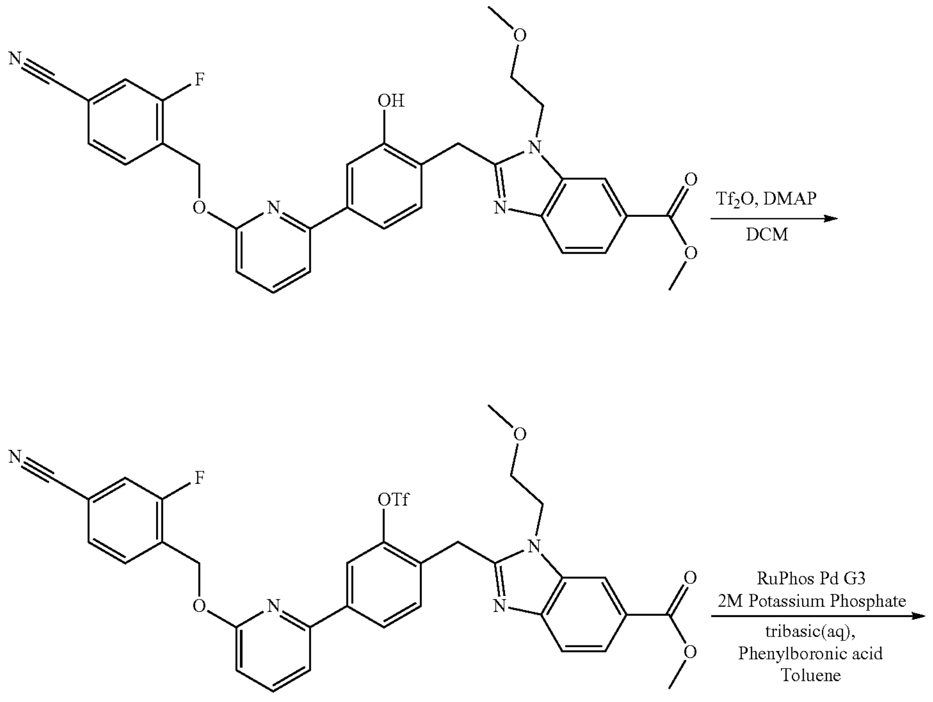

-continued

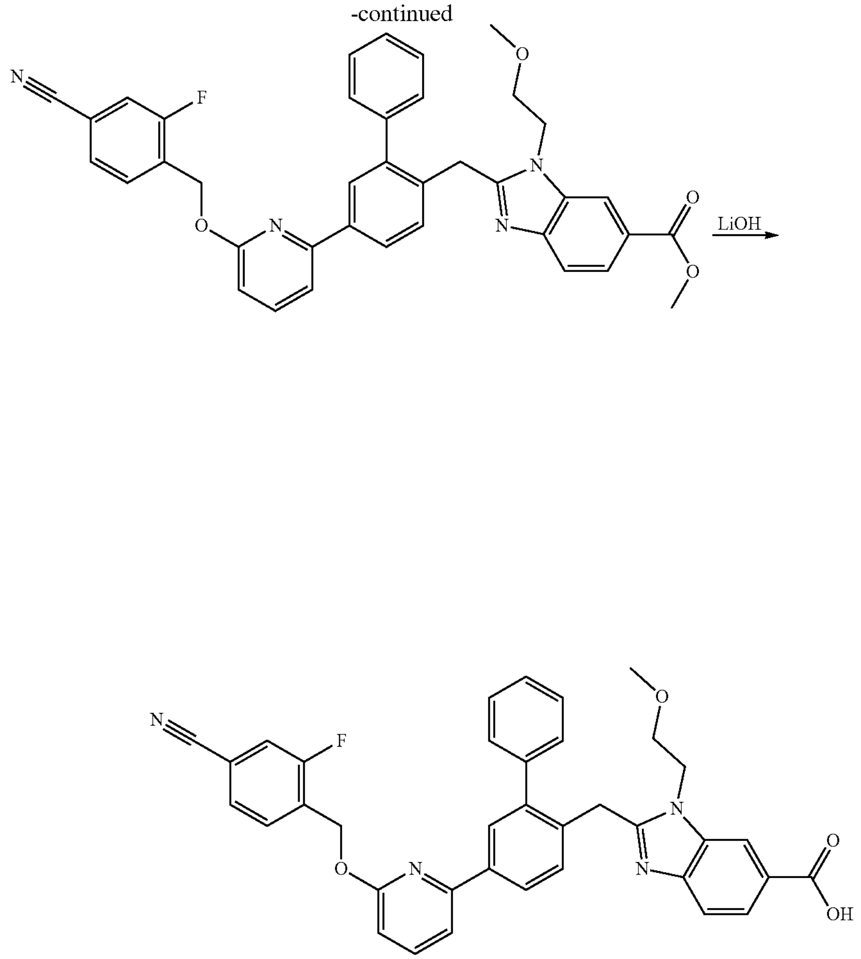

Example 184

Methyl 2-(4-(6-((4-cyano-2-fluorobenzyl)oxy)pyridin-2-yl)-2-(((trifluoromethyl)sulfonyl)oxy)benzyl)-1-(2-methoxyethyl)-1H-benzo[d]imidazole-6-carboxylate: In a 25 mL RBF containing methyl 2-(4-(6-((4-cyano-2-fluorobenzyl)oxy)pyridin-2-yl)-2-hydroxybenzyl)-1-(2-methoxyethyl)-1H-benzo[d]imidazole-6-carboxylate (400 mg, 0.706 mmol) and DMAP (259 mg, 2.12 mmol) was added anhydrous DCM (10 mL), after purging with argon into a heat gun dried flask. The solution was cooled to −78° C. Trifluoromethylsulfonyl trifluoromethanesulfonate (1 M in DCM, 0.741 mL, 0.741 mmol) was added dropwise down the side of the flask. The solution was warmed slowly to 0° C. by transferring to an ice water bath. The solution was poured into water, then extracted with DCM and dried over $Na_2SO_4$. The mixture was filtered and concentrated, then purified on a normal phase column (65-100% EtOAc in hexane) to give the title compound. ES/MS: 699.1 ($M+H^+$).

Methyl 2-((5-(6-((4-cyano-2-fluorobenzyl)oxy)pyridin-2-yl)-[1,1'-biphenyl]-2-yl)methyl)-1-(2-methoxyethyl)-1H-benzo[d]imidazole-6-carboxylate: In a 2 mL microwave vial was added methyl 2-(4-(6-((4-cyano-2-fluorobenzyl)oxy) pyridin-2-yl)-2-(((trifluoromethyl)sulfonyl)oxy)benzyl)-1-(2-methoxyethyl)-1H-benzo[d]imidazole-6-carboxylate (20.0 mg, 0.03 mmol), phenyl boronic acid (5.24 mg, 0.04 mmol), RuPhos Pd G3 (4.79 mg, 5.72 μmol), potassium phosphate tribasic (2 M, 0.07 mL, 0.143 mmol), and toluene (2 mL). The mixture was degassed by bubbling argon through for five minutes, then sealed, and heated to 110° C. on a heating block for 2 hours. The mixture was cooled to RT, diluted with EtOAc, filtered, and concentrated. The concentrate was purified by reverse phase chromatography to give the title compound. ES/MS: 627.2 ($M+H^+$).

2-((5-(6-((4-cyano-2-fluorobenzyl)oxy)pyridin-2-yl)-[1,1'-biphenyl]-2-yl)methyl)-1-(2-methoxyethyl)-1H-benzo[d]imidazole-6-carboxylic acid (Example 184): To a mixture of methyl 2-((5-(6-((4-cyano-2-fluorobenzyl)oxy)pyridin-2-yl)-[1,1'-biphenyl]-2-yl)methyl)-1-(2-methoxyethyl)-1H-benzo[d]imidazole-6-carboxylate (17.9 mg, 28.6 μmol) in acetonitrile (3.00 mL) and water (1.00 mL) was added lithium hydroxide monohydrate (3.60 mg, 0.08 mmol) and the mixture was stirred at RT for 12 hours. An aliquot of trifluoroacetic acid (7.65 μL, 0.08 mmol) was added, the mixture was concentrated under reduced pressure, and the crude material was taken up in DMF (1.5 mL). The mixture was filtered through a syringe filter and purified by RP-HPLC (eluent: water/MeCN*0.1% TFA) to yield the product Example 184 as a trifluoroacetate salt. ES/MS: 613.3 ($M+H^+$); 1H NMR (400 MHz, Acetonitrile-d3) δ 8.40-8.35 (m, 1H), 8.17 (dd, J=8.6, 1.5 Hz, 1H), 8.08 (dd, J=8.1, 2.1 Hz, 1H), 7.91 (d, J=2.0 Hz, 1H), 7.82 (t, J=7.8 Hz, 1H), 7.74 (d, J=8.6 Hz, 1H), 7.68 (t, J=7.6 Hz, 1H), 7.59 (d, J=7.5 Hz, 1H), 7.55-7.48 (m, 2H), 7.42-7.35 (m, 3H), 7.33-7.27 (m, 2H), 6.91 (d, J=8.2 Hz, 1H), 5.60 (s, 2H), 4.64 (s, 2H), 4.32 (t, J=4.9 Hz, 2H), 3.54 (t, J=4.9 Hz, 2H), 3.13 (s, 3H).

Examples 171, 173, 175, 176, 178, 185, 187, 188, 190, 193. Compounds Prepared Using Procedure 59

Other compounds of the present disclosure prepared using the general route described in Procedure 59 include the following Examples.

| Example | Structure/Name/Characterization |
|---|---|
| 171 | 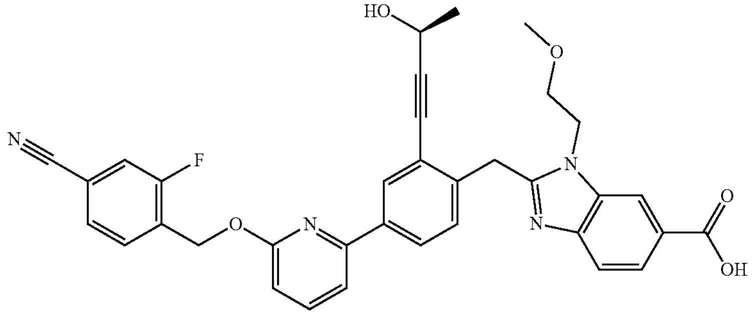 [SMILES: COCCn1c(Cc2ccc(-c3cccc(OCc4ccc(C#N)cc4F)n3)cc2C#C[C@H](C)O)nc2ccc(C(=O)O)cc21] And 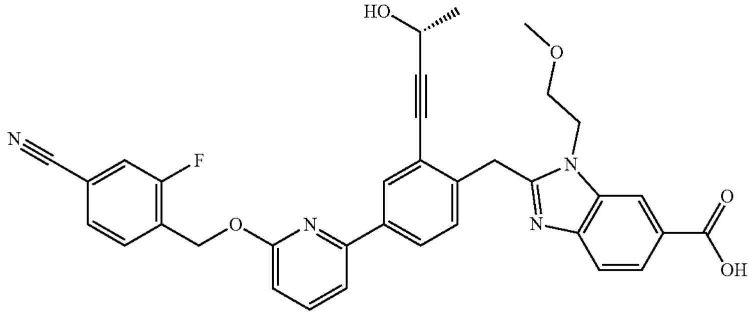 [SMILES: COCCn1c(Cc2ccc(-c3cccc(OCc4ccc(C#N)cc4F)n3)cc2C#C[C@@H](C)O)nc2ccc(C(=O)O)cc21] 2-(4-(6-((4-cyano-2-fluorobenzyl)oxy)pyridin-2-yl)-2-(3-hydroxybut-1-yn-1-yl)benzyl)-1-(2-methoxyethyl)-1H-benzo[d]imidazole-6-carboxylic acid: ES/MS m/z 605.3; $^1$H NMR (400 MHz, Methanol-d4) δ 8.48 (s, 1H), 8.20-8.12 (m, 2H), 8.02 (d, J = 16.8 Hz, 3H), 7.81 (t, J = 7.9 Hz, 1H), 7.74 (d, J = 8.2 Hz, 1H), 7.64 (d, J = 9.8 Hz, 1H), 7.56 (dd, J = 13.2, 7.8 Hz, 1H), 7.45 (d, J = 8.1 Hz, 1H), 6.90 (d, J = 8.1 Hz, 1H), 5.65 (s, 2H), 4.79 (s, 1H), 4.74 (s, 1H), 4.66 (d, J = 6.6 Hz, 0H), 3.78 (s, 2H), 1.96 (s, 9H). |
| 173 | 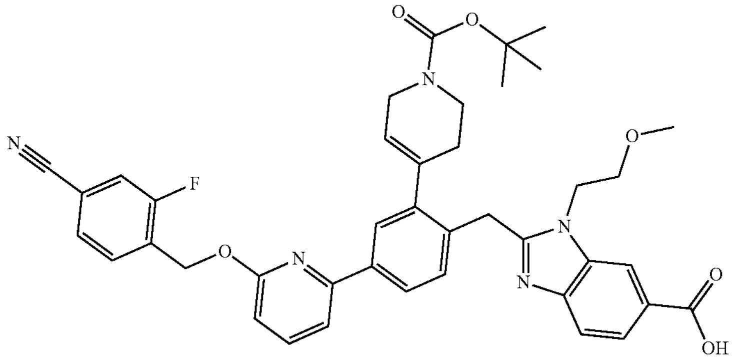 [SMILES: COCCn1c(Cc2ccc(-c3cccc(OCc4ccc(C#N)cc4F)n3)cc2C2=CCN(C(=O)OC(C)(C)C)CC2)nc2ccc(C(=O)O)cc21] 2-(2-(1-(tert-butoxycarbonyl)-1,2,3,6-tetrahydropyridin-4-yl)-4-(6-((4-cyano-2-fluorobenzyl)oxy)pyridin-2-yl)benzyl)-1-(2-methoxyethyl)-1H-benzo[d]imidazole-6-carboxylic acid: ES/MS m/z 718.2; $^1$H NMR (400 MHz, Acetonitrile-d3) δ 8.42 (s, 1H), 8.14 (d, J = 8.5 Hz, 1H), 7.92 (d, J = 8.6 Hz, 1H), 7.87-7.76 (m, 3H), 7.71 (d, J = 8.5 Hz, 1H), 7.56 (d, J = 9.4 Hz, 4H), 7.33 (d, J = 8.1 Hz, 1H), 6.88 (d, J = 8.1 Hz, 1H), 5.64 (s, 3H), 4.68 (s, 2H), 4.50 (d, J = 5.4 Hz, 2H), 3.94 (s, 2H), 3.67 (s, 2H), 3.53 (s, 2H), 3.25 (s, 3H), 2.32 (s, 2H), 1.47 (s, 8H). |

-continued

| Example | Structure/Name/Characterization |
|---|---|
| 175 | 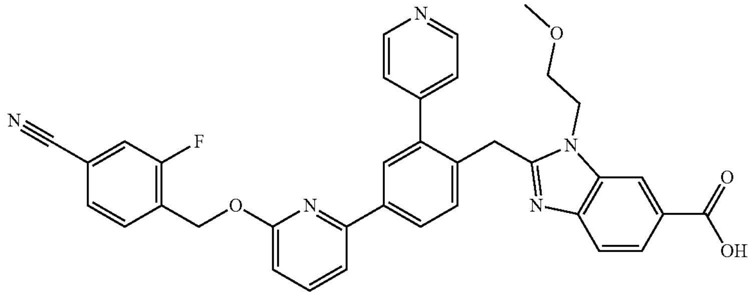 [SMILES: COCCn1c(Cc2ccc(-c3cccc(OCc4ccc(C#N)cc4F)n3)cc2-c2ccncc2)nc2ccc(C(=O)O)cc21]<br>2-(4-(6-((4-cyano-2-fluorobenzyl)oxy)pyridin-2-yl)-2-(pyridin-4-yl)benzyl)-1-(2-methoxyethyl)-1H-benzo[d]imidazole-6-carboxylic acid: ES/MS m/z 614.2; $^{1}$H NMR (400 MHz, Acetonitrile-d3) δ 8.68 (d, J = 5.2 Hz, 2H), 8.20 (s, 1H), 8.10-8.03 (m, 1H), 7.94 (d, J = 9.7 Hz, 2H), 7.82 (t, J = 7.9 Hz, 1H), 7.73-7.63 (m, 4H), 7.55 (dd, J = 16.8, 7.7 Hz, 1H), 7.46 (d, J = 8.8 Hz, 2H), 6.89 (d, J = 8.2 Hz, 1H), 5.62 (s, 2H), 4.40 (s, 2H), 4.29 (t, J = 5.0 Hz, 2H), 3.56 (t, J = 5.0 Hz, 2H), 3.13 (s, 3H). |
| 176 | 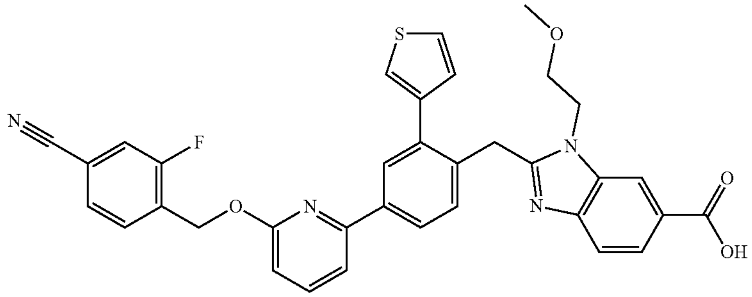 [SMILES: COCCn1c(Cc2ccc(-c3cccc(OCc4ccc(C#N)cc4F)n3)cc2-c2ccsc2)nc2ccc(C(=O)O)cc21]<br>2-(4-(6-((4-cyano-2-fluorobenzyl)oxy)pyridin-2-yl)-2-(thiophen-3-yl)benzyl)-1-(2-methoxyethyl)-1H-benzo[d]imidazole-6-carboxylic acid: ES/MS m/z 619.3; $^{1}$H NMR (400 MHz, Acetonitrile-d3) δ 8.40 (s, 1H), 8.15 (dd, J = 8.6, 1.5 Hz, 1H), 8.05 (dd, J = 8.1, 2.0 Hz, 1H), 7.97 (d, J = 2.0 Hz, 1H), 7.89-7.73 (m, 2H), 7.69 (t, J = 7.6 Hz, 1H), 7.58 (d, J = 7.5 Hz, 1H), 7.56-7.41 (m, 3H), 7.35 (dd, J = 3.0, 1.4 Hz, 1H), 7.12 (dd, J = 4.9, 1.5 Hz, 1H), 6.90 (d, J = 8.3 Hz, 1H), 5.62 (s, 2H), 4.68 (s, 2H), 4.40 (t, J = 5.0 Hz, 2H), 3.59 (t, J = 4.9 Hz, 2H), 3.19 (s, 3H). |
| 178 | 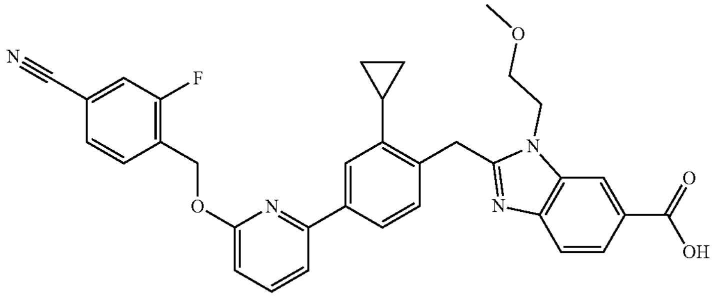 [SMILES: COCCn1c(Cc2ccc(-c3cccc(OCc4ccc(C#N)cc4F)n3)cc2C2CC2)nc2ccc(C(=O)O)cc21]<br>2-(4-(6-((4-cyano-2-fluorobenzyl)oxy)pyridin-2-yl)-2-cyclopropylbenzyl)-1-(2-methoxyethyl)-1H-benzo[d]imidazole-6-carboxylic acid: ES/MS m/z 577.4; $^{1}$H NMR (400 MHz, Acetonitrile-d3) δ 8.44 (d, J = 1.5 Hz, 1H), 8.13 (dd, J = 8.5, 1.5 Hz, 1H), 7.85-7.67 (m, 6H), 7.62-7.56 (m, 2H), 7.52 (d, J = 7.5 Hz, 1H), 7.28 (d, J = 8.0 Hz, 1H), 6.88 (d, J = 8.2 Hz, 1H), 5.66 (s, 2H), 4.82 (s, 2H), 4.61 (t, J = 5.0 Hz, 2H), 3.74 (t, J = 5.0 Hz, 2H), 3.27 (d, J = 1.5 Hz, 3H), 0.94-0.86 (m, 2H), 0.70 (dd, J = 5.4, 1.9 Hz, 2H). |

-continued

| Example | Structure/Name/Characterization |
|---|---|
| 185 | 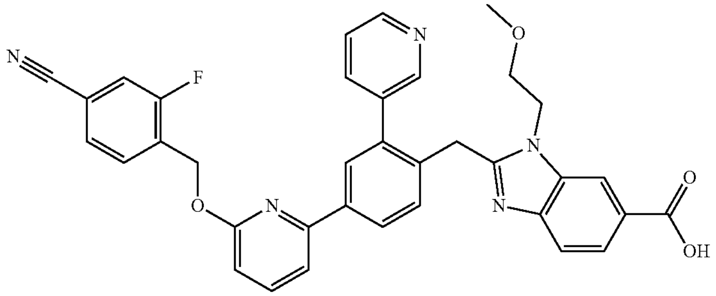 [SMILES: COCCn1c(Cc2ccc(-c3cccc(OCc4ccc(C#N)cc4F)n3)cc2-c2cccnc2)nc2ccc(C(=O)O)cc21]<br>2-(4-(6-((4-cyano-2-fluorobenzyl)oxy)pyridin-2-yl)-2-(pyridin-3-yl)benzyl)-1-(2-methoxyethyl)-1H-benzo[d]imidazole-6-carboxylic acid: ES/MS m/z 614.3; $^{1}$H NMR (400 MHZ, Acetonitrile-d3) δ 8.73 (d, J = 2.3 Hz, 1H), 8.70-8.66 (m, 1H), 8.23 (d, J = 1.6 Hz, 1H), 8.10-8.03 (m, 2H), 8.01-7.95 (m, 2H), 7.82 (t, J = 7.9 Hz, 1H), 7.69 (dt, J = 7.7, 3.4 Hz, 2H), 7.64-7.50 (m, 3H), 7.50-7.44 (m, 2H), 6.89 (d, J = 8.1 Hz, 1H), 5.62 (s, 2H), 4.46 (s, 2H), 4.30 (t, J = 5.0 Hz, 2H), 3.56 (t, J = 5.0 Hz, 2H), 3.13 (s, 2H). |
| 187 | 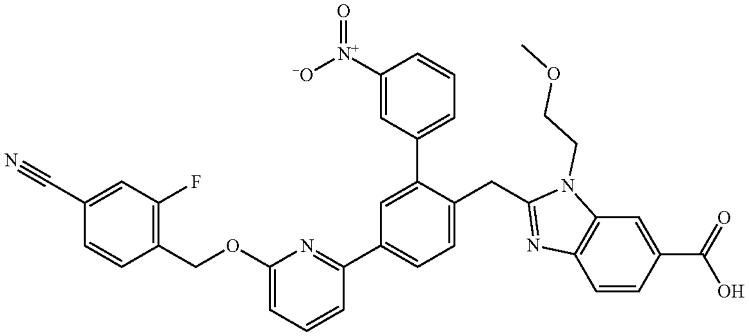<br>2-((5-(6-((4-cyano-2-fluorobenzyl)oxy)pyridin-2-yl)-3'-nitro-[1,1'-biphenyl]-2-yl)methyl)-1-(2-methoxyethyl)-1H-benzo[d]imidazole-6-carboxylic acid: ES/MS m/z 658.2; $^{1}$H NMR (400 MHz, Acetonitrile-d3) δ 8.38 (t, J = 3.5 Hz, 1H), 8.23 (t, J = 6.1 Hz, 1H), 8.14 (t, J = 6.8 Hz, 3H), 7.96 (d, J = 4.5 Hz, 1H), 7.89-7.64 (m, 5H), 7.59 (s, 1H), 7.51 (d, J = 6.4 Hz, 2H), 7.45-7.33 (m, 1H), 6.91 (t, J = 6.6 Hz, 1H), 5.60 (t, J = 3.4 Hz, 2H), 4.63 (t, J = 3.3 Hz, 2H), 4.36 (d, J = 5.2 Hz, 2H), 3.59-3.52 (m, 2H), 3.14-3.05 (m, 3H). |
| 188 | 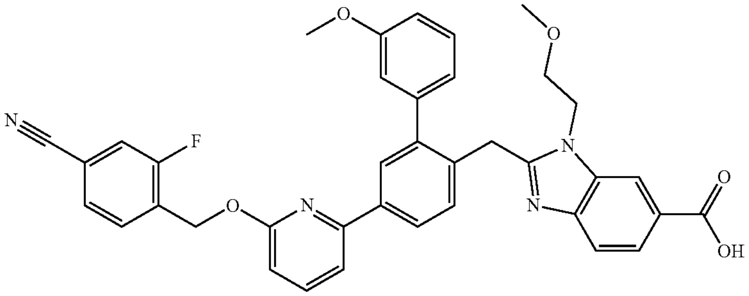 [SMILES: COCCn1c(Cc2ccc(-c3cccc(OCc4ccc(C#N)cc4F)n3)cc2-c2cccc(OC)c2)nc2ccc(C(=O)O)cc21]<br>2-((5-(6-((4-cyano-2-fluorobenzyl)oxy)pyridin-2-yl)-3'-methoxy-[1,1'-biphenyl]-2-yl)methyl)-1-(2-methoxyethyl)-1H-benzo[d]imidazole-6-carboxylic acid: ES/MS m/z 643.4; $^{1}$H NMR (400 MHz, Acetonitrile-d3) δ 8.33 (s, 1H), 8.11 (d, J = 8.8 Hz, 1H), 8.03 (d, J = 8.2 Hz, 1H), 7.87 (s, 1H), 7.80 (d, J = 6.1 Hz, 1H), 7.77-7.71 (m, 1H), 7.67 (d, J = 6.0 Hz, 1H), 7.58-7.53 (m, 1H), 7.53-7.45 (m, 2H), 7.39 (d, J = 10.0 Hz, 1H), 7.31 (q, J = 6.0, 3.5 Hz, 1H), 6.89 (q, J = 10.4, 8.5 Hz, 4H), 6.78 (s, 1H), 5.59 (s, 2H), 4.62 (s, 2H), 4.32-4.23 (m, 2H), 3.66 (d, J = 3.1 Hz, 3H), 3.56-3.46 (m, 2H), 3.14 (d, J = 3.2 Hz, 3H). |

-continued

| Example | Structure/Name/Characterization |
|---|---|
| 190 | 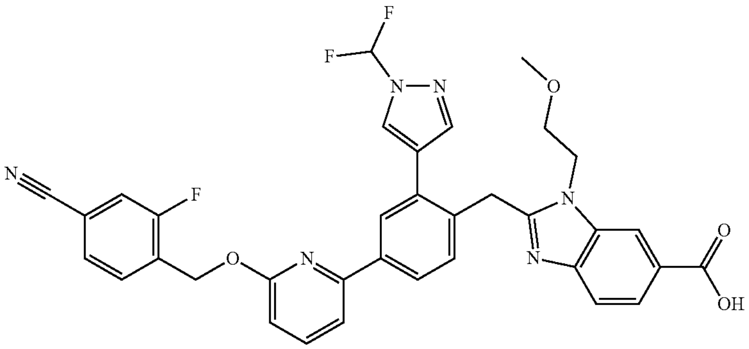 [SMILES: COCCn1c(Cc2ccc(-c3cccc(OCc4ccc(C#N)cc4F)n3)cc2-c2cnn(C(F)F)c2)nc2ccc(C(=O)O)cc21]<br>2-(4-(6-((4-cyano-2-fluorobenzyl)oxy)pyridin-2-yl)-2-(1-(difluoromethyl)-1H-pyrazol-4-yl)benzyl)-1-(2-methoxyethyl)-1H-benzo[d]imidazole-6-carboxylic acid: ES/MS m/z 653.3; $^1$H NMR (400 MHz, Acetonitrile-d3) δ 8.31-8.25 (m, 1H), 8.13 (s, 1H), 8.07-7.96 (m, 2H), 7.86-7.77 (m, 2H), 7.71 (dd, J = 10.1, 5.4 Hz, 2H), 7.60-7.49 (m, 3H), 7.39 (d, J = 8.8 Hz, 2H), 6.89 (d, J = 8.3 Hz, 1H), 5.64 (s, 2H), 4.59 (s, 2H), 4.38 (t, J = 4.9 Hz, 2H), 3.61 (t, J = 5.0 Hz, 2H), 3.19 (s, 3H). |
| 193 | 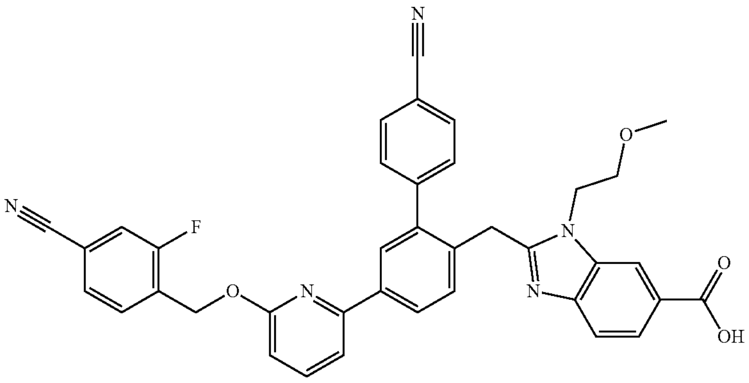 [SMILES: COCCn1c(Cc2ccc(-c3cccc(OCc4ccc(C#N)cc4F)n3)cc2-c2ccc(C#N)cc2)nc2ccc(C(=O)O)cc21]<br>2-((4'-cyano-5-(6-((4-cyano-2-fluorobenzyl)oxy)pyridin-2-yl)-[1,1'-biphenyl]-2-yl)methyl)-1-(2-methoxyethyl)-1H-benzo[d]imidazole-6-carboxylic acid: ES/MS m/z 638.3; $^1$H NMR (400 MHz, Acetonitrile-d3) δ 8.30 (s, 1H), 8.05 (d, J = 9.0 Hz, 2H), 7.88 (s, 1H), 7.79 (dd, J = 19.3, 7.0 Hz, 4H), 7.67 (s, 1H), 7.61-7.36 (m, 7H), 6.90 (t, J = 6.1 Hz, 1H), 5.60 (s, 2H), 4.52 (s, 2H), 4.28 (s, 2H), 3.54 (s, 2H), 3.13 (d, J = 4.8 Hz, 3H). |

Example 72. 2-(4-(3-((4-chloro-2-fluorobenzyl)oxy)isothiazol-4-yl)-2,6-difluorobenzyl)-1-(2-methoxyethyl)-1H-benzo[d]imidazole-6-carboxylic acid Procedure 60

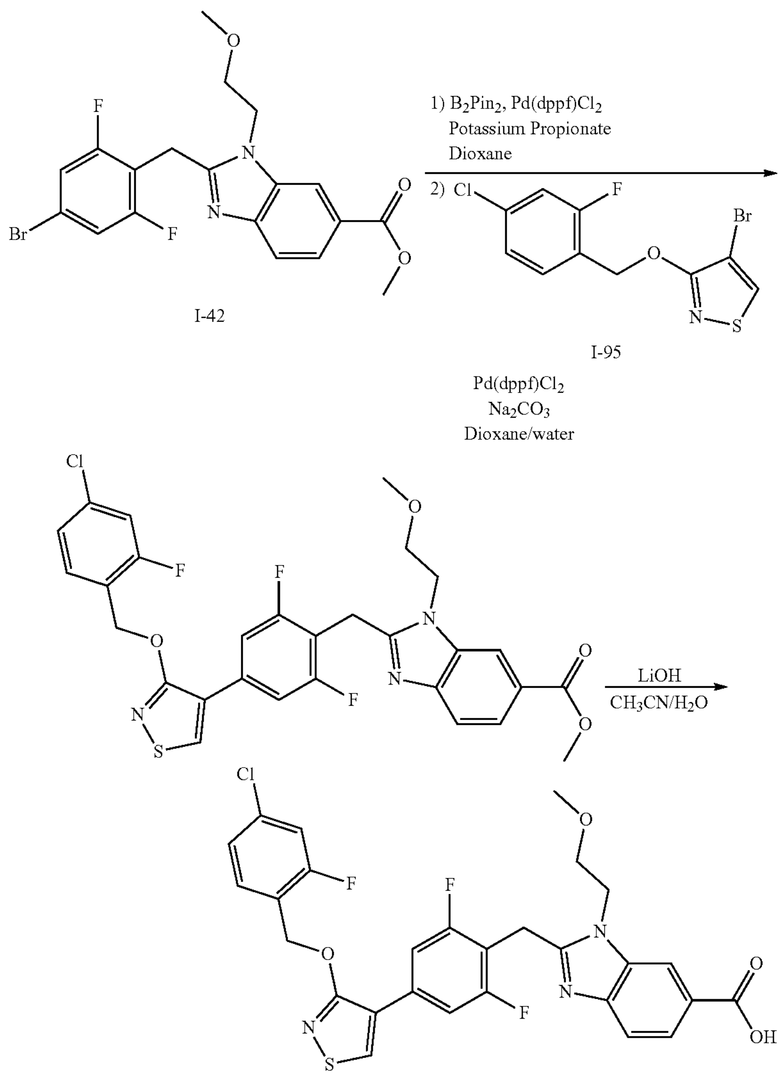

I-42

I-95

Example 72

Methyl 2-(4-(3-((4-chloro-2-fluorobenzyl)oxy)isothiazol-4-yl)-2,6-difluorobenzyl)-1-(2-methoxyethyl)-1H-benzo[d]imidazole-6-carboxylate: To a vial was added methyl 2-[(4-bromo-2,6-difluoro-phenyl)methyl]-3-(2-methoxyethyl)benzimidazole-5-carboxylate (I-42, 80.0 mg, 0.000182 mol), [1,1'-bis(diphenylphosphino)ferrocene]dichloropalladium(II) (0.0203 g, 2.73e-5 mol), and bis(pinacolato)diboron (0.0601 g, 0.000237 mol), potassium propionate (0.0613 g, 0.000546 mol) followed by 1,4-dioxane (1.50 mL). Argon was bubbled through the solution for 3 min then the mixture was heated to 110° C. for 45 min. To the mixture was added aqueous sodium carbonate (2.0 M, 0.182 mL, 0.000364 mol), [1,1'-bis(diphenylphosphino)ferrocene]dichloropalladium(II) (0.0101 g, 1.37e-5 mol), and 4-bromo-3-[(4-chloro-2-fluoro-phenyl)methoxy]isothiazole (I-95, 0.0588 g, 0.000182 mol). Argon was bubbled through the solution for 3 min then the mixture was heated to 80° C. for 1 h. The mixture was filtered through Celite, eluting with DCM and the filtrate was concentrated in vacuo. The crude residue was purified by column chromatography (0-100% EtOAc in hexane) to give the title compound. ES/MS m/z: 602.4 ($M+H^+$).

2-(4-(3-((4-chloro-2-fluorobenzyl)oxy)isothiazol-4-yl)-2,6-difluorobenzyl)-1-(2-methoxyethyl)-1H-benzo[d]imidazole-6-carboxylic acid (Example 72): To a mixture of methyl 2-[[4-[3-[(4-chloro-2-fluoro-phenyl)methoxy]isothiazol-4-yl]-2,6-difluoro-phenyl]methyl]-3-(2-methoxyethyl)benzimidazole-5-carboxylate (76.4 mg, 127 μmol) in acetonitrile (1.00 mL) and water (0.33 mL) was added lithium hydroxide monohydrate (16.0 mg, 0.381 mmol) and the vial was sealed and heated at 100° C. for 10 m). The reaction was quenched by the addition of 50 μL of TFA and the crude mixture was purified directly by RP-HPLC (0.7 TFA-ACN in 0.1, TFA Water, 15 min gradient, Column: Gemini 5 uM, NX-C18 110

Angstrom, 250×21.2 mm) to give the title compound as a bis-TFA salt as a lyophilized solid. ES/MS m/z: 588.3 (M+H$^+$); $^1$H NMR (400 MHz, DMSO-d6) δ 8.92 (d, J=1.9 Hz, 1H), 8.57 (d, J=2.0 Hz, 1H), 7.93 (dd, J=10.0, 1.4 Hz, 1H), 7.90 (s, 1H), 7.89-7.84 (m, 2H), 7.80-7.75 (m, 1H), 7.73 (dd, J=7.9, 1.5 Hz, 1H), 7.68 (d, J=7.5 Hz, 1H), 7.47 (t, J=7.9 Hz, 1H), 6.93 (d, J=8.1 Hz, 1H), 5.63 (s, 2H), 4.58 (s, 2H), 4.49 (s, 2H), 4.23 (s, 1H), 4.11 (s, 1H), 0.90-0.83 (m, 2H), 0.78-0.69 (n, 2H).

Example 76, 594. Compounds Prepared Using Procedure 60

Other compounds of the present disclosure prepared using the general route described in Procedure 60 include the following Examples.

| Example | Structure/Name/Characterization |
|---|---|
| 76 | 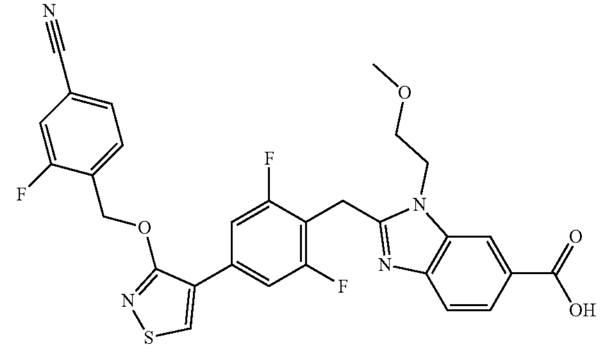 [SMILES: COCCn1c(Cc2c(F)cc(-c3csnc3OCc3ccc(C#N)cc3F)cc2F)nc2ccc(C(=O)O)cc21] 2-(4-(3-((4-cyano-2-fluorobenzyl)oxy)isothiazol-4-yl)-2,6-difluorobenzyl)-1-(2-methoxyethyl)-1H-benzo[d]imidazole-6-carboxylic acid: ES/MS m/z 579.3; $^1$H NMR (400 MHz, Methanol-d4) δ 9.02 (d, J = 1.9 Hz, 1H), 8.51 (d, J = 1.3 Hz, 1H), 8.19 (dd, J = 8.6, 1.5 Hz, 1H), 7.78-7.70 (m, 2H), 7.66-7.58 (m, 3H), 7.33 (dd, J = 10.3, 6.2 Hz, 1H), 5.66 (s, 2H), 4.78 (t, J = 5.0 Hz, 2H), 4.70 (s, 2H), 3.81 (t, J = 4.9 Hz, 2H), 3.29 (s, 3H). 1H NMR (400 MHz, Methanol-d4) δ 9.02 (d, J = 1.9 Hz, 1H), 8.51 (d, J = 1.3 Hz, 1H), 8.19 (dd, J = 8.6, 1.5 Hz, 1H), 7.78-7.70 (m, 2H), 7.66-7.58 (m, 3H), 7.33 (dd, J = 10.3, 6.2 Hz, 1H), 5.66 (s, 2H), 4.78 (t, J = 5.0 Hz, 2H), 4.70 (s, 2H), 3.81 (t, J = 4.9 Hz, 2H), 3.29 (s, 3H). |
| 594 | 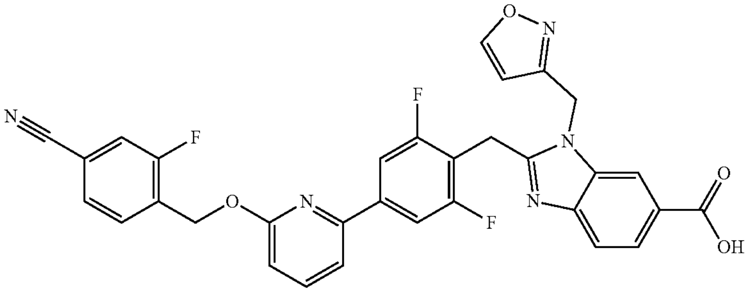 [SMILES: N#Cc1ccc(COc2cccc(-c3cc(F)c(Cc4nc5ccc(C(=O)O)cc5n4Cc4ccon4)c(F)c3)n2)c(F)c1] 2-(4-(6-((4-cyano-2-fluorobenzyl)oxy)pyridin-2-yl)-2,6-difluorobenzyl)-1-(isoxazol-3-ylmethyl)-1H-benzo[d]imidazole-6-carboxylic acid: ES/MS m/z 596.2; $^1$H NMR (400 MHz, DMSO-d6) δ 8.93 (d, J = 1.7 Hz, 1H), 8.23 (d, J = 1.5 Hz, 1H), 7.95-7.85 (m, 2H), 7.85-7.68 (m, 7H), 7.58 (d, J = 8.4 Hz, 1H), 6.97 (d, J = 8.2 Hz, 1H), 6.56 (d, J = 1.7 Hz, 1H), 5.90 (s, 2H), 5.63 (s, 2H), 4.47 (s, 2H).; Multiplet Report 1H NMR (400 MHz, Chloroform-d) δ 8.38 (d, J = 1.7 Hz, 1H), 8.14 (dd, J = 1.5, 0.6 Hz, 1H), 8.01 (dd, J = 8.5, 1.5 Hz, 1H), 7.79 (d, J = 8.5 Hz, 1H), 7.19-7.01 (m, 3H), 5.56 (s, 2H), 4.36 (s, 2H), 3.94 (s, 3H). |

Example 73. 2-(4-(6-((4-cyano-2-fluorobenzyl)oxy)-3,5-difluoropyridin-2-yl)-2-fluorobenzyl)-1-(2-methoxyethyl)-1H-benzo[d]imidazole-6-carboxylic acid Procedure 61

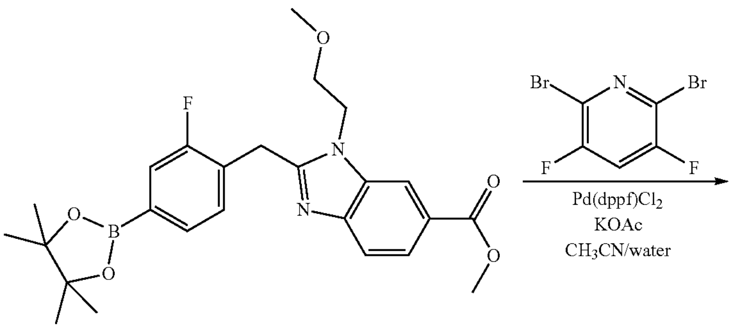

I-5

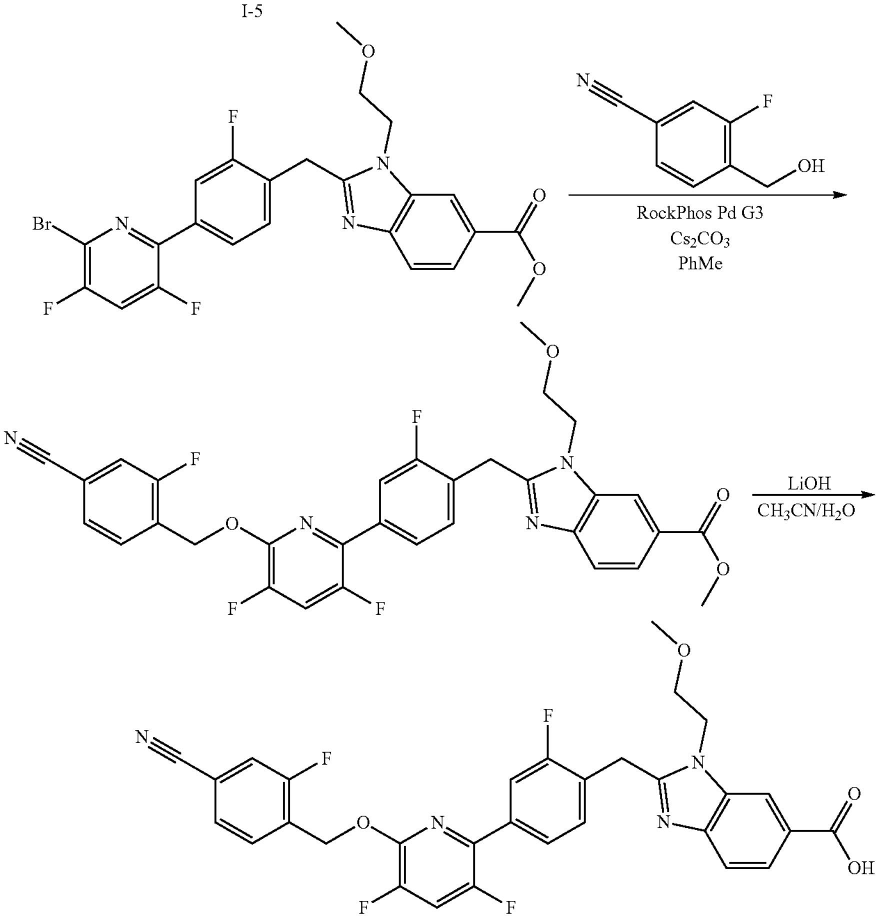

Example 73

Methyl 2-(4-(6-bromo-3,5-difluoropyridin-2-yl)-2-fluorobenzyl)-1-(2-methoxyethyl)-1H-benzo[d]imidazole-6-carboxylate: To a microwave vial was added 2,6-dibromo-3,5-difluoro-pyridine (100 mg, 0.366 mmol), methyl 2-[[2-fluoro-4-(4,4,5,5-tetramethyl-1,3,2-dioxaborolan-2-yl)phenyl]methyl]-3-(2-methoxyethyl)benzimidazole-5-carboxylate (I-5, 177 mg, 0.37 mmol) and (1,1'-bis(diphenylphosphino)ferrocene)-dichloropalladium(II) (0.0207 g, 2.93e-5 mol). Acetonitrile (3.0 mL) and 1.0 M potassium acetate in water (1.00 M, 0.916 mL, 0.92 mmol) were added, argon was bubbled through the mixture for 3 min, and the mixture was heated to 100° C. in a microwave for 20 min. The mixture was filtered through Celite, eluting with DCM and the filtrate was concentrated in vacuo. The crude residue was purified by column chromatography (0-100% EtOAc in hexane) to give the title compound. ES/MS m/z: 554.6 (M+H[+]).

Methyl 2-(4-(6-((4-cyano-2-fluorobenzyl)oxy)-3,5-difluoropyridin-2-yl)-2-fluorobenzyl)-1-(2-methoxyethyl)-1H-benzo[d]imidazole-6-carboxylate: To a vial was added methyl 2-[[4-(6-bromo-3,5-difluoro-2-pyridyl)-2-fluoro-phenyl]methyl]-3-(2-methoxyethyl)benzimidazole-5-carboxylate (57.0 mg, 0.000107 mol), 3-fluoro-4-(hydroxymethyl)benzonitrile (0.0322 g, 0.000213 mol), Pd RockPhos G3 (0.0134 g, 1.60e-5 mol) and cesium carbonate (0.104 g, 0.000320 mol) followed by toluene (1.50 mL). Argon was bubbled through the mixture for 3 min and the mixture was heated to 110° C. for 16 h. Another portion of Pd RockPhos G3 (0.0134 g, 1.60e-5 mol) was added, argon was bubbled through the mixture for 3 min, and the mixture was heated to 110° C. for an additional 24 h. The mixture was filtered through Celite, eluting with DCM and the filtrate was concentrated in vacuo. The crude residue was purified by column chromatography (0-100% EtOAc in hexane) to give the title compound. ES/MS m/z: 605.2 ($M+H^+$).

2-(4-(6-((4-cyano-2-fluorobenzyl)oxy)-3,5-difluoropyridin-2-yl)-2-fluorobenzyl)-1-(2-methoxyethyl)-1H-benzo[d]imidazole-6-carboxylic acid (Example 73): To a mixture of methyl 2-[[4-[6-[(4-cyano-2-fluoro-phenyl)methoxy]-3,5-difluoro-2-pyridyl]-2-fluoro-phenyl]methyl]-3-(2-methoxyethyl)benzimidazole-5-carboxylate (22.4 mg, 37.1 μmol) in acetonitrile (1.00 mL) and water (0.33 mL) was added lithium hydroxide monohydrate (4.66 mg, 0.111 mmol) and the vial was sealed and heated at 80° C. for 20 min. The reaction was quenched by the addition of 50 μL of TFA and the crude mixture was purified directly by RP-HPLC (0.1% TFA-ACN in 0.10% TFA water, 15 min gradient, Column: Gemini 5 μM, NX-C18 110 Angstrom, 250×21.2 mm) to give the title compound as a TFA salt. ES/MS m/z: 591.3 ($M+H^+$); $^1$H NMR (400 MHz, Methanol-d4) δ 8.56-8.54 (m, 1H), 8.22 (dd, J=8.6, 1.5 Hz, 1H), 7.88-7.83 (m, 1H), 7.81-7.71 (m, 4H), 7.67-7.59 (m, 2H), 7.54 (t, J=8.0 Hz, 1H), 5.70 (s, 2H), 4.85 (s, 3H), 4.82-4.79 (m, 2H), 4.77 (s, 2H), 3.82 (t, J=4.9 Hz, 2H).

Example 538. Compounds Prepared Using Procedure 61

Other compounds of the present disclosure prepared using the general route described in Procedure 61 include the following Example.

| Example | Structure/Name/Characterization |
|---|---|
| 538 | 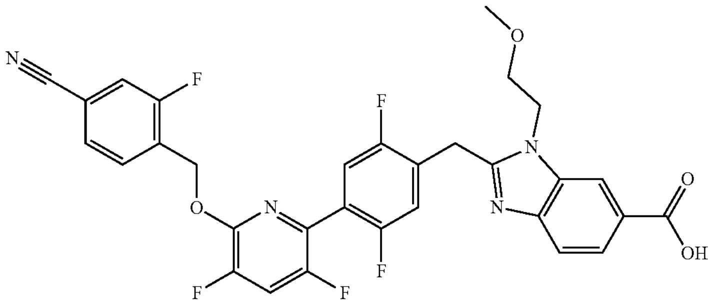 [SMILES: COCCn1c(Cc2cc(F)c(-c3nc(OCc4ccc(C#N)cc4F)c(F)cc3F)cc2F)nc2ccc(C(=O)O)cc21]<br>2-(4-(6-((4-cyano-2-fluorobenzyl)oxy)-3,5-difluoropyridin-2-yl)-2,5-difluorobenzyl)-1-(2-methoxyethyl)-1H-benzo[d]imidazole-6-carboxylic acid: ES/MS m/z 609.1; $^1$H NMR (400 MHz, Methanol-d4) δ 8.27 (t, J = 1.0 Hz, 1H), 8.07 (dd, J = 8.5, 1.5 Hz, 1H), 7.84 (d, J = 8.6 Hz, 1H), 7.61 (dd, J = 9.5, 8.6 Hz, 1H), 7.57-7.51 (m, 1H), 7.42 (dd, J = 3.2, 1.5 Hz, 2H), 7.38-7.29 (m, 2H), 4.85 (s, 2H), 4.51-4.35 (m, 2H), 3.84-3.65 (m, 2H), 3.64-3.51 (m, 2H), 3.14 (s, 3H). |

Example 74. 2-(4-(6-((4-chloro-2-methoxybenzyl)oxy)pyridin-2-yl)-3-fluorobenzyl)-1-((1-(cyanomethyl)cyclopropyl)methyl)-1H-benzo[d]imidazole-6-carboxylic acid Procedure 62

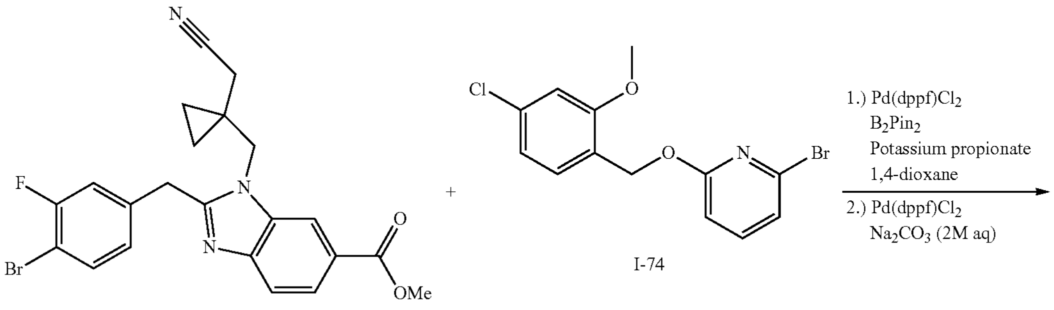

I-96 I-74

-continued

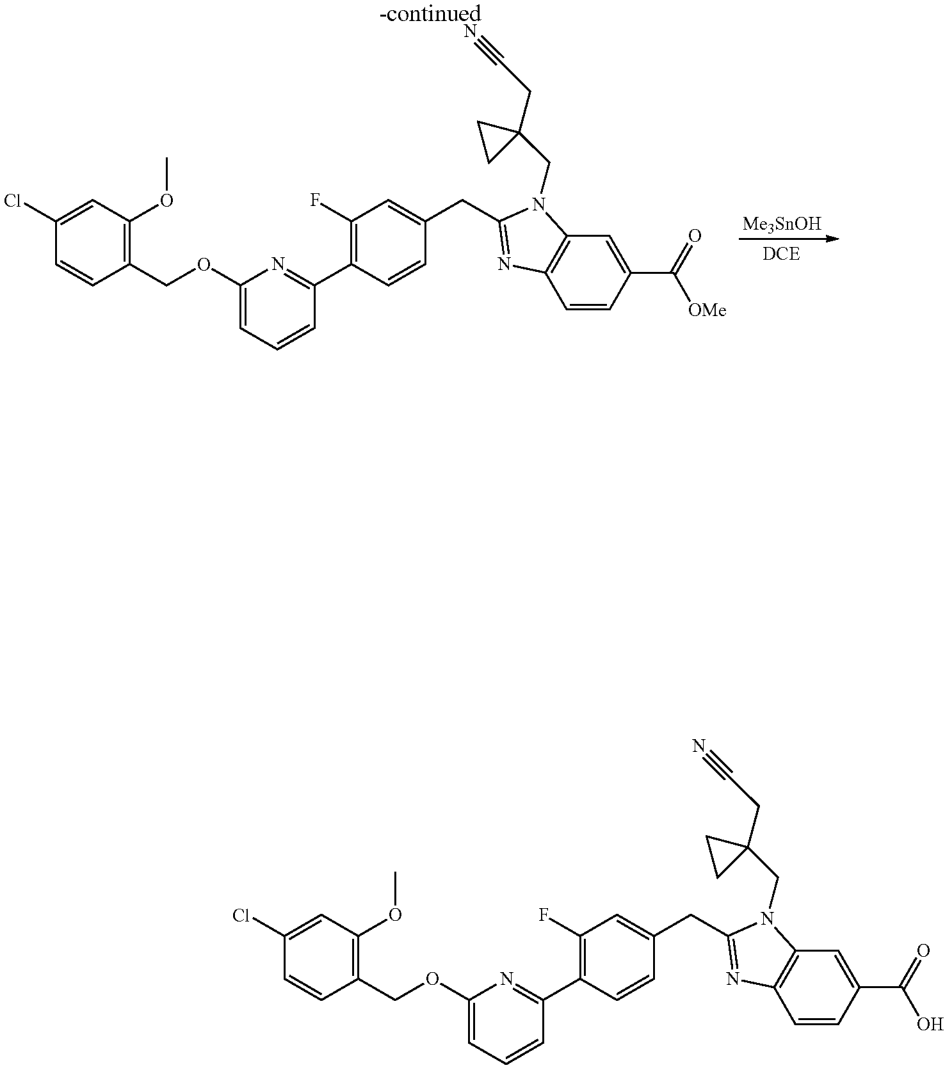

Example 74

Methyl 2-(4-(6-((4-chloro-2-methoxybenzyl)oxy)pyridin-2-yl)-3-fluorobenzyl)-1-((1-(cyanomethyl)cyclopropyl)methyl)-1H-benzo[d]imidazole-6-carboxylate: To a vial was added methyl 2-[(4-bromo-3-fluoro-phenyl)methyl]-3-[[1-(cyanomethyl)cyclopropyl]methyl]benzimidazole-5-carboxylate (I-96, 80.0 mg, 0.18 mmol), [1,1'-bis(diphenylphosphino)ferrocene]dichloropalladium(II) (0.0195 g, 2.63e-5 mol), bis(pinacolato)diboron (0.0579 g, 0.23 mmol) and potassium propionate (0.089 g, 0.56 mmol) followed by 1,4-dioxane (1.60 mL). Argon was bubbled through the solution for 3 min then the mixture was heated to 110° C. for 45 min. To the mixture was added aqueous sodium carbonate (2.00 M, 0.18 mL, 0.29 mmol), [1,1'-bis(diphenylphosphino)ferrocene]dichloropalladium(II) (0.0098 g, 1.31e-5 mol), and 2-bromo-6-[(4-chloro-2-methoxy-phenyl)methoxy]pyridine (I-74, 0.0578 g, 0.18 mmol). Argon was bubbled through the solution for 3 min then the mixture was heated to 80° C. for 1 h. The mixture was filtered through CCelite, eluting with DCM and the filtrate was concentrated in vacuo. The crude residue was purified by column chromatography (0-100% EtOAc in hexane) to give the title compound. ES/MS m/z: 625.2 ($M+H^+$).

2-(4-(6-((4-chloro-2-methoxybenzyl)oxy)pyridin-2-yl)-3-fluorobenzyl)-1-((1-(cyanomethyl)cyclopropyl)methyl)-1H-benzo[d]imidazole-6-carboxylic acid (Example 74): To a solution of methyl 2-[[4-[6-[(4-chloro-2-methoxy-phenyl)methoxy]-2-pyridyl]-3-fluoro-phenyl]methyl]-3-[[1-(cyanomethyl)cyclopropyl]methyl]benzimidazole-5-carboxylate (48.7 mg, 77.9 μmol) in DCE (1.00 mL) was added trimethyltin hydroxide (0.14 g, 0.78 mmol) and the mixture was stirred at 80° C. for 30 min. The reaction was quenched by the addition of 50 μL of TFA and the crude mixture was purified directly by RP-HPLC (15-71.60% 0.1% TFA-ACN in 0.1% TFA water, 15 min gradient, Column: Gemini 5 uM, NX-C18 110 Angstrom, 250×21.2 mm) to give the title compound as a bis TFA-salt. ES/MS m/z: 611.4 ($M+H^+$); $^1H$ NMR (400 MHz, DMSO-d6) δ 8.34-8.32 (m, 1H), 7.96 (t, J=8.3 Hz, 1H), 7.88 (dd, J=8.5, 1.5 Hz, 1H), 7.86-7.80 (m, 1H), 7.69 (d, J=8.4 Hz, 1H), 7.45-7.41 (m, 2H), 7.39-7.32 (m, 2H), 7.13 (d, J=2.0 Hz, 1H), 7.02 (dd, J=8.1, 2.0 Hz, 1H), 6.89 (d, J=8.2 Hz, 1H), 5.39 (s, 2H), 4.54 (d, J=10.8 Hz, 4H), 3.85 (s, 3H), 2.69 (s, 2H), 0.74-0.68 (m, 4H).

Example 75, 93. Compounds Prepared Using Procedure 62

Other compounds of the present disclosure prepared using the general route described in Procedure 62 include the following Examples.

| Example | Structure/Name/Characterization |
|---|---|
| 75 | 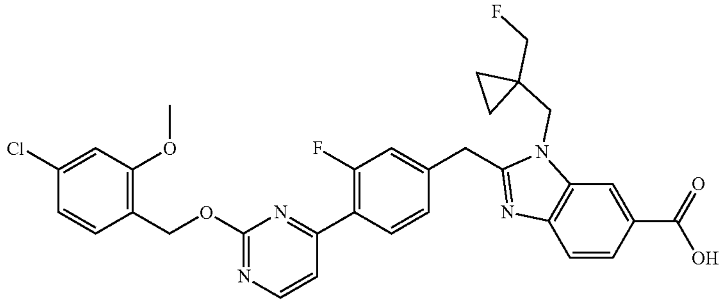 [SMILES: COc1cc(Cl)ccc1COc1nccc(-c2ccc(Cc3nc4ccc(C(=O)O)cc4n3CC3(CF)CC3)cc2F)n1]<br>2-(4-(2-((4-chloro-2-methoxybenzyl)oxy)pyrimidin-4-yl)-3-fluorobenzyl)-1-((1-(fluoromethyl)cyclopropyl)methyl)-1H-benzo[d]imidazole-6-carboxylic acid: ES/MS m/z 605.2; $^{1}$H NMR (400 MHz, DMSO-d6) δ 8.72 (d, J = 5.2 Hz, 1H), 8.27 (s, 1H), 8.07 (t, J = 8.1 Hz, 1H), 7.84 (dd, J = 8.5, 1.5 Hz, 1H), 7.66 (d, J = 8.4 Hz, 1H), 7.55 (dd, J = 5.2, 2.0 Hz, 1H), 7.44 (d, J = 8.1 Hz, 1H), 7.42-7.34 (m, 2H), 7.15 (d, J = 2.0 Hz, 1H), 7.04 (dd, J = 8.0, 2.0 Hz, 1H), 5.42 (s, 2H), 4.55-4.49 (m, 4H), 4.23 (s, 1H), 4.11 (s, 1H), 3.86 (s, 3H), 0.84-0.77 (m, 2H), 0.72-0.68 (m, 2H). |
| 93 | 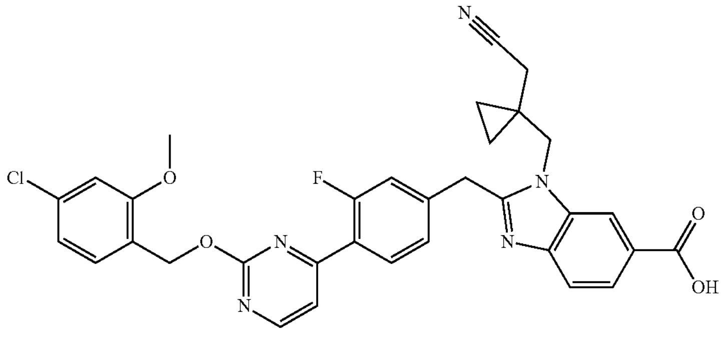 [SMILES: COc1cc(Cl)ccc1COc1nccc(-c2ccc(Cc3nc4ccc(C(=O)O)cc4n3CC3(CC#N)CC3)cc2F)n1]<br>2-(4-(2-((4-chloro-2-methoxybenzyl)oxy)pyrimidin-4-yl)-3-fluorobenzyl)-1-((1-(cyanomethyl)cyclopropyl)methyl)-1H-benzo[d]imidazole-6-carboxylic acid: ES/MS m/z 612.2; $^{1}$H NMR (400 MHz, DMSO-d6) δ 8.72 (d, J = 5.2 Hz, 1H), 8.29 (d, J = 1.5 Hz, 1H), 8.07 (t, J = 8.1 Hz, 1H), 7.84 (dd, J = 8.4, 1.5 Hz, 1H), 7.66 (d, J = 8.4 Hz, 1H), 7.55 (dd, J = 5.2, 2.1 Hz, 1H), 7.46-7.36 (m, 3H), 7.15 (d, J = 2.0 Hz, 1H), 7.04 (dd, J = 8.1, 2.0 Hz, 1H), 5.42 (s, 2H), 4.55-4.49 (m, 4H), 3.86 (s, 3H), 2.68 (s, 2H), 0.72-0.66 (m, 4H). |

Example 92. 2-(4-(6-((4-cyano-2-fluorobenzyl)oxy)pyridin-2-yl)-2-fluorobenzyl)-1-((1-(fluoromethyl)cyclopropyl)methyl)-1H-imidazo[4,5-b]pyridine-6-carboxylic acid Procedure 63

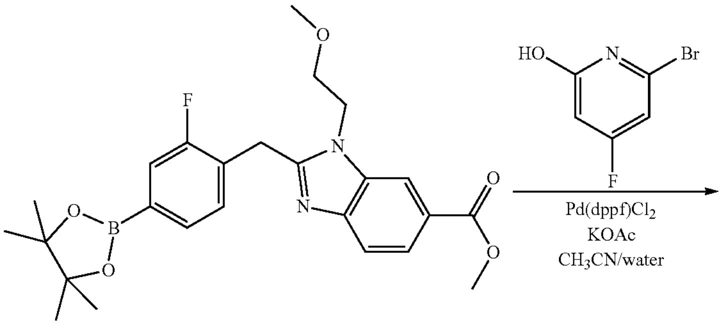

I-5

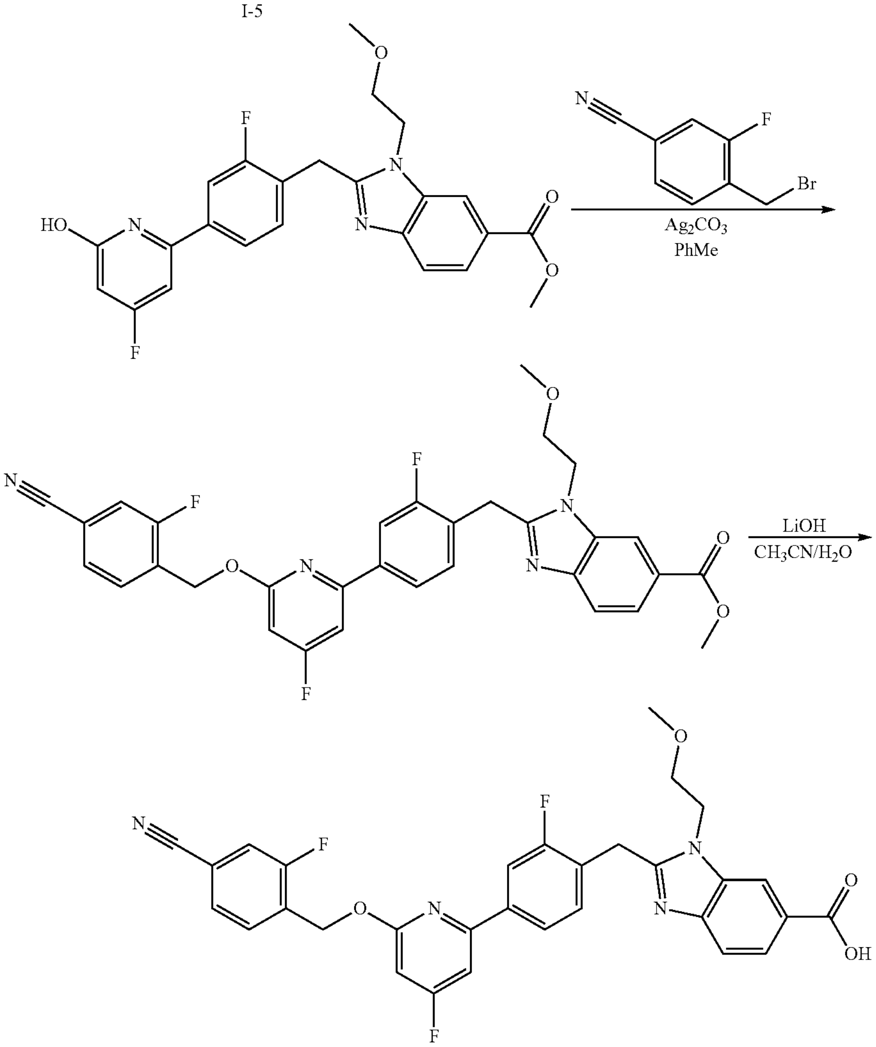

Example 92

Methyl 2-(2-fluoro-4-(4-fluoro-6-hydroxypyridin-2-yl)benzyl)-1-(2-methoxyethyl)-1H-benzo[d]imidazole-6-carboxylate: To a microwave vial was added methyl 2-[[2-fluoro-4-(4,4,5,5-tetramethyl-1,3,2-dioxaborolan-2-yl)phenyl]methyl]-3-(2-methoxyethyl)benzimidazole-5-carboxylate (I-5) (60.0 mg, 0.128 mmol), 6-chloro-4-fluoro-pyridin-2-ol (22.7 mg, 0.154 mmol) and (1,1'-bis(diphenylphosphino)ferrocene)-dichloropalladium(II) (7.25 mg, 1.02e-5 mol). Acetonitrile (1.10 mL) and 1.0 M potassium acetate in water (1.00 M, 0.256 mL, 0.256 mmol) were added, argon was bubbled through the mixture for 3 min and the mixture was heated to 80° C. in a microwave for 10 min. The mixture was filtered through CCelite, eluting with DCM and the filtrate was concentrated in vacuo. The crude residue was purified by column chromatography (0-100% EtOAc in hexane) to give the title compound. ES/MS m/z: 454.3 (M+H$^+$).

Methyl 2-(4-(6-((4-cyano-2-fluorobenzyl)oxy)-4-fluoropyridin-2-yl)-2-fluorobenzyl)-1-(2-methoxyethyl)-1H-benzo[d]imidazole-6-carboxylate: To a vial was added methyl 2-[[2-fluoro-4-(4-fluoro-6-hydroxy-2-pyridyl)phenyl]methyl]-3-(2-methoxyethyl)benzimidazole-5-carboxylate (21.0 mg, 0.0463 mmol), 4-(bromomethyl)-3-fluorobenzonitrile (0.0124 g, 0.0579 mmol) and Silver carbonate (0.0383 g, 0.139 mmol) followed by toluene (0.750 mL) and the mixture was stirred at 90° C. for 14 h. The mixture was filtered through a fritted funnel, eluting with DCM and the filtrate was concentrated in vacuo. The residue was used directly in the following step without further purification. ES/MS m/z: 599.2 (M+H$^+$).

2-(4-(6-((4-cyano-2-fluorobenzyl)oxy)pyridin-2-yl)-2-fluorobenzyl)-1-((1-(fluoromethyl)cyclopropyl)methyl)-1H-imidazo[4,5-b]pyridine-6-carboxylic acid (Example 92): To a mixture of methyl 2-[[4-[6-[(4-cyano-2-methoxyphenyl)methoxy]-4-fluoro-2-pyridyl]-2-fluoro-phenyl]methyl]-3-(2-methoxyethyl)benzimidazole-5-carboxylate (27.7 mg, 46.3 μmol) in acetonitrile (1.00 mL) and water (0.33 mL) was added lithium hydroxide monohydrate (5.83 mg, 0.139 mmol) and the mixture was stirred at 60° C. for 1 h. The reaction was quenched by the addition of 50 μL of TFA and the crude mixture was purified directly by RP-HPLC (15-65.44% 0.1% TFA-ACN in 0.1% TFA water, 15 min gradient, Column: Gemini 5 uM, NX-C18 110 Angstrom, 250×21.2 mm) to give the title compound as a TFA salt. ES/MS m/z: 585.3 (M+H$^+$); $^1$H NMR (400 MHz, Methanol-d4) δ 8.44 (s, 1H), 8.13 (d, J=8.6 Hz, 1H), 7.88 (d, J=9.6 Hz, 2H), 7.73 (d, J=8.6 Hz, 1H), 7.58 (d, J=7.8 Hz, 1H), 7.49-7.37 (m, 3H), 7.33 (d, J=8.1 Hz, 1H), 6.71-6.65 (m, 1H), 5.61 (s, 2H), 4.72-4.68 (m, 2H), 4.66 (s, 2H), 3.98 (s, 3H), 3.77 (t, J=4.9 Hz, 2H), 3.30 (s, 3H).

Example 77. Compounds Prepared Using Procedure 63

Other compounds of the present disclosure prepared using the general route described in Procedure 63 include the following Example.

| Example | Structure/Name/Characterization |
| --- | --- |
| 77 | 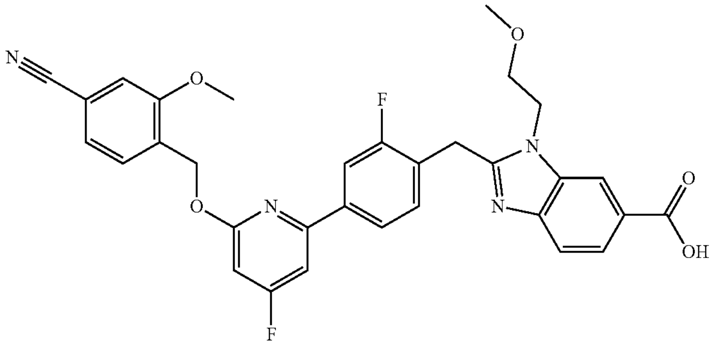 [SMILES: COCCn1c(Cc2ccc(-c3cc(F)cc(OCc4ccc(C#N)cc4OC)n3)cc2F)nc2ccc(C(=O)O)cc21] 2-(4-(6-((4-cyano-2-methoxybenzyl)oxy)-4-fluoropyridin-2-yl)-2-fluorobenzyl)-1-(2-methoxyethyl)-1H-benzo[d]imidazole-6-carboxylic acid: ES/MS m/z 585.3; $^1$H NMR (400 MHz, Methanol-d4) δ 8.44 (s, 1H), 8.13 (d, J = 8.6 Hz, 1H), 7.88 (d, J = 9.6 Hz, 2H), 7.73 (d, J = 8.6 Hz, 1H), 7.58 (d, J = 7.8 Hz, 1H), 7.49-7.37 (m, 3H), 7.33 (d, J = 8.1 Hz, 1H), 6.71-6.65 (m, 1H), 5.61 (s, 2H), 4.72-4.68 (m, 2H), 4.66 (s, 2H), 3.98 (s, 3H), 3.77 (t, J = 4.9 Hz, 2H), 3.30 (s, 3H). |

Example 78. 2-((4-(2-((4-cyano-2-fluorobenzyl)oxy)thiazol-4-yl)-1H-pyrazol-1-yl)methyl)-1-(2-methoxyethyl)-1H-benzo[d]imidazole-6-carboxylic acid Procedure 64

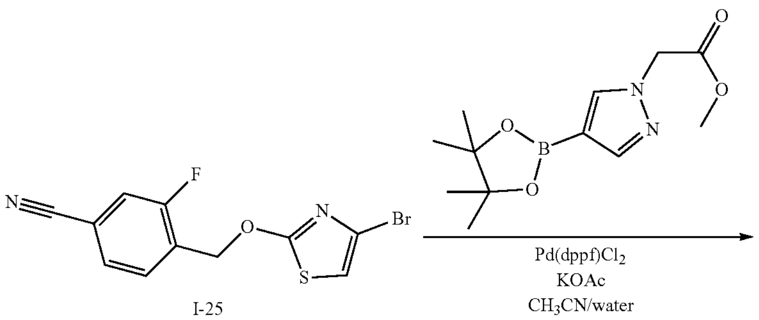

I-25

-continued

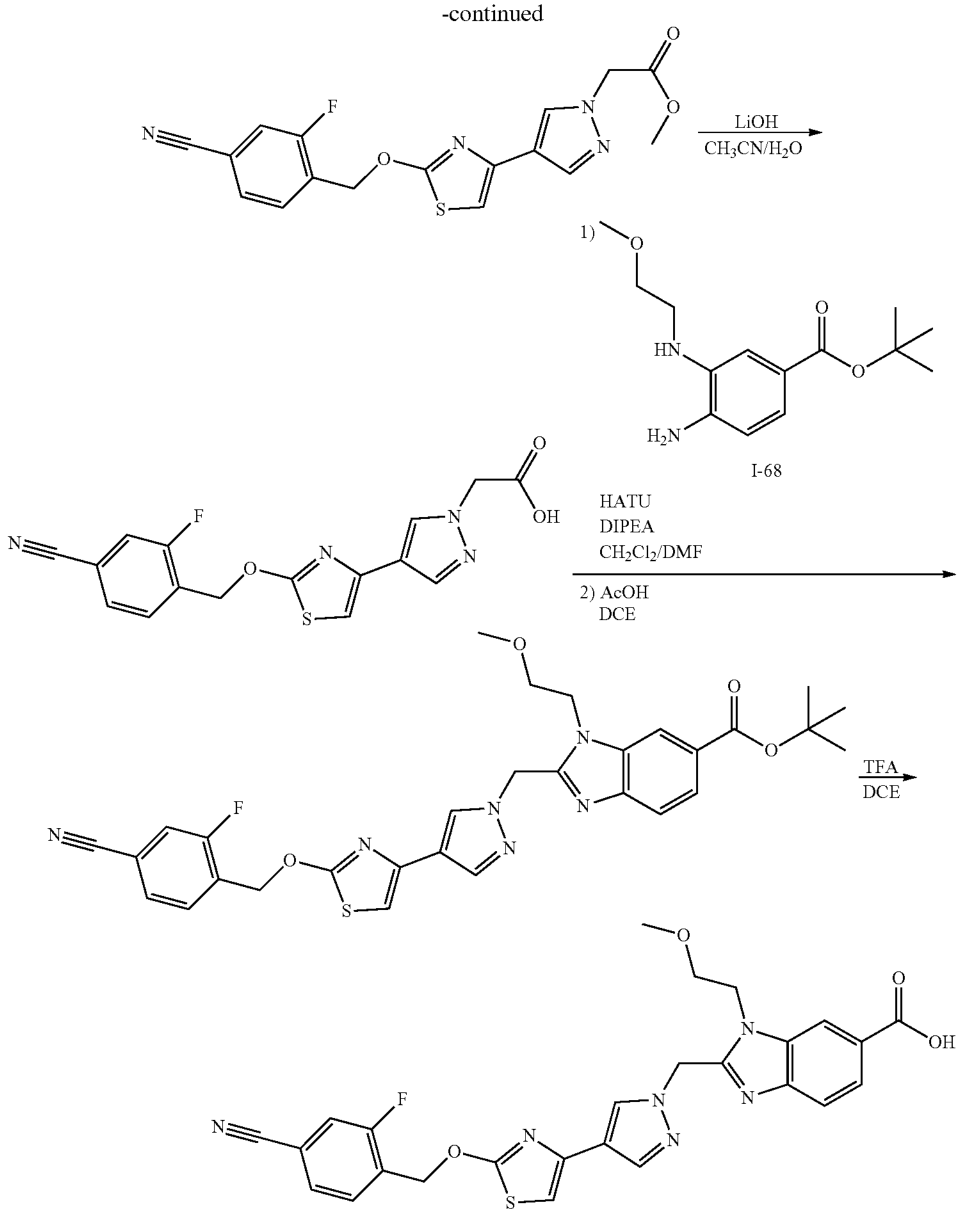

Example 78

Methyl 2-(4-(2-((4-cyano-2-fluorobenzyl)oxy)thiazol-4-yl)-1H-pyrazol-1-yl)acetate: To a microwave vial was added ethyl 2-[4-(4,4,5,5-tetramethyl-1,3,2-dioxaborolan-2-yl)pyrazol-1-yl]acetate (86.4 mg, 0.31 mmol) and acetonitrile (2.11 mL) followed by 4-[(4-bromothiazol-2-yl)oxymethyl]-3-fluoro-benzonitrile (I-25, 69.0 mg, 0.22 mmol), (1,1'-bis(diphenylphosphino)ferrocene)-dichloropalladium(II) (0.0187 g, 2.64e-5 mol) and 1.0 M potassium acetate in water (1.00 M, 0.661 mL, 0.66 mmol), argon was bubbled through the mixture for 3 min and the mixture was heated to 110° C. in a microwave for 45 min. The mixture was filtered through Celite, eluting with DCM and the filtrate was concentrated in vacuo. The crude residue was purified by column chromatography (0-100% EtOAc in hexane) to give the title compound. ES/MS m/z: 387.1 (M+H$^+$).

2-(4-(2-((4-cyano-2-fluorobenzyl)oxy)thiazol-4-yl)-1H-pyrazol-1-yl)acetic acid: To a mixture of ethyl 2-[4-[2-[(4-cyano-2-fluoro-phenyl)methoxy]thiazol-4-yl]pyrazol-1-yl]acetate (61.5 mg, 159 μmol) in acetonitrile (1.00 mL) and water (1.00 mL) was added lithium hydroxide monohydrate (20.0 mg, 0.477 mmol) and the mixture was heated to 60° C. for 30 min. The reaction was quenched by the addition of 5% aqueous citric acid and the mixture was extracted with EtOAc (3×). The combined organic extracts were washed with brine, dried over sodium sulfate, filtered and the filtrate was concentrated in vacuo to give the title compound which was used directly in the next step without further purification. ES/MS m/z: 359.1 (M+H$^+$)

Tert-butyl 2-((4-(2-((4-cyano-2-fluorobenzyl)oxy)thiazol-4-yl)-1H-pyrazol-1-yl)methyl)-1-(2-methoxyethyl)-1H-benzo[d]imidazole-6-carboxylate: To a solution of tert-butyl 4-amino-3-(2-methoxyethylamino)benzoate (I-68) (40.7 mg, 0.153 mmol) in DMF (1.00 mL) was added 2-[4-[2-[(4-cyano-2-fluoro-phenyl)methoxy]thiazol-4-yl]

pyrazol-1-yl]acetic acid (49.8 mg, 0.139 mmol), 2-(7-Aza-1H-benzotriazole-1-yl)-1,1,3,3-tetramethyluronium hexafluorophosphate (HATU) (63.4 mg, 0.167 mmol) and N,N-Diisopropylethylamine (redistilled, 99.5%) (0.121 mL, 0.695 mmol) and stirred for 2 h. The reaction was quenched by the addition of water and the mixture was extracted with DCM (3×). The combined organic extracts were dried over sodium sulfate, filtered and the filtrate was concentrated in vacuo. The crude residue was dissolved in AcOH (1.5 mL) and the mixture was heated to 60° C. for 1 h. The mixture was concentrated in vacuo, the crude residue was taken up in DCM and washed with saturated aqueous sodium bicarbonate. The layers were separated and the aqueous layer was extracted with DCM (2×). The combined organic extracts were dried over sodium sulfate, filtered and the filtrate was concentrated in vacuo. The crude residue was purified by column chromatography (0-100% EtOAc in hexane) to give the title compound. ES/MS m/z: 589.1 (M+H$^+$).

mmol), the vial was capped and the mixture was heated to 50° C. for 2 h. The crude residue was purified by RP-HPLC (15-55.75% 0.1% TFA-ACN in 0.1% TFA Water, 15 min gradient, Column: Gemini 5 uM, NX-C18 110 Angstrom, 250×21.2 mm) to give the title compound as a TFA salt. ES/MS m/z: 533.3 (M+H$^+$); $^1$H NMR (400 MHz, Methanol-d4) δ 8.44-8.39 (m, 1H), 8.14-8.07 (m, 2H), 7.94-7.90 (m, 1H), 7.82-7.75 (m, 2H), 7.65-7.59 (m, 2H), 6.95 (s, 1H), 5.90 (s, 2H), 5.64 (s, 2H), 4.72 (t, J=5.0 Hz, 2H), 3.71 (t, J=5.0 Hz, 2H), 3.30 (s, 3H).

Example 79. 2-(4-(2-((4-chloro-2-fluorobenzyl)oxy)pyrimidin-4-yl)-2-fluorobenzyl)-1-((1-(cyanomethyl)cyclopropyl)methyl)-1H-benzo[d]imidazole-6-carboxylic acid Procedure 65

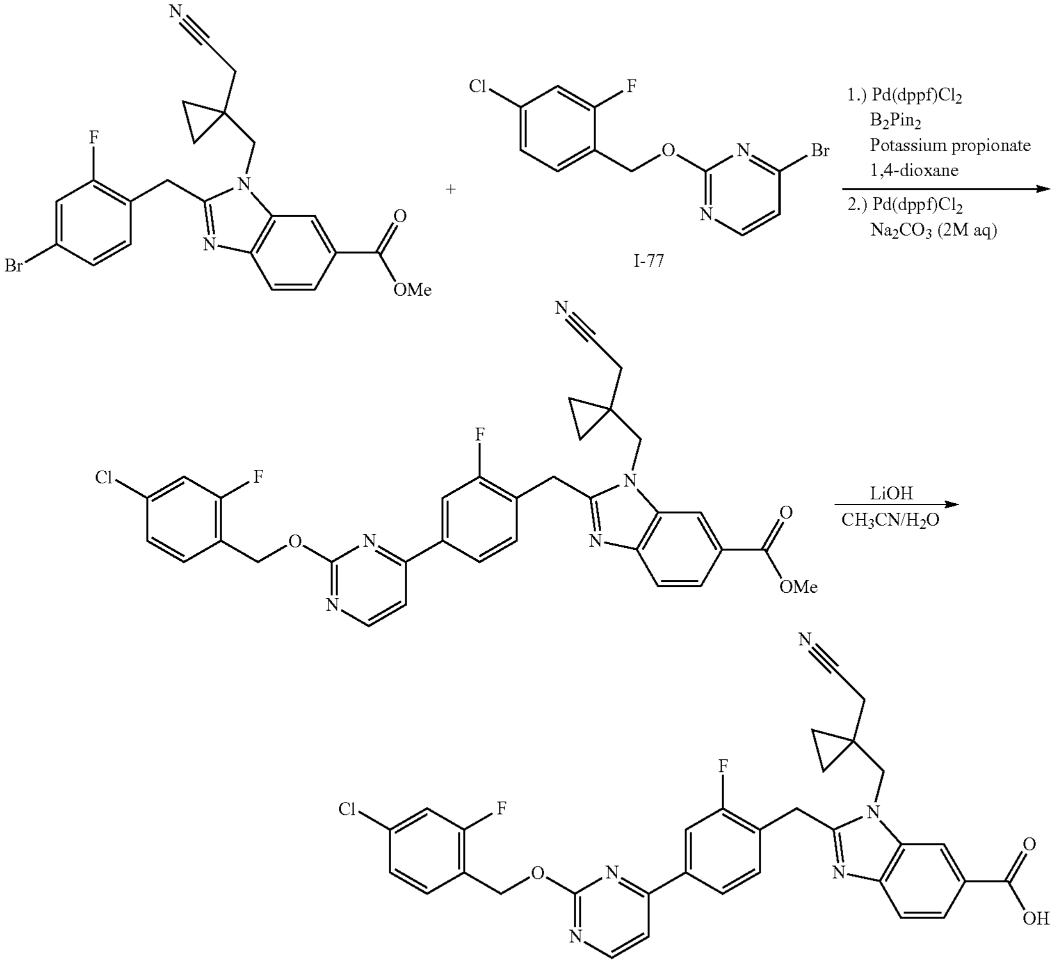

I-77

Example 79

2-((4-(2-((4-cyano-2-fluorobenzyl)oxy)thiazol-4-yl)-1H-pyrazol-1-yl)methyl)-1-(2-methoxyethyl)-1H-benzo[d]imidazole-6-carboxylic acid (Example 78): To a mixture of tert-butyl 2-[[4-[2-[(4-cyano-2-fluoro-phenyl)methoxy]thiazol-4-yl]pyrazol-1-yl]methyl]-3-(2-methoxyethyl)benzimidazole-5-carboxylate (17.8 mg, 30.2 μmol) in DCM (1.00 mL) was added trifluoroacetic acid (4.63e-2 mL, 0.605

Methyl 2-(4-(2-((4-chloro-2-fluorobenzyl)oxy)pyrimidin-4-yl)-2-fluorobenzyl)-1-((1-(cyanomethyl)cyclopropyl)methyl)-1H-benzo[d]imidazole-6-carboxylate: To a vial was added methyl 2-[(4-bromo-3-fluoro-phenyl)methyl]-3-[[1-(cyanomethyl)cyclopropyl]methyl]benzimidazole-5-carboxylate (60 mg, 0.13 mmol) (synthesized in a manner analogous to I-96), [1,1'-bis(diphenylphosphino)ferrocene]

dichloropalladium(II) (0.015 g, 1.97e-5 mol), bis(pinacolato)diboron (0.043 g, 0.17 mmol) and potassium propionate (0.044 g, 0.39 mmol) followed by 1,4-dioxane (1.20 mL). Argon was bubbled through the solution for 3 min then the mixture was heated to 110° C. for 45 min. To the mixture was added aqueous sodium carbonate (2.00 M, 0.13 mL, 0.26 mmol), [1,1'-bis(diphenylphosphino)ferrocene]dichloropalladium(II) (0.0073 g, 9.86e-6 mol), and 4-bromo-2-[(4-chloro-2-fluoro-phenyl)methoxy]pyrimidine (I-77, 0.044 g, 0.14 mmol). Argon was bubbled through the solution for 3 min then the mixture was heated to 80° C. for 90 min. The mixture was filtered through CCelite, eluting with DCM and the filtrate was concentrated in vacuo. The crude residue was purified by column chromatography (0-100% EtOAc in hexane) to give the title compound. ES/MS m/z: 614.2 ($M+H^+$).

2-(4-(2-((4-chloro-2-fluorobenzyl)oxy)pyrimidin-4-yl)-2-fluorobenzyl)-1-((1-(cyanomethyl)cyclopropyl)methyl)-1H-benzo[d]imidazole-6-carboxylic acid (Example 79): To a mixture of methyl 2-[[4-[2-[(4-chloro-2-fluoro-phenyl)methoxy]pyrimidin-4-yl]-3-fluoro-phenyl]methyl]-3-[[1-(cyanomethyl)cyclopropyl]methyl]benzimidazole-5-carboxylate (49.0 mg, 79.8 μmol) in acetonitrile (1.00 mL) and water (0.33 mL) was added lithium hydroxidemonohydrate (10.0 mg, 0.239 mmol) and the mixture was stirred at 60° C. for 30 min. The mixture was poured into 5% aqueous citric acid and the mixture was extracted with EtOAc (3×). The combined organic extracts were washed with brine, dried over sodium sulfate, filtered and the filtrate was concentrated in vacuo. The crude residue was taken up in DMF and purified by RP-HPLC (15-63.67% 0.1% TFA-ACN in 0.1% TFA Water, 15 min gradient, Column: Gemini 5 uM, NX-C18 110 Angstrom, 250×21.2 mm) to give the title compound as a TFA salt. ES/MS m/z: 600.3 ($M+H^+$); $^1H$ NMR (400 MHz, DMSO-d6) δ 8.73 (d, J=5.2 Hz, 1H), 8.30 (d, J=1.5 Hz, 1H), 8.09 (t, J=8.2 Hz, 1H), 7.85 (dd, J=8.5, 1.5 Hz, 1H), 7.67 (d, J=8.5 Hz, 1H), 7.63 (t, J=8.2 Hz, 1H), 7.58 (dd, J=5.2, 2.0 Hz, 1H), 7.52 (dd, J=10.0, 2.1 Hz, 1H), 7.46-7.33 (m, 3H), 5.51 (s, 2H), 4.54 (s, 4H), 2.68 (s, 2H), 0.73-0.67 (m, 4H).

Example 95. Compounds Prepared Using Procedure 65

Other compounds of the present disclosure prepared using the general route described in Procedure 65 include the following Example.

| Example | Structure/Name/Characterization |
|---|---|
| 95 | 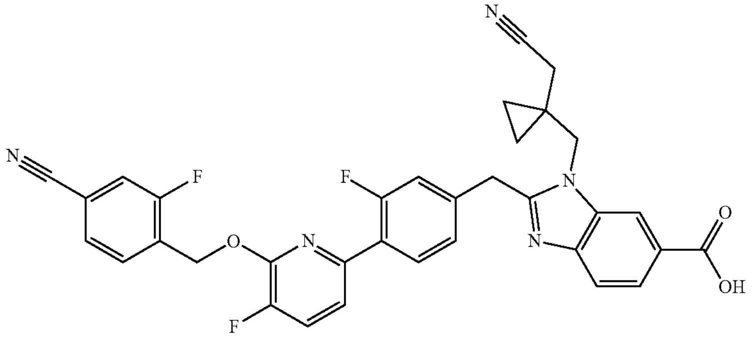 [SMILES: N#CCC1(Cn2c(Cc3ccc(-c4ccc(F)c(OCc5ccc(C#N)cc5F)n4)c(F)c3)nc3ccc(C(=O)O)cc32)CC1] 2-(4-(6-((4-cyano-2-fluorobenzyl)oxy)-5-fluoropyridin-2-yl)-3-fluorobenzyl)-1-((1-(cyanomethyl)cyclopropyl)methyl)-1H-benzo[d]imidazole-6-carboxylic acid: ES/MS m/z 608.2; $^1H$ NMR (400 MHz, Methanol-d4) δ 8.59 (s, 1H), 8.19 (dd, J = 8.6, 1.5 Hz, 1H), 8.00 (t, J = 8.2 Hz, 1H), 7.83-7.73 (m, 2H), 7.69-7.50 (m, 4H), 7.37-7.27 (m, 2H), 5.70 (s, 2H), 4.71 (d, J = 23.4 Hz, 4H), 2.61 (s, 2H), 1.00-0.85 (m, 4H). |

Example 82. 2-((4'-amino-3'-((4-cyano-2-fluorobenzyl)oxy)-3-fluoro-[1,1'-biphenyl]-4-yl)methyl)-1-(2-methoxyethyl)-1H-benzo[d]imidazole-6-carboxylic acid Procedure 66

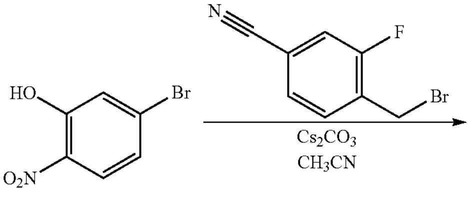

-continued

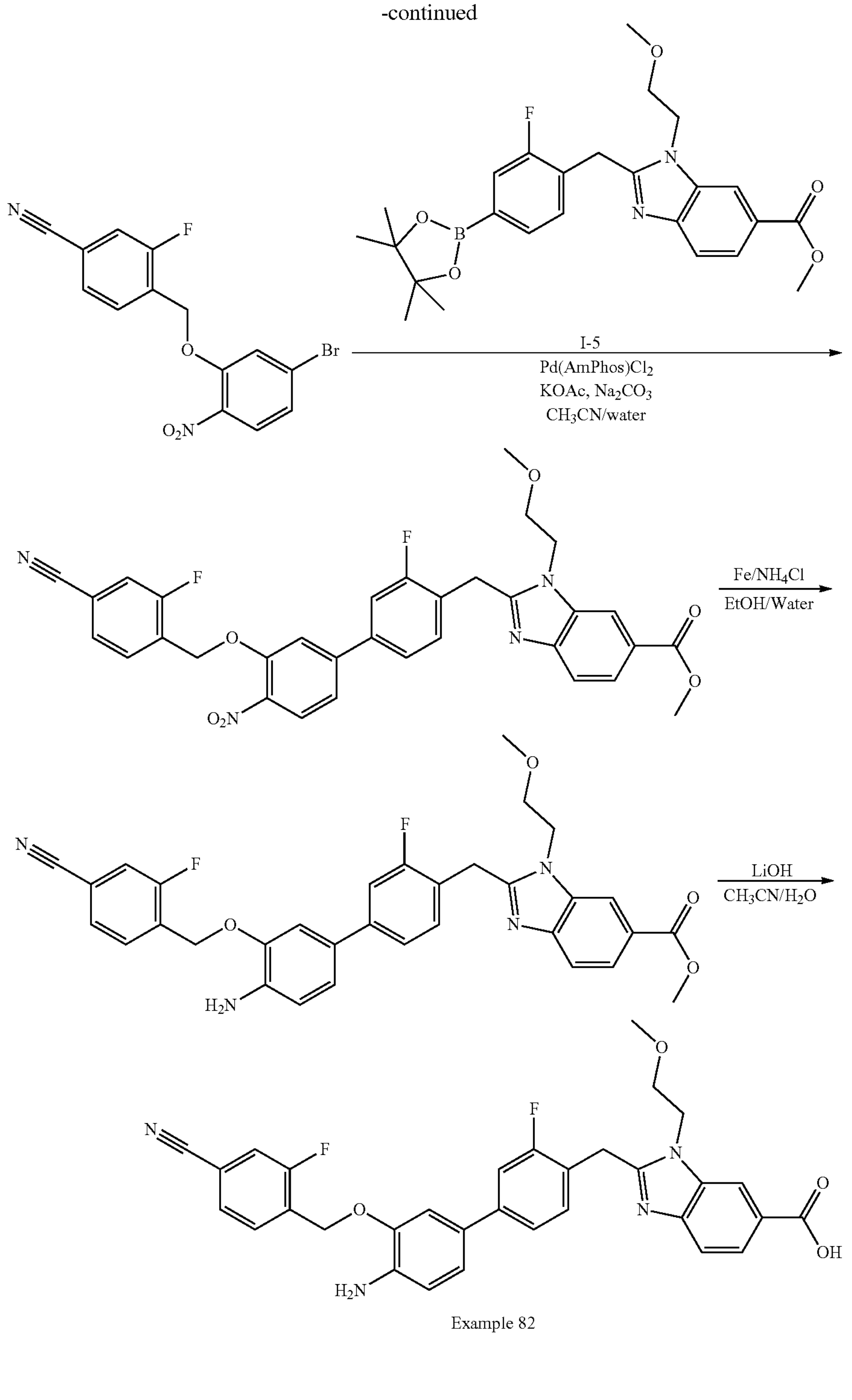

Example 82

4-((5-bromo-2-nitrophenoxy)methyl)-3-fluorobenzonitrile: To a vial was added 3-bromo-5-fluoro-phenol (300 mg, 1.57 mmol), 4-(bromomethyl)-3-fluoro-benzonitrile (370 mg, 1.73 mmol) and cesium carbonate (930 mg, 2.86 mmol) followed by acetonitrile (5.00 mL) and the mixture was stirred for 16 h at 60° C. The mixture was poured into water and the precipitate was filtered off, washed with water and dried under vacuum to yield the title compound. $^1$H NMR (400 MHz, Chloroform-d) δ 7.89-7.85 (m, 2H), 7.61-7.57 (m, 1H), 7.45 (dd, J=9.4, 1.5 Hz, 1H), 7.36 (d, J=1.9 Hz, 1H), 7.33-7.29 (m, 1H), 5.34 (s, 2H).

Methyl 2-((3'-((4-cyano-2-fluorobenzyl)oxy)-3-fluoro-4'-nitro-[1,1'-biphenyl]-4-yl)methyl)-1-(2-methoxyethyl)-1H-benzo[d]imidazole-6-carboxylate: To a microwave vial was added methyl 2-[[2-fluoro-4-(4,4,5,5-tetramethyl-1,3,2-dioxaborolan-2-yl)phenyl]methyl]-3-(2-methoxyethyl)benzimidazole-5-carboxylate (100 mg, 0.21 mmol), 4-[(5-bromo-2-nitro-phenoxy)methyl]-3-fluoro-benzonitrile (79 mg, 0.22 mmol), bis(di-tert-butyl(4-dimethylaminophenyl) phosphine)dichloropalladium(II) (0.012 g, 1.71e-5 mol), sodium carbonate (0.068 g, 0.64 mmol) and potassium acetate (0.042 g, 0.43 mol). Acetonitrile (1.10 mL) and water (0.55 mL) were added, argon was bubbled through the mixture for 3 min, and the mixture was heated to 110° C. in a microwave for 30 min. The mixture was filtered through CCelite, eluted with DCM, and the filtrate was concentrated in vacuo. The crude residue was purified by column chromatography (0-100% EtOAc in hexane) to give the title compound. ES/MS m/z: 613.3 (M+H$^+$).

Methyl 2-((4'-amino-3'-((4-cyano-2-fluorobenzyl)oxy)-3-fluoro-[1,1'-biphenyl]-4-yl)methyl)-1-(2-methoxyethyl)-1H-benzo[d]imidazole-6-carboxylate: To a vial containing methyl 2-[[4-[3-[(4-cyano-2-fluoro-phenyl)methoxy]-4-nitro-phenyl]-2-fluoro-phenyl]methyl]-3-(2-methoxyethyl) benzimidazole-5-carboxylate (61.0 mg, 0.0996 mmol) in ethanol (1.80 mL) and water (0.200 mL) was added ammonium chloride (0.0107 g, 0.199 mmol) and iron (0.0556 g, 0.996 mmol) and the mixture was heated to 80° C. for 1 h. The mixture was filtered through Celite, eluted with DCM and the filtrate was concentrated in vacuo. The residue was taken up in DCM and saturated aqueous sodium bicarbonate, the layers were separated, and the aqueous layer was extracted with DCM (2×). The combined organic extracts were dried over sodium sulfate, filtered and the filtrate was concentrated in vacuo to give the crude product. ES/MS m/z: 583.3 (M+H$^+$).

2-((4'-amino-3'-((4-cyano-2-fluorobenzyl)oxy)-3-fluoro-[1,1'-biphenyl]-4-yl)methyl)-1-(2-methoxyethyl)-1H-benzo[d]imidazole-6-carboxylic acid (Example 82): To a mixture of methyl 2-[[4-[3-[(4-cyano-2-fluoro-phenyl)methoxy]-5-methoxy-phenyl]-2-fluoro-phenyl]methyl]-3-(2-methoxyethyl)benzimidazole-5-carboxylate (119 mg, 199 μmol) in acetonitrile (3.00 mL) and water (1.00 mL) was added lithium hydroxide, monohydrate (25.1 mg, 0.597 mmol) and the mixture was heated to 60° C. for 30 min. The reaction was quenched by the addition of 5% aqueous citric acid and the mixture was extracted with EtOAc (3×). The combined organic extracts were washed with brine, dried over sodium sulfate, filtered and the filtrate was concentrated in vacuo. The crude residue was purified by RP-HPLC (15-45.99% 0.1% TFA-ACN in 0.1% TFA Water, 15 min gradient, Column: Gemini 5 uM, NX-C18 110 Angstrom, 250×21.2 mm) to give the title compound as a bis-TFA salt. ES/MS m/z: 569.5 (M+H$^+$); $^1$H NMR (400 MHz, Methanol-d4) δ 8.55-8.52 (m, 1H), 8.21 (dd, J=8.6, 1.4 Hz, 1H), 7.89-7.83 (m, 1H), 7.79-7.75 (m, 1H), 7.69-7.63 (m, 2H), 7.55-7.45 (m, 3H), 7.40 (d, J=1.9 Hz, 1H), 7.31 (dd, J=8.2, 1.9 Hz, 1H), 7.19 (d, J=8.1 Hz, 1H), 5.46 (s, 2H), 4.86 (s, 3H), 4.79 (t, J=5.0 Hz, 2H), 4.73 (s, 2H), 3.81 (t, J=4.9 Hz, 3H).

Example 85. 2-(4-(4-cyano-6-((4-cyano-2-fluorobenzyl)oxy)pyridin-2-yl)-2-fluorobenzyl)-1-(2-methoxyethyl)-1H-benzo[d]imidazole-6-carboxylic acid Procedure 67

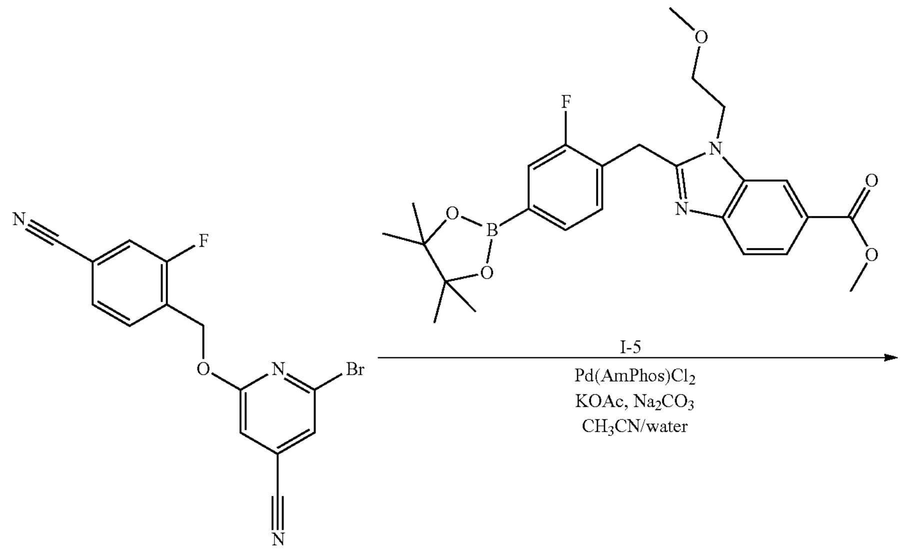

I-100

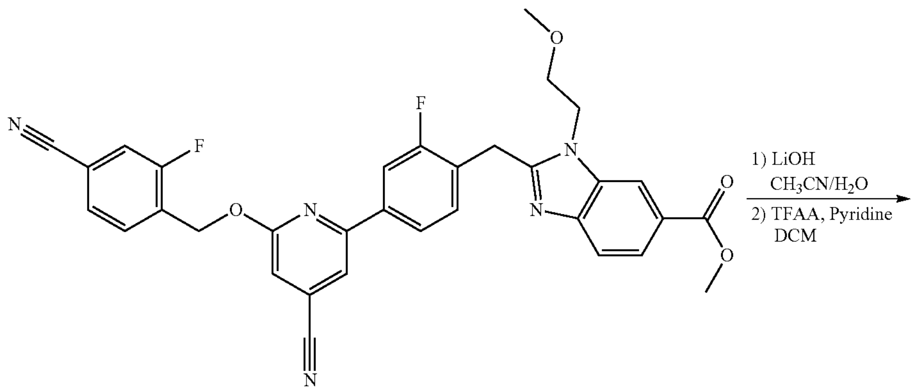

-continued

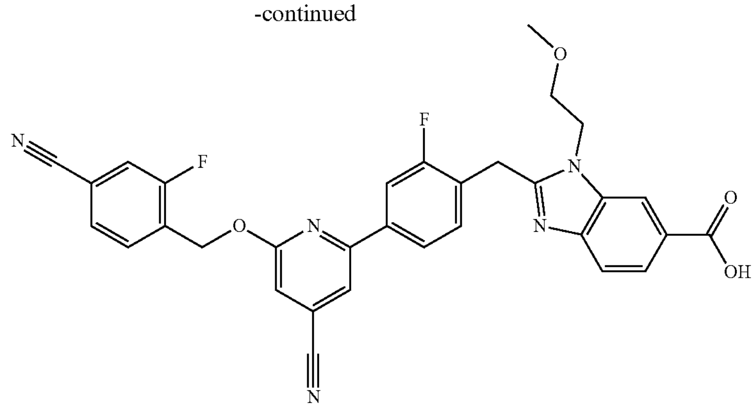

Example 85

Methyl 2-(4-(4-cyano-6-((4-cyano-2-fluorobenzyl)oxy)pyridin-2-yl)-2-fluorobenzyl)-1-(2-methoxyethyl)-1H-benzo[d]imidazole-6-carboxylate: To a microwave vial was added methyl 2-[[2-fluoro-4-(4,4,5,5-tetramethyl-1,3,2-dioxaborolan-2-yl)phenyl]methyl]-3-(2-methoxyethyl)benzimidazole-5-carboxylate (I-5, 100 mg, 0.21 mmol), 2-bromo-6-[(4-cyano-2-fluoro-phenyl)methoxy]pyridine-4-carbonitrile (I-100, 65 mg, 0.22 mmol), bis(di-tert-butyl(4-dimethylaminophenyl)phosphine)dichloropalladium(II) (0.012 g, 1.71e-5 mol), sodium carbonate (0.068 g, 0.64 mmol) and potassium acetate (0.042 g, 0.427 mol). Acetonitrile (1.10 mL) and water (0.55 mL) were added, argon was bubbled through the mixture for 3 min and the mixture was heated to 110° C. in a microwave for 30 min. The mixture was filtered through Celite, eluted with DCM and the filtrate was concentrated in vacuo. The crude residue was purified by column chromatography (0-100% EtOAc in hexane) to give the title compound. ES/MS m/z: 594.3 ($M+H^+$).

2-(4-(4-cyano-6-((4-cyano-2-fluorobenzyl)oxy)pyridin-2-yl)-2-fluorobenzyl)-1-(2-methoxyethyl)-1H-benzo[d]imidazole-6-carboxylic acid (Example 85): To a mixture of methyl 2-[[4-[4-cyano-6-[(4-cyano-2-fluoro-phenyl)methoxy]-2-pyridyl]-2-fluoro-phenyl]methyl]-3-(2-methoxyethyl)benzimidazole-5-carboxylate (16.3 mg, 27.5 μmol) in acetonitrile (1.00 mL) and water (0.33 mL) was added lithium hydroxide, monohydrate (3.5 mg, 0.082 mmol) and the reaction vial was sealed and heated at 100° C. for 4 min. The reaction was quenched by the addition of 5% aqueous citric acid and the mixture was extracted with EtOAc (3×). The combined organic extracts were washed with brine, dried over sodium sulfate, filtered and the filtrate was concentrated in vacuo. The crude residue was taken up in dichloromethane (1.00 mL) and pyridine (11 μL, 0.137 mmol) and cooled to 0° C. Trifluoroacetic anhydride (9.5 μL, 0.07 mmol) was added and the mixture was stirred for 30 min at 0° C. The crude residue was purified by RP-HPLC (15-62.49% 0.1% TFA-ACN in 0.1% TFA Water, 15 min gradient, Column: Gemini 5 uM, NX-C18 110 Angstrom, 250×21.2 mm) to give the title compound as a bis-TFA salt. ES/MS m/z: 580.4 ($M+H^+$); $^1H$ NMR (400 MHz, Methanol-d4) δ 8.44 (s, 1H), 8.16-8.11 (m, 1H), 7.97-7.90 (m, 3H), 7.79-7.71 (m, 2H), 7.66-7.57 (m, 2H), 7.49 (t, J=7.9 Hz, 1H), 7.29 (d, J=1.0 Hz, 1H), 5.71 (s, 2H), 4.71 (t, J=5.2 Hz, 2H), 4.68 (s, 2H), 3.78 (t, J=5.0 Hz, 2H), 3.30 (s, 3H).

Example 89. 2-(4-(3-(benzyloxy)-1H-pyrazol-1-yl)-2-fluorobenzyl)-1-(2-methoxyethyl)-1H-benzo[d]imidazole-6-carboxylic acid Procedure 68

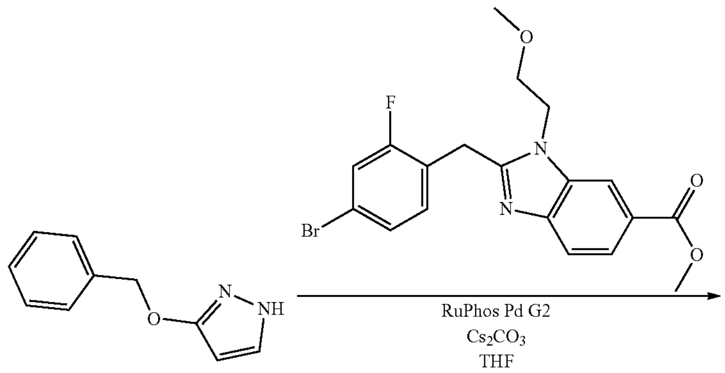

-continued

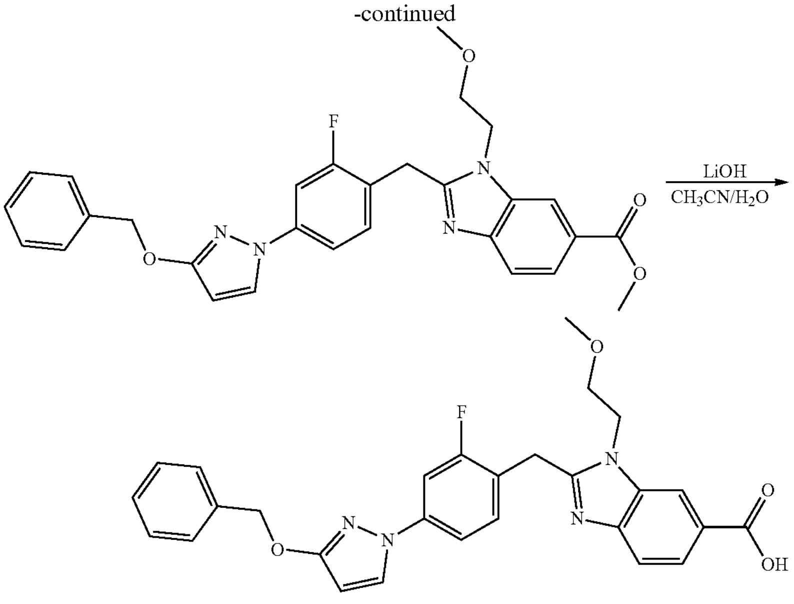

Example 89

Methyl 2-(4-(3-(benzyloxy)-1H-pyrazol-1-yl)-2-fluorobenzyl)-1-(2-methoxyethyl)-1H-benzo[d]imidazole-6-carboxylate: To a vial containing 3-(benzyloxy)-1H-pyrazole (76.0 mg, 0.345 mmol) was added tetrahydrofuran (1.00 mL), methyl 2-[(4-bromo-2-fluoro-phenyl)methyl]-3-(2-methoxyethyl)benzimidazole-5-carboxylate (155 mg, 0.367 mmol) (obtained as described in the synthesis of I-5), RuPhos Pd G2 (0.0256 g, 0.0345 mmol) and cesium carbonate (0.281 g, 0.863 mmol). Argon was bubbled through the mixture for 3 min and the mixture was heated to 85° C. for 16 h. LCMS showed complete conversion to desired product. The mixture was filtered through CCelite, eluted with DCM and the filtrate was concentrated in vacuo. ES/MS m/z: 515.6 (M+H$^+$).

2-(4-(3-(benzyloxy)-1H-pyrazol-1-yl)-2-fluorobenzyl)-1-(2-methoxyethyl)-1H-benzo[d]imidazole-6-carboxylic acid (Example 89): To a mixture of methyl 2-[[4-(3-benzyloxypyrazol-1-yl)-2-fluoro-phenyl]methyl]-3-(2-methoxyethyl)benzimidazole-5-carboxylate (24.9 mg, 48.4 μmol) in acetonitrile (1.00 mL) and water (0.33 mL) was added lithium hydroxide, monohydrate (6.09 mg, 0.145 mmol) and the mixture was heated to 60° C. for 30 min. The reaction was quenched by the addition of TFA (50 μL) and the crude mixture was purified directly by RP-HPLC (15-58.37% 0.1% TFA-ACN in 0.1% TFA Water, 15 min gradient, Column: Gemini 5 μM, NX-C18 110 Angstrom, 250×21.2 mm) to give the title compound as a TFA salt. ES/MS m/z: 501.2 (M+H$^+$); $^1$H NMR (400 MHz, Methanol-d4) δ 8.54 (dd, J=1.4, 0.7 Hz, 1H), 8.21 (dd, J=8.6, 1.5 Hz, 1H), 8.15 (d, J=2.7 Hz, 1H), 7.77 (dd, J=8.6, 0.7 Hz, 1H), 7.68-7.59 (m, 2H), 7.52-7.46 (m, 3H), 7.42-7.30 (m, 3H), 6.06 (d, J=2.7 Hz, 1H), 5.31 (s, 2H), 4.79 (t, J=5.0 Hz, 2H), 4.71 (s, 2H), 3.84-3.79 (m, 2H), 3.32 (s, 3H).

Example 94. 2-(4-(6-((4-cyano-2-fluorobenzyl)oxy)pyridin-2-yl)-2-fluorobenzyl)-1-((1-(fluoromethyl)cyclopropyl)methyl)-1H-imidazo[4,5-b]pyridine-6-carboxylic acid Procedure 69

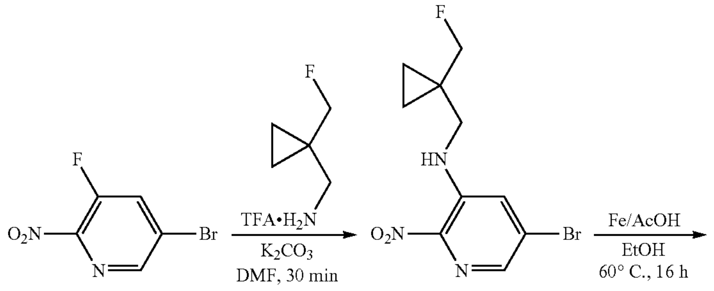

-continued

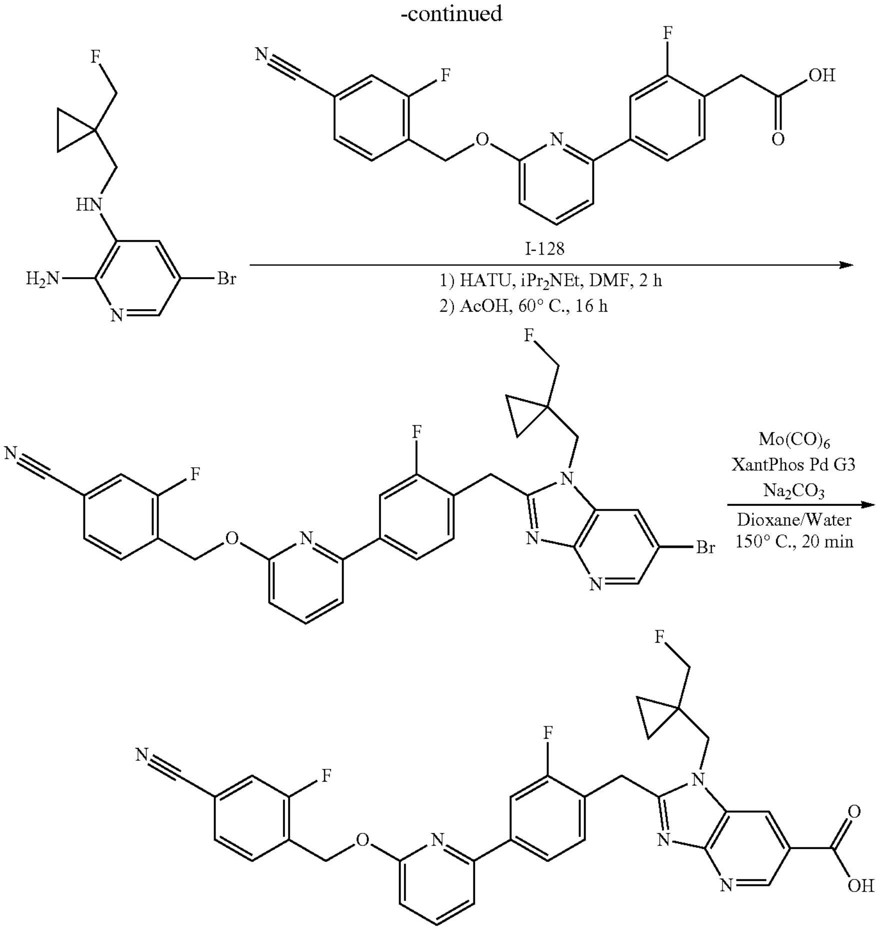

Example 94

5-bromo-N-((1-(fluoromethyl)cyclopropyl)methyl)-2-nitropyridin-3-amine: To a vial was added 5-bromo-3-fluoro-2-nitropyridine (300 mg, 1.36 mmol), potassium carbonate (0.563 g, 4.07 mmol) followed by DMF (5 mL) and [1-(fluoromethyl)cyclopropyl]methanamine 2,2,2-trifluoroacetic acid (0.324 g, 1.49 mmol) and the mixture was stirred at room temperature for 30 min. The mixture was poured into water and the precipitate was filtered off, washed with water, and dried under vacuum to yield the title compound. ES/MS m/z: 304.0 (M+H$^+$).

5-bromo-N3-((1-(fluoromethyl)cyclopropyl)methyl) pyridine-2,3-diamine

To solution of 5-bromo-N-[[1-(fluoromethyl)cyclopropyl]methyl]-2-nitro-pyridin-3-amine (323 mg, 1.06 mmol) in ethanol (5.00 mL) and acetic acid (5.00 mL, 87.4 mmol) was added iron (0.297 g, 5.31 mmol) and the mixture was heated to 60° C. for 16 h. The mixture was filtered through Celite, eluted with MeOH, and the filtrate was concentrated in vacuo. The crude residue was purified by column chromatography (0-100% EtOAc in hexane) to give the title compound. ES/MS m/z: 274.1 (M+H$^+$).

4-(((6-(4-((6-bromo-1-((1-(fluoromethyl)cyclopropyl)methyl)-1H-imidazo[4,5-b]pyridin-2-yl)methyl)-3-fluorophenyl)pyridin-2-yl)oxy)methyl)-3-fluorobenzonitrile: To a solution of 5-bromo-N3-[[1-(fluoromethyl)cyclopropyl]methyl]pyridine-2,3-diamine (65.0 mg, 0.237 mmol) in DMF (3.00 mL) was added 2-(4-(6-((4-cyano-2-fluorobenzyl)oxy)pyridin-2-yl)-2-fluorophenyl)acetic acid (I-128, 95.4 mg, 0.251 mmol), 2-(7-aza-1H-benzotriazole-1-yl)-1,1,3,3-tetramethyluronium hexafluorophosphate (HATU), 99% (66.9 mg, 0.285 mmol) and N,N-diisopropylethylamine (0.207 mL, 1.19 mmol) and stirred for 1 hour. The reaction was quenched by the addition of water and the mixture was extracted with DCM (3×). The combined organic extracts were dried over sodium sulfate, filtered and the filtrate was concentrated in vacuo. The crude residue was dissolved in AcOH (2.9 mL) and the mixture was heated to 70° C. for 16 h. The mixture was concentrated in vacuo, the crude residue was taken up in DCM and washed with saturated aqueous sodium bicarbonate. The layers were separated and the aqueous layer was extracted with DCM (2×). The combined organic extracts were dried over sodium sulfate, filtered and the filtrate was concentrated in vacuo. The crude residue was purified by column chromatography (0-100% EtOAc in hexane) to give the title compound. ES/MS m/z: 618.0 (M+H$^+$).

2-(4-(6-((4-cyano-2-fluorobenzyl)oxy)pyridin-2-yl)-2-fluorobenzyl)-1-((1-(fluoromethyl)cyclopropyl)methyl)-1H-imidazo[4,5-b]pyridine-6-carboxylic acid (Example 94): A suspension of [6-bromo-1-(2-methoxyethyl)benzimidazol-2-yl]-[4-[6-[(4-chloro-2-fluoro-phenyl)methoxy]-2-pyridyl]-1-piperidyl]methanone (17.8 mg, 0.0288 mmol), hexacarbonylmolybdenum (7.60 mg, 0.0288 mmol), Xantphos Pd G3 (2.73 mg, 0.00288 mmol), and sodium carbonate (9.64 mg, 0.0910 mmol) in dioxane (1 mL) and water (0.3 mL), was degassed with Ar for 5 min, then heated at 150° C. for 20 min in a microwave. The reaction was quenched by the addition of TFA (50 μL) and the crude mixture was purified directly by RP-HPLC (15-70.29% 0.1% TFA-ACN in 0.1% TFA Water, 15 min gradient, Column: Gemini 5 uM, NX-C18 110 Angstrom, 250×21.2 mm) to give the title compound as a bis-TFA salt. ES/MS m/z: 584.2 (M+H$^+$); $^1$H NMR (400 MHz, DMSO-d6) δ 8.92 (d, J=1.9 Hz, 1H), 8.57 (d, J=2.0 Hz, 1H), 7.93 (dd, J=10.0, 1.4 Hz, 1H), 7.90 (s, 1H), 7.89-7.84 (m, 2H), 7.80-7.75 (m, 1H), 7.73 (dd, J=7.9, 1.5 Hz, 1H), 7.68 (d, J=7.5 Hz, 1H), 7.47 (t, J=7.9 Hz, 1H), 6.93 (d, J=8.1 Hz, 1H), 5.63 (s, 2H), 4.58 (s, 2H), 4.49 (s, 2H), 4.23 (s, 1H), 4.11 (s, 1H), 0.90-0.83 (m, 2H), 0.78-0.69 (m, 2H).

Example 71. Compounds Prepared Using Procedure 69

Other compounds of the present disclosure prepared using the general route described in Procedure 69 include the following Example.

| Example | Structure/Name/Characterization |
| --- | --- |
| 71 | 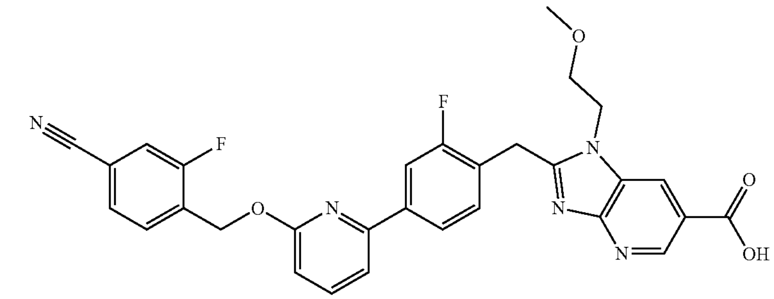 [SMILES: COCCn1c(Cc2ccc(-c3cccc(OCc4ccc(C#N)cc4F)n3)cc2F)nc2ncc(C(=O)O)cc21] 2-(4-(6-((4-cyano-2-fluorobenzyl)oxy)pyridin-2-yl)-2-fluorobenzyl)-1-(2-methoxyethyl)-1H-imidazo[4,5-b]pyridine-6-carboxylic acid: Es/MS m/z 556.3; $^1$H NMR (400 MHz, Methanol-d4) δ 9.07 (d, J = 1.9 Hz, 1H), 8.68-8.62 (m, 1H), 7.87-7.77 (m, 3H), 7.74 (t, J = 7.5 Hz, 1H), 7.65-7.50 (m, 3H), 7.38 (t, J = 7.7 Hz, 1H), 6.88 (d, J = 8.2 Hz, 1H), 5.65 (s, 2H), 4.59 (t, J = 5.4 Hz, 2H), 4.57 (s, 2H), 3.69 (t, J = 4.9 Hz, 2H), 3.26 (s, 3H). |

Example 96. 2-(3-fluoro-4-(6-((3-methoxypyridin-4-yl)methoxy)pyridin-2-yl)benzyl)-1-(2-methoxyethyl)-1H-benzo[d]imidazole-6-carboxylic acid Procedure 70

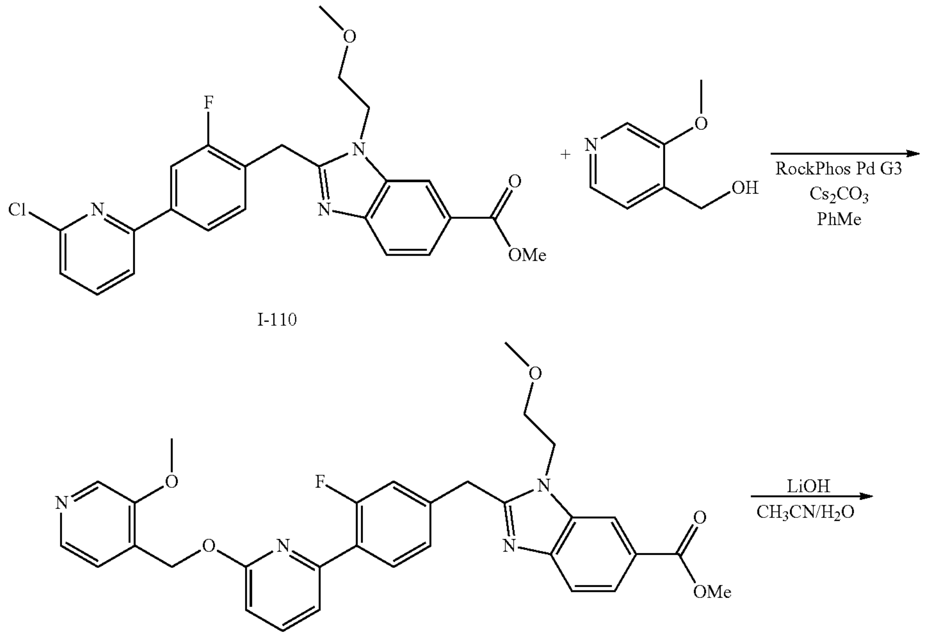

-continued

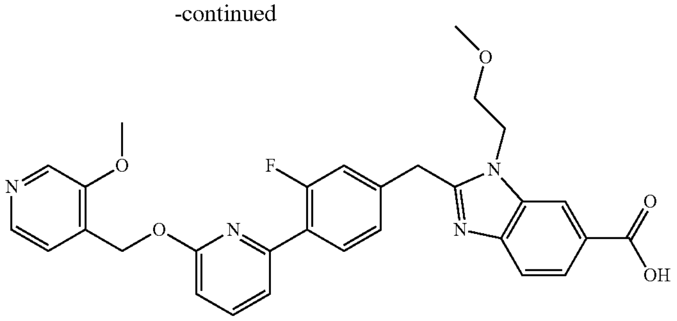

Example 96

Methyl 2-(3-fluoro-4-(6-((3-methoxypyridin-4-yl) methoxy)pyridin-2-yl)benzyl)-1-(2-methoxyethyl)-1H-benzo[d]imidazole-6-carboxylate: To a vial was added methyl 2-[[4-(6-chloro-2-pyridyl)-2-fluoro-phenyl]methyl]-3-(2-methoxyethyl)benzimidazole-5-carboxylate (I-110, 50 mg, 0.11 mmol), (3-methoxy-4-pyridyl)methanol (0.031 g, 0.22 mmol), Pd RockPhos G3 (0.0139 g, 1.65e-5 mol) and cesium carbonate (0.108 g, 0.33 mmol) followed by toluene (1.50 mL). Argon was bubbled through the mixture for 3 min and the mixture was heated to 110° C. for 16 h. The mixture was filtered through Celite, eluting with DCM and the filtrate was concentrated in vacuo. The crude residue was purified by column chromatography (0-100% EtOAc in hexane) to give the title compound. ES/MS m/z: 557.2 ($M+H^+$).

2-(3-fluoro-4-(6-((3-methoxypyridin-4-yl)methoxy)pyridin-2-yl)benzyl)-1-(2-methoxyethyl)-1H-benzo[d]imidazole-6-carboxylic acid (Example 96): To a mixture of methyl 2-[[2-fluoro-4-[6-[(3-methoxy-4-pyridyl)methoxy]-2-pyridyl]phenyl]methyl]-3-(2-methoxyethyl)benzimidazole-5-carboxylate (47.0 mg, 84.4 μmol) in acetonitrile (1.00 mL) and water (0.33 mL) was added lithium hydroxide monohydrate (10.6 mg, 0.253 mmol) and the mixture was stirred at 60° C. for 30 min. The reaction was quenched by the addition of TFA (50 μL) and the crude mixture was purified directly by RP-HPLC (15-38.19% 0.1% TFA-ACN in 0.1% TFA Water, 15 min gradient, Column: Gemini 5 uM, NX-C18 110 Angstrom, 250x21.2 mm) to give the title compound as a bis-TFA salt. ES/MS m/z: 543.3 ($M+H^+$); $^1H$ NMR (400 MHz, Methanol-d4) δ 8.58 (s, 1H), 8.49 (s, 1H), 8.42 (d, J=5.5 Hz, 1H), 8.17 (dd, J=8.5, 1.5 Hz, 1H), 7.98 (d, J=5.7 Hz, 1H), 7.93-7.80 (m, 3H), 7.75 (d, J=8.6 Hz, 1H), 7.62 (d, J=7.5 Hz, 1H), 7.47 (t, J=7.8 Hz, 1H), 7.04 (d, J=8.1 Hz, 1H), 5.76 (s, 2H), 4.74 (t, J=5.0 Hz, 2H), 4.70 (s, 2H), 4.17 (s, 3H), 3.79 (t, J=4.8 Hz, 2H), 3.30 (s, 3H).

Example 98 and 802-805. Compounds Prepared Using Procedure 70

Other compounds of the present disclosure prepared using the general route described in Procedure 70 include the following Examples.

| Example | Structure/Name/Characterization |
|---|---|
| 98 | 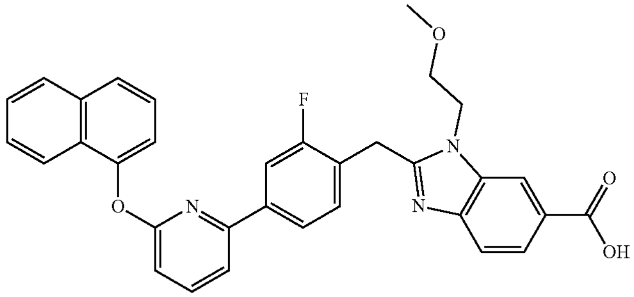 [SMILES: COCCn1c(Cc2ccc(-c3cccc(Oc4cccc5ccccc45)n3)cc2F)nc2ccc(C(=O)O)cc21] 2-(2-fluoro-4-(6-(naphthalen-1-yloxy)pyridin-2-yl)benzyl)-1-(2-methoxyethyl)-1H-benzo[d]imidazole-6-carboxylic acid: ES/MS m/z 548.4; $^1H$ NMR (400 MHz, Methanol-d4) δ 8.54 (t, J = 1.0 Hz, 1H), 8.22 (dd, J = 8.6, 1.4 Hz, 1H), 8.00-7.89 (m, 3H), 7.82 (d, J = 8.3 Hz, 1H), 7.77-7.70 (m, 2H), 7.67 (d, J = 7.4 Hz, 1H), 7.61 (dd, J = 11.6, 1.8 Hz, 1H), 7.60-7.43 (m, 3H), 7.41 (t, J = 7.9 Hz, 1H), 7.31 (dd, J = 7.5, 1.1 Hz, 1H), 7.04 (d, J = 8.2 Hz, 1H), 4.77 (t, J = 5.0 Hz, 2H), 4.71 (s, 2H), 3.78 (t, J = 4.9 Hz, 2H), 3.28 (s, 3H). |
| 802 | ES/MS m/z 600.1; 1H NMR (400 MHz, DMSO-d6) δ 8.29 (d, J = 1.5 Hz, 1H), 7.95-7.85 (m, 2H), 7.81 (dd, J = 10.5, 6.4 Hz, 1H), 7.65 (d, J = 8.4 Hz, 1H), 7.53 (dd, J = 7.5, 1.7 Hz, 1H), 7.45 (ddt, J = 15.7, 11.5, 7.4 Hz, 3H), 6.97 (d, J = 8.2 Hz, 1H), 5.56 (s, 2H), 4.65 (t, J = 5.1 Hz, 2H), 4.52 (s, 2H), 3.70 (t, J = 5.0 Hz, 2H), 3.21 (s, 3H). |

-continued
| Example | Structure/Name/Characterization |
|---|---|
| 803 | 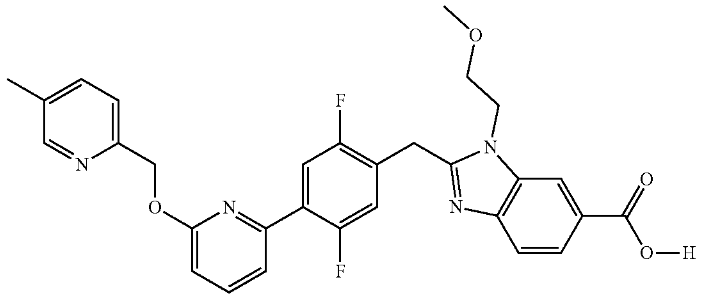 [SMILES: COCCn1c(Cc2cc(F)c(-c3cccc(OCc4ccc(C)cn4)n3)cc2F)nc2ccc(C(=O)O)cc21]<br>ES/MS m/z 545.2; 1H NMR (400 MHz, DMSO-d6) δ 8.53 (d, J = 2.1 Hz, 1H), 8.28 (d, J = 1.4 Hz, 1H), 7.99-7.83 (m, 3H), 7.72 (dd, J = 10.5, 6.4 Hz, 1H), 7.62 (dd, J = 14.3, 8.2 Hz, 2H), 7.53 (dd, J = 7.4, 1.7 Hz, 1H), 7.40 (dd, J = 11.6, 6.1 Hz, 1H), 7.02 (d, J = 8.2 Hz, 1H), 5.58 (s, 2H), 4.64 (t, J = 5.2 Hz, 2H), 4.50 (s, 2H), 3.70 (t, J = 5.0 Hz, 2H), 3.21 (s, 3H), 2.35 (s, 3H). |
| 804 | 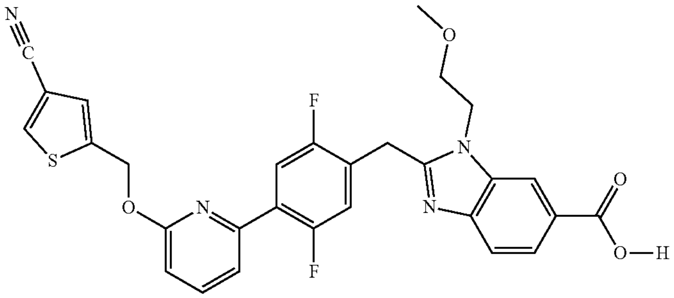 [SMILES: COCCn1c(Cc2cc(F)c(-c3cccc(OCc4cc(C#N)cs4)n3)cc2F)nc2ccc(C(=O)O)cc21]<br>ES/MS m/z 561.3; 1H NMR (400 MHz, DMSO-d6) δ 8.53 (d, J = 1.4 Hz, 1H), 8.28 (d, J = 1.4 Hz, 1H), 8.02-7.80 (m, 3H), 7.65 (dd, J = 4.9, 3.6 Hz, 2H), 7.56 (dd, J = 7.5, 1.7 Hz, 1H), 7.43 (dd, J = 11.6, 6.1 Hz, 1H), 6.94 (d, J = 8.2 Hz, 1H), 5.69 (s, 2H), 4.65 (t, J = 5.1 Hz, 2H), 4.52 (s, 2H), 3.70 (t, J = 5.0 Hz, 2H), 3.22 (s, 3H). |
| 805 | 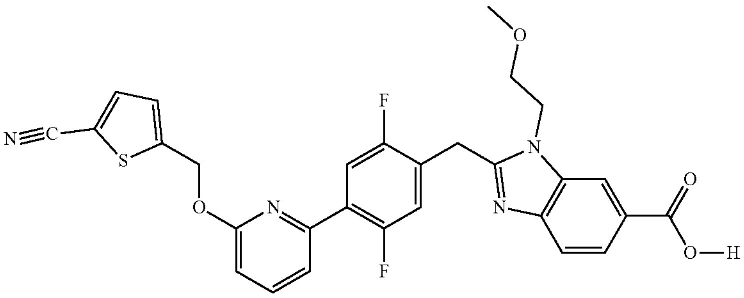 [SMILES: COCCn1c(Cc2cc(F)c(-c3cccc(OCc4ccc(C#N)s4)n3)cc2F)nc2ccc(C(=O)O)cc21]<br>ES/MS m/z 561.4; 1H NMR (400 MHz, DMSO-d6) δ 8.30 (d, J = 1.5 Hz, 1H), 8.00-7.83 (m, 4H), 7.66 (d, J = 8.4 Hz, 1H), 7.57 (dd, J = 7.4, 1.6 Hz, 1H), 7.49-7.37 (m, 2H), 6.97 (d, J = 8.2 Hz, 1H), 5.76 (s, 2H), 4.66 (t, J = 5.1 Hz, 2H), 4.54 (s, 2H), 3.70 (t, J = 5.0 Hz, 2H), 3.21 (s, 3H). |

Example 97. 2-(4-(4-carboxy-6-((4-cyano-2-fluorobenzyl)oxy)pyridin-2-yl)-2-fluorobenzyl)-1-(2-methoxyethyl)-1H-benzo[d]imidazole-6-carboxylic acid
Procedure 71
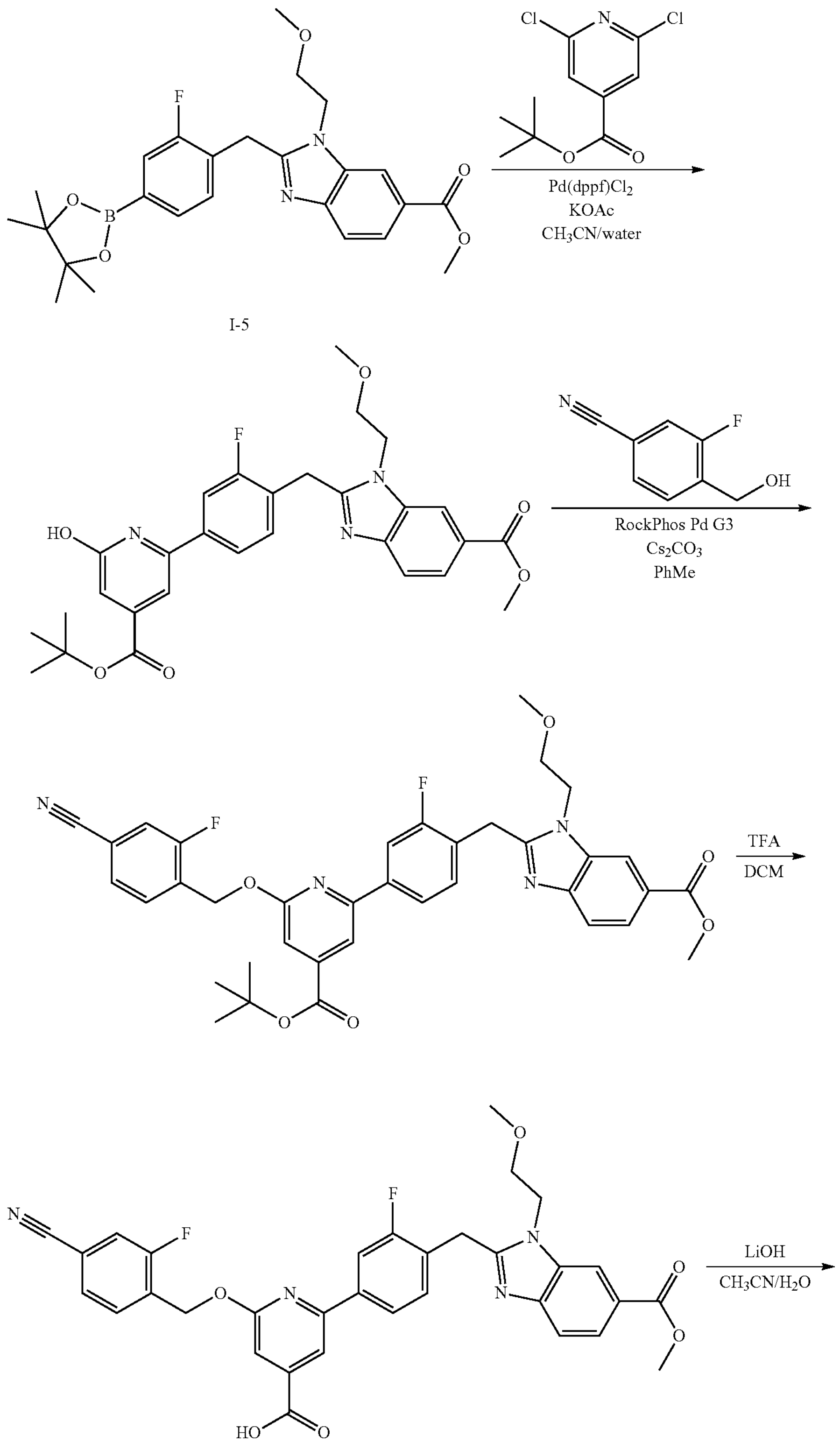

-continued

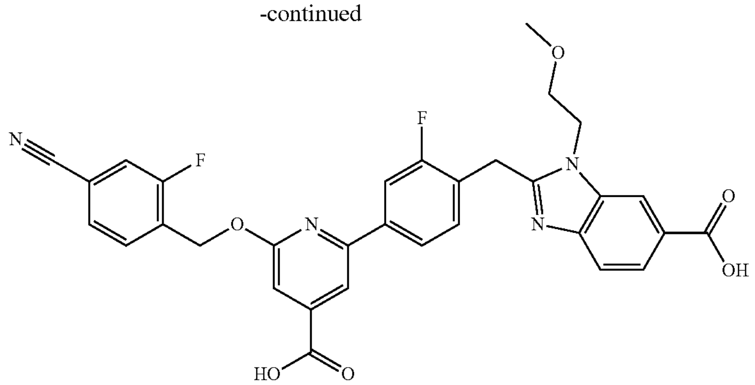

Example 97

Methyl 2-(4-(4-(tert-butoxycarbonyl)-6-hydroxypyridin-2-yl)-2-fluorobenzyl)-1-(2-methoxyethyl)-1H-benzo[d]imidazole-6-carboxylate: To a microwave vial was added methyl 2-[[2-fluoro-4-(4,4,5,5-tetramethyl-1,3,2-dioxaborolan-2-yl)phenyl]methyl]-3-(2-methoxyethyl)benzimidazole-5-carboxylate (I-6, 800 mg, 1.71 mmol), tert-butyl 2,6-dichloropyridine-4-carboxylate (445 mg, 1.79 mmol) and (1,1'-bis(diphenylphosphino)ferrocene)-dichloropalladium (II) (0.0967 g, 0.14 mmol). Acetonitrile (12 mL) and 1.0 M potassium acetate in water (4.3 mL, 1.07 mmol) were added, argon was bubbled through the mixture for 3 min and the mixture was heated to 100° C. in a microwave for 15 min. The mixture was filtered through Celite, eluting with DCM and the filtrate was concentrated in vacuo. The crude residue was purified by column chromatography (0-100% EtOAc in hexane) to give the title compound. ES/MS m/z: 554.7 ($M+H^+$).

Methyl 2-(4-(4-(tert-butoxycarbonyl)-6-((4-cyano-2-fluorobenzyl)oxy)pyridin-2-yl)-2-fluorobenzyl)-1-(2-methoxyethyl)-1H-benzo[d]imidazole-6-carboxylate: To a vial was added methyl 2-[[4-(4-tert-butoxycarbonyl-6-chloro-2-pyridyl)-2-fluoro-phenyl]methyl]-3-(2-methoxyethyl)benzimidazole-5-carboxylate (200 mg, 0.36 mmol), 3-fluoro-4-(hydroxymethyl)benzonitrile (0.109 g, 0.72 mmol), Pd RockPhos G3 (0.0454 g, 5.42e-5 mol) and cesium carbonate (0.353 g, 1.08 mmol) followed by toluene (6.0 mL). Argon was bubbled through the mixture for 3 min and the mixture was heated to 110° C. for 16 h. The mixture was filtered through Celite, eluted with DCM and the filtrate was concentrated in vacuo. The crude residue was purified by column chromatography (0-100% EtOAc in hexane) to give the title compound. ES/MS m/z: 669.3 ($M+H^+$).

2-((4-cyano-2-fluorobenzyl)oxy)-6-(3-fluoro-4-((6-(methoxycarbonyl)-1-(2-methoxyethyl)-1H-benzo[d]imidazol-2-yl)methyl)phenyl)isonicotinic acid: To a solution of methyl 2-[[4-[4-tert-butoxycarbonyl-6-[(4-cyano-2-fluoro-phenyl)methoxy]-2-pyridyl]-2-fluoro-phenyl]methyl]-3-(2-methoxyethyl)benzimidazole-5-carboxylate (60.0 mg, 0.0897 mmol) in dichloromethane (1.00 mL) was added trifluoroacetic acid (0.0343 mL, 0.449 mmol) and the mixture was stirred for 16 h at 45° C. Ammonium hydroxide (0.15 mL) was added and the mixture was concentrated in vacuo. The crude residue was used directly in the following step: ES/MS m/z: 613.2 ($M+H^+$).

2-(4-(4-carboxy-6-((4-cyano-2-fluorobenzyl)oxy)pyridin-2-yl)-2-fluorobenzyl)-1-(2-methoxyethyl)-1H-benzo[d]imidazole-6-carboxylic acid (Example 97): To a mixture of 2-[(4-cyano-2-fluoro-phenyl)methoxy]-6-[3-fluoro-4-[[6-methoxycarbonyl-1-(2-methoxyethyl)benzimidazol-2-yl]methyl]phenyl]pyridine-4-carboxylic acid (43 mg, 70.2 μmol) in acetonitrile (1.00 mL) and water (0.33 mL) was added lithium hydroxide monohydrate (75.4 mg, 1.80 mmol) and the mixture was stirred at 60° C. for 3 h. The reaction was quenched by the addition of TFA (50 μL) and the crude mixture was purified directly by RP-HPLC (15-55.29% 0.1% TFA-ACN in 0.1% TFA Water, 15 min gradient, Column: Gemini 5 uM, NX-C18 110 Angstrom, 250×21.2 mm) to give the title compound as a TFA salt. ES/MS m/z: 599.2 ($M+H^+$); $^1H$ NMR (400 MHz, DMSO-d6) δ 8.24 (s, 1H), 7.99 (d, J=1.0 Hz, 1H), 7.95 (t, J=1.8 Hz, 1H), 7.94-7.90 (m, 2H), 7.85-7.77 (m, 2H), 7.73 (dd, J=7.9, 1.5 Hz, 1H), 7.62 (d, J=8.4 Hz, 1H), 7.46 (t, J=8.0 Hz, 1H), 7.30 (d, J=0.9 Hz, 1H), 5.68 (s, 2H), 4.60 (t, J=5.2 Hz, 2H), 4.48 (s, 2H), 3.67 (t, J=5.0 Hz, 2H), 3.21 (s, 3H).

Example 99. 2-(4-(6-((4-cyano-2-fluorobenzyl)oxy)-4-(1-methyl-1H-pyrazol-4-yl)pyridin-2-yl)-2-fluorobenzyl)-1-(2-methoxyethyl)-1H-benzo[d]imidazole-6-carboxylic acid Procedure 72

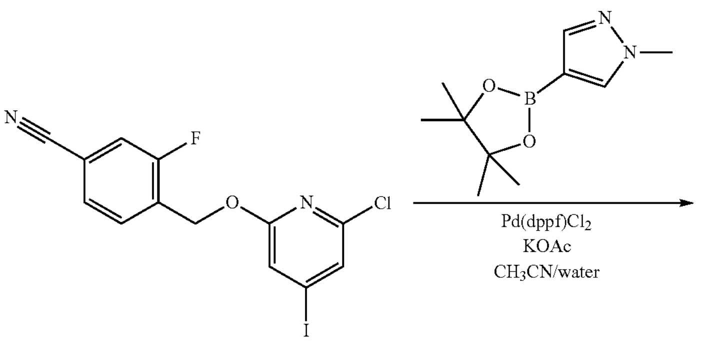

I-108

-continued

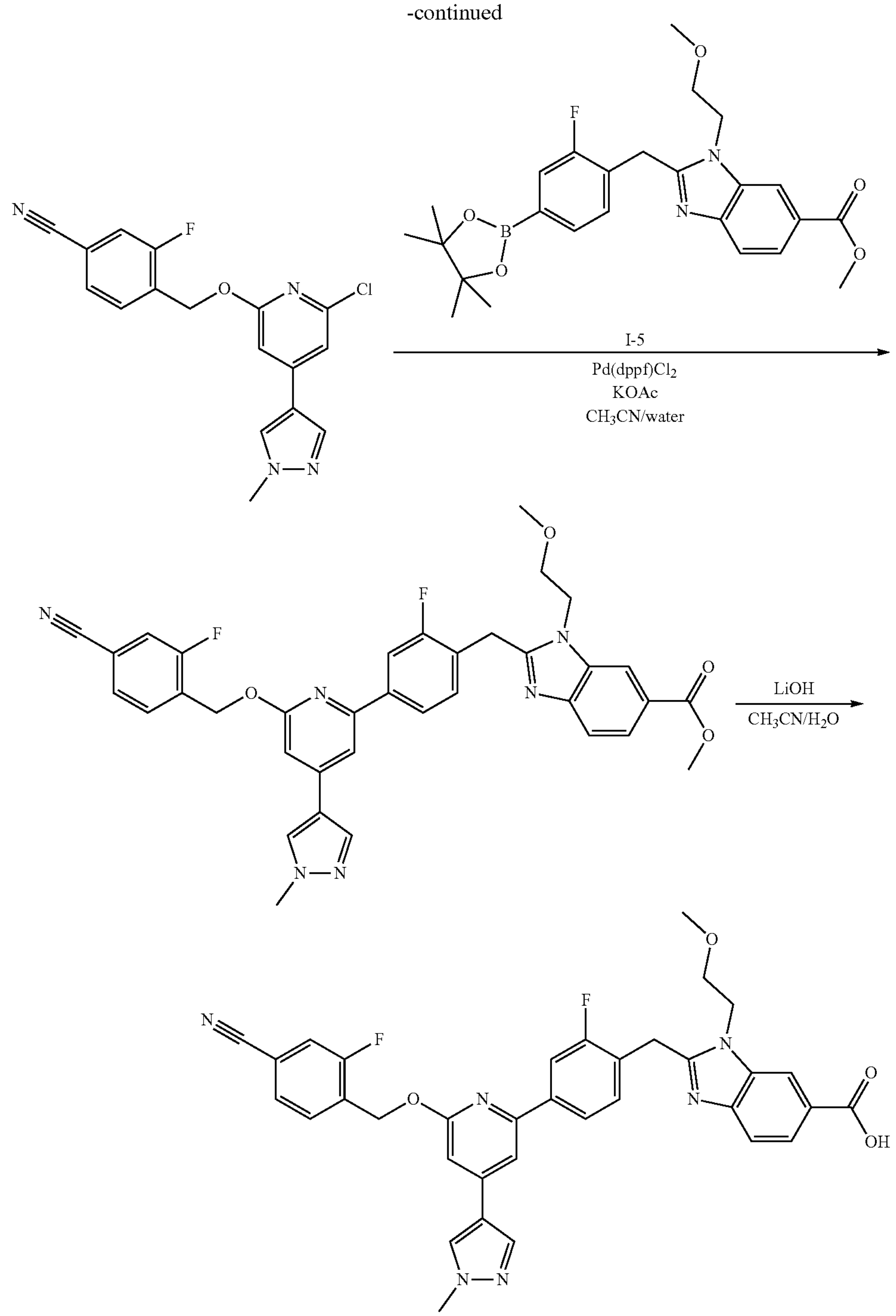

Example 99

4-(((6-chloro-4-(1-methyl-1H-pyrazol-4-yl)pyridin-2-yl)oxy)methyl)-3-fluorobenzonitrile: To a microwave vial was added 4-[(6-chloro-4-iodo-2-pyridyl)oxymethyl]-3-fluoro-benzonitrile (I-108, 30.0 mg, 7.72e-5 mol), 1-methyl-4-(4,4,5,5-tetramethyl-1,3,2-dioxaborolan-2-yl)pyrazole (16.9 mg, 8.11e-5 mol) and (1,1'-bis(diphenylphosphino)ferrocene)-dichloropalladium(II) (43.7 mg, 6.18e-6 mol). Acetonitrile (0.75 mL) and 1.0 M potassium acetate in water (0.19 mL, 0.19 mmol) were added, argon was bubbled through the mixture for 3 min and the mixture was heated to 100° C. in a microwave for 15 min. The mixture was filtered through Celite, eluting with DCM and the filtrate was concentrated in vacuo. The crude residue was purified by column chromatography (0-100% EtOAc in hexane) to give the title compound. ES/MS m/z. 343.1 ($M+H^+$).

Methyl 2-(4-(6-((4-cyano-2-fluorobenzyl)oxy)-4-(1-methyl-1H-pyrazol-4-yl)pyridin-2-yl)-2-fluorobenzyl)-1-(2-methoxyethyl)-1H-benzo[d]imidazole-6-carboxylate: To a microwave vial was added methyl 2-[[2-fluoro-4-(4,4,5,5-tetramethyl-1,3,2-dioxaborolan-2-yl)phenyl]methyl]-3-

(2-methoxyethyl)benzimidazole-5-carboxylate (I-5, 26.7 mg, 5.71e-5 mol), 4-[[6-chloro-4-(1-methylpyrazol-4-yl)-2-pyridyl]oxymethyl]-3-fluoro-benzonitrile (16.3 mg, 4.76e-5 mol) and (1,1'-bis(diphenylphosphino)ferrocene)-dichloropalladium(II) (2.7 mg, 3.80e-6 mol). Acetonitrile (1.10 mL) and 1.0 M potassium acetate in water (0.12 mL, 0.12 mmol) were added, argon was bubbled through the mixture for 3 min and the mixture was heated to 100° C. in a microwave for 20 min. The mixture was filtered through Celite, eluting with DCM and the filtrate was concentrated in vacuo. The crude residue was purified by column chromatography (0-100% EtOAc in hexane) to give the title compound. ES/MS m/z: 649.3 ($M+H^+$).

2-(4-(6-((4-cyano-2-fluorobenzyl)oxy)-4-(1-methyl-1H-pyrazol-4-yl)pyridin-2-yl)-2-fluorobenzyl)-1-(2-methoxyethyl)-1H-benzo[d]imidazole-6-carboxylic acid (Example 99): To a mixture of methyl 2-[[4-[6-[(4-cyano-2-fluoro-phenyl)methoxy]-4-(1-methylpyrazol-4-yl)-2-pyridyl]-2-fluoro-phenyl]methyl]-3-(2-methoxyethyl)benzimidazole-5-carboxylate (17.0 mg, 26.2 μmol) in acetonitrile (1.00 mL) and water (0.33 mL) was added lithium hydroxide monohydrate (3.30 mg, 0.0786 mmol) and the reaction vial was sealed and heated at 80° C. for 15 min. The reaction was quenched by the addition of TFA (50 μL) and the crude mixture was purified directly by RP-HPLC (15-58.24% 0.1% TFA-ACN in 0.1% TFA Water, 15 min gradient, Column: Gemini 5 uM, NX-C18 110 Angstrom, 250×21.2 mm) to give the title compound. ES/MS m/z: 635.3 ($M+H^+$); $^1H$ NMR (400 MHz, Methanol-d4) δ 8.61 (s, 1H), 8.30-8.25 (m, 2H), 8.08 (s, 1H), 8.05-8.01 (m, 1H), 8.01-7.95 (m, 1H), 7.84-7.78 (m, 2H), 7.76 (t, J=7.5 Hz, 1H), 7.66-7.53 (m, 3H), 7.11 (s, 1H), 5.68 (s, 2H), 4.90 (s, 2H), 4.86 (s, 3H), 4.83 (s, 2H), 3.98 (s, 3H), 3.85 (t, J=4.9 Hz, 2H).

Example 100. 2-(4-(6-((4-cyano-2-fluorobenzyl)oxy)-4-(phenylethynyl)pyridin-2-yl)-2-fluorobenzyl)-1-(2-methoxyethyl)-1H-benzo[d]imidazole-6-carboxylic acid Procedure 73

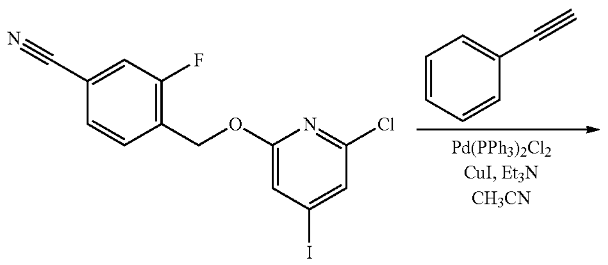

I-108

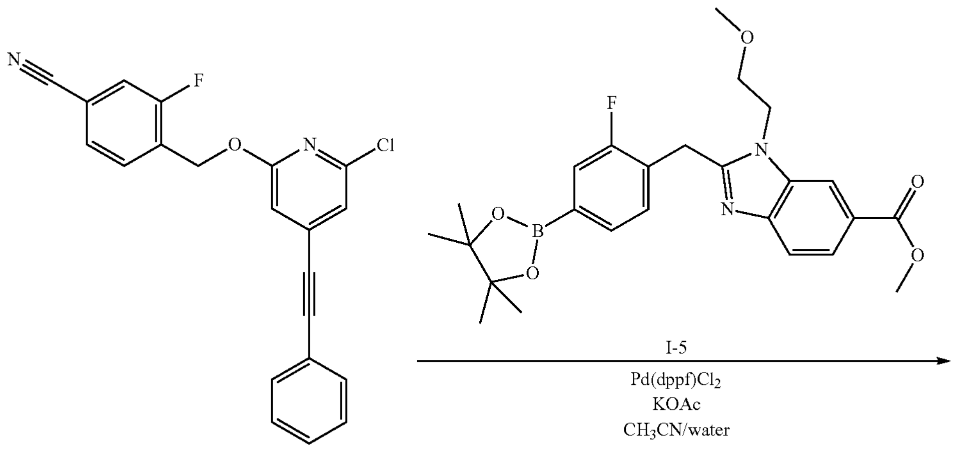

-continued

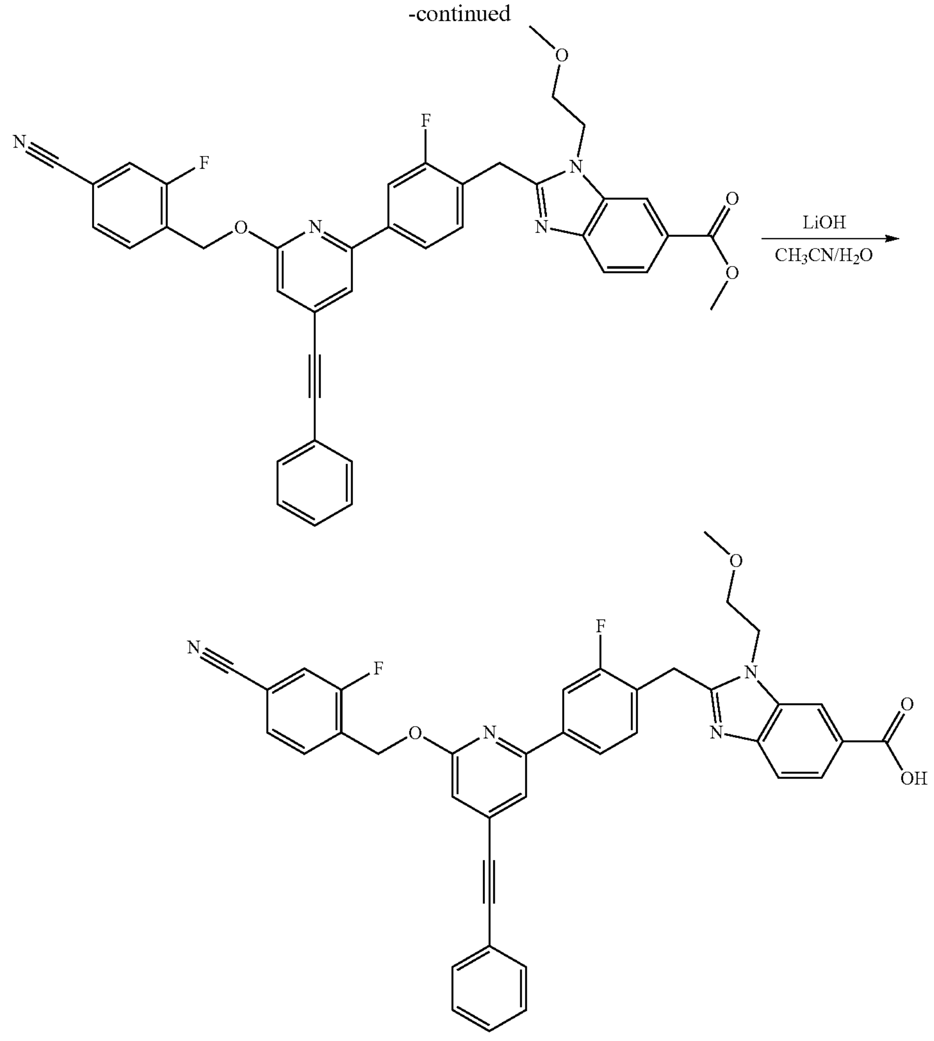

Example 100

4-(((6-chloro-4-(phenylethynyl)pyridin-2-yl)oxy)methyl)-3-fluorobenzonitrile: To a vial was added 4-[(6-chloro-4-iodo-2-pyridyl)oxymethyl]-3-fluoro-benzonitrile (I-108, 30.0 mg, 0.077 mmol), bis(triphenylphosphine)palladium chloride (5.4 mg, 0.0077 mmol) and copper(I) iodide (0.7 mg, 0.0039 mmol). The vial was sparged with argon, and acetonitrile (1.30 mL) was added followed by ethynylbenzene (12 mg, 0.12 mmol) and triethylamine (0.027 mL, 0.19 mmol), and the mixture was stirred for 1 h at room temperature. The mixture was filtered through Celite, eluting with DCM and the filtrate was concentrated in vacuo. The crude residue was used as crude in the following step, assuming full conversion. ES/MS m/z: 363.1 ($M+H^+$).

Methyl 2-(4-(6-((4-cyano-2-fluorobenzyl)oxy)-4-(phenylethynyl)pyridin-2-yl)-2-fluorobenzyl)-1-(2-methoxyethyl)-1H-benzo[d]imidazole-6-carboxylate: To a microwave vial was added methyl 2-[[2-fluoro-4-(4,4,5,5-tetramethyl-1,3,2-dioxaborolan-2-yl)phenyl]methyl]-3-(2-methoxyethyl)benzimidazole-5-carboxylate (I-5, 43.4 mg, 9.26e-5 mol), 4-[[6-chloro-4-(2-phenylethynyl)-2-pyridyl]oxymethyl]-3-fluoro-benzonitrile (28.0 mg, 7.72e-5 mol), (1,1'-bis(diphenylphosphino)ferrocene)-dichloropalladium(II) (4.4 mg, 6.17e-6 mol) and sodium carbonate (24.5 mg, 0.23 mmol). Acetonitrile (1.10 mL) and 1.0 M potassium acetate in water (0.25 mL, 0.25 mmol) were added, argon was bubbled through the mixture for 3 min and the mixture was heated to 100° C. in a microwave for 20 min. The mixture was filtered through Celite, eluting with DCM and the filtrate was concentrated in vacuo. The crude residue was purified by column chromatography (0-100% EtOAc in hexane) to give the title compound. ES/MS m/z: 669.3 ($M+H^+$).

2-(4-(6-((4-cyano-2-fluorobenzyl)oxy)-4-(phenylethynyl)pyridin-2-yl)-2-fluorobenzyl)-1-(2-methoxyethyl)-1H-benzo[d]imidazole-6-carboxylic acid (Example 100): To a mixture of methyl 2-[[4-[6-[(4-cyano-2-fluoro-phenyl)methoxy]-4-(2-phenylethynyl)-2-pyridyl]-2-fluoro-phenyl]methyl]-3-(2-methoxyethyl)benzimidazole-5-carboxylate (20.5 mg, 30.7 μmol) in acetonitrile (1.00 mL) and water (0.33 mL) was added lithium hydroxidemonohydrate (3.86 mg, 0.0920 mmol) and the mixture was stirred at 60° C. for 30 min. The reaction was quenched by the addition of TFA (50 μL) and the crude mixture was purified directly by RP-HPLC (15-79.59% 0.1% TFA-ACN in 0.1% TFA Water, 15 min gradient, Column: Gemini 5 uM, NX-C18 110 Angstrom, 250×21.2 mm) to give the title compound as a TFA salt. ES/MS m/z: 655.2 ($M+H^+$); $^1H$ NMR (400 MHz, Methanol-d4) δ 8.37 (s, 1H), 8.07 (d, J=8.3 Hz, 1H), 7.89 (d, J=9.8 Hz, 2H), 7.76 (t, J=7.6 Hz, 1H), 7.71 (d, J=8.5 Hz, 1H), 7.68-7.66 (m, 1H), 7.66-7.56 (m, 4H), 7.47-7.38 (m, 4H), 7.01 (d, J=1.0 Hz, 1H), 5.68 (s, 2H), 4.63 (t, J=5.1 Hz, 2H), 4.60 (s, 2H), 3.75 (t, J=5.0 Hz, 2H), 3.29 (s, 3H).

Example 468. 2-[[4-[6-[(4-cyano-2-fluoro-phenyl)methoxy]-2-pyridyl]-2-fluoro-phenyl]methyl]-3-(2,4-dihydroxybutyl)-7-fluoro-benzimidazole-5-carboxylic acid Procedure 74

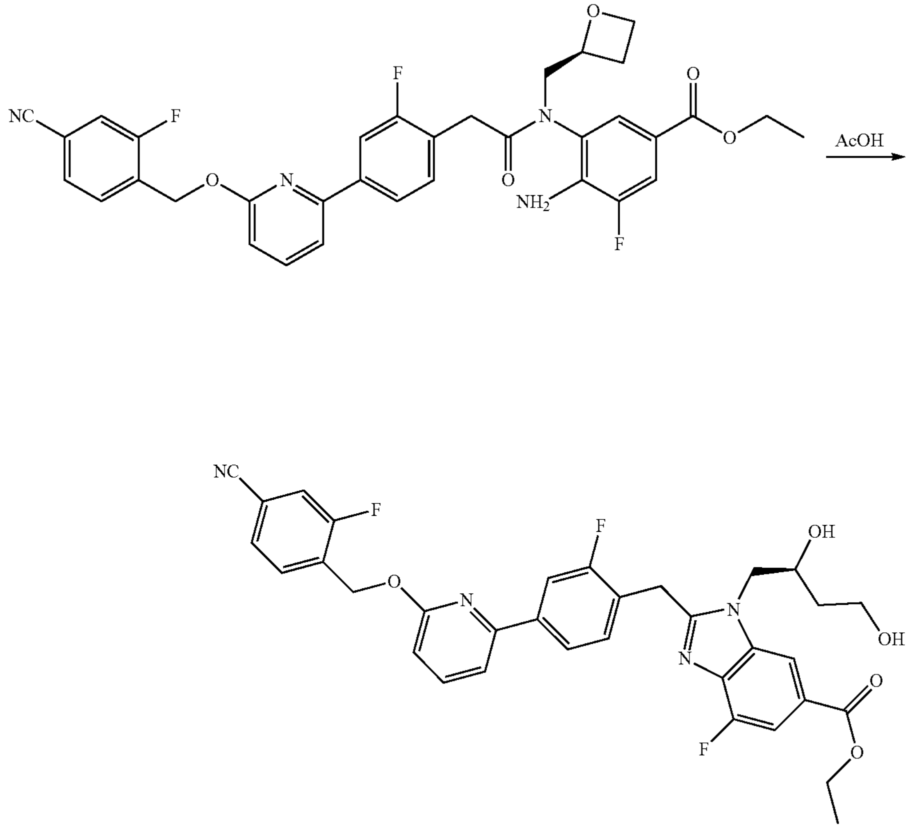

Ethyl 2-[[4-[6-[(4-cyano-2-fluoro-phenyl)methoxy]-2-pyridyl]-2-fluoro-phenyl]methyl]-3-(2,4-dihydroxybutyl)-7-fluoro-benzimidazole-5-carboxylate: Crude Ethyl 4-[[2-[4-[6-[(4-cyano-2-fluoro-phenyl)methoxy]-2-pyridyl]-2-fluoro-phenyl]acetyl]amino]-3-fluoro-5-(oxetan-2-ylmethylamino)benzoate (56 mg, 0.089 mmol) (synthesized in a manner analogous to Procedure 1) was dissolved in AcOH (2 mL) and the mixture was heated to 90° C. overnight. The mixture was cooled, concentrated and used without further purification. ES/MS m/z: 631.0 (M+H$^+$).

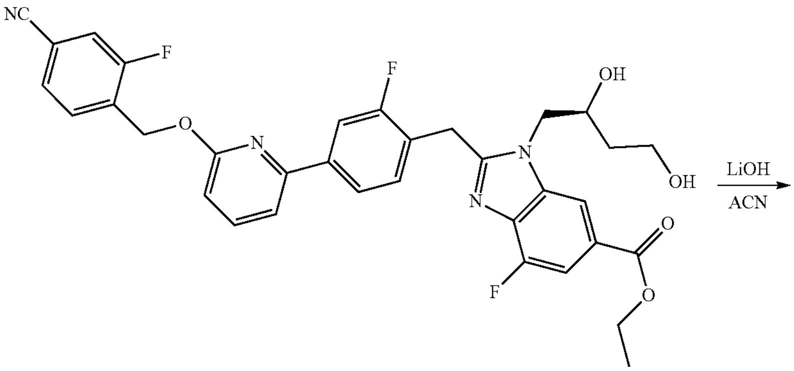

-continued

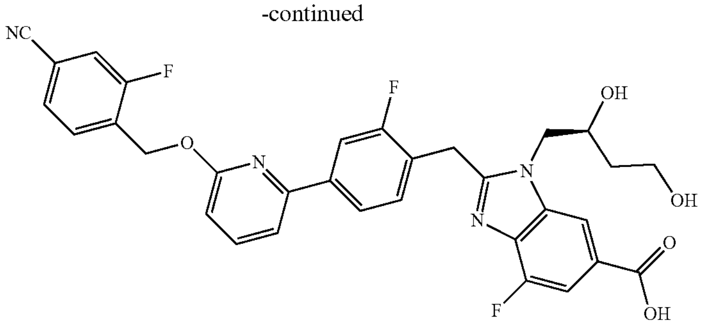

Example 468

2-[[4-[6-[(4-cyano-2-fluoro-phenyl)methoxy]-2-pyridyl]-2-fluoro-phenyl]methyl]-3-(2,4-dihydroxybutyl)-7-fluoro-benzimidazole-5-carboxylic acid (Example 468): Crude ethyl 2-[[4-[6-[(4-cyano-2-fluoro-phenyl)methoxy]-2-pyridyl]-2-fluoro-phenyl]methyl]-3-(2,4-dihydroxybutyl)-7-fluoro-benzimidazole-5-carboxylate (56 mg, 0.089 mmol) was dissolved in acetonitrile (2 mL) and 1 M aq. LiOH (0.5 mL) was added. The reaction vial was sealed and heated to 80° C. for 2 hours. The reaction was cooled to ambient temperature and quenched with excess trifluoroacetic acid (0.1 mL). The mixture was purified by RP-HPLC (eluent: water/MeCN 0.10% TFA) to yield the titled product. ES/MS m/z: 603.2 ($M+H^+$); $^1H$ NMR (400 MHz, Methanol-d4) δ 8.17 (d, J=1.2 Hz, 1H), 7.87-7.72 (m, 4H), 7.67 (dd, J=11.2, 1.3 Hz, 1H), 7.64-7.47 (m, 3H), 7.35 (t, J=8.0 Hz, 1H), 6.87 (t, J=7.9 Hz, 1H), 5.64 (d, J=8.5 Hz, 2H), 4.85 (s, 4H), 4.65 (d, J=16.5 Hz, 1H), 4.56-4.35 (m, 2H), 4.29 (dt, J=15.1, 8.2 Hz, 1H), 4.08 (s, 1H), 3.76 (q, J=7.0, 6.2 Hz, 1H), 2.04-1.68 (m, 1H). 19F NMR (377 MHz, Methanol-d4) δ −78.00 (d, J=28.3 Hz), −116.91--118.33 (m), −119.20, −131.41.

Example 471. Compounds Prepared Using Procedure 74

Other compounds of the present disclosure prepared using the general route described in Procedure 74 include the following Example.

| Example | Structure/Name/Characterization |
|---|---|
| 471 | 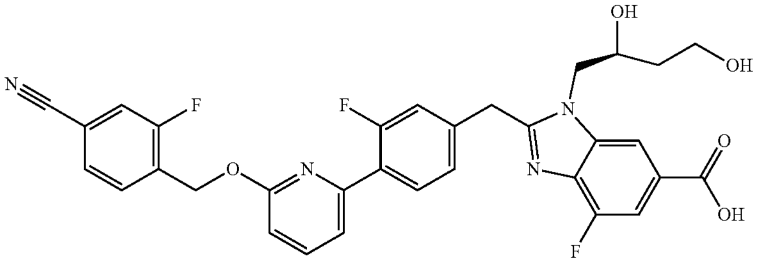 [SMILES: N#Cc1ccc(COc2cccc(-c3ccc(Cc4nc5c(F)cc(C(=O)O)cc5n4C[C@@H](O)CCO)cc3F)n2)c(F)c1] (S)-2-(4-(6-((4-cyano-2-fluorobenzyl)oxy)pyridin-2-yl)-3-fluorobenzyl)-1-(2,4-dihydroxybutyl)-4-fluoro-1H-benzo[d]imidazole-6-carboxylic acid: ES/MS m/z 603.2; $^1H$ NMR (400 MHz, Methanol-d4) δ 8.22 (dd, J = 9.7, 1.2 Hz, 1H), 7.97 (t, J = 8.1 Hz, 1H), 7.85-7.65 (m, 3H), 7.58 (ddd, J = 11.6, 9.4, 1.6 Hz, 2H), 7.53-7.42 (m, 1H), 7.30-7.14 (m, 2H), 6.88 (d, J = 8.3 Hz, 1H), 5.61 (s, 2H), 4.67-4.57 (m, 2H), 4.49 (dd, J = 14.9, 3.2 Hz, 1H), 4.31 (dd, J = 14.9, 9.6 Hz, 1H), 4.08 (s, 1H), 3.77 (td, J = 9.0, 7.3, 5.2 Hz, 1H), 1.92-1.81 (m, 2H), 1.81-1.68 (m, 1H). |

Example 476. 2-[[4-[3-[(4-chloro-2-fluoro-phenyl)methoxy]-4-fluoro-phenyl]-2-fluoro-phenyl]methyl]-3-(2-hydroxyethyl)benzimidazole-5-carboxylic acid Procedure 75

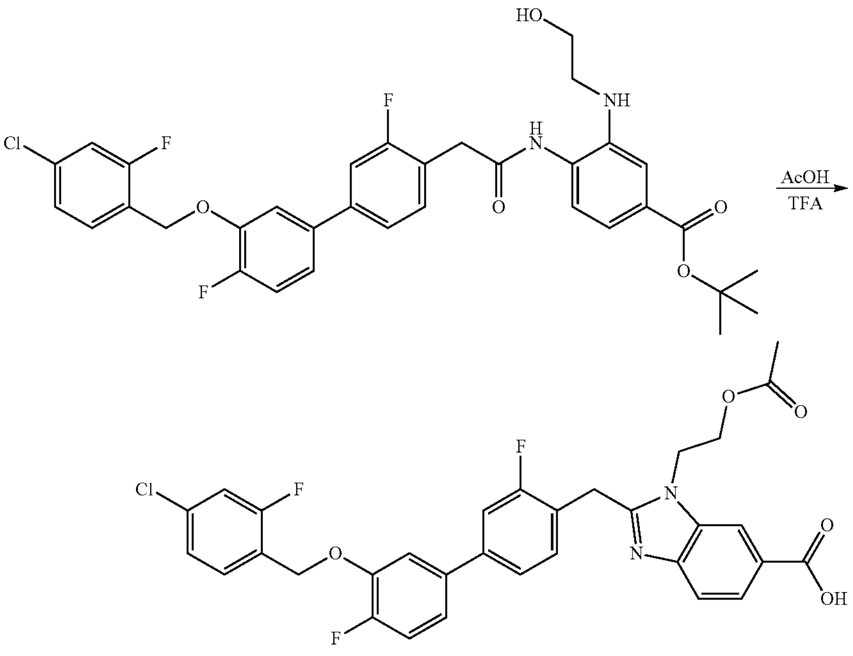

3-(2-acetoxyethyl)-2-[[4-[3-[(4-chloro-2-fluoro-phenyl)methoxy]-4-fluoro-phenyl]-2-fluoro-phenyl]methyl]benzimidazole-5-carboxylic acid: Crude tert-butyl 4-[[2-[4-[3-[(4-chloro-2-fluoro-phenyl)methoxy]-4-fluoro-phenyl]-2-fluoro-phenyl]acetyl]amino]-3-(2-hydroxyethylamino)benzoate (35 mg, 0.055 mmol) (synthesized in a manner analogous to Procedure 1), was dissolved in acetic acid (1 mL) and heated to 90° C. overnight. The mixture was cooled to ambient temperature and excess trifluoroacetic acid (0.1 mL) was added. The mixture was heated to 80° C. for 2 hours, concentrated directly and used without further purification. ES/MS m/z: 609.1 ($M+H^+$).

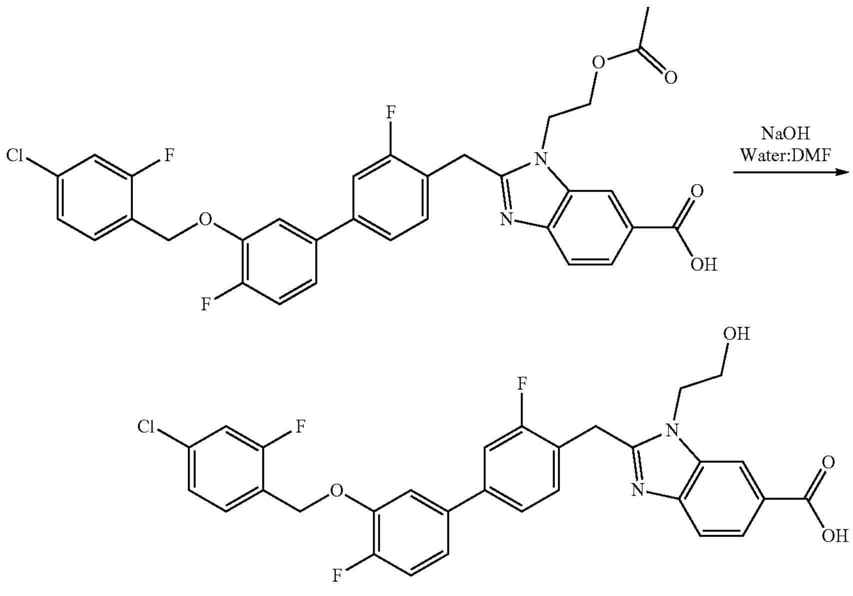

Example 476

2-[[4-[3-[(4-chloro-2-fluoro-phenyl)methoxy]-4-fluoro-phenyl]-2-fluoro-phenyl]methyl]-3-(2-hydroxyethyl)benzimidazole-5-carboxylic acid (Example 476): Crude 3-(2-acetoxyethyl)-2-[[4-[3-[(4-chloro-2-fluoro-phenyl)methoxy]-4-fluoro-phenyl]-2-fluoro-phenyl]methyl]benzimidazole-5-carboxylic acid (33 mg, 0.055 mmol) was dissolved in DMF (2.5 mL) and 2 M aq. NaOH (1 mL) was added. The mixture was heated to 30° C. for 6 hours. The reaction was cooled to ambient temperature and quenched with excess trifluoroacetic acid (0.1 mL). The mixture was purified by RP-HPLC (eluent: water/MeCN 0.1% TFA) to yield the titled product. ES/MS m/z: 567.1 $(M+H^+)$; $^1H$ NMR (400 MHz, Methanol-d4) δ 8.58 (s, 1H), 8.24 (dd, J=8.6, 1.4 Hz, 1H), 7.80 (d, J=8.6 Hz, 1H), 7.62-7.50 (m, 4H), 7.44 (dd, J=7.9, 2.2 Hz, 1H), 7.34-7.19 (m, 4H), 5.29 (s, 2H), 4.80 (s, 2H), 4.74 (t, J=5.0 Hz, 2H), 4.00 (t, J=4.9 Hz, 2H).

Example 212. 2-(4-(6-(2-(4-Chlorophenyl)-2-oxoethoxy)pyridin-2-yl)-2-fluorobenzyl)-1-(2-methoxyethyl)-1H-benzo[d]imidazole-6-carboxylic acid Procedure 76

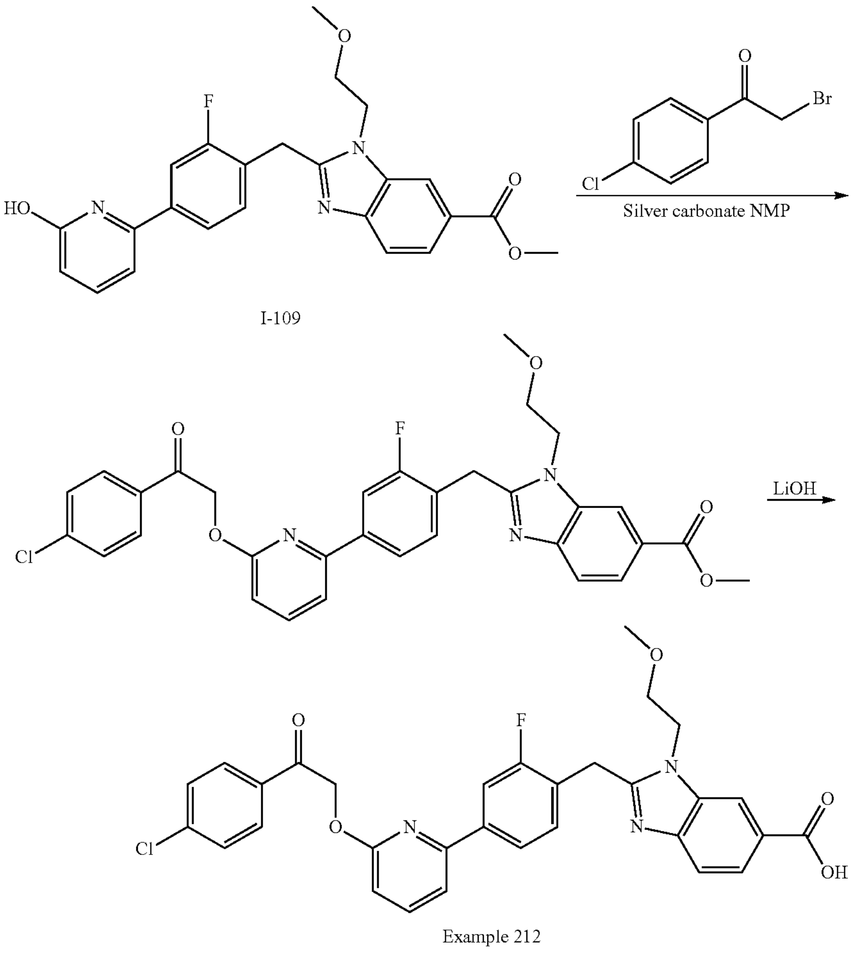

I-109

Example 212

Step 1. Methyl 2-(4-(6-(2-(4-chlorophenyl)-2-oxoethoxy)pyridin-2-yl)-2-fluorobenzyl)-1-(2-methoxyethyl)-1H-benzo[d]imidazole-6-carboxylate. To a solution of methyl 2-(2-fluoro-4-(6-hydroxypyridin-2-yl)benzyl)-1-(2-methoxyethyl)-1H-benzo[d]imidazole-6-carboxylate (I-109, 20 mg, 0.046 mmol) in NMP (0.5 mL) was added 2-bromo-1-(4-chlorophenyl)ethanone (21.0 mg, 0.0899 mmol) and silver carbonate (38.0 mg, 0.138 mmol). The slurry was heated to 70° C. (external temperature) for 36 hours and filtered. The crude solution was purified by $SiO_2$ chromatography (eluent: 10-100% EtOAc/hexanes) to provide methyl 2-(4-(6-(2-(4-chlorophenyl)-2-oxoethoxy)pyridin-2-yl)-2-fluorobenzyl)-1-(2-methoxyethyl)-1H-benzo[d]imidazole-6-carboxylate with residual NMP present. ES/MS: 295.1 $(M+H^+)$.

Step 2. 2-(4-(6-(2-(4-Chlorophenyl)-2-oxoethoxy)pyridin-2-yl)-2-fluorobenzyl)-1-(2-methoxyethyl)-1H-benzo[d]imidazole-6-carboxylic acid (Example 212). To a solution of methyl 2-(4-(6-(2-(4-chlorophenyl)-2-oxoethoxy)pyridin-2-yl)-2-fluorobenzyl)-1-(2-methoxyethyl)-1H-benzo[d]imidazole-6-carboxylate (26.8 mg, 0.459 with residual NMP present) in MeCN (1 mL) was added lithium hydroxide (1.00 M aqueous, 0.250 mL, 0.250 mmol). The reaction vessel was sealed and heated to 70° C. (external temperature) for 1.5 hours. The solution was neutralized with trifluoroacetic acid, diluted with DMF, and concentrated to remove the MeCN. The crude solution was purified by RP-HPLC (eluent: 10-65% water/MeCN/0.1% TFA). The resulting fractions were lyophilized to provide 2-(4-(6-(2-(4-chlorophenyl)-2-oxoethoxy)pyridin-2-yl)-2-fluorobenzyl)-1-(2-methoxyethyl)-1H-benzo[d]imidazole-6-carboxylic acid as the trifluoroacetic acid salt. ES/MS: 574.3 $(M+H^+)$; $^1H$ NMR (400 MHz, MeOD) δ 8.58 (s, 1H), 8.26 (d, J=8.6 Hz, 1H), 8.08 (d, J=8.4 Hz, 2H), 7.82 (t, J=7.9 Hz, 1H), 7.77 (t, J=8.1 Hz, 2H), 7.70-7.63 (m, 1H), 7.54 (dd, J=8.2, 2.5 Hz, 3H), 7.40 (t, J=7.9 Hz, 1H), 6.96 (d, J=8.2 Hz, 1H), 5.66 (s, 2H), 4.81 (t, J=4.9 Hz, 2H), 4.74 (s, 2H), 3.81 (t, J=5.0 Hz, 2H), 3.30 (s, 3H).

Examples 214-216 and 806-810. Compounds Prepared Using Procedure 76

Other compounds of the present disclosure prepared using the general route described in Procedure 76 include the following Examples.

| Example | Structure/Name/Characterization |
|---|---|
| 214 | 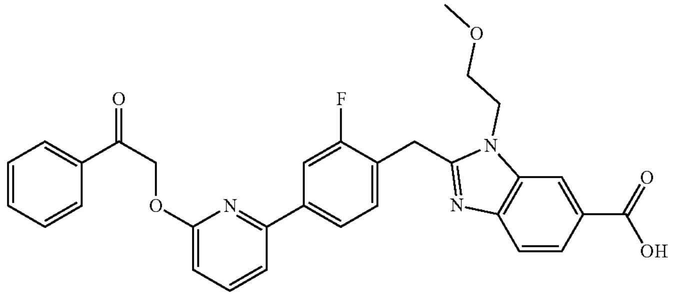 [SMILES: COCCn1c(Cc2ccc(-c3cccc(OCC(=O)c4ccccc4)n3)cc2F)nc2ccc(C(=O)O)cc21] 2-(2-fluoro-4-(6-(2-oxo-2-phenylethoxy)pyridin-2-yl)benzyl)-1-(2-methoxyethyl)-1H-benzo[d]imidazole-6-carboxylic acid: ES/MS m/z 540.25; $^1H$ NMR (400 MHz, MeOD) δ 8.40 (s, 1H), 8.09 (td, J = 8.6, 1.5 Hz, 3H), 7.80 (t, J = 7.9 Hz, 1H), 7.74-7.59 (m, 4H), 7.57-7.48 (m, 3H), 7.26 (t, J = 7.9 Hz, 1H), 6.93 (d, J = 8.2 Hz, 1H), 5.70 (s, 2H), 4.63 (t, J = 5.0 Hz, 2H), 4.56 (s, 2H), 3.72 (t, J = 5.0 Hz, 2H), 3.26 (s, 3H). |
| 215 | 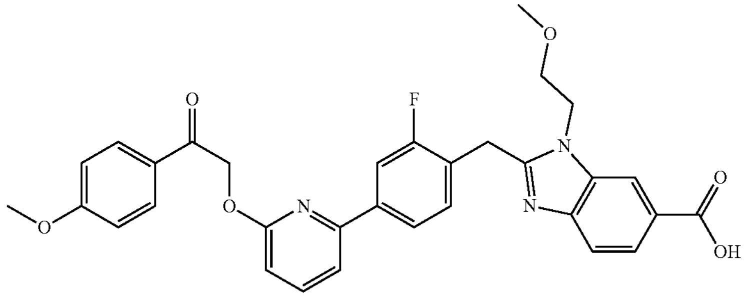 [SMILES: COCCn1c(Cc2ccc(-c3cccc(OCC(=O)c4ccc(OC)cc4)n3)cc2F)nc2ccc(C(=O)O)cc21] 2-(2-fluoro-4-(6-(2-(4-methoxyphenyl)-2-oxoethoxy)pyridin-2-yl)benzyl)-1-(2-methoxyethyl)-1H-benzo[d]imidazole-6-carboxylic acid: ES/MS m/z 570.32; $^1H$ NMR (400 MHz, MeOD) δ 8.50 (t, J = 0.9 Hz, 1H), 8.19 (dd, J = 8.6, 1.4 Hz, 1H), 8.13-8.04 (m, 2H), 7.80 (dd, J = 8.3, 7.5 Hz, 1H), 7.77-7.70 (m, 2H), 7.65 (dd, J = 11.8, 1.7 Hz, 1H), 7.52 (d, J = 7.4 Hz, 1H), 7.32 (t, J = 8.0 Hz, 1H), 7.09-7.01 (m, 2H), 6.94 (d, J = 8.2 Hz, 1H), 5.65 (s, 2H), 4.73 (t, J = 5.0 Hz, 2H), 4.66 (s, 2H), 3.85 (s, 3H), 3.77 (t, J = 4.9 Hz, 2H), 3.28 (s, 3H). |
| 216 | 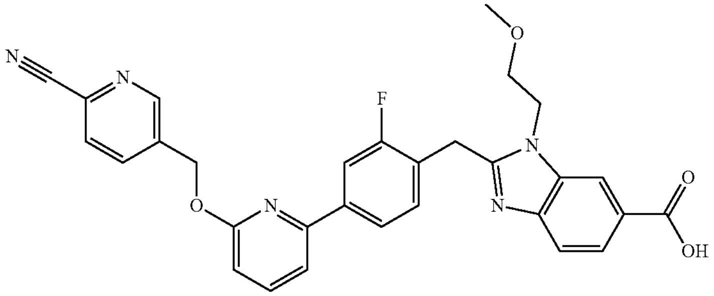 [SMILES: COCCn1c(Cc2ccc(-c3cccc(OCc4ccc(C#N)nc4)n3)cc2F)nc2ccc(C(=O)O)cc21] 2-(4-(6-((6-cyanopyridin-3-yl)methoxy)pyridin-2-yl)-2-fluorobenzyl)-1-(2-methoxyethyl)-1H-benzo[d]imidazole-6-carboxylic acid: ES/MS m/z 538.29; $^1H$ NMR (400 MHz, MeOD) δ 8.89-8.84 (m, 1H), 8.46 (t, J = 1.0 Hz, 1H), 8.13 (ddd, J = 10.0, 8.3, 1.8 Hz, 2H), 7.92-7.78 (m, 4H), 7.74 (d, J = 8.6 Hz, 1H), 7.57 (d, J = 7.4 Hz, 1H), 7.45 (t, J = 8.0 Hz, 1H), 6.93 (d, J = 8.1 Hz, 1H), 5.67 (s, 2H), 4.72 (t, J = 5.0 Hz, 2H), 4.68 (s, 2H), 3.78 (t, J = 4.9 Hz, 2H), 3.30 (s, 3H). |

-continued

| Example | Structure/Name/Characterization |
| --- | --- |
| 806 | 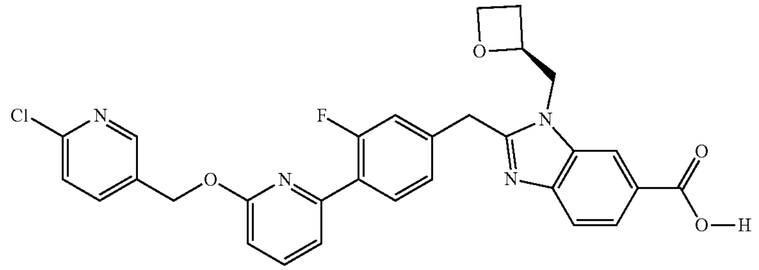 [SMILES: O=C(O)c1ccc2nc(Cc3ccc(-c4cccc(OCc5ccc(Cl)nc5)n4)c(F)c3)n(C[C@@H]3CCO3)c2c1]<br>ES/MS m/z 559.28; 1H NMR (400 MHz, Methanol-d4) δ 8.58 (dd, J = 1.5, 0.7 Hz, 1H), 8.51 (d, J = 2.4 Hz, 1H), 8.22 (dd, J = 8.6, 1.5 Hz, 1H), 8.07 (t, J = 8.2 Hz, 1H), 7.95 (dd, J = 8.2, 2.5 Hz, 1H), 7.86-7.74 (m, 2H), 7.55-7.42 (m, 2H), 7.40-7.24 (m, 2H), 6.89 (dd, J = 8.3, 0.7 Hz, 1H), 5.54 (s, 2H), 5.23 (qd, J = 7.6, 2.4 Hz, 1H), 4.96 (dd, J = 15.5, 7.7 Hz, 1H), 4.80 (d, J = 7.8 Hz, 3H), 4.70 (ddd, J = 8.4, 7.4, 5.9 Hz, 1H), 4.56 (dt, J = 9.2, 6.0 Hz, 1H), 2.86 (dtd, J = 11.5, 8.2, 6.1 Hz, 1H), 2.58 (ddt, J = 11.6, 9.1, 7.2 Hz, 1H). |
| 807 | 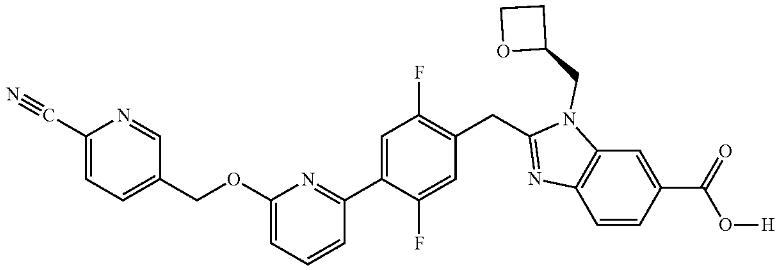 [SMILES: N#Cc1ccc(COc2cccc(-c3cc(F)c(Cc4nc5ccc(C(=O)O)cc5n4C[C@@H]4CCO4)cc3F)n2)cn1]<br>ES/MS m/z 568.32; 1H NMR (400 MHz, Methanol-d4) δ 8.85 (d, J = 2.1 Hz, 1H), 8.57 (d, J = 1.3 Hz, 1H), 8.21 (dd, J = 8.6, 1.4 Hz, 1H), 8.11 (dd, J = 8.1, 2.1 Hz, 1H), 7.96-7.70 (m, 4H), 7.58 (dd, J = 7.3, 1.6 Hz, 1H), 7.37 (dd, J = 11.2, 6.0 Hz, 1H), 6.98 (d, J = 8.2 Hz, 1H), 5.65 (s, 2H), 5.26 (qd, J = 7.5, 2.5 Hz, 1H), 4.99 (dd, J = 15.5, 7.5 Hz, 1H), 4.87-4.65 (m, 4H), 4.54 (dt, J = 9.2, 6.0 Hz, 1H), 2.88 (dtd, J = 11.6, 8.2, 6.1 Hz, 1H), 2.58 (ddt, J = 11.6, 9.2, 7.2 Hz, 1H). |
| 808 | 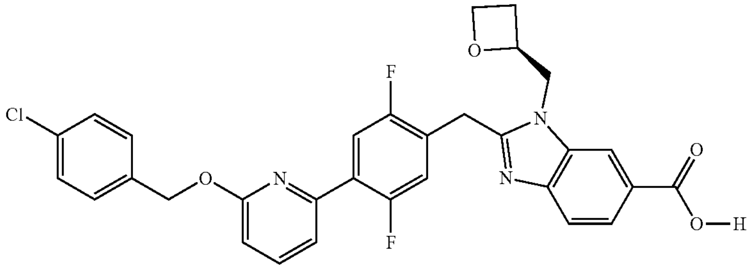 [SMILES: O=C(O)c1ccc2nc(Cc3cc(F)c(-c4cccc(OCc5ccc(Cl)cc5)n4)cc3F)n(C[C@@H]3CCO3)c2c1]<br>ES/MS m/z 576.74; 1H NMR (400 MHz, Methanol-d4) δ 8.56 (dd, J = 1.4, 0.7 Hz, 1H), 8.20 (dd, J = 8.6, 1.5 Hz, 1H), 7.88 (dd, J = 10.8, 6.3 Hz, 1H), 7.84-7.72 (m, 2H), 7.55 (dd, J = 7.1, 1.7 Hz, 1H), 7.52-7.42 (m, 2H), 7.41-7.22 (m, 3H), 6.91 (dd, J = 8.3, 0.6 Hz, 1H), 5.48 (s, 2H), 5.26 (qd, J = 7.5, 2.5 Hz, 1H), 4.97 (dd, J = 15.5, 7.5 Hz, 1H), 4.85-4.64 (m, 4H), 4.54 (dt, J = 9.2, 6.0 Hz, 1H), 2.87 (dtd, J = 11.5, 8.2, 6.1 Hz, 1H), 2.67-2.46 (m, 1H). |
| 809 | 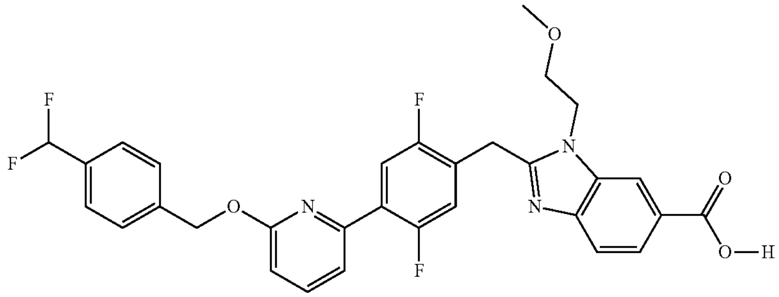 [SMILES: COCCn1c(Cc2cc(F)c(-c3cccc(OCc4ccc(C(F)F)cc4)n3)cc2F)nc2ccc(C(=O)O)cc21] |

-continued

| Example | Structure/Name/Characterization |
| --- | --- |
| | ES/MS m/z 580.3; 1H NMR (400 MHz, Methanol-d4) δ 8.54 (dd, J = 1.5, 0.7 Hz, 1H), 8.21 (dd, J = 8.6, 1.4 Hz, 1H), 7.92-7.69 (m, 3H), 7.67-7.48 (m, 6H), 7.34 (dd, J = 11.2, 6.1 Hz, 1H), 6.99-6.86 (m, 1H), 5.55 (s, 2H), 4.80 (t, J = 5.0 Hz, 2H), 4.74 (s, 2H), 3.83 (dd, J = 5.4, 4.4 Hz, 2H), 3.33 (td, J = 2.9, 1.3 Hz, 3H). |
| 810 | 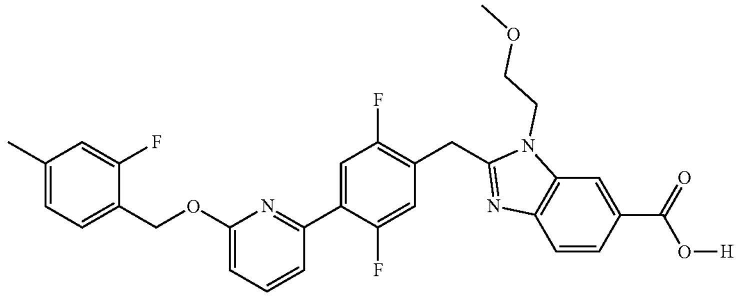 [SMILES: COCCn1c(Cc2cc(F)c(-c3cccc(OCc4ccc(C)cc4F)n3)cc2F)nc2ccc(C(=O)O)cc21] ES/MS m/z 562.27; 1H NMR (400 MHz, Methanol-d4) δ 8.55 (d, J = 1.4 Hz, 1H), 8.22 (dd, J = 8.6, 1.4 Hz, 1H), 7.94 (dd, J = 10.8, 6.3 Hz, 1H), 7.87-7.74 (m, 2H), 7.55 (dd, J = 7.4, 1.7 Hz, 1H), 7.50-7.25 (m, 2H), 6.98 (ddd, J = 12.5, 10.1, 1.6 Hz, 2H), 6.88 (d, J = 8.2 Hz, 1H), 5.49 (s, 2H), 4.86-4.69 (m, 4H), 3.84 (dd, J = 5.4, 4.4 Hz, 2H), 2.35 (s, 3H). |

Example 604. 2-(4-(6-((4-cyanobenzyl)oxy)pyridin-2-yl)-2,5-difluorobenzyl)-1-(2-methoxyethyl)-1H-benzo[d]imidazole-6-carboxylic acid Procedure 77

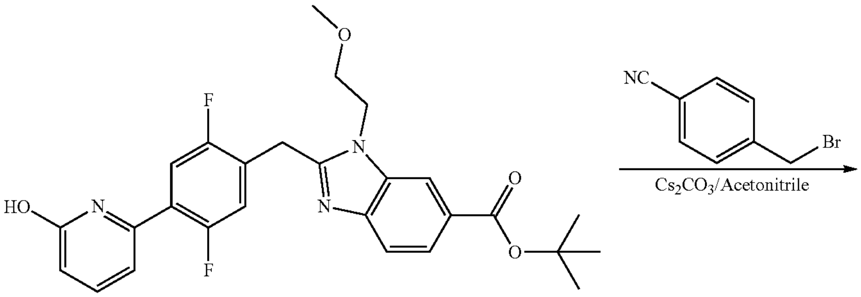

I-135

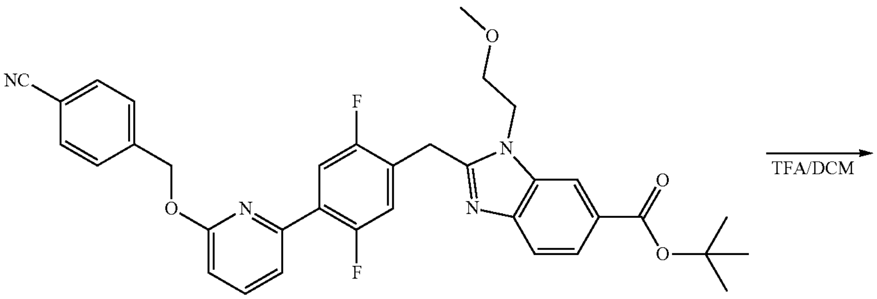

-continued

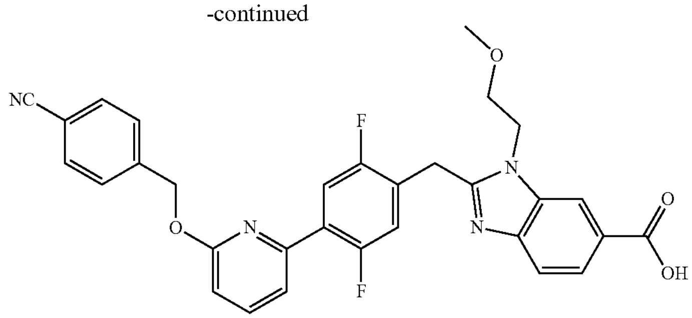

Example 604

Step 1. tert-butyl 2-(4-(6-((4-cyanobenzyl)oxy)pyridin-2-yl)-2,5-difluorobenzyl)-1-(2-methoxyethyl)-1H-benzo[d]imidazole-6-carboxylate: To a solution of tert-butyl 2-(2,5-difluoro-4-(6-hydroxypyridin-2-yl)benzyl)-1-(2-methoxyethyl)-1H-benzo[d]imidazole-6-carboxylate (I-135, 25 mg, 0.051 mmol) in acetonitrile (0.7 mL) was added 4-(bromomethyl)benzonitrile (10 mg, 0.051 mmol) and cesium carbonate (33 mg, 0.138 mmol). The mixture was stirred at RT for 3 hours and filtered. The crude solution was purified by $SiO_2$ chromatography (eluent: 15-100% EtOAc/hexanes) to provide tert-butyl 2-(4-(6-((4-cyanobenzyl)oxy)pyridin-2-yl)-2,5-difluorobenzyl)-1-(2-methoxyethyl)-1H-benzo[d]imidazole-6-carboxylate. ES/MS: 628.7 ($M+H^+$).

Step 2. 2-(4-(6-((4-cyanobenzyl)oxy)pyridin-2-yl)-2,5-difluorobenzyl)-1-(2-methoxyethyl)-1H-benzo[d]imidazole-6-carboxylic acid (Example 604): To a solution of tert-butyl 2-(4-(6-((4-cyanobenzyl)oxy)pyridin-2-yl)-2,5-difluorobenzyl)-1-(2-methoxyethyl)-1H-benzo[d]imidazole-6-carboxylate (19 mg, 0.031 mmol) in DCM (1 mL) was added TFA (71 mg, 0.62 mmol). The mixture was stirred at RT for 2.5 hours. The crude solution was purified by RP-HPLC (eluent: 25-75% water/MeCN/0.1% TFA). The resulting fractions were lyophilized to provide 2-(4-(6-((4-cyanobenzyl)oxy)pyridin-2-yl)-2,5-difluorobenzyl)-1-(2-methoxyethyl)-1H-benzo[d]imidazole-6-carboxylic acid (Example 604) as the trifluoroacetic acid salt. ES/MS: 555.4 ($M+H^+$); $^1H$ NMR (400 MHz, Methanol-d4) δ 8.55 (dd, J=1.4, 0.7 Hz, 1H), 8.22 (dd, J=8.6, 1.4 Hz, 1H), 7.90-7.71 (m, 5H), 7.71-7.62 (m, 2H), 7.57 (dd, J=7.4, 1.8 Hz, 1H), 7.35 (dd, J=11.2, 6.1 Hz, 1H), 6.97 (dd, J=8.3, 0.6 Hz, 1H), 5.59 (s, 2H), 4.87-4.80 (m, 2H), 4.75 (s, 2H), 3.84 (dd, J=5.4, 4.4 Hz, 2H), 3.33-3.27 (m, 3H).

Examples 602-603 and 811-823. Compounds Prepared Using Procedure 77

Other compounds of the present disclosure prepared using the general route described in Procedure 77 include the following Examples.

| Example | Structure/Name/Characterization |
|---|---|
| 602 | 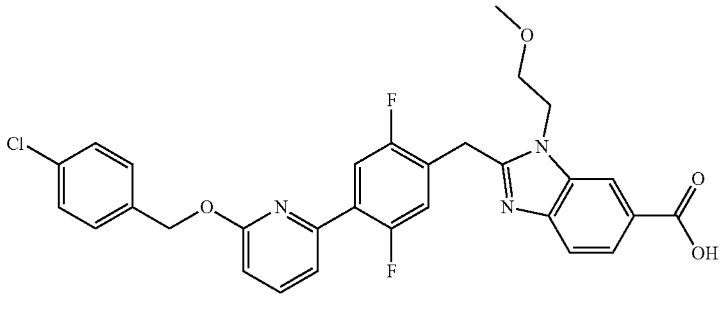 [SMILES: COCCn1c(Cc2cc(F)c(-c3cccc(OCc4ccc(Cl)cc4)n3)cc2F)nc2ccc(C(=O)O)cc21]<br>2-(4-(6-((4-chlorobenzyl)oxy)pyridin-2-yl)-2,5-difluorobenzyl)-1-(2-methoxyethyl)-1H-benzo[d]imidazole-6-carboxylic acid: ES/MS m/z 564.6; $^1H$ NMR (400 MHz, Methanol-d4) δ 8.49 (d, J = 1.3 Hz, 1H), 8.16 (dd, J = 8.5, 1.5 Hz, 1H), 7.93-7.67 (m, 3H), 7.54 (dd, J = 7.3, 1.6 Hz, 1H), 7.52-7.43 (m, 2H), 7.42-7.24 (m, 3H), 6.90 (d, J = 8.2 Hz, 1H), 5.47 (s, 2H), 4.81-4.63 (m, 4H), 3.88-3.79 (m, 2H), 3.73-3.62 (m, 1H), 3.34-3.26 (m, 3H). |

-continued

| Example | Structure/Name/Characterization |
|---|---|
| 603 | 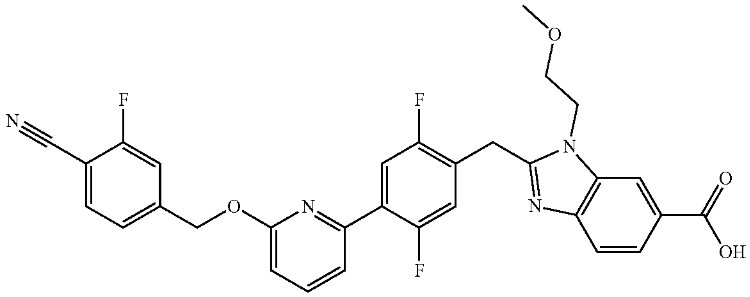 [SMILES: COCCn1c(Cc2cc(F)c(-c3cccc(OCc4ccc(C#N)c(F)c4)n3)cc2F)nc2ccc(C(=O)O)cc21]<br>2-(4-(6-((4-cyano-3-fluorobenzyl)oxy)pyridin-2-yl)-2,5-difluorobenzyl)-1-(2-methoxyethyl)-1H-benzo[d]imidazole-6-carboxylic acid: ES/MS m/z 573.2; $^1$H NMR (400 MHz, Methanol-d4) δ 8.51 (d, J = 1.5 Hz, 1H), 8.19 (dd, J = 8.6, 1.5 Hz, 1H), 7.93-7.71 (m, 4H), 7.58 (dd, J = 7.4, 1.6 Hz, 1H), 7.53-7.43 (m, 2H), 7.32 (dd, J = 11.3, 6.1 Hz, 1H), 6.97 (dd, J = 11.1, 8.3 Hz, 1H), 5.62 (d, J = 16.3 Hz, 2H), 4.18 (ddd, J = 12.3, 9.0, 3.7 Hz, 2H), 3.83 (t, J = 4.9 Hz, 2H), 3.55 (dt, J = 11.8, 2.8 Hz, 2H), 3.29 (s, 3H). |
| 811 | 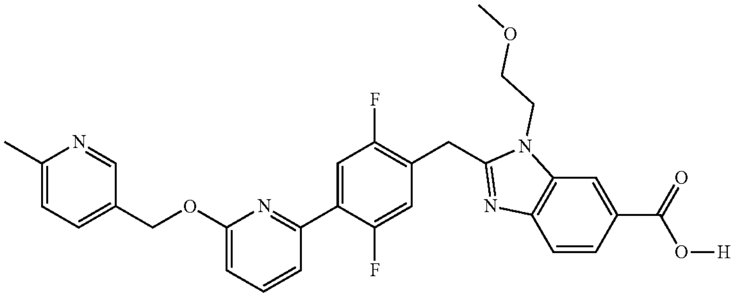<br>ES/MS m/z 545.51; 1H NMR (400 MHz, Methanol-d4) δ 8.86 (d, J = 1.9 Hz, 1H), 8.60 (dd, J = 8.3, 2.0 Hz, 1H), 8.52 (d, J = 1.4 Hz, 1H), 8.19 (dd, J = 8.6, 1.4 Hz, 1H), 7.99-7.82 (m, 3H), 7.77 (d, J = 8.6 Hz, 1H), 7.60 (dd, J = 7.5, 1.6 Hz, 1H), 7.36 (dd, J = 11.2, 6.1 Hz, 1H), 7.00 (d, J = 8.2 Hz, 1H), 5.70 (s, 2H), 4.84-4.67 (m, 4H), 3.84 (t, J = 4.9 Hz, 2H), 3.33 (s, 4H), 2.79 (s, 3H). |
| 812 | 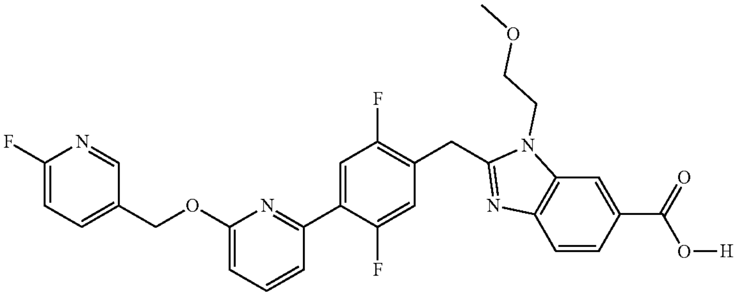<br>ES/MS m/z 549.52; 1H NMR (400 MHz, Methanol-d4) δ 8.55 (d, J = 1.3 Hz, 1H), 8.35 (d, J = 2.3 Hz, 1H), 8.22 (dd, J = 8.6, 1.4 Hz, 1H), 8.09 (td, J = 8.1, 2.5 Hz, 1H), 7.93 (dd, J = 10.7, 6.3 Hz, 1H), 7.89-7.72 (m, 2H), 7.57 (dd, J = 7.4, 1.6 Hz, 1H), 7.37 (dd, J = 11.2, 6.1 Hz, 1H), 7.10 (dd, J = 8.5, 2.5 Hz, 1H), 6.92 (d, J = 8.3 Hz, 1H), 5.55 (s, 2H), 4.82 (t, J = 4.9 Hz, 2H), 4.76 (s, 2H), 3.84 (t, J = 4.9 Hz, 2H), 3.33 (s, 3H). |

-continued
| Example | Structure/Name/Characterization |
|---|---|
| 813 | 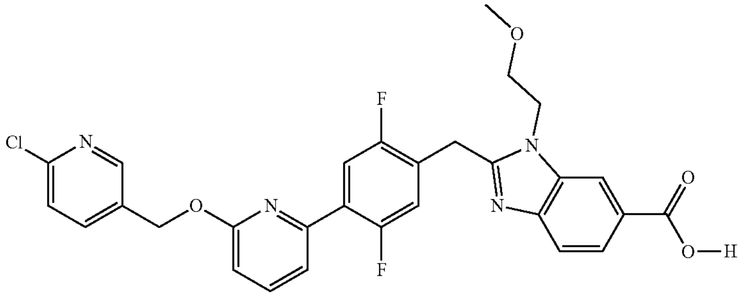 [SMILES: COCCn1c(Cc2cc(F)c(-c3cccc(OCc4ccc(F)nc4)n3)cc2F)nc2ccc(C(=O)O)cc21]<br>ES/MS m/z 565.75; 1H NMR (400 MHz, Methanol-d4) δ 8.53 (dd, J = 11.5, 1.9 Hz, 2H), 8.21 (dd, J = 8.6, 1.5 Hz, 1H), 8.00-7.86 (m, 2H), 7.87-7.68 (m, 2H), 7.57 (dd, J = 7.4, 1.6 Hz, 1H), 7.48 (d, J = 8.2 Hz, 1H), 7.36 (dd, J = 11.2, 6.1 Hz, 1H), 6.93 (d, J = 8.2 Hz, 1H), 5.55 (s, 2H), 4.81 (t, J = 5.0 Hz 2H), 4.75 (s, 2H), 3.90-3.78 (m, 2H), 3.33 (s, 3H). |
| 814 | 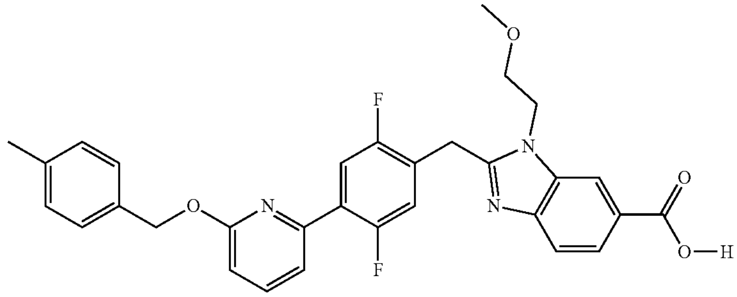 [SMILES: COCCn1c(Cc2cc(F)c(-c3cccc(OCc4ccc(C)cc4)n3)cc2F)nc2ccc(C(=O)O)cc21]<br>ES/MS m/z 544.37; 1H NMR (400 MHz, Methanol-d4) δ 8.65-8.38 (m, 1H), 8.20 (dd, J = 8.6, 1.4 Hz, 1H), 7.91 (dd, J = 10.8, 6.4 Hz, 1H), 7.83-7.65 (m, 2H), 7.53 (dd, J = 7.4, 1.7 Hz, 1H), 7.43-7.27 (m, 3H), 7.19 (d, J = 7.8 Hz, 2H), 6.88 (d, J = 8.2 Hz, 1H), 5.44 (s, 2H), 4.83-4.68 (m, 4H), 3.83 (t, J = 4.9 Hz, 2H), 3.30 (s, 3H), 2.34 (s, 3H). |
| 815 | 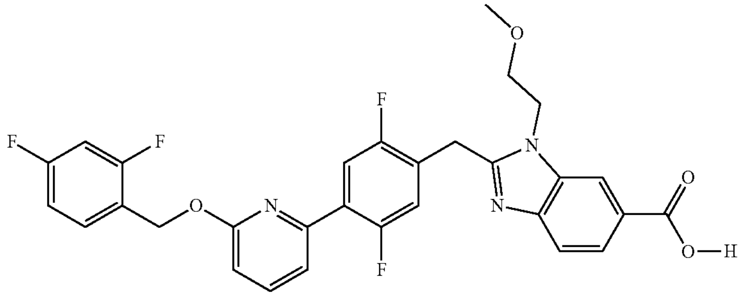 [SMILES: COCCn1c(Cc2cc(F)c(-c3cccc(OCc4ccc(F)cc4F)n3)cc2F)nc2ccc(C(=O)O)cc21]<br>ES/MS m/z 566.33; 1H NMR (400 MHz, Methanol-d4) δ 8.56 (d, J = 1.3 Hz, 1H), 8.22 (dd, J = 8.6, 1.4 Hz, 1H), 7.93 (dd, J = 10.8, 6.3 Hz, 1H), 7.85-7.72 (m, 2H), 7.65-7.49 (m, 2H), 7.37 (dd, J = 11.2, 6.1 Hz, 1H), 7.07-6.94 (m, 2H), 6.89 (d, J = 8.2 Hz, 1H), 5.51 (s, 2H), 4.86-4.70 (m, 4H), 3.89-3.74 (m, 2H), 3.31 (s, 3H). |
| 816 | 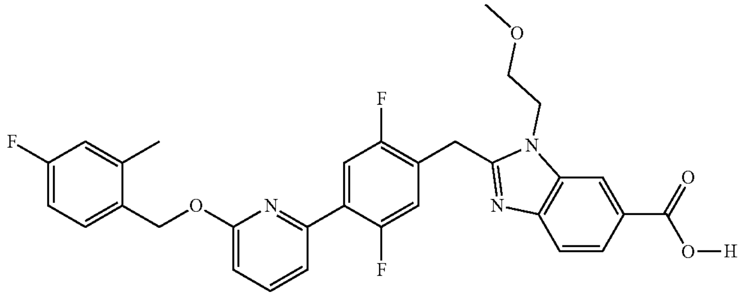 [SMILES: COCCn1c(Cc2cc(F)c(-c3cccc(OCc4ccc(F)cc4C)n3)cc2F)nc2ccc(C(=O)O)cc21] |

-continued

| Example | Structure/Name/Characterization |
|---|---|
| | ES/MS m/z 562.55; 1H NMR (400 MHz, Methanol-d4) δ 8.58 (d, J = 1.6 Hz, 1H), 8.25 (dd, J = 8.6, 1.4 Hz, 1H), 7.94 (dt, J = 10.8, 6.4 Hz, 1H), 7.80 (dq, J = 8.0, 3.2 Hz, 2H), 7.62-7.48 (m, 1H), 7.48-7.34 (m, 2H), 7.03-6.78 (m, 3H), 5.58-5.34 (m, 2H), 4.89-4.75 (m, 4H), 3.91-3.75 (m, 2H), 3.32 (d, J = 1.7 Hz, 2H), 2.50-2.31 (m, 3H). |
| 817 | 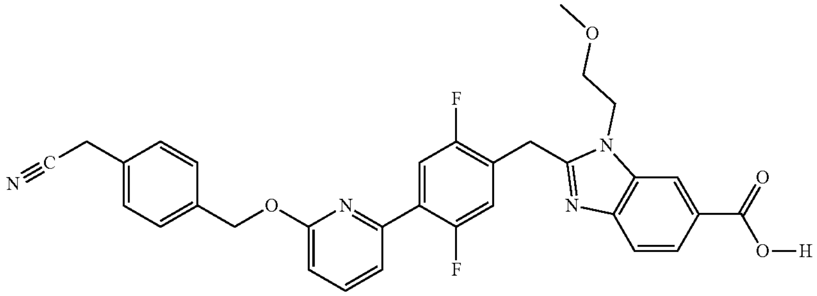 [SMILES: COCCn1c(Cc2cc(F)c(-c3cccc(OCc4ccc(CC#N)cc4)n3)cc2F)nc2ccc(C(=O)O)cc21] ES/MS m/z 569.34; 1H NMR (400 MHz, Methanol-d4) δ 8.55 (dd, J = 1.4, 0.7 Hz, 1H), 8.22 (dd, J = 8.6, 1.4 Hz, 1H), 7.88 (dd, J = 10.8, 6.3 Hz, 1H), 7.85-7.76 (m, 2H), 7.63-7.47 (m, 3H), 7.36 (dd, J = 18.6, 7.2 Hz, 3H), 6.92 (dd, J = 8.3, 0.7 Hz, 1H), 5.50 (s, 2H), 4.87-4.73 (m, 6H), 3.91 (s, 2H), 3.84 (dd, J = 5.4, 4.4 Hz, 2H), 3.32 (s, 3H). |
| 818 | 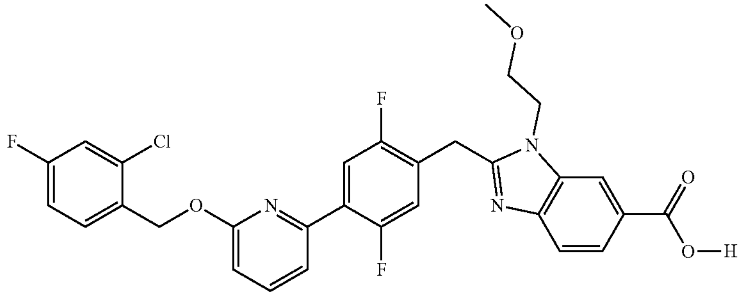 [SMILES: COCCn1c(Cc2cc(F)c(-c3cccc(OCc4ccc(F)cc4Cl)n3)cc2F)nc2ccc(C(=O)O)cc21] ES/MS m/z 582.7; 1H NMR (400 MHz, DMSO-d6) δ 8.30 (d, J = 1.5 Hz, 1H), 7.97-7.75 (m, 3H), 7.74-7.59 (m, 2H), 7.60-7.48 (m, 2H), 7.42 (dd, J = 11.5, 6.1 Hz, 1H), 7.27 (td, J = 8.5, 2.7 Hz, 1H), 6.98 (d, J = 8.2 Hz, 1H), 5.52 (s, 2H), 4.66 (t, J = 5.0 Hz, 2H), 4.53 (s, 2H), 3.70 (t, J = 5.0 Hz, 2H), 3.21 (s, 3H). |
| 819 | 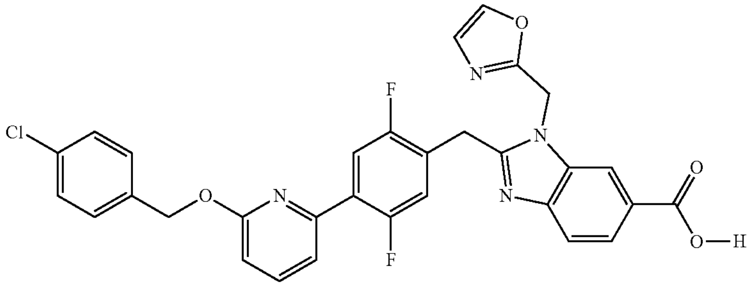 [SMILES: O=C(O)c1ccc2nc(Cc3cc(F)c(-c4cccc(OCc5ccc(Cl)cc5)n4)cc3F)n(Cc3ncco3)c2c1] ES/MS m/z 587.34; 1H NMR (400 MHz, Methanol-d4) d 8.39 (d, J = 1.4 Hz, 1H), 8.10 (dd, J = 8.6, 1.5 Hz, 1H), 7.85 (d, J = 0.8 Hz, 1H), 7.83-7.70 (m, 3H), 7.58-7.44 (m, 3H), 7.43-7.32 (m, 2H), 7.18 (dd, J = 11.3, 6.0 Hz, 1H), 7.07 (d, J = 0.8 Hz, 1H), 6.89 (d, J = 8.2 Hz, 1H), 5.89 (s, 2H), 5.47 (s, 2H), 4.92 (t, J = 2.7 Hz, 1H), 4.63 (s, 2H), 4.18 (ddd, J = 12.3, 9.0, 3.7 Hz, 1H), 3.80-3.63 (m, 4H), 3.55 (dt, J = 11.8, 2.8 Hz, 1H). |

-continued

| Example | Structure/Name/Characterization |
| --- | --- |
| 820 | 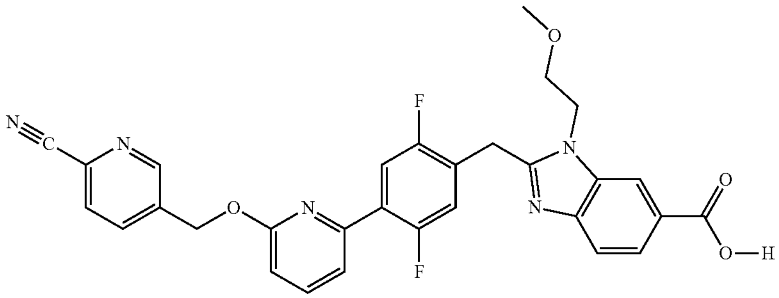 [SMILES: COCCn1c(Cc2cc(F)c(-c3cccc(OCc4ccc(C#N)nc4)n3)cc2F)nc2ccc(C(=O)O)cc21] ES/MS m/z 556.39; 1H NMR (400 MHz, Methanol-d4) δ 8.85 (dd, J = 2.1, 0.8 Hz, 1H), 8.53 (d, J = 1.4 Hz, 1H), 8.20 (dd, J = 8.6, 1.4 Hz, 1H), 8.11 (dd, J = 8.0, 2.1 Hz, 1H), 7.94-7.71 (m, 4H), 7.58 (dd, J = 7.2, 1.6 Hz, 1H), 7.34 (dd, J = 11.2, 6.1 Hz, 1H), 6.98 (dd, J = 8.3, 0.6 Hz, 1H), 5.65 (s, 2H), 4.79 (t, J = 5.0 Hz, 2H), 4.73 (s, 2H), 3.88-3.77 (m, 2H), 3.33-3.31 (s, 3H). |
| 821 | 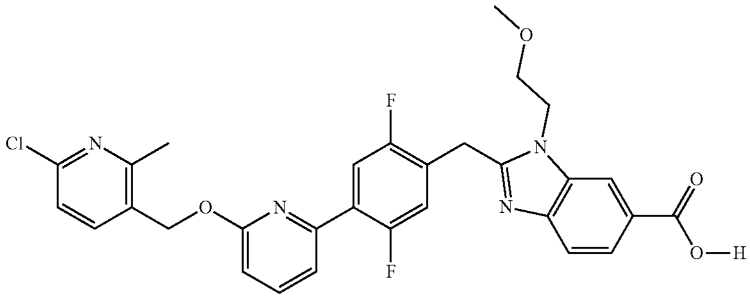 [SMILES: COCCn1c(Cc2cc(F)c(-c3cccc(OCc4ccc(Cl)nc4C)n3)cc2F)nc2ccc(C(=O)O)cc21] ES/MS m/z 579.5; 1H NMR (400 MHz, Methanol-d4) δ 8.53 (t, J = 1.0 Hz, 1H), 8.20 (dd, J = 8.6, 1.5 Hz, 1H), 7.92-7.81 (m, 3H), 7.77 (d, J = 8.6 Hz, 1H), 7.56 (dd, J = 7.5, 1.7 Hz, 1H), 7.41-7.34 (m, 1H), 7.34-7.25 (m, 1H), 6.94 (d, J = 8.2 Hz, 1H), 5.53 (s, 2H), 4.80 (t, J = 5.0 Hz, 2H), 4.74 (s, 2H), 3.83 (t, J = 4.9 Hz, 2H), 3.32 (s, 3H), 2.60 (s, 3H). |
| 822 | 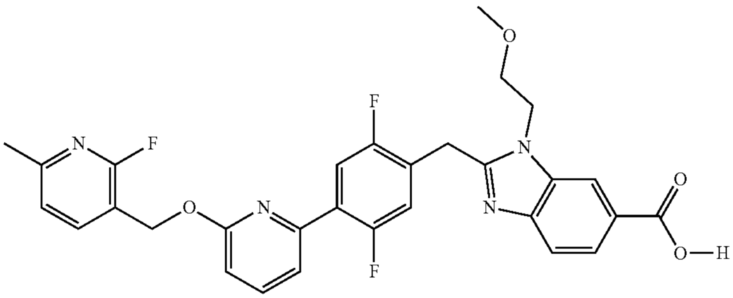 [SMILES: COCCn1c(Cc2cc(F)c(-c3cccc(OCc4ccc(C)nc4F)n3)cc2F)nc2ccc(C(=O)O)cc21] ES/MS m/z 563.4; 1H NMR (400 MHz, Methanol-d4) δ 8.49 (d, J = 1.3 Hz, 1H), 8.17 (dd, J = 8.6, 1.4 Hz, 1H), 7.92 (ddd, J = 22.4, 10.3, 7.0 Hz, 2H), 7.81 (t, J = 7.9 Hz, 1H), 7.75 (d, J = 8.6 Hz, 1H), 7.56 (dd, J = 7.4, 1.6 Hz, 1H), 7.33-7.23 (m, 1H), 7.19 (dd, J = 7.6, 1.7 Hz, 1H), 6.91 (d, J = 8.2 Hz, 1H), 5.51 (s, 2H), 4.77 (t, J = 5.0 Hz, 2H), 4.70 (s, 2H), 3.82 (t, J = 4.9 Hz, 2H), 3.31 (s, 3H), 2.47 (s, 3H). |

-continued

| Example | Structure/Name/Characterization |
|---|---|
| 823 | 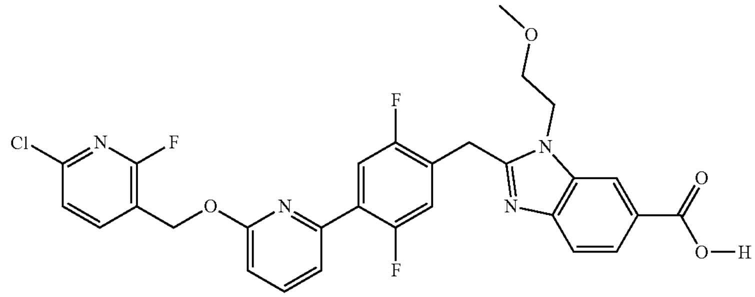<br>ES/MS m/z 583.5; 1H NMR (400 MHz, Methanol-d4) δ 8.51 (d, J = 1.4 Hz, 1H), 8.18 (dd, J = 8.6, 1.5 Hz, 1H), 8.07 (dd, J = 9.4, 7.8 Hz, 1H), 7.88 (dd, J = 10.7, 6.3 Hz, 1H), 7.83 (t, J = 7.9 Hz, 1H), 7.76 (d, J = 8.6 Hz, 1H), 7.57 (dd, J = 7.3, 1.6 Hz, 1H), 7.38 (dd, J = 7.8, 0.9 Hz, 1H), 7.33 (dd, J = 11.3, 6.1 Hz, 1H), 6.94 (d, J = 8.2 Hz, 1H), 5.53 (s, 2H), 4.78 (t, J = 5.0 Hz, 2H), 4.72 (s, 2H), 3.88-3.78 (m, 2H), 3.31 (s, 3H). |

Example 599. 2-(4-(2-((4-cyano-2-fluorobenzyl)oxy)pyrimidin-4-yl)-2,5-difluorobenzyl)-3-((1-(cyanomethyl)cyclopropyl)methyl)-3H-imidazo[4,5-b]pyridine-5-carboxamide Procedure 78:

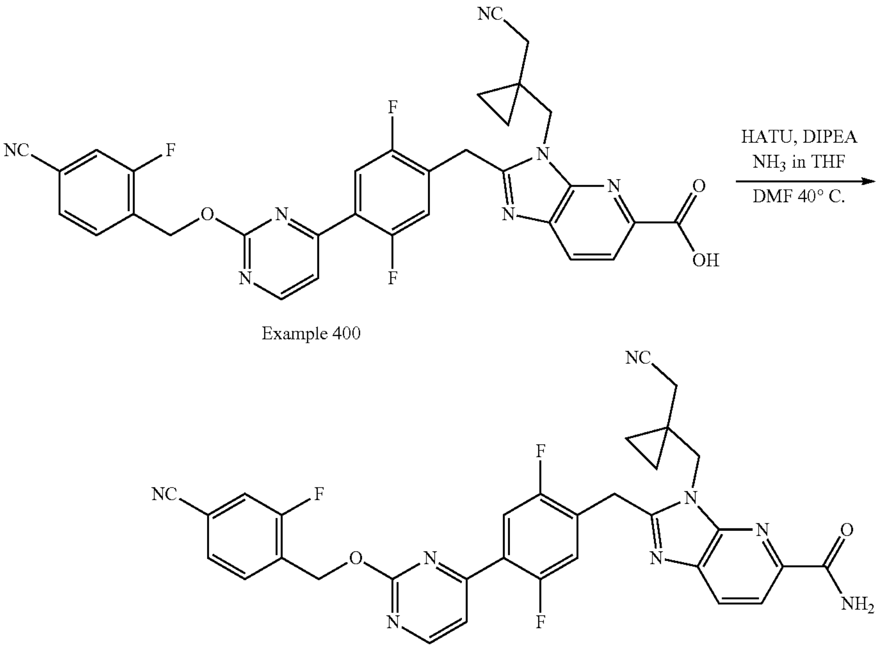

Example 400

Example 599

2-(4-(2-((4-cyano-2-fluorobenzyl)oxy)pyrimidin-4-yl)-2,5-difluorobenzyl)-3-((1-(cyanomethyl)cyclopropyl)methyl)-3H-imidazo[4,5-b]pyridine-5-carboxamide (Example 599): 2-(4-(2-((4-cyano-2-fluorobenzyl)oxy)pyrimidin-4-yl)-2,5-difluorobenzyl)-3-((1-(cyanomethyl)cyclopropyl)methyl)-3H-imidazo[4,5-b]pyridine-5-carboxylic acid, Example 400 (12 mg, 0.0197 mmol), 2-(7-aza-1H-benzotriazole-1-yl)-1,1,3,3-tetramethyluronium hexafluorophosphate (HATU) (6 mg, 0.024 mmol) in DMF (0.125 mL) was treated with ammonia in THF (0.4 M, 0.246 mL, 0.098 mmol) and heated at 40° C. for 40 minutes. The mixture was acidified with formic acid (0.5 mL) and purified by RP-HPLC (eluent: water/MeCN 0.10 TFA) to yield 2-(4-(2-((4-cyano-2-fluorobenzyl)oxy)pyrimidin-4-yl)-2,5-difluorobenzyl)-3-((1-(cyanomethyl)cyclopropyl)methyl)-3H-imidazo[4,5-b]pyridine-5-carboxamide (Example 599). ES/MS m/z: 609.20 ($M+H^+$); $^1H$ NMR (400 MHz, Methanol-d4) δ 8.71 (d, J=5.2 Hz, 1H), 8.18 (d, J=8.3 Hz, 1H), 8.15-8.05 (m, 1H), 7.97 (dd, J=10.3, 6.2 Hz, 1H), 7.80 (t, J=7.6 Hz, 1H), 7.71-7.55 (m, 3H), 7.39 (dd, J=11.4, 5.9 Hz, 1H), 5.70 (s, 2H), 4.63 (m, 4H), 2.64 (d, J=54.1 Hz, 2H), 1.08 (q, J=5.4 Hz, 2H), 0.82 (q, J=4.8, 3.9 Hz, 2H).

Examples 597-598. Compounds Prepared Using Procedure 78

Other compounds of the present disclosure prepared using the general route described in Procedure 78 include the following Examples.

| Example | Structure/Name/Characterization |
| --- | --- |
| 597 | 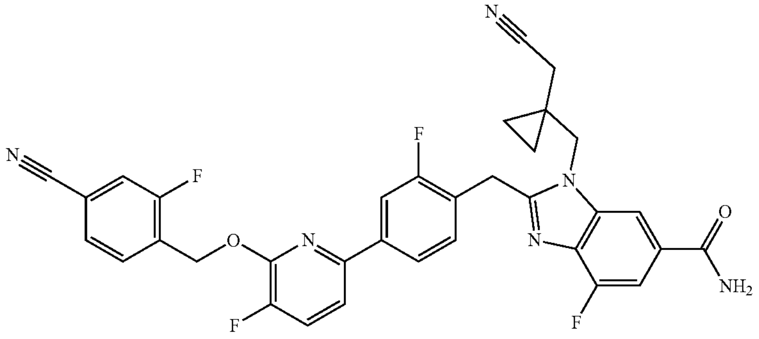 [SMILES: N#CCC1(Cn2c(Cc3ccc(-c4ccc(F)c(OCc5ccc(C#N)cc5F)n4)cc3F)nc3c(F)cc(C(N)=O)cc32)CC1] 2-(4-(6-((4-cyano-2-fluorobenzyl)oxy)-5-fluoropyridin-2-yl)-2-fluorobenzyl)-1-((1-(cyanomethyl)cyclopropyl)methyl)-4-fluoro-1H-benzo[d]imidazole-6-carboxamide: ES/MS m/z 625.2; Multiplet Report $^1$H NMR (400 MHz, DMSO-d6) δ 8.09 (d, J = 1.2 Hz, 1H), 8.03-7.90 (m, 2H), 7.90-7.67 (m, 6H), 7.55 (dd, J = 11.8, 1.2 Hz, 1H), 7.52-7.43 (m, 2H), 5.71 (s, 2H), 4.51 (s, 2H), 4.45 (s, 2H), 2.70 (s, 2H), 0.79-0.66 (m, 4H). |
| 598 | 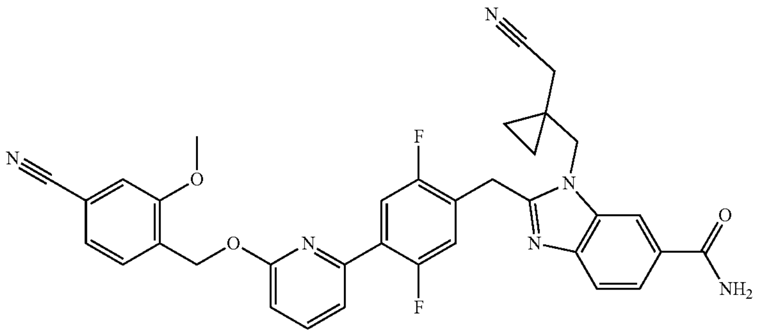 [SMILES: COc1cc(C#N)ccc1COc1cccc(-c2cc(F)c(Cc3nc4ccc(C(N)=O)cc4n3CC3(CC#N)CC3)cc2F)n1] 2-(4-(6-((4-cyano-2-methoxybenzyl)oxy)pyridin-2-yl)-2,5-difluorobenzyl)-1-((1-(cyanomethyl)cyclopropyl)methyl)-1H-benzo[d]imidazole-6-carboxamide: ES/MS 619.2; Multiplet Report $^1$H NMR (400 MHz, DMSO-d6) δ 8.20 (d, J = 1.5 Hz, 1H), 7.94 (s, 1H), 7.92-7.86 (m, 1H), 7.78-7.66 (m, 2H), 7.61-7.48 (m, 5H), 7.48-7.38 (m, 2H), 7.34 (s, 1H), 7.00 (d, J = 8.2 Hz, 1H), 5.51 (s, 2H), 4.51 (s, 2H), 4.44 (s, 2H), 3.92 (s, 3H), 2.71 (s, 2H), 0.79-0.67 (m, 4H). |

Example 589. (R)-2-(4-(6-((4-cyano-2-fluorobenzyl)oxy)pyridin-2-yl)-2,5-difluorobenzyl)-1-((1-(methoxycarbonyl)pyrrolidin-2-yl)methyl)-1H-benzo[d]imidazole-6-carboxylic acid Procedure 79

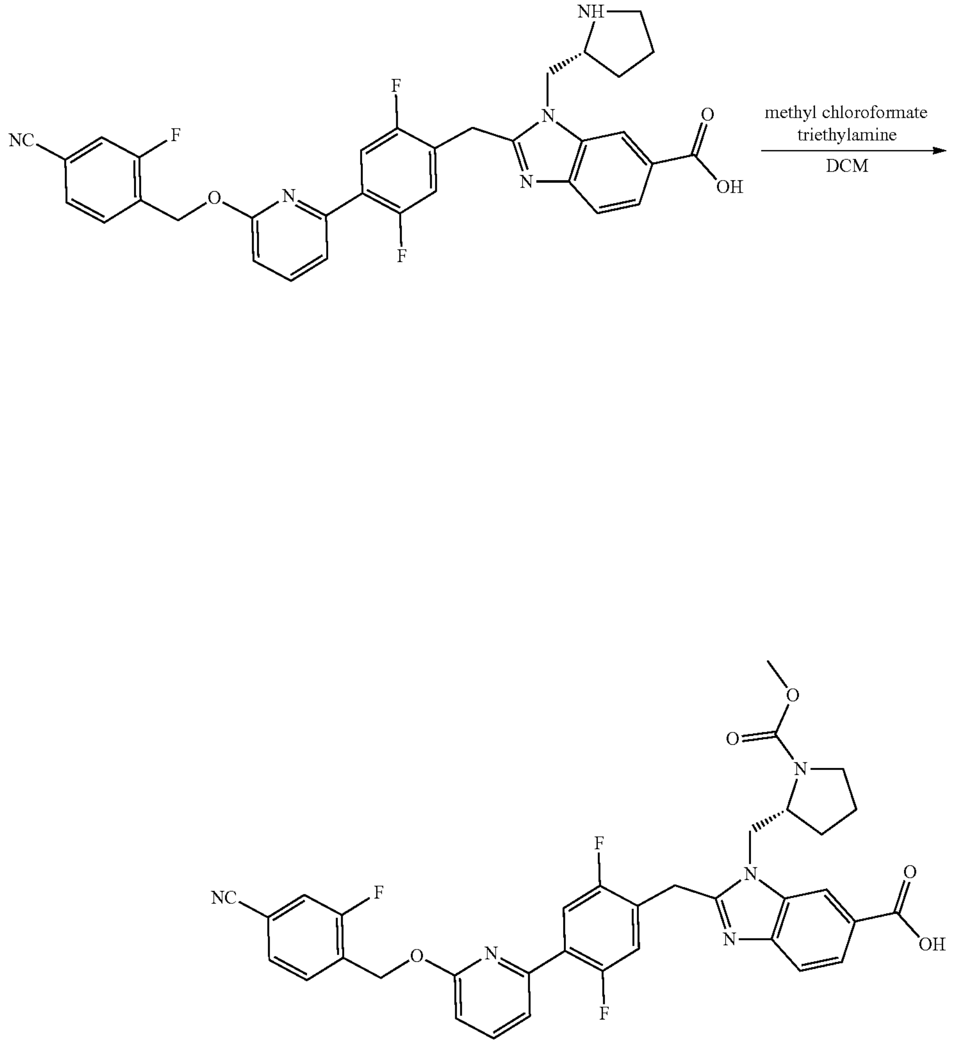

Example 589

(R)-2-(4-(6-((4-cyano-2-fluorobenzyl)oxy)pyridin-2-yl)-2,5-difluorobenzyl)-1-((1-(methoxycarbonyl)pyrrolidin-2-yl)methyl)-1H-benzo[d]imidazole-6-carboxylic acid (Example 589): 2-[[4-[6-[(4-cyano-2-fluoro-phenyl)methoxy]-2-pyridyl]-2,5-difluoro-phenyl]methyl]-3-[[(2R)-pyrrolidin-2-yl]methyl]benzimidazole-5-carboxylic acid (prepared in an analogous manner as described in Procedure 30) (25.0 mg, 0.0303 mmol) was added to DCM (3 mL). Triethylamine (0.0211 mL, 0.151 mmol) followed by methyl chloroformate (0.00936 mL, 0.121 mmol) were added. The mixture was stirred at ambient temperature overnight. The reaction was quenched with excess aq. LiOH (1 M, 1 mL) and the mixture was heated to 40° C. for 2 hours. The mixture was acidified with excess conc. HCl and extracted with EtOAc (3×). The combined organic extracts were washed with brine, dried over sodium sulfate, and filtered and the filtrate was concentrated in vacuo. The crude residue was purified by RP-HPLC (15-54.18% 0.1% TFA-ACN in 0.1% TFA Water, 15 min gradient, Column: Gemini 5 μM, NX-C18 110 Angstrom, 250×21.2 mm) to give the titled product as a lyophilized solid. ES/MS m/z: 656.3 ($M+H^+$). $^1H$ NMR (400 MHz, Methanol-d4) δ 8.43 (d, J=25.1 Hz, 1H), 8.25-7.98 (m, 1H), 7.83 (t, J=7.9 Hz, 1H), 7.73 (dd, J=8.3, 5.5 Hz, 2H), 7.59 (ddd, J=12.5, 8.8, 1.6 Hz, 3H), 6.95 (d, J=8.2 Hz, 1H), 5.63 (s, 2H), 4.59 (dd, J=74.4, 27.9 Hz, 5H), 3.56-3.41 (m, 4H), 3.39 (s, 1H), 3.19-3.05 (m, 1H), 2.26-1.99 (m, 3H), 1.94 (q, J=7.2, 6.8 Hz, 1H).

Example 824. Compounds Prepared Using Procedure 79

Other compounds of the present disclosure prepared using the general route described in Procedure 79 include the following Examples.

| Example | Structure/Name/Characterization |
| --- | --- |
| 824 | 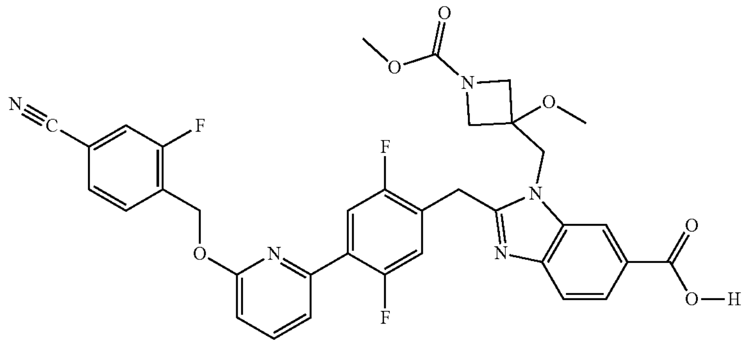 [SMILES: COC(=O)N1CC(Cn2c(Cc3cc(F)c(-c4cccc(OCc5ccc(C#N)cc5F)n4)cc3F)nc3ccc(C(=O)O)cc32)(OC)C1] ES/MS m/z: 672.2; 1H NMR (400 MHz, DMSO-d6) δ 8.48 (d, J = 1.5 Hz, 1H), 7.95-7.87 (m, 2H), 7.84 (dd, J = 8.4, 1.5 Hz, 1H), 7.79-7.69 (m, 3H), 7.62 (d, J = 8.5 Hz, 1H), 7.53 (dd, J = 7.5, 1.7 Hz, 1H), 7.40 (dd, J = 11.5, 6.1 Hz, 1H), 7.00 (d, J = 8.2 Hz, 1H), 5.60 (s, 2H), 4.93 (s, 2H), 4.50 (s, 2H), 4.09 (d, J = 9.8 Hz, 2H), 4.01 (d, J = 9.8 Hz, 2H), 3.62 (s, 3H), 3.37 (s, 3H). |

Example 582. 3-fluoro-4-[[6-[3-fluoro-4-[[1-(2-methoxyethyl)-6-vinyl-benzimidazol-2-yl]methyl]phenyl]-2-pyridyl]oxymethyl]benzonitrile Procedure 80

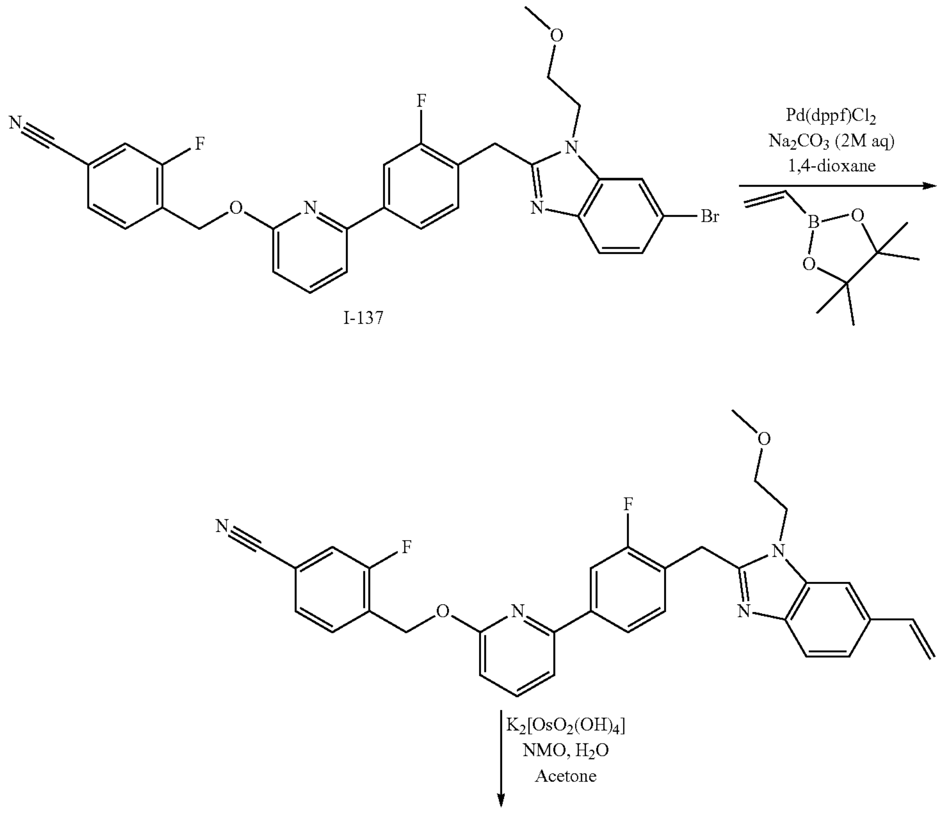

I-137

-continued

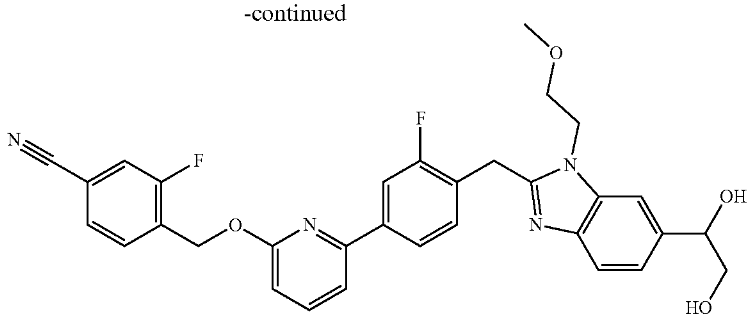

Example 582

3-fluoro-4-[[6-[3-fluoro-4-[[1-(2-methoxyethyl)-6-vinyl-benzimidazol-2-yl]methyl]phenyl]-2-pyridyl]oxymethyl] benzonitrile: 4-[[6-[4-[[6-bromo-1-(2-methoxyethyl)benzimidazol-2-yl]methyl]-3-fluoro-phenyl]-2-pyridyl] oxymethyl]-3-fluoro-benzonitrile (I-137, 50.0 mg, 8.48e-5 mol), 4,4,5,5-tetramethyl-2-vinyl-1,3,2-dioxaborolane (0.0261 g, 0.000170 mol), [1,1'-Bis(diphenylphosphino)ferrocene]dichloropalladium(II) ($PdCl_2$(dppf)) (0.00944 g, 1.27e-5 mol), and sodium carbonate (2.00 M, 0.0848 mL, 0.000170 mol) were combined in a solution of 1,4-dioxane (3.00 mL). Nitrogen was bubbled through the solution for 3 min and the reaction vial was then sealed and heated to 90° C. for 45 min. The mixture was filtered through Celite, eluted with DCM and the filtrate was concentrated in vacuo. The crude residue was purified by column chromatography (0-100% EtOAc in hexane) to give the title compound.

3-fluoro-4-[[6-[3-fluoro-4-[[1-(2-methoxyethyl)-6-vinyl-benzimidazol-2-yl]methyl]phenyl]-2-pyridyl]oxymethyl] benzonitrile (Example 582): 3-fluoro-4-[[6-[3-fluoro-4-[[1-(2-methoxyethyl)-6-vinyl-benzimidazol-2-yl]methyl] phenyl]-2-pyridyl]oxymethyl]benzonitrile (18.6 mg, 0.0347 mmol), potassium osmate (0.0063 g, 0.00173 mol), and N-methylmorpholine N-oxide (6.1 mg, 0.052 mmol) were combined in a solution of water (1.0 mL) and acetone (3.0 mL). The mixture was stirred at room temperature overnight. Upon completion, the reaction mixture was quenched with a concentrated solution of $Na_2SO_3$, extracted with EtOAc and concentrated under vacuum. The crude residue was purified by RP-HPLC (eluent: 10-80% MeCN/$H_2O$) to yield the product (Example 582) as the trifluoroacetate salt and as a racemic mixture. ES/MS: 571.2 ($M+H^+$); $^1$H NMR (400 MHz, DMSO-d6) δ 7.93 (d, J=10.0 Hz, 3H), 7.91-7.84 (m, 2H), 7.79-7.66 (m, 4H), 7.62 (d, J=8.3 Hz, 1H), 7.51 (t, J=8.0 Hz, 1H), 7.45 (d, J=8.6 Hz, 1H), 6.95 (dd, J=8.2, 4.1 Hz, 1H), 5.62 (s, 2H), 4.78-4.39 (m, 4H), 3.70 (t, J=5.1 Hz, 2H), 3.51-3.46 (m, 2H), 3.20 (s, 3H). Isomers of Example 582 are depicted below:

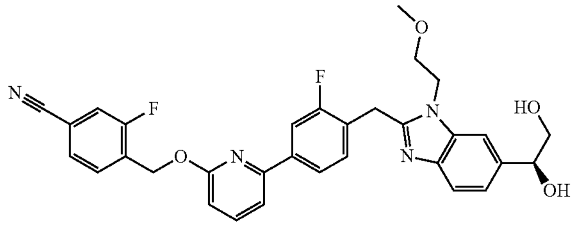

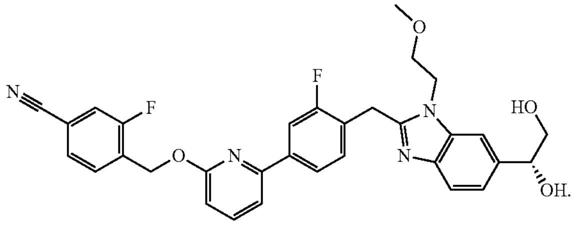

Example 554. 2-(4-(6-((4-carbamoyl-2-fluorobenzyl)oxy)pyridin-2-yl)-2,5-difluorobenzyl)-1-(2-methoxyethyl)-1H-benzo[d]imidazole-6-carboxylic acid Procedure 81

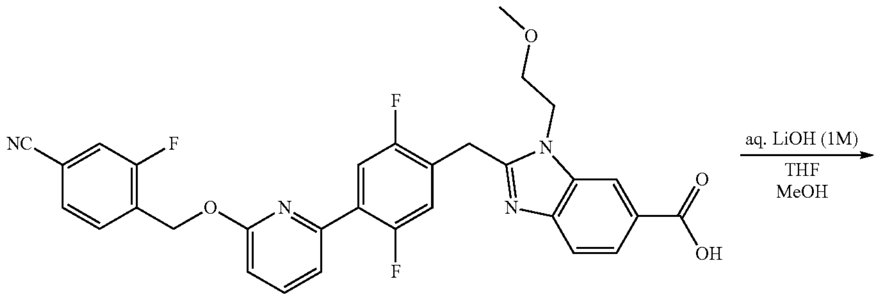

Example 426

-continued

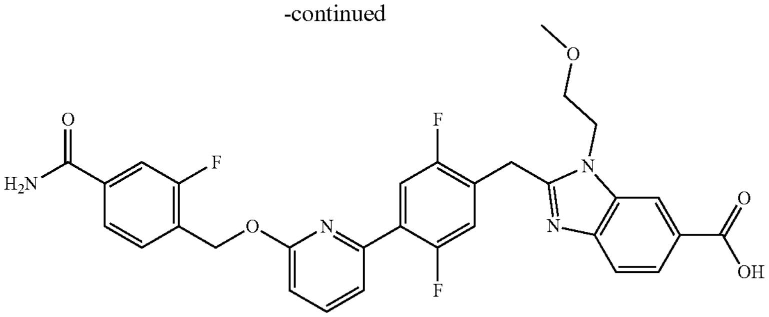

Example 554

2-(4-(6-((4-carbamoyl-2-fluorobenzyl)oxy)pyridin-2-yl)-2,5-difluorobenzyl)-1-(2-methoxyethyl)-1H-benzo[d]imidazole-6-carboxylic acid (Example 554): 2-(4-(6-((4-cyano-2-fluorobenzyl)oxy)pyridin-2-yl)-2,5-difluorobenzyl)-1-(2-methoxyethyl)-1H-benzo[d]imidazole-6-carboxylic acid (Example 426) (8 mg, 0.0136 mmol) was taken up in THF/MeOH solution (3:1, 0.6 mL), and LiOH (1 M in water, 0.035 mL, 0.035 mmol) was added. The solution was heated to 60° C. and stirred for 2 hrs. Following this time, the mixture was diluted with EtOAc (5 mL), the pH adjusted to ~5 with 1 M aqueous citric acid solution and the mixture extracted with EtOAc (3x5 mL). The combined organics were dried over $Na_2SO_4$, concentrated in vacuo, and purified by RP-HPLC (eluent: 0-100% MeCN/water with 0.1% TFA) to yield the product (Example 554) as the trifluoroacetate salt. ES/MS: 591.2 ($M+H^+$); $^1H$ NMR (400 MHz, DMSO-d6) δ 12.83 (s, 1H), 8.23 (d, J=1.5 Hz, 1H), 8.06 (s, 1H), 7.89 (t, J=7.9 Hz, 1H), 7.85-7.78 (m, 2H), 7.77-7.69 (m, 2H), 7.64 (dd, J=14.6, 8.0 Hz, 2H), 7.58-7.48 (m, 2H), 7.39 (dd, J=11.5, 6.1 Hz, 1H), 6.97 (d, J=8.2 Hz, 1H), 5.57 (s, 2H), 4.61 (t, J=5.1 Hz, 2H), 4.47 (s, 2H), 3.69 (t, J=5.1 Hz, 2H), 3.21 (s, 3H).

Examples 825-826. Compounds Prepared Using Procedure 81

Other compounds of the present disclosure prepared using the general route described in Procedure 81 include the following Examples.

| Example | Structure/Name/Characterization |
|---|---|
| 825 | 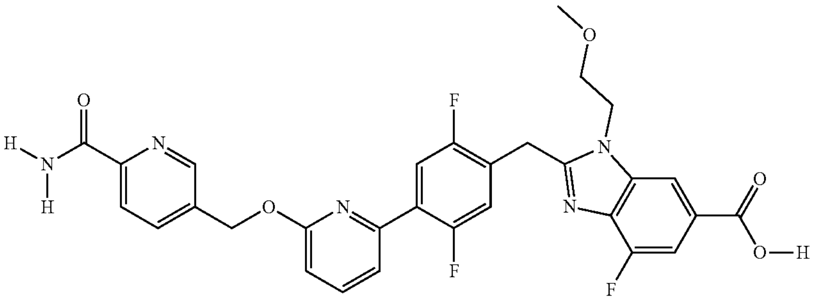 [SMILES: COCCn1c(Cc2cc(F)c(-c3cccc(OCc4ccc(C(N)=O)nc4)n3)cc2F)nc2c(F)cc(C(=O)O)cc21]<br>ES/MS m/z: 592.34; 1H NMR (400 MHz, DMSO-d6) δ 8.77 (d, J = 2.0 Hz, 1H), 8.22-8.00 (m, 4H), 7.98-7.73 (m, 2H), 7.63 (s, 1H), 7.59-7.47 (m, 2H), 7.39 (dd, J = 11.5, 6.1 Hz, 1H), 6.99 (d, J = 8.2 Hz, 1H), 5.61 (s, 2H), 4.62 (t, J = 5.1 Hz, 2H), 4.46 (s, 2H), 3.72-3.58 (m, 3H), 3.21 (s, 3H). |
| 826 | 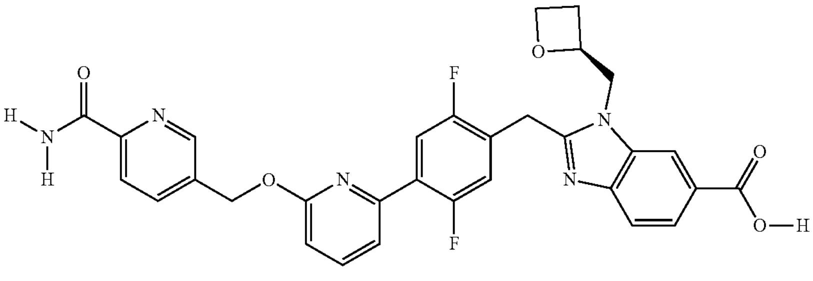 [SMILES: NC(=O)c1ccc(COc2cccc(-c3cc(F)c(Cc4nc5ccc(C(=O)O)cc5n4C[C@@H]4CCO4)cc3F)n2)cn1]<br>ES/MS m/z: 586.4; 1H NMR (400 MHz, Methanol-d4) δ 8.84-8.68 (m, 1H), 8.62-8.52 (m, 1H), 8.26-8.16 (m, 1H), 8.16-8.01 (m, 2H), 7.96-7.70 (m, 3H), 7.58 (dd, J = 7.4, 1.7 Hz, 1H), 7.37 (dd, J = 11.2, 6.0 Hz, 1H), 6.97 (d, J = 8.2 Hz, 1H), 5.64 (s, 2H), 5.26 (tt, J = 7.5, 3.9 Hz, 1H), 4.98 (dd, J = 15.5, 7.5 Hz, 1H), 4.84-4.65 (m, 3H), 4.54 (dt, J = 9.2, 5.9 Hz, 1H), 2.95-2.79 (m, 1H), 2.70-2.49 (m, 1H) |

Example 555. (2-(4-(6-((4-cyano-2-fluorobenzyl)oxy)pyridin-2-yl)-2-fluorobenzyl)-1-(2-methoxyethyl)-1H-benzo[d]imidazol-6-yl)phosphonic Acid Procedure 82

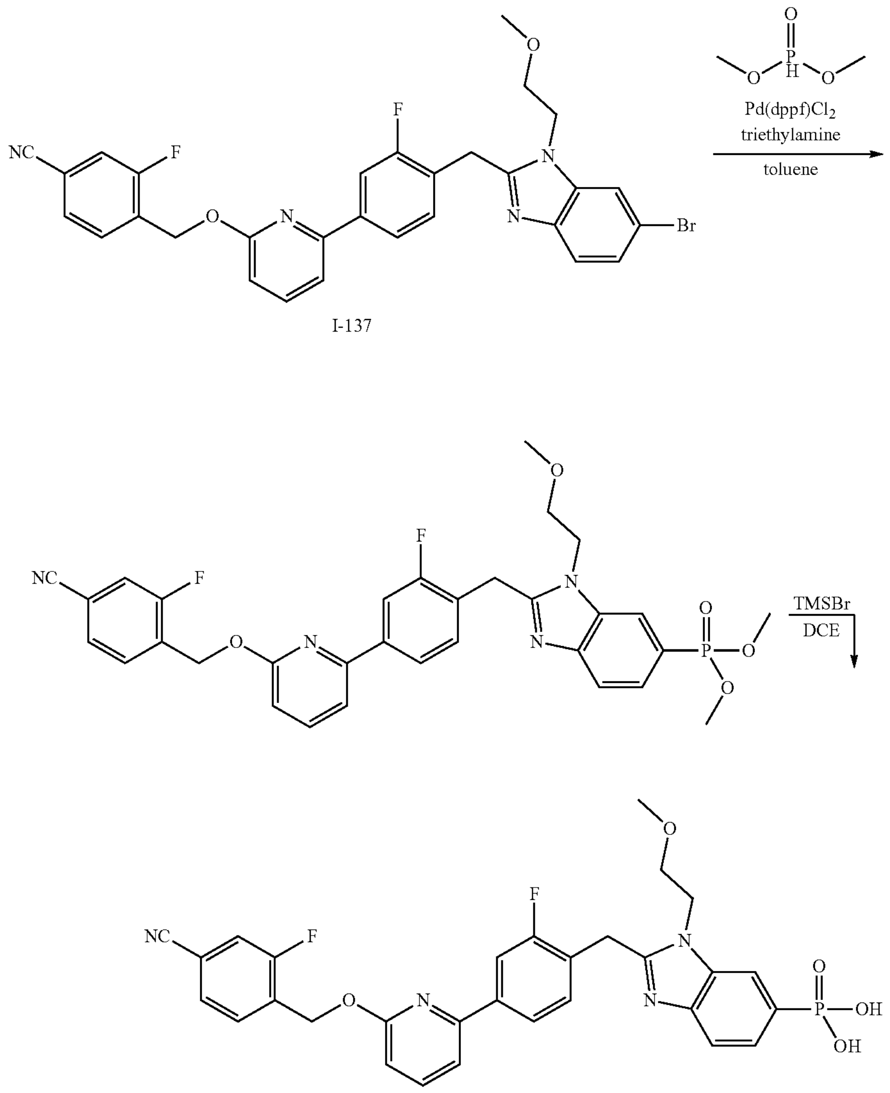

I-137

Example 555

Dimethyl (2-(4-(6-((4-cyano-2-fluorobenzyl)oxy)pyridin-2-yl)-2-fluorobenzyl)-1-(2-methoxyethyl)-1H-benzo[d]imidazol-6-yl)phosphonate: A suspension of 4-(((6-(4-((6-bromo-1-(2-methoxyethyl)-1H-benzo[d]imidazol-2-yl)methyl)-3-fluorophenyl)pyridin-2-yl)oxy)methyl)-3-fluorobenzonitrile (I-137, 40 mg, 0.068 mmol), dimethyl phosphite (22 mg, 0.22 mmol), triethylamine (0.045 mL, 0.34 mmol), and [1,1'-bis(diphenylphosphino)ferrocene]dichloropalladium(II) (5 mg, 0.0068 mmol) in toluene (2.0 mL) was degassed by bubbling argon for 30 seconds, then heated in a sealed tube at 85° C. for 2 hrs. Following this time, the crude mixture was loaded directly onto silica gel and purified by silica gel chromatography (eluent: EtOAc in hexanes). ES/MS: 619.2 ($M+H^+$).

(2-(4-(6-((4-cyano-2-fluorobenzyl)oxy)pyridin-2-yl)-2-fluorobenzyl)-1-(2-methoxyethyl)-1H-benzo[d]imidazol-6-yl)phosphonic acid (Example 555): Dimethyl (2-(4-(6-((4-cyano-2-fluorobenzyl)oxy)pyridin-2-yl)-2-fluorobenzyl)-1-(2-methoxyethyl)-1H-benzo[d]imidazol-6-yl)phosphonate (26 mg, 0.025 mmol) was taken up in DCE (0.4 mL) and bromotrimethylsilane (0.056 mL, 0.42 mmol) was added. The mixture was stirred at RT for 2 hrs. Following this time, MeOH (1.0 mL) was added and the solution was concentrated in vacuo. The mixture was then purified by RP-HPLC (eluent: 0-60% MeCN/water with 0.1% TFA) to yield the product (Example 555) as the trifluoroacetate salt. ES/MS: 591.2 ($M+H^+$); $^1$H NMR (400 MHz, Methanol-d4) δ 8.23 (d, J=14.1 Hz, 1H), 7.92 (dt, J=18.9, 10.0 Hz, 3H), 7.82 (t, J=7.9 Hz, 1H), 7.79-7.71 (m, 2H), 7.62 (d, J=10.2 Hz, 1H), 7.58 (d, J=7.6 Hz, 2H), 7.49 (t, J=7.9 Hz, 1H), 6.92 (d, J=8.2 Hz, 1H), 5.66 (s, 2H), 4.80-4.69 (m, 4H), 3.81 (t, J=4.9 Hz, 2H), 3.30 (s, 3H).

Example 556. Diethyl (2-(4-(6-((4-cyano-2-fluorobenzyl)oxy)pyridin-2-yl)-2-fluorobenzyl)-1-(2-methoxyethyl)-1H-benzo[d]imidazol-6-yl)phosphonate Procedure 83

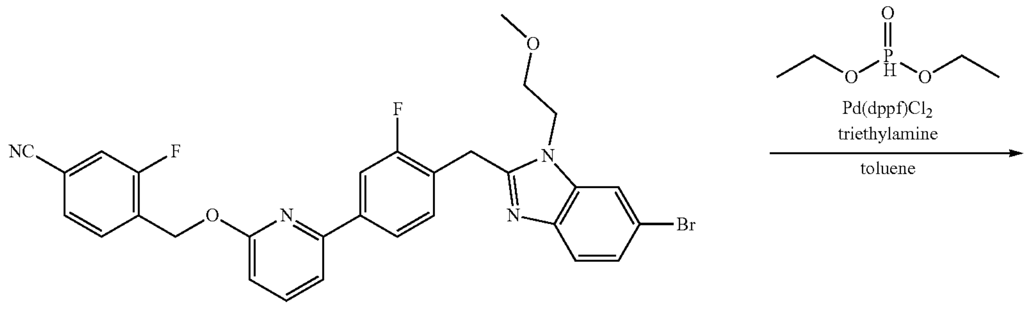

I-137

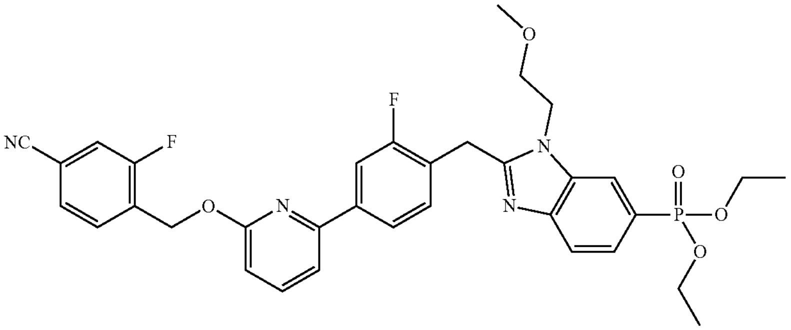

Example 556

Diethyl (2-(4-(6-((4-cyano-2-fluorobenzyl)oxy)pyridin-2-yl)-2-fluorobenzyl)-1-(2-methoxyethyl)-1H-benzo[d]imidazol-6-yl)phosphonate (Example 556): A suspension of 4-(((6-(4-((6-bromo-1-(2-methoxyethyl)-1H-benzo[d]imidazol-2-yl)methyl)-3-fluorophenyl)pyridin-2-yl)oxy)methyl)-3-fluorobenzonitrile (I-137, 30 mg, 0.051 mmol), diethyl phosphite (21 mg, 0.15 mmol), triethylamine (0.034 mL, 0.25 mmol), and [1,1'-bis(diphenylphosphino)ferrocene]dichloropalladium(II) (4 mg, 0.0051 mmol) in toluene (2.0 mL) was degassed by bubbling argon for 30 seconds, then heated in a sealed tube at 85° C. for 2 hrs. Following this time, the crude mixture was loaded directly onto silica gel and purified by silica gel chromatography (eluent: EtOAc in hexanes). The product was subsequently purified by RP-HPLC (eluent: 0-100% MeCN/water with 0.1% TFA) to yield the product (Example 556) as the trifluoroacetate salt. ES/MS: 647.2 (M+$H^+$); $^1$H NMR (400 MHz, Methanol-d4) δ 8.28 (dt, J=14.7, 1.0 Hz, 1H), 7.94-7.84 (m, 4H), 7.82 (dd, J=8.2, 7.5 Hz, 1H), 7.73 (t, J=7.5 Hz, 1H), 7.61 (dd, J=9.7, 1.5 Hz, 1H), 7.59-7.53 (m, 2H), 7.48 (t, J=7.9 Hz, 1H), 6.94-6.89 (m, 1H), 5.65 (s, 2H), 4.77 (t, J=4.9 Hz, 2H), 4.73 (s, 2H), 4.28-4.09 (m, 4H), 3.86-3.74 (m, 2H), 3.30 (s, 3H), 1.37 (t, J=7.0 Hz, 6H).

Example 562. Diethyl (2-(4-(6-((4-cyano-2-fluorobenzyl)oxy)pyridin-2-yl)-2-fluorobenzyl)-1-(2-methoxyethyl)-1H-benzo[d]imidazol-6-yl)phosphonate Procedure 84

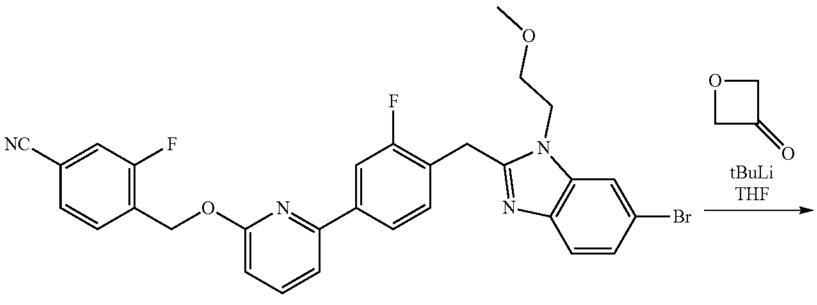

I-137

-continued

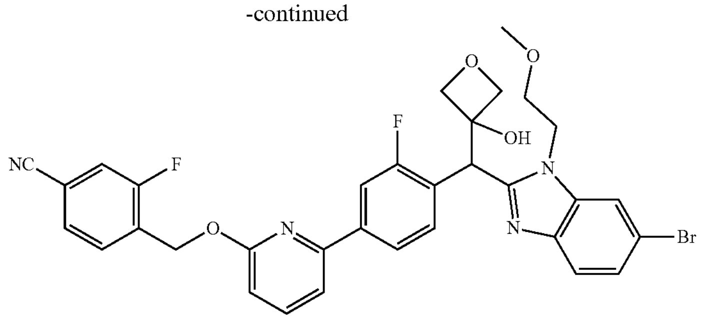

Example 562

Diethyl (2-(4-(6-((4-cyano-2-fluorobenzyl)oxy)pyridin-2-yl)-2-fluorobenzyl)-1-(2-methoxyethyl)-1H-benzo[d]imidazol-6-yl)phosphonate (Example 562): To a solution of 4-(((6-(4-((6-bromo-1-(2-methoxyethyl)-1H-benzo[d]imidazol-2-yl)methyl)-3-fluorophenyl)pyridin-2-yl)oxy)methyl)-3-fluorobenzonitrile (I-137, 50 mg, 0.085 mmol) in THF (1.0 mL) at −78° C. was added t-BuLi (1.4 M, 0.12 mL, 0.17 mmol). The resulting solution was stirred at −78° C. for 90 minutes before addition of oxetan-3-one (12 mg, 0.17 mmol). The mixture was slowly warmed to 0° C. and quenched with saturated aqueous. $NH_4Cl$ (1 mL) and diluted with EtOAc (2 mL). The organic phase was collected and the aqueous phase extracted with EtOAc (2×5 mL). The combined organic phases were washed with brine (20 mL), dried over $Na_2SO_4$, and concentrated in vacuo. The crude material was purified by silica gel chromatography (eluent: EtOAc in hexanes) to yield the product (Example 562) as a racemic mixture. ES/MS: 663.0 ($M+H^+$); $^1H$ NMR (400 MHz, Chloroform-d) δ 7.79 (dd, J=11.5, 1.7 Hz, 1H), 7.73-7.69 (m, 1H), 7.68-7.65 (m, 1H), 7.65-7.60 (m, 2H), 7.51 (d, J=1.8 Hz, 1H), 7.48 (dd, J=7.9, 1.6 Hz, 1H), 7.43 (ddd, J=9.3, 4.4, 1.7 Hz, 2H), 7.40-7.32 (m, 2H), 6.83 (d, J=8.1 Hz, 1H), 5.71-5.51 (m, 3H), 4.82 (d, J=6.5 Hz, 1H), 4.60 (s, 2H), 4.48 (d, J=6.4 Hz, 1H), 4.22 (ddd, J=15.2, 8.9, 4.2 Hz, 1H), 4.10 (dt, J=15.2, 3.6 Hz, 1H), 3.56 (qd, J=10.1, 4.7 Hz, 2H), 3.28 (s, 3H).

Isomers of Example 562 are depicted below:

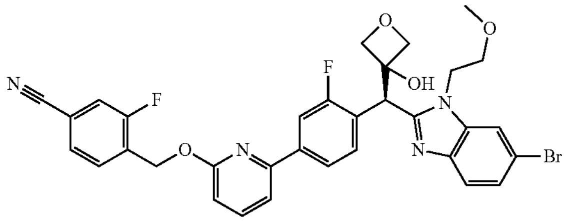

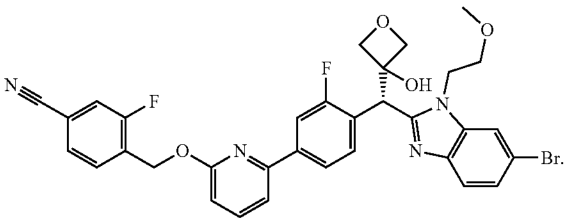

Example 552. 2-(4-(6-((4-Cyano-2-fluorobenzyl)oxy)pyridin-2-yl)-2-fluorobenzyl)-1-((1-(fluoromethyl)cyclopropyl)methyl)-1H-benzo[d]imidazole-5-carboxylic acid Procedure 85

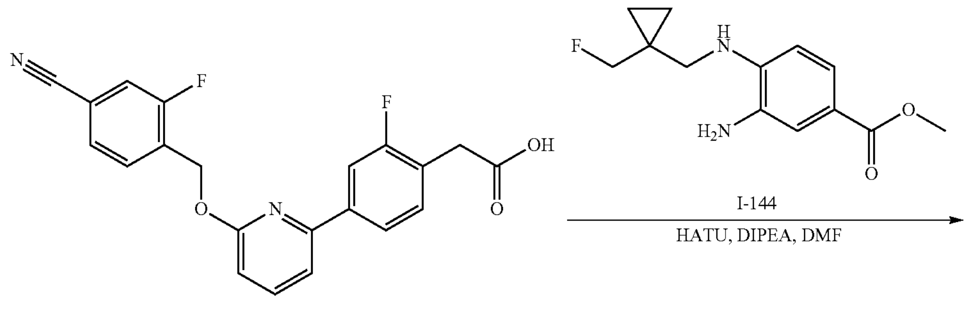

I-128

-continued

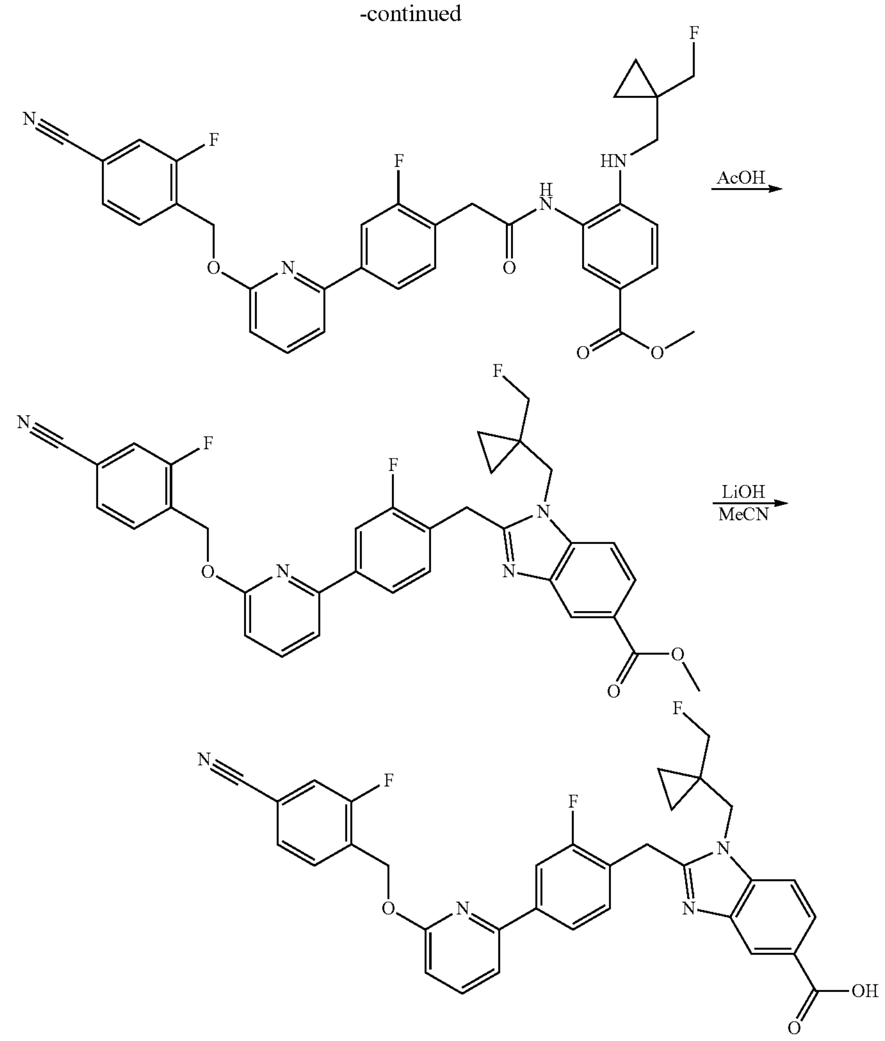

Example 552

Step 1. Methyl 3-(2-(4-(6-((4-cyano-2-fluorobenzyl)oxy)pyridin-2-yl)-2-fluorophenyl)acetamido)-4-(((1-(fluoromethyl)cyclopropyl)methyl)amino)benzoate. To a solution of 2-(4-(6-((4-cyano-2-fluorobenzyl)oxy)pyridin-2-yl)-2-fluorophenyl)acetic acid (I-128, 50 mg, 0.13 mmol), methyl 3-amino-4-(((1-(fluoromethyl)cyclopropyl)methyl)amino)benzoate (I-144, 87 mg, 0.35 mmol), in DMF (1.5 mL) was added o-(7-azabenzotriazol-1-yl)-N,N,N',N'-tetramethyluronium hexafluorophosphate (HATU, 75.0 mg, 0.197 mmol) and DIPEA (0.125 mL, 0.72 mmol). The resulting solution was stirred at room temperature for 18 hours. The solution was then diluted with EtOAc and washed with HCl (aqueous, 1 M, 2×). The aqueous layers were back-extracted with EtOAc and the combined organic layers were dried over magnesium sulfate and concentrated to dryness. The crude material was purified by RP-HPLC (eluent: 10-100% water/MeCN/0.1% TFA) and the desired fractions were concentrated, diluted with $CH_2Cl_2$ and washed with aqueous sodium bicarbonate. The organic layers were dried over magnesium sulfate and concentrated to provide methyl 3-(2-(4-(6-((4-cyano-2-fluorobenzyl)oxy)pyridin-2-yl)-2-fluorophenyl)acetamido)-4-(((1-(fluoromethyl)cyclopropyl)methyl)amino)benzoate. ES/MS: 615.127 ($M+H^+$).

Step 2. Methyl 2-(4-(6-((4-cyano-2-fluorobenzyl)oxy)pyridin-2-yl)-2-fluorobenzyl)-1-((1-(fluoromethyl)cyclopropyl)methyl)-1H-benzo[d]imidazole-5-carboxylate. A solution of methyl 3-(2-(4-(6-((4-cyano-2-fluorobenzyl)oxy)pyridin-2-yl)-2-fluorophenyl)acetamido)-4-(((1-(fluoromethyl)cyclopropyl)methyl)amino)benzoate (80 mg, 0.13 mmol) in acetic acid (1.75 mL) was heated to 70° C. for 72 h. The resulting solution was cooled to room temperature and concentrated to dryness. The residue was dissolved in $CH_2Cl_2$ and washed with aqueous bicarbonate. The aqueous layer was back-extracted with $CH_2Cl_2$ and the combined organic layers were dried over magnesium sulfate and concentrated to dryness to provide methyl 2-(4-(6-((4-cyano-2-fluorobenzyl)oxy)pyridin-2-yl)-2-fluorobenzyl)-1-((1-(fluoromethyl)cyclopropyl)methyl)-1H-benzo[d]imidazole-5-carboxylate, which was used directly in the next step. ES/MS: 597.350 ($M+H^+$).

Step 3. 2-(4-(6-((4-cyano-2-fluorobenzyl)oxy)pyridin-2-yl)-2-fluorobenzyl)-1-((1-(fluoromethyl)cyclopropyl)methyl)-1H-benzo[d]imidazole-5-carboxylic acid (Example 552). To a solution of methyl 2-(4-(6-((4-cyano-2-fluorobenzyl)oxy)pyridin-2-yl)-2-fluorobenzyl)-1-((1-(fluoromethyl)cyclopropyl)methyl)-1H-benzo[d]imidazole-5-carboxylate (40 mg, 0.07 mmol) in MeCN (1.5 mL) was added $H_2O$ (0.2 mL) and lithium hydroxide (1 M, aqueous, 0.2 mL, 0.2 mmol). The resulting reaction vessel was sealed and heated to 100° C. for 15 min. The solution was cooled to room temperature, acidified with trifluoroacetic acid (1 drop) and concentrated. The resulting material was diluted with DMF and purified by RP-HPLC (eluent: 10-65% water/MeCN/0.1% TFA). The resulting fractions were lyophilized to provide 2-(4-(6-((4-cyano-2-fluorobenzyl)oxy)pyridin-2-yl)-2-fluorobenzyl)-1-((1-(fluoromethyl)cyclopropyl)methyl)-1H-benzo[d]imidazole-5-carboxylic acid (Example 552). ES/MS: 583.278 ($M+H^+$); $^1H$ NMR (400

MHz, DMSO) δ 8.11 (d, J=1.5 Hz, 1H), 7.97-7.83 (m, 5H), 7.82-7.63 (m, 4H), 7.43 (t, J=7.9 Hz, 1H), 6.93 (d, J=8.2 Hz, 1H), 5.62 (s, 2H), 4.49 (s, 2H), 4.43 (s, 2H), 4.18 (d, J=48.7 Hz, 2H), 0.82 (t, J=5.2 Hz, 2H), 0.71 (d, J=5.0 Hz, 2H).

Example 553 and 827-840. Compounds Prepared Using Procedure 85

Other compounds of the present disclosure prepared using the general route described in Procedure 85 include the following Examples.

| Example | Structure/Name/Characterization |
|---|---|
| 553 | 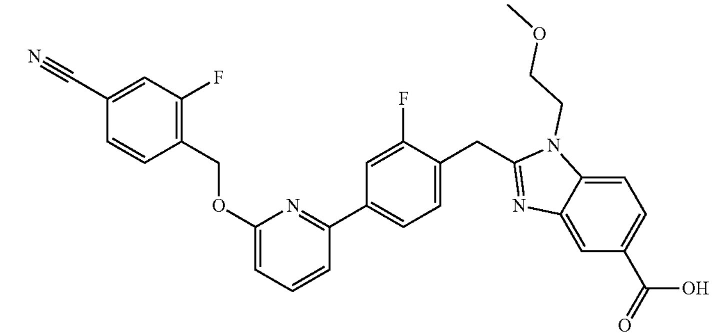 [SMILES: COCCn1c(Cc2ccc(-c3cccc(OCc4ccc(C#N)cc4F)n3)cc2F)nc2cc(C(=O)O)ccc21]<br>2-(4-(6-((4-cyano-2-fluorobenzyl)oxy)pyridin-2-yl)-2-fluorobenzyl)-1-(2-methoxyethyl)-1H-benzo[d]imidazole-5-carboxylic acid: ES/MS m/z 555.5; $^1H$ NMR (400 MHz, DMSO) δ 8.13 (d, J = 1.5 Hz, 1H), 7.96-7.82 (m, 5H), 7.81-7.64 (m, 4H), 7.43 (t, J = 8.1 Hz, 1H), 6.94 (d, J = 8.1 Hz, 1H), 5.62 (s, 2H), 4.54 (t, J = 5.2 Hz, 2H), 4.46 (s, 2H), 3.65 (t, J = 5.1 Hz, 2H), 3.20 (s, 3H). |
| 827 | ES/MS m/z 641; Multiplet Report<br>1H NMR (400 MHz, DMSO-d6) δ 8.28 (d, J = 1.4 Hz, 1H), 7.96-7.86 (m, 2H), 7.84 (dd, J = 8.4, 1.5 Hz, 1H), 7.81-7.70 (m, 3H), 7.63 (d, J = 8.5 Hz, 1H), 7.53 (dd, J = 7.6, 1.7 Hz, 1H), 7.37 (dd, J = 11.5, 6.1 Hz, 1H), 7.00 (d, J = 8.3 Hz, 1H), 5.61 (s, 2H), 4.68 (t, J = 5.1 Hz, 2H), 4.48 (s, 2H), 4.07 (q, J = 9.3 Hz, 2H), 3.97 (t, J = 5.0 Hz, 2H). |
| 828 | 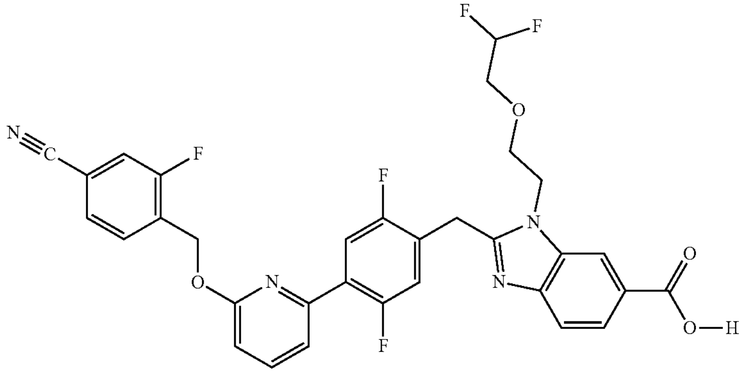 [SMILES: N#Cc1ccc(COc2cccc(-c3cc(F)c(Cc4nc5ccc(C(=O)O)cc5n4CCOCC(F)F)cc3F)n2)c(F)c1]<br>ES/MS m/z 623.2; (Multiplet Report) 1H NMR (400 MHz, DMS0-d6) δ 8.26 (d, J = 1.4 Hz, 1H), 7.96-7.86 (m, 2H), 7.82 (dd, J = 8.4, 1.6 Hz, 1H), 7.81-7.70 (m, 3H), 7.62 (d, J = 8.4 Hz, 1H), 7.53 (dd, J = 7.6, 1.7 Hz, 1H), 7.37 (dd, J = 11.4, 6.1 Hz, 1H), 7.00 (d, J = 8.3 Hz, 1H), 6.06 (tt, J = 56, 5.0 Hz, 1H), 5.61 (s, 2H), 4.65 (d, J = 5.2 Hz, 2H), 4.48 (s, 2H), 3.90 (t, J = 5.0 Hz, 2H), 3.68 (td, J = 15.3, 3.6 Hz, 2H). |

-continued

| Example | Structure/Name/Characterization |
|---|---|
| 829 | 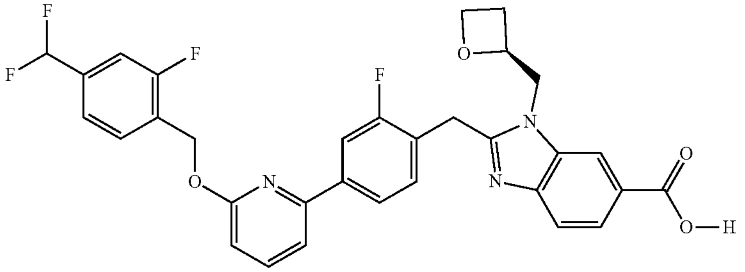 [SMILES: O=C(O)c1ccc2nc(Cc3ccc(-c4cccc(OCc5ccc(C(F)F)cc5F)n4)cc3F)n(C[C@@H]3CCO3)c2c1] |
| | ES/MS m/z 592.2; (Multiplet Report) 1H NMR (400 MHz, DMSO-d6) δ 12.76 (br s, 1H), 8.25 (d, J = 1.5 Hz, 1H), 7.94-7.81 (m, 3H), 7.83-7.69 (m, 2H), 7.66 (d, J = 7.5 Hz, 1H), 7.59 (d, J = 8.4 Hz, 1H), 7.56-7.39 (m, 3H), 7.05 (s, 1H), 6.94-6.87 (m, 1H), 5.60 (s, 2H), 5.05 (d, J = 7.5 Hz, 1H), 4.73 (dd, J = 15.5, 7.0 Hz, 1H), 4.60 (d, J = 14.4 Hz, 1H), 4.57-4.45 (m, 2H), 4.43 (t, J = 16.7 Hz, 1H), 4.36 (m, 1H), 2.70 (s, 1H), 2.38 (s, 1H), 1.3-1.1 (m, 5H). |
| 830 | 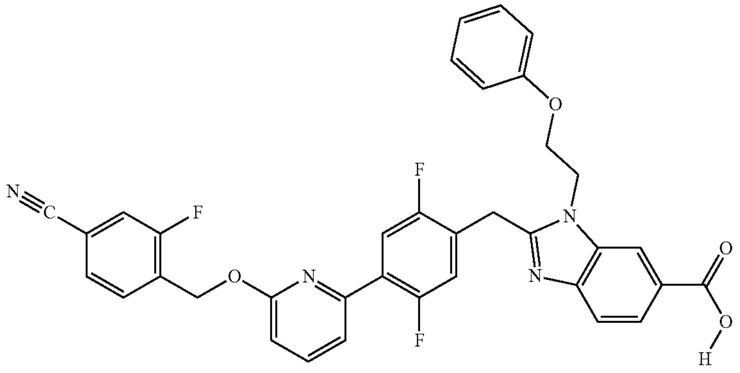 [SMILES: N#Cc1ccc(COc2cccc(-c3cc(F)c(Cc4nc5ccc(C(=O)O)cc5n4CCOc4ccccc4)cc3F)n2)c(F)c1] |
| | ES/MS m/z 635.2; 1H NMR (400 MHz, DMSO-d6) δ 8.37 (d, J = 1.5 Hz, 1H), 7.96-7.87 (m, 2H), 7.86-7.71 (m, 4H), 7.62 (d, J = 8.5 Hz, 1H), 7.53 (dd, J = 7.5, 1.7 Hz, 1H), 7.43 (dd, J = 11.5, 6.1 Hz, 1H), 7.28-7.20 (m, 2H), 7.00 (d, J = 8.3 Hz, 1H), 6.91 (t, J = 7.3 Hz, 1H), 6.85 (dd, J = 7.5, 1.6 Hz, 2H), 5.61 (s, 2H), 4.91-4.82 (m, 2H), 4.57 (s, 2H), 4.35 (t, J = 4.9 Hz, 2H), 19F NMR (376 MHz, DMSO-d6) δ −115.90 (dd, J = 10.0, 6.5 Hz), −121.95, −122.17-−122.47 (m). |
| 831 | 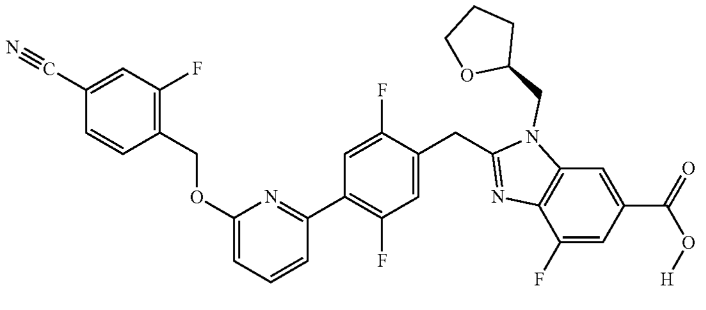 [SMILES: N#Cc1ccc(COc2cccc(-c3cc(F)c(Cc4nc5c(F)cc(C(=O)O)cc5n4C[C@@H]4CCCO4)cc3F)n2)c(F)c1] |
| | ES/MS m/z 617.2; 1H NMR (400 MHz, DMSO-d6) δ 8.12 (d, J = 1.3 Hz, 1H), 8.00-7.87 (m, 2H), 7.82-7.70 (m, 3H), 7.59-7.46 (m, 2H), 7.40 (dd, J = 11.5, 6.1 Hz, 1H), 6.99 (d, J = 8.3 Hz, 1H), 5.61 (s, 2H), 4.67-4.36 (m, 4H), 4.17 (qd, J = 7.1, 2.7 Hz, 1H), 2.16-2.03 (m, 1H), 1.93-1.78 (m, 2H), 1.70-1.55 (m, 1H). (Multiplet Report) 19F NMR (376 MHz, DMSO-d6) δ −115.89 (dd, J = 10.0, 6.4 Hz), −121.86 (ddd, J = 18.0, 10.9, 6.3 Hz), −122.42 (ddd, J = 17.3, 10.5, 6.0 Hz), −129.63 (d, J = 11.2 Hz). |

-continued

| Example | Structure/Name/Characterization |
| --- | --- |
| 832 | 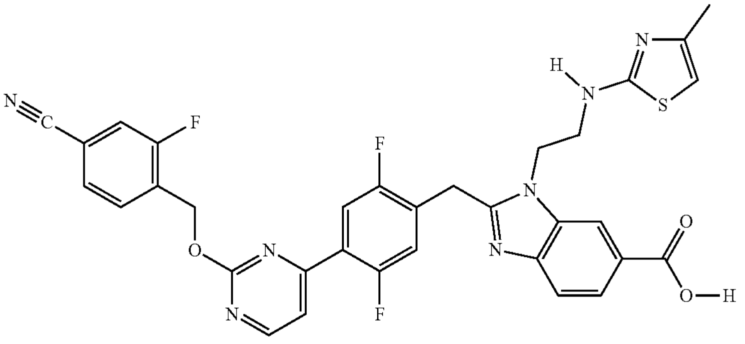 [SMILES: Cc1csc(NCCn2c(Cc3cc(F)c(-c4ccnc(OCc5ccc(C#N)cc5F)n4)cc3F)nc3ccc(C(=O)O)cc32)n1] ES/MS m/z 656.2; 1H NMR (400 MHz, Acetonitrile-d3) δ 10.95 (s, 1H), 8.69 (d, J = 5.2 Hz, 1H), 8.41 (s, 1H), 8.13 (d, J = 8.5 Hz, 1H), 7.94 (dd, J = 10.5, 6.2 Hz, 1H), 7.86 (d, J = 8.6 Hz, 1H), 7.75 (t, J = 7.6 Hz, 1H), 7.67-7.54 (m, 3H), 7.38 (dd, J = 11.2, 5.5 Hz, 1H), 7.15 (t, J = 47.3 Hz, 6H), 6.23 (d, J = 1.5 Hz, 1H), 5.64 (s, 2H), 4.74 (t, J = 5.5 Hz, 2H), 4.68 (s, 2H), 3.86 (d, J = 6.1 Hz, 3H), 2.10 (d, J = 1.2 Hz, 3H). 19F NMR (377 MHz, Acetonitrile-d3) δ  −117.18-−117.38 (m), −119.76 (ddd, J = 17.7, 11.2, 6.4 Hz), −122.34 (dt, J = 17.6, 7.5 Hz). |
| 833 | 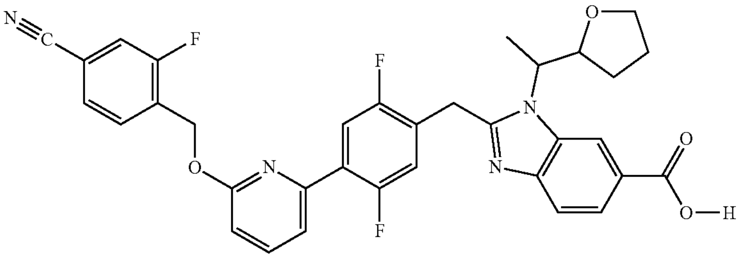 [SMILES: CC(C1CCCO1)n1c(Cc2cc(F)c(-c3cccc(OCc4ccc(C#N)cc4F)n3)cc2F)nc2ccc(C(=O)O)cc21] ES/MS m/z 613.2; 1H NMR (400 MHz, Acetonitrile-d3) δ 8.54 (s, 1H), 8.00 (dd, J = 8.5, 1.5 Hz, 1H), 7.89-7.68 (m, 4H), 7.64-7.50 (m, 3H), 7.26 (dd, J = 11.5, 6.1 Hz, 1H), 6.93 (dd, J = 8.3, 0.7 Hz, 1H), 5.62 (s, 3H), 4.72 (d, J = 7.2 Hz, 1H), 4.57 (s, 2H), 4.33 (q, J = 6.4 Hz, 1H), 3.93 (dt, J = 8.2, 6.7 Hz, 1H), 3.87-3.74 (m, 1H), 1.91-1.81 (m, 2H), 1.67 (d, J = 7.0 Hz, 3H). (Multiplet Report) 19F NMR (377 MHz, Acetonitrile-d3) δ , −117.43-−117.67 (m), −122.20, −123.80 (ddd, J = 17.6, 10.7, 6.1 Hz). |
| 834 | 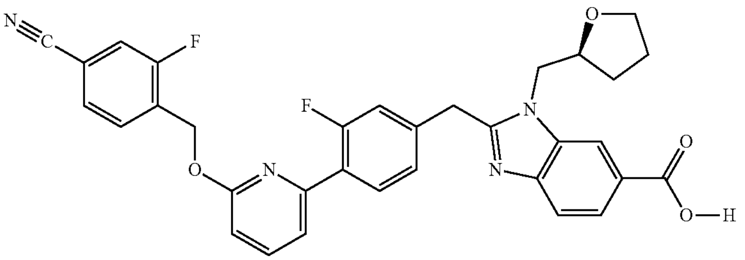 [SMILES: N#Cc1ccc(COc2cccc(-c3ccc(Cc4nc5ccc(C(=O)O)cc5n4C[C@@H]4CCCO4)cc3F)n2)c(F)c1] ES/MS m/z 581.2; 1H NMR (400 MHz, Acetonitrile-d3) δ 8.50 (d, J = 1.3 Hz, 1H), 8.16 (dd, J = 8.6, 1.4 Hz, 1H), 8.00 (t, J = 8.1 Hz, 1H), 7.89-7.77 (m, 2H), 7.71 (t, J = 7.7 Hz, 1H), 7.63-7.54 (m, 2H), 7.49 (dd, J = 7.5, 1.9 Hz, 1H), 7.36-7.24 (m, 2H), 6.90 (d, J = 8.2 Hz, 1H), 5.59 (s, 2H), 4.80-4.57 (m, 3H), 4.43 (dd, J = 15.1, 8.9 Hz, 1H), 4.30-4.09 (m, 1H), 3.96-3.81 (m, 1H), 3.70 (td, J = 7.8, 6.0 Hz, 2H), 2.19 (dtd, J = 12.5, 7.4, 5.2 Hz, 1H), 1.71 (dq, J = 12.4, 7.6 Hz, 1H). (Multiplet Report) 19F NMR (377 MHz, Acetonitrile-d3) δ  −116.51-−116.72 (m), −117.57 (dd, J = 9.8, 7.3 Hz). |

-continued

| Example | Structure/Name/Characterization |
| --- | --- |
| 835 | 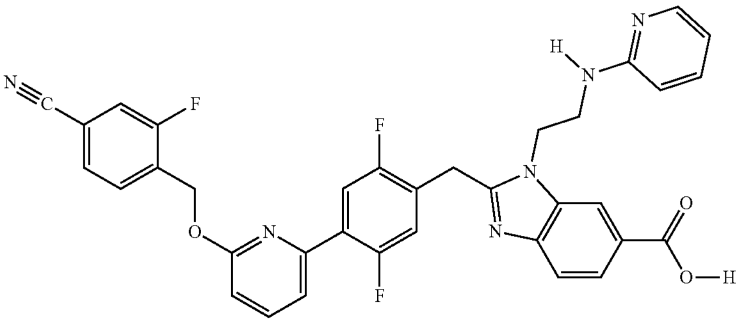 [SMILES: N#Cc1ccc(COc2cccc(-c3cc(F)c(Cc4nc5ccc(C(=O)O)cc5n4CCNc4ccccn4)cc3F)n2)c(F)c1] ES/MS m/z 635.2; 1H NMR (400 MHz, Acetonitrile-d3) δ 8.23 (d, J = 1.5 Hz, 1H), 7.93 (dd, J = 8.5, 1.6 Hz, 1H), 7.82 (t, J = 7.9 Hz, 1H), 7.78-7.67 (m, 3H), 7.65 (d, J = 8.6 Hz, 1H), 7.61-7.51 (m, 3H), 7.20 (dd, J = 11.5, 6.1 Hz, 1H), 6.92 (d, J = 8.2 Hz, 1H), 6.73 (t, J = 6.6 Hz, 1H), 6.59 (d, J = 9.1 Hz, 1H), 5.63 (s, 2H), 4.60 (t, J = 5.7 Hz, 2H), 4.41 (s, 2H), 3.84 (s, 2H). 19F NMR (377 MHz, Acetonitrile-d3) δ  −117.34-−117.74 (m), −122.43, −123.88-−124.23 (m). |
| 836 | 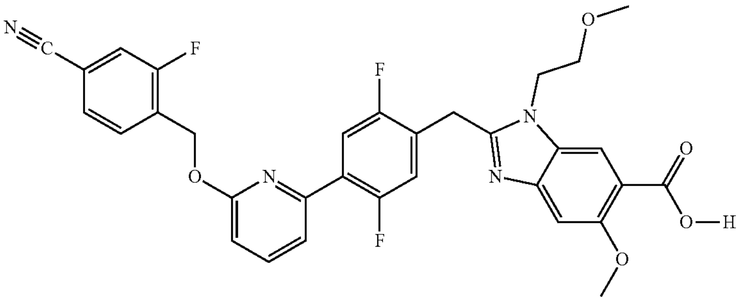 [SMILES: COCCn1c(Cc2cc(F)c(-c3cccc(OCc4ccc(C#N)cc4F)n3)cc2F)nc2cc(OC)c(C(=O)O)cc21] ES/MS m/z 603.2; 1H NMR (400 MHz, Acetonitrile-d3) δ 8.33 (s, 1H), 7.82 (ddd, J = 14.1, 9.6, 6.9 Hz, 2H), 7.76-7.69 (m, 1H), 7.64-7.53 (m, 3H), 7.46 (s, 1H), 7.27 (dd, J = 11.5, 6.1 Hz, 1H), 6.94 (dd, J = 8.3, 0.7 Hz, 1H), 5.62 (s, 2H), 4.60-4.54 (m, 4H), 4.07 (s, 3H), 3.74 (dd, J = 5.4, 4.5 Hz, 2H), 3.26 (s, 3H). 19F NMR (376 MHz, Acetonitrile-d3) δ −117.51-−117.59 (m), −122.19 (ddd, J = 17.4, 11.0, 6.1 Hz), −123.72 (ddd, J = 17.7, 10.9, 6.2 Hz). |
| 837 | 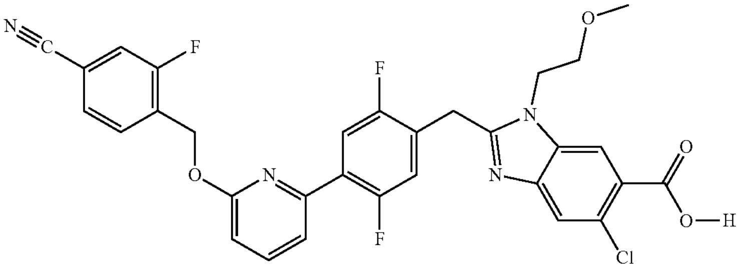 [SMILES: COCCn1c(Cc2cc(F)c(-c3cccc(OCc4ccc(C#N)cc4F)n3)cc2F)nc2cc(Cl)c(C(=O)O)cc21] ES/MS m/z 607; 1H NMR (400 MHz, Acetonitrile-d3) δ 8.14 (s, 1H), 7.88-7.75 (m, 3H), 7.73 (t, J = 7.5 Hz, 1H), 7.58 (dd, J = 11.0, 8.2 Hz, 3H), 7.22 (dd, J = 11.5, 6.1 Hz, 1H), 6.93 (dd, J = 8.3, 0.7 Hz, 1H), 5.63 (s, 2H), 4.55-4.45 (m, 4H), 3.72 (t, J = 5.0 Hz, 2H), 3.26 (s, 3H). 19F NMR (376 MHz, Acetonitrile-d3) δ −117.44-−117.69 (m), −122.54-−122.81 (m), −124.07 (ddd, J = 17.3, 10.7, 6.1 Hz). |

-continued

| Example | Structure/Name/Characterization |
| --- | --- |
| 838 | 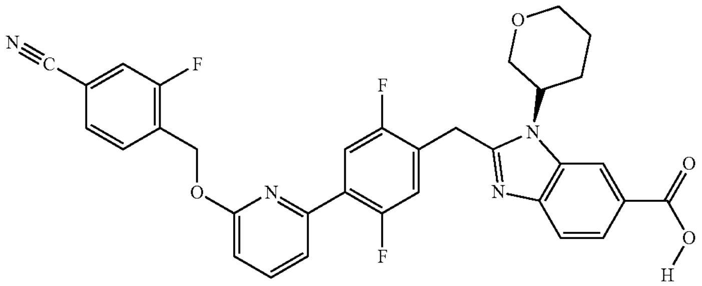 ES/MS m/z 599.2; 1H NMR (400 MHz, Acetonitrile-d3) δ 8.53-8.47 (m, 1H), 8.03 (dd, J = 8.6, 1.4 Hz, 1H), 7.89-7.76 (m, 3H), 7.71 (t, J = 7.5 Hz, 1H), 7.58 (d, J = 8.7 Hz, 2H), 7.54 (dd, J = 7.5, 1.7 Hz, 1H), 7.27 (dd, J = 11.5, 6.1 Hz, 1H), 6.92 (d, J = 8.2 Hz, 1H), 5.61 (s, 2H), 4.70 (tt, J = 10.9, 4.5 Hz, 1H), 4.62 (s, 2H), 4.09 (t, J = 10.8 Hz, 1H), 4.04-3.89 (m, 3H), 3.63 (td, J = 11.2, 4.2 Hz, 1H), 2.48 (qd, J = 12.1, 5.6 Hz, 1H), 2.10 (d, J = 12.3 Hz, 1H), 1.92-1.84 (m, 2H). Multiplet Report 19F NMR (376 MHz, Acetonitrile-d3) δ −117.43--117.59 (m), −121.92 (ddd, J = 17.7, 11.4, 6.7 Hz), −123.64 (ddd, J = 17.7, 10.9, 6.2 Hz). |
| 839 | 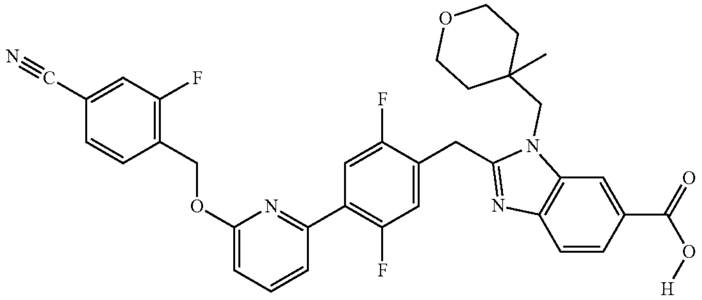 [SMILES: CC1(Cn2c(Cc3cc(F)c(-c4cccc(OCc5ccc(C#N)cc5F)n4)cc3F)nc3ccc(C(=O)O)cc32)CCOCC1] ES/MS m/z 627.2; 1H NMR (400 MHz, Acetonitrile-d3) δ 8.43 (dd, J = 1.5, 0.6 Hz, 1H), 8.06 (dd, J = 8.6, 1.4 Hz, 1H), 7.86-7.67 (m, 4H), 7.62-7.49 (m, 3H), 7.32 (dd, J = 11.4, 6.1 Hz, 1H), 6.93 (dd, J = 8.3, 0.7 Hz, 1H), 5.60 (s, 2H), 4.60 (s, 2H), 4.36 (s, 2H), 3.76 (ddd, J = 12.2, 4.9, 2.3 Hz, 2H), 3.60 (td, J = 11.8, 2.1 Hz, 2H), 1.83-1.71 (m, 2H), 1.44 (dd, J = 13.3, 2.1 Hz, 2H), 1.21 (s, 3H). 19F NMR (376 MHz, Acetonitrile-d3) δ −117.51 (dd, J = 9.8, 7.3 Hz), −121.85--122.08 (m), −123.45 (ddd, J = 17.6, 10.8, 6.1 Hz). |
| 840 | 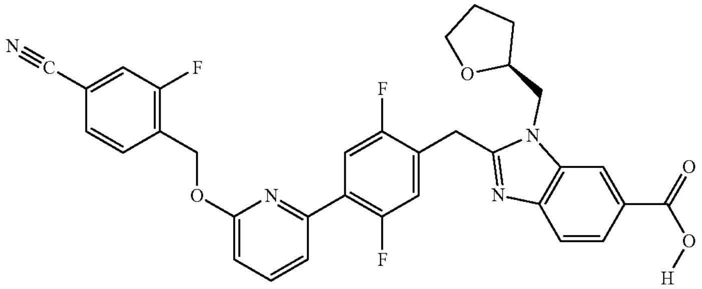 [SMILES: N#Cc1ccc(COc2cccc(-c3cc(F)c(Cc4nc5ccc(C(=O)O)cc5n4C[C@@H]4CCCO4)cc3F)n2)c(F)c1] ES/MS m/z 599.2; 1H NMR (400 MHz, Acetonitrile-d3) δ 8.38 (d, J = 1.5 Hz, 1H), 8.04 (dd, J = 8.5, 1.5 Hz, 1H), 7.88-7.67 (m, 4H), 7.65-7.52 (m, 3H), 7.28 (dd, J = 11.5, 6.1 Hz, 1H), 6.93 (d, J = 8.3 Hz, 1H), 5.63 (s, 2H), 4.59 (d, J = 2.9 Hz, 2H), 4.56 (d, J = 2.6 Hz, 1H), 4.38 (dd, J = 15.1, 8.5 Hz, 1H), 4.26 (dd, J = 11.1, 4.8 Hz, 1H), 3.85 (dt, J = 8.3, 6.8 Hz, 1H), 3.69 (dt, J = 8.3, 6.8 Hz, 1H), 2.24-2.14 (m, 1H), 1.87 (d, J = 4.8 Hz, 1H), 1.69 (dq, J = 12.3, 7.6 Hz, 1H). 19F NMR (376 MHz, Acetonitrile-d3) δ −117.49--117.61 (m), −122.33, −123.78--123.92 (m). |

Example 540. (S)-2-((6-((4-cyano-2-fluorobenzyl)oxy)-5'-fluoro-2'-oxo-[2,4'-bipyridin]-1'(2'H)-yl)methyl)-1-(oxetan-2-ylmethyl)-1H-benzo[d]imidazole-6-carboxylic acid Procedure 86

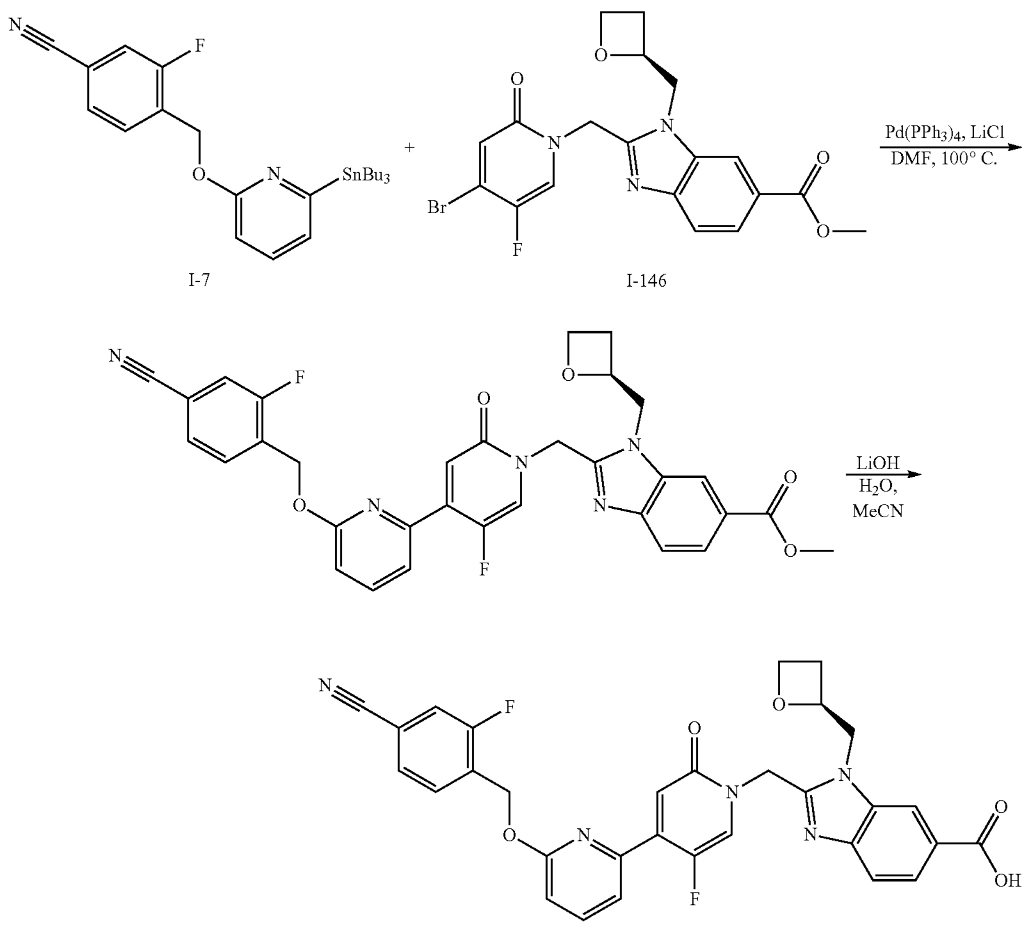

I-7 I-146

Example 540

Methyl (S)-2-((6-((4-cyano-2-fluorobenzyl)oxy)-5'-fluoro-2'-oxo-[2,4'-bipyridin]-1'(2'H)-yl)methyl)-1-(oxetan-2-ylmethyl)-1H-benzo[d]imidazole-6-carboxylate: A seal tube was charged with methyl (S)-2-((4-bromo-5-fluoro-2-oxopyridin-1(2H)-yl)methyl)-1-(oxetan-2-ylmethyl)-1H-benzo[d]imidazole-6-carboxylate (I-146, 100 mg, 0.22 mmol), 3-fluoro-4-(((6-(tributylstannyl)pyridin-2-yl)oxy)methyl)benzonitrile (I-7, 172 mg, 0.33 mmol), tetrakis(triphenylphosphine)palladium(0) (38.5 mg, 0.033 mmol), and lithium chloride (28.2 mg, 0.67 mmol). DMF (1 mL) was added, and the suspension was degassed with bubbling argon for 60 seconds. The reaction vessel was sealed and heated at 100° C. for 16 h. Upon cooling, the mixture was concentrated in vacuo and purified by silica gel column chromatography (eluent: Hex/EtOAc then EtOAc/MeOH) to provide the desired product. ES/MS: 598.2 ($M+H^+$).

(S)-2-((6-((4-cyano-2-fluorobenzyl)oxy)-5'-fluoro-2'-oxo-[2,4'-bipyridin]-1'(2'H)-yl)methyl)-1-(oxetan-2-ylmethyl)-1H-benzo[d]imidazole-6-carboxylic acid (Example 540): To a solution of methyl (S)-2-((6-((4-cyano-2-fluorobenzyl)oxy)-5'-fluoro-2'-oxo-[2,4'-bipyridin]-1'(2'H)-yl)methyl)-1-(oxetan-2-ylmethyl)-1H-benzo[d]imidazole-6-carboxylate (26.0 mg, 0.044 mmol) in acetonitrile (0.75 mL) was added aqueous 0.3 M lithium hydroxide (0.19 mL, 0.057 mmol). The reaction vessel was sealed, and the mixture was heated at 100° C. for 2 minutes. The mixture was immediately cooled, concentrated in vacuo, and purified by RP-HPLC (eluent: water/MeCN 0.1% TFA). Fractions containing the product were immediately poured into brine and extracted with three portions of ethyl acetate. The combined organic layers were washed with water until the washes tested at pH~7. The organic layer was dried over sodium sulfate, isolated by vacuum filtration, and concentrated in vacuo to provide Example 540. ES/MS: 584.2 ($M+H^+$); $^1$H NMR (400 MHz, DMSO) δ 8.30 (d, J=1.6 Hz, 1H), 8.25 (d, J=7.0 Hz, 1H), 7.97-7.87 (m, 2H), 7.81 (dd, J=8.4, 1.6 Hz, 1H), 7.77-7.69 (m, 2H), 7.65 (d, J=8.5 Hz, 1H), 7.51 (dd, J=7.4, 1.9 Hz, 1H), 7.08 (d, J=8.3 Hz, 1H), 6.88 (d, J=7.5 Hz, 1H), 5.58-5.50 (m, 3H), 5.42 (d, J=15.9 Hz, 1H), 5.14-5.04 (m, 1H), 4.84 (dd, J=15.5, 6.9 Hz, 1H), 4.71 (dd, J=15.4, 2.7 Hz, 1H), 4.54-4.44 (m, 1H), 4.40-4.30 (m, 1H), 2.79-2.68 (m, 1H), 2.43-2.34 (m, 1H).

Example 842. 2-(2-fluoro-4-(6-((2-fluoro-4-(pyrimidin-5-ylethynyl)benzyl)oxy)pyridin-2-yl)benzyl)-1-(2-methoxyethyl)-1H-benzo[d]imidazole-6-carboxylic acid Procedure 87

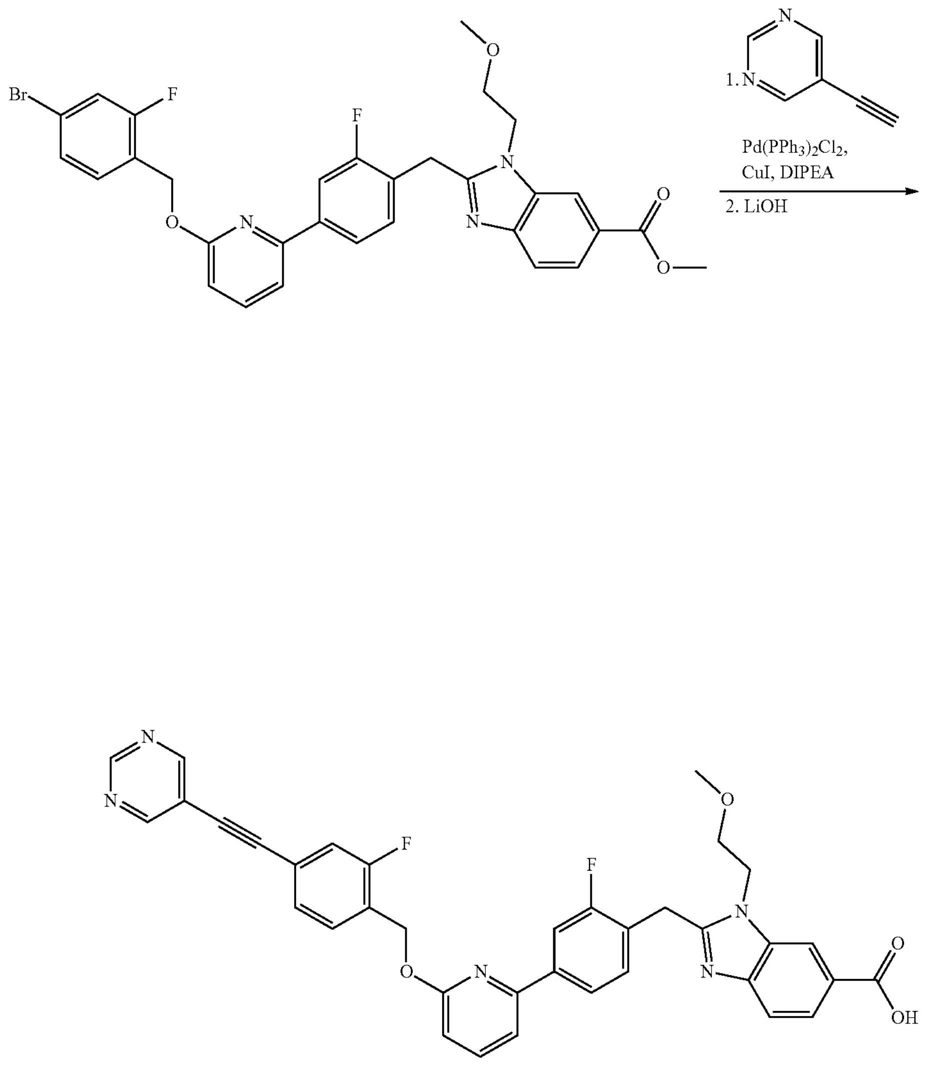

Example 842

2-(2-fluoro-4-(6-((2-fluoro-4-(pyrimidin-5-ylethynyl) benzyl)oxy)pyridin-2-yl)benzyl)-1-(2-methoxyethyl)-1H-benzo[d]imidazole-6-carboxylic acid (Example 842): Methyl 2-(4-(6-((4-bromo-2-fluorobenzyl)oxy)pyridin-2-yl)-2-fluorobenzyl)-1-(2-methoxyethyl)-1H-benzo[d]imidazole-6-carboxylate (40.0 mg, 0.064 mmol) was obtained as described in Procedure 32 substituting 1-(bromomethyl)-2-cyclopropyl-benzene with 4-bromo-1-(bromomethyl)-2-fluorobenzene. This was combined with $Pd(PPh_3)_2Cl_2$ (11.3 mg, 0.016 mmol), CuI (5.8 mg, 0.030 mmol), diisopropylethylamine (0.22 mL, 1.29 mmol), and DMF (1 mL) in a vial. The mixture was degassed through bubbling argon for 1 minute after which the vial was sealed and heated to 90° C. for 2 hours. Upon completion the reaction contents were concentrated directly and the resulting crude residue purified by flash chromatography (0-100% EtOAc in hexane) to yield methyl 2-(2-fluoro-4-(6-((2-fluoro-4-(pyrimidin-5-ylethynyl)benzyl)oxy)pyridin-2-yl)benzyl)-1-(2-methoxyethyl)-1H-benzo[d]imidazole-6-carboxylate which was then converted to 2-(2-fluoro-4-(6-((2-fluoro-4-(pyrimidin-5-ylethynyl)benzyl)oxy)pyridin-2-yl)benzyl)-1-(2-methoxyethyl)-1H-benzo[d]imidazole-6-carboxylic acid (Example 842) in an identical manner as described for the final step of Procedure 32. ES/MS m/z: 632.3 ($M+H^+$); 1H NMR (400 MHz, DMSO-d6) δ 9.23 (s, 1H), 9.04 (s, 2H), 8.30 (d, J=1.6 Hz, 1H), 7.98-7.80 (m, 4H), 7.72-7.59 (m, 4H), 7.59-7.53 (m, 1H), 7.52-7.42 (m, 2H), 6.93 (d, J=8.2 Hz, 1H), 5.59 (s, 2H), 4.65 (t, J=5.1 Hz, 2H), 4.53 (s, 2H), 3.68 (t, J=5.0 Hz, 2H), 3.21 (s, 3H).

Example 841, 843. Compounds Prepared Using Procedure 87

Other compounds of the present disclosure prepared using the general route described in Procedure 87 include the following Examples.

| Example | Structure/Name/Characterization |
|---|---|
| 841 | 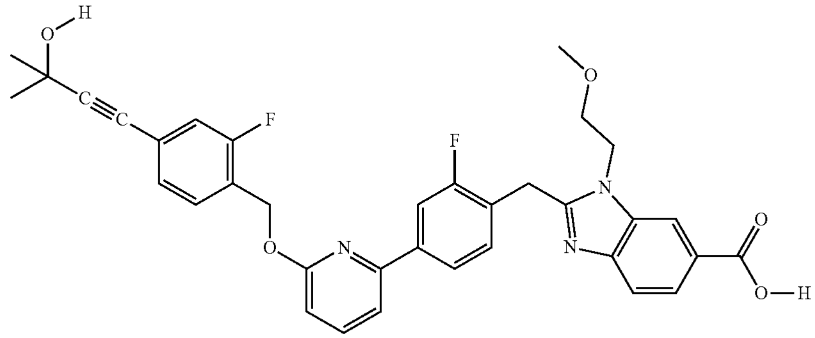 [SMILES: COCCn1c(Cc2ccc(-c3cccc(OCc4ccc(C#CC(C)(C)O)cc4F)n3)cc2F)nc2ccc(C(=O)O)cc21]<br>ES/MS m/z 612.2; 1H NMR (400 MHz, DMSO) δ 8.34 (d, J = 1.5 Hz, 1H), 7.97-7.88 (m, 3H), 7.85 (t, J = 7.8 Hz, 1H), 7.67 (dd, J = 8.0, 4.9 Hz, 2H), 7.55 (t, J = 7.8 Hz, 1H), 7.48 (t, J = 8.1 Hz, 1H), 7.30-7.20 (m, 2H), 6.90 (d, J = 8.2 Hz, 1H), 5.53 (s, 2H), 4.68 (t, J = 5.1 Hz, 2H), 4.57 (s, 2H), 3.68 (t, J = 5.0 Hz, 2H), 3.21 (s, 3H), 1.45 (s, 6H). |
| 843 | 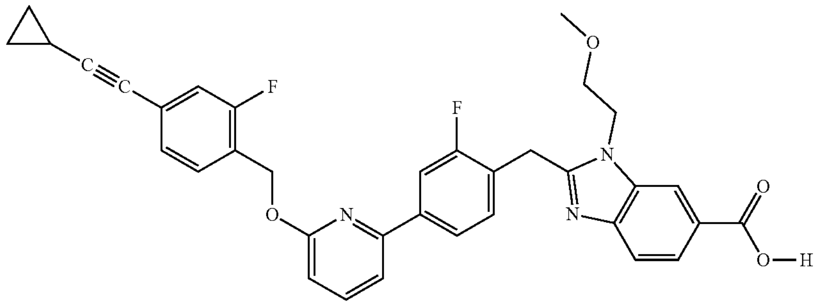 [SMILES: COCCn1c(Cc2ccc(-c3cccc(OCc4ccc(C#CC5CC5)cc4F)n3)cc2F)nc2ccc(C(=O)O)cc21]<br>ES/MS m/z 594.6; 1H NMR (400 MHz, DMSO-d6) δ 8.31 (d, J = 1.5 Hz, 1H), 8.00-7.78 (m, 4H), 7.71-7.60 (m, 2H), 7.60-7.40 (m, 2H), 7.36-7.13 (m, 2H), 6.90 (d, J = 8.2 Hz, 1H), 5.52 (s, 2H), 4.66 (t, J = 5.1 Hz, 2H), 4.54 (s, 2H), 3.68 (t, J = 5.0 Hz, 2H), 1.61-1.49 (m, 1H), 0.95-0.84 (m, 2H), 0.80-0.67 (m, 2H). |

Example 844. 2-(4-(6-((4-cyano-2-(methoxymethyl)benzyl)oxy)pyridin-2-yl)-2,5-difluorobenzyl)-1-(2-methoxyethyl)-1H-benzo[d]imidazole-6-carboxylic acid Procedure 88

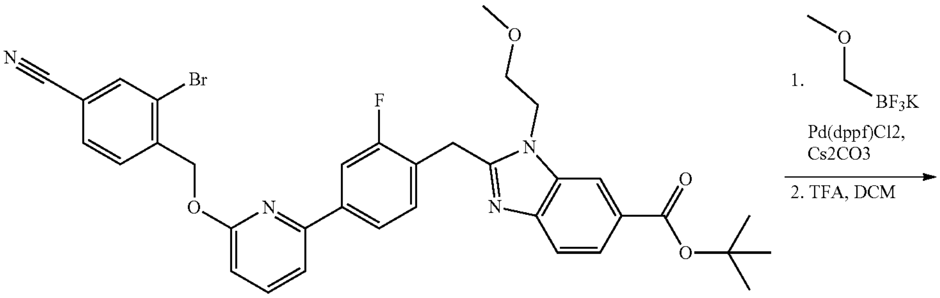

-continued

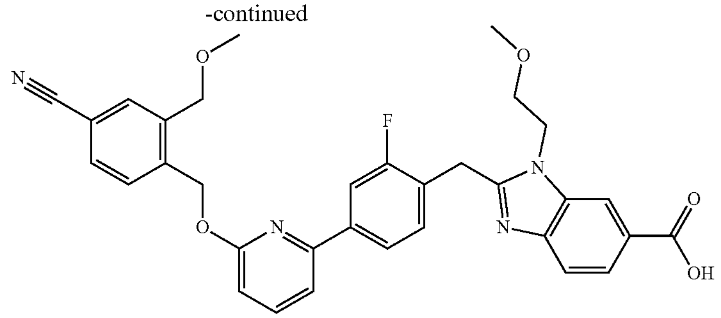

Example 844

2-(4-(6-((4-cyano-2-(methoxymethyl)benzyl)oxy)pyridin-2-yl)-2,5-difluorobenzyl)-1-(2-methoxyethyl)-1H-benzo[d]imidazole-6-carboxylic acid (Example 844): Tert-butyl 2-(4-(6-((2-bromo-4-cyanobenzyl)oxy)pyridin-2-yl)-2,5-difluorobenzyl)-1-(2-methoxyethyl)-1H-benzo[d]imidazole-6-carboxylate (50 mg, 0.073 mmol) was obtained as described in Procedure 77 substituting 4-(bromomethyl)benzonitrile with 3-bromo-4-(bromomethyl)benzonitrile. This was combined with potassium trifluoro(methoxymethyl)boranuide (110 mg, 0.73 mmol), cesium carbonate (71 mg, 0.22 mmol), Pd(dppf)$Cl_2$ (16 mg, 0.022 mmol) and dioxane (2 mL). Argon was bubbled through the solution for 2 minutes after which the reaction vial was sealed and heated to 100° C. for 2 hours. Upon completion the reaction contents were poured into water (5 mL) and extracted with EtOAc (2×15 mL). The organic layers were combined, washed with brine (5 mL), dried over $MgSO_4$, filtered, concentrated, and purified by flash chromatography (0-100% EtOAc in hexane). The resulting tert-butyl 2-(4-(6-((4-cyano-2-(methoxymethyl)benzyl)oxy)pyridin-2-yl)-2,5-difluorobenzyl)-1-(2-methoxyethyl)-1H-benzo[d]imidazole-6-carboxylate (43 mg, 0.066 mmol) was then converted to the final product 2-(4-(6-((4-cyano-2-(methoxymethyl)benzyl)oxy)pyridin-2-yl)-2,5-difluorobenzyl)-1-(2-methoxyethyl)-1H-benzo[d]imidazole-6-carboxylic acid (Example 844) in an identical manner as described for the final step of Procedure 77. ES/MS m/z: 599.5 ($M+H^+$); 1H NMR (400 MHz, DMSO-d6) δ 8.29 (d, J=1.5 Hz, 1H), 7.98-7.83 (m, 3H), 7.81 (dd, J=7.9, 1.8 Hz, 1H), 7.74 (dd, J=10.5, 6.4 Hz, 1H), 7.66 (dd, J=11.6, 8.2 Hz, 2H), 7.53 (dd, J=7.3, 1.7 Hz, 1H), 7.41 (dd, J=11.5, 6.1 Hz, 1H), 7.02 (d, J=8.2 Hz, 1H), 5.61 (s, 2H), 4.65 (t, J=5.0 Hz, 2H), 4.62 (s, 2H), 4.51 (s, 2H), 3.69 (t, J=5.0 Hz, 2H), 3.34 (s, 3H), 3.21 (s, 3H).

Example 845. 2-(2-fluoro-4-(6-((2-fluoro-4-(methoxymethyl)benzyl)oxy)pyridin-2-yl)benzyl)-1-(2-methoxyethyl)-1H-benzo[d]imidazole-6-carboxylic acid Procedure 89

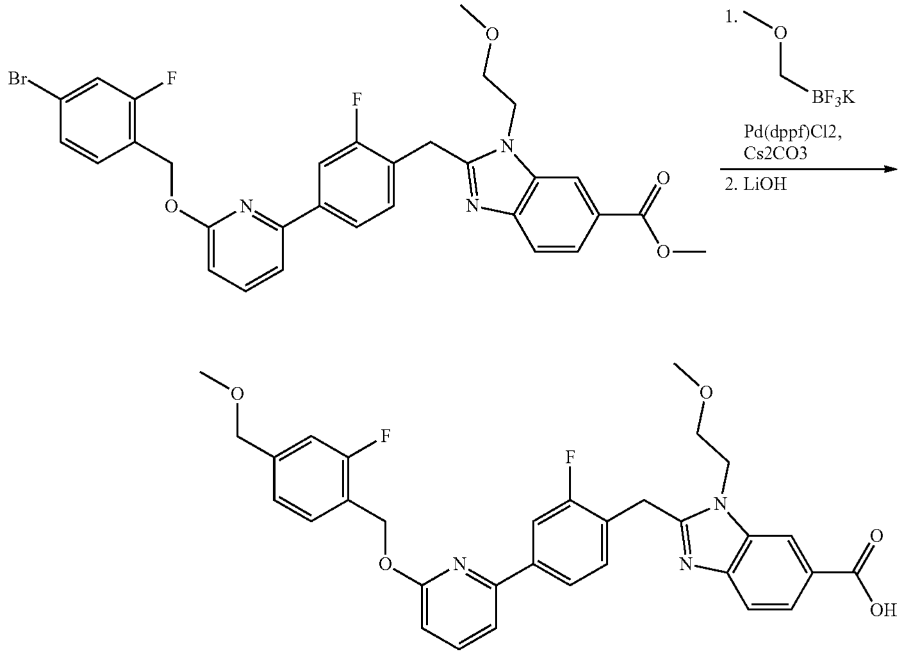

Example 845

2-(2-fluoro-4-(6-((2-fluoro-4-(methoxymethyl)benzyl)oxy)pyridin-2-yl)benzyl)-1-(2-methoxyethyl)-1H-benzo[d]imidazole-6-carboxylic acid (Example 845): Methyl 2-(4-(6-((4-bromo-2-fluorobenzyl)oxy)pyridin-2-yl)-2-fluorobenzyl)-1-(2-methoxyethyl)-1H-benzo[d]imidazole-6-carboxylate (50 mg, 0.080 mmol) was obtained as described in Procedure 32 substituting 1-(bromomethyl)-2-cyclopropyl-benzene with 4-bromo-1-(bromomethyl)-2-fluorobenzene. This was combined with potassium trifluoro(methoxymethyl)boranuide (122 mg, 0.80 mmol), cesium carbonate (79 mg, 0.24 mmol), Pd(dppf)$Cl_2$ (18 mg, 0.024 mmol) and dioxane (2 mL). Argon was bubbled through the solution for 2 minutes after which the reaction vial was sealed and heated to 100° C. for 2 hours. Upon completion the reaction contents were poured into water (5 mL) and extracted with EtOAc (2×15 mL). The organic layers were combined, washed with brine (5 mL), dried over $MgSO_4$, filtered, concentrated, and purified by flash chromatography (0-100% EtOAc in hexane) to give methyl 2-(2-fluoro-4-(6-((2-fluoro-4-(methoxymethyl)benzyl)oxy)pyridin-2-yl)benzyl)-1-(2-methoxyethyl)-1H-benzo[d]imidazole-6-carboxylate then converted to 2-(2-fluoro-4-(6-((2-fluoro-4-(methoxymethyl)benzyl)oxy)pyridin-2-yl)benzyl)-1-(2-methoxyethyl)-1H-benzo[d]imidazole-6-carboxylic acid (Example 845) in an identical manner as described for the final step of Procedure 32. ES/MS m/z: 574.6 (M+H$^+$); 1H NMR (400 MHz, DMSO-d6) δ 8.29 (d, J=1.5 Hz, 1H), 8.01-7.90 (m, 2H), 7.90-7.80 (m, 2H), 7.65 (dd, J=8.0, 3.5 Hz, 2H), 7.56 (t, J=7.8 Hz, 1H), 7.46 (t, J=8.1 Hz, 1H), 7.24-7.07 (m, 2H), 6.88 (d, J=8.2 Hz, 1H), 5.53 (s, 2H), 4.64 (t, J=5.1 Hz, 2H), 4.52 (s, 2H), 4.43 (s, 2H), 3.68 (t, J=5.0 Hz, 2H), 3.29 (s, 3H), 3.21 (s, 3H).

Example 846. (phosphonooxy)methyl 2-(4-(6-((4-cyano-2-fluorobenzyl)oxy)pyridin-2-yl)-2,5-difluorobenzyl)-1-(2-methoxyethyl)-1H-benzo[d]imidazole-6-carboxylate Procedure 90

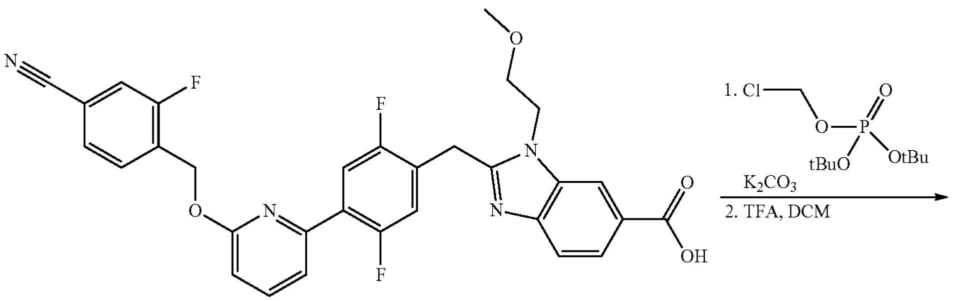

Example 426

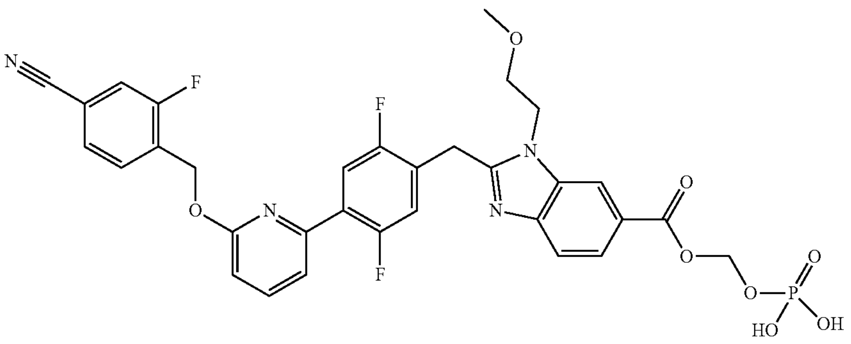

Example 846

(Phosphonooxy)methyl 2-(4-(6-((4-cyano-2-fluorobenzyl)oxy)pyridin-2-yl)-2,5-difluorobenzyl)-1-(2-methoxyethyl)-1H-benzo[d]imidazole-6-carboxylate (Example 846): Example 426 (50 mg, 0.087 mmol), potassium carbonate (36 mg, 0.26 mmol) and DMF (1.5 mL) were stirred at 25° C. for 20 minutes at which point di-tert-butyl chloromethyl phosphate (41 uL, 0.18 mmol) was added and the resultant mixture stirred for 2 hours. Upon completion the reaction mixture was poured into water (5 mL) and extracted with EtOAc (2×15 mL). The organic layers were combined, washed with brine (5 mL), dried over $MgSO_4$, filtered, concentrated, and purified by flash chromatography (0-100% EtOAc in hexane) to give ((di-tert-butoxyphosphoryl)oxy)methyl 2-(4-(6-((4-cyano-2-fluorobenzyl)oxy)pyridin-2-yl)-2,5-difluorobenzyl)-1-(2-methoxyethyl)-1H-benzo[d]imidazole-6-carboxylate. This intermediate (35 mg, 0.044 mmol) was then dissolved in DCM (2 mL) and trifluoroacetic acid (0.5 mL) and stirred at 40° C. for 3 hrs. The reaction mixture was concentrated directly and purified by RP-HPLC (eluent: $MeCN/H_2O$) to yield the product (Example 846) as the trifluoroacetate salt. ES/MS m/z: 683.1 $(M+H^+)$; 1H NMR (400 MHz, DMSO-d6) δ 8.31 (d, J=1.5 Hz, 1H), 8.00-7.82 (m, 3H), 7.82-7.72 (m, 3H), 7.69 (d, J=8.5 Hz, 1H), 7.53 (dd, J=7.5, 1.7 Hz, 1H), 7.40 (dd, J=11.5, 6.1 Hz, 1H), 7.00 (d, J=8.3 Hz, 1H), 5.77 (d, J=13.4 Hz, 2H), 5.60 (s, 2H), 4.64 (t, J=5.1 Hz, 2H), 4.49 (s, 2H), 3.70 (t, J=5.0 Hz, 2H), 3.22 (s, 3H).

Example 847. Ethyl 2-(4-(6-((4-cyano-2-fluorobenzyl)oxy)pyridin-2-yl)-2,5-difluorobenzyl)-1-(2-methoxyethyl)-1H-benzo[d]imidazole-6-carboxylate Procedure 91

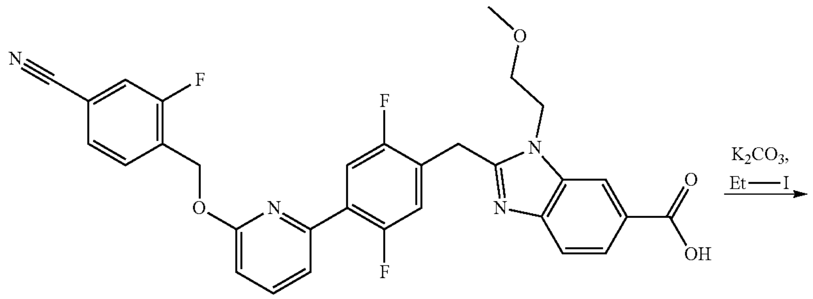

Example 426

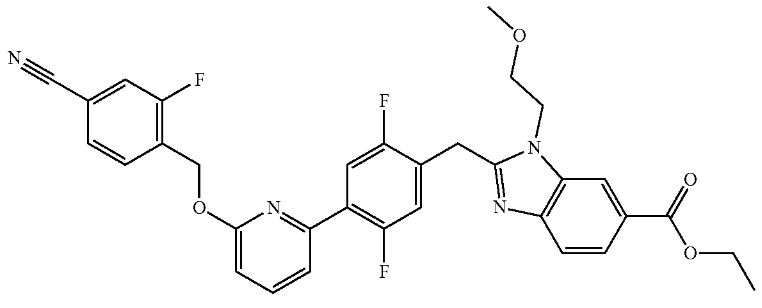

Example 847

Ethyl 2-(4-(6-((4-cyano-2-fluorobenzyl)oxy)pyridin-2-yl)-2,5-difluorobenzyl)-1-(2-methoxyethyl)-1H-benzo[d]imidazole-6-carboxylate (Example 847): Example 426 (50 mg, 0.087 mmol) was dissolved in DMF (1 mL) after which potassium carbonate was added (36 mg, 0.26 mmol) and the resultant mixture stirred for 20 minutes. Ethyl iodide (9 uL, 0.11 mmol) was then added and the resultant mixture stirred for 2 hours. Upon completion, the reaction mixture was poured into water (5 mL) and extracted with EtOAc (2×15 mL). The organic layers were combined, washed with brine (5 mL), dried over $MgSO_4$, filtered, concentrated, and purified by RP-HPLC (eluent: $MeCN/H_2O$) to yield the product (Example 847) as the trifluoroacetate salt. ES/MS m/z: 601.6 ($M+H^+$); 1H NMR (400 MHz, DMSO-d6) δ 8.30 (d, J=1.5 Hz, 1H), 8.00-7.84 (m, 3H), 7.80-7.71 (m, 3H), 7.67 (d, J=8.4 Hz, 1H), 7.53 (dd, J=7.5, 1.7 Hz, 1H), 7.41 (dd, J=11.5, 6.1 Hz, 1H), 7.00 (d, J=8.2 Hz, 1H), 5.60 (s, 2H), 4.66 (t, J=5.1 Hz, 2H), 4.52 (s, 2H), 4.36 (q, J=7.1 Hz, 2H), 3.70 (t, J=5.0 Hz, 2H), 3.21 (s, 3H), 1.36 (t, J=7.1 Hz, 3H).

Example 849. 1-((2-acetyl-2-azabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylic Acid Procedure 92

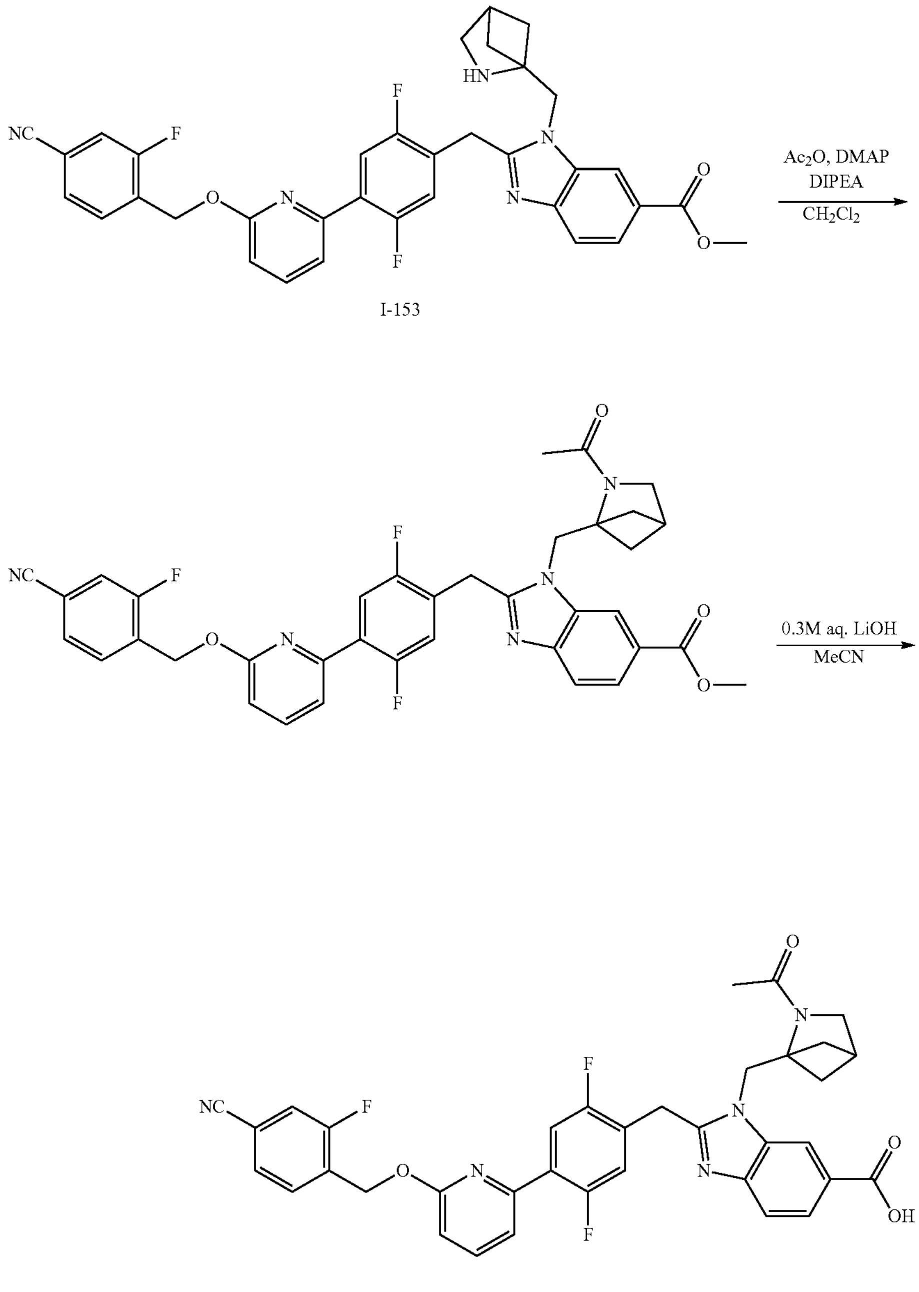

Methyl 1-((2-acetyl-2-azabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylate: Methyl 1-((2-azabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylate (65.0 mg, 0.104 mmol) was taken up in dichloromethane (1.50 mL) and the mixture cooled to 0° C. N,N-diisopropylethylamine (0.109 mL, 0.625 mol) and 4-dimethylaminopyridine (1.3 mg, 0.01 mmol) were then added to the mixture followed by acetic anhydride (49 μL, 0.521 mmol). The mixture was slowly warmed from 0° C. to r.t. and stirred at r.t. for one hour. The mixture was then partitioned between EtOAc (5 mL) and water (5 mL). The organic phase was collected and the aqueous phase was extracted with EtOAc (2×5 mL) and the combined organic extracts were dried over $MgSO_4$, concentrated in vacuo and used in the subsequent step without purification. ES/MS: 666.2 $(M+H^+)$ 1-((2-acetyl-2-azabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylic acid (Example 624): Methyl 1-((2-acetyl-2-azabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylate (69 mg, 0.104 mmol) was taken up in acetonitrile (1.0 mL) and aqueous lithium hydroxide (0.3 M, 1.0 mL, 0.313 mmol) was added. The mixture was heated to 100° C. for 7 minutes then cooled to r.t. and diluted with 5% aqueous citric acid to a pH~5. The mixture was extracted with EtOAc (3×5 mL) and the combined organic extracts dried over $MgSO_4$ and concentrated in vacuo. The material was purified by RP-HPLC (eluent: MeCN/water gradient with 0.1% TFA) to yield Example 849 as the trifluoroacetate salt. ES/MS: 652.2 $(M+H^+)$; 1H NMR (400 MHz, DMSO-d6) δ 8.08 (s, 1H), 7.98-7.82 (m, 3H), 7.82-7.71 (m, 3H), 7.67 (d, J=8.4 Hz, 1H), 7.54 (dd, J=7.5, 1.7 Hz, 1H), 7.47 (dd, J=11.5, 6.1 Hz, 1H), 7.00 (d, J=8.3 Hz, 1H), 5.60 (s, 2H), 5.29 (s, 2H), 4.41 (s, 2H), 3.55 (s, 2H), 2.66 (q, J=4.6, 3.3 Hz, 1H), 2.04 (s, 3H), 1.56 (dd, J=4.6, 1.7 Hz, 2H), 1.49-1.35 (m, 2H).

Example 848. Compounds Prepared Using Procedure 92

Other compounds of the present disclosure prepared using the general route described in Procedure 92 include the following Example.

| Example | Structure/Name/Characterization |
|---|---|
| 848 | 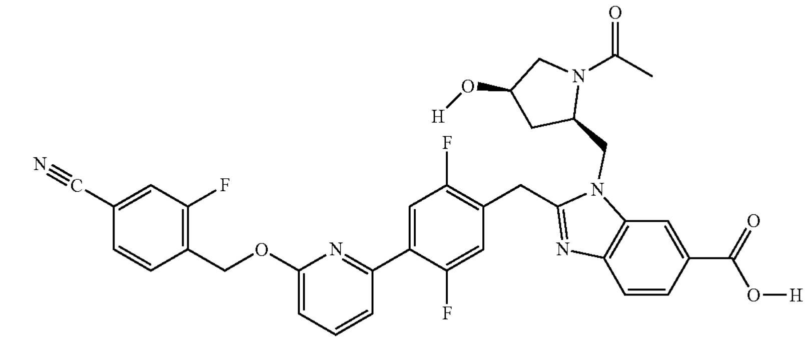 [SMILES: CC(=O)N1C[C@H](O)C[C@@H]1Cn1c(Cc2cc(F)c(-c3cccc(OCc4ccc(C#N)cc4F)n3)cc2F)nc2ccc(C(=O)O)cc21] ES/MS m/z: 656.2; 1H NMR (400 MHz, DMSO-d6) δ 8.51 (d, J = 1.5 Hz, 1H), 7.97-7.86 (m, 4H), 7.80-7.70 (m, 4H), 7.67 (d, J = 8.5 Hz, 1H), 7.58-7.46 (m, 2H), 7.00 (dd, J = 8.3, 2.7 Hz, 1H), 5.60 (s, 2H), 4.76 (dd, J = 14.2, 6.1 Hz, 1H), 4.65 (d, J = 17.4 Hz, 3H), 4.53 (q, J = 7.2 Hz, 1H), 4.48 (d, J = 4.7 Hz, 1H), 3.69 (dd, J = 11.0, 4.5 Hz, 1H), 3.49 (d, J = 10.9 Hz, 1H), 1.97 (ddd, J = 13.4, 8.7, 4.6 Hz, 1H), 1.86 (s, 3H), 1.84-1.72 (m, 1H). |

Example 850. (S)-2-(4-(6-((6-Cyano-4-methoxypyridin-3-yl)methoxy)pyridin-2-yl)-2,5-difluorobenzyl)-1-(oxetan-2-ylmethyl)-1H-benzo[d]imidazole-6-carboxylic acid Procedure 93

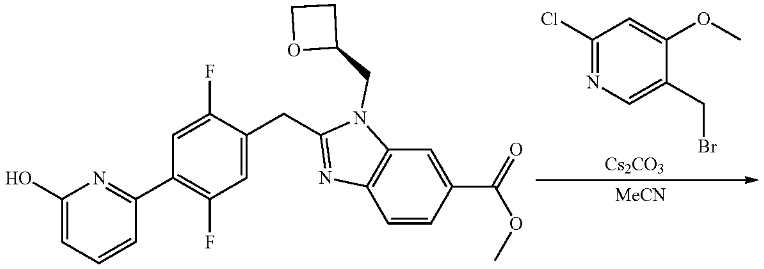

I-155

-continued

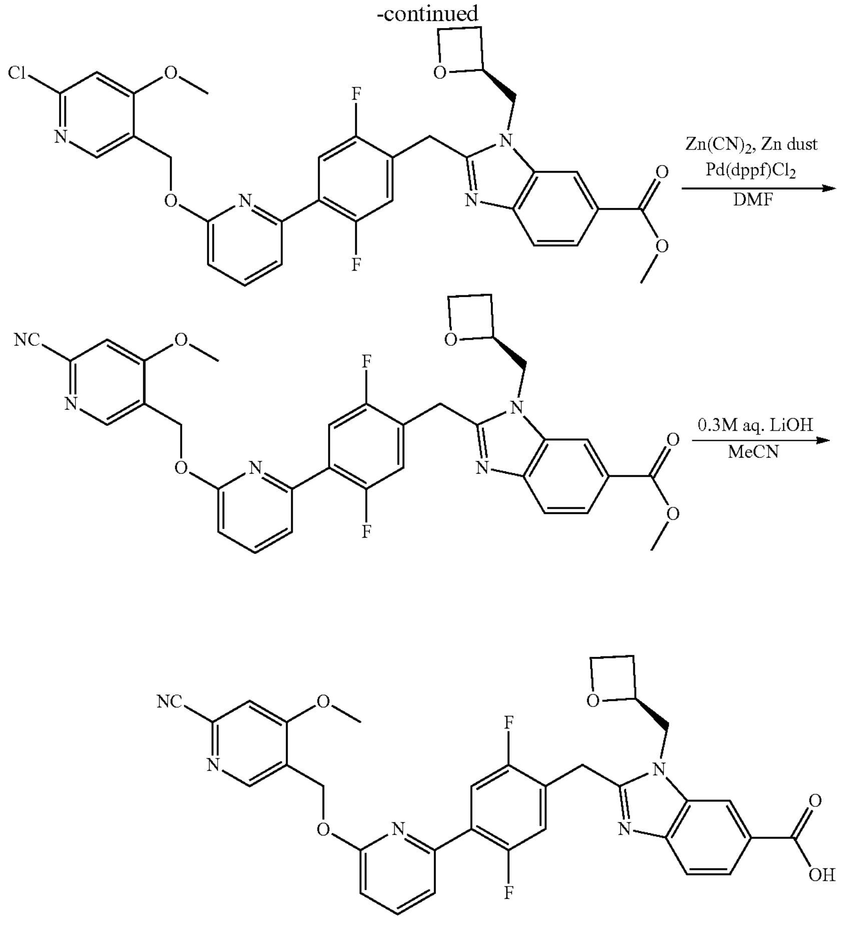

Example 850

Methyl (S)-2-(4-(6-((6-chloro-4-methoxypyridin-3-yl)methoxy)pyridin-2-yl)-2,5-difluorobenzyl)-1-(oxetan-2-ylmethyl)-1H-benzo[d]imidazole-6-carboxylate: I-155 (100 mg, 0.210 mmol) and 5-(bromomethyl)-2-chloro-4-methoxypyridine (72 mg, 0.300 mmol) were dissolved in acetonitrile (2.0 mL) and cesium carbonate (100 mg, 0.310 mmol) was added. The suspension was heated to 60° C. After 30 minutes the mixture was cooled to r.t., filtered through celite (washed with EtOAc), and the filtrate concentrated in vacuo. The residue was purified by column chromatography (eluent: EtOAc/dichloromethane) to afford the desired product. ES/MS: 621.2 ($M+H^+$)

Methyl (S)-2-(4-(6-((6-cyano-4-methoxypyridin-3-yl)methoxy)pyridin-2-yl)-2,5-difluorobenzyl)-1-(oxetan-2-ylmethyl)-1H-benzo[d]imidazole-6-carboxylate: Methyl (S)-2-(4-(6-((6-chloro-4-methoxypyridin-3-yl)methoxy)pyridin-2-yl)-2,5-difluorobenzyl)-1-(oxetan-2-ylmethyl)-1H-benzo[d]imidazole-6-carboxylate (88 mg, 0.140 mmol), $Zn(CN)_2$ (10 mg, 0.085 mmol), zinc dust (0.9 mg, 0.014 mmol), and $Pd(dppf)Cl_2$ (12 mg, 0.014 mmol) were combined in N,N-dimethylformamide (1.0 mL) and the mixture sparged with argon for 5 minutes. The reaction was then sealed and heated to 120° C. for one hour. Upon reaction completion the mixture was cooled to r.t. and partitioned between EtOAc (10 mL) and saturated aqueous $NH_4Cl$ (10 mL). The organic phase was collected and the aqueous phase extracted with EtOAc (2×5 mL). The combined organic extracts were dried over $MgSO_4$, concentrated under reduced pressure, and purified by column chromatography (eluent: EtOAc/dichloromethane) to yield the product.

(S)-2-(4-(6-((6-Cyano-4-methoxypyridin-3-yl)methoxy)pyridin-2-yl)-2,5-difluorobenzyl)-1-(oxetan-2-ylmethyl)-1H-benzo[d]imidazole-6-carboxylic acid (Example 850): Methyl (S)-2-(4-(6-((6-cyano-4-methoxypyridin-3-yl)methoxy)pyridin-2-yl)-2,5-difluorobenzyl)-1-(oxetan-2-ylmethyl)-1H-benzo[d]imidazole-6-carboxylate (71.0 mg, 0.116 mmol) was taken up in acetonitrile (0.5 mL) and aqueous lithium hydroxide (0.3 M, 0.5 mL, 0.151 mmol) was added. The mixture was heated to 100° C. for 5 minutes then cooled to r.t. and diluted with N,N-dimethylformamide (1 mL) and acetic acid (0.1 mL). The solution was injected directly onto the RP-HPLC (eluent: MeCN/water gradient with 0.10% TFA) and purified. Fractions containing the product were immediately diluted with EtOAc and washed with water until the washes tested at pH~7. The organic layer was dried over $MgSO_4$, isolated by vacuum filtration, and concentrated in vacuo to provide Example 850. ES/MS: 598.2 ($M+H^+$); 1H NMR (400 MHz, DMSO-d6) δ 8.65 (s, 1H), 8.24 (d, J=1.4 Hz, 1H), 7.98-7.84 (m, 2H), 7.83-7.73 (m, 2H), 7.64-7.48 (m, 2H), 7.39 (dd, J=11.5, 6.1 Hz, 1H), 6.98 (d, J=8.2 Hz, 1H), 5.52 (s, 2H), 5.08 (qd, J=7.0, 2.7 Hz, 1H), 4.75 (dd, J=15.6, 7.0 Hz, 1H), 4.62 (dd, J=15.6, 2.8 Hz, 1H), 4.58-4.40 (m, 3H), 4.36 (dt, J=9.0, 5.9 Hz, 1H), 4.00 (s, 3H), 2.71 (tdd, J=11.2, 7.9, 4.7 Hz, 1H), 2.48-2.30 (m, 1H).

Example 852. (S)-2-(4-(6-((6-cyanopyridin-3-yl)methoxy)-3-fluoropyridin-2-yl)-2,5-difluorobenzyl)-4-fluoro-1-(oxetan-2-ylmethyl)-1H-benzo[d]imidazole-6-carboxylic acid Procedure 94

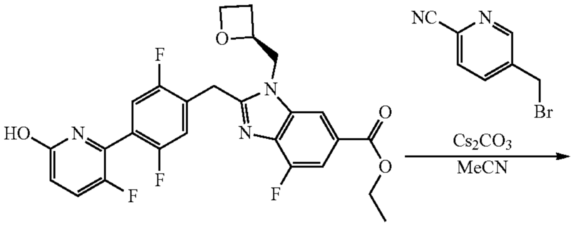

I-162

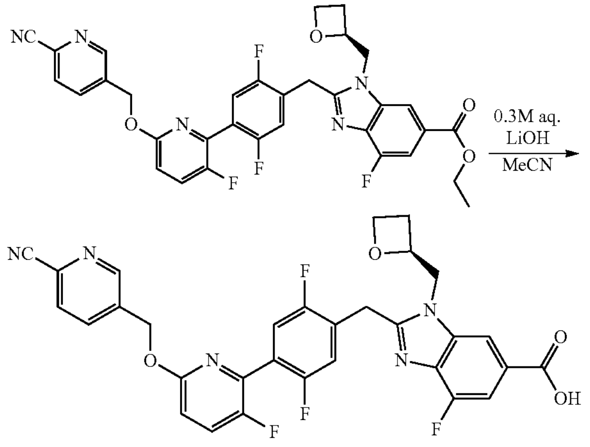

Example 852

Ethyl (S)-2-(4-(6-((6-cyanopyridin-3-yl)methoxy)-3-fluoropyridin-2-yl)-2,5-difluorobenzyl)-4-fluoro-1-(oxetan-2-ylmethyl)-1H-benzo[d]imidazole-6-carboxylate: I-162

(30 mg, 0.059 mmol) and 5-(bromomethyl)picolinonitrile (16 mg, 0.083 mmol) were dissolved in acetonitrile (1.0 mL) and cesium carbonate (27 mg, 0.084 mmol) was added. The suspension was heated to 60° C. After 30 minutes the mixture was cooled to r.t., filtered through celite (washed with EtOAc), and the filtrate concentrated in vacuo. The residue was purified by column chromatography (eluent: EtOAc/dichloromethane) to afford the desired product. (Note: in some examples using this procedure, $K_2CO_3$ is used in place of $Cs_2CO_3$). ES/MS: 632.2 ($M+H^+$)

(S)-2-(4-(6-((6-cyanopyridin-3-yl)methoxy)-3-fluoropyridin-2-yl)-2,5-difluorobenzyl)-4-fluoro-1-(oxetan-2-ylmethyl)-1H-benzo[d]imidazole-6-carboxylic acid (Example 852): Ethyl (S)-2-(4-(6-((6-cyanopyridin-3-yl)methoxy)-3-fluoropyridin-2-yl)-2,5-difluorobenzyl)-4-fluoro-1-(oxetan-2-ylmethyl)-1H-benzo[d]imidazole-6-carboxylate (23 mg, 0.037 mmol) was taken up in acetonitrile (0.5 mL) and aqueous lithium hydroxide (0.3 M, 0.16 mL, 0.048 mmol) was added. The mixture was heated to 100° C. for 5 minutes then cooled to r.t. and diluted with N,N-dimethylformamide (1 mL) and acetic acid (0.1 mL). The solution was injected directly onto the RP-HPLC (eluent: MeCN/water gradient with 0.1% TFA) and purified. Fractions containing the product were immediately diluted with EtOAc and washed with water until the washes tested at pH~7. The organic layer was dried over $MgSO_4$, isolated by vacuum filtration, and concentrated in vacuo to provide Example 852. ES/MS: 604.2 ($M+H^+$); 1H NMR (400 MHz, DMSO-d6) δ 8.88 (s, 1H), 8.26-7.99 (m, 3H), 7.91 (t, J=9.0 Hz, 1H), 7.57-7.37 (m, 3H), 7.13 (dd, J=8.9, 2.9 Hz, 1H), 5.55 (s, 2H), 5.08 (d, J=7.5 Hz, 1H), 4.81-4.69 (m, 1H), 4.70-4.42 (m, 4H), 4.42-4.29 (m, 1H), 2.82-2.69 (m, J=18.9 Hz, 1H), 2.46-2.36 (m, 1H).

Examples 851, 853. Compounds Prepared Using Procedure 94

Other compounds of the present disclosure prepared using the general route described in Procedure 94 include the following Examples.

| Example | Structure/Name/Characterization |
|---|---|
| 851 | 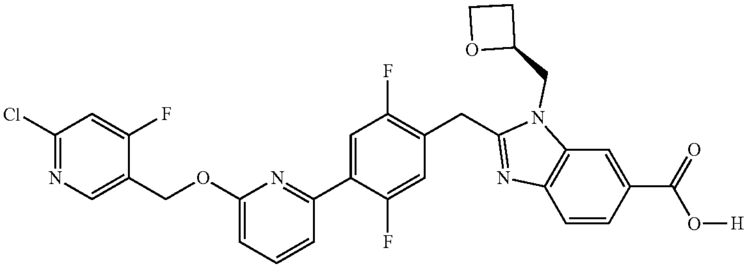 [SMILES: O=C(O)c1ccc2nc(Cc3cc(F)c(-c4cccc(OCc5cnc(Cl)cc5F)n4)cc3F)n(C[C@@H]3CCO3)c2c1] ES/MS m/z 595.2; 1H NMR (400 MHz, DMSO-d6) δ 8.66 (d, J = 9.9 Hz, 1H), 8.25 (d, J = 1.5 Hz, 1H), 7.98-7.82 (m, 2H), 7.79 (dd, J = 8.3, 1.5 Hz, 1H), 7.71 (d, J = 9.4 Hz, 1H), 7.60 (d, J = 8.4 Hz, 1H), 7.53 (dd, J = 7.4, 1.7 Hz, 1H), 7.40 (dd, J = 11.5, 6.1 Hz, 1H), 6.95 (d, J = 8.2 Hz, 1H), 5.56 (s, 2H), 5.08 (tt, J = 9.5, 4.7 Hz, 1H), 4.76 (dd, J = 15.6, 7.0 Hz, 1H), 4.62 (dd, J = 15.5, 2.8 Hz, 1H), 4.58-4.41 (m, 3H), 4.36 (dt, J = 8.9, 5.9 Hz, 1H), 2.73 (ddt, J = 14.4, 11.4, 7.2 Hz, 1H), 2.47-2.34 (m, 1H). |

-continued

| Example | Structure/Name/Characterization |
| --- | --- |
| 853 | 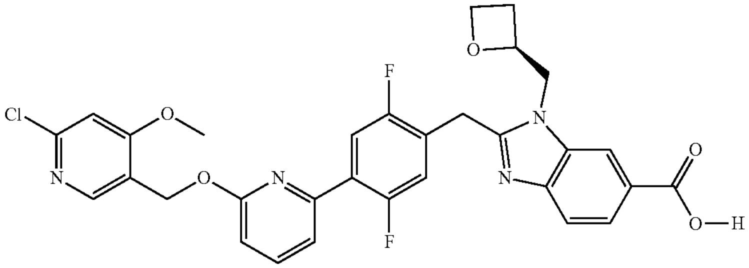 [SMILES: COc1cc(Cl)ncc1COc1cccc(-c2cc(F)c(Cc3nc4ccc(C(=O)O)cc4n3C[C@@H]3CCO3)cc2F)n1] ES/MS m/z 607.2; 1H NMR (400 MHz, Methanol-d4) δ 8.34-8.25 (m, 2H), 7.98 (dd, J = 8.5, 1.5 Hz, 1H), 7.85 (dd, J = 10.7, 6.4 Hz, 1H), 7.79 (t, J = 7.9 Hz, 1H), 7.66 (d, J = 8.5 Hz, 1H), 7.54 (dd, J = 7.4, 1.5 Hz, 1H), 7.18 (q, J = 6.2 Hz, 2H), 6.87 (d, J = 8.2 Hz, 1H), 5.50 (s, 2H), 5.20 (qd, J = 7.1, 2.6 Hz, 1H), 4.73 (dd, J = 15.7, 6.9 Hz, 1H), 4.69-4.51 (m, 4H), 4.51-4.36 (m, 1H), 4.01 (s, 3H), 2.80 (dtd, J = 11.5, 8.1, 6.0 Hz, 1H), 2.50 (ddt, J = 11.5, 9.2, 7.2 Hz, 1H). |

Example 854. (S)-2-(4-(6-((6-carbamoyl-4-fluoropyridin-3-yl)methoxy)pyridin-2-yl)-2,5-difluorobenzyl)-1-(oxetan-2-ylmethyl)-1H-benzo[d]imidazole-6-carboxylic acid Procedure 95

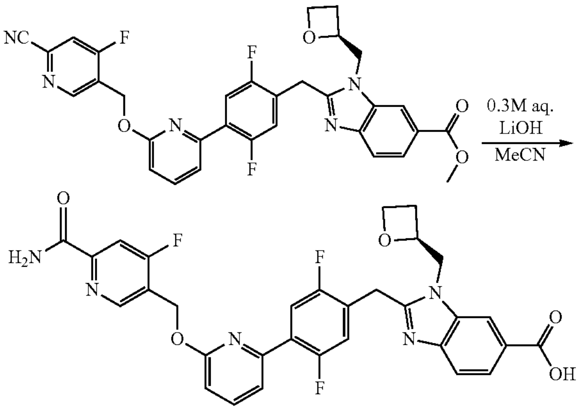

Example 854

(S)-2-(4-(6-((6-Carbamoyl-4-fluoropyridin-3-yl)methoxy)pyridin-2-yl)-2,5-difluorobenzyl)-1-(oxetan-2-ylmethyl)-1H-benzo[d]imidazole-6-carboxylic acid (Example 854): Methyl (S)-2-(4-(6-((6-cyano-4-fluoropyridin-3-yl)methoxy)pyridin-2-yl)-2,5-difluorobenzyl)-1-(oxetan-2-ylmethyl)-1H-benzo[d]imidazole-6-carboxylate was prepared according to Procedure 93 5-(bromomethyl)-2-chloro-4-fluoropyridine for 5-(bromomethyl)-2-chloro-4-methoxypyridine. Methyl (S)-2-(4-(6-((6-cyano-4-fluoropyridin-3-yl)methoxy)pyridin-2-yl)-2,5-difluorobenzyl)-1-(oxetan-2-ylmethyl)-1H-benzo[d]imidazole-6-carboxylate (58 mg, 0.096 mmol) was taken up in acetonitrile (0.5 mL) and aqueous lithium hydroxide (0.3 M, 0.41 mL, 0.125 mmol) was added. The mixture was heated to 100° C. for 5 minutes then cooled to r.t. and diluted with N,N-dimethylformamide (1 mL) and acetic acid (0.1 mL). The solution was injected directly onto the RP-HPLC (eluent: MeCN/water gradient with 0.1% TFA) and purified. Fractions containing the product were immediately diluted with EtOAc and washed with water until the washes tested at pH~7. The organic layer was dried over $MgSO_4$, isolated by vacuum filtration, and concentrated in vacuo to provide Example 854. ES/MS: 604.2 ($M+H^+$); 1H NMR (400 MHz, DMSO-d6) δ 8.84 (d, J=9.5 Hz, 1H), 8.26 (d, J=1.7 Hz, 1H), 7.97-7.76 (m, 4H), 7.61 (dd, J=8.4, 2.5 Hz, 1H), 7.54 (dd, J=7.4, 1.6 Hz, 1H), 7.40 (dd, J=11.6, 6.2 Hz, 1H), 6.97 (d, J=8.3 Hz, 1H), 5.65 (s, 1H), 5.08 (d, J=7.4 Hz, 1H), 4.76 (dd, J=15.7, 7.1 Hz, 1H), 4.71-4.59 (m, 1H), 4.59-4.40 (m, 3H), 4.36 (dt, J=8.8, 5.8 Hz, 1H), 2.80-2.65 (m, 1H), 2.48-2.30 (m, 1H).

Example 856. 2-(4-(6-((4-cyano-2-fluorobenzyl)oxy)pyridin-2-yl)-2,3,5-trifluorobenzyl)-1-(2-methoxyethyl)-1H-benzo[d]imidazole-6-carboxylic acid Procedure 96

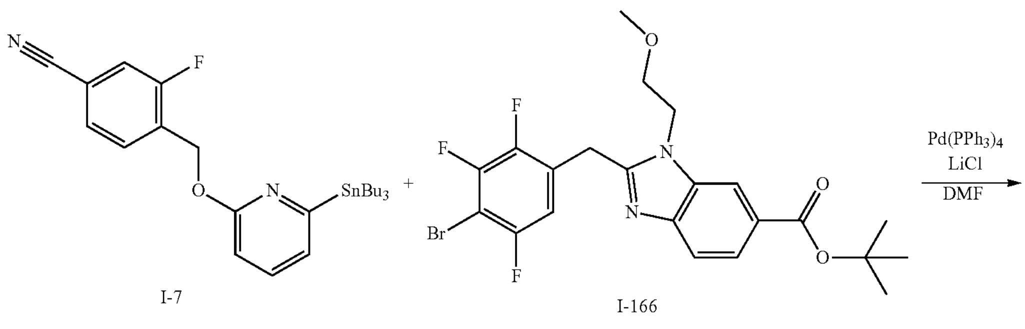

I-7 I-166

-continued

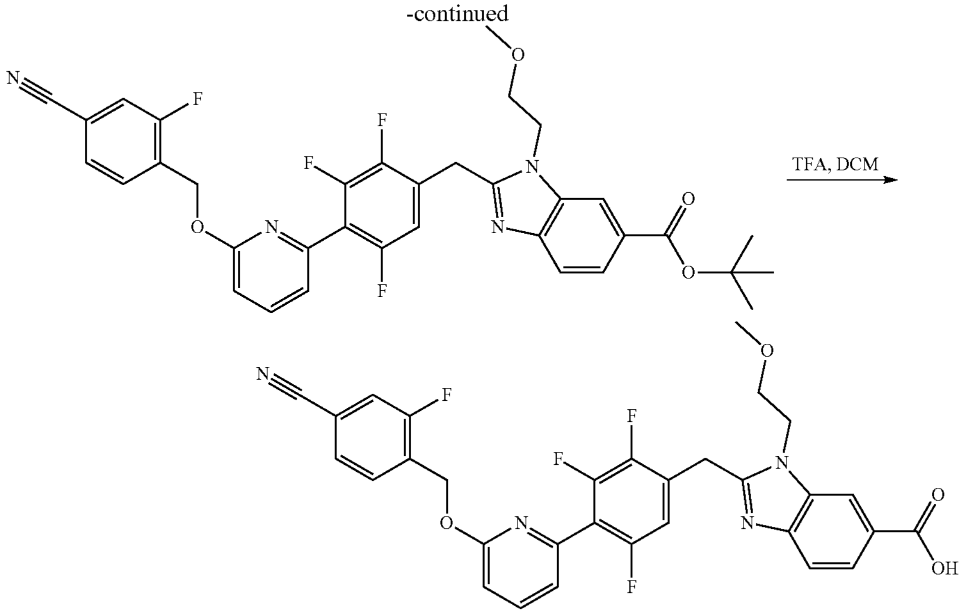

Example 856 tert-butyl 2-(4-(6-((4-cyano-2-fluorobenzyl)oxy)pyridin-2-yl)-2,3,5-trifluorobenzyl)-1-(2-methoxyethyl)-1H-benzo[d]imidazole-6-carboxylate: tert-butyl 2-(4-(6-((4-cyano-2-fluorobenzyl)oxy)pyridin-2-yl)-2,3,5-trifluorobenzyl)-1-(2-methoxyethyl)-1H-benzo[d]imidazole-6-carboxylate was prepared in a manner analogous to Procedure 7, Step 2, replacing methyl 2-[(6-bromo-3-pyridyl)methyl]-3-(2-methoxyethyl)benzimidazole-5-carboxylate with tert-butyl 2-(4-bromo-2,3,5-trifluorobenzyl)-1-(2-methoxyethyl)-1H-benzo[d]imidazole-6-carboxylate (I-166). ES/MS: 647.2 $[M+H]^+$.

2-(4-(6-((4-cyano-2-fluorobenzyl)oxy)pyridin-2-yl)-2,3,5-trifluorobenzyl)-1-(2-methoxyethyl)-1H-benzo[d]imidazole-6-carboxylic acid (Example 856): Example 856 was prepared in a manner analogous to Procedure 50, Step 4, replacing methyl 2-(4-(6-((4-cyano-2-fluorobenzyl)oxy)pyridin-2-yl)benzyl)-1-(2-methoxyethyl)-1H-benzo[d]imidazole-6-carboxylate with tert-butyl 2-(4-(6-((4-cyano-2-fluorobenzyl)oxy)pyridin-2-yl)-2,3,5-trifluorobenzyl)-1-(2-methoxyethyl)-1H-benzo[d]imidazole-6-carboxylate. ES/MS: 591.2 $[M+H]^+$ 1H NMR (400 MHz, DMSO) δ 8.25 (d, J=1.5 Hz, 1H), 7.94 (dd, J=8.4, 7.3 Hz, 1H), 7.91-7.87 (m, 1H), 7.83 (dd, J=8.4, 1.5 Hz, 1H), 7.77-7.70 (m, 2H), 7.64 (d, J=8.4 Hz, 1H), 7.34-7.27 (m, 2H), 7.05 (d, J=8.4 Hz, 1H), 5.47 (s, 2H), 4.63 (t, J=5.0 Hz, 2H), 4.54 (s, 2H), 3.70 (t, J=5.0 Hz, 2H), 3.22 (s, 3H).

Example 855. Compounds Prepared Using Procedure 96

Other compounds of the present disclosure prepared using the general route described in Procedure 96 include the following Example.

| Example | Structure/Name/Characterization |
| --- | --- |
| 855 | 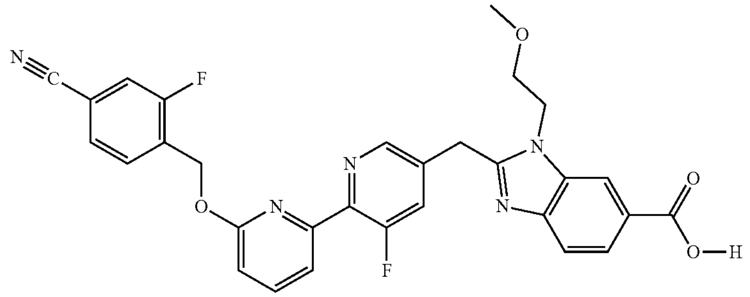 [SMILES: COCCn1c(Cc2cnc(-c3cccc(OCc4ccc(C#N)cc4F)n3)c(F)c2)nc2ccc(C(=O)O)cc21] ES/MS m/z 556.2; 1H NMR (400 MHz, DMSO) δ 8.60-8.53 (m, 1H), 8.31 (s, 1H), 7.93 (t, J = 7.9 Hz, 1H), 7.91-7.81 (m, 3H), 7.79-7.64 (m, 4H), 7.04 (d, J = 8.3 Hz, 1H), 5.55 (s, 2H), 4.68 (t, J = 5.1 Hz, 2H), 4.59 (s, 2H), 3.69 (t, J = 5.0 Hz, 2H), 3.19 (s, 3H). |

Example 857 (S)-2-(4-(6-((6-carbamoyl-2-(difluoromethoxy)pyridin-3-yl)methoxy)pyridin-2-yl)-2,5-difluorobenzyl)-1-(oxetan-2-ylmethyl)-1H-benzo[d]imidazole-6-carboxylic acid Example 858 (S)-2-(4-(6-((6-cyano-2-(difluoromethoxy)pyridin-3-yl)methoxy)pyridin-2-yl)-2,5-difluorobenzyl)-1-(oxetan-2-ylmethyl)-1H-benzo[d]imidazole-6-carboxylic acid and Procedure 97

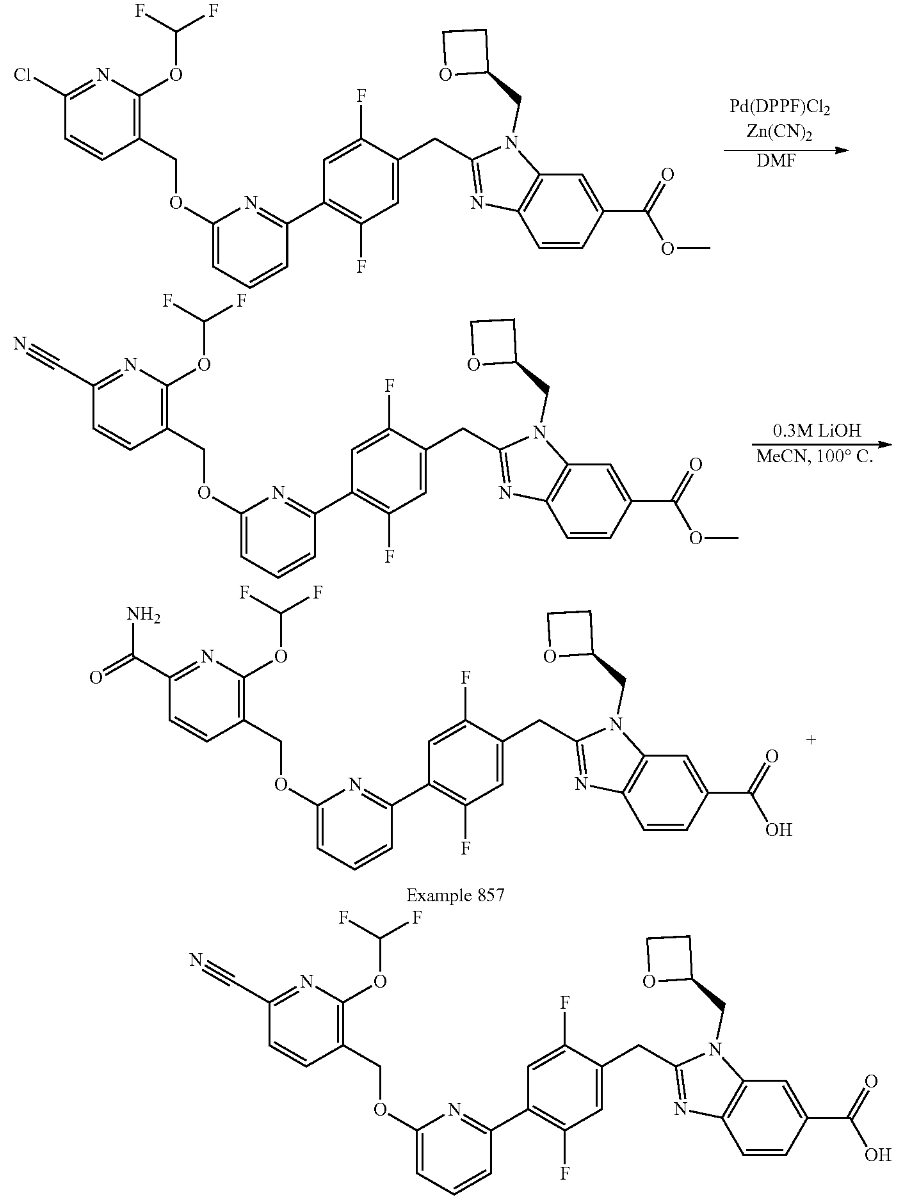

Example 857

Example 858

Methyl (S)-2-(4-(6-((6-cyano-2-(difluoromethoxy)pyridin-3-yl)methoxy)pyridin-2-yl)-2,5-difluorobenzyl)-1-(oxetan-2-ylmethyl)-1H-benzo[d]imidazole-6-carboxylate: A vial was charged with methyl (S)-2-(4-(6-((6-chloro-2-(difluoromethoxy)pyridin-3-yl)methoxy)pyridin-2-yl)-2,5-difluorobenzyl)-1-(oxetan-2-ylmethyl)-1H-benzo[d]imidazole-6-carboxylate (synthesized in a manner analogous to Procedure 52, Step 2 replacing I-76 with 3-(((6-bromopyridin-2-yl)oxy)methyl)-6-chloro-2-(difluoromethoxy)pyridine) (53.0 mg, 0.081 mmol), Pd(DPPF)$Cl_2$ (66.0 mg, 0.081 mmol), and zinc cyanide (11.4 mg, 0.097 mmol). The solids were suspended in DMF (1.0 mL), and the suspension was degassed by bubbling argon through the suspension for 60 seconds. The suspension was sealed in the vial and heated thermally at 100° C. for 3 hours. The mixture was cooled, concentrated in vacuo, and purified by silica gel column chromatography (eluent: EtOAc/Hexanes) to provide the desired product. ES/MS: 648.2 $[M+H]^+$ (S)-2-(4-(6-((6-carbamoyl-2-(difluoromethoxy)pyridin-3-yl)methoxy)pyridin-2-yl)-2,5-difluorobenzyl)-1-(oxetan-2-ylmethyl)-1H-benzo[d]imidazole-6-carboxylic acid (Example 857) and (S)-2-(4-(6-((6-cyano-2-(difluoromethoxy)

pyridin-3-yl)methoxy)pyridin-2-yl)-2,5-difluorobenzyl)-1-(oxetan-2-ylmethyl)-1H-benzo[d]imidazole-6-carboxylic acid (Example 858): To a solution of methyl (S)-2-(4-(6-((6-cyano-2-(difluoromethoxy)pyridin-3-yl)methoxy)pyridin-2-yl)-2,5-difluorobenzyl)-1-(oxetan-2-ylmethyl)-1H-benzo[d]imidazole-6-carboxylate (41.6 mg, 0.064 mmol) in MeCN (0.75 mL) was added 0.3 M aqueous lithium hydroxide (0.28 mL, 0.084 mmol). The mixture was heated to 100° C. for 3 minutes, then concentrated and purified by RP-HPLC (eluent: water/MeCN*0.1% TFA) to provide the desired product Example 858 and over hydrolysis product Example 857. Fractions containing the products were separately pooled and worked up. The fractions were partitioned between EtOAc and brine. The organic layer was isolated and washed with three additional portions of water followed by one portion of brine. The organic layer was again isolated, dried over sodium sulfate, and concentrated in vacuo to provide the free form of the products described.

Example 857: ES/MS: 652.2 $[M+H]^+$ 1H NMR (400 MHz, DMSO) δ 8.38-7.98 (m, 4H), 7.89 (t, J=7.9 Hz, 1H), 7.78 (dd, J=8.4, 1.6 Hz, 1H), 7.73 (s, 1H), 7.66 (dd, J=10.4, 6.4 Hz, 1H), 7.58 (d, J=8.4 Hz, 1H), 7.54-7.48 (m, 1H), 7.35 (dd, J=11.6, 6.0 Hz, 1H), 7.27 (d, J=8.5 Hz, 1H), 7.00 (d, J=8.3 Hz, 1H), 5.92 (s, 2H), 5.13-4.99 (m, 1H), 4.73 (dd, J=15.7, 6.9 Hz, 1H), 4.64-4.57 (m, 1H), 4.52-4.38 (m, 3H), 4.34 (dt, J=9.1, 5.9 Hz, 1H), 2.76-2.66 (m, 1H), 2.41-2.31 (m, 1H).

Example 858: ES/MS: 634.2 $[M+H]^+$ 1H NMR (400 MHz, DMSO) δ 12.77 (s, 1H), 8.31 (d, J=8.7 Hz, 1H), 8.25 (d, J=1.6 Hz, 1H), 7.96-7.48 (m, 7H), 7.38 (dd, J=11.5, 6.0 Hz, 1H), 6.98 (d, J=8.2 Hz, 1H), 5.65 (s, 2H), 5.13-5.01 (m, 1H), 4.75 (dd, J=15.6, 7.0 Hz, 1H), 4.67-4.60 (m, 1H), 4.56-4.41 (m, 3H), 4.35 (dt, J=8.9, 5.9 Hz, 1H), 2.84-2.67 (m, 1H), 2.43-2.34 (m, 1H).

Example 866. 2-[[2,5-difluoro-4-[6-[(6-methoxy-3-pyridyl)methoxy]-2-pyridyl]phenyl]methyl]-3-(2-methoxyethyl)benzimidazole-5-carboxylic acid Procedure 98

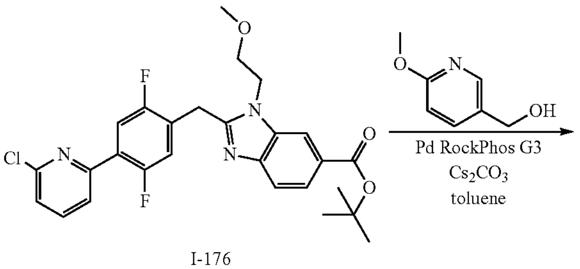

I-176

-continued

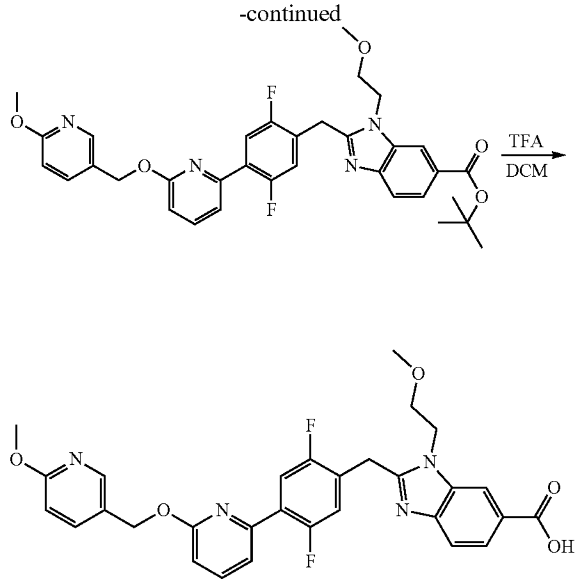

Example 866 tert-butyl 2-[[2,5-difluoro-4-[6-[(6-methoxy-3-pyridyl)methoxy]-2-pyridyl]phenyl]methyl]-3-(2-methoxyethyl)benzimidazole-5-carboxylate: A suspension of tert-butyl 2-[[4-(6-chloro-2-pyridyl)-2,5-difluoro-phenyl]methyl]-3-(2-methoxyethyl)benzimidazole-5-carboxylate (102 mg, 0.199 mmol), (6-methoxy-3-pyridyl)methanol (55.3 mg, 0.398 mmol), Pd RockPhos G3 (12.5 mg, 0.0149 mmol), and cesium carbonate (194 mg, 0.597 mmol) in toluene (2 mL) was degassed with Ar for 5 min, then heated at 90° C. overnight. The mixture was diluted with EtOAc and washed with brine. The organic extract was dried over sodium sulfate, filtered and concentrated. The crude residue was purified by flash chromatography (20-40% EtOAc in hexane) to yield desired product. ES/MS: 617.2 $(M+H^+)$; 1H NMR (400 MHz, Chloroform-d) δ 8.30 (d, J=2.4 Hz, 1H), 8.10-8.02 (m, 1H), 7.96 (dd, J=8.5, 1.5 Hz, 1H), 7.88 (dd, J=10.6, 6.3 Hz, 1H), 7.78-7.68 (m, 2H), 7.69-7.54 (m, 1H), 7.54-7.41 (m, 1H), 7.07 (dd, J=11.3, 6.1 Hz, 1H), 6.78 (ddd, J=8.3, 6.8, 0.7 Hz, 2H), 5.42 (s, 2H), 4.45 (s, 2H), 4.38 (t, J=5.2 Hz, 2H), 3.96 (d, J=3.1 Hz, 4H), 3.69 (t, J=5.2 Hz, 2H), 3.28 (s, 3H), 1.65 (s, 9H).

2-[[2,5-difluoro-4-[6-[(6-methoxy-3-pyridyl)methoxy]-2-pyridyl]phenyl]methyl]-3-(2-methoxyethyl)benzimidazole-5-carboxylic acid (Example 866): A solution of tert-butyl 2-[[2,5-difluoro-4-[6-[(6-methoxy-3-pyridyl)methoxy]-2-pyridyl]phenyl]methyl]-3-(2-methoxyethyl)benzimidazole-5-carboxylate (80.4 mg, 0.130 mmol) and TFA (0.198 mL, 2.61 mmol) in DCM (3 mL) was heated at 40° C. Upon completion, the mixture was concentrated directly and purified by RP-HPLC (eluent: $MeCN/H_2O$) to yield the product as a trifluoroacetate salt. ES/MS: 561.2 $(M+H^+)$; 1H NMR (400 MHz, DMSO-d6) δ 8.31 (d, J=2.5 Hz, 2H), 8.00-7.76 (m, 5H), 7.67 (d, J=8.5 Hz, 1H), 7.51 (dd, J=7.4, 1.7 Hz, 1H), 7.44 (dd, J=11.5, 6.1 Hz, 1H), 6.92 (d, J=8.3 Hz, 1H), 6.85 (d, J=8.5 Hz, 1H), 5.42 (s, 2H), 4.67 (t, J=5.1 Hz, 2H), 4.54 (s, 2H), 3.85 (s, 3H), 3.71 (t, J=5.0 Hz, 2H), 3.22 (s, 3H); 19F NMR (376 MHz, DMSO-d6) δ −75.27, −121.20--122.09 (m), −122.09--122.81 (m).

Examples 859-865, 867. Compounds Prepared Using Procedure 98

Other compounds of the present disclosure prepared using the general route described in Procedure 98 include the following Examples.

| Example | Structure/Name/Characterization |
|---|---|
| 859 | 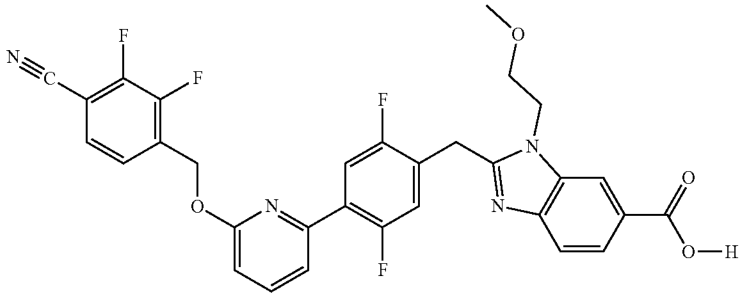 [SMILES: COCCn1c(Cc2cc(F)c(-c3cccc(OCc4ccc(C#N)c(F)c4F)n3)cc2F)nc2ccc(C(=O)O)cc21] ES/MS m/z 591.2; 1H NMR (400 MHz, DMSO-d6) δ 8.30 (d, J = 1.5 Hz, 1H), 7.95-7.84 (m, 2H), 7.84-7.71 (m, 2H), 7.66 (d, J = 8.5 Hz, 1H), 7.61-7.51 (m, 2H), 7.42 (dd, J = 11.5, 6.1 Hz, 1H), 7.01 (d, J = 8.2 Hz, 1H), 5.64 (s, 2H), 4.66 (t, J = 5.1 Hz, 2H), 4.53 (s, 2H), 3.70 (t, J = 5.0 Hz, 2H), 3.21 (s, 3H). |
| 860 | 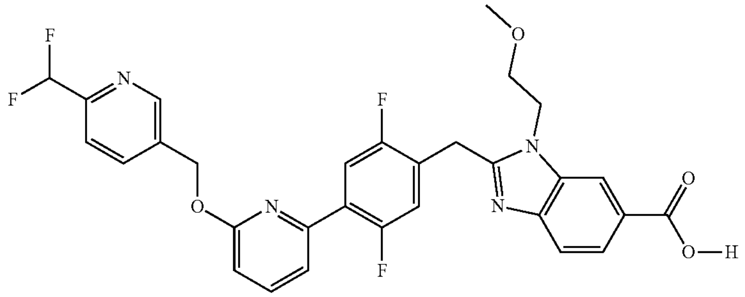 [SMILES: COCCn1c(Cc2cc(F)c(-c3cccc(OCc4ccc(C(F)F)nc4)n3)cc2F)nc2ccc(C(=O)O)cc21] ES/MS m/z 581.2; 1H NMR (400 MHz, DMSO-d6) δ 8.83 (d, J = 2.0 Hz, 1H), 8.26 (d, J = 1.5 Hz, 1H), 8.11 (dd, J = 8.1, 2.1 Hz, 1H), 7.90 (t, J = 7.9 Hz, 1H), 7.86-7.79 (m, 2H), 7.74 (d, J = 8.0 Hz, 1H), 7.63 (d, J = 8.5 Hz, 1H), 7.53 (dd, J = 7.6, 1.8 Hz, 1H), 7.40 (dd, J = 11.5, 6.1 Hz, 1H), 6.99 (d, J = 8.2 Hz, 1H), 6.97 (t, J = 55.0 Hz, 1H), 5.60 (s, 2H), 4.63 (t, J = 5.0 Hz, 2H), 4.49 (s, 2H), 3.69 (t, J = 5.1 Hz, 2H), 3.21 (s, 3H). |
| 861 | 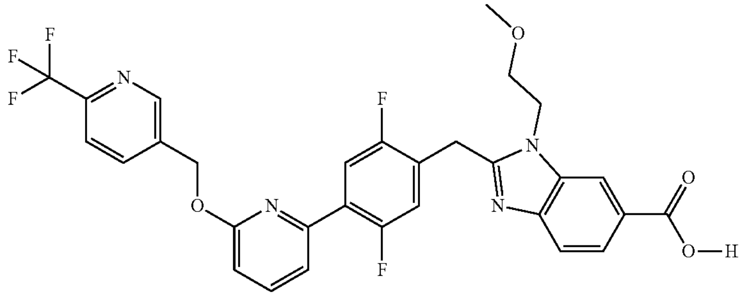 [SMILES: COCCn1c(Cc2cc(F)c(-c3cccc(OCc4ccc(C(F)(F)F)nc4)n3)cc2F)nc2ccc(C(=O)O)cc21] ES/MS m/z 599.2; 1H NMR (400 MHz, DMSO-d6) δ 8.91 (d, J = 2.0 Hz, 1H), 8.26 (d, J = 1.4 Hz, 1H), 8.20 (dd, J = 8.0, 2.0 Hz, 1H), 7.99-7.88 (m, 2H), 7.84 (dd, J = 8.5, 1.5 Hz, 1H), 7.78 (dd, J = 10.4, 6.4 Hz, 1H), 7.63 (d, J = 8.5 Hz, 1H), 7.53 (dd, J = 7.5, 1.7 Hz, 1H), 7.40 (dd, J = 11.5, 6.1 Hz, 1H), 7.01 (d, J = 8.2 Hz, 1H), 5.65 (s, 2H), 4.63 (t, J = 5.1 Hz, 2H), 4.49 (s, 2H), 3.69 (t, J = 5.0 Hz, 2H), 3.21 (s, 3H). |

-continued

| Example | Structure/Name/Characterization |
|---|---|
| 862 | 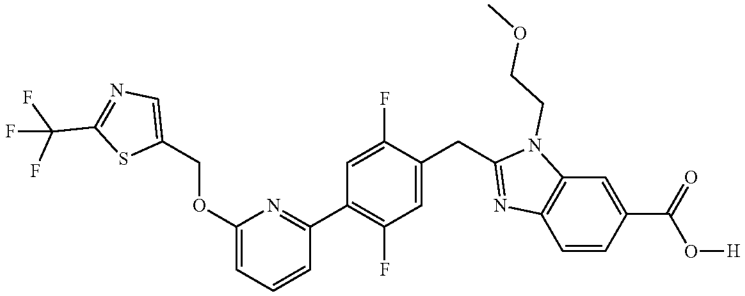 [SMILES: COCCn1c(Cc2cc(F)c(-c3cccc(OCc4cnc(C(F)(F)F)s4)n3)cc2F)nc2ccc(C(=O)O)cc21]<br>ES/MS m/z 605.2; 1H NMR (400 MHz, DMSO-d6) δ 8.33-8.25 (m, 2H), 7.97 (dd, J = 10.5, 6.5 Hz, 1H), 7.92 (t, J = 7.9 Hz, 1H), 7.87 (dd, J = 8.4, 1.5 Hz, 1H), 7.65 (d, J = 8.5 Hz, 1H), 7.58 (dd, J = 7.5, 1.6 Hz, 1H), 7.44 (dd, J = 11.6, 6.0 Hz, 1H), 6.97 (d, J = 8.3 Hz, 1H), 5.85 (s, 2H), 4.66 (t, J = 5.1 Hz, 2H), 4.53 (s, 2H), 3.70 (t, J = 5.0 Hz, 2H), 3.21 (s, 3H). |
| 863 | 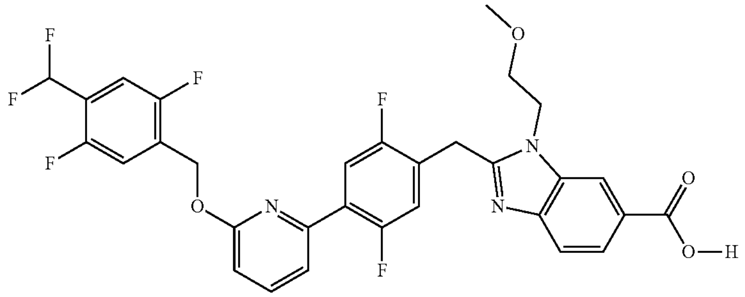 [SMILES: COCCn1c(Cc2cc(F)c(-c3cccc(OCc4cc(F)c(C(F)F)cc4F)n3)cc2F)nc2ccc(C(=O)O)cc21]<br>ES/MS m/z 616.2; 1H NMR (400 MHz, DMSO-d6) δ 8.29 (d, J = 1.5 Hz, 1H), 7.94-7.89 (m, 1H), 7.89-7.83 (m, 1H), 7.84-7.76 (m, 1H), 7.69-7.49 (m, 4H), 7.42 (dd, J = 11.5, 6.1 Hz, 1H), 7.23 (td, J = 54.0, 13.7 Hz, 1H), 7.00 (dd, J = 8.2, 3.1 Hz, 1H), 5.56 (s, 2H), 4.65 (t, J = 5.0 Hz, 2H), 4.51 (s, 2H), 3.70 (t, J = 5.0 Hz, 2H), 3.21 (d, J = 1.0 Hz, 3H). |
| 864 | 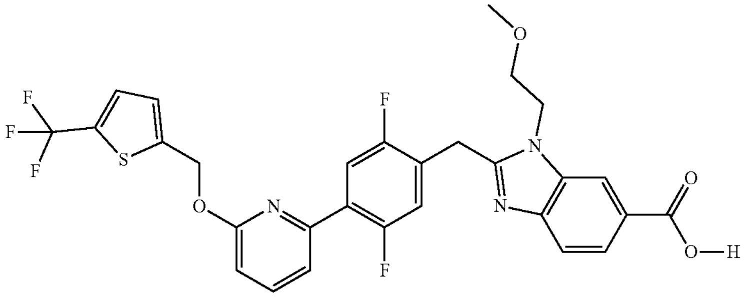 [SMILES: COCCn1c(Cc2cc(F)c(-c3cccc(OCc4ccc(C(F)(F)F)s4)n3)cc2F)nc2ccc(C(=O)O)cc21]<br>ES/MS m/z 604; 1H NMR (400 MHz, DMSO-d6) δ 8.27 (d, J = 1.5 Hz, 1H), 7.95 (dd, J = 10.6, 6.5 Hz, 1H), 7.93-7.88 (m, 1H), 7.85 (dd, J = 8.5, 1.5 Hz, 1H), 7.67-7.61 (m, 2H), 7.56 (dd, J = 7.5, 1.7 Hz, 1H), 7.42 (dd, J = 11.6, 6.1 Hz, 1H), 7.36 (dd, J = 3.8, 1.4 Hz, 1H), 6.96 (d, J = 8.2 Hz, 1H), 5.75 (s, 2H), 4.64 (t, J = 5.1 Hz, 2H), 4.51 (s, 2H), 3.69 (t, J = 5.0 Hz, 2H), 3.21 (s, 3H). |
| 865 | 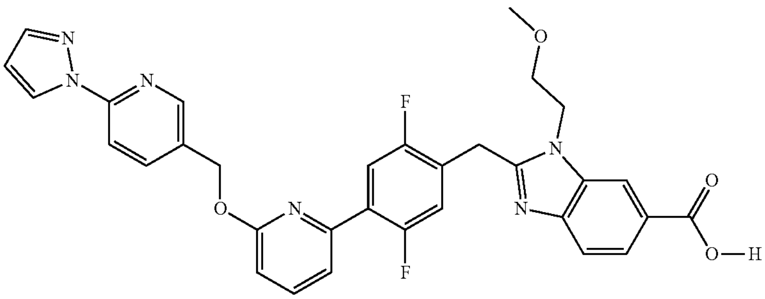 [SMILES: COCCn1c(Cc2cc(F)c(-c3cccc(OCc4ccc(-n5cccn5)nc4)n3)cc2F)nc2ccc(C(=O)O)cc21] |

-continued

| Example | Structure/Name/Characterization |
|---|---|
| | ES/MS MH+ 597.2; 1H NMR (400 MHz, DMSO-d6) δ 8.62 (dd, J = 4.8, 2.4 Hz, 2H), 8.30 (d, J = 1.4 Hz, 1H), 8.12 (dd, J = 8.5, 2.3 Hz, 1H), 7.96 (d, J = 8.4 Hz, 1H), 7.93-7.79 (m, 4H), 7.66 (d, J = 8.5 Hz, 1H), 7.53 (dd, J = 7.5, 1.7 Hz, 1H), 7.43 (dd, J = 11.5, 6.1 Hz, 1H), 6.98 (d, J = 8.2 Hz, 1H), 6.63-6.54 (m, 1H), 5.56 (s, 2H), 4.66 (t, J = 5.1 Hz, 2H), 4.53 (s, 2H), 3.70 (t, J = 5.0 Hz, 2H), 3.21 (s, 3H). Multiplet Report 19F NMR (376 MHz, DMSO-d6) δ −75.24, −121.28--122.01 (m), −122.10--122.74 (m). |
| 867 | 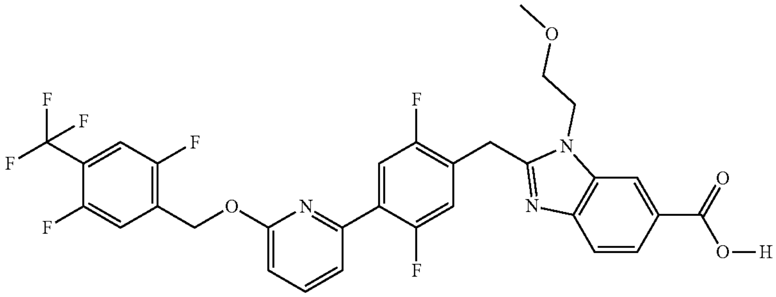 [SMILES: COCCn1c(Cc2cc(F)c(-c3cccc(OCc4cc(F)c(C(F)(F)F)cc4F)n3)cc2F)nc2ccc(C(=O)O)cc21] |
| | ES/MS m/z 634.2; Multiplet Report 1H NMR (400 MHz, DMSO-d6) δ 8.30 (d, J = 1.5 Hz, 1H), 7.96-7.70 (m, 5H), 7.66 (d, J = 8.5 Hz, 1H), 7.54 (dd, J = 7.4, 1.7 Hz, 1H), 7.42 (dd, J = 11.5, 6.1 Hz, 1H), 7.02 (d, J = 8.2 Hz, 1H), 4.66 (t, J = 5.1 Hz, 2H), 4.53 (s, 2H), 3.70 (t, J = 5.0 Hz, 2H), 3.21 (s, 3H). Multiplet Report 19F NMR (376 MHz, DMSO-d6) δ −75.26 (d, J = 6.0 Hz), −120.98- −121.50 (m), −121.81 (d, J = 17.2 Hz), −122.42 (ddd, J = 17.3, 9.9, 6.1 Hz). |

Example 872. 2-[[4-[6-[[2,3-difluoro-4-(trifluoromethyl)phenyl]methoxy]-2-pyridyl]-2,5-difluoro-phenyl]methyl]-3-(2-methoxyethyl)benzimidazole-5-carboxylic acid Procedure 99

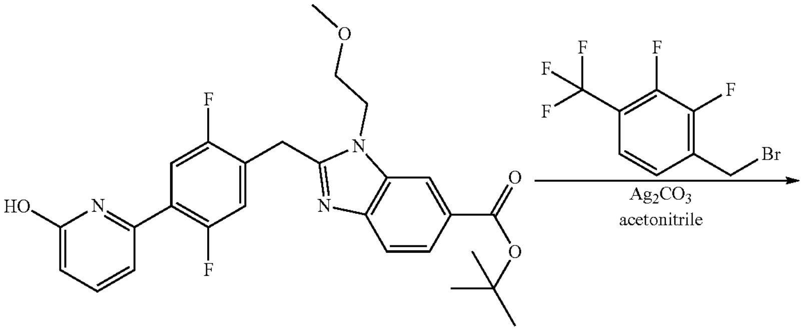

I-135

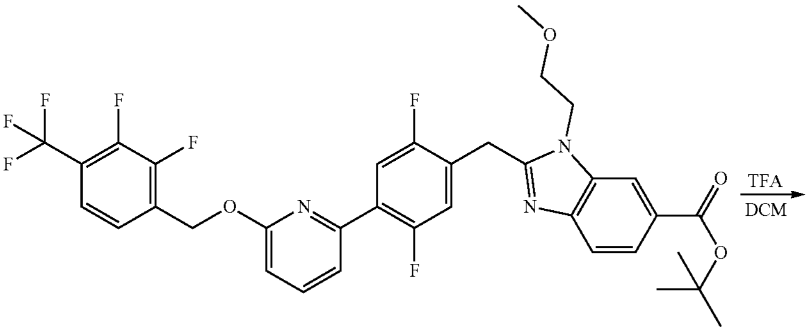

-continued

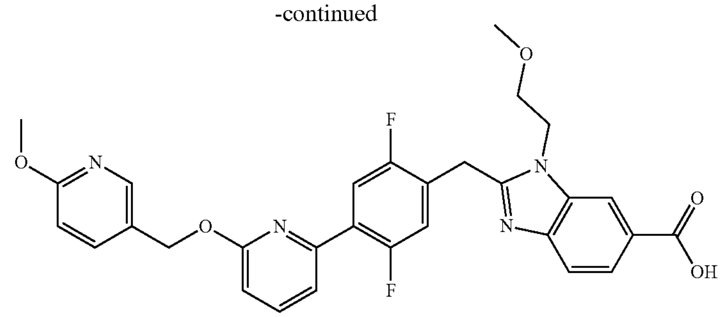

Example 866 tert-butyl 2-[[4-[6-[[2,3-difluoro-4-(trifluoromethyl)phenyl]methoxy]-2-pyridyl]-2,5-difluoro-phenyl]methyl]-3-(2-methoxyethyl)benzimidazole-5-carboxylate: A suspension of 1-(bromomethyl)-2,3-difluoro-4-(trifluoromethyl)benzene (73 mg, 0.26 mmol), tert-butyl 2-[[2,5-difluoro-4-(6-hydroxy-2-pyridyl)phenyl]methyl]-3-(2-methoxyethyl)benzimidazole-5-carboxylate (100 mg, 0.20 mmol), and silver carbonate (119 mg, 0.43 mmol) in CH3CN (2 mL) was heated at 50° C. overnight. The mixture was diluted with EtOAc and washed with brine twice. The organic extract was dried over sodium sulfate, filtered and concentrated. The crude residue was purified by flash chromatography (20-40% EtOAc in hexane) to yield desired product. ES/MS: 690.5 ($M+H^+$); 1H (400 MHz, Chloroform-d) δ 8.07 (d, J=1.5 Hz, 1H), 7.96 (dd, J=8.5, 1.5 Hz, 1H), 7.83-7.74 (m, 2H), 7.71 (t, J=7.9 Hz, 1H), 7.56-7.47 (m, 1H), 7.46-7.34 (m, 2H), 7.09 (dd, J=11.3, 6.0 Hz, 1H), 6.84 (dd, J=8.3, 0.7 Hz, 1H), 5.61 (s, 2H), 4.45 (s, 2H), 4.38 (t, J=5.2 Hz, 2H), 3.69 (t, J=5.2 Hz, 2H), 3.28 (s, 3H), 1.65 (s, 9H).

2-[[4-[6-[[2,3-difluoro-4-(trifluoromethyl)phenyl]methoxy]-2-pyridyl]-2,5-difluoro-phenyl]methyl]-3-(2-methoxyethyl)benzimidazole-5-carboxylic acid (Example 872): A solution of tert-butyl 2-[[4-[6-[[2,3-difluoro-4-(trifluoromethyl)phenyl]methoxy]-2-pyridyl]-2,5-difluoro-phenyl]methyl]-3-(2-methoxyethyl)benzimidazole-5-carboxylate (56.9 mg, 0.0825 mmol) and TFA (0.125 mL, 1.65 mmol) in DCM (3 mL) was heated at 40° C. Upon completion, the reaction mixture was concentrated directly and purified by RP-HPLC (eluent: MeCN/$H_2O$) to yield the product as a trifluoroacetate salt. ES/MS: 634.1 ($M+H^+$); 1H NMR (400 MHz, DMSO-d6) δ 8.27 (d, J=1.4 Hz, 1H), 7.94-7.87 (m, 1H), 7.85 (dd, J=8.5, 1.5 Hz, 1H), 7.73 (dd, J=10.5, 6.4 Hz, 1H), 7.70-7.55 (m, 3H), 7.54 (dd, J=7.5, 1.7 Hz, 1H), 7.44-7.35 (m, 1H), 7.01 (d, J=8.3 Hz, 1H), 5.65 (s, 2H), 4.64 (t, J=5.1 Hz, 2H), 4.50 (s, 2H), 3.69 (d, J=5.2 Hz, 2H), 3.21 (s, 3H).

Examples 868-871 and 873-876. Compounds Prepared Using Procedure 99

Other compounds of the present disclosure prepared using the general route described in Procedure 99 include the following Examples.

| Example | Structure/Name/Characterization |
| --- | --- |
| 868 | 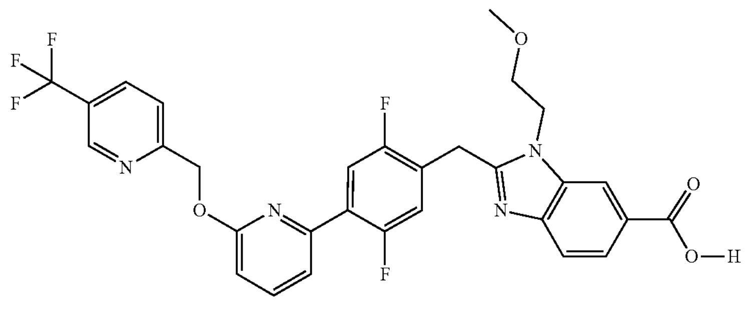 [SMILES: COCCn1c(Cc2cc(F)c(-c3cccc(OCc4ccc(C(F)(F)F)cn4)n3)cc2F)nc2ccc(C(=O)O)cc21]<br>ES/MS m/z 599.2; 1H NMR (400 MHz, DMSO-d6) δ 9.02-8.93 (m, 1H), 8.30 (d, J = 1.4 Hz, 1H), 8.24 (dd, J = 8.4, 2.4 Hz, 1H), 7.96-7.89 (m, 1H), 7.87 (dd, J = 8.5, 1.5 Hz, 1H), 7.70 (d, J = 8.3 Hz, 1H), 7.65 (d, J = 8.5 Hz, 1H), 7.56-7.49 (m, 2H), 7.39 (dd, J = 11.5, 6.1 Hz, 1H), 7.07 (d, J = 8.2 Hz, 1H), 5.65 (s, 2H), 4.65 (t, J = 5.1 Hz, 2H), 4.50 (s, 2H), 3.69 (t, J = 5.0 Hz, 2H), 3.20 (s, 3H). |

-continued

| Example | Structure/Name/Characterization |
| --- | --- |
| 869 | 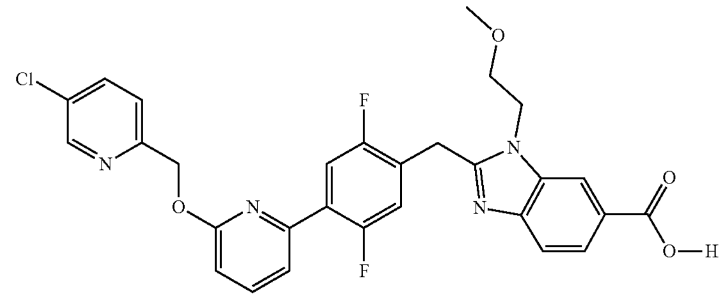 [SMILES: COCCn1c(Cc2cc(F)c(-c3cccc(OCc4ccc(Cl)cn4)n3)cc2F)nc2ccc(C(=O)O)cc21] ES/MS m/z 565.2; 1H NMR (400 MHz, DMSO-d6) δ 8.63 (d, J = 2.4 Hz, 1H), 8.31 (d, J = 1.5 Hz, 1H), 7.95 (dd, J = 8.4, 2.5 Hz, 1H), 7.93-7.85 (m, 2H), 7.70-7.64 (m, 2H), 7.56-7.50 (m, 2H), 7.41 (dd, J = 11.5, 6.1 Hz, 1H), 7.02 (d, J = 8.2 Hz, 1H), 5.54 (s, 2H), 4.66 (t, J = 5.1 Hz, 2H), 4.52 (s, 2H), 3.70 (t, J = 5.0 Hz, 2H), 3.21 (s, 3H). |
| 870 | 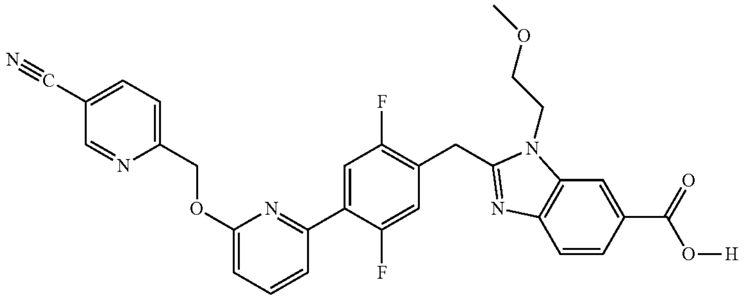 [SMILES: COCCn1c(Cc2cc(F)c(-c3cccc(OCc4ccc(C#N)cn4)n3)cc2F)nc2ccc(C(=O)O)cc21] ES/MS m/z 556.2; 1H NMR (400 MHz, DMSO-d6) δ 9.03 (d, J = 2.1 Hz, 1H), 8.33 (dd, J = 8.2, 2.2 Hz, 1H), 8.28 (d, J = 1.4 Hz, 1H), 7.92 (t, J = 7.9 Hz, 1H), 7.86 (dd, J = 8.4, 1.5 Hz, 1H), 7.66 (dd, J = 14.0, 8.3 Hz, 2H), 7.59-7.50 (m, 2H), 7.39 (dd, J = 11.5, 6.1 Hz, 1H), 7.06 (d, J = 8.2 Hz, 1H), 5.64 (s, 2H), 4.64 (t, J = 5.1 Hz, 2H), 4.49 (s, 2H), 3.69 (t, J = 5.0 Hz, 2H), 3.21 (s, 3H). |
| 871 | 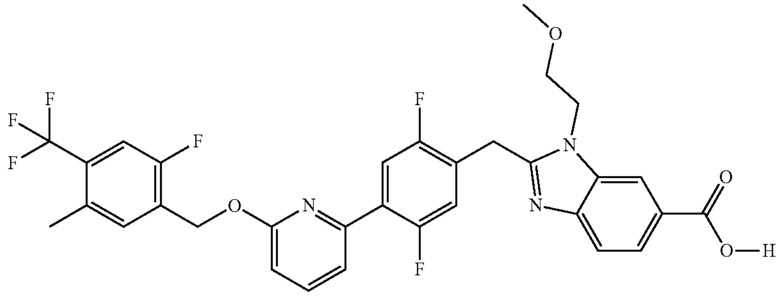 [SMILES: COCCn1c(Cc2cc(F)c(-c3cccc(OCc4cc(C)c(C(F)(F)F)cc4F)n3)cc2F)nc2ccc(C(=O)O)cc21] ES/MS MH+ 630.2; 1H NMR (400 MHz, DMSO-d6) δ 8.29 (d, J = 1.4 Hz, 1H), 7.95-7.82 (m, 2H), 7.79 (dd, J = 10.5, 6.4 Hz, 1H), 7.72-7.56 (m, 4H), 7.53 (dd, J = 7.5, 1.7 Hz, 1H), 7.42 (dd, J = 11.5, 6.0 Hz, 1H), 6.98 (d, J = 8.2 Hz, 1H), 5.55 (s, 2H), 4.65 (t, J = 5.0 Hz, 2H), 4.52 (s, 2H), 3.70 (t, J = 5.0 Hz, 2H), 3.21 (s, 3H), 2.42 (s, 3H). Multiplet Report 19F NMR (376 MHz, DMSO-d6) δ −61.18, −75.19, −119.56--121.54 (m), −121.83 (d, J = 10.9 Hz), −122.21- −123.52 (m). |

-continued

| Example | Structure/Name/Characterization |
|---|---|
| 873 | 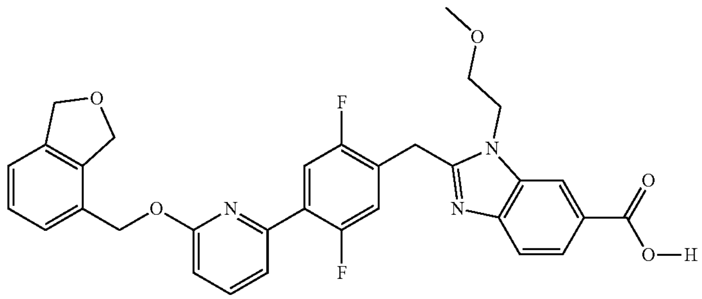 [SMILES: COCCn1c(Cc2cc(F)c(-c3cccc(OCc4cccc5c4COC5)n3)cc2F)nc2ccc(C(=O)O)cc21] ES/MS m/z 572.2; 1H NMR (400 MHz, DMSO) δ 8.31 (d, J = 1.6 Hz, 1H), 7.91-7.83 (m, 2H), 7.79 (dd, J = 10.5, 6.4 Hz, 1H), 7.66 (d, J = 8.5 Hz, 1H), 7.50 (dd, J = 7.2, 1.8 Hz, 1H), 7.47-7.36 (m, 2H), 7.35-7.24 (m, 2H), 6.97 (d, J = 8.2 Hz, 1H), 5.45 (s, 2H), 5.11 (d, J = 2.1 Hz, 2H), 5.03 (d, J = 2.2 Hz, 2H), 4.66 (t, J = 5.1 Hz, 2H), 4.53 (s, 2H), 3.70 (t, J = 5.0 Hz, 2H), 3.22 (s, 3H) 19F NMR (377 MHz, DMSO) δ −121.66--121.99 (m), −122.30 (ddd, J = 17.5, 10.6, 6.2 Hz). |
| 874 | 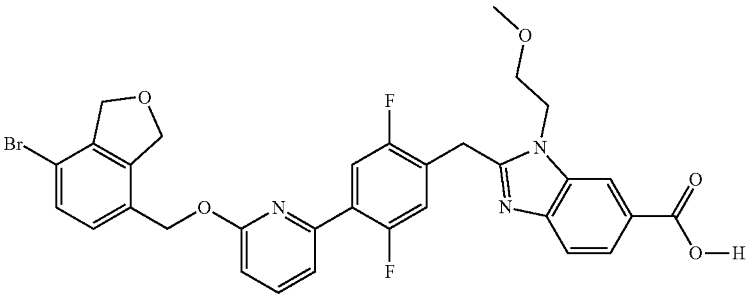 [SMILES: COCCn1c(Cc2cc(F)c(-c3cccc(OCc4ccc(Br)c5c4COC5)n3)cc2F)nc2ccc(C(=O)O)cc21] ES/MS m/z 650; 1H NMR (400 MHz, DMSO) δ 8.27 (d, J = 1.6 Hz, 1H), 7.92-7.81 (m, 2H), 7.78 (dd, J = 10.5, 6.4 Hz, 1H), 7.64 (d, J = 8.5 Hz, 1H), 7.55-7.46 (m, 2H), 7.45-7.31 (m, 2H), 6.97 (d, J = 8.3 Hz, 1H), 5.42 (s, 2H), 5.24 (d, J = 2.3 Hz, 2H), 5.00 (d, J = 2.3 Hz, 2H), 4.64 (t, J = 5.1 Hz, 2H), 4.50 (s, 2H), 3.70 (t, J = 5.0 Hz, 2H), 3.22 (s, 3H). 19F NMR (377 MHz, DMSO) δ −121.91, −122.34 (ddd, J = 17.2, 10.2, 5.9 Hz). |
| 875 | 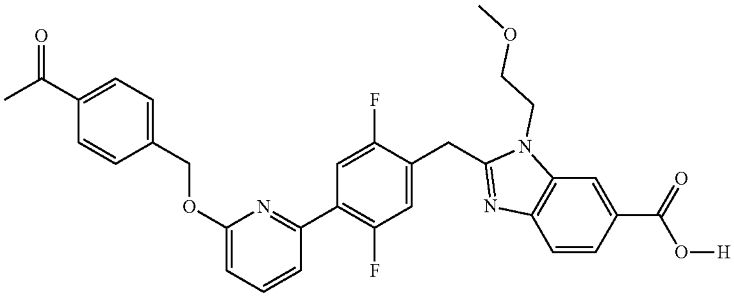 [SMILES: COCCn1c(Cc2cc(F)c(-c3cccc(OCc4ccc(C(C)=O)cc4)n3)cc2F)nc2ccc(C(=O)O)cc21] ES/MS m/z 572.3; 1H NMR (400 MHz, DMSO-d6) δ 8.27 (d, 1H), 8.00-7.95 (m, 2H), 7.92-7.87 (m, 1H), 7.85 (dd, 1H), 7.76 (dd, 1H), 7.63 (dd, 3H), 7.51 (dd, 1H), 7.40 (dd, 1H), 7.00 (d, 1H), 5.57 (s, 2H), 4.63 (t, 2H), 4.49 (s, 2H), 3.69 (t, 2H), 3.21 (s, 3H), 2.58 (s, 3H). |

-continued
| Example | Structure/Name/Characterization |
| --- | --- |
| 876 | 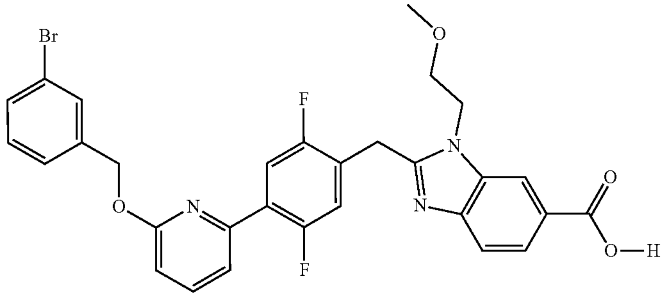 [SMILES: COCCn1c(Cc2cc(F)c(-c3cccc(OCc4cccc(Br)c4)n3)cc2F)nc2ccc(C(=O)O)cc21] ES/MS m/z 608.9, 610.1; 1H NMR (400 MHz, DMSO-d6) δ 8.31 (d, 1H), 7.88 (ddd, 2H), 7.81 (dd, 1H), 7.71 (t, 1H), 7.66 (d, 1H), 7.55-7.48 (m, 3H), 7.42 (dd, 1H), 7.36 (t, 1H), 6.98 (d, 1H), 5.47 (s, 2H), 4.67 (t, 2H), 4.53 (s, 2H), 3.70 (t, 2H), 3.22 (s, 3H). |
Example 879. 2-[[4-[2-[(4-cyano-2-fluoro-phenyl)methoxy]-5-fluoro-pyrimidin-4-yl]-2,5-difluoro-phenyl]methyl]-3-[[(2S)-oxetan-2-yl]methyl]benzimidazole-5-carboxylic acid
Procedure 100
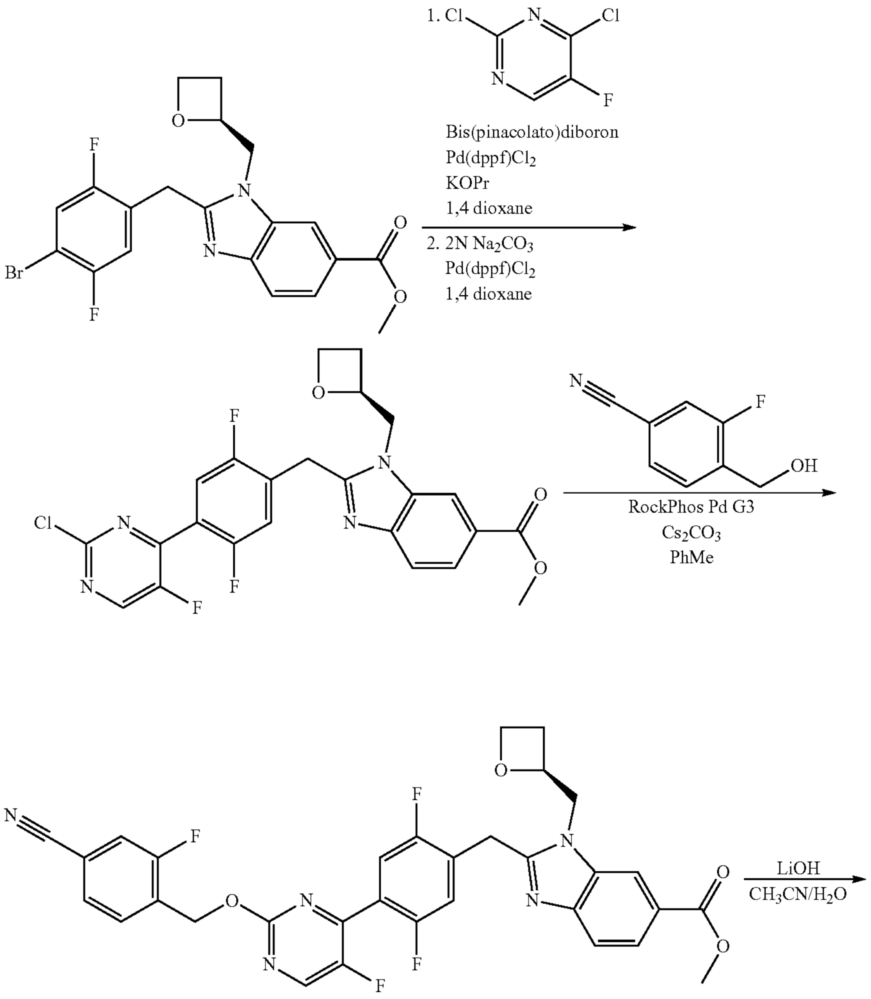

-continued

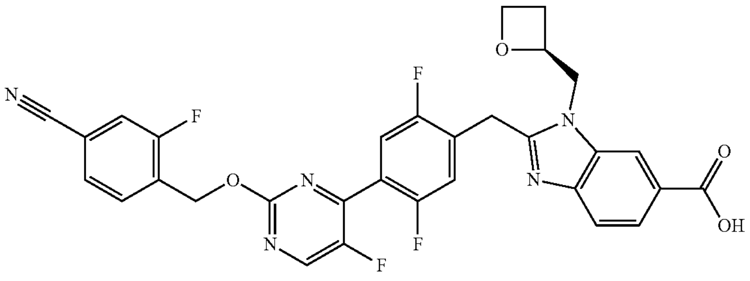

Example 879

Methyl 2-[[4-(2-chloro-5-fluoro-pyrimidin-4-yl)-2,5-difluoro-phenyl]methyl]-3-[[(2S)-oxetan-2-yl]methyl]benzimidazole-5-carboxylate: A suspension of methyl 2-[(4-bromo-2,5-difluoro-phenyl)methyl]-3-[[(2S)-oxetan-2-yl]methyl]benzimidazole-5-carboxylate (350 mg, 0.776 mmol), made as described for I-164 substituting ethyl (S)-4-amino-3-fluoro-5-((oxetan-2-ylmethyl)amino)benzoate (I-62) with methyl (S)-4-amino-3-((oxetan-2-ylmethyl)amino)benzoate and 2-(4-bromo-2-fluorophenyl)acetic acid with 2-(4-bromo-2,5-difluorophenyl)acetic acid, Bis(pinacolato)diboron (256 mg, 1.01 mmol), [1,1'-Bis(diphenylphosphino)ferrocene]dichloropalladium(II); PdCl2 (dppf) (86.3 mg, 0.116 mmol), and potassium propionate (261 mg, 2.33 mmol) in dioxane (5 mL) was degassed with argon for 4 min, then heated at 110° C. for 40 min. The mixture was cooled to rt, then sodium carbonate was added (2 M, 0.776 mL, 1.55 mmol). After 5 min, added 2,4-dichloro-5-fluoro-pyrimidine (130 mg, 0.776 mmol) and [1,1'-Bis(diphenylphosphino)ferrocene]dichloropalladium (II); PdCl2(dppf) (43.1 mg, 0.0582 mmol) were added. The mixture was degassed for 5 min with argon, then heated at 80° C. for 2 hr. The mixture was diluted with EtOAc and washed with brine and saturated sodium bicarbonate solution. The organic extract was dried over sodium sulfate, filtered and concentrated. The crude residue was purified by flash chromatography (50-75% EtOAc in hexane) to yield desired product. ES/MS m/z: 503.0 (M+H$^+$); 1H NMR (400 MHz, Chloroform-d) δ 8.59 (d, J=1.5 Hz, 1H), 8.11 (d, J=1.6 Hz, 1H), 8.01 (dd, J=8.5, 1.5 Hz, 1H), 7.79 (d, J=8.5 Hz, 1H), 7.50 (dd, J=9.2, 5.5 Hz, 1H), 7.23 (dd, J=9.8, 5.8 Hz, 1H), 5.19 (tt, J=7.2, 3.4 Hz, 1H), 4.72-4.44 (m, 5H), 4.42-4.31 (m, 2H), 3.97 (s, 3H), 2.77 (dtd, J=11.5, 8.1, 6.0 Hz, 1H), 2.43 (ddt, J=11.5, 9.2, 7.2 Hz, 1H).

Methyl 2-[[4-[2-[(4-cyano-2-fluoro-phenyl)methoxy]-5-fluoro-pyrimidin-4-yl]-2,5-difluoro-phenyl]methyl]-3-[[(2S)-oxetan-2-yl]methyl]benzimidazole-5-carboxylate: A suspension of methyl 2-[[4-(2-chloro-5-fluoro-pyrimidin-4-yl)-2,5-difluoro-phenyl]methyl]-3-[[(2S)-oxetan-2-yl]methyl]benzimidazole-5-carboxylate (100 mg, 0.199 mmol), 3-fluoro-4-(hydroxymethyl)benzonitrile (60.1 mg, 0.398 mmol), Pd RockPhos G3 (12.5 mg, 0.0149 mmol), and cesium carbonate (194 mg, 0.597 mmol) in toluene (2 mL) was degassed with Ar for 5 min, then heated at 90° C. overnight. The mixture was diluted with EtOAc and washed with brine. The organic extract was dried over sodium sulfate, filtered and concentrated. The crude residue was purified by flash chromatography (40-60% EtOAc in hexane) to yield desired product. ES/MS m/z: 618.2 (M+H$^+$); $^1$H NMR (400 MHz, Chloroform-d) δ 8.50 (d, J=1.5 Hz, 1H), 8.12 (d, J=1.5 Hz, 1H), 8.02 (dd, J=8.5, 1.5 Hz, 1H), 7.80 (d, J=8.6 Hz, 1H), 7.72 (t, J=7.5 Hz, 1H), 7.50 (dd, J=8.0, 1.5 Hz, 1H), 7.46-7.38 (m, 2H), 7.22 (dd, J=9.9, 5.8 Hz, 1H), 5.58 (s, 2H), 5.20 (q, J=6.2 Hz, 1H), 4.71-4.63 (m, 1H), 4.63-4.44 (m, 3H), 4.40 (ddd, J=12.0, 6.2, 3.0 Hz, 2H), 3.97 (s, 3H), 2.85-2.60 (m, 1H), 2.50-2.33 (m, 1H).

2-[[4-[2-[(4-cyano-2-fluoro-phenyl)methoxy]-5-fluoro-pyrimidin-4-yl]-2,5-difluoro-phenyl]methyl]-3-[[(2S)-oxetan-2-yl]methyl]benzimidazole-5-carboxylic acid (Example 879): A suspension of methyl 2-[[4-[2-[(4-cyano-2-fluoro-phenyl)methoxy]-5-fluoro-pyrimidin-4-yl]-2,5-difluoro-phenyl]methyl]-3-[[(2S)-oxetan-2-yl]methyl]benzimidazole-5-carboxylate (28.8 mg, 0.0466 mmol) and lithium hydroxide, monohydrate (0.300 M, 0.466 mL, 0.140 mmol) in CH3CN (3 mL) in a 40 ml reaction vial was heated at 90° C. for 3 hr. The mixture was diluted with EtOAc and brine. Added 0.150 mL of 1 M citric acid. The organic extract was dried over sodium sulfate, filtered and concentrated. The crude residue was purified by RP-HPLC (eluent: MeCN/$H_2O$). The resulting product fractions were diluted with EtOAc and neutralized with sodium bicarbonate solution. The organic extract was dried over sodium sulfate, filtered and concentrated to give the titled product. ES/MS m/z: 604.2 (M+H$^+$); 1H NMR (400 MHz, DMSO-d6) δ 8.90 (d, J=1.8 Hz, 1H), 8.26 (d, J=1.5 Hz, 1H), 7.94 (d, J=10.1 Hz, 1H), 7.84-7.71 (m, 3H), 7.66-7.54 (m, 2H), 7.51 (dd, J=10.2, 5.9 Hz, 1H), 5.58 (s, 2H), 5.09 (d, J=7.8 Hz, 1H), 4.77 (dd, J=15.7, 7.0 Hz, 1H), 4.71-4.43 (m, 4H), 4.35 (dt, J=8.9, 5.9 Hz, 1H), 2.71 (dd, J=18.9, 10.1 Hz, 1H), 2.45-2.25 (m, 1H); 19F NMR (376 MHz, DMSO-d6) δ −73.96, −115.67 (d, J=10.6 Hz), −119.20, −120.30--124.71 (m), −145.39 (d, J=35.7 Hz).

Example 877-878, 880-886. Compounds Prepared Using Procedure 100

Other compounds of the present disclosure prepared using the general route described in Procedure 100 include the following Examples.

| Example | Structure/Name/Characterization |
|---|---|
| 877 | 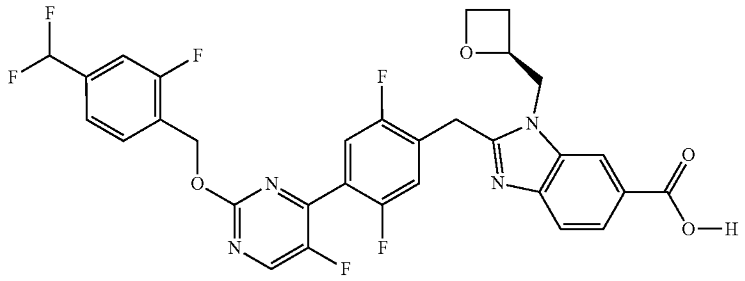 [SMILES: O=C(O)c1ccc2nc(Cc3cc(F)c(-c4nc(OCc5ccc(C(F)F)cc5F)ncc4F)cc3F)n(C[C@@H]3CCO3)c2c1]<br>ES/MS (M + H +) 629.1; 1H NMR (400 MHz, DMSO-d6) δ 8.90 (d, J = 1.7 Hz, 1H), 8.26 (s, 1H), 7.84-7.76 (m, 1H), 7.74 (t, J = 7.6 Hz, 1H), 7.60 (dd, J = 10.3, 6.9 Hz, 2H), 7.50 (dd, J = 14.8, 8.9 Hz, 3H), 7.08 (t, J = 55.6 Hz, 1H), 5.55 (s, 2H), 5.09 (d, J = 7.3 Hz, 1H), 4.77 (dd, J = 15.6, 7.0 Hz, 1H), 4.70-4.57 (m, 1H), 4.56-4.43 (m, 3H), 4.42-4.30 (m, 1H), 2.72 (m, 1H), 2.41 (m, 1H). Multiplet Report 19F NMR (376 MHz, DMSO-d6) δ −73.95, −110.90 (d, J = 55.4 Hz), −113.95--118.73 (m), −119.26, −121.88, −145.64. |
| 878 | 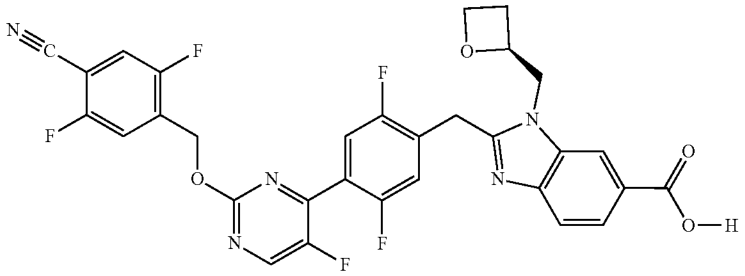 [SMILES: N#Cc1cc(F)c(COc2ncc(F)c(-c3cc(F)c(Cc4nc5ccc(C(=O)O)cc5n4C[C@@H]4CCO4)cc3F)n2)cc1F]<br>ES/MS (M + H +) 622.1; 1H NMR (400 MHz, DMSO-d6) δ 8.90 (d, J = 1.7 Hz, 1H), 8.26 (d, J = 1.5 Hz, 1H), 8.07 (dd, J = 9.2, 5.2 Hz, 1H), 7.79 (dd, J = 8.4, 1.5 Hz, 1H), 7.74 (dd, J = 9.3, 5.6 Hz, 1H), 7.65-7.54 (m, 2H), 7.51 (dd, J = 10.2, 5.8 Hz, 1H), 5.56 (s, 2H), 5.15-5.03 (m, 1H), 4.77 (dd, J = 15.6, 7.0 Hz, 1H), 4.69-4.38 (m, 4H), 4.36 (dt, J = 9.0, 5.9 Hz, 1H), 2.81-2.59 (m, 1H), 2.46-2.24 (m, 1H). Multiplet Report 19F NMR (376 MHz, DMSO-d6) δ −73.95, −112.13--113.98 (m), −118.02--120.06 (m), −120.81 (ddd, J = 15.9, 9.2, 5.7 Hz), −121.65--123.42 (m), −145.24 (d, J = 36.0 Hz). |
| 880 | 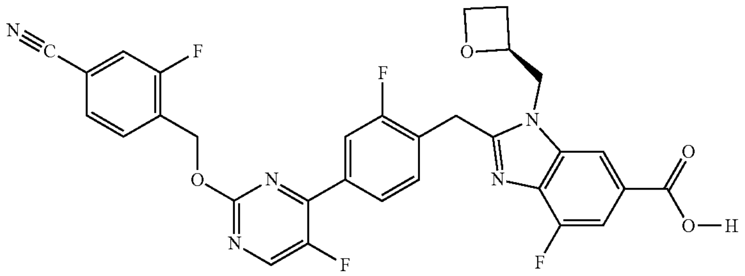 [SMILES: N#Cc1ccc(COc2ncc(F)c(-c3ccc(Cc4nc5c(F)cc(C(=O)O)cc5n4C[C@@H]4CCO4)c(F)c3)n2)c(F)c1]<br>ES/MS m/z 604.2; 1H NMR (400 MHz, DMSO) δ 8.84 (d, J = 3.2 Hz, 1H), 8.14 (d, J = 1.3 Hz, 1H), 7.94 (dd, J = 10.0, 1.4 Hz, 1H), 7.91-7.84 (m, 2H), 7.81-7.72 (m, 2H), 7.57 (t, J = 7.9 Hz, 1H), 7.49 (dd, J = 11.4, 1.2 Hz, 1H), 5.60 (s, 2H), 5.11-5.00 (m, 1H), 4.77 (dd, J = 15.6, 7.1 Hz, 1H), 4.68-4.45 (m, 4H), 4.35 (dt, J = 9.1, 6.0 Hz, 1H), 2.76-2.67 (m, 1H), 2.41-2.34 (m, 1H). |

-continued

| Example | Structure/Name/Characterization |
|---|---|
| 881 | 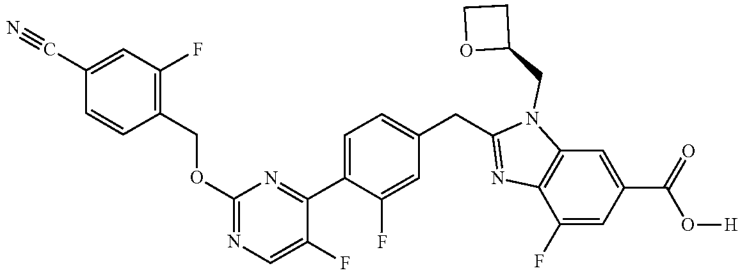 [SMILES: N#Cc1ccc(COc2ncc(F)c(-c3ccc(Cc4nc5c(F)cc(C(=O)O)cc5n4C[C@@H]4CCO4)cc3F)n2)c(F)c1]<br>ES/MS m/z 604.2; 1H NMR (400 MHz, DMSO) δ 8.84 (d, J = 1.8 Hz, 1H), 8.13 (d, J = 1.3 Hz, 1H), 7.96-7.89 (m, 1H), 7.79-7.72 (m, 2H), 7.66 (t, J = 7.7 Hz, 1H), 7.51 (dd, J = 11.4, 1.3 Hz, 1H), 7.42 (d, J = 11.3 Hz, 1H), 7.38 (dd, J = 8.0, 1.5 Hz, 1H), 5.54 (s, 2H), 5.06-4.94 (m, 1H), 4.75 (dd, J = 15.5, 7.2 Hz, 1H), 4.64-4.56 (m, 1H), 4.54 (d, J = 3.3 Hz, 2H), 4.50-4.42 (m, 1H), 4.35 (dt, J = 9.0, 5.9 Hz, 1H), 2.74-2.61 (m, 1H), 2.40-2.29 (m, 1H). |
| 882 | 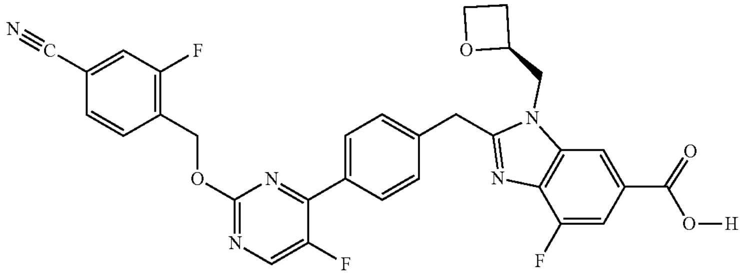 [SMILES: N#Cc1ccc(COc2ncc(F)c(-c3ccc(Cc4nc5c(F)cc(C(=O)O)cc5n4C[C@@H]4CCO4)cc3)n2)c(F)c1]<br>ES/MS m/z 586.2; 1H NMR (400 MHz, DMSO) δ 13.05 (s, 1H), 8.78 (d, J = 3.3 Hz, 1H), 8.13 (d, J = 1.3 Hz, 1H), 8.06-7.99 (m, 2H), 7.97-7.90 (m, 1H), 7.81-7.71 (m, 2H), 7.58-7.46 (m, 3H), 5.57 (s, 2H), 5.02-4.89 (m, 1H), 4.71 (dd, J = 15.5, 7.2 Hz, 1H), 4.62-4.41 (m, 4H), 4.34 (dt, J = 9.1, 5.9 Hz, 1H), 2.72-2.57 (m, 1H), 2.41-2.27 (m, 1H). |
| 883 | 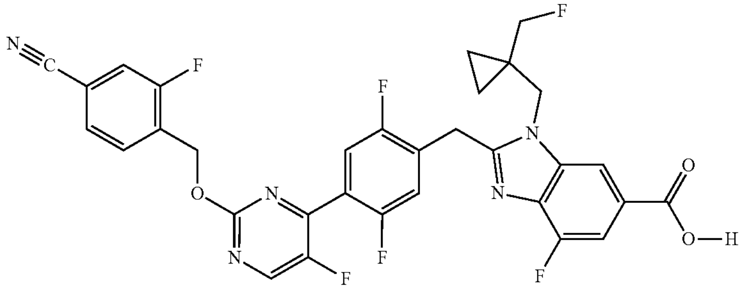 [SMILES: N#Cc1ccc(COc2ncc(F)c(-c3cc(F)c(Cc4nc5c(F)cc(C(=O)O)cc5n4CC4(CF)CC4)cc3F)n2)c(F)c1]<br>ES/MS 638.0; 1H NMR (400 MHz, DMSO) δ 8.89 (d, J = 1.8 Hz, 1H), 8.13 (d, J = 1.3 Hz, 1H), 7.97-7.89 (m, 1H), 7.81-7.71 (m, 2H), 7.60 (dd, J = 9.5, 5.7 Hz, 1H), 7.56-7.47 (m, 2H), 5.57 (s, 2H), 4.58 (s, 2H), 4.50 (s, 2H), 4.24 (s, 1H), 4.12 (s, 1H), 0.89-0.81 (m, 2H), 0.76-0.68 (m, 2H). |
| 884 | 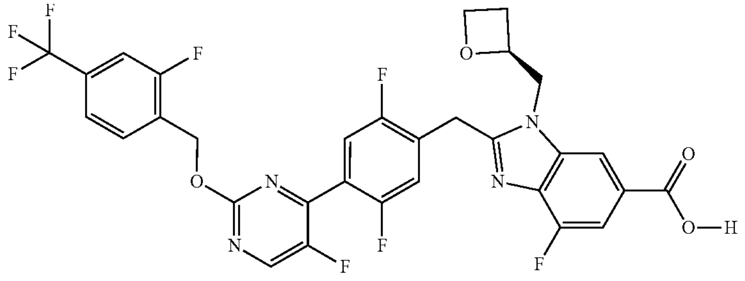 [SMILES: O=C(O)c1cc(F)c2nc(Cc3cc(F)c(-c4nc(OCc5ccc(C(F)(F)F)cc5F)ncc4F)cc3F)n(C[C@@H]3CCO3)c2c1]<br>ES/MS m/z 665.0; 1H NMR (400 MHz, DMSO) δ 13.08 (s, 1H), 8.89 (d, J = 1.8 Hz, 1H), 8.15 (d, J = 1.3 Hz, 1H), 7.81 (t, J = 7.6 Hz, 1H), 7.76 (dd, J = 10.1, 1.7 Hz, 1H), 7.65 (dd, J = 8.2, 1.8 Hz, 1H), 7.59 (dd, J = 9.5, 5.7 Hz, 1H), |

-continued

| Example | Structure/Name/Characterization |
| --- | --- |
| | 7.55-7.46 (m, 2H), 5.58 (s, 2H), 5.08 (qd, J = 7.1, 2.7 Hz, 1H), 4.80 (dd, J = 15.5, 7.0 Hz, 1H), 4.66 (dd, J = 15.5, 2.7 Hz, 1H), 4.62-4.46 (m, 3H), 4.35 (dt, J = 9.0, 5.9 Hz, 1H), 2.78-2.64 (m, 1H), 2.44-2.30 (m, 1H). |
| 885 | 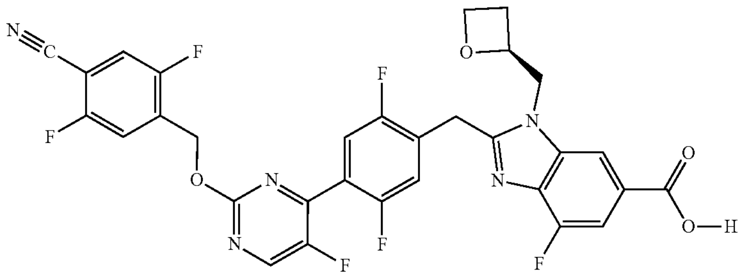 [SMILES: N#Cc1cc(F)c(COc2ncc(F)c(-c3cc(F)c(Cc4nc5c(F)cc(C(=O)O)cc5n4C[C@@H]4CCO4)cc3F)n2)cc1F] ES/MS m/z 640.2; 1H NMR (400 MHz, DMSO) δ 13.09 (s, 1H), 8.90 (d, J = 1.7 Hz, 1H), 8.15 (d, J = 1.3 Hz, 1H), 8.06 (dd, J = 9.1, 5.2 Hz, 1H), 7.74 (dd, J = 9.2, 5.6 Hz, 1H), 7.59 (dd, J = 9.5, 5.7 Hz, 1H), 7.54-7.47 (m, 2H), 5.55 (s, 2H), 5.08 (qd, J = 7.0, 2.7 Hz, 1H), 4.80 (dd, J = 15.6, 7.1 Hz, 1H), 4.66 (dd, J = 15.6, 2.7 Hz, 1H), 4.62-4.46 (m, 3H), 4.35 (dt, J = 9.0, 5.9 Hz, 1H), 2.83-2.63 (m, 1H), 2.43-2.32 (m, 1H). |
| 886 | 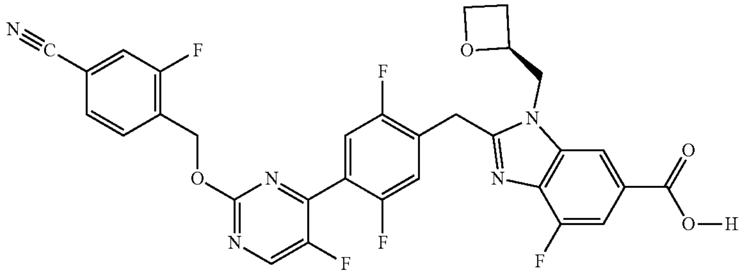 [SMILES: N#Cc1ccc(COc2ncc(F)c(-c3cc(F)c(Cc4nc5c(F)cc(C(=O)O)cc5n4C[C@@H]4CCO4)cc3F)n2)c(F)c1] ES/MS m/z 622.0; 1H NMR (400 MHz, DMSO) δ 13.08 (s, 1H), 8.89 (d, J = 1.8 Hz, 1H), 8.15 (d, J = 1.3 Hz, 1H), 7.97-7.91 (m, 1H), 7.83-7.72 (m, 2H), 7.60 (dd, J = 9.5, 5.7 Hz, 1H), 7.54-7.46 (m, 2H), 5.57 (s, 2H), 5.12-5.02 (m, 1H), 4.80 (dd, J = 15.5, 7.1 Hz, 1H), 4.66 (dd, J = 15.5, 2.7 Hz, 1H), 4.62-4.46 (m, 3H), 4.35 (dt, J = 9.0, 6.0 Hz, 1H), 2.81-2.63 (m, 1H), 2.44-2.30 (m, 1H). |

Example 887. 2-[[4-[6-[(4-cyano-2-fluoro-phenyl)methoxy]-2-pyridyl]-2-fluoro-phenyl]methyl]-3-[[(2R)-1-(2,2-dimethylpropanoyl)azetidin-2-yl]methyl]benzimidazole-5-carboxylic acid Procedure 101

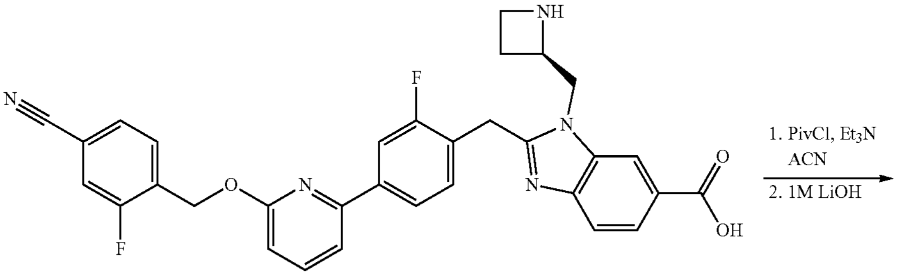

Example 395

-continued

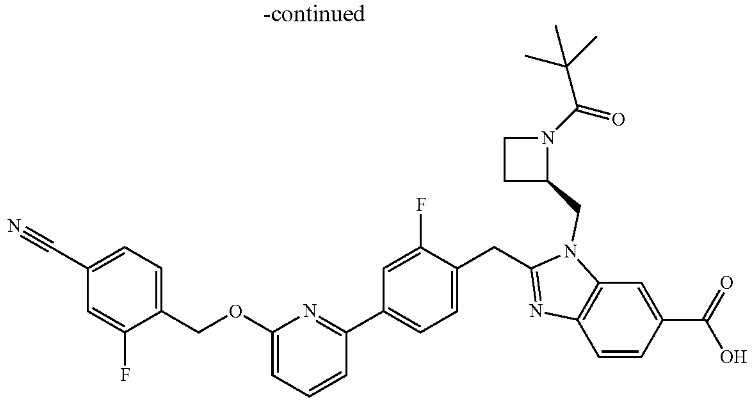

Example 887

2-[[4-[6-[(4-cyano-2-fluoro-phenyl)methoxy]-2-pyridyl]-2-fluoro-phenyl]methyl]-3-[[(2R)-1-(2,2-dimethylpropanoyl)azetidin-2-yl]methyl]benzimidazole-5-carboxylic acid (Example 887): 3-[[(2R)-azetidin-2-yl]methyl]-2-[[4-[6-[(4-cyano-2-fluoro-phenyl)methoxy]-2-pyridyl]-2-fluoro-phenyl]methyl]benzimidazole-5-carboxylic acid (0.181 g, 0.319 mmol) was dissolved in ACN (4 mL). Triethylamine (0.178 mL, 1.28 mmol) was added followed by pivaloyl chloride (96.2 mg, 0.798 mmol, 2.5 equiv.). The mixture was stirred at ambient temperature for 5 hours. ES/MS: 734.098 ($M+H^+$)

The reaction was quenched with water (1 mL) and excess LiOH (1 M, 2 mL) was added. The mixture was heated to 90° C. and stirred until starting material was consumed as shown by LCMS, about 7 hours. The mixture was cooled and acidified with 10% citric acid. The reaction was extracted with EtOAc (3x5 mL). The combined organic layers were washed with brine (10 mL), dried with sodium sulfate, filtered and concentrated in vacuo. The product was purified by preparatory HPLC to yield the titled product. ES/MS: 650.177 ($M+H^+$) 1H NMR (400 MHz, Methanol-d4) δ 8.60 (d, J=1.3 Hz, 1H), 8.20 (dd, J=8.6, 1.4 Hz, 1H), 7.97-7.87 (m, 2H), 7.82 (t, J=7.9 Hz, 1H), 7.78-7.64 (m, 2H), 7.67-7.50 (m, 4H), 6.92 (d, J=8.2 Hz, 1H), 5.65 (s, 2H), 5.04 (dd, J=14.4, 8.4 Hz, 1H), 4.79-4.69 (m, 2H), 4.50 (td, J=8.9, 6.1 Hz, 1H), 4.39 (td, J=9.1, 5.9 Hz, 1H), 2.72-2.47 (m, 1H), 2.21 (ddd, J=11.3, 9.1, 5.7 Hz, 1H), 0.98 (s, 9H) 19F NMR (376 MHz, Methanol-d4) δ −77.76, −117.47-−118.32 (m), −118.33-−119.12 (m).

Example 888. 2-[[4-[6-[(4-cyano-2-fluoro-phenyl)methoxy]-2-pyridyl]-2-fluoro-phenyl]methyl]-3-[[(2R)-1-methylsulfonylazetidin-2-yl]methyl]benzimidazole-5-carboxylic Acid Procedure 102

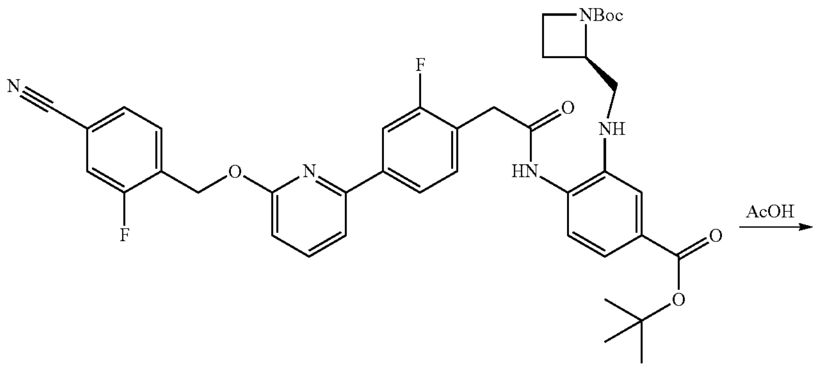

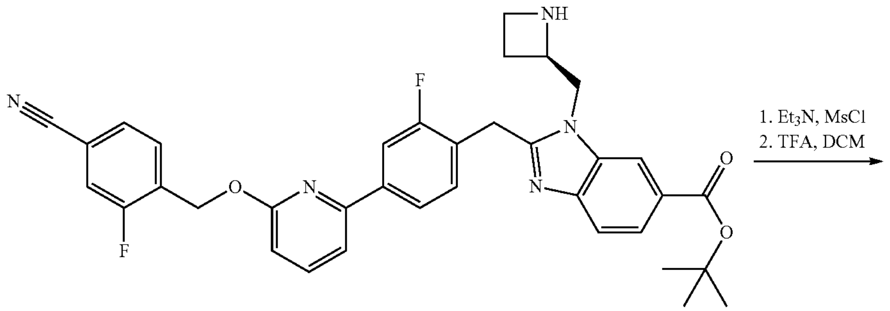

-continued

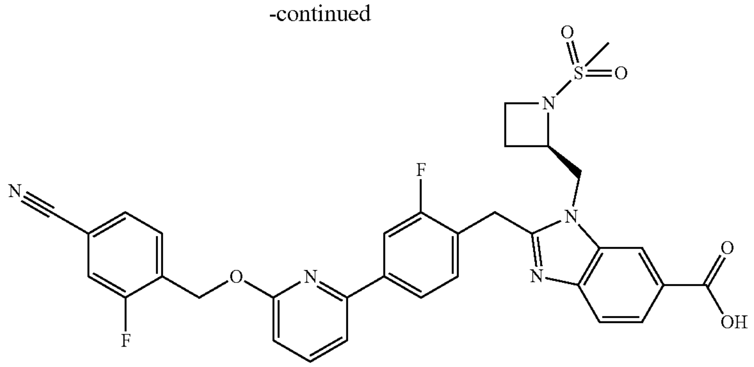

Example 888

2-[[4-[6-[(4-cyano-2-fluoro-phenyl)methoxy]-2-pyridyl]-2-fluoro-phenyl]methyl]-3-[[(2R)-1-methylsulfonylazetidin-2-yl]methyl]benzimidazole-5-carboxylic acid (Example 888): Tert-butyl 2-[[5-tert-butoxycarbonyl-2-[[2-[4-[6-[(4-cyano-2-fluoro-phenyl)methoxy]-2-pyridyl]-2-fluoro-phenyl]acetyl]amino]anilino]methyl]azetidine-1-carboxylate (0.598 g, 0.000808 mol), obtained as described in Procedure 43 substituting tert-butyl (S)-2-(((2-amino-5-(methoxycarbonyl)phenyl)amino)methyl)azetidine-1-carboxylate with tert-butyl (S)-2-(((2-amino-5-(tert-butoxycarbonyl)phenyl)amino)methyl)azetidine-1-carboxylate, was dissolved in acetic acid (10.0 mL) and heated to 110° C. for 3 hours. The mixture was cooled to ambient temperature and concentrated by rotary evaporation. The residue was purified by column chromatography (0-100% EtOAc in hexane). ES/MS: 622.200 ($M+H^+$).

Tert-butyl 3-[[(2R)-azetidin-2-yl]methyl]-2-[[4-[6-[(4-cyano-2-fluoro-phenyl)methoxy]-2-pyridyl]-2-fluoro-phenyl]methyl]benzimidazole-5-carboxylate (55.0 mg, 8.85e-2 mmol) was dissolved in DCM (1 mL). Triethylamine (0.0370 mL, 0.265 mmol) was added followed by methane sulfonyl chloride (0.060 g, 0.524 mmol). The mixture was stirred at ambient temperature overnight. ES/MS: 700.45 ($M+H^+$).

Excess TFA (0.5 mL) was added and the mixture was stirred at ambient temperature for 3 hours. The reaction was concentrated and purified by preparatory HPLC yielding the title compound. ES/MS: 644.197 ($M+H^+$) 1H NMR (400 MHz, Methanol-d4) δ 8.62 (d, J=1.0 Hz, 1H), 8.24 (dd, J=8.6, 1.4 Hz, 1H), 7.97-7.85 (m, 2H), 7.85-7.66 (m, 3H), 7.66-7.47 (m, 4H), 6.91 (d, J=8.2 Hz, 1H), 5.65 (s, 2H), 5.11-4.91 (m, 3H), 4.08-3.80 (m, 2H), 2.80 (s, 3H), 2.58 (d, J=14.9 Hz, 1H), 2.32 (q, J=9.8, 8.9 Hz, 1H). 19F NMR (376 MHz, Methanol-d4) δ −77.93, −117.75–−118.20 (m), −118.53 (dd, J=12.6, 8.2 Hz).

Example 889. 2-(4-(6-((4-cyano-2-fluorobenzyl)oxy)pyridin-2-yl)-2,5-difluorobenzyl)-1-((1-(cyclopropanecarbonyl)-3-methoxyazetidin-3-yl)methyl)-1H-benzo[d]imidazole-6-carboxylic acid Procedure 103

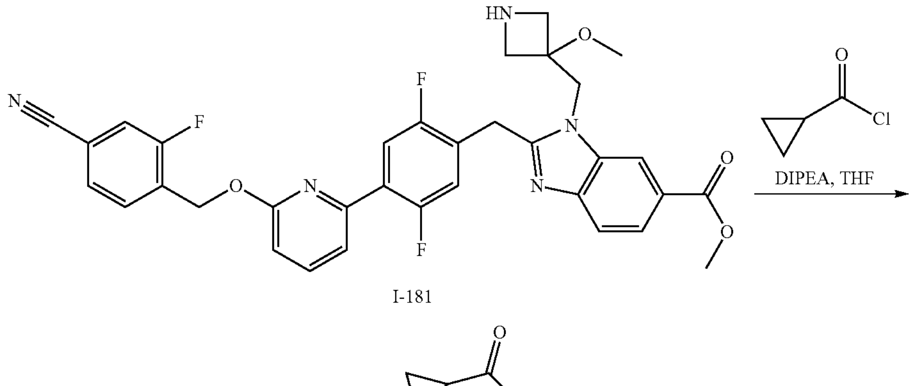

I-181

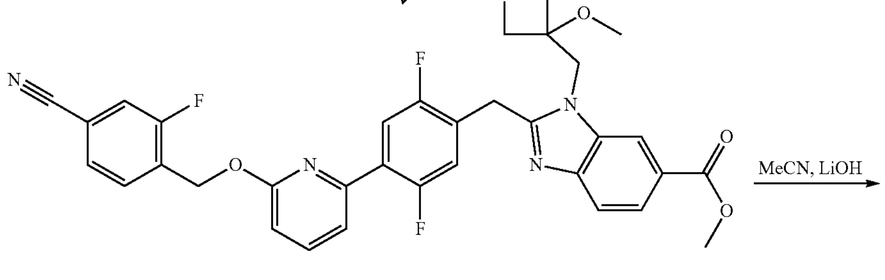

-continued

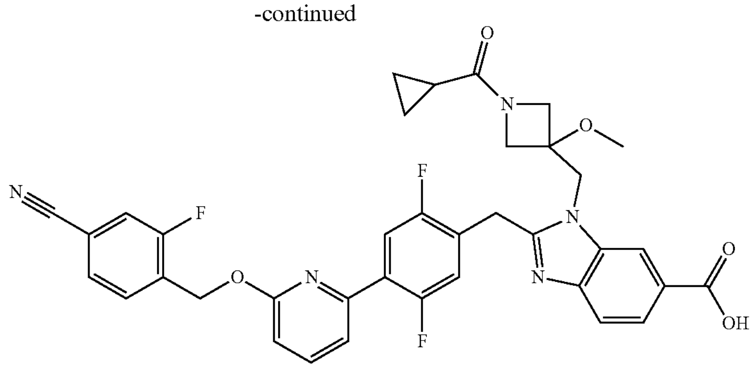

Example 889

Methyl 2-(4-(6-((4-cyano-2-fluorobenzyl)oxy)pyridin-2-yl)-2,5-difluorobenzyl)-1-((1-(cyclopropanecarbonyl)-3-methoxyazetidin-3-yl)methyl)-1H-benzo[d]imidazole-6-carboxylate: Methyl 2-(4-(6-((4-cyano-2-fluorobenzyl)oxy)pyridin-2-yl)-2,5-difluorobenzyl)-1-((3-methoxyazetidin-3-yl)methyl)-1H-benzo[d]imidazole-6-carboxylate (I-181, 75 mg, 0.12 mmol) was taken up in THF (1.0 mL). DIPEA (0.062 mL, 0.36 mmol) was added followed by cyclopropanecarbonyl chloride (0.013 mL, 0.14 mmol) and the mixture was stirred at room temperature. After 30 minutes, the mixture was diluted with EtOAc (5 mL) and $H_2O$ (5 mL). The organic phase was collected, and the aqueous phase was extracted with EtOAc (2x5 mL). The combined organics were dried over $Na_2SO_4$, concentrated in vacuo, and purified by silica gel column chromatography (eluent: EtOAc/hexanes) to afford the product: ES/MS: 696.2 ($M+H^+$).

2-(4-(6-((4-cyano-2-fluorobenzyl)oxy)pyridin-2-yl)-2,5-difluorobenzyl)-1-((1-(cyclopropanecarbonyl)-3-methoxyazetidin-3-yl)methyl)-1H-benzo[d]imidazole-6-carboxylic acid (Example 889): Methyl 2-(4-(6-((4-cyano-2-fluorobenzyl)oxy)pyridin-2-yl)-2,5-difluorobenzyl)-1-((1-(cyclopropanecarbonyl)-3-methoxyazetidin-3-yl)methyl)-1H-benzo[d]imidazole-6-carboxylate (60 mg, 0.088 mmol) was taken up in acetonitrile (1.8 mL) and aqueous lithium hydroxide (0.3 M, 1.5 mL, 0.442 mmol) was added. The mixture was heated to 50° C. for two hours. Following this time, the mixture was diluted with water (5 mL), the pH adjusted to ~5 with 5% aqueous citric acid solution and the mixture extracted with EtOAc (3x5 mL). The combined organics were dried over $Na_2SO_4$, concentrated in vacuo, and purified by RP-HPLC (eluent: MeCN/water with 0.1% TFA) to yield the product (Example 889) as the trifluoroacetate salt: ES/MS: 682.2 ($M+H^+$); $^1H$ NMR (400 MHz, DMSO-d6) δ 8.46 (d, J=1.5 Hz, 1H), 7.95-7.87 (m, 2H), 7.83 (dd, J=8.4, 1.5 Hz, 1H), 7.79-7.70 (m, 3H), 7.62 (d, J=8.4 Hz, 1H), 7.53 (dd, J=7.5, 1.7 Hz, 1H), 7.41 (dd, J=11.5, 6.1 Hz, 1H), 7.00 (d, J=8.3 Hz, 1H), 5.60 (s, 2H), 4.96 (s, 2H), 4.50 (s, 2H), 4.43 (d, J=9.7 Hz, 1H), 4.28 (d, J=9.8 Hz, 1H), 4.02 (d, J=10.6 Hz, 1H), 3.94 (d, J=11.5 Hz, 1H), 3.38 (s, 3H), 1.59 (p, J=6.4 Hz, 1H), 0.74 (d, J=8.1 Hz, 4H).

Example 890. 2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylic acid isomer 1

Example 891. 2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylic acid isomer 2 Procedure 104

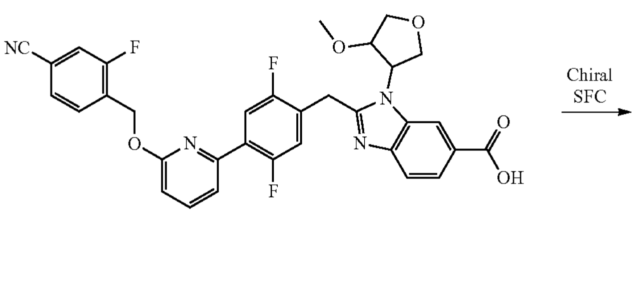

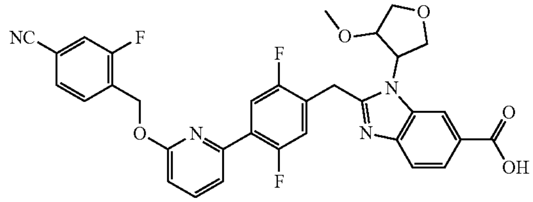

Example 890

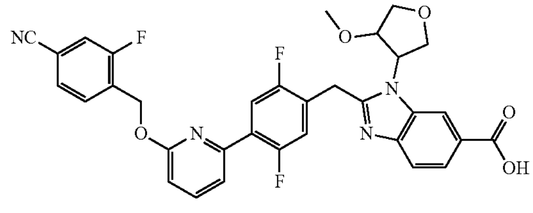

Example 891

2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylic acid: 2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylic acid (obtained as described in procedure 50) as a mixture of stereoisomers was separated by chiral SFC (AD-H column with MeOH cosolvent) to give two separate stereoisomers.

2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylic acid isomer 1 (Example 890): ES/MS: 615.2 ($M+H^+$); $^1H$ NMR (400 MHz, DMSO-d6) δ 8.29 (d, J=1.5 Hz, 1H), 7.95-7.85 (m, 2H), 7.81 (dd, J=10.5, 6.4 Hz, 1H), 7.65 (d, J=8.4 Hz, 1H), 7.53 (dd, J=7.5, 1.7 Hz, 1H), 7.45 (ddt, J=15.7, 11.5, 7.4 Hz, 3H), 6.97 (d, J=8.2 Hz, 1H), 5.56 (s, 2H), 4.65 (t, J=5.1 Hz, 2H), 4.52 (s, 2H), 3.70 (t, J=5.0 Hz, 2H), 3.21 (s, 3H).

2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylic acid isomer 2 (Example 891): ES/MS: 615.2 ($M+H^+$); $^1H$ NMR (400 MHz, DMSO-d6) δ 8.38 (s, 1H), 7.97-7.86 (m, 2H), 7.75 (dt, J=6.5, 5.2 Hz, 4H), 7.60-7.43 (m, 2H), 7.29 (dd, J=11.4, 6.1 Hz, 1H), 6.99 (d, J=8.2 Hz, 1H), 5.60 (s, 2H), 5.53 (d, J=10.2 Hz, 1H), 4.49 (s, 2H), 4.42 (dd, J=10.3, 3.8 Hz, 1H), 4.17-4.06 (m, 2H), 4.02 (dd, J=10.3, 8.3 Hz, 1H), 3.82 (dd, J=10.1, 4.5 Hz, 1H), 2.87 (s, 3H).

Example 893. 1-(2-(tert-butoxy)ethyl)-2-(4-(6-((4-cyano-2-fluorobenzyl)oxy)pyridin-2-yl)-2,5-difluorobenzyl)-1H-benzo[d]imidazole-6-carboxylic acid Procedure 105

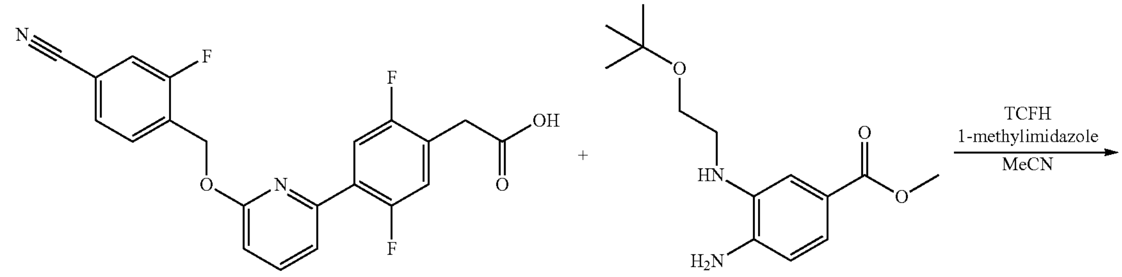

I-81 I-187

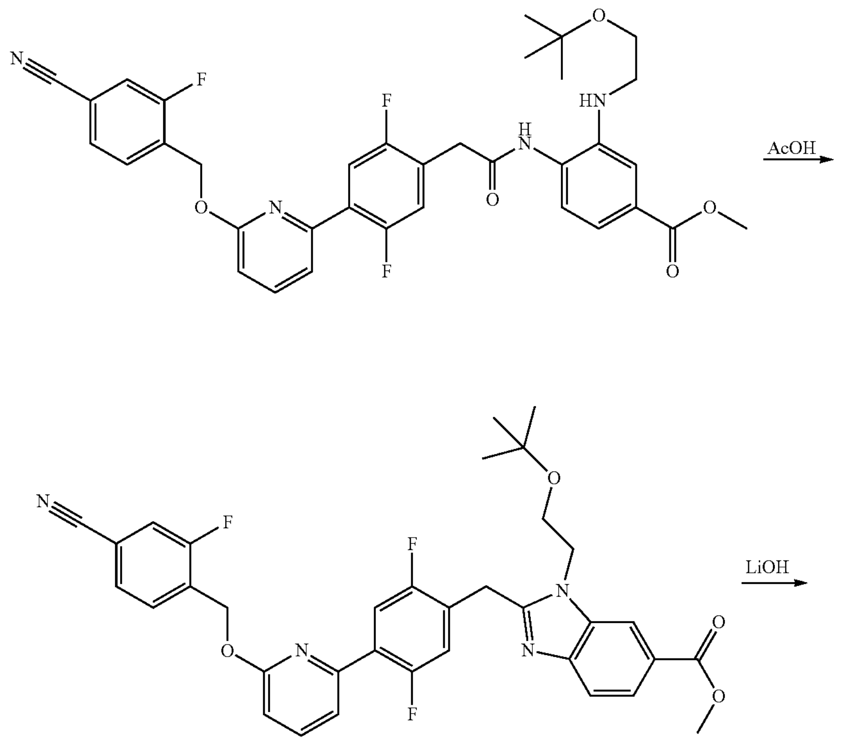

-continued

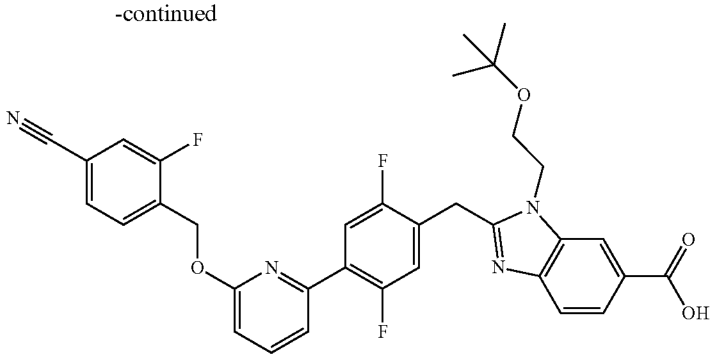

Example 893

Methyl 3-((2-(tert-butoxy)ethyl)amino)-4-(2-(4-(6-((4-cyano-2-fluorobenzyl)oxy)pyridin-2-yl)-2,5-difluorophenyl)acetamido)benzoate: To a solution of 2-(4-(6-((4-cyano-2-fluorobenzyl)oxy)pyridin-2-yl)-2,5-difluorophenyl)acetic acid (40 mg, 0.1 mmol) and methyl 4-amino-3-((2-(tert-butoxy)ethyl)amino)benzoate (34 mg, 0.13 mmol) in MeCN (1 mL) was added 1-methylimidazole (0.04 mL, 0.50 mmol) and TCFH (34 mg, 0.12 mmol). The resulting slurry was stirred at room temperature for 1 hour. The slurry was diluted with EtOAc and washed with HCl (1 M). The aqueous layer was back extracted with EtOAc and the combine organic layers were dried over $MgSO_4$ and concentrated to dryness. The resulting crude material was used directly in the next step. ES/MS m/z: 647.2 ($M+H^+$).

Methyl 1-(2-(tert-butoxy)ethyl)-2-(4-(6-((4-cyano-2-fluorobenzyl)oxy)pyridin-2-yl)-2,5-difluorobenzyl)-1H-benzo[d]imidazole-6-carboxylate: A solution of methyl 3-((2-(tert-butoxy)ethyl)amino)-4-(2-(4-(6-((4-cyano-2-fluorobenzyl)oxy)pyridin-2-yl)-2,5-difluorophenyl)acetamido)benzoate (64 mg, 0.1 mmol) in AcOH (1 mL) was heated to 70° C. for 2 hours. The resulting solution was diluted with $CH_2Cl_2$ and washed with $H_2O$ and aqueous sodium bicarbonate. The aqueous layers were back extracted with $CH_2Cl_2$ and the combine organic layers were dried over $MgSO_4$ and concentrated to dryness. The resulting crude material was purified by column chromatography (eluent: EtOAc/Hexanes) to yield methyl 1-(2-(tert-butoxy)ethyl)-2-(4-(6-((4-cyano-2-fluorobenzyl)oxy)pyridin-2-yl)-2,5-difluorobenzyl)-1H-benzo[d]imidazole-6-carboxylate. ES/MS m/z: 629.2 ($M+H^+$).

1-(2-(Tert-butoxy)ethyl)-2-(4-(6-((4-cyano-2-fluorobenzyl)oxy)pyridin-2-yl)-2,5-difluorobenzyl)-1H-benzo[d]imidazole-6-carboxylic acid (Example 893): To a slurry of methyl 1-(2-(tert-butoxy)ethyl)-2-(4-(6-((4-cyano-2-fluorobenzyl)oxy)pyridin-2-yl)-2,5-difluorobenzyl)-1H-benzo[d]imidazole-6-carboxylate (42 mg, 0.67 mmol) in MeCN (1.5 mL) was added $H_2O$ (0.25 mL) and lithium hydroxide (0.2 mL, 1 M aqueous). The reaction vial was sealed and heated to 100° C. for 5 min and cooled to room temperature. The resulting solution was diluted with MeCN and DMF and neutralized with TFA. Purification via reverse phase HPLC (eluent: MeCN/$H_2O$/0.1% TFA) provided 1-(2-(tert-butoxy)ethyl)-2-(4-(6-((4-cyano-2-fluorobenzyl)oxy)pyridin-2-yl)-2,5-difluorobenzyl)-1H-benzo[d]imidazole-6-carboxylic acid (Example 893) as a trifluoroacetate salt. ES/MS m/z: 615.2 ($M+H^+$); 1H NMR (400 MHz, DMSO) δ 12.85 (s, 1H), 8.30 (d, J=1.6 Hz, 1H), 7.96-7.87 (m, 2H), 7.85 (dd, J=8.5, 1.5 Hz, 1H), 7.82-7.70 (m, 3H), 7.64 (d, J=8.4 Hz, 1H), 7.53 (dd, J=7.5, 1.7 Hz, 1H), 7.40 (dd, J=11.4, 6.0 Hz, 1H), 7.00 (d, J=8.3 Hz, 1H), 5.60 (s, 2H), 4.55 (d, J=3.5 Hz, 4H), 3.65 (t, J=4.9 Hz, 2H), 0.94 (s, 9H).

Examples 892, 894-897. Compounds Prepared Using Procedure 105

Other compounds of the present disclosure prepared using the general route described in Procedure 105 include the following Examples.

| Example | Structure/Name/Characterization |
|---|---|
| 892 | 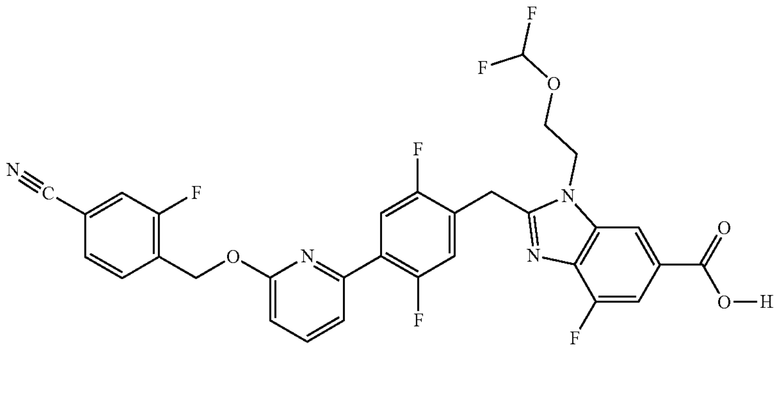 [SMILES: N#Cc1ccc(COc2cccc(-c3cc(F)c(Cc4nc5c(F)cc(C(=O)O)cc5n4CCOC(F)F)cc3F)n2)c(F)c1] |

-continued

| Example | Structure/Name/Characterization |
|---|---|
| | ES/MS m/z 627.2; 1H NMR (400 MHz, DMSO-d6) δ 8.14 (d, J = 1.3 Hz, 1H), 7.97-7.86 (m, 3H), 7.80-7.70 (m, 4H), 7.59-7.48 (m, 2H), 7.40 (dd, J = 11.5, 6.1 Hz, 1H), 6.99 (d, J = 8.3 Hz, 1H), 6.64 (t, J = 75.3 Hz, 1H), 5.61 (s, 5H), 4.75 (t, J = 5.1 Hz, 2H), 4.46 (s, 2H), 4.21 (t, J = 5.0 Hz, 2H). |
| 894 | 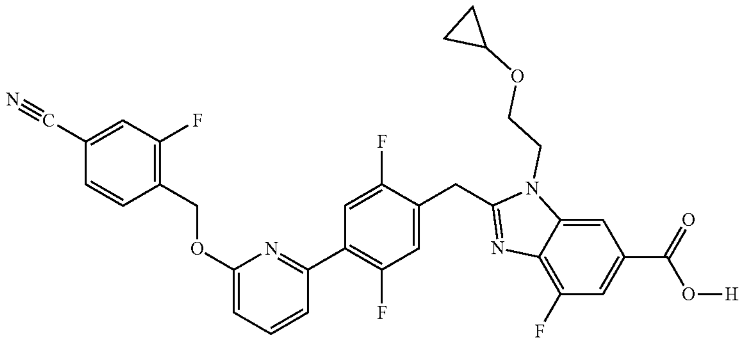 [SMILES: N#Cc1ccc(COc2cccc(-c3cc(F)c(Cc4nc5c(F)cc(C(=O)O)cc5n4CCOC4CC4)cc3F)n2)c(F)c1] ES/MS m/z 617.2; 1H NMR (400 MHz, DMSO) δ 8.10 (d, J = 1.3 Hz, 1H), 7.96-7.86 (m, 2H), 7.81-7.70 (m, 3H), 7.57-7.47 (m, 2H), 7.37 (dd, J = 11.5, 6.1 Hz, 1H), 6.99 (d, J = 8.2 Hz, 1H), 5.61 (s, 2H), 4.58 (t, J = 5.2 Hz, 2H), 4.43 (s, 2H), 3.77 (t, J = 5.1 Hz, 2H), 3.24 (tt, J = 6.0, 2.9 Hz, 1H), 0.38-0.28 (m, 2H), 0.28-0.20 (m, 2H). 19F NMR (377 MHz, DMSO) δ −115.88 (dd, J = 9.9, 6.5 Hz), −121.88 (ddd, J = 17.9, 11.1, 6.1 Hz), −122.46 (ddd, J = 17.1, 10.5, 6.3 Hz), −129.52 (d, J = 11.3 Hz). |
| 895 | 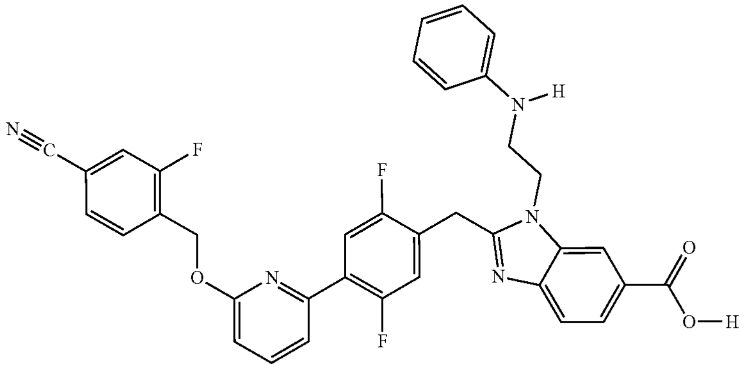 [SMILES: N#Cc1ccc(COc2cccc(-c3cc(F)c(Cc4nc5ccc(C(=O)O)cc5n4CCNc4ccccc4)cc3F)n2)c(F)c1] ES/MS m/z 634.2; 1H NMR (400 MHz, DMSO) δ 8.30 (d, J = 1.5 Hz, 1H), 7.96-7.85 (m, 3H), 7.81-7.71 (m, 3H), 7.67 (d, J = 8.5 Hz, 1H), 7.51 (dd, J = 7.4, 1.7 Hz, 1H), 7.27 (dd, J = 11.5, 6.0 Hz, 1H), 7.06 (t, J = 7.8 Hz, 2H), 7.00 (d, J = 8.3 Hz, 1H), 6.59-6.51 (m, 3H), 5.60 (s, 2H), 4.57 (t, J = 5.9 Hz, 2H), 4.38 (s, 2H), 3.52 (t, J = 5.9 Hz, 2H). 19F NMR (377 MHz, DMSO) δ −115.92 (dd, J = 10.1, 6.2 Hz), −121.64, −122.17 (dd, J = 18.0, 9.0 Hz). |
| 896 | 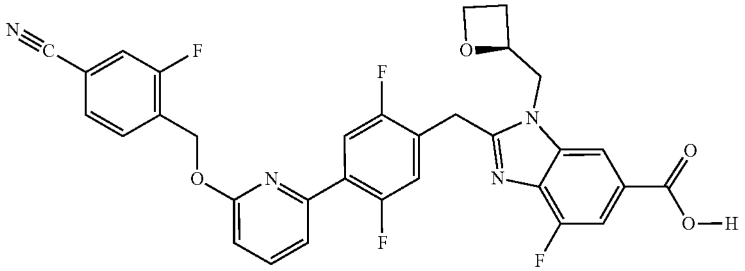 [SMILES: N#Cc1ccc(COc2cccc(-c3cc(F)c(Cc4nc5c(F)cc(C(=O)O)cc5n4C[C@@H]4CCO4)cc3F)n2)c(F)c1] ES/MS m/z 603.496; 1H NMR (400 MHz, DMSO) δ 13.08 (s, 1H), 8.16 (d, J = 1.3 Hz, 1H), 7.97-7.86 (m, 2H), 7.80-7.70 (m, 3H), 7.57-7.47 (m, 2H), 7.40 (dd, J = 11.5, 6.1 Hz, 1H), 6.99 (d, J = 8.2 Hz, 1H), 5.61 (s, 2H), 5.13-5.02 (m, 1H), 4.79 (dd, J = 15.6, 7.0 Hz, 1H), 4.66 (dd, J = 15.4, 2.7 Hz, 1H), 4.61-4.42 (m, 3H), 4.36 (dt, J = 9.1, 5.9 Hz, 1H), 2.78-2.64 (m, 1H), 2.43-2.35 (m, 1H). 19F NMR (377 MHz, DMSO) δ −115.87 (dd, J = 9.9, 6.5 Hz), −121.83 (ddd, J = 18.2, 11.5, 6.4 Hz), −122.36 (ddd, J = 17.1, 10.5, 6.2 Hz), −129.61 (d, J = 11.6 Hz). |

-continued
| Example | Structure/Name/Characterization |
|---|---|
| 897 | 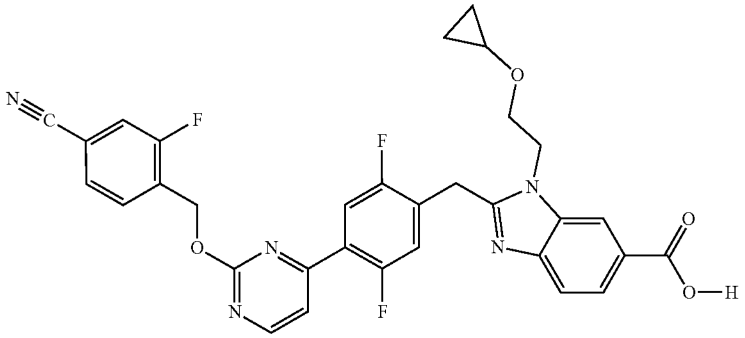 [SMILES: N#Cc1ccc(COc2nccc(-c3cc(F)c(Cc4nc5ccc(C(=O)O)cc5n4CCOC4CC4)cc3F)n2)c(F)c1] ES/MS m/z 600.243; 1H NMR (400 MHz, DMSO) δ 12.80 (s, 1H), 8.78 (d, J = 5.2 Hz, 1H), 8.23 (d, J = 1.6 Hz, 1H), 7.98-7.93 (m, 1H), 7.93-7.87 (m, 1H), 7.84-7.72 (m, 3H), 7.64 (dd, J = 5.2, 1.9 Hz, 1H), 7.60 (d, J = 8.5 Hz, 1H), 7.46 (dd, J = 11.6, 6.0 Hz, 1H), 5.64 (s, 2H), 4.58 (t, J = 5.1 Hz, 2H), 4.45 (s, 2H), 3.78 (t, J = 5.1 Hz, 2H), 3.24 (tt, J = 6.1, 3.0 Hz, 1H), 0.37-0.28 (m, 2H), 0.28-0.19 (m, 2H). 19F NMR (377 MHz, DMSO) δ −115.76 (dd, J = 9.9, 6.4 Hz), −120.27, −121.52-−122.07 (m). |
Example 898. 1-((2-oxabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylic Acid
Procedure 106
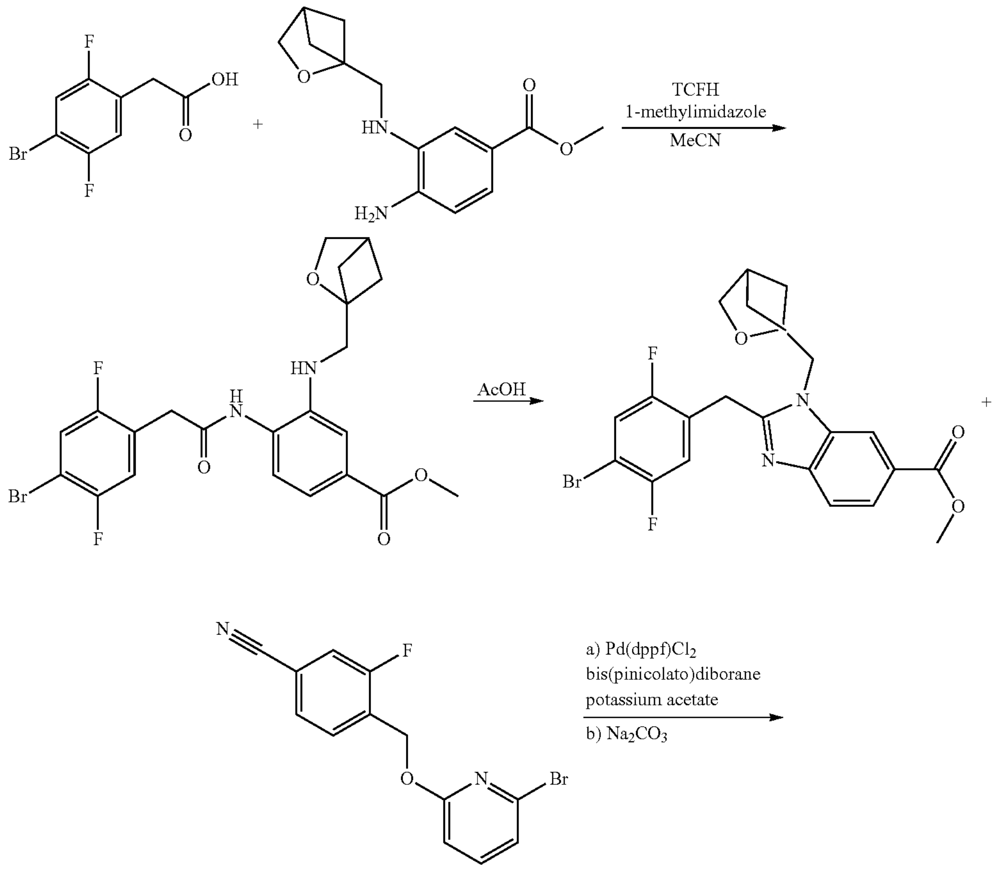

-continued

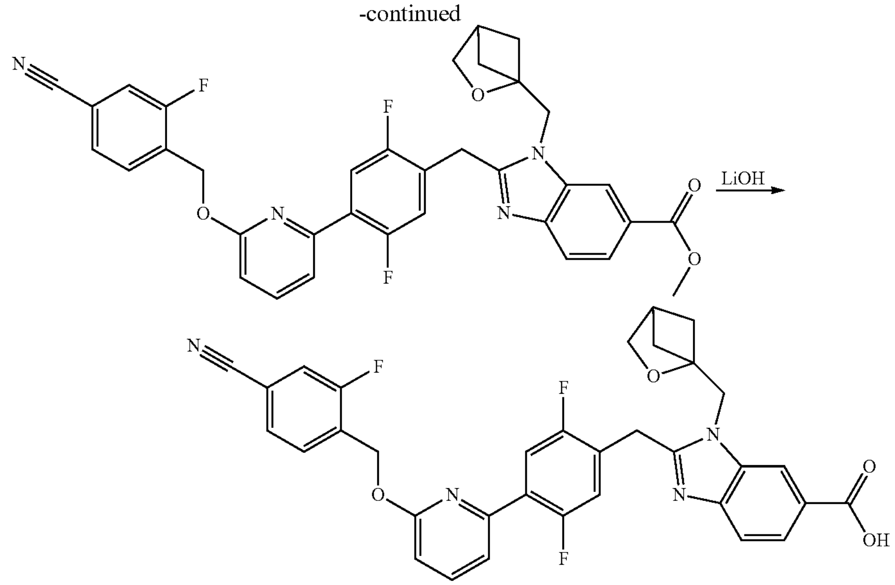

Example 898

Methyl 3-(((2-oxabicyclo[2.1.1]hexan-1-yl)methyl)amino)-4-(2-(4-bromo-2,5-difluorophenyl)acetamido)benzoate: To a solution of 2-(4-bromo-2,5-difluorophenyl)acetic acid (500 mg, 1.99 mmol) and methyl 3-(((2-oxabicyclo[2.1.1]hexan-1-yl)methyl)amino)-4-aminobenzoate (549 mg, 2.09 mmol) in MeCN (10 mL) was added 1-methylimidazole (0.9 mL, 11.3 mmol) and TCFH (600 mg, 2.14 mmol). The resulting solution was stirred at room temperature for 45 min, diluted with EtOAc and washed twice with aqueous HCl (1 M). The organic layer was dried over $MgSO_4$ and concentrated to dryness. The resulting crude material was used directly in the next step. ES/MS m/z: 496.075 ($M+H^+$).

Methyl 1-((2-oxabicyclo[2.1.1]hexan-1-yl)methyl)-2-(4-bromo-2,5-difluorobenzyl)-1H-benzo[d]imidazole-6-carboxylate: A solution of methyl 3-(((2-oxabicyclo[2.1.1]hexan-1-yl)methyl)amino)-4-(2-(4-bromo-2,5-difluorophenyl)acetamido)benzoate (987 mg, 1.99 mmol) in AcOH (4.5 mL) and DCE (4.5 mL) was heated to 70° C. for 4 hours. The resulting solution was diluted with $CH_2Cl_2$ and washed with $H_2O$ and aqueous sodium bicarbonate. The aqueous layers were backextracted with $CH_2Cl_2$ and the combined organic layers were dried over $MgSO_4$ and concentrated to dryness. The resulting crude material was purified by column chromatography (eluent: EtOAc/Hexanes) to yield methyl 1-((2-oxabicyclo[2.1.1]hexan-1-yl)methyl)-2-(4-bromo-2,5-difluorobenzyl)-1H-benzo[d]imidazole-6-carboxylate. ES/MS m/z: 478.990 ($M+H^+$).

Methyl 1-((2-oxabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylate: To a solution of methyl 1-((2-oxabicyclo[2.1.1]hexan-1-yl)methyl)-2-(4-bromo-2,5-difluorobenzyl)-1H-benzo[d]imidazole-6-carboxylate (50 mg, 0.11 mmol), 4,4,5,5-tetramethyl-2-(4,4,5,5-tetramethyl-1,3,2-dioxaborolan-2-yl)-1,3,2-dioxaborolane (35.0 mg, 0.138 mmol), potassium acetate (32 mg, 0.33 mmol), [1,1'-Bis(diphenylphosphino)ferrocene]dichloropalladium(II) (9 mg, 0.14 mmol) in dioxane (2 mL) was degassed with argon and heated to 120° C. for 30 min in a microwave. To the resulting solution was added 4-(((6-bromopyridin-2-yl)oxy)methyl)-3-fluorobenzonitrile (45 mg, 0.14 mmol) and aqueous sodium carbonate (0.15 mL, 2 M, 0.30 mmol). The solution was heated to 120° C. for 20 min in a microwave and then diluted with EtOAc and filtered through celite. The resulting crude material was purified by column chromatography (eluent: EtOAc/Hexanes) to yield methyl 1-((2-oxabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylate. ES/MS m/z: 643.20 ($M+H^+$).

1-((2-Oxabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylic acid (Example 898): To a slurry of methyl 1-((2-oxabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylate (52 mg, 0.081 mmol) in MeCN (1.5 mL) was added $H_2O$ (0.25 mL) and aqueous lithium hydroxide (0.15 mL, 1 M, 0.15 mmol). The reaction vessel was sealed and heating to 100° C. for 20 min and cooled to room temperature. The solution was diluted with MeCN and DMF and neutralized with TFA. Purification via reverse phase HPLC (eluent: MeCN/$H_2O$/0.1% TFA) provided 1-((2-oxabicyclo[2.1.1]hexan-1-yl)methyl)-2-(4-(6-((4-cyano-2-fluorobenzyl)oxy)pyridin-2-yl)-2,5-difluorobenzyl)-1H-benzo[d]imidazole-6-carboxylic acid (Example 898) as a trifluoroacetate salt. ES/MS m/z: 629.2 ($M+H^+$); 1H NMR (400 MHz, DMSO) δ 8.32 (d, J=1.5 Hz, 1H), 7.95-7.87 (m, 2H), 7.84 (dd, J=8.5, 1.5 Hz, 1H), 7.76 (d, J=4.9 Hz, 2H), 7.64 (d, J=8.5 Hz, 1H), 7.46 (ddd, J=9.6, 5.9, 3.1 Hz, 2H), 7.12 (dd, J=9.0, 3.0 Hz, 1H), 5.51 (s, 2H), 4.85 (s, 2H), 4.55 (s, 2H), 3.64 (s, 2H), 2.90 (t, J=3.2 Hz, 1H), 1.95 (d, J=4.5 Hz, 2H), 1.31 (dd, J=4.4, 1.8 Hz, 2H).

Example 899-900. Compounds Prepared Using Procedure 106

Other compounds of the present disclosure prepared using the general route described in Procedure 106 include the following Example.

| Example | Structure/Name/Characterization |
|---|---|
| 899 | 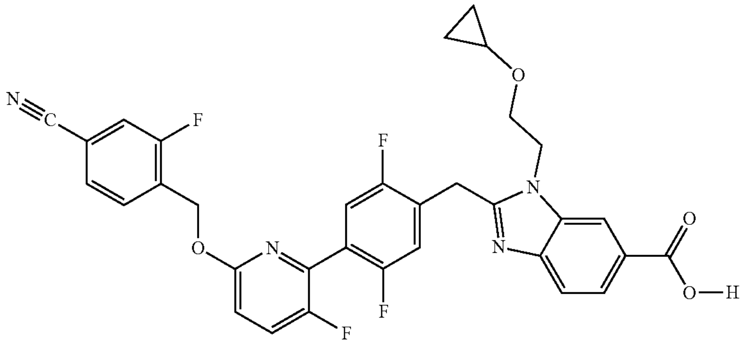 [SMILES: N#Cc1ccc(COc2ccc(F)c(-c3cc(F)c(Cc4nc5ccc(C(=O)O)cc5n4CCOC4CC4)cc3F)n2)c(F)c1] ES/MS m/z 617.5; 1H NMR (400 MHz, DMSO) δ 12.83 (s, 1H), 8.24 (d, J = 1.6 Hz, 1H), 7.95-7.85 (m, 2H), 7.82 (dd, J = 8.5, 1.6 Hz, 1H), 7.79-7.71 (m, 2H), 7.63 (d, J = 8.4 Hz, 1H), 7.46 (dd, J = 9.7, 5.8 Hz, 1H), 7.42 (s, 1H), 7.12 (dd, J = 9.0, 3.0 Hz, 1H), 5.51 (s, 2H), 4.59 (t, J = 5.1 Hz, 2H), 4.45 (s, 2H), 3.79 (t, J = 5.0 Hz, 2H), 3.25 (tt, J = 6.0, 3.0 Hz, 1H), 0.32 (pd, J = 6.0, 3.3 Hz, 2H), 0.28-0.21 (m, 2H). 19F NMR (377 MHz, DMSO) δ −115.80 (dd, J = 10.1, 5.2 Hz), −120.06--120.53 (m), −122.47--122.78 (m), −132.47 (ddd, J = 33.8, 9.0, 3.0 Hz). |
| 900 | 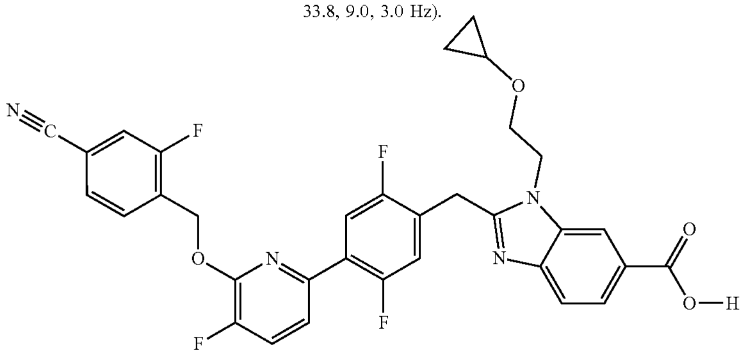 ES/MS m/z 617.34; 1H NMR (400 MHz, DMSO) δ 8.27 (s, 1H), 7.98-7.91 (m, 1H), 7.91-7.82 (m, 2H), 7.76 (h, J = 7.3, 6.8 Hz, 3H), 7.64 (d, J = 8.4 Hz, 1H), 7.58-7.51 (m, 1H), 7.39 (dd, J = 11.4, 6.1 Hz, 1H), 5.69 (s, 2H), 4.60 (t, J = 5.2 Hz, 2H), 4.46 (s, 2H), 3.79 (t, J = 5.1 Hz, 2H), 3.25 (tt, J = 6.1, 2.9 Hz, 1H), 0.36-0.29 (m, 2H), 0.25 (q, J = 4.8, 4.2 Hz, 2H). 19F NMR (377 MHz, DMSO) δ −115.73 (dd, J = 10.1, 6.4 Hz), −122.15 (q, J = 10.7 Hz), −122.27--122.42 (m), −140.52 (dd, J = 10.3, 3.0 Hz). |

Example 901. 2-(2,5-difluoro-4-(6-((2-fluoro-4-(1,2,3,6-tetrahydropyridin-4-yl)benzyl)oxy)pyridin-2-yl)benzyl)-1-(2-methoxyethyl)-1H-benzo[d]imidazole-6-carboxylic Acid Procedure 107

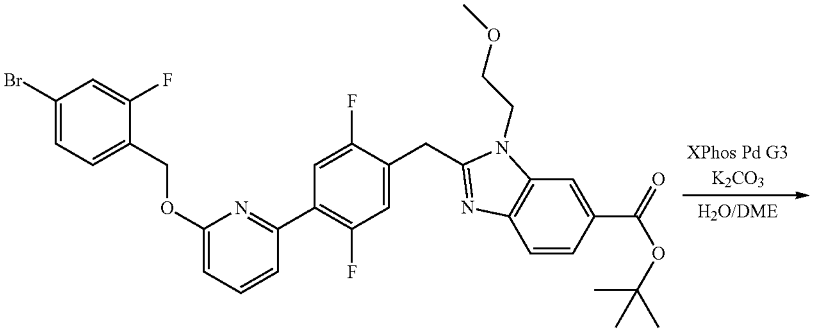

I-194

-continued

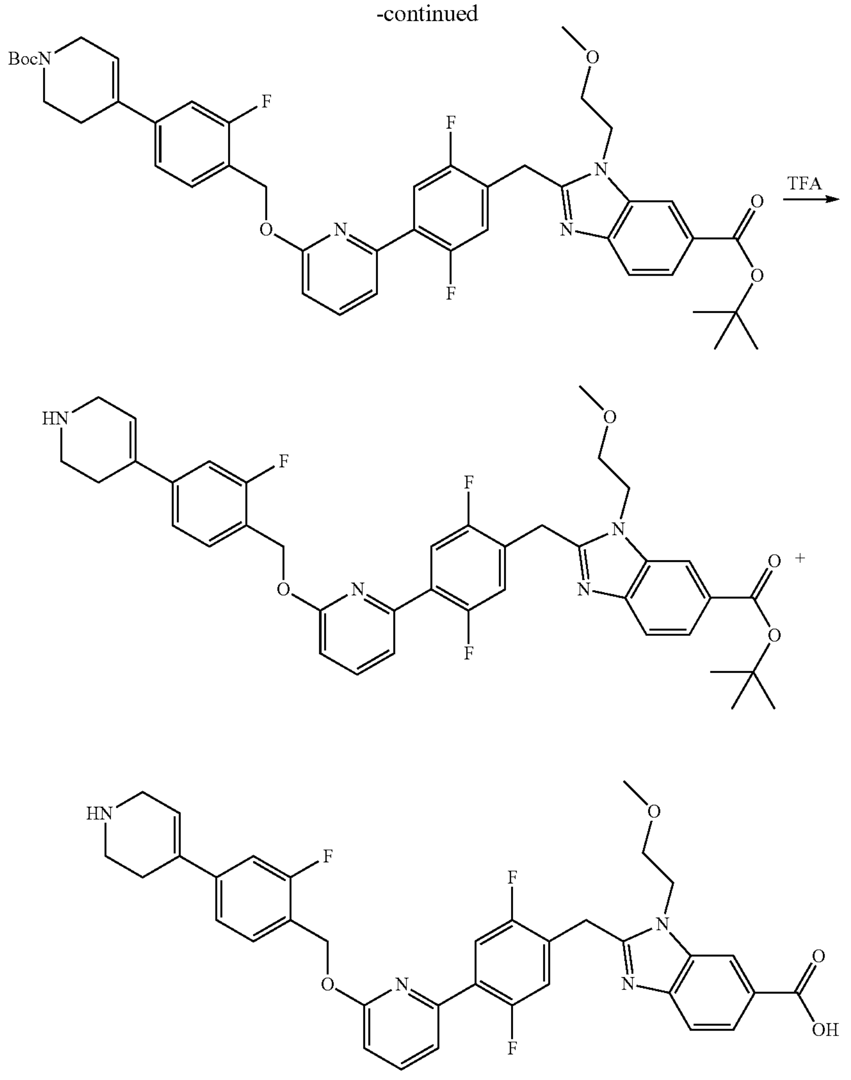

Example 901

Tert-butyl 2-(4-(6-((4-(1-(tert-butoxycarbonyl)-1,2,3,6-tetrahydropyridin-4-yl)-2-fluorobenzyl)oxy)pyridin-2-yl)-2,5-difluorobenzyl)-1-(2-methoxyethyl)-1H-benzo[d]imidazole-6-carboxylate: To a solution of tert-butyl 2-(4-(6-((4-bromo-2-fluorobenzyl)oxy)pyridin-2-yl)-2,5-difluorobenzyl)-1-(2-methoxyethyl)-1H-benzo[d]imidazole-6-carboxylate (30 mg, 0.044 mmol), XPhos Pd G3 (5 mg, 0.006 mmol) in DME (0.5 mL) was added aqueous potassium carbonate (2 M, 0.05 mL, 0.1 mmol). The resulting solution was degassed with argon, sealed, and heated to 120° C. for 60 min in a microwave. The solution was then diluted with EtOAc, filtered through celite and concentrated to dryness. The resulting crude material was purified by column chromatography (eluent: EtOAc/hexanes) to provide tert-butyl 2-(4-(6-((4-(1-(tert-butoxycarbonyl)-1,2,3,6-tetrahydropyridin-4-yl)-2-fluorobenzyl)oxy)pyridin-2-yl)-2,5-difluorobenzyl)-1-(2-methoxyethyl)-1H-benzo[d]imidazole-6-carboxylate. ES/MS m/z: 785.691 $(M+H^+)$.

2-(2,5-Difluoro-4-(6-((2-fluoro-4-(1,2,3,6-tetrahydropyridin-4-yl)benzyl)oxy)pyridin-2-yl)benzyl)-1-(2-methoxyethyl)-1H-benzo[d]imidazole-6-carboxylic acid (Example 901): To a solution of tert-butyl 2-(4-(6-((4-(1-(tert-butoxycarbonyl)-1,2,3,6-tetrahydropyridin-4-yl)-2-fluorobenzyl)oxy)pyridin-2-yl)-2,5-difluorobenzyl)-1-(2-methoxyethyl)-1H-benzo[d]imidazole-6-carboxylate (35 mg, 0.045 mmol) in $CH_2Cl_2$ (0.5 mL) was added trifluoroacetic acid (0.06 mL, 0.78 mmol). The solution was stirred at room temperature for 3.5 h, diluted with DMF and concentrated. Purification via reverse phase HPLC (eluent: $MeCN/H_2O/0.1\%$ TFA) provided tert-butyl 2-(2,5-difluoro-4-(6-((2-fluoro-4-(1,2,3,6-tetrahydropyridin-4-yl)benzyl)oxy)pyridin-2-yl)benzyl)-1-(2-methoxyethyl)-1H-benzo[d]imidazole-6-carboxylate and 2-(2,5-difluoro-4-(6-((2-fluoro-4-(1,2,3,6-tetrahydropyridin-4-yl)benzyl)oxy)pyridin-2-yl)benzyl)-1-(2-methoxyethyl)-1H-benzo[d]imidazole-6-carboxylic acid (Example 901) as a trifluoroacetate salt. ES/MS m/z: 629.2 $(M+H^+)$; 1H NMR (400 MHz, DMSO) δ 8.80 (s, 2H), 8.23 (d, J=1.6 Hz, 1H), 7.92-7.78 (m, 3H), 7.64-7.49 (m, 3H), 7.45-7.32 (m, 3H), 6.94 (d, J=8.3 Hz, 1H), 6.32 (d, J=4.0 Hz, 1H), 5.53 (s, 2H), 4.61 (t, J=5.0 Hz, 2H), 4.46 (s, 2H), 3.81-3.75 (m, 2H), 3.69 (t, J=5.0 Hz, 2H), 3.33 (d, J=6.4 Hz, 2H), 3.22 (s, 3H), 2.68 (s, 2H).

Example 902. 2-(4-(6-((4-(1-acetyl-1,2,3,6-tetrahydropyridin-4-yl)-2-fluorobenzyl)oxy)pyridin-2-yl)-2,5-difluorobenzyl)-1-(2-methoxyethyl)-1H-benzo[d]imidazole-6-carboxylic acid Procedure 108

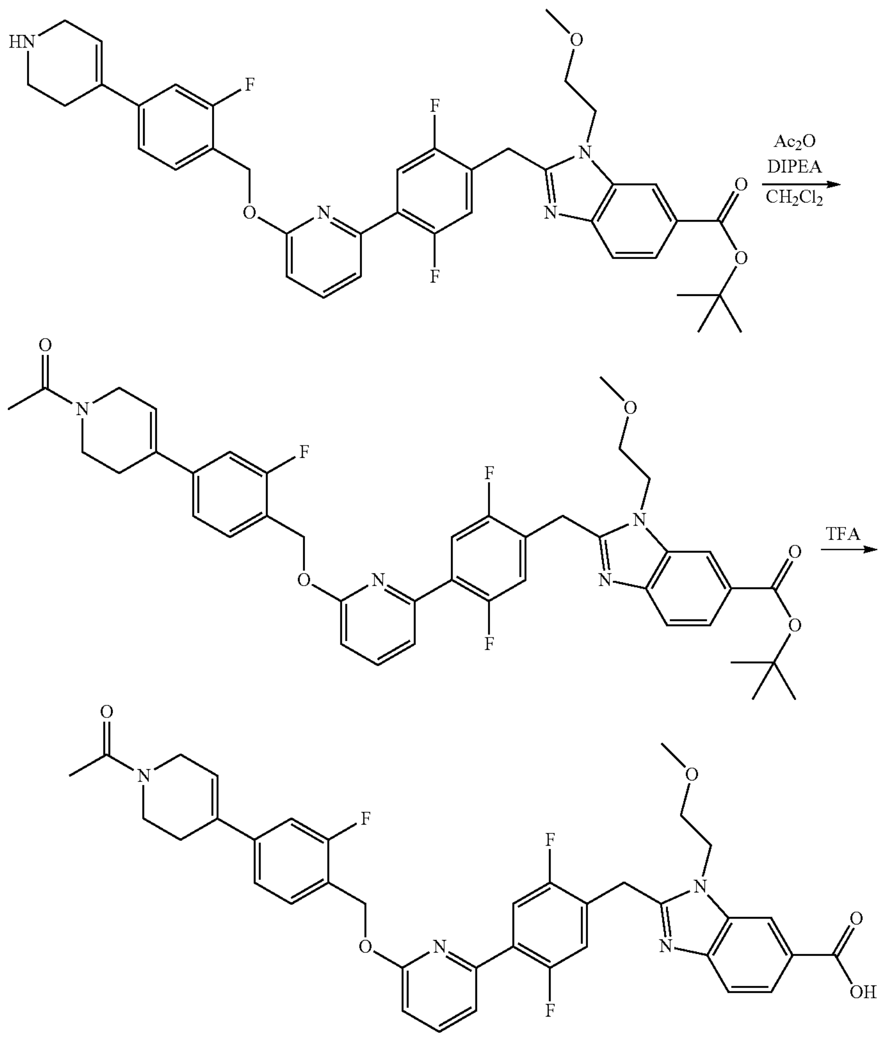

Example 902

Tert-butyl 2-(4-(6-((4-(1-acetyl-1,2,3,6-tetrahydropyridin-4-yl)-2-fluorobenzyl)oxy)pyridin-2-yl)-2,5-difluorobenzyl)-1-(2-methoxyethyl)-1H-benzo[d]imidazole-6-carboxylate: To a solution of tert-butyl 2-(2,5-difluoro-4-(6-((2-fluoro-4-(1,2,3,6-tetrahydropyridin-4-yl)benzyl)oxy)pyridin-2-yl)benzyl)-1-(2-methoxyethyl)-1H-benzo[d]imidazole-6-carboxylate (12 mg, 0.017 mmol) in $CH_2Cl_2$ (0.25 mL) was added acetic anhydride (0.01 mL, 0.10 mmol) and DIPEA (0.015 mL, 0.09 mmol). The resulting solution was stirred at room temperature for 30 min and concentrated to dryness. The resulting crude material was used directly in the next step. ES/MS m/z: 727.610 ($M+H^+$).

2-(4-(6-((4-(1-acetyl-1,2,3,6-tetrahydropyridin-4-yl)-2-fluorobenzyl)oxy)pyridin-2-yl)-2,5-difluorobenzyl)-1-(2-methoxyethyl)-1H-benzo[d]imidazole-6-carboxylic acid (Example 902): To a solution of tert-butyl 2-(4-(6-((4-(1-acetyl-1,2,3,6-tetrahydropyridin-4-yl)-2-fluorobenzyl)oxy)pyridin-2-yl)-2,5-difluorobenzyl)-1-(2-methoxyethyl)-1H-benzo[d]imidazole-6-carboxylate (12.7 mg, 0.017 mmol) in 1,2-dichloroethane (0.5 mL) was added trifluoroacetic acid (0.025 mL, 0.33 mmol). The reaction vessel was sealed and heated to 50° C. for 6 hours. The resulting solution was diluted with MeCN and DMF and concentrated. Purification via reverse phase HPLC (eluent: $MeCN/H_2O/0.1\%$ TFA) provided 2-(4-(6-((4-(1-acetyl-1,2,3,6-tetrahydropyridin-4-yl)-2-fluorobenzyl)oxy)pyridin-2-yl)-2,5-difluorobenzyl)-1-(2-methoxyethyl)-1H-benzo[d]imidazole-6-carboxylic acid (Example 902) as a trifluoroacetate salt. ES/MS m/z: 671.2 ($M+H^+$); 1H NMR (400 MHz, DMSO) δ 8.22 (d, J=1.6 Hz, 1H), 7.91-7.77 (m, 3H), 7.61 (d, J=8.4 Hz, 1H), 7.58-7.47 (m, 2H), 7.43-7.27 (m, 3H), 6.94 (d, J=8.2 Hz, 1H), 6.29 (s, 1H), 5.51 (s, 2H), 4.60 (t, J=5.1 Hz, 2H), 4.46

(s, 2H), 4.12 (dd, J=21.0, 3.2 Hz, 2H), 3.72-3.59 (m, 4H), 3.22 (s, 3H), 2.05 (d, J=14.2 Hz, 3H). 2H obscured by solvent.

Example 903. 2-((7-(6-((4-cyano-2-fluorobenzyl)oxy)pyridin-2-yl)-1,3-dihydroisobenzofuran-4-yl)methyl)-1-(2-methoxyethyl)-1H-benzo[d]imidazole-6-carboxylic acid Procedure 109

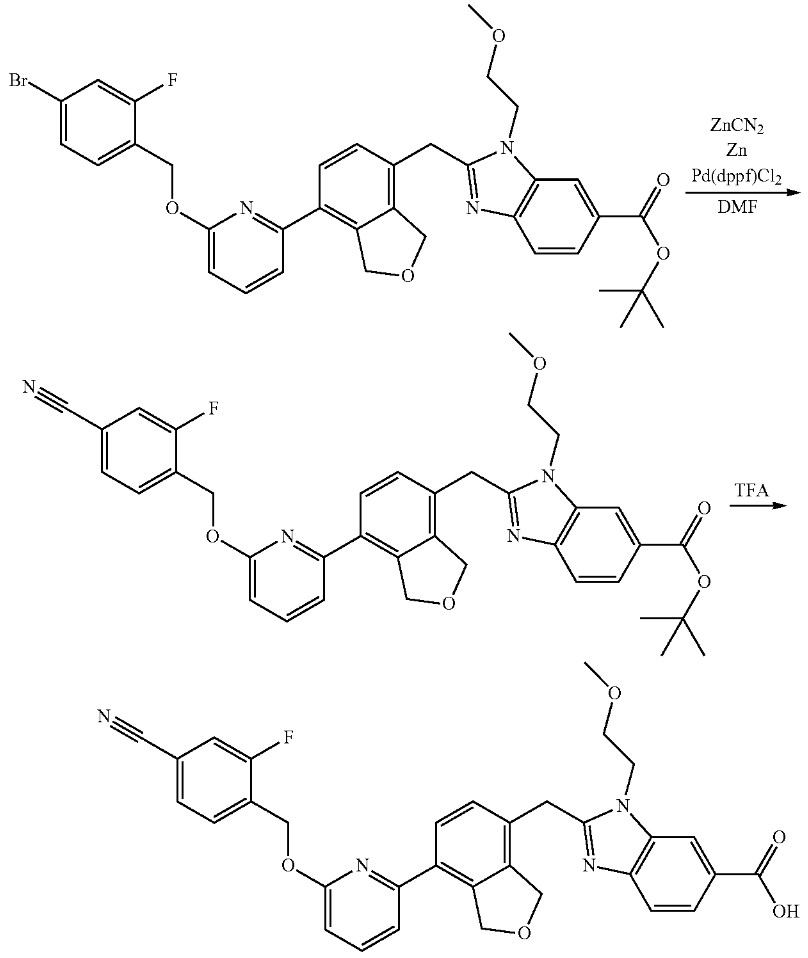

Example 903

Tert-butyl 2-((7-(6-((4-cyano-2-fluorobenzyl)oxy)pyridin-2-yl)-1,3-dihydroisobenzofuran-4-yl)methyl)-1-(2-methoxyethyl)-1H-benzo[d]imidazole-6-carboxylate: A solution of tert-butyl 2-((7-(6-((4-bromo-2-fluorobenzyl)oxy)pyridin-2-yl)-1,3-dihydroisobenzofuran-4-yl)methyl)-1-(2-methoxyethyl)-1H-benzo[d]imidazole-6-carboxylate (50 mg, 0.071 mmol), obtained in the same manner as described for I-194, zinc cyanide (16 mg, 0.14 mmol), zinc (5 mg, 0.076 mmol) and $Pd(dppf)Cl_2$ (5.5 mg, 0.008 mmol) in DMF (0.75 mL) was degassed, sealed, and heated to 150° C. for 90 min in a microwave. The resulting solution was diluted with EtOAc, filtered through celite, and concentrated to dryness. The crude material was then purified by column chromatography (eluent: EtOAc/hexanes) to provide tert-butyl 2-((7-(6-((4-cyano-2-fluorobenzyl)oxy)pyridin-2-yl)-1,3-dihydroisobenzofuran-4-yl)methyl)-1-(2-methoxyethyl)-1H-benzo[d]imidazole-6-carboxylate. ES/MS m/z: 653.510 ($M+H^+$).

2-((7-(6-((4-cyano-2-fluorobenzyl)oxy)pyridin-2-yl)-1,3-dihydroisobenzofuran-4-yl)methyl)-1-(2-methoxyethyl)-1H-benzo[d]imidazole-6-carboxylic acid (Example 903): To a solution of tert-butyl 2-((7-(6-((4-cyano-2-fluorobenzyl)oxy)pyridin-2-yl)-1,3-dihydroisobenzofuran-4-yl)methyl)-1-(2-methoxyethyl)-1H-benzo[d]imidazole-6-carboxylate (46 mg, 0.07 mmol) in 1,2-dichloroethane (1.5 mL) was added trifluoroacetic acid (0.11 mL, 1.4 mmol). The reaction vessel was sealed and heated to 50° C. for 12 hours. The resulting solution was diluted with MeCN and DMF and concentrated. Purification via reverse phase HPLC (eluent: $MeCN/H_2O/0.1\%$ TFA) provided 2-((7-(6-((4-cyano-2-fluorobenzyl)oxy)pyridin-2-yl)-1,3-dihydroisobenzofuran-4-yl)

methyl)-1-(2-methoxyethyl)-1H-benzo[d]imidazole-6-carboxylic acid (Example 903) as a trifluoroacetate salt. ES/MS m/z: 597.2 (M+H$^+$); 1H NMR (400 MHz, DMSO) δ 8.28 (d, J=1.6 Hz, 1H), 7.94-7.83 (m, 2H), 7.80 (d, J=7.8 Hz, 1H), 7.72 (dd, J=10.5, 6.4 Hz, 1H), 7.64 (d, J=8.4 Hz, 1H), 7.59 (d, J=7.9 Hz, 1H), 7.52 (dd, J=7.4, 1.8 Hz, 1H), 7.40 (dd, J=11.5, 6.1 Hz, 1H), 7.01 (d, J=8.2 Hz, 1H), 5.53 (s, 2H), 5.20 (s, 4H), 4.64 (t, J=5.1 Hz, 2H), 4.50 (s, 2H), 3.70 (t, J=5.0 Hz, 2H), 3.21 (s, 3H).

Example 904. 2-((7-(6-((4-cyano-2-fluorobenzyl)oxy)pyridin-2-yl)-1,3-dihydroisobenzofuran-4-yl)methyl)-1-(2-methoxyethyl)-1H-benzo[d]imidazole-6-carboxylic acid; Isomer 1

Example 905. 2-((7-(6-((4-cyano-2-fluorobenzyl)oxy)pyridin-2-yl)-1,3-dihydroisobenzofuran-4-yl)methyl)-1-(2-methoxyethyl)-1H-benzo[d]imidazole-6-carboxylic acid; Isomer 2

Procedure 110

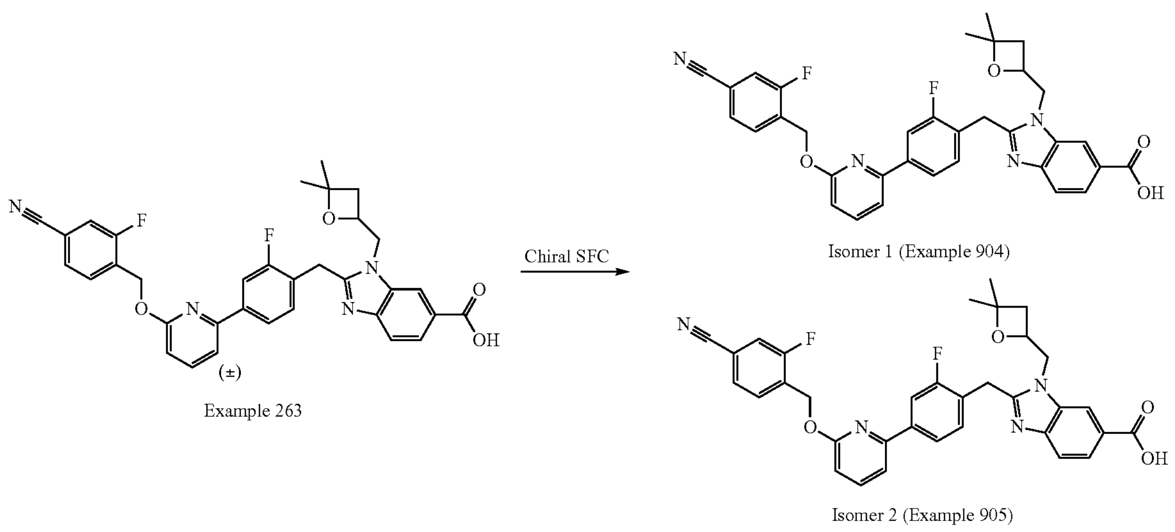

2-(4-(6-((4-cyano-2-fluorobenzyl)oxy)pyridin-2-yl)-2-fluorobenzyl)-1-((4,4-dimethyloxetan-2-yl)methyl)-1H-benzo[d]imidazole-6-carboxylic acid (Isomer 1, Example 904; Isomer 2, Example 905): Example 263 was subjected to SFC (ADH column, 30% EtOH) to afford the corresponding enantiomers. Isomer 1 (Example 904): ES/MS m/z: 595.2 (M+H$^+$); 1H NMR (400 MHz, DMSO) δ 8.23 (d, J=1.5 Hz, 1H), 7.95-7.90 (m, 1H), 7.90-7.84 (m, 3H), 7.83-7.70 (m, 3H), 7.66 (d, J=7.5 Hz, 1H), 7.60 (d, J=8.4 Hz, 1H), 7.42 (t, J=8.1 Hz, 1H), 6.93 (d, J=8.2 Hz, 1H), 5.62 (s, 2H), 4.87 (d, J=5.4 Hz, 1H), 4.59 (d, J=4.7 Hz, 2H), 4.57-4.40 (m, 2H), 2.43 (dd, J=11.1, 7.6 Hz, 1H), 2.13 (dd, J=11.2, 7.1 Hz, 1H), 1.35 (s, 3H), 1.10 (s, 3H). Isomer 2 (Example 905): ES/MS m/z: 595.2 (M+H$^+$); 1H NMR (400 MHz, DMSO) δ 8.23 (d, J=1.6 Hz, 1H), 7.93 (dd, J=10.0, 1.5 Hz, 1H), 7.90-7.84 (m, 3H), 7.82-7.70 (m, 3H), 7.66 (d, J=7.5 Hz, 1H), 7.60 (d, J=8.4 Hz, 1H), 7.42 (t, J=8.1 Hz, 1H), 6.93 (d, J=8.2 Hz, 1H), 5.62 (s, 2H), 4.87 (h, J=5.7, 4.9 Hz, 1H), 4.59 (d, J=4.7 Hz, 2H), 4.57-4.35 (m, 2H), 2.48-2.39 (m, 1H), 2.13 (dd, J=11.1, 7.2 Hz, 1H), 1.35 (s, 3H), 1.10 (s, 3H).

Example 906. 2-(4-(6-((4-cyano-2-fluorobenzyl)oxy)pyridin-2-yl)-2,5-difluorobenzyl)-1-(2-(cyclopropylamino)ethyl)-1H-benzo[d]imidazole-6-carboxylic acid
Procedure 111
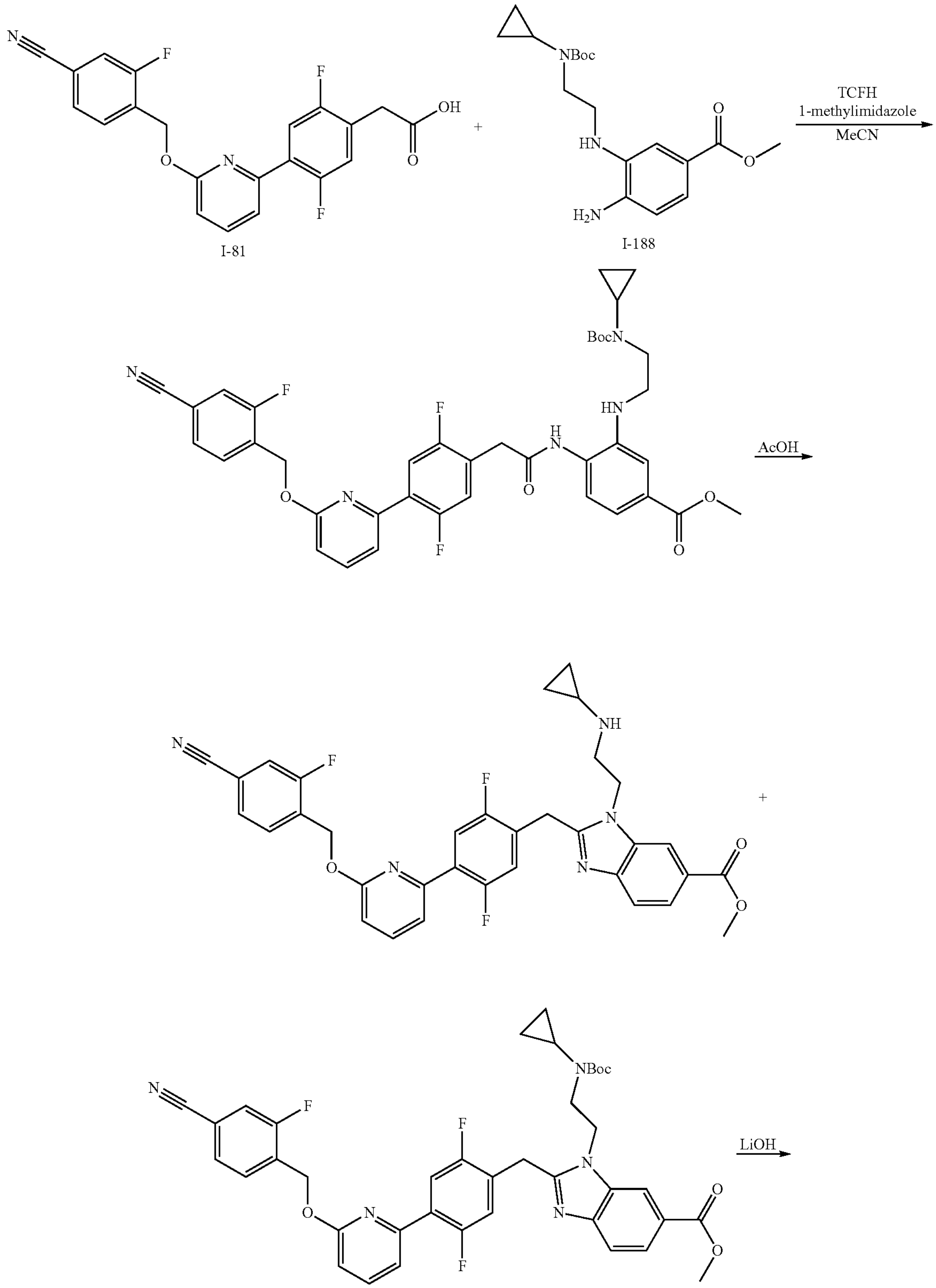

-continued

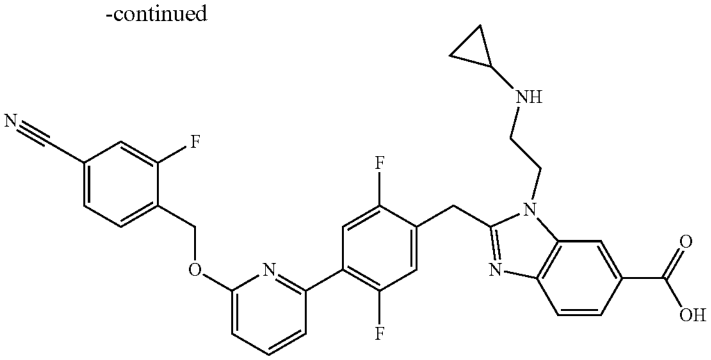

Example 906

Methyl 3-((2-((tert-butoxycarbonyl)(cyclopropyl)amino)ethyl)amino)-4-(2-(4-(6-((4-cyano-2-fluorobenzyl)oxy)pyridin-2-yl)-2,5-difluorophenyl)acetamido)benzoate: To a solution of 2-(4-(6-((4-cyano-2-fluorobenzyl)oxy)pyridin-2-yl)-2,5-difluorophenyl)acetic acid (51 mg, 0.13 mmol) and methyl 4-amino-3-((2-((tert-butoxycarbonyl)(cyclopropyl)amino)ethyl)amino)benzoate (55 mg, 0.16 mmol) in MeCN (1.25 mL) was added 1-methylimidazole (0.06 mL, 0.75 mmol) and TCFH (43 mg, 0.15 mmol). The resulting slurry was stirred at room temperature for 1 hour. The slurry was diluted with EtOAc and washed with HCl (1 M). The aqueous layer was backextracted with EtOAc and the combine organic layers were dried over $MgSO_4$ and concentrated to dryness. The resulting crude material was used directly in the next step. ES/MS m/z: 730.2 ($M+H^+$).

Methyl 2-(4-(6-((4-cyano-2-fluorobenzyl)oxy)pyridin-2-yl)-2,5-difluorobenzyl)-1-(2-(cyclopropylamino)ethyl)-1H-benzo[d]imidazole-6-carboxylate and methyl 1-(2-((tert-butoxycarbonyl)(cyclopropyl)amino)ethyl)-2-(4-(6-((4-cyano-2-fluorobenzyl)oxy)pyridin-2-yl)-2,5-difluorobenzyl)-1H-benzo[d]imidazole-6-carboxylate: A solution of methyl 3-((2-((tert-butoxycarbonyl)(cyclopropyl)amino)ethyl)amino)-4-(2-(4-(6-((4-cyano-2-fluorobenzyl)oxy)pyridin-2-yl)-2,5-difluorophenyl)acetamido)benzoate (93 mg, 0.13 mmol) in AcOH (1.25 mL) was heated to 70° C. for 2 hours. The resulting solution was diluted with $CH_2Cl_2$ and washed with $H_2O$ and aqueous sodium bicarbonate. The aqueous layers were backextracted with $CH_2Cl_2$ and the combine organic layers were dried over $MgSO_4$ and concentrated to dryness. The resulting crude material was purified by column chromatography (eluent: EtOAc/Hexanes) to yield methyl 2-(4-(6-((4-cyano-2-fluorobenzyl)oxy)pyridin-2-yl)-2,5-difluorobenzyl)-1-(2-(cyclopropylamino)ethyl)-1H-benzo[d]imidazole-6-carboxylate; ES/MS m/z: 612.2 ($M+H^+$) and methyl 1-(2-((tert-butoxycarbonyl)(cyclopropyl)amino)ethyl)-2-(4-(6-((4-cyano-2-fluorobenzyl)oxy)pyridin-2-yl)-2,5-difluorobenzyl)-1H-benzo[d]imidazole-6-carboxylate; ES/MS m/z: 712.0 ($M+H^+$).

2-(4-(6-((4-cyano-2-fluorobenzyl)oxy)pyridin-2-yl)-2,5-difluorobenzyl)-1-(2-(cyclopropylamino)ethyl)-1H-benzo[d]imidazole-6-carboxylic acid (Example 906): To a slurry of methyl 2-(4-(6-((4-cyano-2-fluorobenzyl)oxy)pyridin-2-yl)-2,5-difluorobenzyl)-1-(2-(cyclopropylamino)ethyl)-1H-benzo[d]imidazole-6-carboxylate (40 mg, 0.65 mmol) in MeCN (1.5 mL) was added $H_2O$ (0.25 mL) and lithium hydroxide (0.2 mL, 1 M aqueous). The reaction vial was sealed and heated to 100° C. for 5 min and cooled to room temperature. The resulting solution was diluted with MeCN and DMF and neutralized with TFA. Purification via reverse phase HPLC (eluent: $MeCN/H_2O/0.1\%$ TFA) provided 2-(4-(6-((4-cyano-2-fluorobenzyl)oxy)pyridin-2-yl)-2,5-difluorobenzyl)-1-(2-(cyclopropylamino)ethyl)-1H-benzo[d]imidazole-6-carboxylic acid (Example 906) as a trifluoroacetate salt. ES/MS m/z: 589.2 ($M+H^+$); 1H NMR (400 MHz, DMSO) δ 12.90 (s, 1H), 8.88 (s, 1H), 8.30 (d, J=1.5 Hz, 1H), 7.98-7.87 (m, 2H), 7.84 (dd, J=8.4, 1.5 Hz, 1H), 7.81-7.71 (m, 3H), 7.65 (d, J=8.4 Hz, 1H), 7.54 (dd, J=7.5, 1.7 Hz, 1H), 7.42 (dd, J=11.5, 6.1 Hz, 1H), 7.01 (d, J=8.3 Hz, 1H), 5.61 (s, 2H), 4.64 (t, J=7.2 Hz, 2H), 4.46 (s, 2H), 3.50 (s, 2H), 2.88 (d, J=16.3 Hz, 1H), 0.90-0.83 (m, 2H), 0.83-0.77 (m, 2H).

Example 907. 1-(2-((tert-butoxycarbonyl)(cyclopropyl)amino)ethyl)-2-(4-(6-((4-cyano-2-fluorobenzyl)oxy)pyridin-2-yl)-2,5-difluorobenzyl)-1H-benzo[d]imidazole-6-carboxylic Acid Procedure 112

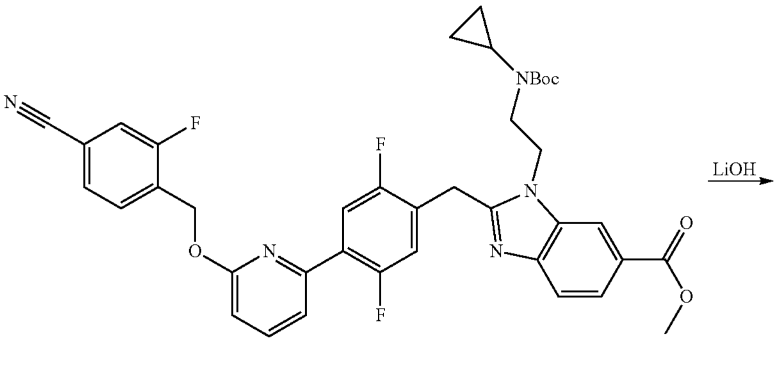

-continued

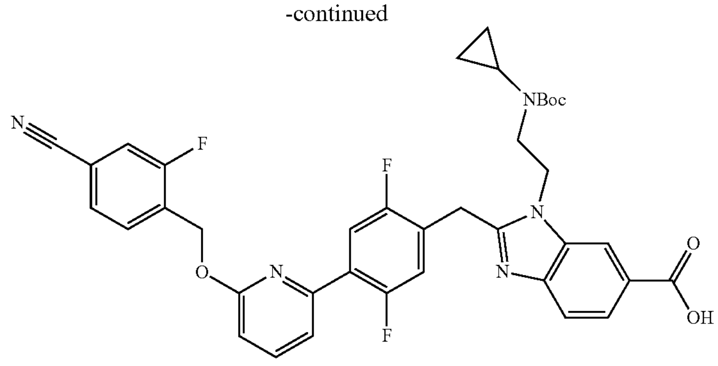

Example 907

1-(2-((tert-butoxycarbonyl)(cyclopropyl)amino)ethyl)-2-(4-(6-((4-cyano-2-fluorobenzyl)oxy)pyridin-2-yl)-2,5-difluorobenzyl)-1H-benzo[d]imidazole-6-carboxylic acid (Example 907): To a slurry of methyl 1-(2-((tert-butoxycarbonyl)(cyclopropyl)amino)ethyl)-2-(4-(6-((4-cyano-2-fluorobenzyl)oxy)pyridin-2-yl)-2,5-difluorobenzyl)-1H-benzo[d]imidazole-6-carboxylate (24 mg, 0.34 mmol), obtained as described in Procedure 111 in MeCN (1.0 mL) was added $H_2O$ (0.20 mL) and lithium hydroxide (0.2 mL, 1 M aqueous). The reaction vial was sealed and heated to 100° C. for 5 min and cooled to room temperature. The resulting solution was diluted with MeCN and DMF and neutralized with TFA. Purification via reverse phase HPLC (eluent: MeCN/$H_2O$/0.1% TFA) provided 1-(2-((tert-butoxycarbonyl)(cyclopropyl)amino)ethyl)-2-(4-(6-((4-cyano-2-fluorobenzyl)oxy)pyridin-2-yl)-2,5-difluorobenzyl)-1H-benzo[d]imidazole-6-carboxylic acid (Example 907) as a trifluoroacetate salt. ES/MS m/z: 698.2 ($M+H^+$); 1H NMR (400 MHz, DMSO) δ 12.78 (s, 1H), 8.14 (d, J=1.5 Hz, 1H), 7.96-7.86 (m, 2H), 7.83-7.70 (m, 4H), 7.61 (d, J=8.4 Hz, 1H), 7.53 (dd, J=7.5, 1.8 Hz, 1H), 7.40 (dd, J=11.4, 6.0 Hz, 1H), 7.00 (d, J=8.2 Hz, 1H), 5.61 (s, 2H), 4.53 (t, J=6.0 Hz, 2H), 4.39 (s, 2H), 3.56 (t, J=5.8 Hz, 2H), 2.30 (s, 1H), 1.25 (d, J=10.4 Hz, 9H), 0.52 (s, 2H), 0.27 (s, 2H).

Example 911. 2-[[2,5-difluoro-4-[6-[(2-fluoro-4-pyrimidin-2-yl-phenyl)methoxy]-2-pyridyl]phenyl]methyl]-3-(2-methoxyethyl)benzimidazole-5-carboxylic acid Procedure 113

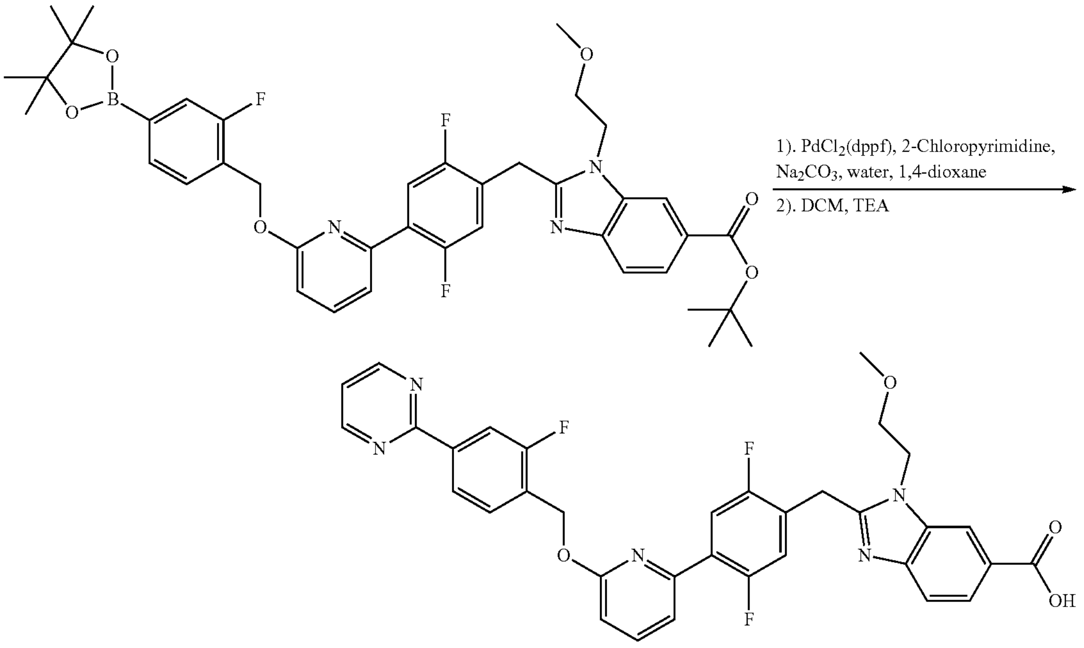

Example 911

2-[[2,5-difluoro-4-[6-[(2-fluoro-4-pyrimidin-2-yl-phenyl)methoxy]-2-pyridyl]phenyl]methyl]-3-(2-methoxyethyl)benzimidazole-5-carboxylic acid (Example 911): A microwave vial was charged with tert-butyl 2-[[2,5-difluoro-4-[6-[[2-fluoro-4-(4,4,5,5-tetramethyl-1,3,2-dioxaborolan-2-yl)phenyl]methoxy]-2-pyridyl]phenyl]methyl]-3-(2-methoxyethyl)benzimidazole-5-carboxylate (I-195, 20 mg, 0.03 mml), 2-Chloropyrimidine (6.3 mg, 0.06 mml), sodium carbonate (8.7 mg, 0.08 mmol), $PdCl_2$(dppf) (2 mg, 0.003 mmol), 1,4-dioxane (1.5 ml) and water (0.5 ml). The mixture was heated in a microwave at 100° C. for 10 minutes. The reaction was cooled, diluted with 2 ml 4:1 acetonitrile:water with 0.1% HCl, passed through a C18 SPE column eluting with another 3 ml of 4:1 acetonitrile:water with 0.1% HCl. The solution was concentrated, dissolved in 2 ml DCM and transferred to a vial and 1 ml TFA was added. The resulting mixture was stirred 1 hour, concentrated and purified by HPLC to yield 2-[[2,5-difluoro-4-[6-[(2-fluoro-4-pyrimidin-2-yl-phenyl)methoxy]-2-pyridyl]phenyl]methyl]-3-(2-methoxyethyl)benzimidazole-5-carboxylic acid (Example 911). ES/MS m/z: $^1$H NMR (400 MHz, DMSO-d6) δ 8.94 (d, 2H), 8.26 (dd, 1H), 8.22 (d, 1H), 8.15 (dd, 1H), 7.89 (t, 1H), 7.86-7.78 (m, 2H), 7.74 (t, 1H), 7.61 (d, 1H), 7.55-7.48 (m, 2H), 7.38 (dd, 1H), 6.99 (d, 1H), 5.61 (s, 2H), 4.60 (t, 2H), 4.45 (s, 2H), 3.68 (t, 2H), 3.21 (s, 3H).

Examples 908-910. Compounds Prepared Using Procedure 113

Other compounds of the present disclosure prepared using the general route described in Procedure 113 include the following Examples.

| Example | Structure/Name/Characterization |
|---|---|
| 908 | 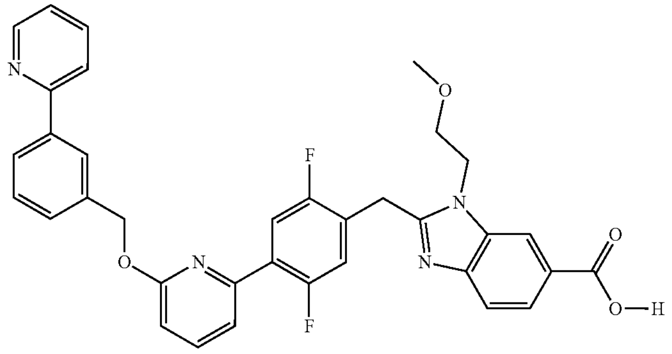 [SMILES: COCCn1c(Cc2cc(F)c(-c3cccc(OCc4cccc(-c5ncccn5)c4)n3)cc2F)nc2ccc(C(=O)O)cc21]<br>ES/MS m/z 607.1; 1H NMR (400 MHz, Acetonitrile-d3) δ 8.72 (d, 1H), 8.40 (d, 1H), 8.21 (s, 1H), 8.11-8.05 (m, 2H), 8.03-7.94 (m, 2H), 7.88-7.74 (m, 3H), 7.67 (d, 1H), 7.60 (d, 1H), 7.58-7.49 (m, 2H), 7.27 (dd, 1H), 6.93 (d, 1H), 5.61 (s, 2H), 4.66-4.56 (m, 4H), 3.76 (t, 2H), 3.27 (s, 3H). |
| 909 | 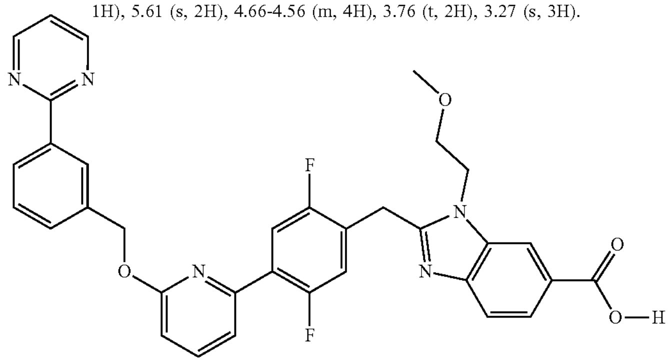<br>ES/MS m/z 608.3; 1H NMR (400 MHz, Acetonitrile-d3) δ 8.82 (d, 2H), 8.62 (d, 1H), 8.44-8.39 (m, 2H), 8.11 (dd, 1H), 7.93 (dd, 1H), 7.85-7.74 (m, 2H), 7.68-7.63 (m, 1H), 7.58-7.50 (m, 2H), 7.29 (q, 2H), 6.93 (d, 1H), 5.61 (s, 2H), 4.67-4.58 (m, 4H), 3.76 (t, 2H), 3.26 (s, 3H). |
| 910 | 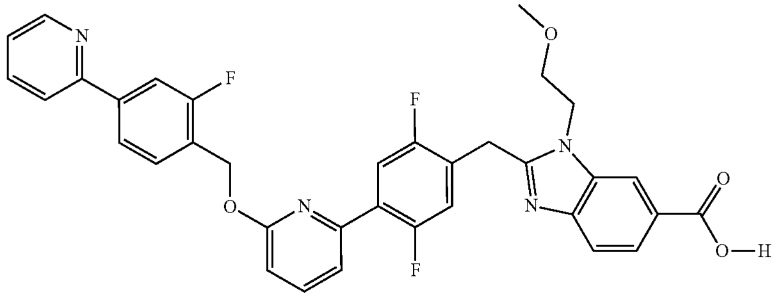 [SMILES: COCCn1c(Cc2cc(F)c(-c3cccc(OCc4ccc(-c5ccccn5)cc4F)n3)cc2F)nc2ccc(C(=O)O)cc21]<br>ES/MS m/z 625.2; 1H NMR (400 MHz, DMSO-d6) δ 8.71-8.67 (m, 1H), 8.24-8.21 (m, 1H), 8.04 (d, 1H),7.98 (s, 1H), 7.97-7.95 (m, 1H), 7.94-7.83 (m, 3H), 7.81 (dd, 1H), 7.69 (t, 1H), 7.61 (d, 1H), 7.53 (dd, 1H), 7.43-7.35 (m, 2H), 6.98 (d, 1H), 5.58 (s, 2H), 4.60 (t, 2H), 4.46 (s, 2H), 3.68 (t, 2H), 3.21 (s, 3H). |

Example 915. 2-[[2,5-difluoro-4-[6-[[2-fluoro-4-(1-methylpyrazol-4-yl)phenyl]methoxy]-2-pyridyl]phenyl]methyl]-3-(2-methoxyethyl)benzimidazole-5-carboxylic acid Procedure 114

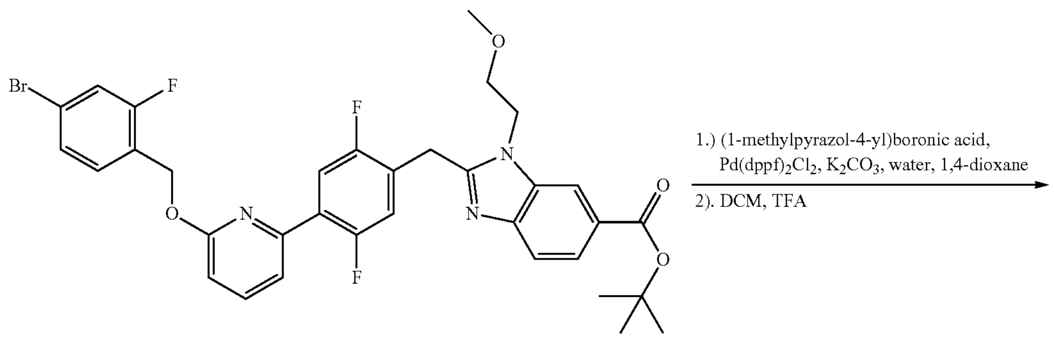

I-194

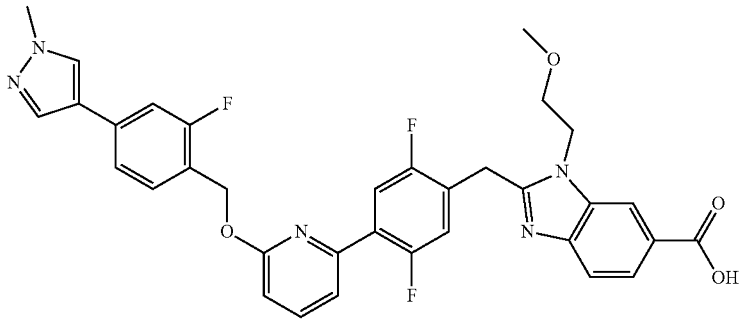

Example 915

2-[[2,5-difluoro-4-[6-[[2-fluoro-4-(1-methylpyrazol-4-yl)phenyl]methoxy]-2-pyridyl]phenyl]methyl]-3-(2-methoxyethyl)benzimidazole-5-carboxylic acid (Example 915): A microwave vial was charged tert-butyl 2-[[4-[6-[(4-bromo-2-fluoro-phenyl)methoxy]-2-pyridyl]-2,5-difluoro-phenyl]methyl]-3-(2-methoxyethyl)benzimidazole-5-carboxylate (I-194, 25 mg, 0.04 mml), (1-methylpyrazol-4-yl)boronic acid (9.2 mg, 0.07 mml), potassium carbonate (10 mg, 0.07 mmol), $PdCl_2$(dppf) (2 mg, 0.004 mmol), 1,4-dioxane (1.5 ml) and water (0.5 ml). The mixture was heated in a microwave at 100° C. for 10 minutes. The reaction was cooled, diluted with 2 ml 4:1 acetonitrile:water with 0.1% HCl, passed through a C18 SPE column eluting with another 3 ml of 4:1 acetonitrile:water with 0.1% HCl. The solution was concentrated, dissolved in 2 ml DCM and transferred to a vial and 1 ml TFA was added. The resulting mixture was stirred 1 hour, concentrated and purified by HPLC to yield 2-[[2,5-difluoro-4-[6-[[2-fluoro-4-(1-methylpyrazol-4-yl)phenyl]methoxy]-2-pyridyl]phenyl]methyl]-3-(2-methoxyethyl)benzimidazole-5-carboxylic acid (Example 915). ES/MS m/z: 628.2 ($M+H^+$); $^1H$ NMR (400 MHz, DMSO-d6) δ 8.25 (d, 1H), 8.22 (s, 1H), 7.93 (s, 1H), 7.90-7.81 (m, 3H), 7.63 (d, 1H), 7.57-7.46 (d, 3H), 7.45-7.36 (i, 2H), 6.94 (d, 1H), 5.49 (s, 2H), 4.63 (t, 2H), 4.49 (s, 2H), 3.86 (s, 3H), 3.75-3.66 (m, 2H), 3.22 (s, 3H).

Examples 912-914, 916-917. Compounds Prepared Using Procedure 114

Other compounds of the present disclosure prepared using the general route described in Procedure 114 include the following Examples.

| Example | Structure/Name/Characterization |
|---|---|
| 912 | 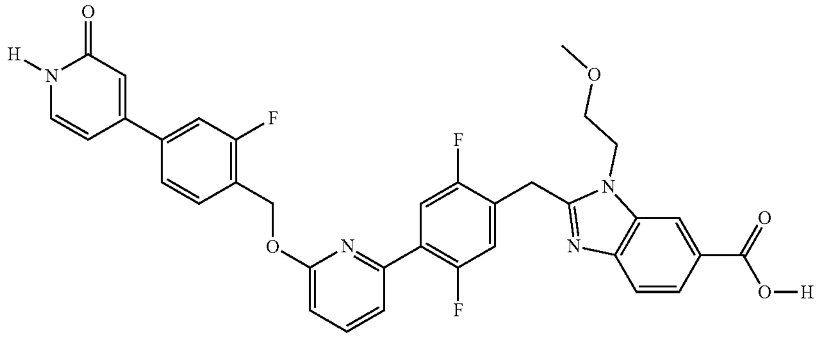 [SMILES: COCCn1c(Cc2cc(F)c(-c3cccc(OCc4ccc(-c5cc[nH]c(=O)c5)cc4F)n3)cc2F)nc2ccc(C(=O)O)cc21] ES/MS m/z 641.1; 1H NMR (400 MHz, DMSO-d6) δ 8.22 (s, 1H), 7.96 (s, 1H), 7.92-7.86 (m, 1H), 7.86-7.78 (m, 2H), 7.70-7.55 (m, 5H), 7.52 (d, 1H), 7.46 (d, 1H), 7.38 (dd, 1H), 6.97 (d, 1H), 6.66 (s, 1H), 6.57-6.50 (m, 1H), 5.57 (s, 2H), 4.60 (s, 2H), 4.46 (s, 2H), 3.69 (t, 3H), 3.21 (s, 3H). |
| 913 | 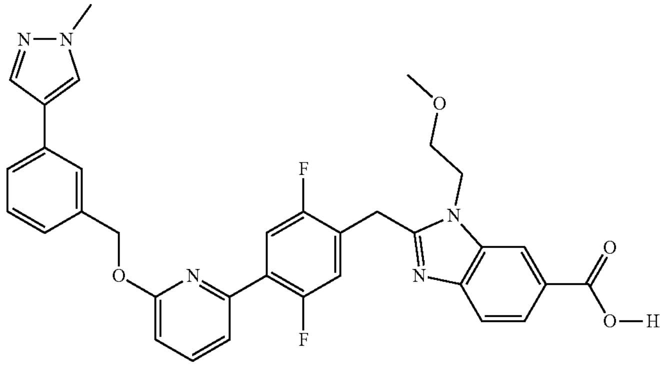 ES/MS m/z 610.1; 1H NMR (400 MHz, DMSO-d6) δ 8.30 (d, 1H), 8.13 (s, 1H), 7.91-7.84 (m, 4H), 7.71 (d, 1H), 7.66 (d, 1H), 7.51 (td, 2H), 7.43 (dd, 1H), 7.37 (t, 1H), 7.33-7.29 (m, 1H), 6.97 (d, 1H), 5.47 (s, 2H), 4.66 (t, 2H), 4.53 (s, 2H), 3.85 (s, 3H), 3.70 (t, 2H), 3.21 (s, 3H). |
| 914 | 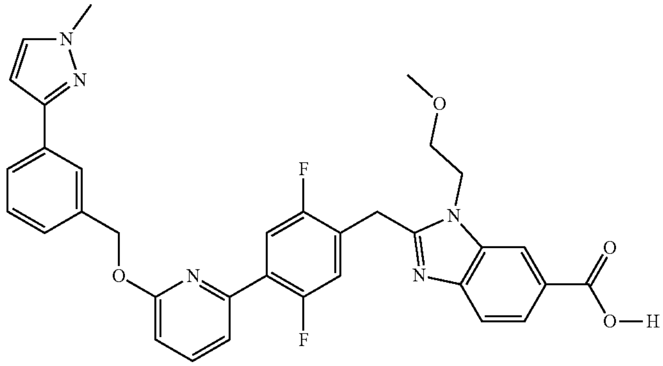 [SMILES: COCCn1c(Cc2cc(F)c(-c3cccc(OCc4cccc(-c5ccn(C)n5)c4)n3)cc2F)nc2ccc(C(=O)O)cc21] ES/MS m/z 610.3; 1H NMR (400 MHz, DMSO-d6) δ 8.22 (d, 1H), 7.94 (d, 1H), 7.90-7.83 (m, 2H), 7.83-7.79 (m, 1H), 7.73 (td, 1H), 7.71 (d, 1H), 7.61 (d, 1H), 7.50 (dd, 1H), 7.44-7.34 (m, 3H), 6.97 (d, 1H), 6.68 (d, 1H), 5.51 (s, 2H), 4.60 (t, 2H), 4.46 (s, 2H), 3.86 (s, 3H), 3.69 (t, 2H), 3.21 (s, 3H). |

-continued
| Example | Structure/Name/Characterization |
| --- | --- |
| 916 | 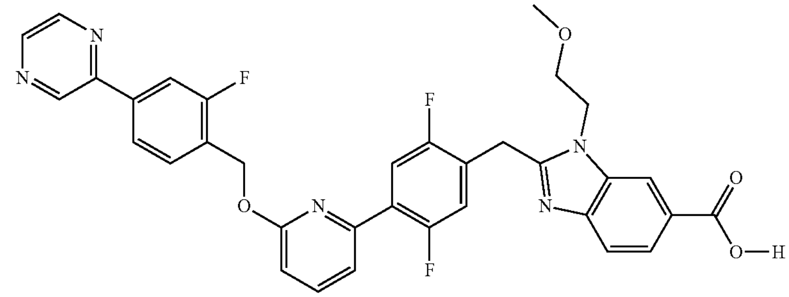 [SMILES: COCCn1c(Cc2cc(F)c(-c3cccc(OCc4ccc(-c5cnccn5)cc4F)n3)cc2F)nc2ccc(C(=O)O)cc21]<br>ES/MS m/z 628.2; 1H NMR (400 MHz, DMSO-d6) δ 8.25 (d, 1H), 8.22 (s, 1H), 7.93 (s, 1H), 7.90-7.81 (m, 3H), 7.63 (d, 1H), 7.57-7.46 (m, 3H), 7.45-7.36 (m, 2H), 6.94 (d, 1H), 5.49 (s, 2H), 4.63 (t, 2H), 4.49 (s, 2H), 3.86 (s, 3H), 3.75-3.66 (m, 2H), 3.22 (s, 3H). |
| 917 | 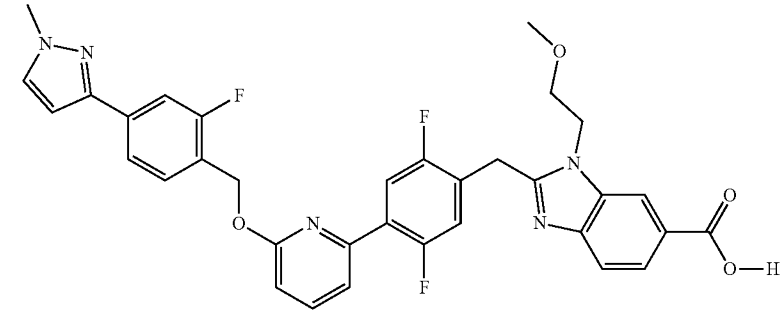 [SMILES: COCCn1c(Cc2cc(F)c(-c3cccc(OCc4ccc(-c5ccn(C)n5)cc4F)n3)cc2F)nc2ccc(C(=O)O)cc21]<br>ES/MS m/z 626.3; 1H NMR (400 MHz, DMSO-d6) δ 8.30 (d, 1H), 7.90-7.85 (m, 3H), 7.76 (d, 1H), 7.67-7.63 (m, 3H), 7.62-7.56 (m, 2H), 7.52 (dd, 1H), 7.42 (dd, 1H), 6 96 (d, 1H), 6.77 (d, 1H), 5.52 (s, 2H), 4.66 (t, 2H), 4.53 (s, 2H), 3.89 (s, 3H), 3.70 (t, 2H), 3.22 (s, 3H). |
Example 918. 3-[(3R,4S)-1-acetyl-4-methoxy-pyrrolidin-3-yl]-2-[[4-[6-[(4-cyano-2-fluoro-phenyl)methoxy]-2-pyridyl]-2,5-difluoro-phenyl]methyl]benzimidazole-5-carboxylic acid
Procedure 115
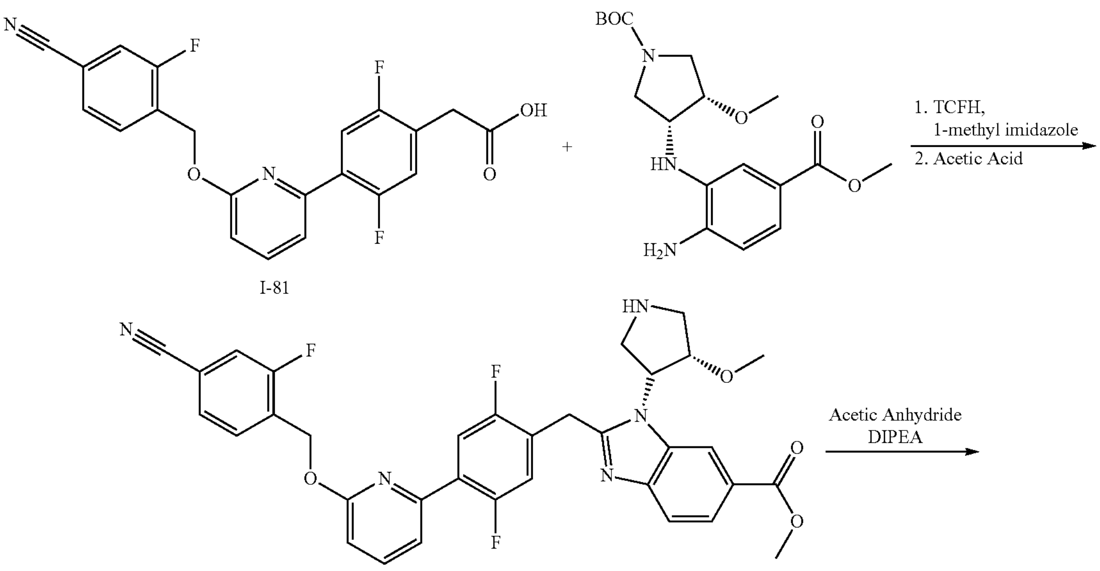

-continued

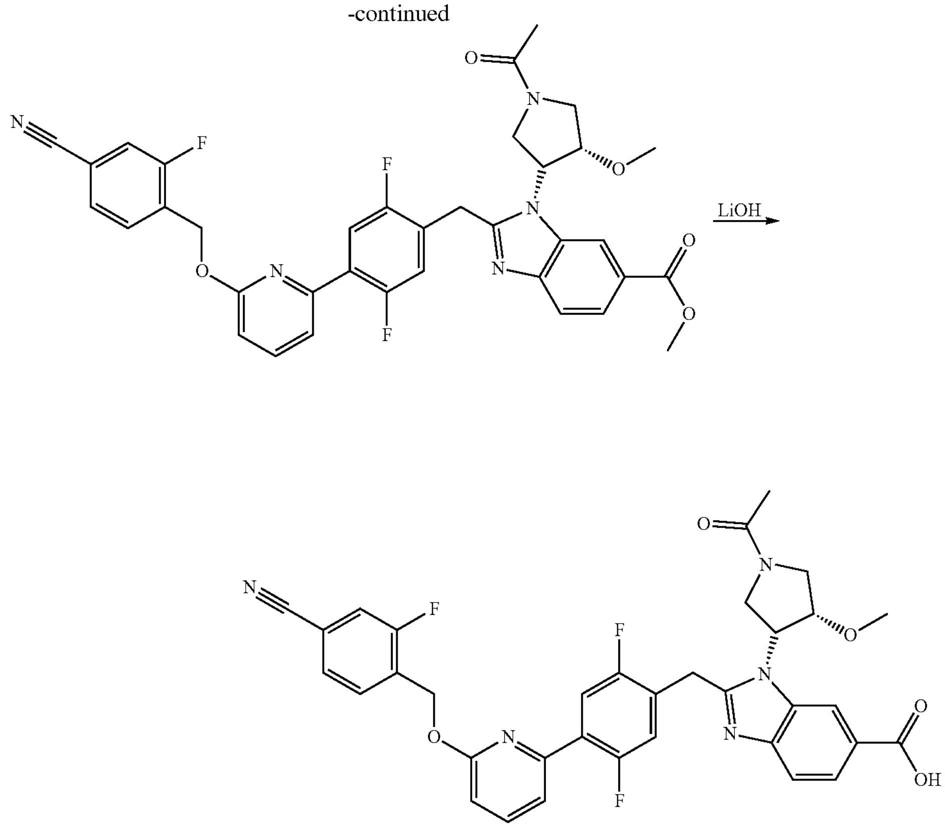

Example 918

Methyl 2-[[4-[6-[(4-cyano-2-fluoro-phenyl)methoxy]-2-pyridyl]-2,5-difluoro-phenyl]methyl]-3-[(4S)-4-methoxy-pyrrolidin-3-yl]benzimidazole-5-carboxylate: tert-Butyl (3R,4S)-3-(2-amino-5-methoxycarbonyl-anilino)-4-methoxy-pyrrolidine-1-carboxylate (398 mg, 1.09 mmol) was obtained as described in for I-198 substituting [(2S)-tetrahydrofuran-2-yl]methanamine with tert-butyl (3R,4S)-3-amino-4-methoxy-pyrrolidine-1-carboxylate. This was combined with 2-(4-(6-((4-cyano-2-fluorobenzyl)oxy)pyridin-2-yl)-2,5-difluorophenyl)acetic acid (I-81, 299 mg, 0.75 mmol), TCFH (225 mg, 0.802 mmol), 1-Methylimidazole (0.333 mL, 343 mg, 4.18 mmol), and ACN (3 mL) in a vial. The mixture was stirred at rt for 30 minutes. Upon completion the reaction contents were diluted with EtOAc, washed with 1 M HCl, back extracted with EtOAc, then washed with brine, dried over $MgSO_4$, filtered, and concentrated. The crude material was then taken up in 3 mL of acetic acid and transferred to a microwave vial. The solution was heated in a microwave at 120° C. for 1 h. The mixture was then concentrated, diluted with EtOAc, washed with bicarb, then water, then brine, and dried over $MgSO_4$, filtered over a small silica plug, and concentrated. This material was carried forward without further purification.

Methyl 3-[(3R,4S)-1-acetyl-4-methoxy-pyrrolidin-3-yl]-2-[[4-[6-[(4-cyano-2-fluoro-phenyl)methoxy]-2-pyridyl]-2,5-difluoro-phenyl]methyl]benzimidazole-5-carboxylate: Methyl 2-[[4-[6-[(4-cyano-2-fluoro-phenyl)methoxy]-2-pyridyl]-2,5-difluoro-phenyl]methyl]-3-[(4S)-4-methoxy-pyrrolidin-3-yl]benzimidazole-5-carboxylate (51 mg, 0.08 mmol) was transferred to a vial with 2 mL of DCM. Then diisopropylethylamine (0.03 mL, 0.16 mmol) was added by syringe followed by acetic anhydride (0.012 mL, 0.12 mmol). The mixture was stirred overnight at rt. The mixture was diluted with DCM, washed with saturated ammonium chloride, dried over $MgSO_4$, filtered, and concentrated. The crude material was used in the next step without further purification.

3-[(3R,4S)-1-acetyl-4-methoxy-pyrrolidin-3-yl]-2-[[4-[6-[(4-cyano-2-fluoro-phenyl)methoxy]-2-pyridyl]-2,5-difluoro-phenyl]methyl]benzimidazole-5-carboxylic acid (Example 918): Methyl 3-[(3R,4S)-1-acetyl-4-methoxy-pyrrolidin-3-yl]-2-[[4-[6-[(4-cyano-2-fluoro-phenyl)methoxy]-2-pyridyl]-2,5-difluoro-phenyl]methyl]benzimidazole-5-carboxylate (55 mg, 0.082 mmol) was added via 3 mL of ACN to a scintillation vial. An aliquot of 1 mL of $H_2O$ was added followed by lithium hydroxide (10.3 mg, 0.25 mmol). The mixture was stirred for 8 hours at rt, then 1 hour at 60° C. An aliquot of 1 mL of DMF was added and the mixture was concentrated, filtered through a syringe filter, and purified by reverse phase chromatography (10-63% ACN/water with 0.1% TFA) to give 3-[(3R,4S)-1-acetyl-4-methoxy-pyrrolidin-3-yl]-2-[[4-[6-[(4-cyano-2-fluoro-phenyl)methoxy]-2-pyridyl]-2,5-difluoro-phenyl]methyl]benzimidazole-5-carboxylic acid. (Example 918) ES/MS m/z: 656.2 $(M+H^+)$; 1H NMR (400 MHz, DMSO-d6) δ 8.29 (dd, J=41.5, 1.4 Hz, 1H), 7.98-7.87 (m, 2H), 7.82-7.71 (m, 4H), 7.67-7.51 (m, 2H), 7.36 (ddd, J=11.5, 6.1, 2.7 Hz, 1H), 7.00 (d, J=8.2 Hz, 1H), 5.61 (s, 2H), 5.49 (dtd, J=17.0, 8.5, 4.8 Hz, 1H), 4.63-4.45 (m, 2H), 4.34 (t, J=9.6 Hz, 0H), 4.22 (q, J=4.6 Hz, 1H), 4.18-4.08 (m, 1H), 4.02 (dd, J=10.4, 8.7 Hz, 0H), 3.96-3.84 (m, 1H), 3.12 (d, J=12.5 Hz, 3H), 2.06 (d, J=13.2 Hz, 3H).

Example 919-921. Compounds Prepared Using Procedure 115

Other compounds of the present disclosure prepared using the general route described in Procedure 115 include the following Example.

| Example | Structure/Name/Characterization |
|---|---|
| 919 | 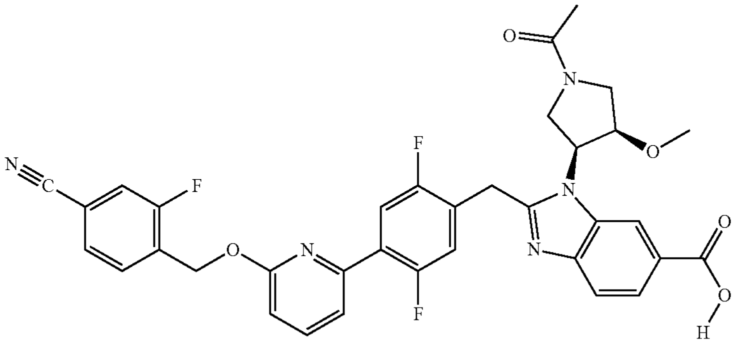 [SMILES: CO[C@@H]1CN(C(C)=O)C[C@@H]1n1c(Cc2cc(F)c(-c3cccc(OCc4ccc(C#N)cc4F)n3)cc2F)nc2ccc(C(=O)O)cc21] ES/MS m/z 656.2; 1H NMR (400 MHz, DMSO-d6) δ 8.30 (dd, J = 41.0, 1.4 Hz, 1H), 8.00-7.85 (m, 2H), 7.84-7.70 (m, 4H), 7.62 (dd, J = 8.5, 2.2 Hz, 1H), 7.54 (d, J = 7.3 Hz, 1H), 7.37 (ddd, J = 11.6, 6.2, 2.0 Hz, 1H), 7.00 (d, J = 8.3 Hz, 1H), 5.61 (s, 2H), 5.50 (dtd, J = 16.7, 8.6, 4.8 Hz, 1H), 4.68-4.46 (m, 2H), 4.40-3.99 (m, 2H), 3.95-3.83 (m, 1H), 3.78-3.57 (m, 2H), 3.12 (d, J = 12.4 Hz, 3H), 2.07 (d, J = 13.2 Hz, 3H). 19F NMR (376 MHz, DMSO-d6) δ −115.93 (dd, J = 10.0, 6.2 Hz), −121.87 (td, J = 11.5, 6.1 Hz), −122.02-−122.35 (m). |
| 920 | 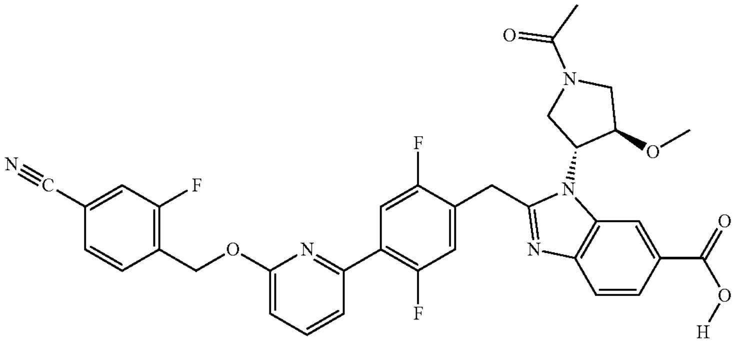 [SMILES: CO[C@@H]1CN(C(C)=O)C[C@H]1n1c(Cc2cc(F)c(-c3cccc(OCc4ccc(C#N)cc4F)n3)cc2F)nc2ccc(C(=O)O)cc21] ES/MS m/z 656.2; 1H NMR (400 MHz, DMSO-d6) δ 8.12 (dd, J = 37.6, 1.4 Hz, 1H), 7.98-7.82 (m, 3H), 7.80-7.65 (m, 5H), 7.53 (dd, J = 7.5, 1.6 Hz, 1H), 7.39 (ddd, J = 11.5, 6.1, 3.4 Hz, 1H), 7.00 (d, J = 8.3 Hz, 1H), 5.60 (s, 2H), 5.34 (dq, J = 27.0, 8.1 Hz, 1H), 4.74-4.39 (m, 3H), 4.29-3.95 (m, 2H), 3.99-3.78 (m, 1H), 3.51 (dd, J = 10.7, 6.6 Hz, 1H), 3.30 (dd, J = 12.0, 6.6 Hz, 0H), 3.17 (d, J = 5.7 Hz, 3H), 2.05 (d, J = 24.2 Hz, 3H). 19F NMR (376 MHz, DMSO-d6) δ −115.93 (dd, J = 10.0, 6.2 Hz), −121.96 (dtd, J = 18.4, 12.3, 6.5 Hz), −122.25 (tdd, J = 17.1, 10.3, 6.2 Hz). |
| 921 | 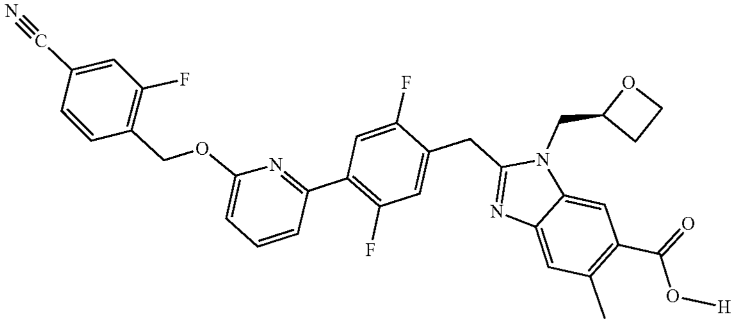 [SMILES: Cc1cc2nc(Cc3cc(F)c(-c4cccc(OCc5ccc(C#N)cc5F)n4)cc3F)n(C[C@@H]3CCO3)c2cc1C(=O)O] ES/MS m/z 599.2; 1H NMR (400 MHz, Chloroform-d) δ 8.19 (s, 1H), 7.78-7.63 (m, 4H), 7.53-7.46 (m, 2H), 7.42 (dd, J = 9.2, 1.5 Hz, 1H), 7.28 (s, 1H), 7.15 (dd, J = 11.2, 6.0 Hz, 1H), 6.84 (d, J = 8.2 Hz, 1H), 5.59 (s, 2H), 5.17 (qd, |

-continued

| Example | Structure/Name/Characterization |
|---|---|
| | J = 6.9, 2.7 Hz, 1H), 4.66 (ddd, J = 11.1, 8.4, 4.6 Hz, 1H), 4.57 (d, J = 13.1 Hz, 2H), 4.53-4.34 (m, 3H), 2.78 (s, 3H), 2.43 (ddt, J = 11.5, 8.9, 7.2 Hz, 1H). 19F NMR (376 MHz, Chloroform-d) δ −114.77−-116.23 (m), −118.96−-120.82 (m), −123.68 (ddd, J = 17.5, 10.7, 6.1 Hz). |

Example 922. 2-[[4-[6-[(4-cyano-2-fluoro-phenyl) methoxy]-2-pyridyl]-2,5-difluoro-phenyl]methyl]-3-[(3R,4S)-4-methoxypyrrolidin-3-yl]benzimidazole-5-carboxylic acid Procedure 116

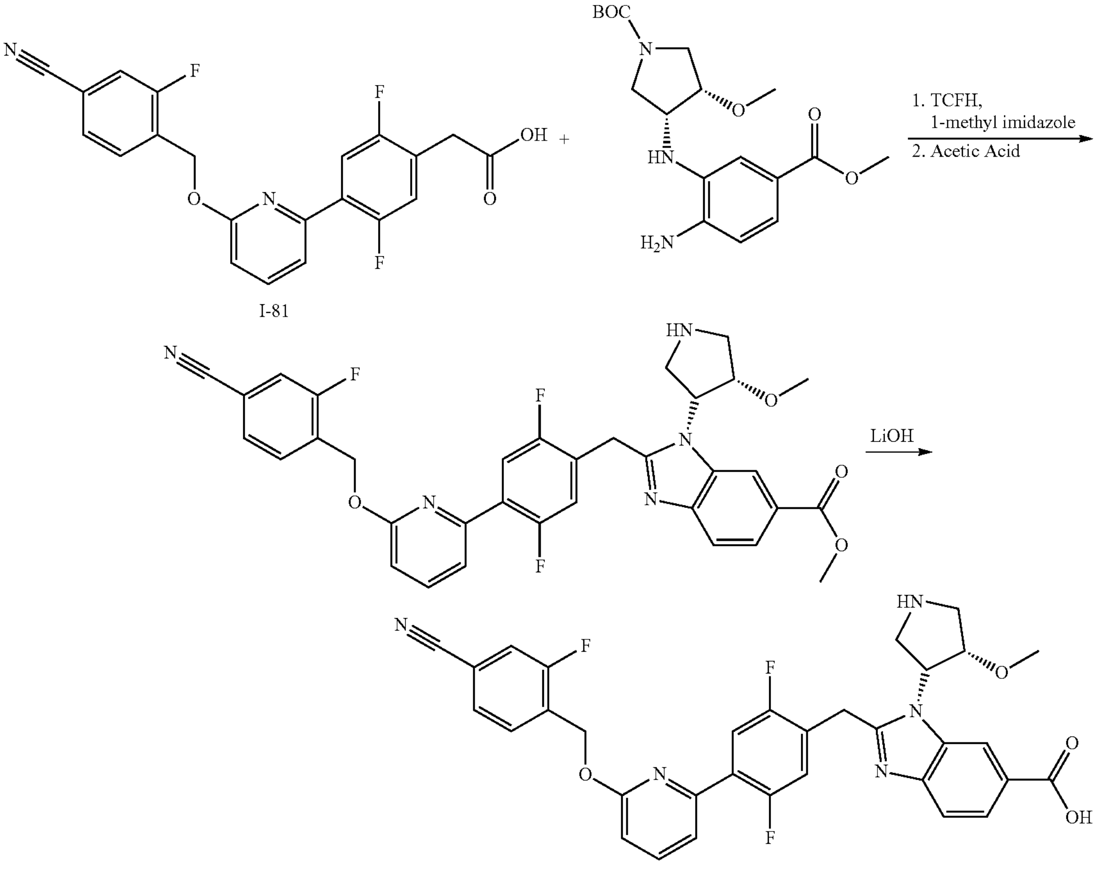

I-81

Example 922

Methyl 2-[[4-[6-[(4-cyano-2-fluoro-phenyl)methoxy]-2-pyridyl]-2,5-difluoro-phenyl]methyl]-3-[(4S)-4-methoxy-pyrrolidin-3-yl]benzimidazole-5-carboxylate: tert-Butyl (3R,4S)-3-(2-amino-5-methoxycarbonyl-anilino)-4-methoxy-pyrrolidine-1-carboxylate (398 mg, 1.09 mmol) was obtained as described for I-198 substituting [(2S)-tetrahydrofuran-2-yl]methanamine with tert-butyl (3R,4S)-3-amino-4-methoxy-pyrrolidine-1-carboxylate. This was combined with 2-(4-(6-((4-cyano-2-fluorobenzyl)oxy)pyridin-2-yl)-2,5-difluorophenyl)acetic acid (I-81, 299 mg, 0.75 mmol), TCFH (225 mg, 0.802 mmol), 1-Methylimidazole (0.333 mL, 343 mg, 4.18 mmol), and ACN (3 mL) in a vial. The mixture was stirred at rt for 30 minutes. Upon completion the reaction contents were diluted with EtOAc, washed with 1 M HCl, back extracted with EtOAc, then washed with brine, dried over $MgSO_4$, filtered, and concentrated. The crude material was then taken up in 3 mL of acetic acid and transferred to a microwave vial. The solution was heated in a microwave at 120° C. for 1 h. The mixture was then concentrated, diluted with EtOAc, washed with bicarb, then water, then brine, and dried over $MgSO_4$, filtered over a small silica plug, and concentrated. This material was carried forward without further purification.

2-[[4-[6-[(4-cyano-2-fluoro-phenyl)methoxy]-2-pyridyl]-2,5-difluoro-phenyl]methyl]-3-[(3R,4S)-4-methoxypyrrolidin-3-yl]benzimidazole-5-carboxylic acid (Example 922): Methyl 2-[[4-[6-[(4-cyano-2-fluoro-phenyl)methoxy]-2-pyridyl]-2,5-difluoro-phenyl]methyl]-3-[(4S)-4-methoxy-pyrrolidin-3-yl]benzimidazole-5-carboxylate (51 mg, 0.081 mmol) was added via 3 mL of ACN to a scintillation vial. An aliquot of 1 mL of $H_2O$ was added followed by lithium hydroxide (10.3 mg, 0.25 mmol). The mixture was stirred for 8 hours at rt, then 1 hour at 60° C. An aliquot of 1 mL of DMF was added and the mixture was concentrated, filtered through a syringe filter, and purified by reverse phase chromatography (10-58% ACN/water with 0.1% TFA) to give 2-[[4-[6-[(4-cyano-2-fluoro-phenyl)methoxy]-2-pyridyl]-2,5-difluoro-phenyl]methyl]-3-[(3R,4S)-4-methoxypyrrolidin-3-yl]benzimidazole-5-carboxylic acid. (Example 922) ES/MS m/z: 614.2 (M+H$^+$); 1H NMR (400 MHz, DMSO-d6) δ 9.67 (s, 1H), 9.34 (s, 1H), 8.40 (d, J=1.5 Hz, 1H), 7.97-7.88 (m, 2H), 7.84-7.72 (m, 4H), 7.62 (d, J=8.4 Hz, 1H), 7.54 (dd, J=7.5, 1.7 Hz, 1H), 7.34 (dd, J=11.4, 6.1 Hz, 1H), 7.01 (d, J=8.3 Hz, 1H), 5.61 (s, 2H), 5.55 (td, J=10.2, 4.4 Hz, 1H), 4.60-4.45 (m, 2H), 4.26 (t, J=3.8 Hz, 1H), 4.02 (d, J=10.5 Hz, 1H), 3.81-3.68 (m, 2H), 3.45 (d, J=11.6 Hz, 1H), 3.13 (s, 3H).

Examples 923-924. Compounds Prepared Using Procedure 116

Other compounds of the present disclosure prepared using the general route described in Procedure 116 include the following Examples.

| Example | Structure/Name/Characterization |
|---|---|
| 923 | 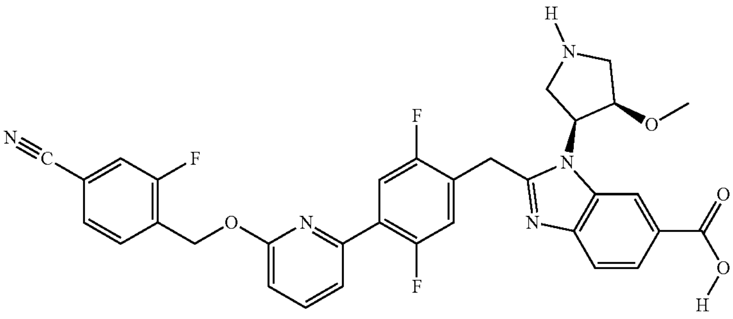 [SMILES: CO[C@@H]1CNC[C@@H]1n1c(Cc2cc(F)c(-c3cccc(OCc4ccc(C#N)cc4F)n3)cc2F)nc2ccc(C(=O)O)cc21]<br>ES/MS m/z 614.2; 1H NMR (400 MHz, DMSO-d6) δ 9.65 (s, 1H), 9.26 (s, 1H), 8.40 (d, J = 1.4 Hz, 1H), 7.98-7.85 (m, 2H), 7.85-7.69 (m, 5H), 7.62 (d, J = 8.4 Hz, 1H), 7.54 (dd, J = 7.5, 1.6 Hz, 1H), 7.34 (dd, J = 11.4, 6.1 Hz, 1H), 7.01 (d, J = 8.3 Hz, 1H), 5.61 (s, 2H), 5.54 (td, J = 10.2, 4.3 Hz, 1H), 4.61-4.45 (m, 2H), 4.26 (t, J = 3.7 Hz, 1H), 3.45 (s, 1H), 3.13 (s, 3H). "  19F NMR (376 MHz, DMSO-d6) δ −115.96 (dd, J = 10.0, 5.8 Hz), −121.78-−122.02 (m), −122.16 (ddd, J = 17.4, 10.5, 6.1 Hz)." |
| 924 | 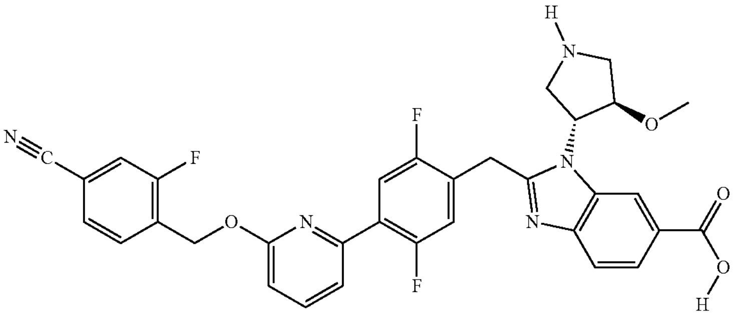 [SMILES: CO[C@@H]1CNC[C@H]1n1c(Cc2cc(F)c(-c3cccc(OCc4ccc(C#N)cc4F)n3)cc2F)nc2ccc(C(=O)O)cc21]<br>ES/MS m/z 614.2, 1H NMR (400 MHz, DMSO-d6) δ 9.35 (s, 2H), 8.27 (d, J = 1.4 Hz, 1H), 8.06-7.87 (m, 3H), 7.82-7.61 (m, 4H), 7.53 (dd, J = 7.5, 1.7 Hz, 1H), 7.34 (dd, J = 11.5, 6.1 Hz, 1H), 7.01 (d, J = 8.3 Hz, 1H), 5.60 (s, 2H), 5.28 (q, J = 9.4 Hz, 1H), 4.67 (q, J = 7.0 Hz, 1H), 4.57-4.38 (m, 2H), 3.74 (s, 2H), 3.34 (d, J = 12.7 Hz, 1H), 3.15 (s, 3H). 19F NMR (376 MHz, DMSO-d6) δ −115.97 (dd, J = 9.8, 5.8 Hz), −121.79-−122.01 (m), −122.24 (ddd, J = 17.4, 10.4, 6.0 Hz). |

Example 925. (R)-1-((1-acetylazetidin-2-yl)methyl)-2-(4-(6-((4-cyano-2-fluorobenzyl)oxy)pyridin-2-yl)-2,5-difluorobenzyl)-1H-benzo[d]imidazole-6-carboxylic Acid
Procedure 117
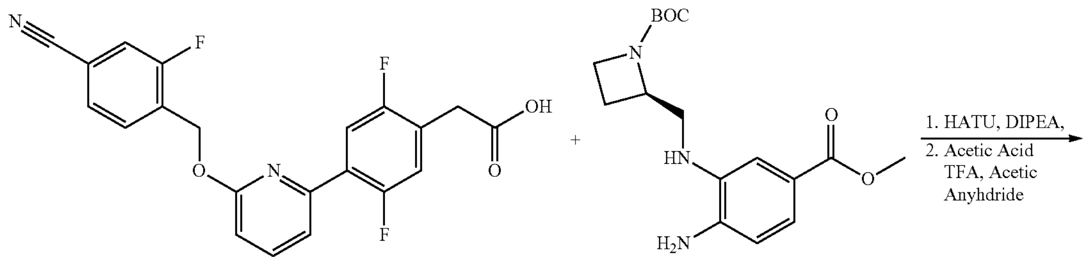
I-81
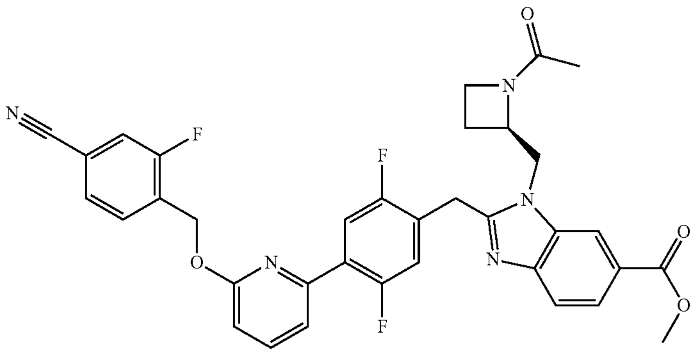
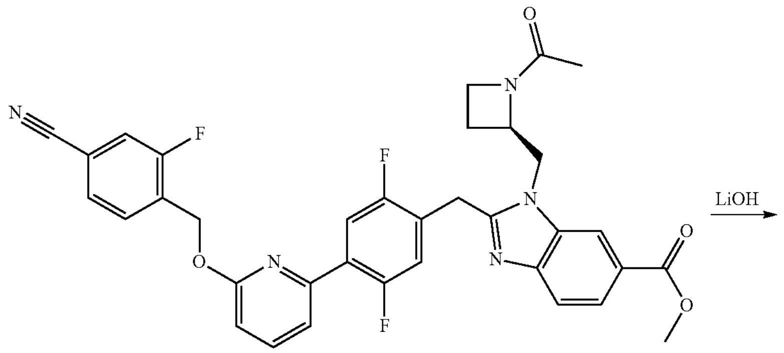
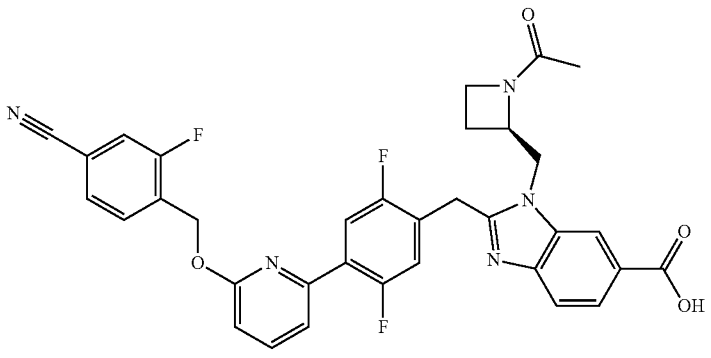
Example 925

Methyl (R)-1-((1-acetylazetidin-2-yl)methyl)-2-(4-(6-((4-cyano-2-fluorobenzyl)oxy)pyridin-2-yl)-2,5-difluorobenzyl)-1H-benzo[d]imidazole-6-carboxylate: tert-butyl (R)-2-(((2-amino-5-(methoxycarbonyl)phenyl)amino)methyl)azetidine-1-carboxylate (279 mg, 0.789 mmol) was added to a vial along with 2-(4-(6-((4-cyano-2-fluorobenzyl)oxy)pyridin-2-yl)-2,5-difluorophenyl)acetic acid (I-81, 200 mg, 0.526 mmol), and o-(7-azabenzotriazol-1-yl)-N,N,N',N'-tetramethyluronium hexafluorophosphate (240 mg, 0.631 mmol) in 3 mL DMF. The solution was stirred at rt for 10 minutes before adding diisopropylethylamine (0.458 mL, 2.63 mmol). The mixture was stirred at rt overnight. The mixture was then concentrated, and dissolved in 4 mL of acetic acid and stirred at 60° C. overnight. An aliquot of 0.1 mL of TFA was added and the temperature increased to 80° C. for 2 h. The mixture was cooled to 60° C. and acetic anhydride (0.5 mL, 5.29 mmol) was added and the mixture stirred for 3 h. The mixture was concentrated, diluted with EtOAc, washed two times with bicarb, then water, brine, dried over $MgSO_4$, filtered, and concentrated. The crude material was purified by flash chromatography (35-100% EtOAc/Hexanes).

(R)-1-((1-acetylazetidin-2-yl)methyl)-2-(4-(6-((4-cyano-2-fluorobenzyl)oxy)pyridin-2-yl)-2,5-difluorobenzyl)-1H-benzo[d]imidazole-6-carboxylic acid. (Example 925): Methyl (R)-1-((1-acetylazetidin-2-yl)methyl)-2-(4-(6-((4-cyano-2-fluorobenzyl)oxy)pyridin-2-yl)-2,5-difluorobenzyl)-1H-benzo[d]imidazole-6-carboxylate (127 mg, 0.199 mmol) was added via 3 mL of ACN to a scintillation vial. An aliquot of 1 mL of $H_2O$ was added followed by lithium hydroxide (25.0 mg, 0.596 mmol). The mixture was stirred for 8 hours at rt, then 2 hours at 60° C. An aliquot of 1 mL of DMF was added and the mixture was concentrated, filtered through a syringe filter, and purified by reverse phase chromatography (10-70% ACN/water with 0.1% TFA) to give (R)-1-((1-acetylazetidin-2-yl)methyl)-2-(4-(6-((4-cyano-2-fluorobenzyl)oxy)pyridin-2-yl)-2,5-difluorobenzyl)-1H-benzo[d]imidazole-6-carboxylic acid. (Example 925) ES/MS m/z: 626.2 ($M+H^+$); 1H NMR (400 MHz, DMSO-d6) δ 8.12 (d, J=1.3 Hz, 1H), 7.97-7.80 (m, 3H), 7.79-7.69 (m, 2H), 7.59-7.40 (m, 2H), 7.40-7.24 (m, 2H), 6.94 (d, J=8.2 Hz, 1H), 5.57 (s, 2H), 4.97-4.54 (m, 3H), 4.45 (dd, J=24.9, 4.5 Hz, 2H), 4.02-3.76 (m, 2H), 2.36-2.17 (m, 1H), 1.91 (ddd, J=11.6, 9.1, 5.6 Hz, 1H), 1.67 (s, 2H).

Example 926. 2-(4-(6-((4-cyano-2-fluorobenzyl)oxy)pyridin-2-yl)-2,5-difluorobenzyl)-1-(2-methoxyethyl)-5-methyl-1H-benzo[d]imidazole-6-carboxylic acid Procedure 118

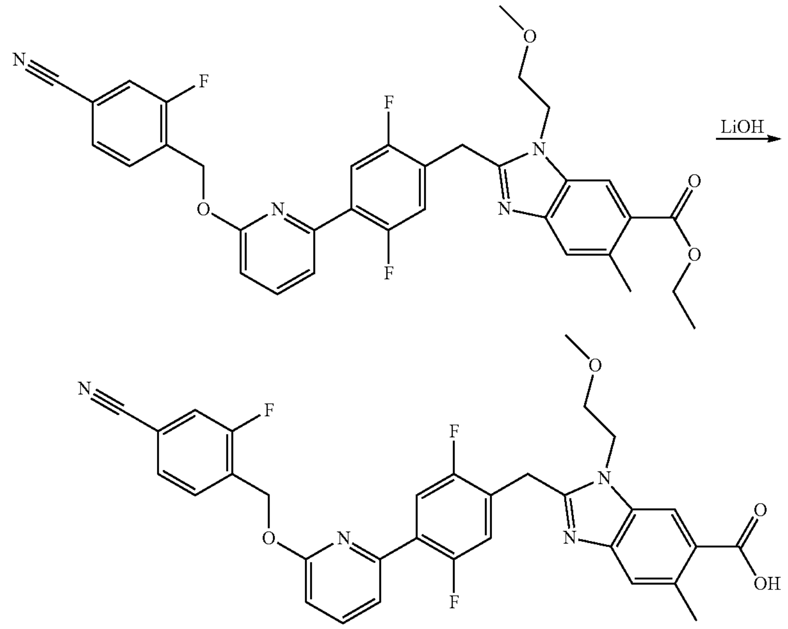

Example 926

2-(4-(6-((4-cyano-2-fluorobenzyl)oxy)pyridin-2-yl)-2,5-difluorobenzyl)-1-(2-methoxyethyl)-5-methyl-1H-benzo[d]imidazole-6-carboxylic acid (Example 926): Ethyl 2-(4-(6-((4-cyano-2-fluorobenzyl)oxy)pyridin-2-yl)-2,5-difluorobenzyl)-1-(2-methoxyethyl)-5-methyl-1H-benzo[d]imidazole-6-carboxylate (77 mg, 0.13 mmol), synthesized as described for Procedure 52 substituting methyl (S)-4-amino-3-((oxetan-2-ylmethyl)amino)benzoate with ethyl 4-amino-5-((2-methoxyethyl)amino)-2-methylbenzoate, was added to a vial using 9 mL of ACN. Lithium Hydroxide (16 mg, 0.38 mmol) was added along with 3 mL of water and 3 mL of THF. The solution was stirred for 24 hours at rt followed by 24 hours at 60° C., before heating in a sealed tube at 100° C. for 5 h. The mixture was cooled to rt, then diluted with EtOAc, washed with 1 M citric acid, water, brine, dried over $MgSO_4$, filtered, concentrated, and purified by reverse phase chromatography (10-100% ACN/$H_2O$ with 0.1% TFA) to give -(4-(6-((4-cyano-2-fluorobenzyl)oxy)pyridin-2-yl)-2,5-difluorobenzyl)-1-(2-methoxyethyl)-5-methyl-1H-benzo[d]imidazole-6-carboxylic acid. (Example 926) ES/MS m/z: 587.2 ($M+H^+$); 1H NMR (400 MHz, Methanol-d4) δ 8.40 (s, 1H), 7.87-7.78 (m, 2H), 7.73 (t, J=7.5 Hz, 1H), 7.65-7.55 (m, 4H), 7.31 (dd, J=11.3, 6.1 Hz, 1H), 6.99-6.94 (m, 1H), 5.63 (s, 2H), 4.73 (t, J=5.0 Hz, 2H), 4.69 (s, 2H), 3.83-3.78 (m, 2H), 3.31 (s, 3H), 2.74 (d, J=0.8 Hz, 3H).

Biological Data

GLP-1R Activation

GLP-1R activation by a compound of the present disclosure was quantified by measuring cAMP increase in CHO cells stably expressing GLP-1R (MultiSpan product #C1267-1a). The cells were harvested and plated in growth medium (DMEM/F-12 (Corning product #10-090-CV) supplemented with 10% FBS (HyClone product #SH30071-03), penicillin/streptomycin (Corning product #30-002CI) and 10 µg/ml puromycin (Gibco product #A11138-03)) at 1,000 cells/well in a 384-well plate (Greiner product #781080). The cells were then incubated overnight at 37° C., 5% $CO_2$. The next day, the medium was removed and the cells were washed with DPBS (Corning product #21-031-CM) before adding the assay medium (HBSS, Corning product #21-023-CV) with 20 mM Hepes (Gibco product #15630-080) and 0.1% BSA (Rockland Immunochemicals product #BSA-1000)). Following the medium change, the cells were incubated for 1 hour at 37° C., 5% 0 $CO_2$. The tested GLP-1 compound was added to the cells in a 10 point dose response followed by a 30 minutes incubation at 37° C., 500 $CO_2$. cAMP concentration increase was then detected using Cisbio's cAMP Gs Dynamic Kit (product #62AM4PEC) according to the manufacturer's protocol. The response was plotted against the log of the agonist concentration and fitted to a sigmoidal equation to determine the $EC_{50}$.

The following table shows exemplary data for GLP-1 compounds of the disclosure.

| Example | $EC_{50}$ (nM) |
|---|---|
| 1 | 25.4 |
| 2 | 2.3 |
| 3 | 10.3 |
| 4 | 1574 |
| 5 | 1.94 |
| 6 | 56.1 |
| 7 | 6.34 |
| 8 | 26.4 |
| 9 | 1.75 |
| 10 | 0.57 |
| 11 | 2.7 |
| 12 | 1.77 |
| 13 | 2.7 |
| 14 | 3.14 |
| 15 | 0.63 |
| 16 | 0.55 |
| 17 | 11 |
| 18 | 3.6 |
| 19 | 4.03 |
| 20 | 24.1 |
| 21 | 70.9 |
| 22 | 0.78 |
| 23 | 1104 |
| 24 | 1721 |
| 25 | 25.9 |
| 26 | 115 |
| 27 | 78 |
| 28 | 94 |
| 29 | 57 |
| 30 | 1350 |
| 31 | 32 |
| 32 | >1000 |
| 33 | 26.9 |
| 34 | 2182 |
| 35 | 1002 |
| 36 | 107 |
| 37 | 927 |
| 38 | 6.18 |
| 39 | 8.79 |
| 40 | 456.3 |
| 41 | 1455 |

-continued

| Example | $EC_{50}$ (nM) |
|---|---|
| 42 | 38.2 |
| 43 | 163 |
| 44 | 212.5 |
| 45 | 36 |
| 46 | 62.4 |
| 47 | 1442 |
| 48 | 575 |
| 49 | >1000 |
| 50 | 19 |
| 51 | 63 |
| 52 | 56 |
| 53 | 1008 |
| 54 | 806 |
| 55 | 3.4 |
| 56 | 72 |
| 57 | 6.7 |
| 58 | 28.8 |
| 59 | 5.6 |
| 60 | 30 |
| 61 | 18 |
| 62 | 1426 |
| 63 | 164 |
| 64 | 67 |
| 65 | 1225 |
| 66 | 1027 |
| 67 | 0.44 |
| 68 | 36 |
| 69 | 12 |
| 70 | 64 |
| 71 | 1.34 |
| 72 | 23.79 |
| 73 | 6.13 |
| 74 | 0.46 |
| 75 | 0.60 |
| 76 | 22.34 |
| 77 | 0.19 |
| 78 | 10000.00 |
| 79 | 1.04 |
| 80 | 2629.04 |
| 81 | 290.82 |
| 82 | 264.47 |
| 83 | 29.34 |
| 84 | 54.34 |
| 85 | 4.90 |
| 86 | 273.94 |
| 87 | 5.66 |
| 88 | 295.51 |
| 89 | 1648.10 |
| 90 | 72.39 |
| 91 | 2633.21 |
| 92 | 2.64 |
| 93 | 0.28 |
| 94 | 0.66 |
| 95 | 0.26 |
| 96 | 30.90 |
| 97 | 2779.79 |
| 98 | 913.50 |
| 99 | 10000.00 |
| 100 | 10000.00 |
| 101 | 25.86 |
| 102 | 56.52 |
| 103 | 4979.86 |
| 104 | 21.41 |
| 105 | 0.45 |
| 106 | 1.50 |
| 107 | 3638.74 |
| 108 | 388.29 |
| 109 | 3.38 |
| 110 | 21.80 |
| 111 | 0.51 |
| 112 | 3.76 |
| 113 | 2151.47 |
| 114 | 932.31 |
| 115 | 80.87 |
| 116 | 2521.80 |
| 117 | 62.18 |
| 118 | 6.01 |

-continued

| Example | $EC_{50}$ (nM) |
|---|---|
| 119 | 0.56 |
| 120 | 1.24 |
| 121 | 0.66 |
| 122 | 30.56 |
| 123 | 3.12 |
| 124 | 0.67 |
| 125 | 0.34 |
| 126 | 3.70 |
| 127 | 0.34 |
| 128 | 0.51 |
| 129 | 0.70 |
| 130 | 0.11 |
| 131 | 0.08 |
| 132 | 0.05 |
| 133 | 0.26 |
| 134 | 0.34 |
| 135 | 1.76 |
| 136 | 24.47 |
| 137 | 32.20 |
| 138 | 84.74 |
| 139 | 26.42 |
| 140 | 197.26 |
| 141 | 80.31 |
| 142 | 161.69 |
| 143 | 2.59 |
| 144 | 20.74 |
| 145 | 1730.71 |
| 146 | 36.37 |
| 147 | 760.03 |
| 148 | 2054.49 |
| 149 | 2044.32 |
| 150 | 3.35 |
| 151 | 7.93 |
| 152 | 129.88 |
| 153 | 0.11 |
| 154 | 0.51 |
| 155 | 73.16 |
| 156 | 51.47 |
| 157 | 533.77 |
| 158 | 37.10 |
| 159 | 7.78 |
| 160 | 10.18 |
| 161 | 1.00 |
| 162 | 0.17 |
| 163 | 1.41 |
| 164 | 32.88 |
| 165 | 0.01 |
| 166 | 0.06 |
| 167 | 0.11 |
| 168 | 1.06 |
| 169 | 4.31 |
| 170 | 509.20 |
| 172 | 37.98 |
| 173 | 774.34 |
| 174 | 32.89 |
| 175 | 9268.79 |
| 176 | 273.18 |
| 177 | 334.93 |
| 178 | 32.55 |
| 179 | 45.62 |
| 180 | 257.13 |
| 181 | 15.49 |
| 182 | 448.93 |
| 183 | 3960.12 |
| 184 | 368.87 |
| 186 | 812.17 |
| 187 | 722.66 |
| 188 | 36.94 |
| 189 | 3053.13 |
| 190 | 251.61 |
| 191 | 10000.00 |
| 192 | 436.54 |
| 193 | 131.35 |
| 194 | 0.86 |
| 195 | 15.77 |
| 196 | 4.61 |
| 197 | 7.77 |

-continued

| Example | $EC_{50}$ (nM) |
|---|---|
| 198 | 8.69 |
| 199 | 20.79 |
| 200 | 17.98 |
| 201 | 4419.34 |
| 202 | 3.34 |
| 203 | 420.47 |
| 204 | 7.37 |
| 205 | 3.23 |
| 206 | 0.86 |
| 207 | 35.16 |
| 208 | 4.67 |
| 209 | 48.81 |
| 210 | 1000.00 |
| 211 | 125.55 |
| 212 | 80.08 |
| 213 | 10000.00 |
| 214 | 744.51 |
| 215 | 62.72 |
| 216 | 109.79 |
| 217 | 1.72 |
| 218 | 19.08 |
| 219 | 0.69 |
| 220 | 37.78 |
| 221 | 5.28 |
| 222 | 6.79 |
| 223 | 16.37 |
| 224 | 23.60 |
| 225 | 13.07 |
| 226 | 138.81 |
| 227 | 14.31 |
| 228 | 4.87 |
| 229 | 35.43 |
| 230 | 27.45 |
| 231 | 35.45 |
| 232 | 17.79 |
| 233 | 1.35 |
| 234 | 6.95 |
| 235 | 316.95 |
| 236 | 305.96 |
| 237 | 19.22 |
| 238 | 12.05 |
| 239 | 7.49 |
| 240 | 6.82 |
| 241 | 35.10 |
| 242 | 18.38 |
| 243 | 0.88 |
| 244 | 158.57 |
| 245 | 140.14 |
| 246 | 1110.27 |
| 247 | 2.20 |
| 248 | 3556.14 |
| 249 | 172.21 |
| 250 | 11.70 |
| 251 | 3.13 |
| 252 | 3.78 |
| 253 | 10000.00 |
| 254 | 68.63 |
| 255 | 3.31 |
| 256 | 30.57 |
| 257 | 1.43 |
| 258 | 10.75 |
| 259 | 66.89 |
| 260 | 112.98 |
| 261 | 184.03 |
| 262 | 28.59 |
| 263 | 91.67 |
| 264 | 26.19 |
| 265 | 2.08 |
| 266 | 51.38 |
| 267 | 171.50 |
| 268 | 15.70 |
| 269 | 51.70 |
| 270 | 1.82 |
| 271 | 2.59 |
| 272 | 1.66 |
| 273 | 0.52 |
| 274 | 0.23 |

-continued

| Example | $EC_{50}$ (nM) |
|---|---|
| 275 | 5.51 |
| 276 | 0.23 |
| 277 | 1.57 |
| 278 | 1644.28 |
| 279 | 3.07 |
| 280 | 0.62 |
| 281 | 2.30 |
| 282 | 10000.00 |
| 283 | 3.94 |
| 284 | 2.87 |
| 285 | 2.19 |
| 286 | 21.21 |
| 287 | 0.14 |
| 288 | 0.76 |
| 289 | 3.02 |
| 290 | 62.34 |
| 291 | 1.06 |
| 292 | 49.42 |
| 293 | 3.13 |
| 294 | 0.75 |
| 295 | 2.12 |
| 296 | 0.08 |
| 297 | 1.71 |
| 298 | 4.75 |
| 299 | 0.40 |
| 300 | 0.68 |
| 301 | 0.73 |
| 302 | 1.21 |
| 303 | 1.33 |
| 304 | 0.50 |
| 305 | 1.25 |
| 306 | 1.86 |
| 307 | 7.96 |
| 308 | 1.26 |
| 309 | 2.16 |
| 310 | 16.26 |
| 311 | 95.65 |
| 312 | 250.38 |
| 313 | 3.25 |
| 314 | 12.48 |
| 315 | 2.08 |
| 316 | 13.95 |
| 317 | 1.05 |
| 318 | 1.07 |
| 319 | 2.43 |
| 320 | 18.01 |
| 321 | 0.27 |
| 322 | 0.58 |
| 323 | 27.53 |
| 324 | 5.22 |
| 325 | 1.61 |
| 326 | 6.81 |
| 327 | 7.73 |
| 328 | 26.47 |
| 329 | 285.95 |
| 330 | 17.21 |
| 331 | 12.32 |
| 332 | 120.36 |
| 333 | 623.74 |
| 334 | 7.11 |
| 335 | 138.83 |
| 336 | 4.90 |
| 337 | 13.67 |
| 338 | 2513.58 |
| 339 | 565.93 |
| 340 | 44.14 |
| 341 | 19.67 |
| 342 | 3355.87 |
| 343 | 1.70 |
| 344 | 1.56 |
| 345 | 175.35 |
| 346 | 94.59 |
| 347 | 92.63 |
| 348 | 48.07 |
| 349 | 3.05 |
| 350 | 0.79 |
| 351 | 0.96 |

-continued

| Example | $EC_{50}$ (nM) |
|---|---|
| 352 | 1.45 |
| 353 | 1.67 |
| 354 | 146.10 |
| 355 | 0.97 |
| 356 | 48.73 |
| 357 | 56.21 |
| 358 | 33.06 |
| 359 | 3.09 |
| 360 | 0.94 |
| 361 | 0.74 |
| 362 | 21.83 |
| 363 | 8.96 |
| 364 | 1.76 |
| 365 | 0.60 |
| 366 | 20.76 |
| 367 | 0.86 |
| 368 | 0.77 |
| 369 | 0.13 |
| 370 | 3.34 |
| 371 | 1.61 |
| 372 | 242.57 |
| 373 | 4767.84 |
| 374 | 1927.20 |
| 375 | 5.46 |
| 376 | 1.53 |
| 377 | 10.93 |
| 378 | 12.37 |
| 379 | 2.80 |
| 380 | 7.72 |
| 381 | 7.43 |
| 382 | 8.70 |
| 383 | 123.39 |
| 384 | 1.45 |
| 385 | 1.34 |
| 386 | 156.82 |
| 387 | 504.44 |
| 388 | 0.24 |
| 389 | 26.60 |
| 390 | 26.35 |
| 391 | 1000.00 |
| 392 | 14.48 |
| 393 | 33.50 |
| 394 | 6.06 |
| 395 | 42.26 |
| 396 | 45.49 |
| 397 | 14.41 |
| 398 | 0.10 |
| 399 | 2.81 |
| 400 | 0.47 |
| 401 | 1.34 |
| 402 | 2.11 |
| 403 | 0.89 |
| 404 | 1.71 |
| 405 | 1.71 |
| 406 | 0.18 |
| 407 | 4.69 |
| 408 | 1000.00 |
| 409 | 0.37 |
| 410 | 20.84 |
| 411 | 140.49 |
| 412 | 0.33 |
| 413 | 0.07 |
| 414 | 0.44 |
| 415 | 0.15 |
| 416 | 0.09 |
| 417 | 0.10 |
| 418 | 18.30 |
| 419 | 20.65 |
| 420 | 0.05 |
| 421 | 327.32 |
| 422 | 0.87 |
| 423 | 4.12 |
| 424 | 15.71 |
| 425 | 4.29 |
| 426 | 2.34 |
| 427 | 0.06 |
| 428 | 0.13 |

-continued

| Example | $EC_{50}$ (nM) |
|---|---|
| 429 | 0.61 |
| 430 | 0.67 |
| 431 | 0.73 |
| 432 | 2.01 |
| 433 | 0.64 |
| 434 | 2.86 |
| 435 | 8.70 |
| 436 | 0.44 |
| 437 | 69.78 |
| 438 | 64.67 |
| 439 | 10000.00 |
| 440 | 2.12 |
| 441 | 0.21 |
| 442 | 0.14 |
| 443 | 0.15 |
| 444 | 0.25 |
| 445 | 0.50 |
| 446 | 0.15 |
| 447 | 1102.53 |
| 448 | 1.23 |
| 449 | 0.17 |
| 450 | 0.77 |
| 451 | 0.16 |
| 452 | 0.16 |
| 453 | 40.34 |
| 454 | 5.53 |
| 455 | 1.87 |
| 456 | 665.97 |
| 457 | 1.40 |
| 458 | 2.78 |
| 459 | 2.35 |
| 460 | 15.65 |
| 461 | 2.47 |
| 462 | 158.97 |
| 463 | 10000.00 |
| 464 | 18.53 |
| 465 | 1606.73 |
| 466 | 1.87 |
| 467 | 10000.00 |
| 468 | 26.94 |
| 469 | 1000.00 |
| 470 | 1245.80 |
| 471 | 13.71 |
| 472 | 20.86 |
| 473 | 10000.00 |
| 474 | 10000.00 |
| 475 | 325.16 |
| 476 | 366.48 |
| 477 | 145.93 |
| 478 | 9.19 |
| 479 | 10000.00 |
| 480 | 6.59 |
| 481 | 2.90 |
| 482 | 1.43 |
| 483 | 3.94 |
| 484 | 1.06 |
| 485 | 103.47 |
| 486 | 1.05 |
| 487 | 100.10 |
| 488 | 1090.89 |
| 489 | 88.70 |
| 490 | 5.53 |
| 491 | 19.42 |
| 492 | 5.16 |
| 493 | 254.72 |
| 494 | 4553.48 |
| 495 | 777.41 |
| 496 | 1996.15 |
| 497 | 1351.64 |
| 498 | 10000.00 |
| 499 | 8.18 |
| 500 | 474.16 |
| 501 | 102.04 |
| 502 | 2381.62 |
| 503 | 100.00 |
| 504 | 28.46 |
| 505 | 41.17 |

-continued

| Example | $EC_{50}$ (nM) |
|---|---|
| 506 | 2175.42 |
| 507 | 361.05 |
| 508 | 16.46 |
| 509 | 102.12 |
| 510 | 10000.00 |
| 511 | 29.73 |
| 512 | 6557.99 |
| 513 | 55.09 |
| 514 | 60.80 |
| 515 | 875.73 |
| 516 | 2464.18 |
| 517 | 0.06 |
| 518 | 43.09 |
| 519 | 39.33 |
| 520 | 0.36 |
| 521 | 0.54 |
| 522 | 136.66 |
| 523 | 0.51 |
| 524 | 66.52 |
| 525 | 0.60 |
| 526 | 70.93 |
| 527 | 1.84 |
| 528 | 0.45 |
| 529 | 1.10 |
| 530 | 0.43 |
| 531 | 12.82 |
| 532 | 58.58 |
| 533 | 47.06 |
| 534 | 49.92 |
| 535 | 0.66 |
| 536 | 0.04 |
| 537 | 6.89 |
| 538 | 4249.00 |
| 539 | 0.70 |
| 540 | 0.12 |
| 541 | 28.25 |
| 542 | 8.60 |
| 543 | 1.51 |
| 544 | 0.96 |
| 545 | 6.90 |
| 546 | 0.33 |
| 547 | 3.43 |
| 548 | 9.01 |
| 549 | 45.51 |
| 551 | 608.98 |
| 552 | 18.13 |
| 553 | 19.77 |
| 554 | 48.17 |
| 555 | 57.87 |
| 556 | 10000.00 |
| 557 | 0.47 |
| 558 | 22.43 |
| 559 | 2.62 |
| 560 | 1.92 |
| 561 | 24.13 |
| 562 | 10000.00 |
| 563 | 1.00 |
| 564 | 1.96 |
| 565 | 4.91 |
| 566 | 254.93 |
| 567 | 1128.23 |
| 568 | 2.27 |
| 569 | 10.36 |
| 570 | 2.14 |
| 571 | 95.33 |
| 573 | 0.89 |
| 574 | 0.63 |
| 575 | 37.23 |
| 576 | 0.86 |
| 577 | 0.40 |
| 578 | 13.80 |
| 579 | 0.35 |
| 580 | 1.94 |
| 581 | 0.40 |
| 582 | 3462.80 |
| 583 | 2.39 |
| 584 | 0.23 |

-continued

| Example | $EC_{50}$ (nM) |
|---|---|
| 585 | 0.81 |
| 586 | 0.54 |
| 587 | 2.15 |
| 588 | 1.33 |
| 589 | 5.46 |
| 590 | 3188.90 |
| 591 | 0.17 |
| 592 | 33.27 |
| 593 | 144.53 |
| 594 | 0.77 |
| 595 | 10000.00 |
| 596 | 816.43 |
| 597 | 13.78 |
| 598 | 0.28 |
| 599 | 0.98 |
| 600 | 0.10 |
| 601 | 31.70 |
| 602 | 1.17 |
| 603 | 4.13 |
| 604 | 0.92 |
| 605 | 1.57 |
| 606 | 177.92 |
| 607 | 108.11 |
| 608 | 0.74 |
| 609 | 0.15 |
| 610 | 258.58 |
| 611 | 0.29 |
| 612 | 0.22 |
| 613 | 0.54 |
| 614 | 0.79 |
| 615 | 1418.77 |
| 616 | 26.90 |
| 617 | 0.55 |
| 618 | 1.48 |
| 619 | 3.10 |
| 620 | 7.50 |
| 621 | 17.36 |
| 622 | 2.68 |
| 623 | 4.04 |
| 624 | 1.68 |
| 625 | 0.63 |
| 626 | 23.87 |
| 627 | 2.19 |
| 628 | 13.44 |
| 629 | 1.26 |
| 630 | 39.38 |
| 631 | 74.95 |
| 632 | 0.24 |
| 633 | 0.17 |
| 634 | 0.51 |
| 635 | 0.46 |
| 636 | 1.27 |
| 637 | 1.18 |
| 638 | 2.24 |
| 639 | 78.23 |
| 640 | 16.55 |
| 641 | 65.86 |
| 642 | 5.14 |
| 643 | 0.03 |
| 644 | 0.69 |
| 645 | 2.05 |
| 646 | 1.78 |
| 647 | 3.02 |
| 648 | 0.09 |
| 649 | 0.20 |
| 650 | 19.61 |
| 651 | 2785.18 |
| 652 | 8.79 |
| 653 | 16.96 |
| 654 | 24.88 |
| 655 | 1.26 |
| 656 | 1.52 |
| 657 | 5.88 |
| 658 | 0.11 |
| 659 | 0.17 |
| 660 | 50.49 |
| 661 | 1.95 |

-continued

| Example | $EC_{50}$ (nM) |
|---|---|
| 662 | 0.39 |
| 663 | 0.51 |
| 664 | 0.67 |
| 665 | 0.51 |
| 666 | 0.51 |
| 667 | 0.10 |
| 668 | 0.56 |
| 669 | 0.28 |
| 670 | 0.51 |
| 671 | 1.76 |
| 672 | 0.58 |
| 673 | 3.54 |
| 674 | 2.73 |
| 675 | 0.16 |
| 676 | 0.52 |
| 677 | 0.06 |
| 678 | 0.88 |
| 679 | 0.06 |
| 680 | 0.11 |
| 681 | 5.64 |
| 682 | 0.59 |
| 683 | 2.41 |
| 684 | 0.29 |
| 685 | 1.05 |
| 686 | 0.55 |
| 687 | 181.07 |
| 688 | 1216.00 |
| 689 | 0.56 |
| 690 | 3.98 |
| 691 | 0.06 |
| 692 | 12.27 |
| 693 | 15.89 |
| 694 | 41.73 |
| 695 | 27.27 |
| 696 | 592.28 |
| 697 | 25.64 |
| 698 | 63.25 |
| 699 | 83.90 |
| 700 | 3.48 |
| 701 | 145.44 |
| 702 | 8.14 |
| 703 | 1.01 |
| 704 | 0.98 |
| 705 | 73.17 |
| 706 | 1.31 |
| 707 | 4.81 |
| 708 | 0.64 |
| 709 | 4.77 |
| 710 | 1.45 |
| 711 | 0.08 |
| 712 | 2.55 |
| 713 | 5.76 |
| 714 | 24.94 |
| 715 | 4.01 |
| 716 | 2739.48 |
| 717 | 41.53 |
| 718 | 0.05 |
| 719 | 0.37 |
| 720 | 27.76 |
| 721 | 1.31 |
| 722 | 2.56 |
| 723 | 5.19 |
| 724 | 15.12 |
| 725 | 3.68 |
| 726 | 7.26 |
| 727 | 46.27 |
| 728 | 93.56 |
| 729 | 1.03 |
| 730 | 0.98 |
| 731 | 290.00 |
| 732 | 169.13 |
| 733 | 2.47 |
| 734 | 167.86 |
| 735 | 1.70 |
| 736 | 0.80 |
| 737 | 1.89 |
| 738 | 1.87 |

-continued

| Example | $EC_{50}$ (nM) |
|---|---|
| 739 | 0.74 |
| 740 | 1164.94 |
| 741 | 22.61 |
| 742 | 54.78 |
| 743 | 2.48 |
| 744 | 10.55 |
| 745 | 83.50 |
| 746 | 0.87 |
| 747 | 0.81 |
| 748 | 1319.16 |
| 749 | 0.33 |
| 750 | 1.26 |
| 751 | 0.19 |
| 752 | 0.51 |
| 753 | 0.74 |
| 754 | 0.15 |
| 755 | 0.42 |
| 756 | 1.42 |
| 757 | 0.03 |
| 758 | 0.03 |
| 759 | 0.64 |
| 760 | 0.26 |
| 761 | 0.51 |
| 762 | 0.90 |
| 764 | 0.76 |
| 765 | 0.51 |
| 766 | 0.13 |
| 767 | 0.51 |
| 768 | 0.04 |
| 769 | 0.03 |
| 770 | 2.62 |
| 771 | 2.17 |
| 772 | 0.61 |
| 773 | 0.12 |
| 774 | 0.06 |
| 775 | 0.10 |
| 776 | 26.85 |
| 777 | 0.73 |
| 778 | 0.13 |
| 779 | 0.17 |
| 780 | 0.12 |
| 781 | 0.03 |
| 782 | 3.31 |
| 783 | 0.11 |
| 784 | 0.55 |
| 785 | 0.05 |
| 786 | 0.22 |
| 787 | 0.08 |
| 788 | 0.17 |
| 789 | 1.18 |
| 790 | 0.44 |
| 791 | 2.75 |
| 792 | 0.04 |
| 793 | 0.17 |
| 794 | 0.97 |
| 795 | 0.65 |
| 796 | 0.03 |
| 797 | 0.27 |
| 798 | 0.12 |
| 799 | 134.59 |
| 800 | 0.10 |
| 801 | 0.12 |
| 802 | 3.64 |
| 803 | 5.95 |
| 804 | 43.58 |
| 805 | 7.12 |
| 806 | 0.54 |
| 807 | 0.18 |
| 808 | 0.05 |
| 809 | 1.05 |
| 810 | 0.33 |
| 811 | 3.57 |
| 812 | 24.88 |
| 813 | 2.98 |
| 814 | 2.14 |
| 815 | 2.49 |
| 816 | 1.00 |

-continued

| Example | $EC_{50}$ (nM) |
|---|---|
| 817 | 10.3 |
| 818 | 4.30 |
| 819 | 0.86 |
| 820 | 11.52 |
| 821 | 14.76 |
| 822 | 3.49 |
| 823 | 19.75 |
| 824 | 196.70 |
| 825 | 9.09 |
| 826 | 0.28 |
| 827 | 1.97 |
| 828 | 3.50 |
| 829 | 0.18 |
| 830 | 447.85 |
| 831 | 0.24 |
| 832 | 2325.68 |
| 833 | 6.41 |
| 834 | 0.69 |
| 835 | 515.47 |
| 836 | 9.29 |
| 837 | 29.28 |
| 838 | 3.60 |
| 839 | 7.04 |
| 840 | 1.11 |
| 841 | 164.41 |
| 842 | 4.73 |
| 843 | 17.16 |
| 844 | 12.99 |
| 845 | 18.01 |
| 847 | 537.23 |
| 848 | 4.08 |
| 849 | 14.18 |
| 850 | 0.23 |
| 851 | 0.25 |
| 852 | 0.24 |
| 853 | 0.15 |
| 854 | 0.55 |
| 855 | 12.56 |
| 856 | 4.55 |
| 857 | 0.35 |
| 858 | 2.27 |
| 859 | 11.59 |
| 860 | 22.64 |
| 861 | 16.49 |
| 862 | 16.24 |
| 863 | 5.51 |
| 864 | 3.71 |
| 865 | 29.79 |
| 866 | 16.09 |
| 867 | 2.41 |
| 868 | 5.48 |
| 869 | 6.28 |
| 870 | 17.64 |
| 871 | 30.78 |
| 872 | 5.09 |
| 873 | 83.79 |
| 874 | 34.71 |
| 875 | 2.32 |
| 876 | 27.56 |
| 877 | 0.51 |
| 878 | 0.78 |
| 879 | 0.51 |
| 880 | 0.26 |
| 881 | 0.29 |
| 882 | 0.18 |
| 883 | 0.30 |
| 884 | 0.19 |
| 885 | 0.22 |
| 886 | 0.18 |
| 887 | 8314.15 |
| 888 | 6.01 |
| 889 | 69.51 |
| 890 | 0.49 |
| 891 | 0.25 |
| 892 | 0.78 |
| 893 | 35.26 |
| 894 | 2.68 |

-continued

| Example | $EC_{50}$ (nM) |
|---|---|
| 895 | 79.92 |
| 896 | 0.03 |
| 897 | 4.10 |
| 898 | 1.50 |
| 899 | 2.26 |
| 900 | 1.26 |
| 901 | 160.41 |
| 902 | 6.19 |
| 903 | 107.21 |
| 904 | 311.25 |
| 905 | 30.91 |
| 906 | 2.09 |
| 907 | 9960.04 |
| 908 | 6.68 |
| 909 | 2.25 |
| 910 | 33.41 |
| 911 | 55.64 |
| 912 | 15.27 |
| 913 | 112.24 |
| 914 | 51.54 |
| 915 | 2.26 |
| 916 | 2.18 |
| 917 | 56.70 |
| 918 | 24.94 |
| 919 | 839.90 |
| 920 | 58.45 |
| 921 | 0.33 |
| 922 | 2.65 |
| 923 | 2.83 |
| 924 | 2.17 |
| 925 | 3.63 |
| 926 | 11.80 |

Microsomal Stability

Metabolic stability of compounds was assessed using human or rat liver microsomal assays (Corning). In these assays, 10 nL of each analyte at a concentration of 1 mM in 100% DMSO was dispensed into a well of a polypropylene plate using the Echo 550 acoustic liquid dispenser (Labcyte®). Each plate contained 384 wells with a single analyte in each well.

A solution of human (Corning® Gentest™ Human Mixed Pooled Microsomes or rat (Corning® Gentest™ Rat [Sprague-Dawley] Pooled Liver Microsomes) liver microsomes at 2 mg/ml in 100 mM $K_2HPO_4/KH_2PO_4$ at pH 7.4 was combined with alamethicin from *Trichoderma viride* (Sigma-Aldrich) 0.0225 mg/ml. The mixture was incubated on ice for 15 minutes. 5 µL of this mixture was added to individual wells following a 15 minute incubation at room temperature and supplemented with 5 µL NADPH Regenerating Solution of cofactors (Corning® Gentest™ UGT Reaction Mix) containing 100 mM $K_2HPO_4/KH_2PO_4$ at pH 7.4, 2.6 mM NADP+, 6.6 mM glucose-6-phosphate, 6.6 mM $MgCl_2$, 0.8 U/mL glucose-6-phosphate dehydrogenase, 0.1 mM sodium citrate, and 6.8 mM uridine diphosphate-glucuronic acid. The final concentration of each analyte compound at the beginning of the reaction was 1 µM. The reactions were incubated at 37° C. and samples were collected at time points of 0, 5, 15, 30, 40, 50, 60, and 70 minutes for further analysis. Background data were collected using reactions without analyte compounds.

Upon collection of the sample time points, samples were quenched with 30 µL of a solution of 72% acetonitrile, 8% methanol, 0.1% formic acid, 19.9% water, and internal standard (IS). Reaction plates were spun in a centrifuge at speed of 4,000 rcf for 30 minutes at 4° C., following a dilution of the 10 µL quenched reaction into 40 µL de-ionized water, yielding assay plates.

Assay plates were analyzed using solid-state extraction coupled with quadrupole time-of-flight mass spectrometer, using Agilent QToF 6530 RapidFire 360 system, with C4 type A solid state cartridges. Analysis was performed in either positive or negative ionization modes. Mobile phases contained 0.1% formic acid in water for loading analytes onto solid state extraction cartridges and 0.1% formic acid in acetonitrile for elution into a mass spectrometer in positive ionization mode, or 0.1% acetic acid in water for loading and 0.1% acetic acid in acetonitrile for extraction in negative ionization mode. Peak-area ratios of integrated counts for individual compounds to IS were plotted as semi-logarithmic chart of log vs time. The initial linear portion of decay was fitted to a linear regression equation to derive the half-time of analyte decay.

Pharmacological parameters for an analyte compound metabolism were calculated using the following equations:

| Parameter | Equation |
|---|---|
| Half Life | $T_{1/2} = \frac{\log_{10} 2}{-1 * \text{Slope}}$ |
| Intrinsic Clearance (in vitro) | $Cl_{int,in\ vitro} = \frac{\ln 2}{T_{1/2} * Conc}$ |
| Intrinsic Clearance | $Cl_{int} = \frac{Cl_{int,in\ vitro} * \text{Liver Mass} * \text{Yield}}{\text{Body Weight}}$ |
| Predicted Hepatic Clearance | $Cl = \frac{Cl_{int} * Q_H}{Cl_{int} + Q_H}$ |
| Hepatic Extraction | $E = \frac{Cl}{Q_H} * 100\%$ |

Where:

Calculation of In Vitro Intrinsic Clearance $$CL_{int,in\ vitro} = \frac{\ln 2}{\text{Half-Life} * \text{Concentration}}$$

wherein concentration refers to the protein concentration (mg/ml) in the reaction.

| System | Concentration |
|---|---|
| "Mixed cofactor" Hepatic microsomes (+UDPGA + NADPH) | 1.0 mg protein/mL |

Calculation of In Vivo Intrinsic Clearance

This scales the in vitro intrinsic clearance up to the value that would be predicted for the entire mass of liver tissue (but with no restriction by blood flow). The value depends upon the size of the liver (species-dependent) and the yield of microsomal protein as appropriate (assumed to be species-independent).

$$CL_{int} = \frac{CL_{int,in\ vitro} * \text{Liver mass} * \text{Yield}}{\text{Body weight}}$$

| Matrix | Yield |
|---|---|
| Microsomal fraction | 45 mg/g liver |

| Species | Body weight kg | Liver weight g |
|---|---|---|
| Huan | 70 | 1800 |

Calculation of Predicted Clearance

Hepatic clearance will depend upon the inter-relationship of intrinsic clearance and hepatic blood flow and was predicted from in vitro data using a variety of approaches.

$$CL = \frac{CL_{int} * Q_H}{CL_{int} + Q_H}$$

| Species | Hepatic blood flow L/hr/kg |
|---|---|
| Human | 1.3 |

Calculation of Hepatic Extraction

The hepatic extraction is reported as the predicted clearance expressed as a proportion of hepatic blood flow.

$$E = CL/QH*100\%$$

The Predicted Hepatic Clearance is reported in the table below.

| Example | Predicted Hepatic Clearance (Pred. Cl.) (L/h/kg) |
|---|---|
| 1 | 0.2 |
| 2 | 0.14 |
| 3 | 0.23 |
| 4 | 0.82 |
| 5 | 0.21 |
| 6 | 0.21 |
| 7 | 0.31 |
| 8 | 0.26 |
| 9 | <0.11 |
| 10 | 0.17 |
| 13 | 0.25 |
| 14 | 0.3 |
| 15 | 0.2 |
| 16 | 0.33 |
| 17 | 0.16 |
| 18 | 0.15 |
| 19 | 0.38 |
| 20 | 0.14 |
| 21 | <0.11 |
| 22 | 0.18 |
| 23 | 0.83 |
| 24 | 0.13 |
| 25 | 0.44 |
| 26 | 0.28 |
| 27 | 0.15 |
| 28 | 0.19 |
| 29 | 0.31 |
| 30 | 0.28 |
| 31 | 0.28 |
| 32 | 0.47 |
| 33 | 0.3 |
| 34 | 0.59 |
| 35 | 0.31 |
| 36 | 0.24 |

-continued

| Example | Predicted Hepatic Clearance (Pred. Cl.) (L/h/kg) |
|---|---|
| 37 | 0.52 |
| 38 | 0.32 |
| 39 | <0.11 |
| 40 | <0.11 |
| 41 | 0.36 |
| 42 | 0.23 |
| 43 | 0.35 |
| 44 | 0.18 |
| 45 | 0.23 |
| 46 | 0.3 |
| 47 | 0.28 |
| 48 | 0.22 |
| 49 | 0.78 |
| 50 | <0.11 |
| 51 | <0.11 |
| 52 | <0.11 |
| 53 | 0.54 |
| 54 | 0.23 |
| 55 | 0.26 |
| 56 | <0.11 |
| 57 | <0.11 |
| 59 | <0.11 |
| 60 | <0.11 |
| 61 | <0.11 |
| 62 | 0.4 |
| 63 | <0.11 |
| 64 | 0.21 |
| 65 | 0.43 |
| 66 | 0.74 |
| 67 | 0.31 |
| 68 | <0.11 |
| 69 | <0.11 |
| 70 | 0.13 |
| 71 | <0.11 |
| 72 | 0.74 |
| 73 | 0.27 |
| 74 | 0.79 |
| 75 | 0.83 |
| 76 | 0.805 |
| 77 | 0.55 |
| 78 | 0.42 |
| 79 | 0.53 |
| 80 | 0.31 |
| 81 | 0.64 |
| 82 | 0.22 |
| 83 | <0.11 |
| 84 | 0.38 |
| 85 | 0.22 |
| 86 | <0.11 |
| 87 | <0.11 |
| 88 | 0.51 |
| 89 | 0.53 |
| 90 | 0.6 |
| 91 | 0.3 |
| 92 | 0.19 |
| 93 | 0.87 |
| 94 | <0.11 |
| 95 | 0.4 |
| 96 | 1.07 |
| 97 | 0.21 |
| 98 | 0.44 |
| 99 | 0.14 |
| 100 | <0.11 |
| 101 | 0.4 |
| 102 | 0.31 |
| 103 | 0.31 |
| 104 | 0.76 |
| 105 | 0.38 |
| 106 | <0.11 |
| 107 | 0.83 |
| 108 | 0.26 |
| 109 | 0.74 |
| 110 | 0.42 |
| 111 | 0.195 |
| 112 | 0.55 |
| 113 | 0.59 |

-continued

| Example | Predicted Hepatic Clearance (Pred. Cl.) (L/h/kg) |
|---|---|
| 114 | 0.355 |
| 115 | 0.5 |
| 116 | 0.44 |
| 117 | <0.11 |
| 118 | 0.7 |
| 119 | <0.11 |
| 120 | <0.11 |
| 121 | 0.16 |
| 122 | <0.11 |
| 123 | 0.31 |
| 124 | 0.19 |
| 125 | 0.155 |
| 126 | 0.28 |
| 127 | 0.4 |
| 128 | <0.11 |
| 129 | 0.19 |
| 130 | 0.33 |
| 131 | 0.24 |
| 132 | 0.215 |
| 133 | 0.335 |
| 134 | <0.11 |
| 135 | <0.11 |
| 136 | 0.54 |
| 137 | 0.29 |
| 138 | 0.45 |
| 139 | 0.43 |
| 140 | 0.56 |
| 141 | 0.33 |
| 142 | 0.53 |
| 143 | 0.32 |
| 145 | 0.5 |
| 146 | 0.44 |
| 147 | 0.7 |
| 148 | 0.69 |
| 152 | 0.7 |
| 153 | 0.31 |
| 154 | 0.29 |
| 155 | 0.33 |
| 156 | 0.33 |
| 157 | 0.46 |
| 158 | 0.23 |
| 159 | 0.36 |
| 160 | 0.3 |
| 161 | 0.23 |
| 162 | <0.11 |
| 163 | 0.3 |
| 164 | 0.4 |
| 165 | 0.24 |
| 166 | 0.29 |
| 167 | 0.36 |
| 168 | <0.11 |
| 169 | 0.32 |
| 170 | 0.38 |
| 172 | 0.57 |
| 173 | 0.3 |
| 174 | 0.34 |
| 175 | 0.94 |
| 176 | <0.11 |
| 177 | 0.42 |
| 178 | 0.59 |
| 179 | 0.21 |
| 180 | 0.38 |
| 181 | 0.17 |
| 182 | 0.46 |
| 184 | <0.11 |
| 185 | 0.72 |
| 186 | 0.69 |
| 187 | 0.89 |
| 188 | 1.05 |
| 189 | 0.51 |
| 190 | 0.41 |
| 191 | 0.47 |
| 192 | 0.78 |
| 193 | 0.41 |
| 194 | 0.28 |
| 195 | 0.57 |

-continued

| Example | Predicted Hepatic Clearance (Pred. Cl.) (L/h/kg) |
|---|---|
| 196 | 0.35 |
| 197 | 0.36 |
| 198 | 0.31 |
| 199 | <0.11 |
| 200 | 0.17 |
| 201 | 0.18 |
| 202 | 0.315 |
| 203 | 0.29 |
| 204 | 0.32 |
| 205 | 0.3 |
| 206 | 0.21 |
| 207 | 0.36 |
| 208 | 0.23 |
| 209 | 0.51 |
| 210 | 0.265 |
| 211 | 0.49 |
| 212 | <0.11 |
| 213 | 0.55 |
| 214 | 0.98 |
| 216 | <0.11 |
| 217 | 0.165 |
| 218 | 0.47 |
| 219 | 0.17 |
| 220 | 0.39 |
| 221 | 0.21 |
| 222 | 0.3 |
| 223 | 0.21 |
| 224 | 0.45 |
| 225 | 0.21 |
| 226 | 0.22 |
| 228 | 0.29 |
| 229 | 0.52 |
| 230 | 0.7 |
| 231 | 0.49 |
| 232 | 1.12 |
| 233 | 0.62 |
| 234 | <0.11 |
| 235 | 0.505 |
| 236 | <0.11 |
| 237 | 0.67 |
| 238 | 0.52 |
| 239 | <0.11 |
| 240 | 0.82 |
| 241 | 0.59 |
| 242 | <0.11 |
| 243 | 0.61 |
| 244 | 0.34 |
| 245 | 0.27 |
| 246 | 0.28 |
| 247 | 0.41 |
| 248 | 1.07 |
| 249 | 0.93 |
| 250 | <0.11 |
| 251 | <0.11 |
| 252 | <0.11 |
| 253 | 0.84 |
| 254 | <0.11 |
| 255 | 0.49 |
| 256 | 0.32 |
| 257 | 0.35 |
| 258 | 0.43 |
| 259 | 0.2 |
| 260 | 0.65 |
| 261 | 0.48 |
| 262 | <0.11 |
| 263 | 0.42 |
| 264 | 0.24 |
| 265 | 0.34 |
| 266 | 0.37 |
| 267 | 0.275 |
| 268 | 0.22 |
| 269 | 0.35 |
| 270 | 0.27 |
| 271 | <0.11 |
| 272 | 0.58 |
| 273 | 0.42 |

-continued

| Example | Predicted Hepatic Clearance (Pred. Cl.) (L/h/kg) |
|---|---|
| 274 | 0.48 |
| 275 | 0.73 |
| 276 | 0.385 |
| 277 | 0.43 |
| 278 | 0.18 |
| 279 | 0.5 |
| 280 | 0.24 |
| 281 | 0.4 |
| 282 | 0.49 |
| 283 | 0.52 |
| 284 | <0.11 |
| 285 | <0.11 |
| 286 | 0.157 |
| 287 | 0.63 |
| 288 | 0.305 |
| 289 | 0.115 |
| 290 | 0.505 |
| 291 | <0.11 |
| 292 | 0.57 |
| 293 | <0.11 |
| 294 | 0.5 |
| 295 | 0.5 |
| 296 | 0.32 |
| 297 | 0.15 |
| 298 | <0.11 |
| 299 | 0.31 |
| 300 | <0.11 |
| 301 | 0.303 |
| 302 | 0.16 |
| 303 | 0.24 |
| 304 | 0.32 |
| 305 | 0.28 |
| 306 | 0.36 |
| 307 | 0.32 |
| 308 | 0.35 |
| 309 | 0.31 |
| 310 | 0.38 |
| 311 | 0.42 |
| 312 | 0.28 |
| 313 | 0.43 |
| 314 | 0.3 |
| 315 | 0.34 |
| 316 | 0.28 |
| 317 | 0.16 |
| 318 | <0.11 |
| 319 | <0.11 |
| 320 | 0.25 |
| 321 | 0.38 |
| 322 | 0.74 |
| 323 | 0.26 |
| 324 | 0.17 |
| 325 | 0.34 |
| 326 | 0.74 |
| 327 | 0.18 |
| 328 | 0.66 |
| 329 | 0.47 |
| 330 | 0.19 |
| 331 | 0.24 |
| 332 | <0.11 |
| 333 | <0.11 |
| 334 | 0.2 |
| 335 | 0.29 |
| 336 | 0.42 |
| 337 | 0.29 |
| 338 | 0.78 |
| 339 | <0.11 |
| 340 | <0.11 |
| 341 | 0.34 |
| 342 | 0.24 |
| 343 | 0.38 |
| 344 | <0.11 |
| 345 | 0.23 |
| 346 | 0.47 |
| 347 | 0.33 |
| 348 | 0.57 |
| 349 | <0.11 |
| 350 | 0.38 |
| 351 | 0.12 |
| 352 | <0.11 |
| 353 | <0.11 |
| 354 | 0.45 |
| 355 | 0.2 |
| 356 | 0.43 |
| 357 | <0.11 |
| 358 | 0.39 |
| 359 | <0.11 |
| 360 | <0.11 |
| 361 | 0.17 |
| 362 | 0.97 |
| 363 | 0.465 |
| 364 | 0.23 |
| 365 | 0.28 |
| 366 | 0.33 |
| 367 | 0.65 |
| 368 | <0.11 |
| 369 | 0.26 |
| 370 | 0.4 |
| 371 | 0.18 |
| 372 | 0.47 |
| 373 | 1.17 |
| 374 | 0.39 |
| 375 | 0.255 |
| 376 | 0.23 |
| 377 | 0.19 |
| 378 | 0.33 |
| 379 | 0.21 |
| 380 | <0.11 |
| 381 | <0.11 |
| 382 | <0.11 |
| 383 | 0.52 |
| 384 | <0.11 |
| 385 | 0.32 |
| 386 | 0.12 |
| 387 | 0.5 |
| 388 | 0.31 |
| 389 | <0.11 |
| 390 | 0.45 |
| 391 | 0.325 |
| 392 | 0.19 |
| 393 | 0.3 |
| 394 | 0.25 |
| 395 | <0.11 |
| 396 | 0.52 |
| 397 | 0.17 |
| 398 | 0.61 |
| 399 | 0.2 |
| 400 | <0.11 |
| 401 | 0.415 |
| 402 | 0.7 |
| 403 | 0.297 |
| 404 | <0.11 |
| 405 | 0.33 |
| 406 | 0.23 |
| 407 | 0.225 |
| 408 | 0.605 |
| 409 | <0.11 |
| 410 | 0.89 |
| 411 | 0.56 |
| 412 | <0.11 |
| 413 | <0.11 |
| 414 | 0.7 |
| 415 | 0.26 |
| 416 | 0.25 |
| 417 | 0.76 |
| 418 | 0.29 |
| 419 | 0.44 |
| 420 | 0.21 |
| 421 | <0.11 |
| 422 | 0.16 |
| 423 | <0.11 |
| 424 | 0.14 |
| 425 | 0.4 |

-continued

| Example | Predicted Hepatic Clearance (Pred. Cl.) (L/h/kg) |
|---|---|
| 426 | 0.276 |
| 427 | <0.11 |
| 428 | 0.535 |
| 429 | 0.23 |
| 430 | <0.11 |
| 431 | 0.23 |
| 432 | <0.11 |
| 433 | <0.11 |
| 434 | 0.19 |
| 435 | 0.37 |
| 436 | <0.11 |
| 437 | 0.16 |
| 438 | 1.12 |
| 439 | 0.36 |
| 440 | 0.3 |
| 441 | 0.18 |
| 442 | 0.22 |
| 443 | 0.66 |
| 444 | 0.248 |
| 445 | 0.58 |
| 447 | 0.3 |
| 448 | <0.11 |
| 449 | 0.26 |
| 450 | <0.11 |
| 451 | 0.29 |
| 452 | 0.43 |
| 453 | 0.23 |
| 454 | 0.28 |
| 455 | <0.11 |
| 456 | <0.11 |
| 457 | 0.47 |
| 458 | <0.11 |
| 459 | <0.11 |
| 460 | 0.75 |
| 461 | 0.43 |
| 462 | <0.11 |
| 463 | 0.14 |
| 464 | 0.24 |
| 465 | <0.11 |
| 466 | 0.23 |
| 468 | 0.13 |
| 470 | <0.11 |
| 471 | 0.24 |
| 472 | <0.11 |
| 475 | 0.12 |
| 476 | 0.13 |
| 477 | 0.3 |
| 478 | 0.19 |
| 479 | 0.56 |
| 480 | <0.11 |
| 481 | <0.11 |
| 482 | 0.29 |
| 483 | 0.15 |
| 484 | 0.207 |
| 485 | 0.22 |
| 486 | 0.3 |
| 487 | 0.32 |
| 488 | 0.6 |
| 489 | <0.11 |
| 490 | 0.22 |
| 491 | 0.76 |
| 492 | <0.11 |
| 493 | 1.15 |
| 494 | 0.79 |
| 495 | 0.35 |
| 496 | 1.09 |
| 497 | 0.32 |
| 498 | <0.11 |
| 499 | 0.21 |
| 500 | 0.58 |
| 501 | 0.69 |
| 502 | 0.16 |
| 503 | <0.11 |
| 504 | 0.21 |
| 505 | <0.11 |
| 506 | 0.75 |

-continued

| Example | Predicted Hepatic Clearance (Pred. Cl.) (L/h/kg) |
|---|---|
| 507 | 1.15 |
| 508 | 0.15 |
| 509 | 0.7 |
| 510 | 0.87 |
| 511 | 1.12 |
| 512 | 0.46 |
| 513 | 0.31 |
| 514 | 0.91 |
| 515 | 0.45 |
| 516 | <0.11 |
| 517 | <0.11 |
| 518 | 0.32 |
| 519 | 0.21 |
| 520 | 0.375 |
| 521 | 0.405 |
| 522 | <0.11 |
| 523 | 0.3 |
| 524 | 0.43 |
| 525 | 0.12 |
| 526 | 0.45 |
| 527 | 0.22 |
| 528 | 0.45 |
| 529 | 0.27 |
| 530 | 0.63 |
| 531 | 0.135 |
| 532 | <0.11 |
| 533 | 0.6 |
| 534 | 0.91 |
| 535 | 0.25 |
| 536 | 0.145 |
| 537 | 0.2 |
| 539 | 0.38 |
| 540 | 0.20 |
| 541 | 0.22 |
| 542 | 1.2 |
| 543 | 0.28 |
| 544 | 0.19 |
| 545 | 0.40 |
| 546 | 0.53 |
| 547 | 0.44 |
| 548 | 0.45 |
| 549 | 0.72 |
| 552 | <0.11 |
| 553 | 0.25 |
| 554 | 0.25 |
| 555 | 0.11 |
| 556 | 1.17 |
| 557 | 0.13 |
| 558 | 0.24 |
| 559 | 0.41 |
| 560 | 0.35 |
| 561 | 0.57 |
| 563 | 0.22 |
| 564 | 0.205 |
| 565 | 0.36 |
| 567 | 0.46 |
| 568 | 0.29 |
| 569 | 1.02 |
| 570 | 0.11 |
| 571 | 0.53 |
| 573 | 0.39 |
| 574 | 0.115 |
| 575 | 0.52 |
| 576 | 0.48 |
| 577 | 0.45 |
| 578 | 0.28 |
| 579 | 0.96 |
| 580 | 0.35 |
| 581 | 0.38 |
| 582 | 0.91 |
| 583 | 0.62 |
| 585 | 0.14 |
| 586 | 0.46 |
| 587 | 0.41 |
| 588 | 0.39 |
| 589 | 0.49 |

-continued

| Example | Predicted Hepatic Clearance (Pred. Cl.) (L/h/kg) |
|---|---|
| 591 | 0.42 |
| 592 | 0.7 |
| 593 | 0.5 |
| 594 | 0.26 |
| 595 | 0.37 |
| 596 | 1.17 |
| 597 | 0.59 |
| 598 | 1.15 |
| 599 | 0.74 |
| 600 | 0.4 |
| 601 | 0.23 |
| 602 | 0.17 |
| 603 | 0.17 |
| 604 | 0.27 |
| 605 | 0.3 |
| 606 | 0.11 |
| 607 | 0.18 |
| 608 | 0.11 |
| 609 | 0.11 |
| 610 | 0.21 |
| 611 | 0.29 |
| 612 | 0.23 |
| 613 | 0.39 |
| 614 | 0.11 |
| 615 | 0.14 |
| 616 | 0.50 |
| 617 | 0.22 |
| 619 | 0.40 |
| 620 | 0.40 |
| 621 | 0.64 |
| 622 | 0.38 |
| 623 | 0.64 |
| 624 | 0.30 |
| 625 | 0.16 |
| 626 | 0.47 |
| 627 | 0.47 |
| 628 | 0.19 |
| 629 | 0.11 |
| 630 | 0.16 |
| 631 | 0.18 |
| 632 | 0.11 |
| 633 | 0.29 |
| 634 | 0.33 |
| 635 | 0.11 |
| 636 | 0.39 |
| 638 | 0.11 |
| 639 | 0.30 |
| 640 | 0.51 |
| 641 | 0.17 |
| 642 | 0.16 |
| 643 | 0.30 |
| 644 | 0.48 |
| 645 | 0.55 |
| 646 | 0.35 |
| 647 | 0.21 |
| 648 | 0.14 |
| 649 | 0.35 |
| 650 | 0.66 |
| 651 | 0.20 |
| 652 | 0.48 |
| 653 | 0.16 |
| 654 | 0.21 |
| 655 | 0.32 |
| 656 | 0.28 |
| 657 | 0.24 |
| 658 | 0.18 |
| 659 | 0.21 |
| 660 | 0.25 |
| 661 | 0.24 |
| 662 | 0.22 |
| 663 | 0.11 |
| 664 | 0.28 |
| 665 | 0.11 |
| 666 | 0.20 |
| 667 | 0.36 |
| 668 | 0.22 |

-continued

| Example | Predicted Hepatic Clearance (Pred. Cl.) (L/h/kg) |
|---|---|
| 669 | 0.11 |
| 670 | 0.19 |
| 671 | 0.11 |
| 672 | 0.11 |
| 673 | 0.27 |
| 674 | 0.36 |
| 675 | 0.17 |
| 676 | 0.14 |
| 677 | 0.11 |
| 678 | 0.25 |
| 679 | 0.30 |
| 680 | 0.33 |
| 681 | 0.20 |
| 682 | 0.15 |
| 683 | 0.39 |
| 684 | 0.18 |
| 685 | 0.14 |
| 686 | 0.24 |
| 687 | 0.52 |
| 688 | 0.62 |
| 689 | 0.31 |
| 690 | 0.36 |
| 691 | 0.25 |
| 692 | 0.11 |
| 693 | 0.58 |
| 694 | 0.11 |
| 695 | 0.11 |
| 696 | 0.65 |
| 697 | 0.11 |
| 698 | 0.38 |
| 699 | 0.28 |
| 700 | 0.31 |
| 701 | 0.23 |
| 702 | 0.16 |
| 703 | 0.34 |
| 704 | 0.11 |
| 705 | 0.80 |
| 706 | 0.73 |
| 707 | 0.24 |
| 708 | 0.45 |
| 709 | 0.53 |
| 710 | 0.66 |
| 711 | 0.38 |
| 712 | 0.41 |
| 713 | 0.15 |
| 714 | 0.11 |
| 715 | 0.12 |
| 716 | 0.13 |
| 717 | 0.45 |
| 718 | 0.11 |
| 719 | 0.11 |
| 720 | 0.32 |
| 721 | 0.47 |
| 722 | 0.11 |
| 723 | 0.21 |
| 724 | 0.40 |
| 725 | 0.57 |
| 726 | 0.33 |
| 727 | 0.33 |
| 728 | 0.50 |
| 729 | 0.11 |
| 730 | 0.11 |
| 731 | 0.62 |
| 732 | 0.49 |
| 733 | 0.23 |
| 734 | 0.48 |
| 735 | 0.43 |
| 736 | 0.14 |
| 737 | 0.11 |
| 738 | 0.56 |
| 739 | 0.11 |
| 740 | 0.13 |
| 742 | 0.11 |
| 743 | 0.40 |
| 744 | 0.11 |
| 745 | 0.11 |

-continued

| Example | Predicted Hepatic Clearance (Pred. Cl.) (L/h/kg) |
|---|---|
| 746 | 0.30 |
| 747 | 0.44 |
| 748 | 0.11 |
| 749 | 0.26 |
| 750 | 0.25 |
| 751 | 0.43 |
| 752 | 0.11 |
| 753 | 0.62 |
| 754 | 0.36 |
| 755 | 0.59 |
| 756 | 0.46 |
| 757 | 0.26 |
| 758 | 0.27 |
| 759 | 0.11 |
| 760 | 0.39 |
| 761 | 0.11 |
| 762 | 0.11 |
| 763 | 0.11 |
| 764 | 0.19 |
| 765 | 0.11 |
| 766 | 0.18 |
| 767 | 0.11 |
| 768 | 0.165 |
| 769 | 0.22 |
| 770 | 0.11 |
| 771 | 0.11 |
| 772 | 0.11 |
| 773 | 0.11 |
| 774 | 0.125 |
| 775 | 0.19 |
| 776 | 0.19 |
| 777 | 0.27 |
| 778 | 0.22 |
| 779 | 0.11 |
| 780 | 0.11 |
| 781 | 0.19 |
| 782 | 0.67 |
| 783 | 0.11 |
| 784 | 0.11 |
| 785 | 0.11 |
| 786 | 0.11 |
| 788 | 0.33 |
| 789 | 0.34 |
| 790 | 0.18 |
| 791 | 0.29 |
| 792 | 0.37 |
| 793 | 0.34 |
| 794 | 0.37 |
| 795 | 0.11 |
| 796 | 0.11 |
| 797 | 0.43 |
| 798 | 0.32 |
| 799 | 0.16 |
| 800 | 0.11 |
| 801 | 0.19 |
| 802 | 0.14 |
| 803 | 0.80 |
| 804 | 0.69 |
| 805 | 0.72 |
| 806 | 0.43 |
| 807 | 0.20 |
| 808 | 0.21 |
| 809 | 0.17 |
| 810 | 0.41 |
| 811 | 0.60 |
| 812 | 0.11 |
| 813 | 0.11 |
| 814 | 0.37 |
| 815 | 0.11 |
| 816 | 0.57 |
| 817 | 0.54 |
| 818 | 0.36 |
| 819 | 0.19 |
| 820 | 0.16 |
| 821 | 0.16 |
| 822 | 0.11 |

-continued

| Example | Predicted Hepatic Clearance (Pred. Cl.) (L/h/kg) |
|---|---|
| 823 | 0.11 |
| 824 | 0.46 |
| 825 | 0.11 |
| 826 | 0.22 |
| 827 | 0.43 |
| 828 | 0.51 |
| 829 | 0.11 |
| 830 | 0.15 |
| 831 | 0.17 |
| 832 | 0.86 |
| 833 | 0.59 |
| 834 | 0.38 |
| 835 | 0.67 |
| 836 | 0.11 |
| 837 | 0.11 |
| 838 | 0.26 |
| 839 | 0.35 |
| 840 | 0.29 |
| 841 | 0.37 |
| 842 | 0.11 |
| 843 | 0.16 |
| 844 | 0.15 |
| 845 | 0.74 |
| 847 | 0.36 |
| 848 | 0.17 |
| 849 | 0.32 |
| 850 | 0.20 |
| 851 | 0.15 |
| 852 | 0.27 |
| 853 | 0.54 |
| 854 | 0.14 |
| 855 | 0.33 |
| 857 | 0.19 |
| 858 | 0.53 |
| 859 | 0.11 |
| 860 | 0.11 |
| 861 | 0.11 |
| 862 | 0.26 |
| 863 | 0.29 |
| 865 | 0.26 |
| 866 | 0.49 |
| 867 | 0.11 |
| 868 | 0.21 |
| 869 | 0.39 |
| 870 | 0.11 |
| 871 | 0.12 |
| 872 | 0.11 |
| 873 | 0.73 |
| 874 | 0.11 |
| 875 | 0.56 |
| 876 | 0.11 |
| 877 | 0.43 |
| 878 | 0.53 |
| 879 | 0.36 |
| 880 | 0.45 |
| 881 | 0.53 |
| 882 | 0.37 |
| 883 | 0.45 |
| 884 | 0.19 |
| 885 | 0.55 |
| 886 | 0.35 |
| 887 | 0.53 |
| 888 | 0.35 |
| 890 | 0.31 |
| 891 | 0.40 |
| 892 | 0.33 |
| 893 | 0.11 |
| 894 | 0.25 |
| 895 | 0.48 |
| 896 | 0.27 |
| 897 | 0.13 |
| 898 | 0.58 |
| 899 | 0.24 |
| 900 | 0.11 |
| 901 | 0.27 |
| 902 | 0.52 |

-continued

| Example | Predicted Hepatic Clearance (Pred. Cl.) (L/h/kg) |
|---|---|
| 903 | 0.11 |
| 904 | 0.67 |
| 905 | 0.26 |
| 906 | 0.26 |
| 907 | 0.51 |
| 908 | 0.31 |
| 909 | 0.22 |
| 910 | 0.17 |
| 911 | 0.11 |
| 912 | 0.11 |
| 913 | 0.23 |
| 914 | 0.36 |
| 915 | 0.24 |
| 916 | 0.11 |
| 917 | 0.11 |
| 918 | 0.29 |
| 919 | 0.25 |
| 920 | 0.28 |
| 921 | 0.17 |
| 922 | 0.11 |
| 923 | 0.11 |
| 924 | 0.14 |
| 925 | 0.35 |
| 926 | 0.11 |

Although the foregoing has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating a GLP-1R mediated disease or condition comprising administering to a subject in need thereof a pharmaceutically effective amount of a compound, or pharmaceutically acceptable salt thereof, wherein the compound has the structure:

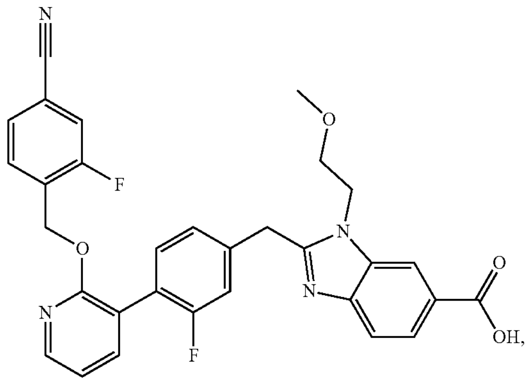

-continued

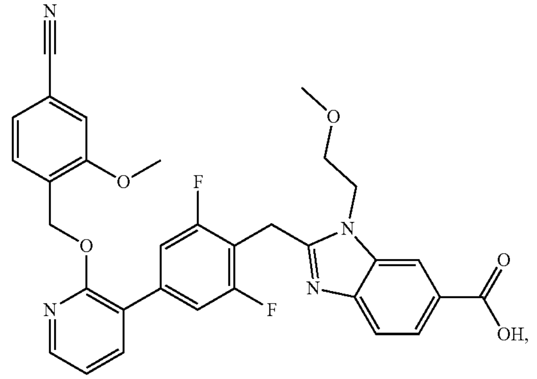

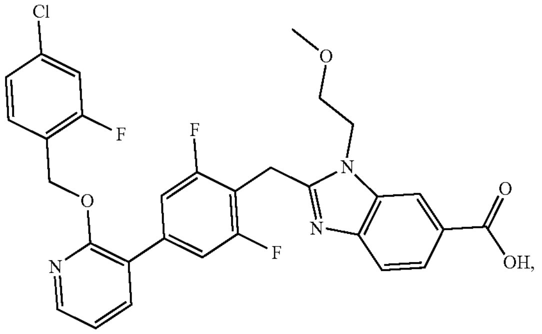

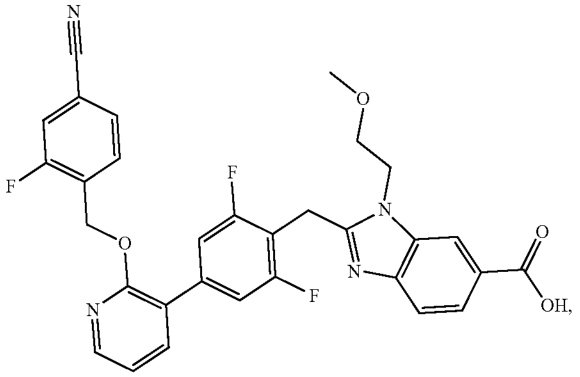

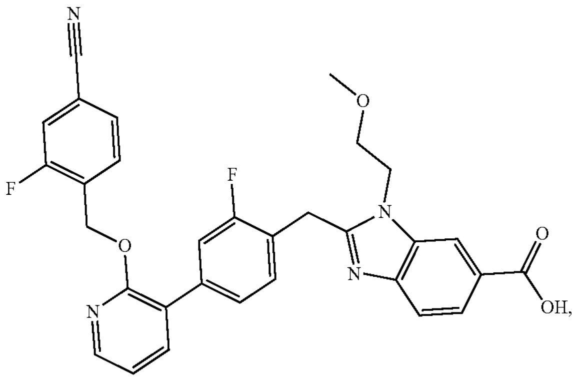

-continued

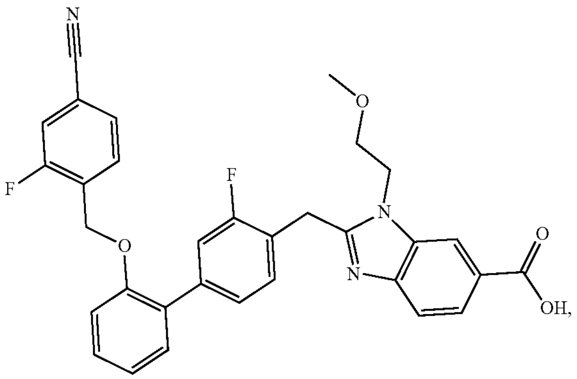

,

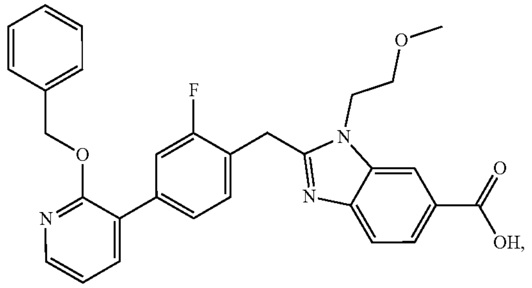

,

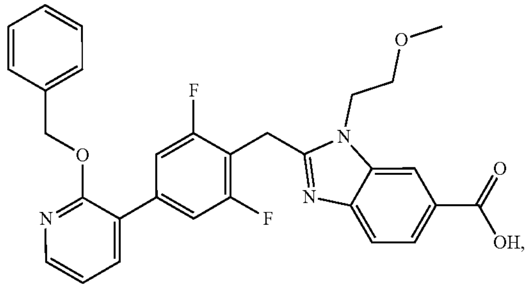

,

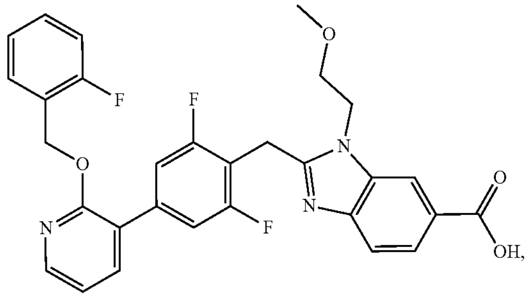

,

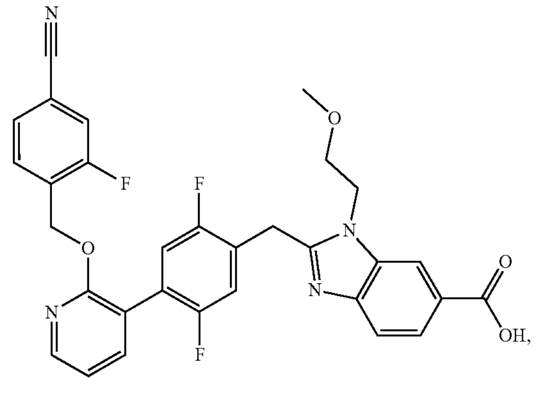

, or

-continued

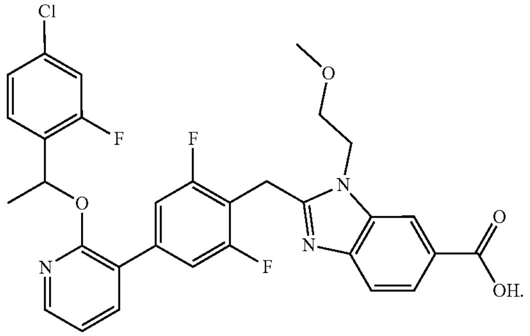

.

2. The method of claim 1, wherein the disease or condition comprises a liver disease.

3. The method of claim 2, wherein the disease or condition comprises liver fibrosis, non-alcoholic fatty liver disease (NAFLD), non-alcoholic steatohepatitis (NASH), liver cirrhosis, compensated liver fibrosis, decompensated liver fibrosis, hepatocellular carcinoma, Primary Biliary Cirrhosis (PBC), or Primary Sclerosing Choleangitis (PSC).

4. The method of claim 3, wherein the disease or condition comprises non-alcoholic fatty liver disease (NAFLD).

5. The method of claim 3, wherein the disease or condition comprises non-alcoholic steatohepatitis (NASH).

6. The method of claim 1, wherein the disease or condition comprises a metabolic disease.

7. The method of claim 1, wherein the disease or condition comprises type 1 diabetes, type 2 diabetes, pre-diabetes, idiopathic type 1 diabetes, latent autoimmune diabetes, maturity onset diabetes of the young, early onset diabetes, malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, obesity, eating disorders, sleep apnea, weight gain, sugar craving, dyslipidemia, hyperinsulinemia, congestive heart failure, myocardial infarction, stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, left ventricular hypertrophy, Parkinson's Disease, peripheral arterial disease, macular degeneration, cataract, glomerulosclerosis, chronic renal failure, metabolic syndrome, angina pectoris, premenstrual syndrome, thrombosis, atherosclerosis, impaired glucose metabolism, vascular restenosis, dementia, or Alzheimer's disease.

8. The method of claim 1, wherein the compound or pharmaceutically acceptable salt thereof is administered in combination with an additional therapeutic agent.

9. The method of claim 8, wherein the additional therapeutic agent is selected from the group consisting of: peptide YY or an analogue thereof, a neuropeptide Y receptor type 2 (NPYR2) agonist, a NPYR1 agonist, an NPYR5 antagonist, a cannabinoid receptor type 1 (CB1 R) antagonist, a lipase inhibitor, orlistat, a human proislet peptide (HIP), a melanocortin receptor 4 agonist (MC4R), setmelanotide, a melanin concentrating hormone receptor 1 antagonist, a famesoid X receptor (FXR) agonist, obeticholic acid, apoptotic signal-regulating kinase (ASK-1) inhibitor, zonisamide, phentermine alone or in combination with topiramate, a norepinephrine/dopamine reuptake inhibitor, buproprion, an opioid receptor antagonist, naltrexone, a combination of norepinephrine/dopamine reuptake inhibitor and opioid receptor antagonist, a combination of bupropion and naltrexone, a GDF-15 analog, sibutramine, a cholecystokinin agonist, amylin and analogues thereof, pramlintide, leptin and analogues thereof, metroleptin, a serotonergic agent, lorcaserin, a methionine aminopeptidase 2 (MetAP2) inhibitor, beloranib, ZGN-1061, phendimetrazine, diethylpropion, benzphetamine, an SGLT2 inhibitor, empagliflozin, canagliflozin, dapagliflozin, ipragliflozin, tofogliflozin, sergliflozin etabonate, remogliflozin etabonate, ertugliflozin, an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, a glucagon receptor agonist alone or in combination with another GLP-1 R agonist, liraglutide, exenatide, dulaglutide, albiglutide, lixisenatide, semaglutide, a peroxisome proliferator-activated receptor alpha (PPARα) agonist, fish oil, an acetyl-coA carboxylase (ACC) inhibitor, a TGFβ antagonist, GFRAL agonist, and a pharmaceutically acceptable salt thereof.

10. The method of claim 1, wherein the compound has the structure:

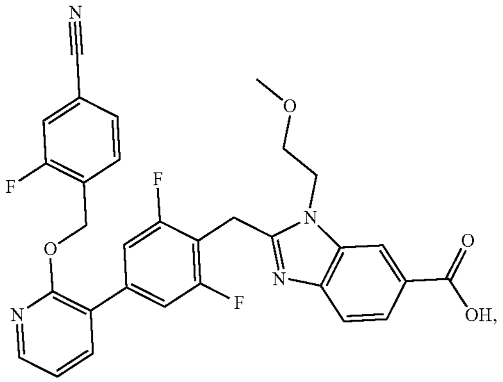

-continued

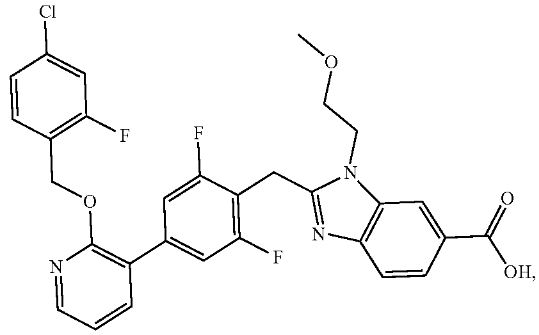

or

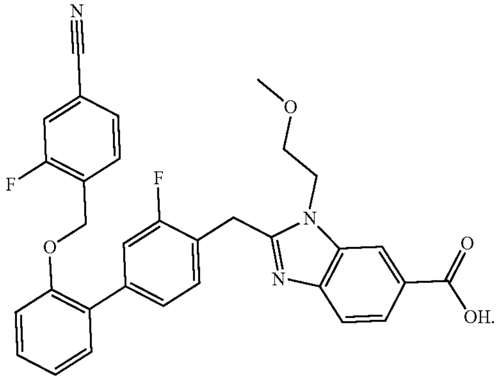

* * * * *